US011912699B2

(12) United States Patent
Crew et al.

(10) Patent No.: US 11,912,699 B2
(45) Date of Patent: Feb. 27, 2024

(54) TAU-PROTEIN TARGETING COMPOUNDS AND ASSOCIATED

(71) Applicant: Arvinas Operations, Inc., New Haven, CT (US)

(72) Inventors: Andrew P. Crew, Guilford, CT (US); Michael Berlin, Flemington, NJ (US); Angela M. Cacace, Haddam Neck, CT (US); Julian T. Chandler, Old Lyme, CT (US)

(73) Assignee: ARVINAS OPERATIONS, INC., New Haven, CT (US)

( * ) Notice: Subject to any disclaimer, the term of this patent is extended or adjusted under 35 U.S.C. 154(b) by 49 days.

(21) Appl. No.: 16/932,590

(22) Filed: Jul. 17, 2020

(65) Prior Publication Data

US 2022/0315575 A1 Oct. 6, 2022

Related U.S. Application Data

(60) Provisional application No. 62/875,500, filed on Jul. 17, 2019.

(51) Int. Cl.

| | |
|---|---|
| ***C07D 417/14*** | (2006.01) |
| ***A61K 47/54*** | (2017.01) |
| ***C07D 401/04*** | (2006.01) |
| ***C07D 487/04*** | (2006.01) |
| ***A61K 45/06*** | (2006.01) |

(52) U.S. Cl.

CPC ............ *C07D 417/14* (2013.01); *A61K 47/54* (2017.08); *C07D 401/04* (2013.01); *C07D 487/04* (2013.01); *A61K 45/06* (2013.01)

(58) Field of Classification Search

CPC .. C07D 417/14; C07D 401/04; C07D 487/04; C07D 401/14; C07D 471/14; C07D 519/00; C07D 471/04; A61K 47/54; A61K 45/06; A61K 38/00; A61P 25/28; A61P 9/00; A61P 21/00; A61P 25/00; A61P 25/04; A61P 25/06; A61P 25/08; A61P 25/14; A61P 25/16; A61P 25/24; A61P 35/00; A61P 37/06; C07K 5/06026; C07K 5/06034; C07K 5/06052; C07K 5/0606; C07K 5/06078; C07K 5/06139; C07K 5/0806

See application file for complete search history.

(56) References Cited

U.S. PATENT DOCUMENTS

| | | | |
|---|---|---|---|
| 6,306,663 | B1 | 10/2001 | Kenten et al. |
| 6,670,348 | B1 | 12/2003 | Rosen et al. |
| 7,030,141 | B2 | 4/2006 | Bigge et al. |
| 7,041,298 | B2 | 5/2006 | Deshaies et al. |
| 7,208,157 | B2 | 4/2007 | Dashaies et al. |
| 7,244,851 | B2 | 7/2007 | Cohen et al. |
| 7,345,081 | B2 | 3/2008 | Cohen et al. |
| 7,419,975 | B2 | 9/2008 | Palermo et al. |
| 7,517,906 | B2 | 4/2009 | Condon et al. |
| 9,447,070 | B2 | 9/2016 | Muller et al. |
| 9,500,653 | B2 | 11/2016 | Crews et al. |
| 9,632,089 | B2 | 4/2017 | Crews et al. |
| 2003/0096841 | A1 | 5/2003 | Robarge et al. |
| 2006/0128632 | A1 | 6/2006 | Sharma et al. |
| 2008/0051432 | A1 | 2/2008 | Zhang |
| 2008/0214501 | A1 | 9/2008 | Pan et al. |
| 2008/0219929 | A1 | 9/2008 | Wischik et al. |
| 2008/0269140 | A1 | 10/2008 | Wang et al. |
| 2010/0203012 | A1 | 8/2010 | Laurent et al. |
| 2011/0195043 | A1 | 8/2011 | Sun et al. |
| 2011/0196150 | A1 | 8/2011 | Man et al. |
| 2011/0269793 | A1 | 11/2011 | Macconi et al. |
| 2012/0270800 | A1 | 10/2012 | Verdine et al. |
| 2014/0302523 | A1 | 10/2014 | Crews et al. |
| 2014/0356322 | A1 | 12/2014 | Crews et al. |
| 2015/0119435 | A1 | 4/2015 | Crews et al. |
| 2015/0291562 | A1 | 10/2015 | Crew et al. |
| 2015/0344473 | A1 | 10/2015 | Du et al. |

(Continued)

FOREIGN PATENT DOCUMENTS

| | | | |
|---|---|---|---|
| CN | 1844118 | A | 10/2006 |
| CN | 103688176 | A | 3/2014 |

(Continued)

OTHER PUBLICATIONS

Bohnert, et al., Plasma Protein Binding: From Discovery to Development, Journal of Pharmaceutical Sciences, vol. 102, No. 9, Sep. 2013, 2953-2994.

Gadhave, et al., The ubiquitin proteasomal system: a potential target for the management of Alzheimer's disease, J. Cell. Mol. Med. vol. 20, No. 7, 2016 pp. 1392-1407 (Jan. 17, 2016).

Harrington, et al., Cellular Models of Aggregation-dependent Template-directed Proteolysis to Characterize Tau Aggregation Inhibitors for Treatment of Alzheimer Disease, The Journal of Biological Chemistry vol. 290, No. 17, pp. 10862-10875, Apr. 24, 2015.

(Continued)

*Primary Examiner* — Brandon J Fetterolf
*Assistant Examiner* — Lauren Wells
(74) *Attorney, Agent, or Firm* — Brian C. Trinque; Lathrop GPM LLP

(57) ABSTRACT

The present disclosure relates to bifunctional compounds, which find utility as modulators of tau protein. In particular, the present disclosure is directed to bifunctional compounds, which contain on one end a VHL or cereblon ligand which binds to the E3 ubiquitin ligase and on the other end a moiety which binds tau protein, such that tau protein is placed in proximity to the ubiquitin ligase to effect degradation (and inhibition) of tau. The present disclosure exhibits a broad range of pharmacological activities associated with degradation/inhibition of tau protein. Diseases or disorders that result from aggregation or accumulation of tau protein are treated or prevented with compounds and compositions of the present disclosure.

21 Claims, 7 Drawing Sheets

(56) References Cited

U.S. PATENT DOCUMENTS

| | | | |
|---|---|---|---|
| 2016/0022642 | A1 | 1/2016 | Crews et al. |
| 2016/0045607 | A1 | 2/2016 | Crew et al. |
| 2016/0058872 | A1 | 3/2016 | Arvinas |
| 2016/0136230 | A1 | 5/2016 | Campos et al. |
| 2016/0214972 | A1 | 7/2016 | Jin et al. |
| 2016/0243247 | A1 | 8/2016 | Bradner et al. |
| 2016/0272639 | A1 | 9/2016 | Crew et al. |
| 2016/0368911 | A1 | 12/2016 | Campos et al. |
| 2017/0008904 | A1 | 1/2017 | Crew et al. |
| 2017/0037004 | A1 | 2/2017 | Crew et al. |
| 2017/0065719 | A1 | 3/2017 | Qian et al. |
| 2017/0121321 | A1 | 5/2017 | Crews et al. |
| 2017/0281784 | A1 | 10/2017 | Wang et al. |
| 2017/0307614 | A1 | 10/2017 | Crews et al. |
| 2017/0327469 | A1 | 11/2017 | Crew et al. |
| 2018/0015087 | A1 | 1/2018 | Liu et al. |
| 2018/0072711 | A1 | 3/2018 | Crew et al. |
| 2018/0099940 | A1 | 4/2018 | Crew et al. |
| 2018/0125821 | A1 | 5/2018 | Crew et al. |
| 2018/0147202 | A1 | 5/2018 | Crew et al. |
| 2018/0155322 | A1 | 6/2018 | Crew et al. |
| 2018/0177750 | A1 | 6/2018 | Crew et al. |
| 2018/0179183 | A1 | 6/2018 | Crew et al. |
| 2018/0193470 | A1 | 7/2018 | Crew et al. |
| 2018/0215731 | A1 | 8/2018 | Crew et al. |
| 2018/0228907 | A1 | 8/2018 | Crew et al. |
| 2018/0237418 | A1 | 8/2018 | Crew et al. |
| 2018/0256586 | A1 | 9/2018 | Crew et al. |
| 2018/0353501 | A1 | 12/2018 | Crew et al. |
| 2019/0151295 | A1 | 5/2019 | Crew et al. |

FOREIGN PATENT DOCUMENTS

| | | | |
|---|---|---|---|
| EA | 201390803 | A1 | 9/2013 |
| EP | 2909197 | B1 | 8/2015 |
| EP | 2985285 | | 2/2016 |
| EP | 3468560 | A1 | 4/2019 |
| JP | A 2010-502627 | | 1/2010 |
| RU | 2008112221 | A | 10/2009 |
| RU | 2448101 | C2 | 4/2012 |
| RU | 2011121567 | A | 10/2012 |
| RU | 2012138709 | A | 3/2014 |
| WO | WO 2000/066119 | | 11/2000 |
| WO | WO 2002/066512 | | 8/2002 |
| WO | WO 2002/100845 | | 12/2002 |
| WO | WO 2005/016326 | | 2/2005 |
| WO | WO 2005/097791 | | 10/2005 |
| WO | WO 2006/069063 | | 6/2006 |
| WO | WO 2006/113942 | | 10/2006 |
| WO | WO 2007/101347 | | 9/2007 |
| WO | WO 2007/106670 | | 9/2007 |
| WO | WO 2007/115289 | | 10/2007 |
| WO | WO 2007/130626 | | 11/2007 |
| WO | WO 2008/011392 | | 1/2008 |
| WO | WO 2008/014236 | | 1/2008 |
| WO | WO 2008/109057 | | 9/2008 |
| WO | WO 2008/128121 | | 10/2008 |
| WO | WO 2008/128171 | | 10/2008 |
| WO | WO 2008/134679 | | 11/2008 |
| WO | WO 2009/015254 | | 1/2009 |
| WO | WO 2009/060292 | | 5/2009 |
| WO | WO 2010/053732 | A1 | 5/2010 |
| WO | WO 2010/141805 | | 12/2010 |
| WO | WO 2011/119565 | | 9/2011 |
| WO | WO 2012/003281 | | 1/2012 |
| WO | WO 2012/040527 | | 3/2012 |
| WO | WO 2012/078559 | | 6/2012 |
| WO | WO 2012/090104 | | 7/2012 |
| WO | WO 2017/176958 | | 10/2012 |
| WO | WO 2013/071035 | | 5/2013 |
| WO | WO 2013/071039 | | 5/2013 |
| WO | WO 2013/106643 | | 7/2013 |
| WO | WO 2013/106646 | | 7/2013 |
| WO | WO 2013/170147 | | 11/2013 |
| WO | WO 2013/176698 | A1 | 11/2013 |
| WO | WO 2014/011712 | | 1/2014 |
| WO | WO 2014/025759 | | 2/2014 |
| WO | WO 2014/047024 | | 3/2014 |
| WO | WO 2014/055461 | | 4/2014 |
| WO | WO 2014/074658 | | 5/2014 |
| WO | WO 2014/108452 | | 7/2014 |
| WO | WO 2014/123418 | | 8/2014 |
| WO | WO 2015/000868 | | 1/2015 |
| WO | WO 2015/006524 | | 1/2015 |
| WO | WO 2015/110263 | A1 | 7/2015 |
| WO | WO 2015/160845 | | 10/2015 |
| WO | WO 2015/173225 | A1 | 11/2015 |
| WO | WO 2016/105518 | | 6/2016 |
| WO | WO 2016/124508 | A1 | 8/2016 |
| WO | WO 2016/146985 | | 9/2016 |
| WO | WO 2016/169989 | | 10/2016 |
| WO | WO 2016/172134 | | 10/2016 |
| WO | WO 2016/197114 | | 12/2016 |
| WO | WO 2017/007612 | A1 | 1/2017 |
| WO | WO 2017/011590 | | 1/2017 |
| WO | WO 2017/024317 | | 2/2017 |
| WO | WO 2017/024318 | A1 | 2/2017 |
| WO | WO 2017/024319 | A1 | 2/2017 |
| WO | WO 2017/030814 | | 2/2017 |
| WO | WO 2017/046036 | | 3/2017 |
| WO | WO 2017/079267 | | 5/2017 |
| WO | WO 2017/117473 | | 7/2017 |
| WO | WO 2017/117474 | | 7/2017 |
| WO | WO 2017/161119 | | 9/2017 |
| WO | WO 2017/176957 | | 10/2017 |
| WO | WO 2017/185023 | | 10/2017 |
| WO | WO 2017/185031 | | 10/2017 |
| WO | WO 2017/185034 | | 10/2017 |
| WO | WO 2017/185036 | | 10/2017 |
| WO | WO2017184995 | A1 | 10/2017 |
| WO | WO 2017/197051 | | 11/2017 |
| WO | WO 2017/197055 | | 11/2017 |
| WO | WO 2017/197056 | A1 | 11/2017 |
| WO | WO 2017/223415 | | 12/2017 |
| WO | WO 2017/223452 | | 12/2017 |
| WO | WO 2018/052945 | A1 | 3/2018 |
| WO | WO 2018/052949 | | 3/2018 |
| WO | WO 2018/064589 | A1 | 4/2018 |
| WO | WO 2018/089736 | A1 | 5/2018 |
| WO | WO 2018/098275 | | 5/2018 |
| WO | WO 2018/098280 | A1 | 5/2018 |
| WO | WO 2018/098288 | | 5/2018 |
| WO | WO 2018/106870 | | 6/2018 |
| WO | WO2018102067 | A2 | 6/2018 |
| WO | WO 2018/148440 | | 8/2018 |
| WO | WO2018144649 | A1 | 8/2018 |
| WO | WO 2019/014429 | | 1/2019 |
| WO | WO 2019/060742 | A1 | 3/2019 |
| WO | WO 2019/084026 | A1 | 5/2019 |
| WO | WO 2019/084030 | A1 | 5/2019 |
| WO | WO 2019/099868 | | 5/2019 |
| WO | WO 2019/195201 | A1 | 10/2019 |
| WO | WO2019199816 | A1 | 10/2019 |
| WO | WO2020041331 | A1 | 2/2020 |
| WO | WO2020176424 | A1 | 9/2020 |

OTHER PUBLICATIONS

Kovacs, G.G., Chapter 25—Tauopathies—Handbook of Clinical Neurology, vol. 145 (3rd series)—Neuropathology, 2018, pp. 355-368.

Li, et al., Thiadiazole—a Promising Structure in Medicinal Chemistry, ChemMedChem 2013, 8, 27-41 (Jan. 2013).

Pickhardt, et al., Identification of small molecule inhibitors of Tau aggregation by targeting monomeric Tau as a potential therapeutic approach for Tauopathies, Curr Alzheimer Res. 2015 ; 12(9): 814-828, (Author manuscript; available in PMC Aug. 8, 2016).

Rapoport, et al. (2002) Tau is essential to β-amyloid-induced neurotoxicity, Apr. 30, 2002, PNAS, vol. 99, No. 9, 6364-6369.

Seo, et al., A Smart Near-Infrared Fluorescence Probe for Selective Detection of Tau Fibrils in Alzheimer's Disease, ACS Chem. Neurosci. 2016, 7, 1474-1481, Aug. 30, 2016.

(56) References Cited

OTHER PUBLICATIONS

Wood, et al., [11C]PBB3—a new PET ligand that identifies tau pathology in the brains of patients with AD, Nature Reviews Neurology 9, 599 (2013); published online Oct. 22, 2013; doi:10.1038/nrneurol.2013.216.
Popovic, Natalia, Neuroprotective effect of chronic verapamil treatment on cognitive and noncognitive deficits in an experimental alzheimer's disease in rats, Jun. 26, 1997, Intern J. Neuroscience, vol. 92: 1-2, 79-93.
Beveridge, R., et al., Native Mass Spectrometry Can Effectively Predict PROTAC Efficacy, ACS Cent. Sci. Jul. 6, 2020, 6, 1223-1230.
International Search Report and Written Opinion for PCT/US2020/042645 dated Dec. 8, 2020.
Ahn, et al., "HIF-lalpha peptide derivatives with modifications at the hydroxyproline residue as activators of HIF-lalpha", Bioorg Med Chem Lett. 19(15), 2009, 4403-4405 (May 27, 2009).
Ardecky, RJ, et al., "Design, synthesis and evaluation of inhibitor of apoptosis protein (IAP) antagonists that are highly selective for the BIR2 domain of XIAP", Bioorg. Med. Chem., 23(14): 4253-4257 (May 14, 2013).
Asano M, et al., "Design, sterioselective synthesis, and biological evaluation of novel tri-cyclic compounds as inhibitor of apoptosis proteins (IAP) antagonists", Bioorg. Med. Chem., 21(18): 5725-5737 (Sep. 15, 2013).
Bargagna-Mohan, et al., "Use of PROTACS as molecular probes of angiogenesis", Bioorg Med Chem Left. 15(11) 2005, 2724-2727 (Jun. 2, 2005).
Bondeson DP, et al. (Jan. 18, 2018) "Lessons in PROTAC Design from Selective Degradation with a Promiscuous Warhead." *Cell Chem Biol* 25(1):78-87 e75.
Bondeson, et al., (Jan. 2017) "Targeted Protein Degradation by Small Molecules." *Annu Rev Pharmacol Toxicol* 57:107-123.
Bondeson, et al., "Catalytic in vivo protein knockdown by small-molecule PROTACS", National Chem Biol. 11(8) Aug. 2015, 611-617.
Buckley, et al., "HaloPROTACS: use of small molecule PROTACS to induce degradation of HaloTag fusion proteins", ACS Chem Biol. 10(8), 2015, 1831-1837 Aug. 21, 2015.
Buckley, et al., "Small-molecule inhibitors of the interaction between the E3 ligase VHL and HIF1a", Angew Chem Int Ed Engl.51(46), Nov. 12, 2012, 11463-11467.
Buckley, et al., "Targeting the von Hippel-Lindau E3 ubiquitin ligase using small molecules to disrupt the VHL/HIF-1α interaction", Journal of the American Chemical Society, Feb. 27, 2012, 134(10): 4465-4468.
Burslem GM, et al. (Jan. 18, 2018) "The Advantages of Targeted Protein Degradation Over Inhibition: An RTK Case Study." *Cell Chem Biol* 25(1):67-77 e63.
Burslem, et al., (Sep. 13, 2017) "Small-Molecule Modulation of Protein Homeostasis." *Chem Rev* 117(17):11269-11301.
Capitosti, S., et al., "Thalidomide analogues demonstrate dual inhibition of both angiogenesis and prostate cancer", Bioorganic & Medicinal Chemistry 12, (2004) 327-336 Jan. 1, 2004.
Carmony, KC, et al., "PROTAC-Induced Proteolytic Targeting", Methods Mol. Biol., 2012, vol. 832, pp. 627-638. Dec. 5, 2013.
CAS Registry No. 1004933-70-3, which entered STN on Feb. 21, 2008.
CAS Registry No. 871986-52-6 entered STN Jan. 16, 2006.
CAS RN 1542127-97-8 STN Entry, Feb. 11, 2014.
Cas STN Registry No. 1036376-76-7 [Entered STN: Jul. 27, 2008]. (Year: 2008).
CAS STN Registry No. 1808162-87-9 [Entered STN: Sep. 25, 2015]. (Year: 2015).
Chan, et al., (Jun. 8, 2018) "Impact of Target Warhead and Linkage Vector on Inducing Protein Degradation: Comparison of Bromodomain and Extra-Terminal (BET) Degraders Derived from Triazolodiazepine (JQ1) and Tetrahydroquinoline (I-BET726) Bet Inhibitor Scaffolds." *J Med Chem* 61(2):504-513.
Chu, Ting-Ting, et al., Specific Knockdown of Endogenous Tau Protein by Peptide-Directed Ubiquitin-Proteasome Degradation, Cell Chem Biol., Apr. 21, 2016, 23(4):453-461, doi: 10.1016/j.chembiol.2016.02.016.
Churcher I, (Jan. 25, 2018) "Protac-Induced Protein Degradation in Drug Discovery: Breaking the Rules or Just Making New Ones?" *J Med Chem* 61(2):444-452.
Cohen, F, et al., "Orally bioavailable antagonists of inhibitor of apoptosis proteins based on an azabicyclooctane scaffold", J. Med. Chem., 52(6), 1723-1730 Mar. 26, 2009.
Cohen, F. et al., "Antogonists of inhibitors of apoptosis proteins based on thiazole amide isosteres", Bioorg. Med. Chem. Lett., 20(7), 2229-2233 ( Feb. 8, 2010).
Contino-Pepin, Christiane, et al., "Preliminary biological evaluations of new thalidomide analogues for multiple sclerosis application", Bioorganic & Medicinal Chemistry Letter 19 (2009), 878-881 Dec. 7, 2008.
Corson, et al., "Design and applications of bifunctional small molecules: why two heads are better than one", ACS Chemical Biology vol. 3 No. 11, pp. 677-692; Nov. 21, 2008.
Crew AP, et al. (Jan. 25, 2018) "Identification and Characterization of Von Hippel-Lindau-Recruiting Proteolysis Targeting Chimeras (PROTACs) of TANK-Binding Kinase 1." *J Med Chem* 61(2):583-598.
Crews, C. M., "Targeting the undruggable proteome: the small molecules of my dreams", *Chem Biol* 17, 551-555, doi:S1074-5521(10)00196-1 [pii] 10.1016/j.chembiol.2010.05.011 (Jun. 25, 2010).
Cromm, et al., (Sep. 21, 2017) "Targeted Protein Degradation: from Chemical Biology to Drug Discovery." *Cell Chem Biol* 24(9):1181-1190.
Cyrus, et al., "Jostling for position: optimizing linker location in the design of estrogen receptor-targeting PROTACs", Chem Med Chem. 5(7), Jul. 5, 2010, 979-985.
Cyrus, K. et al., "Impact of Linker Length on the Activity of PROTACs," Mol. Biosyst., 2011, vol. 7, No. 2, pp. 359-364 (Feruary 2011).
Cyrus, K. et al., "Two-Headed PROTAC: An Effective New Tool for Targeted Protein Degradation," Chembiochem., 2010, vol. 11, pp. 1531-1534 Jul. 26, 2010.
Fischer, et al., "Structure of the DDB1-DRBN E3 Ubiquitin ligase in complex with thalidomide", Nature, vol. 512, pp. 49-53 (Jul. 16, 2014).
Flygare, J.A., et al. "Small-molecule pan-IAP antagonists: a patent review", Expert Opin. Ther. Pat., 20 (2), 251-267 (Feb. 2010).
Gadd, M.S., et al., "Structural basis of PROTAC cooperative recognition for selective protein degradation", Nat Chem Biol 13, 514-521 ( Mar. 13, 2017).
Galdeano, et al., "Structure-guided design and optimization of small molecules targeting the protein-protein interaction between the von hippel-lindau (VHL) E3 ubiquitin ligase and the Hypoxia inducible factor (HIF) alpha subunit with in vitro nanomolar affinities", Journal Med Chem, Aug. 2014, vol. 57, pp. 8657-8663.
Gosink, M et al., "Redirecting the specificity of ubiquitination by modifying ubiquitin-conjugating enzymes", Pro. Natl. Acad Sci, vol. 92, pp. 9117-9121, 1995 (Sep. 26, 1995).
Han, Xin, et al., Discovery of ARD-69 as a Highly Potent Proteolysis Targeting Chimera (PROTAC) Degrader of Androgen Receptor (AR) for the Treatment of Prostate Cancer, Journal of Medicinal Chemistry 2019 62 (2), 941-964, DOI: 10.1021/acs.jmedchem.8b01631 Jan. 24, 2019.
Hennessy, EJ, et al., "Discovery of aminopiperidine-based Smac mimetics as IAP antagonists", Bioorg. Med. Chem. Lett., 22(4), 1690-1694 (Feb. 15, 2012).
Hines, J., et al., "Posttranslational protein knockdown coupled to receptor tyrosine kinase activation with phosphoPROTACs", Proc Natl Acad Sci USA 110, 8942-8947 (May 14, 2013).
Hird, AW, et al., "Structure-based design and synthesis of tricyclic IAP (Inhibitors of Apoptosis Proteins) inhibitors", Bioorg. Med. Chem. Lett., 24(7): 1820-1824 (Apr. 1, 2014).
Hon, et al., "Structural basis for the recognition of hydroxyproline in HIf-1 alpha by pVHL", Nature 417, Jun. 2, 20027, 975-978.

(56) References Cited

OTHER PUBLICATIONS

Hu, Jiantao, et al., Discovery of ERD-308 as a Highly Potent Proteolysis Targeting Chimera (PROTAC) Degrader of Estrogen Receptor (ER), DOI: 10.1021/acs.jmedchem.8b01572, Journal of Medicinal Chemistry, vol. 62, pp. 1420-1442, Jan. 18, 2019, http://dx.doi.org/10.1021/acs.jmedchem.8b01572.
Huang HT, et al. (Jan. 18, 2018) "A Chemoproteomic Approach to Query the Degradable Kinome Using a Multi-kinase Degrader." *Cell Chem Biol* 25(1):88-99 e86.
Huang, et al., (Apr. 2016) "Drugging the undruggables: exploring the ubiquitin system for drug development." *Cell Res* 26(4):484-498.
Hughes, et al., (Nov. 8, 2017) "Molecular recognition of ternary complexes: a new dimension in the structure-guided design of chemical degraders." *Essays Biochem* 61(5):505-516.
Itoh, et al., "Development of target protein selective degradation inducer for protein knockdown," Bioorg. Med. Chem., 2011, 19, 3229-3241. Mar. 28, 2011.
Itoh, et al., "Protein knockdown using methyl bestatin-ligand hybrid molecules: design and synthesis of inducers of ubiquitination-mediated degradation of cellular retinoic acid-binding proteins," J. Am. Chem. Soc., 2010, 132, 5820-5826.Apr. 28, 2010.
Ivan, M., et al., "HIFa Targeted for VHL-Mediated Destruction by Proline Hydroxylation: Implications for O2 Sensing", Science, vol. 292, No. 5516, pp. 464-468, Apr. 20, 2001.
Jang, E.R. et al., "Targeted Degradation of Proteins by PROTACs," Curr. Protoc. Chem. Biol., 2010, vol. 2, No. 2, pp. 71-87 Jun. 1, 2010.
Kim, K.S., "Discovery of tetrahydroisoquinoline-based bivalent heterodimeric IAP antagonists", Bioorg. Med. Chem. Lett. 24(21), 5022-5029 (Sep. 16, 2014).
Knott, Edward (1955). "Compounds containing sulphur chromophores. Part I. The action of bases on heterocyclic sulphide quarternary salts", Journal of The Chemical Society (resumed). 10.1039/jr9550000916. 949-954.
Kronke, et al., "Lenalidomide Causes Selective Degradation of IKZF1 and IKZF3 in Multiple Myeloma Cells", Science 343, 301-305 (Jan. 17, 2014).
Lai, A.C., et al., "Modular PROTAC Design for the Degradation of Oncogenic BCR-ABL", Angew Chem Int Ed Engl 55, 807-810 (Jan. 11, 2016).
Lai, et al., (Feb. 2017) "Induced protein degradation: an emerging drug discovery paradigm." *Nat Rev Drug Discov* 16(2):101-114.
Lebraud, H., et al., "Protein Degradation by In-Cell Self-Assembly of Proteolysis Targeting Chimeras", ACS Central Science, 2, 927-934 (Dec. 5, 2016).
Lee, et al., "Targeted Degradation of the Aryl Hydrocarbon Receptor by the PROTAC Approach: A Useful Chemical Genetic Tool", ChemBioChem vol. 8, Issue 17, pp. 2058-2062, Nov. 23, 2007.
Levine, et al., Targeting the androgen receptor with steroid conjugates, J. Med. Chem., vol. 57., No. 20. pp. 8224-8237, (Sep. 14, 2014).
Li, Yan, et al., "Single polymer-drug conjugate carrying two drugs for fixed-dose co-delivery", Medicinal Chemistry, 2014, vol. 4(10): 676-683 Jan. 2014.
Liu, K., et al., "Design and biological characterization of hybrid compounds of curcumin and thalidomide for multiple myeloma", Org. Biomol. Chem. 2013, 11, 4757-476 , Jun. 11, 2013.
Lonskaya, et al. "Nilotinib-induced autophagic changes increase endogenous parkin level and ubiquitination, leading to amyloid clearance" J. Mol. Med. 2014, 92, 373-386. (Year: 2014).
Lopez-Girona, A. et al., Cereblon is a direct protein target for immunomodulatory and antiproliferative activities of lenalidomide and pomalidomide, Leukemia 26: 2326-2335, Nov. 2012.
Lu M, Liu T, Jiao Q, Ji J, Tao M, Liu Y, You Q, Jiang Z. Discovery of a Keap1-dependent peptide PROTAC to knockdown Tau by ubiquitination-proteasome degradation pathway. Eur J Med Chem. Feb. 25, 2018;146:251-259.
Lu, et al., "Hijacking the E3 ubiquitin ligase cereblon to efficiently target BRD4", Chem Biol 22(6), 2015, 755-763, Jun. 18, 2015.
Lu, et al., "The myeloma drug lenalidomide promotes the cereblon-dependent destruction of ikaros proteins", Science 343, 305-309 (Jan. 17, 2014).
Maniaci C, et al. (Oct. 10, 2017) "Homo-PROTACs: bivalent small-molecule dimerizers of the VHL E3 ubiquitin ligase to induce self-degradation." *Nat Commun* 8(1):830 1-13.
Mannhold, R., et al., "IAP antagonists: promising candidates for cancer therapy", Drug Discov. Today, 15 (5-6), 210-219 (Jan. 20, 2010).
Mendelsohn, A.R., et al. "Rapamycin As an Antiaging Therapeutic ?: Targeting Mammalian Target of Rapamycin to Treat Hutchinson-Gilford Progeria and Neurodegenerative Diseases" Rejuv. Res. 2011, 14, 437-441. (Year: 2011).
Min, Jung-hyun, et al., "Structure of an HIV-1-alpha—pVHL complex: hydroxyproline recognition in signaling", Jun. 7, 2002, 296: 1886-1889.
Muller, G., et al., "Amino-Substituted Thalodomide Analogs: Potent Inhibitors of TNF-α Production", Bioorganic & Medicinal Chemistry Letters 9 (Jun. 7, 1999) 1625-1630.
Ndubaku, C, et al., "Antagonism of c-IAP and XIAP proteins is required for efficient induction of cell death by small-molecule IAP antagonists", ACS Chem Biol. Jul. 17, 2009;4(7):557-566.
Neklesa, T.K., et al., "Chemical biology: Greasy tags for protein removal", Nature 487, 308-309 (Jul. 18, 2012).
Neklesa, Targeted protein degradation by PROTACs. Pharmacology & Therapeutics 174, 138-144 (Jun. 2017).
Nikolovska-Coleska, et al., "Interaction of a cyclic, Bivalent Smac Mimetic with the X-linked inhibitor of apoptosis protein", Biochemistry, 2008, 47(37), pp. 9811-9824 Aug. 22, 2008.
Noguchi-Yachide, et al., BET Bromodomain as a Target of Epigenitic Therapy, Chemical and Pharmaceutical Bulletin, Jun. 1, 2016, vol. 64, Iss 6, pp. 540-547.
Ohoka, N. et al. SNIPER(TACC3) induces cytoplasmic vacuolization and sensitizes cancer cells to Bortezomib. Cancer Sci. 108, 1032-1041 (May 2017).
Oost, T.K. et al., "Discovery of potent antagonists of the antiapoptotic protein XIAP for the treatment of cancer", Journal of Medicinal Chemistry 2004, 47, 4417-4426 Jul. 31, 2004.
Ottis P, et al. (Oct. 20, 2017) "Assessing Different E3 Ligases for Small Molecule Induced Protein Ubiquitination and Degradation." *ACS Chem Biol* 12(10):2570-2578.
Ottis, et al., (Apr. 21, 2017) "Proteolysis-Targeting Chimeras: Induced Protein Degradation as a Therapeutic Strategy." *ACS Chem Biol* 12(4):892-898.
Perez, HL, "Discovery of potent heterodimeric antagonists of inhibitor of apoptosis proteins (IAPs) with sustained antitumor activity", J. Med. Chem. 58(3), 1556-1562 (Jan. 13, 2015).
Powell, C. E. et al. Chemically Induced Degradation of Anaplastic Lymphoma Kinase (ALK). J. Med. Chem. 61, 4249-4255 (May 10, 2018).
Puppala, D. et al., "Development of an Aryl Hydrocarbon Receptor Antagonist Using the Proteolysis-Targeting chimeric Molecules Approach: A Potential Tool for Chemoprevention," Mol. Pharmacol., (Apr. 2008), vol. 73, No. 4, pp. 1064-1071.
Raina et al., "Chemical Inducers of Targeted Protein Degradation," The Journal of Biological Chemistry, 2010, vol. 285, No. 15, pp. 11057-11060. Feb. 10, 2010.
Raina, et al., (Aug. 2017) "Targeted protein knockdown using small molecule degraders." *Curr Opin Chem Biol* 39:46-53.
Raina, K., et al., "PROTAC-induced BET protein degradation as a therapy for castration-resistant prostate cancer", Proc Natl Acad Sci USA 113, 7124-7129 (Jun. 28, 2016).
Remillard D, et al. (May 15, 2017) "Degradation of the BAF Complex Factor BRD9 by Heterobifunctional Ligands." *Angew Chem Int Ed Engl* 56(21):5738-5743.
Rodriguez-Gonzalez, et al., "Targeting steroid hormone receptors for ubiquitination and degradation in breast and prostate cancer", Oncogene. 27(57), Dec. 4, 2008, 7201-7211.
Rotili, D., et al., "Photoactivable peptides for identifying enzyme-substrate and protein-protein interactions", Chem Commun (Carob) 47(5), Feb. 2011, 1488-1490.

(56) References Cited

OTHER PUBLICATIONS

Ruchelman, A., et al., "Isosteric analogs of lenalidominde and pomalidomide: Synthesis and biological activity", Bioorganic & Medicinal Chemistry Letters 23 (Jan. 1, 2013) 360-365.
Sakamoto, et al., "Development of Protacs to target cancer-promoting proteins for ubiquitination and degradation", Mol Cell Proteomics. 2(12), Dec. 2003, 1350-1358.
Sakamoto, et al., "Protacs: chimeric molecules that target proteins to the Skp 1 -Cullin-F box complex for ubiquitination and degradation", Proc Natl Acad Sci U S A.98(15), Jul. 17, 2001, 8554-8559.
Salami, J. & Crews, C. M. Waste disposal—An attractive strategy for cancer therapy. Science 355, 1163-1167 (Mar. 17, 2017).
Schiedel, M., et al., "Chemically Induced Degradation of Sirtuin 2 (Sirt2) by a Proteolysis Targeting Chimera (PROTAC) Based on Sirtuin Rearranging Ligands (SirReals)", J Med Chem. (2017), 61:482-491 (Jan. 25, 2018).
Schneekloth, et al., "Chemical Genetic Control of Protein Levels: Selective in Vivo Targeted Degradation", J Am Chem Soc. 126(12), Mar. 31, 2004, 3748-3754.
Schneekloth, et al., Targeted intracellular protein degradation induced by a small molecule: En route to chemical proteomics, Bioorg. Med. Chem. Lett. 18 (Nov. 15, 2008) 5904-5908.
Smith, et al., "Targeted Intracellular Protein Degradation Induced by a Small Molecule: En Route to Chemical Proteomics", Bioorg Med Chem Lett. 18(22), Nov. 15, 2008, 5904-5908.
Stanton, et al., (Mar. 9, 2018) "Chemically induced proximity in biology and medicine." *Science* 359(6380).
Stewart, Scott G., et al., "Efforts toward elucidating Thalidomide's molecular target: An Expedient Synthesis of the first Thalidomide Biotin Analogue" Org. Biomol., Chem., Jul. 13, 2010; 8, 4059-4062.
STN transcript excerpt Nov. 24, 2017, "Compounds containing sulfur Chromophores v. Complex cyanines".
Stoppler, Melissa Conrad., Endometriosis [online], "Endometriosis Definition and Facts" URL http://www.medicinenet.com/endometriosis/article.htm, retrieved on Apr. 5, 2017.
Stoppler, Melissa Conrad., Endometriosis [online], "What about surgery for Endometriosis?" URL http://www.medicinenet.com/endometriosis/article.htm, retrieved on Apr. 5, 2017.
Sun, B. et al. BET protein proteolysis targeting chimera (PROTAC) exerts potent lethal activity against mantle cell lymphoma cells. Leukemia 32, 343-352 (Feb. 2018).
Sun, et al., "Potent bivalent Smac mimetics: effect of the linker on binding to inhibitor apoptosis proteins (IAPs) and anticancer activity", J. Med. Chem. 53, 3306-3318 (May 12, 2011).
Toure, et al., (Feb. 5, 2016) "Small-Molecule PROTACS: New Approaches to Protein Degradation." *Angew Chem Int Ed Engl* 55(6):1966-1973.
Turk, B. E., "Binding of thalidomide to alphal-acid glycoprotein may be involved in its inhibition of tumor necrosis factor alpha production", Proc. Natl. Acad. Sci. U.S.A. 1996, 93, 7552-7556 (Jul. 23, 1996).
Vamos M., et al., "Expedient synthesis of highly potent antagonists of inhibitor of apoptosis proteins (IAPs) with unique selectivity for ML-IAP", ACS Chem. Biol., 8(4), 725-732 (Jan. 16, 2013).
Van Molle, et al., "Dissecting fragment-based lead discovery at the von Hippel-Lindau protein:hypoxia inducible factor 1a protein-protein interface", Chem Biol. 19(10), Oct. 26, 2012, 1300-1312.
Wang J, et al., "Discovery of novel second mitochondrial-derived activator of caspase mimetics as selective inhibitor or apoptosis protein inhibitors", J. Pharmacol. Exp. Ther., 349(2): 319-29 (May 2014).
Winter, et al., "Phthalimide Conjugation as a strategy for in vivo target protein degradation", Science, 2015 vol. 348 (6241), pp. 1376-1381 [Pub online: May 21, 2015].
Zengerle, et al., "Selective Small Molecule Induced Degradation of the BET Bromodomain Protein BRD4" ACS Chemical Biology, Jun. 2, 2015, vol. 10, pp. 1770-1777.
Zhang, D. et al., "Targeted Degradation of Proteins by Small Molecules: A Novel Tool for Functional Proteomics," comb Chem. High Throughput Screen., Nov. 2004, vol. 7, No. 7, pp. 689-697.
Zhou, B., et al. "Discovery of a Small-Molecule Degrader of Bromodomain and Extra-Terminal (BET) Proteins with Picomolar Cellular Potencies and Capable of Achieving Tumor Regression", J Med Chem. 61(2), 462-481 (2018) (DOI:10.1021/acs.jmedchem.6b01816) (Mar. 24, 2017).

Pomalidomide

Flortaucipir

****Tukey's multiple comparisons test P < 0.0001

24 hours post does:

- 95% of pathologic tau was degraded
- No significant change in total soluble tau observed (data not shown)

TAU-PROTEIN TARGETING COMPOUNDS AND ASSOCIATED

CROSS-REFERENCE TO RELATED APPLICATION

The present application claims priority and benefit to U.S. Provisional Application No. 62/875,500, filed 17 Jul. 2019 and titled: TAU-PROTEIN TARGETING COMPOUNDS AND ASSOCIATED METHODS OF USE, which are incorporated herein by reference in its entirety for all purposes.

INCORPORATION BY REFERENCE

U.S. patent application Ser. No. 15/230,354, filed on Aug. 5, 2016, published as U.S. Patent Application Publication No. 2017/0065719; and U.S. patent application Ser. No. 15/206,497 filed 11 Jul. 2016, published as U.S. Patent Application Publication No. 2017/0008904; and U.S. patent application Ser. No. 15/209,648 filed 13 Jul. 2016, published as U.S. Patent Application Publication No. 2017/0037004; and U.S. patent application Ser. No. 15/730,728, filed on Oct. 11, 2017, published as U.S. Patent Application Publication No. 2018/0099940; and U.S. patent application Ser. No. 14/686,640, filed on Apr. 14, 2015, published as U.S. Patent Application Publication No. 2015/0291562; and U.S. patent application Ser. No. 14/792,414, filed on Jul. 6, 2015, published as U.S. Patent Application Publication No. 2016/0058872; and U.S. patent application Ser. No. 14/371,956, filed on Jul. 11, 2014, published as U.S. Patent Application Publication No. 2014/0356322; and U.S. patent application Ser. No. 15/074,820, filed on Mar. 18, 2016, published as U.S. Patent Application Publication No. 2016/0272639; and U.S. patent application Ser. No. 15/885,671, filed Jan. 31, 2018, published as U.S. Patent Application Publication No. 2018/0215731 A1; and International Patent Application No. PCT/US2016/023258, filed Mar. 18, 2016, published as International Patent Application Publication No. WO2016/149668, are incorporated herein by reference in their entirety. Furthermore, all references cited herein are incorporated by reference herein in their entirety.

BACKGROUND

1. Field of the Discovery

The present disclosure provides heterobifunctional compounds comprising a target protein binding moiety and an E3 ubiquitin ligase binding moiety, and associated methods of use. The bifunctional compounds are useful as modulators of targeted ubiquitination of Tau protein, which is then degraded and/or inhibited.

2. Background Information

Most small molecule drugs bind enzymes or receptors in tight and well-defined pockets. On the other hand, protein-protein interactions are notoriously difficult to target using small molecules due to their large contact surfaces and the shallow grooves or flat interfaces involved. E3 ubiquitin ligases (of which hundreds are known in humans) confer substrate specificity for ubiquitination, and therefore, are more attractive therapeutic targets than general proteasome inhibitors due to their specificity for certain protein substrates. The development of ligands of E3 ligases has proven challenging, in part due to the fact that they must disrupt protein-protein interactions. However, recent developments have provided specific ligands that bind to these ligases. For example, since the discovery of nutlins, the first small molecule E3 ligase inhibitors, additional compounds have been reported that target E3 ligases.

Von Hippel-Lindau (VHL) tumor suppressor is the substrate recognition subunit of the E3 ligase complex VCB, which also consists of elongins B and C, Cul2 and Rbx1. The primary substrate of VHL is Hypoxia Inducible Factor 1α (HIF-1α), a transcription factor that upregulates genes such as the pro-angiogenic growth factor VEGF and the red blood cell inducing cytokine erythropoietin in response to low oxygen levels. The first small molecule ligands of Von Hippel Lindau (VHL) to the substrate recognition subunit of the E3 ligase were generated, and crystal structures were obtained confirming that the compound mimics the binding mode of the transcription factor HIF-1α, the major substrate of VHL.

Cereblon is a protein that in humans is encoded by the CRBN gene. CRBN orthologs are highly conserved from plants to humans, which underscores its physiological importance. Cereblon forms an E3 ubiquitin ligase complex with damaged DNA binding protein 1 (DDB1), Cullin-4A (CUL4A), and regulator of cullins 1 (ROC1). This complex ubiquitinates a number of other proteins. Through a mechanism which has not been completely elucidated, cereblon ubquitination of target proteins results in increased levels of fibroblast growth factor 8 (FGF8) and fibroblast growth factor 10 (FGF10). FGF8 in turn regulates a number of developmental processes, such as limb and auditory vesicle formation. The net result is that this ubiquitin ligase complex is important for limb outgrowth in embryos. In the absence of cereblon, DDB1 forms a complex with DDB2 that functions as a DNA damage-binding protein.

Bifunctional compounds such as those described in U.S. Patent Application Publications 2015/0291562 and 2014/0356322 (incorporated herein by reference), function to recruit endogenous proteins to an E3 ubiquitin ligase for ubiquitination and subsequent degradation in the proteasome degradation pathway. In particular, the publications cited above describe bifunctional or proteolysis-targeting chimeric (PROTAC®) protein degrader compounds, which find utility as modulators of targeted ubiquitination of a variety of polypeptides and proteins, which are then degraded and/or inhibited by the bifunctional compounds.

The Tau protein is an abundant protein in the central nervous system primarily found in neuronal cells, although Tau is expressed at lower levels in other cells of the central nervous system. In a healthy neuron, Tau binds to microtubules and regulates microtubule stability, which is critical for axonal outgrowth and neuronal plasticity. When pathologically altered, Tau molecules are not able to stabilize microtubules and are prone to form insoluble aggregates. Once the Tau protein forms insoluble aggregates in cells, cellular dysfunction occurs, axonal transport is compromised, and neuronal loss ensues. Accumulation of abnormal Tau aggregates in neurons is an important pathological signature in multiple neurodegenerative disorders including Alzheimer's disease. In certain pathological conditions, Tau aggregation results in paired-helical filaments (PHFs), straight filaments (SFs) and/or neurofibrillary tangles (NFTs). The accumulation of PHFs and NFTs in neurons directly correlates with microtubule dysfunction and neuronal degeneration. Neurons containing tau PHFs, SFs, and or NFTs activate diverse cellular mechanisms to try and rid the cell of the abnormal protein aggregates.

More recent studies suggest that, instead of the large insoluble filaments, soluble Tau oligomers might play a more critical role in the onset and progression of disease prior to the development of PHF- or NFT-induced neurotoxicity. Oligomeric species of Tau may act as seeds for the aggregation of native Tau, thereby promoting neurotoxic Tau aggregation. Accumulating evidence has suggested that Tau aggregates can be transmitted from one cell to another by propagating in a prion-like manner.

Tau alteration and dysfunction and extensive neuron loss has long been associated with several neurodegenerative diseases now collectively called tauopathies. The term "tauopathy" or "tauopathies" refers to a class of neurodegenerative diseases associated with the pathological aggregation of Tau protein in neurofibrillary or gliofibrillary tangles in the human brain. Examples of tauopathies include but are not limited to AD, Down's syndrome, frontotemporal lobular dementia (FTLD), cotricobasal degeneration (CBD) and progressive supranuclear palsy (PSP)

Due to its pathological significance in multiple neurodegenerative diseases, Tau is an important therapeutic target. Preventing Tau aggregation is a potential strategy to treat neurodegenerative disorders associated with Tau. Significant effort has been made to identify molecular mechanisms of Tau aggregation, and to find therapeutics to halt the progression of neurodegeneration. However, Tau aggregation inhibitors which demonstrated promising pre-clinical data have proven ineffective in recent clinical trials for the treatment of various tauopathies.

Therefore, a need exists in the art for effective treatments of diseases and conditions that are related to the aggregation of Tau in neurodegenerative disorders such as tauopathies.

SUMMARY

The present disclosure describes hetero-bifunctional compounds that function to recruit Tau protein to an E3 ubiquitin ligase for targeted ubiquitination and subsequent proteasomal degradation, and methods of making and using the same. In particular, the present disclosure provides hetero-bifunctional compounds that find utility as modulators of targeted ubiquitination and degradation of Tau protein aggregates. In addition, the description provides methods of using an effective amount of the compounds of the present disclosure for the treatment or amelioration of disease conditions due to accumulation or aggregation of Tau proteins, such as tauopathies. These diseases or disorders include but are not limited to neurological or neurodegenerative disorders.

Where applicable or not specifically disclaimed, any one of the embodiments described herein are contemplated to be able to combine with any other one or more embodiments, even though the embodiments are described under different aspects of the disclosure. As such, the preceding general areas of utility are given by way of example only and are not intended to be limiting on the scope of the present disclosure and appended claims. Additional objects and advantages associated with the compositions, methods, and processes of the present disclosure will be appreciated by one of ordinary skill in the art in light of the instant claims, description, and examples. For example, the various aspects and embodiments of the disclosure may be utilized in numerous combinations, all of which are expressly contemplated by the present description. These additional advantages, objects, and embodiments are expressly included within the scope of the present disclosure. The publications and other materials used herein to illuminate the background of the disclosure, and in particular cases, to provide additional details respecting the practice, are incorporated by reference.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating embodiments of the disclosure and are not to be construed as limiting the disclosure. Further objects, features and advantages of the disclosure will become apparent from the following detailed description taken in conjunction with the accompanying figures showing illustrative embodiments of the disclosure.

FIG. 2C). Partial inhibition of tau degradation was observed by similar competition with the tau warhead ligand (flortaucipir; FIG. 2C). These data indicate that tau degradation is dependent on both the E3 ligase and tau binding components of the bifunctional compounds, thereby confirming that the targeted degradation of tau is mediated by the bifunctional compound through the proteolysis targeting chimeric mechanism.

FIG. 3A is a graphical representation of the averaged analysis of pathologic tau shown for each animal tested comparing lanes from the vehicle control to either exemplary compound 82 or exemplary compound 382 as indicated in FIG. 3B. Greater than 95% reduction of pathologic tau was observed following treatment of the Tg2508 animals with either exemplary compound 82 or exemplary compound 382.

FIG. 4B shows induction of seeded conformational tau induced by K18 PFFs compared to no doxycycline-induced tau or the negative control antibody background staining. FIG. 4C shows significant seeding induction by Tg2508 cortical (CTX) brain extracts and that this seeding competent tau species was effectively degraded by 24 hours of a single parenteral treatment of Tg2508 mice with 15 mpk exemplary compound 82 or with 30 mpk of exemplary compound 382.

DETAILED DESCRIPTION

Figure 1:
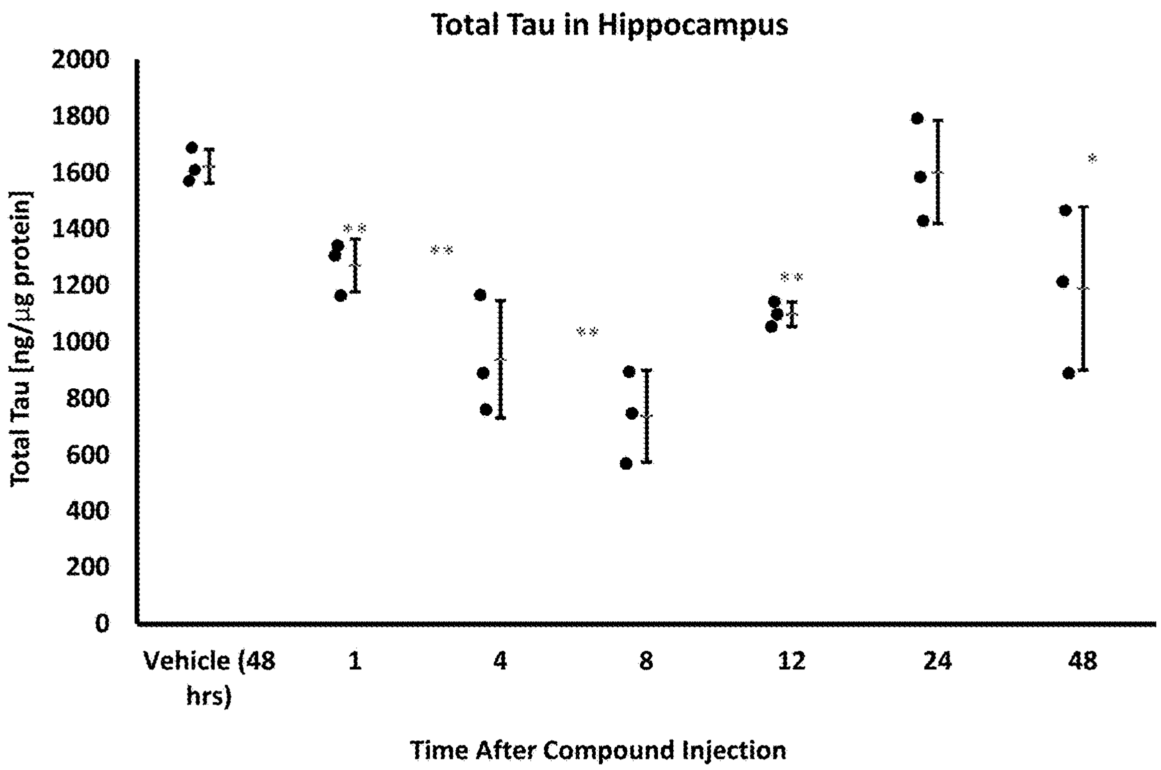
FIG. 1 shows total tau levels in hippocampal homogenates. Data are displayed as in the chart where each data point represents and individual animal. Statistically significant differences between the test item (TI) treated groups versus the vehicle control group according to One-way ANOVA followed by Dunneett's Multiple Comparison Test are indicated by asterisk ** $p<0.01$, * $p<0.05$.

Presently described are compounds, compositions and methods that relate to the surprising discovery that an E3 ubiquitin ligase (e.g., a Von Hippel-Lindau (VHL) E3 ubiquitin ligase, a cereblon E3 ubiquitin ligase, or an IAP E3 ubiquitin ligase) facilitates ubiquitination of the Tau protein when the E3 ubiquitin ligase and the Tau protein are placed in proximity via a hetero-bifunctional compound that binds both the E3 ubiquitin ligase and the Tau protein. Accordingly, the present disclosure provides compounds and compositions comprising an E3 ubiquitin ligase binding moiety ("ULM") coupled by a chemical linking group (L) to a protein targeting moiety ("PTM") that targets the Tau protein, which results in the ubiquitination of the Tau protein, and which leads to degradation of the Tau protein by the proteasome.

In certain aspects, the present disclosure provides a Tau protein targeting moiety ("PTM") that binds Tau protein. In certain embodiments the PTM inhibits Tau protein-protein interactions. In certain embodiments, the PTM is a PTM is a moiety as described herein.

In an additional aspect, the present disclosure provides hetero-bifunctional compounds, which comprise an E3 ubiquitin ligase binding moiety (i.e., a ligand for an E3 ubiquitin ligase (a "ULM" group)), and a moiety that bind Tau (i.e., a protein targeting moiety or "PTM" group that is a Tau ligand/moiety) such that the Tau protein is thereby placed in proximity to the ubiquitin ligase to effect ubiquitination and subsequent degradation (and/or inhibition) of the Tau protein. In a preferred embodiment, the ULM (ubiquitin ligase binding moiety) is a cereblon E3 ubiquitin ligase binding moiety (CLM), inhibitor of apoptosis E3 ubiquitin ligase binding moiety (ILM) or a Von Hippel Lindau (VHL) E3 ubiquitin ligase binding moiety (VLM). For example, the structure of the heterobifunctional compound can be depicted as follows wherein PTM and ULM are directly covalently linked together:

PTM-ULM

The respective positions of the PTM and ULM moieties (e.g., CLM, ILM or VLM), as well as their number as illustrated herein, is provided by way of example only and is not intended to limit the compounds in any way.

As would be understood by the skilled artisan, the bifunctional compounds as described herein can be synthesized such that the number and position of the respective functional moieties can be varied as desired.

In any of the embodiments, the heterobifunctional compound further comprises a chemical linker ("L"). In this example, the structure of the bifunctional compound can be depicted as:

PTM-L-ULM, wherein: PTM is a Tau-targeting moiety, L is a linker, e.g., a bond or a chemical linking group coupling PTM to ULM, and ULM is an E3 ubiquitin ligase binding moiety.

In certain embodiments, the compounds have the following general structures (A)

PTM-L-VLM (A)

wherein: PTM is a Tau-targeting moiety; "L" is a linker (e.g. a bond or a chemical linking group) coupling the PTM and VLM; and VLM is a VHL E3 ubiquitin ligase binding moiety In certain embodiments, the compounds have the following general structures (B)

PTM-L-ILM (B)

wherein: PTM is a Tau-targeting moiety; "L" is a linker (e.g. a bond or a chemical linking group) coupling the PTM and ILM; and ILM is an IAP E3 ubiquitin ligase binding moiety (ILM).

In certain embodiments, the compounds have the following general structures (C)

PTM-L-CLM (C)

wherein: PTM is a Tau-targeting moiety; "L" is a linker (e.g. a bond or a chemical linking group) coupling the PTM and CLM; and CLM is a cereblon E3 ubiquitin ligase binding moiety. As would be understood by the skilled artisan, the hetero-bifunctional compounds as described herein can be synthesized such that the number and position of the respective functional moieties can be varied as desired.

In certain embodiments, the PTMs in structure (A) are the ligands that bind to Tau as well as VHL E3 ubiquitin ligase.

In certain embodiments, the PTMs in structure (B) are the ligands that bind to Tau as well as an IAP E3 ubiquitin ligase.

In certain embodiments, the PTMs in structure (C) are the ligands that bind to Tau as well as cereblon E3 ubiquitin ligase.

In any aspect or embodiment described herein, the compounds as described herein comprise multiple independently selected ULMs, multiple independently selected PTMs, multiple chemical linkers, or a combination thereof.

In any of the aspects or embodiments described herein, the PTM is a small molecule that binds Tau protein. In any of the aspects or embodiments described herein, the PTM is a small molecule that binds Tau protein. In any aspect or embodiment described herein, the small molecule binds Tau protein as described herein.

In an embodiment, the VLM is a derivative of trans-3-hydroxyproline, where both nitrogen and carboxylic acid in trans-3-hydroxyproline are functionalized as amides. Other contemplated VLMs are described in U.S. Patent Application Publication No. 2016/0272639, U.S. Patent Application Publication No. 2014/0356322, each of which is incorporated herein by reference in its entirety.

In any aspect or embodiment described herein, the CLM comprises a chemical group derived from an imide, a thioimide, an amide, or a thioamide. In a particular embodiment, the chemical group is a phthalimido group, or an analog or derivative thereof. In a certain embodiment, the CLM is selected from thalidomide, lenalidomide, pomalidomide, analogs thereof, isosteres thereof, and derivatives thereof. Other contemplated CLMs are described in U.S. Patent Application Publication No. 2015/0291562, which is incorporated herein by reference in its entirety.

In any aspect or embodiment described herein, "L" is a bond. In additional embodiments, the linker "L" is a chemical linking moiety/group with a linear non-hydrogen atom number in the range of 1 to 40 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40). The connector "L" can contain, but is not limited to one or more functional groups such as ether, amide, alkane, alkene, alkyne, ketone, hydroxyl, carboxylic acid, thioether, sulfoxide, and sulfone. The linker can contain aromatic, heteroaromatic, cyclic, bicyclic or tricyclic moieties. Substitution with halogen, such as Cl, F, Br and I, or alkyl, such as methyl, ethyl, isopropyl, and tert-butyl, can be included in the linker. In the case of fluorine substitution, single or multiple fluorines can be included.

In an additional aspect, the present disclosure provides therapeutic compositions comprising an effective amount of a compound as described herein or a pharmaceutically acceptable salt form thereof, and a pharmaceutically acceptable carrier. The therapeutic compositions can be used to trigger targeted degradation of Tau in a patient or subject, for example, an animal such as a human, and can be used for treating or ameliorating one or more disease states, conditions, or symptoms casually related to Tau, which treated is accomplished through degradation or inhibition of Tau protein, or controlling or lowering Tau protein levels in a patent or subject. In any aspect or embodiment described herein, the therapeutic compositions as described herein may be used to effectuate the degradation of Tau for the treatment or amelioration of a disease or condition causally related, e.g., to accumulation or aggregation of Tau protein (e.g., neuronal disease).

In yet another aspect, the present disclosure provides a method of ubiquitinating TAU in a cell (e.g., in vitro or in vivo). In any aspect or embodiment described herein, the method comprises administering a hetero-bifunctional compound as described herein comprising a PTM that binds Tau protein, and a ULM (such as CLM or VLM), preferrably linked through a chemical linker moiety, as described herein, to effectuate degradation of the Tau protein. Though not wanted to be limited by theory, the inventors believe that, pursuant to the present disclosure, poly-ubiquitination of Tau protein will occur when it is placed in proximity to the E3 ubiquitin ligase with use of the hetero-bifunctional compound, thereby triggering subsequent degradation of the Tau via the proteasomal pathway and control or reduction of Tau protein levels in cells, such as cells of a subject in need of such treatment. The control or reduction in levels of the Tau protein afforded by the present disclosure provides treatment of a Tau causally related disease state, condition or related symptom, as modulated, e.g., through a lowering of the amount of Tau protein or mutated form thereof in cells of the subject.

In still another aspect, the present disclosure provides methods for treating or ameliorating a disease, condition, or symptom thereof causally related to TAU thereof in a subject or a patient, e.g., an animal such as a human, comprising administering to a subject in need thereof a composition comprising an effective amount, e.g., a therapeutically effective amount, of a hetero-bifunctional compound as described herein or pharmaceutically acceptable salt form thereof, and a pharmaceutically acceptable carrier, wherein the composition is effective for treating or ameliorating the disease or disorder or symptom thereof in the subject.

In any aspect or embodiment described herein, PTM are molecules that bind to Tau protein (TBM), and ULM are molecules that bind to cereblon E3 ubiquitin ligase (CLM), inhibitor of apoptosis E3 ubiquitin ligase (ILM) or VHL E3 ubiquitin ligase (VLM) exemplified by the following general structures, respectively:

TBM-L-CLM;

TBM-L-ILM; and

TBM-L-VLM.

It will be understood that the general structures are exemplary and the respective moieties can be arranged spatially in any desired order, number or configuration.

In any aspect or embodiment described herein, the description provides a bifunctional compound having a structure selected from the group consisting of Compounds 332, 335, 337-586, and 589-686 (e.g., a compound selected from Table 1), a salt, a polymorph, and a prodrug thereof.

In further embodiments, the description provides a composition comprising a bifunctional compound having a structure selected from Table 1 (e.g., a chemical structure selected from Compounds 332, 335, 337-586, and 589-686), a salt, a polymorph, and a prodrug thereof. For example, the description provides compositions comprising compounds as described herein, and a pharmaceutically acceptable carrier. In any aspect or embodiment described herein, the compositions are therapeutic or pharmaceutical compositions comprising an effective amount of a compound as described herein and a pharmaceutically acceptable carrier. In any aspect or embodiment described herein, the therapeutic or pharmaceutical compositions comprise an additional biologically active agent, e.g., an agent effective for the treatment of neuronal disease.

In any of the aspects or embodiments described herein, the therapeutic compositions comprising compounds described herein can be in any suitable dosage form, e.g., solid, or liquid, and configured to be delivered by any suitable route, e.g., oral, parenteral, intravenous, intraperitoneal, subcutaneous, intramuscular, etc.

In another aspect, the description provides methods of modulating Tau protein, their ubiquitination and the subsequent degradation in a subject, e.g., a cell, a tissue, mammal, or human patient, the method comprising administering an effective amount of a compound as described herein or a composition comprising an effective amount of the same to a subject, wherein the compound or composition comprising the same is effective in modulating Tau ubquitination and degradation in the subject.

In yet another aspect, the description provides methods of treating or ameliorating a symptom of a disease related to TAU activity in a subject, e.g., a cell, a tissue, mammal, or human patient, the method comprising administering an effective amount of a compound as described herein or a composition comprising an effective amount of the same to a subject in need thereof, wherein the compound or composition comprising the same is effective in treating or ameliorating a symptom of a disease related to TAU activity in the subject. In certain embodiments, the disease to be treated is neurological or neurodegenerative disease, e.g. Alzeimer, Parkinson, Dementia etc.

In any aspect or embodiment described herein, the subject is a human.

In an additional aspect, the description provides methods for identifying the effects of the degradation of proteins of interest (i.e., Tau protein) in a biological system using compounds according to the present disclosure.

In another aspect, the description provides processes and intermediates for making a hetero-bifunctional compound of the present disclosure capable of targeted ubiquitination and degradation of Tau protein in a cell (e.g., in vivo or in vitro).

In an aspect, the description provides compounds in which the PTM binds to the Tau protein. The present disclosure also provides a library of compositions and the use thereof to produce targeted degradation of the Tau protein in a cell.

The following is a detailed description provided to aid those skilled in the art in practicing the present disclosure. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

In any aspect or embodiment described herein, the present disclosure provides hetero-bifunctional compounds which comprise a ligand, e.g., a small molecule ligand (i.e., having a molecular weight of below 2,000, 1,000, 500, or 200 Daltons), which is capable of binding to an E3 ubiquitin ligase, such as the cereblon, IAP, or VHL E3 ubiquitin ligase. The compounds also comprise a small molecule moiety that is capable of binding to the Tau protein in such a way that the Tau protein is placed in proximity to the E3 ubiquitin ligase protein (e.g., VHL, IAP, and cereblon) to effect ubiquitination and degradation (and/or inhibition) of the Tau protein. "Small molecule" means, in addition to the above, that the molecule is non-peptidyl, that is, it is not considered a peptide, e.g., comprises fewer than 4, 3, or 2 amino acid residues. In accordance with the present description, each of the PTM, ULM and hetero-bifunctional molecule is a small molecule.

Unless otherwise defined, all technical and scientific terms used herein have the same meaning as commonly understood by one of ordinary skill in the art to which this disclosure belongs. The terminology used in the description is for describing particular embodiments only and is not intended to be limiting of the disclosure.

Where a range of values is provided, it is understood that each intervening value in the range, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either/or both of those included limits are also included in the disclosure.

The following terms are used to describe the present disclosure. In instances where a term is not specifically defined herein, that term is given an art-recognized meaning by those of ordinary skill applying that term in context to its use in describing the present disclosure.

The articles "a" and "an" as used herein and in the appended claims are used herein to refer to one or to more than one (i.e., to at least one) of the grammatical object of the article unless the context clearly indicates otherwise. By way of example, "an element" means one element or more than one element, unless otherwise indicated.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods or processes described herein that include more than one step or act, the order of the steps or acts of the method is not necessarily limited to the order in which the steps or acts of the method are recited unless the context indicates otherwise.

The terms "co-administration" and "co-administering" or "combination therapy" refer to both concurrent administration (administration of two or more therapeutic agents at the same time) and time-varied administration (administration of one or more therapeutic agents at a time different from that of the administration of an additional therapeutic agent or agents), as long as the two or more therapeutic agents are present in the patient to some extent, preferably at effective amounts, at the same time. In certain preferred aspects, one or more of the hetero-bifunctional compounds described herein are coadministered with at least one additional bioactive agent, e.g., an anti-neurodegenerative agent. In particularly preferred aspects, the co-administration of such compounds results in synergistic activity and/or therapy such as, e.g., anti-neurodegenerative activity.

The term "compound", as used herein, unless otherwise indicated, refers to any specific hetero-bifunctional compound disclosed herein, pharmaceutically acceptable salts and solvates thereof, and deuterated forms of any of the aforementioned molecules, where applicable. Deuterated compounds contemplated are those in which one or more of the hydrogen atoms contained in the drug molecule have been replaced by deuterium. Such deuterated compounds preferably have one or more improved pharmacokinetic or pharmacodynamic properties (e.g., longer half-life) compared to the equivalent "undeuterated" compound.

The term "patient" or "subject" is used throughout the specification to describe an animal, preferably a human or a domesticated animal, to whom treatment, including prophylactic treatment, with the compositions according to the present disclosure is provided. For treatment of those diseases, conditions or symptoms that are specific for a specific animal such as a human patient, the term patient refers to that specific animal, including a domesticated animal such as a dog or cat or a farm animal such as a horse, cow, sheep, etc. In general, in the present disclosure, the terms "patient" and "subject" refer to a human patient unless otherwise stated or implied from the context of the use of the term.

The terms "effective" and "therapeutically effective" are used to describe an amount of a compound or composition which, when used within the context of its intended use, and either in a single dose or, more preferably after multiple doses within the context of a treatment regimen, effects an intended result such as an improvement in a disease or condition, or amelioration or reduction in one or more symptoms associated with a disease or condition. The terms "effective" and "therapeutically effective" subsume all other "effective amount" or "effective concentration" terms, which are otherwise described or used in the present application.

The term "Ubiquitin Ligase" refers to a family of proteins that facilitate the transfer of one or more ubiquitins to a specific substrate protein. Addition of a chain of several ubiquitins (poly-ubiquitination) targets the substrate protein for degradation. For example, cereblon, VHL, and IAP are E3 Ubiquitin Ligase proteins that alone or in combination with an E2 ubiquitin-conjugating enzyme, can ultimately cause the attachment of four ubiquitins to a lysine on a target protein, thereby targeting the protein for degradation by the proteasome. The ubiquitin ligase is involved in polyubiquitination such that a first ubiquitin is attached to a lysine on the target protein, a second ubiquitin is attached to the first; a third is attached to the second, and so forth is attached to the third. Such poly-ubiquitination marks proteins for degradation by the proteasome.

The term "independently" is used herein to indicate that the variable, which is independently applied, varies independently from application to application.

The term "hydrocarbyl" shall mean a compound which contains carbon and hydrogen and which may be fully saturated, partially unsaturated or aromatic and includes aryl groups, alkyl groups, alkenyl groups and alkynyl groups.

The term "alkyl" shall mean within its context a linear, branch-chained or cyclic fully saturated hydrocarbon radical, preferably a $C_1$-$C_{10}$, preferably a $C_1$-$C_6$, or more preferably a $C_1$-$C_3$ alkyl group, which may be optionally substituted with any suitable functional group or groups. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopentylethyl, cyclohexylethyl and cyclohexyl, among others. In certain embodiments, the alkyl group is end-capped with a halogen group (At, Br, Cl, F, or I).

The term "lower alkyl" refers to alkyl groups with no more than six carbon atoms, such as methyl, ethyl, or propyl.

The term "lower alkoxy" refers to alkoxy groups with no more than six carbon atoms, such as methozy, ethoxy, or propoxy.

The term "Alkenyl" refers to linear, branch-chained or cyclic $C_2$-$C_{10}$ (preferably $C_2$-$C_6$) hydrocarbon radicals containing at least one C═C bond.

The term "Alkynyl" refers to linear, branch-chained or cyclic $C_2$-$C_{10}$ (preferably $C_2$-$C_6$) hydrocarbon radicals containing at least one C═C bond.

The term "alkylene" when used, refers to a $-(CH_2)_n-$ group (n is an integer generally from 0-6), which may be optionally substituted. When substituted, the alkylene group preferably is substituted on one or more of the methylene groups with a $C_1$-$C_6$ alkyl group (including a cyclopropyl group or a t-butyl group), but may also be substituted with one or more halo groups, preferably from 1 to 3 halo groups or one or two hydroxyl groups, O—($C_1$-$C_6$ alkyl) groups or amino acid sidechains as otherwise disclosed herein. In certain embodiments, an alkylene group may be substituted with a urethane or alkoxy group (or other suitable functional group) which may be further substituted with a polyethylene glycol chain (of from 1 to 10, preferably 1 to 6, or more preferably 1 to 4 ethylene glycol units) to which is substituted (preferably, but not exclusively on the distal end of the polyethylene glycol chain) an alkyl chain substituted with a single halogen group, preferably a chlorine group. In still other embodiments, the alkylene (e.g., methylene) group, may be substituted with an amino acid sidechain group such as a sidechain group of a natural or unnatural amino acid, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine.

The term "unsubstituted" shall mean substituted only with hydrogen atoms. A range of carbon atoms which includes $C_0$ means that carbon is absent and is replaced with H. Thus, a range of carbon atoms which is $C_0$-$C_6$ includes carbons atoms of 1, 2, 3, 4, 5 and 6 and for $C_0$, H stands in place of carbon.

The term "substituted" or "optionally substituted" shall mean independently (i.e., where more than one substituent occurs, each substituent is selected independent of another substituent) one or more substituents (independently up to five substituents, preferably up to three substituents, more preferably 1 or 2 substituents on a moiety in a compound according to the present disclosure and may include substituents which themselves may be further substituted) at a carbon (or nitrogen) position anywhere on a molecule within context, and includes as possible substituents hydroxyl, thiol, carboxyl, cyano (C≡N), nitro ($NO_2$), halogen (preferably, 1, 2 or 3 halogens, especially on an alkyl, especially a methyl group such as a trifluoromethyl), an alkyl group (preferably, $C_1$-$C_{10}$, more preferably, $C_1$-$C_6$), aryl (especially phenyl and substituted phenyl for example benzyl or benzoyl), alkoxy group (preferably, $C_1$-$C_6$ alkyl or aryl, including phenyl and substituted phenyl), thioether (preferably, $C_1$-$C_6$ alkyl or aryl), acyl (preferably, $C_1$-$C_6$ acyl), ester or thioester (preferably, $C_1$-$C_6$ alkyl or aryl) including alkylene ester (such that attachment is on the alkylene group, rather than at the ester function which is preferably substituted with a $C_1$-$C_6$ alkyl or aryl group), halogen (preferably, F or Cl), amine (including a five- or six-membered cyclic alkylene amine, further including a $C_1$-$C_6$ alkyl amine or a $C_1$-$C_6$ dialkyl amine which alkyl groups may be substituted with one or two hydroxyl groups) or an optionally substituted —N($C_0$-$C_6$ alkyl)C(O)(O—$C_1$-$C_6$ alkyl) group (which may be optionally substituted with a polyethylene glycol chain to which is further bound an alkyl group containing a single halogen, preferably chlorine substituent), hydrazine, amido, which are preferably independently substituted with one or two $C_1$-$C_6$ alkyl groups (including a carboxamide which is optionally substituted with one or two $C_1$-$C_6$ alkyl groups), alkanol (preferably, $C_1$-$C_6$ alkyl or aryl), or alkanoic acid (preferably, $C_1$-$C_6$ alkyl or aryl). Substituents according to the present disclosure may include, for example —$SiR_1R_2R_3$ groups where each of $R_1$ and $R_2$ is as otherwise described herein and $R_3$ is H or a $C_1$-$C_6$ alkyl group, preferably $R_1$, $R_2$, $R_3$ together is a $C_1$-$C_3$ alkyl group (including an isopropyl or t-butyl group). Each of the above-described groups may be linked directly to the substituted moiety or alternatively, the substituent may be linked to the substituted moiety (preferably in the case of an aryl or heteroaryl moiety) through an optionally substituted —$(CH_2)_m$— or alternatively an optionally substituted —$(OCH_2)_m$—, —$(OCH_2CH_2)_m$— or —$(CH_2CH_2O)_m$— group, which may be substituted with any one or more of the above-described substituents. Alkylene groups —$(CH_2)_m$— or —$(CH_2)_n$— groups or other chains such as ethylene glycol chains, as identified above, may be substituted anywhere on the chain. Preferred substituents on alkylene groups include halogen or $C_1$-$C_6$ (preferably $C_1$-$C_3$) alkyl groups, which may be optionally substituted with one or two hydroxyl groups, one or two ether groups (O—$C_1$-$C_6$ groups), up to three halo groups (preferably F), or a side chain of an amino acid as otherwise described herein and optionally substituted amide (preferably carboxamide substituted as described above) or urethane groups (often with one or two $C_0$-$C_6$ alkyl substituents, which group(s) may be further substituted). In certain embodiments, the alkylene group (often a single methylene group) is substituted with one or two optionally substituted $C_1$-$C_6$ alkyl groups, preferably $C_1$-$C_4$ alkyl group, most often methyl or O-methyl groups or a sidechain of an amino acid as otherwise described herein. In the present disclosure, a moiety in a molecule may be optionally substituted with up to five substituents, preferably up to three substituents. Most often, in the present disclosure moieties which are substituted are substituted with one or two substituents.

The term "substituted" (each substituent being independent of any other substituent) shall also mean within its context of use $C_1$-$C_6$ alkyl, $C_1$-$C_6$ alkoxy, halogen, amido, carboxamido, sulfone, including sulfonamide, keto, carboxy, $C_1$-$C_6$ ester (oxyester or carbonylester), $C_1$-$C_6$ keto, urethane —O—C(O)—$NR_1R_2$ or —N($R_1$)—C(O)—O—$R_1$, nitro, cyano and amine (especially including a $C_1$-$C_6$ alkylene-$NR_1R_2$, a mono- or di-$C_1$-$C_6$ alkyl substituted amines which may be optionally substituted with one or two hydroxyl groups). Each of these groups contain unless otherwise indicated, within context, between 1 and 6 carbon atoms. In certain embodiments, preferred substituents will include for example, —NH—, —NHC(O)—, —O—, =O, —$(CH_2)_m$— (here, m and n are in context, 1, 2, 3, 4, 5 or 6), —S—, —S(O)—, $SO_2$— or —NH—C(O)—NH—, —$(CH_2)_n$OH, —$(CH_2)_n$SH, —$(CH_2)_n$COOH, $C_1$-$C_6$ alkyl, —$(CH_2)_n$O—($C_1$-$C_6$ alkyl), —$(CH_2)_n$C(O)—($C_1$-$C_6$ alkyl), —$(CH_2)_n$OC(O)—($C_1$-$C_6$ alkyl), —$(CH_2)_n$C(O)O—($C_1$-$C_6$ alkyl), —$(CH_2)_n$NHC(O)—$R_1$, —$(CH_2)_n$C(O)—$NR_1R_2$, —$(OCH_2)_n$OH, —$(CH_2O)_n$COOH, $C_1$-$C_6$ alkyl, —$(OCH_2)_n$O—($C_1$-$C_6$ alkyl), —$(CH_2O)_n$C(O)—($C_1$-$C_6$ alkyl), —$(OCH_2)_n$NHC(O)—$R_1$, —$(CH_2O)_n$C(O)—$NR_1R_2$, —$S(O)_2$—$R_S$, —S(O)—$R_S$ ($R_S$ is $C_1$-$C_6$ alkyl or a —$(CH_2)_m$—$NR_1R_2$ group), $NO_2$, CN or halogen (F, Cl, Br, I, preferably F or Cl), depending on the context of the use of the substituent. $R_1$ and $R_2$ are each, within context, H or a $C_1$-$C_6$ alkyl group (which may be optionally substituted with one or two hydroxyl groups or up to three halogen groups, preferably fluorine). The term "substituted" shall also mean, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted $C_1$-$C_6$ alkyl groups (methyl, ethyl or hydroxymethyl or hydroxyethyl is preferred, thus providing a chiral center), a sidechain of an amino acid group as otherwise described herein, an amido group as described hereinabove, or a urethane group O—C(O)—$NR_1R_2$ group where $R_1$ and $R_2$ are as otherwise described herein, although numerous other groups may also be used as substituents. Various optionally substituted moieties may be substituted with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

The term "aryl" or "aromatic", in context, refers to a substituted (as otherwise described herein) or unsubstituted monovalent aromatic radical (e.g., a 5-16 membered ring) having a single ring (e.g., benzene, phenyl, benzyl, or 5, 6, 7, or 8 membered ring) or condensed rings (e.g., naphthyl, anthracenyl, phenanthrenyl, 10-16 membered ring, etc.) and can be bound to the compound according to the present disclosure at any available stable position on the ring(s) or as otherwise indicated in the chemical structure presented. Other examples of aryl groups, in context, may include heterocyclic aromatic ring systems "heteroaryl" groups having one or more nitrogen, oxygen, or sulfur atoms in the ring (moncyclic) such as imidazole, furyl, pyrrole, furanyl, thiene, thiazole, pyridine, pyrimidine, pyrazine, triazole, oxazole or fused ring systems such as indole, quinoline, indolizine, azaindolizine, benzofurazan, etc., among others, which may be optionally substituted as described above. Among the heteroaryl groups which may be mentioned include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, azaindolizine, purine, indazole, quinoline, dihydroquinoline, tetrahydroquinoline, isoquinoline, dihydroisoquinoline, tetrahydroisoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, pyrimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "substituted aryl" refers to an aromatic carbocyclic group comprised of at least one aromatic ring or of multiple condensed rings at least one of which being aromatic, wherein the ring(s) are substituted with one or more substituents. For example, an aryl group can comprise a substituent(s) selected from: $-(CH_2)_nOH$, $-(CH_2)_n-O-(C_1-C_6)$alkyl, $-(CH_2)_n-O-(CH_2)_n-(C_1-C_6)$alkyl, $-(CH_2)_n-C(O)(C_0-C_6)$ alkyl, $-(CH_2)_n-C(O)O(C_0-C_6)$ alkyl, $-(CH_2)_n-OC(O)(C_0-C_6)$alkyl, amine, mono- or di-$(C_1-C_6$ alkyl) amine wherein the alkyl group on the amine is optionally substituted with 1 or 2 hydroxyl groups or up to three halo (preferably F, Cl) groups, OH, COOH, $C_1-C_6$ alkyl, preferably $CH_3$, $CF_3$, OMe, $OCF_3$, $NO_2$, or CN group (each of which may be substituted in ortho-, meta- and/or para-positions of the phenyl ring, preferably para-), an optionally substituted phenyl group (the phenyl group itself is preferably connected to a PTM group, including a ULM group, via a linker group), and/or at least one of F, Cl, OH, COOH, $CH_3$, $CF_3$, OMe, $OCF_3$, $NO_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methyl substituted isoxazole, an optionally substituted oxazole including a methyl substituted oxazole, an optionally substituted thiazole including a methyl substituted thiazole, an optionally substituted isothiazole including a methyl substituted isothiazole, an optionally substituted pyrrole including a methyl substituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo-(preferably, F) or methyl substituted pyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, and combinations thereof.

"Carboxyl" denotes the group $-C(O)OR$, where R is hydrogen, alkyl, substituted alkyl, aryl, substituted aryl, heteroaryl or substituted heteroaryl, whereas these generic substituents have meanings which are identical with definitions of the corresponding groups defined herein.

The term "heteroaryl" or "hetaryl" can mean but is in no way limited to a 5-16 membered heteroaryl (e.g., 5, 6, 7 or 8 membered monocylic ring or a 10-16 membered heteroaryl having multiple condensed rings), an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted $-(CH_2)_m-O-C_1-C_6$ alkyl group or an optionally substituted $-(CH_2)_m-C(O)-O-C_1-C_6$ alkyl group), an optionally substituted pyridine (2-, 3, or 4-pyridine) or a group according to the chemical structure:

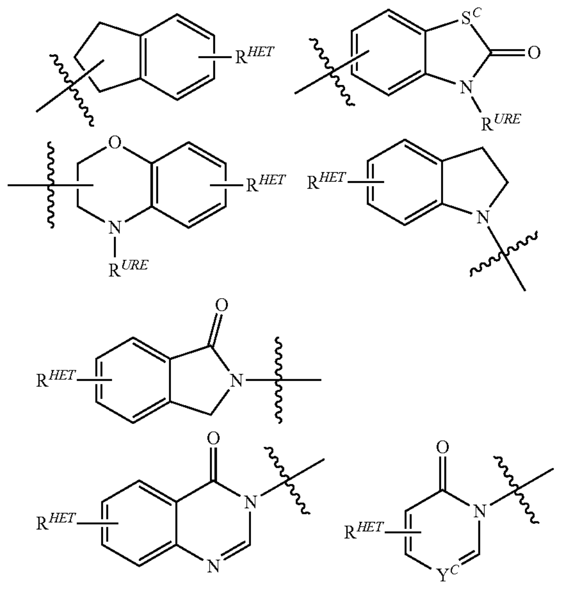

wherein:

S° is $CHR_{SS}$, $NR^{URE}$, or O;

$R^{HET}$ is H, CN, $NO_2$, halo (preferably Cl or F), optionally substituted $C_1-C_6$ alkyl (preferably substituted with one or two hydroxyl groups or up to three halo groups (e.g. $CF_3$), optionally substituted $O(C_1-C_6$ alkyl) (preferably substituted with one or two hydroxyl groups or up to three halo groups) or an optionally substituted acetylenic group —C═C—$R_a$ where $R_a$ is H or a $C_1$-$C_6$ alkyl group (preferably $C_1$-$C_3$ alkyl);

$R^{SS}$ is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl).

The terms "aralkyl" and "heteroarylalkyl" refer to groups that comprise both aryl or, respectively, heteroaryl as well as alkyl and/or heteroalkyl and/or carbocyclic and/or heterocycloalkyl ring systems according to the above definitions.

The term "arylalkyl" as used herein refers to an aryl group as defined above appended to an alkyl group defined above. The arylalkyl group is attached to the parent moiety through an alkyl group wherein the alkyl group is one to six carbon atoms. The aryl group in the arylalkyl group may be substituted as defined above.

The term "heterocycle" refers to a cyclic group which contains at least one heteroatom, e.g., O, N or S, and may be aromatic (heteroaryl) or non-aromatic. Thus, the heteroaryl moieties are subsumed under the definition of heterocycle, depending on the context of its use. Exemplary heteroaryl groups are described hereinabove. Exemplary heterocyclics include: azetidinyl, benzimidazolyl, 1,4-benzodioxanyl, 1,3-benzodioxolyl, benzoxazolyl, benzothiazolyl, benzothienyl, dihydroimidazolyl, dihydropyranyl, dihydrofuranyl, dioxanyl, dioxolanyl, ethyleneurea, 1,3-dioxolane, 1,3-dioxane, 1,4-dioxane, furyl, homopiperidinyl, imidazolyl, imidazolinyl, imidazolidinyl, indolinyl, indolyl, isoquinolinyl, isothiazolidinyl, isothiazolyl, isoxazolidinyl, isoxazolyl, morpholinyl, naphthyridinyl, oxazolidinyl, oxazolyl, pyridone, 2-pyrrolidone, pyridine, piperazinyl, N-methylpiperazinyl, piperidinyl, phthalimide, succinimide, pyrazinyl, pyrazolinyl, pyridyl, pyrimidinyl, pyrrolidinyl, pyrrolinyl, pyrrolyl, quinolinyl, tetrahydrofuranyl, tetrahydropyranyl, tetrahydroquinoline, thiazolidinyl, thiazolyl, thienyl, tetrahydrothiophene, oxane, oxetanyl, oxathiolanyl, thiane among others.

Heterocyclic groups can be optionally substituted with a member selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO— alkyl, —SO-substituted alkyl, —SOaryl, —SO-heteroaryl, —$SO_2$-alkyl, —$SO_2$-substituted alkyl, —$SO_2$-aryl, oxo (═O), and —$SO_2$-heteroaryl. Such heterocyclic groups can have a single ring or multiple condensed rings. Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles. The term "heterocyclic" also includes bicyclic groups in which any of the heterocyclic rings is fused to a benzene ring or a cyclohexane ring or another heterocyclic ring (for example, indolyl, quinolyl, isoquinolyl, tetrahydroquinolyl, and the like).

The term "cycloalkyl" can mean but is in no way limited to univalent groups derived from monocyclic or polycyclic alkyl groups or cycloalkanes, as defined herein, e.g., saturated monocyclic hydrocarbon groups having from three to twenty carbon atoms in the ring, including, but not limited to, cyclopropyl, cyclobutyl, cyclopentyl, cyclohexyl, cycloheptyl and the like. The term "substituted cycloalkyl" can mean but is in no way limited to a monocyclic or polycyclic alkyl group and being substituted by one or more substituents, for example, amino, halogen, alkyl, substituted alkyl, carbyloxy, carbylmercapto, aryl, nitro, mercapto or sulfo, whereas these generic substituent groups have meanings which are identical with definitions of the corresponding groups as defined in this legend.

"Heterocycloalkyl" refers to a monocyclic or polycyclic alkyl group in which at least one ring carbon atom of its cyclic structure being replaced with a heteroatom selected from the group consisting of N, O, S or P. "Substituted heterocycloalkyl" refers to a monocyclic or polycyclic alkyl group in which at least one ring carbon atom of its cyclic structure being replaced with a heteroatom selected from the group consisting of N, O, S or P and the group is containing one or more substituents selected from the group consisting of halogen, alkyl, substituted alkyl, carbyloxy, carbylmercapto, aryl, nitro, mercapto or sulfo, whereas these generic substituent group have meanings which are identical with definitions of the corresponding groups as defined in this legend.

An aspect of the present disclosure provides compounds useful for regulating protein activity. The compound comprises an E3 ubiquitin ligase binding moiety and a protein targeting moiety that are linked or coupled together, preferably through a chemical linking group, wherein the E3 ubiquitin ligase binding moiety recognizes an E3 ubiquitin ligase, such as cereblon, VHL or IAP, and the protein targeting moiety recognizes a target protein (e.g., Tau). Such compounds may be referred to herein as hetero-bifunctional compounds/molecules or compounds with the following general chemical structure:

PTM-L-ULM, or a pharmaceutically acceptable salt, enantiomer, stereoisomer, solvate, polymorph or prodrug thereof, wherein:

ULM is a small molecule E3 ubiquitin ligase binding moiety that binds an E3 ubiquitin ligase;

PTM is a small molecule comprising a Tau protein targeting moiety that degrades the Tau protein; and L is a bond or a chemical linking moiety connecting ULM and PTM.

In any aspect or embodiment described herein, the E3 ubiquitin ligase binding moiety targets a member of the group consisting of Von Hippel-Lindau (VLM), cereblon (CLM), and IAP (ILM).

In one aspect, the description provides Tau protein binding moieties (PTM). In any aspect or embodiment described herein, PTM is represented by Formula I, Formula II, Formula III, Formula IV, Formula V, Formula VI, Formula, VII, Formula, VIII, Formula IX, Formula X, Formula XI, Formula XII, Formula XIII, Formula XIV, or Formula XV:

I

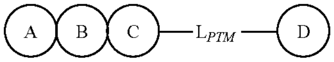

II

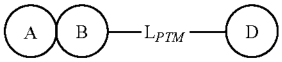

III

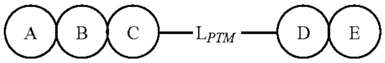

IV

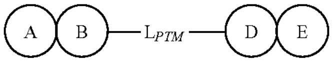

V

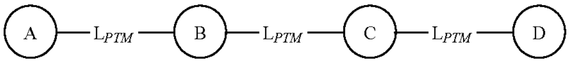

VI

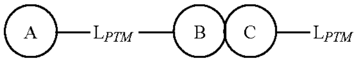

VII

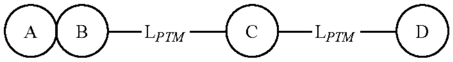

VIII

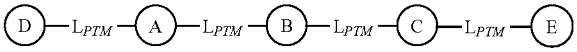

IX

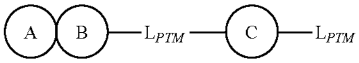

X

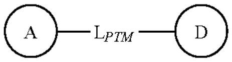

XI

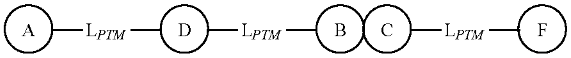

XII

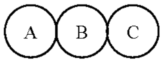

XIII

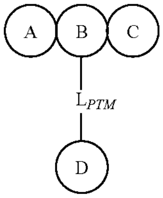

XIV

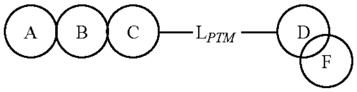

-continued

XV

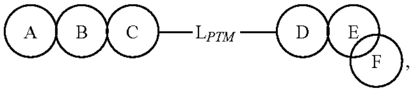

, wherein:

A, B, C, D, E, and F are independently selected from an optionally substituted 5- or 6-membered aryl or heteroaryl ring, an optionally substituted 4- to 7-membered cycloalkyl or a heterocycloalkyl, where contact between circles indicates ring fusion and overlapping circules indicates spirocyclic rings; and $L_{PTM}$ is selected from a bond, an alkyl, an alkenyl or an alkynyl, optionally interrupted by one or more rings (i.e., cycloalkyl, heterocycloalkyl, aryl or heteroaryl), or one or more functional groups selected from the groups —O—, —S—, —$NR^1_{PTM}$— (where $R^1_{PTM}$ is selected from H or alkyl), —N═N—, —S(O)—, —$SO_2$—, —C(O)—, —NHC(O)—, —C(O)NH—, —$NHSO_2$—, —NHC(O)NH—, —NHC(O)O—, or —OC(O)NH—, wherein the said functional group are optionally located at either end of the linker.

In any aspect or embodiment described herein, PTM is represented by Formula I, II, III, IV, XII, XIII, XIV, and XV:

I

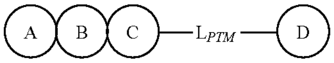

II

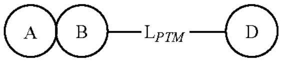

III

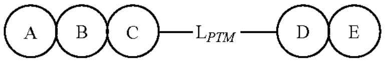

IV

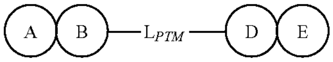

XII

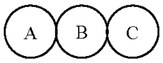

XIII

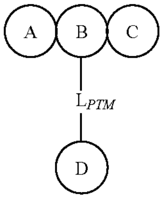

XIV

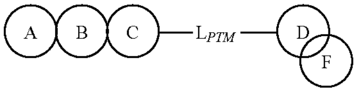

or

XV

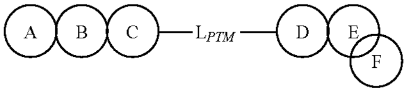

wherein:

A, B, C, D, E, and F are independently selected from an optionally substituted 5- or 6-membered aryl or heteroaryl ring, an optionally substituted 4- to 7-membered cycloalkyl or a heterocycloalkyl, where contact between circles indicates ring fusion and overlapping circles indicates spirocyclic rings;

$L_{PTM}$ is selected from a bond, an alkyl, an alkenyl or an alkynyl, optionally interrupted by one or more rings (i.e., cycloalkyl, heterocycloalkyl, aryl or heteroaryl), or one or more functional groups selected from the groups —O—, —S—, —$NR^{1PTM}$—, —N═N—, —S(O)—, —$SO_2$—, —C(O)—, —NHC(O)—, —C(O)NH—, —$NHSO_2$—, —NHC(O)NH—, —NHC(O)O—, or —OC(O)NH—, wherein the said functional group is optionally located at either end of the linker; and $R^{1PTM}$ is selected from H, alkyl, or fluoroalkyl wherein the PTM is coupled via a chemical linking group (L) to a ULM via at least one of A, B, C, D, E, or F (e.g., A, C, D or E; or A, C, D, E, or F).

In any aspect or embodiment described herein, PTM is represented by Formula I, II, III, IV, XII, XIII, XIV, and XV:

I

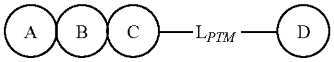

II

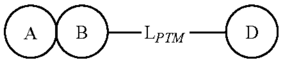

III

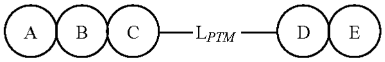

IV

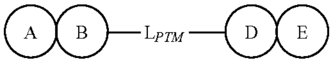

XII

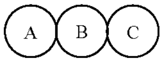

XIII

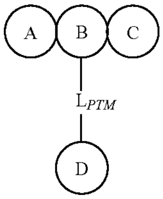

XIV

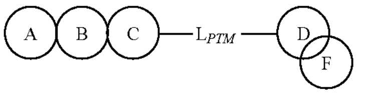

XV

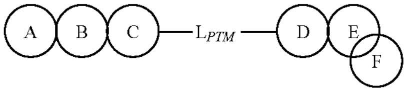

wherein:

A, B, C, D, E, and F are independently selected from an optionally substituted 5- or 6-membered aryl or heteroaryl ring, an optionally substituted 4- to 7-membered cycloalkyl or a heterocycloalkyl, where contact between circles indicates ring fusion and overlapping circles indicates spirocyclic rings;

$L_{PTM}$ is selected from a bond, an alkyl, an alkenyl or an alkynyl, optionally interrupted by one or more functional groups selected from the groups —O—, —$NR^{1PTM}$—, —C(O)—, wherein the said functional group is optionally located at either end of the linker; and $R^{1PTM}$ is selected from H, alkyl, or fluorolkyl In any aspect or embodiment described herein, aryl and heteroaryl rings of A, B, C, D, E, and F of PTM are optionally substituted with 1-8 (e.g., 1-3) substituents each independently selected from alkyl, alkenyl, haloalkyl, halogen, hydroxyl, alkoxy, fluoroalkoxy, amino, alkylamino, dialkylamino, acylamino, trifluoromethyl, and cyano, wherein the said alkyl and alkenyl groups are further optionally substituted.

In any aspect or embodiment described herein, the rings of at least one of A, B, C, F, or a combination thereof is selected from optionally substituted 5- or 6-membered aryl or heteroaryl rings;

In any aspect or embodiment described herein, the PTM has the chemical structure of Formula I, wherein:

A, B and C rings are independently 5- or 6-membered fused aryl or heteroaryl rings;

$L_{PTM}$ is selected from a bond or an alkyl, and

D is selected from a 6-membered aryl, heteroaryl or heterocycloalkyl, wherein A, B, C and D are optionally substituted with alkyl, haloalkyl, halogen, hydroxyl, alkoxy, amino, alkylamino, dialkylamino or cyano.

In any aspect or embodiment described herein, the PTM has the chemical structure of Formula I, wherein:

A and C are a phenyl or a 6-membered heteroaryl ring;

B is a 5-membered heteroaryl ring;

$L_{PTM}$ is a bond; and

D is a 6-membered heteroaryl or a 6-membered heterocycloalkyl ring;

wherein each A, B, C and D is optionally independently substituted with alkyl, haloalkyl, halogen, hydroxyl, alkoxy, amino, dialkylamino or cyano, and wherein a nitrogen atom of any of the A, B, C and D rings is not directly connected to a heteroatom or to a carbon atom, to which another heteroatom is directly attached.

In any aspect or embodiment described herein, the PTM has the chemical structure of Formula III or IV, wherein A, B and C are 5- or 6-membered fused aryl or heteroaryl rings, $L_{PTM}$ is selected from a bond or an alkyl, and D and E are 5- or 6-membered fused aryl or heteroaryl rings, wherein A, B, C, D and E are optionally substituted with alkyl, haloalkyl, halogen, hydroxyl, alkoxy, amino, alkylamino, dialkylamino or cyano.

In any aspect or embodiment described herein, the PTM is has the chemical structure of Formula I or III, wherein:

two rings of rings A, B, and C are independently selected from 5- or 6-membered aryl or heteroaryl rings, each optionally substituted with 1-3 substituents independently selected from optionally substituted linear or branched alkyl, optionally substituted linear or branched alkenyl, haloalkyl, halogen, hydroxyl, alkoxy, fluoroalkoxy, amino, alkylamino, dialkylamino, acylamino and cyano; and $L^{PTM}$ is selected from a bond, an alkyl, an alkenyl or an alkynyl, optionally interrupted by one or more rings (i.e., cycloalkyl, heterocycloalkyl, aryl or heteroaryl), or one or more functional groups which could include —O—, —S—, —$NR^1$— (where $R^1$ is selected from H or alkyl), —S(O)—, —$SO_2$—, —C(O)—, —NHC(O)—, —C(O)NH—, —$NHSO_2$—, —NHC(O)NH—, —NHC(O)O—, —OC(O)NH—, wherein the said functional group can be optionally located at either end of the linker (i.e., directly adjacent to the C or D rings).

In any aspect or embodiment described herein, the PTM is represented by a chemical structure selected from the group consisting of:

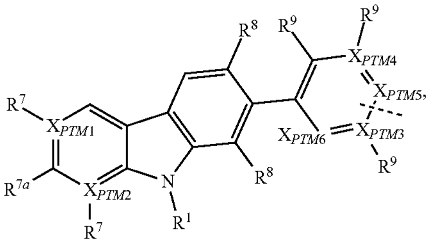

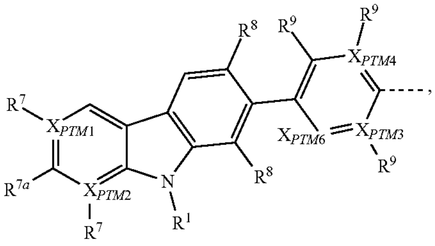

, or

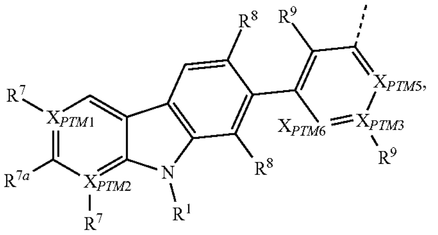

wherein one of $X_{PTM1}$ and $X_{PTM2}$ is N and the other is C;

$X_{PTM3}$, $X_{PTM4}$, $X_{PTM5}$ are independently C or N;

$X_{PTM6}$ is CH or N;

$R^1$ is H, $C_{1-4}$ alkyl (e.g., methyl), or $C_{1-3}$ fluoroalkyl (e.g., —$CH_2CF_3$, —$CHF_2$);

each $R^7$ is independently: (i) H, halogen, $C_{1-4}$ alkyl (e.g., methyl), or $C_{1-3}$ fluoroalkyl (e.g., —CF3), when the atom it is attached to is a carbon; or (ii) absent, when the atom it is attached to is a nitrogen;

$R^{7a}$ is H, halogen, $C_{1-4}$ alkyl (e.g., methyl), or $C_{1-3}$ fluoroalkyl (e.g., —$CF_3$);

each $R^8$ is independently H or halogen (e.g., F, Cl, Br);

each $R^9$ is independently: (i) H, halogen (e.g., F, Cl, Br), $C_{1}$-$C_4$ alkyl (e.g., methyl), $C_{1-3}$ fluoroalkyl (e.g., —$CF_3$), or —CN, when the atom it is attached to is a carbon; or (ii) absent, when the atom it is attached to is a nitrogen; and

 is the point of attachment of the PTM to a chemical linker group (L) or directly to a ULM, wherein:

only one $R^7$ or $R^{7a}$ is a halogen, $C_{1-4}$ alkyl, or $C_{1-3}$ fluoroalkyl;

no more than two (e.g., 0, 1, or 2) $R^9$ are a halogen or —CN; and 0, 1, or 2 of $X_{PTM3}$, $X_{PTM4}$, $X_{PTM5}$, and $X_{PTM6}$ are N.

In any aspect or embodiment described herein, the PTM is represented by a chemical structure selected from the group consisting of:

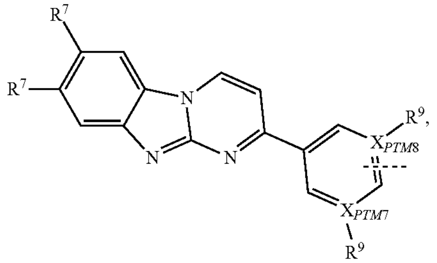

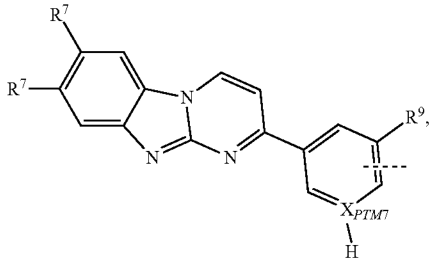

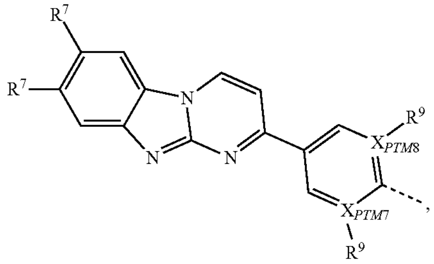

, or

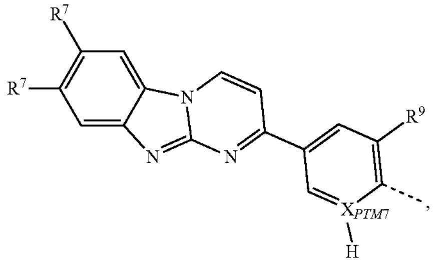

wherein:

$X_{PTM7}$ and $X_{PTM8}$ are independently a nitrogen or carbon;

each $R^7$ is independently H or halogen (e.g., F, Cl, Br);

each $R^9$ is independently: (i) halogen, H, or $C_{1-3}$ fluoroalkyl (e.g., —$CF_3$) when the atom it is attached to is a carbon; or (ii) absent, when the atom it is attached to is a nitrogen; and

 is the point of attachment of the PTM to a chemical linking group (L) or directly to a ULM.

In any aspect or embodiment described herein, the PTM is represented by a chemical structure selected from the group consisting of:

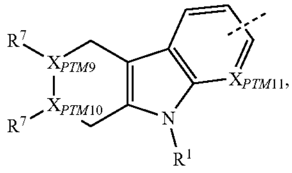

-continued

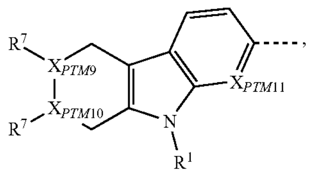

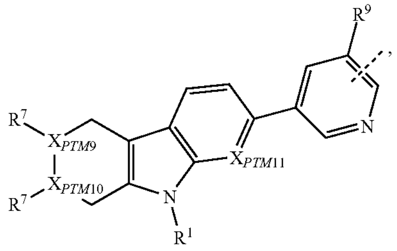

or

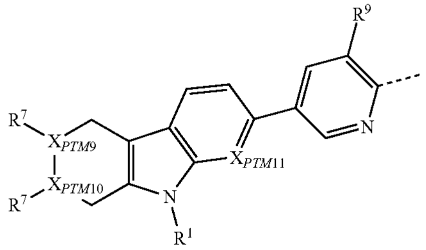

wherein:

one of $X_{PTM9}$ or $X_{PTM10}$ is nitrogen and the other $CH_2$;

$X_{PTM11}$ is nitrogen or CH;

$R^1$ is H, $C_{1-4}$ alkyl (e.g., methyl), $C_{1-3}$ fluoroalkyl (e.g., —$CH_2CF_3$, —$CHF_2$);

$R^7$ is (i) H when the atom it is attached to is a carbon; or (ii) H or a C1-3 alkyl when the atom it is attached to is a nitrogen;

$R^9$ is H, halogen, halogen (e.g., F, Cl, Br), or $C_{1-2}$ fluoroalkyl (—$CF_3$); and is the point of attachment of the PTM to a chemical linking group (L) or directly to a ULM.

In any aspect or embodiment described herein, the PTM is represented by a chemical structure selected from the group consisting of:

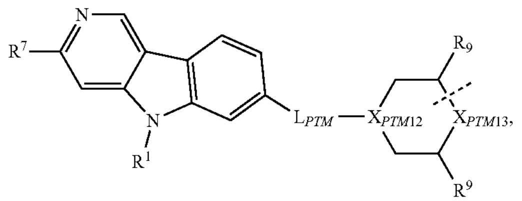

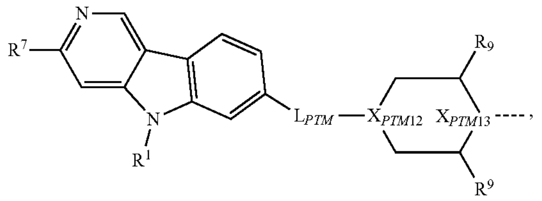

-continued

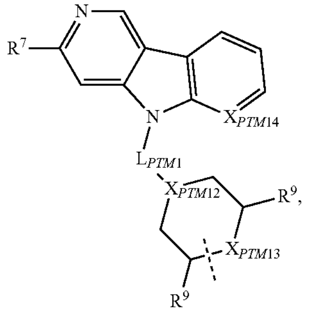

or

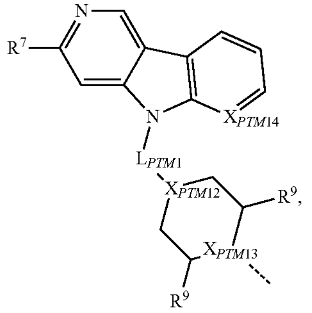

wherein:

each $X_{PTM12}$ and $X_{PTM13}$ is independently nitrogen or carbon with hydrogen atoms to complete valency, wherein at least one of $X_{PTM12}$ and $X_{PTM13}$ is nitrogen;

$X_{PTM14}$ is a nitrogen or CH;

$L_{PTM}$ is bond, $C_{1-3}$ alkyl, $C_{2-3}$ alkynyl (e.g., C3 alkynyl), wherein a carbon of the alkyl is optionally replaced with an O or C(═O);

$L_{PTM1}$ is a $C_{1-C4}$ alkyl;

$R^1$ is H, $C_{1-4}$ alkyl (e.g., methyl), $C_{1-3}$ fluoroalkyl (e.g., —$CH_2CF_3$, —$CHF_2$);

$R^7$ is H, halogen, $C_{1-4}$ alkyl (e.g., methyl), or $C_{1-3}$ fluoroalkyl (e.g., —$CF_3$);

each $R^9$ is independently H or halogen (e.g., F, Cl, Br); and is the point of attachment of the PTM to a chemical linking group (L) or directly to a ULM.

In any aspect or embodiment described herein, the PTM is represented by a chemical structure selected from the group consisting of:

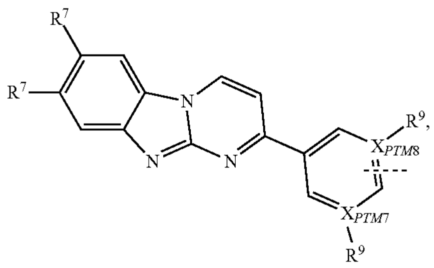

-continued

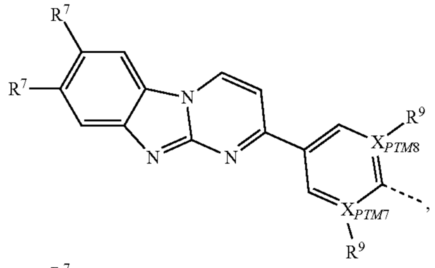

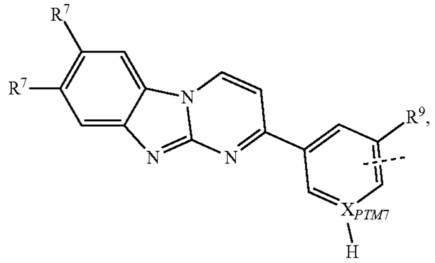

or

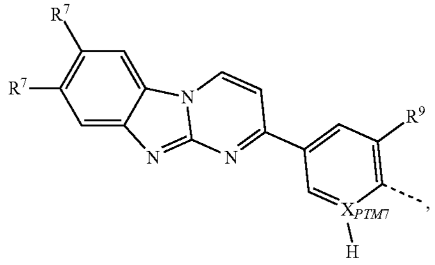

wherein:

$X_{PTM7}$ and $X_{PTM8}$ are independently a nitrogen or carbon;

each $R^7$ is independently H or halogen (e.g., F, Cl, Br);

each $R^9$ is independently: (i) halogen or H, when the atom it is attached to is a carbon; or (ii) absent, when the atom it is attached to is a nitrogen; and is the point of attachment of the PTM to a chemical linking group (L) or directly to a ULM.

In any aspect or embodiment described herein, the PTM is represented by a chemical structure selected from the group consisting of:

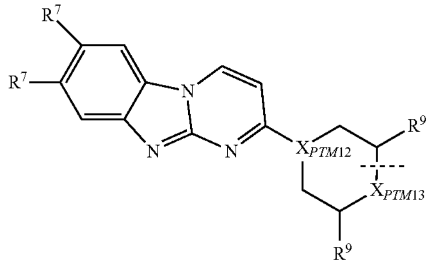

or

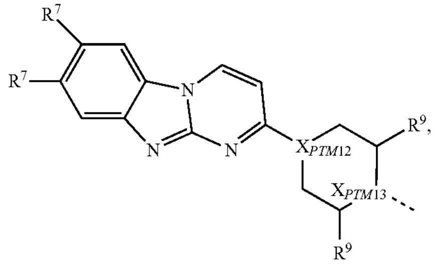

wherein:

each $X_{PTM12}$ and $X_{PTM13}$ is independently nitrogen or carbon with hydrogen atoms to complete valency, wherein at least one of $X_{PTM12}$ and $X_{PTM13}$ is nitrogen;

each $R^7$ is independently H or halogen (e.g., F, Cl, Br);

each $R^9$ is independently H or halogen (e.g., F, Cl, Br); and is the point of attachment of the PTM to a chemical linking group (L) or directly to a ULM.

In any aspect or embodiment described herein, the PTM is represented by a chemical structure selected from the group consisting of:

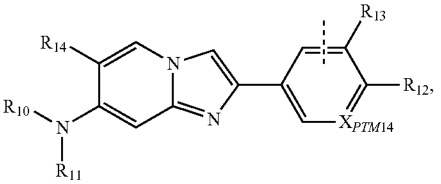

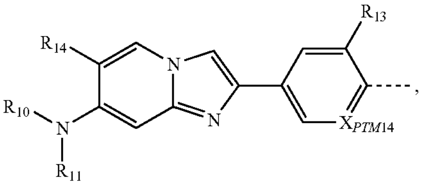

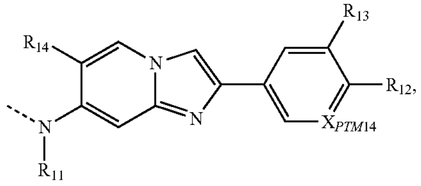

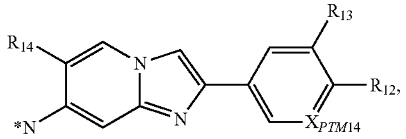

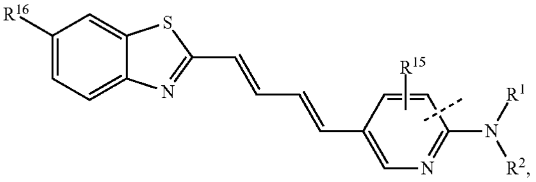

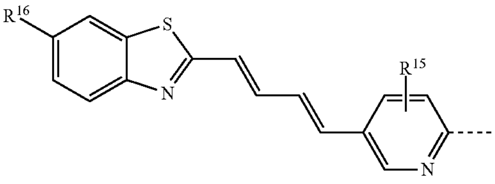

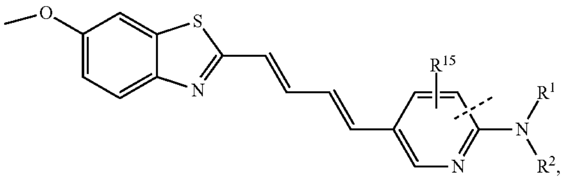

-continued

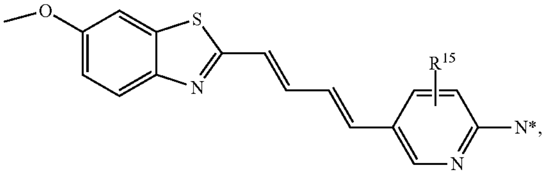

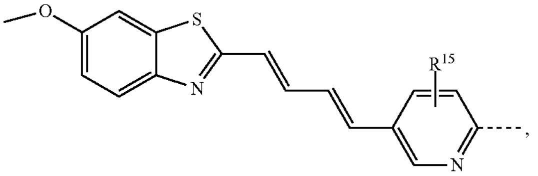

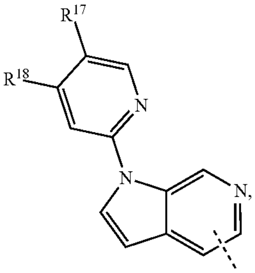

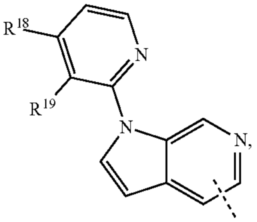

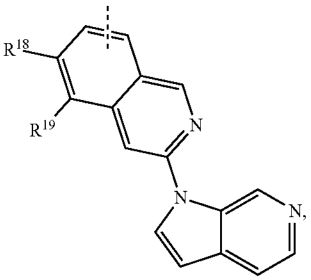

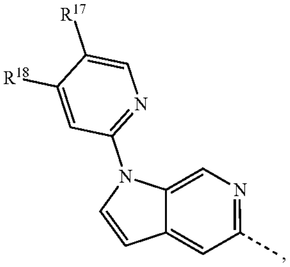

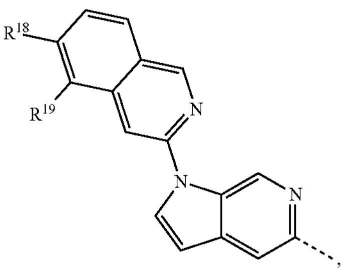

or

-continued

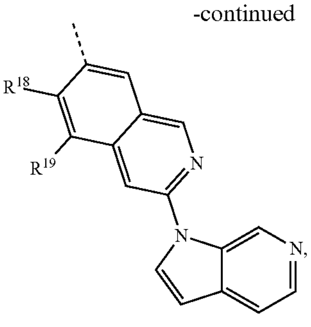

wherein:

$X_{PTM14}$ is N or CH;

$R^{10}$ and $R^{11}$ are independently selected from H, methyl, and ethyl;

$R^{12}$ and $R^{13}$ are independently selected from H, methyl, ethyl, halogen (e.g., F, Cl, Br), $C_{1-3}$ alkyl (e.g., methyl) and $C_{1-2}$ haloalkyl;

$R^{14}$ is selected from H, methyl, ethyl, and halogen (e.g., F, Cl, Br);

$R^{15}$ is 1 to 2 substituents independently selected from H, methyl, ethyl and halogen;

$R^{16}$ is H, OH, or $C_{1-3}$ alkoxyl (e.g., methoxy);

$R^{17}$ is H, halogen (e.g., F, Cl, Br), or $C_{1-3}$ alkyl (e.g., methyl)

$R^{18}$ is H, halogen (e.g., F, Cl, Br), or $C_{1-2}$haloalkyl (e.g., —$CF_3$) $R^{19}$ is H, halogen (e.g., F, Cl, Br.), $C_{1-2}$ haloalkyl (e.g., —$CF_3$), or —$NH_2$, $N(R^{20})_2$ each $R^{20}$ is independently H or $C_{1-3}$ alkyl (e.g., methyl);

N* is the point of attachment of the PTM to the chemical linking group (L) or directly to the ULM; and

 is the point of attachment of the PTM to the chemical linking group (L) or directly to the ULM.

In any aspect or embodiment described herein, the PTM is represented by a chemical structure selected from the group consisting of:

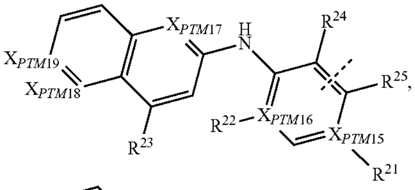

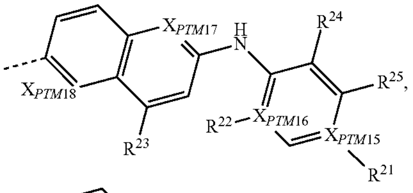

or

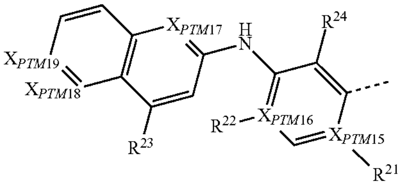

wherein:

each of $X_{PTM17}$, $X_{PTM18}$, and $X_{PTM19}$ is independently N or CH;

each of $X_{PTM15}$ and $X_{PTM16}$ is N or C;

US 11,912,699 B2

$R^{21}$ is: (i) H or $C_{1-3}$ alkyl (e.g., methyl), when the atom it is attached to is a carbon; or (ii) absent, when the atom it is attached to is a nitrogen;

$R^{22}$ is (i) H or halogen (e.g., F, Cl, Br), when the atom it is attached to is a carbon; or (ii) absent, when the atom it is attached to is a nitrogen;

$R^{23}$ is H or halogen (e.g., F, Cl, Br);

$R^{24}$ is H or halogen (e.g., F, Cl, Br);

$R^{25}$ is H or $C_{1-3}$ alkyl (e.g., methyl); and

 is the point of attachment of the PTM to the chemical linking group (L) or directly to the ULM.

In any aspect or embodiment described herein, there is zero or one nitrogen per ring of the PTM In any aspect or embodiment described herein, the PTM is represented by a chemical structure selected from the group consisting of:

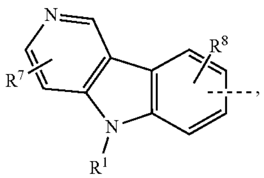
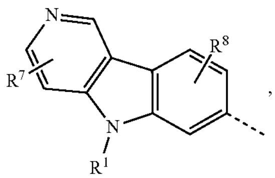
,
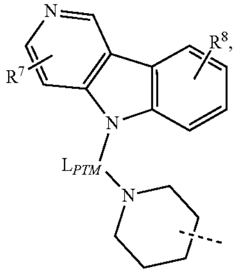
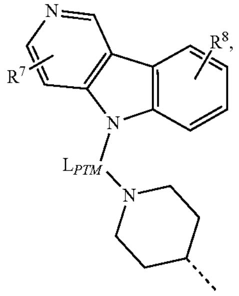
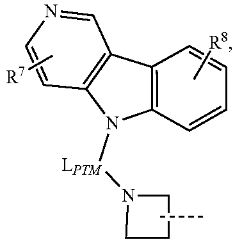
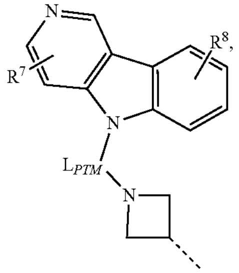

wherein:

$R^1$ is selected from H, optionally substituted alkyl (e.g., a haloalkyl, fluoroalkyl, difluromethyl, or triflurom-ethyl), methyl, ethyl, 2-fluoroethyl and 2,2,2-trifluoro-ethyl; and each of $R^7$ and $R^8$ are independently 1 or 2 substituents independently selected from H, optionally substituted alkyl, haloalkyl, halogen, hydroxyl, alkoxy, amino, dialkylamino, acetylamino, trifluoromethyl, or cyano;

$L_{PTM}$ is selected from a bond, an $C_{1-3}$ alkyl, an $C_{2-3}$ alkenyl or a $C_{2-3}$ alkynyl, optionally interrupted one or more functional groups selected from the groups —O—, —$NR^{1PTM}$—, —C(O)—, wherein the said functional group is optionally located at either end of the linker; and

 is the point of attachment of the PTM to the chemical linking group (L) or directly to the ULM.

In any aspect or embodiment described herein, the PTM is represented by a chemical structure selected from the group consisting of:

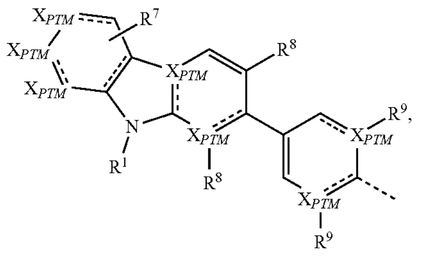

wherein:

each $R^1$ and $R^7$ is independently selected from H, halo, F, $C_{1-3}$ alkyl, —$CH(F_2)$, —$CH_2C(F_3)$, CN;

each $R^8$ and each $R^9$ is independently selected from H, halo, F, $C_{1-3}$ alkyl, —$CH(F_2)$, —$CH_2C(F_3)$, CN;

each $X_{PTM}$ is independently C or N;

 is a single bond or a double bond; and

 is the site of attachment to chemical linking group (L).

In any aspect or embodiment described herein, the PTM is represented by a chemical structure selected from the group consisting of:

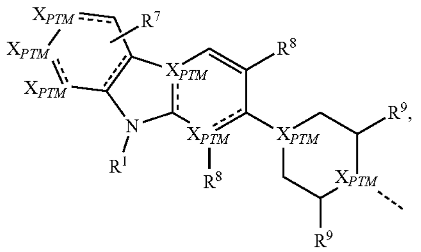

wherein:

each $R^1$ and $R^7$ is independently selected from H, halo, F, $C_{1-3}$ alkyl, —$CH(F_2)$, —$CH_2C(F_3)$, CN;

each $R^8$ and each $R^9$ is independently selected from H, halo, F, $C_{1-3}$ alkyl, —$CH(F_2)$, —$CH_2C(F_3)$, CN;

each $X_{PTM}$ is independently C or N;

 is a single bond or a double bond; and

 is the site of attachment to chemical linking group (L).

In any aspect or embodiment described herein, the PTM is represented by a chemical structure selected from the group consisting of:

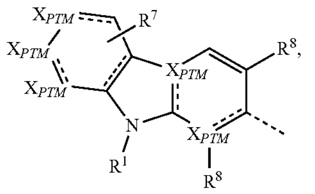

wherein:

each $R^1$ and $R^7$ is independently selected from H, halo, F, $C_{1-3}$ alkyl, —$CH(F_2)$, —$CH_2C(F_3)$, CN; each $R^1$ is independently selected from H, halo, F, $C_{1-3}$ alkyl, —$CH(F_2)$, —$CH_2C(F_3)$, CN;

each $X_{PTM}$ is independently C or N;

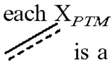 is a single bond or a double bond; and

 is the site of attachment to chemical linking group (L).

In any aspect or embodiment described herein, the PTM is represented by a chemical structure selected from the group consisting of:

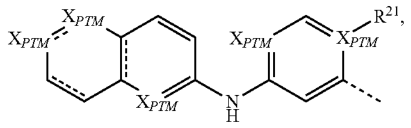

wherein:

each $R^{21}$ is independently selected from H, halo, F, $C_{1-3}$ alkyl, —$CH(F_2)$, —$CH_2C(F_3)$, CN;

each $X_{PTM}$ is independently C or N;

 is a single bond or a double bond; and

 is the site of attachment to chemical linking group (L).

In any aspect or embodiment described herein, the PTM is represented by a chemical structure selected from the group consisting of:

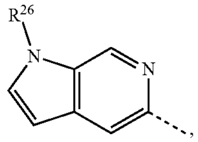

wherein:

each $R^{26}$ is H, optionally substituted cyclic, heterocyclic, heterobicyclic, or a member selected from

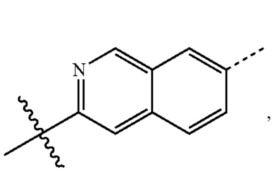

,

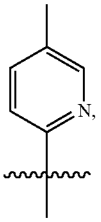

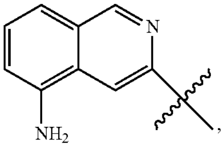

,

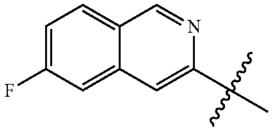

, or

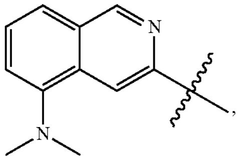

,

is the site of coupling to the pyrrolyl nitrogen and

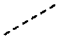 is the site of attachment to chemical linking group (L).

In an aspect, the present disclosure provides a compound of the structure:

PTM-L-ULM, wherein: PTM is a Tau protein targeting moiety, L is a chemical linking moiety, and ULM is an E3 ubiquitin ligase binding moiety, and wherein (i) PTM is a structure selected from:

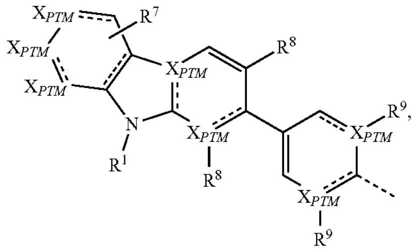

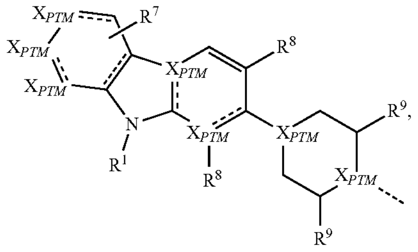

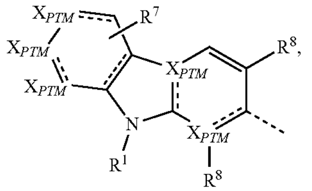

and

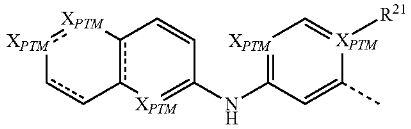

wherein:

each $R^1$ and $R^7$ is independently selected from H, halo, F, $C_{1-3}$ alkyl, —$CH(F_2)$, —$CH_2C(F_3)$, CN;

each $R^8$ and each $R^9$ is independently selected from H, halo, F, $C_{1-3}$ alkyl, —$CH(F_2)$, —$CH_2C(F_3)$, CN;

each $R^{21}$ is independently selected from H, halo, F, $C_{1-3}$ alkyl, —$CH(F_2)$, —$CH_2C(F_3)$, CN;

each $X_{PTM}$ is independently C or N;

 is a single bond or a double bond; and

 is the site of attachment to chemical linking group (L);

(ii) L is a structure selected from:

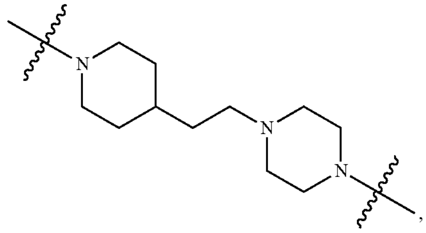,

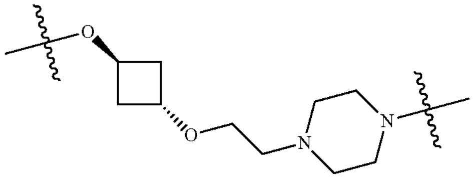,

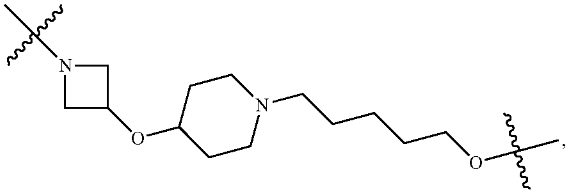,

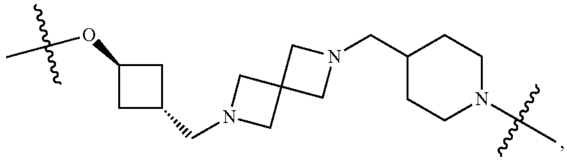,

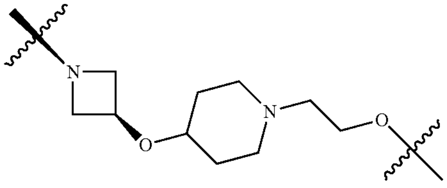,

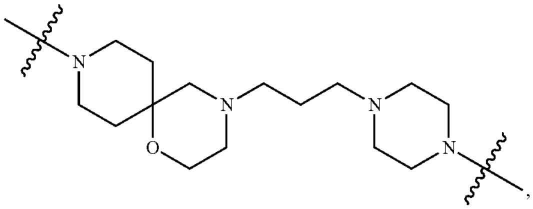,

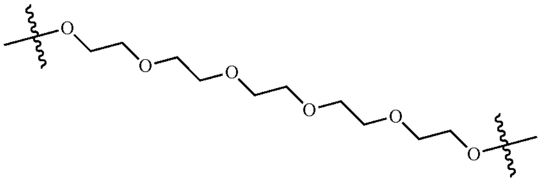, or

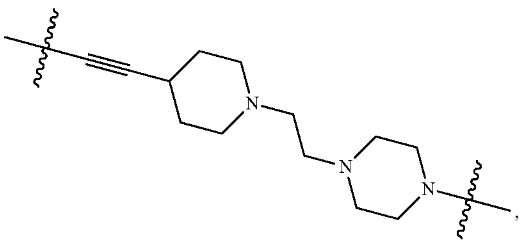, wherein

is the site of attachment to the ULM or PTM; and (iii) ULM is a structure according to:

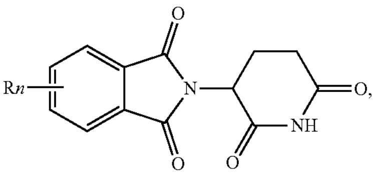

wherein:

R is independently H, halo, methoxy, or site of attachment of a chemical linking group (L), and n is an integer selected from 1, 2, 3, or 4, wherein at least one R is a site of attachment to a chemical linking group (L), or a pharmaceutically acceptable salt thereof.

In an aspect, the present disclosure provides a compound of the structure:

PTM-L-ULM, wherein: PTM is a Tau protein targeting moiety, L is a chemical linking moiety, and ULM is an E3 ubiquitin ligase binding moiety, and wherein (i) PTM is a structure selected from:

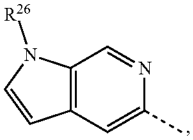, wherein:

each $R^{26}$ is H, optionally substituted cyclic, heterocyclic, heterobicyclic, or a member selected from

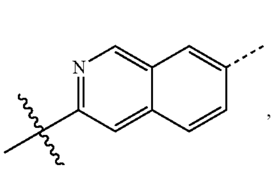, 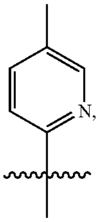

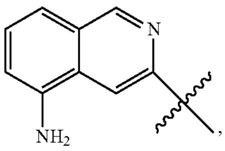, 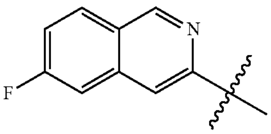, or

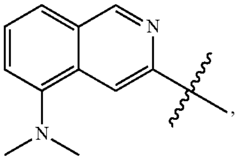, 

is the site of coupling to pyrroyl nitrogen and

 is the site of attachment to chemical linking group (L).

(ii) L is a structure selected from:

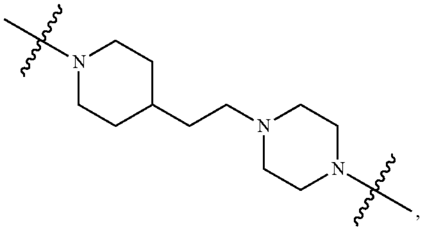

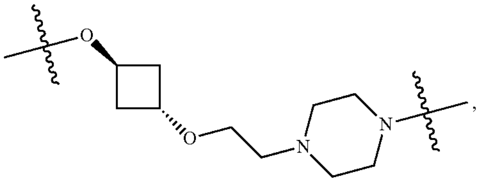

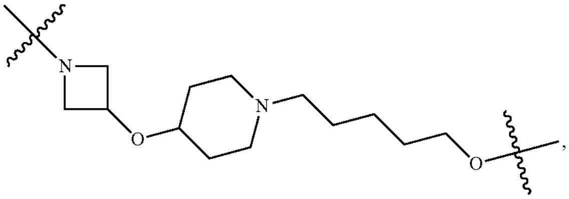

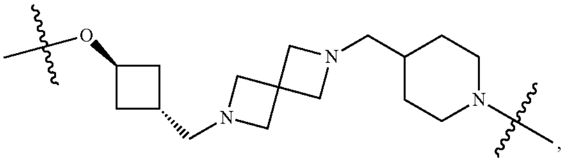

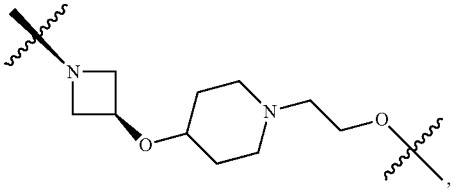

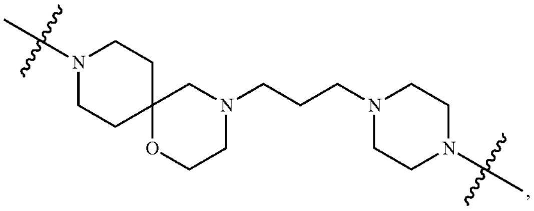

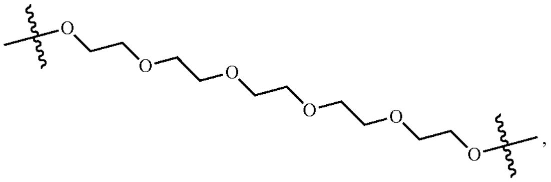

or

-continued

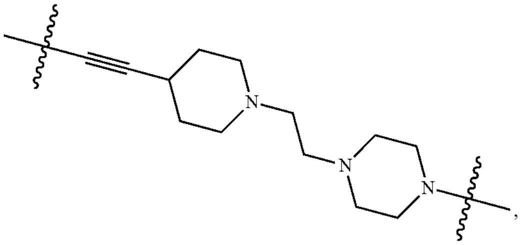

wherein

is the site of attachment to the ULM or PTM; and (iii) ULM is a structure according to:

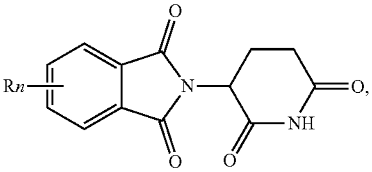

wherein:

R is independently H, halo, methoxy, or site of attachment of a chemical linking group (L), and n is an integer selected from 1, 2, 3, or 4, wherein at least one R is a site of attachment to a chemical linking group (L), or a pharmaceutically acceptable salt thereof.

In any aspect or embodiment described herein, the PTM is a chemical structure selected from the group consisting of:

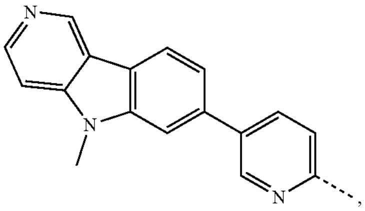

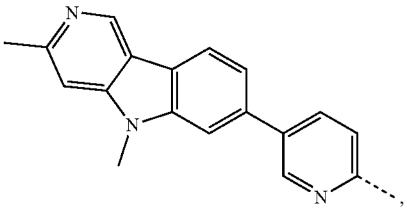

-continued
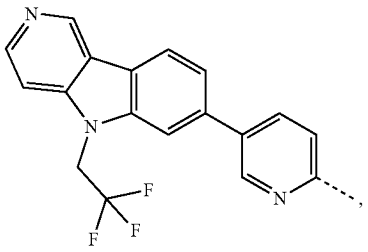
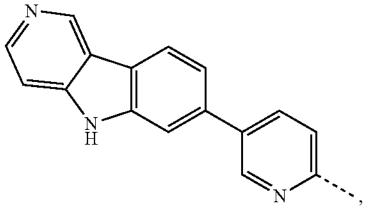
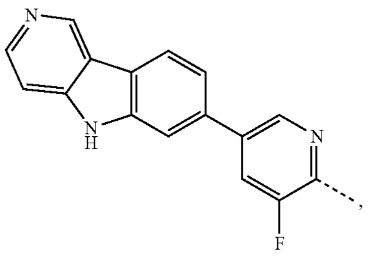
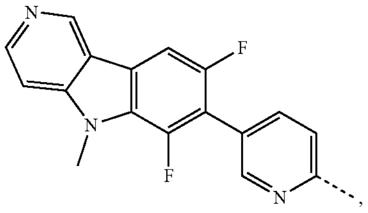
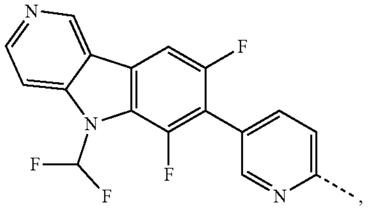
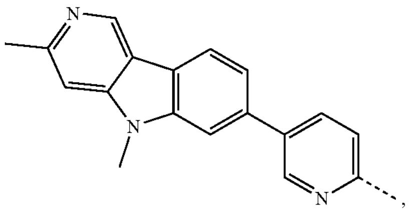
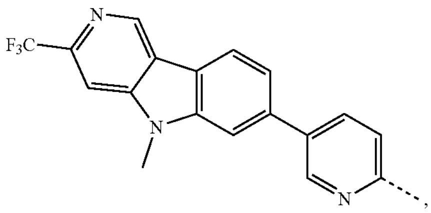
-continued
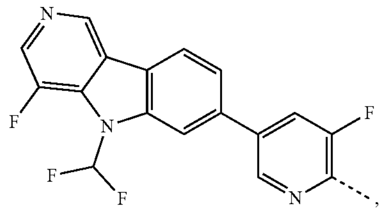
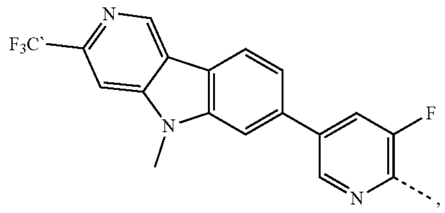
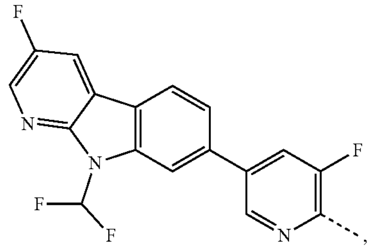
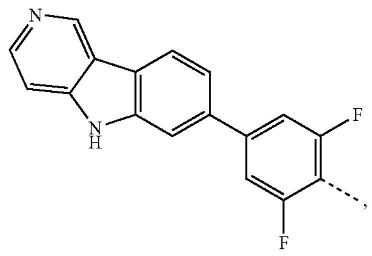
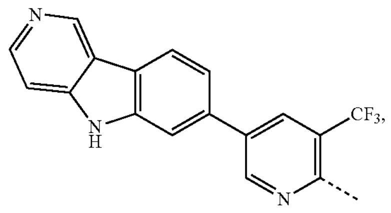
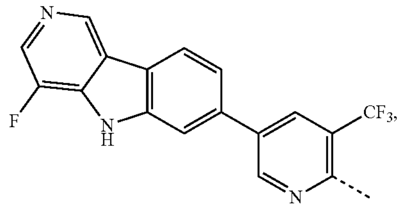
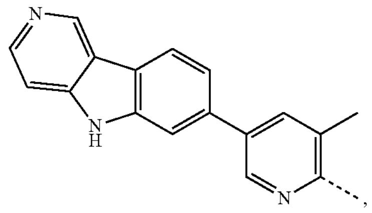

-continued
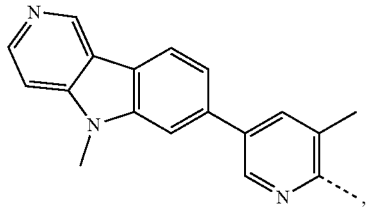
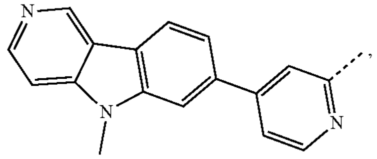
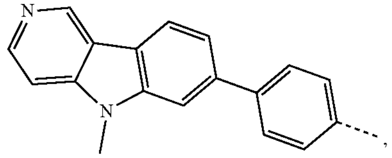
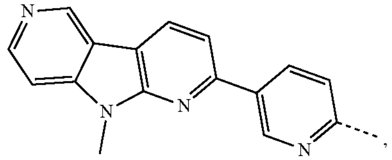
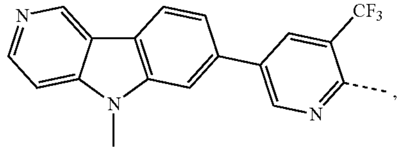
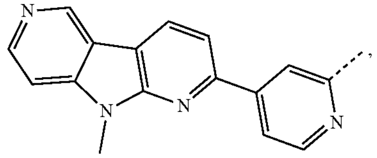
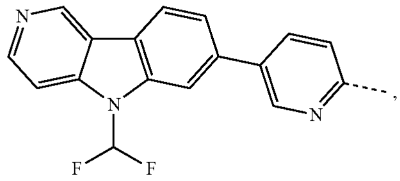
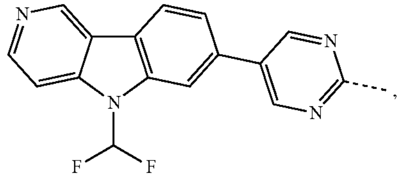
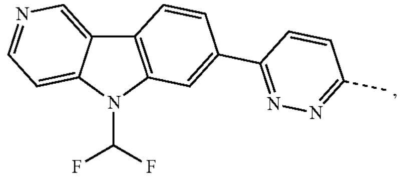
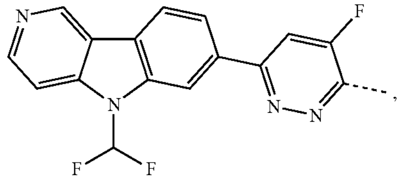
-continued
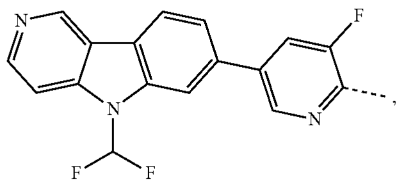
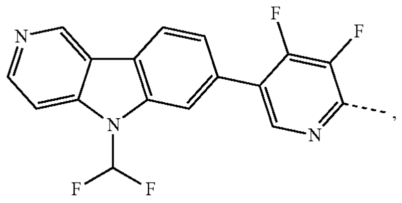
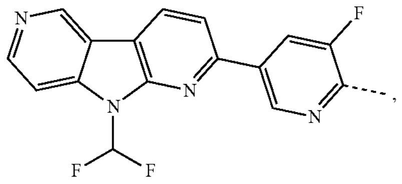
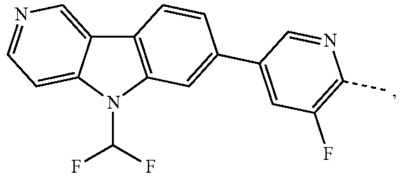
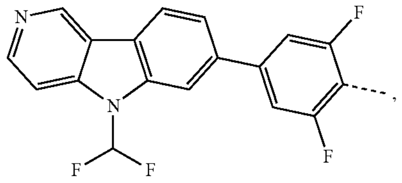
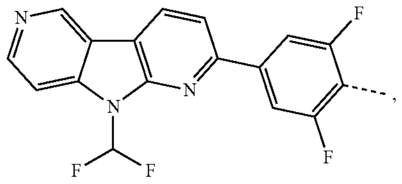
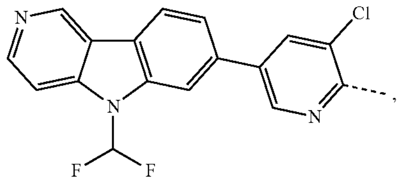
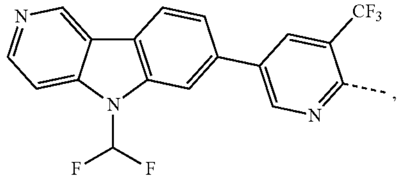
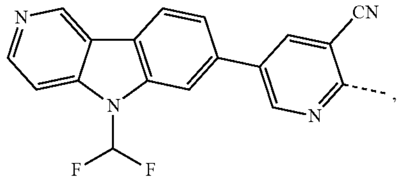

-continued
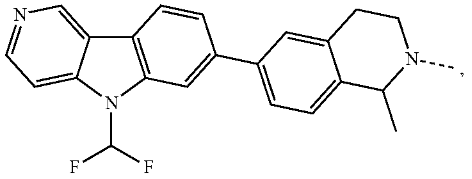
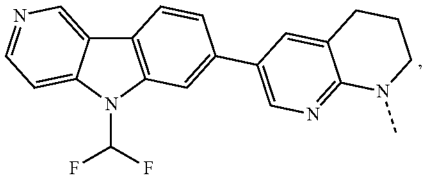
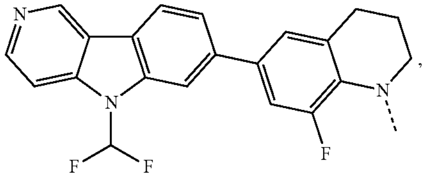
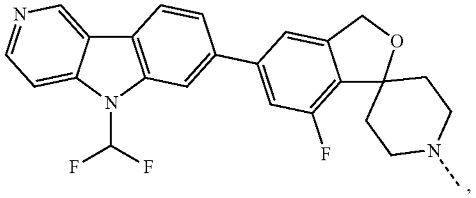
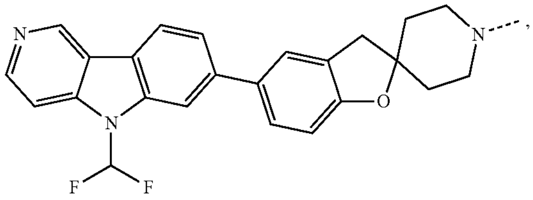
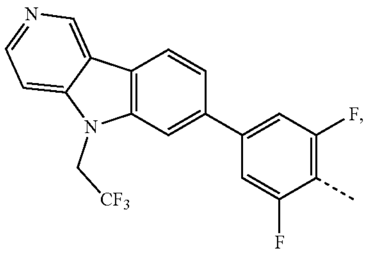
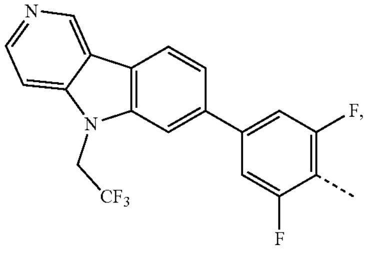
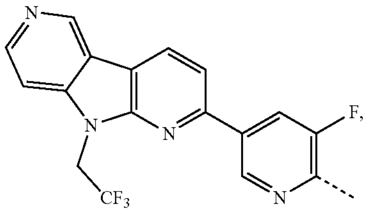
-continued
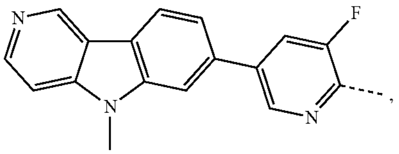
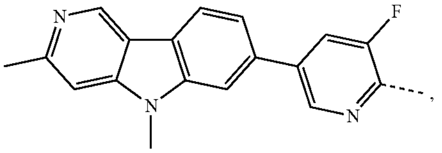
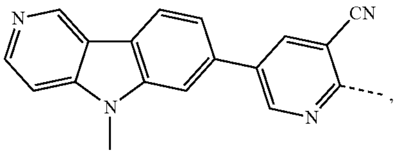
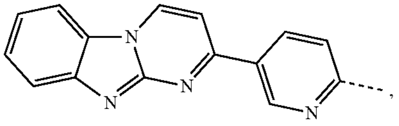
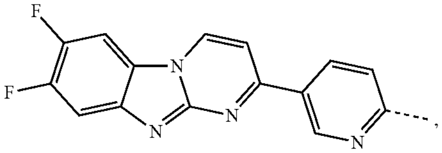
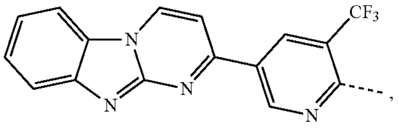
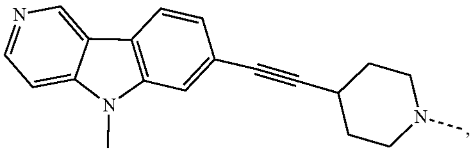
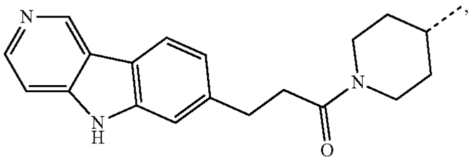
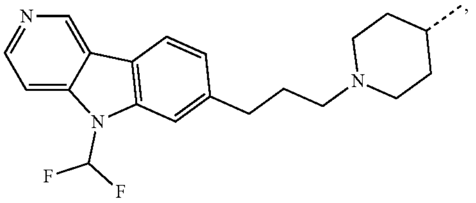
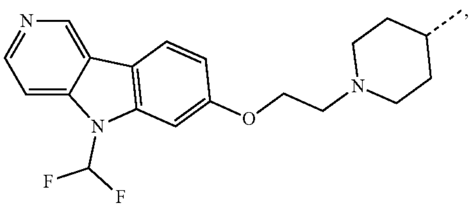

-continued
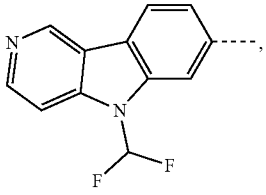
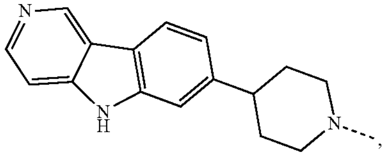
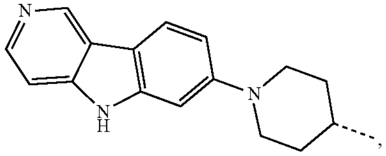
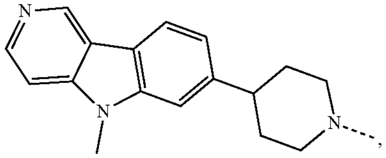
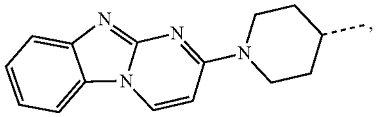
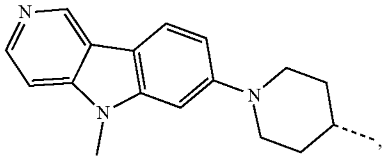
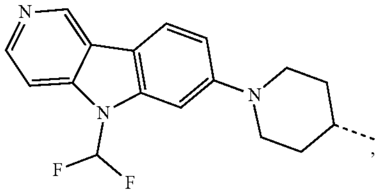
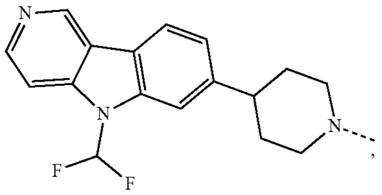
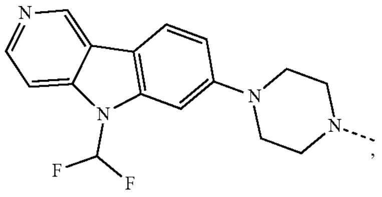
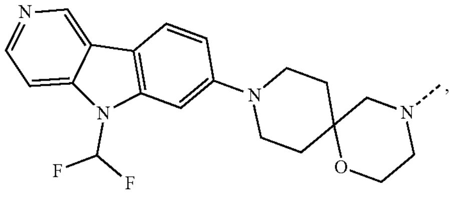
-continued
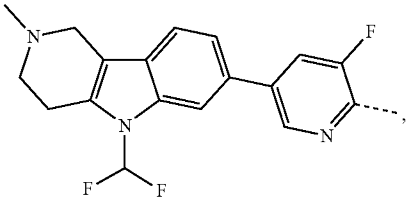
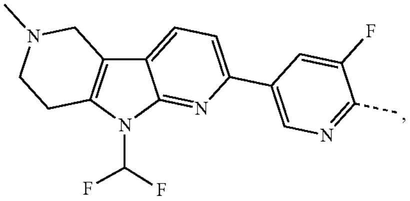
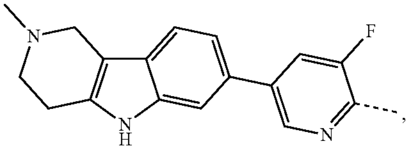
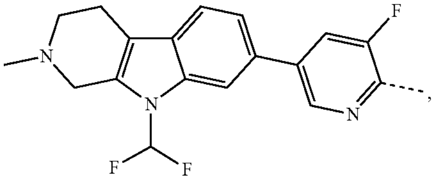
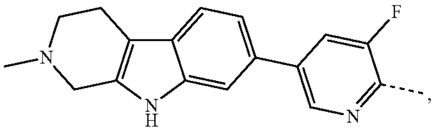
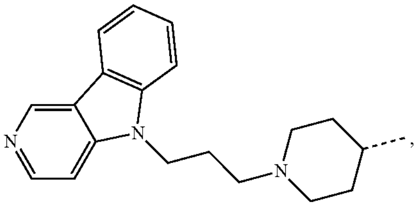
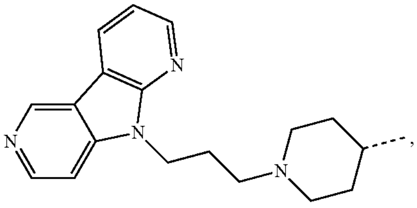
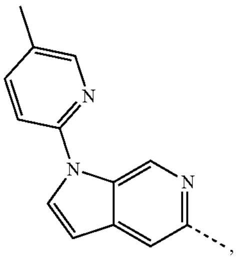
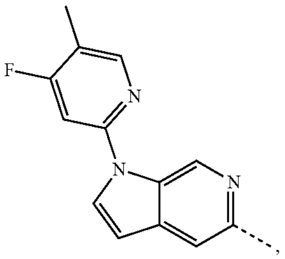

-continued
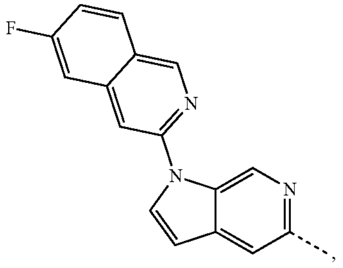
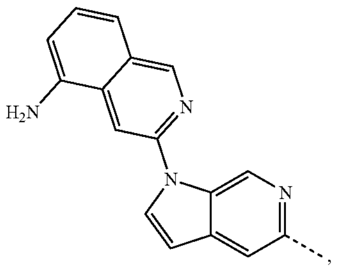
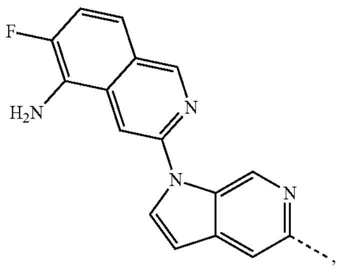
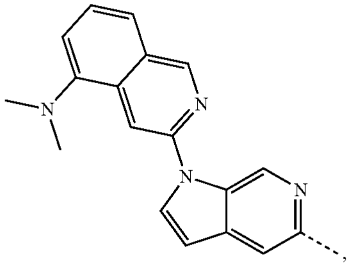
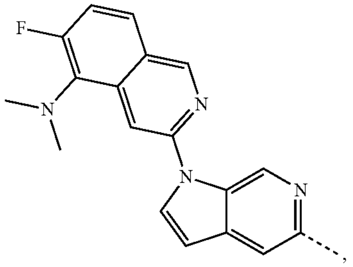
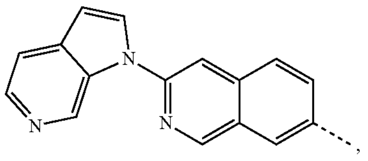
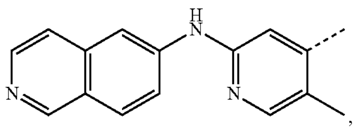
-continued
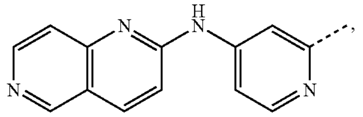
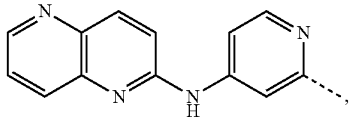
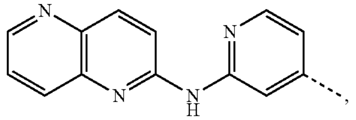
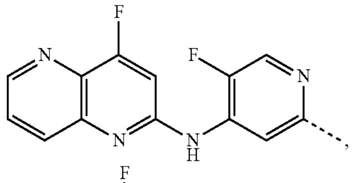
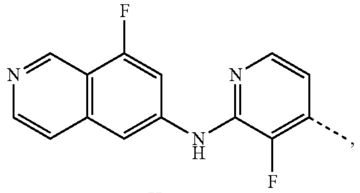
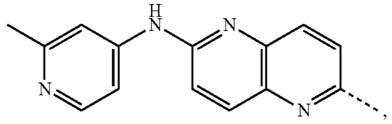
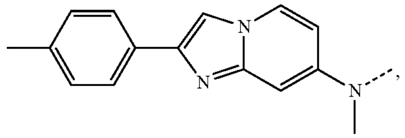
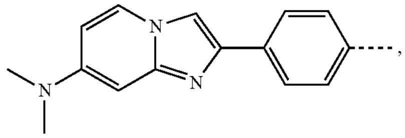
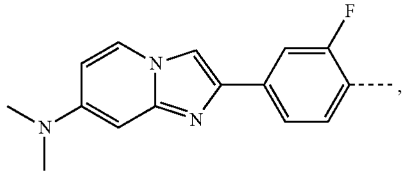
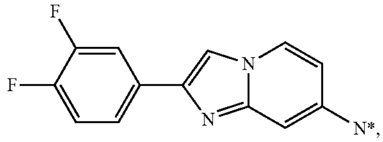
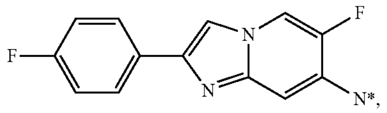
and
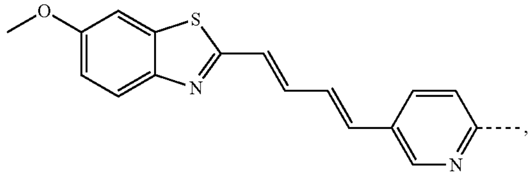

wherein the * and  is the point of attachment of the PTM to the chemical linking group (L) or directly to the ULM.
In any aspect or embodiment described herein, the PTM is a chemical structure selected from the group consisting of:
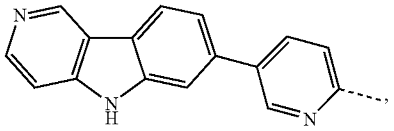
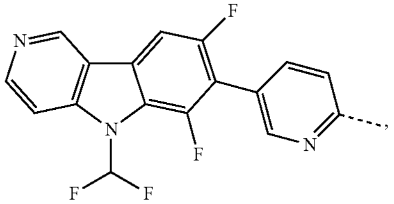
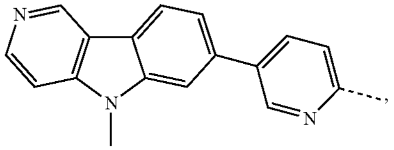
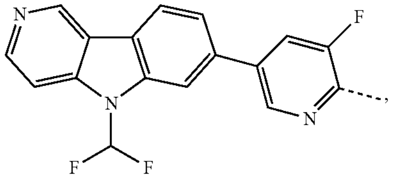
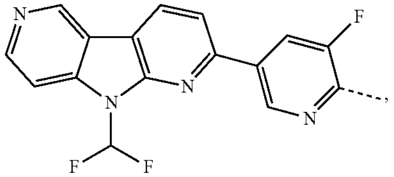
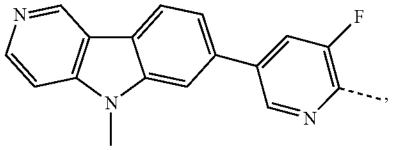
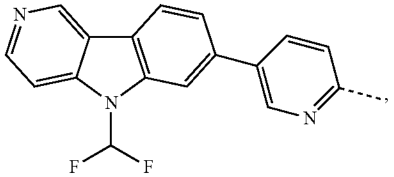
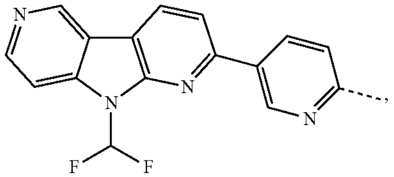
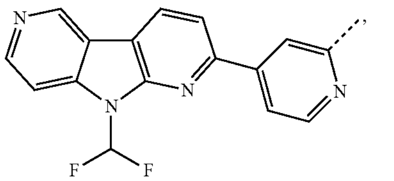
-continued
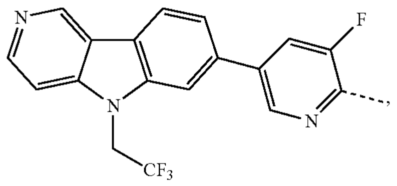
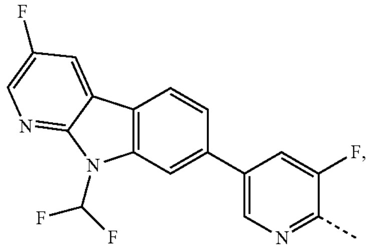
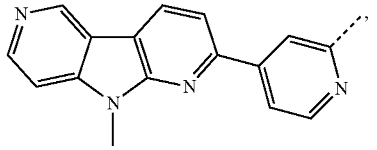
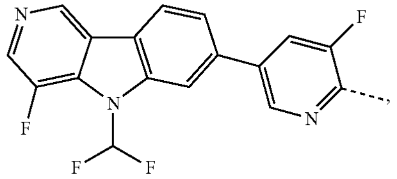
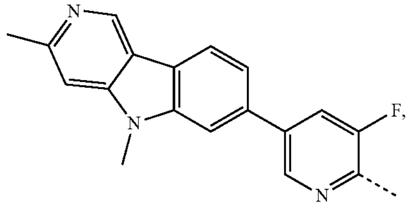
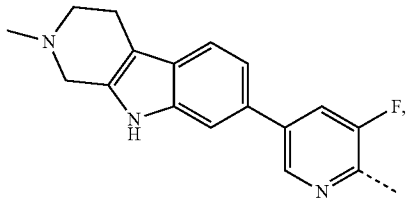
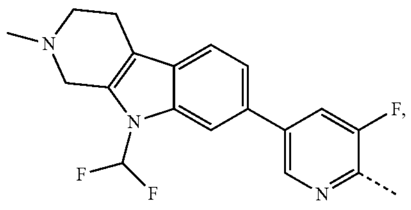
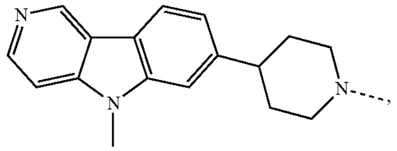
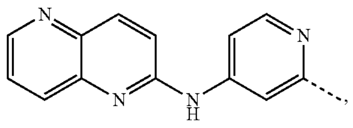

-continued
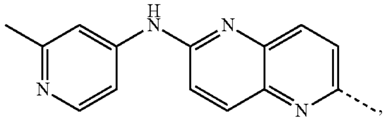
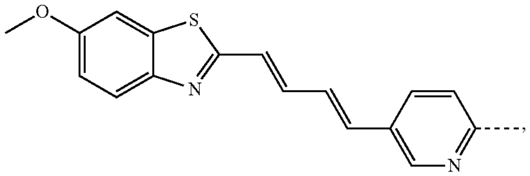
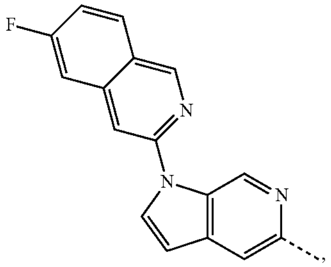
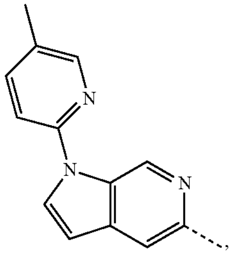
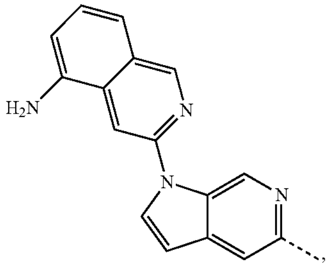
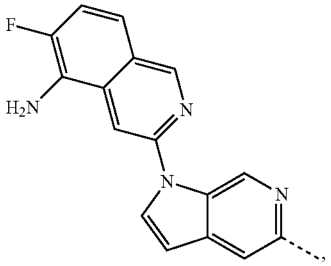
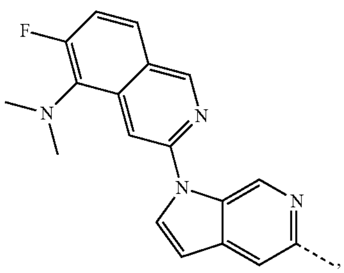
and
-continued
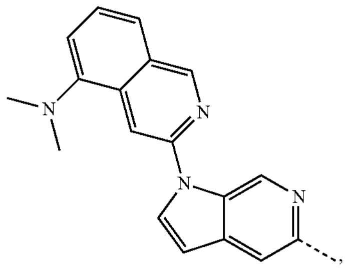
wherein  is the point of attachment of the PTM to the chemical linking group (L) or directly to the ULM.
In any aspect or embodiment described herein, the PTM is represented by following chemical structure:
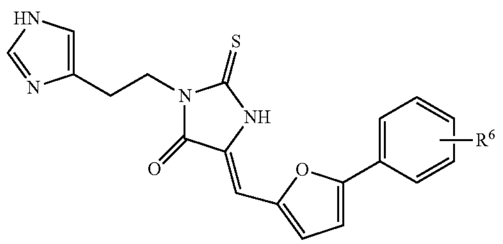
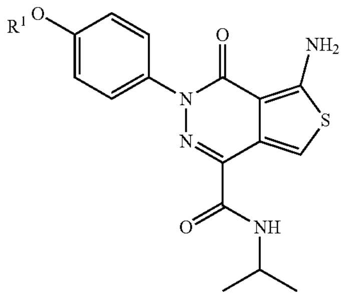
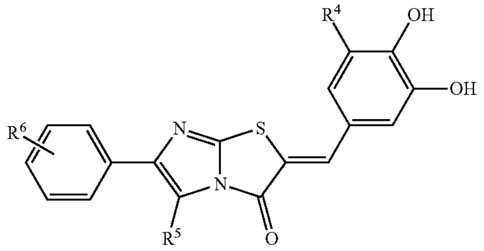
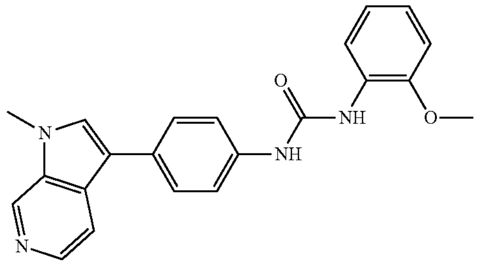
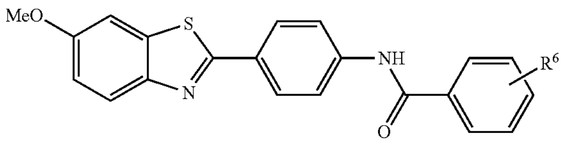

-continued
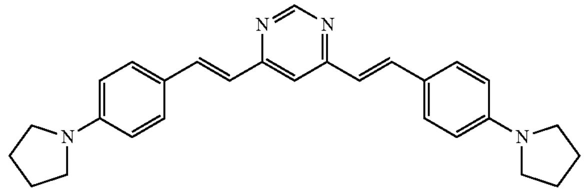
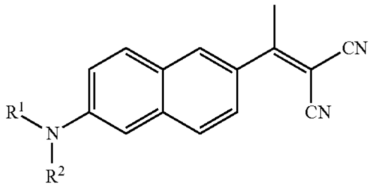
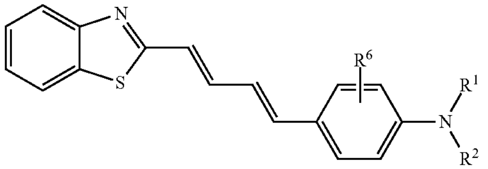
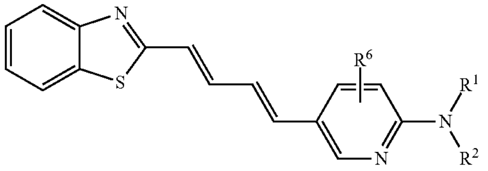
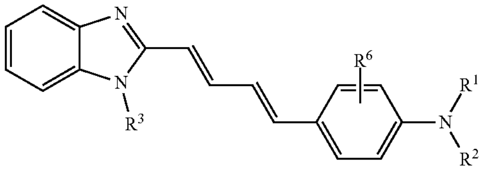
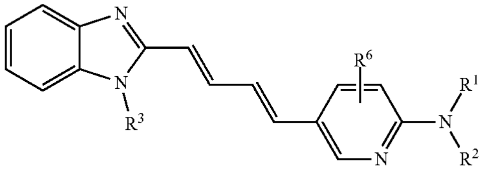
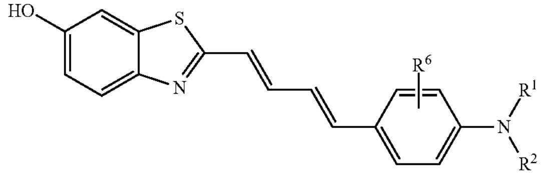
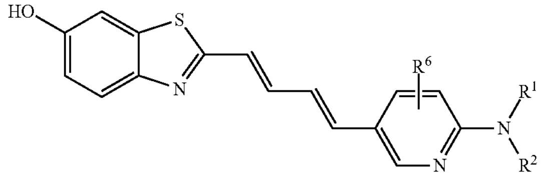
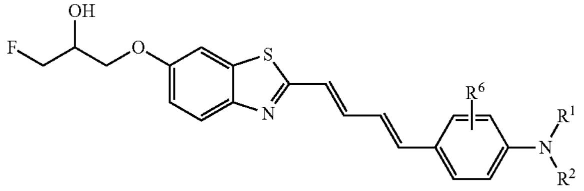
-continued
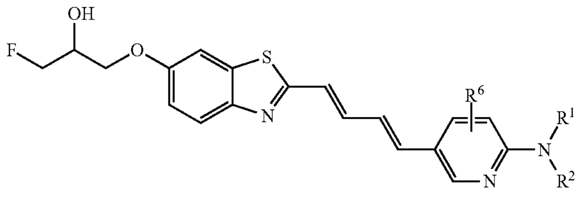
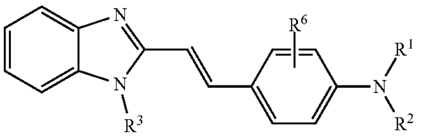
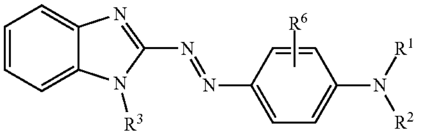
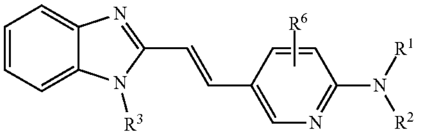
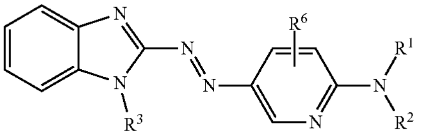
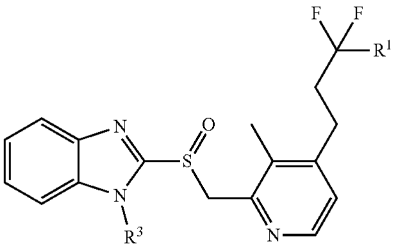
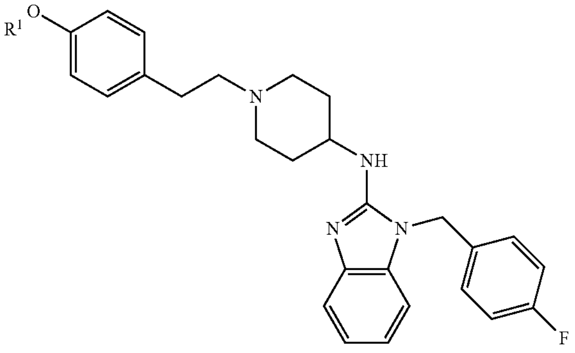
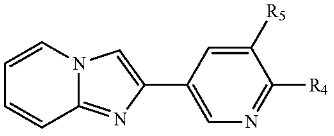
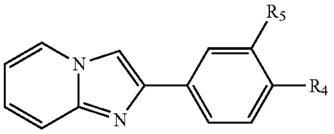

-continued

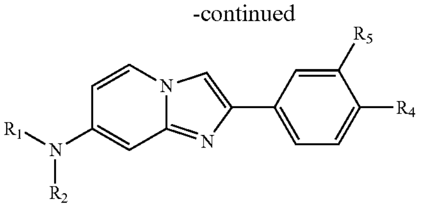

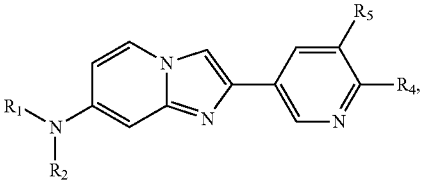

wherein:

$R^1$, $R^2$ and $R^3$ are independently selected from H, methyl, ethyl, 2-fluoroethyl and 2,2,2-trifluoroethyl;

$R^4$ and $R^5$ are independently selected from H, methyl, ethyl, halogen, haloalkyl, and cyano; and $R^6$ is 1 to 2 substituents independently selected from H, methyl, ethyl and halogen, wherein the PTM is coupled to a ULM via L.

In any aspect or embodiment described herein, the PTM is covalently coupled to one or more ULM (VLM or CLM) groups, or a linker to which is attached one or more ULM (VLM or CLM) groups as described herein.

In any aspect or embodiment described herein, PTM is represented by chemical structure:

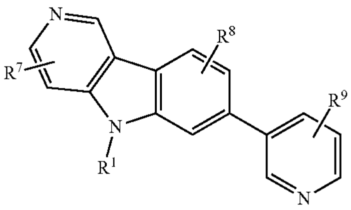

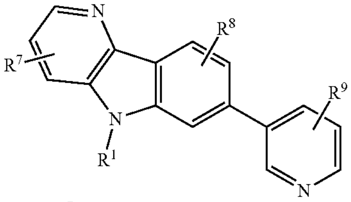

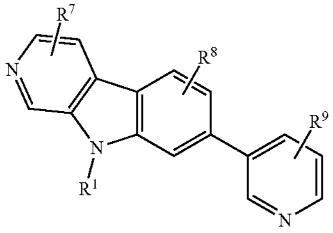

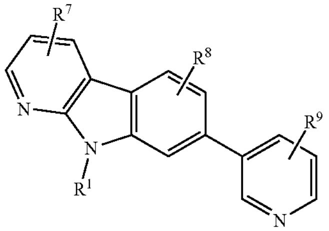

-continued

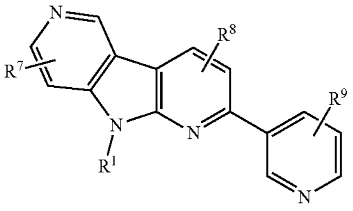

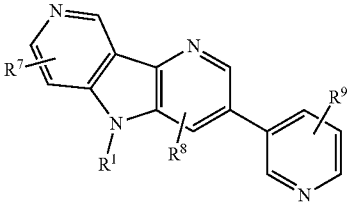

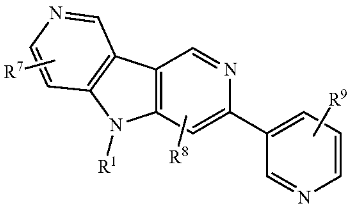

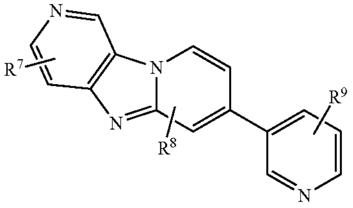

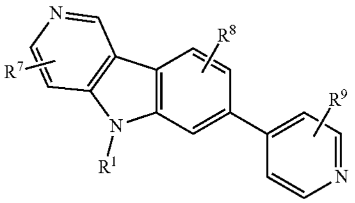

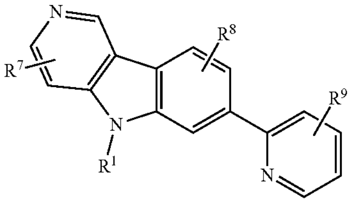

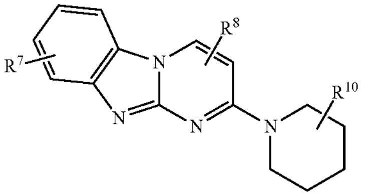

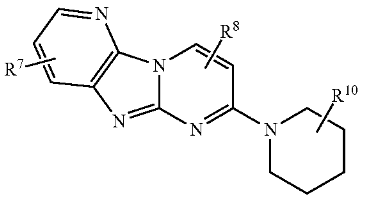

-continued
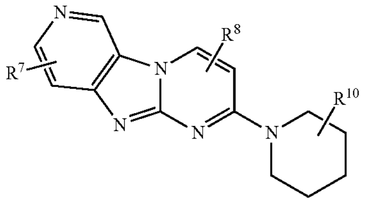
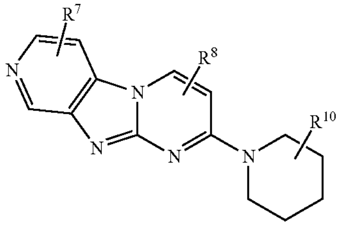
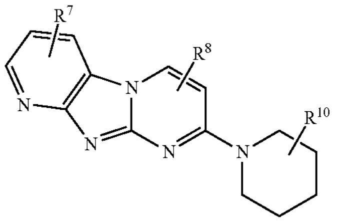
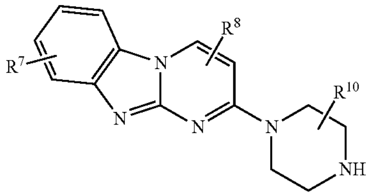
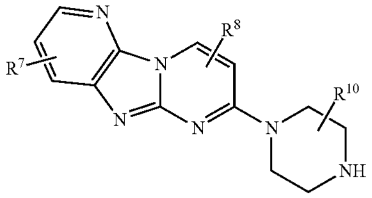
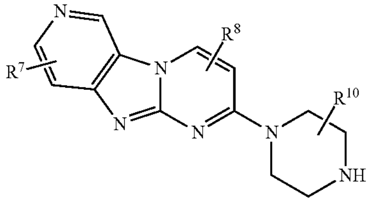
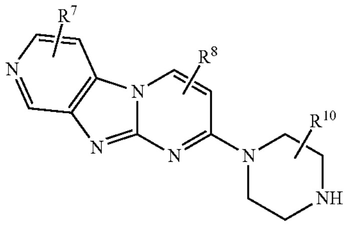
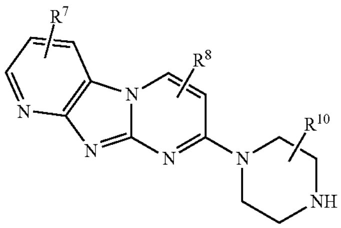
-continued
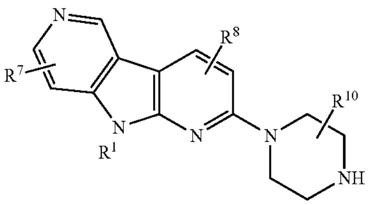
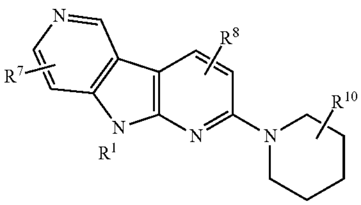
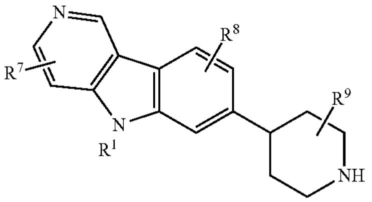
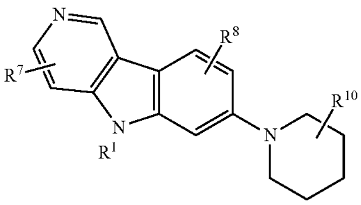
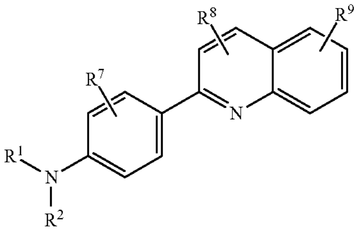
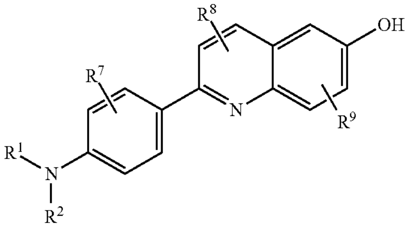
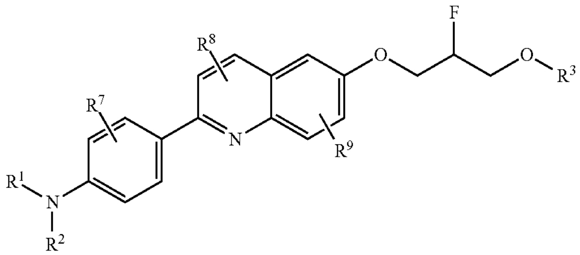

-continued
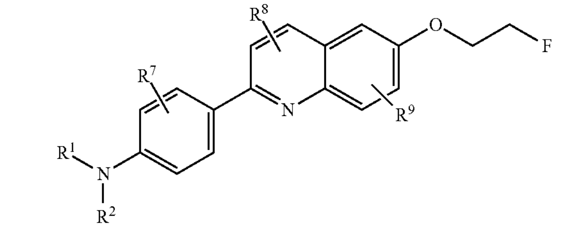
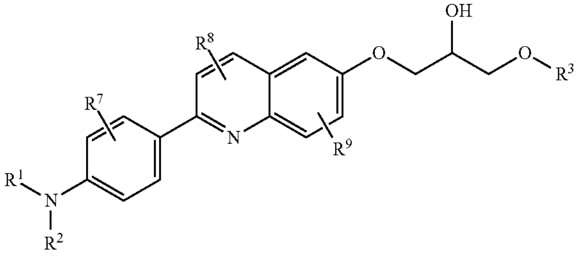
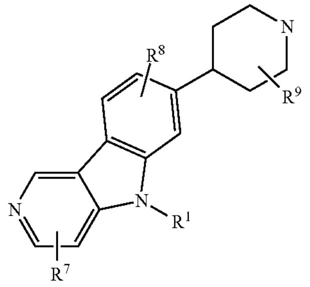
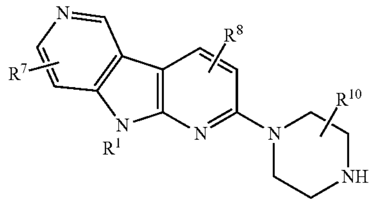
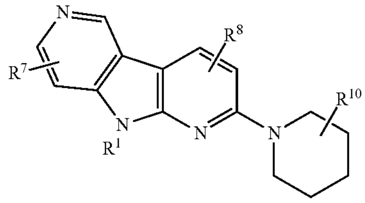
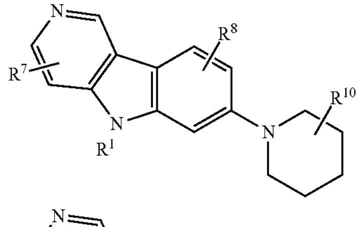
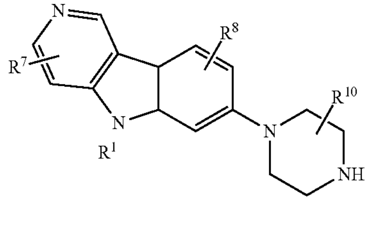
-continued
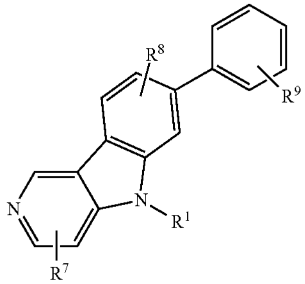
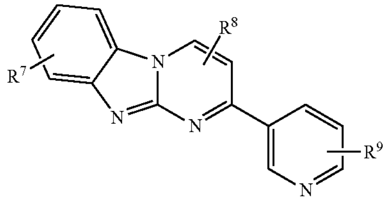
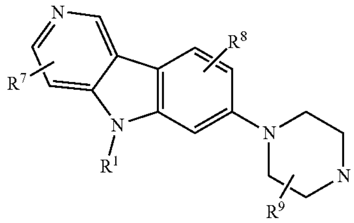
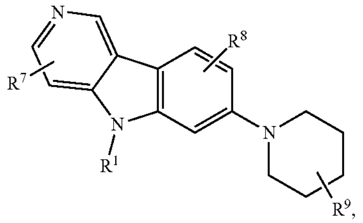
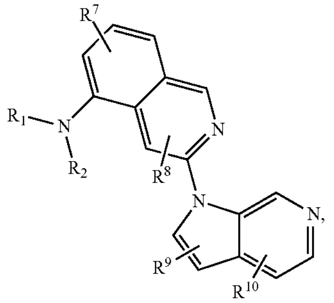
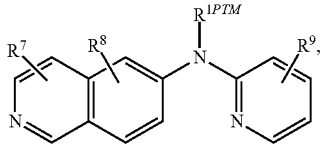
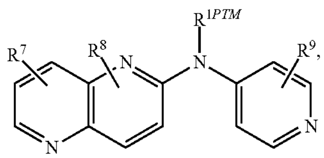

-continued

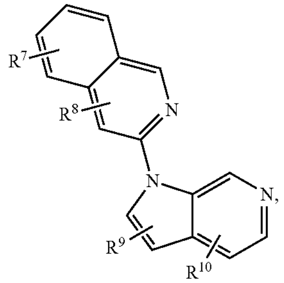
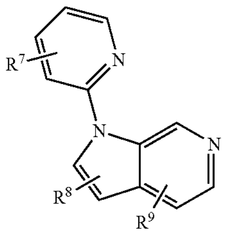
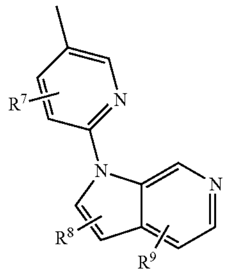
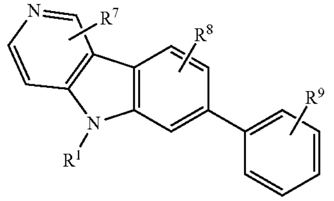
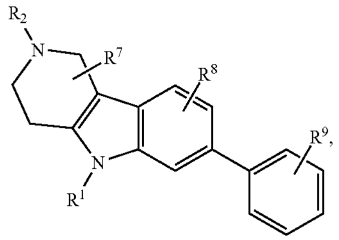
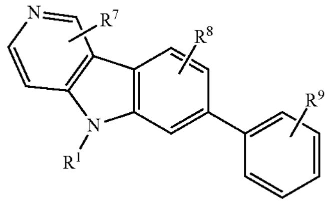
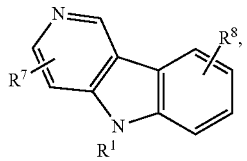
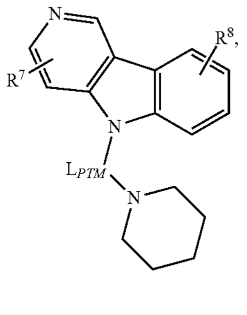
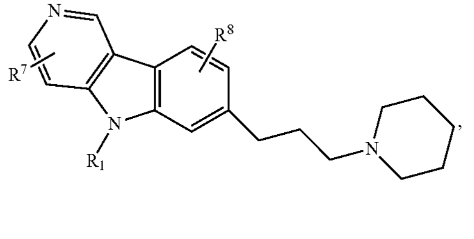

-continued

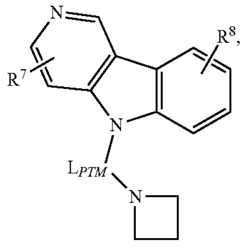

wherein:

$R^1$, $R^2$ and $R^3$ are independently selected from H, optionally substituted alkyl (e.g., a haloalkyl, fluoroalkyl, difluromethyl, or trifluromethyl), methyl, ethyl, 2-fluoroethyl and 2,2,2-trifluoroethyl; and $R^7$, $R^8$, $R^9$ and $R^{10}$ are 1 to 8 substituents independently selected from H, optionally substituted alkyl, haloalkyl, halogen, hydroxyl, alkoxy, amino, dialkylamino, acetylamino, trifluoromethyl or cyano, and wherein the PTM is coupled to a ULM (VLM or CLM) via L.

In any aspect or embodiment described herein, PTM is represented by chemical structure:

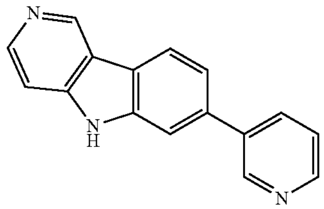
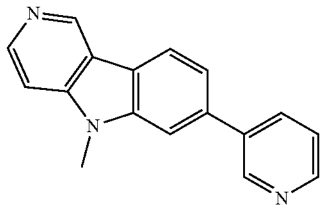
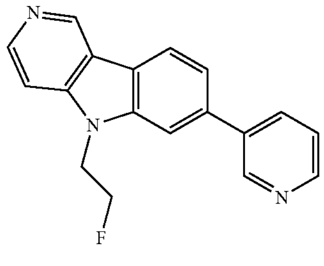
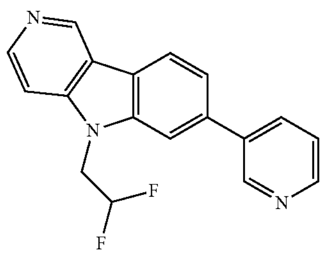

-continued
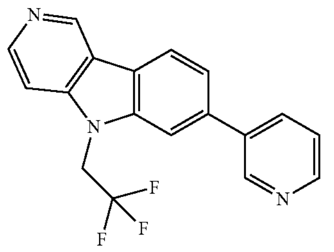
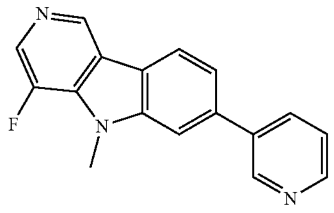
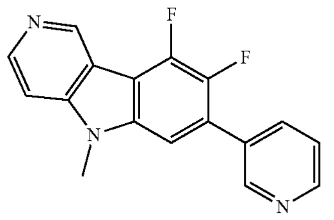
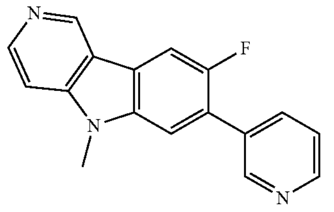
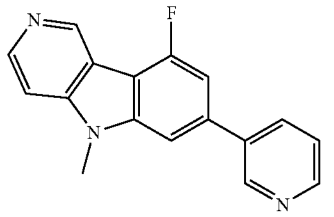
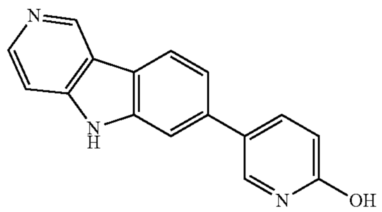
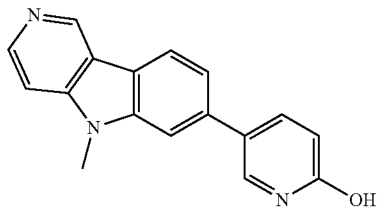
-continued
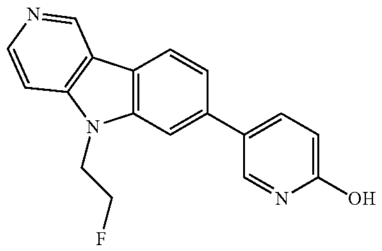
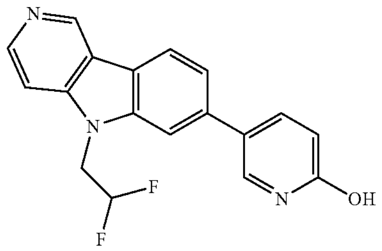
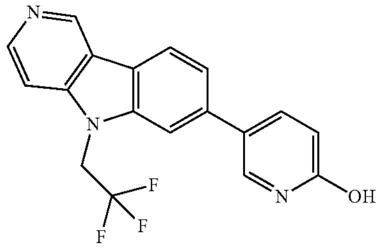
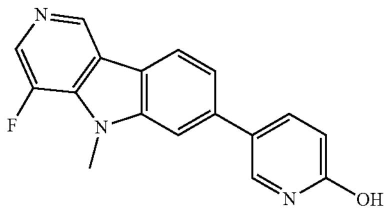
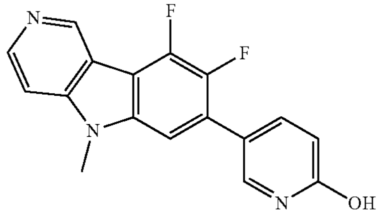
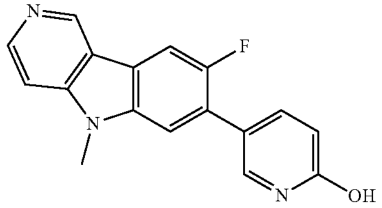
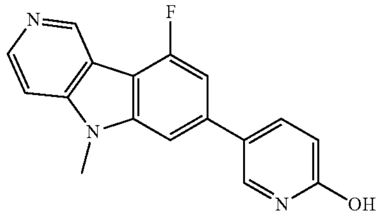

-continued
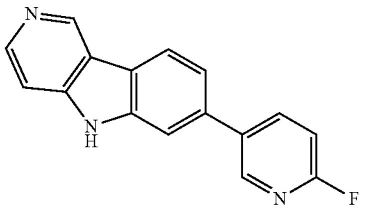
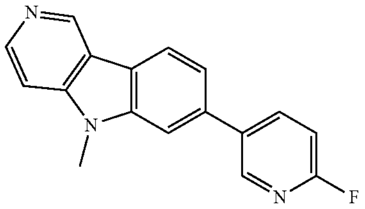
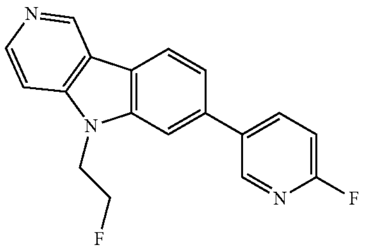
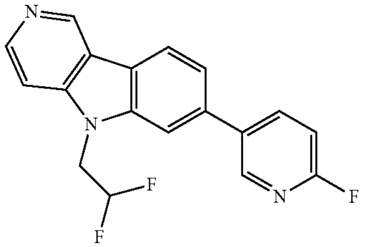
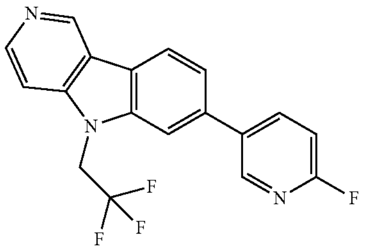
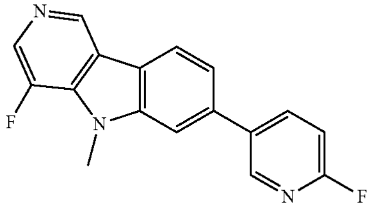
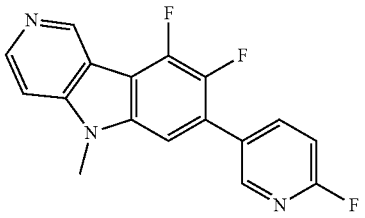
-continued
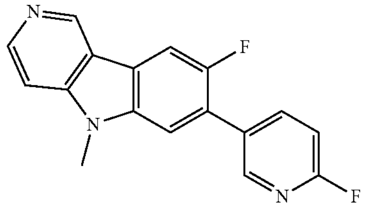
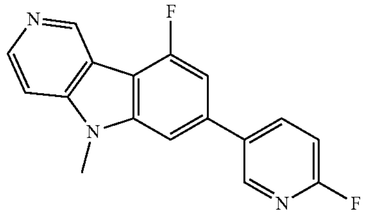
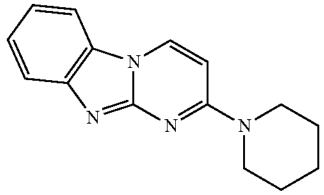
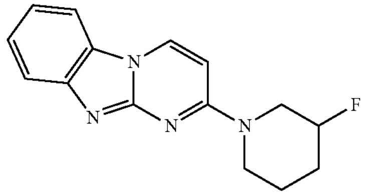
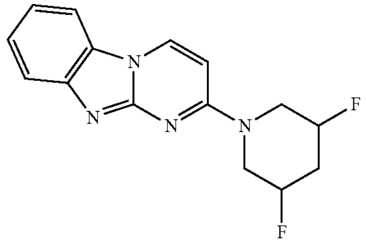
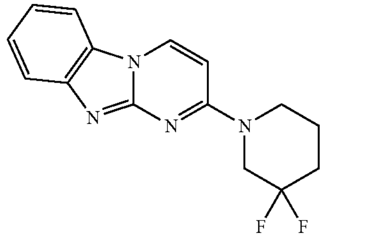
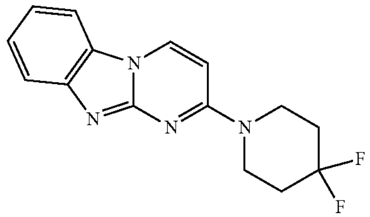

-continued
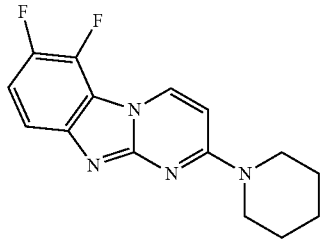
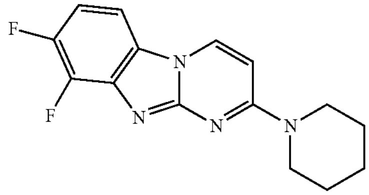
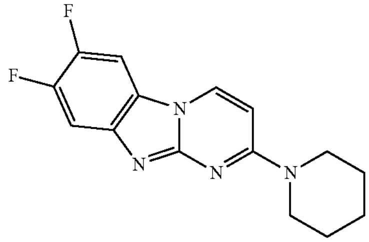
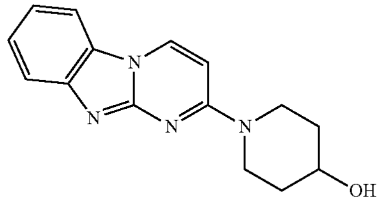
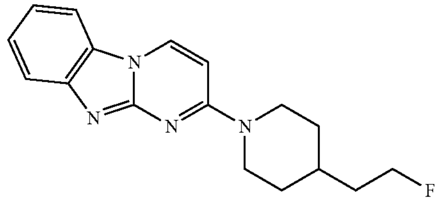
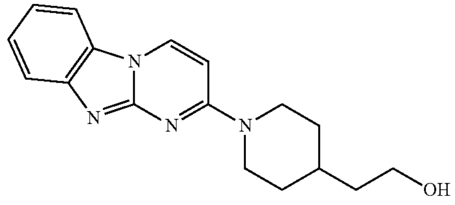
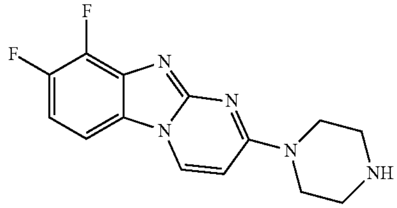
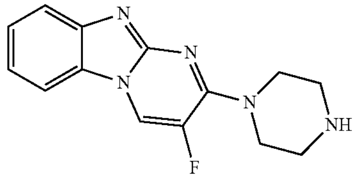
-continued
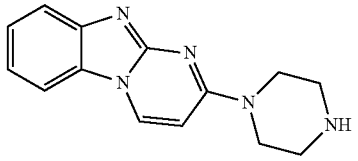
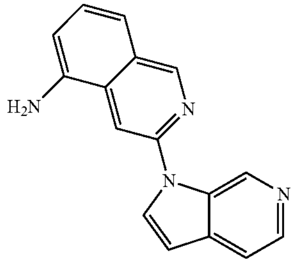
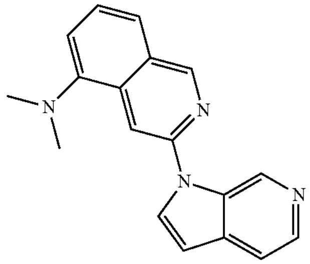
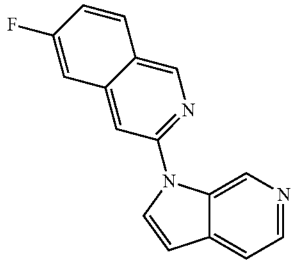
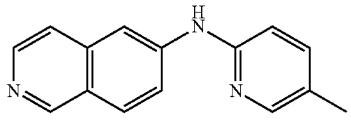
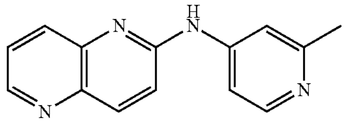
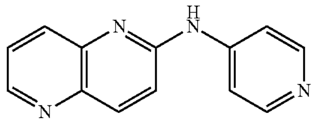
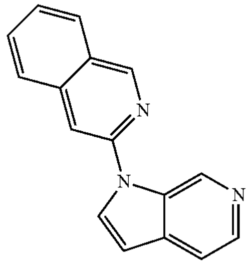

-continued
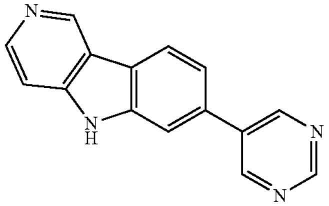
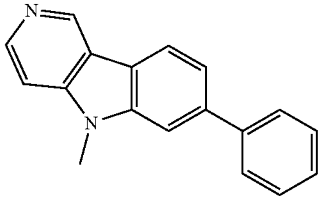
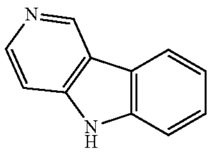
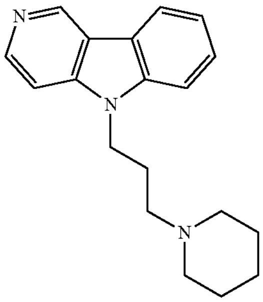
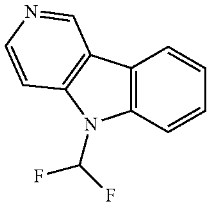
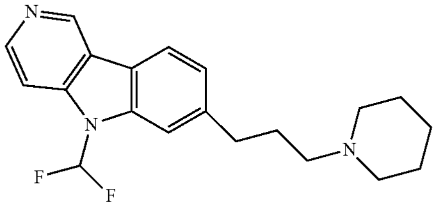
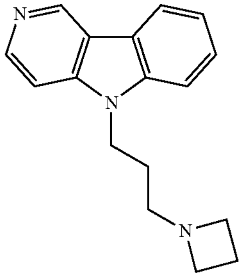
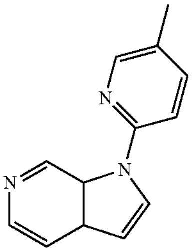
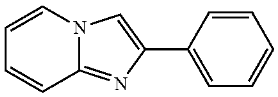
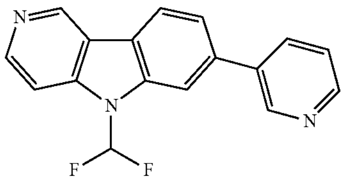
-continued
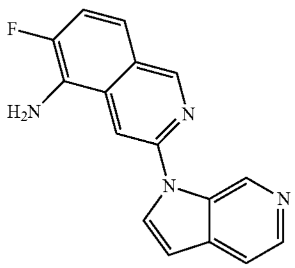
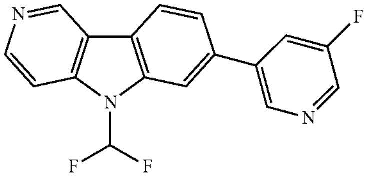
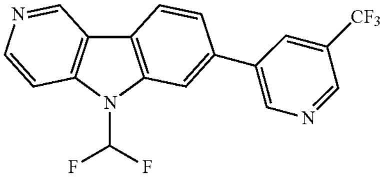
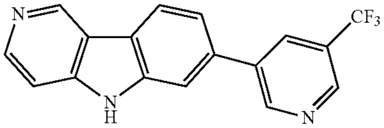
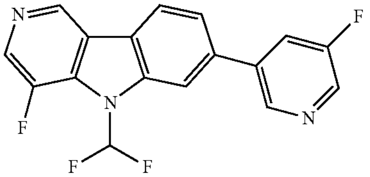
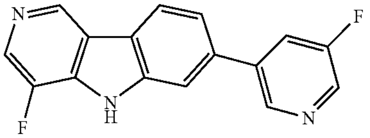
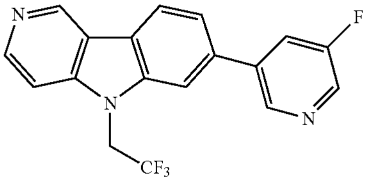
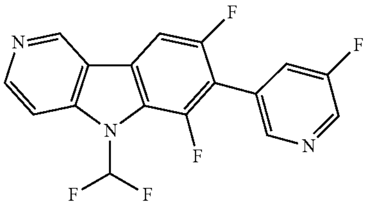
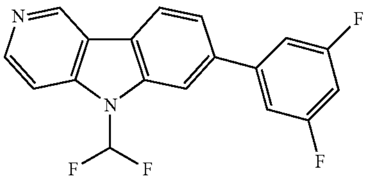

-continued
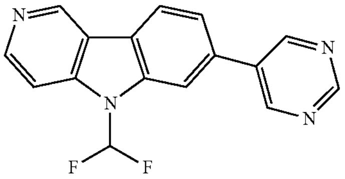
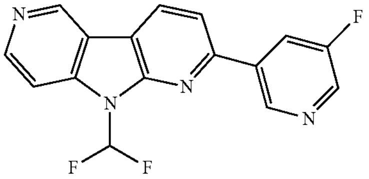
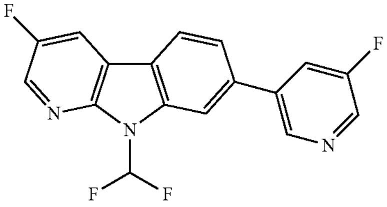
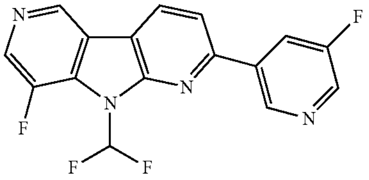
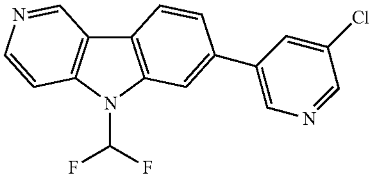
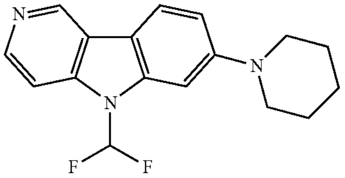
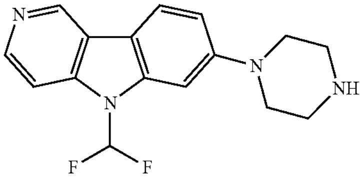
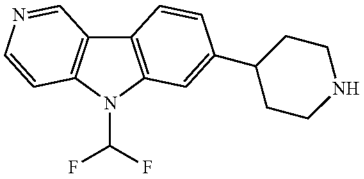
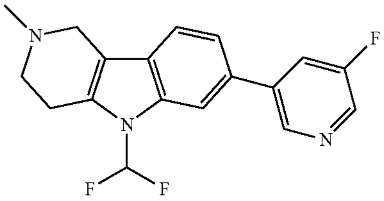
-continued
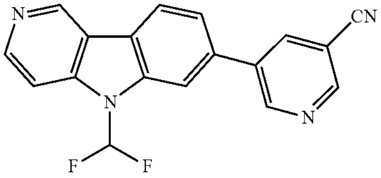
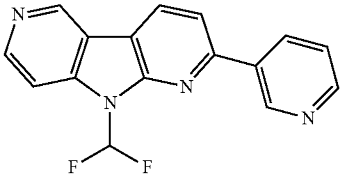
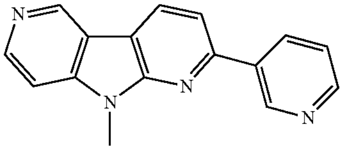
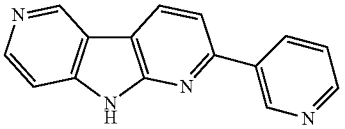
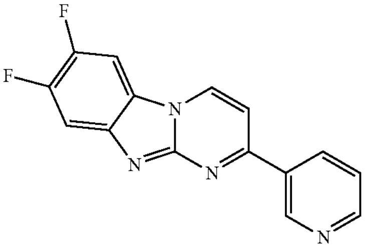
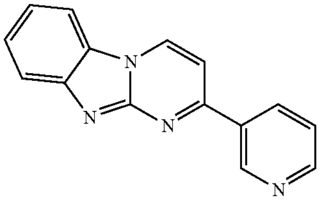
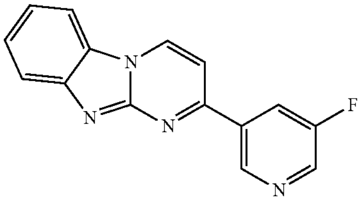
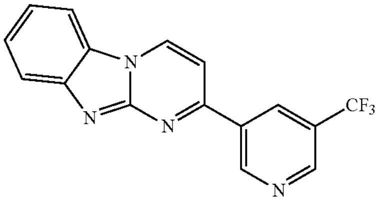
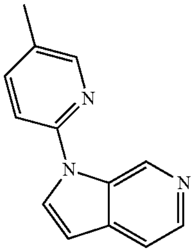
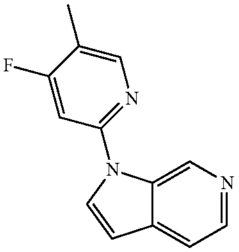

-continued
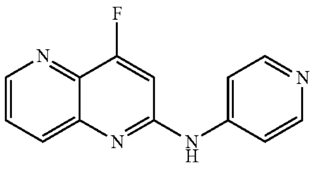
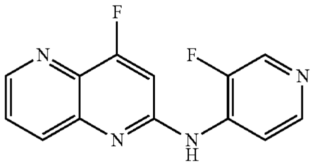
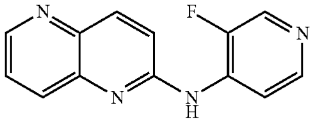
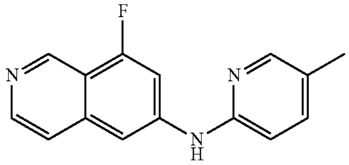
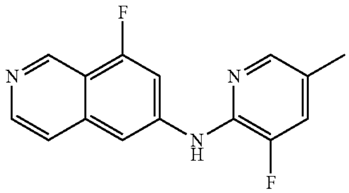
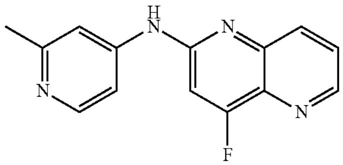
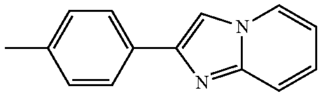
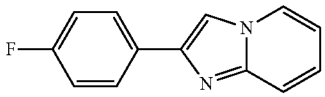
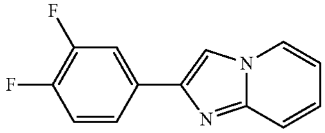
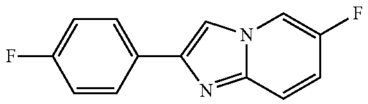
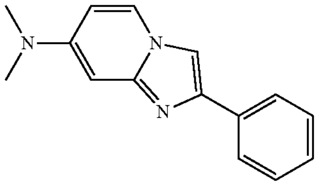
-continued
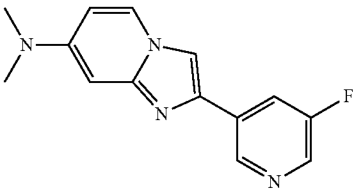
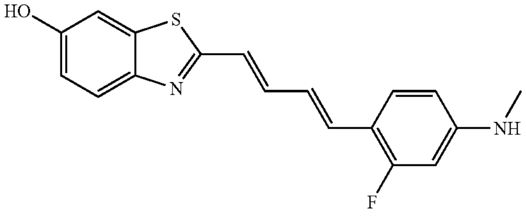
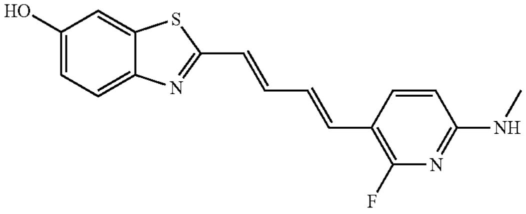
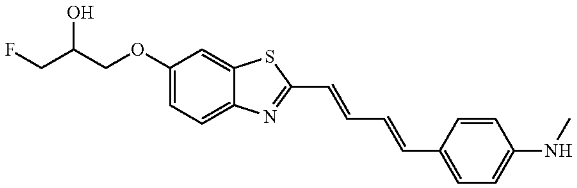
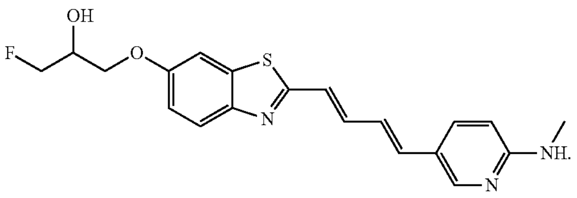
In any aspect or embodiment described herein, the PTM has a chemical structure selected from:
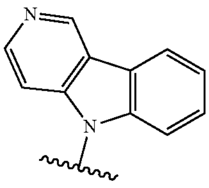
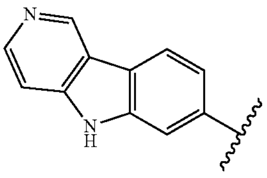
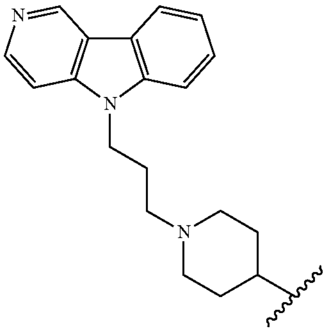

-continued
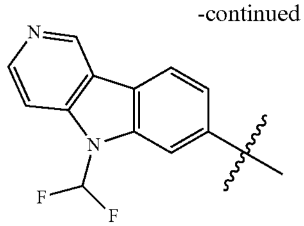
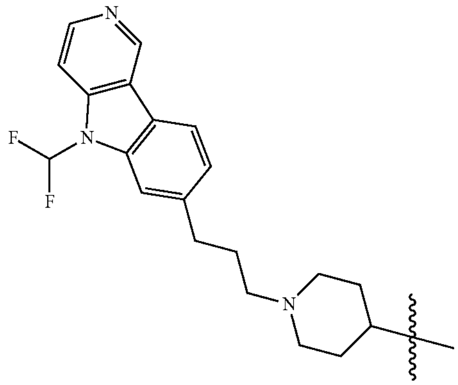
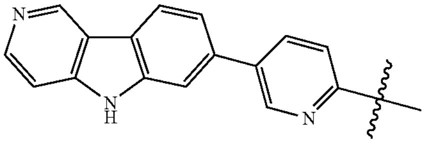
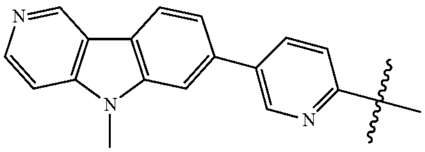
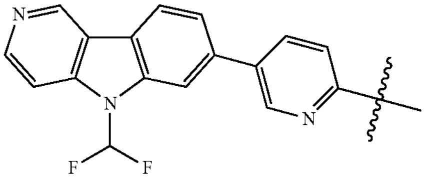
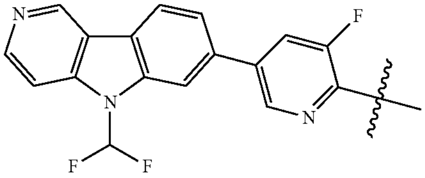
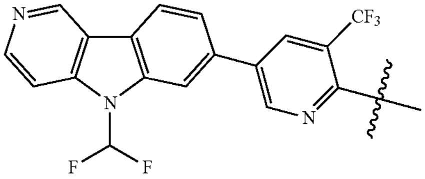
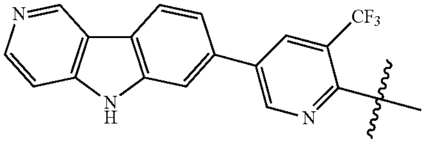
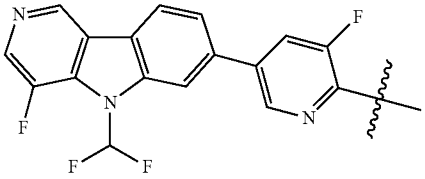
-continued
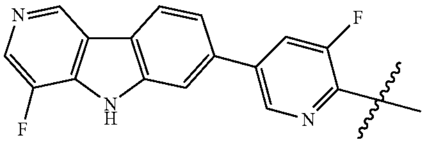
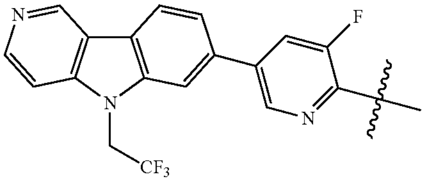
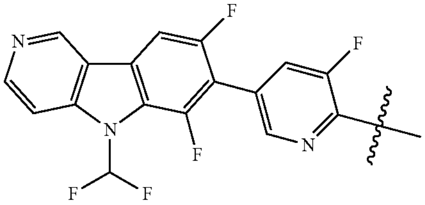
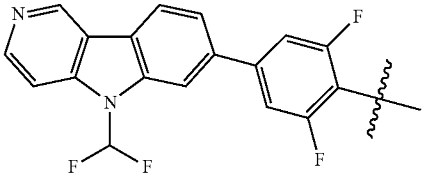
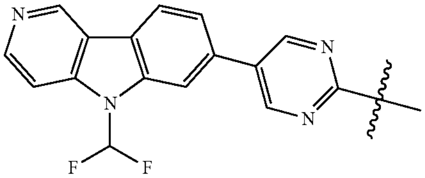
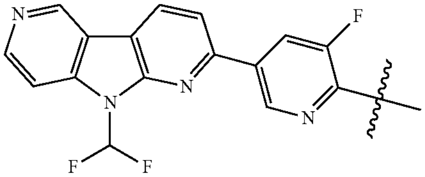
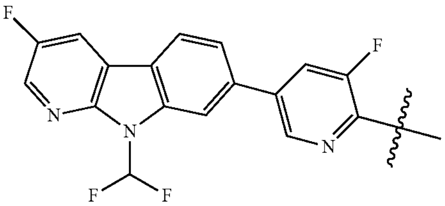
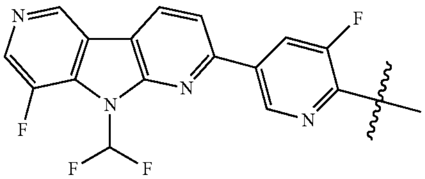
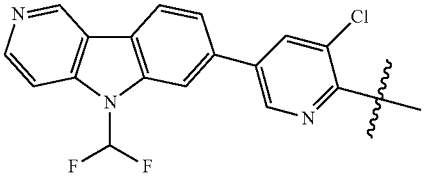

-continued
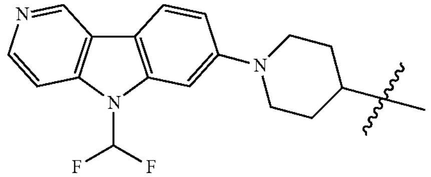
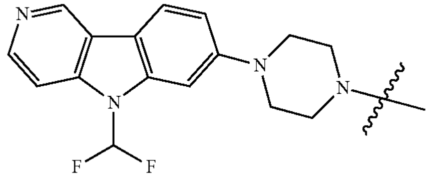
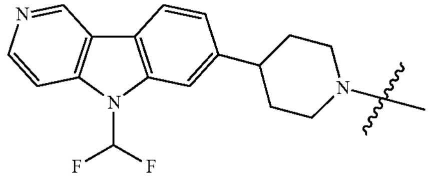
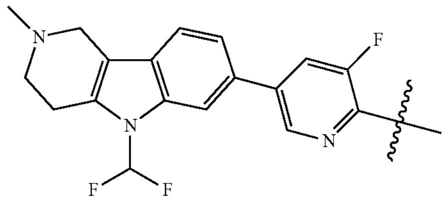
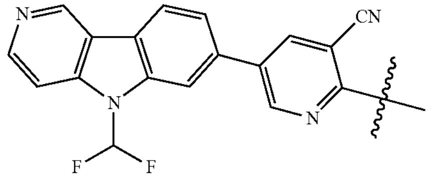
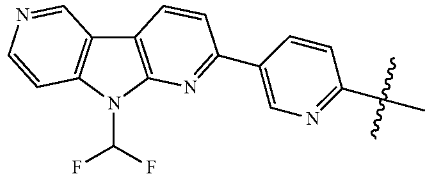
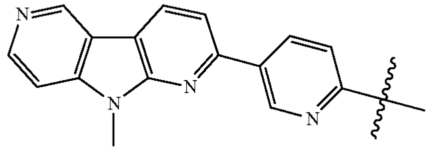
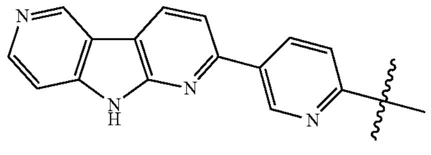
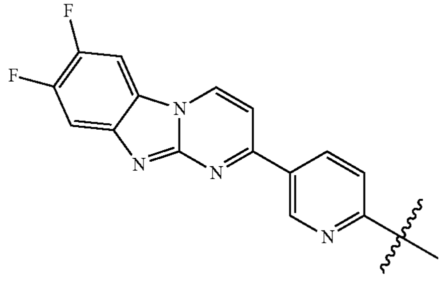
-continued
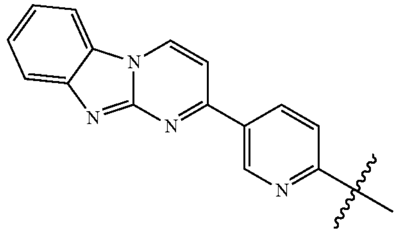
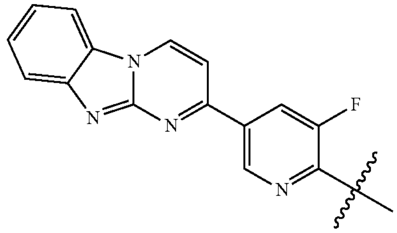
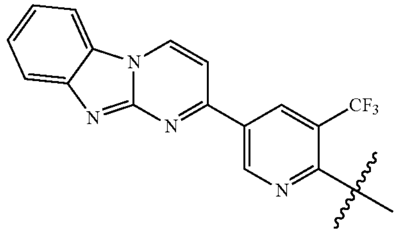
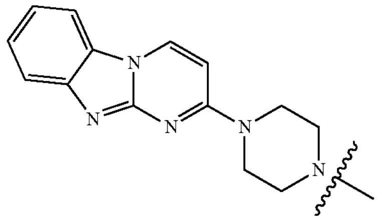
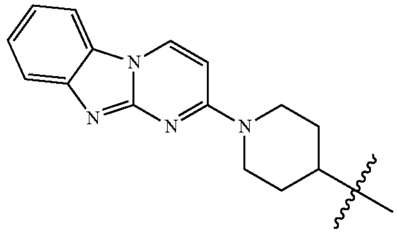
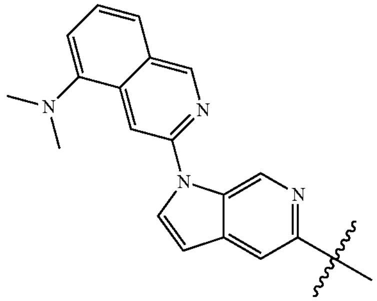

-continued
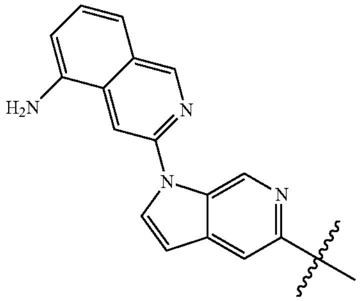
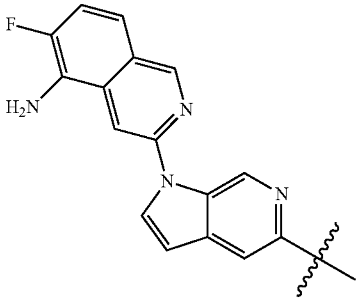
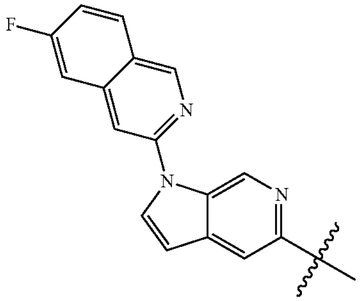
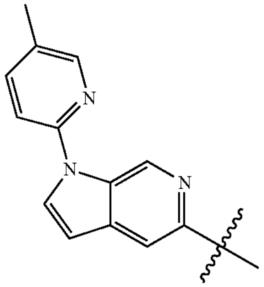
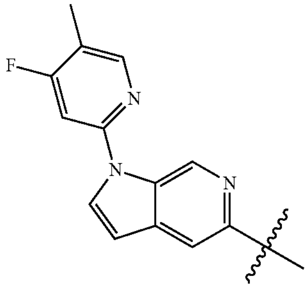
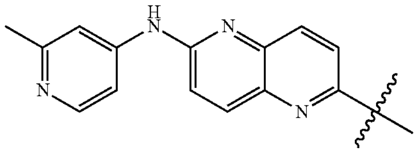
-continued
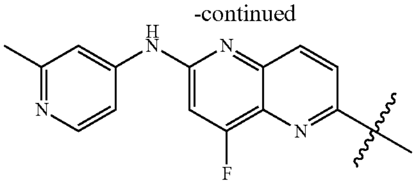
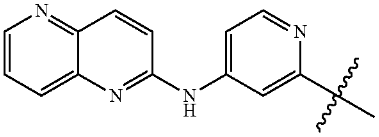
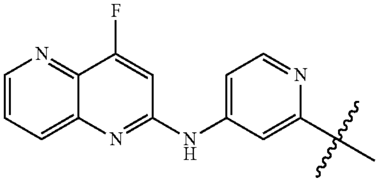
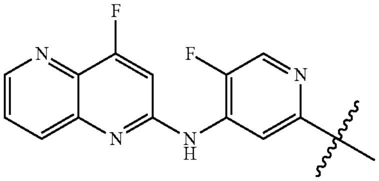
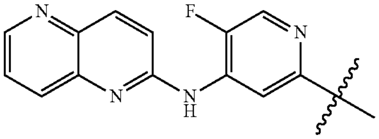
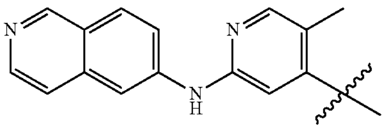
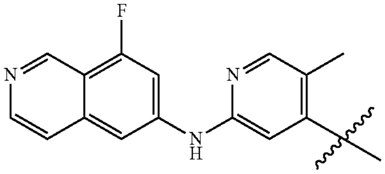
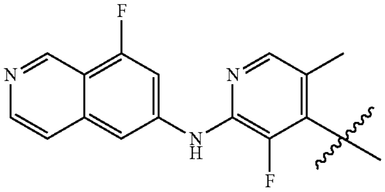
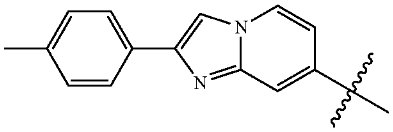
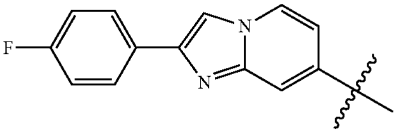
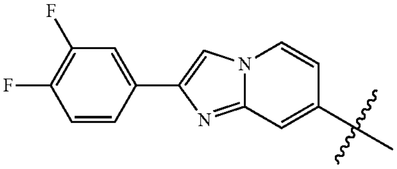

-continued
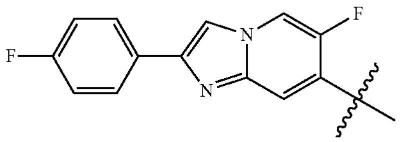
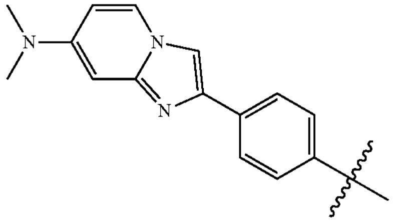
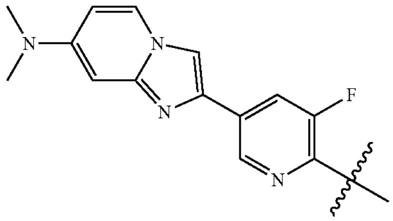
wherein
represents the point of attachment to a linker group or ULM, as described herein.
In any aspect or embodiment described herein, the linker attachment point to the PTM is as indicated by the dotted line:
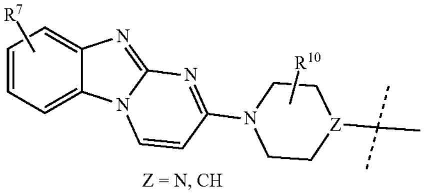
Z = N, CH
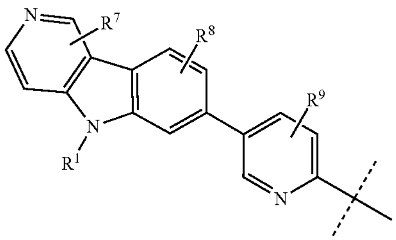
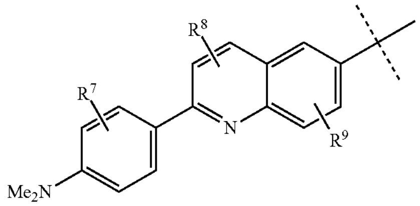
-continued
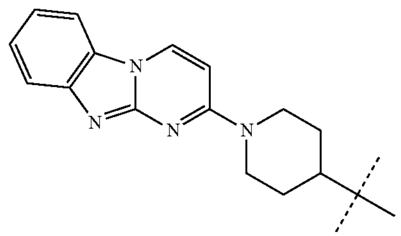
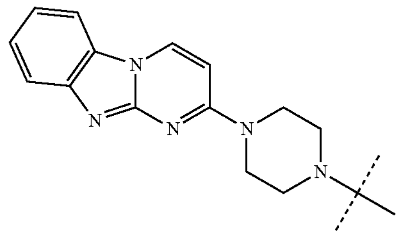
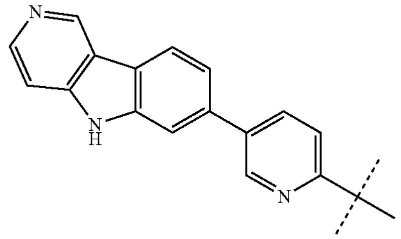
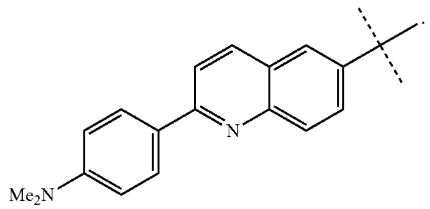
In any aspect or embodiment described herein, the PTM has a chemical structure selected from:
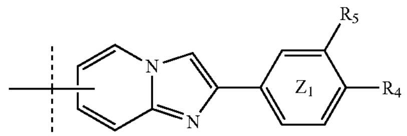
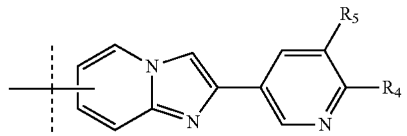
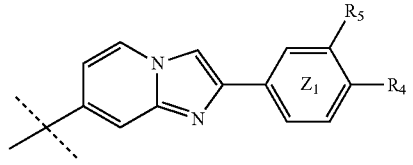
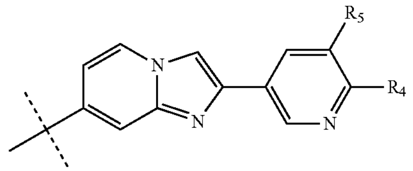

-continued
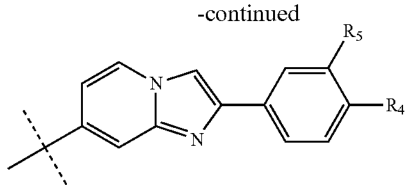
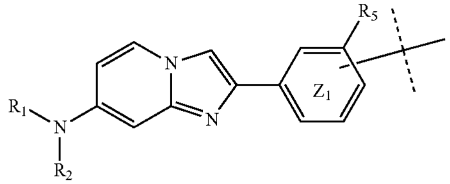
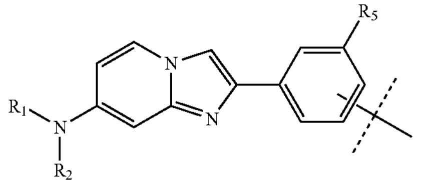
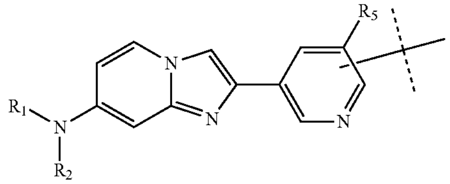
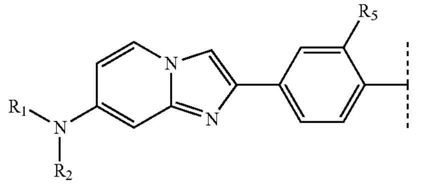
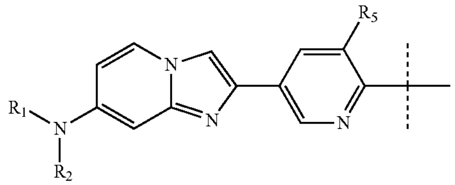
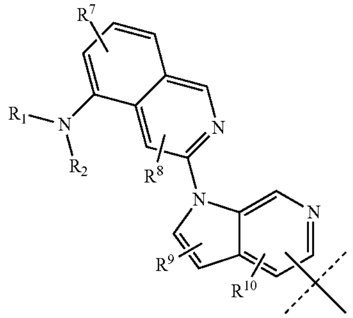
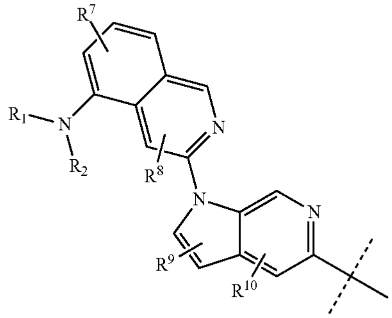
-continued
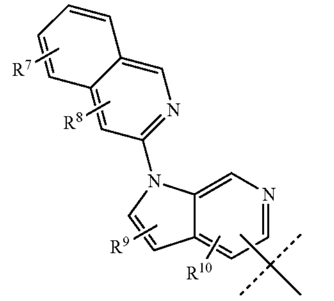
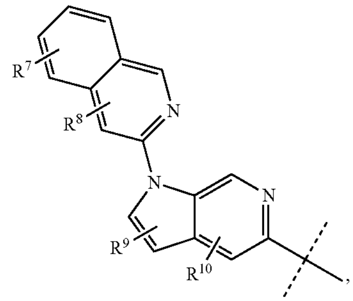
,
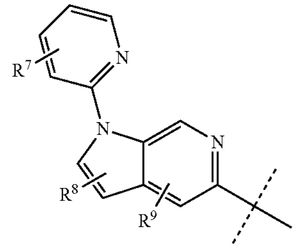
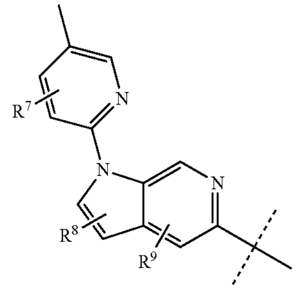
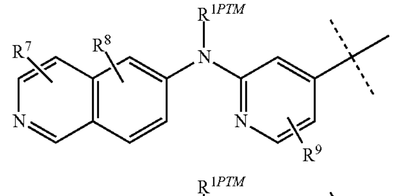
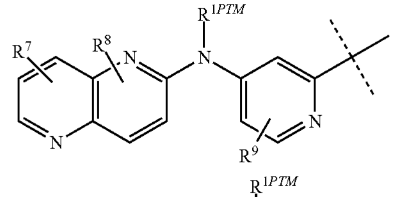
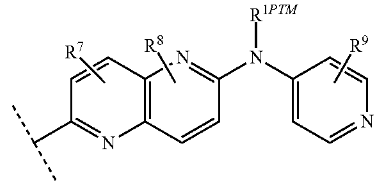

-continued
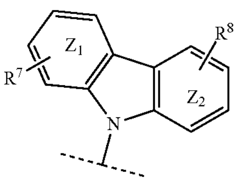
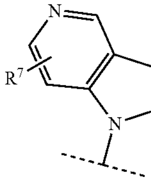
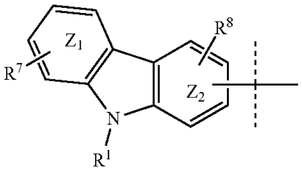
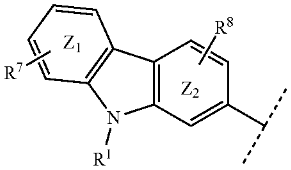
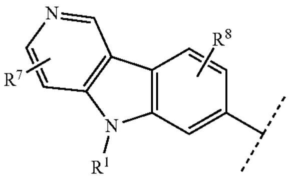
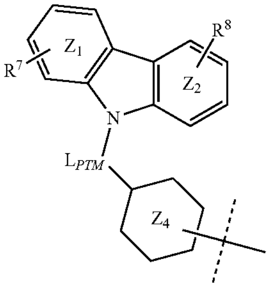
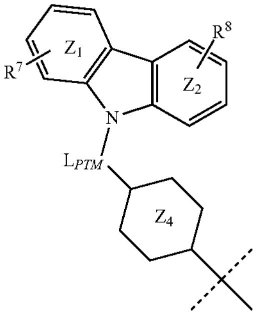
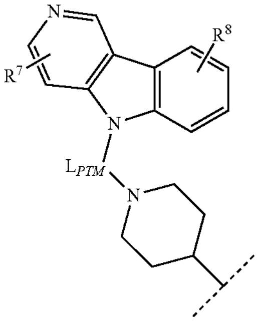
-continued
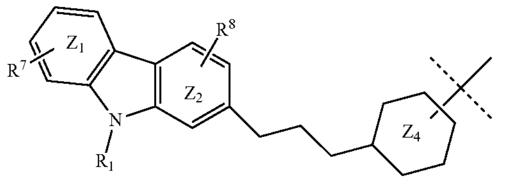
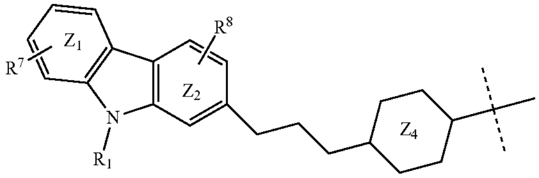
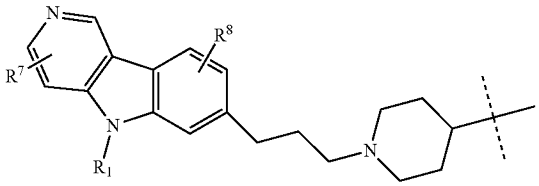
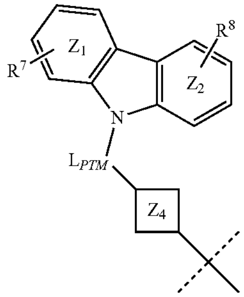
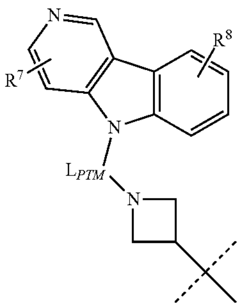
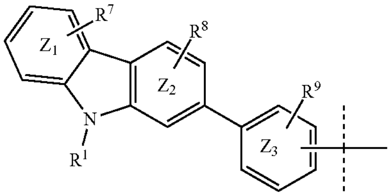
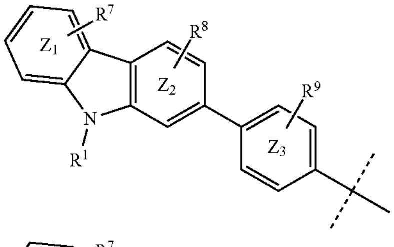
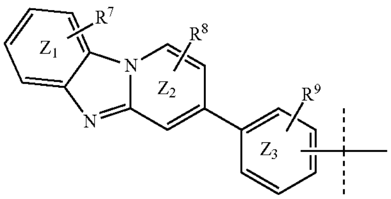
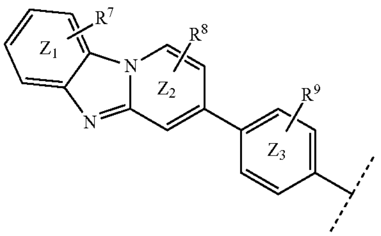

-continued

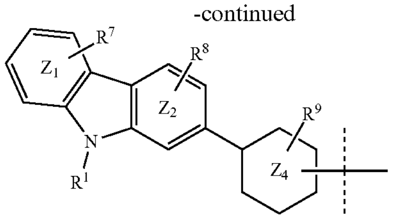

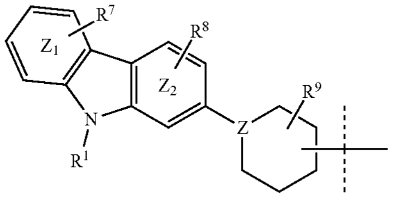

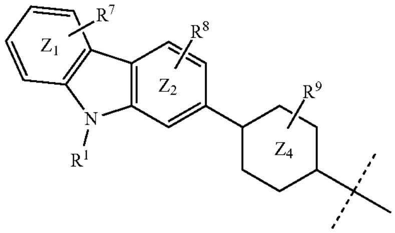

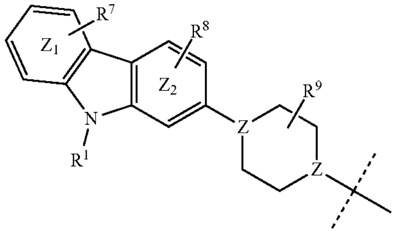

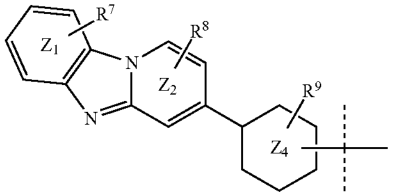

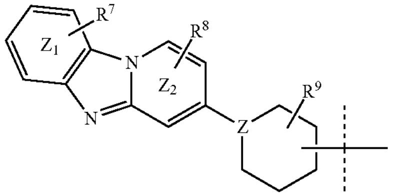

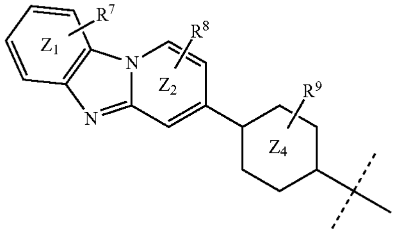

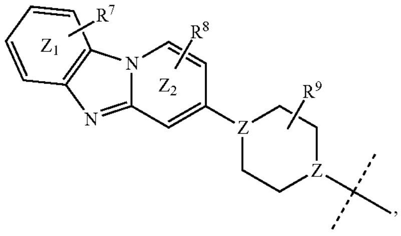

wherein:

each Z is N or CH;

each of rings $Z_1$, $Z_2$, and $Z_3$ is independently an aryl or heteroaryl (e.g., each carbon of rings $Z_1$, $Z_2$, and $Z_3$ is optionally substituted by a heteroatom, such as N, O, or S);

ring $Z_4$ is a cycloalkyl or heterocycloalkyl (e.g., each carbon of ring $Z_4$ is optionally substituted by a heteroatom, such as N, O, or S); and

represents a point of attachment with a linker group or a ULM, as described herein (e.g., CLM, VLM, ILM, or MLM).

In any aspect or embodiment described herein, ring $Z_1$ is a heteroaryl (e.g., ring $Z_1$ has one, two, or three carbons substituted with N, O, or S).

In any aspect or embodiment described herein, ring $Z_2$ is a heteroaryl (e.g., ring $Z_2$ has one, two, or three carbons substituted with N, O, or S).

In any aspect or embodiment described herein, ring $Z_3$ is a heteroaryl (e.g., ring $Z_2$ has one, two, or three carbons substituted with N, O, or S).

In any aspect or embodiment described herein, ring $Z_4$ is a heteroalkyl (e.g., ring $Z_4$ has one, two or three carbons substituted with N, NH, O, or S).

Exemplary VLMs

In one aspect ULM is a VHL E3 ubiquitin ligase binding moiety (VLM).

In any aspect or embodiment described herein, the ULM is a VLM and is represented by the chemical structure:

(VLM-I)

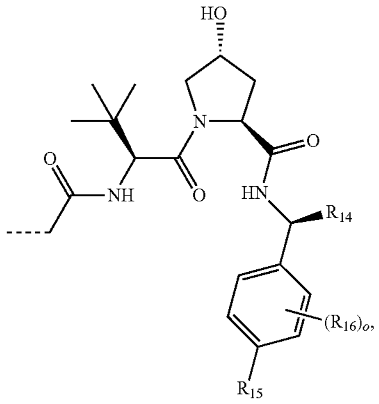

-continued (VLM-II)

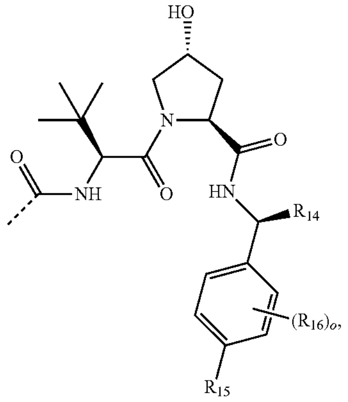

(VLM-III)

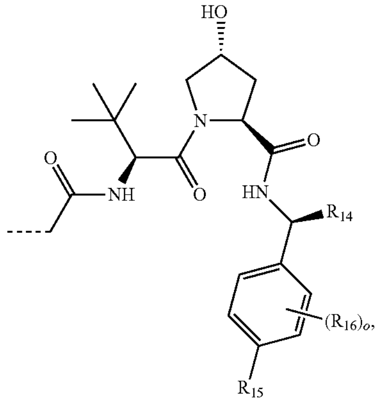

(VLM-IV)

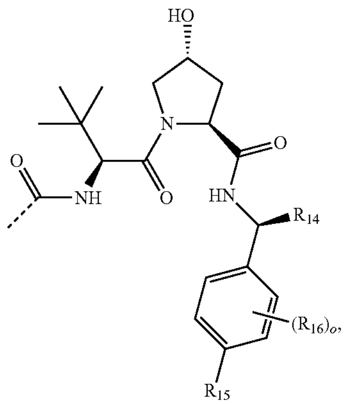

(VLM-V)

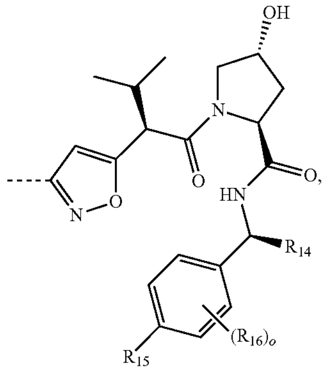

or

-continued (VLM-VI)

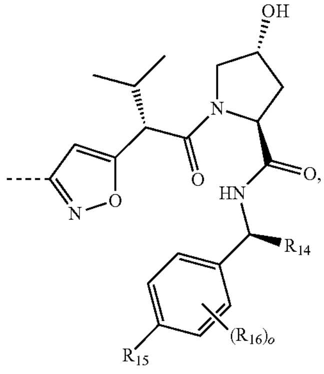

wherein:

$R_{14}$ is as defined in $R_{14}$, $R_{14a}$, or $R_{14b}$ in any aspect or embodiment described herein;

$R_{15}$ is as defined in any aspect or embodiment described herein;

$R_{16}$ is as defined in any aspect or embodiment described herein;

o is as defined in any aspect or embodiment described herein; and the dashed line indicates the site of attachment to a PTM via a chemical linking group (L), or alternatively the site of attachment is at $R_{16}$.

For example, in any aspect or embodiment described herein, the ULM is a VLM and is represented by the chemical structure:

(VLM-I)

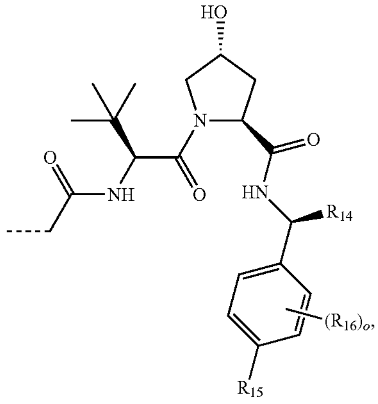

(VLM-II)

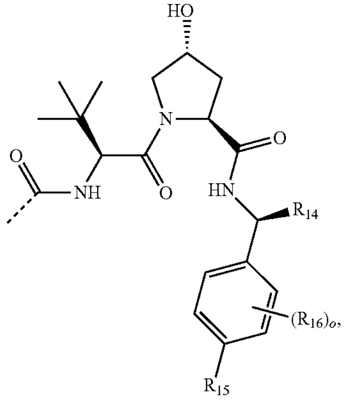

-continued (VLM-III)

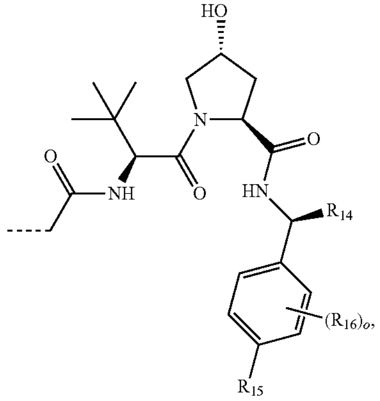

(VLM-IV)

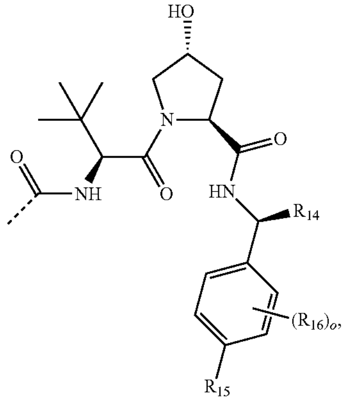

(VLM-V)

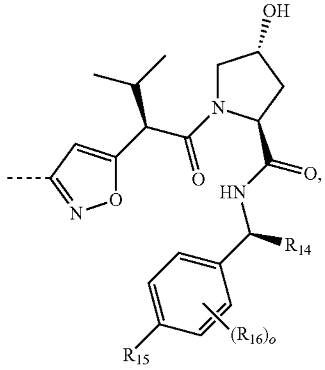

or (VLM-VI)

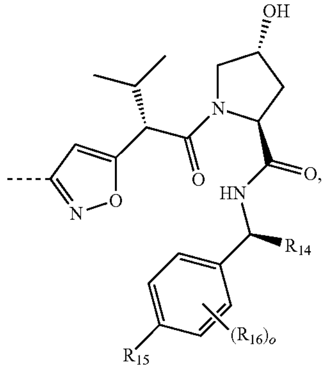

wherein:

$R_{14}$ is H, a linear or branched $C_1$-$C_3$ alkyl (e.g., methyl), $C_{1-3}$ haloalkyl (e.g., fluoromethyl), or hydroxymethyl;

$R_{15}$ is a 5-membered heteroaryl having one or two heteroatoms selected from N, S, and O, optionally substituted with a methyl;

$R_{16}$ is a halo, optionally substituted $C_1$-$C_3$ alkyl, optionally substituted $C_1$-$C_3$ haloalkyl, hydroxy, optionally substituted $C_1$-$C_3$ alkoxy, or optionally substituted $C_1$-$C_3$ haloalkoxy;

is an integer from 0-2 (e.g., 0, 1, or 2); and the dashed line indicates the site of attachment to a PTM via a chemical linking group (L), or alternatively the site of attachment is at $R_{16}$.

In any aspect or embodiment described herein, the VLM is represented by the structure selected from:

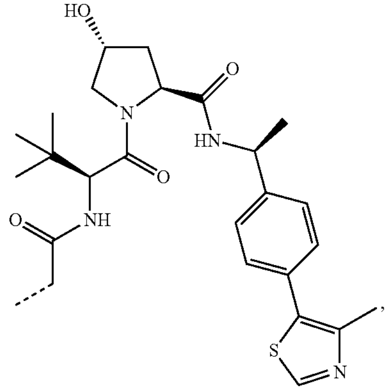

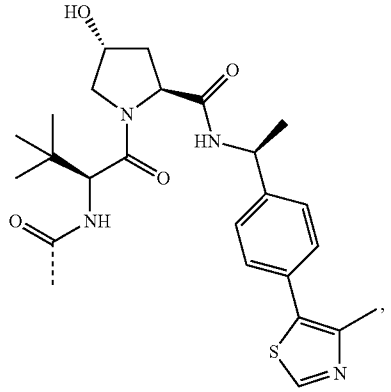

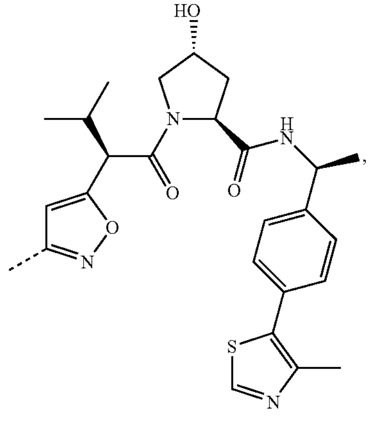

-continued

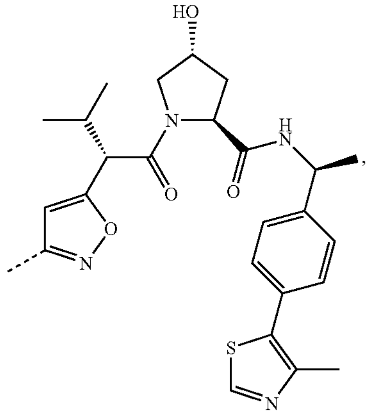

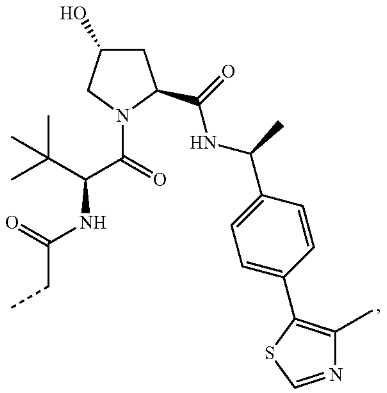

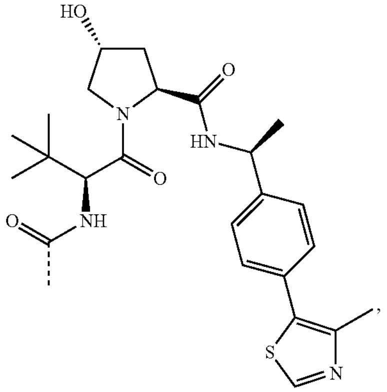

wherein the dashed line indicates the site of attachment to a PTM via a chemical linking group (L).

In any aspect or embodiment described herein, the ULM is a VLM and comprises a chemical structure selected from the group ULM-a:

ULM-a

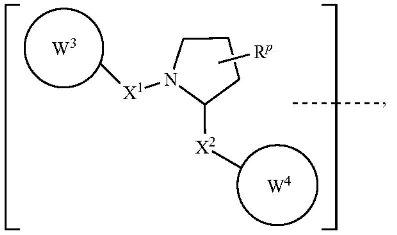

wherein:

where a dashed line indicates the attachment of at least one PTM, another ULM or VLM or CLM or ILM (i.e., ULM' or VLM' or CLM' or ILM'), or a chemical linker moiety coupling at least one PTM, a ULM' or VLM' or CLM' or ILM' to the ULM;

$X^1$ and $X^2$ of Formula ULM-a are each independently selected from the group of a bond, O, $NR^{Y3}$, $CR^{Y3}R^{Y4}$, C═O, C═S, SO, and $SO_2$;

$R^{Y3}$ and $R^{Y4}$ of Formula ULM-a are each independently selected from the group of H, linear or branched $C_{1-6}$ alkyl, optionally substituted by 1 or more halo, optionally substituted $C_{1-6}$ alkoxyl (e.g., optionally substituted by 0-3 $R^P$ groups);

$R^P$ of Formula ULM-a is 0, 1, 2, or 3 groups, each independently selected from the group H, halo, —OH, $C_{1-3}$ alkyl, C═O;

$W^3$ of Formula ULM-a is selected from the group of an optionally substituted T, an optionally substituted -T-N($R^{1a}R^{1b}$)$X^3$, optionally substituted -T-N($R^{1a}R^{1b}$), optionally substituted -T-Aryl, an optionally substituted -T-heteroaryl, an optionally substituted T-biheteroaryl, an optionally substituted -T- heterocycle, an optionally substituted -T-biheterocycle, an optionally substituted —$NR^1$-T-Aryl, an optionally substituted —$NR^1$-T-heteroaryl or an optionally substituted —$NR^1$-T-heterocycle;

$X^3$ of Formula ULM-a is C═O, $R^1$, $R^{1a}$, $R^{1b}$;

each $R^1$, $R^{1a}$, and $R^{1b}$ of Formula ULM-a is independently selected from the group consisting of H, linear or branched $C_1$-$C_6$ alkyl group optionally substituted by 1 or more halo or —OH groups, $R^{Y3}$C═O, $R^{Y3}$C═S, $R^{Y3}$SO, $R^{Y3}SO_2$, N($R^{Y3}R^{Y4}$)C═O, N($R^{Y3}R^{Y4}$)C═S, N($R^{Y3}R^{Y4}$)SO, and N($R^{Y3}R^{Y4}$)$SO_2$;

T of Formula ULM-a is selected from the group of an optionally substituted alkyl, —$(CH_2)_n$— group, —$(CH_2)_n$—O—$C_{1-6}$ alkyl that is linear or branched, or —$(CH_2)_n$—O-heterocyclyl that is optionally substituted, wherein each methylene groups is optionally substituted with one or two substituents selected from the group of halogen, methyl, optionally substituted alkoxy, a linear or branched $C_1$-$C_6$ alkyl group optionally substituted by 1 or more halogen, C(O) $NR^1R^{1a}$, or $NR^1R^{1a}$ or $R^1$ and $R^{1a}$ are joined to form an optionally substituted heterocyclyl, or —OH groups or an amino acid side chain optionally substituted;

$W^4$ of Formula ULM-a is an optionally substituted —$NR_1$-T-Aryl wherein the aryl group may be optionally substituted with an optionally substituted 5-6 membered heteroaryl, an optionally substituted —NR I-T-Heteroaryl group or an optionally substituted —$NR_1$-T-heterocycle, where —$NR_1$ is covalently bonded to $X^2$ and $R_1$ is H or $CH_3$, preferably H; and n of Formula ULM-a is 0 to 6, often 0, 1, 2, or 3, preferably 0 or 1.

In any aspect or embodiment described herein, T is selected from the group of an optionally substituted alkyl, —$(CH_2)_n$— group, wherein each one of the methylene groups is optionally substituted with one or two substituents selected from the group of halogen, methyl, optionally substituted alkoxy, a linear or branched $C_1$-$C_6$ alkyl group optionally substituted by 1 or more halogen, C(O) $NR^1R^{1a}$, or $NR^1R^{1a}$ or $R^1$ and $R^{1a}$ are joined to form an optionally substituted heterocycle, or —OH groups or an amino acid side chain optionally substituted; and n is 0 to 6, often 0, 1, 2, or 3, preferably 0 or 1.

In any aspect or embodiment described herein, $W^4$ of Formula ULM-a is

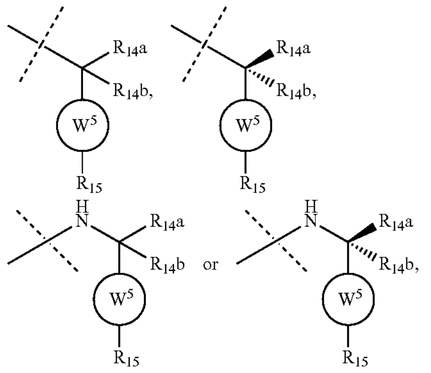

or wherein:

$W^5$ is optionally substituted (e.g., $W^5$ is an optionally substituted phenyl, an optionally substituted napthyl, or an optionally substituted 5-10 membered heteroaryl) (e.g., $W^5$ is optionally substituted with one or more [such as 1, 2, 3, 4, or 5] halo, CN, optionally substituted alkyl, optionally substituted haloalkyl, optionally substituted alkoxy, hydroxy, or optionally substituted haloalkoxy);

$R_{14a}$ and $R_{14b}$ are each independently selected from the group of H, haloalkyl (e.g., fluoroalkyl), optionally substituted alkyl, optionally substituted alkoxy, optionally substituted hydroxyl alkyl, optionally substituted alkylamine, optionally substituted heteroalkyl, optionally substituted alkyl-heterocycloalkyl, optionally substituted alkoxy-heterocycloalkyl, $COR_{26}$, $CONR_{27a}R_{27b}$, $NHCOR_{26}$, or $NHCH_3COR_{26}$; and the other of $R_{14a}$ and $R_{14b}$ is H; or $R_{14a}$, $R_{14b}$, together with the carbon atom to which they are attached, form an optionally substituted 3 to 5 membered cycloalkyl, heterocycloalkyl, spirocycloalkyl or spiroheterocyclyl, wherein the spiroheterocyclyl is not epoxide or aziridine;

is an integer from 0-4 (e.g., 0, 1, 2, 3, or 4); and $R_{16}$ is independently selected from the group of halo, optionally substituted alkyl, optionally substituted haloalkyl, hydroxy, or optionally substituted haloalkoxy;

In any aspect or embodiment described herein, $W^5$ is selected from an optionally substituted phenyl, an optionally substituted napthyl, or an optionally substituted 5-10 membered heteroaryl (e.g., $W^5$ is optionally substituted with one or more [such as 1, 2, 3, 4, or 5] halo, CN, optionally substituted alkyl, optionally substituted haloalkyl, optionally substituted alkoxy, hydroxy, or optionally substituted haloalkoxy); and $R_{15}$ is selected from the group of H, halogen, CN, OH, $NO_2$, $NR_{14a}R_{14b}$, $OR_{14a}$, $CONR_{14a}R_{14b}$, $NR_{14a}COR_{14b}$, $SO_2NR_{14a}R_{14b}$, $NR_{14a}$ $SO_2R_{14b}$, optionally substituted alkyl, optionally substituted haloalkyl, optionally substituted haloalkoxy, optionally substituted aryl, optionally substituted heteroaryl, optionally substituted cycloalkyl, or optionally substituted cycloheteroalkyl.

In any aspect or embodiment described herein, $W^4$ of Formula ULM-a substituents for use in the present disclosure also include specifically (and without limitation to the specific compound disclosed) the $W^4$ substituents which are found in the identified compounds disclosed herein. Each of these $W^4$ substituents may be used in conjunction with any number of $W^3$ substituents which are also disclosed herein.

In any aspect or embodiment described herein, ULM-a, is optionally substituted by 1-3 $R^P$ groups in the pyrrolidine moiety, each $R^P$ is independently H, halo, —OH, $C_{1-3}$alkyl, or C═O.

In any aspect or embodiment described herein, the $W^3$ and the $W^4$ can independently be covalently coupled to a chemical linking group which is attached one or more PTM groups.

In any aspect or embodiment described herein, the ULM is a VLM and is represented by the structure:

(ULM-b)

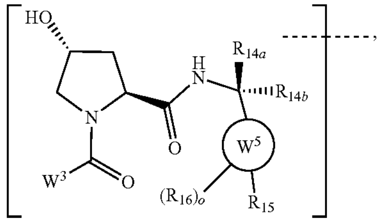

wherein:

$W^3$ of Formula ULM-b is selected from the group of an optionally substituted aryl, optionally substituted heteroaryl, or

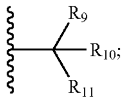

$R_9$ and $R_{10}$ of Formula ULM-b are independently hydrogen, optionally substituted alkyl, optionally substituted cycloalkyl, optionally substituted hydroxyalkyl, optionally substituted heteroaryl, or haloalkyl, or $R_9$, $R_{10}$, and the carbon atom to which they are attached form an optionally substituted cycloalkyl;

$R_{11}$ of Formula ULM-b is selected from the group of an optionally substituted heterocyclyl, optionally substituted alkoxy, optionally substituted heteroaryl, optionally substituted aryl,

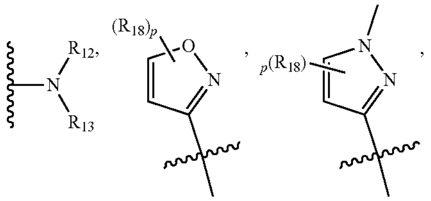

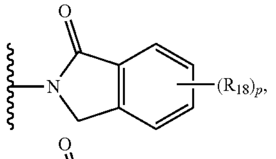

or

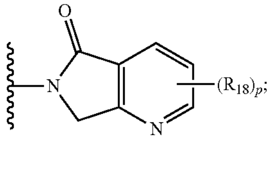

$R_{12}$ of Formula ULM-b is selected from the group of H or optionally substituted alkyl;

$R_{13}$ of Formula ULM-b is selected from the group of H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;

$R_{14a}$ and $R_{14b}$ of Formula ULM-b are each independently selected from the group of H, haloalkyl (e.g., fluoroalkyl), optionally substituted alkyl, optionally substitute alkoxy, aminomethyl, alkylaminomethyl, alkoxymethyl, optionally substituted hydroxyl alkyl, optionally substituted alkylamine, optionally substituted heterolkyl, optionally substituted alkyl-heterocycloalkyl, optionally substituted alkoxy-heterocycloalkyl, $CONR_{27a}R_{27b}$, $CH_2NHCOR_{26}$, or $(CH_2)N(CH_3)COR_{26}$; and the other of $R_{14a}$ and $R_{14b}$ is H; or $R_{14a}$, $R_{14b}$, together with the carbon atom to which they are attached, form an optionally substituted 3 to 6 membered cycloalkyl, heterocycloalky, spirocycloalkyl or spiroheterocyclyl, wherein the spiroheterocyclyl is not epoxide or aziridine;

$W^5$ of Formula ULM-b is selected from the group of an optionally substituted phenyl or an optionally substituted 5-10 membered heteroaryl (e.g., $W^5$ is optionally substituted with one or more [such as 1, 2, 3, 4, or 5] halo, CN, optionally substituted alkyl, optionally substituted haloalkyl, optionally substituted alkoxy, hydroxy, or optionally substituted haloalkoxy);

$R_{15}$ of Formula ULM-b is selected from the group of H, halogen, CN, OH, $NO_2$, $NR_{14a}R_{14b}$, $OR_{14a}$, $CONR_{14a}R_{14b}$, $NR_{14a}COR_{14b}$, $SO_2NR_{14a}R_{14b}$, $NR_{14a}SO_2R_{14b}$, optionally substituted alkyl, optionally substituted haloalkyl, optionally substituted haloalkoxy; optionally substituted aryl; optionally substituted heteroaryl; optionally substituted cycloalkyl; or optionally substituted cycloheteroalkyl;

each $R_{16}$ of Formula ULM-b is independently selected from the group of H, CN, halo, optionally substituted alkyl, optionally substituted haloalkyl, hydroxy, or optionally substituted haloalkoxy;

o of Formula ULM-b is 0, 1, 2, 3, or 4;

$R_{18}$ of Formula ULM-b is independently selected from the group of halo, optionally substituted alkoxy, cyano, optionally substituted alkyl, haloalkyl, haloalkoxy or a linker; and p of Formula ULM-b is 0, 1, 2, 3, or 4; and the dashed line indicates the site of attachment of at least one PTM, another ULM (ULM') or a chemical linker moiety coupling at least one PTM or a ULM' or both to ULM.

In any aspect or embodiment described herein, $R_{15}$ is selected from the group of H, halogen, CN, OH, $NO_2$, $NR_{27a}R_{27b}$, $OR_{27a}$, $CONR_{27a}R_{27b}$, $NR_{27a}COR_{27b}$, $SO_2NR_{27a}R_{27b}$, $NR_{27a}SO_2R_{27b}$, optionally substituted alkyl, optionally substituted haloalkyl, optionally substituted haloalkoxy, optionally substituted aryl, optionally substituted heteroaryl, optionally substituted cycloalkyl, or optionally substituted heterocyclyl, wherein each $R_{26}$ is independently selected from H, optionally substituted alkyl or $NR_{27a}R_{27b}$; and each $R_{27a}$ and $R_{27b}$ is independently H, optionally substituted alkyl, or $R_{27a}$ and $R_{27b}$ together with the nitrogen atom to which they are attached form a 4-6 membered heterocyclyl.

In any aspect or embodiment described herein, $R_{15}$ is

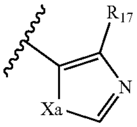

wherein:

$R_{17}$ is H, halo, optionally substituted $C_{3-6}$cycloalkyl, optionally substituted $C_{1-6}$alkyl, optionally substituted $C_{1-6}$alkenyl, and $C_{1-6}$haloalkyl; and Xa is S or O.

In any aspect or embodiment described herein, $R_{17}$ is selected from the group methyl, ethyl, isopropyl, and cyclopropyl.

In any aspect or embodiment described herein, $R_{15}$ is selected from the group consisting of:

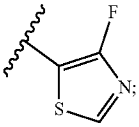 ; 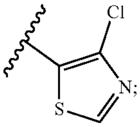 ; 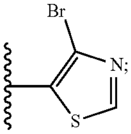 ;

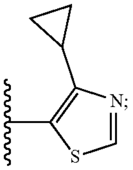 ; 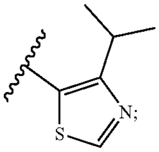 ; 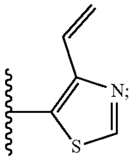 ;

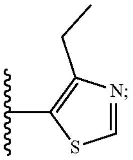 ; 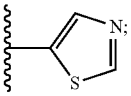 ; 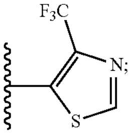 ;

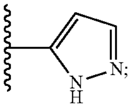 ; 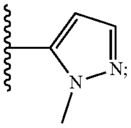 ; 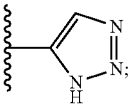 ;

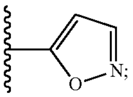 ; 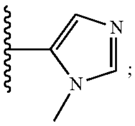 ; 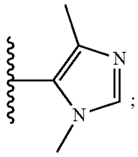 ;

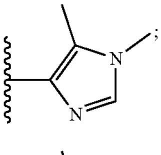 ; 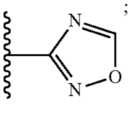 ; 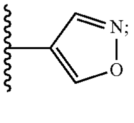 ;

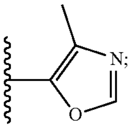 ; 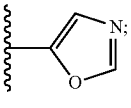 ; 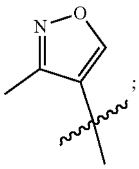 ;

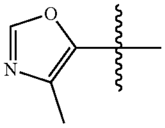 ; 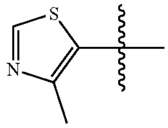 ;

-continued

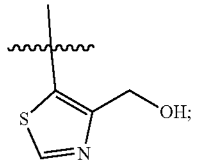

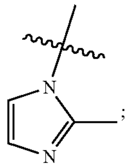

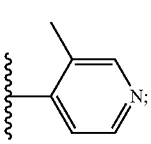

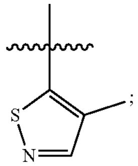

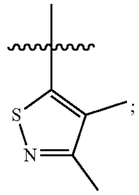

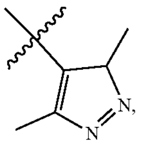

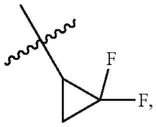

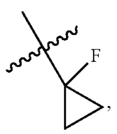

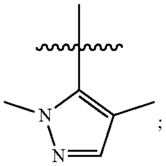

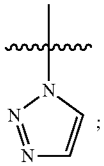

; and

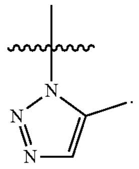 [SMILES: *n1nncc1C]

In any aspect or embodiment described herein, $R_{11}$ is selected from the group consisting of:

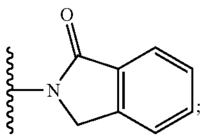

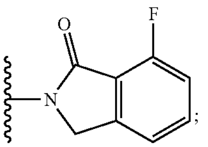

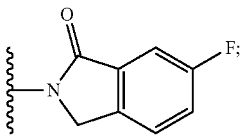

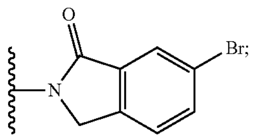

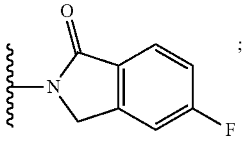

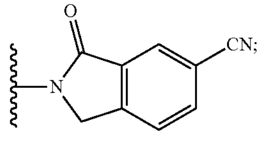

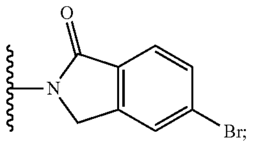

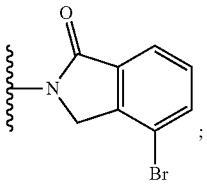

-continued

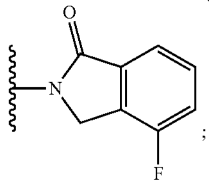

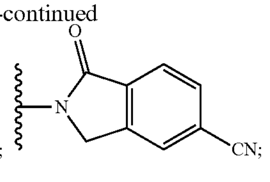

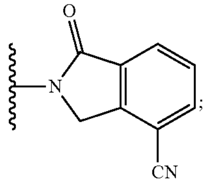

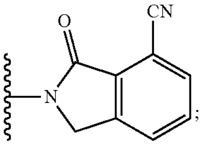

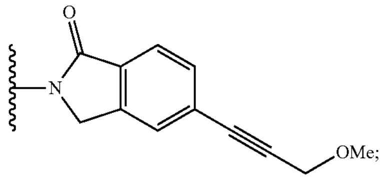

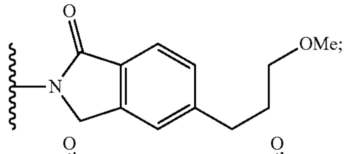

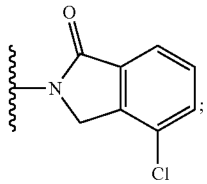

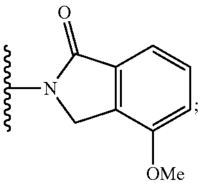

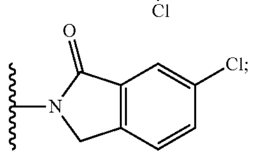

and

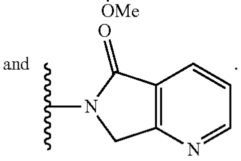

In any aspect or embodiment described herein, $R_{14a}$ and $R_{14b}$ are each independently selected from the group of H, optionally substituted haloalkyl, optionally substituted alkyl, optionally substituted alkoxy, optionally substituted hydroxyl alkyl, optionally substituted alkylamine, optionally substituted heterolkyl, optionally substituted alkyl-heterocycloalkyl, optionally substituted alkoxy-heterocycloalkyl, $CH_2OR_{30}$, $CH_2NHR_{30}$, $CH_2NCH_3R_{30}$, $CONR_{27a}R_{27b}$, $CH_2CONR_{27a}R_{27b}$, $CH_2NHCOR_{26}$, or $CH_2NCH_3COR_{26}$; and the other of $R_{14a}$ and $R_{14b}$ is H; or $R_{14a}$, $R_{14b}$, together with the carbon atom to which they are attached, form an optionally substituted 3- to 6-membered cycloalkyl, heterocycloalkyl, spirocycloalkyl or spiroheterocyclyl, wherein the spiroheterocyclyl is not epoxide or aziridine, the said spirocycloalkyl or spiroheterocycloalkyl itself being optionally substituted with an alkyl, a haloalkyl, or —$COR_{33}$ where $R_{33}$ is an alkyl or a haloalkyl, wherein $R_{30}$ is selected from H, alkyl, alkynylalkyl, cycloalkyl, heterocycloalkyl, cycloalkylalkyl, heterocycloalkylalkyl, arylalkyl or heteroarylalkyl further optionally substituted; $R_{26}$ and $R_{27}$ are as described above.

In any aspect or embodiment described herein, $R_{15}$ is selected from H, halogen, CN, OH, $NO_2$, $NR_{27a}R_{27b}$, $OR_{27a}$, $CONR_{27a}R_{27b}$, $NR_{27a}COR_{27b}$, $SO_2NR_{27a}R_{27b}$, $NR_{27a}$ $SO_2R_{27b}$, optionally substituted alkyl, optionally substituted haloalkyl (e.g. optionally substituted fluoroalkyl), optionally substituted haloalkoxy, optionally substituted aryl, optionally substituted heteroaryl, optionally substituted cycloalkyl, or optionally substituted heterocyclyl wherein optional substitution of the said aryl, heteroaryl, cycloalkyl and heterocycloalkyl includes $CH_2OR_{30}$, $CH_2NHR_{30}$, $CH_2NCH_3R_{30}$, $CONR_{27a}R_{27b}$, $CH_2CONR_{27a}R_{27b}$, $CH_2NHCOR_{26}$, $CH_2NCH_3COR_{26}$ or

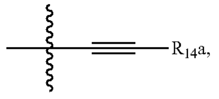

wherein $R_{26}$, $R_{27}$, $R_{30}$ and $R_{14a}$ are as described above.

In any aspect or embodiment described herein, $R_{14a}$ and $R_{14b}$ are each independently selected from the group of H, optionally substituted haloalkyl, optionally substituted alkyl, $CH_2OR_{30}$, $CH_2NHR_{30}$, $CH_2NCH_3R_{30}$, $CONR_{27a}R_{27b}$, $CH_2CONR_{27a}R_{27b}$, $CH_2NHCOR_{26}$, or $CH_2NCH_3COR_{26}$; and the other of $R_{14a}$ and $R_{14b}$ is H; or $R_{14a}$, $R_{14b}$, together with the carbon atom to which they are attached, form an optionally substituted 3- to 6-membered spirocycloalkyl or spiroheterocyclyl, wherein the spiroheterocyclyl is not epoxide or aziridine, the said spirocycloalkyl or spiroheterocycloalkyl itself being optionally substituted with an alkyl, a haloalkyl, or —$COR_{33}$ where $R_{33}$ is an alkyl or a haloalkyl, wherein $R_{30}$ is selected from H, alkyl, alkynylalkyl, cycloalkyl, heterocycloalkyl, cycloalkylalkyl, heterocycloalkylalkyl, arylalkyl or heteroarylalkyl further optionally substituted;

$R_{15}$ of Formula ULM-b is selected from H, halogen, CN, OH, $NO_2$, $NR_{27a}R_{27b}$, $OR_{27}a$, $CONR_{27a}R_{27b}$, $NR_{27a}COR_{27b}$, $SO_2NR_{27a}R_{27b}$, $NR_{27a}$ $SO_2R_{27b}$, optionally substituted alkyl, optionally substituted haloalkyl, optionally substituted haloalkoxy, optionally substituted aryl, optionally substituted heteroaryl, optionally substituted cycloalkyl, or optionally substituted heterocyclyl wherein optional substitution of the said aryl, heteroaryl, cycloalkyl and heterocycloalkyl includes $CH_2OR_{30}$, $CH_2NHR_{30}$, $CH_2NCH_3R_{30}$, $CONR_{27a}R_{27b}$, $CH_2CONR_{27a}R_{27b}$, $CH_2NHCOR_{26}$, $CH_2NCH_3COR_{26}$ or

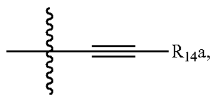

wherein $R_{26}$, $R_{27}$, $R_{30}$ and $R_{14a}$ are as described above.

In any aspect or embodiment described herein, the ULM has a chemical structure selected from the group of:

ULM-c

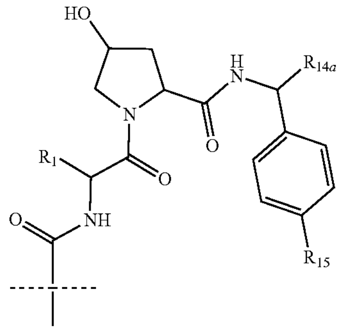

ULM-d

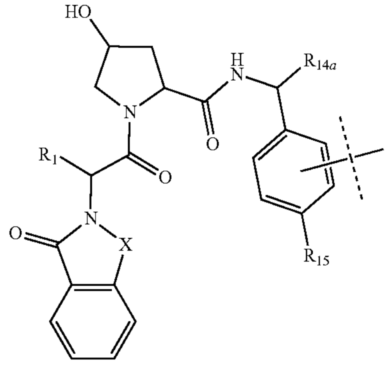

ULM-e

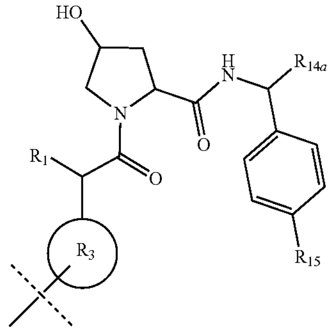

wherein:

$R_1$ of Formulas ULM-c, ULM-d, and ULM-e is H, ethyl, isopropyl, tert-butyl, sec-butyl, cyclopropyl, cyclobutyl, cyclopentyl, or cyclohexyl; optionally substituted alkyl, optionally substituted cycloalkyl, optionally substituted hydroxyalkyl, optionally substituted heteroaryl, or haloalkyl;

$R_{14a}$ of Formulas ULM-c, ULM-d, and ULM-e is H, haloalkyl, optionally substituted alkyl, methyl, fluoromethyl, hydroxymethyl, ethyl, isopropyl, or cyclopropyl;

$R_{15}$ of Formulas ULM-c, ULM-d, and ULM-e is selected from the group consisting of H, halogen, CN, OH, $NO_2$, optionally substituted heteroaryl, optionally substituted aryl, optionally substituted alkyl, optionally substituted haloalkyl, optionally substituted haloalkoxy, optionally substituted cycloalkyl, or optionally substituted cycloheteroalkyl;

X of Formulas ULM-c, ULM-d, and ULM-e is C, $CH_2$, or C═O $R_3$ of Formulas ULM-c, ULM-d, and ULM-e is absent or an optionally substituted 5 or 6 membered heteroaryl; and the dashed line indicates the site of attachment of at least one PTM, another ULM (ULM') or a chemical linker group coupling at least one PTM or a ULM' or both to ULM (ULM-a).

In any aspect or embodiment described herein, the ULM comprises a group according to the chemical structure:

ULM-f

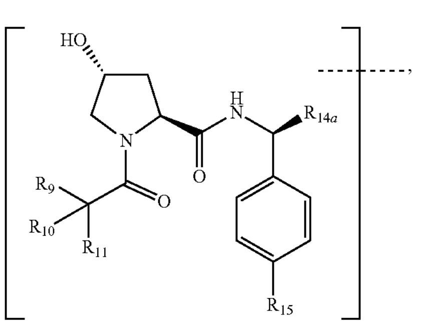

wherein:

$R_{14a}$ of Formula ULM-f is H, haloalkyl, optionally substituted alkyl, methyl, fluoromethyl, hydroxymethyl, ethyl, isopropyl, or cyclopropyl;

$R_9$ of Formula ULM-f is H;

$R_{10}$ of Formula ULM-f is H, ethyl, isopropyl, tert-butyl, sec-butyl, cyclopropyl, cyclobutyl, cyclopentyl, or cyclohexyl; R11 of Formula ULM-f is

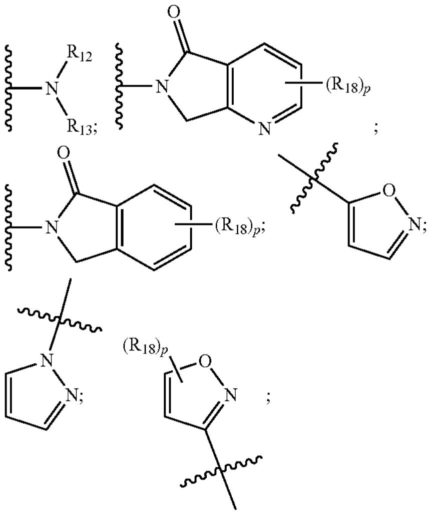

or optionally substituted heteroaryl;

p of Formula ULM-f is 0, 1, 2, 3, or 4;

each $R_{18}$ of Formula ULM-f is independently halo, optionally substituted alkoxy, cyano, optionally substituted alkyl, haloalkyl, haloalkoxy or a linker;

$R_{12}$ of Formula ULM-f is H, C═O;

$R_{13}$ of Formula ULM-f is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl, $R_{15}$ of Formula ULM-f is selected from the group consisting of H, halogen, Cl, CN, OH, $NO_2$, optionally substituted haloalkyl, optionally substituted heteroaryl, optionally substituted aryl;

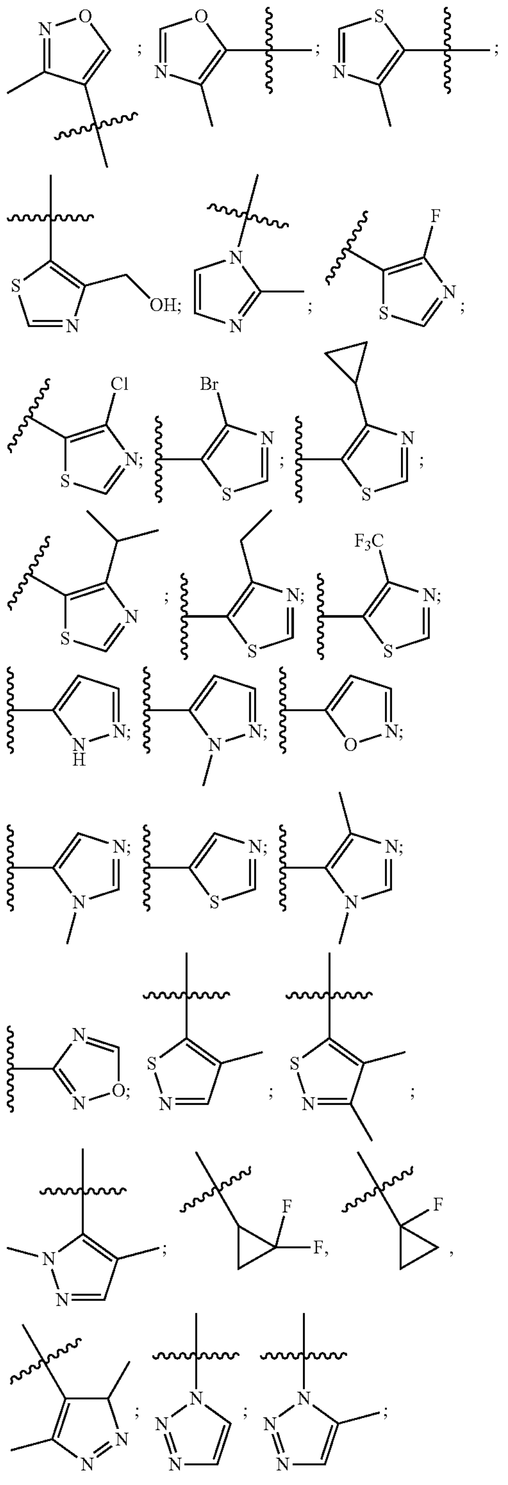

and the dashed line of Formula ULM-f indicates the site of attachment of at least one PTM, another ULM (ULM') or a chemical linker moiety coupling at least one PTM or a ULM' or both to ULM (ULM-f).

In any aspect or embodiment described herein, the VLM is covalently joined to a PTM, or a chemical linker group (L) via an R group (such as, $R^P$, $R^1$, $R^{1a}$, $R^{1b}$, $R^{Y3}$, $R^{Y4}$, $R_9$, $R_{10}$, $R_{11}$, $R_{12}$, $R_{13}$, $R_{14a}$, $R_{14b}$, $R_{15}$, $R_{16}$, $R_{17}$, $R_{18}$, $R_{26}$, R27a, $R_{27b}$, $R_{30}$, $R_{33}$), $W^3$, $W^4$, $W^5$, X, $X^1$, $X^2$, $X^3$, or T.

In any aspect or embodiment described herein, the VLM is covalently joined to a PTM, or a chemical linker group (L) via $R^P$, $R^1$, $R^{1a}$, $R^{1b}$, $R^{Y3}$, $R^{Y4}$, $R_9$, $R_{10}$, $R_{11}$, $R_{12}$, $R_{13}$, $R_{14a}$, $R_{14b}$, $R_{15}$, $R_{16}$, $R_{17}$, $R_{18}$, $R_{26}$, R27a, $R_{27b}$, $R_{30}$, $R_{33}$, $W^3$, $W^4$, $W^5$, X, $X^1$, $X^2$, $X^3$, or T.

In any aspect or embodiment described herein, the $R^P$, $R^1$, $R^{1a}$, $R^{1b}$, $R^{Y3}$, $R^{Y4}$, $R_9$, $R_{10}$, $R_{11}$, $R_{12}$, $R_{13}$, $R_{14a}$, $R_{14b}$, $R_{15}$, $R_{16}$, $R_{17}$, $R_{18}$, $R_{26}$, R27a, $R_{27b}$, $R_{30}$, $R_{33}$, $W^3$, $W^4$, X, $X^1$, $X^2$, $X^3$, or T can independently be covalently coupled to a linker and/or a linker to which is attached to one or more PTM, ULM, and VLM group.

In any aspect or embodiment described herein, the ULM is selected from the following structures:

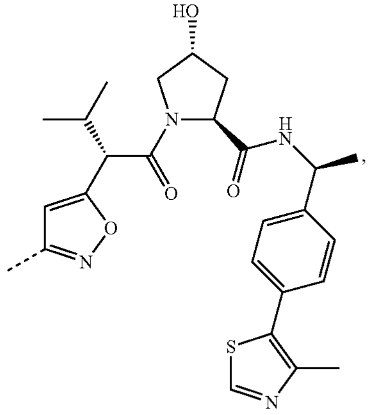

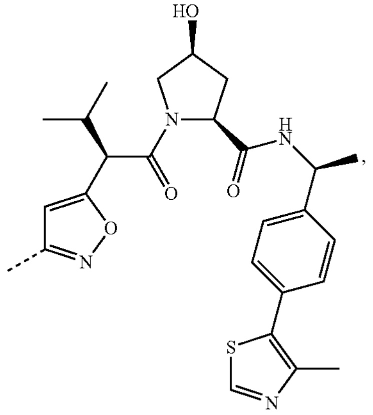

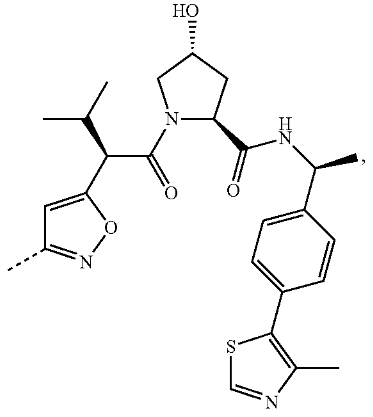

-continued

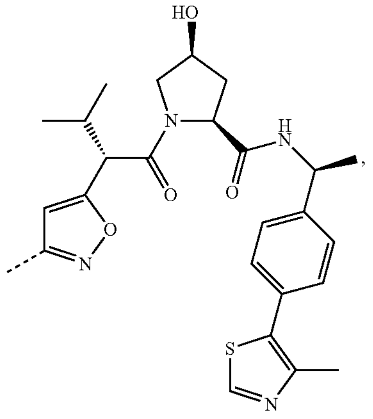

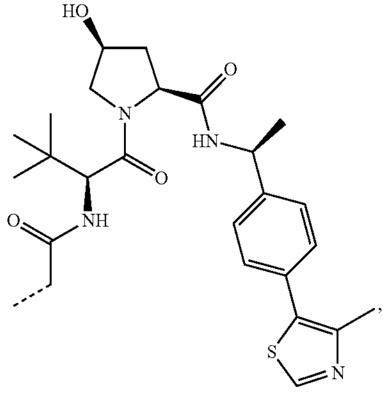

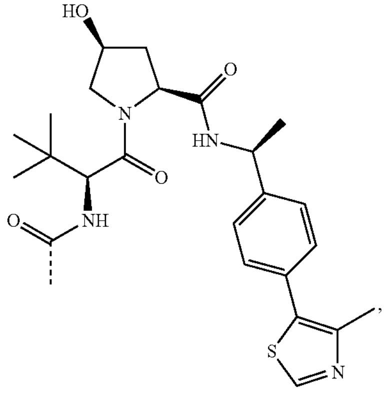

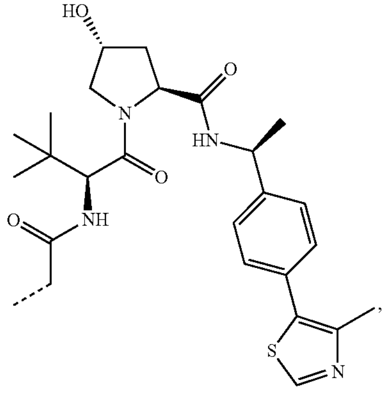

-continued
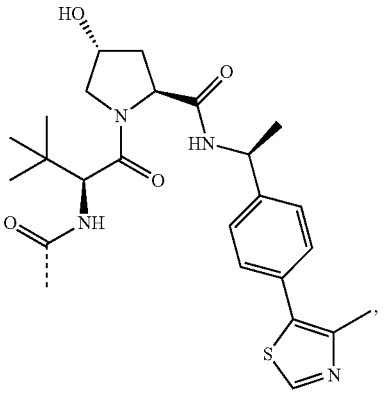
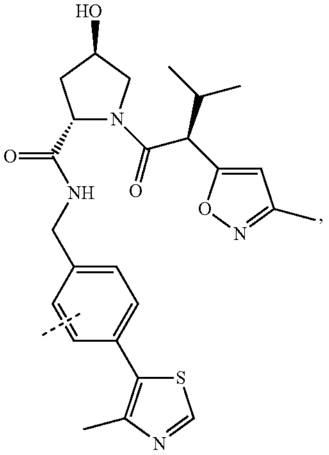
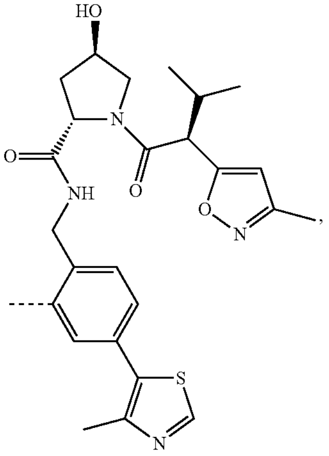
-continued
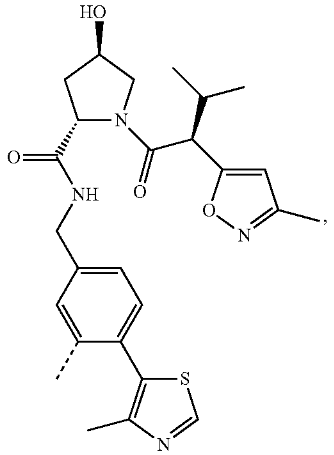
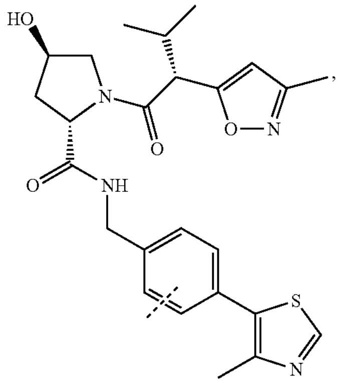
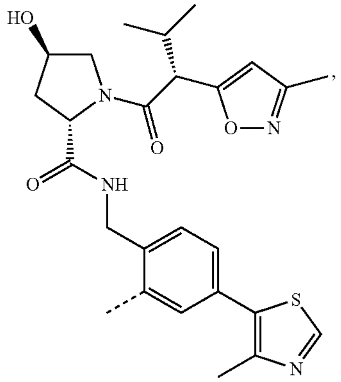
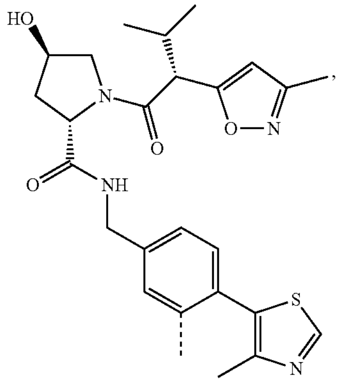

-continued
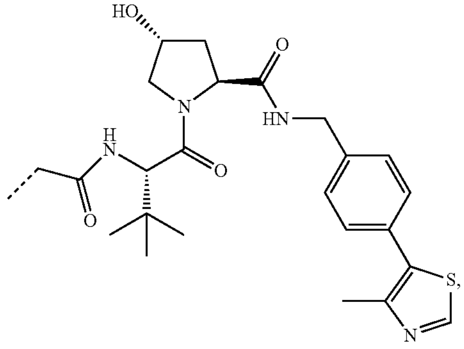
, or
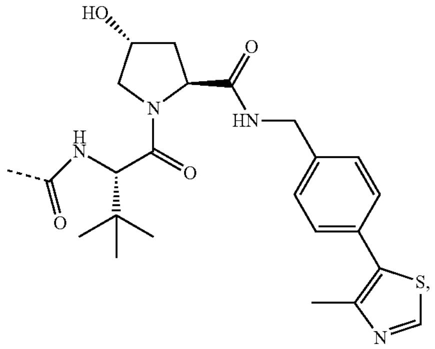
,
wherein the dashed line indicates the site of attachment of at least one PTM, another ULM (ULM') or a chemical linker moiety coupling at least one PTM or a ULM' or both to ULM.
In any aspect or embodiment described herein, the ULM is selected from the following structures:
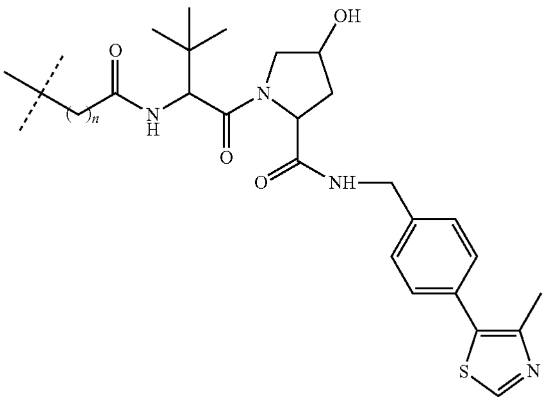
-continued
ULM-a2
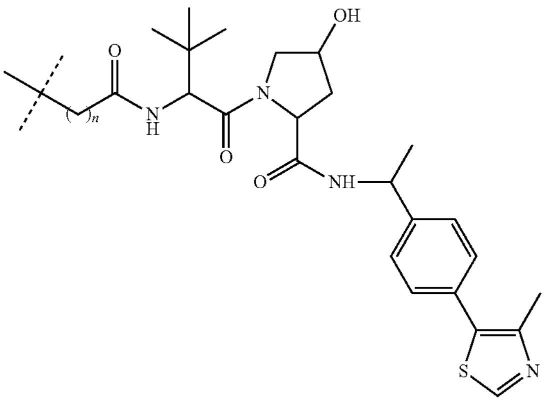
ULM-a3
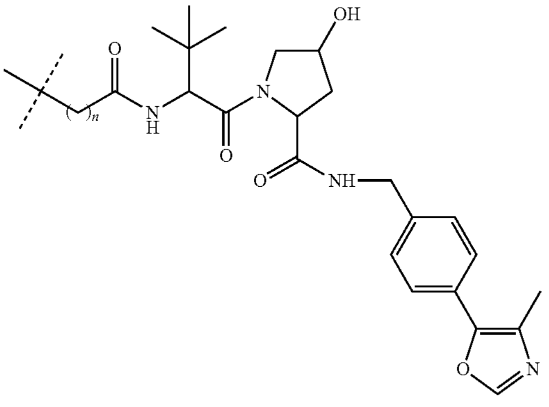
ULM-a4
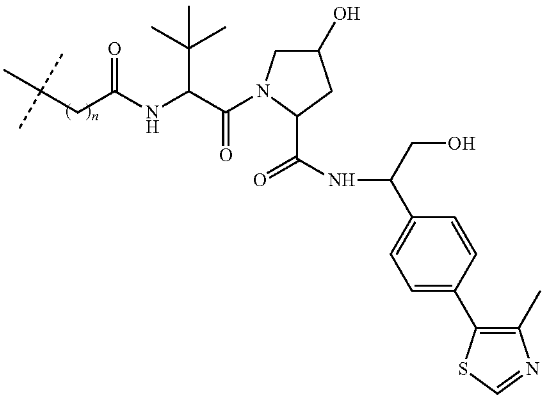

-continued
ULM-a5
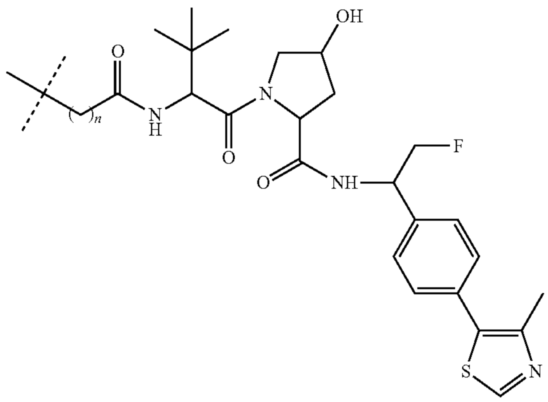
ULM-a6
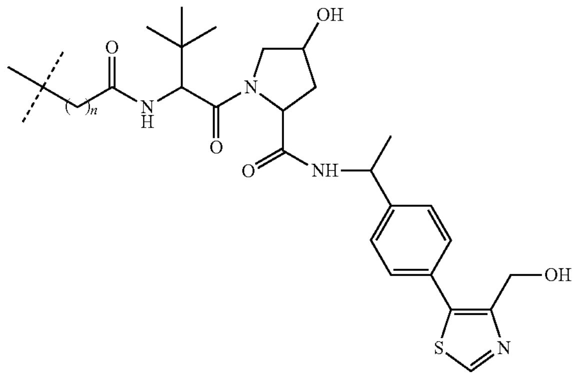
ULM-a7
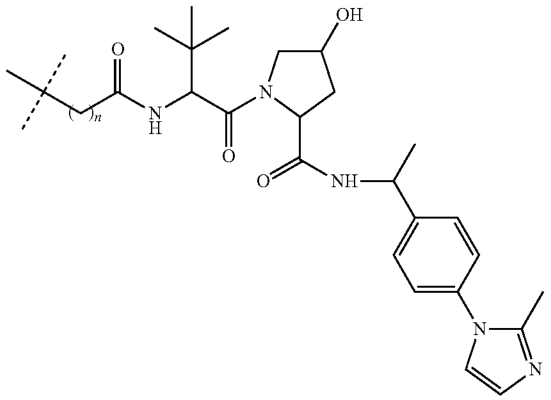
-continued
ULM-a8
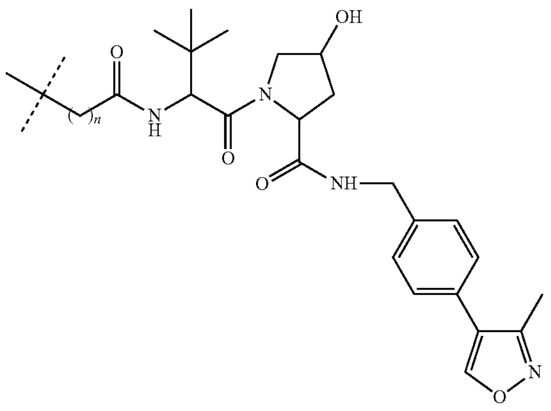
ULM-a9
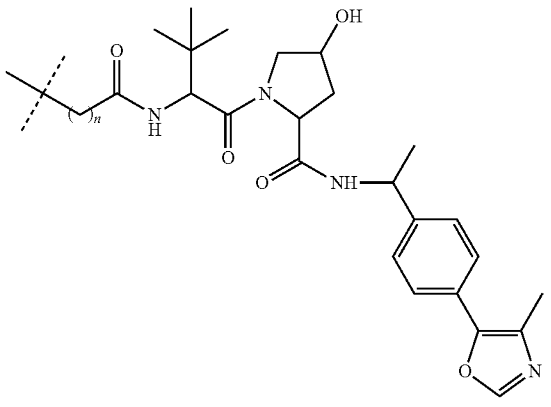
ULM-a10
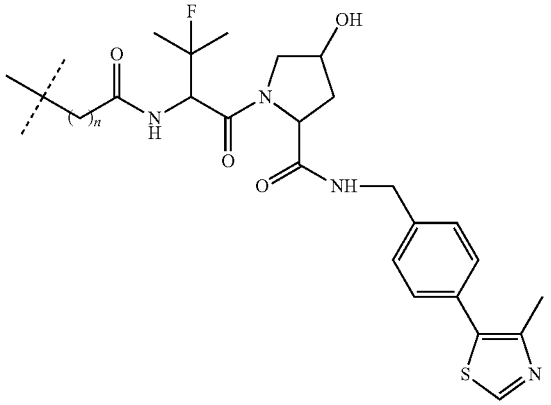

-continued
ULM-a11
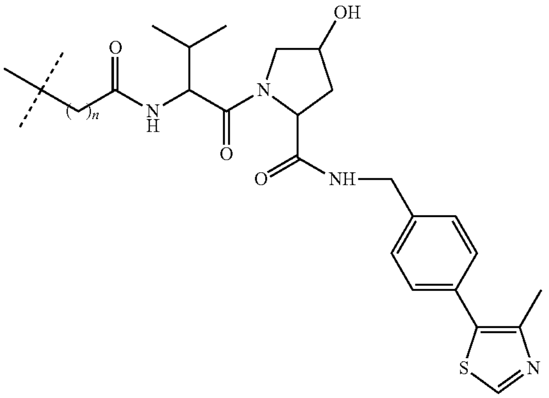
ULM-a12
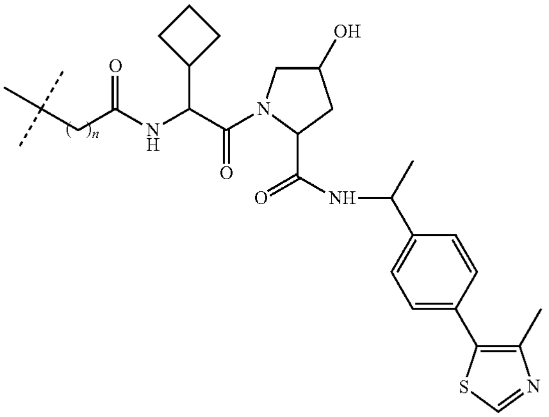
ULM-a13
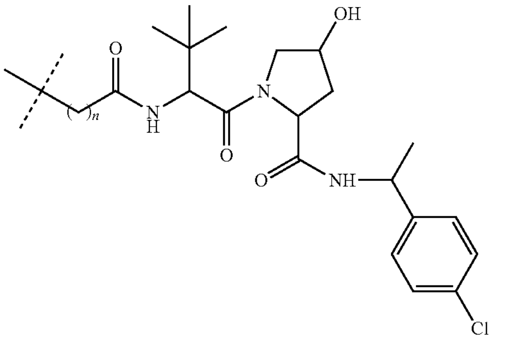
ULM-a14
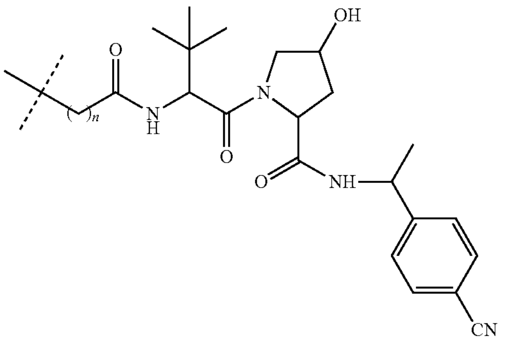
-continued
ULM-a15
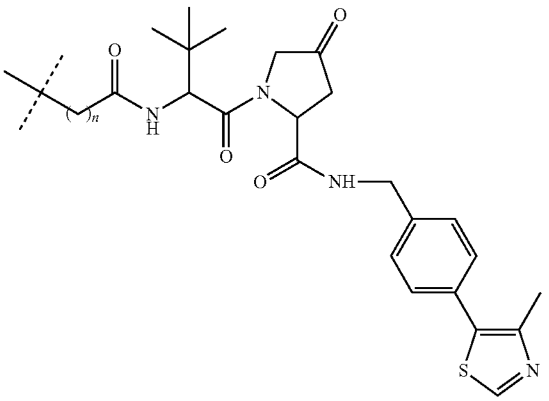
where n is 0 or 1, and the dashed line indicates the site of attachment of at least one PTM, another ULM (ULM') or a chemical linker moiety coupling at least one PTM or a ULM' or both to ULM.
In any aspect or embodiment described herein, the ULM is selected from the following structures:
ULM-b1
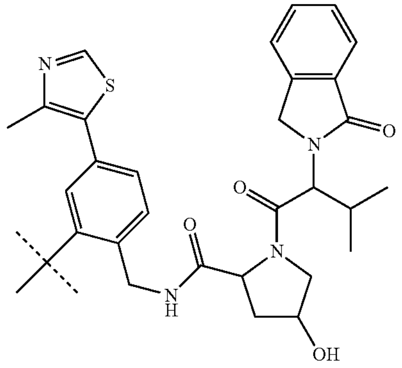
ULM-b2
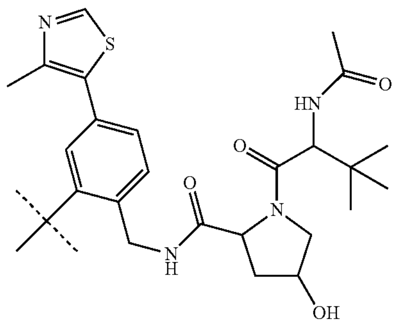

ULM-b3
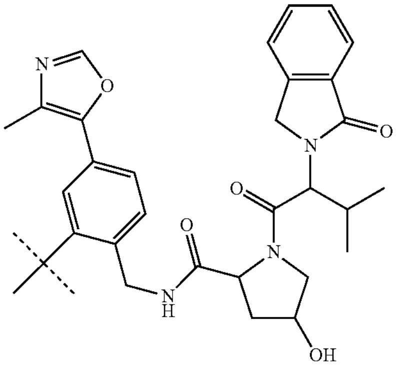
ULM-b4
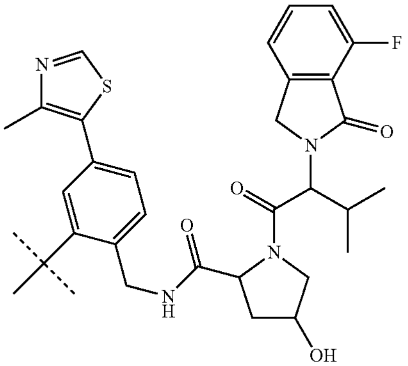
ULM-b5
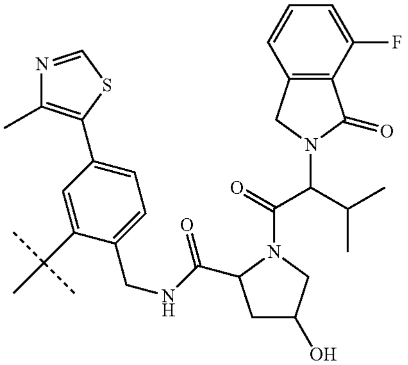
ULM-b6
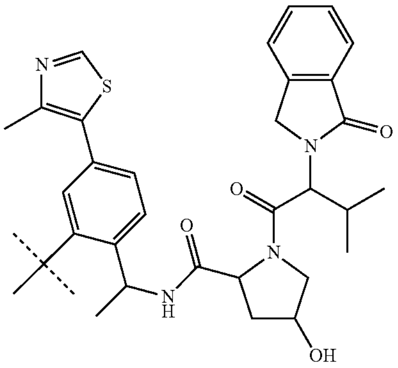
ULM-b7
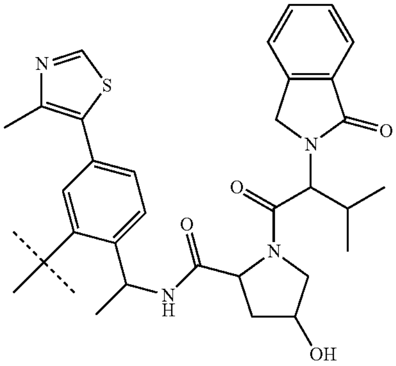
ULM-b8
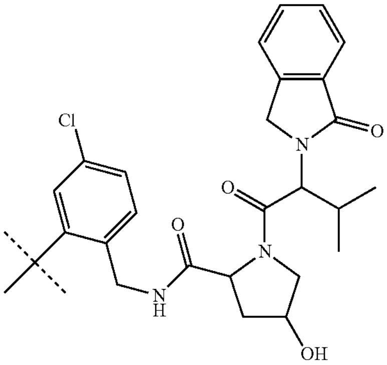
ULM-b9
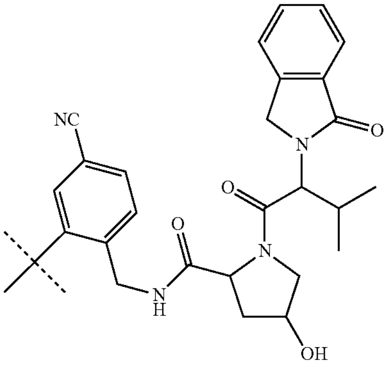
ULM-b7
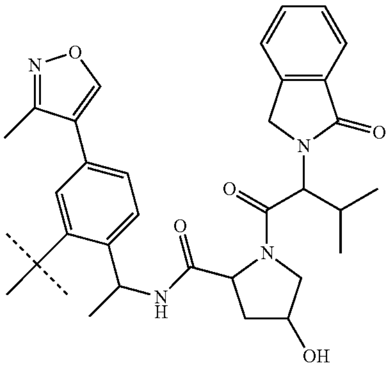

-continued
ULM-b8
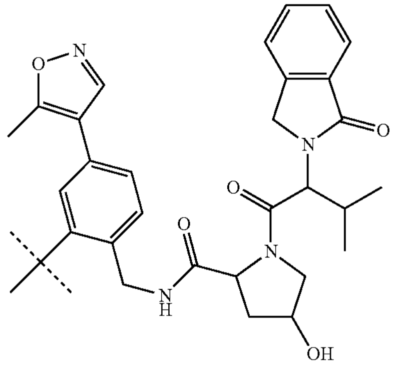
ULM-b9
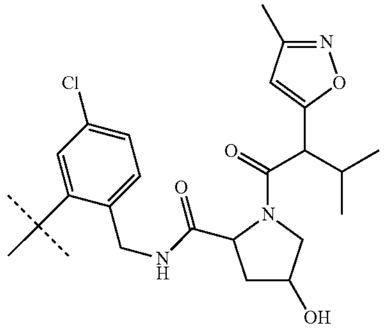
ULM-c1
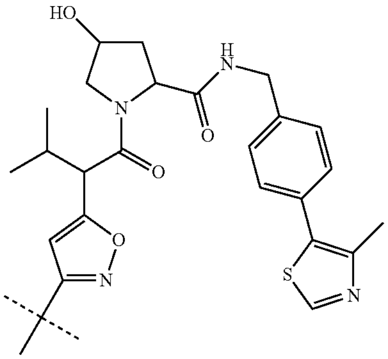
ULM-c2
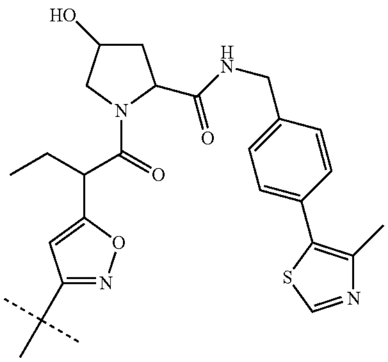
-continued
ULM-c3
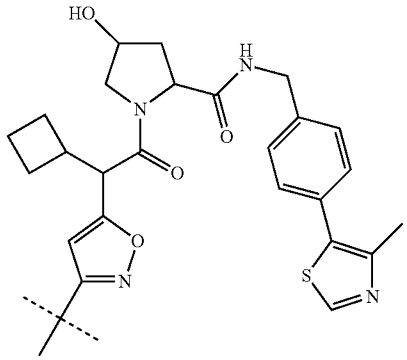
ULM-c4
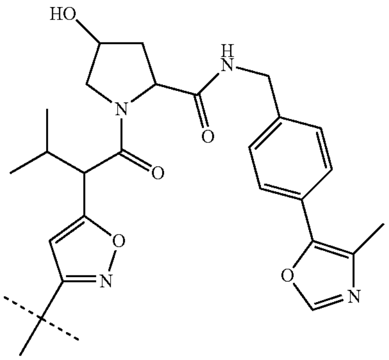
ULM-c5
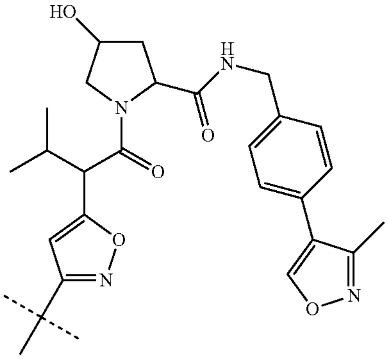
ULM-c6
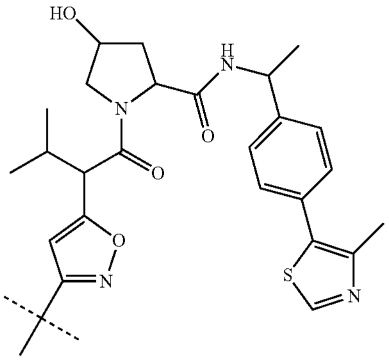

-continued
ULM-c7
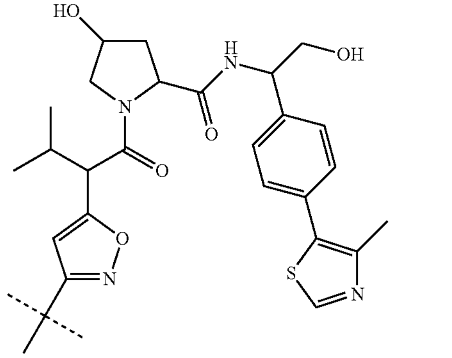
ULM-c8
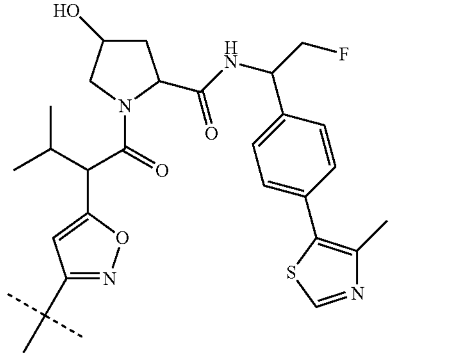
ULM-c9
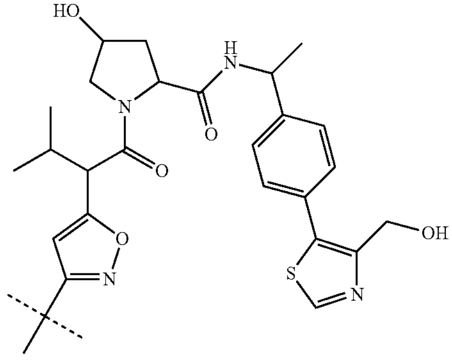
ULM-c10
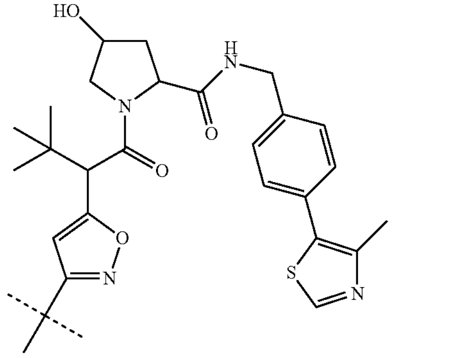
-continued
ULM-c11
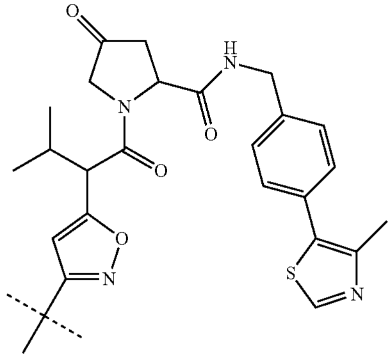
ULM-c12
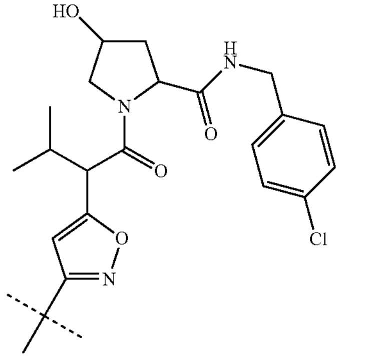
ULM-c13
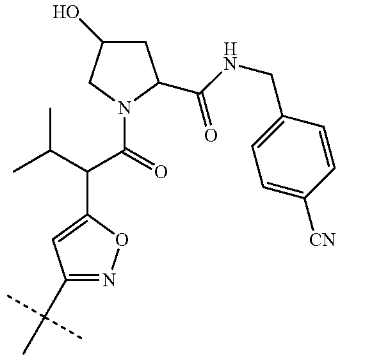
ULM-c14
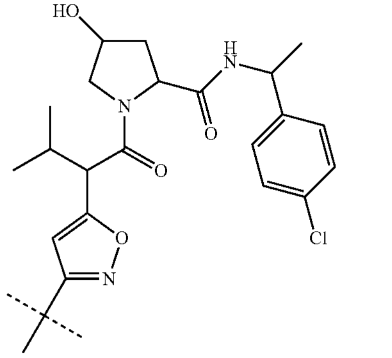

-continued
ULM-c15
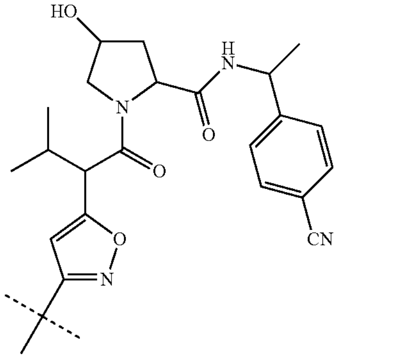
ULM-d1
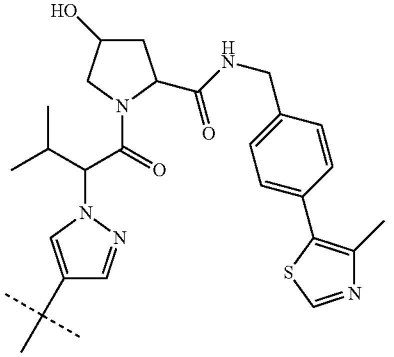
ULM-d2
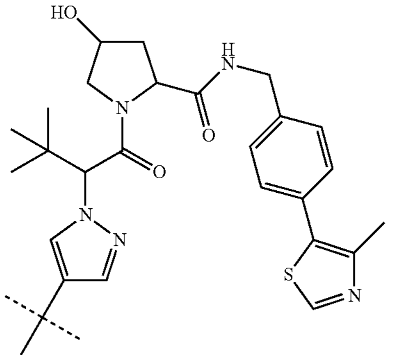
ULM-d3
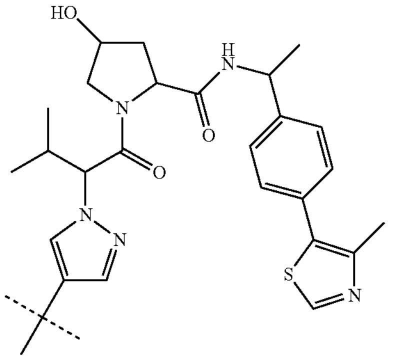
-continued
ULM-d4
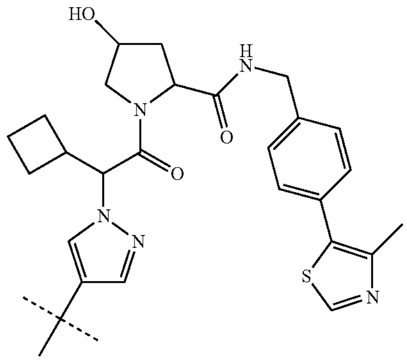
ULM-d5
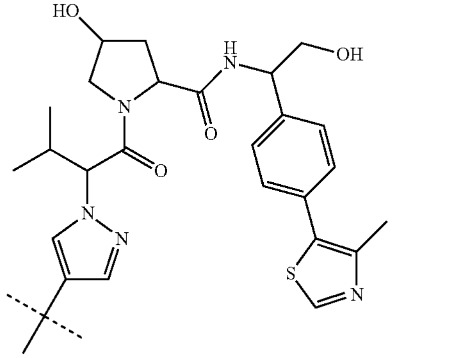
ULM-d6
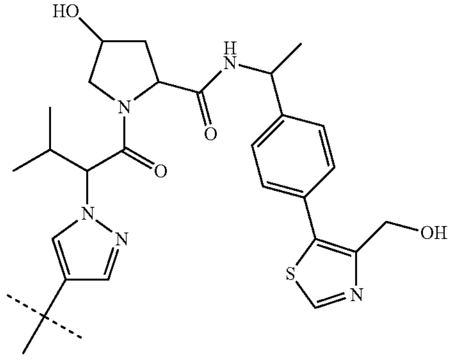
ULM-d7
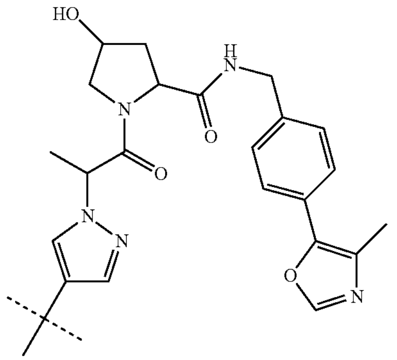

-continued

ULM-d8

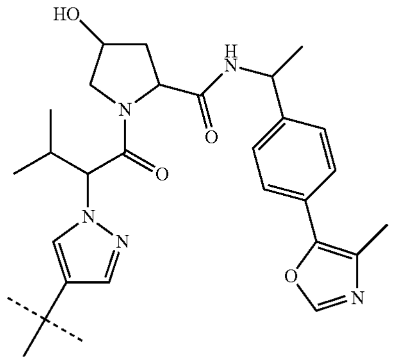

ULM-d9

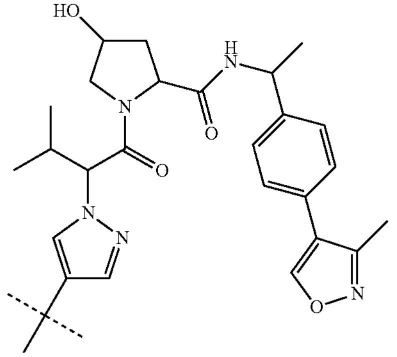

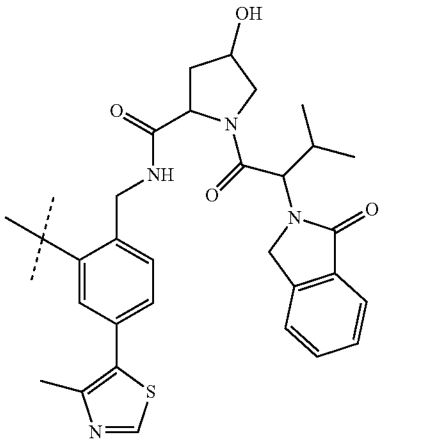

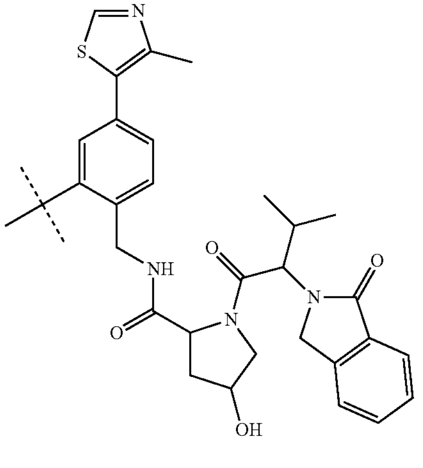

-continued

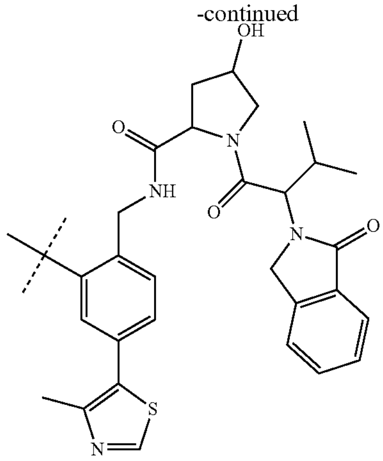

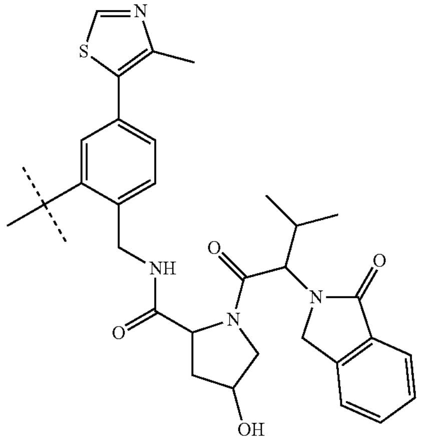

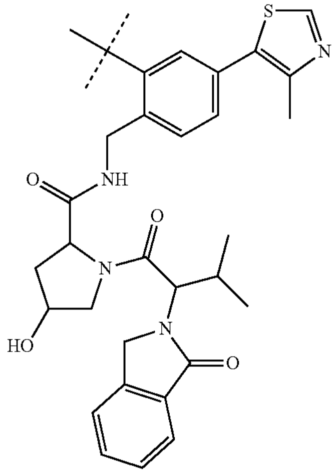

wherein the phenyl ring in ULM-a1 through ULM-a15, ULM-b1 through ULM-b12, ULM-c1 through ULM-c15 and ULM-d1 through ULM-d9 is optionally substituted with fluorine, lower alkyl and alkoxy groups, and wherein the dashed line indicates the site of attachment of at least one PTM, another ULM (ULM') or a chemical linker moiety coupling at least one PTM or a ULM' or both to ULM-a.

In any aspect or embodiment described herein, the phenyl ring in ULM-a1 through ULM-a15, ULM-b1 through ULM-b12, ULM-c1 through ULM-c15 and ULM-d1 through ULM-d9 can be functionalized as the ester to make it a part of the prodrug.

In any aspect or embodiment described herein, the hydroxyl group on the pyrrolidine ring of ULM-a1 through ULM-a15, ULM-b1 through ULM-b12, ULM-c1 through ULM-c15 and ULM-d1 through ULM-d9, respectively, comprises an ester-linked prodrug moiety.

In any aspect or embodiment described herein, the ULM or VLM is represented by:

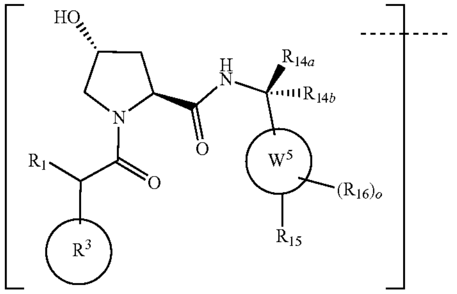

or

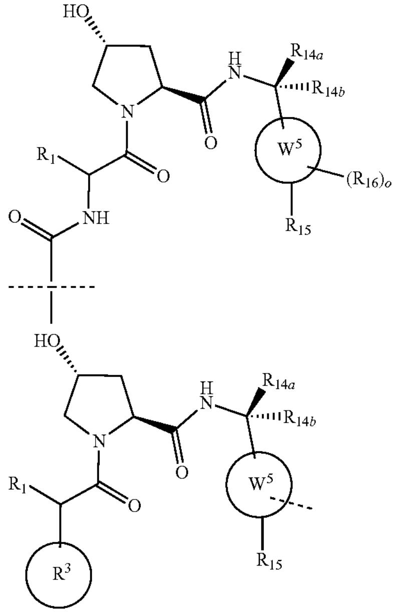

or or a pharmaceutically acceptable salt thereof, wherein:

$R_1$ is H, optionally substituted alkyl or optionally substituted cycloalkyl;

$R_3$ is an optionally substituted 5-6 membered heteroaryl; $W^5$ is optionally substituted phenyl, optionally substituted napthyl or optionally substituted pyridinyl;

one of $R_{14a}$ and $R_{14b}$ is H, optionally substituted alkyl, optionally substituted haloalkyl (e.g., fluoroalkyl), optionally substituted alkoxy, optionally substituted hydroxyl alkyl, optionally substituted alkylamine, optionally substituted heterolkyl, optionally substituted alkyl-heterocycloalkyl, optionally substituted alkoxy-heterocycloalkyl, $COR_{26}$, $CONR_{27a}R_{27b}$, $NHCOR_{26}$, or $NHCH_3COR_{26}$; and the other of $R_{14a}$ and $R_{14b}$ is H; or $R_{14a}$, $R_{14b}$, together with the carbon atom to which they are attached, form an optionally substituted 3 to 6 membered cycloalkyl, heterocycloalkyl, spirocycloalkyl or spiroheterocyclyl, wherein the spiroheterocyclyl is not epoxide or aziridine;

$R_{15}$ is CN, optionally substituted fluoroalkyl,

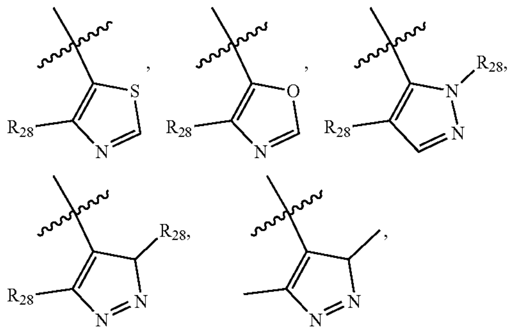

optionally substituted

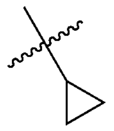

(e.g.,

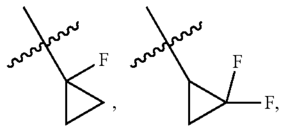

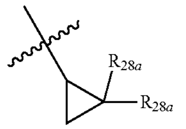

or

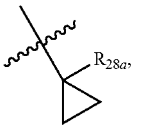

wherein $R_{28a}$ is halo, optionally substituted alkyl or fluoroalkyl), or

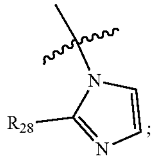

each $R_{16}$ is independently selected from halo, CN, optionally substituted alkyl, optionally substituted haloalkyl, hydroxy, or haloalkoxy;

each $R_{26}$ is independently H, optionally substituted alkyl or $NR_{27a}R_{27b}$;

each $R_{27a}$ and $R_{27b}$ is independently H, optionally substituted alkyl, or $R_{27a}$ and $R_{27b}$ together with the nitrogen atom to which they are attached form a 4-6 membered heterocyclyl;

$R_{28}$ is H, optionally substituted alkyl, optionally substituted alkoxy, optionally substituted heteroalkyl, optionally substituted alkylamine, optionally substituted hydroxyalkyl, amine, optionally substituted alkynyl, or optionally substituted cycloalkyl;

o is 0, 1 or 2; and the dashed line indicates the site of attachment of at least one PTM, another ULM (ULM') or a chemical linker moiety coupling at least one PTM or a ULM' or both to ULM.

In any of the aspects or embodiments described herein, the ULM is of the formula:

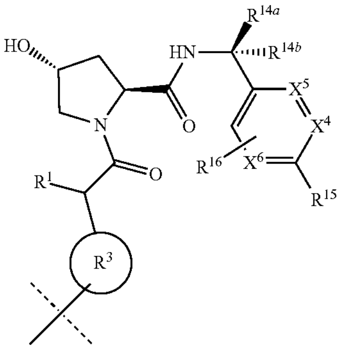

or

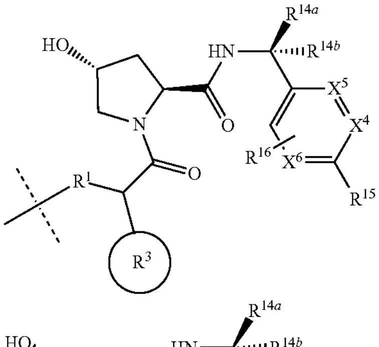

or

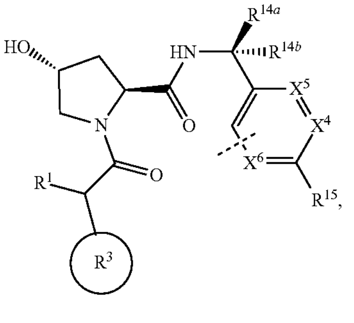

wherein:

each of $X^4$, $X^5$, and $X^6$ is selected from CH and N, wherein no more than 2 are N;

$R^1$ is $C_{1-6}$ alkyl;

$R_3$ is an optionally substituted 5-6 membered heteroaryl;

one of $R^{14a}$ and $R^{14b}$ is H, optionally substituted alkyl, optionally substituted haloalkyl, optionally substituted alkoxy, optionally substituted hydroxyl alkyl, optionally substituted alkylamine, optionally substituted heterolkyl, optionally substituted alkyl-heterocycloalkyl, optionally substituted alkoxy-heterocycloalkyl, $COR^{26}$, $CONR^{27a}R^{27b}$, $NHCOR^{26}$, or $NHCH_3COR^{26}$; and the other of $R^{14a}$ and $R^{14b}$ is H; or $R^{14a}$ and $R^{14b}$, together with the carbon atom to which they are attached, form an optionally substituted 3 to 5 membered cycloalkyl, heterocycloalkyl, spirocycloalkyl or spiroheterocyclyl, wherein the spiroheterocyclyl is not epoxide or aziridine;

each $R_{27a}$ and $R_{27b}$ is independently H or $C_{1-6}$ alkyl;

q is 1, 2, 3 or 4;

$R^{15}$ is

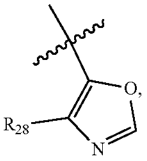

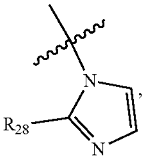

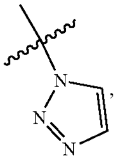

-continued

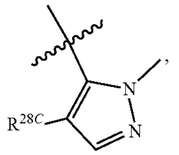

or CN;

$R^{28}$ is H, methyl, $CH_2N(Me)_2$, $CH_2OH$, $CH_2O(C_{1-4}alkyl)$, $CH_2NHC(O)C_{1-4}alkyl$, $NH_2$,

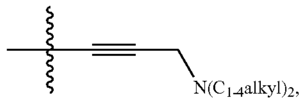

or

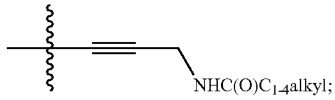

$R^{28C}$ is H, methyl, fluoro, or chloro;

$R^{16}$ is H, $C_{1-4}$alkyl, fluoro, chloro, CN, or $C_{1-4}$alkoxy; and the dashed line indicates the site of attachment of at least one PTM, another ULM (ULM') or a chemical linker moiety coupling at least one PTM or a ULM' or both to ULM.

In any aspect or embodiment described herein, $R^{14a}$ and $R^{14b}$ are selected from: H, $C_{1-4}$ alkyl, $C_{1-4}$ cycloalkyl, $C_{1-4}$ haloalkyl, $C_{1-4}$ hydroxyalkyl, $C_{1-4}$ alkyloxyalkyl, $C_{1-4}$ alkyl-$NR_{27a}R_{27b}$ and $CONR_{27a}R_{27b}$.

In any aspect or embodiment described herein, at least one of $R^{14a}$ and $R^{14b}$ is H (e.g., both $R^{14a}$ and $R_{14b}$ are H).

In any aspect or embodiment described herein, at least one of $R^{14a}$ and $R^{14b}$ is optionally substituted alkyl, optionally substituted haloalkyl, optionally substituted alkoxy, optionally substituted hydroxyl alkyl, optionally substituted alkylamine, optionally substituted heterolkyl, optionally substituted alkyl-heterocycloalkyl, optionally substituted alkoxy-heterocycloalkyl, $COR^{26}$, $CONR^{27a}R^{27b}$, $NHCOR^{26}$, or $NHCH_3COR^{26}$. Alternatively, in any aspect or embodiment described herein, one of $R^{14a}$ and $R^{14b}$ is optionally substituted alkyl, optionally substituted haloalkyl, optionally substituted alkoxy, optionally substituted hydroxyl alkyl, optionally substituted alkylamine, optionally substituted heterolkyl, optionally substituted alkyl-heterocycloalkyl, optionally substituted alkoxy-heterocycloalkyl, $COR^{26}$, $CONR^{27a}R^{27b}$, $NHCOR^{26}$, or $NHCH_3COR^{26}$; and the other of $R^{14a}$ and $R^{14b}$ is H.

In any aspect or embodiment described herein, $R^{14a}$ and $R^{14b}$ together with the carbon atom to which they are attached form

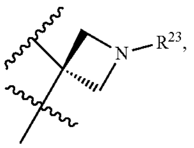

wherein $R^{23}$ is selected from H, $C_{1-4}$alkyl, —$C(O)C_{1-4}$alkyl.

In any aspect or embodiment described herein, ULM and where present, ULM', are each independently a group according to the chemical structure:

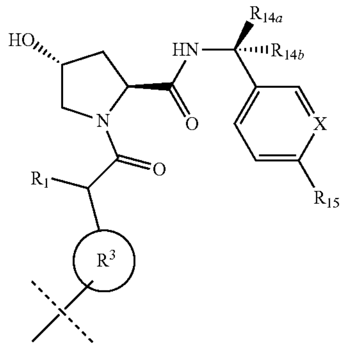

or

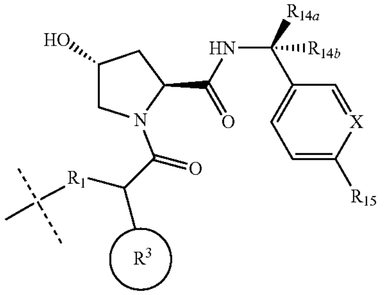

or

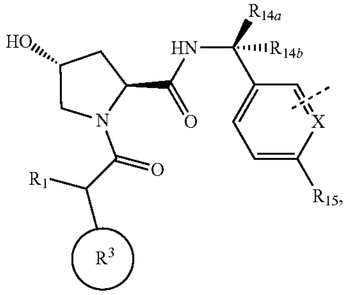

or a pharmaceutically acceptable salt thereof, wherein:

X is CH or N;

$R_1$ is H, optionally substituted alkyl or optionally substituted cycloalkyl;

$R_3$ is an optionally substituted 5-6 membered heteroaryl;

one of $R_{14a}$ and $R_{14b}$ is H, optionally substituted alkyl, optionally substituted haloalkyl (e.g., fluoroalkyl), optionally substituted alkoxy, optionally substituted hydroxyl alkyl, optionally substituted alkylamine, optionally substituted heterolkyl, optionally substituted alkyl-heterocycloalkyl, optionally substituted alkoxy-heterocycloalkyl, $COR_{26}$, $CONR_{27a}R_{27b}$, $NHCOR_{26}$, or $NHCH_3COR_{26}$; and the other of $R_{14a}$ and $R_{14b}$ is H; or $R_{14a}$, $R_{14b}$, together with the carbon atom to which they are attached, form an optionally substituted 3 to 6 membered cycloalkyl, heterocycloalkyl, spirocycloalkyl or spiroheterocyclyl, wherein the spiroheterocyclyl is not epoxide or aziridine;

$R_{15}$ is CN, optionally substituted fluoroalkyl,

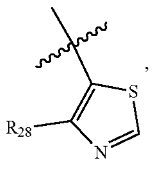

,

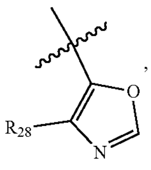

,

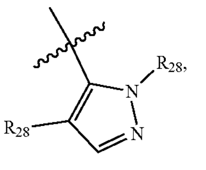

-continued

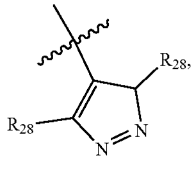

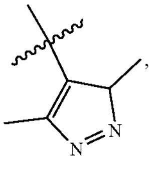

optionally substituted

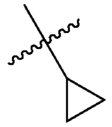

(e.g.,

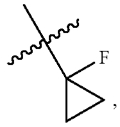

,

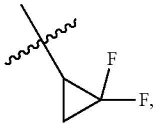

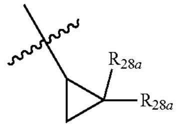

or

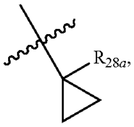

wherein $R_{28a}$ is halo, optionally substituted alkyl or fluoroalkyl), or

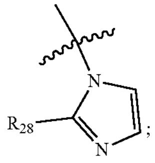

;

each $R_{26}$ is independently H, optionally substituted alkyl or $NR_{27a}R_{27b}$;

each $R_{27a}$ and $R_{27b}$ is independently H, optionally substituted alkyl, or $R_{27a}$ and $R_{27b}$ together with the nitrogen atom to which they are attached form a 4-6 membered heterocyclyl;

$R_{28}$ is H, optionally substituted alkyl, optionally substituted alkoxy, optionally substituted heteroalkyl, optionally substituted alkylamine, optionally substituted hydroxyalkyl, amine, optionally substituted alkynyl, or optionally substituted cycloalkyl; and the dashed line indicates the site of attachment of at least one PTM, another ULM (ULM') or a chemical linker moiety coupling at least one PTM or a ULM' or both to ULM.

In any of the aspects or embodiments described herein, $R_1$ is $C_{1-6}$ alkyl.

In any of the aspects or embodiments described herein, one of $R_{14a}$ and $R_{14b}$ is H, $C_{1-6}$ alkyl, $C_{1-6}$haloalkyl, optionally substitute $C_{1-4}$ alkylamine, $C_{1-6}$alkoxy, $(CH_2)_qC_{1-6}$ alkoxy, $(CH_2)_qC_{1-6}$ alkoxy-$C_3$-$C_7$ heterocycloalkyl, $(CH_2)_q$OH, $(CH_2)_qNR_{27a}R_{27b}$, $(CH_2)_q$NHCOC$_{1-6}$ alkyl, $C_{3-6}$ cycloalkyl, or $NR_{27a}R_{27b}$; each $R_{26}$ is independently H, $C_{1-6}$ alkyl or $NR_{27a}R_{27b}$; each $R_{27a}$ and $R_{27b}$ is independently H or $C_{1-6}$ alkyl; and q is 1, 2, 3 or 4.

In any of the aspects or embodiments described herein, one of $R_{14a}$ and $R_{14b}$ is H, $C_{1-4}$ alkyl, $C_{1-4}$ haloalkyl, $C_{1-4}$ alkoxy, optionally substituted $C_{1-4}$ alkylamine, $(CH_2)_qC_{1-6}$ alkoxy, $(CH_2)_qC_{1-6}$ alkoxy-$C_3$-$C_7$ heterocycloalkyl, $(CH_2)_q$OH, $(CH_2)_qNR_{27a}R_{27b}$, $(CH_2)_q$NHCOC$_{1-6}$ alkyl, $C_{3-6}$ cycloalkyl, or $NR_{27a}R_{27b}$; each $R_{26}$ is independently H, $C_{1-4}$ alkyl or $NR_{27a}R_{27b}$; each $R_{27a}$ and $R_{27b}$ is independently H or $C_{1-4}$ alkyl; and q is 1 or 2.

In any of the aspects or embodiments described herein, $R_{28}$ is $C_{1-6}$ alkyl, $C_{3-6}$ cycloalkyl, $C_{1-6}$ haloalkyl, $(CH_2)_q OC_{1-6}$alkyl, $(CH_2)_qOH$, $(CH_2)_qNR_{27a}R_{27b}$, $(CH_2)_q NHCOC_{1-6}$ alkyl, or

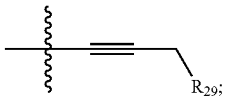

$R_{29}$ is H, $C_{1-6}$ alkyl, $NR_{27a}R_{27b}$ or $_qNHCOC_{1-6}$ alkyl; and wherein q is 1 or 2.

In any of the aspects or embodiments described herein, $R^3$ is isoxazolyl, 4-chloroisoxazolyl, 4-fluoroisoxazolyl, or pyrazolyl. In any of the aspects or embodiments described herein, X is CH.

In any aspect or embodiment described herein, the ULM is according to the formula:

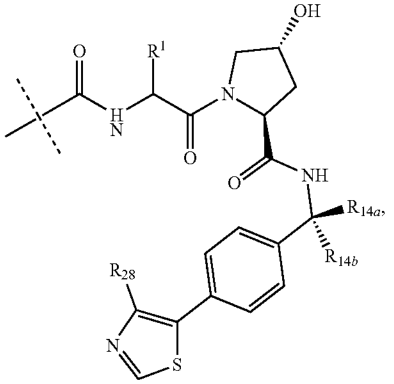

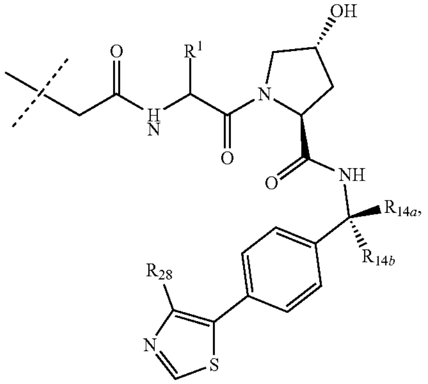

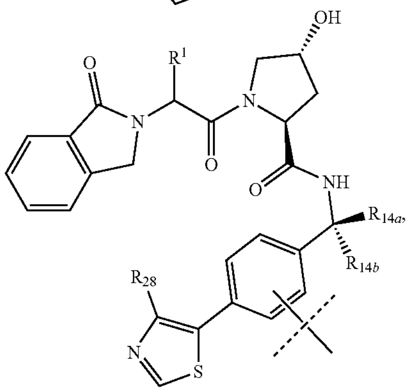

-continued

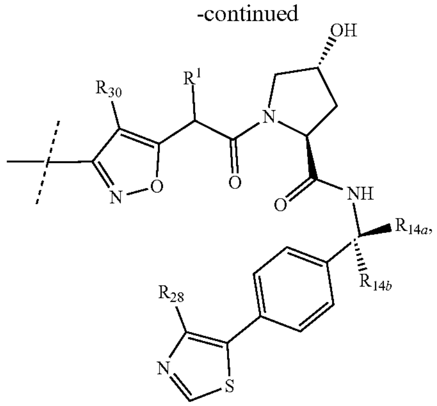

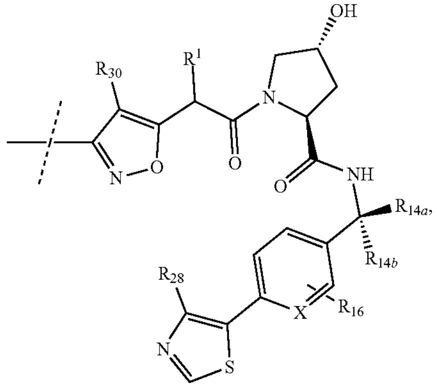

or a pharmaceutically acceptable salt thereof, wherein:

$R_1$, $R_{14a}$ and $R_{14b}$ are as described herein;

X is CH or N;

$R_{30}$ is H, F or Cl;

$R^{16}$ is H, $C_{1-4}$ alkyl, fluoro, chloro, CN, or $C_{1-4}$ alkoxy;

$R_{28}$ is H, methyl, $CH_2N(Me)_2$, $CH_2OH$, $CH_2O(C_{1-4}alkyl)$, $CH_2NHC(O)C_{1-4}alkyl$, $NH_2$,

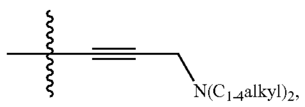

or

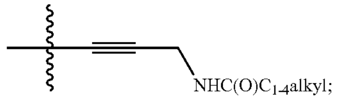

and the dashed line indicates the site of attachment of at least one PTM, another ULM (ULM') or a chemical linker moiety coupling at least one PTM or a ULM' or both to ULM.

In any of the aspects or embodiments described herein, the ULM is according to the formula:

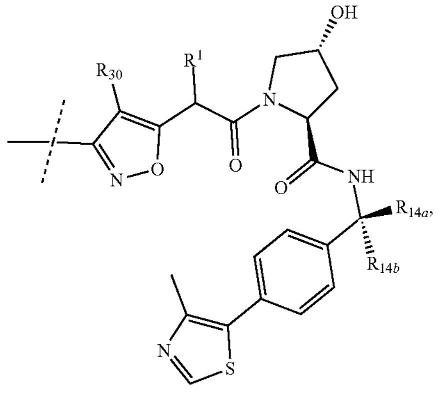

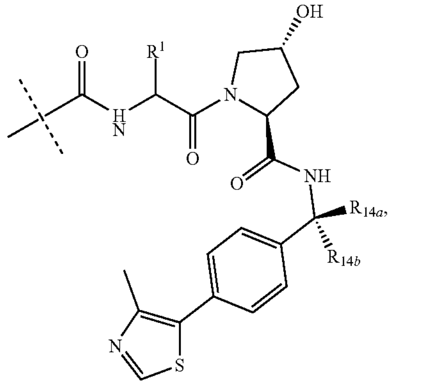

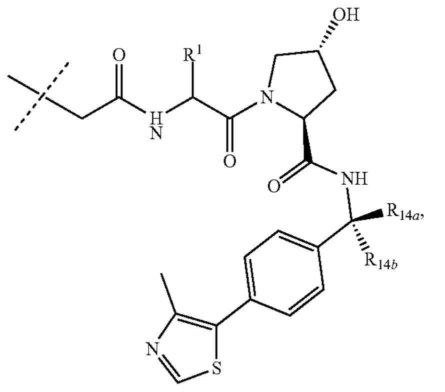

-continued

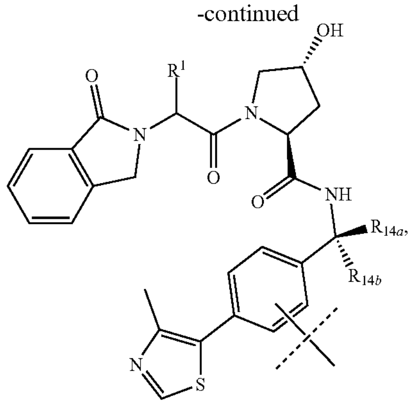

or a pharmaceutically acceptable salt thereof, wherein:

each of $R_1$, $R_{14a}$, $R_{14b}$ are as described herein;

$R_{30}$ is H, F or Cl; and the dashed line indicates the site of attachment of at least one PTM, another ULM (ULM') or a chemical linker moiety coupling at least one PTM or a ULM' or both to ULM.

In any aspect or embodiment described herein, the VLM is covalently joined to a PTM, or a chemical linker group (L) via an R group (such as, $R^1$, $R^3$, $R_{14a}$, $R_{14b}$, $R_{15}$, $R_{16}$, $R^{23}$, $R^{26}$, $R_{27a}$, $R_{27b}$, $R_{28}$, $R_{28a}$, $R_{28c}$, $R_{29}$, $R_{30}$), X, $X^4$, $X^5$, or $X^6$.

In any aspect or embodiment described herein, the VLM is covalently joined to a PTM, or a chemical linker group (L) via $R^1$, $R^3$, $R_{14a}$, $R_{14b}$, $R_{15}$, $R_{16}$, $R^{23}$, $R^{26}$, $R_{27a}$, $R_{27b}$, $R_{28}$, $R_{28a}$, $R_{28c}$, $R_{29}$, $R_{30}$, X, $X^4$, $X^5$, or $X^6$.

In any aspect or embodiment described herein, the $R^1$, $R^3$, $R_{14a}$, $R_{14b}$, $R_{15}$, $R_{16}$, $R^{23}$, $R^{26}$, $R_{27a}$, $R_{27b}$, $R_{28}$, $R_{28a}$, $R_{28c}$, $R_{29}$, $R_{30}$, X, $X^4$, $X^5$, or $X^6$ can independently be covalently coupled to a linker and/or a linker to which is attached to one or more PTM, ULM, and VLM group.

In any aspect or embodiment described herein, the ULM (or when present, ULM') as described herein may be a pharmaceutically acceptable salt, enantiomer, diastereomer, solvate or polymorph thereof. In addition, in any of the aspects or embodiments described herein, the ULM (or when present, ULM') as described herein may be coupled to a PTM directly via a bond or by a chemical linker.

In any aspect or embodiment described herein, the ULM moiety is selected from the group consisting of:

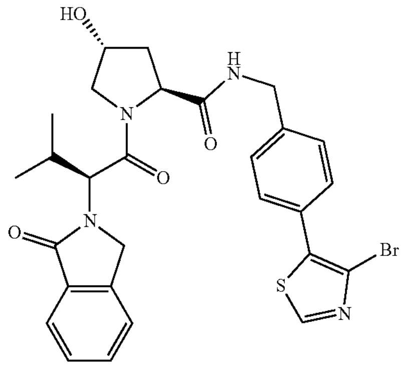

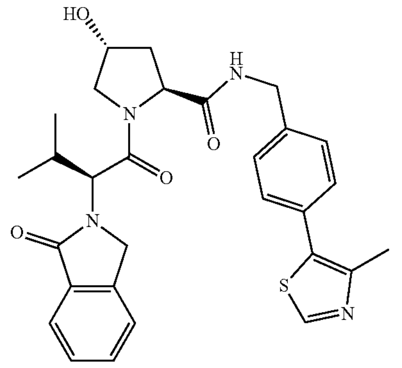

-continued
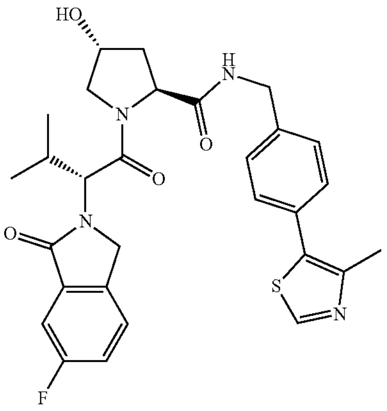
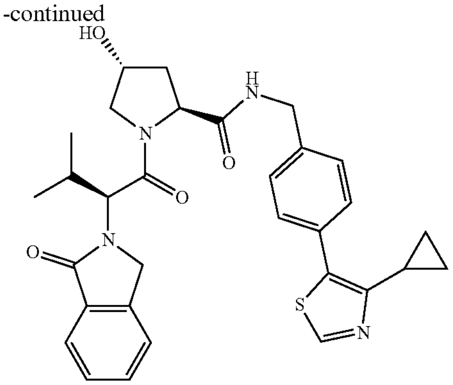
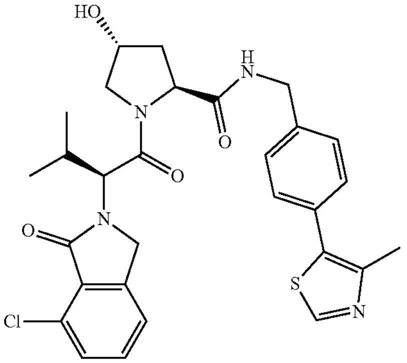
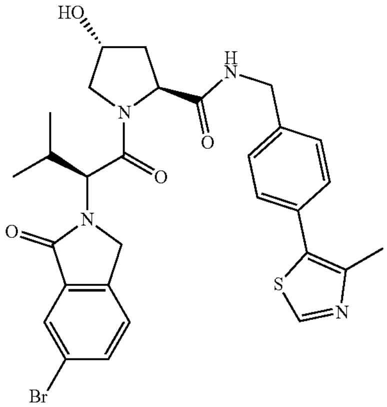
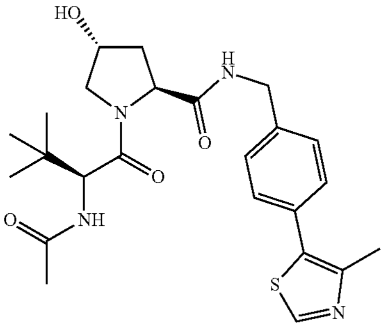
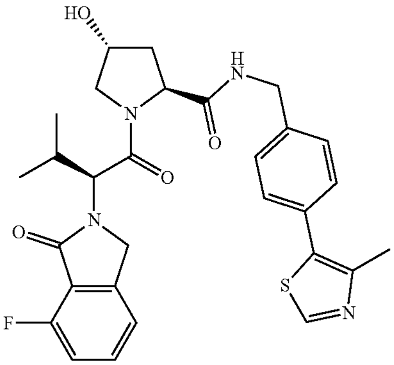
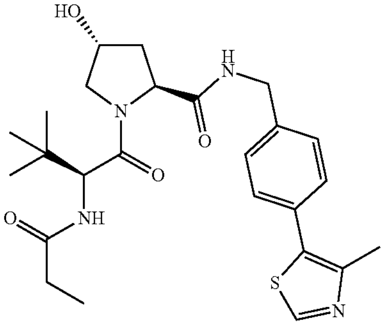
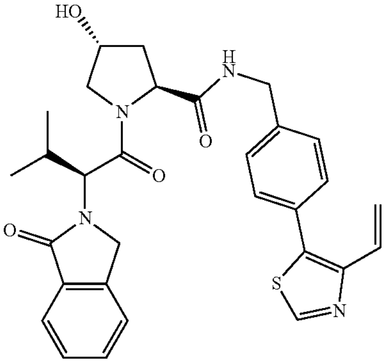

-continued
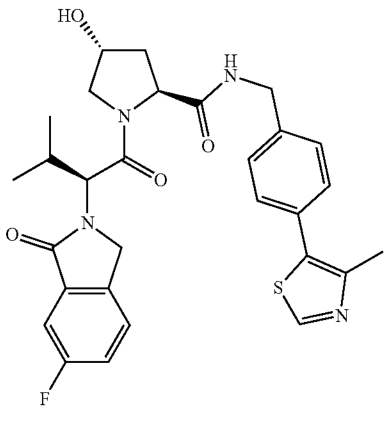
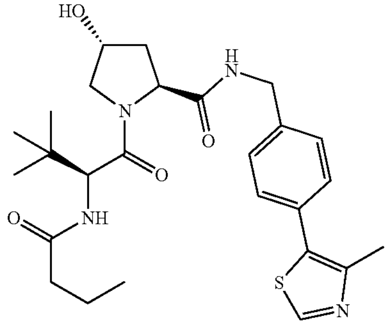
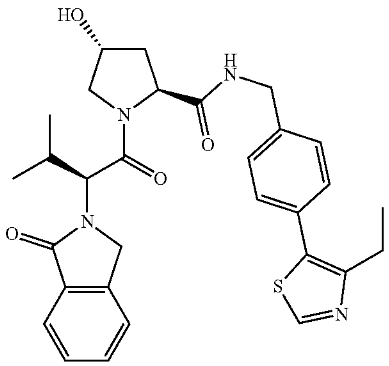
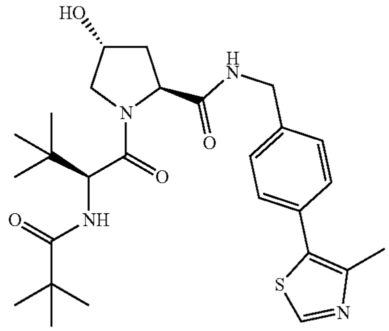
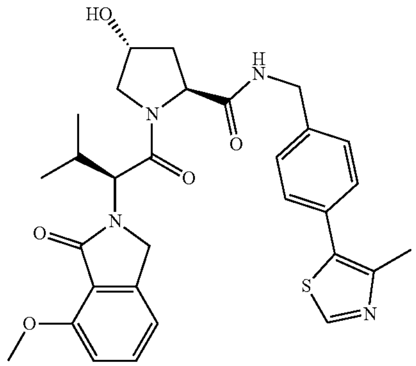
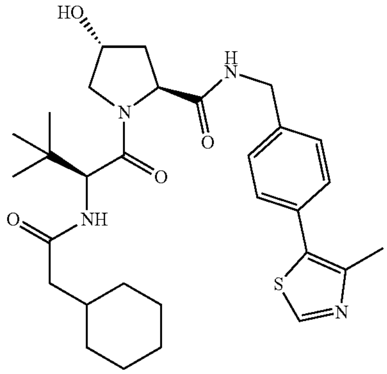
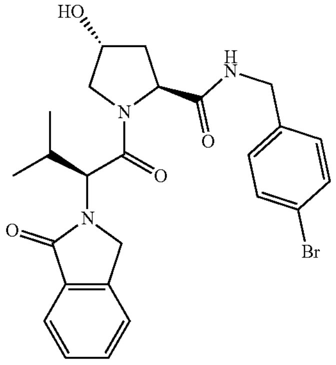
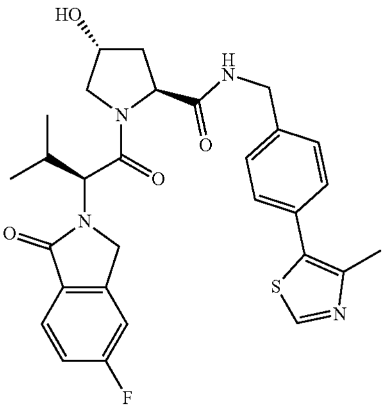

-continued
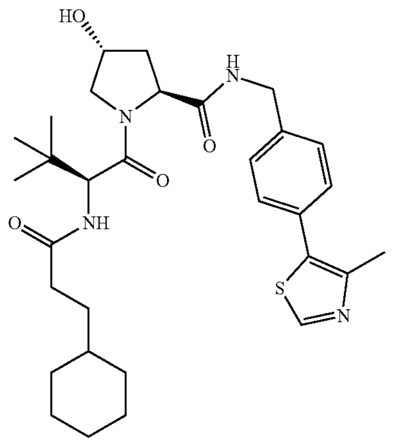
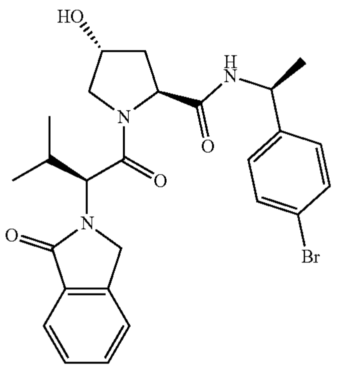
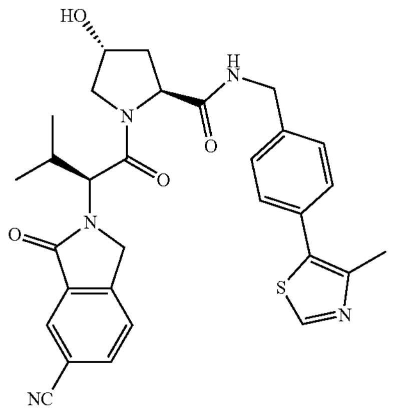
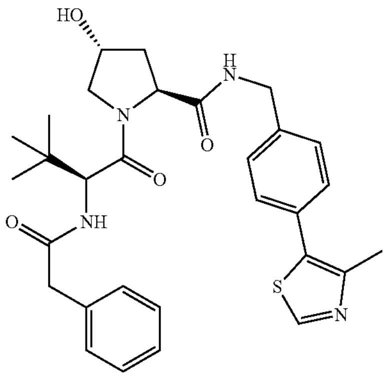
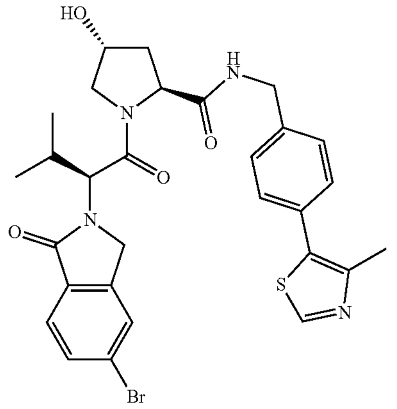
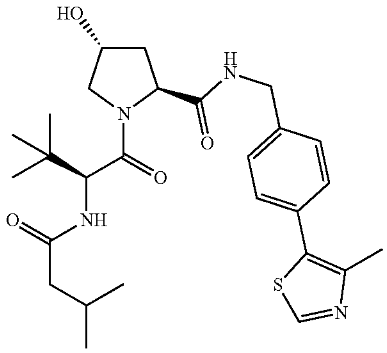
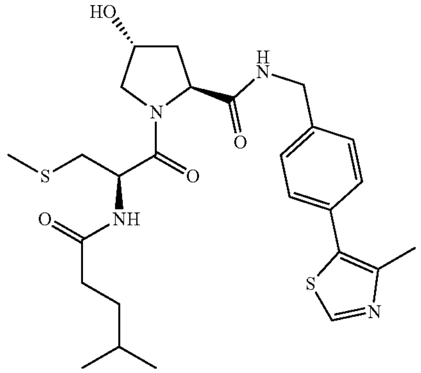
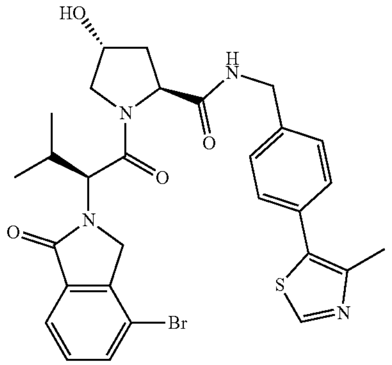

-continued
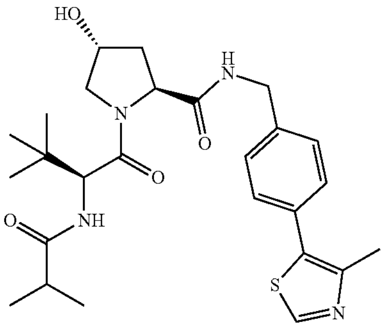
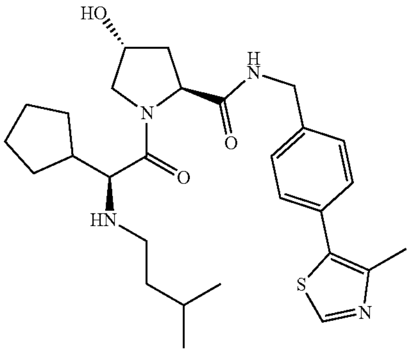
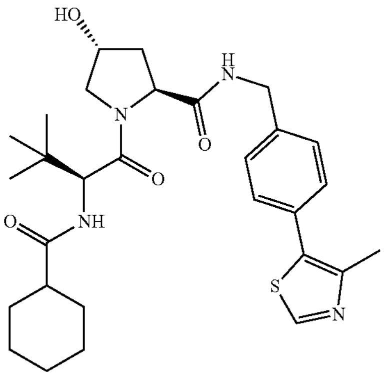
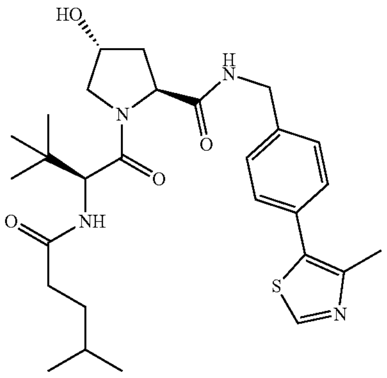
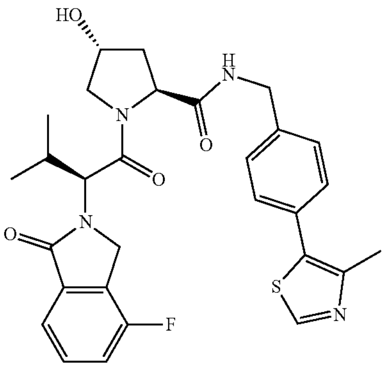
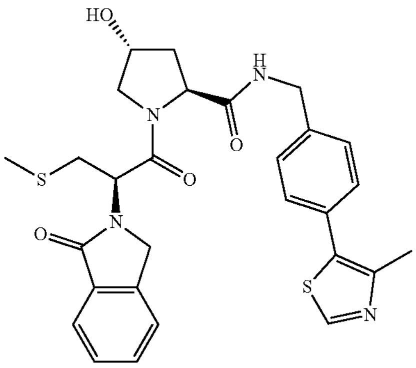
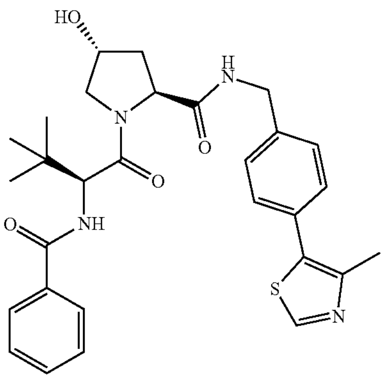
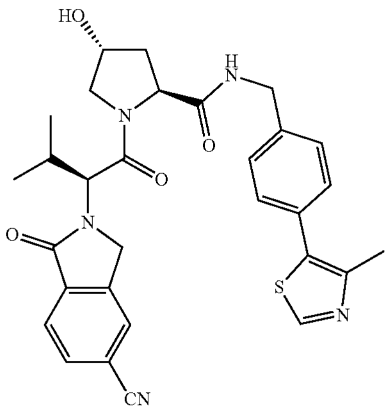

-continued
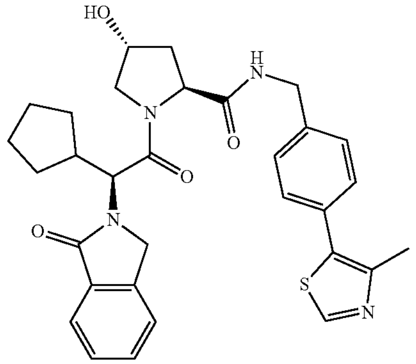
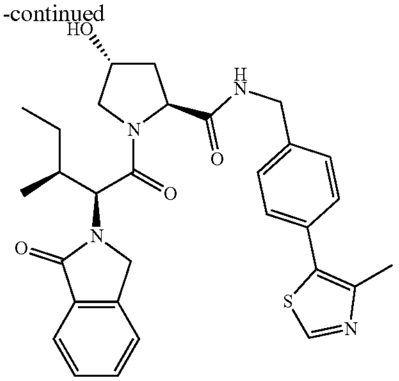
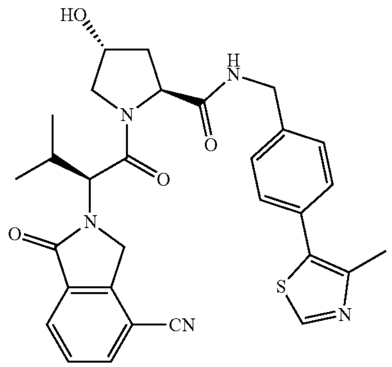
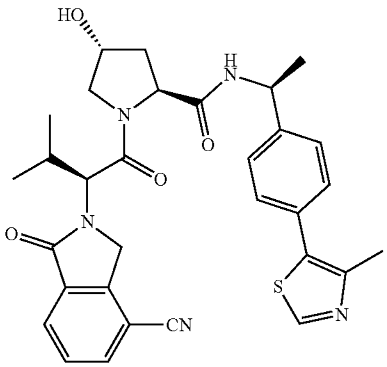
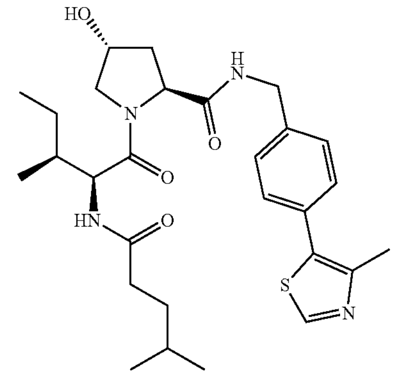
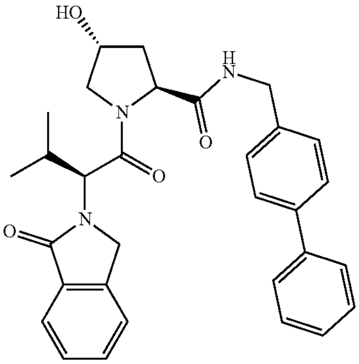
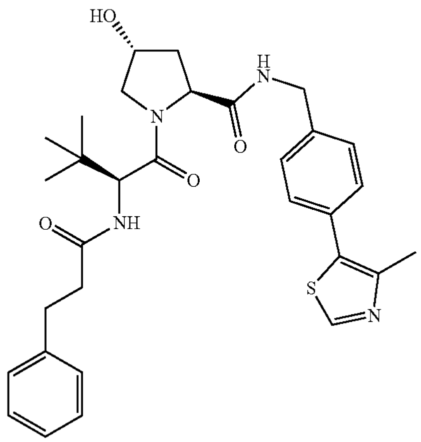
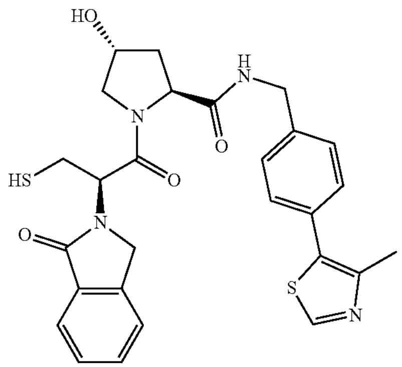

-continued
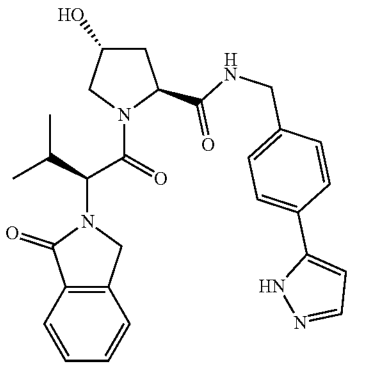
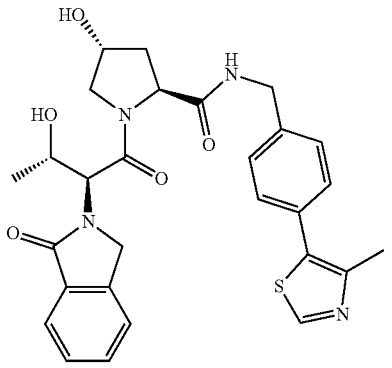
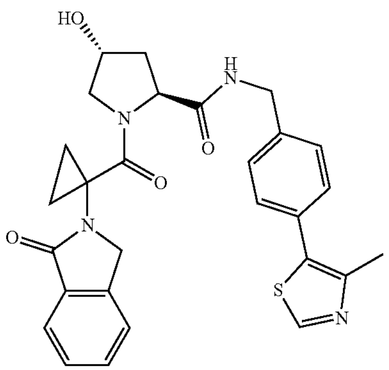
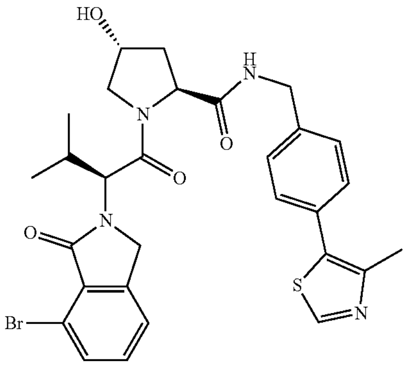
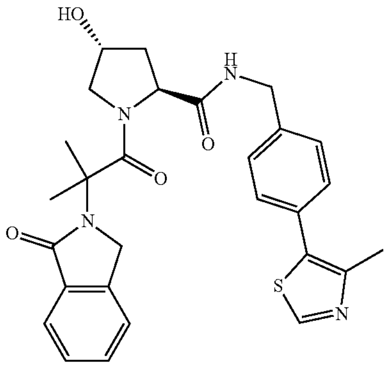
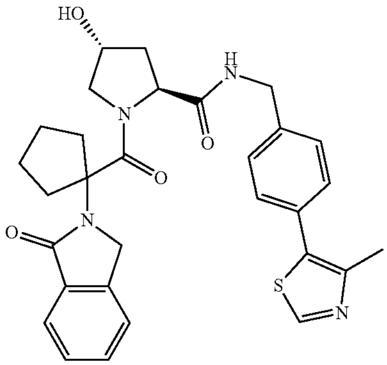
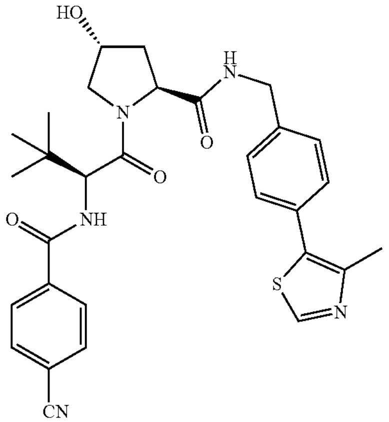
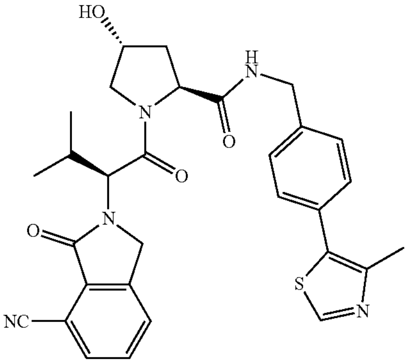

-continued
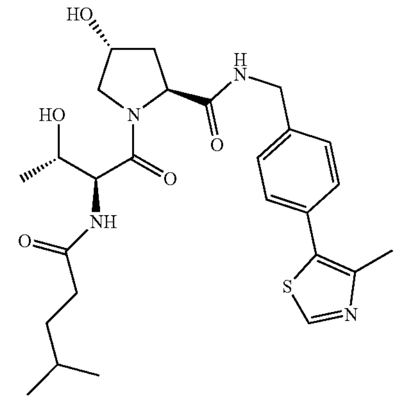
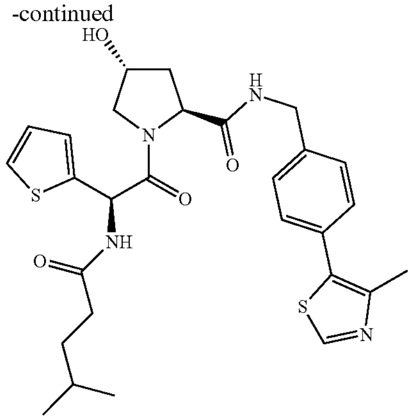
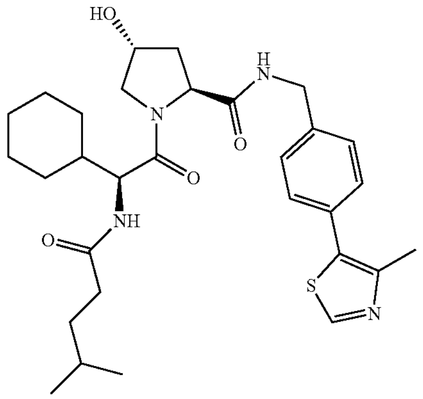
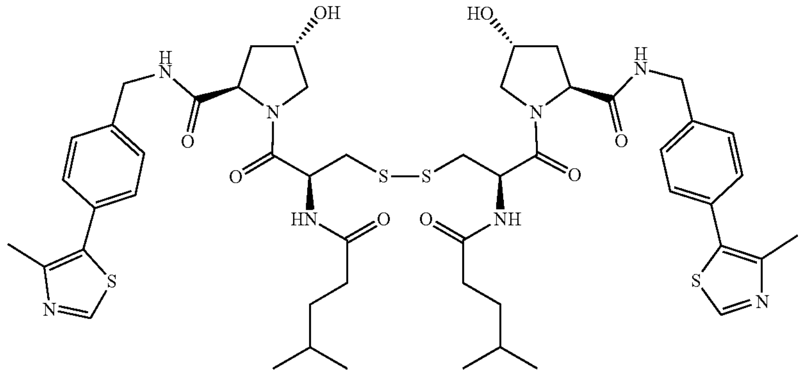
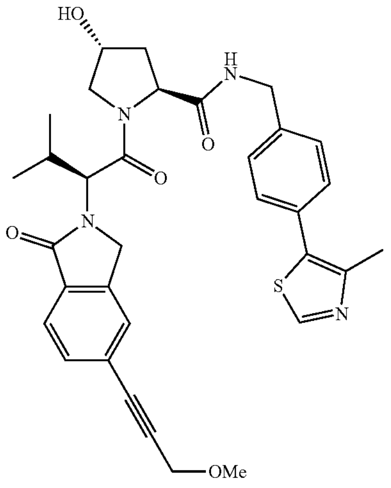
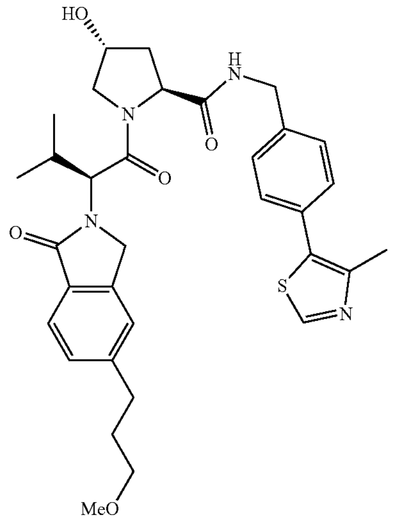

-continued
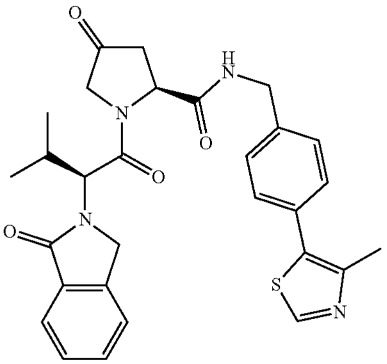
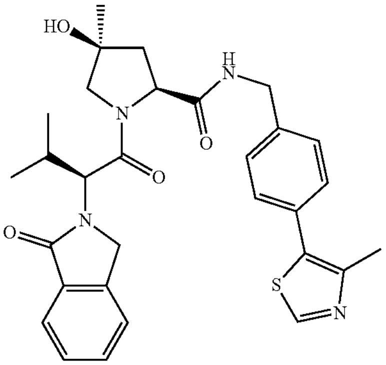
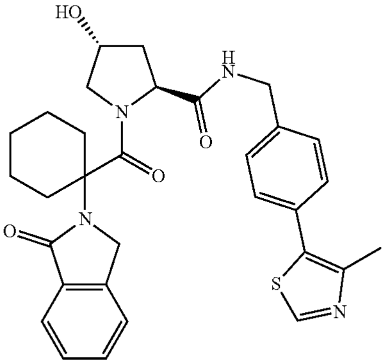
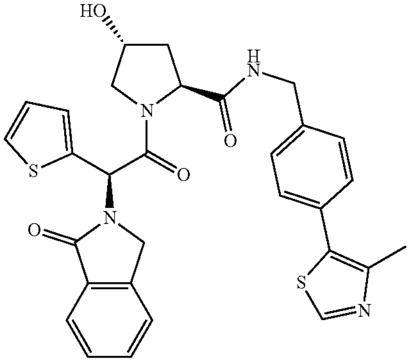
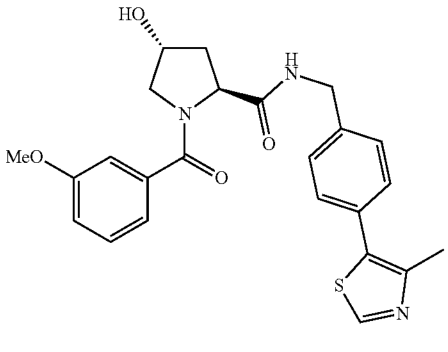
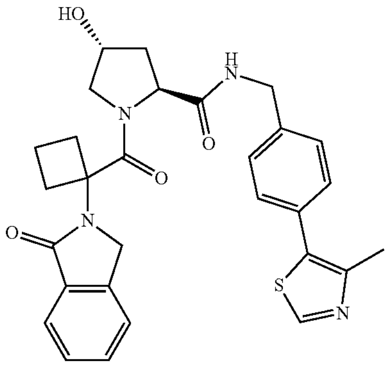
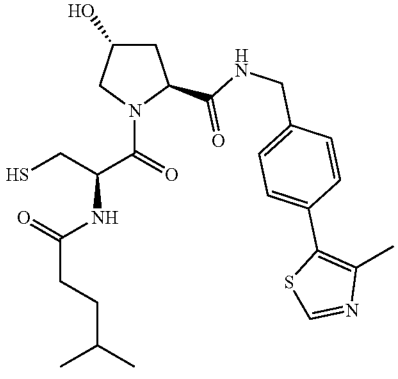
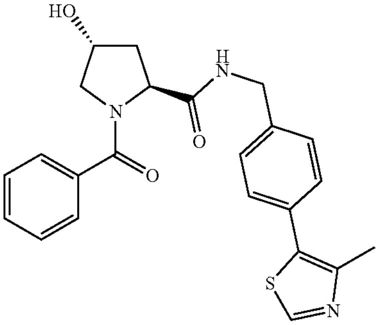

-continued
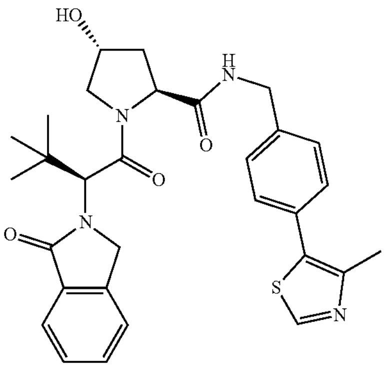
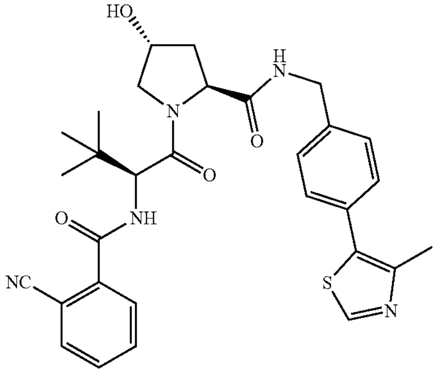
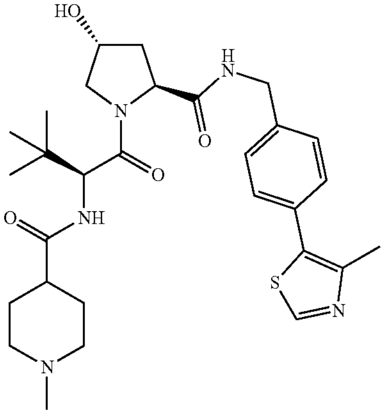
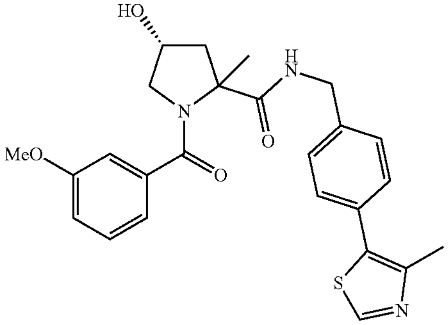
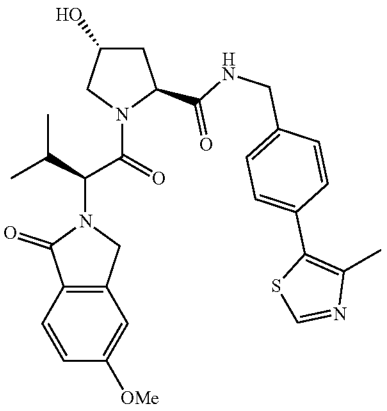
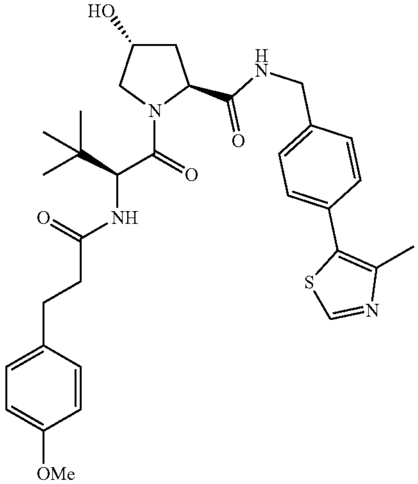
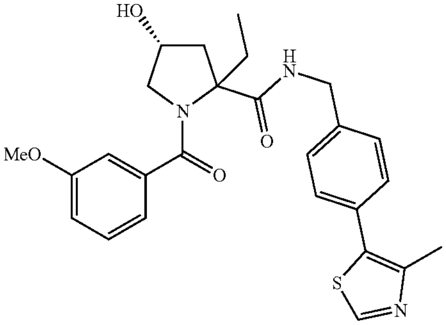
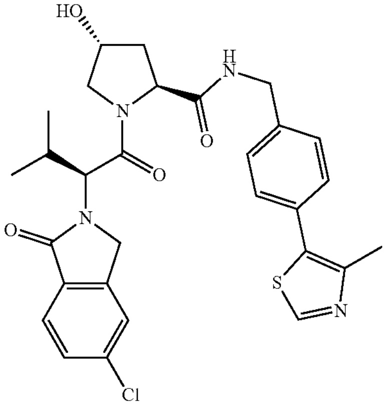

-continued
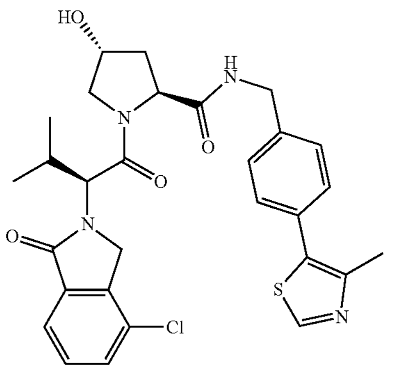
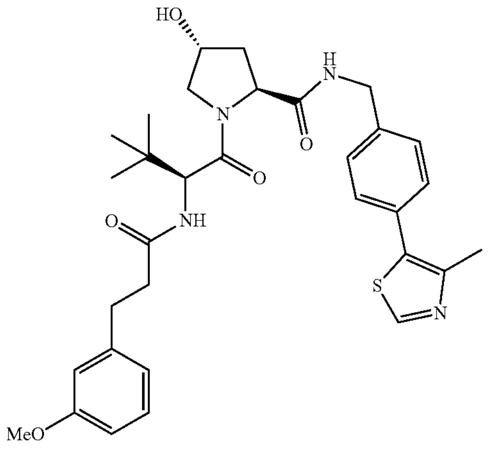
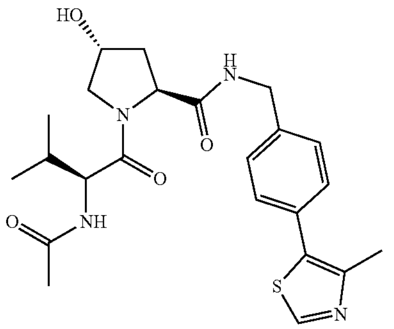
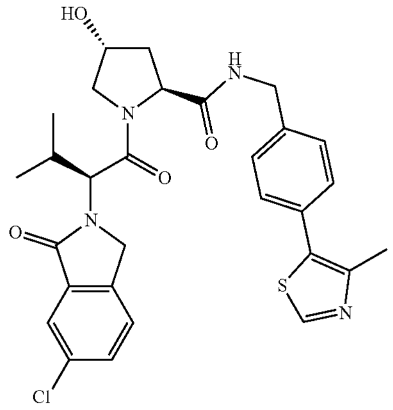
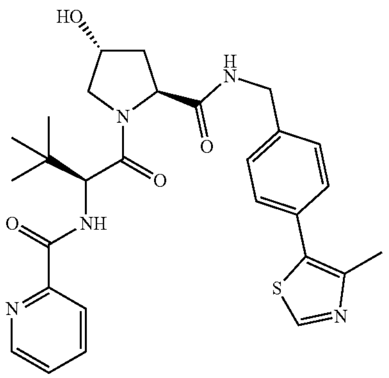
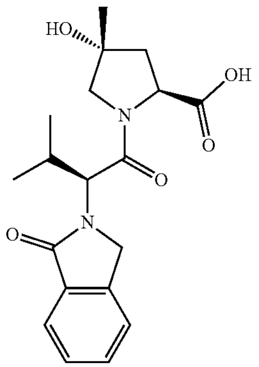
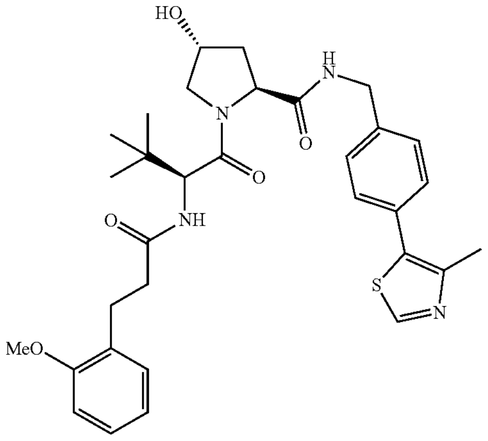
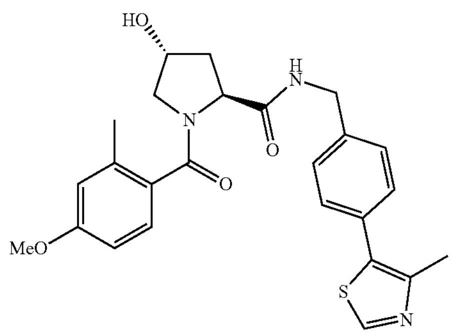

-continued
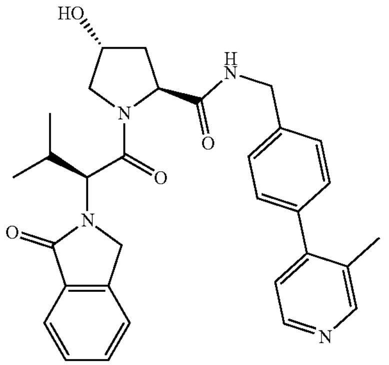
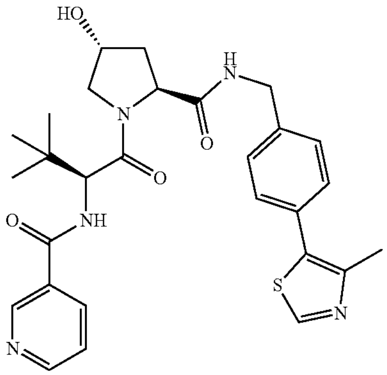
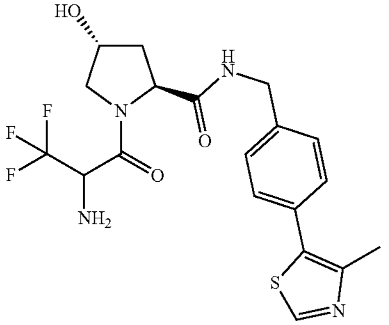
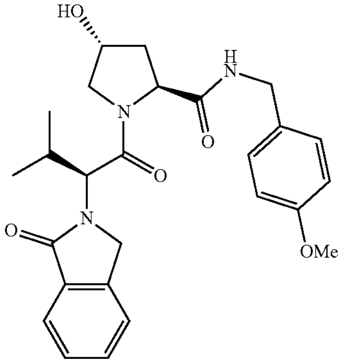
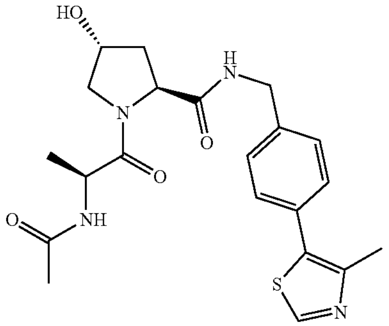
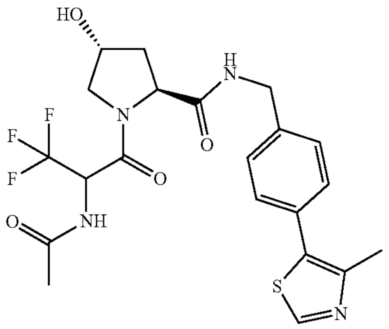
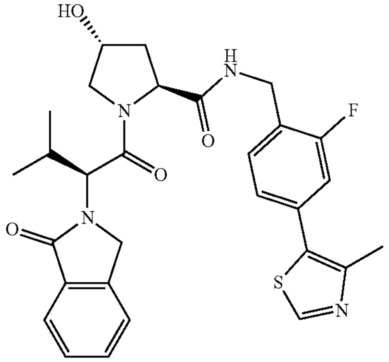
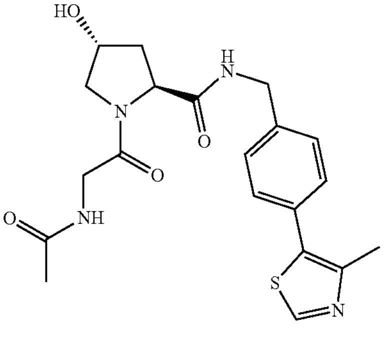

-continued
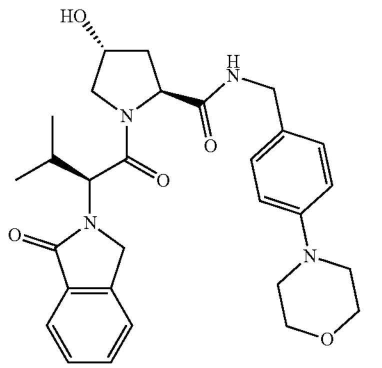
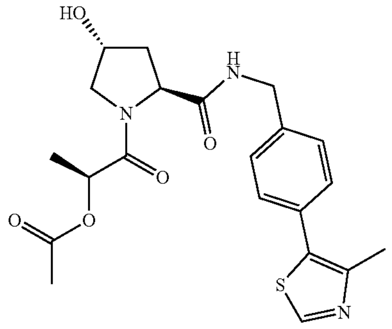
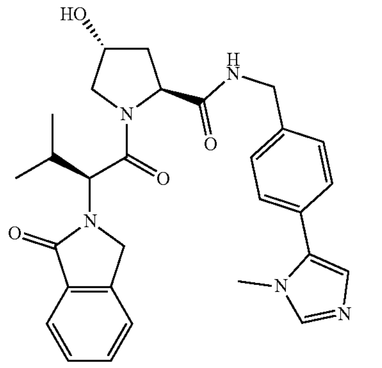
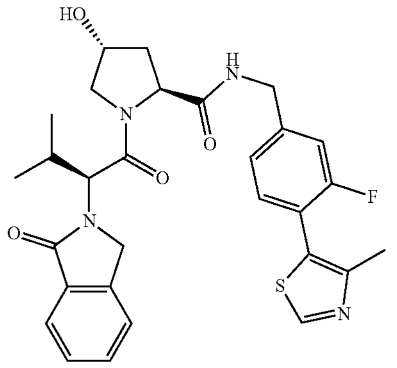
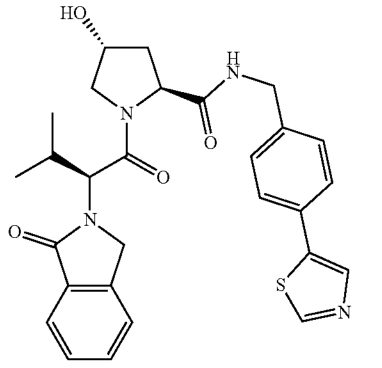
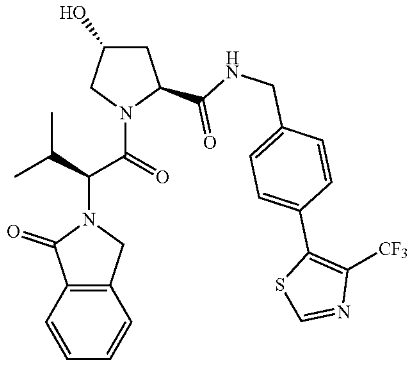
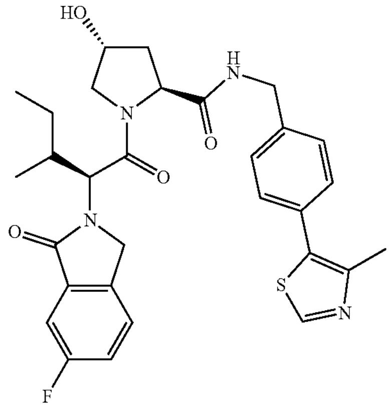
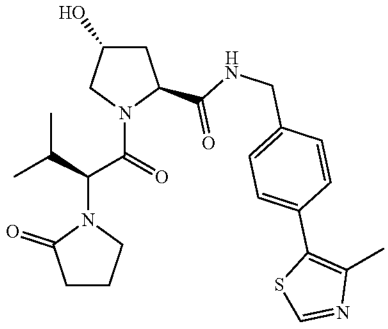

-continued
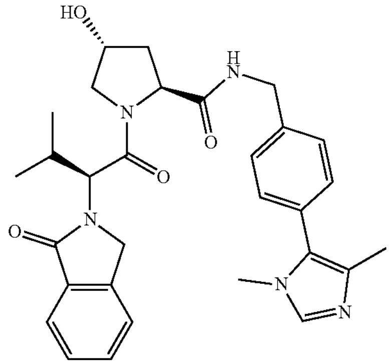
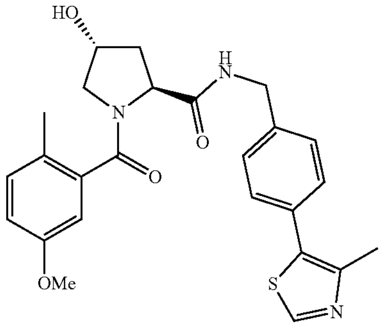
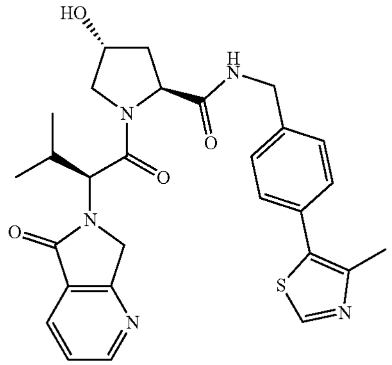
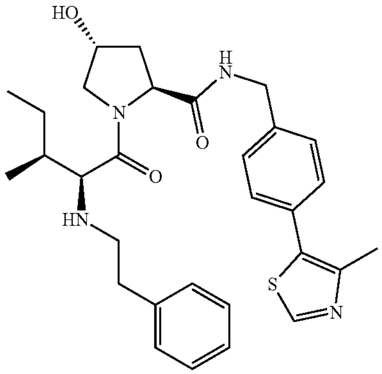
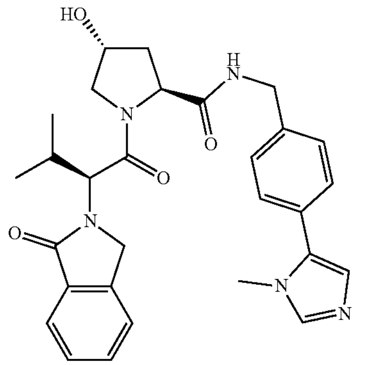
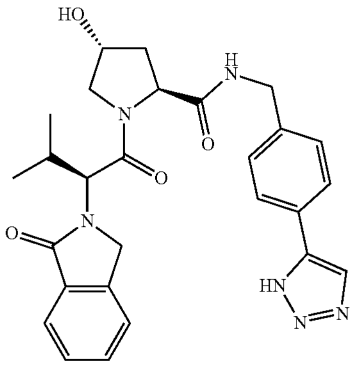
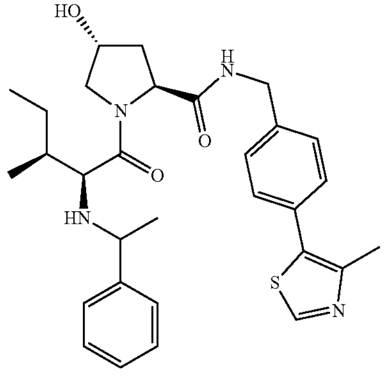
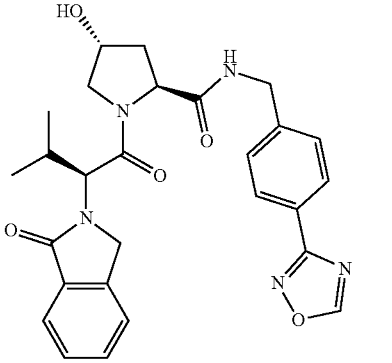

-continued
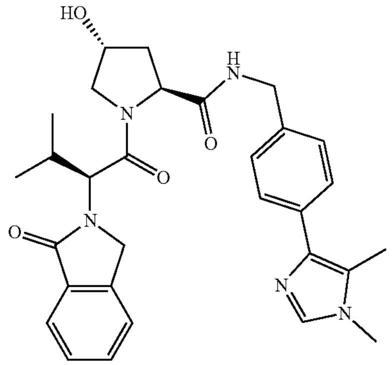
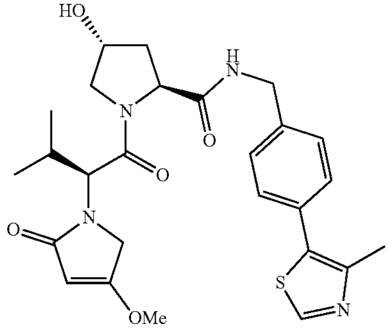
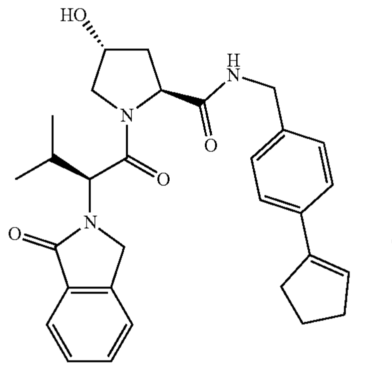
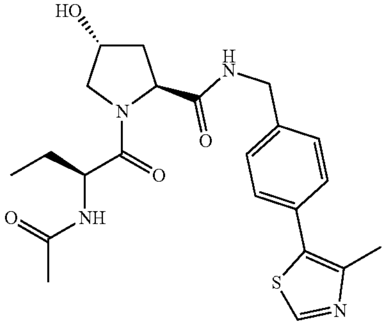
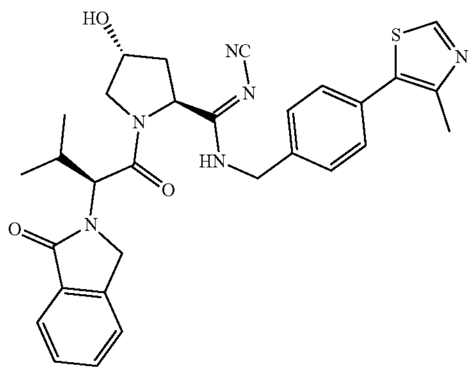
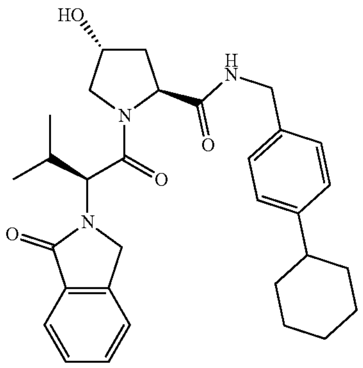
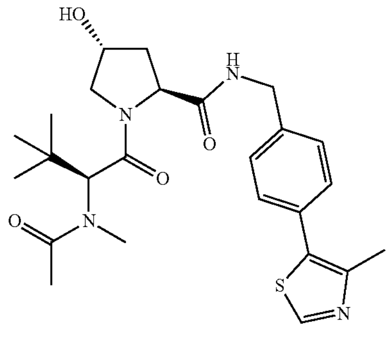
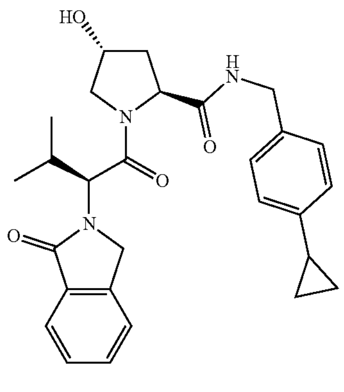

-continued
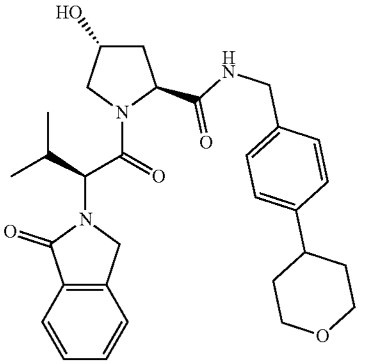
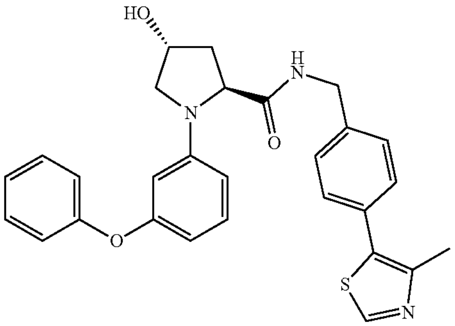
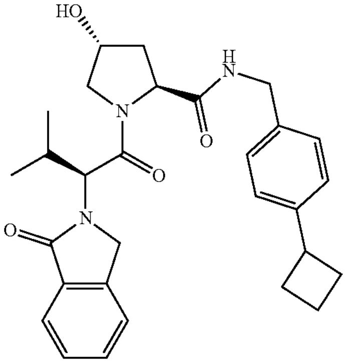
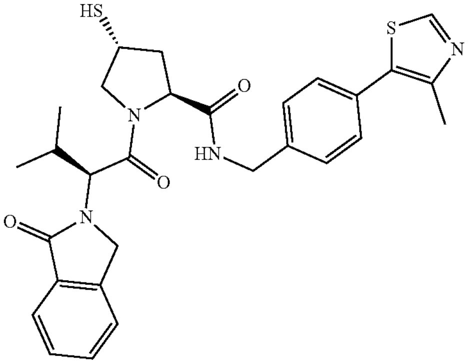
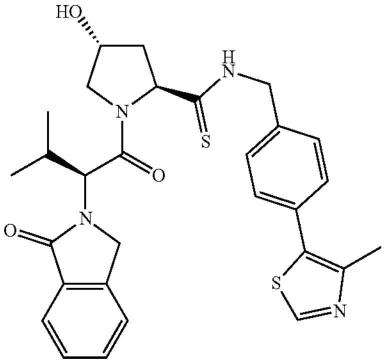
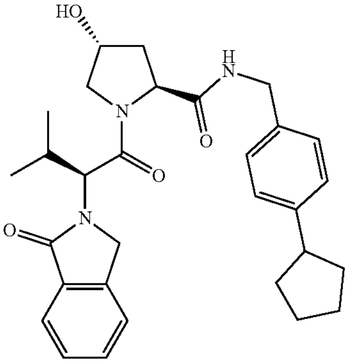
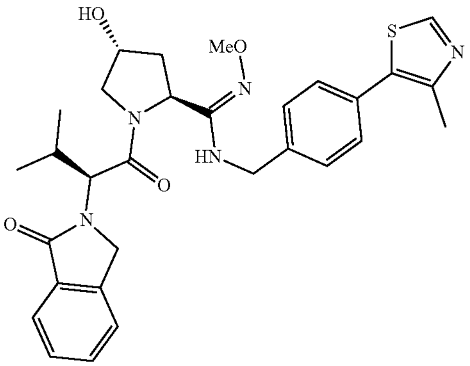
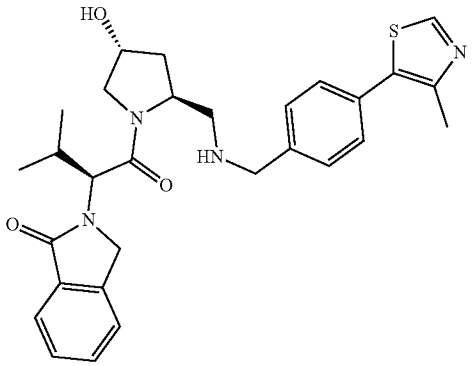

-continued
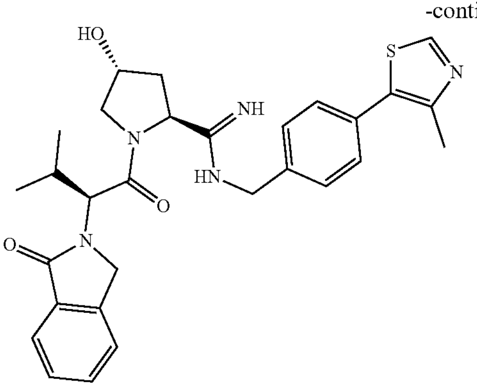
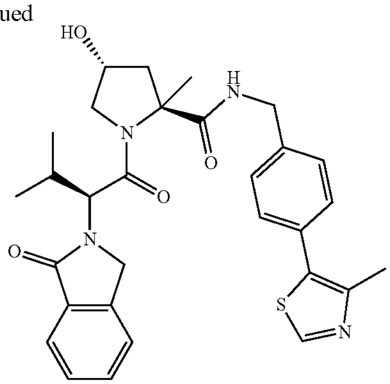
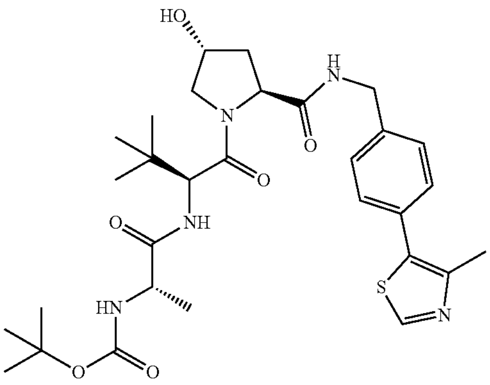
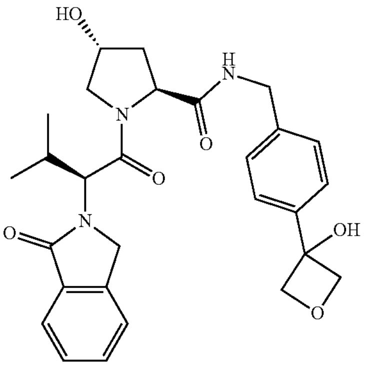
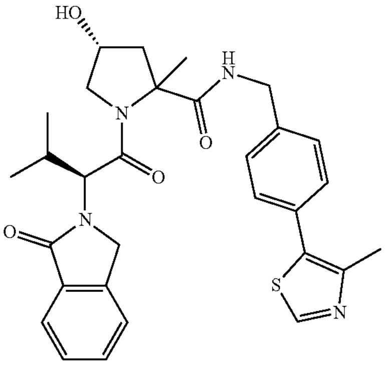
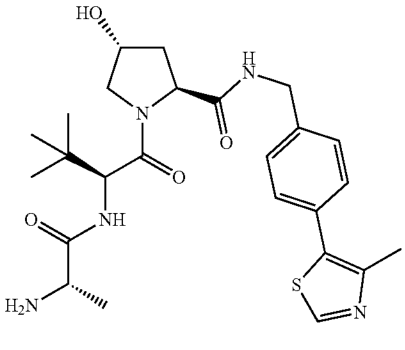
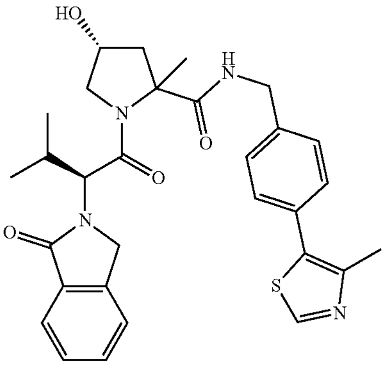
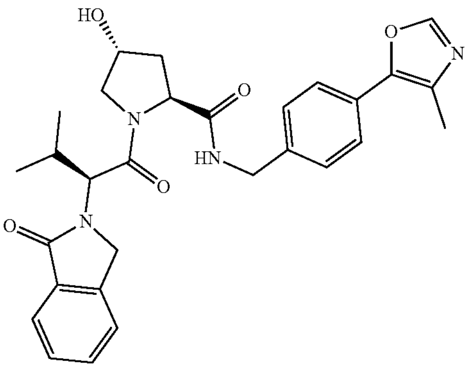

-continued
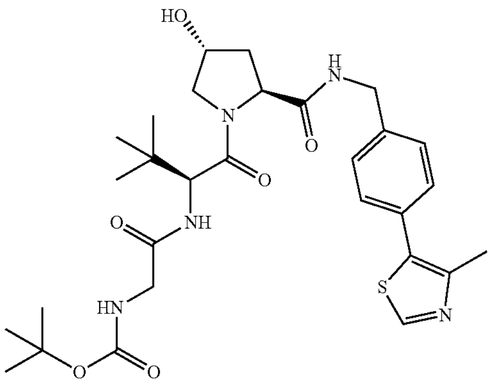
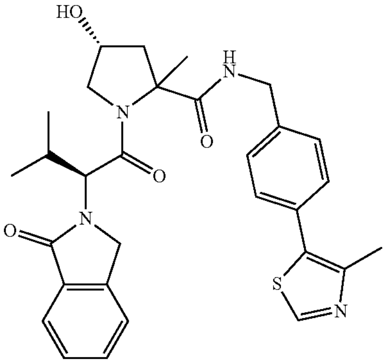
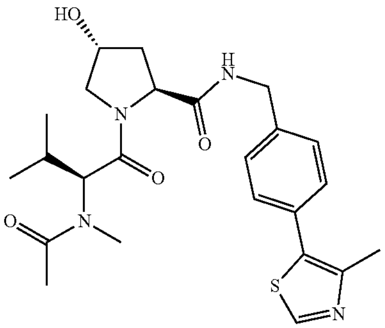
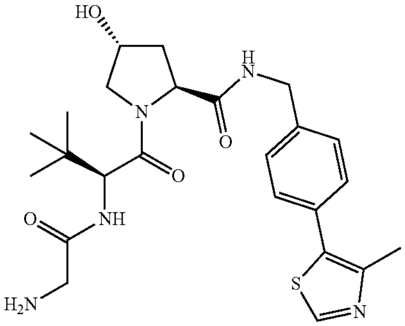
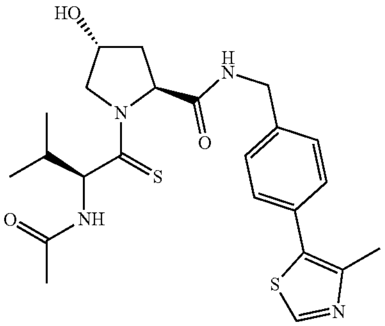
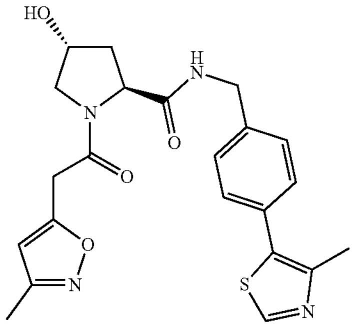
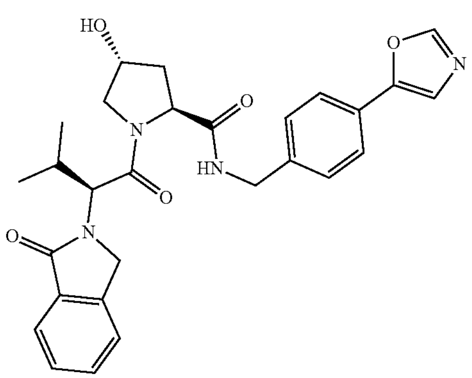
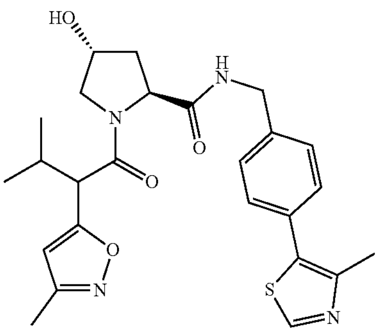

-continued
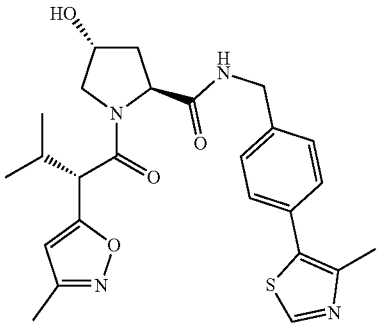
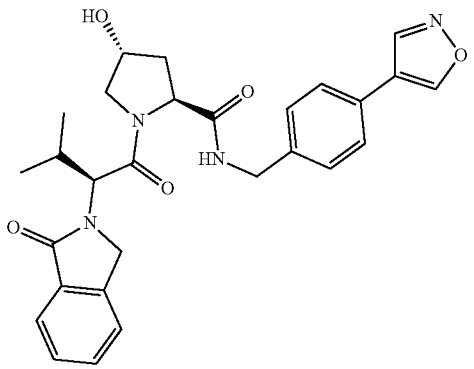
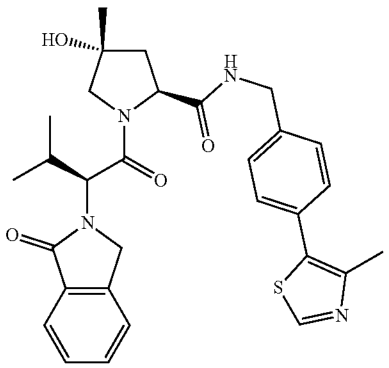
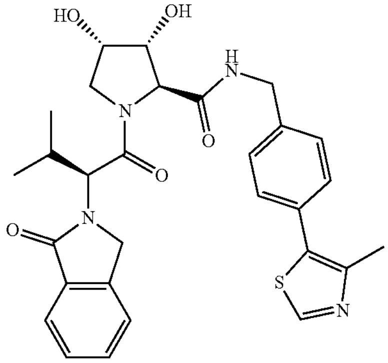
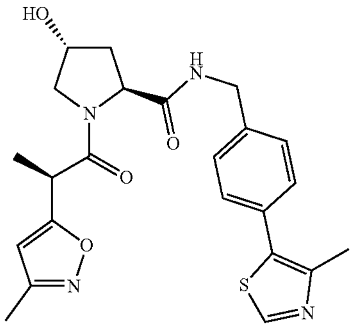
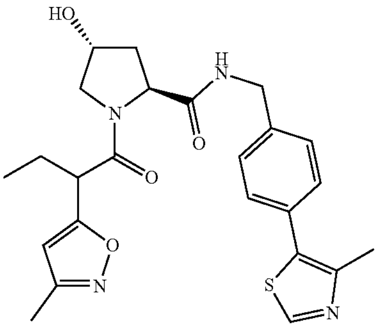
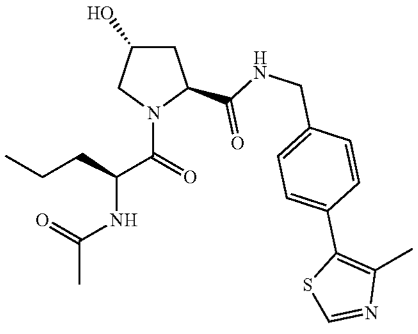
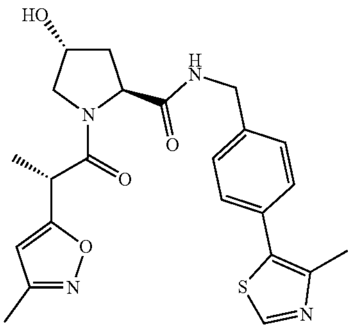

-continued
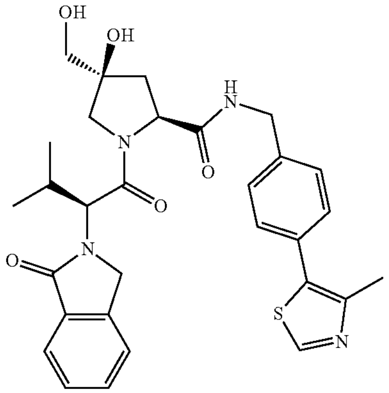
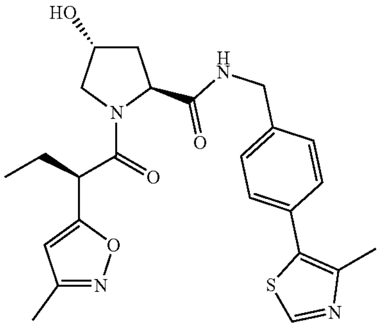
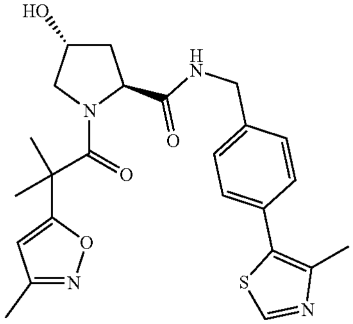
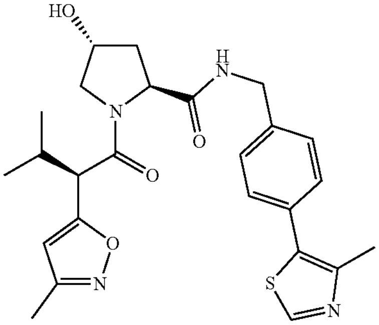
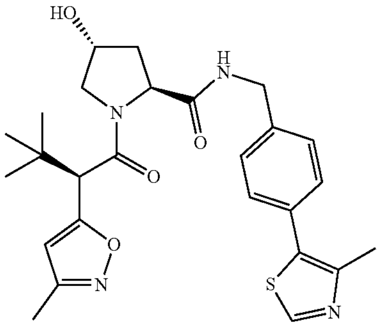
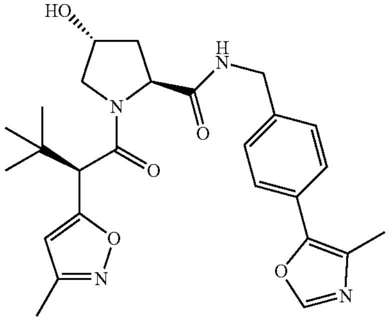
-continued
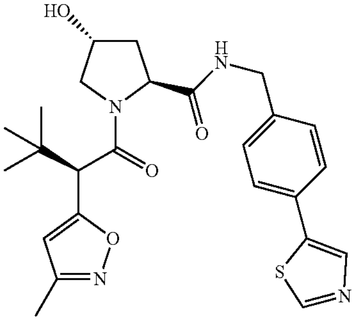

-continued
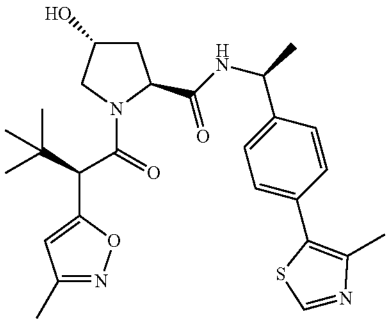
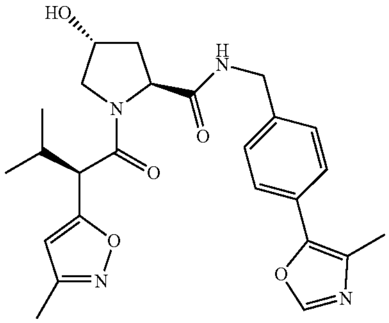
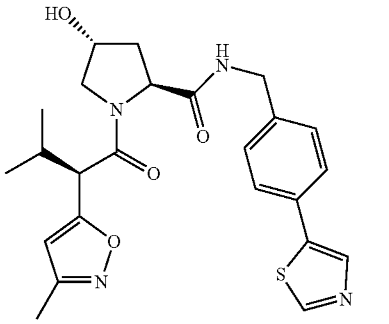
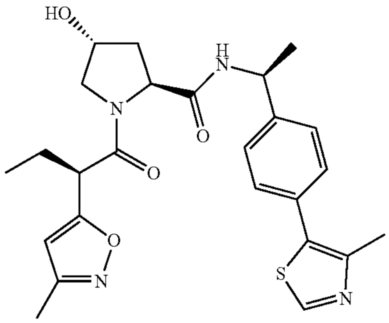
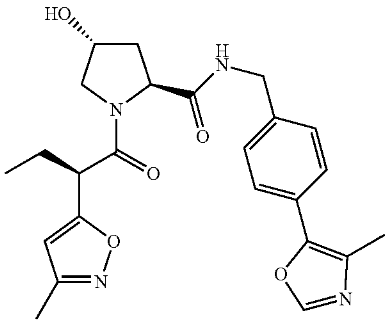
-continued
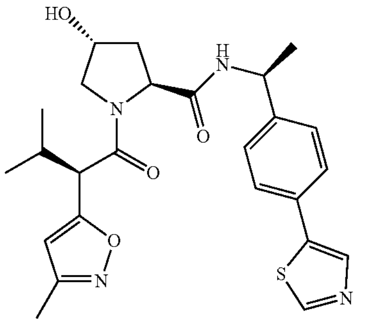
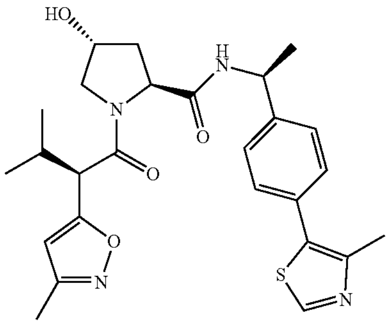
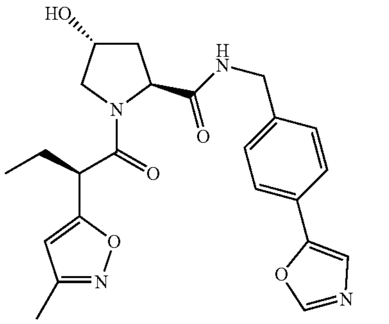
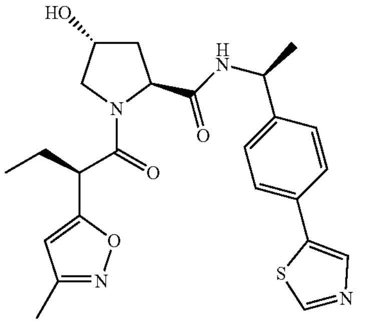
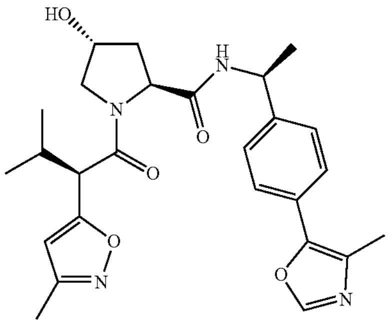

-continued
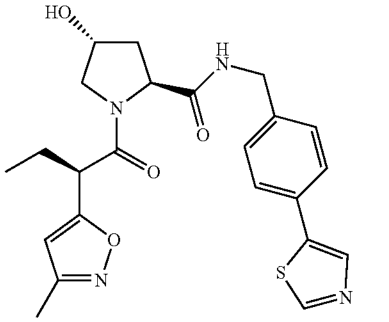
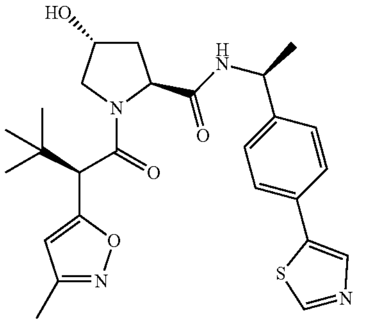
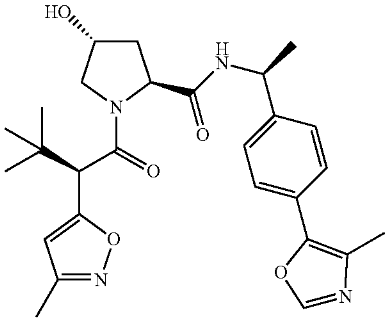
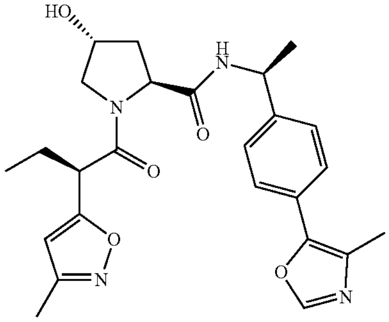
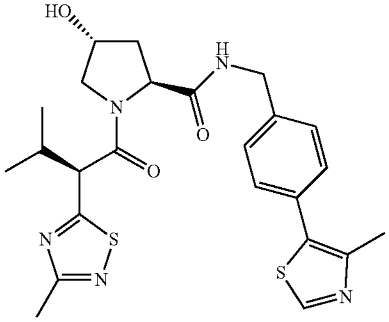
-continued
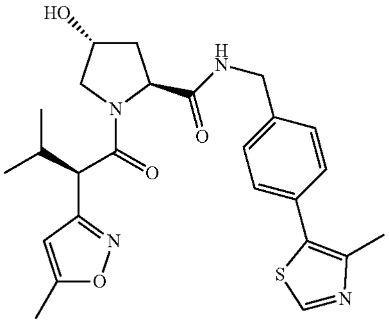
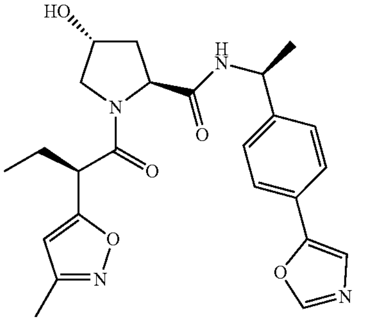
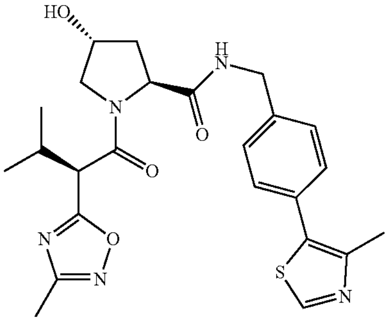
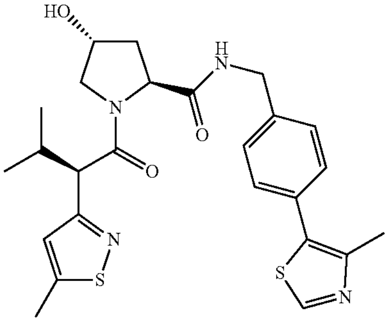
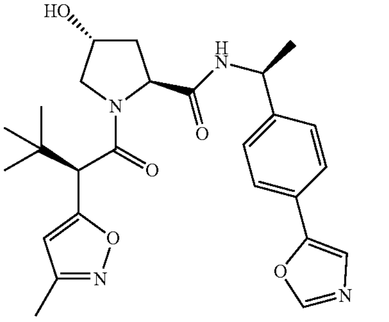

-continued
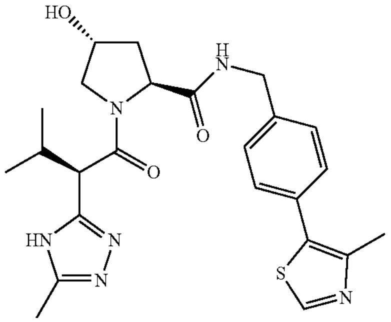
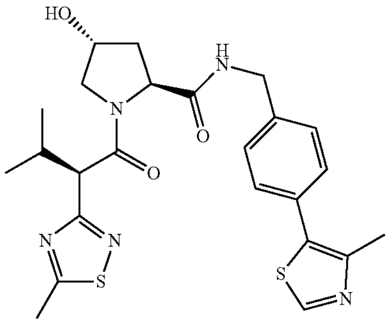
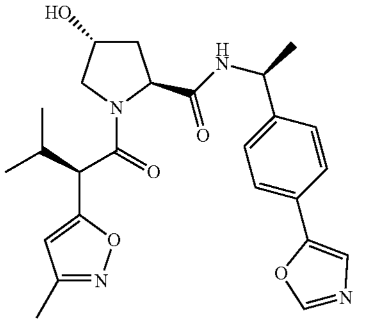
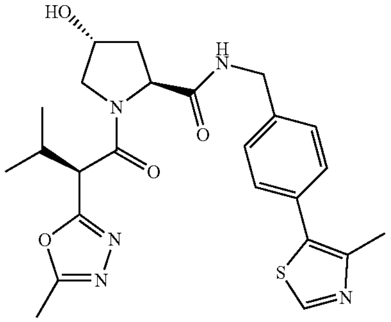
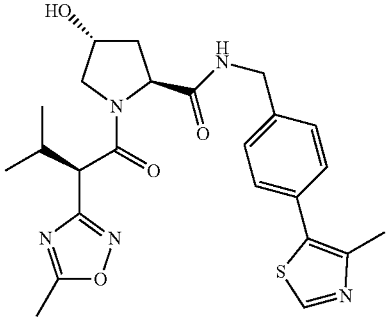
-continued
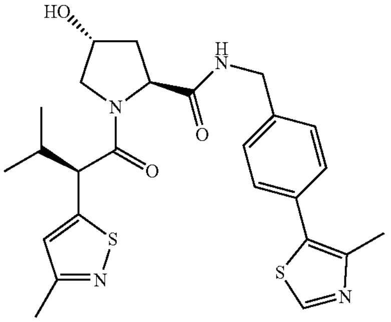
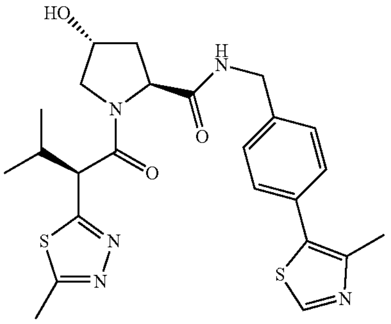
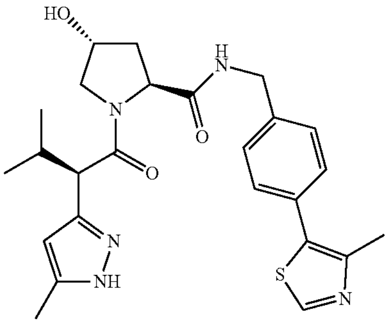
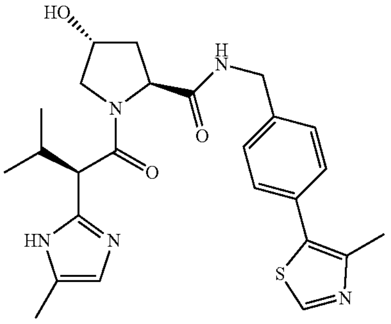
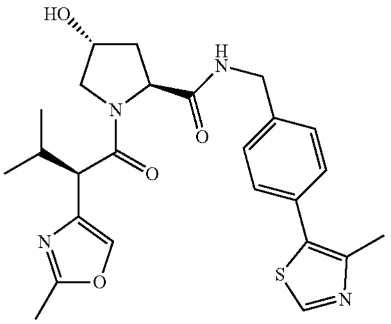

-continued
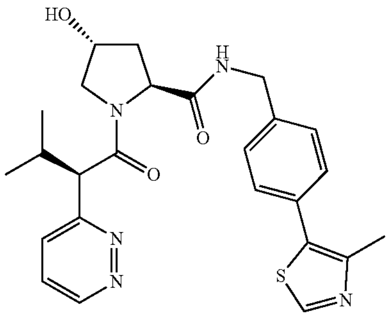
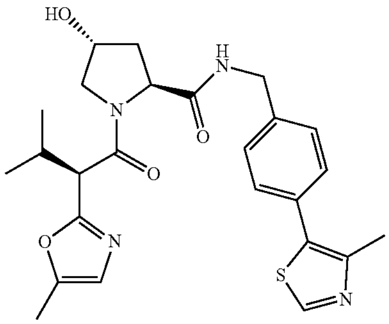
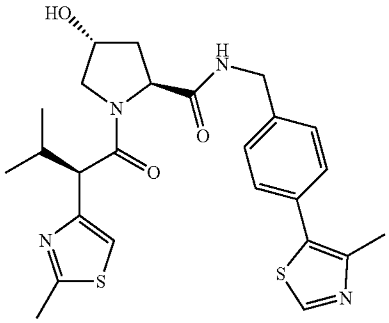
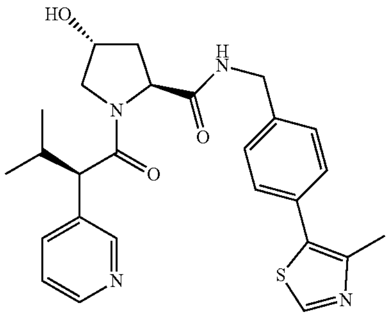
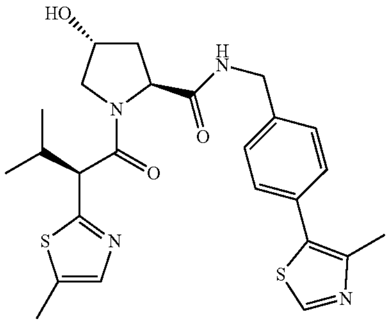
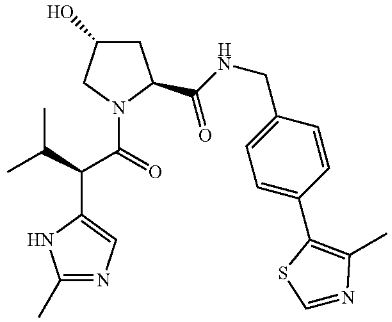
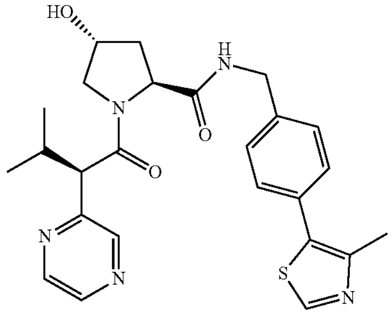
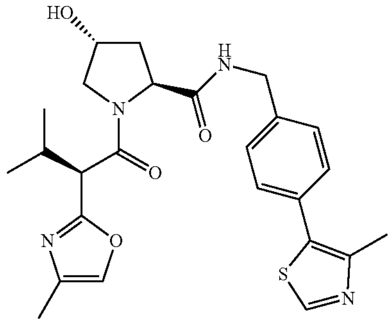
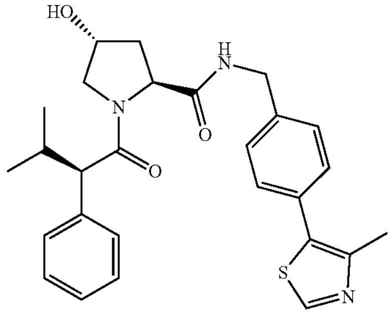
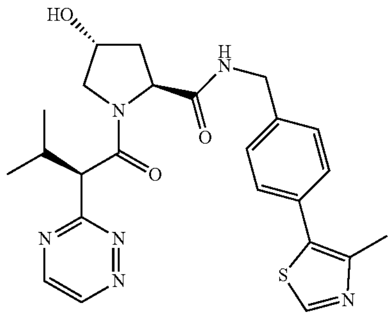

-continued
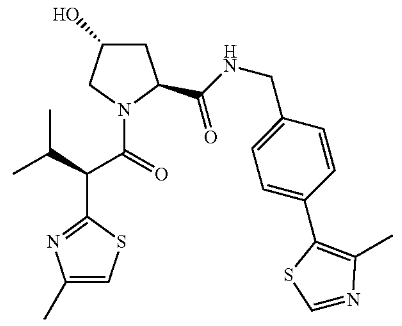
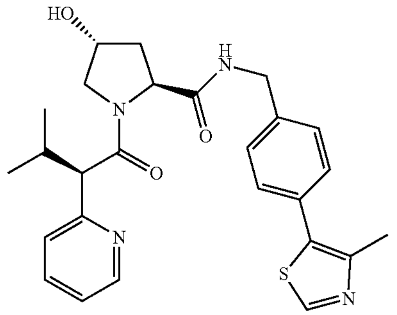
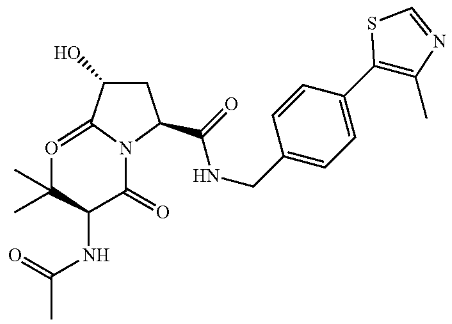
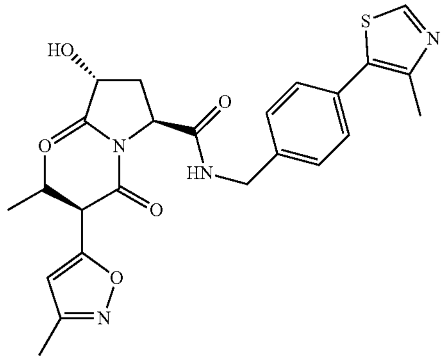
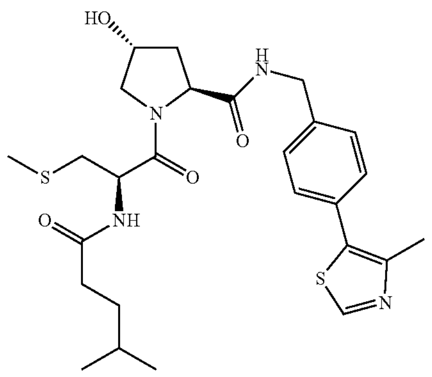
-continued
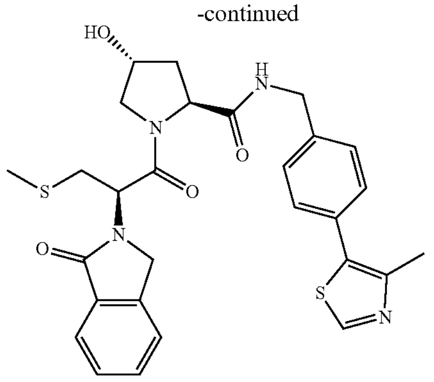
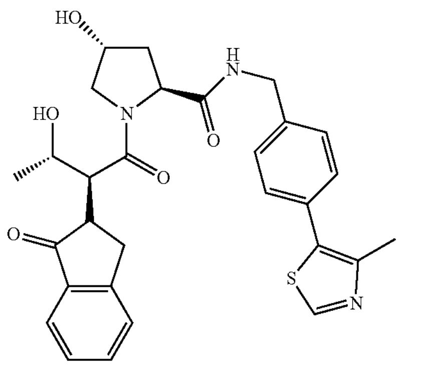
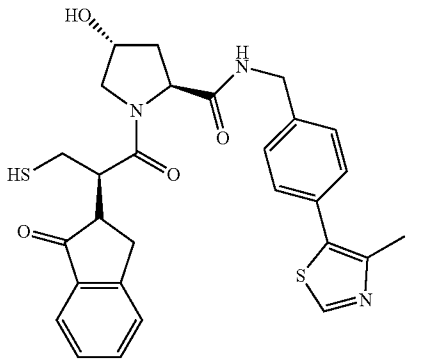
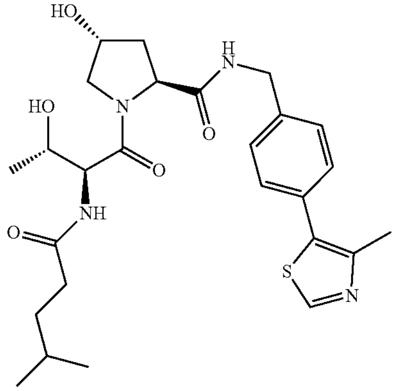

-continued
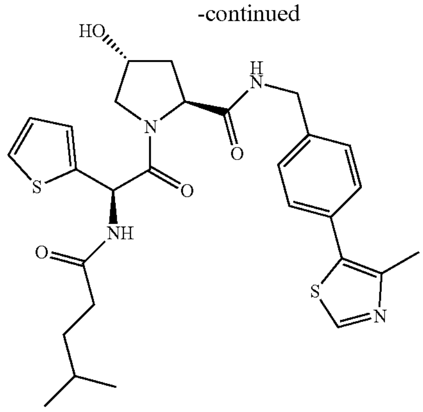
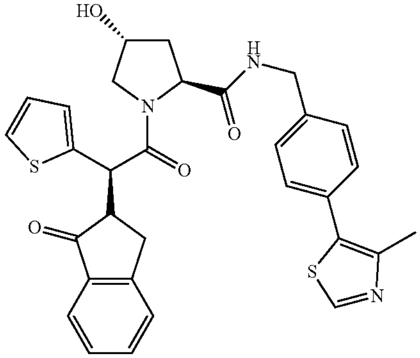
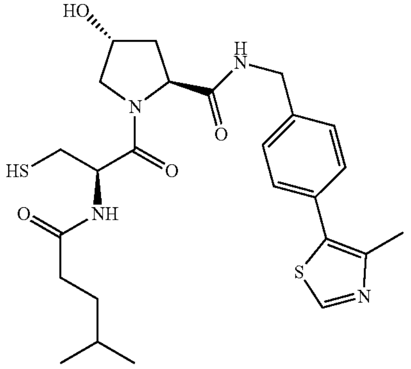
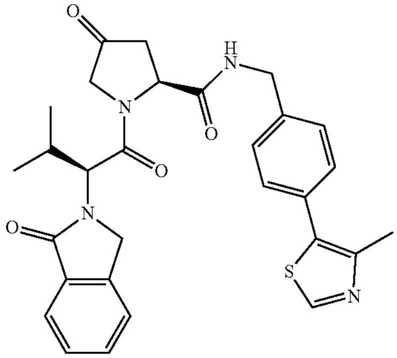
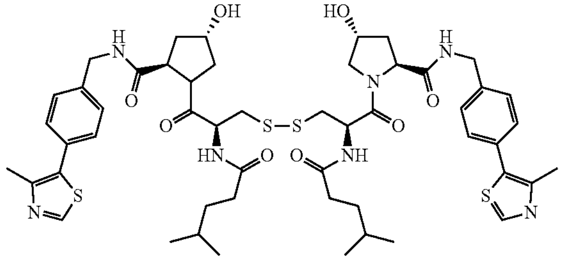
-continued
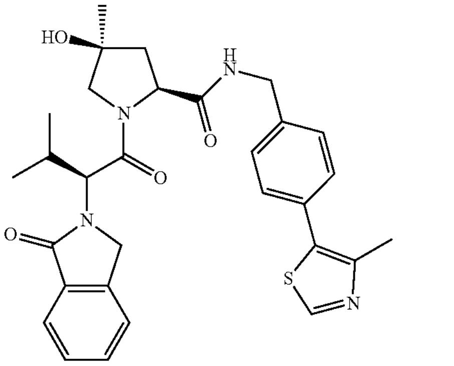
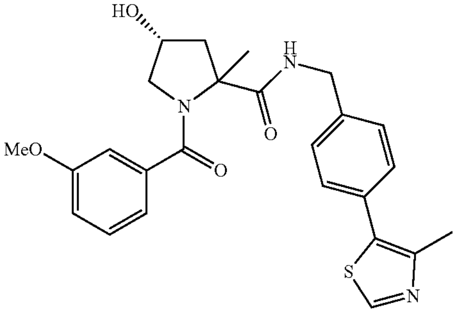
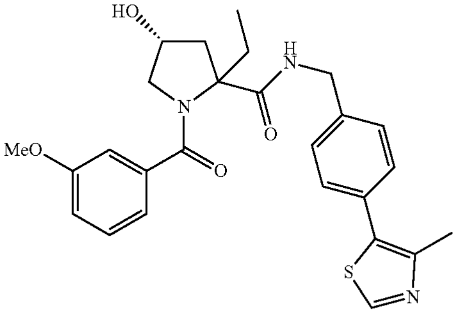
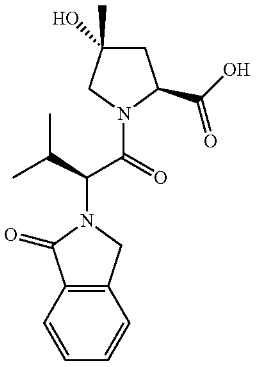
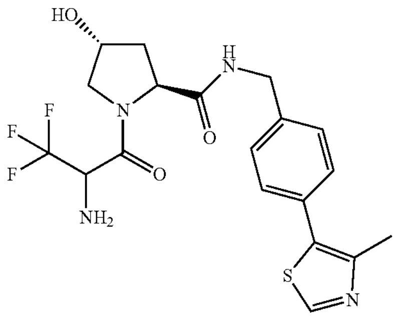

-continued
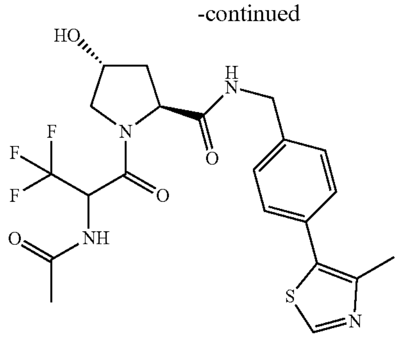
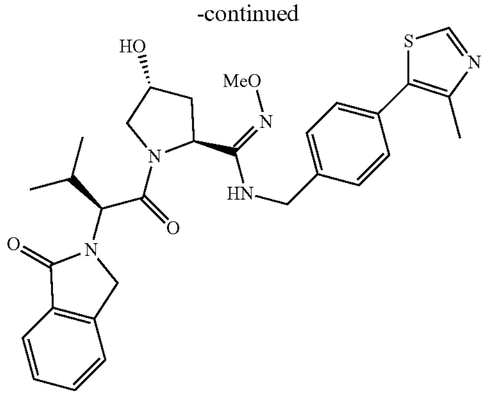
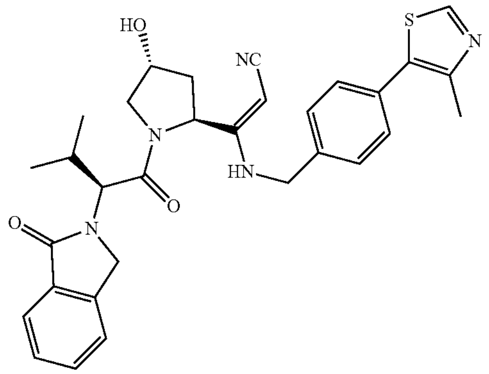
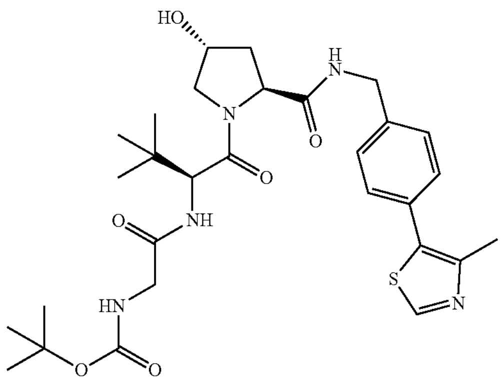
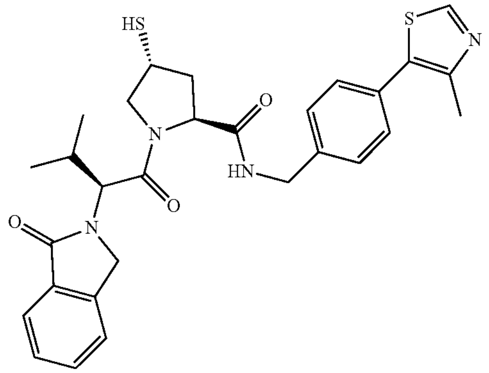
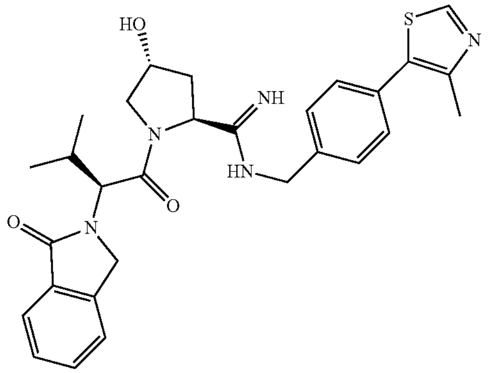
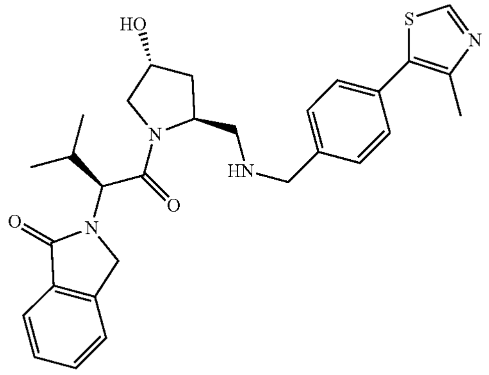
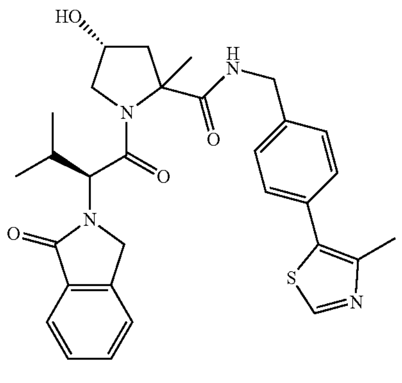
-continued -continued
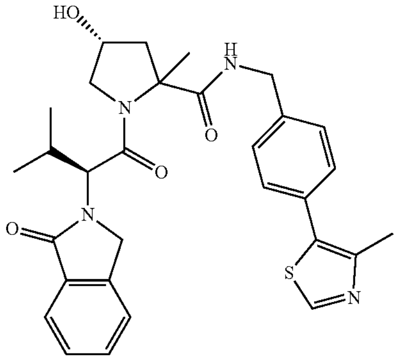
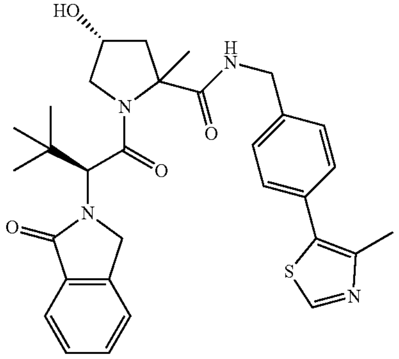
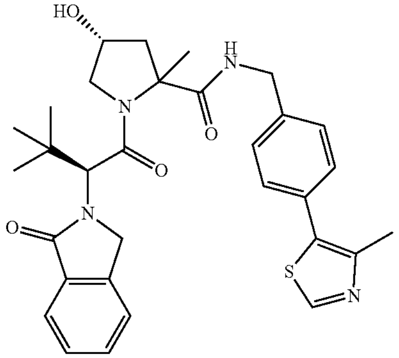
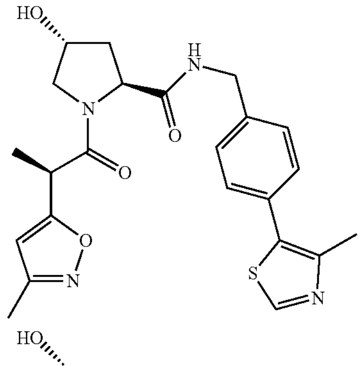
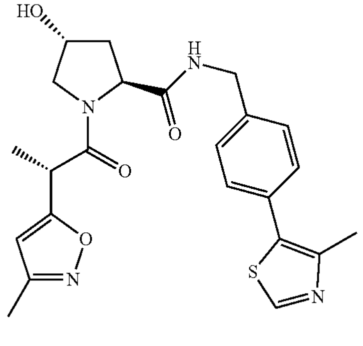
-continued
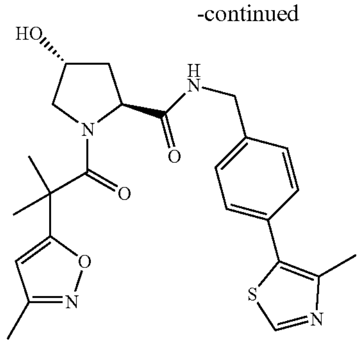
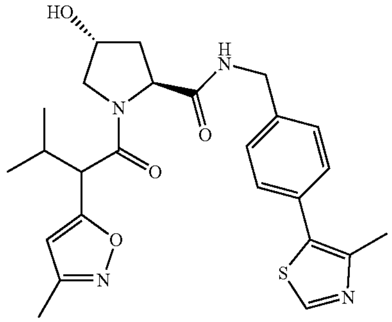
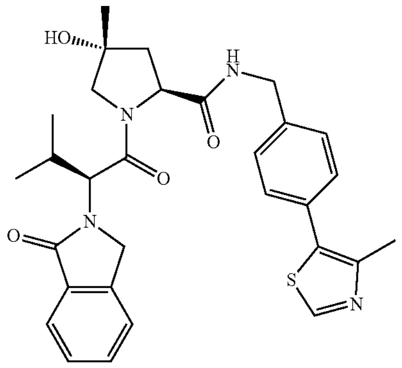
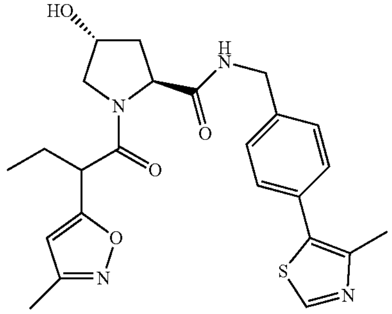
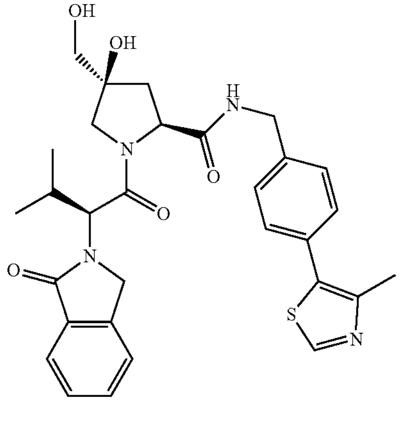

-continued
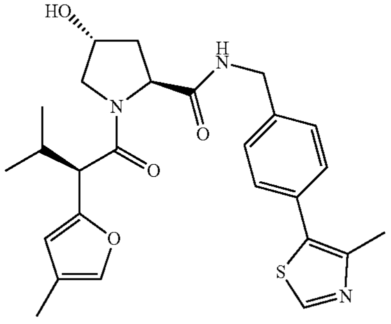
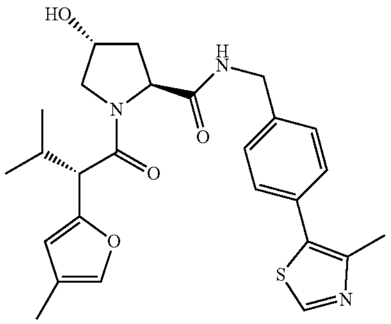
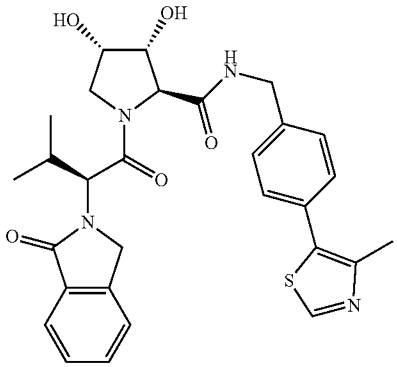
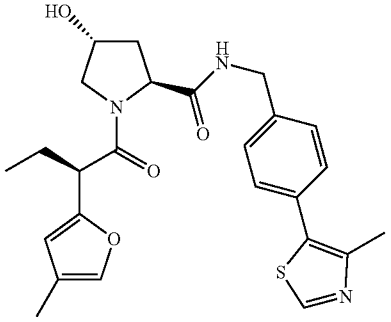
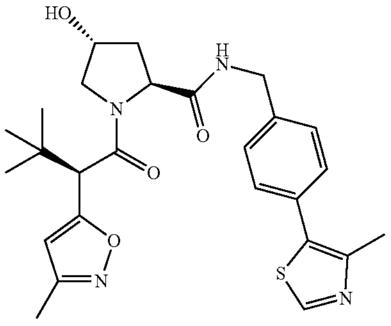
-continued
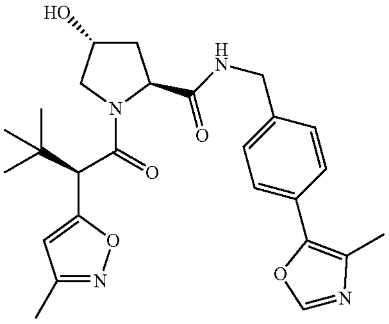
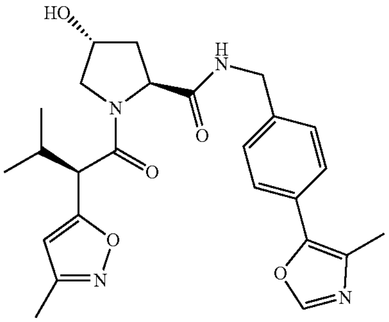
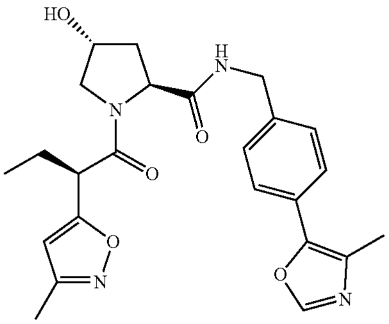
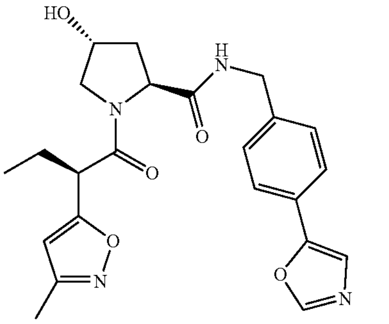
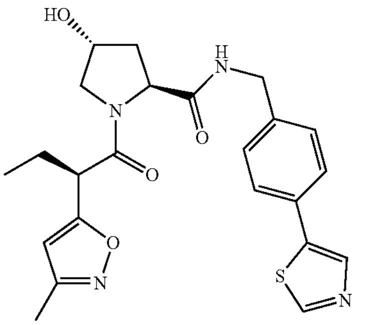

-continued
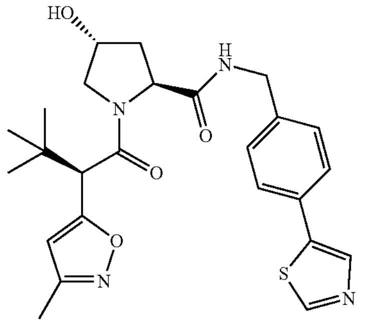
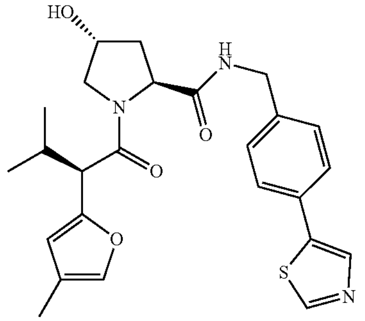
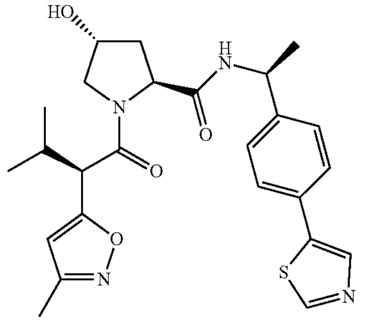
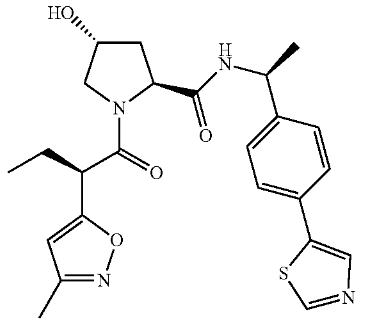
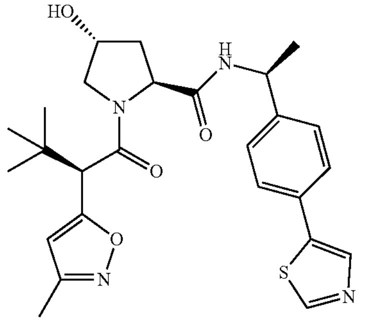
-continued
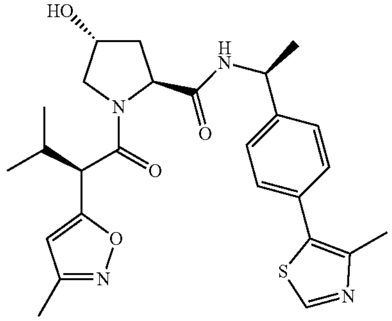
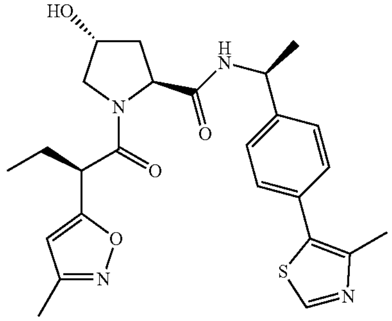
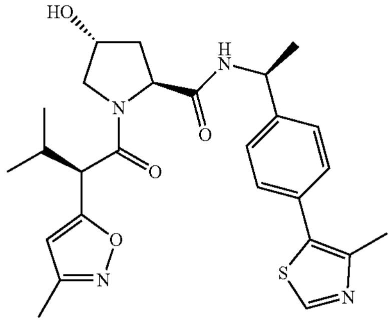
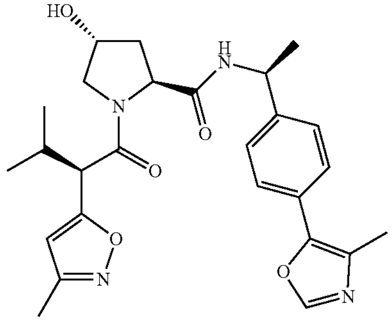
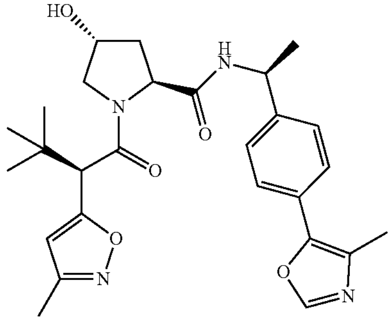

-continued
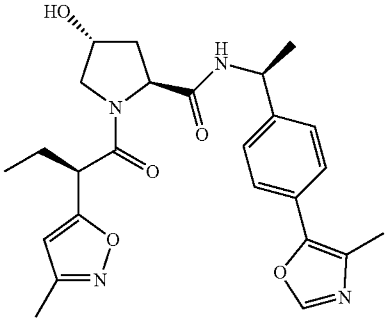
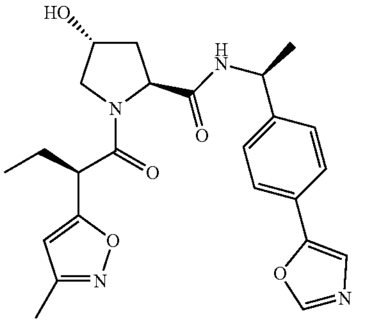
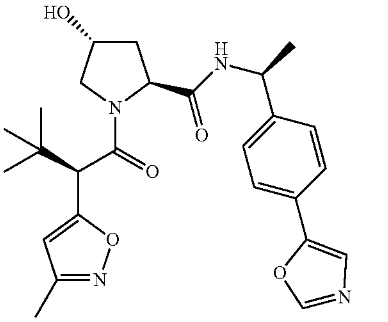
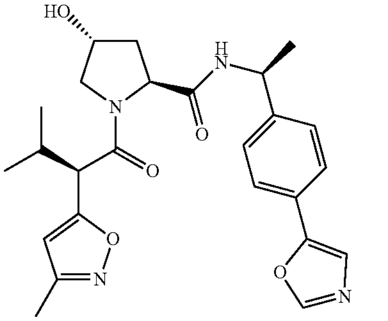
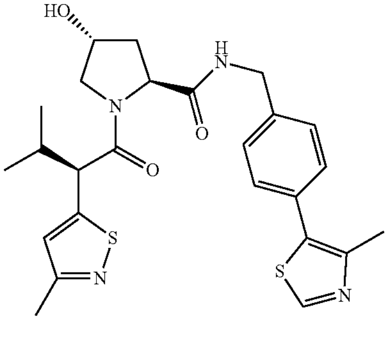
-continued
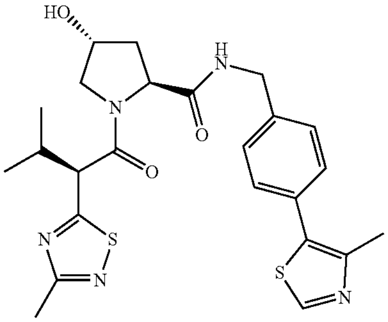
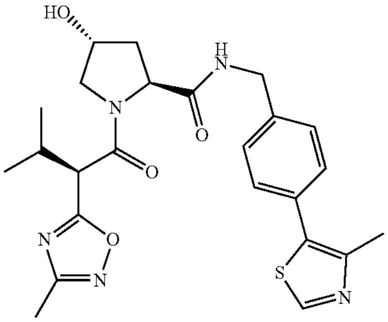
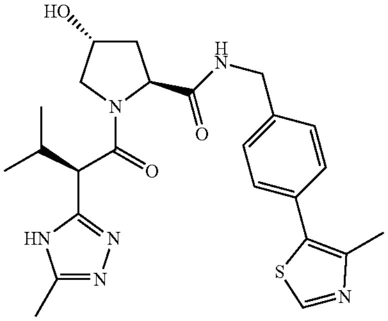
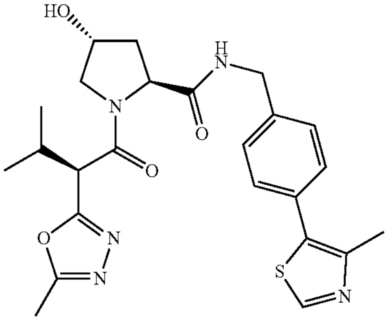
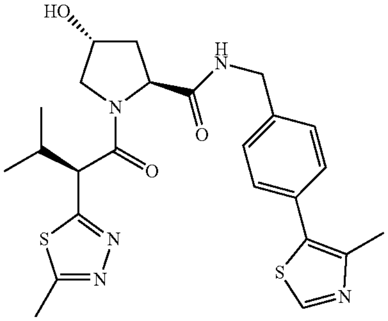

-continued
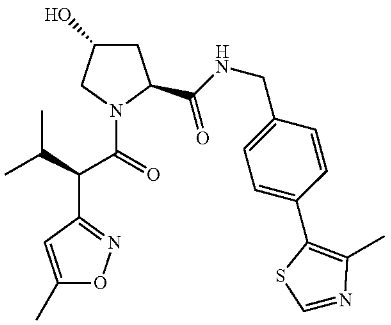
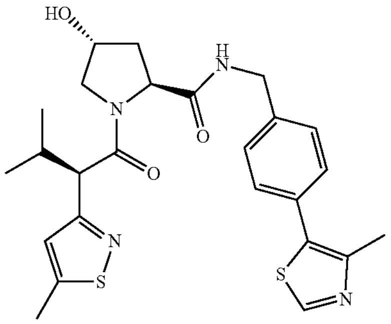
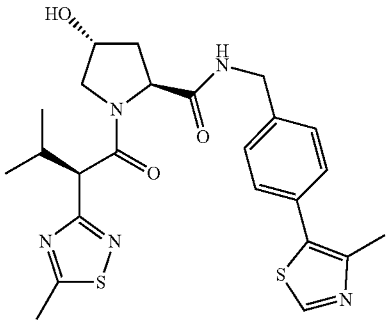
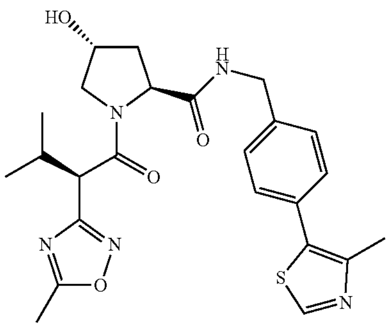
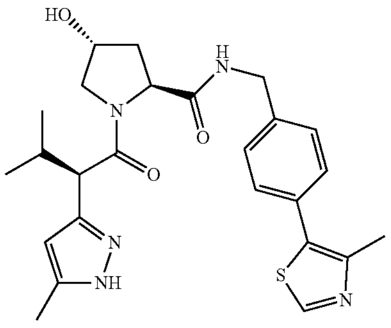
-continued
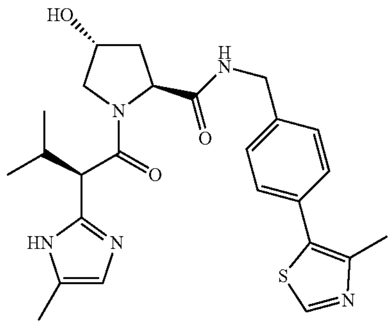
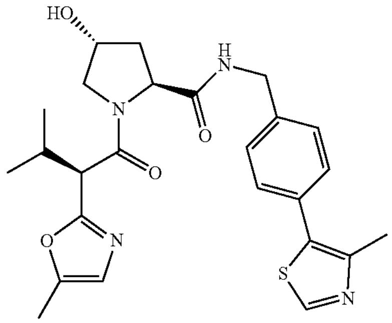
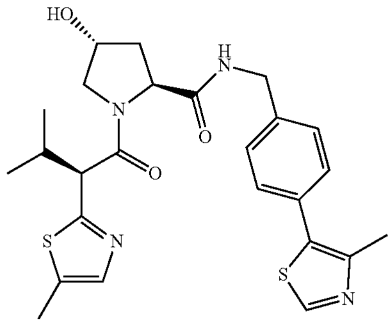
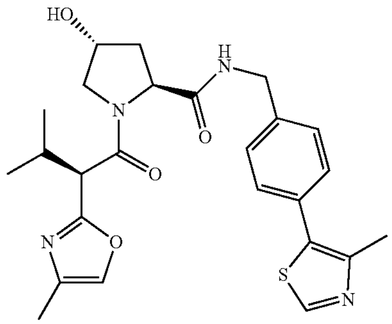
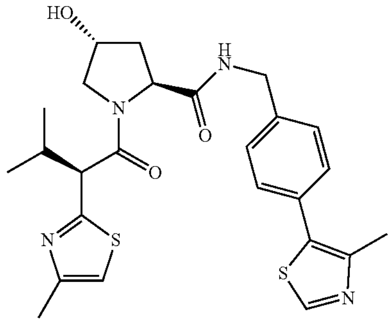

-continued
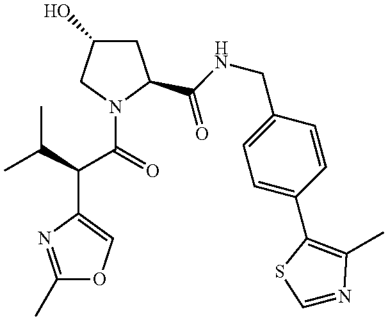
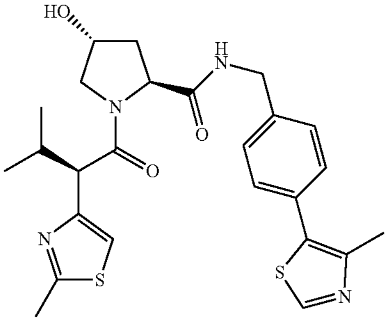
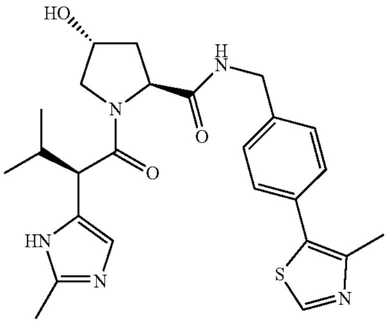
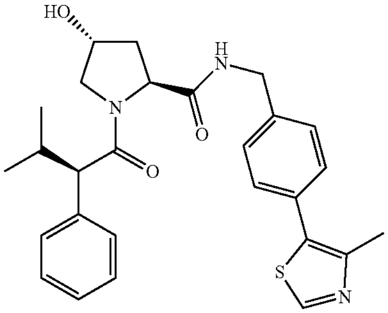
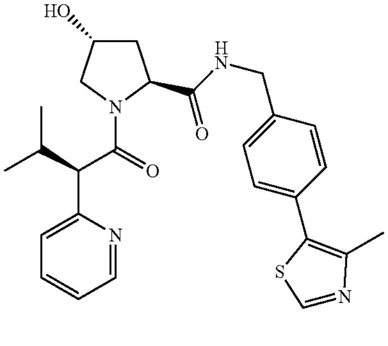
-continued
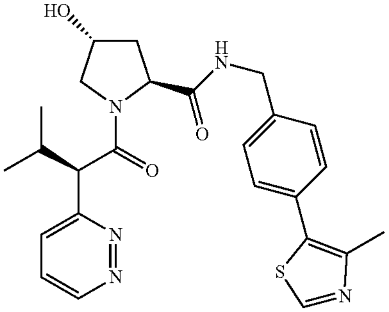
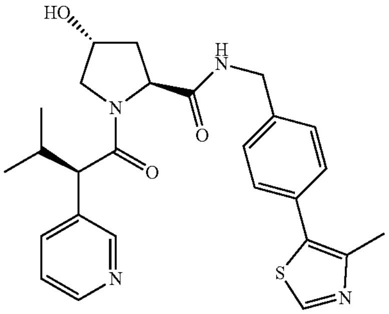
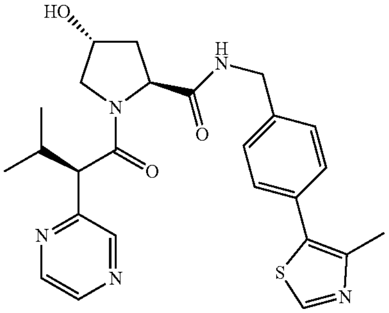
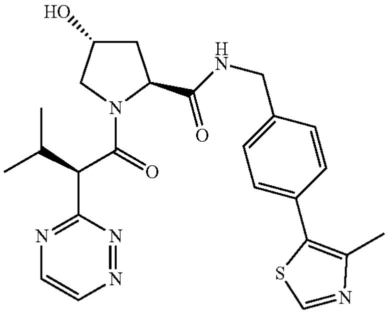
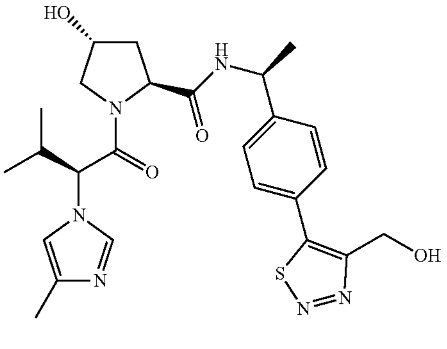

-continued
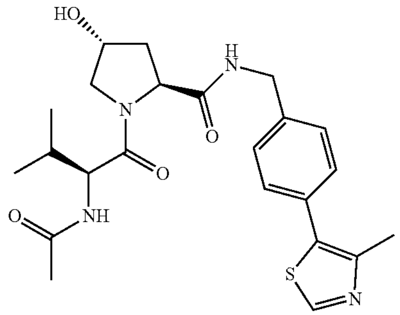
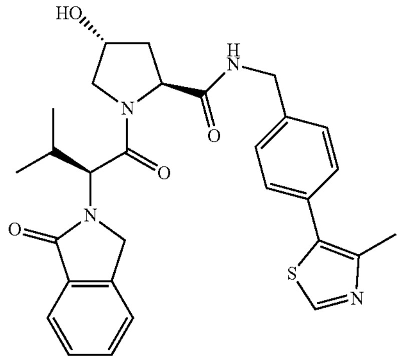
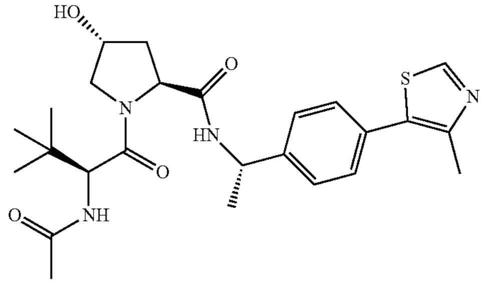
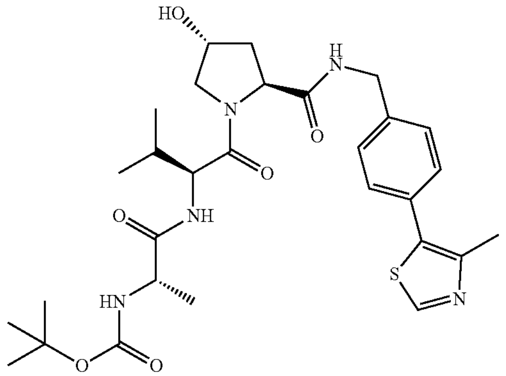
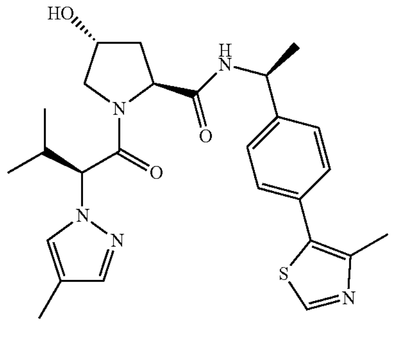
-continued
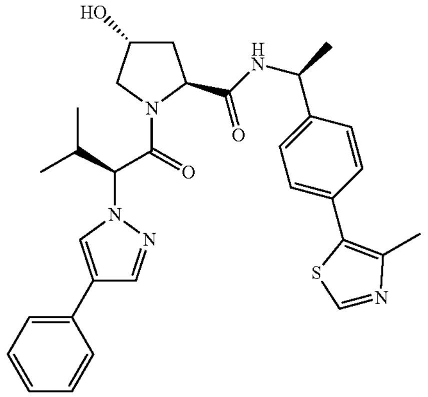
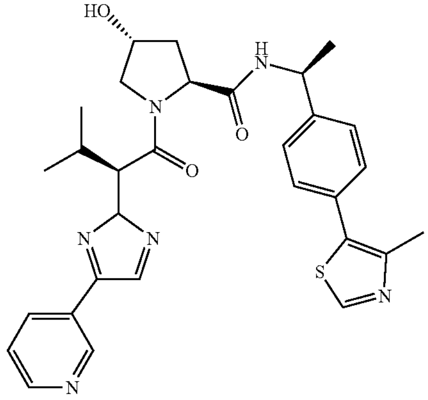
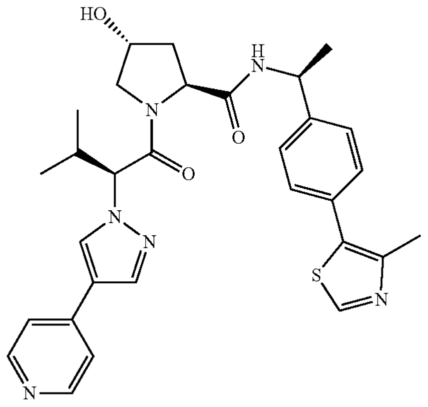
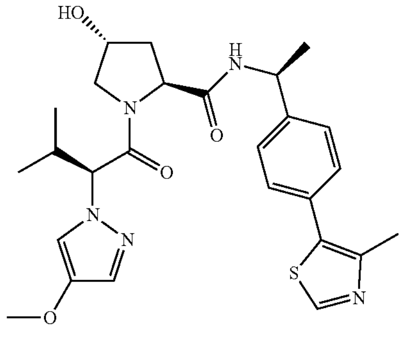

-continued
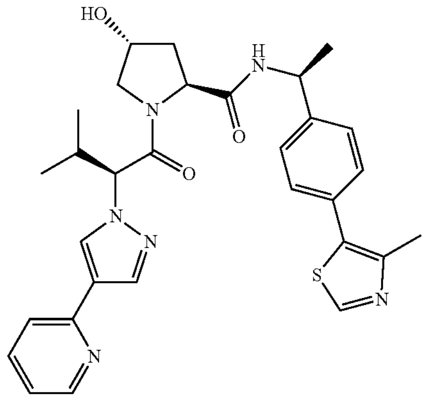
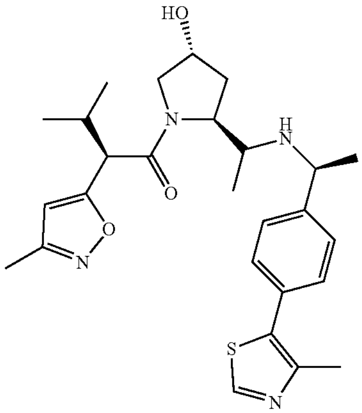
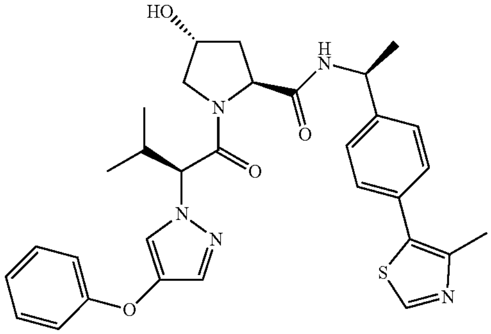
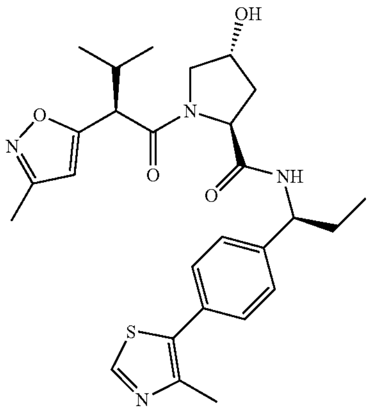
-continued
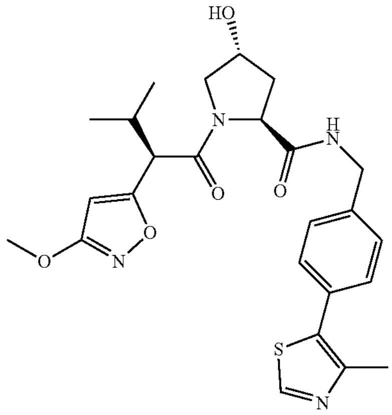
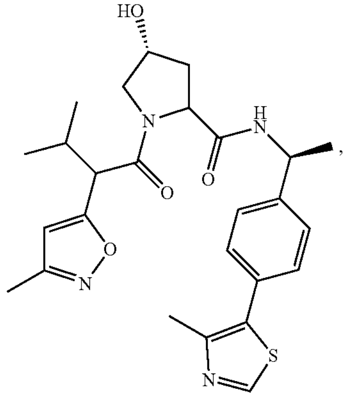
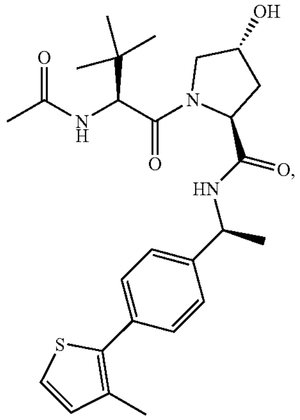
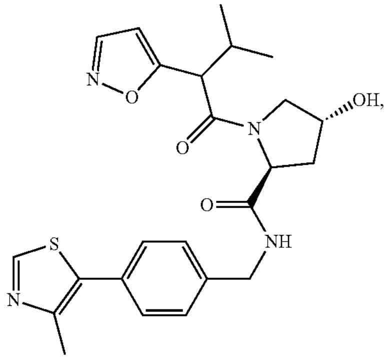

-continued

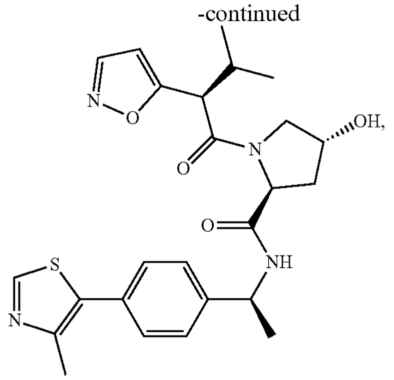

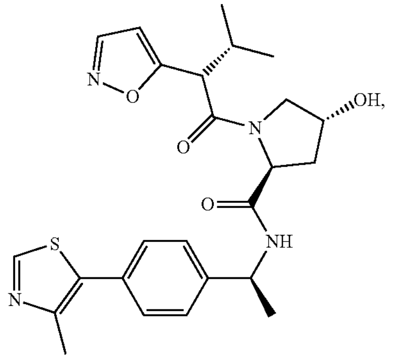 [SMILES: Cc1ncsc1-c1ccc([C@H](C)NC(=O)[C@@H]2C[C@@H](O)CN2C(=O)C(c2ccno2)C(C)C)cc1]

and

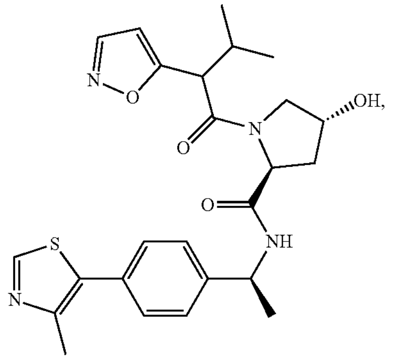

wherein the VLM may be connected to a PTM via a linker, as described herein, at any appropriate location, including, e.g., an aryl, heteroaryl, phenyl, or phenyl of an indole group, optionally via any appropriate functional group, such as an amine, ester, ether, alkyl, or alkoxy.

Exemplary CLMs

In any aspect or embodiment described herein, the present disclosure provides CLMs useful for binding and and recruiting cereblon.

In any aspect or embodiment described herein, the CLM is selected from the group consisting of chemical structures:

(a1)

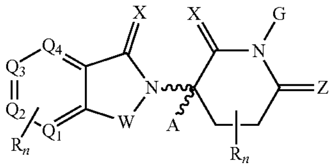

-continued (b)

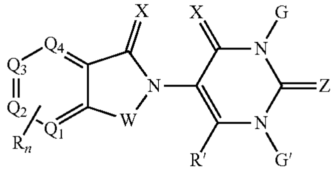

(c)

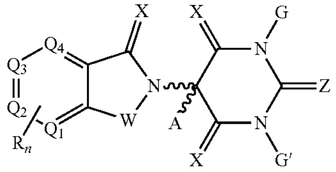

(d1)

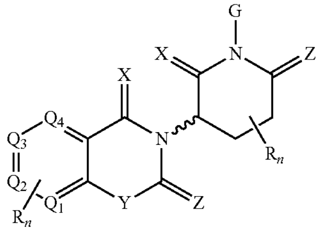

(e)

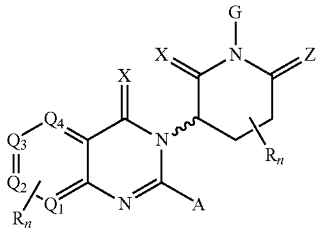

(a2)

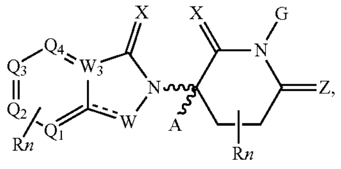

(d2)

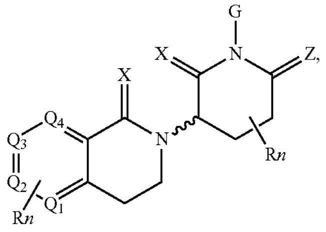

(a3)

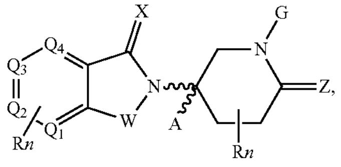

or (a4)

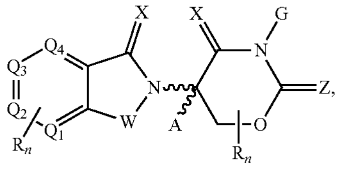

wherein:

W of Formulae (a1) through (e) (i.e., (a1), (a2), (a3), (a4), (b), (c), (d1), (d2), and (e)) is independently selected from $CH_2$, O, CHR, C═O, $SO_2$, NH, N, optionally substituted cyclopropyl group, optionally substituted cyclobutyl group, and N-alkyl;

$W_3$ of Formula (a2) is C or N;

each X of Formulas (a) through (f) is independently selected from the group absent, O, S and $CH_2$;

each Y of Formulae (a1) through (e) is independently selected from $CH_2$, —C═CR', NH, N-alkyl, N-aryl, N-heteroaryl, N-cycloalkyl, N-heterocyclyl, O, and S;

each Z of Formulas (a1) through (e) is independently selected from absent, O, and S or $CH_2$, except that both X and Z cannot be $CH_2$ or absent;

each G and G' of Formulas (a1) through (e) is independently selected from H, optionally substituted linear or branched alkyl (e.g., optionally substituted with R'), OH, R'OCOOR, R'OCONRR", $CH_2$-heterocyclyl optionally substituted with R', and benzyl optionally substituted with $R^1$;

each of Q1, Q2, Q3, and Q4 of Formulae (a1) through (e) represent a N or a carbon C substituted with a group independently selected from H, R, N, and N-oxide;

A of Formulae (a1) through (e) is independently selected from H, optionally substituted linear or branched alkyl, cycloalkyl, Cl and F;

each n of Formulae (a1) through (e) represents an integer independently selected from 1 to 10 (e.g., 1-4, 1, 2, 3, 4, 5, 6, 7, 8, 9, or 10);

each R of Formulae (a1) through (e) is independently selected from: H, —C(═O)R' (e.g., a carboxy group), —CONR'R" (e.g., an amide group), —OR' (e.g., OH), —NR'R" (e.g., an amine group), —SR', —$SO_2$R', —$SO_2$NR'R", —CR'R"—, —CR'NR'R"—, (—CR'O)$_{n'}$R", optionally substituted aryl (e.g., an optionally substituted $C_5$-$C_7$ aryl), optionally substituted alkyl-aryl (e.g., an alkyl-aryl comprising at least one of an optionally substituted $C_1$-$C_6$ alkyl, an optionally substituted $C_5$-$C_7$ aryl, or a combination thereof), optionally substituted heteroaryl (e.g., an optionally substituted 5-7 membered heteroaryl), unsubstitute or substituted linear or branched alkyl (e.g., a $C_1$-$C_6$ linear or branched alkyl optionally substituted with one or more halogen, cycloalkyl (e.g., a 3-6 membered cycloalkyl), or aryl (e.g., a 5-7 membered aryl)), optionally substituted alkoxyl group (e.g., a methoxy, ethoxy, butoxy, propoxy, pentoxy, or hexoxy; wherein the alkoxyl may be substituted with one or more halogen, alkyl, haloalky, fluoroalkyl, cycloalkyl (e.g., a $C_3$-$C_6$ cycloalkyl), or aryl (e.g., $C_5$-$C_7$ aryl)), optionally substituted cycloalkyl (e.g., an optionally substituted 3-7 membered cycloalkyl), optionally substituted heterocyclyl (e.g., an optionally substituted 3-7 membered heterocyclyl), —P(O)(OR')R", —P(O)R'R", —OP(O)(OR')R", —OP(O)R'R", —Cl, —F, —Br, —I, —$CF_3$, —CN, —NR'$SO_2$NR'R", —NR'CONR'R", —CONR'COR", —NR'C(═N—CN)NR'R", —C(═N—CN)NR'R", —NR'C(═N—CN)R", —NR'C(═C—$NO_2$)NR'R", —$SO_2$NR'COR", —$NO_2$, —$CO_2$R', —C(C═N—OR')R", —CR'═CR'R", —CCR', —S(C═O)(C═N—R')R", —$SF_5$, or —$OCF_3$, wherein at least one W, X, Y, Z, G, G', R, R', R", Q1, Q2, Q3, Q4, or A is modified to be covalently joined to a PTM, a chemical linking group (L), a ULM, a CLM, or a combination thereof;

R' and R" of Formulae (a1) through (e) are each independently selected from a bond, H, optionally substituted linear or branched alkyl, optionally substituted cycloalkyl, optionally substituted aryl, optionally substituted heteroaryl, optionally substituted heterocyclic, —C(═O)R, and optionally substituted heterocyclyl;

n' of Formulae (a1) through (e) is an integer from 1-10 (e.g. 1-4, 1, 2, 3, 4, 5, 6, 7, 8, 9, or 10);

 represents a single bond or a double bond; and each  of Formulae (a1) through (e) independently represents a bond that is stereospecific ((R) or (S)) or non-stereospecific In any aspect or embodiment described herein, the CLM comprises a chemical structure selected from the group consisting of:

(a1)

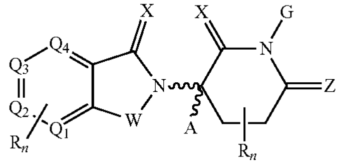

(b)

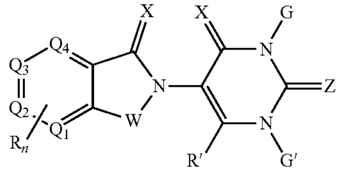

(c)

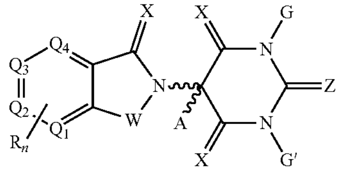

(d1)

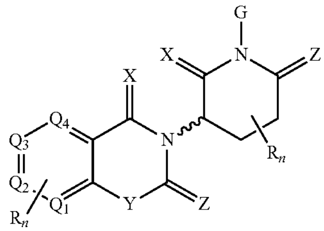

(e)

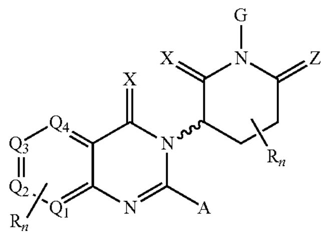

(a2)

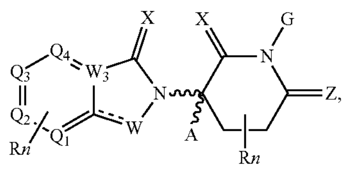

-continued (d2)

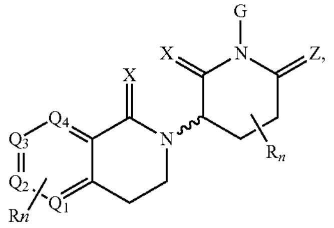

(a3)

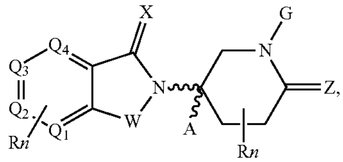

and (a4)

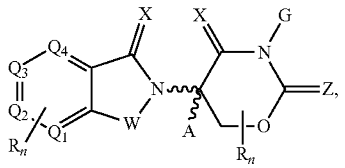

wherein:

each W of Formulae (a1) through (e) (i.e., (a1), (a2), (a3), (a4), (b), (c), (d1), (d2), and (e)) is independently selected from $CH_2$, O, CHR, C═O, $SO_2$, NH, N, optionally substituted cyclopropyl group, optionally substituted cyclobutyl group, and N-alkyl;

$W_3$ of Formula (a2) is selected from C and N;

each X of Formulae (a1) through (e) is independently selected from absent, O, S and $CH_2$;

each Y of Formulae (a1) through (e) is independently selected from $CH_2$, —C═$CR^1$, NH, N-alkyl, N-aryl, N-hetaryl, N-cycloalkyl, N-heterocyclyl, O, and S;

each Z of Formulae (a1) through (e) is independently selected from absent, O, S, and $CH_2$, except that both X and Z cannot be $CH_2$ or absent;

each of G and G' of Formulae (a1) through (e) are independently selected from H, optionally substituted linear or branched alkyl (e.g., optionally substituted with R'), OH, R'OCOOR, R'OCONRR", $CH_2$-heterocyclyl optionally substituted with R', and benzyl optionally substituted with R';

Q1, Q2, Q3, and Q4 of Formulae (a1) through (e) each independently represent a nitrogen or a carbon substituted with a group independently selected from H, R, N and N-oxide;

A of Formulae (a1) through (e) is independently selected from H, optionally substituted linear or branched alkyl, cycloalkyl, Cl and F;

n of Formulae (a1) through (e) represents an integer independently selected from 1 to 10 (e.g., 1-4, 1, 2, 3, 4, 5, 6, 7, 8, 9, or 10);

R of Formulae (a1) through (e) is selected from the group consisting of: H, —C(═O)R' (e.g., a carboxy group), —CONR'R" (e.g., an amide group), —OR' (e.g., OH), —NR'R" (e.g., an amine group), —SR', —$SO_2$R', —$SO_2$NR'R", —CR'R"—, —CR'NR'R"—, $(—CR'O)_{n'}$-R", optionally substituted -aryl (e.g., an optionally substituted C5-C7 aryl), optionally substituted alkyl-aryl (e.g., an alkyl-aryl comprising at least one of an optionally substituted C1-C6 alkyl, an optionally substituted C5-C7 aryl, or a combination thereof), optionally substituted heteroaryl (e.g., an optionally substituted 5-7 membered heteroaryl), -optionally substituted linear or branched alkyl (e.g., a C1-C6 linear or branched alkyl optionally substituted with one or more halogen, cycloalkyl (e.g., a C3-C6 cycloalkyl), or aryl (e.g., C5-C7 aryl)), optionally substituted alkoxyl group (e.g., a methoxy, ethoxy, butoxy, propoxy, pentoxy, or hexoxy; wherein the alkoxyl may be substituted with one or more halogen, alkyl, haloalky, fluoroalkyl, cycloalkyl (e.g., a C3-C6 cycloalkyl), or aryl (e.g., C5-C7 aryl)), optionally substituted cycloalkyl (e.g., an optionally substituted C3-C6 cycloalkyl), optionally substituted heterocyclyl (e.g., (an optionally substituted 3-7 membered heterocyclyl)), —P(O)(OR')R", —P(O)R'R", —OP(O)(OR')R", —OP(O)R'R", —Cl, —F, —Br, —I, —$CF_3$, —CN, —NR'$SO_2$NR'R", —NR'CONR'R", —CONR'COR", —NR'C(═N—CN)NR'R", —C(═N—CN)NR'R", —NR'C(═N—CN)R", —NR'C(═C—NO2)NR'R", —SO2NR'COR", —NO2, —CO2R', —C(C═N—OR')R", —CR'═CR'R", —CCR', —S(C═O)(C═N—R')R", —SF5 and —$OCF_3$, wherein at least one W, X, Y, Z, G, G', R, R', R", Q1, Q2, Q3, Q4, or A is covalently joined (cirectly or indirectly, e.g., via a functional group or an atom, such as O, S, N) to a PTM, a chemical linking group (L), a ULM, a CLM, or a combination thereof;

R' and R" of Formulae (a1) through (e) are each independently selected from a bond, H, optionally substituted linear or branched alkyl, optionally substituted cycloalkyl, optionally substituted aryl, optionally substituted heteroaryl, optionally substituted heterocyclic, —C(═O)R, optionally substituted heterocyclyl;

n' of Formulae (a1) through (e) is an integer selected from 1-10 (e.g., 1-4, 1, 2, 3, 4, 5, 6, 7, 8, 9, or 10); and ⸌⸌⸌ represents a single bond or a double bond;

each ∿∿∿ of Formulae (a1) through (e) independently represents a bond that is stereospecific ((R) or (S)) or non-stereospecific.

In any aspect or embodiment described herein, the CLM or ULM has the chemical structure of Formula (g):

Formula (g)

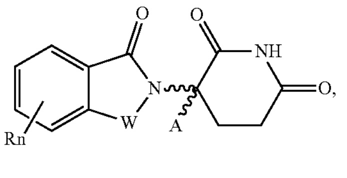

wherein:

W of Formula (g) is selected from $CH_2$, 0, C═O, NH, and N-alkyl;

A of Formula (g) is selected from H, methyl, or optionally substituted linear or branched alkyl;

n is an integer selected from 1 to 4;

R of Formula (g) is independently selected from H, O, OH, N, NH, $NH_2$, —Cl, —F, —Br, —I, methyl, optionally substituted linear or branched alkyl (e.g., optionally substituted linear or branched C1-C6 alkyl), optionally substituted linear or branched alkoxy (e.g., optionally substituted linear or branched C1-C6 alkoxy), -alkyl-aryl (e.g., an -alkyl-aryl comprising at least one of C1-C6 alkyl, C4-C7 aryl, or a combination thereof), aryl (e.g., C5-C7 aryl), amine, amide, or carboxy), wherein at least one R or W is modified to be covalently joined to a PTM, a chemical linking group (L), a ULM, CLM, or combination thereof; and each ~~~ of Formula (g) independently represents a bond that is stereospecific ((R) or (S)) or non-stereospecific.

In any aspect or embodiment described herein, the CLM or ULM is selected from the group consisting of:

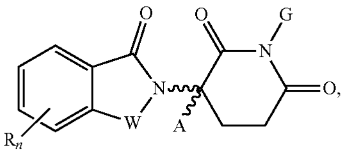

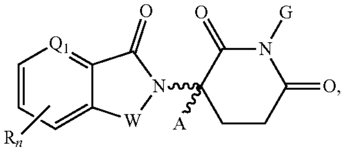

or

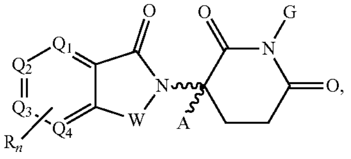

wherein:

$Q_1$, $Q_2$, $Q_3$, $Q_4$, $Q_5$ are each independently represent a nitrogen or a carbon substituted with a group independently selected from R, N or N-oxide;

W is selected from $CH_2$ and C═O;

A is H or linear or branched $C_{1-3}$ alkyl (e.g., a methyl or ethyl);

n is an integer selected from 1-4 (e.g., 1, 2, or 3; or 1 or 2);

G is a H or a linear or branched $C_{1-3}$ alkyl (e.g., methyl);

each R is independently selected from a H, O, OH, N, NH, $NH_2$, —Cl, —F, —Br, linear or branched $C_{1-3}$ alkyl (e.g., methyl or ethyl), linear or branched $C_{1-3}$ fluoroalkyl (e.g., $—CH^3$ or $CHF_2$), or a linear or branched $C_{1-3}$ alkoxy (e.g., methoxy or ethoxy), wherein one R is modified to be covalently joined to a PTM via a chemical linking group (L); and each ~~~ independently represents a bond that is stereospecific ((R) or (S)) or non-stereospecific.

In any aspect or embodiment described herein, the CLM or ULM is represented by the chemical structure:

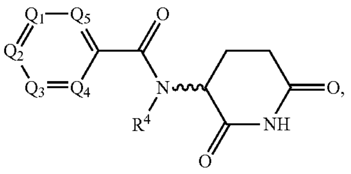

wherein:

$Q_1$, $Q_2$, $Q_3$, $Q_4$, $Q_5$ are each independently represent a nitrogen or a carbon substituted with a group independently selected from R', N or N-oxide;

$R^4$ is a H or methyl;

R' is a H, halogen (e.g., F, Cl, Br), a $C_{1-3}$ alkyl (e.g., methyl or ethyl), or $C_{1-3}$ alkoxyl (e.g., a methoxy or ethoxy); and ~~~ represents a bond that may be stereospecific ((R) or (S)) or non-stereospecific.

In any aspect or embodiment described herein, the CLM or ULM is selected from the group consisting of:

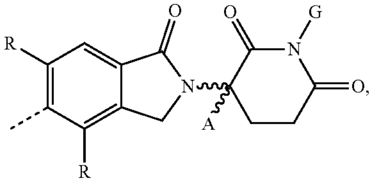

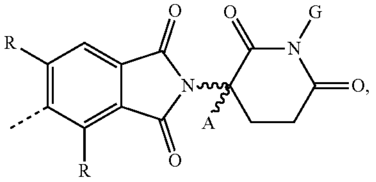

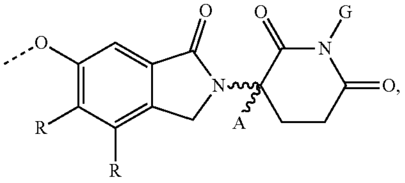

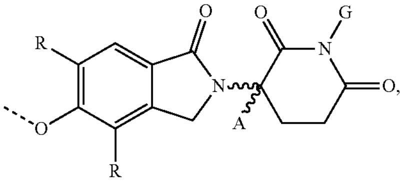

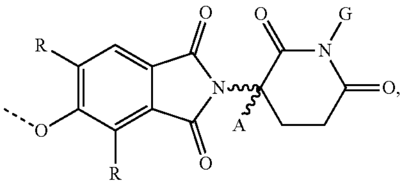

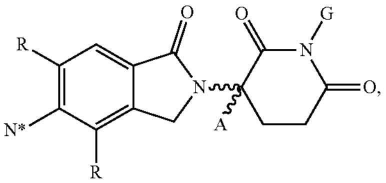

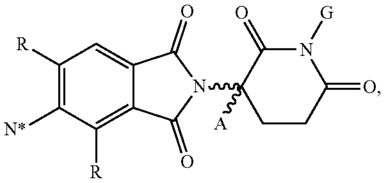

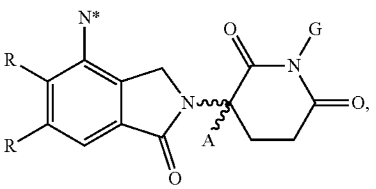
~~~

-continued

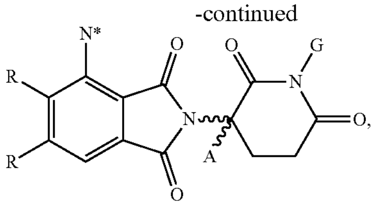

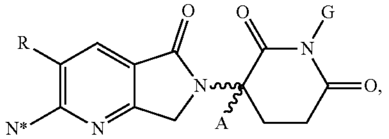

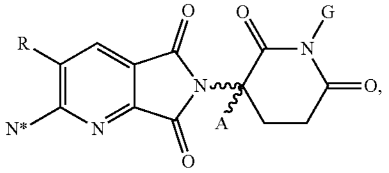

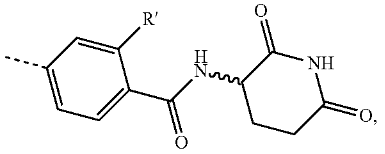

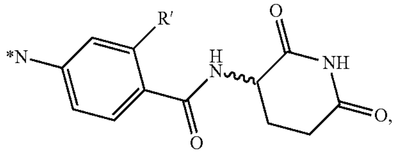

or

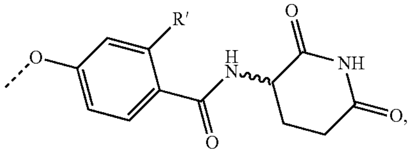

wherein:

A is a H or linear or branched $C_{1-3}$ alkyl (e.g., a methyl or ethyl);

G is a H or a linear or branched $C_{1-3}$ alkyl (e.g., methyl);

one R is a hydrogen and the other R is a H, O, OH, N, NH, $NH_2$, —Cl, —F, —Br, linear or branched $C_{1-3}$ alkyl (e.g., methyl or ethyl), linear or branched $C_{1-3}$ fluoroalkyl (e.g., —$CH^3$ or $CHF_2$), or a linear or branched $C_{1-3}$ alkoxy (e.g., methoxy or ethoxy); and R' is a H, halogen (e.g., F, Cl, Br), a $C_{1-3}$ alkyl (e.g., methyl or ethyl), or $C_{1-3}$ alkoxyl (e.g., a methoxy or ethoxy);

represents a bond that may be stereospecific ((R) or (S)) or non-stereospecific;

N* is the point of attachment of the PTM to the chemical linking group (L) or directly to the ULM (e.g., N* is a nitrogen atom (i) that is covalently linked to the PTM via the chemical linking group (L) with a H or methyl completing valency or (ii) that is shared with the chemical linking group (L) (e.g., a heteroatom shared with an optionally substituted heterocyloalkyl of the chemical linking group (L));

is a single or double bond; and the indicates the site of attachment of a PTM via a chemical linking group.

In any aspect or embodiment described herein, the CLM or ULM is selected from the group consisting of:

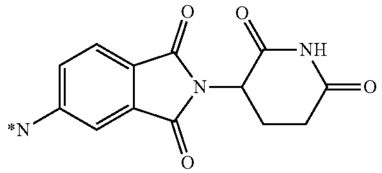

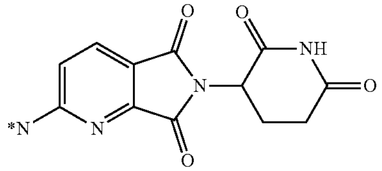

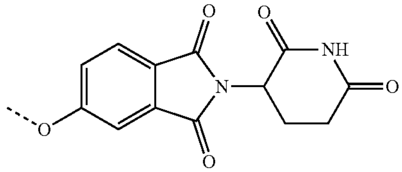

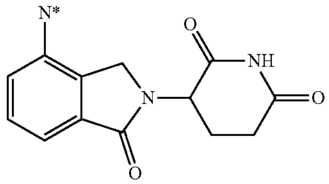

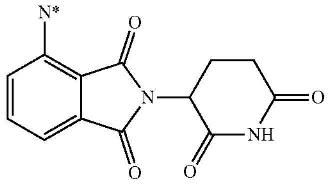

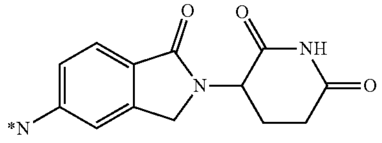

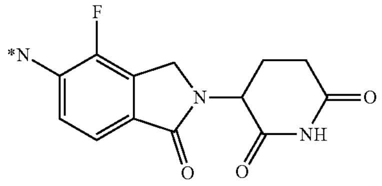

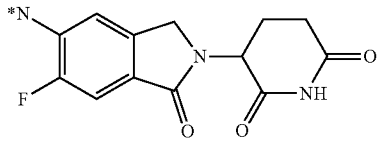

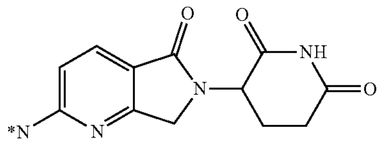

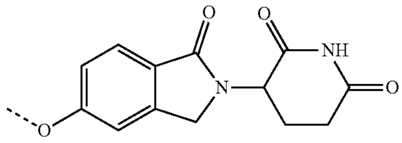

-continued

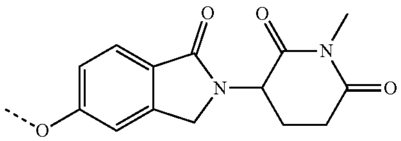

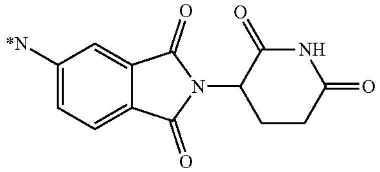

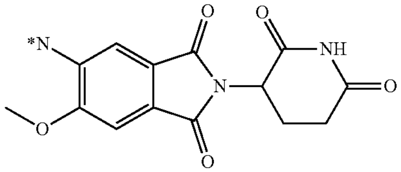

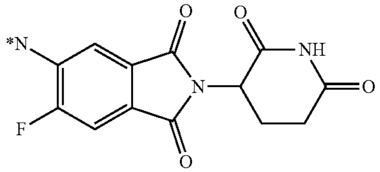

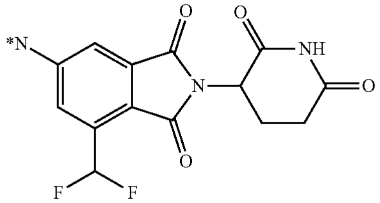

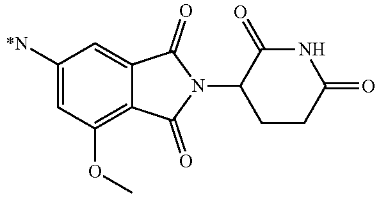

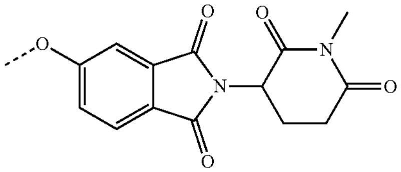

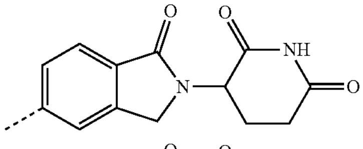

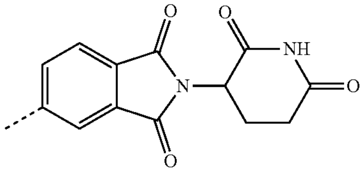

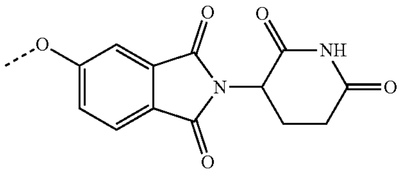

-continued

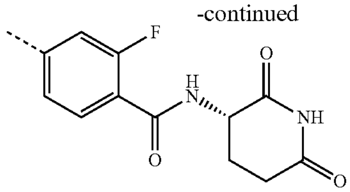

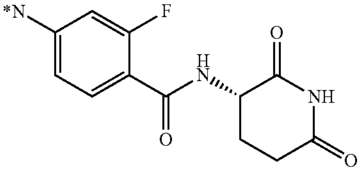

or

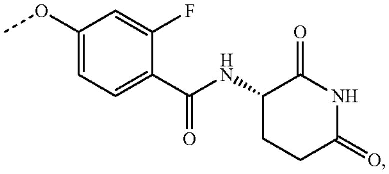

wherein:

N* is the point of attachment of the PTM to the chemical linking group (L) or directly to the ULM (e.g., N* is a nitrogen atom (i) that is covalently linked to the PTM via the chemical linking group (L) with a H or methyl completing valency or (ii) that is shared with the chemical linking group (L) (e.g., a heteroatom shared with an optionally substituted heterocyloalkyl of the chemical linking group (L)); and the 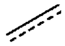 indicates the site of attachment of a PTM via a chemical linking group (L).

In any aspect or embodiment described herein, the CLM or ULM is selected from the group consisting of:

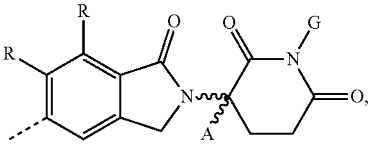

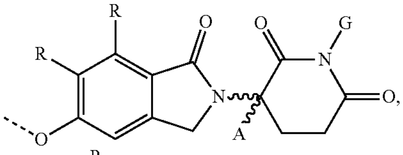

or

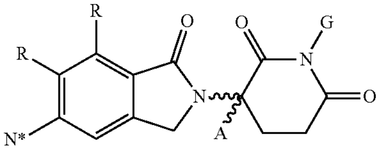

wherein:

A is a H or linear or branched $C_{1-3}$ alkyl (e.g., a methyl or ethyl);

G is a H or a linear or branched $C_{1-3}$ alkyl (e.g., methyl);

each R is independently a H, OH, $NH_2$, —Cl, —F, —Br, linear or branched $C_{1-3}$ alkyl (e.g., methyl or ethyl), or a linear or branched $C_{1-3}$ alkoxy (e.g., methoxy or ethoxy); and N* is a nitrogen atom that is covalently linked to the PTM via the chemical linker group (L) with a H or methyl completing valency or that is shared with the chemical linker group (L) (e.g., a heteroatom shared with an optionally substituted heterocyloalkyl of the chemical linker group (L).

In any aspect or embodiment described herein, the CLM or ULM is selected from the group consisting of:

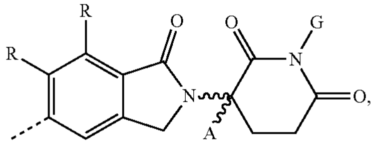

,

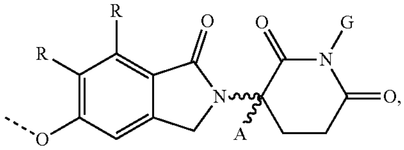

, or

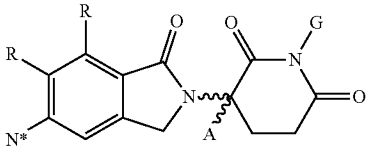

wherein:

A is a H or linear or branched $C_{1-3}$ alkyl (e.g., a methyl or ethyl);

G is a H or a linear or branched $C_{1-3}$ alkyl (e.g., methyl);

one R is a hydrogen and the other R is a H, OH, $NH_2$, —Cl, —F, —Br, linear or branched $C_{1-3}$ alkyl (e.g., methyl or ethyl), or a linear or branched $C_{1-3}$ alkoxy (e.g., methoxy or ethoxy); and N* is a nitrogen atom that is covalently linked to the PTM via the chemical linker group (L) with a H or methyl completing valency or that is shared with the chemical linker group (L) (e.g., a heteroatom shared with an optionally substituted heterocyloalkyl of the chemical linker group (L).

In any aspect or embodiment described herein, the CLM or ULM is selected from the group consisting of:

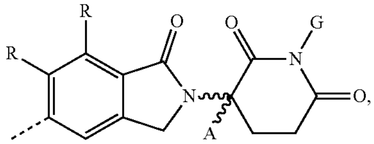

,

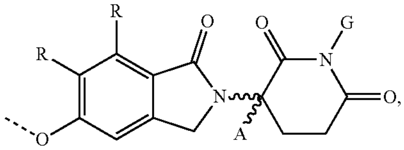

, or

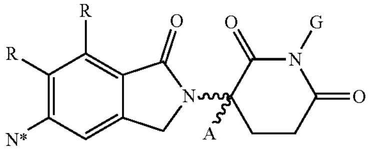

wherein:

A is a H or linear or branched $C_{1-3}$ alkyl (e.g., a methyl or ethyl);

G is a H or a linear or branched $C_{1-3}$ alkyl (e.g., methyl), preferably H;

one R is a hydrogen and the other R is a H, —Cl, —F, —Br, linear or branched $C_{1-3}$ alkyl (e.g., methyl or ethyl), or a linear or branched $C_{1-3}$ alkoxy (e.g., methoxy or ethoxy); and N* is a nitrogen atom that is covalently linked to the PTM via the chemical linker group (L) with a H or methyl completing valency or that is shared with the chemical linker group (L) (e.g., a heteroatom shared with an optionally substituted heterocyloalkyl of the chemical linker group (L).

In any aspect or embodiment described herein, the W, X, Y, Z, G, G', R, $R^1$, R'', Q1-Q4, or A of the CLM can independently be covalently coupled to a linker and/or a linker to which is attached one or more PTM, ULM, or CLM groups.

In any aspect or embodiment described herein, R is selected from H, O, OH, N, NH, $NH_2$, C1-C6 alkyl, C1-C6 alkoxy, -alkyl-aryl (e.g., an -alkyl-aryl comprising at least one of C1-C6 alkyl, C4-C7 aryl, or a combination thereof), aryl (e.g., C5-C7 aryl), amine, amide, and carboxy.

In any aspect or embodiment described herein, at least one R (e.g., an R group) is selected from from the following H, O, OH, N, NH, $NH_2$, C1-C6 alkyl, C1-C6 alkoxy, -alkyl-aryl (e.g., an -alkyl-aryl comprising at least one of C1-C6 alkyl, C4-C7 aryl, or a combination thereof), aryl (e.g., C5-C7 aryl), amine, amide, or carboxy, or W is modified to be covalently joined to a PTM, a chemical linking group (L), a ULM, a CLM, or a combination thereof.

In any aspect or embodiment described herein, n is an integer from 1 to 4, and each R is independently selected functional group or atom, for example, O, OH, N, —Cl, —F, C1-C6 alkyl, C1-C6 alkoxy, -alkyl-aryl (e.g., an -alkyl-aryl comprising at least one of C1-C6 alkyl, C4-C7 aryl, or a combination thereof), aryl (e.g., C5-C7 aryl), amine, amide, or carboxy, on the aryl or heteroaryl of the CLM, and optionally, one of which is modified to be covalently joined to a PTM, a chemical linker group (L), a ULM, CLM or combination thereof.

More specifically, non-limiting examples of CLMs include those shown below as well as those "hybrid" molecules that arise from the combination of one or more of the different features shown in the molecules below, wherein at least one R or W is modified to be covalently joined to a PTM, a chemical linking group (L), a ULM, CLM, or combination thereof.

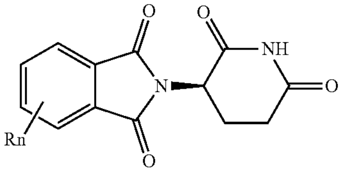

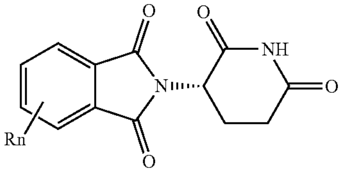

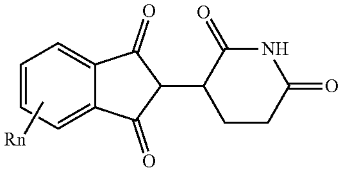

-continued
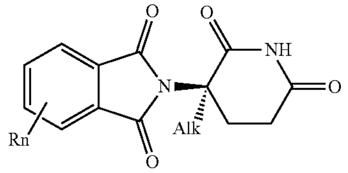
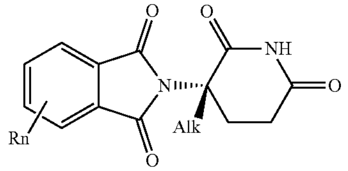
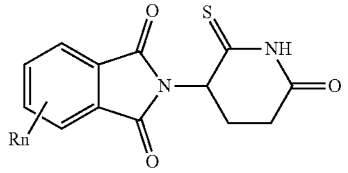
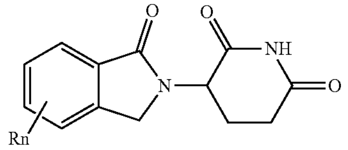
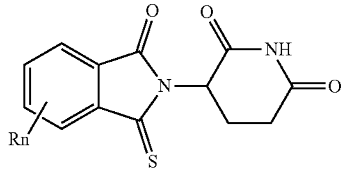
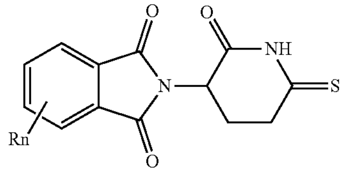
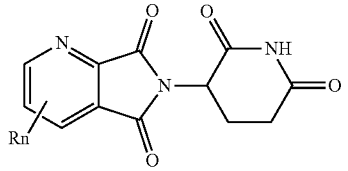
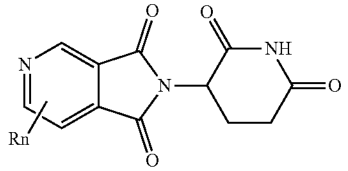
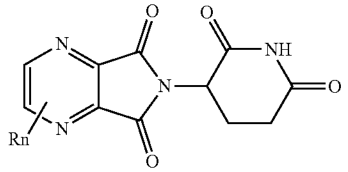
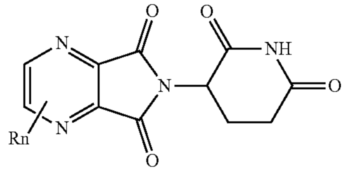
-continued
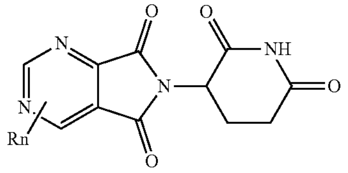
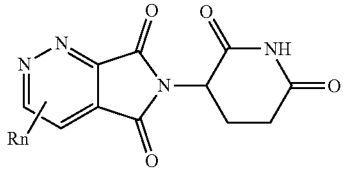
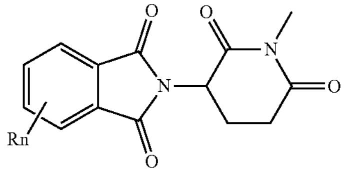
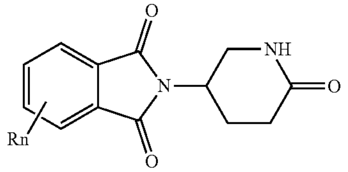
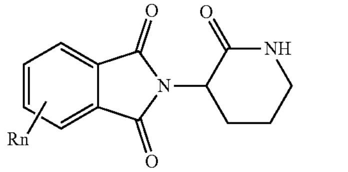
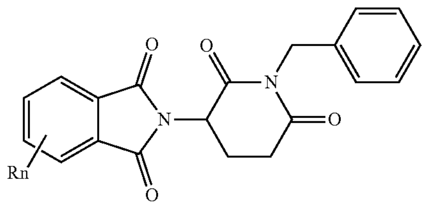
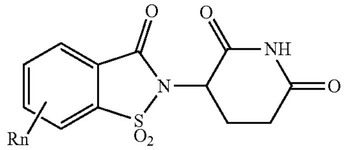
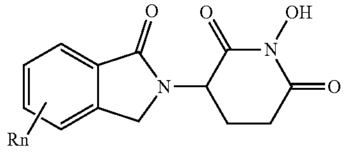
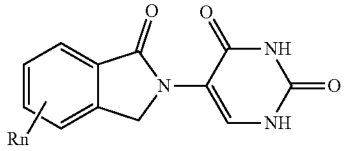
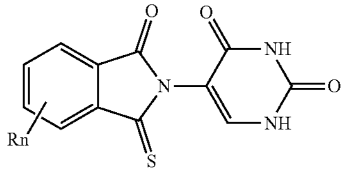

-continued
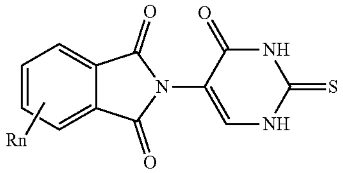
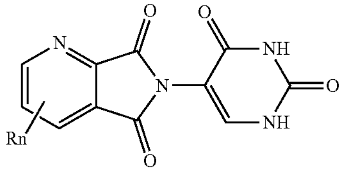
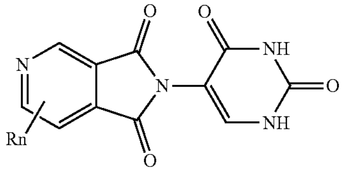
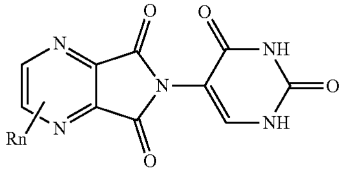
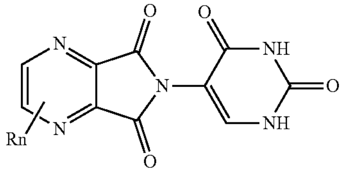
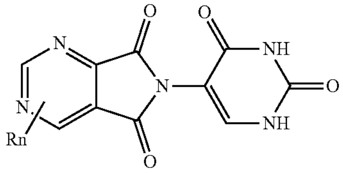
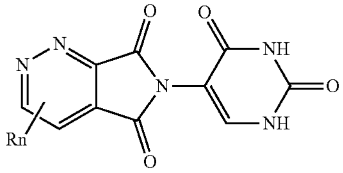
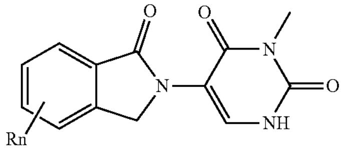
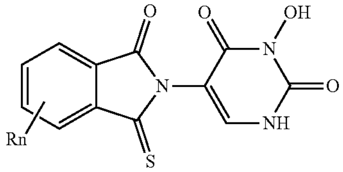
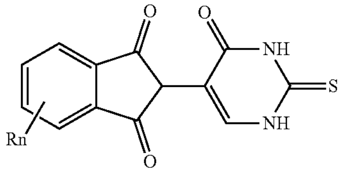
-continued
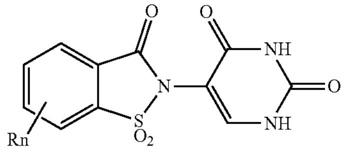
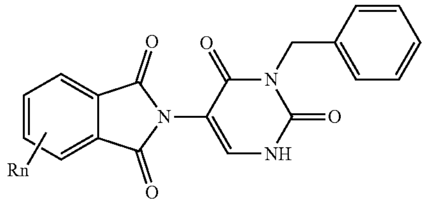
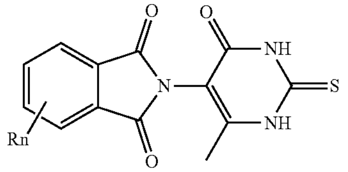
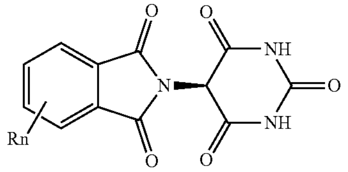
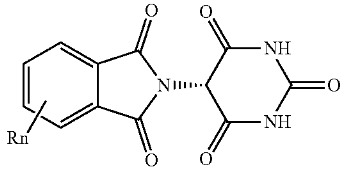
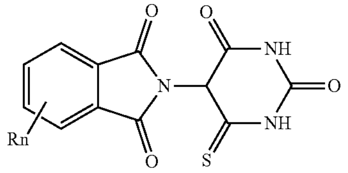
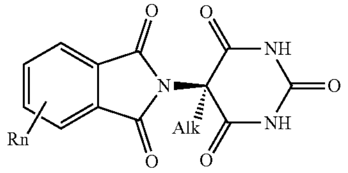
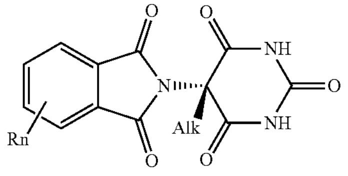
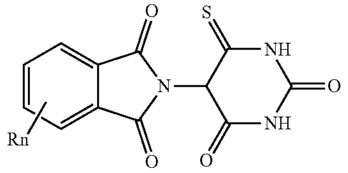
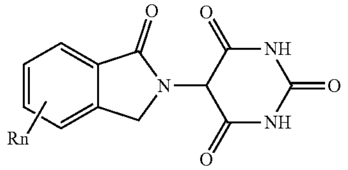

-continued
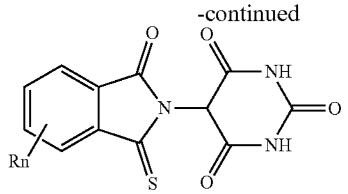
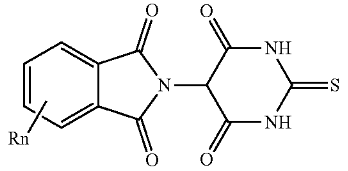
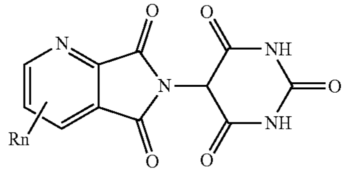
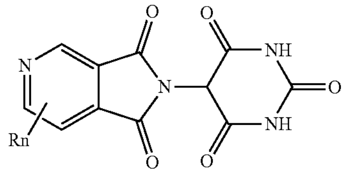
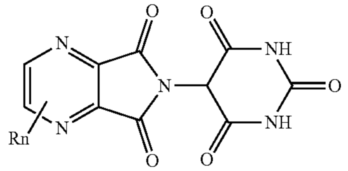
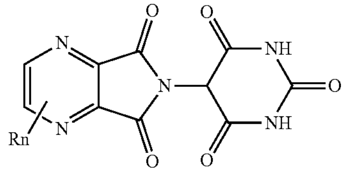
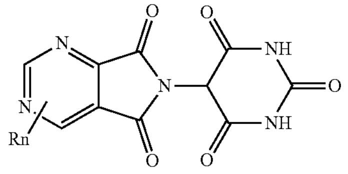
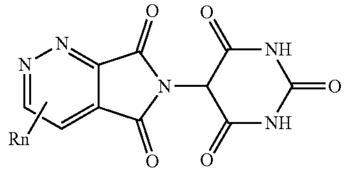
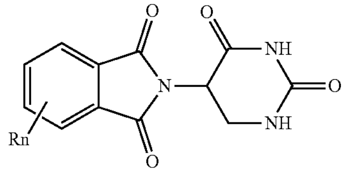
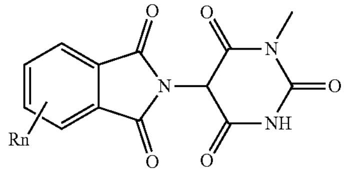
-continued
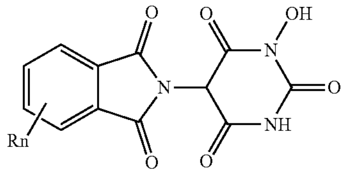
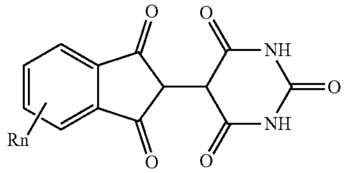
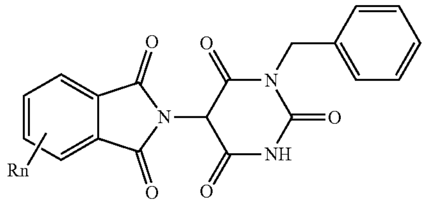
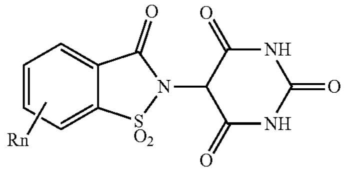
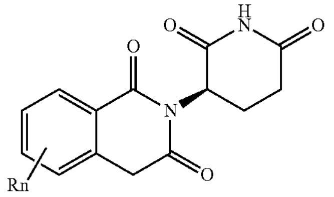
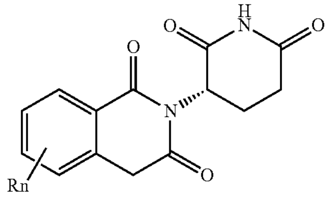
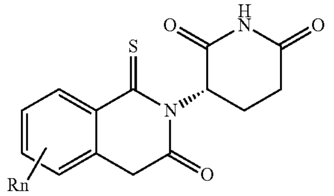
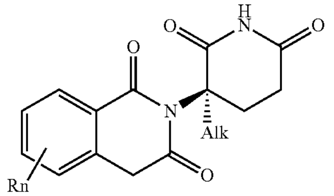
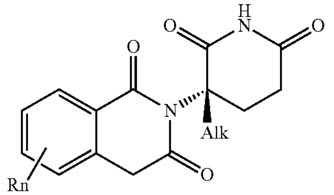

-continued
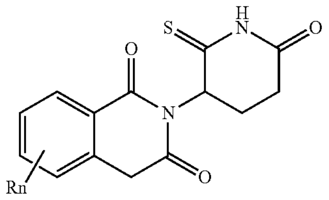
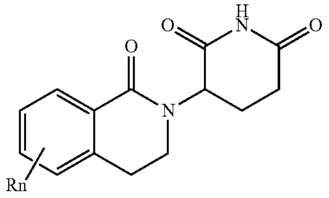
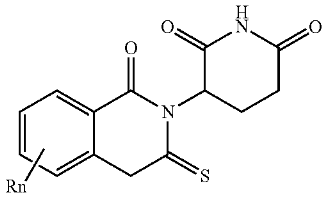
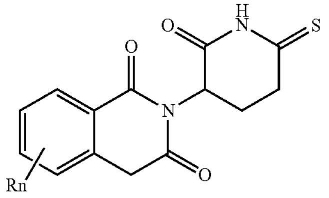
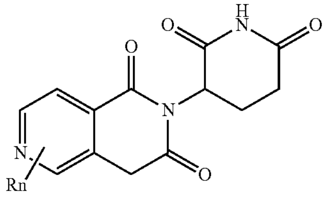
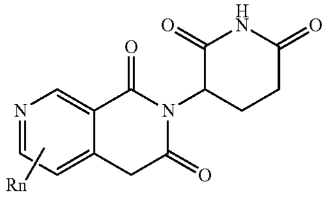
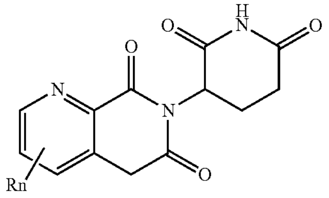
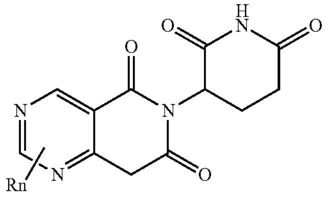
-continued
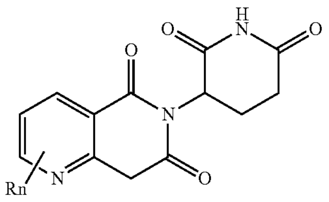
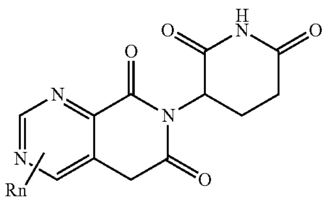
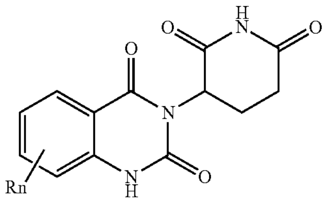
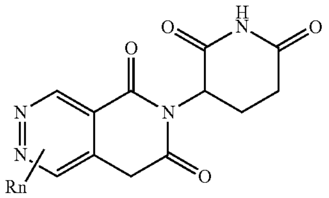
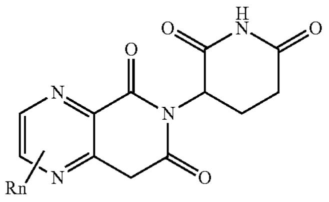
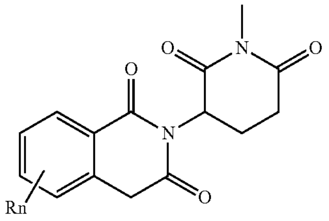
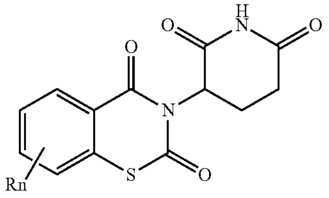
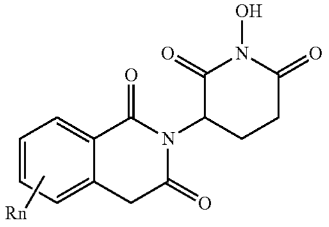

-continued
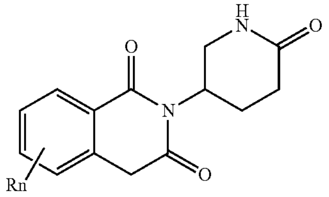
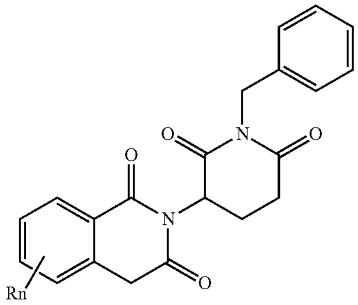
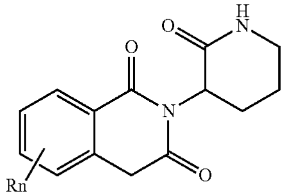
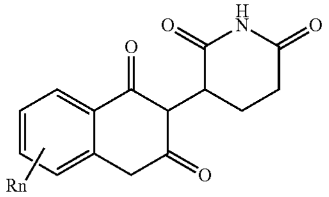
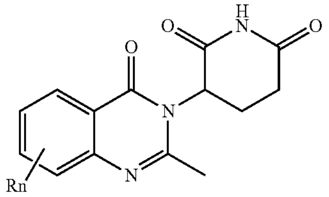
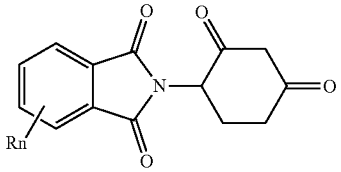
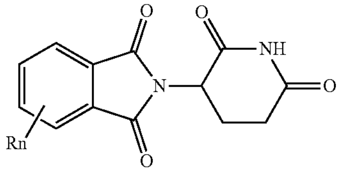
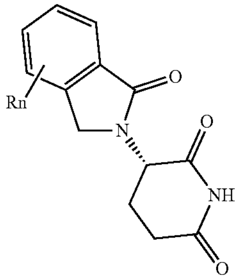
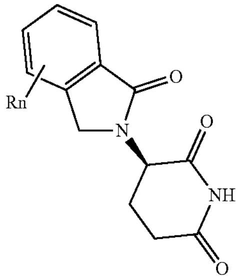
-continued
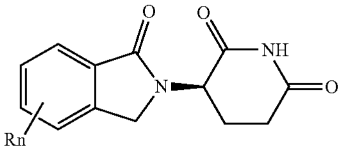
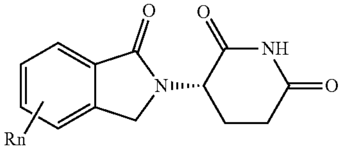
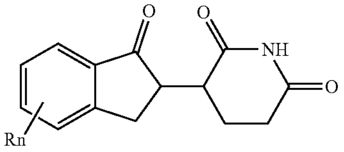
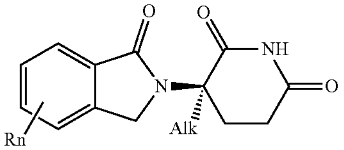
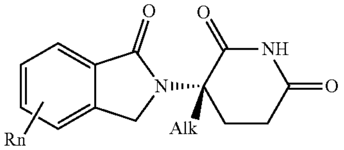
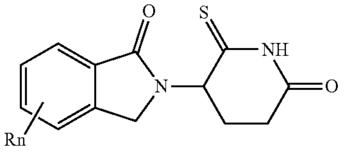
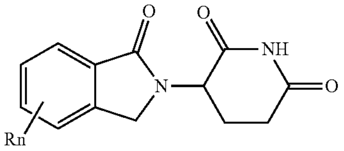
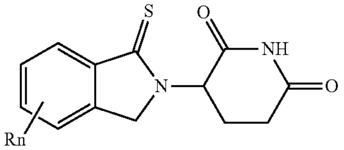
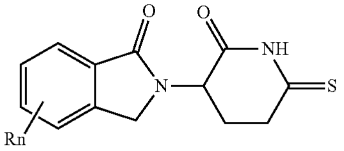
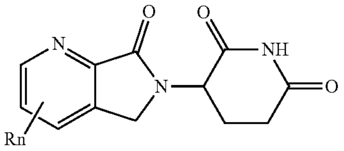
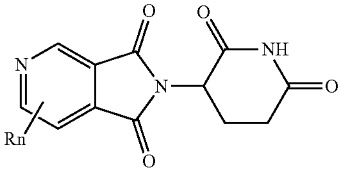

227
-continued
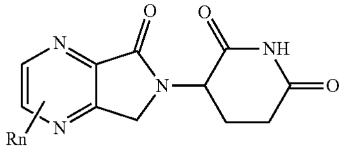
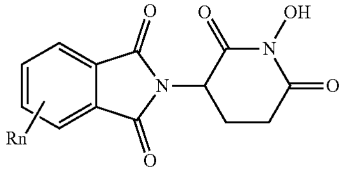
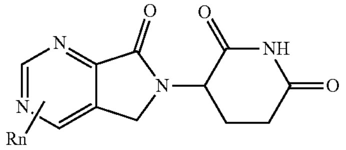
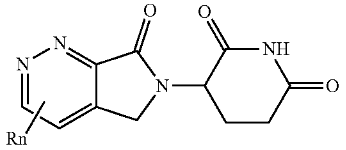
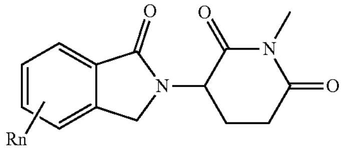
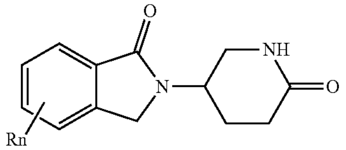
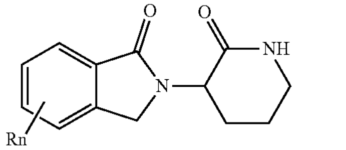
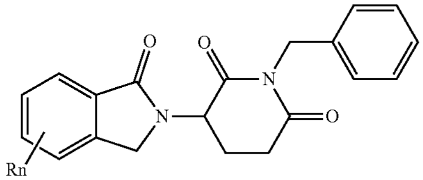
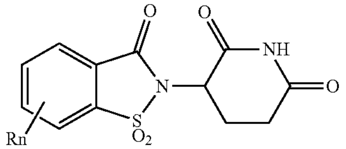
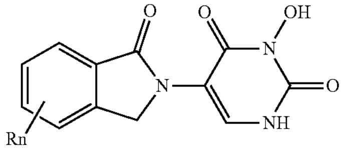
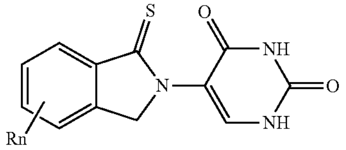
228
-continued
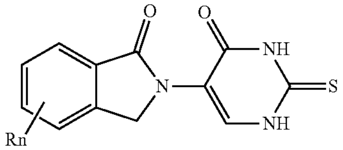
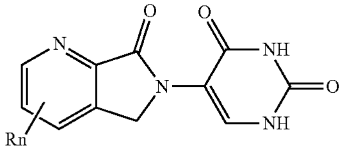
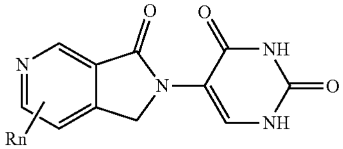
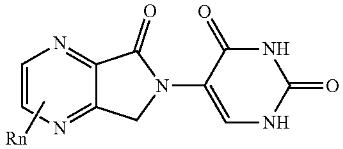
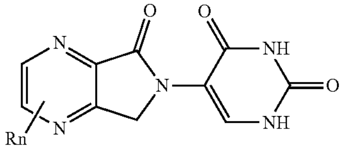
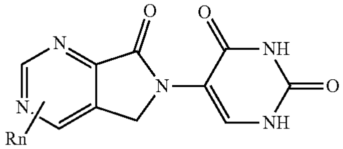
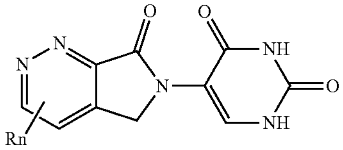
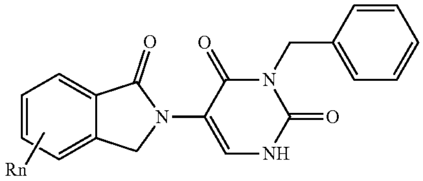
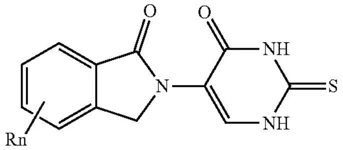
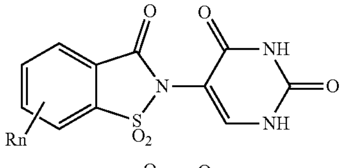
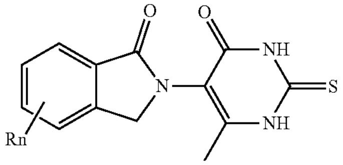

-continued
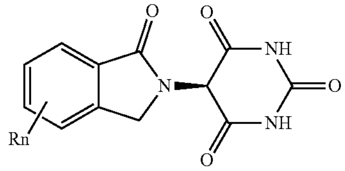
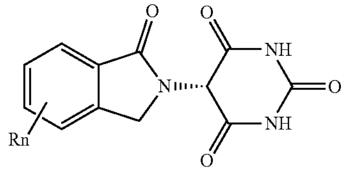
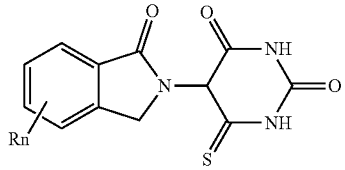
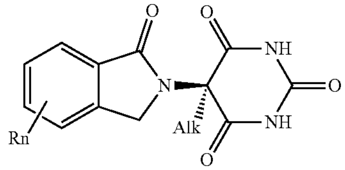
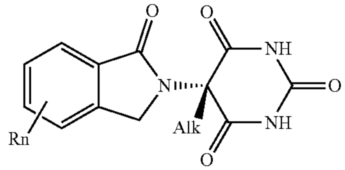
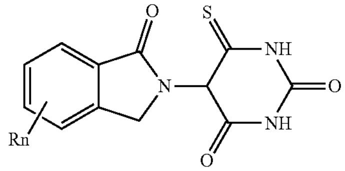
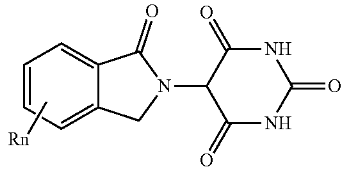
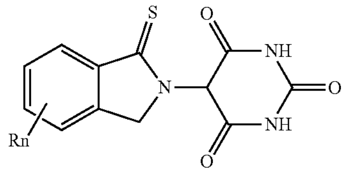
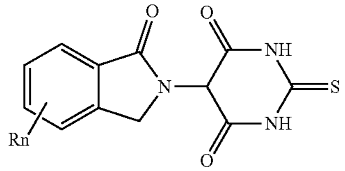
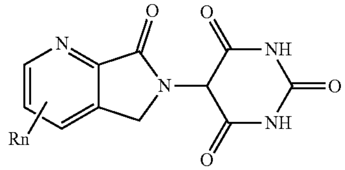
-continued
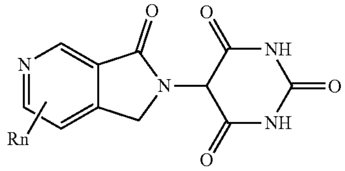
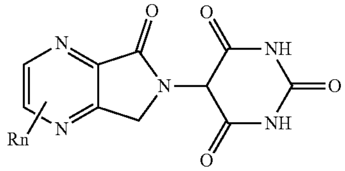
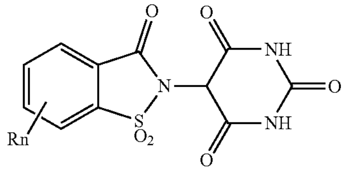
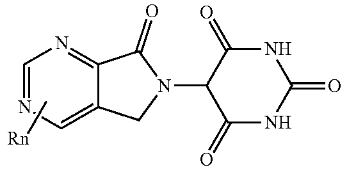
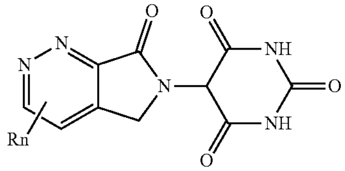
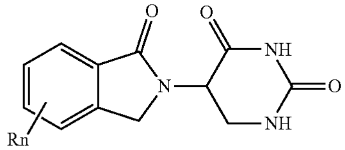
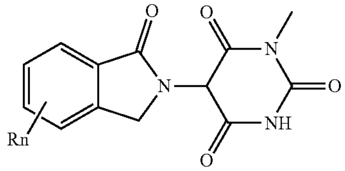
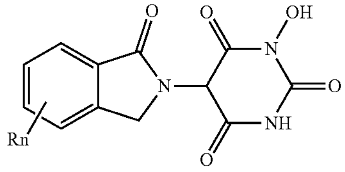
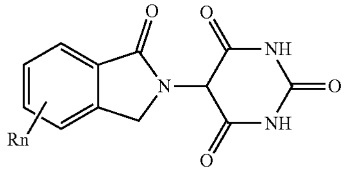
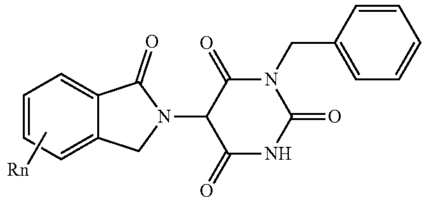

-continued
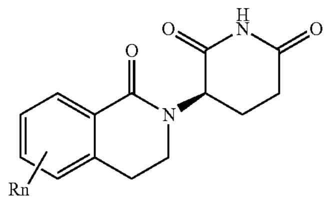
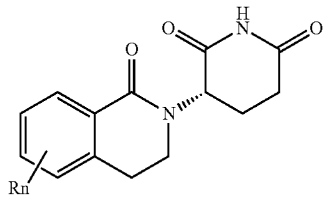
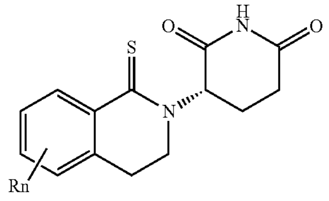
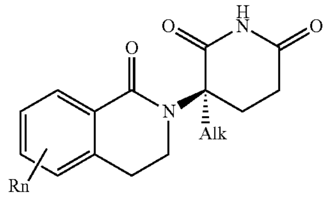
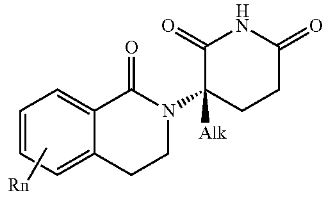
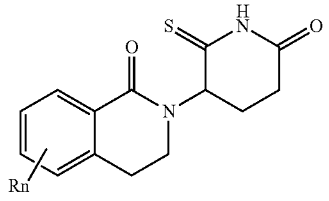
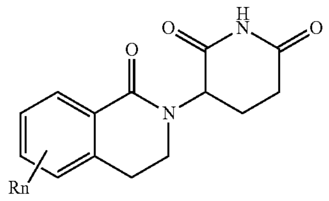
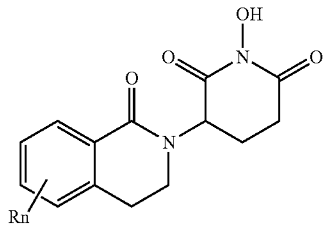
-continued
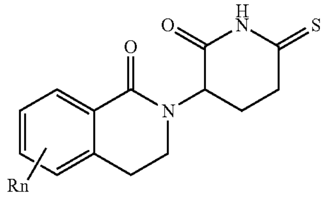
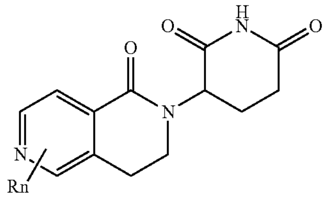
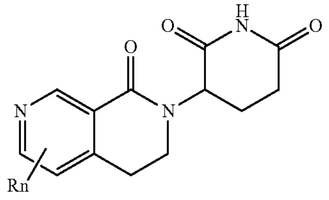
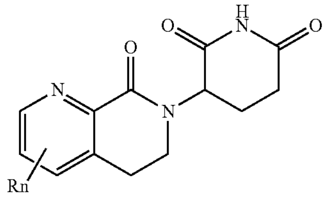
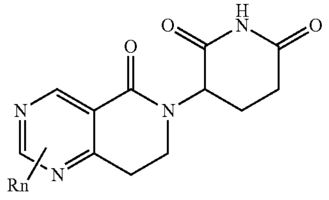
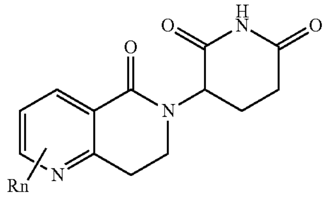
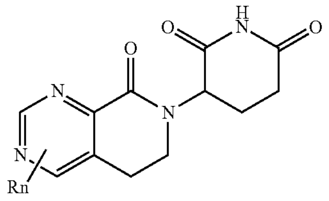
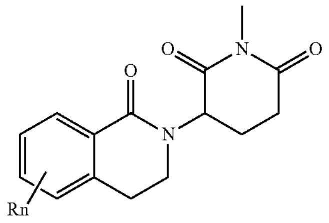

-continued
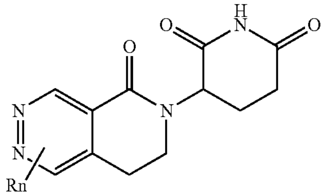
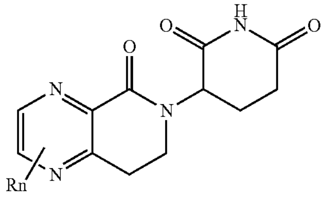
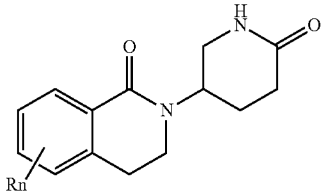
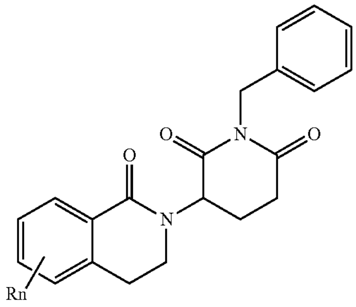
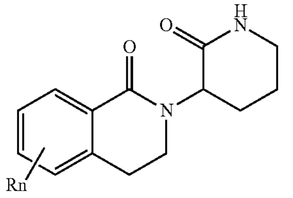
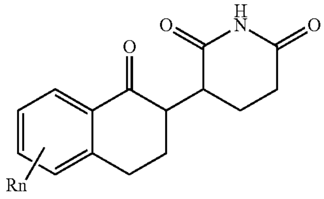
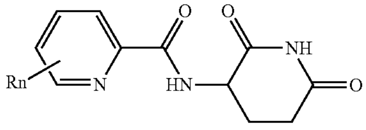
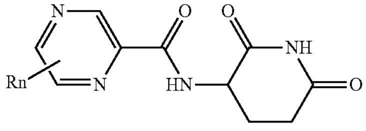
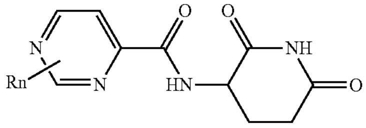
-continued
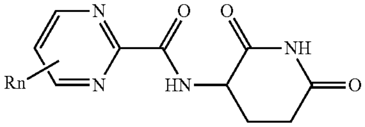
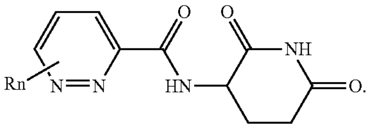
In any aspect or embodiment described herein, the CLM comprises a chemical structure selected from the group:
(h)
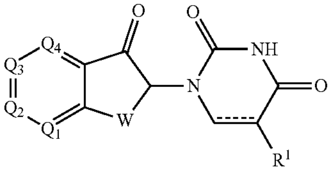
(i)
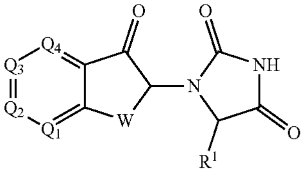
(j)
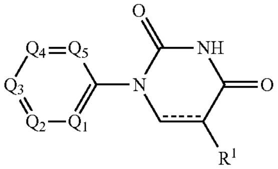
(k)
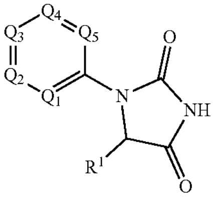
(l)
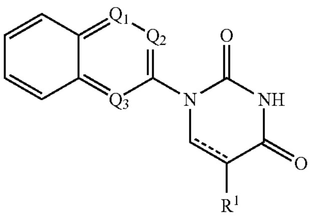
(m)
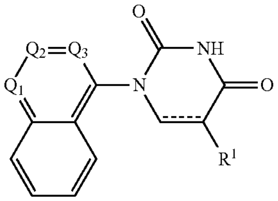

-continued
(n)
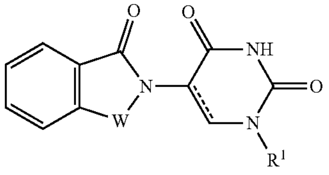
(o)
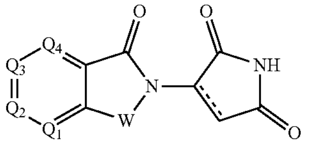
(p)
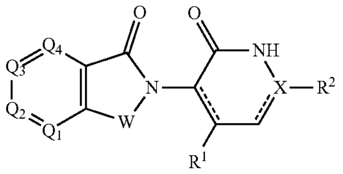
(q)
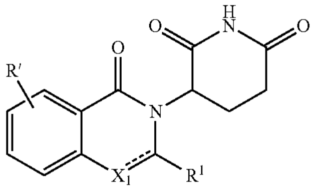
(r)
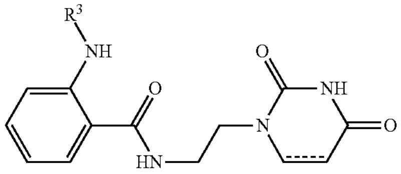
(s)
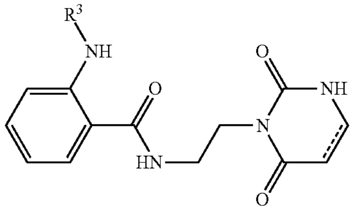
(t)
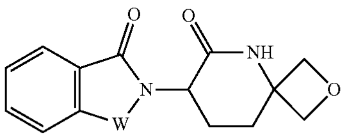
(u)
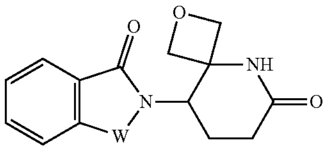
(v)
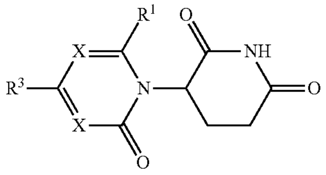
-continued
(w)
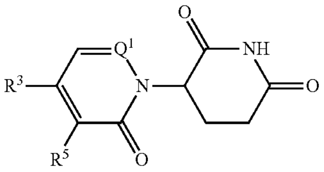
(x)
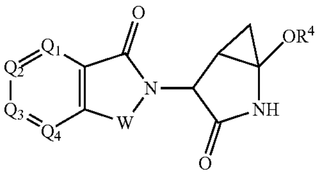
(y)
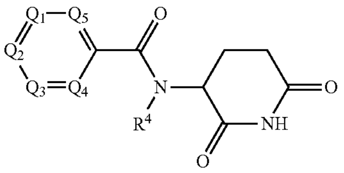
(z)
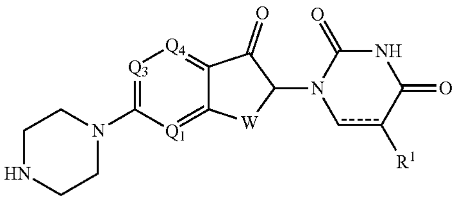
(aa)
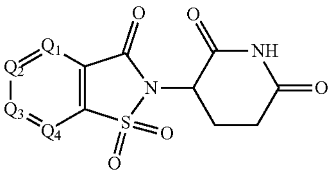
(ab)
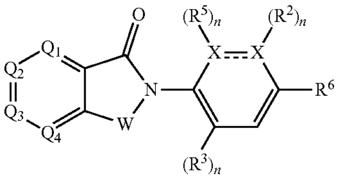
(ac)
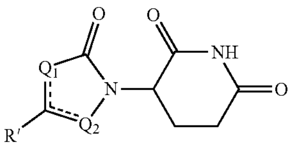
(ad)
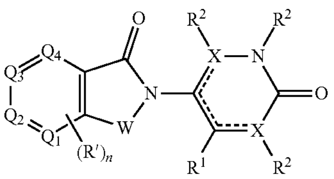
(ae)
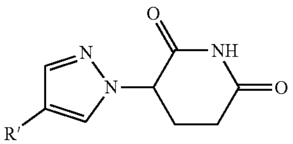

-continued (af)

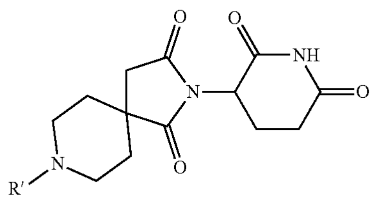

(ag)

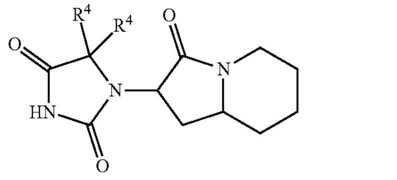

(ah)

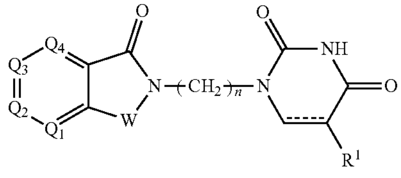

(ai)

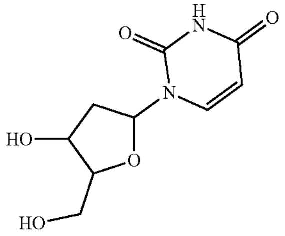

(aj)

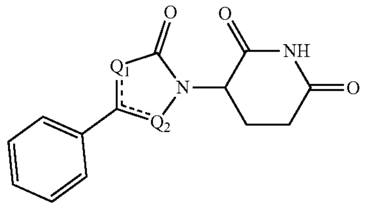

(ak)

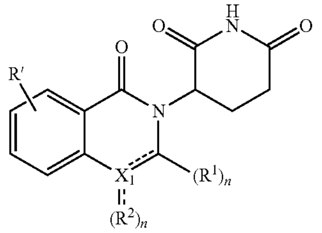

(al)

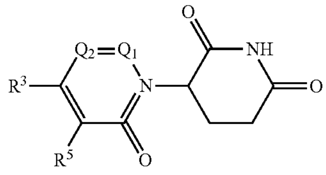

-continued (am)

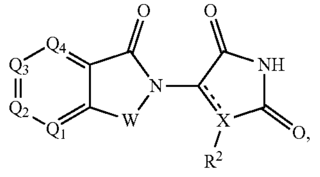

wherein:

W is independently selected from O, $CH_2$, CHR, C═O, $SO_2$, NH, N, optionally substituted cyclopropyl group, optionally substituted cyclobutyl group, and N-alkyl (e.g., $CH_2$, CHR, C═O, $SO_2$, NH, and N-alkyl);

$Q_1$, $Q_2$, $Q_3$, $Q_4$, $Q_5$ are each independently represent a nitrogen or a carbon substituted with a group independently selected from $R^1$, N and N-oxide;

$R^1$ is selected from absent, H, OH, CN, C1-C3 alkyl, and C═O;

$R^2$ is selected from the group absent, H, OH, CN, C1-C3 alkyl, $CHF_2$, $CF_3$, CHO, C(═O)$NH_2$;

$R^3$ is selected from H, alkyl (e.g., C1-C6 or C1-C3 alkyl), substituted alkyl (e.g., substituted C1-C6 or C1-C3 alkyl), alkoxy (e.g., C1-C6 or C1-C3 alkoxyl), and substituted alkoxy (e.g., substituted C1-C6 or C1-C3 alkoxyl);

$R^4$ is selected from H, alkyl, and substituted alkyl;

$R^5$ and $R^6$ are each independently selected from H, halogen, C(═O)$R^1$, CN, OH, and $CF_3$;

X is C, CH, C═O, or N;

$X_1$ is C═O, N, CH, or $CH_2$;

R' is selected from H, halogen, amine, alkyl (e.g., C1-C3 alkyl), substituted alkyl (e.g., substituted C1-C3 alkyl), alkoxy (e.g., C1-C3 alkoxyl), substituted alkoxy (e.g., substituted C1-C3 alkoxyl), $NR^2R_3$, C(═O)$OR^2$, and optionally substituted phenyl;

n is 0-4;

 is a single or double bond; and the CLM is covalently joined to a PTM either by a covalent bond or through, a chemical linking group (L).

In any aspect or embodiment described herein, the CLM is covalently joined directly to a PTM, or through a chemical linking group (L), via an R group (such as, R, $R^1$, $R_2$, $R_3$, $R_4$ or R'), W, X, or a Q group (such as, $Q_1$, $Q_2$, $Q_3$, $Q_4$, or $Q_5$).

In any aspect or embodiment described herein, the CLM is covalently joined directly to a PTM, or through a chemical linking group (L), via W, X, R, $R^1$, $R^2$, $R^3$, $R^4$, $R^5$, R', $Q_1$, $Q_2$, $Q_3$, $Q_4$, and $Q_5$.

In any aspect or embodiment described herein, the W, X, $R^1$, $R^2$, $R^3$, $R^4$, R', $Q_1$, $Q_2$, $Q_3$, $Q_4$, or $Q_5$ can independently be covalently coupled to a linker to which is attached one or more PTM, ULM, or CLM groups.

More specifically, non-limiting examples of CLMs include those shown below as well as "hybrid" molecules or compounds that arise from combining one or more features of the following compounds:

(an)

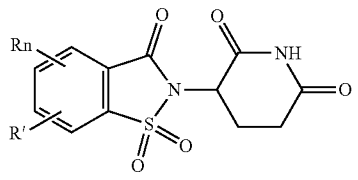

-continued
(ao)
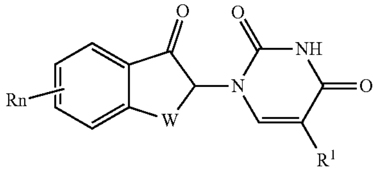
(ap)
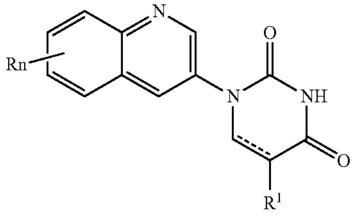
(aq)
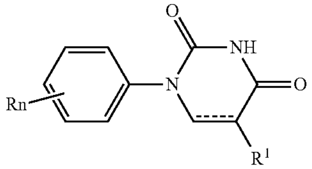
(ar)
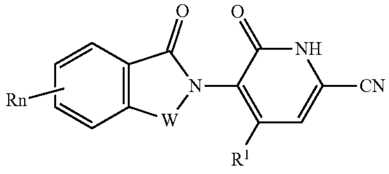
(as)
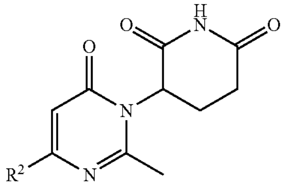
(at)
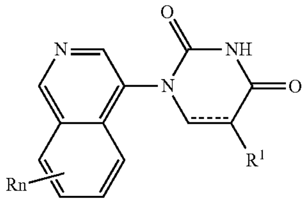
(au)
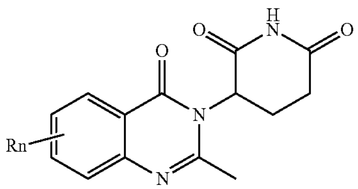
(av)
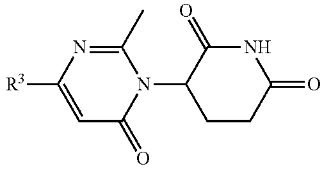
-continued
(aw)
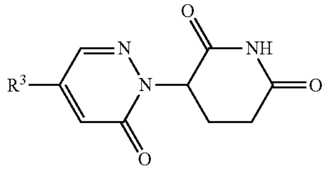
(ax)
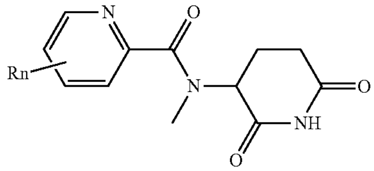
(ay)
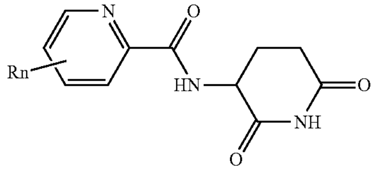
(az)
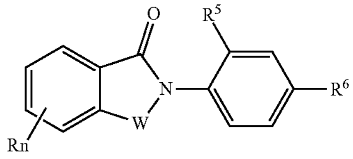
(ba)
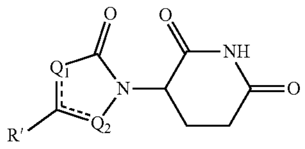
(bb)
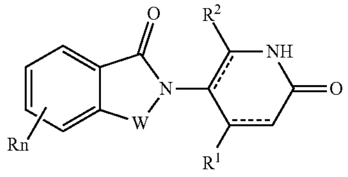
(bc)
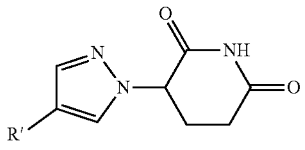
(bd)
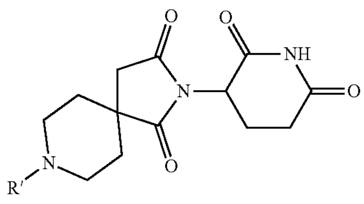
(be)
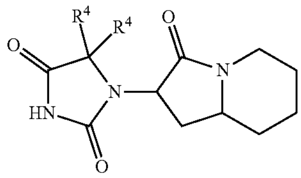

-continued (bf)

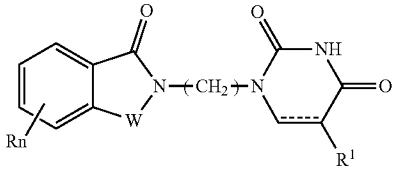

(bg)

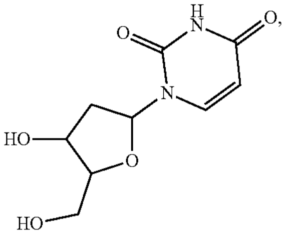

wherein:

W is independently selected from the group $CH_2$, CHR, C═O, $SO_2$, NH, and N-alkyl;

$R^1$ is selected from the group absent, H, CH, CN, and C1-C3 alkyl;

$R^2$ is H or a C1-C3 alkyl;

$R^3$ is selected from H, alkyl, substituted alkyl, alkoxy, and substituted alkoxy;

$R^4$ is methyl or ethyl;

$R^5$ is H or halo;

$R^6$ is H or halo;

n is an integer from 0 to 4;

R and R' is H are independently H, a functional group or atom (e.g., H, halogen (such as —Cl or —F), amine, C13 alkyl, C13 alkoxyl, $NR^2R_3$, or C(═O)$OR^2$); or an attachment point for a PTM or a chemical linking group (L);

$Q_1$ and $Q_2$ are each independently C or N substituted with a group independently selected from H and C1-C3 alkyl; and ∿∿ is a single or double bond.

In any of the embodiments described herein, the W, $R^1$, $R^2$, $Q_1$, $Q_2$, $Q_3$, $Q_4$, R, or R' can independently be covalently coupled to a linker to which is attached one or more PTM groups.

In any of the embodiments described herein, the $R^1$, $R^2$, $Q_1$, $Q_2$, $Q_3$, $Q_4$, R, and R' can independently be covalently coupled to a linker to which is attached one or more PTM groups.

In any of the embodiments described herein, the $Q_1$, $Q_2$, $Q_3$, $Q_4$, R, and R' can independently be covalently coupled to a linker to which is attached one or more PTM groups.

In any aspect or embodiment described herein, R is modified to be covalently joined to the linker group (L) or directly to a PTM, or combination thereof.

In any aspect or embodiment described herein, the CLM is selected from:

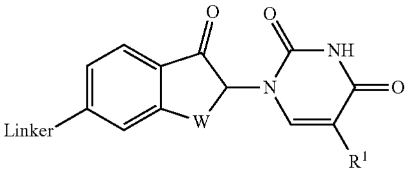

-continued

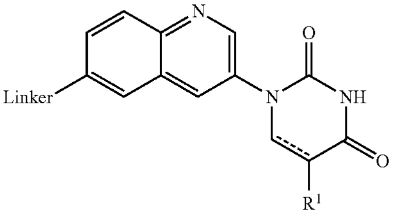

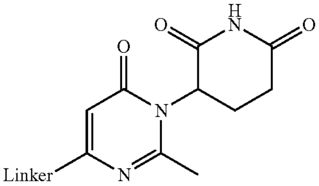

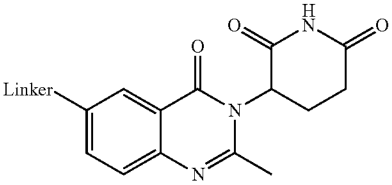

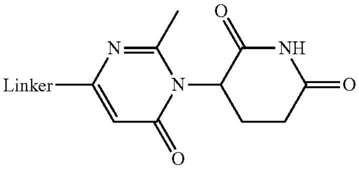

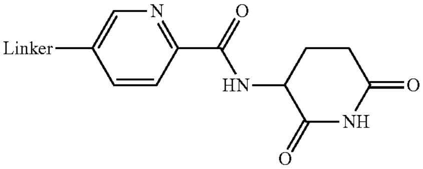

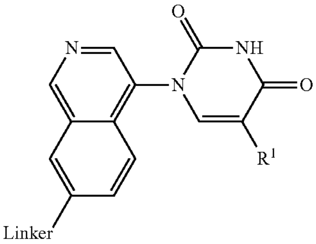

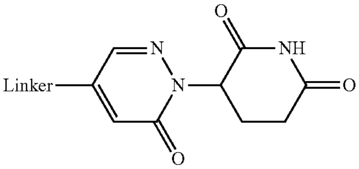

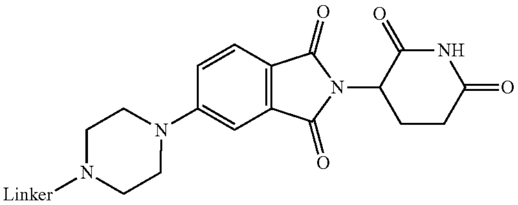

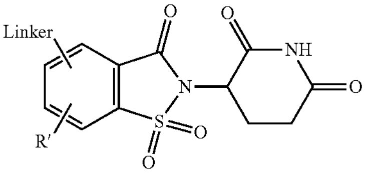

-continued
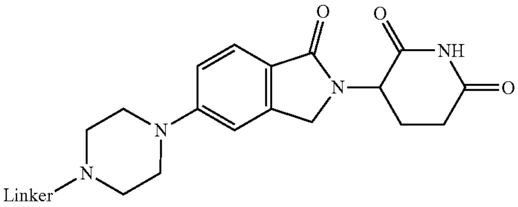
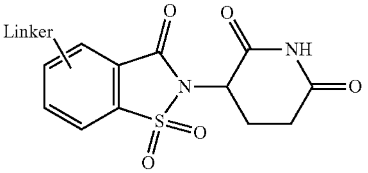
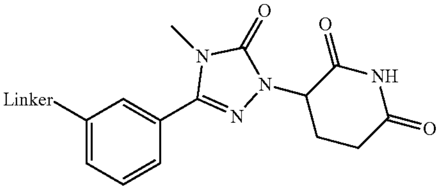
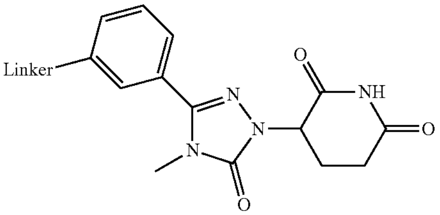
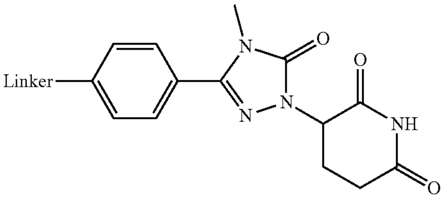
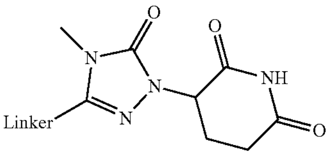
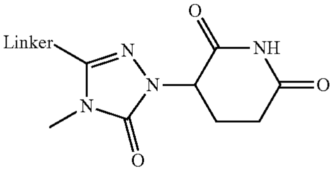
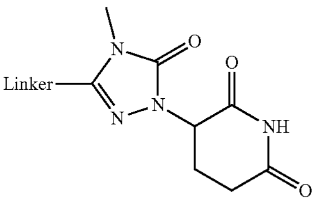
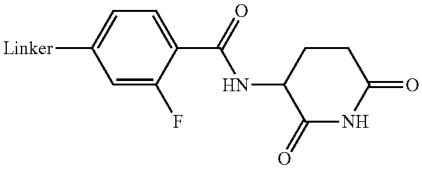
-continued
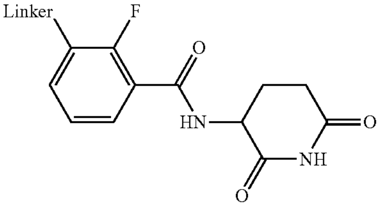
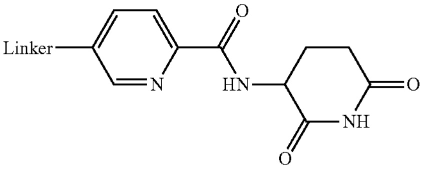
and
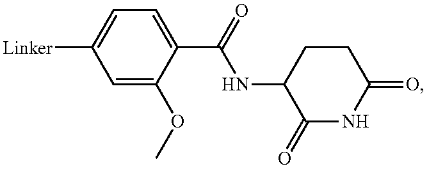
wherein R' is a halogen and $R^1$ is as described in any aspect or embodiment described herein.
In any aspect or embodiment described herein, "CLM" can be an imide that binds to cereblon E3 ligase. These imides and linker attachment point can be, but not limited to, one of the following structures:
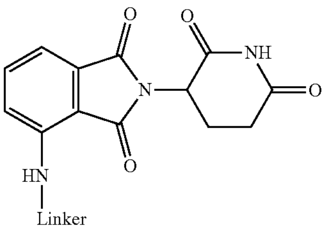
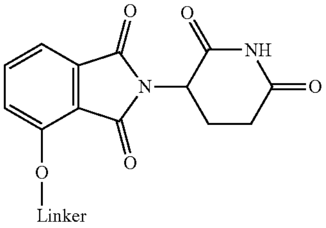
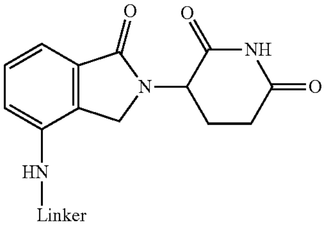
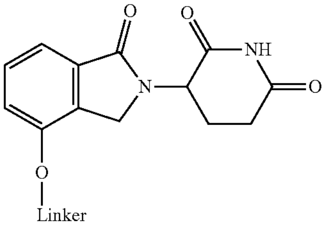

-continued
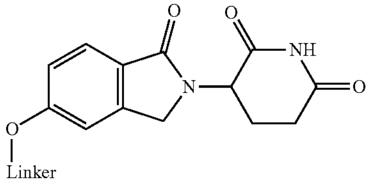
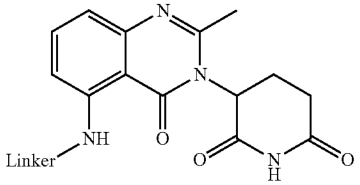
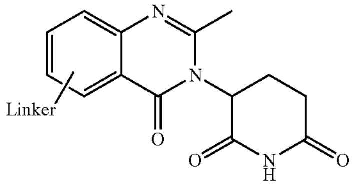
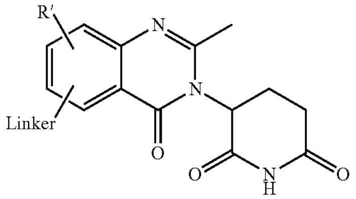
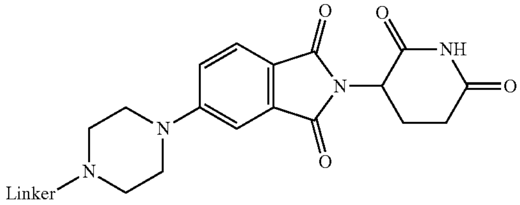
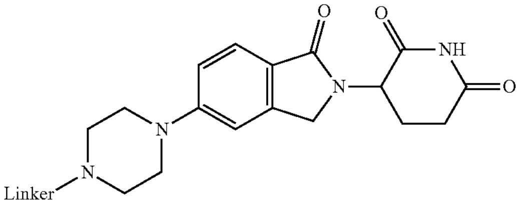
or
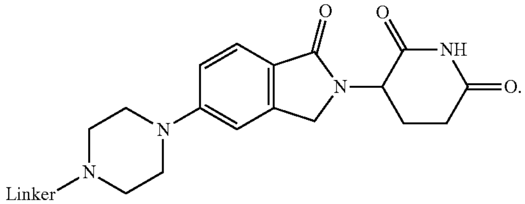
In any aspect or embodiment described herein, the CLM or ULM is selected from the group consisting of:
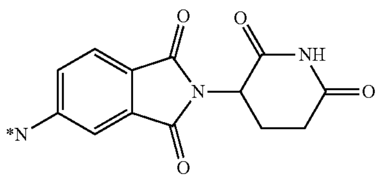
-continued
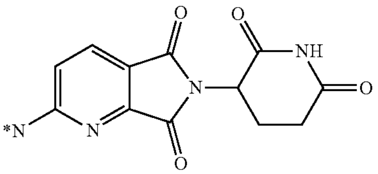
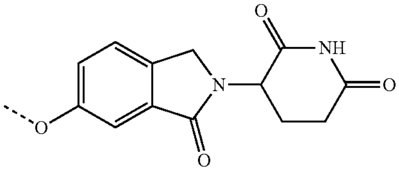
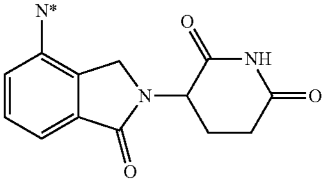
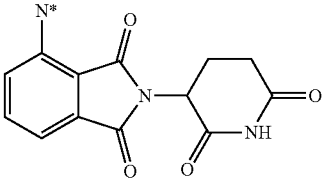
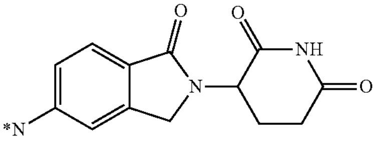
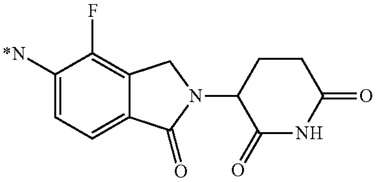
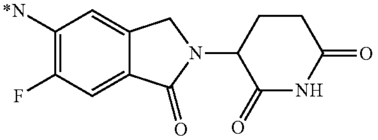
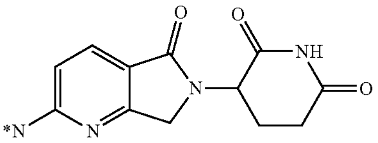
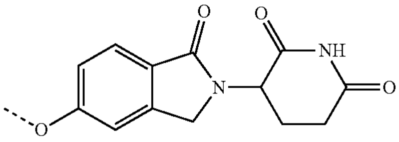
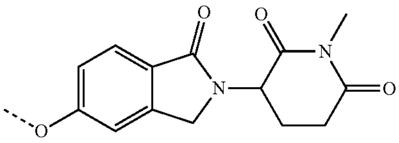

-continued

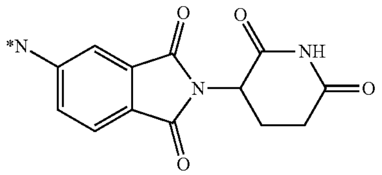

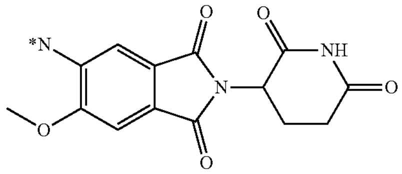

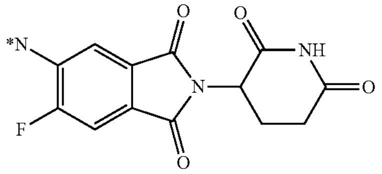

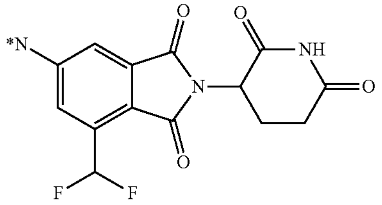

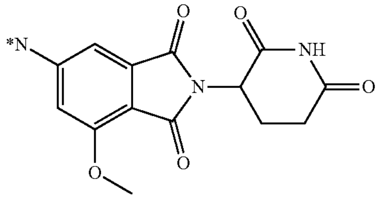

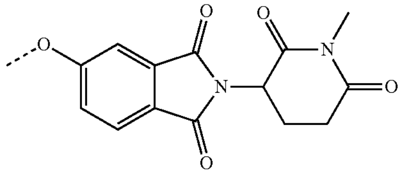

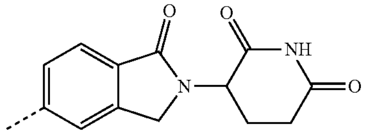

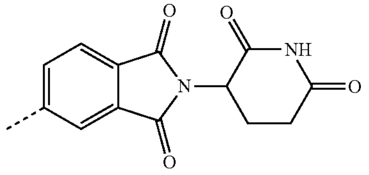

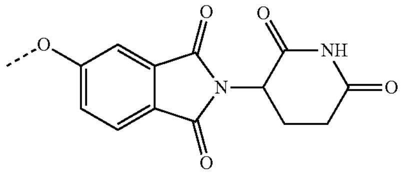

-continued

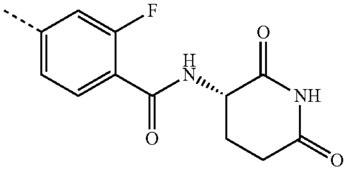

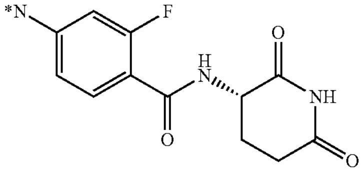

or

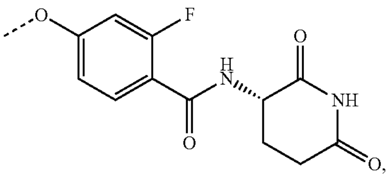
, wherein:

N* is a nitrogen atom (i) that is covalently linked to the PTM via the chemical linker group (L) with a H or methyl completing valency or (ii) that is shared with the chemical linker group (L) (e.g., a heteroatom shared with an optionally substituted heterocycloalkyl of the chemical linker group (L); and

 of the CLM indicates the point of attachment with a linker group or a PTM.

In any aspect or embodiment described herein, the CLM is selected from the group consisting of:

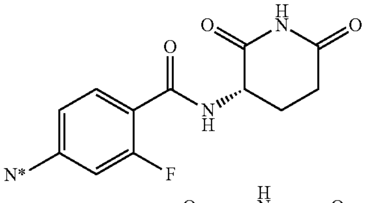

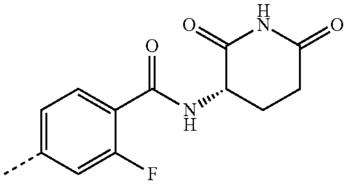

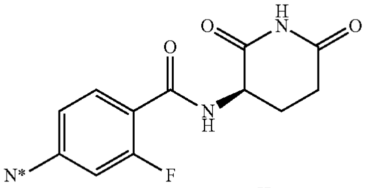

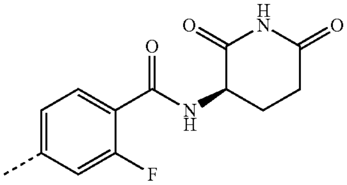

wherein:
N* is a nitrogen atom that is shared with the chemical linker group (L) (e.g., a heteroatom shared with an optionally substituted heterocyloalkyl of the chemical linker group (L); and
 of the CLM indicates the point of attachment with a linker group or a PTM.
In any aspect or embodiment described herein, the CLM is selected from the group consisting of:
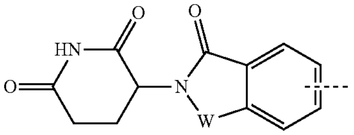,
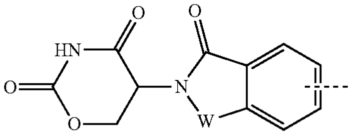,
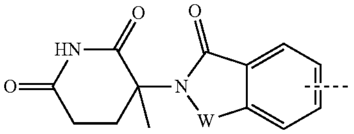,
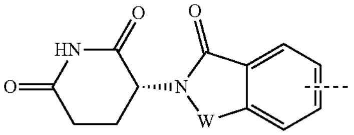,
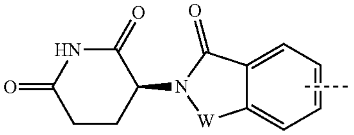,
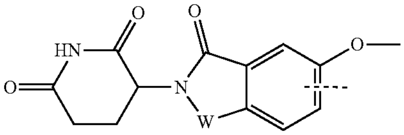,
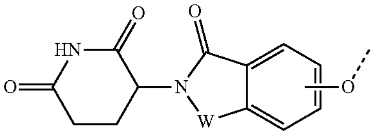,
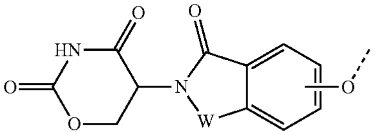,
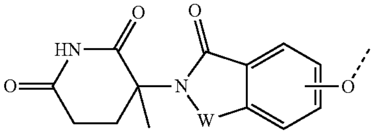,
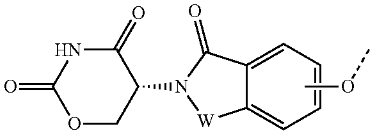,
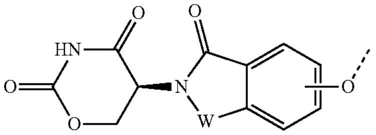,
-continued
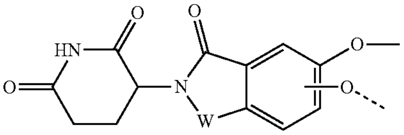,
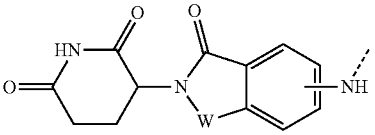,
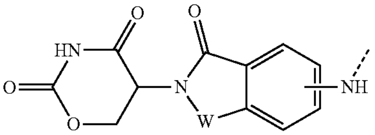,
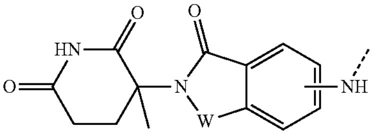,
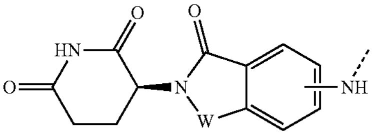,
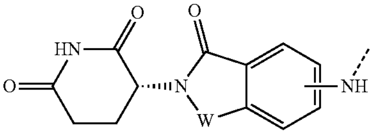,
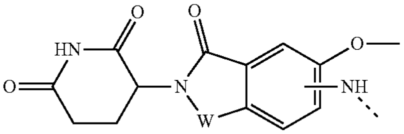,
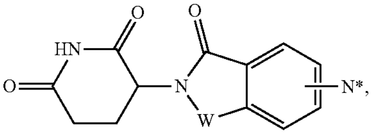,
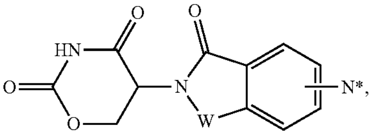,
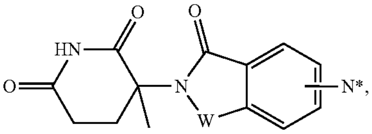,
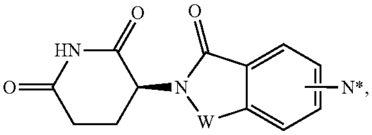,
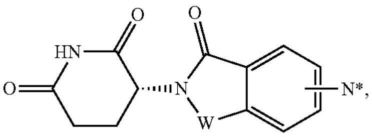, -continued

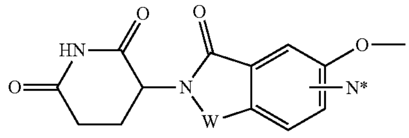
,

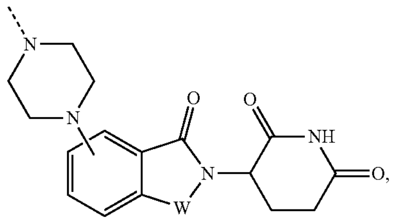

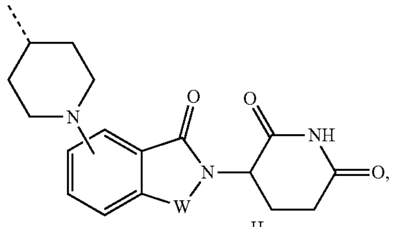

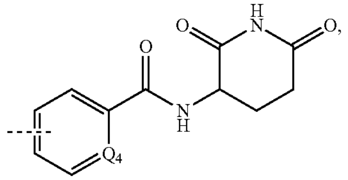
and

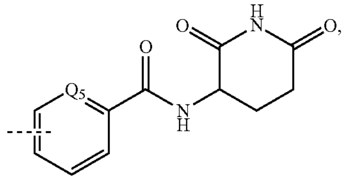

wherein:

 of the CLM indicates the point of attachment with a linker group or a PTM;

N* is a nitrogen atom that is shared with the chemical linker group or PTM; and

W, Q4, and Q5 are each defined as described in any aspect or embodiment described herein.

Exemplary ILMs

AVPI Tetrapeptide Fragments

In any aspect or embodiment described herein, the ILM can comprise an alanine-valine-proline-isoleucine (AVPI) tetrapeptide fragment or an unnatural mimetic thereof. In any aspect or embodiment described herein, the ILM is selected from the group consisting of chemical structures represented by ILM-I, ILM-II, ILM-III, and ILM-IV:

(ILM-I)

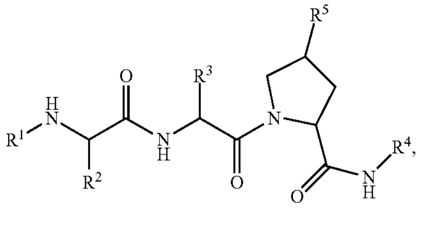

-continued (ILM-II)

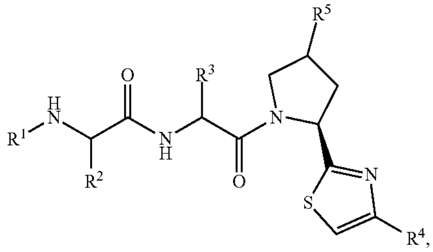

(ILM-III)

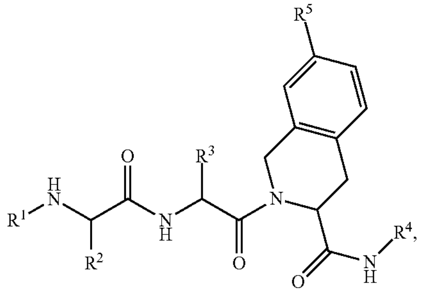
and (ILM-IV)

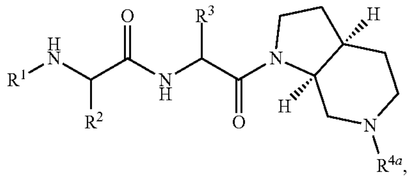

wherein:

$R^1$ for ILM-I, ILM-II, ILM-III, and ILM-IV is selected from H or $C_{1-3}$ alkyl (e.g., methyl or ethyl);

$R^2$ for ILM-I, ILM-II, ILM-III, and ILM-IV is selected from H or $C_{1-3}$ alkyl (e.g., methyl or ethyl);

$R^3$ for ILM-I, ILM-II, ILM-III, and ILM-IV is selected from cycloalkyl and heterocycloalkyl;

$R^5$ for ILM-I, ILM-II, ILM-III, and ILM-IV is H;

$R^4$ ILM-I, ILM-II, and ILM-III is selected from cycloalkyl (e.g., 5-7 cycloalkyl), heterocycloalkyl (e.g., 5-7 heterocycloalkyl), aryl (e.g., 5-7 membered aryl), heteroaryl (e.g., 5-7 membered heteroaryl), bicyclic group optionally having 1, 2, or 3 heteroatoms, such as O or N (e.g., a 9-12 membered bicyclic group optionally having 1, 2, or 3 heteroatoms, such as O or N), further optionally substituted with 1-3 substituents as described above; and $R^{4a}$ for ILM-IV is selected from $-(CH_2)_x$-aryl (e.g., 5-7 membered aryl), $-(CH_2)_x$-heteroaryl (e.g., 5-7 membered heteroaryl), further optionally substituted with 1-3 substituents as described above;

x for ILM-IV is 0, 1, 2, or 3; and the ILM is attached to a chemical linking group (L) or a PTM via $R^4$, $R^{4a}$, $R^5$.

In any aspect or embodiment described herein, at least one of:

$R^1$ for ILM-I, ILM-II, ILM-III, and ILM-IV is a methyl group;

$R^2$ for ILM-I, ILM-II, ILM-III, and ILM-IV is a methyl group;

$R^3$ for ILM-I, ILM-II, ILM-III, and ILM-IV is C6 cycloalkyl or C6 heterocycloalkyl (e.g., 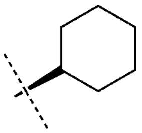 );

$R^4$ for ILM-I, ILM-II, and ILM-III is an 11-membered bicyclic group optionally including one heteroatom (wherein the bicylic group is optionally the attachment point of the ILM to a chemical linker group (L) or a PTM, as described herein), or $R^{4a}$ for ILM-IV is $—CH_2CH_2—C_{5-7}$ aryl, such as phenyl (wherein the $C_{5-7}$ aryl or phenyl is the point of attachment for the ILM to a chemical linker group (L) or a PTM, as described herein); or a combination thereof.

In any aspect or embodiment described herein, $R^4$ for ILM-I, ILM-II, and ILM-III is:

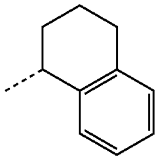

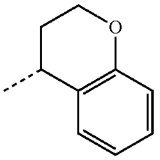

or

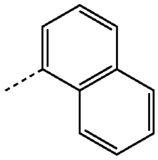

.

In any aspect or embodiment described herein, the ILM or ULM is selected from the group consisting of:

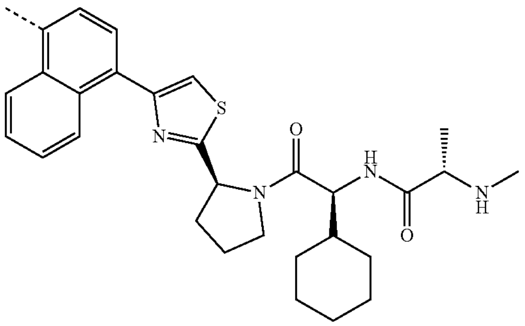

,

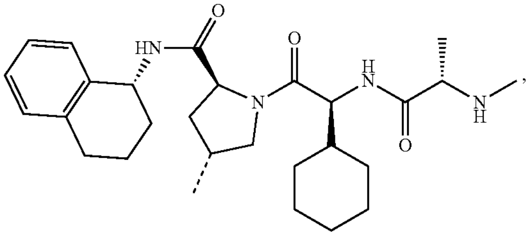

,

-continued

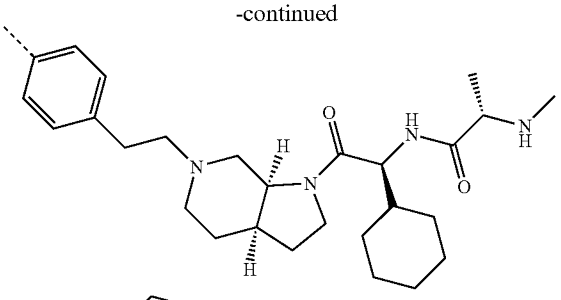

,

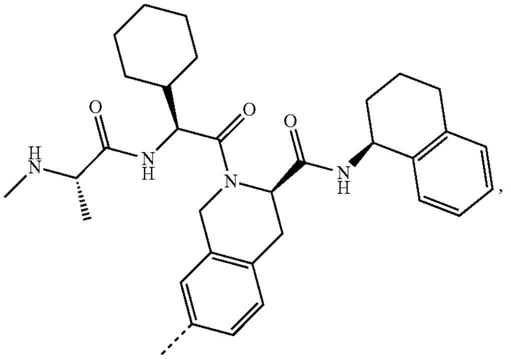

, and

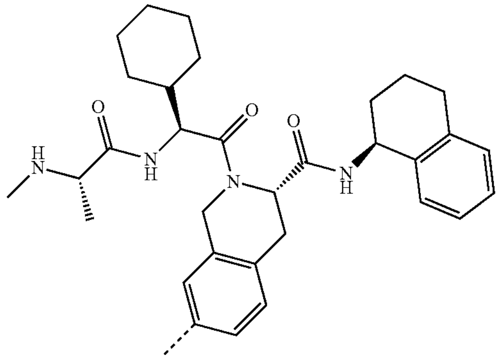

, wherein the  indicates the site of attachment of a PTM via a chemical linking group (L).

In any aspect or embodiment described herein, the ILM can have the structure of Formula (XVII), which is based on the IAP ligands described in Cohen, F. et al., Antogonists of inhibitors of apoptosis proteins based on thiazole amide isosteres, Bioorg. Med. Chem. Lett., 20(7), 2229-33 (2010), or an unnatural mimetic thereof:

(XVII)

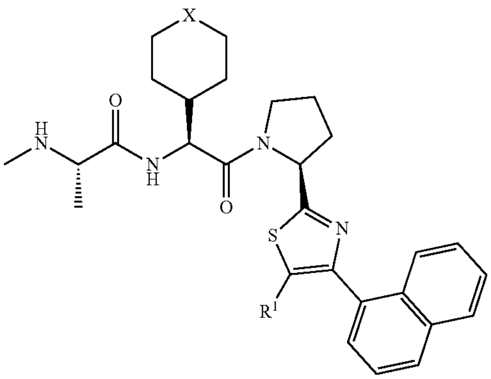

, wherein:

$R^1$ of Formula (XVII) is selected from the group halogen (e.g. fluorine), cyano,

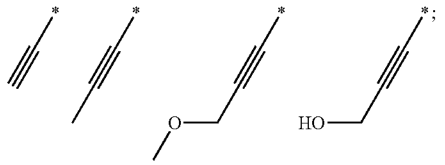

X of Formula (XVII) is selected from the group O or $CH_2$.

In any aspect or embodiment described herein, the ILM of the composition is selected from the group consisting of:

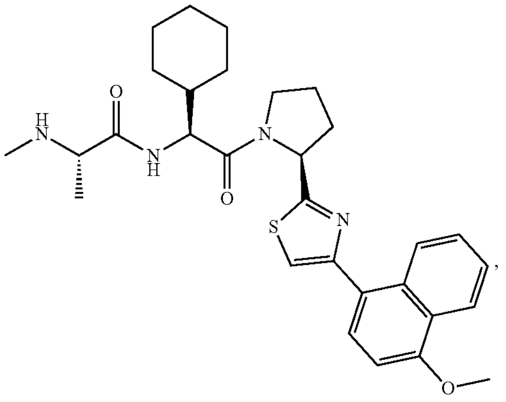

and

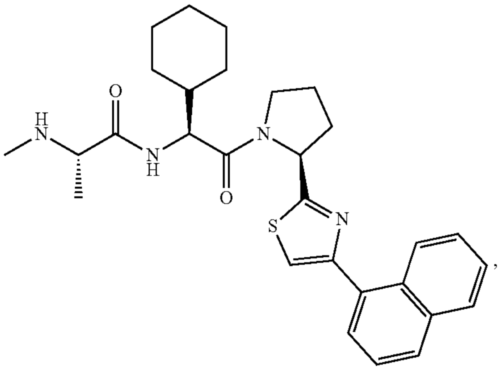

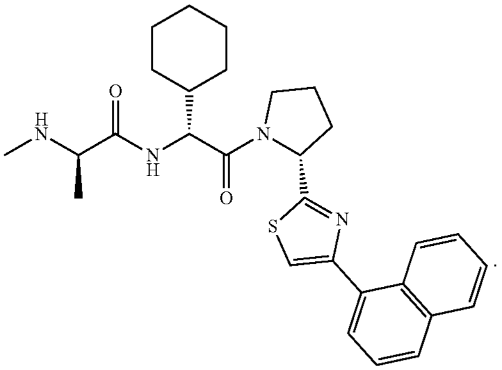

In any aspect or embodiment described herein, the ILM of the compound is:

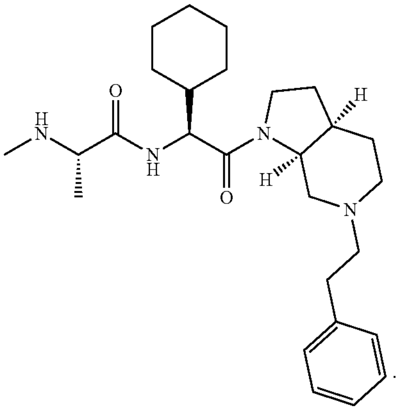 [SMILES: CN[C@@H](C)C(=O)N[C@H](C(=O)N1CC[C@H]2CCN(CCc3ccccc3)C[C@H]21)C1CCCCC1]

In any aspect or embodiment described herein, the ILM of the compound has a chemical structure selected from the group consisting of:

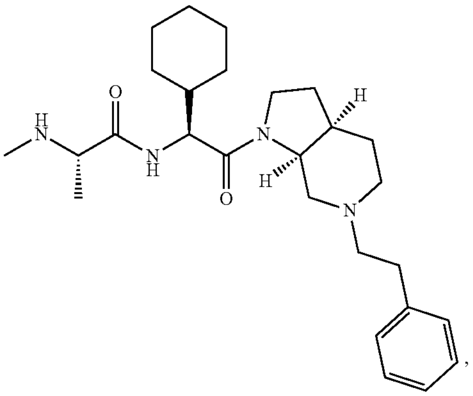

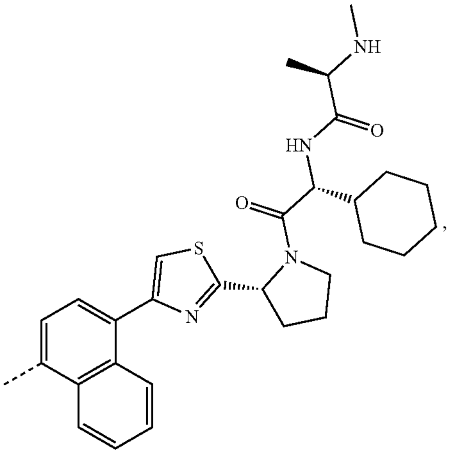

-continued

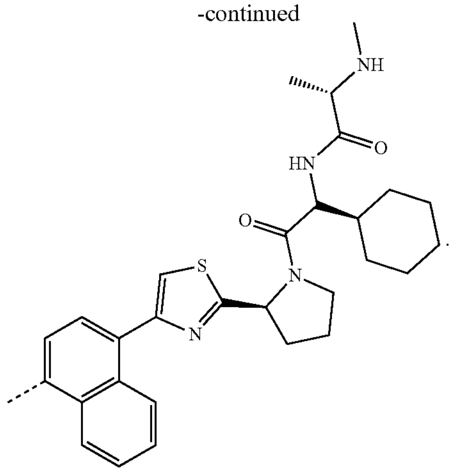

Exemplary Linkers

In any aspect or embodiment described herein, the compounds as described herein include a PTM chemically linked to a ULM (e.g., CLM, VLM, ILM, or a combination thereof) via a chemical linker (L). In certain embodiments, the linker group L comprises one or more covalently connected structural units (e.g., $-A^L{}_1 \ldots (A^L)_q-$ or $-(A^L)_q-$), wherein $A^{L1}$ is a group coupled to PTM, and $(A^L)_q$ is a group coupled to ULM.

In any aspect or embodiment described herein, the linker (L) to a ULM (e.g., VLM, ILM, or CLM) connection is a stable L-ULM connection. For example, in any aspect or embodiment described herein, when a linker (L) and a ULM are connected via a heteroatom (e.g., N, O, S), any additional heteroatom, if present, is separated by at least one carbon atom (e.g., —$CH_2$—), such as with an acetal or aminal group. By way of further example, in any aspect or embodiment described herein, when a linker (L) and a ULM are connected via a heteroatom, the heteroatom is not part of an ester.

In any aspect or embodiment described herein, the linker group L is a bond or a chemical linker group represented by the formula $-(A^L)_q-$, wherein A is a chemical moiety, as described in any aspect or embodiment described herein, and q is an integer from 1-100 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80), and wherein L is covalently bound to both the PTM and the ULM, and provides for binding of the PTM to the protein target and the ULM to an E3 ubiquitin ligase to effectuate target protein ubiquitination.

In any aspect or embodiment described herein, the linker group L is a bond or a chemical linker group represented by the formula $-(A^L)_q-$, wherein A is a chemical moiety, as described in any aspect or embodiment described herein, and q is an integer from 6-30 (e.g., 1, 2, 3, 4, 5, 6, 7, 8, 9, 10, 11, 12, 13, 14, 15, 16, 17, 18, 19, 20, 21, 22, 23, 24, or 25), and wherein L is covalently bound to both the PTM and the ULM, and provides for binding of the PTM to the protein target and the ULM to an E3 ubiquitin ligase in sufficient proximity to result in target protein ubiquitination.

In any aspects or embodiment described herein, the linker group (L) is: $-(A^L)_q-$, wherein:

$(A^L)_q$ is a group which connects a ULM (such as CLM, ILM, or VLM) to PTM; q of the linker is an integer greater than or equal to 1;

each $A^L$ is independently selected from the group consisting of, a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, C=O, $CR^{L1}$=$CR^{L2}$, C≡C, $SiR^{L1}R^{L2}$, $P(O)R^{L1}$, $P(O)OR^{L1}$, $NR^{L3}C(=NCN)NR^{L4}$, $NR^{L3}C(=NCN)$, $NR^{L3}C(=CNO_2)NR^{L4}$, $C_{3-11}$cycloalkyl optionally substituted with 1-6 $R^{L1}$ and/or $R^{L2}$ groups, $C_{5-13}$ spirocycloalkyl optionally substituted with 1-9 $R^{L1}$ and/or $R^{L2}$ groups, $C_{3-11}$ heterocyclyl optionally substituted with 1-6 $R^{L1}$ and/or $R^{L2}$ groups, $C_{5-13}$ spiroheterocyclyl optionally substituted with 1-8 $R^{L1}$ and/or $R^{L2}$ groups, aryl optionally substituted with 1-6 $R^{L1}$ and/or $R^{L2}$ groups, heteroaryl optionally substituted with 1-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 1-4 $R^{L5}$ groups; and $R^{L1}$, $R^{L2}$, $R^{L3}$, $R^{L4}$ and $R^{L5}$ are, each independently selected from H, halo, $C_{18}$alkyl, $OC_{1-8}$alkyl, $SC_{1-8}$alkyl, $NHC_{1-8}$alkyl, $N(C_{1-8}alkyl)_2$, $C_{3-11}$cycloalkyl, aryl (e.g., 5-, 6-, 7-, or 8-membered aryl), heteroaryl (e.g., 5-, 6-, 7-, or 8-membered heteroaryl), $C_{3-11}$heterocyclyl, $OC_{3-8}$cycloalkyl, $SC_{3-8}$cycloalkyl, $NHC_{3-8}$cycloalkyl, $N(C_{3-8}cycloalkyl)_2$, $N(C_{3-8}cycloalkyl)(C_{1-8}alkyl)$, OH, $NH_2$, SH, $SO_2C_{1-6}$alkyl, $P(O)(OC_{1-8}alkyl)(C_{1-8}alkyl)$, $P(O)(OC_{1-8}alkyl)_2$, C≡C—$C_{1-8}$alkyl, C≡CH, CH=$CH(C_{1-8}alkyl)$, $C(C_{1-8}alkyl)$=$CH(C_{1-8}alkyl)$, $C(C_{1-8}alkyl)$=$C(C_{1-8}alkyl)_2$, $Si(OH)_3$, $Si(C_{1-8}alkyl)_3$, $Si(OH)(C_{1-8}alkyl)_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}alkyl)_2$, $N(C_{1-8}alkyl)CONH(C_{1-8}alkyl)$, $N(C_{1-8}alkyl)CON(C_{1-8}alkyl)_2$, $NHCONH(C_{1-8}alkyl)$, $NHCON(C_{1-8}alkyl)_2$, $NHCONH_2$, $N(C_{1-8}alkyl)SO_2NH(C_{1-8}alkyl)$, $N(C_{1-8}alkyl)$ $SO_2N(C_{1-8}alkyl)_2$, NH $SO_2NH(C_{1-8}alkyl)$, NH $SO_2N(C_{1-6}alkyl)_2$, and NH $SO_2NH_2$.

In any aspect or embodiment described herein, q is an integer greater than or equal to 1.

In any aspect or embodiment described herein, e.g., where q of the linker is greater than 2, $(A^L)_q$ is a group which is $A^{L1}$ and $(A^L)_q$ wherein the linker couples a PTM to a ULM.

In any aspect or embodiment described herein, e.g., where q of the linker is 2, $A^{L2}$ is a group which is connected to $A^L{}_1$ and to a ULM.

In any aspect or embodiment described herein, q of the chemical linking group (L) is an integer from 1-100 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80).

In any aspect or embodiment described herein, e.g., where q of the linker is 1, the structure of the linker group L is $-A^{L1}-$, and $A^{L1}$ is a group which connects a ULM moiety to a PTM moiety.

In any aspect or embodiment described herein, the unit $A^L$ of linker (L) comprises a group represented by a general structure selected from the group consisting of:

—$NR(CH_2)_n$-(lower alkyl)-, —$NR(CH_2)_n$-(lower alkoxyl)-, —$NR(CH_2)_n$-(lower alkoxyl)-$OCH_2$—, —$NR(CH_2)_n$-(lower alkoxyl)-(lower alkyl)-$OCH_2$—, —NR($CH_2$)$_n$-(cycloalkyl)-(lower alkyl)-$OCH_2$—, —NR($CH_2$)$_n$-(heterocycloalkyl)-, —NR($CH_2CH_2O$)$_n$-(lower alkyl)-O—$CH_2$—, —NR($CH_2CH_2O$)$_n$-(heterocycloalkyl)-O—$CH_2$—, —NR($CH_2CH_2O$)$_n$-Aryl-O—$CH_2$—, —NR($CH_2CH_2O$)$_n$-(heteroaryl)-O—$CH_2$—, —NR($CH_2CH_2O$)$_n$-(cyclo alkyl)-O-(hetero aryl)-O—$CH_2$—, —NR($CH_2CH_2O$)$_n$-(cycloalkyl)-O-Aryl-O—$CH_2$—, —NR($CH_2CH_2O$)$_n$-(lower alkyl)-NH-Aryl-O—$CH_2$—, —NR($CH_2CH_2C$)$_n$-(lower alkyl)-O-Aryl-$CH_2$, —NR($CH_2CH_2O$)$_n$-cycloalkyl-O-Aryl-, —NR($CH_2CH_2O$)$_n$-cycloalkyl-O-(heteroaryl)l-, —NR($CH_2CH_2$)$_n$-(cycloalkyl)-O-(heterocyclyl)-$CH_2$, —NR($CH_2CH_2$)$_n$-(heterocyclyl)-(heterocyclyl)-$CH_2$, and —N(R1R2)-(heterocyclyl)-$CH_2$; where n of the linker can be 0 to 10;

R of the linker can be H, or lower alkyl; and $R_1$ and $R_2$ of the linker can form a ring with the connecting N.

In any aspect or embodiment described herein, the linker (L) includes an optionally substituted $C_1$-$C_{50}$ alkyl (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ alkyl, and including all subranges, e.g., C1-C10, C1-C20; C2-C10, C2-20; C10-C20, C10-C50 etc.), wherein each carbon is optionally independently substituted or replaced with (1) a heteroatom selected from N, O, S, P, or Si atoms that has an appropriate number of hydrogens, substitutions, or both to complete valency, (2) an optionally substituted cycloalkyl or bicyclic cycloalkly, (3) an optionally substituted heterocyloalkyl or bicyclic heterocyloalkyl, (4) an optionally substituted aryl or bicyclic aryl, or (5) optionally substituted heteroaryl or bicyclic heteroaryl. In any aspect or embodiment described herein, the linker (L) does not have heteroatom-heteroatom bonding (e.g., no heteroatoms are covalently linked or adjacently located).

In any aspect or embodiment described herein, the linker (L) includes an optionally substituted $C_1$-$C_{50}$ alkyl (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ alkyl), wherein:

each carbon is optionally independently substituted or replaced with a group independently selected from $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, C═O, $CR^{L1}$═$CR^{L2}$, C═C, $SiR^{L1}R^{L2}$, $P(O)R^{L1}$, $P(O)OR^{L1}$, $NR^{L3}C$(═NCN)$NR^{L4}$, $NR^{L3}C$(═NCN), $NR^{L3}C$(═$CNO_2$)$NR^{L4}$, $C_{3-11}$cycloalkyl optionally substituted with 1-6 $R^{L1}$ and/or $R^{L2}$ groups, $C_{5-13}$ spirocycloalkyl optionally substituted with 1-9 $R^{L1}$ and/or $R^{L2}$ groups, $C_{3-11}$ heterocyclyl optionally substituted with 1-6 $R^{L1}$ and/or $R^{L2}$ groups, $C_{5-13}$ spiroheterocyclyl optionally substituted with 1-8 $R^{L1}$ and/or $R^{L2}$ groups, aryl optionally substituted with 1-6 $R^{L1}$ and/or $R^{L2}$ groups, or heteroaryl optionally substituted with 1-6 $R^{L1}$ and/or $R^{L2}$ groups, where $R^{L1}$ or $R^{L2}$, each independently, are optionally linked to other groups to form a cycloalkyl and/or a heterocyclyl moiety, optionally substituted with 1-4 $R^{L5}$ groups; and $R^L$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}alkyl)_2$, $C_{3-8}$cycloalkyl, 5-8 membered aryl (e.g., 5-, 6-, 7-, or 8-membered aryl), 5-8 membered heteroaryl (e.g., 5-, 6-, 7-, or 8-membered heteroaryl), $C_{3-11}$heterocyclyl, $OC_{3-8}$cycloalkyl, $SC_{3-8}$cycloalkyl, $NHC_{3-8}$cycloalkyl, $N(C_{3-8}cycloalkyl)_2$, $N(C_{3-8}cycloalkyl)(C_{1-8}alkyl)$, OH, $NH_2$, SH, $SO_2C_{1-8}$alkyl, $P(O)(OC_{1-8}alkyl)(C_{1-8}alkyl)$, $P(O)(OC_{1-8}alkyl)_2$, C≡C—$C_{1-8}$alkyl, C═CH, CH═CH($C_{1-8}$alkyl), C($C_{1-8}$alkyl)═CH($C_{1-8}$alkyl), C($C_{1-8}$alkyl)═C($C_{1-8}alkyl)_2$, $Si(OH)_3$, $Si(C_{1-8}alkyl)_3$, $Si(OH)(C_{18}alkyl)_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}alkyl)_2$, $N(C_{1-8}alkyl)CONH(C_{1-8}alkyl)$, $N(C_{1-8}alkyl)CON(C_{1-8}alkyl)_2$. $NHCONH(C_{1-8}alkyl)$, $NHCON(C_{1-8}alkyl)_2$, $NHCONH_2$, $N(C_{1-8}alkyl)SO_2NH(C_{1-8}alkyl)$, $N(C_{1-8}alkyl)$ $SO_2N(C_{1-8}alkyl)_2$, NH $SO_2NH(C_{1-8}alkyl)$, NH $SO_2N(C_{1-8}alkyl)_2$, or NH $SO_2NH_2$.

In any aspect or embodiment described herein, the linker group is an optionally substituted $C_1$-$C_{50}$ alkyl (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ alkyl, and including all subranges, e.g., C1-C10, C1-C20; C2-C10, C2-20; C10-C20, C10-C50 etc.), wherein each carbon atom is optionally substituted or replaced with:

a O, N, S, P or Si atom that has an appropriate number of hydrogens, substitutions (e.g., OH, halo, $C_{1-8}$alkyl, methyl, ethyl, $C_{1-8}$haloalkyl, $C_{1-8}$hydroxyalkyl, $C_{1-8}$alkoxy, or methoxy), or both to complete valency;

an optionally substituted aryl (e.g., an optionally substituted 5- or 6-membered aryl) or bicyclic aryl (e.g, an optionally substituted 9-20 membered bicyclic heteraryl), such as an optionally substituted aryl or bicyclic aryl optionally substituted with OH, halo, $C_{1-8}$alkyl, methyl, ethyl, $C_{1-8}$haloalkyl, $C_{1-8}$hydroxyalkyl, $C_{1-8}$alkoxy, or methoxy;

an optionally substituted heteroaryl (e.g., an optionally substituted 5- or 6-membered heteroaryl) or bicyclic heteroaryl (e.g., an optionally substituted 9-20 membered bicyclic heteroaryl), such as an optionally substituted heteroaryl or bicyclic heteroaryl having one or more heteroatoms selected from N, O, S, P, and Si that has an appropriate number of hydrogens, substitutions (e.g., OH, halo, $C_{1-8}$alkyl, methyl, ethyl, $C_{1-8}$haloalkyl, $C_{1-8}$hydroxyalkyl, $C_{1-8}$alkoxy, or methoxy), or both to complete valency);

an optionally substituted C1-C6 alkyl, such as optionally substituted with OH, halo, $C_{1-8}$alkyl, methyl, ethyl, $C_{1-8}$haloalkyl, $C_{1-8}$hydroxyalkyl, $C_{1-8}$alkoxy, or methoxy;

an optionally substituted C2-C6 alkenyl, such as optionally substituted with OH, halo, $C_{1-8}$alkyl, methyl, ethyl, $C_{1-8}$haloalkyl, $C_{1-8}$hydroxyalkyl, $C_{1-8}$alkoxy, or methoxy;

an optionally substituted C2-C6 alkynyl, such as optionally substituted with OH, halo, $C_{1-8}$alkyl, methyl, ethyl, $C_{1-8}$haloalkyl, $C_{1-8}$hydroxyalkyl, $C_{1-8}$alkoxy, or methoxy;

an optionally substituted cycloalkyl (e.g., an optionally substituted C3-C7 cycloalkyl) or bicyclic cycloalkyl (e.g., an optionally substituted C5-C20 bicyclic cycloalkyl), such as an optionally substituted cycloalkyl or bicyclic cycloalkyl optionally substituted with OH, halo, $C_{1-8}$alkyl, methyl, ethyl, $C_{1-8}$haloalkyl, $C_{1-8}$hydroxyalkyl, $C_{1-8}$alkoxy, or methoxy; or an optionally substituted heterocycloalkyl (e.g., an optionally substituted 3-, 4-, 5-, 6-, or 7-membered heterocyclic group) or bicyclic heterocycloalkyl (e.g., an optionally substituted 5-20 membered bicyclic heterocycloalkyl), such as an optionally substituted heterocycloalkyl or bicyclic heterocycloalkyl having one or more heteroatoms independently selected from N, O, S, P, or Si atoms that has an appropriate number of hydrogens, substitutions (e.g., OH, halo, $C_{1-8}$alkyl, methyl, ethyl, $C_{1-8}$haloalkyl, $C_{1-8}$hydroxyalkyl, $C_{1-8}$ alkoxy, or methoxy), or both to complete valency. In any aspect or embodiment described herein, the optionally substituted alkyl linker is optionally substituted with one or more OH, halo, linear or branched C1-C6 alkyl (such as methyl or ethyl), linear or branched C1-C6 haloalkyl, linear or branched C1-C6 hydroxyalkyl, or linear or branched C1-C6 alkoxy (e.g., methoxy).

In any aspect or embodiment described herein, the linker (L) does not have heteroatom-heteroatom bonding (e.g., no heteroatoms are covalently linked or adjacently located).

In any aspect or embodiment described herein, the linker (L) includes 1 to 50 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) alkylene glycol units that are optionally substituted, wherein carbon or oxygen may be substituted or replaced with a heteroatom selected from N, S, P, or Si atoms with an appropriate number of hydrogens to complete valency.

In any aspect or embodiment described herein, the linker (L) is represented by the chemical structure:

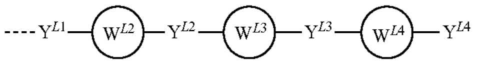

or

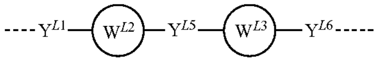

or

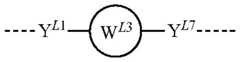

or

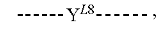

, wherein:

$Y^{L1}$ is a bond, O, or NH, C═O, or a C1-C3 alkyl;

$W^{L2}$ is 3-7 membered ring (e.g., 4-6 membered cycloalkyl or 4-6 membered heterocycloalkyl), optionally substituted;

$Y^{L2}$ is a bond, O, an unsubstituted or substituted linear or branched C1-C6 alkyl (e.g., optionally substituted with one or more (e.g., 1, 2, or 3) halogen (e.g., F, Cl, Br), OH, C1-C3 alkyl, C1-C2 hydroxyalkyl, —$CF_3$, methyl, ethyl, isopropyl group, or C═O), a unsubstituted or substituted linear or branched C2-C6 alkenyl (e.g., an optionally substituted C1-C4 alkenyl and/or optionally substituted with one or more (e.g., 1, 2, or 3) halogen, OH, C1-C3 alkyl, C1-C2 hydroxyalkyl, —$CF_3$, methyl, ethyl, isopropyl group, or C═O), or an unsubstituted or substituted linear or branched C1-C6 alkynyl (e.g., an optionally substituted C2-C4 alkynyl and/or optionally substituted with one or more (e.g., 1, 2, or 3) halogen, OH, C1-C3 alkyl, C1-C2 hydroxyalkyl, —$CF_3$, methyl, ethyl, isopropyl group, or C═O), each of the alkyl, the alkenyl, and the alkyl optionally having one or more (e.g., 1, 2, or 3) C atoms replaced with O, NH, $NCH_3$, or $NCH(CH_3)_2$;

$W^{L3}$ is a 3-7 membered ring (e.g., 3-6 membered cycloalkyl, 3-6 membered heterocycloalkyl, 5-6 membered aryl, or 5-6 membered heteroaryl), a 8-11 membered spirocyclic, or a 8-11 membered non-aromatic bicyclic group, each with 0-4 heteroatoms and optionally substituted with one or more (e.g., 1, 2, or 3) halogen, OH, C1-C3 alkyl, C1-C2 hydroxyalkyl, —$CF_3$, methyl, ethyl, isopropyl group, or C═O;

$Y^{L3}$ is a bond, O, an unsubstituted or substituted linear or branched C1-C6 alkyl (e.g., optionally substituted with one or more (e.g., 1, 2, or 3) halogen (e.g., F, Cl, Br), OH, C1-C3 alkyl, C1-C2 hydroxyalkyl, —$CF_3$, methyl, ethyl, isopropyl group, or C═O), a unsubstituted or substituted linear or branched C2-C6 alkenyl (e.g., an optionally substituted C1-C4 alkenyl and/or optionally substituted with one or more (e.g., 1, 2, or 3) halogen, OH, C1-C3 alkyl, C1-C2 hydroxyalkyl, —$CF_3$, methyl, ethyl, isopropyl group, or C═O), or an unsubstituted or substituted linear or branched C1-C6 alkynyl (e.g., an optionally substituted C2-C4 alkynyl and/or optionally substituted with one or more (e.g., 1, 2, or 3) halogen, OH, C1-C3 alkyl, C1-C2 hydroxyalkyl, —$CF_3$, methyl, ethyl, isopropyl group, or C═O), each of the alkyl, the alkenyl, and the alkyl optionally having one or more (e.g., 1, 2, or 3) C atoms replaced with O, NH, $NCH_3$, or $NCH(CH_3)_2$;

$W^{L4}$ is a 3-7 membered ring (e.g., 4-6 membered cycloalkyl, 4-6 membered heterocycloalkyl, 5-6 membered aryl, or 5-6 membered heteroaryl), or a 8-11 membered spirocyclic, each with 0-4 heteroatoms and optionally substituted with one or more (e.g., 1, 2, or 3) halogen, OH, C1-C3 alkyl, C1-C2 hydroxyalkyl, —$CF_3$, methyl, ethyl, isopropyl group, or C═0); $Y^{L4}$ is a bond, O, an unsubstituted or substituted linear or branched C1-C4 alkyl (e.g., optionally substituted with one or more (e.g., 1, 2, or 3) halogen (e.g., F, Cl, Br), OH, C1-C3 alkyl, C1-C2 hydroxyalkyl, —$CF_3$, methyl, ethyl, isopropyl group, or C═O), a unsubstituted or substituted linear or branched C2-C4 alkenyl (e.g., an optionally substituted C2-C3 alkenyl and/or optionally substituted with one or more (e.g., 1, 2, or 3) halogen, OH, C1-C3 alkyl, C1-C2 hydroxyalkyl, —$CF_3$, methyl, ethyl, isopropyl group, or C═O), or an unsubstituted or substituted linear or branched C1-C4 alkynyl (e.g., an optionally substituted C2-C3 alkynyl and/or optionally substituted with one or more (e.g., 1, 2, or 3) halogen, OH, C1-C3 alkyl, C1-C2 hydroxyalkyl, —$CF_3$, methyl, ethyl, isopropyl group, or C═O), each of the alkyl, the alkenyl, and the alkyl optionally having one or more (e.g., 1, 2, or 3) C atoms replaced with O, NH, $NCH_3$, or $NCH(CH_3)_2$;

$Y^{L5}$ is a bond, O, an unsubstituted or substituted linear or branched C1-C9 alkyl (e.g., optionally substituted with one or more (e.g., 1, 2, or 3) halogen (e.g., F, Cl, Br), OH, C1-C3 alkyl, C1-C2 hydroxyalkyl, —$CF_3$, methyl, ethyl, isopropyl group, or C═O), a unsubstituted or substituted linear or branched C2-C9 alkenyl (e.g., an optionally substituted C2-C6 alkenyl and/or optionally substituted with one or more (e.g., 1, 2, or 3) halogen, OH, C1-C3 alkyl, C1-C2 hydroxyalkyl, —$CF_3$, methyl, ethyl, isopropyl group, or C═O), or an unsubstituted or substituted linear or branched C1-C6 alkynyl (e.g., an optionally substituted C2-C6 alkynyl and/or optionally substituted with one or more (e.g., 1, 2, or 3) halogen, OH, C1-C3 alkyl, C1-C2 hydroxyalkyl, —$CF_3$, methyl, ethyl, isopropyl group, or C═O), each of the alkyl, the alkenyl, and the alkyl optionally having one or more (e.g., 1, 2, or 3) C atoms replaced with O, NH, $NCH_3$, or $NCH(CH_3)_2$;

$Y^{L6}$ is a bond, O, an unsubstituted or substituted linear or branched C1-C8 alkyl (e.g., optionally substituted with one or more (e.g., 1, 2, or 3) halogen (e.g., F, Cl, Br), OH, C1-C3 alkyl, C1-C2 hydroxyalkyl, —$CF_3$, methyl, ethyl, isopropyl group, or C═O), a unsubstituted or substituted linear or branched C2-C8 alkenyl (e.g., an optionally substituted C2-C6 alkenyl and/or optionally substituted with one or more (e.g., 1, 2, or 3) halogen, OH, C1-C3 alkyl, C1-C2 hydroxyalkyl, —$CF_3$, methyl, ethyl, isopropyl group, or C═O), or an unsubstituted or substituted linear or branched C1-C8 alkynyl (e.g., an optionally substituted C2-C6 alkynyl and/or optionally substituted with one or more (e.g., 1, 2, or 3) halogen, OH, C1-C3 alkyl, C1-C2 hydroxyalkyl, —$CF_3$, methyl, ethyl, isopropyl group, or C═O), each of the alkyl, the alkenyl, and the alkyl optionally having one or more (e.g., 1, 2, or 3) C atoms replaced with O, NH, $NCH_3$, or $NCH(CH_3)_2$;

$Y^{L7}$ is a bond, O, an unsubstituted or substituted linear or branched C1-C10 alkyl (e.g., optionally substituted with one or more (e.g., 1, 2, or 3) halogen (e.g., F, Cl, Br), OH, C1-C3 alkyl, C1-C2 hydroxyalkyl, —$CF_3$, methyl, ethyl, isopropyl group, or C═O), a unsubstituted or substituted linear or branched C2-C10 alkenyl (e.g., an optionally substituted C2-C8 alkenyl and/or optionally substituted with one or more (e.g., 1, 2, or 3) halogen, OH, C1-C3 alkyl, C1-C2 hydroxyalkyl, —$CF_3$, methyl, ethyl, isopropyl group, or C═O), or an unsubstituted or substituted linear or branched C1-C10 alkynyl (e.g., an optionally substituted C2-C8 alkynyl and/or optionally substituted with one or more (e.g., 1, 2, or 3) halogen, OH, C1-C3 alkyl, C1-C2 hydroxyalkyl, —$CF_3$, methyl, ethyl, isopropyl group, or C═O), each of the alkyl, the alkenyl, and the alkyl optionally having one or more (e.g., 1, 2, or 3) C atoms replaced with O, NH, $NCH_3$, or $NCH(CH_3)_2$; and $Y^{L7}$ is a bond, O, or an unsubstituted or substituted linear or branched C1-C25 alkyl (e.g., an unsubstituted or substituted linear or branched C1-C25 alkyl and/or optionally substituted with one or more (e.g., 1, 2, or 3) halogen (e.g., F, Cl, Br), OH, C1-C3 alkyl, C1-C2 hydroxyalkyl, —$CF_3$, methyl, ethyl, isopropyl group, or C═O), the alkyl optionally having one or more (e.g., 1, 2, or 3) C atoms replaced with O, NH, $NCH_3$, or $NCH(CH_3)_2$; and the  indicates the site of attachment of a PTM or a ULM, In any aspect or embodiment described herein, the linker (L) comprises a chemical structure selected from:

I

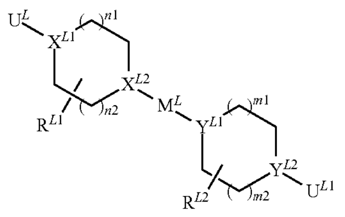

II

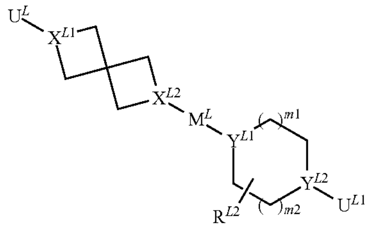

-continued

III

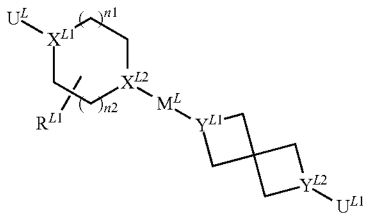

wherein:

$U^L$ and $U^{L1}$ are independently selected from a bond or O;

$X^{L1}$, $X^{L2}$, $Y^{L1}$, and $Y^{L2}$ are independently selected from N or CH with the proviso that if $X^L$ is N, then $U^L$ is a bond, and if $Y^{L2}$ is N, then $U^{L1}$ is a bond;

n1 and n2 are each independently 0 or 1, wherein when both $X^{L1}$ and $X^{L2}$ are N, n1 is 1 and n2 is 1;

m1 and m2 are each independently 0 or 1, wherein when both $Y^{L1}$ and $Y^{L2}$ are N, m1 is 1 and m2 is 1;

$R^{L1}$ and $R^{L2}$ each represent optional 1 or 2 substituents independently selected from methyl, halogen (e.g., F, Cl, Br), fluoroalkyl (e.g., $C_{1-3}$ fluoroalkyl), OH, and CN, wherein the halogen (e.g., F), OH, and CN substituents are not on a carbon atom adjacent to $X^{L1}$ when $X^{L1}$ is N, $X^{L2}$ when $X^{L2}$ is N, $Y^{L1}$ when $Y^{L1}$ is N, or $Y^{L2}$ when $Y^{L2}$ is N;

$M^L$ is selected from the following:

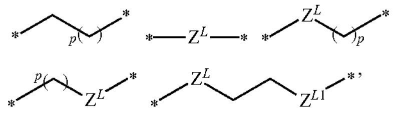

wherein $M^L$ is optionally substituted with 1 or 2 substituents independently selected from methyl, halogen (e.g., F), fluoroalkyl (e.g., $C_{1-3}$ fluoroalkyl), OH and CN with the proviso that the above mentioned F, OH and CN substituents are not on the carbon atom adjacent to a heteroatom;

$Z^L$ and $Z^{L1}$ are each independently selected from O or $NR^3$;

$R^{L3}$ is an H, methyl, ethyl or isopropyl;

p is 0, 1, or 2; and $U^L$ and $U^{L1}$ are the sites of attachment of a PTM or a ULM.

In any aspect or embodiment described herein, the linker (L) comprises a chemical structure selected from:

IV

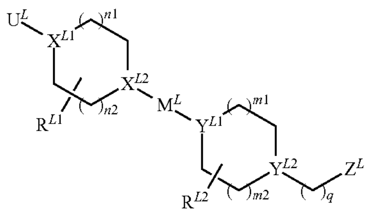

-continued

V

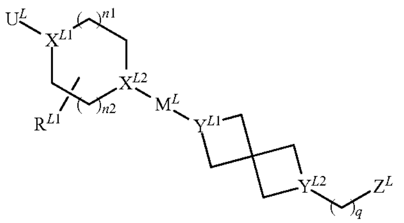

VI

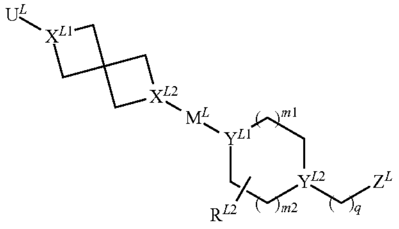

wherein:

$U^L$ and $U^{L1}$ are independently selected from a bond or O;

$X^{L1}$, $X^{L2}$, $Y^{L1}$, and $Y^{L2}$ are independently selected from N or CH with the proviso that if $X^{L1}$ is N, then $U^L$ is a bond, and if $Y^{L2}$ is N, then $U^{L1}$ is a bond;

n1 and n2 are each independently 0 or 1, wherein when both $X^{L1}$ and $X^{L2}$ are N, n1 is 1 and n2 is 1;

m1 and m2 are each independently 0 or 1, wherein when both $Y^{L1}$ and $Y^{L2}$ are N, m1 is 1 and m2 is 1;

$R^{L1}$ and $R^{L2}$ each represent optional 1 or 2 substituents independently selected from methyl, halogen (e.g., F, Cl, Br), fluoroalkyl (e.g., $C_{1-3}$ fluoroalkyl), OH, and CN, wherein the halogen (e.g., F), OH, and CN substituents are not on a carbon atom adjacent to $X^{L1}$ when $X^{L1}$ is N, $X^{L2}$ when $X^{L2}$ is N, $Y^{L1}$ when $Y^{L1}$ is N, or $Y^{L2}$ when $Y^{L2}$ is N;

$M^L$ is selected from the following:

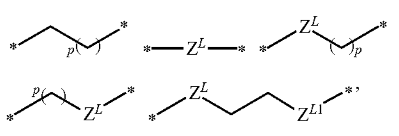

wherein $M^L$ is optionally substituted with 1 or 2 substituents independently selected from methyl, halogen (e.g., F), fluoroalkyl (e.g., $C_{1-3}$ fluoroalkyl), OH and CN with the proviso that the above mentioned F, OH and CN substituents are not on the carbon atom adjacent to a heteroatom;

$Z^L$ and $Z^{L1}$ are each independently selected from O or $NR^{L3}$;

$R^{L3}$ is an H, methyl, ethyl or isopropyl;

p is 0, 1, or 2;

q is 0, 1, 2, 3, 4 or 5, wherein when $Y^{L2}$ is N, q is not 0 or 1; and $U^L$ and $Z^L$ are the sites of attachment of a PTM or a ULM.

In any aspect or embodiment described herein, the linker (L) comprises a chemical structure selected from:

VII

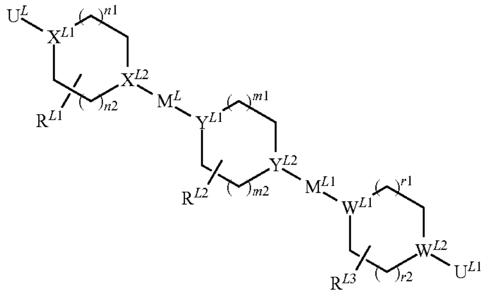

VIII

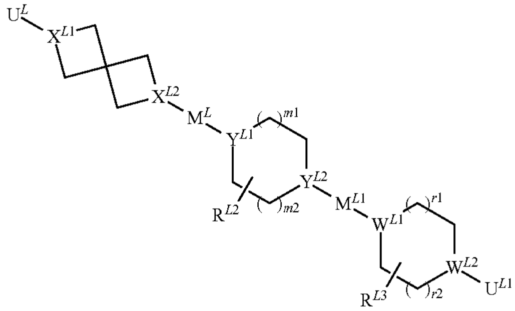

IX

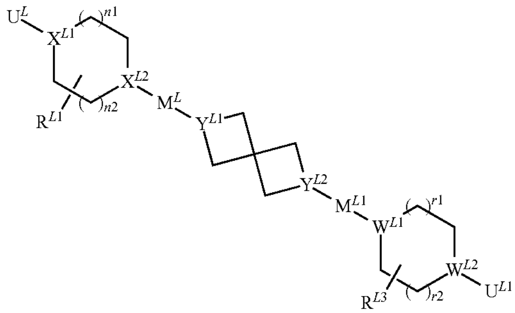

X

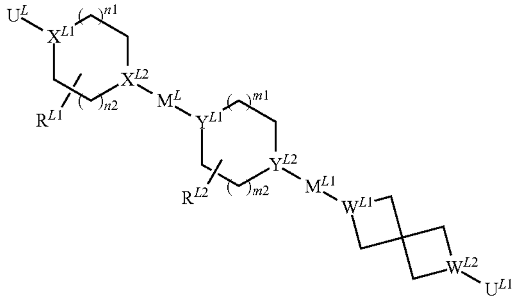

wherein:

$U^L$ and $U^{L1}$ are independently selected from a bond or O;

$X^{L1}$, $X^{L2}$, $Y^L$, and $Y^{L2}$ are independently selected from N or CH with the proviso that if $X^L$ is N, then $U^L$ is a bond, and if $Y^{L2}$ is N, then $U^{L1}$ is a bond;

n1 and n2 are each independently 0 or 1, wherein when both $X^{L1}$ and $X^{L2}$ are N, n1 is 1 and n2 is 1;

m1 and m2 are each independently 0 or 1, wherein when both $Y^{L1}$ and $Y^{L2}$ are N, m1 is 1 and m2 is 1;

$R^{L1}$ and $R^{L2}$ each represent optional 1 or 2 substituents independently selected from methyl, halogen (e.g., F, Cl, Br), fluoroalkyl (e.g., $C_{1-3}$ fluoroalkyl), OH, and CN, wherein the halogen (e.g., F), OH, and CN substituents are not on a carbon atom adjacent to $X^{L1}$ when $X^{L1}$ is N, $X^{L2}$ when $X^{L2}$ is N, $Y^{L1}$ when $Y^{L1}$ is N, or $Y^{L2}$ when $Y^{L2}$ is N;

$W^{L1}$ and $W^{L2}$ are each independently selected from N or CH, wherein when $W^{L2}$ is N, then $U^{L1}$ is a bond;

r1 is 1 or 2, and r2 is 0, 1, or 2, wherein when both $W^{L1}$ and $W^{L2}$ are N, r1 is 2 and r2 is 1 or 2;

$R^{L3}$ represents optional 1 or 2 substituents independently selected from methyl, halogen (e.g., F), fluoroalkyl (e.g., $C_{1-3}$ fluoroalkyl), OH and CN, wherein the halogen (e.g., F), OH, and CN substituents are not on a carbon atom adjacent to $X^{L1}$ when $X^{L1}$ is N, $X^{L2}$ when $X^{L2}$ is N, $Y^{L1}$ when $Y^{L1}$ is N, or $Y^{L2}$ when $Y^{L2}$ is N;

$M^{L1}$ is selected from the following:

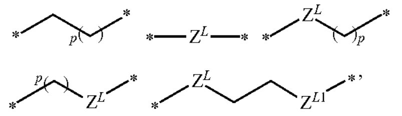

wherein $M^{L1}$ is optionally substituted with 1 or 2 substituents independently selected from methyl, halogen (e.g., F), fluoroalkyl (e.g., $C_{1-3}$ fluoroalkyl), OH and CN with the proviso that the above mentioned F, OH and CN substituents are not on the carbon atom adjacent to a heteroatom;

$Z^L$ and $Z^{L1}$ are each independently selected from O or $NR^3$;

p is 0, 1, or 2; and $U^L$ and $U^{L1}$ are the sites of attachment of a PTM or a ULM.

In any aspect or embodiment described herein, the linker (L) is selected from:

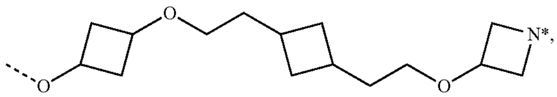,

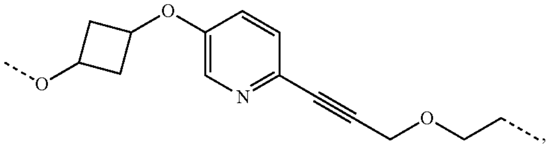,

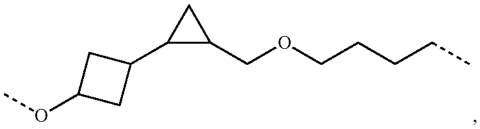,

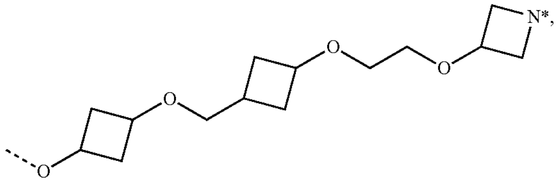,

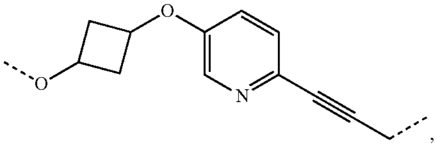,

-continued

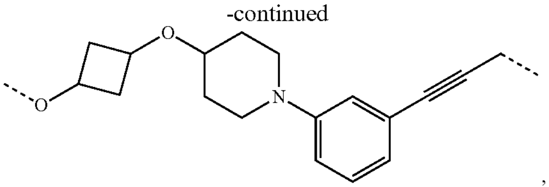,

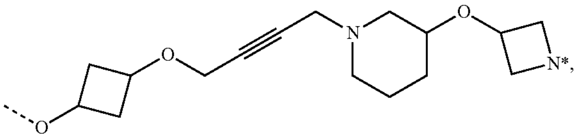,

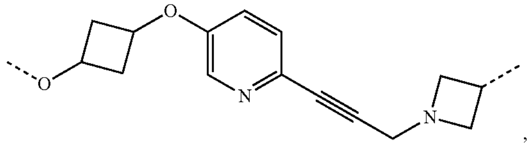,

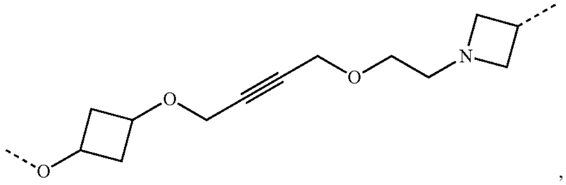,

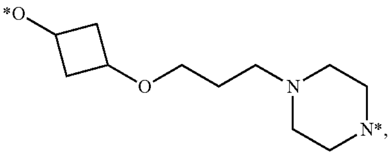,

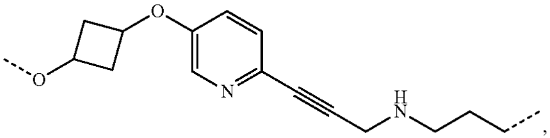,

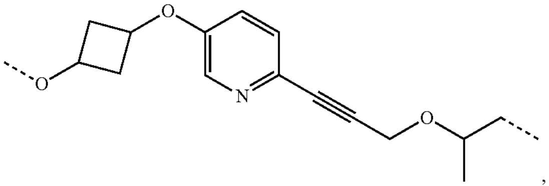,

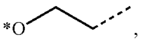, 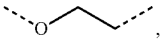, 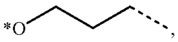,

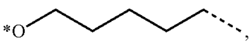, 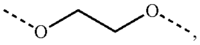,

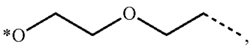,

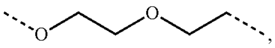,

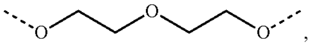,

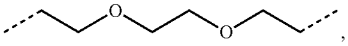,

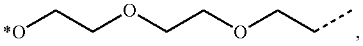,

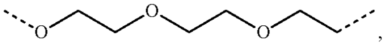,

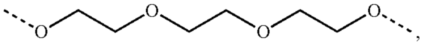,

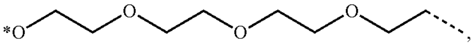,

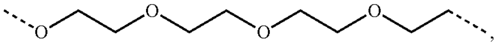,

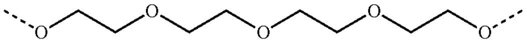,

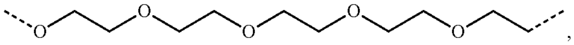,

-continued
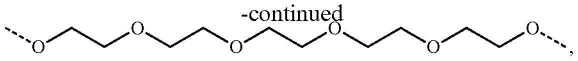
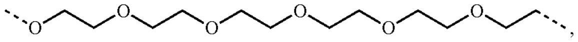
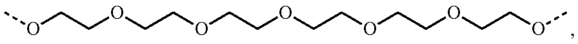
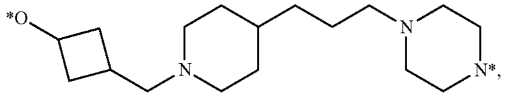
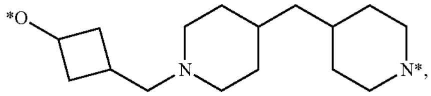
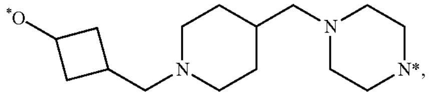
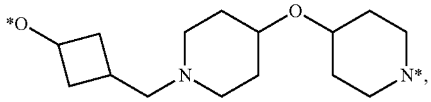
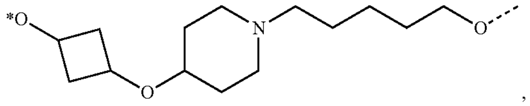
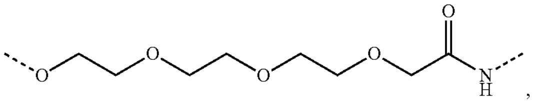
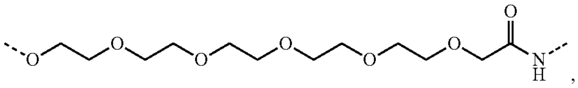
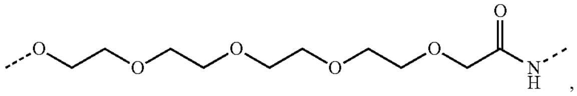
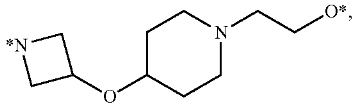
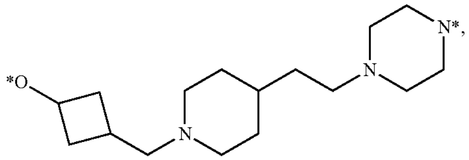
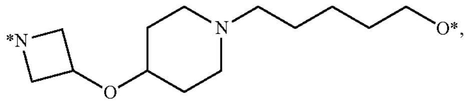
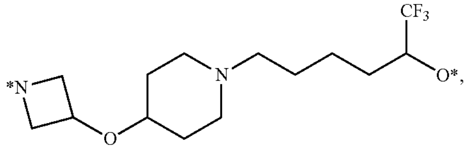
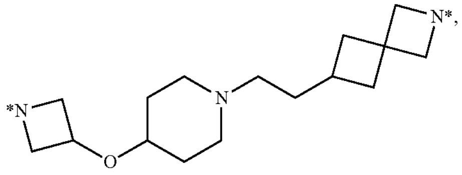
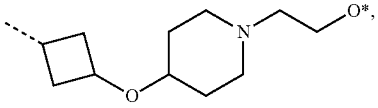
-continued
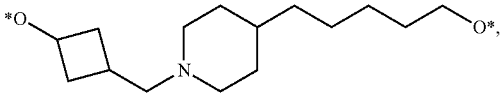
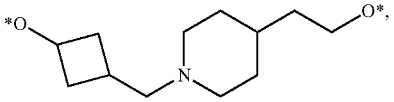
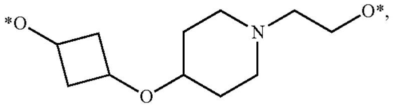
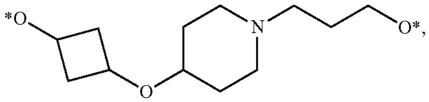
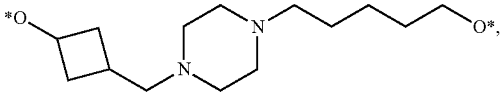
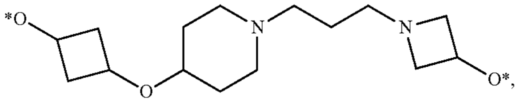
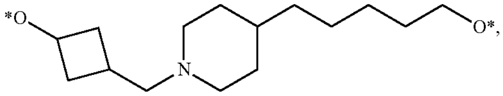
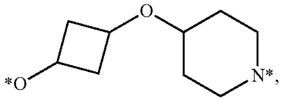
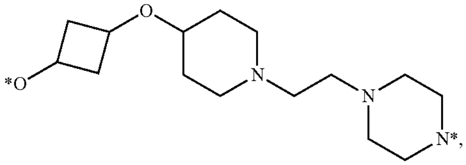
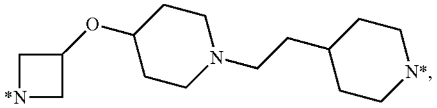
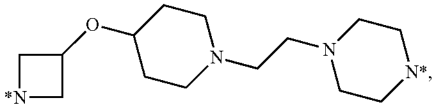
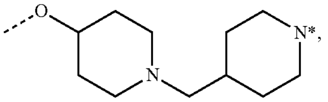
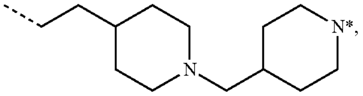
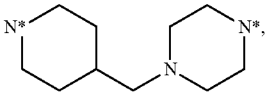
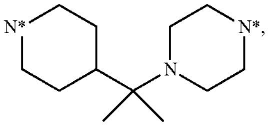
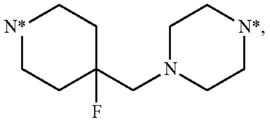

-continued
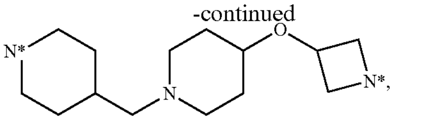
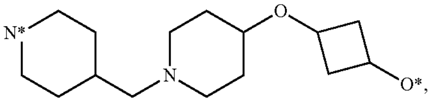
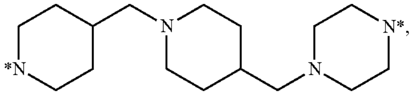
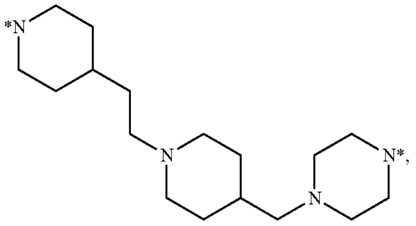
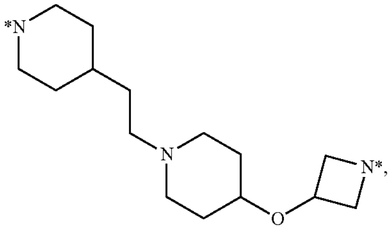
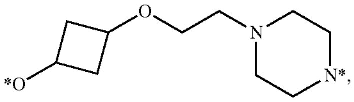
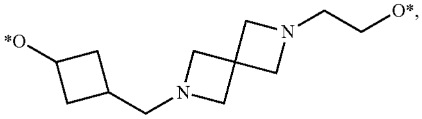
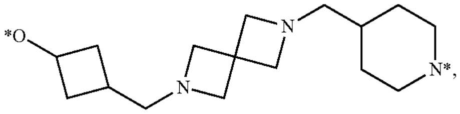
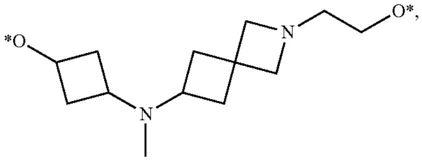
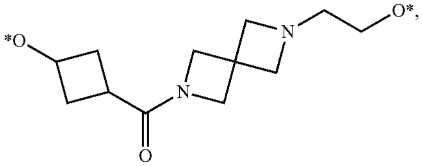
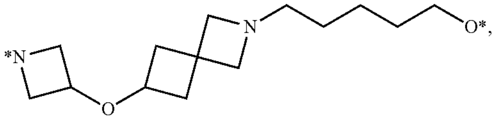
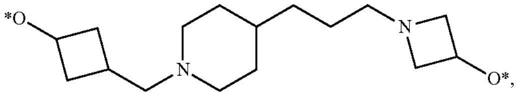
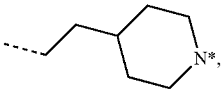
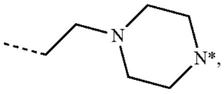
-continued
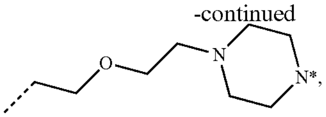
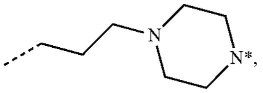
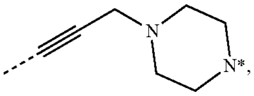
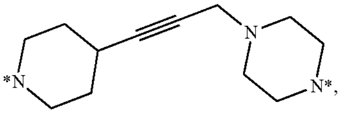
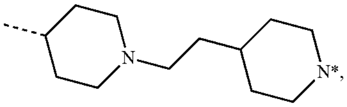
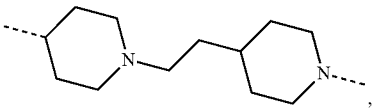
,
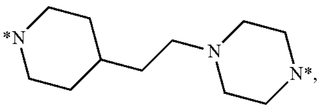
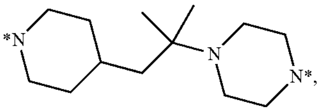
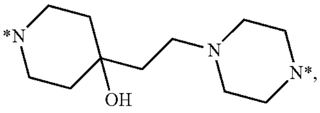
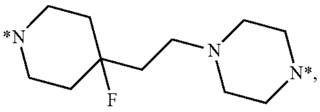
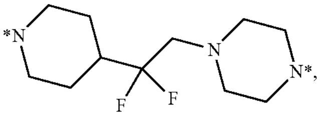
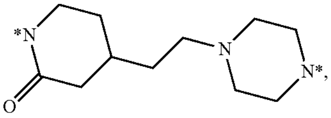
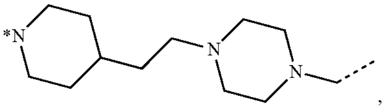
,
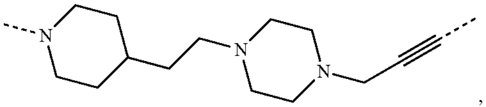
,
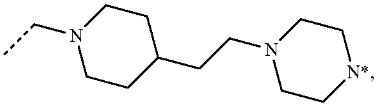
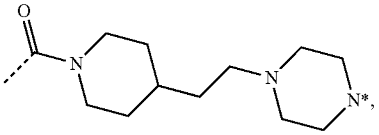

-continued
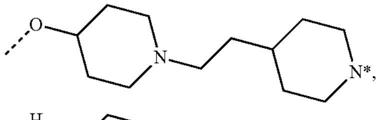,
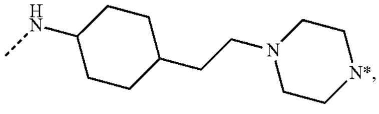,
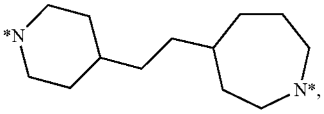,
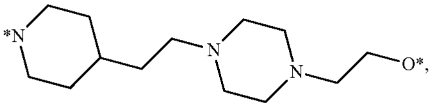,
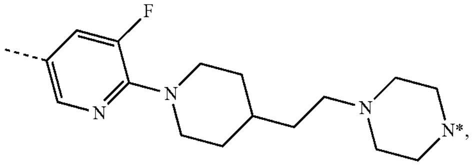,
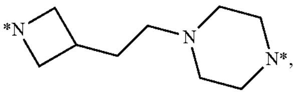,
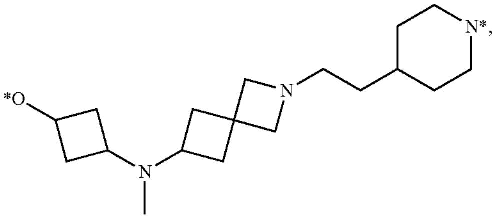,
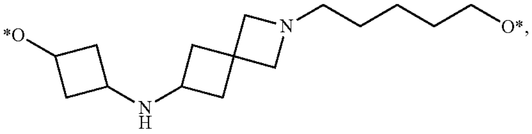,
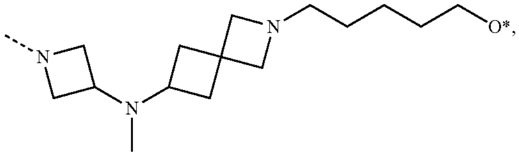,
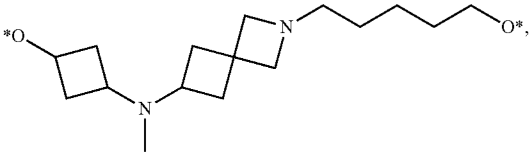,
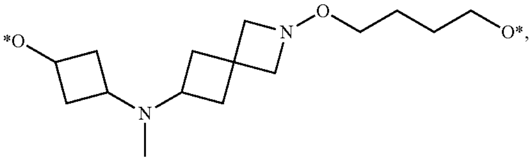,
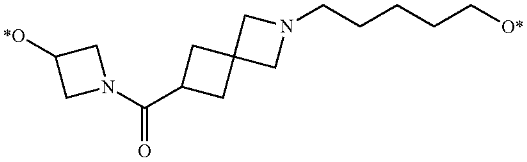
-continued
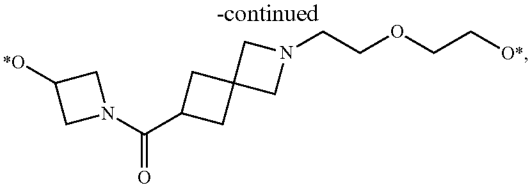,
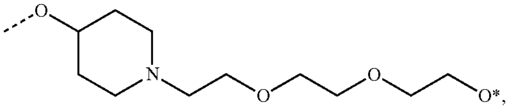,
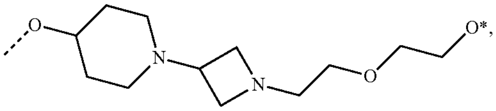,
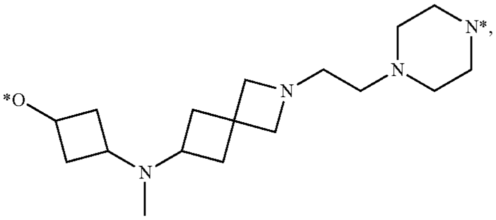,
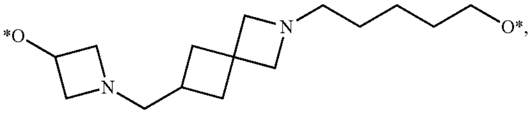,
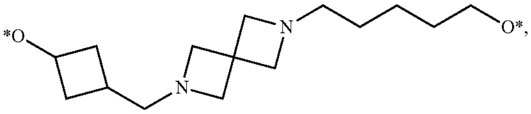,
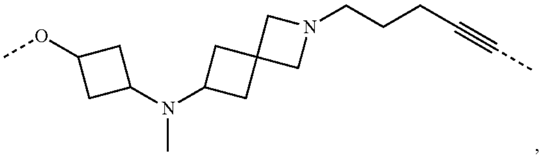
,
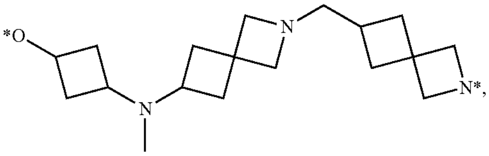,
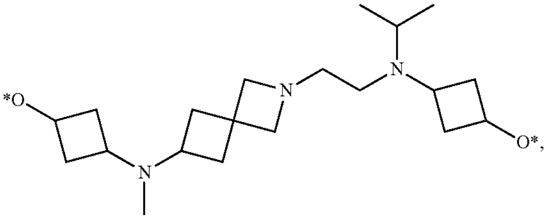,
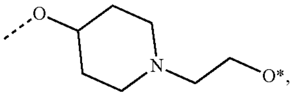,
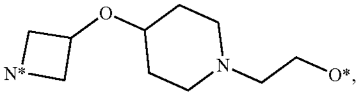,
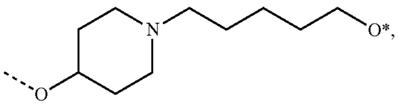, -continued
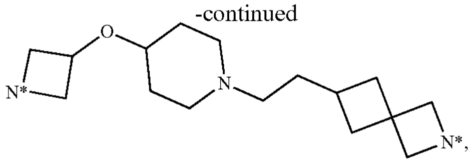
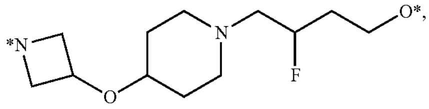
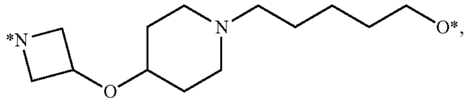
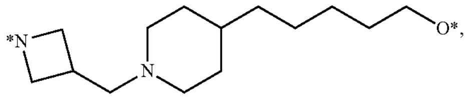
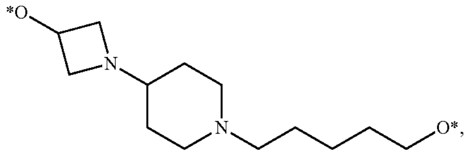
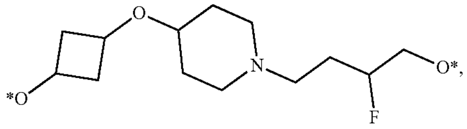
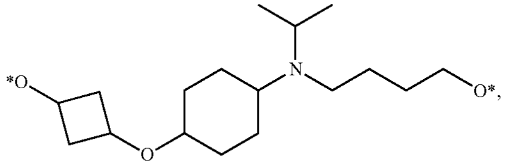
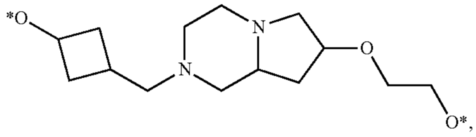
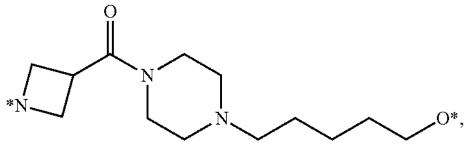
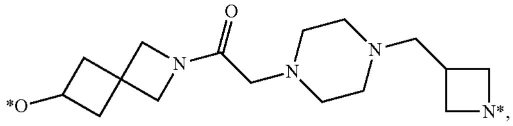
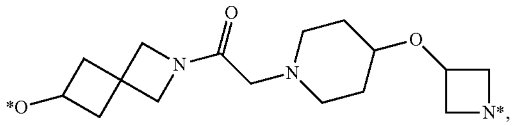
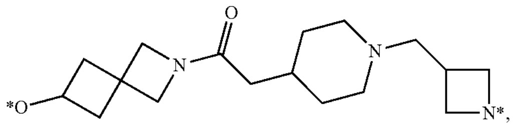
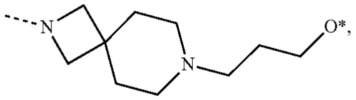
-continued
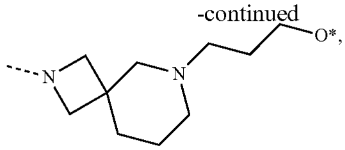
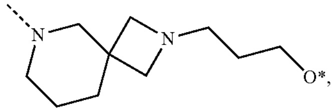
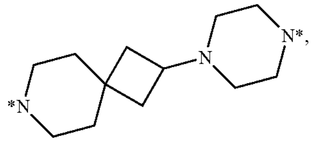
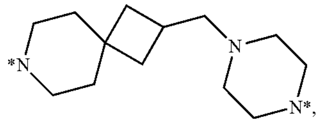
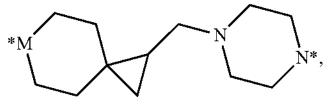
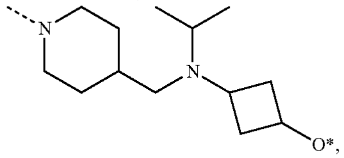
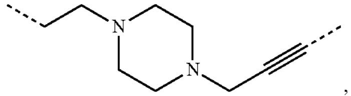
,
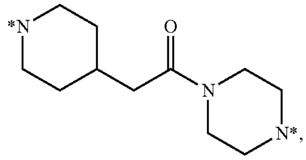
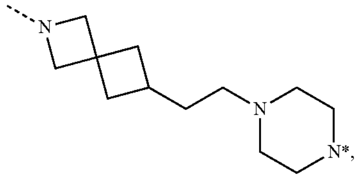
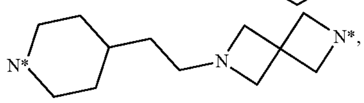
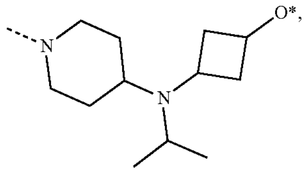
and
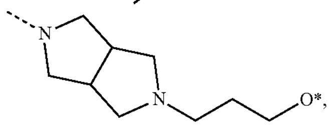
wherein each * and  is a site of attachment of a PTM or a ULM.
In any aspect or embodiment described herein, the linker (L) is selected from:

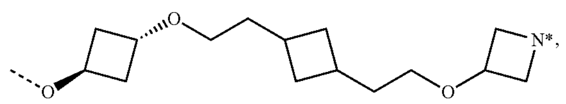
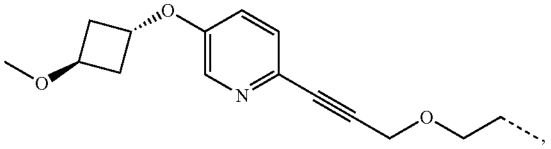
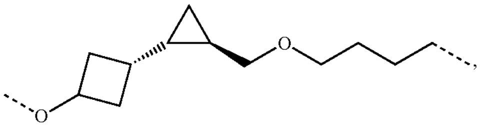
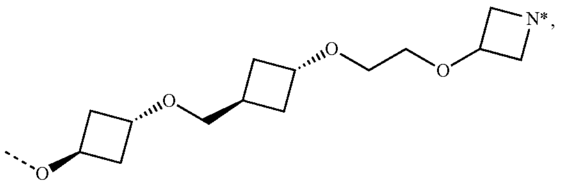
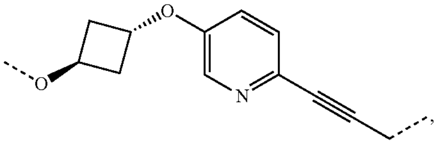
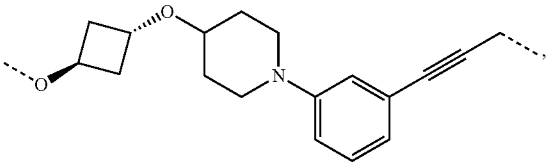
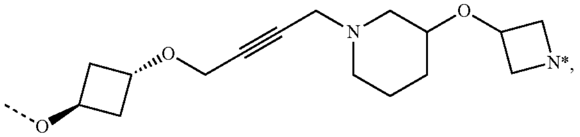
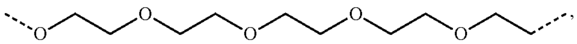
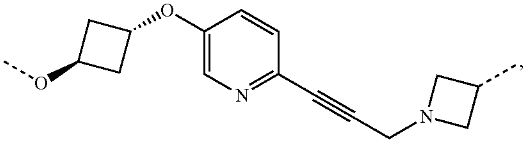
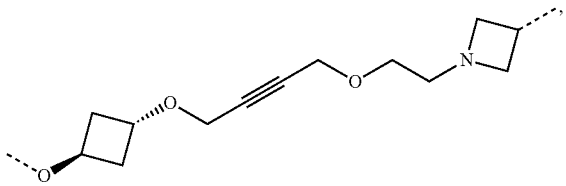
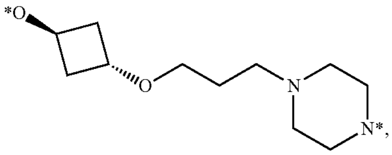
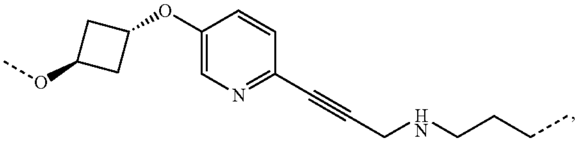
-continued
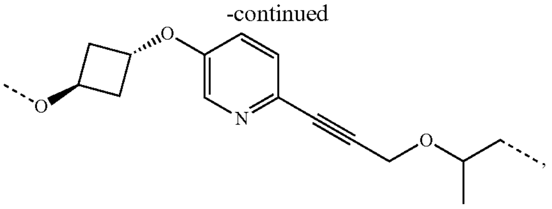
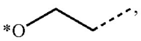 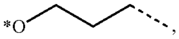
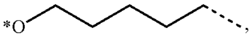 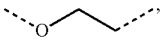
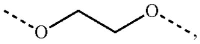 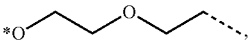
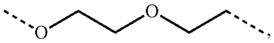
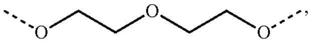
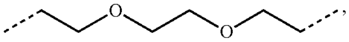
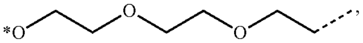
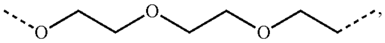
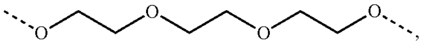
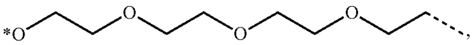
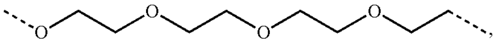
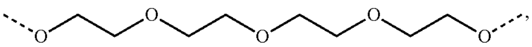
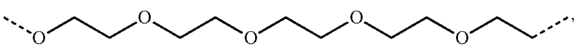
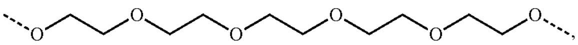
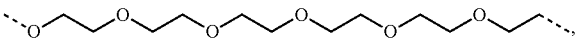
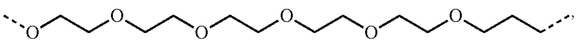
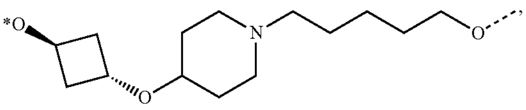
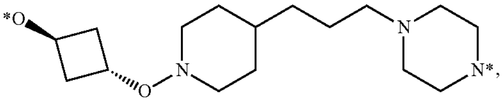
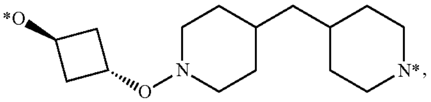
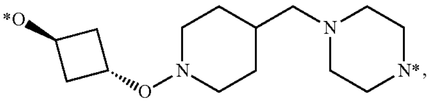
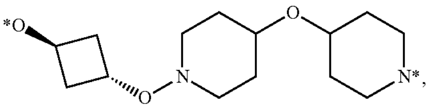
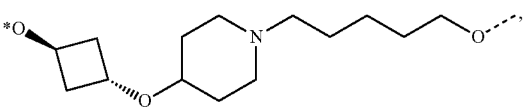
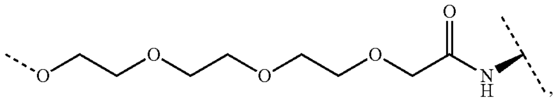

-continued
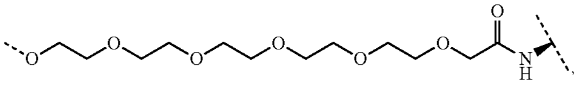
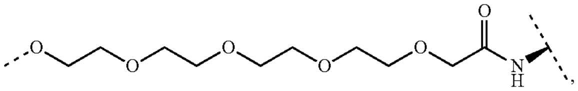
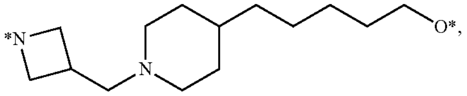
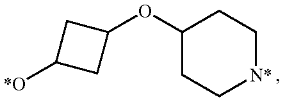
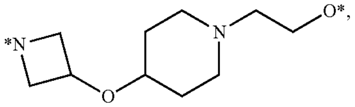
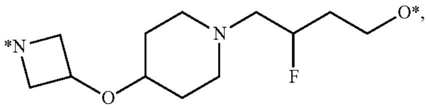
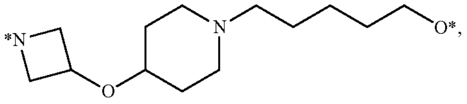
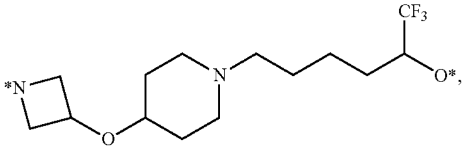
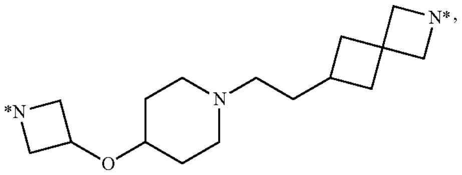
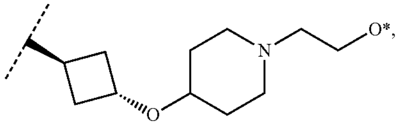
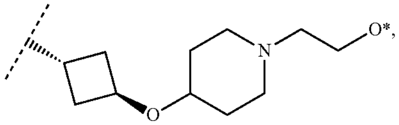
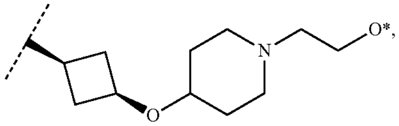
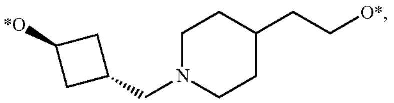
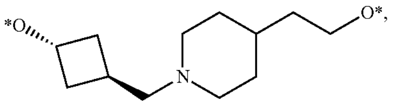
-continued
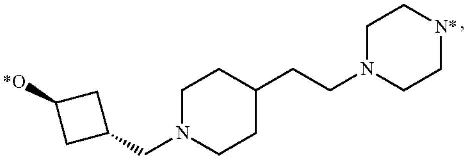
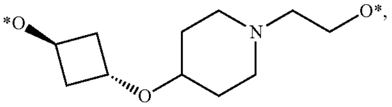
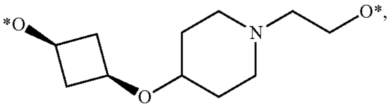
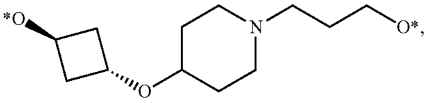
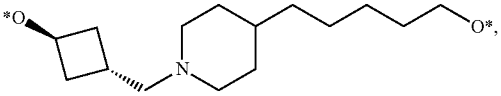
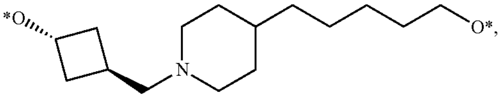
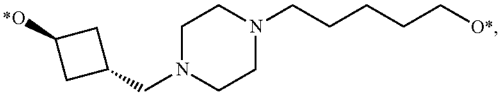
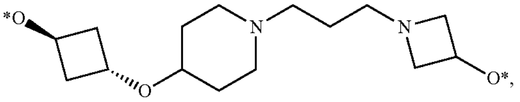
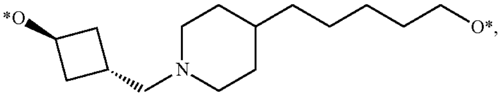
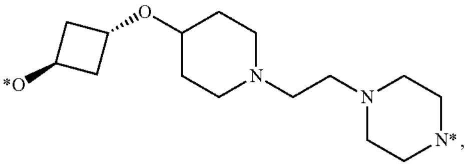
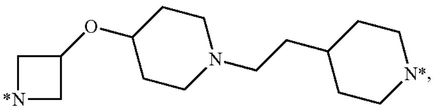
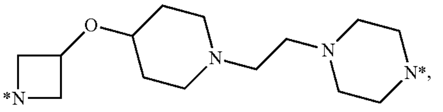
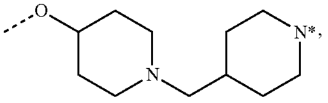
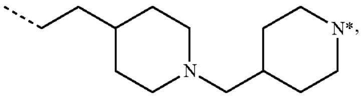
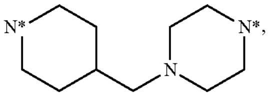

-continued
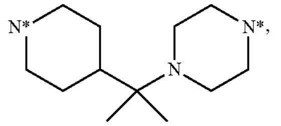
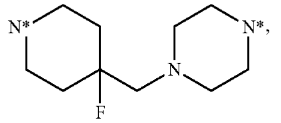
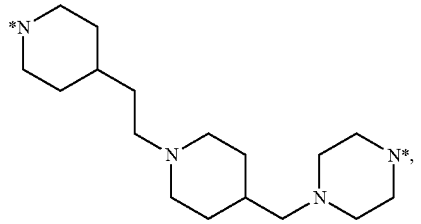
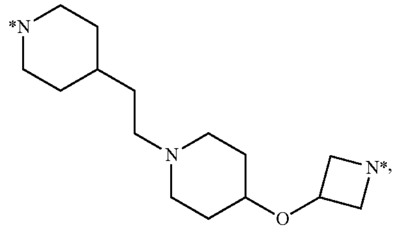
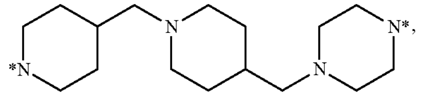
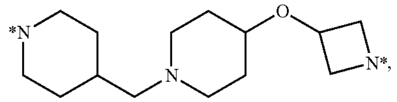
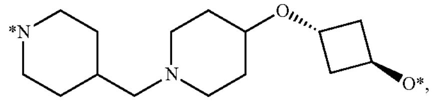
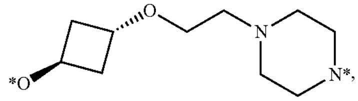
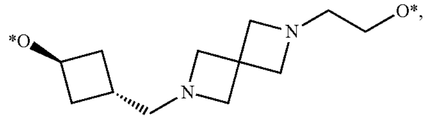
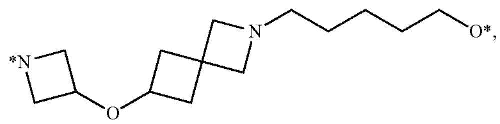
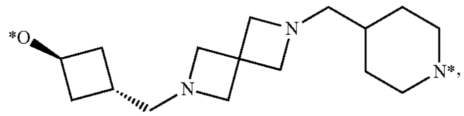
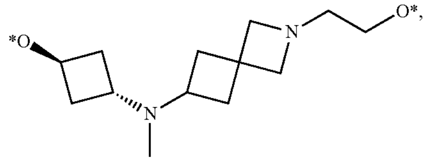
-continued
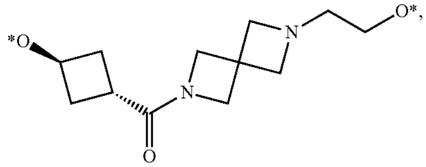
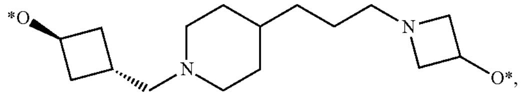
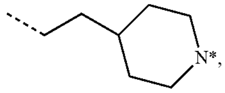 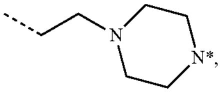
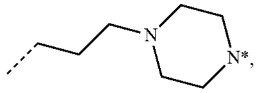
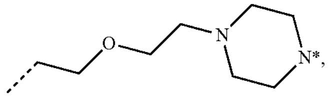
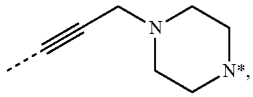
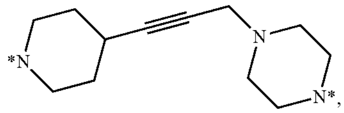
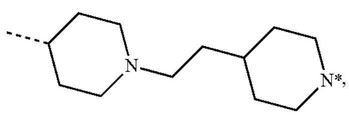
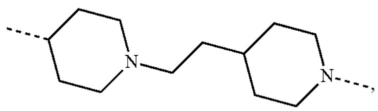
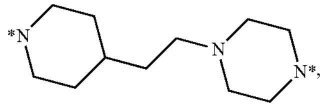
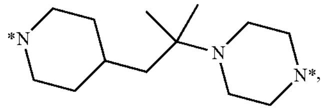
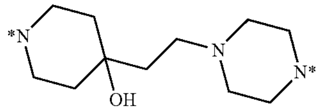
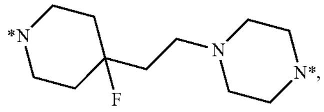
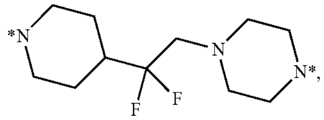
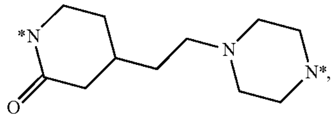

-continued
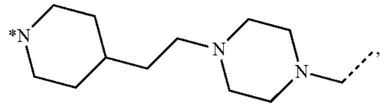
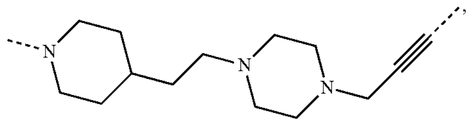
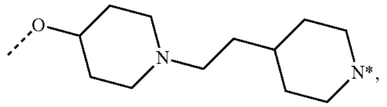
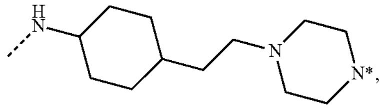
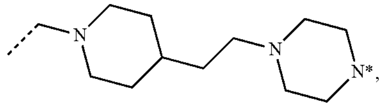
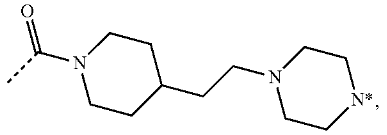
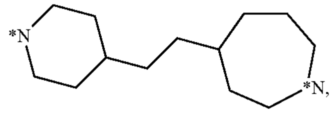
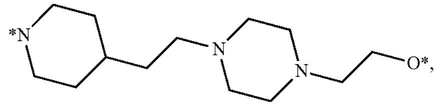
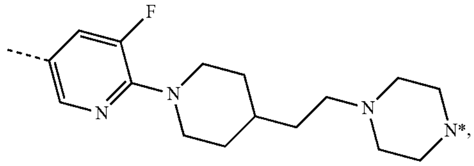
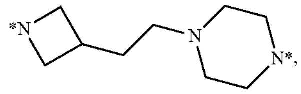
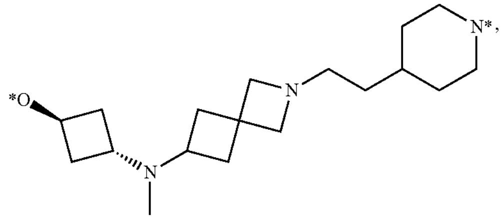
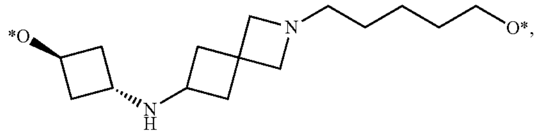
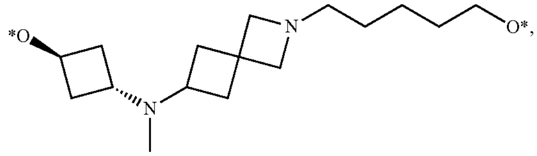
-continued
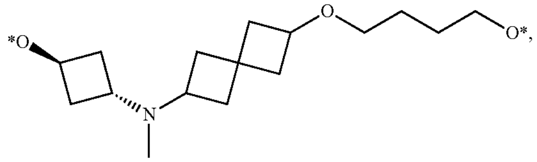
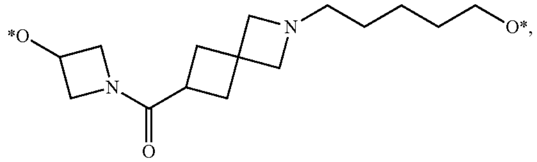
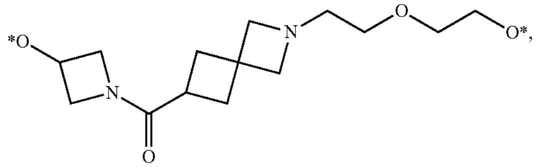
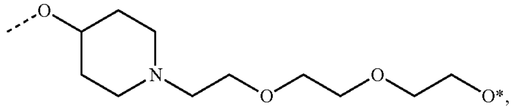
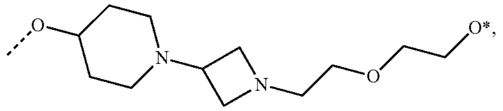
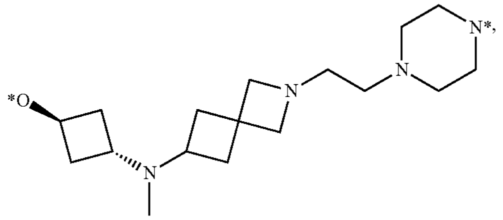
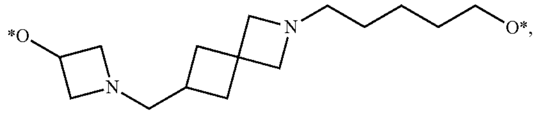
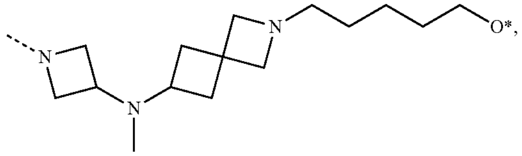
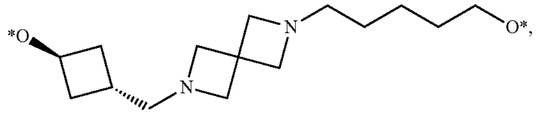
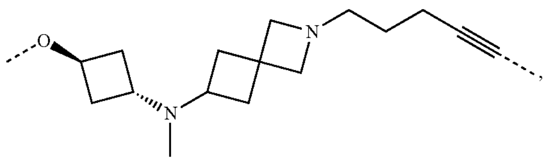
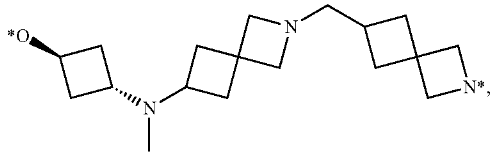

-continued
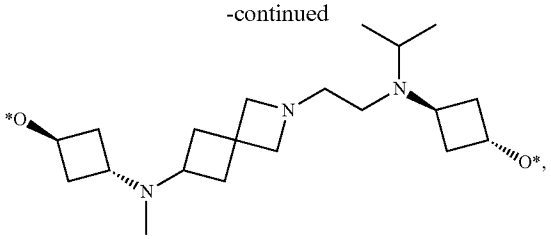
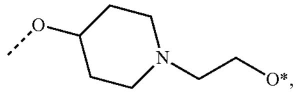
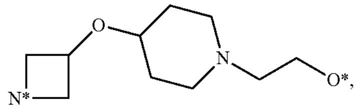
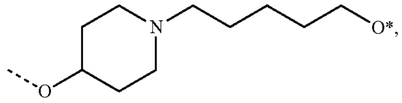
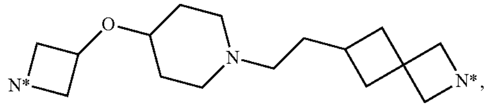
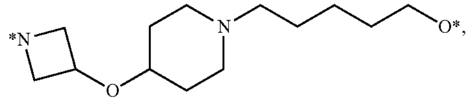
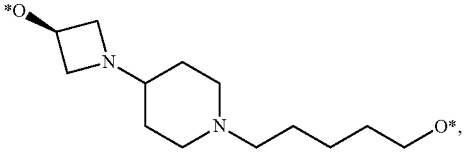
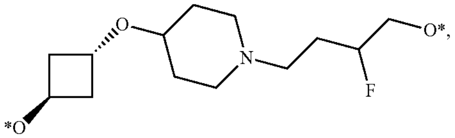
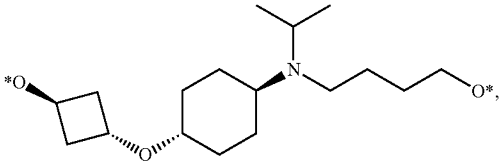
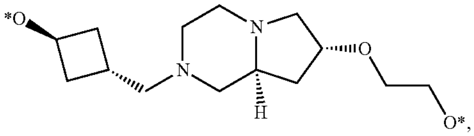
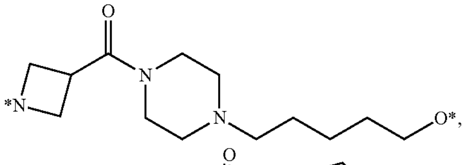
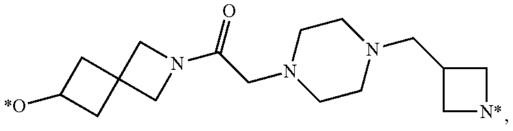
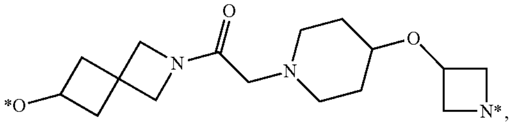
-continued
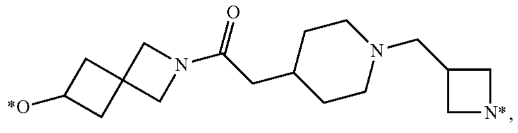
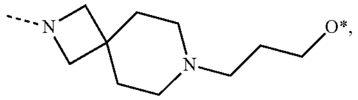
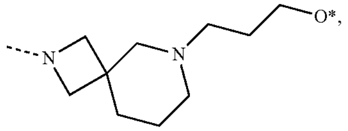
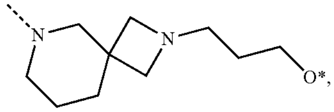
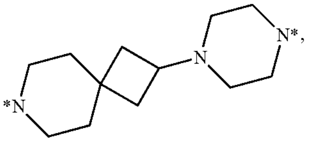
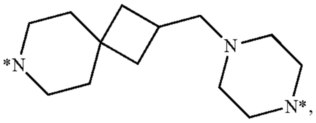
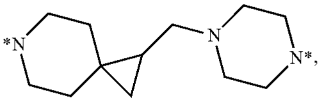
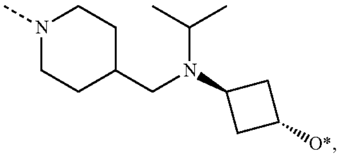
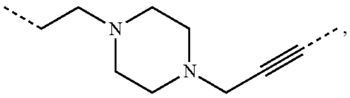
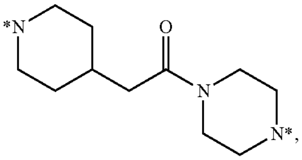
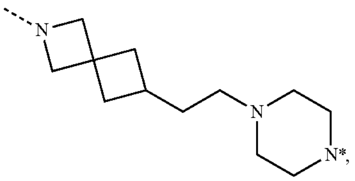
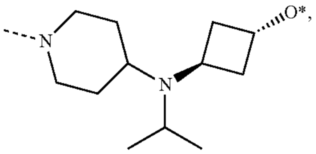
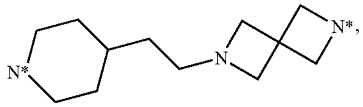
and -continued
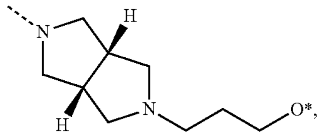
wherein each * and  is a site of attachment of a PTM or a ULM.
In any aspect or embodiment described herein, the linker (L) is selected from:
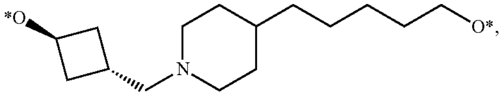
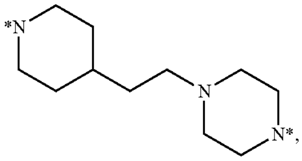
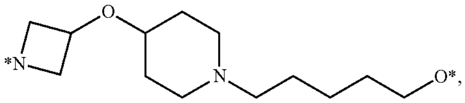
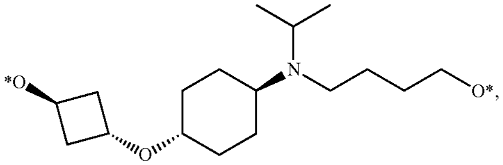
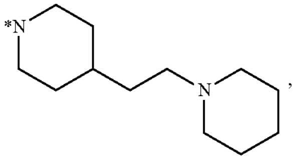
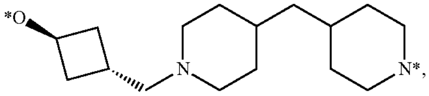
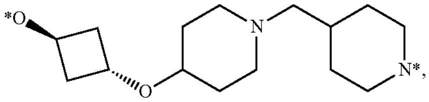
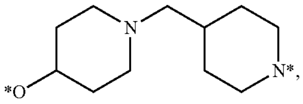
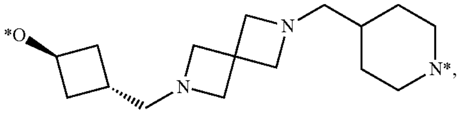
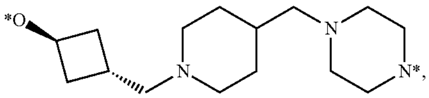
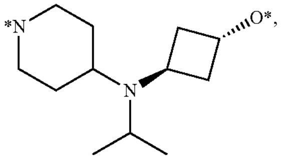
-continued
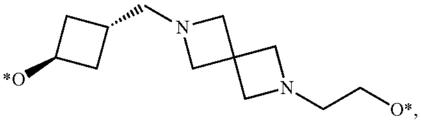
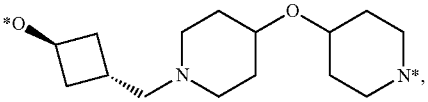
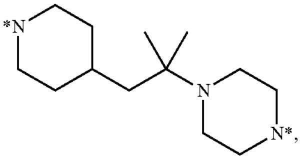
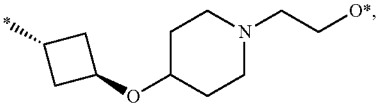
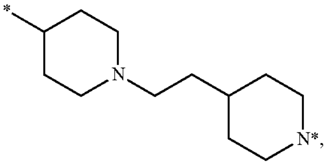
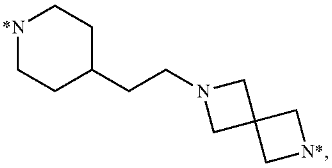
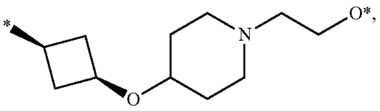
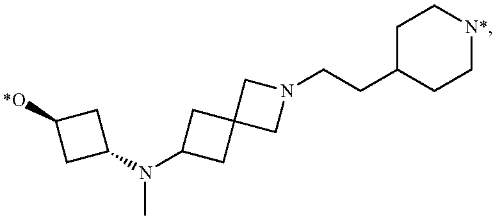
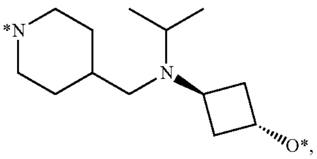
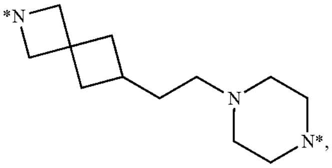
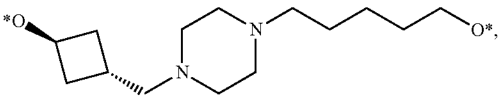
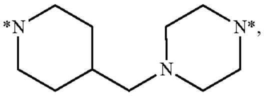

-continued

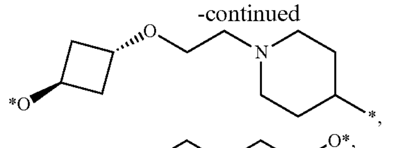

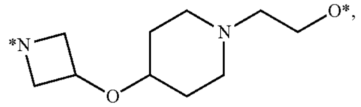

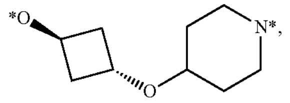

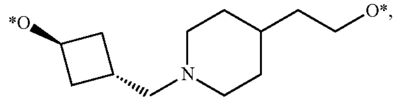

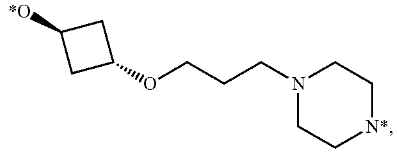

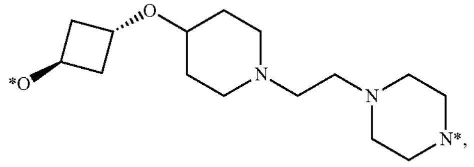

and

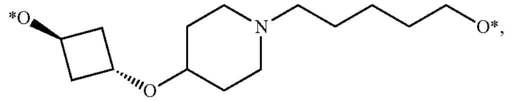

wherein each * is a site of attachment of a PTM or a ULM.

In any aspect or embodiment described herein, the linker (L) comprises the following chemical structure:

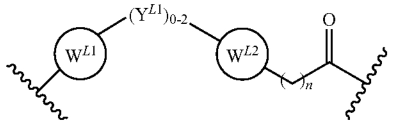

or

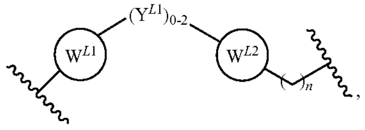

wherein:

$W^{L1}$ and $W^{L2}$ are each independently absent, a 4-8 membered ring with 0-4 heteroatoms, optionally substituted with $R^Q$, each $R^Q$ is independently a H, halo, OH, CN, $CF_3$, optionally substituted linear or branched $C_1$-$C_6$ alkyl, optionally substituted linear or branched $C_1$-$C_6$ alkoxy, or 2 $R^Q$ groups taken together with the atom they are attached to, form a 4-8 membered ring system containing 0-4 heteroatoms;

$Y^{L1}$ is each independently a bond, optionally substituted linear or branched $C_1$-$C_6$ alkyl and optionally one or more C atoms are replaced with O or $NR^{YL1}$, optionally substituted $C_1$-$C_6$ alkene and optionally one or more C atoms are replaced with O, optionally substituted $C_1$-$C_6$ alkyne, and optionally one or more C atoms are replaced with O, or optionally substituted linear or branched $C_1$-$C_6$ alkoxy;

$R^{YL1}$ is H, or optionally substituted linear or branched $C_{1-6}$ alkyl;

n is 0-10; and

 and  indicates the attachment point to the PTM or ULM moieties.

In any aspect or embodiment described herein, the linker (L) comprises a structure selected from the structure shown below:

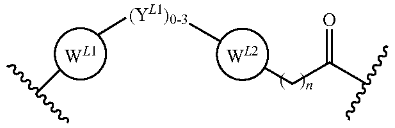

or

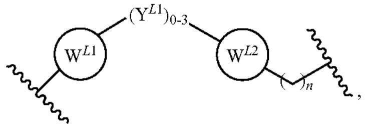

wherein:

$W^{L1}$ and $W^{L2}$ are each independently absent, piperazine, piperidine, morpholine, optionally substituted with $R^Q$, each $R^Q$ is independently a H, —Cl—, —F—, OH, CN, $CF_3$, optionally substituted linear or branched $C_1$-$C_6$ alkyl (e.g. methyl, ethyl), optionally substituted linear or branched $C_1$-$C_6$ alkoxy (e.g. methoxy, ethoxy);

$Y^{L1}$ is each independently a bond, optionally substituted linear or branched $C_1$-$C_6$ alkyl and optionally one or more C atoms are replaced with O or $NR^{YL1}$; optionally substituted $C_1$-$C_6$ alkene and optionally one or more C atoms are replaced with O, optionally substituted $C_1$-$C_6$ alkyne and optionally one or more C atoms are replaced with O, or optionally substituted linear or branched $C_1$-$C_6$ alkoxy;

$R^{YL1}$ is H, or optionally substituted linear or branched $C_{1-6}$ alkyl (e.g. methyl, ethyl);

n is 0-10; and

 and  indicates the attachment point to the PTM or ULM moieties.

In any aspect or embodiment described herein, the linker (L) comprises a structure selected from the structures shown below:

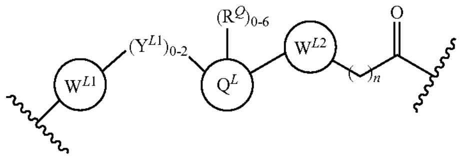

or

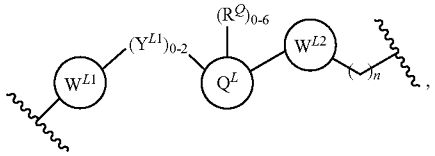

wherein:

$W^{L1}$ and $W^{L2}$ are each independently absent, aryl, heteroaryl, cyclic, heterocyclic, $C_{1-6}$ alkyl and optionally one or more C atoms are replaced with O or or $NR^{YL1}$, $C_{1-6}$ alkene and optionally one or more C atoms are replaced with O, $C_{1-6}$ alkyne and optionally one or more C atoms are replaced with O, bicyclic, biaryl, biheteroaryl, or biheterocyclic, each optionally substituted with $R^Q$, each $R^Q$ is independently a H, halo, OH, CN, $CF_3$, hydroxyl, nitro, C≡CH, $C_{2-6}$ alkenyl, $C_{2-6}$ alkynyl, optionally substituted linear or branched $C_1$-$C_6$ alkyl, optionally substituted linear or branched $C_1$-$C_6$ alkoxy, optionally substituted $OC_{1-3}$alkyl (e.g., optionally substituted by I or more —F), OH, $NH_2$, $NR^{YL1}R^{YL2}$, CN, or 2 $R^Q$ groups taken together with the atom they are attached to, form a 4-8 membered ring system containing 0-4 heteroatoms;

$Y^{L1}$ is each independently a bond, $NR^{YL1}$, O, S, $NR^{YL2}$, $CR^{YL1}R^{YL2}$, C═O, C═S, SO, $SO_2$, optionally substituted linear or branched $C_1$-$C_6$ alkyl and optionally one or more C atoms are replaced with O; optionally substituted linear or branched $C_1$-$C_6$ alkoxy;

$Q^L$ is a 3-6 membered alicyclic, bicyclic, or aromatic ring with 0-4 heteroatoms, optionally bridged, optionally substituted with 0-6 $R^Q$, each $R^Q$ is independently H, optionally substitute linear or branched $C_{1-6}$ alkyl (e.g., optionally substituted by 1 or more halo, $C_{1-6}$ alkoxyl), or 2 $R^Q$ groups taken together with the atom they are attached to, form a 3-8 membered ring system containing 0-2 heteroatoms;

$R^{YL1}$, $R^{YL2}$ are each independently H, OH, optionally substituted linear or branched $C_{1-6}$ alkyl (e.g., optionally substituted by 1 or more halo, $C_{1-6}$ alkoxyl), or $R^{YL1}$, $R^{YL2}$ together with the atom they are attached to, form a 3-8 membered ring system containing 0-2 heteroatoms;

n is 0-10; and

 and  indicates the attachment point to the PTM or ULM moieties.

In any aspect or embodiment described herein, the linker (L) comprises a structure selected from the structure shown below:

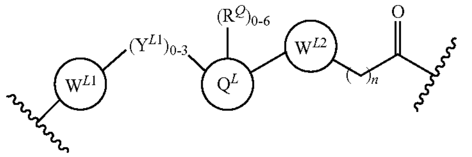

or

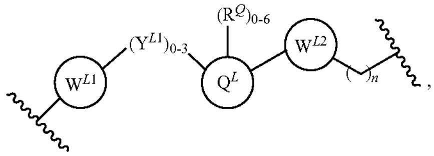

, wherein:

$W^{L1}$ and $W^{L2}$ are each independently absent, cyclohexane, cyclopentane, piperazine, piperidine, morpholine, $C_{1-6}$ alkyl and optionally one or more C atoms are replaced with O or $NR^{YL1}$, $C_{1-6}$ alkene and optionally one or more C atoms are replaced with O, $C_{1-6}$ alkene and optionally one or more C atoms are replaced with O, or $C_{1-6}$ alkyne and optionally one or more C atoms are replaced with O, each optionally substituted with $R^Q$, each $R^Q$ is independently a H, —Cl, —F, OH, CN, $CF_3$, hydroxyl, optionally substituted linear or branched $C_1$-$C_6$ alkyl (e.g., methyl, ethyl), or optionally substituted linear or branched $C_1$-$C_6$ alkoxy;

$Y^{L1}$ is each independently a bond, $NR^{YL1}$, O, $CR^{YL1}R^{YL2}$, C═O, optionally substituted linear or branched $C_1$-$C_6$ alkyl and optionally one or more C atoms are replaced with O or $NR^{YL1}$, $C_{1-6}$ alkene and optionally one or more C atoms are replaced with O, $C_{1-6}$ alkyne and optionally one or more C atoms are replaced with O, or optionally substituted linear or branched $C_1$-$C_6$ alkoxy;

$Q^L$ is a 3-6 membered heterocyclic, heterobicyclic, or heteroaryl ring, optionally substituted with 0-6 $R^Q$, each $R^Q$ is independently H, or optionally substituted linear or branched $C_{1-6}$ alkyl (e.g., optionally substituted by 1 or more halo, $C_{1-6}$ alkoxyl);

$R^{YL1}$, $R^{YL2}$ are each independently H, optionally substituted linear or branched $C_{1-6}$ alkyl (e.g., methyl, ethyl, optionally substituted by 1 or more halo, $C_{1-6}$ alkoxyl);

n is 0-10; and

 and  indicates the attachment point to the PTM or ULM moieties.

In any aspect or embodiment described herein, the linker group is optionally substituted (poly)ethyleneglycol having between 1 and about 100 ethylene glycol units (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, etc., ethylene glycol units), between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interdispersed with optionally substituted, O, N, S, P or Si atoms. In certain embodiments, the linker is substituted with an aryl, phenyl, benzyl, alkyl, alkylene, or heterocycle group. In certain embodiments, the linker may be asymmetric or symmetrical.

In any aspect or embodiment described herein, the linker group may be any suitable moiety as described herein. In any aspect or embodiment described herein, the linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

In any aspect or embodiment described herein, the linker (L) includes an optionally substituted $C_1$-$C_{50}$ alkyl (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ alkyl), wherein each carbon is optionally substituted with (1) a heteroatom selected from N, S, P, or Si atoms that has an appropriate number of hydrogens, substitutions, or both to complete valency, (2) an optionally substituted cycloalkyl or bicyclic cycloalkly, (3) an optionally substituted heterocyloalkyl or bicyclic heterocyloalkyl, (4) an optionally substituted aryl or bicyclic aryl, or (5) optionally substituted heteroaryl or bicyclic heteroaryl. In any aspect or embodiment described herein, the linker (L) does not have heteroatom-heteroatom bonding (e.g., no heteroatoms are covalently linker or adjacently located).

In any aspect or embodiment describe herein, the linker (L) includes an optionally substituted $C_1$-$C_{50}$ alkyl (e.g., $C_1$, $C_2$, $C_3$, $C_4$, $C_5$, $C_6$, $C_7$, $C_8$, $C_9$, $C_{10}$, Cu, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ alkyl), wherein: each carbon is optionally substituted with $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}{=}CR^{L2}$, C≡C, $SiR^{L1}R^{L2}$, $P(O)R^{L1}$, $P(O)OR^{L1}$, $NR^{L3}C({=}NCN)NR^{L4}$, $NR^{L3}C({=}NCN)$, $NR^{L3}C({=}CNO_2)NR^{L4}$, $C_{3-11}$ cycloalkyl optionally substituted with 0-6 $R^{L1}$ and/or $R^{L2}$ groups, $C_{5-13}$ spirocycloalkyl optionally substituted with 0-9 $R^{L1}$ and/or $R^{L2}$ groups, $C_{3-11}$ heteocyclyl optionally substituted with 0-6 $R^{L1}$ and/or $R^{L2}$ groups, $C_{3-11}$ spiroheterocyclyl optionally substituted with 0-8 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 0-4 $R^{L5}$ groups; and $R^{L1}$, $R^{L2}$, $R^{L3}$, $R^{L4}$ and $R^{L5}$ are, each independently, H, halo, $C_{1-8}$alkyl, $OC_{1-6}$alkyl, $SC_{1-8}$alkyl, $NHC_{1-8}$alkyl, $N(C_{1-8}alkyl)_2$, $C_{3-11}$cycloalkyl, aryl, heteroaryl, $C_{3-11}$heterocyclyl, $OC_{1-8}$cycloalkyl, $SC_{1-8}$cycloalkyl, $NHC_{1-8}$cycloalkyl, $N(C_{1-8}cycloalkyl)_2$, $N(C_{1-8}cycloalkyl)(C_{1-8}alkyl)$, OH, $NH_2$, SH, $SO_2C_{1-8}$alkyl, $P(O)(OC_{1-8}alkyl)(C_{1-8}alkyl)$, $P(O)(OC_{1-8}alkyl)_2$, CC—$C_{1-8}$alkyl, CCH, $CH{=}CH(C_{1-8}alkyl)$, $C(C_{1-8}alkyl){=}CH(C_{1-8}alkyl)$, $C(C_{1-8}alkyl){=}C(C_{1-88}alkyl)_2$, $Si(OH)_3$, $Si(C_{1-8}alkyl)_3$, $Si(OH)(C_{1-8}alkyl)_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}alkyl)_2$, $N(C_{1-8}alkyl)CONH(C_{1-8}alkyl)$, $N(C_{1-8}alkyl)CON(C_{1-8}alkyl)_2$, $NHCONH(C_{1-8}alkyl)$, $NHCON(C_{1-8}alkyl)_2$, $NHCONH_2$, $N(C_{1-8}alkyl)SO_2NH(C_{1-8}alkyl)$, $N(C_{1-8}alkyl)SO_2N(C_{1-8}alkyl)_2$, NH $SO_2NH(C_{1-8}alkyl)$, NH $SO_2N(C_{1-8}alkyl)_2$, NH $SO_2NH_2$. In any aspect or embodiment described herein, the linker (L) does not have heteroatom-heteroatom bonding (e.g., no heteroatoms are covalently linker or adjacently located).

In any aspect or embodiment described herein, the linker (L) includes about 1 to about 50 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) alkylene glycol units that are optionally substituted, wherein carbon or oxygen may be substituted with a heteroatom selected from N, S, P, or Si atoms with an appropriate number of hydrogens to complete valency. For example, in any aspect or embodiment described herein, the linker (L) has a chemical structure selected from:

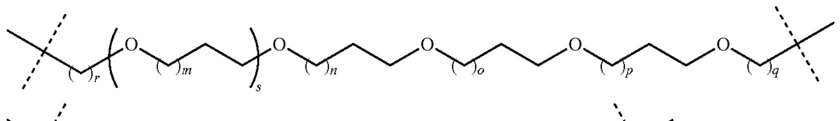

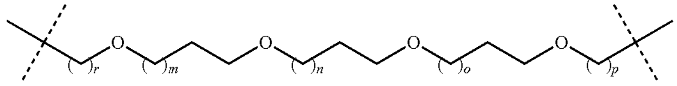

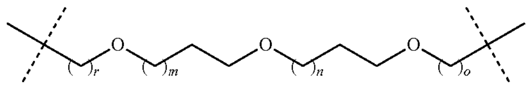

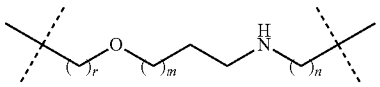

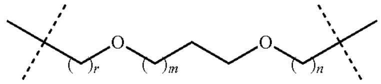

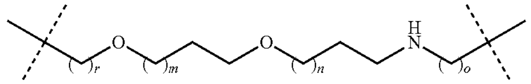

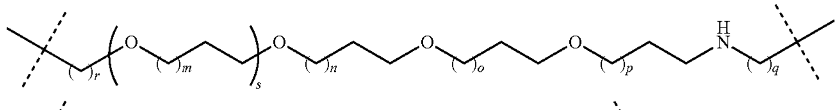

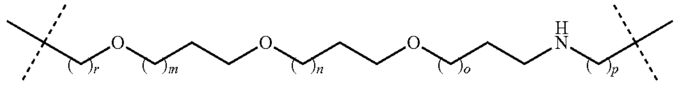

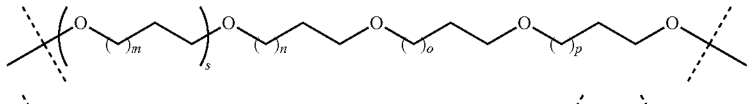

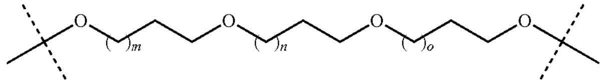

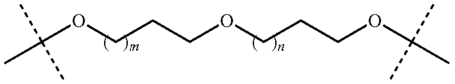

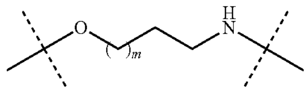

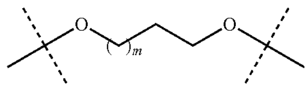

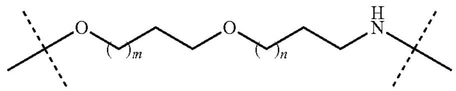

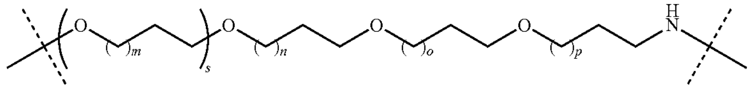

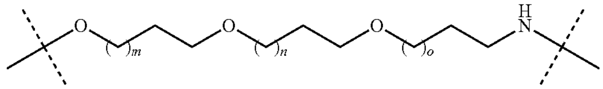

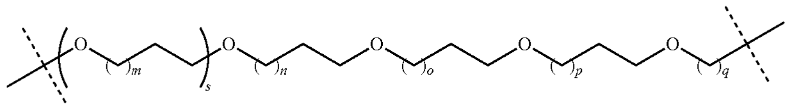

-continued

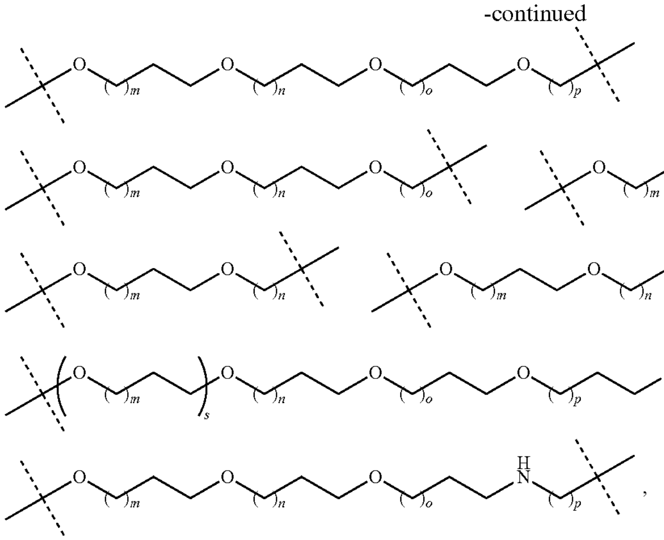

wherein carbon or oxygen may be substituted with a heteroatom selected from N, S, P, or Si atoms with an appropriate number of hydrogens to complete valency, and m, n, o, p, q, r, and s are independently selected from 0, 1, 2, 3, 4, 5, 6, 7, 8, 9, 10, 11, 12, 13, 14, 15, 16, 17, 18, 19, and 20.

In some embodiments, L is an optionally substituted polyethylenoxy group comprising from 1 to 10 units.

In some additional embodiments, L is a polyethylene group optionally substituted with aryl or phenyl comprising from 1 to 10 ethylene glycol units.

In any of the embodiments, the compound comprises multiple ULMs, multiple PTMs, multiple linkers or any combinations thereof.

Although the ULM group and PTM group may be covalently linked to the linker group through any group which is appropriate and stable to the chemistry of the linker, in preferred aspects of the present disclosure, the linker is independently covalently bonded to the ULM group and the PTM group preferably through an amide, ester, thioester, keto group, carbamate (urethane), carbon or ether, each of which groups may be inserted anywhere on the ULM group and PTM group to provide maximum binding of the ULM group on the ubiquitin ligase and the PTM group on the target protein to be degraded. (It is noted that in certain aspects where the PTM group is a ULM group, the target protein for degradation may be the ubiquitin ligase itself). In certain preferred aspects, the linker may be linked to an optionally substituted alkyl, alkylene, alkene or alkyne group, an aryl group or a heterocyclic group on the ULM and/or PTM groups.

Exemplary Tau-Bifunctional Degradation Compounds

As described above, in certain aspects, the description provides bifunctional compounds comprising at least one PTM group, a linker, and at least one ULM (VLM or CLM) group as described herein.

In certain embodiments, the compound is selected from the group consisting of compounds 332, 335, 337-586, and 589-686 (e.g., selected from Table 1), and salts and polymorphs thereof.

In certain embodiments, the compound is selected from Table 1 (i.e., the compound is selected from Compounds 332, 335, 337-586, and 589-686), and salts and polymorphs thereof.

In any aspect or embodiment described herein, the compound is selected from Formulas CI through CV:

Formula CI

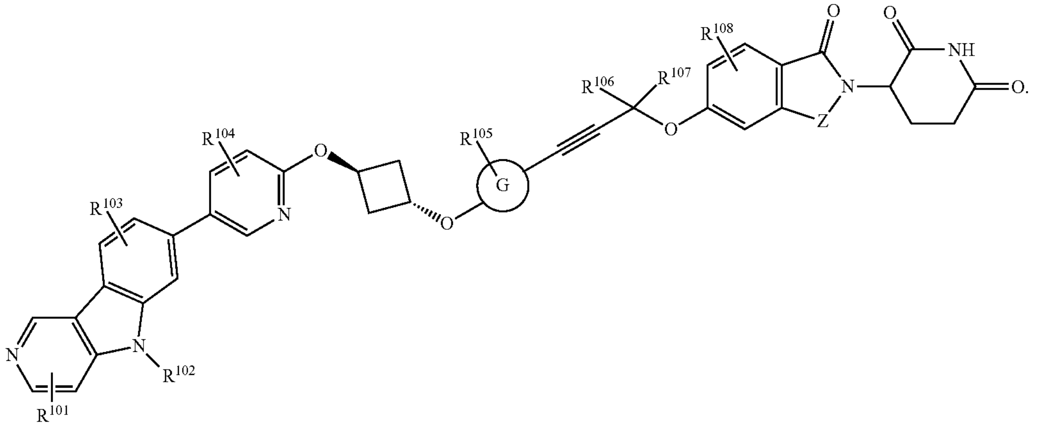

-continued

Formula CII

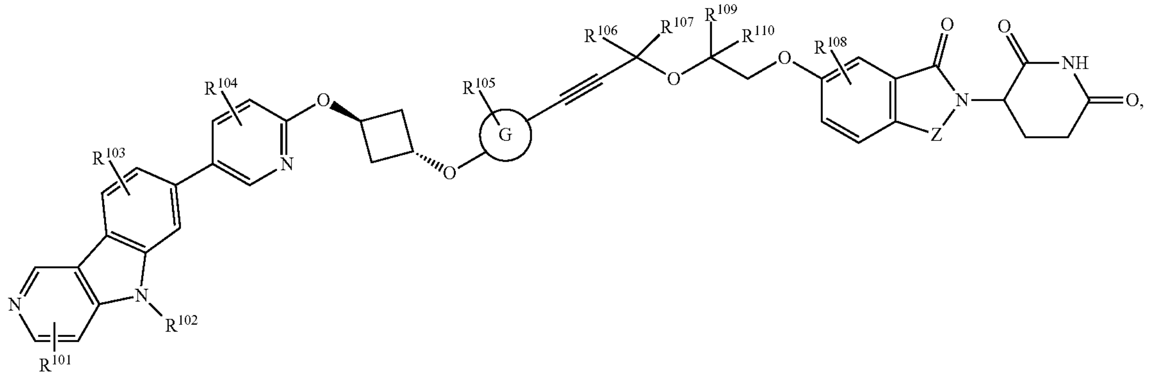

Formula CIII

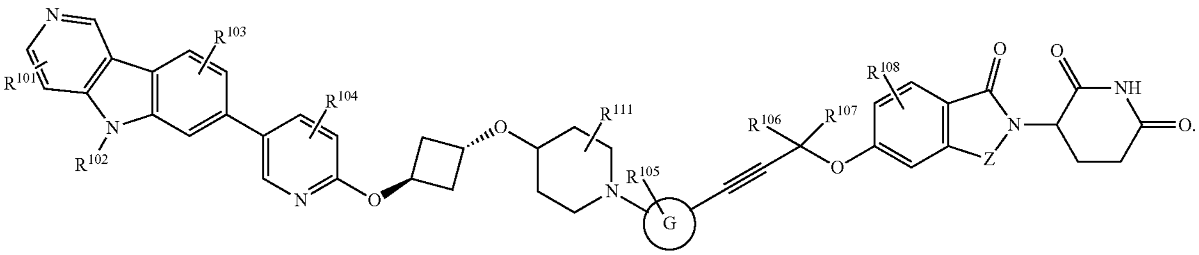

Formula CIV

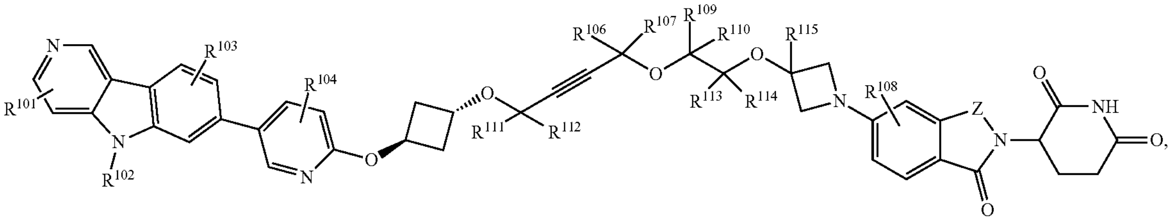

or

Formula CV

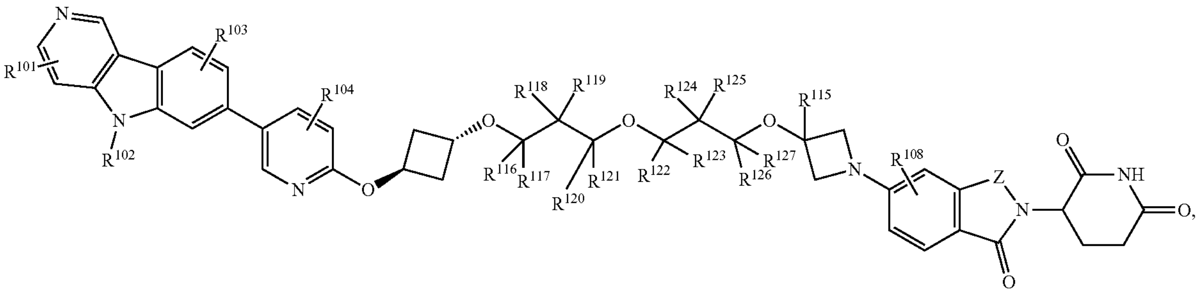

wherein:

$R^{101}$ is 1-2 substituents independently selected from H, alkyl, halogen, haloalkyl or cyano;

$R^{102}$ is selected from H, alkyl, haloalkyl, cycloalkyl or heterocycloalkyl;

$R^{103}$ is 1-2 substituents independently selected from H, alkyl, halogen, haloalkyl or cyano;

$R^{104}$ is 1-2 substituents independently selected from H, alkyl, halogen, haloalkyl or cyano;

$R^{105}$ is 1-2 substituents independently selected from H, alkyl, halogen, haloalkyl or cyano;

$R^{106}$, $R^{107}$, $R^{109}$, $R^{110}$, $R^{111}$, $R^{112}$, $R^{113}$, $R^{114}$, $R^{116}$, $R^{117}$, $R^{120}$, $R^{121}$, $R^{126}$, $R^{127}$, $R^{122}$ and $R^{123}$ are each independently selected from H, alkyl, halogen or haloalkyl;

$R^{108}$ is 1-2 substituents independently selected from H, alkyl, halogen, haloalkyl, cyano or methoxy;

$R^{115}$ is selected from H, alkyl and haloalkyl;

$R^{118}$ and $R^{19}$ are independently selected from H, alkyl, halogen or haloalkyl, or $R^{118}$ and $R^{119}$ taken together with the carbon atom to which they are attached represent a 3-6-membered cycloalkyl or heterocycloalkyl ring, such as cyclopropane or an oxetane;

$R^{124}$ and $R^{125}$ are independently selected from H, alkyl, halogen or haloalkyl, or $R^{124}$ and $R^{125}$ taken together with the carbon atom to which they are attached represent a 3-6-membered cycloalkyl or heterocycloalkyl ring, such as cyclopropane or an oxetane;

G is a phenyl or a 5- or 6-membered heteroaryl ring; and

Z is $CH_2$ or C=O.

In any aspect or embodiment described herein, at least one of:

$R^{101}$ is H, F or Cl;

$R^{102}$ is H, $CH_3$, or $CF_2H$;

$R^{103}$ is H or F;

$R^{104}$ is H, $CH_3$, F or CN;

$R^{105}$ is H, CN, $CH_3$ or $CF_3$;

$R^{106}$ and $R^{107}$ are each independently H, F or $CH_3$;

$R^{108}$ is H, F or $CH_3O$;

$R^{109}$ and $R^{110}$ are each independently H or $CH_3$;

$R^{111}$ and $R^{112}$ are each independently H, F or $CH_3$;

$R^{113}$ and $R^{114}$ are each independently H or $CH_3$;

$R^{115}$ is H or $CH_3$;

$R^{116}$ and $R^{117}$ are each independently H or $CH_3$;

$R^{118}$ and $R^{119}$ are each independently H, $CH_3$, F, or $R^{118}$ and $R^{119}$ taken together with the carbon atom to which they are attached represent a cyclopropane or an oxetane ring;

$R^{120}$ and $R^{121}$ are each independently H or $CH_3$;

$R^{122}$ and $R^{123}$ are each independently H or $CH_3$;

$R^{124}$ and $R^{125}$ are each independently H, $CH_3$, F, or $R^{124}$ and $R^{125}$ taken together with the carbon atom to which they are attached represent a cyclopropane or an oxetane ring;

$R^{126}$ and $R^{127}$ are each independently H or $CH_3$;

A is a pyridine or a pyrimidine;

Z is $CH_2$ or C═O; or a combination thereof.

Therapeutic Compositions

The present invention further provides pharmaceutical compositions comprising therapeutically effective amounts of at least one bifunctional compound as described herein, in combination with a pharmaceutically acceptable carrier, additive or excipient.

In an additional aspect, the description provides therapeutic compositions comprising an effective amount of a compound as described herein or a pharmaceutically acceptable salt form thereof, and a pharmaceutically acceptable carrier, additive or excipient, and optionally an additional bioactive agent. The therapeutic compositions effect targeted protein degradation in a patient or subject, for example, an animal such as a human, and can be used for treating or ameliorating disease states or conditions which are modulated by degrading the target protein. In certain embodiments, the therapeutic compositions as described herein may be used to effectuate the degradation of protein for the treatment or amelioration of a Tau-related disease or disorder, e.g., accumulation or aggregation of Tau protein or a neurodegenerative disease associated with Tau accumulation and/or aggregation. In any aspect or embodiment described herein, the disease or disorder includes at least one of: Acquired Epileptiform Aphasia, Acute Disseminated Encephalomyelitis, ADHD, Adie's Pupil, Adie's Syndrome, Adrenoleukodystrophy, Agenesis of the Corpus Callosum, Agnosia, Aicardi Syndrome, AIDS Neurological Complications, Alexander Disease, Alpers' Disease, Alternating Hemiplegia, Alzheimer's Disease, Amyotrophic Lateral Sclerosis, Anencephaly, Aneurysm, Angelman Syndrome, Angiomatosis, Anoxia, Aphasia, Apraxia, Arachnoid Cysts, Arachnoiditis, Arnold-Chiari Malformation, Arteriovenous Malformation, Asperger Syndrome, Ataxia, Ataxia, Telangiectasia, Ataxias and Cerebellar/Spinocerebellar Degeneration, Attention Deficit-Hyperactivity Disorder, Autism, Autonomic Dysfunction, Back Pain, Barth Syndrome Batten Disease, Becker's Myotonia, Behcet's Disease, Bell's Palsy, Benign Essential Blepharospasm, Benign Focal Amyotrophy, Benign Intracranial Hypertension, Bernhardt-Roth Syndrome, Binswanger's Disease, Blepharospasm, Bloch-Sulzberger Syndrome, Brachial Plexus Birth Injuries, Brachial Plexus Injuries, Bradbury-Eggleston Syndrome, Brain and Spinal Tumors, Brain Aneurysm, Brain Injury, Brown-Sequard Syndrome, Bulbospinal Muscular Atrophy, Canavan Disease, Carpal Tunnel Syndrome Causalgia, Cavernomas, Cavernous Angioma, Cavernous Malformation, Central Cervical Cord Syndrome, Central Cord Syndrome, Central Pain Syndrome, Cephalic Disorders, Cerebellar Degeneration, Cerebellar Hypoplasia, Cerebral Aneurysm, Cerebral Arteriosclerosis, Cerebral Atrophy, Cerebral Beriberi, Cerebral Gigantism, Cerebral Hypoxia, Cerebral Patsy, Cerebro-Oculo-Facio-Skeletal Syndrome, Charcot-Marie-Tooth Disease, Chiari Malformation, Chorea, Choreoacanthocytosis, Chronic Inflammatory Demyelinating Polyneuropathy (CIDP), Chronic Orthostatic Intolerance, Chronic Pain Cockayne Syndrome Type II, Coffin Lowry Syndrome, COFS, Colpocephaly, Coma and Persistent Vegetative State, Complex Regional Pain Syndrome, Congenital Facial Diplegia, Congenital Myasthenia, Congenital Myopathy, Congenital Vascular Cavernous, Malformations, Corticobasal Degeneration, Cranial Arteritis, Craniosynostosis, Creutzfeldt-Jakob Disease, Cumulative Trauma Disorders, Cushing's Syndrome, Cytomegalic Inclusion Body Disease, Cytomegalovirus Infection, Dancing Eyes-Dancing Feet Syndrome, Dandy-Walker Syndrome, Dawson Disease, De Morsier's Syndrome, Deep Brain Stimulation for Parkinson's Disease, Dejerine-Klumpke Palsy, Dementia, Dementia-Multi-Infarct, Dementia-Semantic, Dementia-Subcortical, Dementia With Lewy Bodies, Dentate Cerebellar Ataxia, Dentatorubral Atrophy, Dermatomyositis, Developmental Dyspraxia, Devic's Syndrome, Diabetic Neuropathy, Diffuse Sclerosis, Dysautonomia, Dysgraphia, Dyslexia, Dysphagia, Dyspraxia, Dyssynergia Cerebellaris, Myoclonica, Dyssynergia Cerebellaris Progressiva, Dystonias, Early Infantile Epileptic, Encephalopathy, Empty Sella Syndrome, Encephalitis Lethargica, Encephaloceles, Encephalopathy, Encephalotrigeminal Angiomatosis, Epilepsy, Erb-Duchenne and Dejerine-Klumpke Palsies, Erb's Palsy, Fabry's Disease, Fahr's Syndrome, Fainting, Familial Dysautonomia, Familial Hemangioma, Familial Idiopathic Basal Ganglia, Calcification, Familial Periodic Paralyses, Familial Spastic Paralysis, Febrile Seizures, Fisher Syndrome, Floppy Infant Syndrome, Friedreich's Ataxia, Frontotemporal, Dementia, Gaucher's Disease, Gerstmann's Syndrome, Gerstmann-Straussler-Scheinker, Disease, Giant Cell Arteritis, Giant Cell Inclusion Disease, Globoid Cell Leukodystrophy, Glossopharyngeal Neuralgia, Guillain-Barre Syndrome, Hallervorden-Spatz Disease, Head Injury, Headache, Hemicrania Continua, Hemifacial Spasm, Hemiplegia Alterans, Hereditary Neuropathies, Hereditary Spastic Paraplegia, Heredopathia Atactica Polyneuritiformis, Herpes Zoster, Herpes Zoster Oticus, Hirayama Syndrome, Holmes-Adie syndrome, Holoprosencephaly, HTLV-1 Associated, Myelopathy, Huntington's Disease, Hydranencephaly, Hydrocephalus, Hydrocephalus—Normal Pressure, Hydromyelia, Hyperactivity, Hypercortisolism, Hypersomnia, Hypertonia, Hypotonia—Infantile, Hypoxia, Immune-Mediated Encephalomyelitis, Inclusion Body Myositis, Incontinentia Pigmenti, Infantile Hypotonia, Infantile Neuroaxonal Dystrophy, Infantile Phytanic Acid Storage Disease, Infantile Refsum Disease, Infantile Spasms, Inflammatory Myopathy, Iniencephaly, Intestinal Lipodystrophy, Intracranial Cysts, Intracranial Hypertension, Isaac's Syndrome, Joubert Syndrome, Kearns-Sayre Syndrome, Kennedy's Disease, Kinsbourne syndrome, Kleine-Levin Syndrome, Klippel-Feil Syndrome, Klippel- Trenaunay Syndrome (KTS), Kluver-Bucy Syndrome, Korsakoffs Amnesic Syndrome, Krabbe Disease, Kugelberg-Welander Disease, Kuru, Lambert-Eaton Myasthenic Syndrome, Landau-Kleffner Syndrome, Lateral Femoral, Cutaneous Nerve Entrapment, Lateral Medullary Syndrome, Learning Disabilities, Leigh's Disease, Lennox-Gastaut Syndrome, Lesch-Nyhan Syndrome, Leukodystrophy, Levine-Critchley Syndrome, Lewy Body Dementia, Lipid Storage Diseases, Lissencephaly, Locked-In Syndrome, Lou Gehrig's Disease, Lupus—Neurological, Sequelae, Lyme Disease—Neurological Complications, Machado-Joseph Disease, Macrencephaly, Mania, Megalencephaly, Melkersson-Rosenthal Syndrome, Meningitis, Meningitis and Encephalitis, Menkes Disease, Meralgia Paresthetica, Metachromatic, Leukodystrophy, Microcephaly, Migraine, Miller Fisher Syndrome, Mini-Strokes, Mitochondrial Myopathies, Mobius Syndrome, Monomelic Amyotrophy, Motor Neuron Diseases, Moyamoya Disease, Mucolipidoses, Mucopolysaccharidoses, Multifocal Motor Neuropathy, Multi-Infarct Dementia, Multiple Sclerosis, Multiple System Atrophy, Multiple System Atrophy with Orthostatic Hypotension, Muscular Dystrophy, Myasthenia—Congenital, Myasthenia Gravis, Myelinoclastic Diffuse Sclerosis, Myoclonic Encephalopathy of Infants, Myoclonus, Myopathy, Myopathy—Congenital, Myopathy-Thyrotoxic, Myotonia, Myotonia Congenita, Narcolepsy, Neuroacanthocytosis, Neurodegeneration with Brain Iron Accumulation, Neurofibromatosis, Neuroleptic Malignant Syndrome, Neurological Complications of AIDS, Neurological Complications Of Lyme Disease, Neurological Consequences of Cytomegalovirus Infection, Neurological Manifestations of Pompe Disease, Neurological Sequelae Of Lupus, Neuromyelitis Optica, Neuromyotonia, Neuronal Ceroid, Lipofuscinosis, Neuronal Migration Disorders, Neuropathy—Hereditary, Neurosarcoidosis, Neurotoxicity, Nevus Cavernosus, Niemann-Pick Disease, Normal Pressure Hydrocephalus, Occipital Neuralgia, Obesity, Occult Spinal Dysraphism Sequence, Ohtahara Syndrome, Olivopontocerebellar Atrophy, Opsoclonus Myoclonus, Orthostatic Hypotension, O'Sullivan-McLeod Syndrome, Overuse Syndrome, Pain—Chronic, Paine, Pantothenate Kinase-Associated Neurodegeneration, Paraneoplastic Syndromes, Paresthesia, Parkinson's Disease, Paroxysmal Choreoathetosis, Paroxysmal Hemicrania, Parry-Romberg, Pelizaeus-Merzbacher Disease, Pena Shokeir II Syndrome, Perineural Cysts, Periodic Paralyses, Peripheral Neuropathy, Periventricular Leukomalacia, Persistent Vegetative State, Pervasive Developmental Disorders, Phytanic Acid Storage Disease, Pick's Disease, Pinched Nerve, Piriformis Syndrome, Pituitary Tumors, Polymyositis, Pompe Disease, Porencephaly, Postherpetic Neuralgia, Postinfectious Encephalomyelitis, Post-Polio Syndrome, Postural Hypotension, Postural Orthostatic, Tachycardia Syndrome, Postural Tachycardia Syndrome, Primary Dentatum Atrophy, Primary Lateral Sclerosis, Primary Progressive Aphasia, Prion Diseases, Progressive Hemifacial Atrophy, Progressive Locomotor Ataxia, Progressive Multifocal, Leukoencephalopathy, Progressive Sclerosing Poliodystrophy, Progressive Supranuclear, Palsy, Prosopagnosia, Pseudotumor Cerebri, Ramsay Hunt Syndrome I (formerly known as), Ramsay Hunt Syndrome II (formerly known as), Rasmussen's Encephalitis, Reflex Sympathetic Dystrophy Syndrome, Refsum Disease, Refsum Disease-Infantile, Repetitive Motion Disorders, Repetitive Stress Injuries, Restless Legs Syndrome, Retrovirus-Associated Myelopathy, Rett Syndrome, Reye's Syndrome, Riley-Day Syndrome, Sacral Nerve Root Cysts, Saint Vitus Dance, Salivary Gland Disease, Sandhoff Disease, Schilder's Disease, Schizencephaly, Seitelberger Disease, Seizure Disorder, Semantic Dementia, Septo-Optic Dysplasia, Shaken Baby Syndrome, Shingles Shy-Drager Syndrome, Sjogren's Syndrome, Sleep Apnea, Sleeping Sickness, Sotos Syndrome, Spasticity, Spina Bifida, Spinal Cord Infarction, Spinal Cord Injury, Spinal Cord Tumors, Spinal Muscular Atrophy, Spinocerebellar Atrophy, Spinocerebellar, Degeneration, Steele-Richardson-Olszewski Syndrome, Stiff-Person Syndrome, Striatonigral Degeneration, Stroke, Sturge-Weber Syndrome, Subacute Sclerosing Panencephalitis, Subcortical Arteriosclerotic Encephalopathy, SUNCT Headache Swallowing Disorders, Sydenham Chorea, Syncope, Syphilitic Spinal Sclerosis, Syringohydromyelia, Syringomyelia, Systemic Lupus Erythematosus, Tabes Dorsalis Tardive Dyskinesia, Tarlov Cysts, Tay-Sachs Disease, Temporal Arteritis, Tethered Spinal Cord Syndrome, Thomsen's Myotonia, Thoracic Outlet Syndrome, Thyrotoxic Myopathy, Tic Douloureux, Todd's Paralysis, Tourette Syndrome, Transient Ischemic Attack, Transmissible Spongiform Encephalopathies, Transverse Myelitis, Traumatic Brain Injury, Tremor, Trigeminal Neuralgia, Tropical Spastic Paraparesis, Tuberous Sclerosis, Vascular Erectile Tumor, Vasculitis including Temporal Arteritis, Von Economo's Disease, Von Hippel-Lindau Disease (VHL), Von Recklinghausen's Disease, Wallenberg's Syndrome, Werdnig-Hoffman Disease, Wernicke-Korsakoff Syndrome, West Syndrome, Whiplash, Whipple's Disease, Williams Syndrome, Wilson's Disease, X-Linked Spinal and Bulbar Muscular Atrophy, or Zellweger Syndrome. For example, in any aspect or embodiment described herein, the disease or disorder is a neurological disorder with at least one of: Huntington's disease, muscular dystrophy, Parkinson's disease, Alzheimer's disease, Batten disease, Injuries to the spinal cord and brain, Seizure disorders, epilepsy, brain tumors, meningitis, autoimmune diseases such as multiple sclerosis, neurofibromatosis, Depression, Amyotrophic Lateral Sclerosis, Arteriovenous Malformation, Brain Aneurysm, Dural Arteriovenous Fistulae, Headache, Memory Disorders, Peripheral Neuropathy, Post-Herpetic Neuralgia, Spinal Cord Tumor and Stroke. For example, in any aspect or embodiment described herein, the disease or disorder is at least one of: Primary tauopathies (FTDP-17, Progressive Supranuclear Palsy (PSP), Corticobasal disease (CBD) and most frontotemporal dementias, Secondary tauopathies (Alzheimer's disease), Huntington's disease, muscular dystrophy, Parkinson's disease, Batten disease, Injuries to the spinal cord and brain, Seizure disorders, epilepsy, brain tumors, meningitis, autoimmune diseases such as multiple sclerosis, neurofibromatosis, Depression, Amyotrophic Lateral Sclerosis, Arteriovenous Malformation, Brain Aneurysm, Dural Arteriovenous Fistulae, Headache, Memory Disorders, Peripheral Neuropathy, Post-Herpetic Neuralgia, Spinal Cord Tumor and Stroke.

In alternative aspects, the present disclosure relates to a method for treating a disease state or ameliorating one or more symptoms of a disease or condition in a subject in need thereof by degrading the Tau protein, the method comprising administering to said patient or subject an effective amount, e.g., a therapeutically effective amount, of at least one compound as described herein, optionally in combination with a pharmaceutically acceptable carrier, additive or excipient, and optionally coadministered with an additional bioactive agent, wherein the composition is effective for treating or ameliorating the disease or disorder or one or more symptoms thereof in the subject. The method according to the present disclosure may be used to treat certain disease states, conditions or symptoms including neurological diseases or disorders, such as neurodegenerative diseases or disorders, by virtue of the administration of effective amounts of at least one therapeutically effective compound described herein. For example, the method according to the present disclosure may be used to treat a condition causally related to the accumulation and/or aggregation of a Tau protein, such as, e.g., a neurological/neurodegenerative disease or disorder.

The present disclosure further includes pharmaceutical compositions comprising a pharmaceutically acceptable salt, in particular, an acid or base addition salt of compounds as described in the present disclosure.

The acids which are used to prepare the pharmaceutically acceptable acid addition salts of the aforementioned compounds useful according to this aspect are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds or derivatives according to the present disclosure. The chemical bases that may be used as reagents to prepare pharmaceutically acceptable base salts of the present compounds are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium, zinc and magnesium), ammonium or water-soluble amine addition salts such as N-methylglucamine-(meglumine), and the lower alkanolammonium and other base salts of pharmaceutically acceptable organic amines, among others.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

The therapeutically effective compounds as described herein may, in accordance with the present disclosure, may be administered in single or divided doses by the oral, parenteral or topical routes. Administration of the active compound may range from continuous (intravenous drip) to several administrations per day (for example, Q.I.D.) and may include administration routes such as oral, topical, parenteral, intramuscular, intravenous, sub-cutaneous, transdermal (which may include a penetration enhancement agent), buccal, sublingual, intranasal, intraocular, intrathecal, vaginal, and suppository administration, among other routes of administration. The term "parenteral" as used herein includes subcutaneous, intravenous, intramuscular, intra-articular, intra-synovial, intrasternal, intrathecal, intrahepatic, intralesional and intracranial injection or infusion techniques. Enteric coated oral tablets may be used to enhance bioavailability of the compounds from an oral route of administration. The most effective dosage form will depend upon the pharmacokinetics of the particular agent chosen as well as the type, location and severity of disease, condition or symptom, and the health of the patient.

Administration of compounds according to the present disclosure as sprays, mists, or aerosols for intra-nasal, intratracheal or pulmonary administration may also be used. The present disclosure therefore also is directed to pharmaceutical compositions comprising an effective amount of compound as described herein or a pharmaceutically acceptable salt thereof, optionally in combination with a pharmaceutically acceptable carrier, additive or excipient. Compounds according to the present disclosure may be administered in intermediate release or sustained or controlled release forms. Sustained or controlled release forms are preferably administered orally, but also in suppository and transdermal or other topical forms. Intramuscular injections in liposomal form or in depot formulation may also be used to control or sustain the release of compound at an injection site.

The compositions as described herein may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat, and combinations thereof.

Sterile injectable forms of the compositions as described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution, dimethyl sulfoxide (DMSO), betacyclodextrin and derivatives thereof, and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn, among others known in the art. For oral administration in a capsule form, useful diluents include lactose and corn starch. When aqueous suspensions are required for oral use, the active ingredient may be combined with emulsifying and suspending agents. If desired, certain sweetening, flavoring or coloring agents may also be added. Lubricating agents, such as magnesium stearate, are also typically added.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions as described herein may also be administered topically. For topical applications, the pharmaceutical composition can be formulated in a transdermal patch, which can either be a reservoir patch or a matrix patch comprising the active compound combined with one or more carriers, buffers, absorption enhancers, and providing from 1 day to two weeks of continuous administration.

Alternatively, the pharmaceutical compositions of the present disclosure may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water.

Alternatively, the pharmaceutical compositions of the present disclosure can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Alternatively, the pharmaceutical compositions of the present disclosure can be formulated for ophthalmic use. For example, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of as described herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of active pharmaceutical ingredient in a pharmaceutical composition as described herein that may be combined with the carrier materials to produce a single dosage form will vary depending upon the condition of the subject and disease, condition or symptom treated, the particular mode of administration, and the condition of the subject. Preferably, the compositions should be formulated to contain between about 0.05 milligram and about 750 milligrams or more, more preferably about 1 milligram to about 600 milligrams, and even more preferably about 10 milligrams to about 500 milligrams of active ingredient, alone or in combination with another compound according to the present disclosure.

It should also be understood that a specific dosage and treatment regimen for any particular patient will depend on the judgment of the treating physician as based upon a variety of factors, including the activity and bioavailability of the specific compound employed, the age, body weight, general health, sex, diet, time of administration, rate of excretion, drug combination, and the severity of the particular disease or condition being treated.

A patient or subject in need of therapy using a compound according to the methods described herein can be treated by administering to the patient (subject) an effective amount of the compound according to the present disclosure, either alone, or in combination with another known therapeutic agent.

In any aspect or embodiment described herein, the active compound is combined with the pharmaceutically acceptable carrier or diluent in an amount sufficient to deliver to a patient a therapeutically effective amount for the desired indication, without causing an undue degree of serious toxic effects in the patient treated. A preferred dose of the active compound for all of the herein-mentioned conditions is in the range from about 10 nanograms per kilograms (ng/kg) to 300 milligrams per kilograms (mg/kg), preferably 0.1 to 100 mg/kg per day, such as 0.5 to about 25 mg per kilogram body weight of the recipient/patient per day.

In any aspect or embodiment described herein, the compound is conveniently administered in any suitable unit dosage form, including but not limited to a dosage form containing less than 1 milligrams (mg), 1 mg to 3000 mg, or 5 mg to 500 mg of active ingredient per unit dosage form. An oral dosage of about 25 mg-250 mg is often convenient.

In certain aspects, the active ingredient is preferably administered to achieve peak plasma concentrations of the active compound of about 0.00001-30 millimole (mM), preferably about 0.1-30 micromole (μM). This may be achieved, for example, by the intravenous injection of a solution or formulation of the active ingredient, optionally in saline, or an aqueous medium or administered as a bolus of the active ingredient. Oral administration may also be appropriate to generate effective plasma concentrations of active agent.

The concentration of active compound in the drug composition will depend on absorption, distribution, metabolism, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the physician administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as anti-neurodegenerative agents, as described herein among others. In certain preferred aspects of the disclosure, one or more compounds according to the present disclosure are coadministered with another bioactive agent, such as an anti-neurodegenerative agent, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In any aspect or embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Therapeutic Methods

In an additional aspect, the description provides a therapeutic methods comprising administering an effective amount of a compound as described herein or pharmaceutically acceptable salt form thereof, and a pharmaceutically acceptable carrier. In any aspect or embodiment described herein, the composition further comprises an effective or synergistic amount of another bioactive agent that is not a bifunctional degradative compound.

The term "bioactive agent" is used to describe an agent, other than the bifunctional compounds described herein, which is used in combination with the present compounds as an agent with biological activity to assist in effecting an intended therapy, inhibition and/or prevention/prophylaxis for which the present compounds are used. Preferred bioactive agents for use herein include those agents which assist in effecting an intended therapy, for example, P-gp inhibitors or agents that have pharmacological activity similar to that for which the present compounds are used or administered and include for example, anti-neurodegenerative agents.

The term "P-gp" is used to describe "permeability glycoprotein" or P-glycoprotein (ABCB1) which was discovered in 1976 in rodent cells. The presence of "endogenous or physiological" P-gp is a potential problem to achieving targeted exposure with therapeutic agents. P-gp is expressed at barrier tissue to sanctuary sites (e.g., blood-brain barrier) and at secretory/absorptive tissues (e.g., gastrointestinal tract) (Cordon-Cardo et al., 1989, 1990). The protein acts as a cellular defender and influences the overall pharmacokinetic profile of numerous drugs by actively pumping them out of the intracellular environment (effluxing) thereby reducing drug penetration of the barrier tissues. In particular, P-gp efflux reduces drug permeability across the gastrointestinal tract membranes and may lead to reduced systemic exposure of the drug. P-gp efflux also reduces drug access across the blood-brain barrier. P-gp inhibitors could indirectly contribute to efficacy by increasing bifunctional compound exposure, particularly CNS exposure The term "additional anti-neurodegenerative agent" is used to describe an anti-neurodegenerative agent, which may be combined with bifunctional compounds according to the present description to treat neurodenerative diseases.

In any aspect or embodiment described herein, the bifunctional compounds are used along with P-gp inhibitors.

In any aspect or embodiment described herein, the P-gp inhibitors are selected from the group consisting of, but not limited to, Amiodarone, Azithromycin, Captopril, Clarithromycin, Cyclosporine, Piperine, Quercetin, Quinidine, Quinine, Reserpine, Ritonavir, Tariquidar, Elacridar and Verapamil.

The therapeutic methods are useful to effect protein degradation in a patient or subject in need thereof, for example, an animal such as a human, for treating or ameliorating a disease state, condition or related symptom that may be treated through targeted protein degradation.

In another aspect, the disclosure provides methods of modulating protein ubiquitination and degradation in a subject, e.g., a cell, a tissue, mammal, or human patient, the method comprising administering an effective amount of a hetero-bifunctional compound as described herein or a composition comprising an effective amount of a hetero-bifunctional compound as described herein to a subject, wherein the compound or composition comprising the same is effective in modulating protein ubquitination and degradation of the protein in the subject. In certain embodiments, the protein is Tau protein.

In certain embodiments, the description provides a method for regulating protein activity of Tau protein by degenerating Tau aggregates in a patient in need comprising administering to said patient an amount of a compound as described herein to a patient.

In still additional embodiments, the description provides a method of treating a disease state or condition in a patient wherein dysregulated protein activity (Tau aggregation and accumulation) is responsible for said disease state or condition, said method comprising administering to said patient an effective amount of a compound as described herein to said patient in order to regulate said protein activity in said patient. In certain embodiments, the protein is Tau.

The terms "treat", "treating", and "treatment", etc., as used herein, refer to any action providing a benefit to a patient for which the present compounds may be administered, including the treatment of any disease state, condition, or symptom which is related to the protein to which the present compounds bind. Disease states or conditions, including neurological and neurodegenerative diseases or disorders, which may be treated using compounds according to the present disclosure are set forth hereinabove.

The description provides therapeutic methods for effectuating the degradation of proteins of interest for the treatment or amelioration of a disease, e.g., neurological and neurodegenerative diseases or disorders. As such, in another aspect, the disclosure provides a method of ubiquitinating/degradint a target protein in a cell. In any aspect or embodiment described herein, the method comprises administering a bifunctional compound of the present disclosure. The control or reduction of specific protein levels in cells of a subject as afforded by the present disclosure provides treatment of a disease state, condition, or symptom. In any aspect or embodiment, the method comprises administering an effective amount of a compound as described herein optionally including a pharmaceutically acceptable excipient, carrier, adjuvant, another bioactive agent, or a combination thereof.

In additional embodiments, the description provides methods for treating or ameliorating a disease, disorder or symptom thereof in a subject or a patient, e.g., an animal such as a human, comprising administering to a subject in need thereof a composition comprising an effective amount, e.g. a therapeutically effective amount, of a compound as described herein or a falt form thereof, and a pharmaceutically acceptable excipient, carrier, adjuvant, another bioactive agent, or a combination thereof, wherein the composition is effective for treating or ameliorating the disease or disorder or symptom in the subject.

In any aspect or embodiment described herein, the disease or disorder is related to Tau accumulation or aggregation in a subject, e.g., a cell, a tissue, mammal, or human patient.

In any aspect or embodiment described herein, the disease or disorder is a neurological disorder including but not limited to Absence of the Septum Pellucidum, Acquired Epileptiform Aphasia, Acute Disseminated Encephalomyelitis, ADHD, Adie's Pupil, Adie's Syndrome, Adrenoleukodystrophy, Agenesis of the Corpus Callosum, Agnosia, Aicardi Syndrome, AIDS-Neurological Complications, Alexander Disease, Alpers' Disease, Alternating Hemiplegia, Alzheimer's Disease, Amyotrophic Lateral Sclerosis, Anencephaly, Aneurysm, Angelman Syndrome, Angiomatosis, Anoxia, Aphasia, Apraxia, Arachnoid Cysts, Arachnoiditis, Arnold-Chiari Malformation, Arteriovenous Malformation, Asperger Syndrome, Ataxia, Ataxia, Telangiectasia, Ataxias and Cerebellar/Spinocerebellar Degeneration, Attention Deficit-Hyperactivity Disorder, Autism, Autonomic Dysfunction, Back Pain, Barth Syndrome Batten Disease, Becker's Myotonia, Behcet's Disease, Bell's Palsy, Benign Essential Blepharospasm, Benign Focal Amyotrophy, Benign Intracranial Hypertension, Bernhardt-Roth Syndrome, Binswanger's Disease, Blepharospasm, Bloch-Sulzberger Syndrome, Brachial Plexus Birth Injuries, Brachial Plexus Injuries, Bradbury-Eggleston Syndrome, Brain and Spinal Tumors, Brain Aneurysm, Brain Injury, Brown-Sequard Syndrome, Bulbospinal Muscular Atrophy, Canavan Disease, Carpal Tunnel Syndrome Causalgia, Cavernomas, Cavernous Angioma, Cavernous Malformation, Central Cervical Cord Syndrome, Central Cord Syndrome, Central Pain Syndrome, Cephalic Disorders, Cerebellar Degeneration, Cerebellar Hypoplasia, Cerebral Aneurysm, Cerebral Arteriosclerosis, Cerebral Atrophy, Cerebral Beriberi, Cerebral Gigantism, Cerebral Hypoxia, Cerebral Patsy, Cerebro-Oculo-Facio-Skeletal Syndrome, Charcot-Marie-Tooth Disease, Chiari Malformation, Chorea, Choreoacanthocytosis, Chronic Inflammatory Demyelinating Polyneuropathy (CIDP), Chronic Orthostatic Intolerance, Chronic Pain Cockayne Syndrome Type II, Coffin Lowry Syndrome, COFS, Colpocephaly, Coma and Persistent Vegetative State, Complex Regional Pain Syndrome, Congenital Facial Diplegia, Congenital Myasthenia, Congenital Myopathy, Congenital Vascular Cavernous, Malformations, Corticobasal Degeneration, Cranial Arteritis, Craniosynostosis, Creutzfeldt-Jakob Disease, Cumulative Trauma Disorders, Cushing's Syndrome, Cytomegalic Inclusion Body Disease, Cytomegalovirus Infection, Dancing Eyes-Dancing Feet Syndrome, Dandy-Walker Syndrome, Dawson Disease, De Morsier's Syndrome, Deep Brain Stimulation for Parkinson's Disease, Dejerine-Klumpke Palsy, Dementia, Dementia—Multi-Infarct, Dementia—Semantic, Dementia—Subcortical, Dementia With Lewy Bodies, Dentate Cerebellar Ataxia, Dentatorubral Atrophy, Dermatomyositis, Developmental Dyspraxia, Devic's Syndrome, Diabetic Neuropathy, Diffuse Sclerosis, Dysautonomia, Dysgraphia, Dyslexia, Dysphagia, Dyspraxia, Dyssynergia Cerebellaris, Myoclonica, Dyssynergia Cerebellaris Progressiva, Dystonias, Early Infantile Epileptic, Encephalopathy, Empty Sella Syndrome, Encephalitis Lethargica, Encephaloceles, Encephalopathy, Encephalotrigeminal Angiomatosis, Epilepsy, Erb-Duchenne and Dejerine-Klumpke Palsies, Erb's Palsy, Fabry's Disease, Fahr's Syndrome, Fainting, Familial Dysautonomia, Familial Hemangioma, Familial Idiopathic Basal Ganglia, Calcification, Familial Periodic Paralyses, Familial Spastic Paralysis, Febrile Seizures, Fisher Syndrome, Floppy Infant Syndrome, Friedreich's Ataxia, Frontotemporal, Dementia, Gaucher's Disease, Gerstmann's Syndrome, Gerstmann-Straussler-Scheinker, Disease, Giant Cell Arteritis, Giant Cell Inclusion Disease, Globoid Cell Leukodystrophy, Glossopharyngeal Neuralgia, Guillain-Barre Syndrome, Hallervorden-Spatz Disease, Head Injury, Headache, Hemicrania Continua, Hemifacial Spasm, Hemiplegia Alterans, Hereditary Neuropathies, Hereditary Spastic Paraplegia, Heredopathia Atactica Polyneuritiformis, Herpes Zoster, Herpes Zoster Oticus, Hirayama Syndrome, Holmes-Adie syndrome, Holoprosencephaly, HTLV-1 Associated, Myelopathy, Huntington's Disease, Hydranencephaly, Hydrocephalus, Hydrocephalus—Normal Pressure, Hydromyelia, Hyperactivity, Hypercortisolism, Hypersomnia, Hypertonia, Hypotonia—Infantile, Hypoxia, Immune-Mediated Encephalomyelitis, Inclusion Body Myositis, Incontinentia Pigmenti, Infantile Hypotonia, Infantile Neuroaxonal Dystrophy, Infantile Phytanic Acid Storage Disease, Infantile Refsum Disease, Infantile Spasms, Inflammatory Myopathy, Iniencephaly, Intestinal Lipodystrophy, Intracranial Cysts, Intracranial Hypertension, Isaac's Syndrome, Joubert Syndrome, Kearns-Sayre Syndrome, Kennedy's Disease, Kinsbourne syndrome, Kleine-Levin Syndrome, Klippel-Feil Syndrome, Klippel-Trenaunay Syndrome (KTS), Klüver-Bucy Syndrome, Korsakoffs Amnesic Syndrome, Krabbe Disease, Kugelberg-Welander Disease, Kuru, Lambert-Eaton Myasthenic Syndrome, Landau-Kleffner Syndrome, Lateral Femoral, Cutaneous Nerve Entrapment, Lateral Medullary Syndrome, Learning Disabilities, Leigh's Disease, Lennox-Gastaut Syndrome, Lesch-Nyhan Syndrome, Leukodystrophy, Levine-Critchley Syndrome, Lewy Body Dementia, Lipid Storage Diseases, Lissencephaly, Locked-In Syndrome, Lou Gehrig's Disease, Lupus—Neurological, Sequelae, Lyme Disease-Neurological Complications, Machado-Joseph Disease, Macrencephaly, Mania, Megalencephaly, Melkersson-Rosenthal Syndrome, Meningitis, Meningitis and Encephalitis, Menkes Disease, Meralgia Paresthetica, Metachromatic, Leukodystrophy, Microcephaly, Migraine, Miller Fisher Syndrome, Mini-Strokes, Mitochondrial Myopathies, Mobius Syndrome, Monomelic Amyotrophy, Motor Neuron Diseases, Moyamoya Disease, Mucolipidoses, Mucopolysaccharidoses, Multifocal Motor Neuropathy, Multi-Infarct Dementia, Multiple Sclerosis, Multiple System Atrophy, Multiple System Atrophy with Orthostatic Hypotension, Muscular Dystrophy, Myasthenia—Congenital, Myasthenia Gravis, Myelinoclastic Diffuse Sclerosis, Myoclonic Encephalopathy of Infants, Myoclonus, Myopathy, Myopathy—Congenital, Myopathy-Thyrotoxic, Myotonia, Myotonia Congenita, Narcolepsy, Neuroacanthocytosis, Neurodegeneration with Brain Iron Accumulation, Neurofibromatosis, Neuroleptic Malignant Syndrome, Neurological Complications of AIDS, Neurological Complications Of Lyme Disease, Neurological Consequences of Cytomegalovirus Infection, Neurological Manifestations of Pompe Disease, Neurological Sequelae Of Lupus, Neuromyelitis Optica, Neuromyotonia, Neuronal Ceroid, Lipofuscinosis, Neuronal Migration Disorders, Neuropathy—Hereditary, Neurosarcoidosis, Neurotoxicity, Nevus Cavernosus, Niemann-Pick Disease, Normal Pressure Hydrocephalus, Occipital Neuralgia, Obesity, Occult Spinal Dysraphism Sequence, Ohtahara Syndrome, Olivopontocerebellar Atrophy, Opsoclonus Myoclonus, Orthostatic Hypotension, O'Sullivan-McLeod Syndrome, Overuse Syndrome, Pain—Chronic, Paine, Pantothenate Kinase-Associated Neurodegeneration, Paraneoplastic Syndromes, Paresthesia, Parkinson's Disease, Paroxysmal Choreoathetosis, Paroxysmal Hemicrania, Parry-Romberg, Pelizaeus-Merzbacher Disease, Pena Shokeir II Syndrome, Perineural Cysts, Periodic Paralyses, Peripheral Neuropathy, Periventricular Leukomalacia, Persistent Vegetative State, Pervasive Developmental Disorders, Phytanic Acid Storage Disease, Pick's Disease, Pinched Nerve, Piriformis Syndrome, Pituitary Tumors, Polymyositis, Pompe Disease, Porencephaly, Postherpetic Neuralgia, Postinfectious Encephalomyelitis, Post-Polio Syndrome, Postural Hypotension, Postural Orthostatic, Tachycardia Syndrome, Postural Tachycardia Syndrome, Primary Dentatum Atrophy, Primary Lateral Sclerosis, Primary Progressive Aphasia, Prion Diseases, Progressive Hemifacial Atrophy, Progressive Locomotor Ataxia, Progressive Multifocal, Leukoencephalopathy, Progressive Sclerosing Poliodystrophy, Progressive Supranuclear, Palsy, Prosopagnosia, Pseudotumor Cerebri, Ramsay Hunt Syndrome I (formerly known as), Ramsay Hunt Syndrome II (formerly known as), Rasmussen's Encephalitis, Reflex Sympathetic Dystrophy Syndrome, Refsum Disease, Refsum Disease-Infantile, Repetitive Motion Disorders, Repetitive Stress Injuries, Restless Legs Syndrome, Retrovirus-Associated Myelopathy, Rett Syndrome, Reye's Syndrome, Riley-Day Syndrome, Sacral Nerve Root Cysts, Saint Vitus Dance, Salivary Gland Disease, Sandhoff Disease, Schilder's Disease, Schizencephaly, Seitelberger Disease, Seizure Disorder, Semantic Dementia, Septo-Optic Dysplasia, Shaken Baby Syndrome, Shingles Shy-Drager Syndrome, Sjogren's Syndrome, Sleep Apnea, Sleeping Sickness, Sotos Syndrome, Spasticity, Spina Bifida, Spinal Cord Infarction, Spinal Cord Injury, Spinal Cord Tumors, Spinal Muscular Atrophy, Spinocerebellar Atrophy, Spinocerebellar, Degeneration, Steele-Richardson-Olszewski Syndrome, Stiff-Person Syndrome, Striatonigral Degeneration, Stroke, Sturge-Weber Syndrome, Subacute Sclerosing Panencephalitis, Subcortical Arteriosclerotic Encephalopathy, SUNCT Headache Swallowing Disorders, Sydenham Chorea, Syncope, Syphilitic Spinal Sclerosis, Syringohydromyelia, Syringomyelia, Systemic Lupus Erythematosus, Tabes Dorsalis Tardive Dyskinesia, Tarlov Cysts, Tay-Sachs Disease, Temporal Arteritis, Tethered Spinal Cord Syndrome, Thomsen's Myotonia, Thoracic Outlet Syndrome, Thyrotoxic Myopathy, Tic Douloureux, Todd's Paralysis, Tourette Syndrome, Transient Ischemic Attack, Transmissible Spongiform Encephalopathies, Transverse Myelitis, Traumatic Brain Injury, Tremor, Trigeminal Neuralgia, Tropical Spastic Paraparesis, Tuberous Sclerosis, Vascular Erectile Tumor, Vasculitis including Temporal Arteritis, Von Economo's Disease, Von Hippel-Lindau Disease (VHL), Von Recklinghausen's Disease, Wallenberg's Syndrome, Werdnig-Hoffman Disease, Wernicke-Korsakoff Syndrome, West Syndrome, Whiplash, Whipple's Disease, Williams Syndrome, Wilson's Disease, X-Linked Spinal and Bulbar Muscular Atrophy, or Zellweger Syndrome.

In any aspect or embodiment described herein, the disease or disorder is at least one of Huntington's disease, muscular dystrophy, Parkinson's disease, Alzheimer's disease, Batten disease, Injuries to the spinal cord and brain, Seizure disorders, epilepsy, brain tumors, meningitis, autoimmune diseases such as multiple sclerosis, Neurofibromatosis, Depression, Amyotrophic Lateral Sclerosis, Arteriovenous Malformation, Brain Aneurysm, Dural Arteriovenous Fistulae, Headache, Memory Disorders, Peripheral Neuropathy, Post-Herpetic Neuralgia, Spinal Cord Tumor and Stroke.

In any aspect or embodiment described herein, the disease or disorder is Alzheimer's disease.

In another aspect, the disclosure provides methods for identifying the effects of the degradation of proteins of interest in a biological system using compounds according to the present disclosure.

In another aspect, the description provides a process for making a molecule that can cause degradation of Tau protein in a cell (e.g., in vivo or in vitro), comprising the steps of: (i) providing a small molecule that binds to the Tau protein or a mutated form thereof; (ii) providing an E3 ubiquitin ligase binding moiety (ULM), preferably a CLM or VLM or ILM as described herein; and (iii) covalently coupling the small molecule of step (i) to the ULM of step (ii) via a chemical linking group (L) to form a compound which binds to both an E3 ubiquitin ligase and Tau protein in the cell, such that the E3 ubiquitin ligase is brought in proximity to, and ubiquitinates the Tau protein bound thereto, such that the ubiquitinated Tau is then degraded.

In another aspect, the description provides a method for detecting whether a molecule can trigger degradation of a Tau protein in a cell (e.g., in vivo or in vitro), the method comprising the steps of: (i) providing a molecule for which the ability to trigger degradation of Tau protein in a cell is to be detected, said molecule comprising the structure: ULM-L-PTM, wherein ULM is an E3 ubiquitin ligase binding moietycapable of binding an E3 ubiquitin ligase in a cell, wherein the ULM is as described herein (e.g., CLM, VLM, or ILM); PTM is a protein targeting moiety, which is a small molecule that binds to Tau protein, said Tau having at least one lysine residue available to be ubiquitinated by an E3 ubiquitin ligase bound to the ULM of the molecule; and L is a chemical linking group that covalently links the ULM to the PTM to form the molecule; (ii) incubating a Tau protein-expressing cell in the presence of the molecule of step (i); and (iii) detecting whether the Tau protein in the cell has been degraded.

In any aspect or embodiment described herein, the small molecule capable of binding Tau protein, is a small molecule that binds Tau protein. In any aspect or embodiment described herein, the small molecule that binds the Tau protein is as described herein.

In another aspect of said treatment, the present disclosure provides a method of treating a human patient in need of said treatment of a disease state, condition, or symptom causally related to Tau protein (e.g., expression, over-expression, mutation, aggregation, accumulation, misfolding or dysregulation), where the degradation of the Tau protein will produce a therapeutic effect in the patient, the method comprising administering to the patient an effective amount of a compound according to the present disclosure, optionally in combination with another bioactive agent.

The disease state, condition, or symptom may be caused by a microbial agent or other exogenous agent such as a virus, bacteria, fungus, protozoa or other microbe, or may be a disease state, which is caused by expression, overexpression, mutation, misfolding, or dysregulation of the Tau protein, which leads to a disease state, condition, or symptom.

In another aspect, the present disclosure provides a method of treating or ameliorating at least one symptom of a disease or condition in a subject, comprising the steps of: providing a subject identified as having a symptom of a disease or condition causally related to expression, overexpression, mutation, misfolding, or dysregulation of Tau protein in the subject, wherein the symptom of the disease or condition is treated or ameliorated by degrading Tau protein in cells of the subject; and administering to the subject therapeutically effective amount of a compound comprising a small molecule of the present invention such that the Tau protein is degraded, thereby treating or ameliorating at least one symptom of a disease or condition in the subject.

The term "disease state" or "condition" is used to describe any disease state or condition wherein protein expression, overexpression, mutation, misfolding, or dysregulation (i.e., the amount of protein expressed in a patient is elevated) occurs and where degradation of Tau protein in a patient provides beneficial therapy or relief of symptoms to a patient in need thereof. In certain instances, the disease state or condition may be cured.

Disease states or conditions which may be treated using compounds according to the present disclosure include neurological/neuroal disorders or diseases, for example, neurodegeneration, Huntington's disease and muscular dystrophy, Parkinson's disease, Alzheimer's disease, Batten disease, Injuries to the spinal cord and brain, Seizure disorders, epilepsy, brain tumors, meningitis, autoimmune diseases such as multiple sclerosis, Neurofibromatosis, Depression, Amyotrophic Lateral Sclerosis, Arteriovenous Malformation, Brain Aneurysm, Dural Arteriovenous Fistulae, Headache, Memory Disorders, Peripheral Neuropathy, Post-Herpetic Neuralgia, Spinal Cord Tumor, Stroke.

The term "neurological disorder" or "neurological disorders", as used herein, refers to any disorder, disease, and/or syndrome due to or resulting from neurologic, psychiatric, psychological, and/or cerebrovascular symptomology or origin. The term "neurological disorder" or "neurological disorders", as used herein, also refers to diseases, disorder or condition of the brain and nervous system or psychiatric disorders or conditions. Neurological disorders include, but are not limited to Absence of the Septum Pellucidum, Acquired Epileptiform Aphasia, Acute Disseminated Encephalomyelitis, ADHD, Adie's Pupil, Adie's Syndrome, Adrenoleukodystrophy, Agenesis of the Corpus Callosum, Agnosia, Aicardi Syndrome, AIDS-Neurological Complications, Alexander Disease, Alpers' Disease, Alternating Hemiplegia, Alzheimer's Disease, Amyotrophic Lateral Sclerosis, Anencephaly, Aneurysm, Angelman Syndrome, Angiomatosis, Anoxia, Aphasia, Apraxia, Arachnoid Cysts, Arachnoiditis, Arnold-Chiari Malformation, Arteriovenous Malformation, Asperger Syndrome, Ataxia, Ataxia, Telangiectasia, Ataxias and Cerebellar/Spinocerebellar Degeneration, Attention Deficit-Hyperactivity Disorder, Autism, Autonomic Dysfunction, Back Pain, Barth Syndrome Batten Disease, Becker's Myotonia, Behcet's Disease, Bell's Palsy, Benign Essential Blepharospasm, Benign Focal Amyotrophy, Benign Intracranial Hypertension, Bernhardt-Roth Syndrome, Binswanger's Disease, Blepharospasm, Bloch-Sulzberger Syndrome, Brachial Plexus Birth Injuries, Brachial Plexus Injuries, Bradbury-Eggleston Syndrome, Brain and Spinal Tumors, Brain Aneurysm, Brain Injury, Brown-Sequard Syndrome, Bulbospinal Muscular Atrophy, Canavan Disease, Carpal Tunnel Syndrome Causalgia, Cavernomas, Cavernous Angioma, Cavernous Malformation, Central Cervical Cord Syndrome, Central Cord Syndrome, Central Pain Syndrome, Cephalic Disorders, Cerebellar Degeneration, Cerebellar Hypoplasia, Cerebral Aneurysm, Cerebral Arteriosclerosis, Cerebral Atrophy, Cerebral Beriberi, Cerebral Gigantism, Cerebral Hypoxia, Cerebral Patsy, Cerebro-Oculo-Facio-Skeletal Syndrome, Charcot-Marie-Tooth Disease, Chiari Malformation, Chorea, Choreoacanthocytosis, Chronic Inflammatory Demyelinating Polyneuropathy (CIDP), Chronic Orthostatic Intolerance, Chronic Pain Cockayne Syndrome Type II, Coffin Lowry Syndrome, COFS, Colpocephaly, Coma and Persistent Vegetative State, Complex Regional Pain Syndrome, Congenital Facial Diplegia, Congenital Myasthenia, Congenital Myopathy, Congenital Vascular Cavernous, Malformations, Corticobasal Degeneration, Cranial Arteritis, Craniosynostosis, Creutzfeldt-Jakob Disease, Cumulative Trauma Disorders, Cushing's Syndrome, Cytomegalic Inclusion Body Disease, Cytomegalovirus Infection, Dancing Eyes-Dancing Feet Syndrome, Dandy-Walker Syndrome, Dawson Disease, De Morsier's Syndrome, Deep Brain Stimulation for Parkinson's Disease, Dejerine-Klumpke Palsy, Dementia, Dementia-Multi-Infarct, Dementia-Semantic, Dementia-Subcortical, Dementia With Lewy Bodies, Dentate Cerebellar Ataxia, Dentatorubral Atrophy, Dermatomyositis, Developmental Dyspraxia, Devic's Syndrome, Diabetic Neuropathy, Diffuse Sclerosis, Dysautonomia, Dysgraphia, Dyslexia, Dysphagia, Dyspraxia, Dyssynergia Cerebellaris, Myoclonica, Dyssynergia Cerebellaris Progressiva, Dystonias, Early Infantile Epileptic, Encephalopathy, Empty Sella Syndrome, Encephalitis Lethargica, Encephaloceles, Encephalopathy, Encephalotrigeminal Angiomatosis, Epilepsy, Erb-Duchenne and Dejerine-Klumpke Palsies, Erb's Palsy, Fabry's Disease, Fahr's Syndrome, Fainting, Familial Dysautonomia, Familial Hemangioma, Familial Idiopathic Basal Ganglia, Calcification, Familial Periodic Paralyses, Familial Spastic Paralysis, Febrile Seizures, Fisher Syndrome, Floppy Infant Syndrome, Friedreich's Ataxia, Frontotemporal, Dementia, Gaucher's Disease, Gerstmann's Syndrome, Gerstmann-Straussler-Scheinker, Disease, Giant Cell Arteritis, Giant Cell Inclusion Disease, Globoid Cell Leukodystrophy, Glossopharyngeal Neuralgia, Guillain-Barre Syndrome, Hallervorden-Spatz Disease, Head Injury, Headache, Hemicrania Continua, Hemifacial Spasm, Hemiplegia Alterans, Hereditary Neuropathies, Hereditary Spastic Paraplegia, Heredopathia Atactica Polyneuritiformis, Herpes Zoster, Herpes Zoster Oticus, Hirayama Syndrome, Holmes-Adie syndrome, Holoprosencephaly, HTLV-1 Associated, Myelopathy, Huntington's Disease, Hydranencephaly, Hydrocephalus, H-fydrocephalus-Normal Pressure, Hydromyelia, Hyperactivity, Hypercortisolism, Hypersomnia, Hypertonia, Hypotonia, —Infantile, Hypoxia, Immune-Mediated Encephalomyelitis, Inclusion Body Myositis, Incontinentia Pigmenti, Infantile Hypotonia, Infantile Neuroaxonal Dystrophy, Infantile Phytanic Acid Storage Disease, Infantile Refsum Disease, Infantile Spasms, Inflammatory Myopathy, Iniencephaly, Intestinal Lipodystrophy, Intracranial Cysts, Intracranial Hypertension, Isaac's Syndrome, Joubert Syndrome, Kearns-Sayre Syndrome, Kennedy's Disease, Kinsbourne syndrome, Kleine-Levin Syndrome, Klippel-Feil Syndrome, Klippel-Trenaunay Syndrome (KTS), Klüver-Bucy Syndrome, Korsakoffs Amnesic Syndrome, Krabbe Disease, Kugelberg-Welander Disease, Kuru, Lambert-Eaton Myasthenic Syndrome, Landau-Kleffner Syndrome, Lateral Femoral, Cutaneous Nerve Entrapment, Lateral Medullary Syndrome, Learning Disabilities, Leigh's Disease, Lennox-Gastaut Syndrome, Lesch-Nyhan Syndrome, Leukodystrophy, Levine-Critchley Syndrome, Lewy Body Dementia, Lipid Storage Diseases, Lissencephaly, Locked-In Syndrome, Lou Gehrig's Disease, Lupus—Neurological, Sequelae, Lyme Disease—Neurological Complications, Machado-Joseph Disease, Macrencephaly, Mania, Megalencephaly, Melkersson-Rosenthal Syndrome, Meningitis, Meningitis and Encephalitis, Menkes Disease, Meralgia Paresthetica, Metachromatic, Leukodystrophy, Microcephaly, Migraine, Miller Fisher Syndrome, Mini-Strokes, Mitochondrial Myopathies, Mobius Syndrome, Monomelic Amyotrophy, Motor Neuron Diseases, Moyamoya Disease, Mucolipidoses, Mucopolysaccharidoses, Multifocal Motor Neuropathy, Multi-Infarct Dementia, Multiple Sclerosis, Multiple System Atrophy, Multiple System Atrophy with Orthostatic Hypotension, Muscular Dystrophy, Myasthenia—Congenital, Myasthenia Gravis, Myelinoclastic Diffuse Sclerosis, Myoclonic Encephalopathy of Infants, Myoclonus, Myopathy, Myopathy—Congenital, Myopathy-Thyrotoxic, Myotonia, Myotonia Congenita, Narcolepsy, Neuroacanthocytosis, Neurodegeneration with Brain Iron Accumulation, Neurofibromatosis, Neuroleptic Malignant Syndrome, Neurological Complications of AIDS, Neurological Complications Of Lyme Disease, Neurological Consequences of Cytomegalovirus Infection, Neurological Manifestations of Pompe Disease, Neurological Sequelae Of Lupus, Neuromyelitis Optica, Neuromyotonia, Neuronal Ceroid, Lipofuscinosis, Neuronal Migration Disorders, Neuropathy-Hereditary, Neurosarcoidosis, Neurotoxicity, Nevus Cavernosus, Niemann-Pick Disease, Normal Pressure Hydrocephalus, Occipital Neuralgia, Obesity, Occult Spinal Dysraphism Sequence, Ohtahara Syndrome, Olivopontocerebellar Atrophy, Opsoclonus Myoclonus, Orthostatic Hypotension, O'Sullivan-McLeod Syndrome, Overuse Syndrome, Pain—Chronic, Paine, Pantothenate Kinase-Associated Neurodegeneration, Paraneoplastic Syndromes, Paresthesia, Parkinson's Disease, Paroxysmal Choreoathetosis, Paroxysmal Hemicrania, Parry-Romberg, Pelizaeus-Merzbacher Disease, Pena Shokeir II Syndrome, Perineural Cysts, Periodic Paralyses, Peripheral Neuropathy, Periventricular Leukomalacia, Persistent Vegetative State, Pervasive Developmental Disorders, Phytanic Acid Storage Disease, Pick's Disease, Pinched Nerve, Piriformis Syndrome, Pituitary Tumors, Polymyositis, Pompe Disease, Porencephaly, Postherpetic Neuralgia, Postinfectious Encephalomyelitis, Post-Polio Syndrome, Postural Hypotension, Postural Orthostatic, Tachycardia Syndrome, Postural Tachycardia Syndrome, Primary Dentatum Atrophy, Primary Lateral Sclerosis, Primary Progressive Aphasia, Prion Diseases, Progressive Hemifacial Atrophy, Progressive Locomotor Ataxia, Progressive Multifocal, Leukoencephalopathy, Progressive Sclerosing Poliodystrophy, Progressive Supranuclear, Palsy, Prosopagnosia, Pseudotumor Cerebri, Ramsay Hunt Syndrome I (formerly known as), Ramsay Hunt Syndrome II (formerly known as), Rasmussen's Encephalitis, Reflex Sympathetic Dystrophy Syndrome, Refsum Disease, Refsum Disease—Infantile, Repetitive Motion Disorders, Repetitive Stress Injuries, Restless Legs Syndrome, Retrovirus-Associated Myelopathy, Rett Syndrome, Reye's Syndrome, Riley-Day Syndrome, Sacral Nerve Root Cysts, Saint Vitus Dance, Salivary Gland Disease, Sandhoff Disease, Schilder's Disease, Schizencephaly, Seitelberger Disease, Seizure Disorder, Semantic Dementia, Septo-Optic Dysplasia, Shaken Baby Syndrome, Shingles Shy-Drager Syndrome, Sjogren's Syndrome, Sleep Apnea, Sleeping Sickness, Sotos Syndrome, Spasticity, Spina Bifida, Spinal Cord Infarction, Spinal Cord Injury, Spinal Cord Tumors, Spinal Muscular Atrophy, Spinocerebellar Atrophy, Spinocerebellar, Degeneration, Steele-Richardson-Olszewski Syndrome, Stiff-Person Syndrome, Striatonigral Degeneration, Stroke, Sturge-Weber Syndrome, Subacute Sclerosing Panencephalitis, Subcortical Arteriosclerotic Encephalopathy, SUNCT Headache Swallowing Disorders, Sydenham Chorea, Syncope, Syphilitic Spinal Sclerosis, Syringohydromyelia, Syringomyelia, Systemic Lupus Erythematosus, Tabes Dorsalis Tardive Dyskinesia, Tarlov Cysts, Tay-Sachs Disease, Temporal Arteritis, Tethered Spinal Cord Syndrome, Thomsen's Myotonia, Thoracic Outlet Syndrome, Thyrotoxic Myopathy, Tic Douloureux, Todd's Paralysis, Tourette Syndrome, Transient Ischemic Attack, Transmissible Spongiform Encephalopathies, Transverse Myelitis, Traumatic Brain Injury, Tremor, Trigeminal Neuralgia, Tropical Spastic Paraparesis, Tuberous Sclerosis, Vascular Erectile Tumor, Vasculitis including Temporal Arteritis, Von Economo's Disease, Von Hippel-Lindau Disease (VHL), Von Recklinghausen's Disease, Wallenberg's Syndrome, Werdnig-Hoffman Disease, Wernicke-Korsakoff Syndrome, West Syndrome, Whiplash, Whipple's Disease, Williams Syndrome, Wilson's Disease, X-Linked Spinal and Bulbar Muscular Atrophy, or Zellweger Syndrome.

The term "bioactive agent" is used to describe an agent, other than a compound according to the present disclosure, which is used in combination with the compounds of the present disclosure as an agent with biological activity to assist in effecting an intended therapy, inhibition and/or prevention/prophylaxis for which the present compounds are used.

The term "pharmaceutically acceptable salt" is used throughout the specification to describe, where applicable, a salt form of one or more of the compounds described herein which are presented to increase the solubility of the compound in the gastric juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present disclosure.

Examples

The bifunctional compounds of the instant disclosure are effective in Tau degradation. Exemplary compounds are presented in Tables 1 with data of some exemplary compounds in. In vivo, in vivo, and ex vivo studies showing degradation of tau protein are illustrated in the figures.

General Methods of Chemical Synthesis

The synthesis of the claimed chimeric compounds can be carried out according to the general synthetic procedures known in literature. Synthetic routes shown in the schemes in the present disclosure are described as one of the methods that can be used to obtain the desired compounds. Other methods can also be used for those skilled in the art of synthesis. The ULM and PTM described in schemes only represent one of many ULMs and PTMs in this application.

LC-MS Method for Purity Analysis (Quality Control)

LCMS Method:

Instrumentations: Agilent infinity 1260 LC; Agilent 6230 TOF mass spectrometer

The analysis is conducted on a Poroshell 120 EC C18 column (50 mm×3.0 mm internal diameter 2.7 μm packing diameter) at 45° C.

The solvents employed are:

A=0.1% v/v solution of fonnic acid in water.

B=0.1% v/v solution of formic acid in acetonitrile.

The gradient employed are as follows:

| Time (minutes) | Flow Rate (mL/min) | % A | % B |
|---|---|---|---|
| 0 | 1 | 95 | 5 |
| 0.5 | 1 | 95 | 5 |
| 3.0 | 1 | 1 | 99 |
| 4.0 | 1 | 1 | 99 |
| 4.1 | 1 | 95 | 5 |
| 4.5 | 1 | 95 | 5 |

The UV detection is an averaged signal from wavelength of 210 nm to 350 nm and mass spectra are recorded on a mass spectrometer using positive mode electrospray ionization.

Abbreviations

ACN: acetonitrile
$Boc_2O$: di-tert-butyl dicarbonate
DCM: dichloromethane.
DIPEA: N,N-diisopropylethylamine
DMA: N,N-dimethylacetamide
DMF: N,N-dimethylformamide
EA: ethyl acetate
HATU: 2-(7-aza-1H-benzotriazole-1-yl)-1,1,3,3-tetramethyluronium hexafluorophosphate
HPLC: high-performance liquid chromatography
LC-MS: liquid chromatography-mass spectrometry
Min: minutes
MTBE: methyl tert-butyl ether
PE: petroleum ether
RT: room temperature
SPB: sodium perborate
tBu: tert-butyl
TBACl: tetra-butyl ammonium chloride
TFA: trifluoroacetic acid
THF: tetrahydrofuran
TLC: thin layer chromatography
TMS: trimethylsilyl
$t_R$: retention rime
TsCl: p-toluene sulfonyl chloride Intermediates of Ubiquitin E3 Ligase Targeting Moiety (ULM) and Protein Targeting Moiety (PTM)

Intermediate 1: (2S, 4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide hydrochloride (ULM-1)

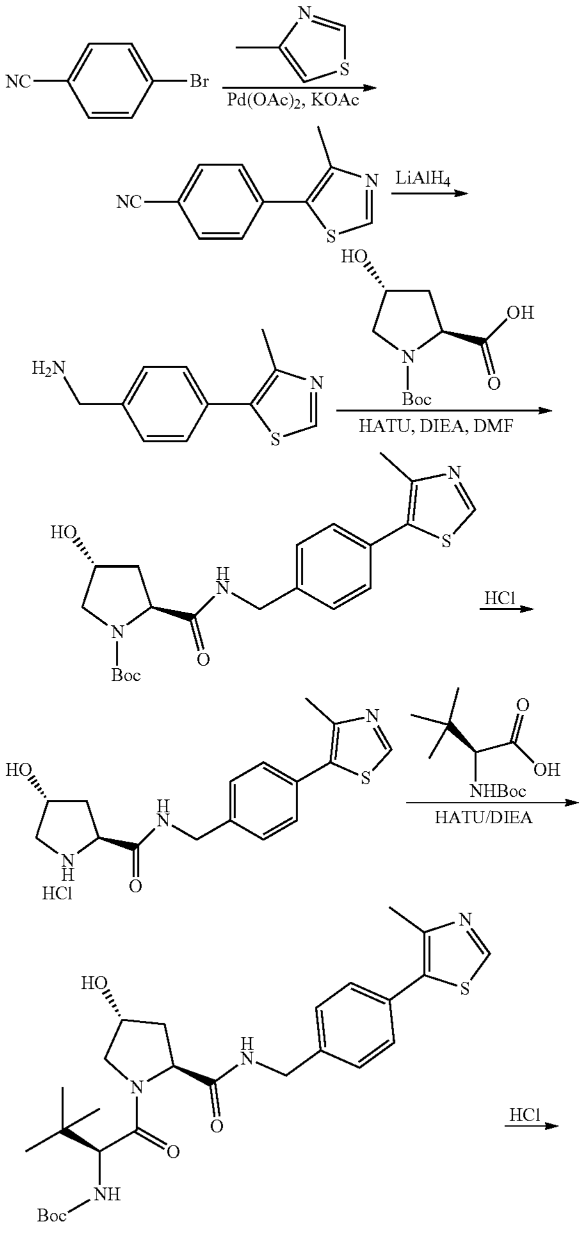

-continued

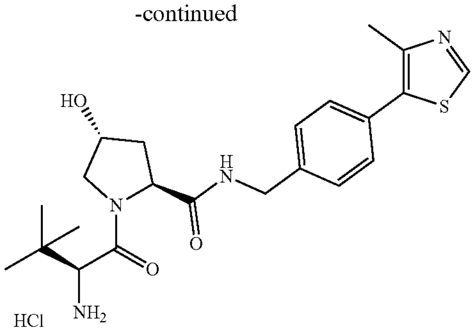

HCl

Step 1: Preparation of 4-(4-methyl-1,3-thiazol-5-yl)benzonitrile

To a stirred solution of 4-bromobenzonitrile (20 g, 109.88 mmol) in DMA (250 mL) under a nitrogen atmosphere was added 4-methyl-1,3-thiazole (21.88 g, 220.67 mmol), palladium (II) acetate (743 mg, 3.31 mmol) and potassium acetate (21.66 g, 220.71 mmol) at room temperature. The resulting mixture was heated to 150° C. and stirred at this temperature for 5 hours, at which time LC-MS indicated completion of the reaction. The mixture was cooled to room temperature, diluted with 1 L of water and extracted with ethyl acetate (300 mL×3). The organic layers were combined, washed with brine (200 mL), dried over anhydrous sodium sulfate and then concentrated under reduced pressure to give a crude residue, which was purified by flash silica gel column chromatography (eluent: ethyl acetate/petroleum ether, v:v=1:5) to give the titled compound (yield: 91%) as a white solid.

Step 2: Preparation of of [4-(4-methyl-1,3-thiazol-5-yl)phenyl]methanamine

To a stirred solution of 4-(4-methyl-1,3-thiazol-5-yl)benzonitrile (35 g, 174.77 mmol) in tetrahydrofuran (1000 mL) was added $LiAlH_4$ (20 g, 526.32 mmol) in portions at 0° C. in 10 minutes under a nitrogen atmosphere. The resulting mixture was then stirred at 60° C. for 3 hours, at which time LC-MS indicated completion of reaction. The mixture was cooled to 0° C., then quenched by the addition of water (20 mL, added slowly), aq. solution of NaOH (15%, 20 mL) and water (60 mL). The resulting mixture was then extracted with ethyl acetate (300 mL×2). The organic layers were combined, washed with brine (100 mL), dried over anhydrous sodium sulfate and then concentrated under reduced pressure to give a crude residue, which was purified by flash silica gel column chromatography (eluent: dichloromethane/methanol (v:v=10:1)) to give the titled compound (yield: 56%) as a yellow oil.

Step 3: Preparation of tert-butyl (2S,4R)-4-hydroxy-2-([[4-(4-methyl-1,3-thiazol-5-yl)phenyl]methyl]carbamoyl)pyrrolidine-1-carboxylate To a stirred solution of (2S,4R)-1-[(tert-butoxy)carbonyl]-4-hydroxypyrrolidine-2-carboxylic acid (2.7 g, 11.68 mmol) in N,N-dimethylformamide (20 mL) was added DIPEA (2.52 g, 19.50 mmol), HATU (4.47 g, 11.76 mmol) and [4-(4-methyl-1,3-thiazol-5-yl)phenyl]methanamine (2 g, 9.79 mmol) at room temperature. The resulting mixture was stirred at room temperature overnight, at which time LC-MS indicated completion of reaction. The reaction mixture was diluted with 20 mL of water and extracted with ethyl acetate (50 mL×3). The organic layers were combined, washed with brine (50 mL), dried over anhydrous sodium sulfate and then concentrated under reduced pressure to give a crude residue, which was purified by flash silica gel column chromatography (eluent: dichloromethane/methanol (v:v=20:1)) to give the titled compound (yield: 56%) as a yellow solid.

Step 4: Preparation of (2S,4R)-4-hydroxy-N-[[4-(4-methyl-1,3-thiazol-5-yl)phenyl]methyl]pyrrolidine-2-carboxamide hydrochloride To 1 L round bottom flask containing tert-butyl (2S,4R)-4-hydroxy-2-([[4-(4-methyl-1,3-thiazol-5-yl)phenyl]methyl]carbamoyl)pyrrolidine-1-carboxylate (45 g, 107.78 mmol) in dioxane was added hydrogen chloride in dioxane (4N, 300 mL). The resulting solution was stirred for 2 hours at room temperature. The solids were collected by filtration to give the titled product (yield: 98%) as a yellow solid.

Step 5: Preparation of tert-butyl N-[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamate To a stirred solution of (2S)-2-{[(tert-butoxy)carbonyl]amino}-3,3-dimethylbutanoic acid (15.7 g, 68.0 mmol) in N,N-dimethylformamide (500 mL) was added DIPEA (29.2 g, 225.9 mmol), HATU (25.9 g, 68.1 mmol) and (2S,4R)-4-hydroxy-N-{[4-(4-methyl-1,3-thiazol-5-yl)-phenyl]methyl} pyrrolidine-2-carboxamide hydrochloride (20.0 g, 56.5 mmol) at room temperature.

The resulting solution was stirred at room temperature for 16 hours, LC-MS indicated formation of the desired product. The reaction mixture was diluted by water (200 mL) and extracted with ethyl acetate (200 mL×3). The organic layers were combined, washed with saturated aqueous solution of sodium chloride (50 mL×2), dried over anhydrous sodium sulfate and then concentrated under reduced pressure to give a crude residue, which was purified by flash silica gel chromatography (eluent: ethyl acetate/petroleum ether (v:v=2:1)) to give the title compound (yield: 51%) as a yellow solid.

Step 6: Synthesis of (2S, 4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide hydrochloride (ULM-1)

To a stirred solution of tert-butyl N-[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamate (12 g, 22.61 mmol) in dioxane (20 mL) was added a solution of hydrogen chloride in dioxane (4N, 80 mL) at room temperature. The resulting solution was stirred at room temperature for 2 hours, at which time LC-MS indicated completion of reaction. Precipitated solids were collected by filtration to give the titled product (yield: 48%) as a yellow solid.

d: 48%) as a yellow solid.

$^1$HNMR (400 MHz, $CD_3OD$): δ 9.84-9.82 (s, 1H), 7.58-7.54 (m, 4H), 4.71-4.41 (m, 4H), 4.13-4.08 (m, 1H), 3.86-3.71 (m, 2H), 3.36 (s, 1H), 2.60-2.58 (s, 3H), 2.35-2.07 (m, 2H), 1.19-1.12 (m, 9H). LC-MS ($ES^+$): m/z 431.11 [$MH^+$], $t_R$=0.73 min.

Intermediate 2: (2S,4R)-1-[(S)-2-amino-3,3-dimethylbutanoyl]-4-hydroxy-N-[(S)-1-(4-(4-methylthiazol-5-yl)phenyl)ethyl]-pyrrolidine-2-carboxamide hydrochloride (ULM-2)

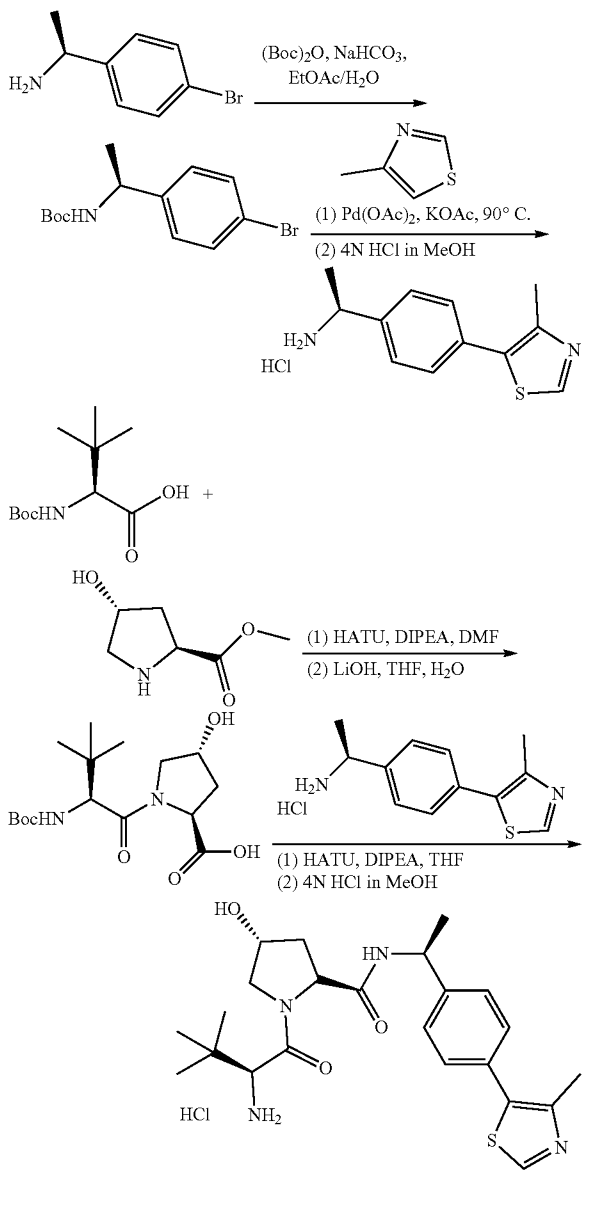

Step 1: Preparation of (S)-tert-butyl-1-(4-bromophenyl)-ethyl carbamate

To a mixture of (S)-1-(4-bromophenyl)ethanamine (3.98 g, 19.9 mmol) and $NaHCO_3$ (1.24 g, 14.8 mmol) in $H_2O$ (10 mL) and ethyl acetate (10 mL) was added $(Boc)_2O$ (5.20 g, 23.8 mmol) at 5° C. The reaction was continued to react for 2 hours. TLC showed reaction was complete. The reaction mixture was filtered. The solid was collected and suspended in a mixture of hexane (10 mL) and $H_2O$ (10 mL) for 0.5 hours. The mixture was filtered and the solid was collected and dried in oven at 50° C. to afford the title compound as white solid (5.9 g, 98.7%).

$^1$HNMR (400 MHz, DMSO-$d_6$): δ 1.28 (d, J=7.2 Hz, 3H), 1.36 (s, 9H), 4.55-4.60 (m, 1H), 7.25 (d, J=8.4 Hz, 2H), 7.39 (br, 1H), 7.49 (d, J=8.4 Hz, 2H).

Step 2: Preparation of (S)-1-(4-(4-methylthiazol-5-yl)phenyl)ethanamine hydrochloride A mixture of (S)-tert-butyl-1-(4-bromophenyl)-ethyl carbamate (4.0 g, 13.3 mmol), 4-methylthiazole (2.64 g, 26.6 mmol), palladium (II) acetate (29.6 mg, 0.13 mmol) and potassium acetate (2.61 g, 26.6 mmol) in DMF (10 mL) was stirred at 90° C. under N2 for 18 hours. After cooling to ambient temperature, the reaction mixture was filtered. To the filtrate was added $H_2O$ (50 mL) and the resulting mixture was stirred at ambient temperature for 4 hours. The reaction mixture was filtered. The solid was collected by filtration and dried in oven at 50° C. to afford (S)-tert-butyl 1-(4-(4-methylthiazol-5-yl)phenyl)ethylcarbamate (3.48 g, 82.3%) as gray solid.

$^1$HNMR (400 MHz, DMSO-$d_6$): δ 1.33 (d, J=7.2 Hz, 3H), 1.38 (s, 9H), 2.46 (s, 3H), 4.64-4.68 (m, 1H), 7.23 (br d, 0.5H), 7.39 (d, J=8 Hz, 2H), 7.44 (d, J=8.4 Hz, 2H), 7.50 (br d, 0.5H), 8.99 (s, 1H); LC-MS $[M+1]^+$: 319.5

This solid material (1.9 g, 6.0 mmol) was dissolved in 4N hydrochloride in methanol (5 mL, 20 mmol, prepared from acetyl chloride and methanol) and the mixture was stirred at ambient temperature for 3 h then concentrated and triturated with ether. The mixture was filtered and the solid was collected and dried in oven at 60° C. to afford (S)-1-(4-(4-methylthiazol-5-yl)phenyl)ethanamine hydrochloride (1.3 g, 85%) as a light green solid.

$^1$HNMR (400 MHz, DMSO-d6): δ 1.56 (d, J=6.8 Hz, 3H), 2.48 (s, 3H), 4.41-4.47 (m, 1H), 7.57 (d, J=8.4 Hz, 2H), 7.67 (d, J=8.4 Hz), 8.75 (s, 3H), 9.17 (s, 1H); LC-MS [M+1]+: 219.2

Step 3: Preparation of (2S, 4R)-1-{(S)-2-[(tert-butoxycarbonyl)amino]-3,3-dimethylbutanoyl}-4-hydroxypyrrolidine-2-carboxylic acid HATU (2.15 g, 5.7 mmol) was added to a solution of (S)-2-(tert-butoxycarbonyl)amino-3,3-dimethylbutanoic acid (1.25 g, 5.4 mol), (2S,4R)-methyl 4-hydroxypyrrolidine-2-carboxylate hydrochloride (0.98 g, 5.4 mmol) and DIPEA (2.43 g, 18.9 mmol) in DMF (10 mL) at 0° C. under nitrogen. The mixture was stirred at ambient temperature for 18 hours. TLC showed the reaction complete. The reaction mixture was quenched with water (30 mL) and extracted with ethyl acetate (15 mL×4). The combined organic layer was washed with the 5% citric acid (10 mL×2), saturated $NaHCO_3$ solution (10 mL×2), brine (10 mL×2) and dried over $Na_2SO_4$. The organic solution was filtered and concentrated to afford (2S, 4R)-methyl 1-{(S)-2-[(tert-butoxycarbonyl)amino]-3,3-dimethylbutanoyl}-4-hydroxypyrrolidine-2-carboxylate as pale yellow oil (1.93 g, 100% yield). This crude product (1.93 g) and lithium hydroxide hydrate (2.2 g, 54 mmol) were taken into THF (20 mL) and $H_2O$ (10 mL). The resulting mixture was stirred at ambient temperature for 18 hours. THF was removed by concentration. The residue was diluted with ice-water (10 mL) and slowly adjusted to pH 2-3 with 3N HCl. The resulting suspension was filtered, washed with $H_2O$ (6 mL×2). The solid was collected by filtration and dried in oven at 50° C. to afford the title compound as a white solid (1.4 g, 75% for two steps).

$^1$HNMR (400 MHz, DMSO-$d_6$): δ 6.50 (d, J=9.6 Hz, 1H), 5.19 (br s, 1H), 4.32 (br s, 1H), 4.25 (t, J=8.4 Hz, 1H), 4.16

(d, J=9.2 Hz, 1H), 3.57-3.66 (m, 2H), 2.08-2.13 (m, 1H), 1.85-1.91 (m, 1H), 1.38 (s, 9H), 0.94 (s, 9H).

Step 4: Preparation of (2S,4R)-1-[(S)-2-amino-3,3-dimethylbutanoyl]-4-hydroxy-N-[(S)-1-(4-(4-methylthiazol-5-yl)phenyl)ethyl]-pyrrolidine-2-carboxamide hydrochloride (ULM-2)

HATU (1.6 g, 4.2 mmol) was added to a stirred solution containing (2S, 4R)-1-{(S)-2-[(tert-butoxycarbonyl)amino]-3,3-dimethylbutanoyl}-4-hydroxypyrrolidine-2-carboxylic acid (1.21 g, 3.5 mmol), (S)-1-(4-(4-methylthiazol-5-yl) phenyl)ethanamine hydrochloride (0.9 g, 3.5 mmol), and DIPEA (1.36 g, 10.5 mmol) in anhydrous THF (15 mL) at 0° C. The resulting mixture was allowed to warm up to ambient temperature and continued to stir for 2 hours. TLC showed reaction completed. THF was removed by concentration. To the residue was added water (15 mL) and the resulting mixture was stirred for 4 hours. The resulting mixture was filtered. The solid was collected and dried in oven at 50° C. to give a white solid. This solid was taken into methanol (10 mL) and activated carbon (150 mg) was added. The resulting mixture was heated at 80° C. and stirred for 1 h. The mixture was filtered while it was hot. Water (5 mL) was added to the filtrate at 80° C. The resulting mixture was cooled to ambient temperature and continued to stir for 18 hours. The suspension was filtered. The solid was collected and dried in oven at 50° C. to afford tert-butyl-{(S)-1-[(2S, 4R)-4-hydroxy]-2-[(S)-1-(4-(4-methylthiazol-5-yl)phenyl)-ethylcarbamoyl]pyrrolidin-1-yl}-3,3-dimethyl-1-oxobutan-2-yl-carbamate (1.41 g, 74.2%) as a white solid.

$^1$H NMR (400 MHz, $CDCl_3$): δ 1.05 (s, 9H), 1.42 (s, 9H), 1.47 (d, J=7.2 Hz, 3H), 2.04-2.10 (m, 1H), 2.53 (s, 3H), 2.58-2.64 (m, 1H), 3.23 (s, 1H), 3.58 (dd, J=11.2 Hz, 3.2 Hz, 1H), 4.11 (d, J=11.6 Hz, 1H), 4.22 (d, J=9.2 Hz, 1H), 4.51 (br, 1H), 4.79 (t, J=8.0 Hz, 1H), 5.04-5.11 (m, 1H), 5.22 (d, J=8.8 Hz, 1H), 7.36-7.42 (m, 4H), 7.61 (d, J=7.6 Hz 1H), 8.68 (s, 1H).

This solid (1.04 g, 1.9 mmol) was dissolved in 4N hydrogen chloride in methanol (3.0 mL) and the mixture was stirred at ambient temperature for 3 hours. TLC showed reaction complete. The reaction mixture was concentrated to remove all volatiles under reduced pressure to give a light yellow solid. The solid was added to TBME (5 mL) and the resulting mixture was stirred at ambient temperature for 4 hours. The reaction mixture was filtered and the solid was collected and dried in oven at 50° C. to afford the title compound (0.92 g, 100%).

$^1$H NMR (400 MHz, DMSO-d6): δ 1.03 (s, 9H), 1.38 (d, J=7.2 Hz, 3H), 1.72-1.79 (m, 1H), 2.09-2.14 (m, 1H), 2.49 (s, 3H), 3.48-3.52 (m, 1H), 3.75-3.79 (m, 1H), 3.88-3.90 (m, 1H), 4.31 (br, 1H), 4.56 (t, J=8.4 Hz, 1H), 4.89-4.95 (m, 1H), 7.41 (d, J=8.4 Hz, 2H), 7.47 (d, J=8.4 Hz, 2H), 8.20 (br, 3H), 8.67 (d, J=7.6 Hz, 1H), 9.22 (s, 1H); $^{13}$C NMR (400 MHz, DMSO-d6): δ 170.7, 167.1, 153.0, 146.5, 145.7, 132.5, 129.4, 129.3, 126.9, 69.4, 59.3, 58.5, 56.9, 48.3, 38.4, 34.8, 26.6, 23.0, 15.7; LC-MS $[M+1]^+$: 445.6

Intermediate 3: (2S,4R)-4-hydroxy-N-(2-hydroxy-4-(4-methylthiazol-5-yl)benzyl)-1-((S)-3-methyl-2-(1-oxoisoindolin-2-yl)butanoyl)pyrrolidine-2-carboxamide (ULM-3)

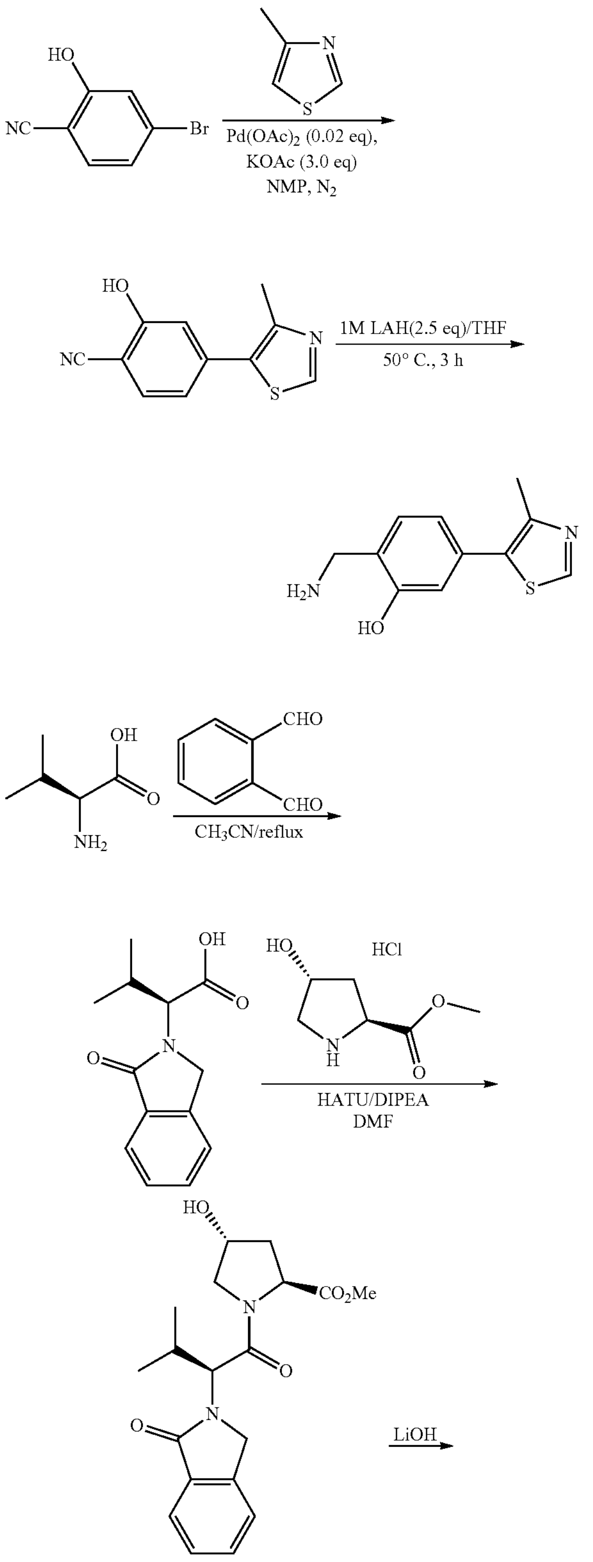

-continued

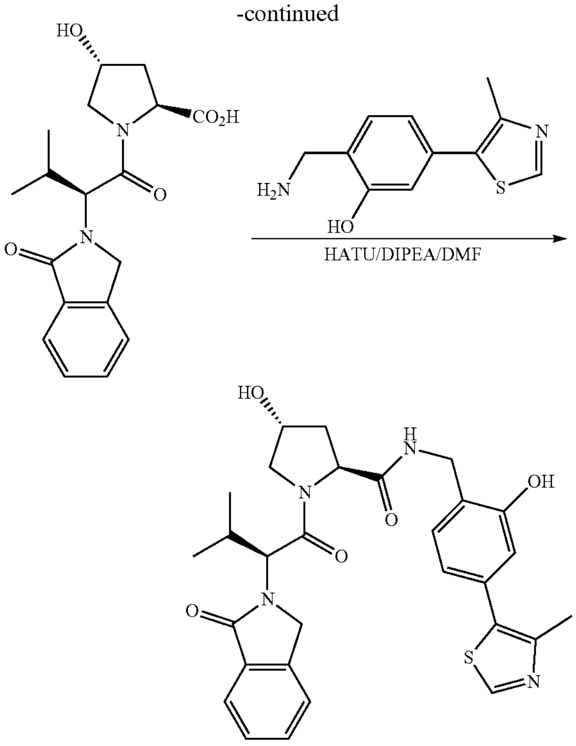

Step 1: Preparation of 2-hydroxy-4-(4-methylthiazol-5-yl) benzonitrile

A mixture of 4-bromo-2-hydroxybenzonitrile (15 g, 76 mmol), 4-methylthiazole (14 mL, 152 mmol), KOAc (14.9 g, 152 mmol) and $Pd(OAc)_2$ (0.34 g, 1.52 mmol) in dry NMP (125 mL) was stirred at 110° C. for 6 hours under nitrogen atmosphere. TLC showed the reaction was complete. The mixture was first cooled to room temperature, then partitioned between EtOAc and water. The combined organic fraction was filtered and the filtrate was washed with water, brine, dried over anhydrous $Na_2SO_4$, and concentrated. The residue was dissolved in toluene (100 mL) and re-evaporated to afford the crude product. The crude product was treated with cold MeOH (80 mL). The resulting precipitate was collected by filtration, washed with MeOH (20 mL), and dried under vacuum to afford the title compound as a light yellow solid (10.5 g, 64%).

LC/MS: 217.2 $[M+1]^+$.

$^1$HNMR (400 MHz, DMSO-d6): δ2.49 (s, 3H), 7.07 (dd, J=8.0, 1.6 Hz, 1H), 7.13 (d, J=1.6 Hz, 1H), 7.70 (d, J=8.0 Hz, 1H), 9.07 (s, 1H), 11.34 (s, 1H).

Step 2: Preparation of 2-(aminomethyl)-5-(4-methylthiazol-5-yl)phenol

To a solution of 2-hydroxy-4-(4-methylthiazol-5-yl)benzonitrile (2.9 g, 13.41 mmol) in dry THF (150 mL), was added $LiAlH_4$ (1.5 g, 40.23 mmol) in portions at 0° C. The resulting mixture was stirred at 50° C. for 3 h under nitrogen atmosphere. TLC showed the reaction was complete. The mixture was cooled in ice-water bath then $Na_2SO_4 \cdot 10H_2O$ (5 g) was added carefully and stirred at this temperature for 1 h. The mixture was filtered and the filter cake was washed with 10% MeOH in DCM for four times. The combined filtrates were concentrated to afford the crude 2-(aminomethyl)-5-(4-methylthiazol-5-yl)phenol as a light yellow solid (2.0 g, 68%). It was used in next step without further purification.

LCMS: 221.2$[M+H]^+$.

$^1$HNMR (400 MHz, DMSO-d6): δ2.43 (s, 3H), 3.54 (br, 2H), 6.11 (d, J=7.2 Hz, 1H), 6.40 (d, J=11.6 Hz, 1H), 6.83 (d, J=7.6 Hz, 1H), 8.81 (s, 1H).

Step 3: Preparation of (S)-3-methyl-2-(1-oxoisoindolin-2-yl) butanoic acid

L-Valine (4.37 g, 37.3 mmol) was added to a solution of phthalic dicarboxaldehyde (5.0 g, 37.3 mmol) in acetonitrile (350 mL). The resulting mixture was refluxed for 5 hours. The reaction mixture was filtered whilst hot and the filtrate was cooled to room temperature slowly. The resulting precipitate was filtered and dried to afford (S)-3-methyl-2-(1-oxoisoindolin-2-yl)butanoic acid as a white solid (6.45 g, 74%).

$^1$HNMR (400 MHz, DMSO-d6): δ 0.85 (d, J=6.8 Hz, 3H), 1.0 (d, J=6.8 Hz, 3H), 2.25-2.34 (m, 11H), 4.51 (d, J=4.4 Hz, 1H), 4.54 (d, J=3.6 Hz, 1H), 4.64 (d, J=18.0 Hz, 1H), 7.48-7.54 (m, 1H), 7.63 (d, J=3.6 Hz, 2H), 7.72 (d, J=7.6 Hz, 1H), 13.01 (br, 1H).

Step 4: Preparation of (2S,4R)-methyl 4-hydroxy-1-((S)-3-methyl-2-(1-oxoisoindolin-2-yl)butanoyl) pyrrolidine-2-carboxylate To a solution containing 4-hydroxy-L-proline methyl ester hydrochloride (1.0 g, 5.52 mmol), (S)-3-methyl-2-(1-oxoisoindolin-2-yl)butanoic acid (1.16 g, 4.97 mmol), and DIPEA (2.58 g, 20 mmol) in dry DMF (15 mL) was added HATU (3.8 g, 10 mmol) at 0° C. The resulting mixture was stirred at room temperature for 2 hours. The mixture was partitioned between EtOAc and water. The organic phase was washed with water, brine and dried over anhydrous $Na_2SO_4$. The residue was purified by silica gel chromatography using 30-50% EtOAc in hexane as eluent to afford the title compound as a light yellow solid (1.21 g, 67.6%).

LCMS: 361.3$[M+1]^+$.

Step 5: Preparation of (2S,4R)-4-hydroxy-1-((S)-3-methyl-2-(1-oxoisoindolin-2-yl)butanoyl)pyrrolidine-2-carboxylic acid A mixture containing (2S,4R)-methyl 4-hydroxy-1-((S)-3-methyl-2-(1-oxoisoindolin-2-yl)butanoyl)pyrrolidine-2-carboxylate (1.2 g, 3.33 mmol), $LiOH \cdot H_2O$ (559 mg, 13.32 mmol) in THF (20 mL) and $H_2O$ (10 mL) was stirred at room temperature for 2 hours. TLC showed the reaction was complete. The reaction mixture was acidified with 1N HCl to pH 1-2, and extracted with EtOAc. The combined organic layer was washed with brine, dried over $Na_2SO_4$ and concentrated to afford the title compound as a light yellow solid (1.05 g, 91% yield).

$^1$HNMR (400 MHz, $CDCl_3$): δ0.91 (d, J=6.4 Hz, 3H), 1.05 (d, J=6.8 Hz, 3H), 2.30 (dd, J=8.4, 2.8 Hz, 2H), 2.44-2.50 (m, 1H), 3.75 (dd, J=11.2, 3.2 Hz, 1H), 4.42 (d, J=17.6 Hz, 1H), 4.50-4.55 (m, 2H), 4.66 (t, J=8.4 Hz, 1H), 4.75 (d, J=17.6 Hz, 1H), 4.83 (d, J=11.2 Hz, 1H), 7.42-7.45 (m, 2H), 7.51-7.56 (m, 1H), 7.78 (d, J=7.6 Hz, 1H).

Step 6: Preparation of (2S,4R)-4-hydroxy-N-(2-hydroxy-4-(4-methylthiazol-5-yl)benzyl)-1-((S)-3-methyl-2-(1-oxoisoindolin-2-yl)butanoyl)pyrrolidine-2-carboxamide To a solution containing (2S,4R)-4-hydroxy-1-((S)-3-methyl-2-(1-oxoisoindolin-2-yl)butanoyl)pyrrolidine-2-carboxylic acid (1.0 g, 2.89 mmol), 2-(aminomethyl)-5-(4-methylthiazol-5-yl)phenol (954 mg, 4.33 mmol), and DIPEA (1.5 g, 11.55 mmol) in DMF (20 mL) was added HATU (2.2 g, 5.77 mmol) at 0° C. The resulting mixture was stirred at room temperature for 1 h. TLC showed the reaction was complete. The mixture was partitioned between EtOAc and water. The organic phase was washed with water, brine and dried over anhydrous $Na_2SO_4$. The residue was purified by silica gel column chromatography using 2-5% MeOH in DCM to afford the title compound as a light yellow solid (650 mg, 43% yield).

LCMS: 549.2$[M+H]^+$ $^1$HNMR (400 MHz, $CDCl_3$): δ0.80 (d, J=6.8 Hz, 3H), 0.88 (d, J=6.8 Hz, 3H), 1.96-2.01 (m, 1H), 2.34-2.40 (m, 1H), 2.47-2.53 (m, 4H), 3.61 (dd, J=11.6, 3.6 Hz, 1H), 4.29-4.37 (m, 2H), 4.38-4.41 (m, 1H), 4.47-4.50 (m, 2H), 4.64-4.69 (m, 2H), 4.72 (s, 1H), 6.90 (dd, J=8.0, 2.0 Hz, 1H), 7.01 (d, J=2.0 Hz, 1H), 7.14 (d, J=8.0 Hz, 1H), 7.39-7.44 (m, 2H), 7.51-7.54 (m, 1H), 7.76 (d, J=7.6 Hz, 1H), 8.03 (t, J=6.4 Hz, 1H), 8.66 (s, 1H), 9.27 (br, 1H).

Intermediate 4: (2R,4S)-1-[(S)-2-amino-3,3-dimethylbutanoyl]-4-hydroxy-N-[(S)-1-(4-(4-methylthiazol-5-yl)phenyl)ethyl]-pyrrolidine-2-carboxamide hydrochloride (ULM-4)

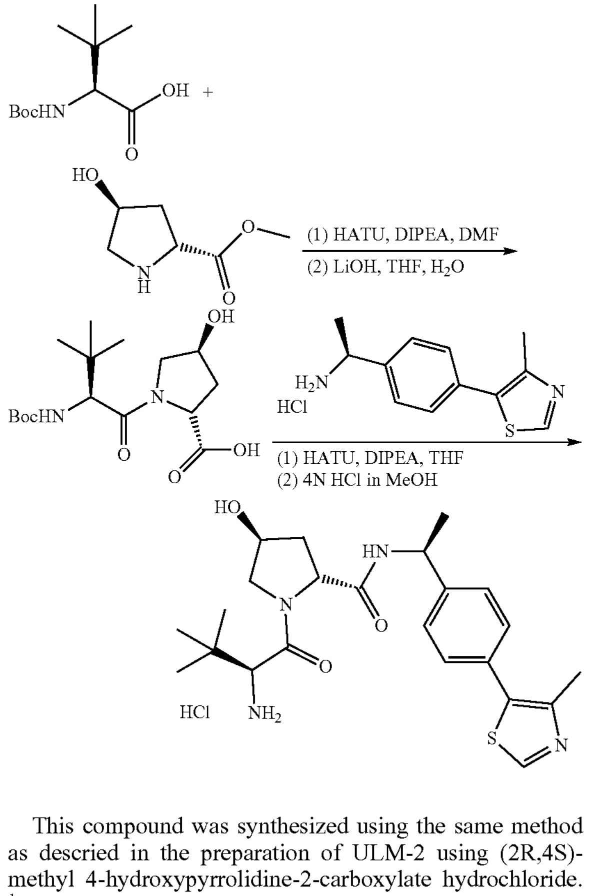

This compound was synthesized using the same method as descried in the preparation of ULM-2 using (2R,4S)-methyl 4-hydroxypyrrolidine-2-carboxylate hydrochloride. $^1$HNMR (400 MHz, $CD_3OD$): δ 1.14 (s, 9H), 1.55 (d, J=6.8 Hz, 3H), 2.00-2.05 (m, 1H), 2.51-2.58 (m, 1H), 2.65 (s, 3H), 3.77-3.81 (m, 1H), 3.88-3.92 (m, 1H), 4.06 (br, 1H), 4.41-4.46 (m, 1H), 4.56-4.60 (m, 1H), 5.07-5.12 (m, 1H), 7.58 (d, J=8.0 Hz, 2H), 7.67 (d, J=8.0 Hz, 2H), 10.02 (s, 1H). LC-MS $[M+H]^+$: 445.3

Intermediate 5 and Intermediate 6: tert-butyl-N-[(2S)-1-[(2S,4R)-4-hydroxy-2-{[(1R)-2-hydroxy-1-[4-(4-methyl-1,3-thiazol-5-yl)phenyl]ethyl]carbamoyl}pyrrolidin-1-yl]-3,3-dimethyl-1-oxobutan-2-yl]carbamate (ULM-5-A) and tert-butyl N-[(2S)-1-[(2S,4R)-4-hydroxy-2-{[(1S)-2-hydroxy-1-[4-(4-methyl-1,3-thiazol-5-yl)phenyl]ethyl]carbamoyl}pyrrolidin-1-yl]-3,3-dimethyl-1-oxobutan-2-yl]carbamate (ULM-5-B)

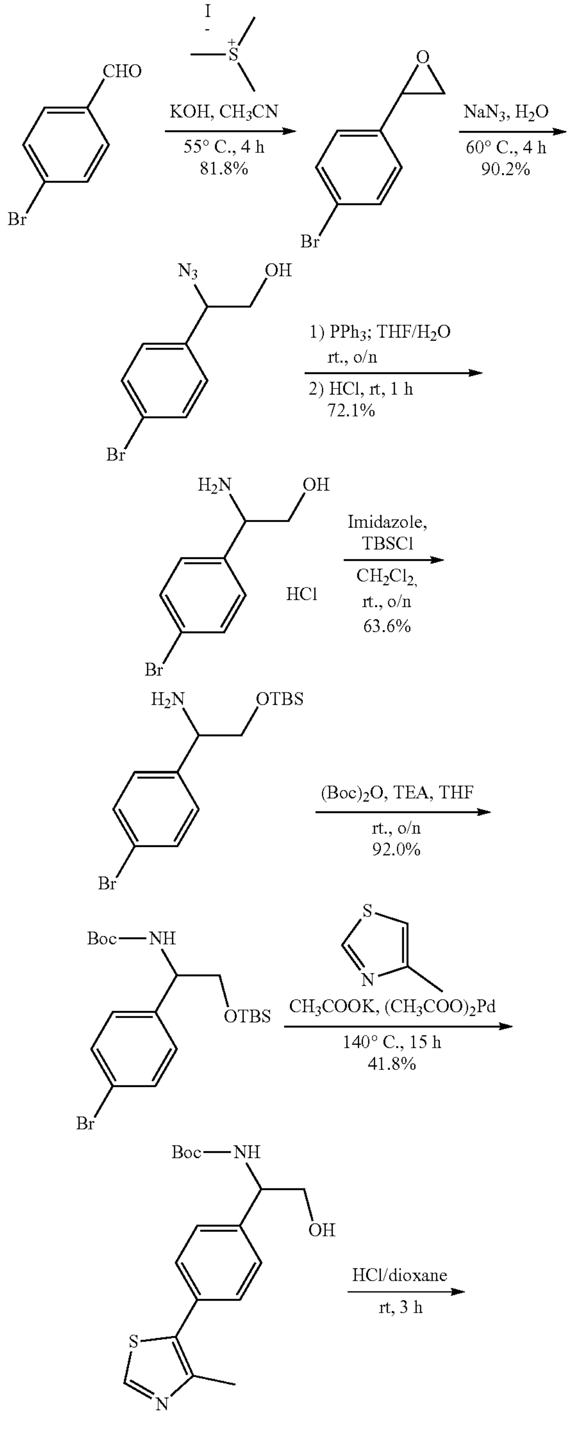

-continued

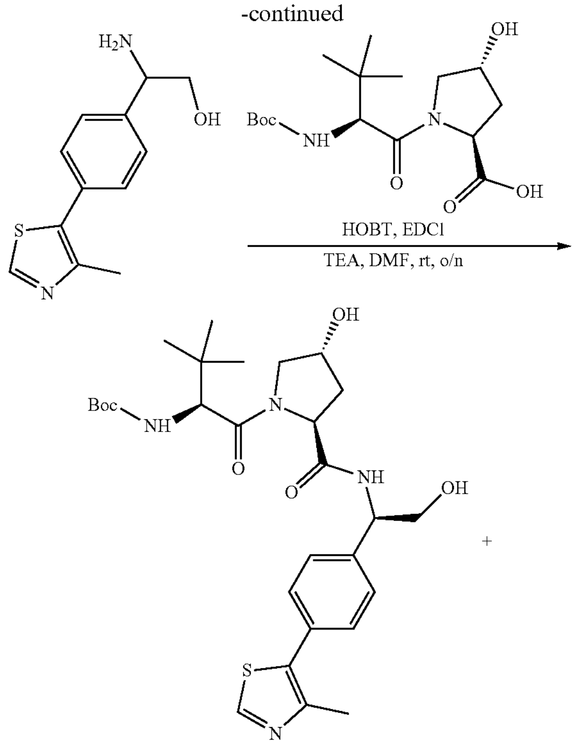

ULM-5-A

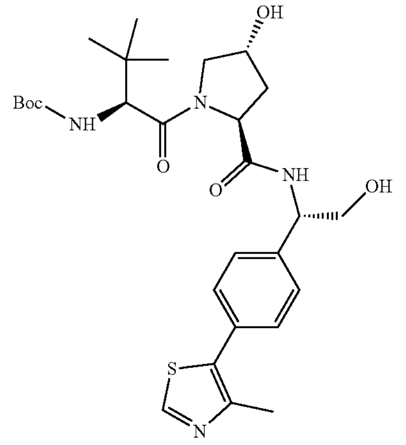

ULM-5-B

Step 1: The synthesis of 2-(4-bromophenyl)oxirane

A mixture of 4-bromobenzaldehyde (2.52 g, 13.6 mmol), trimethylsulfonium iodide (2.87 g, 14.1 mmol), water (0.65 mL, 36.1 mmol) and potassium hydroxide (1.56 g, 27.7 mmol) in acetonitrile (20 mL) was warmed to 55° C. for 4 hours. The resulting solution was partitioned between water and diethyl ether, and the organic layer was washed with water, diluted hydrochloric acid, and brine, and dried over sodium sulfate. Crude product of 2-(4-bromophenyl)oxirane (2.20 g, 81.8% yield) was obtained by removal of organic solvent under reduced pressure, which was used for next reaction without purification.

$^1$H NMR (400 MHz, $CDCl_3$) δ 2.74 (1H, q, J=2.8 Hz), 3.14 (1H, dd, J=4.0 Hz, 5.2 Hz), 3.82 (1H, dd, J=2.4 Hz, 4.0 Hz), 7.15 (2H, d, J=8.4 Hz), 7.47 (2H, d, J=8.8 Hz).

Step 2: The synthesis of 2-azido-2-(4-bromophenyl)ethanol

To a stirred suspension of 2-(4-bromophenyl)oxirane (5.0 g, 25.3 mmol) in distilled water (70 mL) was added the sodium azide (3.28 g, 50.5 mmol), the resulting mixture was stirred at 60° C. for 4 hour and was monitored by TLC. After reaction completion, the mixture was extracted with EtOAc, washed with brine, dried over anhydrous sodium sulfate, filtered, and concentrated in vacuo to give 2-azido-2-(4-bromophenyl)ethanol (5.5 g, 90.2%) as pale yellow oils. The crude product was used for next step directly. 1H NMR (400 MHz, $CDCl_3$) δ 1.94 (1H, s), 3.63-3.66 (2H, m), 4.57 (1H, dd, J=5.2 Hz, 7.6 Hz), 7.15 (2H, d, J=8.4 Hz), 7.46 (2H, d, J=8.4 Hz).

Step 3: The synthesis of 2-amino-2-(4-bromophenyl)ethanol hydrochloride

To a solution of 2-azido-2-(4-bromophenyl)ethanol (2.0 g, 8.30 mmol) in tetrahydrofuran (20.0 mL) and water (5.00 mL) was added triphenylphosphine (4.35 g, 16.6 mmol). The reaction mixture was stirred at room temperature overnight and the solvent was removed in vacuo. The residue was dissolved in HCl/dioxane (4M, 10.0 mL) and stirred at room temperature for 1 hour. After being concentrated, the solid was washed with dichloromethane to give 2-amino-2-(4-bromophenyl)ethanol hydrochloride (1.5 g, 72.1% yield) as white solids.

$^1$H NMR (400 MHz, $CDCl_3$) δ 3.70 (211, s), 4.28 (1H, s), 5.55 (1H, s), 7.47 (2H, d, J=8.4 Hz), 7.63 (2H, d, J=8.4 Hz), 8.61 (31H, s); LC/MS 216.2 $[M+H]^+$.

Step 4: The synthesis of 1-(4-bromophenyl)-2-(tert-butyldimethylsilyloxy)ethanamine To a solution of 2-amino-2-(4-bromophenyl)ethanol hydrochloride (1.80 g, 7.17 mmol) in dichloromethane (50 mL) was added imidazole (1.95 g, 2.87 mmol) and tert-butyldimethylsilyl chloride (TBSCl) (1.63 g, 10.8 mmol) arE room temperature. The reaction mixture was stirred at room temperature overnight and then quenched with water. The aqueous phase was extracted with dichloromethane (30 mL×3), the combined organic phases were dried over anhydrous sodium sulfate, filtered, and concentrated in vacuo to give crude compound. The crude product was purified by silica gel column chromatography (petroether/ethyl acetate=5:1) to give 1-(4-bromophenyl)-2-(tert-butyldimethylsilyloxy)ethanamine (1.50 g, 63.6%) as white solids.

LC/MS: 330.1 $[M+H]^+$;

Step 5: The synthesis of tert-butyl 1-(4-bromophenyl)-2-(tert-butyldimethylsilyloxy)ethylcarbamate To a solution of 1-(4-bromophenyl)-2-(tert-butyldimethylsilyloxy)ethanamine (1.50 g, 4.56 mmol) in tetrahydrofuran (20 mL) was added triethylamine (0.69 g, 6.84 mmol) and di-tert-butyl dicarbonate (1.49 g, 6.84 mmol). The reaction mixture was stirred at room temperature overnight and then quenched with water. The aqueous phase was extracted with ethyl acetate (50 mL×3) and washed with brine. The combined organic phases were dried over anhydrous sodium sulfate, filtered, and concentrated in vacuo to give crude compound. The crude product was purified by silica gel column chromatography (petroether/ethyl acetate=100:1) to give tert-butyl 1-(4-bromophenyl)-2-(tert-butyldimethylsilyloxy)ethylcarbamate (1.80 g, 92.0%) as pale yellow oils.

$^1$H NMR (400 MHz, $CDCl_3$) δ 0.01 (6H, d, J=9.6 Hz), 0.86 (9H, s), 1.42 (9H, s), 3.65-3.70 (2H, m), 4.60-4.63 (1H, m), 7.34 (2H, d, J=8.0 Hz), 7.39 (1H, d, J=8.8 Hz), 7.56 (2H, d, J=8.4 Hz).

Step 6: The synthesis of tert-butyl 2-hydroxy-1-(4-(4-methylthiazol-5-yl)phenyl)-ethylcarbamate A mixture of tert-butyl 1-(4-bromophenyl)-2-(tert-butyldimethylsilyloxy)ethylcarbamate (4.0 g, 9.32 mmol), 4-methylthiazole (1.85 g, 18.6 mmol), potassium acetate (1.82 g, 18.6 mmol), palladium (II) acetate (0.11 g, 0.47 mmol) were dissolved in dimethylacetamide and stirred under argon. The mixture was heated to 140° C. and stirred for 15 hours, then diluted with water. The aqueous phase was extracted with ethyl acetate (50 mL×3) and washed with brine. The combined organic layer was dried over sodium sulfate, filtered and concentrated under vacuum to give crude compound which was purified by silica gel column chromatography (petroether/ethyl acetate=100:1) to give tert-butyl 2-hydroxy-1-(4-(4-methylthiazol-5-yl)phenyl) ethylcarbamate (1.30 g, 41.8%) as pale yellow solids.

$^1$H NMR (400 MHz, $CDCl_3$) δ 1.38 (911, s), 2.46 (3H, s), 3.52 (2H, t, J=6.0 Hz), 4.55-4.58 (11H, m), 4.84 (1H, t, J=6.0 Hz), 7.30 (1H, d, J=8.0 Hz), 7.38-7.45 (4H, m), 8.99 (1H, s); LC/MS 335.2 $[M+H]^+$; Rt=1.859 min Step 7: The synthesis of 2-amino-2-(4-(4-methylthiazol-5-yl)phenyl)ethanol hydrochloride The tert-butyl 2-hydroxy-1-(4-(4-methylthiazol-5-yl)phenyl)ethylcarbamate (300 mg, 0.536 mmol) was dissolved in hydrochloric acid/dioxane (5 mL, 4M). The resulting reaction mixture was stirred at room temperature for 3 hours. The solvent was concentrated in vacuo to give 2-amino-2-(4-(4-methylthiazol-5-yl)phenyl)ethanol hydrochloride as white solids, which was used for the next step without further purification.

Step 8: The synthesis of tert-butyl N-[(2S)-1-[(2S,4R)-4-hydroxy-2-{[(1R)-2-hydroxy-1-[4-(4-methyl-1,3-thiazol-5-yl)phenyl]ethyl]carbamoyl}pyrrolidin-1-yl]-3,3-dimethyl-1-oxobutan-2-yl]carbamate (ULM-5-A) and tert-butyl N-[(2S)-1-[(2S,4R)-4-hydroxy-2-{[(1 S)-2-hydroxy-1-[4-(4-methyl-1,3-thiazol-5-yl)phenyl]ethyl]carbamoyl}pyrrolidin-1-yl]-3,3-dimethyl-1-oxobutan-2-yl]carbamate (ULM-5-B)

A solution of 2-amino-2-(4-(4-methylthiazol-5-yl)phenyl) ethanol hydrochloride (1000 mg, 3.70 mmol), N-(3-dimethylaminopropyl)-N-ethylcarbodiimide hydrochloride (EDCI) (995 mg, 5.19 mmol), 1-hydroxybenzotriazole (HOBT) (695 mg, 5.19 mmol), (2S,4R)-1-((S)-2-(tert-butoxycarbonylamino)-3,3-dimethylbutanoyl)-4-hydroxypyrrolidine-2-carboxylic acid (1273 mg, 3.70 mmol) and triethylamine (747 mg, 7.40 mmol) in N,N-dimethylformamide (50 mL) was stirred at room temperature overnight under agron, and then water (80 mL) was added to the mixture. The aqueous layer was extracted with ethyl acetate (50 mL×5). The combined organic layer was washed with brine (50 mL×3), dried over anhydrous sodium sulfate, and concentrated in vacuo. The crude product was purified by preparative TLC (dichloromethyl/methanol=15:1) to give tert-butyl (S)-1-((2S,4R)-4-hydroxy-2-((R)-2-hydroxy-1-(4-(4-methylthiazol-5-yl)phenyl)ethylcarbamoyl)pyrrolidin-1-yl)-3,3-dimethyl-1-oxobutan-2-ylcarbamate (700 mg) as pale yellow oils and tert-butyl (S)-1-((2S,4R)-4-hydroxy-2-((S)-2-hydroxy-1-(4-(4-methylthiazol-5-yl)phenyl) ethyl carbamoyl) pyrrolidin-1-yl)-3,3-dimethyl-1-oxobutan-2-ylcarbamate (500 mg) as pale yellow oils.

ULM-5-A: $^1$H NMR (400 MHz, $CDCl_3$) δ 0.93 (911, s), 1.39 (9H, s), 1.77-1.83 (1H, m), 2.01-2.06 (1H, m), 2.46 (3H, s), 3.54-3.60 (4H, m), 4.13-4.19 (111, m), 4.29-4.36 (1H, m), 4.50 (1H, t, J=8.0 Hz), 4.78 (11H, t, J=5.6 Hz), 4.81-4.88 (1H, m), 5.12-5.16 (1H, m), 6.46 (11H, d, J=9.2 Hz), 7.36-7.46 (4H, m), 8.41 (1H, d, J=8.0 Hz), 8.99 (1H, s); LC/MS 561.2 $[M+H]^+$; Rt=1.897 min ULM-5-B: $^1$H NMR (400 MHz, $CDCl_3$) δ 0.87 (9H, s), 1.38 (9H, s), 1.92-2.06 (211, m), 2.45 (3H, s), 3.56-3.69 (4H, m), 4.06-4.14 (11H, m), 4.36 (1H, s), 4.56 (11H, t, J=7.6 Hz), 4.76-4.81 (1H, m), 4.87 (1H, t, J=5.6 Hz), 5.146 (1H, d, J=2.8 Hz), 6.47 (1H, d, J=8.8 Hz), 7.37 (2H, d, J=8.0 Hz), 7.51 (2H, d, J=8.0 Hz), 8.37 (1H, d, J=7.6 Hz), 8.98 (11H, s); LC/MS 561.2 $[M+H]^+$; Rt=1.887 min Intermediate 7: (2S,4R)-N-[(4-chloro-2-hydroxyphenyl)methyl]-4-hydroxy-1-[3-methyl-2-(3-methyl-1,2-oxazol-5-yl)butanoyl]pyrrolidine-2-carboxamide (ULM-6)

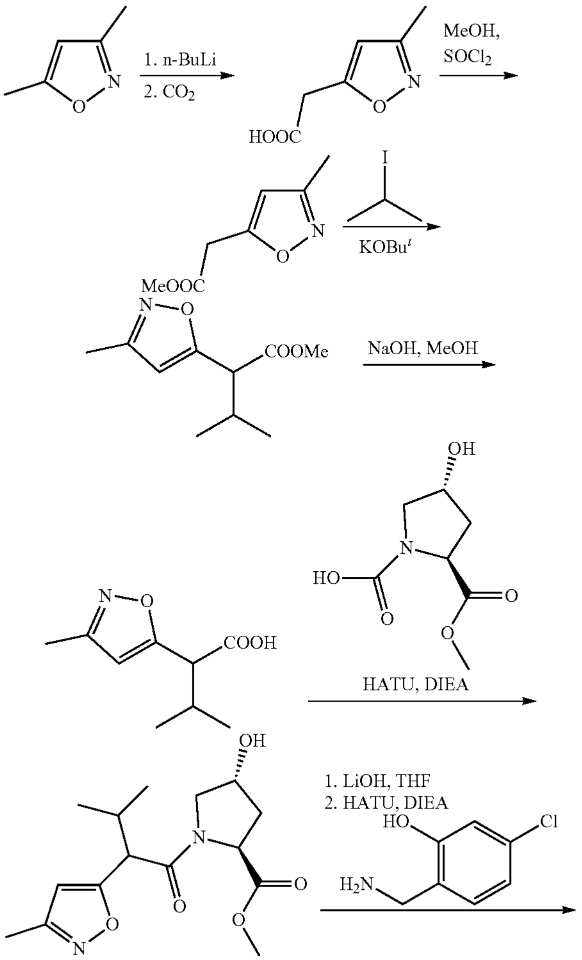

-continued

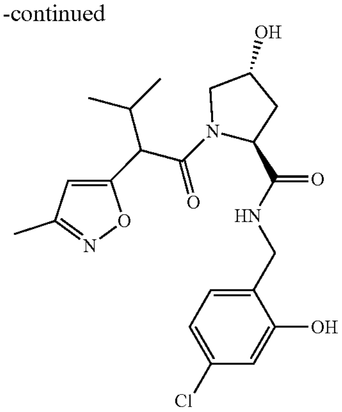

ULM-6

This key intermediate was prepared using the synthetic route above. The required 3-methylisoxazole-5-acetic acid was prepared according to the literature (J. Org. Chem. 66, 6595-6603, 2001). The alkylation with 2-iodopropane has been described in the literature. The desired ULM-6 was prepared using the same synthetic method as described in the preparation of intermediate ULM-3.

$^1$H NMR (400 MHz, $CDCl_3$): δ 9.33 (s, 0.5H), 9.20 (s, 0.5H), 8.07 (t, J=6.4 Hz, 0.5H), 7.83 (t, J=6.0 Hz, 0.5H), 6.99 (dd, J=2.4, 8.0 Hz, 1H), 6.89-6.90 (m, 1H), 6.76-6.78 (m, 1H), 6.02 (s, 0.5H), 5.99 (s, 0.5H), 5.80-5.83 (m, 0.5H), 4.35 (q, J=6.4 Hz, 1.5), 4.16-4.25 (m, 2H), 3.72-3.76 (m, 0.5H), 3.61 (d, J=9.2 Hz, 1.0H), 3.51-3.55 (m, 1.5H), 2.30-2.46 (m, 2.5H), 2.26 (s, 1.5H), 2.24 (s, 1.5H), 1.95-2.05 (m, 1H), 1.01 (d, J=6.8 Hz, 1.5H), 0.82-0.87 (m, 4.5H); LC-MS 436.1 $[M+1]^+$; Rt=3.57 min.

PTM Synthesis:

Preferred PTM embodiments of the current disclosure can be prepared according to the synthetic routes in the schemes below. These routes can be modified and adapted to the synthesis of the particular PTM embodiment using general methods known to those skilled in the art.

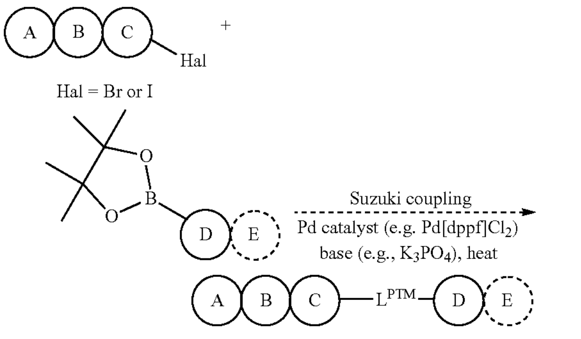

$L^{PTM}$ = bond, C, D = aryl or heteroaryl, E = optional ring

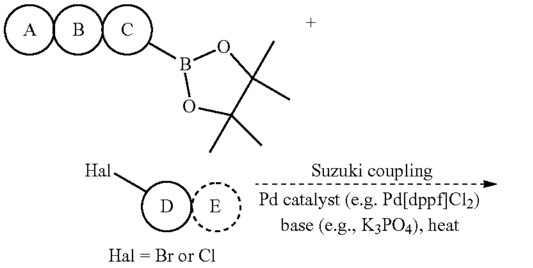

-continued

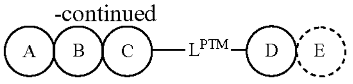

$L^{PTM}$ = bond, C, D = aryl or heteroaryl, E = optional ring wherein the above approaches are most relevant to the cases where both C and D are aromatic rings (aryl or heteroaryl).

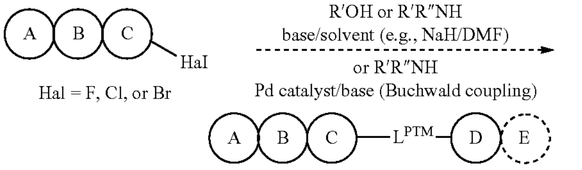

D = aryl, heteroaryl, cycloalkyl, or heterocycloalkyl; E = optional ring

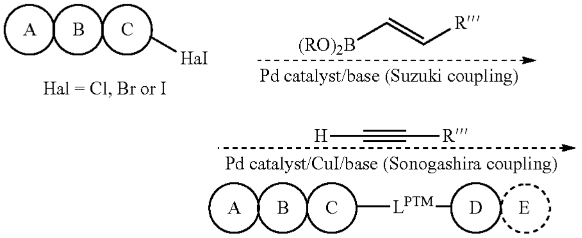

D = aryl, heteroaryl, cycloalkyl, or heterocycloalkyl; E = optional ring wherein the above approaches are relevant to the cases where C is an aromatic ring and D (and optional ring E) is either a (hetero)aryl or a (hetero)cycloalkyl ring which can be inherent in R', R" and R"', or can be installed subsequently following functional manipulation of $R^1$, R" and R"'.

The general approaches depicted above would also apply to the cases where ring C in not present, and the tricyclic fused ring system of ABC is instead represented by the bicyclic fused ring system of AB, and, also, to the cases where single ring D is instead represented by the fused bicyclic ring system DE.

One skilled in the art will recognize that the above mentioned approaches can include cases where the hetero-bifunctional linker has already been preattached to ring D or ring E (with or without ULM present), as shown in the example below and applicable to other examples.

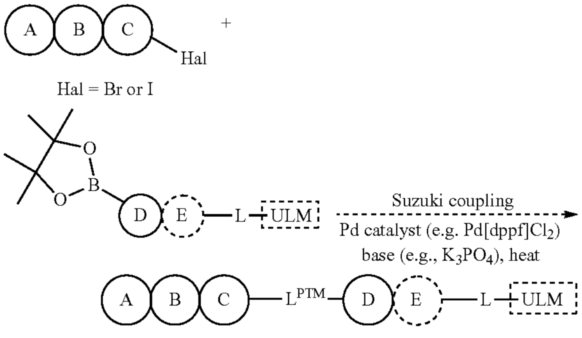

$L^{PTM}$ = bond, C, D = aryl or heteroaryl, E = optional ring

-continued

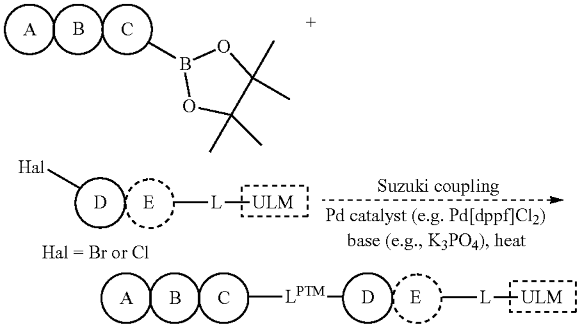

$L^{PTM}$ = bond, C, D = aryl or heteroaryl, E = optional ring

In addition, full hetero-bifunctional molecules can be assembled using other sequences of steps. For example, PTM can be connected to the rest of the molecule using a functional group on ring D to be reacted with the functional group on the hetero-bifunctional linker, preattached to ULM, in the process of nucleophilic substitution or reductive amination as shown in the scheme below.

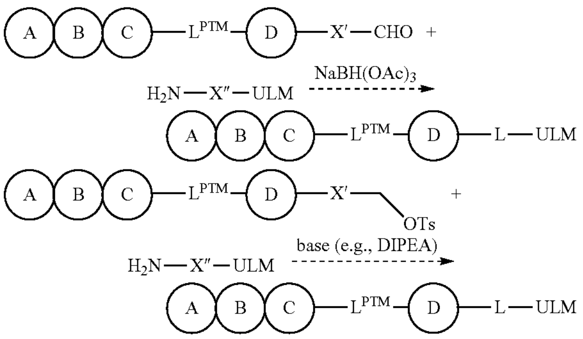

Alternatively, functional groups on the PTM and ULM fragments can be reversed as shown in the scheme below.

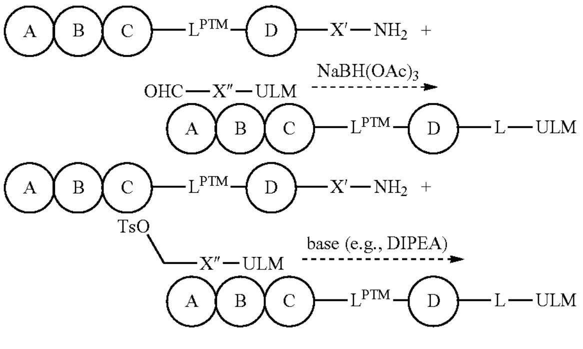

Alternatively, the sequence of steps can be reversed, and one end of the PROTAC linker can be first attached to the PTM, and subsequently the functional group on the other end of the linker can be reacted with ULM via one of the nonlimiting approaches as shown in the scheme below, depending on the exact nature of the ULM group. One skilled in the art will appreciate that certain protecting group manipulations may be required in the course of these transformations.

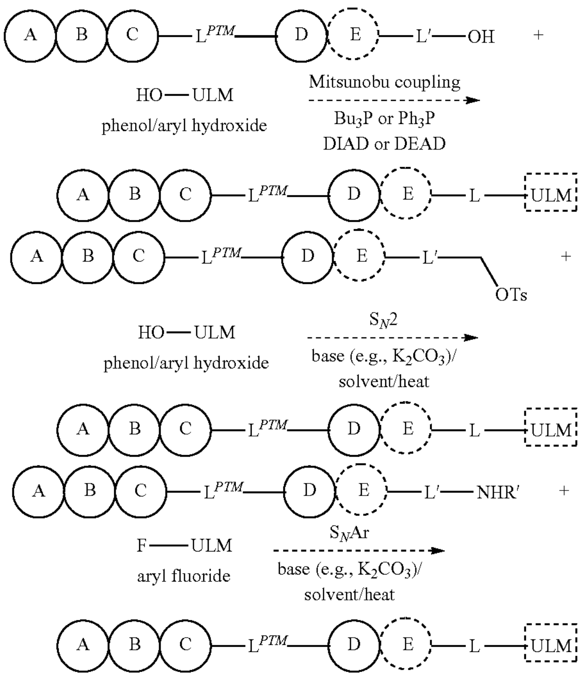

Preferred examples of the current invention of the current invention can be prepared utilizing approaches described previously in US 20180125821, as well as additionally detailed in the schemes below.

In particular, preferred PTMs of the current invention can be prepared as described below.

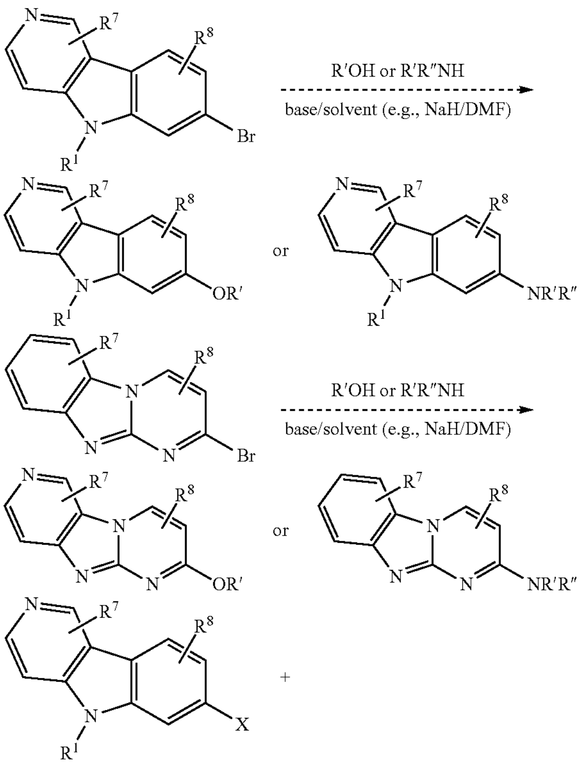

X = Cl, Br or OTf

-continued

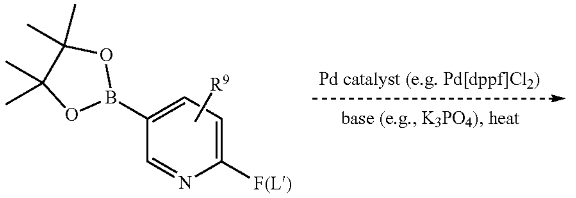

L′ implies preattached linker or other functional group

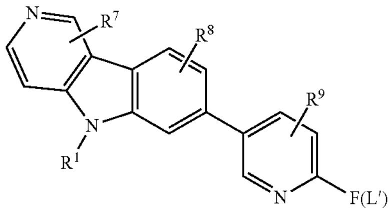

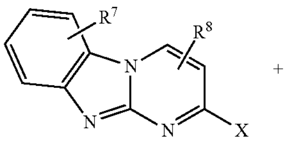

X = Cl, Br or OTf

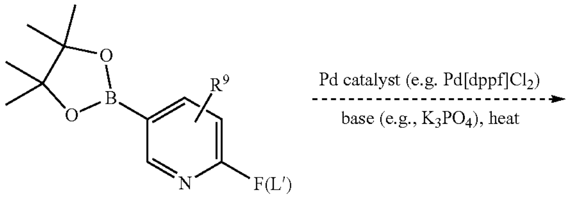

L′ implies preattached linker or other functional group

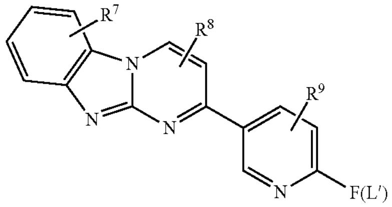

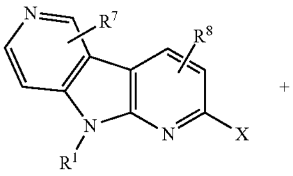

X = Cl, Br or OTf

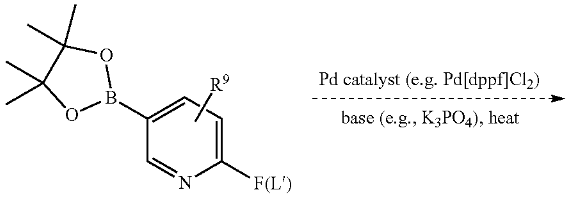

L′ implies preattached linker, partial linker or an alternative functional group -continued

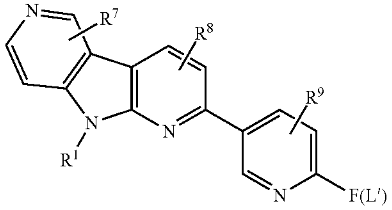

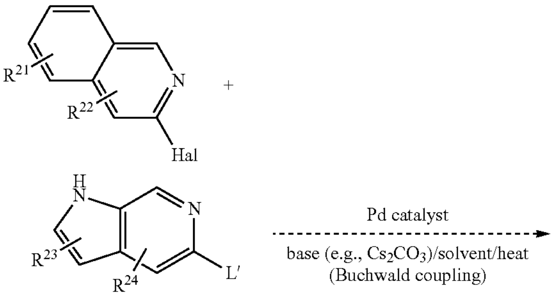

L′ implies preattached linker or partial linker

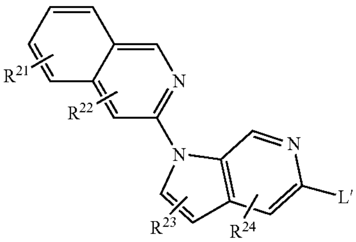

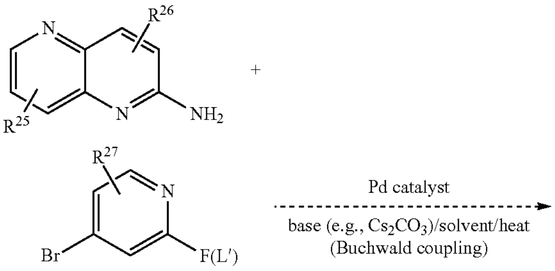

L′ implies preattached linker, partial linker or an alternative functional group

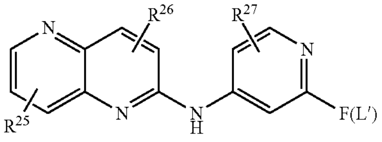

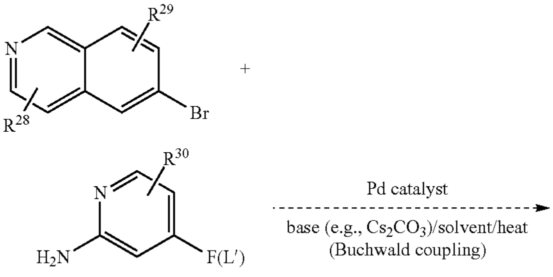

L′ implies preattached linker, partial linker or an alternative functional group -continued
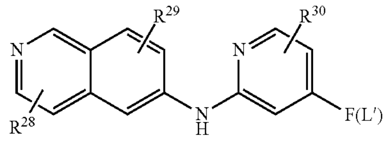
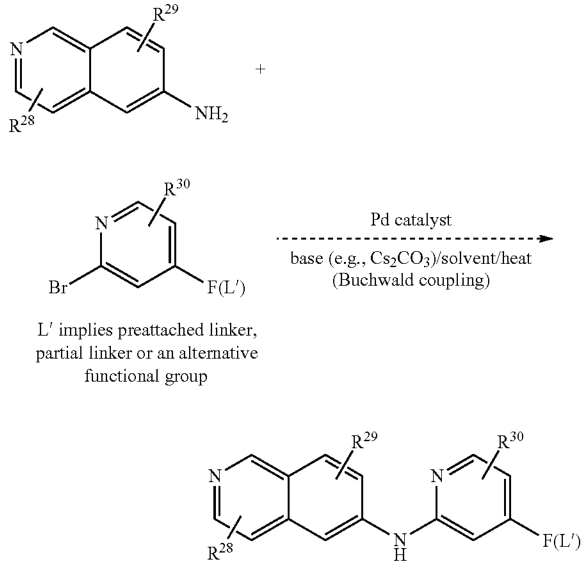
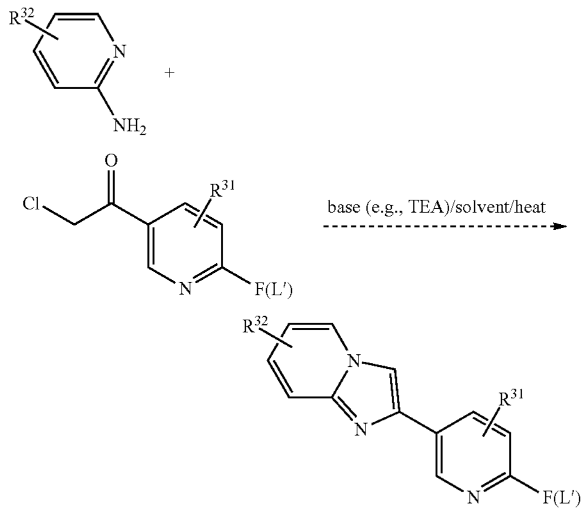
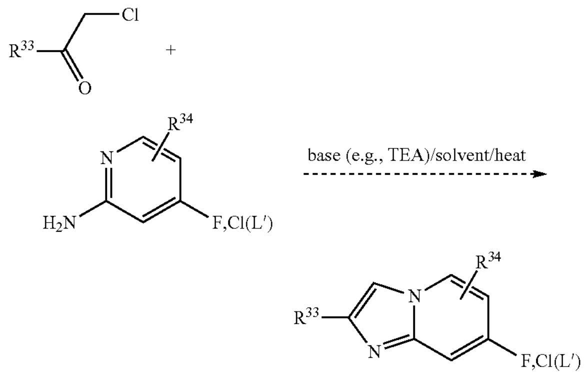
Most preferred PTMs of the current invention are as detailed below:
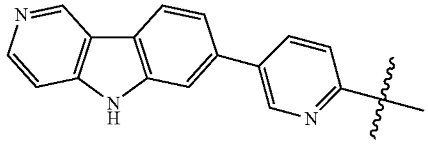
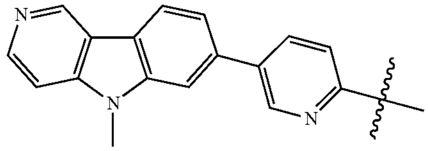
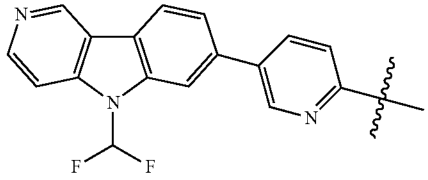
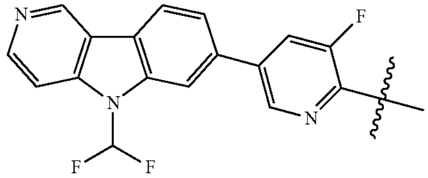
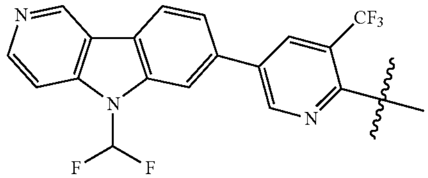
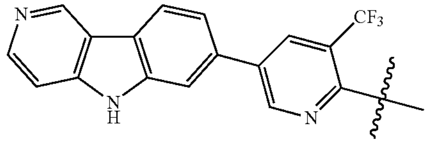
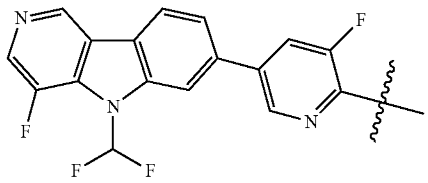
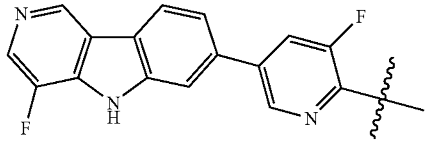
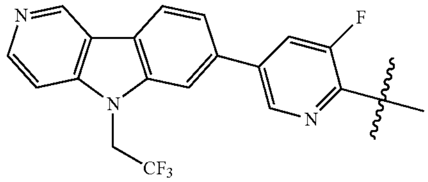
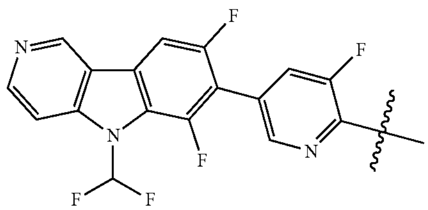

-continued
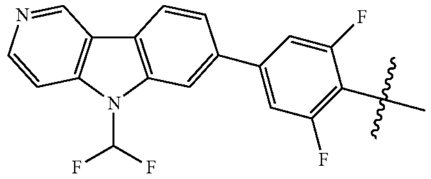
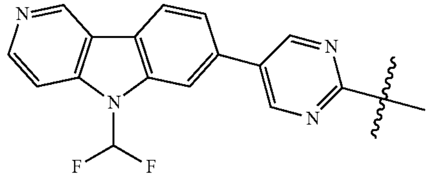
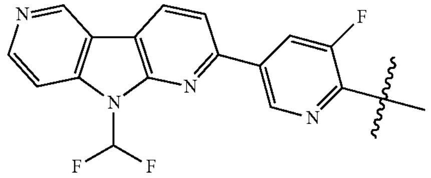
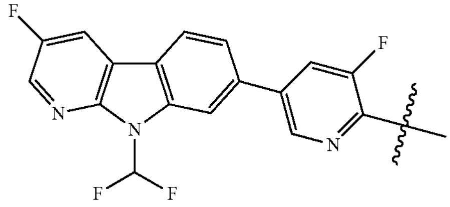
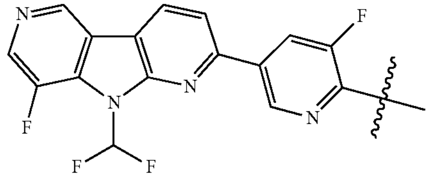
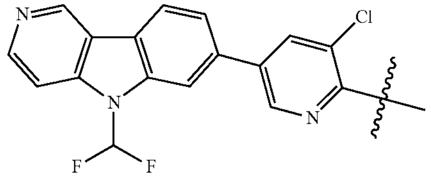
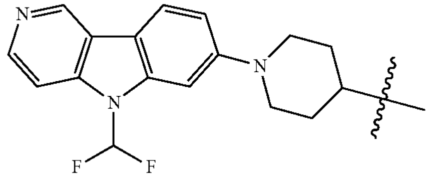
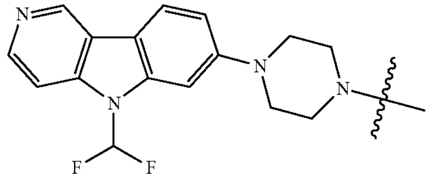
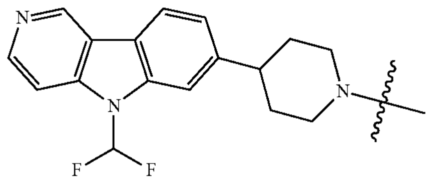
-continued
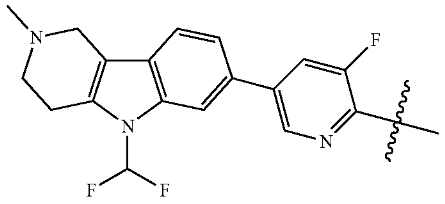
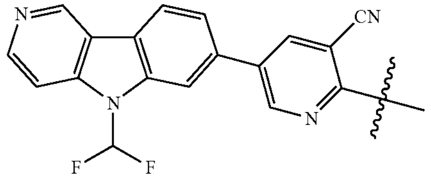
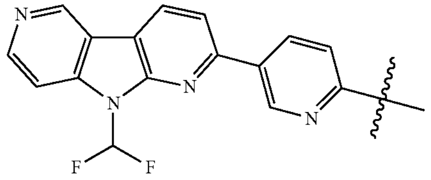
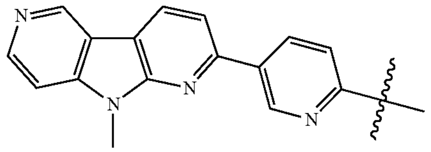
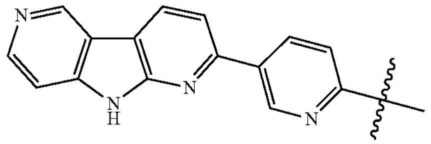
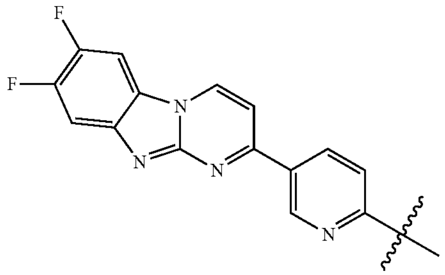
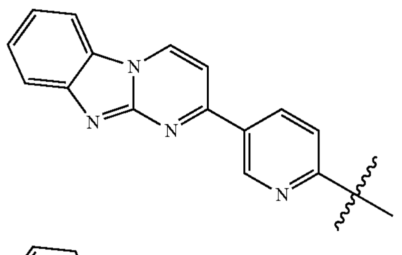
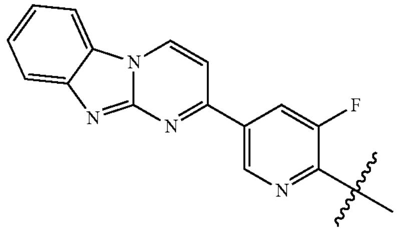

-continued
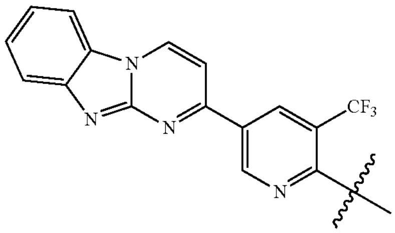
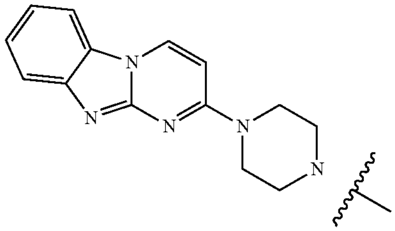
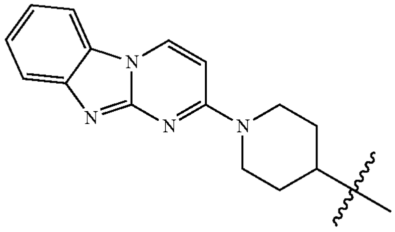
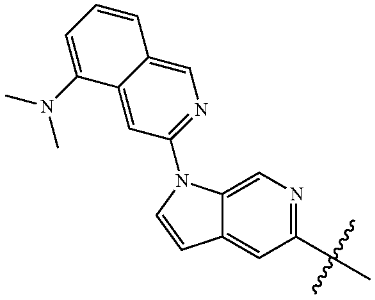
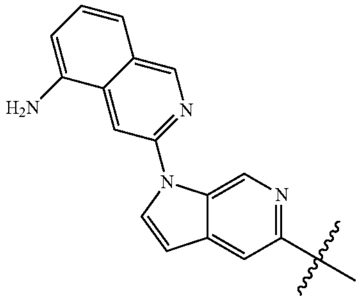
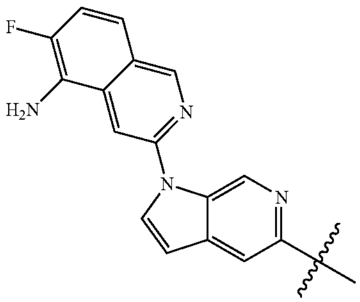
-continued
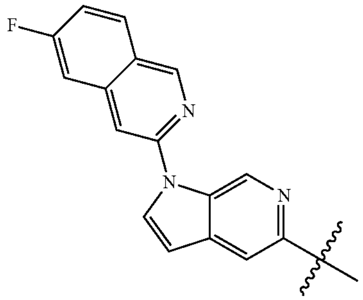
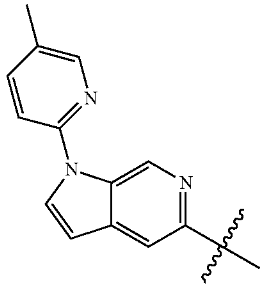
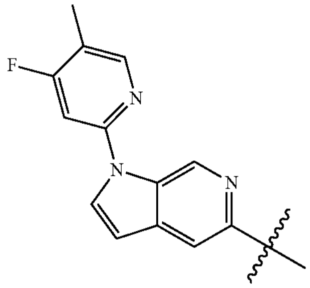
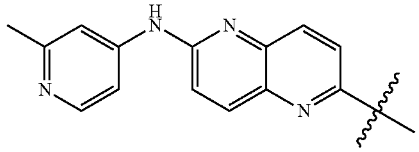
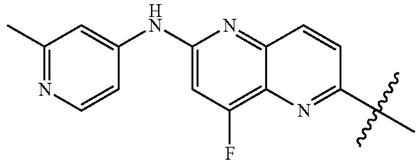
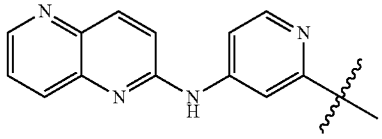
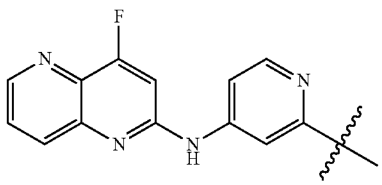
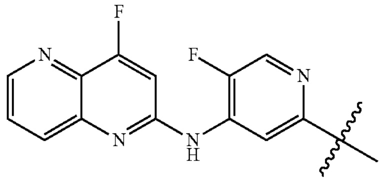

-continued
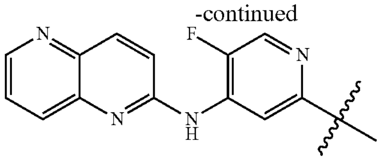
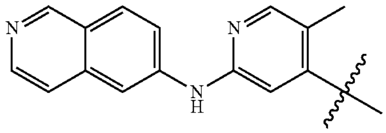
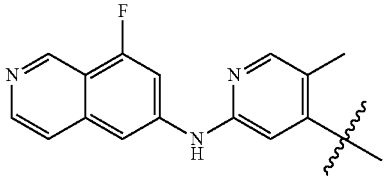
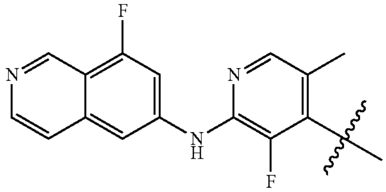
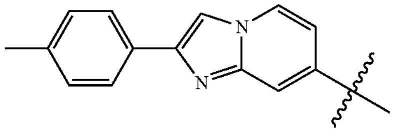
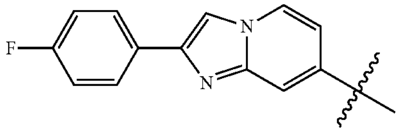
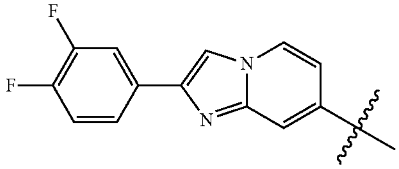
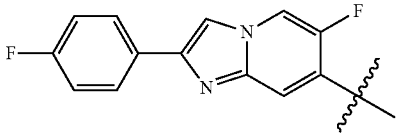
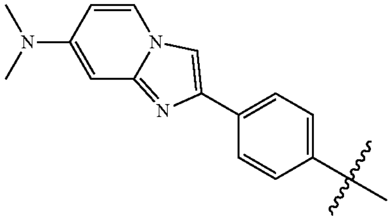
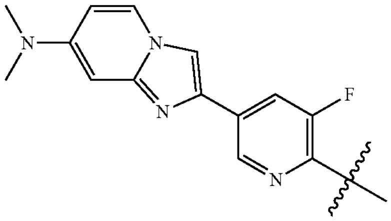
Further synthetic routes that may be utilized to prepare exemplary PTM of the current disclosure are shown below.
Scheme 1
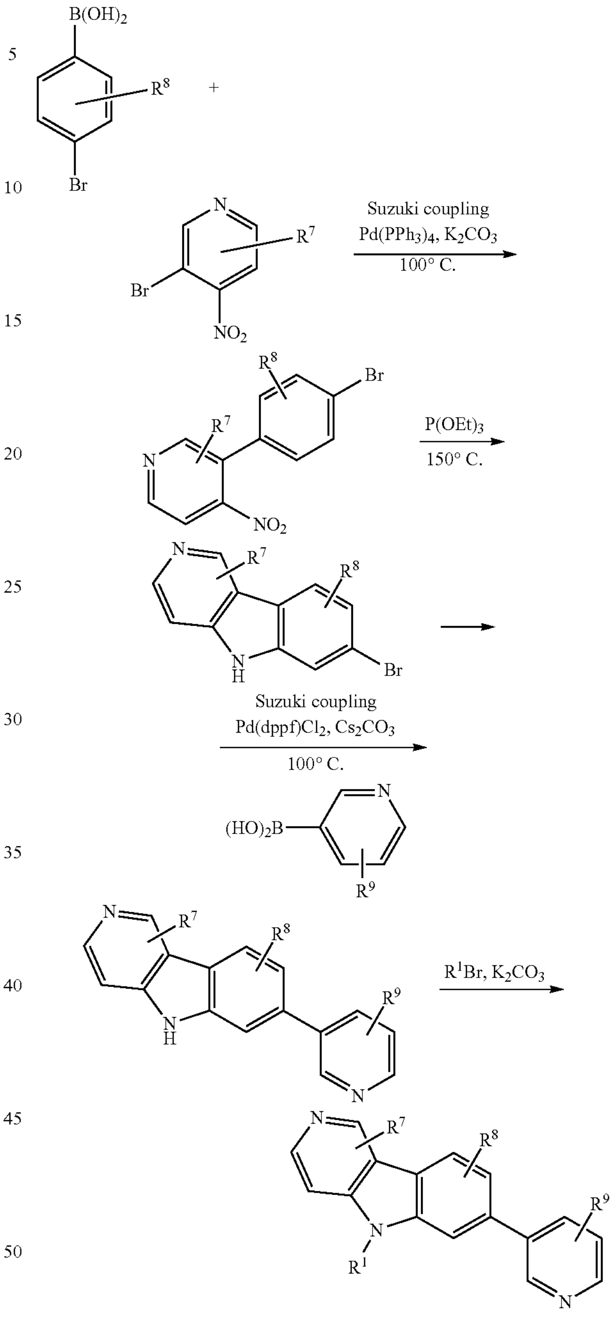
Scheme 2
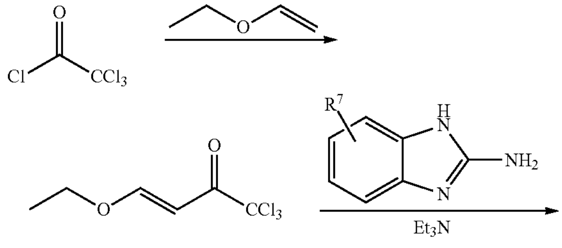

-continued

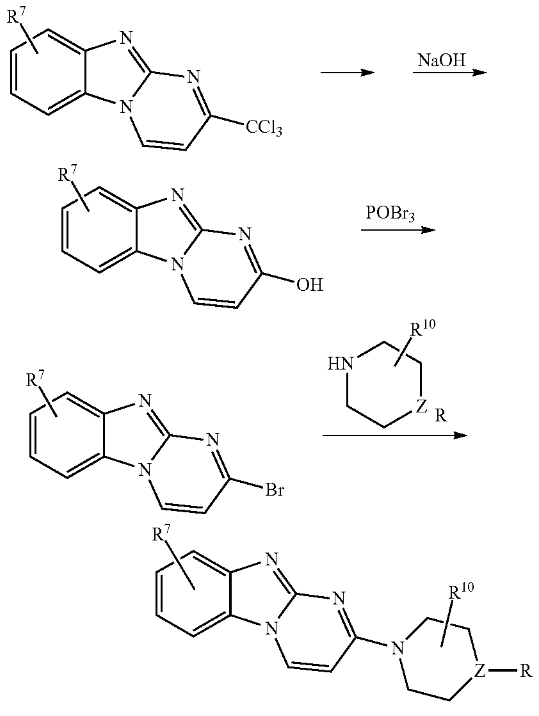

Z = N, CH

Scheme 3

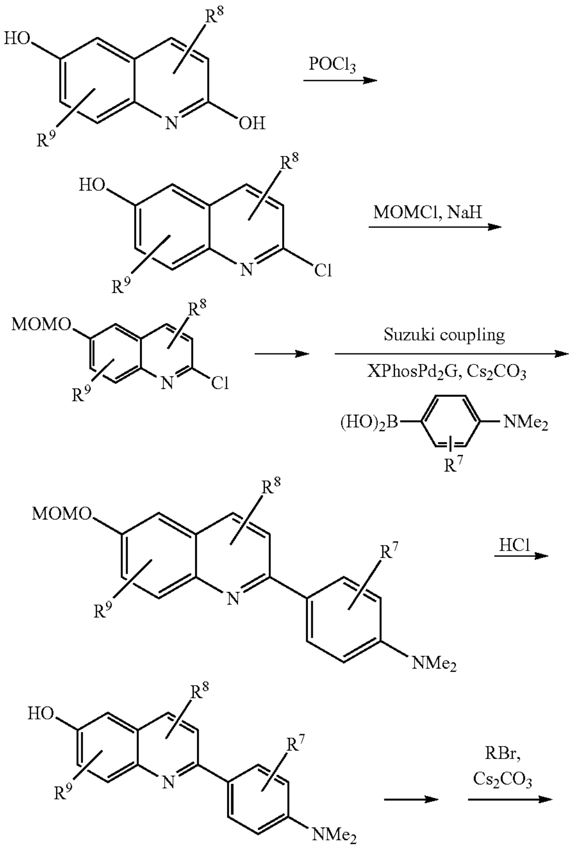

-continued

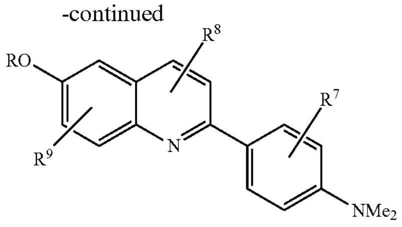

Exemplary Bifunctional Compound Synthesis

Intermediate 1

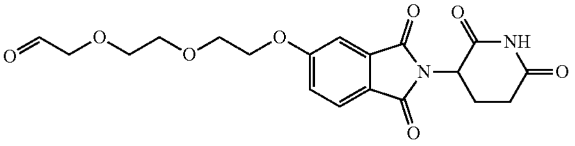 [SMILES: O=CCOCCOCCOc1ccc2c(c1)C(=O)N(C1CCC(=O)NC1=O)C2=O]

Step 1: 2-(2,6-dioxopiperidin-3-yl)-5-(2-(2-(2-hydroxyethoxy)ethoxy)ethoxy)isoindoline-1,3-dione

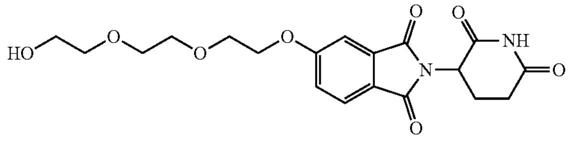 [SMILES: O=C1CCC(N2C(=O)c3ccc(OCCOCCOCCO)cc3C2=O)C(=O)N1]

To a solution of 2-(2,6-dioxopiperidin-3-yl)-5-hydroxyisoindoline-1,3-dione (500 mg, 1.82 mmol) in DMF (10 mL) were added $K_2CO_3$ (756 mg, 5.47 mmol) and 2-(2-(2-hydroxyethoxy)ethoxy)ethyl 4-methyl-benzenesulfonate (832 mg, 2.73 mmol) at 25° C. The resulting solution was stirred at 70° C. for 5 hours. After cooling to room temperature, the reaction was quenched with $H_2O$ (10 mL), and the mixture was extracted with EtOAc (10 mL×2). The combined organic layers were dried over anhydrous sodium sulfate and concentrated. The residue was purified with silica gel column to afford the desired product (95 mg, 13% yield).

Step 2: 2-(2-(2-((2-(2,6-dioxopiperidin-3-yl)-1,3-dioxoisoindolin-5-yl)oxy)ethoxy)ethoxy)acetaldehyde

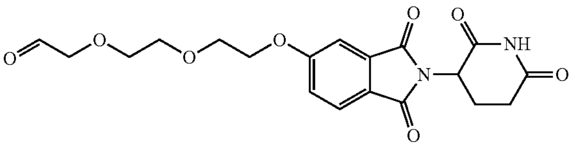 [SMILES: O=CCOCCOCCOc1ccc2c(c1)C(=O)N(C1CCC(=O)NC1=O)C2=O]

To a solution of 2-(2,6-dioxopiperidin-3-yl)-5-(2-(2-(2-hydroxyethoxy)ethoxy)ethoxy)isoindoline-1,3-dione (95 mg, 0.23 mmol) in $CH_3CN$ (5 mL) was added IBX (130 mg, 0.46 mmol) at 25° C. The reaction was stirred at 80° C. for 2 hours. After cooling to room temperature, the mixture was filtered through Celite, and the filtrate was concentrated to afford crude intermediate 1, 2-(2-(2-((2-(2,6-dioxopiperidin-3-yl)-1,3-dioxoisoindolin-5-yl)oxy)ethoxy)ethoxy)acetaldehyde, (90 mg), which was used without further purification.

Intermediate 2

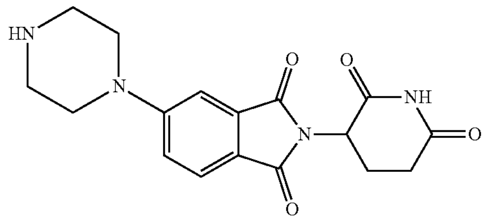 [SMILES: O=C1CCC(N2C(=O)c3ccc(N4CCNCC4)cc3C2=O)C(=O)N1]

To a solution of 2-(2,6-dioxopiperidin-3-yl)-5-fluoroisoindoline-1,3-dione (10 g, 36.2 mmol) in NMP (70 mL) was added tert-butyl piperazine-1-carboxylate (13.47 g, 72.5 mmol) and DIPEA (18.6 g, 14.5 mmol). The resulting mixture was stirred at 90° C. for 16 hours. After cooling to room temperature, the reaction was quenched with water (100 mL), and the mixture was extracted with ErOAc (300 mL×2). The combined organic layers were dried over $Na_2SO_4$, filtered and concentrated under reduced pressure. The residue was purified by silica gel column chromatography (PE/EA=100-2/1) to afford the desired product, 2-(2, 6-dioxopiperidin-3-yl)-5-(piperazin-1-yl)isoindoline-1,3-dione (14 g, 31.67 mmol, 87.5% yield) as a light yellow solid.

Synthetic Scheme for Exemplary Compound 51

Step 1: 3-(4-bromophenyl)-4-nitropyridine

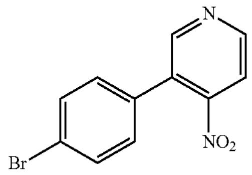 [SMILES: O=[N+]([O-])c1ccncc1-c1ccc(Br)cc1]

To a stirred solution of 3-bromo-4-nitropyridine (100 g, 492.6 mmol), (4-bromophenyl)boronic acid (98.6 g, 492.6 mmol), and potassium carbonate (203.9 g, 1.47 mol) in toluene (1000 ml)-water (100 ml) was added tetrakis(triphenylphosphine)palladium (14.8 g, 12.8 mmol) at room temperature under nitrogen atmosphere; the mixture was degassed with nitrogen three times. The resulting mixture was stirred at 50° C. overnight. TLC showed the reaction was complete. The solid was removed through filtration and washed with ethyl acetate (100 ml×3). The organic layer was collected and the aqueous layer was extracted with ethyl acetate (100 ml×2). The combined organic layers were washed with brine (400 ml), dried over anhydrous sodium sulfate, and concentrated under reduced pressure to give a crude residue which was purified by silica gel pad (eluted with 10-33% ethyl acetate in hexane) to afford 3-(4-bromophenyl)-4-nitropyridine (89 g, yield 65%) as yellow solid.

Step 2: 7-bromo-5H-pyrido[4,3-b]indole

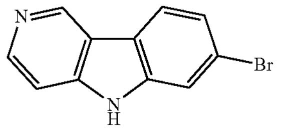 [SMILES: Brc1ccc2c(c1)[nH]c1ccncc12]

A mixture of 3-(4-bromophenyl)-4-nitropyridine (20.0 g, 71.7 mmol) in triethyl phosphate (400 ml) was stirred at 110° C. for 2 hours under nitrogen atmosphere. TLC showed the reaction was complete. The volatiles were evaporated under reduced pressure to give a residue which was purified by recrystallization (methanol) to afford 7-bromo-5H-pyrido[4,3-b]indole (11.0 g, yield 62%) as brown solid.

Step 3: 7-(6-Fluoropyridin-3-yl)-5H-pyrido[4,3-b]indole

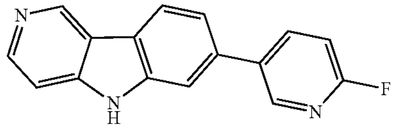 [SMILES: Fc1ccc(-c2ccc3c(c2)[nH]c2ccncc23)cn1]

A mixture of 7-bromo-5H-pyrido[4,3-b]indole (400 mg, 1.63 mmol), (6-fluoropyridin-3-yl)boronic acid (344 mg, 2.44 mmol), $PdCl_2(dppf)$ (120 mg, 0.163 mmol), $tBu_3PHBF_4$ (95 mg, 0.326 mmol) and $Cs_2CO_3$ (1.1 g, 3.26 mmol) in dioxane/water (20 mL, 20:1) was heated to 90° C. for 4 hours under $N_2$. The solid was filtered and the filtrate was evaporated. The residue was purified by chromatography (silica gel, 200-300 mesh, $CH_2Cl_2$:MeOH=30:1) to afford 7-(6-Fluoropyridin-3-yl)-5H-pyrido[4,3-b]indole (250 mg, 59% yield).

Step 4: 14-((5-(5H-pyrido[4,3-b]indol-7-yl)pyridin-2-yl)oxy)-3,6,9,12-tetraoxatetradecan-1-ol

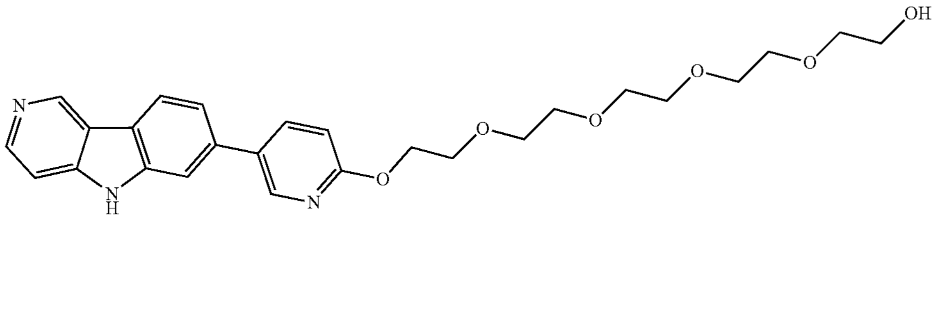 [SMILES: OCCOCCOCCOCCOCCOc1ccc(-c2ccc3c(c2)[nH]c2ccncc23)cn1]

To a solution of 3,6,9,12-tetraoxatetradecane-1,14-diol (270 mg, 1.13 mmol) in THF (10 mL) was added NaH (45 mg, 60%, 1.13 mmol) at 0° C. After stirring at 20° C. for 1 hour, a solution of 7-(6-Fluoropyridin-3-yl)-5H-pyrido[4,3-b]indole (150 mg, 0.57 mmol) in DMF (2.0 mL) was added. The resulting solution was stirred at 80° C. for 4 hours. After cooling to room temperature, the reaction was diluted with EA (30 mL), and the mixture was washed with brine. The organic phase was evaporated under reduced pressure. The residue was purified by silica gel column chromatography on silica gel (DCM/MeOH=4/1) to afford the desired product (200 mg. 72.89% yield) as a colorless oil.

Step 5: tert-butyl 7-(6-((14-hydroxy-3,6,9,12-tetraoxatetradecyl)oxy)pyridin-3-yl)-5H-pyrido[4,3-b]indole-5-carboxylate

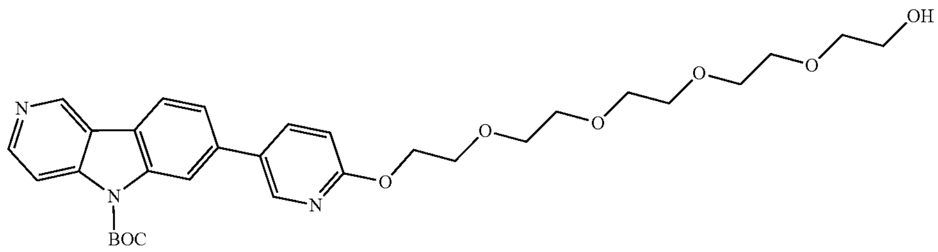 [SMILES: CC(C)(C)OC(=O)n1c2ccncc2c2ccc(-c3ccc(OCCOCCOCCOCCOCCO)nc3)cc21]

To a solution of 14-((5-(5H-pyrido[4,3-b]indol-7-yl)pyridin-2-yl)oxy)-3,6,9,12-tetraoxatetradecan-1-ol (150 mg, 0.31 mmol) in DCM (10 mL) were added $NEt_3$ (94.5 mg, 0.93 mmol) and $Boc_2O$ (102.0 mg, 0.47 mmol). The resulting solution was stirred at ambient temperature for 12 hours. The solvent was removed under vacuum. The residue was diluted with EA (30 mL), and the mixture was washed with brine. The organic phase was dried over anhydrous sodium sulfate, and concentrated in vacuo to afford the desired product (120 mg, 66% yield), which was used in the next step without further purification.

Step 6: tert-butyl 7-(6-((14-((2-(2,6-dioxopiperidin-3-yl)-1,3-dioxoisoindolin-5-yl)oxy)-3,6,9,12-tetraoxatetradecyl)oxy)pyridin-3-yl)-5H-pyrido[4,3-b]indole-5-carboxylate

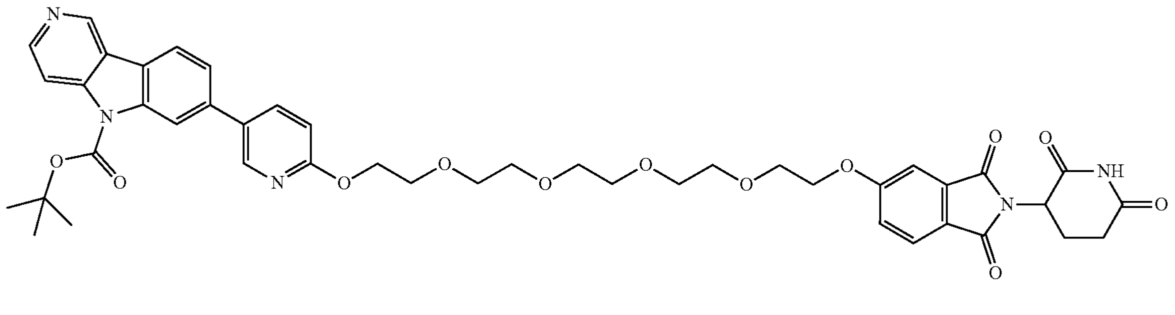 [SMILES: CC(C)(C)OC(=O)n1c2ccncc2c2ccc(-c3ccc(OCCOCCOCCOCCOCCOc4ccc5c(c4)C(=O)N(C4CCC(=O)NC4=O)C5=O)nc3)cc21]

To a solution of tert-butyl 7-(6-((14-hydroxy-3,6,9,12-tetraoxatetradecyl)oxy)pyridin-3-yl)-5H-pyrido[4,3-b]indole-5-carboxylate (120 mg, 0.31 mmol) and $NEt_3$ (93.9 mg, 0.93 mmol) in DCM (10 mL) was added MsCl (38.9 mg, 0.34 mmol) at 0° C. After stirring at 30° C. for 1 hour, the solvent was removed. The residue was diluted with EA (30 mL), and washed with brine. The organic phase was concentrated to give the intermediate mesylate.

To the stirred solution of mesylate (100 mg, 0.15 mmol) in dry DMF (10 mL) were added 2-(2,6-dioxopiperidin-3-yl)-5-hydroxyisoindoline-1,3-dione (45.6 mg, 0.17 mmol) and $K_2CO_3$ (31.4 mg, 0.23 mmol). The resulting mixture was stirred at 68° C. for 4 hours. The mixture was diluted by EtOAc (40 mL), washed with brine twice, and dried over anhydrous sodium sulfate. The organic phase was evaporated under reduced pressure. The residue was purified by prep-TLC (DCM/MeOH=20/1) to afford the desired product as a yellow solid (15 mg, 23.6% yield).

Step 7: 5-((14-((5-(5H-pyrido[4,3-b]indol-7-yl)pyridin-2-yl)oxy)-3,6,9,12-tetraoxatetradecyl)oxy)-2-(2,6-dioxopiperidin-3-yl)isoindoline-1,3-dione

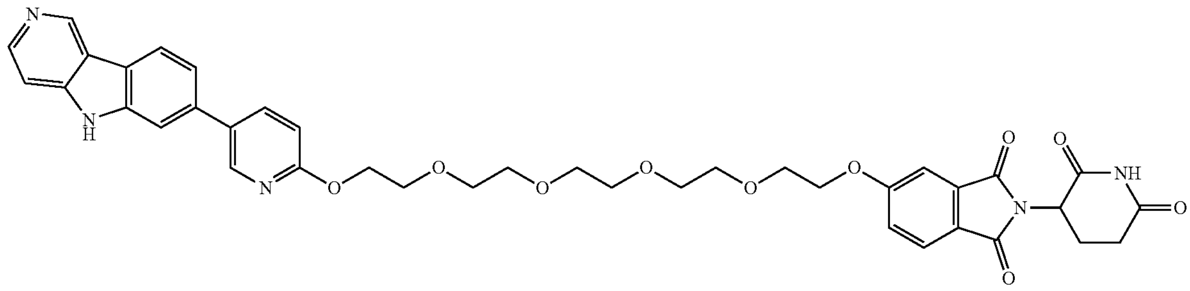

To a solution of tert-butyl 7-(6-((14-((2-(2,6-dioxopiperidin-3-yl)-1,3-dioxoisoindolin-5-yl)oxy)-3,6,9,12-tetraoxatetradecyl)oxy)pyridin-3-yl)-5H-pyrido[4,3-b]indole-5-carboxylate (30 mg, 0.036 mmol) in DCM (2 mL) was added TFA (5 mL). The mixture was stirred at ambient temperature for 4 hours. The mixture was evaporated under reduced pressure. The residue was purified by prep-HPLC to afford the title compound as a white solid (10 mg, 38% yield). $^1$H NMR (400 MHz, $CDCl_3$): δ 12.34-12.48 (m, 1H), 9.19-9.29 (m, 1H), 8.80 (s, 1H), 8.29-8.42 (m, 1H), 8.02-8.14 (m, 1H), 7.95 (s, 1H), 7.69-7.81 (m, 1H), 7.60 (s, 2H), 7.17 (s, 1H), 7.09 (s, 1H), 6.62 (s, 1H), 4.97 (s, 1H), 4.43 (s, 2H), 4.14 (s, 2H), 3.88 (d, J=24.1 Hz, 3H), 3.78 (d, J=8.2 Hz, 3H), 3.69 (d, J=10.0 Hz, 6H), 2.80 (m, 4H), 1.99-2.29 (m, 4H). $(M+H)^+$ 738.3.

Using procedures analogous to those for Compound 51, Compound 50 was also prepared.

Synthetic Scheme for Exemplary Compound 52

Step 1: tert-butyl 4-(2-hydroxyethyl)piperazine-1-carboxylate

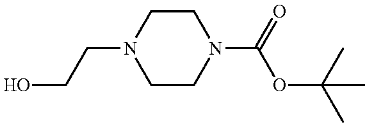 [SMILES: CC(C)(C)OC(=O)N1CCN(CCO)CC1]

The solution of 2-(piperazin-1-yl)ethanol (5 g, 38.5 mmol) and TEA (12 g, 115 mmol) was stirred in DCM at 0° C., $Boc_2O$ was added, then the mixture was stirred at 10° C. overnight. Water was added. Then the mixture was extracted with DCM, dried and concentrated, and filtered through a silica gel pad to get 8.1 g product (92% yield).

Step 2: tert-butyl 4-(2-(prop-2-yn-1-yloxy)ethyl)piperazine-1-carboxylate

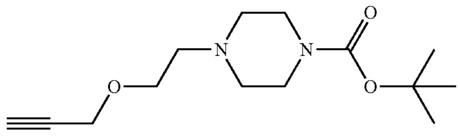 [SMILES: C#CCOCCN1CCN(C(=O)OC(C)(C)C)CC1]

The solution of tert-butyl 4-(2-hydroxyethyl)piperazine-1-carboxylate (3 g, 13 mmol) in THF was stirred at 0° C. NaH (624 mg, 15.6 mmol) was added, then, the mixture was stirred at room temperature for 1 hour. 3-bromoprop-1-yne (1.85 g, 15.6 mmol) was added, and stirring was continued at 70° C. overnight. Then the mixture was cooled to room temperature. Water was added, then the mixture was extracted with EA, dried with $Na_2SO_4$ and concentrated. Filtered through a silica gel pad (EA) to get 1.5 g product (43% yield).

Step 3: tert-butyl 4-(2-((3-(5-bromopyridin-2-yl)prop-2-yn-1-yl)oxy)ethyl)piperazine-1-carboxylate

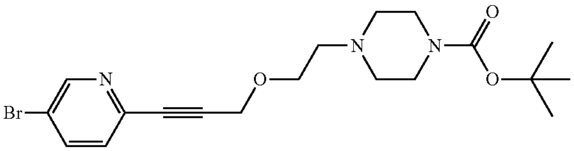 [SMILES: CC(C)(C)OC(=O)N1CCN(CCOCC#Cc2ccc(Br)cn2)CC1]

tert-butyl 4-(2-(prop-2-yn-1-yloxy)ethyl)piperazine-1-carboxylate (500 mg, 1.86 mmol), 2,5-dibromopyridine (442 mg, 1.86 mmol), $Pd(PPh_3)_2Cl_2$ (10%), CuI (11%), DIPEA and $CH_3CN$ were stirred at 5° C. overnight, and EA was added. The mixture was washed by water, concentrated. Then filtered through a silica gel (EA) to get 450 mg product (57% yield).

Step 4: tert-butyl 4-(2-(3-(5-(5H-pyrido[4,3-b]indol-7-yl)pyridin-2-yl)propoxy)ethyl)piperazine-1-carboxylate

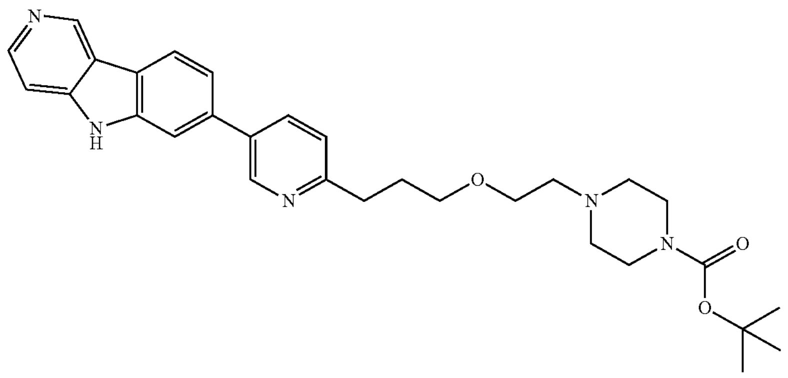 [SMILES: CC(C)(C)OC(=O)N1CCN(CCOCCCc2ccc(-c3ccc4c(c3)[nH]c3ccncc34)cn2)CC1]

7-(4,4,5,5-tetramethyl-1,3,2-dioxaborolan-2-yl)-5H-pyrido[4,3-b]indole-5-carboxylate [prepared by using procedure analogous to that of step 1 of Exemplary Compound 63] (300 mg, 0.76 mmol), Pd(aMphose)$Cl_2$ (50 mg, 10%), and CsF (450 mg, 2.96 mmol) was stirred in $CH_3CN/H_2O$ (10:1) at 120° C. in the microwave for 40 minutes. The mixture was cooled to room temperature, and EA was added. The organic layer was washed by water, then filtered through a silica gel pad (DCM:MeOH=20:1) to get 100 mg tert-butyl 4-(2-(3-(5-(5H-pyrido[4,3-b]indol-7-yl)pyridin-2-yl)prop-2-ynyloxy)ethyl)piperazine-1-carboxylate. The crude product was dissolved in MeOH, Pd/C was added, and the mixture was stirred at 30° C. under 2 Mpa of $H_2$ for 2 hours, filtered and concentrated to produce 100 mg of product (26% yield).

Step 5: 7-(6-(3-(2-(piperazin-1-yl)ethoxy)propyl)pyridin-3-yl)-5H-pyrido[4,3-b]indole

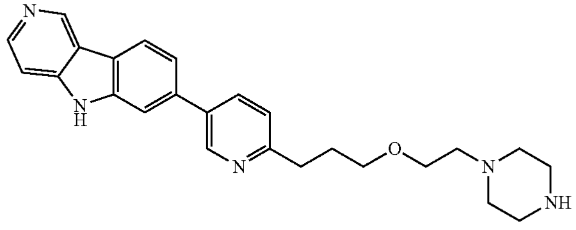 [SMILES: c1cc2[nH]c3cc(-c4ccc(CCCOCCN5CCNCC5)nc4)ccc3c2cn1]

tert-butyl 4-(2-(3-(5-(5H-pyrido[4,3-b]indol-7-yl)pyridin-2-yl)propoxy)ethyl)piperazine-1-carboxylate (100 mg, 0.2 mmol) in HCl/dioxane solution (2 mL) was stirred at 5° C. for 1 hour. Concentrated to obtain 100 mg of crude product.

Step 6: 5-((5-(4-(2-(3-(5-(5H-pyrido[4,3-b]indol-7-yl)pyridin-2-yl)propoxy)ethyl)piperazin-1-yl)pentyl)oxy)-2-(2,6-dioxopiperidin-3-yl)isoindoline-1,3-dione

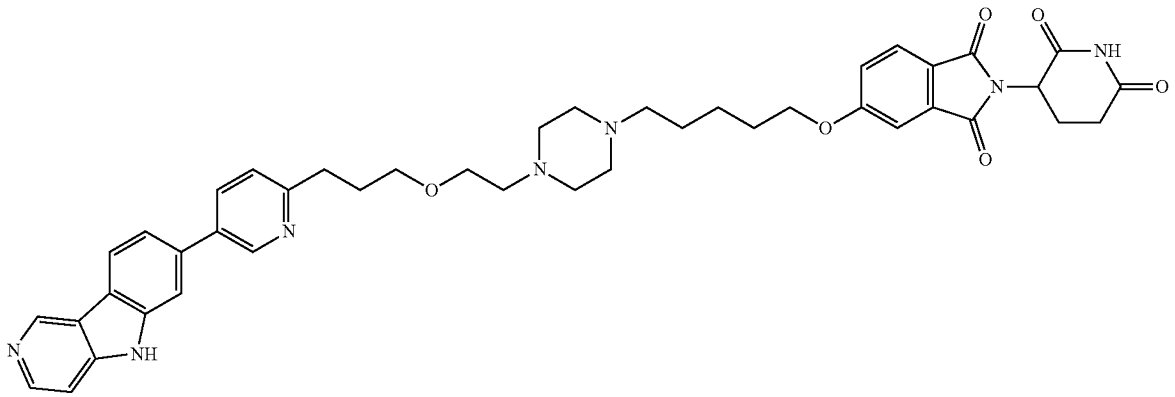 [SMILES: O=C1CCC(N2C(=O)c3ccc(OCCCCCN4CCN(CCOCCCc5ccc(-c6ccc7c(c6)[nH]c6ccncc67)cn5)CC4)cc3C2=O)C(=O)N1]

5-(2-(2,6-dioxopiperidin-3-yl)-1,3-dioxoisoindolin-5-yloxy)pentanal (86 mg, 0.24 mmol), $NaBH_4CN$ (55 mg, 0.48 mmol) and $CH_3COOH$ (cat.) was stirred in MeOH at 5° C. for 3 hours. Then DCM added. The organic layer was washed by water, concentrated, and filtered through silica gel pad (DCM:MeOH=8:1) to afford 11 mg of product.

$^1$HNMR (400 MHz, MeOD): δ 9.25 (s, 1H), 8.79 (s, 1H), 8.37-8.39 (d, J=8 Hz, 1H), 8.28-8.30 (d, J=8 Hz, 1H), 8.11-8.13 (d, J=8 Hz, 1H), 7.80 (s, 1H), 7.75-7.77 (d, J=8 Hz, 1H), 7.60 (s, 1H), 7.49-7.51 (d, J=8 Hz, 1H), 7.43-7.45 (d, J=8 Hz, 1H), 7.33 (s, 1H), 5.07-5.09 (m, 1H), 4.06-4.09 (m, 2H), 3.57-3.60 (m, 2H), 3.51-3.54 (m, 2H), 2.93-2.95 (m, 2H), 2.91-2.93 (m, 1H), 2.59-2.75 (m, 12H), 2.37-2.41 (m, 2H), 2.04-2.06 (m, 3H), 1.78-1.80 (m, 2H), 1.46-1.55 (m, 5H). $(M+H)^+$ 758.3.

Synthetic Scheme for Exemplary Compound 53

Step 1: (((1s,3s)-3-(allyloxy)cyclobutoxy)methyl)benzene

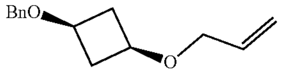 [SMILES: C=CCO[C@H]1C[C@@H](OCc2ccccc2)C1]

To a solution of (1s, 3s)-3-(benzyloxy)cyclobutanol (1.0 g, 5.61 mmol) in DMF (10 mL) was added NaH (60%, 0.336 g, 8.4 mmol) at 0° C. After stirring for 30 min, 3-bromoprop-1-ene was added dropwise at room temperature. The resulting solution was stirred at room temperature for 3 hours. After it was quenched with saturated solution $NH_4Cl$ (20 mL), the mixture was extracted with EtOAc (20 mL×2). The combined organic layers were dried with $Na_2SO_4$ and concentrated under vacuum. The residue was purified by silica gel column with PE/EA=10~1: as eluent to afford the desired product (1.0 g, 82%) as a colorless oil.

Step 2: 3-((1s,3s)-3-(benzyloxy)cyclobutoxy)propan-1-ol

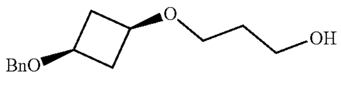 [SMILES: OCCCO[C@H]1C[C@@H](OCc2ccccc2)C1]

To a solution of (((1s,3s)-3-(allyloxy)cyclobutoxy)methyl)benzene (1.0 g, 4.58 mmol) in THF (20 mL) was added dicyclohexylborane in THF (1.0 M, 9.0 mL) at 0° C. After it was stirred at room temperature for 4 hours, NaOH (37%, 3.0 mL) and $H_2O_2$ (30%, 3.0 mL) were added to the mixture at 0° C. The resulting solution was stirred at room temperature overnight. The reaction was quenched with $Na_2S_2O_3$ (20 mL). The mixture was taken up in DCM. The organic phase was dried with $Na_2SO_4$ and concentrated under vacuum. The residue was purified on silica gel column with PE/EA=2:1 as eluent to afford the desired product (1.0 g, 100%) as a colorless oil.

Step 3: tert-butyl 4-(3-((1s,3s)-3-(benzyloxy)cyclobutoxy)propyl)piperazine-1-carboxylate

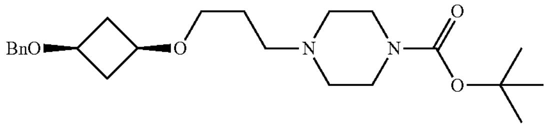 [SMILES: CC(C)(C)OC(=O)N1CCN(CCCO[C@H]2C[C@@H](OCc3ccccc3)C2)CC1]

To a solution of 3-((1s,3s)-3-(benzyloxy)cyclobutoxy)propan-1-ol (1.0 g, 4.58 mmol) and TEA (2.0 g, 19.8 mmol) in DCM (10 mL) was added MsCl (0.97 g, 9.2 mmol) at 0° C. After stirring at room temperature for 2 hours, the reaction was quenched with saturated solution of sodium bicarbonate (20 mL), and the mixture was extracted DCM (20 mL×2). The combined organic layers were dried with $Na_2SO_4$, and concentrated under vacuum to afford the desired product (1.1 g, crude), which was used in the next reaction without further purification.

To a solution of the above intermediate (1.1 g, crude) in DMF (10 mL) was added tert-butyl piperazine-1-carboxylate (1.60 g, 9.2 mmol). The resulting solution was heated to 90° C. for 4 hours. After cooling to room temperature, the reaction was quenched with water (20 mL) and the mixture was extracted with EtOAc (20 mL×3). The combined organic layers were dried over $Na_2SO_4$, and concentrated under vacuum. The residue was purified by silica gel column with PE/EA=2:1 as eluent to afford the desired product (980 mg, 58%) as a colorless oil.

Step 4: tert-butyl 4-(3-((1s,3s)-3-hydroxycyclobutoxy)propyl)piperazine-1-carboxylate

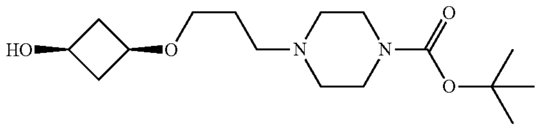 [SMILES: CC(C)(C)OC(=O)N1CCN(CCCO[C@H]2C[C@@H](O)C2)CC1]

A mixture of tert-butyl 4-(3-((1s,3s)-3-(benzyloxy)cyclobutoxy)propyl)piperazine-1-carboxylate (980 mg, 2.42 mmol) and $Pd(OH)_2/C$ (300 mg, 20%) in $CH_3OH$ (10 mL) was stirred at room temperature overnight under $H_2$ at 1 atm. The mixture was filtered through Celite, and the filtrate was concentrated to afford the desired product (700 mg, crude) which was used in the next reaction without further purification.

Step 5: tert-butyl 4-(3-((1s,3s)-3-((5-(5H-pyrido[4,3-b]indol-7-yl)pyridin-2-yl)oxy)cyclobutoxy)propyl)piperazine-1-carboxylate

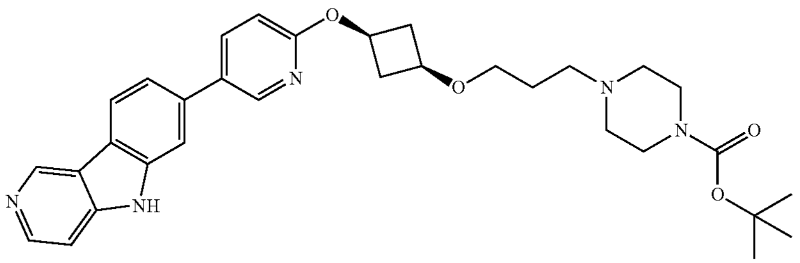 [SMILES: CC(C)(C)OC(=O)N1CCN(CCCO[C@H]2C[C@@H](Oc3ccc(-c4ccc5c(c4)[nH]c4ccncc45)cn3)C2)CC1]

To a solution of tert-butyl 4-(3-((1s,3s)-3-hydroxycyclobutoxy)propyl)piperazine-1-carboxylate (180 mg, 0.57 mmol) and 7-(6-Fluoropyridin-3-yl)-5H-pyrido[4,3-b]indole (100 mg, 0.379 mmol) in NMP (10 mL) was added NaH (60%, 100 mg, 2.5 mmol) at room temperature. The resulting solution was heated to 90° C. for 2 hours. After cooling to room temperature, the reaction was quenched with saturated solution of $NH_4Cl$ (20 mL), and the mixture was extracted with EtOAc (20 mL×3). The combined organic layers were dried with $Na_2SO_4$ and concentrated under vacuum. The residue was purified by prep-TLC with DCM/$CH_3OH$ (15:1) to afford the desired product (120 mg, 0.21 mmol) as a brown solid.

Step 6: 7-(6-((1s,3s)-3-(3-(piperazin-1-yl)propoxy)cyclobutoxy)pyridin-3-yl)-5H-pyrido[4,3-b]indole

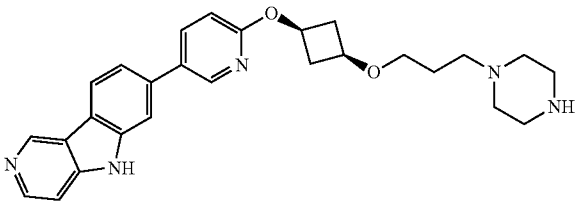 [SMILES: c1cc2[nH]c3cc(-c4ccc(O[C@H]5C[C@@H](OCCCN6CCNCC6)C5)nc4)ccc3c2cn1]

A mixture of tert-butyl 4-(3-((1s,3s)-3-((5-(5H-pyrido[4,3-b]indol-7-yl)pyridin-2-yl)oxy)cyclobutoxy)propyl)piperazine-1-carboxylate (120 mg, 0.21 mmol) in $CH_3OH$ (2.0 mL) and HCl in 1,4-dioxane (4.0 mL) was stirred at room temperature for 2 hours. The solvent was removed under vacuum to afford the desired product (100 mg, crude), which was used in the next reaction without further purification.

Step 7: 5-(4-(3-((1s,3s)-3-((5-(5H-pyrido[4,3-b]indol-7-yl)pyridin-2-yl)oxy)cyclobutoxy)propyl)piperazin-1-yl)-2-(2,6-dioxopiperidin-3-yl)isoindoline-1,3-dione

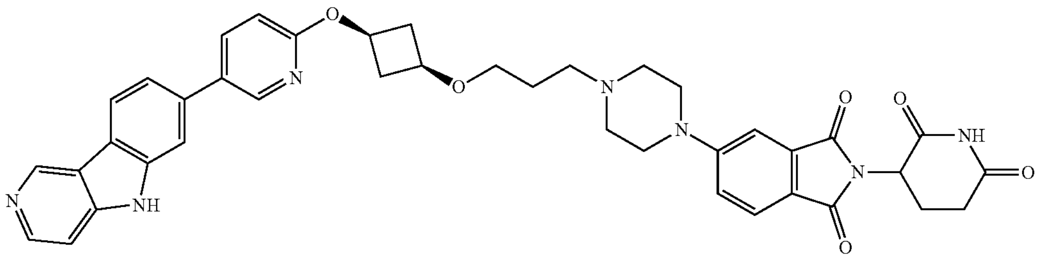 [SMILES: O=C1CCC(N2C(=O)c3ccc(N4CCN(CCCO[C@H]5C[C@@H](Oc6ccc(-c7ccc8c(c7)[nH]c7ccncc78)cn6)C5)CC4)cc3C2=O)C(=O)N1]

To a mixture of 7-(6-((1s,3s)-3-(3-(piperazin-1-yl)propoxy)cyclobutoxy)pyridin-3-yl)-5H-pyrido[4,3-b]indole (80 mg, crude) and DIEA (300 mg, 2.36 mmol) in NMP (2.0 mL) was added 2-(2,6-dioxopiperidin-3-yl)-5-fluoroisoindoline-1,3-dione (100 mg, 0.36 mmol). The mixture was microwave heated at 130° C. for 45 minutes. After cooling to room temperature, the reaction was taken up with EtOAc (100 mL). The mixture was washed with brine (20 mL×3). The organic phase was dried with $Na_2SO_4$, and concentrated under vacuum. The residue was purified by prep-TLC with DCM/$CH_3OH$/$NH_3H_2O$ (15:1:0.1) to afford the title product (16.0 mg, 13%) as a yellow solid.

$^1H$ NMR (400 MHz, $CDCl_3$): δ 9.34 (s, 1H), 8.55 (d, J=5.6 Hz, 1H), 8.44 (m, 2H), 8.20 (d, J=8.4 Hz, 1H), 7.87-7.92 (m, 3H), 7.68 (d, J=8.4 Hz, 1H), 7.60 (s, 1H), 7.48-7.50 (m, 1H), 7.38 (d, J=5.6 Hz, 1H), 7.06 (m, 1H), 6.84 (d, J=8.8 Hz, 2H), 4.93-4.94 (m, 2H), 3.75 (m, 2H), 3.42-3.49 (m, 6H), 2.72-2.98 (m, 5H), 2.61 (s, 4H), 2.53 (t, J=7.2 Hz, 2H), 2.15-2.18 (m, 2H), 1.81 (t, J=6.8 Hz, 2H). $(M+H)^+$ 714.3

Synthetic Scheme for Exemplary Compound 55

Step 1: tert-butyl 1-4-(5-(3-methoxy-3-oxoprop-1-en-1-yl)pyridin-2-yl)piperazine-1-carboxylate

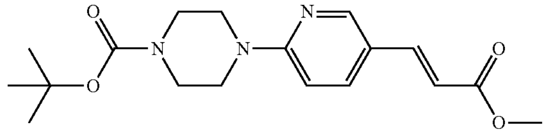 [SMILES: COC(=O)/C=C/c1ccc(N2CCN(C(=O)OC(C)(C)C)CC2)nc1]

To a solution of tert-butyl 4-(5-formylpyridin-2-yl)piperazine-1-carboxylate (1.0 g, 3.44 mmol) and methyl 2-(dimethoxyphosphoryl)acetate (750 mg, 4.12 mmol) in THF (15 ml) was added DBU (1.57 g, 10.3 mmol). The reaction mixture was stirred at room temperature overnight. After it was quenched with water $H_2O$ (10 mL), the mixture was extracted with ethyl acetate (50 mL). The organic phase was washed with brine, and dried over $Na_2SO_4$. It was filtered, and concentrated under vacuum. The residue was broken with petroleum ether to afford the desired product (800 mg, 2.3 mmol, yield: 66.9%) as a pale solid.

Step 2: tert-butyl 4-(5-(3-hydroxypropyl)pyridin-2-yl)piperazine-1-carboxylate

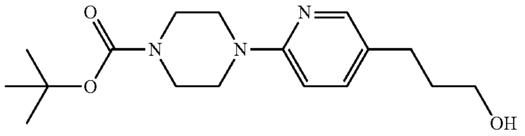 [SMILES: CC(C)(C)OC(=O)N1CCN(c2ccc(CCCO)cn2)CC1]

To a solution of tert-butyl 1-4-(5-(3-methoxy-3-oxoprop-1-en-1-yl)pyridin-2-yl)piperazine-1-carboxylate (800 mg, 2.3 mmol) in $CH_3OH$ (8 mL) and THE (35 mL) was added $NaBH_4$ (874 mg, 23.0 mmol). The mixture was heated to 80° C. for 3 hours. After cooling to room temperature, the reaction was quenched with 2N $NH_4Cl$, and the mixture was extracted with EtOAc (80 mL×3). The combined organic layers were washed with brine, and dried ($Na_2SO_4$), filtered and concentrated under reduced pressure. The residue was purified by silica gel column (EA:PE=1:1) to give the desired compound (420 mg, 1.31 mmol, yield: 57.0%) as a yellow oil.

Step 3: tert-butyl 4-(5-(3-((methylsulfonyl)oxy)propyl)pyridin-2-yl)piperazine-1-carboxylate

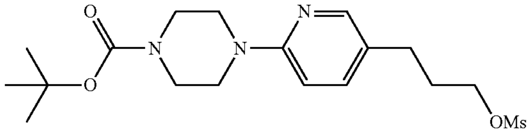 [SMILES: CC(C)(C)OC(=O)N1CCN(c2ccc(CCCOS(C)(=O)=O)cn2)CC1]

To a solution of tert-butyl 4-(5-(3-hydroxypropyl)pyridin-2-yl)piperazine-1-carboxylate (50 mg, 0.16 mmol) and $Et_3N$ (48 mg, 0.48 mmol) in DCM (2 mL) was added MsCl (27 mg, 0.23 mmol). The reaction was stirred at room temperature for 1 hour. After it was quenched with water $H_2O$ (30 mL), the mixture was extracted with DCM (20 mL). The organic phase was washed with brine, dried over $Na_2SO_4$, filtered, and concentrated under vacuum to give the crude desired compound (64 mg) as a yellow oil which was used in the next reaction without further purification.

Step 4: tert-butyl 4-(5-(3-((2-(2,6-dioxopiperidin-3-yl)-1,3-dioxoisoindolin-5-yl)oxy)propyl)pyridin-2-yl)piperazine-1-carboxylate

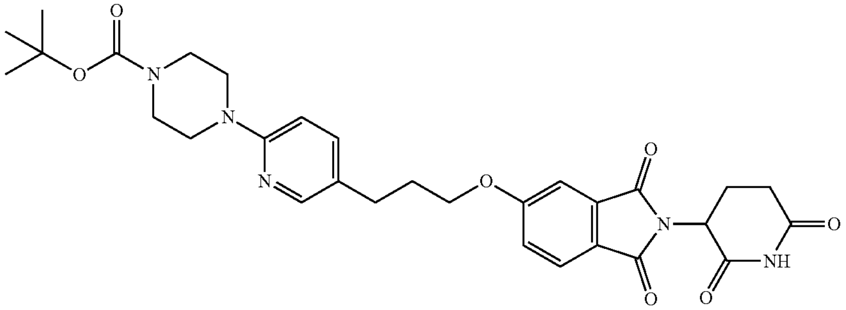 [SMILES: CC(C)(C)OC(=O)N1CCN(c2ccc(CCCOc3ccc4c(c3)C(=O)N(C3CCC(=O)NC3=O)C4=O)cn2)CC1]

To a solution of tert-butyl 4-(5-(3-((methylsulfonyl)oxy)propyl)pyridin-2-yl)piperazine-1-carboxylate (64 mg, 0.16 mmol) and 2-(2,6-dioxopiperidin-3-yl)-5-hydroxyisoindoline-1,3-dione (66 mg, 0.24 mmol) in DMF (5 ML) was added $K_2CO_3$ (55 mg, 0.40 mmol). The reaction mixture was stirred at 90° C. for 2 hours. After cooling to room temperature, the reaction was quenched water (5 mL), and the mixture was extracted with dichloromethane (30 mL). The organic phase was washed with water and brine, dried over $Na_2SO_4$, filtered, and concentrated under reduced pressure. The residue was purified by silica gel column (MeOH:DCM=1:100-1:20) to give the title product (30 mg, 0.052 mmol, yield: 32%).

Step 5: 2-(2,6-dioxopiperidin-3-yl)-5-(3-(6-(piperazin-1-yl)pyridin-3-yl)propoxy)isoindoline-1,3-dione

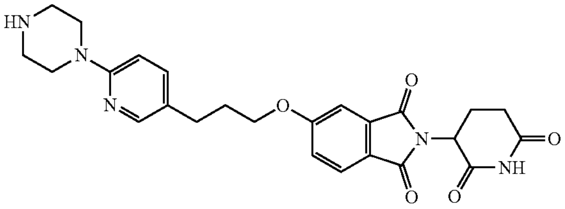 [SMILES: O=C1CCC(N2C(=O)c3ccc(OCCCc4ccc(N5CCNCC5)nc4)cc3C2=O)C(=O)N1]

To a solution of tert-butyl 4-(5-(3-((2-(2,6-dioxopiperidin-3-yl)-1,3-dioxoisoindolin-5-yl)oxy)propyl)pyridin-2-yl)piperazine-1-carboxylate (200 mg, 0.39 mmol) in dioxane (10 mL) was added 6N HCl in dioxane (2 mL, 12.0 mmol). The reaction mixture was stirred at room temperature for 2 hours. The solvent was removed under reduced pressure to give the crude title product (200 mg) as a yellow solid.

Step 6: (6-(3-Hydroxyprop-1-yn-1-yl)pyridin-3-yl)boronic acid

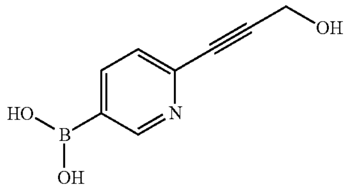 [SMILES: OCC#Cc1ccc(B(O)O)cn1]

To a solution of (6-bromopyridin-3-yl)boronic acid (1.0 g, 4.95 mmol) and prop-2-yn-1-ol (830 mg, 14.8 mmol) in THF (30 mL) were added $PdCl_2(PPh_3)_2$ (350 mg, 0.50 mmol), $^{i}Pr_2NH$ (2 g, 19.8 mmol) and CuI (95 mg, 0.5 mmol). The reaction mixture was stirred at room temperature overnight. The mixture was filtered through Celite, and to the filtrate was added 1N NaOH (10 mL). The mixture was extracted with DCM. The pH was adjusted to around 6 with 2N HCl. The aqueous solution was extracted with ethyl acetate. The combined EtOAc layers were dried over $Na_2SO_4$, filtered, and evaporated to dryness under reduced pressure to give the desired compound (500 mg, 2.82 mmol, yield 57%) as a pale solid.

Step 7: 3-(5-(5H-pyrido[4,3-b]indol-7-yl)pyridin-2-yl)prop-2-yn-1-ol

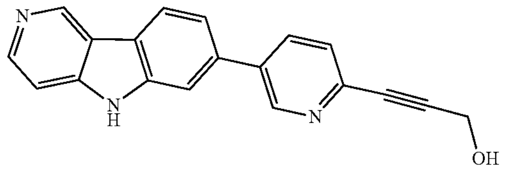 [SMILES: OCC#Cc1ccc(-c2ccc3c(c2)[nH]c2ccncc23)cn1]

To the mixture of 7-bromo-5H-pyrido[4,3-b]indole (50 mg, 0.20 mmol) and (6-(3-Hydroxyprop-1-yn-1-yl)pyridin-3-yl)boronic acid (53 mg, 0.30 mmol) in dioxane (10 mL) and water (1.0 mL) were added $PdCl_2(dppf)$ (29 mg, 0.04 mmol), $Cs_2CO_3$ (130 mg, 0.40 mmol) and $^{t}Bu_3PHBF_4$ (23 mg, 0.08 mmol). The mixture was stirred at 100° C. for 3 hours under $N_2$ atmosphere. After cooling to room temperature, the reaction was quenched with water (3 mL), and the mixture was extracted with EtOAc (20 ml×3). The combined organic layers were washed with brine, dried ($Na_2SO_4$), filtered and concentrated under reduced pressure. The residue was purified on silica gel column (MeOH:DCM=1:20-1:10) to give the desired compound (30 mg, 0.10 mmol, yield: 50.0%) as a yellow solid.

Step 8: 3-(5-(5H-pyrido[4,3-b]indol-7-yl)pyridin-2-yl)propan-1-ol

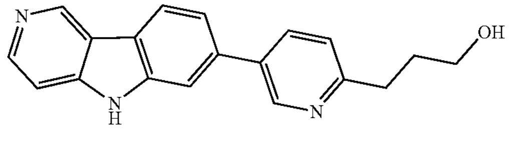 [SMILES: OCCCc1ccc(-c2ccc3c(c2)[nH]c2ccncc23)cn1]

To a solution of 3-(5-(5H-pyrido[4,3-b]indol-7-yl)pyridin-2-yl)prop-2-yn-1-ol (30 mg, 0.10 mmol) in MeOH (2 mL) was added $Pd(OH)_2/C$ (20%, 10 mg) and cat. Conc. HCl (0.1 mL). The reaction was stirred at room temperature for 2 hours under $H_2$ atmosphere. The mixture was filtered through Celite, and the filtrate was concentrated to give the crude desired compound (30 mg) as a yellow oil.

Step 9: 3-(5-(5H-pyrido[4,3-b]indol-7-yl)pyridin-2-yl)propanal

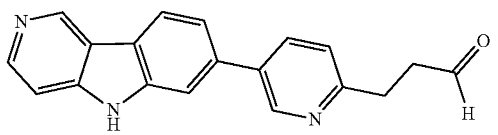 [SMILES: O=CCCc1ccc(-c2ccc3c(c2)[nH]c2ccncc23)cn1]

A solution of 3-(5-(5H-pyrido[4,3-b]indol-7-yl)pyridin-2-yl)propan-1-ol (100 mg, 0.33 mmol) in DMSO (4 mL) was mixed with IBX (231 mg, 0.82 mmol). The reaction mixture was stirred at 25° C. for 2 hours. The reaction was quenched with saturated $Na_2S_2O_3$ (2 mL) and saturated $NaHCO_3$ (2 mL). The mixture was extracted with dichloromethane (30 mL). The organic phase was washed with water and brine. It was dried over $Na_2SO_4$, filtered, and concentrated under reduced pressure to give the crude title product (60 mg) as a yellow oil.

Step 10: 5-(3-(6-(4-(3-(5-(5H-pyrido[4,3-b]indol-7-yl)pyridin-2-yl)propyl)piperazin-1-yl)pyridin-3-yl)propoxy)-2-(2,6-dioxopiperidin-3-yl)isoindoline-1,3-dione

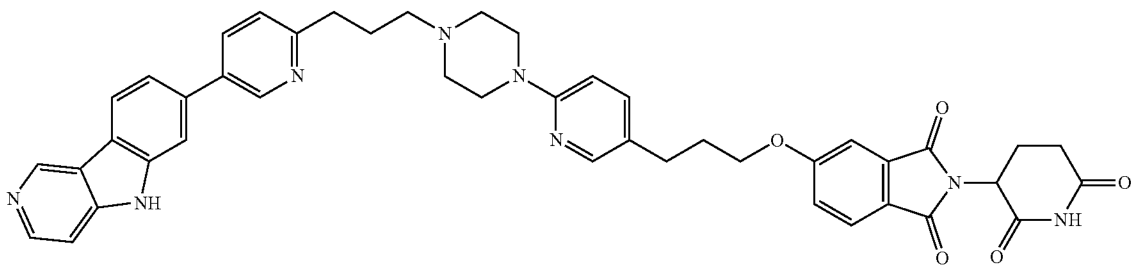 [SMILES: O=C1CCC(N2C(=O)c3ccc(OCCCc4ccc(N5CCN(CCCc6ccc(-c7ccc8c(c7)[nH]c7ccncc78)cn6)CC5)nc4)cc3C2=O)C(=O)N1]

To a solution of 3-(5-(511-pyrido[4,3-b]indol-7-yl)pyridin-2-yl)propanal (100 mg, crude) in MeOH (10 mL) were added 2-(2,6-dioxopiperidin-3-yl)-5-(3-(6-(piperazin-1-yl)pyridin-3-yl)propoxy)isoindoline-1,3-dione (100 mg, 0.21 mmol) and $NaBH_3CN$ (41 mg, 0.66 mmol). The reaction mixture was stirred at room temperature for 1 hour. The mixture was diluted with water (6 ml) and extracted with DCM (20 mL×2). The combined organic layers were washed with water and brine, dried over $Na_2SO_4$, filtered, and concentrated under reduced pressure. The residue was purified by prep-HPLC to give the desired product (15 mg, 0.02 mmol) as a white solid.

$^1$H NMR (400 MHz, MeOD): δ 9.62 (s, 1H), 9.03 (s, 1H), 8.58 (d, J=6.8 Hz, 1H), 8.52 (d, J=8.0 Hz, 1H), 8.31-8.40 (m, 1H), 8.08 (s, 1H), 7.87-7.99 (m, 2H), 7.78-7.87 (m, 3H), 7.68-7.72 (m, 1H), 7.26-7.30 (m, 2H), 7.10-7.14 (m, 1H), 5.08-5.12 (m, 1H), 4.17 (t, J=6.0 Hz, 2H), 3.81-3.92 (m, 4H), 3.50-3.60 (m, 4H), 3.30-3.40 (m, 2H), 3.10-3.18 (m, 2H), 2.71-2.86 (m, 5H), 2.30-2.33 (m, 2H), 2.10-2.16 (m, 3H). $(M+H)^+$ 763.3

Synthetic Scheme for Exemplary Compound 56

5-((5-(4-(2-((1s,3s)-3-((5-(5H-pyrido[4,3-b]indol-7-yl)pyridin-2-yl)oxy)cyclobutoxy)ethyl)piperazin-1-yl)pentyl)oxy)-2-(2,6-dioxopiperidin-3-yl)isoindoline-1,3-dione

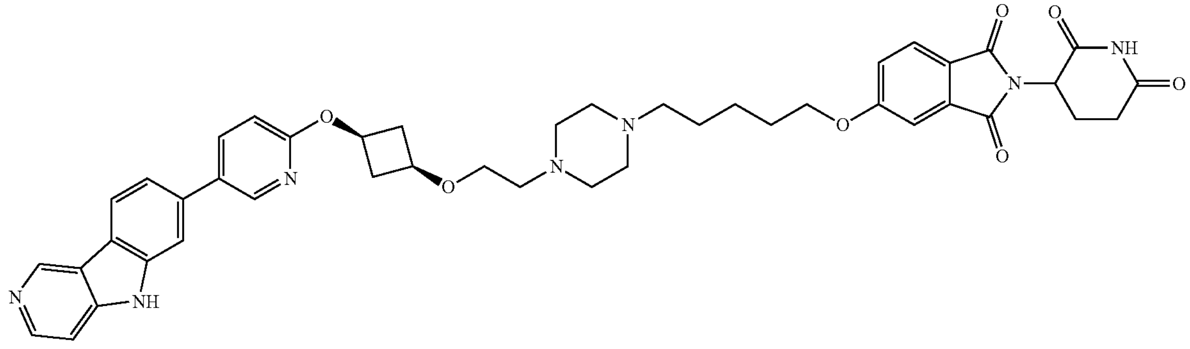 [SMILES: O=C1CCC(N2C(=O)c3ccc(OCCCCCN4CCN(CCO[C@H]5C[C@@H](Oc6ccc(-c7ccc8c(c7)[nH]c7ccncc78)cn6)C5)CC4)cc3C2=O)C(=O)N1]

Step 1: (1s,3s)-3-(benzyloxy)cyclobutan-1-ol

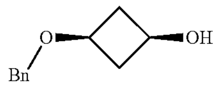 [SMILES: O[C@H]1C[C@@H](OCc2ccccc2)C1]

To a solution of 3-(benzyloxy)cyclobutanone (10.0 g, 56.75 mmol) in EtOH (100 mL) was added $NaBH_4$ (4.3 g, 68.1 mmol) at 0° C. The mixture was stirred at 10° C. for 2 hours. After the reaction was quenched with 10% $NH_4Cl$, the mixture was extracted with ethyl acetate (200 mL). The combined organic layers were washed with brine (150 mL), dried over anhydrous sodium sulfate and concentrated under vacuum to give crude the desired product (9.5 g) as a colorless oil, which was used in the next step without further purification.

Step 2: (((1s,3s)-3-(2,2-diethoxyethoxy)cyclobutoxy)methyl)benzene

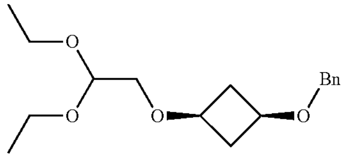 [SMILES: CCOC(CO[C@H]1C[C@@H](OCc2ccccc2)C1)OCC]

To a solution of (1s,3s)-3-(benzyloxy)cyclobutan-1-ol (300 mg, crude, 1.69 mmol) in THF (10 mL) was added NaH (168 mg, 4.22 mmol, 60%). After stirring at 5° C. for 0.5 hours, 2-bromo-1,1-diethoxyethane (333 mg, 3.38 mmol) was added. The resulting mixture was stirred at 70° C. for 18 hours. After cooling to room temperature, the reaction was diluted with water (50 mL), and the mixture was extracted with EA. The organic phase was washed with brine, dried over $MgSO_4$, and concentrated. The residue was purified by chromatography (silica gel, PE:EA (50:1, v:v)) to afford the desired compound (220 mg) as a yellow solid.

Step 3: 2-((1s,3s)-3-(benzyloxy)cyclobutoxy)acetaldehyde

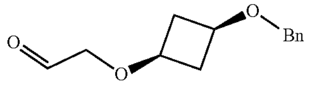 [SMILES: O=CCO[C@H]1C[C@@H](OCc2ccccc2)C1]

To a solution of (((1s,3s)-3-(2,2-diethoxyethoxy)cyclobutoxy)methyl)benzene (220 mg, 0.74 mmol) in $CH_3CN$ (5 mL) was added HCl (2 mL, 2.5 mol/L in $H_2O$). The resulting mixture was stirred at 70° C. for 2 hours. TLC (PE:EA=3:1, Rf=0.5) showed that starting material was consumed. The mixture was diluted with water (50 mL) and extracted with EA. The organic phase was washed with $NaHCO_3$, brine. The solution was dried over $MgSO_4$ and concentrated to afford the desired compound (170 mg, crude) as a yellow oil, which was used in the next step without further purification.

Step 4: tert-butyl 4-(2-((1s,3s)-3-(benzyloxy)cyclobutoxy)ethyl)piperazine-1-carboxylate

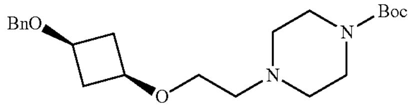 [SMILES: CC(C)(C)OC(=O)N1CCN(CCO[C@H]2C[C@@H](OCc3ccccc3)C2)CC1]

To a solution of 2-((1s,3s)-3-(benzyloxy)cyclobutoxy)acetaldehyde (170 mg, crude, 0.772 mmol) in MeOH (10 mL) were added tert-butyl piperazine-1-carboxylate (215 mg, 1.16 mmol), AcOH (1 drop) and $NaBH_3CN$ (97 mg, 154 mmol). The resulting mixture was stirred at 10° C. for 18 hours. The reaction mixture was diluted with water (50 mL) and the mixture was extracted with EA. The organic phase was washed with brine, dried over $MgSO_4$, and concentrated. The residue was purified by chromatography (silica gel, PE:EA (1:1, v:v)) to afford the desired compound (280 mg) as a colorless oil.

Tert-Butyl 4-(2-((1s,3s)-3-(benzyloxy)cyclobutoxy)ethyl)piperazine-1-carboxylate was converted to the title compound, 5-((5-(4-(2-((1s,3s)-3-((5-(5H-pyrido[4,3-b]indol-7-yl)pyridin-2-yl)oxy)cyclobutoxy)ethyl)piperazin-1-yl)pentyl)oxy)-2-(2,6-dioxopiperidin-3-yl)isoindoline-1,3-dione, according to the scheme below using procedures described above for Exemplary Compound 42 and Exemplary Compound 53.

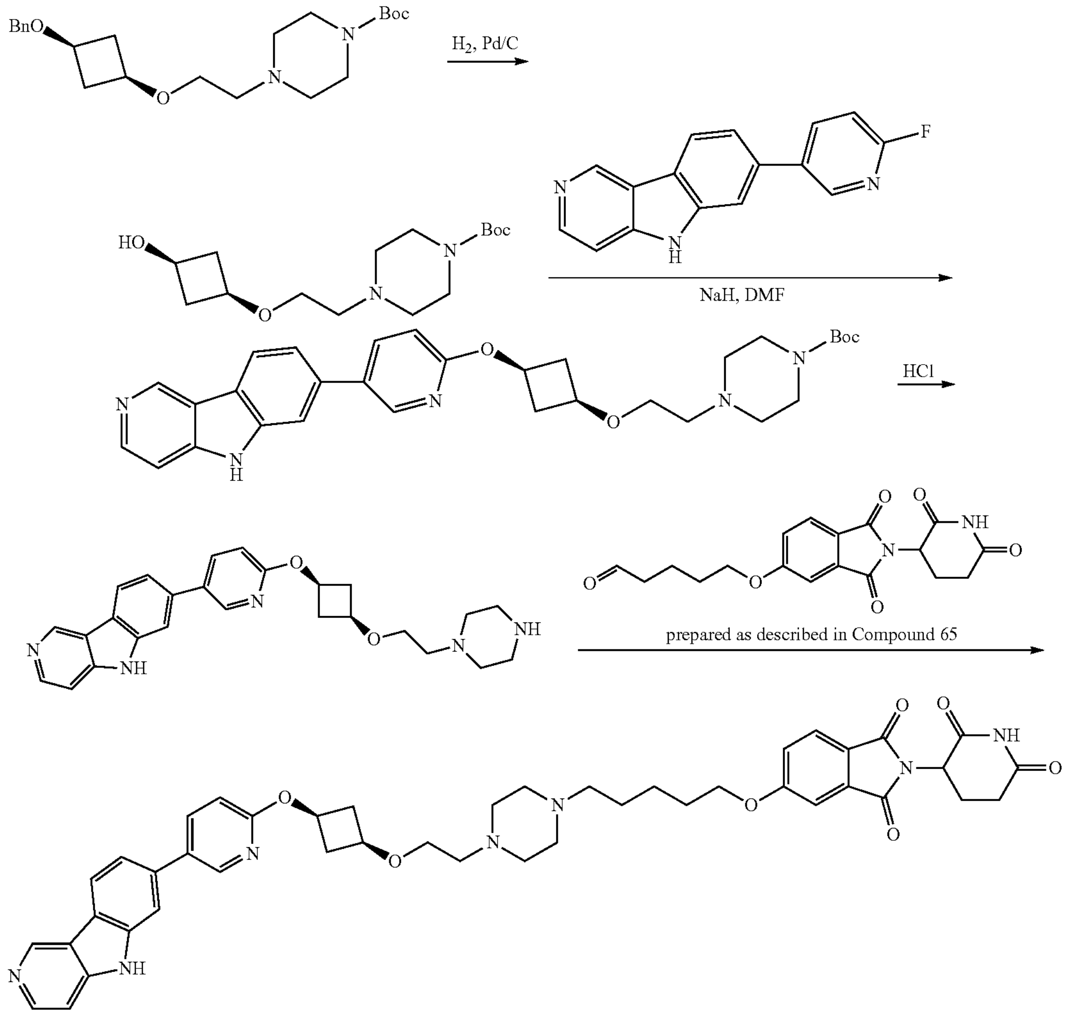
Compound 56
Exemplary Compound 56: $^1$H NMR (400 MHz, $CDCl_3$) δ 9.33 (s, 1H), 8.89 (s, 1H), 8.53 (s, 1H), 8.42 (s, 1H), 8.18 (d, J=8.2 Hz, 1H), 7.87 (d, J=6.2 Hz, 1H), 7.77 (d, J=8.2 Hz, 1H), 7.62 (s, 1H), 7.49 (d, J=7.7 Hz, 1H), 7.42 (s, 1H), 7.29 (d, J=11.5 Hz, 1H), 7.17 (d, J=6.5 Hz, 1H), 6.82 (d, J=8.2 Hz, 1H), 5.34 (s, 2H), 5.00-4.87 (m, 1H), 4.07 (s, 2H), 3.75 (s, 1H), 3.57 (s, 1H), 3.04-2.49 (m, 10H), 2.20 (m, 4H), 2.01 (s, 4H), 1.85 (s, 3H), 1.75-1.55 (m, 3H), 1.52 (s, 2H).
Exemplary Compound 54 and Exemplary Compound 58 were prepared according to the schemes below and using procedures analogous to those described above.
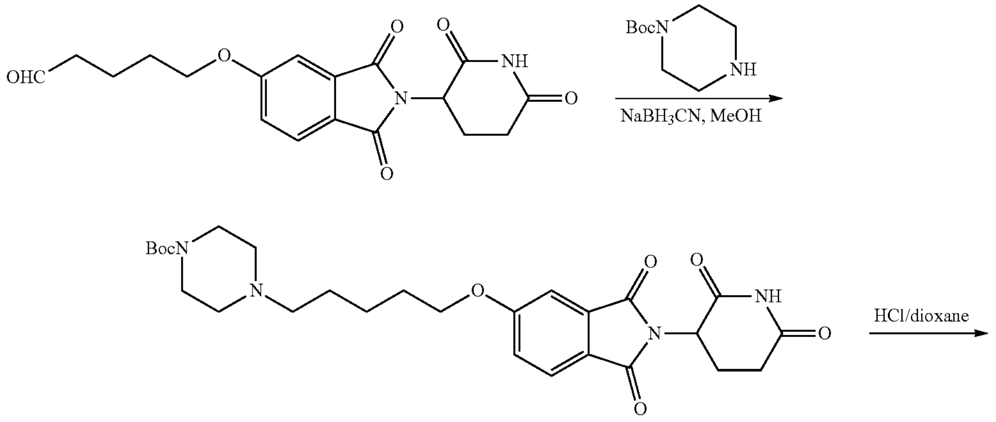

-continued
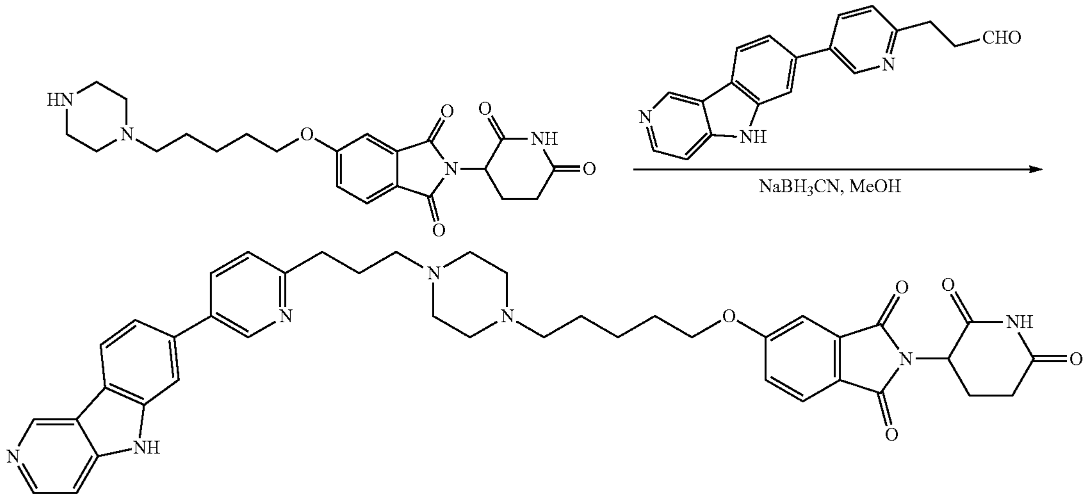
Exemplary Compound 54
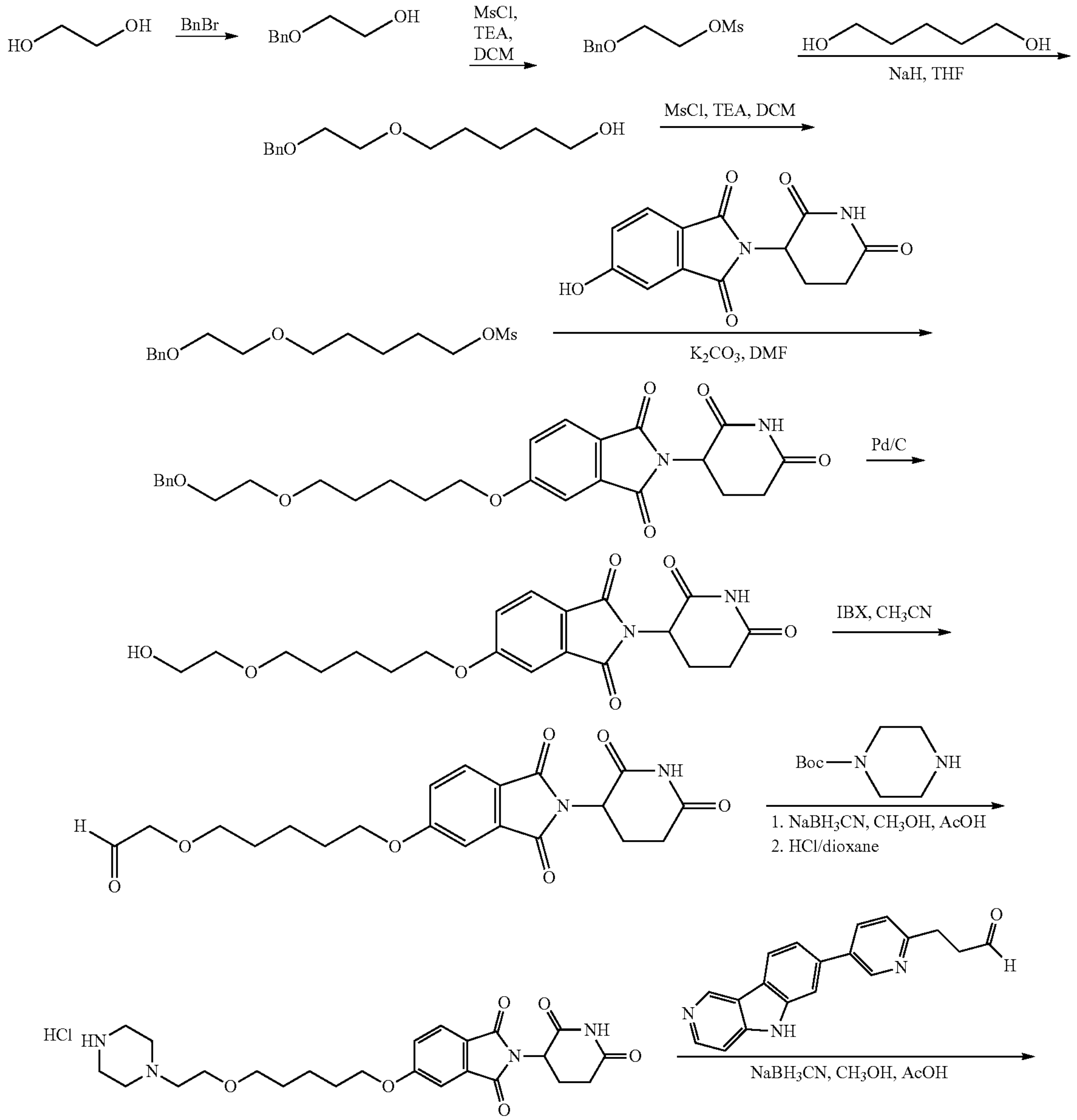

-continued

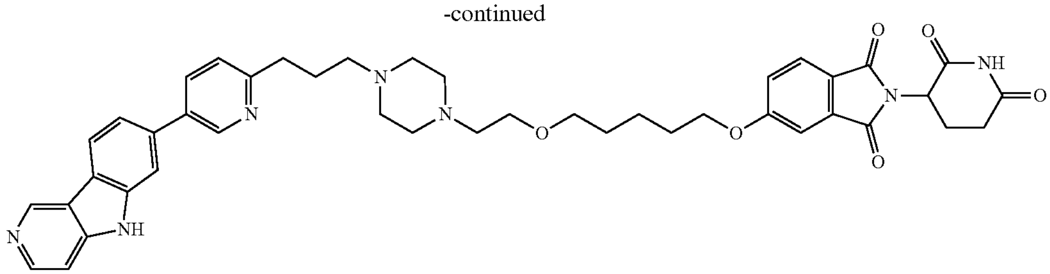

Exempry Compound 58

Synthetic Scheme for Exemplary Compound 57

Step 1: Benzyl 4-(5H-pyrido[4,3-b]indol-7-yl)-3,6-dihydropyridine-1(2H)-carboxylate

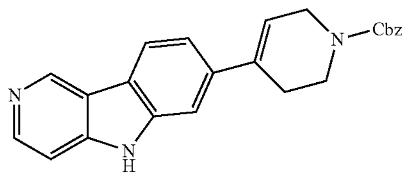 [SMILES: O=C(OCc1ccccc1)N1CC=C(c2ccc3c(c2)[nH]c2ccncc23)CC1]

A mixture of 7-bromo-5H-pyrido[4,3-b]indole (492 mg, 2 mmol), benzyl 4-(4,4,5,5-tetramethyl-1,3,2-dioxaborolan-2-yl)-3,6-dihydropyridine-1(2H)-carboxylate (755 mg, 2.2 mmol), Pd(aMphose)$Cl_2$ (146 mg, 0.2 mmol) and CsF (1.2 g, 8 mmol) in dioxane/$H_2O$ (20 mL/2 mL) was stirred at 90° C. for 16 hours. After cooling to room temperature, the reaction was quenched by the addition of water (30 mL). The mixture was extracted with ethyl acetate (20 mL×3). The combined organic layers were washed with brine (20 mL×2), dried over anhydrous sodium sulfate and concentrated under vacuum. The residue was applied onto a silica gel column eluting with dichloromethane/methanol to afford 260 mg (0.68 mmol, 34%) of the desired product.

Step 2: 7-(piperidin-4-yl)-5H-pyrido[4,3-b]indole

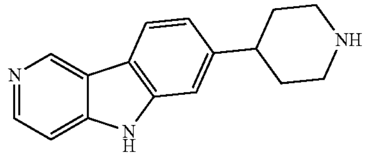 [SMILES: c1cc2[nH]c3cc(C4CCNCC4)ccc3c2cn1]

To a solution of benzyl 4-(5H-pyrido[4,3-b]indol-7-yl)-3,6-dihydropyridine-1(2H)-carboxylate (130 mg, 0.34 mmol) and one drop conc. HCl in $CH_3OH$ (10 mL) was added Pd/C (13 mg, 10%) at room temperature. The resulting solution was stirred at room temperature overnight under 1 atm of $H_2$. Then the solid was filtered off and the filtrate was concentrated under vacuum to afford crude product (80 mg), which was used in the next reaction without further purification.

Step 3: 5-((14-(4-(5H-pyrido[4,3-b]indol-7-yl)piperidin-1-yl)-3,6,9,12-tetraoxatetradecyl)oxy)-2-(2,6-dioxopiperidin-3-yl)isoindoline-1,3-dione

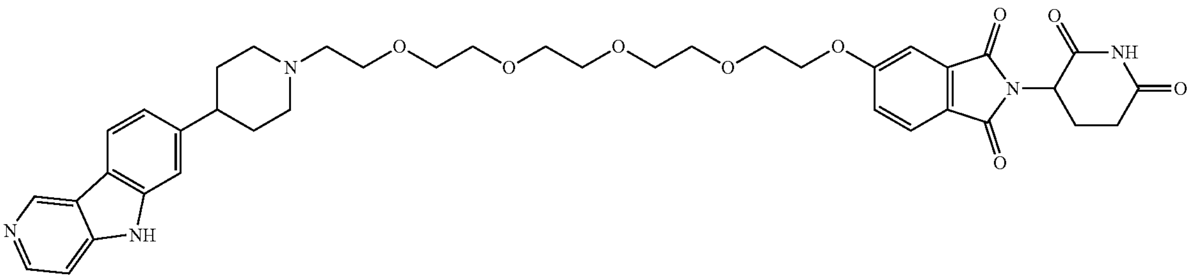 [SMILES: O=C1CCC(N2C(=O)c3ccc(OCCOCCOCCOCCOCCN4CCC(c5ccc6c(c5)[nH]c5ccncc56)CC4)cc3C2=O)C(=O)N1]

To a solution of 7-(piperidin-4-yl)-5H-pyrido[4,3-b]indole (80 mg, 0.32 mmol) and 14-((2-(2,6-dioxopiperidin-3-yl)-1,3-dioxoisoindolin-5-yl)oxy)-3,6,9,12-tetraoxatetradecanal (175 mg, 0.36 mmol) [prepared as described for intermediate 101 above] in $CH_3OH$ (10 mL) were added $NaBH_3CN$ (40 mg, 0.64 mmol) and one drop of $CH_3COOH$ at room temperature. After stirring for 2 hours, the reaction was quenched by the addition of water (20 mL). The resulting solution was extracted with DCM (20 mL×3). The combined organic layers were washed with brine (20 mL×2), dried over anhydrous sodium sulfate and concentrated under vacuum. The residue was purified by prep-TLC with DCM/$CH_3OH$ (10:1) to afford the desired product (18 mg, 0.025 mmol, 8%). $^1H$ NMR (400 MHz, $CD_3OD$): δ 9.30 (s, 1H), 8.42-8.60 (m, 2H), 8.19 (d, J=8.0 Hz, 1H), 7.60-7.65 (m, 2H), 7.52 (s, 1H), 7.31 (d, J=8.0 Hz, 1H), 7.19 (s, 1H), 7.12-7.14 (m, 1H), 5.07-5.10 (m, 1H), 4.12 (t, J=4.0 Hz, 2H), 3.66-3.86 (m, 18H), 3.37 (s, 2H), 3.15-3.20 (m, 3H), 2.71-2.76 (m, 3H), 2.09-2.22 (m, 5H). $(M+H)^+$ 728.3.

Synthetic Scheme for Exemplary Compound 60

5-(4-(3-((1r,3r)-3-((5-(5H-pyrido[4,3-b]indol-7-yl)pyridin-2-yl)oxy)cyclobutoxy)propyl)piperazin-1-yl)-2-(2,6-dioxopiperidin-3-yl)isoindoline-1,3-dione

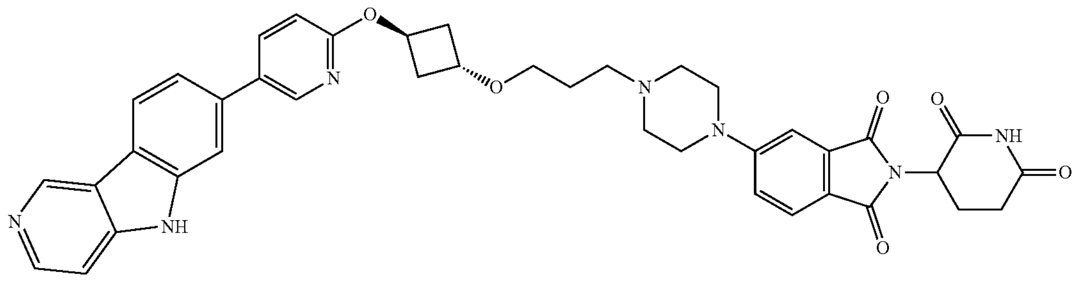 [SMILES: O=C1CCC(N2C(=O)c3ccc(N4CCN(CCCO[C@H]5C[C@H](Oc6ccc(-c7ccc8c(c7)[nH]c7ccncc78)cn6)C5)CC4)cc3C2=O)C(=O)N1]

Step 1: tert-butyl 4-(3-((1r,3r)-3-((4-nitrobenzoyl)oxy)cyclobutoxy)propyl)piperazine-1-carboxylate

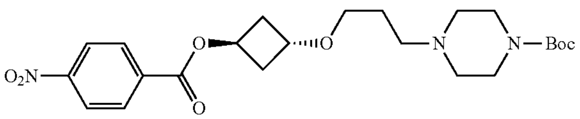 [SMILES: CC(C)(C)OC(=O)N1CCN(CCCO[C@H]2C[C@H](OC(=O)c3ccc([N+](=O)[O-])cc3)C2)CC1]

To a solution of tert-butyl-4-(3-((1s,3s)-3-hydroxycyclobutoxy)propyl)piperazine-1-carboxylate (530 mg, 1.68 mmol), triphenylphosphine (1.32 g, 5.06 mmol) and 4-nitrobenzoic acid (310 mg, 1.85 mmol) in THF (10 mL) was added DIAD (1.02 g, 5.06 mmol) dropwise at room temperature under $N_2$. After stirring at room temperature for 3 hours, it was quenched with water (20 mL), and the mixture was extracted with EtOAc (20 mL×2). The combined organic layers were concentrated under vacuum. The residue was purified by silica gel column with PE/EA from 2:1 to 1:1 as eluent to afford the desired product (350 mg, 45%) as a semi-solid.

Tert-butyl 4-(3-((1r,3r)-3-((4-nitrobenzoyl)oxy)cyclobutoxy)propyl)piperazine-1-carboxylate was converted to the title compound, 5-(4-(3-((1r,3r)-3-((5-(5H-pyrido[4,3-b]indol-7-yl)pyridin-2-yl)oxy)cyclobutoxy)propyl)piperazin-1-yl)-2-(2,6-dioxopiperidin-3-yl)isoindoline-1,3-dione, according to the following scheme and using procedures described above for Exemplary Compound 53.

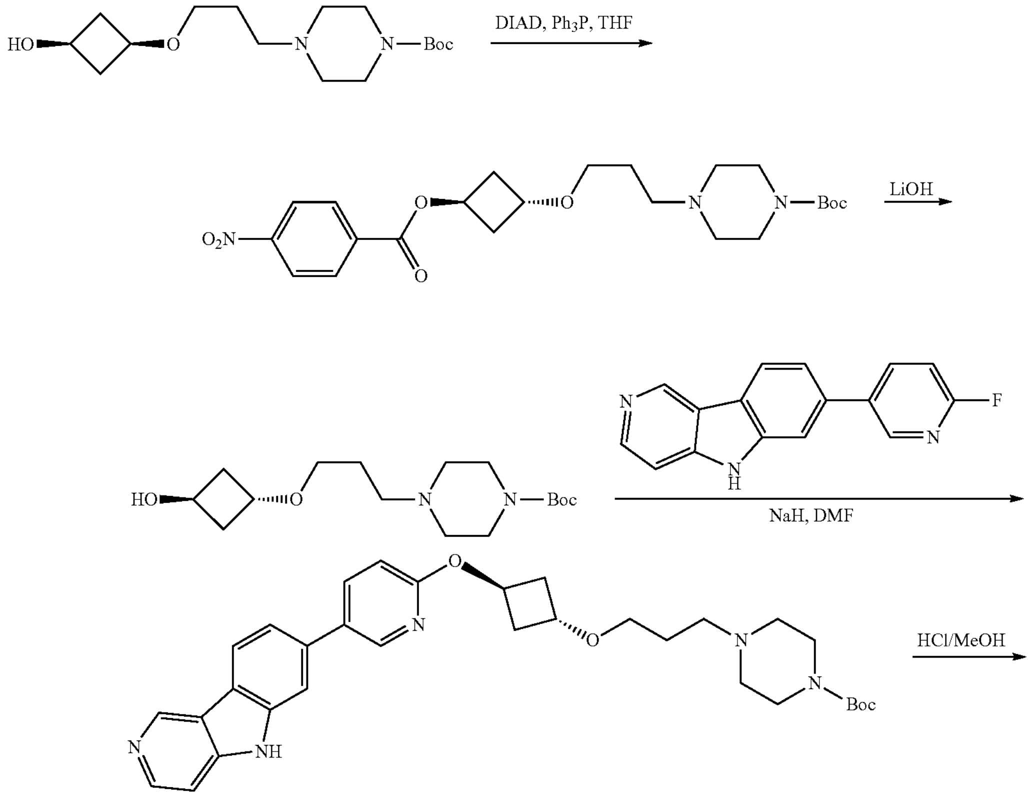

-continued

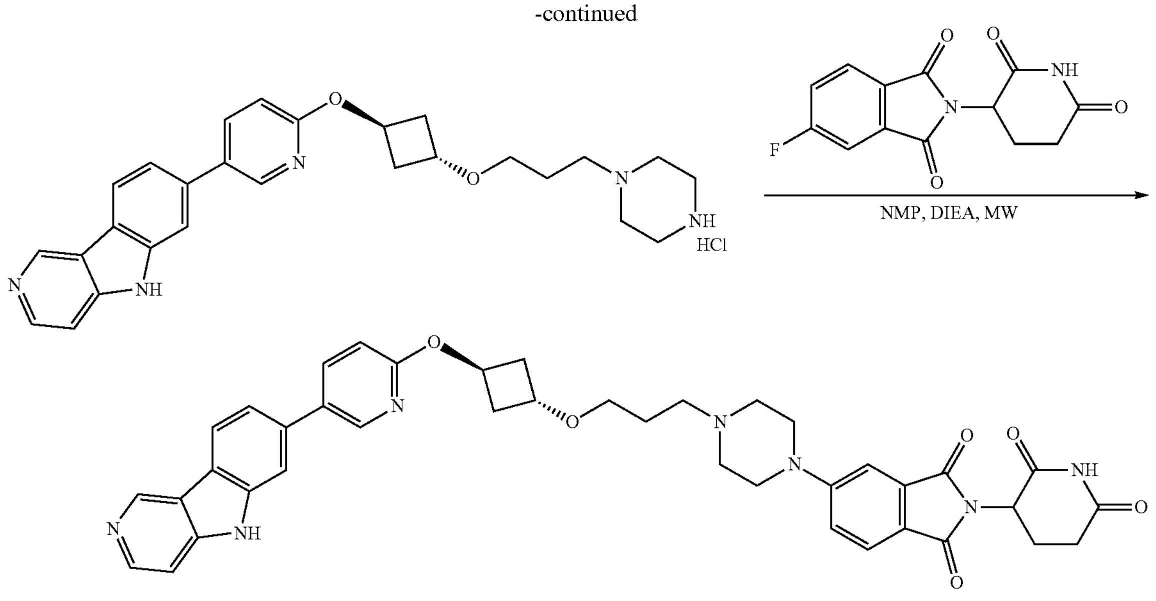

Compound 60

Compound 60: $^{1}H$ NMR (400 MHz, DMSO-$d_6$): δ 11.07 (s, 1H), 9.76 (s, 1H), 8.67 (d, J=6.0 Hz, 1H), 8.60 (s, 1H), 8.52 (d, J=8.4 Hz, 1H), 8.16 (d, J=8.4 Hz, 1H), 8.80-8.02 (m, 2H), 7.77 (t, J=8.4 Hz, 2H), 7.50 (s, 1H), 7.37 (d, J=8.0 Hz, 1H), 6.96 (d, J=8.8 Hz, 1H), 5.36 (m, 1H), 5.07-5.11 (m, 1H), 4.24 (br, 3H), 3.62 (br, 9H), 3.55 (s, 3H), 3.17-3.25 (m, 6H), 2.86-2.93 (m, 1H), 2.38-2.62 (m, 4H), 1.97-2.04 (m, 1H). $(M+H)^+$ 714.3.

Synthetic Scheme for Exemplary Compound 61

2-(2,6-dioxopiperidin-3-yl)-5-((5-(4-(3-(5-(5-(2,2,2-trifluoroethyl)-5H-pyrido[4,3-b]indol-7-yl)pyridin-2-yl)propyl)piperazin-1-yl)pentyl)oxy)isoindoline-1,3-dione

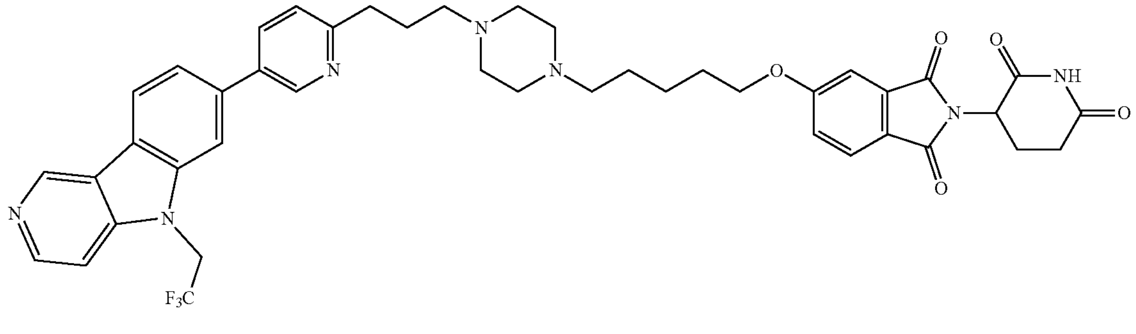 [SMILES: O=C1CCC(N2C(=O)c3ccc(OCCCCCN4CCN(CCCc5ccc(-c6ccc7c8cnccc8n(CC(F)(F)F)c7c6)cn5)CC4)cc3C2=O)C(=O)N1]

Step 1: 7-(6-(3-((tert-butyldimethylsilyl)oxy)propyl) pyridin-3-yl)-5H-pyrido[4,3-b]indole

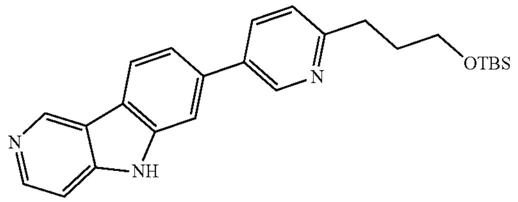 [SMILES: CC(C)(C)[Si](C)(C)OCCCc1ccc(-c2ccc3c(c2)[nH]c2ccncc23)cn1]

To a solution of 3-(5-(5H-pyrido[4,3-b]indol-7-yl)pyridin-2-yl)propan-1-ol (prepared as described for Compound 55; 100 mg, 0.33 mmol) in DCM (5 mL) were added imidazole (44.8 mg, 0.66 mmol) and TBSCl (59.6 mg, 0.40 mmol). The resulting solution was stirred at 40° C. for 3 hours. The solvent was removed under reduced pressure. The residue was diluted with EA (30 mL), the mixture was washed with brine. The organic layer was dried over anhydrous sodium sulfate, filtered and concentrated under vacuum. The residue was purified by silica gel column chromatography (DCM/MeOH=20/1, 0.2% $Net_3$) to afford the title product (100 mg. 73% yield).

Step 2: 7-(6-(3-((tert-butyldimethylsilyl)oxy)propyl)pyridin-3-yl)-5-(2,2,2-trifluoroethyl)-5H-pyrido[4,3-b]indole

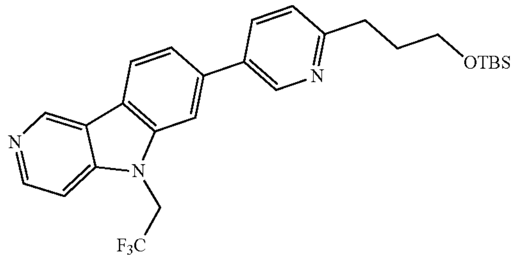 [SMILES: CC(C)(C)[Si](C)(C)OCCCc1ccc(-c2ccc3c4cnccc4n(CC(F)(F)F)c3c2)cn1]

To a solution of 7-(6-(3-((tert-butyldimethylsilyl)oxy)propyl)pyridin-3-yl)-5H-pyrido[4,3-b]indole (60 mg, 0.14 mmol) in DMF (5 mL) was added NaH (8.6 mg, 0.22 mmol) at 5° C. After stirring for 20 min, a solution of $CF_3CH_2Otf$ (66.6 mg, 0.29 mmol) in DMF (1 mL) was added dropwise. The mixture was stirred for another 1 hour, and the reaction was diluted by EtOAc (40 mL), washed with brine, dried over anhydrous sodium sulfate. The filtrate was evaporated under reduced pressure. The residue was purified by column chromatography on silica gel (DCM/MeOH=40:1, 0.2% $NH_3 \cdot H_2O$) to afford the title product (55 mg, 92%).

Step 3: 3-(5-(5-(2,2,2-trifluoroethyl)-5H-pyrido[4,3-b]indol-7-yl)pyridin-2-yl)propan-1-ol

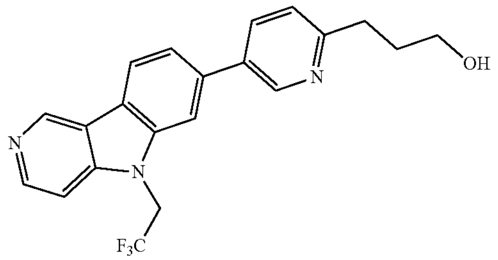 [SMILES: OCCCc1ccc(-c2ccc3c4cnccc4n(CC(F)(F)F)c3c2)cn1]

To a solution of 7-(6-(3-((tert-butyldimethylsilyl)oxy)propyl)pyridin-3-yl)-5-(2,2,2-trifluoroethyl)-5H-pyrido[4,3-b]indole (110 mg, 0.22 mmol) in $CH_3OH$ (2 mL) was added HCl/Dioxane (6 N, 3 mL). The resulting solution was stirred at 5° C. for 1 hour. Then it was diluted with EtOAc (40 mL), and the mixture was washed with sat. $NaHCO_3$ (a.q.) and brine, and dried over anhydrous sodium sulfate. The organic phase was evaporated under reduced pressure to afford crude title product (84.9 mg) which was used in the next reaction without further purification.

Step 4: 3-(5-(5-(2,2,2-trifluoroethyl)-5H-pyrido[4,3-b]indol-7-yl)pyridin-2-yl)propanal

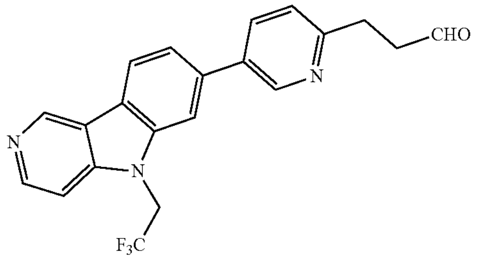 [SMILES: O=CCCc1ccc(-c2ccc3c4cnccc4n(CC(F)(F)F)c3c2)cn1]

To a solution of 3-(5-(5-(2,2,2-trifluoroethyl)-5H-pyrido[4,3-b]indol-7-yl)pyridin-2-yl)propan-1-ol (90 mg, 0.23 mmol) in DMSO (2 mL) was added IBX (130.9 mg, 0.47 mL). The resulting mixture was stirred at 40° C. for 2 hours. The mixture was quenched by sat. $Na_2S_2O_3$ a.q. (5 mL) and sat. $NaHCO_3$ a.q. (5 mL). The mixture was extracted with EtOAc (20 mL×5). The combined organic layer was dried over anhydrous sodium sulfate, concentrated under vacuum to afford crude desired product (89.5 mg) which was used in the next reaction without further purification.

Step 5: tert-butyl 4-(5-((2-(2,6-dioxopiperidin-3-yl)-1,3-dioxoisoindolin-5-yl)oxy)pentyl)piperazine-1-carboxylate

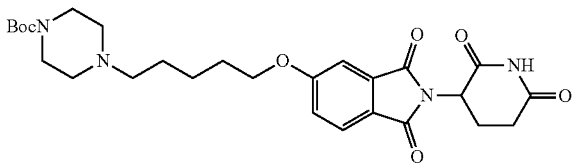 [SMILES: CC(C)(C)OC(=O)N1CCN(CCCCCOc2ccc3c(c2)C(=O)N(C2CCC(=O)NC2=O)C3=O)CC1]

To a solution of 5-((2-(2,6-dioxopiperidin-3-yl)-1,3-dioxoisoindolin-5-yl)oxy)pentanal (150 mg, 0.42 mmol) [prepared according to the procedures described above] in MeOH (5 mL) were added tert-butyl piperazine-1-carboxylate (77.9 mg, 0.42 mmol) and $NaBH_3CN$ (52.6 mg, 0.84 mmol). The resulting solution was stirred at 40° C. for 2 hours. The solvent was evaporated under reduced pressure. The residue was diluted with EA (30 mL), and the mixture was washed with brine. The organic phase was dried over anhydrous sodium sulfate, filtered. The filtrate was concentrated in vacuo. The residue was purified by silica gel column chromatography (DCM/MeOH=60/1) to afford the desired product (200 mg, 90% yield).

Using BOC-deprotection and reductive amination procedures analogous to those described above, compounds of the steps 4 and 5 were converted into the final compound, 2-(2,6-dioxopiperidin-3-yl)-5-((5-(4-(3-(5-(5-(2,2,2-trifluoroethyl)-5H-pyrido[4,3-b]indol-7-yl)pyridin-2-yl)propyl)piperazin-1-yl)pentyl)oxy)isoindoline-1,3-dione.

$^1H$ NMR (400 MHz, $CD_3OD$) S 9.35 (s, 1H), 8.89 (s, 1H), 8.55 (d, J=5.8 Hz, 1H), 8.40 (d, J=8.0 Hz, 1H), 8.17-8.22 (m, 1H), 8.05 (s, 1H), 7.81 (d, J=8.3 Hz, 1H), 7.74 (d, J=5.6 Hz, 1H), 7.51 (d, J=8.2 Hz, 1H), 7.40 (s, 1H), 7.33 (s, 1H), 5.40 (d, J=9.1 Hz, 2H), 5.08-5.16 (m, 1H), 4.95 (s, 4H), 4.59 (s, 2H), 4.18 (t, J=6.2 Hz, 1H), 2.91-3.00 (m, 2H), 2.58-2.91

(m, 9H), 2.12-2.18 (m, 1H), 2.06 (s, 2H), 1.89 (s, 2H), 1.69 (s, 2H), 1.57 (s, 2H). $(M+H)^+$ 796.3.

Synthetic Scheme for Exemplary Compound 62

3-(5-((5-(4-(3-(5-(5-methyl-5H-pyrido[4,3-b]indol-7-yl)pyridin-2-yl)propyl)piperazin-1-yl)pentyl)oxy)-1-oxoisoindolin-2-yl)piperidine-2,6-dione temperature and quenched by the addition of water (10 mL). The resulting solution was extracted with ethyl acetate (15 mL×3). The combined organic layers were washed with brine (10 mL×2), dried over anhydrous sodium sulfate and concentrated under vacuum. The residue was applied onto a silica gel column with dichloromethane/methanol (10:1) to afford the desired product (190 mg, 0.55 mmol, 46%).

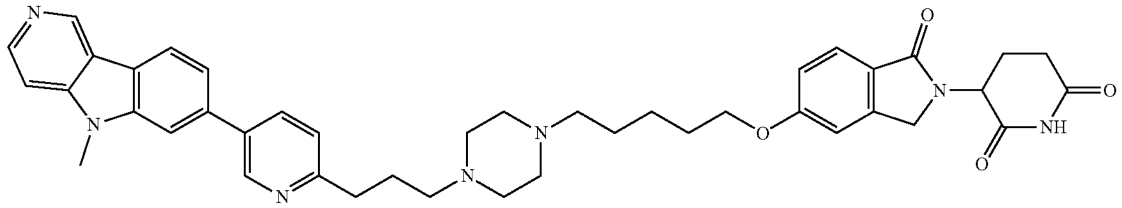 [SMILES: Cn1c2ccncc2c2ccc(-c3ccc(CCCN4CCN(CCCCCOc5ccc6c(c5)CN(C5CCC(=O)NC5=O)C6=O)CC4)nc3)cc21]

Step 1: tert-butyl 5-amino-4-(5-((5-hydroxypentyl)oxy)-1-oxoisoindolin-2-yl)-5-oxopentanoate

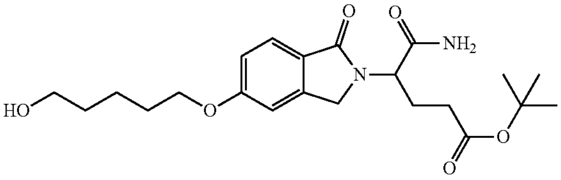 [SMILES: CC(C)(C)OC(=O)CCC(C(N)=O)N1Cc2cc(OCCCCCO)ccc2C1=O]

To a solution of tert-butyl 5-amino-4-(5-hydroxy-1-oxoisoindolin-2-yl)-5-oxopentanoate (500.0 mg, 1.0 eq), pentane-1,5-diol (187 mg, 1.2 eq) and PPh3 (590.0 mg, 1.5 eq) in anhydrous tetrahydrofuran (50 mL) was added DIAD (455 mg, 2.25 mmol, 1.5 eq). The resulting solution was stirred at room temperature for 16 hours. Then the reaction was quenched by the addition of water (100 mL). The resulting solution was extracted with ethyl acetate (50 mL×3). The combined organic layers were washed with brine (20 mL×2), dried over anhydrous sodium sulfate and concentrated under vacuum. The residue was applied onto a silica gel column with dichloromethane/methanol (10:1) to afford the desired product (560 mg. 1.33 mmol, 89%).

Step 2: 3-(5-((5-hydroxypentyl)oxy)-1-oxoisoindolin-2-yl)piperidine-2,6-dione

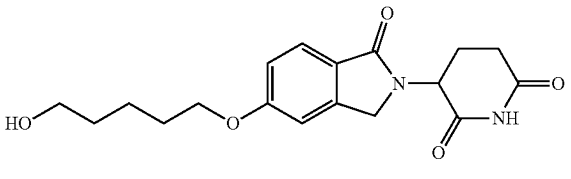 [SMILES: O=C1CCC(N2Cc3cc(OCCCCCO)ccc3C2=O)C(=O)N1]

To a solution of tert-butyl 5-amino-4-(5-((5-hydroxypentyl)oxy)-1-oxoisoindolin-2-yl)-5-oxopentanoate (560 mg, 1.0 eq) in MeCN (20 mL) was added p-TsA (253 mg, 3.0 eq) at room temperature. The resulting solution was stirred at 90° C. for 6 hours. Then the reaction was cooled to room Step 3: 5-((2-(2,6-dioxopiperidin-3-yl)-1-oxoisoindolin-5-yl)oxy)pentanal

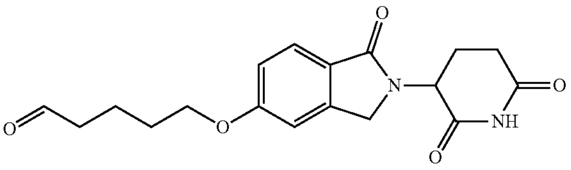 [SMILES: O=CCCCCOc1ccc2c(c1)CN(C1CCC(=O)NC1=O)C2=O]

To a solution of 3-(5-((5-hydroxypentyl)oxy)-1-oxoisoindolin-2-yl)piperidine-2,6-dione (190 mg, 1.0 equiv) in DCM (20 mL) was added IBX (100 mg, 2 eq) at room temperature. The resulting solution was stirred at room temperature for 2 hours. Then the solid was filtered off and the filtrate was concentrated under vacuum to afford crude product (190 mg) which was used into next reaction without further purification.

Step 4: 7-bromo-5-methyl-5H-pyrido[4,3-b]indole]

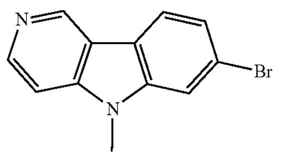

To a solution of 7-bromo-5H-pyrido[4,3-b]indole (8.0 g, 32.4 mmol) in N,N-dimethylformamide (50 ml) was added sodium hydride (1.4 g, 35.6 mmol, 60% in mineral oil) at 0° C., and the reaction mixture was stirred at 0° C. for 30 minutes. To the resulting mixture was added iodomethane (4.6 g, 32.4 mmol) at 0° C., and the reaction mixture was allowed to warm up to room temperature and stirred overnight. TLC showed the reaction was complete. The reaction mixture was quenched with water (30 ml) at 0° C., and extracted with ethyl acetate (50 ml×2). The combined organic layers were washed with water (80 ml) then brine (90 ml), dried over anhydrous sodium sulfate, and concentrated under reduced pressure to give a crude residue which was purified by silica gel flash chromatography (eluted with 20-40% ethyl acetate in hexane) to afford 7-bromo-5-methyl-5H-pyrido[4,3-b]indole (6.0 g, yield 71%) as brown solid.

Using procedures described above for the Exemplary Compound 61, 5-((2-(2,6-dioxopiperidin-3-yl)-1-oxoisoindolin-5-yl)oxy)pentanal was converted into the title compound, 3-(5-((5-(4-(3-(5-(5-methyl-5H-pyrido[4,3-b]indol-7-yl)pyridin-2-yl)propyl)piperazin-1-yl)pentyl)oxy)-1-oxoisoindolin-2-yl)piperidine-2,6-dione according to the scheme below.

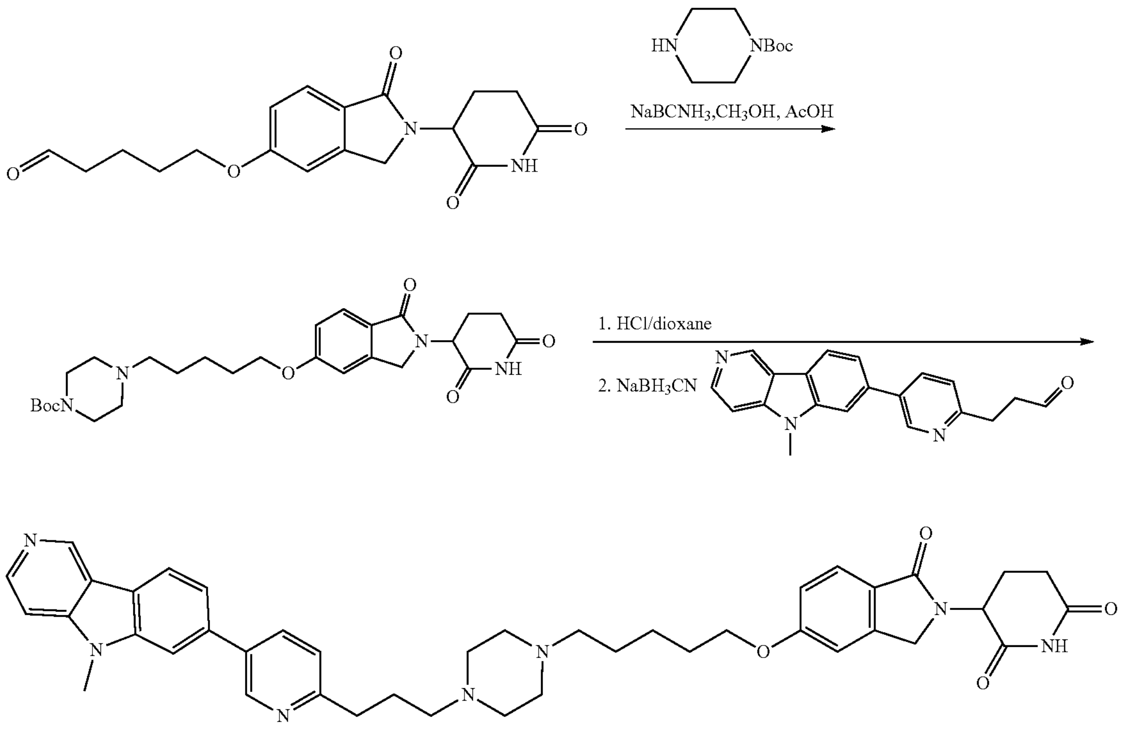

Compound 62

Exemplary Compound 62: $^{1}$HNMR (400 MHz, MeOD): δ 9.27 (s, 1H), 8.86 (d, J=2.0 Hz, 1H), 8.46 (d, J=6.0 Hz, 1H), 8.33 (d, J=8.0 Hz, 1H), 8.16 (d, J=2.4 Hz, 1H), 7.90 (s, 1H), 7.59-7.70 (m, 3H), 7.47 (d, J=6.0 Hz, 1H), 7.03-7.09 (m, 2H), 5.06-5.12 (m, 1H), 4.42 (d, J=5.6 Hz, 2H), 4.07 (t, J=6.4 Hz, 2H), 3.99 (s, 3H), 2.89-2.96 (m, 3H), 2.51-2.75 (m, 13H), 2.12-2.24 (m, 1H), 2.01-2.03 (m, 3H), 1.82-1.84 (m, 2H), 1.52-1.63 (m, 6H). $(M+H)^+$ 714.3.

Exemplary Compound 63

2-(2,6-dioxopiperidin-3-yl)-5-((5-(4-(3-(5-(5-methyl-5H-pyrido[4,3-b]indol-7-yl)-3-(trifluoromethyl)pyridin-2-yl)propyl)piperazin-1-yl)pentyl)oxy)isoindoline-1,3-dione

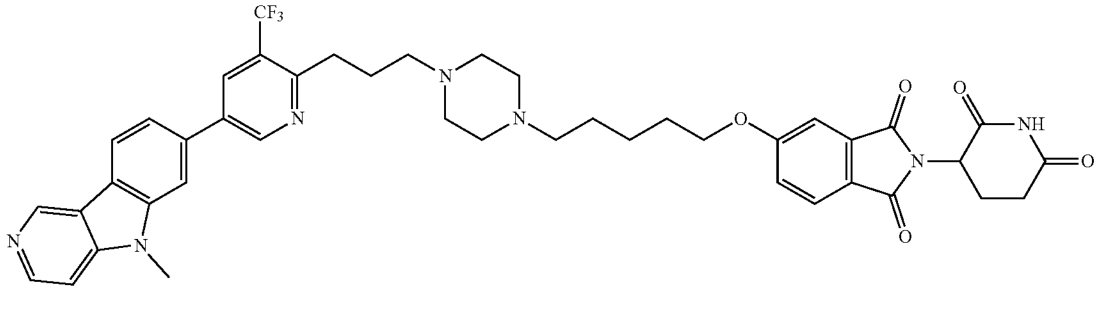 [SMILES: Cn1c2ccncc2c2ccc(-c3cnc(CCCN4CCN(CCCCCOc5ccc6c(c5)C(=O)N(C5CCC(=O)NC5=O)C6=O)CC4)c(C(F)(F)F)c3)cc21]

Step 1: 5-methyl-7-(4,4,5,5-tetramethyl-1,3,2-dioxaborolan-2-yl)-5H-pyrido[4,3-b]indole

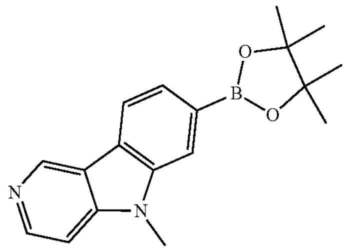 [SMILES: Cn1c2ccncc2c2ccc(B3OC(C)(C)C(C)(C)O3)cc21]

To a solution of 7-bromo-5-methyl-5H-pyrido[4,3-b]indole (150 mg, 0.577 mmol) in dioxane were added KOAc (114 mg, 1.15 mmol), Pd(dppf)$Cl_2$ (35 mg, 0.05 mmol), and 4,4,4',4',5,5,5',5'-octamethyl-2,2'-bi(1,3,2-dioxaborolane) (294 mg, 1.15 mmol) subsequently. The resulting solution was heated to 100° C. overnight under $N_2$. After cooling to room temperature, the reaction was quenched with water, the mixture was extracted with EtOAc (10 mL×2). The combined organic layers were washed with brine (10 mL). The organic phase was dried over $Na_2SO_4$, concentrated under vacuum to afford crude desired product (180 mg, crude), which was used into next reaction without further purification.

Step 2: 7-(6-chloro-5-(trifluoromethyl)pyridin-3-yl)-5-methyl-5H-pyrido[4,3-b]indole

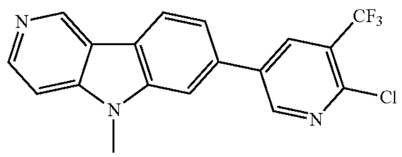 [SMILES: Cn1c2ccncc2c2ccc(-c3cnc(Cl)c(C(F)(F)F)c3)cc21]

To a mixture of 5-bromo-2-chloro-3-trifluoromethylpyridine (135 mg, 0.7 mmol) and 5-methyl-7-(4,4,5,5-tetramethyl-1,3,2-dioxaborolan-2-yl)-5H-pyrido[4,3-b]indole (180 mg, 0.58 mmol) in dioxane/$H_2O$ (v/v=10/1, 10 mL) were added Pd(dppf)$_2Cl_2$ (20 mg, 10%) and CsF (180 mg, 1.16 mmol). The mixture was stirred at 80° C. overnight. The solution was quenched with water. The mixture was extracted with ethyl acetate (20 mL), and the combined organic layers were washed with brine (10 mL). The organic layer was dried over anhydrous sodium sulfate, filtered and concentrated under vacuum. The residue was purified by silica gel column chromatography to afford the desired product (170 mg, 95% yield).

Step 3: tert-butyl 4-(3-(5-(5-methyl-5H-pyrido[4,3-b]indol-7-yl)-3-(trifluoromethyl)pyridin-2-yl)prop-2-yn-1-yl)piperazine-1-carboxylate

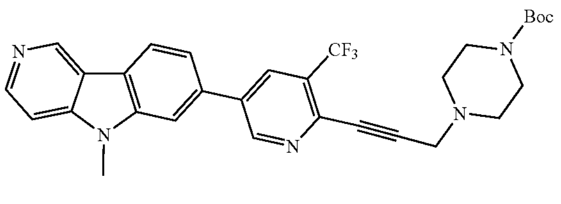 [SMILES: Cn1c2ccncc2c2ccc(-c3cnc(C#CCN4CCN(C(=O)OC(C)(C)C)CC4)c(C(F)(F)F)c3)cc21]

To a mixture of 7-(6-chloro-5-(trifluoromethyl)pyridin-3-yl)-5-methyl-5H-pyrido[4,3-b]indole (170 mg, 0.58 mmol) and tert-butyl 4-(prop-2-ynyl)piperazine-1-carboxylate (156 mg, 0.69 mmol) in DMF (10 mL) were added Pd($PPh_3$)$_2Cl_2$ (17 mg, 10%), $Cs_2CO_3$ (378 mg, 1.16 mmol), DBU (30 mg, 0.116 mmol) and t-$Bu_3P$ (25 mg, 0.116 mmol). The mixture was microwave-heated at 150° C. for 10 minutes. The reaction mixture was quenched with water. The mixture was extracted with ethyl acetate (20 mL). The combined organic layers were washed with brine (10 mL). The organic layer was dried over anhydrous sodium sulfate, filtered and concentrated under vacuum. The residue was purified by silica gel column chromatography to afford the desired product (200 mg).

Step 4: tert-butyl 4-(3-(5-(5-methyl-5H-pyrido[4,3-b]indol-7-yl)-3-(trifluoromethyl)pyridin-2-yl)propyl)piperazine-1-carboxylate

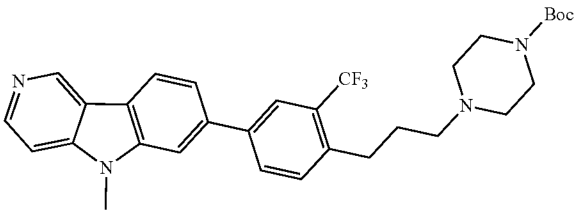 [SMILES: Cn1c2ccncc2c2ccc(-c3ccc(CCCN4CCN(C(=O)OC(C)(C)C)CC4)c(C(F)(F)F)c3)cc21]

To a solution of tert-butyl 4-(3-(5-(5-methyl-5H-pyrido[4,3-b]indol-7-yl)-3-(trifluoromethyl)pyridin-2-yl)prop-2-yn-1-yl)piperazine-1-carboxylate (200 mg) in ethanol was added Pd/C (20 mg). The mixture was stirred at 30° C. under $H_2$ atmosphere (3 Mpa) for 8 hours. The mixture was filtered through Celite, and the filtrate was concentrated under vacuum. The residue was purified by prep-HPLC to afford the desired product (25 mg).

Using BOC-deprotection and reductive amination procedures described above tert-butyl 4-(3-(5-(5-methyl-5H-pyrido[4,3-b]indol-7-yl)-3-(trifluoromethyl)pyridin-2-yl)propyl)piperazine-1-carboxylate was converted into the title compound, 2-(2,6-dioxopiperidin-3-yl)-5-((5-(4-(3-(5-(5-methyl-5H-pyrido[4,3-b]indol-7-yl)-3-(trifluoromethyl)pyridin-2-yl)propyl)piperazin-1-yl)pentyl)oxy)isoindoline-1,3-dione according to the scheme below.

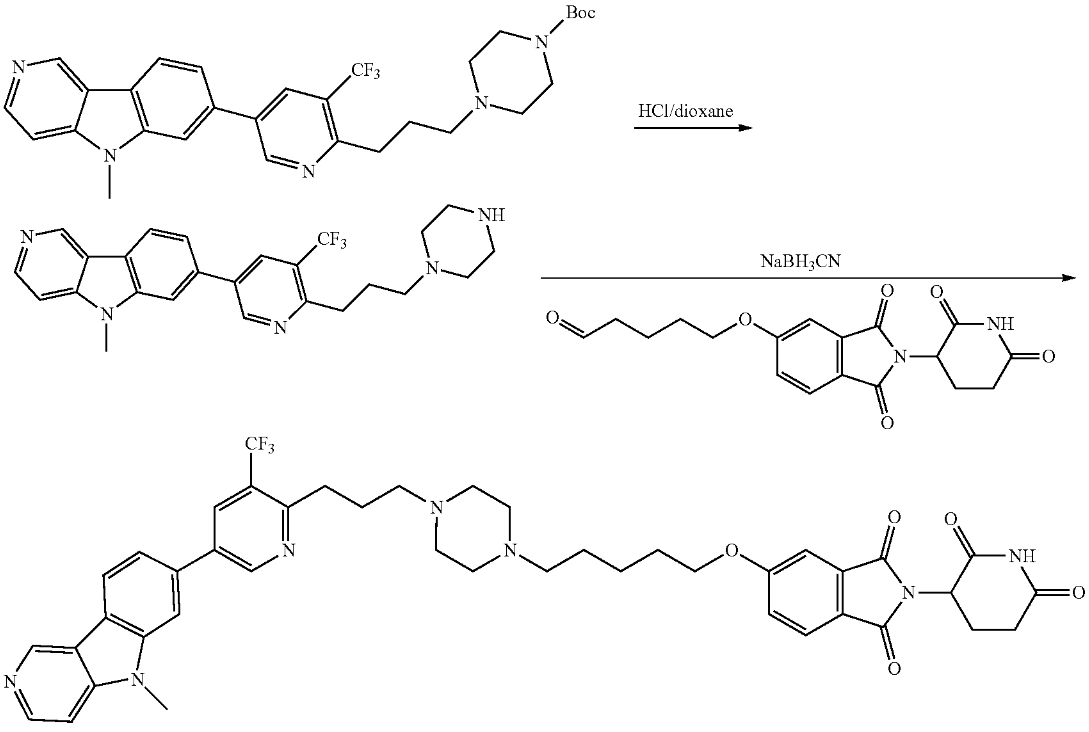

Compound 63

Exemplary Compound 63: $^1$H NMR (400 MHz, $CD_3OD$): δ 9.25 (s, 1H), 8.45 (s, 1H), 8.23 (d, J=7.6 Hz, 1H), 7.76 (d, J=8.4 Hz, 1H), 7.66 (s, 1H), 7.59 (d, J=8.0 Hz, 1H), 7.39 (d, J=8.4 Hz, 1H), 7.35 (s, 2H), 7.26-7.28 (m, 1H), 6.06 (s, 1H), 5.72 (s, 1H), 5.06-5.08 (m, 1H), 4.30 (d, J=6.4 Hz, 1H), 4.11-4.15 (m, 2H), 3.90-3.94 (m, 4H), 3.70-3.74 (m, 2H), 3.03-3.06 (m, 2H), 2.82-2.88 (m, 4H), 2.71-2.75 (m, 6H), 2.51-2.55 (m, 3H), 2.05-2.25 (m, 2H), 1.82-1.86 (m, 2H), 1.61-1.63 (m, 2H), 1.51-1.52 (m, 2H). $(M+H)^+$ 796.2.

Exemplary Compound 73

Step 1: 7-(6-((1s,3s)-3-(benzyloxy)cyclobutoxy) pyridin-3-yl)-5H-pyrido[4,3-b]indole

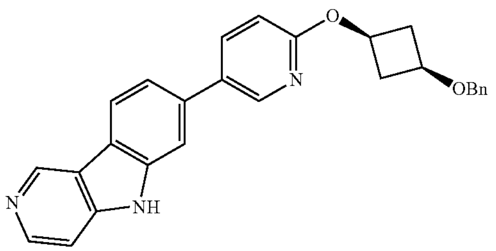 [SMILES: c1ccc(CO[C@H]2C[C@@H](Oc3ccc(-c4ccc5c(c4)[nH]c4ccncc45)cn3)C2)cc1]

To a solution of 7-(6-fluoropyridin-3-yl)-5H-pyrido[4,3-b]indole (1.1 g, 4.18 mmol) and (1s,3s)-3-(benzyloxy)cyclobutanol (745 mg, 4.18 mmol) in 1-methylpyrrolidin-2-one (2 ml) was added sodium hydride (60% in mineral oil) (334 mg, 8.35 mmol) at 0° C. The mixture was stirred at room temperature for 2 hours. TLC showed the reaction was complete. The mixture was partitioned between ethyl acetate (20 ml) and water (20 ml). The organic layer was collected, washed with brine (30 ml), dried over anhydrous sodium sulfate, and concentrated under reduced pressure to give a crude residue which was purified by silica gel flash chromatography (eluted with 2-5% methanol in dichloromethane) to afford 7-(6-((1s,3s)-3-(benzyloxy)cyclobutoxy)pyridin-3-yl)-5H-pyrido[4,3-b]indole (1.42 g, 82%) as white solid.

Step 2: (1s,3s)-3-((5-(5H-pyrido[4,3-b]indol-7-yl) pyridin-2-yl)oxy)cyclobutan-1-ol

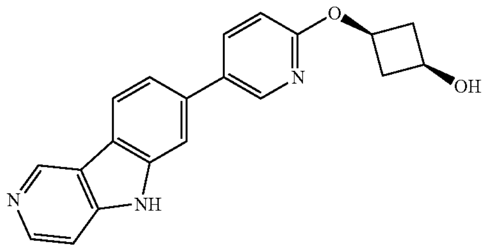 [SMILES: O[C@H]1C[C@@H](Oc2ccc(-c3ccc4c(c3)[nH]c3ccncc34)cn2)C1]

A mixture of 7-(6-((1s,3s)-3-(benzyloxy)cyclobutoxy) pyridin-3-yl)-5H-pyrido[4,3-b]indole (1.42 g, 3.37 mmol) and palladium on carbon (10%, 150 mg) in methanol (30 ml)-tetrahydrofuran (10 ml) was stirred at 50° C. for 2 hours under hydrogen atmosphere (hydrogen balloon). TLC showed the reaction was complete. Palladium on carbon was removed through filtration and washed with methanol (10 ml×2). The combined filtrate was concentrated under reduced pressure to afford (1s,3s)-3-((5-(5H-pyrido[4,3-b]indol-7-yl)pyridin-2-yl)oxy)cyclobutanol (1.57 g, crude) as white solid.

Step 3: tert-butyl 7-(6-((1s,3s)-3-hydroxycyclobutoxy)pyridin-3-yl)-5H-pyrido[4,3-b]indole-5-carboxylate

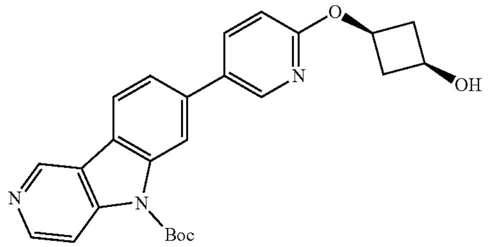 [SMILES: CC(C)(C)OC(=O)n1c2ccncc2c2ccc(-c3ccc(O[C@H]4C[C@@H](O)C4)nc3)cc21]

To a suspension of (1s,3s)-3-((5-(5H-pyrido[4,3-b]indol-7-yl)pyridin-2-yl)oxy)cyclobutanol (1.57 g, 4.27 mmol) and sodium carbonate (1.1 g, 10.69 mmol) in tetrahydrofuran (20 ml)-water (5 ml) was added di-tert-butyl carbonate (1.2 g, 5.55 mmol) at room temperature. The mixture was stirred at room temperature for 17 hours. TLC showed the reaction was complete. The mixture was concentrated and the residue was partitioned between ethyl acetate (20 ml) and water (30 ml). The organic layer was collected, washed with brine (20 ml), dried over anhydrous sodium sulfate, and concentrated under reduced pressure to give a crude residue which was purified by silica gel flash chromatography (eluted with 1-2% methanol in dichloromethane) to afford tert-butyl 7-(6-((1s,3s)-3-hydroxycyclobutoxy)pyridin-3-yl)-5H-pyrido[4,3-b]indole-5-carboxylate (1.1 g, two steps 73%) as white solid.

Step 4: tert-butyl 7-(6-((1s,3s)-3-((methylsulfonyl)oxy)cyclobutoxy)pyridin-3-yl)-5H-pyrido[4,3-b]indole-5-carboxylate

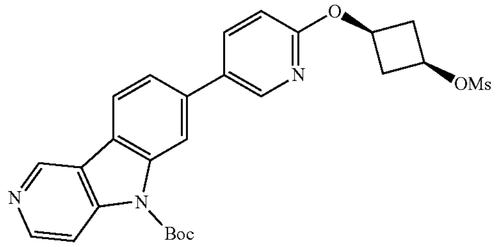 [SMILES: CC(C)(C)OC(=O)n1c2ccncc2c2ccc(-c3ccc(O[C@H]4C[C@@H](OS(C)(=O)=O)C4)nc3)cc21]

To a suspension of tert-butyl 7-(6-((1s,3s)-3-hydroxycyclobutoxy)pyridin-3-yl)-5H-pyrido[4,3-b]indole-5-carboxylate (500 mg, 1.16 mmol) and triethylamine (352 mg, 3.47 mmol) in dichloromethane (10 ml) was added methanesulfonyl chloride (530 mg, 4.63 mmol) at 0° C. The resulting mixture was allowed to warm up to room temperature and stirred at room temperature for 5 hours. TLC showed the reaction was completed. The mixture was diluted with dichloromethane (10 ml) and washed with water (10 ml). The organic layer was washed with brine (20 ml), dried over anhydrous sodium sulfate, and concentrated under reduced pressure to afford tert-butyl 7-(6-((1s,3s)-3-hydroxycyclobutoxy)pyridin-3-yl)-5H-pyrido[4,3-b]indole-5-carboxylate (700 mg, crude) which was used in next step without further purification.

Step 5: 7-(6-((1r,3r)-3-((6-iodopyridin-3-yl)oxy)cyclobutoxy)pyridin-3-yl)-5H-pyrido[4,3-b]indole

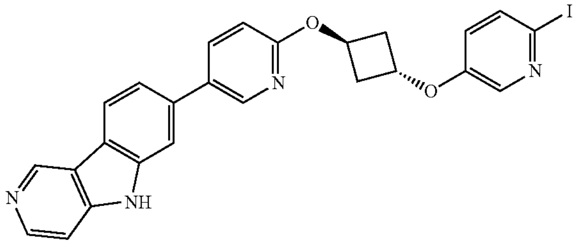 [SMILES: Ic1ccc(O[C@H]2C[C@H](Oc3ccc(-c4ccc5c(c4)[nH]c4ccncc45)cn3)C2)cn1]

A mixture of tert-butyl 7-(6-((1s,3s)-3-hydroxycyclobutoxy)pyridin-3-yl)-5H-pyrido[4,3-b]indole-5-carboxylate (350 mg, 0.69 mmol), 6-iodopyridin-3-ol (155 mg, 0.69 mmol) and cesium carbonate (452 mg, 1.39 mmol) in dry N,N-dimethylformamide (4 ml) was stirred at 90° C. for 12 hours. TLC showed the reaction was complete. The mixture was partitioned between ethyl acetate (30 ml) and water (40 ml). The organic layer was collected, washed with brine (30 ml), dried over anhydrous sodium sulfate, and concentrated under reduced pressure to give a crude residue which was purified by silica gel flash chromatography (eluted with 1-2% methanol in dichloromethane) to afford 7-(6-((1r,3r)-3-((6-iodopyridin-3-yl)oxy)cyclobutoxy)pyridin-3-yl)-5H-pyrido[4,3-b]indole (250 mg, 68%) as light yellow solid.

Step 6: [5-((3-(5-((1r,3r)-3-((5-(5H-pyrido[4,3-b]indol-7-yl)pyridin-2-yl)oxy)cyclobutoxy)pyridin-2-yl)prop-2-yn-1-yl)oxy)-2-(2,6-dioxopiperidin-3-yl)isoindoline-1,3-dione]

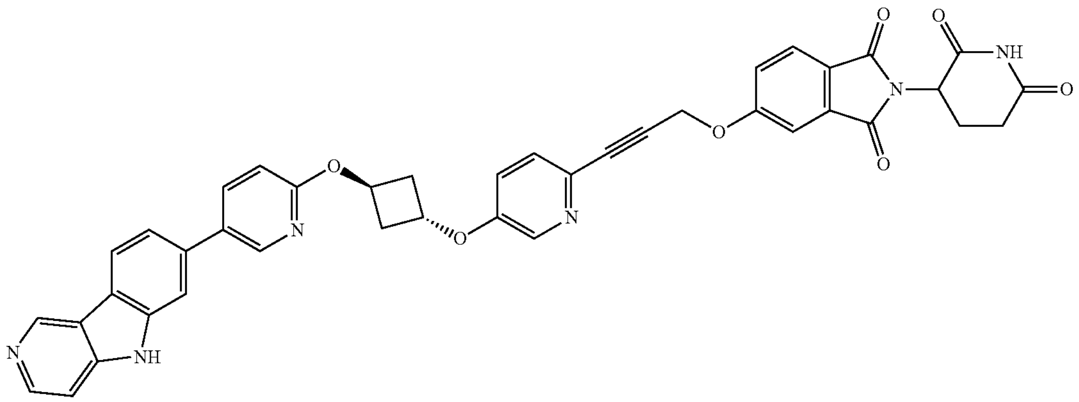 [SMILES: O=C1CCC(N2C(=O)c3ccc(OCC#Cc4ccc(O[C@H]5C[C@H](Oc6ccc(-c7ccc8c(c7)[nH]c7ccncc78)cn6)C5)cn4)cc3C2=O)C(=O)N1]

To a stirred solution of 7-(6-((1r,3r)-3-((6-iodopyridin-3-yl)oxy)cyclobutoxy)pyridin-3-yl)-5H-pyrido[4,3-b]indole (150 mg, 0.24 mmol), 2-(2,6-dioxopiperidin-3-yl)-5-(prop-2-yn-1-yloxy)isoindoline-1,3-dione (111 mg, 0.35 mmol) [prepared using procedure of step 1 from Exemplary Compound 180] and triethylamine (121 mg, 1.20 mmol) in N,N-dimethylformamide (2 ml) were added Bis(triphenylphosphine)palladium(II) chloride (8 mg, 0.01 mmol) and cuprous iodide (2 mg, 0.01 mmol) at room temperature under nitrogen atmosphere; the mixture was degassed with nitrogen three times. The resulting mixture was stirred at 65° C. under nitrogen overnight. TLC showed the reaction was complete. The mixture was partitioned between water (30 ml) and ethyl acetate (30 ml). The organic layer was collected and washed with brine (30 ml×2), dried over anhydrous sodium sulfate, and concentrated under reduced pressure to give a crude residue which was purified by silica gel flash column chromatography (eluted with 2% methanol in dichloromethane) to afford 5-((3-(5-((1r,3r)-3-((5-(5H-pyrido[4,3-b]indol-7-yl)pyridin-2-yl)oxy)cyclobutoxy)pyridin-2-yl)prop-2-yn-1-yl)oxy)-2-(2,6-dioxopiperidin-3-yl) isoindoline-1,3-dione (45 mg, yield 26%) as white solid.

$^1$H NMR (400 MHz, DMSOd-6): δ 2.04-2.07 (m, 1H), 2.57-2.77 (m, 6H), 2.86-2.93 (m, 1H), 5.10-5.14 (m, 2H), 5.32 (s, 2H), 5.39-5.48 (m, 1H), 6.97 (d, J=8.0 Hz, 1H), 7.32-7.33 (m, 1H), 7.46-7.58 (m, 5H), 7.77 (s, 1H), 7.90 (d, J=7.2 Hz, 1H), 8.14 (d, J=7.2 Hz, 1H), 8.25 (s, 1H), 8.30 (d, J=7.6 Hz, 1H), 8.43 (s, 1H), 8.56 (s, 1H), 9.36 (s, 1H), 11.12 (s, 1H), 11.82 (s, 1H). $(M+H)^+$ 719.4.

Synthetic Scheme for Exemplary Compound 77

Step 1: tert-butyl 7-(6-((1r,3r)-3-((6-(3-((2-(2,6-dioxopiperidin-3-yl)-1,3-dioxoisoindolin-5-yl)oxy) propyl)pyridin-3-yl)oxy)cyclobutoxy)pyridin-3-yl)-5H-pyrido[4,3-b]indole-5-carboxylate

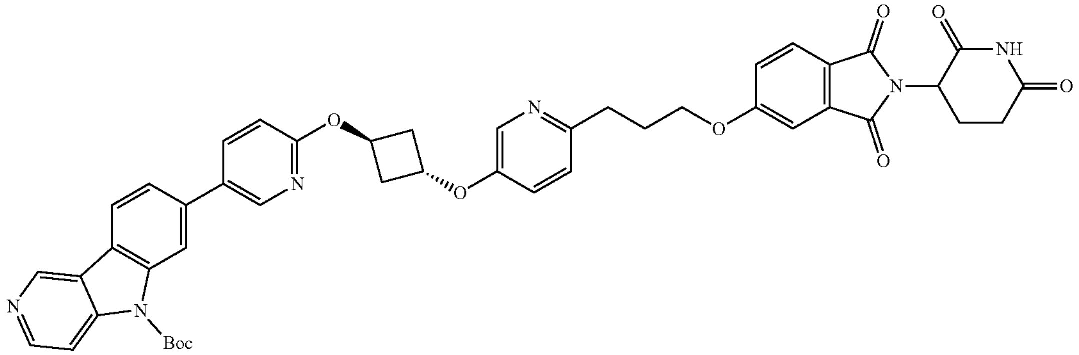 [SMILES: CC(C)(C)OC(=O)n1c2ccncc2c2ccc(-c3ccc(O[C@H]4C[C@H](Oc5ccc(CCCOc6ccc7c(c6)C(=O)N(C6CCC(=O)NC6=O)C7=O)nc5)C4)nc3)cc21]

To a solution of tert-butyl 7-(6-((1r,3r)-3-((6-(3-((2-(2,6-dioxopiperidin-3-yl)-1,3-dioxoisoindolin-5-yl)oxy)prop-1-yn-1-yl)pyridin-3-yl)oxy)cyclobutoxy)pyridin-3-yl)-5H-pyrido[4,3-b]indole-5-carboxylate (15 mg) in MeOH was added Pd/C. The solution was stirred at 30° C. for 2 hours under $H_2$ (2 Mpa). The mixture was filtered through Celite, and the filtrate was concentrated under vacuum. The residue was purified by silica gel to afford the desired product (6 mg).

Step 2: 5-(3-(5-((1r,3r)-3-((5-(5H-pyrido[4,3-b]indol-7-yl)pyridin-2-yl)oxy)cyclobutoxy)pyridin-2-yl) propoxy)-2-(2,6-dioxopiperidin-3-yl)isoindoline-. 3-dione

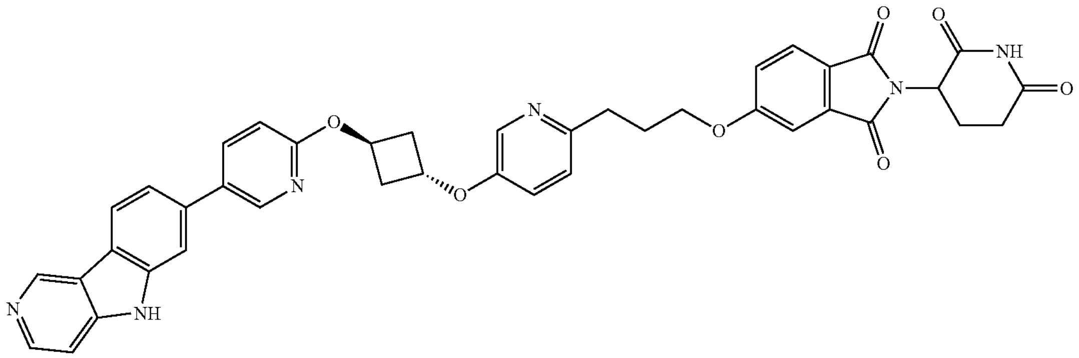 [SMILES: O=C1CCC(N2C(=O)c3ccc(OCCCc4ccc(O[C@H]5C[C@H](Oc6ccc(-c7ccc8c(c7)[nH]c7ccncc78)cn6)C5)cn4)cc3C2=O)C(=O)N1]

A solution of tert-butyl 7-(6-((1r,3r)-3-((6-(3-((2-(2,6-dioxopiperidin-3-yl)-1,3-dioxoisoindolin-5-yl)oxy)propyl) 331pyridin-3-yl)oxy)cyclobutoxy)pyridin-3-yl)-5H-pyrido [4,3-b]indole-5-carboxylate (6 mg) in DCM/TFA (2 mL/1 mL) was stirred at room temperature for 4 hours. The solvent was removed under vacuum to afford 5-(3-(5-((1r,3r)-3-((5-(5H-pyrido[4,3-b]indol-7-yl)pyridin-2-yl)oxy)cyclobutoxy) pyridin-2-yl)propoxy)-2-(2,6-dioxopiperidin-3-yl)isoindoline-1,3-dione (5.5 mg).

$^1$H NMR (400 MHz, $CD_3OD$): δ 9.56 (s, 1H), 8.54-8.56 (m, 2H), 8.45 (d, J=8.4 Hz, 1H), 8.37 (d, J=2.4 Hz, 1H), 8.13 (d, J=8.0 Hz, 1H), 7.97 (d, J=8.0 Hz, 1H), 7.88 (d, J=8.8 Hz, 2H), 7.81 (d, J==8.4 Hz, 1H), 7.79 (s, 1H), 7.76-7.78 (d, J=8 Hz, 1H), 7.29 (s, 1H), 7.21 (d, J=8.0 Hz, 1H), 6.98 (d, J=8.0 Hz, 1H), 5.48-5.52 (m, 1H), 5.32-5.34 (m, 1H), 5.18-5.22 (m, 1H), 5.06-5.10 (m, 1H), 4.25-4.28 (m, 2H), 3.21-3.23 (m, 3H), 2.78-2.81 (m, 5H), 2.67-2.70 (m, 2H), 2.30-2.33 (m, 2H), 2.17-2.19 (m, 1H), 1.97-2.07 (m, 3H). $(M+H)^+$ 723.5.

Synthetic Scheme for Exemplary Compound 94

Step 1: (1r,3r)-3-((6-(5-((triisopropylsilyl)oxy)pent-1-yn-1-yl)pyridin-3-yl)oxy)cyclobutan-1-ol

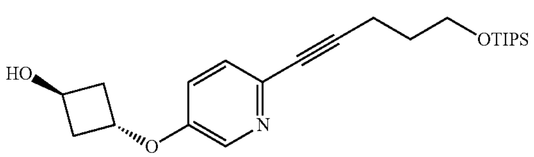

To a solution of (1r,3r)-3-((6-bromopyridin-3-yl)oxy)cyclobutan-1-ol (530 mg, 2.17 mmol) in dry THF (10 mL) was added triisopropyl(pent-4-yn-1-yloxy)silane (626 mg, 2.61 mmol), TEA (1.1 g, 10.86 mmol), CuI (45 mg, 0.24 mmol) and $Pd(PPh_3)_2Cl_2$ (110 mg, 4.34 mmol) at 25° C. under $N_2$. The resulting solution was stirred at 45° C. for 16 hours. The reaction was diluted with $H_2O$ (10 mL). The resulting mixture was extracted with EtOAc (10 mL×2). The combined organic layers were dried over anhydrous sodium sulfate and concentrated. The residue was purified with silica gel column to afford the desired product (1r,3r)-3-((6-(5-((triisopropylsilyl)oxy)pent-1-yn-1-yl)pyridin-3-yl)oxy) cyclobutan-1-ol (600 mg, 68% yield) as a colorless oil.

Step 2: 5-bromo-2-((1r,3r)-3-((6-(5-((triisopropylsilyl)oxy)pent-1-yn-1-yl)pyridin-3-yl)oxy)cyclobutoxy)pyridine

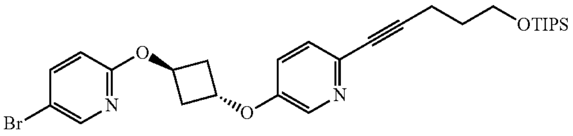

To a solution of (1r,3r)-3-((6-(5-((triisopropylsilyl)oxy) pent-1-yn-1-yl)pyridin-3-yl) oxy)cyclobutan-1-ol (300 mg, 0.74 mmol) in DMF (5 mL) was added NaH (45 mg, 1.11 mmol) at 0° C. The reaction was stirred at 0° C. for 0.5 hours, and 5-bromo-2-fluoropyridine (144 mg, 0.82 mmol) was added dropwise at 0° C. The reaction was stirred at 20° C. for 2 hours. The reaction was diluted with a solution of $H_2O$ (10 mL). The resulting mixture was extracted with EtOAc (10 mL×2), the combined organic layers were dried over anhydrous sodium sulfate and concentration. The residue was purified with silica gel column to afford the desired product 5-bromo-2-((1r,3r)-3-((6-(5-((triisopropylsilyl)oxy) pent-1-yn-1-yl)pyridin-3-yl)oxy)cyclobutoxy)pyridine (240 mg, 58% yield) as a white solid.

Step 3: 5-methyl-7-(6-((1r,3r)-3-((6-(5-((triisopropylsilyl)oxy)pent-1-yn-1-yl)pyridin-3-yl)oxy)cyclobutoxy)pyridin-3-yl)-5H-pyrido[4,3-b]indole

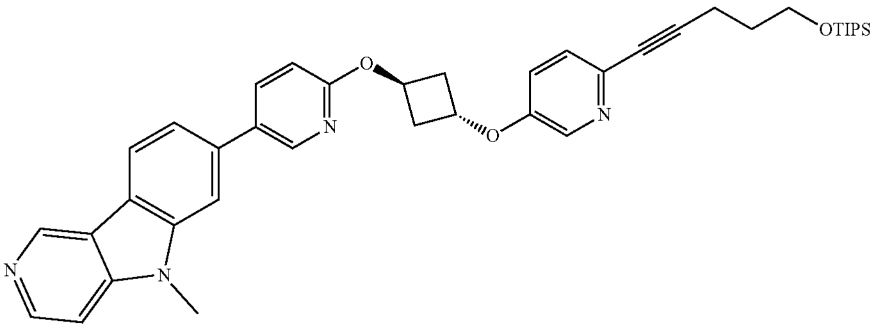

To a solution of 5-bromo-2-((1r,3r)-3-((6-(5-((triisopropylsilyl)oxy)pent-1-yn-1-yl) pyridin-3-yl)oxy)cyclobutoxy) pyridine (180 mg, 0.32 mmol) in 1,4-dioxane (5 ml) and $H_2O$ (1 mL) was added 5-methyl-7-(6-(4,4,5,5-tetramethyl-1,3,2-dioxaborolan-2-yl)pyridin-3-yl)-5H-pyrido[4,3-b]indole (119 mg, 0.39 mmol), CsF (147 mg, 0.96 mmol) and $Pd(aMphos)Cl_2$ (34 mg, 0.06 mmol) at 15° C. under $N_2$. The resulting mixture was stirred at 80° C. for 5 hours. The mixture was quenched with $H_2O$ (20 mL), extracted with EtOAc (10 mL×2). Then the combined organic layers were washed with brine (20 mL×2), dried over anhydrous sodium sulfate and concentrated. The residue was purified with silica gel column to afford the desired product 5-methyl-7-(6-((1r,3r)-3-((6-(5-((triisopropylsilyl)oxy)pent-1-yn-1-yl) pyridin-3-yl)oxy)cyclobutoxy)pyridin-3-yl)-5H-pyrido[4,3-b]indole (80 mg, 38% yield).

Step 4: 5-(5-((1r,3r)-3-((5-(5-methyl-5H-pyrido[4,3-b]indol-7-yl)pyridin-2-yl)oxy)cyclobutoxy)pyridin-2-yl)pent-4-yn-1-ol

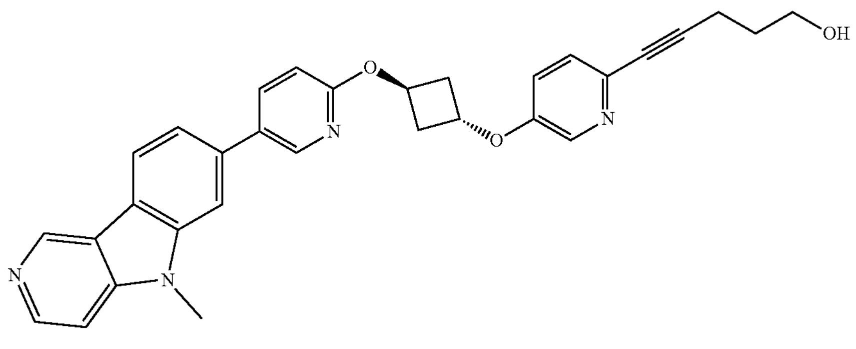 [SMILES: Cn1c2ccncc2c2ccc(-c3ccc(O[C@H]4C[C@H](Oc5ccc(C#CCCCO)nc5)C4)nc3)cc21]

To a solution of 5-methyl-7-(6-((1r,3r)-3-((6-(5-((triisopropylsilyl)oxy)pent-1-yn-1-yl)pyridin-3-yl)oxy)cyclobutoxy)pyridin-3-yl)-5H-pyrido[4,3-b]indole (90 mg, 0.14 mmol) in dry THF (10 mL) was added 1 M TBAF in THF (1 mL, 0.7 mmol) under $N_2$ at 15° C. The mixture was stirred at 40° C. for 1 hour under $N_2$ balloon. The mixture was concentrated. The residue was purified with prep-TLC to afford the desired product 5-(5-((1r,3r)-3-((5-(5-methyl-5H-pyrido[4,3-b]indol-7-yl)pyridin-2-yl)oxy)cyclobutoxy)pyridin-2-yl)pent-4-yn-1-ol (30 mg, 43% yield) as a white solid.

Step 5: 2-(2,6-dioxopiperidin-3-yl)-5-((5-(5-((1r,3r)-3-((5-(5-methyl-5H-pyrido[4,3-b]indol-7-yl)pyridin-2-yl)oxy)cyclobutoxy)pyridin-2-yl)pent-4-yn-1-yl)oxy)isoindoline-1,3-dione

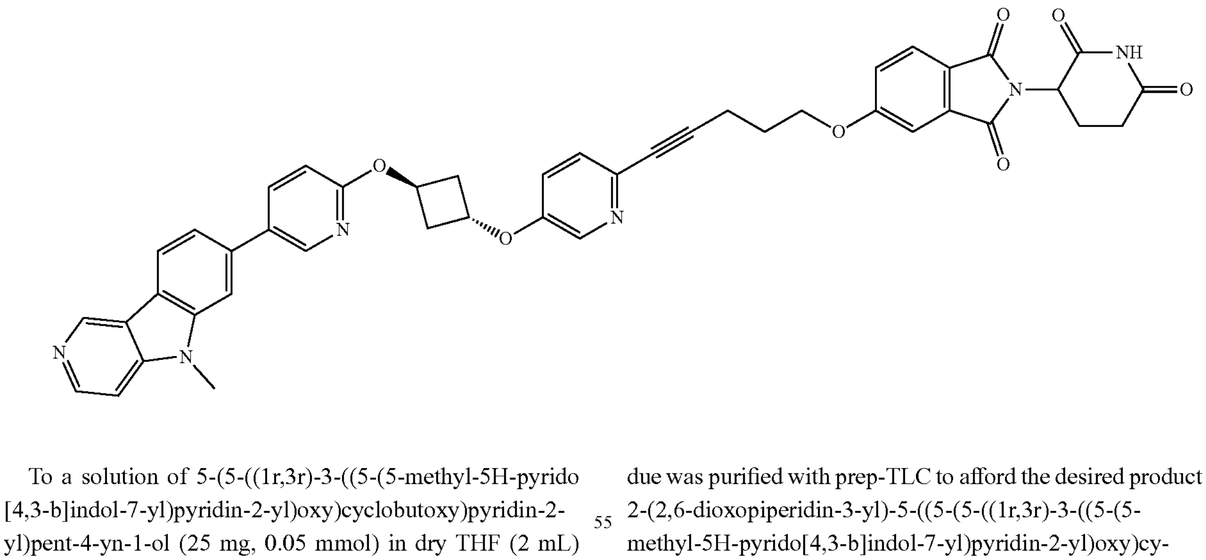

To a solution of 5-(5-((1r,3r)-3-((5-(5-methyl-5H-pyrido[4,3-b]indol-7-yl)pyridin-2-yl)oxy)cyclobutoxy)pyridin-2-yl)pent-4-yn-1-ol (25 mg, 0.05 mmol) in dry THF (2 mL) was added 2-(2,6-dioxopiperidin-3-yl)-5-hydroxyisoindoline-1,3-dione (20 mg, 0.07 mmol), $PPh_3$ (40 mg, 0.14 mmol) at 15° C. under $N_2$. DIAD (32 mg, 0.14 mmol) was added to the mixture at 40° C. under $N_2$. The resulting mixture was stirred at 40° C. for 0.5 hours. Cooled the mixture to 20° C. and quenched with $H_2O$ (10 mL), extracted with EtOAc (10 mL×2). Then the combined organic layers were washed with brine (20 mL×5), dried over anhydrous sodium sulfate and concentrated. The residue was purified with prep-TLC to afford the desired product 2-(2,6-dioxopiperidin-3-yl)-5-((5-(5-((1r,3r)-3-((5-(5-methyl-5H-pyrido[4,3-b]indol-7-yl)pyridin-2-yl)oxy)cyclobutoxy)pyridin-2-yl)pent-4-yn-1-yl)oxy)isoindoline-1,3-dione (22 mg, 58% yield) as a white solid.

$^1$HNMR (400 MHz, DMSO-$d_6$): δ: 11.04 (s, 1H), 9.29 (s, 1H), 8.58 (d, J=2.0 Hz, 1H), 8.43 (d, J=5.6 Hz, 1H), 8.25 (d, J=8.0 Hz, 1H), 8.12-8.16 (m, 2H), 7.92 (s, 1H), 7.78 (d, J=7.6 Hz, 1H), 7.56 (d, J=6.0 Hz, 2H), 7.40 (s, 1H), 7.33 (d, J=8.4 Hz, 2H), 7.20-7.22 (m, 1H), 6.92 (d, J=4.4 Hz, 1H), 5.37 (s, 1H), 5.01-5.37 (m, 2H), 4.25 (t, J=6.0 Hz, 2H), 3.89 (s, 3H), 2.43-2.65 (m, 9H), 1.98 (t, J=6.4 Hz, 3H). $(M+H)^+$ 761.5.

Synthetic Scheme for Exemplary Compound 117

Step 1: 5-methyl-7-(6-((1r,3r)-3-((6-(3-((tetrahydro-2H-pyran-2-yl)oxy)prop-1-yn-1-yl)pyridin-3-yl)oxy)cyclobutoxy)pyridin-3-yl)-5H-pyrido[4,3-b]indole

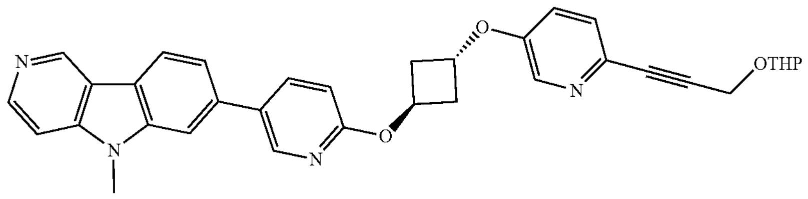

A mixture of (1s,3s)-3-((5-(5-methyl-5H-pyrido[4,3-b]indol-7-yl)pyridin-2-yl)oxy)cyclobutyl methanesulfonate (480 mg, 1.1 mmol) [prepared using procedure described in step 4 of Exemplary Compound 73], 6-(3-((tetrahydro-2H-pyran-2-yl)oxy)prop-1-yn-1-yl)pyridin-3-ol (256 mg, 1.1 mmol) and cesium carbonate (715 mg, 2.2 mmol) in N,N-dimethylformamide (15 ml) was stirred at 70° C. for 16 hours. TLC showed the reaction was complete. The reaction mixture was partitioned between water (20 ml) and ethyl acetate (40 ml). The organic layer was collected, washed with brine (50 ml), dried over sodium sulfate and evaporated under reduced pressure to give a crude residue which was purified by silica gel flash column chromatography (eluted with 0-30% ethyl acetate in hexane) to afford 5-methyl-7-(6-((1r,3r)-3-((6-(3-((tetrahydro-2H-pyran-2-yl)oxy)prop-1-yn-1-yl)pyridin-3-yl)oxy)cyclobutoxy)pyridin-3-yl)-5H-pyrido[4,3-b]indole (350 mg, yield 57%) as white solid.

Step 2: 3-(5-((1r,3r)-3-((5-(5-methyl-5H-pyrido[4,3-b]indol-7-yl)pyridin-2-yl)oxy)cyclobutoxy)pyridin-2-yl)prop-2-yn-1-ol

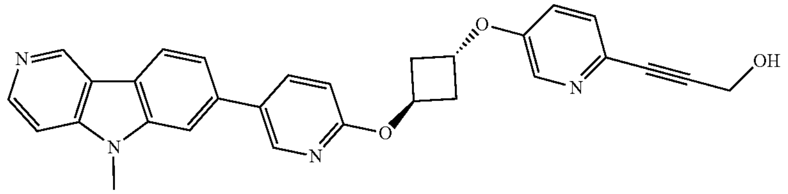 [SMILES: Cn1c2ccncc2c2ccc(-c3ccc(O[C@H]4C[C@H](Oc5ccc(C#CCO)nc5)C4)nc3)cc21]

To the solution of 5-methyl-7-(6-((1r,3r)-3-((6-(3-((tetrahydro-2H-pyran-2-yl)oxy)prop-1-yn-1-yl)pyridin-3-yl)oxy)cyclobutoxy)pyridin-3-yl)-5H-pyrido[4,3-b]indole (350 mg, 0.62 mmol) in tetrahydrofuran (10 ml) was added aqueous hydrogen chloride (5 ml, 2M), and the reaction mixture was stirred at room temperature for 1 hours. TLC showed the reaction was complete. The reaction mixture was quenched with aqueous sodium bicarbonate solution (20 ml), and the reaction mixture was extracted with ethyl acetate (20 ml). The organic layer was collected, and the aqueous layer was extracted with ethyl acetate (10 ml×2). The combined organic layers were washed with brine (10 ml), dried over anhydrous sodium sulfate, and concentrated under reduced pressure to give 3-(5-((1r,3r)-3-((5-(5-methyl-5H-pyrido[4,3-b]indol-7-yl)pyridin-2-yl)oxy)cyclobutoxy)pyridin-2-yl)prop-2-yn-1-ol (270 mg, crude) as white solid which was used in the next step without purification.

Step 3: 3-(5-((1r,3r)-3-((5-(5-methyl-5H-pyrido[4,3-b]indol-7-yl)pyridin-2-yl)oxy)cyclobutoxy)pyridin-2-yl)prop-2-yn-1-yl 4-methylbenzenesulfonate

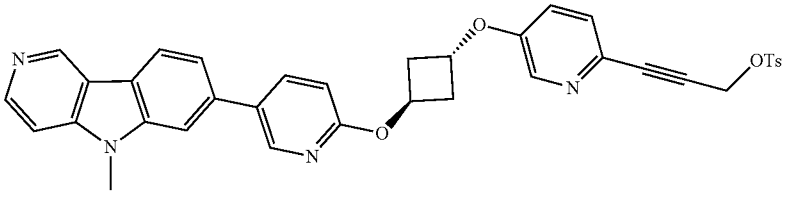 [SMILES: Cc1ccc(S(=O)(=O)OCC#Cc2ccc(O[C@H]3C[C@H](Oc4ccc(-c5ccc6c7cnccc7n(C)c6c5)cn4)C3)cn2)cc1]

A mixture of 3-(5-((1r,3r)-3-((5-(5-methyl-5H-pyrido[4,3-b]indol-7-yl)pyridin-2-yl)oxy)cyclobutoxy)pyridin-2-yl)prop-2-yn-1-ol (200 mg, crude), triethylamine (127 mg, 1.26 mmol) and 4-methyl-benzenesulfonyl chloride (120 mg, 0.63 mmol) in dichloromethane (10 ml) was stirred at room temperature for 1 hour. The reaction mixture was quenched with water (20 ml), extracted with dichloromethane (30 ml). The organic layer was washed with brine (20 ml), dried over sodium sulfate and evaporated under reduced pressure to give a crude residue which was purified by silica gel flash column chromatography (eluted with 5% methanol in dichloromethane) to afford 3-(5-((1r,3r)-3-((5-(5-methyl-5H-pyrido[4,3-b]indol-7-yl)pyridin-2-yl)oxy)cyclobutoxy)pyridin-2-yl)prop-2-yn-1-yl 4-methylbenzenesulfonate (130 mg, yield 49%) as white solid.

Step 4: 2-(2,6-dioxopiperidin-3-yl)-5-((3-(5-((1r,3r)-3-((5-(5-methyl-5H-pyrido[4,3-b]indol-7-yl)pyridin-2-yl)oxy)cyclobutoxy)pyridin-2-yl)prop-2-yn-1-yl)oxy)isoindoline-1,3-dione

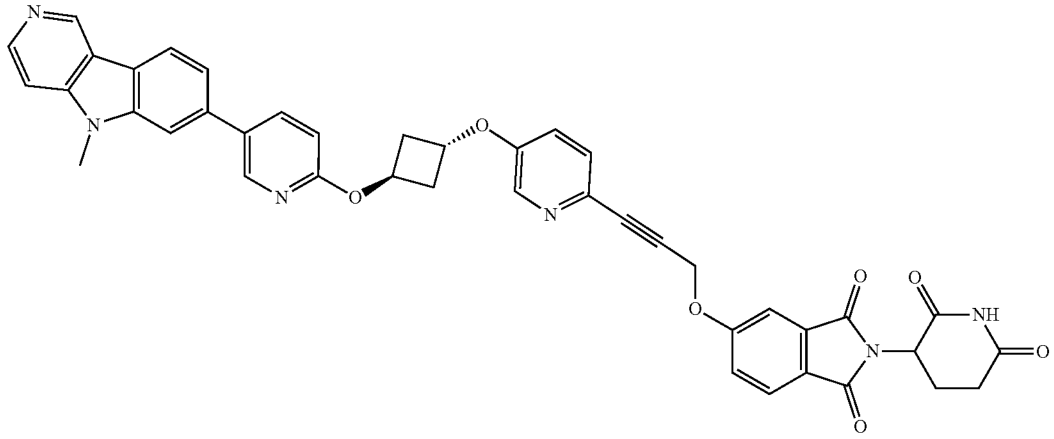 [SMILES: Cn1c2ccncc2c2ccc(-c3ccc(O[C@H]4C[C@H](Oc5ccc(C#CCOc6ccc7c(c6)C(=O)N(C6CCC(=O)NC6=O)C7=O)nc5)C4)nc3)cc21]

To a solution of 3-(5-((1r,3r)-3-((5-(5-methyl-5H-pyrido[4,3-b]indol-7-yl)pyridin-2-yl)oxy)cyclobutoxy)pyridin-2-yl)prop-2-yn-1-yl 4-methylbenzenesulfonate (130 mg, 0.21 mmol), potassium carbonate (85 mg, 0.62 mmol) and 2-(2,6-dioxopiperidin-3-yl)-5-hydroxyisoindoline-1,3-dione (57 mg, 0.21 mmol) in N,N-dimethylformamide (10 ml) was added potassium iodide (35 mg, 0.21 mmol) under nitrogen atmosphere. The resulting mixture was warmed to 50° C. and stirred for 16 hours. TLC showed the reaction was complete. The reaction mixture was partitioned between water (20 ml) and ethyl acetate (20 ml). The organic layer was collected, washed with brine (10 ml), dried over anhydrous sodium sulfate, and concentrated under reduced pressure to give the crude product which was purified by silica gel flash column chromatography (eluted with 8% methanol in dichloromethane) to afford 2-(2,6-dioxopiperidin-3-yl)-5-((3-(5-((1r,3r)-3-((5-(5-methyl-5H-pyrido[4,3-b]indol-7-yl)pyridin-2-yl)oxy)cyclobutoxy)pyridin-2-yl)prop-2-yn-1-yl)oxy)isoindoline-1,3-dione (21.3 mg, yield 14%) as yellow solid.

$^1$H NMR (400 MHz, $CD_3OD$): δ 1.92-1.94 (m, 1H), 2.02-2.10 (m, 2H), 2.62-2.65 (m, 5H), 3.90 (s, 3H), 4.97-5.02 (m, 2H), 5.10 (s, 2H), 5.37 (t, J=6 Hz, 1H), 6.85 (d, J=8.4 Hz, 1H), 7.20-7.22 (m, 1H), 7.34-7.41 (m, 2H), 7.45 (d, J=2.0 Hz, 1H), 7.50-7.56 (m, 2H), 7.75-7.77 (m, 2H), 8.02-8.06 (m, 2H), 8.21 (d, J=8.0 Hz, 1H), 8.37 (d, J=6.0 Hz, 1H), 8.42 (d, J=2.4 Hz, 1H), 9.18 (s, 1H). $(M+H)^+$ 733.4.

Using procedures analogous to those described above for Compound 83 (method of Compound 94), Compound 95, Compound 97 (method of Compound 94), Compound 98, Compound 183 (method of Compound 73), Compound 204 (combination of methods of Compound 73 and Compound 176) were prepared.

Synthetic Scheme for Exemplary Compound 102 and Exemplary Compound 110

2-(2,6-dioxopiperidin-3-yl)-5-((6-(6-((1r,3r)-3-((5-(5-methyl-5H-pyrido[4,3-b]indol-7-yl)pyridin-2-yl)oxy)cyclobutoxy)pyridin-3-yl)hex-5-yn-1-yl)oxy)isoindoline-1,3-dione (Exemplary Compound 102) and 2-(2,6-dioxopiperidin-3-yl)-5-((6-(6-((1r,3r)-3-((5-(5-methyl-5H-pyrido[4,3-b]indol-7-yl)pyridin-2-yl)oxy)cyclobutoxy)pyridin-3-yl)hexyl)oxy)isoindoline-1,3-dione (Exemplary Compound 110)

mmol) (prepared by using procedures analogous to the ones described for steps 1 and 2 for Compound 73] in 1-methylpyrrolidin-2-one (5 ml) was added sodium hydride (60% in mineral oil) (58 mg, 1.45 mmol) at 0° C., and the reaction mixture was stirred for 1 hour. Then to the reaction mixture 2-fluoro-5-iodopyridine (65 mg, 0.29 mmol) was added, and the mixture was stirred at room temperature for 2 hours. TLC showed the reaction complete. The reaction was quenched with water (10 ml) at 0° C., extracted with ethyl acetate (20 ml×2). The combined organic layers were washed with water (20 ml×2), dried over anhydrous sodium

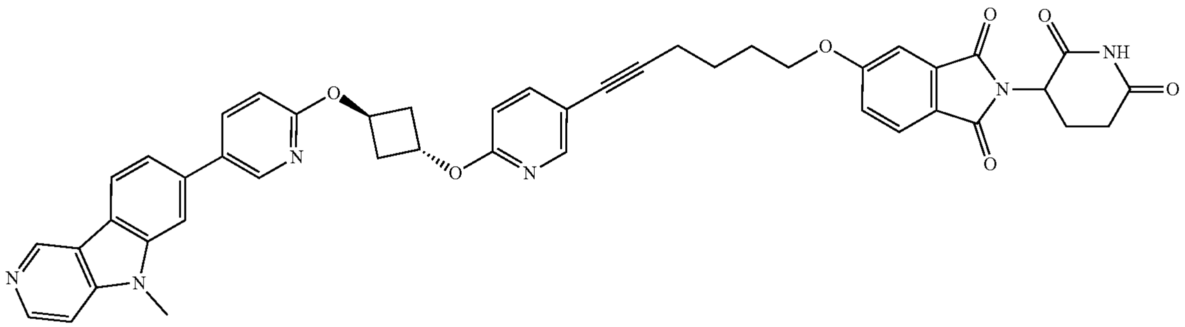

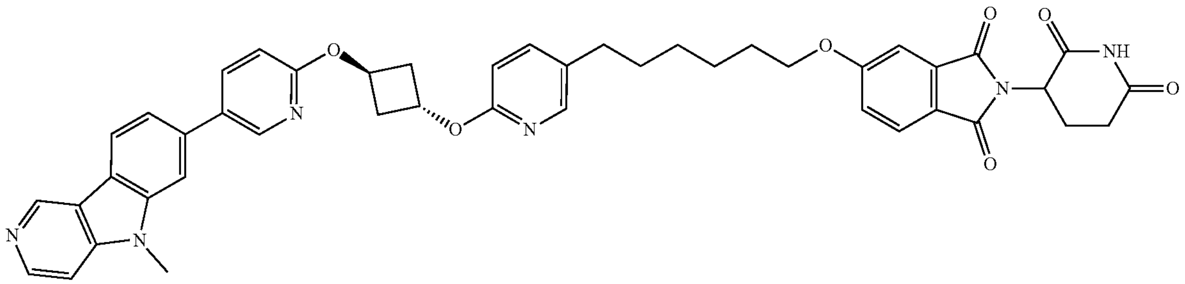

Step 1: 7-(6-((1r,3r)-3-((5-iodopyridin-2-yl)oxy)cyclobutoxy)pyridin-3-yl)-5-methyl-5H-pyrido[4,3-b]indole

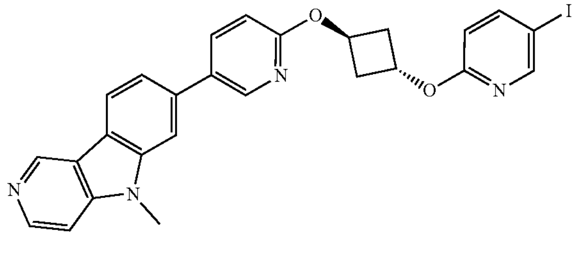 [SMILES: Cn1c2ccncc2c2ccc(-c3ccc(O[C@H]4C[C@H](Oc5ccc(I)cn5)C4)nc3)cc21]

To a solution of (1r,3r)-3-((5-(5-methyl-5H-pyrido[4,3-b]indol-7-yl)pyridin-2-yl)oxy)cyclobutanol (100 mg, 0.29 sulfate, and concentrated under reduced pressure to give a crude residue which was purified by silica gel flash chromatography (eluted with 5% methanol in dichloromethane) to afford 7-(6-((1r,3r)-3-((5-iodopyridin-2-yl)oxy)cyclobutoxy)pyridin-3-yl)-5-methyl-5H-pyrido[4,3-b]indole (100 mg, yield 63%) as a white solid.

Using procedures described for Compound 73, 7-(6-((1r,3r)-3-((5-iodopyridin-2-yl)oxy)cyclobutoxy)pyridin-3-yl)-5-methyl-SH-pyrido[4,3-b]indole was converted to the title compounds, 2-(2,6-dioxopiperidin-3-yl)-5-((6-(6-((1r,3r)-3-((5-(5-methyl-5H-pyrido[4,3-b]indol-7-yl)pyridin-2-yl)oxy)cyclobutoxy)pyridin-3-yl)hex-5-yn-1-yl)oxy)isoindoline-1,3-dione (Compound 102) and 2-(2,6-dioxopiperidin-3-yl)-5-((6-(6-((1r,3r)-3-((5-(5-methyl-5H-pyrido[4,3-b]indol-7-yl)pyridin-2-yl)oxy)cyclobutoxy)pyridin-3-yl)hexyl)oxy)isoindoline-1,3-dione (Compound 110) according to the scheme below.

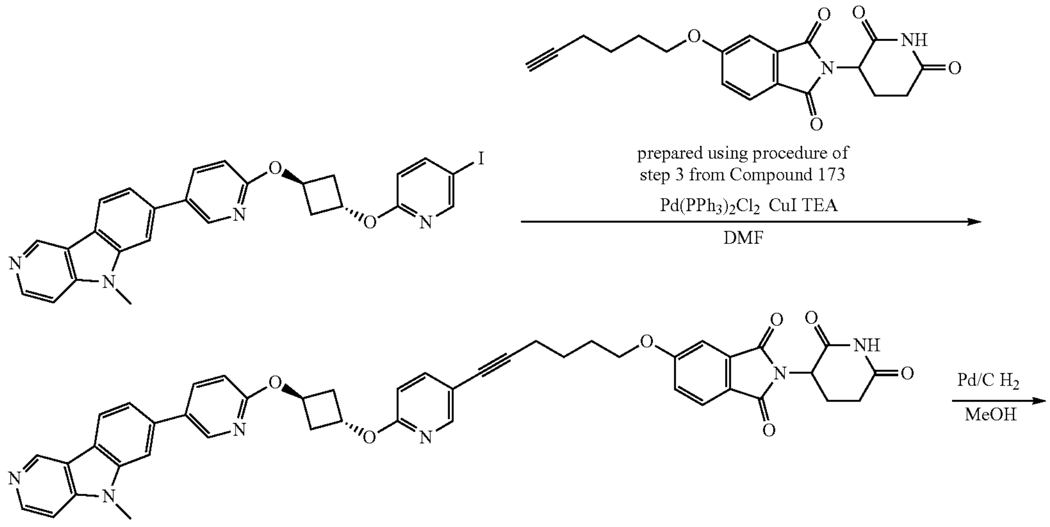

Compound 102

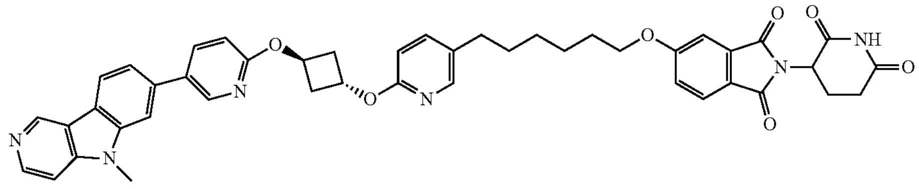

Compound 110

Compound 102: $^{1}$HNMR (400 MHz, DMSO-$d_6$): δ 1.73 (d, J=7.2 Hz, 2H), 1.91 (d, J=7.2 Hz, 2H), 2.01-2.08 (m, 1H), 2.51-2.67 (m, 8H), 2.83-2.94 (m, 1H), 3.96 (s, 3H), 4.24 (t, J=6.0 Hz, 2H), 5.12 (dd, J=12.8, 5.2 Hz, 1H), 5.31-5.52 (m, 2H), 6.99 (d, J=8.4 Hz, 1H), 6.83 (d, J=8.6 Hz, 1H), 7.36 (d, J=8.2 Hz, 1H), 7.44 (s, 1H), 7.75-7.58 (m, 3H), 7.82 (d, J=8.2 Hz, 1H), 7.99 (s, 1H), 8.10-8.28 (m, 2H), 8.33 (d, J=8.2 Hz, 1H), 8.52 (s, 1H), 8.64 (d, J=1.6 Hz, 1H), 9.40 (s, 1H), 11.11 (s, 1H). $(M+H)^+$ 775.5

Compound 110: $^{1}$H NMR (400 MHz, DMSO-$d_6$): δ 1.36 (d, J=7.6 Hz, 2H), 1.45 (d, J=6.8 Hz, 2H), 1.52-1.61 (m, 2H), 1.70-1.80 (m, 2H), 1.98-2.02 (m, 3H), 2.54-2.70 (m, 6H), 2.89 (t, J=16.6 Hz, 1H), 3.96 (s, 3H), 4.16 (d, J=5.0 Hz, 2H), 5.12 (dd, J=12.8, 4.4 Hz, 1H), 5.36-5.43 (m, 2H), 6.77 (d, J=8.4 Hz, 1H), 6.99 (d, J=8.0 Hz, 1H), 7.34 (d, J=8.8 Hz, 1H), 7.42 (s, 1H), 7.60-7.64 (m, 3H), 7.83 (d, J=8.0 Hz, 1H), 7.97 (dd, J=14.0, 6.4 Hz, 2H), 8.33 (d, J=8.4 Hz, 1H), 8.21 (d, J=8.0 Hz, 1H), 8.50 (d, J=4.8 Hz, 1H), 8.65 (s, 1H), 9.37 (s, 1H), 11.11 (s, 1H). $(M+H)^+$ 779.5

Synthetic Scheme for Exemplary Compound 173

5-(2-((3-(5-((1r,3r)-3-((5-(5H-pyrido[4,3-b]indol-7-yl)pyridin-2-yl)oxy)cyclobutoxy)pyridin-2-yl)prop-2-yn-1-yl)oxy)ethoxy)-2-(2,6-dioxopiperidin-3-yl) isoindoline-1,3-dione

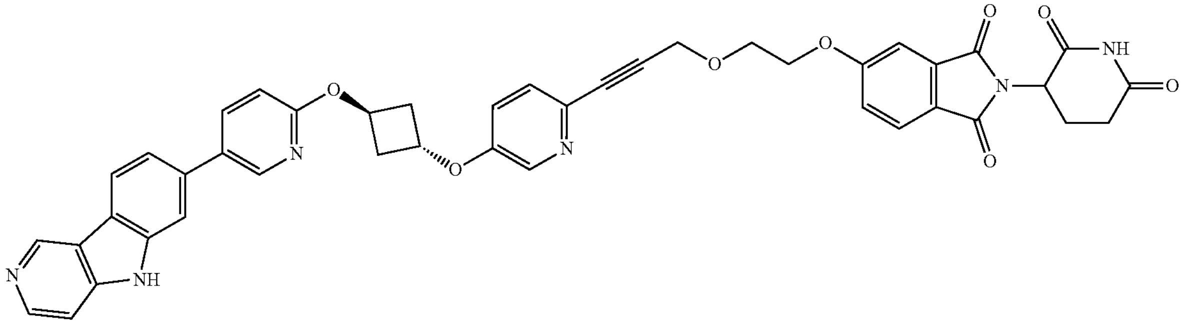 [SMILES: O=C1CCC(N2C(=O)c3ccc(OCCOCC#Cc4ccc(O[C@H]5C[C@H](Oc6ccc(-c7ccc8c(c7)[nH]c7ccncc78)cn6)C5)cn4)cc3C2=O)C(=O)N1]

Step 1: 2-(prop-2-yn-1-yloxy)ethan-1-ol

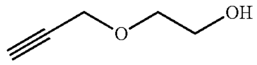

To a stirred mixture of sodium hydride (60% in mineral oil, 115 mg, 2.8 mmol) in anhydrous N,N-dimethylformamide (20 ml) at 0° C. was added ethane-1,2-diol (3.9 g, 63 mmol) and stirred at 0° C. for 0.5 hour. To the resulting mixture was added 3-bromoprop-1-yne (5.0 g, 42 mmol) at 0° C. and stirred at 50° C. overnight. TLC showed the reaction was complete. The reaction mixture was quenched with ice water (20 ml) and partitioned between ethyl acetate (80 ml) and water (100 ml). The organic layer was collected, and the aqueous layer was extracted with ethyl acetate (50 ml×2). The combined organic layers were washed with brine (80 ml), dried over anhydrous sodium sulfate, and concentrated under reduced pressure to give a crude residue which was purified by silica gel flash chromatography (eluted with 0-20% ethyl acetate in hexane) to afford 2-(prop-2-yn-1-yloxy)ethanol (3.4 g, yield 80%) as colorless oil.

Step 2: 2-(prop-2-yn-1-yloxy)ethyl 4-methylbenzenesulfonate

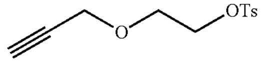 [SMILES: C#CCOCCOS(=O)(=O)c1ccc(C)cc1]

To a stirred solution of 2-(prop-2-yn-1-yloxy)ethanol (1 g, 10 mmol), triethylamine (3 g, 3 mmol) and N,N-dimethylpyridin-4-amine (20 mg, 1 mmol), in dichloromethane (20 ml) was added p-toluenesulfonic acid 2.9 g, 15 mmol) at 0° C. The reaction mixture was allowed to warm up to room temperature and stirred at room temperature overnight. The reaction mixture was diluted with dichloromethane (20 ml), washed with brine (50 ml), dried over anhydrous sodium sulfate and concentrated under reduced pressure to afford crude residue. It was purified by silica gel flash column chromatography (eluent 10-20% ethyl acetate in hexane) to afford 2-(prop-2-yn-1-yloxy)ethyl 4-methylbenzenesulfonate (700 mg, yield: 40%) as light yellow oil.

Step 3: 2-(2,6-dioxopiperidin-3-yl)-5-(2-(prop-2-yn-1-yloxy)ethoxy)isoindoline-1,3-dione

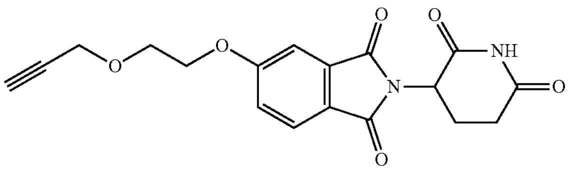 [SMILES: C#CCOCCOc1ccc2c(c1)C(=O)N(C1CCC(=O)NC1=O)C2=O]

To a stirred solution of 2-(prop-2-yn-1-yloxy)ethyl 4-methylbenzenesulfonate (700 mg, 2.8 mmol) and potassium carbonate (1.1 g, 8.3 mmol) in N,N-dimethylformamide (15 ml) was added 2-(2,6-dioxopiperidin-3-yl)-5-hydroxyisoindoline-1,3-dione (755 mg, 2.8 mmol) at room temperature. The resulting mixture was stirred at 50° C. overnight. TLC showed the reaction was complete. The mixture solution was cooled to room temperature. The reaction mixture was partitioned between ethyl acetate (20 ml) and water (30 ml); the organic layer was collected and the aqueous layer was extracted with ethyl acetate (20 ml×2). The combined organic layers were washed with brine (30 ml), dried over anhydrous sodium sulfate, and concentrated under reduced pressure to give a crude residue which was purified by silica gel flash chromatography (eluted with 0-50% ethyl acetate in hexane) to afford 2-(2,6-dioxopiperidin-3-yl)-5-(2-(prop-2-yn-1-yloxy)ethoxy)isoindoline-1,3-dione (290 mg, yield 30%) as light yellow solid.

2-(2,6-dioxopiperidin-3-yl)-5-(2-(prop-2-yn-1-yloxy)ethoxy)isoindoline-1,3-dione was reacted with 7-(6-((1r,3r)-3-((6-iodopyridin-3-yl)oxy)cyclobutoxy)pyridin-3-yl)-5H-pyrido[4,3-b]indole using procedure described for Compound 73 to produce the title compound, 5-(2-((3-(5-((1r,3r)-3-((5-(5H-pyrido[4,3-b]indol-7-yl)pyridin-2-yl)oxy)cyclobutoxy)pyridin-2-yl)prop-2-yn-1-yl)oxy)ethoxy)-2-(2,6-dioxopiperidin-3-yl)isoindoline-1,3-dione.

$^1H$ NMR (400 MHz, DMSO-d6): δ 2.02-2.08 (m, 1H), 2.52-2.76 (m, 6H), 2.85-2.93 (m, 1H), 3.89-3.95 (m, 2H), 4.37-4.42 (m, 2H), 4.49 (s, 2H), 5.06-5.14 (m, 2H), 5.40-5.47 (m, 1H), 6.99 (d, J=8.4 Hz, 1H), 7.30-7.33 (m, 1H), 7.38-7.40 (m, 1H), 7.46-7.48 (m, 2H), 7.62-7.64 (m, 2H), 7.82-7.84 (m, 2H), 8.14-8.17 (m, 1H), 8.24 (d, J=2.8 Hz, 1H), 8.36-8.38 (m, 1H), 8.49 (d, J=6 Hz, 1H), 8.58 (d, J=2.0 Hz, 1H), 9.47 (s, 1H), 11.11 (s, 1H), 12.14-12.28 (m, 1H). $(M+H)^+$ 763.5.

Using procedures analogous to those described above Compounds 110 (method of Compound 102), 124, 144 (method of Compound 102), 145, 146, 147 (method of Compound 94), 172 (method of Compound 73), 179 (method of Compound 173), 188 (method of Compound 173), 189 (method of Compound 73) were prepared.

Synthetic Scheme for Exemplary Compound 180

Step 1: tert-butyl (S)-5-amino-5-oxo-4-(1-oxo-5-(prop-2-yn-1-yloxy)isoindolin-2-yl)pentanoate

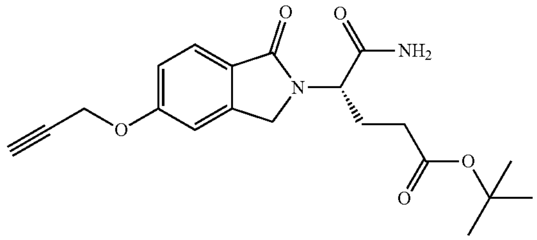 [SMILES: C#CCOc1ccc2c(c1)CN([C@@H](CCC(=O)OC(C)(C)C)C(N)=O)C2=O]

To a stirred solution of (S)-tert-butyl 5-amino-4-(5-hydroxy-1-oxoisoindolin-2-yl)-5-oxopentanoate (450 mg, 1.35 mmol), and 3-bromoprop-1-yne (192 mg, 1.62 mmol) in N,N-dimethylformamide (4 ml) was added potassium carbonate (372 mg, 2.69 mmol) and potassium iodide (22.4 mg, 0.135 mmol), and the mixture was stirred at 50° C. overnight under nitrogen. LCMS showed formation of desired product. The mixture was partitioned between ethyl acetate (50 ml) and water (30 ml). The organic layer was washed with brine (30 ml), dried over anhydrous sodium sulfate, and concentrated under reduced pressure to give a crude residue which was purified by silica gel flash chromatography (eluted with 50% ethyl acetate in hexane and added 5% methanol) to afford (S)-tert-butyl 5-amino-5-oxo-4-(1-oxo-5-(prop-2-yn-1-yloxy)isoindolin-2-yl)pentanoate (489 mg, yield 97%) as colorless oil.

Step 2: 3-(1-oxo-5-(prop-2-yn-1-yloxy)isoindolin-2-yl)piperidine-2,6-dione

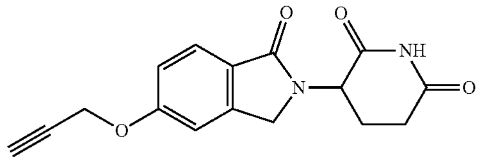 [SMILES: C#CCOc1ccc2c(c1)CN(C1CCC(=O)NC1=O)C2=O]

To a stirred solution of (S)-tert-butyl 5-amino-5-oxo-4-(1-oxo-5-(prop-2-yn-1-yloxy)isoindolin-2-yl)pentanoate (325 mg, 0.873 mmol) in anhydrous tetrahydrofuran (20 ml) was added dropwise potassium tert-butoxide (1N, in THF) (107.7 mg, 0.96 mmol) at 0° C. under nitrogen atmosphere. The reaction mixture was stirred at the same temperature for 20 minutes. LCMS showed formation of desired product. The reaction mixture was quenched with water (20 ml), and extracted with ethyl acetate (50 ml). The organic layer was collected, washed with water (20 ml), dried over anhydrous sodium sulfate, and concentrated under reduced pressure to give a crude residue which was purified by silica gel flash chromatography (eluted with 50% ethyl acetate in hexane and added 10% methanol) to afford 3-(1-oxo-5-(prop-2-yn-1-yloxy)isoindolin-2-yl)piperidine-2,6-dione (128 mg, yield 49%) as white solid.

Step 3: 3-(5-((3-(5-((1r,3r)-3-((5-(5H-pyrido[4,3-b]indol-7-yl)pyridin-2-yl)oxy)cyclobutoxy)pyridin-2-yl)prop-2-yn-1-yl)oxy)-1-oxoisoindolin-2-yl)piperidine-2,6-dione

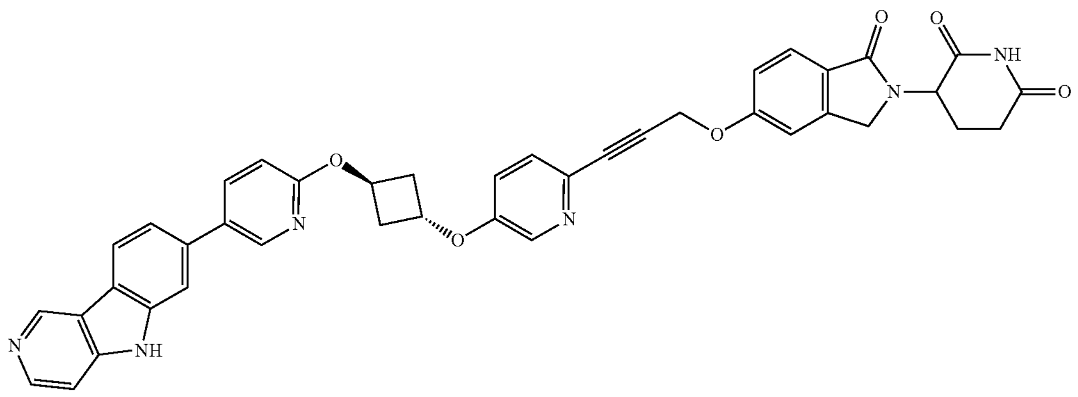 [SMILES: O=C1CCC(N2Cc3cc(OCC#Cc4ccc(O[C@H]5C[C@H](Oc6ccc(-c7ccc8c(c7)[nH]c7ccncc78)cn6)C5)cn4)ccc3C2=O)C(=O)N1]

To a stirred solution of 3-(1-oxo-5-(prop-2-yn-1-yloxy)isoindolin-2-yl)piperidine-2,6-dione (50 mg, 0.168 mmol), 7-(6-((1r,3r)-3-((6-iodopyridin-3-yl)oxy)cyclobutoxy)pyridin-3-yl)-5H-pyrido[4,3-b]indole (74 mg, 0.14 mmol) and triethylamine (70.7 mg, 0.70 mmol) in N,N-dimethylformamide (1 ml) were added trans-dichlorobis(triphenylphosphine) palladium(II) (4.91 mg, 0.007 mmol) and copper iodide (1.33 mg, 0.007 mmol) at room temperature under nitrogen atmosphere; the mixture was degassed with nitrogen three times. The resulting mixture was stirred at 65° C. for 12 hours. TLC showed the reaction was complete. TLC showed the reaction was complete. The mixture was partitioned between ethyl acetate (50 ml) and water (30 ml). The organic layer was washed with brine (30 ml), dried over anhydrous sodium sulfate, and concentrated under reduced pressure to give a crude residue which was purified by prep TLC (eluted with 10% methanol in dichloroethane) to afford 3-(5-((3-(5-((1r,3r)-3-((5-(5H-pyrido[4,3-b]indol-7-yl)pyridin-2-yl)oxy)cyclobutoxy)pyridin-2-yl)prop-2-yn-1-yl)oxy)-1-oxoisoindolin-2-yl)piperidine-2,6-dione (19 mg, 16%) as white solid.

$^{1}$HNMR (400 MHz, DMSO-d6): δ 1.97-2.00 (m, 1H), 2.33-2.44 (m, 2H), 2.55-2.67 (m, 4H), 2.86-2.96 (m, 1H), 4.29 (d, J=17.2 Hz, 1H), 4.42 (d, J=16.8 Hz, 1H), 5.06-5.10 (m, 2H), 5.18 (s, 2H), 5.42-5.45 (m, 1H), 6.99 (d, J=8.4 Hz, 1H), 7.17 (d, J=8.0 Hz, 1H), 7.29-7.33 (m, 2H), 7.50 (d, J=8.4 Hz, 1H), 7.68 (d, J=8.0 Hz, 2H), 7.74 (d, J=5.6 Hz, 1H), 7.89 (s, 1H), 8.16 (d, J=7.6 Hz, 1H), 8.24 (s, 1H), 8.41 (d, J=7.6 Hz, 1H), 8.53-8.59 (m, 2H), 9.56 (s, 1H), 10.97 (s, 1H), 12.54 (br, 1H). $(M+H)^+$ 705.4.

Synthetic Scheme for Exemplary Compound 64

5-(4-(3-(5-((1r,3r)-3-((5-(5H-pyrido[4,3-b]indol-7-yl)pyridin-2-yl)oxy)cyclobutoxy)pyridin-2-yl)propyl)piperazin-1-yl)-2-(2,6-dioxopiperidin-3-yl)isoindoline-1,3-dione

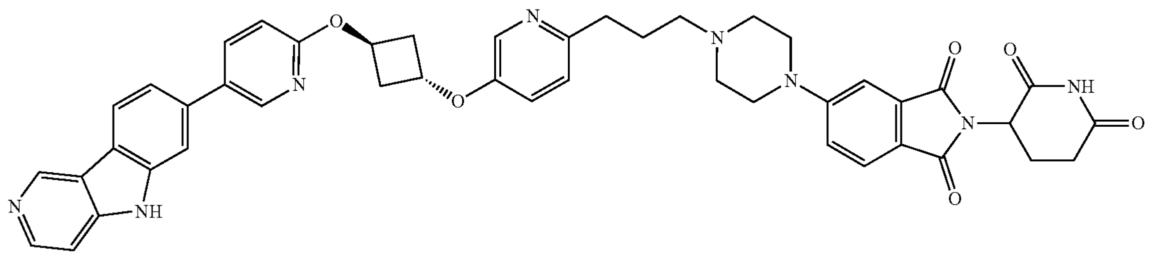 [SMILES: O=C1CCC(N2C(=O)c3ccc(N4CCN(CCCc5ccc(O[C@H]6C[C@H](Oc7ccc(-c8ccc9c(c8)[nH]c8ccncc89)cn7)C6)cn5)CC4)cc3C2=O)C(=O)N1]

The title compound was prepared according to the scheme below using procedures described above for other targets and common procedures known to those skilled in the art. The starting tert-butyl 7-(6-((1r,3r)-3-((6-(3-hydroxyprop-1-yn-1-yl)pyridin-3-yl)oxy)cyclobutoxy)pyridin-3-yl)-5H-pyrido[4,3-b]indole-5-carboxylate was prepared according to the procedures described for the Compound 117.

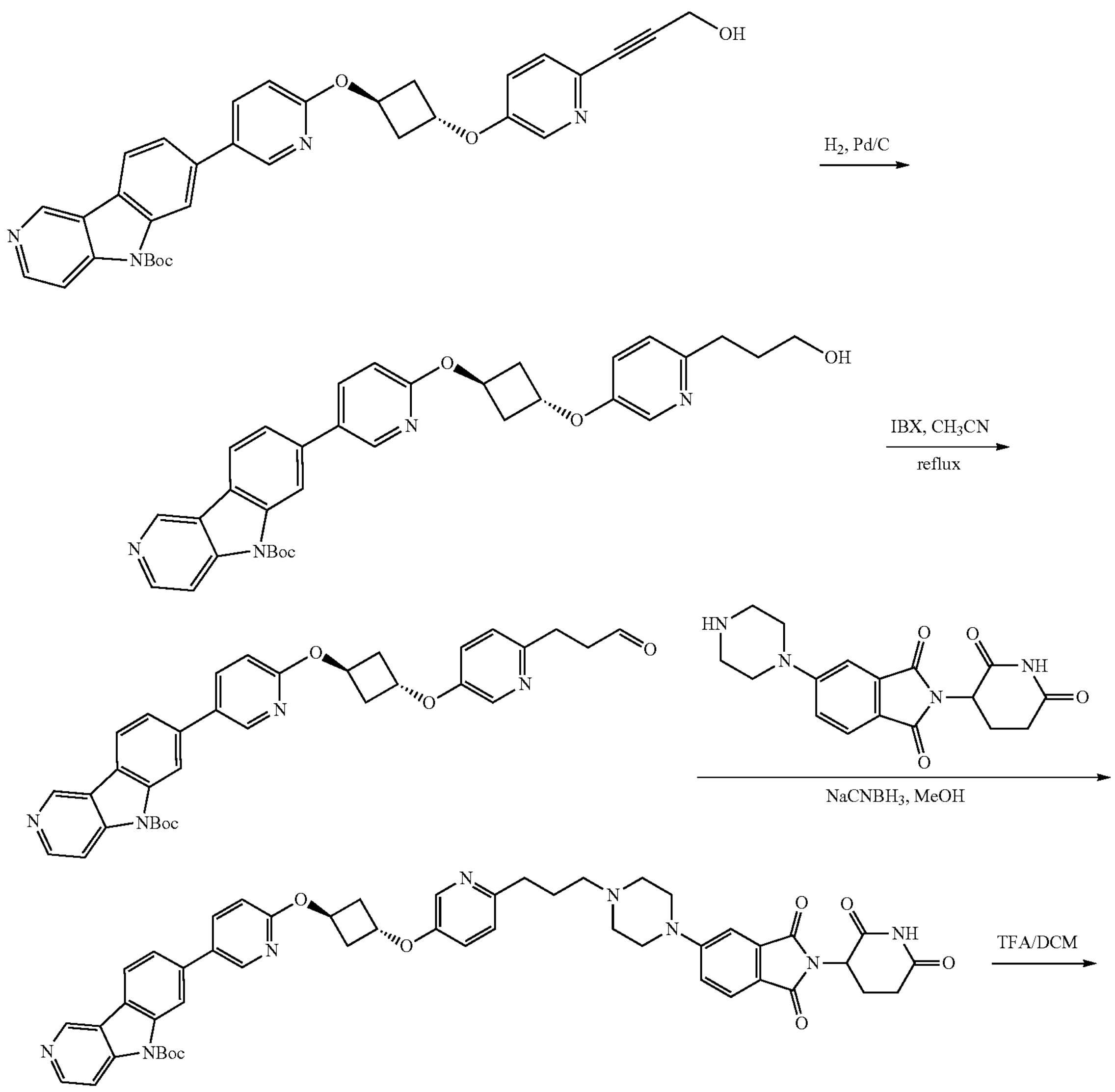

-continued

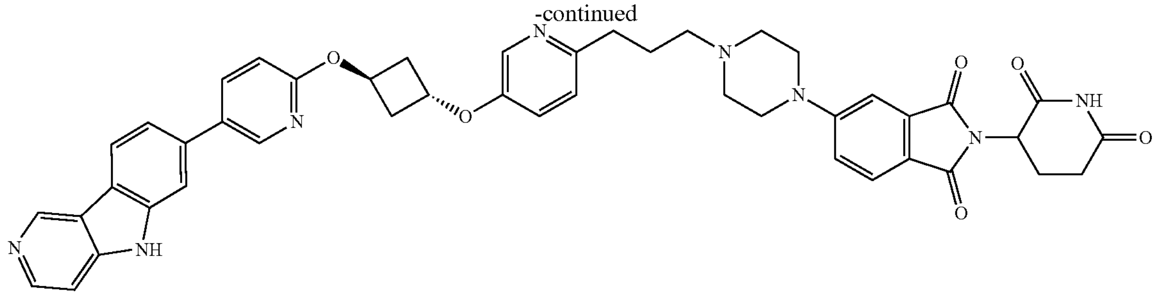

5-(4-(3-(5-((1r,3r)-3-((5-(5H-pyrido[4,3-b]indol-7-yl)pyridin-2-yl)oxy)cyclobutoxy)pyridin-2-yl)propyl)piperazin-1-yl)-2-(2,6-dioxopiperidin-3-yl)isoindoline-1,3-dione

$^1$H NMR (400 MHz, $CD_3OD$) δ 9.42 (s, 1H), 8.53 (d, J=2.3 Hz, 1H), 8.50 (d, J=6.1 Hz, 1H), 8.38 (d, J=8.1 Hz, 1H), 8.13 (d, J=8.0 Hz, 2H), 7.87 (s, 1H), 7.71-7.78 (m, 2H), 7.68 (d, J=8.3 Hz, 1H), 7.42 (s, 1H), 7.33 (s, 2H), 7.29 (d, J=8.6 Hz, 1H), 6.99 (d, J=8.6 Hz, 1H), 5.51 (s, 2H), 5.06-5.14 (m, 2H), 3.55 (s, 4H), 2.58-3.03 (m, 15H), 2.04 (m, 3H).

Synthetic Scheme for Exemplary Compound 67

Step 1: 14-((5-bromo-3-(trifluoromethyl)pyridin-2-yl)oxy)-3,6,9,12-tetraoxatetradecan-1-ol

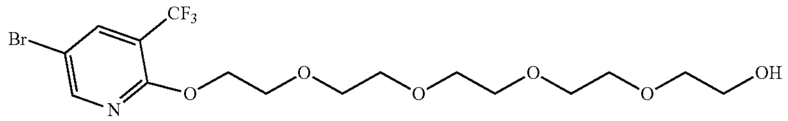 [SMILES: OCCOCCOCCOCCOCCOc1ncc(Br)cc1C(F)(F)F]

To a solution of pentaethylene glycol (330 mg, 1.38 mmol) in THF (5 mL) was added NaH (30 mg, 0.76 mmol) at 0° C. The solution was stirred at room temperature for 1 hour. Then 5-bromo-2-chloro-3-(trifluoromethyl)pyridine (180 mg, 0.69 mmol) was added. The resulting solution was stirred at 80° C. for 2 hours. The reaction solution was quenched with water. The mixture was extracted with ethyl acetate (20 mL). The combined organic layers were washed with brine (10 mL). The organic layer was dried over anhydrous sodium sulfate, filtered and concentrated to afford the desired compound (400 mg, crude), which was used into the next step without further purification.

Step 2: 14-((5-(5-methyl-5H-pyrido[4,3-b]indol-7-yl)-3-(trifluoromethyl)pyridin-2-yl)oxy)-3,6,9,12-tetraoxatetradecan-1-ol

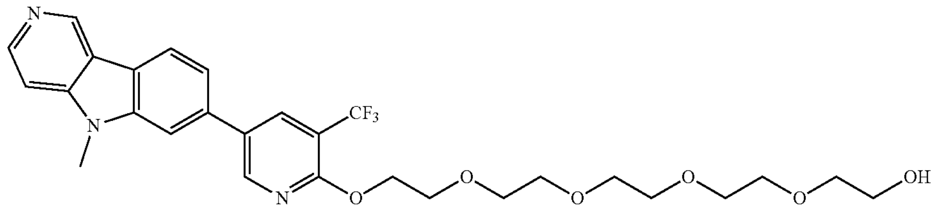 [SMILES: Cn1c2ccncc2c2ccc(-c3cnc(OCCOCCOCCOCCOCCO)c(C(F)(F)F)c3)cc21]

A mixture of 14-((5-bromo-3-(trifluoromethyl)pyridin-2-yl)oxy)-3,6,9,12-tetraoxatetradecan-1-ol (180 mg, 0.39 mmol), 5-methyl-7-(4,4,5,5-tetramethyl-1,3,2-dioxaborolan-2-yl)-5H-pyrido[4,3-b]indole (120 mg, 0.39 mmol) [prepared as described in step 1 of Compound 63], Pd(amphos)$Cl_2$ (20 mg, 10%) and CsF (118 mg, 0.78 mmol) in dioxane/$H_2O$ (10/1, 5 mL) was stirred at 80° C. for 2 hours. The reaction mixture was quenched with water. The mixture was extracted with ethyl acetate (20 mL). The organic layer was dried over $Na_2SO_4$, filtered and concentrated under vacuum. The residue was purified by silica gel column chromatography to afford the desired compound (85 mg, 47% yield).

Step 3: 2-(2,6-dioxopiperidin-3-yl)-5-((14-((5-(5-methyl-5H-pyrido[4,3-b]indol-7-yl)-3-(trifluoromethyl)pyridin-2-yl)oxy)-3,6,9,12-tetraoxatetradecyl)oxy)isoindoline-1,3-dione

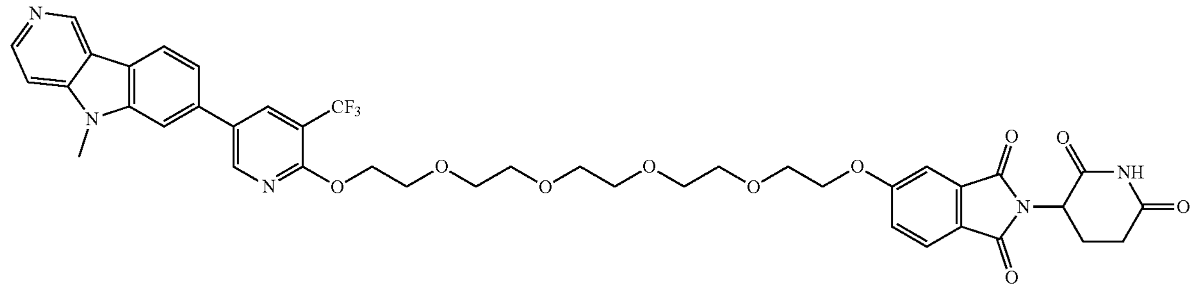 [SMILES: Cn1c2ccncc2c2ccc(-c3cnc(OCCOCCOCCOCCOCCOc4ccc5c(c4)C(=O)N(C4CCC(=O)NC4=O)C5=O)c(C(F)(F)F)c3)cc21]

To a solution of 14-((5-(5-methyl-5H-pyrido[4,3-b]indol-7-yl)-3-(trifluoromethyl)pyridin-2-yl)oxy)-3,6,9,12-tetraoxatetradecan-1-ol (85 mg, 0.15 mmol), 2-(2,6-dioxopiperidin-3-yl)-5-hydroxyisoindoline-1,3-dione (41 mg, 0.15 mmol) and PPh3 (47 mg, 0.18 mmol) in THF was added DIAD (45 mg, 0.22 mmol) at 40° C. The mixture was stirred at 40° C. for 1 hour. The reaction solution was quenched with water. The mixture was extracted with ethyl acetate (20 mL). The combined organic layers were washed with brine (10 mL). The organic layer was dried over $Na_2SO_4$, filtered and concentrated under vacuum. The residue was purified by silica gel column chromatography to afford the title compound (34 mg, 28% yield).

$^1H$ NMR (400 MHz, $CD_3OD$): δ 9.25 (s, 1H), 8.79 (s, 1H), 8.37-8.39 (d, J=8.0 Hz, 1H), 8.28-8.30 (d, J=8.0 Hz, 2H), 7.89 (s, 1H), 7.63-7.65 (d, J=8.0 Hz, 1H), 7.54-7.56 (m, 2H), 7.26 (s, 1H), 7.18-7.20 (m, 1H), 5.02-5.05 (m, 1H), 4.62-4.64 (m, 2H), 4.17-4.19 (m, 2H), 3.95 (s, 3H), 3.88-3.90 (m, 2H), 3.82-3.84 (m, 2H), 3.61-3.71 (m, 13H), 2.55-2.81 (m, 3H), 2.95-2.99 (m, 1H). $(M+H)^+$ 820.5.

Using procedures of Compound 67 the following were prepared: Compound 69, Compound 113.

Synthetic Scheme for Exemplary Compound 65

Step 1: 4-((1r,3r)-3-(benzyloxy)cyclobutoxy)pyridine

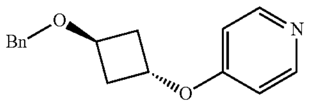 [SMILES: c1ccc(CO[C@H]2C[C@H](Oc3ccncc3)C2)cc1]

To a solution of pyridin-4-ol (3.20 g, 33.66 mmol, 1.5 eq) and 3-benzyloxycyclobutanol (4 g, 22.44 mmol, 1 eq) in tetrahydrofuran (200 mL) was added triphenylphosphine (7.06 g, 26.93 mmol, 1.2 eq) and diisopropyl azodicarboxylate (5.45 g, 26.93 mmol, 1.2 eq) in one portion at 10° C. under nitrogen. The mixture was stirred at 50° C. for 12 hours. The reaction mixture was concentrated under reduced pressure to remove tetrahydrofuran. Water (50 mL) was poured into the mixture and stirred for 1 minute. The aqueous phase was extracted with dichloromethane (50 mL×3). The combined organic phase was washed with brine (50 mL×2), dried with anhydrous sodium sulfate, filtered and concentrated in vacuum. The residue was purified by silica gel column chromatography (petroleum ether:tetrahydrofuran from 20:1 to 5:1). HPLC showed 41% of the product in 254 mm. The residue was purified by flash C18 column chromatography [acetonitrile:water (0.5% ammonium hydroxide)=5%-50%]. Compound 4-(3-benzyloxycyclobutoxy) pyridine (3.2 g, 12.53 mmol, 55% yield) was obtained as a white solid.

Step 2: 1-benzyl-4-((1r,3r)-3-(benzyloxy)cyclobutoxy)pyridin-1-ium bromide

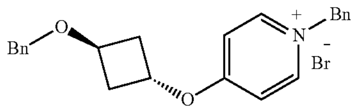

To a solution of 4-(3-benzyloxycyclobutoxy)pyridine (4.2 g, 16.45 mmol, 1 eq) in toluene (65 mL) was added benzyl bromide (2.81 g, 16.45 mmol, 1 eq). The mixture was stirred at 80° C. for 12 hours. The reaction mixture was concentrated under reduced pressure to remove toluene. The crude product was triturated with petroleum ether (80 mL). Compound 1-benzyl-4-((1r,3r)-3-(benzyloxy)cyclobutoxy)pyridin-1-ium bromide (6.5 g, 15.25 mmol, 92% yield) was obtained as a white solid.

Step 3: 1-benzyl-4-((1r,3r)-3-(benzyloxy)cyclobutoxy)-1,2,3,6-tetrahydropyridine

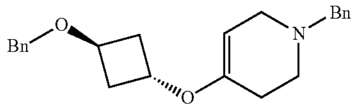 [SMILES: C1=C(O[C@H]2C[C@H](OCc3ccccc3)C2)CCN(Cc2ccccc2)C1]

To a solution of 1-benzyl-4-((1r,3r)-3-(benzyloxy)cyclobutoxy)pyridin-1-ium bromide (6.5 g, 15.25 mmol, 1 eq) in ethanol (120 mL) was added sodium borohydride (3.46 g, 91.47 mmol, 6 eq) at 0° C. The mixture was stirred at 15° C. for 4 hours. The reaction mixture was concentrated under reduced pressure to remove ethanol. The residue was diluted with water (25 mL) and extracted with ethyl acetate (50 mL×2). The combined organic phase was washed with saturated brine (40 mL×3), dried with anhydrous sodium sulfate, filtered and concentrated in vacuum. Compound 1-benzyl-4-(3-benzyloxycyclobutoxy)-3,6-dihydro-2H-pyridine (4.5 g, 12.88 mmol, 84% yield) was obtained as a colorless oil.

Step 4: (1r,3r)-3-((1-benzylpiperidin-4-yl)oxy)cyclobutan-1-ol

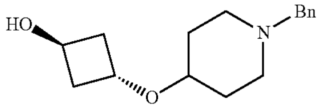 [SMILES: O[C@H]1C[C@H](OC2CCN(Cc3ccccc3)CC2)C1]

To a solution of 1-benzyl-4-(3-benzyloxycyclobutoxy)-3,6-dihydro-2H-pyridine (4.5 g, 12.88 mmol, 1 eq) in tetrahydrofuran (95 mL) and ethanol (70 mL) was added palladium on activated carbon catalyst (0.5 g, 10% purity) under nitrogen atmosphere. The suspension was degassed and purged with hydrogen for 3 times. The mixture was stirred under hydrogen (50 Psi) at 25° C. for 24 hours. LCMS showed the reaction was not completed. The mixture was then stirred at 35° C. for 12 hours. The reaction mixture was filtered and the filtrate was concentrated. The residue was purified by silica gel column chromatography (dichloromethane:methanol:ammonium hydroxide from 20:1:0 to 10:1:0.1). Compound 3-[(1-benzyl-4-piperidyl)oxy]cyclobutanol (2.8 g, 10.71 mmol, 83% yield) was obtained as a colorless oil.

Step 5: tert-butyl 4-((1r,3r)-3-hydroxycyclobutoxy) piperidine-1-carboxylate

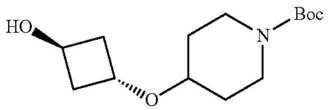 [SMILES: CC(C)(C)OC(=O)N1CCC(O[C@H]2C[C@H](O)C2)CC1]

To a solution of 3-[(1-benzyl-4-piperidyl)oxy]cyclobutanol (1.1 g, 4.21 mmol, 1 eq) in methanol (10 mL) was added palladium hydroxide (591 mg) and di-tert-butyl carbonate (1.84 g, 8.42 mmol, 2 eq) under nitrogen atmosphere. The suspension was degassed and purged with hydrogen for 3 times. The mixture was stirred under hydrogen (50 Psi) at 25° C. for 12 hours. The reaction mixture was filtered and the filter was concentrated. The residue was purified by silica gel chromatography (petroleum ether:ethyl acetate=20:1 to 2:1). Compound tert-butyl 4-(3-hydroxycyclobutoxy)piperidine-1-carboxylate (820 mg, 3.02 mmol, 71% yield) was obtained as a colorless oil.

Step 6: tert-butyl 4-((1r,3r)-3-((5-bromopyridin-2-yl)oxy)cyclobutoxy)piperidine-1-carboxylate

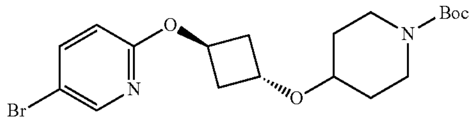 [SMILES: CC(C)(C)OC(=O)N1CCC(O[C@H]2C[C@H](Oc3ccc(Br)cn3)C2)CC1]

To a mixture of tert-butyl 4-(3-hydroxycyclobutoxy)piperidine-1-carboxylate (400 mg, 1.47 mmol, 1 eq) and 5-bromo-2-fluoro-pyridine (285 mg, 1.62 mmol, 1.1 eq) in dimethylformamide (8 mL) was added cesium carbonate (960 mg, 2.95 mmol, 2 eq) in one portion at 25° C. under nitrogen atmosphere. The mixture was stirred at 100° C. for 2 hours. The reaction mixture was poured into water (30 mL) and stirred for 5 minutes. The aqueous phase was extracted with ethyl acetate (20 mL×3). The combined organic phase was washed with brine (30 mL×3), dried with anhydrous sodium sulfate, filtered and concentrated in vacuum. The residue was purified by silica gel chromatography (1000 mesh silica gel, petroleum ether/ethyl acetate from 200:1 to 20:1). The product, tert-butyl 4-[3-[(5-bromo-2-pyridyl) oxy]cyclobutoxy] piperidine-1-carboxylate (560 mg, 1.30 mmol, 88% yield), was obtained as a colorless oil.

Step 7: tert-butyl 4-((1r,3r)-3-((5-(4,4,5,5-tetramethyl-1,3,2-dioxaborolan-2-yl)pyridin-2-yl)oxy)cyclobutoxy)piperidine-1-carboxylate

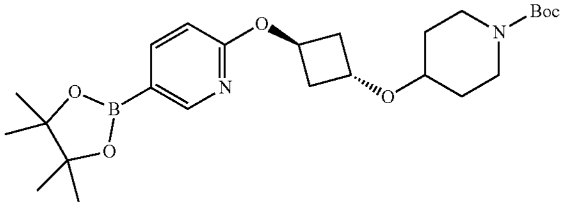 [SMILES: CC(C)(C)OC(=O)N1CCC(O[C@H]2C[C@H](Oc3ccc(B4OC(C)(C)C(C)(C)O4)cn3)C2)CC1]

To a suspension of tert-butyl 4-[3-[(5-bromo-2-pyridyl) oxy]cyclobutoxy]piperidine-1-carboxylate (560 mg, 1.31 mmol, 1 eq), 4,4,4',4',5,5,5',5'-octamethyl-2,2'-bi(1,3,2-dioxaborolane) (432 mg, 1.70 mmol, 1.3 eq) and potassium acetate (257 mg, 2.62 mmol, 2 eq) in dioxane (20 mL) was added [1,1'-bis(diphenylphosphino) ferrocene]dichloropalladium(II) (95 mg, 0.13 mmol, 0.1 eq). The mixture was degassed in vacuum and purged with nitrogen for 3 times. The mixture was heated to 80° C. and stirred at 80° C. for 15 hours. The mixture was filtered, and the filtrate was concentrated in vacuum. The residue was purified by silica gel column chromatography (petroleum ether/ethyl acetate from 20:1 to 10:1). Tert-butyl 4-[3-[[5-(4,4,5,5-tetramethyl-1,3,2-dioxaborolan-2-yl)-2-pyridyl]oxy]cyclobutoxy]piperidine-1-carboxylate (500 mg, 1.05 mmol, 80% yield) as a colorless oil was obtained.

Step 8: tert-butyl 4-((1r,3r)-3-((5-(5H-pyrido[4,3-b]indol-7-yl)pyridin-2-yl)oxy)cyclobutoxy)piperidine-1-carboxylate

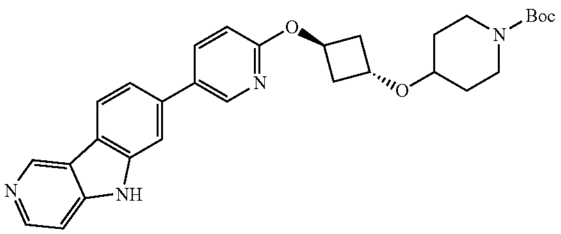 [SMILES: CC(C)(C)OC(=O)N1CCC(O[C@H]2C[C@H](Oc3ccc(-c4ccc5c(c4)[nH]c4ccncc45)cn3)C2)CC1]

To a solution of tert-butyl 4-[3-[[5-(4,4,5,5-tetramethyl-1,3,2-dioxaborolan-2-yl)-2-pyridyl] oxy]cyclobutoxy]piperidine-1-carboxylate (240 mg, 0.50 mmol, 1 eq), 7-bromo-5H-pyrido [4,3-b]indole (125 mg, 0.50 mmol, 1 eq) and potassium carbonate (140 mg, 1.01 mmol, 2 eq) in a mixture of dimethylformamide (8 mL) and water (2 mL) was added [1,1'-bis(diphenylphosphino)ferrocene]dichloropalladium (II) (37 mg, 0.05 mmol, 0.1 eq). The mixture was degassed in vacuum and purged with nitrogen three times. The mixture was stirred at 100° C. for 3 hours. The mixture was poured into 50 mL saturated brine, and then extracted with ethyl acetate (50 mL×2). The combined organic layer was washed with brine (50 mL×3), dried over anhydrous sodium sulfate, filtered and concentrated in vacuum. The residue was purified by preparative thin layer chromatography (dichloromethane:methanol=20:1). Tert-butyl 4-[3-[[5-(5H-pyrido[4,3-b]indol-7-yl)-2-pyridyl]oxy]cyclobutoxy]piperidine-1-carboxylate (175 mg, 0.34 mmol, 67% yield) as an off-white solid was obtained.

Step 9: 7-(6-((1r,3r)-3-(piperidin-4-yloxy)cyclobutoxy)pyridin-3-yl)-5H-pyrido[4,3-b]indole

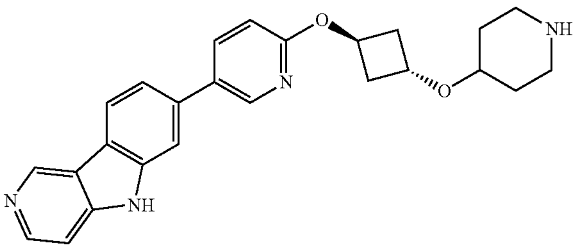 [SMILES: c1cc2[nH]c3cc(-c4ccc(O[C@H]5C[C@H](OC6CCNCC6)C5)nc4)ccc3c2cn1]

Tert-butyl 4-[3-[[5-(5H-pyrido[4,3-b]indol-7-yl)-2-pyridyl]oxy]cyclobutoxy]piperidine-1-carboxylate (170 mg, 0.33 mmol, 1 eq) in hydrochloric acid (4 M in dioxane, 8 mL, 100 eq) was stirred at 25° C. for 10 minutes. The mixture was concentrated in vacuum. The product 7-[6-[3-(4-piperidyloxy)cyclobutoxy]-3-pyridyl]-5H-pyrido[4,3-b]indole (190 mg, crude, hydrochloride) was obtained as a brown solid and was directly used in the next step without further purification.

Step 10: 5-((5,5-dimethoxypentyl)oxy)-2-(2,6-dioxopiperidin-3-yl)isoindoline-1,3-dione

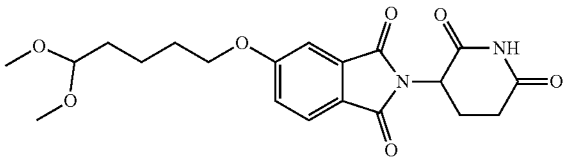 [SMILES: COC(CCCCOc1ccc2c(c1)C(=O)N(C1CCC(=O)NC1=O)C2=O)OC]

To a solution of 2-(2,6-dioxopiperidin-3-yl)-5-hydroxyisoindoline-1,3-dione (548 mg, 2.00 mmol, 1 eq) and 5-bromo-1,1-dimethoxypentane (506 mg, 2.40 mmol, 1.2 eq) in a mixture of acetone (3 mL) and dimethylformamide (3 mL) was added potassium carbonate (552 mg, 4.00 mmol, 2 eq). The mixture was heated to 50° C. and stirred at 50° C. for 2 hours. The mixture was poured into 50 mL 0.1 M aqueous hydrochloric acid, and then extracted with ethyl acetate (50 mL×2). The combined organic layer was washed with brine (50 mL×3), dried over anhydrous sodium sulfate, filtered and concentrated in vacuum. The residue was purified by preparative thin layer chromatography (dichloromethane:methanol=20:1). 5-((5,5-dimethoxypentyl)oxy)-2-(2,6-dioxopiperidin-3-yl)isoindoline-1,3-dione (120 mg, 0.30 mmol, 14% yield) as a colorless oil was obtained.

Step 11: 5-((2-(2,6-dioxopiperidin-3-yl)-1,3-dioxoisoindolin-5-yl)oxy)pentanal

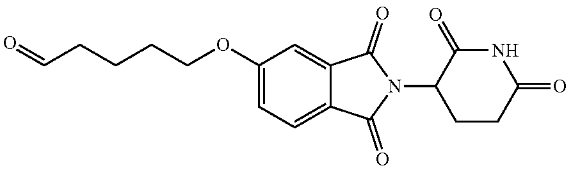 [SMILES: O=CCCCCOc1ccc2c(c1)C(=O)N(C1CCC(=O)NC1=O)C2=O]

To a mixture of 5-(5,5-dimethoxypentoxy)-2-(2,6-dioxo-3-piperidyl)isoindoline-1,3-dione (120 mg, 0.29 mmol, 1 eq) in tetrahydrofuran (10 mL) was added sulfuric acid (2 M in water, 7 mL, 50 eq) in one portion at 25° C. under nitrogen atmosphere. The mixture was stirred at 70° C. for 1 hour. The aqueous phase was extracted with ethyl acetate (20 mL×3). The combined organic phase was washed with saturated aqueous sodium bicarbonate (20 mL×2), and then brine (20 mL×3), dried with anhydrous sodium sulfate, filtered and concentrated in vacuum. The product 5-[2-(2,6-dioxo-3-piperidyl)-1,3-dioxo-isoindolin-5-yl]oxypentanal (93 mg, crude) was obtained as a light yellow solid.

Step 12: 5-((5-(4-((1r,3r)-3-((5-(5H-pyrido[4,3-b]indol-7-yl)pyridin-2-yl)oxy)cyclobutoxy)piperidin-1-yl)pentyl)oxy)-2-(2,6-dioxopiperidin-3-yl)isoindoline-1,3-dione

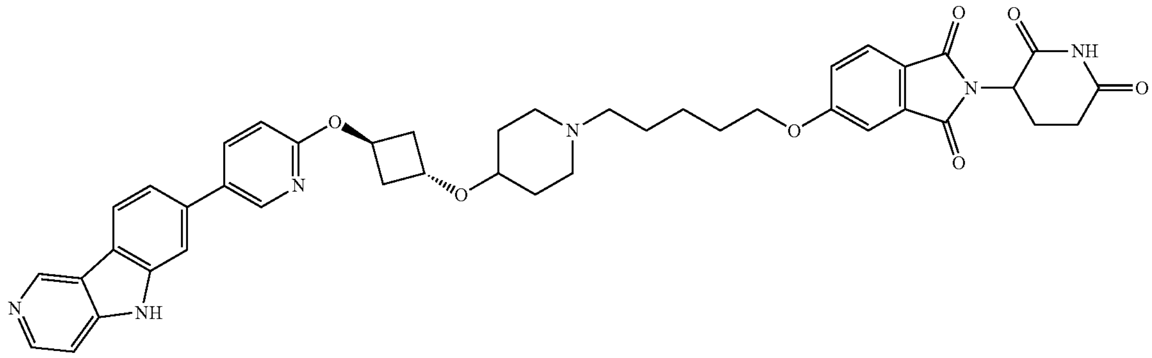 [SMILES: O=C1CCC(N2C(=O)c3ccc(OCCCCCN4CCC(O[C@H]5C[C@H](Oc6ccc(-c7ccc8c(c7)[nH]c7ccncc78)cn6)C5)CC4)cc3C2=O)C(=O)N1]

To a mixture of 7-[6-[3-(4-piperidyloxy)cyclobutoxy]-3-pyridyl]-5H-pyrido[4,3-b]indole (110 mg, 0.24 mmol, 1 eq, hydrochloride) in dichloroethane (2 mL) and methanol (5 mL) was added sodium acetate (40 mg, 0.49 mmol, 2 eq) in one portion at 20° C. The mixture was stirred at 20° C. for 10 minutes. 5-[2-(2,6-dioxo-3-piperidyl)-1,3-dioxo-isoindolin-5-yl]oxypentanal (88 mg, 0.24 mmol, 1 eq) was added. The mixture was stirred at 20° C. for 10 minutes. And then acetic acid (0.02 mL) and sodium cyanoborohydride (31 mg, 0.49 mmol, 2 eq) was added in one portion. The mixture was stirred at 35° C. for 40 minutes. The mixture was filtered and the filtrate was concentrated in vacuum. The residue was purified by Semi-preparative reverse phase HPLC (column: Phenomenex Synergi C18 150*25*10 um; mobile phase: [water (0.225% formic acid)-acetonitrile]; B %: 3%-33%, 10 min). The product 2-(2,6-dioxo-3-piperidyl)-5-[5-[4-[3-[[5-(5H-pyrido[4,3-b]indol-7-yl)-2-pyridyl]oxy] cyclobutoxy]-1-piperidyl]pentoxy]isoindoline-1,3-dione triformate (50.2 mg, 0.05 mmol, 21% yield) was obtained as an off-white solid.

$^1$H NMR: (400 MHz, DMSO-d6) δ: 11.80 (s, 1H), 11.11 (s, 1H), 9.35 (s, 1H), 8.55 (d, J=2.4 Hz, 1H), 8.42 (d, J=5.6 Hz, 1H), 8.29 (d, J=8.4 Hz, 1H), 8.18 (s, 3H), 8.11 (dd, J=2.4, 8.8 Hz, 1H), 7.83 (d, J=8.4 Hz, 1H), 7.76 (s, 1H), 7.55 (d, J=8.4 Hz, 1H), 7.48 (d, J=5.6 Hz, 1H), 7.42 (d, J=2.0 Hz, 1H), 7.35 (dd, J=2.0, 8.4 Hz, 1H), 6.92 (d, J=8.4 Hz, 1H), 5.30 (d, J=3.6 Hz, 1H), 5.11 (dd, J=5.6, 13.2 Hz, 1H), 4.35 (t, J=6.4 Hz, 1H), 4.17 (t, J=6.4 Hz, 2H), 2.93-2.84 (m, 2H), 2.77 (s, 2H), 2.63-2.54 (m, 3H), 2.37 (d, J=6.0 Hz, 4H), 2.22-1.98 (m, 4H), 1.87-1.74 (m, 4H), 1.53-1.38 (m, 6H). $(M+H)^+$ 757.5

Using procedures, analogous to those described above, the following were prepared: Compounds 82,123 (as described for Compounds 65 and 67 and detailed in the scheme below).

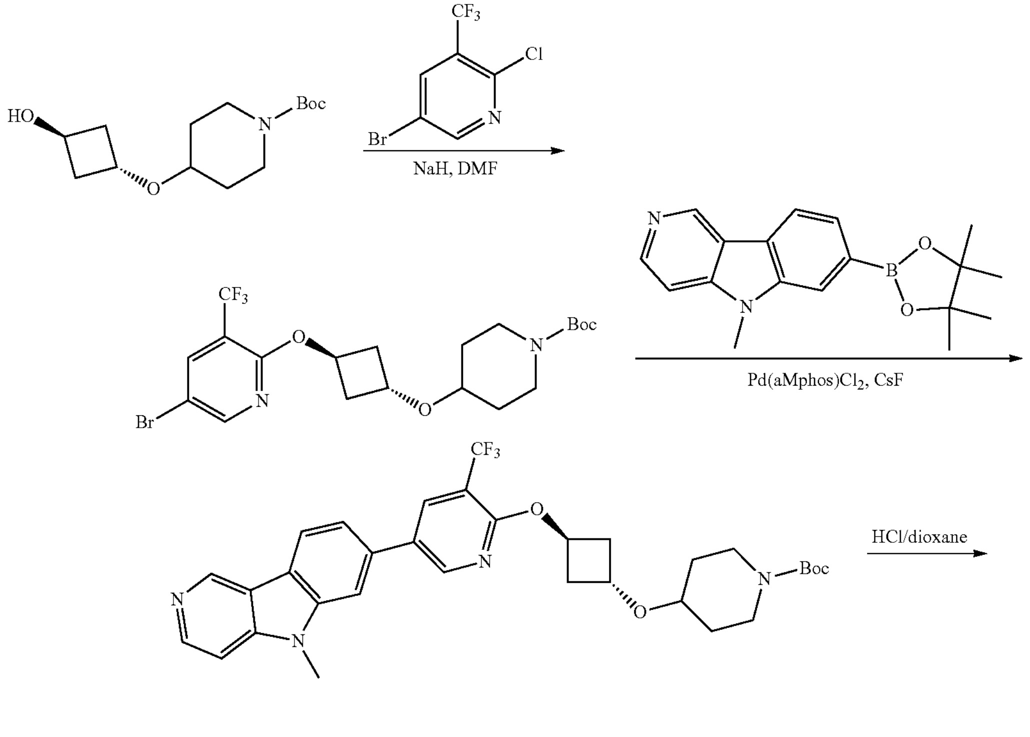

-continued

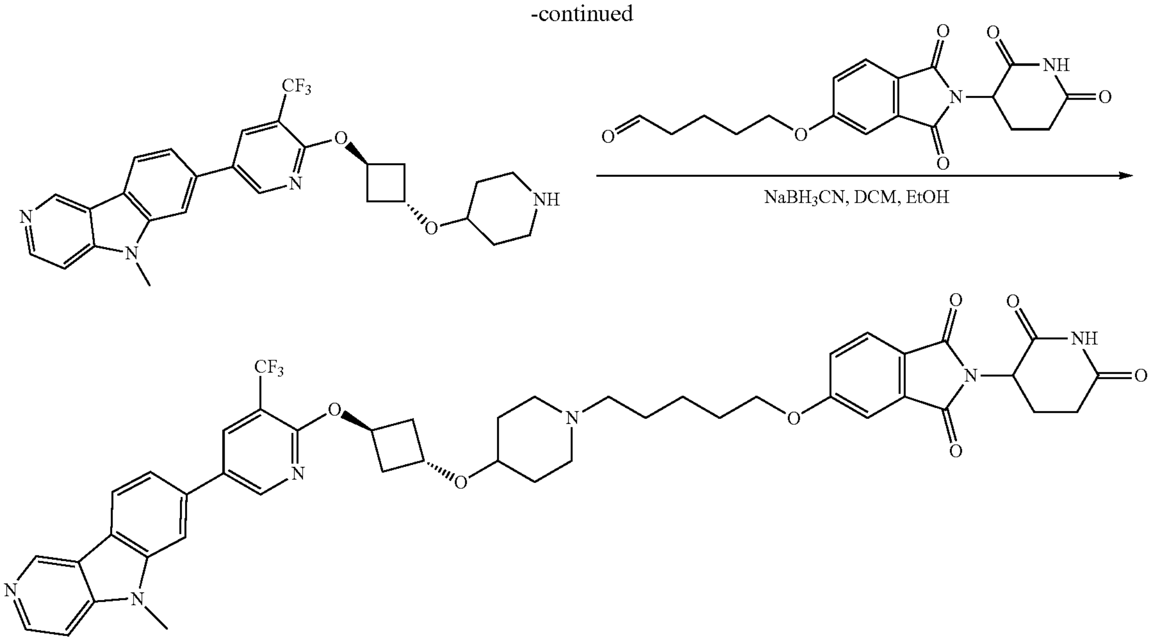

Compound 123

Synthetic Scheme for Exemplary Compound 66

5-(4-(2-(4-((1r,3r)-3-((5-(5H-pyrido[4,3-b]indol-7-yl)pyridin-2-yl)oxy)cyclobutoxy)piperidin-1-yl)ethyl)piperazin-1-yl)-2-(2,6-dioxopiperidin-3-yl)isoindoline-1,3-dione

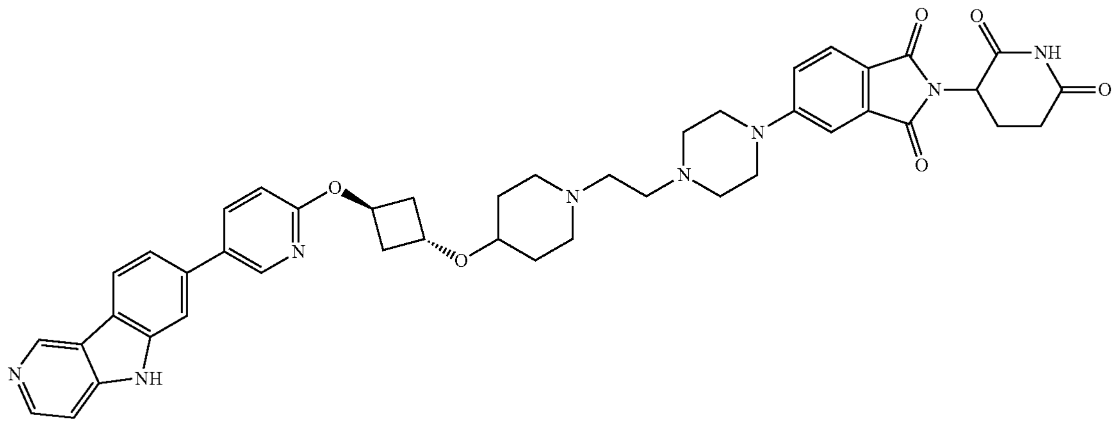 [SMILES: O=C1CCC(N2C(=O)c3ccc(N4CCN(CCN5CCC(O[C@H]6C[C@H](Oc7ccc(-c8ccc9c(c8)[nH]c8ccncc89)cn7)C6)CC5)CC4)cc3C2=O)C(=O)N1]

Step 1: benzyl 4-(2,2-diethoxyethyl)piperazine-1-carboxylate

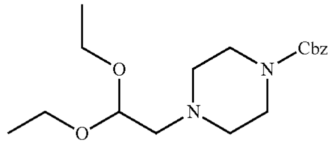 [SMILES: CCOC(CN1CCN(C(=O)OCc2ccccc2)CC1)OCC]

To a solution of benzyl piperazine-1-carboxylate (1.0, 4.54 mmol) in DMF (20 mL) was added $K_2CO_3$ (1.25 g, 9.0 mmol) and 2-bromo-1,1-diethoxyethane (1.0 g, 4.54 mmol). The resulting mixture was stirred at 80° C. for 20 hours. Then the reaction mixture was diluted with water (50 mL) and extracted with EA. The organic phase was washed with brine, dried over $MgSO_4$, and concentrated. The residue was purified by chromatography (silica gel, PE:EA=1:1) to afford the desired compound benzyl 4-(2,2-diethoxyethyl)piperazine-1-carboxylate (1.55 g) as a colorless oil.

Step 2: 1-(2,2-diethoxyethyl)piperazine

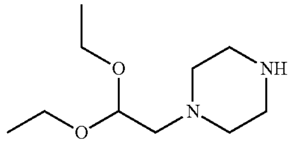

To a solution of benzyl 4-(2,2-diethoxyethyl)piperazine-1-carboxylate (1.55 g, 4.6 mmol) in MeOH (30 mL) was added $Pd(OH)_2/C$ (0.3 g, 20%). The resulting mixture was stirred at 30° C. for 3 hours. Then the reaction mixture was filtered and concentrated to afford the desired compound 1-(2,2-diethoxyethyl)piperazine (0.9 g, crude) as a white solid, which was used to next step without further purification.

Step 3: 5-(4-(2,2-diethoxyethyl)piperazin-1-yl)-2-(2,6-dioxopiperidin-3-yl)isoindoline-1,3-dione

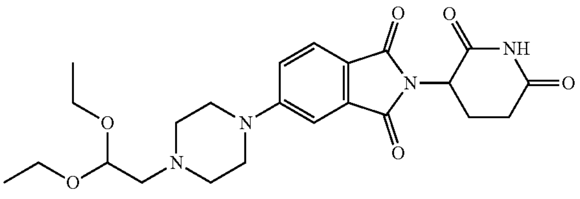 [SMILES: CCOC(CN1CCN(c2ccc3c(c2)C(=O)N(C2CCC(=O)NC2=O)C3=O)CC1)OCC]

To a solution of 1-(2,2-diethoxyethyl)piperazine (0.9 g, 4.45 mmol) in NMP (15 mL) was added DIEA (2.3 g, 17.8 mmol) and 2-(2,6-dioxopiperidin-3-yl)-5-fluoroisoindoline-1,3-dione (1.35 g, 4.9 mmol). The resulting mixture was stirred at 90° C. for 20 hours. Then the reaction mixture was diluted with water (50 mL) and extracted with DCM/MeOH (10/1). The organic phase was washed with brine, dried over $MgSO_4$, and concentrated. The residue was purified by chromatography (silica gel, DCM:MeOH (20:1) to afford the desired compound (1.4 g) as a yellow solid.

Step 4: 2-(4-(2-(2,6-dioxopiperidin-3-yl)-1,3-dioxoisoindolin-5-yl)piperazin-1-yl)acetaldehyde

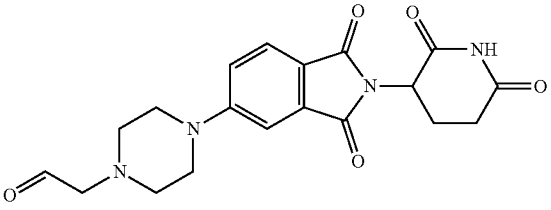 [SMILES: O=CCN1CCN(c2ccc3c(c2)C(=O)N(C2CCC(=O)NC2=O)C3=O)CC1]

A solution of 5-(4-(2,2-diethoxyethyl)piperazin-1-yl)-2-(2,6-dioxopiperidin-3-yl)isoindoline-1,3-dione (300 mg, 0.65 mmol) in HCl (5 mL in $H_2O$, 2.5 mol/L) was stirred at 50° C. for 20 hours. The mixture was basified with $NaHCO_3$ (20 mL) and extracted with EA. The organic phase was washed with brine, dried over $MgSO_4$, and concentrated to afford the desired compound (220 mg, crude) as yellow solid, which was used in the next step without further purification.

Step 5: 5-(4-(2-(4-((1r,3r)-3-((5-(5H-pyrido[4,3-b]indol-7-yl)pyridin-2-yl)oxy)cyclobutoxy)piperidin-1-yl)ethyl)piperazin-1-yl)-2-(2,6-dioxopiperidin-3-yl)isoindoline-1,3-dione To a solution of 2-(4-(2-(2,6-dioxopiperidin-3-yl)-1,3-dioxoisoindolin-5-yl)piperazin-1-yl)acetaldehyde (180 mg, 0.41 mmol) in MeOH/DMSO (8 mL, 1/1) was added 7-(6-((1r,3r)-3-(piperidin-4-yloxy)cyclobutoxy)pyridin-3-yl)-5H-pyrido[4,3-b]indole (97 mg, 0.24 mmol) [prepared as described in Compound 65], AcOH (1 drop) and $NaBH_3CN$ (60 mg, 0.94 mmol). The resulting mixture was stirred at 10° C. for 2 hours. Then the reaction mixture was diluted with water (10 mL) and extracted with EA. The organic phase was washed with brine and filtered, and the crude material was purified by prep-HPLC to give the title compound (21.2 mg) as a yellow solid.

$^1H$ NMR (400 MHz, DMSO-$d_6$): δ 13.21 (s, 1H), 11.08 (s, 2H), 9.76 (s, 1H), 8.67 (d, J=6.6 Hz, 1H), 8.61 (s, 1H), 8.52 (d, =8.3 Hz, 1H), 8.17 (d, J=8.3 Hz, 1H), 8.02 (d, J=7.1 Hz, 2H), 7.82-7.72 (m, 3H), 7.46 (s, 2H), 7.35 (s, 2H), 6.96 (d, J=8.5 Hz, 1H), 5.34 (s, 1H), 5.08 (d, J=7.7 Hz, 2H), 4.40 (s, 2H), 3.23 (s, 4H), 3.15 (s, 4H), 3.02 (s, 4H), 2.95-2.83 (m, 4H), 2.59 (d, J=15.7 Hz, 4H), 2.44 (s, 2H), 2.01 (s, 5H), 1.77 (d, J=14.7 Hz, 2H). $(M+H)^+$ 783.6.

Synthetic Scheme for Exemplary Compound 171

5-((4,4-difluoro-5-(4-((1r,3r)-3-((5-(5-methyl-5H-pyrido[4,3-b]indol-7-yl)pyridin-2-yl)oxy)cyclobutoxy)piperidin-1-yl)pentyl)oxy)-2-(2,6-dioxopiperidin-3-yl)isoindoline-1,3-dione

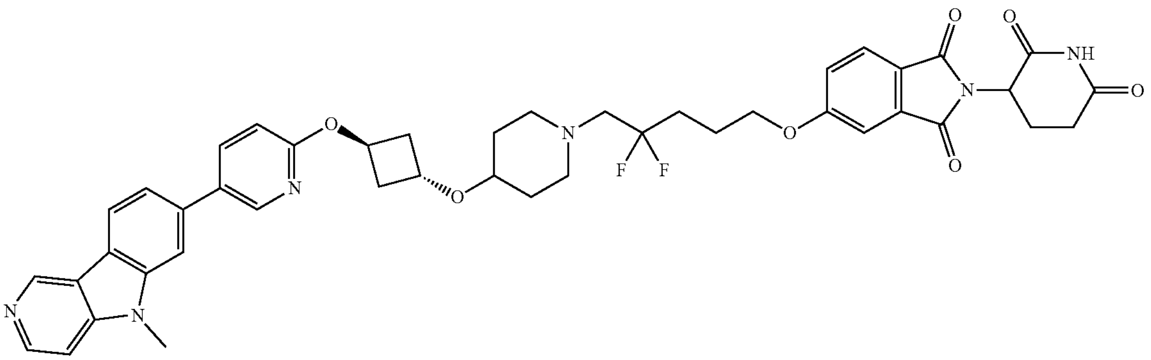 [SMILES: Cn1c2ccncc2c2ccc(-c3ccc(O[C@H]4C[C@H](OC5CCN(CC(F)(F)CCCOc6ccc7c(c6)C(=O)N(C6CCC(=O)NC6=O)C7=O)CC5)C4)nc3)cc21]

Step 1: 05-tert-butyl O1-ethyl 2,2-difluoropentanedioate

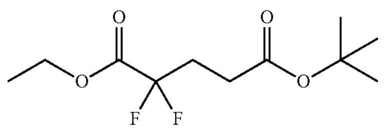 [SMILES: CCOC(=O)C(F)(F)CCC(=O)OC(C)(C)C]

A mixture of tert-butyl prop-2-enoate (10 g, 78.02 mmol, 1.00 eq), ethyl 2-bromo-2,2-difluoro-acetate (28.51 g, 140.44 mmol, 1.8 eq) and copper (10.41 g, 163.85 mmol, 2.10 eq) in tetrahydrofuran (100 mL) was heated to 55° C. under intense stirring; then N,N,N',N'-tetramethylethylenediamine (4.53 g, 39.01 mmol, 0.50 eq) followed by acetate acid (4.22 g, 70.22 mmol, 0.90 eq) were added. The dark blue-brown reaction mixture was stirred for 1 hour at 55° C. A 10% aqueous solution of ammonium chloride (100 mL) and ethyl acetate (500 mL) was added. The resulting mixture was stirred for 0.5 hours at room temperature and filtered through celite. The organic phase was washed with another portion of ammonium chloride solution (100 mL×5) to remove remaining copper complexes (blue color). The solution was dried with anhydrous sodium sulfate, filtered, and evaporated under vacuum. The residue was purified by silica gel chromatography (Petroleum ether/Ethyl acetate=500/1, 100/1) to afford 05-tert-butyl 01-ethyl 2,2-difluoropentanedioate (18.6 g, 73.74 mmol, 95% yield) as a yellow oil.

Step 2: tert-butyl 4,4-difluoro-5-hydroxy-pentanoate

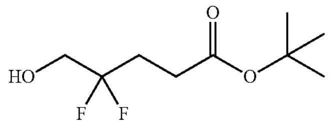

A suspension of sodium borohydride (3.24 g, 85.63 mmol, 1.20 eq) in ethanol (100 mL) was cooled to 0° C. in an ice bath, and a solution of 05-tert-butyl O1-ethyl 2,2-difluoropentanedioate (18 g, 71.36 mmol, 1.00 eq) in ethanol (100 mL) was added drop-wise from the addition funnel under vigorous stirring. The rate of dropping was carefully controlled to keep the reaction mixture temperature between 0-15° C. Then the mixture was stirred at 15° C. for 1 hour. The reaction mixture was quenched by dropwise addition of 5% aqueous citric acid (40 mL) with cooling. The aqueous phase was extracted with ethyl acetate (200 mL×3). The combined organic phase was washed with brine (200 mL×3), dried with anhydrous sodium sulfate, filtered and concentrated under vacuum. The residue was purified by silica gel chromatography (Petroleum ether/Ethyl acetate=20/1, 10/1) to afford tert-butyl 4,4-difluoro-5-hydroxy-pentanoate (14.2 g, 67.55 mmol, 95% yield) as a colorless oil.

Step 3: tert-butyl 4,4-difluoro-5-tetrahydropyran-2-yloxypentanoate

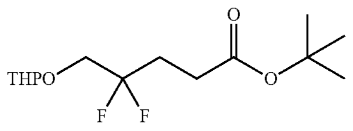

To a mixture of tert-butyl 4,4-difluoro-5-hydroxy-pentanoate (14.2 g, 67.55 mmol, 1.00 eq) and 4-methylbenzenesulfonic acid (642 mg, 3.38 mmol, 0.05 eq) in dichloromethane (50 mL) was added 3,4-dihydro-2H-pyran (17.05 g, 202.65 mmol, 3.00 eq) at −10° C. under nitrogen. Then the mixture was warmed to 25° C. and stirred for 16 hours. The reaction was quenched by saturated sodium bicarbonate solution (50 mL) and then extracted with dichloromethane (50 mL×3). The combined organic phase was washed with brine (50 mL×3), dried over anhydrous sodium sulfate, filtered and concentrated in vacuo. The residue was purified by silica gel chromatography (Petroleum ether/Ethyl acetate=500/1, 100/1) to afford tert-butyl 4,4-difluoro-5-tetrahydropyran-2-yloxypentanoate (17.2 g, crude) as a colorless oil.

Step 4: 4,4-Difluoro-5-tetrahydropyran-2-yloxy-pentan-1-ol

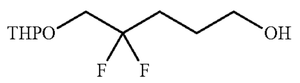

To a solution of lithium aluminum hydride (2.66 g, 70.12 mmol, 1.20 eq) in tetrahydrofuran (300 mL) was added a solution of tert-butyl 4,4-difluoro-5-tetrahydropyran-2-yloxy-pentanoate (17.2 g, 58.44 mmol, 1.00 eq) in tetrahydrofuran (60 mL) dropwise at 0° C. under nitrogen during which the temperature was maintained below 0° C. The reaction mixture was stirred at 0° C. for 1 hour. The reaction was quenched by water (2.6 mL), solution of sodium hydroxide in water (15%, 5.2 mL) and water (8 mL) at 0° C. The suspension was filtered through a pad of celite. The cake was washed with ethyl acetate (500 mL). The combined organic phase was washed with brine (200 mL×3), dried over anhydrous sodium sulfate, filtered and concentrated under vacuo. The residue was purified by silica gel chromatography (Petroleum ether/Ethyl acetate=20/1 to 10:1). 4,4-Difluoro-5-tetrahydropyran-2-yloxy-pentan-1-ol (10.9 g, 48.61 mmol, 83% yield) was obtained as a colorless oil.

Step 5: (4,4-difluoro-5-tetrahydropyran-2-yloxy-pentyl)4-methylbenzenesulfonate

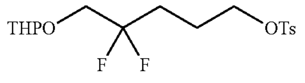

To a mixture of 4,4-difluoro-5-tetrahydropyran-2-yloxy-pentan-1-ol (10.9 g, 48.61 mmol, 1.00 eq) and p-toluenesulfonyl chloride (13.90 g, 72.91 mmol, 1.50 eq) in dichloromethane (100 mL) was added triethylamine (9.84 g, 97.22 mmol, 2.00 eq) in one portion at 0° C. under nitrogen. The mixture was warmed to 25° C. and stirred for 16 hours. The mixture was poured into ice-water (w/w=1/1) (30 mL) and stirred for 15 minutes. The aqueous phase was extracted with ethyl acetate (50 mL×3). The combined organic phase was washed with brine (50 mL×2), dried with anhydrous sodium sulfate, filtered and concentrated under vacuum. The residue was purified by silica gel chromatography (Petroleum ether/Ethyl acetate=20/1, 10/1) to afford (4,4-difluoro-5-tetrahydropyran-2-yloxy-pentyl)4-methylbenzenesulfonate (16.6 g, 43.87 mmol, 90% yield) as a colorless oil.

Step 6: Dimethyl 4-(4,4-difluoro-5-hydroxy-pentoxy)benzene-1,2-dicarboxylate

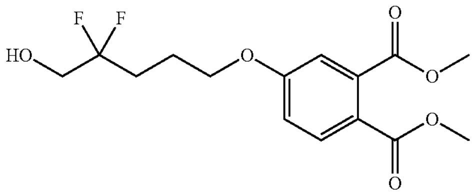 [SMILES: COC(=O)c1ccc(OCCCC(F)(F)CO)cc1C(=O)OC]

To a solution of (4,4-difluoro-5-tetrahydropyran-2-yloxy-pentyl) 4-methylbenzenesulfonate (1 g, 2.64 mmol, 1 eq) in N N-dimethylformamide (6 mL) was added cesium carbonate (1.72 g, 5.28 mmol, 2 eq) and dimethyl 4-hydroxybenzene-1,2-dicarboxylate (555 mg, 2.64 mmol, 1 eq). The mixture was stirred at 50° C. for 12 hours. LCMS showed starting material was consumed and desired compound was found. The mixture was filtered and poured into hydrochloric acid (1N, 30 mL), the aqueous phase was extracted with dichloromethane (20 mL×3). The combined organic phase was washed with brine (20 mL×2), dried with anhydrous sodium sulfate, filtered and concentrated in vacuum. The residue was purified by silica gel chromatography (Petroleum ether/Ethyl acetate=20/1, 5/1). Dimethyl 4-(4,4-difluoro-5-hydroxy-pentoxy)benzene-1,2-dicarboxylate (700 mg, 2.11 mmol, 79% yield) was obtained as a colorless oil.

Step 7: Dimethyl 4-[4,4-difluoro-5-(trifluoromethylsulfonyloxy)pentoxy]benzene-1,2-dicarboxylate

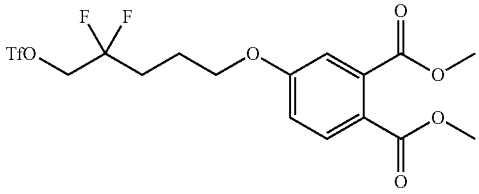 [SMILES: COC(=O)c1ccc(OCCCC(F)(F)COS(=O)(=O)C(F)(F)F)cc1C(=O)OC]

To a solution of dimethyl 4-(4,4-difluoro-5-hydroxy-pentoxy)benzene-1,2-dicarboxylate (600 mg, 1.81 mmol, 1 eq) in dichloromethane (10 mL) was added dropwise 2,6-dimethylpyridine (580 mg, 5.42 mmol, 3 eq) at 0° C. After addition, the mixture was stirred at this temperature for 10 minutes and then trifluoromethylsulfonyl trifluoromethanesulfonate (2.55 g, 9.03 mmol, 5 eq) was added dropwise at 0° C. The resulting mixture was stirred at 25° C. for 50 minutes. LCMS showed starting material was disappeared and desired compound was found. The mixture was concentrated in vacuum. The residue was further purified by Pre-thin-layer chromatography (petroleum ether:ethyl acetate=4:1). Dimethyl 4-[4,4-difluoro-5-(trifluoromethylsulfonyloxy)pentoxy]benzene-1,2-dicarboxylate (600 mg, 1.29 mmol, 71% yield) was obtained as a white solid.

Step 8: Dimethyl 4-[4,4-difluoro-5-[4-[3-[[5-(5-methylpyrido[4,3-b]indol-7-yl)-2-pyridyl]oxy]cyclobutoxy]-1-piperidyl]pentoxy]benzene-1,2-dicarboxylate

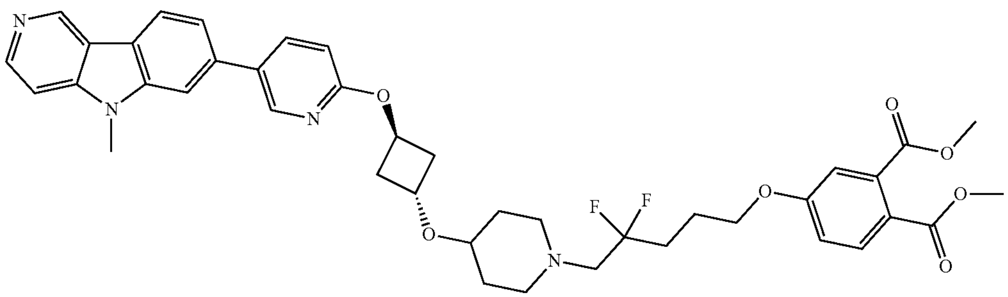 [SMILES: COC(=O)c1ccc(OCCCC(F)(F)CN2CCC(O[C@H]3C[C@H](Oc4ccc(-c5ccc6c7cnccc7n(C)c6c5)cn4)C3)CC2)cc1C(=O)OC]

To a solution of dimethyl 4-[4,4-difluoro-5-(trifluoromethylsulfonyloxy)pentoxy]benzene-1,2-dicarboxylate (150 mg, 0.3 mmol, 1 eq) in acetonitrile (1 mL) and dimethylsulfoxide (0.5 mL) was added potassium carbonate (133 mg, 1 mmol, 3 eq) and 5-methyl-7-[6-[3-(4-piperidyloxy)cyclobutoxy]-3-pyridyl]pyrido[4,3-b]indole (138 mg, 0.3 mmol, 1 eq) [prepared as described for Compound 82]. The mixture was stirred at 50° C. for 16 hr. LCMS showed starting material was almost disappeared and desired compound was found. The mixture was poured into water (20 mL) and the aqueous phase was extracted with ethyl acetate (20 mL×3). The combined organic phase was washed with brine (20 mL×2), dried with anhydrous sodium sulfate, filtered and concentrated in vacuum. The residue was further purified by Pre-thin-layer chromatography (petroleum ether: ethyl acetate=4:1). Dimethyl 4-[4,4-difluoro-5-[4-[3-[[5-(5-methylpyrido[4,3-b]indol-7-yl)-2-pyridyl]oxy]cyclobutoxy]-1-piperidyl]pentoxy]benzene-1,2-dicarboxylate (160 mg, 0.2 mmol, 66% yield) was obtained as a yellow oil.

Step 9: 4-[4,4-Difluoro-5-[4-[3-[[5-(5-methylpyrido[4,3-b]indol-7-yl)-2-pyridyl]oxy]cyclobutoxy]-1-piperidyl]pentoxy]phthalic acid

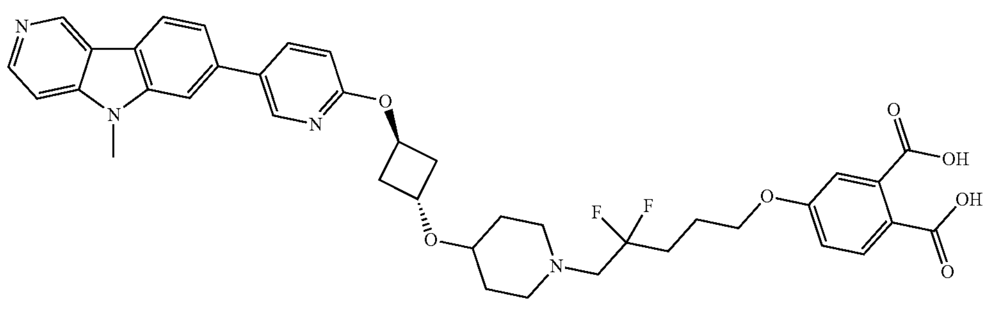 [SMILES: Cn1c2ccncc2c2ccc(-c3ccc(O[C@H]4C[C@H](OC5CCN(CC(F)(F)CCCOc6ccc(C(=O)O)c(C(=O)O)c6)CC5)C4)nc3)cc21]

To a solution of dimethyl 4-[4,4-difluoro-5-[4-[3-[[5-(5-methylpyrido(4,3-b]indol-7-yl)-2-pyridyl]oxy]cyclobutoxy]-1-piperidyl]pentoxy]benzene-1,2-dicarboxylate (120 mg, 0.16 mmol, 1 eq) in methanol (3 mL) and water (1.5 mL) was added potassium hydroxide (36 mg, 0.6 mmol, 4 eq). The mixture was stirred at 55° C. for 2 hr. LCMS showed starting material was consumed and desired compound was found. The reaction mixture was adjusted to pH=(7) by hydrochloric acid (1 M) and concentrated under reduced pressure to remove methanol and water. The residue was directly used for next step without further purification. 4-[4,4-Difluoro-5-[4-[3-[[5-(5-methylpyrido[4,3-b]indol-7-yl)-2-pyridyl]oxy]cyclobutoxy]-1-piperidyl]pentoxy] phthalic acid (110 mg, 0.1 mmol, 95% yield) was obtained as a yellow solid.

Step 10: 5-[4,4-Difluoro-5-[4-[3-[[5-(5-methylpyrido[4,3-b]indol-7-yl)-2-pyridyl]oxy]cyclobutoxy]-1-piperidyl]pentoxy]-2-(2,6-dioxo-3-piperidyl) isoindoline-1,3-dione

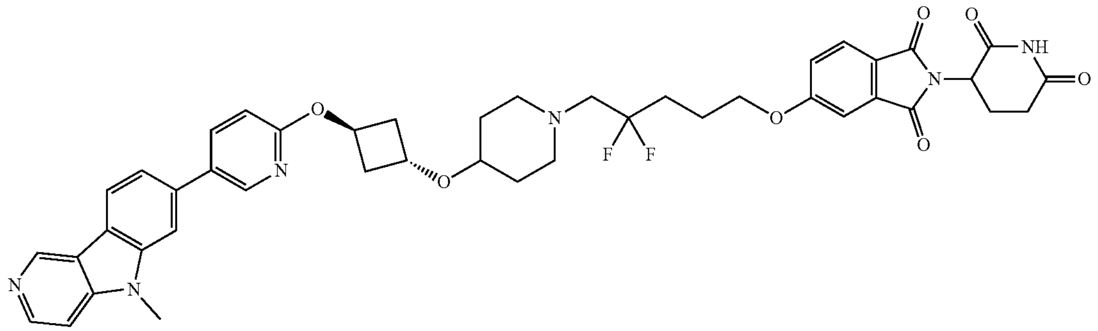 [SMILES: Cn1c2ccncc2c2ccc(-c3ccc(O[C@H]4C[C@H](OC5CCN(CC(F)(F)CCCOc6ccc7c(c6)C(=O)N(C6CCC(=O)NC6=O)C7=O)CC5)C4)nc3)cc21]

To a solution of 4-[4,4-difluoro-5-[4-[3-[[5-(5-methylpyrido[4,3-b]indol-7-yl)-2-pyridyl]oxy]cyclobutoxy]-1-piperidyl]pentoxy]phthalic acid (110 mg, 0.2 mmol, 1 eq) in acetic acid (2 mL) was added sodium acetate (37 mg, 0.5 mmol, 3 eq) the mixture was stirred at 25° C. for 1 hour. Then 3-aminopiperidine-2,6-dione (30 mg, 0.2 mmol, 1.2 eq, hydrochloric acid) was added into the mixture and heated to 120° C., stirred for additional 11 hours. LCMS showed starting material was consumed and desired compound was found. The mixture was concentrated in vacuum. The residue was purify by Pre-High Performance Liquid Chromatography column: Phenomenex Synergi C18 150*25*10 um; mobile phase: [water (0.225% formic acid)-acetonitrile]; B %: 14%-35%, 7 minutes. 5-[4,4-Difluoro-5-[4-[3-[[5-(5-methylpyrido[4,3-b]indol-7-yl)-2-pyridyl]oxy]cyclobutoxy]-1-piperidyl]pentoxy]-2-(2,6-dioxo-3-piperidyl) isoindoline-1,3-dione (67 mg, 0.08 mmol, 50% yield, 98% purity, formic acid) was obtained as a gray solid.

$^1$H NMR: (400 MHz, DMSO-$d_6$) δ=11.11 (s, 1H), δ=9.35 (s, 1H) δ=8.64 (s, 1H), 8.49-8.48 (d, J=4 Hz 1H), 8.33-8.31 (d, J=8 Hz 1H), δ=8.17 (s, 1H), δ=7.97 (s, 1H) 7.85-7.83 (d, J=8 Hz 1H), 7.62-7.61 (d, J=4 Hz 2H), 7.43 (s, 1H), 6.94-6.92 (d, J=8 Hz 1H), 5.31-5.29 (m, 1H), 5.12-5.10 (m, 1H), 4.34 (s, 5H), 4.25-4.23 (d, J=8 Hz 1H), 3.95 (s, 3H), 2.77 (m, 2H), 2.73 (m, 4H), 2.53-2.52 (m, 1H), 2.39-2.38 (m, 4H), 1.91-1.90 (m, 4H), 1.75 (m, 2H), 1.43 (m, 2H), 1.41 (m, 2H). $(M+H)^+$ 807.5.

Synthetic Scheme for Exemplary Compound 164

Step 1: benzyl 6-(tosyloxy)hexanoate

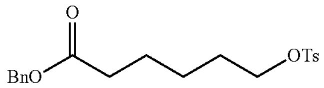 [SMILES: Cc1ccc(S(=O)(=O)OCCCCCC(=O)OCc2ccccc2)cc1]

To a mixture of benzyl 6-hydroxyhexanoate (1.1 g, 4.95 mmol) and triethylamine (1.0 g, 9.90 mmol) in dichloromethane (10 ml) was added 4-toluenesulfonyl chloride (1.88 g, 9.90 mmol) at 0° C. The mixture was stirred at room temperature for 1 hour. TLC showed the reaction was complete. The reaction mixture was diluted with dichloromethane (20 ml), washed with brine (20 ml), dried over anhydrous sodium sulfate, and concentrated under reduced pressure to give a crude residue which was purified by silica gel flash chromatography (eluted with 30-50% ethyl acetate in hexane) to afford benzyl 6-(tosyloxy)hexanoate (960 mg, yield 54%) as colorless oil.

Step 2: benzyl 6-(2-(2,6-dioxopiperidin-3-yl)-1,3-dioxoisoindolin-5-yloxy)hexanoate

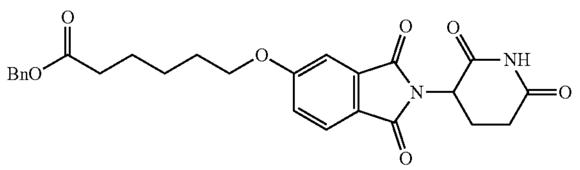 [SMILES: O=C1CCC(N2C(=O)c3ccc(OCCCCCC(=O)OCc4ccccc4)cc3C2=O)C(=O)N1]

A mixture of benzyl 6-(tosyloxy)hexanoate (200 mg, 0.53 mmol) and 2-(2,6-dioxopiperidin-3-yl)-5-hydroxyisoindoline-1,3-dione (146 mg, 0.53 mmol), potassium carbonate (147 mg, 1.06 mmol) and potassium iodide (9 mg, 0.05 mmol) in N,N-dimethylformamide (3 ml) was stirred at 50° C. for 12 hours. TLC showed the reaction was complete. The reaction mixture was partitioned between water (15 ml) and with ethyl acetate (15 ml). The organic layer was collected, washed with brine (10 ml), dried over anhydrous sodium sulfate, and concentrated under reduced pressure to give a crude residue which was purified by silica gel flash chromatography (eluted with 2-5% methanol in dichloromethane) to afford benzyl 6-(2-(2,6-dioxopiperidin-3-yl)-1,3-dioxoisoindolin-5-yloxy)hexanoate (100 mg, yield 40%) as yellow solid.

Step 3: 6-(2-(2,6-dioxopiperidin-3-yl)-1,3-dioxoisoindolin-5-yloxy)hexanoic acid

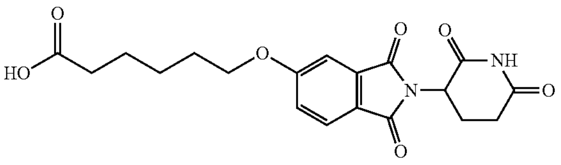 [SMILES: O=C(O)CCCCCOc1ccc2c(c1)C(=O)N(C1CCC(=O)NC1=O)C2=O]

A mixture of benzyl 6-(2-(2,6-dioxopiperidin-3-yl)-1,3-dioxoisoindolin-5-yloxy)hexanoate (100 mg, 0.21 mmol) and palladium on activated carbon (20%, 50 mg) in methanol (2 ml) was stirred at room temperature for 1 hour under hydrogen atmosphere (hydrogen balloon). TLC showed the reaction was complete. The reaction mixture was filtered, and concentrated under reduced pressure to afford 6-(2-(2,6-dioxopiperidin-3-yl)-1,3-dioxoisoindolin-5-yloxy) hexanoic acid (70 mg, yield 86%) as yellow oil which was used in next step directly without further purification.

Step 4: 5-(6-(4-((1r,3r)-3-(5-(5H-pyrido[4,3-b]indol-7-yl)pyridin-2-yloxy)cyclobutoxy)piperidin-1-yl)-6-oxohexyloxy)-2-(2,6-dioxopiperidin-3-yl)isoindoline-1,3-dione)

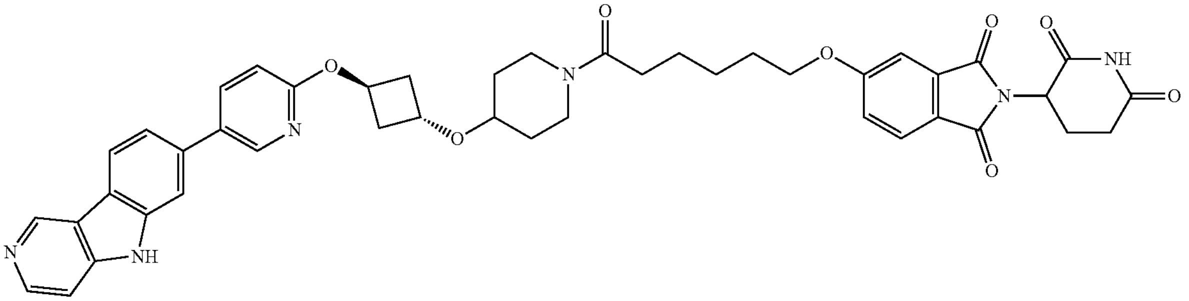 [SMILES: O=C1CCC(N2C(=O)c3ccc(OCCCCCC(=O)N4CCC(O[C@H]5C[C@H](Oc6ccc(-c7ccc8c(c7)[nH]c7ccncc78)cn6)C5)CC4)cc3C2=O)C(=O)N1]

To a mixture of 6-(2-(2,6-dioxopiperidin-3-yl)-1,3-dioxoisoindolin-5-yloxy)hexanoic acid (70 mg, 0.18 mmol) and 7-(6-((1r,3r)-3-(piperidin-4-yloxy)cyclobutoxy)pyridin-3-yl)-5H-pyrido[4,3-b]indole (75 mg, 0.18 mmol) [prepared as described in Compound 65] and triethylamine (56 mg, 0.56 mmol) in N,N-dimethylformamide (2 ml) was added (2-(7-aza-1H-benzotriazole-1-yl)-1,1,3,3-tetramethyluronium hexafluorophosphate) (212 mg, 0.56 mmol) at room temperature. The mixture was stirred at room temperature for 1 hour. TLC showed the reaction was complete. The reaction mixture was diluted with dichloromethane (50 ml), washed with brine (50 ml), dried over anhydrous sodium sulfate, and concentrated under reduced pressure to give a crude residue which was purified by silica gel flash chromatography (eluted with 2-5% methanol in dichloromethane) to afford the title compound (6.6 mg, yield 5%) as white solid.

$^1H$ NMR (400 MHz, $CDCl_3$): δ 1.52-1.57 (m, 3H), 1.61-1.65 (m, 2H), 1.70-1.74 (m, 2H), 1.98-2.01 (m, 2H), 2.13-2.17 (m, 1H), 2.34-2.41 (m, 2H), 2.47-2.50 (m, 2H), 2.78-2.88 (m, 2H), 3.20-3.28 (m, 2H), 3.54-3.72 (m, 3H), 4.00-4.10 (m, 3H), 4.39-4.44 (m, 1H), 4.95 (dd, J=5.2, 12.0 Hz, 1H), 5.31-5.42 (m, 4H), 6.82 (d, J=8.4 Hz, 1H), 7.17 (d, J=8.8 Hz, 1H), 7.31-7.34 (m, 2H), 7.48-7.51 (m, 2H), 7.68 (s, 1H), 7.77 (d, J=8.8 Hz, 1H), 7.87 (d, J=7.2 Hz, 1H), 8.11 (d, J=8.0 Hz, 1H), 8.32 (s, 1H), 8.41-8.45 (m, 2H), 9.23 (s, 1H).

Synthetic Scheme for Exemplary Compounds 198 and 205

2-(2,6-dioxopiperidin-3-yl)-5-((3-(3-(4-((1r,3r)-3-((5-(5-methyl-5H-pyrido[4,3-b]indol-7-yl)pyridin-2-yl)oxy)cyclobutoxy)piperidin-1-yl)phenyl)prop-2-yn-1-yl)oxy)isoindoline-1,3-dione

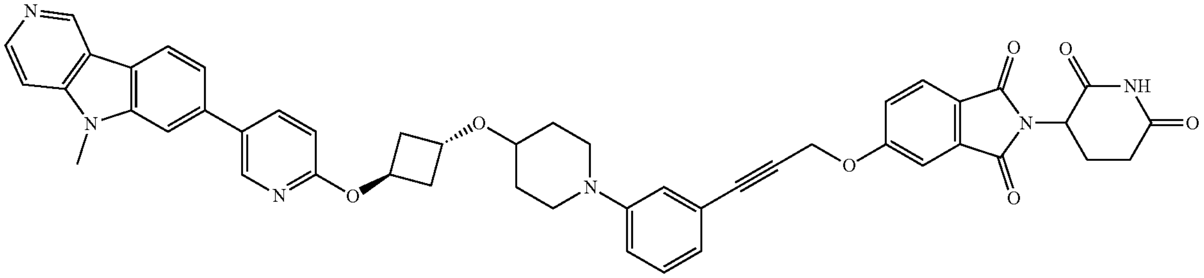 [SMILES: Cn1c2ccncc2c2ccc(-c3ccc(O[C@H]4C[C@H](OC5CCN(c6cccc(C#CCOc7ccc8c(c7)C(=O)N(C7CCC(=O)NC7=O)C8=O)c6)CC5)C4)nc3)cc21]

2-(2,6-dioxopiperidin-3-yl)-5-(3-(3-(4-((1r,3r)-3-((5-(5-methyl-5H-pyrido[4,3-b]indol-7-yl)pyridin-2-yl)oxy)cyclobutoxy)piperidin-1-yl)phenyl)propoxy)isoindoline-1,3-dione

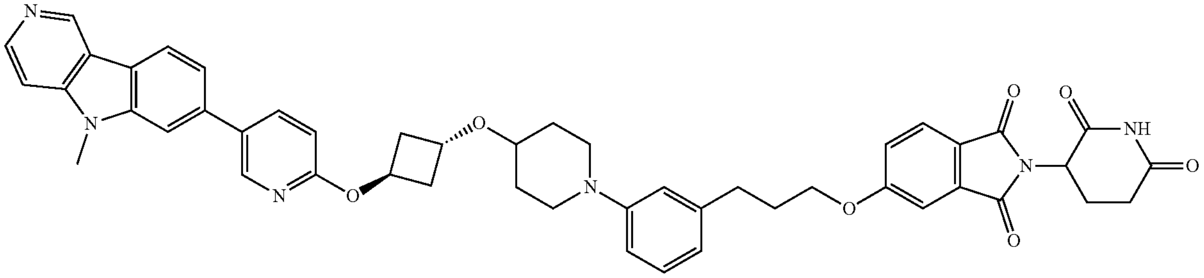 [SMILES: Cn1c2ccncc2c2ccc(-c3ccc(O[C@H]4C[C@H](OC5CCN(c6cccc(CCCOc7ccc8c(c7)C(=O)N(C7CCC(=O)NC7=O)C8=O)c6)CC5)C4)nc3)cc21]

Compounds 198 and 205 were prepared according to the synthetic scheme below using procedures described above and common procedures known to those skilled in the art:

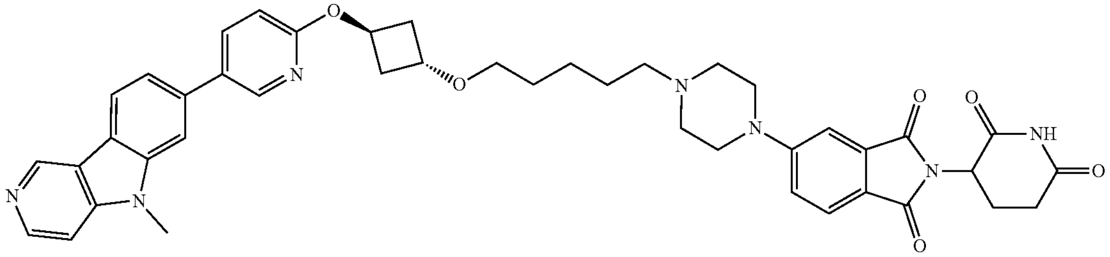 [SMILES: Cn1c2ccncc2c2ccc(-c3ccc(O[C@H]4C[C@H](OCCCCCN5CCN(c6ccc7c(c6)C(=O)N(C6CCC(=O)NC6=O)C7=O)CC5)C4)nc3)cc21]

Synthetic Scheme for Exemplary Compound 68

2-(2,6-dioxopiperidin-3-yl)-5-(4-(5-((1r,3r)-3-((5-(5-methyl-5H-pyrido[4,3-b]indol-7-yl)pyridin-2-yl)oxy)cyclobutoxy)pentyl)piperazin-1-yl)isoindoline-1,3-dione

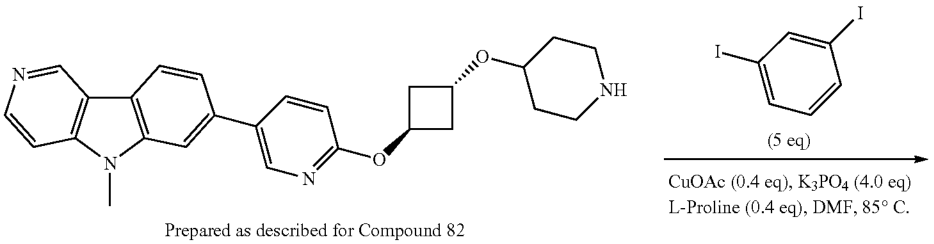

Prepared as described for Compound 82

-continued
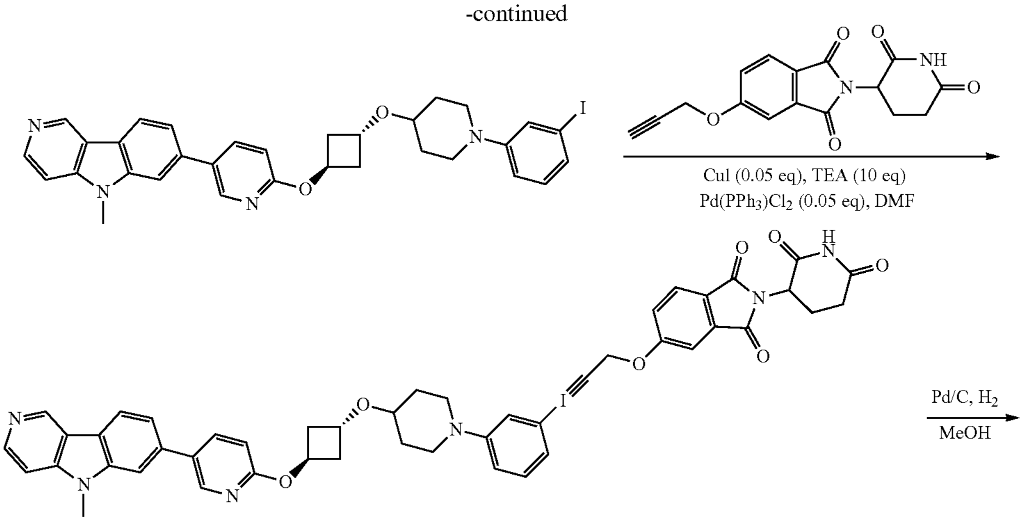
Compound 198
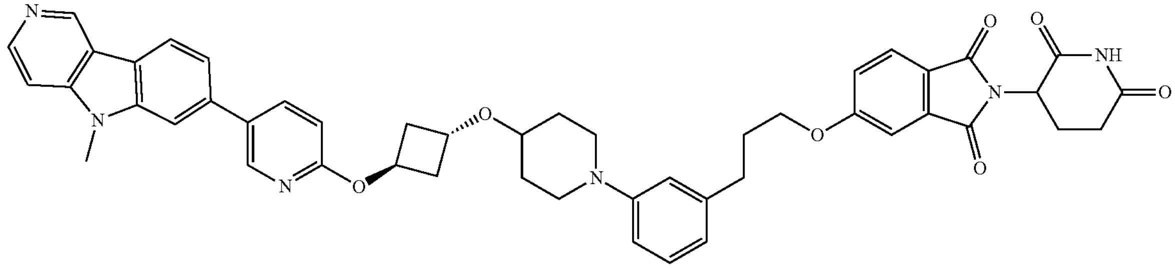
Compound 205
Prepared according to the synthetic scheme below using procedures described above and common procedures known to those skilled in the art.
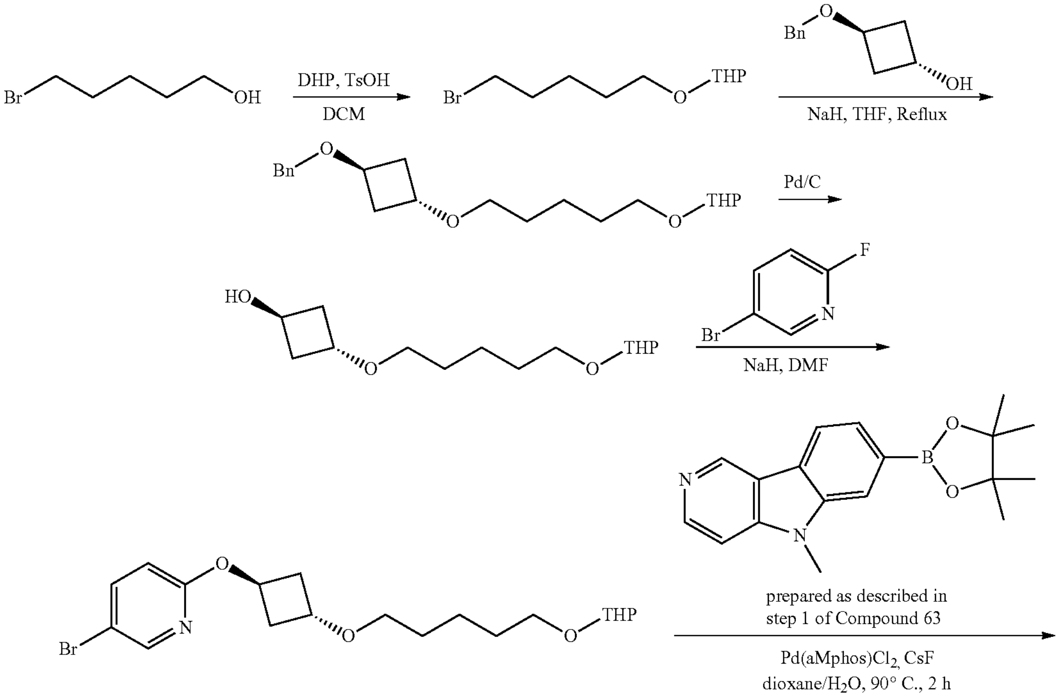

-continued

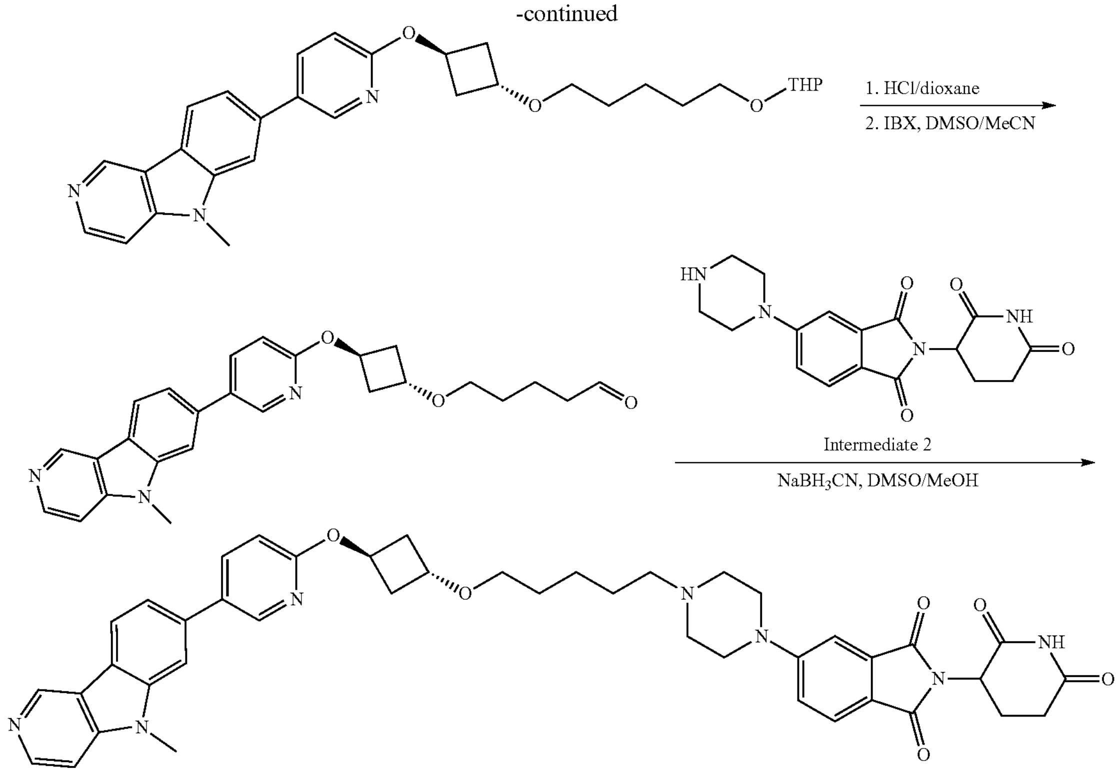

Compound 68

$^1$H NMR (400 MHz, DMSO-d6): δ11.12 (s, 1H), 9.37 (s, 1H), 8.64 (s, 1H), 8.50 (d, J=4.0 Hz, 1H), 8.33 (d, J=12.0 Hz, 1H), 8.00 (s, 1H), 7.68-7.60 (m, 3H), 7.34 (d, J=4.0 Hz, 1H), 7.25 (dd, J=8.0 Hz, 4.0 Hz, 1H), 6.94 (d, J=8.0 Hz, 1H), 5.32 (t, J=4.0 Hz, 1H), 5.07 (dd, J=12.0 Hz, 8.0 Hz, 1H), 4.20-4.17 (m, 1H), 3.96 (s, 3H), 4.46 (s, 6H), 2.88-2.84 (m, 1H), 2.59-2.54 (m, 7H), 2.43-2.32 (m, 6H), 2.02-1.98 (m, 1H), 1.57-1.49 (m, 4H), 1.38-1.34 (m, 2H). $(M+H)^+$ 756.6

Synthetic Scheme for Exemplary Compound 70

2-(2,6-dioxopiperidin-3-yl)-5-(2-(2-(2-(2-((1r,3r)-3-((5-(5-methyl-5H-pyrido[4,3-b]indol-7-yl)pyridin-2-yl)oxy)cyclobutoxy)ethoxy)ethoxy)ethoxy)ethoxy)isoindoline-1,3-dione Step 1: 2-((1r,3r)-3-(benzyloxy)cyclobutoxy)-5-bromopyridine

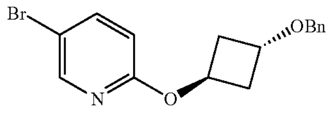

To a solution of (1r,3r)-3-(benzyloxy)cyclobutan-1-ol (500 mg, 2.8 mmol) in DMF (15 mL) was added NaH (336 mg, 8.4 mmol, 60%) at 0° C. The solution was stirred at 0° C. for 30 minutes. 5-bromo-2-fluoropyridine (1.0 g, 5.6 mmol) in DMF (3 mL) was added. The resulting solution was heated at 80° C. overnight. After cooling to room temperature, the mixture was quenched with water. The mixture was extracted with ethyl acetate, and the organic layer was washed with water and brine. The organic phase was dried over anhydrous sodium sulfate, filtered and concentrated under vacuum. The residue was purified by col-

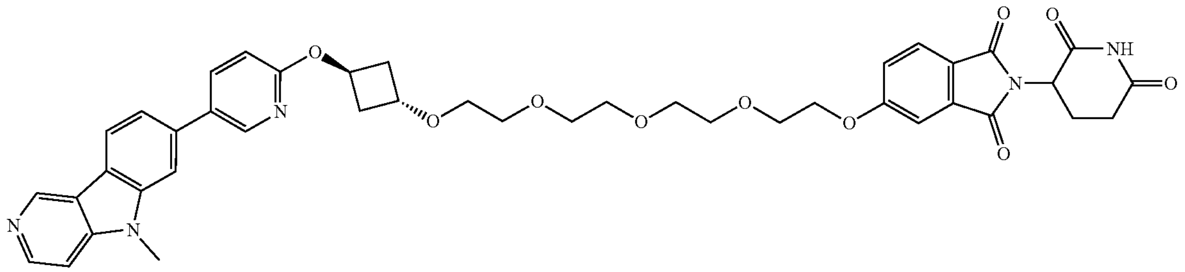 [SMILES: Cn1c2ccncc2c2ccc(-c3ccc(O[C@H]4C[C@H](OCCOCCOCCOCCOc5ccc6c(c5)C(=O)N(C5CCC(=O)NC5=O)C6=O)C4)nc3)cc21]

umn chromatography on silica gel (PE:EA=100:1) to afford the desired compound (630 mg, 67% yield) as a colorless oil.

Step 2: (1r,3r)-3-((5-bromopyridin-2-yl)oxy)cyclobutan-1-ol

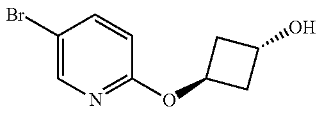 [SMILES: O[C@H]1C[C@H](Oc2ccc(Br)cn2)C1]

To a solution of 2-((1r,3r)-3-(benzyloxy)cyclobutoxy)-5-bromopyridine (630 mg, 1.88 mmol) in DCM (15 mL) was added $BBr_3$ (1.42 g, 5.65 mmol) at −78° C. The resulting solution was stirred at −78° C. for 0.5 hours. The solution was quenched with $NaHCO_3$. The layers were separated and the aqueous layer was extracted with DCM. The combined organic layers were concentrated to afford the desired compound (390 mg, crude) as a yellow solid, which was used directly in the next step without further purification.

Step 3: 5-bromo-2-((1r,3r)-3-((1-phenyl-2,5,8,11-tetraoxatridecan-13-yl)oxy)cyclobutoxy)pyridine

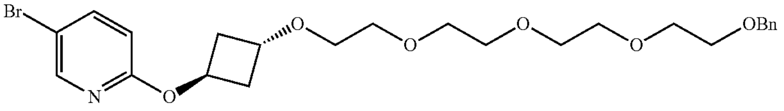 [SMILES: Brc1ccc(O[C@H]2C[C@H](OCCOCCOCCOCCOCc3ccccc3)C2)nc1]

To a solution of (1r,3r)-3-((5-bromopyridin-2-yl)oxy)cyclobutan-1-ol (390 mg, 1.64 mmol) in THF (15 mL) was added NaH (262 mg, 60%) at 0° C. The solution was stirred at 10° C. for 0.5 hours, and then 13-bromo-1-phenyl-2,5,8,11-tetraoxatridecane (570 mg, 1.64 mmol) was added. The resulting solution was stirred at 70° C. for 20 hours. The solution was quenched with water. The layers were separated and the aqueous layer was extracted with EA. The combined organic layers were washed with brine. The organic layer was dried over $Na_2SO_4$, filtered and concentrated. The residue was purified by column chromatography on silica gel with PE:EA (1:1) to afford the desired compound (350 mg) as a yellow solid.

5-bromo-2-((1r,3r)-3-((1-phenyl-2,5,8,11-tetraoxatridecan-13-yl)oxy)cyclobutoxy)pyridine was converted to the final compound, 2-(2,6-dioxopiperidin-3-yl)-5-(2-(2-(2-(2-((1r,3r)-3-((5-(5-methyl-5H-pyrido[4,3-b]indol-7-yl)pyridin-2-yl)oxy)cyclobutoxy)ethoxy)ethoxy)ethoxy)ethoxy)isoindoline-1,3-dione, according to the following scheme and using procedures described above and common procedures known to those skilled in the art.

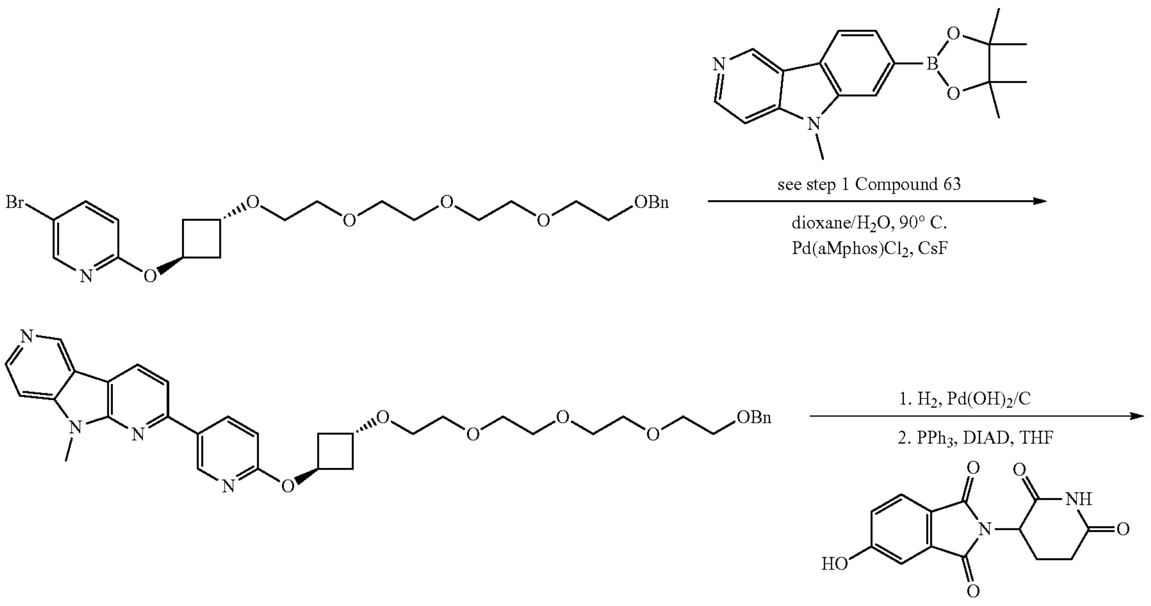

-continued

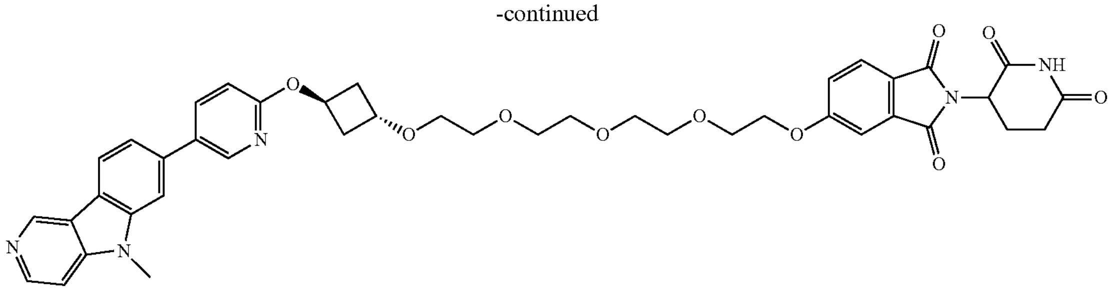

Compound 70

Compound 70: $^1H$ NMR (400 MHz, DMSO-d6): δ 11.10 (s, 1H), 9.36 (s, 1H), 8.62 (s, 1H), 8.50 (s, 1H), 8.31 (d, J=8.2 Hz, 1H), 8.18 (d, J=8.8 Hz, 1H), 7.97 (s, 1H), 7.81 (d, J=8.3 Hz, 1H), 7.60 (d, J=8.0 Hz, 2H), 7.43 (s, 1H), 7.35 (d, J=7.8 Hz, 1H), 6.93 (d, J=8.7 Hz, 1H), 5.31 (s, 1H), 5.11 (dd, J=12.8, 5.1 Hz, 1H), 4.31 (s, 2H), 4.22 (s, 1H), 3.95 (s, 3H), 3.79 (s, 2H), 3.64-3.48 (m, 10H), 3.45 (d, J=4.9 Hz, 3H), 2.86 (d, J=13.2 Hz, 1H), 2.45-2.40 (m, 2H), 2.37-2.30 (m, 2H), 2.02 (d, J=6.5 Hz, 1H). $(M+H)^+$ 778.5.

Synthetic Scheme for Exemplary Compound 71

2-(2,6-dioxopiperidin-3-yl)-5-((15-(5-(5-methyl-5H-pyrido[4,3-b]indol-7-yl)pyridin-2-yl)-3,6,9,12-tetraoxapentadec-14-yn-1-yl)oxy)isoindoline-1,3-dione

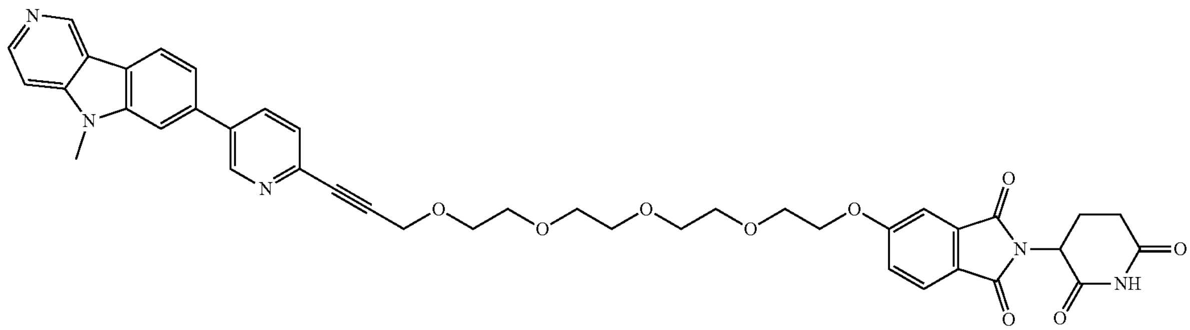 [SMILES: Cn1c2ccncc2c2ccc(-c3ccc(C#CCOCCOCCOCCOCCOc4ccc5c(c4)C(=O)N(C4CCC(=O)NC4=O)C5=O)nc3)cc21]

Step 1: 15-(5-bromopyridin-2-yl)-3,6,9,12-tetraoxapentadec-14-yn-1-ol

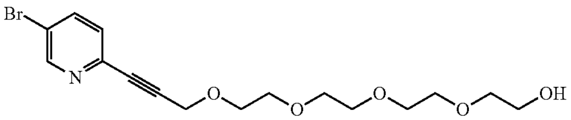 [SMILES: OCCOCCOCCOCCOCC#Cc1ccc(Br)cn1]

To a solution of 3,6,9,12-tetraoxapentadec-14-yn-1-ol (570 mg, 2.45 mmol) in dried THF (10 mL) were added 2,5-dibromopyridine (697.6 mg, 2.94 mmol), CuI (51.4 mg, 0.27 mmol) and $Pd(PPh_3)_2Cl_2$ (80 mg, 0.24 mmol) at 15° C. under $N_2$ atmosphere subsequently. The solution was stirred at 40° C. for 1.5 hours. The solution was quenched with $H_2O$ (10 mL) and the mixture was extracted with EtOAc (10 mL×2). The combined organic layers were dried over anhydrous sodium sulfate, filtered and concentrated under vacuum. The residue was purified by silica gel column chromatography to afford the desired compound (530 mg, 56% yield) as a yellow oil.

15-(5-bromopyridin-2-yl)-3,6,9,12-tetraoxapentadec-14-yn-1-ol was converted to the final compound, 2-(2,6-dioxopiperidin-3-yl)-5-((15-(5-(5-methyl-5H-pyrido[4,3-b]indol-7-yl)pyridin-2-yl)-3,6,9,12-tetraoxapentadec-14-yn-1-yl)oxy)isoindoline-1,3-dione, according to the following scheme and using procedures described above and common procedures known to those skilled in the art.

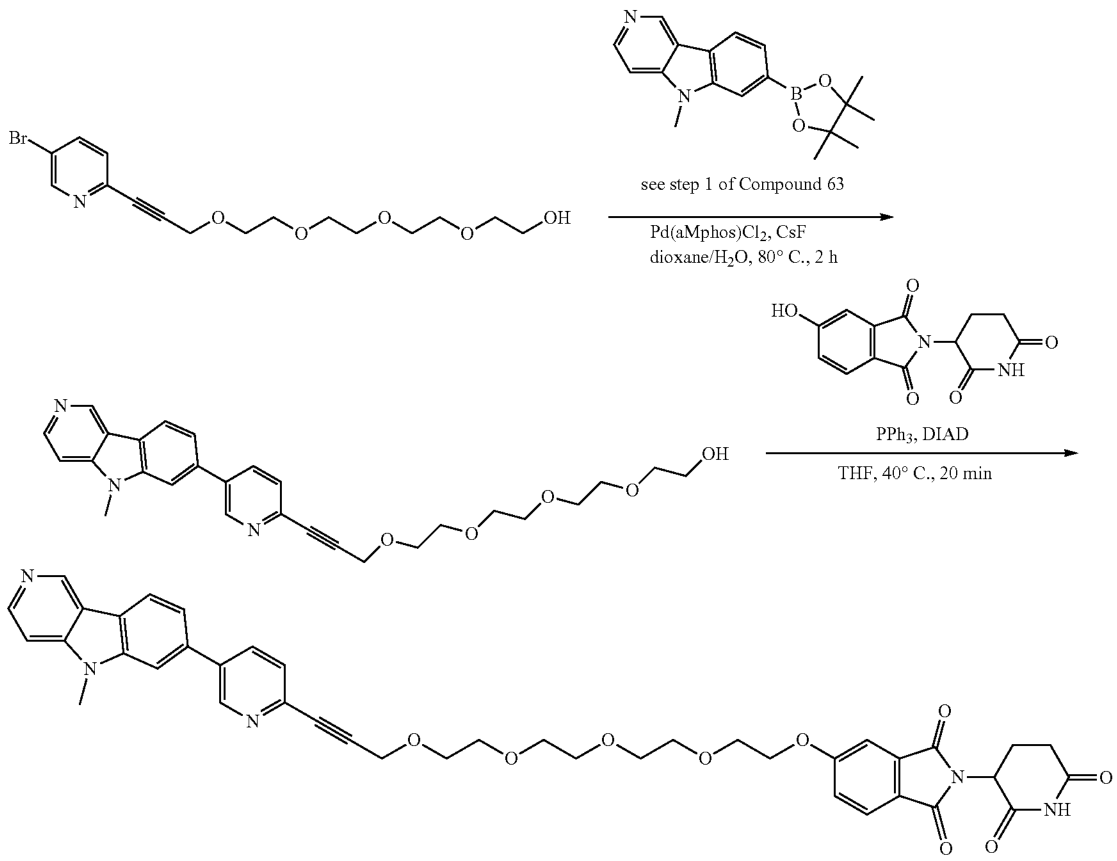

Compound 71

Compound 71: $^1$H NMR (400 MHz, DMSO-d$_6$): δ 9.39 (s, 1H), 8.38 (d, J=8.4 Hz, 1H), 8.30 (d, J=2.0 Hz, 1H), 8.28 (d, J=3.0 Hz, 1H), 8.11 (s, 1H), 7.80 (d, J=8.4 Hz, 1H), 7.72 (d, J=7.6 Hz, 1H), 7.63-7.68 (m, 2H), 7.44 (d, J=2.0 Hz, 1H), 7.34-7.36 (m, 1H), 5.08-5.12 (m, 1H), 4.48 (s, 2H), 4.31 (t, J=3.6 Hz, 2H), 3.98 (s, 3H), 3.80 (s, 3H), 3.53-3.79 (m, 12H), 1.95-2.08 (m, 2H). (M+H)$^+$ 746.5.

Synthetic Scheme for Exemplary Compound 74

2-(2,6-dioxopiperidin-3-yl)-5-((15-(5-(5-methyl-5H-pyrido[4,3-b]indol-7-yl)pyridin-2-yl)-3,6,9,12-tetraoxapentadecyl)oxy)isoindoline-1,3-dione

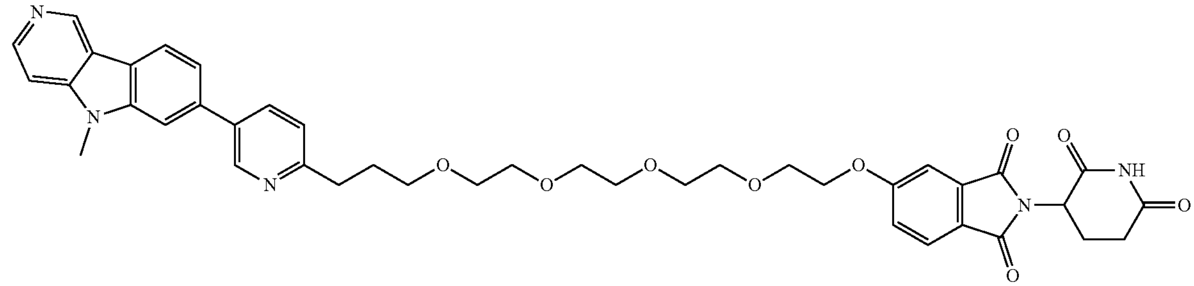 [SMILES: Cn1c2ccncc2c2ccc(-c3ccc(CCCOCCOCCOCCOCCOc4ccc5c(c4)C(=O)N(C4CCC(=O)NC4=O)C5=O)nc3)cc21]

Prepared according to the synthetic scheme below using procedures described above and common procedures known to those skilled in the art.

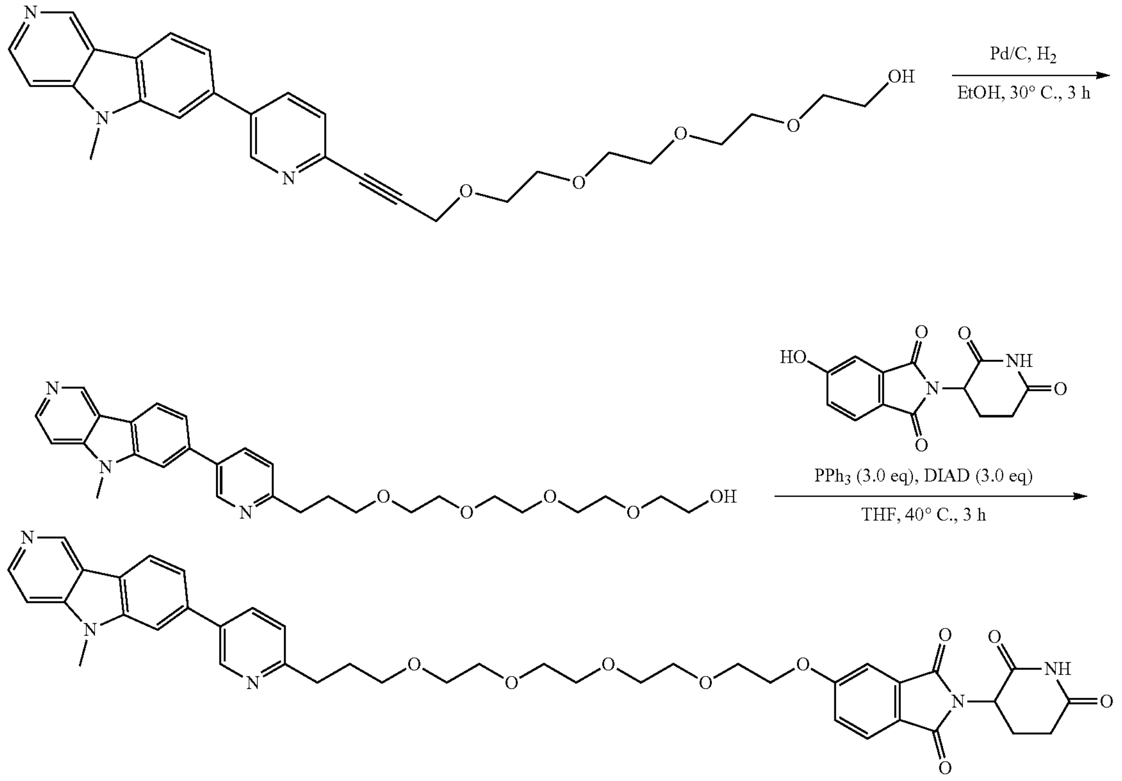

Compound 74

Compound 74: $^1$H NMR (400 MHz, $CDCl_3$): δ 9.65 (s, 1H), 9.22 (s, 1H), 8.67-8.73 (m, 2H), 8.47 (d, J=7.6 Hz, 1H), 8.36 (d, J=8.0 Hz, 1H), 7.97 (s, 1H), 7.83 (s, 1H), 7.81 (s, 1H), 7.59-7.71 (m, 2H), 7.04 (d, J=9.2 Hz, 2H), 4.93-4.96 (m, 1H), 4.10 (s, 5H), 3.87 (s, 1H), 3.55-3.76 (m, 18H), 3.26 (s, 2H), 2.12-2.16 (m, 2H). $(M+H)^+$ 750.5.

Synthetic Scheme for Exemplary Compound 72

5-((14-((5-(5H-pyrido[4,3-b]indol-7-yl)pyridin-2-yl)oxy)-3,6,9,12-tetraoxatetradecyl)oxy)-2-(2,6-dioxopiperidin-3-yl)-4,6,7-trifluoroisoindoline-1,3-dione

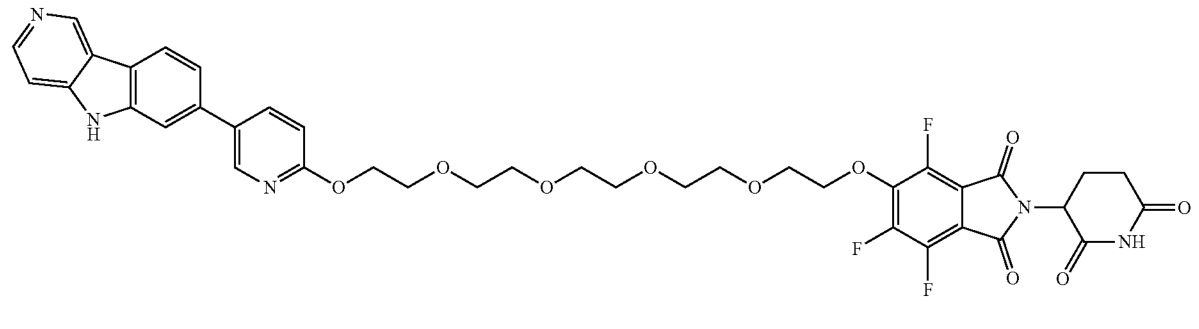 [SMILES: O=C1CCC(N2C(=O)c3c(F)c(F)c(OCCOCCOCCOCCOCCOc4ccc(-c5ccc6c(c5)[nH]c5ccncc56)cn4)c(F)c3C2=O)C(=O)N1]

Prepared according to the synthetic scheme below using procedures described above and common procedures known to those skilled in the art.

2-(2,6-dioxopiperidin-3-yl)-4,5,7-trifluoro-6-hydroxyisoindoline-1,3-dione was prepared as described below.

Step 1: 3,4,6-trifluoro-5-hydroxyphthalic acid

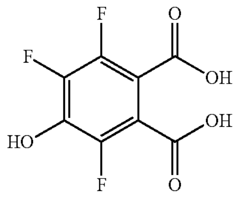 [SMILES: O=C(O)c1c(F)c(O)c(F)c(F)c1C(=O)O]

To a solution of 3,4,5,6-tetrafluorophthalic acid (1.18 g, 5 mmol) in water (20 mL) was added potassium hydroxide (2.24 g, 40 mmol, 8 eq). The resulting solution was heated to 90° C. for 9 hours. Then the reaction was cooled to room temperature and neutralized by HCl (1 N). The resulting solution was extracted with ethyl acetate (50 mL×3). The combined organic layers were washed with brine (20 mL×2), dried over anhydrous sodium sulfate and concentrated under vacuum to afford crude desired product (1.15 g) as white solid, which was used in the next step without purification.

Step 2: 2-(2,6-dioxopiperidin-3-yl)-4,5,7-trifluoro-6-hydroxyisoindoline-1,3-dione

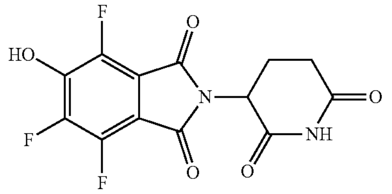 [SMILES: O=C1CCC(N2C(=O)c3c(F)c(O)c(F)c(F)c3C2=O)C(=O)N1]

To a solution of 3,4,6-trifluoro-5-hydroxyphthalic acid (500 mg, 2.12 mmol), 3-aminopiperidine-2,6-dione (383 mg, 2.33 mmol) in AcOH was added AcONa (209 mg, 2.54 mmol). The resulting solution was stirred at 120° C. for 4 h. After cooling to room temperature, the solvent was removed under vacuum. Then it was quenched with water (30 mL). The resulting solution was extracted with EA (30 mL×3). The combined organic layers were washed with brine (10 mL×2), dried over anhydrous sodium sulfate and concentrated under vacuum to afford 2-(2,6-dioxopiperidin-3-yl)-4,5,7-trifluoro-6-hydroxyisoindoline-1,3-dione (400 mg, 1.22 mmol, 58%.

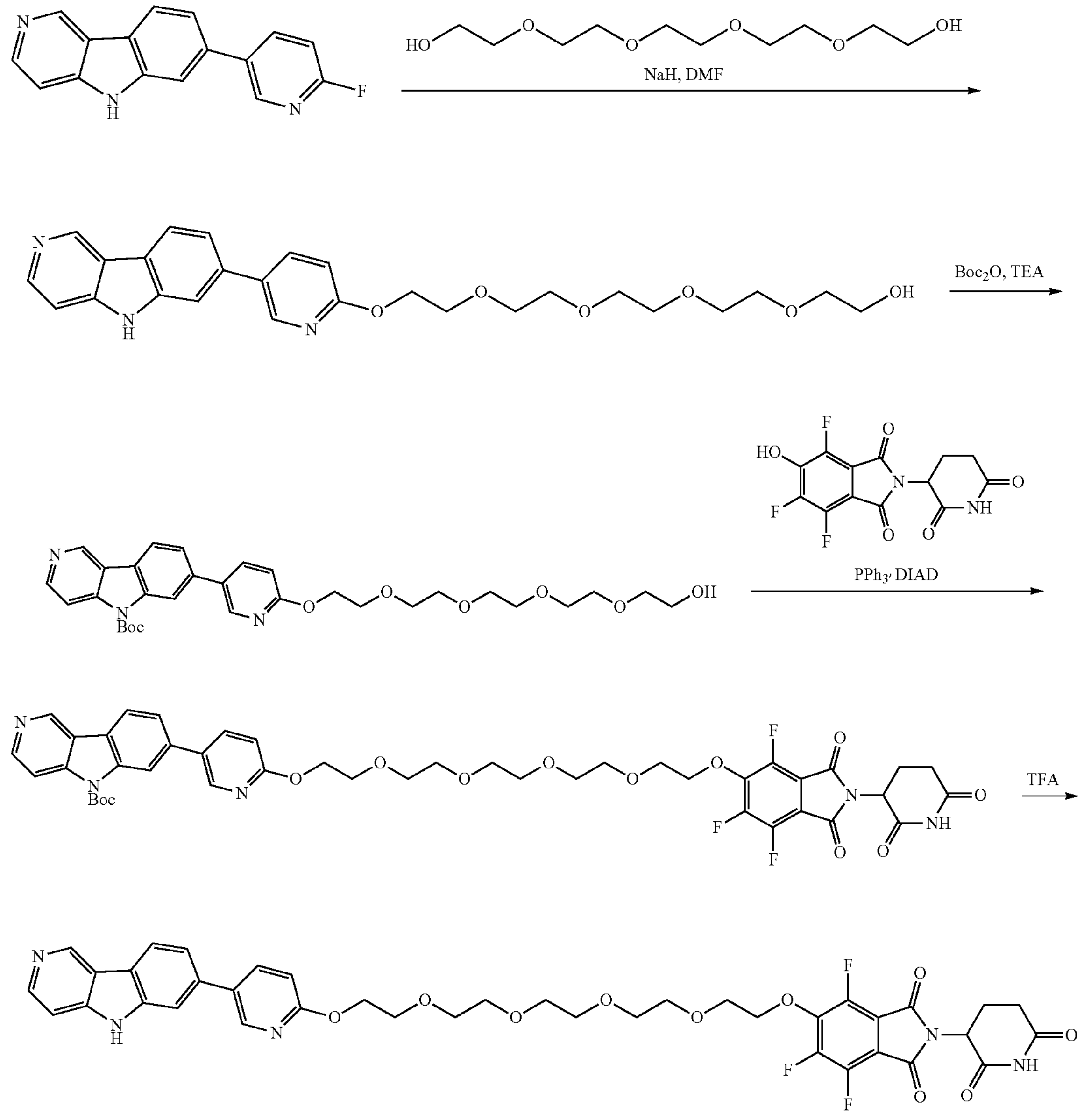

Comp

Compound 72: $^1H$ NMR (400 MHz, $CD_3OD$): δ 13.19 (s, 1H), 9.77 (s, 1H), 8.62-8.68 (m, 2H), 8.52 (d, J=8.0 Hz, 1H), 8.16 (s, 1H), 8.01-8.02 (m, 2H), 7.80-7.81 (m, 1H), 7.15-7.28 (m, 1H), 6.99 (d, J=8.0 Hz, 1H), 5.15-5.23 (m, 1H), 4.43-4.45 (m, 2H), 3.77-3.89 (m, 4H), 3.49-3.60 (m, 12H), 2.86-3.05 (m, 3H), 1.99-2.01 (m, 1H). $(M+H)^+$ 792.5.
Synthetic Scheme for Exemplary Compound 81
5-((14-((5-(5H-pyrido[4,3-b]indol-7-yl)pyridin-2-yl)oxy)-3,6,9,12-tetraoxatetradecyl)oxy)-2-(2,6-dioxopiperidin-3-yl)-6-fluoroisoindoline-1,3-dione
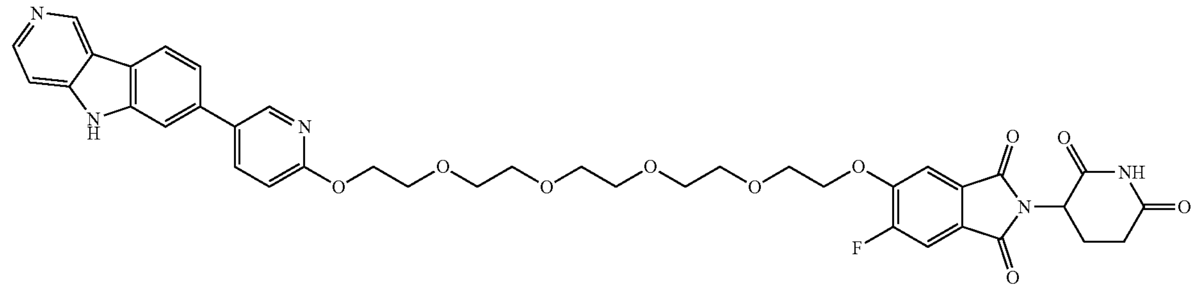 [SMILES: O=C1CCC(N2C(=O)c3cc(F)c(OCCOCCOCCOCCOCCOc4ccc(-c5ccc6c(c5)[nH]c5ccncc56)cn4)cc3C2=O)C(=O)N1]
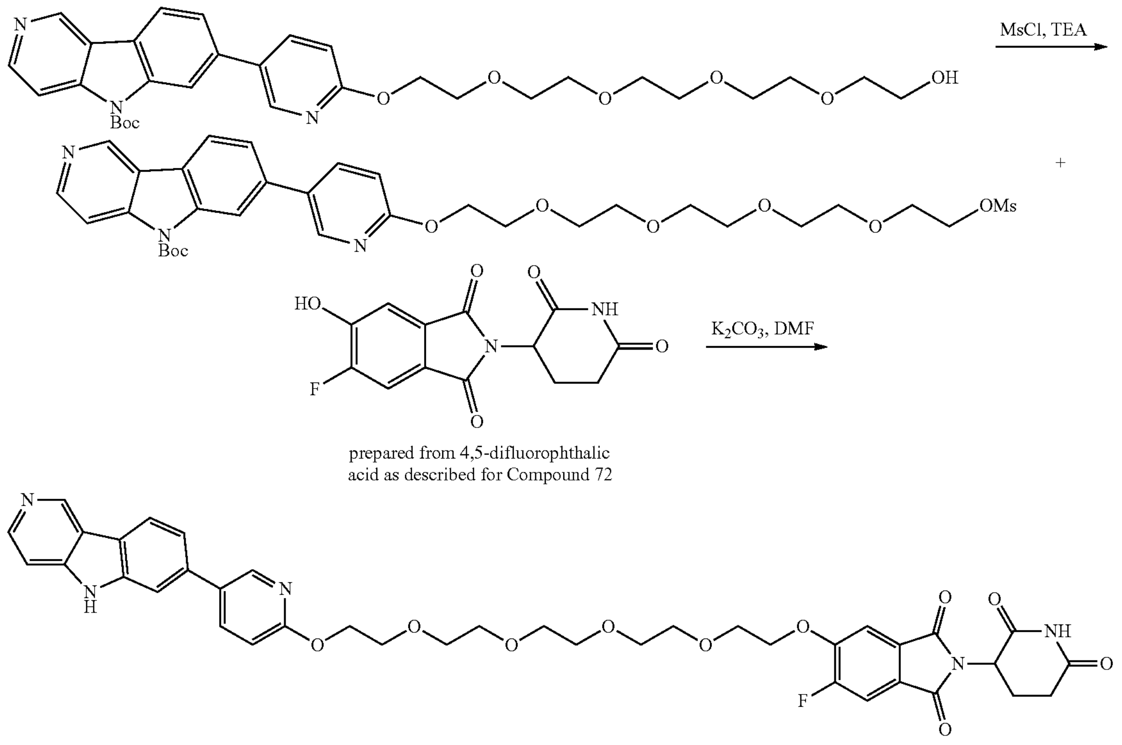
Compound 81
Compound 81: $^1H$ NMR (400 MHz, $CDCl_3$): δ 39.31 (s, 1H), 8.51 (s, 1H), 8.40 (s, 1H), 8.11 (d, J=8.0 Hz, 1H), 7.82-7.83 (m, 1H), 7.60 (s, 1H), 7.37-7.45 (m, 3H), 6.84 (d, J=8.0 Hz, 1H), 4.92-4.95 (m, 1H), 4.53 (t, J=4.8 Hz, 2H), 4.24 (t, J=4.8 Hz, 2H), 3.89-3.91 (m, 4H), 3.67-3.75 (m, 12H), 2.74-2.92 (m, 3H), 2.12-2.16 (m, 1H). $(M+H)^+$ 756.5.

Synthetic Scheme of Exemplary Compound 75
2-(2,6-dioxopiperidin-3-yl)-5-(4-(5-((5-((5-(5-methyl-5H-pyrido[4,3-b]indol-7-yl)pyridin-2-yl)oxy)pentyl)oxy)pentyl)piperidin-1-yl)isoindoline-1,3-dione
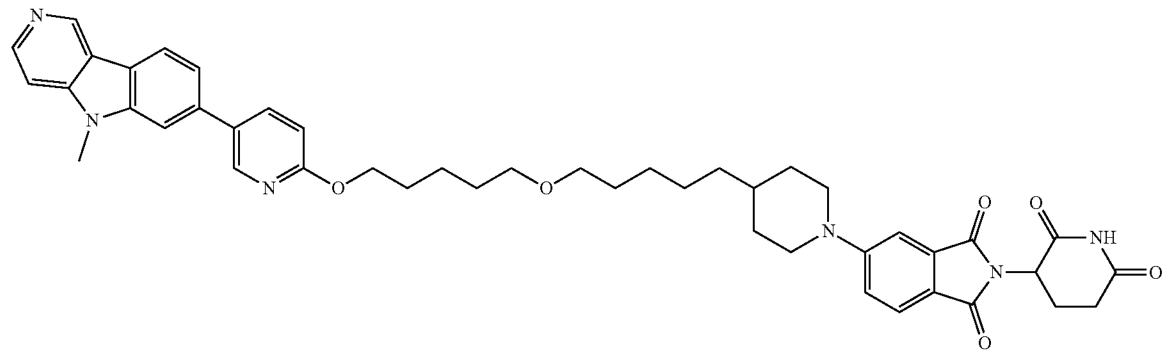 [SMILES: Cn1c2ccncc2c2ccc(-c3ccc(OCCCCCOCCCCCC4CCN(c5ccc6c(c5)C(=O)N(C5CCC(=O)NC5=O)C6=O)CC4)nc3)cc21]
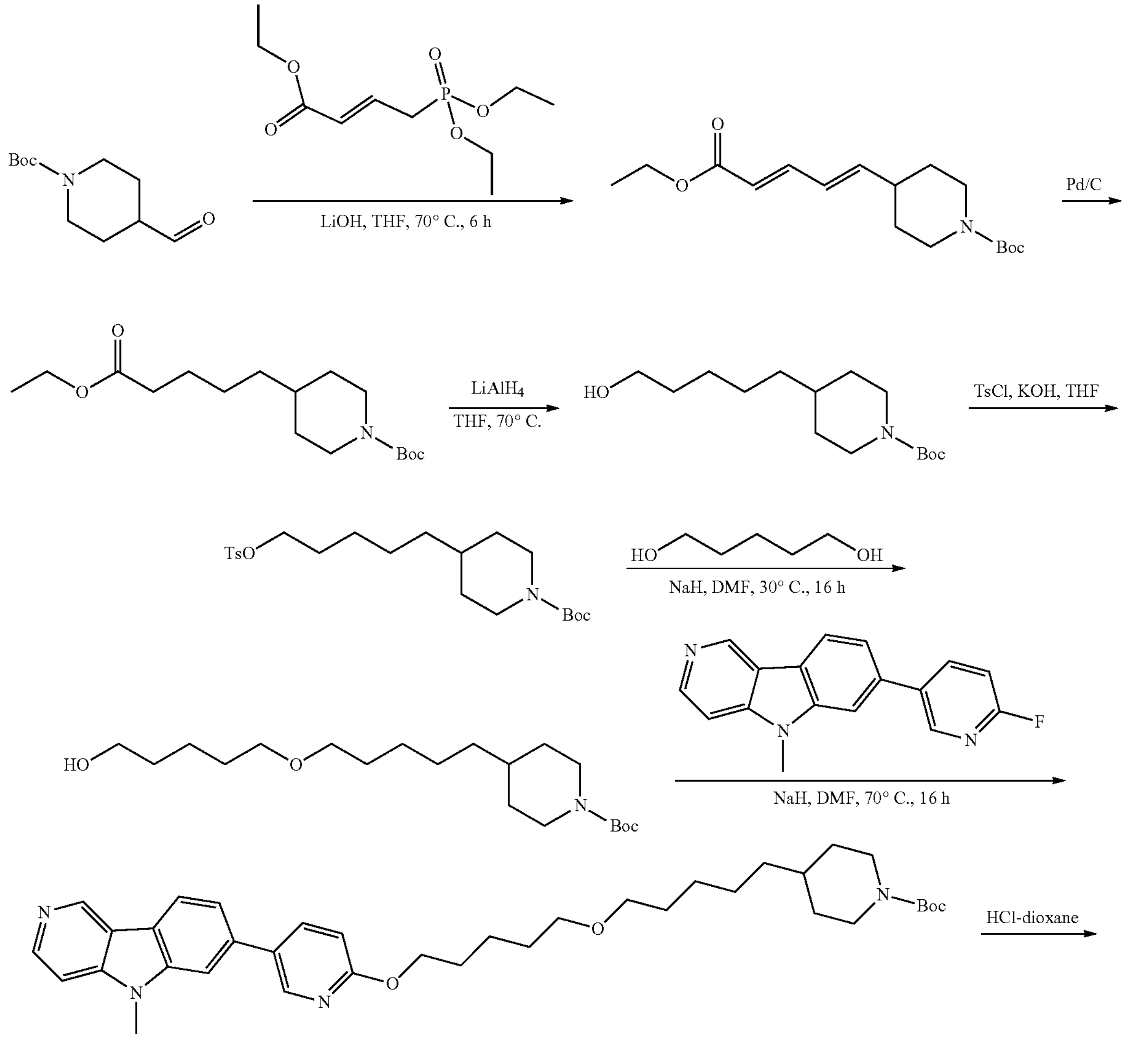

-continued

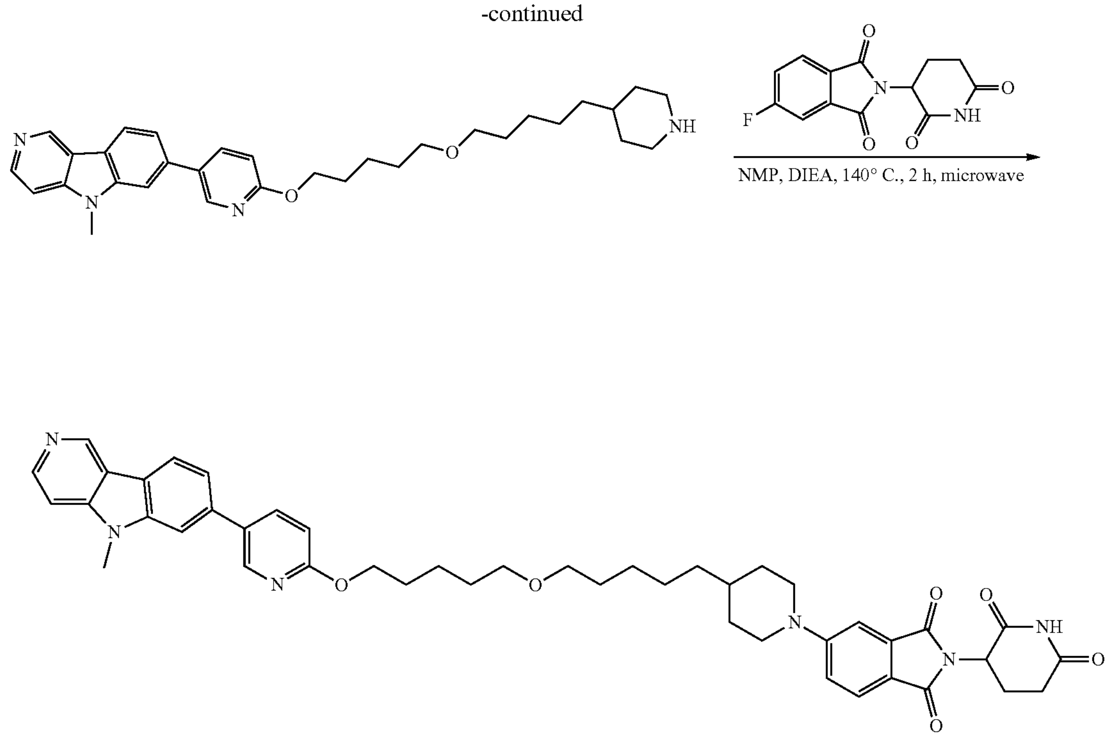

Compound 75

Compound 75: $^1$H NMR (400 MHz, DMSO-$d_6$): δ=11.07 (s, 1H), 9.38-9.32 (m, 1H), 8.66-8.63 (d, J=12 Hz 1H), 8.50-8.48 (m, J=8 Hz 1H), 8.36 (s, 2H), 8.34-8.29 (m, 1H), 8.21-8.14 (m, 1H), 7.99-7.94 (m, 1H), 7.61 (s, 3H), 7.28-7.22 (m, 1H), 7.19-7.12 (m, 1H), 6.96-6.89 (m, 1H), 5.09-5.00 (m, 1H), 4.36-4.29 (m, 2H), 3.95 (s, 5H), 3.34 (s, 4H), 2.87 (s, 2H), 2.99-2.78 (m, 1H), 2.82-2.73 (m, 1H), 2.04-1.93 (m, 1H), 1.82-1.65 (m, 4H), 1.61-1.52 (m, 2H), 1.52-1.41 (m, 5H), 1.28 (s, 4H), 1.22-1.05 (m, 4H). $(M+H)^+$ 771.6.

Synthetic Scheme for Exemplary Compound 76

2-(2,6-dioxopiperidin-3-yl)-5-(3-(3-(4-(3-(5-(5-methyl-5H-pyrido[4,3-b]indol-7-yl)pyridin-2-yl) prop-2 yn-ln-yl)piperazin-1-yl)propoxy)azetidin-1-yl)isoindoline-1,3-dione

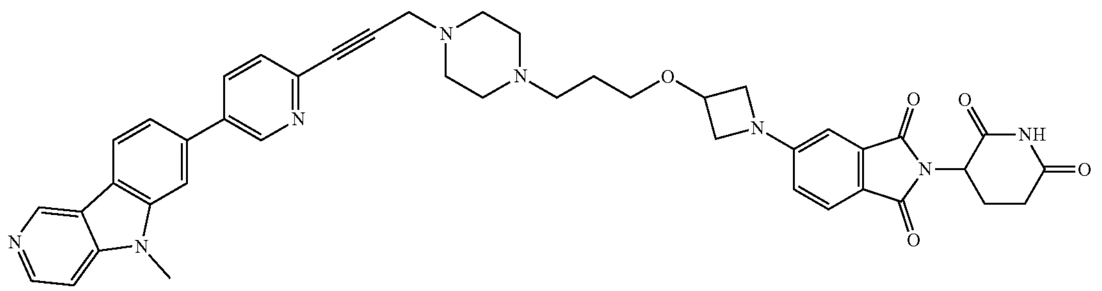 [SMILES: Cn1c2ccncc2c2ccc(-c3ccc(C#CCN4CCN(CCCOC5CN(c6ccc7c(c6)C(=O)N(C6CCC(=O)NC6=O)C7=O)C5)CC4)nc3)cc21]

Prepared according to the synthetic scheme below using procedures described above and common procedures to those skilled in the art.

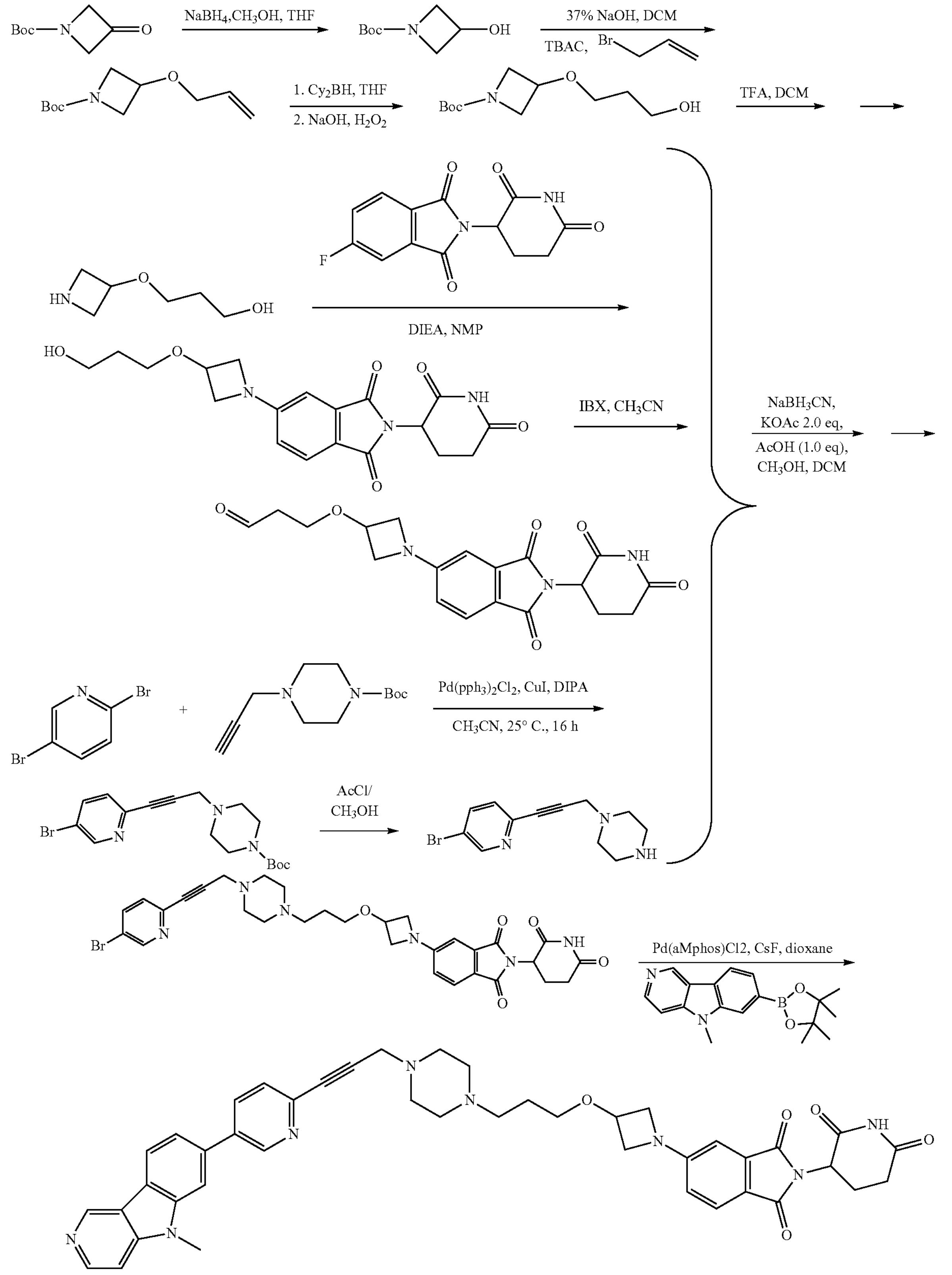
Compound 76
Compound 76: $^1$H NMR (400 MHz, CD$_3$OD): δ 9.32 (s, 1H), 8.96 (s, 1H), 8.45-8.52 (m, 2H), 8.37 (d, J=8.0 Hz, 1H), 8.27-8.31 (m, 1H), 7.98 (s, 1H), 7.61-7.98 (m, 4H), 6.82 (s, 1H), 6.65-6.67 (m, 1H), 5.01-5.05 (m, 1H), 4.59 (m, 1H), 4.27 (t, J=8.4 Hz, 1H), 4.02 (s, 3H), 3.88-3.91 (m, 2H), 3.70 (s, 2H), 3.57 (t, J=6.0 Hz, 2H), 3.41 (m, 1H), 3.13-3.17 (m, 2H), 2.66-2.86 (m, 11H), 2.02-2.03 (m, 3H). (M+H) 751.5.
Synthetic Scheme for Exemplary Compound 78
2-(2,6-dioxopiperidin-3-yl)-5-(4-(6-((1r,3r)-3-((5-(5-methyl-5H-pyrido[4,3-b]indol-7-yl)pyridin-2-yl)oxy)cyclobutoxy)hexyl)piperazin-1-yl)isoindoline-1,3-dione
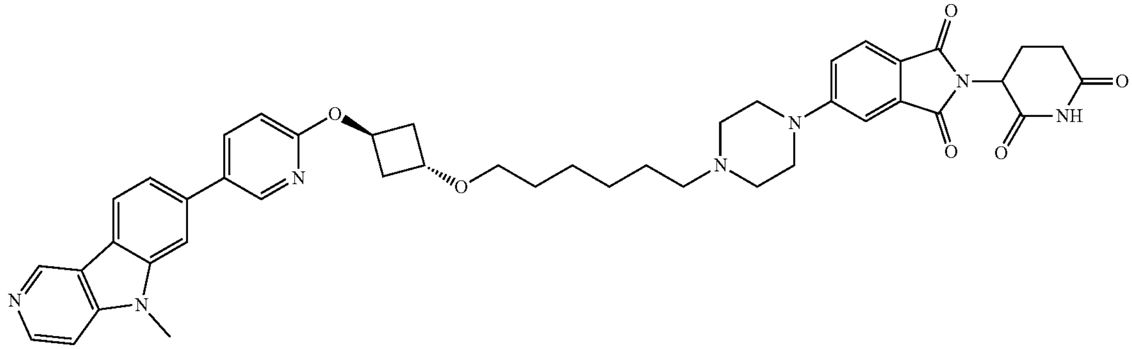 [SMILES: Cn1c2ccncc2c2ccc(-c3ccc(O[C@H]4C[C@H](OCCCCCCN5CCN(c6ccc7c(c6)C(=O)N(C6CCC(=O)NC6=O)C7=O)CC5)C4)nc3)cc21]
Prepared according to the synthetic scheme below using procedures described above and common procedures known to those skilled in the art.
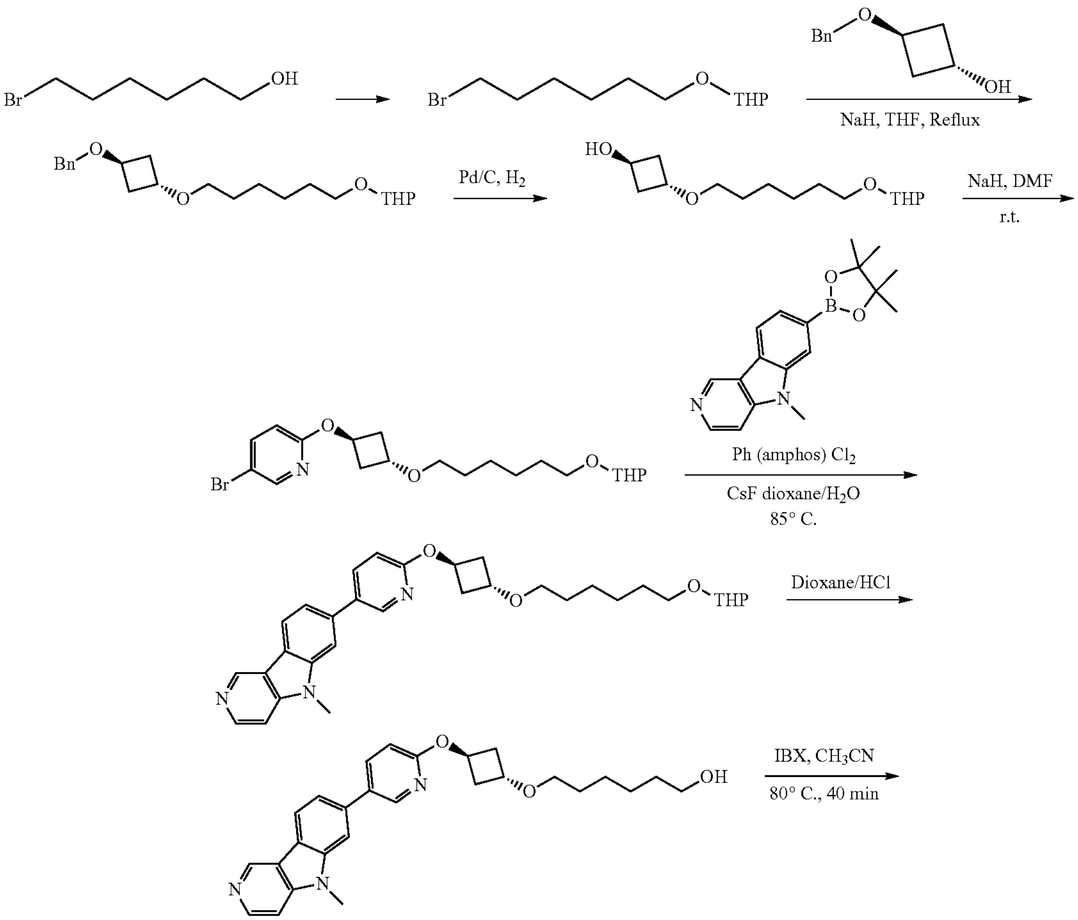

-continued

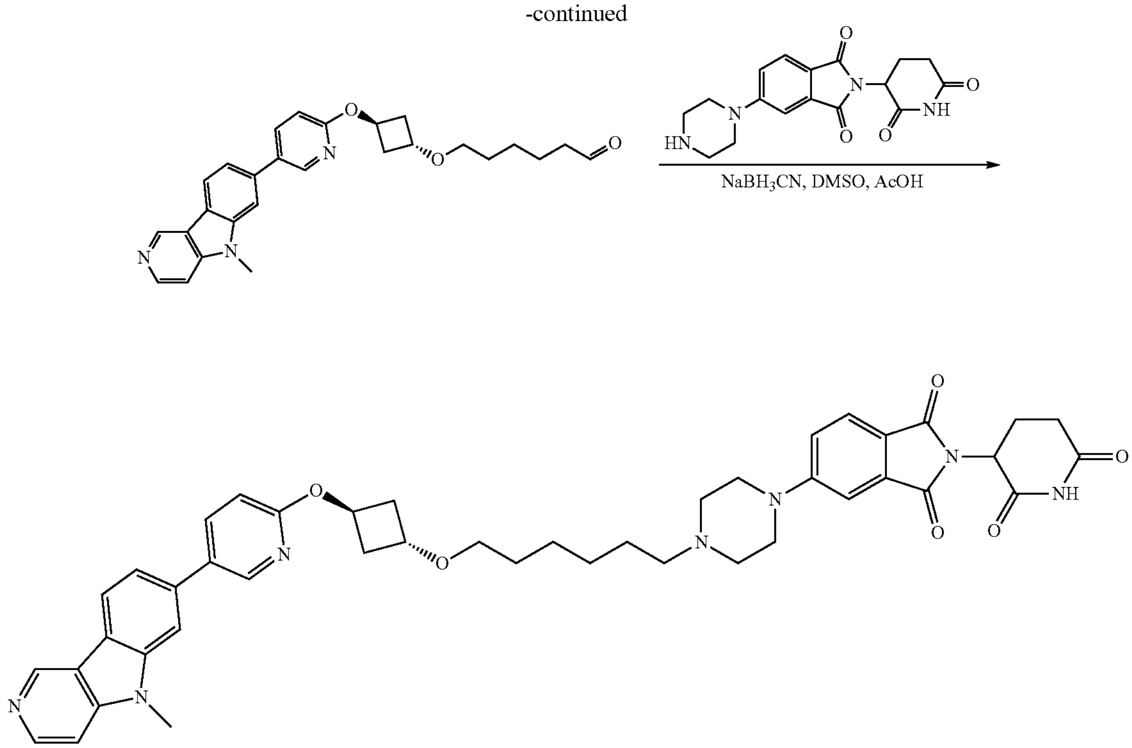

Compount 78

Compound 78: $^1$H NMR (400 MHz, DMSO-d6): δ 11.08 (s, 1H), 9.35 (s, 1H), 8.64 (t, J=3.9 Hz, 1H), 8.49 (d, J=4.7 Hz, 1H), 8.32 (d, J=8.1 Hz, 1H), 8.19 (dd, J=8.6, 2.5 Hz, 1H), 7.98 (s, 1H), 7.68-7.48 (m, 3H), 7.31 (d, J=7.8 Hz, 1H), 7.20 (t, J=9.5 Hz, 1H), 6.94 (d, J=8.6 Hz, 1H), 5.07 (dd, J=12.9, 5.3 Hz, 1H), 4.33 (t, J=6.5 Hz, 2H), 3.95 (s, 3H), 3.65 (m, 1H), 3.51-3.41 (m, 3H), 3.36-3.23 (m, 5H), 2.95-2.83 (m, 1H), 2.43-2.28 (m, 6H), 2.05-1.96 (m, 1H), 1.79-1.73 (m, 1H), 1.67-1.61 (m, 1H), 1.42 (m, 7H). $(M+H)^+$ 770.6.

Synthetic Scheme of Exemplary Compound 85

2-(2,6-dioxopiperidin-3-yl)-5-((1r,3r)-3-((5-((5-((5-(5-methyl-5H-pyrido[4,3-b]indol-7-yl)pyridin-2-yl)oxy)pentyl)oxy)pentyl)oxy)cyclobutoxy)isoindoline-1,3-dione

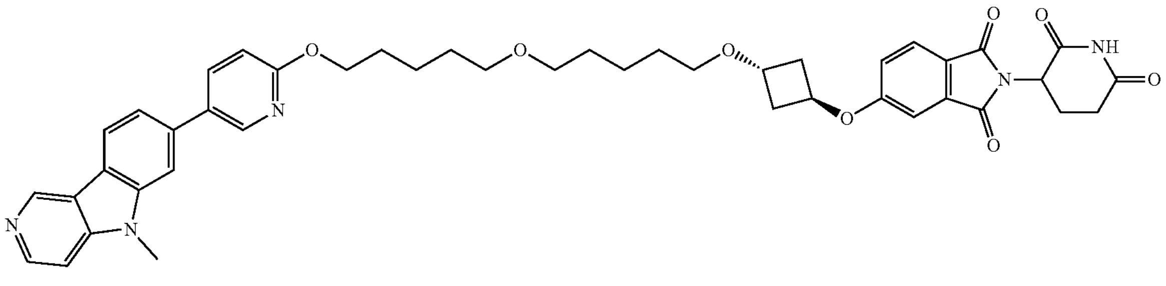 [SMILES: Cn1c2ccncc2c2ccc(-c3ccc(OCCCCCOCCCCCO[C@H]4C[C@H](Oc5ccc6c(c5)C(=O)N(C5CCC(=O)NC5=O)C6=O)C4)nc3)cc21]

Prepared according to the synthetic scheme below using procedures described above and common procedures to those skilled in the art.

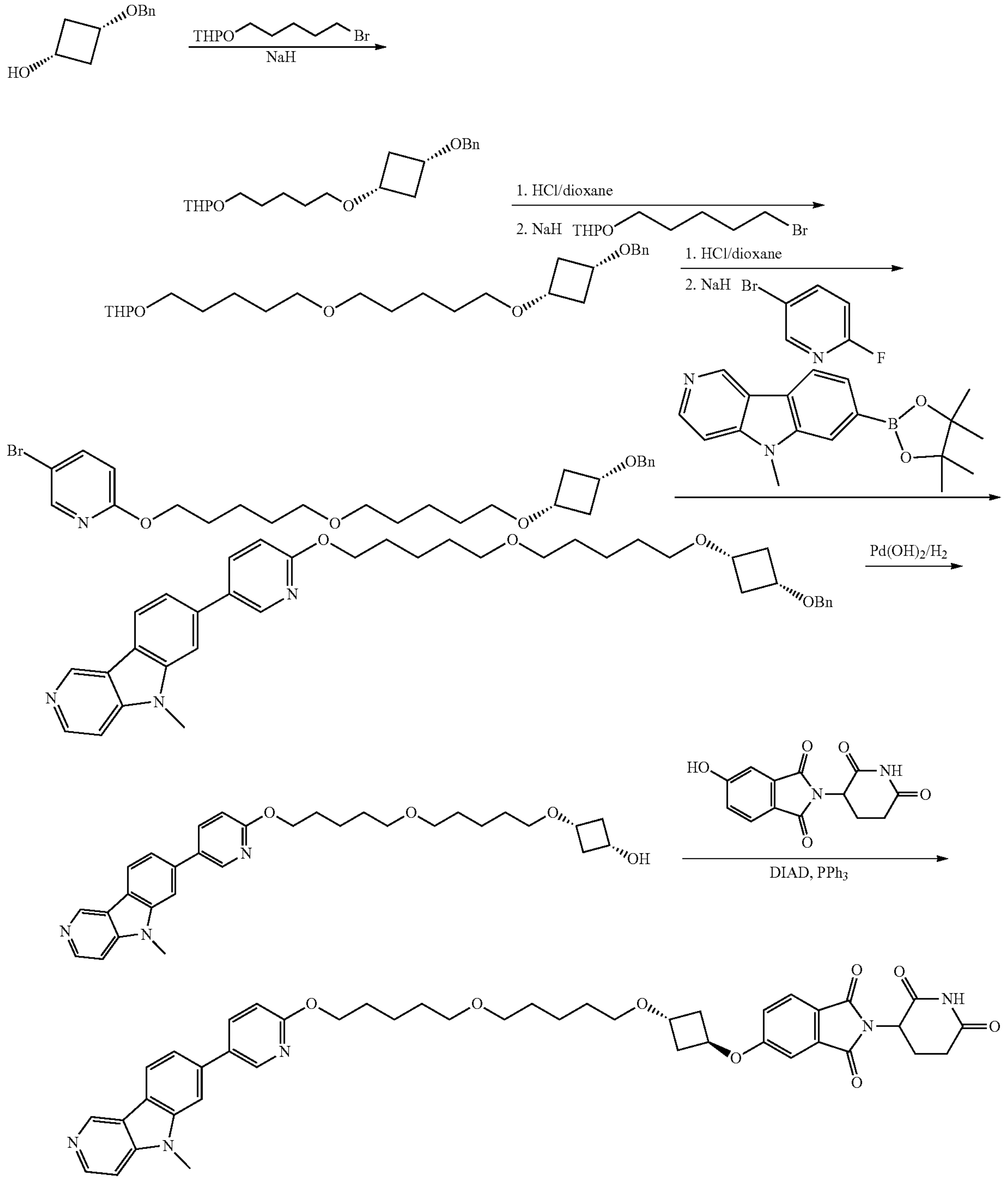
Compound 85
Compound 85: $^1$H NMR (400 MHz, $CDCl_3$): δ 9.32 (s, 1H), 8.58-8.59 (d, J=4.0 Hz, 2H), 8.48 (s, 1H), 8.16-8.18 (d, J=8.0 Hz, 1H), 7.89-7.91 (d, J=8.0 Hz, 1H), 7.74-7.76 (d, J=8.0 Hz, 1H), 7.56 (s, 1H), 7.47-7.49 (d, J=8.0 Hz, 1H), 7.32-7.33 (d, J=4.0 Hz, 1H), 7.19 (s, 1H), 7.06-7.08 (d, J=8.0 Hz, 1H), 6.84-6.86 (d, J=8.0 Hz, 1H), 4.93 (m, 2H), 4.35-4.38 (m, 2H), 4.21 (s, 1H), 3.90 (s, 3H), 3.35-3.49 (m, 7H), 2.68-2.95 (m, 3H), 2.44-2.51 (m, 4H), 2.15 (m, 1H), 1.88 (m, 2H), 1.56-1.68 (m, 9H), 1.44 (d, J=8.0 Hz, 2H). $(M+H)^+$ 774.6.

Synthetic Scheme of Exemplary Compound 79
2-(2,6-dioxopiperidin-3-yl)-5-(3-((5-((5-((5-(5-methyl-5H-pyrido[4,3-b]indol-7-yl)pyridin-2-yl)oxy)pentyl)oxy)pentyl)oxy)azetidin-1-yl)isoindoline-1,3-dione
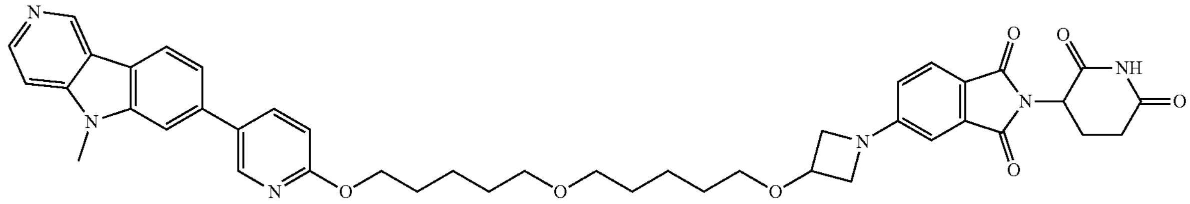 [SMILES: Cn1c2ccncc2c2ccc(-c3ccc(OCCCCCOCCCCCOC4CN(c5ccc6c(c5)C(=O)N(C5CCC(=O)NC5=O)C6=O)C4)nc3)cc21]
Prepared according to the synthetic scheme below using procedures described above and common procedures to those skilled in the art.
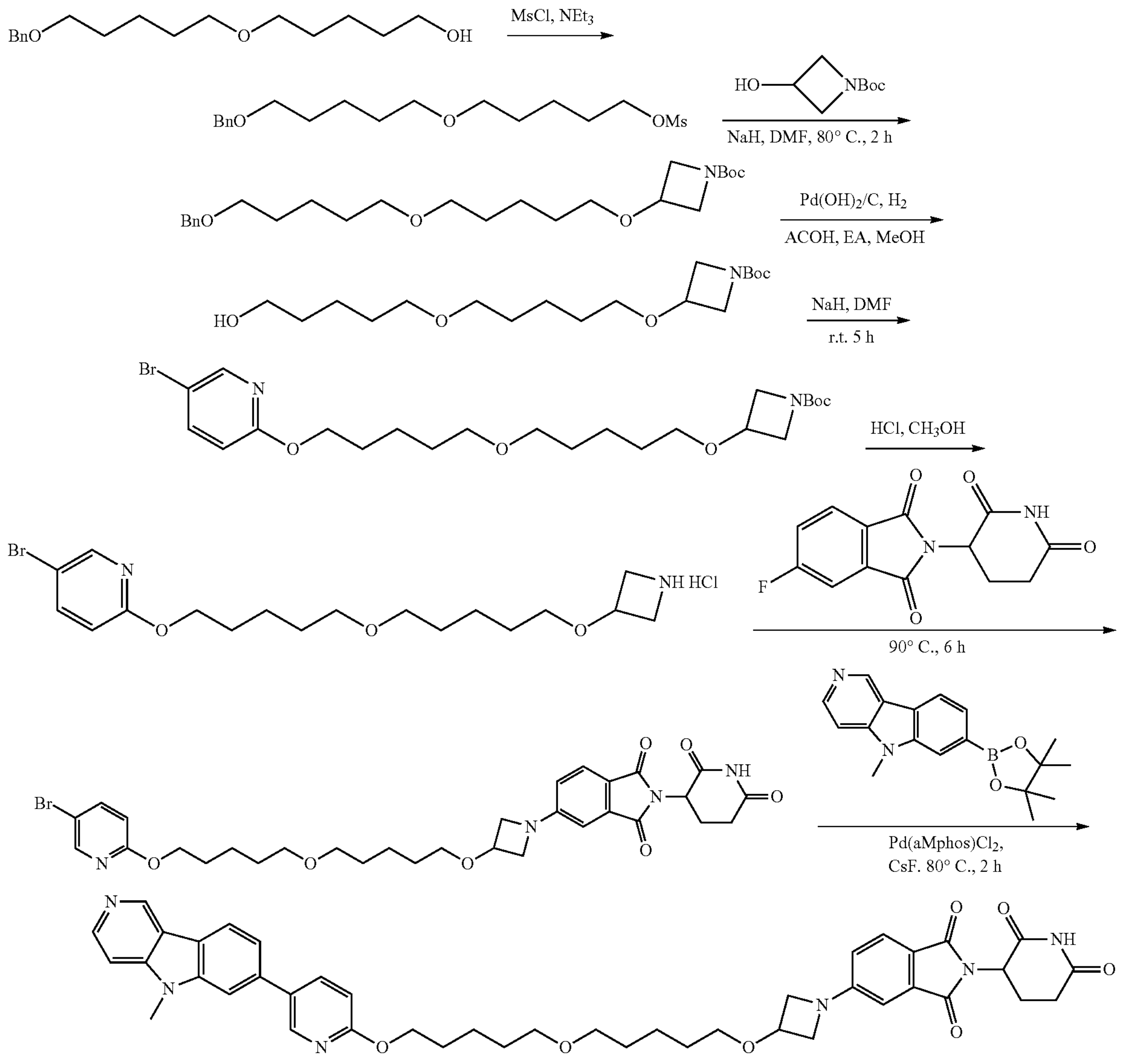
Compound 79

Compound 79: $^1$H NMR (400 MHz, $CDCl_3$): δ 9.35 (s, 1H), 8.59 (d, J=5.7 Hz, 1H), 8.49 (s, 1H), 8.28 (s, 1H), 8.21 (d, J=10.6 Hz, 1H), 8.00 (s, 1H), 7.91 (d, J=11.0 Hz, 1H), 7.63 (d, J=8.2 Hz, 1H), 7.57 (s, 1H), 7.51 (d, J=9.3 Hz, 1H), 7.37 (d, J=5.9 Hz, 1H), 6.85 (d, J=8.6 Hz, 1H), 6.77 (s, 1H), 4.92 (m, 1H), 4.45 (s, 1H), 4.36 (t, J=6.6 Hz, 2H), 4.16-4.26 (m, 2H), 3.83-3.98 (m, 4H), 3.44 (m, 4H), 2.63-2.92 (m, 3H), 2.11 (d, J=6.4 Hz, 2H), 1.79-1.89 (m, 3H), 1.44-1.70 (m, 10H). $(M+H)^+$ 759.6.

Synthetic Scheme for Exemplary Compound 80

2-(2,6-dioxopiperidin-3-yl)-5-((1-(5-((5-((5-(5-methyl-5H-pyrido[4,3-b]indol-7-yl)pyridin-2-yl)oxy)pentyl)oxy)pentyl)azetidin-3-yl)oxy)isoindoline-1,3-dione

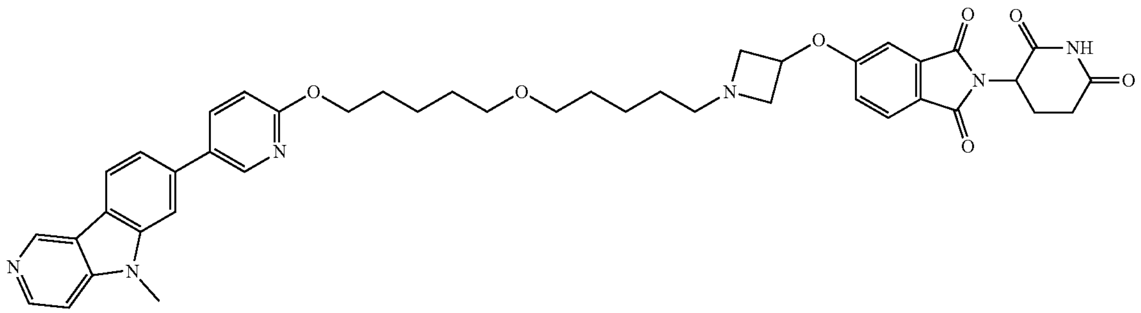 [SMILES: Cn1c2ccncc2c2ccc(-c3ccc(OCCCCCOCCCCCN4CC(Oc5ccc6c(c5)C(=O)N(C5CCC(=O)NC5=O)C6=O)C4)nc3)cc21]

Prepared according to the synthetic scheme below using procedures described above and common procedures to those skilled in the art.

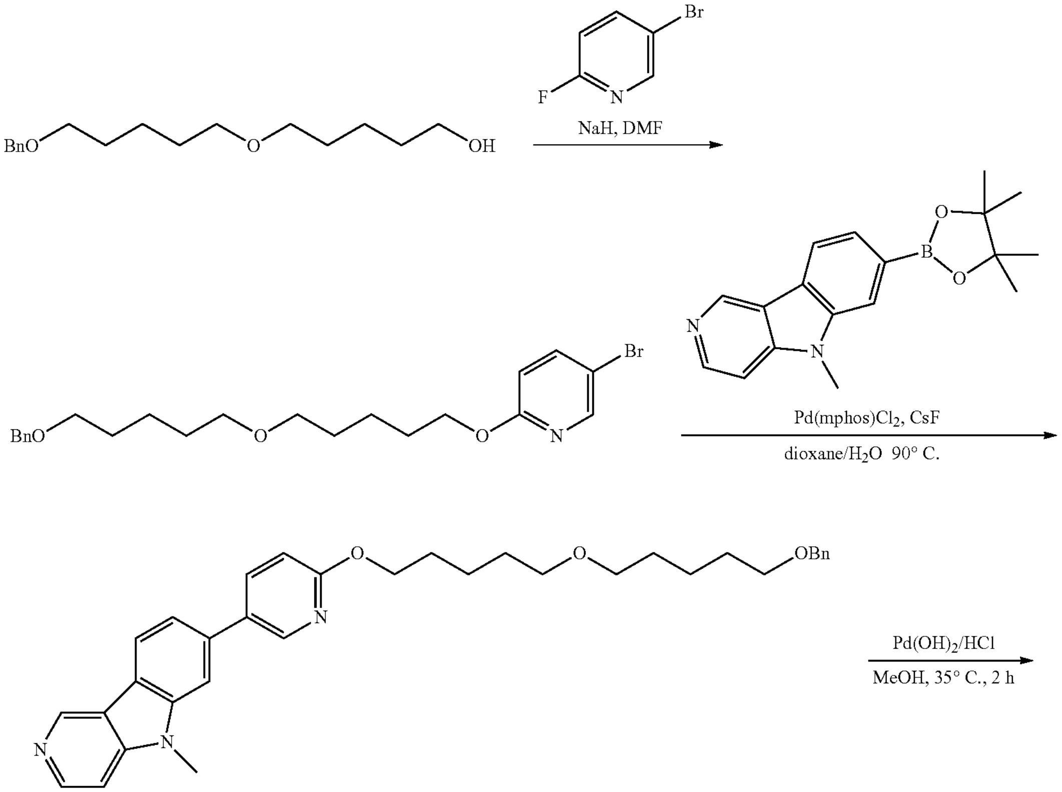

-continued
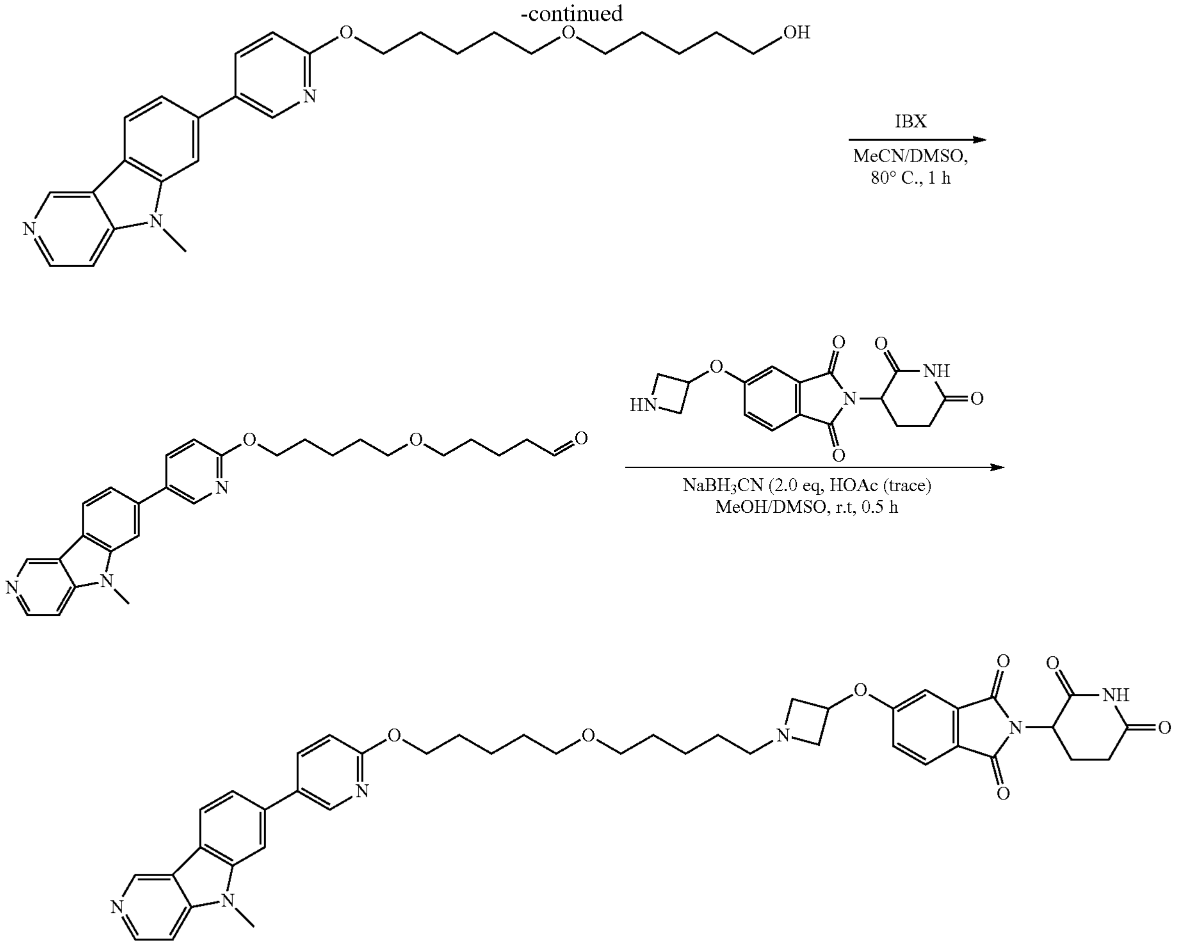
Compound 80
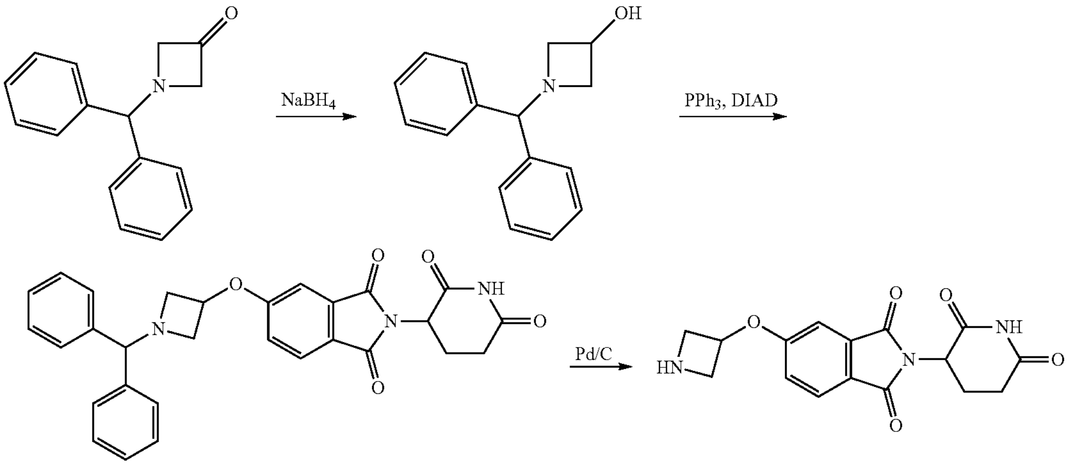
Compound 80: $^1H$ NMR (400 MHz, DMSO-$d_6$): δ 11.12 (s, 1H), 9.35 (s, 1H), 8.63 (d, J=2.3 Hz, 1H), 8.50 (s, 1H), 8.31 (d, J=8.1 Hz, 1H), 8.18 (dd, J=8.6, 2.5 Hz, 1H), 7.96 (s, 1H), 7.80 (d, J=8.8 Hz, 1H), 7.60 (d, J=6.8 Hz, 2H), 7.23 (d, J=7.2 Hz, 2H), 6.93 (d, J=8.6 Hz, 1H), 5.10 (m, 1H), 5.02-4.95 (m, 1H), 4.32 (t, J=6.6 Hz, 2H), 3.95 (s, 3H), 3.70 (t, J=6.8 Hz, 2H), 2.99-2.95 (m, 2H), 2.86 (d, J=12.1 Hz, 2H), 2.64 (br, 1H), 2.55 (br, 2H), 2.33 (s, 2H), 2.06-1.96 (m, 3H), 1.81-1.70 (m, 3H), 1.60-1.40 (m, 8H). $(M+H)^+$ 759.6.

Synthetic Scheme for Exemplary Compound 84

2-(2,6-dioxopiperidin-3-yl)-5-((6-(3-((1r,3r)-3-((5-(5-methyl-5H-pyrido[4,3-b]indol-7-yl)pyridin-2-yl)oxy)cyclobutoxy)phenoxy)hexyl)oxy)isoindoline-1,3-dione

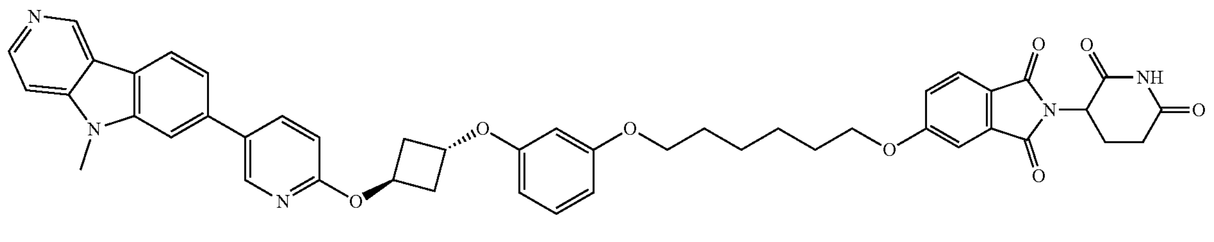 [SMILES: Cn1c2ccncc2c2ccc(-c3ccc(O[C@H]4C[C@H](Oc5cccc(OCCCCCCOc6ccc7c(c6)C(=O)N(C6CCC(=O)NC6=O)C7=O)c5)C4)nc3)cc21]

Step 1: 2-((6-(3-(benzyloxy)phenoxy)hexyl)oxy)tetrahydro-2H-pyran

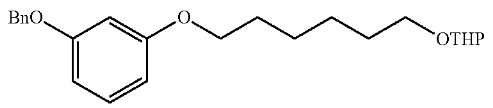

A solution of 3-(benzyloxy)phenol (1.13 g, 5.66 mmol), 2-((6-bromohexyl)oxy)tetrahydro-2H-pyran (1.0 g, 3.77 mmol) and $Cs_2CO_3$ (2.45 g, 7.55 mmol) in acetone (30 mL) was stirred at 70° C. overnight. The mixture was cooled to room temperature and quenched with water. The mixture was extracted with EA (200 mL), and the solution was washed with water (30 mL×3) and brine (30 mL). The organic phase was dried over anhydrous sodium sulfate and concentrated under vacuum. The residue was purified to afford the desired product (PE:EA=20:1) (1.2 g, yield=83%) as colorless oil.

Step 2: 3-((6-((tetrahydro-2H-pyran-2-yl)oxy)hexyl)oxy)phenol

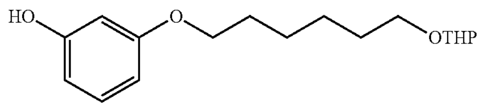

To a solution of 2-((6-(3-(benzyloxy)phenoxy)hexyl)oxy)tetrahydro-2H-pyran (1.2 g, 3.13 mmol) in MeOH (30 mL) was added Pd/C (200 mg) at room temperature. The resulting solution was stirred at room temperature overnight under $H_2$ 1 atm. The mixture was filtered, the filtrate was concentrated under vacuum to afford crude desired product (900 mg) as light yellow oil, which was used in the next step directly.

Step 3: 2-((6-(3-((1r,3r)-3-(benzyloxy)cyclobutoxy)phenoxy)hexyl)oxy)tetrahydro-2H-pyran

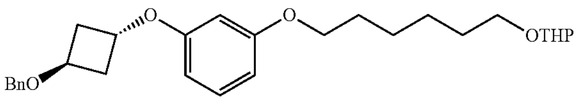

To a solution of 3-((6-((tetrahydro-2H-pyran-2-yl)oxy)hexyl)oxy)phenol (100 mg, 0.34 mmol), (1s,3s)-3-(benzyloxy)cyclobutanol (91 mg, 0.51 mmol), $PPh_3$ (267 mg, 1.02 mmol) in THF (5.0 mL) were added DIAD (206 mg, 1.02 mmol) at 40° C. under a nitrogen atmosphere. The resulting mixture was heated to 80° C. overnight. After cooling to room temperature, the reaction was quenched with water. The mixture was extracted with EA (50 mL), and the organic phase was washed with water (20 mL×3), brine (20 mL), dried over anhydrous sodium sulfate and concentrated under vacuum. The residue was purified to afford the desired product (PE:EA=5:1) (130 mg, yield=84%) as colorless oil.

2-((6-(3-((1r,3r)-3-(benzyloxy)cyclobutoxy)phenoxy)hexyl)oxy)tetrahydro-2H-pyran was converted into the final compound, 2-(2,6-dioxopiperidin-3-yl)-5-((6-(3-((1r,3r)-3-((5-(5-methyl-5H-pyrido[4,3-b]indol-7-yl)pyridin-2-yl)oxy)cyclobutoxy)phenoxy)hexyl)oxy)isoindoline-1,3-dione, according to the synthetic scheme below using procedures described above and common procedures known to those skilled in the art.

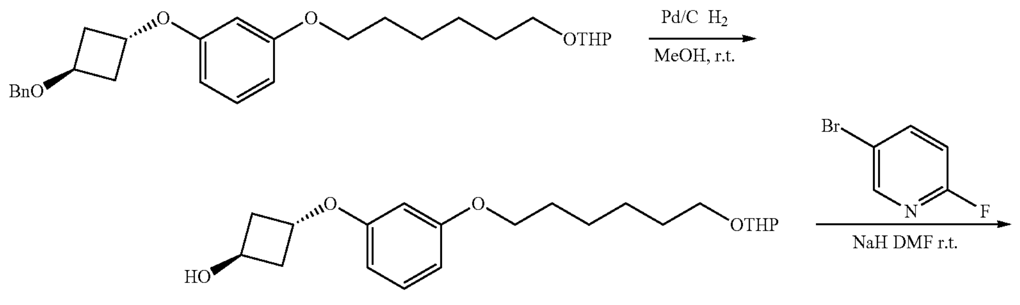

-continued
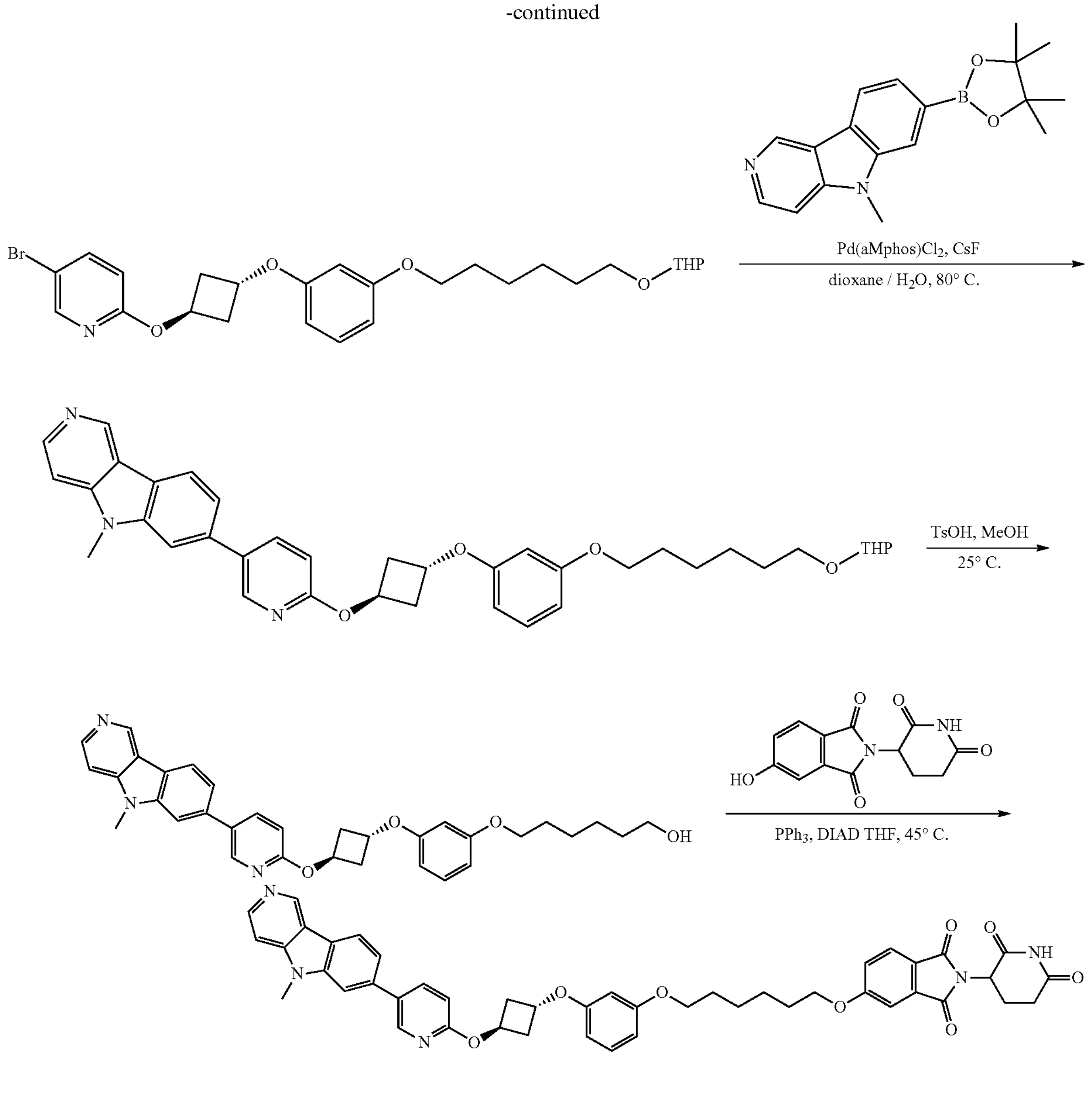
Compound 84
Compound 84: 1 H NMR (400 MHz, $CDCl_3$): δ 93.4 (s, 1H), 8.58 (d, J=5.6 Hz, 1H), 8.21-8.48 (m, 2H), 8.20 (d, J=8.4 Hz, 1H), 7.88-7.91 (m, 1H), 7.76 (d, J=8.4 Hz, 1H), 7.56 (s, 1H), 7.51 (d, J=8.0 Hz, 1H), 7.33-7.36 (m, 2H), 7.16-7.18 (m, 2H), 6.86 (d, J=8.4 Hz, 1H), 6.39-6.51 (m, 3H), 5.52-5.54 (m, 1H), 4.94-4.96 (m, 2H), 4.07-4.10 (m, 2H), 3.91-3.97 (m, 5H), 3.22-3.24 (m, 1H), 2.69-2.76 (m, 7H), 2.14-2.16 (m, 1H), 1.82-1.86 (m, 4H), 1.54-1.57 (m, 4H). $(M+H)^+$ 794.5.
Synthetic Scheme for Exemplary Compound 86
4-((14-(4-(5H-pyrido[4,3-b]indol-7-yl)phenoxy)-3,6,9,12-tetraoxatetradecyl)amino)-2-(2,6-dioxopiperidin-3-yl)isoindoline-1,3-dione
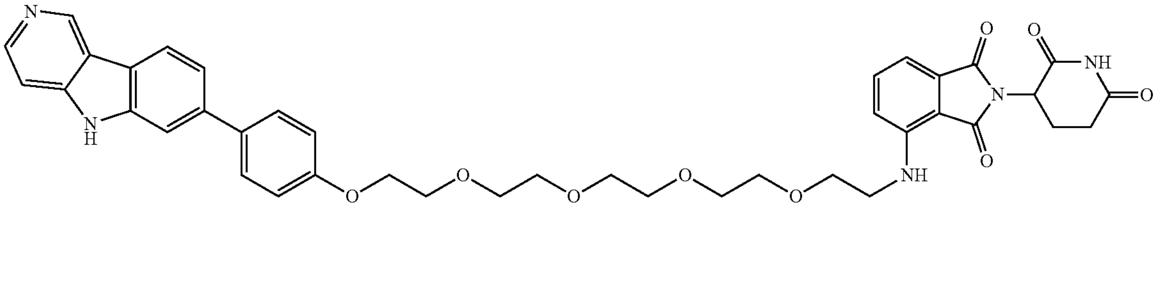 [SMILES: O=C1CCC(N2C(=O)c3cccc(NCCOCCOCCOCCOCCOc4ccc(-c5ccc6c(c5)[nH]c5ccncc56)cc4)c3C2=O)C(=O)N1]

Prepared according to the synthetic scheme below using procedures described above and common procedures to those skilled in the art.
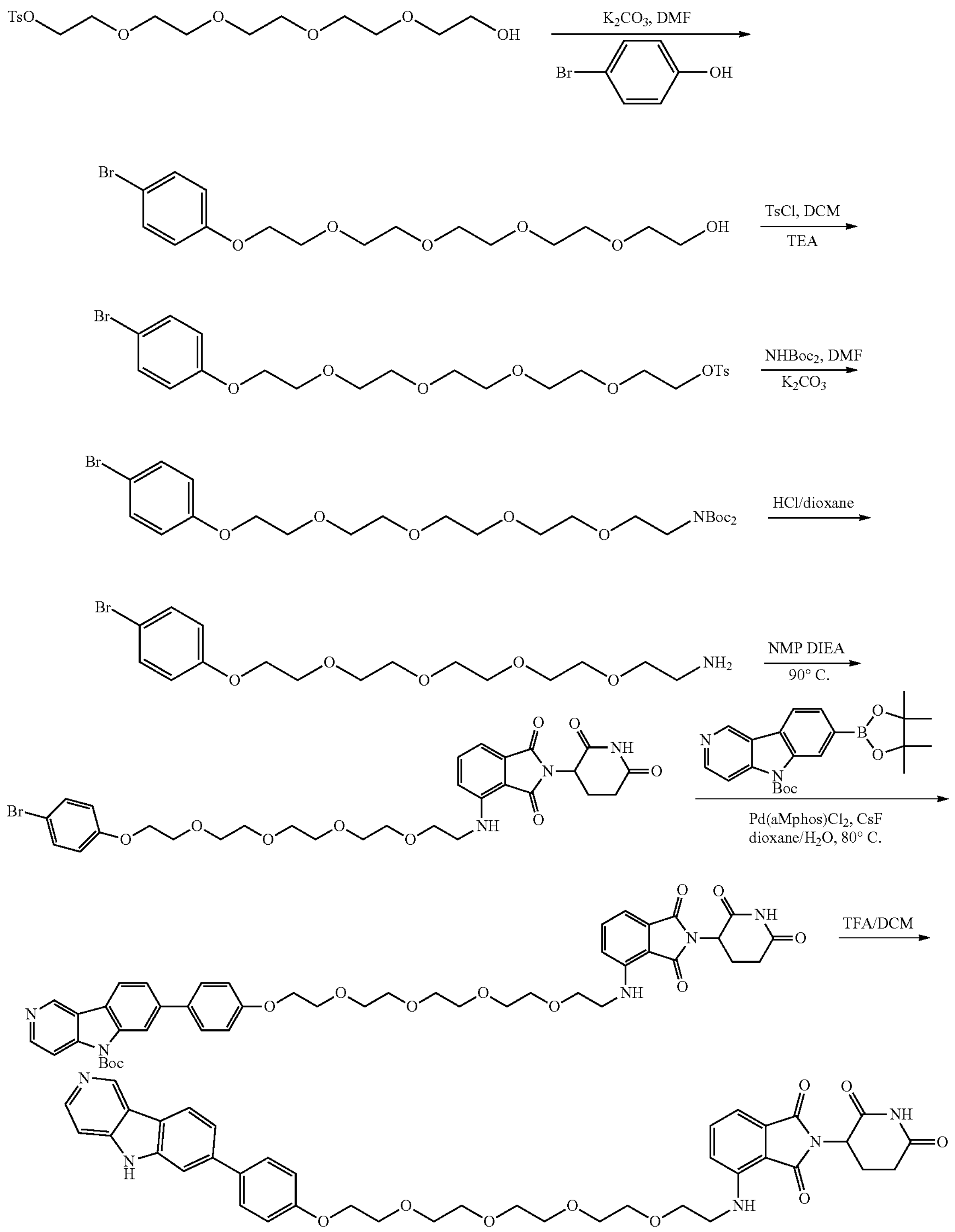
Compound 86
Compound 86: $^1$H NMR (400 MHz, $CDCl_3$): δ 9.28 (s, 2H), 8.50 (s, 1H), 8.08 (s, 1H), 7.35-7.57 (m, 6H), 6.94-6.96 (m, 3H), 6.77 (s, 1H), 6.38 (s, 1H), 4.88-4.90 (m, 1H), 4.14 (s, 2H), 3.60-3.86 (m, 17H), 3.31-3.34 (m, 2H), 2.66-2.86 (m, 3H), 2.03-2.05 (m, 1H). $(M+H)^+$ 736.5.

Synthetic Schedule for Exemplary Compound 87

6-((14-((5-(5H-pyrido[4,3-b]indol-7-yl)pyridin-2-yl)oxy)-3,6,9,12-tetraoxatetradecyl)oxy)-2-(2,6-dioxopiperidin-3-yl)-1H-pyrrolo[3,4-c]pyridine-1,3(2H)-dione

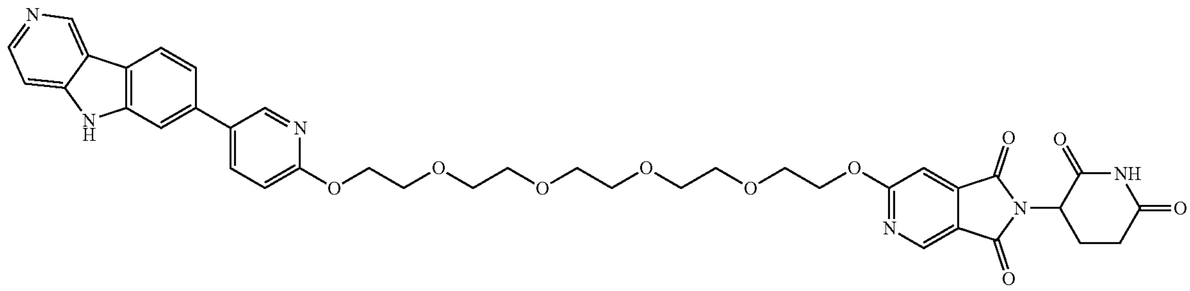 [SMILES: O=C1CCC(N2C(=O)c3cnc(OCCOCCOCCOCCOCCOc4ccc(-c5ccc6c(c5)[nH]c5ccncc56)cn4)cc3C2=O)C(=O)N1]

Step 1: 6-((14-((5-(5H-pyrido[4,3-b]indol-7-yl)pyridin-2-yl)oxy)-3,6,9,12-tetraoxatetradecyl)oxy)pyridine-3,4-dicarboxylic acid

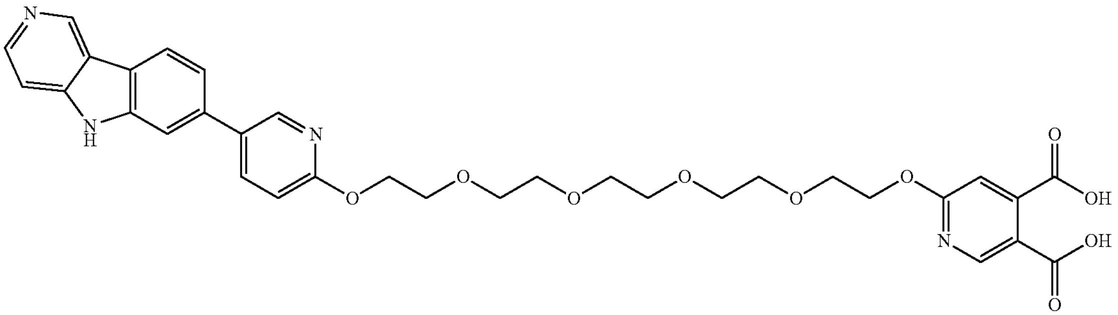 [SMILES: O=C(O)c1cnc(OCCOCCOCCOCCOCCOc2ccc(-c3ccc4c(c3)[nH]c3ccncc34)cn2)cc1C(=O)O]

To a solution of 14-((5-(5H-pyrido[4,3-b]indol-7-yl)pyridin-2-yl)oxy)-3,6,9,12-tetraoxatetradecan-1-ol (200.0 mg, 0.42 mmol) and 6-chloropyridine-3,4-dicarboxylic acid (166 mg, 0.83 mmol) in anhydrous tetrahydrofuran (4 mL) was added sodium hydride (162.0 mg, 4.2 mmol). The resulting solution was stirred at 100° C. with MW for 2 hour under $N_2$ atmosphere. The solution was cooled to room temperature and quenched with water (20 mL). The mixture was extracted with ethyl acetate (20 mL×3). The combined organic layers were washed with brine (20 mL×2). The organic layer was dried over anhydrous sodium sulfate, filtered and concentrated under vacuum. The residue was purified by silica gel column chromatography to afford the desired compound (50 mg, 0.077 mmol, 9% yield).

Step 2: 6-((14-((5-(5H-pyrido[4,3-b]indol-7-yl)pyridin-2-yl)oxy)-3,6,9,12-tetraoxatetradecyl)oxy)-2-(2,6-dioxopiperidin-3-yl)-1H-pyrrolo[3,4-c]pyridine-1,3(2H)-dione

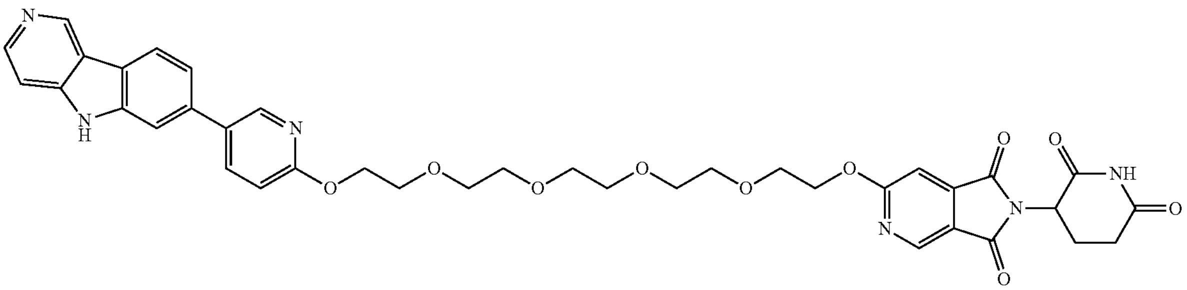 [SMILES: O=C1CCC(N2C(=O)c3cnc(OCCOCCOCCOCCOCCOc4ccc(-c5ccc6c(c5)[nH]c5ccncc56)cn4)cc3C2=O)C(=O)N1]

To a solution of 6-((14-((5-(5H-pyrido[4,3-b]indol-7-yl)pyridin-2-yl)oxy)-3,6,9,12-tetraoxatetradecyl)oxy)pyridine-3,4-dicarboxylic acid (50 mg, 0.077 mmol) and 3-aminopiperidine-2,6-dione (12 mg, 0.092 mmol) in AcOH (6 mL) was added NaOAc (6 mg, 0.092 mmol). The resulting solution was stirred at 120° C. for 16 hours. After cooling to room temperature, the reaction was quenched by the addition of water (20 mL). The mixture was extracted with EA (20 mL×3). The combined organic layers were washed with brine (20 mL×2), dried over anhydrous sodium sulfate and concentrated under vacuum. The residue was purified by prep-TLC with DCM/$CH_3OH$ (10:1) to afford the title compound (4.0 mg, 0.005 mmol, 7% yield).

Compound 87: $^1H$ NMR (400 MHz, $CDCl_3$): δ 9.28 (s, 1H), 8.42 (s, 1H), 8.37-8.39 (m, 2H), 8.06 (d, J=8.0 Hz, 1H), 7.80 (d, J=8.0 Hz, 1H), 7.62 (s, 1H), 7.40-7.45 (m, 3H), 6.09 (s, 1H), 6.82 (d, J=8.8 Hz, 1H), 4.94-4.99 (m, 1H), 4.54 (t, J=4.8 Hz, 4H), 3.86-3.91 (m, 4H), 3.66-3.75 (m, 12H), 2.73-2.92 (m, 3H), 2.20-2.22 (m, 1H). $(M+H)^+$ 739.5.

Synthetic Scheme for Exemplary Compound 88

2-(2,6-dioxopiperidin-3-yl)-5-((14-((5-(5-(2,2,2-trifluoroethyl)-5H-pyrido[4,3-b]indol-7-yl)pyridin-2-yl)oxy)-3,6,9,12-tetraoxatetradecyl)oxy)isoindoline-1,3-dione

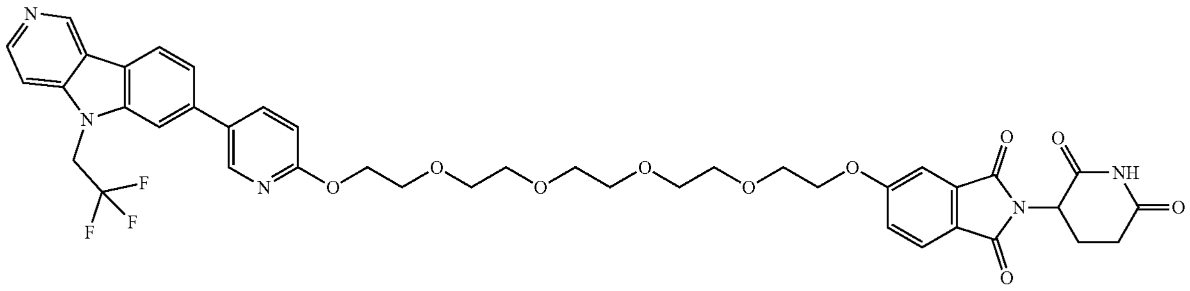 [SMILES: O=C1CCC(N2C(=O)c3ccc(OCCOCCOCCOCCOCCOc4ccc(-c5ccc6c7cnccc7n(CC(F)(F)F)c6c5)cn4)cc3C2=O)C(=O)N1]

Prepared according to the synthetic scheme below using procedures described above and common procedures to those skilled in the art.

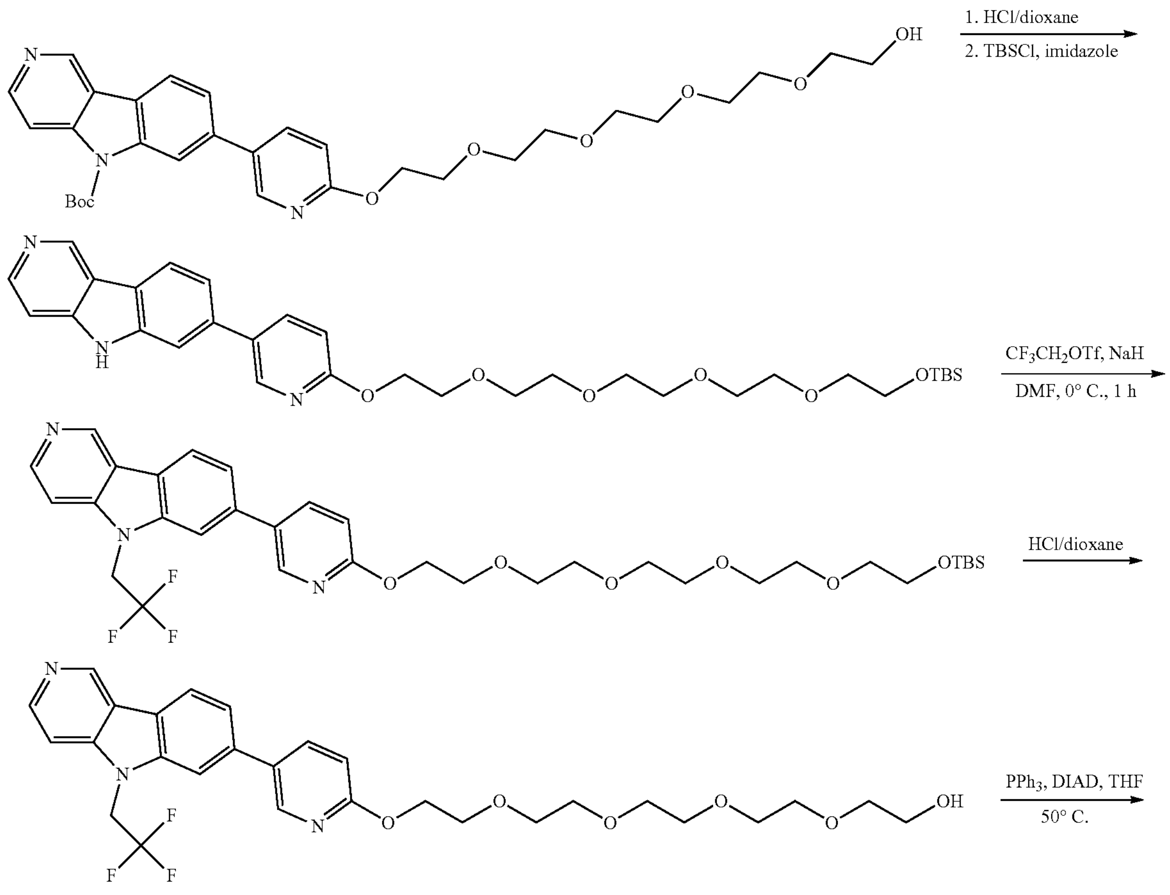

-continued

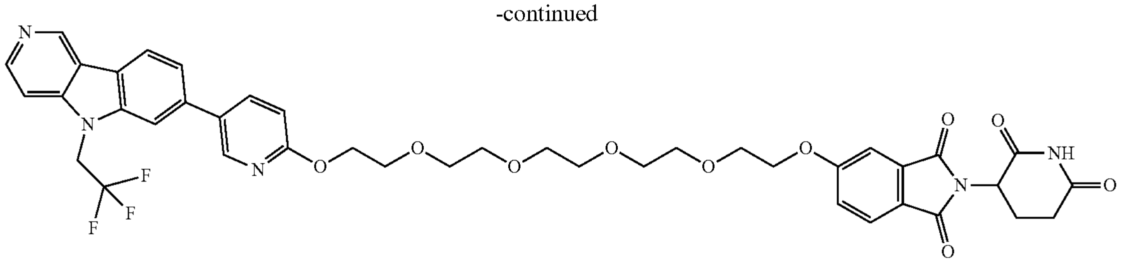

Compound 88

Compound 88: $^1$H NMR (400 MHz, $CDCl_3$): δ 9.35 (s, 1H), 8.63 (d, J=7.6 Hz, 1H), 8.45 (s, 1H), 8.21 (d, J=8.0 Hz, 1H), 8.16 (s, 1H), 7.87-7.90 (m, 1H), 7.75 (d, J=8.4 Hz, 1H), 7.53-7.58 (m, 2H), 7.39 (s, 1H), 7.35 (s, 1H), 7.21 (d, J=8.4 Hz, 1H), 6.91 (d, J=8.8 Hz, 1H), 4.87-4.92 (m, 3H), 4.55 (t, J=4.8 Hz, 2H), 4.24 (t, J=4.8 Hz, 2H), 3.90 (t, J=4.4 Hz, 3H), 3.66-3.73 (m, 12H), 2.76-2.87 (m, 3H), 2.09-2.16 (m, 1H). $(M+H)^+$ 820.5

Synthetic Scheme for Exemplary Compound 89

2-(2,6-dioxopiperidin-3-yl)-5-(4-(3,3,3-trifluoro-2-(2-((5-((5-(5-methyl-5H-pyrido[4,3-b]indol-7-yl)pyridin-2-yl)oxy)pentyl)oxy)ethoxy)propyl)piperidin-1-yl)isoindoline-1-dione

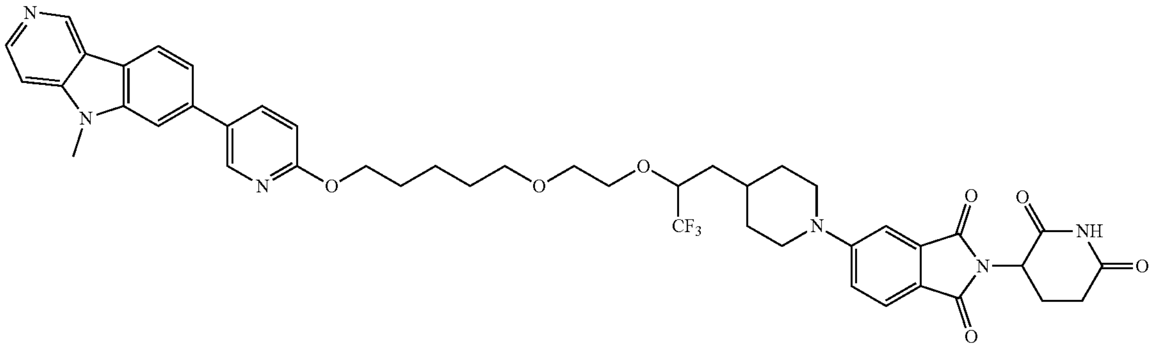 [SMILES: Cn1c2ccncc2c2ccc(-c3ccc(OCCCCCOCCOC(CC4CCN(c5ccc6c(c5)C(=O)N(C5CCC(=O)NC5=O)C6=O)CC4)C(F)(F)F)nc3)cc21]

Step: 2-(5-benzyloxypentoxy)acetate

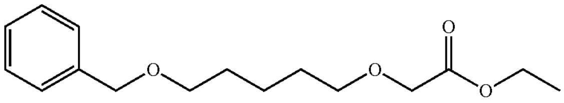 [SMILES: CCOC(=O)COCCCCCOCc1ccccc1]

To a solution of 5-benzyloxypentan-1-ol (1 g, 5.15 mmol, 1.0 eq) in dichloromethane (20 mL) was added ethyl 2-diazoacetate (704 mg, 6.18 mmol, 1.2 eq) and dirhodium tetraacetate (11 mg, 0.03 mmol). Then the mixture was stirred at 20° C. for 0.5 hour. The mixture was quenched with ethyl alcohol (10 mL) and then concentrated. The residue was purified by silica column chromatography (petroleum ether; ethyl acetate=50:1 to 4:1) to afford ethyl 2-(5-benzyloxypentoxy)acetate (700 mg, 2.50 mmol, 49% yield) as a yellow oil.

Step 2: 2-(5-benzyloxypentoxy)ethanol

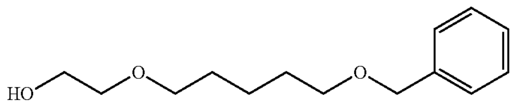 [SMILES: OCCOCCCCCOCc1ccccc1]

To a mixture of $LiAlH_4$ (189 mg, 4.99 mmol, 2.0 eq) in tetrahydrofuran (4 mL) was added a solution of ethyl 2-(5-benzyloxypentoxy)acetate (700 mg, 2.50 mmol, 1.0 eq) in tetrahydrofuran (10 mL) at 0° C. Then the mixture was stirred at 20° C. for 2 hours. The mixture was quenched with water (0.2 mL), aqueous sodium hydroxide (1 M, 0.2 mL), and more water (0.8 mL). Then filtered and concentrated. The residue was purified by silica column chromatography (petroleum ether:ethyl acetate=30:1 to 10:1) to afford 2-(5-benzyloxypentoxy)ethanol (400 mg, 1.68 mmol, 67% yield) was obtained as a white oil.

Step 3: 2-(5-benzyloxypentoxy)ethyl4-methylbenzenesulfonate

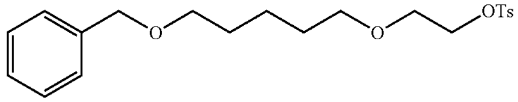 [SMILES: Cc1ccc(S(=O)(=O)OCCOCCCCCOCc2ccccc2)cc1]

To a mixture of 2-(5-benzyloxypentoxy)ethanol (400 mg, 1.68 mmol, 1.0 eq) and toluene sulfonyl chloride (640 mg, 3.36 mmol, 2.0 eq) in tetrahydrofuran (3 mL) was added potassium hydroxide (2.83 g, 50.35 mmol, 30.0 eq). Then the mixture was stirred at 20° C. for 0.5 hour. The mixture was diluted with water (10 mL), extracted with ethyl acetate (20 mL), washed with brine (20 mL), dried over anhydrous sodium sulfate and then concentrated. The mixture was purified by silica column chromatography (petroleum ether: ethyl acetate=30:1 to 10:1) to afford 2-(5-benzyloxypentoxy)ethyl4-methylbenzenesulfonate (570 mg, 1.45 mmol, 86% yield) as a white oil.

Step 4: tert-butyl 4-(3,3,3-trifluoro-2-hydroxy-propyl) piperidine-1-carboxylate

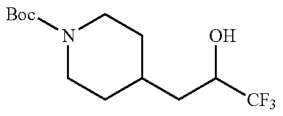

To a mixture of tert-butyl 4-(2-oxoethyl)piperidine-1-carboxylate (1.9 g, 8.36 mmol, 1.0 eq) and trimethyl(trifluoromethyl)silane (1.43 g, 10.03 mmol, 1.2 eq) in tetrahydrofuran (20 mL) was added tetrabutylammonium fluoride (1 M, 0.1 mL) at 0° C. Then the mixture was stirred at 20° C. for 1 hour. Then aqueous hydrochloric acid (1 M, 17 mL, 2.0 eq) was added into the mixture and stirred at 20° C. for additional 2 hours. The mixture was extracted with dichloromethane (100 mL), washed with brine (50 mL), dried over anhydrous sodium sulfate and then concentrated. The residue was purified by silica column chromatography (petroleum ether:ethyl acetate=100:1 to 10:1) to afford tert-butyl 4-(3,3,3-trifluoro-2-hydroxy-propyl) piperidine-1-carboxylate (2.0 g, 6.73 mmol, 80% yield) as a white solid.

Step 5: tert-butyl4-[2-[2-(5-benzyloxypentoxy) ethoxy]-3,3,3-trifluoro-propyl]piperidine-1-carboxylate

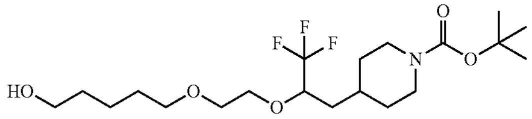 [SMILES: CC(C)(C)OC(=O)N1CCC(CC(OCCOCCCCCO)C(F)(F)F)CC1]

To a solution of tert-butyl 4-(3,3,3-trifluoro-2-hydroxy-propyl)piperidine-1-carboxylate (216 mg, 0.73 mmol, 1.0 eq) in dimethyl formamide (2 mL) was added sodium hydride (58 mg, 1.46 mmol, 60% in mineral oil, 2.0 eq) at 15° C. Then the mixture was stirred at 15° C. for 0.5 hour under nitrogen. 2-(5-benzyloxypentoxy)ethyl 4-methylbenzenesulfonate (200 mg, 0.51 mmol, 0.7 eq) was added into the mixture and stirred at 50° C. for additional 2.5 hours. The mixture was quenched with water (5 mL), extracted with ethyl acetate (20 mL×2), washed with brine (20 mL), dried over anhydrous sodium sulfate and then concentrated. The mixture was purified by silica column chromatography (petroleum ether:ethyl acetate=200:1 to 10:1) to afford tert-butyl4-[2-[2-(5-benzyloxypentoxy)ethoxy]-3,3,3-trifluoro-propyl]piperidine-1-carboxylate (300 mg, 0.58 mmol, 80% yield) as a white oil.

Tert-butyl4-[2-[2-(5-benzyloxypentoxy)ethoxy]-3,3,3-trifluoro-propyl]piperidine-1-carboxylate was converted to the title compound, 2-(2,6-dioxopiperidin-3-yl)-5-(4-(3,3,3-trifluoro-2-(2-((5-((5-(5-methyl-5H-pyrido[4,3-b]indol-7-yl) pyridin-2-yl)oxy)pentyl)oxy)ethoxy)propyl)piperidin-1-yl) isoindoline-1,3-dione, according to the synthetic scheme below using procedures described above and common procedures known to those skilled in the art.

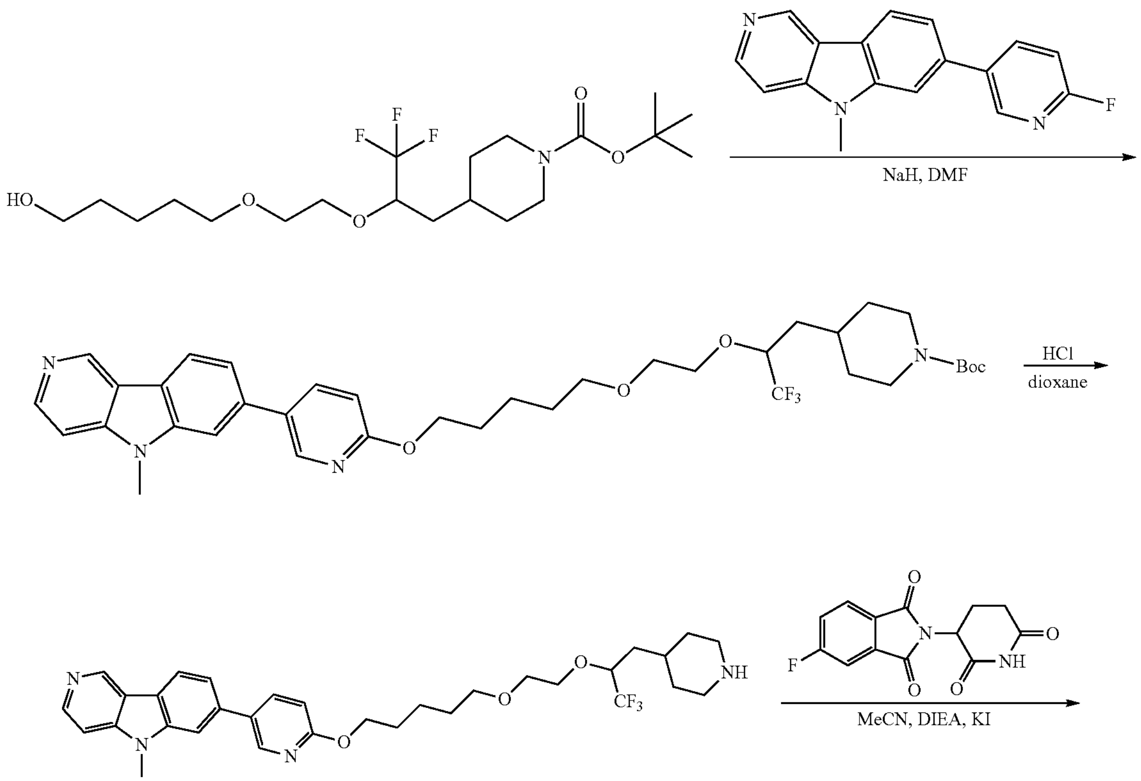

-continued

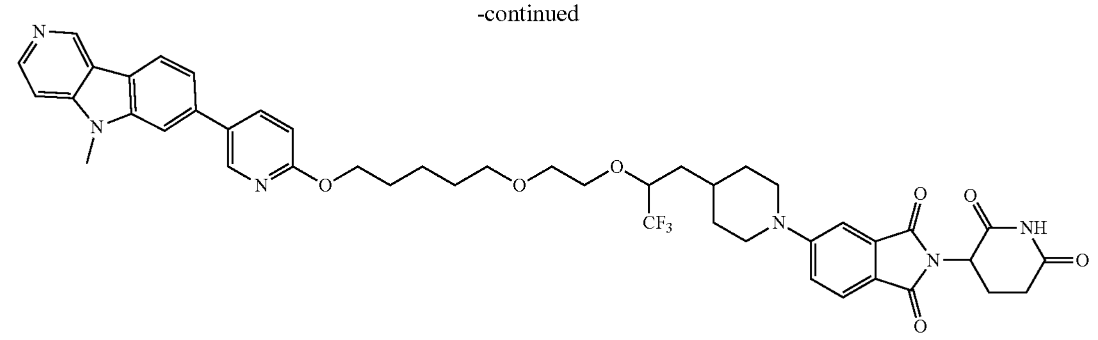

Compound 89

Compound 89: $^{1}H$ NMR (400 MHz, DMSO-$d_6$) δ: 11.09 (s, 1H), 9.36 (s, 1H), 8.61 (d, J=2.4 Hz, 1H), 8.50 (d, J=5.6 Hz, 1H), 8.31 (d, J=8.0 Hz, 1H), 8.21 (s, 1H), 8.15 (dd, J=2.8, 8.8 Hz, 1H), 7.95 (s, 1H), 7.65-7.57 (m, 3H), 7.29 (s, 1H), 7.23-7.18 (m, 1H), 6.90 (d, J=8.8 Hz, 1H), 5.04 (dd, J=5.6, 12.8 Hz, 1H), 4.31 (t, J=6.4 Hz, 2H), 4.14 (br s, 1H), 4.10-3.99 (m, 3H), 3.96 (s, 3H), 3.87 (d, J=11.6 Hz, 2H), 3.74 (dd, J=5.6, 10.8 Hz, 2H), 3.02-2.81 (m, 4H), 1.98-1.86 (m, 2H), 1.85-1.72 (m, 4H), 1.63-1.15 (m, 9H). $(M+H)^+$ 841.6.

Synthetic Scheme for Exemplary Compound 90

2-(2,6-dioxopiperidin-3-yl)-5-(4-(4-((4-((5-(5-methyl-5H-pyrido[4,3-b]indol-7-yl)pyridin-2-yl)oxy)but-2-yn-1-yl)oxy)butoxy)butoxy)isoindoline-1,3-dione

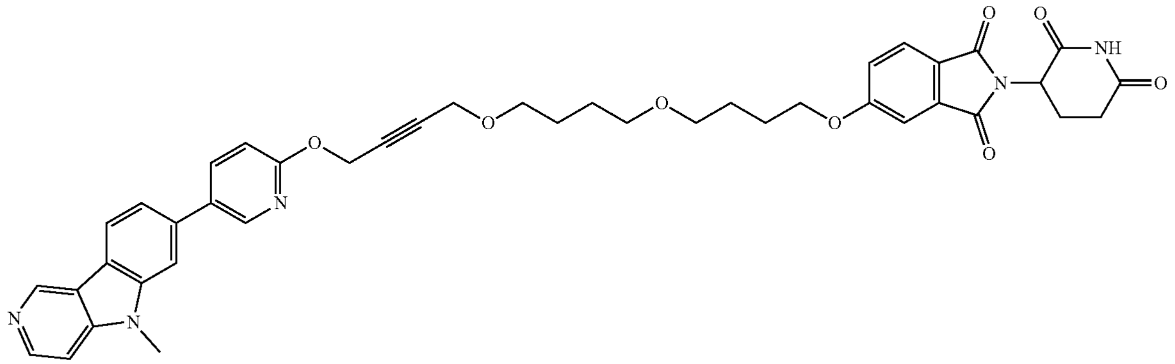 [SMILES: Cn1c2ccncc2c2ccc(-c3ccc(OCC#CCOCCCCOCCCCOc4ccc5c(c4)C(=O)N(C4CCC(=O)NC4=O)C5=O)nc3)cc21]

Prepared according to the synthetic scheme below using procedures described above and common procedures to those skilled in the art.

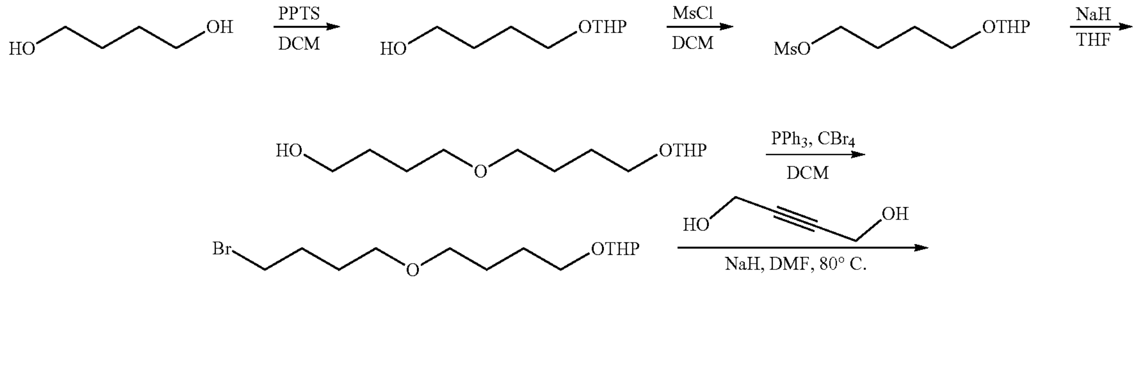

-continued
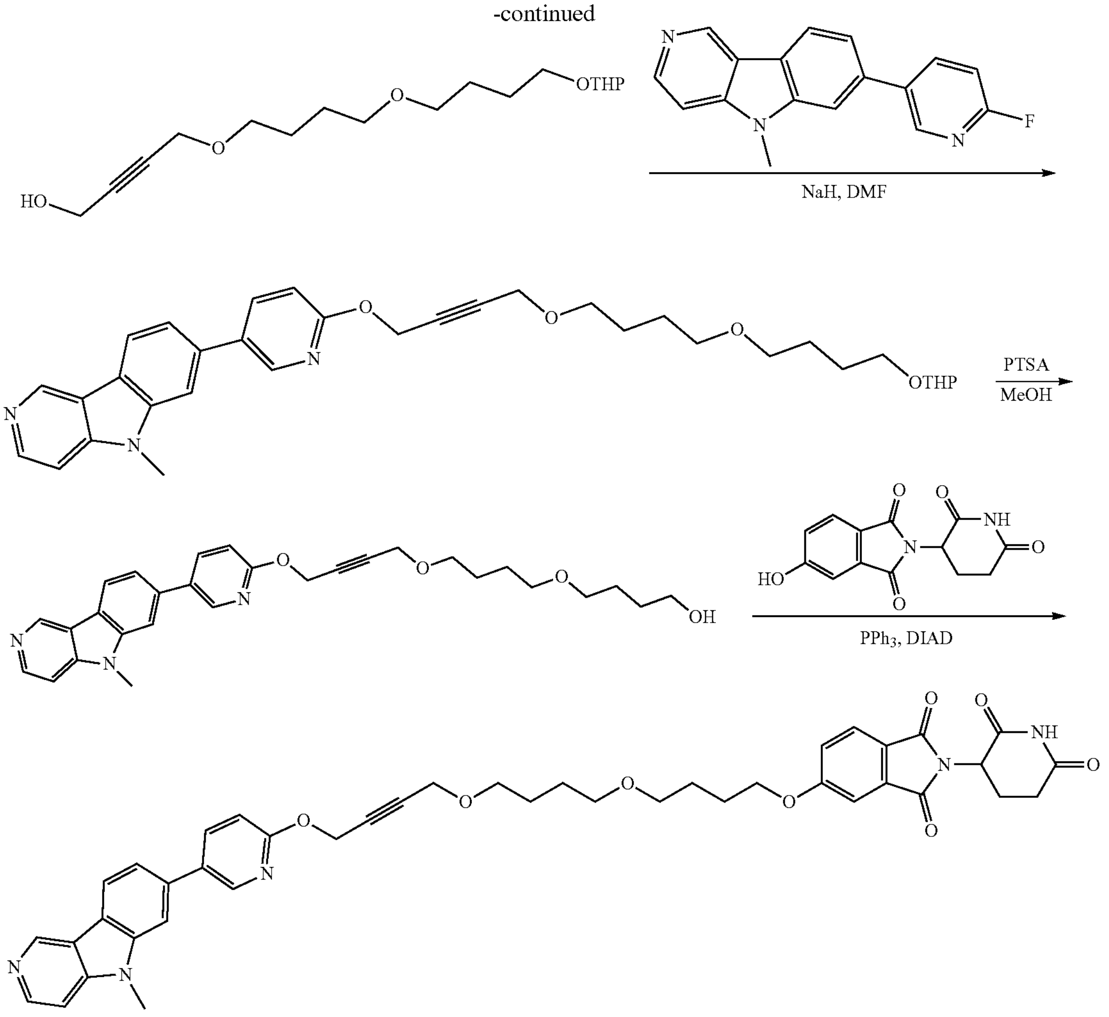
Compound 90
Compound 90: $^1$HNMR (400 MHz, $CDCl_3$): δ 9.35 (s, 1H), 8.60 (s, 1H), 8.50 (s, 1H), 8.20 (d, J=8.0 Hz, 2H), 7.75 (d, J=8.0 Hz, 1H), 7.55 (s, 1H), 7.49 (d, J=8.0 Hz, 1H), 7.32 (d, J=10.0 Hz, 2H), 7.16 (d, J=8.0 Hz, 1H), 6.92 (d, J=8.4 Hz, 1H), 5.10 (s, 2H), 4.98-5.00 (m, 1H), 4.21 (s, 2H), 4.07-4.10 (m, 2H), 3.90 (s, 3H), 3.44-3.54 (m, 7H), 2.76-2.87 (m, 3H), 2.18-2.23 (m, 2H), 1.88-1.92 (m, 3H), 1.72-1.75 (m, 4H). M+H)$^+$ 744.5.
Synthetic Scheme for Exemplary Compound 91
2-(2,6-dioxopiperidin-3-yl)-5-(4-(8-((1r,3r)-3-((5-(5-methyl-5H-pyrido[4,3-b]indol-7-yl)pyridin-2-yl)oxy)cyclobutoxy)octyl)piperazin-1-yl)isoindoline-1,3-dione
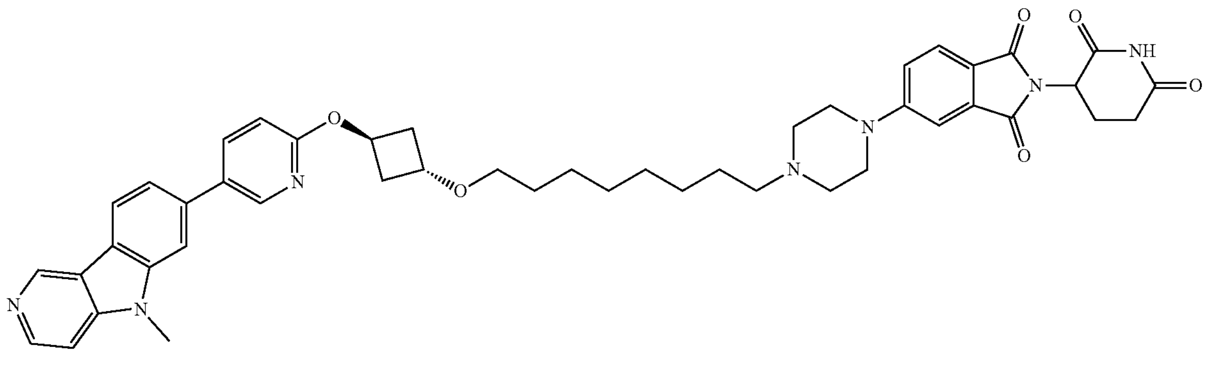 [SMILES: Cn1c2ccncc2c2ccc(-c3ccc(O[C@H]4C[C@H](OCCCCCCCCN5CCN(c6ccc7c(c6)C(=O)N(C6CCC(=O)NC6=O)C7=O)CC5)C4)nc3)cc21]

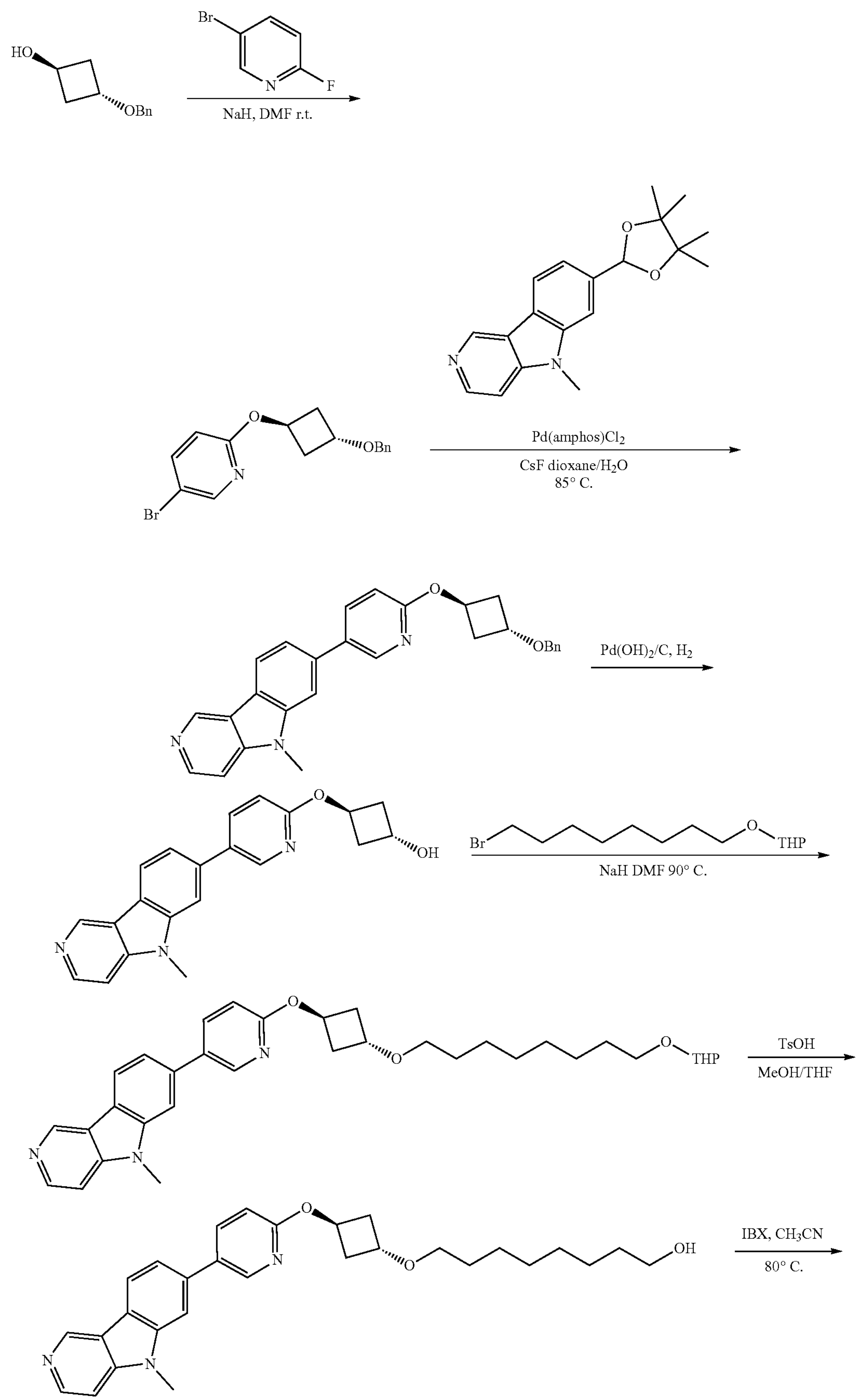
NaH, DMF r.t.
Pd(amphos)Cl2
CsF dioxane/H2O
85° C.
Pd(OH)2/C, H2
NaH DMF 90° C.
TsOH
MeOH/THF
IBX, CH3CN
80° C.

-continued

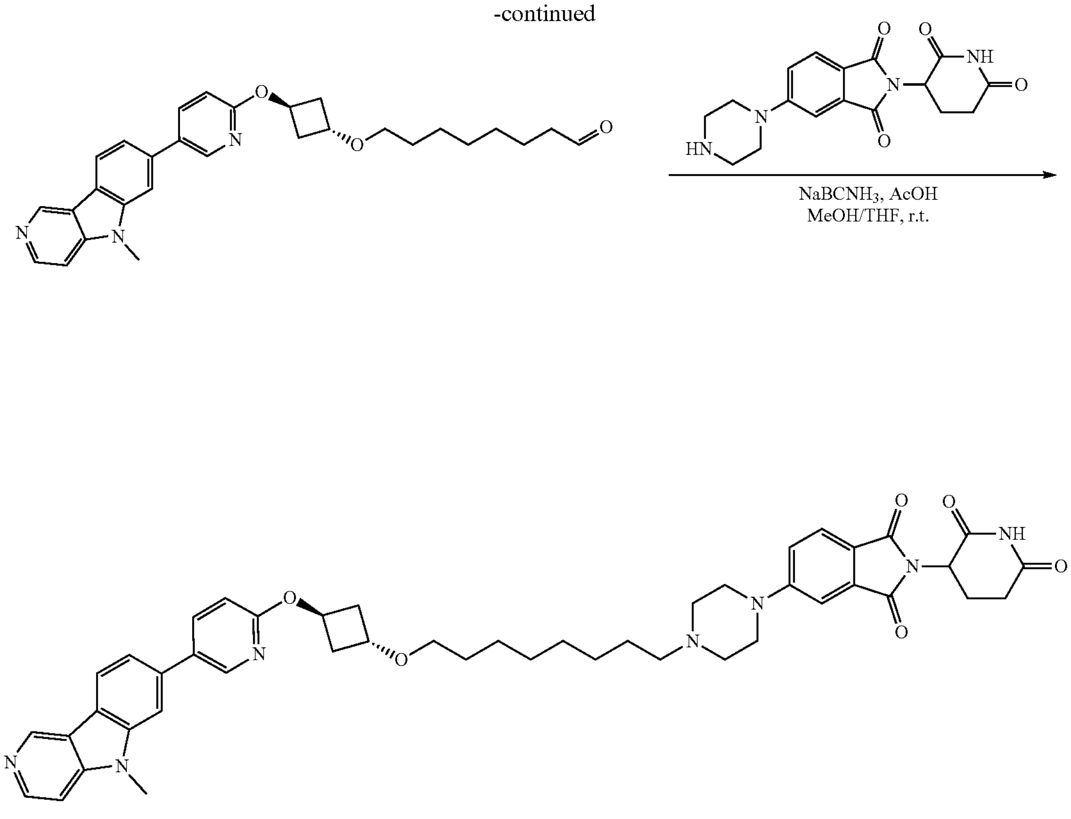

Compound 91

Compound 91: $^{1}H$ NMR (400 MHz, $CD_3OD$): δ 9.33 (s, 1H), 8.51-8.53 (m, 2H), 8.33-8.34 (m, 1H), 8.09-8.11 (m, 1H), 7.84 (s, 1H), 7.59-7.62 (m, 3H), 7.30 (s, 1H), 7.17 (d, J=8.4 Hz, 1H), 6.90 (d, J=8.4 Hz, 1H), 5.32-5.35 (m, 1H), 3.99 (s, 3H), 3.40-3.47 (m, 13H), 2.69-2.71 (m, 6H), 2.50-2.52 (m, 4H), 2.03-2.18 (m, 5H), 1.59-1.60 (m, 6H). $(M+H)^+$ 798.6.

Synthetic Scheme for Exemplary Compound 92

5-((14-((3-chloro-5-(5-methyl-5H-pyrido[4,3-b]indol-7-yl)pyridin-2-yl)oxy)-3,6,9,12-tetraoxatetradecyl)oxy)-2-(2,6-dioxopiperidin-3-yl)isoindoline-1,3-dione

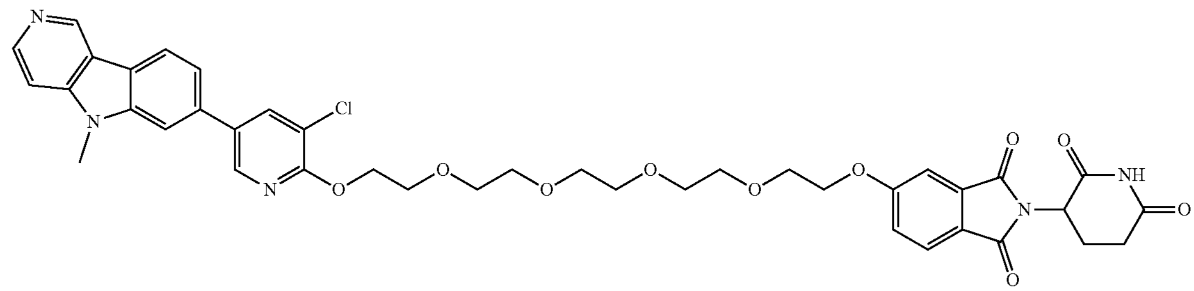 [SMILES: Cn1c2ccncc2c2ccc(-c3cnc(OCCOCCOCCOCCOCCOc4ccc5c(c4)C(=O)N(C4CCC(=O)NC4=O)C5=O)c(Cl)c3)cc21]

Prepared according to the synthetic scheme below using procedures described above and common procedures known to those skilled in the art.

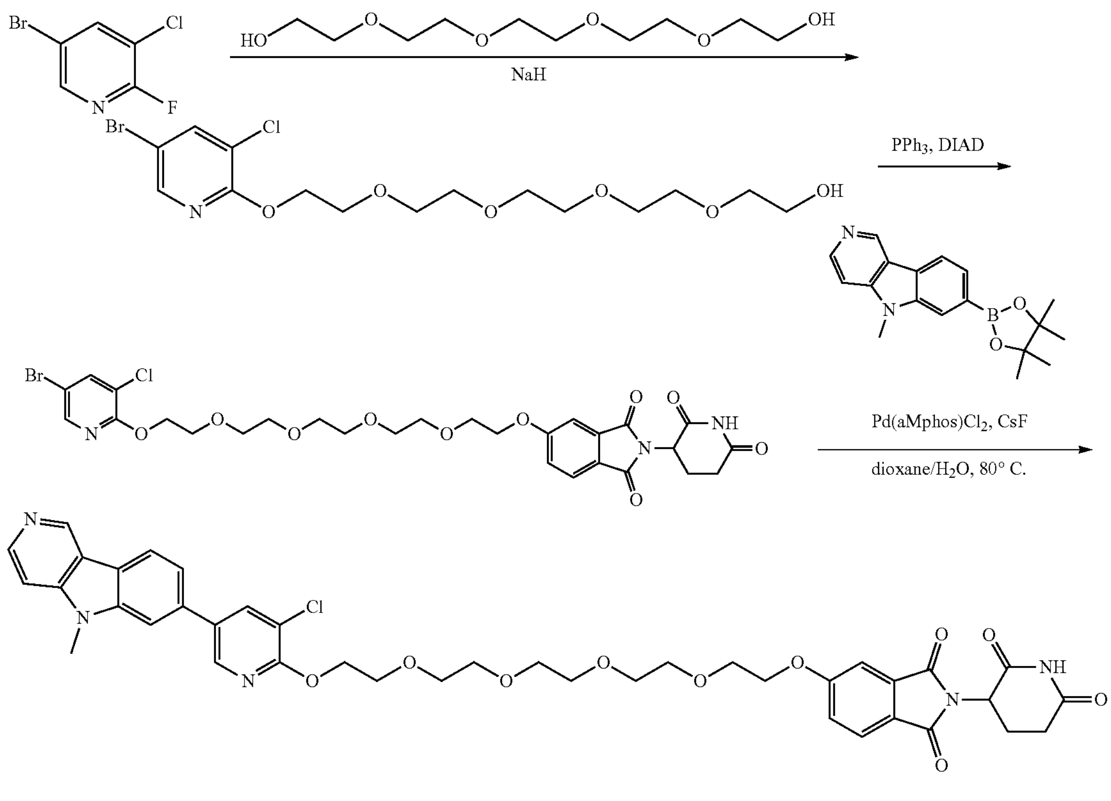

Compound 92

Compound 92: $^1$H NMR (400 MHz, $CDCl_3$): δ 9.32 (s, 1H), 8.68 (s, 1H), 8.58 (s, 1H), 8.35 (s, 1H), 8.18 (d, J=8.0 Hz, 1H), 7.97 (s, 1H), 7.74 (d, J=8.4 Hz, 1H), 7.52 (s, 1H), 7.45 (d, J=8.0 Hz, 1H), 7.27-7.34 (m, 2H), 7.20 (d, J=7.6 Hz, 1H), 4.92-4.96 (m, 1H), 4.61 (s, 2H), 4.23 (s, 2H), 3.89-3.94 (m, 8H), 3.68-3.78 (m, 1H), 2.72-2.90 (m, 3H), 2.01-2.12 (m, 1H). $(M+H)^+$ 786.5, 788.5.

Synthetic Scheme for Exemplary Compound 93

5-((6-((5-(2,2-difluoro-2-(5-(5-methyl-5H-pyrido[4,3-b]indol-7-yl)pyridin-2-yl)ethoxy)pentyl)oxy)hexyl)oxy)-2-(2,6-dioxopiperidin-3-yl)isoindoline-1,3-dione

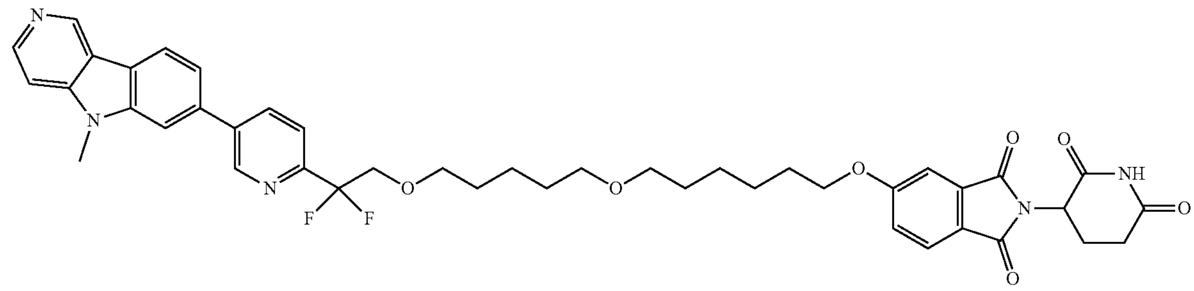 [SMILES: Cn1c2ccncc2c2ccc(-c3ccc(C(F)(F)COCCCCCOCCCCCCOc4ccc5c(c4)C(=O)N(C4CCC(=O)NC4=O)C5=O)nc3)cc21]

Prepared according to the synthetic scheme below using procedures described above and common procedures known to those skilled in the art.

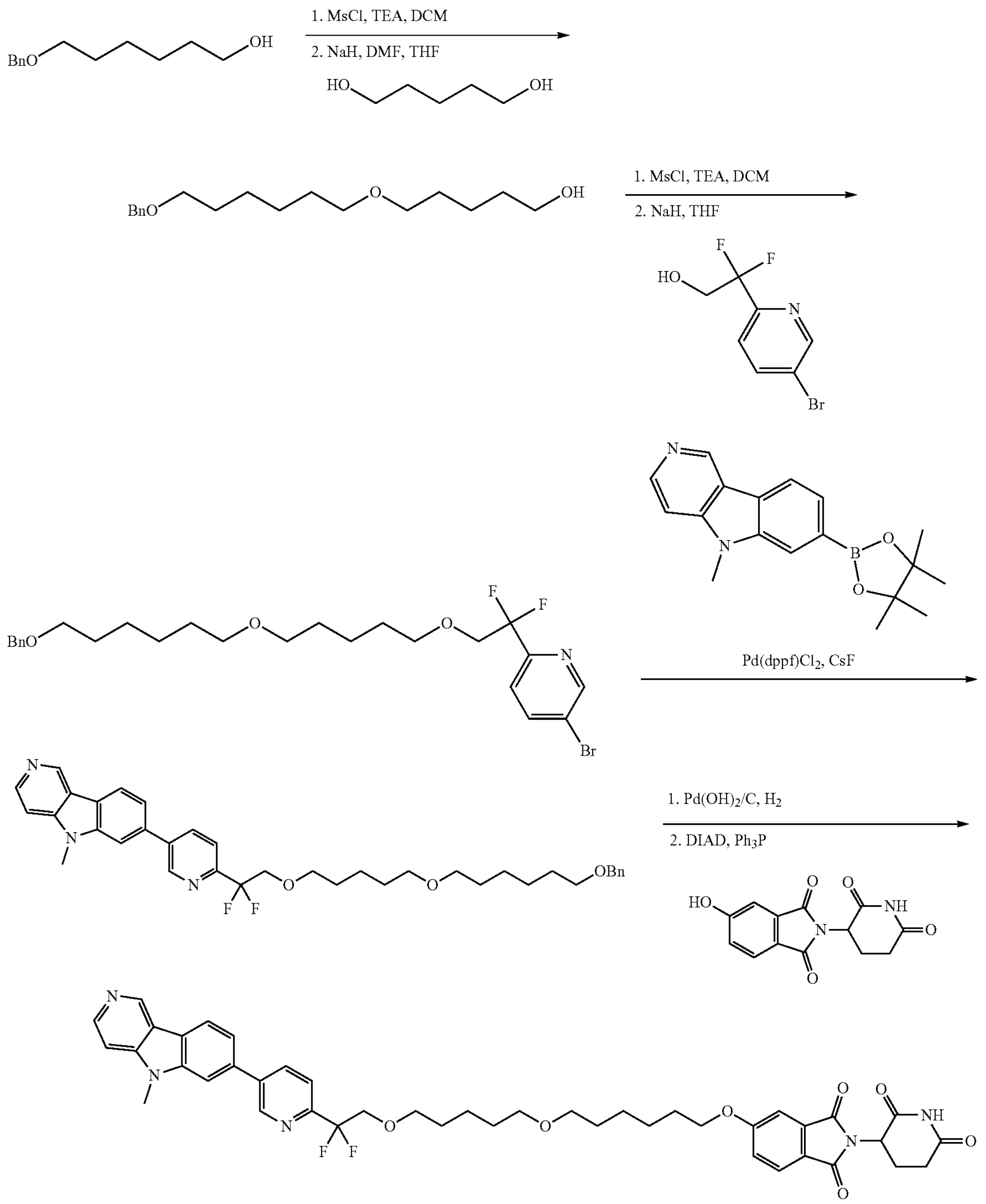
Compound 93
Compound 93: $^1$H NMR (400 MHz, $CDCl_3$): δ 9.35 (br, 1H), 8.94 (s, 1H), 8.59 (s, 1H), 8.21 (d, J=8.0 Hz, 1H), 8.01-8.09 (m, 2H), 7.73 (d, J=8.4 Hz, 1H), 7.69 (d, J=8.0 Hz, 1H), 7.58 (s, 1H), 7.51 (d, J=8.4 Hz, 1H), 7.31 (d, J=5.2 Hz, 1H), 7.24 (s, 1H), 7.09 (dd, J=8.0, 2.0 Hz, 1H), 4.85-4.90 (m, 1H), 4.10 (t, J=8.0 Hz, 1H), 3.98 (t, J=6.4 Hz, 1H), 3.87 (s, 3H), 3.51 (t, J=6.4 Hz, 1H), 3.27-3.32 (m, 4H), 2.65-2.85 (m, 3H), 2.04-2.08 (m, 1H), 1.71-1.76 (m, 4H), 1.45-1.52 (m, 8H), 0.75-0.85 (m, 4H). $(M+H)^+$ 782.5.

Synthetic Scheme for Exemplary Compound 96
2-(2,6-dioxopiperidin-3-yl)-5-(4-(6-((1r,3r)-3-((5-(5-methyl-5H-pyrido[4,3-b]indol-7-yl)pyridin-2-yl)oxy)cyclobutoxy)hexyl)-3-(trifluoromethyl)piperazin-1-yl)isoindoline-1,3-dione
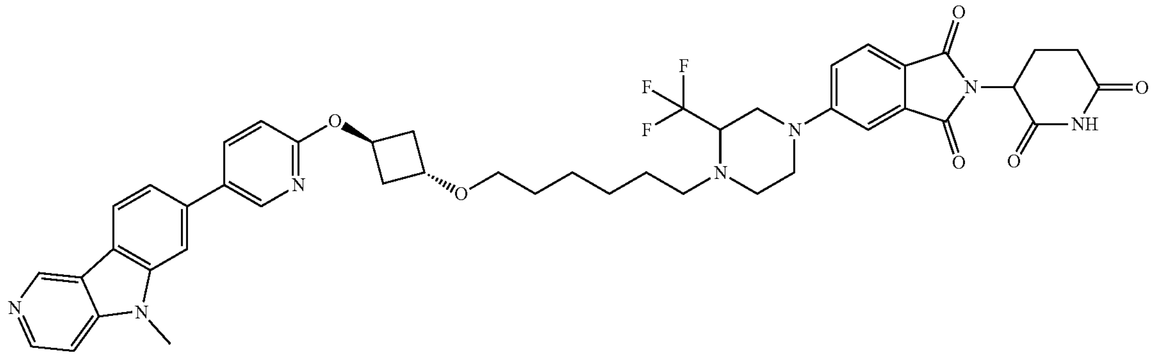 [SMILES: Cn1c2ccncc2c2ccc(-c3ccc(O[C@H]4C[C@H](OCCCCCCN5CCN(c6ccc7c(c6)C(=O)N(C6CCC(=O)NC6=O)C7=O)CC5C(F)(F)F)C4)nc3)cc21]
Prepared according to the synthetic schemes below using procedures described above and common procedures known to those skilled in the art.
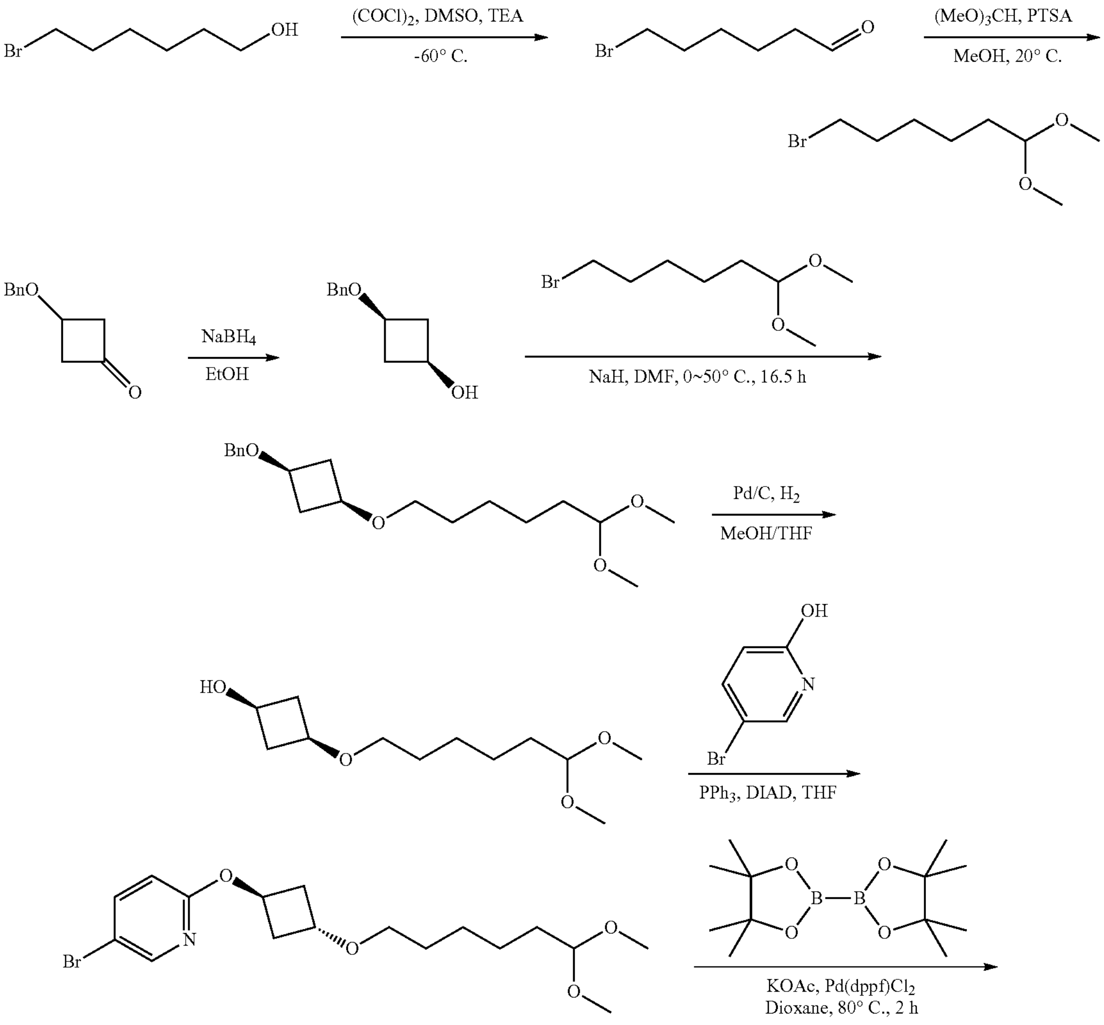

-continued
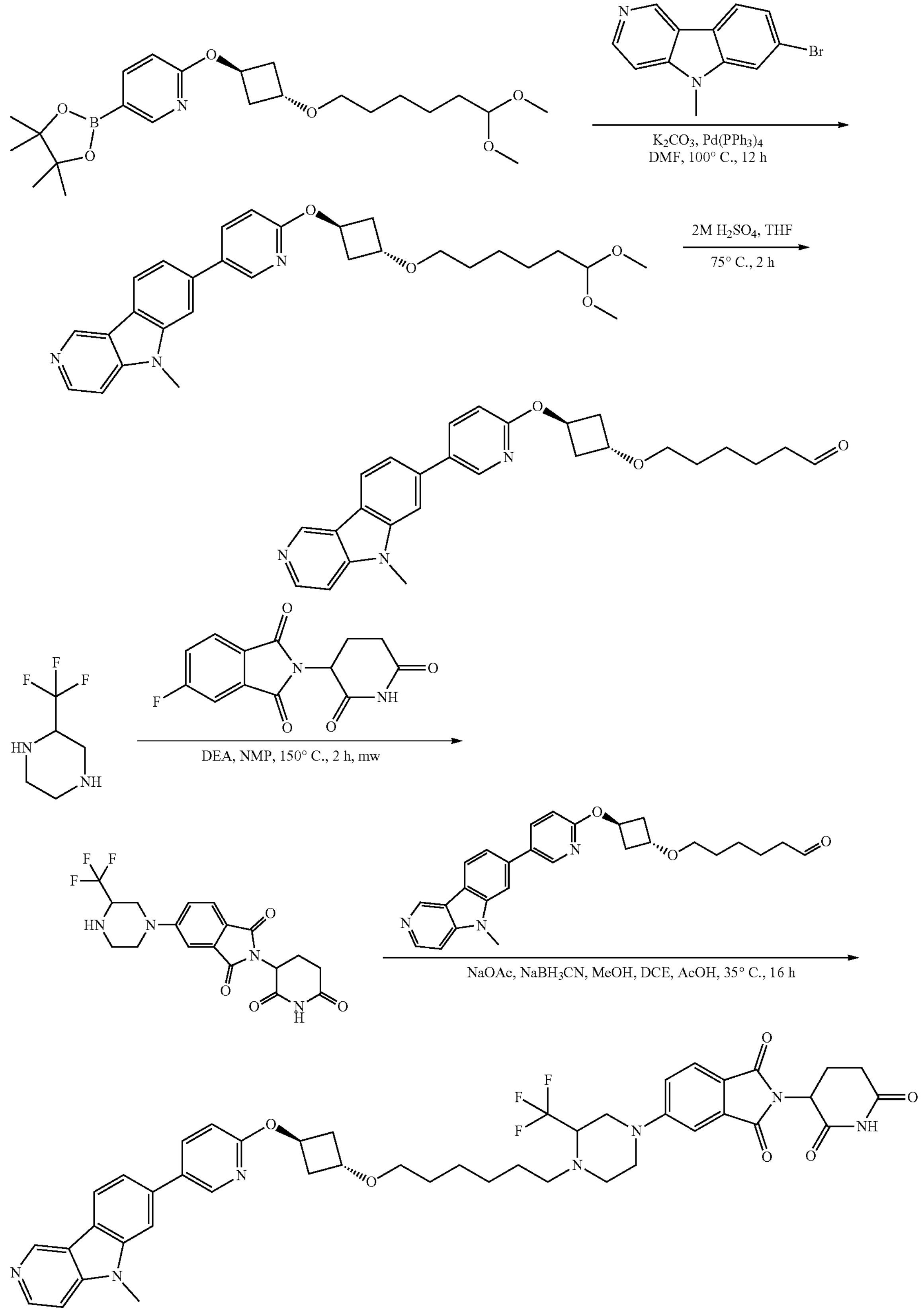
Compound 96

Compound 96: $^1$H NMR: 400 MHz, DMSO-d6 δ: 11.09 (s, 1H), 9.38 (s, 1H), 8.64 (d, J=2.4 Hz, 1H), 8.51 (d, J=5.6 Hz, 1H), 8.33 (d, J=8.0 Hz, 1H), 8.19 (dd, J=2.4, 8.8 Hz, 1H), 8.14 (s, 1H), 7.99 (s, 1H), 7.72-7.59 (m, 3H), 7.21 (d, J=2.0 Hz, 1H), 7.12 (dd, J=2.0, 8.8 Hz, 1H), 6.94 (d, J=8.4 Hz, 1H), 5.38-5.26 (m, 1H), 5.06 (dd, J=5.3, 12.9 Hz, 1H), 4.24-4.13 (m, 1H), 3.96 (s, 3H), 3.95-3.88 (m, 1H), 3.72 (d, J=15.2 Hz, 1H), 3.68-3.63 (m, 1H), 3.53 (d, J=7.2 Hz, 1H), 3.31 (s, 2H), 3.07-2.75 (m, 4H), 2.74-2.54 (m, 4H), 2.44-2.29 (m, 4H), 2.06-1.94 (m, 1H), 1.50 (td, J=7.0, 13.8 Hz, 4H), 1.33 (s, 4H). $(M+H)^+$ 838.6.

Synthetic Scheme for Exemplary Compound 99

2-(2,6-dioxopiperidin-3-yl)-5-((1-(3-(3-((1r,3r)-3-((5-(5-methyl-5H-pyrido[4,3-b]indol-7-yl)pyridin-2-yl)oxy)cyclobutoxy)propoxy)propyl)azetidin-3-yl)oxy)isoindoline-1,3-dione

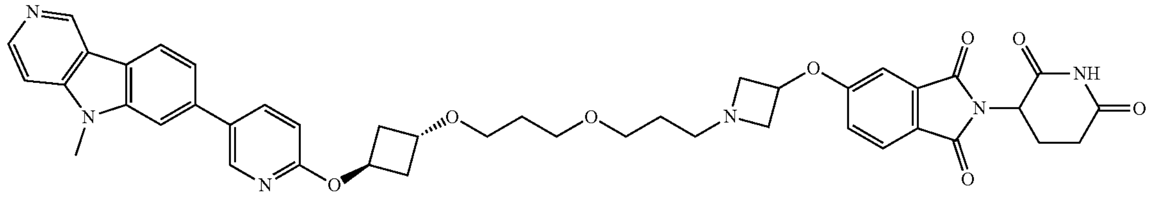 [SMILES: Cn1c2ccncc2c2ccc(-c3ccc(O[C@H]4C[C@H](OCCCOCCCN5CC(Oc6ccc7c(c6)C(=O)N(C6CCC(=O)NC6=O)C7=O)C5)C4)nc3)cc21]

Step 1: 2-(3-bromopropoxy)tetrahydro-2H-pyran

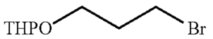

A mixture of 3-bromopropan-1-ol (5.56 g, 40 mmol), dihydropyran (4.0 g, 48 mmol) and p-toluenesulfonic acid (0.76 g, 4 mmol) in tetrahydrofuran (80 ml) was stirred at room temperature overnight. The reaction mixture was quenched with aqueous sodium bicarbonate solution (sat. 10 ml) and extracted with tert-butyl methyl ether (50 ml×3). The combined organic layers were washed with brine (50 ml), dried over anhydrous sodium sulfate, and concentrated under reduced pressure to give a crude residue which was purified by silica gel flash chromatography (eluted 10% ethyl acetate in hexane) to afford 2-(3-bromopropoxy)tetrahydro-2H-pyran (6.4 g, yield 72%) as colorless oil.

Step 2: 3-(3-((tetrahydro-2H-pyran-2-yl)oxy)propoxy propan-1-ol

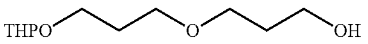

To a solution of propane-1,3-diol (4.6 g, 60 mmol) in N,N-dimethylformamide (50 ml) was added sodium hydride (60% in mineral oil) (0.88 g, 222 mmol) at 0° C., and the resulting mixture was stirred at 0° C. for 30 minutes. To the reaction mixture was added 2-(3-bromopropoxy)tetrahydro-2H-pyran (2.2 g, 20 mmol), and the resulting reaction mixture was stirred at 65° C. for 16 hours. The reaction mixture was quenched with water (150 ml) at 0° C. and extracted with ethyl acetate (200 ml×2). The combined organic layers were washed with brine (50 ml×2), dried over anhydrous sodium sulfate, and concentrated under reduced pressure to give a residue which was purified by silica gel flash chromatography (eluted with 30% ethyl acetate in hexane) to afford 3-(3-((tetrahydro-2H-pyran-2-yl)oxy)propoxy)propan-1-ol (0.9 g, yield 45%) as colorless oil.

Step 3: 3-(3-((tetrahydro-2H-pyran-2-yl)oxy)propoxy)propyl 4-methylbenzenesulfonate

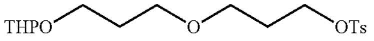

To a stirred solution of 3-(3-((tetrahydro-2H-pyran-2-yl)oxy)propoxy)propan-1-ol (900 mg, 4.1 mmol), triethylamine (1.1 ml, 8.25 mmol) in dichloromethane (30 ml) was added tosyl chloride (0.94 g, 4.95 mmol) and 4-dimethylaminopyridine (50 mg, 0.4 mmol) at 0° C. The resulting solution was allowed to warm up to room temperature and stirred at room temperature for 2 hours. The mixture was poured into water (20 ml) and extracted with dichloromethane (20 ml×2). The combined organic layers were washed with brine (20 ml), dried over anhydrous sodium sulfate, and concentrated under reduced pressure to give a crude residue which was purified by silica gel flash column chromatography (eluted with 10-20% ethyl acetate in hexane) to afford 3-(3-((tetrahydro-2H-pyran-2-yl)oxy)propoxy)propyl 4-methylbenzenesulfonate (1.2 g, yield 78%) as colorless oil.

Step 4: 2-(3-(3-((1r,3r)-3-(benzyloxy)cyclobutoxy)propoxy)propoxy)tetrahydro-2H-pyran

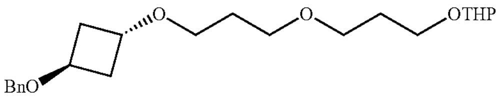

To a solution of (1r,3r)-3-(benzyloxy)cyclobutanol (200 mg, 1.12 mmol) in N,N-dimethylformamide (6 ml) was added sodium hydride (60% in mineral oil) (63 mg, 1.57 mmol) at 0° C., and the resulting mixture was stirred at room temperature for 30 minutes. 3-(3-((tetrahydro-2H-pyran-2-yl)oxy)propoxy)propyl 4-methylbenzenesulfonate (501 mg, 1.34 mmol) was added, and the resulting reaction mixture was stirred at room temperature for 2 hours. The reaction mixture was quenched with water (30 ml) at 0° C. and extracted with ethyl acetate (60 ml×2). The combined organic layers were washed with brine (30 ml), dried over anhydrous sodium sulfate, and concentrated under reduced pressure to give a residue which was purified by silica gel flash chromatography (eluted with 30% ethyl acetate in hexane) to afford 2-(3-(3-((1r,3r)-3-(benzyloxy)cyclobutoxy)propoxy)propoxy)tetrahydro-2H-pyran (234 g, yield 47%) as colorless oil.

Step 5: (1r,3r)-3-(3-(3-hydroxypropoxy)propoxy)cyclobutanol

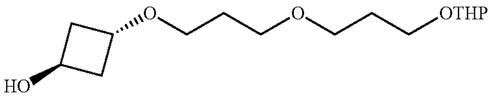

A mixture of 2-(3-(3-((1r,3r)-3-(benzyloxy)cyclobutoxy)propoxy)propoxy)tetrahydro-2H-pyran (468 g, 1.23 mmol), palladium on carbon (10%, 60 mg) in methanol (30 ml) was stirred at room temperature overnight under hydrogen atmosphere (hydrogen balloon). Palladium on carbon was removed through filtration and washed with methanol (5 ml×2). The combined filtrates were concentrated under reduced pressure to afford (1r,3r)-3-(3-(3-hydroxypropoxy)propoxy)cyclobutanol (240 mg, yield: 95%) as colorless oil.

Step 6: 3-(3-((1r,3r)-3-((5-(5-methyl-5H-pyrido[4,3-b]indol-7-yl)pyridin-2-yl)oxy)cyclobutoxy)propoxy)propan-1-ol

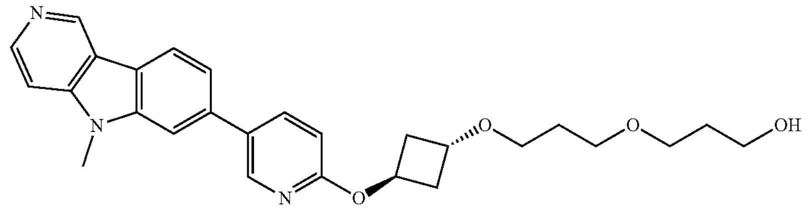 [SMILES: Cn1c2ccncc2c2ccc(-c3ccc(O[C@H]4C[C@H](OCCCOCCCO)C4)nc3)cc21]

To a solution of (1r,3r)-3-(3-(3-hydroxypropoxy)propoxy)cyclobutanol (100 mg, 0.49 mmol) in N,N-dimethylformamide (3 ml) was added sodium hydride (60% in mineral oil) (28 mg, 0.69 mmol) at 0° C., and the resulting mixture was stirred at room temperature for 30 minutes. 7-(6-fluoropyridin-3-yl)-5-methyl-5H-pyrido[4,3-b]indole (96 mg, 0.35 mmol) was added, and the resulting reaction mixture was stirred at room temperature for 3 hours. The reaction mixture was quenched with water (30 ml) at 0° C. and extracted with ethyl acetate (60 ml×2). The combined organic layers were washed with brine (30 ml), dried over anhydrous sodium sulfate, and concentrated under reduced pressure to give a residue which was purified by silica gel flash chromatography (eluted with 5% methanol in dichloromethane) to afford 3-(3-((1r,3r)-3-((5-(5-methyl-5H-pyrido[4,3-b]indol-7-yl)pyridin-2-yl)oxy)cyclobutoxy)propoxy)propan-1-ol (75 mg, yield 34%) as white solid.

Step 7: 3-(3-((1r,3r)-3-((5-(5-methyl-5H-pyrido[4,3-b]indol-7-yl)pyridin-2-yl)oxy)cyclobutoxy)propoxy)propanal

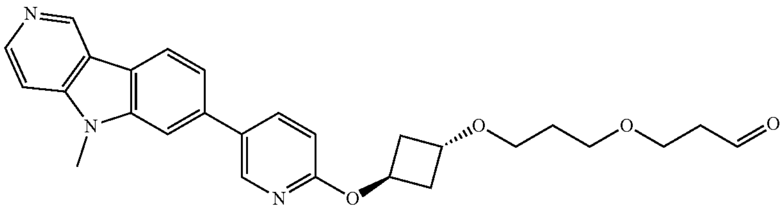 [SMILES: Cn1c2ccncc2c2ccc(-c3ccc(O[C@H]4C[C@H](OCCCOCCC=O)C4)nc3)cc21]

To a stirred solution of 3-(3-((1r,3r)-3-((5-(5-methyl-5H-pyrido[4,3-b]indol-7-yl)pyridin-2-yl)oxy)cyclobutoxy)propoxy)propan-1-ol (70 mg, 0.15 mmol) in dichloromethane (5 ml) was added Dess-Martin periodinane (129 mg, 0.3 mmol) at 0° C. The resulting reaction mixture was allowed to warm up to room temperature and stirred at this temperature for additional 30 minutes. The reaction mixture was quenched with aqueous solution of sodium bicarbonate (10 ml) and extracted with dichloromethane (20 ml×2), washed with brine (20 ml), dried over anhydrous sodium sulfate and concentrated under reduced pressure to afford crude 3-(3-((1r,3r)-3-((5-(5-methyl-5H-pyrido[4,3-b]indol-7-yl)pyridin-2-yl)oxy)cyclobutoxy)propoxy)propanal (80 mg, crude) as white solid which was used in next step without further purification.

Step 8: 2-(2,6-dioxopiperidin-3-yl)-5-((1-(3-(3-((1r,3r)-3-((5-(5-methyl-5H-pyrido[4,3-b]indol-7-yl)pyridin-2-yl)oxy)cyclobutoxy)propoxy)propyl)azetidin-3-yl)oxy)isoindoline-1,3-dione

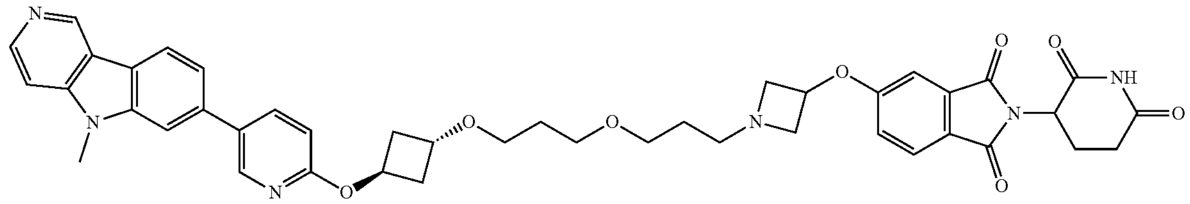 [SMILES: Cn1c2ccncc2c2ccc(-c3ccc(O[C@H]4C[C@H](OCCCOCCCN5CC(Oc6ccc7c(c6)C(=O)N(C6CCC(=O)NC6=O)C7=O)C5)C4)nc3)cc21]

A mixture of 5-(azetidin-3-yloxy)-2-(2,6-dioxopiperidin-3-yl)isoindoline-1,3-dione hydrochloride (70 mg, 0.17 mmol) [prepared as shown in scheme below using procedures described above and common procedures known to those skilled in the art], N-ethyl-N-isopropylpropan-2-amine (44 mg, 0.35 mmol), acetic acid (1 drop) and 3-(3-((1r,3r)-3-((5-(5-methyl-5H-pyrido[4,3-b]indol-7-yl)pyridin-2-yl)oxy)cyclobutoxy)propoxy)propanal (80 mg, 0.17 mmol) in methanol (5 ml) was stirred at room temperature for 30 min, followed by addition of sodium cyonobrohydriole (22 mg, 0.35 mmol) at room temperature. The resulting mixture was stirred at room temperature for 30 minutes. The reaction mixture was quenched with aqueous solution of sodium bicarbonate (sat. 10 ml) and extracted with ethyl acetate (20 ml), washed with brine (10 ml), dried over anhydrous sodium sulfate, and concentrated under reduced pressure to afford a crude residue which was purified by prep. TLC (eluted with 10% methanol in dichloromethane) to afford 2-(2,6-dioxopiperidin-3-yl)-5-((1-(3-(3-((1r,3r)-3-((5-(5-methyl-5H-pyrido[4,3-b]indol-7-yl)pyridin-2-yl)oxy)cyclobutoxy)propoxy)propyl)azetidin-3-yl)oxy)isoindoline-1,3-dione (20 mg, yield: 15%) as white solid.

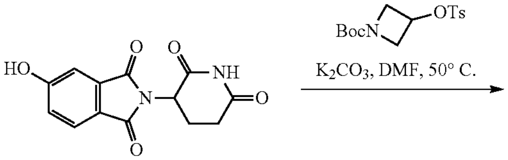

-continued

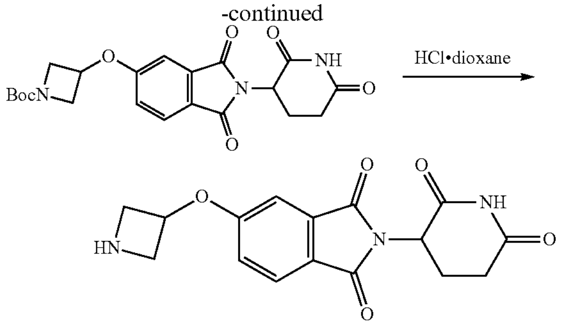

Compound 99: $^1$H NMR (400 Hz, DMSO-d6): δ 1.40-1.56 (m, 2H), 1.62-1.75 (m, 2H), 1.83-2.09 (m, 2H), 2.34-2.50 (m, 3H), 2.58-2.73 (m, 2H), 2.83-2.93 (m, 1H), 3.01-3.13 (m, 2H), 3.37-3.52 (m, 8H), 3.77 (s, 2H), 3.95 (s, 3H), 4.18 (s, 1H), 5.02-5.13 (m, 2H), 5.29-5.37 (m, 1H), 6.94 (d, J=8.0 Hz, 1H), 7.21-7.29 (m, 2H), 7.59-7.65 (m, 2H), 7.80 (d, J=7.2 Hz, 1H), 7.97 (s, 1H), 8.18 (d, J=7.6 Hz, 1H), 8.31 (d, J=7.6 Hz, 1H), 8.50 (d, J=5.2 Hz, 1H), 8.63 (s, 1H), 9.35 (s, 1H), 11.11 (s, 1H). $(M+H)^+$ 773.5.

Synthetic Scheme for Exemplary Compound 100

2-(2,6-dioxopiperidin-3-yl)-5-(6-(4-(4-((5-(5-methyl-5H-pyrido[4,3-b]indol-7-yl)pyridin-2-yl)oxy)butoxy)butoxy)-2-azaspiro[3.3]heptan-2-yl)isoindoline-1,3-dione

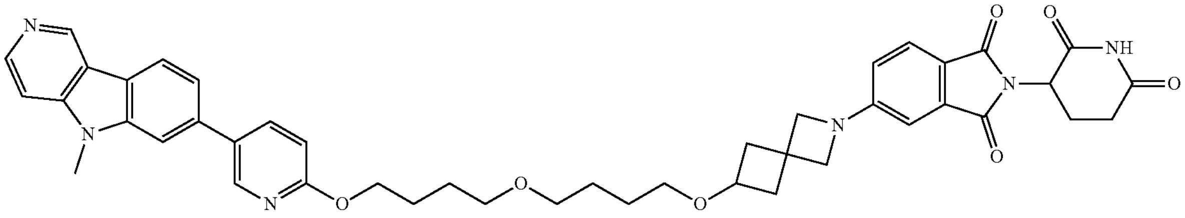 [SMILES: Cn1c2ccncc2c2ccc(-c3ccc(OCCCCOCCCCOC4CC5(C4)CN(c4ccc6c(c4)C(=O)N(C4CCC(=O)NC4=O)C6=O)C5)nc3)cc21]

Prepared according to the synthetic scheme below using procedures described above and common procedures known to those skilled in the art.

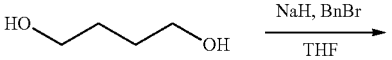

-continued
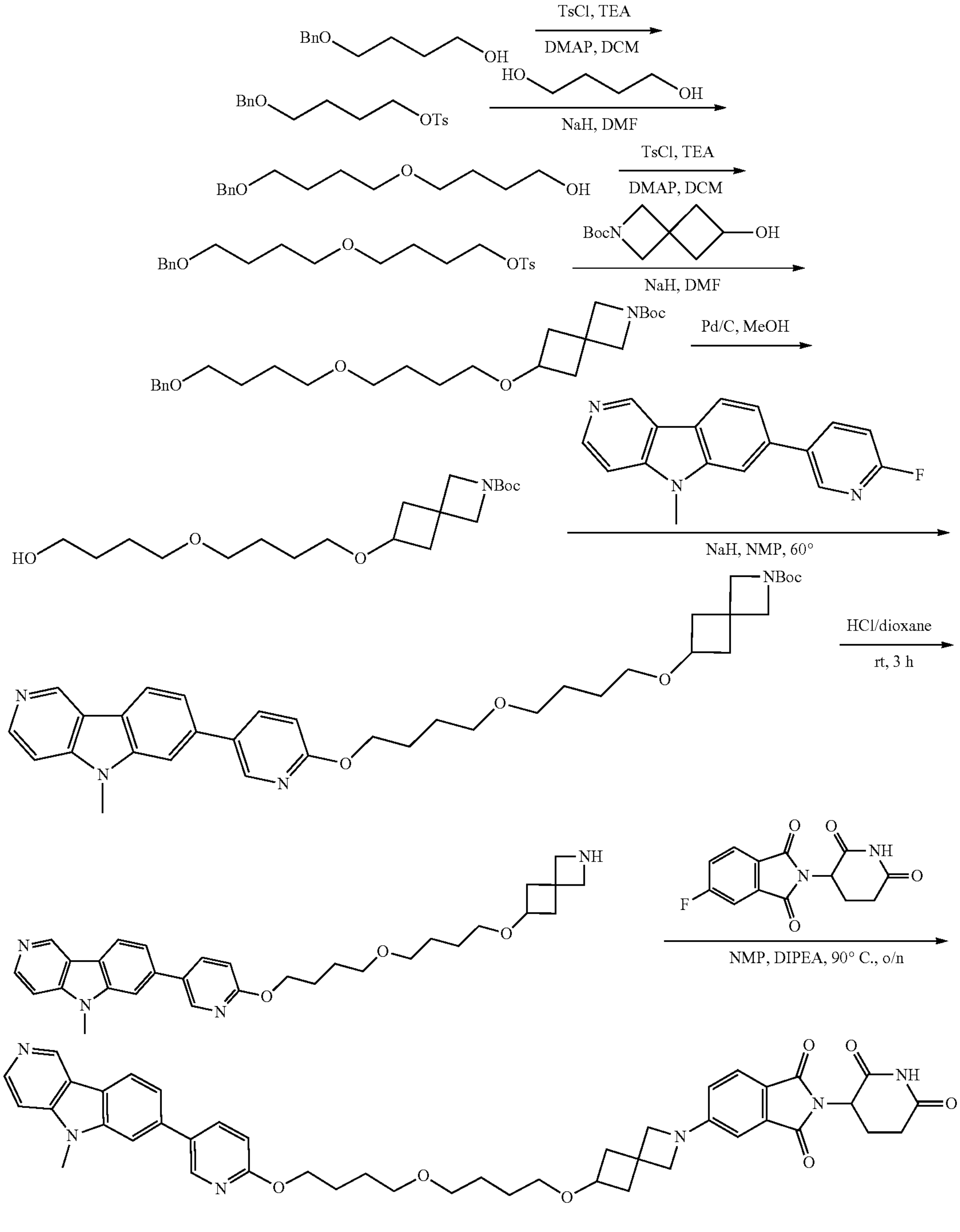
Compound 100
Compound 100: $^1$H NMR (400 MHz, $CDCl_3$): δ 1.65-1.67 (m, 6H), 1.74-1.81 (m, 2H), 1.87-1.94 (m, 2H), 2.00-2.06 (m, 1H), 2.09-2.14 (m, 1H), 2.18-2.24 (m, 2H), 2.54-2.59 (m, 2H), 2.68-2.90 (m, 3H), 3.37-3.53 (m, 5H), 3.91 (t, J=7.6 Hz, 3H), 3.98 (d, J=8.0 Hz, 3H), 4.39 (t, J=6.4 Hz, 2H), 4.90-4.94 (n, 1H), 6.45 (d, J=1.6 Hz, 1H), 6.72 (d, 1=1.6 Hz, 1H), 6.85 (d, J=8.4 Hz, 1H), 7.35 (d, J=6 Hz, 1H), 7.50 (d, J=8.0 Hz, 1H), 7.56 (s, 1H), 7.61 (d, J=8.0 Hz, 1H), 7.91 (d, J=2.4 Hz, 1H), 8.05 (s, 1H), 8.21 (d, J=8.0 Hz, 1H), 8.49 (d, J=2.4 Hz, 1H), 8.60 (d, J=5.6 Hz, 1H), 9.34 (s, 1H). $(M+H)^+$ 771.6.

Synthetic Scheme of Exemplary Compound 101
5-((1-(3-(3-((1r,3r)-3-((5-(5H-pyrido[4,3-b]indol-7-yl)-3-(trifluoromethyl)pyridin-2-yl)oxy)cyclobutoxy)propoxy)propyl)azetidin-3-yl)oxy)-2-(2,6-dioxopiperidin-3-yl)isoindoline-1,3-dione
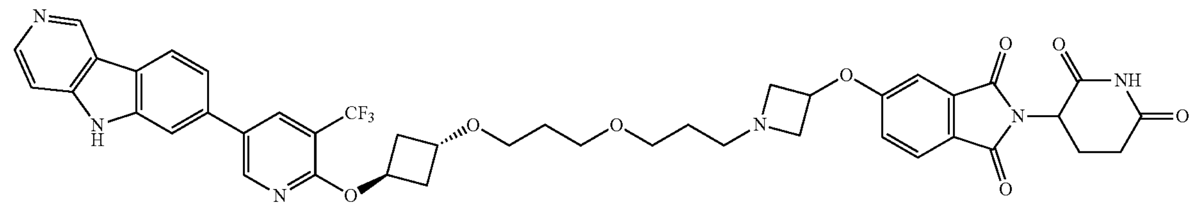 [SMILES: O=C1CCC(N2C(=O)c3ccc(OC4CN(CCCOCCCO[C@H]5C[C@H](Oc6ncc(-c7ccc8c(c7)[nH]c7ccncc78)cc6C(F)(F)F)C5)C4)cc3C2=O)C(=O)N1]
Prepared according to the synthetic scheme below using procedures described above and common procedures known to those skilled in the art.
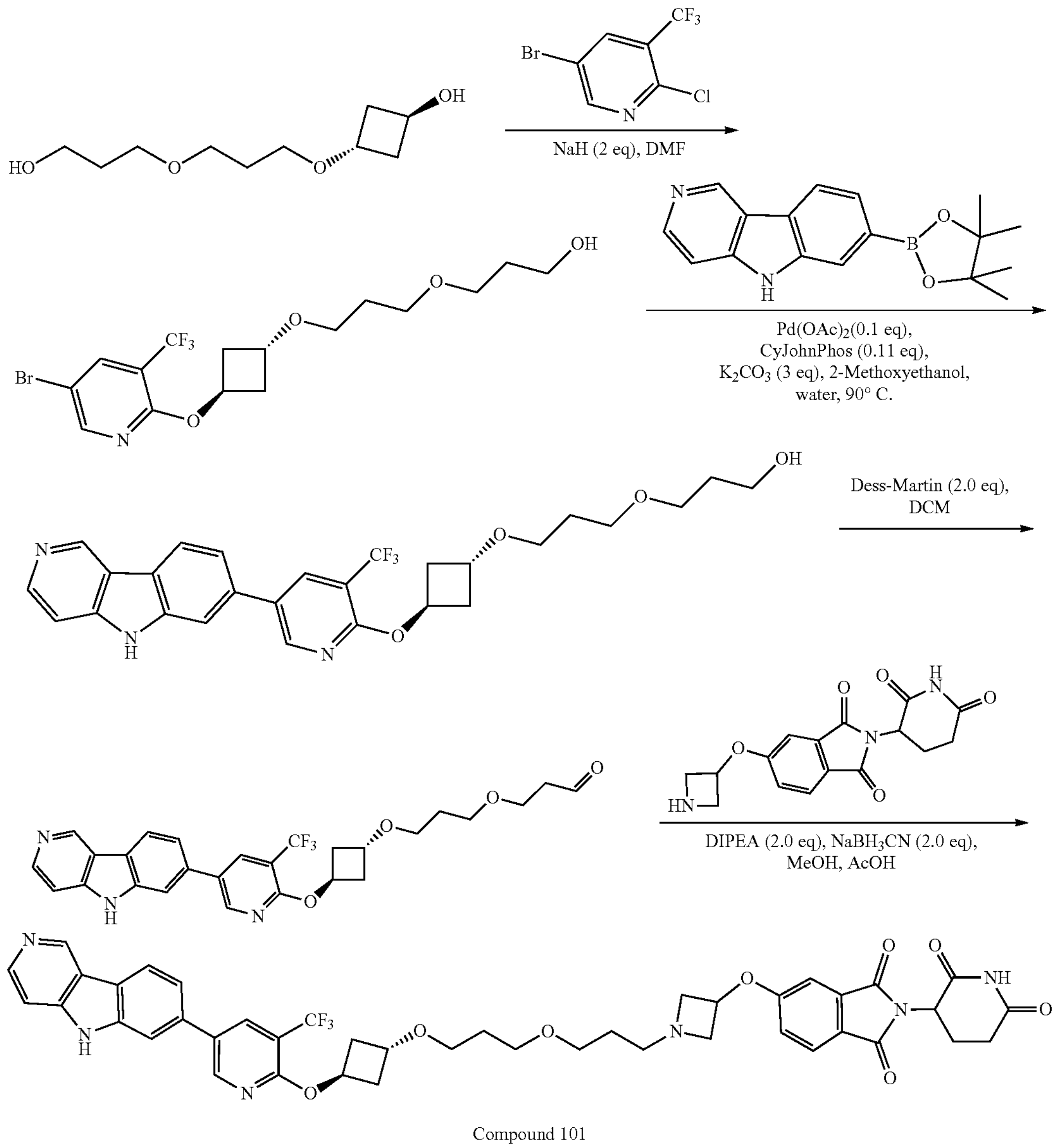
Compound 101

Compound 101: $^1$H NMR (400 Hz, D6-DMSO): δ 1.56-1.59 (m, 2H), 1.71-1.77 (m, 2H), 1.95-2.05 (m, 2H), 2.34-2.46 (m, 3H), 2.50-2.67 (m, 3H), 2.83-2.93 (m, 1H), 3.32-3.49 (m, 9H), 3.88-3.92 (m, 1H), 4.17-4.20 (m, 1H), 4.55 (t, J=5.6 Hz, 1H), 5.05-5.13 (m, 2H), 5.46-5.49 (m, 1H), 7.25-7.28 (m, 2H), 7.52 (d, J=5.6 Hz, 1H), 7.63 (d, J=8.0 Hz, 1H), 7.82 (d, J=8.0 Hz, 1H), 7.87 (s, 1H), 8.33 (d, J=8.0 Hz, 1H), 8.39 (s, 1H), 8.45 (d, J=6.0 Hz, 1H), 8.83 (s, 1H), 9.39 (s, 1H), 11.11 (s, 1H), 11.86 (s, 1H). $(M+H)^+$ 827.5.

Using analogous procedures the following were prepared: Compound 105.

Synthetic Scheme for Exemplary Compound 103

5-((14-((5-(8,9-difluoro-5H-pyrido[4,3-b]indol-7-yl)pyridin-2-yl)oxy)-3,6,9,12-tetraoxatetradecyl)oxy)-2-(2,6-dioxopiperidin-3-yl)isoindoline-1,3-dione

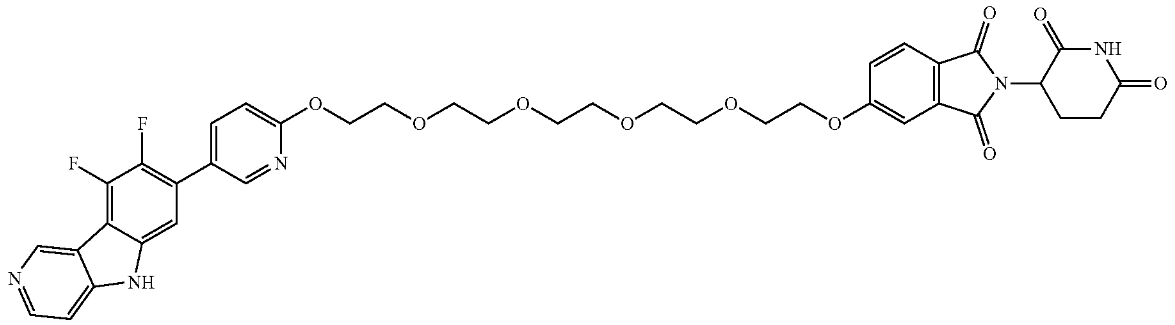 [SMILES: O=C1CCC(N2C(=O)c3ccc(OCCOCCOCCOCCOCCOc4ccc(-c5cc6[nH]c7ccncc7c6c(F)c5F)cn4)cc3C2=O)C(=O)N1]

Step 1: 5-bromo-2-((1-phenyl-2,5,8,11,14-pentaoxahexadecan-16-yl)oxy)pyridine

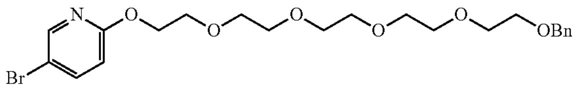 [SMILES: Brc1ccc(OCCOCCOCCOCCOCCOCc2ccccc2)nc1]

To a solution of compound 5-bromo-2-fluoropyridine (2.0 g, 9.5 mmol) in DMF (20 mL) was added 1-phenyl-2,5,8,11,14-pentaoxahexadecan-16-ol (2.6 g, 7.91 mmol) and NaH (950 mg, 24 mmol, 60%) at 0° C. The resulting mixture was stirred at 20° C. for 18 hours. TLC (PE:EA=1:1, Rf=0.5) showed 5-bromo-2-fluoropyridine was consumed. The mixture was diluted with EA (30 mL), washed with water (3*30 mL) and brine (30 mL). The organic layer was dried and concentrated to give crude product, which was purified by column chromatography on silica gel with PE:EA (1:1) to give the desired product (3.6 g) as a colorless oil.

Step 2: 2-((1-phenyl-2,5,8,11,14-pentaoxahexadecan-16-yl)oxy)-5-(4,4,5,5-tetramethyl-1,3,2-dioxaborolan-2-yl)pyridine

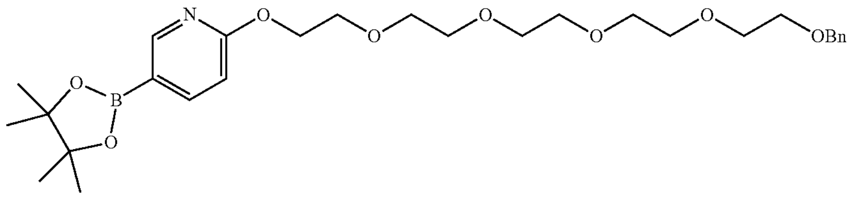 [SMILES: CC1(C)OB(c2ccc(OCCOCCOCCOCCOCCOCc3ccccc3)nc2)OC1(C)C]

-

To a solution of 5-bromo-2-((1-phenyl-2,5,8,11,14-pentaoxahexadecan-16-yl)oxy) pyridine (3.6 g, 7.22 mmol) in dioxane (50 mL) was added 4,4,4',4',5,5,5',5'-octamethyl-2,2'-bi (1,3,2-dioxaborolane) (3.7 g, 14.45 mmol), Pd(dppf)$Cl_2$ (530 mg) and AcOK (1.42 g, 14.45 mmol). The resulting solution was stirred at 90° C. for 18 hours. The mixture was filtered and concentrated. The crude was purified by column chromatography on silica gel with PE:EA (1:1) to afford the desired product (3.0 g, yield=78%) as a yellow oil.-

Step 3: 5-(4-bromo-2,3-difluorophenyl)-2-((1-phenyl-2,5,8,11,14-pentaoxahexadecan-16-yl)oxy)pyridine

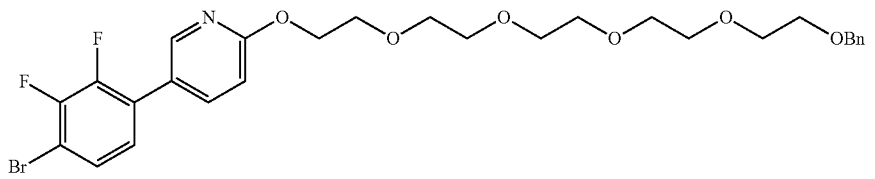 [SMILES: Fc1c(Br)ccc(-c2ccc(OCCOCCOCCOCCOCCOCc3ccccc3)nc2)c1F]

To a solution of 2-((1-phenyl-2,5,8,11,14-pentaoxahexadecan-16-yl) oxy)-5-(4,4,5,5-tetramethyl-1,3,2-dioxaborolan-2-yl)pyridine (2.8 g, 5.27 mmol) in dioxane/$H_2O$ (55 mL, 10/1, v/v) was added 1,4-dibromo-2,3-difluorobenzene (1.72 g, 6.32 mmol, CsF (1.6 g, 10.54 mmol) and $Pd(PPh_3)$ (300 mg). The resulting solution was stirred at 90° C. for 18 hours under $N_2$. After the reaction was over, the mixture was quenched with EA and extracted with EA. The organic layer was washed with brine, dried over $Na_2SO_4$, filtered and concentrated. The crude was purified by column chromatography on silica gel with PE:EA (1:1) to afford the desired product (1.5 g, yield=48%) as a brown oil.

Step 4: 5-(2,3-difluoro-4-(4,4,5,5-tetramethyl-1,3,2-dioxaborolan-2-yl)phenyl)-2-((1-phenyl-2,5,8,11,14-pentaoxahexadecan-16-yl)oxy)pyridine

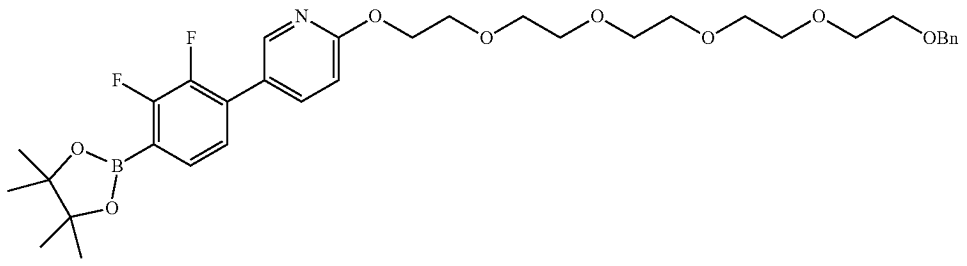 [SMILES: CC1(C)OB(c2ccc(-c3ccc(OCCOCCOCCOCCOCCOCc4ccccc4)nc3)c(F)c2F)OC1(C)C]

To a solution of 5-(4-bromo-2,3-difluorophenyl)-2-((1-phenyl-2,5,8,11,14-pentaoxahexadecan-16-yl)oxy) pyridine (1.0 g, 1.68 mmol) in dioxane (20 mL) was added 4,4,4',4',5,5,5',5'-octamethyl-2,2'-bi(1,3,2-dioxaborolane) (640 mg, 2.52 mmol), $Pd(dppf)Cl_2$ (120 mg) and AcOK (330 mg, 3.36 mmol). The resulting solution was stirred at 90° C. for 18 hours. LCMS showed 5-(4-bromo-2,3-difluorophenyl)-2-((1-phenyl-2,5,8,11,14-pentaoxahexadecan-16-yl) oxy)pyridine was consumed completely. The mixture was filtered and concentrated. The crude was purified by column chromatography on silica gel with PE:EA (3:2) to afford the desired product the desired product (660 mg, yield=95%) as a brown oil.

Step 5: 5-(2,3-difluoro-4-(4-nitropyridin-3-yl)phenyl)-2-((1-phenyl-2,5,8,11,14-pentaoxahexadecan-16-yl)oxy)pyridine

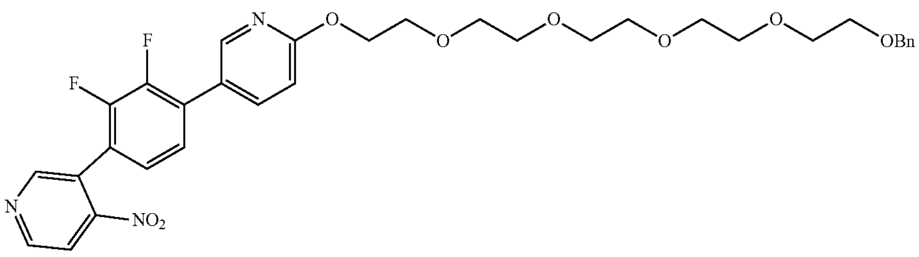 [SMILES: O=[N+]([O-])c1ccncc1-c1ccc(-c2ccc(OCCOCCOCCOCCOCCOCc3ccccc3)nc2)c(F)c1F]

To a solution of 5-(2,3-difluoro-4-(4,4,5,5-tetramethyl-1,3,2-dioxaborolan-2-yl) phenyl)-2-((1-phenyl-2,5,8,11,14-pentaoxahexadecan-16-yl) oxy) pyridine (350 mg, 0.544 mmol) in dioxane/$H_2O$ (11 mL, 10/1, v/v) was added 3-bromo-4-nitropyridine (121 mg, 0.6 mmol), $Na_2CO_3$ (120 mg, 1.1 mmol) and $Pd(PPh_3)_4$ (63 mg). The mixture was stirred at 110° C. for 1 h under $N_2$. After the reaction, the mixture was extracted with ethyl acetate (20 mL) and washed with brine (30 mL). The organic solution was dried over anhydrous sodium sulfate and concentrated. The crude was purified by column chromatography on silica gel with PE/EA (1:3) to give the desired product (170 mg) as a yellow oil.

Step 6: 8,9-difluoro-7-(6-((1-phenyl-2,5,8,11,14-pentaoxahexadecan-16-yl)oxy)pyridin-3-yl)-5H-pyrido[4,3-b]indole

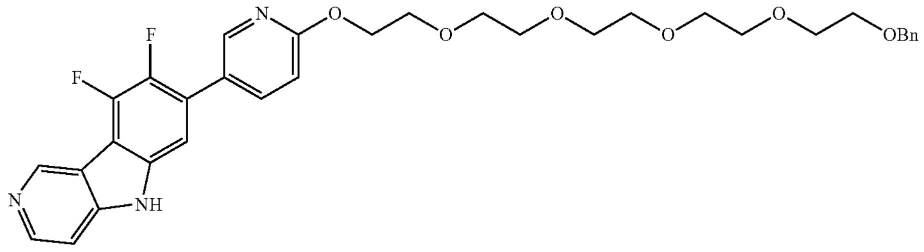 [SMILES: Fc1c(-c2ccc(OCCOCCOCCOCCOCCOCc3ccccc3)nc2)cc2[nH]c3ccncc3c2c1F]

A solution of 5-(2,3-difluoro-4-(4-nitropyridin-3-yl)phenyl)-2-((1-phenyl-2,5,8,11,14-pentaoxahexadecan-16-yl) oxy) pyridine (340 mg, 0.53 mmol) in $P(Oet)_3$ (3 mL) was stirred at 110° C. for 3 h. After the reaction, the mixture was purified by column chromatography on silica gel with DCM/MeOH (30:1) to give the desired product (205 mg) as a brown solid.

8,9-difluoro-7-(6-((1-phenyl-2,5,8,11,14-pentaoxahexadecan-16-yl)oxy)pyridin-3-yl)-5H-pyrido[4,3-b]indole was converted into the final compounds, 5-((14-((5-(8,9-difluoro-5H-pyrido[4,3-b]indol-7-yl)pyridin-2-yl)oxy)-3,6,9,12-tetraoxatetradecyl)oxy)-2-(2,6-dioxopiperidin-3-yl) isoindoline-1,3-dione (Compound 103) and 5-((14-((5-(8,9-difluoro-5-methyl-5H-pyrido[4,3-b]indol-7-yl)pyridin-2-yl) oxy)-3,6,9,12-tetraoxatetradecyl)oxy)-2-(2,6-dioxopiperidin-3-yl)isoindoline-1,3-dione (Compound 112), according to the synthetic scheme below using procedures described above and common procedures known to those skilled in the art.

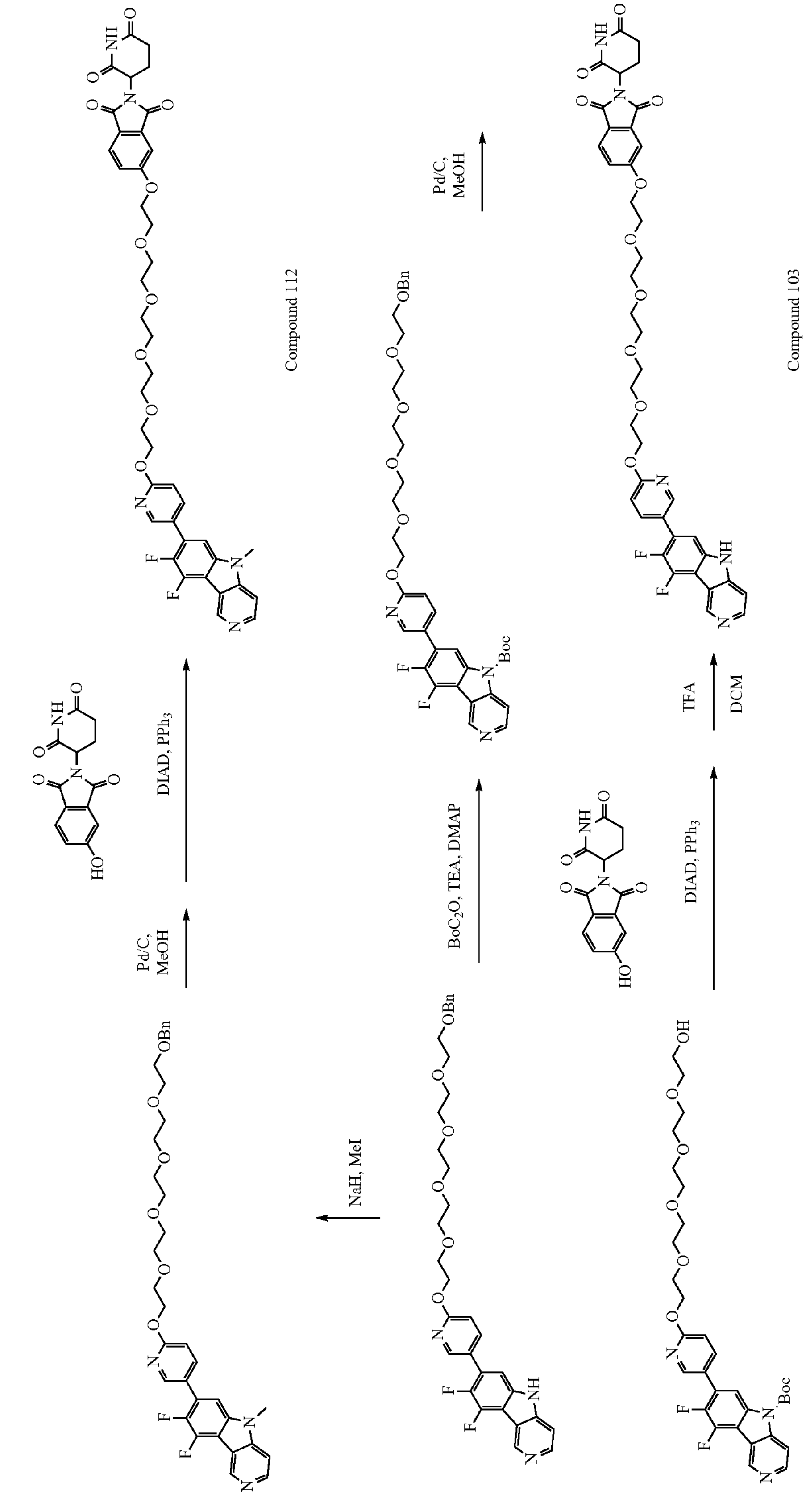
Compound 112
Compound 103

Compound 103: $^1$H NMR (400 MHz, $CD_3OD$): δ 9.46 (s, 1H), 8.63 (d, J=6.8 Hz, 1H), 8.38 (s, 1H), 8.00 (d, J=6.8 Hz, 1H), 7.96 (d, J=8.8 Hz, 1H), 7.67 (d, J=8.4 Hz, 1H), 7.61 (d, J=4.8 Hz, 1H), 7.29 (s, 1H), 7.23 (d, J=8.4 Hz, 1H), 6.93 (d, J=8.8 Hz, 1H), 5.05 (m, 1H), 4.54-4.45 (m, 2H), 4.26-4.19 (m, 2H), 3.86 (m, 4H), 3.70-3.65 (m, 12H), 2.86-2.62 (m, 3H), 2.10-2.04 (m, 1H). $(M+H)^+$ 774.5.

Compound 112: $^1$HNMR (400 MHz, $CDCl_3$): δ: 11.09 (s, 1H), 9.25 (s, 1H), 8.50 (s, 1H), 8.59 (s, 1H), 8.07 (d, J=8.4 Hz, 1H), 7.79 (d, J=8.4 Hz, 1H), 7.69-7.73 (m, 2H), 7.75 (d, J=8.4 Hz, 1H), 7.42 (s, 1H), 7.34 (d, J=8.4 Hz, 1H), 7.02 (d, J=8.4 Hz, 1H), 5.08-5.13 (m, 1H), 4.46 (d, J=4.4 Hz, 2H), 4.30-4.34 (m, 2H), 3.95 (s, 3H), 3.79 (s, 4H), 3.60 (s, 4H), 3.56 (s, 4H), 3.53 (s, 4H), 2.85-2.88 (m, 1H), 2.61 (s, 2H). $(M+H)^+$ 788.5.

Synthetic Scheme for Exemplary Compound 104

2-(2,6-dioxopiperidin-3-yl)-5-(3-(3-(3-((1r,3r)-3-((5-(5-methyl-5H-pyrido[4,3-b]indol-7-yl)pyridin-2-yl)oxy)cyclobutoxy)propoxy)propoxy)azetidin-1-yl)isoindoline-1,3-dione

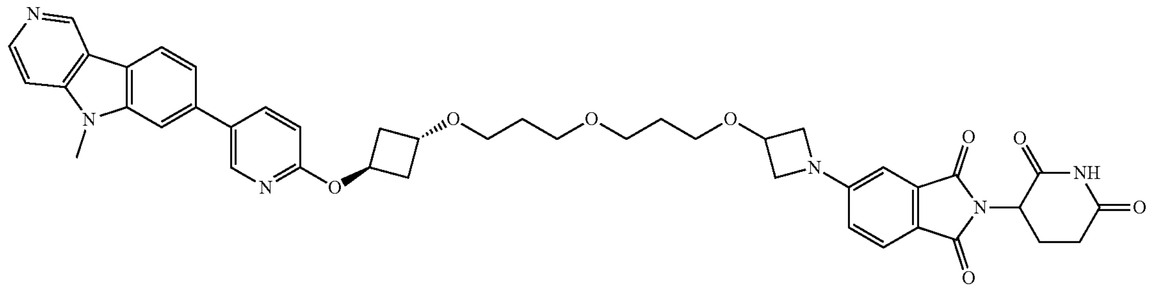 [SMILES: Cn1c2ccncc2c2ccc(-c3ccc(O[C@H]4C[C@H](OCCCOCCCOC5CN(c6ccc7c(c6)C(=O)N(C6CCC(=O)NC6=O)C7=O)C5)C4)nc3)cc21]

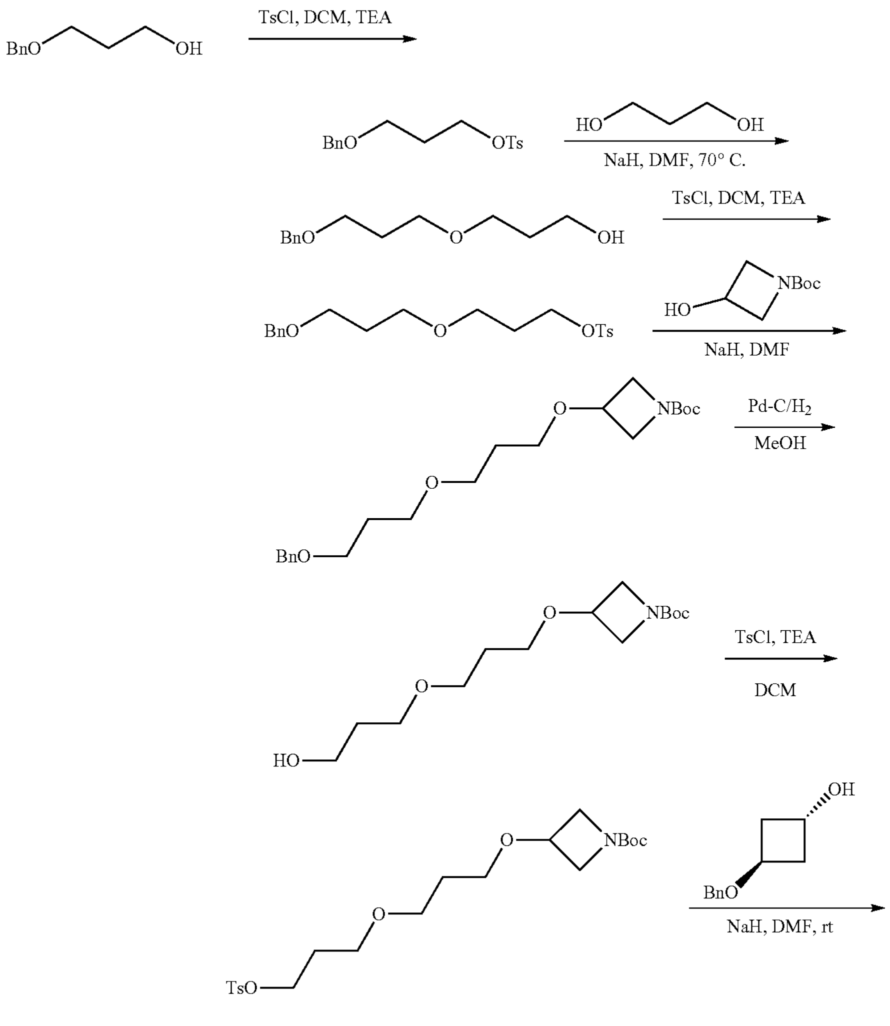

-continued

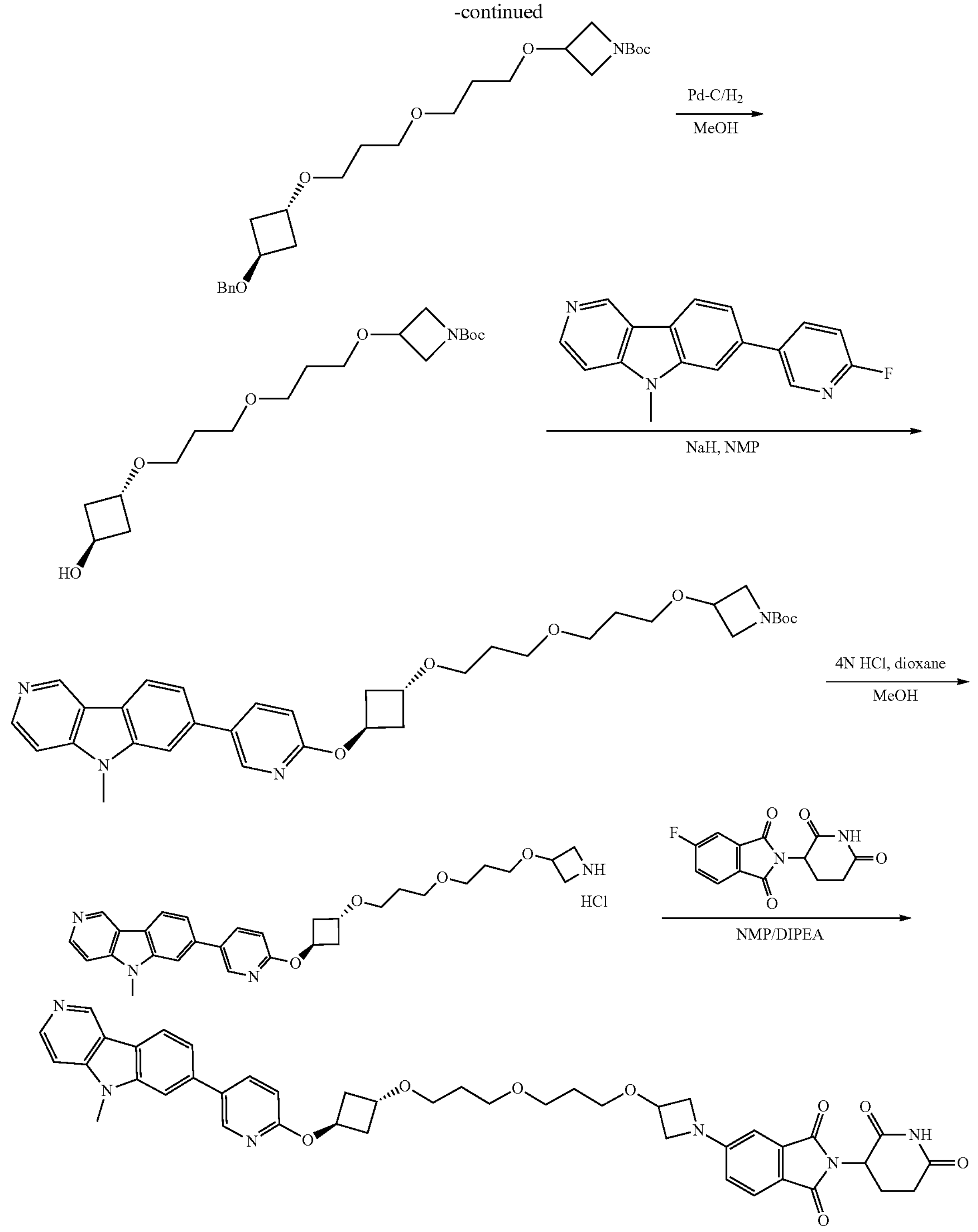

Compound 104

Compound 104: $^{1}H$ NMR (400 MHz, DMSO-d6): δ 1.73-1.79 (m, 4H), 1.97-1.99 (m, 2H), 2.31-2.37 (m, 2H), 2.40-2.49 (m, 2H), 2.54-2.59 (m, 1H), 2.83-2.88 (m, 1H), 3.38 (t, J=6.4 Hz, 2H), 3.43-3.49 (m, 6H), 3.82-3.85 (m, 2H), 3.75 (s, 3H), 4.16-4.18 (m, 1H), 4.20-4.26 (m, 2H), 4.43-4.47 (m, 1H), 5.02-5.07 (m, 1H), 5.31-5.34 (m, 1H), 6.62-6.64 (m, 1H), 6.78-6.79 (m, 1H), 6.93 (t, J=8.4 Hz, 1H), 7.59-6.72 (m, 3H), 7.96 (s, 1H), 8.17-8.19 (m, 1H), 8.30 (d, J=8.0 Hz, 1H), 8.49 (d, J=6.4 Hz, 1H), 8.62-8.63 (m, 1H), 9.35 (s, 1H), 11.06 (s, 1H). $(M+H)^+$ 773.5.

Using procedures analogous to those described above the following compounds were prepared: 125 (while also using procedures described in Compound 67), 148 (while also using procedures described in Compound 67), Compound 170.

Synthetic Scheme for Exemplary Compound 106

Prepared according to the synthetic scheme below using procedures described above and common procedures to those skilled in the art.

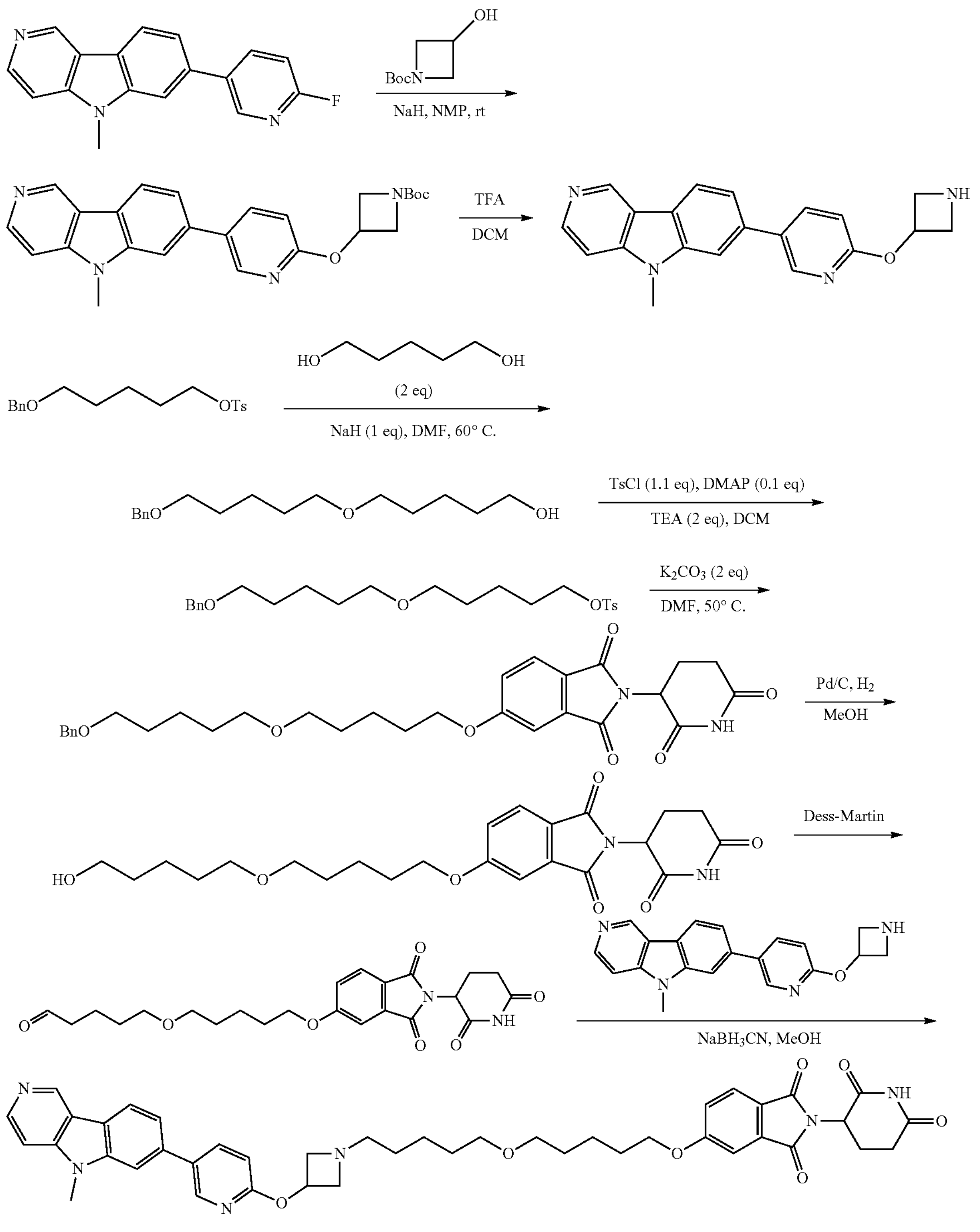
Compound 106
Compound 106: $^1$H NMR (400 MHz, DMSO-d6): δ 1.54-1.68 (m, 10H), 1.84-1.88 (m, 2H), 2.12-2.14 (m, 1H), 2.77-2.93 (m, 5H), 3.40-3.45 (m, 4H), 3.64-3.75 (m, 4H), 3.91 (s, 3H), 4.09 (t, J=6.4 Hz, 2H), 4.39-4.46 (m, 1H), 4.89-4.99 (m, 1H), 5.41-5.50 (m, 1H), 6.90 (d, J=8.4 Hz, 1H), 7.14-7.2 (m, 1H), 7.32-7.35 (m, 2H), 7.48 (d, J=8.0 Hz, 1H), 7.55 (s, 1H), 7.76 (d, J=8.0 Hz, 1H), 7.92-8.00 (m, 1H), 8.21 (d, J=8.0 Hz, 1H), 8.43 (d, J=2.0 Hz, 1H), 8.59 (d, J=5.6 Hz, 1H), 9.33 (s, 1H). $(M+H)^+$ 759.6.

Synthetic Scheme for Exemplary Compound 107
2-(2,6-dioxopiperidin-3-yl)-5-(4-(4-(6-((5-(5-methyl-5H-pyrido[4,3-b]indol-7-yl)pyridin-2-yl)oxy)-2-azaspiro[3.3]heptan-2-yl)butoxy)butoxy)isoindoline-1,3-dione
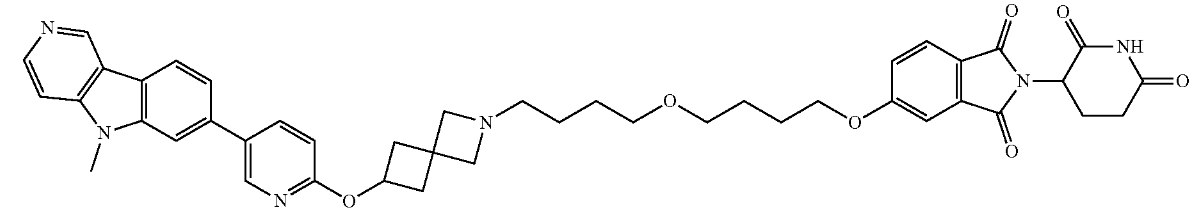 [SMILES: Cn1c2ccncc2c2ccc(-c3ccc(OC4CC5(C4)CN(CCCCOCCCCOc4ccc6c(c4)C(=O)N(C4CCC(=O)NC4=O)C6=O)C5)nc3)cc21]
Prepared according to the synthetic schemes below using procedures described above and common procedures known to those skilled in the art.
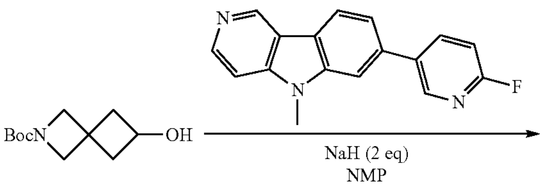
-continued
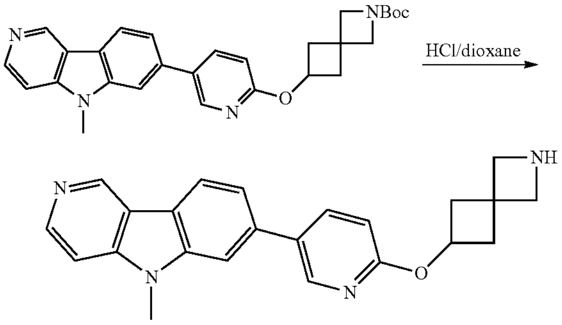
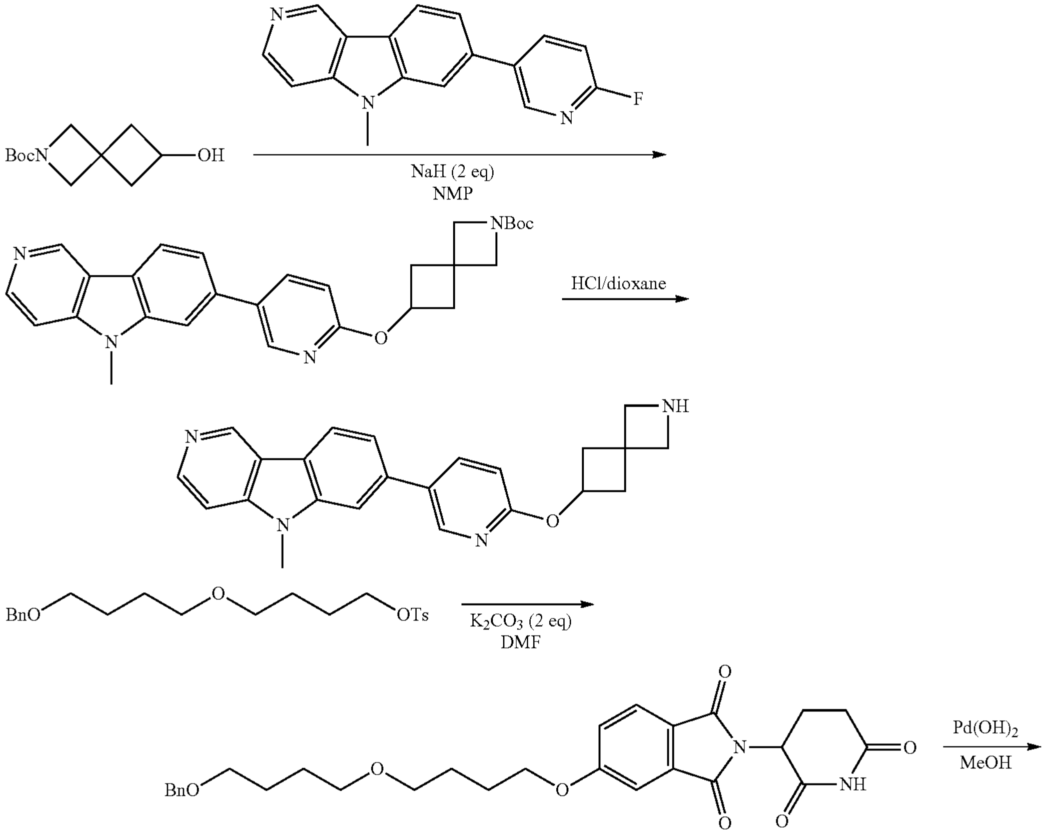

-continued

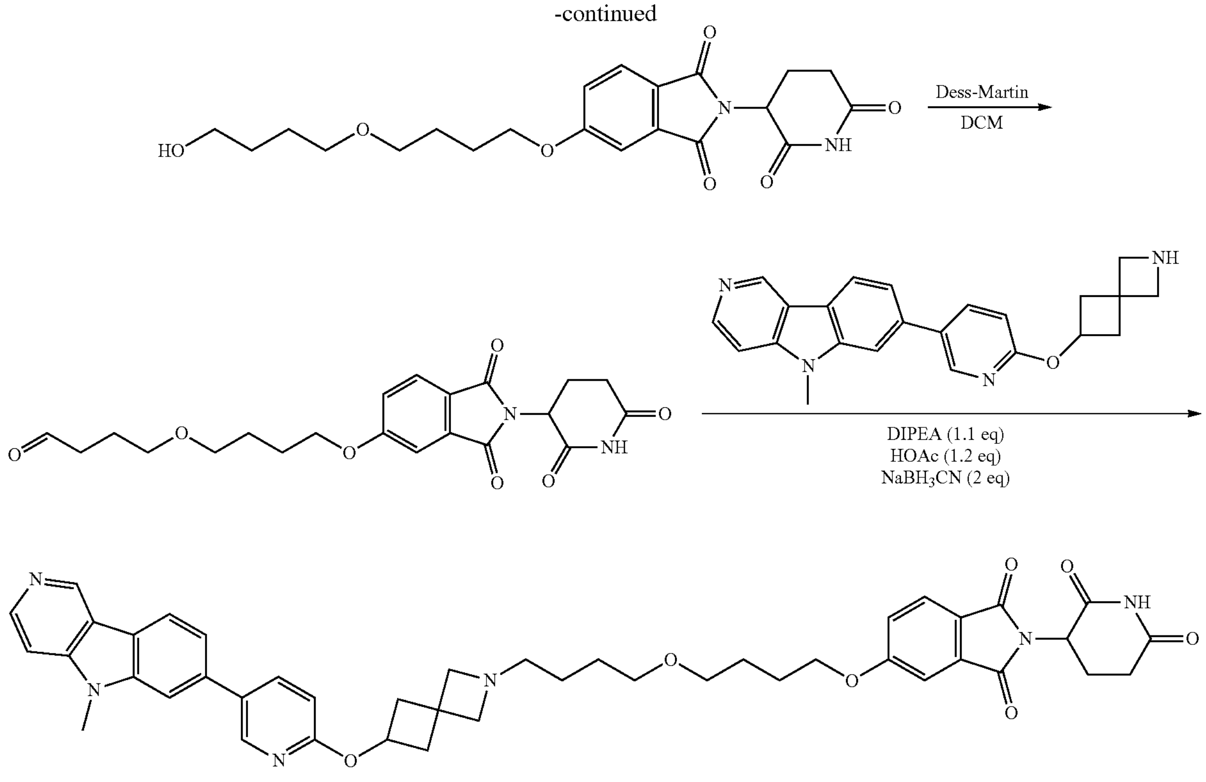

Compound 107

Compound 107: 1HNMR (400 MHz, $CDCl_3$): δ 1.61-1.65 (m, 2H), 1.72-1.77 (m, 4H), 1.90-1.93 (m, 2H), 1.99-2.04 (m, 1H), 2.14-2.22 (m, 3H), 2.44-2.49 (m, 2H), 2.78-3.01 (m, 6H), 3.44-3.49 (m, 4H), 3.92 (s, 3H), 3.99-4.05 (m, 2H), 4.14 (t, J=6.2 Hz, 2H), 4.94-4.98 (m, 1H), 5.17-5.20 (m, 1H), 6.81 (d, J=8.4 Hz, 1H), 7.19-7.21 (m, 1H), 7.33-7.37 (m, 2H), 7.49 (d, J=8.4 Hz, 1H), 7.56 (s, 1H), 7.78 (d, J=8.4 Hz, 1H), 7.90-7.93 (m, 1H), 8.21 (d, J=8.4 Hz, 1H), 8.35 (br, 1H), 8.45-8.46 (m, 1H), 8.59 (d, J=5.6 Hz, 1H), 9.34 (s, 1H). $(M+H)^+$ 771.6.

Synthetic Scheme for Exemplary Compound 108

2-(2,6-dioxopiperidin-3-yl)-5-((6-((6-((1r,3r)-3-((5-(5-methyl-5H-pyrido[4,3-b]indol-7-yl)pyridin-2-yl)oxy)cyclobutoxy)pyridin-2-yl)oxy)hexyl)oxy)isoindoline-1,3-dione

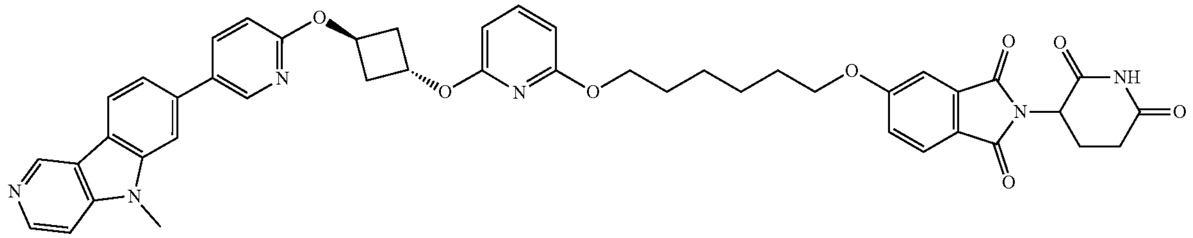 [SMILES: Cn1c2ccncc2c2ccc(-c3ccc(O[C@H]4C[C@H](Oc5cccc(OCCCCCCOc6ccc7c(c6)C(=O)N(C6CCC(=O)NC6=O)C7=O)n5)C4)nc3)cc21]

Prepared according to the synthetic scheme below using procedures described above and common procedures to those skilled in the art.

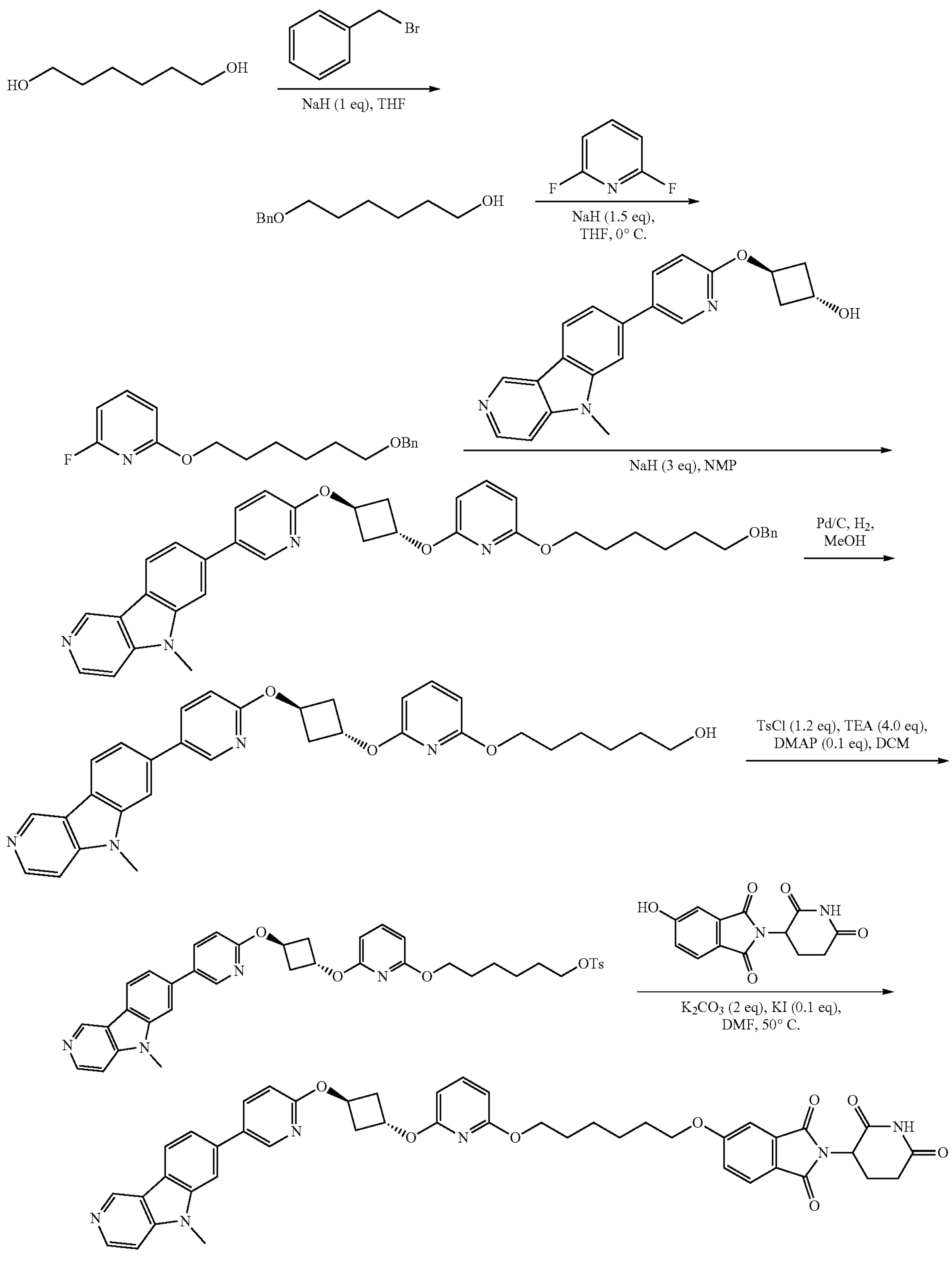
Compound 108
Compound 108: $^1$H NMR (400 MHz, DMSOd-6): δ 1.43-1.44 (m, 4H), 1.70-1.74 (m, 4H), 1.98-2.04 (m, 1H), 2.44-2.47 (m, 1H), 2.56-2.60 (m, 1H), 2.65 (t, J=6.0 Hz, 4H), 2.83-2.92 (m, 1H), 3.95 (s, 3H), 4.10 (t, J=6.0 Hz, 2H), 4.22 (t, J=6.4 Hz, 2H), 5.07-5.11 (m, 1H), 5.30-5.35 (m, 1H), 5.39-5.45 (m, 1H), 6.34-6.37 (m, 2H), 6.98 (d, J=8.4 Hz, 1H), 7.24-7.26 (m, 1H), 7.33 (d, J=2.0 Hz, 1H), 7.59-7.65 (m, 3H), 7.72 (d, J=8.0 Hz, 1H), 7.97 (s, 1H), 8.17-8.21 (m, 1H), 8.31 (d, J=8.0 Hz, 1H), 8.50 (d, J=6.0 Hz, 1H), 8.65 (d, J=2.0 Hz, 1H), 9.36 (s, 1H), 11.10 (s, 1H). $(M+H)^+$ 795.5.
Synthetic Scheme for Exemplary Compound 109
2-(2,6-dioxopiperidin-3-yl)-5-((6-((4-((1r,3r)-3-((5-(5-methyl-5H-pyrido[4,3-b]indol-7-yl)pyridin-2-yl)oxy)cyclobutoxy)pyridin-2-yl)oxy)hexyl)oxy)isoindoline-1,3-dione
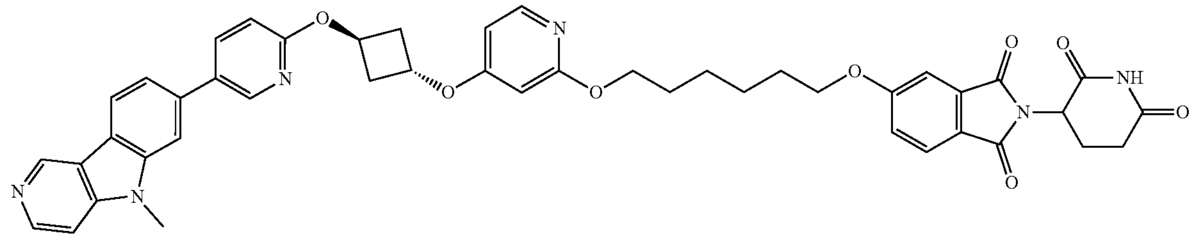
Prepared according to the synthetic scheme below using procedures described above and common procedures to those skilled in the art.
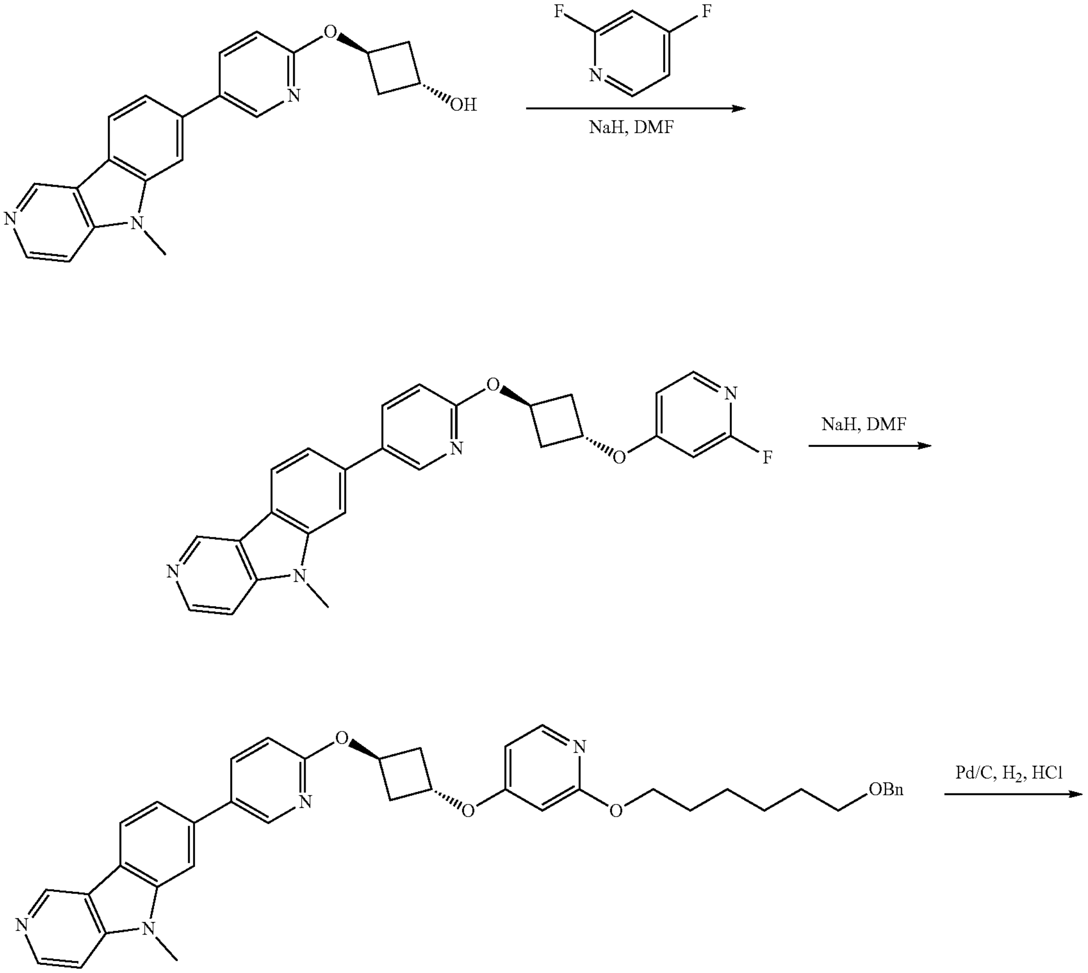

-continued
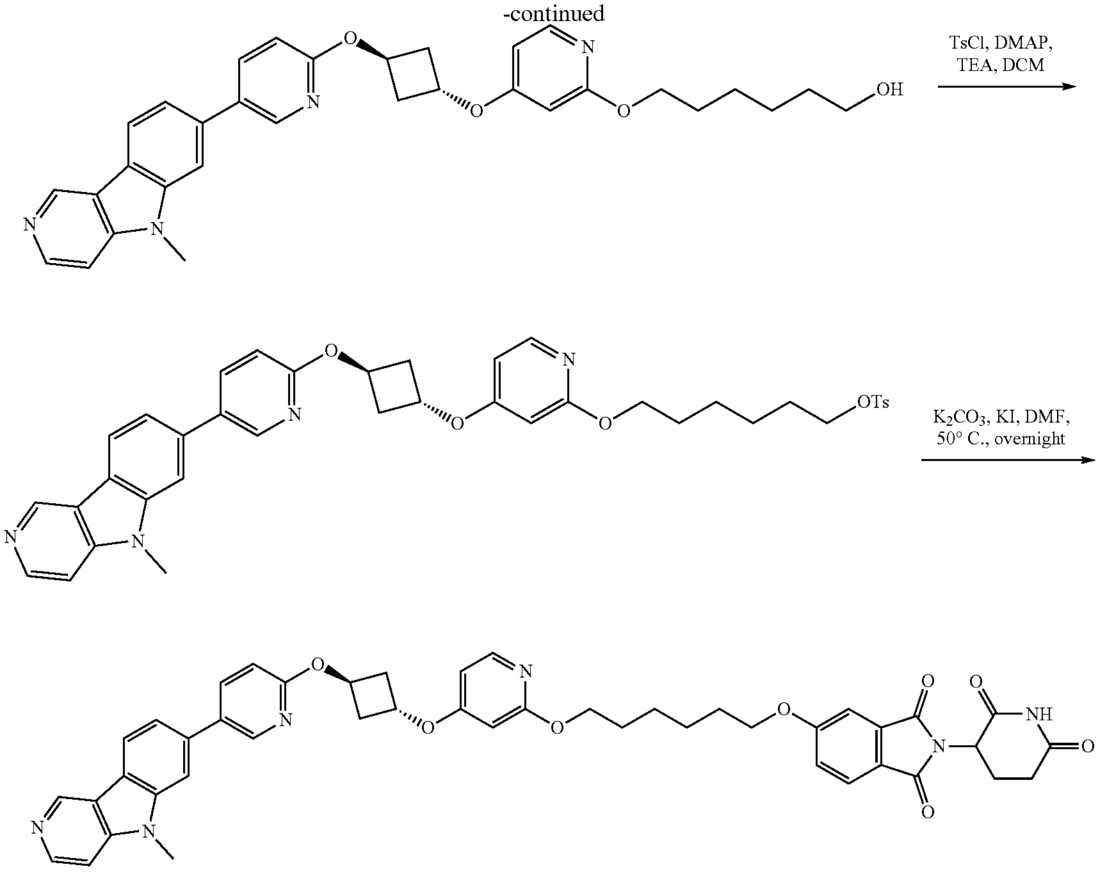
Compound 109
Compound 109: $^1$H NMR (400 MHz, DMSOd-6): δ 1.47 (s, 4H), 1.72-1.78 (m, 4H), 2.02-2.05 (m, 2H), 2.33 (s, 1H), 2.63-2.66 (m, 4H), 2.88-2.89 (m, 1H), 3.41-3.49 (m, 2H), 3.96 (s, 2H), 4.18-4.23 (m, 3H), 5.04-5.12 (m, 2H), 5.42 (br, 1H), 6.19 (s, 1H), 6.55-6.56 (m, 1H), 6.98 (d, J=8.4 Hz, 1H), 7.34 (d, J=7.2 Hz, 1H), 7.41 (s, 1H), 6.63 (s, 2H), 7.81-7.83 (m, 1H), 7.95-7.97 (m, 2H), 8.21 (d, J=8.4 Hz, 1H), 8.32 (d, J=7.2 Hz, 1H), 8.50 (d, J=4.0 Hz, 1H), 8.64 (s, 1H), 9.36 (s, 1H), 11.11 (s, 1H). $(M+H)^+$ 795.5.
Synthetic Scheme for Exemplary Compound 111
2-(2,6-dioxopiperidin-3-yl)-5-(3-((3-(5-((1r,3r)-3-((5-(5-methyl-5H-pyrido[4,3-b]indol-7-yl)pyridin-2-yl)oxy)cyclobutoxy)pyridin-2-yl)prop-2-yn-1-yl)oxy)azetidin-1-yl)isoindoline-1,3-dione
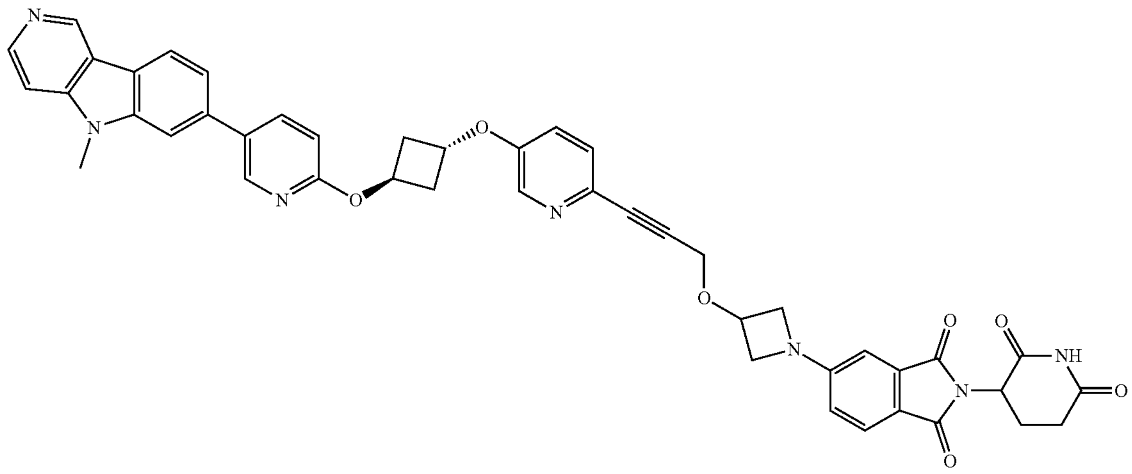 [SMILES: Cn1c2ccncc2c2ccc(-c3ccc(O[C@H]4C[C@H](Oc5ccc(C#CCOC6CN(c7ccc8c(c7)C(=O)N(C7CCC(=O)NC7=O)C8=O)C6)nc5)C4)nc3)cc21]

Step 1: tert-butyl 3-(prop-2-yn-1-yloxy)azetidine-1-carboxylate

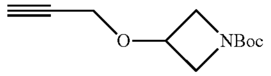

To a stirred solution of tert-butyl 3-hydroxyazetidine-1-carboxylate (1.0 g, 12.2 mmol) in N,N-dimethylformamide (10 ml) was added sodium hydride (60% in mineral oil) (255 mg, 6.36 mmol) at 0° C., and the resulting mixture was stirred at 0° C. for 30 minutes. The reaction mixture was allowed to warm up to room temperature and stirred for additional 30 min, then 3-bromoprop-1-yne (818 mg, 6.94 mmol) was added, and the resulting reaction mixture was stirred at 50° C. overnight. LCMS showed the reaction was complete. The reaction mixture was quenched with water (10 ml) at 0° C. and extracted with ethyl acetate (30 ml×2). The combined organic layers were washed with brine (30 ml×2), dried over anhydrous sodium sulfate, and concentrated under reduced pressure to give a residue which was purified by silica gel flash chromatography (eluted with 10% ethyl acetate in hexane) to afford tert-butyl 3-(prop-2-yn-1-yloxy)azetidine-1-carboxylate (1.03 g, yield 84%) as colorless oil.

Step 2: tert-butyl 3-((3-(5-hydroxypyridin-2-yl) prop-2-yn-1-yl)oxy)azetidine-1-carboxylate

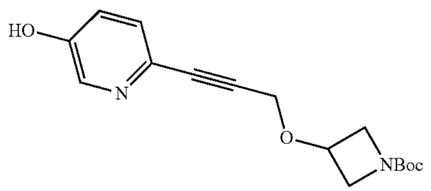 [SMILES: CC(C)(C)OC(=O)N1CC(OCC#Cc2ccc(O)cn2)C1]

To a stirred solution of tert-butyl-3-(prop-2-yn-1-yloxy) azetidine-1-carboxylate (900 mg, 4.27 mmol) and 6-bromopyridin-3-ol (734 mg, 4.27 mmol) in acetonitrile (10 ml) was added triethylamine (863 mg, 8.54 mmol) followed by bis(triphenylphosphine)palladium(II) chloride (150 mg, 0.214 mmol) and cuprous iodide (41 mg, 0.214 mmol) at room temperature under nitrogen atmosphere; the mixture was degassed with nitrogen three times. The reaction mixture was allowed to warm up to 65° C. and stirred overnight. TLC showed the reaction was complete. The mixture was partitioned between ethyl acetate (100 ml) and water (50 ml). The organic layer was washed with brine (50 ml), dried over anhydrous sodium sulfate, and concentrated under reduced pressure to give crude residue which was purified by silica gel flash column chromatography (eluted with 100% ethyl acetate in hexane) to afford tert-butyl 3-((3-(5-hydroxypyridin-2-yl)prop-2-yn-1-yl)oxy)azetidine-1-carboxylate (550 mg, yield 42%) as brown oil.

Step 3: tert-butyl 3-((3-(5-((1r,3r)-3-((5-(5-methyl-5H-pyrido[4,3-b]indol-7-yl)pyridin-2-yl)oxy)cyclobutoxy)pyridin-2-yl)prop-2-yn-1-yl)oxy)azetidine-1-carboxylate

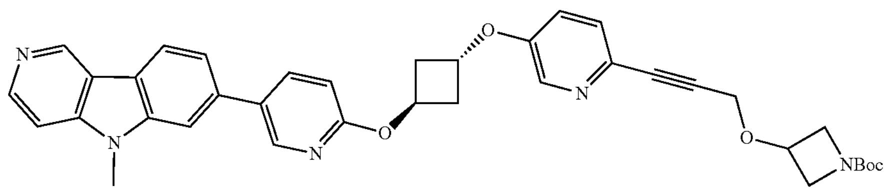 [SMILES: Cn1c2ccncc2c2ccc(-c3ccc(O[C@H]4C[C@H](Oc5ccc(C#CCOC6CN(C(=O)OC(C)(C)C)C6)nc5)C4)nc3)cc21]

A solution of tert-butyl 3-((3-(5-hydroxypyridin-2-yl) prop-2-yn-1-yl)oxy)azetidine-1-carboxylate (100 mg, 0.325 mmol), (1s,3s)-3-((5-(5-methyl-5H-pyrido[4,3-b]indol-7-yl) pyridin-2-yl)oxy)cyclobutyl methanesulfonate (137 mg, 0.325 mmol) and cesium carbonate (211 mg, 0.65 mmol) in dry N,N-dimethylformamide (2 ml) was stirred at 70° C. for 36 hours. TLC showed the reaction was complete. The mixture was partitioned between ethyl acetate (50 ml) and water (25 ml). The organic layer was collected, washed with brine (25 ml), dried over anhydrous sodium sulfate, and concentrated under reduced pressure to give crude residue which was purified by silica gel flash column chromatography (eluted with 3% methanol in dichloromethane) to afford tert-butyl 3-((3-(5-((1r,3r)-3-((5-(5-methyl-5H-pyrido[4,3-b]indol-7-yl)pyridin-2-yl)oxy)cyclobutoxy)pyridin-2-yl)prop-2-yn-1-yl)oxy)azetidine-1-carboxylate (60 mg, yield 29%) as white solid.

Tert-butyl 3-((3-(5-((1r,3r)-3-((5-(5-methyl-5H-pyrido[4,3-b]indol-7-yl)pyridin-2-yl)oxy)cyclobutoxy)pyridin-2-yl) prop-2-yn-1-yl)oxy)azetidine-1-carboxylate was converted into the final compound, 2-(2,6-dioxopiperidin-3-yl)-5-(3-((3-(5-((1r,3r)-3-((5-(5-methyl-5H-pyrido[4,3-b]indol-7-yl) pyridin-2-yl)oxy)cyclobutoxy)pyridin-2-yl)prop-2-yn-1-yl) oxy)azetidin-1-yl)isoindoline-1,3-dione, according to the synthetic scheme below using procedures described above and common procedures known to those skilled in the art.

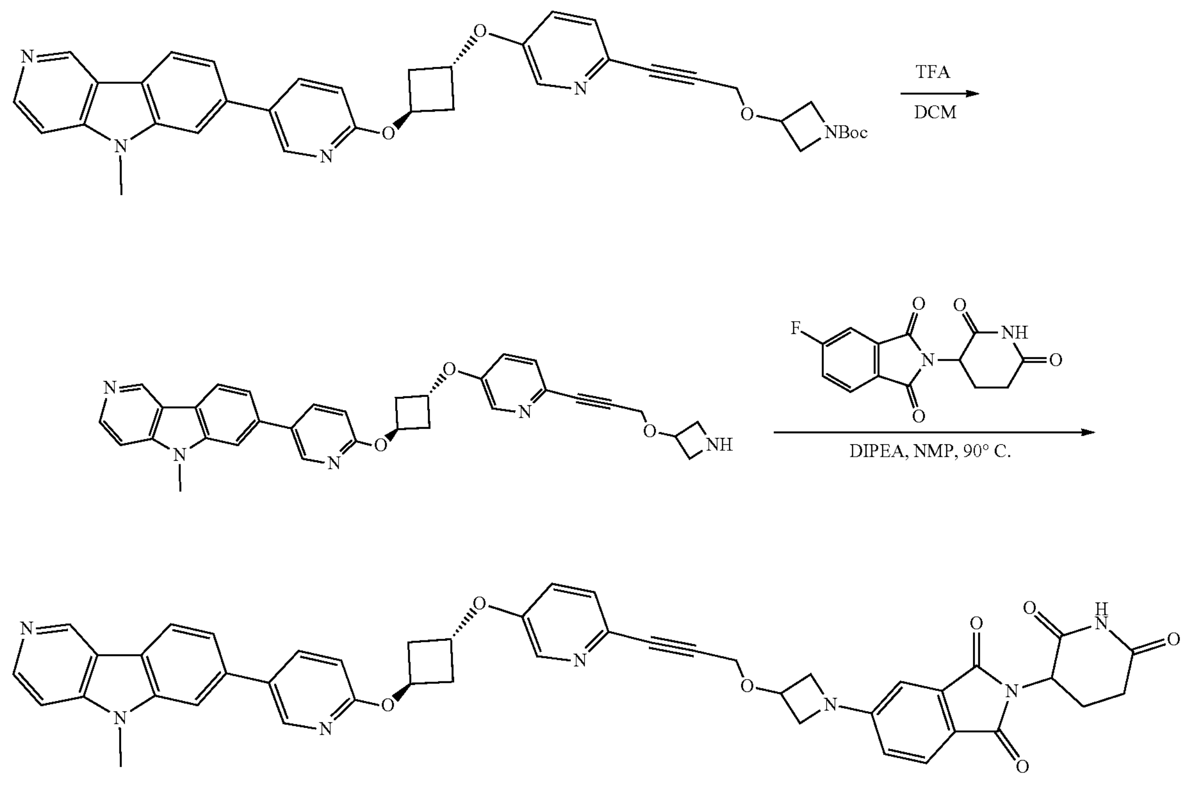

Compound 111

Compound 111: $^1$HNMR (400 MHz, DMSO-d6): δ 1.98-2.02 (m, 1H), 2.54-2.73 (m, 6H), 2.83-2.92 (m, 1H), 3.95-3.97 (m, 5H), 4.31-4.34 (m, 2H), 4.50 (s, 2H), 4.67-4.72 (m, 1H), 5.04-5.13 (m, 2H), 5.42-5.48 (m, 1H), 6.67-6.69 (m, 1H), 6.82 (s, 1H), 6.69-7.01 (m, 1H), 7.33-7.36 (m, 1H), 7.53-7.55 (m, 1H), 7.63-7.67 (m, 3H), 8.01 (s, 1H), 8.21-8.26 (m, 2H), 8.33-8.37 (m, 1H), 8.51-8.55 (m, 1H), 8.65-8.66 (m, 1H), 9.39 (s, 1H), 11.07 (s, 1H). $(M+H)^+$ 788.5.

Using analogous procedures the following exemplary compounds were prepared: 194.

Synthetic Scheme for Exemplary Compound 114

2-(2,6-dioxopiperidin-3-yl)-5-((5-(4-((1r,3r)-3-((5-(5-methyl-5H-pyrido[4,3-b]indol-7-yl)pyridin-2-yl)oxy)cyclobutoxy)butoxy)pentyl)oxy)isoindoline-1,3-dione

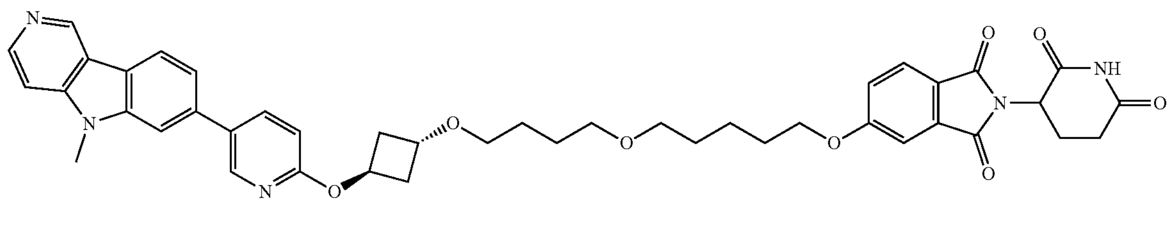 [SMILES: Cn1c2ccncc2c2ccc(-c3ccc(O[C@H]4C[C@H](OCCCCOCCCCCOc5ccc6c(c5)C(=O)N(C5CCC(=O)NC5=O)C6=O)C4)nc3)cc21]

Prepared according to the synthetic scheme below using procedures described above and common procedures known to those skilled in the art.

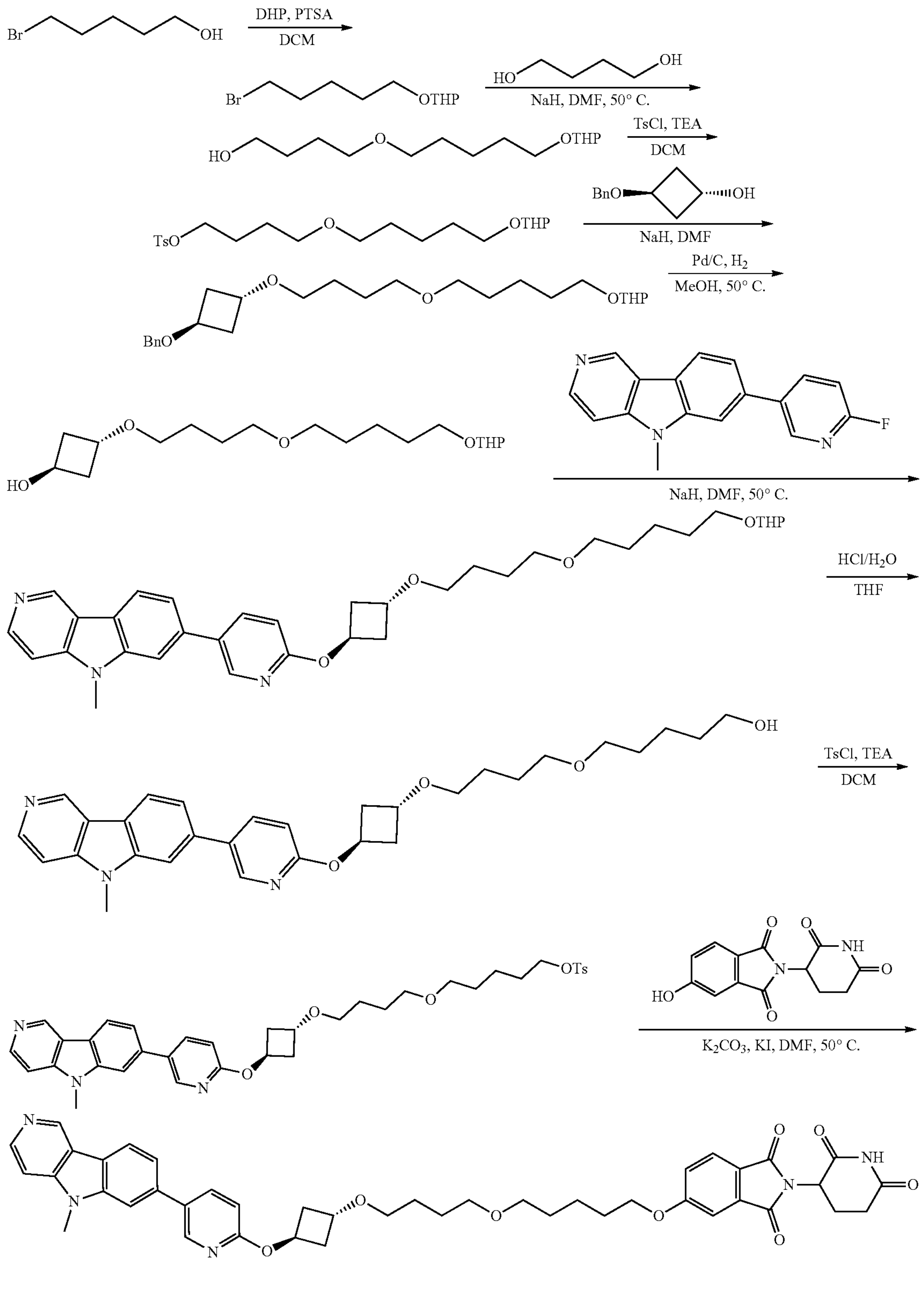
Compound 114
Compound 114: $^1$H NMR (400 MHz, CDCl$_3$): δ 1.52-1.59 (m, 2H), 1.63-1.67 (m, 5H), 1.83-1.90 (m, 1H), 2.11-2.16 (m, 2H), 2.43-2.54 (m, 4H), 2.71-2.92 (m, 4H), 3.39-3.49 (m, 6H), 3.95 (s, 3H), 4.08 (t, J=6.4 Hz, 2H), 4.23-4.29 (m, 1H), 4.94 (dd, J=5.2, 12.0 Hz, 1H), 6.83 (d, J=8.4 Hz, 1H), 7.17 (dd, J=2.0, 8.0 Hz, 1H), 7.32 (d, J=1.6 Hz, 1H), 7.44 (d, J=6.0 Hz, 1H), 7.54 (d, J=8.0 Hz, 1H), 7.60 (s, 1H), 7.75 (d, J=8.4 Hz, 1H), 7.91 (dd, J=2.4, 8.8 Hz, 1H), 8.14 (m, 1H), 8.21 (d, J=8.0 Hz, 1H), 8.48 (d, J=2.4 Hz, 1H), 8.58 (d, J=5.2 Hz, 1H), 9.34 (s, 1H). $(M+H)^+$ 760.5.

Using procedures analogous to those for Compound 140, the following were prepared: Compound 115.

Synthetic Scheme for Exemplary Compound 116

2-(2,6-dioxopiperidin-3-yl)-5-((2-(4-(4-((5-(5-methyl-5H-pyrido[4,3-b]indol-7-yl)pyridin-2-yl)oxy)butoxy)butyl)-2-azaspiro[3.3]heptan-6-yl)oxy)isoindoline-1,3-dione

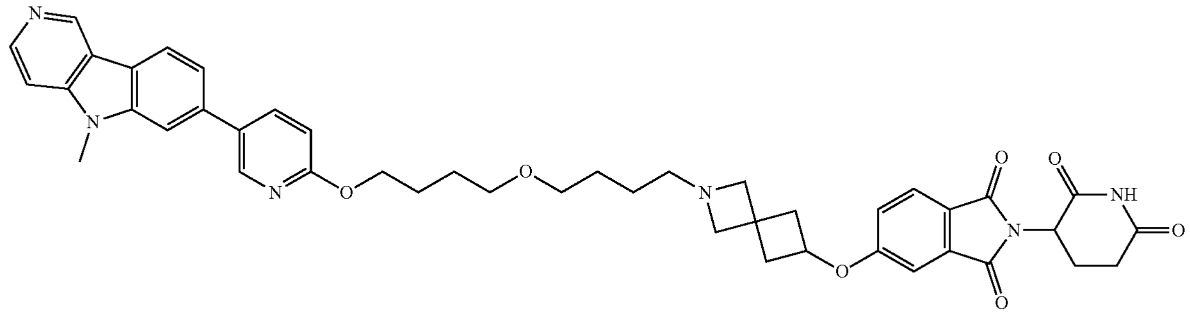 [SMILES: Cn1c2ccncc2c2ccc(-c3ccc(OCCCCOCCCCN4CC5(CC(Oc6ccc7c(c6)C(=O)N(C6CCC(=O)NC6=O)C7=O)C5)C4)nc3)cc21]

Prepared according to the synthetic scheme below using procedures described above and common procedures to those skilled in the art.

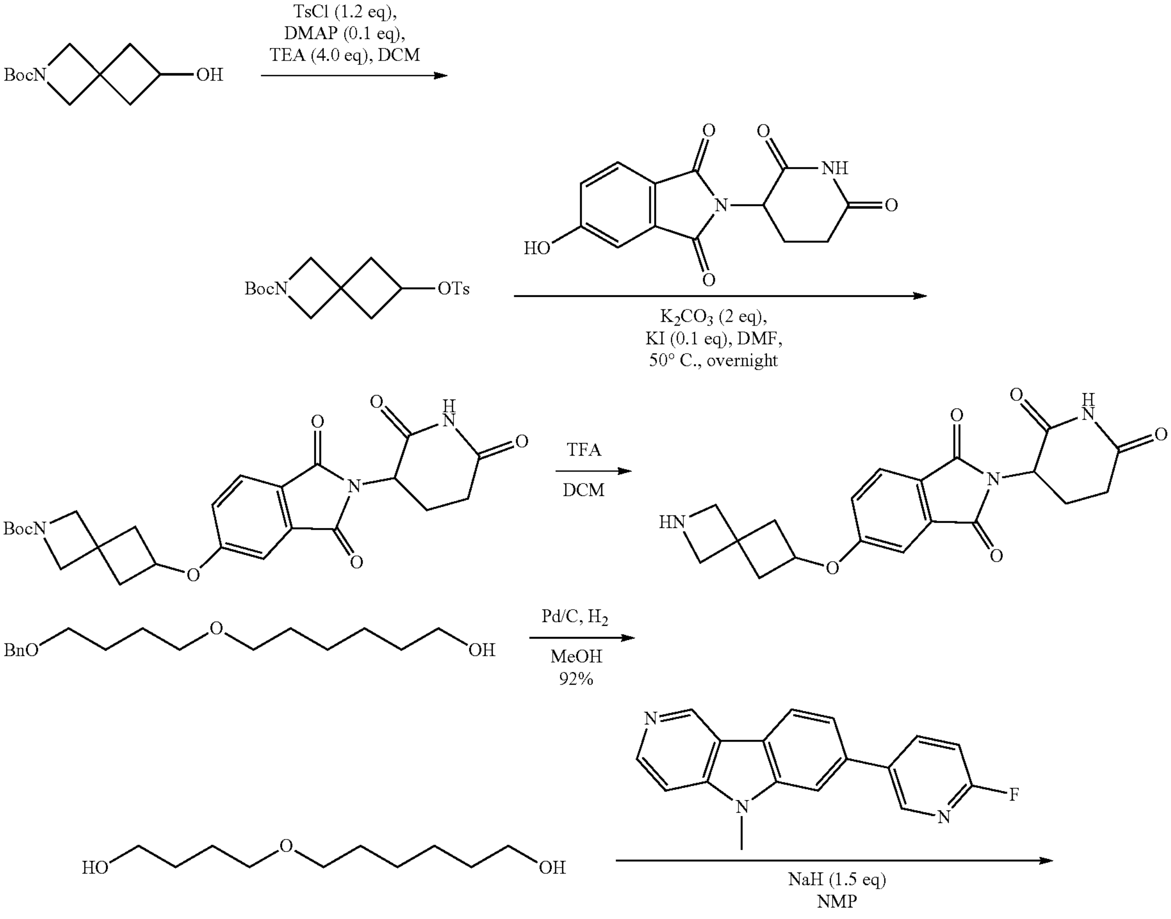

-continued

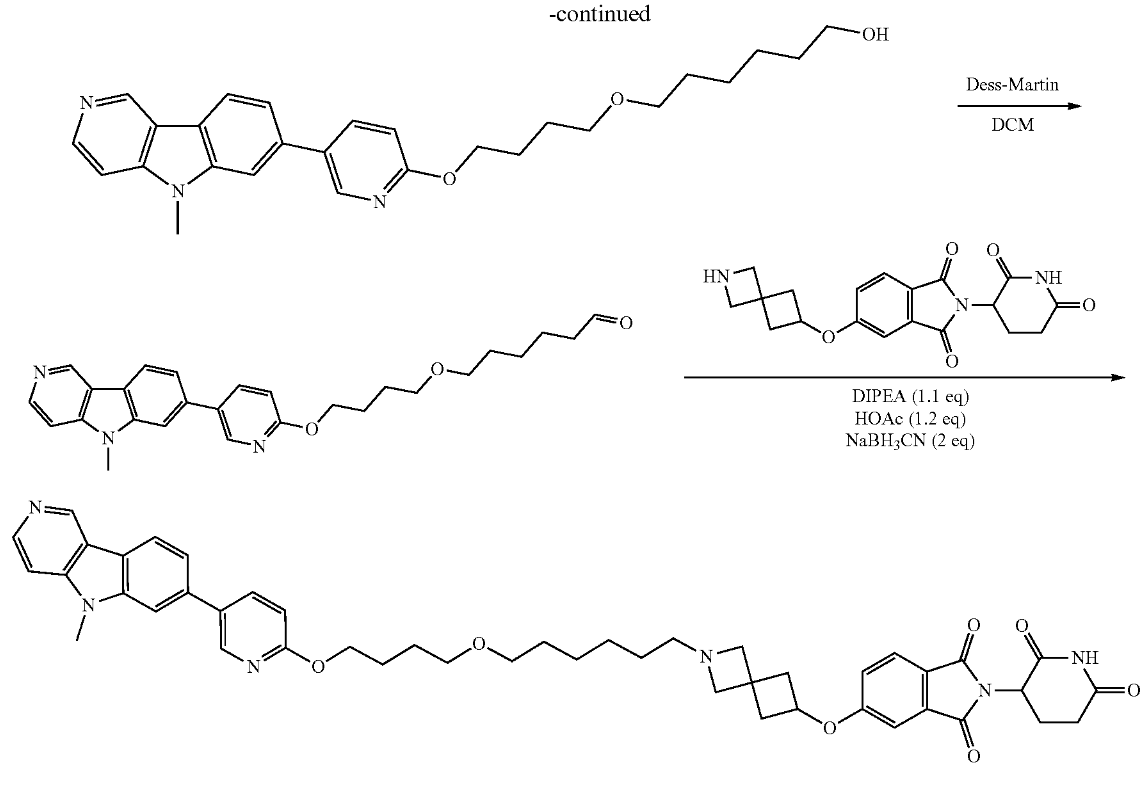

Compound 116

Compound 116: 1HNMR (400 MHz, $CDCl_3$): δ 1.39-1.42 (m, 2H), 1.47-1.52 (m, 2H), 1.64-1.70 (m, 2H), 1.77-1.82 (m, 2H), 2.01-2.07 (m, 1H), 2.21-2.26 (m, 2H), 2.54-2.64 (m, 3H), 2.75-2.90 (m, 5H), 3.42-3.45 (m, 3H), 3.61-3.71 (m, 4H), 3.95 (s, 3H), 4.35 (t, J=6.2 Hz, 2H), 4.78-4.82 (m, 1H), 5.09-5.13 (m, 1H), 6.94 (d, J=8.4 Hz, 1H), 7.20-7.25 (m, 2H), 7.60-7.63 (m, 2H), 7.79 (d, J=8.0 Hz, 1H), 7.97 (s, 1H), 8.18-8.20 (m, 1H), 8.31 (d, J=8.0 Hz, 1H), 8.48 (d, J=5.2 Hz, 1H), 8.65 (s, 1H), 9.34 (s, 1H), 11.11 (s, 1H). $(M+H)^+$ 771.6.

Synthetic Scheme for Compound 118

2-(2,6-dioxopiperidin-3-yl)-5-(3-((3-(5-((1r,3r)-3-((5-(5-methyl-5H-pyrido[4,3-b]indol-7-yl)-3-(trifluoromethyl)pyridin-2-yl)oxy)cyclobutoxy)pyridin-2-yl)prop-2-yn-1-yl)oxy)azetidin-1-yl)isoindoline-1,3-dione

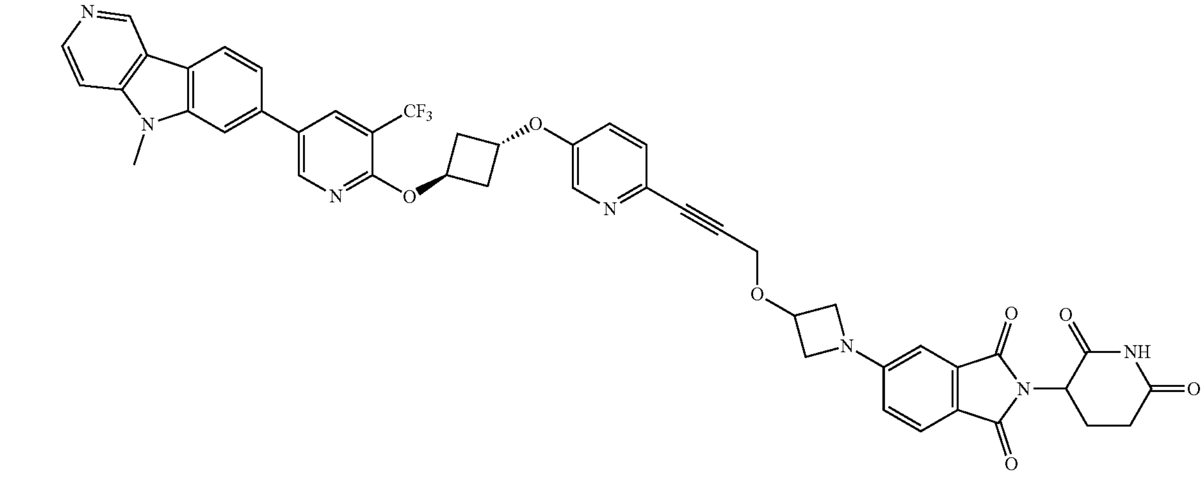 [SMILES: Cn1c2ccncc2c2ccc(-c3cnc(O[C@H]4C[C@H](Oc5ccc(C#CCOC6CN(c7ccc8c(c7)C(=O)N(C7CCC(=O)NC7=O)C8=O)C6)nc5)C4)c(C(F)(F)F)c3)cc21]

Prepared according to the synthetic schemes below using procedures described above and common procedures known to those skilled in the art.

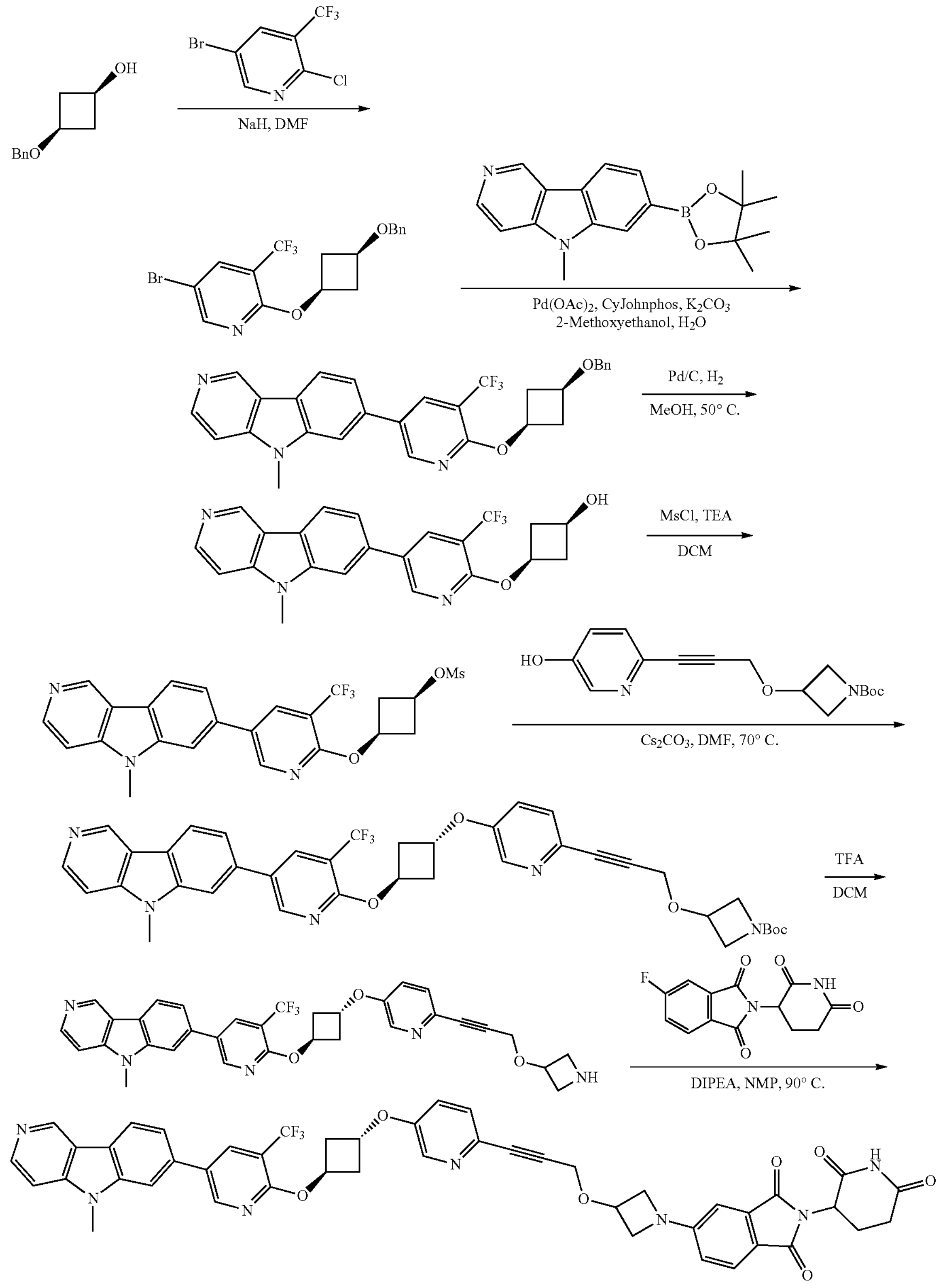
Compound 118
Compound 118: $^1H$ NMR (400 MHz, DMSO-d6): δ 1.98-2.03 (m, 1H), 2.09-2.15 (m, 1H), 2.20-2.24 (m, 1H), 2.70-2.87 (m, 5H), 4.01-4.04 (m, 4H), 4.29-4.34 (m, 1H), 4.46 (s, 2H), 4.75-4.79 (m, 1H), 4.89-4.95 (m, 1H), 5.00-5.06 (m, 1H), 5.33-5.40 (m, 2H), 5.65-5.70 (m, 1H), 6.53-6.55 (m, 1H), 6.79 (s, 1H), 7.08-7.11 (m, 1H), 7.40 (d, J=8.0 Hz, 1H), 7.56-7.65 (m, 4H), 7.95 (s, 1H), 8.19-8.30 (m, 3H), 8.60-8.64 (m, 2H), 9.38 (s, 1H). $(M+H)^+$ 856.5.

Synthetic Scheme for Exemplary Compound 121

(2S,4R)-1-((S)-20-((5-(5H-pyrido[4,3-b]indol-7-yl)pyridin-2-yl)oxy)-2-(tert-butyl)-4-oxo-6,9,12,15,18-pentaoxa-3-azaicosanoyl)-4-hydroxy-N-((S)-1-(4-(4-methylthiazol-5-yl)phenyl)ethyl)pyrrolidine-2-carboxamide

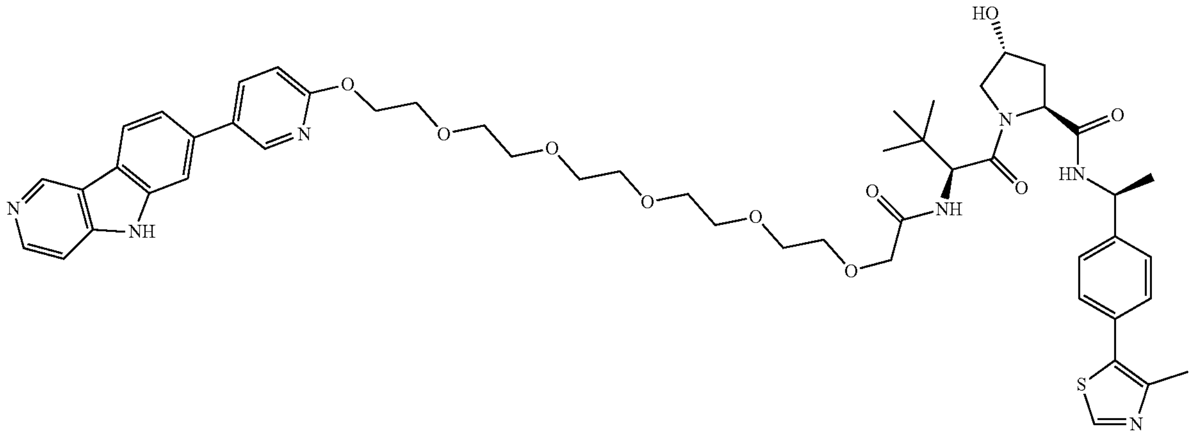 [SMILES: Cc1ncsc1-c1ccc([C@H](C)NC(=O)[C@@H]2C[C@@H](O)CN2C(=O)[C@@H](NC(=O)COCCOCCOCCOCCOCCOc2ccc(-c3ccc4c(c3)[nH]c3ccncc34)cn2)C(C)(C)C)cc1]

Step 1: 14-((5-bromopyridin-2-yl)oxy)-3,6,9,12-tetraoxatetradecan-1-ol

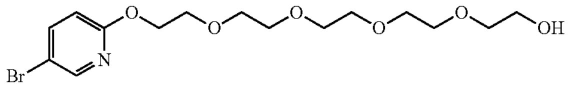 [SMILES: OCCOCCOCCOCCOCCOc1ccc(Br)cn1]

To a solution of 3,6,9,12-tetraoxatetradecane-1,14-diol (20 g, 83.93 mmol) in N,N-dimethylformamide (100 ml) was added sodium hydride (60% in mineral oil) (1.36 g, 34.09 mmol) at 0° C., and the resulting mixture was stirred at 0° C. for 30 minutes. Then 5-bromo-2-fluoropyridine (5 g, 28.41 mmol) was added, and the resulting reaction mixture was stirred at 50° C. for 2 hour. TLC showed the reaction was complete. The reaction mixture was quenched with water (150 ml) at 0° C. and extracted with ethyl acetate (150 ml×2). The combined organic layers was washed with brine (200 ml×2), dried over anhydrous sodium sulfate, and concentrated under reduced pressure to afford a crude residue which was purified by silica gel flash chromatography (eluted with 2% methanol in dichloromethane) to afford 14-((5-bromopyridin-2-yl)oxy)-3,6,9,12-tetraoxatetradecan-1-ol (8 g, yield 72%) as colorless oil.

Step 2: tert-butyl 17-((5-bromopyridin-2-yl)oxy)-3,6,9,12,15-pentaoxaheptadecan-1-oate

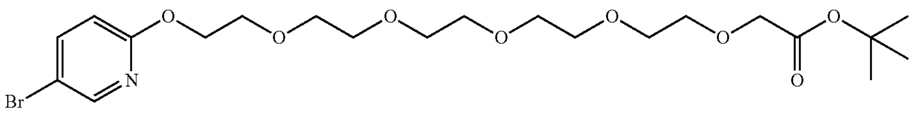 [SMILES: CC(C)(C)OC(=O)COCCOCCOCCOCCOCCOc1ccc(Br)cn1]

To a stirred solution of 14-((5-bromopyridin-2-yl)oxy)-3,6,9,12-tetraoxatetradecan-1-ol (2.00 g, 5.07 mmol) and tetrabutyl ammonium chloride (1.41 g, 5.07 mmol) in dichloromethane (20 ml) and sodium hydroxide (20 ml, 35% in water) was added tert-butyl 2-bromoacetate (2.97 g, 15.22 mmol) at 0° C. The reaction mixture was then allowed to warm up to room temperature and stirred at room temperature overnight. The organic layer was collected, the aqueous layer was extracted with dichloromethane (20 ml). The combined organic layers were washed with brine (20 ml), dried over anhydrous sodium sulfate, and concentrated under reduced pressure to give a crude residue which was purified by silica gel flash column chromatography (eluted with 50% ethyl acetate in hexane) to afford tert-butyl 17-((5-bromopyridin-2-yl)oxy)-3,6,9,12,15-pentaoxaheptadecan-1-oate (1.64 g, yield 64%) as colorless oil.

Step 3: tert-butyl 17-((5-(5H-pyrido[4,3-b]indol-7-yl)pyridin-2-yl)oxy)-3,6,9,12,15-pentaoxaheptadecan-1-oate

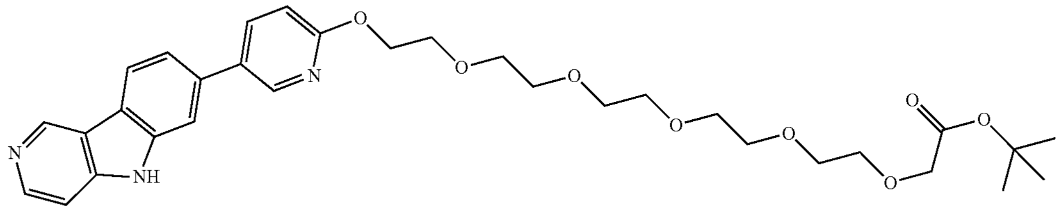 [SMILES: CC(C)(C)OC(=O)COCCOCCOCCOCCOCCOc1ccc(-c2ccc3c(c2)[nH]c2ccncc23)cn1]

To a stirred solution of 7-bromo-5H-pyrido[4,3-b]indole (300 mg, 1.22 mmol), 4,4,4',4',5,5,5',5'-octamethyl-2,2'-bi(1,3,2-dioxaborolane) (620 mg, 2.44 mmol), and potassium acetate (239 mg, 2.44 mmol) in dioxane (5 ml) was added 1,1'-Bis(diphenylphosphino)ferrocene palladium(II)dichloride (176 mg, 0.24 mmol) at room temperature under nitrogen atmosphere, the mixture was degassed with nitrogen three times. The result mixture was stirred at 90° C. overnight. LCMS showed the reaction was complete. To the reaction mixture were added 14-((5-bromopyridin-2-yl)oxy)-3,6,9,12-tetraoxatetradecan-1-ol (930 mg, 1.83 mmol), aqueous sodium carbonate solution (2N, 3.2 ml) and tetrakis(triphenylphosphine)palladium (70 mg, 0.06 mmol); the mixture was degassed with nitrogen three times. The resulting mixture was stirred at 80° C. for 3 hours under nitrogen atmosphere. The reaction mixture was partitioned between ethyl acetate (30 ml) and water (20 ml). The organic layer was collected and the aqueous layer was extracted with ethyl acetate (20 ml). The combined organic layers were washed with brine (30 ml), dried over anhydrous sodium sulfate, and concentrated under reduced pressure to give a crude residue which was purified by silica gel flash chromatography (eluted with 2% methanol in dichloromethane) to afford tert-butyl 17-((5-(5H-pyrido[4,3-b]indol-7-yl)pyridin-2-yl)oxy)-3,6,9,12,15-pentaoxaheptadecan-1-oate (260 mg, yield 36%) as grey oil.

Step 4: 17-((5-(5H-pyrido[4,3-b]indol-7-yl)pyridin-2-yl)oxy)-3,6,9,12,15-pentaoxaheptadecan-1-oic acid

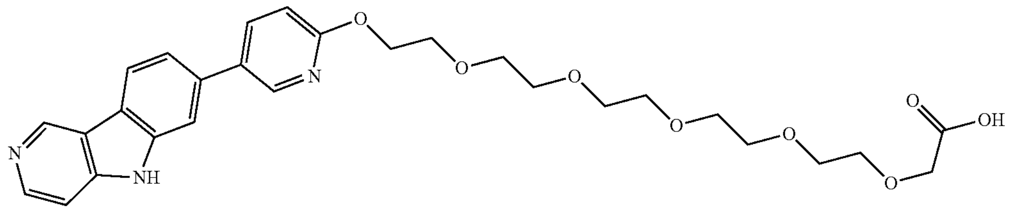 [SMILES: O=C(O)COCCOCCOCCOCCOCCOc1ccc(-c2ccc3c(c2)[nH]c2ccncc23)cn1]

A mixture of tert-butyl 17-((5-(5H-pyrido[4,3-b]indol-7-yl)pyridin-2-yl)oxy)-3,6,9,12,15-pentaoxaheptadecan-1-oate (130 mg, 0.22 mmol) and 2,2,2-trifluoroacetic acid (2 ml) in dichloromethane (1 ml) was stirred at room temperature for one hours. The volatiles were evaporated under reduced pressure to give 17-((5-(5H-pyrido[4,3-b]indol-7-yl)pyridin-2-yl)oxy)-3,6,9,12,15-pentaoxaheptadecan-1-oic acid (120 mg, crude) as brown solid which was used in next step directly without further purification.

Step 5: (2S,4R)-1-((S)-20-((5-(5H-pyrido[4,3-b]indol-7-yl)pyridin-2-yl)oxy)-2-(tert-butyl)-4-oxo-6,9,12,15,18-pentaoxa-3-azaicosan-1-oyl)-4-hydroxy-N-((S)-1-(4-(4-methylthiazol-5-yl)phenyl)ethyl)pyrrolidine-2-carboxamide

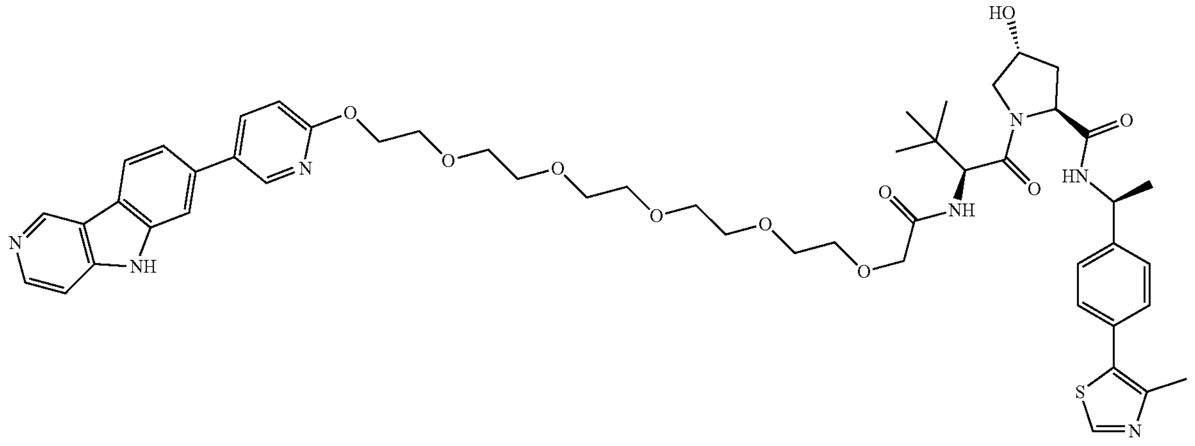 [SMILES: Cc1ncsc1-c1ccc([C@H](C)NC(=O)[C@@H]2C[C@@H](O)CN2C(=O)[C@@H](NC(=O)COCCOCCOCCOCCOCCOc2ccc(-c3ccc4c(c3)[nH]c3ccncc34)cn2)C(C)(C)C)cc1]

To a stirred solution of 17-((5-(5H-pyrido[4,3-b]indol-7-yl)pyridin-2-yl)oxy)-3,6,9,12,15-pentaoxaheptadecan-1-oic acid (120 mg, crude), (2S,4R)-1-((S)-2-amino-3,3-dimethylbutanoyl)-4-hydroxy-N-((S)-1-(4-(4-methylthiazol-5-yl)phenyl)ethyl)pyrrolidine-2-carboxamide hydrochloride (105 mg, 0.22 mmol), and N-ethyl-N-isopropylpropan-2-amine (142 mg, 1.10 mmol) in anhydrous N,N-dimethylformamide (3 ml) was added HATU (2-(7-Aza-1H-benzotriazole-1-yl)-1,1,3,3-tetramethyluronium hexafluorophosphate) (167 mg, 0.44 mmol) at room temperature and stirred for 20 minutes. The mixture was partitioned between ethyl acetate (20 ml) and water (20 ml). The organic layer was collected, washed with brine (20 ml×2), dried over anhydrous sodium sulfate, and concentrated under reduced pressure to give a crude residue which was purified by preparative TLC (eluted with 10% methanol in dichloromethane) to afford (2S,4R)-1-((S)-20-((5-(5H-pyrido[4,3-b]indol-7-yl)pyridin-2-yl)oxy)-2-(tert-butyl)-4-oxo-6,9,12,15,18-pentaoxa-3-azaicosan-1-oyl)-4-hydroxy-N-((S)-1-(4-(4-methylthiazol-5-yl)phenyl)ethyl)pyrrolidine-2-carboxamide (28 mg, yield 13%) as white solid.

$^1$H NMR (400 MHz, DMSOd-6): δ 0.93 (s, 9H), 1.36-1.47 (m, 3H), 1.73-1.80 (m, 1H), 1.96-2.09 (m, 2H), 3.23-3.60 (m, 16H), 3.79 (t, J=3.6 Hz, 2H), 3.96 (s, 2H), 4.28 (s, 1H), 4.42-4.46 (m, 3H), 4.54 (d, J=9.6 Hz, 1H), 4.90 (t, J=7.6 Hz, 1H), 5.12 (s, 1H), 6.97 (d, J=8.4 Hz, 1H), 7.35-7.43 (m, 5H), 7.65-7.69 (m, 2H), 7.87 (s, 1H), 8.12-8.15 (m, 1H), 8.37-8.43 (m, 2H), 8.51 (d, J=5.6 Hz, 1H), 8.59 (d, J=1.6 Hz, 1H), 8.97 (s, 1H), 9.51 (s, 1H), 12.28 (s, 1H). $(M+H)^+$ 966.7.

Using analogous procedures the following were prepared: Compound 1, Compound 5, Compound 6, Compound 120, and Compound 122.

Synthetic Scheme for Exemplary Compound 119

(2S,4R)-1-((S)-17-((5-(5H-pyrido[4,3-b]indol-7-yl)-3-(trifluoromethyl)pyridin-2-yl)oxy)-2-(tert-butyl)-4-oxo-6,9,12,15-tetraoxa-3-azaheptadecanoyl)-4-hydroxy-N-((S)-1-(4-(4-methylthiazol-5-yl)phenyl)ethyl)pyrrolidine-2-carboxamide

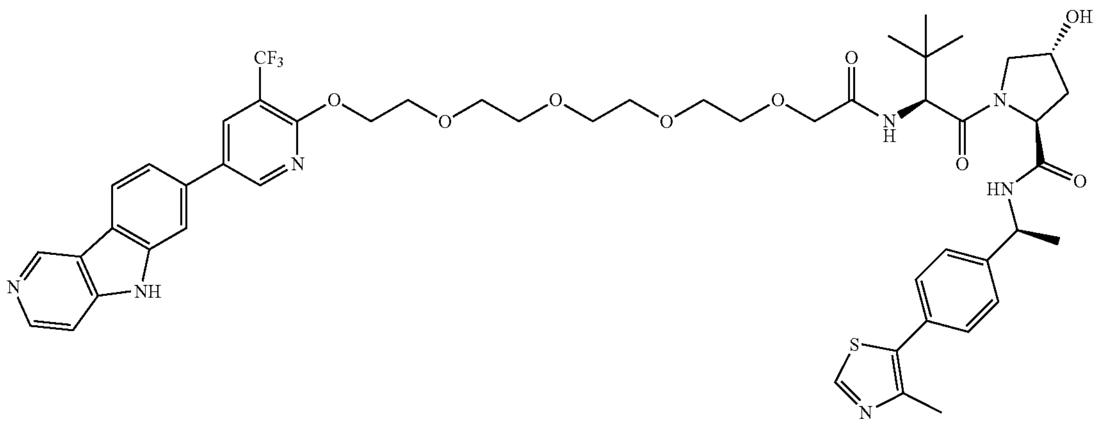 [SMILES: Cc1ncsc1-c1ccc([C@H](C)NC(=O)[C@@H]2C[C@@H](O)CN2C(=O)[C@@H](NC(=O)COCCOCCOCCOCCOc2ncc(-c3ccc4c(c3)[nH]c3ccncc34)cc2C(F)(F)F)C(C)(C)C)cc1]

Prepared according to the synthetic scheme below using procedures described above and common procedures known to those skilled in the art.
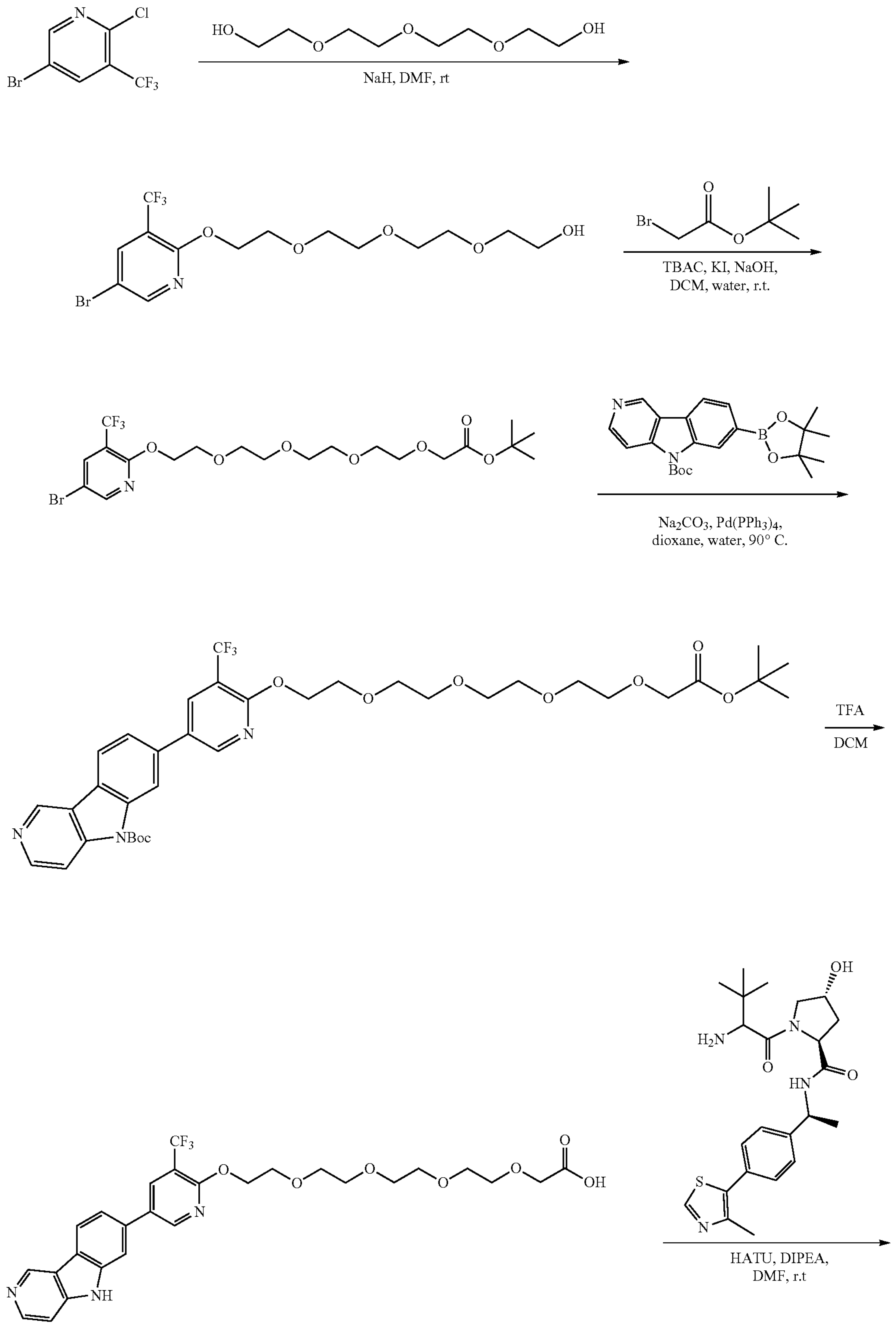

-continued

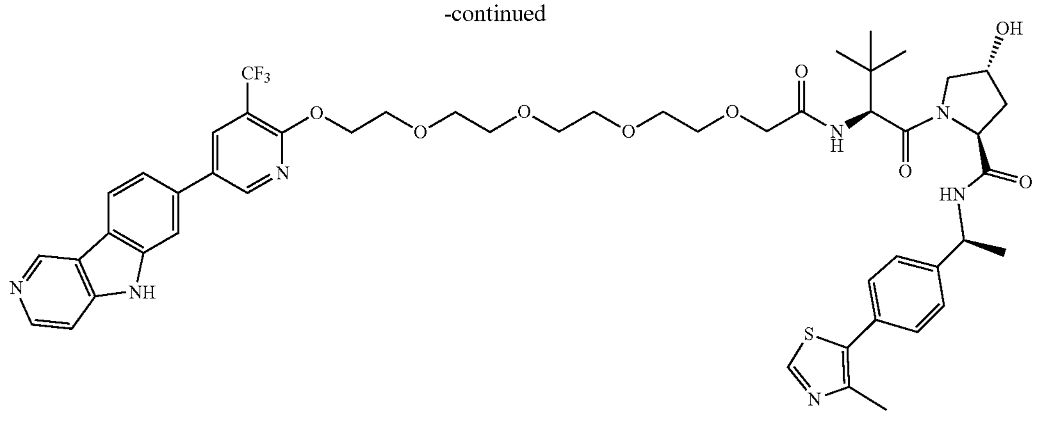

Compound 119

Compound 119: $^1$H NMR (400 MHz, DMSO-$d_6$): δ 0.93 (s, 9H), 1.35 (t, J=6.8 Hz, 3H), 1.77-1.78 (s, 1H), 2.02-2.04 (m, 1H), 2.44 (s, 3H), 3.53-3.64 (m, 14H), 3.80-3.85 (m, 2H), 3.95 (s, 2H), 4.28 (s, 1H), 4.44 (d, J=8.2 Hz, 1H), 4.54 (d, J=9.6 Hz, 1H), 4.58-4.63 (m, 2H), 4.90 (s, 1H), 5.12 (s, 1H), 7.26-7.50 (m, 5H), 7.54 (d, J=5.8 Hz, 1H), 7.66 (d, J=8.2 Hz, 1H), 7.90 (s, 1H), 8.35 (d, J=8.0 Hz, 1H), 8.42-8.45 (m, 3H), 8.85 (s, 1H), 8.97 (s, 1H), 9.41 (s, 1H), 11.92 (s, 1H). $(M+H)^+$ 990.7.

Synthetic Scheme for Exemplary Compound 126

2-(2,6-dioxopiperidin-3-yl)-5-((5-(6-(methyl((1r,3r)-3-((5-(5-methyl-5H-pyrido[4,3-b]indol-7-yl)pyridin-2-yl)oxy)cyclobutyl)amino)-2-azaspiro[3.3]heptan-2-yl)pentyl)oxy)isoindoline-1,3-dione

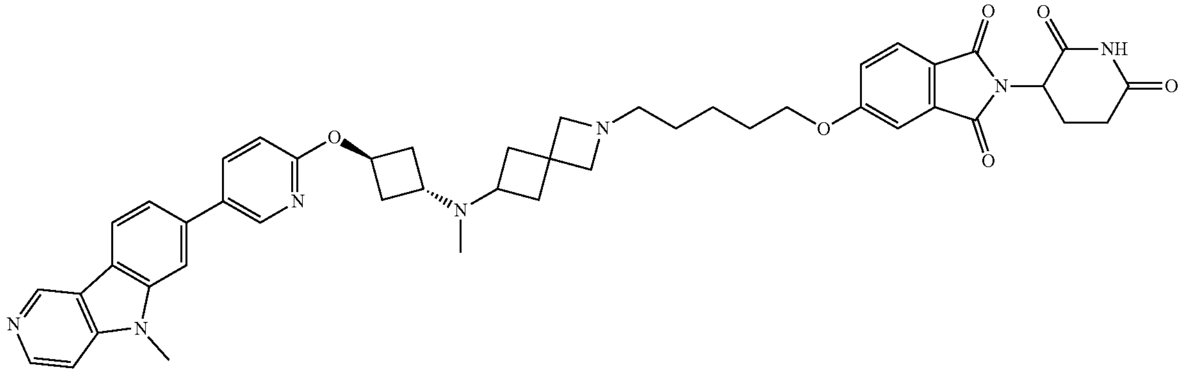 [SMILES: Cn1c2ccncc2c2ccc(-c3ccc(O[C@H]4C[C@H](N(C)C5CC6(C5)CN(CCCCCOc5ccc7c(c5)C(=O)N(C5CCC(=O)NC5=O)C7=O)C6)C4)nc3)cc21]

Step 1: (1r,3r)-3-(methylamino)cyclobutanol

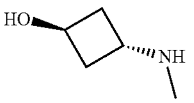

To a solution of tert-butyl ((1r,3r)-3-hydroxycyclobutyl) carbamate (2 g, 10.7 mmol) in tetrahydrofuran (30 ml) was added lithium aluminum hydride (1.6 g, 42.7 mmol) at 0° C. The mixture was stirred at 65° C. for 2 hours. TLC showed the reaction was complete. The mixture was quenched with water (1.6 ml), sodium hydroxide (1.6 ml, 15% in water) and water (4.8 ml) at 0° C. The mixture was stirred at room temperature for 15 minutes and filtered. The filtrate was dried over anhydrous sodium sulfate, and concentrated under reduced pressure to give a crude (1r,3r)-3-(methylamino)cyclobutanol (1.3 g) as colorless oil which was used in the next step without further purification.

Step 2: tert-butyl ((1r,3r)-3-hydroxycyclobutyl)(methyl)carbamate

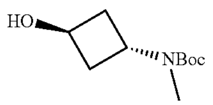

To a solution of (1r,3r)-3-(methylamino)cyclobutanol (1.3 g, 12.8 mmol) and triethylamine (2.6 g, 25.7 mmol) in dichloromethane (10 ml) was added di-tert-butyl carbonate (4.2 g, 19.28 mmol) at room temperature. The mixture was stirred at room temperature for 12 hours. TLC showed the reaction was complete. The mixture was diluted with dichloromethane (10 ml) and washed with aqueous hydrochloride acid (1N, 10 ml). The organic layer was collected, washed with brine (20 ml), dried over anhydrous sodium sulfate, and concentrated under reduced pressure to give a crude residue which was purified by silica gel flash chromatography (eluted with 33-50% ethyl acetate in hexane) to afford tert-butyl ((1r,3r)-3-hydroxycyclobutyl)(methyl)carbamate (1.2 g, two steps 56%) as colorless oil.

Step 3: tert-butyl methyl((1r,3r)-3-((5-(5-methyl-5H-pyrido[4,3-b]indol-7-yl)pyridin-2-yl)oxy)cyclobutyl)carbamate

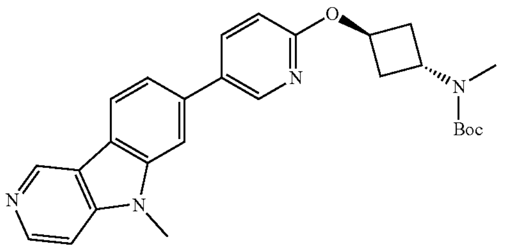 [SMILES: Cn1c2ccncc2c2ccc(-c3ccc(O[C@H]4C[C@H](N(C)C(=O)OC(C)(C)C)C4)nc3)cc21]

To a solution of 7-(6-fluoropyridin-3-yl)-5-methyl-5H-pyrido[4,3-b]indole (300 mg, 1.1 mmol) and tert-butyl ((1r,3r)-3-hydroxycyclobutyl)(methyl)carbamate (218 mg, 1.1 mmol) in 1-methylpyrrolidin-2-one (3 ml) was added sodium hydride (60% in mineral oil) at 0° C. The mixture was allowed to cool to room temperature and stirred at room temperature for 30 minutes. LC-MS showed the reaction was complete. The mixture was partitioned between ethyl acetate (30 ml) and water (30 ml). The organic layer was collected, washed with brine (20 ml), dried over anhydrous sodium sulfate, and concentrated under reduced pressure to give a crude residue which was purified by silica gel flash chromatography (eluted with 1-2% methanol in dichloromethane) to afford tert-butyl methyl((1r,3r)-3-((5-(5-methyl-5H-pyrido[4,3-b]indol-7-yl)pyridin-2-yl)oxy)cyclobutyl)carbamate (450 mg, 91%) as light yellow oil.

Step 4: afford tert-butyl 6-(methyl((1r,3r)-3-((5-(5-methyl-5H-pyrido[4,3-b]indol-7-yl)pyridin-2-yl)oxy)cyclobutyl)amino)-2-azaspiro[3.3]heptane-2-carboxylate

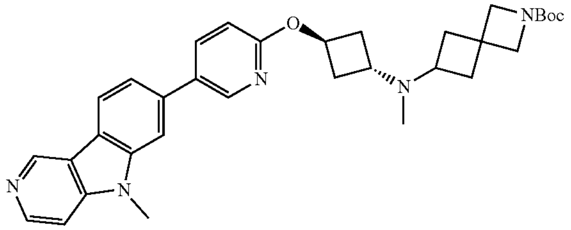 [SMILES: Cn1c2ccncc2c2ccc(-c3ccc(O[C@H]4C[C@H](N(C)C5CC6(C5)CN(C(=O)OC(C)(C)C)C6)C4)nc3)cc21]

A mixture of tert-butyl methyl((1r,3r)-3-((5-(5-methyl-5H-pyrido[4,3-b]indol-7-yl)pyridin-2-yl)oxy)cyclobutyl)carbamate (450 mg, 0.98 mmol) and 2,2,2-trifluoroacetic acid (2 ml) in dichloromethane (2 ml) was stirred at room temperature for 1 hour. TLC showed the reaction was complete. The volatiles were evaporated under reduced pressure. The residue was taken up in methanol (5 ml), followed by sequential addition of N-ethyl-N-isopropylpropan-2-amine (380 mg, 2.94 mmol), tert-butyl 6-oxo-2-azaspiro[3.3]heptane-2-carboxylate (207 mg, 0.98 mmol) and acetic acid (71 mg, 1.18 mmol) at 0° C. The resulting mixture was stirred at room temperature for 30 minutes and sodium cyanoborohydride (124 mg, 1.96 mmol) was added. The mixture was stirred at room temperature for 18 hours. TLC showed the reaction was complete. The mixture was concentrated and the residue was partitioned between ethyl acetate (20 ml) and water (20 ml). The organic layer was collected, washed with brine (20 ml), dried over anhydrous sodium sulfate, and concentrated under reduced pressure to give a crude residue which was purified by silica gel flash chromatography (eluted with 2-5% methanol in dichloromethane) to afford tert-butyl 6-(methyl((1r,3r)-3-((5-(5-methyl-5H-pyrido[4,3-b]indol-7-yl)pyridin-2-yl)oxy)cyclobutyl)amino)-2-azaspiro[3.3]heptane-2-carboxylate (240 mg, two steps 44%) as white solid.

Step 5: N-methyl-N-((1r,3r)-3-((5-(5-methyl-5H-pyrido[4,3-b]indol-7-yl)pyridin-2-yl)oxy)cyclobutyl)-2-azaspiro[3.3]heptan-6-amine

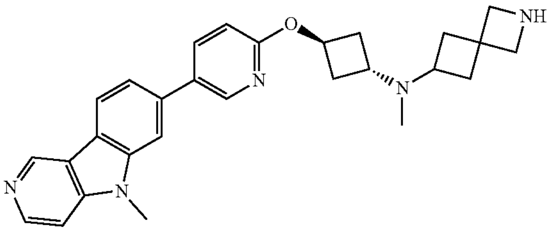 [SMILES: Cn1c2ccncc2c2ccc(-c3ccc(O[C@H]4C[C@H](N(C)C5CC6(CNC6)C5)C4)nc3)cc21]

A mixture of tert-butyl 6-(methyl((1r,3r)-3-((5-(5-methyl-5H-pyrido[4,3-b]indol-7-yl)pyridin-2-yl)oxy)cyclobutyl)amino)-2-azaspiro[3.3]heptane-2-carboxylate (100 mg, 0.18 mmol) and 2,2,2-trifluoroacetic acid (0.5 ml) in anhydrous dichloromethane (0.5 ml) was stirred at room temperature for 1 hour. TLC showed the reaction was complete. The mixture was concentrated under reduced pressure to give crude N-methyl-N-((1r,3r)-3-((5-(5-methyl-5H-pyrido[4,3-b]indol-7-yl)pyridin-2-yl)oxy)cyclobutyl)-2-azaspiro[3.3]heptan-6-amine (100 mg) which was used in the next step without further purification.

Step 6: 2-(2,6-dioxopiperidin-3-yl)-5-((5-(6-(methyl((1r,3r)-3-((5-(5-methyl-5H-pyrido[4,3-b]indol-7-yl)pyridin-2-yl)oxy)cyclobutyl)amino)-2-azaspiro[3.3]heptan-2-yl)pentyl)oxy)isoindoline-1,3-dione

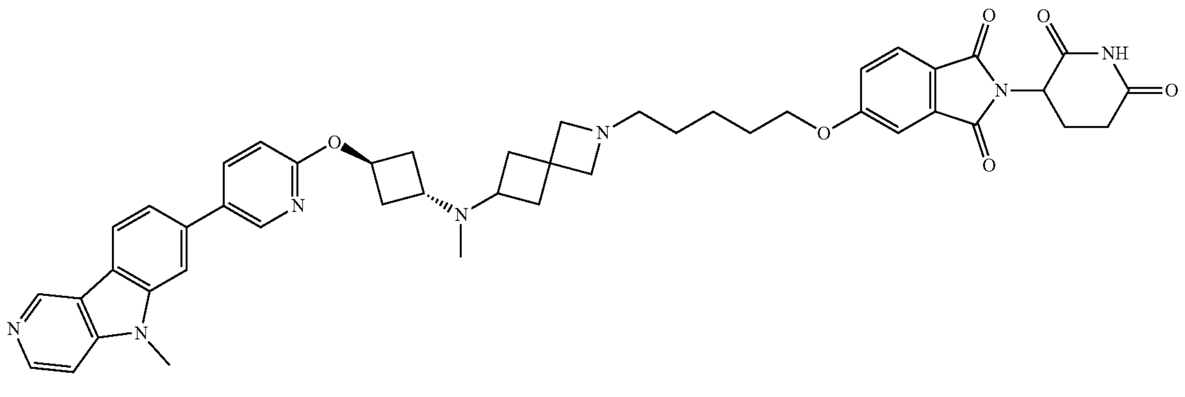 [SMILES: Cn1c2ccncc2c2ccc(-c3ccc(O[C@H]4C[C@H](N(C)C5CC6(C5)CN(CCCCCOc5ccc7c(c5)C(=O)N(C5CCC(=O)NC5=O)C7=O)C6)C4)nc3)cc21]

N-methyl-N-((1r,3r)-3-((5-(5-methyl-5H-pyrido[4,3-b]indol-7-yl)pyridin-2-yl)oxy)cyclobutyl)-2-azaspiro[3.3]heptan-6-amine (100 mg, crude) and N-ethyl-N-isopropyl-propan-2-amine (70 mg, 0.54 mmol) in methanol (10 ml) was added 5-((2-(2,6-dioxopiperidin-3-yl)-1,3-dioxoisoindolin-5-yl)oxy)pentanal (65 mg, 0.18 mmol) and acetic acid (13 mg, 0.21 mmol) at 0° C. The mixture was stirred at room temperature for 30 minutes and then sodium cyanoborohydride (23 mg, 0.36 mmol) was added. The mixture was stirred at room temperature for 16 hours. TLC showed the reaction was complete. The mixture was concentrated under reduced pressure to give a crude residue which was purified by HPLC to afford 2-(2,6-dioxopiperidin-3-yl)-5-((5-(6-(methyl((1r,3r)-3-((5-(5-methyl-5H-pyrido[4,3-b]indol-7-yl)pyridin-2-yl)oxy)cyclobutyl)amino)-2-azaspiro[3.3]heptan-2-yl)pentyl)oxy)isoindoline-1,3-dione (57.3 mg, two steps 40%) as white solid.

$^1$H NMR (400 MHz, DMSO-d6): δ 1.42-1.51 (m, 4H), 1.75-1.79 (m, 2H), 2.03-2.06 (m, 1H), 2.54 (s, 3H), 2.58-2.68 (m, 5H), 2.81-2.94 (m, 2H), 3.11-3.17 (m, 2H), 3.61-3.71 (m, 3H), 3.98-4.11 (m, 6H), 4.15 (s, 3H), 4.17-4.23 (m, 3H), 5.10-5.14 (m, 1H), 5.25-5.31 (m, 1H), 7.03 (d, J=8.4 Hz, 1H), 7.33-7.42 (m, 2H), 7.84-7.89 (m, 1H), 8.22-8.32 (m, 3H), 8.55 (d, J=8.0 Hz, 11H), 8.71 (s, 1H), 8.78 (d, J=6.4 Hz, 1H), 9.78 (s, 1H), 10.05 (brs, 1H), 10.51 (brs, 1H), 11.11 (s, 11H). $(M+H)^+$ 796.6.

Synthetic Scheme for Exemplary Compound 127

3-(5-(4-((1-(5-(5-methyl-5H-pyrido[4,3-b]indol-7-yl)pyridin-2-yl)piperidin-4-yl)methyl)piperazin-1-yl)-1-oxoisoindolin-2-yl)piperidine-2,6-dione

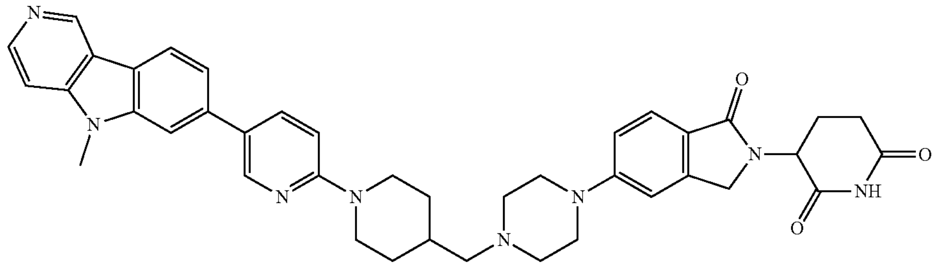 [SMILES: Cn1c2ccncc2c2ccc(-c3ccc(N4CCC(CN5CCN(c6ccc7c(c6)CN(C6CCC(=O)NC6=O)C7=O)CC5)CC4)nc3)cc21]

Step 1: (1-(5-(5-methyl-5H-pyrido[4,3-b]indol-7-yl)pyridin-2-yl)piperidin-4-yl)methanol

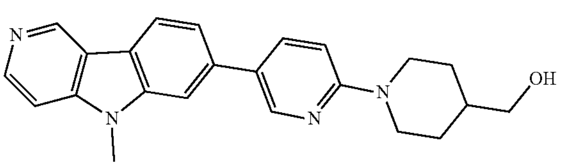 [SMILES: Cn1c2ccncc2c2ccc(-c3ccc(N4CCC(CO)CC4)nc3)cc21]

To the mixture of 7-(6-fluoropyridin-3-yl)-5-methyl-5H-pyrido[4,3-b]indole (200 mg, 0.72 mmol) and piperidin-4-ylmethanol (108 mg, 0.93 mmol) in 1-methylpyrrolidin-2-one (5 ml) was added potassium carbonate (298 mg, 2.16 mmol), and it was stirred at 100° C. overnight under nitrogen atmosphere. The cooled reaction mixture was partitioned between ethyl acetate (30 ml) and water (30 ml). The organic layer was collected, washed with brine (30 ml), dried over anhydrous sodium sulfate, and concentrated under reduced pressure to give a crude residue which was purified by silica gel flash chromatography (eluted with 2-5% methanol in dichloromethane) to afford (1-(5-(5-methyl-5H-pyrido[4,3-b]indol-7-yl)pyridin-2-yl)piperidin-4-yl)methanol (205 mg, yield 76%) as light yellow solid.

Step 2: 1-(5-(5-methyl-5H-pyrido[4,3-b]indol-7-yl)pyridin-2-yl)piperidine-4-carbaldehyde

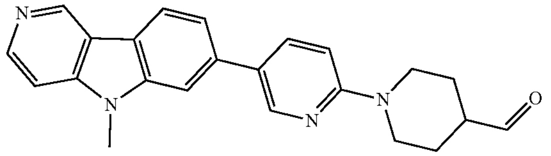 [SMILES: Cn1c2ccncc2c2ccc(-c3ccc(N4CCC(C=O)CC4)nc3)cc21]

To a solution of Dess-Martin periodinane (136 mg, 0.32 mmol) in dichloromethane (3 ml) (1-(5-(5-methyl-5H-pyrido[4,3-b]indol-7-yl)pyridin-2-yl)piperidin-4-yl)methanol (60 mg, 0.16 mmol) was added and stirred at room temperature for 1 hour under nitrogen atmosphere. The reaction mixture was partitioned between dichloromethane (20 ml) and water (20 ml). The organic layer was collected, washed with brine (20 ml), dried over anhydrous sodium sulfate, and concentrated under reduced pressure to give a crude residue which was purified by prep TLC (eluted with 3% methanol in dichloromethane) to afford 1-(5-(5-methyl-5H-pyrido[4,3-b]indol-7-yl)pyridin-2-yl)piperidine-4-carbaldehyde (58 mg, yield 97%) as white solid.

Step 3: tert-Butyl 4-(1-oxo-3H-isobenzofuran-5-yl)piperazine-1-carboxylate

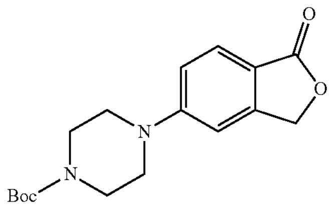 [SMILES: CC(C)(C)OC(=O)N1CCN(c2ccc3c(c2)COC3=O)CC1]

To a solution of 5-bromo-3H-isobenzofuran-1-one (45 g, 211.24 mmol, 1.00 eq) and tert-butyl piperazine-1-carboxylate (39.34 g, 211.24 mmol, 1.00 eq) in dioxane (500 mL) was added tris(dibenzylideneacetone)dipalladium(0) (19.34 g, 21.12 mmol, 0.10 eq), 4,5-bis (diphenylphosphino)-9,9-dimethylxanthene (12.22 g, 21.12 mmol, 0.10 eq) and potassium phosphate (89.68 g, 422.48 mmol, 2.00 eq). The mixture was heated to 100° C. for 16 hr under nitrogen protection. The mixture was filtered through a pad of celite and filtrate was concentrated in vacuum. The residue was triturated in ethyl acetate:petroleum ether (500 mL, v/v=1:2). Tert-Butyl 4-(1-oxo-3H-isobenzofuran-5-yl)piperazine-1-carboxylate (50 g, 122.5 mmol, 58% yield, 78% purity) was obtained as yellow solid.

Step 4: 4-(4-tert-butoxycarbonyl piperazin-1-yl)-2-(hydroxymethyl)benzoic acid

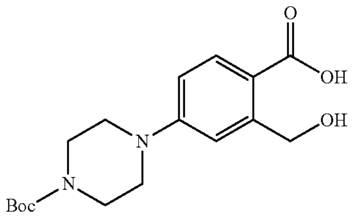 [SMILES: CC(C)(C)OC(=O)N1CCN(c2ccc(C(=O)O)c(CO)c2)CC1]

To a mixture of tert-butyl 4-(1-oxo-3H-isobenzofuran-5-yl)piperazine-1-carboxylate (47.8 g, 150.14 mmol, 1.00 eq) in tetrahydrofuran (150 mL), methanol (150 mL) and water (150 mL) was added sodium hydroxide (24 g, 600 mmol, 4.00 eq). The mixture was stirred at 25° C. for 1 hr. The solution was adjusted to pH=4-5 with aqueous hydrochloride solution (1M) and extracted with ethyl acetate (100 mL×5). The organic layers were concentrated in vacuum. The crude was triturated in ethyl acetate:petroleum ether (450 mL, v:v=1:2). 4-(4-tert-butoxycarbonyl piperazin-1-yl)-2-(hydroxymethyl)benzoic acid (40 g, 118.91 mmol, 79% yield) was obtained as yellow solid.

Step 5: tert-Butyl 4-[3-(hydroxymethyl)-4-methoxy-carbonyl-phenyl]piperazine-1-carboxylate

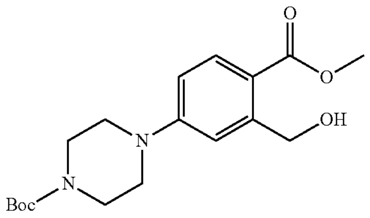 [SMILES: COC(=O)c1ccc(N2CCN(C(=O)OC(C)(C)C)CC2)cc1CO]

To a solution of 4-(4-tert-butoxycarbonylpiperazin-1-yl)-2-(hydroxymethyl)benzoic acid (20 g, 59.46 mmol, 1.00 eq) in methanol (100 mL) and ethyl acetate (100 mL) was added TMS-diazomethane (2 M, 89 mL, 3.00 eq) at −10° C. The solution was stirred at −10° C. for 0.25 hr. The solution was quenched with water (300 mL) and extracted with ethyl acetate (150 mL×3). The organic layer was dried over sodium sulfate and filtered. The filtrate was concentrated. Tert-Butyl 4-[3-(hydroxymethyl)-4-methoxycarbonyl-phenyl]piperazine-1-carboxylate (20.84 g, crude) was obtained as brown oil.

Step 6: tert-Butyl 4-[3-(bromomethyl)-4-methoxy-carbonyl-phenyl]piperazine-1-carboxylate

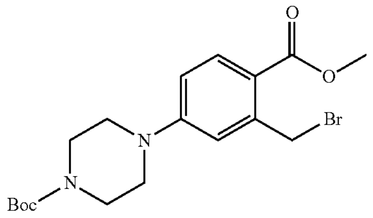 [SMILES: COC(=O)c1ccc(N2CCN(C(=O)OC(C)(C)C)CC2)cc1CBr]

To a solution of tert-butyl 4-[3-(hydroxymethyl)-4-methoxycarbonyl-phenyl]piperazine-1-carboxylate (20.84 g, 59.47 mmol, 1.00 eq) in tetrahydrofuran (200 mL) was added triphenylphosphine (23.4 g, 89.21 mmol, 1.50 eq) and tetrabromomethane (29.58 g, 89.21 mmol, 1.50 eq). The solution was stirred at 25° C. for 1 hr. The solution was quenched with water (200 mL) and extracted with ethyl acetate (100 mL×2). The organic layer was dried over sodium sulfate and filtered. The filtrate was concentrated in vacuum. The residue was purified by silica gel column chromatography (ethyl acetate:petroleum ether=1:50-1:8). Tert-Butyl 4-[3-(bromomethyl)-4-methoxycarbonyl-phenyl]piperazine-1-carboxylate (12 g, 29.03 mmol, 49% yield) was obtained as a pale-yellow oil.

Step 7: tert-Butyl 4-[2-(2,6-dioxo-3-piperidyl)-1-oxo-isoindolin-5-yl]piperazine-1-carboxylate

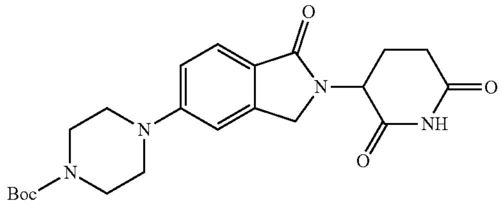 [SMILES: CC(C)(C)OC(=O)N1CCN(c2ccc3c(c2)CN(C2CCC(=O)NC2=O)C3=O)CC1]

To a solution of tert-butyl 4-[3-(bromomethyl)-4-methoxycarbonyl-phenyl]piperazine-1-carboxylate (12 g, 29.03 mmol, 1.00 eq) in acetonitrile (300 mL) was added 3-aminopiperidine-2,6-dione; hydrochloride (7.17 g, 43.55 mmol, 1.50 eq) and N-ethyl-N-isopropylpropan-2-amine (11.26 g, 87.09 mmol, 15 mL, 3.00 eq). The solution was stirred at 80° C. for 16 hr. LCMS showed reaction was almost complete. The reaction mixture was cooled to 20° C. and filtered. The solid was washed with acetonitrile (30 mL). tert-Butyl 4-[2-(2,6-dioxo-3-piperidyl)-1-oxo-isoindolin-5-yl]piperazine-1-carboxylate (6 g, 14 mmol, 48% yield) was obtained as a white solid.

Step 8: 3-(1-oxo-5-piperazin-1-yl-isoindolin-2-yl) piperidine-2,6-dione

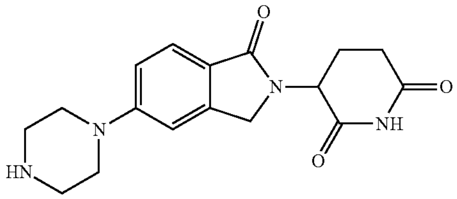 [SMILES: O=C1CCC(N2Cc3cc(N4CCNCC4)ccc3C2=O)C(=O)N1]

To a mixture of tert-butyl 4-[2-(2,6-dioxo-3-piperidyl)-1-oxo-isoindolin-5-yl]piperazine-1-carboxylate (6 g, 14 nmol, 1.00 eq) in dioxane (70 mL) was added hydrochloride/dioxane (4 M, 100 mL, 28.57 eq). The mixture was stirred at 25° C. for 2 hr. The mixture was poured into ethyl acetate (400 mL) and stirred for 30 minutes. The suspension was filtered and solid was collected. 3-(1-oxo-5-piperazin-1-yl-isoindolin-2-yl) piperidine-2,6-dione (5 g, 13.71 mmol, 98% yield, hydrochloric salt) was obtained as a white solid.

Step 9: 3-(5-(4-((1-(5-(5-methyl-5H-pyrido[4,3-b]indol-7-yl)pyridin-2-yl)piperidin-4-yl)methyl)piperazin-1-yl)-1-oxoisoindolin-2-yl)piperidine-2,6-dione

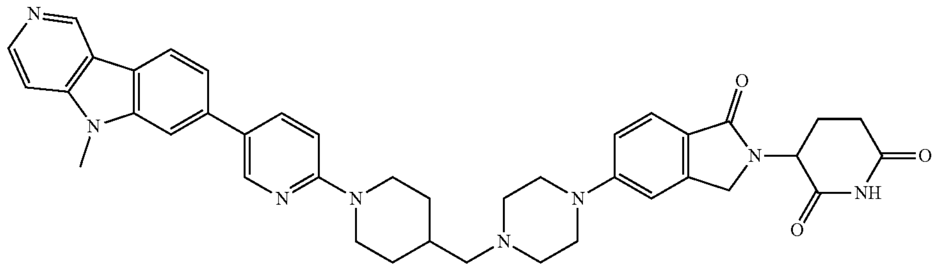 [SMILES: Cn1c2ccncc2c2ccc(-c3ccc(N4CCC(CN5CCN(c6ccc7c(c6)CN(C6CCC(=O)NC6=O)C7=O)CC5)CC4)nc3)cc21]

A mixture of 1-(5-(5-methyl-5H-pyrido[4,3-b]indol-7-yl) pyridin-2-yl)piperidine-4-carbaldehyde (58 mg, 0.15 mmol), N-ethyl-N-isopropylpropan-2-amine (32 mg, 0.23 mmol), 3-(1-oxo-5-(piperazin-1-yl)isoindolin-2-yl)piperidine-2,6-dione (51 mg, 0.15 mmol) and acetic acid (0.5 ml) in methanol (4 ml) was stirred at room temperature for 30 minutes. It was followed by the addition of sodium cyanoborohydride (21 mg, 2.10 mmol) and stirring for 1 hour at room temperature. The mixture was partitioned between ethyl acetate (30 ml) and brine (30 ml), dried over anhydrous sodium sulfate, and concentrated under reduced pressure to give a crude residue which was purified by prep TLC (eluted with 10% methanol in dichloromethane) to afford 3-(5-(4-((1-(5-(5-methyl-5H-pyrido[4,3-b]indol-7-yl)pyridin-2-yl) piperidin-4-yl)methyl)piperazin-1-yl)-1-oxoisoindolin-2-yl) piperidine-2,6-dione (57 mg, yield 53%) as light yellow solid.

$^1$H NMR (400 MHz, DMSO-d6): δ 1.11-1.23 (m, 4H), 1.82-1.99 (m, 4H), 2.30-2.39 (m, 3H), 2.60 (br, 4H), 2.86-2.94 (m, 3H), 3.17 (s, 2H), 3.98 (s, 3H), 4.10 (br, 1H), 4.21 (d, J=16.8 Hz, 1H), 4.32-4.41 (m, 31H), 5.05 (dd, J=13.2 Hz, 1H), 6.96 (d, J=9.2 Hz, 1H), 706-7.08 (m, 2H), 7.53 (d, J=8.4 Hz, 1H), 7.62 (d, J=8.0 Hz, 1H), 7.69 (d, J=6.0 Hz, 1H), 7.95 (s, 1H), 8.02 (dd, J=9.2 Hz, 1H), 8.30 (dd, J=8.4 Hz, 1H), 8.51 (d, J=5.6 Hz, 1H), 8.64 (s, 1H), 9.38 (s, 1H), 10.95 (s, 1H). $(M+H)^+$ 683.5.

Synthetic Scheme for Exemplary Compound 128
3-(5-(4-(2-(1-(5-(5-methyl-5H-pyrido[4,3-b]indol-7-yl)pyridin-2-yl)piperidin-4-yl)ethyl)piperazin-1-yl)-1-oxoisoindolin-2-yl)piperidine-2,6-dione
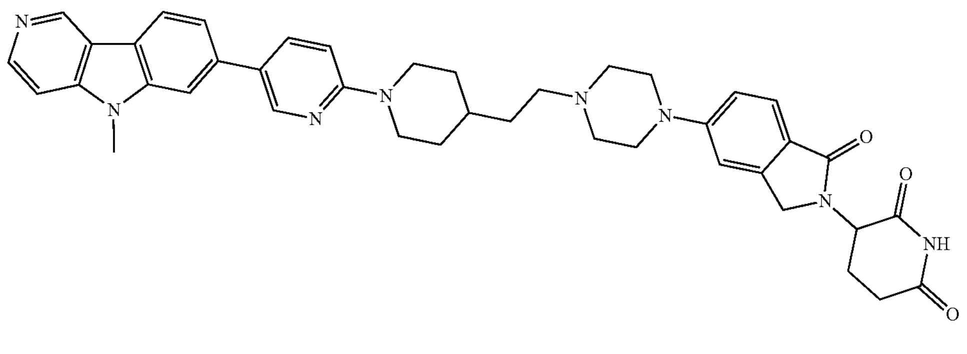 [SMILES: Cn1c2ccncc2c2ccc(-c3ccc(N4CCC(CCN5CCN(c6ccc7c(c6)CN(C6CCC(=O)NC6=O)C7=O)CC5)CC4)nc3)cc21]
Prepared according to the synthetic scheme below using procedures described for Compound 127.
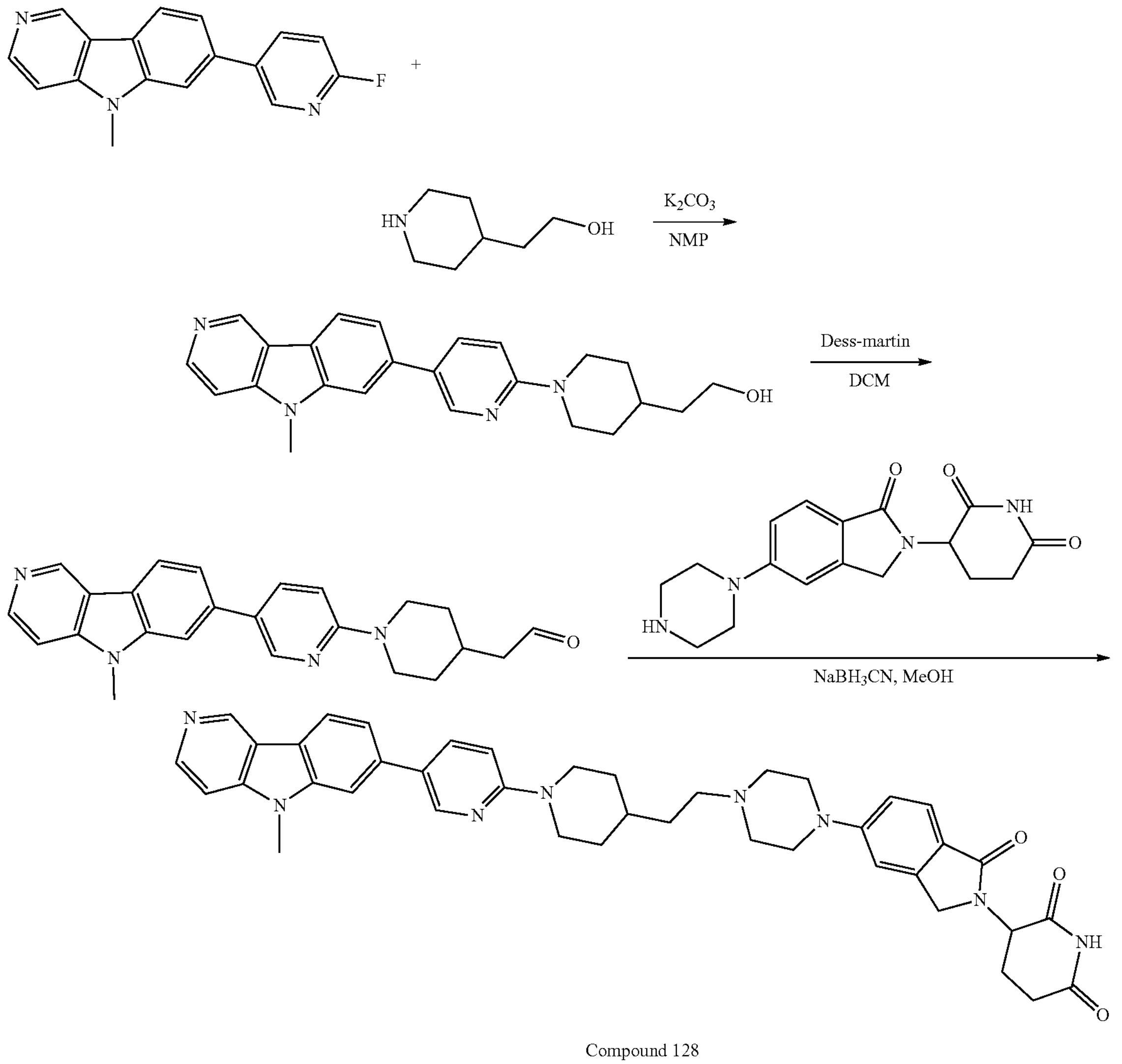
Compound 128
Compound 128: $^1H$ NMR (400 MHz, DMSO-d6) δ 1.16-1.23 (m, 3H), 1.40-1.50 (m, 2H), 1.61 (br, 1H), 1.76-1.78 (m, 2H), 1.94-1.96 (m, 1H), 2.38-2.41 (s, 3H), 2.51-2.56 (m, 4H), 2.82-2.90 (m, 3H), 3.29-3.33 (m, 4H), 3.95 (s, 3H), 4.18-4.22 (m, 1H), 4.30-4.39 (m, 3H), 5.02-5.08 (m, 1H), 6.95 (d, J=8.8 Hz, 1H), 7.05-7.06 (m, 2H), 7.50-7.69 (m, 3H), 7.91 (s, 1H), 8.00 (dd, J=8.8, 2.2 Hz, 1H), 8.28 (d, J=8.0 Hz, 1H), 8.48 (d, J=5.8 Hz, 1H), 8.62 (d, J=2.0 Hz, 1H), 9.33 (s, 1H), 10.95 (s, 1H). $(M+H)^+$ 697.6.
Synthetic Scheme for Exemplary Compound 130
2-(2,6-dioxopiperidin-3-yl)-5-(3-(3-(3-(4-((5-(5-methyl-5H-pyrido[4,3-b]indol-7-yl)-3-(trifluoromethyl)pyridin-2-yl)oxy)piperidin-1-yl)propoxy)propoxy)azetidin-1-yl)isoindoline-1,3-dione
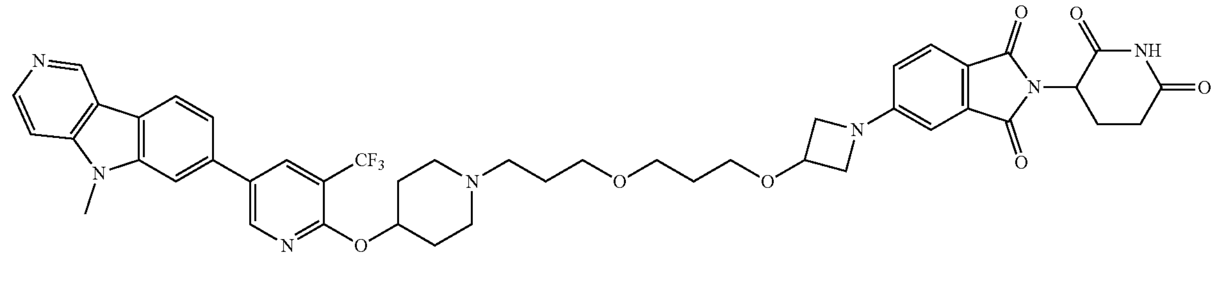 [SMILES: Cn1c2ccncc2c2ccc(-c3cnc(OC4CCN(CCCOCCCOC5CN(c6ccc7c(c6)C(=O)N(C6CCC(=O)NC6=O)C7=O)C5)CC4)c(C(F)(F)F)c3)cc21]
Prepared according to the synthetic scheme below using procedures described above and common procedures known to those skilled in the art.
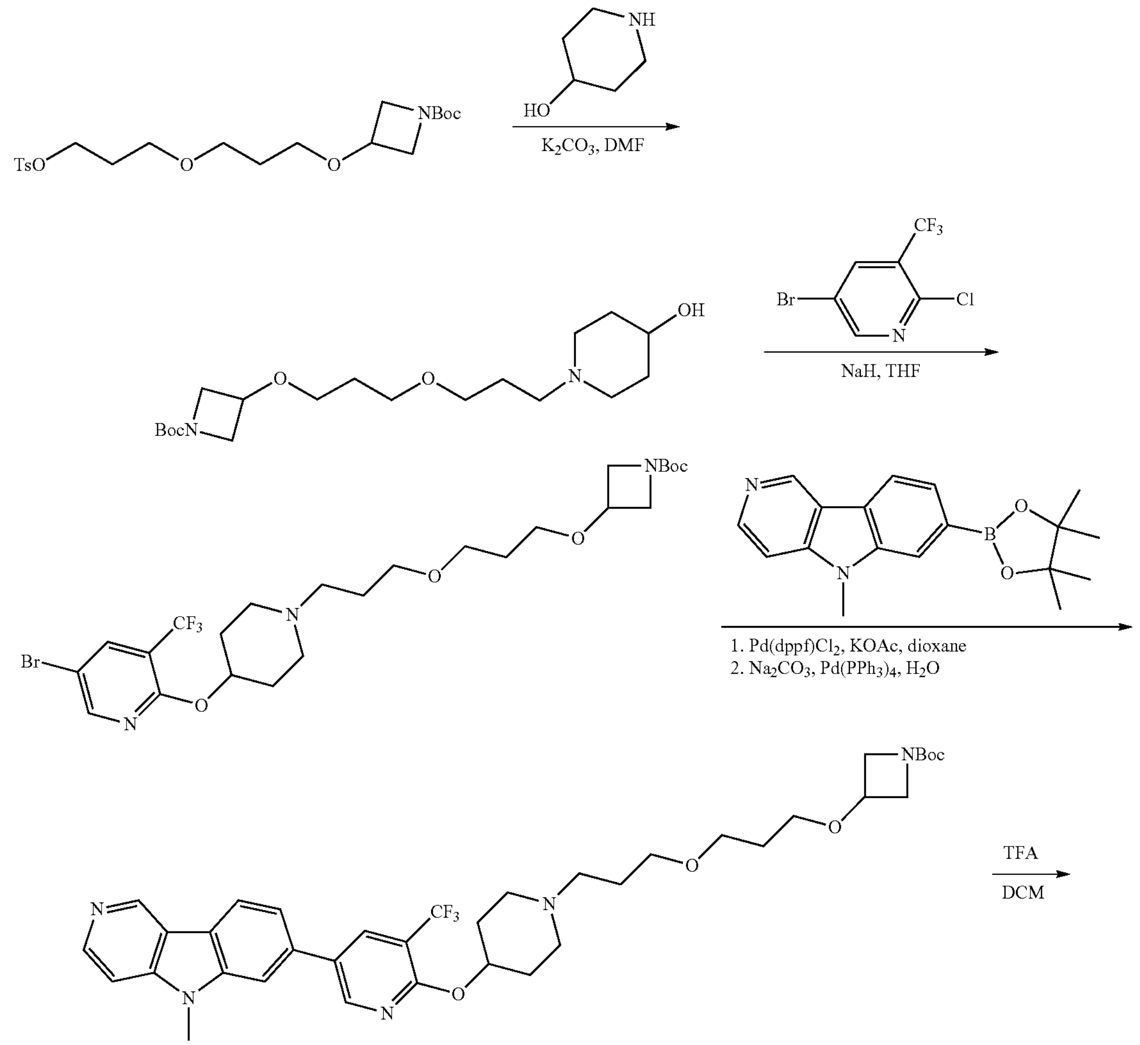

-continued

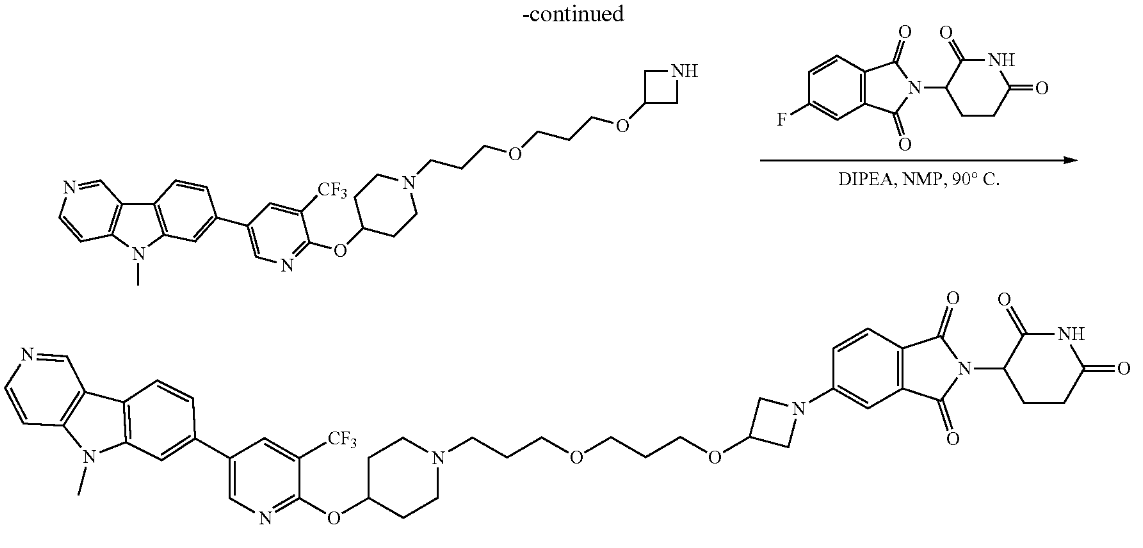

Compound 130

Compound 130: $^{1}$H NMR (400 MHz, DMSO-d6): δ 1.74-1.80 (m, 4H), 1.85-1.92 (m, 2H), 1.97-2.02 (m, 2H), 2.02-2.15 (m, 2H), 2.54-2.58 (m, 2H), 2.67-2.91 (m, 4H), 3.41-3.50 (m, 8H), 3.81-3.88 (m, 2H), 3.98 (s, 3H), 4.25 (t, J=7.8 Hz, 2H), 4.44-4.49 (m, 1H), 5.05 (dd, J=5.2, 12.8 Hz, 1H), 5.33-5.40 (m, 1H), 6.66 (dd, J=1.6, 8.4 Hz, 1H), 6.80 (d, J=1.2 Hz, 1H), 7.63-7.72 (m, 3H), 8.10 (s, 1H), 8.36 (d, J=8.4 Hz, 1H), 8.51 (d, J=4.8 Hz, 2H), 8.92 (s, 1H), 9.39 (s, 1H), 11.06 (s, 1H). $(M+H)^+$ 854.6.

Synthetic Scheme for Exemplary Compound 129

2-(2,6-dioxopiperidin-3-yl)-5-((1,1,1-trifluoro-6-(2-(2-(2-((5-(5-methyl-5H-pyrido[4,3-b]indol-7-yl)pyridin-2-yl)oxy)ethoxy)ethoxy)ethoxy)hexan-2-yl)oxy)isoindoline-1,3-dione To a solution of 5-(2-(2-(2-(5-bromopyridin-2-yloxy)ethoxy)ethoxy)ethoxy) pentanal (575 mg, 1.47 mmol) [prepared according to the scheme below and using procedures described above and common procedures known to those skilled in the art] and $CF_3Si(CH_3)_3$ (320 mg, 2.21 mmol) in THF was added TBAF (1M, 2.2 mL, 2.20 mmol) at room temperature. The reaction was stirred at room temperature for 3 hours. After quenched with 1N HCl (3 mL), the mixture was extracted with EA (30 mL), washed with brine. The organic phase was dried, concentrated under vacuum. The residue was purified by a silica gel (PE:EA=2:1) to get 6-(2-(2-(2-(5-bromopyridin-2-yloxy)ethoxy)ethoxy)ethoxy)-1,1,1-trifluorohexan-2-ol (400 mg, 60% yield).

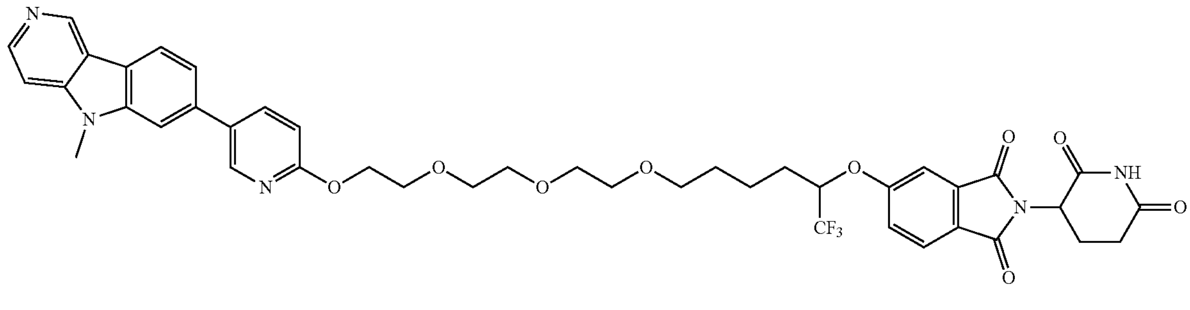 [SMILES: Cn1c2ccncc2c2ccc(-c3ccc(OCCOCCOCCOCCCCC(Oc4ccc5c(c4)C(=O)N(C4CCC(=O)NC4=O)C5=O)C(F)(F)F)nc3)cc21]

Step 1: 6-(2-(2-(2-(5-bromopyridin-2-yloxy)ethoxy)ethoxy)ethoxy)-1,1,1-trifluorohexan-2-ol

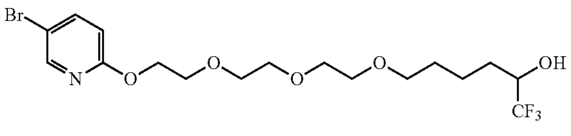 [SMILES: OC(CCCCOCCOCCOCCOc1ccc(Br)cn1)C(F)(F)F]

Step 2: 6-(2-(2-(2-(5-bromopyridin-2-yloxy)ethoxy)ethoxy)ethoxy)-1,1,1-trifluorohexan-2-yltrifluoromethanesulfonate

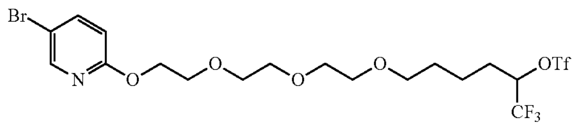 [SMILES: O=S(=O)(OC(CCCCOCCOCCOCCOc1ccc(Br)cn1)C(F)(F)F)C(F)(F)F]

To a solution of 6-(2-(2-(2-(5-bromopyridin-2-yloxy) ethoxy)ethoxy)ethoxy)-1,1,1-trifluorohexan-2-ol (130 mg, 0.28 mmol) and pyridine (67 mg, 0.85 mmol) in DCM was added $Tf_2O$ (120 mg, 0.42 mmol) at 0° C. The resulting solution warmed to room temperature for 1 hour. The reaction was diluted with DCM (10 mL), washed with water, brine and concentrated under vacuum to afford 6-(2-(2-(2-(5-bromopyridin-2-yloxy) ethoxy)ethoxy)ethoxy)-1,1,1-trifluorohexan-2-yltrifluoromethanesulfonate (160 mg, 96%).

Compound 129: $^1$HNMR (400 MHz, $CDCl_3$): δ 9.25 (s, 1H), 8.48 (s, 1H), 8.39 (s, 1H), 8.09 (d, J=8.0 Hz, 1H), 7.82 (d, J=8.0 Hz, 1H), 7.72 (d, J=8.4 Hz, 1H), 7.46 (s, 1H), 7.36-7.41 (m, 2H), 7.19-7.24 (m, 2H), 6.82 (d, J=8.8 Hz, 1H), 4.86-4.91 (m, 1H), 4.58-4.63 (m, 1H), 4.45-4.48 (m, 2H), 3.78-3.82 (m, 5H), 3.55-3.80 (m, 9H), 3.39-3.50 (m, 3H), 2.69-2.82 (m, 6H), 1.96-2.05 (m, 2H), 1.81-1.89 (m, 2H). $(M+H)^+$ 818.5.

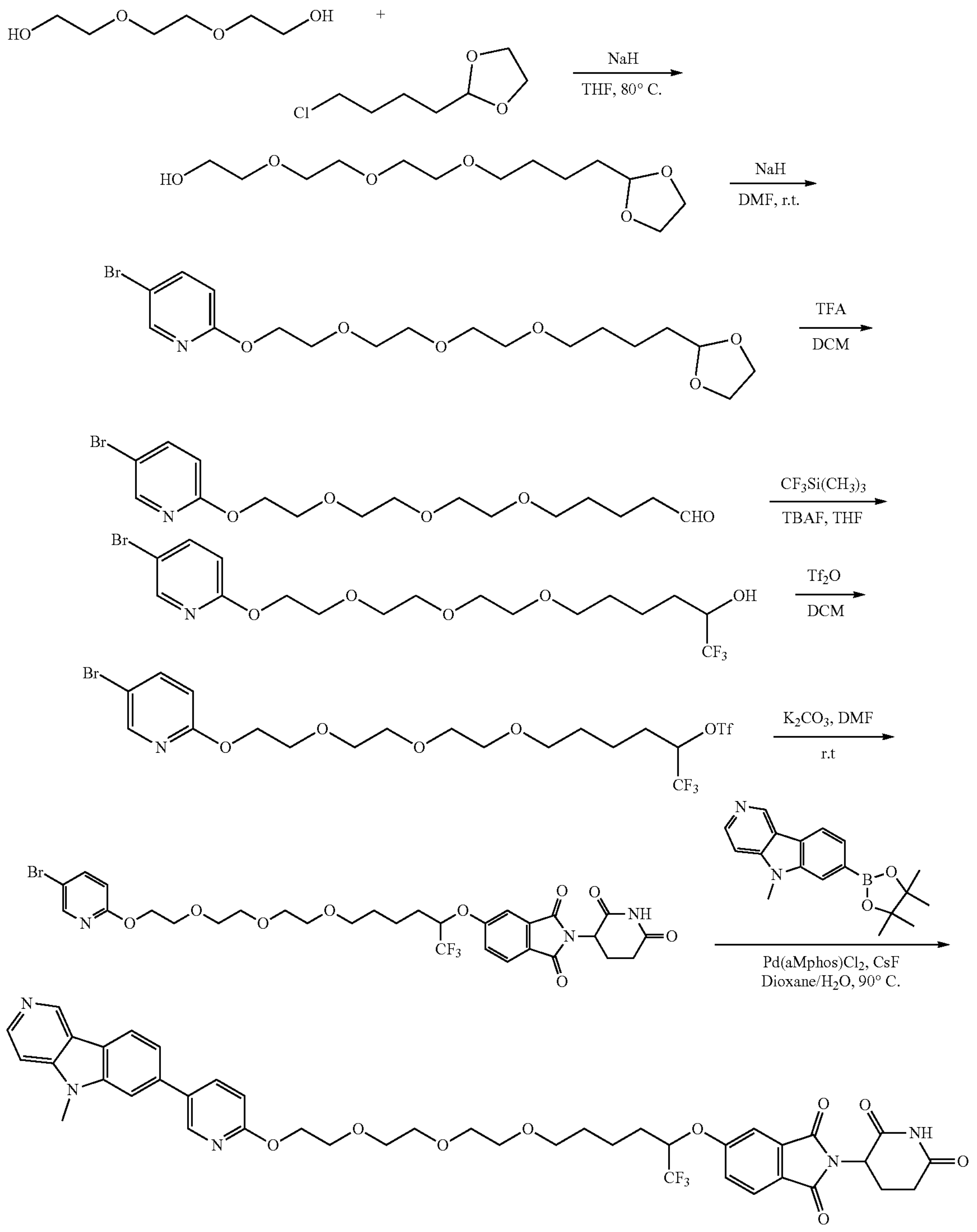

Compound 129

Synthetic Scheme for Exemplary Compound 131

2-(2,6-dioxopiperidin-3-yl)-5-((17-((5-(5-methyl-5H-pyrido[4,3-b]indol-7-yl)pyridin-2-yl)oxy)-3,6,9,12,15-pentaoxaheptadecyl)oxy)isoindoline-1,3-dione

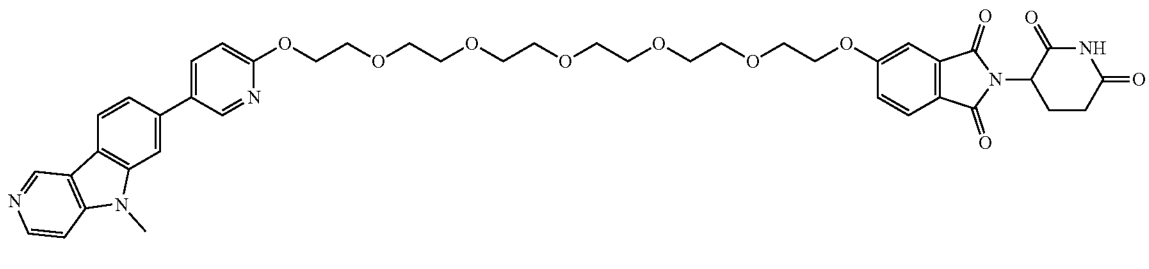 [SMILES: Cn1c2ccncc2c2ccc(-c3ccc(OCCOCCOCCOCCOCCOCCOc4ccc5c(c4)C(=O)N(C4CCC(=O)NC4=O)C5=O)nc3)cc21]

Prepared according to the scheme below using procedures described above and common procedures known to those skilled in the art.

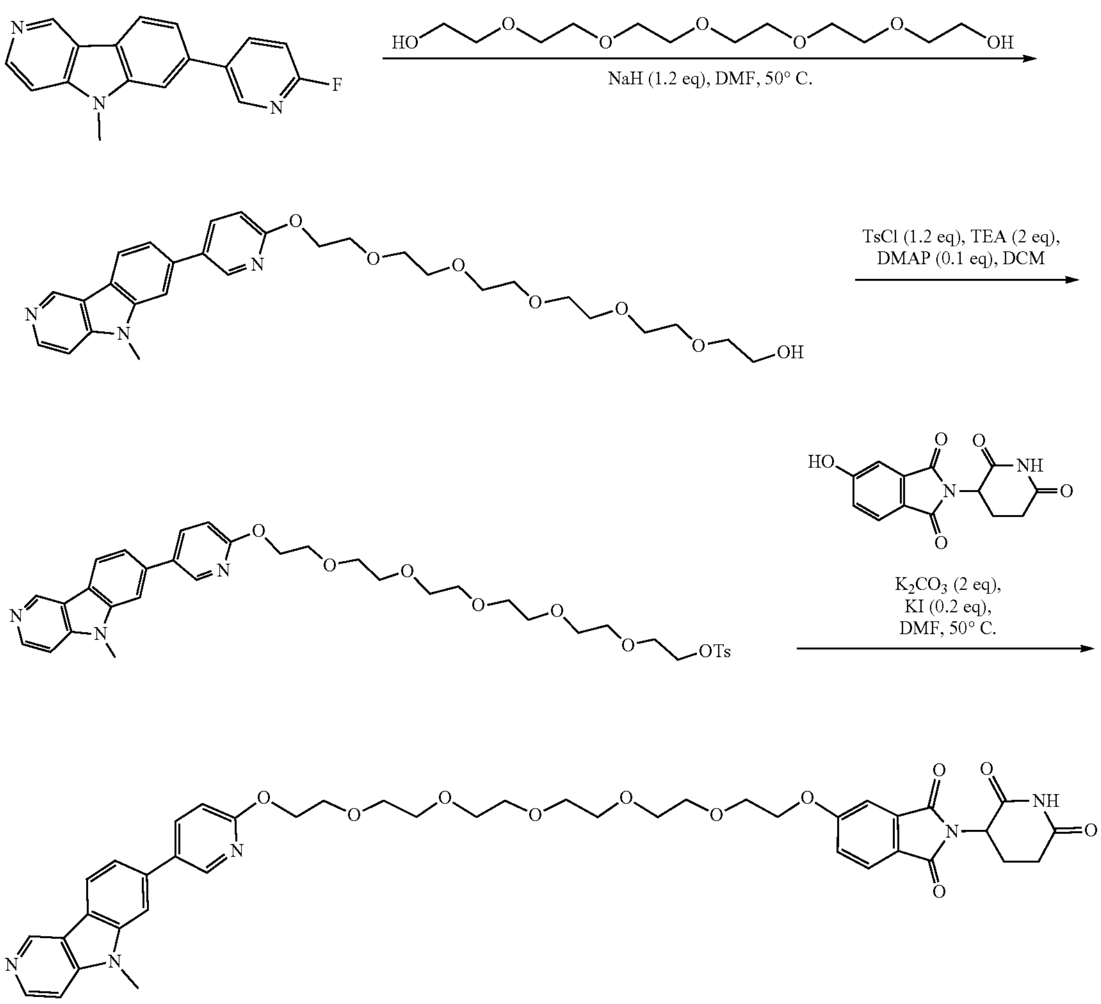

Compound 132

Using procedures analogous to those for Compound 131, the following were prepared: Compound 132.

Synthetic Scheme for Exemplary Compound 133

2-(2,6-dioxopiperidin-3-yl)-5-(3-(6-((5-((5-(5-methyl-5H-pyrido[4,3-b]indol-7-yl)pyridin-2-yl)oxy)pentyl)oxy)hexyl)azetidin-1-yl)isoindoline-1,3-dione

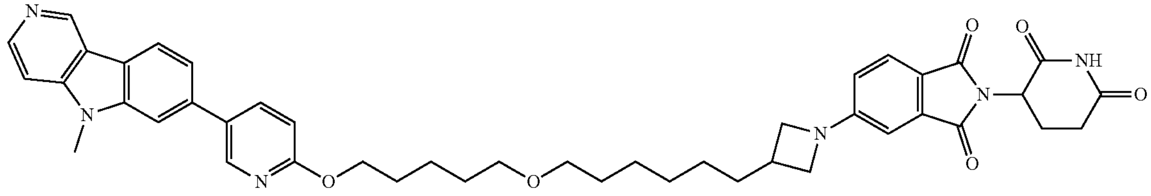 [SMILES: Cn1c2ccncc2c2ccc(-c3ccc(OCCCCCOCCCCCCC4CN(c5ccc6c(c5)C(=O)N(C5CCC(=O)NC5=O)C6=O)C4)nc3)cc21]

Step 1: (6-(benzyloxy)hexyl)magnesium bromide

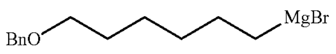

A suspension of (((6-bromohexyl)oxy)methyl)benzene (10 g, 0.037 mol), magnesium (1.33 g, 0.055 mol) and iodine (200 mg) in anhydrous tetrahydrofuran (100 ml) was stirred at 50° C. for 2 hours. Iodine disappeared and the mixture was stirred for another 1 hour to afford (6-(benzyloxy)hexyl) magnesium bromide (crude) which was used in the next step without further purification.

Step 2: tert-butyl 3-(6-(benzyloxy)hexyl)-3-hydroxyazetidine-1-carboxylate

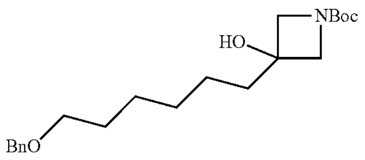 [SMILES: CC(C)(C)OC(=O)N1CC(O)(CCCCCCOCc2ccccc2)C1]

To the solution of tert-butyl 3-oxoazetidine-1-carboxylate (5.2 g, 0.031 mol) in anhydrous tetrahydrofuran (50 ml) was added (6-(benzyloxy)hexyl)magnesium bromide at 0° C. The resulting mixture was allowed to warm up to room temperature and stirred at room temperature for 16 hours. The mixture was filtered and the filtrate was concentrated. The residue was partitioned between ethyl acetate (50 ml) and water (100 ml). The organic layer was collected, washed with brine (30 ml), dried over anhydrous sodium sulfate, and concentrated under reduced pressure to give a crude residue which was purified by silica gel flash chromatography (eluted with 33-50% ethyl acetate in hexane) to afford tert-butyl 3-(6-(benzyloxy)hexyl)-3-hydroxyazetidine-1-carboxylate (1.7 g, two steps 12%) as colorless oil.

Step 3: tert-butyl 3-(6-(benzyloxy)hexylidene)azetidine-1-carboxylate

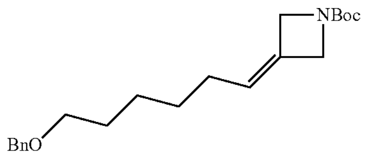 [SMILES: CC(C)(C)OC(=O)N1CC(=CCCCCCOCc2ccccc2)C1]

To a stirred solution of tert-butyl 3-(6-(benzyloxy)hexyl)-3-hydroxyazetidine-1-carboxylate (800 mg, 2.2 mmol) in toluene (10 ml) was added 1-methoxy-N-triethylammonio-sulfonyl-methanimidate (Burgess reagent) (1.57 g, 6.6 mmol). The resulting solution was allowed to warm up to 90° C. and stirred at this temperature for 2 hours. The mixture was poured into water (20 ml) and extracted with ethyl acetate (20 ml×2). The combined organic layers were washed with brine (20 ml), dried over anhydrous sodium sulfate, and concentrated under reduced pressure to give a crude residue which was purified by silica gel flash column chromatography (eluted with 30% ethyl acetate in hexane) to afford tert-butyl 3-(6-(benzyloxy)hexylidene)azetidine-1-carboxylate (125 mg, yield 16%) as colorless oil.

Step 4: tert-butyl 3-(6-hydroxyhexyl)azetidine-1-carboxylate

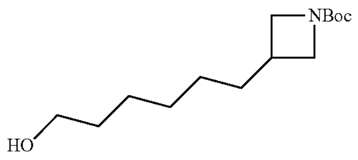 [SMILES: CC(C)(C)OC(=O)N1CC(CCCCCCO)C1]

A mixture of tert-butyl 3-(6-(benzyloxy)hexylidene)azetidine-1-carboxylate (125 mg, 0.36 mmol), palladium on carbon (10%, 50 mg) in methanol (30 ml) was stirred at room temperature for 3 hours under hydrogen atmosphere (hydrogen balloon). TLC showed the reaction was complete. Palladium on carbon was removed through filtration and washed with methanol (5 ml×2). The combined filtrates were concentrated under reduced pressure to afford tert-butyl 3-(6-hydroxyhexyl)azetidine-1-carboxylate (88 mg, yield: 95%) as colorless oil.

Tert-butyl 3-(6-hydroxyhexyl)azetidine-1-carboxylate was converted to the final compound, 2-(2,6-dioxopiperidin-3-yl)-5-(3-(6-((5-((5-(5-methyl-5H-pyrido[4,3-b]indol-7-yl)pyridin-2-yl)oxy)pentyl)oxy)hexyl)azetidin-1-yl)isoindoline-1,3-dione, according to the scheme below and using procedures described above and common procedures known to those skilled in the art.

Compound 133: 1H NMR (400 Hz, D6-DMSO): δ 1.24-1.35 (m, 7H), 1.46-1.57 (m, 8H), 1.72-1.82 (m, 2H), 1.98-2.01 (m, 3H), 2.57-2.74 (m, 3H), 2.81-2.99 (m, 2H), 3.57-3.59 (m, 2H), 3.98 (s, 3H), 4.06-4.08 (m, 2H), 4.33 (s, 2H), 5.03-5.06 (m, 1H), 6.54-6.66 (m, 1H), 6.69 (s, 1H), 6.93-6.95 (m, 1H), 7.57-7.71 (m, 3H), 8.02 (s, 1H), 8.19-8.21 (m, 1H), 8.34-8.36 (m, 1H), 8.53-8.58 (m, 1H), 8.66 (s, 1H), 9.41 (s, 1H), 11.08 (s, 1H). $(M+H)^+$ 757.6.

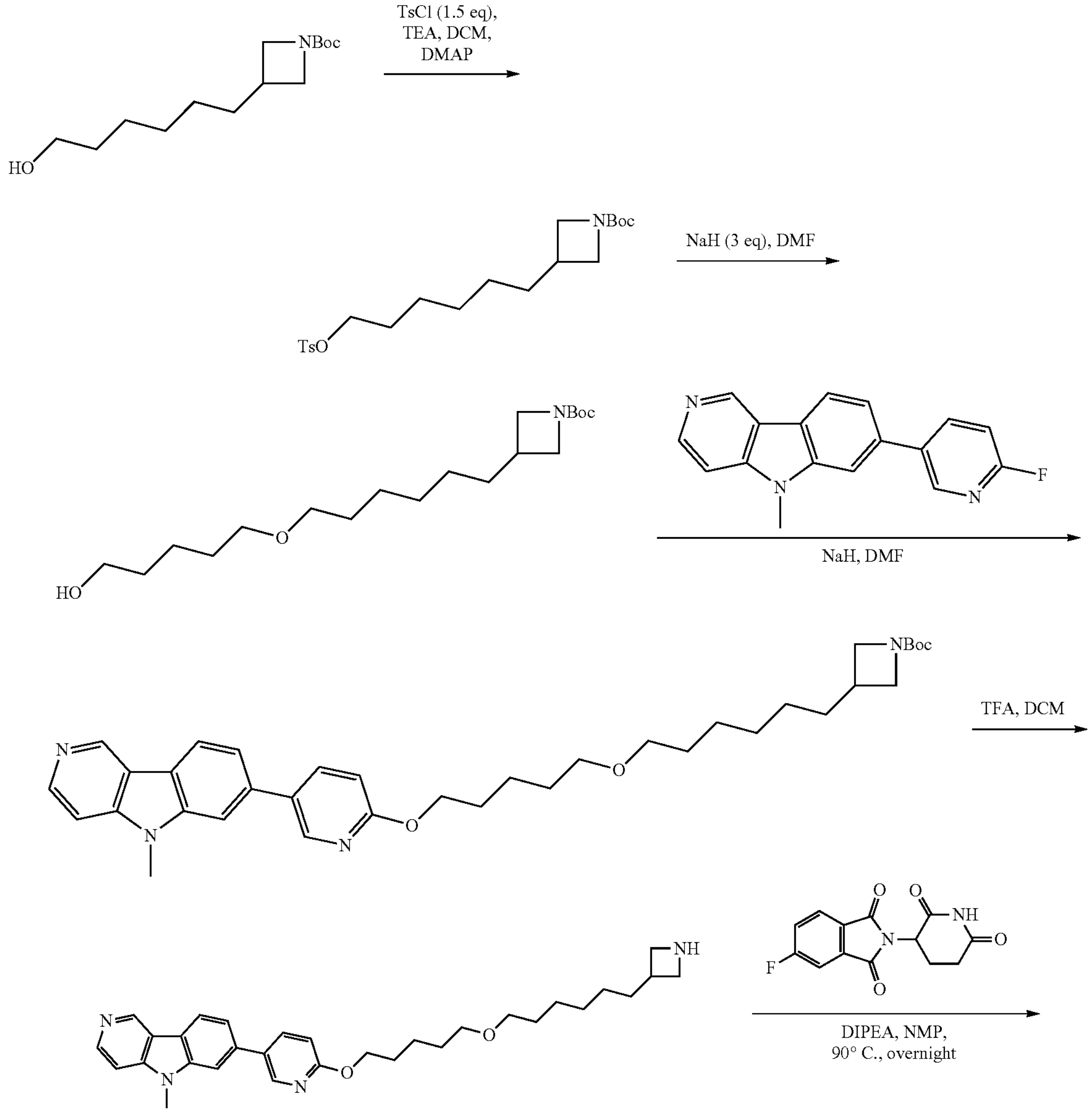

MB-016-E-8

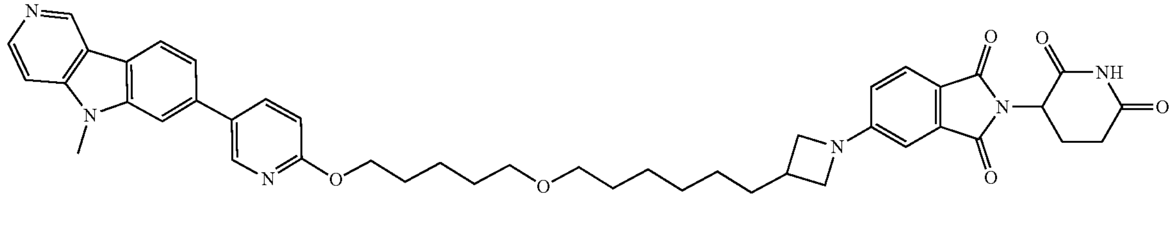

Compound 133

Synthetic Scheme for Exemplary Compound 134

2-(2,6-dioxopiperidin-3-yl)-5-((6-(6-((1r,3r)-3-((5-(5-methyl-5H-pyrido[4,3-b]indol-7-yl)pyridin-2-yl)oxy)cyclobutoxy)pyridazin-3-yl)hex-5-yn-1-yl)oxy)isoindoline-1,3-dione

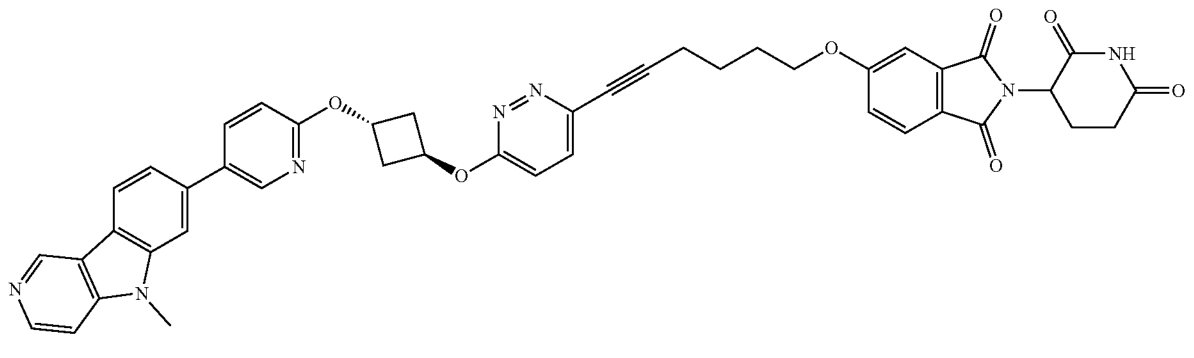 [SMILES: Cn1c2ccncc2c2ccc(-c3ccc(O[C@H]4C[C@H](Oc5ccc(C#CCCCCOc6ccc7c(c6)C(=O)N(C6CCC(=O)NC6=O)C7=O)nn5)C4)nc3)cc21]

Step 1: 3,6-diiodopyridazine

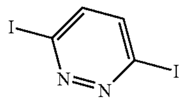

A mixture of 3,6-dichloropyridazine (5.0 g, 34.0 mmol) and sodium iodide (50 g, 0.68 mol) in acetone (50 ml) was stirred at 65° C. for 3 hours. The reaction mixture was quenched with water (100 ml) and extracted with ethyl acetate (200 ml×2). The combined organic layers were washed with brine (200 ml×2), dried over anhydrous sodium sulfate, and concentrated under reduced pressure to give a residue which was purified by silica gel flash column chromatography (eluted with 40% ethyl acetate in hexane) to afford 3,6-diiodopyridazine (5.4 g, 4.9 mol, 48% yield) as brown solid.

Step 2: 3-fluoro-6-iodopyridazine

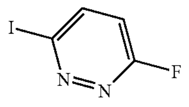

A mixture of 3,6-dichloropyridazine (1 g, 3.0 mmol), cesium fluoride (413 mg, 0.9 mol) in dimethyl sulphoxide (10 ml) was stirred at 140° C. overnight. The reaction mixture was partitioned between water (50 ml) and ethyl acetate (100 ml). The organic layer was collected, washed with brine (100 ml), dried over anhydrous sodium sulfate, and concentrated under reduced pressure to give a residue which was purified by silica gel flash column chromatography (eluted with 20% ethyl acetate in hexane) to afford 3-fluoro-6-iodopyridazine (840 mg).

Step 3: 7-(6-((1r,3r)-3-((6-iodopyridazin-3-yl)oxy)cyclobutoxy)pyridin-3-yl)-5-methyl-5H-pyrido[4,3-b]indole

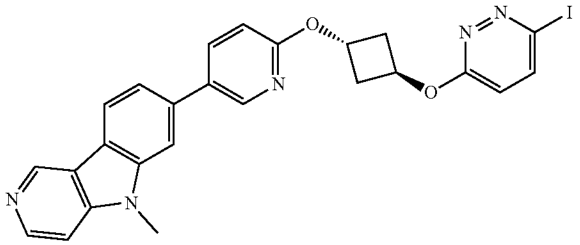 [SMILES: Cn1c2ccncc2c2ccc(-c3ccc(O[C@H]4C[C@H](Oc5ccc(I)nn5)C4)nc3)cc21]

(1r,3r)-3-((5-(5-methyl-5H-pyrido[4,3-b]indol-7-yl)pyridin-2-yl)oxy)cyclobutanol (100 mg, 0.29 mmol), 3-fluoro-6-iodopyridazine (300 mg, 0.10 mmol) in 1-methylpyrrolidin-2-one (5 ml) was added sodium hydride (60% in mineral oil) (110 mg, 2.7 mmol) at 0° C. The resulting mixture was allowed to warm up to room temperature for 1 hour. The reaction mixture was quenched with water (10 ml) at 0° C. and extracted with ethyl acetate (20 ml×3). The combined organic layers were washed with brine (20 ml), dried over anhydrous sodium sulfate, and concentrated under reduced pressure to give a crude residue which was purified by silica gel flash chromatography (eluted with 20% methanol in dichloromethane) to afford 7-(6-((1r,3r)-3-((6-iodopyridazin-3-yl)oxy)cyclobutoxy)pyridin-3-yl)-5-methyl-5H-pyrido[4,3-b]indole (70 mg, 0.13 mmol, yield 44%) as brown solid.

7-(6-((1r,3r)-3-((6-iodopyridazin-3-yl)oxy)cyclobutoxy)pyridin-3-yl)-5-methyl-5H-pyrido[4,3-b]indole was converted to the final compound, 2-(2,6-dioxopiperidin-3-yl)-5-((6-(6-((1r,3r)-3-((5-(5-methyl-5H-pyrido[4,3-b]indol-7-yl)pyridin-2-yl)oxy)cyclobutoxy)pyridazin-3-yl)hex-5-yn-1-yl)oxy)isoindoline-1,3-dione, according to the scheme below and using procedures described above (step 6 of Compound 73 and step 1 of Compound 180).

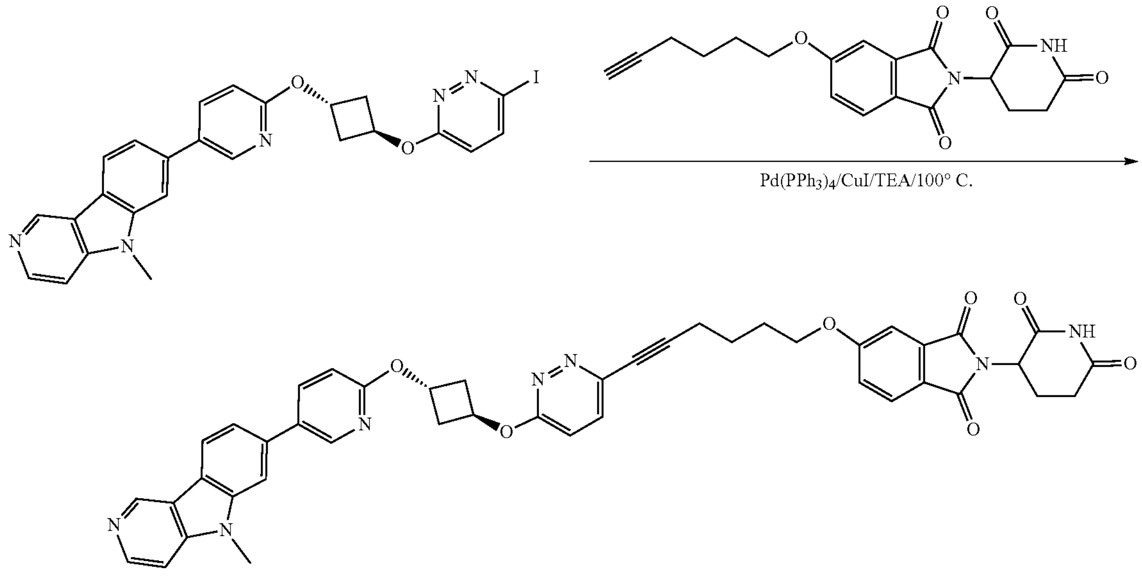

Compound 134

Compound 134: $^1$HNMR (400 MHz, DMSO-$d_6$): δ 1.74-1.78 (m, 2H), 1.92-1.95 (m, 2H), 2.03-2.07 (m, 1H), 2.54-2.62 (m, 4H), 2.68-2.71 (m, 4H), 2.85-2.93 (m, 1H), 3.96 (s, 3H), 4.23-4.27 (m, 2H), 5.09-5.14 (m, 1H), 5.45-5.48 (m, 1H), 5.55-5.58 (m, 1H), 7.01 (d, J=8.8 Hz, 1H), 7.24-7.26 (m, 1H), 7.36-7.38 (m, 1H), 7.45 (m, 1H), 7.62-7.68 (m, 3H), 7.82 (d, J=8.0 Hz, 1H), 7.99 (s, 1H), 8.21-8.24 (m, 1H), 8.33 (d, J=8.0 Hz, 1H), 8.49-8.51 (m, 1H), 8.64-8.65 (m, 1H), 9.37 (s, 1H), 11.12 (s, 1H). $(M+H)^+$ 776.5.

Additionally, Compound 149 was prepared from Compound 134 using hydrogenation procedure described previously for the conversion of Compound 102 to Compound 110.

Synthetic Scheme for Exemplary Compound 145

2-(2,6-dioxopiperidin-3-yl)-5-(4-((2-(((1r,3r)-3-((5-(5-methyl-5H-pyrido[4,3-b]indol-7-yl)pyridin-2-yl)oxy)cyclobutyl)methyl)-2-azaspiro[3.3]heptan-6-yl)oxy)butoxy)isoindoline-1,3-dione

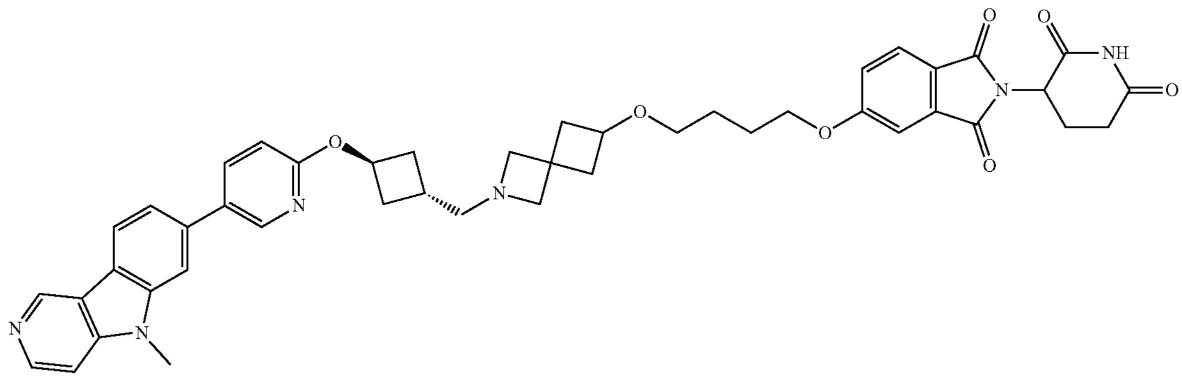 [SMILES: Cn1c2ccncc2c2ccc(-c3ccc(O[C@H]4C[C@H](CN5CC6(CC(OCCCCOc7ccc8c(c7)C(=O)N(C7CCC(=O)NC7=O)C8=O)C6)C5)C4)nc3)cc21]

Prepared according to the schemes below and using procedures described above and common procedures known to those skilled in the art.

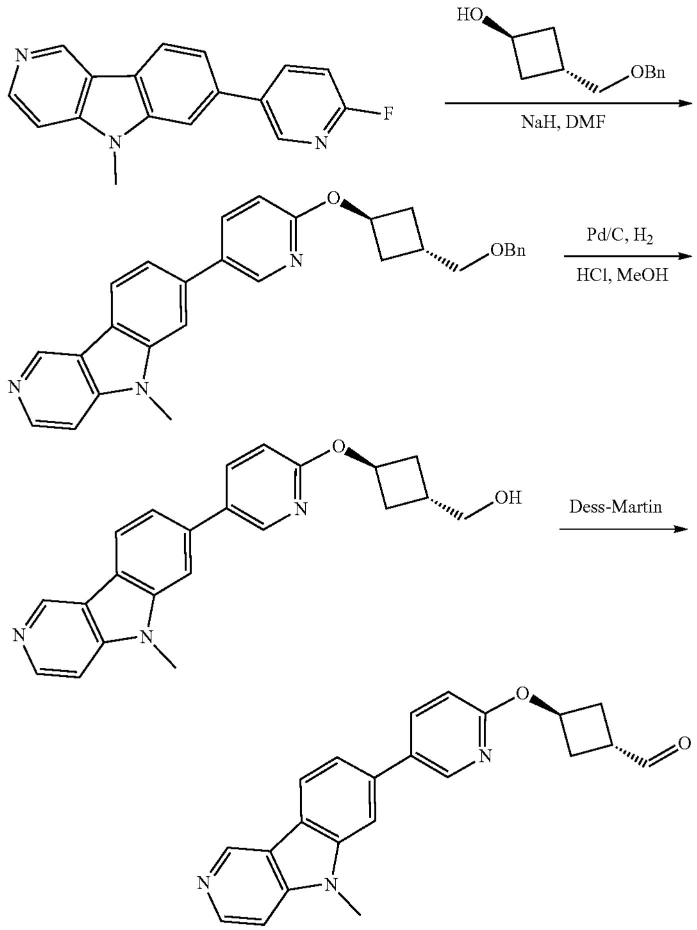
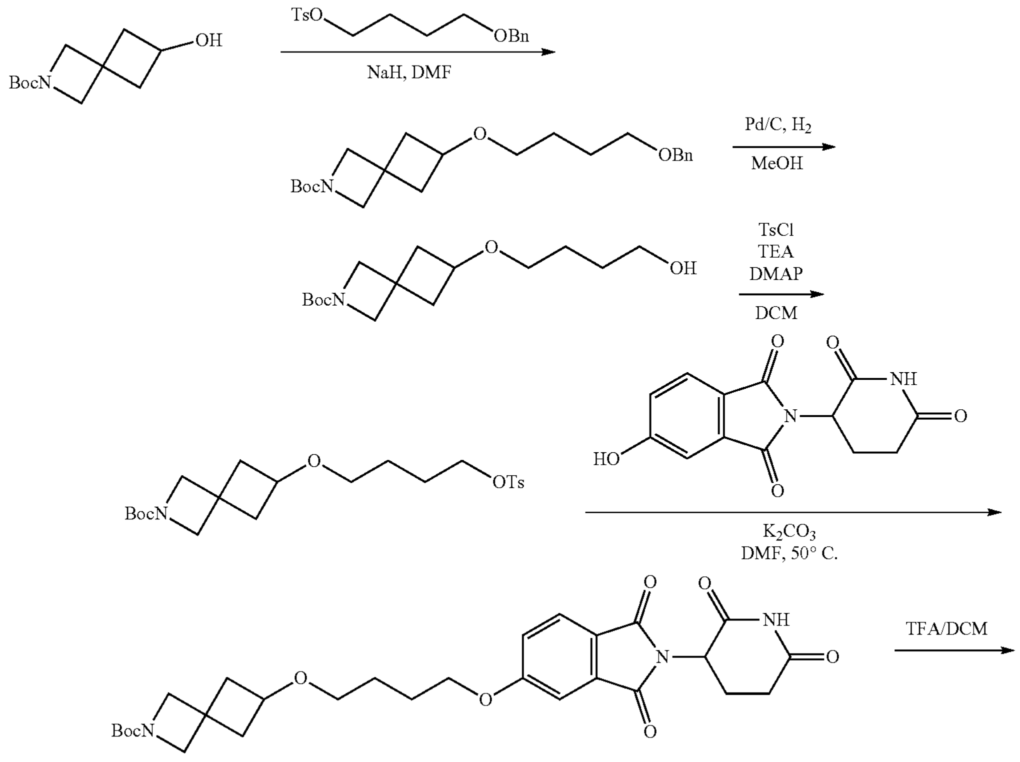
MB-019-C-7

-continued

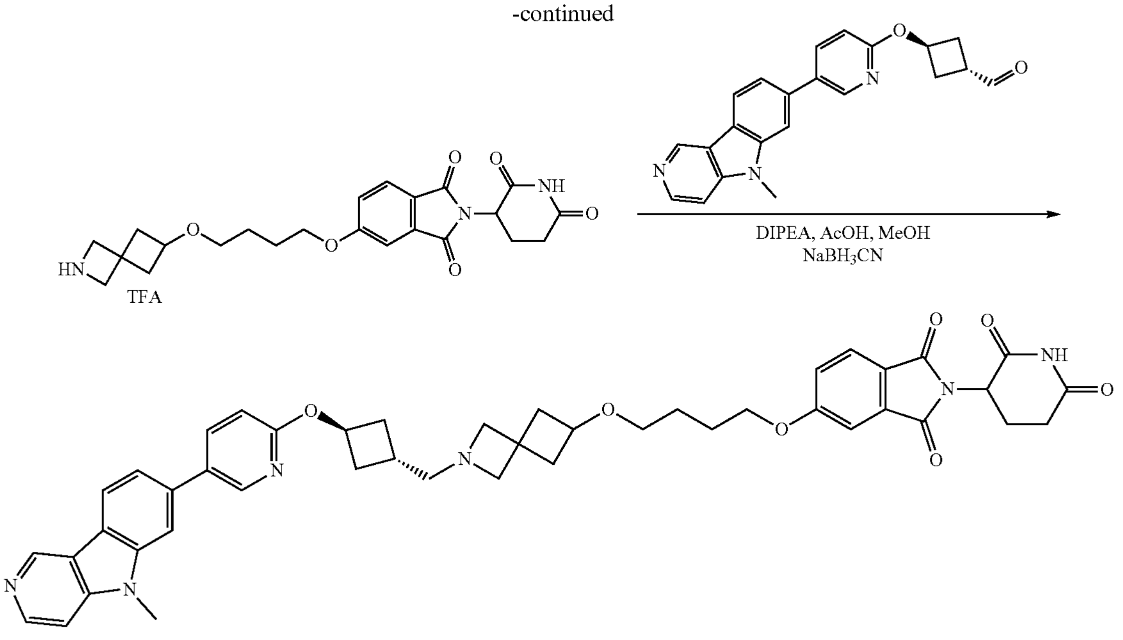

Compound 135

Compound 135: $^1$H NMR (400 MHz, DMSO-$d_6$): 1.60-1.80 (m, 6H), 1.92-2.07 (m, 5H), 2.16-2.26 (m, 3H), 2.34-2.40 (m, 2H), 2.55-2.67 (m, 4H), 2.84-2.93 (m, 1H), 3.26-3.31 (m, 4H), 3.78-3.82 (m, 1H), 3.96 (s, 3H), 4.18 (t, J=6.0 Hz, 2H), 5.05-5.27 (m, 2H), 6.90-6.94 (m, 1H), 7.33-7.35 (m, 1H), 7.42 (s, 1H), 7.60-7.63 (m, 2H), 7.83 (d, J=8.4 Hz, 1H), 7.98 (s, 1H), 8.17-8.20 (m, 1H), 8.32 (d, J=8.0 Hz, 1H), 8.51 (d, J=6.0 Hz, 1H), 8.62 (s, 1H), 9.36 (s, 1H), 11.12 (s, 1H). $(M+H)^+$ 783.6.

Synthetic Scheme for Exemplary Compound 136

2-(2,6-dioxopiperidin-3-yl)-5-(4-((2-((1s,3s)-3-((5-(5-methyl-5H-pyrido[4,3-b]indol-7-yl)pyridin-2-yl)oxy)cyclobutane-1-carbonyl)-2-azaspiro[3.3]heptan-6-yl)oxy)butoxy)isoindoline-1,3-dione

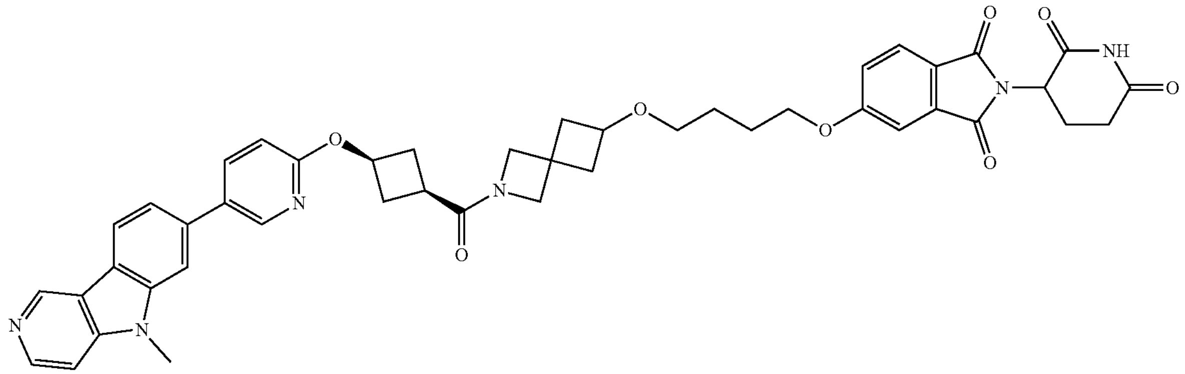 [SMILES: Cn1c2ccncc2c2ccc(-c3ccc(O[C@H]4C[C@@H](C(=O)N5CC6(CC(OCCCCOc7ccc8c(c7)C(=O)N(C7CCC(=O)NC7=O)C8=O)C6)C5)C4)nc3)cc21]

Prepared according to the schemes below and using procedures described above and common procedures known to those skilled in the art.

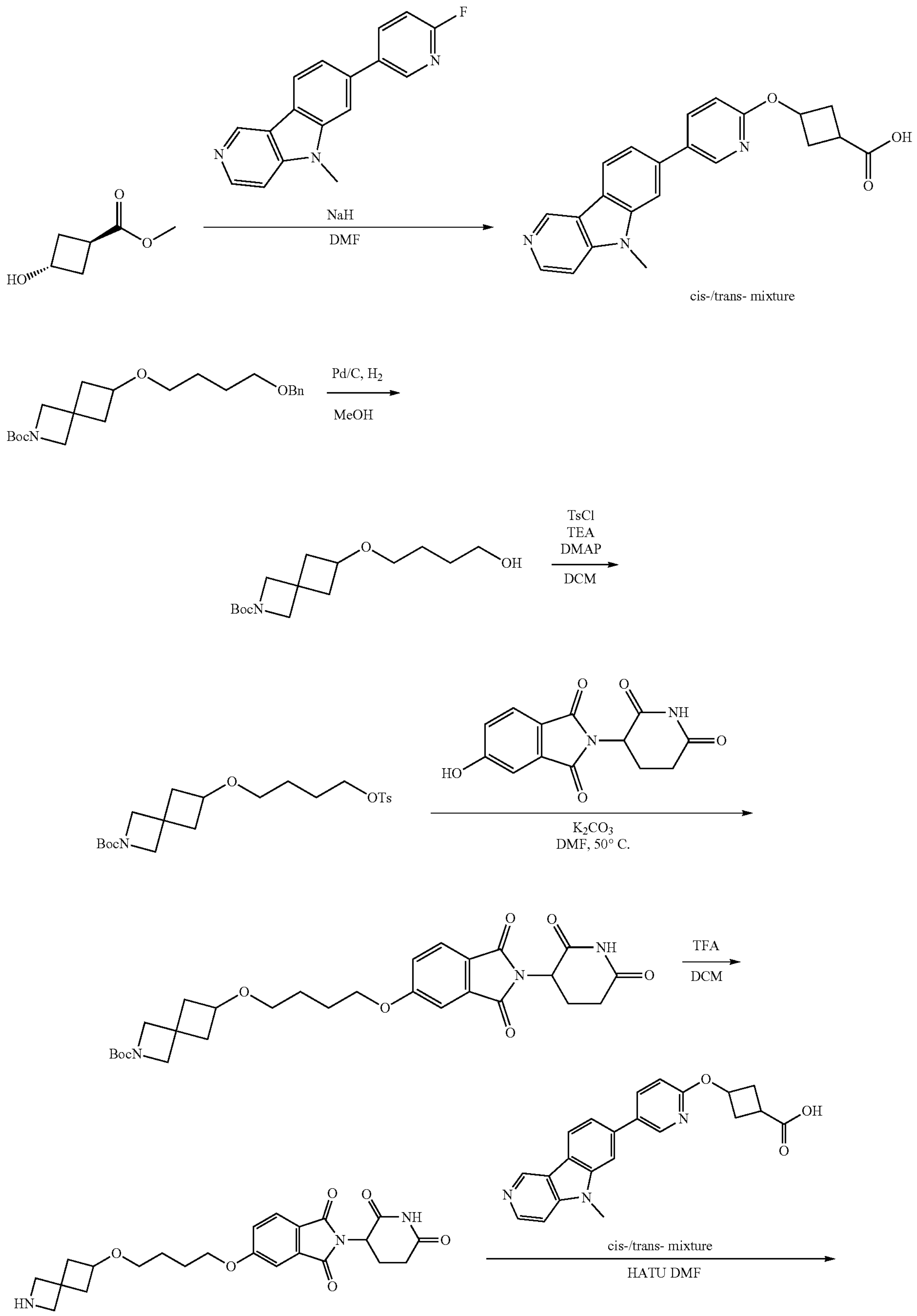
NaH
DMF
cis-/trans- mixture
Pd/C, H2
MeOH
TsCl
TEA
DMAP
DCM
K2CO3
DMF, 50° C.
TFA
DCM
cis-/trans- mixture
HATU DMF -continued

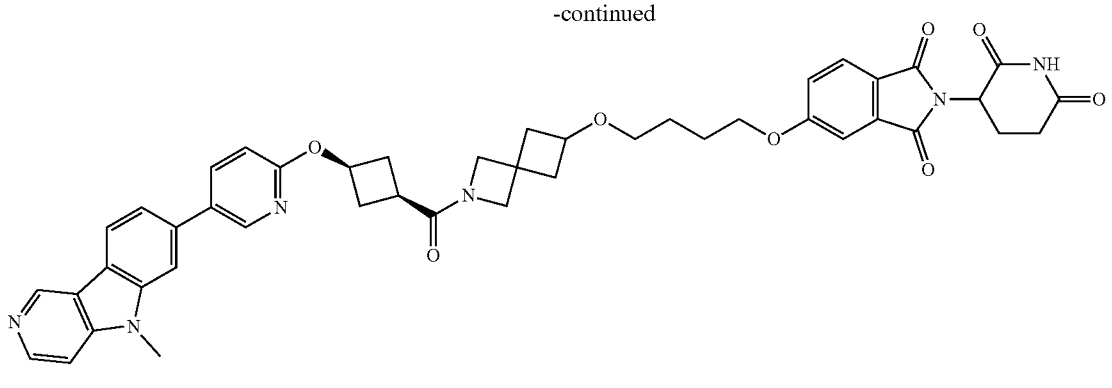

Compound 136
pure cis-isomer isolated from the cis-/trans- mixture

Compound 136: 1HNMR (400 MHz, DMSO-$d_6$): δ 1.61-1.65 (m, 2H), 1.77-1.80 (m, 2H), 1.99-2.08 (m, 4H), 2.14-2.20 (m, 2H), 2.44-2.46 (m, 3H), 2.55-2.61 (m, 4H), 2.72-2.76 (m, 1H), 2.85-2.93 (m, 1H), 3.79-3.84 (m, 3H), 3.96 (s, 3H), 4.04-4.09 (m, 2H), 4.17-4.20 (m, 2H), 5.10-5.14 (m, 2H), 6.93 (d, J=8.4 Hz, 1H), 7.34-7.42 (m, 2H), 7.61-7.65 (m, 2H), 7.83 (d, J=8.0 Hz, 1H), 7.99 (s, 1H), 8.18-8.20 (m, 1H), 8.32 (d, J=8.4 Hz, 1H), 8.50 (d, J=6.0 Hz, 1H), 8.62 (d, J=0.8 Hz, 1H), 9.37 (s, 1H), 11.12 (s, 1H). $(M+H)^+$ 797.5.

Synthetic Scheme for Exemplary Compound 137

2-(2,6-dioxopiperidin-3-yl)-5-((5-(6-(methyl((1r,3r)-3-((5-(5-methyl-5H-pyrido[4,3-b]indol-7-yl)pyridin-2-yl)oxy)cyclobutyl)amino)-2-azaspiro[3.3]heptan-2-yl)-5-oxopentyl)oxy)isoindoline-1,3-dione

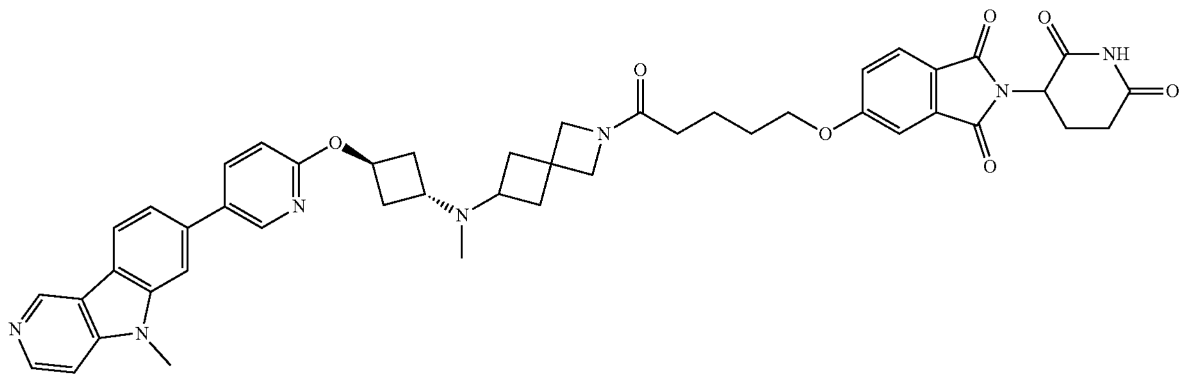 [SMILES: Cn1c2ccncc2c2ccc(-c3ccc(O[C@H]4C[C@H](N(C)C5CC6(C5)CN(C(=O)CCCCOc5ccc7c(c5)C(=O)N(C5CCC(=O)NC5=O)C7=O)C6)C4)nc3)cc21]

Step 1: Benzyl 5-hydroxypentanoate

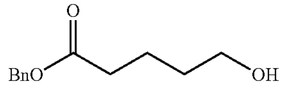 [SMILES: O=C(CCCCO)OCc1ccccc1]

A mixture of tetrahydro-2H-pyran-2-one (1 g, 10 mmol) and sodium hydroxide (400 mg, 10 mmol) in water (15 ml) was stirred at 70° C. for 16 hours. The mixture was concentrated under reduced pressure to give a crude residue which was dissolved in acetone (20 ml), followed by sequential addition of tetrabutylammonium bromide (161 mg, 0.5 mmol) and benzyl bromide (2 g, 12 mmol) at room temperature. The mixture was stirred at 60° C. for 4 hours. TLC showed the reaction was complete. The mixture was concentrated and the residue was partitioned between ethyl acetate (30 ml) and water (50 ml). The organic layer was collected, washed with brine (30 ml), dried over anhydrous sodium sulfate, and concentrated under reduced pressure to give a crude residue which was purified by silica gel flash chromatography (eluted with 33-50% ethyl acetate in hexane) to afford benzyl 5-hydroxypentanoate (500 mg, 24%) as light yellow solid.

Benzyl 5-hydroxypentanoate was converted to the final compound, 2-(2,6-dioxopiperidin-3-yl)-5-((5-(6-(methyl((1r,3r)-3-((5-(5-methyl-5H-pyrido[4,3-b]indol-7-yl)pyridin-2-yl)oxy)cyclobutyl)amino)-2-azaspiro[3.3]heptan-2-yl)-5-oxopentyl)oxy)isoindoline-1,3-dione, according to the schemes below and using procedures described above and common procedures known to those skilled in the art.

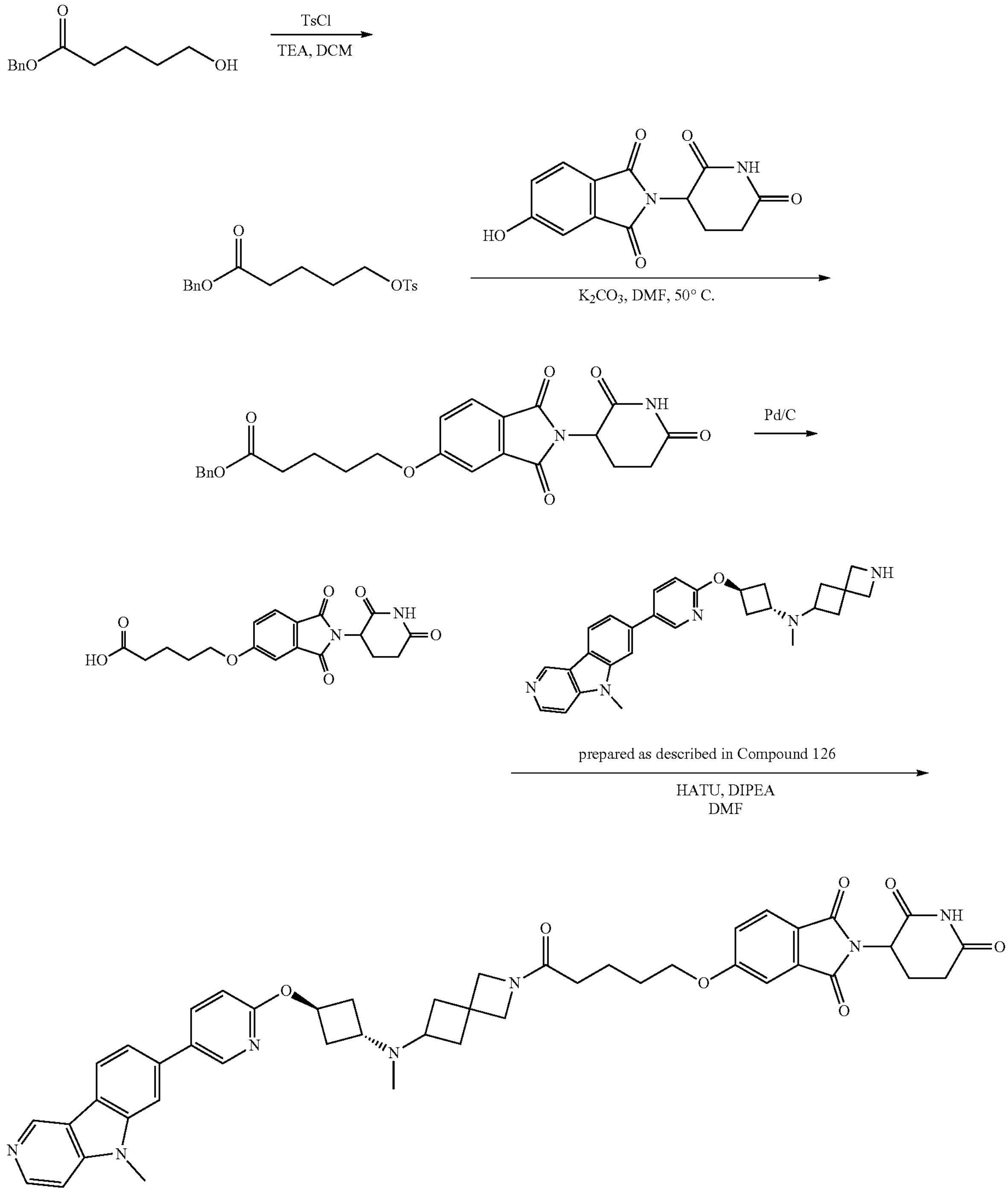
Compound 137
Compound 137: $^1$H NMR (400 MHz, DMSO-d6): δ 1.58-1.63 (m, 2H), 1.72-1.77 (m, 2H), 2.03-2.11 (m, 3H), 2.33-2.47 (m, 8H), 2.54-2.62 (m, 2H), 2.78-2.90 (m, 3H), 3.41-3.48 (m, 3H), 3.75-3.79 (m, 1H), 3.80-3.87 (m, 1H), 4.02 (s, 3H), 4.06 (s, 1H), 4.13-4.18 (m, 3H), 5.10-5.14 (m, 1H), 5.25-5.28 (m, 1H), 6.96-7.00 (m, 1H), 7.33-7.42 (m, 2H), 7.70 (d, J=8.4 Hz, 1H), 7.80-7.84 (m, 2H), 8.06 (s, 1H), 8.23-8.26 (m, 1H), 8.39 (d, J=8.0 Hz, 1H), 8.57-8.67 (m, 2H), 9.49 (s, 11H), 11.12 (s, 1H). $(M+H)^+$ 810.6.

Synthetic Scheme for Exemplary Compound 138

5-((14-((5-(5-(difluoromethyl)-5H-pyrido[4,3-b]indol-7-yl)pyridin-2-yl)oxy)-3,6,9,12-tetraoxatetradecyl)oxy)-2-(2,6-dioxopiperidin-3-yl)isoindoline-1,3-dione

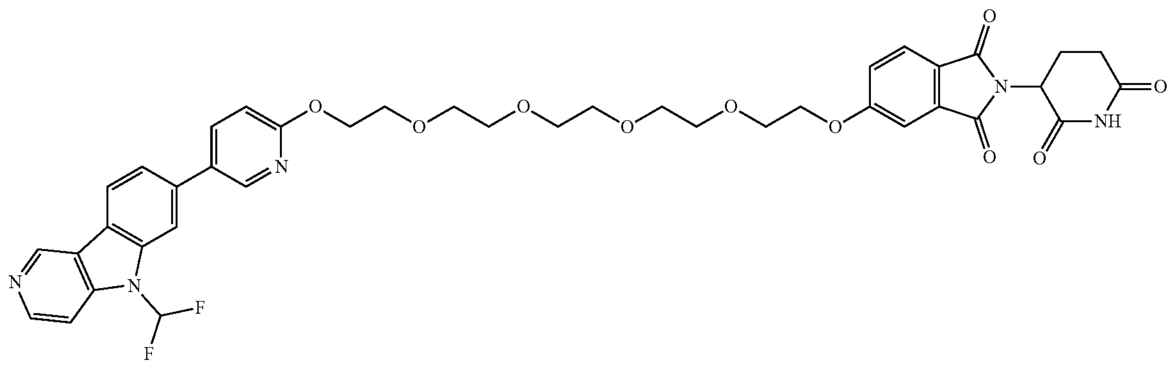 [SMILES: O=C1CCC(N2C(=O)c3ccc(OCCOCCOCCOCCOCCOc4ccc(-c5ccc6c7cnccc7n(C(F)F)c6c5)cn4)cc3C2=O)C(=O)N1]

Step 1: 5-(difluoromethyl)-7-(6-fluoropyridin-3-yl)-5H-pyrido[4,3-b]indole

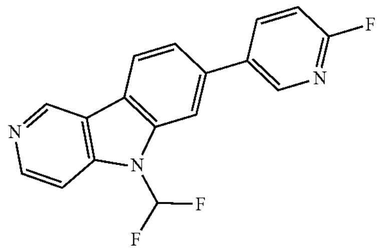 [SMILES: Fc1ccc(-c2ccc3c4cnccc4n(C(F)F)c3c2)cn1]

To a solution of 7-(6-fluoropyridin-3-yl)-5H-pyrido[4,3-b]indole (500 m g, 1.90 mmol) in dry N,N-dimethylformamide (6 ml) was added sodium hydride (60% in mineral oil) (380 mg, 9.50 mmol) at 0° C., and the resulting mixture was stirred at room temperature for 30 minutes. Then sodium 2-chloro-2,2-difluoroacetate (580 mg, 3.80 mmol) was added, and the resulting reaction mixture was stirred at 80° C. for 5 hours. The reaction mixture was quenched with water (30 ml) at 0° C. and extracted with ethyl acetate (30 ml). The combined organic layers were washed with brine (30 ml), dried over anhydrous sodium sulfate, and concentrated under reduced pressure to give a residue which was purified by silica gel flash chromatography (eluted with 50% ethyl acetate in hexane) to afford 5-(difluoromethyl)-7-(6-fluoropyridin-3-yl)-5H-pyrido[4,3-b]indole (35 mg, yield 6%) as yellow solid.

5-(Difluoromethyl)-7-(6-fluoropyridin-3-yl)-5H-pyrido[4,3-b]indole was converted to the final compound, 5-((14-((5-(5-(difluoromethyl)-5H-pyrido[4,3-b]indol-7-yl)pyridin-2-yl)oxy)-3,6,9,12-tetraoxatetradecyl)oxy)-2-(2,6-dioxopiperidin-3-yl)isoindoline-1,3-dione, according to the scheme below using procedures described above and common procedures known to those skilled in the art.

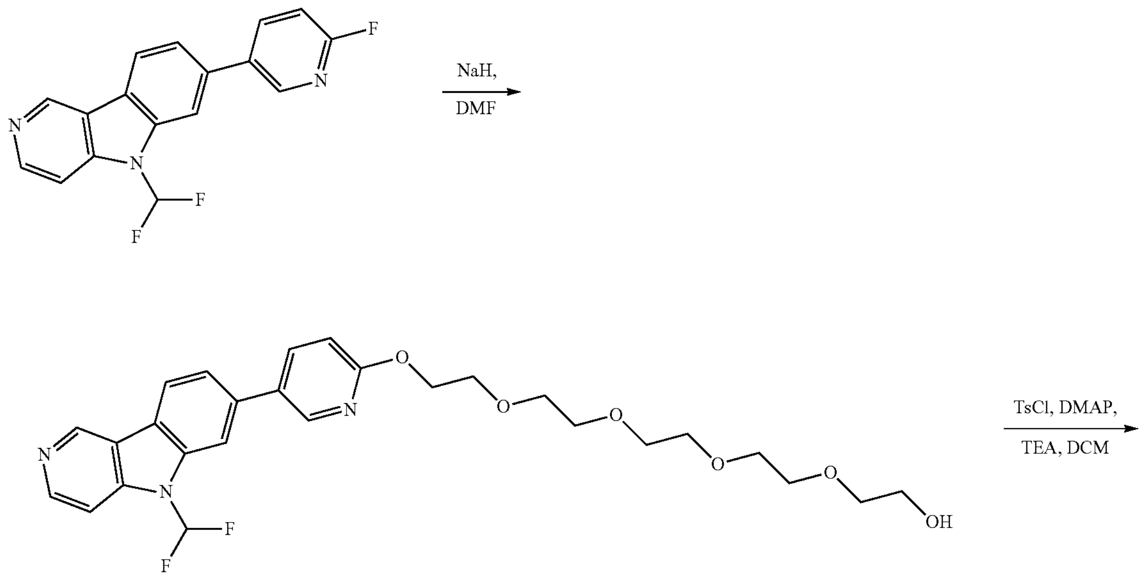

-continued

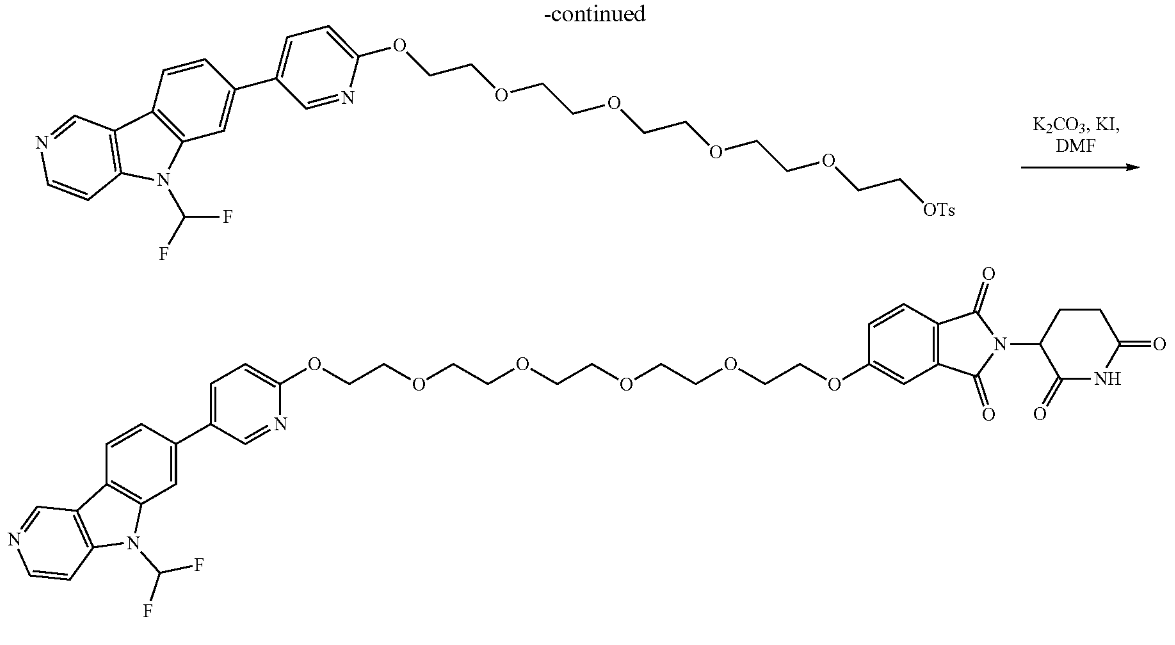

Compound 138

Compound 138: $^1H$ NMR (400 MHz, DMSO-d6): δ 2.01-2.04 (m, 1H), 2.56-2.67 (m, 2H), 2.83-2.93 (m, 1H), 3.52-3.59 (m, 12H), 3.78 (s, 4H), 4.29 (s, 2H), 4.45 (s, 2H), 5.11 (d, J=12.8 Hz, 1H), 6.98 (d, J=8.8 Hz, 1H), 7.34 (d, J=8.4 Hz, 1H), 7.43 (s, 1H), 7.76-7.83 (m, 3H), 8.14-8.18 (m, 2H), 8.36-8.50 (m, 2H), 8.61-8.65 (m, 2H), 9.49 (s, 1H), 11.11 (s, 1H). $(M+H)^+$ 788.5.

Synthetic Scheme for Exemplary Compound 139

2-(2,6-dioxopiperidin-3-yl)-5-((14-((3-fluoro-5-(5-methyl-5H-pyrido[4,3-b]indol-7-yl)pyridin-2-yl)oxy)-3,6,9,12-tetraoxatetradecyl)oxy)isoindoline-1,3-dione

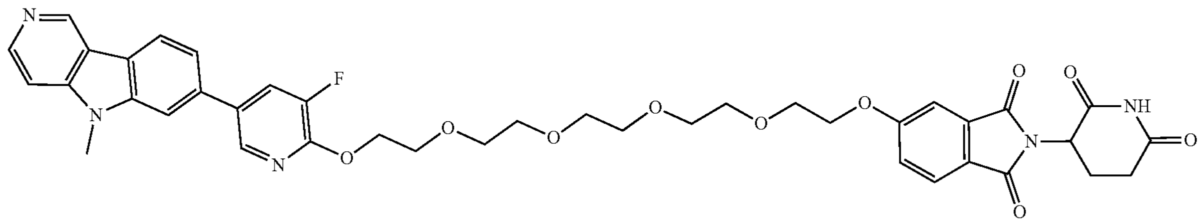 [SMILES: Cn1c2ccncc2c2ccc(-c3cnc(OCCOCCOCCOCCOCCOc4ccc5c(c4)C(=O)N(C4CCC(=O)NC4=O)C5=O)c(F)c3)cc21]

Prepared according to the scheme below using procedures described above and common procedures known to those skilled in the art.

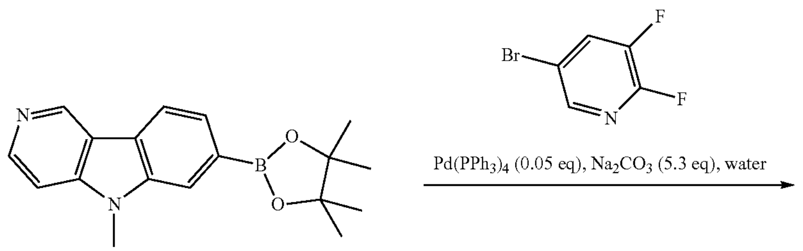

-continued
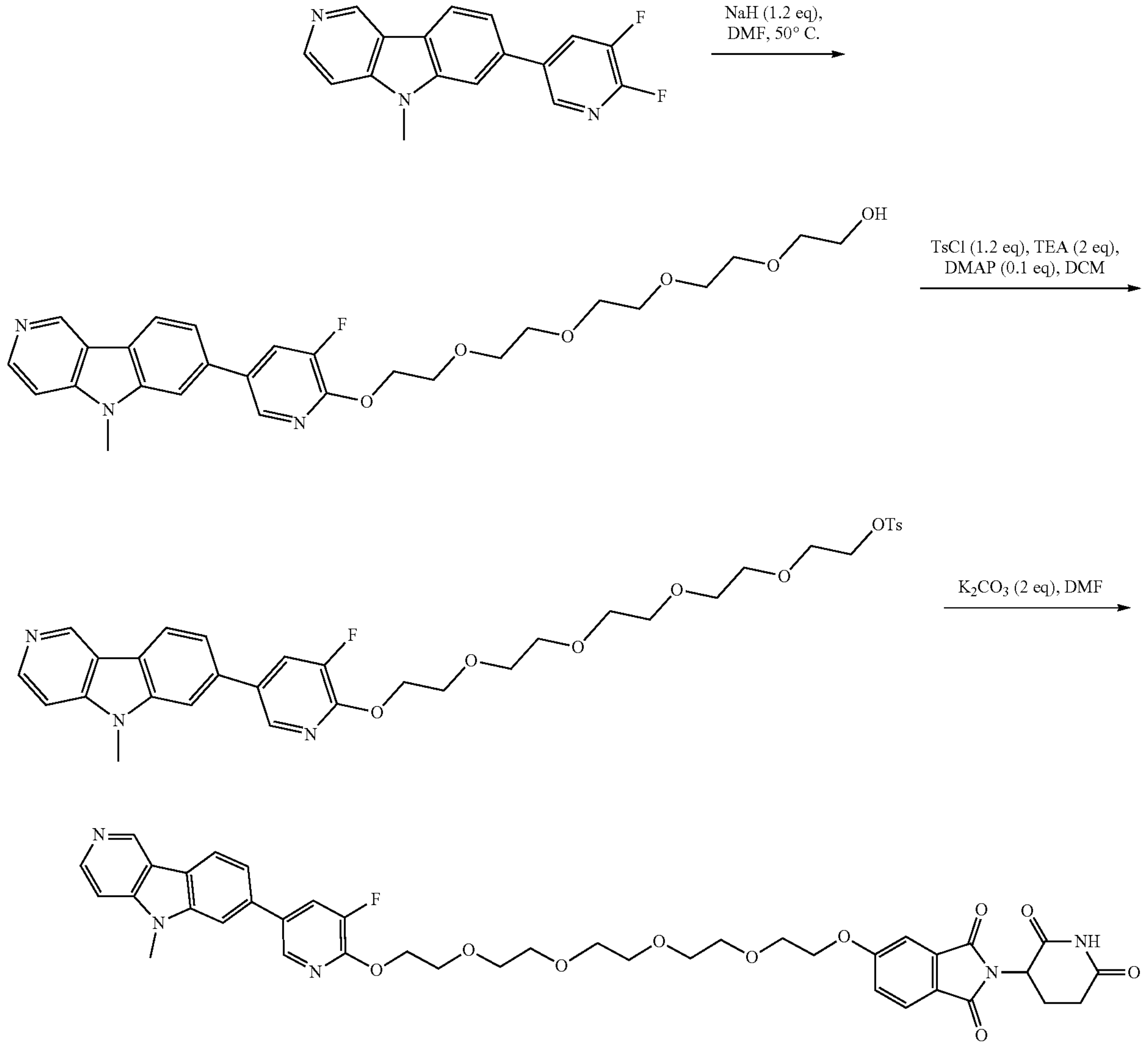
Compound 139
Synthetic Scheme for Exemplary Compound 140
2-(2,6-dioxopiperidin-3-yl)-5-((14-((3-methyl-5-(5-methyl-5H-pyrido[4,3-b]indol-7-yl)pyridin-2-yl)oxy)-3,6,9,12-tetraoxatetradecyl)oxy)isoindoline-1,3-dione
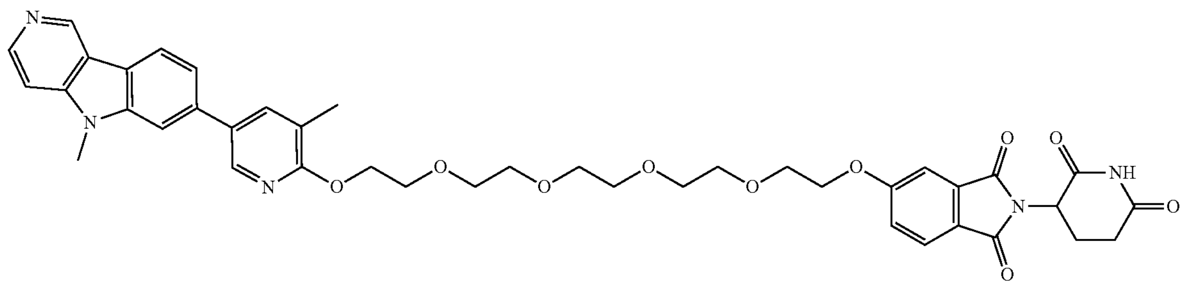 [SMILES: Cc1cc(-c2ccc3c4cnccc4n(C)c3c2)cnc1OCCOCCOCCOCCOCCOc1ccc2c(c1)C(=O)N(C1CCC(=O)NC1=O)C2=O]

Step 1: 2-fluoro-5-iodo-3-methylpyridine

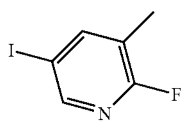

A mixture of 6-fluoro-5-methylpyridin-3-amine (300 mg, 2.4 mmol) in N,N-dimethylacetamide (10 ml) was added potassium iodide (395 mg, 2.4 mmol), iodine (306 g, 1.2 mmol), copper(I) iodide (137 mg, 0.72 mmol) and tert-butyl nitrite (1.7 g, 14.4 mmol) was stirred at 90° C. for 2 hours. The reaction mixture was quenched with water (30 ml) and extracted with ethyl acetate (20 ml). The combined organic layers were washed with brine (30 ml), dried over anhydrous sodium sulfate, and concentrated under reduced pressure to give a residue which was purified by silica gel flash chromatography (eluted with 10% ethyl acetate in hexane) to afford 2-fluoro-5-iodo-3-methylpyridine (350 mg, yield 62%) as white solid.

2-fluoro-5-iodo-3-methylpyridine was converted to the final compound, 2-(2,6-dioxopiperidin-3-yl)-5-((14-((3-methyl-5-(5-methyl-5H-pyrido[4,3-b]indol-7-yl)pyridin-2-yl)oxy)-3,6,9,12-tetraoxatetradecyl)oxy)isoindoline-1,3-dione, according to the scheme below using procedures described above and common procedures known to those skilled in the art.

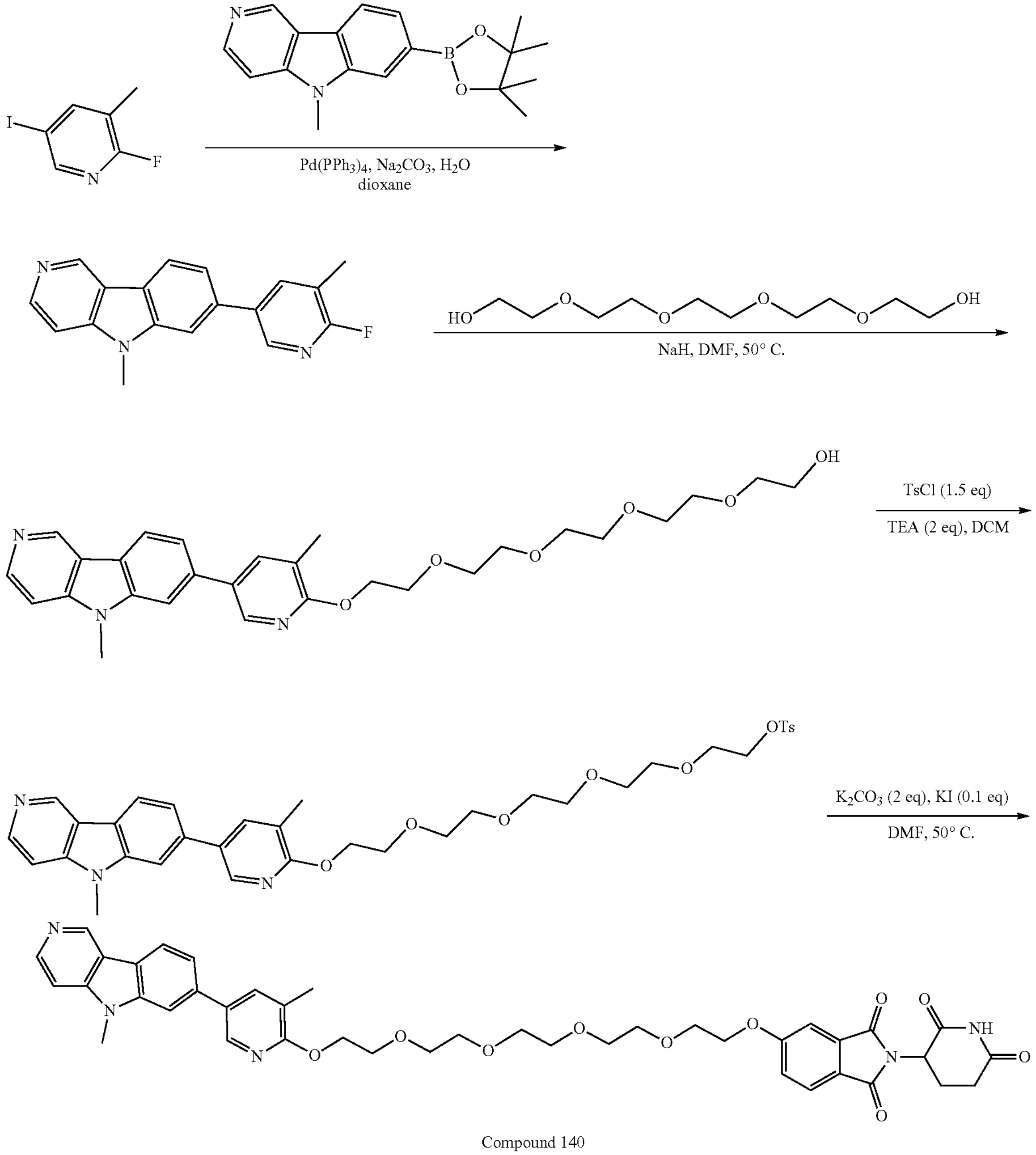

Compound 140

Synthetic Scheme for Exemplary Compound 141

2-(2,6-dioxopiperidin-3-yl)-5-((6-(5-((1r,3r)-3-((5-(5-methyl-5H-pyrido[4,3-b]indol-7-yl)pyridin-2-yl)oxy)cyclobutoxy)pyrimidin-2-yl)hex-5-yn-1-yl)oxy)isoindoline-1,3-dione

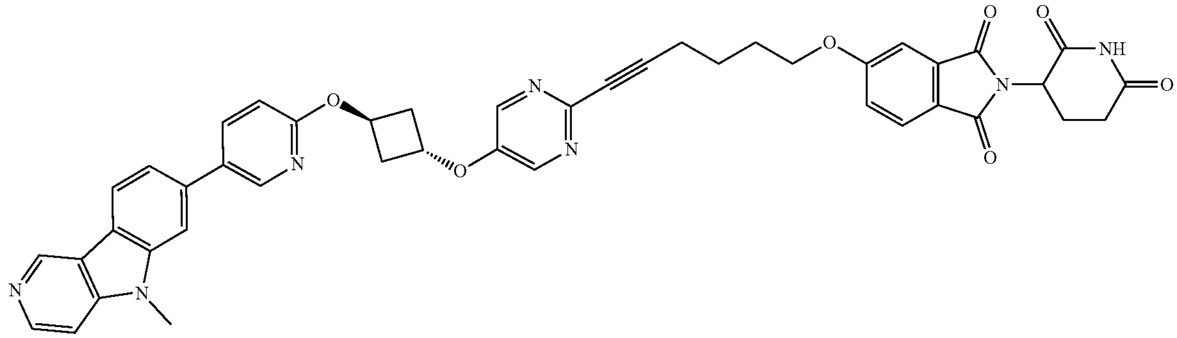 [SMILES: Cn1c2ccncc2c2ccc(-c3ccc(O[C@H]4C[C@H](Oc5cnc(C#CCCCCOc6ccc7c(c6)C(=O)N(C6CCC(=O)NC6=O)C7=O)nc5)C4)nc3)cc21]

Prepared according to the scheme below using procedures described above and common procedures known to those skilled in the art.

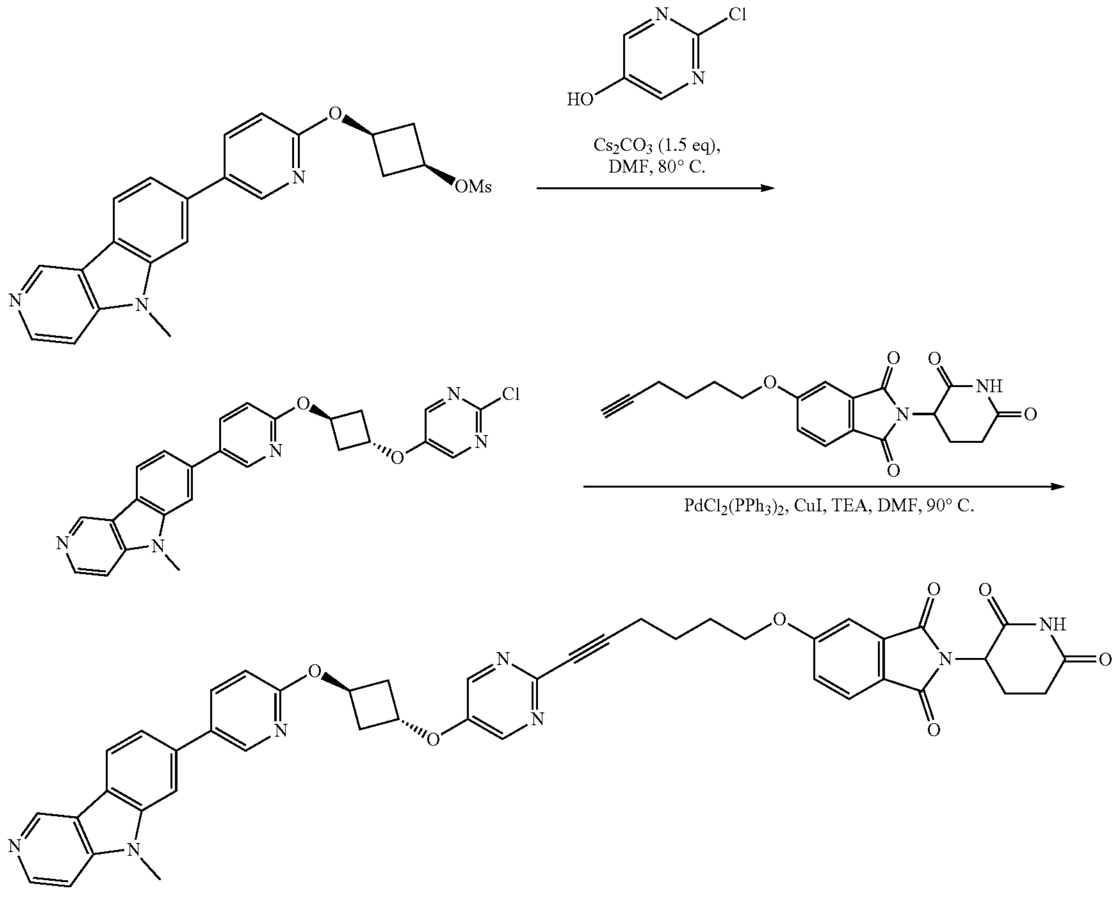

Compound 141

Additionally, Compound 151 was prepared from Compound 141 using hydrogenation procedure described previously for the conversion of Compound 102 to Compound. 110.

Synthetic Scheme for Exemplary Compound 142
2-(2,6-dioxopiperidin-3-yl)-5-((1-(3-(5-((1r,3r)-3-((5-(5-methyl-5H-pyrido[4,3-b]indol-7-yl)-3-(trifluoromethyl)pyridin-2-yl)oxy)cyclobutoxy)pyridin-2-yl)prop-2-yn-1-yl)azetidin-3-yl)oxy)isoindoline-1,3-dione
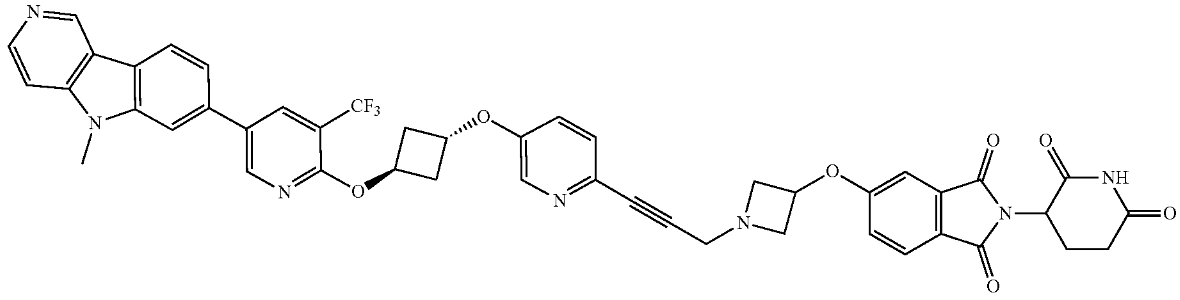 [SMILES: Cn1c2ccncc2c2ccc(-c3cnc(O[C@H]4C[C@H](Oc5ccc(C#CCN6CC(Oc7ccc8c(c7)C(=O)N(C7CCC(=O)NC7=O)C8=O)C6)nc5)C4)c(C(F)(F)F)c3)cc21]
Prepared according to the scheme below using procedures described above and common procedures known to those skilled in the art.
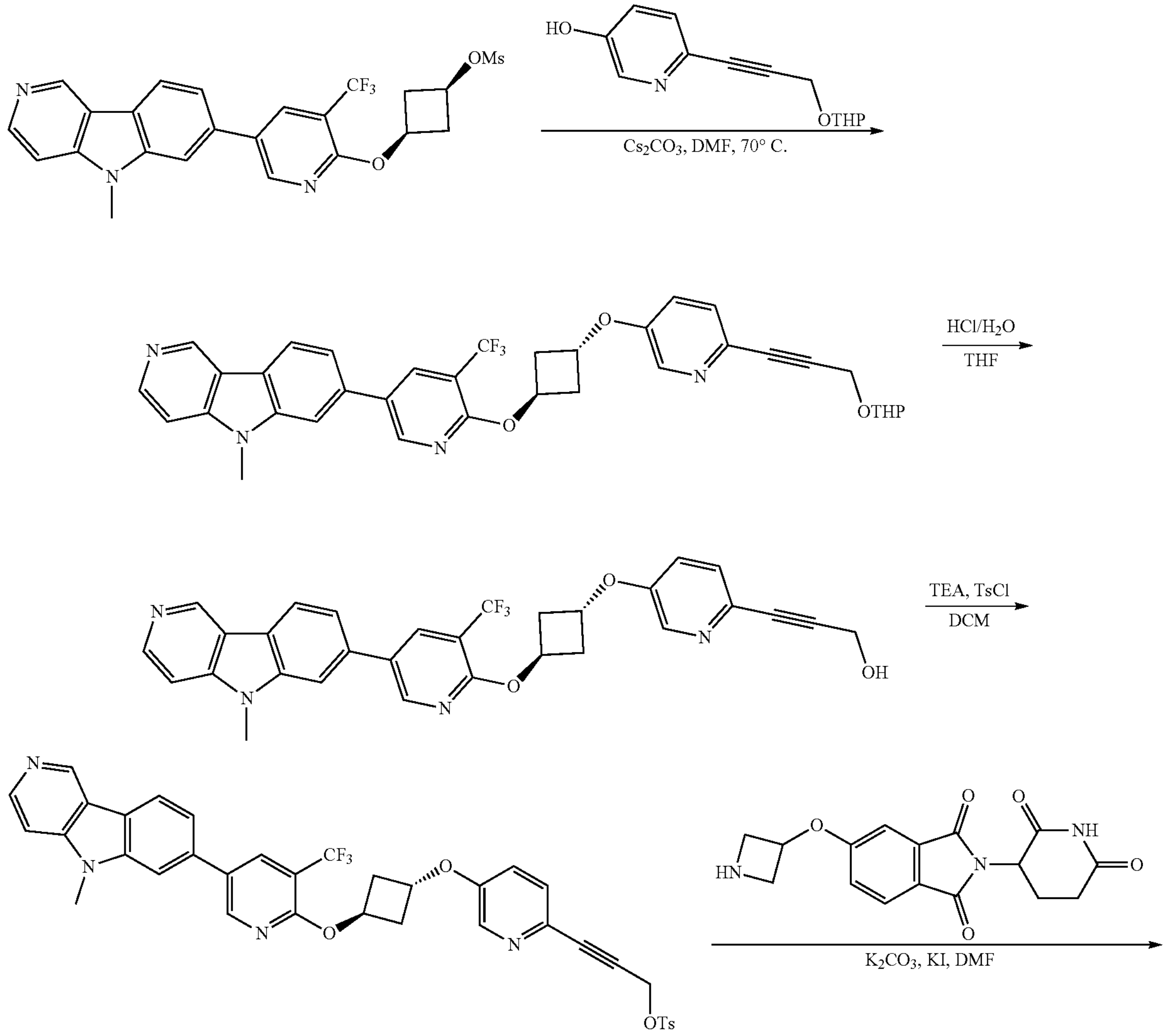

-continued

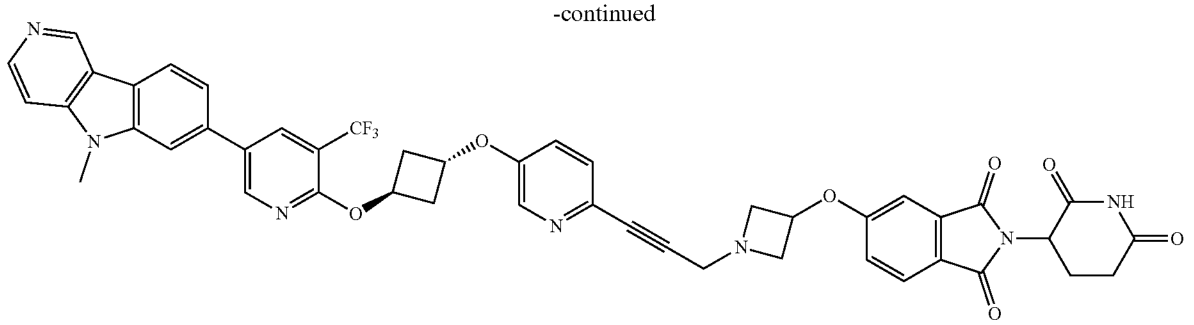

Compound 142

Synthetic Scheme for Exemplary Compound 143

2-(2,6-dioxopiperidin-3-yl)-5-((14-((5-(5-methyl-5H-pyrido[4,3-b]indol-7-yl)-6-(trifluoromethyl)pyridin-2-yl)oxy)-3,6,9,12-tetraoxatetradecyl)oxy)isoindoline-1,3-dione

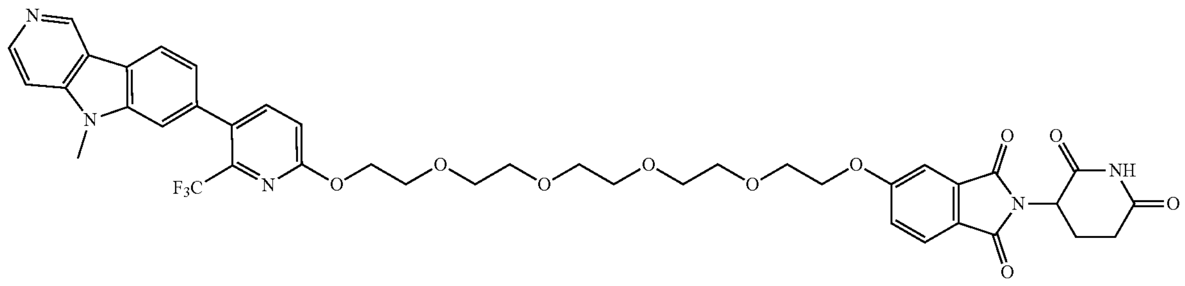 [SMILES: Cn1c2ccncc2c2ccc(-c3ccc(OCCOCCOCCOCCOCCOc4ccc5c(c4)C(=O)N(C4CCC(=O)NC4=O)C5=O)nc3C(F)(F)F)cc21]

Step 1: 6-chloro-3-iodo-2-(trifluoromethyl)pyridine

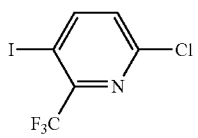 [SMILES: FC(F)(F)c1nc(Cl)ccc1I]

To a solution of lithium diisopropylamide (2 M in THF, 3.03 mmol) in tetrahydrofuran (15 ml) was added a solution of 2-chloro-6-(trifluoromethyl)pyridine (500 mg, 2.75 mmol) in tetrahydrofuran (5 ml) at −65° C. under nitrogen atmosphere. The dark brown solution was stirred at −65° C. for 30 minutes. To the reaction mixture was added a solution of iodine (0.7 g, 2.75 mmol) in tetrahydrofuran (5 ml) was added at −65° C. within 20 minutes. After additional 20 minutes stirring at the same temperature, the reaction mixture was quenched with hydrochloride acid (2M, 6 ml) at 0° C. and stirred for 20 minutes. The reaction mixture was extracted with ethyl acetate (30 ml). The combined organic layers were washed with brine (30 ml), dried over anhydrous sodium sulfate, and concentrated under reduced pressure to give a residue which was purified by silica gel flash chromatography (eluted with 1% ethyl acetate in hexane) to afford 6-chloro-3-iodo-2-(trifluoromethyl)pyridine (316 mg, yield 37%) as brown oil.

6-Chloro-3-iodo-2-(trifluoromethyl)pyridine was converted to the final compound, 2-(2,6-dioxopiperidin-3-yl)-5-((14-((5-(5-methyl-5H-pyrido[4,3-b]indol-7-yl)-6-(trifluoromethyl)pyridin-2-yl)oxy)-3,6,9,12-tetraoxatetradecyl)oxy)isoindoline-1,3-dione, according to the scheme below using procedures described above and common procedures known to those skilled in the art.

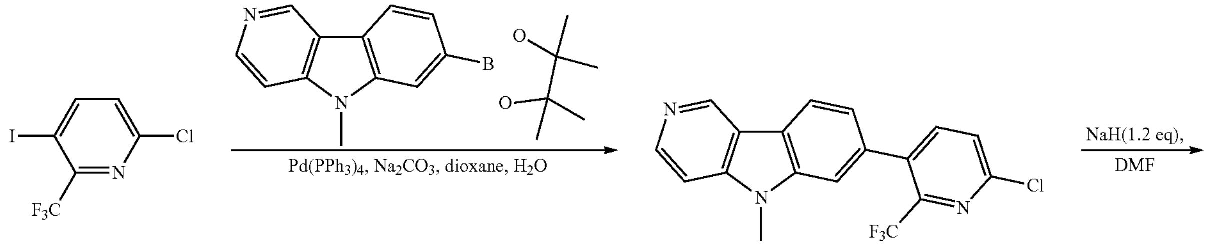

-continued
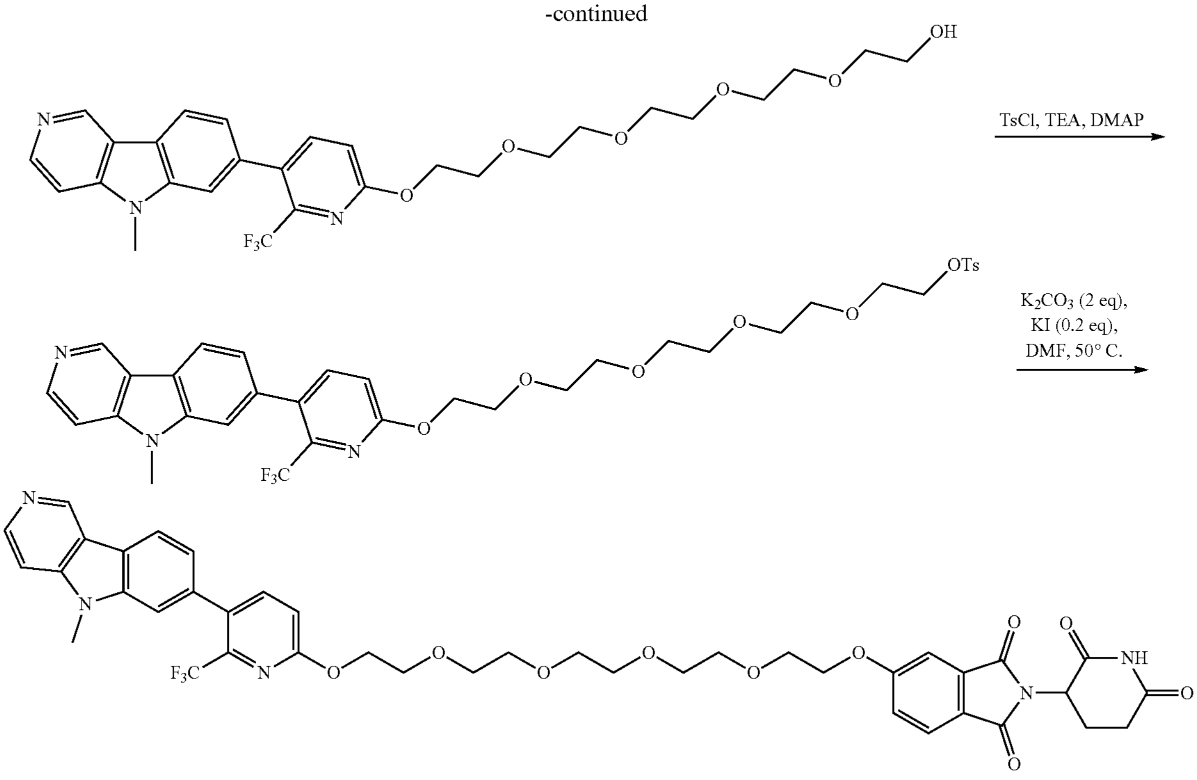
Compound 143
Synthetic Scheme for Exemplary Compound 146
2-(2,6-dioxopiperidin-3-yl)-5-((6-(6-(3-((5-(5-methyl-5H-pyrido[4,3-b]indol-7-yl)pyridin-2-yl)oxy)propoxy)pyridin-3-yl)hex-5-yn-1-yl)oxy)isoindoline-1,3-dione
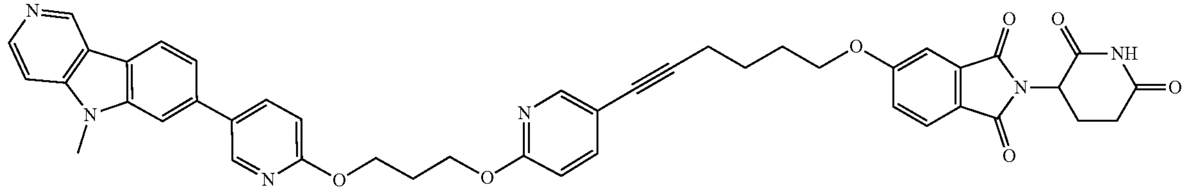 [SMILES: Cn1c2ccncc2c2ccc(-c3ccc(OCCCOc4ccc(C#CCCCCOc5ccc6c(c5)C(=O)N(C5CCC(=O)NC5=O)C6=O)cn4)nc3)cc21]
Prepared according to the scheme below using procedures described above and common procedures known to those skilled in the art.
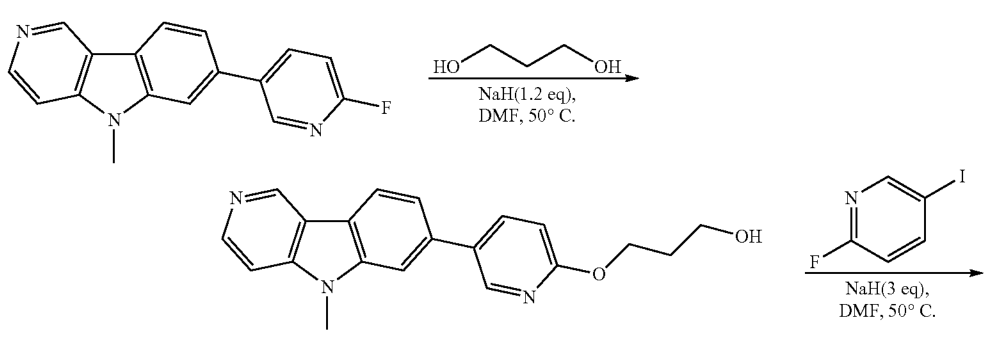

-continued
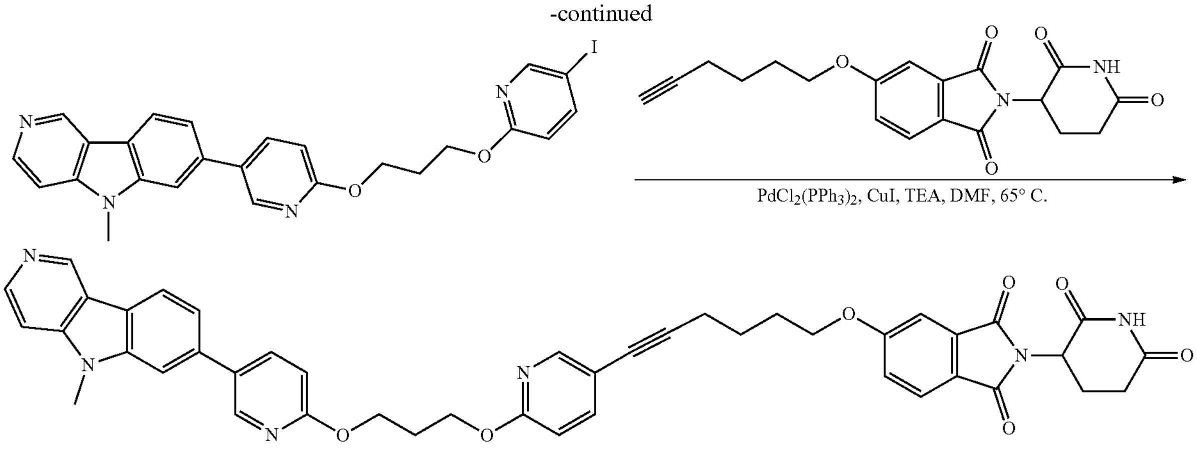
Compound 146
Synthetic Scheme for Exemplary Compound 152
2-(2,6-dioxopiperidin-3-yl)-5-((1-(3-(5-((1r,3r)-3-((5-(5-methyl-5H-pyrido[4,3-b]indol-7-yl)pyridin-2-yl)oxy)cyclobutoxy)pyridin-2-yl)prop-2-yn-1-yl)azetidin-3-yl)oxy)isoindoline-1,3-dione
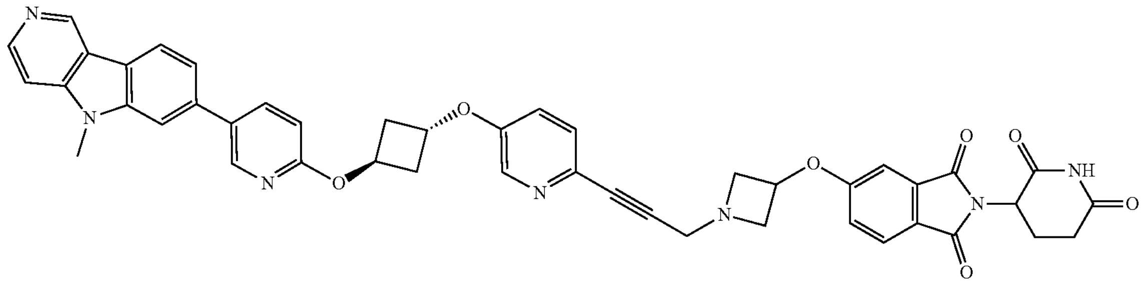 [SMILES: Cn1c2ccncc2c2ccc(-c3ccc(O[C@H]4C[C@H](Oc5ccc(C#CCN6CC(Oc7ccc8c(c7)C(=O)N(C7CCC(=O)NC7=O)C8=O)C6)nc5)C4)nc3)cc21]
Prepared according to the scheme below using procedures described above and common procedures known to those skilled in the art.
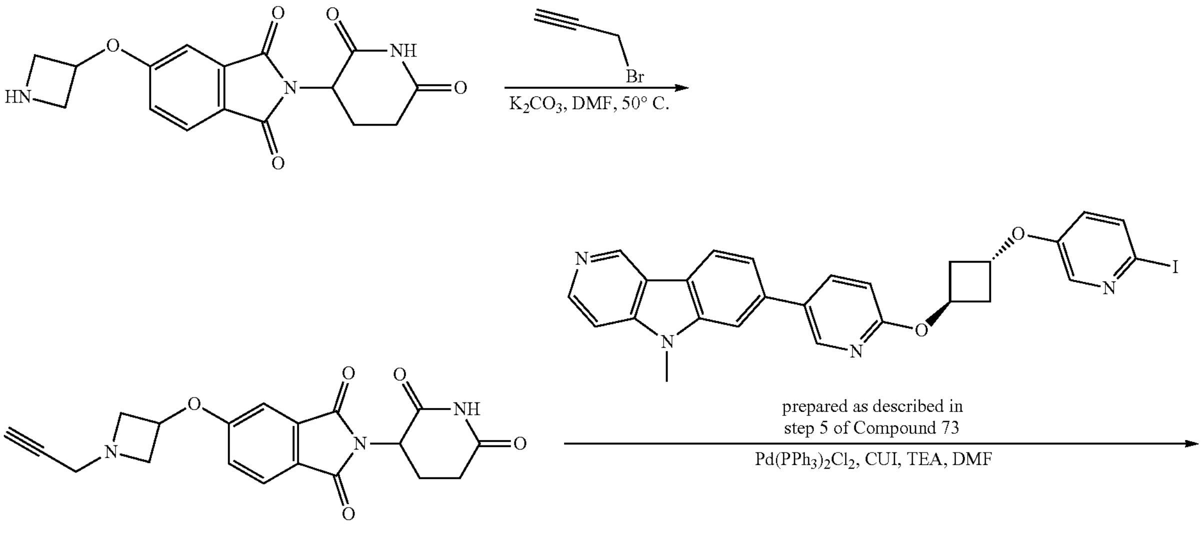

-continued

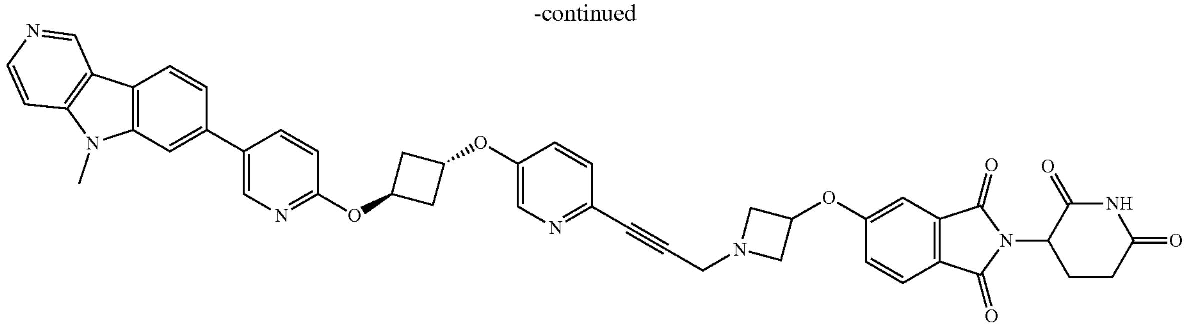

Compound 152

Synthetic Scheme for Exemplary Compound 150

Step 1: 2-[5-(3-benzyloxycyclobutoxy)-2,2-difluoro-pentoxy]tetrahydropyran

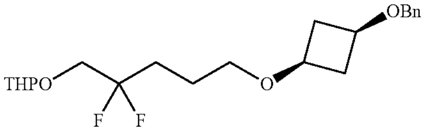

To a solution of 3-benzyloxycyclobutanol (2.59 g, 14.53 mmol, 1.10 eq) in N,N-dimethylformamide (100 mL) was added sodium hydride (581 mg, 14.53 mmol, 60% in mineral oil, 1.10 eq) at 0° C. under nitrogen. The mixture was stirred at 0° C. for 0.5 hours and added a solution of (4,4-difluoro-5-tetrahydropyran-2-yloxy-pentyl) 4-methylbenzenesulfonate (5.0 g, 13.21 mmol, 1.00 eq) [prepared as described for Compound 171] in N,N-dimethylformamide (20 mL) dropwise at 0° C. The reaction mixture was stirred at 60° C. for 6 hours. The mixture was cooled to 25° C. and poured into ice-water (w/w=1/1) (30 mL) and stirred for 15 minutes. The aqueous phase was extracted with ethyl acetate (100 mL×3). The combined organic phase was washed with brine (100 mL×3), dried with anhydrous sodium sulfate, filtered and concentrated under vacuum. The residue was purified by silica gel chromatography (Petroleum ether/Ethyl acetate=1/0, 20/1) to afford 2-[5-(3-benzyloxycyclobutoxy)-2,2-difluoro-pentoxy]tetrahydropyran (1.75 g, 4.21 mmol, 32% yield, 92% purity) as a colorless oil.

Step 2: 3-(4,4-difluoro-5-tetrahydropyran-2-yloxy-pentoxy)cyclobutanol

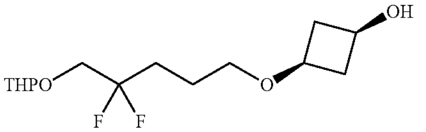

To a solution of 2-[5-(3-benzyloxycyclobutoxy)-2,2-difluoro-pentoxy]tetrahydropyran (1.75 g, 4.55 mmol, 1.00 eq) in methanol (30 mL) was added palladium on activated carbon catalyst (1.0 g, 10% purity) under nitrogen. The suspension was degassed under vacuum and purged with hydrogen several times. The mixture was stirred under hydrogen (15 psi) at 25° C. for 16 hours. The reaction mixture was filtered and the filter was concentrated. The crude product was purified by silica gel chromatography (Petroleum ether/Ethyl acetate=10:1 to 1:1) to give 3-(4,4-difluoro-5-tetrahydropyran-2-yloxy-pentoxy)cyclobutanol (1.2 g, 4.08 mmol, 90% yield) as a colorless oil.

Step 3: 5-Bromo-2-[3-(4,4-difluoro-5-tetrahydropyran-2-yloxy-pentoxy)cyclobutoxy]pyridine

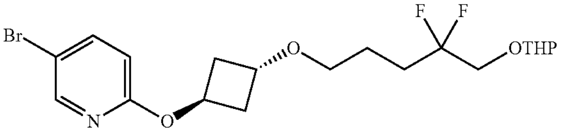

To a mixture of 3-(4,4-difluoro-5-tetrahydropyran-2-yloxy-pentoxy)cyclobutanol (1.2 g, 4.08 mmol, 1.00 eq) and 5-bromopyridin-2-ol (1.06 g, 6.12 mmol, 1.50 eq) in toluene (60 mL) was added 1,1'-(azodicarbonyl)dipiperidine (1.54 g, 6.12 mmol, 1.50 eq) and tributylphosphane (1.24 g, 6.12 mmol, 1.50 eq) in one portion at 0° C. under nitrogen. The mixture was stirred at 110° C. for 16 hours. The mixture was cooled to 25° C. and concentrated at reduced pressure at 45° C. The residue was poured into ice-water (w/w=1/1) (30 mL) and stirred for 15 minutes. The aqueous phase was extracted with ethyl acetate (50 mL×3). The combined organic phase was washed with brine (50 mL×2), dried with anhydrous sodium sulfate, filtered and concentrated in vacuum. The residue was purified by silica gel chromatography (Petroleum ether/Ethyl acetate=100/1, 50/1). 5-Bromo-2-[3-(4,4-difluoro-5-tetrahydropyran-2-yloxy-pentoxy)cyclobutoxy]pyridine (1.36 g, 3.02 mmol, 74.0% yield) was obtained as a yellow oil.

Step 4: 5-[3-[(5-bromo-2-pyridyl)oxy] cyclobutoxy]-2,2-difluoro-pentan-1-ol

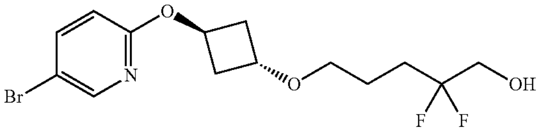 [SMILES: OCC(F)(F)CCCO[C@H]1C[C@H](Oc2ccc(Br)cn2)C1]

To a mixture of 5-bromo-2-[3-(4,4-difluoro-5-tetrahydropyran-2-yloxy-pentoxy) cyclobutoxy]pyridine (1.1 g, 2.44 mmol, 1.00 eq) in tetrahydrofuran (25 mL) was added hydrogen chloride (4 M, 10 mL, 16.38 eq) in one portion under nitrogen. Then the mixture was stirred at 25° C. for 1 hour. The mixture was poured into saturated sodium hydrogencarbonate (20 mL) and stirred for 15 minutes. The aqueous was extracted with ethyl acetate (50 mL×3). The combined organic phase was washed with brine (50 mL×3), dried with anhydrous sodium sulfate, filtered and concentrated under vacuum. The residue was purified by silica gel chromatography (Petroleum ether/Ethyl acetate=10/1, 5/1) to afford 5-[3-[(5-bromo-2-pyridyl)oxy] cyclobutoxy]-2,2-difluoro-pentan-1-ol (700 mg, 1.91 mmol, 78% yield) as a colorless oil.

Step 5: [5-[3-[(5-bromo-2-pyridyl)oxy]cyclobutoxy]-2,2-difluoro-pentyl]trifluoromethanesulfonate

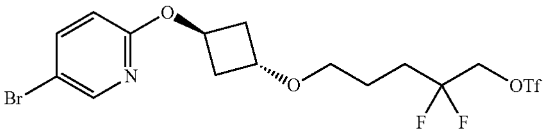 [SMILES: O=S(=O)(OCC(F)(F)CCCO[C@H]1C[C@H](Oc2ccc(Br)cn2)C1)C(F)(F)F]

To a mixture of 5-[3-[(5-bromo-2-pyridyl)oxy]cyclobutoxy]-2,2-difluoro-pentan-1-ol (400 mg, 1.09 mmol, 1.00 eq) and triethylamine (552 mg, 5.46 mmol, 5.00 eq) in dichloromethane (10 mL) was trifluoromethanesulfonyl chloride (368 mg, 2.18 mmol, 2.00 eq) at 0° C. under nitrogen. After the addition had finished, the reaction mixture was stirred at 25° C. for 1 hour. The mixture was concentrated in vacuum at 40° C. The residue was purified by silica gel chromatography (Petroleum ether/Ethyl acetate=5/1) to afford [5-[3-[(5-bromo-2-pyridyl)oxy]cyclobutoxy]-2,2-difluoro-pentyl] trifluoromethanesulfonate (465 mg, 0.93 mmol, 85% yield) as a colorless oil.

Step 6: tert-butyl 6-[2-(2,6-dioxo-3-piperidyl)-1,3-dioxo-isoindolin-5-yl]-2,6-diazaspiro[3.3]heptane-2-carboxylate

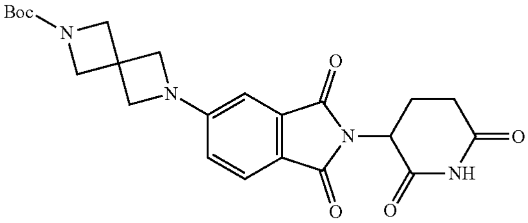 [SMILES: CC(C)(C)OC(=O)N1CC2(C1)CN(c1ccc3c(c1)C(=O)N(C1CCC(=O)NC1=O)C3=O)C2]

To a mixture of 2-(2,6-dioxo-3-piperidyl)-5-fluoro-isoindoline-1,3-dione (300 mg, 1.09 mmol, 1.00 eq) and tert-butyl 2,6-diazaspiro[3.3]heptane-2-carboxylate; oxalic acid (317 mg, 0.65 mmol, 0.60 eq) in (methylsulfinyl)methane (5 mL) was added N,N-diisopropylethylamine (561 mg, 4.34 mmol, 4.00 eq) in one portion under nitrogen. The mixture was heated to 120° C. and stirred for 16 hours. The mixture was poured into ice-water (w/w=1/1) (30 mL) and stirred for 10 minutes. The aqueous phase was extracted with ethyl acetate (50 mL×3). The combined organic phase was washed with brine (50 mL×3), dried with anhydrous sodium sulfate, filtered and concentrated in vacuum. The residue was triturated by Petroleum ether:Ethyl acetate (1:1, 50 mL) to afford tert-butyl 6-[2-(2,6-dioxo-3-piperidyl)-1,3-dioxo-isoindolin-5-yl]-2,6-diazaspiro[3.3]heptane-2-carboxylate (420 mg, 0.92 mmol, 85% yield) as a yellow solid.

Step 7: 5-(2,6-diazaspiro[3.3]heptan-2-yl)-2-(2,6-dioxo-3-piperidyl)isoindoline-1,3-dione

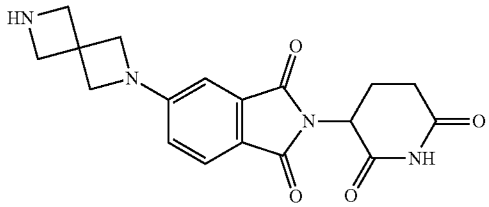 [SMILES: O=C1CCC(N2C(=O)c3ccc(N4CC5(CNC5)C4)cc3C2=O)C(=O)N1]

A mixture of tert-butyl 6-[2-(2,6-dioxo-3-piperidyl)-1,3-dioxo-isoindolin-5-yl]-2,6-diazaspi ro[3.3]heptane-2-carboxylate (420 mg, 0.92 mmol, 1.00 eq) in trifluoroacetic acid (1 mL) and dichloromethane (10 mL) was stirred at 25° C. for 1 hour under nitrogen. TLC showed the reaction was completed. The mixture was concentrated in reduced pressure at 45° C. The mixture was purified by semi-preparative reverse phase HPLC (column: Phenomenex Synergi Max-RP 250*50 mm*10 um; mobile phase: [water (0.225% FA)-ACN]; B %: 5ACN %-30ACN %, 15 min; 50% min) to afford 5-(2,6-diazaspiro[3.3]heptan-2-yl)-2-(2,6-dioxo-3-piperidyl)isoindoline-1,3-dione formate (260 mg, 0.64 mmol, 70% yield) as a yellow solid.

Step 8: 5-[6-[5-[3-[(5-bromo-2-pyridyl)oxy]cyclobutoxy]-2,2-difluoro-pentyl]-2,6-diazaspiro[3.3]heptan-2-yl]-2-(2,6-dioxo-3-piperidyl)isoindoline-1,3-dione

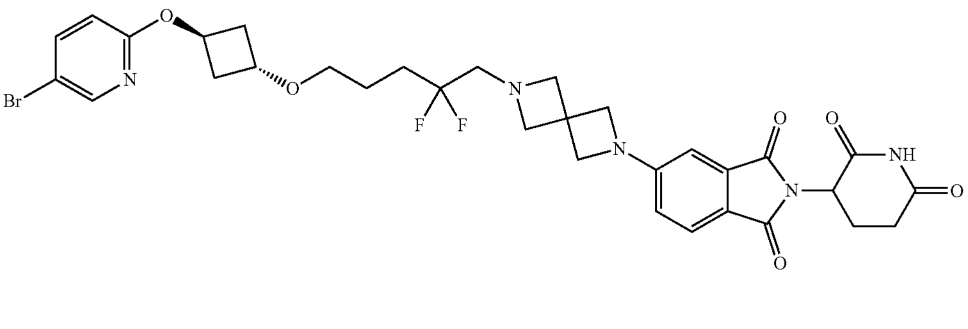 [SMILES: O=C1CCC(N2C(=O)c3ccc(N4CC5(CN(CC(F)(F)CCCO[C@H]6C[C@H](Oc7ccc(Br)cn7)C6)C5)C4)cc3C2=O)C(=O)N1]

To a mixture of [5-[3-[(5-bromo-2-pyridyl)oxy]cyclobutoxy]-2,2-difluoro-pentyl]trifluoromethanesulfonate (460 mg, 0.92 mmol, 1.00 eq) and 5-(2,6-diazaspiro[3.3]heptan-2-yl)-2-(2,6-dioxo-3-piperidyl)isoindoline-1,3-dione formate (443 mg, 1.11 mmol, 1.20 eq) in acetonitrile (25 mL) and (methylsulfinyl)methane (5 mL) was added potassium carbonate (255 mg, 1.85 mmol, 2.00 eq) in one portion at 25° C. under nitrogen. The mixture was stirred at 25° C. for 10 hours. LC-MS showed [5-[3-[(5-bromo-2-pyridyl)oxy]cyclobutoxy]-2,2-difluoro-pentyl]trifluoromethanesulfonate was consumed completely and one main peak with desired MS was detected. The suspension was filtered and concentrated in vacuum. The residue was diluted with ethyl acetate (100 mL), washed with brine (30 mL×3), dried with anhydrous sodium sulfate, filtered and concentrated in vacuum. The residue was purified by silica gel chromatography (Petroleum ether/Ethyl acetate=1/1, 1/3) to afford 5-[6-[5-[3-[(5-bromo-2-pyridyl)oxy]cyclobutoxy]-2,2-difluoro-pentyl]-2,6-diazaspiro[3.3]heptan-2-yl]-2-(2,6-dioxo-3-piperidyl)isoindoline-1,3-dione (320 mg, 0.45 mmol, 49% yield) as a yellow solid.

Step 9: 5-[6-[2,2-difluoro-5-[3-[[5-(4,4,5,5-tetramethyl-1,3,2-dioxaborolan-2-yl)-2-pyridyl]oxy]cyclobutoxy]pentyl]-2,6-diazaspiro[3.3]heptan-2-yl]-2-(2,6-dioxo-3-piperidyl)isoindoline-1,3-dione

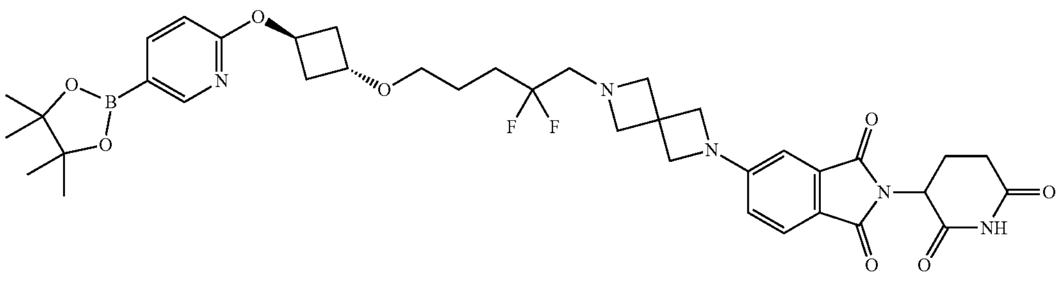 [SMILES: CC1(C)OB(c2ccc(O[C@H]3C[C@H](OCCCC(F)(F)CN4CC5(C4)CN(c4ccc6c(c4)C(=O)N(C4CCC(=O)NC4=O)C6=O)C5)C3)nc2)OC1(C)C]

5-[6-[5-[3-[(5-bromo-2-pyridyl)oxy]cyclobutoxy]-2,2-difluoro-pentyl]-2,6-diazaspiro[3.3]heptan-2-yl]-2-(2,6-dioxo-3-piperidyl)isoindoline-1,3-dione (200 mg, 0.28 mmol, 1.00 eq), 4,4,5,5-tetramethyl-2-(4,4,5,5-tetramethyl-1,3,2-dioxaborolan-2-yl)-1,3,2-dioxaborolane (86 mg, 0.34 mmol, 1.20 eq), potassium acetate (55 mg, 0.56 mmol, 2.00 eq) and 1,1'-bis(diphenylphosphino)ferrocene-palladium(ii)dichloride dichloromethane complex (23 mg, 0.02 mmol, 0.10 eq) in dioxane (10 mL) was de-gassed and then heated to 90° C. for 2 hours under nitrogen. The reaction mixture was filtered and the filter was concentrated. The crude product was purified by prep-TLC (dichloromethane:methanol=20:1) to give 5-[6-[2,2-difluoro-5-[3-[[5-(4,4,5,5-tetramethyl-1,3,2-dioxaborolan-2-yl)-2-pyridyl]oxy]cyclobutoxy]pentyl]-2,6-diazaspiro[3.3]heptan-2-yl]-2-(2,6-dioxo-3-piperidyl)isoindoline-1,3-dione (200 mg, 0.26 mmol, 94% yield) as a yellow oil.

Step 10: 5-[6-[2,2-difluoro-5-[3-[[5-(5-methylpyrido[4,3-b]indol-7-yl)-2-pyridyl]oxy]cyclobutoxy]pentyl]-2,6-diazaspiro[3.3]heptan-2-yl]-2-(2,6-dioxo-3-piperidyl)isoindoline-1,3-dione

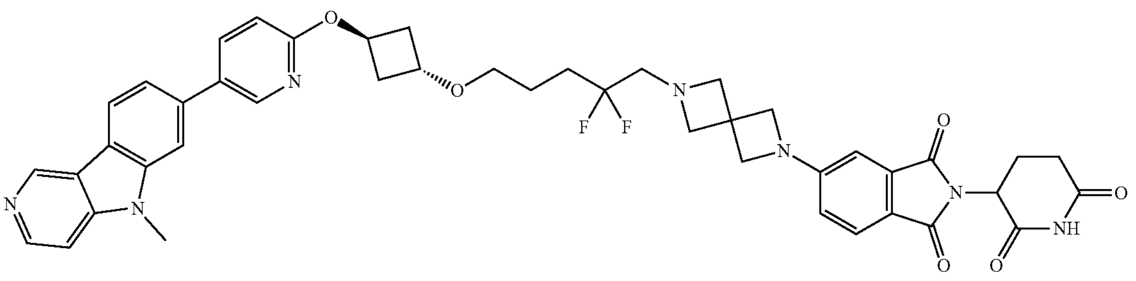 [SMILES: Cn1c2ccncc2c2ccc(-c3ccc(O[C@H]4C[C@H](OCCCC(F)(F)CN5CC6(C5)CN(c5ccc7c(c5)C(=O)N(C5CCC(=O)NC5=O)C7=O)C6)C4)nc3)cc21]

5-[6-[2,2-difluoro-5-[3-[[5-(4,4,5,5-tetramethyl-1,3,2-dioxaborolan-2-yl)-2-pyridyl]oxy]cyclobutoxy]pentyl]-2,6-diazaspiro[3.3]heptan-2-yl]-2-(2,6-dioxo-3-piperidyl)isoindoline-1,3-dione (200 mg, 0.26 mmol, 1.00 eq), 7-bromo-5-methyl-pyrido[4,3-b]indole (69 mg, 0.26 mmol, 1.00 eq), sodium carbonate (56 mg, 0.53 mmol, 2.00 eq) and 1,1'-bis(diphenylphosphino)ferrocene-palladium(ii)dichloride dichloromethane complex (21 mg, 0.02 mmol, 0.10 eq) in N,N-dimethylformamide (5 mL) and water (0.5 mL) was de-gassed and then heated to 90° C. for 2 hours under nitrogen. LCMS showed the reaction was completed. The mixture was cooled to 25° C. and filtered. The residue was diluted with ethyl acetate (50 mL), washed with brine (30 mL×3), dried over anhydrous sodium sulfate, concentrated in vacuum. The mixture was purified by semi-preparative reverse phase HPLC (18-48% acetonitrile+0.225% formic acid in water, over 10 min). Then the collected fraction was concentrated to remove most of the acetonitrile. The solution was lyophilized. 5-[6-[2,2-difluoro-5-[3-[[5-(5-methylpyrido[4,3-b]indol-7-yl)-2-pyridyl]oxy]cyclobutoxy]pentyl]-2,6-diazaspiro[3.3]heptan-2-yl]-2-(2,6-dioxo-3-piperidyl)isoindoline-1,3-dione formate (21.6 mg, 0.02 mmol, 9% yield, 95% purity) was obtained as a yellow solid.

$^1H$ NMR: (400 MHz, DMSO-$d_6$) δ: 10.95 (s, 1H), 9.14 (br s, 1H), 8.15 (s, 1H), 7.52 (d, J=9.0 Hz, 1H), 7.18-7.04 (m, 5H), 6.83 (d, J=6.7 Hz, 2H), 6.65 (d, J=8.5 Hz, 1H), 6.61 (s, 1H), 6.54-6.47 (m, 3H), 6.26 (d, J=8.5 Hz, 2H), 5.05 (dd, J=5.0, 13.3 Hz, 1H), 4.38-4.26 (m, 1H), 4.24-4.11 (m, 1H), 3.78 (br t, J=6.5 Hz, 4H), 3.54-3.31 (m, 3H), 3.03-2.83 (m, 8H), 2.62-2.52 (m, 3H), 2.47-2.31 (m, 1H), 2.21-2.04 (m, 3H), 2.01-1.87 (m, 3H), 1.71 (br d, J=10.7 Hz, 2H). $(M+H)^+$ 804.5.

Synthetic Scheme for Exemplary Compound 153

2-(2,6-dioxopiperidin-3-yl)-5-(3-(3,3,3-trifluoro-2-((5-((1r,3r)-3-((5-(5-methyl-5H-pyrido[4,3-b]indol-7-yl)pyridin-2-yl)oxy)cyclobutoxy)pentyl)oxy)propyl)azetidin-1-yl)isoindoline-1,3-dione

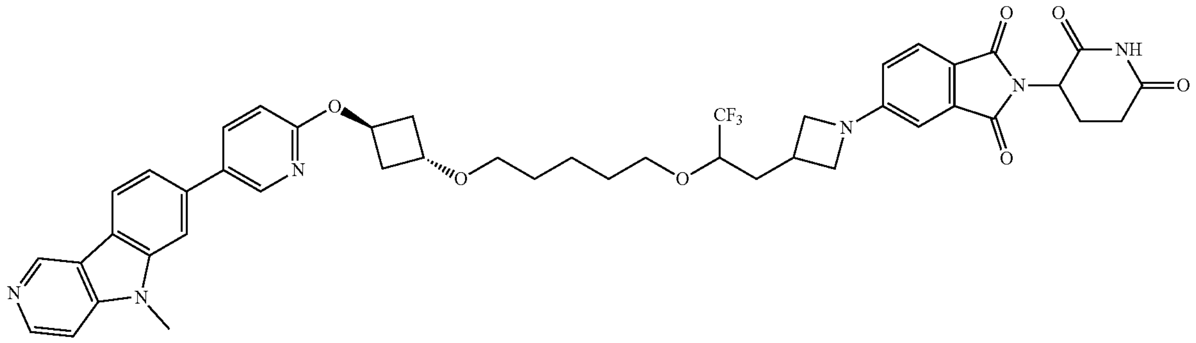 [SMILES: Cn1c2ccncc2c2ccc(-c3ccc(O[C@H]4C[C@H](OCCCCCOC(CC5CN(c6ccc7c(c6)C(=O)N(C6CCC(=O)NC6=O)C7=O)C5)C(F)(F)F)C4)nc3)cc21]

Prepared according to the schemes below using procedures described above and common procedures known to those skilled in the art.

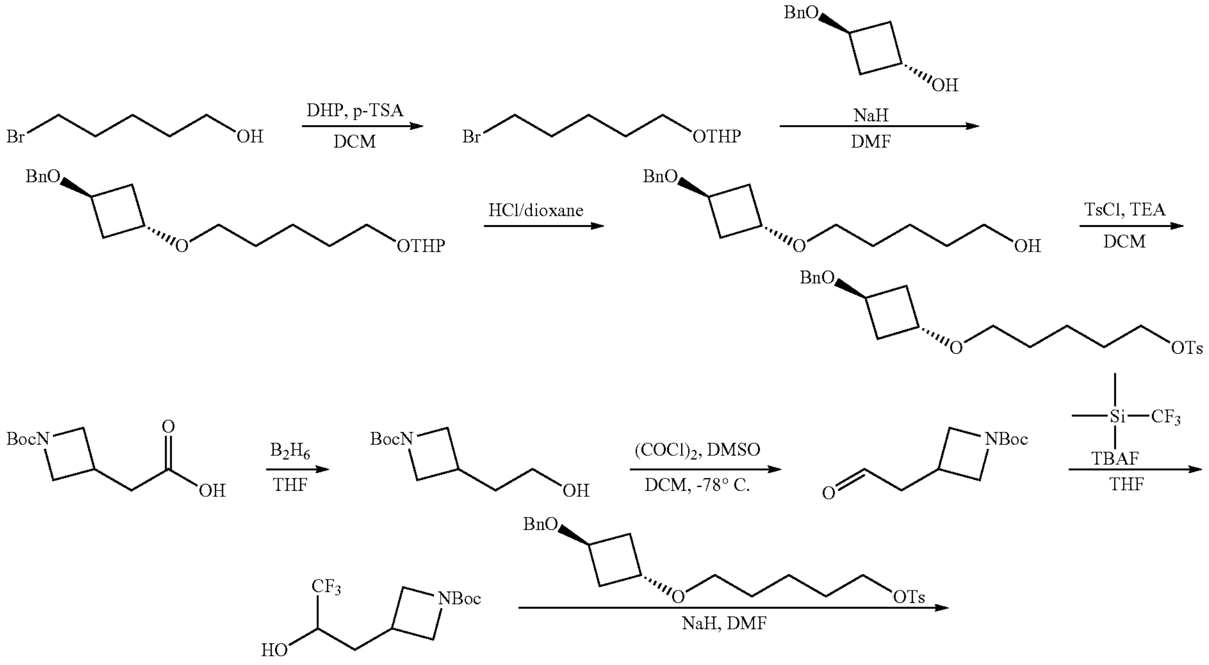

-continued
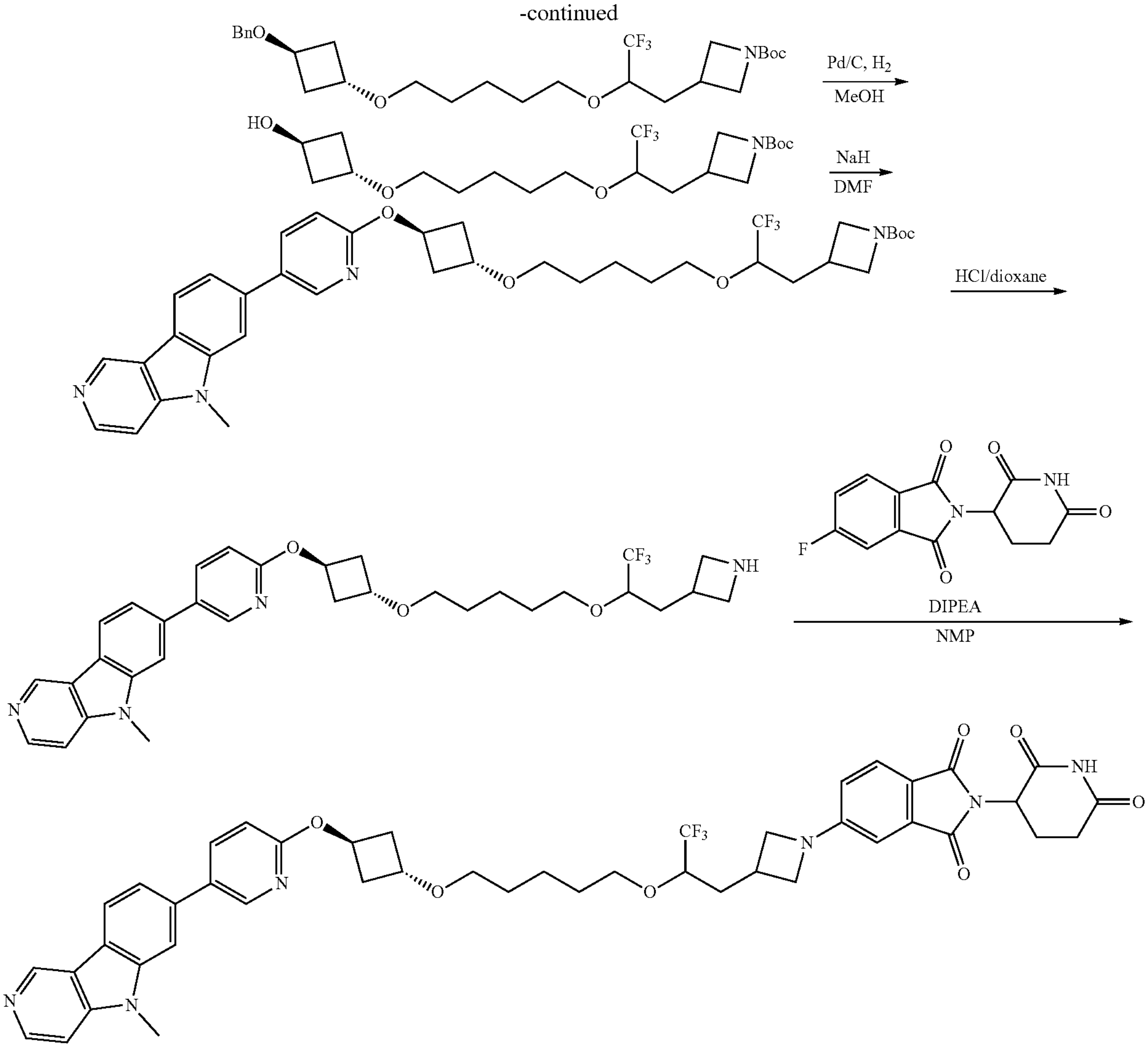
Compound 153
Using procedures of Compound 153 the following were prepared: Compound 154.
Synthetic Scheme for Exemplary Compound 155
2-(2,6-dioxopiperidin-3-yl)-5-(3-((5-(2-((1r,3r)-3-((5-(5-methyl-5H-pyrido[4,3-b]indol-7-yl)pyridin-2-yl)oxy)cyclobutoxy)ethoxy)pyridin-2-yl)oxy)azetidin-1-yl) isoindoline-1,3-dione
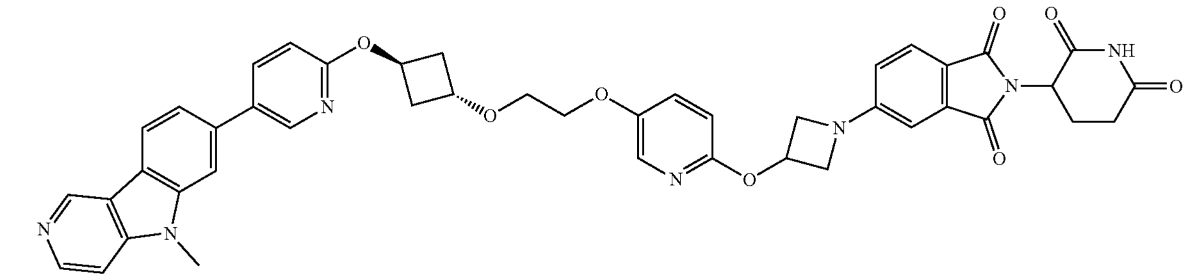 [SMILES: Cn1c2ccncc2c2ccc(-c3ccc(O[C@H]4C[C@H](OCCOc5ccc(OC6CN(c7ccc8c(c7)C(=O)N(C7CCC(=O)NC7=O)C8=O)C6)nc5)C4)nc3)cc21]

Prepared according to the schemes below using procedures described above and common procedures known to those skilled in the art.
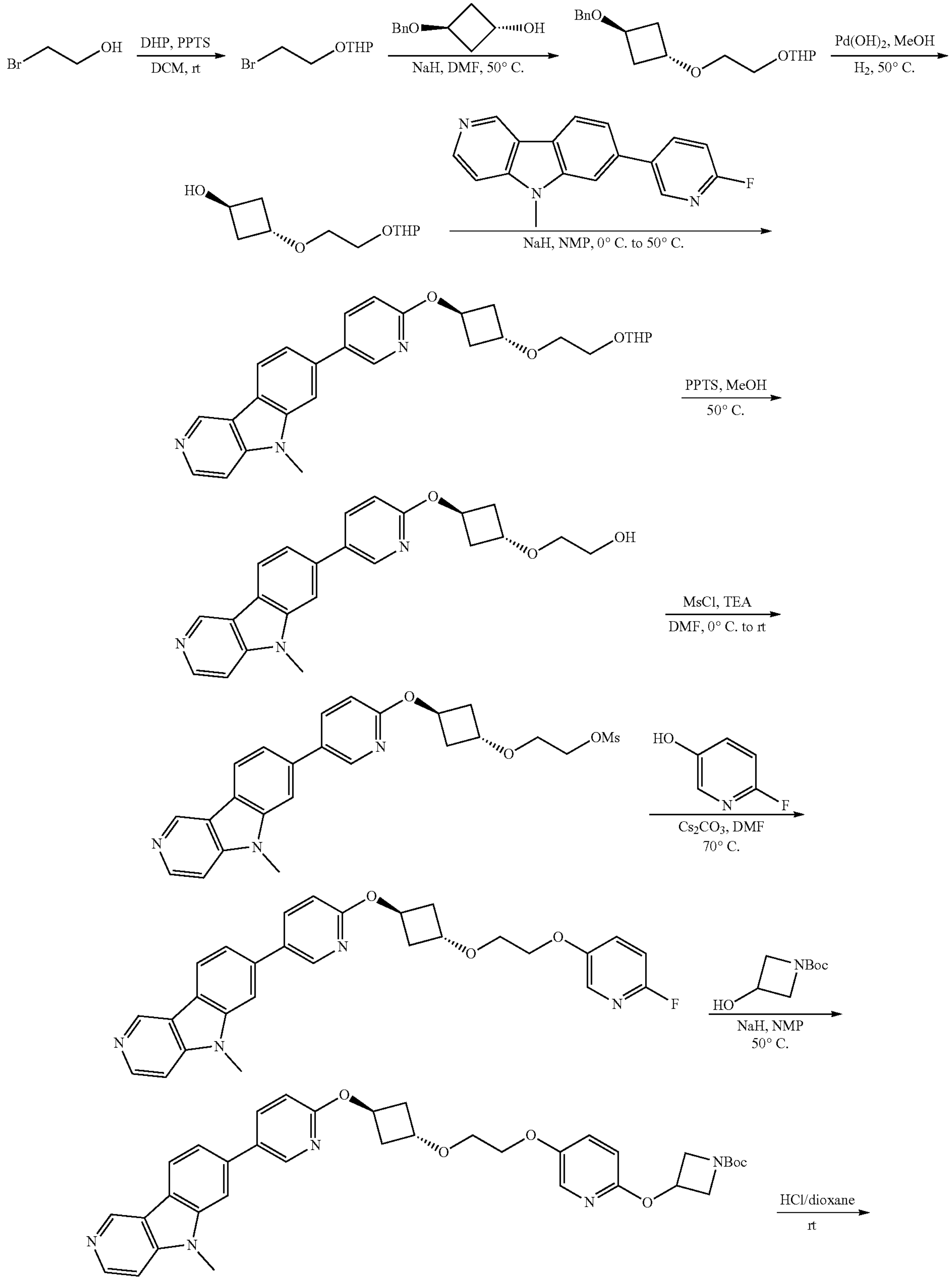

-continued
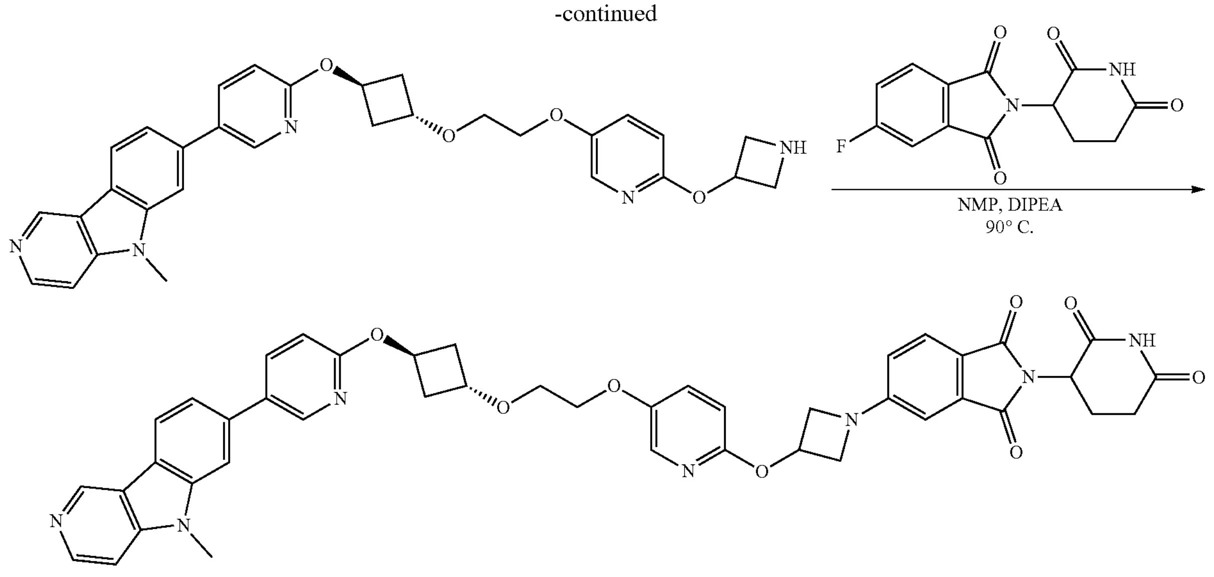
Compound 155
Synthetic Scheme for Exemplary Compound 156
2-(2,6-dioxopiperidin-3-yl)-5-(3-(3-(5-((1r,3r)-3-((5-(5-methyl-5H-pyrido[4,3-b]indol-7-yl)pyridin-2-yl)oxy)cyclobutoxy)pyridin-2-yl)propoxy)azetidin-1-yl)isoindoline-1,3-dione
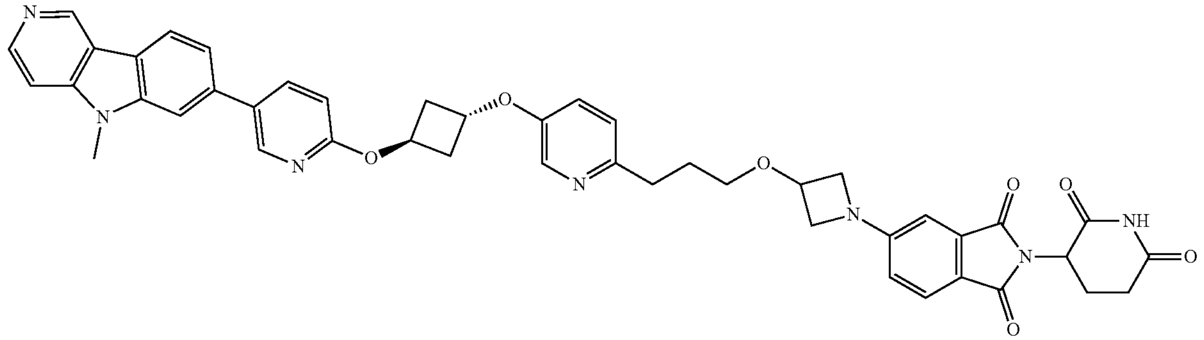 [SMILES: Cn1c2ccncc2c2ccc(-c3ccc(O[C@H]4C[C@H](Oc5ccc(CCCOC6CN(c7ccc8c(c7)C(=O)N(C7CCC(=O)NC7=O)C8=O)C6)nc5)C4)nc3)cc21]
Prepared according to the schemes below and using procedures described above and common procedures known to those skilled in the art.
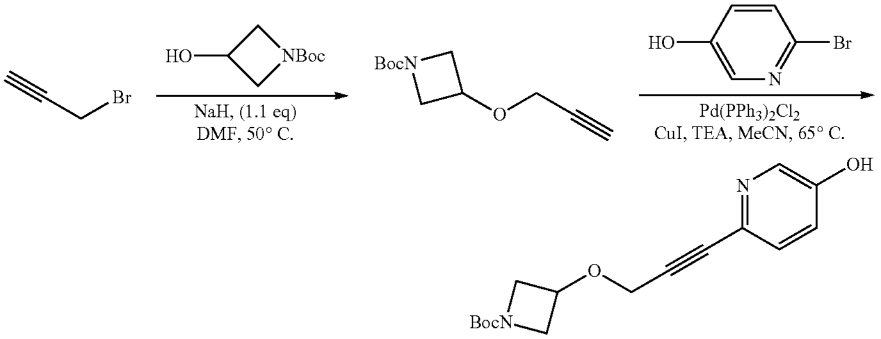

-continued
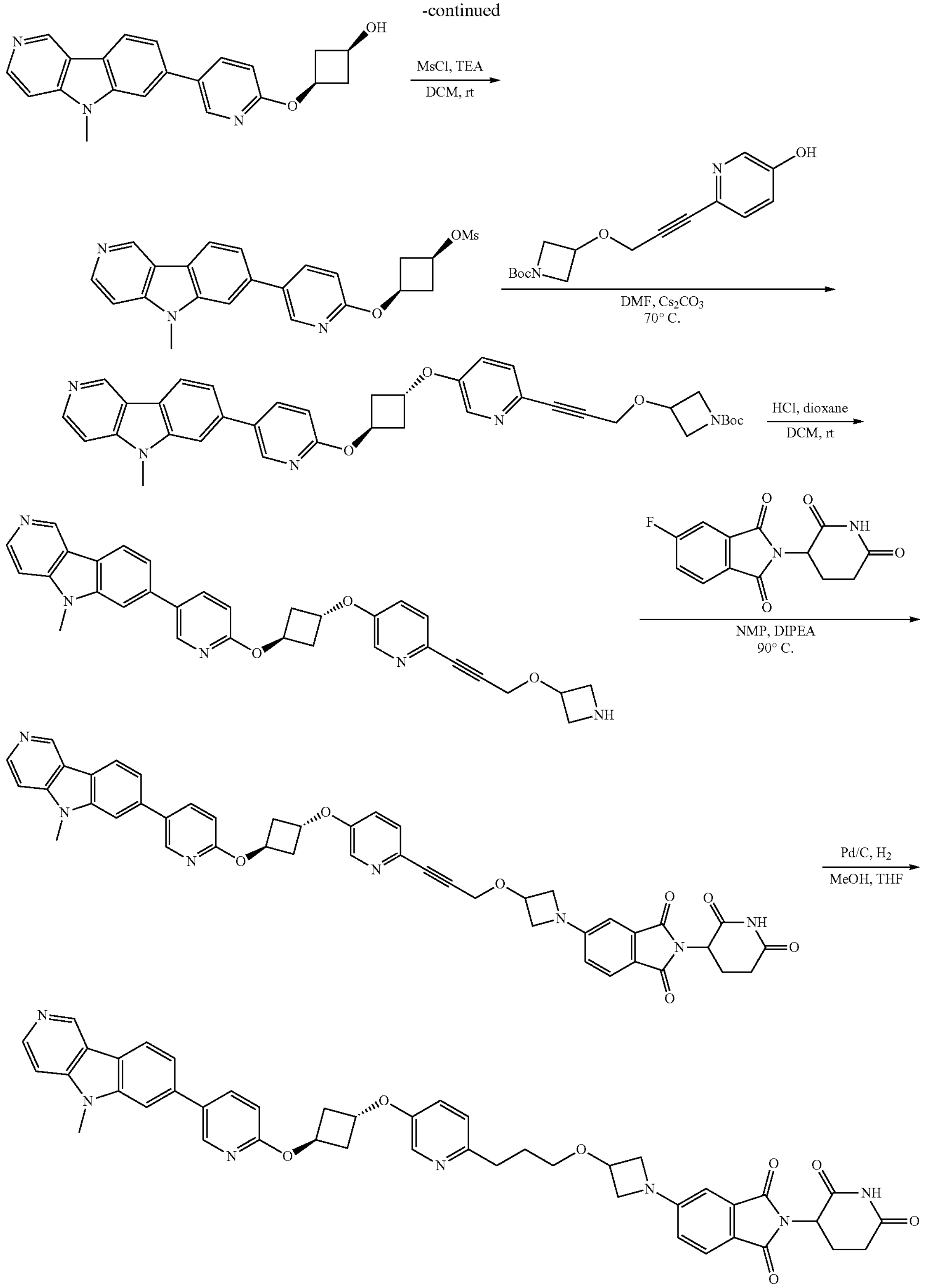
Compound 156

Synthetic Scheme for Exemplary Compound 157

2-(2,6-dioxopiperidin-3-yl)-5-(4-((2-((1r,3r)-3-((5-(5-methyl-5H-pyrido[4,3-b]indol-7-yl)pyridin-2-yl)oxy)cyclobutane-1-carbonyl)-2-azaspiro[3.3]heptan-6-yl)oxy)butoxy)isoindoline-1,3-dione

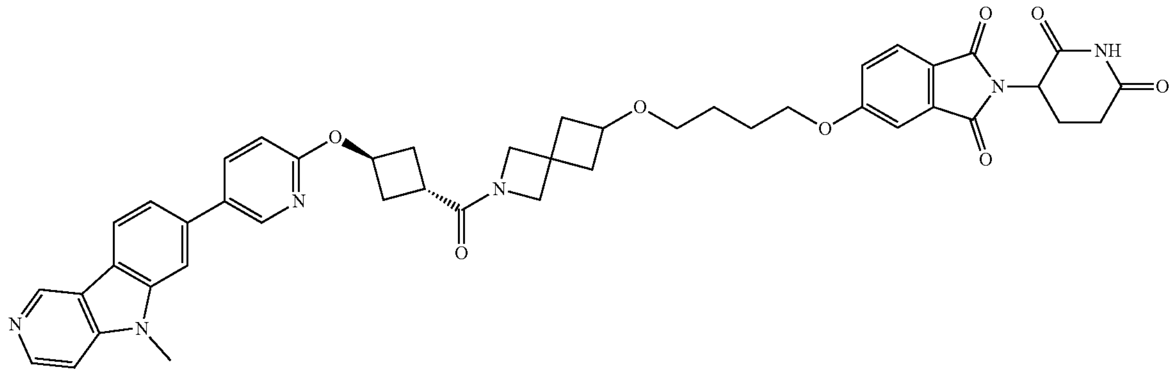 [SMILES: Cn1c2ccncc2c2ccc(-c3ccc(O[C@H]4C[C@H](C(=O)N5CC6(CC(OCCCCOc7ccc8c(c7)C(=O)N(C7CCC(=O)NC7=O)C8=O)C6)C5)C4)nc3)cc21]

Step 1: (1r,3r)-3-((5-(5-methyl-5H-pyrido[4,3-b]indol-7-yl)pyridin-2-yl)oxy)cyclobutanecarboxylic

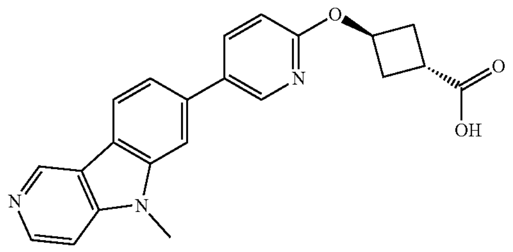 [SMILES: Cn1c2ccncc2c2ccc(-c3ccc(O[C@H]4C[C@H](C(=O)O)C4)nc3)cc21]

To a solution of (1r,3r)-3-((5-(5-methyl-5H-pyrido[4,3-b]indol-7-yl)pyridin-2-yl)oxy)cyclobutanecarbaldehyde (70 mg, 0.20 mmol) in tetrahydrofuran (1 ml) and water (1 ml) was added sodium chlorite (62 mg, 0.63 mmol), sodium dihydrogen phosphate dehydrate (168 mg, 1.08 mmol) and 2-methylbut-2-ene (233 mg, 3.33 mmol), then the mixture was stirred at room temperature overnight. TLC showed the reaction was complete. The reaction mixture was diluted with dichloromethane (20 ml), washed with water (10 ml×3), brine (10 ml), dried over anhydrous sodium sulfate, and concentrated under reduced pressure to give crude (1r,3r)-3-((5-(5-methyl-5H-pyrido[4,3-b]indol-7-yl)pyridin-2-yl)oxy)cyclobutanecarboxylic acid as yellow solid.

(1r,3r)-3-((5-(5-methyl-5H-pyrido[4,3-b]indol-7-yl)pyridin-2-yl)oxy)cyclobutanecarboxylic acid was converted to the final compound, 2-(2,6-dioxopiperidin-3-yl)-5-(4-((2-((1r,3r)-3-((5-(5-methyl-5H-pyrido[4,3-b]indol-7-yl)pyridin-2-yl)oxy)cyclobutane-1-carbonyl)-2-azaspiro[3.3]heptan-6-yl)oxy)butoxy)isoindoline-1,3-dione, according to the scheme below and using procedure described above for Compound 153.

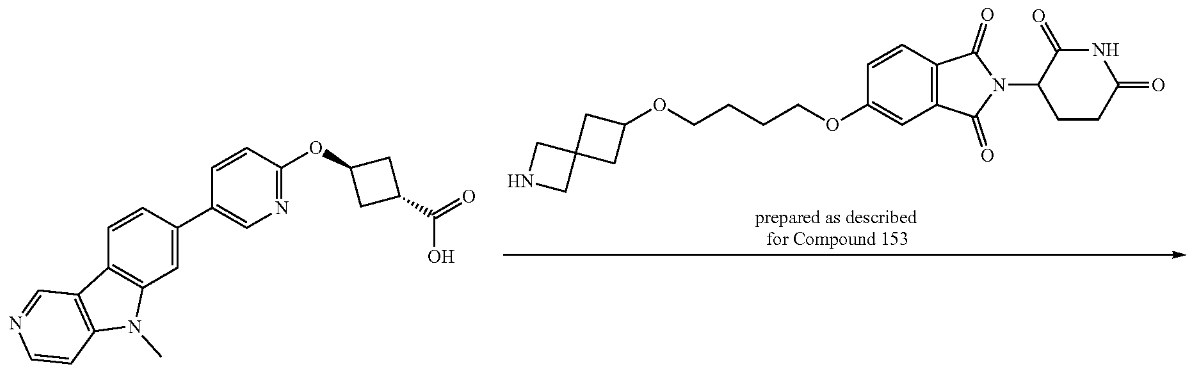

-continued

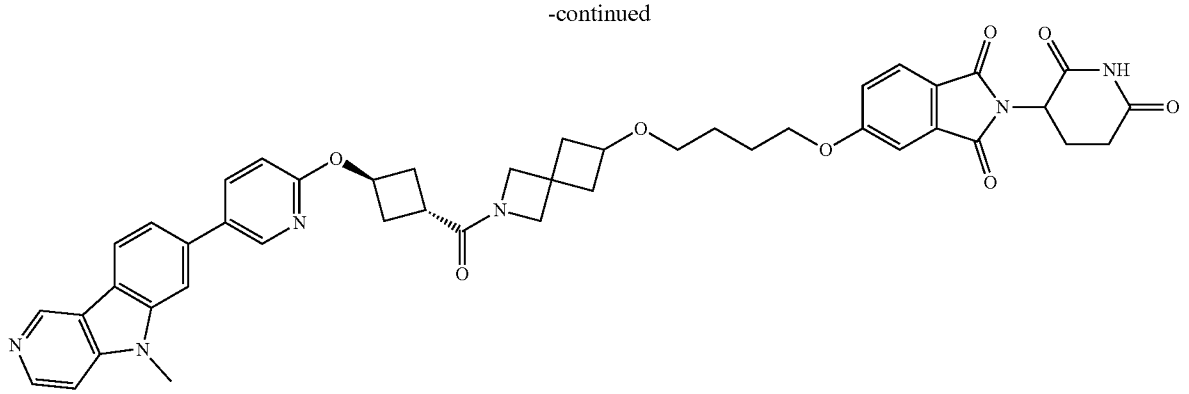

Compound 157

Synthetic Scheme for Exemplary Compound 158

2-(2,6-dioxopiperidin-3-yl)-5-(2-((6-(4-((1r,3r)-3-((5-(5-methyl-5H-pyrido[4,3-b]indol-7-yl)pyridin-2-yl)oxy)cyclobutoxy)piperidin-1-yl)pyridazin-4-yl)oxy)ethoxy)isoindoline-1,3-dione

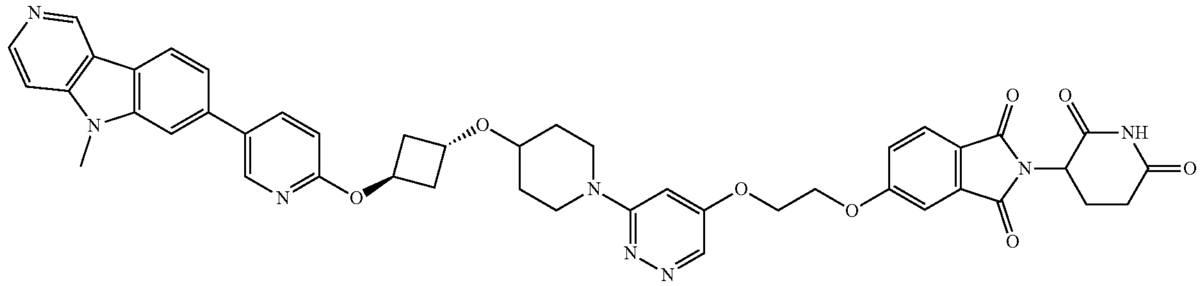 [SMILES: Cn1c2ccncc2c2ccc(-c3ccc(O[C@H]4C[C@H](OC5CCN(c6cc(OCCOc7ccc8c(c7)C(=O)N(C7CCC(=O)NC7=O)C8=O)cnn6)CC5)C4)nc3)cc21]

Step 1: 5-(2-(benzyloxy)ethoxy)-3-chloropyridazine

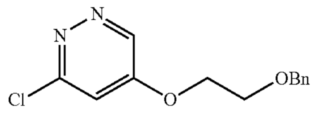 [SMILES: Clc1cc(OCCOCc2ccccc2)cnn1]

To a stirred solution of 2-(benzyloxy)ethanol (440 mg, 2.895 mmol) and 3,5-dichloropyridazine (428 mg, 2.895 mmol) in 1-methyl-2-pyrrolidinone (5 ml) was added sodium hydride (60% in oil) (347 mg, 8.68 mmol) at 0° C. Then the mixture was stirred at room temperature for 1 hour. The reaction mixture was quenched with aqueous ammonium chloride solution (15 ml) at 0° C., and extracted with ethyl acetate (20 ml×3). The organic layer was with brine (20 ml×2), dried over anhydrous sodium sulfate and concentrated under reduced pressure to give a crude residue which was purified by silica gel flash column chromatography (eluted with 15% ethyl acetate in hexane) to give 5-(2-(benzyloxy)ethoxy)-3-chloropyridazine (680 mg, 89% yield) as light brown oil.

Step 2: (1r,3r)-3-((1-(5-(2-(benzyloxy)ethoxy)pyridazin-3-yl)piperidin-4-yl)oxy)cyclobutanol

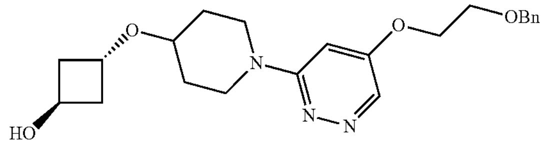 [SMILES: O[C@H]1C[C@H](OC2CCN(c3cc(OCCOCc4ccccc4)cnn3)CC2)C1]

To the mixture of 5-(2-(benzyloxy)ethoxy)-3-chloropyridazine (240 mg, 0.910 mmol) and (1r,3r)-3-(piperidin-4-yloxy)cyclobutanol (155 mg, 0.910 mmol) [prepared via hydrogenation of (1r,3r)-3-((1-benzylpiperidin-4-yl)oxy)cyclobutan-1-ol as described in step 5 of Compound 65 but without di-tert-butyl carbonate present] in toluene (5 ml) were added $Pd_2(dba)_3$ (83 mg, 0.091 mmol), (+/−)-2,2'-Bis (diphenylphosphino)-1,1'-binaphthyl (56 mg, 0.091 mmol) and cesium carbonate (739 mg, 2.27 mmol) under nitrogen. Then the mixture was heated to 90° C. overnight. TLC showed the reaction was complete. The reaction mixture was extracted with ethyl acetate (30 ml×3). The organic layer was with brine (10 ml×2), dried over anhydrous sodium sulfate and concentrated under reduced pressure to give a crude residue which was purified by silica gel flash column chromatography (eluted with 8% ethyl acetate in hexane) to give (1r,3r)-3-((1-(5-(2-(benzyloxy)ethoxy)pyridazin-3-yl)piperidin-4-yl)oxy)cyclobutanol (135 mg, 38% yield) as light yellow oil.

(1r,3r)-3-((1-(5-(2-(benzyloxy)ethoxy)pyridazin-3-yl)piperidin-4-yl)oxy)cyclobutanol was converted to the final compound, 2-(2,6-dioxopiperidin-3-yl)-5-(2-((6-(4-((1r,3r)-3-((5-(5-methyl-5H-pyrido[4,3-b]indol-7-yl)pyridin-2-yl)oxy)cyclobutoxy)piperidin-1-yl)pyridazin-4-yl)oxy)ethoxy)isoindoline-1,3-dione, according to the scheme below and using procedures described above and common procedures known to those skilled in the art.

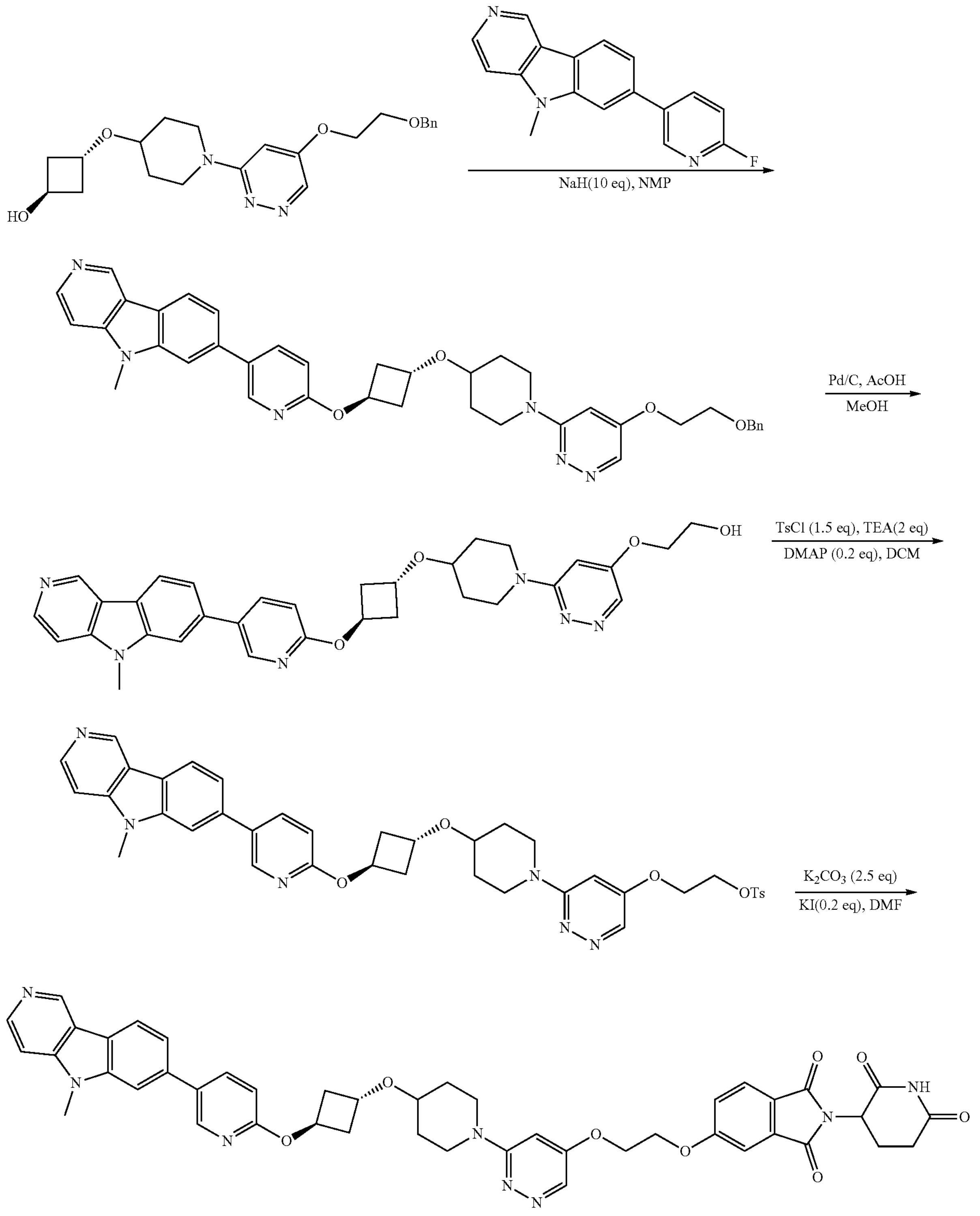

Compoun 158

Synthetic Scheme for Exemplary Compound 159 and Compound 160

2-(2,6-dioxopiperidin-3-yl)-5-(3-((3-(5-((1s,3s)-3-((5-(5-methyl-5H-pyrido[4,3-b]indol-7-yl)pyridin-2-yl)oxy)cyclobutoxy)pyridin-2-yl)prop-2-yn-1-yl)oxy)azetidin-1-yl)isoindoline-1,3-dione

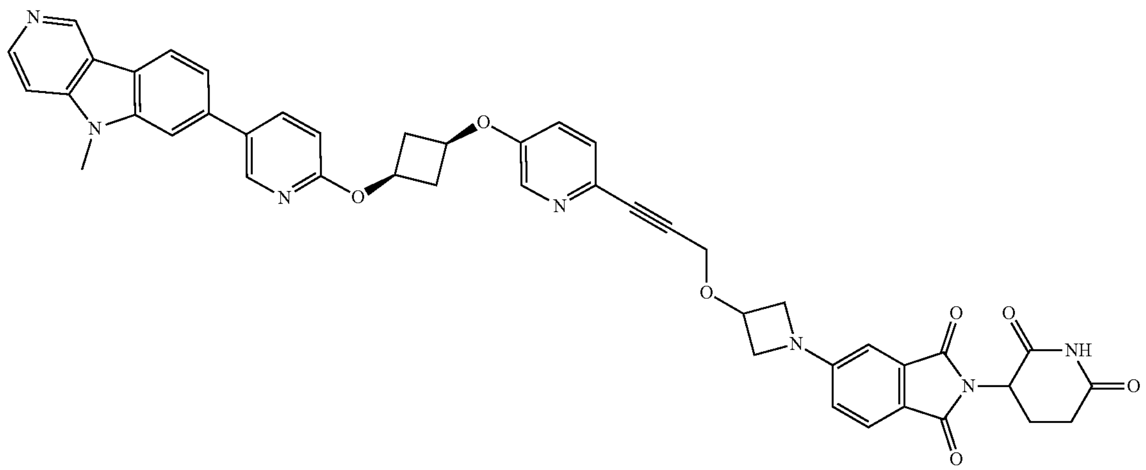 [SMILES: Cn1c2ccncc2c2ccc(-c3ccc(O[C@H]4C[C@@H](Oc5ccc(C#CCOC6CN(c7ccc8c(c7)C(=O)N(C7CCC(=O)NC7=O)C8=O)C6)nc5)C4)nc3)cc21]

2-(2,6-dioxopiperidin-3-yl)-5-(3-(3-(5-((1s,3s)-3-((5-(5-methyl-5H-pyrido[4,3-b]indol-7-yl)pyridin-2-yl)oxy)cyclobutoxy)pyridin-2-yl)propoxy)azetidin-1-yl)isoindoline-1,3-dione

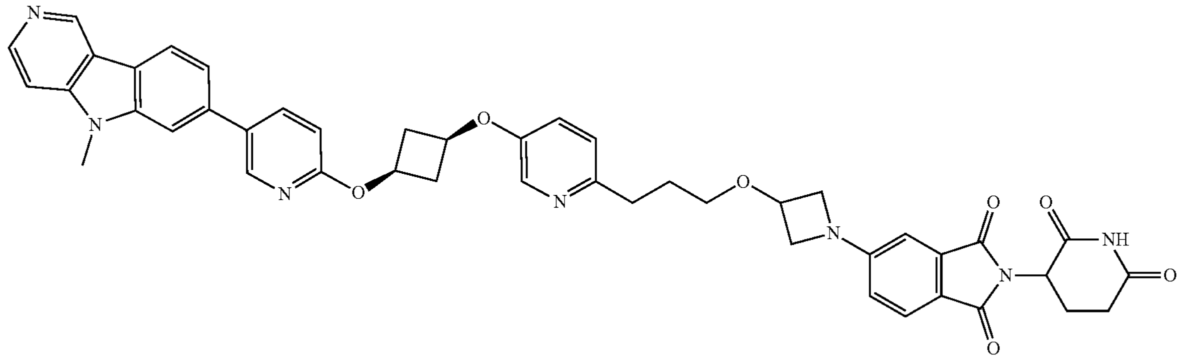 [SMILES: Cn1c2ccncc2c2ccc(-c3ccc(O[C@H]4C[C@@H](Oc5ccc(CCCOC6CN(c7ccc8c(c7)C(=O)N(C7CCC(=O)NC7=O)C8=O)C6)nc5)C4)nc3)cc21]

Prepared according to the scheme below and using procedures described above and common procedures known to those skilled in the art.

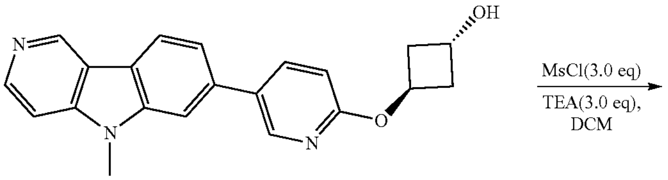

-continued
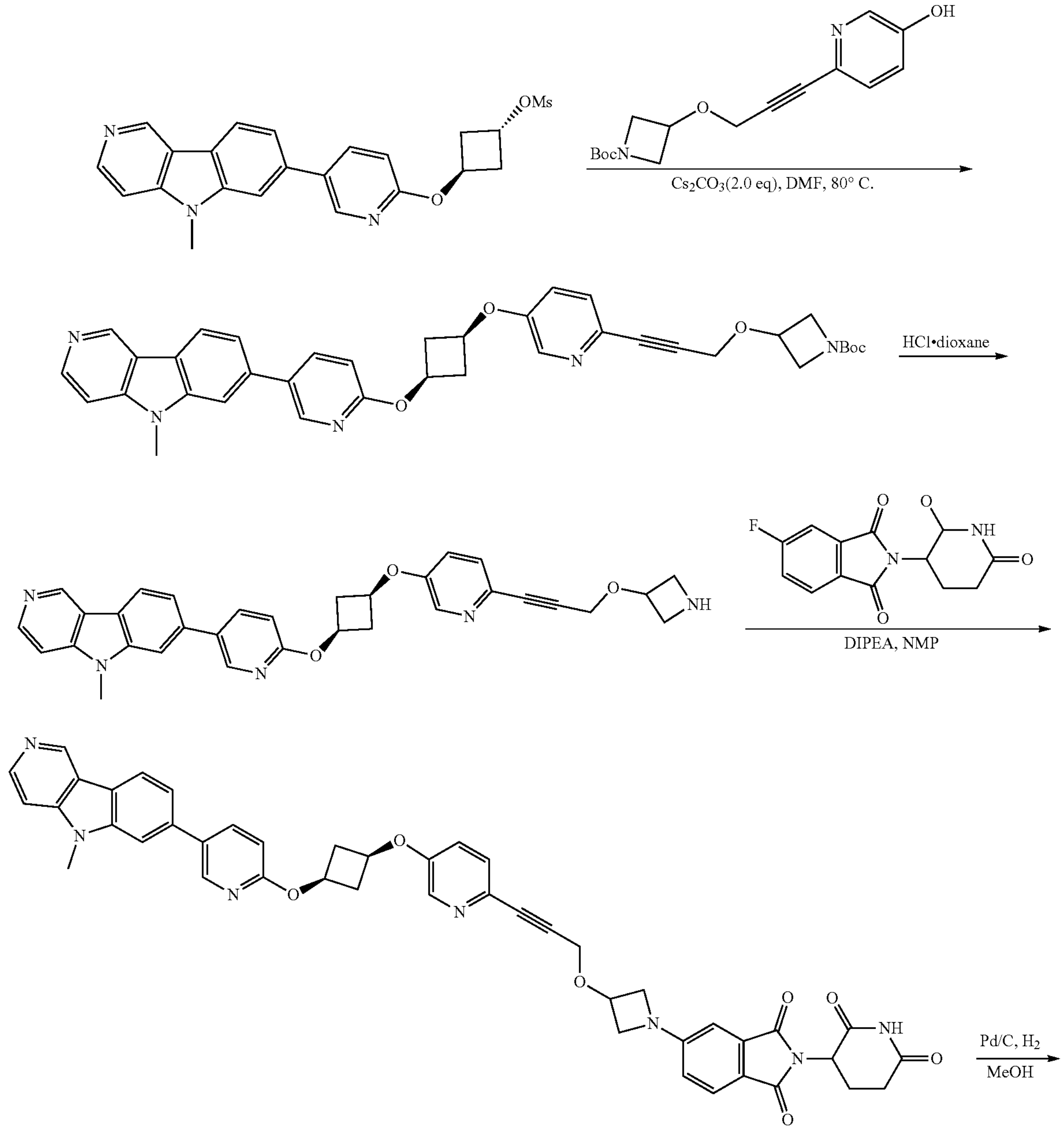
Compound 159
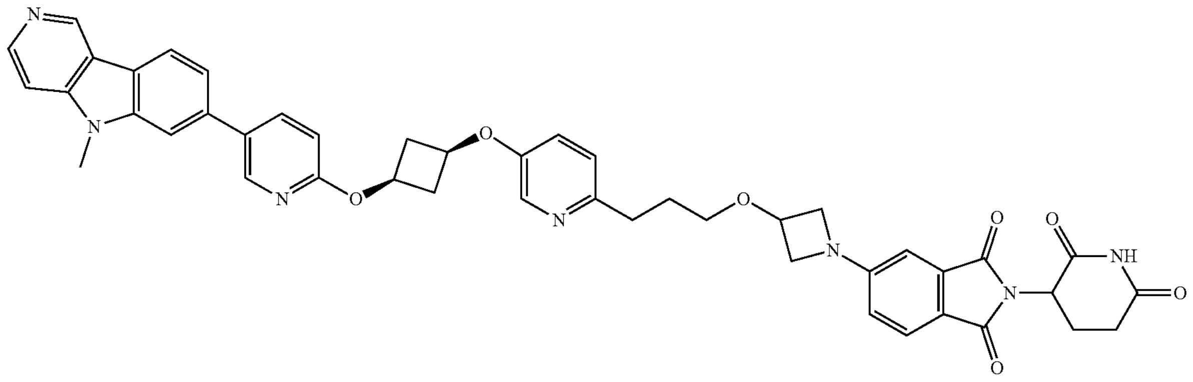
Compound 160

Synthetic Scheme for Exemplary Compound 161
2-(2,6-dioxopiperidin-3-yl)-5-(3-(2-(2-(2-((1r,3r)-3-((5-(5-methyl-5H-pyrido[4,3-b]indol-7-yl)pyridin-2-yl)oxy)cyclobutoxy)ethoxy)ethoxy)ethoxy)azetidin-1-yl)isoindoline-1,3-dione
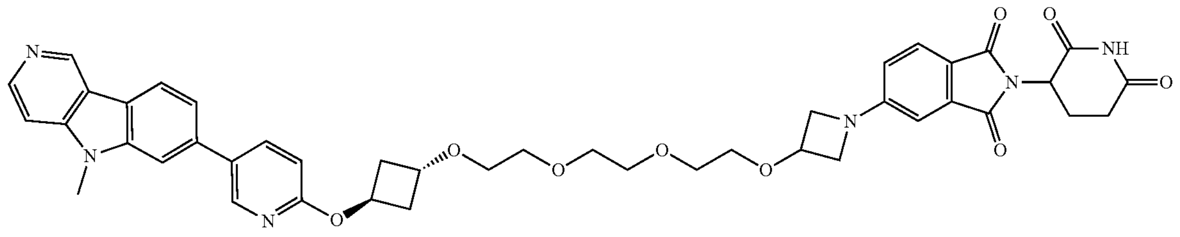 [SMILES: Cn1c2ccncc2c2ccc(-c3ccc(O[C@H]4C[C@H](OCCOCCOCCOC5CN(c6ccc7c(c6)C(=O)N(C6CCC(=O)NC6=O)C7=O)C5)C4)nc3)cc21]
Prepared according to the scheme below and using procedures described above and common procedures known to those skilled in the art.
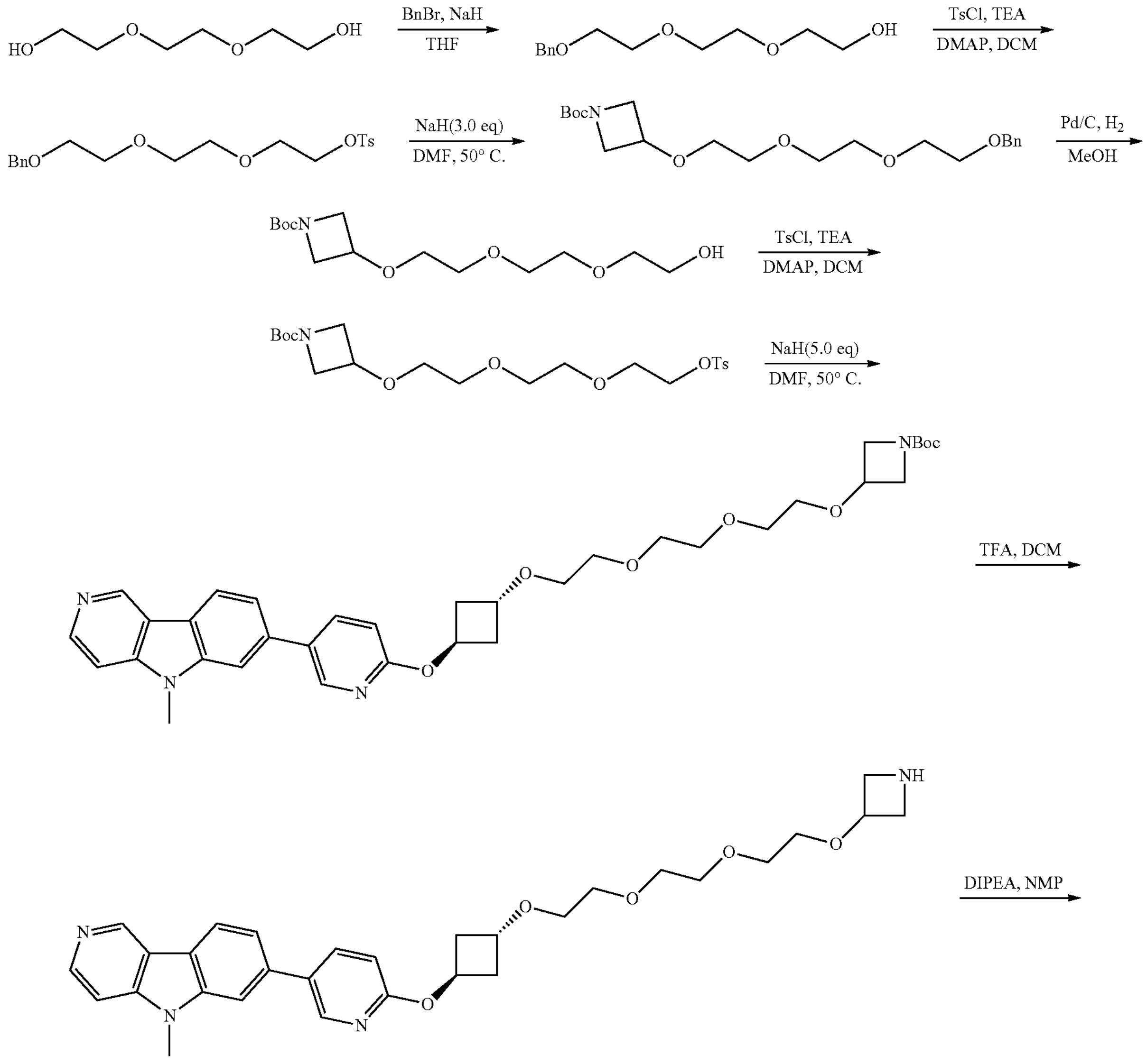

-continued

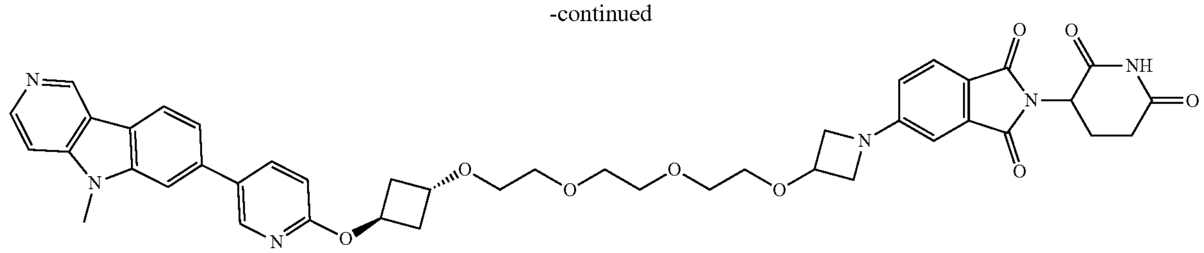

Compound 161

Based on the general approach of the Compound 163 and using common procedures known to those skilled in the art additional compounds were prepared: 162, 165, 178, 181, and 182.

Synthetic Scheme for Exemplary Compounds 165 and 166

5-((5-((1-((1r,3r)-3-((5-(5H-pyrido[4,3-b]indol-7-yl)pyridin-2-yl)oxy)cyclobutane-1-carbonyl)piperidin-4-yl)oxy)pentyl)oxy)-2-(2,6-dioxopiperidin-3-yl)isoindoline-1,3-dione

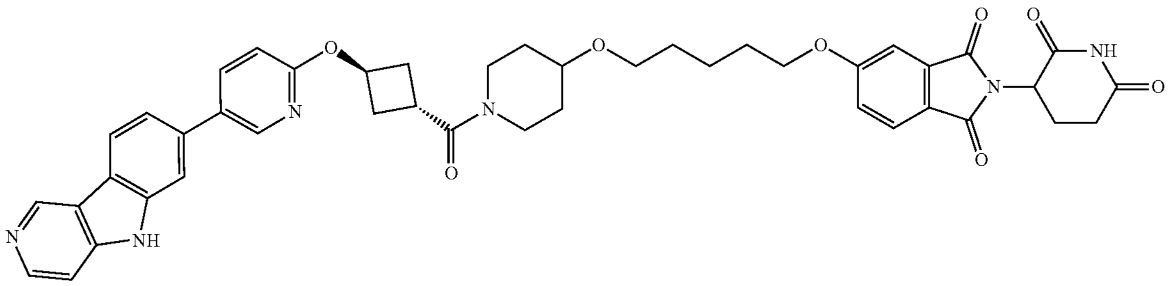 [SMILES: O=C1CCC(N2C(=O)c3ccc(OCCCCCOC4CCN(C(=O)[C@H]5C[C@H](Oc6ccc(-c7ccc8c(c7)[nH]c7ccncc78)cn6)C5)CC4)cc3C2=O)C(=O)N1]

5-((5-((1-((1s,3s)-3-((5-(5H-pyrido[4,3-b]indol-7-yl)pyridin-2-yl)oxy)cyclobutane-1-carbonyl)piperidin-4-yl)oxy)pentyl)oxy)-2-(2,6-dioxopiperidin-3-yl)isoindoline-1,3-dione

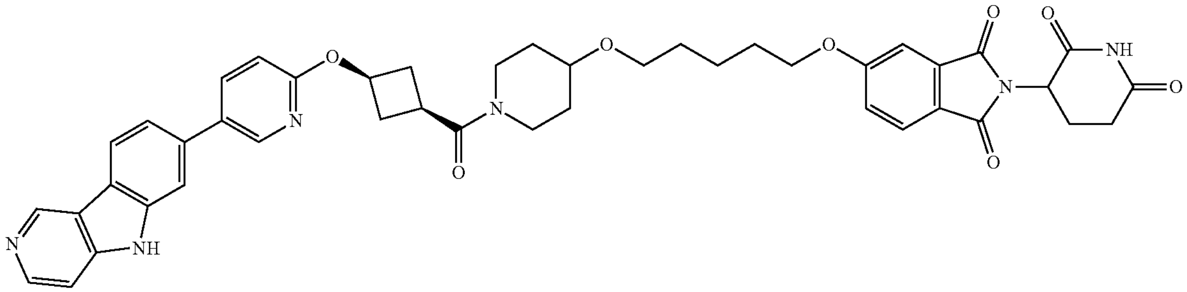 [SMILES: O=C1CCC(N2C(=O)c3ccc(OCCCCCOC4CCN(C(=O)[C@H]5C[C@@H](Oc6ccc(-c7ccc8c(c7)[nH]c7ccncc78)cn6)C5)CC4)cc3C2=O)C(=O)N1]

Prepared according to the scheme below and using procedures described above and common procedures known to those skilled in the art.

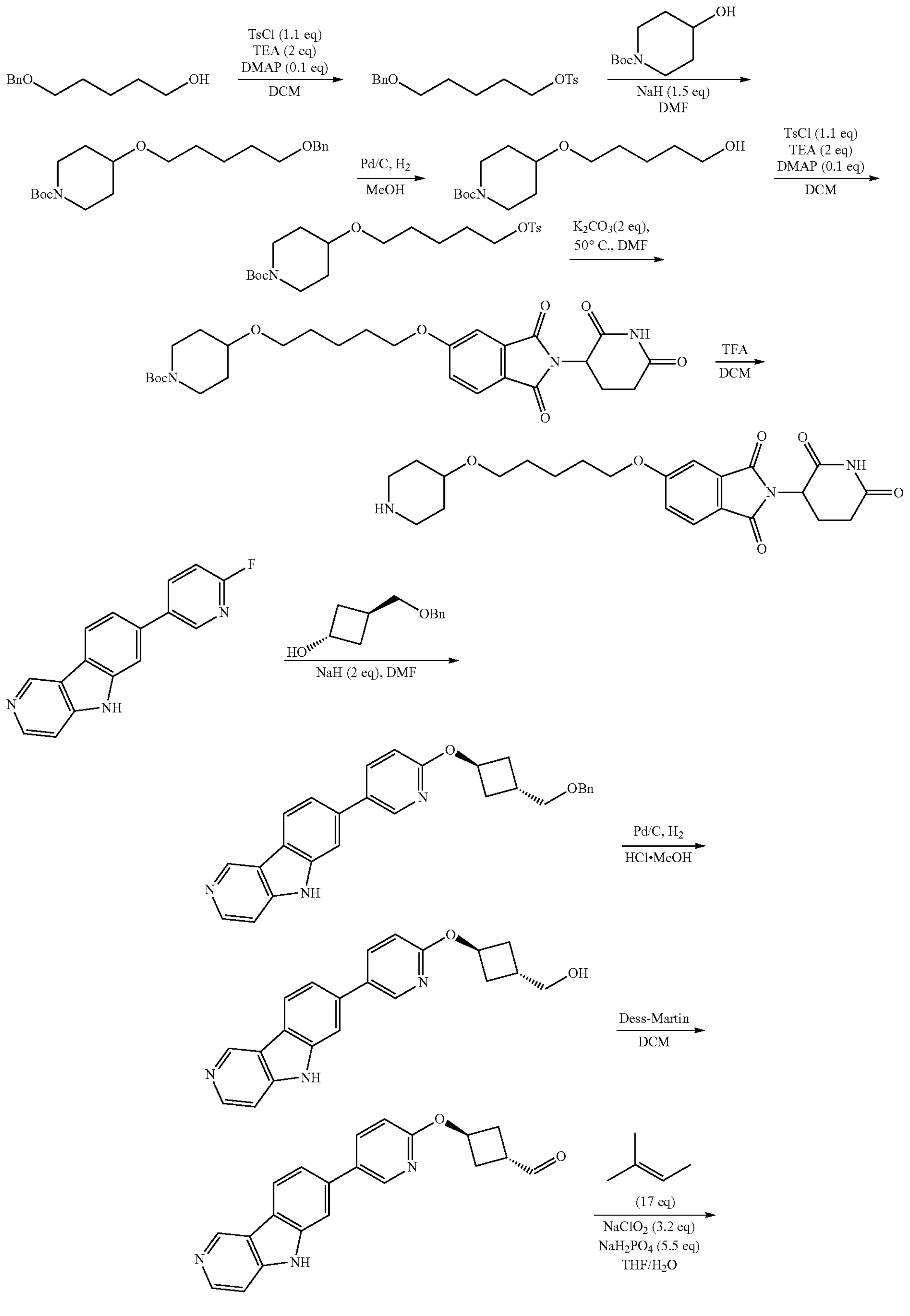
TsCl (1.1 eq)
TEA (2 eq)
DMAP (0.1 eq)
DCM
NaH (1.5 eq)
DMF
Pd/C, H2
MeOH
TsCl (1.1 eq)
TEA (2 eq)
DMAP (0.1 eq)
DCM
K2CO3(2 eq),
50° C., DMF
TFA
DCM
NaH (2 eq), DMF
Pd/C, H2
HCl•MeOH
Dess-Martin
DCM
(17 eq)
NaClO2 (3.2 eq)
NaH2PO4 (5.5 eq)
THF/H2O -continued
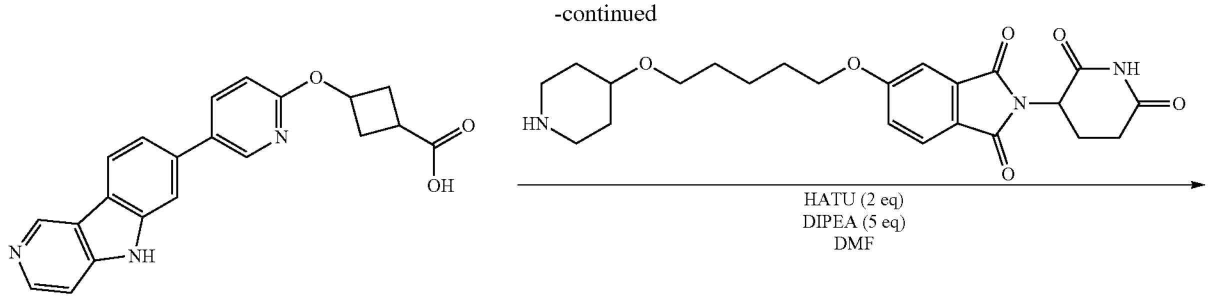
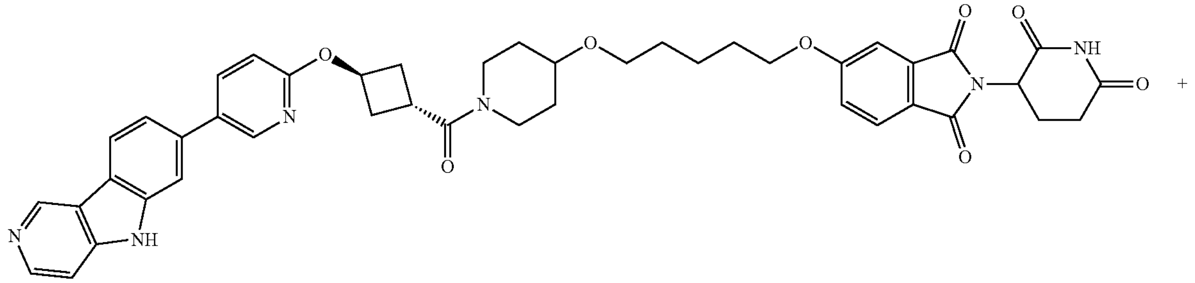
Compoun 165
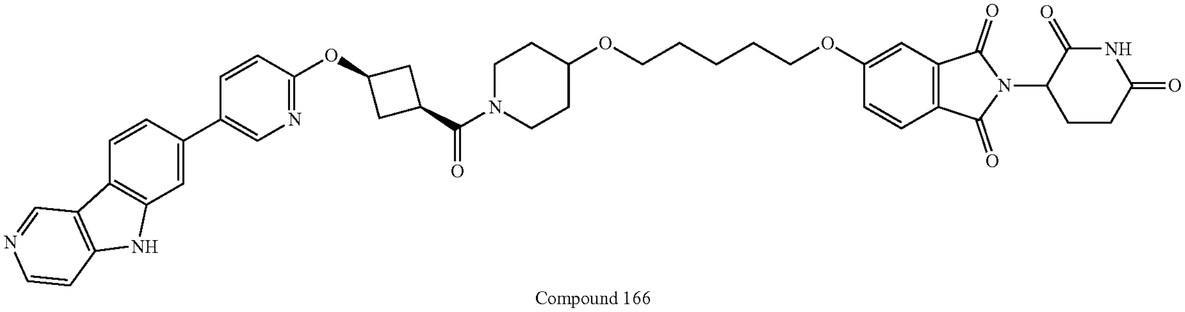
Compound 166
Synthetic Scheme for Exemplary Compounds 167 and 168
2-(2,6-dioxopiperidin-3-yl)-5-(3-((3-(5-(3-((5-(5-methyl-5H-pyrido[4,3-b]indol-7-yl)pyridin-2-yl)oxy)propoxy)pyridin-2-yl)prop-2-yn-1-yl)oxy)azetidin-1-yl)isoindoline-1,3-dione
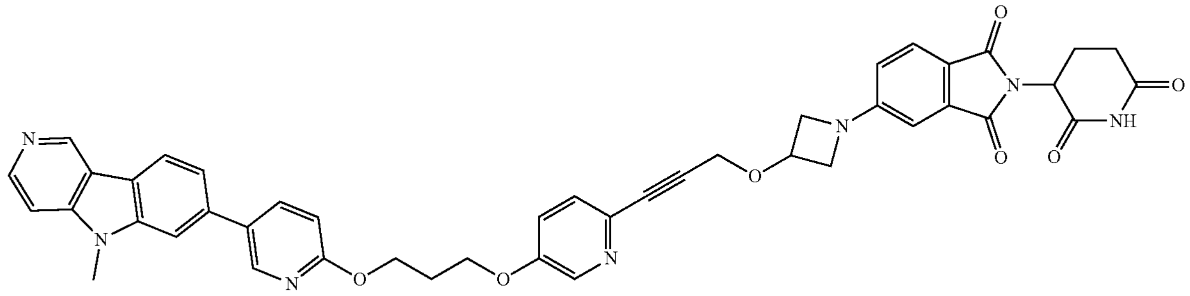 [SMILES: Cn1c2ccncc2c2ccc(-c3ccc(OCCCOc4ccc(C#CCOC5CN(c6ccc7c(c6)C(=O)N(C6CCC(=O)NC6=O)C7=O)C5)nc4)nc3)cc21]

2-(2,6-dioxopiperidin-3-yl)-5-(3-(3-(5-(3-((5-(5-methyl-5H-pyrido[4,3-b]indol-7-yl)pyridin-2-yl)oxy)propoxy)pyridin-2-yl)propoxy)azetidin-1-yl)isoindoline-1,3-dione
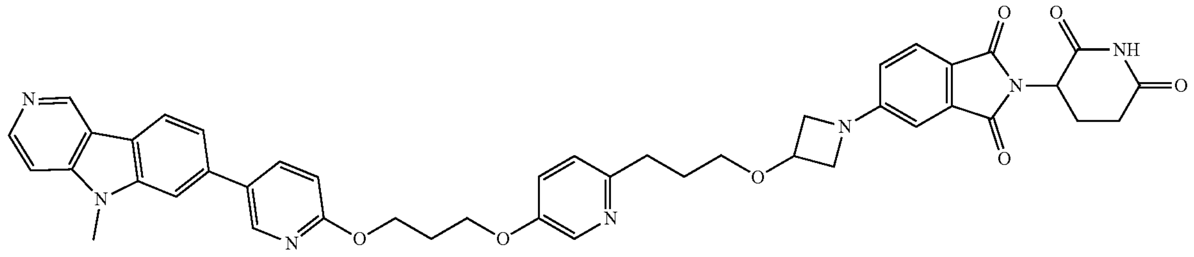 [SMILES: Cn1c2ccncc2c2ccc(-c3ccc(OCCCOc4ccc(CCCOC5CN(c6ccc7c(c6)C(=O)N(C6CCC(=O)NC6=O)C7=O)C5)nc4)nc3)cc21]
Prepared according to the scheme below and using procedures described above and common procedures known to those skilled in the art.
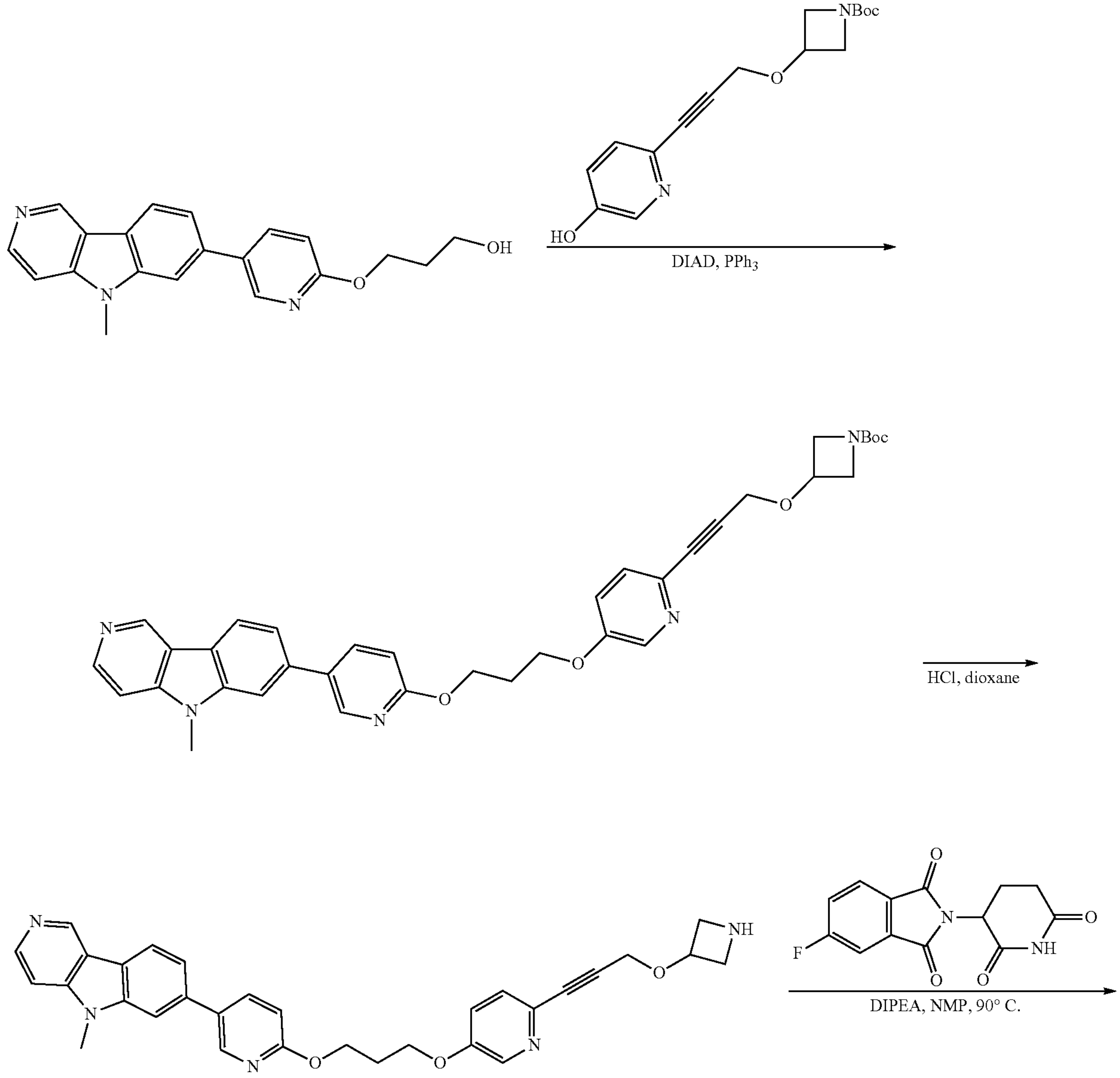

-continued
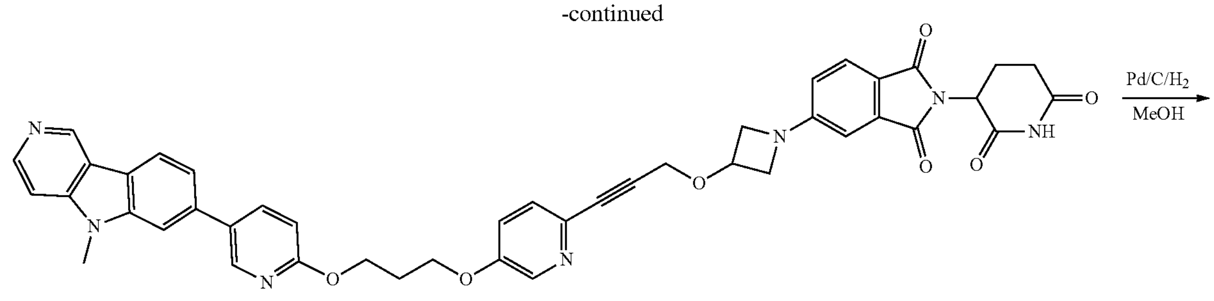
Compounds 167
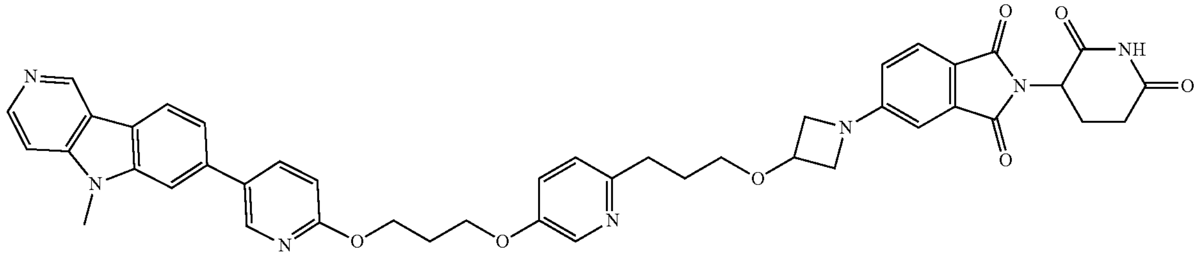
Compounds 168
Synthetic Scheme for Exemplary Compound 169
2-(2,6-dioxopiperidin-3-yl)-5-(3-(3-((3-(((1r,3r)-3-((5-(5-methyl-5H-pyrido[4,3-b]indol-7-yl)pyridin-2-yl)oxy)cyclobutoxy)methyl)oxetan-3-yl)methoxy)propoxy)azetidin-1-yl)isoindoline-1,3-dione
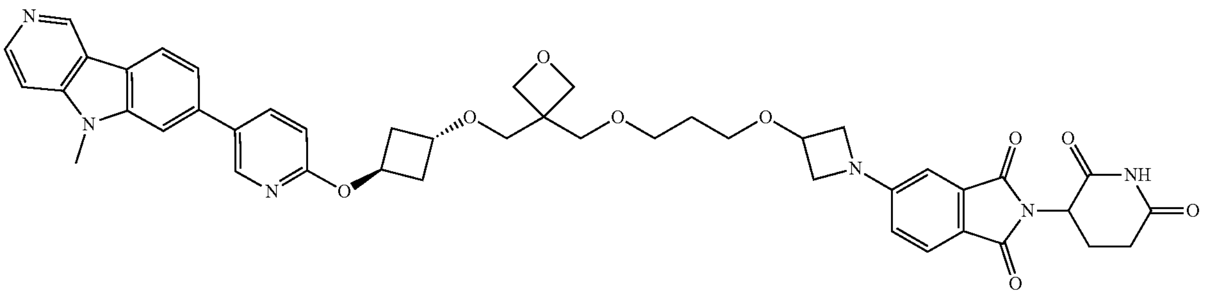 [SMILES: Cn1c2ccncc2c2ccc(-c3ccc(O[C@H]4C[C@H](OCC5(COCCCOC6CN(c7ccc8c(c7)C(=O)N(C7CCC(=O)NC7=O)C8=O)C6)COC5)C4)nc3)cc21]
Prepared according to the scheme below and using procedures described above and common procedures known to those skilled in the art.
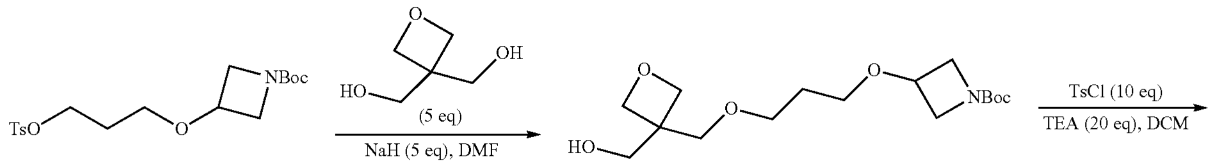
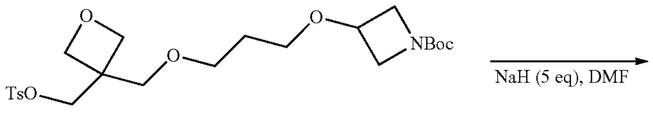

-continued

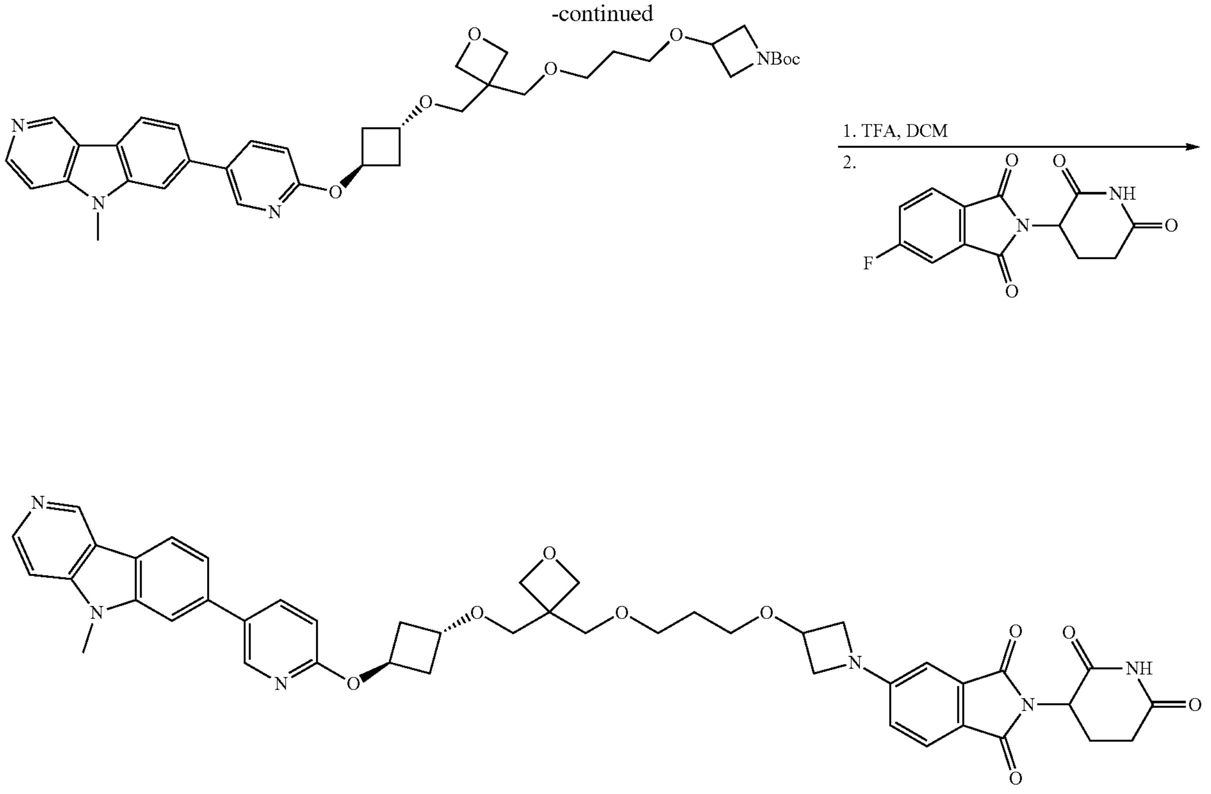

Compound 169

Synthetic Scheme for Exemplary Compound 174

2-(2,6-dioxopiperidin-3-yl)-5-(4-((3-(((1r,3r)-3-((5-(5-methyl-5H-pyrido[4,3-b]indol-7-yl)pyridin-2-yl)oxy)cyclobutoxy)methyl)bicyclo[1.1.1]pentan-1-yl)methoxy)butoxy)isoindoline-1,3-dione

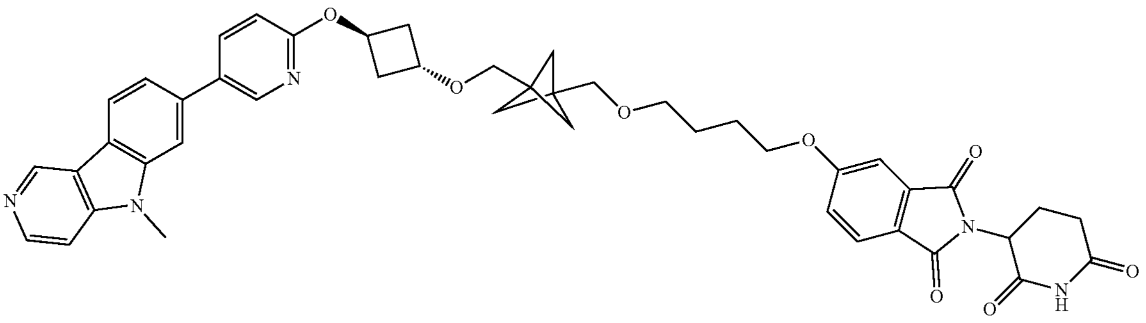 [SMILES: Cn1c2ccncc2c2ccc(-c3ccc(O[C@H]4C[C@H](OCC56CC(COCCCCOc7ccc8c(c7)C(=O)N(C7CCC(=O)NC7=O)C8=O)(C5)C6)C4)nc3)cc21]

Step 1: bicyclo[1.1.1]pentane-1,3-diyldimethanol

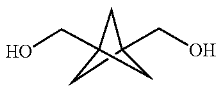

To a solution of dimethyl bicyclo[1.1.1]pentane-1,3-dicarboxylate (500 mg, 2.72 mmol) in tetrahydrofuran (5 ml) was added lithium aluminum hydride (419 mg, 10.87 mmol) at 0° C., and the resulting mixture was stirred at room temperature for 2 hours. TLC showed the reaction was complete. The reaction mixture was quenched with water (1 ml), sodium hydroxide (2 ml, 10% in water) and water (1 ml). The solid was removed through filtration, and the filtrate was dried over anhydrous sodium sulfate, concentrated under reduced pressure to afford to afford bicyclo[1.1.1]pentane-1,3-diyldimethanol (256 mg crude, yield 70%) as light yellow oil.

Bicyclo[1.1.1]pentane-1,3-diyldimethanol was converted to the final compound, 2-(2,6-dioxopiperidin-3-yl)-5-(4-((3-(((1r,3r)-3-((5-(5-methyl-5H-pyrido[4,3-b]indol-7-yl)pyridin-2-yl)oxy)cyclobutoxy)methyl)bicyclo[1.1.1]pentan-1-yl)methoxy)butoxy)isoindoline-1,3-dione, according to the scheme below and using procedures described above and common procedures known to those skilled in the art.

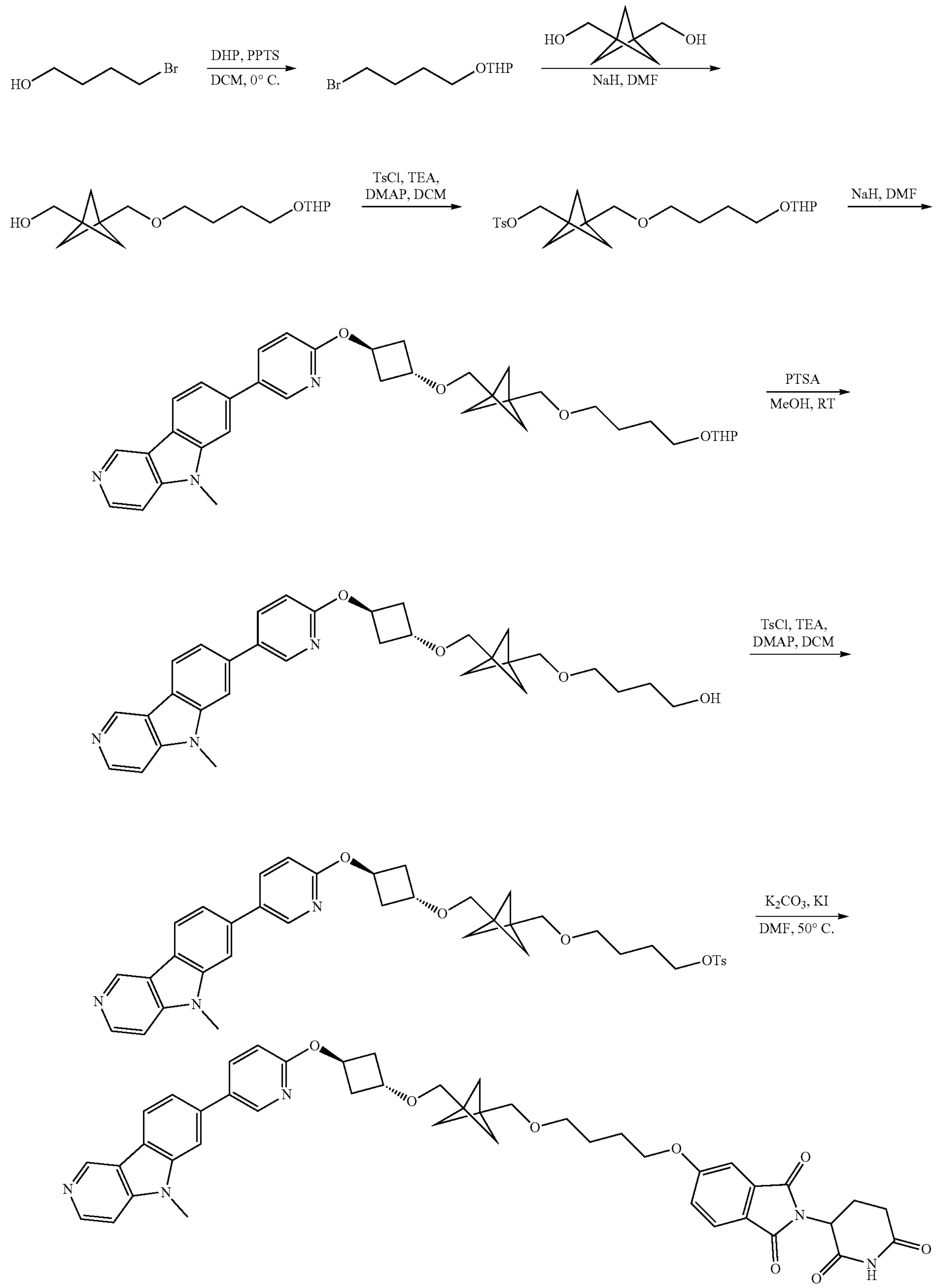
Compound 174

Synthetic Scheme for Exemplary Compound 175

2-(2,6-dioxopiperidin-3-yl)-5-((5-((3-(3-((5-(5-methyl-5H-pyrido[4,3-b]indol-7-yl)pyridin-2-yl)oxy)azetidine-1-carbonyl)bicyclo[1.1.1]pentan-1-yl)methoxy)pentyl)oxy)isoindoline-1,3-dione

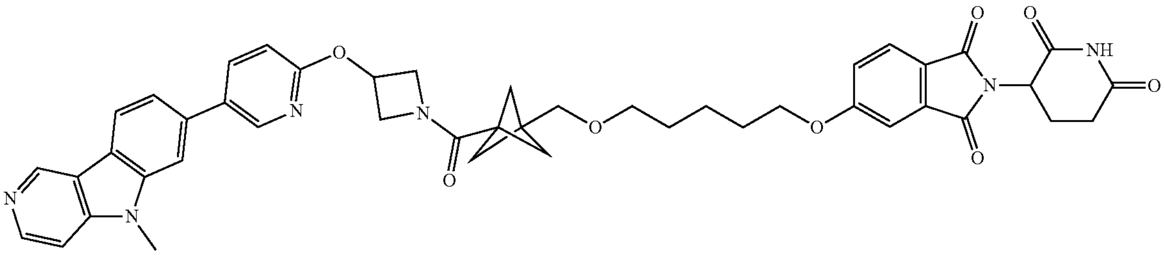 [SMILES: Cn1c2ccncc2c2ccc(-c3ccc(OC4CN(C(=O)C56CC(COCCCCCOc7ccc8c(c7)C(=O)N(C7CCC(=O)NC7=O)C8=O)(C5)C6)C4)nc3)cc21]

Step 1: 3-(Hydroxymethyl)bicyclo[1.1.1]pentane-1-carboxylate

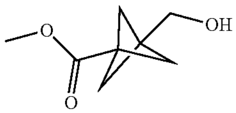

To a solution of dimethyl bicyclo[1.1.1]pentane-1,3-dicarboxylate (1 g, 5.43 mmol) in tetrahydrofuran (10 ml) was added lithium borohydride (120 mg, 5.43 mmol) at 0° C. under nitrogen. The mixture was allowed to warm up to room temperature and stirred at room temperature for 5 hours. The mixture was quenched with aqueous hydrochloride acid (1N) till pH 3-4, and extracted with dichloromethane (10 ml×2). The organic layers were combined, washed with brine (10 ml), dried over sodium sulfate and concentrated under reduced pressure to give a crude residue which was purified by silica gel flash chromatography (eluted with 20-33% ethyl acetate in hexane) to afford methyl 3-(hydroxymethyl)bicyclo[1.1.1]pentane-1-carboxylate (400 mg, 47%) as colorless oil.

3-(Hydroxymethyl)bicyclo[1.1.1]pentane-1-carboxylate was converted to the final compound, 2-(2,6-dioxopiperidin-3-yl)-5-((5-((3-(3-((5-(5-methyl-5H-pyrido[4,3-b]indol-7-yl)pyridin-2-yl)oxy)azetidine-1-carbonyl)bicyclo[1.1.1]pentan-1-yl)methoxy)pentyl)oxy)isoindoline-1,3-dione, according to the schemes below and using procedures described above and common procedures known to those skilled in the art.

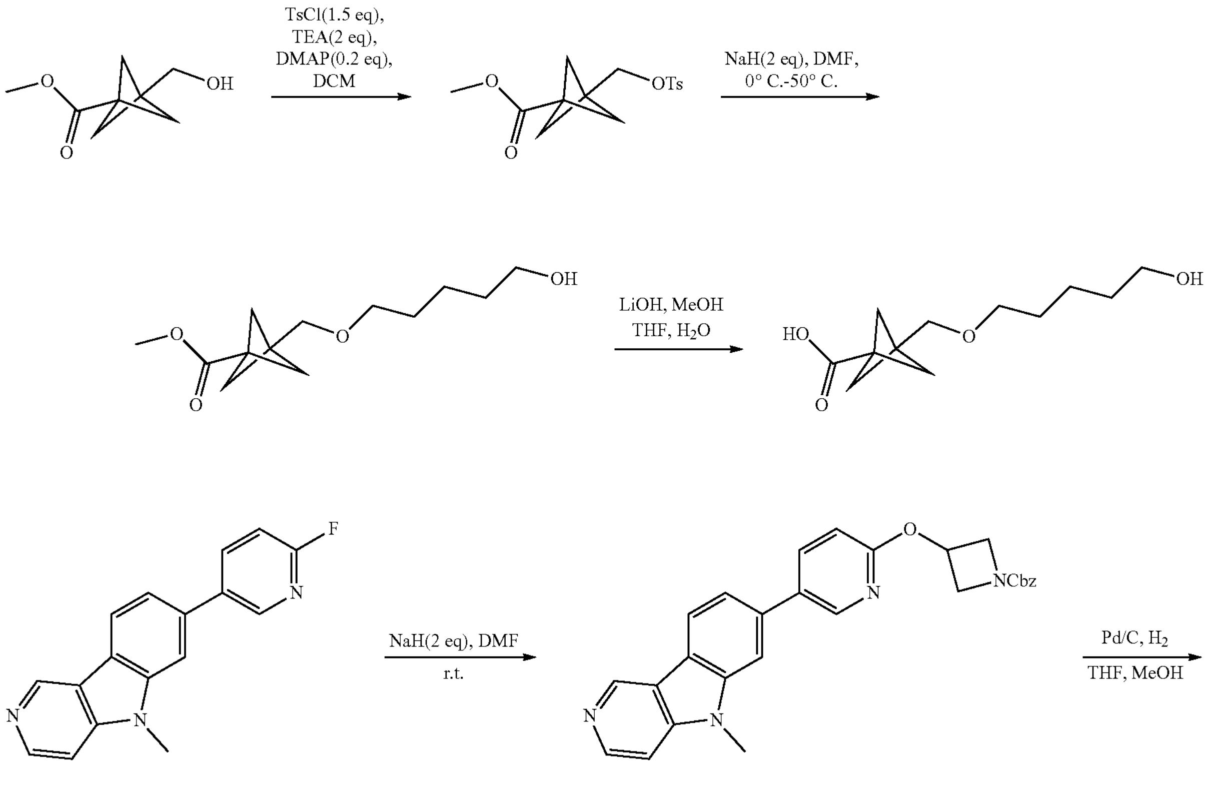

-continued
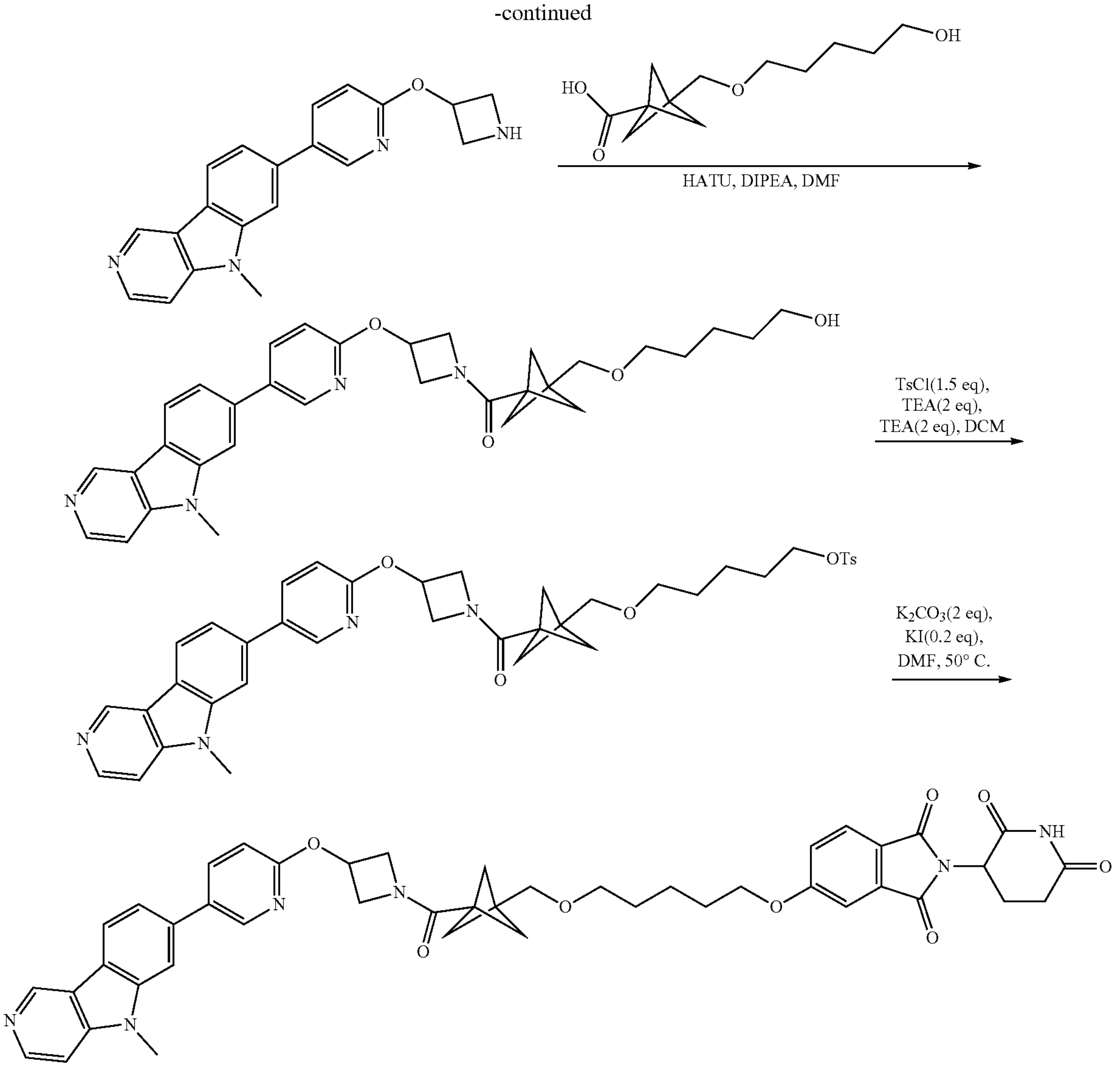
Compound 175
Synthetic Scheme for Exemplary Compound 176
5-(3-(3-(3-((1r,3r)-3-((5-(8,9-difluoro-5-methyl-5H-pyrido[4,3-b]indol-7-yl)pyridin-2-yl)oxy)cyclobutoxy)propoxy)propoxy)azetidin-1-yl)-2-(2,6-dioxopiperidin-3-yl)isoindoline-1,3-dione
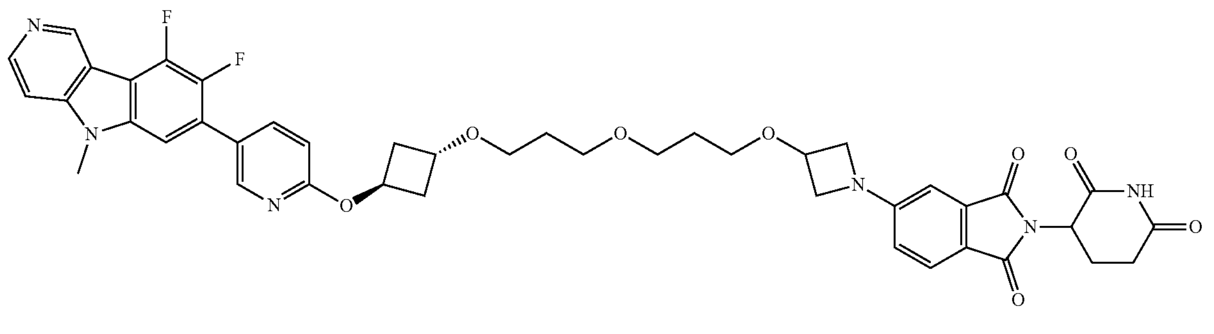 [SMILES: Cn1c2ccncc2c2c(F)c(F)c(-c3ccc(O[C@H]4C[C@H](OCCCOCCCOC5CN(c6ccc7c(c6)C(=O)N(C6CCC(=O)NC6=O)C7=O)C5)C4)nc3)cc21]

Prepared according to the schemes below and using procedures described above for Compound 104 (in modified sequence) and common procedures known to those skilled in the art.
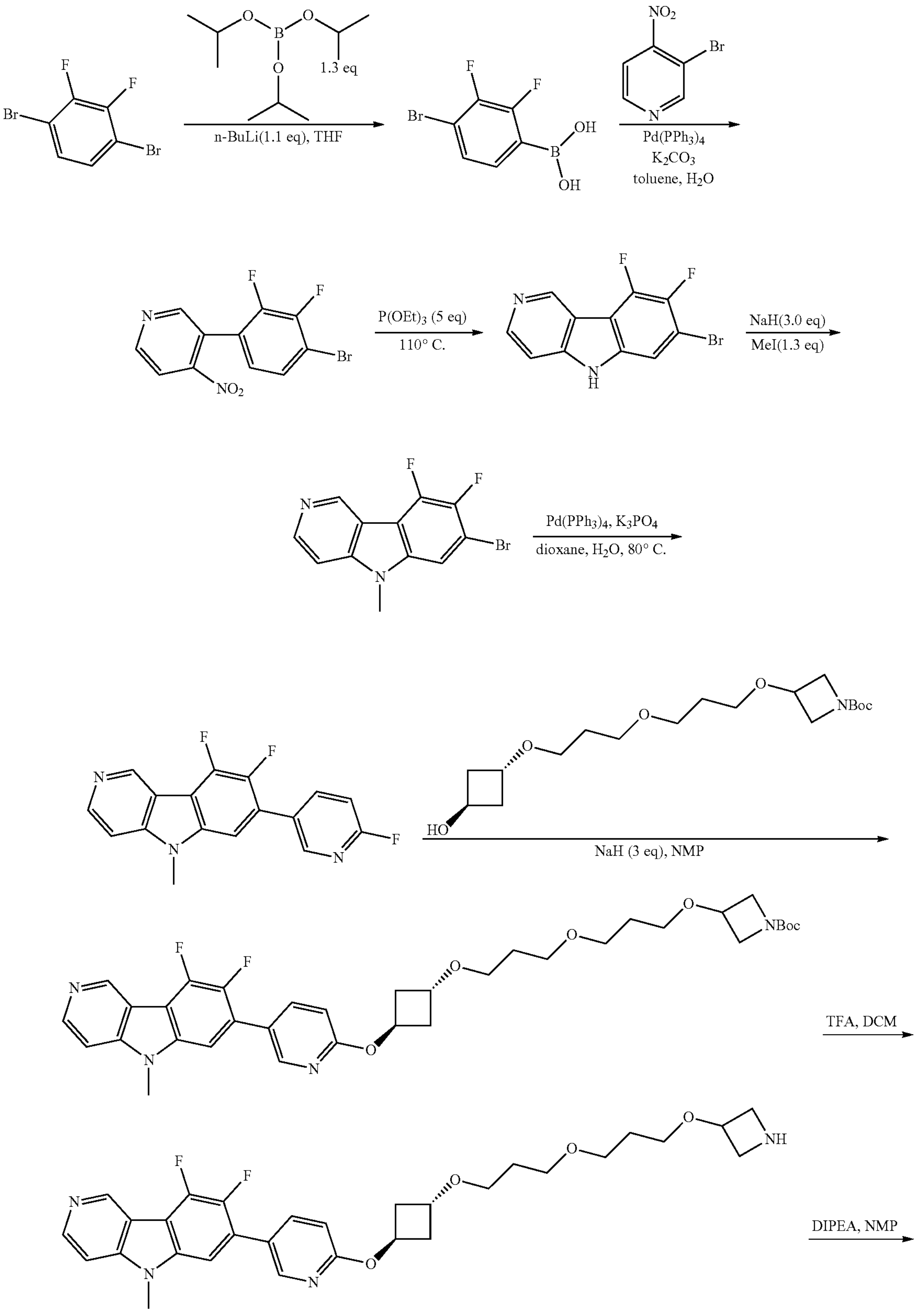

-continued

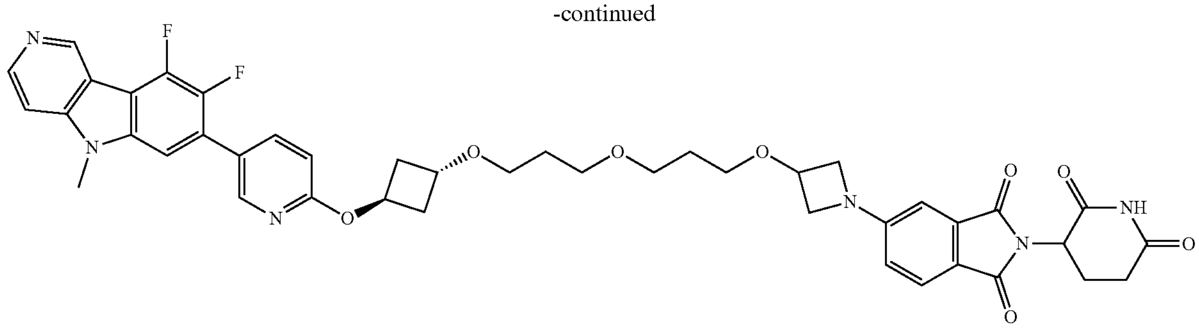

Compond 176

Synthetic Scheme for Exemplary Compound 177

3-(5-(3-(3-(3-((1r,3r)-3-((5-(5-methyl-5H-pyrido[4,3-b]indol-7-yl)pyridin-2-yl)oxy)cyclobutoxy)propoxy)propoxy)azetidin-1-yl)-1-oxoisoindolin-2-yl)piperidine-2,6-dione

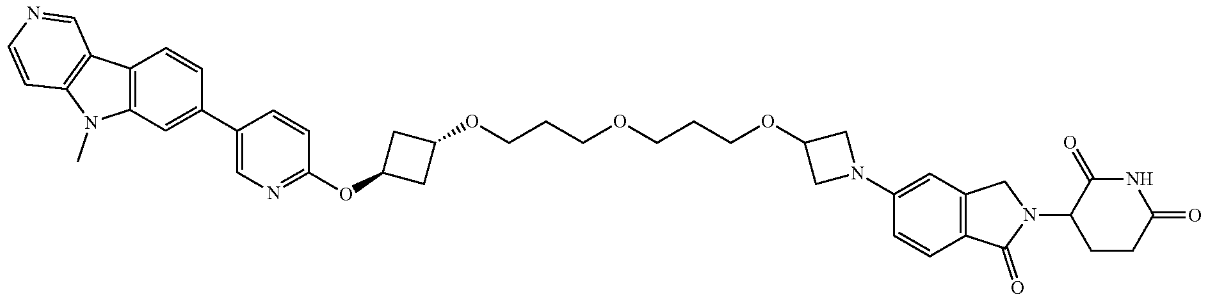 [SMILES: Cn1c2ccncc2c2ccc(-c3ccc(O[C@H]4C[C@H](OCCCOCCCOC5CN(c6ccc7c(c6)CN(C6CCC(=O)NC6=O)C7=O)C5)C4)nc3)cc21]

Step 1: 5-(3-(3-(3-((1r,3r)-3-((5-(5H-pyrido[4,3-b]indol-7-yl)-3-(trifluoromethyl)pyridin-2-yl)oxy)cyclobutoxy)propoxy)propoxy)azetidin-1-yl)-2-(2,6-dioxopiperidin-3-yl)isoindoline-1,3-dione

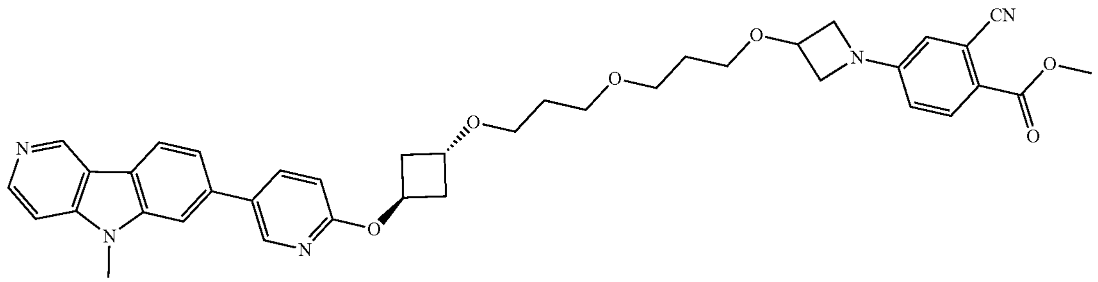 [SMILES: COC(=O)c1ccc(N2CC(OCCCOCCCO[C@H]3C[C@H](Oc4ccc(-c5ccc6c7cnccc7n(C)c6c5)cn4)C3)C2)cc1C#N]

A mixture of 7-(6-((1r,3r)-3-(3-(3-(azetidin-3-yloxy)propoxy)propoxy)cyclobutoxy)pyridin-3-yl)-5-methyl-5H-pyrido[4,3-b]indole (crude, 0.390 mmol) [prepared as described for Compound 104], N-ethyl-N-isopropylpropan-2-amine (86 mg, 1.17 mmol) and methyl 2-cyano-4-fluorobenzoate (90 mg, 0.468 mmol) in 1-methyl-2-pyrrolidinone (3 ml) was stirred at 90° C. for 16 hour. TLC showed the reaction was complete. The reaction mixture was partitioned between ethyl acetate (20 ml) and water (30 ml). The organic layer was collected, washed with brine (20 ml), dried over anhydrous sodium sulfate and concentrated under reduced pressure to give a crude residue which was purified by silica gel flash column chromatography (eluted with 2-4% methanol in dichloromethane) to afford 5-(3-(3-(3-((1r,3r)-3-((5-(5H-pyrido[4,3-b]indol-7-yl)-3-(trifluoromethyl)pyridin-2-yl)oxy)cyclobutoxy)propoxy)propoxy)azetidin-1-yl)-2-(2,6-dioxopiperidin-3-yl)isoindoline-1,3-dione (160 mg, yield 61%) as light yellow oil.

Step 2: Methyl 2-formyl-4-(3-(3-(3-((1r,3r)-3-((5-(5-methyl-5H-pyrido[4,3-b]indol-7-yl)pyridin-2-yl)oxy)cyclobutoxy)propoxy)propoxy)azetidin-1-yl)benzoate

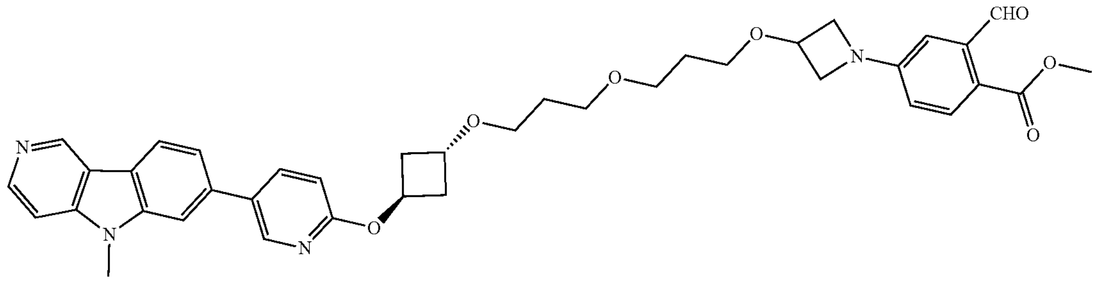 [SMILES: COC(=O)c1ccc(N2CC(OCCCOCCCO[C@H]3C[C@H](Oc4ccc(-c5ccc6c7cnccc7n(C)c6c5)cn4)C3)C2)cc1C=O]

To the mixture of methyl 2-cyano-4-(3-(3-(3-((1r,3r)-3-((5-(5-methyl-5H-pyrido[4,3-b]indol-7-yl)pyridin-2-yl)oxy)cyclobutoxy)propoxy)propoxy)azetidin-1-yl)benzoate (160 mg, 0.237 mmol) in pyridine (3 ml)-water (1.5 ml)-acetic acid (1.5 ml) was added sodium hypophosphite (125 mg, 1.179 mmol) and Raney nickel (85% in water) (300 mg) at room temperature. The resulting mixture was stirred at 50° C. for 2 hours. The mixture was diluted with ethyl acetate (30 ml), washed with water (30 ml×2), diluted hydrochloride acid solution (1 N, 30 ml), brine (50 ml), dried over anhydrous sodium sulfate, and concentrated under reduced pressure to give a crude residue which was purified by silica gel flash chromatography (eluted with 2-5% methanol in dichloromethane:) to afford methyl 2-formyl-4-(3-(3-(3-((1r,3r)-3-((5-(5-methyl-5H-pyrido[4,3-b]indol-7-yl)pyridin-2-yl)oxy)cyclobutoxy)propoxy)propoxy)azetidin-1-yl)benzoate (90 mg, yield 56%) as brown oil.

Step 3: 3-(5-(3-(3-(3-((1r,3r)-3-((5-(5-methyl-5H-pyrido[4,3-b]indol-7-yl)pyridin-2-yl)oxy)cyclobutoxy)propoxy)propoxy)azetidin-1-yl)-1-oxoisoindolin-2-yl)piperidine-2,6-dione

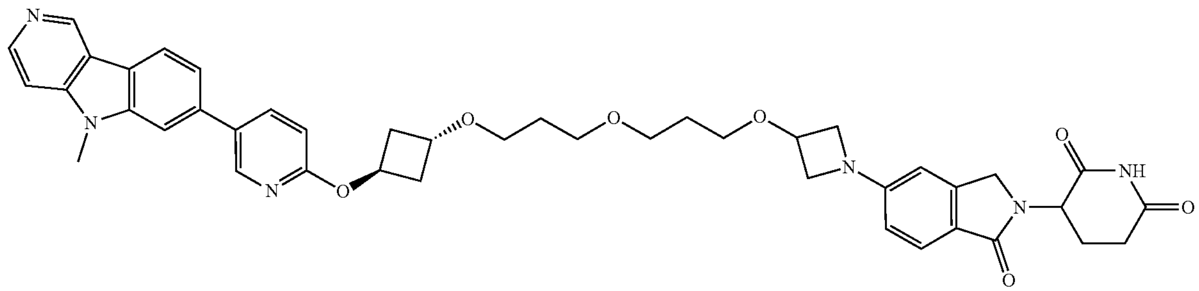 [SMILES: Cn1c2ccncc2c2ccc(-c3ccc(O[C@H]4C[C@H](OCCCOCCCOC5CN(c6ccc7c(c6)CN(C6CCC(=O)NC6=O)C7=O)C5)C4)nc3)cc21]

A mixture of 3-aminopiperidine-2,6-dione (32 mg, 0.199 mmol) N-ethyl-N-isopropylpropan-2-amine (34 mg, 0.199 mmol), acetic acid (0.5 ml) and methyl 2-formyl-4-(3-(3-(3-((1r,3r)-3-((5-(5-methyl-5H-pyrido[4,3-b]indol-7-yl)pyridin-2-yl)oxy)cyclobutoxy)propoxy)propoxy)azetidin-1-yl)benzoate (90 mg, 0.133 mmol) in methanol (5 ml) was stirred at room temperature for 15 min. Then sodium cyanoborohydride (16 mg, 0.400 mmol) was added and stirred at room temperature overnight. TLC showed the reaction was complete. The reaction mixture was partitioned between dichloromethane (30 ml) and water (10 ml), the organic layer was collected, washed with brine (10 ml×2), dried over anhydrous sodium sulfate and concentrated under reduced pressure to give a crude residue which was purified by Prep-TLC (8% methanol in ethyl acetate) to afford the title compound (50 mg, yield 50%) as white solid.

$^1$H NMR (400 MHz, DMSO-d6): δ 1.71-1.80 (m, 4H), 1.90-1.93 (m, 1H), 2.28-2.37 (m, 3H), 2.40-2.44 (m, 2H), 2.56-2.57 (m, 1H), 2.83-2.92 (m, 1H), 3.37 (t, J=6.0 Hz, 2H), 3.43-3.48 (m, 6H), 3.67-3.70 (m, 2H), 3.95 (s, 3H), 4.11-4.19 (m, 4H), 4.23-4.27 (m, 1H), 4.42-4.44 (m, 1H), 4.99-5.03 (m, 1H), 5.31-5.34 (m, 1H), 6.46-6.49 (m, 2H), 6.94 (d, J=8.8 Hz, 1H), 7.47 (d, J=8.4 Hz, 1H), 7.60-7.63 (m, 2H), 7.97 (s, 1H), 8.17-8.20 (m, 1H), 8.32 (d, J=8.0 Hz, 1H), 8.50 (d, J=6.0 Hz, 1H), 8.64 (d, J=2.0 Hz, 1H), 9.37 (s, 1H), 10.92 (s, 1H). $(M+H)^+$ 759.6.

Synthetic Scheme for Exemplary Compound 184

2-(2,6-dioxopiperidin-3-yl)-5-((7-(3-(3-((5-(5-methyl-5H-pyrido[4,3-b]indol-7-yl)pyridin-2-yl)oxy)azetidine-1-carbonyl)bicyclo[1.1.1]pentan-1-yl)heptyl)oxy)isoindoline-1,3-dione

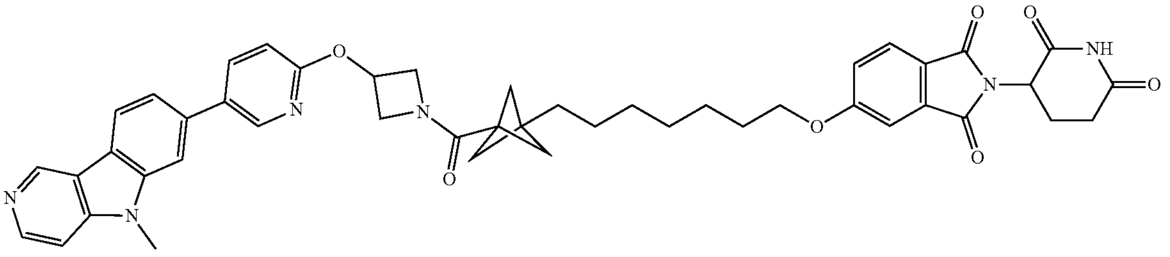

Step 1: (6-(benzyloxy)hexyl)triphenylphosphonium bromide

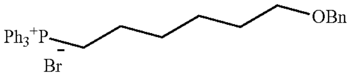

A mixture of (((6-bromohexyl)oxy)methyl)benzene (2.7 g, 10 mmol) and triphenylphosphine (2.6 g, 10 mmol) in acetonitrile (10 ml) was stirred at reflux for 40 hours. The reaction mixture was allowed to cool to room temperature and concentrated under reduced pressure to afford (6-(benzyloxy)hexyl)triphenylphosphonium bromide (5 g, yield: 94%) as colorless oil.

Step 2: Methyl 3-formylbicyclo[1.1.1]pentane-1-carboxylate

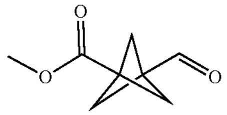

To a stirred solution of methyl 3-(hydroxymethyl)bicyclo[1.1.1]pentane-1-carboxylate (156 mg, 1 mmol) in dichloromethane (10 ml) was added Dess-Martin periodinane (840 mg, 2.0 mmol) at 0° C. The resulting reaction mixture was allowed to warm up to room temperature and stirred at this temperature for additional 1 h. The reaction mixture was quenched with aqueous solution of sodium sulfite (10 ml) and extracted with dichloromethane (20 ml×2), washed with brine (20 ml×2), dried over anhydrous sodium sulfate, and concentrated under reduced pressure to afford a crude residue which was purified by silica gel flash chromatography (eluted with 20% ethyl acetate in hexane) to afford methyl 3-formylbicyclo[1.1.1]pentane-1-carboxylate (110 mg, yield 70%) as colorless oil.

Step 3: Methyl 3-(7-(benzyloxy)hept-1-en-1-yl)bicyclo[1.1.1]pentane-1-carboxylate

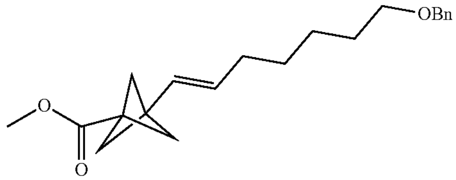 [SMILES: COC(=O)C12CC(/C=C/CCCCCOCc3ccccc3)(C1)C2]

To a solution of (6-(benzyloxy)hexyl)triphenylphosphonium bromide (373 mg, 0.70 mmol) in anhydrous tetrahydrofuran (6 ml) was added n-butyllithium (2.5 M in hexane) (0.28 mL, 0.7 mmol) dropwise at −20° C. and the resulting mixture was stirred at the same temperature for 30 min. Methyl 3-formylbicyclo[1.1.1]pentane-1-carboxylate (90 mg, 0.58 mmol) in anhydrous tetrahydrofuran (1 ml) was added dropwise. The resulting reaction mixture was warmed to room temperature slowly and stirred at the same temperature for 30 min. The reaction mixture was quenched with water (10 ml) at 0° C. and extracted with ethyl acetate (20 ml×2). The combined organic layers were washed with brine (20 ml), dried over anhydrous sodium sulfate, and concentrated under reduced pressure to give a residue which was purified by silica gel flash chromatography (eluted with 10% ethyl acetate in hexane) to afford methyl 3-(7-(benzyloxy)hept-1-en-1-yl)bicyclo[1.1.1]pentane-1-carboxylate (56 mg, yield 29%) as colorless oil.

Methyl 3-(7-(benzyloxy)hept-1-en-1-yl)bicyclo[1.1.1]pentane-1-carboxylate was converted to the final compound, 2-(2,6-dioxopiperidin-3-yl)-5-((7-(3-(3-((5-(5-methyl-5H-pyrido[4,3-b]indol-7-yl)pyridin-2-yl)oxy)azetidine-1-carbonyl)bicyclo[1.1.1]pentan-1-yl)heptyl)oxy)isoindoline-1,3-dione, according to the schemes below and using procedures described above and common procedures known to those skilled in the art.

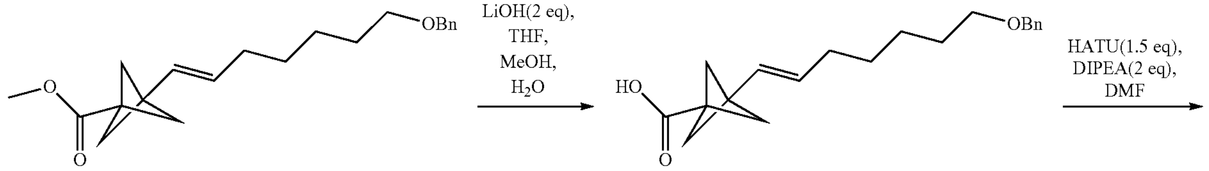

-continued
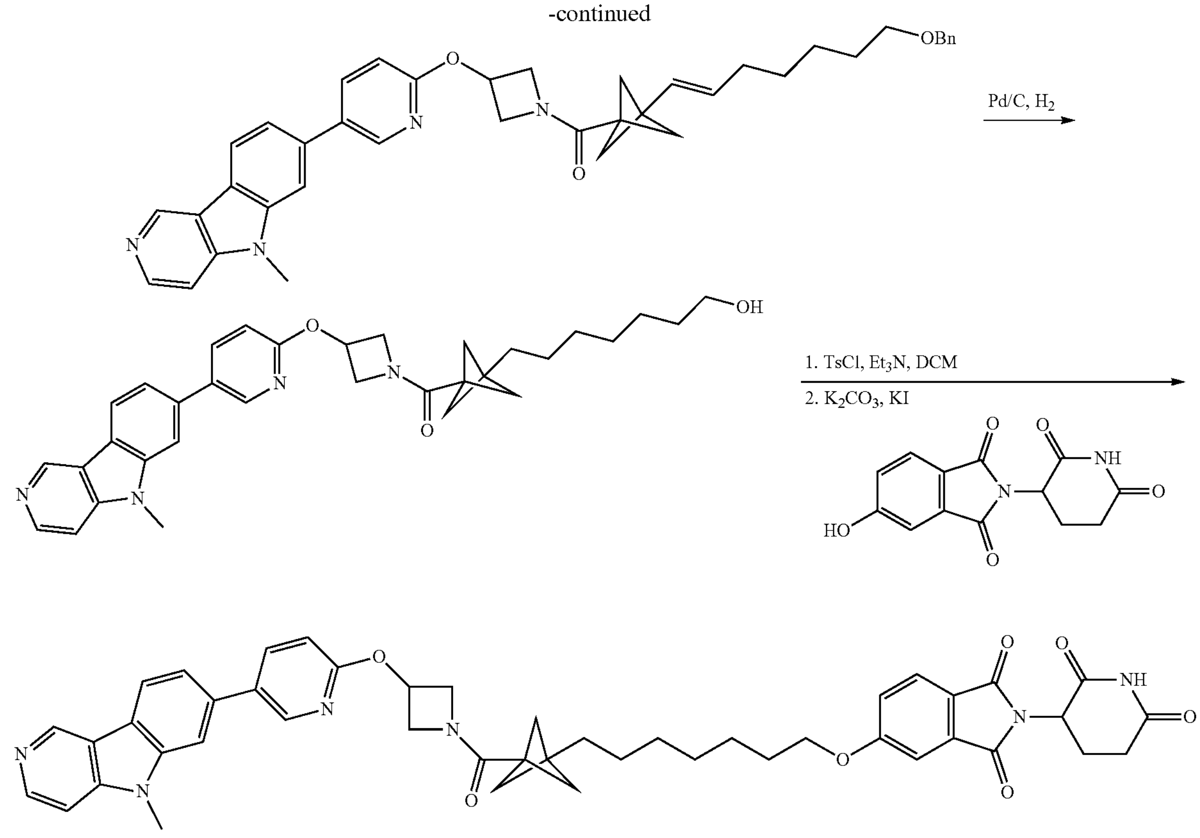
Compound 184
Synthetic Scheme for Exemplary Compound 185
(2S,4R)-N-(2-(2-((5-(5H-pyrido[4,3-b]indol-7-yl)pyridin-2-yl)oxy)ethoxy)-4-(4-methylthiazol-5-yl)benzyl)-4-hydroxy-1-((S)-3-methyl-2-(1-oxoisoindolin-2-yl)butanoyl)pyrrolidine-2-carboxamide
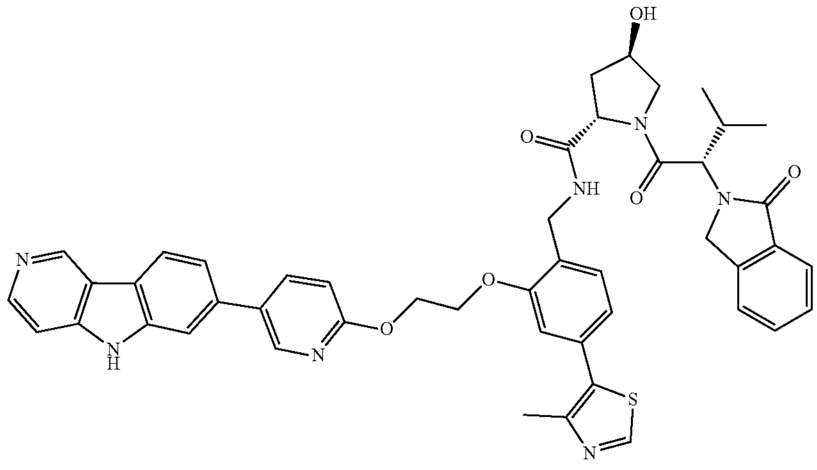 [SMILES: Cc1ncsc1-c1ccc(CNC(=O)[C@@H]2C[C@@H](O)CN2C(=O)[C@H](C(C)C)N2Cc3ccccc3C2=O)c(OCCOc2ccc(-c3ccc4c(c3)[nH]c3ccncc34)cn2)c1]
Prepared according to the scheme below and using procedures described above and common procedures known to those skilled in the art.

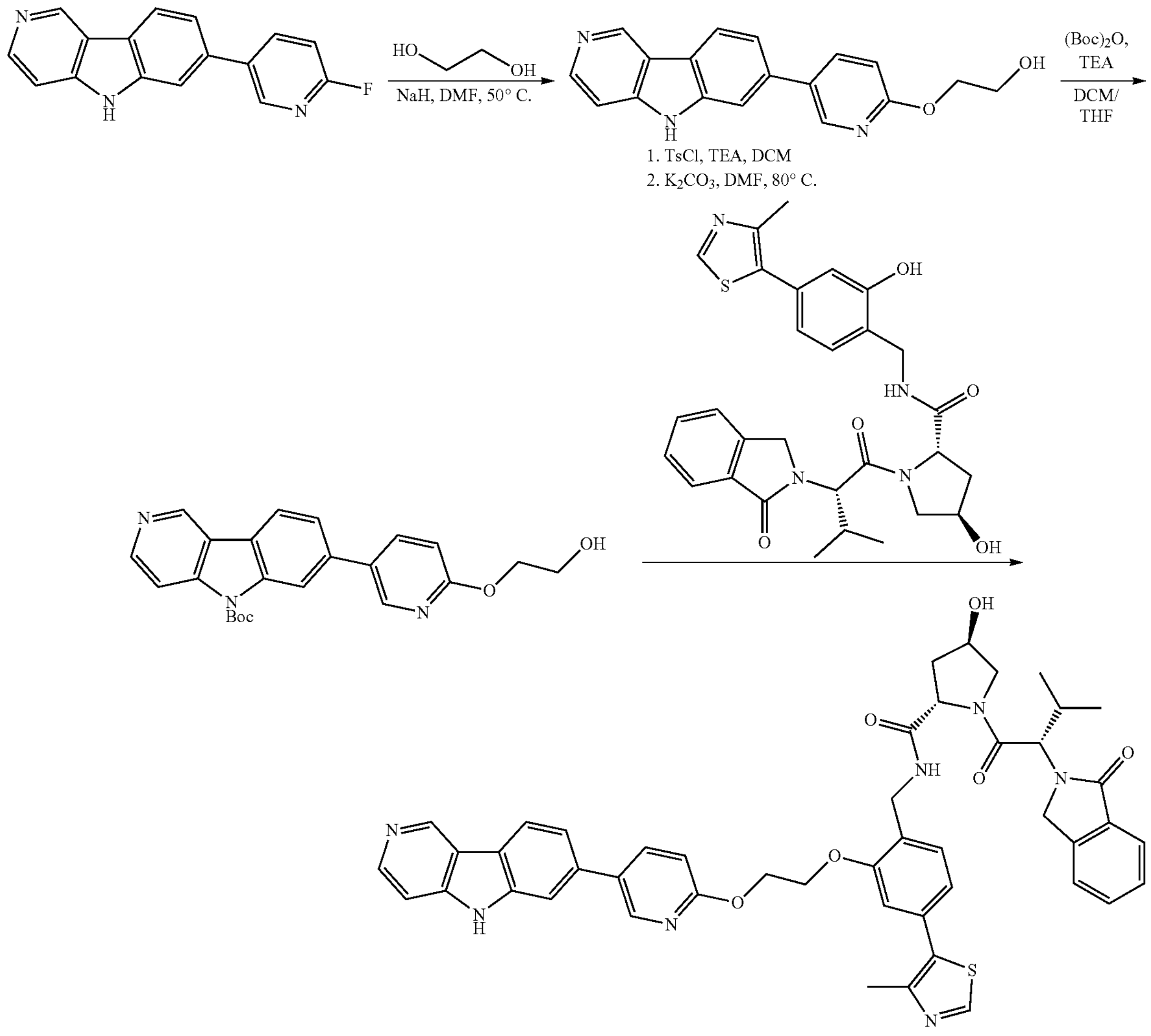
Compound 185
Using procedures analogous to those for Compound 185 the following were prepared: Compounds 186, 187, 196, 201.
Synthetic Scheme for Exemplary Compound 193
2-(2,6-dioxopiperidin-3-yl)-5-(3-(3-(2-(6-((5-(5-methyl-5H-pyrido[4,3-b]indol-7-yl)pyridin-2-yl)oxy)-2-azaspiro[3.3]heptan-2-yl)-2-oxoethoxy)propoxy)azetidin-1-yl)isoindoline-1,3-dione
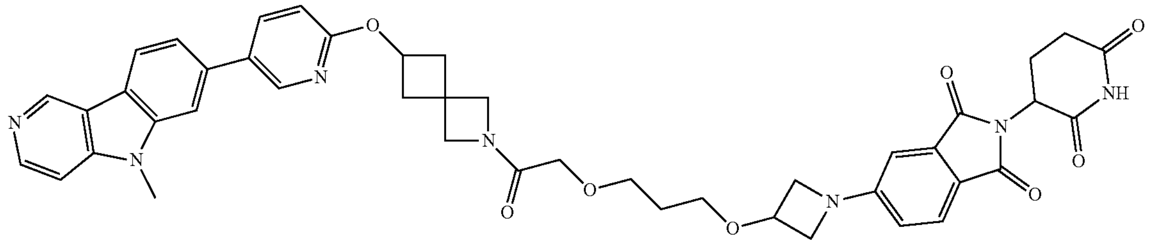 [SMILES: Cn1c2ccncc2c2ccc(-c3ccc(OC4CC5(C4)CN(C(=O)COCCCOC4CN(c6ccc7c(c6)C(=O)N(C6CCC(=O)NC6=O)C7=O)C4)C5)nc3)cc21]

Prepared according to the schemes below and using procedures described above and common procedures known to those skilled in the art.
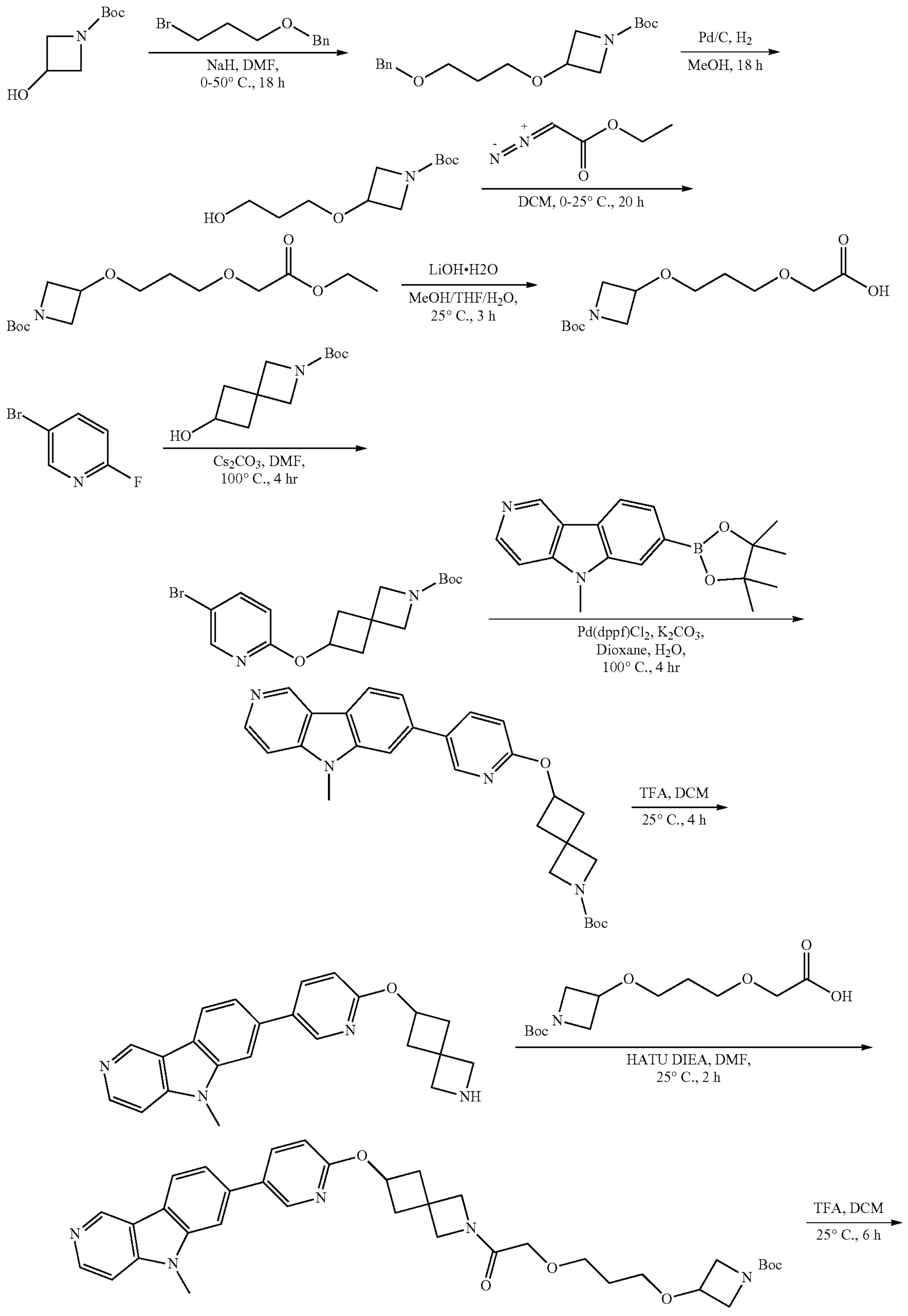

-continued

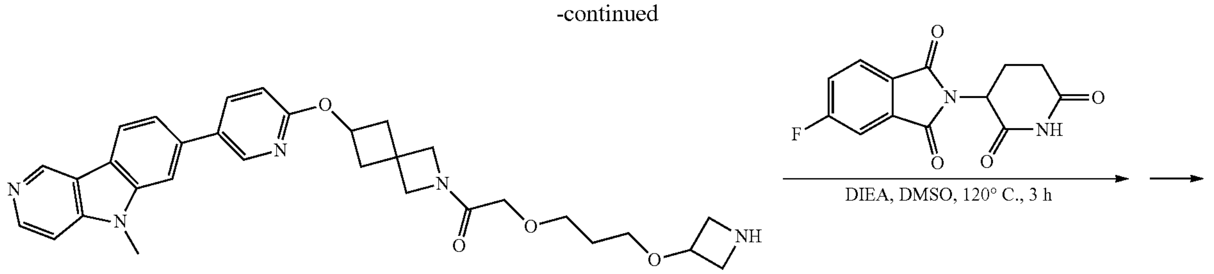

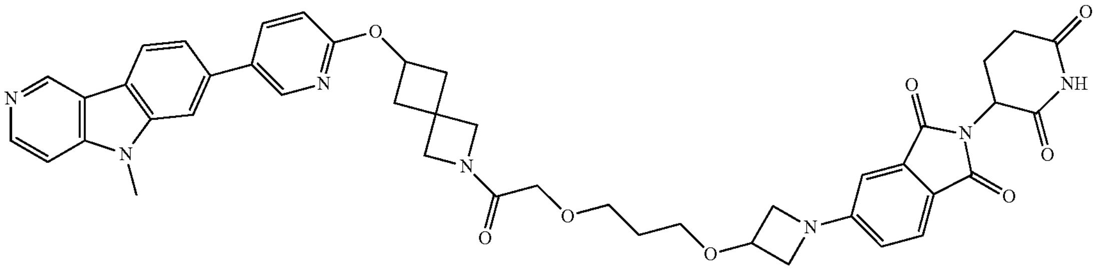

Compound 193

Synthetic Scheme for Exemplary Compound 195

5-((14-((5-(4-chloro-5-methyl-5H-pyrido[4,3-b]indol-7-yl)pyridin-2-yl)oxy)-3,6,9,12-tetraoxatetradecyl)oxy)-2-(2,6-dioxopiperidin-3-yl)isoindoline-1,3-dione

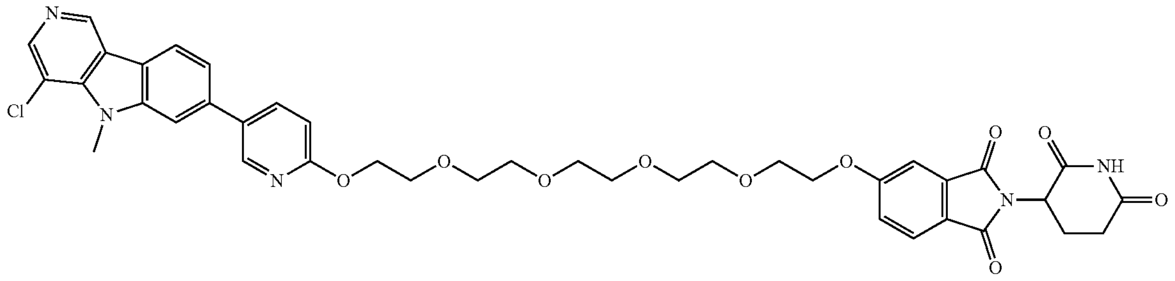 [SMILES: Cn1c2cc(-c3ccc(OCCOCCOCCOCCOCCOc4ccc5c(c4)C(=O)N(C4CCC(=O)NC4=O)C5=O)nc3)ccc2c2cncc(Cl)c21]

Step 1: 3-bromo-5-chloropyridin-4-amine

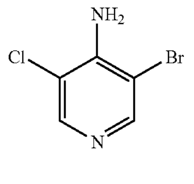

To a solution of 3-chloropyridin-4-amine (10 g, 77.78 mmol) in acetonitrile (100 ml) was added N-bromosuccinimide (14.5 g, 81.67 mmol) at room temperature, and the resulting mixture was stirred at 60° C. for overnight under nitrogen. The reaction mixture was quenched with water (50 ml) and extracted with ethyl acetate (50 ml×2). The combined organic layers were washed with brine (50 ml×2), dried over anhydrous sodium sulfate, and concentrated to give a residue which was purified by silica gel flash chromatography (eluted with 20-50% ethyl acetate in hexane) to afford 3-bromo-5-chloropyridin-4-amine (8.8 g, yield 54%) as white solid.

Step 2: 3-(4-bromophenyl)-5-chloropyridin-4-amine

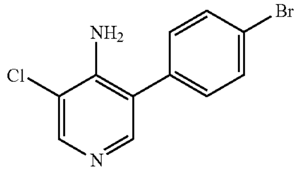 [SMILES: Nc1c(Cl)cncc1-c1ccc(Br)cc1]

A mixture of 3-bromo-5-chloropyridin-4-amine (5 g, 24.10 mmol), bis(pinacolato)diboron (12 g, 48320 mmol), potassium acetate (4.7 g, 48.20 mmol) and 1,1'-bis(diphenylphosphino)ferrocene palladium(II)dichloride (3.5 g, 4.82 mmol) in dioxane (100 ml) was stirred at 90° C. overnight under nitrogen. TLC showed the reaction was complete. To this mixture solution was added 1,4-dibromobenzene (11.4 g, 48.20 mmol), potassium carbonate (6.7 g, 48.20 mmol)

and water (30 ml). tetrakis(triphenylphosphine)palladium (1.4 g, 1.21 mmol) was added and the mixture was stirred at 90° C. overnight under nitrogen. The reaction mixture was filtered and the filtrate was partitioned between ethyl acetate (100 ml) and water (100 ml), the organic layer was washed with brine (20 ml×2), dried over anhydrous sodium sulfate and concentrated under reduced pressure to give a crude residue which was purified by silica gel flash chromatography (eluted with 20-50% ethyl acetate in hexane) to afford 3-(4-bromophenyl)-5-chloropyridin-4-amine (2.3 g, yield 34%) as yellow solid.

Step 3: 4-azido-3-(4-bromophenyl)-5-chloropyridine

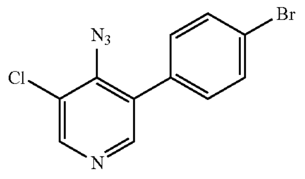 [SMILES: [N-]=[N+]=Nc1c(Cl)cncc1-c1ccc(Br)cc1]

To a solution of 3-(4-bromophenyl)-5-chloropyridin-4-amine (2.5 g, 8.8 mmol) in 2,2,2-trifluoroacetic acid (10 ml) was added sodium nitrite (1.5 g, 22.0 mmol) at 0° C. during 20 min, and the reaction mixture was stirred at 0° C. for 1 hour. To the reaction mixture was added sodium azide (1.43 g, 22.0 mmol) at 0° C.; the resulting mixture was allowed to warm up to room temperature and stirred overnight. The reaction mixture was basified with sodium carbonate till pH 8, and partitioned between ethyl acetate (30 ml) and water (50 ml). The organic layer was collected, and the aqueous layer was extracted with ethyl acetate (30 ml×2). The combined organic layers were washed with brine (20 ml), dried over anhydrous sodium sulfate, and concentrated under reduced pressure to give a crude residue which was purified by silica gel flash chromatography (eluted with 30% ethyl acetate in hexane) as 4-azido-3-(4-bromophenyl)-5-chloropyridine (850 mg, yield 31%) as yellow solid.

Step 4

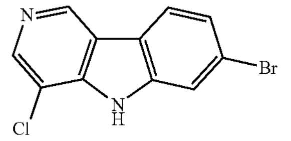 [SMILES: Clc1cncc2c1[nH]c1cc(Br)ccc12]

A mixture of 4-azido-3-(4-bromophenyl)-5-chloropyridine (850 mg, 2.75 mmol) in decalin (10 ml) was stirred in a sealed tube at 150° C. for 10 hours. After cooling to room temperature, the reaction mixture was triturated with hexane (20 ml). The resulting solid was collected by filtration and dried under vacuum to afford 7-bromo-4-chloro-5H-pyrido[4,3-b]indole (600 mg, yield 77%) as yellow solid which was used in next step directly without further purification.

7-bromo-4-chloro-5H-pyrido[4,3-b]indole was converted to the final compound, 5-((14-((5-(4-chloro-5-methyl-5H-pyrido[4,3-b]indol-7-yl)pyridin-2-yl)oxy)-3,6,9,12-tetraoxatetradecyl)oxy)-2-(2,6-dioxopiperidin-3-yl)isoindoline-1,3-dione, according to the scheme below and using procedures described above and common procedures known to those skilled in the art.

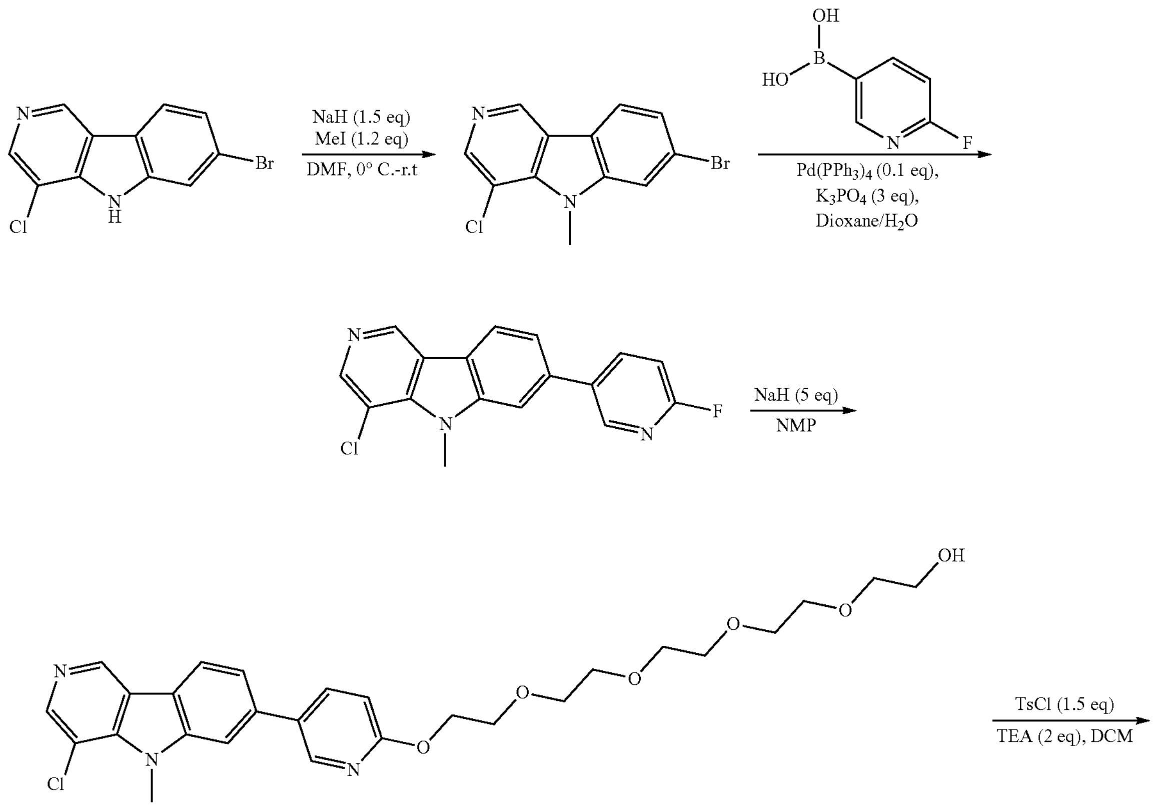

-continued
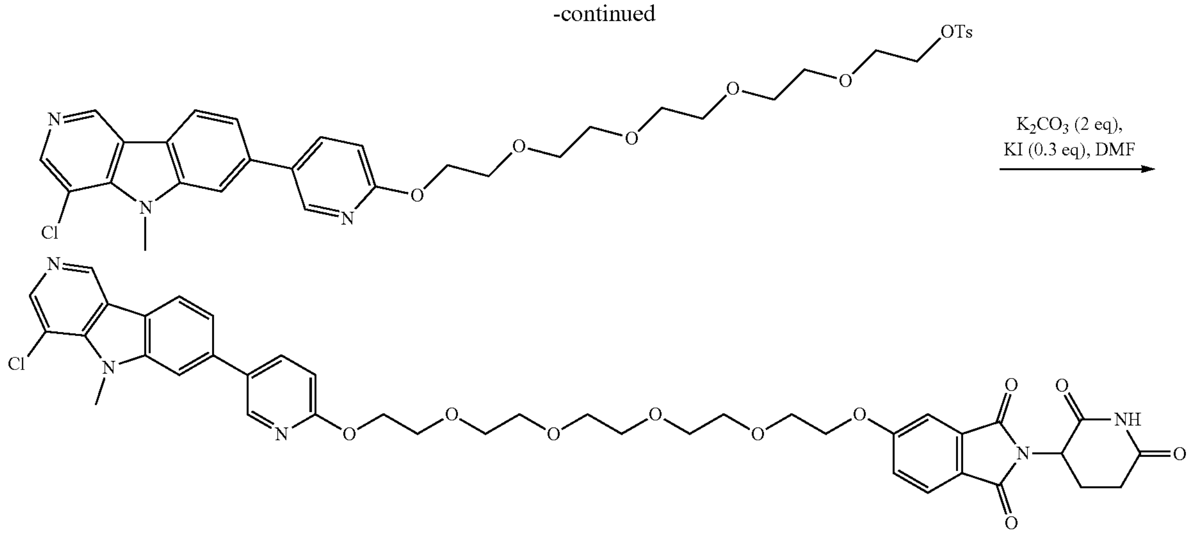
Compound 195
Synthetic Scheme for Exemplary Compound 197
5-(6-((2,2-difluoro-5-((1r,3r)-3-((5-(5-methyl-5H-pyrido[4,3-b]indol-7-yl)pyridin-2-yl)oxy)cyclobutoxy)pentyl)oxy)-2-azaspiro[3.3]heptan-2-yl)-2-(2,6-dioxopiperidin-3-yl)isoindoline-1,3-dione
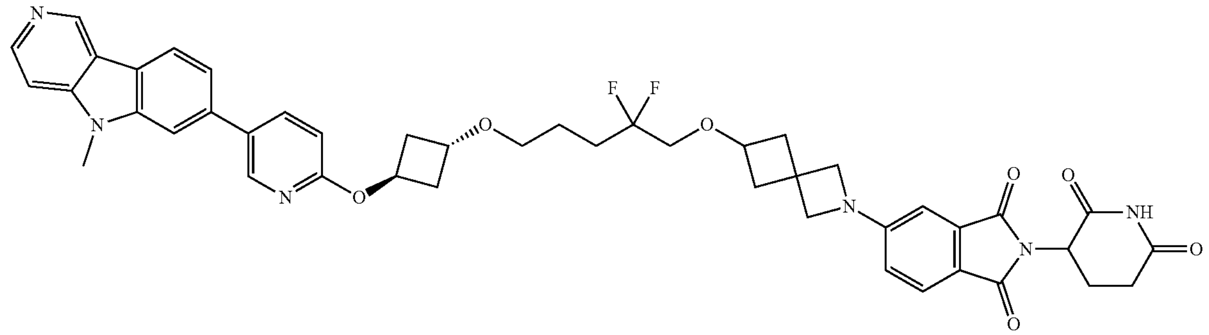 [SMILES: Cn1c2ccncc2c2ccc(-c3ccc(O[C@H]4C[C@H](OCCCC(F)(F)COC5CC6(C5)CN(c5ccc7c(c5)C(=O)N(C5CCC(=O)NC5=O)C7=O)C6)C4)nc3)cc21]
Prepared according to the scheme below and using procedures described above and common procedures known to those skilled in the art.
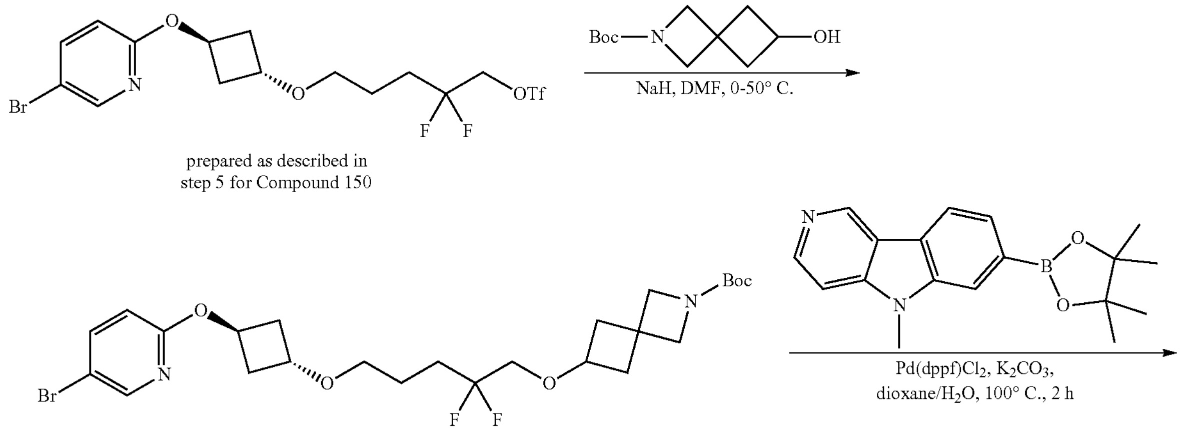

-continued
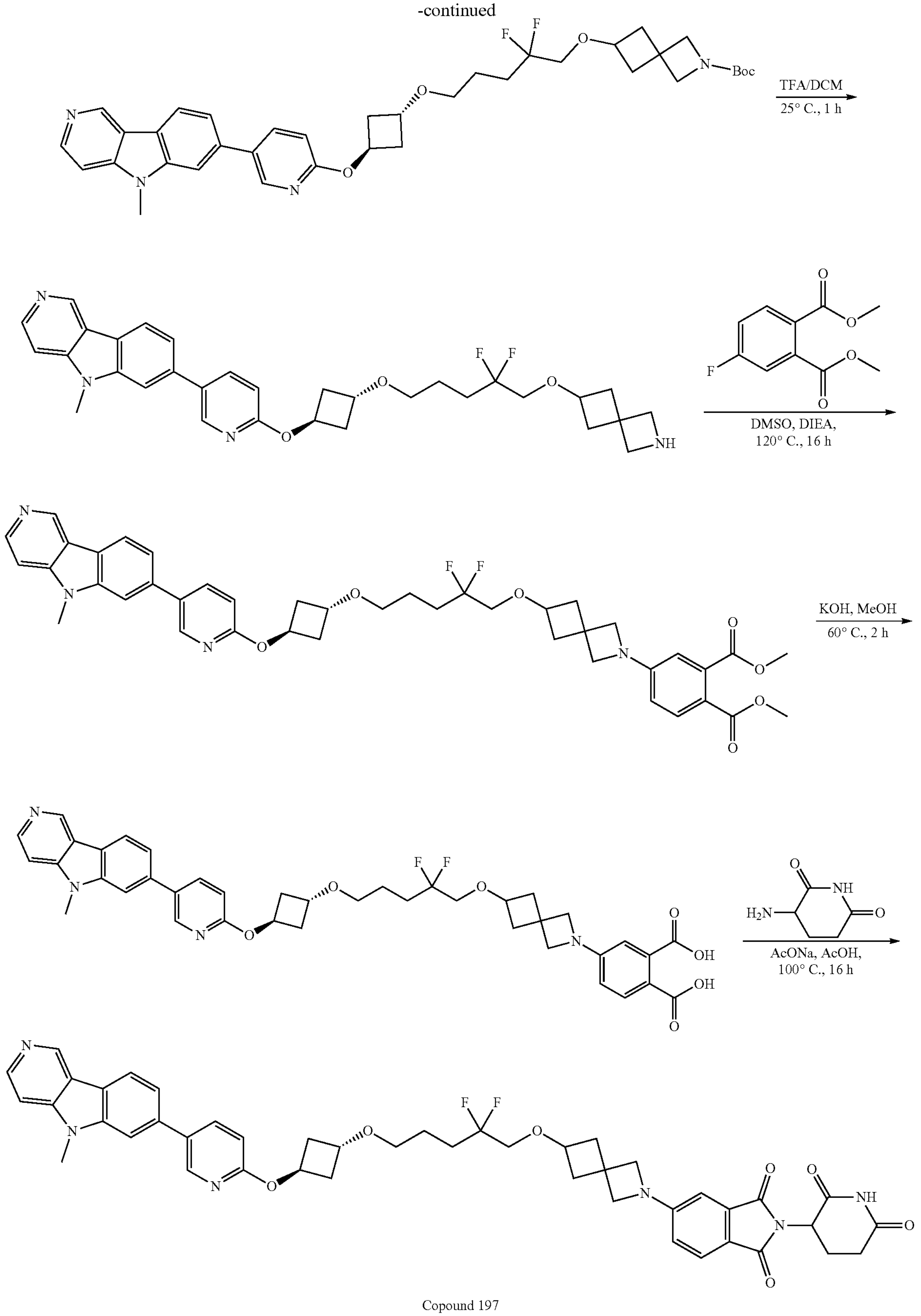
Copound 197

Synthetic Scheme for Exemplary Compound 199
3-((4-((2-(2,6-dioxopiperidin-3-yl)-1,3-dioxoisoindolin-5-yl)oxy)butoxy)methyl)-N-methyl-N-((1r,3r)-3-((5-(5-methyl-5H-pyrido[4,3-b]indol-7-yl)pyridin-2-yl)oxy)cyclobutyl)bicyclo[1.1.1]pentane-1-carboxamide
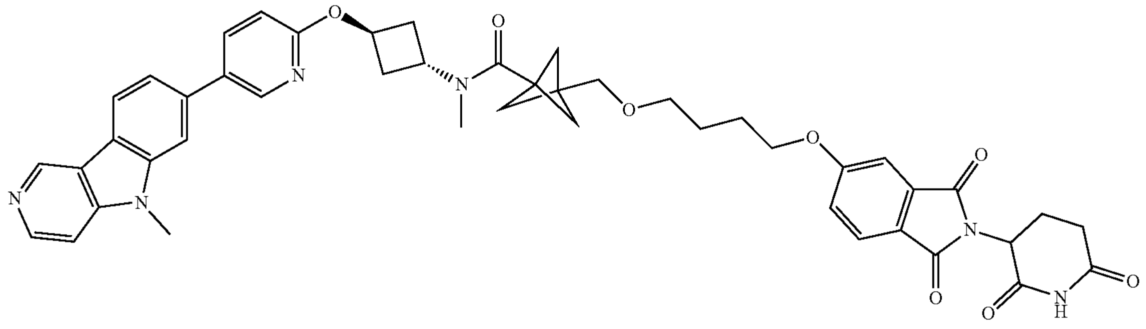 [SMILES: Cn1c2ccncc2c2ccc(-c3ccc(O[C@H]4C[C@H](N(C)C(=O)C56CC(COCCCCOc7ccc8c(c7)C(=O)N(C7CCC(=O)NC7=O)C8=O)(C5)C6)C4)nc3)cc21]
Prepared according to the scheme below and using procedures described above and common procedures known to those skilled in the art.
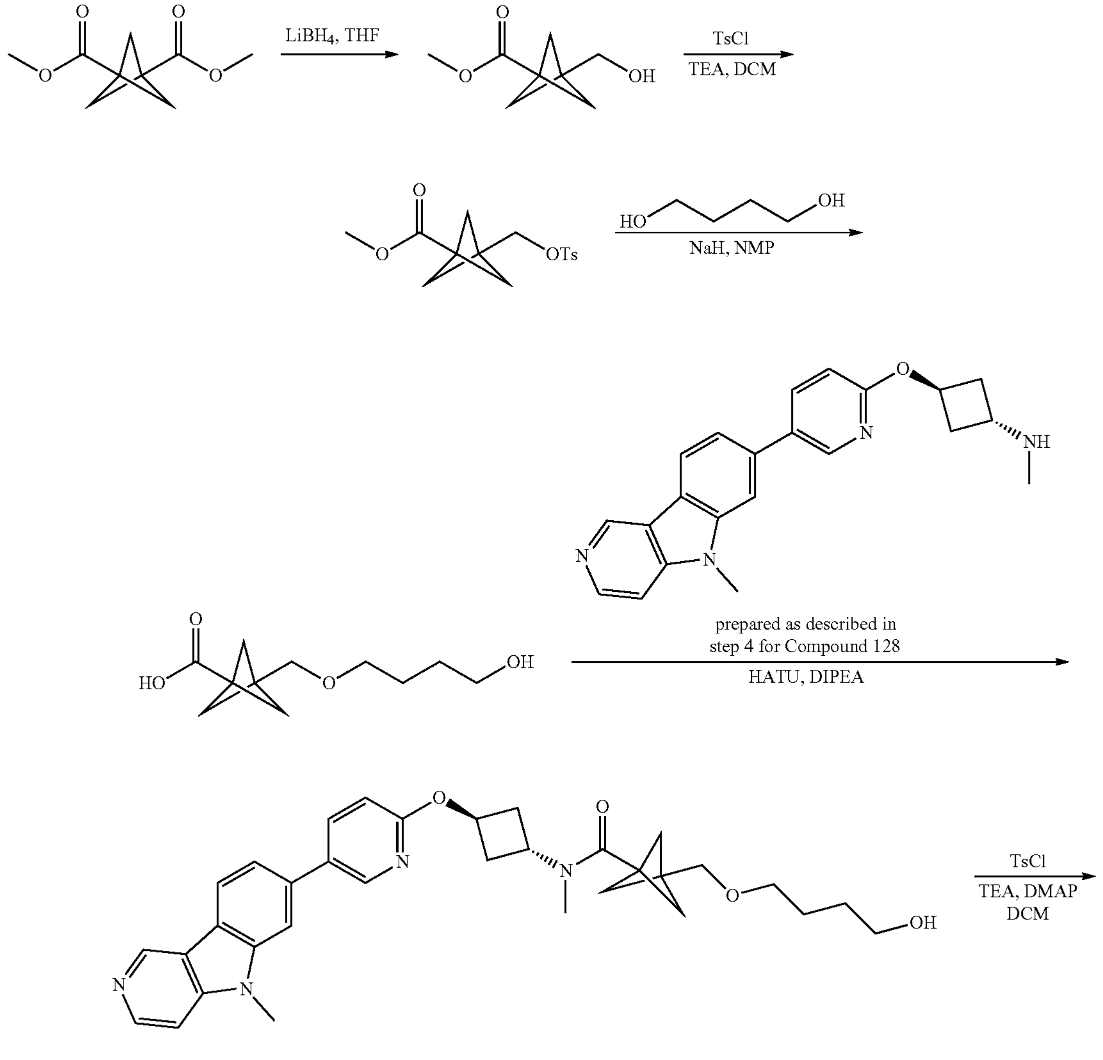

-continued
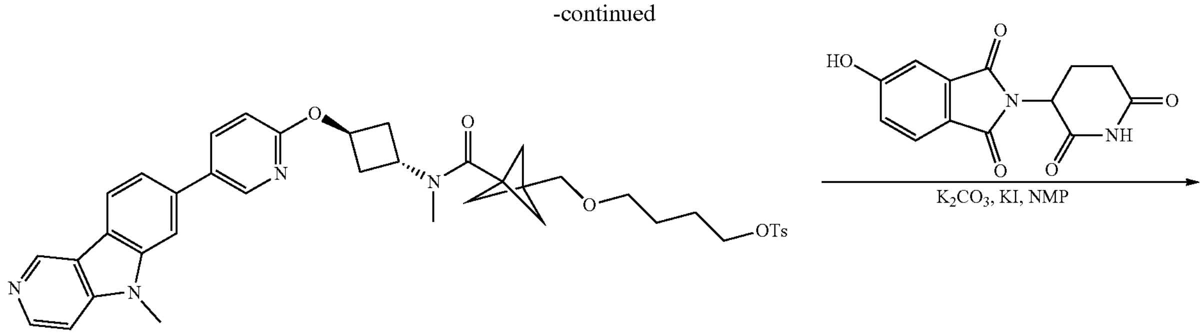
Compound199
Synthetic Scheme for Exemplary Compound 202
2-((1-(2-(2,6-dioxopiperidin-3-yl)-1,3-dioxoisoindolin-5-yl)azetidin-3-yl)methoxy)-N-methyl-N-(3-((1r, 3r)-3-((5-(5-methyl-5H-pyrido[4,3-b]indol-7-yl) pyridin-2-yl)oxy)cyclobutoxy)propyl)acetamide
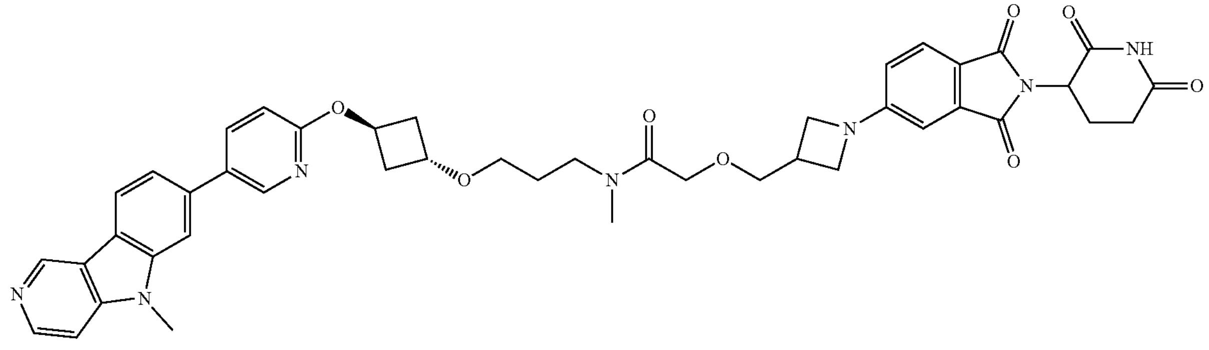 [SMILES: CN(CCCO[C@H]1C[C@H](Oc2ccc(-c3ccc4c5cnccc5n(C)c4c3)cn2)C1)C(=O)COCC1CN(c2ccc3c(c2)C(=O)N(C2CCC(=O)NC2=O)C3=O)C1]
Prepared according to the schemes below and using procedures described above and common procedures known to those skilled in the art.
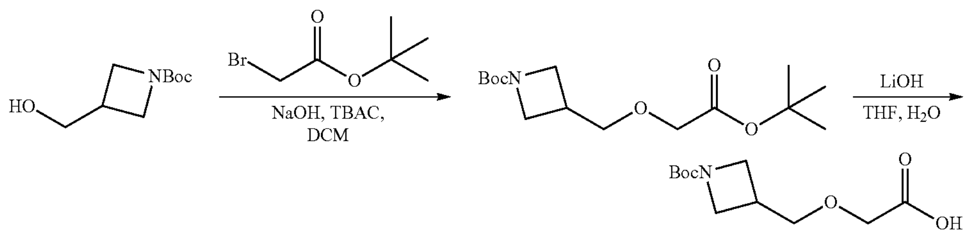

-continued
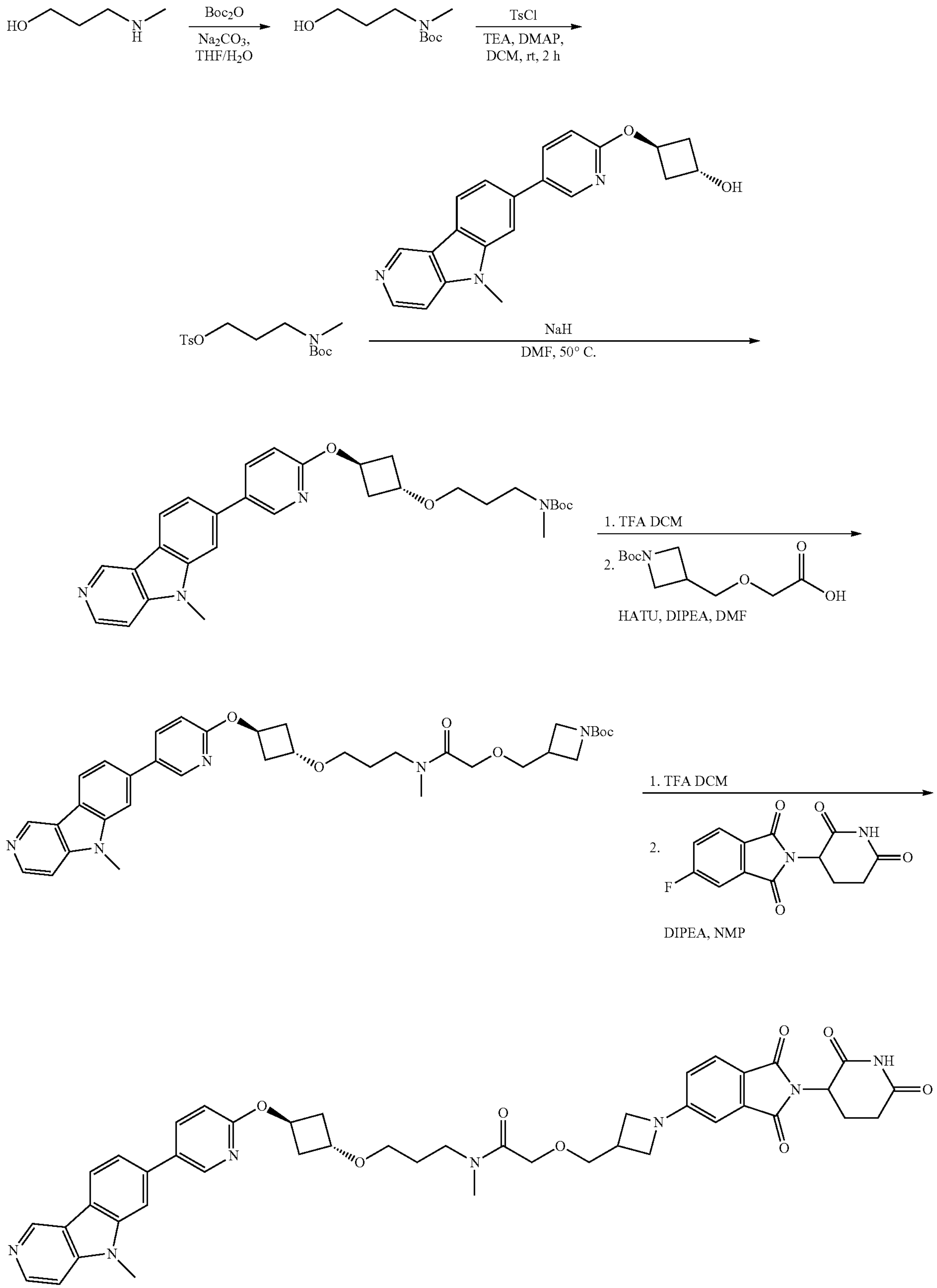
Compound 202

Synthetic Scheme for Exemplary Compound 203
2-((14-((2-(2,6-dioxopiperidin-3-yl)-1,3-dioxoisoindolin-5-yl)oxy)-3,6,9,12-tetraoxatetradecyl)oxy)-5-(5-methyl-5H-pyrido[4,3-b]indol-7-yl)nicotinonitrile
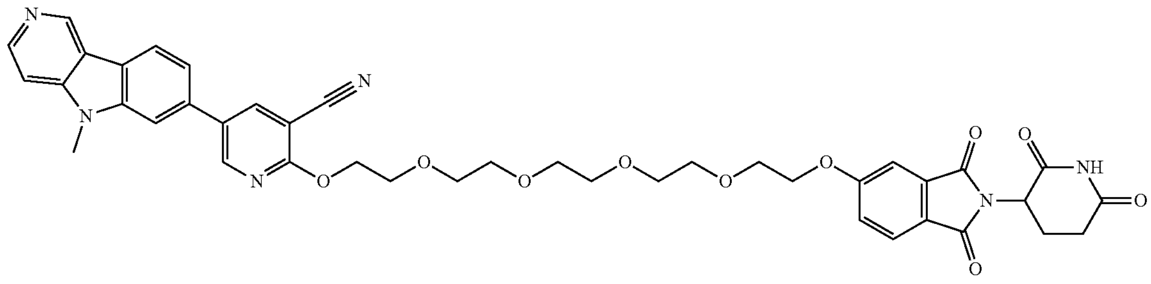 [SMILES: Cn1c2ccncc2c2ccc(-c3cnc(OCCOCCOCCOCCOCCOc4ccc5c(c4)C(=O)N(C4CCC(=O)NC4=O)C5=O)c(C#N)c3)cc21]
Prepared according to the scheme below and using procedures described above and common procedures known to those skilled in the art.
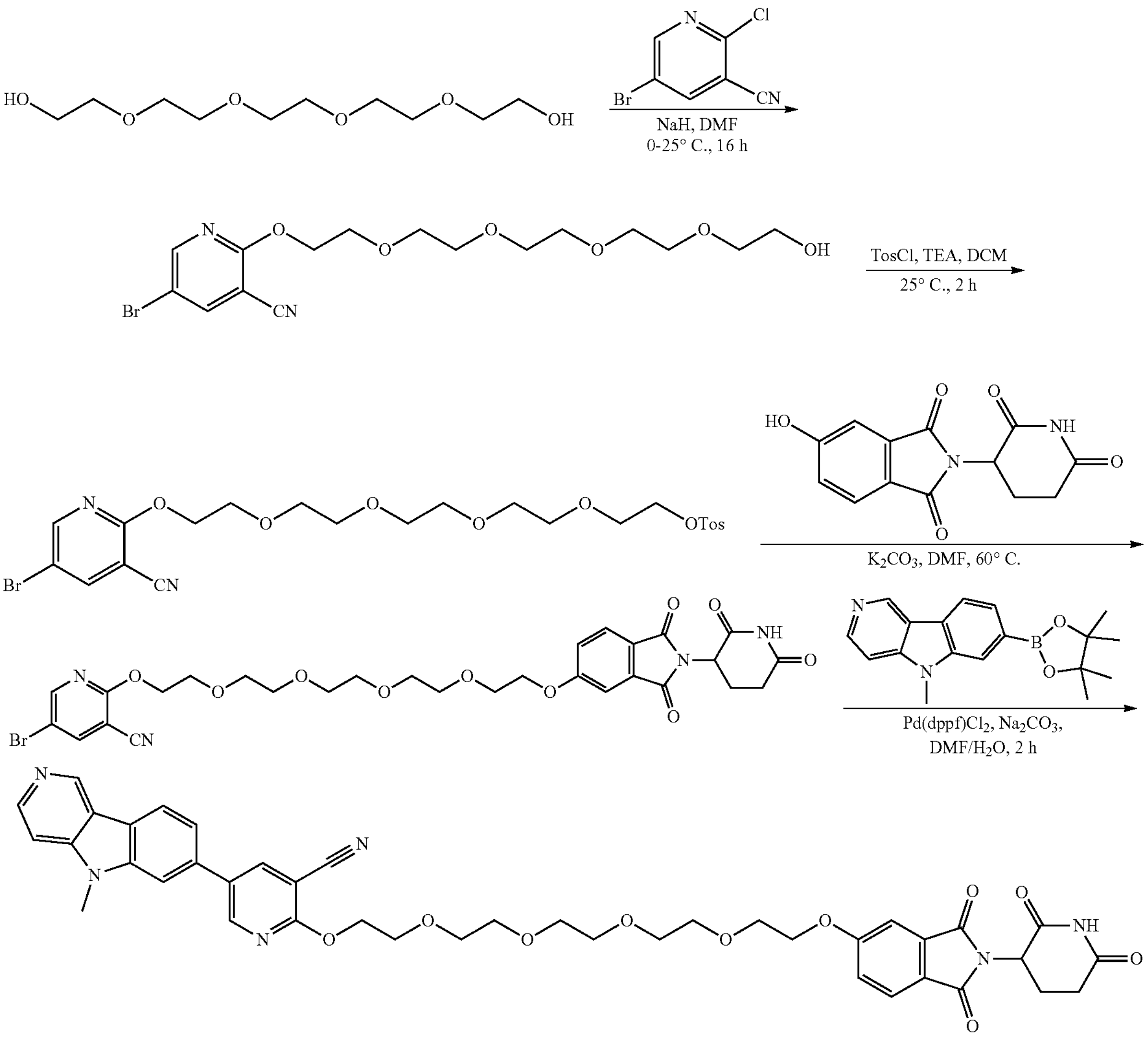
Compound 203

Synthetic Scheme for Exemplary Compound 207

5-((14-((5-(benzo[4,5]imidazo[1,2-a]pyrimidin-2-yl)pyridin-2-yl)oxy)-3,6,9,12-tetraoxatetradecyl)oxy)-2-(2,6-dioxopiperidin-3-yl)isoindoline-1,3-dione

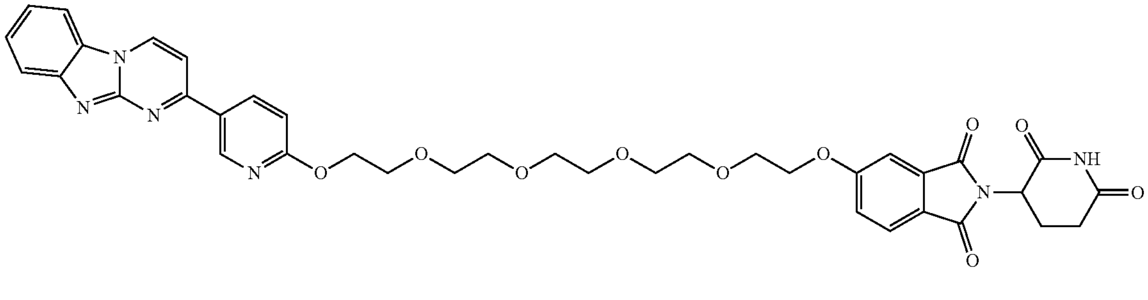 [SMILES: O=C1CCC(N2C(=O)c3ccc(OCCOCCOCCOCCOCCOc4ccc(-c5ccn6c(n5)nc5ccccc56)cn4)cc3C2=O)C(=O)N1]

Step 1: (E)-1,1,1-trichloro-4-ethoxy-but-3-en-2-one

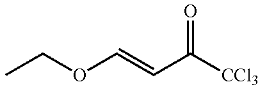

To a solution of 2,2,2-trichloroacetyl chloride (31.52 g, 173.36 mmol, 19 mL, 1 eq) was added dropwise ethyl vinyl ether (25 g, 346.71 mmol, 33 mL, 2 eq) at 0° C. After addition, the mixture was stirred at this temperature for 5 h, and then the mixture was warmed to 25° C. for 16 h. The mixture was stirred at 130° C. under reduced pressure to let gas (hydrogen chloride) evaporate to form a deep black color solution. The process required for 1 h or waited until no gas came out. The residue was concentrated under reduced pressure. The crude product (E)-1,1,1-trichloro-4-ethoxy-but-3-en-2-one (39.3 g, crude) was obtained as a black oil.

Step 2: 2-(trichloromethyl)pyrimido[1,2-a]benzimidazole

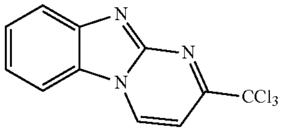

To a mixture of (E)-1,1,1-trichloro-4-ethoxy-but-3-en-2-one (39.2 g, 180.25 mmol, 1.09 eq) and 1H-benzimidazol-2-amine (22 g, 165.23 mmol, 1 eq) in toluene (500 mL) was added triethylamine (20.06 g, 198.27 mmol, 27 mL, 1.2 eq) in one portion at 25° C. under nitrogen. The mixture was stirred at 120° C. for 4 h. The mixture was cooled to 25° C. and concentrated under reduced pressure at 55° C. The crude product 2-(trichloromethyl)pyrimido[1,2-a]benzimidazole (56.3 g, crude) was obtained as brown solid.

Step 3: Pyrimido[1,2-a]benzimidazol-2-ol

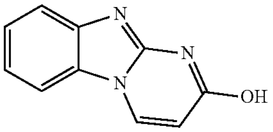 [SMILES: Oc1ccn2c(n1)nc1ccccc12]

To a mixture of 2-(trichloromethyl)pyrimido[1,2-a]benzimidazole (55.2 g, 192.64 mmol, 1 eq) in acetonitrile (950 mL) was added sodium hydroxide (10.2 g, 255.02 mmol, 1.32 eq) in Water (246 mL) in one portion at 20° C. under nitrogen. The mixture was stirred at 100° C. for 2 h. The mixture was cooled to 25° C. and concentrated in reduced pressure at 55° C. Ice was added to the resulting residue, and the pH of the solution was adjusted to 8 with hydrochloric acid (1 N, 130 mL). The solid was filtered, and dried under high vacuum. The filter was cooled to 10° C., some precipitate was formed, the cake was collected by filtered and concentrated under reduced pressure to give a residue. Compound pyrimido[1,2-a]benzimidazol-2-ol (9.3 g, 50.22 mmol, 26% yield) was obtained as a yellow solid, and crude product (about 7.3 g) was obtained.

Step 4: 2-Bromopyrimido[1,2-a]benzimidazole

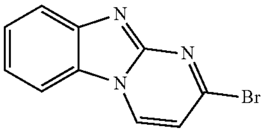 [SMILES: Brc1ccn2c(n1)nc1ccccc12]

To a solution of pyrimido[1,2-a]benzimidazol-2-ol (0.5 g, 2.70 mmol, 1 eq) in 1,1-dichloroethane (18 mL) and N,N-dimethylformamide (0.18 mL) was added phosphoryl tribromide (1.55 g, 5.40 mmol, 2 eq) in one portion at 20° C. under nitrogen. The mixture was stirred at 100° C. for 6 h. The mixture was cooled to 25° C. and concentrated under reduced pressure at 45° C. The residue was poured into ice-water (w/w=1/1, 30 mL) and stirred for 10 min. The aqueous phase was adjusted to pH=8 with a saturated aqueous solution of sodium bicarbonate. During this period, some precipitate was formed. The cake was collected by filtration and dried under high vacuum. The crude product 2-bromopyrimido[1,2-a]benzimidazole (0.65 g, crude) was obtained as a yellow solid.

2-Bromopyrimido[1,2-a]benzimidazole was converted to the final compound, 5-((14-((5-(benzo[4,5]imidazo[1,2-a]pyrimidin-2-yl)pyridin-2-yl)oxy)-3,6,9,12-tetraoxatetradecyl)oxy)-2-(2,6-dioxopiperidin-3-yl)isoindoline-1,3-dione, according to the scheme below and using procedures described above and common procedures known to those skilled in the art.

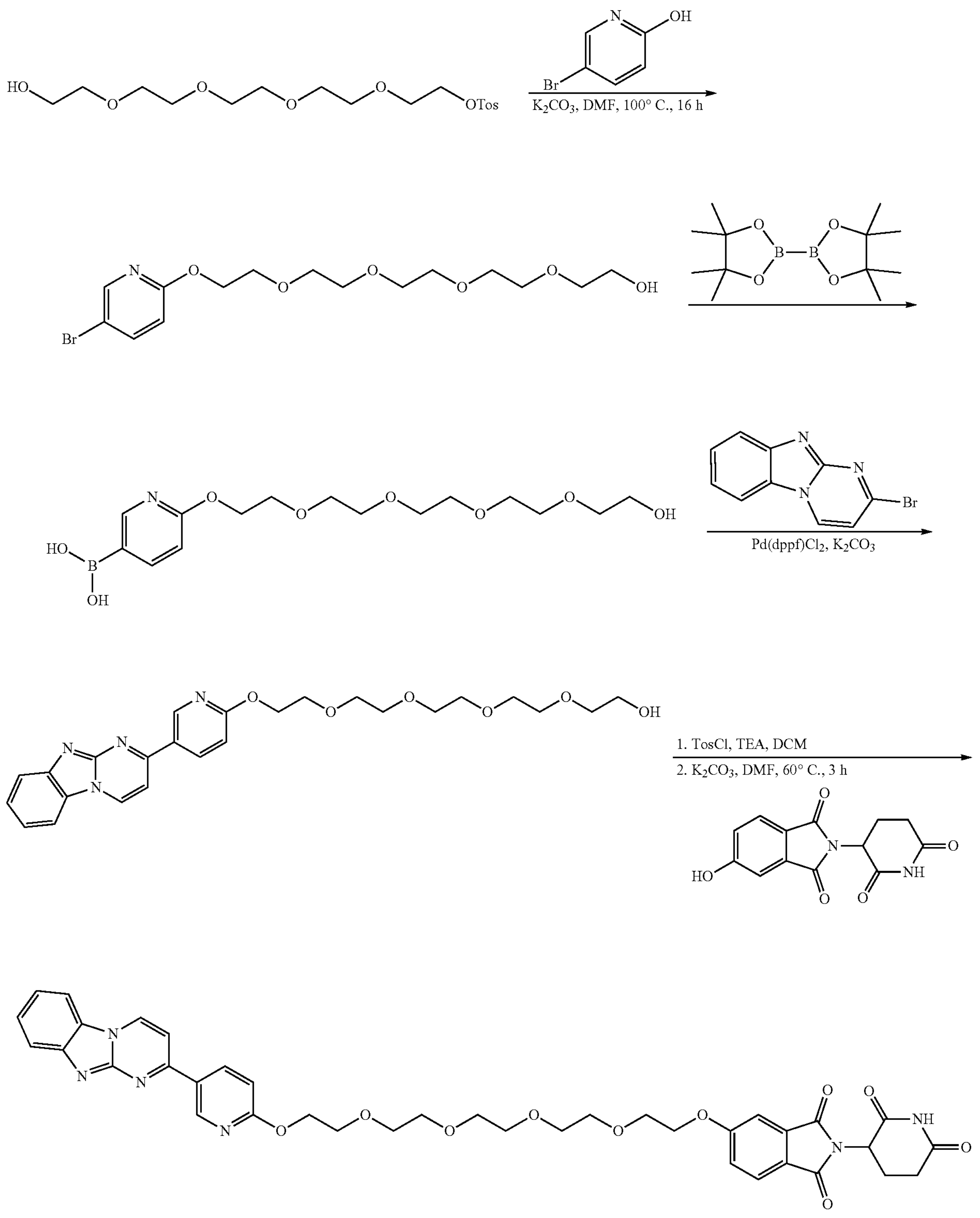

Compound 207

Synthetic Scheme for Exemplary Compound 208
2-(2,6-dioxopiperidin-3-yl)-5-(2-(2-(2-(2-((1-(5-(5-methyl-5H-pyrido[4,3-b]indol-7-yl)pyridin-2-yl)azetidin-3-yl)oxy)ethoxy)ethoxy)ethoxy)ethoxy)isoindoline-1,3-dione
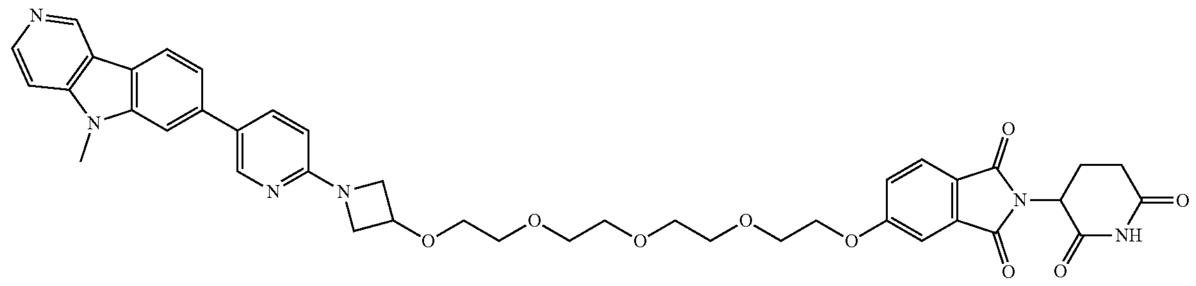 [SMILES: Cn1c2ccncc2c2ccc(-c3ccc(N4CC(OCCOCCOCCOCCOc5ccc6c(c5)C(=O)N(C5CCC(=O)NC5=O)C6=O)C4)nc3)cc21]
Prepared according to the scheme below and using procedures described above and common procedures known to those skilled in the art.
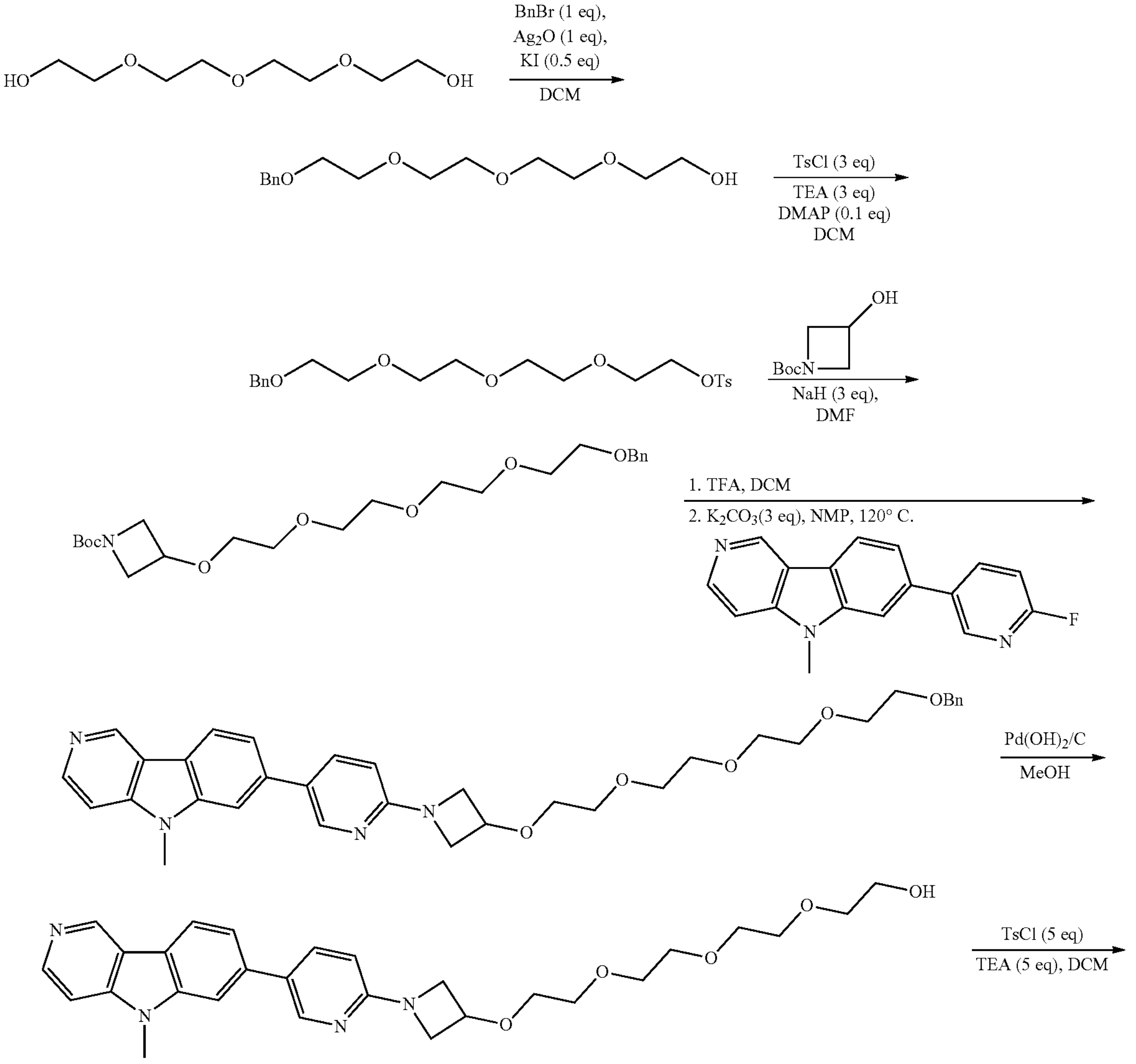

-continued
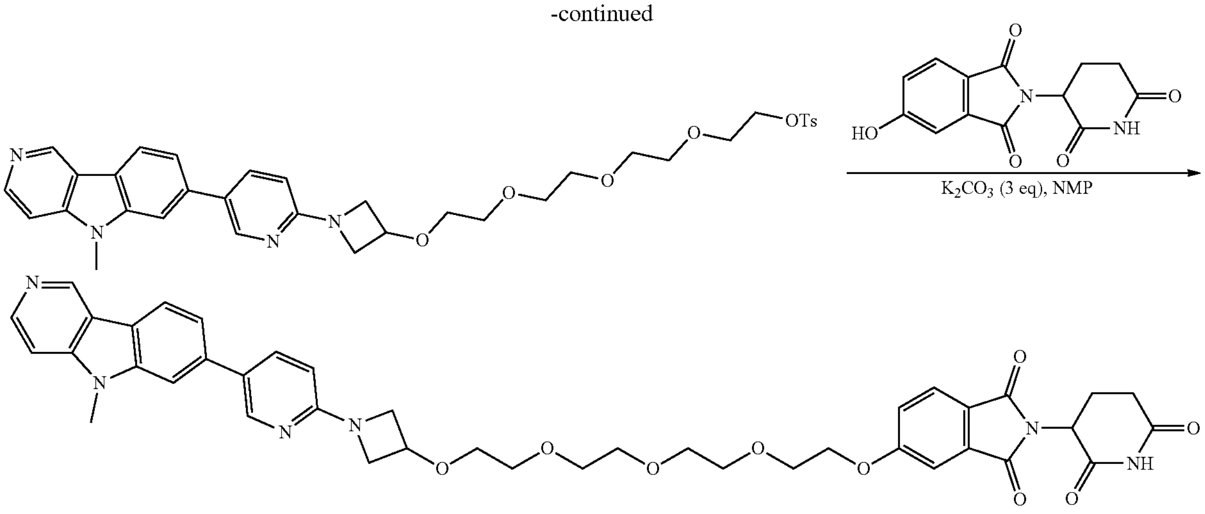
Compound 208
Synthetic Scheme for Exemplary Compound 209
2-(2,6-dioxopiperidin-3-yl)-5-(2-(2-((3-(((1r,3r)-3-((5-(5-methyl-5H-pyrido[4,3-b]indol-7-yl)pyridin-2-yl)oxy)cyclobutoxy)methyl)bicyclo[1.1.1]pentan-1-yl)methoxy)ethoxy)ethoxy)isoindoline-1,3-dione
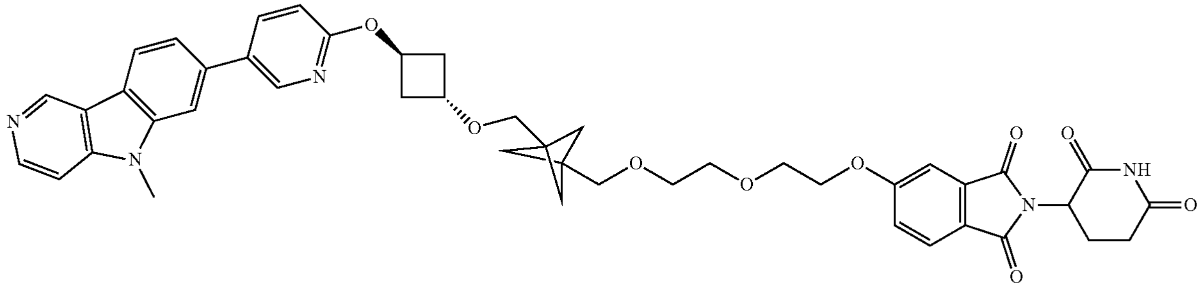 [SMILES: Cn1c2ccncc2c2ccc(-c3ccc(O[C@H]4C[C@H](OCC56CC(COCCOCCOc7ccc8c(c7)C(=O)N(C7CCC(=O)NC7=O)C8=O)(C5)C6)C4)nc3)cc21]
Prepared according to the scheme below and using procedures described above and common procedures known to those skilled in the art.
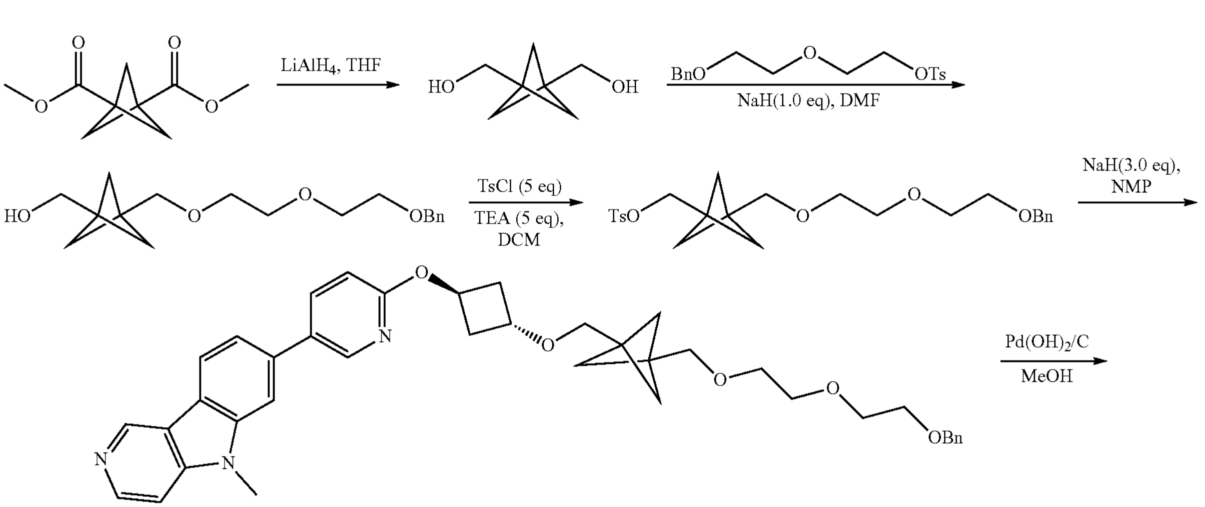

-continued
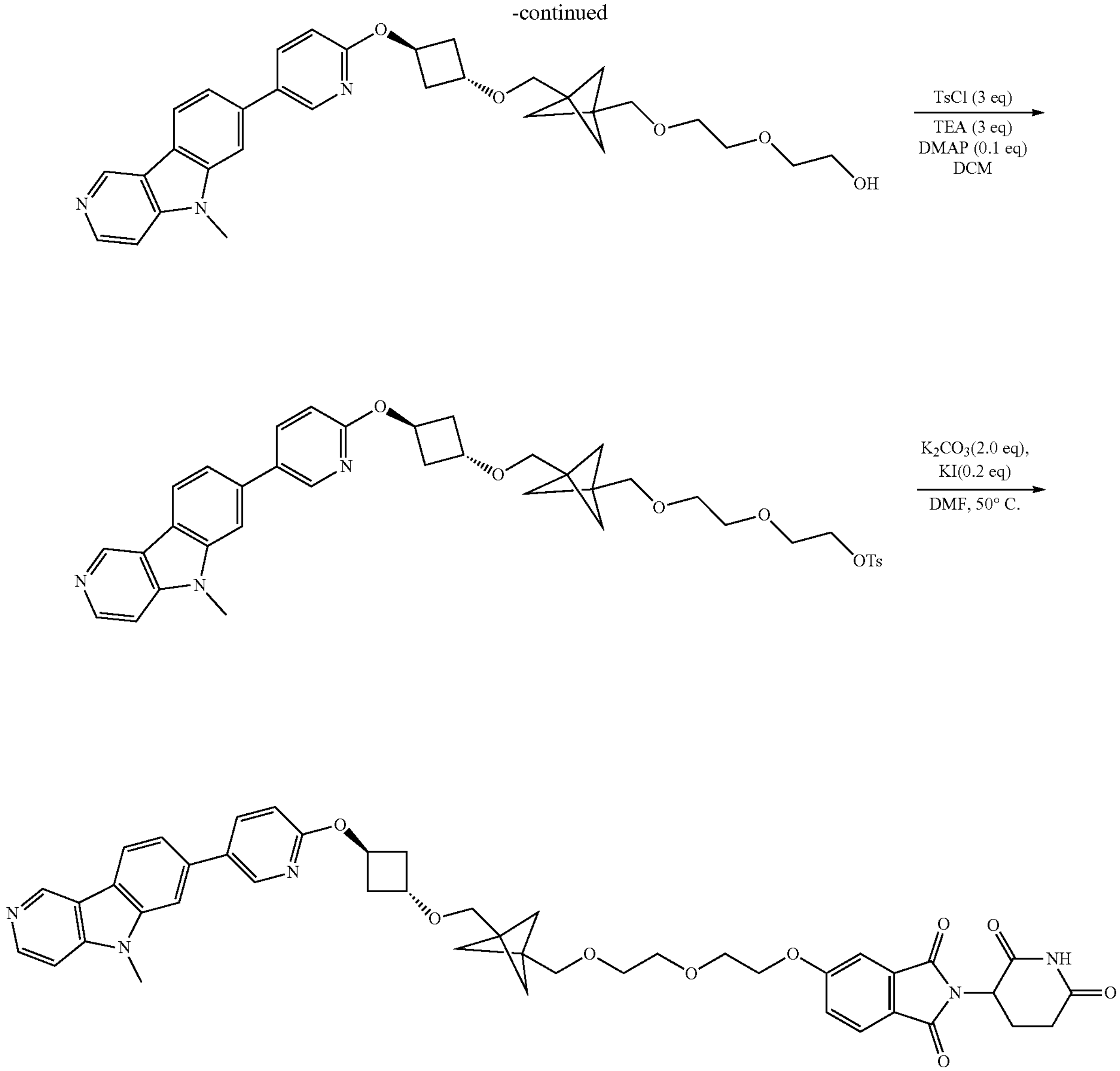
Compoud 209
Synthetic Scheme for Exemplary Compound 210
2-(2,6-dioxopiperidin-3-yl)-5-((15-(4-(5-methyl-5H-pyrido[4,3-b]indol-7-yl)piperazin-1-yl)-3,6,9,12-tetraoxapentadecyl)oxy)isoindoline-1,3-dione
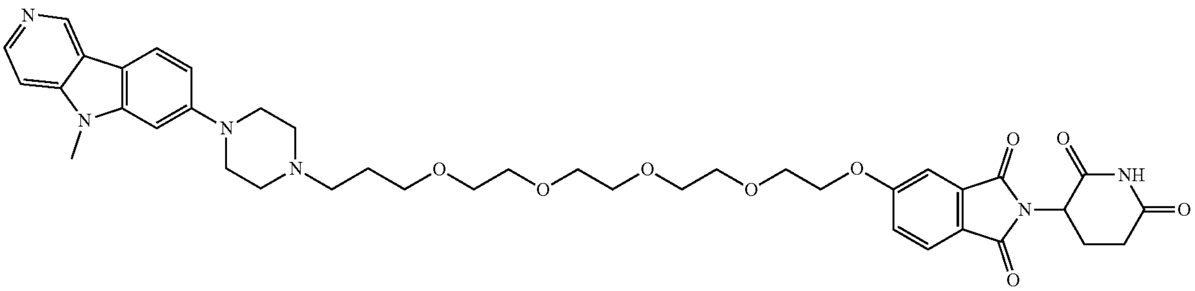 [SMILES: Cn1c2ccncc2c2ccc(N3CCN(CCCOCCOCCOCCOCCOc4ccc5c(c4)C(=O)N(C4CCC(=O)NC4=O)C5=O)CC3)cc21]

Step 1: tert-Butyl 4-(5-methylpyrido[4,3-b]indol-7-yl)piperazine-1-carboxylate

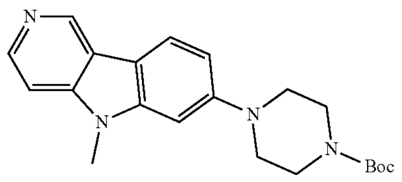 [SMILES: Cn1c2ccncc2c2ccc(N3CCN(C(=O)OC(C)(C)C)CC3)cc21]

To a solution of 7-bromo-5-methyl-pyrido[4,3-b]indole (1 g, 3.83 mmol, 1 eq) and tert-butyl piperazine-1-carboxylate (2.14 g, 11.49 mmol, 3 eq) in dioxane (20 mL) was added (±)-2,2'-bis(diphenylphosphino)-1,1'-binaphthalene (71 mg, 0.11 mmol, 0.03 eq), cesium carbonate (3.74 g, 11.49 mmol, 3 eq) and palladium(II) acetate (86 mg, 0.38 mmol, 0.1 eq) under nitrogen, then degassed under vacuum and purged with nitrogen three times. The mixture was stirred at 100° C. for 16 hours. The reaction mixture was concentrated to remove solvent and then extracted with ethyl acetate (80 mL×3). The combined organic layers were washed with brine 30 mL, dried over anhydrous sodium sulfate, filtered and concentrated under reduced pressure to give a residue. The residue was purified by silica gel column chromatography (petroleum ether/ethyl acetate=2/1 to dichloromethane/methanol=10/1) to give crude product, the crude product was purified by semi-preparative reverse phase HPLC (column: Phenomenex luna C18 250*50 mm*10 um; mobile phase: [water (0.225% FA)-ACN]; B %: 27%-52%, 30; 79% min). tert-Butyl 4-(5-methylpyrido[4,3-b]indol-7-yl)piperazine-1-carboxylate (700 mg, 1.91 mmol, 49% yield) was obtained as a white solid.

Step 2: 5-Methyl-7-piperazin-1-yl-pyrido[4,3-b]indole

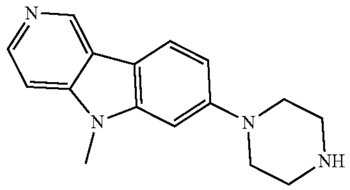 [SMILES: Cn1c2ccncc2c2ccc(N3CCNCC3)cc21]

To a solution of tert-butyl 4-(5-methylpyrido[4,3-b]indol-7-yl)piperazine-1-carboxylate (700 mg, 1.91 mmol, 1 eq) in dichloromethane (4 mL) was added hydrochloric acid/dioxane (4 M, 8 mL, 16.75 eq), then was stirred 25° C. for 1 h. TLC (dichloromethane/methanol=10/1) showed the starting material was consumed completely. The reaction mixture was concentrated to give a residue. 5-Methyl-7-piperazin-1-yl-pyrido[4,3-b]indole (580 mg, crude, HCl) was obtained as a white solid without any purification.

Step 3

To a solution of 5-methyl-7-piperazin-1-yl-pyrido[4,3-b]indole (366 mg, 1.21 mmol, 1 eq, HCl) and dimethyl 4-[2-[2-[2-[2-[3-(p-tolylsulfonyloxy)propoxy]ethoxy]ethoxy]ethoxy]ethoxy]benzene-1,2-dicarboxylate (725 mg, 1.21 mmol, 1 eq) [prepared according to the scheme below and using procedures described above and common procedures known to those skilled in the art]. in N,N-dimethylformamide (10 mL) was added N,N-diisopropylethylamine (626 mg, 4.84 mmol, 0.8 mL, 4 eq), then stirred at 80° C. for 16 h. The reaction mixture was concentrated to give a residue. The residue was purified by semi-preparative reverse phase HPLC (column: Phenomenex luna C18 250*50 mm*10 um; mobile phase: [water (0.225% FA)-ACN]; B %: 10%-40%, 30 min, 40% min). Dimethyl 4-[2-[2-[2-[2-[3-[4-(5-methylpyrido[4,3-b]indol-7-yl) piperazin-1-yl]propoxy]ethoxy]ethoxy]ethoxy]ethoxy]benzene-1,2-dicarboxylate (131 mg, 0.19 mmol, 15% yield, 100% purity) was obtained as a brown oil.

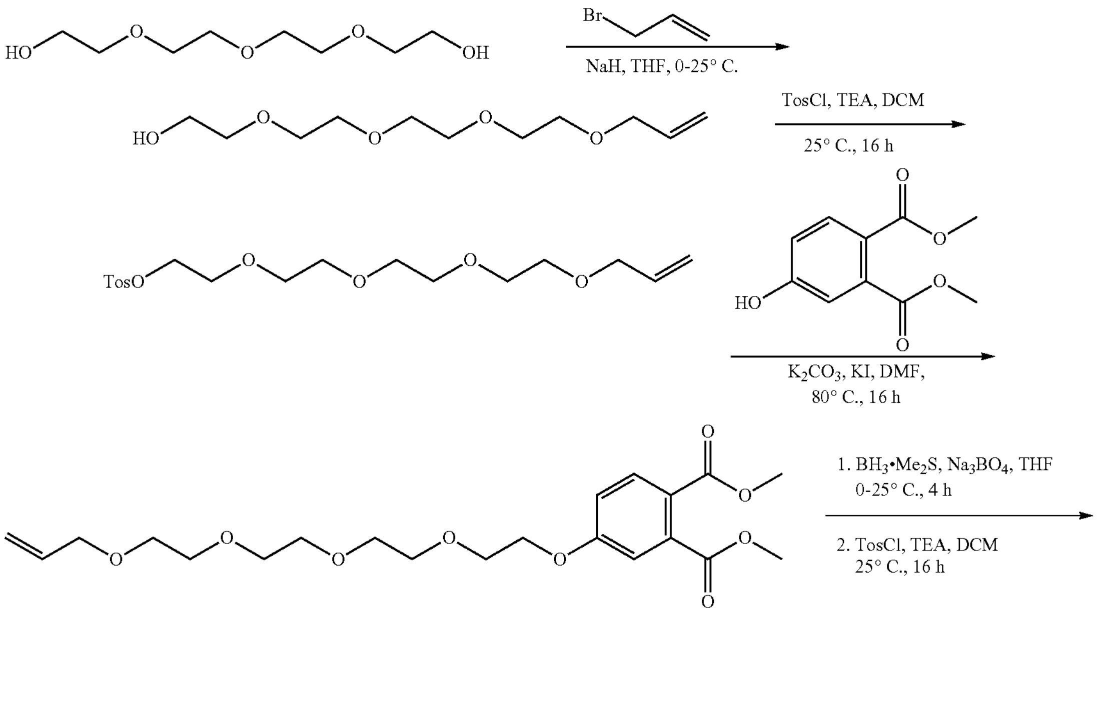

-continued

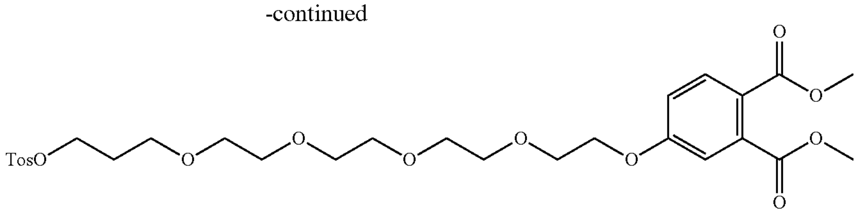

Step 4: 2-(2,6-dioxopiperidin-3-yl)-5-((15-(4-(5-methyl-5H-pyrido[4,3-b]indol-7-yl)piperazin-1-yl)-3,6,9,12-tetraoxapentadecyl)oxy)isoindoline-1,3-dione

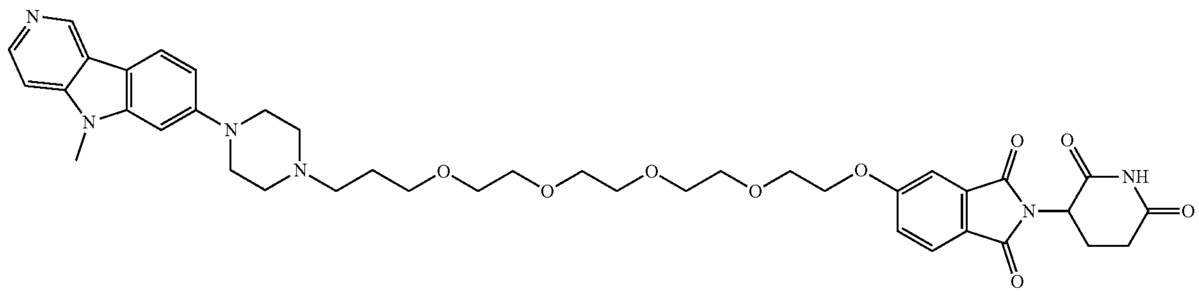 [SMILES: Cn1c2ccncc2c2ccc(N3CCN(CCCOCCOCCOCCOCCOc4ccc5c(c4)C(=O)N(C4CCC(=O)NC4=O)C5=O)CC3)cc21]

Dimethyl 4-[2-[2-[2-[2-[3-[4-(5-methylpyrido[4,3-b]indol-7-yl)piperazin-1-yl]propoxy]ethoxy]ethoxy]ethoxy]ethoxy]benzene-1,2-dicarboxylate (120 mg, 0.17 mmol, 1 eq), 3-aminopiperidine-2,6-dione (142 mg, 0.86 mmol, 5 eq, HCl) and lithium iodide (347 mg, 2.60 mmol, 15 eq) were taken up into a microwave tube in pyridine (4 mL). The sealed tube was heated at 120° C. for 2 h under microwave. The reaction mixture was concentrated to give a residue. The residue was purified by semi-preparative reverse phase HPLC (8-38% acetonitrile+0.225% formic acid in water, over 10 min), then the collected fraction was concentrated to remove most of the acetonitrile and then lyophilized to give crude product. Then the crude product was purified by prep-TLC (dichloromethane/methanol=10/1), 10 mL water and 0.2 mL 1M hydrochloric acid was added and then lyophilized to give the product. 2-(2,6-dioxopiperidin-3-yl)-5-((15-(4-(5-methyl-5H-pyrido[4,3-b]indol-7-yl)piperazin-1-yl)-3,6,9,12-tetraoxapentadecyl)oxy)isoindoline-1,3-dione dihydrochloride (20 mg, 0.02 mmol, 14% yield) was obtained as an off-white solid.

$^1$H NMR: (400 MHz, DMSO-d6) δ: 15.03 (br s, 1H), 11.18-10.95 (m, 2H), 9.55 (s, 1H), 8.64 (br d, J=6.5 Hz, 1H), 8.30 (br d, J=8.3 Hz, 1H), 8.09 (br d, J=6.9 Hz, 1H), 7.81 (br d, J=8.5 Hz, 1H), 7.48-7.23 (m, 4H), 5.11 (br dd, J=5.0, 12.7 Hz, 1H), 4.30 (br s, 2H), 4.11 (br d, J=13.1 Hz, 2H), 4.02 (s, 3H), 3.78 (br s, 2H), 3.70-3.48 (m, 18H), 3.19 (br s, 3H), 2.96-2.82 (m, 1H), 2.62-2.55 (m, 3H), 2.04 (br s, 3H). $(M+H)^+$ 757.6.

Synthetic Scheme for Exemplary Compound 211

2-(2,6-dioxopiperidin-3-yl)-5-(3-(3-(2-(6-((5-(5-methyl-5H-pyrido[4,3-b]indol-7-yl)pyridin-2-yl)oxy)-2-azaspiro[3.3]heptan-2-yl)ethoxy)propoxy)azetidin-1-yl)isoindoline-1,3-dione

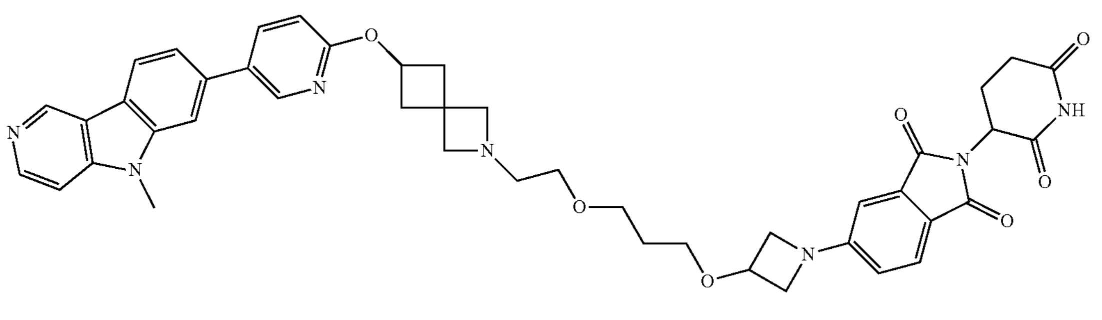 [SMILES: Cn1c2ccncc2c2ccc(-c3ccc(OC4CC5(C4)CN(CCOCCCOC4CN(c6ccc7c(c6)C(=O)N(C6CCC(=O)NC6=O)C7=O)C4)C5)nc3)cc21]

Prepared according to the schemes below and using procedures described above and common procedures known to those skilled in the art.
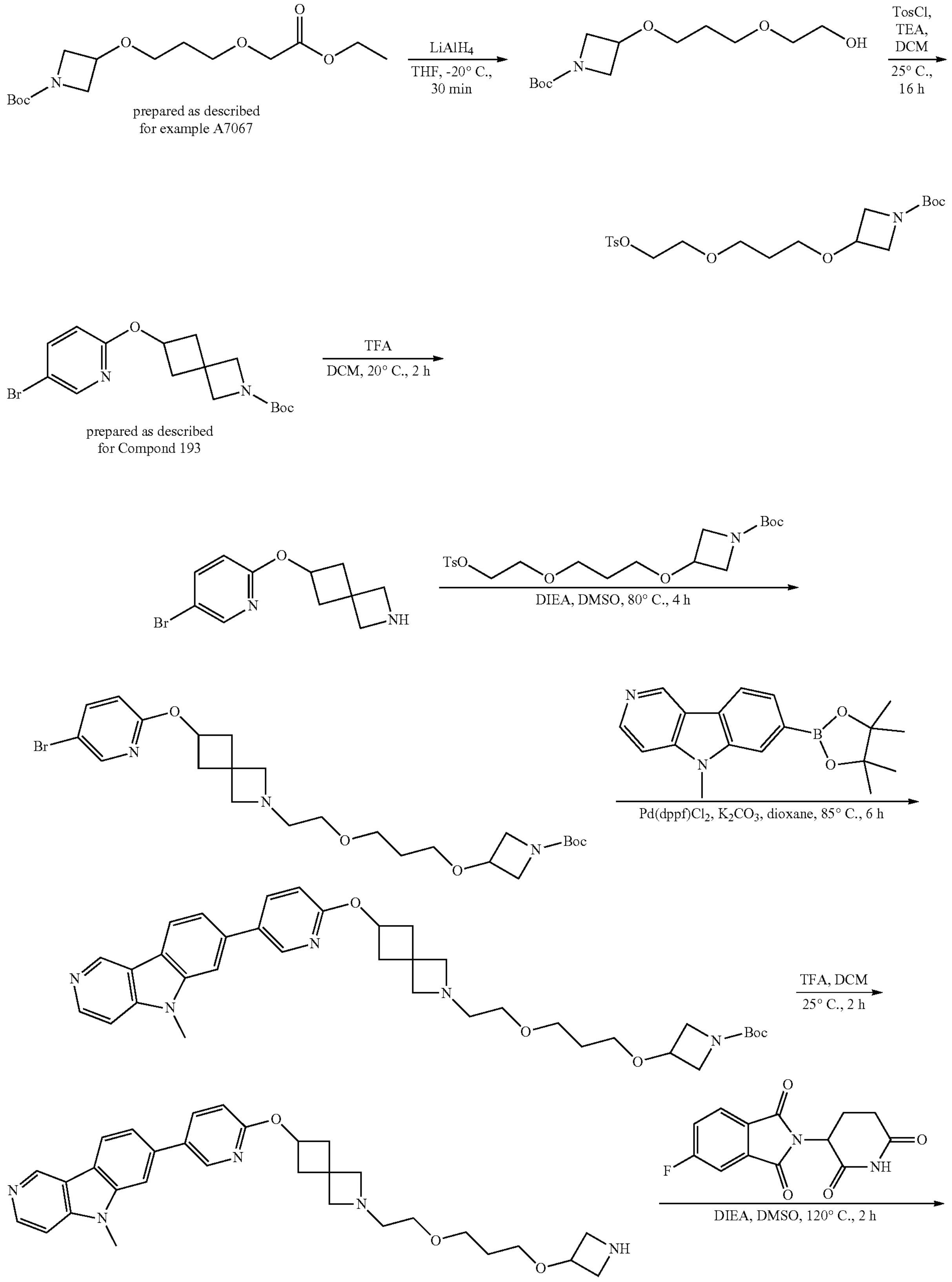

-continued

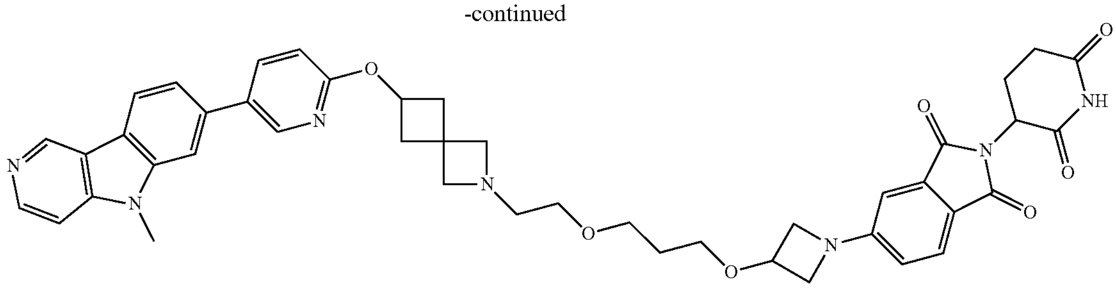

Compound 211

Synthetic Scheme for Exemplary Compound 212

2-(2,6-dioxopiperidin-3-yl)-5-(3-(2-((4-((1r,3r)-3-((5-(5-methyl-5H-pyrido[4,3-b]indol-7-yl)pyridin-2-yl)oxy)cyclobutoxy)but-2-yn-1-yl)oxy)ethoxy)azetidin-1-yl)isoindoline-1,3-dione

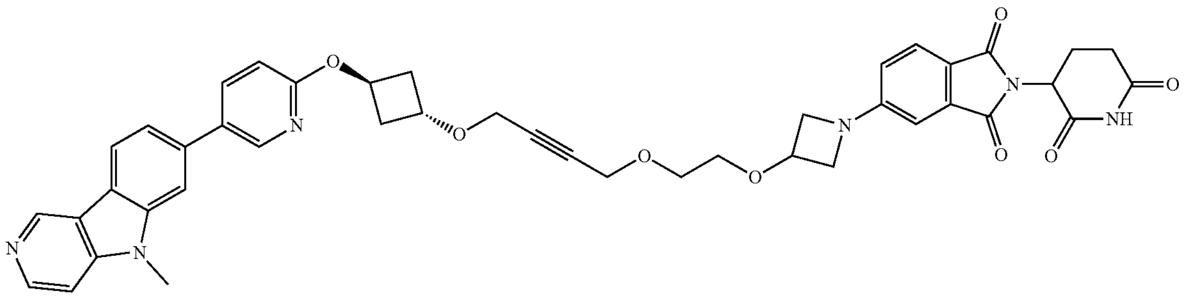 [SMILES: Cn1c2ccncc2c2ccc(-c3ccc(O[C@H]4C[C@H](OCC#CCOCCOC5CN(c6ccc7c(c6)C(=O)N(C6CCC(=O)NC6=O)C7=O)C5)C4)nc3)cc21]

Step 1: tert-Butyl 3-(2-ethoxy-2-oxo-ethoxy)azetidine-1-carboxylate

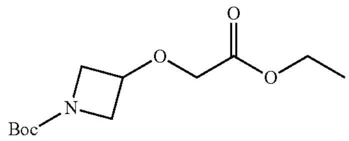 [SMILES: CCOC(=O)COC1CN(C(=O)OC(C)(C)C)C1]

To a mixture of tert-butyl 3-hydroxyazetidine-1-carboxylate (3 g, 17.32 mmol, 1 eq) and diacetoxyrhodium (766 mg, 1.73 mmol, 0.1 eq) in dichloromethane (50 mL) was added ethyl 2-diazoacetate (11.86 g, 103.92 mmol, 6 eq) dropwise at 0° C. Then the reaction mixture was stirred at 25° C. for 4 hours. TLC showed the starting material was not consumed. Then the reaction was stirred at 25° C. for another 16 hours. To the reaction solution was added acetic acid. Then the reaction was extracted with dichloromethane (30 mL×3), and concentrated under vacuum to get the residue. The residue was purified by silica gel column chromatography (Petroleum ether/Ethyl acetate=30/1 to 8:1) to get the product. tert-Butyl 3-(2-ethoxy-2-oxo-ethoxy)azetidine-1-carboxylate (2.24 g, 8.64 mmol, 50% yield) was obtained as a light yellow oil.

Step 2: tert-Butyl 3-(2-hydroxyethoxy)azetidine-1-carboxylate

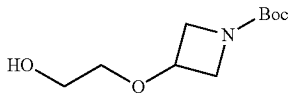 [SMILES: CC(C)(C)OC(=O)N1CC(OCCO)C1]

To a suspension of lithium aluminum hydride (229.51 mg, 6.05 mmol, 0.7 eq) in tetrahydrofuran (30 mL) was added a solution of tert-butyl 3-(2-ethoxy-2-oxo-ethoxy) azetidine-1-carboxylate (2.24 g, 8.64 mmol, 1 eq) in tetrahydrofuran (10 mL) at −20° C. The reaction mixture was stirred at 0° C. for 0.5 hour. The reaction solution was added water (20 mL), the organic layer was extracted with ethyl acetate (40 mL×3). Then the combined organic phase was dried over anhydrous sodium sulfate, filtered and concentrated under reduced pressure to give a residue. The residue was purified silica gel column chromatography (Petroleum ether/Ethyl acetate=200/1 to 1:1) to get the product. tert-Butyl 3-(2-hydroxyethoxy)azetidine-1-carboxylate (828 mg, 3.81 mmol, 44% yield) was obtained as a light yellow oil.

Step 3: 4-[(4-methoxyphenyl)methoxy]but-2-yn-1-ol

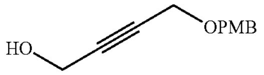

To a solution of but-2-yne-1,4-diol (5 g, 58.08 mmol, 1 eq) N,N-in dimethyl formamide (50 mL) was added sodium hydride (2.32 g, 58.08 mmol, 60% in mineral oil, 1 eq) at 0° C. The mixture was stirred at 0° C. for 0.5 hour. Then methoxybenzylchloride (9.55 g, 60.98 mmol, 8.3 mL, 1.05 eq) was added into the mixture at 0° C. slowly, the mixture was stirred at 25° C. for 4 hours. The reaction was added water (40 mL). The solution was extracted with ethyl acetate (40 mL×3). Then the combined organic phase was washed with brine (20 mL×2), dried with anhydrous sodium sulfate, filtered and concentrated under vacuum to get the residue. The residue was purified by silica gel column chromatography (Petroleum ether/Ethyl acetate=30/1 to 3:1) to get the product. 4-[(4-methoxyphenyl)methoxy]but-2-yn-1-ol (2.64 g, 12.80 mmol, 22% yield) was obtained as a light yellow oil.

Step 4: 1-(4-bromobut-2-ynoxymethyl)-4-methoxybenzene

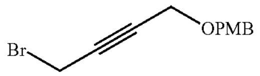

To a solution of 4-[(4-methoxyphenyl)methoxy]but-2-yn-1-ol (1 g, 4.85 mmol, 1 eq) and perbromomethane (1.61 g, 4.85 mmol, 1 eq) in dichloromethane (10 mL) was added triphenylphosphine (1.40 g, 5.33 mmol, 1.1 eq) at 0° C. The solution was stirred at 25° C. for 16 hours. TLC showed the starting material was consumed completely. The reaction solution was concentrated under vacuum to get the residue. The residue was purified by silica gel column chromatography (Petroleum ether/Ethyl acetate=1/0 to 80:1) to get the product. 1-(4-bromobut-2-ynoxymethyl)-4-methoxy-benzene (1 g, 3.72 mmol, 77% yield) was obtained as a light yellow oil.

The final compound, 2-(2,6-dioxopiperidin-3-yl)-5-(3-(2-((4-((1r,3r)-3-((5-(5-methyl-5H-pyrido[4,3-b]indol-7-yl)pyridin-2-yl)oxy)cyclobutoxy)but-2-yn-1-yl)oxy)ethoxy)azetidin-1-yl)isoindoline-1,3-dione, was prepared according to the schemes below and using procedures described above and common procedures known to those skilled in the art.

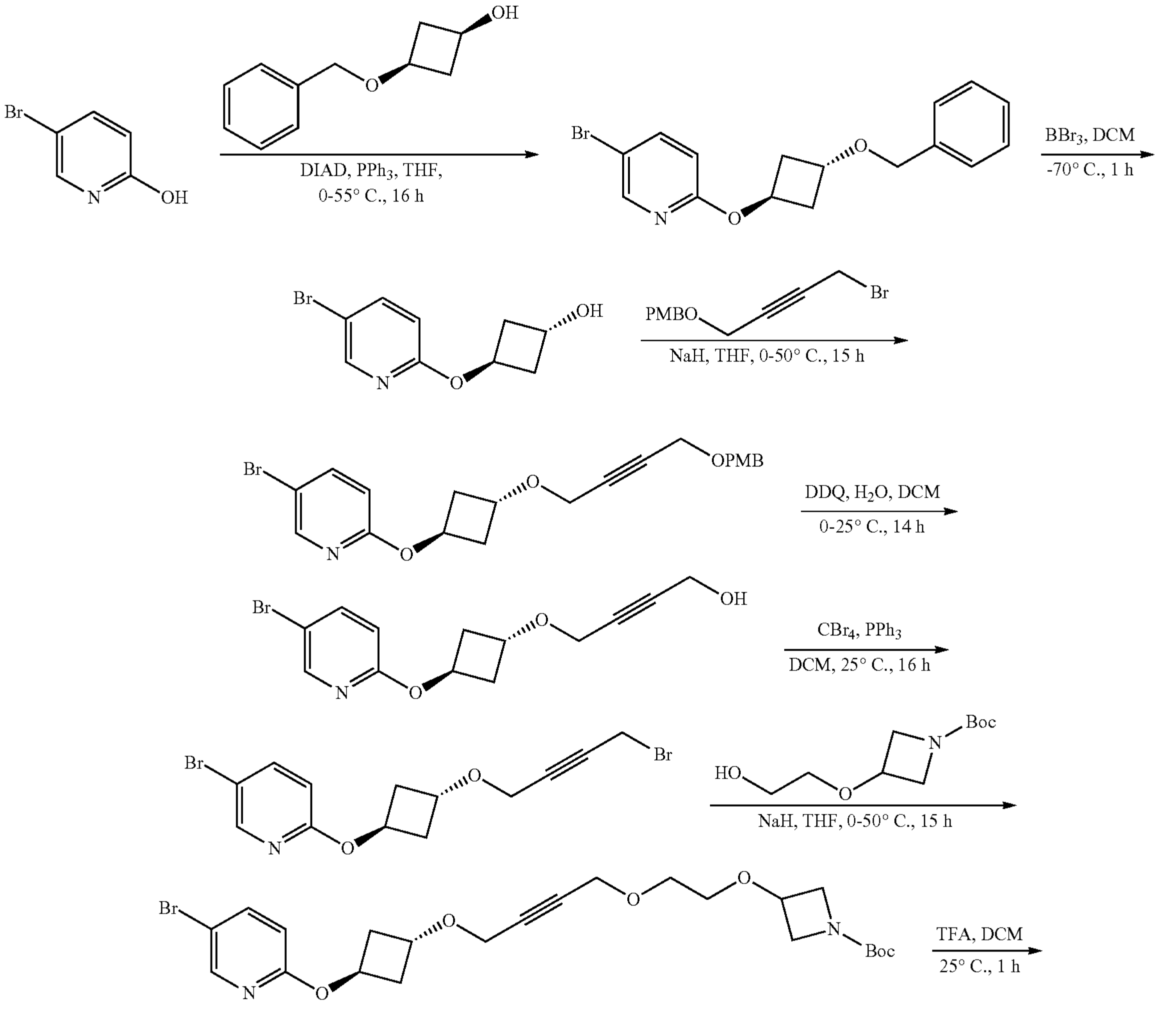

-continued
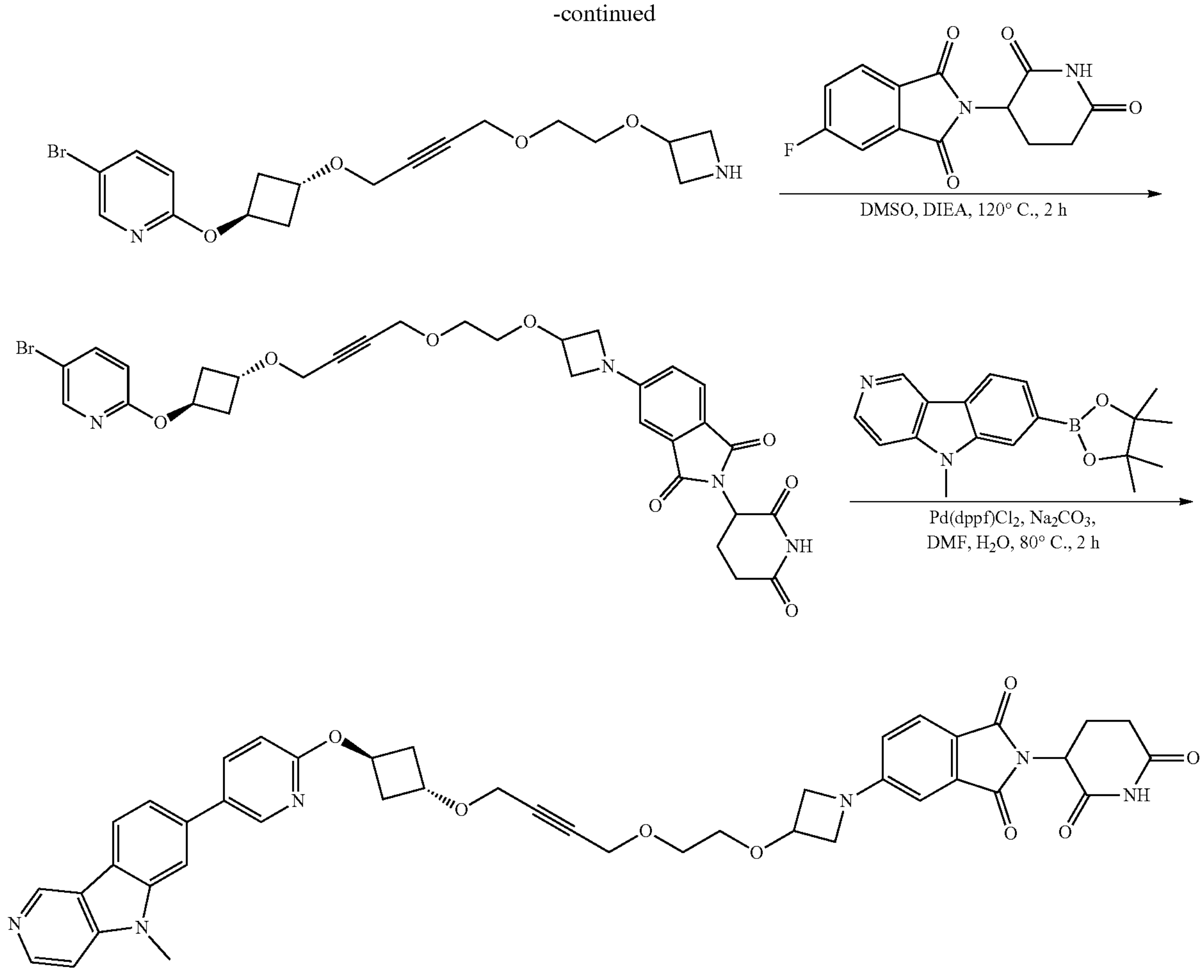
Compound 212
Synthetic Scheme for Exemplary Compound 213
2-(2,6-dioxopiperidin-3-yl)-5-(6-(2-(2-((1r,3r)-3-((5-(5-methyl-5H-pyrido[4,3-b]indol-7-yl)pyridin-2-yl)oxy)cyclobutoxy)ethoxy)ethoxy)-2-azaspiro[3.3]heptan-2-yl)isoindoline-1,3-dione
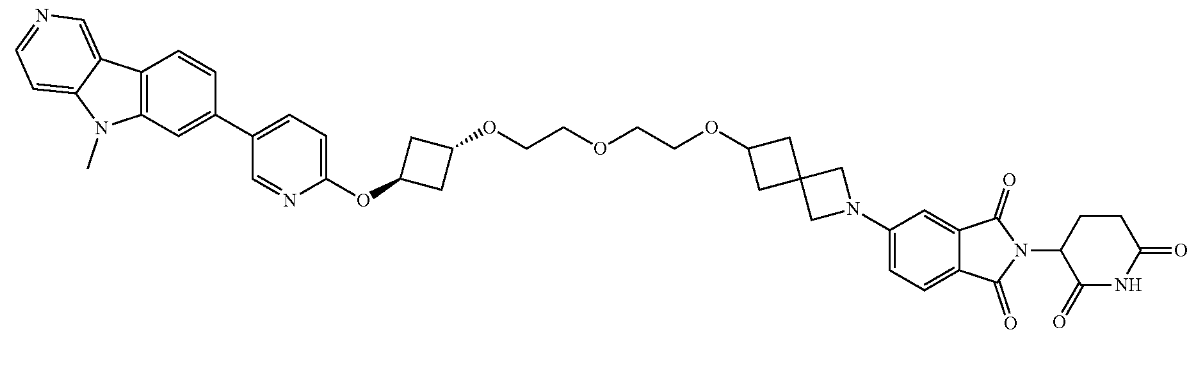 [SMILES: Cn1c2ccncc2c2ccc(-c3ccc(O[C@H]4C[C@H](OCCOCCOC5CC6(C5)CN(c5ccc7c(c5)C(=O)N(C5CCC(=O)NC5=O)C7=O)C6)C4)nc3)cc21]
Prepared according to the schemes below and using procedures described above and common procedures known to those skilled in the art.

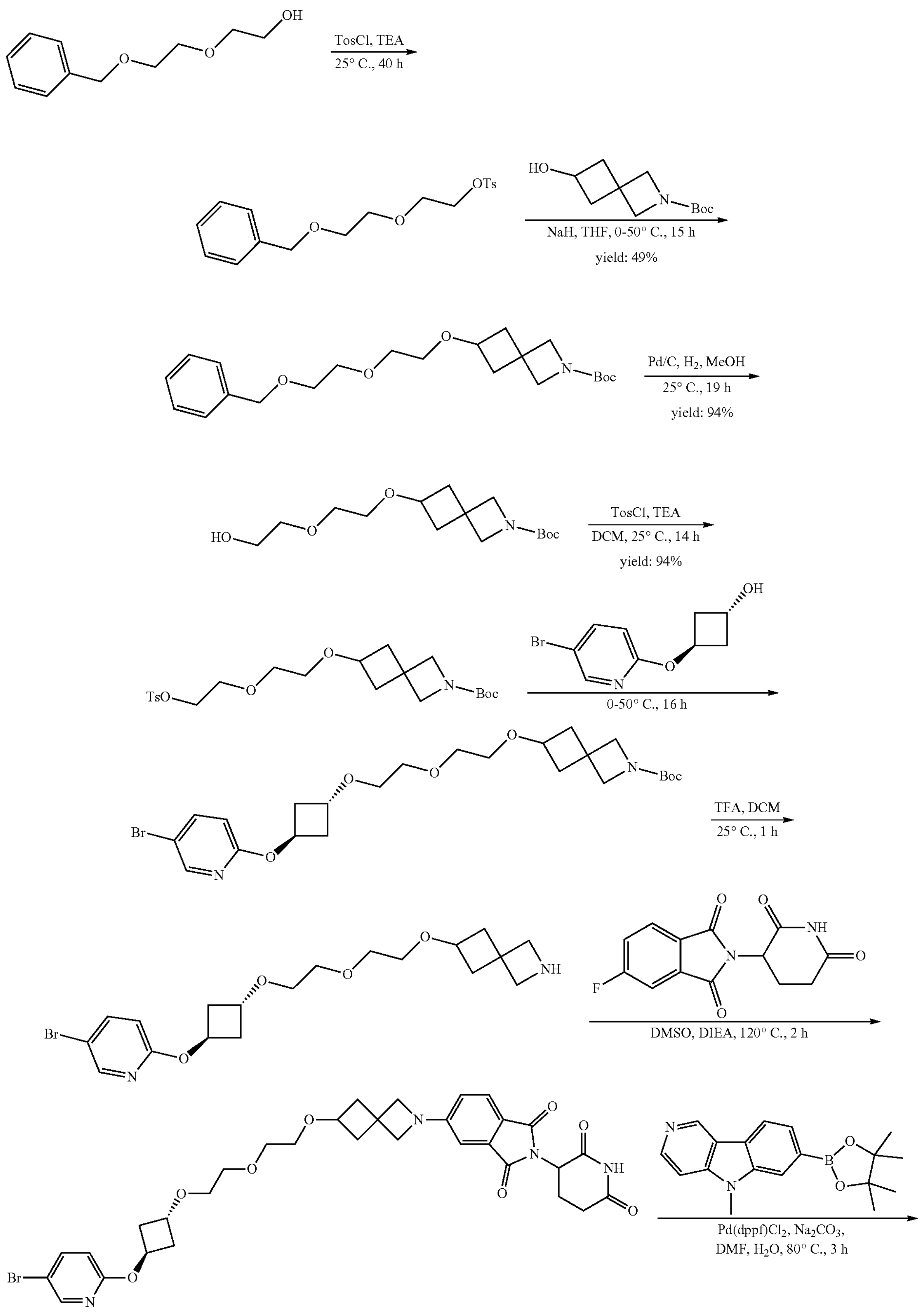
TosCl, TEA
25° C., 40 h
NaH, THF, 0-50° C., 15 h
yield: 49%
Pd/C, $H_2$, MeOH
25° C., 19 h
yield: 94%
TosCl, TEA
DCM, 25° C., 14 h
yield: 94%
0-50° C., 16 h
TFA, DCM
25° C., 1 h
DMSO, DIEA, 120° C., 2 h
Pd(dppf)$Cl_2$, $Na_2CO_3$,
DMF, $H_2O$, 80° C., 3 h -continued

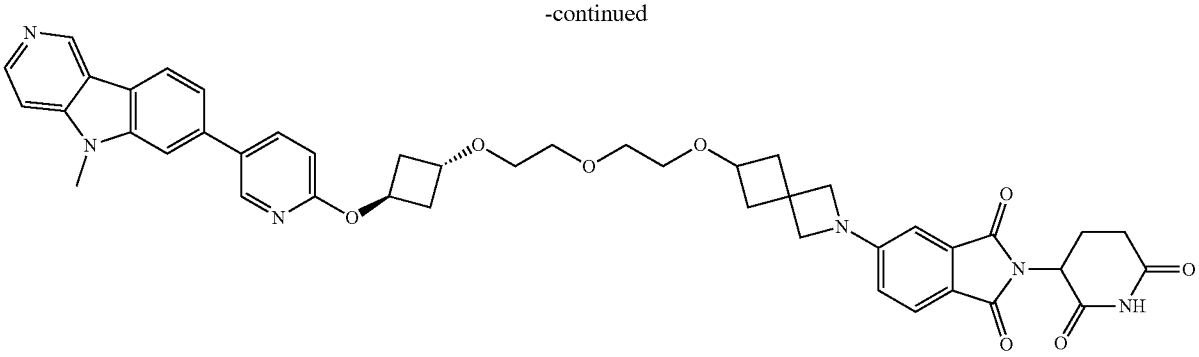

Compound 213

Additional examples are being contemplated in the context of the present disclosure and are detailed below. They can be prepared as described in the accompanying schemes, or by using procedures analogous to those described above (as indicated).

Synthetic Scheme for Compounds 215 and 217

Can be prepared according to the schemes below and using procedures described above and common procedures known to those skilled in the art.

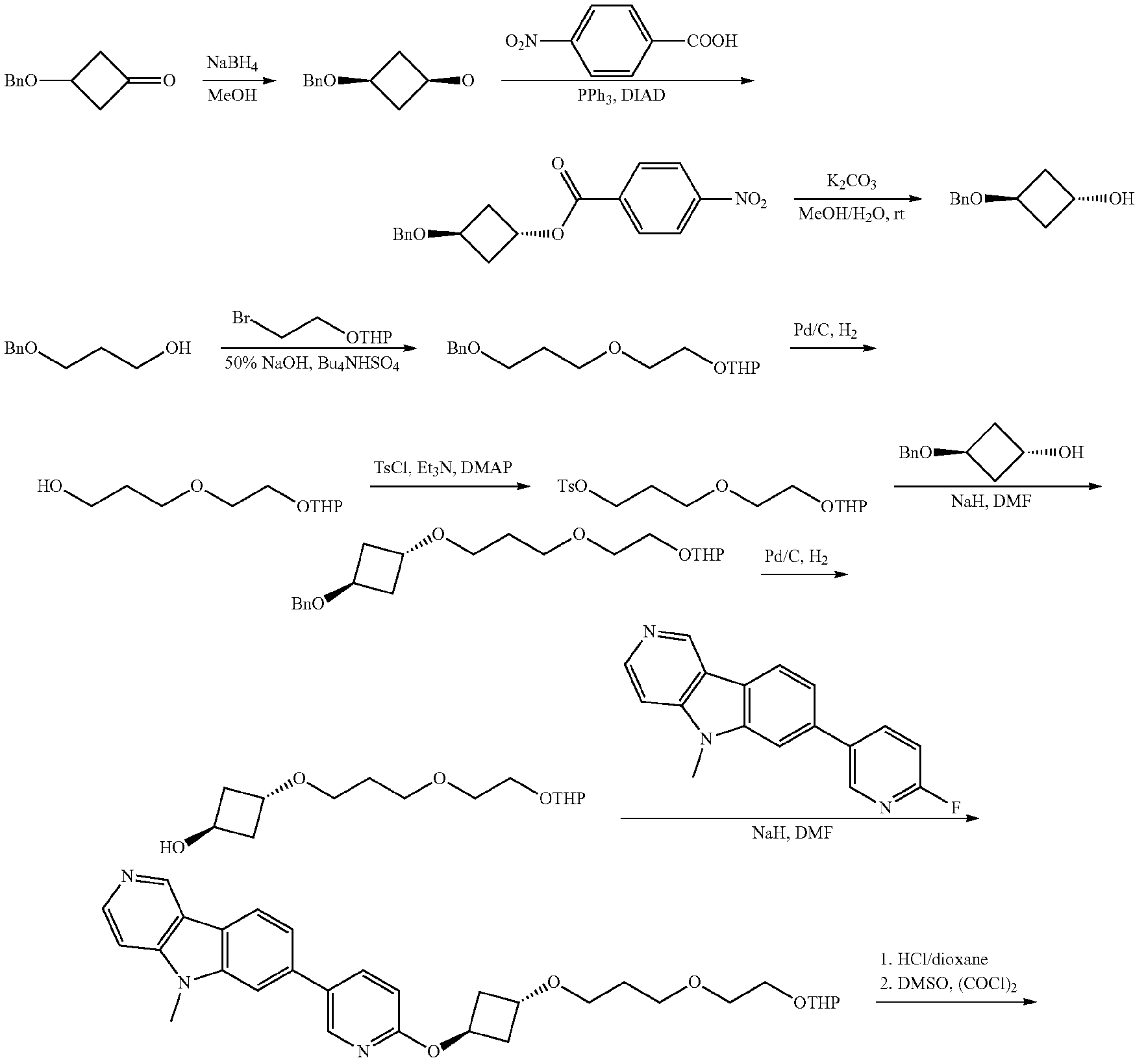

-continued

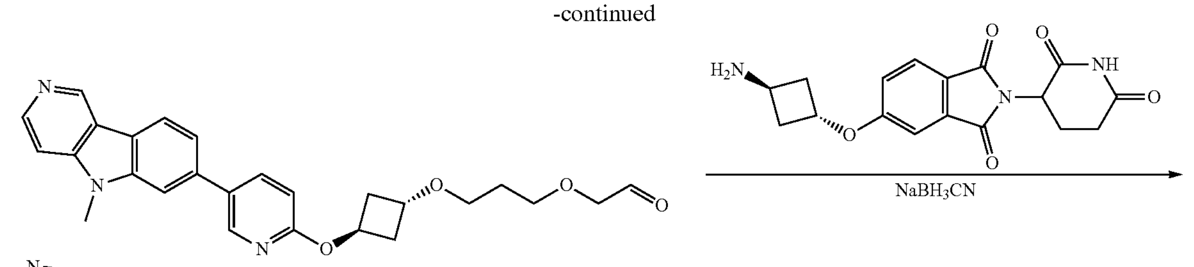

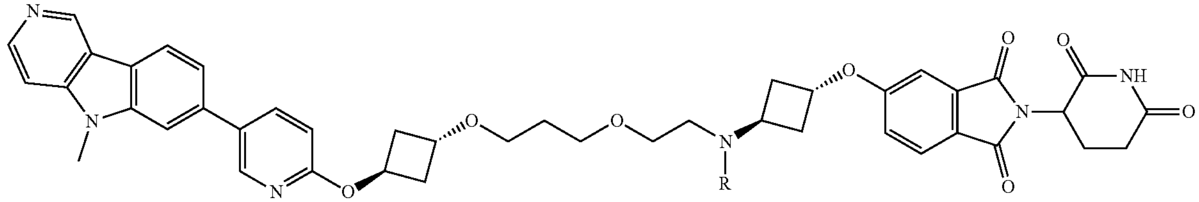

Compound 215 (R = H) $CH_3COCH_3$ / $NaBH_3CN$ Compound 217 (R =  )

Alternatively, one skilled in the art will recognize that different sequence of steps and/or different protecting groups can be used in the assembly of the linkers of the examples described below. In addition, different sequence of attaching the linker to the PTM and ULM can be used for different examples, and sometimes different sequence of linker assembly and PTM/ULM attachment can be used interchangeably for a given example (i.e., attach PTM first, then ULM, or attach ULM first, then PTM). For example, linker for Compound 216 can be assembled as shown in the scheme below.

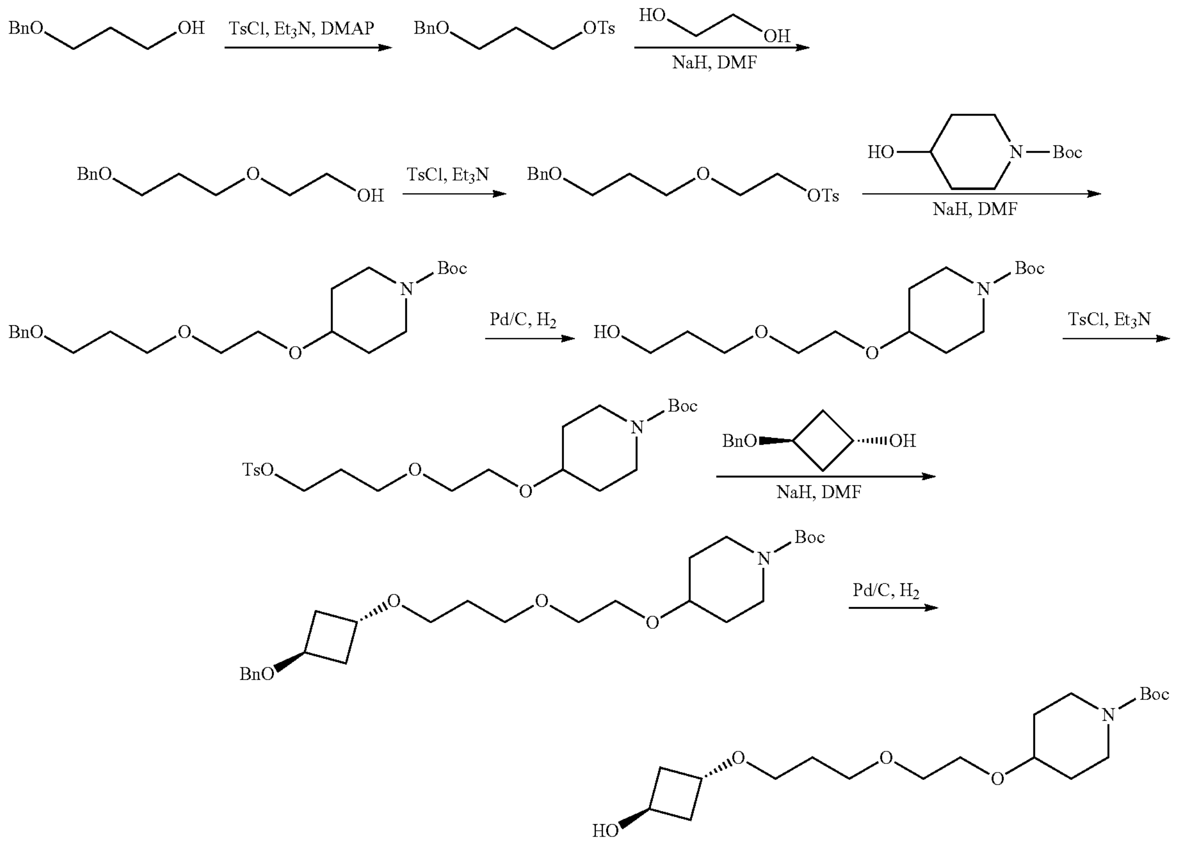

Compound 216 can then be synthesized according to the scheme below.

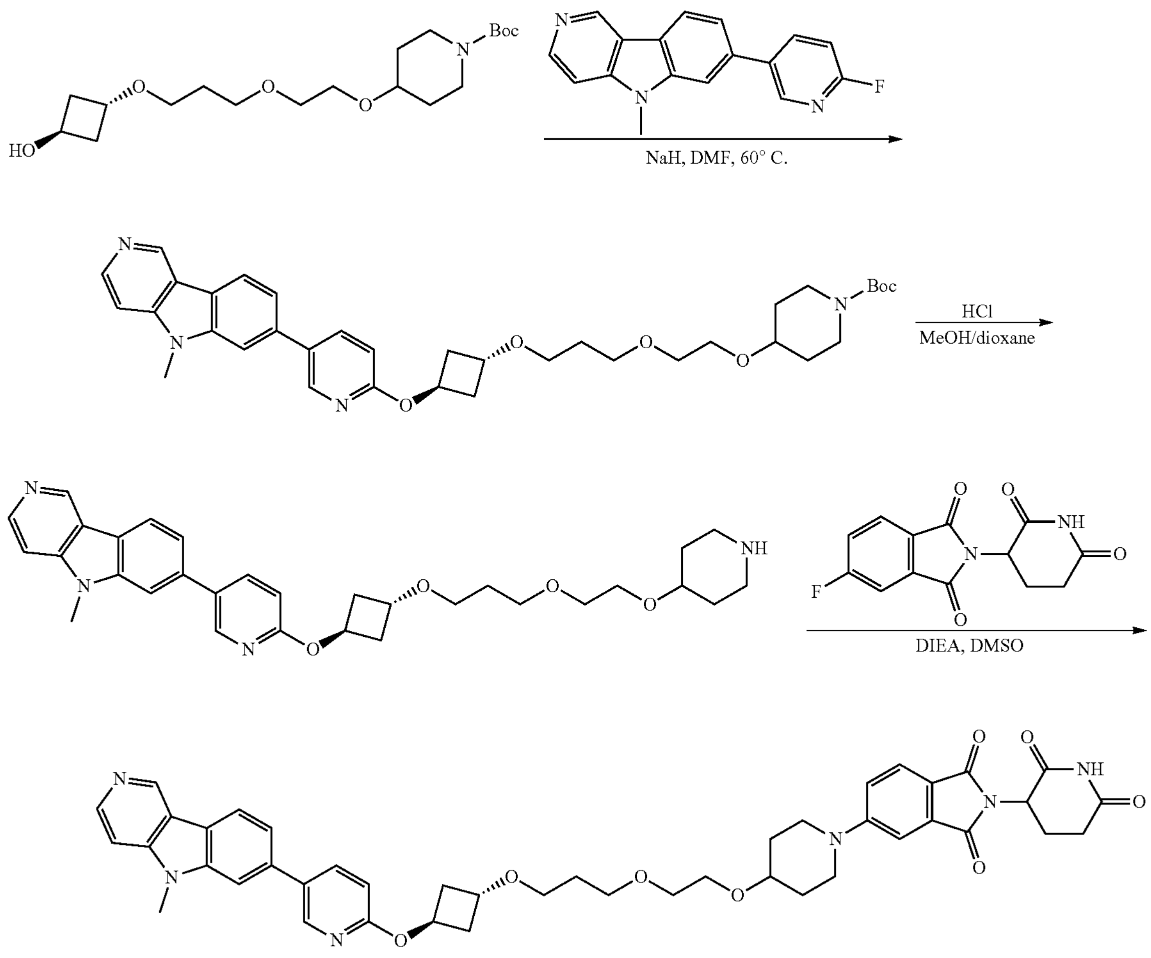
Compound 216
Alternatively, Compound 216 can be synthesized using a different sequence of PTM and ULM attachment according to the scheme below.
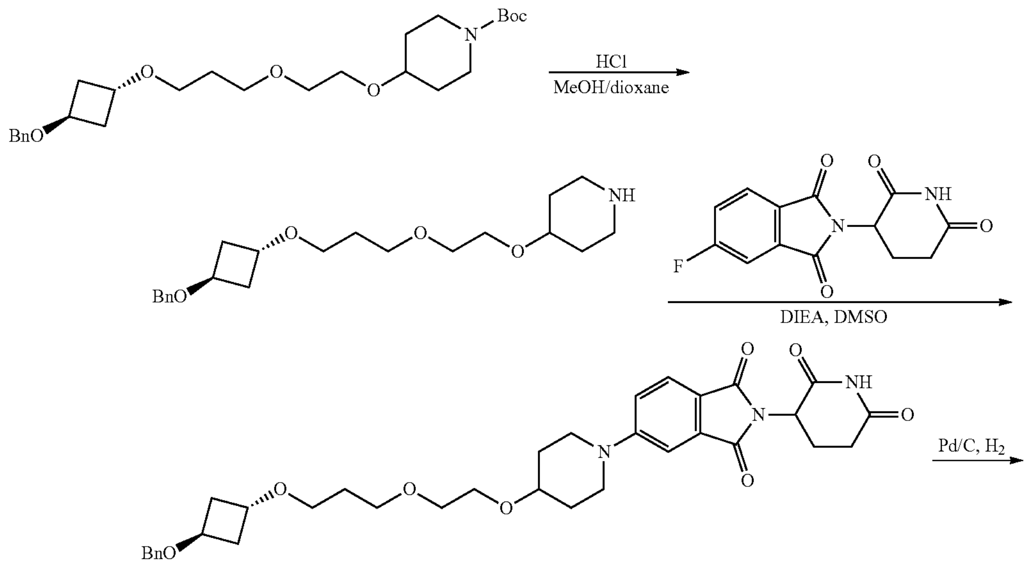

-continued
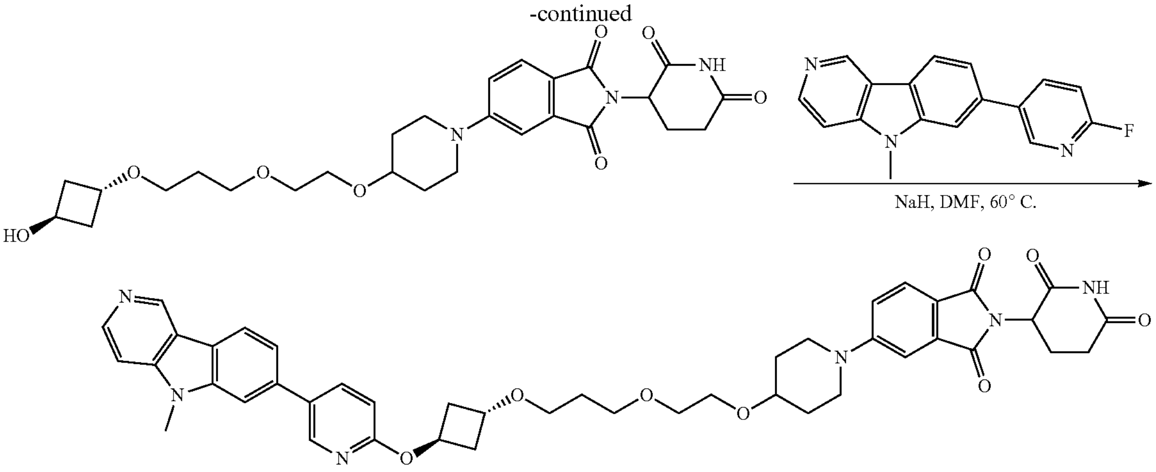
Compound 216
Synthetic Scheme for Exemplary Compound 4
4-((14-((5-(5H-pyrido[4,3-b]indol-7-yl)pyridin-2-yl)oxy)-3,6,9,12-tetraoxatetradecyl)amino)-2-(2,6-dioxopiperidin-3-yl)isoindoline-1,3-dione
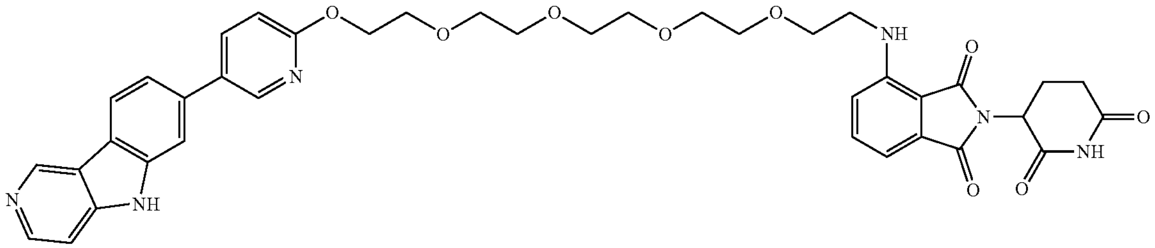 [SMILES: O=C1CCC(N2C(=O)c3cccc(NCCOCCOCCOCCOCCOc4ccc(-c5ccc6c(c5)[nH]c5ccncc56)cn4)c3C2=O)C(=O)N1]
Prepared according to the scheme below using procedures described above and common procedures known to those skilled in the art.
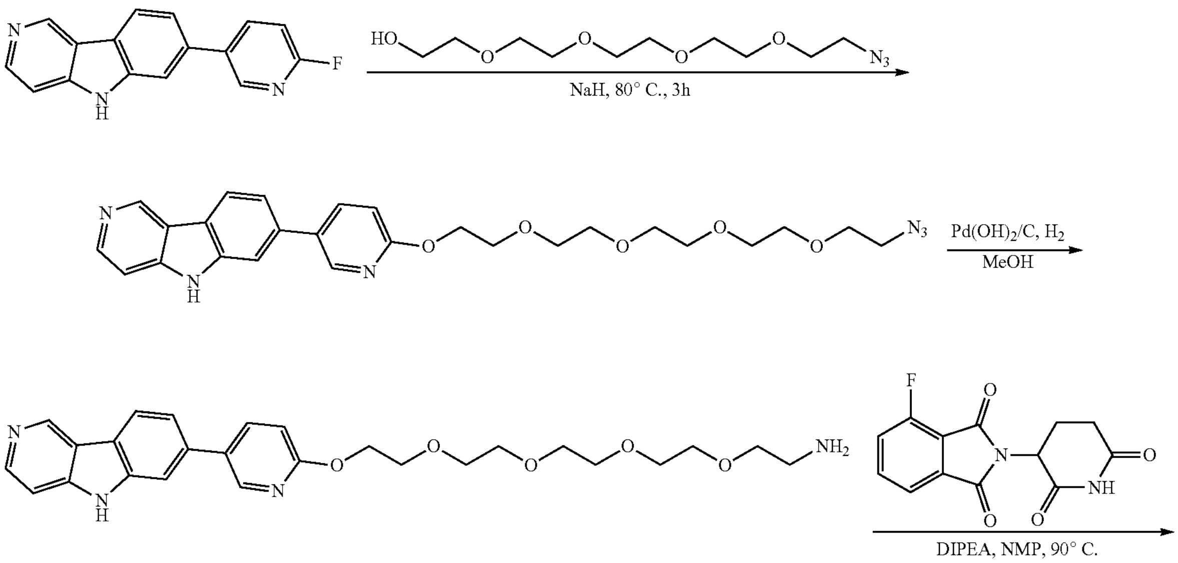

-continued

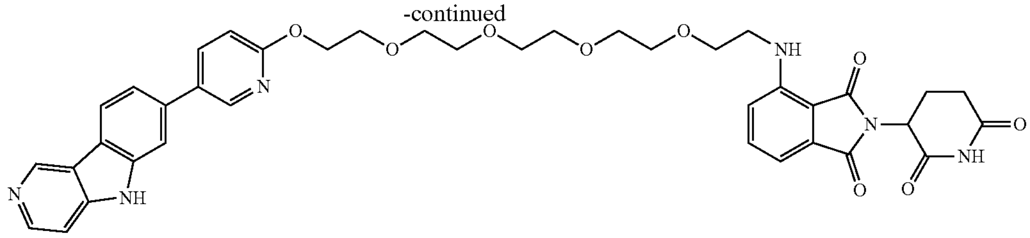

Compound 4

$^1H$ NMR (400 MHz, $CDCl_3$): δ 9.30 (s, 1H), 8.90 (br, 1H), 8.52 (d, J=5.6 Hz, 1H), 8.42 (d, J=2.8 Hz, 1H), 8.14 (d, J=8.0 Hz, 1H), 7.49 (dd, J=2.4, 8.8 Hz, 1H), 7.57 (s, 1H), 7.26-7.46 (m, 3H), 6.97 (d, J=7.2 Hz, 1H), 6.81-6.87 (m, 2H), 6.35-6.46 (m, 1H), 4.89-4.98 (m, 1H), 4.54 (t, J=4.8 Hz, 2H), 3.90 (t, J=4.8 Hz, 2H), 3.61-3-74 (m, 15H), 3.37-3.81 (m, 2H), 2.65-2.92 (m, 3H), 2.07-2.15 (m, 1H).

Using procedures described for Compound 4 the following were prepared: Compound 2, Compound 3, and Compound 48.

Synthetic Scheme for Exemplary Compound 7

(2S,4R)-1-((S)-14-(4-(benzo[4,5]imidazo[1,2-a]pyrimidin-2-yl)piperazin-1-yl)-2-(tert-butyl)-4-oxo-6,9,12-trioxa-3-azatetradecanoyl)-4-hydroxy-N-(4-(4-methylthiazol-5-yl)benzyl)pyrrolidine-2-carboxamide

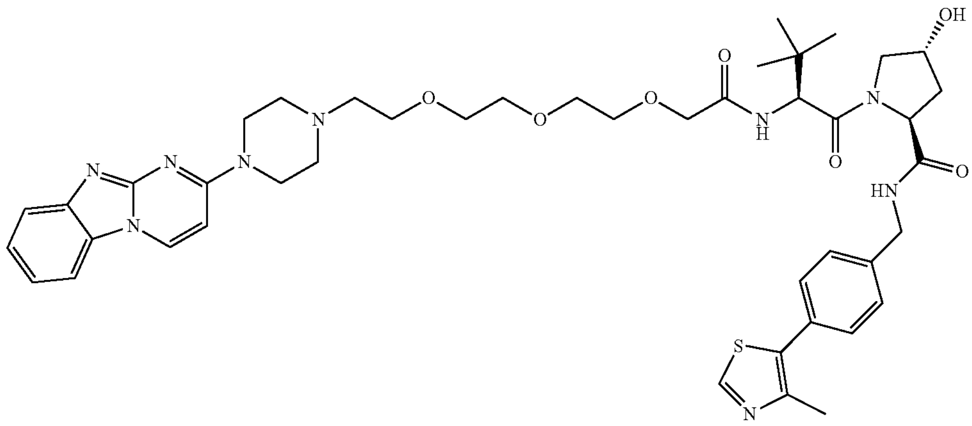 [SMILES: Cc1ncsc1-c1ccc(CNC(=O)[C@@H]2C[C@@H](O)CN2C(=O)[C@@H](NC(=O)COCCOCCOCCN2CCN(c3ccn4c(n3)nc3ccccc34)CC2)C(C)(C)C)cc1]

Prepared according to the scheme below using procedures described above and common procedures known to those skilled in the art.

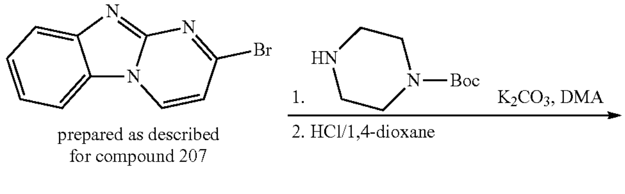

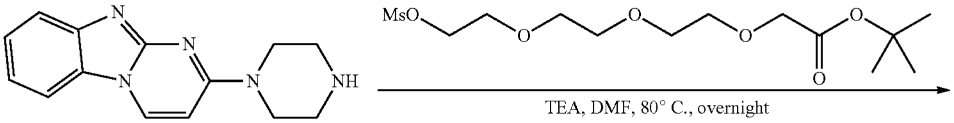

-continued

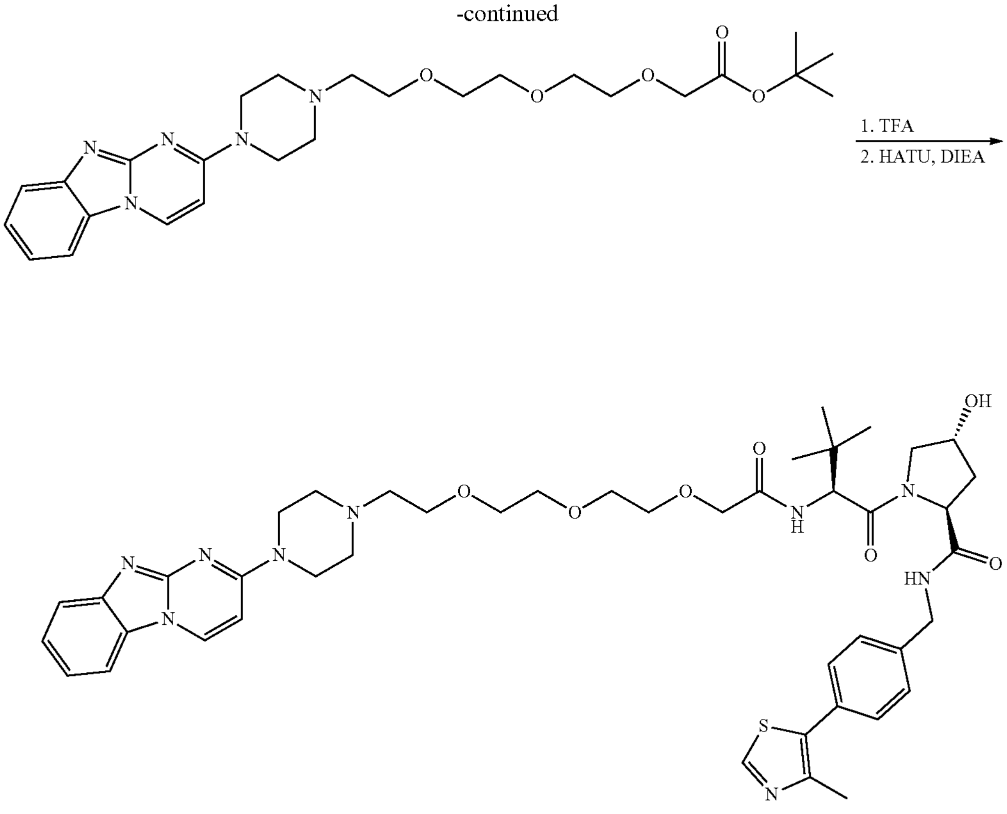

Compound 7

$^1$H NMR (400 MHz, MeOD): δ 8.85 (s, 1H), 8.71 (d, J=7.6 Hz, 1H), 7.70 (d, J=8.0 Hz, 1H), 7.55 (d, J=8.0 Hz, 1H), 7.34-7.42 (m, 5H), 7.22-7.23 (m, 1H), 6.76 (d, J=7.6 Hz, 1H), 4.68 (s, 1H), 4.47-4.57 (m, 4H), 4.30-4.39 (m, 1H), 4.05 (s, 3H), 3.56-4.87 (m, 23H), 2.64 (s, 4H), 2.45 (s, 3H), 2.19 (br, 1H), 2.04 (br, 1H), 1.03 (s, 9H).

Using procedures described for Compound 7 the following were prepared: Compound 11, Compound 12, Compound 15, Compound 16, Compound 19, Compound 20, Compound 23, Compound 25, Compound 26.

Synthetic Scheme for Exemplary Compound 10

(2S,4R)-1-((S)-14-(4-(benzo[4,5]imidazo[1,2-a]pyrimidin-2-yl)piperazin-1-yl)-2-(tert-butyl)-4,14-dioxo-6,9,12-trioxa-3-azatetradecanoyl)-4-hydroxy-N-((S)-1-(4-(4-methylthiazol-5-yl)phenyl)ethyl) pyrrolidine-2-carboxamide

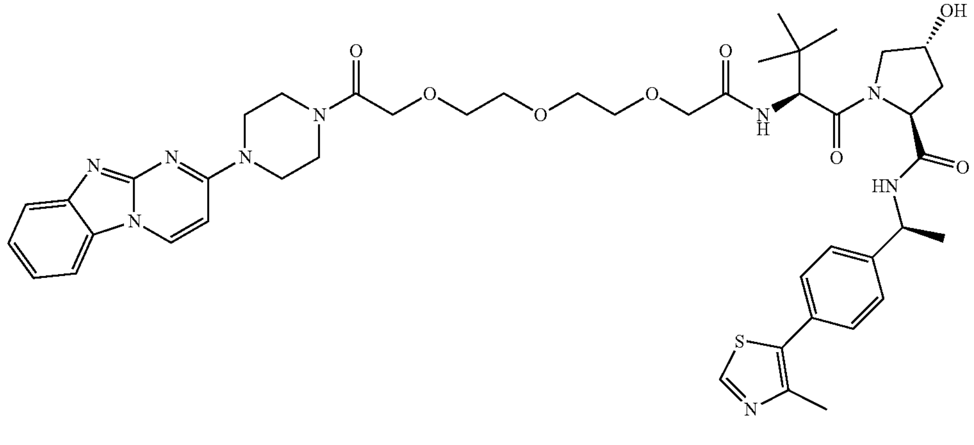 [SMILES: Cc1ncsc1-c1ccc([C@H](C)NC(=O)[C@@H]2C[C@@H](O)CN2C(=O)[C@@H](NC(=O)COCCOCCOCC(=O)N2CCN(c3ccn4c(n3)nc3ccccc34)CC2)C(C)(C)C)cc1]

Prepared according to the scheme below using procedures described above and common procedures known to those skilled in the art.

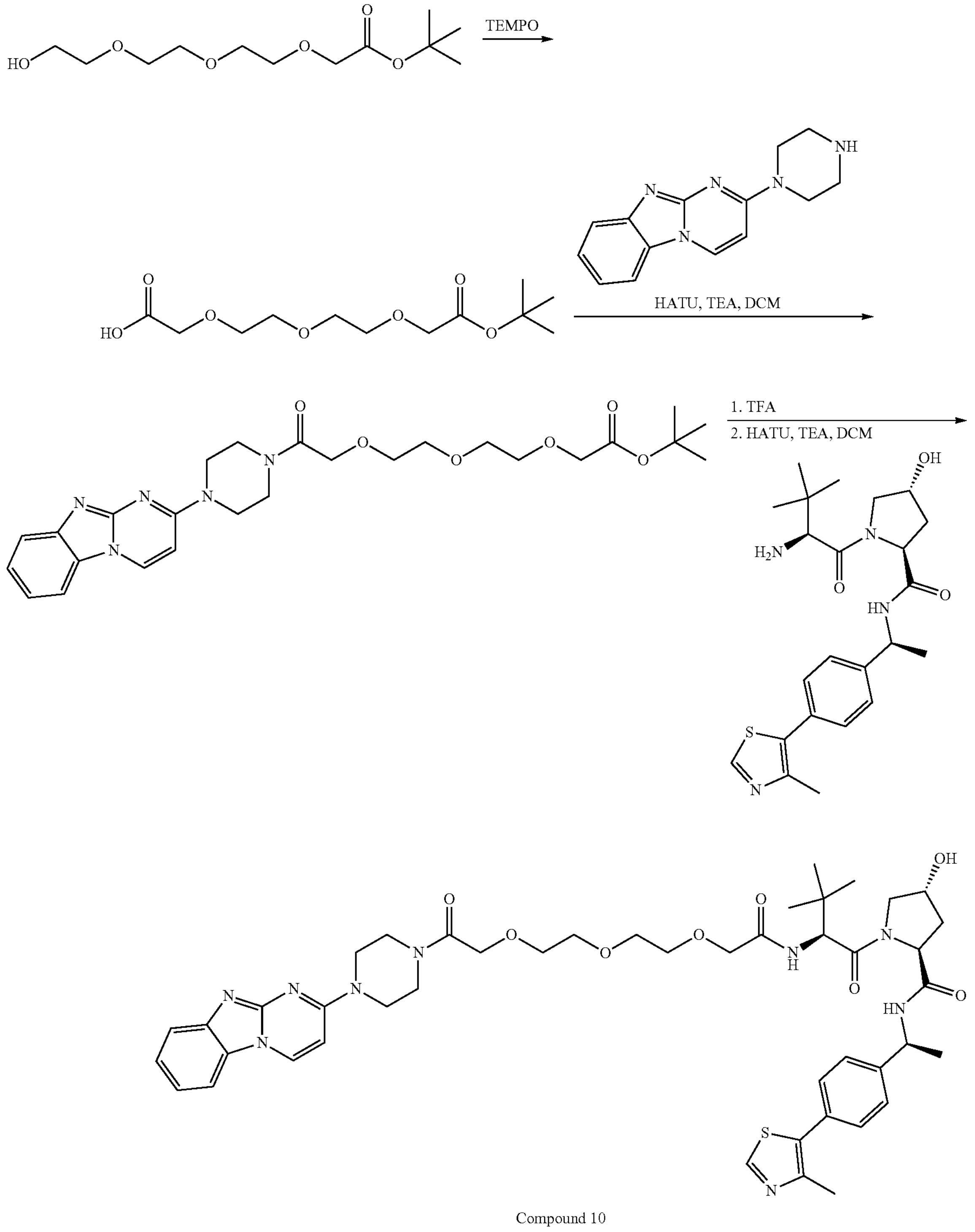
Compound 10
$^1$H NMR (400 MHz, MeOD): δ 8.85 (s, 1H), 8.78 (d, J=7.6 Hz, 1H), 7.83 (d, J=7.6 Hz, 1H), 7.57 (d, J=7.6 Hz, 1H), 7.35-7.40 (m, 6H), 7.23 (t, J=8.0 Hz, 1H), 4.98-5.00 (m, 1H), 4.67 (s, 1H), 4.55-4.57 (m, 1H), 4.34-4.43 (m, 3H), 3.83-4.03 (m, 7H), 3.72-3.74 (m, 16H), 2.46 (s, 3H), 2.17-2.21 (m, 1H), 1.95-2.10 (m, 1H), 1.31 (d, J=8.8 Hz, 3H), 1.03 (s, 9H).
Using procedures described for compound 10 additional compounds were prepared: 13, 14, 17, 18, 21, 22, 24, 41, 42.

Synthetic Scheme for Exemplary Compound 43
(2S,4R)-1-((2S)-2-(tert-butyl)-15-((2-(4-(dimethyl-amino)phenyl)quinolin-6-yl)oxy)-14-hydroxy-4-oxo-6,9,12-trioxa-3-azapentadecanoyl)-4-hydroxy-N-(4-(4-methylthiazol-5-yl)benzyl)pyrrolidine-2-carboxamide
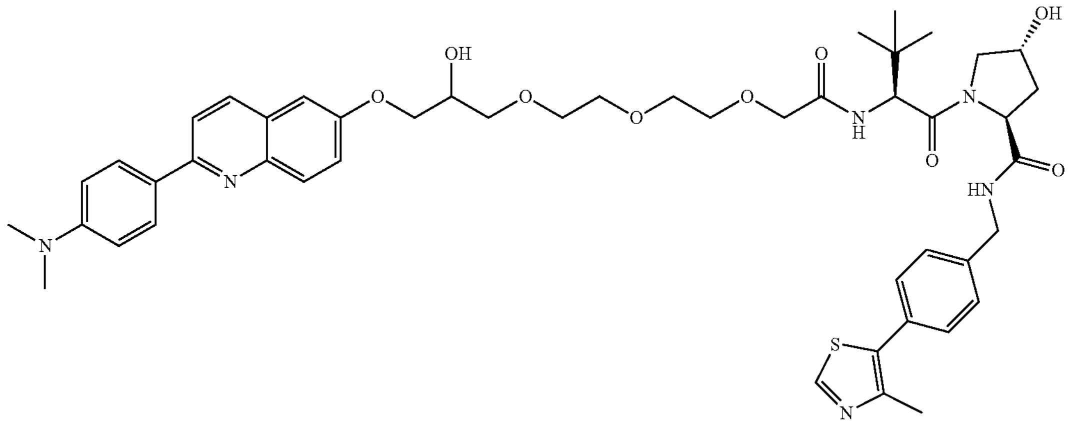 [SMILES: Cc1ncsc1-c1ccc(CNC(=O)[C@@H]2C[C@@H](O)CN2C(=O)[C@@H](NC(=O)COCCOCCOCC(O)COc2ccc3nc(-c4ccc(N(C)C)cc4)ccc3c2)C(C)(C)C)cc1]
Prepared according to the schemes below using procedures described above and common procedures known to those skilled in the art.
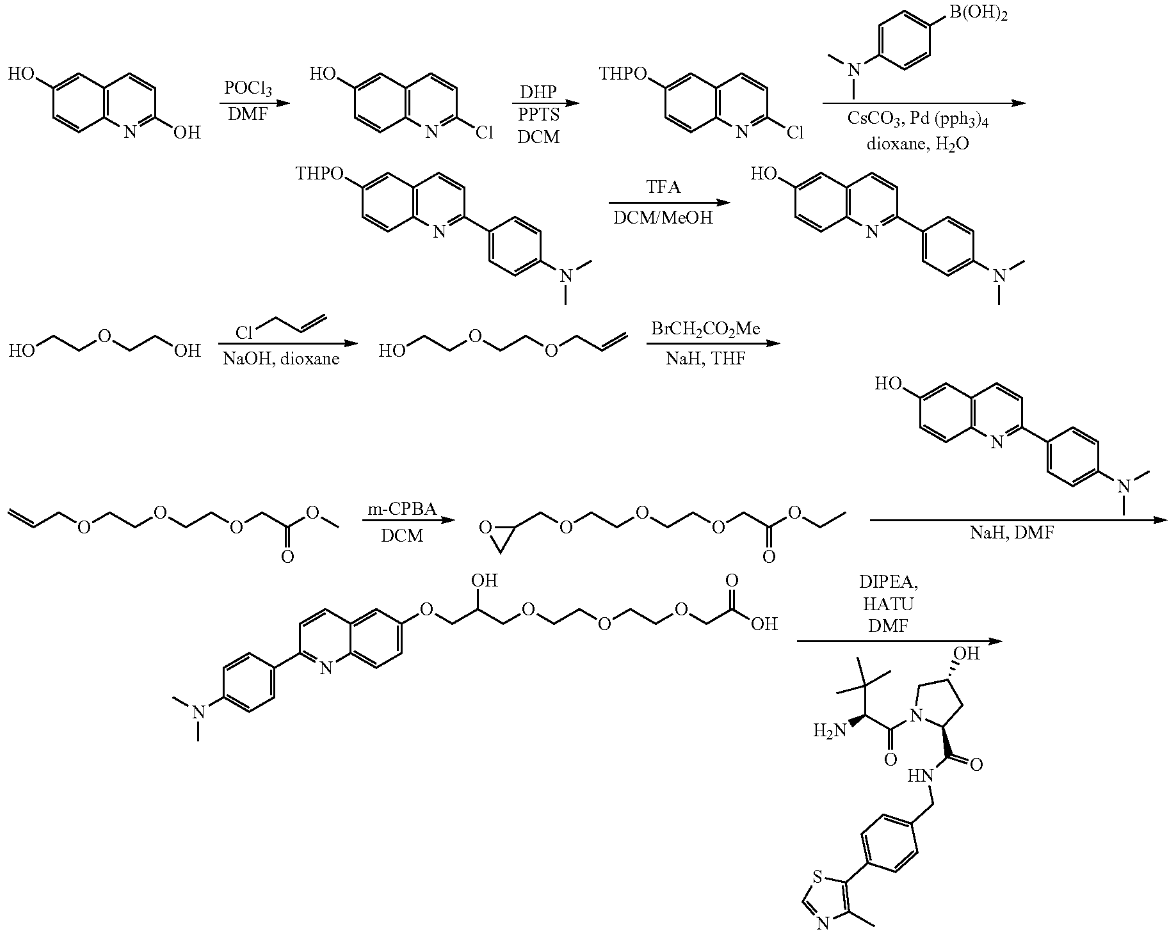

-continued

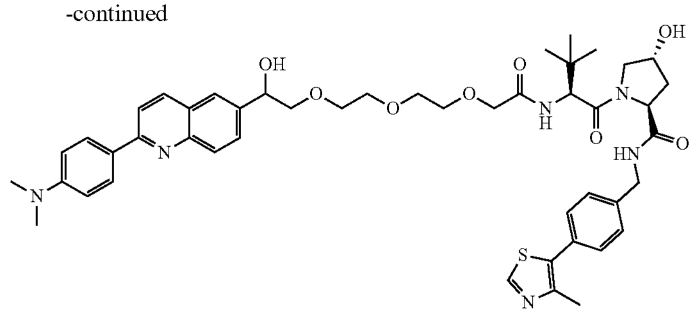

Compound 43

$^1$HNMR (400 MHz, $CD_3OD$): δ 1.04 (s, 9H), 2.05-2.13 (m, 1H), 2.21-2.23 (m, 1H), 2.46 (s, 3H), 3.05 (s, 6H), 3.65-3.74 (m, 10H), 3.79-3.90 (m, 2H), 3.98-4.07 (m, 2H), 4.13-4.22 (m, 3H), 4.33-4.37 (m, 1H), 4.50-4.62 (m, 3H), 4.70 (s, 1H), 6.89 (d, J=8.8 Hz, 2H), 7.25-7.26 (m, 1H), 7.38-7.44 (m, 5H), 7.83 (d, J=8.8 Hz, 1H), 7.94-7.97 (m, 3H), 8.17 (d, J=8.8 Hz, 1H), 8.85 (s, 1H).

Using procedures described for Compound 43 the following were prepared: Compound 45, Compound 46, Compound 47.

Synthetic Scheme for Exemplary Compound 8

(2S,4R)-1-((S)-2-(tert-butyl)-15-((2-(4-(dimethylamino)phenyl)quinolin-6-yl)oxy)-4-oxo-6,9,12-trioxa-3-azapentadecanoyl)-4-hydroxy-N-(4-(4-methylthiazol-5-yl)benzyl)pyrrolidine-2-carboxamide

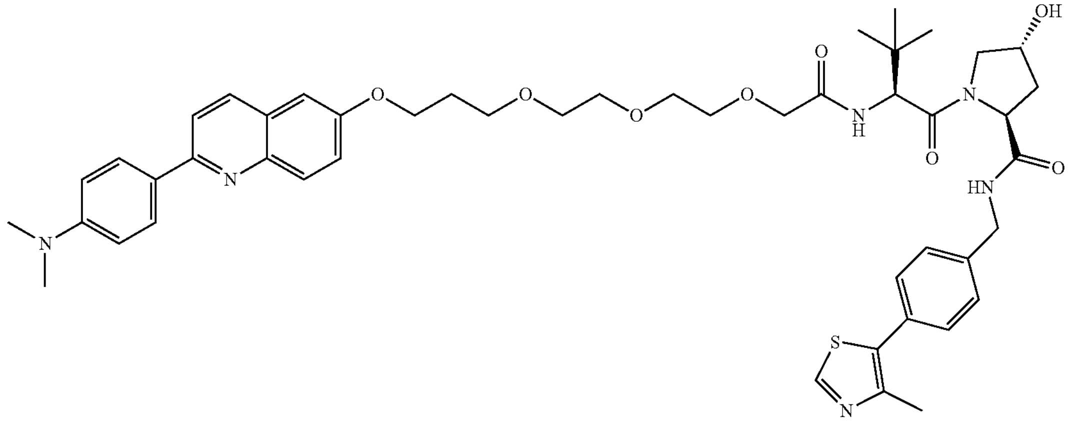 [SMILES: Cc1ncsc1-c1ccc(CNC(=O)[C@@H]2C[C@@H](O)CN2C(=O)[C@@H](NC(=O)COCCOCCOCCCOc2ccc3nc(-c4ccc(N(C)C)cc4)ccc3c2)C(C)(C)C)cc1]

Prepared according to the scheme below using procedures described above and common procedures known to those skilled in the art.

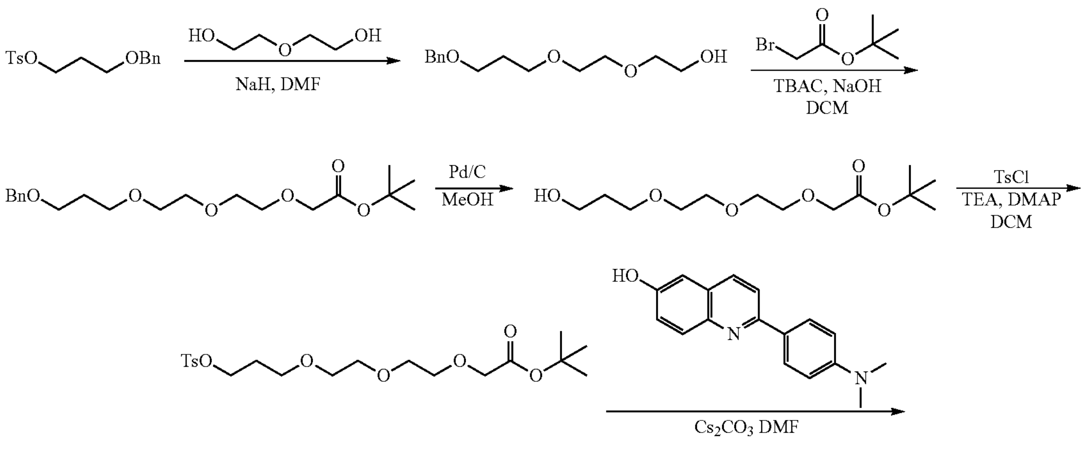

-continued

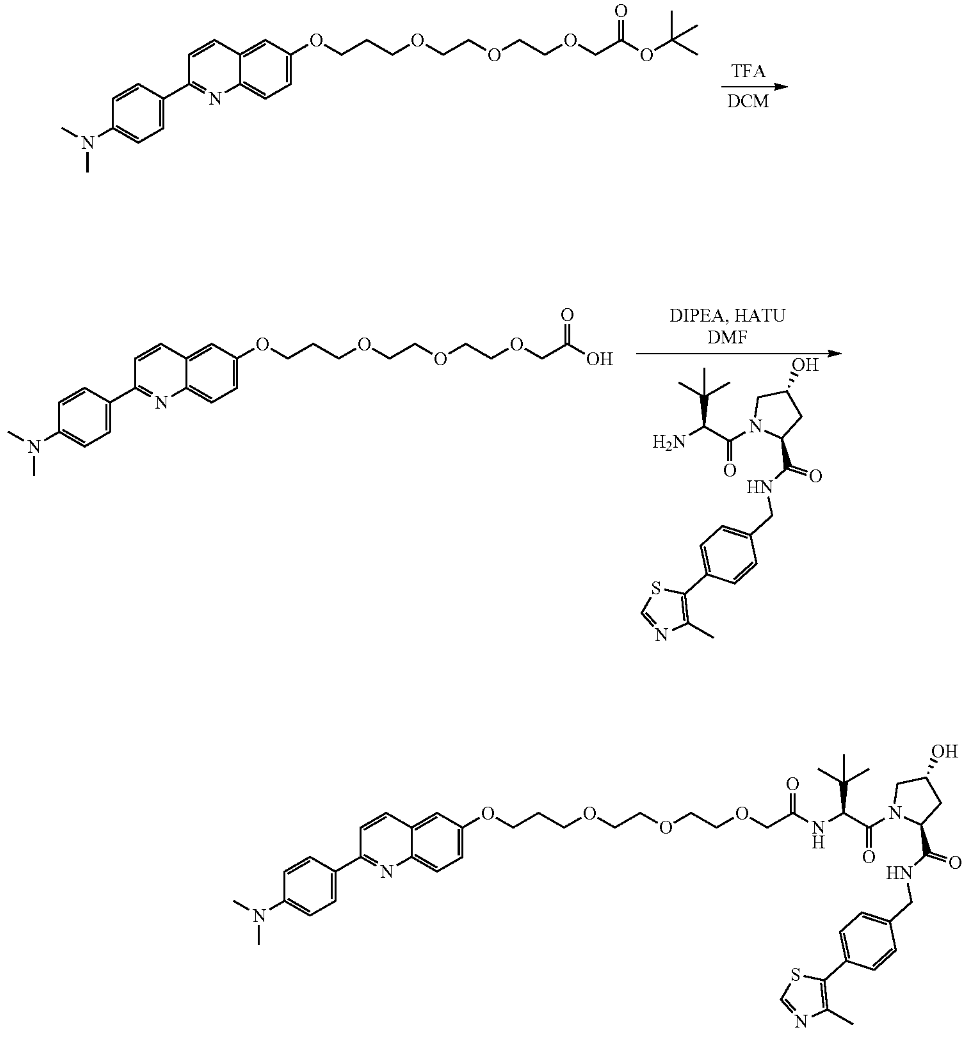

Compound 8

$^1$HNMR (400 MHz, $CD_3OD$): δ 1.01, 1.03 (two singles, 9H), 2.07-2.25 (m, 4H), 2.45, 2.47 (two singles, 3H), 3.04 (s, 6H), 3.65-3.71 (m, 10H), 3.78-3.86 (m, 2H), 4.01-4.06 (m, 2H), 4.18-4.21 (m, 2H), 4.32-4.36 (m, 1H), 4.50-4.60 (m, 3H), 4.68-4.70 (m, 1H), 6.88 (d, J=9.2 Hz, 2H), 7.23-7.26 (m, 1H), 7.34-7.44 (m, 5H), 7.82 (d, J=8.4 Hz, 1H), 7.92-7.96 (m, 3H), 8.16 (d, J=8.8 Hz, 1H), 8.85, 8.86 (two singles, 1H).

Using procedures described for Compound 8 the following were prepared: Compound 9, Compound 27, Compound 28, Compound 29, Compound 30, Compound 31, Compound 32, Compound 33, Compound 34, Compound 35, Compound 36, Compound 37, Compound 38, Compound 39, Compound 40, Compound 44.

Synthetic Scheme of Exemplary Compound 49

3-(4-((14-((5-(5H-pyrido[4,3-b]indol-7-yl)pyridin-2-yl)oxy)-3,6,9,12-tetraoxatetradecyl)amino)-1-oxoisoindolin-2-yl)piperidine-2,6-dione

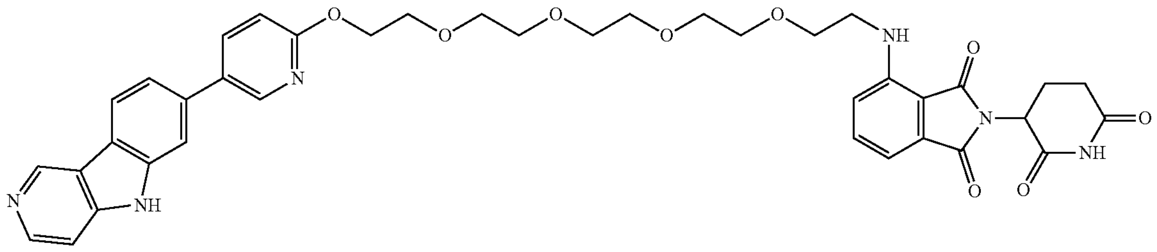 [SMILES: O=C1CCC(N2C(=O)c3cccc(NCCOCCOCCOCCOCCOc4ccc(-c5ccc6c(c5)[nH]c5ccncc56)cn4)c3C2=O)C(=O)N1]

Prepared according to the scheme below using procedures described above and common procedures known to those skilled in the art.

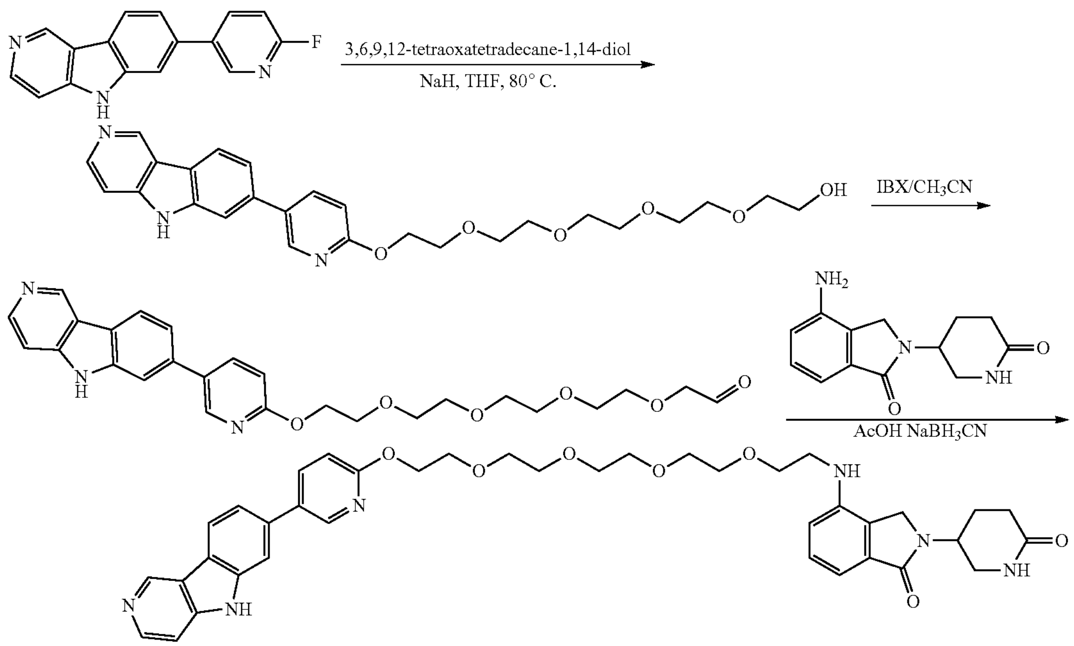

Compound 49

$^1$H NMR (400 MHz, $CD_3OD$): δ 9.36 (s, 1H), 8.39-8.45 (m, 3H), 8.30 (d, J=8.0 Hz, 1H), 8.01 (dd, J=2.4, 6.4 Hz, 1H), 7.78 (s, 1H), 7.70 (d, J=6.0 Hz, 1H), 7.59 (d, J=8.4 Hz, 1H), 7.26 (t, J=7.6 Hz, 1H), 7.03 (d, J=7.6 Hz, 1H), 6.90 (d, J=8.8 Hz, 1H), 6.80 (d, J=8.0 Hz, 1H), 5.12 (dd, J=5.2, 13.6 Hz, 1H), 4.47 (t, J=4.4 Hz, 2H), 4.27 (d, J=2.4 Hz, 2H), 3.85 (d, J=4.4 Hz, 2H), 3.62-3.68 (m, 14H), 3.36 (t, J=5.6 Hz, 2H), 2.75-2.95 (m, 2H), 2.35-2.47 (m, 1H), 2.10-2.21 (m, 1H).

Compound 218 can be prepared using procedures analogous to those of Compound 195.

Compound 219 can be prepared using procedures analogous to those of Compounds 73/180/112.

Compound 220 can be prepared using procedures analogous to those of Compounds 73/173.

Compound 221 can be prepared using procedures analogous to those of Compounds 111/127.

Compound 222 can be prepared using procedures analogous to those of Compounds 141/180.

Compound 223 can be prepared using procedures analogous to those of Compounds 102/180.

Compounds 224 and 225 can be prepared according to the schemes below.

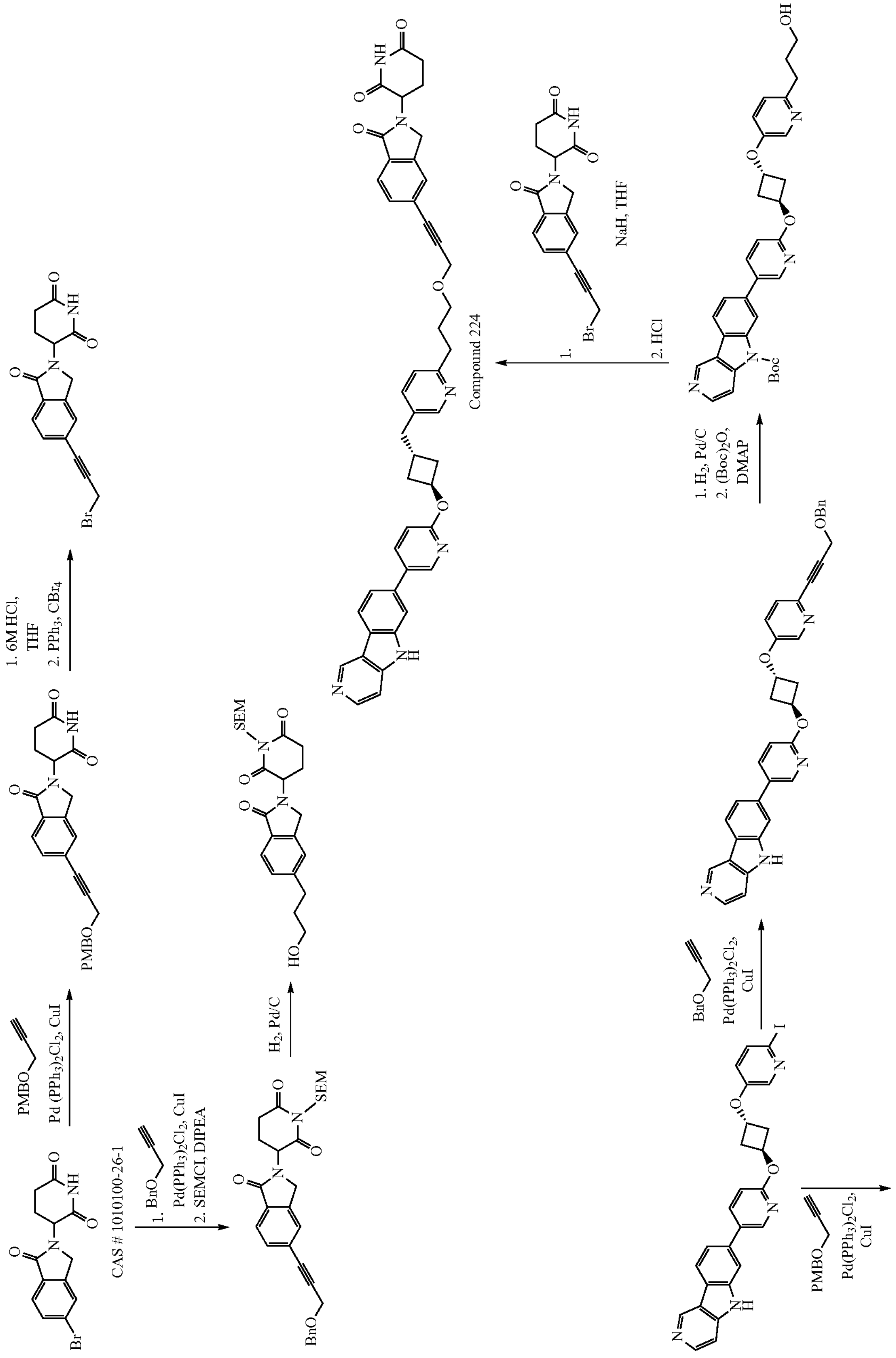
Compound 224

-continued
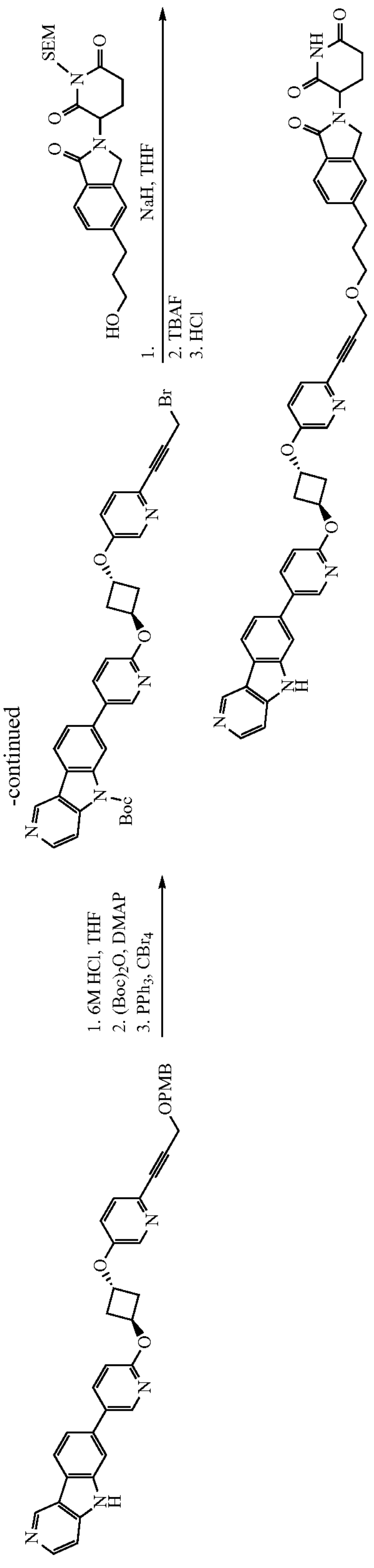
Compound 228

Using approaches described above (including general approaches for Compounds 73, 173 and 180), Compound 226 through 234 can be prepared in analogous ways by using common procedures known to those skilled in the art.

Additionally, combining these approaches with procedures described above for Compounds 138, 139, 140 and 203, Compound 235 through 240 can be prepared.

Compounds 241 through 247 can be prepared by using procedures analogous to those of Compounds 82/198 and 180.

Compounds 248 through 251 can be prepared based on the Compound 82 followed by additional linker elaboration in a manner analogous to approaches described above and known to those skilled in the art.

Compounds 252 through 256 can be prepared based on the approaches to Compounds 104, 99 and 198, and combination thereof.

Additional examples, Compounds 257 through 330, can be prepared based on the fundamental PTM, ULM and linker approaches described above and combined with applicable functional and protecting group elaborations known to those skilled in the art.

Exemplary Synthesis of Exemplary Compound 214

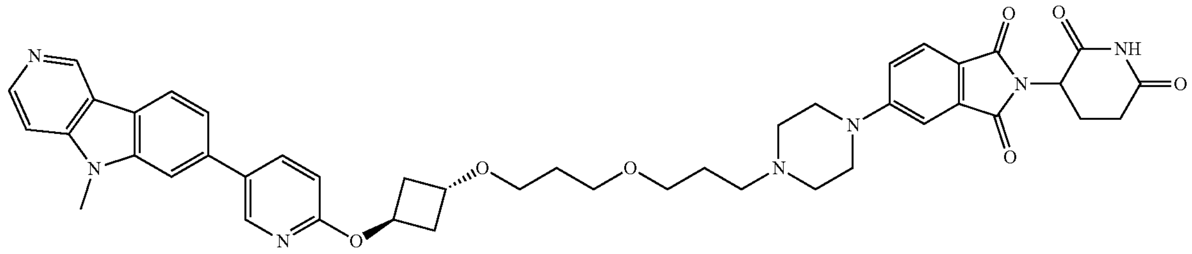 [SMILES: Cn1c2ccncc2c2ccc(-c3ccc(O[C@H]4C[C@H](OCCCOCCCN5CCN(c6ccc7c(c6)C(=O)N(C6CCC(=O)NC6=O)C7=O)CC5)C4)nc3)cc21]

The title compound was prepared according to the scheme below using procedures described in detail by Crew, A. et al. in US 20180125821, as well as variations of those procedures and other methods known to those skilled in the art.

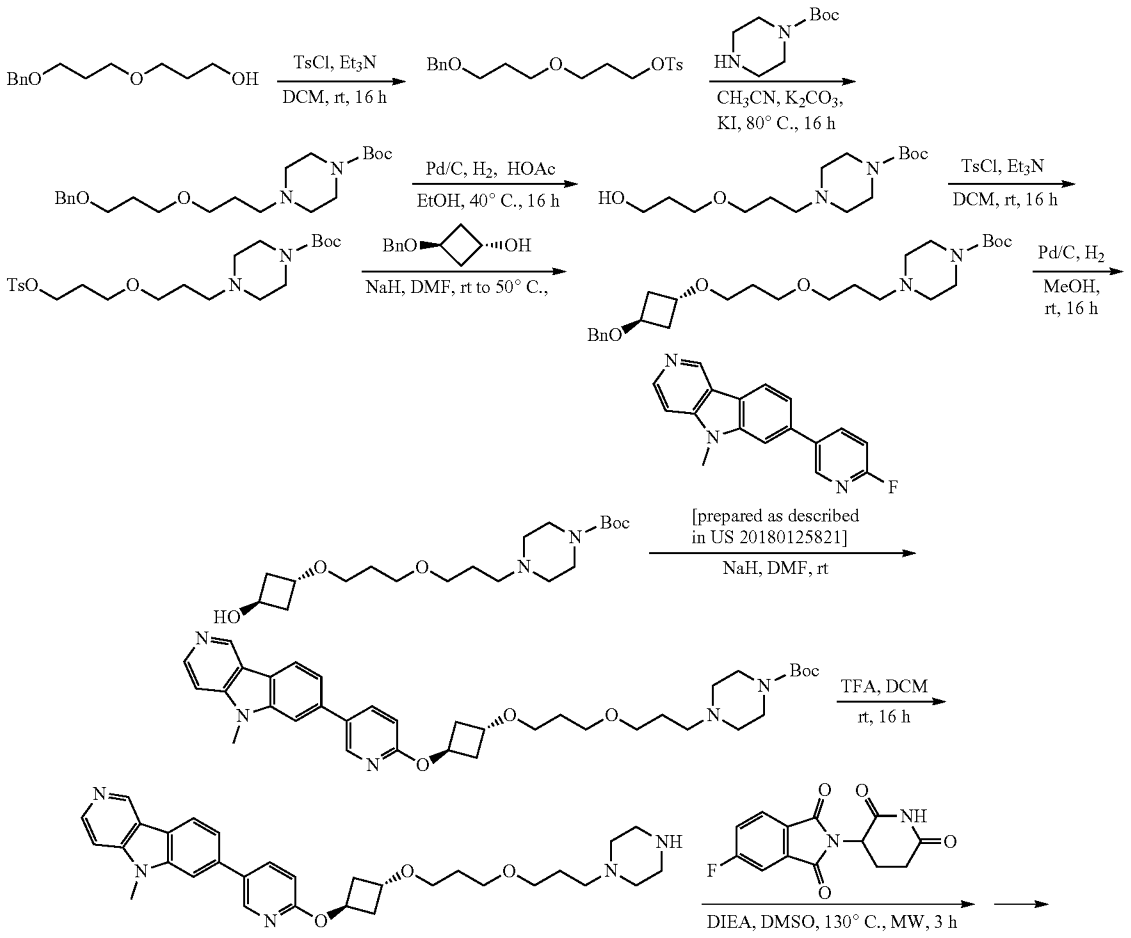

-continued

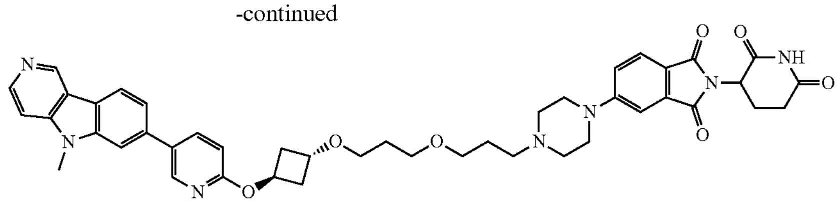

Exemplary Compound 214

Exemplary Synthesis of Exemplary Compound 216

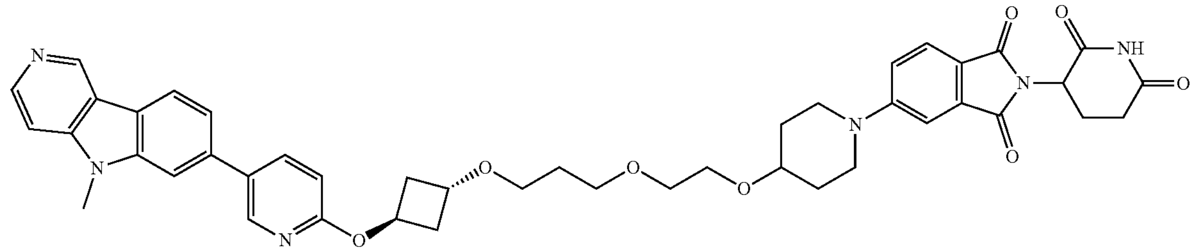 [SMILES: Cn1c2ccncc2c2ccc(-c3ccc(O[C@H]4C[C@H](OCCCOCCOC5CCN(c6ccc7c(c6)C(=O)N(C6CCC(=O)NC6=O)C7=O)CC5)C4)nc3)cc21]

tert-Butyl 4-(2-(3-(tosyloxy)propoxy)ethoxy)piperidine-1-carboxylate was prepared according to the scheme below by using procedures analogous to those of exemplary synthesis of exemplary compound 214.

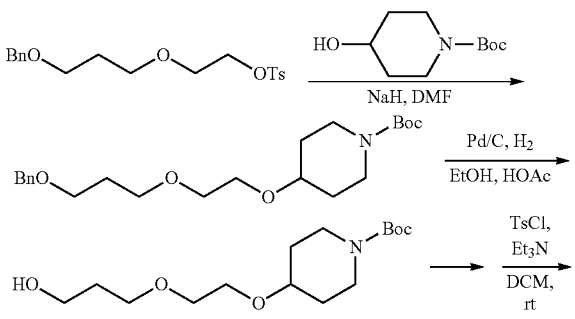

-continued

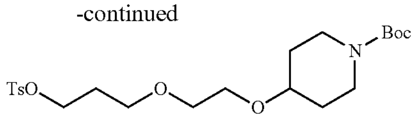

tert-Butyl 4-(2-(3-(tosyloxy)propoxy)ethoxy)piperidine-1-carboxylate was converted to the final compound, exemplary compound 216, 2-(2,6-dioxopiperidin-3-yl)-5-(4-(2-(3-((1r,3r)-3-((5-(5-methyl-5H-pyrido[4,3-b]indol-7-yl)pyridin-2-yl)oxy)cyclobutoxy)propoxy)ethoxy)piperidin-1-yl)isoindoline-1,3-dione, using procedures analogous to those of exemplary compound 214.

Exemplary Synthesis of Exemplary Compound 266

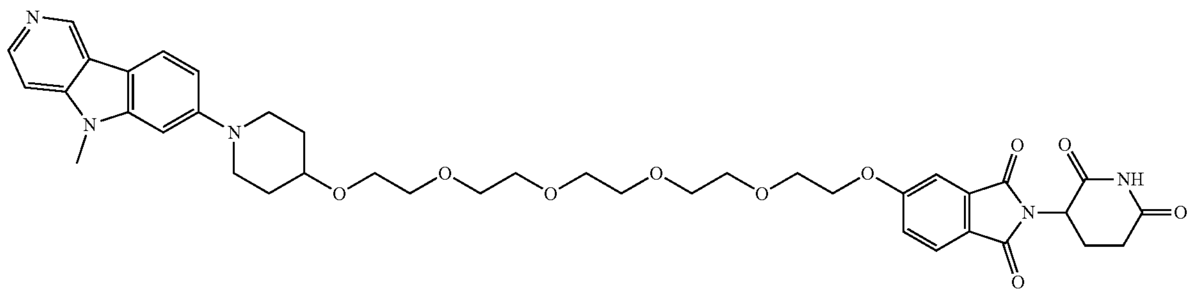 [SMILES: Cn1c2ccncc2c2ccc(N3CCC(OCCOCCOCCOCCOCCOc4ccc5c(c4)C(=O)N(C4CCC(=O)NC4=O)C5=O)CC3)cc21]

Prepared according to the scheme below using procedures analogous to those used for examples above and described in detail in US 20180125821.
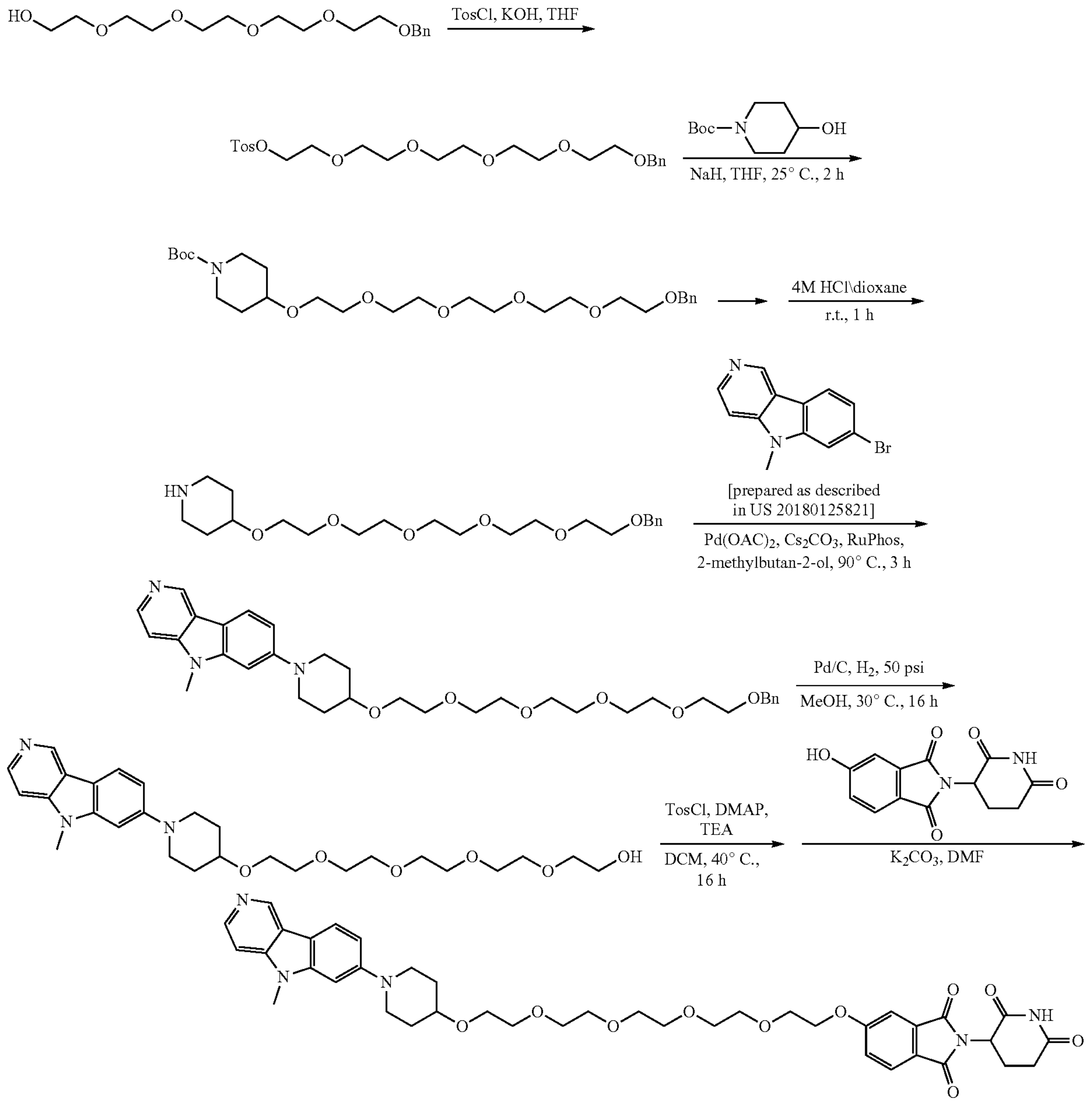
Exemplary Compound 266
Exemplary Synthesis of Exemplary Compound 331
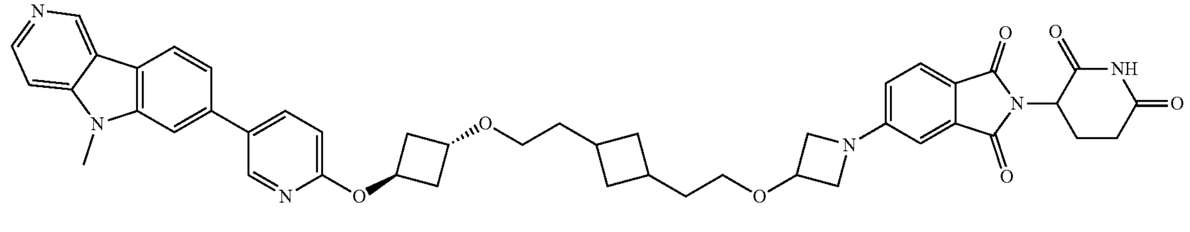 [SMILES: Cn1c2ccncc2c2ccc(-c3ccc(O[C@H]4C[C@H](OCCC5CC(CCOC6CN(c7ccc8c(c7)C(=O)N(C7CCC(=O)NC7=O)C8=O)C6)C5)C4)nc3)cc21]

Step 1

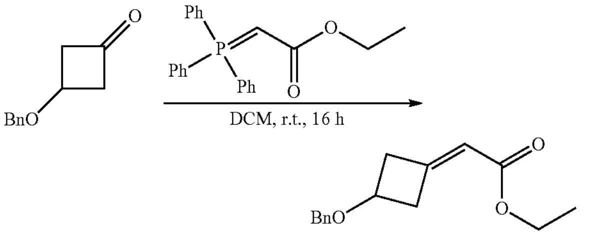

A mixture of 3-benzyloxycyclobutanone (10 g, 56.75 mmol, 1 eq) and ethyl 2-(triphenyl-phosphanylidene)acetate (23.72 g, 68.10 mmol, 1.2 eq) in dichloromethane (100 mL) was degassed and purged with nitrogen for 3 times, and then the mixture was stirred at 40° C. for 16 h under nitrogen. The reaction mixture was quenched by addition water 5 mL, and then diluted with water (20 mL) and extracted with ethyl acetate (20 mL×3). The combined organic layers were washed with solvent brine (20 mL×3), dried over anhydrous sodium sulfate, filtered and concentrated under reduced pressure. The residue was purified by silica gel chromatography (petroleum ether:ethyl acetate=100/1 to 10/1). Compound ethyl 2-(3-benzyloxycyclobutylidene)acetate (12 g, 48.72 mmol, 86% yield) was obtained as a colorless oil.

Step 2

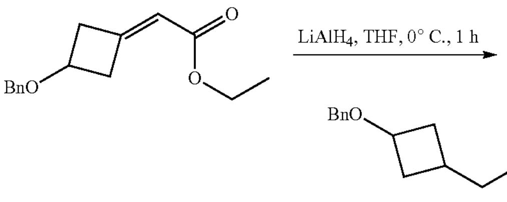

To a suspension of lithium aluminum hydride (3.70 g, 97.44 mmol, 2 eq) in tetrahydrofuran (100 mL) was added ethyl 2-(3-benzyloxycyclobutylidene)acetate (12 g, 48.72 mmol, 1 eq) at 0° C. The reaction mixture was stirred at 0° C. for 1 hour. The reaction mixture was quenched by addition of water (4 mL) at 0° C., followed by 15% aqueous sodium hydroxide (8 mL). 12 mL of water was then added, the mixture was filtered, and the solid was washed. The combined organic layers were concentrated under reduced pressure. The residue was purified by column chromatography (petroleum ether/ethyl acetate=50/1 to 20/1) to give 2-(3-benzyloxycyclobutyl)ethanol (4 g, 19.39 mmol, 39% yield) as a colorless oil.

Step 3

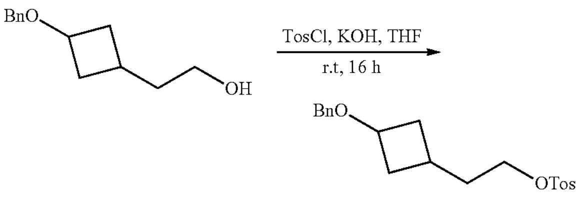

A mixture of 2-(3-benzyloxycyclobutyl)ethanol (4 g, 19.39 mmol, 1 eq), potassium hydroxide (3.26 g, 58.17 mmol, 3 eq) and p-toluenesulfonyl chloride (11.09 g, 58.17 mmol, 3 eq) in tetrahydrofuran (20 mL) was degassed and purged with nitrogen 3 times, and then the mixture was stirred at 20° C. for 1 hour under nitrogen. The reaction mixture was filtered and concentrated under reduced pressure to give a residue. The residue was purified by column chromatography (petroleum ether/ethyl acetate=50/1 to 10/1) to give 2-(3-benzyloxycyclobutyl)ethyl 4-methylbenzenesulfonate (5.2 g, 14.43 mmol, 74% yield) as a yellow oil.

Step 4

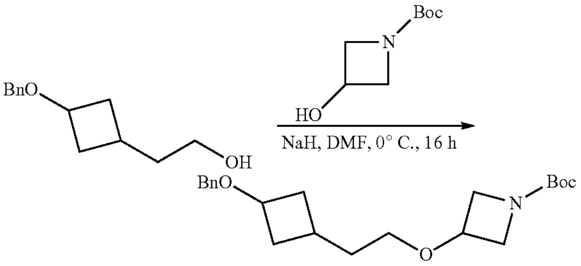

To a solution of tert-butyl 3-hydroxyazetidine-1-carboxylate (2.75 g, 15.87 mmol, 1.1 eq) in N,N-dimethylformamide (30 mL) was added sodium hydride (865 mg, 21.64 mmol, 60%, 1.5 eq) at 0° C. After stirring at 0° C. for 0.5 hours, 2-(3-benzyloxycyclobutyl)ethyl 4-methylbenzenesulfonate (5.2 g, 14.43 mmol, 1 eq) was added at 0° C. The mixture was stirred at 25° C. for 15 hours. The reaction mixture was quenched by the addition of water (100 mL), and extracted with ethyl acetate (200 mL×3). The combined organic layers were washed with brine (100 mL×3), dried over anhydrous sodium sulfate, filtered and concentrated under reduced pressure to give a residue. The residue was purified by Semi-preparative reverse phase-HPLC (column: Phenomenex Synergi Max-RP 250*80 mm*10 um; mobile phase: [water (0.225% formic)-acetonitrile]; B %: 41%-71%, 35 min, 30% min) to give tert-butyl 3-[2-(3-benzyloxycyclobutyl)ethoxy]azetidine-1-carboxylate (1.9 g, 5.26 mmol, 36% yield) as a colorless oil.

Step 5

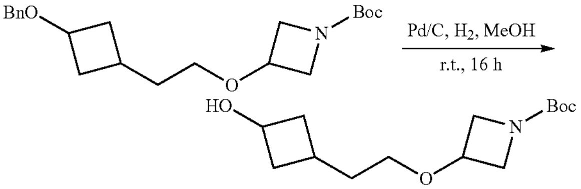

To a solution of tert-butyl 3-[2-(3-benzyloxycyclobutyl) ethoxy]azetidine-1-carboxylate (1.9 g, 5.26 mmol, 1 eq) in methanol (50 mL) was added 10% palladium on activated carbon (200 mg) under nitrogen. The suspension was degassed under vacuum and purged with hydrogen 3 times. The mixture was stirred under hydrogen (50 psi) at 25° C. for 16 hours. The reaction mixture was filtered and concentrated under reduced pressure to give a residue. Compound tert-butyl 3-[2-(3-hydroxycyclobutyl)ethoxy]azetidine-1-carboxylate (1.4 g, 5.16 mmol, 98% yield) was obtained as a yellow oil.

Step 6

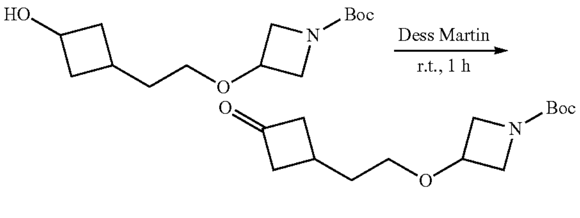

A mixture of tert-butyl 3-[2-(3-hydroxycyclobutyl)ethoxy]azetidine-1-carboxylate (1.3 g, 4.79 mmol, 1 eq) and Dess-Martin periodinane (4.06 g, 9.58 mmol, 2.97 mL, 2 eq) in dichloromethane (30 mL) was degassed and purged with nitrogen 3 times, and then the mixture was stirred at 0° C. for 1 hour under nitrogen. The reaction mixture was filtered and concentrated under reduced pressure to give a residue. The residue was purified by column chromatography (Petroleum ether/Ethyl acetate=20/1 to 3/1). Compound tert-butyl 3-[2-(3-oxocyclobutyl)ethoxy]azetidine-1-carboxylate (1.1 g, 4.08 mmol, 85% yield) was obtained as a colorless oil.

Using procedures analogous to those described above tert-butyl 3-[2-(3-oxocyclobutyl)ethoxy]azetidine-1-carboxylate was converted to tert-butyl 3-(2-(3-(2-((1s,3s)-3-hydroxycyclobutoxy)ethyl)cyclobutyl)ethoxy)azetidine-1-carboxylate as shown in the scheme below.

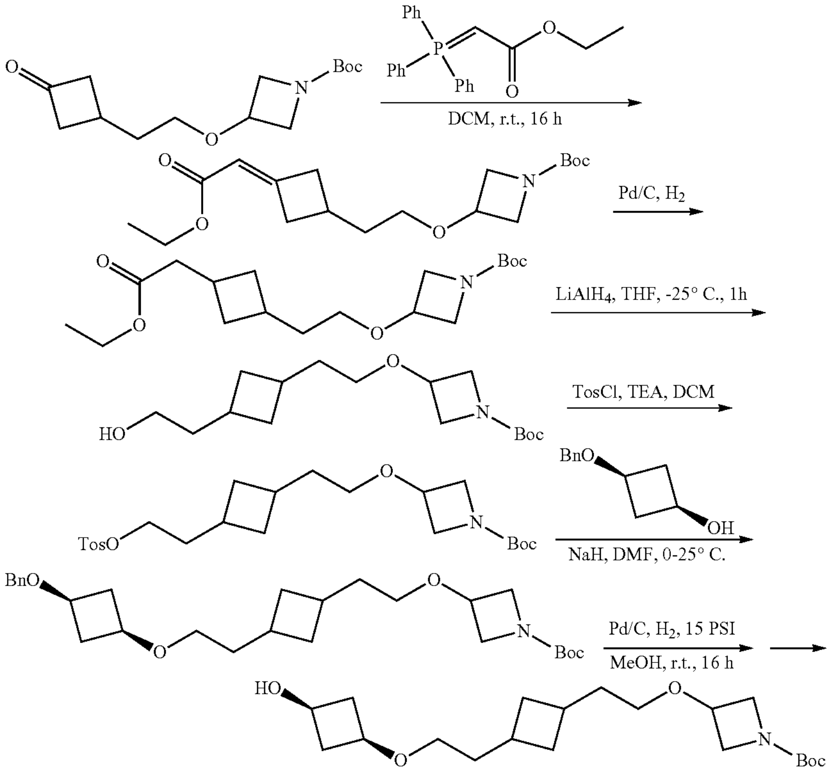

Step 13

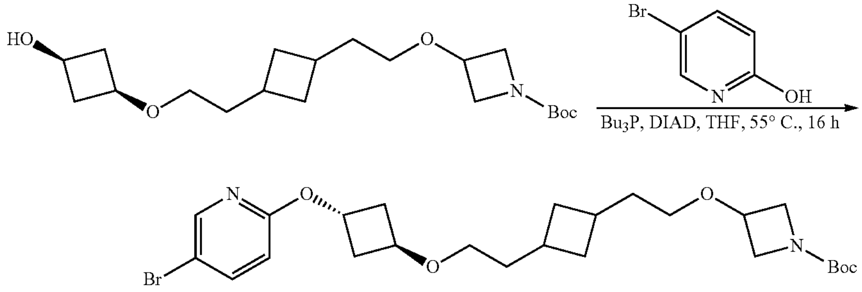

A mixture of tert-butyl 3-[2-[3-[2-(3-hydroxycyclobutoxy)ethyl]cyclobutyl]ethoxy]azetidine-1-carboxylate (70 mg, 0.18 mmol, 0.7 eq), 5-bromopyridin-2-ol (70 mg, 0.40 mmol, 1.5 eq), 1,1'-(azodicarbonyl)dipiperidine (102 mg, 0.40 mmol, 1.5 eq) and tributylphosphine (82 mg, 0.40 mmol, 1.5 eq) in toluene (6 mL) was degassed and purged with nitrogen for 3 times, and then the mixture was stirred at 110° C. for 16 hours under nitrogen. To the reaction was added petroleum ether (10 mL). The suspension was filtered through a pad of silica gel. The mother liquor was concentrated to give a residue. The residue was purified by column chromatography (petroleum ether/ethyl acetate=100/1 to 20/1) to give tert-butyl 3-[2-[3-[2-[3-[(5-bromo-2-pyridyl)oxy]cyclobutoxy]ethyl]cyclobutyl]ethoxy]azetidine-1-carboxylate (80 mg, 0.14 mmol, 54% yield) as a yellow oil.

Step 14

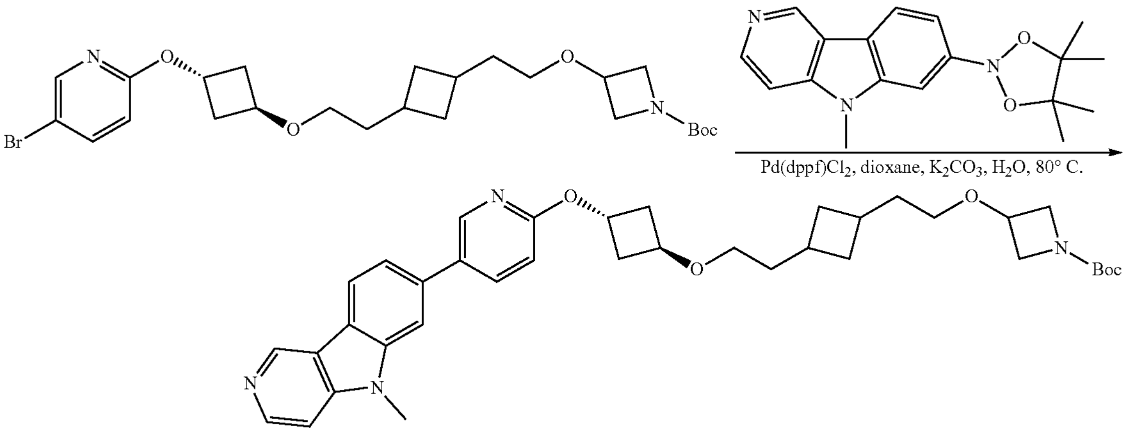

A mixture of 5-methyl-7-(4,4,5,5-tetramethyl-1,3,2-dioxaborolan-2-yl)pyrido[4,3-b]indole (46 mg, 0.15 mmol, 1 eq), tert-butyl 3-[2-[3-[2-[3-[(5-bromo-2-pyridyl)oxy]cyclobutoxy]ethyl]cyclobutyl]ethoxy]azetidine-1-carboxylate (80 mg, 0.15 mmol, 1 eq), [1,1'-bis(diphenylphosphino)ferrocene]dichloropalladium(II) (11 mg, 0.0.01 mmol, 0.1 eq) and sodium carbonate (32 mg, 0.03 mmol, 2 eq) in water (0.2 mL) and dioxane (2 mL) was degassed and purged with nitrogen for 3 times, and then the mixture was stirred at 90° C. for 16 hours under nitrogen. The reaction mixture was filtered and concentrated under reduced pressure to give a residue. The residue was purified by prep-TLC (9% methanol in dichloromethane). Compound tert-butyl 3-[2-[3-[2-[3-[[5-(5-methylpyrido[4,3-b]indol-7-yl)-2-pyridyl]oxy]cyclobutoxy]ethyl]cyclobutyl]ethoxy]azetidine-1-carboxylate (50 mg, 0.08 mol, 52% yield) was obtained as a yellow oil.

Step 15

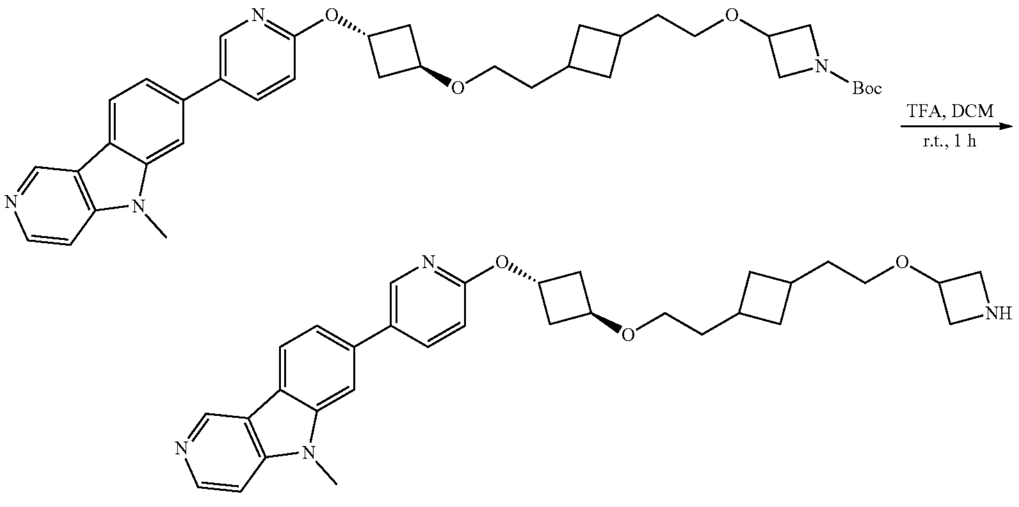

A mixture of tert-butyl 3-[2-[3-[2-[3-[[5-(5-methylpyrido[4,3-b]indol-7-yl)-2-pyridyl]oxy]cyclobutoxy]ethyl]cyclobutyl]ethoxy]azetidine-1-carboxylate (50 mg, 0.08 mmol, 1 eq) and trifluoroacetic acid (770 mg, 6.75 mmol, 84.65 eq) in dichloromethane (3 mL) was stirred at 25° C. for 0.5 hours. The reaction mixture was concentrated under reduced pressure to give a residue. The residue was purified by Semi-preparative reverse phase-HPLC (column: Phenomenex Synergi C18 150*30 mm*4 um; mobile phase: [water (0.225% FA)-ACN]; B %: 10%-40%, 10.5 min). Compound 7-[6-[3-[2-[3-[2-(azetidin-3-yloxy)ethyl]cyclobutyl]ethoxy]cyclobutoxy]-3-pyridyl]-5-methyl-pyrido[4,3-b]indole (20 mg, 0.03 mmol, 43% yield) was obtained as a white solid.

Step 16

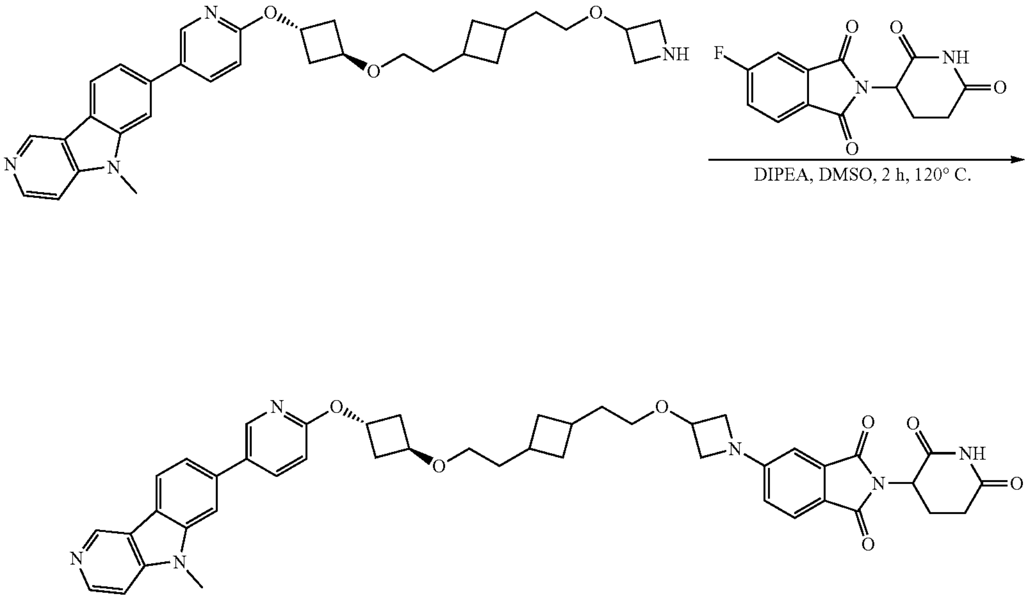

Exemplary Compound 331

A mixture of 7-[6-[3-[2-[3-[2-(azetidin-3-yloxy)ethyl]cyclobutyl]ethoxy]cyclobutoxy]-3-pyridyl]-5-methyl-pyrido[4,3-b]indole (20 mg, 0.03 mmol, 1 eq, formate), 2-(2,6-dioxo-3-piperidyl)-5-fluoro-isoindoline-1,3-dione (10 mg, 0.03 mmol, 1 eq) and diisopropylethylamine (14 mg, 0.11 mmol, 3 eq) in dimethyl sulfoxide (1 mL) was degassed and purged with nitrogen for 3 times, and then the mixture was stirred at 120° C. for 2 hours under nitrogen. The reaction mixture was concentrated under reduced pressure to give a residue. The residue was purified by semi-preparative reverse phase HPLC (column: Phenomenex Synergi C18 150*25*10 um; mobile phase: [water (0.225% FA)-ACN]; B %: 40%-70%, 10 min) to give 2-(2,6-dioxo-3-piperidyl)-5-[3-[2-[3-[2-[3-[[5-(5-methylpyrido[4,3-b]indol-7-yl)-2-pyridyl]oxy]cyclobutoxy]ethyl]cyclobutyl]ethoxy]azetidin-1-yl]isoindoline-1,3-dione (17.8 mg, 0.02 mmol, 56% yield) as a white solid.

Exemplary Synthesis of Exemplary Compound 220

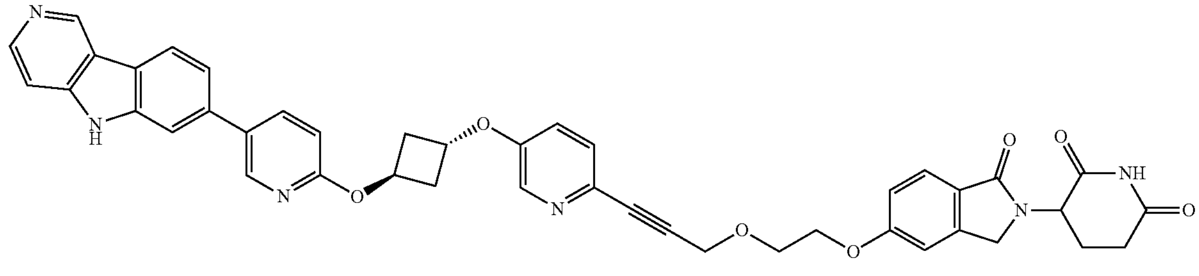 [SMILES: O=C1CCC(N2Cc3cc(OCCOCC#Cc4ccc(O[C@H]5C[C@H](Oc6ccc(-c7ccc8c(c7)[nH]c7ccncc78)cn6)C5)cn4)ccc3C2=O)C(=O)N1]

Step 1

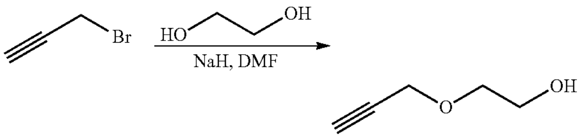

Into a 250-mL round-bottom flask purged and maintained with an inert atmosphere of nitrogen, was placed ethane-1,2-diol (7.8 g, 0.13 mmol, 2.99 equiv) in toluene (60 mL). This was followed by the addition of NaH (60%, 2 g, 8.75 mmol, 2 equiv) at 0° C. The resulting solution was stirred for 0.5 h at room temperature. To this was added 3-bromoprop-1-yne (5 g, 0.04 mmol, 1 equiv) and the resulting solution was stirred overnight at 45° C. The reaction was then quenched by the addition of water/ice (20 mL). The resulting mixture was extracted with ethyl acetate (50 mL×3), and the organic layers were combined and dried over anhydrous sodium sulfate. The organic phase was concentrated under reduced pressure. The residue was purified by silica gel column chromatography, eluted with ethyl acetate/petroleum ether (1:1) to afford 2-(prop-2-yn-1-yloxy)ethan-1-ol (3.5 g, 83%) as a yellow oil.

Step 2

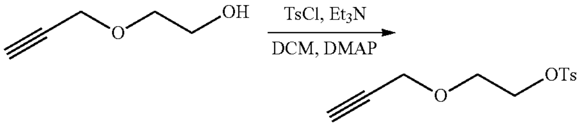

Into a 100-mL round-bottom flask, was placed 2-(prop-2-yn-1-yloxy)ethan-1-ol (300 mg, 3.00 mmol, 1 equiv), TsCl (857 mg, 4.49 mmol, 1.50 equiv), $Et_3N$ (606 mg, 5.99 mmol, 2.00 equiv), DMAP (36.6 mg, 0.30 mmol, 0.1 equiv) in dichloromethane (30 mL). The resulting solution was stirred for 1 h at room temperature. The reaction was then quenched by the addition of water (20 mL). The resulting solution was extracted with dichloromethane (30 mL×3), and the organic layers were combined. The resulting mixture was washed with brine (20 ml×1). The mixture was dried over anhydrous sodium sulfate and concentrated under reduced pressure. The residue was purified by silica gel column chromatography, eluted with ethyl acetate/petroleum ether (1:5) to afford 2-(prop-2-yn-1-yloxy)ethyl 4-methylbenzene-1-sulfonate (700 mg (92%)) as a yellow oil.

Step 3

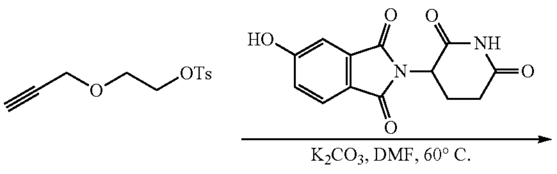

-continued

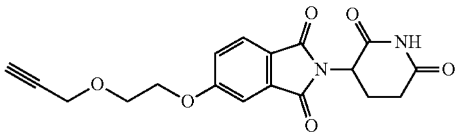

Into a 100-mL round-bottom flask, was placed 2-(prop-2-yn-1-yloxy)ethyl 4-methylbenzene-1-sulfonate (696 mg, 2.73 mmol, 1.50 equiv), 2-(2,6-dioxopiperidin-3-yl)-5-hydroxy-2,3-dihydro-1H-isoindole-1,3-dione (500 mg, 1.82 mmol, 1 equiv), $K2CO_3$ (504 mg, 3.65 mmol, 2 equiv) in DMF (50 mL). The resulting solution was stirred for 2 hours at 60° C. The reaction was then quenched by the addition of brine (20 mL). The resulting mixture was extracted with ethyl acetate (40 mL×3), and the organic layers were combined and dried over anhydrous sodium sulfate. The organic phase was concentrated under reduced pressure. The residue was purified by silica gel column chromatography, eluted with dichloromethane/methanol (20:1) to afford 2-(2,6-dioxopiperidin-3-yl)-5-[2-(prop-2-yn-1-yloxy)ethoxy]-2,3-dihydro-1H-isoindole-1,3-dione (358 mg, 55%) as a yellow solid.

Step 4

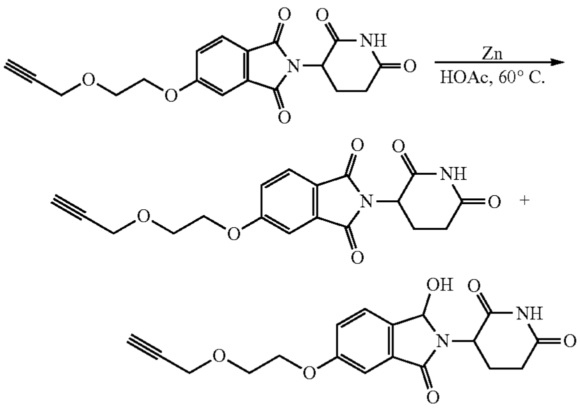

Into a 100-mL round-bottom flask purged and maintained with an inert atmosphere of nitrogen, was placed 2-(2,6-dioxopiperidin-3-yl)-5-[2-(prop-2-yn-1-yloxy)ethoxy]-2,3-dihydro-1H-isoindole-1,3-dione (200 mg, 0.56 mmol, 1 equiv) and zinc (1.8 g, 27.53 mmol, 49.05 equiv) in acetic acid (40 mL). The resulting solution was stirred for 1 hour at 60° C. The solids were filtered out. The filtrate was concentrated under vacuum. This resulted in 15 mg of 3-[1-hydroxy-3-oxo-5-[2-(prop-2-yn-1-yloxy)ethoxy]-2,3-dihydro-1H-isoindol-2-yl]piperidine-2,6-dione as a purple oil and 490 mg of 3-[3-hydroxy-1-oxo-5-[2-(prop-2-yn-1-yloxy)ethoxy]-2,3-dihydro-1H-isoindol-2-yl]piperidine-2,6-dione as a purple oil.

Step 5

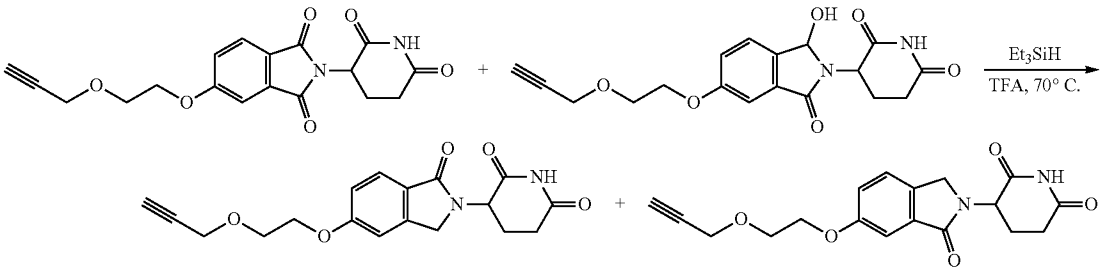

Into a 100-mL round-bottom flask, was placed 3-[3-hydroxy-1-oxo-5-[2-(prop-2-yn-1-yloxy)ethoxy]-2,3-dihydro-1H-isoindol-2-yl]piperidine-2,6-dione (188 mg, 0.53 mmol, 1 equiv), 3-[1-hydroxy-3-oxo-5-[2-(prop-2-yn-1-yloxy)ethoxy]-2,3-dihydro-1H-isoindol-2-yl]piperidine-2,6-dione (11.8 mg, 0.03 mmol, 0.06 equiv), $Et_3SiH$ (305 mg, 2.63 mmol, 5 equiv) in TFA (8 mL). The resulting solution was stirred for 1 hour at 70° C. The resulting mixture was concentrated under vacuum. The crude product was purified by Prep-HPLC with the following conditions: Column, XBridge Prep C18 OBD Column, 5 um, 19*150 mm; mobile phase, water (10 mmol/L $NH_4HCO_3$) and acetonitrile (12% Phase B up to 32% in 10 min); Detector, UV. This resulted in 157 mg of 3-[1-oxo-5-[2-(prop-2-yn-1-yloxy)ethoxy]-2,3-dihydro-1H-isoindol-2-yl]piperidine-2,6-dione as a white solid and 20 mg of 3-[1-oxo-6-[2-(prop-2-yn-1-yloxy)ethoxy]-2,3-dihydro-1H-isoindol-2-yl]piperidine-2,6-dione as a white solid.

Step 6

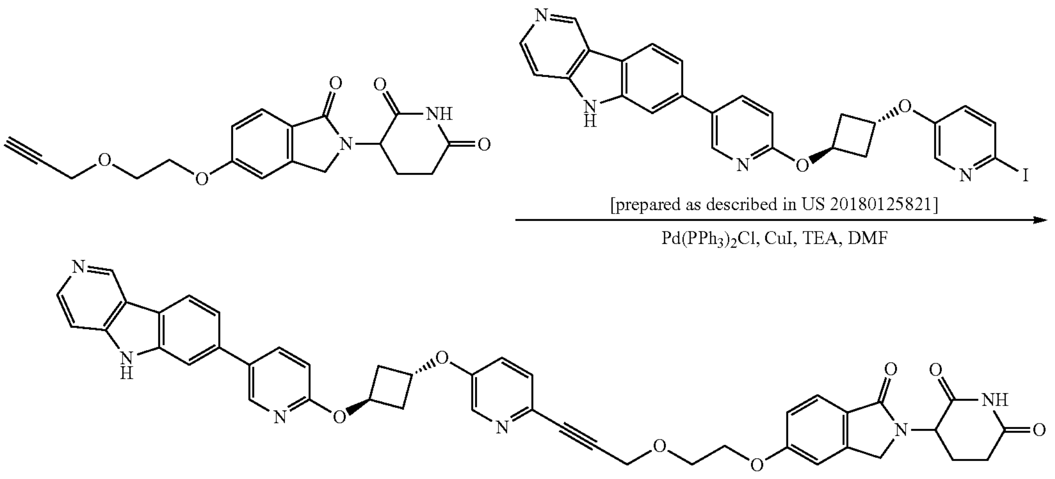

Exemplary Compound 220

Into a 30-mL round bottom flask purged and maintained with an inert atmosphere of nitrogen, was placed 5-[5H-pyrido[4,3-b]indol-7-yl]-2-[(1r,3r)-3-[(6-iodopyridin-3-yl)oxy]cyclobutoxy]pyridine (100 mg, 0.19 mmol, 1 equiv) [prepared as described by Crew, A. et al. in US 20180125821], $Pd(PPh_3)_2Cl_2$ (13 mg, 0.02 mmol, 0.1 equiv), CuI (3.6 mg, 0.02 mmol, 0.1 equiv), TEA (75.7 mg, 0.75 mmol, 4.0 equiv), and 3-[1-oxo-5-[2-(prop-2-yn-1-yloxy)ethoxy]-2,3-dihydro-1H-isoindol-2-yl]piperidine-2,6-dione (77 mg, 0.22 mmol, 1.20 equiv) in DMF (10 mL). The resulting solution was stirred for 2 hr at 65° C. in an oil bath. The crude product was purified by prep-HPLC with the following conditions: Column, XBridge Shield RP18 OBD Column, 5 um, 19*150 mm; mobile phase, water (0.1% FA) and acetonitrile (23% Phase B up to 43% in 8 min); Detector, UV. After lyophilization, this resulted in 19 mg of 3-(1-oxo-5-[2-[(3-[5-[(1r,3r)-3-[(5-[5H-pyrido[4,3-b]indol-7-yl]pyridin-2-yl)oxy]cyclobutoxy]pyridin-2-yl]prop-2-yn-1-yl)oxy]ethoxy]-2,3-dihydro-1H-isoindol-2-yl)piperidine-2,6-dione as a light yellow solid.

Alternatively, 5-[5H-pyrido[4,3-b]indol-7-yl]-2-[(1r,3r)-3-[(6-iodopyridin-3-yl)oxy]cyclobutoxy]pyridine could also be prepared from 7-(6-((1s,3s)-3-(benzyloxy)cyclobutoxy)pyridin-3-yl)-5H-pyrido[4,3-b]indole as described in the procedures below and used in this and other examples.

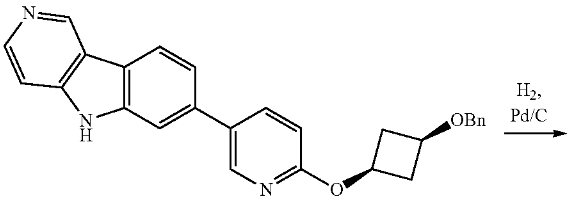

-continued

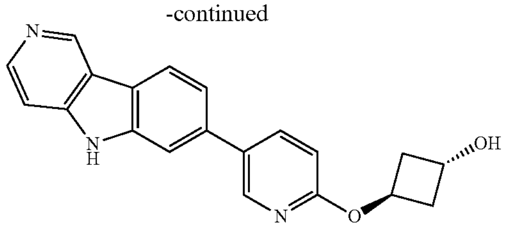

Into a 100-mL round-bottom flask, was placed a mixture of 5-[5H-pyrido[4,3-b]indol-7-yl]-2-[(1s,3s)-3-(benzyloxy)cyclobutoxy]pyridine (5.0 g, 11.86 mmol, 1 equiv), methanol (150 mL), HOAc (5 drops), and 10% Pd/C (3.0 g) under nitrogen atmosphere. The flask was then vacuumed and flushed with hydrogen. The reaction mixture was hydrogenated at 55° C. for 16 hours under hydrogen atmosphere using a hydrogen balloon, then filtered through a celite pad and concentrated under reduced pressure. This resulted in 2.8 g (71%) of (1s,3s)-3-[(5-[5H-pyrido[4,3-b]indol-7-yl]pyridin-2-yl)oxy]cyclobutan-1-ol as an off-white solid.

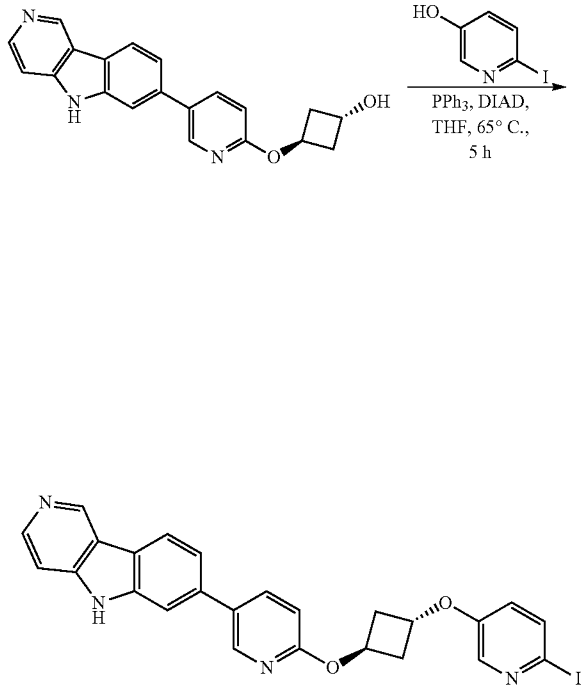

Into a 100-mL round-bottom flask purged and maintained with an inert atmosphere of nitrogen, was placed a mixture (1r,3r)-3-[(5-[5H-pyrido[4,3-b]indol-7-yl]pyridin-2-yl)oxy]cyclobutan-1-ol (1.051 g, 3.17 mmol, 1.0 equiv), 6-iodopyridin-3-ol (0.8 g, 3.62 mmol, 1.15 equiv), $PPh_3$ (1.1 g, 4.12 mmol, 1.3 equiv), and DIAD (0.8 g, 3.96 mmol, 1.25 equiv) in THF (20 mL). The resulting solution was stirred for 5 hours at 60° C. in an oil bath. The resulting solution was extracted with ethyl acetate (50 mL×2), and organic layers were combined and dried over anhydrous sodium sulfate and concentrated under vacuum. The residue was applied onto a silica gel column eluting with dichloromethane/petroleum ether (10/1). This resulted in 939 mg (55%) of 5-[5H-pyrido[4,3-b]indol-7-yl]-2-[(1r,3r)-3-[(6-iodopyridin-3-yl)oxy]cyclobutoxy]pyridine as a brown solid.

Using procedures analogous to that for exemplary compound 220 and those from US 20180125821 the following exemplary compounds were prepared: 332, 223, 234, 224, 233, 222, 231.

Exemplary Synthesis of Exemplary Compound 265

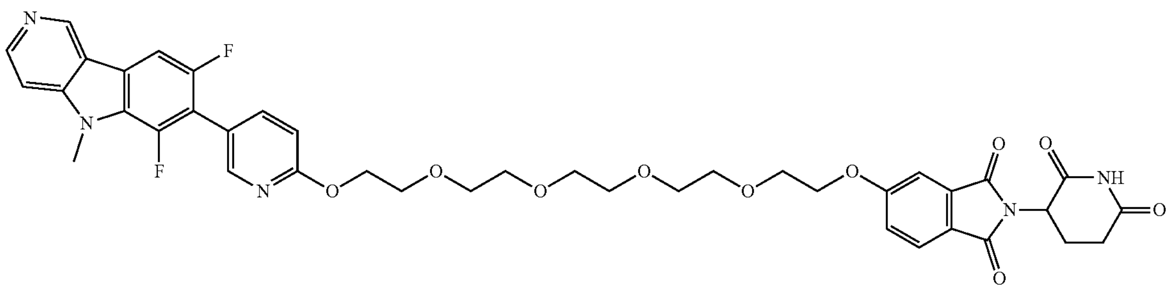 [SMILES: Cn1c2ccncc2c2cc(F)c(-c3ccc(OCCOCCOCCOCCOCCOc4ccc5c(c4)C(=O)N(C4CCC(=O)NC4=O)C5=O)nc3)c(F)c21]

Step 1

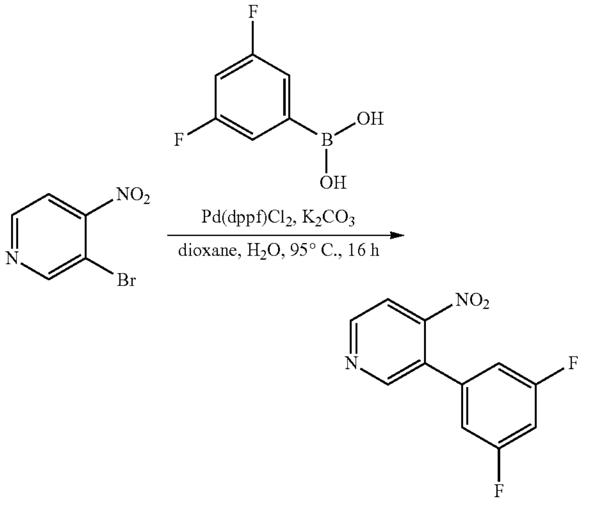

To a solution of 3-bromo-4-nitro-pyridine (5 g, 24.63 mmol, 1 eq) and (3,5-difluorophenyl)boronic acid (4.67 g, 29.56 mmol, 1.2 eq) in dioxane (100 mL) were added water (25 mL), potassium carbonate (6.81 g, 49.26 mmol, 2 eq) and [1,1'-bis(diphenylphosphino)ferrocene]dichloropalladium(ii) (1.80 g, 2.46 mmol, 0.1 eq). The reaction mixture was stirred at 95° C. for 16 hours. The reaction mixture was concentrated under vacuum to remove most of the organic solvents. Then ethyl acetate (60 mL) and water (50 mL) were added. The mixture was separated. The organic layer was dried over sodium sulfate and then concentrated under vacuum. The residue was purified by silica gel column chromatography (5-20% ethyl acetate in petroleum ether) to get 3-(3,5-difluorophenyl)-4-nitro-pyridine (4.7 g, 19.90 mmol, 80% yield) as a white solid.

Step 2

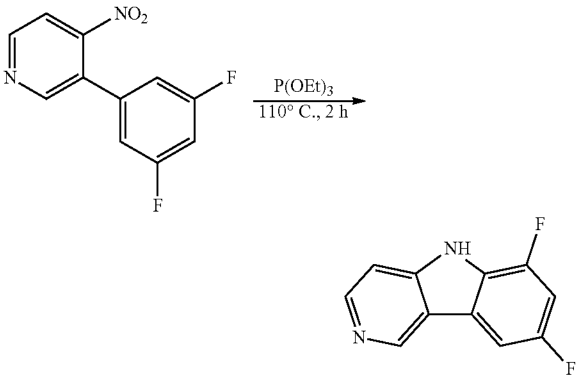

A mixture of 3-(3,5-difluorophenyl)-4-nitro-pyridine (4.7 g, 19.90 mmol, 1 eq) and triethyl phosphite (96.90 g, 583 mmol, 100 mL, 29.31 eq) was heated to 110° C. for 2.5 h under nitrogen atmosphere. The reaction solution was cooled to 15° C. and filtered. The solid was washed with petroleum ether (50 mL). The solid was dried under vacuum to afford 6,8-difluoro-5H-pyrido[4,3-b]indole (1.75 g, 8.57 mmol, 43% yield) as a yellow solid.

Step 3

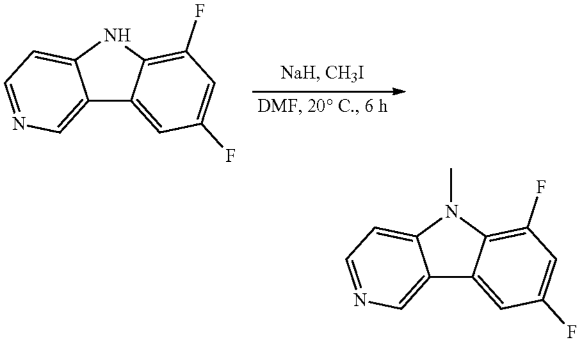

To a suspension of 6,8-difluoro-5H-pyrido[4,3-b]indole (1.75 g, 8.57 mmol, 1 eq) in N,N-dimethylformamide (40 mL) was added sodium hydride (411 mg, 10.29 mmol, 60% purity, 1.2 eq) at 0-5° C. The reaction mixture was stirred at 20° C. for 0.5 h. Then iodomethane (1.22 g, 8.57 mmol, 1 eq) was added and then the reaction mixture stirred at 20° C. for 16 h. Water (20 mL) and brine (30 mL) were added to quench the reaction. The mixture was extracted with ethyl acetate (40 mL×4). The organic layer was dried over sodium sulfate and then concentrated to get the crude product which was purified by silica gel column chromatography (33-100% ethyl acetate in petroleum ether) to afford 6,8-difluoro-5-methyl-pyrido[4,3-b]indole (1.86 g, 8.52 mmol, 99% yield) as a yellow solid.

Step 4

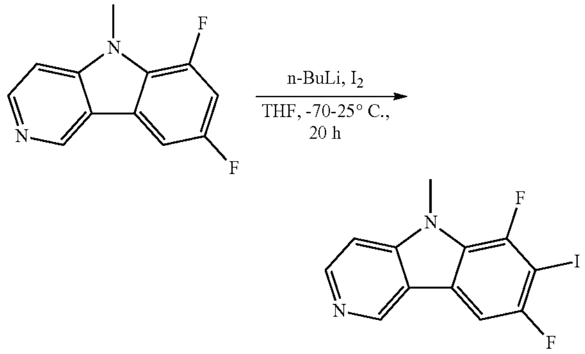

A solution of 6,8-difluoro-5-methyl-pyrido[4,3-b]indole (1.66 g, 7.61 mmol, 1 eq) and tetramethylethylenediamine (884 mg, 7.61 mmol, 1.15 mL, 1 eq) in tetrahydrofuran (30 mL) was cooled to −70° C. Then n-butyllithium (2.5 M, 6.09 mL, 2 eq) was added dropwise, and the reaction mixture was stirred at −70° (for 1 h. A solution of iodine (1.93 g, 7.61 mmol, 1.53 mL, 1 eq) in tetrahydrofuran (10 mL) was added and the reaction mixture was warmed to 15° C. for another 16 h. Water (20 mL) was added to quench the reaction. The mixture was extracted with ethyl acetate (30 mL). The organic layer was washed with water (25 mL×2). The organic layer was dried over sodium sulfate and then concentrated to get the crude product. The crude product was triturated with a mixture of methanol (30 mL) and water (10 mL) to afford 6,8-difluoro-7-iodo-5-methyl-pyrido[4,3-b] indole (1.04 g, 3.02 mmol, 39% yield) as a yellow solid.

Step 5

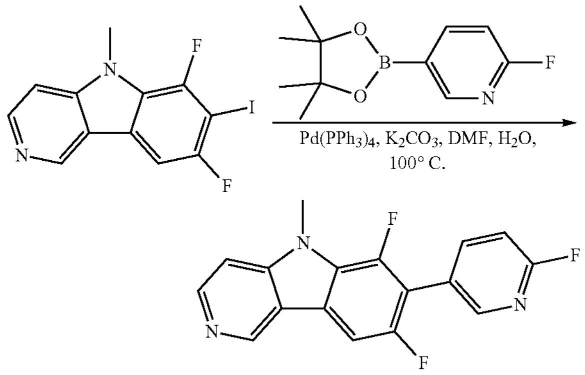

To a solution of 6,8-difluoro-7-iodo-5-methyl-pyrido[4, 3-b]indole (540 mg, 1.57 mmol, 1 eq) and 2-fluoro-5-(4,4, 5,5-tetramethyl-1,3,2-dioxaborolan-2-yl)pyridine (455.05 mg, 2.04 mmol, 1.3 eq) in water (5 mL) were added tetrakis[triphenylphosphine]palladium(0) (181 mg, 0.16 mmol, 0.1 eq), potassium carbonate (434 mg, 3.14 mmol, 2 eq) and N,N-dimethylformamide (10 mL). The reaction mixture was degassed and charged with nitrogen three times and then heated to 100° C. for 2 h. The reaction mixture was separated between ethyl acetate (40 mL) and water (30 mL). The organic layer was washed with brine (30 mL×2), dried over sodium sulfate and then concentrated under vacuum to afford the residue. The residue was triturated with methanol (4 mL) to afford the first portion of the product (195 mg, crude). The filtrate was concentrated under vacuum to get a residue. This residue was purified by silica gel column chromatography (30% ethyl acetate in petroleum ether to 100% ethyl acetate) to afford the second portion of the product (350 mg, crude). 6,8-difluoro-7-(6-fluoro-3-pyridyl)-5-methyl-pyrido[4,3-b]indole (545 mg, crude) was obtained as a yellow solid.

6,8-difluoro-7-(6-fluoro-3-pyridyl)-5-methyl-pyrido[4,3-b]indole was converted to the title compound as shown in the scheme below by using procedures described in US 20180125821, as well as those known to those skilled in the art.

Step 1

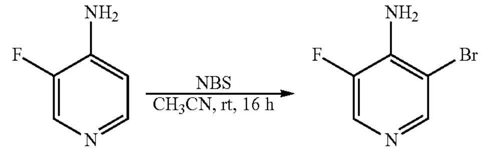

Into a 250-mL round-bottom flask, was placed a solution of 3-fluoropyridin-4-amine (5.0 g, 46.3 mmol, 1 equiv) in acetonitrile (100 mL). This was followed by the addition of a solution of NBS (8.74 g, 49.1 mmol, 1.06 equiv) in acetonitrile (50 mL) dropwise with stirring. The resulting solution was stirred for 16 hr at room temperature. The resulting mixture was concentrated. The residue was applied

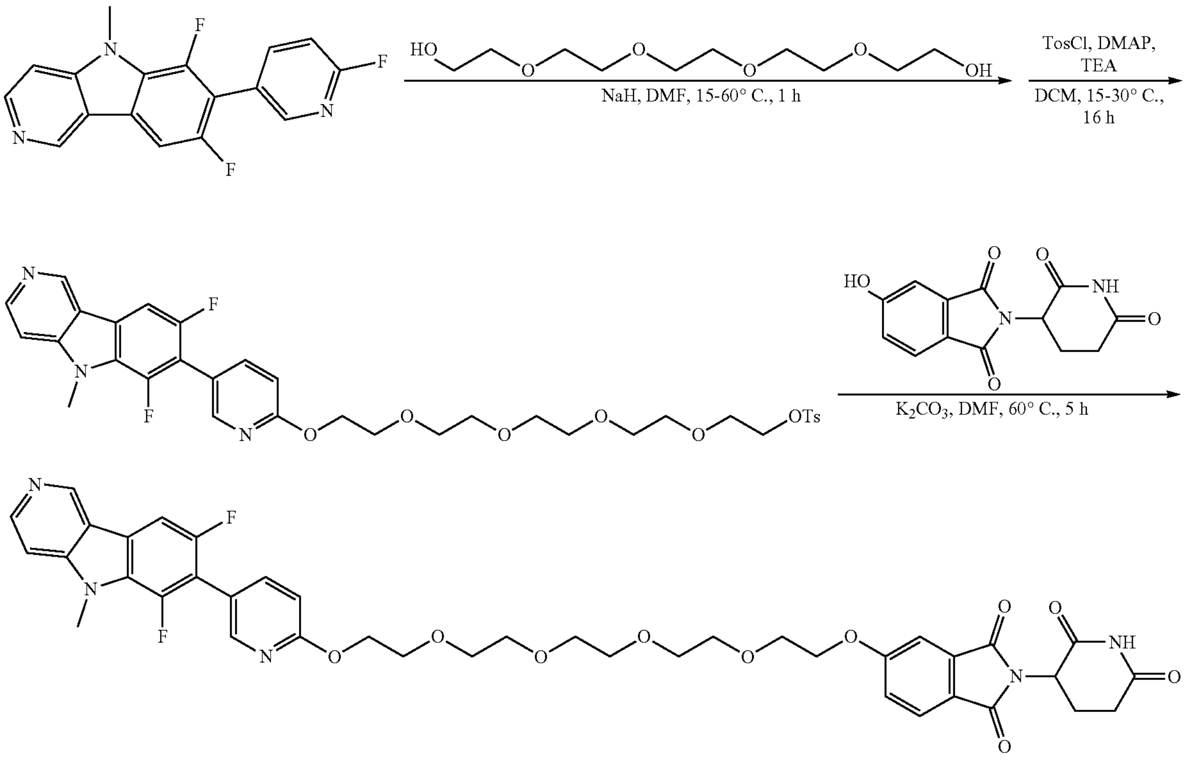

Exemplary Compound 265

Exemplary Synthesis of Exemplary Compound 223

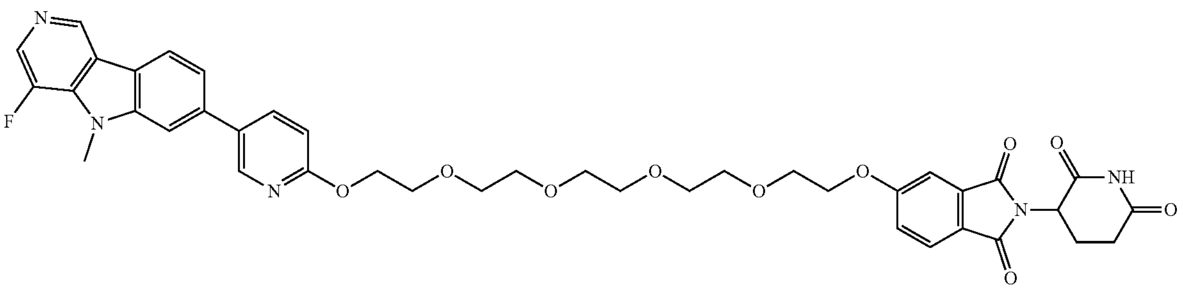 [SMILES: Cn1c2cc(-c3ccc(OCCOCCOCCOCCOCCOc4ccc5c(c4)C(=O)N(C4CCC(=O)NC4=O)C5=O)nc3)ccc2c2cncc(F)c21]

onto a silica gel column with ethyl acetate/petroleum ether (1:1) to afford 3-bromo-5-fluoropyridin-4-amine (7.3 g, 83%) as a yellow solid.

Step 2

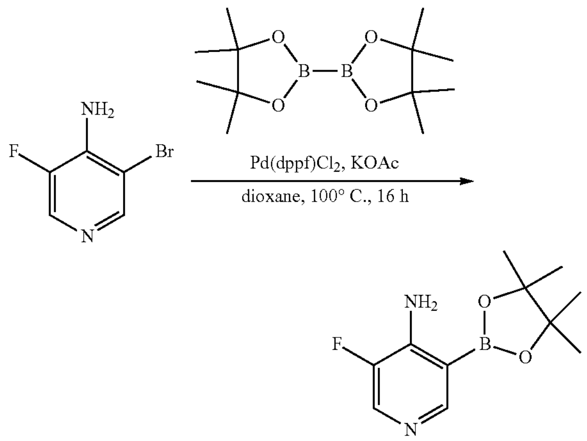

Into a 30-mL sealed tube, was placed a solution of 3-bromo-5-fluoropyridin-4-amine (500 mg, 2.62 mmol, 1 equiv) in dioxane (20 mL), 4,4,5,5-tetramethyl-2-(tetramethyl-1,3,2-dioxaborolan-2-yl)-1,3,2-dioxaborolane (1337 mg, 5.26 mmol, 2 equiv), Pd(dppf)$Cl_2$ (57.8 mg, 0.08 mmol, 0.030 equiv), KOAc (773 mg, 7.88 mmol, 3 equiv). The resulting solution was stirred for 16 hr at 100° C. in an oil bath. The reaction mixture was cooled. The resulting solution was diluted with ethyl acetate (50 mL). The resulting mixture was washed with brine (20 mL×1), dried over anhydrous sodium sulfate, filtered and concentrated under vacuum. The residue was purified by silica gel column (ethyl acetate/petroleum ether=(1:1) to afford 3-fluoro-5-(tetramethyl-1,3,2-dioxaborolan-2-yl)pyridin-4-amine (140 mg, 22%) as a yellow solid.

Step 3

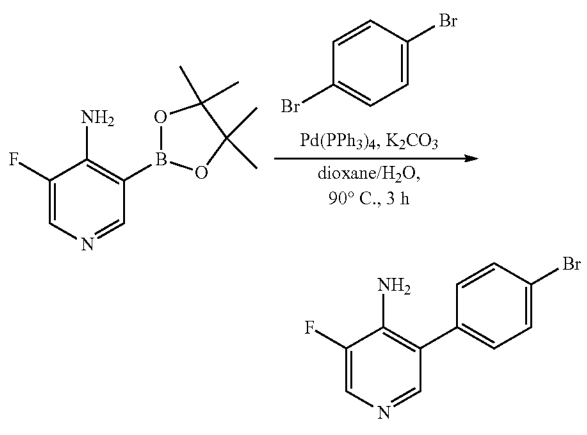

Into a 250-mL round-bottom flask purged and maintained with an inert atmosphere of nitrogen, was placed a solution of 3-fluoro-5-(tetramethyl-1,3,2-dioxaborolan-2-yl)pyridin-4-amine (1.0 g, 4.20 mmol, 1 equiv) in dioxane (100 mL), a solution of $K_2CO_3$ (1.16 g, 8.40 mmol, 2 equiv) in $H_2O$ (40 mL), 1,4-dibromobenzene (1.47 g, 6.23 mmol, 1.48 equiv), $Pd(PPh_3)_4$ (48 mg, 0.04 mmol, 0.010 equiv). The resulting solution was stirred for 3 hr at 90° C. in an oil bath. The resulting solution was diluted with ethyl acetate (100 mL). The resulting mixture was washed with brine (20 mL). The mixture was dried over anhydrous sodium sulfate, filtered and concentrated under vacuum. The residue was purified by silica gel column (ethyl acetate/petroleum ether=1:1) to afford 3-(4-bromophenyl)-5-fluoropyridin-4-amine (1.4 g, 99%) as a yellow oil.

Step 4

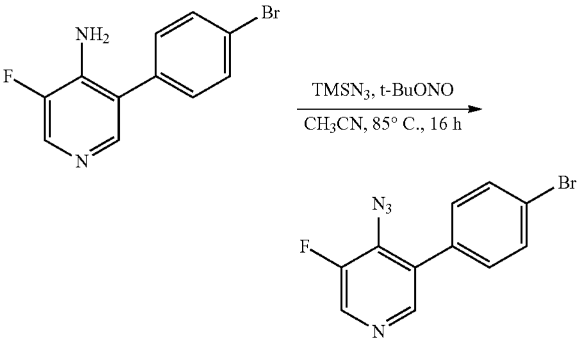

Into a 250-mL round-bottom flask, was placed a solution of 3-(4-bromophenyl)-5-fluoropyridin-4-amine (1.4 g, 5.24 mmol, 1 equiv) in acetonitrile (50 mL), t-BuONO (2.7 g, 26.2 mmol, 5.0 equiv), $TMSN_3$ (3.02 g, 26.2 mmol, 5.0 equiv). The resulting solution was stirred for 16 hr at 80° C. in an oil bath. The resulting mixture was concentrated under vacuum. The residue was applied onto a silica gel column eluting with ethyl acetate/petroleum ether (1:1) to afford 4-azido-3-(4-bromophenyl)-5-fluoropyridine (500 mg, 32%) as a yellow oil.

Step 5

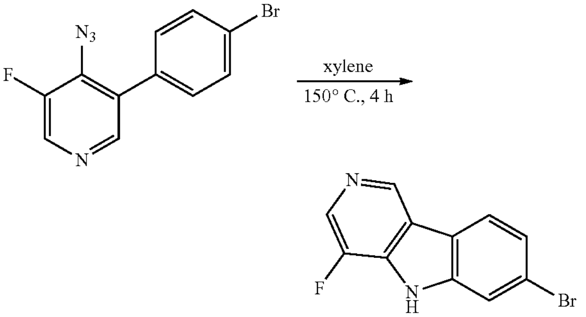

Into a 50-mL round-bottom flask, was placed a solution of 4-azido-3-(4-bromophenyl)-5-fluoropyridine (500 mg, 1.71 mmol) in xylene (10 mL). The resulting solution was stirred for 4 hr at 150° C. in an oil bath. The reaction mixture was cooled. The resulting mixture was concentrated. The residue was purified by silica gel column (ethyl acetate/petroleum ether=1:1) to afford 7-bromo-4-fluoro-5H-pyrido[4,3-b]indole (105 mg, 23%) as a yellow solid.

Step 6

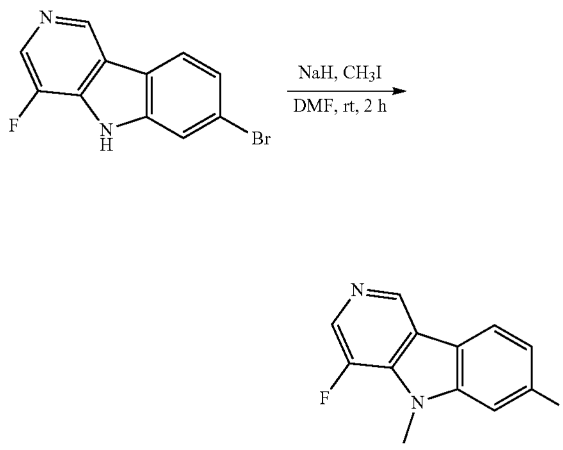

Into a 50-mL round-bottom flask, was placed a solution of 7-bromo-4-fluoro-5H-pyrido[4,3-b]indole (91 mg, 0.34 mmol, 1 equiv) in DMF (5 mL). This was followed by the addition of NaH (25 mg, 1.03 mmol, 3 equiv) and stirring at rt for 0.5 h. To this was added $CH_3I$ (50 mg, 0.35 mmol, 1 equiv). The resulting solution was stirred for 3 hr at room temperature. The reaction was then quenched by the addition of water (10 mL). The resulting solution was extracted with ethyl acetate (30 mL×3). The mixture was dried over anhydrous sodium sulfate, filtered and concentrated under vacuum. The residue was purified by silica gel column (ethyl acetate/petroleum ether=(1:1) to afford 7-bromo-4-fluoro-5-methyl-5H-pyrido[4,3-b]indole (80 mg, 83%) as a yellow solid.

Step 7

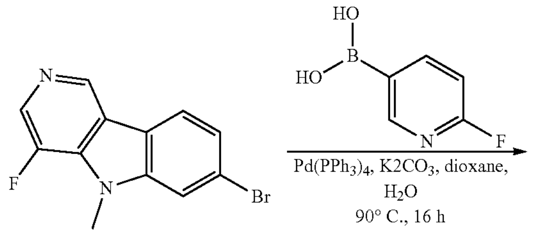

-continued

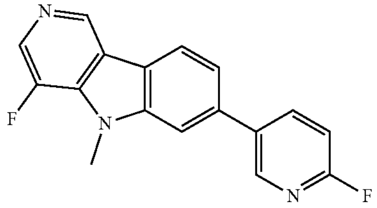

Into a 100-mL round-bottom flask, was placed a solution of 7-bromo-4-fluoro-5-methyl-5H-pyrido[4,3-b]indole (370 mg, 1.33 mmol, 1 equiv) in dioxane (20 mL), (6-fluoropyridin-3-yl)boronic acid (282 mg, 2.00 mmol, 1.5 equiv), $Pd(PPh_3)_4$ (15.4 mg, 0.01 mmol, 0.01 equiv), $K_2CO_3$ (459 mg, 3.32 mmol, 2.5 equiv), and water (4 mL). The resulting solution was stirred for 16 hr at 90° C. in an oil bath. The resulting mixture was concentrated under vacuum. The residue was purified by silica gel column (ethyl acetate/petroleum ether=(1:1) to afford 2-fluoro-5-[4-fluoro-5-methyl-5H-pyrido[4,3-b]indol-7-yl]pyridine (390 mg, 99%) as a yellow solid.

2-fluoro-5-[4-fluoro-5-methyl-5H-pyrido[4,3-b]indol-7-yl]pyridine was converted to the title compound using procedures analogous to those described above for exemplary compound 265.

Exemplary Synthesis of Exemplary Compound 258

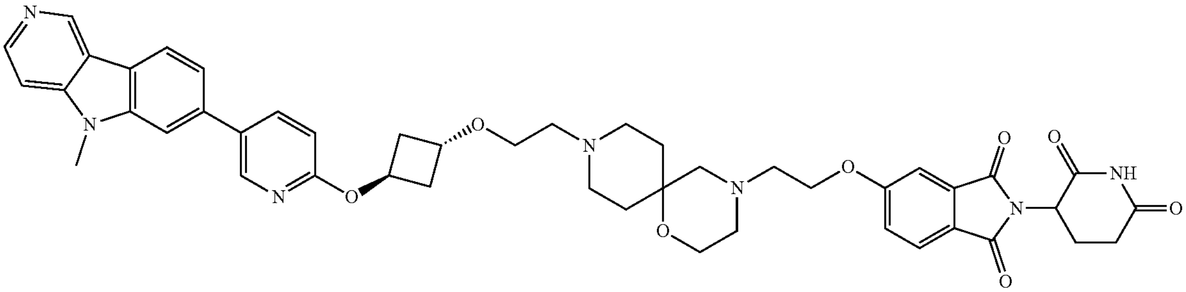 [SMILES: Cn1c2ccncc2c2ccc(-c3ccc(O[C@H]4C[C@H](OCCN5CCC6(CC5)CN(CCOc5ccc7c(c5)C(=O)N(C5CCC(=O)NC5=O)C7=O)CCO6)C4)nc3)cc21]

Step 1

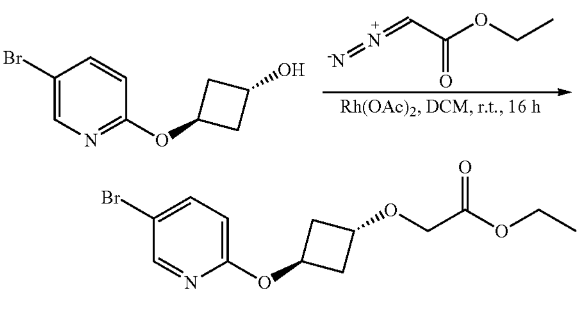

To a solution of 3-[(5-bromo-2-pyridyl)oxy]cyclobutanol (1.0 g, 4.10 mmol, 1 eq) [prepared as described in US 20180125821] and rhodium acetate (91 mg, 0.41 mmol, 0.1 eq) in dichloromethane (10 mL) was added ethyl 2-diazoacetate (1.40 g, 12.29 mmol, 3 eq). The reaction mixture was stirred at 25° C. for 12 h. The reaction mixture was concentrated under reduced pressure to give a residue. The residue was purified by silica gel chromatography (petroleum ether:ethyl acetate=1:0). The desired compound ethyl 2-[3-[(5-bromo-2-pyridyl)oxy]cyclobutoxy]acetate (840 mg, 2.54 mmol, 62% yield) was obtained as a light yellow oil.

Step 2

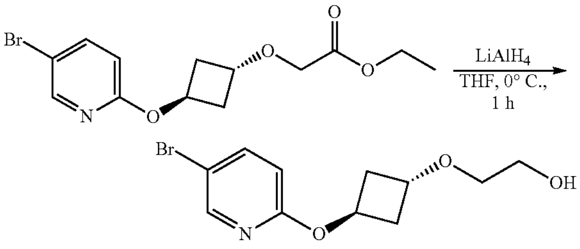

To a suspension of lithium aluminum hydride (92 mg, 2.42 mmol, 2 eq) in tetrahydrofuran (10 mL) was added ethyl 2-[3-[(5-bromo-2-pyridyl)oxy]cyclobutoxy]acetate (400 mg, 1.21 mmol, 1 eq) at 0° C. The reaction mixture was stirred at 0° C. for 1 h. The reaction mixture was quenched by the addition water (0.1 mL) at 0° C., then 15% sodium hydroxide 0.1 mL, and then 0.3 mL of water. The solid was filtered and washed with ethyl acetate (10 mL). The combined organic layers were concentrated under reduced pressure to give a residue. The residue was purified by silica gel chromatography (petroleum ether:ethyl acetate=20:1 to 5:1). The desired compound 2-[3-[(5-bromo-2-pyridyl)oxy]cyclobutoxy]ethanol (200 mg, 0.69 mmol, 57% yield) was obtained as a colorless oil.

Step 3

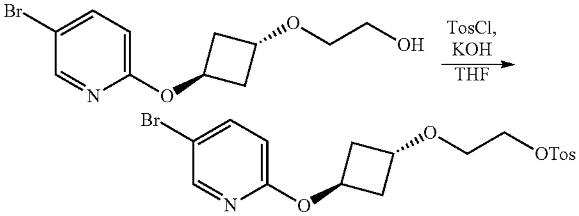

To a solution of 2-[3-[(5-bromo-2-pyridyl)oxy]cyclobutoxy]ethanol (300 mg, 1.04 mmol, 1 eq) and p-toluenesulfonyl chloride (595 mg, 3.12 mmol, 3 eq) in tetrahydrofuran (5 mL) was added potassium hydroxide (584 mg, 10.41 mmol, 10 eq). The reaction mixture was stirred at 25° C. for 0.5 h. The reaction mixture was quenched by the addition of water (10 mL), and then diluted with water (20 mL) and extracted with ethyl acetate (50 mL×3). The combined organic layers were washed with brine (40 mL×2), dried over anhydrous sodium sulfate, filtered and concentrated under reduced pressure to give a residue. The residue was purified by silica gel chromatography (petroleum ether:ethyl acetate=50:1 to 20:1). The desired compound 2-[3-[(5-bromo-2-pyridyl)oxy]cyclobutoxy]ethyl 4-methylbenzenesulfonate (360 mg, 0.81 mmol, 78% yield) was obtained as a colorless oil.

Step 4

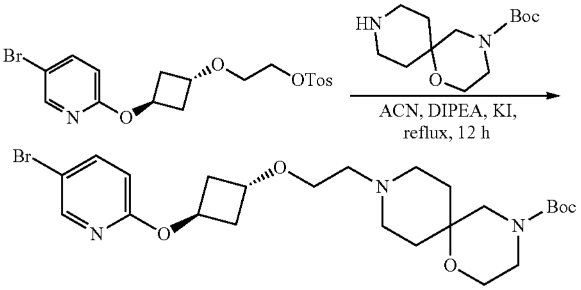

To a solution of 2-[3-[(5-bromo-2-pyridyl)oxy]cyclobutoxy]ethyl 4-methylbenzenesulfonate (300 mg, 0.68 mmol, 1 eq) and tert-butyl 1-oxa-4,9-diazaspiro[5.5]undecane-4-carboxylate (209 mg, 0.81 mmol, 1.2 eq) in acetonitrile (3 mL) was added N,N-diisopropylethylamine (263 mg, 2.03 mmol, 3 eq) and potassium iodide (113 mg, 0.68 mmol, 1 eq). The reaction mixture was stirred at 100° C. for 12 h. The reaction mixture was quenched by addition water 10 mL, and then further diluted with water (20 mL) and extracted with ethyl acetate (50 mL×3). The combined organic layers were washed with brine (40 mL×2), dried over anhydrous sodium sulfate, filtered and concentrated under reduced pressure to give a residue. The residue was purified by silica gel chromatography (dichloromethane:methanol=100:1 to 20:1). The desired compound tert-butyl 9-[2-[3-[(5-bromo-2-pyridyl)oxy]cyclobutoxy] ethyl]-1-oxa-4,9-diazaspiro[5.5]undecane-4-carboxylate (300 mg, 0.55 mmol, 81% yield) was obtained as a light yellow oil.

Step 5

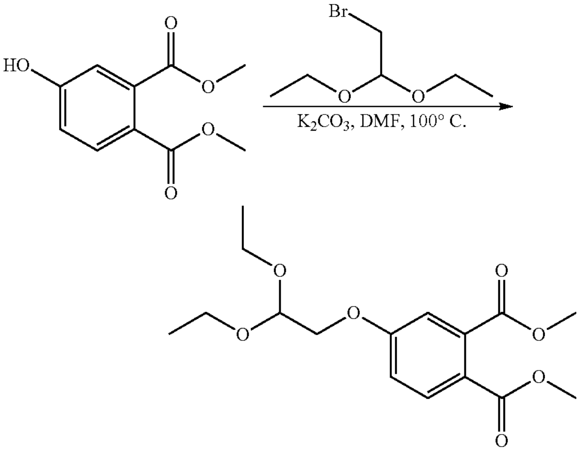

To a solution of dimethyl 4-hydroxybenzene-1,2-dicarboxylate (2 g, 9.52 mmol, 1 eq) and 2-bromo-1,1-diethoxyethane (3.75 g, 19.03 mmol, 2 eq) in N,N-dimethylformamide (5 mL) was added potassium carbonate (3.95 g, 28.55 mmol, 3 eq). The reaction mixture was stirred at 100° C. for 3 h. The reaction mixture was quenched by addition water (30 mL), and then extracted with ethyl acetate (50 mL×3). The combined organic layers were washed with brine (30 mL×3), dried over anhydrous sodium sulfate, filtered and concentrated under reduced pressure to give a residue. The residue was purified by silica gel chromatography (petroleum ether:ethyl acetate=100:1 to 5:1). The desired compound dimethyl 4-(2,2-diethoxyethoxy)benzene-1,2-dicarboxylate (2.86 g, 8.76 mmol, 92% yield) was obtained as a colorless oil.

Step 6

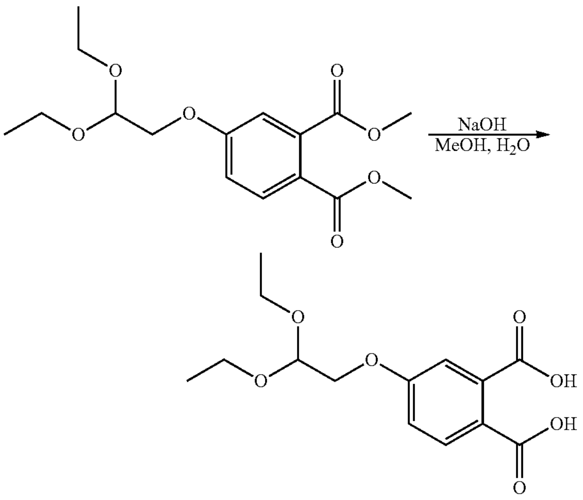

To a solution of dimethyl 4-(2,2-diethoxyethoxy)benzene-1,2-dicarboxylate (3 g, 9.19 mmol, 1 eq) in methanol (10 mL) and water (5 mL) was added sodium hydroxide (3.68 g, 91.93 mmol, 10 eq). The reaction mixture was stirred at 25° C. for 1 h. The pH was adjusted to 4-5 with 1M hydrogen chloride, and the reaction mixture was extracted with ethyl acetate (30 mL×3). The combined organic layers were washed with brine (30 mL×2), dried over anhydrous sodium sulfate, filtered and concentrated under reduced pressure to give a residue. The product was taken to the next step without purification. The crude desired compound 4-(2,2-diethoxyethoxy)phthalic acid (2.5 g, 8.38 mmol) was obtained as a white solid.

Step 7

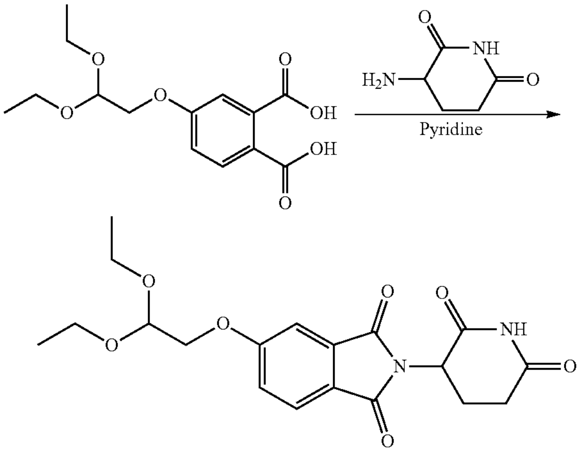

To a solution of 4-(2,2-diethoxyethoxy)phthalic acid (1 g, 3.35 mmol, 1 eq) in pyridine (5 mL) was added 3-aminopiperidine-2,6-dione hydrochloride (828 mg, 5.03 mmol, 1.5 eq). The reaction mixture was stirred at 100° C. for 13 h. The reaction mixture was concentrated under reduced pressure to give a residue, and then diluted with water 50 mL and extracted with ethyl acetate (50 mL×2). The combined organic layers were washed with brine (50 mL×2), dried over anhydrous sodium sulfate, filtered and concentrated under reduced pressure to give a residue. The residue was purified by silica gel chromatography (petroleum ether:ethyl acetate=10:1 to 1:1). The desired compound 5-(2,2-diethoxyethoxy)-2-(2,6-dioxo-3-piperidyl)isoindoline-1,3-dione (330 mg, 0.85 mmol, 25% yield) was obtained as an off-white solid.

Step 8

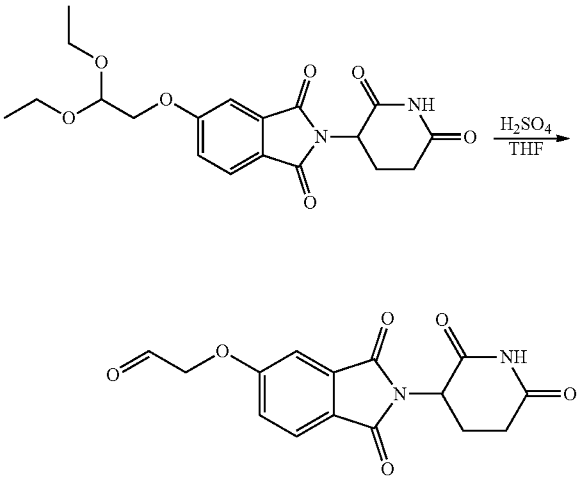

To a solution of 5-(2,2-diethoxyethoxy)-2-(2,6-dioxo-3-piperidyl)isoindoline-1,3-dione (330 mg, 0.85 mmol, 1 eq) in tetrahydrofuran (17 mL) was added sulfuric acid (2 M, 17 mL, 40 eq). The reaction mixture was stirred at 70° C. for 0.5 h. The reaction mixture was quenched by the addition of saturated sodium bicarbonate solution to pH=7~8 and extracted with ethyl acetate (30 mL×2). The combined organic layers were washed with brine (60 mL), dried over sodium sulfate, filtered and concentrated under reduced pressure to give a residue. The product was taken to the next step without purification. The crude desired compound 2-[2-(2,6-dioxo-3-piperidyl)-1,3-dioxo-isoindolin-5-yl]oxyacetaldehyde (200 mg, 0.63 mmol, 75% yield) was obtained as an off-white solid.

tert-Butyl 9-[2-[3-[(5-bromo-2-pyridyl)oxy]cyclobutoxy]ethyl]-1-oxa-4,9-diazaspiro[5.5]undecane-4-carboxylate was converted to the title compound as shown in the scheme below using procedures analogous to those described for the examples above as well as known to those skilled in the art.

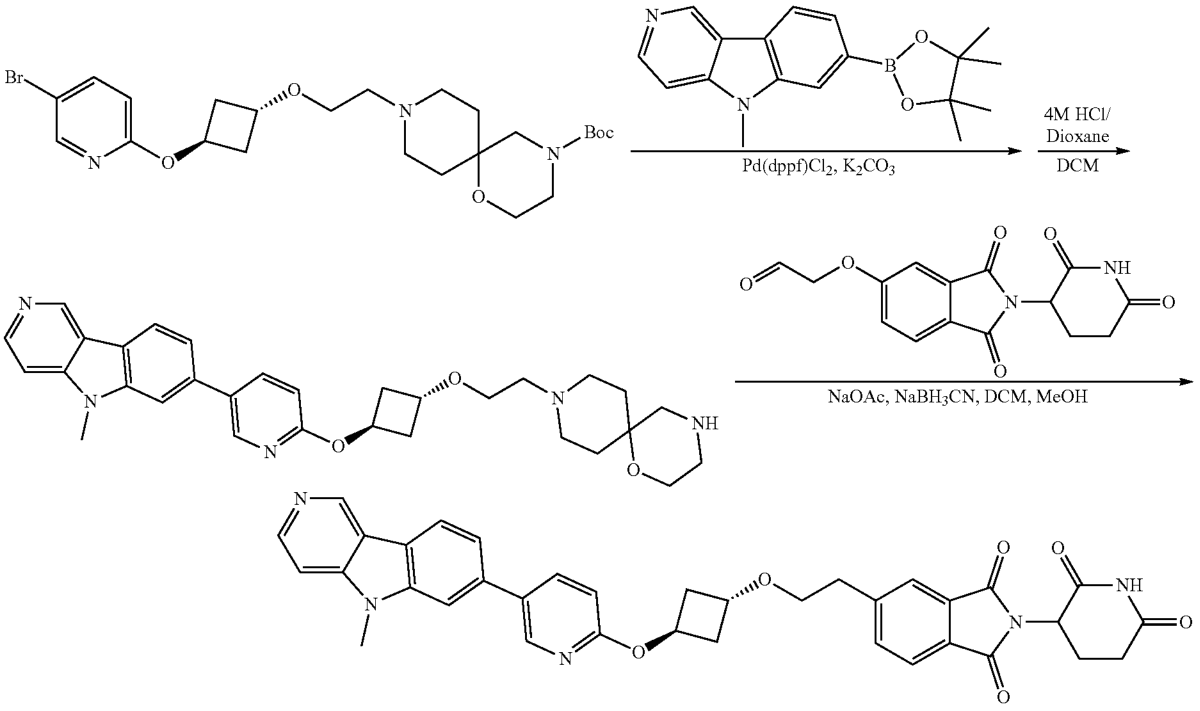

Exemplary Compound 258

Exemplary Synthesis of Exemplary Compound 333

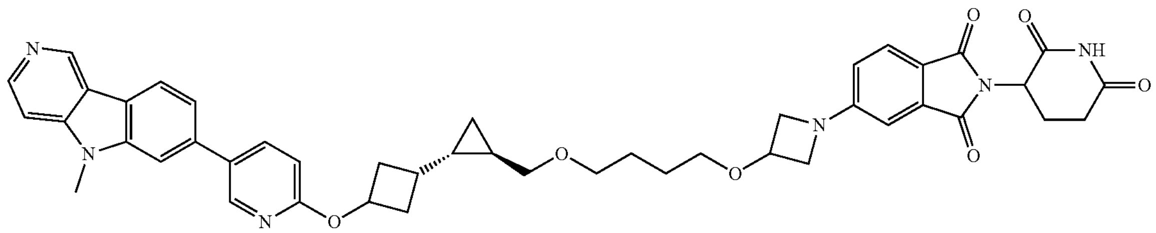 [SMILES: Cn1c2ccncc2c2ccc(-c3ccc(OC4CC([C@@H]5C[C@H]5COCCCCOC5CN(c6ccc7c(c6)C(=O)N(C6CCC(=O)NC6=O)C7=O)C5)C4)nc3)cc21]

Step 1

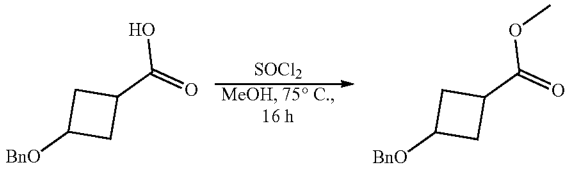 [SMILES: O=C(O)C1CC(OCc2ccccc2)C1 ; "SOCl2" ; "MeOH, 75° C.,16 h" ; COC(=O)C1CC(OCc2ccccc2)C1]

Step 2

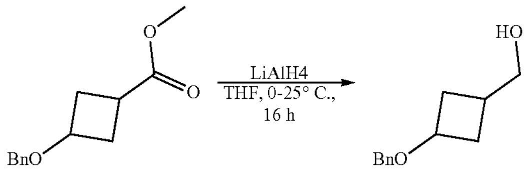 [SMILES: COC(=O)C1CC(OCc2ccccc2)C1 ; "LiAlH4" ; "THF, 0-25° C.,16 h" ; OCC1CC(OCc2ccccc2)C1]

To a solution of 3-benzyloxycyclobutanecarboxylic acid (10 g, 48.49 mmol, 1 eq) in methanol (100 mL) was added thionyl chloride (11.54 g, 96.98 mmol, 7.03 mL, 2 eq) dropwise at 0° C., then heated to 75° C. and stirred for 16 h. The reaction mixture was concentrated to give a residue which was purified by silica gel column chromatography (petroleum ether/ethyl acetate=20/1 to 5/1). Methyl 3-benzyloxycyclobutanecarboxylate (10.13 g, 45.99 mmol, 94% yield) was obtained as a colorless oil.

To a solution of methyl 3-benzyloxycyclobutanecarboxylate (18.65 g, 84.67 mmol, 1 eq) in tetrahydrofuran (180 mL) was slowly added lithium aluminum hydride (3.44 g, 90.60 mmol, 1.07 eq) at 0° C. The reaction was stirred at 25° C. for 16 h. The reaction mixture was quenched with water (3.5 mL), then 15% sodium hydroxide aqueous solution (7 mL) and water (10.5 mL) were added sequentially. The resulting mixture was filtered, and the filtrate was concentrated under reduced pressure. The residue was purified by silica gel column chromatography (petroleum ether/ethyl acetate=10/1 to 3/1). (3-Benzyloxycyclobutyl)methanol (16.34 g, crude) was obtained as a colorless oil.

Step 3

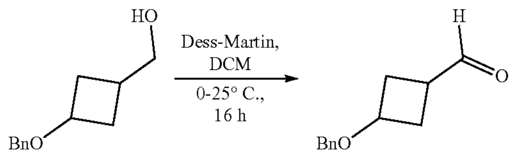 [SMILES: OCC1CC(OCc2ccccc2)C1 ; O=CC1CC(OCc2ccccc2)C1]

To a solution of (3-benzyloxycyclobutyl)methanol (13.7 g, 71.26 mmol, 1 eq) in dichloromethane (150 mL) was added Dess-Martin periodinane (45.34 g, 106.9 mmol, 1.5 eq) in three portions at 0° C., then the reaction mixture was stirred at 25° C. for 16 h. The reaction mixture was diluted with 800 mL of petroleum ether, and then filtered and the filtrate was concentrated to give crude product. The crude product was purified by silica gel column chromatography (petroleum ether/ethyl acetate=100/1 to 20/1). 3-Benzyloxycyclobutanecarbaldehyde (6.58 g, 34.59 mmol, 48% yield) was obtained as a colorless oil.

Step 4

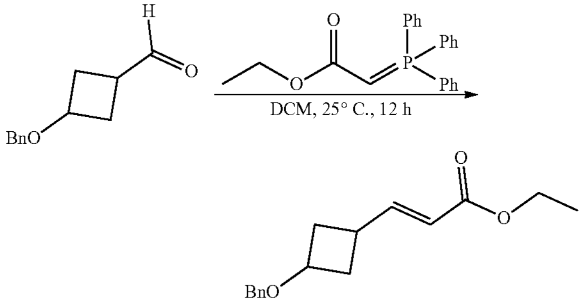

A solution of 3-benzyloxycyclobutanecarbaldehyde (6.58 g, 34.59 mmol, 1 eq) and ethyl 2-(triphenylphosphoranylidene)acetate (14.46 g, 41.51 mmol, 1.2 eq) in dichloromethane (65 mL) was stirred at 25° C. for 12 h. The reaction mixture was concentrated to give a residue which was purified by silica gel column chromatography (petroleum ether/ethyl acetate=100/1 to 30:1). Ethyl (E)-3-(3-benzyloxycyclobutyl)prop-2-enoate (8.24 g, 31.65 mmol, 91% yield) was obtained as a colorless oil.

Step 5

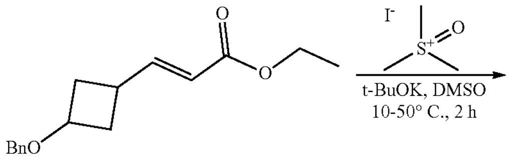

-continued

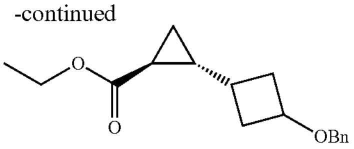

To a solution of trimethylsulfoxonium iodide (7.66 g, 34.82 mmol, 1.1 eq) in dimethyl sulfoxide (20 mL) was added potassium tert-butoxide (3.91 g, 34.82 mmol, 1.1 eq) at 10 to 20° C. under nitrogen. The mixture was stirred at 10 to 20° C. for 1 h and was then added to a solution of ethyl (E)-3-(3-benzyloxycyclobutyl)prop-2-enoate (8.24 g, 31.65 mmol, 1 eq) in dimethyl sulfoxide (40 mL) at 50° C. under nitrogen. The mixture was stirred at 50° C. for 1 h. The reaction mixture was poured into water (100 mL). The aqueous phase was extracted with ethyl acetate (80 mL×3). The combined organic phase was washed with water (30 mL×3), brine (30 mL×2), dried with anhydrous sodium sulfate, filtered and concentrated in vacuum. The residue was purified by silica gel column chromatography (petroleum ether/ethyl acetate=60/1 to 20/1). Ethyl 2-(3-benzyloxycyclobutyl)cyclopropanecarboxylate (2.15 g, 7.84 mmol, 24% yield) was obtained as a colorless oil.

Step 6

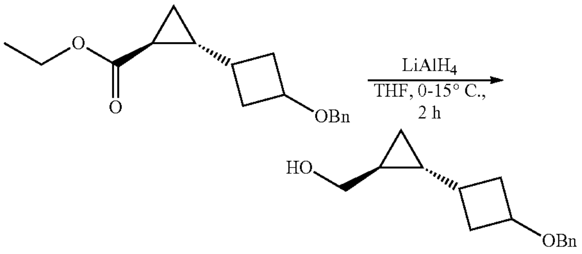

To a solution of ethyl 2-(3-benzyloxycyclobutyl)cyclopropanecarboxylate (2.15 g, 7.84 mmol, 1 eq) in tetrahydrofuran (20 mL) was added lithium aluminum hydride (297 mg, 7.84 mmol, 1 eq) slowly at 0° C. The reaction was stirred at 15° C. for 2 h. The reaction mixture was quenched with water (0.3 mL), then 15% sodium hydroxide aqueous solution (0.3 mL) and water (0.9 mL) were added sequentially. The resulting mixture was filtered and the filtrate was concentrated under reduced pressure. The residue was purified by silica gel column chromatography (Petroleum ether/Ethyl acetate=20/1 to 2/1). [(1R,2S)-2-(3-Benzyloxycyclobutyl)cyclopropyl]methanol (1.6 g, 6.89 mmol, 88% yield) was obtained as a colorless oil.

Step 7

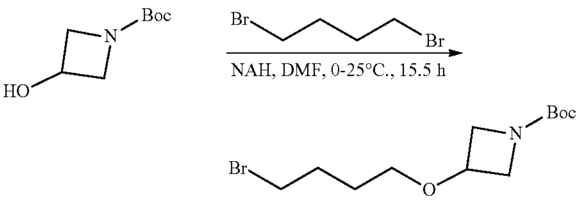

To a solution of tert-butyl 3-hydroxyazetidine-1-carboxylate (5 g, 28.87 mmol, 1 eq) in N,N-dimethylformamide (50 mL) was added sodium hydride (1.73 g, 43.30 mmol, 60% purity, 1.5 eq) at 0° C. over a period of 30 minutes under nitrogen. To the mixture was then added 1,4-dibromobutane (15.58 g, 72.17 mmol, 8.70 mL, 2.5 eq), and the mixture was warmed to 25° C. for 15 h. The residue was poured into water (250 mL) and stirred for 10 min. The aqueous phase was extracted with ethyl acetate (50 mL×3). The combined organic phase was washed with brine (50 mL×2), dried with anhydrous sodium sulfate, filtered and concentrated in vacuum. The residue was purified by silica gel column chromatography (petroleum ether/ethyl acetate=1:0 to 15:1). tert-butyl 3-(4-bromobutoxy)azetidine-1-carboxylate (3.2 g, 10.38 mmol, 35% yield) was obtained as a yellow oil.

Step 8

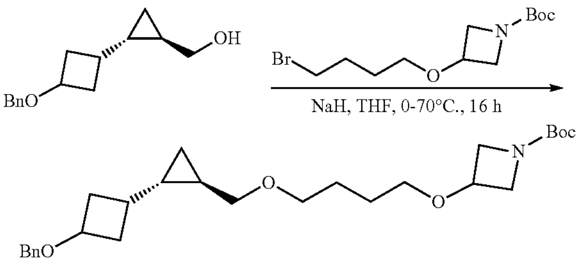

To a solution of [(1S,2R)-2-(3-benzyloxycyclobutyl)cyclopropyl]methanol (1.55 g, 6.67 mmol, 1 eq) in tetrahydrofuran (15 mL) was added sodium hydride (533 mg, 13.34 mmol, 60%, 2 eq) slowly at 0° C., and the mixture was stirred for 1 h at 15° C. Then a solution of tert-butyl 3-(4-bromobutoxy)azetidine-1-carboxylate (2.26 g, 7.34 mmol, 1.1 eq) in tetrahydrofuran (20 mL) was added to the reaction mixture dropwise at 0° C., and the mixture was heated to 70° C. and stirred for 16 h. The reaction mixture was quenched by the addition of water (20 mL) at 0° C., and then extracted with ethyl acetate (50 mL×3). The combined organic layers were washed with brine (10 mL), dried with anhydrous sodium sulfate, filtered and concentrated under reduced pressure to give a residue. The residue was purified by silica gel column chromatography (petroleum ether/ethyl acetate=20/1 to 2/1), then purified by prep-TLC (petroleum ether:ethyl acetate=3:1). tert-Butyl 3-[4-[[(1S,2R)-2-(3-benzyloxycyclobutyl)cyclopropyl]methoxy]butoxy]azetidine-1-carboxylate (535 mg, 1.16 mmol, 17% yield) was obtained as a yellow oil. 783 mg starting material [2-(3-benzyloxycyclobutyl)cyclopropyl]methanol was recovered.

Step 9

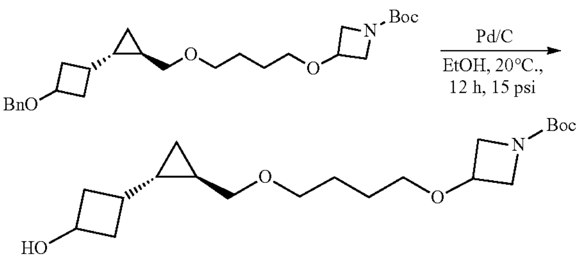

To a solution of tert-butyl 3-[4-[[(1S,2R)-2-(3-benzyloxycyclobutyl)cyclopropyl]methoxy]butoxy]azetidine-1-carboxylate (535 mg, 1.16 mmol, 1 eq) in ethanol (15 mL) was added 10% palladium on carbon (100 mg) under nitrogen. The suspension was degassed under vacuum and purged with hydrogen several times. The mixture was stirred under hydrogen (15 psi) at 20° C. for 12 h. The reaction mixture was filtered, and the filtrate was concentrated. The residue was purified by silica gel column chromatography (petroleum ether/ethyl acetate=10/1 to 1/1). tert-Butyl 3-[4-[[(1S,2R)-2-(3-hydroxycyclobutyl)cyclopropyl]methoxy]butoxy]azetidine-1-carboxylate (377 mg, 1.02 mmol, 87% yield) was obtained as a colorless oil.

tert-Butyl 3-[4-[[(1S,2R)-2-(3-hydroxycyclobutyl)cyclopropyl]methoxy]butoxy]azetidine-1-carboxylate was converted to the title compound as shown in the scheme below using procedures described above as well as common procedures known to those skilled in the art.

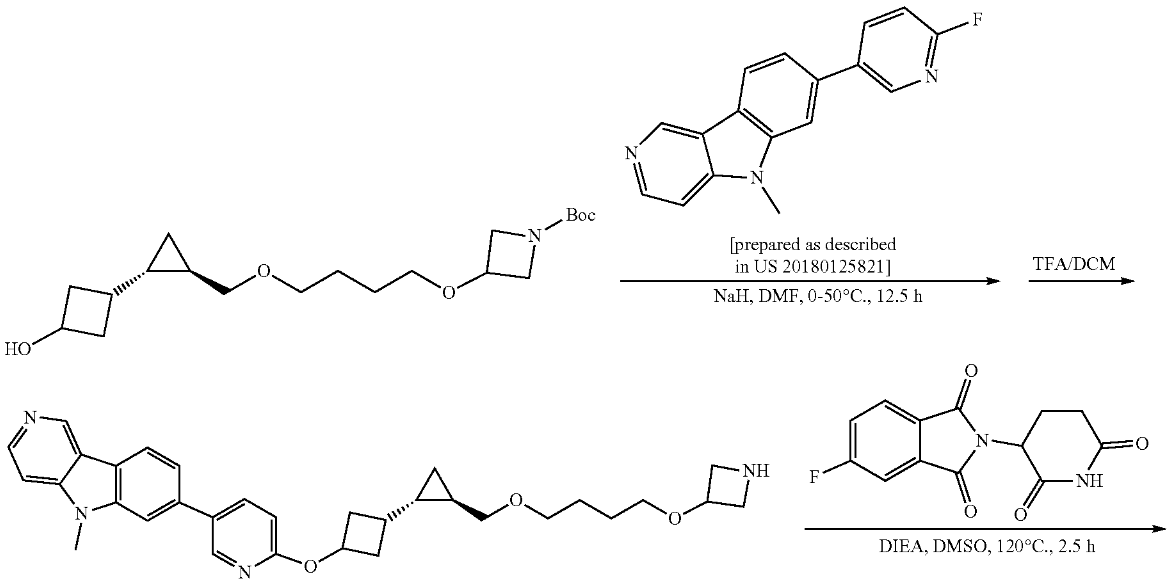

-continued

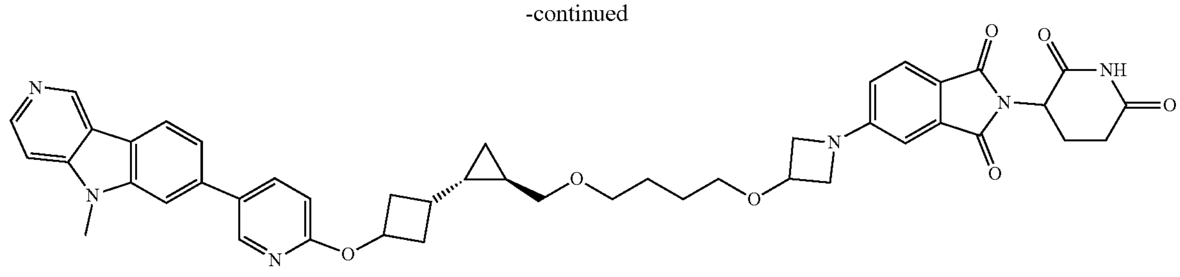

Exemplary Compound 333

Exemplary Synthesis of Exemplary Compound 217

Step 1

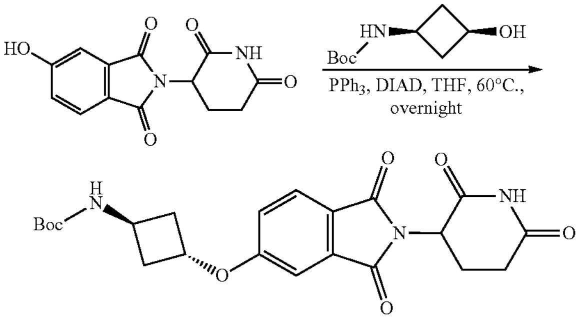

Into a 100-mL round-bottom flask, was placed $PPh_3$ 1.5 equiv), THF (30 mL), DIAD 1.2 equiv), tert-butyl N-[(1s, 3s)-3-hydroxycyclobutyl]carbamate (500 mg, 1 equiv), and 2-(2,6-dioxopiperidin-3-yl)-5-hydroxy-2,3-dihydro-1H-isoindole-1,3-dione 1 equiv). The resulting solution was stirred for overnight at 60° C. in an oil bath. The reaction was then quenched by the addition of water (20 mL). The resulting solution was extracted with ethyl acetate (40 mL). The resulting mixture was washed with brine (40 mL). The mixture was dried over anhydrous sodium sulfate. The residue was applied onto a silica gel column eluting with ethyl acetate/petroleum ether (1/1). The collected fractions were combined and concentrated. This resulted in 1.5 g (crude) of tert-butyl N-[(1r,3r)-3-[[2-(2,6-dioxopiperidin-3-yl)-1,3-dioxo-2,3-dihydro-1H-isoindol-5-yl]oxy]cyclobutyl]carbamate as a yellow solid.

Step 2

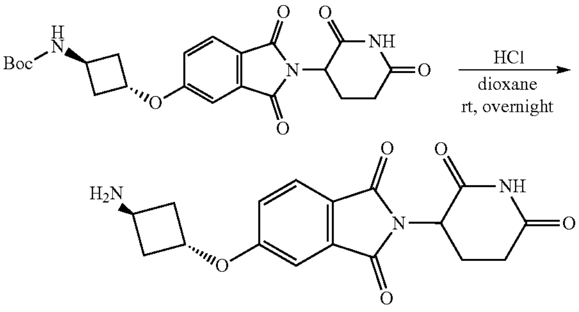

Into a 50-mL round-bottom flask, was placed tert-butyl N-[(1r,3r)-3-[[2-(2,6-dioxopiperidin-3-yl)-1,3-dioxo-2,3-dihydro-1H-isoindol-5-yl]oxy]cyclobutyl]carbamate (1.5 g, crude), and dioxane/hydrogen chloride (4M, 20 mL). The resulting solution was stirred overnight at room temperature. The resulting mixture was concentrated. This resulted in 610 mg of crude 2-(2,6-dioxopiperidin-3-yl)-5-[(1r,3r)-3-aminocyclobutoxy]-2,3-dihydro-1H-isoindole-1,3-dione hydrochloride as a yellow solid.

2-(3-((1r,3r)-3-((5-(5-methyl-5H-pyrido[4,3-b]indol-7-yl)pyridin-2-yl)oxy)cyclobutoxy)propoxy)ethan-1-ol was prepared according to the scheme below using procedures analogous to those described in US 20180125821 and for other examples above and known to those skilled in the art.

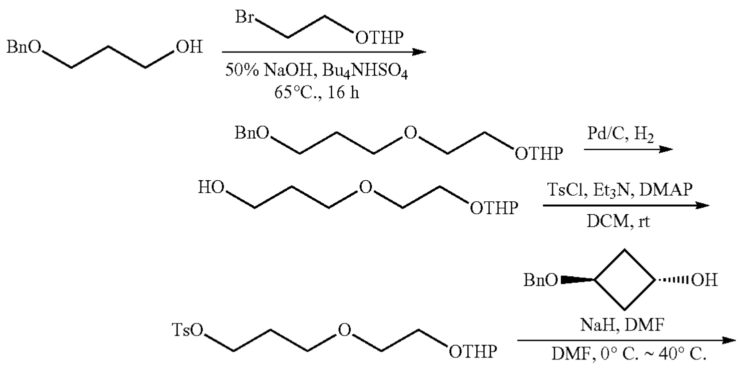

-continued

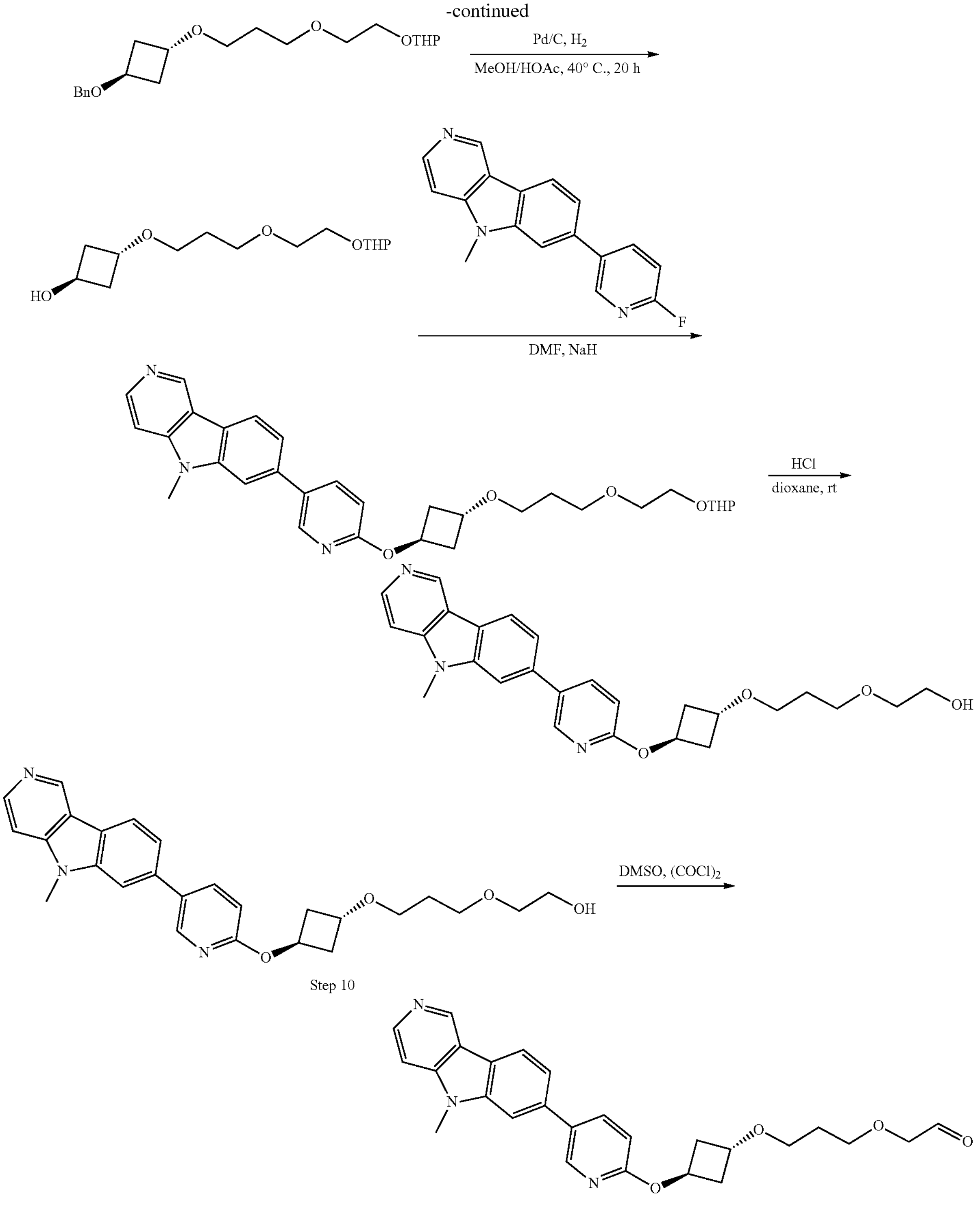

Into a 25-mL round-bottom flask purged and maintained with an inert atmosphere of nitrogen, was placed a solution of $(COCl)_2$ (705 mg, 5.60 mmol, 5.0 equiv) in dichloromethane (10 mL). This was followed by the addition of a solution of DMSO (870 mg, 11.15 mmol, 10.0 equiv) in dichloromethane (5 mL) dropwise with stirring at −60° C. for 3 min. To this was added a solution of 2-[3-[(1r,3r)-3-[(5-[5-methyl-5H-pyrido[4,3-b]indol-7-yl]pyridin-2-yl)oxy]cyclobutoxy]propoxy]ethan-1-ol (500 mg, 1.12 mmol, 1.00 equiv) in dichloromethane (10 mL) dropwise with stirring at −60° C. for 5 min. The resulting solution was stirred for 15 min at −60° C. The reaction was then quenched by the addition of TEA (3 mL). The solids were filtered out. The resulting filtrate was concentrated under vacuum. This resulted in 500 mg (crude) of 2-[3-[(1r,3r)-3-[(5-[5-methyl-5H-pyrido[4,3-b]indol-7-yl]pyridin-2-yl)oxy]cyclobutoxy]propoxy]acetaldehyde as a yellow solid.

Step 11

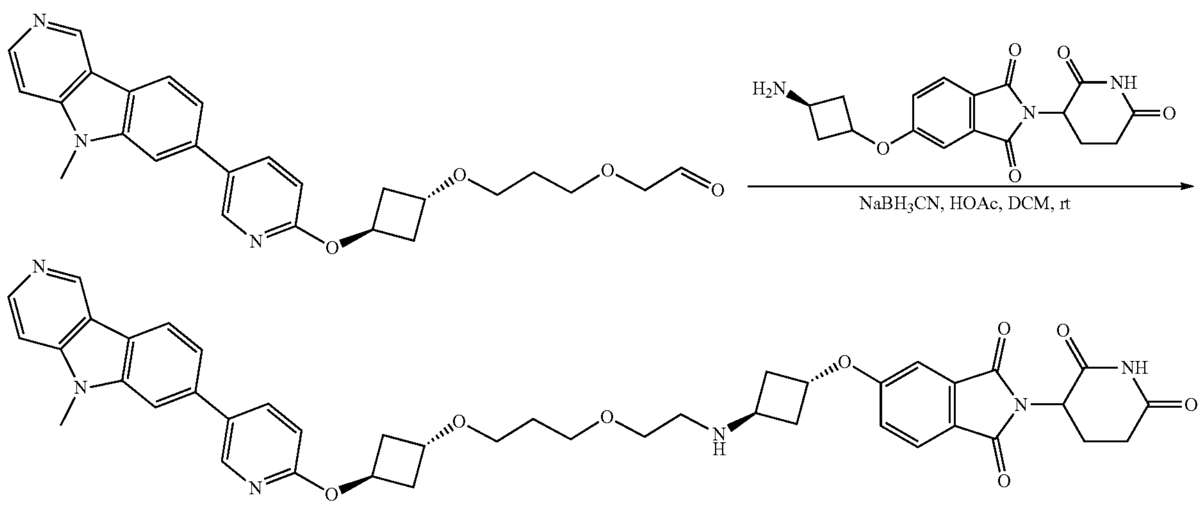

Exemplary Compound 217

Into a 100-mL round-bottom flask, was placed a solution of 2-[3-[(1r,3r)-3-[(5-[5-methyl-5H-pyrido[4,3-b]indol-7-yl]pyridin-2-yl)oxy]cyclobutoxy]propoxy]acetaldehyde (500 mg, crude) in dichloromethane (20 mL). DIEA (0.1 mL) was added. This was followed by the addition of 2-(2,6-dioxopiperidin-3-yl)-5-[(1r,3r)-3-aminocyclobutoxy]-2,3-dihydro-1H-isoindole-1,3-dione hydrochloride (213 mg, 0.56 mmol, 0.50 equiv). The mixture was stirred for 5 h at room temperature. To this was added NaBH$_3$CN (212 mg, 3.37 mmol, 3.00 equiv) and acetic acid (0.2 mL). The resulting solution was stirred for 1 h at room temperature. The reaction was then quenched by the addition of water (5 mL). The resulting mixture was concentrated under vacuum. The crude was purified by Prep-HPLC (two times): Column: XBridge Prep C18 OBD Column, 5 um, 19*150 mm; Mobile Phase A: Water (10 mmol/L $NH_4HCO_3$), Mobile Phase B: acetonitrile; Flow rate: 20 mL/min; Gradient: 45% B to 61% B in 8 min; 254 nm; Rt: 6.67 min. After lyophilization, this resulted in 4.2 mg of 2-(2,6-dioxopiperidin-3-yl)-5-[(1r,3r)-3-[(2-[3-[(1r,3r)-3-[(5-[5-methyl-5H-pyrido[4,3-b]indol-7-yl]pyridin-2-yl)oxy]cyclobutoxy]propoxy]ethyl)amino]cyclobutoxy]-2,3-dihydro-1H-isoindole-1,3-dione as a white solid.

Exemplary Synthesis of Exemplary Compound 268

Step 1

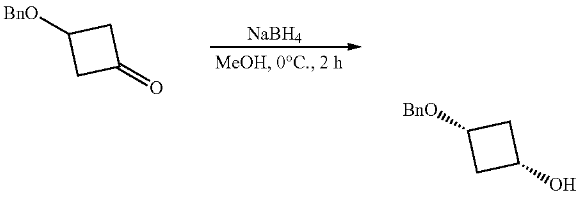

To a solution of 3-benzyloxycyclobutanone (4 g, 22.70 mmol, 1 eq) in methanol (10 mL) was added sodium borohydride (1.72 g, 45.40 mmol, 2 eq) in batches at 0° C. under nitrogen. The mixture was stirred at 0° C. for 2 h. The reaction was quenched by a slow addition of cold water, and then 1M HCl was added slowly until the suspension become clear. The aqueous phase was extracted with ethyl acetate (60 mL×3). The combined organic phase was washed with brine (30 mL), dried with anhydrous sodium sulfate, filtered and concentrated in vacuum. The residue was purified by silica gel chromatography (petroleum ether/ethyl acetate=10/1 to 2/1) to give (1s,3s)-3-(benzyloxy)cyclobutan-1-ol (3.5 g, 19.64 mmol, 86% yield) as a pale yellow oil.

(1s,3s)-3-(Benzyloxy)cyclobutan-1-ol was converted to the title compound according to the scheme below using procedures described for exemplary compound 333 above, as well as common procedures known to those skilled in the art.

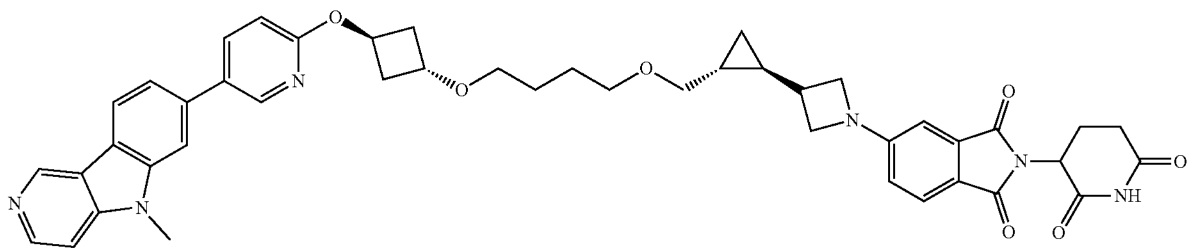 [SMILES: Cn1c2ccncc2c2ccc(-c3ccc(O[C@H]4C[C@H](OCCCCOC[C@@H]5C[C@H]5C5CN(c6ccc7c(c6)C(=O)N(C6CCC(=O)NC6=O)C7=O)C5)C4)nc3)cc21]

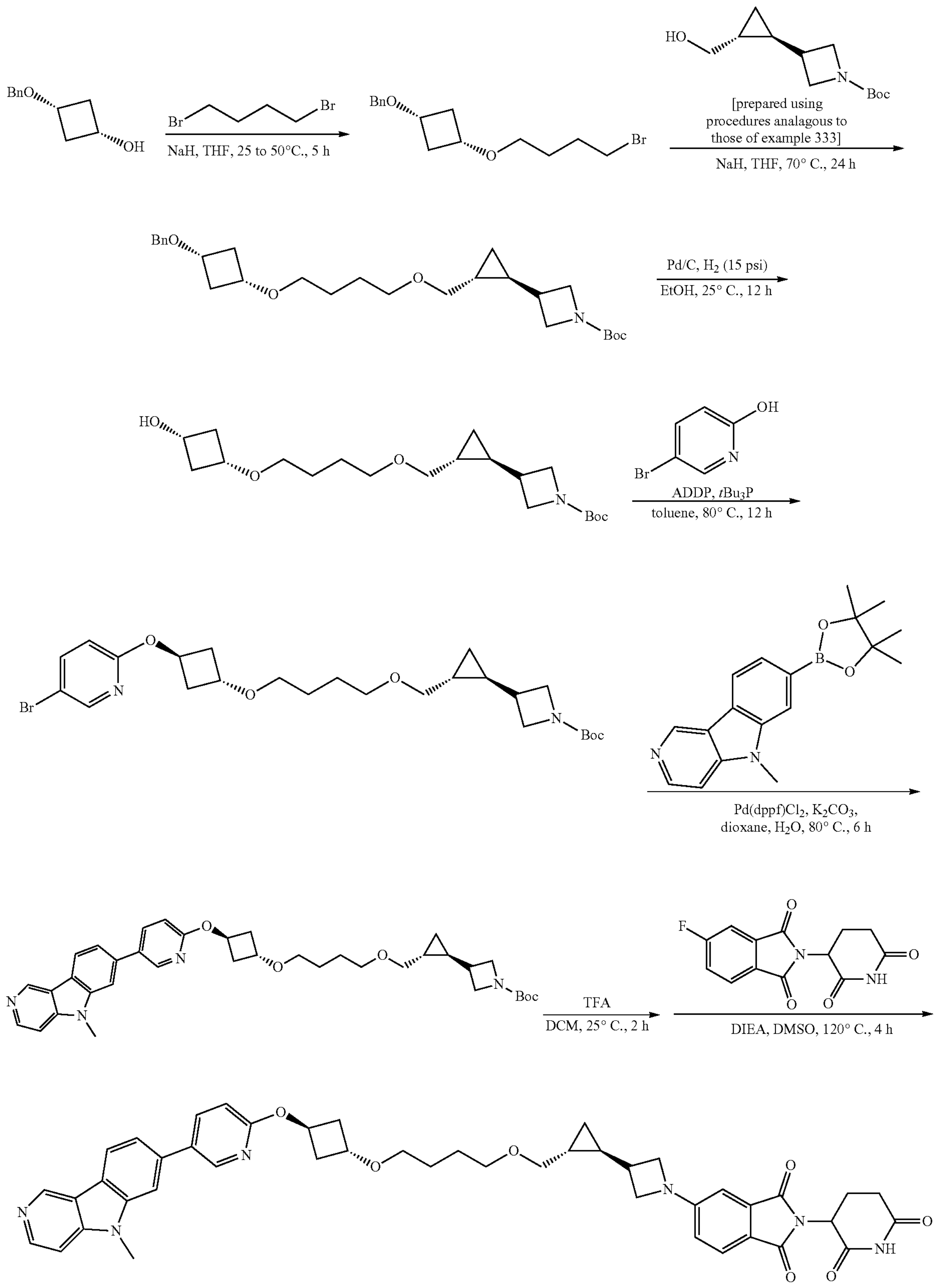
Exemplary Compound 268

Exemplary Synthesis of Exemplary Compound 275

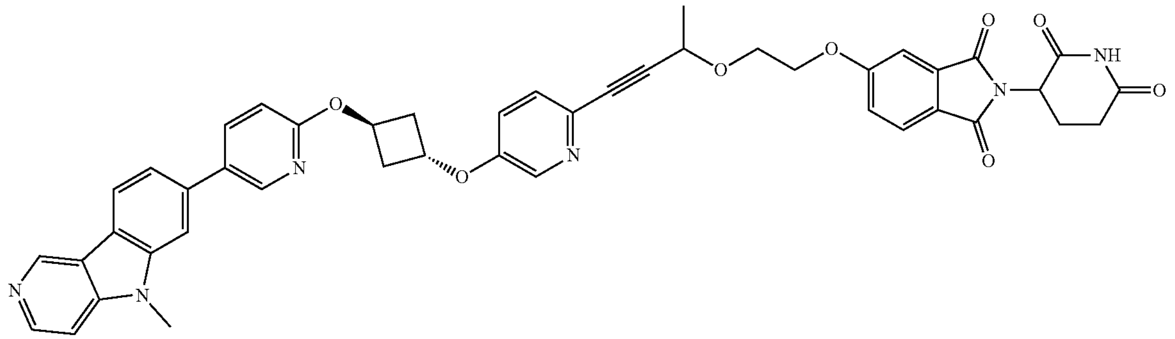 [SMILES: CC(C#Cc1ccc(O[C@H]2C[C@H](Oc3ccc(-c4ccc5c6cnccc6n(C)c5c4)cn3)C2)cn1)OCCOc1ccc2c(c1)C(=O)N(C1CCC(=O)NC1=O)C2=O]

Step 1

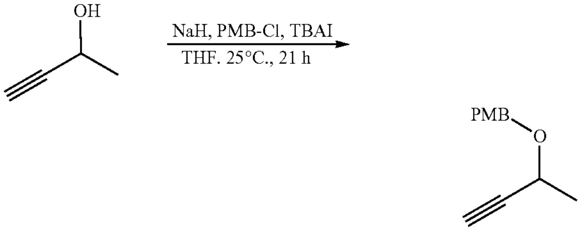

To a mixture of sodium hydride (4.45 g, 111.29 mmol, 60% purity, 1.3 eq) in tetrahydrofuran (240 mL) was added but-3-yn-2-ol (6 g, 85.60 mmol, 6.71 mL, 1 eq) at 0° C. under nitrogen. After 3 hours 1-(chloromethyl)-4-methoxybenzene (17.25 g, 110.15 mmol, 15 mL, 1.29 eq) was added followed by tetrabutylammonium iodide (1.58 g, 4.28 mmol, 0.05 eq). The reaction mixture was stirred at 25° C. for another 16 h. The reaction mixture was quenched by the addition of water (100 mL) and extracted with ethyl acetate (300 mL×3). The combined organic layers were washed with brine (100 mL×3), dried over anhydrous sodium sulfate, filtered and concentrated under reduced pressure to give a residue. The residue was purified by column chromatography (Petroleum ether/Ethyl acetate=100/1 to 20/1). 1-Methoxy-4-(1-methylprop-2-ynoxymethyl)benzene (7.8 g, 41 mmol, 47% yield) was obtained as a yellow solid.

Step 2

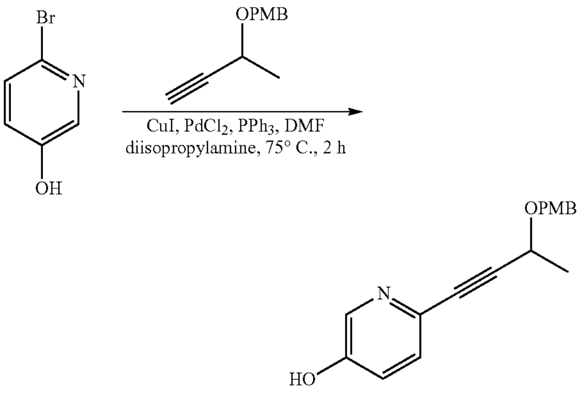

A mixture of 6-bromopyridin-3-ol (5.1 g, 29.31 mmol, 1 eq), 1-methoxy-4-(1-methylprop-2-ynoxymethyl)benzene (6.69 g, 35.17 mmol, 1.2 eq), cuprous iodide (558 mg, 2.93 mmol, 0.1 eq), palladium(II) chloride (260 mg, 1.47 mmol, 0.05 eq), diisopropylamine (14.61 g, 144.35 mmol, 20.40 mL, 4.92 eq) and triphenylphosphine (768 mg, 2.93 mmol, 0.1 eq) in N,N-dimethylformamide (50 mL) was degassed and purged with nitrogen for 3 times, and then the mixture was stirred at 75° C. for 16 h under nitrogen atmosphere. The reaction mixture was quenched by addition water (200 mL) and extracted with ethyl acetate (300 mL×3). The combined organic layers were washed with brine (100 mL×3), dried over anhydrous sodium sulfate, filtered and concentrated under reduced pressure to give a residue. The residue was purified by flash silica gel chromatography (petroleum ether/ethyl acetate=20/1 to 1/1). Compound 6-[3-[(4-methoxyphenyl)methoxy]but-1-ynyl]pyridin-3-ol (5 g, 17.65 mmol, 60% yield) was obtained as a white solid.

Step 3

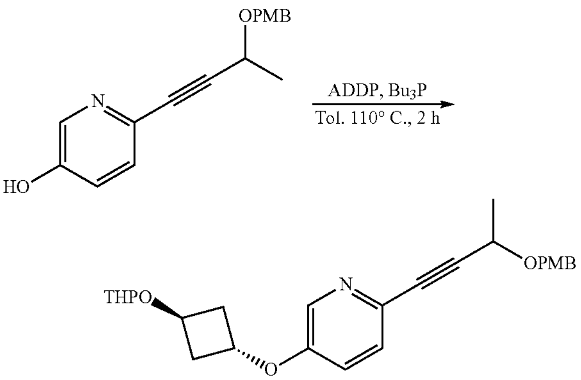

A mixture of 6-[3-[(4-methoxyphenyl)methoxy]but-1-ynyl]pyridin-3-ol (2.4 g, 8.47 mmol, 1 eq), 3-tetrahydropyran-2-yloxycyclobutanol (1.46 g, 8.47 mmol, 1 eq), 1,1-(azodicarbonyl)-dipiperidine (3.21 g, 12.71 mmol, 1.5 eq) and tributylphosphine (2.57 g, 12.71 mmol, 3.14 mL, 1.5 eq) in toluene (140 mL) was degassed and purged with nitrogen for 3 times, and then the mixture was stirred at 110° C. for 16 h under nitrogen atmosphere. The reaction mixture was quenched by the addition of water (200 mL) and extracted with ethyl acetate (300 mL×3). The combined organic layers were washed with brine (100 mL×3), dried over anhydrous sodium sulfate, filtered and concentrated under reduced pressure to give a residue. The residue was purified by column chromatography (Petroleum ether/Ethyl acetate=20/1 to 10/1). Compound 2-[3-[(4-methoxyphenyl)methoxy]but-1-ynyl]-5-(3-tetrahydropyran-2-yloxycyclobutoxy)pyridine (1.9 g, 4.34 mmol, 51% yield) was obtained as a yellow oil.

Step 4

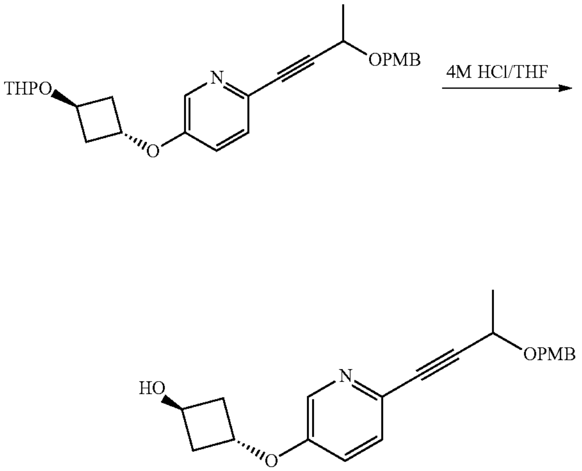

A solution of 2-[3-[(4-methoxyphenyl)methoxy]but-1-ynyl]-5-(3-tetrahydropyran-2-yloxycyclobutoxy)pyridine (1.90 g, 4.34 mmol, 1 eq) and hydrochloric acid (4 M, 19.00 mL, 17.50 eq) in tetrahydrofuran (19 mL) was degassed and purged with nitrogen for 3 times, and then the mixture was stirred at 25° C. for 1 h under nitrogen atmosphere. The pH of the mixture was adjusted to 7-8 by saturated sodium bicarbonate solution (20 mL), and the mixture was then extracted with ethyl acetate (200 mL×2). The combined organic layers were washed with brine (100 mL×2), dried over anhydrous sodium sulfate, filtered and concentrated under reduced pressure to give a residue. The residue was purified by column chromatography (petroleum ether/ethyl acetate=10/1 to 3/1). Compound 3-[[6-[3-[(4-methoxyphenyl)methoxy]but-1-ynyl]-3-pyridyl]oxy]cyclobutanol (1.2 g, 3.40 mmol, 78% yield) was obtained as a yellow oil.

Step 5

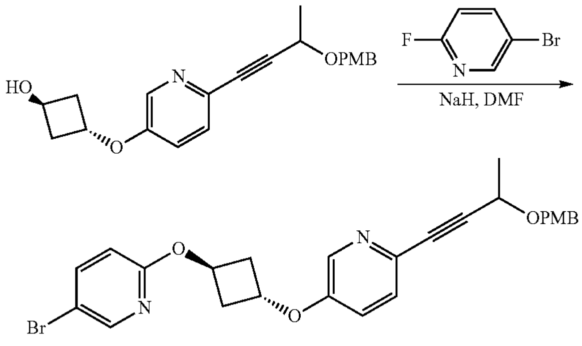

To a mixture of 3-[[6-[3-[(4-methoxyphenyl)methoxy]but-1-ynyl]-3-pyridyl]oxy]cyclobutanol (1 g, 2.83 mmol, 1 eq) in N,N-dimethylformamide (10 mL) was added sodium hydride (81 mg, 2.04 mmol, 60%, 0.72 eq) under nitrogen at 0° C. The reaction mixture was warmed to 25° C. for 1 h. To the reaction mixture was added 5-bromo-2-fluoro-pyridine (647 mg, 3.68 mmol, 1.3 eq) at 0° C. The reaction mixture was warmed to 25° C. for 16 h. The reaction mixture was quenched by the addition of water (200 mL) and extracted with ethyl acetate (300 mL×3). The combined organic layers were washed with brine (100 mL×3), dried over anhydrous sodium sulfate, filtered and concentrated under reduced pressure to give a residue. The residue was purified by column chromatography (petroleum ether/ethyl acetate=50/1 to 10/1). 5-Bromo-2-[3-[[6-[3-[(4-methoxyphenyl)methoxy]but-1-ynyl]-3-pyridyl]oxy]cyclobutoxy]pyridine (830 mg, 1.63 mmol, 57% yield) was obtained as a yellow oil.

Step 6

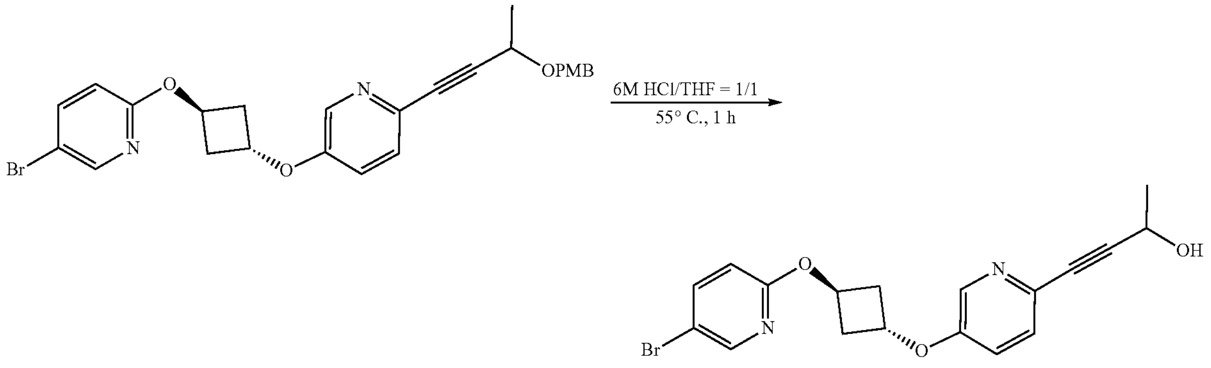

A mixture of 5-bromo-2-[3-[[6-[3-[(4-methoxyphenyl)methoxy]but-1-ynyl]-3-pyridyl]oxy]cyclobutoxy]pyridine (900 mg, 1.77 mmol, 1 eq) and hydrochloric acid (6 M, 9.00 mL, 30.6 eq) in tetrahydrofuran (9 mL) was degassed and purged with nitrogen for 3 times, and then the mixture was stirred at 50° C. for 1 hr under nitrogen atmosphere. The mixture pH was adjusted to 7~8 by saturated sodium bicarbonate solution (20 mL), then extracted with ethyl acetate (200 mL×2). The combined organic layers were washed with brine (100 mL×2), dried over anhydrous sodium sulfate, filtered and concentrated under reduced pressure to give a residue. The residue was purified by column chromatography (petroleum ether/ethyl acetate=10/1 to 1/2). Compound 4-[5-[3-[(5-bromo-2-pyridyl)oxy]cyclobutoxy]-2-pyridyl]but-3-yn-2-ol (490 mg, 1.26 mmol, 71% yield) was obtained as a white solid.

Step 7

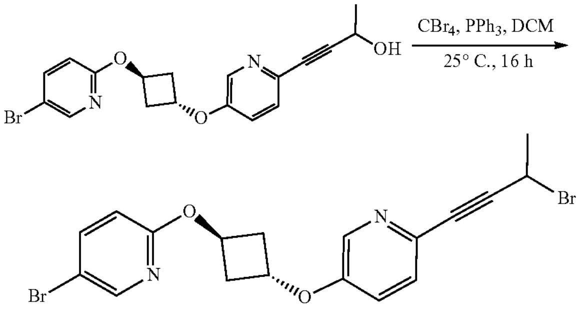

To a solution of 4-[5-[3-[(5-bromo-2-pyridyl)oxy]cyclobutoxy]-2-pyridyl]but-3-yn-2-ol (390 mg, 1.00 mmol, 1 eq) and tetrabromomethane (332 mg, 1.00 mmol, 1 eq) in dichloromethane (10 mL) was added triphenylphosphine (289 mg, 1.10 mmol, 1.1 eq) at 0° C. Then the reaction was stirred at 25° C. for 16 h. The reaction mixture was quenched by the addition of water (100 mL), and extracted with ethyl acetate (200 mL×3). The combined organic layers were washed with brine (100 mL×3), dried over anhydrous sodium sulfate, filtered and concentrated under reduced pressure to give a residue. The residue was purified by column chromatography (petroleum ether/ethyl acetate=10/1 to 2/1). Compound 2-(3-bromobut-1-ynyl)-5-[3-[(5-bromo-2-pyridyl)oxy]cyclobutoxy]pyridine (300 mg, 0.66 mmol, 66% yield) was obtained as a white solid.

Step 8

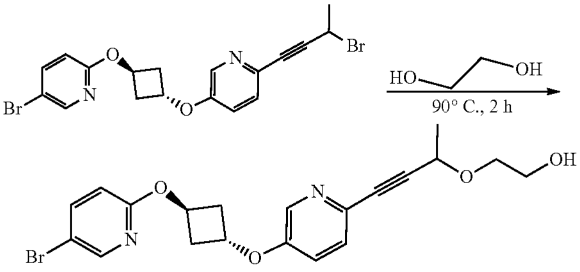

A solution of 2-(3-bromobut-1-ynyl)-5-[3-[(5-bromo-2-pyridyl)oxy]cyclobutoxy]pyridine (200 mg, 0.44 mmol, 1 eq) in ethylene glycol (10 mL) was degassed and purged with nitrogen for 3 times, and then the mixture was stirred at 100° C. for 0.5 h under nitrogen atmosphere. The reaction mixture was quenched by the addition of water (100 mL), and extracted with ethyl acetate (200 mL×3). The combined organic layers were washed with brine (100 mL×3), dried over anhydrous sodium sulfate, filtered and concentrated under reduced pressure to give a residue. The residue was purified by column chromatography (petroleum ether/ethyl acetate=20/1 to 1/1). Compound 2-[3-[5-[3-[(5-bromo-2-pyridyl)oxy]cyclobutoxy]-2-pyridyl]-1-methyl-prop-2-ynoxy]ethanol (150 mg, 0.34 mmol, 78% yield) was obtained as a yellow oil.

2-[3-[5-[3-[(5-Bromo-2-pyridyl)oxy]cyclobutoxy]-2-pyridyl]-1-methyl-prop-2-ynoxy]ethanol was converted to the title compound according to the scheme below using procedures described for other examples above.

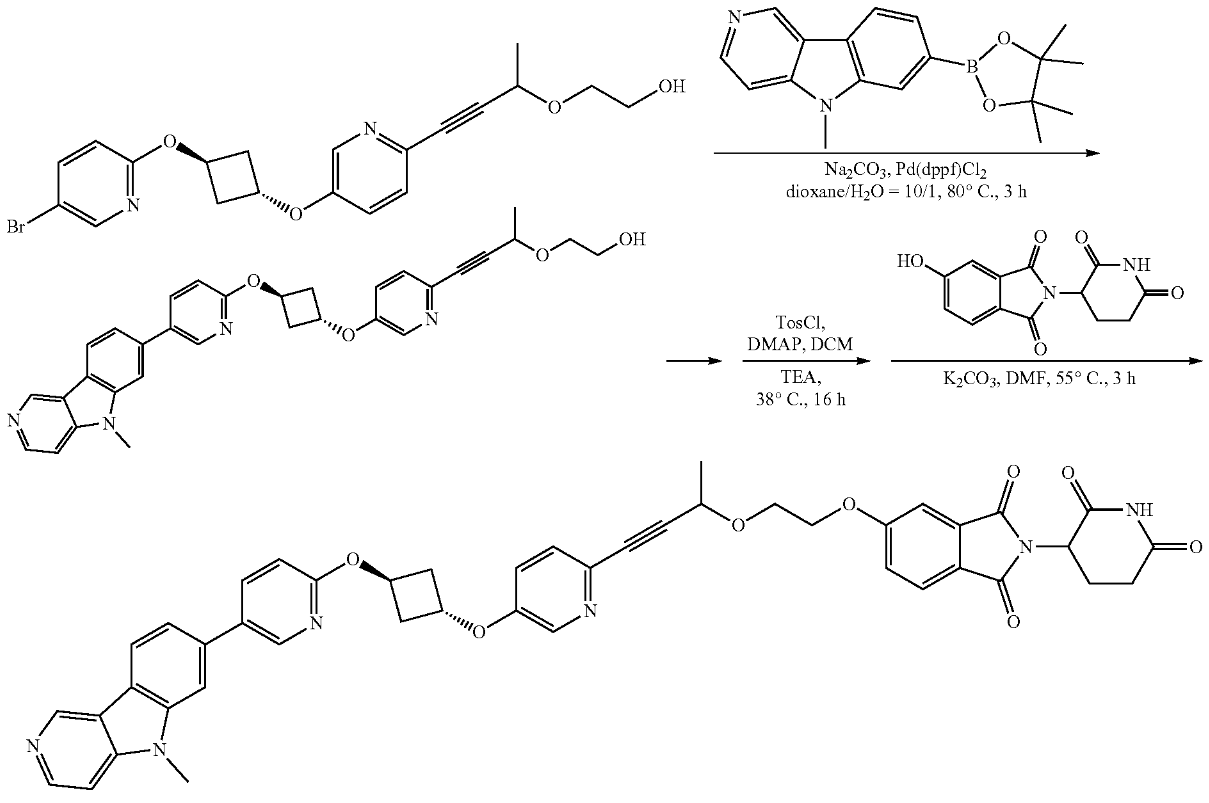

Exemplary Compound 275

Exemplary Synthesis of Exemplary Compound 228

Step 1

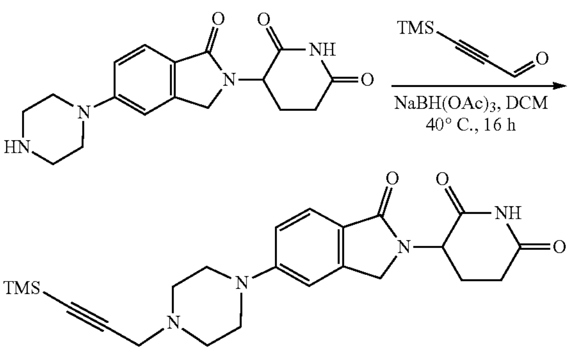

Into a 100-mL round-bottom flask, was placed 3-[1-oxo-5-(piperazin-1-yl)-2,3-dihydro-1H-isoindol-2-yl]piperidine-2,6-dione trifluoroacetic acid salt (400 mg, 1.22 mmol, 1 equiv) [prepared as described in US 20180125821] and DIEA (0.2 mL) in dichloromethane (10 mL). This was followed by the addition of 3-(trimethylsilyl)prop-2-ynal (184.5 mg, 1.46 mmol, 1.20 equiv), and the mixture was stirred at 40° C. for 1 hr. To this was added $NaBH(OAc)_3$ (1033 mg, 4.87 mmol, 4.0 equiv). The resulting solution was stirred for another 16 hr at 40° C. in an oil bath. The reaction was then quenched by the addition of water (100 mL). The resulting solution was extracted with dichloromethane (50 mL×3). The resulting mixture was washed with brine (50 mL×1). The mixture was dried over anhydrous sodium sulfate. The residue was applied onto a silica gel column eluting with dichloromethane/methanol (10/1). This resulted in 273 mg (51%) of 3-(1-oxo-5-[4-[3-(trimethylsilyl)prop-2-yn-1-yl]piperazin-1-yl]-2,3-dihydro-1H-isoindol-2-yl)piperidine-2,6-dione as a light yellow oil.

Step 2

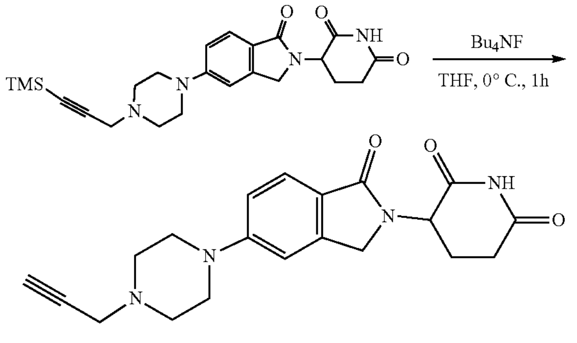

Into a 50-mL round-bottom flask, was placed 3-(1-oxo-5-[4-[3-(trimethylsilyl)prop-2-yn-1-yl]piperazin-1-yl]-2,3-dihydro-1H-isoindol-2-yl)piperidine-2,6-dione (273 mg, 0.62 mmol, 1 equiv) in THF (20 mL). This was followed by the addition of $Bu_4NF$ (0.62 mL, 1.0 equiv, 1 mol/L in THF) at 0° C. The resulting solution was stirred for 1 hr at 0° C. in a water/ice bath. The reaction was then quenched by the addition of water (100 mL). The resulting solution was extracted with ethyl acetate (50 mL×2). The resulting mixture was washed with brine (100 mL). The mixture was dried over anhydrous sodium sulfate. The residue was applied onto a silica gel column eluting with dichloromethane/methanol (12/1). This resulted 174 mg of 3-[1-oxo-5-[4-(prop-2-yn-1-yl)piperazin-1-yl]-2,3-dihydro-1H-isoindol-2-yl]piperidine-2,6-dione.

3-[1-Oxo-5-[4-(prop-2-yn-1-yl)piperazin-1-yl]-2,3-dihydro-1H-isoindol-2-yl]piperidine-2,6-dione was converted to the title compound as shown below using procedure described in Exemplary synthesis of exemplary compound 220.

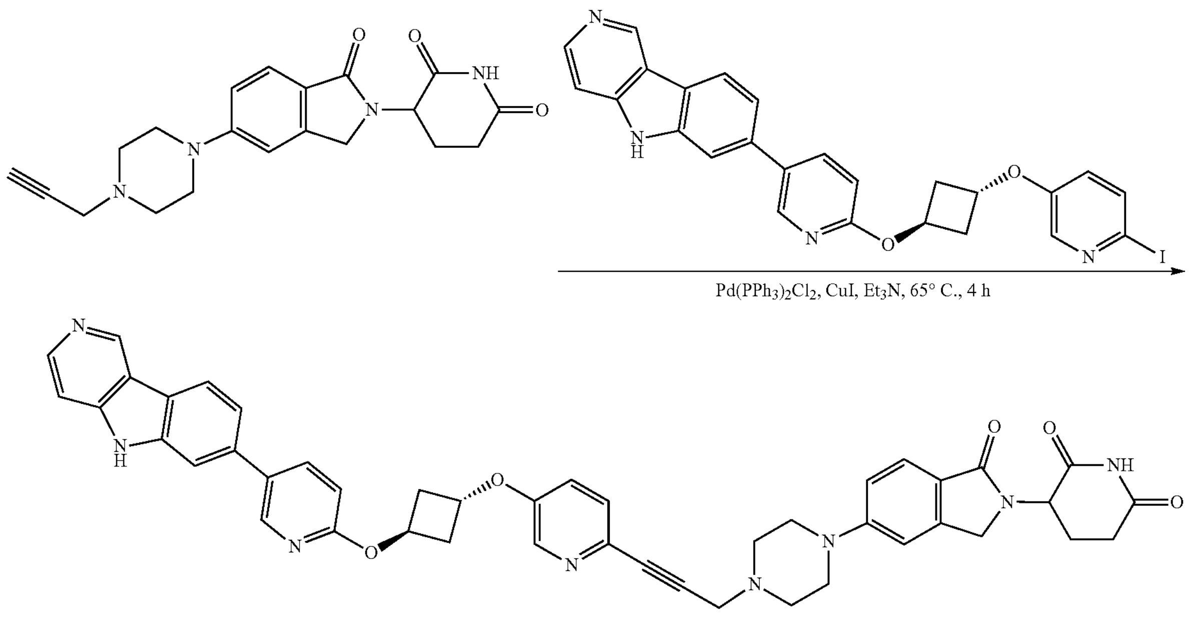

Exemplary Compound 228

Exemplary Synthesis of Exemplary Compound 237

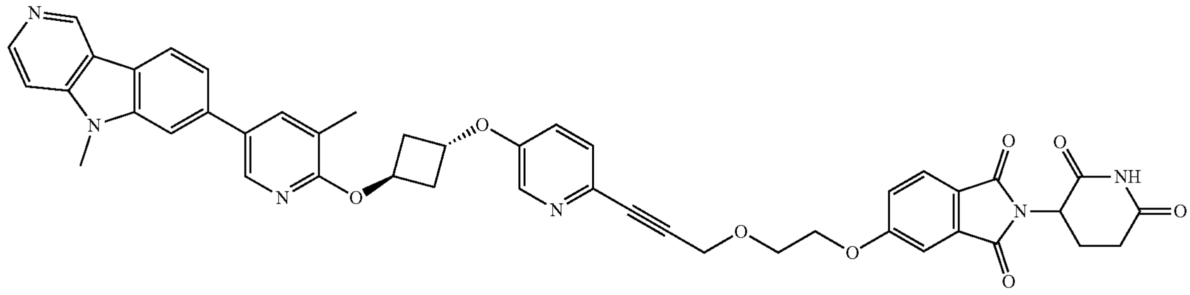 [SMILES: Cc1cc(-c2ccc3c4cnccc4n(C)c3c2)cnc1O[C@H]1C[C@H](Oc2ccc(C#CCOCCOc3ccc4c(c3)C(=O)N(C3CCC(=O)NC3=O)C4=O)nc2)C1]

Step 1

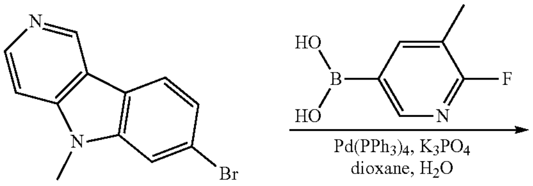

-continued

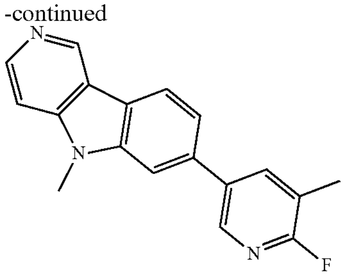

To a solution of (6-fluoro-5-methylpyridin-3-yl)boronic acid (715 mg, 4.61 mmol, 1.20 equiv) and 7-bromo-5-methyl-5H-pyrido[4,3-b]indole (1 g, 3.85 mmol, 1.0 equiv) in 1,4-dioxane/water (10/2 mL) was added $K_3PO_4$ (2.04 g, 9.625 mmol, 2.5 equiv) and $Pd(PPh_3)_4$ (222 mg, 0.19 mmol, 0.05 equiv) at room temperature under nitrogen atmosphere. The resulting mixture was stirred for 2 h at 90° C. in an oil bath. After solvent removal under reduced pressure, the residue was purified by silica gel column chromatography eluting with dichloromethane/methanol (10:1). This resulted in 1.01 g (90% yield) of 7-(6-fluoro-5-methylpyridin-3-yl)-5-methyl-5H-pyrido[4,3-b]indole as a yellow solid.

7-(6-Fluoro-5-methylpyridin-3-yl)-5-methyl-5H-pyrido[4,3-b]indole was converted to the title compound using the corresponding procedures described in US 20180125821 and in exemplary compound 220.

Exemplary Synthesis of Exemplary Compound 334

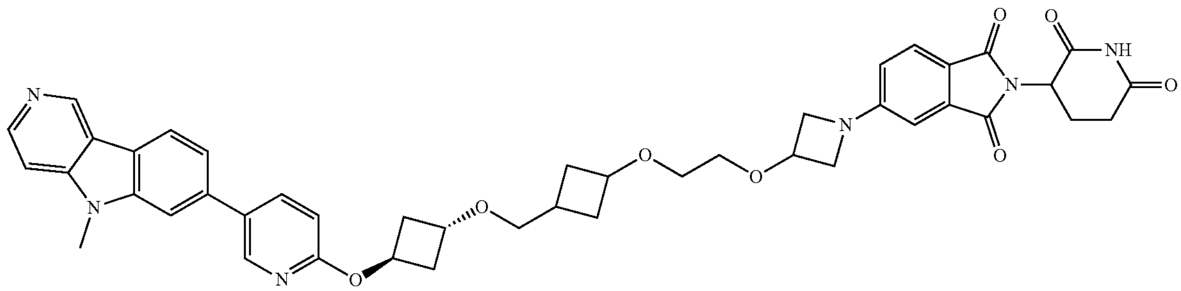 [SMILES: Cn1c2ccncc2c2ccc(-c3ccc(O[C@H]4C[C@H](OCC5CC(OCCOC6CN(c7ccc8c(c7)C(=O)N(C7CCC(=O)NC7=O)C8=O)C6)C5)C4)nc3)cc21]

Prepared according to the scheme below using procedures described for other examples above and common procedures known to those skilled in the art.

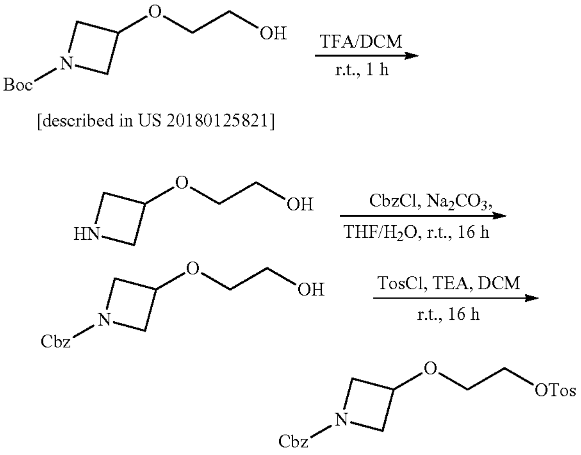

-continued
-continued
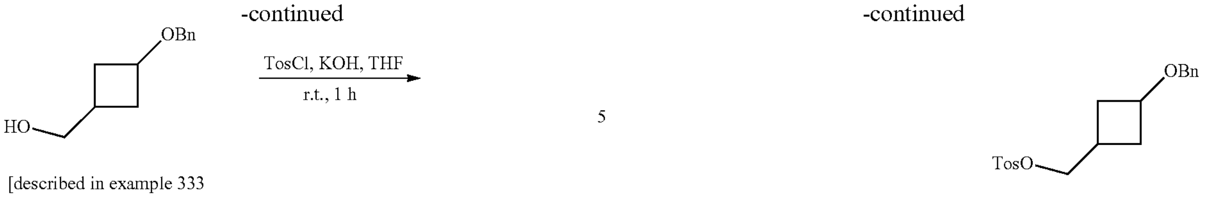
[described in example 333
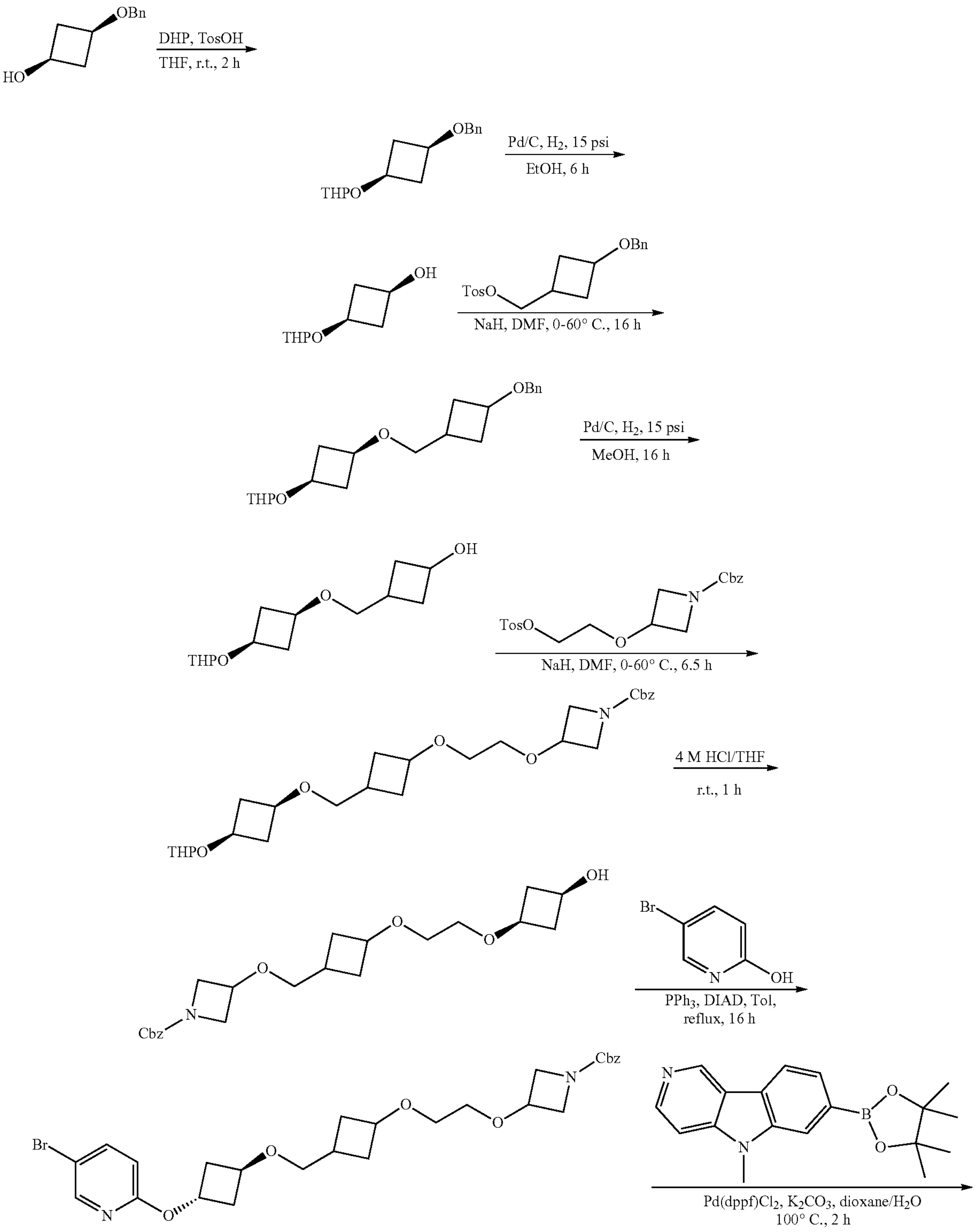

-continued

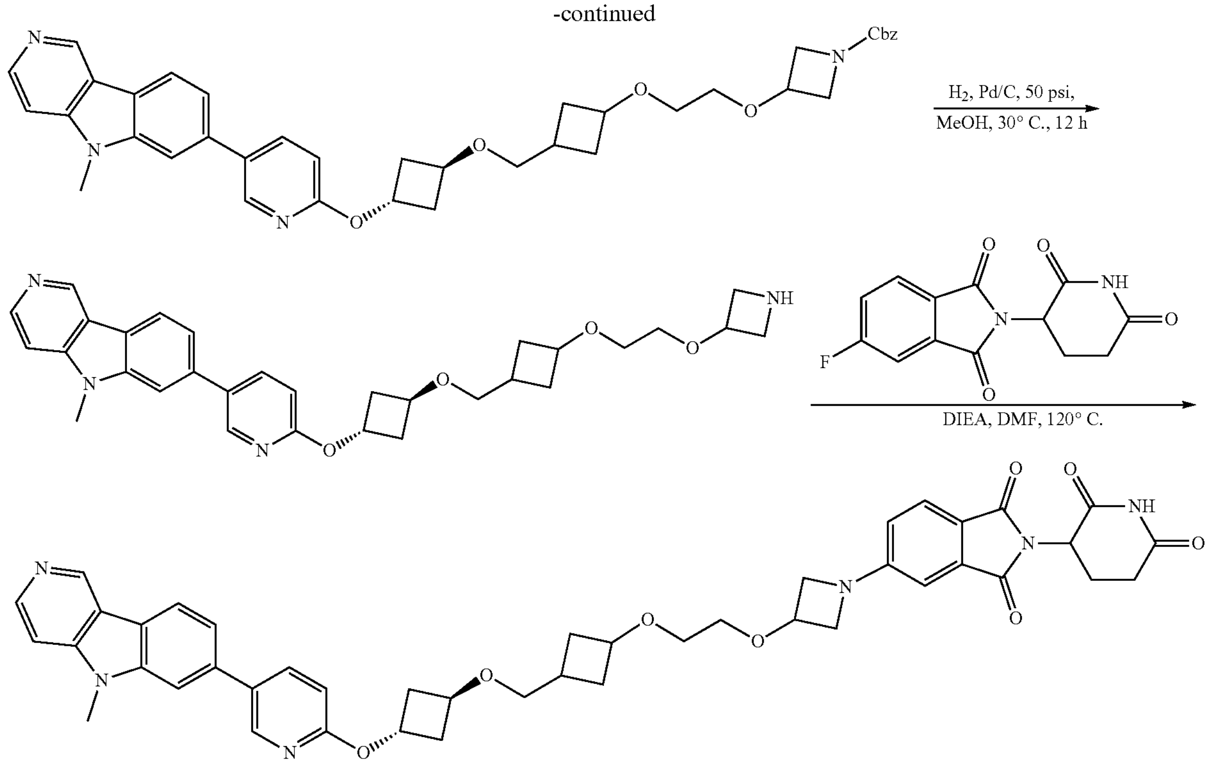

Exemplary Compound 334

Exemplary Synthesis of Exemplary Compound 335

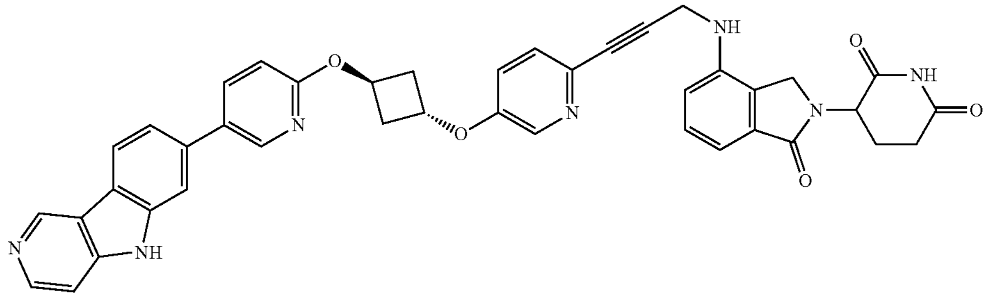 [SMILES: O=C1CCC(N2Cc3c(NCC#Cc4ccc(O[C@H]5C[C@H](Oc6ccc(-c7ccc8c(c7)[nH]c7ccncc78)cn6)C5)cn4)cccc3C2=O)C(=O)N1]

Step 1

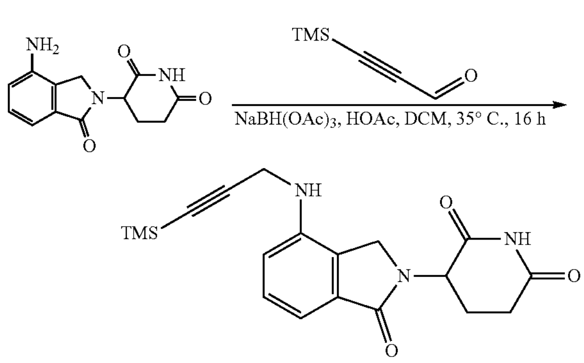

Into a 100-mL round-bottom flask, was placed 3-(4-amino-1-oxo-2,3-dihydro-1H-isoindol-2-yl)piperidine-2,6-dione (1.0 g, 3.86 mmol, 1.0 equiv), 3-(trimethylsilyl)prop-2-ynal (486 mg, 3.85 mmol, 1.0 equiv) in dichloromethane (30 mL). This was followed by the addition of HOAc (5.0 mL), and the reaction mixture was stirred at 40° C. for 1 hr. To this was added $NaBH(OAc)_3$ (3.3 g, 15.57 mmol, 4.0 equiv). The resulting solution was stirred for another 16 hr at 35° C. in an oil bath. The resulting solution was extracted with dichloromethane (100 mL×2). The resulting mixture was washed with brine (50 mL×2) and concentrated. This resulted in 1.14 g (80%) of 3-(1-oxo-4-[[3-(trimethylsilyl)prop-2-yn-1-yl]amino]-2,3-dihydro-1H-isoindol-2-yl)piperidine-2,6-dione as a white solid.

Step 2

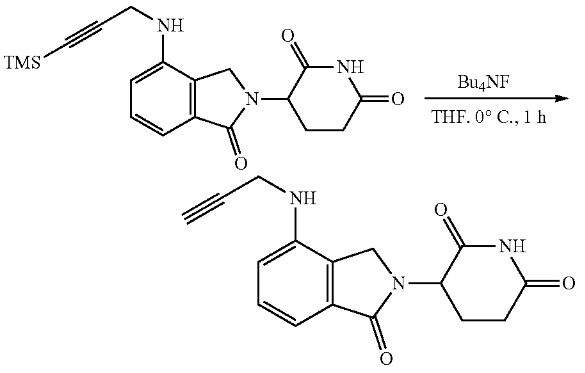

Into a 100-mL round-bottom flask, was placed 3-(1-oxo-4-[[3-(trimethylsilyl)prop-2-yn-1-yl]amino]-2,3-dihydro-1H-isoindol-2-yl)piperidine-2,6-dione (500 mg, 1.35 mmol, 1 equiv) in THF (10 mL). This was followed by the addition of $Bu_4NF$ (1.35 mL, 0.52 mmol, 0.38 equiv, 1 mol/L in THF) at 0° C. The resulting solution was stirred for 1 hr at 0° C. in a water/ice bath. The resulting solution was extracted with ethyl acetate (50 mL×2). The resulting mixture was washed with brine (50 mL×2). The mixture was dried over anhydrous sodium sulfate and concentrated. The residue was applied onto a silica gel column eluting with dichloromethane/methanol (10/1). This resulted in 369 mg (92%) of 3-[1-oxo-4-[(prop-2-yn-1-yl)amino]-2,3-dihydro-1H-isoindol-2-yl]piperidine-2,6-dione as a white solid.

3-[1-Oxo-4-[(prop-2-yn-1-yl)amino]-2,3-dihydro-1H-isoindol-2-yl]piperidine-2,6-dione was converted to the title compound as described for exemplary compound 220.

Exemplary Synthesis of Exemplary Compound 273

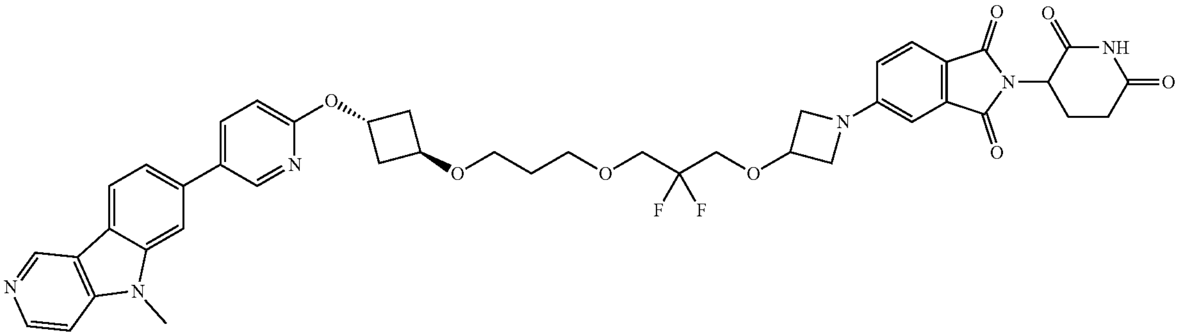 [SMILES: Cn1c2ccncc2c2ccc(-c3ccc(O[C@H]4C[C@H](OCCCOCC(F)(F)COC5CN(c6ccc7c(c6)C(=O)N(C6CCC(=O)NC6=O)C7=O)C5)C4)nc3)cc21]

Step 1

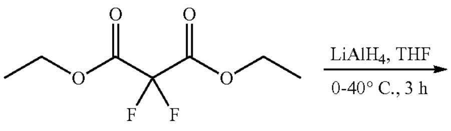

-continued

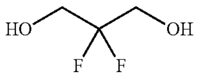

To a solution of lithium aluminum hydride (15.48 g, 408 mmol, 2.0 eq) in tetrahydrofuran (400 mL) was added dropwise a solution of diethyl 2,2-difluoropropanedioate (40 g, 204 mmol, 1.0 eq) in tetrahydrofuran (70 mL) at 0° C. over 30 min under nitrogen. After addition the mixture was stirred at 40° C. for 3 h. The pH was adjusted to 3 with 1M hydrogen chloride, the mixture was concentrated under reduced pressure at 50° C. The residue was diluted with ethyl acetate (1000 mL×5). The combined organic phase was dried with anhydrous sodium sulfate, filtered and concentrated in vacuum. The crude product 2,2-difluoropropane-1,3-diol (20.10 g, 179 mmol, 87% yield) was obtained as a yellow oil.

Step 2

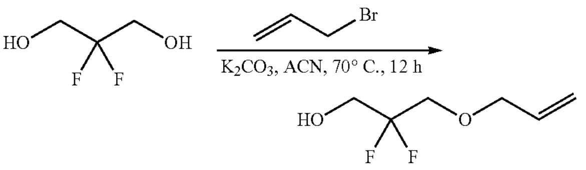

To a solution of 2,2-difluoropropane-1,3-diol (5.00 g, 44.6 mmol, 1.0 eq) and 3-bromoprop-1-ene (5.40 g, 44.6 mmol, 1.0 eq) in acetonitrile (60 mL) was added potassium carbonate (9.25 g, 66.9 mmol, 1.5 eq) at 25° C., and the mixture was stirred at 70° C. for 12 h. The reaction mixture was filtered, washed with ethyl acetate (100 mL), and the filter was concentrated. The residue was purified by silica gel chromatography (petroleum ether/ethyl acetate 50/1 to 10/1) to afford 3-allyloxy-2,2-difluoro-propan-1-ol (3.12 g, 20.5 mmol, 45% yield) as a colorless oil.

Step 3

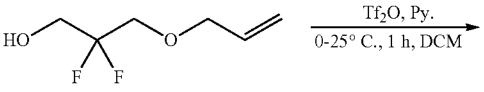

-continued

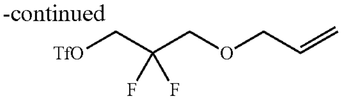

To a solution of 3-allyloxy-2,2-difluoro-propan-1-ol (3.10 g, 20.4 mmol, 1.0 eq) and pyridine (2.42 g, 30.6 mmol, 2.47 mL, 1.5 eq) in dichloromethane (20 mL) was added trifluoromethanesulfonic anhydride (6.90 g, 24.5 mmol, 4.03 mL, 1.20 eq) at 0° C., and the mixture was stirred at 25° C. for 1 h. The mixture was concentrated under reduced pressure at 25° C. The residue was purified by silica gel chromatography (petroleum ether/ethyl acetate=1/0) to afford (3-allyloxy-2,2-difluoro-propyl) trifluoromethanesulfonate (3.75 g, 13.2 mmol, 64% yield) as a colorless oil.

Step 4

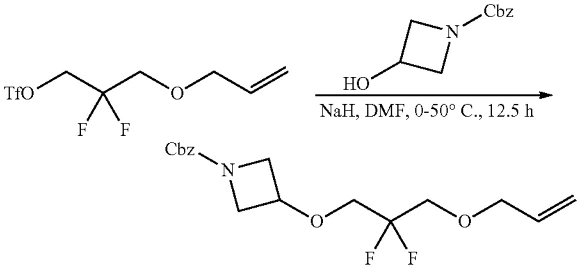

To a solution of benzyl 3-hydroxyazetidine-1-carboxylate (3.28 g, 15.8 mmol, 1.2 eq) in N,N-dimethylformamide (35 mL) was added sodium hydride (791 mg, 19.8 mmol, 60%, 1.5 eq) at 0° C., and the mixture was stirred at 0° C. for 0.5 h under nitrogen. Then to the mixture was added a solution of (3-allyloxy-2,2-difluoro-propyl) trifluoromethanesulfonate (3.75 g, 13.2 mmol, 1.0 eq) in N,N-dimethylformamide (15 mL) at 0° C., the mixture was heated to 50° C. and stirred for 12 h. The residue was poured into ice-water (w/w=1/1) (30 mL) and stirred for 15 min. The aqueous phase was extracted with ethyl acetate (50 mL×3). The combined organic phase was washed with brine (50 mL×3), dried with anhydrous sodium sulfate, filtered and concentrated in vacuum. The residue was purified by prep-HPLC (column: Phenomenex Synergi Max-RP 250*50 mm*10 um; mobile phase: [water (0.225% FA)-ACN]; B %: 40%-70%, 25 MIN, 30% min) to afford benzyl 3-(3-allyloxy-2,2-difluoro-propoxy)azetidine-1-carboxylate (1.32 g, 3.87 mmol, 29% yield) as a yellow oil.

Step 5

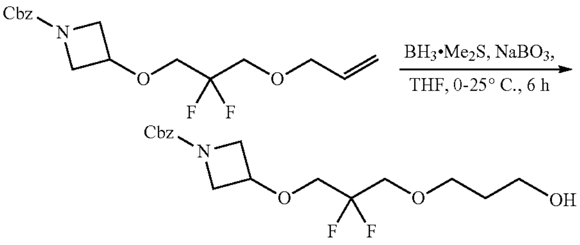

To a solution of benzyl 3-(3-allyloxy-2,2-difluoro-propoxy)azetidine-1-carboxylate (1.3 g, 3.81 mmol, 1.0 eq) in tetrahydrofuran (20 mL) was added borane dimethyl sulfide complex (10 M, 0.76 mL, 2.0 eq) at 0° C., and the mixture was warmed to 25° C. and stirred for 4 h under nitrogen. Then to the mixture was added a solution of sodium perborate tetrahydrate (1.76 g, 11.43 mmol, 3.00 eq) in water (20 mL) at 0° C., the mixture was warmed to 25° C. and stirred for 2 h. The suspension was filtered and concentrated in vacuum. The residue was poured into ice-water (w/w=1/1) (50 mL) and stirred for 15 min. The aqueous phase was extracted with ethyl acetate (50 mL×3). The combined organic phase was washed with brine (50 mL×3), dried with anhydrous sodium sulfate, filtered and concentrated in vacuum. The residue was purified by silica gel chromatography (petroleum ether/ethyl acetate 10/1 to 1/1) to afford benzyl 3-[2,2-difluoro-3-(3-hydroxypropoxy)propoxy]azetidine-1-carboxylate (650 mg, 1.81 mmol, 47% yield) as a colorless oil.

Benzyl 3-[2,2-difluoro-3-(3-hydroxypropoxy)propoxy]azetidine-1-carboxylate was converted to the title compound according to the scheme below using procedures described for the examples above and other procedures commonly known to those skilled in the art.

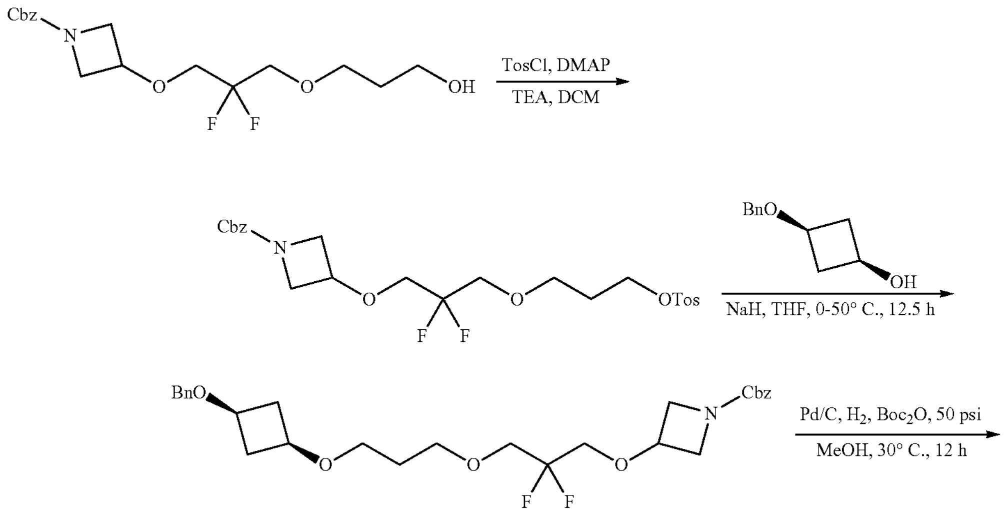

-continued
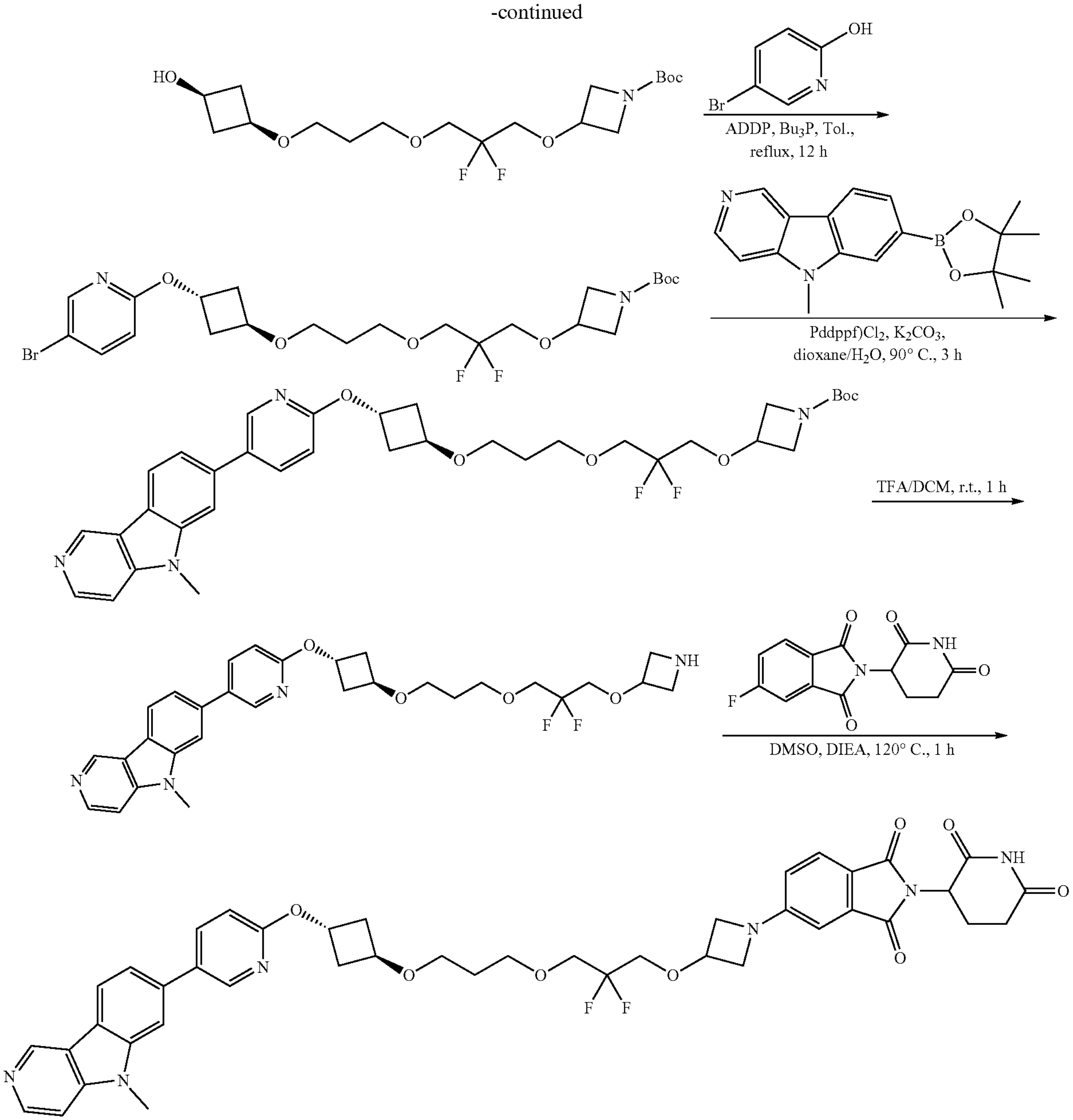
Exemplary Compound 273
Exemplary Synthesis of Exemplary Compound 336
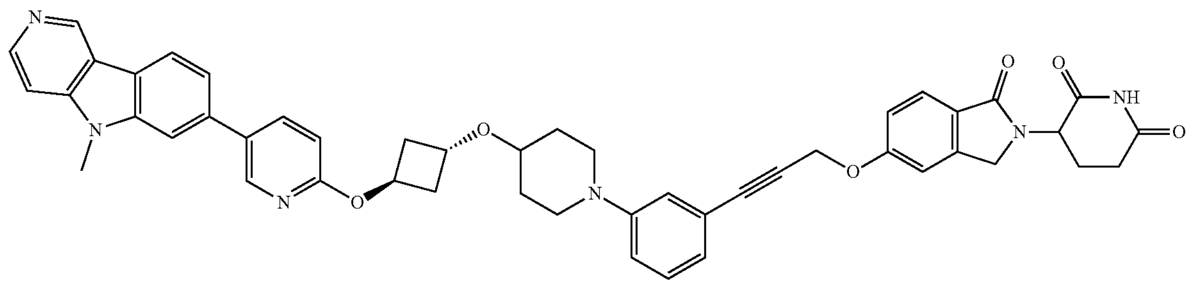 [SMILES: Cn1c2ccncc2c2ccc(-c3ccc(O[C@H]4C[C@H](OC5CCN(c6cccc(C#CCOc7ccc8c(c7)CN(C7CCC(=O)NC7=O)C8=O)c6)CC5)C4)nc3)cc21]

Step 1 ID-41

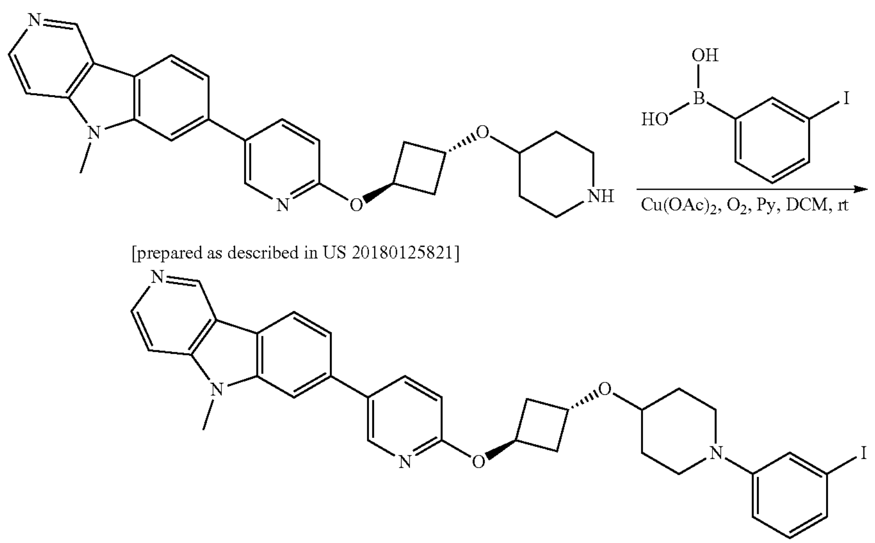

Into a 100-mL 3-neck round-bottom flask was placed 5-[5-methyl-5H-pyrido[4,3-b]indol-7-yl]-2-[(1r,3r)-3-(piperidin-4-yloxy)cyclobutoxy]pyridine hydrochloride (333 mg, 0.72 mmol, 1.0 equiv), DCM (40 mL), (3-iodophenyl) boronic acid (213.0 mg, 0.86 mmol, 1.2 equiv), $Et_3N$ (217.4 mg, 2.15 mmol, 3 equiv), $Cu(OAc)_2$ (65.0 mg, 0.36 mmol, 0.5 equiv), and oxygen was bubbled through the solution. The resulting solution was stirred for 7 hr at room temperature. The reaction was then quenched by the addition of water. The resulting solution was extracted with dichloromethane. The resulting mixture was washed with saturated NaCl. The mixture was dried over anhydrous sodium sulfate. The residue was applied onto a silica gel column eluting with dichloromethane/methanol (20/1). The collected fractions were combined and concentrated under vacuum. This resulted in 95 mg (21%) of 5-[5-methyl-5H-pyrido[4,3-b]indol-7-yl]-2-[(1r,3r)-3-[[1-(3-iodophenyl)piperidin-4-yl]oxy]cyclobutoxy]pyridine as a yellow oil.

5-[5-Methyl-5H-pyrido[4,3-b]indol-7-yl]-2-[(1r,3r)-3-[[1-(3-iodophenyl)piperidin-4-yl]oxy]cyclobutoxy]pyridine was converted to the title compound according to the scheme below using procedures described for examples above.

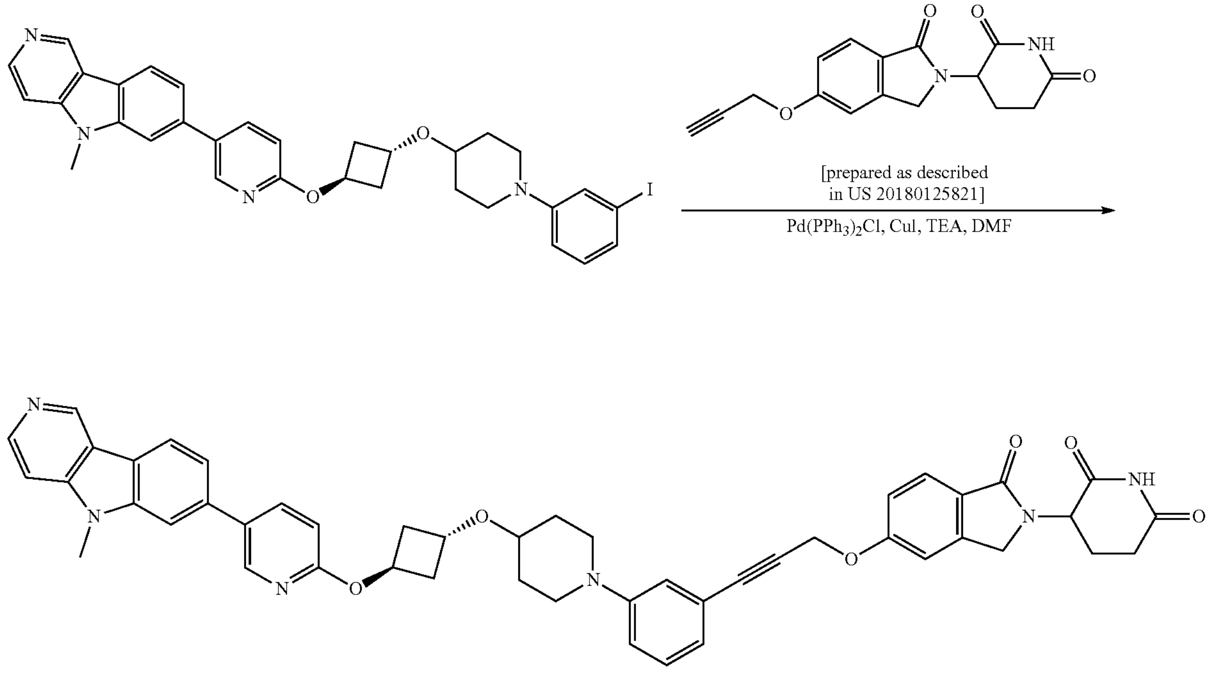

Exemplary Compound 336

Exemplary Synthesis of Exemplary Compound 235

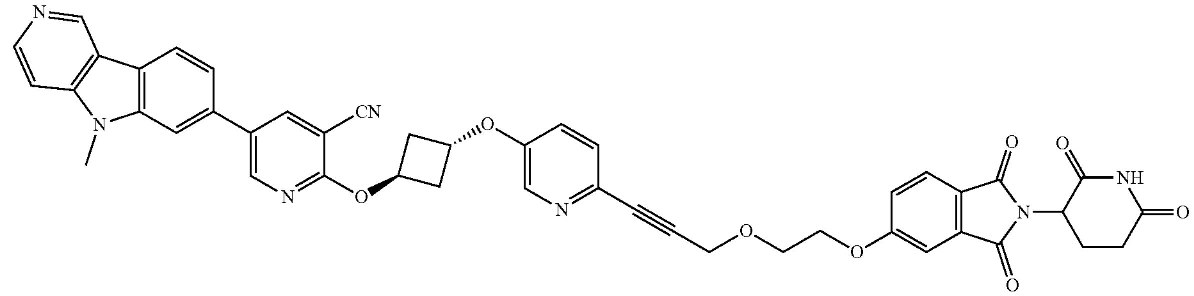 [SMILES: Cn1c2ccncc2c2ccc(-c3cnc(O[C@H]4C[C@H](Oc5ccc(C#CCOCCOc6ccc7c(c6)C(=O)N(C6CCC(=O)NC6=O)C7=O)nc5)C4)c(C#N)c3)cc21]

Step 1

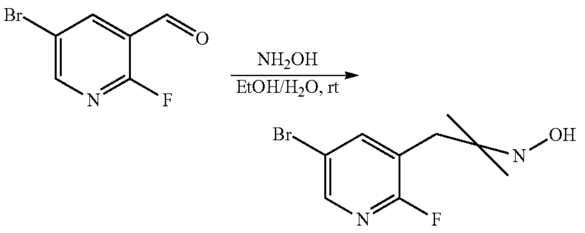

A mixture of 5-bromo-2-fluoropyridine-3-carbaldehyde (5 g, 1 equiv) and hydroxylamine (1.6 g, 2.0 equiv) was stirred in EtOH/water (100/50 mL) for 1 h at room temperature. The mixture was filtered and the filter cake was washed with water (50 mL). The filtrate was concentrated under reduced pressure. This resulted in N-[(5-bromo-2-fluoropyridin-3-yl)methylidene]hydroxylamine (6.1 g) as a white solid.

Step 2

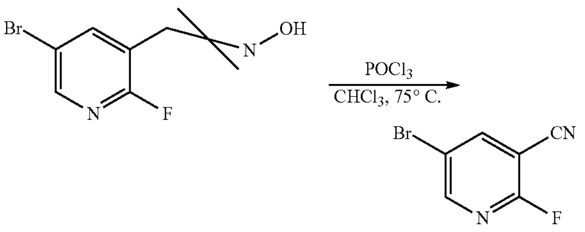

Into a solution of N-[(5-bromo-2-fluoropyridin-3-yl) methylidene]hydroxylamine (500 mg, 2.28 mmol, 1 eq) in chloroform (30 mL) $POCl_3$ (5.6 g, 8 eq) was dropwise at room temperature. The resulting mixture was stirred for 5 h at 75° C. The resulting mixture was concentrated under vacuum. The residue was purified by silica gel column chromatography, eluting with petroleum ether/ethyl acetate (3:1) to afford 5-bromo-2-fluoropyridine-3-carbonitrile (620 mg, crude) as a white solid.

Step 3

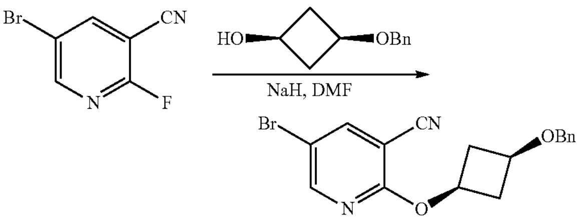

To a solution of (1s,3s)-3-(benzyloxy)cyclobutan-1-ol (3.4 g, 19 mmol) in N,N-dimethylformamide was added sodium hydride (60% in oil, 1.28 g, 32 mmol) at 0° C. The mixture was stirred for 15 min. 5-Bromo-2-fluoropyridine-3-carbonitrile (3.2 g, 20 mmol) was added, and the mixture was allowed to warm to 20° C. and stirred for 2 h. The reaction mixture was quenched by ice water (50 mL). The resulting mixture was extracted with ethyl acetate (50 mL×3). The combined organic layers were washed with brine (30 mL×1) and dried over anhydrous sodium sulfate. After filtration, the filtrate was concentrated under reduced pressure. The residue was purified by silica gel column chromatography eluting with petroleum ether/ethyl acetate (5:1) to afford 5-bromo-2-[(1s,3s)-3-(benzyloxy)cyclobutoxy]pyridine-3-carbonitrile (3.1 g, 29%) as a yellow solid.

Step 4

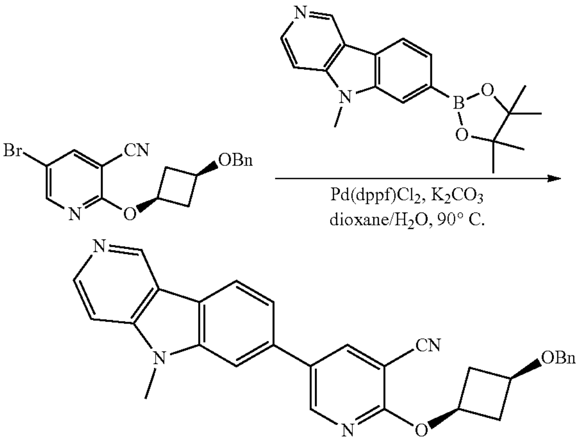

Into a 25-mL sealed tube were added 5-bromo-2-[(1s,3s)-3-(benzyloxy)cyclobutoxy]pyridine-3-carbonitrile (1.16 g, 3.23 mmol), 5-methyl-7-(4,4,5,5-tetramethyl-1,3,2-dioxaborolan-2-yl)-5H-pyrido[4,3-b]indole (1.2 g, 3.89 mmol), $Pd(PPh_3)_4$ (150 mg, 0.13 mmol), potassium carbonate (1.1 g, 0.01 mmol), dioxane (10 mL), and water (2 mL) at room temperature. The resulting mixture was stirred for 2 h at 90° C. under nitrogen atmosphere. The aqueous layer was extracted with ethyl acetate (50 mL×3). The resulting mixture was concentrated under vacuum. The residue was purified by silica gel column chromatography eluting with dichloromethane/methyl alcohol (10:1) to afford 5-[5-methyl-5H-pyrido[4,3-b]indol-7-yl]-2-[(1s,3s)-3-(benzyloxy)cyclobutoxy]pyridine-3-carbonitrile (810 mg, 55%) as a yellow solid.

Step 5

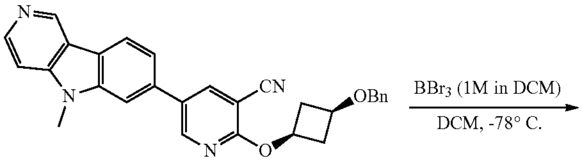

-continued

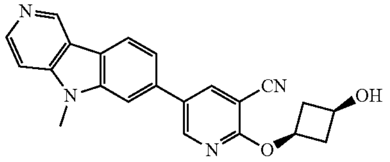

To a stirred solution of 5-[5-methyl-5H-pyrido[4,3-b]indol-7-yl]-2-[(1s,3s)-3-(benzyloxy)cyclobutoxy]pyridine-3-carbonitrile (760 mg, 1 equiv) in dichloromethane (20 ml) were added boron tribromide (15 mL, 5.0 equiv) dropwise at −78° C. under nitrogen atmosphere. The resulting mixture was stirred for 1 h at −78 degrees C. under nitrogen atmosphere. The reaction was quenched with methyl alcohol at room temperature. The mixture was concentrated under vacuum. The residue was purified by silica gel column chromatography eluting with dichloromethane/methyl alcohol (10:1) to afford 5-[5-methyl-5H-pyrido[4,3-b]indol-7-yl]-2-[(1s,3s)-3-hydroxycyclobutoxy]pyridine-3-carbonitrile (300 mg) as a yellow solid.

5-[5-methyl-5H-pyrido[4,3-b]indol-7-yl]-2-[(1s,3s)-3-hydroxycyclobutoxy]pyridine-3-carbonitrile was converted to the title compound according to the scheme below using procedures described for exemplary compound 220.

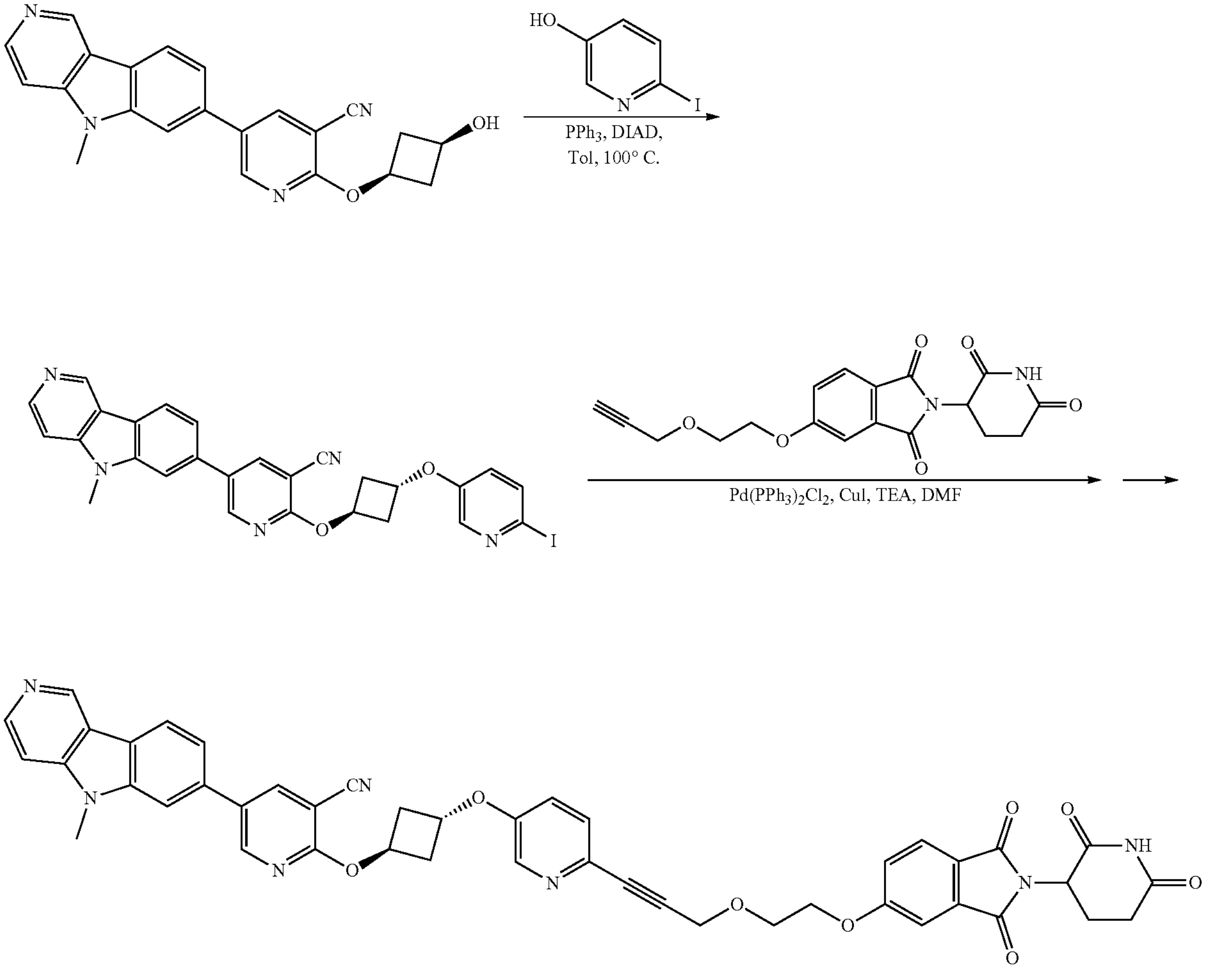

Exemplary Compound 235

Exemplary Synthesis of Exemplary Compound 248
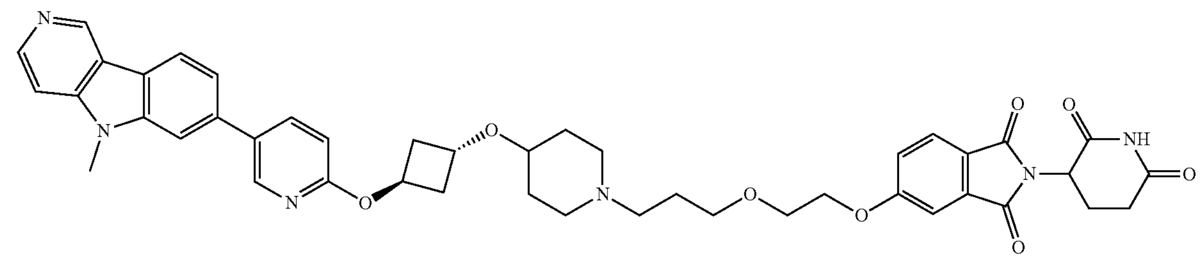 [SMILES: Cn1c2ccncc2c2ccc(-c3ccc(O[C@H]4C[C@H](OC5CCN(CCCOCCOc6ccc7c(c6)C(=O)N(C6CCC(=O)NC6=O)C7=O)CC5)C4)nc3)cc21]
Prepared according to the scheme below using procedures from examples described above and procedures commonly known to those skilled in the art.
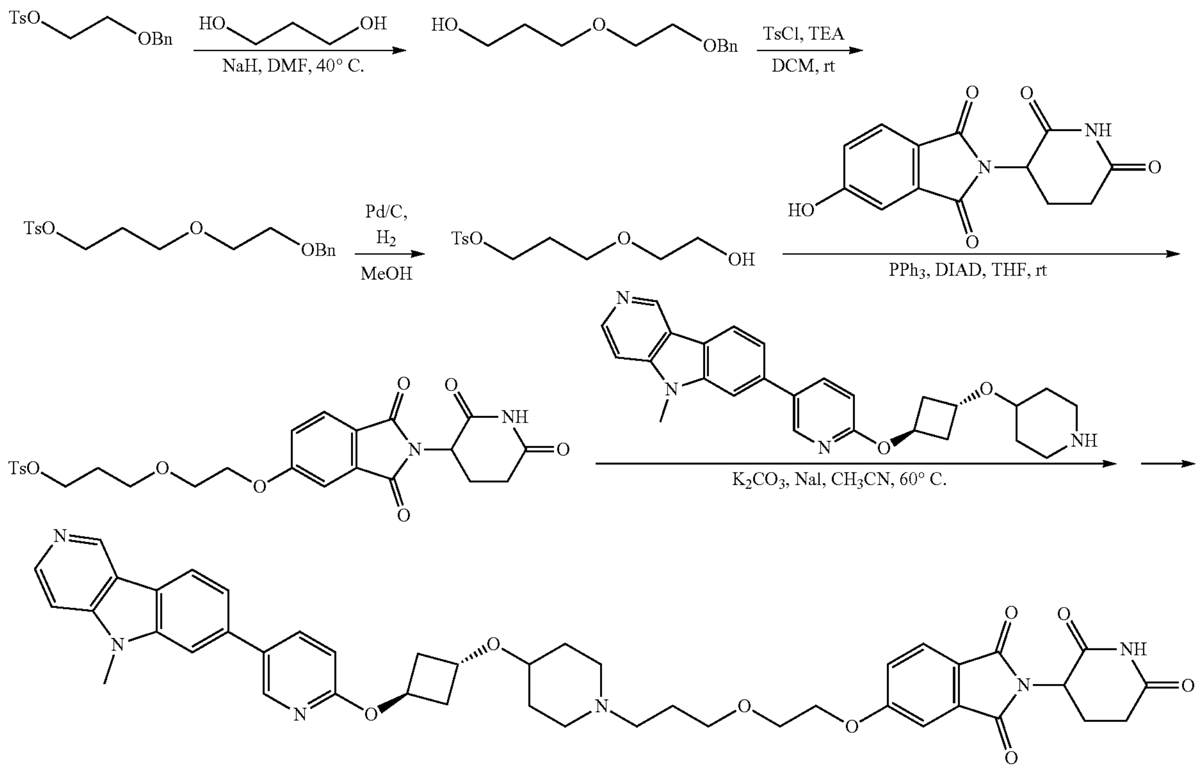
Exemplary Compound 248
Using analogous procedures the following exemplary compound was prepared: 384
Exemplary Synthesis of Exemplary Compound 338
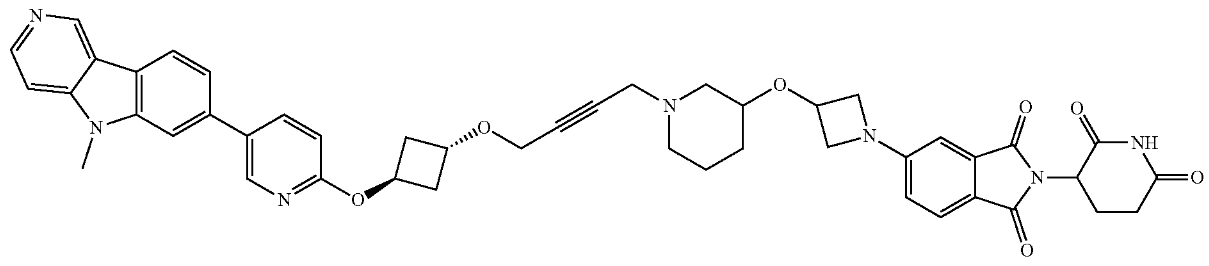 [SMILES: Cn1c2ccncc2c2ccc(-c3ccc(O[C@H]4C[C@H](OCC#CCN5CCCC(OC6CN(c7ccc8c(c7)C(=O)N(C7CCC(=O)NC7=O)C8=O)C6)C5)C4)nc3)cc21]

Step 1

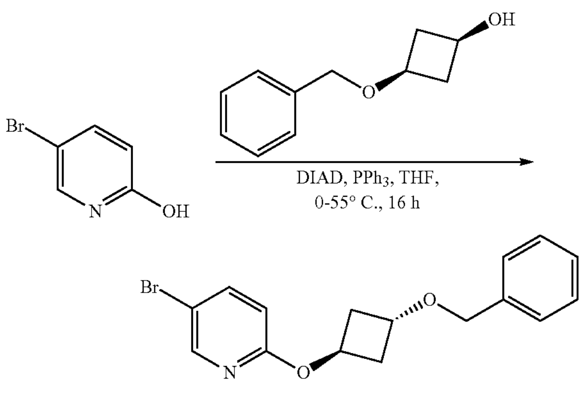

To a mixture of 3-benzyloxycyclobutanol (1 g, 5.61 mmol, 1.0 eq), 5-bromopyridin-2-ol (1.46 g, 8.42 mmol, 1.5 eq) and triphenylphosphine (2.21 g, 8.42 mmol, 1.5 eq) in tetrahydrofuran (30 mL) was added diisopropyl azodicarboxylate (1.70 g, 8.42 mmol, 1.64 mL, 1.5 eq) dropwise at 0° C. under nitrogen. The mixture was stirred at 55° C. for 16 hours. The mixture was then cooled to 25° C. and concentrated under vacuum. The residue was purified by silica gel chromatography (petroleum ether/ethyl acetate=150/1 to 30:1) to get the product. 2-(3-Benzyloxycyclobutoxy)-5-bromopyridine (1.41 g, 4.22 mmol, 75% yield) was obtained as a yellow oil.

Step 2

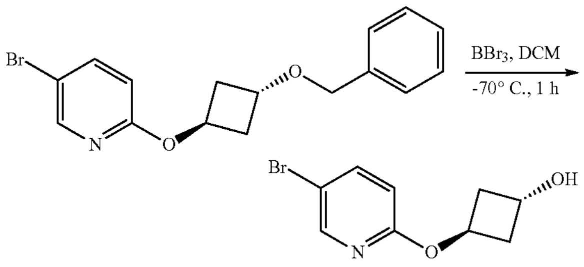

To a solution of 2-(3-benzyloxycyclobutoxy)-5-bromopyridine (3.66 g, 10.95 mmol, 1 eq) in dichloromethane (60 mL) was added boron tribromide (8.23 g, 32.85 mmol, 3.2 mL, 3 eq) dropwise at −70° C. The reaction was stirred at −70° C. for 1 hour. The reaction mixture was poured into a mixture of saturated aqueous solution of sodium bicarbonate (40 mL) and ammonium hydroxide (1 mL). The mixture was extracted with dichloromethane (50 mL×2). The combined organic phase was dried over anhydrous sodium sulfate, filtered and concentrated under vacuum. The residue was purified by silica gel column chromatography (petroleum ether/ethyl acetate=30/1 to 3:1) to get the product. 3-[(5-Bromo-2-pyridyl)oxy]cyclobutanol (1.37 g, 5.61 mmol, 51% yield) was obtained as a yellow solid.

Step 3

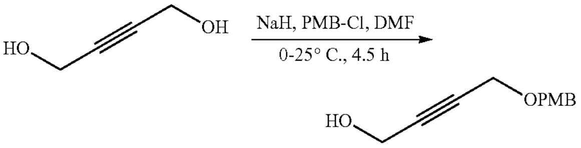

To a solution of but-2-yne-1,4-diol (5 g, 58.08 mmol, 1 eq) in N,N-dimethylformamide (50 mL) was added sodium hydride (2.32 g, 58.08 mmol, 60% in mineral oil, 1 eq) at 0° C. The mixture was stirred at 0° C. for 0.5 hour. Then methoxybenzylchloride (9.55 g, 60.98 mmol, 8.3 mL, 1.05 eq) was added into the mixture at 0° C. slowly, and the mixture was stirred at 25° C. for 4 hours. To the reaction was added water (40 mL). The solution was extracted with ethyl acetate (40 mL×3). Then the combined organic phase was washed with brine (20 mL×2), dried with anhydrous sodium sulfate, filtered and concentrated under vacuum. The residue was purified by silica gel column chromatography (petroleum ether/ethyl acetate=30/1 to 3:1) to get the product. 4-[(4-Methoxyphenyl)methoxy]but-2-yn-1-ol (2.64 g, 12.80 mmol, 22% yield) was obtained as a light yellow oil.

Step 4

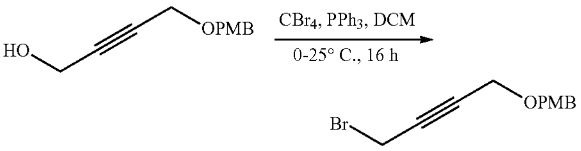

To a solution of 4-[(4-methoxyphenyl)methoxy]but-2-yn-1-ol (1 g, 4.85 mmol, 1 eq) and tetrabromomethane (1.61 g, 4.85 mmol, 1 eq) in dichloromethane (10 mL) was added triphenylphosphine (1.40 g, 5.33 mmol, 1.1 eq) at 0° C. The solution was stirred at 25° C. for 16 hours. The reaction solution was concentrated under vacuum. The residue was purified by silica gel column chromatography (petroleum ether/ethyl acetate=1:0 to 80:1) to get the product. 1-(4-Bromobut-2-ynoxymethyl)-4-methoxy-benzene (1 g, 3.72 mmol, 77% yield) was obtained as a light yellow oil.

Step 5

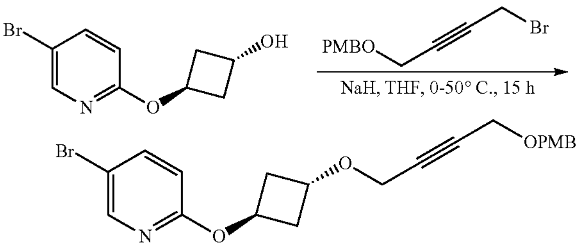

To a solution of 3-[(5-bromo-2-pyridyl)oxy]cyclobutanol (724 mg, 2.97 mmol, 1 eq) in tetrahydrofuran (10 mL) was added sodium hydride (237 mg, 5.93 mmol, 60% in mineral oil, 2 eq) at 0° C. The reaction mixture was stirred at 15° C. for 1 hour. Then a solution of 1-(4-bromobut-2-ynoxymethyl)-4-methoxy-benzene (878 mg, 3.26 mmol, 1.1 eq) in tetrahydrofuran (3 mL) was added, and the reaction mixture was stirred at 50° C. for another 14 hours. To the reaction was added saturated ammonium chloride solution (30 mL). Then the mixture was extracted with ethyl acetate (30 mL×3). Then the combined organic phase was washed with brine (20 mL), dried with anhydrous sodium sulfate, filtered and concentrated under vacuum. The residue was purified by silica gel column chromatography (petroleum ether/ethyl acetate=80:1 to 15:1) to get the product. 5-Bromo-2-[3-[4-[(4-methoxyphenyl)methoxy]but-2-ynoxy]cyclobutoxy]pyridine (974 mg, 2.25 mmol, 76% yield) was obtained as a light yellow gum.

Step 6

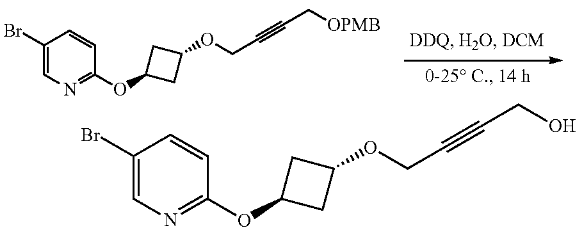

A solution of 5-bromo-2-[3-[4-[(4-methoxyphenyl)methoxy]but-2-ynoxy]cyclobutoxy]pyridine (974 mg, 2.25 mmol, 1 eq), 4,5-dichloro-3,6-dioxo-1,4-cyclohexadiene-1,2-carbonitrile (766 mg, 3.37 mmol, 1.5 eq) and water (1.15 g, 63.70 mmol, 1.2 mL, 28.31 eq) in dichloromethane (10 mL) was stirred at 0° C. for 4 hours. Then the reaction was stirred at 25° C. for another 10 hours. TLC showed a new main spot was detected. The reaction solution was added water (30 mL). The mixture was extracted with ethyl acetate (30 mL×3). Then the combined organic layer was washed with brine (20 mL), dried with anhydrous sodium sulfate, filtered and concentrated under vacuum to get the residue. The residue was purified by silica gel column chromatography (petroleum ether/ethyl acetate=40:1 to 5:1) to get the product. 4-[3-[(5-Bromo-2-pyridyl)oxy]cyclobutoxy]but-2-yn-1-ol (616 mg, 1.97 mmol, 88% yield) was obtained as a yellow gum.

Step 7

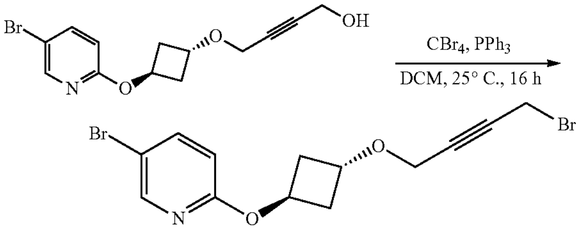

To a solution of 4-[3-[(5-bromo-2-pyridyl)oxy]cyclobutoxy]but-2-yn-1-ol (616 mg, 1.97 mmol, 1 eq) and tetrabromomethane (654 mg, 1.97 mmol, 1 eq) in dichloromethane (10 mL) was added triphenylphosphine (569 mg, 2.17 mmol, 1.1 eq) at 0° C. Then the reaction was stirred at 25° C. for 14 hours. The reaction solution was concentrated under vacuum. The residue was purified by silica gel column chromatography (petroleum ether/ethyl acetate=1:0 to 40:1) to get the product. 5-Bromo-2-[3-(4-bromobut-2-ynoxy)cyclobutoxy]pyridine (500 mg, 1.33 mmol, 68% yield) was obtained as a light yellow gum.

Step 8

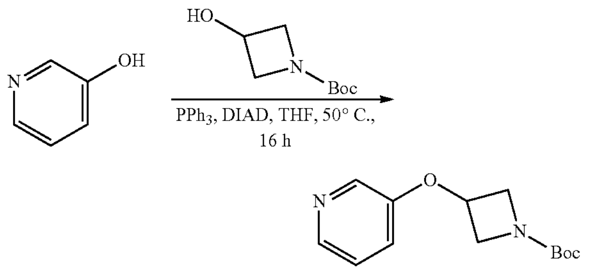

To a solution of pyridin-3-ol (4.94 g, 51.96 mmol, 1.5 eq) and tert-butyl 3-hydroxyazetidine-1-carboxylate (6 g, 34.64 mmol, 1 eq) in tetrahydrofuran (100 mL) was added triphenylphosphine (10.90 g, 41.57 mmol, 1.2 eq) and diisopropyl azodicarboxylate (8.41 g, 41.57 mmol, 8.08 mL, 1.2 eq) in one portion at 15° C., and the mixture was then stirred at 50° C. for 16 h. The reaction mixture was concentrated under reduced pressure to remove tetrahydrofuran. Water (50 mL) was poured into the mixture, and stirring continued for 1 minute. The aqueous phase was extracted with dichloromethane (60 mL×3). The combined organic phase was washed with brine (20 mL×2), dried with anhydrous sodium sulfate, filtered and concentrated in vacuum. The residue was purified by flash silica gel chromatography. tert-Butyl 3-(3-pyridyloxy)azetidine-1-carboxylate (6.24 g, 23.0 mmol, 66% yield) was obtained as a yellow oil.

Step 9

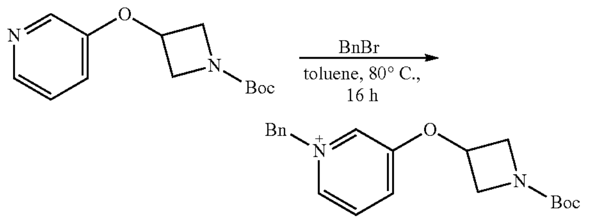

To a solution of tert-butyl 3-(3-pyridyloxy)azetidine-1-carboxylate (3 g, 11.05 mmol, 1 eq) in toluene (30 mL) was added bromomethylbenzene (1.89 g, 11.05 mmol, 1.31 mL, 1 eq). The mixture was stirred at 80° C. for 16 h. The reaction mixture was concentrated under reduced pressure to remove toluene. The crude product was triturated with petroleum ether (100 mL), then filtered to give the filter cake as a crude product. tert-Butyl 3-(1-benzylpyridin-1-ium-3-yl)oxyazetidine-1-carboxylate (3.9 g, crude) was obtained as a light yellow solid.

Step 10

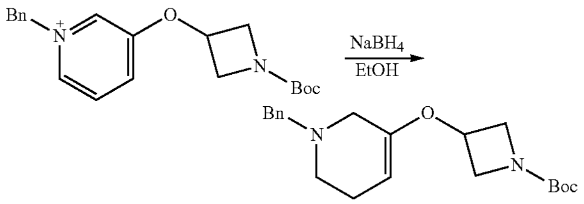

To a solution of tert-butyl 3-(1-benzylpyridin-1-ium-3-yl) oxyazetidine-1-carboxylate (3.77 g, 11.04 mmol, 1 eq) in ethanol (70 mL) was added sodium borohydride (2.51 g, 66.25 mmol, 6 eq) at 0° C. The mixture was stirred at 10° C. for 12 h. The reaction mixture was concentrated to remove solvent and then extracted with ethyl acetate (80 mL×3). The combined organic layers were washed with brine 30 mL, dried over anhydrous sodium sulfate, filtered and concentrated under reduced pressure. The residue was purified by silica gel column chromatography (petroleum ether/ethyl acetate=3/1 to dichloromethane/methanol=20/1) to give crude product, which then was purified by semi-preparative reverse phase HPLC (column: Kromasil 250*50 mm*10 um; mobile phase: [water (0.225% FA)-ACN]; B %: 17%-47%, 30 min, 40% min). tert-Butyl 3-[(1-benzyl-3,6-dihydro-2H-pyridin-5-yl)oxy]azetidine-1-carboxylate (1.29 g, 3.75 mmol, 33% yield) was obtained as a yellow oil.

Step 11

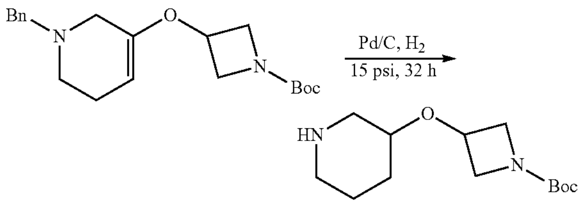

To a solution of tert-butyl 3-[(1-benzyl-3,6-dihydro-2H-pyridin-5-yl)oxy]azetidine-1-carboxylate (1.24 g, 3.60 mmol, 1 eq) in tetrahydrofuran (10 mL) and ethanol (10 mL) was added 10% Pd/C (200 mg) under nitrogen. The suspension was degassed under vacuum and purged with hydrogen three times. The mixture was stirred under hydrogen (15 psi) at 15° C. for 32 h. The reaction mixture was filtered, and the filtrate was concentrated. The residue was purified by silica gel column chromatography (petroleum ether/ethyl acetate=1/1 to dichloromethane/methanol/tetrahydrofuran=10/1/1). tert-Butyl 3-(3-piperidyloxy)azetidine-1-carboxylate (620 mg, 2.42 mmol, 67% yield) was obtained as a yellow oil.

Step 12

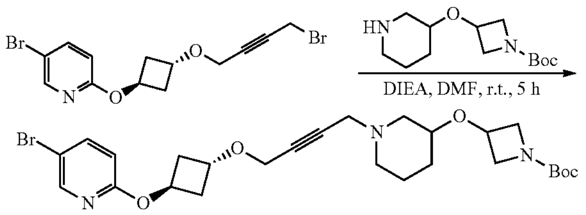

To a solution of 5-bromo-2-[3-(4-bromobut-2-ynoxy)cyclobutoxy]pyridine (300 mg, 0.80 mmol, 1 eq) and tert-butyl 3-(3-piperidyloxy)azetidine-1-carboxylate (205 mg, 0.80 mmol, 1 eq) in N,N-dimethylformamide (5 mL) was added diisopropylethylamine (310 mg, 2.40 mmol, 0.42 mL, 3 eq), and the mixture was stirred at 20° C. for 5.5 h. The reaction mixture was poured into water (30 mL) and then extracted with ethyl acetate (30 mL×3). The combined organic phase was washed with brine (5 mL), dried with anhydrous sodium sulfate, filtered and concentrated in vacuum. The residue was purified by silica gel column chromatography (petroleum ether/ethyl acetate=2/1 to 0/1). tert-Butyl 3-[[1-[4-[3-[(5-bromo-2-pyridyl)oxy]cyclobutoxy]but-2-ynyl]-3-piperidyl]oxy]azetidine-1-carboxylate (445 mg, crude) was obtained as a yellow oil.

tert-butyl 3-((1-(4-((1r,3r)-3-((5-bromopyridin-2-yl)oxy)cyclobutoxy)but-2-yn-1-yl)piperidin-3-yl)oxy)azetidine-1-carboxylate was converted to the title compound according to the scheme below using procedures described for other examples above and common procedures known to those skilled in the art.

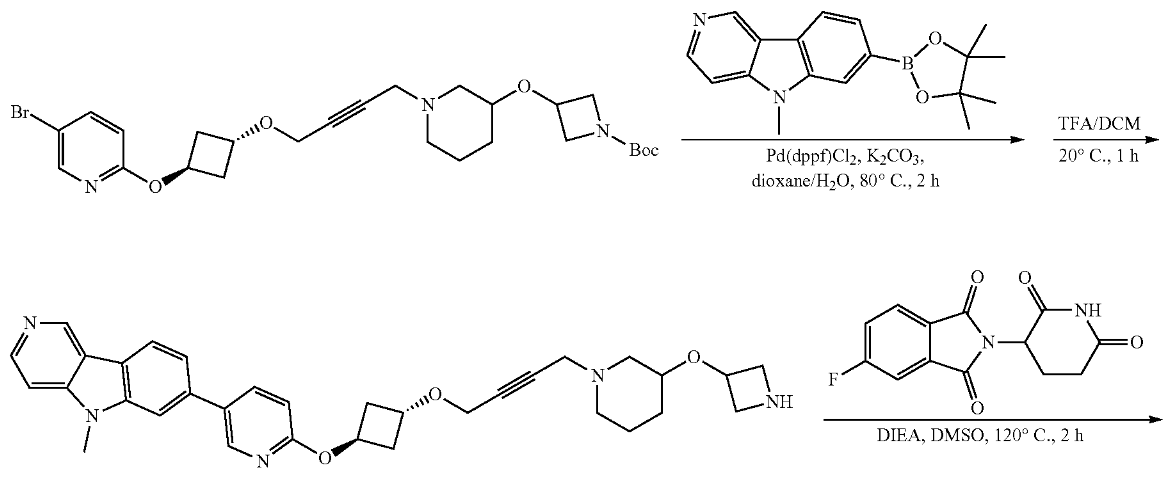

-continued

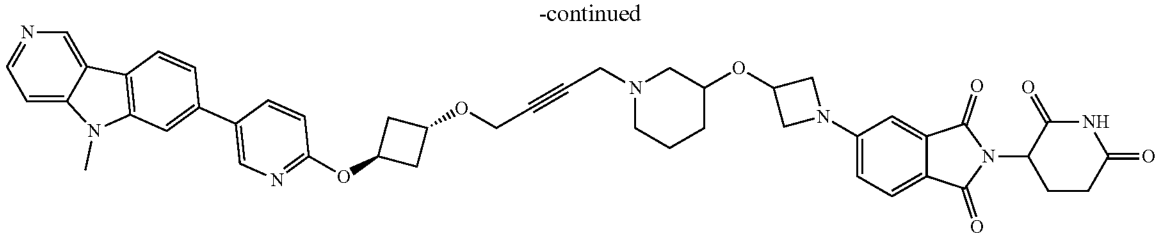

Exemplary Compound 338

Exemplary Synthesis of Exemplary Compound 272

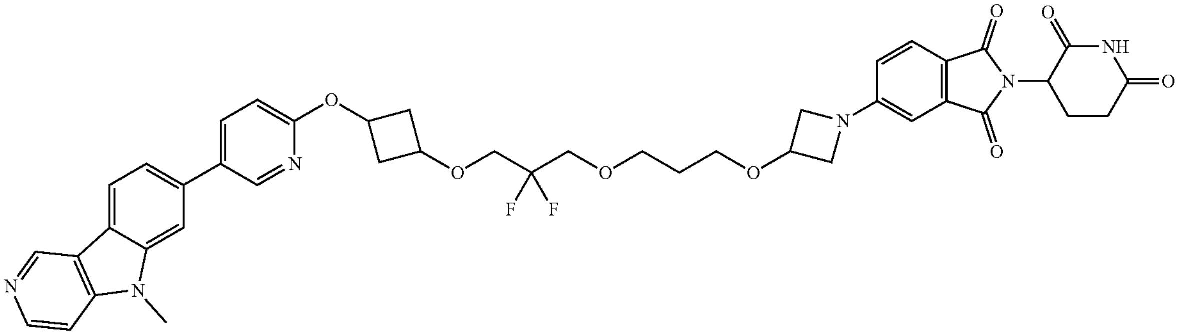 [SMILES: Cn1c2ccncc2c2ccc(-c3ccc(OC4CC(OCC(F)(F)COCCCOC5CN(c6ccc7c(c6)C(=O)N(C6CCC(=O)NC6=O)C7=O)C5)C4)nc3)cc21]

Step 1

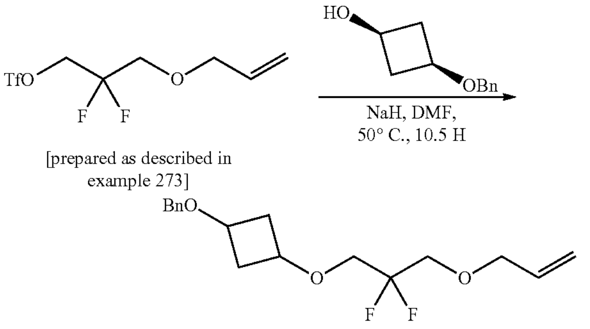

Step 2

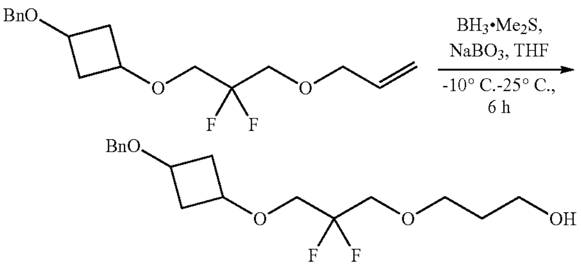

To a mixture of 3-benzyloxycyclobutanol (3.76 g, 21.11 mmol, 1.20 eq) in N,N-dimethylformamide (50 mL) was added 60% sodium hydride (809 mg, 20.23 mmol, 1.15 eq) at 0° C. and stirred for 0.5 h under nitrogen. To the mixture was then added a solution of (3-allyloxy-2,2-difluoro-propyl) trifluoromethanesulfonate (5.00 g, 17.59 mmol, 1.00 eq) in N,N-dimethylformamide (25 mL) at 0° C. The mixture was heated to 50° C. and stirred for 10 h. The mixture was cooled to 25° C. and poured into saturated ammonium chloride solution (50 mL) and stirred for 15 min. The aqueous phase was extracted with ethyl acetate (50 mL×3). The combined organic phase was washed with brine (50 mL×3), dried with anhydrous sodium sulfate, filtered and concentrated under vacuum. The residue was purified by silica gel chromatography (petroleum ether/ethyl acetate=100/1 to 50/1) to afford [3-(3-allyloxy-2,2-difluoro-propoxy)cyclobutoxy]methylbenzene (1.80 g, 5.76 mmol, 32% yield) as a yellow oil.

To a solution of [3-(3-allyloxy-2,2-difluoro-propoxy)cyclobutoxy]methylbenzene (1.80 g, 5.76 mmol, 1 eq) in tetrahydrofuran (36 mL) was added borane-dimethyl sulfide complex (10 M, 1.15 mL, 2 eq) at −10° C., warmed to 25° C. and stirred for 4 h under nitrogen. Then to the mixture was added a solution of sodium perborate tetrahydrate (2.66 g, 17.29 mmol, 3.32 mL, 3 eq) in water (20 mL) at 0° C., and the mixture was warmed to 25° C. and stirred for 2 h. The suspension was filtered and concentrated in vacuum. The residue was poured into ice-water (w/w=1/1) (50 mL) and stirred for 15 min. The aqueous phase was extracted with ethyl acetate (50 mL×3). The combined organic phase was washed with brine (50 mL×3), dried with anhydrous sodium sulfate, filtered and concentrated under vacuum. The residue was purified by silica gel chromatography (petroleum ether/ethyl acetate=10/1 to 3/1) to afford 3-[3-(3-benzyloxycyclobutoxy)-2,2-difluoro-propoxy]propan-1-ol (650 mg, 1.97 mmol, 34% yield) as a colorless oil.

3-[3-(3-Benzyloxycyclobutoxy)-2,2-difluoro-propoxy] propan-1-ol was converted to the title compound according to the scheme below using procedures described for the examples above and common procedures known to those skilled in the art.

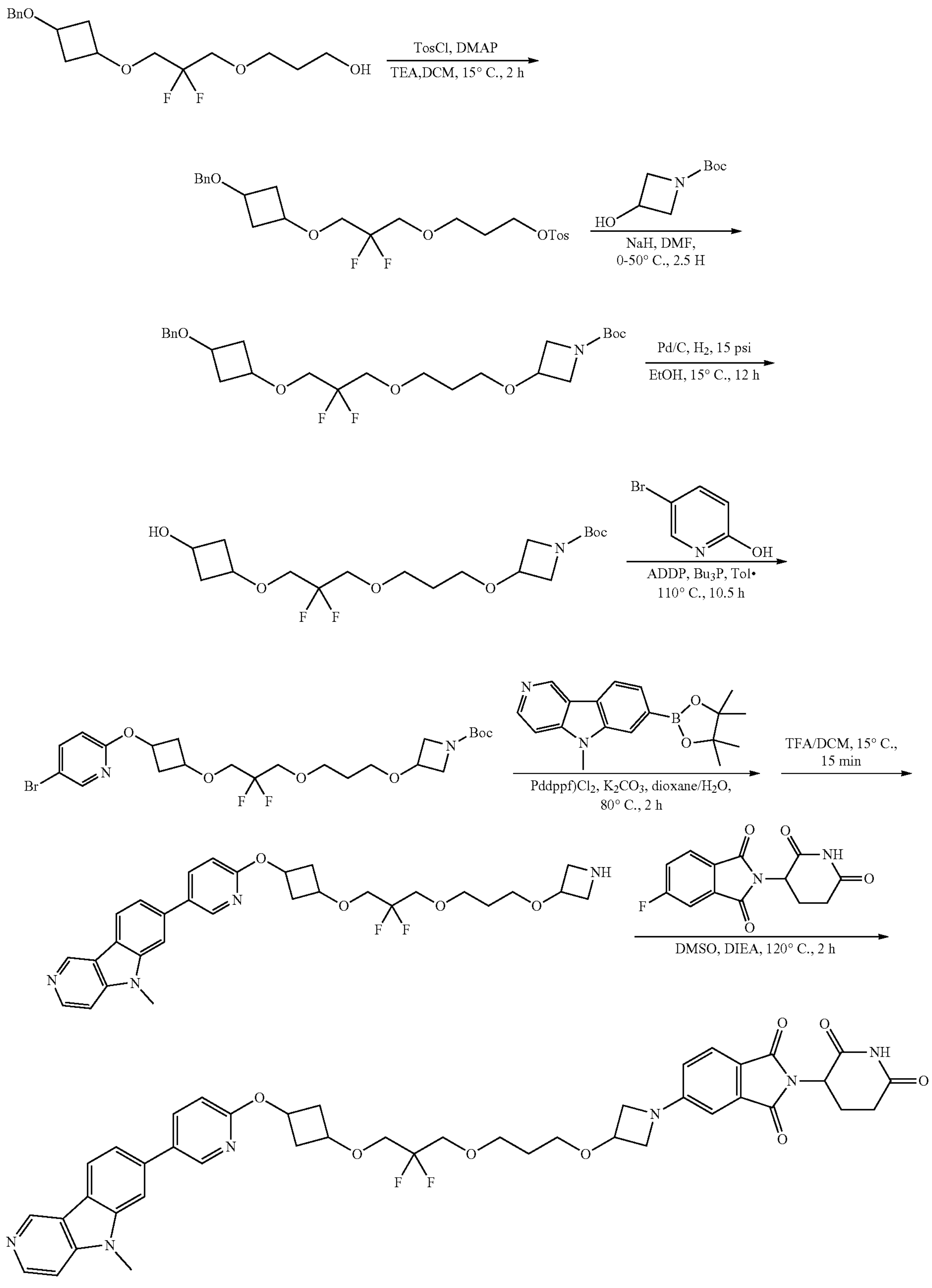
Exemplary Compound 272

Exemplary Synthesis of Exemplary Compound 236

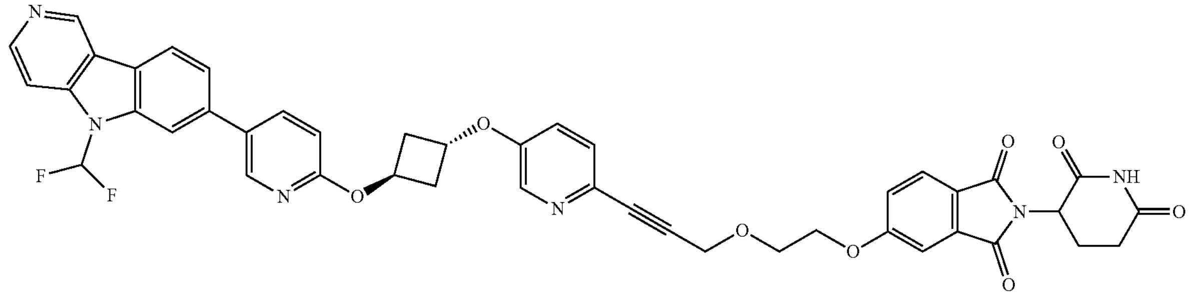 [SMILES: O=C1CCC(N2C(=O)c3ccc(OCCOCC#Cc4ccc(O[C@H]5C[C@H](Oc6ccc(-c7ccc8c9cnccc9n(C(F)F)c8c7)cn6)C5)cn4)cc3C2=O)C(=O)N1]

Step 1

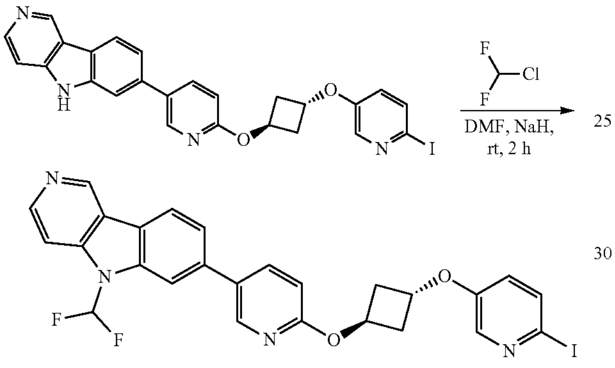

To a solution of 5-[5H-pyrido[4,3-b]indol-7-yl]-2-[(1r,3r)-3-[(6-iodopyridin-3-yl)oxy]cyclobutoxy]pyridine (140 mg, 0.26 mmol, 1 equiv) [prepared as described by Crew, A. et al. in US 20180125821] in DMF (10 mL) was added sodium hydride (60% in oil, 21 mg) at 0° C. The mixture was stirred for 30 min. Chlorodifluoromethane gas was bubbled through the solution while stirring for 2 h at room temperature. The reaction mixture was quenched by water and extracted with dichloromethane (25 mL×3). The organic phase was concentrated under reduced pressure. The residue was purified by silica gel column chromatography eluting with dichloromethane/methyl alcohol (10:1) to afford 5-[5-(difluoromethyl)-5H-pyrido[4,3-b]indol-7-yl]-2-[(1r,3r)-3-[(6-iodopyridin-3-yl)oxy]cyclobutoxy]pyridine (52 mg, 34%) as a yellow solid.

5-[5-(difluoromethyl)-5H]-pyrido[4,3-b]indol-7-yl]-2-[(1r,3r)-3-[(6-iodopyridin-3-yl)oxy]cyclobutoxy]pyridine was converted to the title compound according to the scheme below using procedure described for examples above.

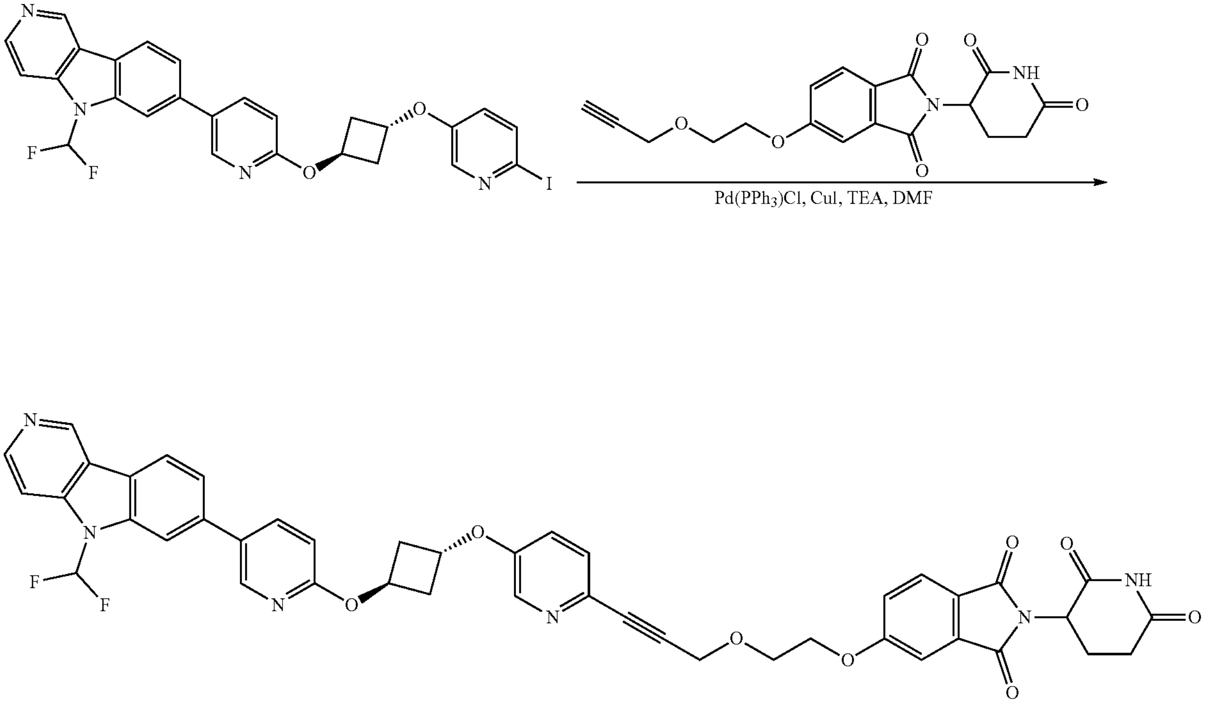

Exemplary Compound 236

Exemplary Synthesis of Exemplary Compound 242

Step 1

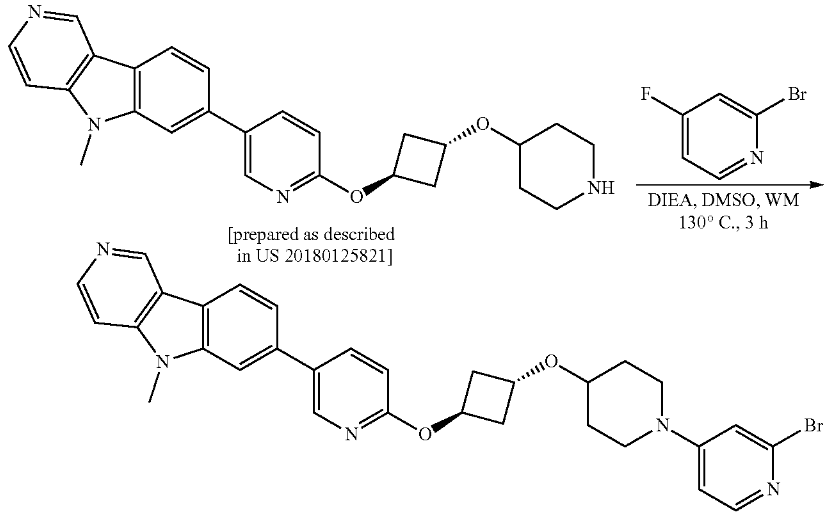

Into a 10-mL microwave tube purged and maintained with an inert atmosphere of nitrogen, was placed 5-[5-methyl-5H-pyrido[4,3-b]indol-7-yl]-2-[(1r,3r)-3-(piperidin-4-yloxy)cyclobutoxy]pyridine hydrochloride (100 mg, 0.22 mmol, 1 equiv), DIEA (1 mL), and 2-bromo-4-fluoropyridine (38 mg, 0.22 mmol, 1 equiv) in DMSO (4 mL). The resulting solution was stirred for 3 h at 130° C. The resulting mixture was diluted with water (10 mL). The aqueous layer was extracted with ethyl acetate (20 mL×3). The residue was washed with brine (10 mL×1). The organic phase was concentrated under reduced pressure. The residue was purified by silica gel column chromatography eluting with methanol/dichloromethane ether (1:10) to afford 5-[5-methyl-5H-pyrido[4,3-b]indol-7-yl]-2-[(1r,3r)-3-[[1-(2-bromopyridin-4-yl)piperidin-4-yl]oxy]cyclobutoxy]pyridine (60 mg, 48%) as a yellow solid.

Step 2

Into a 25-mL microwave tube purged and maintained with an inert atmosphere of nitrogen, was placed 5-[5-methyl-5H-pyrido[4,3-b]indol-7-yl]-2-[(1r,3r)-3-[[1-(2-bromopyridin-4-yl)piperidin-4-yl]oxy]cyclobutoxy]pyridine (69 mg, 0.12 mmol, 1 equiv), NaI (35 mg, 0.24 mmol, 2 equiv), CuI (1.1 mg, 0.01 mmol, 0.05 equiv), methyl[2-(methylamino)ethyl]amine (1 mg, 0.01 mmol, 0.10 equiv) in dioxane (3 mL). The resulting solution was stirred for 12 h at 110° C. The solids were filtered out. The filtrate was diluted with water (30 mL) and extracted with dichloromethane (60 mL). The resulting mixture was washed with brine (10 mL×2). The organic phase was concentrated under reduced pressure. The residue was applied onto a silica gel column eluting with dichloromethane/methanol (1:20). This resulted in 80 mg (crude) of 5-[5-methyl-5H-pyrido[4,3-b]indol-7-yl]-2-[(1r,3r)-3-[[1-(2-iodopyridin-4-yl)piperidin-4-yl]oxy]cyclobutoxy]pyridine as a yellow solid.

5-[5-methyl-5H-pyrido[4,3-b]indol-7-yl]-2-[(1r,3r)-3-[[1-(2-iodopyridin-4-yl)piperidin-4-yl]oxy]cyclobutoxy] pyridine was converted to the title compound as described for the last step of exemplary compound 220.

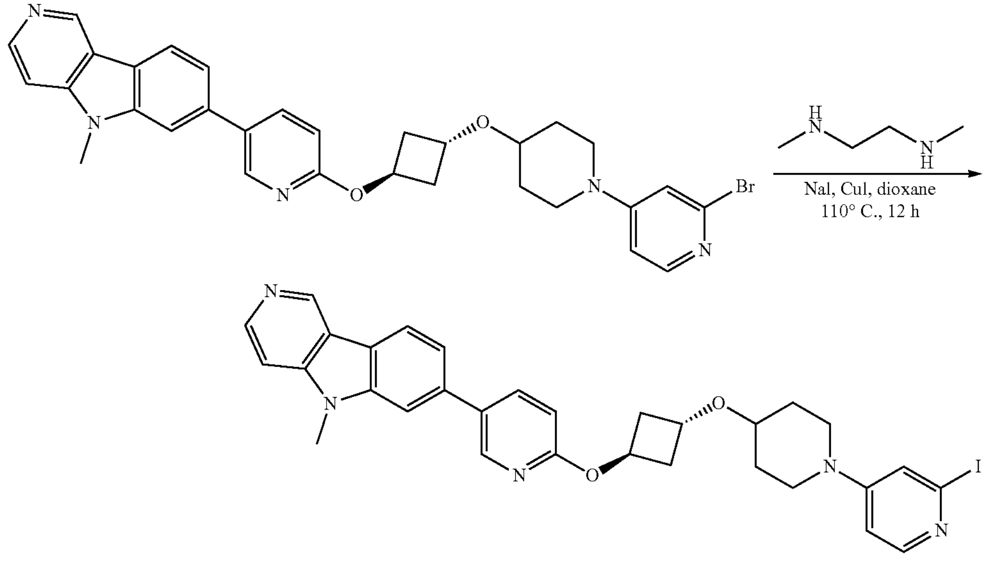

Exemplary Synthesis of Exemplary Compound 250

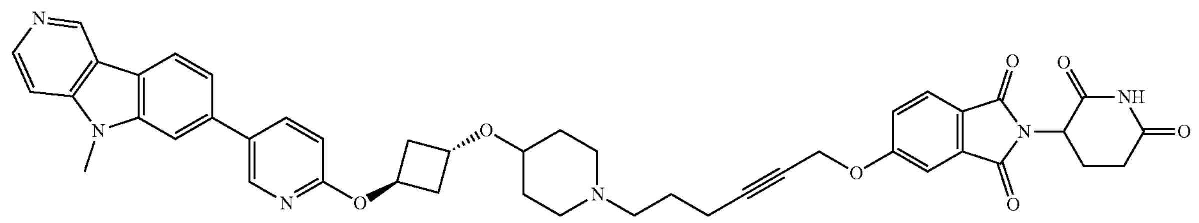 [SMILES: Cn1c2ccncc2c2ccc(-c3ccc(O[C@H]4C[C@H](OC5CCN(CCCC#CCOc6ccc7c(c6)C(=O)N(C6CCC(=O)NC6=O)C7=O)CC5)C4)nc3)cc21]

Step 1

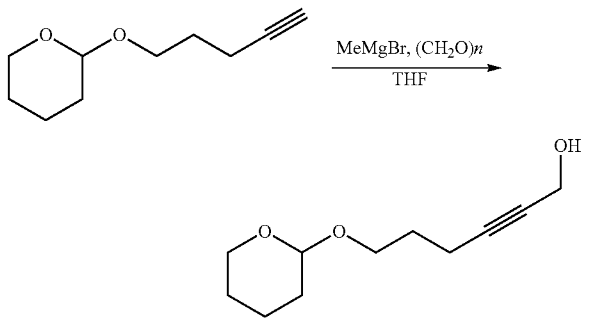

A solution of 2-(pent-4-yn-1-yloxy)oxane (500 mg, 2.97 mmol, 1 equiv) in THF was treated with MeMgBr (1M in THF, 709 mg, 5.94 mmol, 2 equiv) for 1 h at 60° C. under nitrogen atmosphere followed by the addition of paraformaldehyde (268 mg, 8.92 mmol, 3.0 equiv) in portions at room temperature. The resulting mixture was stirred overnight at 65° C. under nitrogen atmosphere. The reaction was quenched by the addition of water (5 mL) at room temperature. The aqueous layer was extracted with ethyl acetate (20 mL×3). The resulting mixture was washed with saturated brine (20 mL×1). The resulting was dried by $Na_2SO_4$. The residue was purified by silica gel column chromatography eluting with ethyl acetate/petroleum ether (1:1) to afford 6-(oxan-2-yloxy)hex-2-yn-1-ol (150 mg, 25%) as a yellow oil.

6-(oxan-2-yloxy)hex-2-yn-1-ol was converted to the title compound according to the scheme below using procedure described for examples above and procedures commonly known to those skilled in the art.

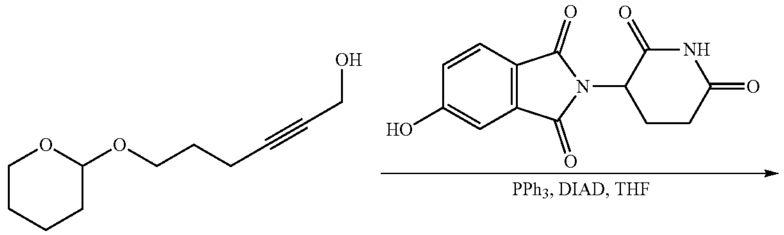

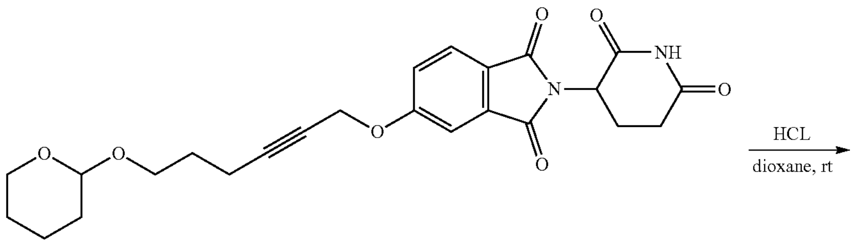

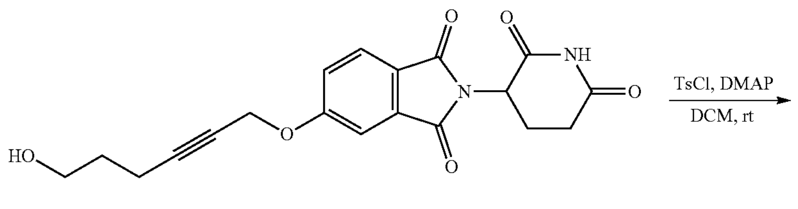

-continued

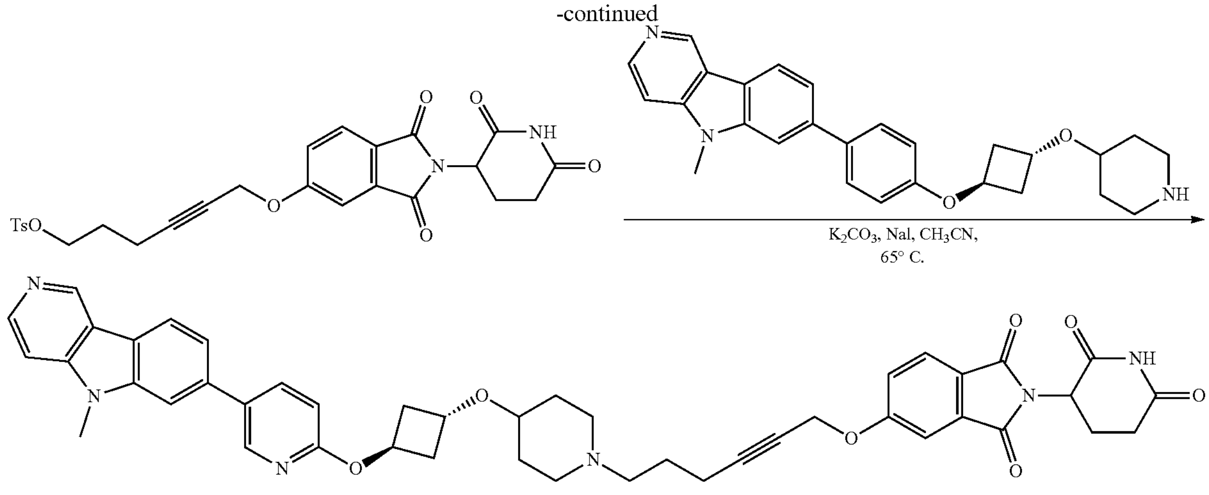

Exemplary Compound 250

Exemplary Synthesis of Exemplary Compound 339

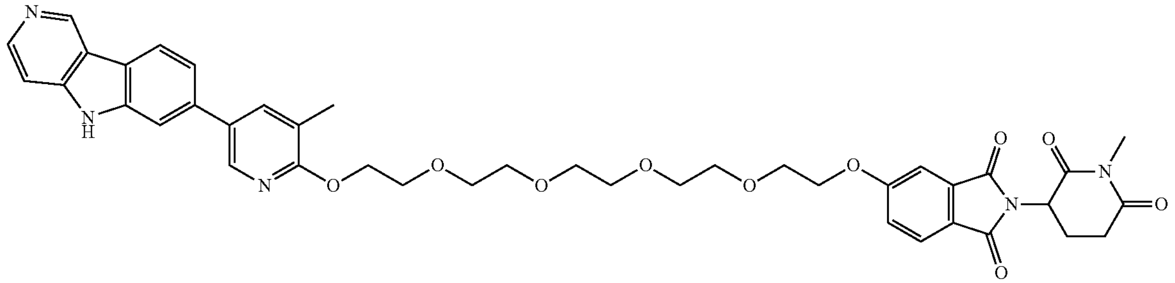 [SMILES: Cc1cc(-c2ccc3c(c2)[nH]c2ccncc23)cnc1OCCOCCOCCOCCOCCOc1ccc2c(c1)C(=O)N(C1CCC(=O)N(C)C1=O)C2=O]

Step 1

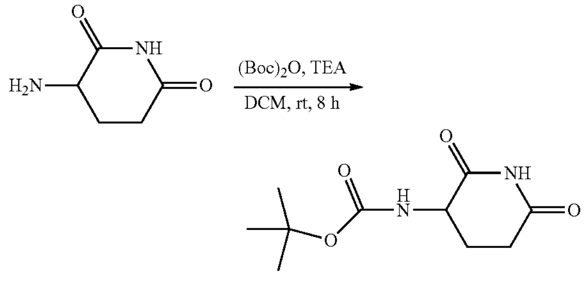

Into a 500-mL round-bottom flask, were placed 3-aminopiperidine-2,6-dione hydrochloride (10 g, 60.8 mmol, 1 equiv), TEA (18.4 g, 182 mmol, 3 equiv), and $(Boc)_2O$ (15.9 g, 73.6 mmol, 1.2 equiv) in dichloromethane (100 mL). The resulting solution was stirred for 8 h at room temperature. The reaction was then quenched by the addition of 20 mL water/ice. The resulting mixture was extracted with dichloromethane (100 mL×3), and the organic layers were combined. The organic phase was washed with brine (20 mL×3), dried over anhydrous sodium sulfate and concentrated. The residue was applied onto a silica gel column eluting with ethyl acetate/petroleum ether (1/1). The collected fractions were combined and concentrated under vacuum. This resulted in 8 g (58%) of tert-butyl N-(2,6-dioxopiperidin-3-yl)carbamate as a white solid.

Step 2

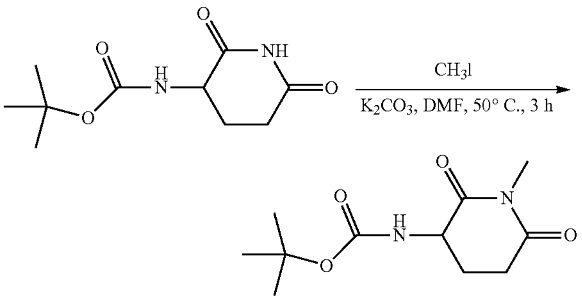

Into a 50-mL round-bottom flask, were placed tert-butyl N-(2,6-dioxopiperidin-3-yl)carbamate (2.0 g, 8.76 mmol, 1 equiv), iodomethane (1.63 mL, 26.1 mmol, 3 equiv), and $K_2CO_3$ (3.6 g, 26.1 mmol, 3 equiv) in DMF (30 mL). The resulting solution was stirred for 3 h at 50° C. in an oil bath. The reaction was then quenched by the addition of 20 mL ice/brine. The resulting mixture was extracted with ethyl acetate (20 mL×3), and the organic layers were combined. The resulting mixture was washed with brine (20 mL), dried over anhydrous sodium sulfate and concentrated. This resulted in 1.77 g (84%) of tert-butyl N-(1-methyl-2,6-dioxopiperidin-3-yl)carbamate as a white solid.

Step 3

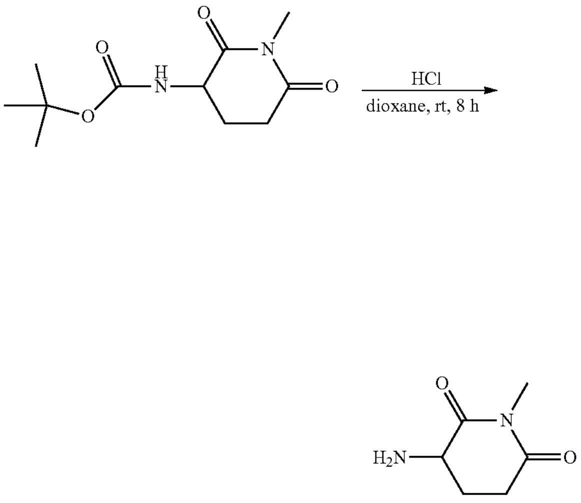

Into a 500-mL round-bottom flask, were placed tert-butyl N-(1-methyl-2,6-dioxopiperidin-3-yl)carbamate (1.77 g, 7.32 mmol) and hydrogen chloride in dioxane (4 mol/L, 10 mL) in dioxane (20 mL). The resulting solution was stirred for 8 h at 25° C. The resulting mixture was concentrated. This resulted in 1.27 g of crude 3-amino-1-methylpiperidine-2,6-dione hydrochloride as a white solid.

Step 4

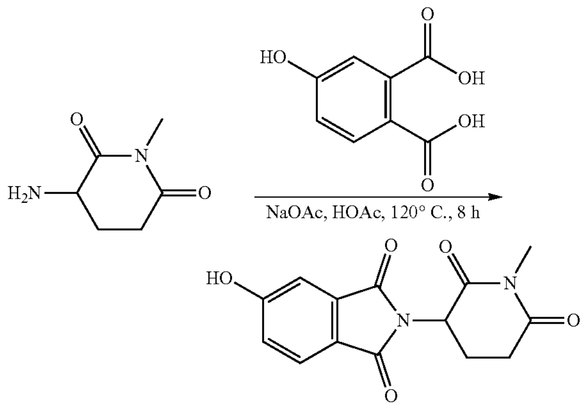

Into a 100-mL round-bottom flask, was placed 3-amino-1-methylpiperidine-2,6-dione hydrochloride (1.22 g, 6.85 mmol, 1 equiv) and NaOAc (2.2 g, 27.4 mmol, 4 equiv) in HOAc (10 mL). This was followed by the addition of 4-hydroxybenzene-1,2-dicarboxylic acid (1.25 g, 6.85 mmol, 1 equiv). The resulting solution was stirred for 8 h at 120° C. in an oil bath, and then was concentrated under vacuum. The residue was diluted with 20 mL water. The solids were collected by filtration. This resulted in 1.21 g (61%) of 5-hydroxy-2-(1-methyl-2,6-dioxopiperidin-3-yl)-2,3-dihydro-1H-isoindole-1,3-dione as a dark brown solid.

5-hydroxy-2-(1-methyl-2,6-dioxopiperidin-3-yl)-2,3-dihydro-1H-isoindole-1,3-dione was converted to the title compound according to the scheme below using procedures described for examples above and in US 20180125821.

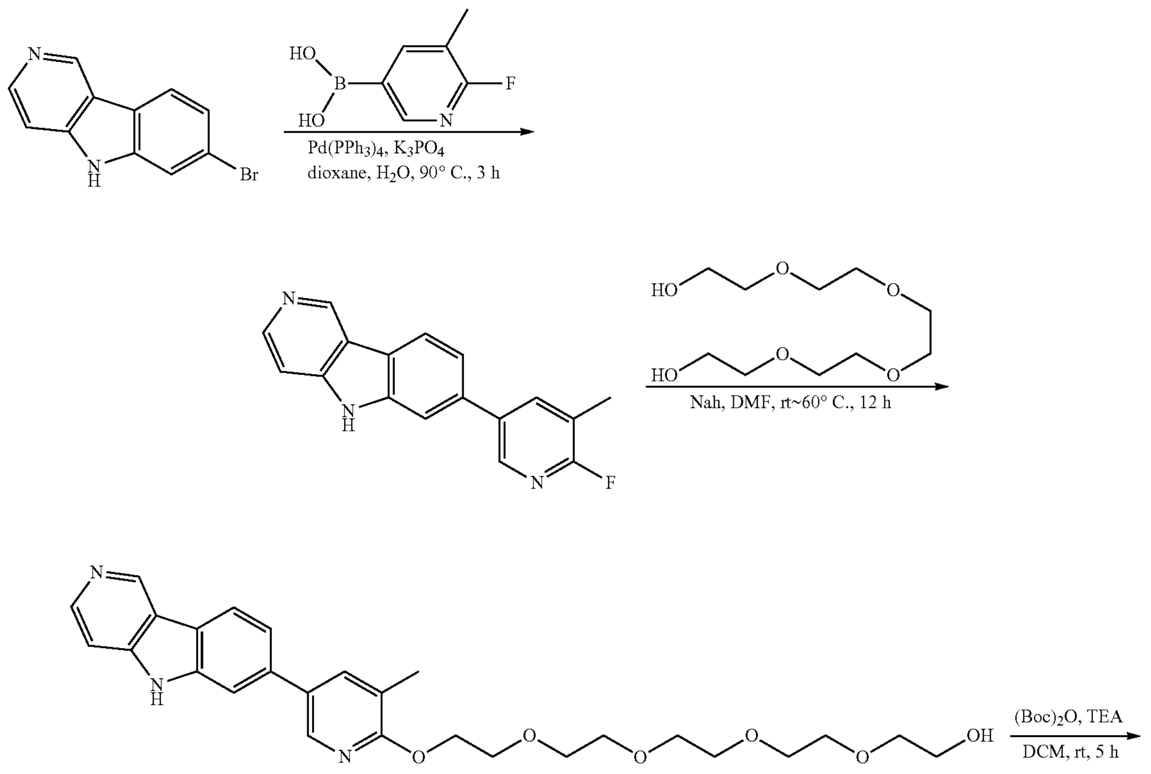

-continued
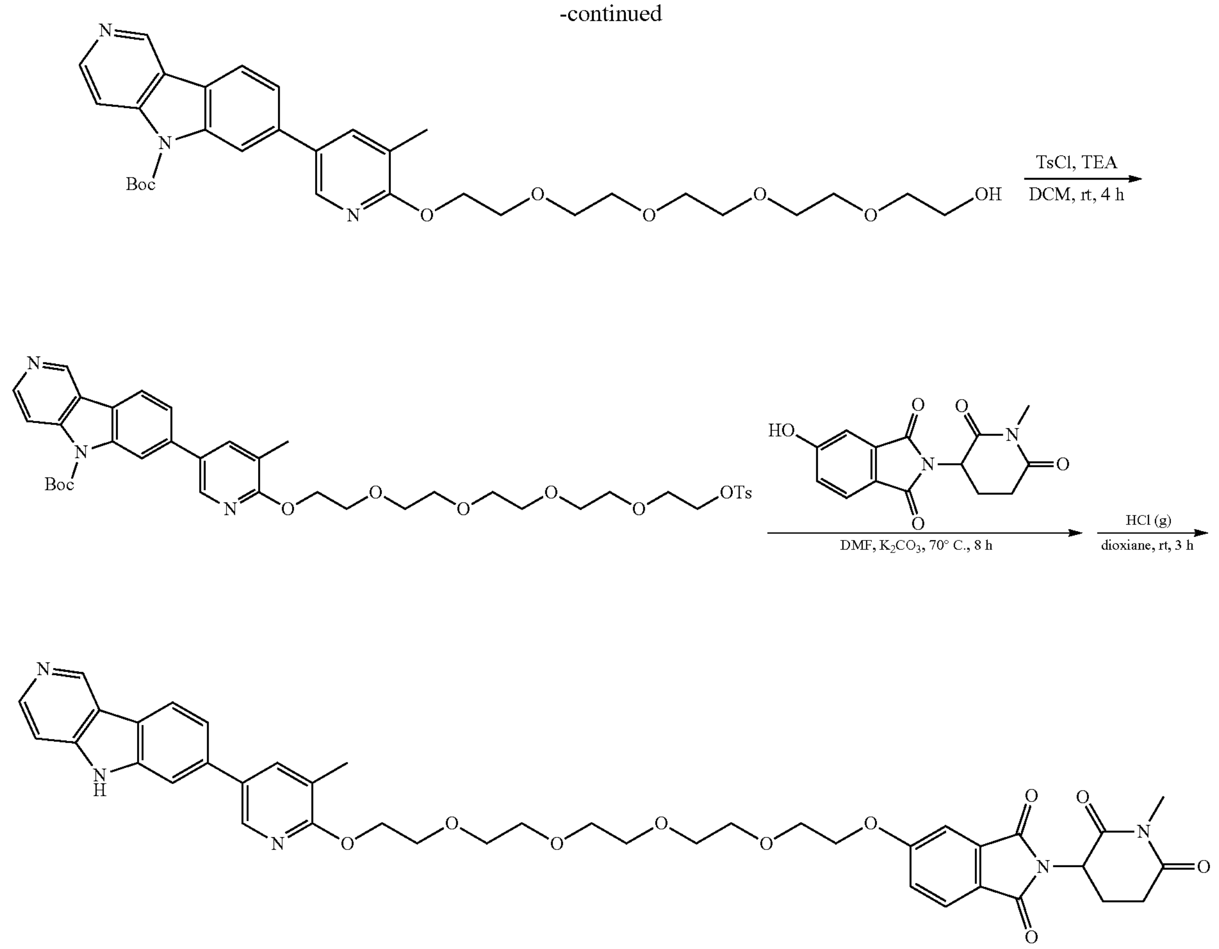
Exemplary Compound 339
Exemplary Synthesis of Exemplary Compound 244 IDC
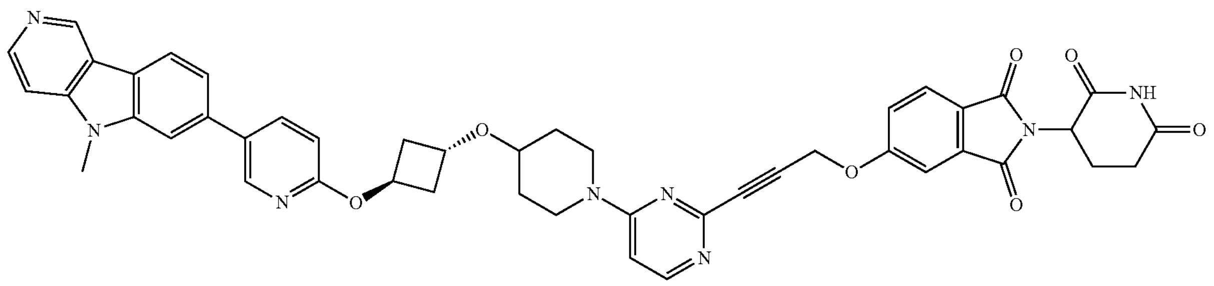 [SMILES: Cn1c2ccncc2c2ccc(-c3ccc(O[C@H]4C[C@H](OC5CCN(c6ccnc(C#CCOc7ccc8c(c7)C(=O)N(C7CCC(=O)NC7=O)C8=O)n6)CC5)C4)nc3)cc21]
Step 1
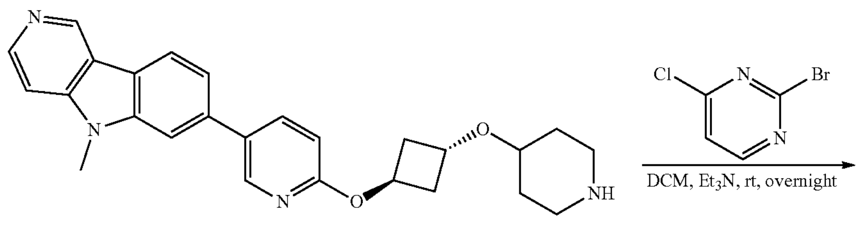

-continued

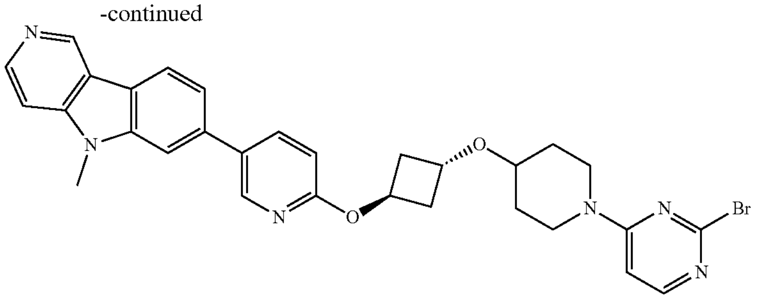

Into a 100-mL round-bottom flask, was placed 5-[5-methyl-5H-pyrido[4,3-b]indol-7-yl]-2-[(1r,3r)-3-(piperidin-4-yloxy)cyclobutoxy]pyridine hydrochloride (300 mg, 0.65 mmol, 1 equiv), TEA (0.5 mL), and 2-bromo-4-chloropyrimidine (125 mg, 0.65 mmol, 1 equiv) in dichloromethane (20 mL). The resulting solution was stirred overnight at room temperature. The resulting mixture was diluted with water (30 mL). The mixture was extracted with ethyl acetate (30 mL×2). The organic layers were combined and washed with brine (20 mL×2), dried over anhydrous sodium sulfate, and concentrated. The residue was purified by silica gel column chromatography eluting with methanol/dichloromethane (1:15) to afford to 2-bromo-4-[4-[(1r,3r)-3-[(5-[5-methyl-5H-pyrido[4,3-b]indol-7-yl]pyridin-2-yl)oxy]cyclobutoxy]piperidin-1-yl]pyrimidine (179 mg, 48%) as a yellow solid.

Step 2

Into a 25-mL microwave tube purged and maintained with an inert atmosphere of nitrogen, was placed 2-bromo-4-[4-[(1r,3r)-3-[(5-[5-methyl-5H-pyrido[4,3-b]indol-7-yl]pyridin-2-yl)oxy]cyclobutoxy]piperidin-1-yl]pyrimidine (179 mg, 0.31 mmol, 1 equiv), CuI (2.9 mg, 0.02 mmol, 0.05 equiv), NaI (92 mg, 0.61 mmol, 2 equiv), and TEA (2.2 mL, 22.1 mmol, 52.7 equiv) in dioxane (18 mL). The resulting solution was stirred overnight at 110° C. The insoluble solids in the reaction mixture were filtered out, and the filtrate was concentrated under vacuum. The residue was purified by silica gel column chromatography eluting with methanol/dichloromethane (1:15) to afford to 2-iodo-4-[4-[(1r,3r)-3-[(5-[5-methyl-5H-pyrido[4,3-b]indol-7-yl]pyridin-2-yl)oxy]cyclobutoxy]piperidin-1-yl]pyrimidine (60 mg, 31%) as a yellow solid.

2-Iodo-4-[4-[(1r,3r)-3-[(5-[5-methyl-5H-pyrido[4,3-b]indol-7-yl]pyridin-2-yl)oxy]cyclobutoxy]piperidin-1-yl]pyrimidine was converted to the title compound using conditions of the last step of exemplary compound 220.

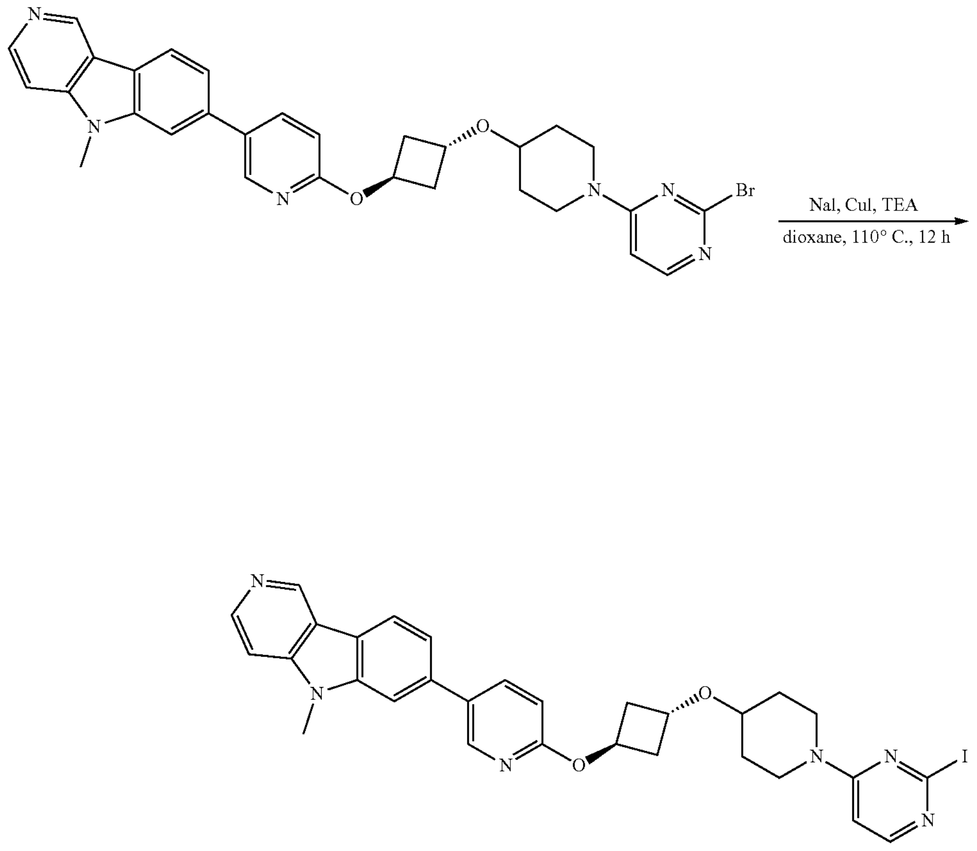

Exemplary Synthesis of Exemplary Compound 229

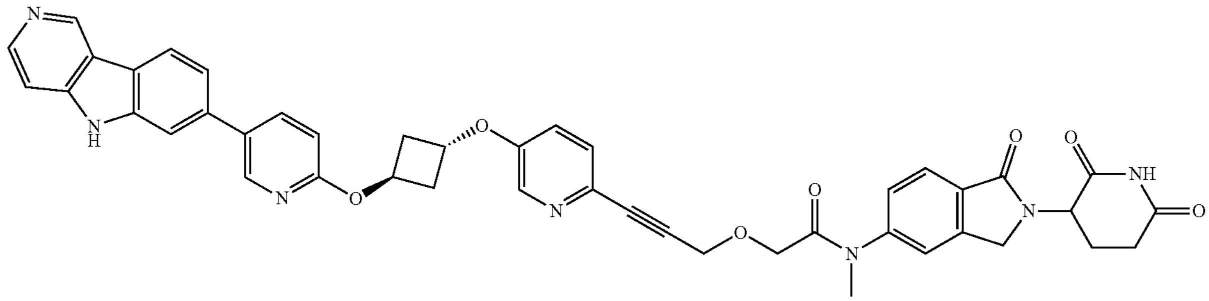 [SMILES: CN(C(=O)COCC#Cc1ccc(O[C@H]2C[C@H](Oc3ccc(-c4ccc5c(c4)[nH]c4ccncc45)cn3)C2)cn1)c1ccc2c(c1)CN(C1CCC(=O)NC1=O)C2=O]

Step 1

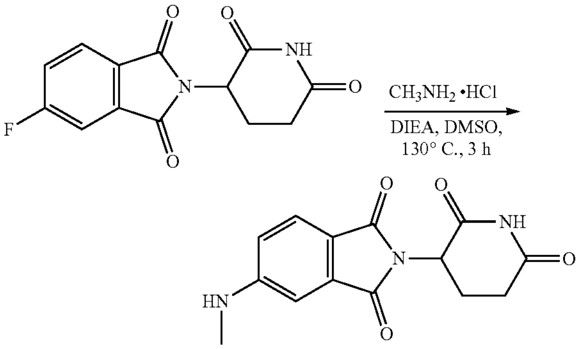

Into a 25-mL sealed tube purged and maintained with an inert atmosphere of nitrogen was placed 2-(2,6-dioxopiperidin-3-yl)-5-fluoro-2,3-dihydro-1H-isoindole-1,3-dione (1.0 g, 3.62 mmol, 1 equiv), DIEA (1.5 mL, 9.08 mmol, 2.5 equiv), and $CH_3NH_2$—HCl (500 mg, 7.41 mmol, 2.05 equiv) in DMSO (8 mL). The resulting solution was stirred for 3 h at 130° C. in an oil bath. The reaction mixture was diluted with water (10 mL) and extracted with ethyl acetate (100 mL×3). The combined organic layer was washed with brine, dried over sodium sulfate and concentrated. The residue was applied onto a silica gel column eluting with ethyl acetate/petroleum ether (2:3). This resulted in 420 mg (40%) of 2-(2,6-dioxopiperidin-3-yl)-5-(methylamino)-2,3-dihydro-1H-isoindole-1,3-dione as a yellow solid.

Step 2

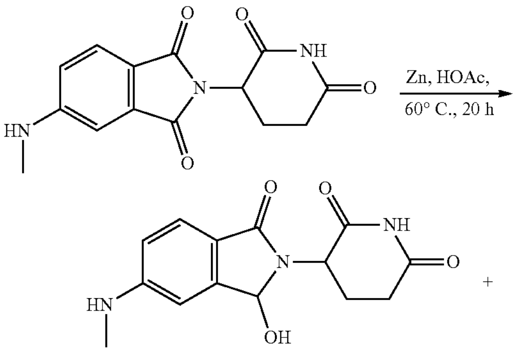

-continued

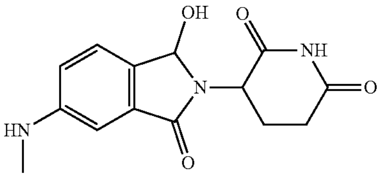

Into a 50-mL round-bottom flask, was placed 2-(2,6-dioxopiperidin-3-yl)-5-(methylamino)-2,3-dihydro-1H-isoindole-1,3-dione (420 mg, 1.46 mmol, 1 equiv), and zinc powder (500 mg, 7.64 mmol, 5.2 equiv) in HOAc (25 mL). The resulting mixture was stirred for 20 h at 60° C. in an oil bath. The solids in the reaction mixture were removed by filtration and the filtrate was concentrated. This resulted in 410 mg (crude, mixture) of 3-[1-hydroxy-5-(methylamino)-3-oxo-2,3-dihydro-1H-isoindol-2-yl]piperidine-2,6-dione and 3-[3-hydroxy-5-(methylamino)-1-oxo-2,3-dihydro-1H-isoindol-2-yl]piperidine-2,6-dione as a white solid.

Step 3

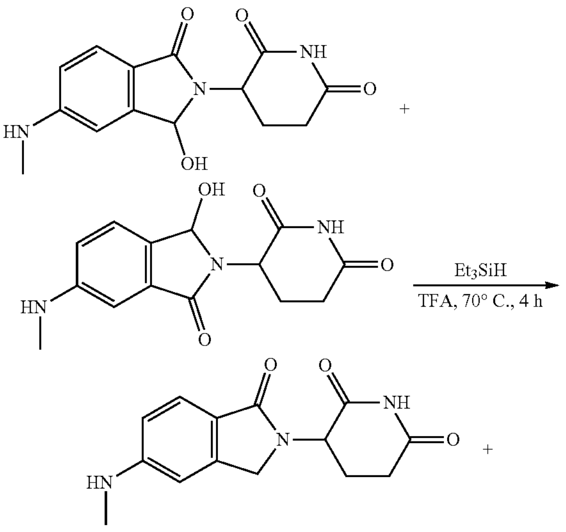

-continued

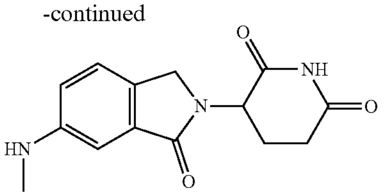

Into a 100-mL round-bottom flask, was placed 3-[1-hydroxy-5-(methylamino)-3-oxo-2,3-dihydro-1H-isoindol-2-yl]piperidine-2,6-dione and 3-[3-hydroxy-5-(methylamino)-1-oxo-2,3-dihydro-1H-isoindol-2-yl]piperidine-2,6-dione (410 mg crude) and triethylsilane (820 mg, 7.05 mmol, 10.20 equiv) in TFA (25 mL). The resulting solution was stirred for 4 h at 70° C. in an oil bath. The reaction mixture was concentrated. The crude product was purified by Prep-HPLC with the following conditions: Column, X B ridge Prep OBD C18 Column, 30*150 mm 5 um; mobile phase, $CH_3CN$ in water (with 0.05% TFA), (8% to 17% gradient in 8 min); Detector, UV. This resulted in 140 mg of 3-[6-(methylamino)-1-oxo-2,3-dihydro-1H-isoindol-2-yl]piperidine-2,6-dione as a white solid and 100 mg of 3-[5-(methylamino)-1-oxo-2,3-dihydro-1H-isoindol-2-yl]piperidine-2,6-dione as a white solid.

Step 4

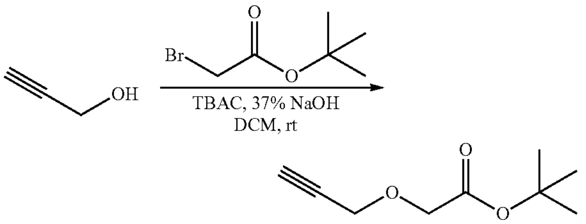

Into a 50-mL round-bottom flask purged and maintained with an inert atmosphere of nitrogen, was placed prop-2-yn-1-ol (1.0 g, 17.8 mmol, 1 equiv) in DMF (20 mL), to which was added 60% NaH (3.8 g, 158 mmol, 8.9 equiv) slowly at 0° C. The resulting mixture was stirred for 30 min at 0° C., which was then followed by the addition of tert-butyl 2-bromoacetate (850 mg, 4.36 mmol, 0.24 equiv). The reaction mixture was stirred for 12 h at room temperature. The reaction mixture was then quenched by the addition of water/ice (100 mL×1), and the resulting mixture was extracted with ethyl acetate (100 mL×3). The combined organic layer was washed with brine, dried over sodium sulfate and concentrated. The residue was applied onto a silica gel column eluting with ethyl acetate/petroleum ether (1:10). This resulted in 2.5 g (82%) of tert-butyl 2-(prop-2-yn-1-yloxy)acetate as a colorless oil.

Step 5

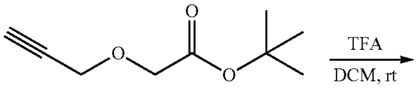

-continued

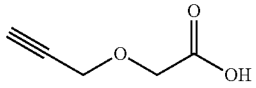

Into a 100-mL round-bottom flask, was placed tert-butyl 2-(prop-2-yn-1-yloxy) acetate (2.5 g, 14.7 mmol, 1 equiv) in DCM (20 mL), to which was added TFA (5 mL, 67.3 mmol, 4.6 equiv) at room temperature. The resulting solution was stirred for 2 h at room temperature, and then was concentrated under vacuum. This resulted in 1.8 g (97%) of 2-(prop-2-yn-1-yloxy) acetic acid as a brown oil.

Step 6

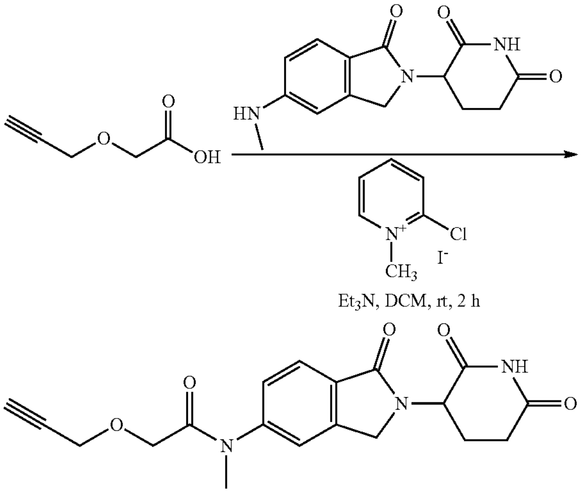

Into a 100-mL round-bottom flask, was placed 2-(prop-2-yn-1-yloxy)acetic acid (1.0 g, 8.76 mmol, 12 equiv) in dichloromethane (20 mL), to which was added $Et_3N$ (1 mL) at 0° C. The resulting mixture was stirred for 10 at 0° C. Then Mukaiyama reagent (2-chloro-1-methylpyridin-1-ium iodide) (300 mg, 1.18 mmol, 1.6 equiv) and 3-[5-(methylamino)-1-oxo-2,3-dihydro-1H-isoindol-2-yl]piperidine-2,6-dione (200 mg, 0.73 mmol, 1 equiv) were added in sequence at 0° C. The resulting solution was stirred for an additional 2 h at room temperature, and then was concentrated. The crude product was purified by Prep-HPLC with the following conditions: Column, XB ridge Prep OBD C18 Column, 30; 150 mm 5 um; mobile phase, $CH_3CN$ in water (with 0.05% TFA), 21% to 30% gradient in 10 min; Detector, UV. This resulted in 50 mg of N-[2-(2,6-dioxopiperidin-3-yl)-1-oxo-2,3-dihydro-1H-isoindol-5-yl]-N-methyl-2-(prop-2-yn-1-yloxy)acetamide as a white solid.

N-[2-(2,6-Dioxopiperidin-3-yl)-1-oxo-2,3-dihydro-1H-isoindol-5-yl]-N-methyl-2-(prop-2-yn-1-yloxy)acetamide was converted to the title compound using procedure described in the last step of exemplary compound 220.

The following exemplary compounds were prepared using procedures analogous to those described in US 20180125821: 340, 341, 343.

Exemplary Synthesis of Exemplary Compound 342
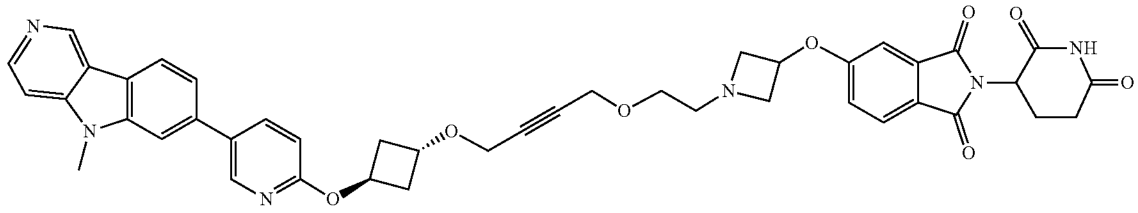 [SMILES: Cn1c2ccncc2c2ccc(-c3ccc(O[C@H]4C[C@H](OCC#CCOCCN5CC(Oc6ccc7c(c6)C(=O)N(C6CCC(=O)NC6=O)C7=O)C5)C4)nc3)cc21]
Prepared according to the scheme below using procedures described for other examples above.
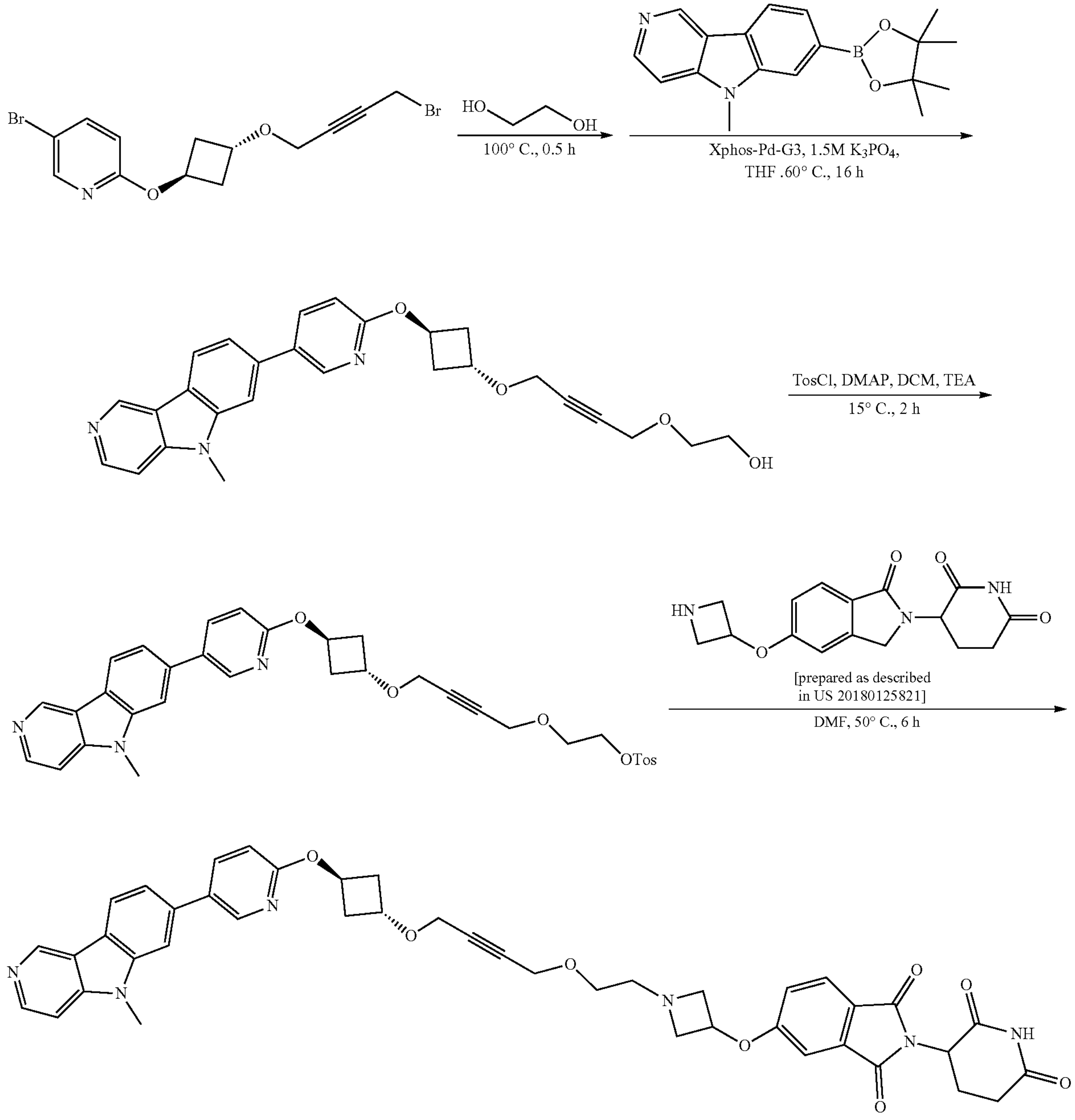
Exemplary Compound 342

Exemplary Synthesis of Exemplary Compound 225

Step 1

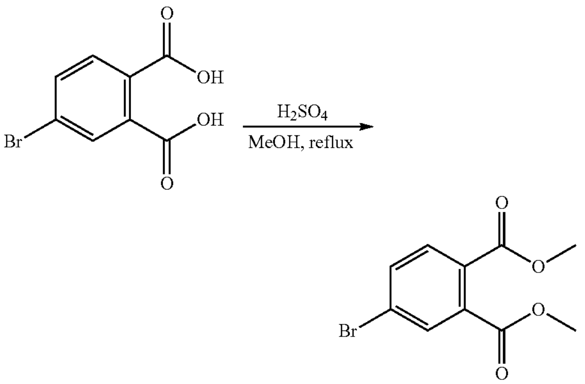

To a solution of 4-bromobenzene-1,2-dicarboxylic acid (30 g, 122.4 mmol, 1 equiv) in methanol (300 mL) was added sulfuric acid (10 mL) slowly at room temperature. The reaction solution was heated to reflux for 20 hr in an oil bath. The reaction mixture was cooled to room temperature and concentrated. The residue was diluted with water (50 mL) and extracted with ethyl acetate (100 mL×3). The combined organic layers were washed with water (50 mL) and brine (50 mL), dried over anhydrous sodium sulfate and concentrated under vacuum. The crude was subjected to a silica gel column chromatography eluting with ethyl acetate/petroleum ether (1:5). This resulted in 29.7 g (89%) of 1,2-dimethyl 4-bromobenzene-1,2-dicarboxylate as a white solid.

Step 2

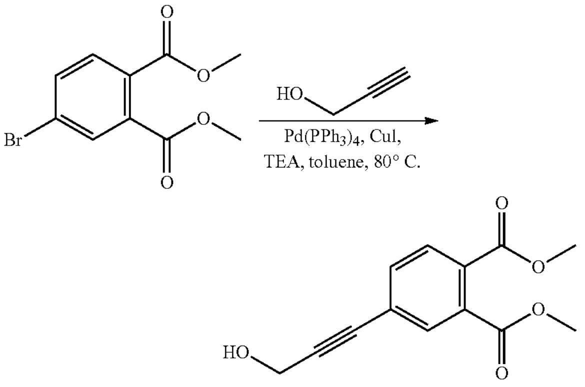

To a degassed solution of 1,2-dimethyl 4-bromobenzene-1,2-dicarboxylate (12 g, 43.9 mmol, 1 equiv) in toluene (160 mL) was added prop-2-yn-1-ol (3.04 g, 54.2 mmol, 1.23 equiv), CuI (1.67 g, 8.77 mmol, 0.20 equiv), TEA (31 mL, 223.03 mmol, 5.08 equiv) and $Pd(PPh_3)_4$ (2.55 g, 2.21 mmol, 0.05 equiv) under argon atmosphere. The reaction mixture was stirred for 16 hr at 80° C., and then was concentrated under vacuum. The residue was subjected to a silica gel column eluting with ethyl acetate/petroleum ether (1:1). This resulted in 7.85 g (72%) of 1,2-dimethyl 4-(3-hydroxyprop-1-yn-1-yl)benzene-1,2-dicarboxylate as a yellow liquid.

Step 3

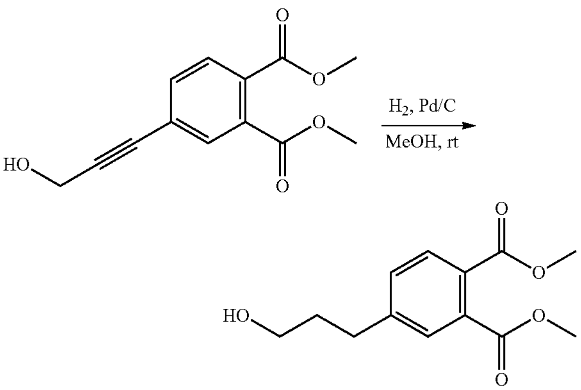

To a solution of 1,2-dimethyl 4-(3-hydroxyprop-1-yn-1-yl)benzene-1,2-dicarboxylate (7.84 g, 31.6 mmol, 1 equiv) in methanol (380 mL) was added 10% Pd/C (1.98 g) under N2. The reaction flask was vacuumed and flushed with $H_2$. The resulting mixture was stirred for 5 hr at room temperature under $H_2$ atmosphere with a hydrogen balloon. The reaction mixture was filtered, and the filter cake was rinsed with MeOH. The combined filtrate was concentrated under vacuum. This resulted in 2.36 g (100%) of 1,2-dimethyl 4-(3-hydroxypropyl)benzene-1,2-dicarboxylate as a yellow liquid.

Step 4

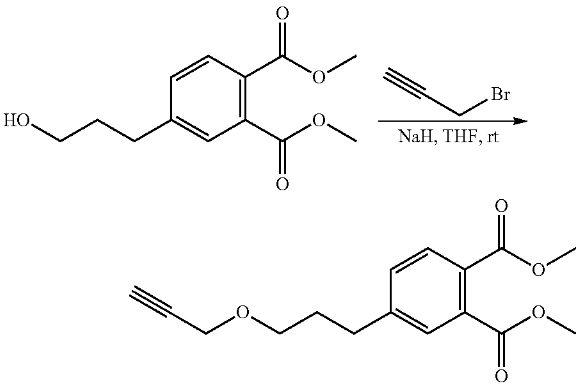

To a stirred solution of 1,2-dimethyl 4-(3-hydroxypropyl)benzene-1,2-dicarboxylate (3.56 g, 14.11 mmol, 1 equiv) in THF (78 mL) was added NaH (1.55 g, 38.75 mmol, 2.75 equiv, 60%). The resulting mixture was stirred for 30 min at 0° C. To the mixture was then added 3-bromoprop-1-yne (3.62 g, 30.43 mmol, 2.16 equiv), and the reaction mixture was allowed to stir for an additional 20 hr at room temperature. The reaction mixture was quenched with water (50 mL) and extracted with EtOAc (50 mL×3). The combined organic layer was washed with brine, dried over sodium sulfate and concentrated under vacuum. The residue was subjected to a silica gel column eluting with ethyl acetate/petroleum ether (1:4). This resulted in 733 mg (18%) of 1,2-dimethyl 4-[3-(prop-2-yn-1-yloxy)propyl]benzene-1,2-dicarboxylate as a light yellow oil.

Step 5

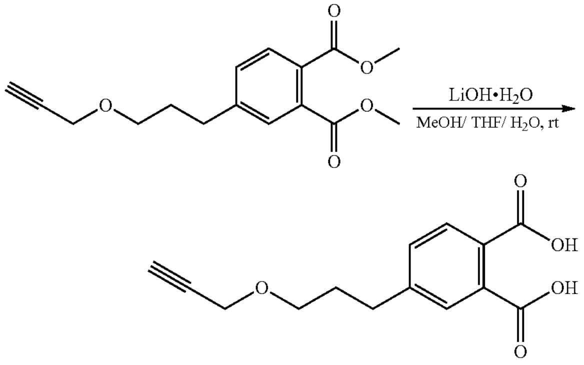

To a stirred solution of 1,2-dimethyl 4-[3-(prop-2-yn-1-yloxy)propyl]benzene-1,2-dicarboxylate (733 mg, 2.53 mmol, 1 equiv) in THF (7.8 mL), MeOH (5.8 mL) and $H_2O$ (4.0 mL) was added LiOH $H_2O$ (436 mg, 10.39 mmol, 4.11 equiv). The reaction mixture was stirred for 15 hr at room temperature. Then the reaction mixture was concentrated. To the residue was added 20 mL $H_2O$ and then 1M HCl to adjust the pH value to ~1. The resulting mixture was extracted with ethyl acetate (30 mL×3), and the combined organic layers were washed with brine (30 mL), dried over anhydrous sodium sulfate and concentrated under vacuum. This resulted in 742 mg (100%) of 4-[3-(prop-2-yn-1-yloxy)propyl] benzene-1, 2-dicarboxylic acid as a light yellow oil.

Step 6

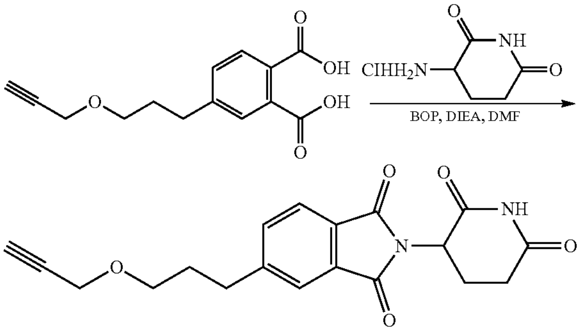

To a solution of 4-[3-(prop-2-yn-1-yloxy)propyl]benzene-1,2-dicarboxylic acid (663 mg, 2.53 mmol, 1 equiv) and 3-aminopiperidine-2,6-dione hydrochloride (502 mg, 3.05 mmol, 1.21 equiv) in N,N-dimethylformamide (20 mL) were added DIEA (2.5 mL, 15.13 mmol, 5.99 equiv) and BOP (2.79 g, 6.31 mmol, 2.50 equiv). The reaction solution was stirred for 5 hr at room temperature. The reaction was then quenched by the addition of water (50 mL). The resulting mixture was extracted with ethyl acetate (100 mL×3). The combined organic layers were washed with brine (100 mL). The organic layers were dried over anhydrous sodium sulfate and concentrated. The crude was subjected to a silica gel column eluting with ethyl acetate/petroleum ether (1:1). This resulted in 730 mg (82%) of 2-(2,6-dioxopiperidin-3-yl)-5-[3-(prop-2-yn-1-yloxy)propyl]-2,3-dihydro-1H-isoindole-1,3-dione as a light yellow oil.

2-(2,6-Dioxopiperidin-3-yl)-5-[3-(prop-2-yn-1-yloxy)propyl]-2,3-dihydro-1H-isoindole-1,3-dione was converted to the title compound according to the scheme below using procedures for other examples above.

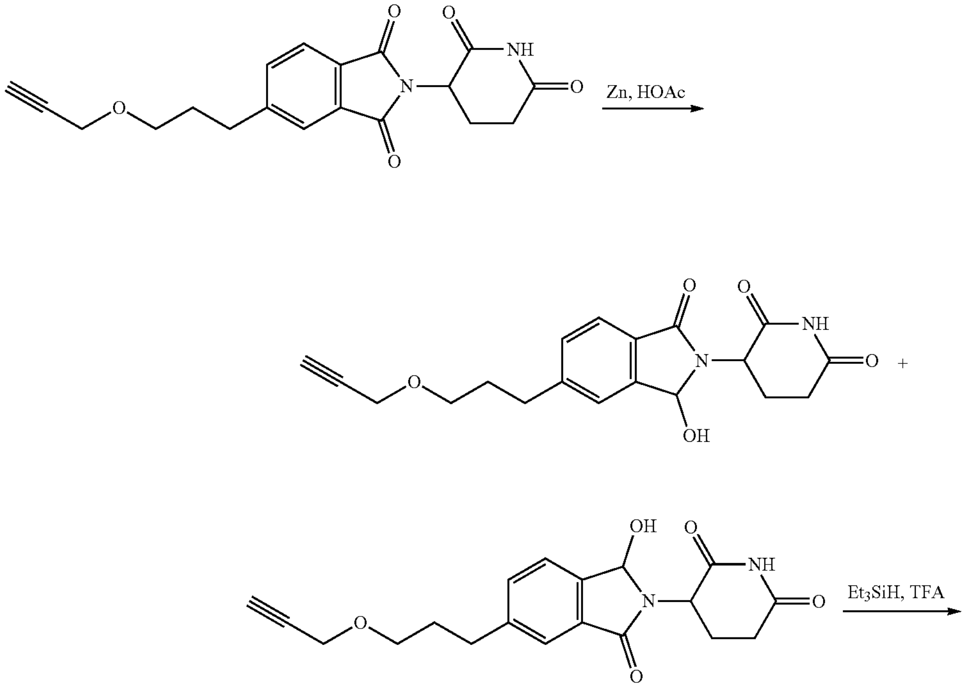

-continued
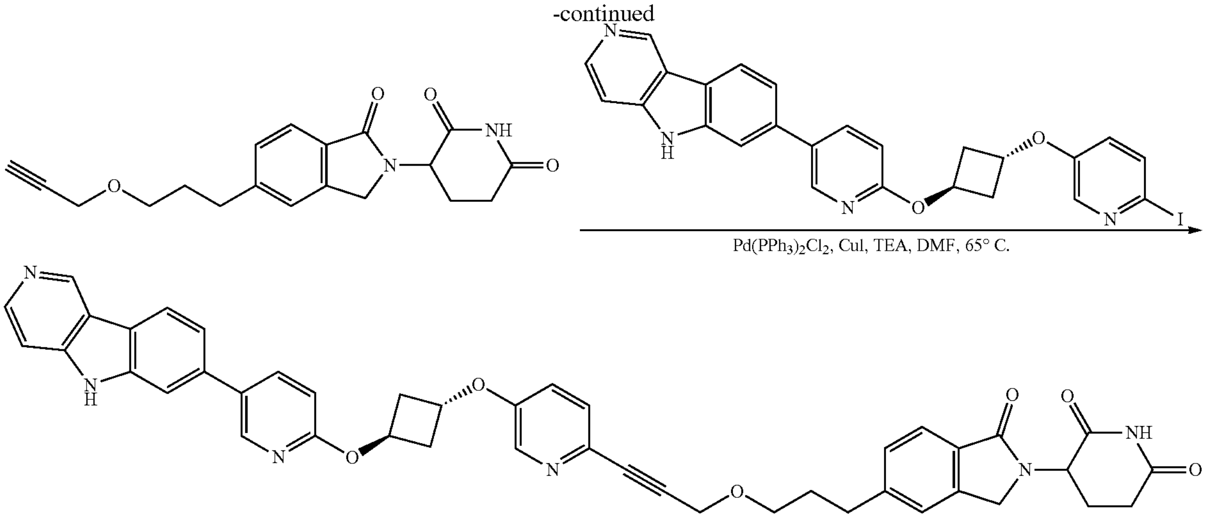
Exemplary Compound 225
The following exemplary compounds were prepared using procedures described by Crew, A. et al. in WO 2017011590 in combination with procedures described in US 20180125821: 344, 345, 347, 348, 349, 350.
Exemplary Synthesis of Exemplary Compound 346
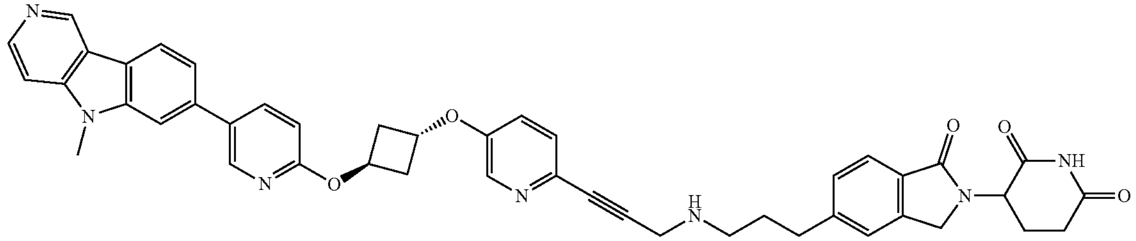 [SMILES: Cn1c2ccncc2c2ccc(-c3ccc(O[C@H]4C[C@H](Oc5ccc(C#CCNCCCc6ccc7c(c6)CN(C6CCC(=O)NC6=O)C7=O)nc5)C4)nc3)cc21]
Prepared according to the scheme below using procedures described for other examples above.
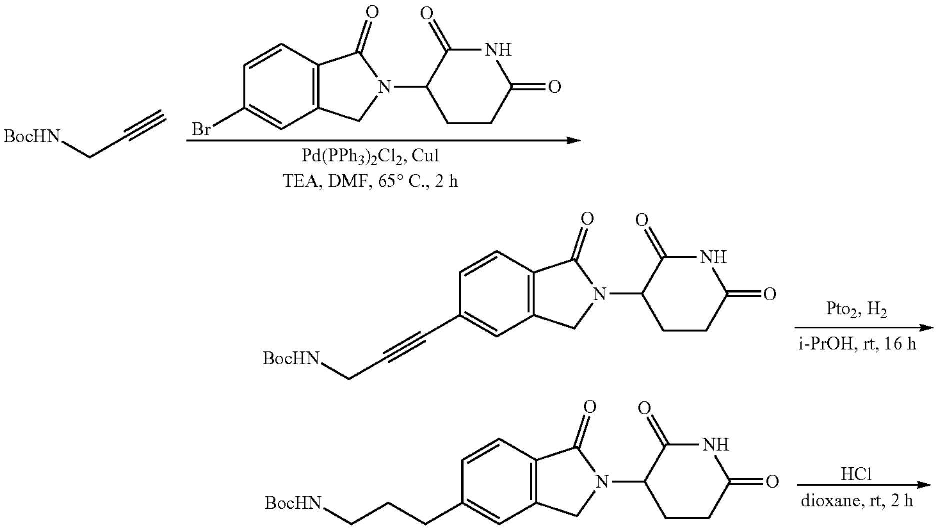

-continued

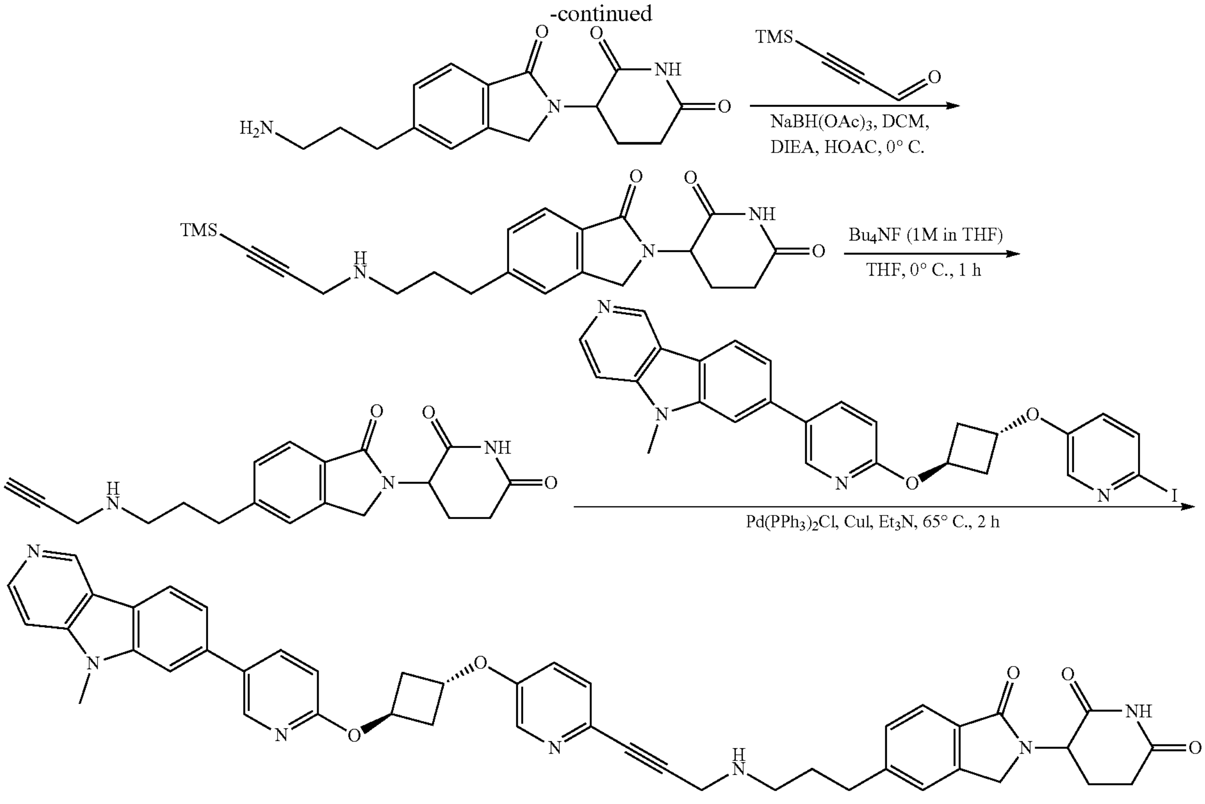

Exemplary Compound 346

Exemplary Synthesis of Exemplary Compound 274

Step 1

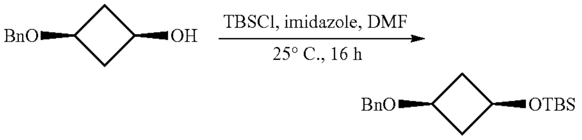

A mixture of 3-benzyloxycyclobutanol (5 g, 28.05 mmol, 1 eq), imidazole (2.86 g, 42.08 mmol, 1.5 eq) and tert-butylchlorodimethylsilane (6.34 g, 42.08 mmol, 5.16 mL, 1.5 eq) in N,N-dimethylformamide (60 mL) was degassed and purged with nitrogen for 3 times, and then the mixture was stirred at 25° C. for 16 h under nitrogen atmosphere. The reaction mixture was quenched by the addition of water 50 mL, and extracted with ethyl acetate (100 mL×3). The combined organic layers were washed with brine (100 mL×3), dried over anhydrous sodium sulfate, filtered and concentrated under reduced pressure to give a residue. The residue was purified by silica gel column chromatography (petroleum ether/ethyl acetate=100/1 to 50/1). Compound (3-benzyloxycyclobutoxy)-tert-butyl-dimethyl-silane (7.2 g, 24.62 mmol, 87% yield) was obtained as a yellow oil.

Step 2

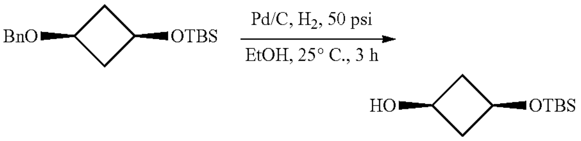

To a solution of (3-benzyloxycyclobutoxy)-tert-butyl-dimethyl-silane (7.2 g, 24.62 mmol, 1 eq) in ethanol (50 mL) was added 10% palladium on activated carbon catalyst (500 mg) under nitrogen. The suspension was degassed under vacuum and purged with hydrogen 3 times. The mixture was stirred under hydrogen (50 psi) at 25° C. for 3 h. The reaction mixture was filtered and concentrated under reduced pressure to give a residue. Compound 3-[tert-butyl(dimethyl)silyl]oxycyclobutanol (4.2 g, 20.75 mmol, 84% yield) was obtained as a light yellow oil.

Step 3

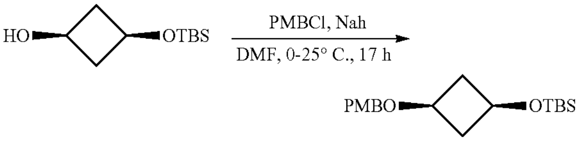

To a mixture of 60% sodium hydride (899 mg, 22.48 mmol, 1.3 eq) in N,N-dimethylformamide (50 mL) was added 3-[tertbutyl(dimethyl)silyl]oxycyclobutanol (3.5 g, 17.30 mmol, 1 eq) at 0° C. under nitrogen. After 1 h, 4-methoxybenzyl chloride (3.52 g, 22.48 mmol, 3.06 mL, 1.3 eq) was added. The reaction mixture was stirred at 25° C. for another 16 h. The reaction mixture was quenched by the addition of water (50 mL), and extracted with ethyl acetate (100 mL×3). The combined organic layers were washed with brine (100 mL×3), dried over anhydrous sodium sulfate, filtered and concentrated under reduced pressure to give a residue. The residue was purified by silica gel column chromatography (petroleum ether/ethyl acetate=200/1 to 100/1). Compound tert-butyl-[3-[(4-methoxyphenyl)methoxy]cyclobutoxy]-dimethyl-silane (3.9 g, 12.09 mmol, 69% yield) was obtained as a colorless oil.

Step 4

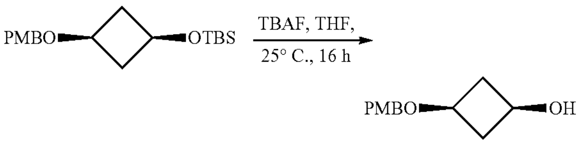

A solution of tert-butyl-[3-[(4-methoxyphenyl)methoxy]cyclobutoxy]-dimethyl-silane (3.7 g, 11.47 mmol, 1 eq) and tetrabutylammonium fluoride (1 M in tetrahydrofuran solution, 22.94 mL, 2 eq) in tetrahydrofuran (80 mL) was degassed and purged with nitrogen 3 times, and then the mixture was stirred at 25° C. for 16 h under nitrogen atmosphere. The reaction mixture was quenched by the addition of water (200 mL) and extracted with ethyl acetate (150 mL×3). The combined organic layers were washed with brine (100 mL×3), dried over anhydrous sodium sulfate, filtered and concentrated under reduced pressure to give a residue. The residue was purified by silica gel column chromatography (petroleum ether/ethyl acetate=100/1 to 1/1). Compound 3-[(4-methoxyphenyl)methoxy]cyclobutanol (1.6 g, 7.68 mmol, 66% yield) was obtained as a colorless oil.

Step 5

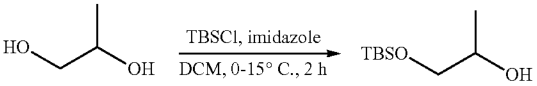

To a solution of propane-1,2-diol (500 mg, 6.57 mmol, 0.48 mL, 1 eq) in dichloromethane (8 mL) was added imidazole (447 mg, 6.57 mmol, 1 eq), then a solution of tert-butylchlorodimethylsilane (990 mg, 6.57 mmol, 0.80 mL, 1 eq) in dichlormethane (8 mL) at 0° C. The reaction mixture was then stirred at 15° C. for 2 h. The reaction mixture was filtered, and the filtrate was concentrated. 1-[tert-Butyl(dimethyl)silyl]oxypropan-2-ol (1.23 g, 6.46 mmol, 98% yield) was obtained as a colorless oil.

Step 6

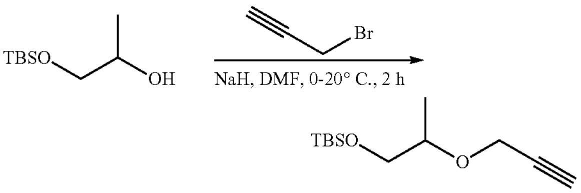

To a mixture of 1-[tert-butyl(dimethyl)silyl]oxypropan-2-ol (1.23 g, 6.46 mmol, 1 eq) and 3-bromoprop-1-yne (1.54 g, 12.92 mmol, 1.11 mL, 2 eq) in N,N-dimethylformamide (20 mL) was added sodium hydride (516 mg, 12.92 mmol, 60% purity, 2 eq) at 0° C., and the reaction mixture was warmed to 20° C. for 2 h. The mixture was quenched by water (30 mL) and filtered, and the filtrate was extracted with ethyl acetate (40 mL×3). The combined organic phase was washed with brine (20 mL), dried over anhydrous sodium sulfate, filtered and concentrated in vacuo. The residue was purified by silica gel column chromatography (petroleum ether/ethyl acetate=1/0 to 100/1). tert-Butyl-dimethyl-(2-prop-2-ynoxypropoxy)silane (790 mg, 3.46 mmol, 53% yield) was obtained as a yellow oil.

tert-Butyl-dimethyl-(2-prop-2-ynoxypropoxy)silane was converted to the title compound according to the scheme below using procedures described for other examples above.

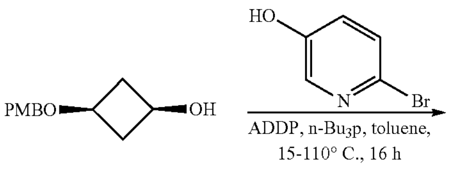

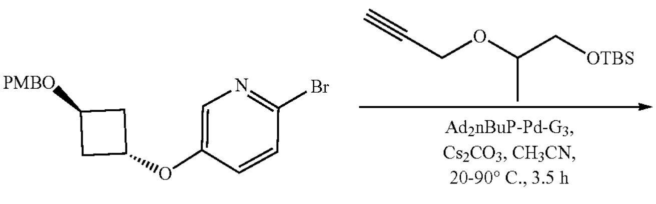

-continued
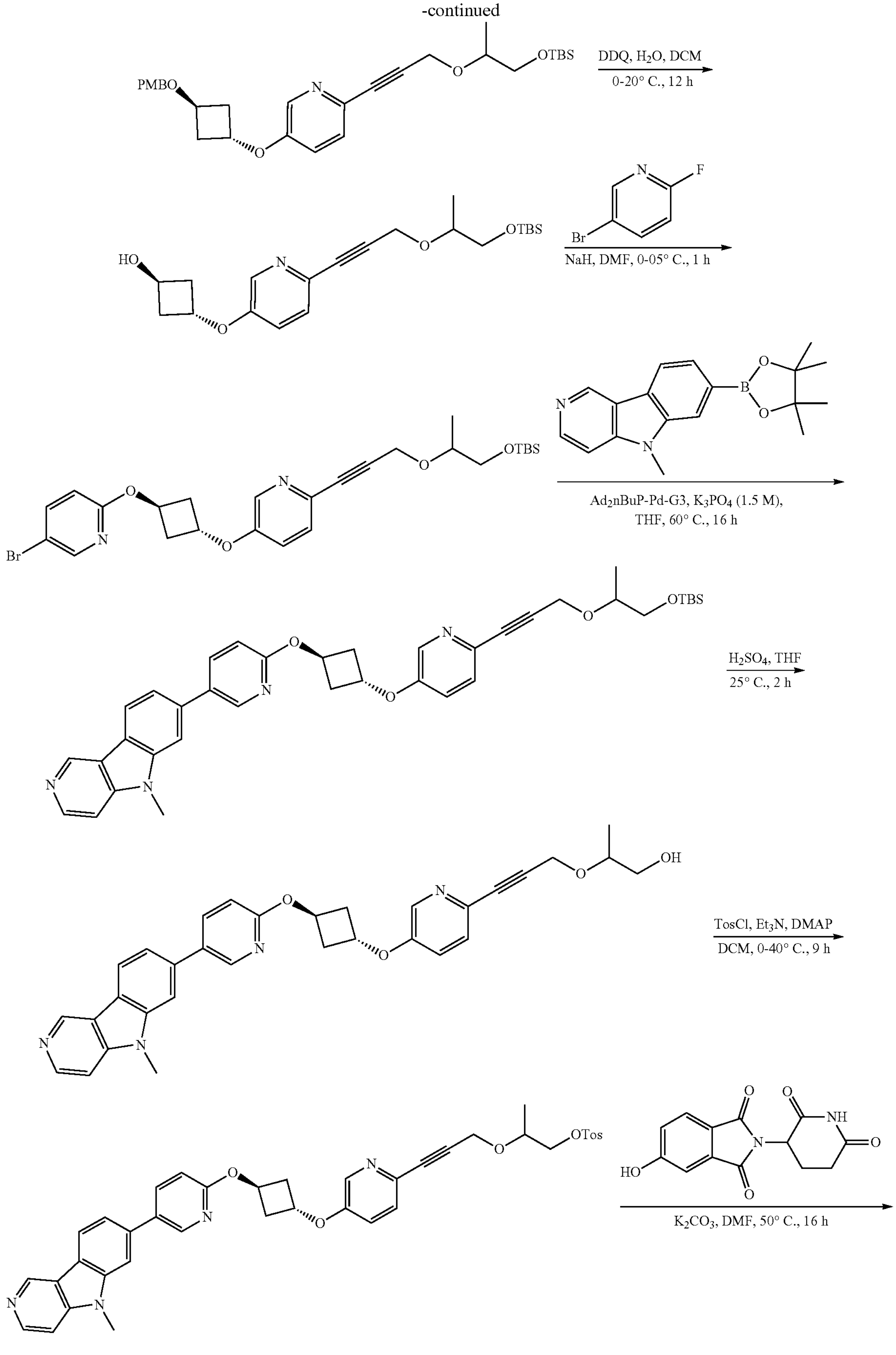

-continued

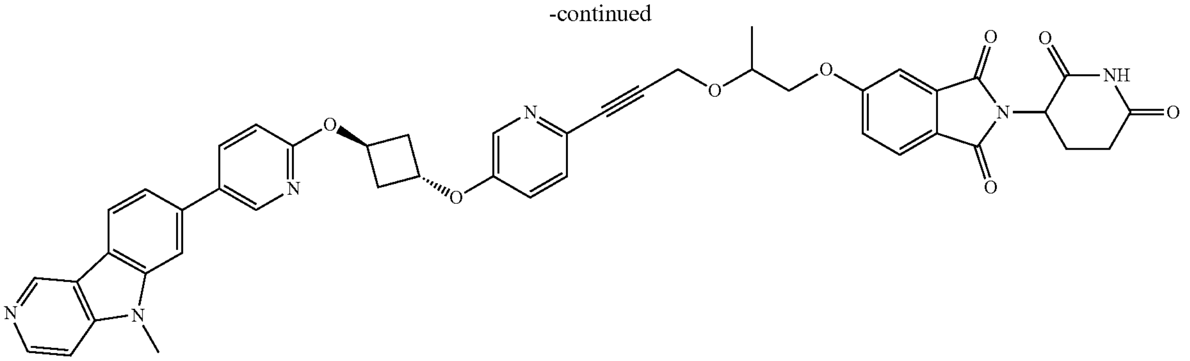

Exemplary Compound 274

Exemplary Synthesis of Exemplary Compound 351

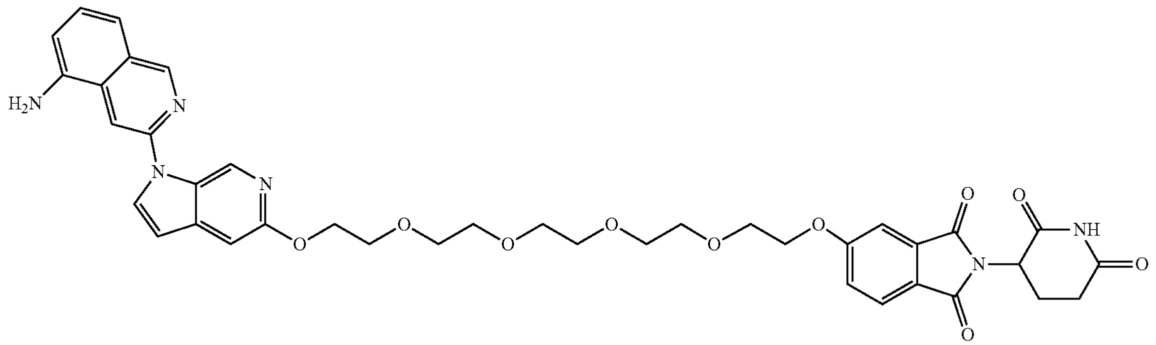 [SMILES: Nc1cccc2cnc(-n3ccc4cc(OCCOCCOCCOCCOCCOc5ccc6c(c5)C(=O)N(C5CCC(=O)NC5=O)C6=O)ncc43)cc12]

Step 1

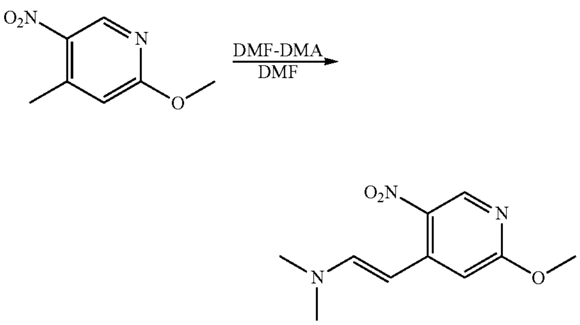

Into a 250-mL round-bottom flask, was placed 2-methoxy-4-methyl-5-nitropyridine (10 g, 59.5 mmol, 1 equiv) in DMF (60 mL), to which was added DMF-DMA (14.17 g, 119 mmol, 2 equiv) at room temperature. The resulting solution was stirred for 16 hr at 90° C. The reaction mixture was cooled to room temperature and quenched by the addition of 500 mL of water/ice. The precipitated solids were collected by filtration and dried under vacuum. This resulted in 12 g (90%) of [(E)-2-(2-methoxy-5-nitropyridin-4-yl)ethenyl]dimethylamine as a red solid.

Step 2

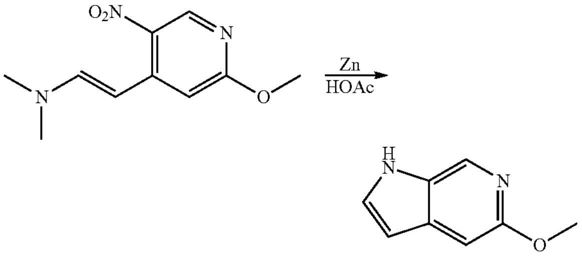

Into a 500-mL round-bottom flask, was placed Zn powder (3.52 g, 537.6 mmol, 10 equiv) and [(E)-2-(2-methoxy-5-nitropyridin-4-yl)ethenyl]dimethylamine (12 g, 53.76 mmol, 1 equiv) in AcOH (350 mL). The resulting mixture was stirred for 16 hr at room temperature. The mixture was concentrated under vacuum. The residue was diluted with 200 mL ethyl acetate. The pH value of the mixture was adjusted to 7 with saturated $NaHCO_3$ solution. The organic phase was separated and concentrated under vacuum. The residue was applied onto a silica gel column eluting with ethyl acetate/hexane (1:2). This resulted in 6 g (75%) of 5-methoxy-1H-pyrrolo[2,3-c]pyridine as a yellow solid.

Step 3

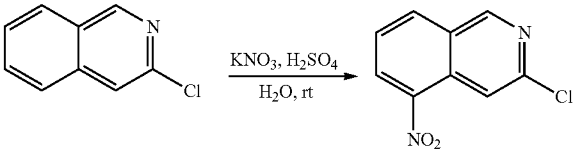 [SMILES: Clc1cc2ccccc2cn1 ; O=[N+]([O-])c1cccc2cnc(Cl)cc12]

Into a 500-mL 3-neck round-bottom flask was placed 3-chloroisoquinoline (5 g, 30.6 mmol, 1 equiv), $KNO_3$ (3.28 g, 32.5 mmol, 1.06 equiv) in $H_2SO_4$ (100 mL) at 0° C. in a water/ice bath. The resulting mixture was stirred for 10 min at 0° C., then warmed up to room temperature and stirred for additional 16 hr at room temperature. The reaction was then quenched by the addition of 500 mL of water/ice. The insoluble solids were removed by filtration, and the filtrate was concentrated under vacuum. This resulted in 6 g (94%) of 3-chloro-5-nitroisoquinoline as a yellow solid.

Step 4

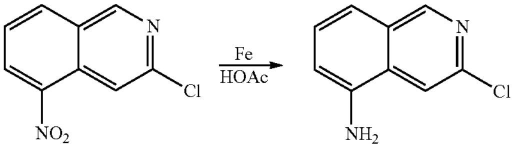

Into a 500-mL round-bottom flask was placed 3-chloro-5-nitroisoquinoline (10 g, 47.9 mmol, 1 equiv), iron powder (13.39 g, 239.7 mmol, 5 equiv) in HOAc (100 mL). The resulting mixture was stirred for 16 hr at room temperature. The insoluble solids were filtered out, and the filtrate was concentrated under vacuum. This resulted in 8.5 g (crude) of 3-chloroisoquinolin-5-amine as a yellow solid.

Step 5

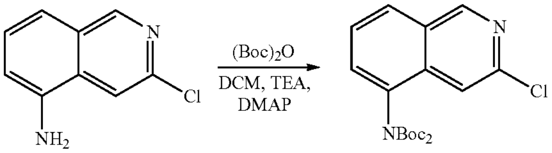

Into a 250-mL round-bottom flask was placed 3-chloroisoquinolin-5-amine (8.5 g, 47.6 mmol, 1 equiv), di-tert-butyl dicarbonate (4.15 g, 190.3 mmol, 4 equiv), DMAP (1.16 g, 9.52 mmol, 0.2 equiv) in THF (85 mL). The resulting solution was stirred for 16 hr at room temperature. The mixture was concentrated. The residue was applied onto a silica gel column eluting with ethyl acetate/hexane (3:47). This resulted in 10.5 g (58% for 2 steps) of tert-butyl N-[(tert-butoxy)carbonyl]-N-(3-chloroisoquinolin-5-yl)carbamate as a yellow solid.

Step 6

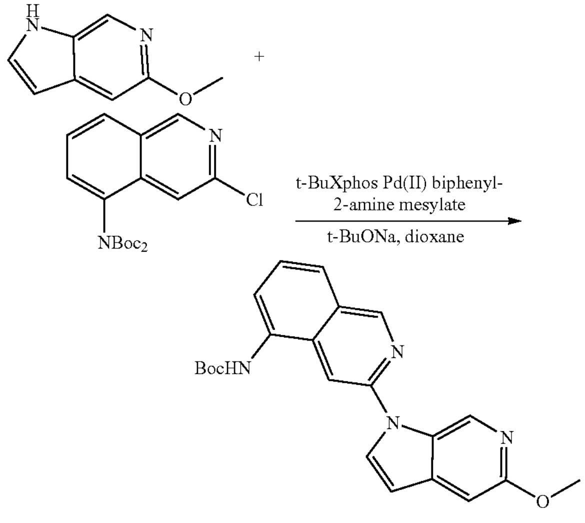

Into a 50-mL round-bottom flask purged and maintained with an inert atmosphere of nitrogen was placed 5-methoxy-1H-pyrrolo[2,3-c]pyridine (510 mg, 1.35 mmol, 2.34 equiv), tert-butyl N-[(tert-butoxy)carbonyl]-N-(3-chloroisoquinolin-5-yl)carbamate (410 mg, 1.47 mmol, 1 equiv), t-BuONa (500 mg, 5.20 mmol, 3.54 equiv), t-BuXphos Pd(II) biphenyl-2-amine mesylate (200 mg, 0.25 mmol, 0.17 equiv) in dioxane (10 mL). The resulting mixture was stirred for 12 hr at 100° C. The mixture was concentrated. The residue was applied onto a silica gel column eluting with dichloromethane/methanol (10:1). This resulted in 410 mg (71%) of tert-butyl N-(3-[5-methoxy-1H-pyrrolo[2,3-c]pyridin-1-yl]isoquinolin-5-yl)carbamate as a yellow solid.

Step 7

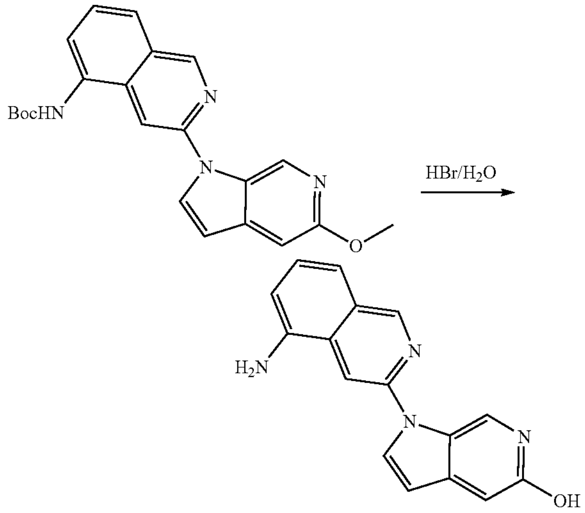

Into a 100-mL round-bottom flask was placed tert-butyl N-(3-[5-methoxy-1H-pyrrolo[2,3-c]pyridin-1-yl]isoquinolin-5-yl)carbamate (450 mg, 1.15 mmol) in HBr (aq) (30 mL, 40%). The resulting mixture was stirred for 2 days at 100° C. in an oil bath. The mixture was concentrated. This resulted in 420 mg (crude) of 1-(5-aminoisoquinolin-3-yl)-1H-pyrrolo[2,3-c]pyridin-5-ol HBr salt as a solid.
1-(5-aminoisoquinolin-3-yl)-1H-pyrrolo[2,3-c]pyridin-5-ol was converted to the title compound according to the scheme below using procedures described in US 20180125821.
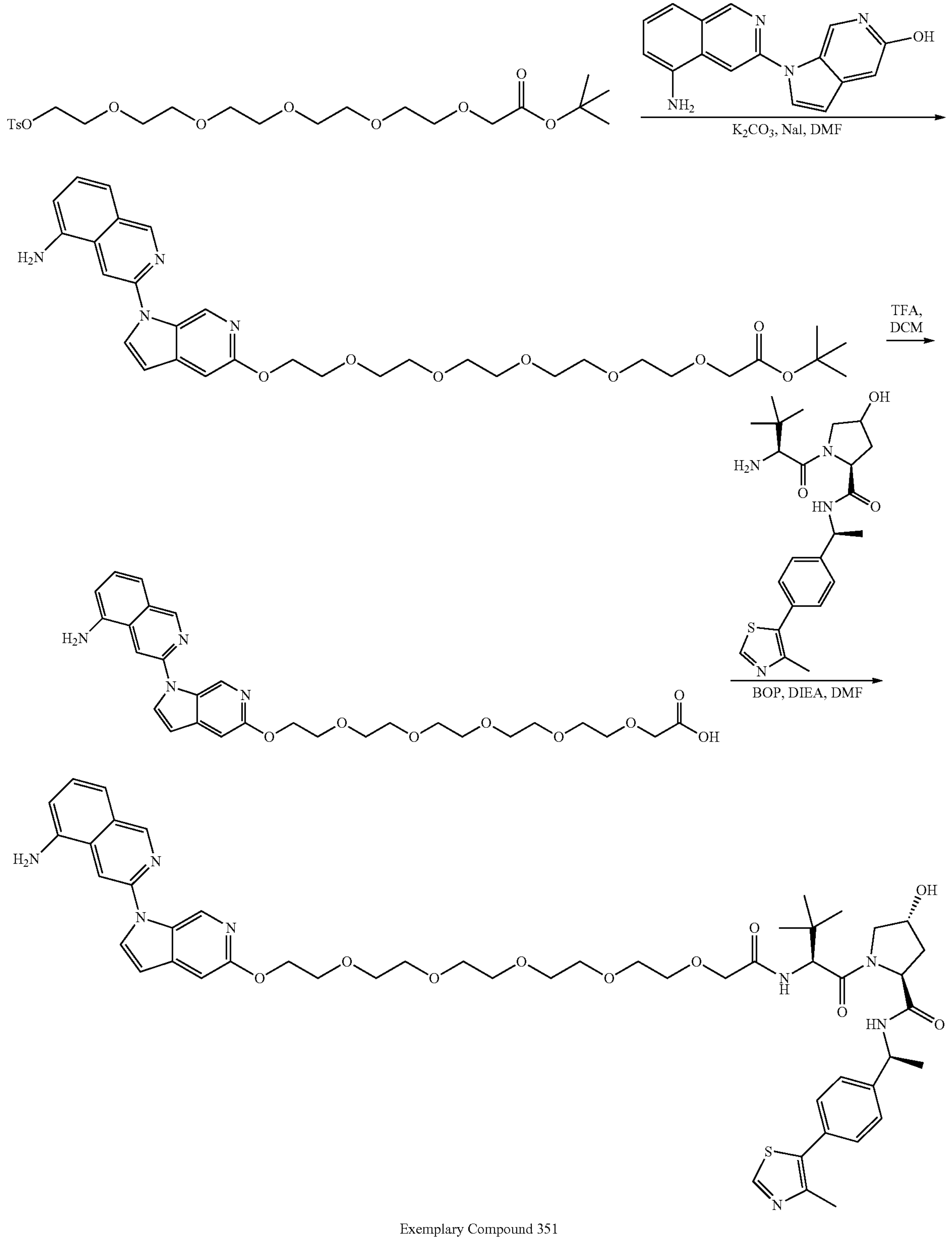
Exemplary Compound 351

Exemplary Synthesis of Exemplary Compound 352
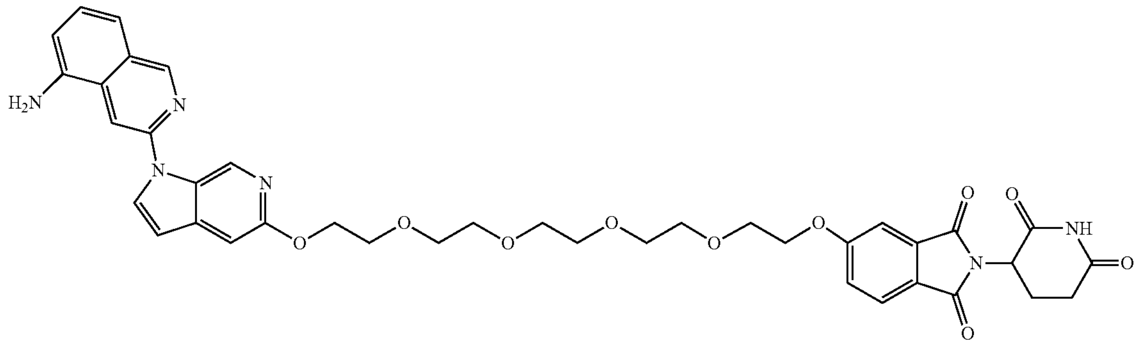 [SMILES: Nc1cccc2cnc(-n3ccc4cc(OCCOCCOCCOCCOCCOc5ccc6c(c5)C(=O)N(C5CCC(=O)NC5=O)C6=O)ncc43)cc12]
Prepared as shown in schemes below using procedures described in US 20180125821 and other examples above.
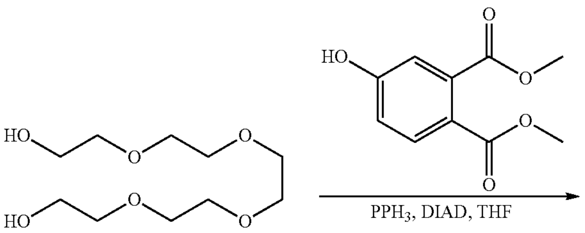
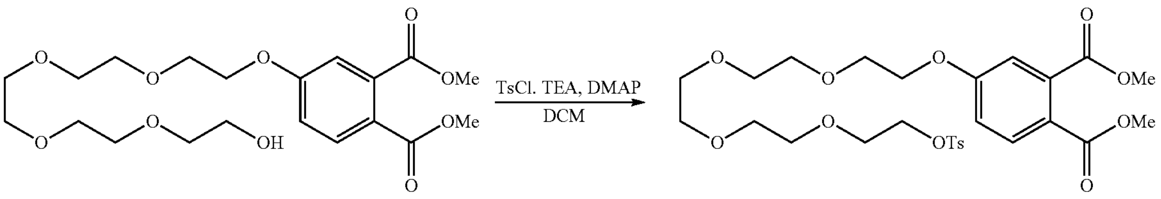
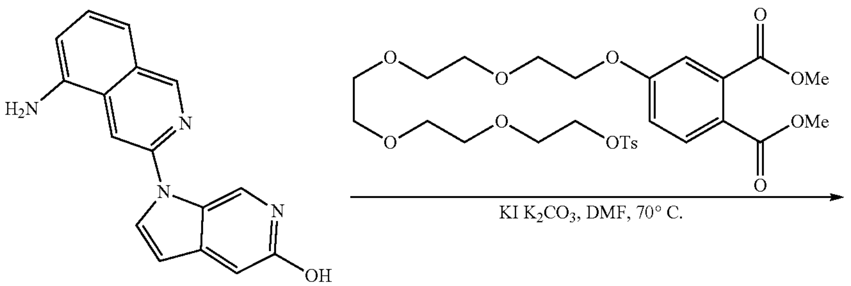
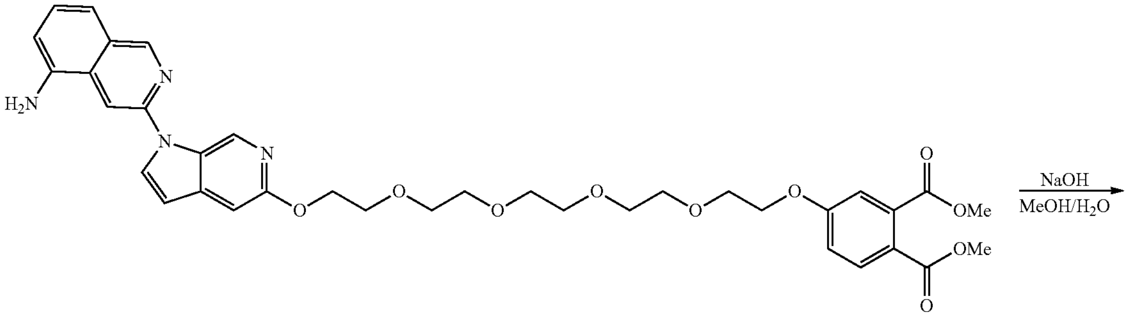

-continued

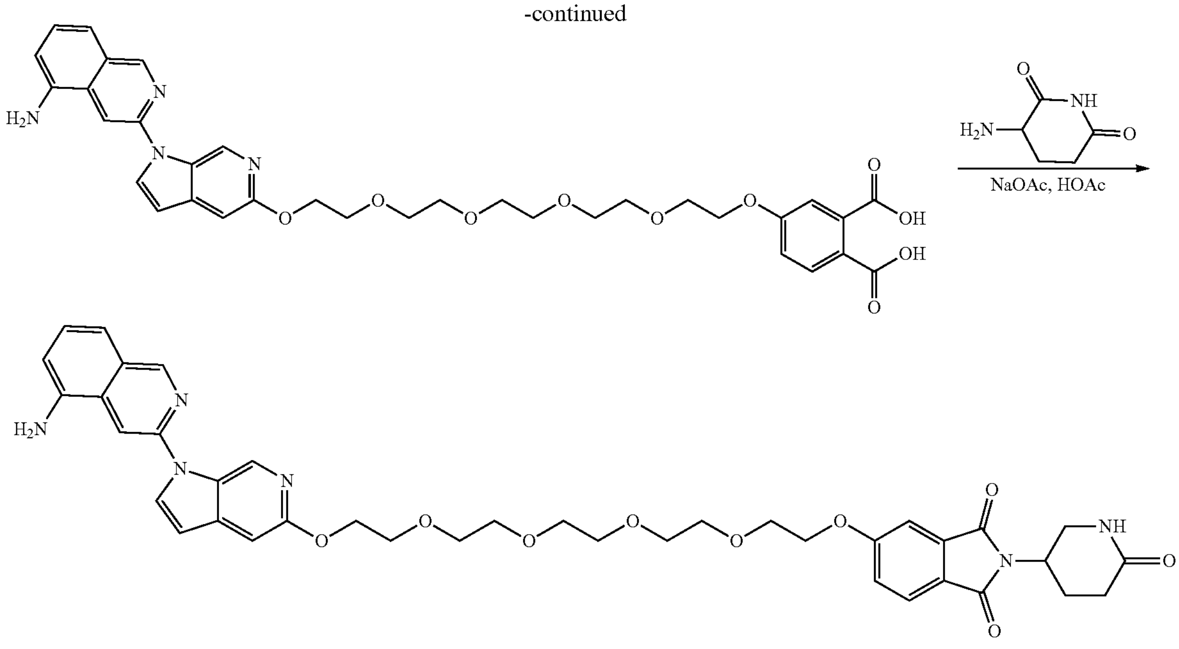

Exmeplary Compound 352

Using analogous procedures, as well as procedures from exemplary compound 315 and WO 2017011590, the following exemplary compounds were prepared: 353, 354, 357, 359, 360, 367.

Exemplary Synthesis of Exemplary Compound 355

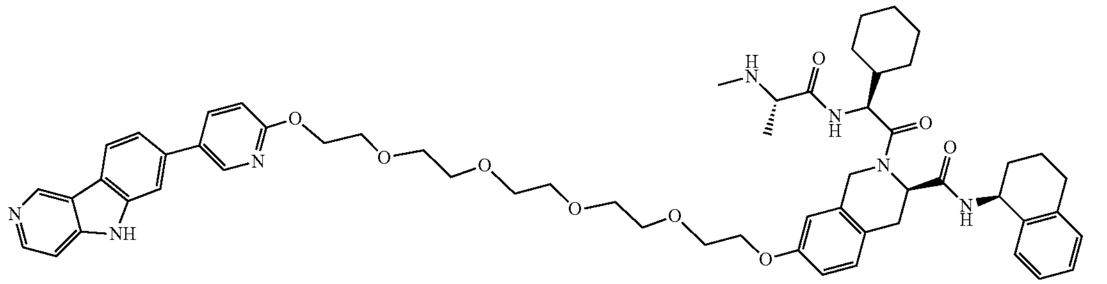 [SMILES: CN[C@@H](C)C(=O)N[C@H](C(=O)N1Cc2cc(OCCOCCOCCOCCOCCOc3ccc(-c4ccc5c(c4)[nH]c4ccncc45)cn3)ccc2C[C@@H]1C(=O)N[C@H]1CCCc2ccccc21)C1CCCCC1]

Step 1

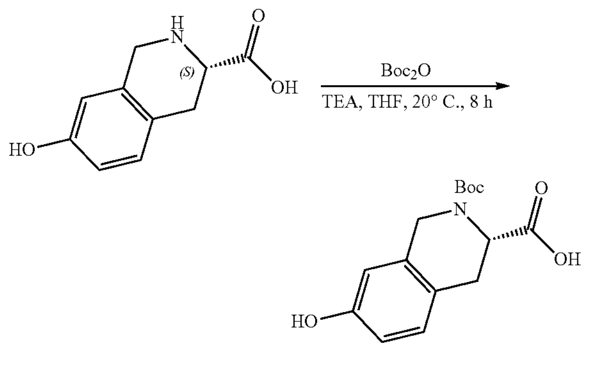

A mixture of (3S)-7-hydroxy-1,2,3,4-tetrahydroisoquinoline-3-carboxylic acid (3 g, 15.53 mmol, 1 eq) di-tert-butyl dicarbonate (4.07 g, 18.63 mmol, 4 mL, 1.2 eq) and triethylamine (1.57 g, 15.53 mmol, 2 mL, 1 eq) in tetrahydrofuran (50 mL) was stirred at 20° C. for 8 hours. The mixture was partitioned between ethyl acetate (250 mL) and 1 M citric acid solution (500 mL), and the organic phase was separated, washed with brine (500 mL) and dried over sodium sulfate. The solvent was concentrated in vacuum. The residue was triturated with petroleum ether (50 mL) to afford the title compound, (3S)-2-tert-butoxycarbonyl-7-hydroxy-3,4-dihydro-1H-isoquinoline-3-carboxylic acid (4 g, 13 mmol, 87% yield), as a white solid.

Step 2

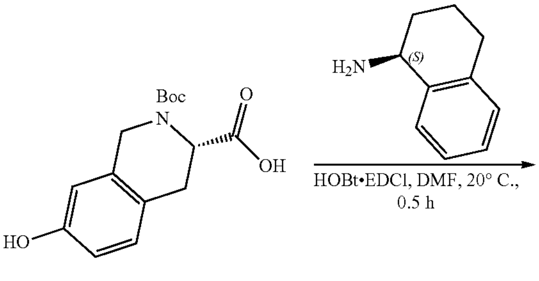

-continued

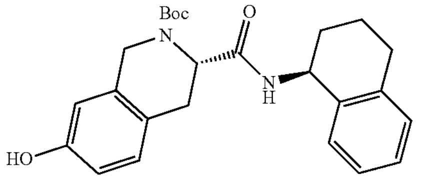

To a solution of (3S)-2-tert-butoxycarbonyl-7-hydroxy-3,4-dihydro-1H-isoquinoline-3-carboxylic acid (2 g, 6.82 mmol, 1 eq) in N,N-dimethylformamide (20 mL) was added (1S)-tetralin-1-amine (1.00 g, 6.82 mmol, 1 eq), hydroxybenzotriazole (1.11 g, 8.18 mmol, 1.2 eq), triethylamine (1.03 g, 10 mmol, 1.5 eq) and 1-ethyl-3-(3-dimethylaminopropyl)carbodiimide hydrochloride (1.57 g, 8 mmol, 1.2 eq). The mixture was stirred at 20° C. for 0.5 hour. The mixture was poured into water (50 mL), and the aqueous phase was extracted with ethyl acetate (50 mL×3). The combined organic phase was washed with brine (30 mL×2), dried with anhydrous sodium sulfate, filtered and concentrated in vacuum. The residue was further purified by silica gel chromatography (petroleum ether:ethyl acetate=3:1). tert-Butyl (3S)-7-hydroxy-3-[[(1S)-tetralin-1-yl] carbamoyl]-3,4-dihydro-1H-isoquinoline-2-carboxylate (2.2 g, 5.21 mmol, 76% yield) was obtained as a white solid.

Step 3

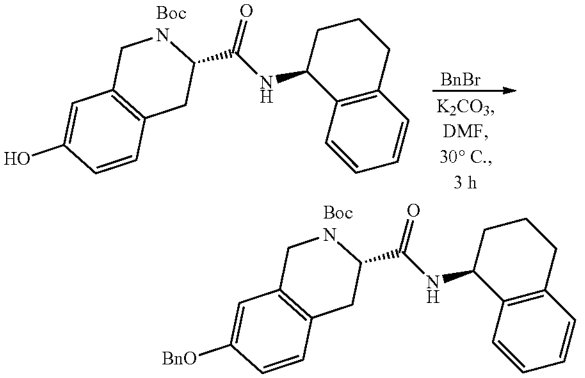

To a solution of tert-butyl (3S)-7-hydroxy-3-[[(1S)-tetralin-1-yl]carbamoyl]-3,4-dihydro-1H-isoquinoline-2-carboxylate (300 mg, 0.7 mmol, 1 eq) in N,N-dimethylformamide (5 mL) was added potassium carbonate (196 mg, 1.42 mmol, 2 eq) and benzyl bromide (242 mg, 1.42 mmol, 2 eq). The mixture was stirred at 30° C. for 3 hours. The mixture was poured into water (20 mL), and the aqueous phase was extracted with ethyl acetate (20 mL×3). The combined organic phase was washed with brine (20 mL×2), dried with anhydrous sodium sulfate, filtered and concentrated in vacuum. The residue was further purified by prep thin-layer chromatography (petroleum ether:ethyl acetate=3:1). tert-Butyl (3S)-7-benzyloxy-3-[[(1S)-tetralin-1-yl]carbamoyl]-3,4-dihydro-1H-isoquinoline-2-carboxylate (220 mg, 0.4 mmol, 60% yield) was obtained as a yellow solid.

Step 4

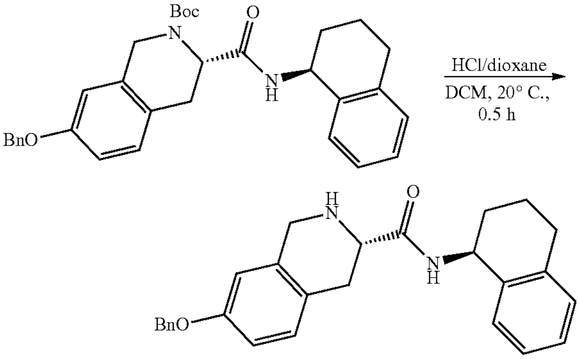

To a solution of tert-butyl (3S)-7-benzyloxy-3-[[(1S)-tetralin-1-yl]carbamoyl]-3,4-dihydro-1H-isoquinoline-2-carboxylate (300 mg, 0.6 mmol, 1 eq) in dichloromethane (2 mL) was added hydrochloric acid in dioxane (4 M, 5 mL, 34 eq). The mixture was stirred at 20° C. for 0.5 hour. The mixture was concentrated in vacuum. (3S)-7-Benzyloxy-N-[(1S)-tetralin-1-yl]-1,2,3,4-tetrahydroisoquinoline-3-carboxamide hydrochloride (300 mg, crude) was obtained as a yellow solid.

Step 5

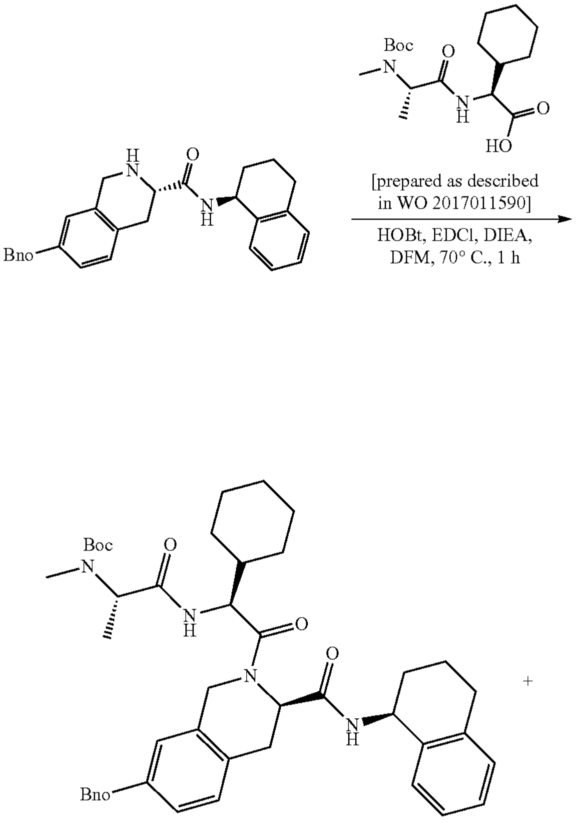

-continued

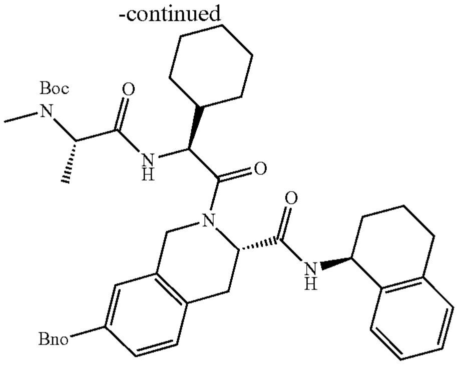

To a solution of (2S)-2-[[(2S)-2-[tert-butoxycarbonyl(methyl)amino]propanoyl]amino]-2-cyclohexyl-acetic acid (170 mg, 0.5 mmol, 1 eq) in N,N-dimethylformamide (20 mL) was added (3S)-7-benzyloxy-N-[(1S)-tetralin-1-yl]-1,2,3,4-tetrahydroisoquinoline-3-carboxamide (222 mg, 0.5 mmol, 1 eq, hydrochloric acid), hydroxybenzotriazole (83 mg, 0.6 mmol, 1.25 eq), 1-ethyl-3-(3-dimethylaminopropyl) carbodiimide hydrochloride (118 mg, 0.6 mmol, 1.25 eq) and diisopropylethylamine (128 mg, 1 mmol, 2 eq)). The resulting reaction was heated at 70° C. and allowed to stir at this temperature for 1 hour. The mixture was poured into water (20 mL), and the aqueous phase was extracted with ethyl acetate (15 mL×3). The combined organic phase was washed with brine (15 mL×2), dried with anhydrous sodium sulfate, filtered and concentrated in vacuum. The residue was further purified by Prep-High Performance Liquid Chromatography (column: Phenomenex luna C18 150*25 10 u; mobile phase: [water (0.225% formic acid)-acetonitrile]; B %: 70%-100%, 7.8 min. tert-Butyl N-[(1S)-2-[[(1S)-2-[(3R)-7-benzyloxy-3-[[(1S)-tetralin-1-yl]carbamoyl]-3,4-dihydro-1H-isoquinolin-2-yl]-1-cyclohexyl-2-oxo-ethyl]amino]-1-methyl-2-oxo-ethyl]-N-methyl-carbamate (70 mg, 0.1 mmol) was obtained as a white solid, and tert-butyl N-[(1S)-2-[[(1S)-2-[(3S)-7-benzyloxy-3-[[(1S)-tetralin-1-yl]carbamoyl]-3,4-dihydro-1H-isoquinolin-2-yl]-1-cyclohexyl-2-oxo-ethyl]amino]-1-methyl-2-oxo-ethyl]-N-methyl-carbamate (70 mg, 0.1 mmol) was obtained as a colorless oil.

Step 6

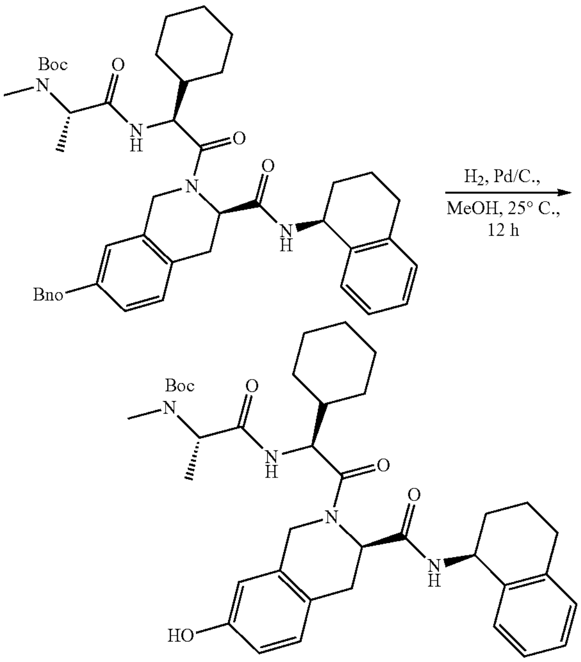

To a solution of tert-butyl N-[(1S)-2-[[(1S)-2-[(3R)-7-benzyloxy-3-[[(1S)-tetralin-1-yl]carbamoyl]-3,4-dihydro-1H-isoquinolin-2-yl]-1-cyclohexyl-2-oxo-ethyl]amino]-1-methyl-2-oxo-ethyl]-N-methyl-carbamate (70 mg, 0.1 mmol, 1 eq) in methanol (3 mL) was added 10% palladium on activated carbon (106 mg, 0.1 mmol). The mixture was stirred at 25° C. for 12 hours under 15 psi of hydrogen. The mixture was filtered and concentrated in vacuum. tert-Butyl N-[(1S)-2-[[(1S)-1-cyclohexyl-2-[(3R)-7-hydroxy-3-[[(1S)-tetralin-1-yl]carbamoyl]-3,4-dihydro-1H-isoquinolin-2-yl]-2-oxo-ethyl]amino]-1-methyl-2-oxo-ethyl]-N-methyl-carbamate (60 mg, crude) was obtained as a colorless oil.

Synthetic procedures similar to those described in steps 1 through 6 have also been described by Casillas, L. et al. in WO 2016172134.

tert-Butyl N-[(1S)-2-[[(1S)-1-cyclohexyl-2-[(3R)-7-hydroxy-3-[[(1S)-tetralin-1-yl]carbamoyl]-3,4-dihydro-1H-isoquinolin-2-yl]-2-oxo-ethyl]amino]-1-methyl-2-oxo-ethyl]-N-methyl-carbamate was converted to the title compound according to the scheme below using procedures described for other examples above.

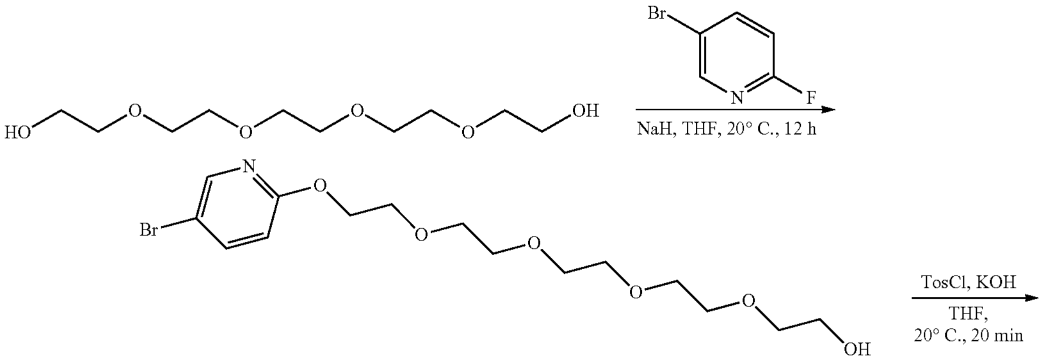

-continued
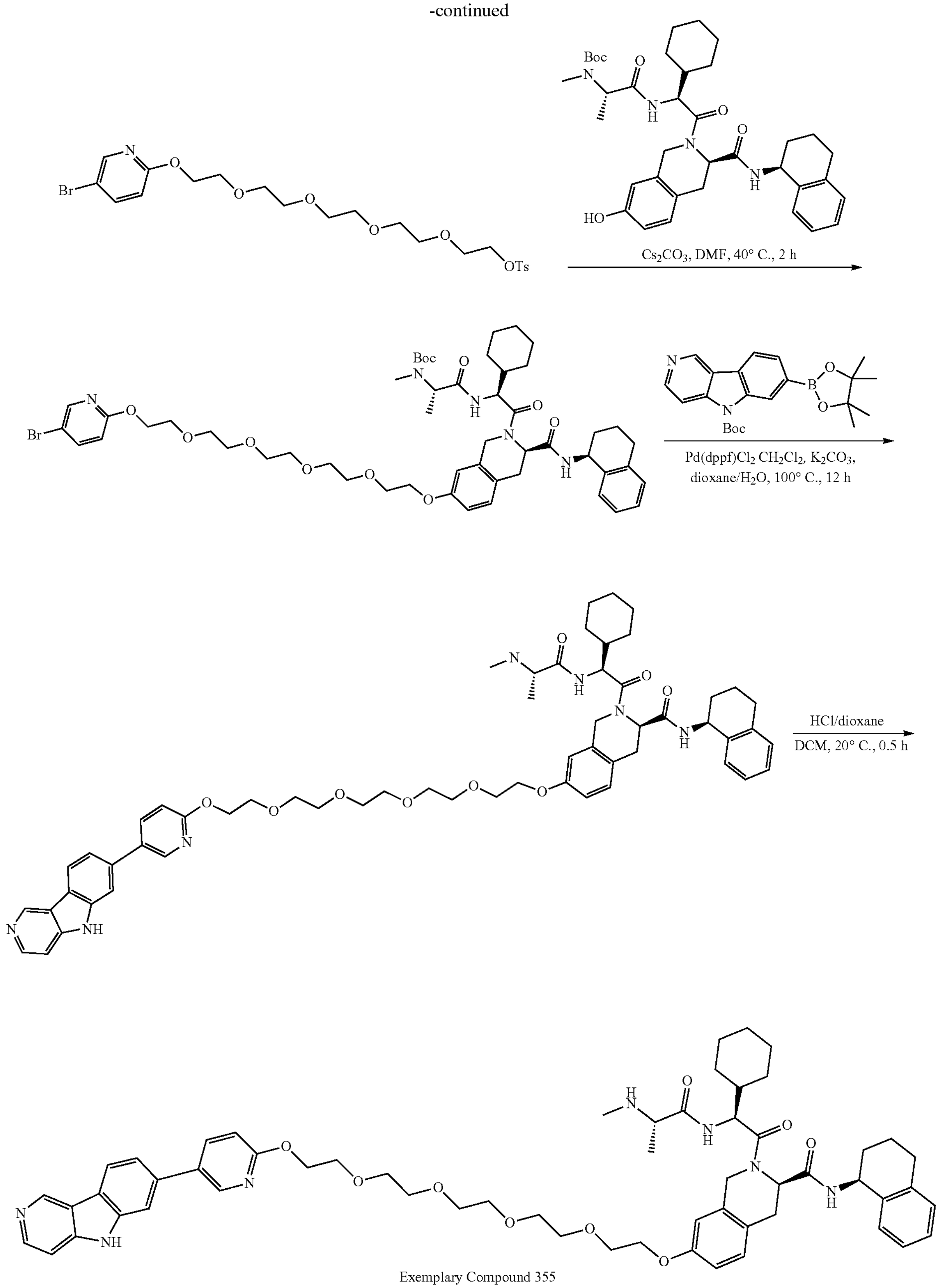
Exemplary Compound 355
Using analogous procedures the following exemplary compounds were prepared: 363, 364, 365, 366, 373.

Exemplary Synthesis of Exemplary Compound 356

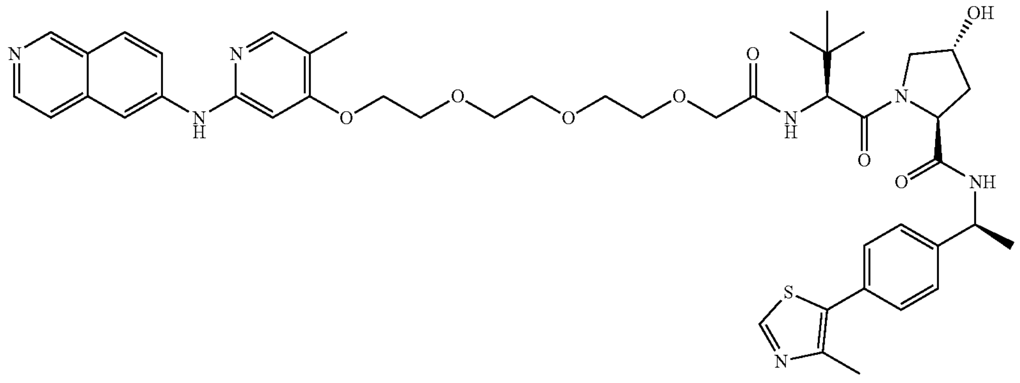 [SMILES: Cc1cnc(Nc2ccc3cnccc3c2)cc1OCCOCCOCCOCC(=O)N[C@H](C(=O)N1C[C@H](O)C[C@H]1C(=O)N[C@@H](C)c1ccc(-c2scnc2C)cc1)C(C)(C)C]

Step 1

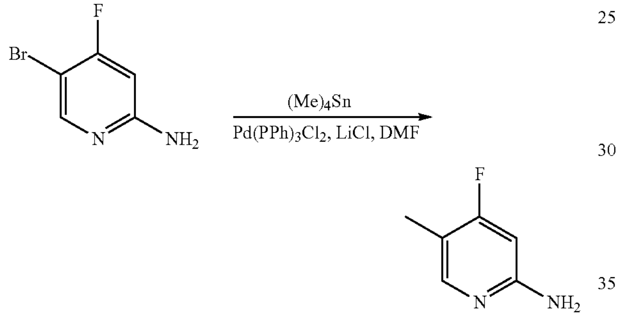

Into a 50-mL round-bottom flask purged and maintained with an inert atmosphere of nitrogen, was placed 5-bromo-4-fluoropyridin-2-amine (9 g, 47.1 mmol, 1 equiv), tetramethylstannane (25.6 g, 143 mmol, 3.04 equiv), LiCl (8 g, 189 mmol, 4 equiv), and $Pd(PPh_3)_2Cl_2$ (3.3 g, 4.70 mmol, 0.10 equiv) in DMF (200 mL) at room temperature under nitrogen atmosphere. The resulting solution was stirred for 15 hr at 100° C. under nitrogen atmosphere. The reaction mixture was cooled to room temperature and was diluted with 500 mL EtOAc. The resulting mixture was washed with $H_2O$ (3×500 mL). The organic phase was dried over anhydrous sodium sulfate and concentrated. The residue was applied onto a silica gel column eluting with ethyl acetate/petroleum ether (1:4). This resulted in 5 g (84%) of 4-fluoro-5-methylpyridin-2-amine as a yellow solid.

Step 2

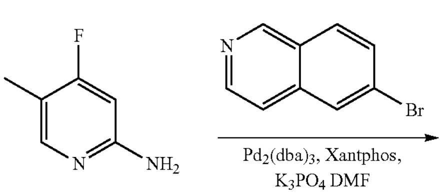

-continued

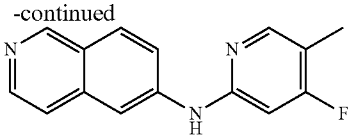

Into a 250-mL round-bottom flask purged and maintained with an inert atmosphere of nitrogen, was placed 4-fluoro-5-methylpyridin-2-amine (3 g, 23.78 mmol, 1 equiv), 6-bromoisoquinoline (5.38 g, 25.86 mmol, 1.09 equiv), $Pd_2(dba)_3$ (1.46 g, 1.59 mmol, 0.07 equiv), Xantphos (1.37 g, 2.36 mmol, 0.10 equiv), and $K_3PO_4$ (15 g, 70.66 mmol, 2.97 equiv) in DMF (100 mL) at room temperature under nitrogen atmosphere. The resulting mixture was stirred for 15 hr at 100° C. under nitrogen atmosphere. The reaction mixture was cooled to room temperature and was diluted with 300 mL EtOAc. The resulting mixture was washed with $H_2O$ (3×300 ml). The organic layer was dried over anhydrous sodium sulfate and concentrated. The residue was applied onto a silica gel column eluting with ethyl acetate/petroleum ether (1:3). This resulted in 5.7 g (95%) of N-(4-fluoro-5-methylpyridin-2-yl)isoquinolin-6-amine as a yellow solid.

Step 3

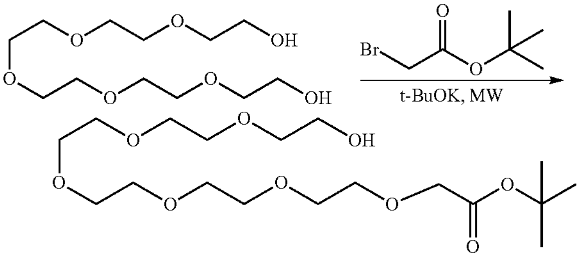

Into a 5-mL sealed tube, was placed a mixture of tert-butyl 2-bromoacetate (200 mg, 1.03 mmol, 1 equiv), t-BuOK (115 mg, 1.03 mmol, 1 equiv) in 3, 6, 9, 12, 15-pentaoxaheptadecane-1, 17-diol (2 mL) under nitrogen atmosphere. The reaction mixture was heated via microwave irradiation for 1.5 hr at 170° C. under nitrogen atmosphere. The reaction mixture was cooled to room temperature and diluted with 90 mL dichloromethane. The resulting mixture was washed with brine (3×30 mL), dried over anhydrous sodium sulfate and concentrated under vacuum. This resulted in 120 mg (crude) of tert-butyl 20-hydroxy-3,6,9,12,15,18-hexaoxaicosanoate as a light yellow oil.

Step 4

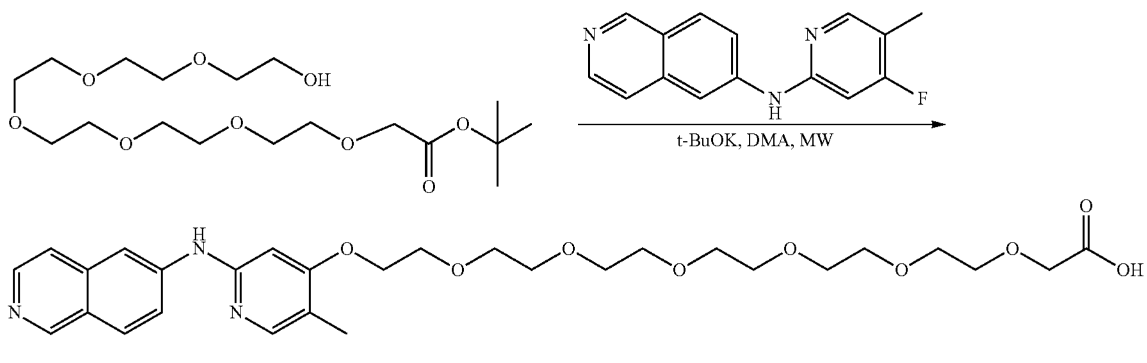

Into a 5-mL sealed tube, was placed tert-butyl 20-hydroxy-3,6,9,12,15,18-hexaoxaicosanoate (300 mg, 0.76 mmol, 1 equiv), N-(4-fluoro-5-methylpyridin-2-yl)isoquinolin-6-amine (100 mg, 0.40 mmol, 0.52 equiv), and t-BuOK (66 mg, 0.59 mmol, 0.78 equiv) in DMA (1 mL) under nitrogen atmosphere. The reaction mixture was heated via microwave irradiation for 1.5 hr at 170° C. under nitrogen atmosphere. The reaction mixture was cooled to room temperature and diluted with 100 mL dichloromethane. The resulting mixture was washed with brine (3x30 ml), dried over anhydrous sodium sulfate and concentrated under vacuum. The residue was applied onto a silica gel column eluting with dichloromethane/methanol (10:1). This resulted in 120 mg (28% for 2 steps) of 20-((2-(isoquinolin-6-ylamino)-5-methylpyridin-4-yl)oxy)-3,6,9,12,15,18-hexaoxaicosanoic acid as a yellow oil.

Step 5

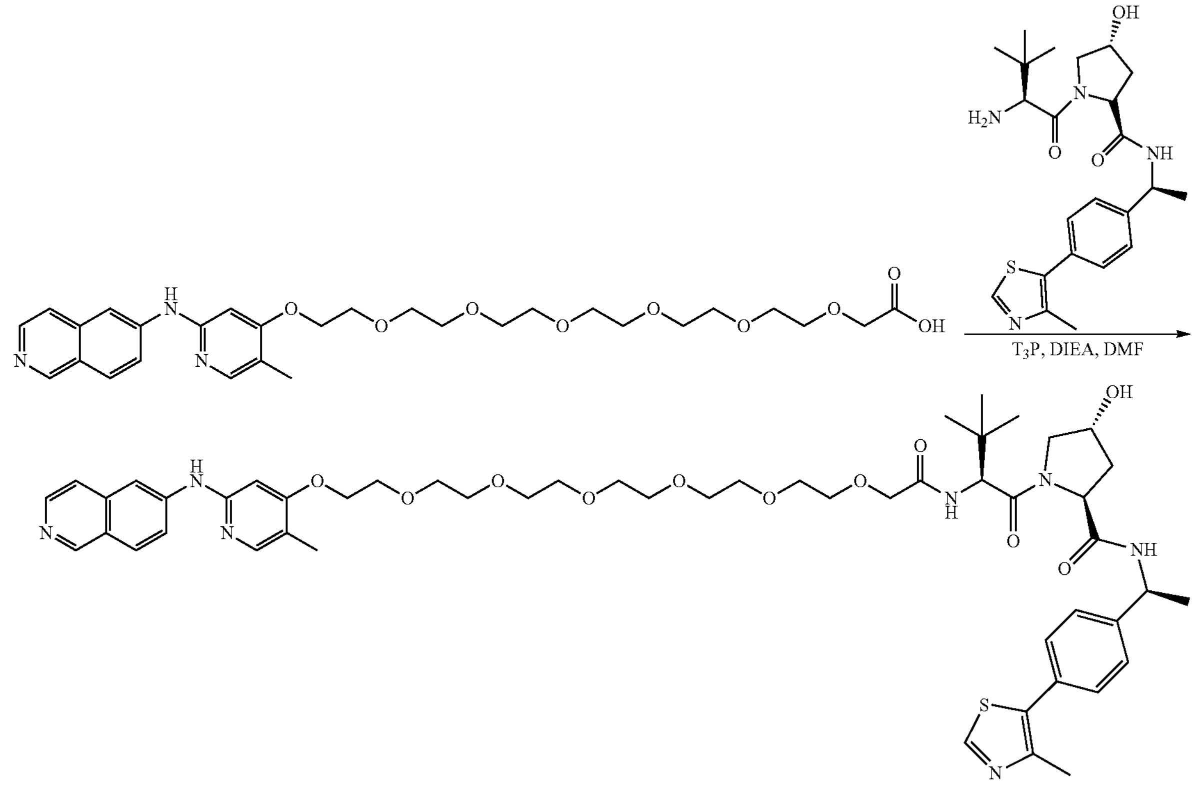

Exemplary Compound 356

Into a 50-mL 3-necked round-bottom flask, was placed 20-((2-(isoquinolin-6-ylamino)-5-methylpyridin-4-yl)oxy)-3,6,9,12,15,18-hexaoxaicosanoic acid (110 mg, 0.20 mmol, 1 equiv) in DMF (5 mL), to which was added (2S,4R)-1-[(2S)-2-amino-3,3-dimethylbutanoyl]-4-hydroxy-N-[(1S)-1-[4-(4-methyl-1,3-thiazol-5-yl)phenyl]ethyl]pyrrolidine-2-carboxamide (100 mg, 0.23 mmol, 1.14 equiv), DIEA (50 mg, 0.39 mmol, 1.97 equiv), $T_3P$ (310 mg, 0.49 mmol, 2.45 equiv, 50%) at room temperature. The resulting solution was stirred for 2 hr at room temperature, and then was concentrated. The crude product was purified by Prep-HPLC with the following conditions: Column, XBridge Prep OBD C18 Column, 19*150 mm, 5 um; Mobile Phase A: Water (with 0.1% FA), Mobile Phase B: $CH_3CN$; Gradient: 10% B to 27% B in 11 min; 254 nm. This resulted in 14.5 mg (7%) of (2S,4R)-4-hydroxy-1-[(2S)-2-[20-([2-[(isoquinolin-6-yl)amino]-5-methylpyridin-4-yl]oxy)-3,6,9,12,15,18-hexaoxaicosanamido]-3,3-dimethylbutanoyl]-N-[(1S)-1-[4-(4-methyl-1,3-thiazol-5-yl)phenyl]ethyl]pyrrolidine-2-carboxamide as a white solid.

Exemplary Synthesis of Exemplary Compound 368

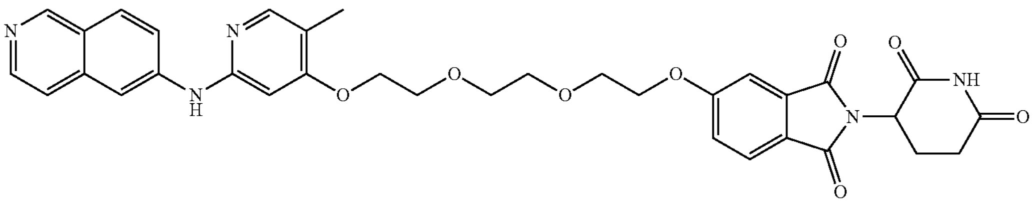 [SMILES: Cc1cnc(Nc2ccc3cnccc3c2)cc1OCCOCCOCCOc1ccc2c(c1)C(=O)N(C1CCC(=O)NC1=O)C2=O]

Prepared according to the scheme below using procedures from exemplary compound 356 and other examples above.

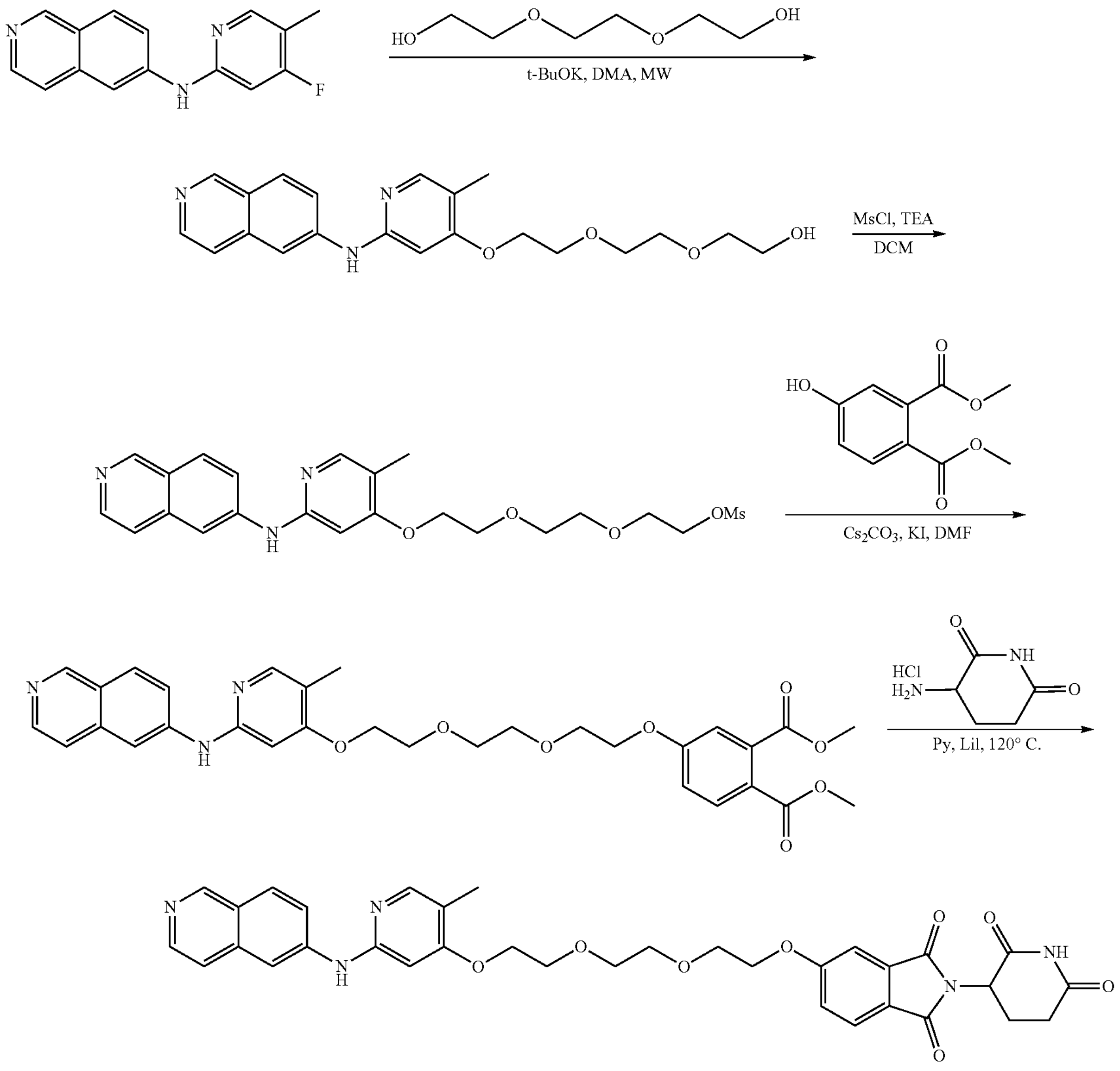

Exemplary Comound 368

Using analogous procedures the following exemplary compounds were prepared: 358, 361, 362, 369, 370.

Exemplary Synthesis of Exemplary Compound 371

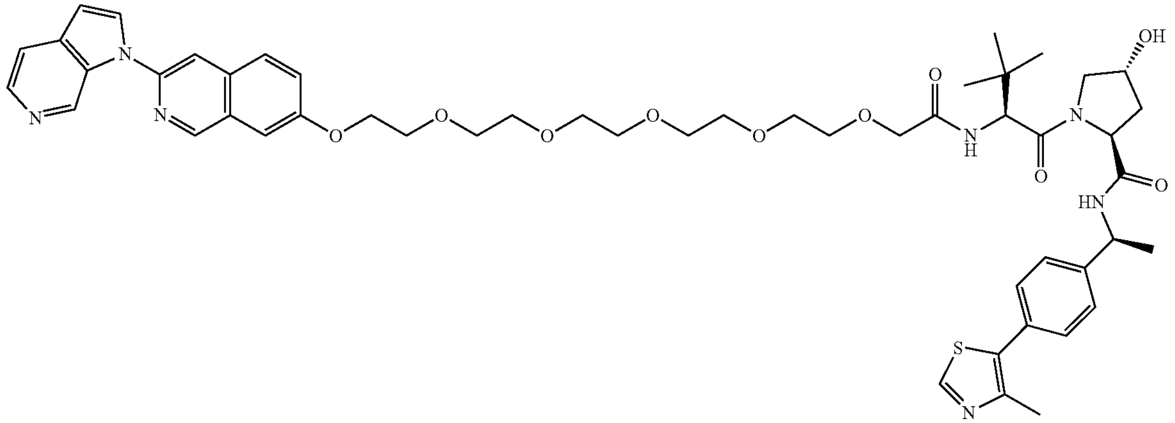 [SMILES: Cc1ncsc1-c1ccc([C@H](C)NC(=O)[C@@H]2C[C@@H](O)CN2C(=O)[C@@H](NC(=O)COCCOCCOCCOCCOCCOc2ccc3cc(-n4ccc5ccncc54)ncc3c2)C(C)(C)C)cc1]

Step 1

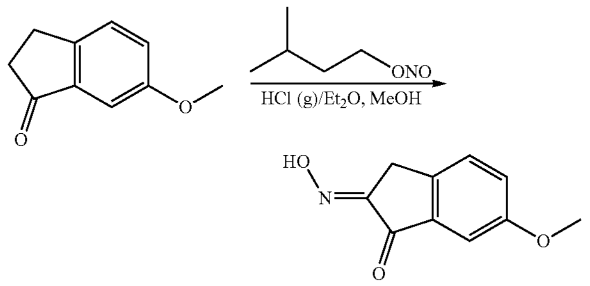

Into a 1000-mL round-bottom flask was placed 6-methoxy-2,3-dihydro-1H-inden-1-one (20 g, 123.3 mmol, 1 equiv) in $Et_2O$ (200 mL), to which was added 3-methylbutyl nitrite (21.67 g, 185.0 mmol, 1.50 equiv). The flask was then flushed with hydrogen HCl (g). The resulting solution was stirred for 3 hr at room temperature. The solids were collected by filtration. The resulting mixture was concentrated. This resulted in 22 g (93%) of (2E)-2-(hydroxyimino)-6-methoxy-2,3-dihydro-1H-inden-1-one as a yellow solid.

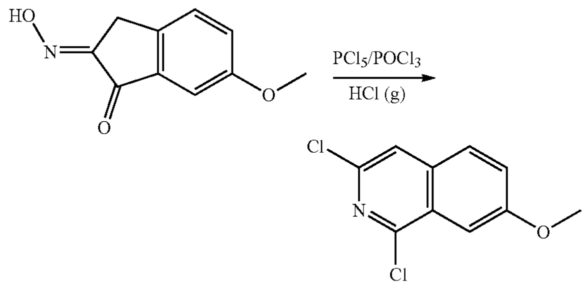

Into a 500-mL 3-neck round-bottom flask, was placed (2E)-2-(hydroxyimino)-6-methoxy-2,3-dihydro-1H-inden-1-one (25 g, 130.8 mmol, 1 equiv) in $POCl_3$ (150 mL), to which was added $PCl_5$ (67 g, 321.7 mmol, 2.5 equiv). The flask was then flushed with hydrogen HCl (g) at 60° C. The resulting solution was stirred for 3 hr at 60° C., and then for an additional 15 hr at 35° C. The reaction mixture was cooled to room temperature. The reaction was then quenched by the addition of 2000 mL of water. The solids were collected by filtration. The resulting mixture was concentrated. This resulted in 12 g (40%) of 1,3-dichloro-6-methoxyisoquinoline as a yellow solid.

Step 3

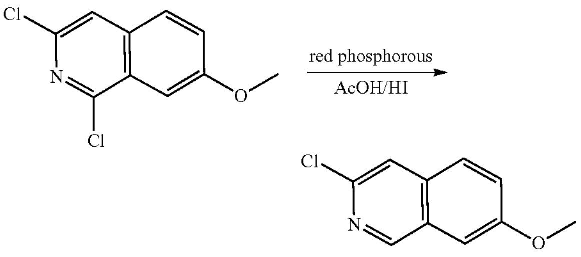

Into a 1000-mL round-bottom flask, was placed 1,3-dichloro-7-methoxyisoquinoline (12 g, 52.6 mmol, 1 equiv), red phosphorus (8.2 g, 264.5 mmol, 5 equiv) in AcOH (100 mL) and HI (aq) (50 mL, 55%). The resulting solution was stirred for 5 hr at 110° C. The reaction mixture was cooled to room temperature. The resulting solution was diluted with 500 mL of EA. The resulting mixture was washed with (3×500 mL) of $H_2O$. The mixture was dried over anhydrous sodium sulfate and concentrated. The residue was applied onto a silica gel column eluting with ethyl acetate/petroleum ether (1:3). This resulted in 4 g (39%) of 3-chloro-7-methoxyisoquinoline as a yellow solid.

Step 4

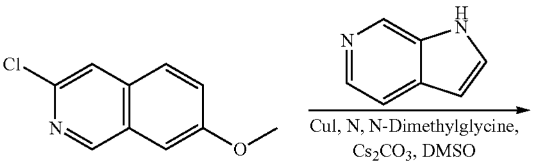

-continued

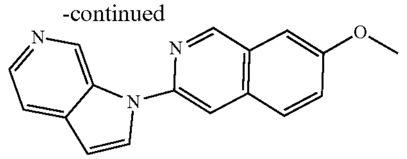

Into a 250-mL round-bottom flask, was placed 3-chloro-7-methoxyisoquinoline (3.6 g, 18.6 mmol, 1.0 equiv), 1H-pyrrolo[2,3-c]pyridine (3.3 g, 27.9 mmol, 1.5 equiv), 2-(dimethylamino)acetic acid (1.9 g, 18.42 mmol, 1.0 equiv) and CuI (3.53 g, 18.5 mmol, 1.0 equiv) in DMSO (100 mL), to which was added $Cs_2CO_3$ (10.1 g, 31.0 mmol, 1.67 equiv). The resulting solution was stirred for 15 hr at 130° C. The reaction mixture was cooled to room temperature. The solids were filtered out. The resulting solution was diluted with 300 mL of EA. The resulting mixture was washed with (3×300 mL) of $H_2O$. The mixture was dried over anhydrous sodium sulfate and concentrated. The residue was applied onto a silica gel column eluting with ethyl acetate/petroleum ether (1:1). This resulted in 1.7 g (33%) of 7-methoxy-3-[1H-pyrrolo[2,3-c]pyridin-1-yl]isoquinoline as a yellow solid.

Step 5

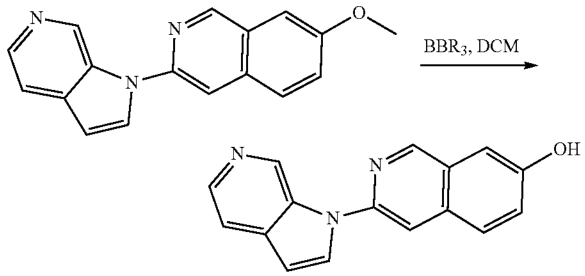

Into a 100-mL round-bottom flask, was placed 7-methoxy-3-[1H-pyrrolo[2,3-c]pyridin-1-yl]isoquinoline (600 mg, 2.17 mmol, 1 equiv) in hydrogen bromide (aq) (10 mL, 48%). The resulting solution was stirred for 48 hr at 100° C. The reaction mixture was cooled to room temperature. The pH value of the solution was adjusted to 7 with $NaHCO_3$ (aq). The resulting mixture was concentrated. The residue was applied onto C18 column eluting with MeCN: water (2:3). This resulted in 220 mg (39%) of 3-[1H-pyrrolo[2,3-c]pyridin-1-yl]isoquinolin-7-ol as a yellow solid.

3-[1H-pyrrolo[2,3-c]pyridin-1-yl]isoquinolin-7-ol was converted to the title compound according to the scheme below using procedures of exemplary compound 3551 and other examples described above.

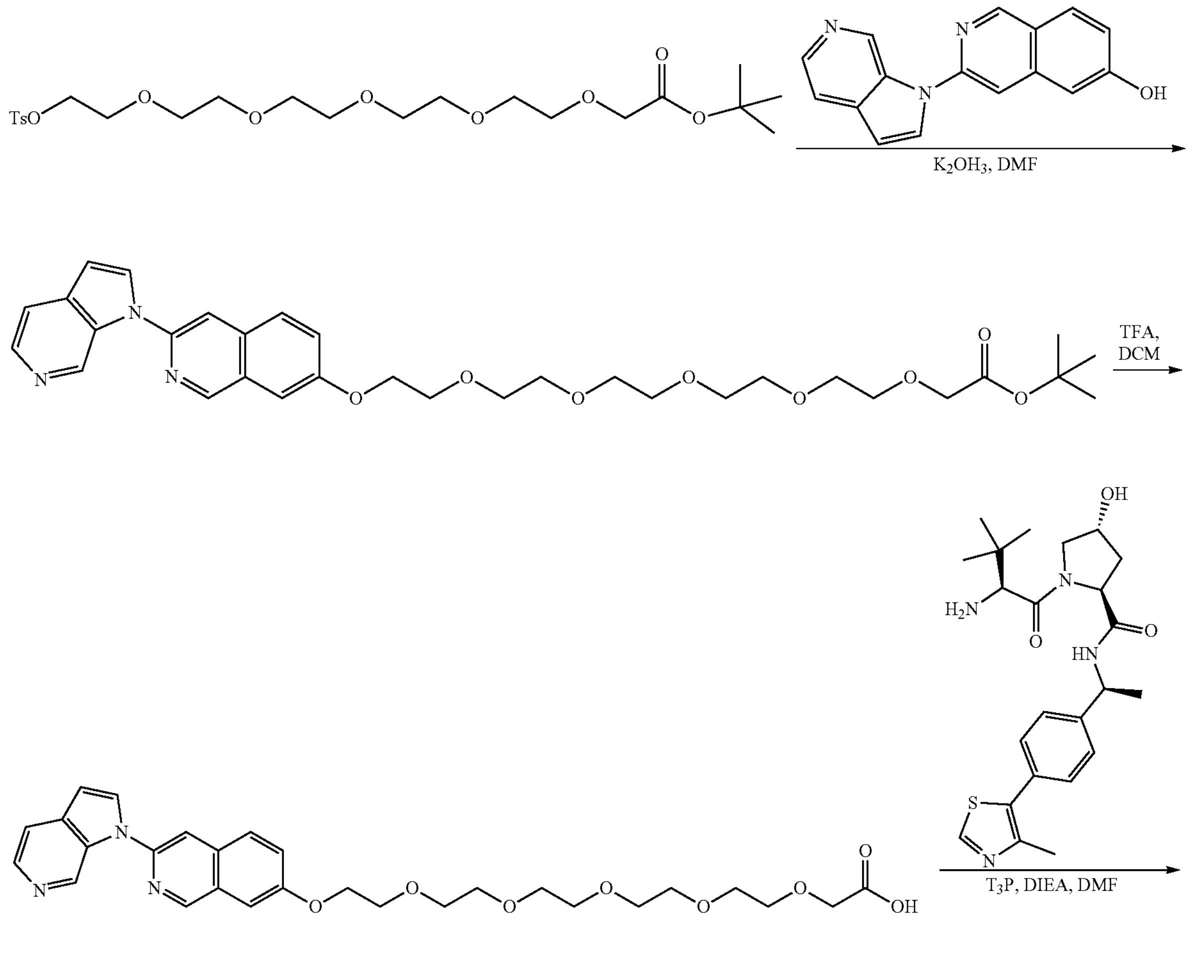

-continued
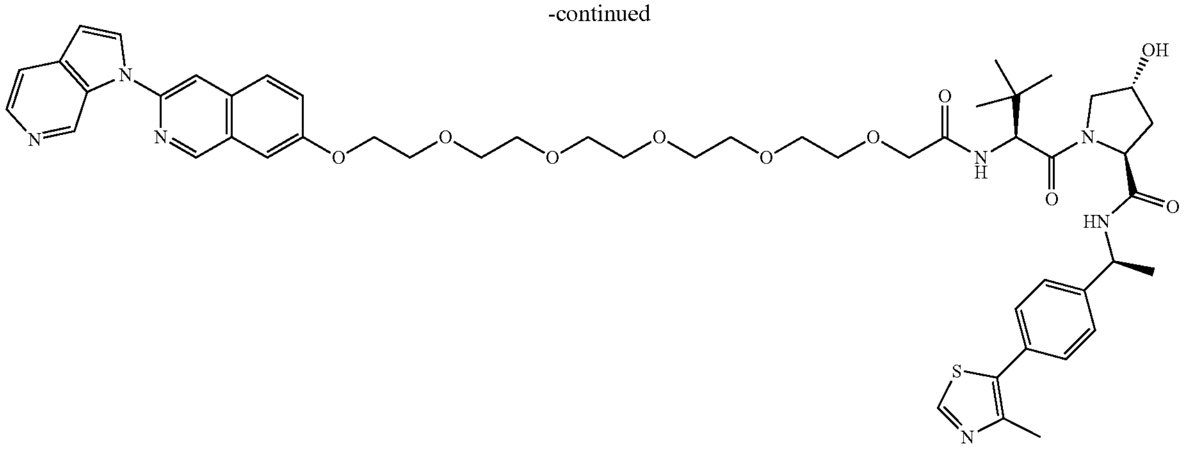
Exemplary Compound 371
Exemplary Synthesis of Exemplary Compound 383
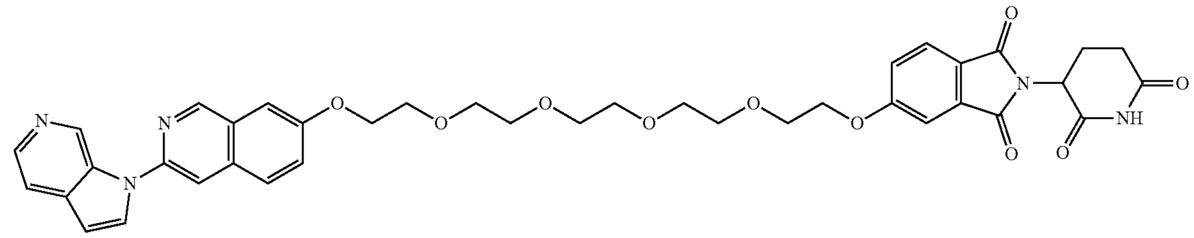 [SMILES: O=C1CCC(N2C(=O)c3ccc(OCCOCCOCCOCCOCCOc4ccc5cc(-n6ccc7ccncc76)ncc5c4)cc3C2=O)C(=O)N1]
Prepared according to the scheme below using procedures described for exemplary compound 352 and other examples above.
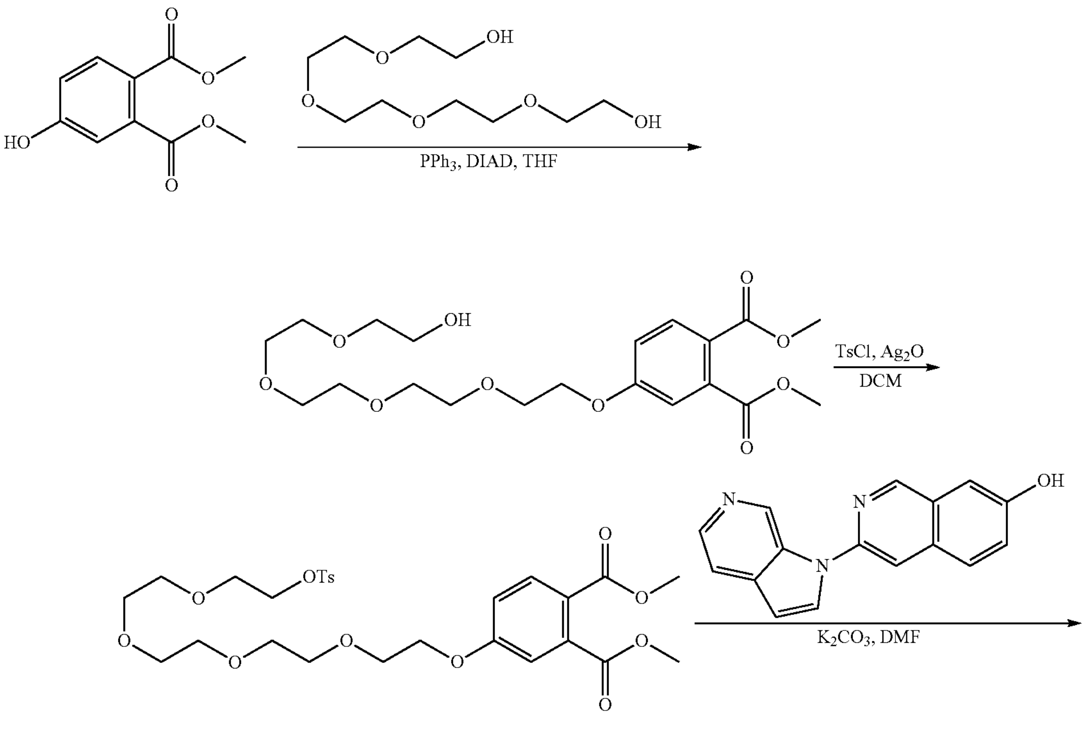

-continued

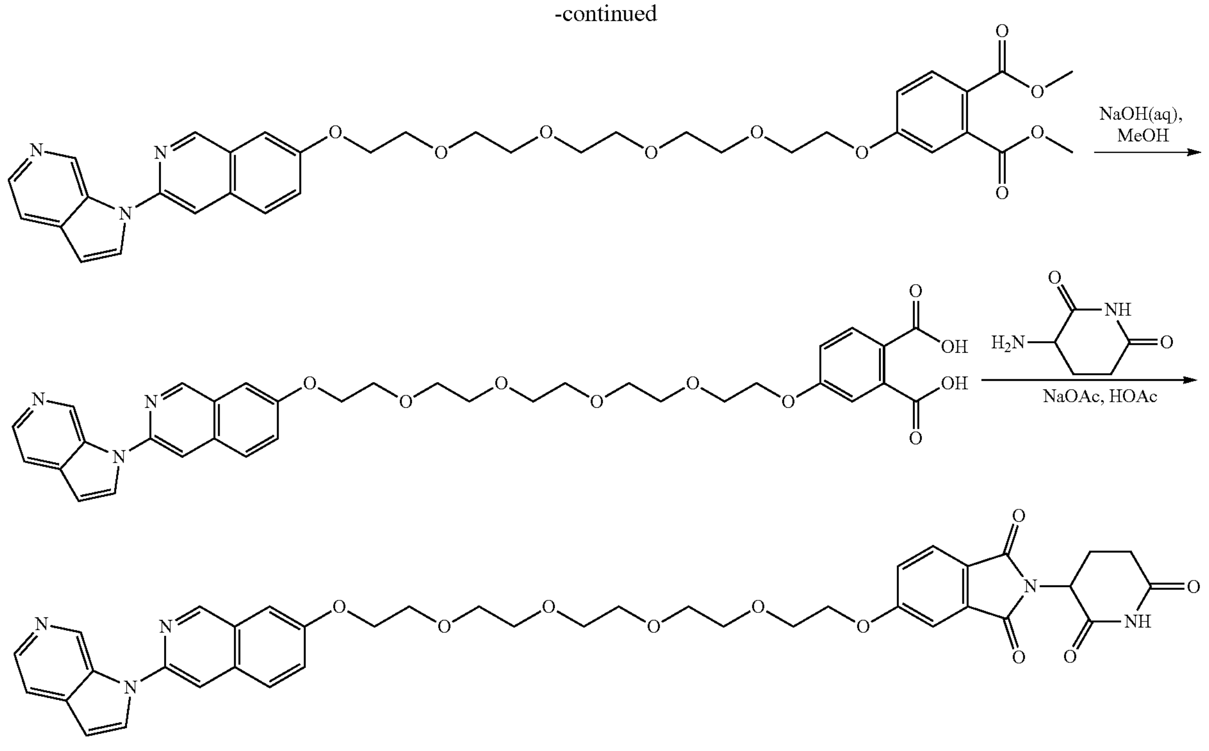

Exemplary Compound 383

Using analogous procedures the following exemplary compounds were prepared: 375, 384.

Exemplary Synthesis of Exemplary Compound 372

Step 1

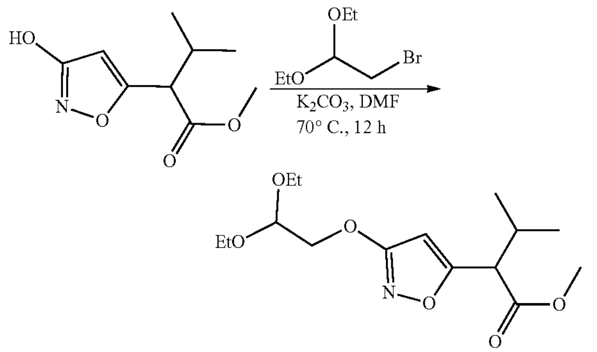

To a solution of methyl 2-(3-hydroxyisoxazol-5-yl)-3-methyl-butanoate (3.5 g, 17.57 mmol, 1 eq) in N,N-dimethylformamide (40 mL) was added 2-bromo-1,1-diethoxyethane (5.19 g, 26.35 mmol, 1.5 eq) and potassium carbonate (4.86 g, 35.14 mmol, 2 eq). The reaction mixture was stirred at 70° C. for 12 h. The reaction mixture was quenched by the addition of water (50 mL), and then diluted with water (100 mL) and extracted with ethyl acetate (80 mL×3). The combined organic layers were washed with brine (100 mL×2), dried over anhydrous sodium sulfate, filtered and concentrated under reduced pressure to give a residue. The residue was purified by silica gel chromatography (petroleum ether:ethyl acetate=100:1 to 50:1). The desired compound methyl 2-[3-(2,2-diethoxyethoxy)isoxazol-5-yl]-3-methyl-butanoate (4.38 g, 12.50 mmol, 71% yield) was obtained as a colorless oil.

Step 2

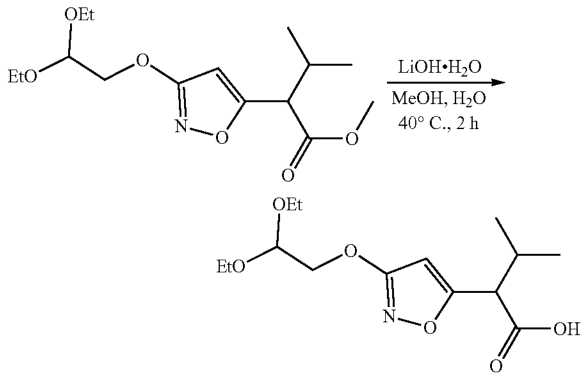

To a solution of methyl 2-[3-(2,2-diethoxyethoxy)isoxazol-5-yl]-3-methyl-butanoate (4.38 g, 12.5 mmol, 1 eq) in methanol (30 mL) and water (15 mL) was added lithium hydroxide monohydrate (2.10 g, 50 mmol, 4 eq). The reaction mixture was stirred at 40° C. for 2 h. The pH was adjusted to 4-5 with 1M hydrogen chloride, and the mixture was then extracted with ethyl acetate (50 mL×2). The combined organic layers were dried over anhydrous sodium sulfate, filtered and concentrated under reduced pressure to give a residue. 2-[3-(2,2-diethoxyethoxy)isoxazol-5-yl]-3-methyl-butanoic acid (4 g, crude) was obtained as a colorless oil.

Step 3

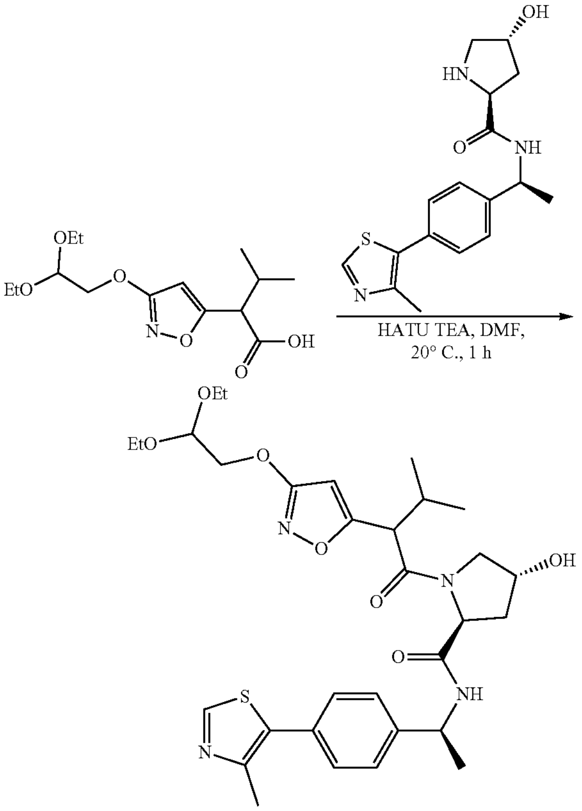

To a solution of 2-[3-(2,2-diethoxyethoxy)isoxazol-5-yl]-3-methyl-butanoic acid (3.84 g, 11.99 mmol, 1 eq) in N,N-dimethylformamide (20 mL) was added O—(7-azabenzotriazol-1-yl)-N,N,N',N'-tetramethyluronium hexafluorophosphate (5.47 g, 14.38 mmol, 1.2 eq) the reaction mixture was stirred at 20° C. for 0.5 h. Then to the mixture was added a solution of (2S,4R)-4-hydroxy-N-[(1S)-1-[4-(4-methylthiazol-5-yl)phenyl]ethyl]pyrrolidine-2-carboxamide hydrochloride (4.41 g, 11.99 mmol, 1 eq) and 573rimethylamine (3.64 g, 35.96 mmol, 5 mL, 3 eq) in N,N-dimethylformamide (10 mL). The reaction mixture was stirred at 20° C. for 0.15 h. The reaction mixture was quenched by the addition of water (30 mL), and then diluted with water (80 mL) and extracted with ethyl acetate (60 mL×3). The combined organic layers were washed with brine (80 mL×2), dried over anhydrous sodium sulfate, filtered and concentrated under reduced pressure to give a residue. The residue was purified by silica gel chromatography (dichloromethane: methanol=100:1 to 50:1). The desired compound (2S,4R)-1-[2-[3-(2,2-diethoxyethoxy)isoxazol-5-yl]-3-methyl-butanoyl]-4-hydroxy-N-[(1S)-1-[4-(4-methylthiazol-5-yl) phenyl]ethyl]pyrrolidine-2-carboxamide (7 g, 10.96 mmol, 91% yield) was obtained as a white solid.

Step 4

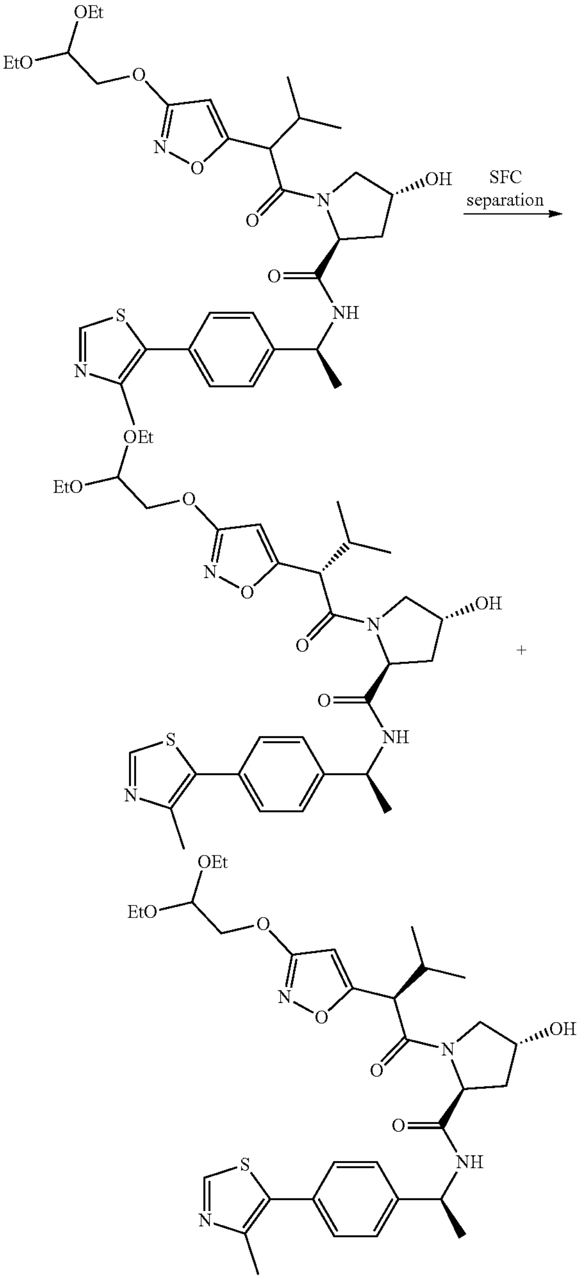

(2S,4R)-1-[2-[3-(2,2-diethoxyethoxy)isoxazol-5-yl]-3-methyl-butanoyl]-4-hydroxy-N-[(1S)-1-[4-(4-methylthiazol-5-yl)phenyl]ethyl]pyrrolidine-2-carboxamide (7 g, 11.39 mmol, 1 eq) was separated by SFC. The condition was column: DAICEL CHIRALPAK AD (250 mm*30 mm, 10 um); mobile phase: [0.1% $NH_3H_2O$ IPA]; B %: 35%-35%, 2.4 min: 550 min. (2S,4R)-1-[(2S)-2-[3-(2,2-diethoxyethoxy)isoxazol-5-yl]-3-methyl-butanoyl]-4-hydroxy-N-[(1S)-1-[4-(4-methylthiazol-5-yl)phenyl]ethyl]pyrrolidine-2-carboxamide (3.2 g, 5.08 mmol, 89% yield, 97% purity) and (2S,4R)-1-[(2R)-2-[3-(2,2-diethoxyethoxy)isoxazol-5-yl]-3-meth yl-butanoyl]-4-hydroxy-N-[(1S)-1-[4-(4-methylthiazol-5-yl)phenyl]ethyl]pyrrolidine-2-carboxamide (2.67 g, 4.17 mmol, 73% yield, 96% purity) were obtained as white solids. (Here and elsewhere in this application configurations of the stereocenter distinguishing the two diastereomers were tentatively assigned at this point and were later ascertained based on the comparative biological activity of the title diastereomeric compounds; see also exemplary compounds 378 and 379).

Step 5

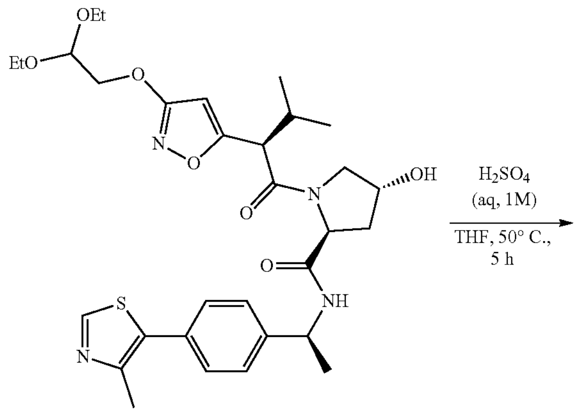

-continued

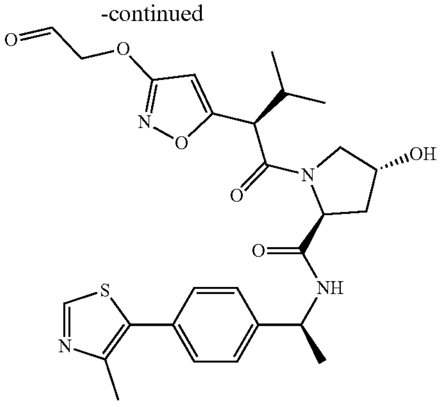

To a solution of (2S,4R)-1-[(2R)-2-[3-(2,2-diethoxyethoxy)isoxazol-5-yl]-3-methyl-butanoyl]-4-hydroxy-N-[(1S)-1-[4-(4-methylthiazol-5-yl)phenyl]ethyl]pyrrolidine-2-carboxamide (2 g, 3.25 mmol, 1 eq) in tetrahydrofuran (40 mL) was added sulfuric acid (1 M, 40 mL, 12.3 eq). The solution was heated to 50° C. for 7 h. The solution was cooled to 20° C. and quenched with saturated sodium bicarbonate solution to pH=8. The mixture was extracted with ethyl acetate (30 mL×3). The combined organic layer was washed with brine (50 mL), dried over sodium sulfate, and concentrated in vacuum. The crude product was used directly in the next step. (2S,4R)-4-hydroxy-1-[(2R)-3-methyl-2-[3-(2-oxoethoxy)isoxazol-5-yl]butanoyl]-N-[(1S)-1-[4-(4-methylthiazol-5-yl)phenyl]ethyl]pyrrolidine-2-carboxamide (1.7 g, 2.52 mmol, 77% yield) was obtained as a white solid.

Step 6

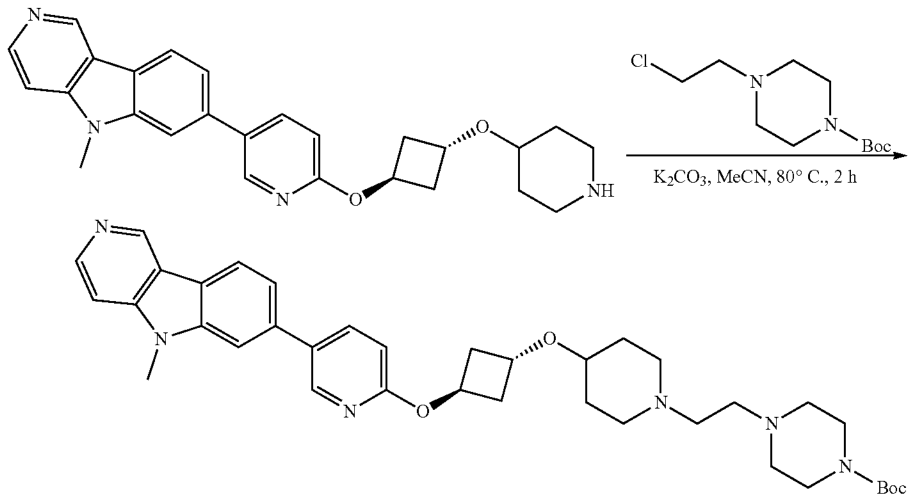

To a mixture of 5-methyl-7-[6-[3-(4-piperidyloxy)cyclobutoxy]-3-pyridyl]pyrido[4,3-b]indole (200 mg, 0.43 mmol, 1 eq, hydrochloride) and tert-butyl 4-(2-chloroethyl) piperazine-1-carboxylate (106 mg, 0.43 mmol, 1 eq) in acetonitrile (10 mL) was added potassium carbonate (118 mg, 0.86 mmol, 2 eq). The mixture was quenched by the addition of water (100 mL), extracted with ethyl acetate (30 mL×3), and the combined organic phase was washed with brine (30 mL), dried over anhydrous sodium sulfate, and concentrated under reduced pressure. The residue was purified by prep-TLC (dichloromethane:methanol=10:1). Compound tert-butyl 4-[2-[4-[3-[[5-(5-methylpyrido[4,3-b]indol-7-yl)-2-pyridyl]oxy]cyclobutoxy]-1-piperidyl]ethyl] piperazine-1-carboxylate (140 mg, 0.21 mmol, 50% yield) was obtained as a brown solid.

tert-Butyl 4-[2-[4-[3-[[5-(5-methylpyrido[4,3-b]indol-7-yl)-2-pyridyl]oxy]cyclobutoxy]-1-piperidyl]ethyl]piperazine-1-carboxylate was converted to the title compound according to the scheme below using procedures described for other examples above and those commonly known to skilled in the art.
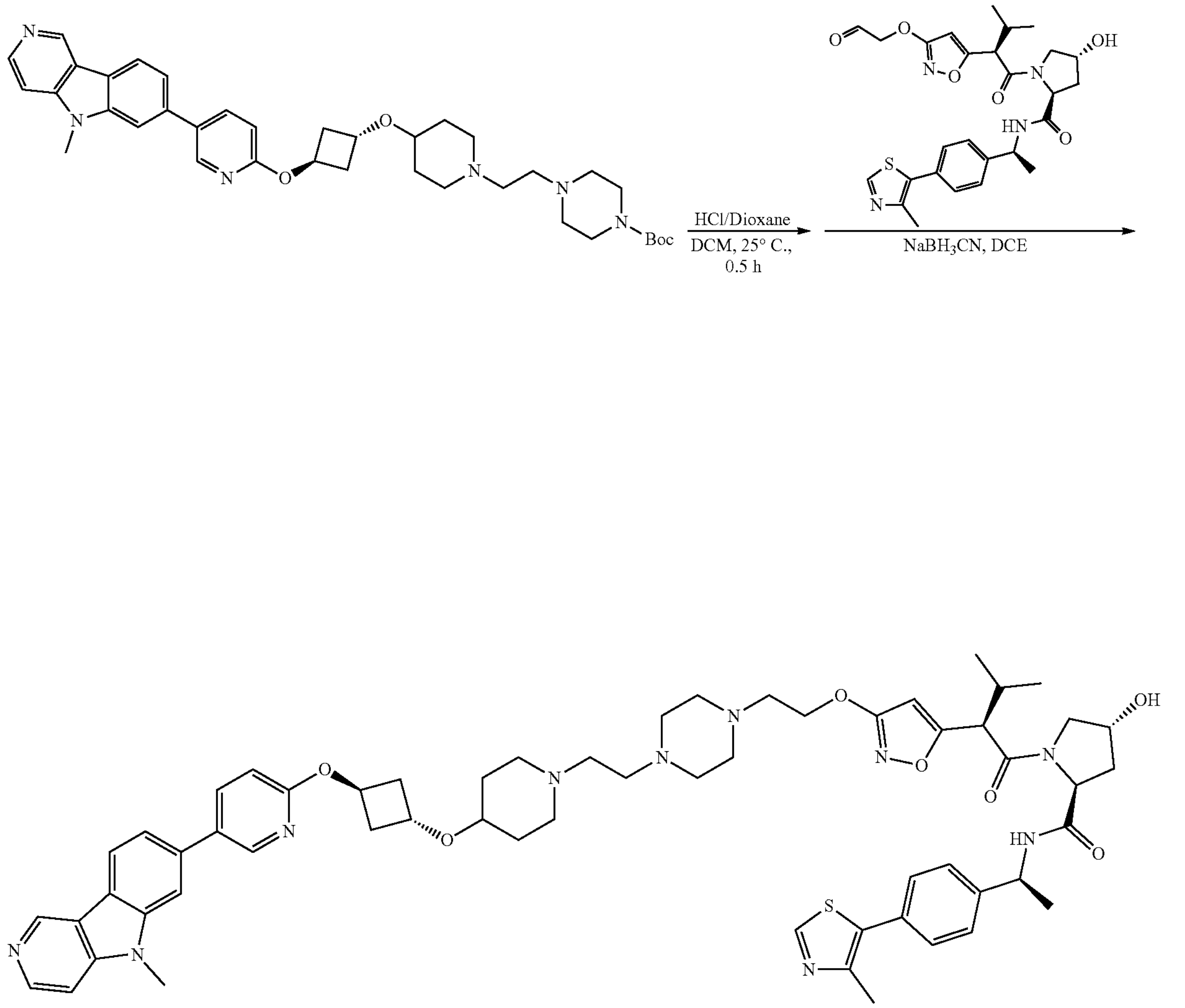
Exemplary Compound 372
Exemplary Synthesis of Exemplary Compound 374
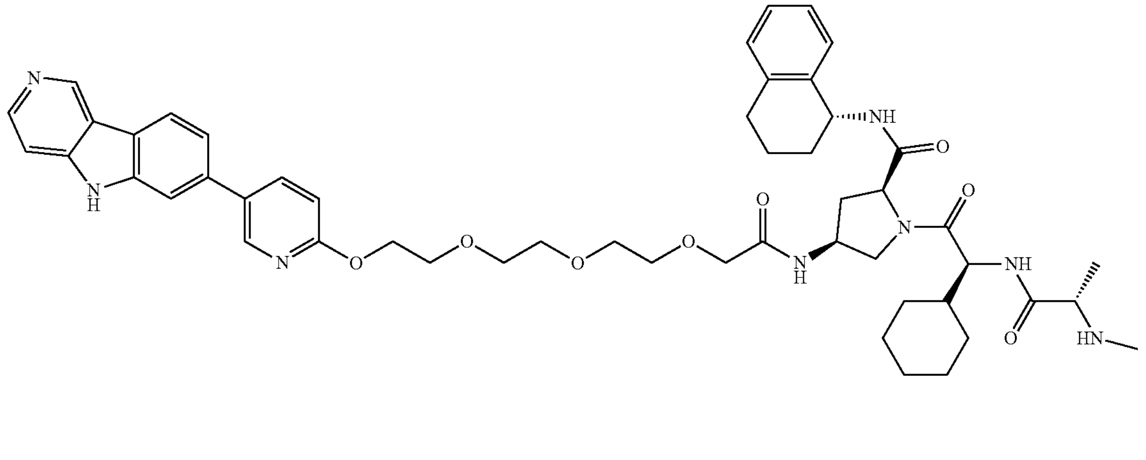 [SMILES: CN[C@@H](C)C(=O)N[C@H](C(=O)N1C[C@@H](NC(=O)COCCOCCOCCOc2ccc(-c3ccc4c(c3)[nH]c3ccncc34)cn2)C[C@H]1C(=O)N[C@@H]1CCCc2ccccc21)C1CCCCC1]

Step 1

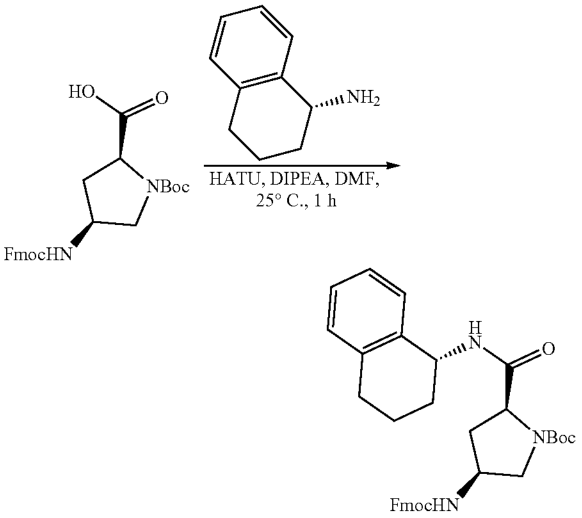

To a solution of (2S,4S)-1-tert-butoxycarbonyl-4-(9H-fluoren-9-ylmethoxycarbonylamino)pyrrolidine-2-carboxylic acid (4.8 g, 10.61 mmol, 1 eq) and (1 R)-tetralin-1-amine (1.56 g, 10.61 mmol, 1 eq) in N,N-dimethylformamide (50 mL) was added N,N-diisopropylethylamine (2.74 g, 21.22 mmol, 3.7 mL, 2 eq). The mixture was stirred at 25° C. for 10 min. Then O—(7-azabenzotriazol-1-yl)-N,N,N',N'-tetramethyluronium hexafluorophosphate (8.07 g, 21.22 mmol, 2 eq) was added to the mixture. The mixture was stirred at 25° C. for 50 min. To the mixture was added brine (100 mL), and it was extracted with ethyl acetate (100 mL×3). The organic layer was dried over sodium sulfate and concentrated. The residue was purified using silica gel chromatography (petroleum ether:ethyl acetate=10:1 to 0:1). Tert-Butyl (2S,4S)-4-(9H-fluoren-9-ylmethoxycarbonylamino)-2-[[(1R)-tetralin-1-yl]carbamoyl]pyrrolidine-1-carboxylate (4.5 g, 7.74 mmol, 72% yield) was obtained as a white solid.

Step 2

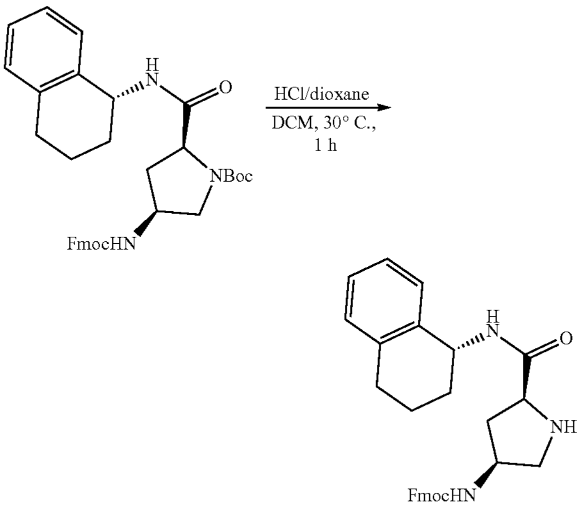

To a solution of tert-butyl (2S,4S)-4-(9H-fluoren-9-ylmethoxycarbonylamino)-2-[[(1R)-tetralin-1-yl]carbamoyl]pyrrolidine-1-carboxylate (4.5 g, 7.74 mmol, 1 eq) in dichloromethane (30 mL) was added hydrogen chloride/dioxane (4 M, 1.93 mL, 1 eq). The mixture was stirred at 30° C. for 1 h. The mixture was concentrated. The residue was used in the next step without further purification. 9H-Fluoren-9-ylmethyl N-[(3S,5S)-5-[[(1R)-tetralin-1-yl]carbamoyl]pyrrolidin-3-yl]carbamate hydrochloride (4 g, crude) was obtained as a white solid.

Step 3

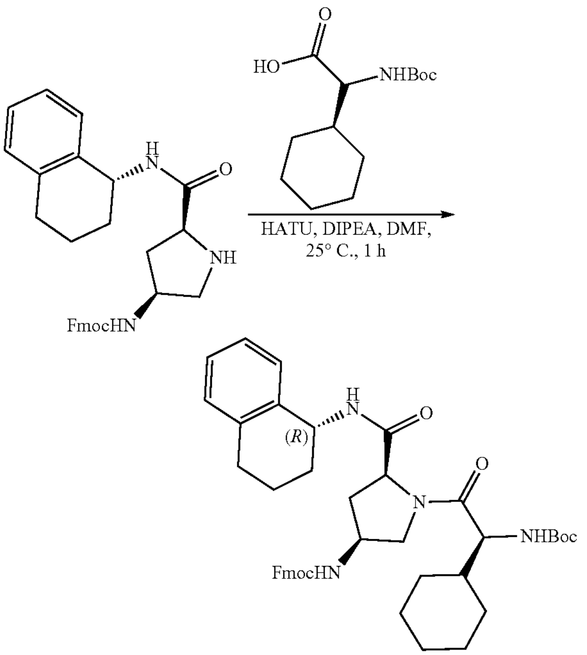

To a solution of 9H-fluoren-9-ylmethyl N-[(3S,5S)-5-[[(1R)-tetralin-1-yl]carbamoyl]pyrrolidin-3-yl]carbamate hydrochlotride (4 g, 7.72 mmol, 1 eq) and (2S)-2-(tert-butoxycarbonylamino)-2-cyclohexyl-acetic acid (1.99 g, 7.72 mmol, 1 eq) in N,N-dimethylformamide (40 mL) was added N,N-diisopropylethylamine (2.00 g, 15.44 mmol, 2.69 mL, 2 eq). The mixture was stirred at 25° C. for 10 min. Then O—(7-azabenzotriazol-1-yl)-N,N,N',N'-tetramethyluronium hexafluorophosphate (5.87 g, 15.44 mmol, 2 eq) was added into the mixture. The mixture was stirred at 25° C. for 50 min. To the mixture was added brine (100 mL), and the mixture was extracted with ethyl acetate (100 mL×3). The organic layer was dried over sodium sulfate and concentrated. The residue was purified using silica gel chromatography (petroleum ether:ethyl acetate=10:1 to 0:1). 9H-Fluoren-9-ylmethyl N-[(3S,5S)-1-[(2S)-2-(tert-butoxycarbonylamino)-2-cyclohexyl-acetyl]-5-[[(1R)-tetralin-1-yl]carbamoyl]pyrrolidin-3-yl]carbamate (3.2 g, 4.44 mmol, 57% yield) was obtained as a white solid.

Step 4

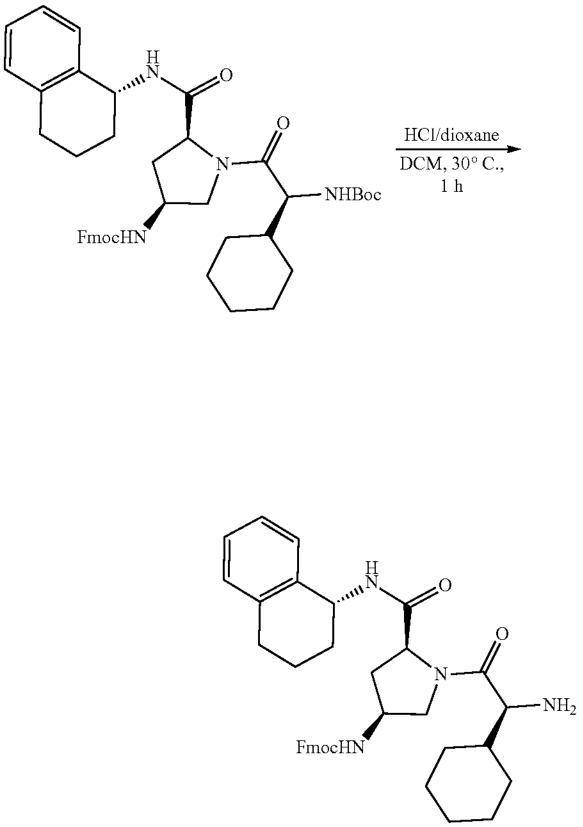

To a solution of 9H-fluoren-9-ylmethyl N-[(3S,5S)-1-[(2S)-2-(tert-butoxycarbonylamino)-2-cyclohexyl-acetyl]-5-[[(1R)-tetralin-1-yl]carbamoyl]pyrrolidin-3-yl]carbamate (3 g, 4.16 mmol, 1 eq) in dichloromethane (20 mL) was added hydrogen chloride/dioxane (4 M, 1.0 mL). The mixture was stirred at 30° C. for 1 h. The mixture was concentrated. The residue was used in the next step without further purification. 9H-Fluoren-9-ylmethyl N-[(3S,5S)-1-[(2S)-2-amino-2-cyclohexyl-acetyl]-5-[[(1R)-tetralin-1-yl]carbamoyl]pyrrolidin-3-yl]carbamate hydrochloride (2.7 g, crude) was obtained as a white solid.

Step 5

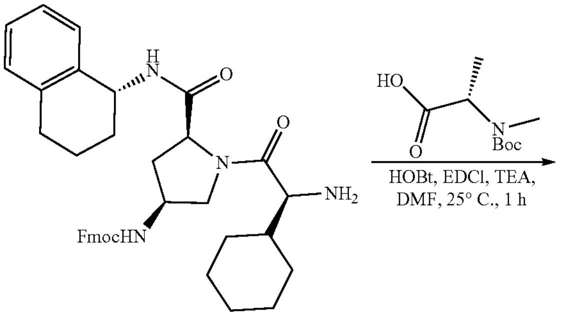

-continued

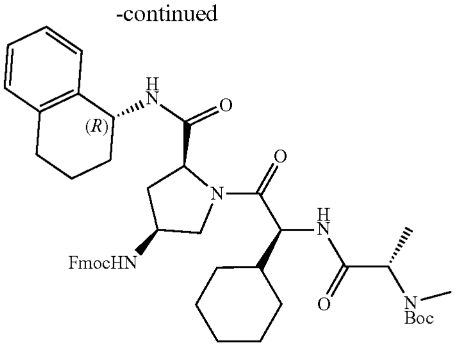

To a solution of 9H-fluoren-9-ylmethyl N-[(3S,5S)-1-[(2S)-2-amino-2-cyclohexyl-acetyl]-5-[[(1R)-tetralin-1-yl]carbamoyl]pyrrolidin-3-yl]carbamate hydrochloride (2.7 g, 4.11 mmol, 1 eq) and (2S)-2-[tert-butoxycarbonyl(methyl)amino]propanoic acid (835 mg, 4.11 mmol, 1 eq) in N,N-dimethylformamide (30 mL) was added 578rimethylamine (415 mg, 4.11 mmol, 1 eq). The mixture was stirred at 25° C. for 10 min. Then hydroxybenzotriazole (666 mg, 4.93 mmol, 1.2 eq) and 1-(3-dimethylaminopropyl)-3-ethylcarbodiimide hydrochloride (945 mg, 4.93 mmol, 1.2 eq) were added to the mixture. The mixture was stirred at 25° C. for 50 min. To the mixture was added brine (100 mL), and the mixture was extracted with ethyl acetate (150 mLx3). The organic layer was dried over sodium sulfate and concentrated. The residue was purified with silica gel chromatography (petroleum ether:ethyl acetate=10:1 to 0:1). Tert-Butyl N-[(1S)-2-[[(1S)-1-cyclohexyl-2-[(2S,4S)-4-(9H-fluoren-9-ylmethoxycarbonylamino)-2-[[(1R)-tetralin-1-yl]carbamoyl]pyrrolidin-1-yl]-2-oxo-ethyl]amino]-1-methyl-2-oxo-ethyl]-N-methyl-carbamate (3 g, 3.35 mmol, 81% yield) was obtained as a white solid.

Step 6

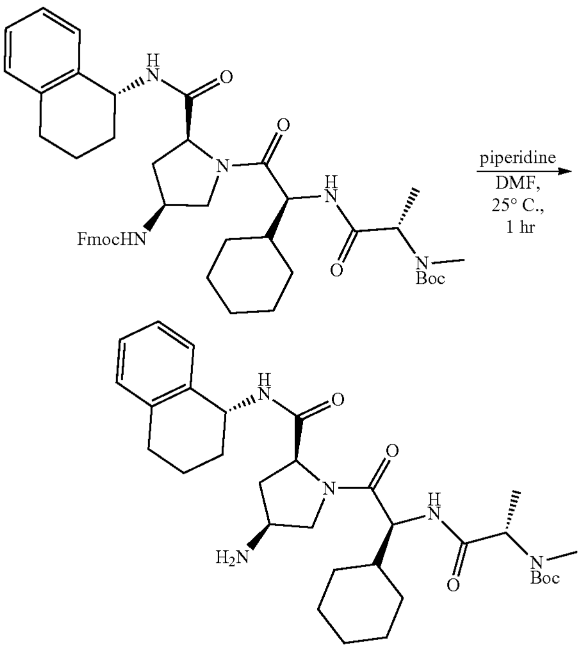

To a mixture of tert-butyl N-[(1S)-2-[[(1S)-1-cyclohexyl-2-[(2S,4S)-4-(9H-fluoren-9-ylmethoxycarbonylamino)-2-[[(1R)-tetralin-1-yl]carbamoyl]pyrrolidin-1-yl]-2-oxo-ethyl]amino]-1-methyl-2-oxo-ethyl]-N-methyl-carbamate (3.00 g, 3.72 mmol, 1 eq) in N,N-dimethylformamide (30 mL) was added piperidine (1.58 g, 18.61 mmol, 1.84 mL, 5 eq). The mixture was stirred at 25° C. for 1 hr. To the mixture was added brine (100 mL), and the mixture was extracted with ethyl acetate (150 mL×3). The organic layer was dried over sodium sulfate and concentrated. The residue was purified with silica gel chromatography (dichloromethane: methanol=100:1 to 10:1). Tert-Butyl N-[(1S)-2-[[(1S)-2-[(2S,4S)-4-amino-2-[[(1R)-tetralin-1-yl]carbamoyl]pyrrolidin-1-yl]-1-cyclohexyl-2-oxo-ethyl]amino]-1-methyl-2-oxo-ethyl]-N-methyl-carbamate (1.9 g, 3.25 mmol, 87% yield) was obtained as a yellow oil.

Synthetic procedures similar to those described in steps 1 through 6 have also been described by Casillas, L. et al. in WO 2016172134.

tert-Butyl N-[(1S)-2-[[(1S)-2-[(2S,4S)-4-amino-2-[[(1R)-tetralin-1-yl]carbamoyl]pyrrolidin-1-yl]-1-cyclohexyl-2-oxo-ethyl]amino]-1-methyl-2-oxo-ethyl]-N-methyl-carbamate was converted to the title compound according to the scheme below using procedures described for other examples above as well as those commonly known to skilled in the art.

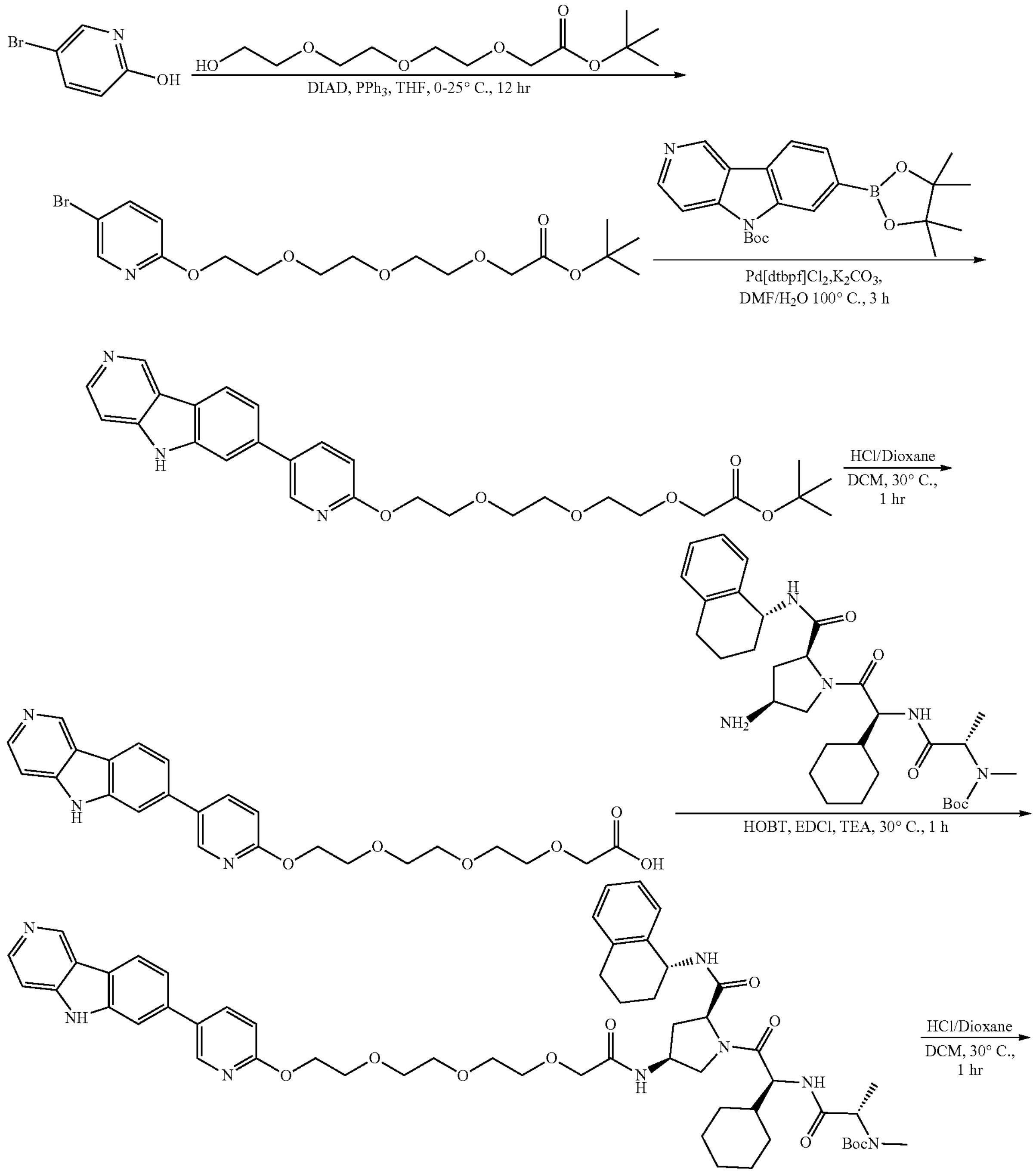

-continued

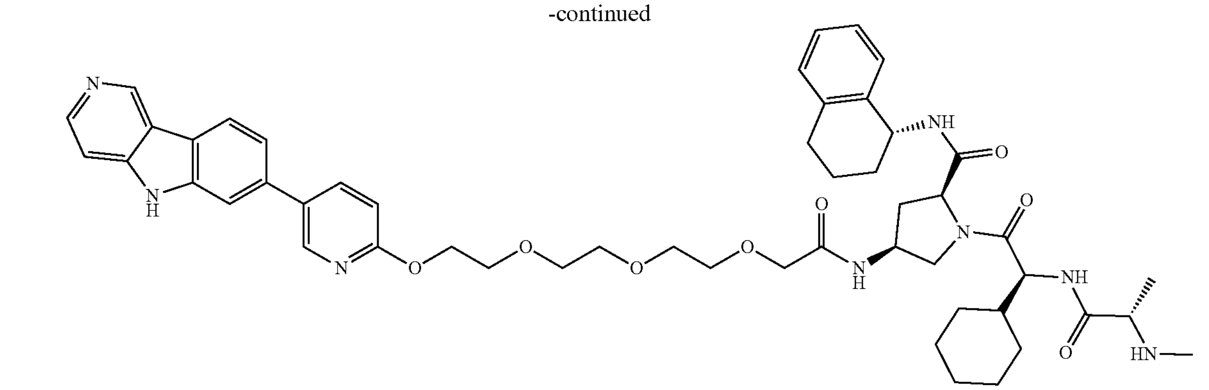

Exemplary Compound 374

Using analogous procedures the following exemplary compounds were prepared: 380, 381.

Exemplary Synthesis of Exemplary Compound 376

Step 1

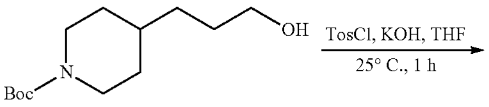

-continued

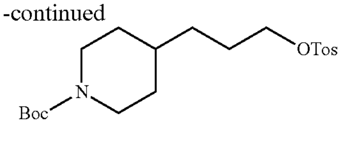

To a solution of tert-butyl 4-(3-hydroxypropyl)piperidine-1-carboxylate (1 g, 4.11 mmol, 1 eq) in tetrahydrofuran (10 mL) was added potassium hydroxide (692 mg, 12.33 mmol, 3 eq), and the mixture was stirred at 25° C. for 10 min. Then 4-methylbenzenesulfonyl chloride (1.18 g, 6.16 mmol, 1.5 eq) was added. The mixture was stirred at 25° C. for 50 min. The reaction mixture was diluted with water (30 mL) and extracted with ethyl acetate (10 mL×2). The combined organic layer was washed with brine (10 mL), dried over sodium sulfate, filtered and concentrated under reduced pressure. The residue was purified by column chromatography (petroleum ether/ethyl acetate=20/1 to 1/1) to afford tert-butyl 4-[3-(p-tolylsulfonyloxy)propyl]piperidine-1-carboxylate (1.55 g, 3.90 mmol, 94% yield) as a yellow oil.

Step 2

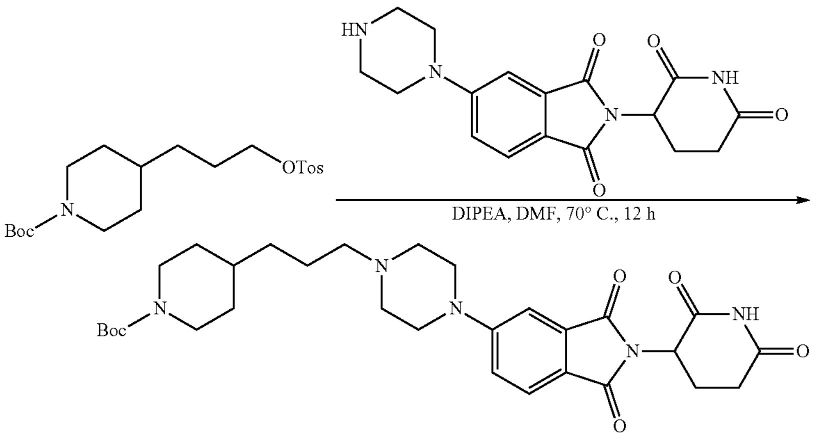

To a stirred solution of 2-(2,6-dioxo-3-piperidyl)-5-piperazin-1-yl-isoindoline-1,3-dione hydrochloride (300 mg, 0.79 mmol, 1 eq) in N,N-dimethylformamide (30 mL) was added N-ethyl-N-isopropyl-propan-2-amine (307 mg, 2.38 mmol, 0.4 mL, 3 eq) and tert-butyl 4-[3-(p-tolylsulfonyloxy)propyl]piperidine-1-carboxylate (377 mg, 0.95 mmol, 1.2 eq). The reaction was stirred at 70° C. for 12 h. The reaction mixture was poured into ethyl acetate (200 mL) and brine (100 mL). The organic phase was separated, washed with brine (100 mL×3), dried over sodium sulfate, filtered and concentrated under reduced pressure. The residue was purified by column chromatography (petroleum ether/ethyl acetate=2/1 to 1/1) to give tert-butyl 4-[3-[4-[2-(2,6-dioxo-3-piperidyl)-1,3-dioxo-isoindolin-5-yl]piperazin-1-yl]propyl]piperidine-1-carboxylate (190 mg, 0.33 mmol, 42% yield) as a yellow green solid.

Step 3

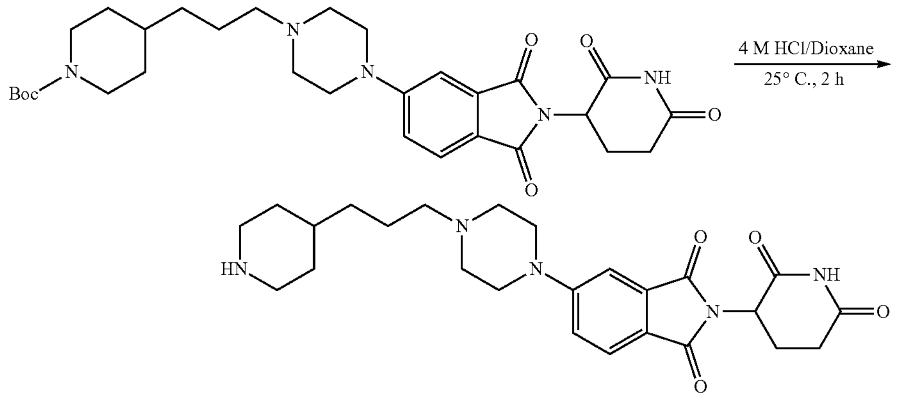

To a stirred of tert-butyl 4-[3-[4-[2-(2,6-dioxo-3-piperidyl)-1,3-dioxo-isoindolin-5-yl]piperazin-1-yl]propyl]piperidine-1-carboxylate (190 mg, 0.33 mmol, 1 eq) in hydrochloric acid/dioxane (4 M, 10 mL) at 25° C. for 4 h. The mixture was concentrated in vacuum to give 2-(2,6-dioxo-3-piperidyl)-5-[4-[3-(4-piperidyl)propyl]piperazin-1-yl]isoindoline-1,3-dione hydrochloride (170 mg, crude) as a yellow solid.

2-(2,6-Dioxo-3-piperidyl)-5-[4-[3-(4-piperidyl)propyl]piperazin-1-yl]isoindoline-1,3-dione was converted to the title compound according to the scheme below using procedures described in US 20180125821, for other examples above, as well as those commonly known to skilled in the art.

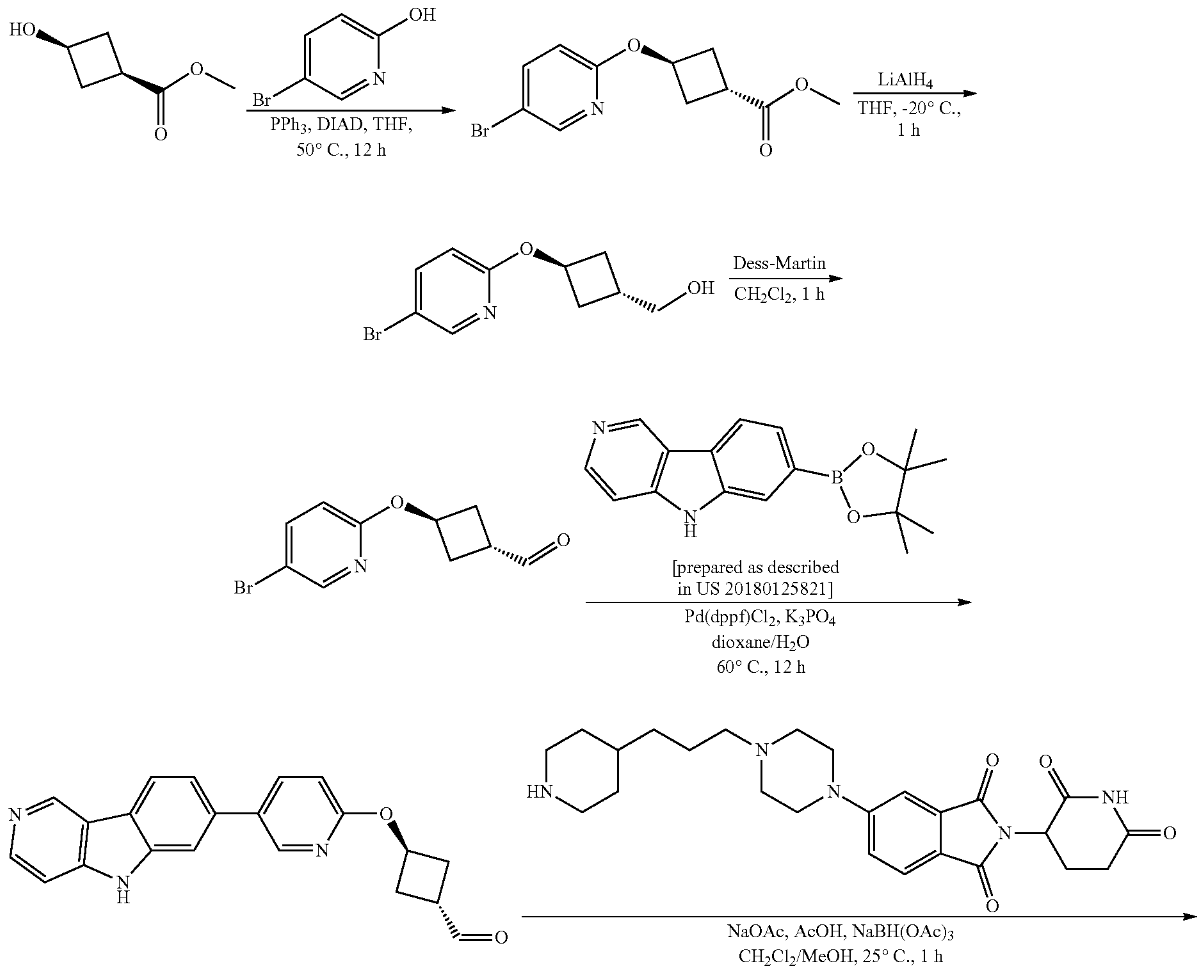

-continued

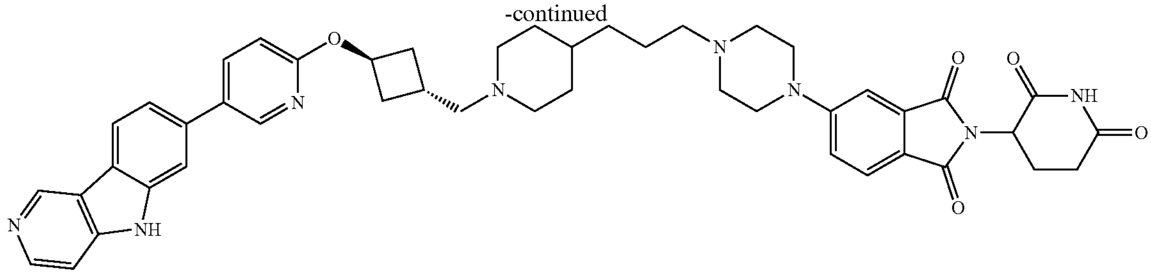

Exemplary Compound 376

Exemplary Synthesis of Exemplary Compound 377

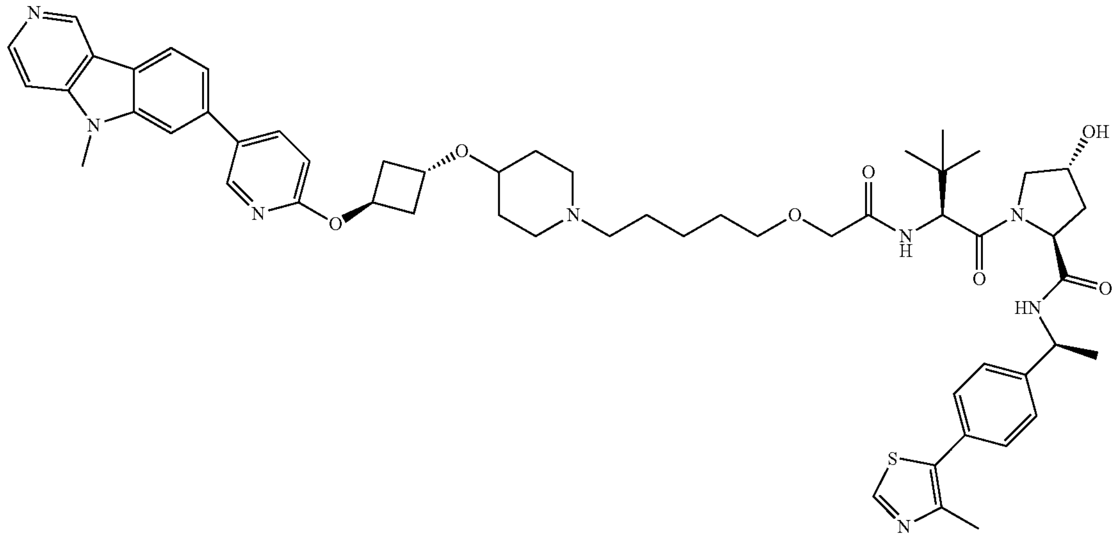 [SMILES: Cc1ncsc1-c1ccc([C@H](C)NC(=O)[C@@H]2C[C@@H](O)CN2C(=O)[C@@H](NC(=O)COCCCCCN2CCC(O[C@H]3C[C@H](Oc4ccc(-c5ccc6c7cnccc7n(C)c6c5)cn4)C3)CC2)C(C)(C)C)cc1]

Step 1

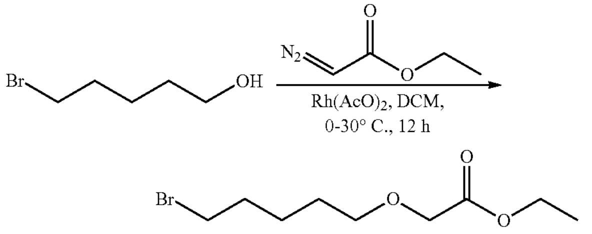

To a solution of 5-bromopentan-1-ol (2 g, 11.97 mmol, 1 eq) in dichloromethane (20 mL) was added ethyl 2-diazoacetate (4.10 g, 35.92 mmol, 3 eq) and diacetoxyrhodium (529 mg, 1.20 mmol, 0.1 eq) at 0° C. over a period of 1 h under nitrogen. The reaction mixture was stirred at 30° C. for 12 h. The mixture was diluted with water (50 mL) and extracted with ethyl acetate (50 mL×3). The organic layer was dried over sodium sulfate and concentrated. The residue was purified using silica gel chromatography (petroleum ether:ethyl acetate=100:1 to 1:1). Ethyl 2-(5-bromopentoxy)acetate (2 g, 3.95 mmol, 33% yield) was obtained as a colorless oil.

Ethyl 2-(5-bromopentoxy)acetate was converted to the title compound according to the scheme below using procedures described for other examples above as well as those commonly known to skilled in the art.

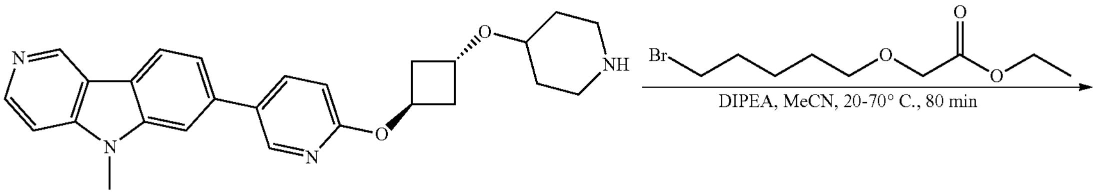

-continued

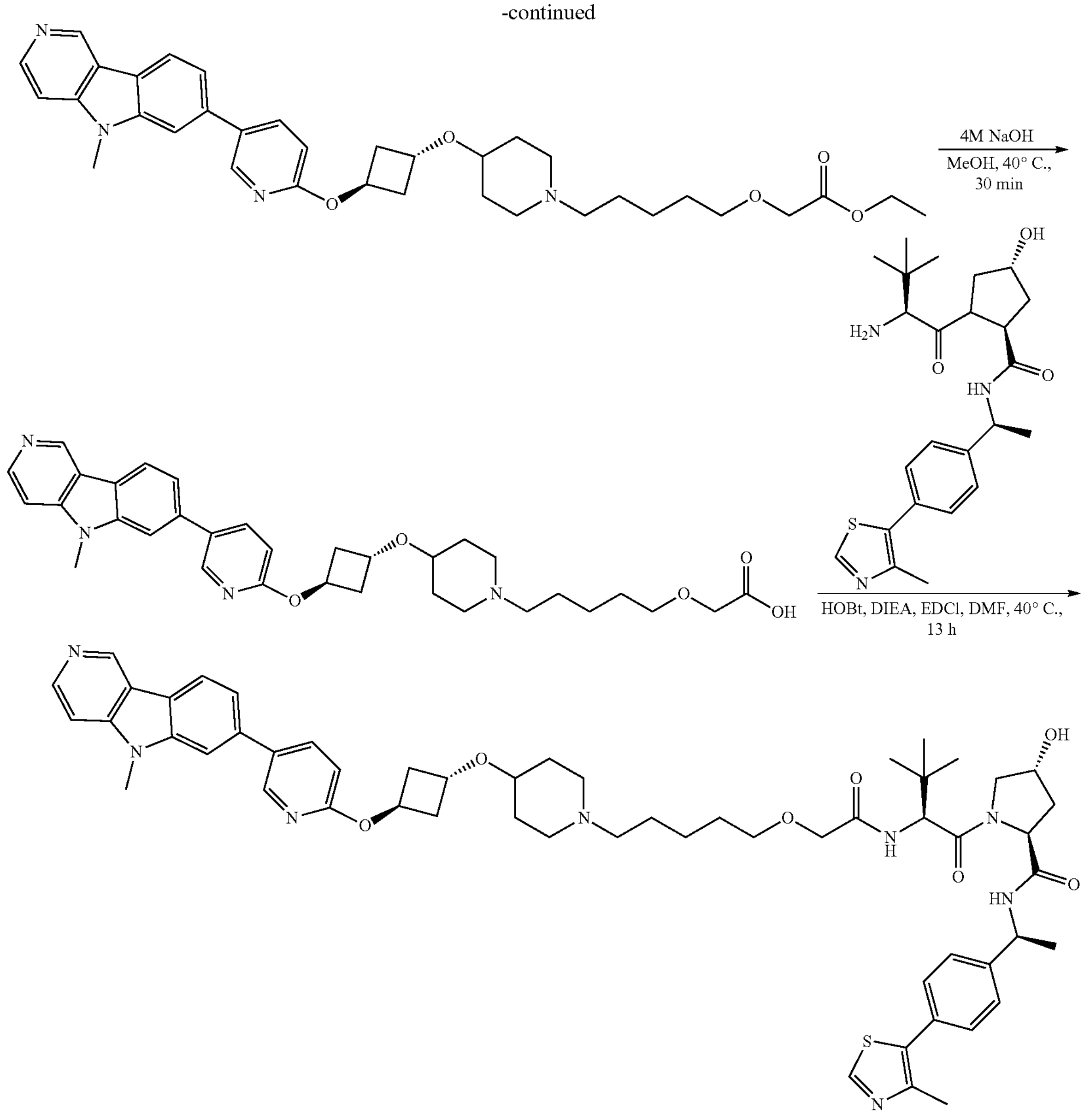

Exemplary Compound 377

Exemplary Synthesis of Exemplary Compounds 378 and 379

Step 1

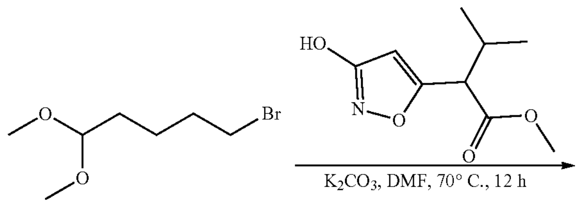

-continued

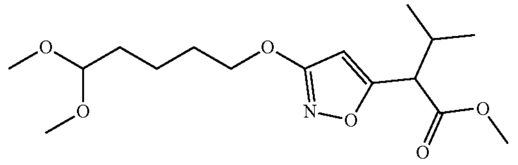

To a solution of methyl 2-(3-hydroxyisoxazol-5-yl)-3-methyl-butanoate (500 mg, 2.51 mmol, 1 eq) and 5-bromo-1,1-dimethoxy-pentane (1.06 g, 5.02 mmol, 2 eq) in N,N-dimethylformamide (5 mL) was added potassium carbonate (693 mg, 5.02 mmol, 2 eq). The mixture was stirred at 70° C. for 12 hours. The solution was quenched with water (50 ml) and extracted with ethyl acetate (50 mL×3). The organic layer was washed with brine (50 mL×3), dried over sodium sulfate, filtered and concentrated under reduced pressure.

The residue was purified by silica gel column chromatography (petroleum ether/ethyl acetate=100/1 to 40/1) to afford methyl 2-[3-(5,5-dimethoxypentoxy)isoxazol-5-yl]-3-methyl-butanoate (403 mg, 1.16 mmol, 46% yield) as a colorless oil.

Step 2

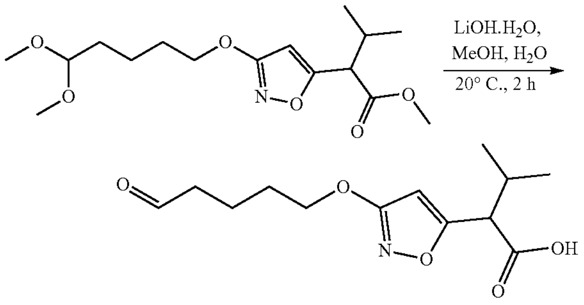

To a solution of methyl 2-[3-(5,5-dimethoxypentoxy)isoxazol-5-yl]-3-methyl-butanoate (403 mg, 1.22 mmol, 1 eq) in methanol (10 mL) and water (5 mL) was added lithium hydroxide monohydrate (205 mg, 4.89 mmol, 4 eq). The mixture was stirred at 20° C. for 2 hours, diluted with 37% hydrochloric acid to pH ~6-7 and concentrated under reduced pressure. The residue was purified by prep-high performance liquid chromatography (Column: Phenomenex Synergi C18 150*25*10 um; mobile phase: [water (0.225% formic acid)-acetonitrile]; B %: 45%-75%, 9 min) to give 3-methyl-2-[3-(5-oxopentoxy)isoxazol-5-yl]butanoic acid (222 mg, 0.82 mmol, 67% yield) as a white solid.

3-Methyl-2-[3-(5-oxopentoxy)isoxazol-5-yl]butanoic acid was converted to (2S,4R)-4-hydroxy-1-(3-methyl-2-(3-((5-(4-((1r,3r)-3-((5-(5-methyl-5H-pyrido[4,3-b]indol-7-yl)pyridin-2-yl)oxy)cyclobutoxy)piperidin-1-yl)pentyl)oxy)isoxazol-5-yl)butanoyl)-N-((S)-1-(4-(4-methylthiazol-5-yl)phenyl)ethyl)pyrrolidine-2-carboxamide as described for exemplary compound 372 which was then separated into individual diastereomers, exemplary compounds 378 and exemplary compound 379 as shown below and described for exemplary compound 372.

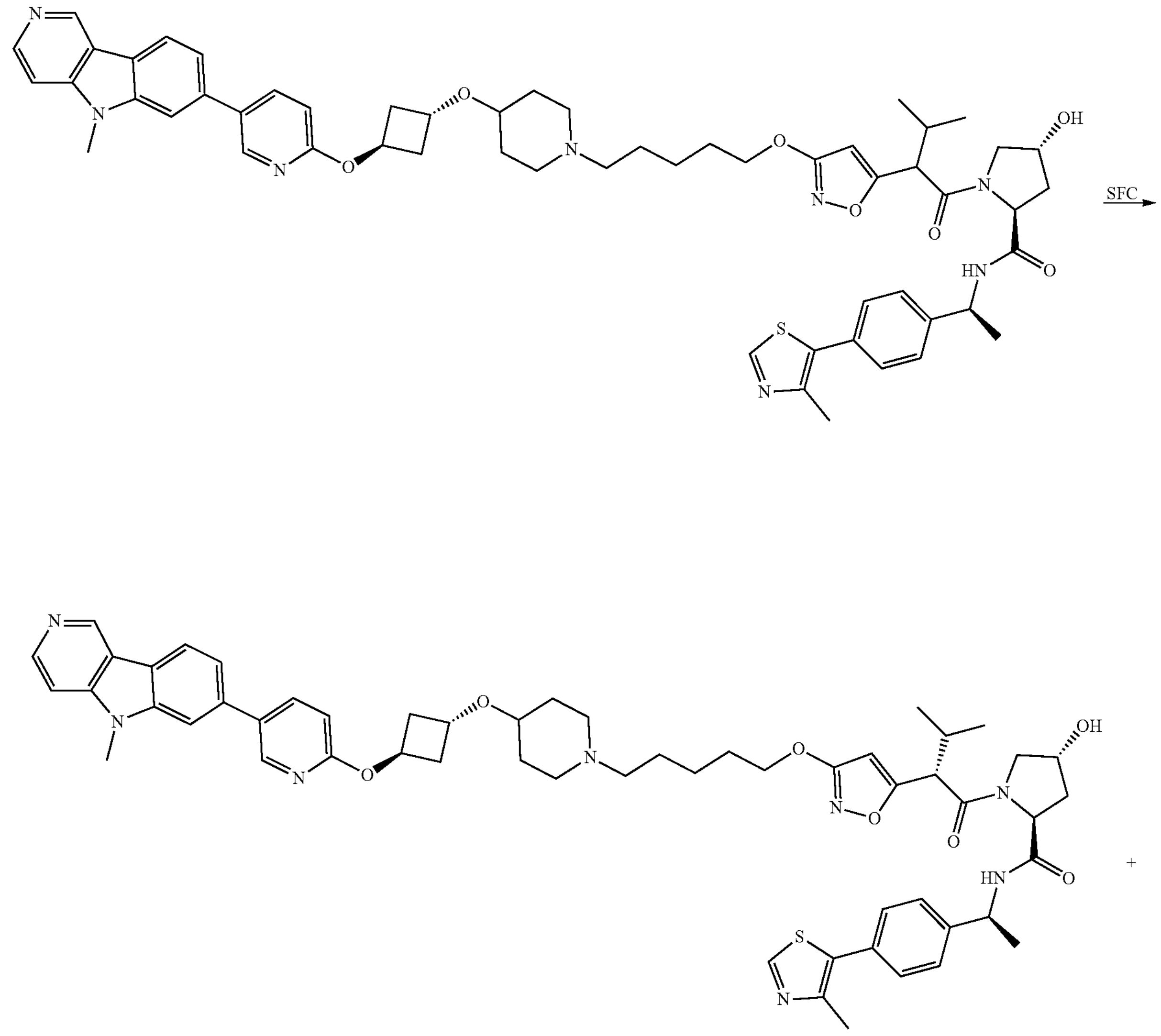

Exemplary Compound 378

-continued

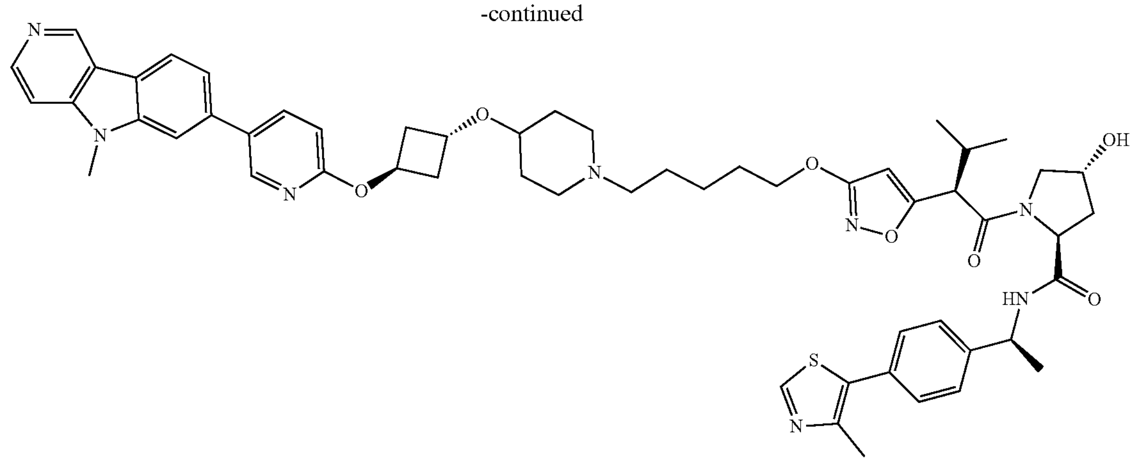

Exemplary Compound 379

Exemplary Synthesis of Exemplary Compound 382

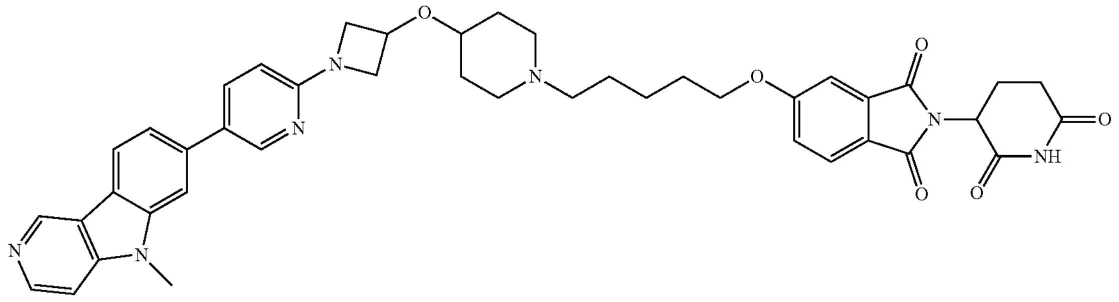 [SMILES: Cn1c2ccncc2c2ccc(-c3ccc(N4CC(OC5CCN(CCCCCOc6ccc7c(c6)C(=O)N(C6CCC(=O)NC6=O)C7=O)CC5)C4)nc3)cc21]

Step 1

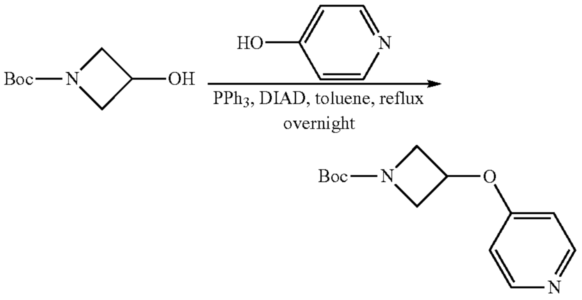

Into a 500-mL round-bottom flask purged and maintained with an inert atmosphere of nitrogen was placed a solution of tert-butyl-3-hydroxyazetidine-1-carboxylate (15 g, 86.60 mmol, 1 equiv), pyridin-4-ol (8.2 g, 86.22 mmol, 1.00 equiv), and $PPh_3$ (27.3 g, 103.9 mmol, 1.2 equiv) in toluene (150 mL). This was followed by the addition of DIAD (21.0 g, 103.9 mmol, 1.2 equiv) at 0° C. The resulting solution was stirred overnight at 110° C. The reaction mixture was concentrated under vacuum. The residue was diluted with water (40 mL) and extracted with ethyl acetate (100 mL×4). The combined organic layer was washed with brine (100 mL×3), dried over anhydrous sodium sulfate and concentrated. The residue was applied to a silica gel column eluting with ethyl acetate/petroleum ether (3:7). This resulted in 22 g (crude) of tert-butyl-3-(pyridin-4-yloxy)azetidine-1-carboxylate as a yellow solid.

Step 2

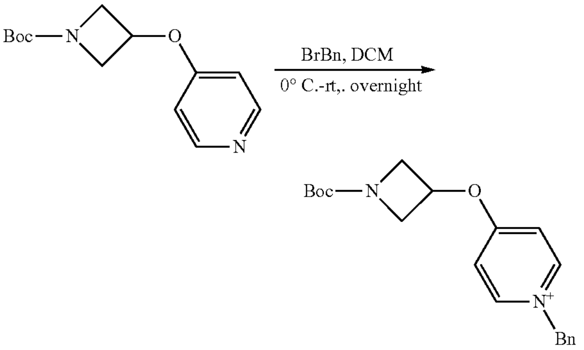

Into a 500-mL round-bottom flask, was placed tert-butyl 3-(pyridin-4-yloxy)azetidine-1-carboxylate (21.8 g, 87.10 mmol, 1 equiv) in dichloromethane (100 mL), to which was added benzyl bromide (20.5 g, 130.64 mmol, 1.5 equiv) slowly at 0° C. The resulting solution was stirred overnight at room temperature. The reaction mixture was concentrated under vacuum. The residue was diluted with water (40 mL) and extracted with 1:1 mixture of ethyl acetate/petroleum ether (100 mL×4). The combined organic layer was washed with brine (100 mL×3), dried over anhydrous sodium sulfate and concentrated. This resulted in 35 g (crude) of 1-benzyl-4-([1-[(tert-butoxy)carbonyl]azetidin-3-yl]oxy)pyridin-1-ium as a white oil.

Step 3

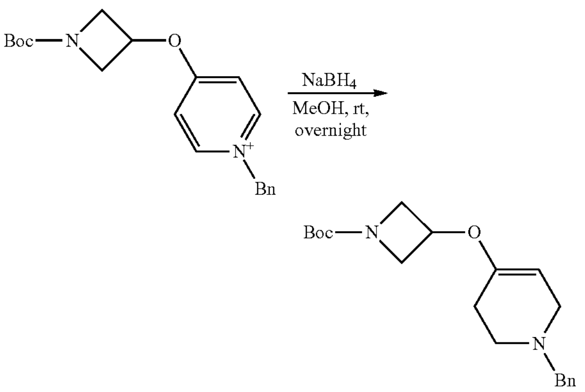

Into a 500-mL round-bottom flask was placed 1-benzyl-4-([1-[(tert-butoxy)carbonyl]azetidin-3-yl]oxy)pyridin-1-ium (35 g, 102.5 mmol, 1 equiv) in MeOH (100 mL), to which was added $NaBH_4$ (7.8 g, 206.2 mmol, 2 equiv) slowly at 0° C. The resulting solution was stirred overnight at room temperature. The reaction was then quenched by the addition of water/ice (100 mL), and the mixture was extracted with ethyl acetate (200 mL×2). The combined organic phase was washed with brine (100 mL), dried over anhydrous sodium sulfate and concentrated. The residue was applied onto a silica gel column eluting with ethyl acetate/petroleum ether (1:1). This resulted in 16 g (45%) of tert-butyl-3-[(1-benzyl-1,2,3,6-tetrahydropyridin-4-yl)oxy]azetidine-1-carboxylate as a yellow oil.

Step 4

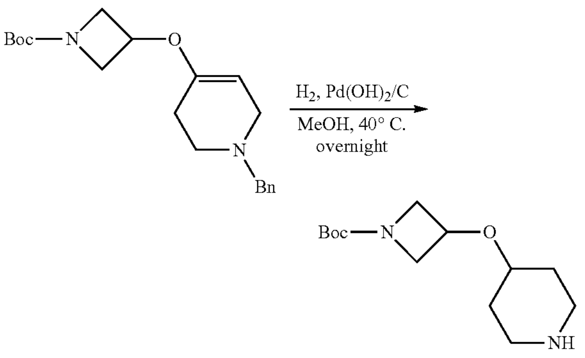

Into a 500-mL round-bottom flask, was placed a solution of tert-butyl 3-[(1-benzyl-1,2,3,6-tetrahydropyridin-4-yl)oxy]azetidine-1-carboxylate (16 g, 46.5 mmol, 1 equiv) and AcOH (0.8 g, 13.3 mmol, 0.3 equiv) in MeOH (100 mL), to which was added $Pd(OH)_2/C$ (12 g) under nitrogen atmosphere. The reaction flask was vacuumed and flushed with $H_2$, the sequence repeated 5 times. The resulting mixture was hydrogenated overnight at 40° C. The solids were filtered, and the filtrate was concentrated under vacuum. This resulted in 10 g (84%) of tert-butyl 3-(piperidin-4-yloxy)azetidine-1-carboxylate as a yellow oil.

Step 5

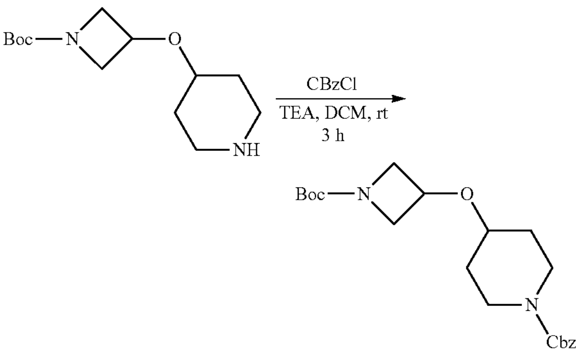

Into a 500-mL round-bottom flask purged and maintained with an inert atmosphere of nitrogen, was placed a solution of tert-butyl 3-(piperidin-4-yloxy)azetidine-1-carboxylate (5 g, 19.50 mmol, 1 equiv) and TEA (6 mL) in dichloromethane (100 mL), to which was added CbzCl (4.0 g, 23.41 mmol, 1.2 equiv) slowly. The resulting solution was stirred for 3 h at room temperature. The reaction was then quenched by the addition of water (100 mL), and the mixture was extracted with dichloromethane (200 mL×3). The combined organic phase was washed with brine (100 mL), dried over anhydrous sodium sulfate and concentrated. The residue was applied onto a silica gel column eluting with ethyl acetate/petroleum ether (1:1). This resulted in 2.3 g (30%) of benzyl-4-([1-[(tert-butoxy)carbonyl]azetidin-3-yl]oxy)piperidine-1-carboxylate as a yellow oil.

Step 6

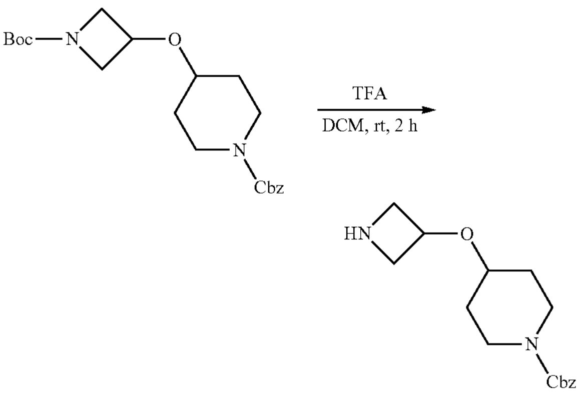

Into a 100-mL round-bottom flask, was placed benzyl-4-([1-[(tert-butoxy)carbonyl]azetidin-3-yl]oxy)piperidine-1-carboxylate (500 mg, 1.28 mmol, 1 equiv) in dichloromethane (40 mL), to which was added TFA (10 mL). The resulting solution was stirred for 2 h at room temperature.

The reaction mixture was concentrated under vacuum and diluted with water (10 mL). The pH of the mixture was adjusted to 7 with TEA, and the mixture was then concentrated under vacuum. The residue was applied onto a silica gel column eluting with ethyl acetate/petroleum ether (100:0). This resulted in 400 mg (crude) of benzyl 4-(azetidin-3-yloxy)piperidine-1-carboxylate as a yellow oil.

Step 7

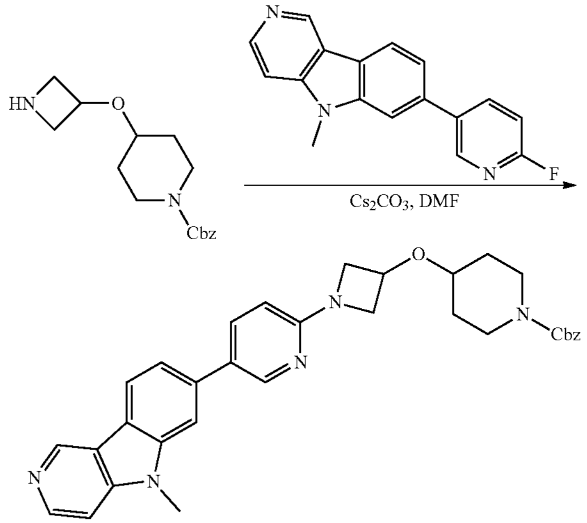

Into a 25-mL vial purged and maintained with an inert atmosphere of nitrogen, was placed benzyl 4-(azetidin-3-yloxy)piperidine-1-carboxylate (628 mg, 2.16 mmol, 1 equiv) in DMF (5 mL), to which was added 2-fluoro-5-[5-methyl-5H-pyrido[4,3-b]indol-7-yl]pyridine (300 mg, 1.1 mmol, 0.50 equiv), and $Cs_2CO_3$ (704 mg, 5.5 mmol, 2.5 equiv). The final reaction mixture was subjected to microwave radiation for 3 hr at 140° C. The reaction mixture was cooled to room temperature. The resulting solution was diluted with 15 mL of $H_2O$. The resulting solution was extracted with (2×20 mL) of ethyl acetate, dried over anhydrous sodium sulfate and concentrated. The residue was applied to a silica gel column eluting with dichloromethane/methanol (15:1). This resulted in 160 mg (14%) of benzyl 4-[[1-(5-[5-methyl-5H-pyrido[4,3-b]indol-7-yl]pyridin-2-yl)azetidin-3-yl]oxy]piperidine-1-carboxylate as a yellow solid.

Step 8

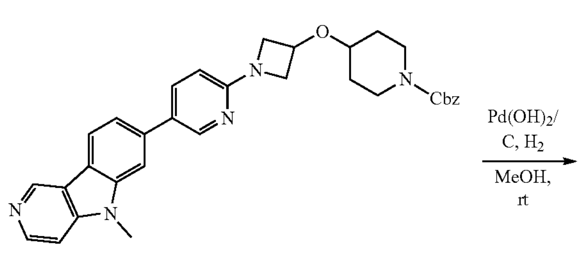

-continued

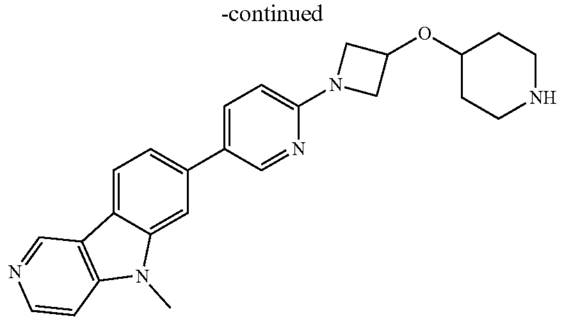

Into a 50-mL round-bottom flask, was placed benzyl 4-[[1-(5-[5-methyl-5H-pyrido[4,3-b]indol-7-yl]pyridin-2-yl)azetidin-3-yl]oxy]piperidine-1-carboxylate (180 mg, 0.33 mmol, 1 equiv) in MeOH (5 mL), and $Pd(OH)_2/C$ (80 mg) under nitrogen atmosphere. The flask was then vacuumed and flushed with hydrogen. The reaction mixture was hydrogenated at room temperature for 2 hours under hydrogen atmosphere using a hydrogen balloon. Then the reaction mixture was filtered through a celite pad, and the filtrate was concentrated under reduced pressure. The residue was applied to a silica gel column eluting with dichloromethane/methanol (10:1). This resulted in 90 mg (66%) of 5-[5-methyl-5H-pyrido[4,3-b]indol-7-yl]-2-[3-(piperidin-4-yloxy)azetidin-1-yl]pyridine as a white solid.

Step 9

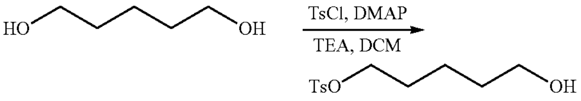

Into a 100-mL 3-neck round-bottom flask purged and maintained with an inert atmosphere of nitrogen, was placed pentane-1,5-diol (1.00 g, 9.60 mmol, 1 equiv) in DCM (10 mL), to which was added $Ag_2O$ (3.30 g, 14.2 mmol, 1.5 equiv), and KI (320 mg, 1.93 mmol, 0.20 equiv). This was followed by the addition of a solution of TsCl (1.82 g, 9.55 mmol, 1.0 equiv) in DCM (5 mL) dropwise with stirring at 0° C. over 3 min. The resulting solution was stirred for 2 hr at 0° C. The resulting mixture was concentrated. The residue was applied to a silica gel column eluting with ethyl acetate/hexane (1:5). This resulted in 1 g (40%) of 5-[(4-methylbenzenesulfonyl)oxy]pentan-1-ol as a colorless oil.

Step 10

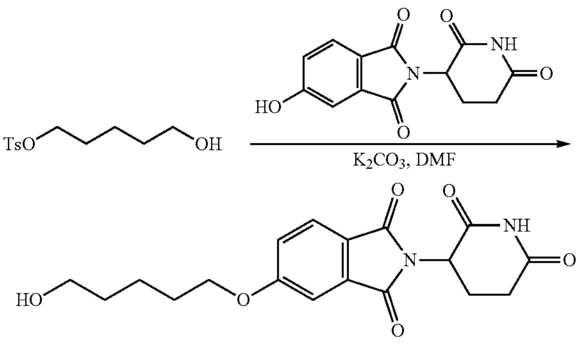

Into a 50-mL round-bottom flask purged and maintained with an inert atmosphere of nitrogen, was placed 5-[(4-methylbenzenesulfonyl)oxy]pentan-1-ol (1 g, 3.87 mmol, 1.0 equiv), 2-(2,6-dioxopiperidin-3-yl)-5-hydroxy-2,3-dihydro-1H-isoindole-1,3-dione (1.06 g, 3.87 mmol, 1.0 equiv) and $K_2CO_3$ (1.07 g, 7.74 mmol, 2.0 equiv) in DMF (10 mL). The resulting solution was stirred for 1 hr at 60° C. The reaction mixture was cooled to room temperature. The reaction was then quenched by the addition of $H_2O$ (20 mL). The resulting solution was extracted with (2×30 mL) of ethyl acetate. The resulting mixture was washed with brine (30 mL×2). The organic phase was concentrated under vacuum. This resulted in 700 mg (crude) of 2-(2,6-dioxopiperidin-3-yl)-5-[(5-hydroxypentyl)oxy]-2,3-dihydro-1H-isoindole-1,3-dione as a yellow solid.

Step 11

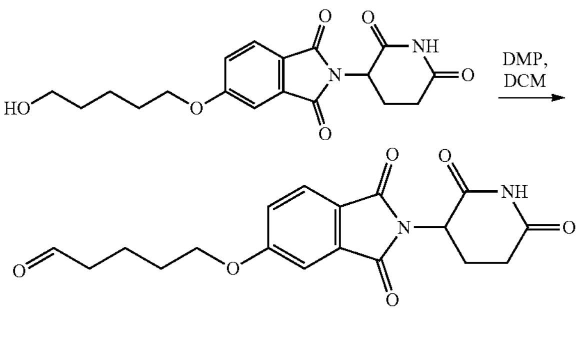

Into a 100-mL round-bottom flask purged and maintained with an inert atmosphere of nitrogen, was placed 2-(2,6-dioxopiperidin-3-yl)-5-[(5-hydroxypentyl)oxy]-2,3-dihydro-1H-isoindole-1,3-dione (700 mg, 1.94 mmol, 1.0 equiv) in DCM (10 mL), to which was added DMP (1.24 g, 2.92 mmol, 1.5 equiv). The resulting solution was stirred for 1 hr at room temperature. The resulting solution was diluted with 10 mL of $H_2O$. The resulting solution was extracted with (2×20 mL) of dichloromethane and concentrated. The residue was applied to a silica gel column eluting with dichloromethane/methanol (1:15). This resulted in 300 mg (43%) of 5-[[2-(2,6-dioxopiperidin-3-yl)-1,3-dioxo-2,3-dihydro-1H-isoindol-5-yl]oxy]pentanal as a white solid.

Step 12

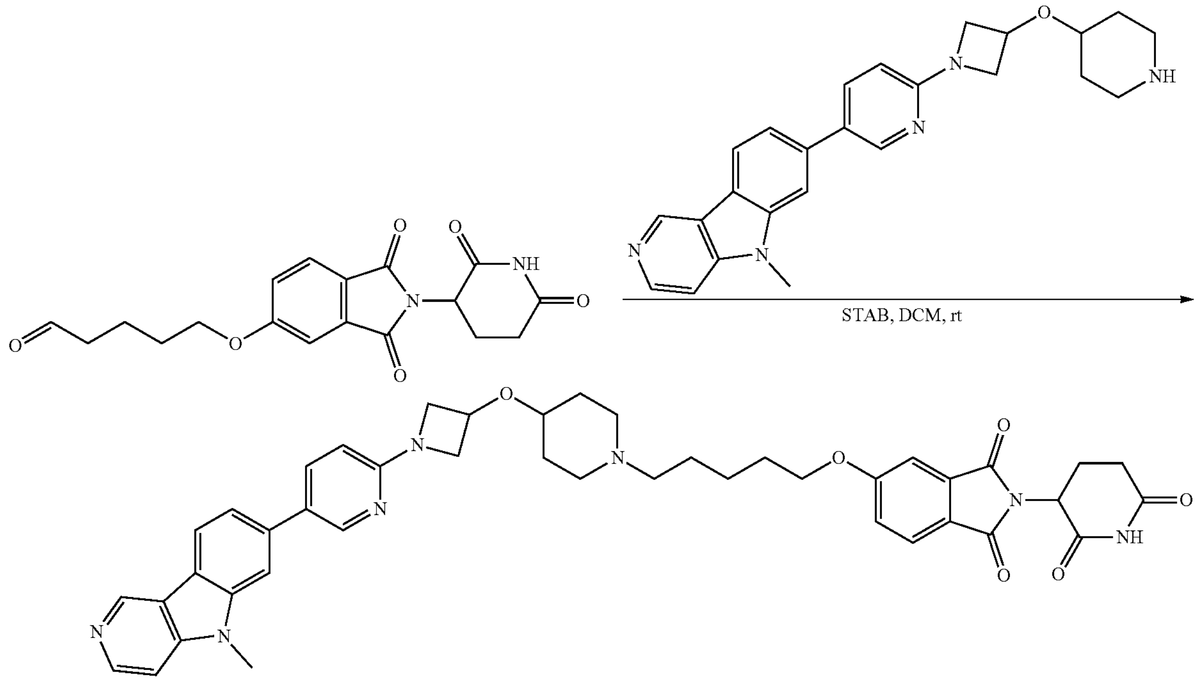

Exemplary Compound 382

Into a 50-mL round-bottom flask purged and maintained with an inert atmosphere of nitrogen, was placed 5-[[2-(2,6-dioxopiperidin-3-yl)-1,3-dioxo-2,3-dihydro-1H-isoindol-5-yl]oxy]pentanal (34.7 mg, 0.10 mmol, 1.0 equiv) and 5-[5-methyl-5H-pyrido[4,3-b]indol-7-yl]-2-[3-(piperidin-4-yloxy)azetidin-1-yl]pyridine (40.0 mg, 0.10 mmol, 1.0 equiv) in DCM (1 mL), to which was added STAB (41.1 mg, 0.19 mmol, 2.0 equiv). The resulting solution was stirred for 2 hr at room temperature. The crude product was purified by prep-HPLC with the following conditions: XBridge Prep OBD C18 Column 30*50 mm 5 um; Mobile Phase A: water (0.1% FA), Mobile Phase B: acetonitrile; Flow rate: 60 mL/min; Gradient: 10% B to 16% B in 9 min; 254 nm; This resulted in 46.2 mg (63%) of 2-(2,6-dioxopiperidin-3-yl)-5-[[5-(4-[[1-(5-[5-methyl-5H-pyrido[4,3-b]indol-7-yl]pyridin-2-yl)azetidin-3-yl]oxy]piperidin-1-yl)pentyl]oxy]-2,3-dihydro-1H-isoindole-1,3-dione as a white solid.

Exemplary Synthesis of Exemplary Compound 386

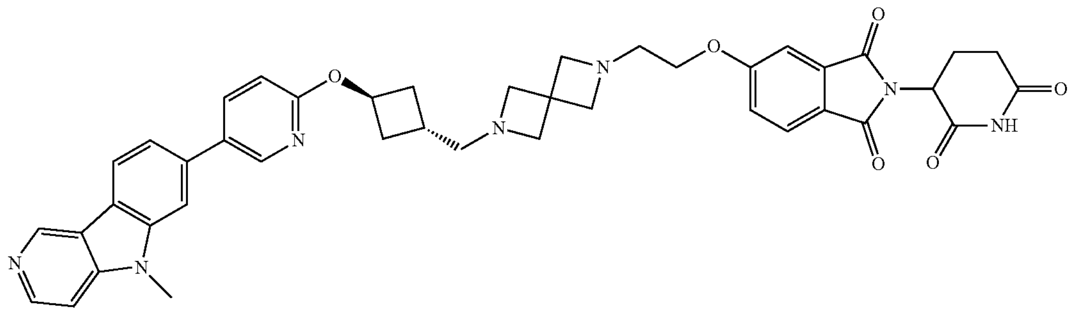 [SMILES: Cn1c2ccncc2c2ccc(-c3ccc(O[C@H]4C[C@H](CN5CC6(CN(CCOc7ccc8c(c7)C(=O)N(C7CCC(=O)NC7=O)C8=O)C6)C5)C4)nc3)cc21]

Step 1

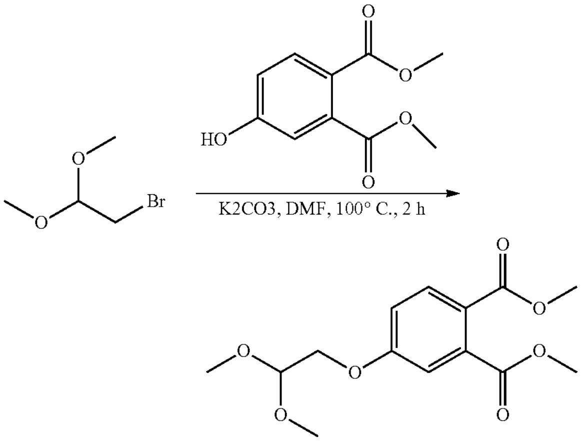

To a solution of 2-bromo-1,1-dimethoxy-ethane (3.22 g, 19.04 mmol, 2 eq) in dimethyl formamide (20 mL) was added potassium carbonate (3.95 g, 28.56 mmol, 3 eq) and dimethyl 4-hydroxybenzene-1,2-dicarboxylate (2 g, 9.52 mmol, 1 eq). The mixture was stirred at 100° C. for 3 hours. The reaction mixture was quenched by water (200 mL) at 25° C., and then extracted with ethyl acetate (50 mL×3). The combined organic layers were washed with brine (50 mL×3), dried over anhydrous sodium sulfate, filtered and concentrated under reduced pressure. The residue was purified by column chromatography (petroleum ether:ethyl acetate=15:1 to 8:1). Dimethyl 4-(2,2-dimethoxyethoxy) benzene-1,2-dicarboxylate (2.64 g, 8.85 mmol, 92% yield) was obtained as a yellow oil.

Step 2

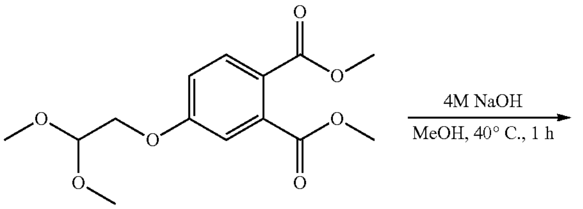

-continued

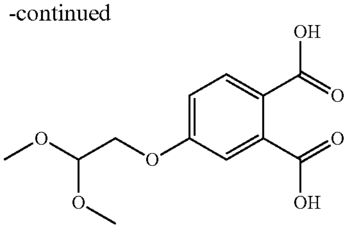

To a solution of dimethyl 4-(2,2-dimethoxyethoxy)benzene-1,2-dicarboxylate (2.64 g, 8.86 mmol, 1 eq) in methyl alcohol (20 mL) was added sodium hydroxide (4 M, 4.43 mL, 2 eq). The mixture was stirred at 40° C. for 12 hours. The reaction mixture was quenched with hydrochloric acid (20 mL) at 20° C., and then diluted with water (100 mL) and extracted with ethyl acetate (50 mL×3). The combined organic layers were washed with brine (50 mL×3), dried over anhydrous sodium sulfate, filtered and concentrated under reduced pressure. The crude product was used in the next step without further purification. 4-(2,2-Dimethoxyethoxy)phthalic acid (2.2 g, 8.14 mmol, 91% yield) was obtained as a yellow oil.

Step 3

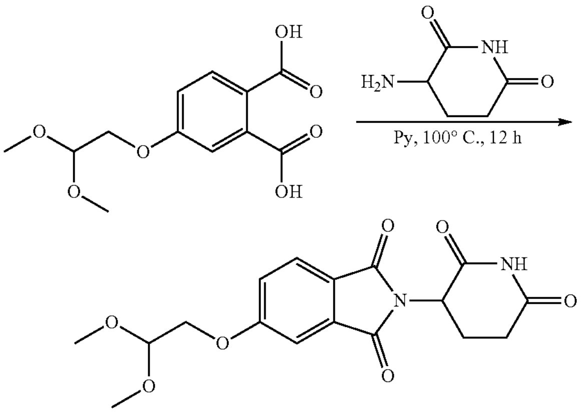

To a solution of 4-(2,2-dimethoxyethoxy)phthalic acid (2.2 g, 8.14 mmol, 1 eq) in pyridine (10 mL) was added 3-aminopiperidine-2,6-dione hydrochloride (2.01 g, 12.2 mmol, 1.5 eq). The mixture was stirred at 100° C. for 12 hours. The reaction mixture was concentrated under reduced pressure to remove pyridine (10 mL). The residue was diluted with water (200 mL) and extracted with ethyl acetate (50 mL×3). The combined organic layers were washed with brine (50 mL×3), dried over anhydrous sodium sulfate, filtered and concentrated under reduced pressure. The residue was purified by column chromatography (petroleum ether/ethyl acetate=10:1 to 3:1). 5-(2,2-Dimethoxyethoxy)-2-(2,6-dioxo-3-piperidyl)isoindoline-1,3-dione (1.6 g, 4.20 mmol, 51% yield) was obtained as a yellow oil.

Step 4

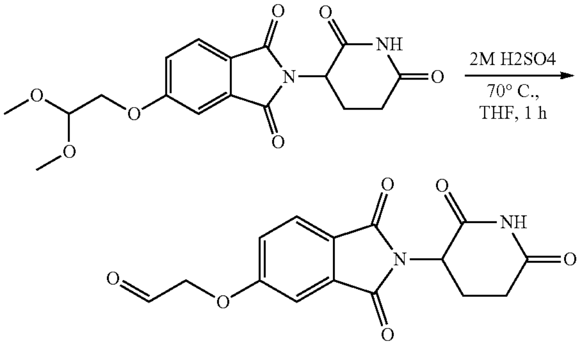

To a solution of 5-(2,2-dimethoxyethoxy)-2-(2,6-dioxo-3-piperidyl)isoindoline-1,3-dione (192 mg, 0.53 mmol, 1 eq) in tetrahydrofuran (10 mL) was added sulfuric acid (2 M, 10.6 mL, 40 eq), and the mixture was stirred at 70° C. for 1 hour. The reaction mixture was quenched by the addition of aqueous sodium bicarbonate (5 mL) at 20° C., and then diluted with water (50 mL) and extracted with ethyl acetate (20 mL×3). The combined organic layers were washed with brine (20 mL×3), dried over anhydrous sodium sulfate, filtered and concentrated under reduced pressure. The crude product was used in the next step without further purification. 2-[2-(2,6-Dioxo-3-piperidyl)-1,3-dioxo-isoindolin-5-yl] oxyacetaldehyde (160 mg, crude) was obtained as a white solid.

Step 5

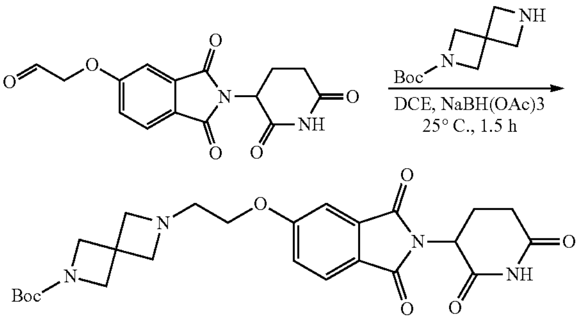

To a mixture of tert-butyl 2,6-diazaspiro[3.3]heptane-2-carboxylate (137 mg, 0.69 mmol, 1.1 eq) in dichloroethane (10 mL) was added triethylamine (127 mg, 1.26 mmol, 2 eq). The mixture was stirred at 25° C. for 15 min. Then 2-[2-(2,6-dioxo-3-piperidyl)-1,3-dioxo-isoindolin-5-yl]oxyacetaldehyde (200 mg, 0.63 mmol, 1 eq) was added to the mixture, and the mixture was stirred at 25° C. for 15 min. Sodium triacetoxyborohydride (268 mg, 1.26 mmol, 2 eq) was added to the mixture, and the mixture was stirred at 25° C. for 1 hr. The mixture was quenched by the addition of water (100 mL), extracted with dichloromethane (30 mL), and the combined organic phase was washed with brine (30 mL), dried over anhydrous sodium sulfate, filtered and concentrated under reduced pressure. The residue was purified by prep-TLC (dichloromethane:methanol=10:1). Compound tert-butyl 6-[2-[2-(2,6-dioxo-3-piperidyl)-1,3-dioxo-isoindolin-5-yl]oxyethyl]-2,6-diazaspiro[3.3]heptane-2-carboxylate (110 mg, 0.22 mmol, 34% yield) was obtained as a white solid.

Step 6

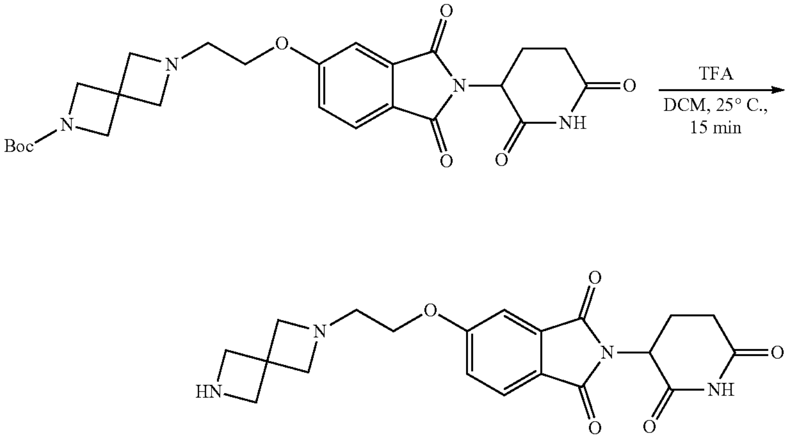

To a mixture of tert-butyl 6-[2-[2-(2,6-dioxo-3-piperidyl)-1,3-dioxo-isoindolin-5-yl]oxyethyl]-2,6-diazaspiro[3.3]heptane-2-carboxylate (110 mg, 0.22 mmol, 1 eq) in dichloromethane (10 mL) was added trifluoroacetic acid (125 mg, 1.10 mmol, 5 eq). The mixture was stirred at 25° C. for 15 min. The mixture was concentrated under reduced pressure. The residue was used in the next step without further purification. Compound 5-[2-(2,6-diazaspiro[3.3]heptan-2-yl)ethoxy]-2-(2,6-dioxo-3-piperidyl)isoindoline-1,3-dione trifluoroacetate (100 mg, crude) was obtained as a brown oil.

Step 7

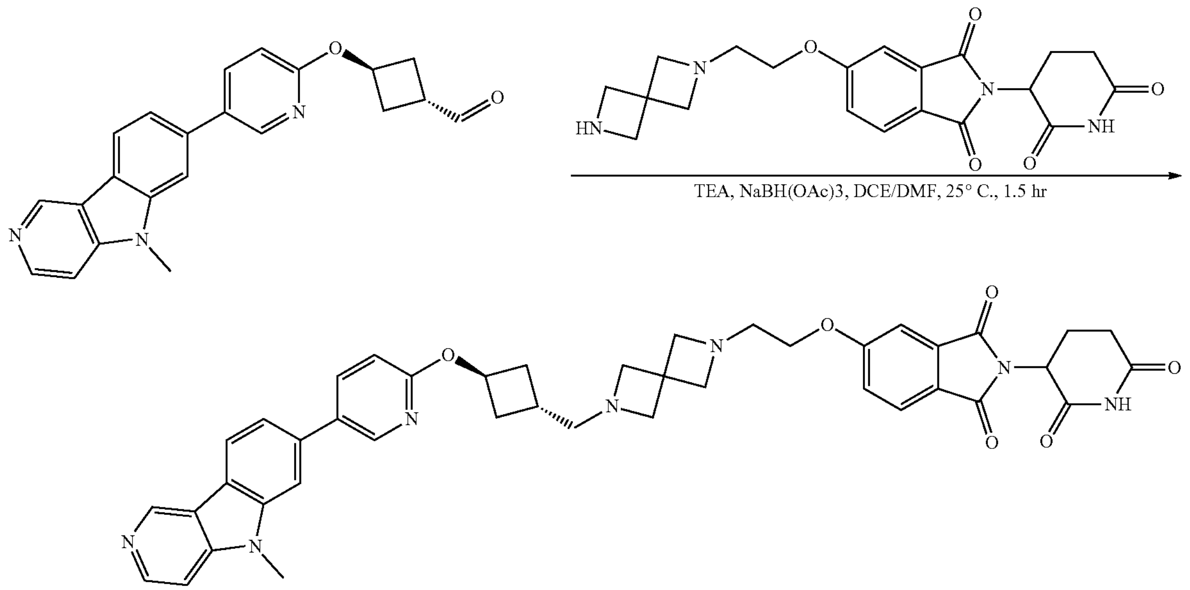

Exemplary Compound 386

To a mixture of 5-[2-(2,6-diazaspiro[3.3]heptan-2-yl) ethoxy]-2-(2,6-dioxo-3-piperidyl) isoindoline-1,3-dione trifluoroacetate (100 mg, 0.19 mmol, 1 eq) in dichloroethane (10 mL) and dimethylformamide (1 mL) was added triethylamine (118 mg, 1.17 mmol, 6 eq). The mixture was stirred at 25° C. for 15 min. Then 3-[[5-(5-methylpyrido[4,3-b] indol-7-yl)-2-pyridyl]oxy]cyclobutanecarbaldehyde (69 mg, 0.19 mmol, 1 eq) [prepared as described in US 20180125821 and exemplary compound 376] was added, and the reaction mixture was stirred at 25° C. for 15 min. Then sodium triacetoxyborohydride (82 mg, 0.39 mmol, 2 eq) was added, and the mixture was stirred at 25° C. for 1 h. The mixture was quenched by the addition of water (100 mL), extracted with ethyl acetate (30 mL×4), and the combined organic phase was washed with brine (30 mL), dried over anhydrous sodium sulfate, filtered and concentrated under reduced pressure. The residue was purified by prep-HPLC (column: Phenomenex Synergi C18 150*25*10 um; mobile phase: [water (0.225% FA)-ACN]; B %: 15%-45%, 9 min). Compound 2-(2,6-dioxo-3-piperidyl)-5-[2-[2-[[3-[[5-(5-methylpyrido[4,3-b]indol-7-yl)-2-pyridyl]oxy]cyclobutyl] methyl]-2,6-diazaspiro[3.3]heptan-6-yl]ethoxy]isoindoline-1,3-dione diformate (61.4 mg, 0.07 mmol, 36% yield) was obtained as an off-white solid.

Exemplary Synthesis of Exemplary Compound 387

Prepared according to the scheme below using procedures described in US20180125821 as well as for other examples above.

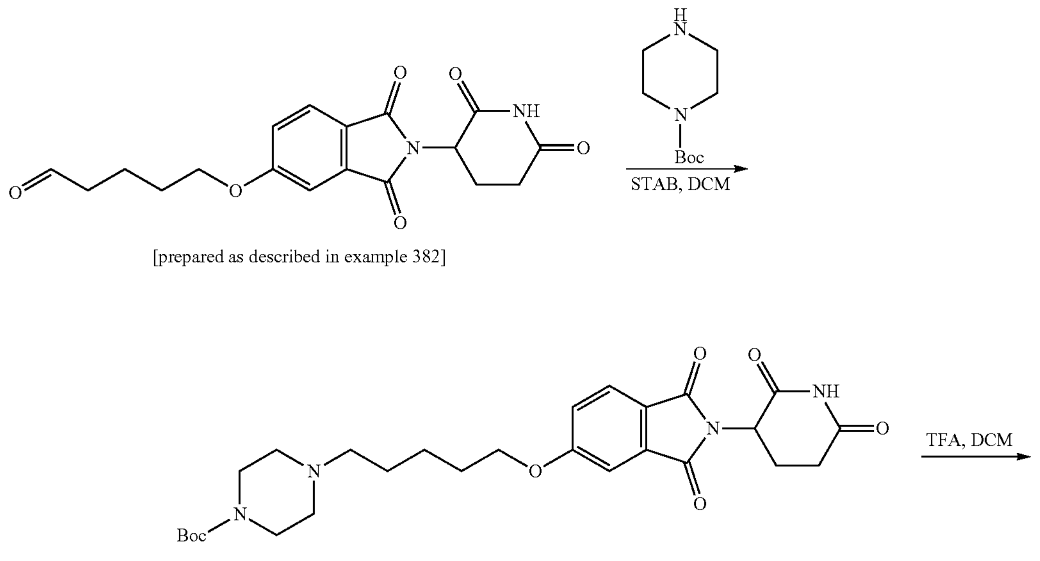

[prepared as described in example 382]

-continued
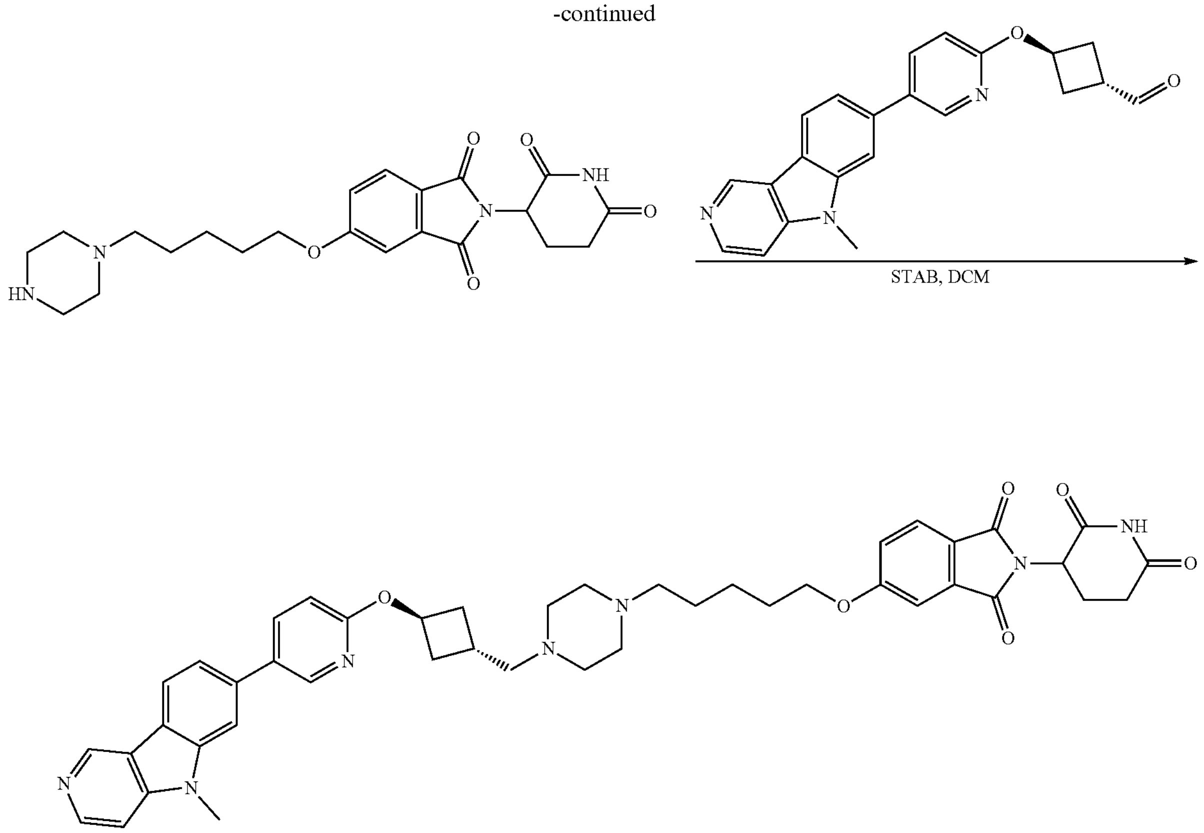
Exemplary Compound 387
Exemplary Synthesis of Exemplary Compound 388
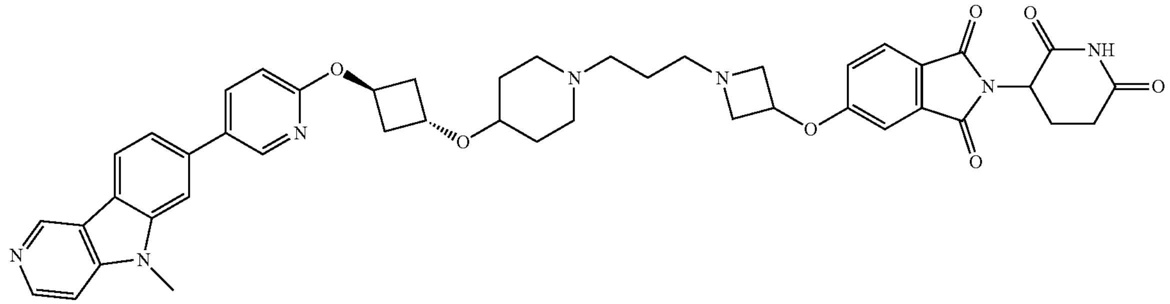 [SMILES: Cn1c2ccncc2c2ccc(-c3ccc(O[C@H]4C[C@H](OC5CCN(CCCN6CC(Oc7ccc8c(c7)C(=O)N(C7CCC(=O)NC7=O)C8=O)C6)CC5)C4)nc3)cc21]
Prepared according to the scheme below using procedures described in US20180125821, other examples above, as well as common procedures known to those skilled in the art.
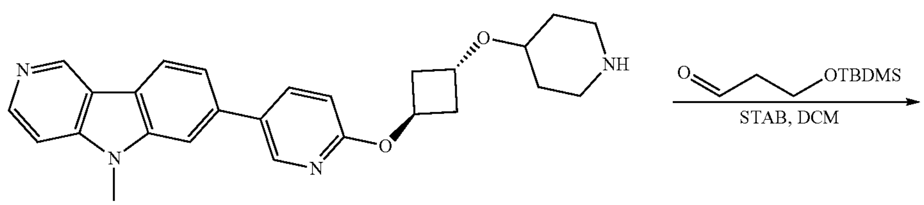

-continued
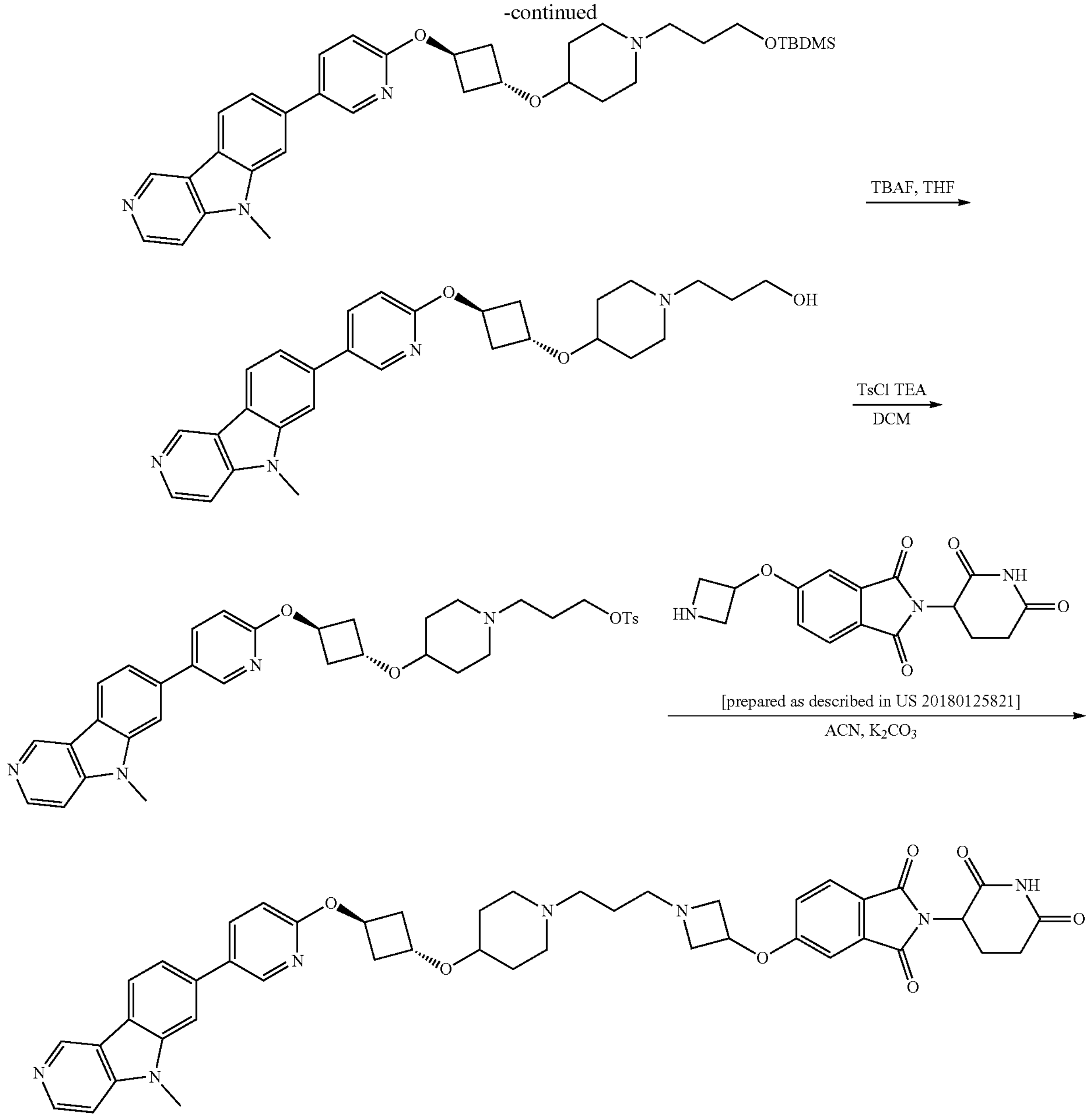
Exemplary Compound 388
Exemplary Synthesis of Exemplary Compound 389
Step 1
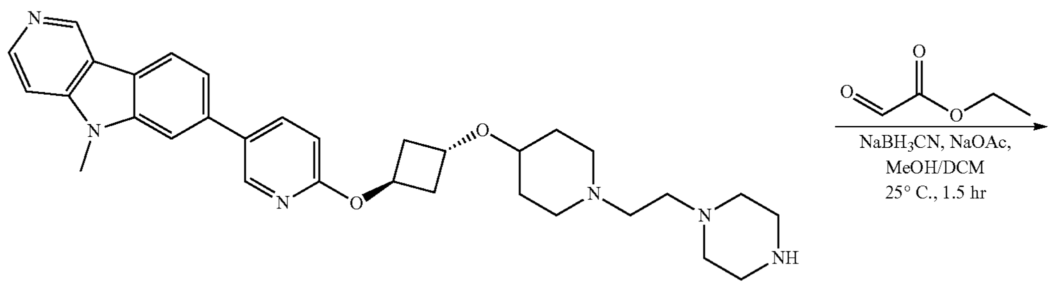
[prepared as described in example 372]

-continued

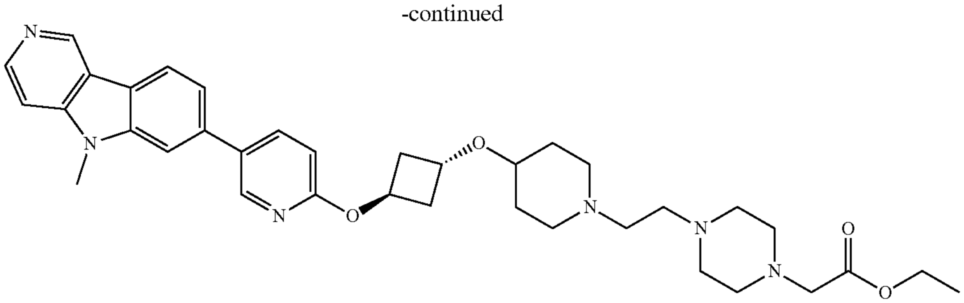

To a mixture of 5-methyl-7-[6-[3-[[1-(2-piperazin-1-yl-ethyl)-4-piperidyl]oxy]cyclobutoxy]-3-pyridyl]pyrido[4,3-b]indole (100 mg, 0.18 mmol, 1 eq) in methanol (1 mL) and dichloromethane (5 mL) was added sodium acetate (30 mg, 0.36 mmol, 2 eq). The mixture stirred at 25° C. for 15 min, and then ethyl 2-oxoacetate (45 mg, 0.22 mmol, 1.2 eq) was added, and the reaction mixture and stirred at 25° C. for 15 min. Then sodium cyanoborohydride (23 mg, 0.36 mmol, 2 eq) was added, and the mixture was stirred at 25° C. for 1 hr. The mixture was quenched by the addition of water (50 mL), extracted with ethyl acetate (30 mL×3), and the combined organic phase was washed with brine (30 mL), dried over anhydrous sodium sulfate, filtered and concentrated under reduced pressure. The residue was purified by prep-TLC (dichloromethane:methanol=10:1). Ethyl 2-[4-[2-[4-[3-[[5-(5-methylpyrido[4,3-b]indol-7-yl)-2-pyridyl]oxy]cyclobutoxy]-1-piperidyl]ethyl]piperazin-1-yl]acetate (30 mg, 0.04 mmol, 24% yield) as a white solid was obtained.

Step 2

To a mixture of ethyl 2-[4-[2-[4-[3-[[5-(5-methylpyrido[4,3-b]indol-7-yl)-2-pyridyl]oxy]cyclobutoxy]-1-piperidyl]ethyl]piperazin-1-yl]acetate (20 mg, 0.03 mmol, 1 eq) in methanol (5 mL) was added sodium hydroxide (4 M, 10 eq). The mixture was stirred at 40° C. for 1 hr. The mixture was concentrated under reduced pressure, the pH was adjusted to 4-5. The residue was purified by prep-HPLC (column: Phenomenex Synergi C18 150*25*10 um; mobile phase: [water (0.225% FA)-ACN]; B %:10%-40%, 9 min). 2-[4-[2-[4-[3-[[5-(5-Methylpyrido[4,3-b]indol-7-yl)-2-pyridyl]oxy]cyclobutoxy]-1-piperidyl]ethyl]piperazin-1-yl]acetic acid (20 mg, 0.03 mmol, 97% yield, formate) was obtained as a white solid.

2-[4-[2-[4-[3-[[5-(5-Methylpyrido[4,3-b]indol-7-yl)-2-pyridyl]oxy]cyclobutoxy]-1-piperidyl]ethyl]piperazin-1-yl]acetic acid was converted to the title compound as described in exemplary compound 377.

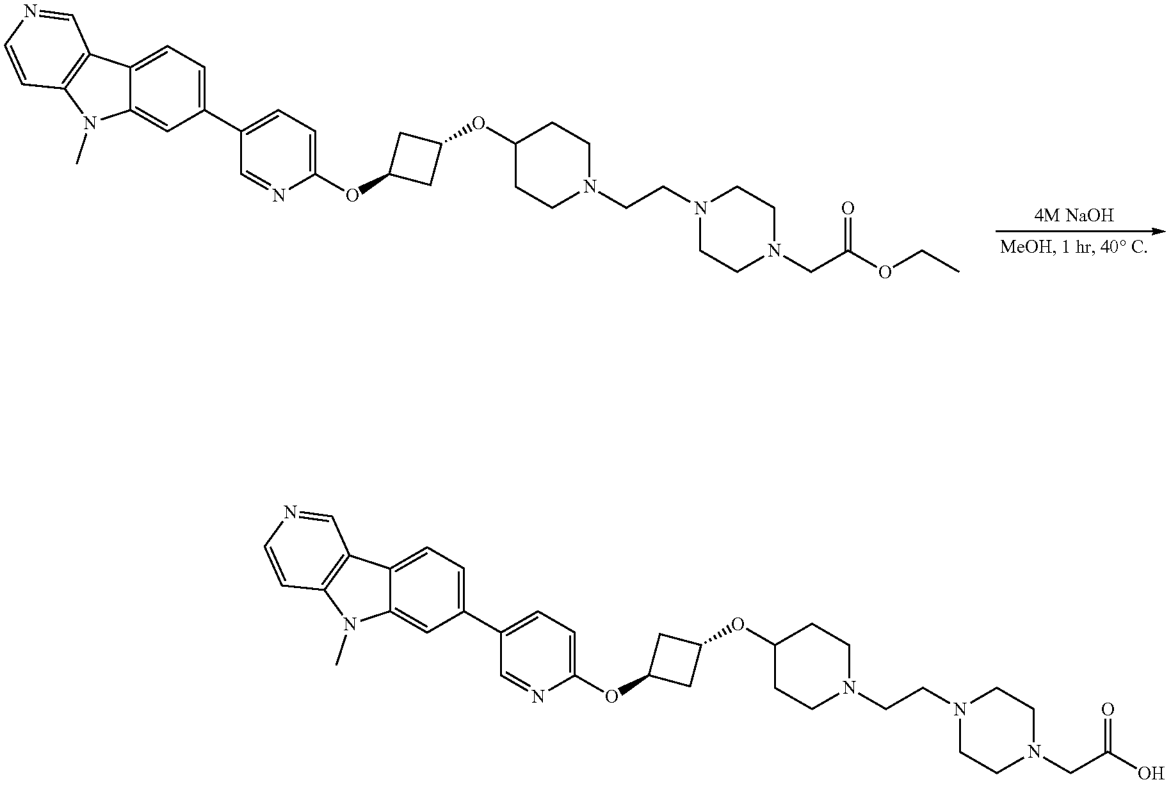

Exemplary Synthesis of Exemplary Compound 390

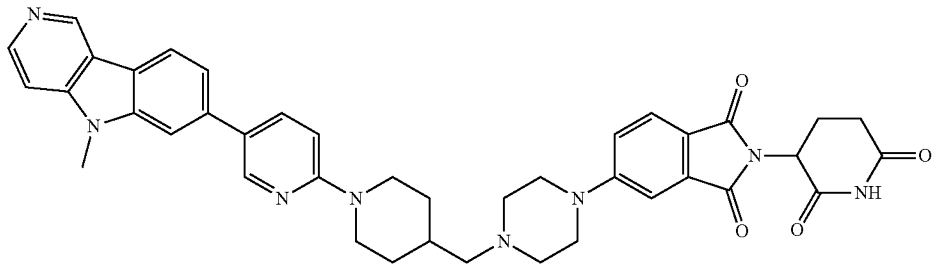 [SMILES: Cn1c2ccncc2c2ccc(-c3ccc(N4CCC(CN5CCN(c6ccc7c(c6)C(=O)N(C6CCC(=O)NC6=O)C7=O)CC5)CC4)nc3)cc21]

Step 1

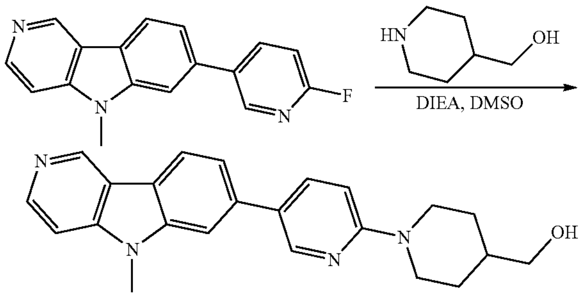

Into a 20-mL sealed tube, was placed 2-fluoro-5-[5-methyl-5H-pyrido[4,3-b]indol-7-yl]pyridine (300 mg, 1.1 mmol, 1.0 equiv) in DMSO (10 mL), to which was added (piperidin-4-yl)methanol (249 mg, 2.16 mmol, 2.0 equiv), DIEA (280 mg, 2.16 mmol, 2.0 equiv). The final reaction mixture was subjected to microwave radiation for 2 hr at 120° C. The reaction was then quenched by the addition of 30 mL of water. The solids were collected by filtration. This resulted in 250 mg (crude) of [1-(5-[5-methyl-5H-pyrido[4,3-b]indol-7-yl]pyridin-2-yl)piperidin-4-yl]methanol as a white solid.

Step 2

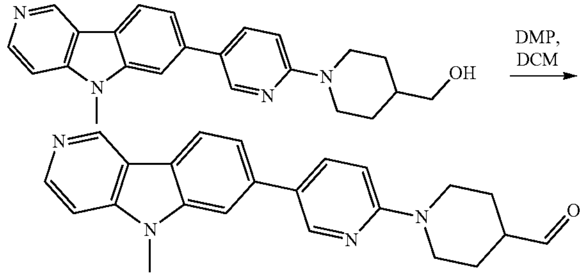

Into a 25-mL round-bottom flask, was placed [1-(5-[5-methyl-5H-pyrido[4,3-b]indol-7-yl]pyridin-2-yl)piperidin-4-yl]methanol (100 mg, 0.27 mmol, 1.0 equiv) in DCM (10 mL), to which was added DMP (228 mg, 0.54 mmol, 2.0 equiv). The resulting solution was stirred for 3 hr at 25° C. The resulting mixture was concentrated under vacuum. The residue was applied to a silica gel column eluting with dichloromethane/methanol (8/1). This resulted in 50 mg (50%) of 1-(5-[5-methyl-5H-pyrido[4,3-b]indol-7-yl]pyridin-2-yl)piperidine-4-carbaldehyde as a yellow oil.

Step 3

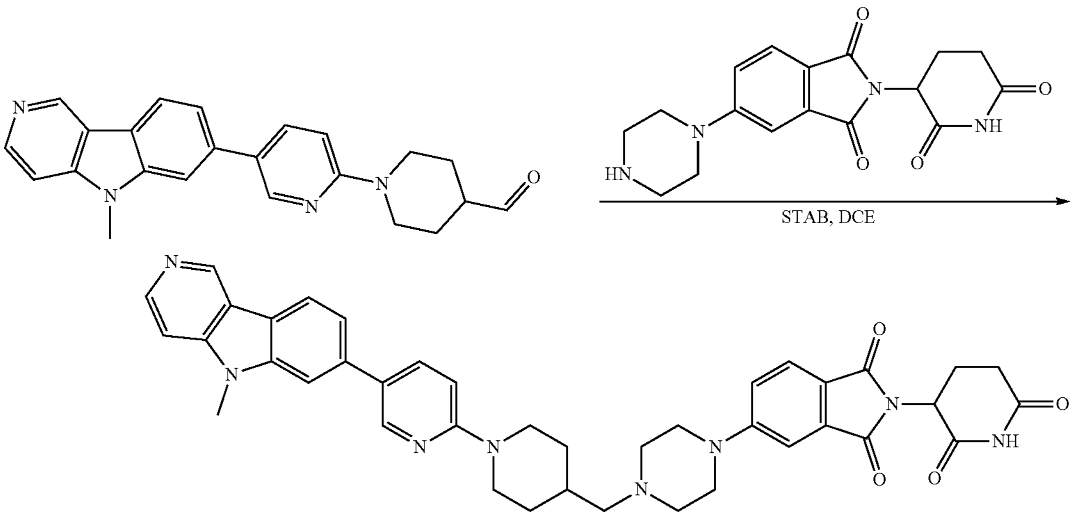

Exemplary Compound 390

Into a 25-mL round-bottom flask, was placed 1-(5-[5-methyl-5H-pyrido[4,3-b]indol-7-yl]pyridin-2-yl)piperidine-4-carbaldehyde (30 mg, 0.08 mmol, 1.0 equiv) and 2-(2,6-dioxopiperidin-3-yl)-5-(piperazin-1-yl)-2,3-dihydro-1H-isoindole-1,3-dione (27.7 mg, 0.08 mmol, 1.0 equiv) in DCE (5 mL), to which was added STAB (34.3 mg, 0.16 mmol, 2.0 equiv). The resulting solution was stirred for 12 hr at 25° C. The reaction mixture was diluted with water (50 mL) and extracted with dichloromethane/MeOH (10/1, 80 mL×2). The organic layers were combined and washed with brine (80 mL×2), dried over anhydrous sodium sulfate and concentrated under vacuum. The crude product was purified by prep-HPLC with the following conditions: XBridge Prep OBD C18 Column 30*50 mm 5 um; Mobile Phase A: water (10 mmol/L $NH_4HCO_3$), Mobile Phase B: acetonitrile; Flow rate: 60 mL/min; Gradient: 53% B to 58% B in 9 min; 254 nm. This resulted in 7.2 mg (13%) of 2-(2,6-dioxopiperidin-3-yl)-5-(4-[[1-(5-[5-methyl-5H-pyrido[4,3-b]indol-7-yl]pyridin-2-yl)piperidin-4-yl]methyl]piperazin-1-yl)-2,3-dihydro-1H-isoindole-1,3-dione as a yellow solid.

Exemplary Synthesis of Exemplary Compound 391

To a solution of methyl 2-(3-hydroxyisoxazol-5-yl)-3-methyl-butanoate (800 mg, 4.02 mmol, 1 eq) in acetonitrile (5 mL) was added potassium carbonate (1.11 g, 8.03 mmol, 2 eq) and perfluorobutyl sulfonyl fluoride (1.46 g, 4.82 mmol, 1.2 eq). The reaction mixture was stirred at 25° C. for 12 hours. The reaction mixture was diluted with water (50 mL) and extracted with ethyl acetate (30 mL×3). The combined organic layers were washed with brine (80 mL×3), dried over anhydrous sodium sulfate, filtered and concentrated under reduced pressure. The residue was purified by silica gel column chromatography (petroleum ether/ethyl acetate=100/1 to 20/1). Methyl 3-methyl-2-[3-(1,1,2,2,3,3,4,4,4-nonafluorobutylsulfonyloxy)isoxazol-5-yl]butanoate (530 mg, 1.10 mmol, 27% yield) was obtained as a colorless oil.

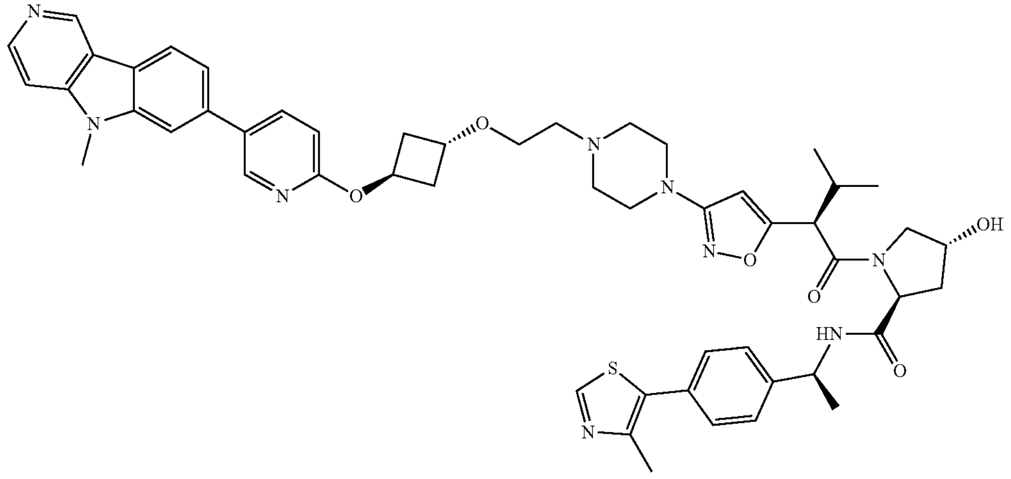 [SMILES: Cc1ncsc1-c1ccc([C@H](C)NC(=O)[C@@H]2C[C@@H](O)CN2C(=O)[C@@H](c2cc(N3CCN(CCO[C@H]4C[C@H](Oc5ccc(-c6ccc7c8cnccc8n(C)c7c6)cn5)C4)CC3)no2)C(C)C)cc1]

Step 1

Step 2

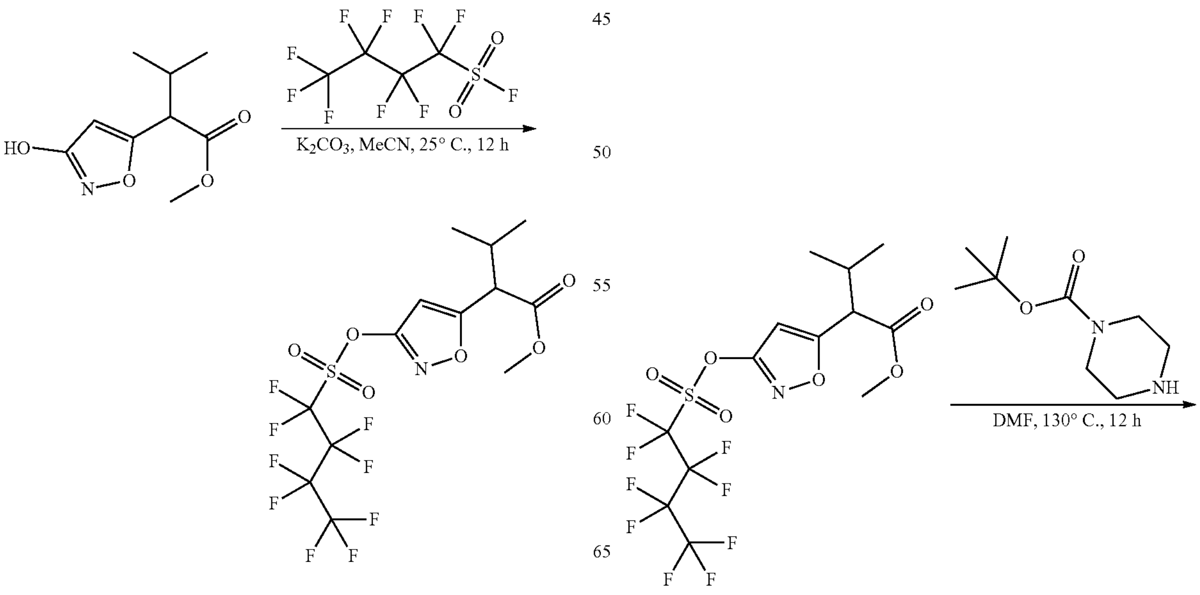

-continued

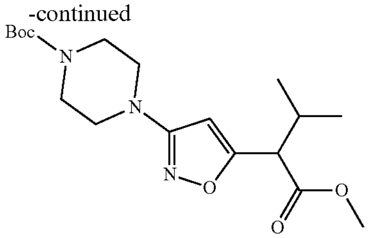

A solution of methyl 3-methyl-2-[3-(1,1,2,2,3,3,4,4,4-nonafluorobutylsulfonyloxy) isoxazol-5-yl]butanoate (400 mg, 0.83 mmol, 1 eq) and tert-butyl piperazine-1-carboxylate (154 mg, 0.83 mmol, 1 eq) in dimethyl formamide (5 mL) was stirred at 130° C. for 12 hours. The reaction mixture was diluted with water (30 mL) and extracted with ethyl acetate (30 mL×3). The combined organic layers were washed with brine (30 mL×3), dried over anhydrous sodium sulfate, filtered and concentrated under reduced pressure. The residue was purified by prep-TLC (petroleum ether: ethyl acetate=3:1). tert-Butyl 4-[5-(1-methoxycarbonyl-2-methyl-propyl)isoxazol-3-yl]piperazine-1-carboxylate (130 mg, 0.35 mmol, 42% yield) was obtained as a colorless oil.

Step 3

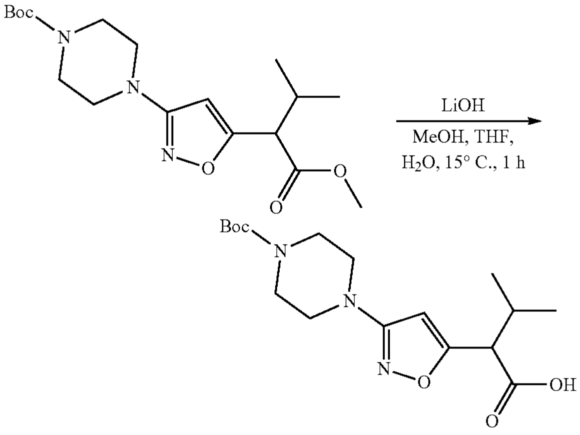

To a solution of tert-butyl 4-[5-(1-methoxycarbonyl-2-methyl-propyl)isoxazol-3-yl]piperazine-1-carboxylate (130 mg, 0.35 mmol, 1 eq) in a mixture of methanol (2 mL), tetrahydrofuran (2 mL) and water (2 mL) was added lithium hydroxide (44 mg, 1.06 mmol, 3 eq). The reaction mixture was stirred at 15° C. for 1 hour. Water (3 mL) was added. The pH was adjusted to 6 with hydrochloric acid (1M in water), and the mixture was extracted with ethyl acetate (10 mL×5). The combined organic layers were washed with brine (50 mL×1), dried over anhydrous sodium sulfate, filtered and concentrated under reduced pressure. 2-[3-(4-tert-Butoxycarbonylpiperazin-1-yl) isoxazol-5-yl]-3-methyl-butanoic acid (100 mg, 0.28 mmol, 79% yield) was obtained as a white solid.

Step 4

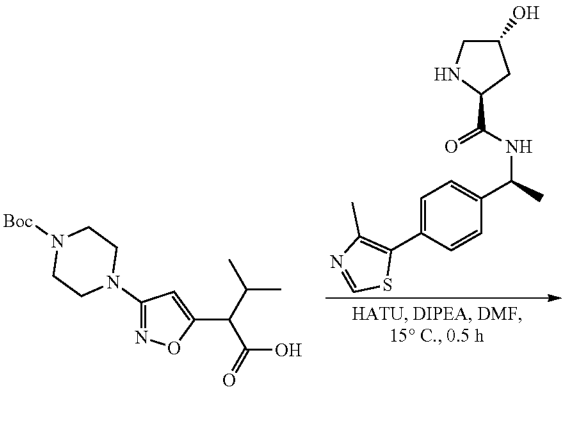

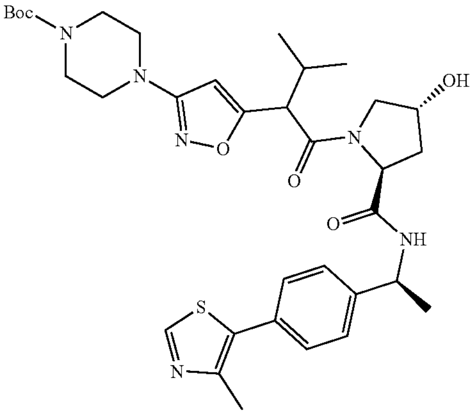

To a solution of 2-[3-(4-tert-butoxycarbonylpiperazin-1-yl)isoxazol-5-yl]-3-methyl-butanoic acid (100 mg, 0.28 mmol, 1 eq) and O—(7-azabenzotriazol-1-yl)-N,N,N',N'-tetramethyluronium hexafluorophosphate (129 mg, 0.33 mmol, 1.2 eq) in dimethyl formamide (5 mL) were added (2S,4R)-4-hydroxy-N-[(1S)-1-[4-(4-methylthiazol-5-yl) phenyl]ethyl]pyrrolidine-2-carboxamide (104 mg, 0.28 mmol, 1 eq, hydrochloride) and diisopropyl ethyl amine (109 mg, 0.84 mmol, 3 eq). The reaction mixture was stirred at 15° C. for 0.5 h. The reaction mixture was poured into water (20 mL), extracted with ethyl acetate (30 mL×3). The combined organic layers were washed with brine (50 mL×3), dried over anhydrous sodium sulfate, filtered and concentrated under reduced pressure. The residue was purified by prep-TLC (dichloromethane:methanol=10:1). Tert-Butyl 4-[5-[1-[(2S,4R)-4-hydroxy-2-[[(1S)-1-[4-(4-methyl-thiazol-5-yl)phenyl]ethyl]carbamoyl]pyrrolidine-1-carbonyl]-2-methyl-propyl]599ecarbona-3-yl]piperazine-1-carboxylate (180 mg, 0.26 mmol, 92% yield) was obtained as a colorless oil.

Step 5

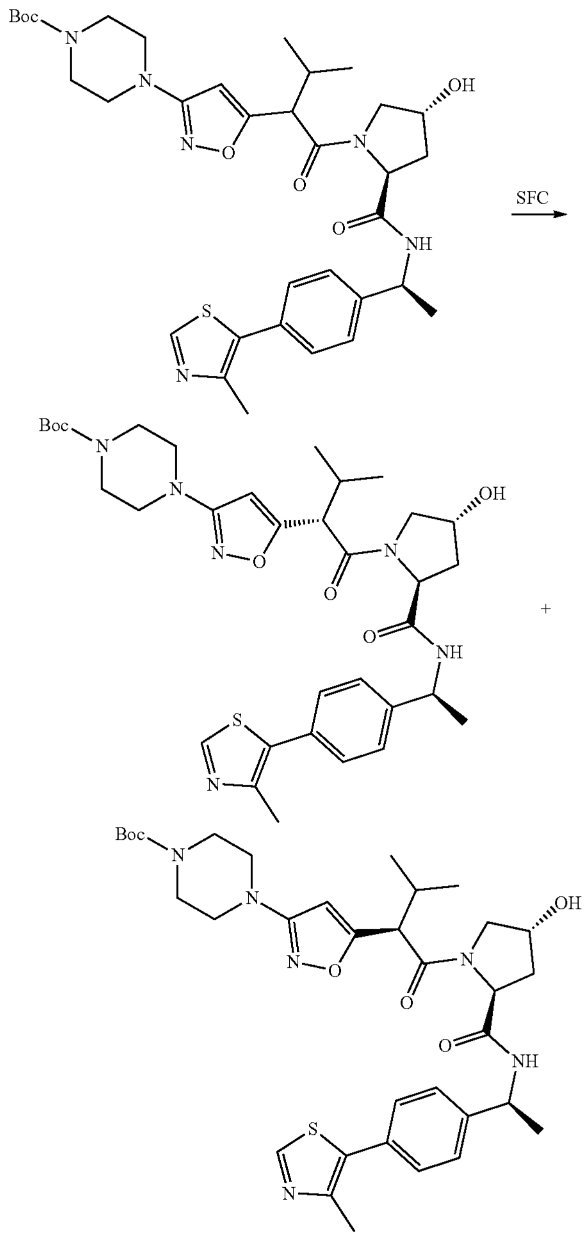

tert-butyl 4-[5-[1-[(2S,4R)-4-hydroxy-2-[[(1S)-1-[4-(4-methylthiazol-5-yl)phenyl]ethyl] carbamoyl]pyrrolidine-1-carbonyl]-2-methyl-propyl]600ecarbona-3-yl]piperazine-1-carboxylate (200 mg, 0.29 mmol, 1 eq) was separated by chiral supercritical fluid chromatography. Tert-butyl 4-[5-[(1S)-1-[(2S,4R)-4-hydroxy-2-[[(1S)-1-[4-(4-methylthiazol-5-yl)phenyl]ethyl] carbamoyl]pyrrolidine-1-carbonyl]-2-methyl-propyl]600ecarbona-3-yl]piperazine-1-carboxylate (80 mg, 0.11 mmol, 76% yield, 95% purity) was obtained as a white solid. Tert-butyl 4-[5-[(1R)-1-[(2S,4R)-4-hydroxy-2-[[(1S)-1-[4-(4-methylthiazol-5-yl)phenyl] ethyl]carbamoyl]pyrrolidine-1-carbonyl]-2-methyl-propyl] 600ecarbona-3-yl]piperazine-1-carboxylate (70 mg, 0.1 mmol, 68% yield, 98% purity) was obtained as a white solid. (Configurations of the stereocenter distinguishing the two diastereomers were tentatively assigned at this point and were later ascertained based on the comparative biological activity of the title compound).

Step 6

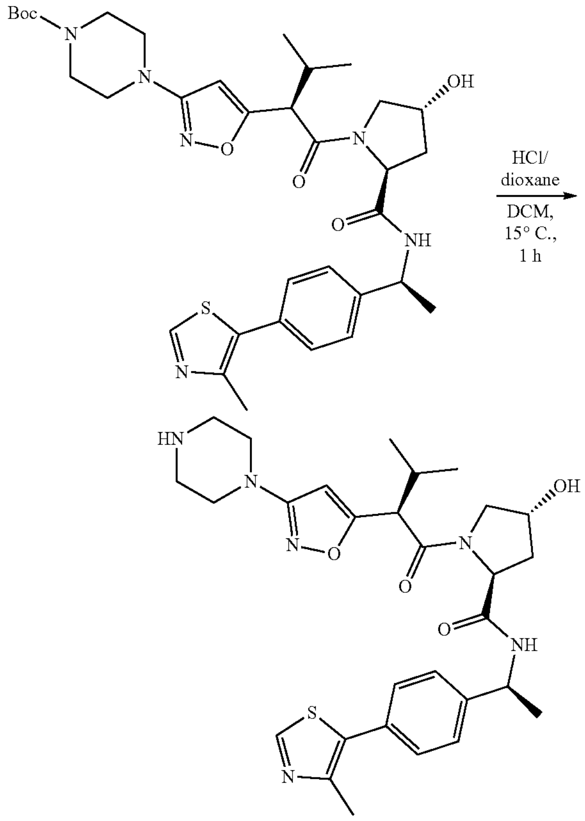

To a solution of tert-butyl 4-[5-[(1R)-1-[(2S,4R)-4-hydroxy-2-[[(1S)-1-[4-(4-methylthiazol-5-yl)phenyl]ethyl] carbamoyl]pyrrolidine-1-carbonyl]-2-methyl-propyl] 600ecarbona-3-yl]piperazine-1-carboxylate (70 mg, 0.1 mmol, 1 eq) in dichloromethane (2 mL) was added hydrochloric acid (4 M in dioxane, 3 mL). The reaction mixture was stirred at 15° C. for 1 hour. The reaction mixture was concentrated under reduced pressure. (2S,4R)-4-hydroxy-1-[(2R)-3-methyl-2-(3-piperazin-1-ylisoxazol-5-yl)butanoyl]-N-[(1S)-1-[4-(4-methylthiazol-5-yl)phenyl]ethyl]pyrrolidine-2-carboxamide (55 mg, 0.09 mmol, 91% yield) was obtained as a white solid.

(2S,4R)-4-hydroxy-1-[(2R)-3-methyl-2-(3-piperazin-1-ylisoxazol-5-yl)butanoyl]-N-[(1S)-1-[4-(4-methylthiazol-5-yl)phenyl]ethyl]pyrrolidine-2-carboxamide was converted to the title compound according to the scheme below using procedures described for other examples above and common procedures known to skilled in the art.

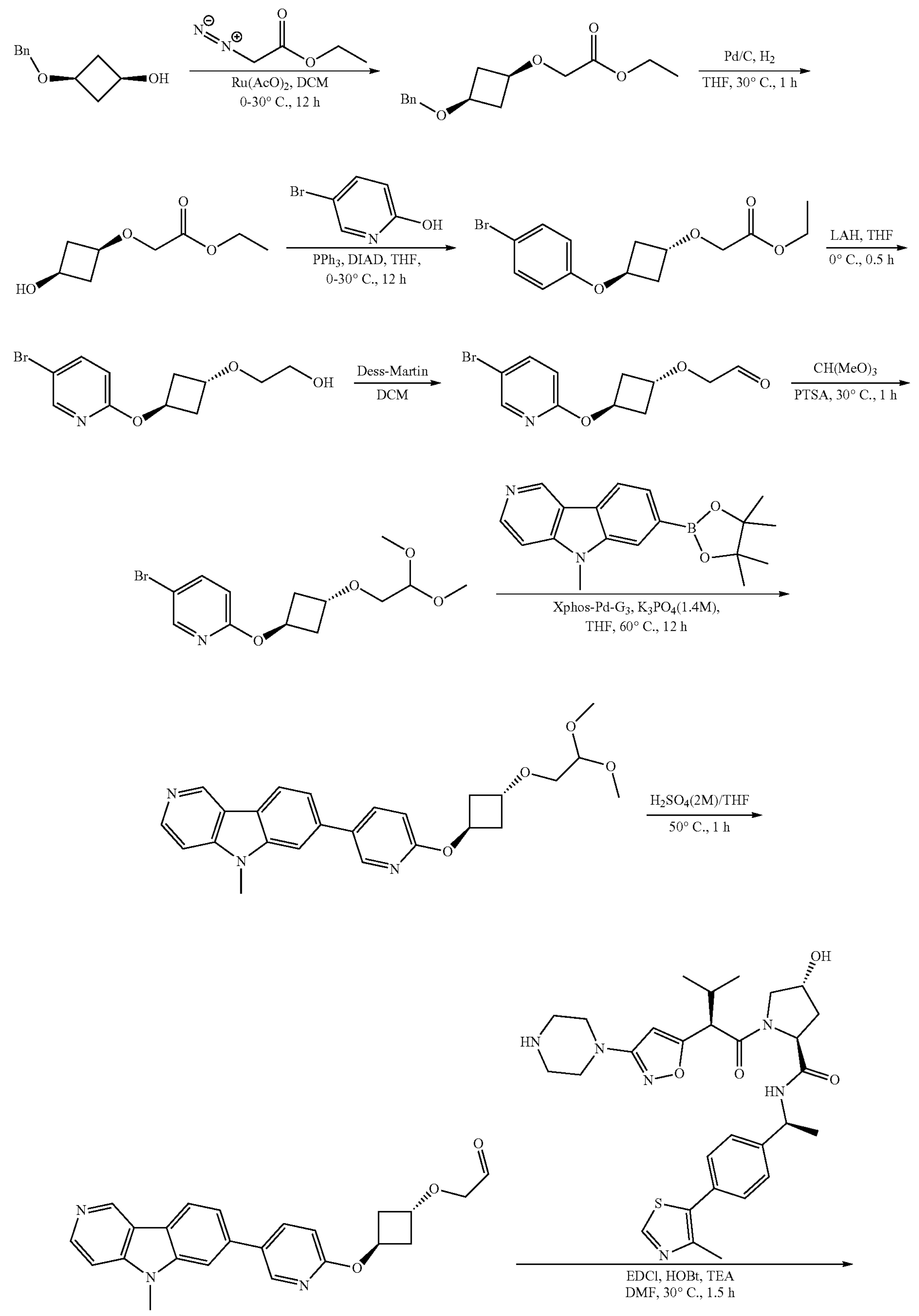
Ru(AcO)2, DCM
0-30° C., 12 h
Pd/C, H2
THF, 30° C., 1 h
PPh3, DIAD, THF,
0-30° C., 12 h
LAH, THF
0° C., 0.5 h
Dess-Martin
DCM
CH(MeO)3
PTSA, 30° C., 1 h
Xphos-Pd-G3, K3PO4(1.4M),
THF, 60° C., 12 h
H2SO4(2M)/THF
50° C., 1 h
EDCl, HOBt, TEA
DMF, 30° C., 1.5 h -continued

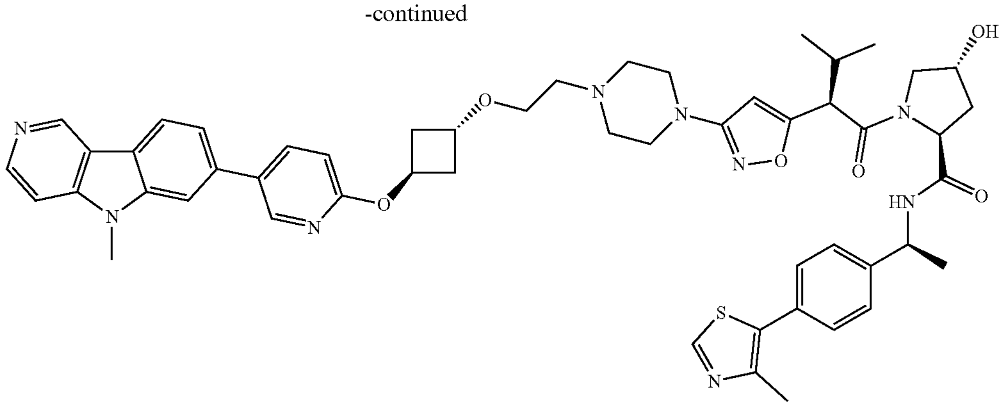

Exemplary Compound 391

Exemplary Synthesis of Exemplary Compound 392

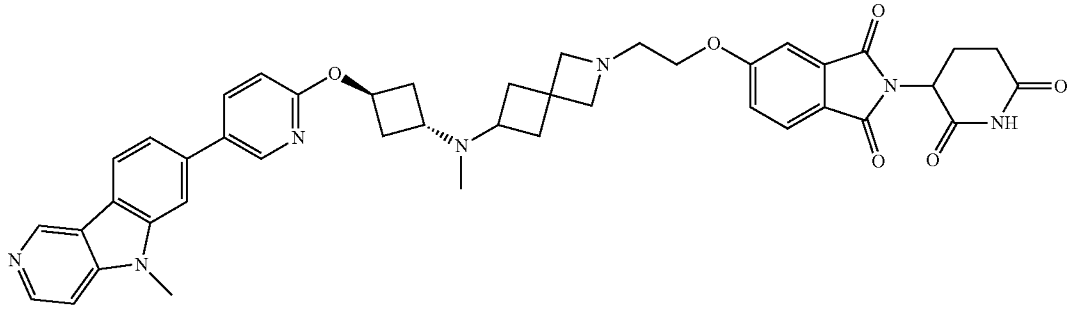

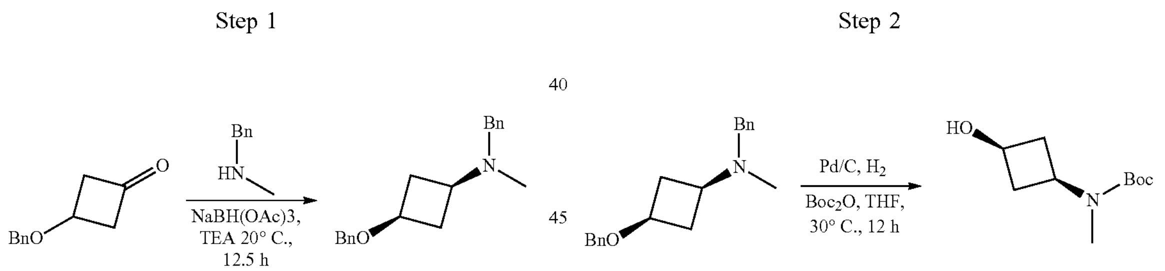

To a solution of N-methyl-1-phenyl-methanamine (6.88 g, 56.75 mmol, 1 eq) in dichloromethane (100 mL) was added triethylamine (5.74 g, 56.75 mmol, 1 eq) and 3-benzyloxycyclobutanone (10 g, 56.75 mmol, 1 eq). The mixture was stirred at 30° C. for 0.5 h. Sodium borohydride acetate (24.06 g, 113.5 mmol, 2 eq) was added at 0° C., and the mixture was stirred at 30° C. for 12 h. To the reaction was added water (300 mL), and the mixture was extracted with ethyl acetate (300 mLx3). The organic layer was dried over sodium sulfate and concentrated. The residue was purified via silica gel chromatography (petroleum ether:ethyl acetate=100:1 to 10:1) and prep-HPLC (column: Phenomenex luna C18 250*80 mm*10 um; mobile phase: [water (0.225% FA)-CAN]; B %: 5ACN %-35ACN %, 35 min). N-Benzyl-3-benzyloxy-N-methyl-cyclobutanamine (5 g, 17.77 mmol, 31% yield) was obtained as a yellow oil.

To a solution of N-benzyl-3-benzyloxy-N-methyl-cyclobutanamine (2 g, 7.11 mmol, 1 eq) in tetrahydrofuran (50 mL) and ethanol (50 mL) was added 10% palladium on carbon (1 g) and di-tert-butyl 602ecarbonate (3.10 g, 14.22 mmol, 2 eq) at 30° C. under hydrogen (15 psi). The mixture was stirred at 30° C. for 12 h. The mixture was filtered and concentrated. The residue was used in the next step without further purification. Tert-Butyl N-(3-hydroxycyclobutyl)-N-methyl-carbamate (0.5 g, 2.48 mmol, 34% yield) was obtained as a yellow oil.

Tert-Butyl N-(3-hydroxycyclobutyl)-N-methyl-carbamate was converted to the title compound according to the scheme below using procedures described for other examples above.

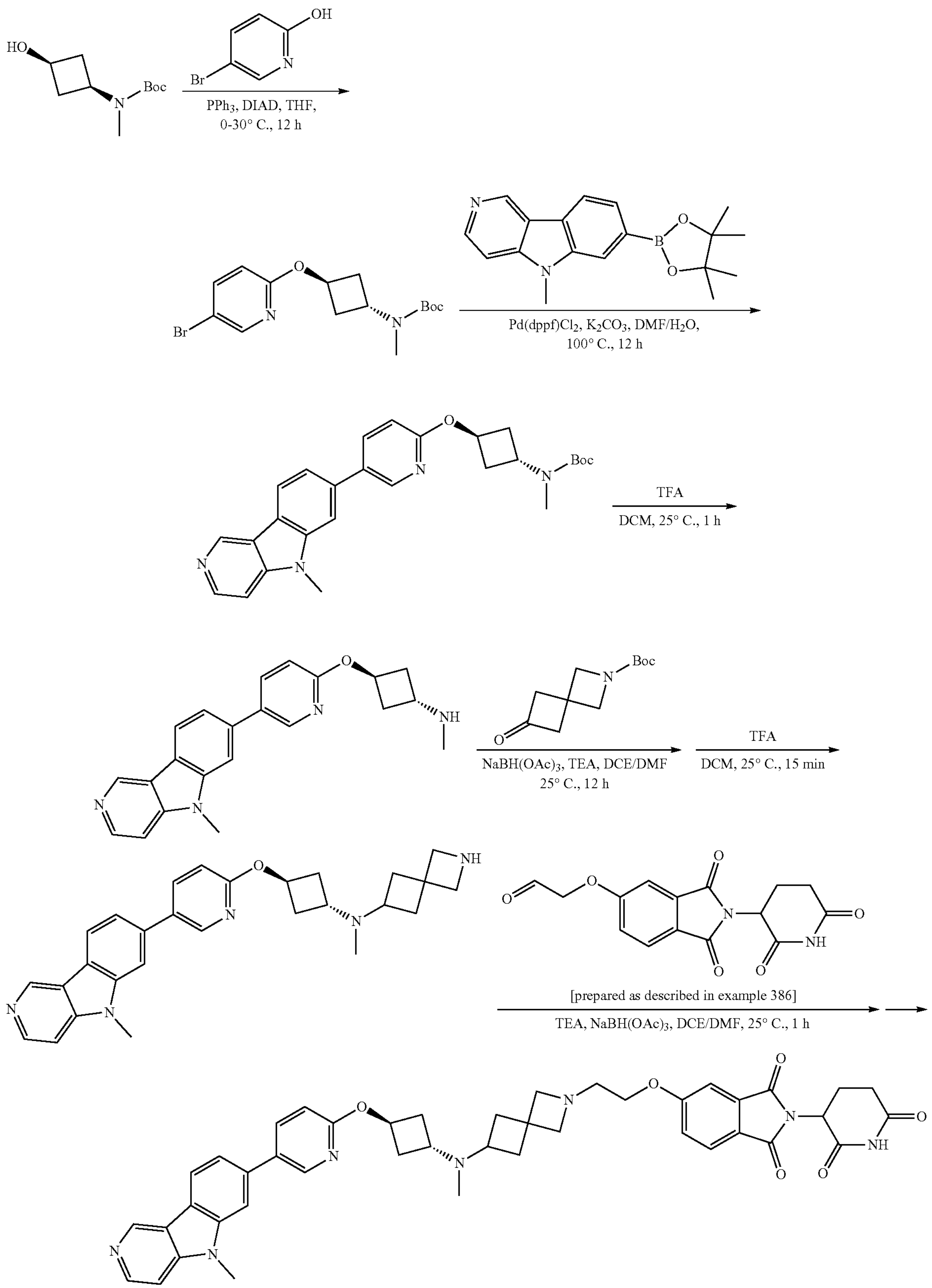
Exemplary Compound 392

Exemplary Synthesis of Exemplary Compound 393

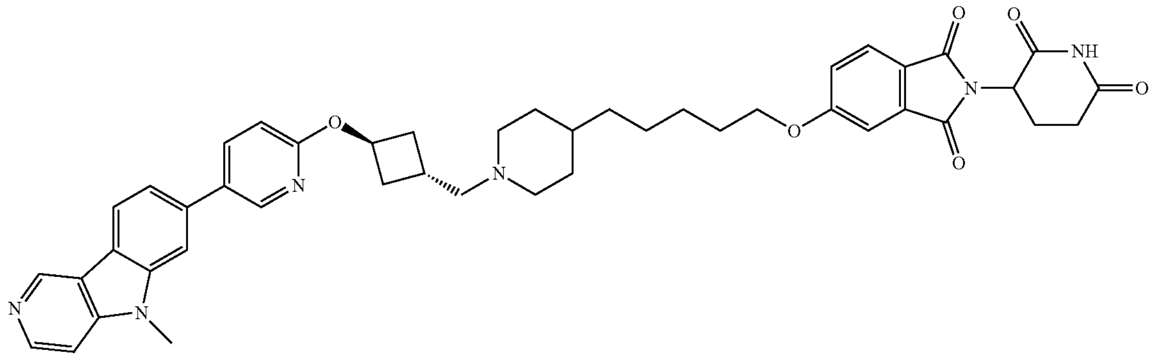 [SMILES: Cn1c2ccncc2c2ccc(-c3ccc(O[C@H]4C[C@H](CN5CCC(CCCCCOc6ccc7c(c6)C(=O)N(C6CCC(=O)NC6=O)C7=O)CC5)C4)nc3)cc21]

Step 1

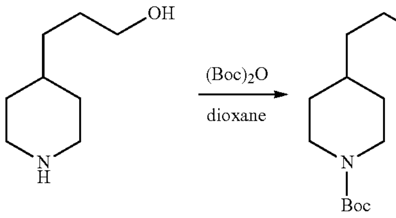

Into a 250-mL round-bottom flask, was placed 3-(piperidin-4-yl)propan-1-ol (4 g, 27.93 mmol, 1 equiv) in dioxane (50 mL), to which was added $(Boc)_2O$ (7.31 g, 33.49 mmol, 1.20 equiv). The resulting solution was stirred for 2 hr at 25° C. The resulting mixture was concentrated under vacuum. The residue was applied onto a silica gel column eluting with ethyl acetate/hexane (0:1 to 1:4). This resulted in 5 g (74%) of tert-butyl 4-(3-hydroxypropyl)piperidine-1-carboxylate as a white solid.

Step 2

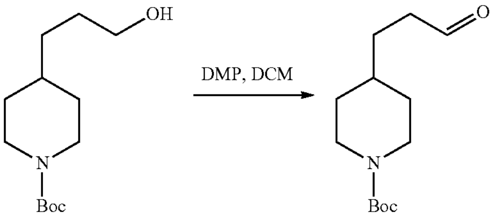

Into a 50-mL round-bottom flask, was placed tert-butyl 4-(3-hydroxypropyl)piperidine-1-carboxylate (300 mg, 1.23 mmol, 1 equiv) in DCM (5 mL), to which was added DMP (800 mg, 1.89 mmol, 1.53 equiv). The resulting solution was stirred for 1 hr at 25° C. The reaction was then quenched by the addition of 10 mL of water. The resulting solution was extracted with (3×10 mL) of dichloromethane, and the organic layers combined and dried over anhydrous sodium sulfate. The solids were filtered out. The resulting mixture was concentrated under vacuum. This resulted in 250 mg (crude) of tert-butyl 4-(3-oxopropyl)piperidine-1-carboxylate as a light yellow oil.

Step 3

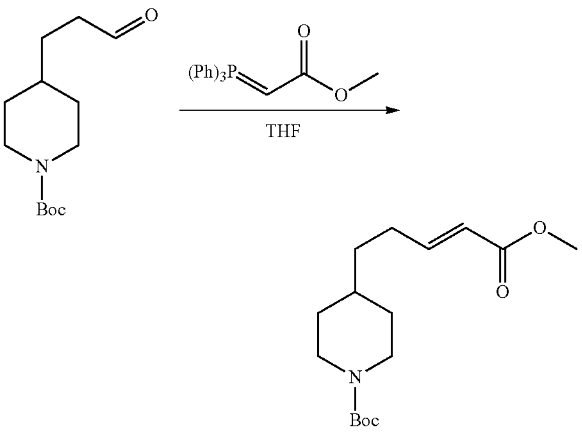

Into a 50-mL round-bottom flask, was placed tert-butyl 4-(3-oxopropyl)piperidine-1-carboxylate (200 mg, 0.83 mmol, 1 equiv) in THF (10 mL), to which was added (triphenylphospharanylidene) methyl acetate (300 mg, 0.90 mmol, 1.1 equiv). The resulting solution was stirred for 12 hr at 50° C. The reaction mixture was cooled to room temperature. The resulting mixture was concentrated under vacuum. The residue was applied to a silica gel column eluting with ethyl acetate/petroleum ether (0:1 to 1:4). This resulted in 200 mg (81%) of tert-butyl 4-[(3E)-5-methoxy-5-oxopent-3-en-1-yl]piperidine-1-carboxylate as a colorless oil.

Step 4

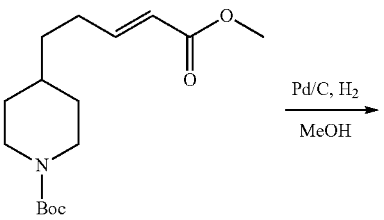

-continued

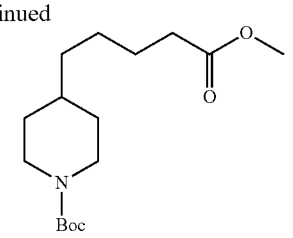

Into a 50-mL round-bottom flask, was placed tert-butyl 4-[(3E)-5-methoxy-5-oxopent-3-en-1-yl]piperidine-1-carboxylate (200 mg, 0.67 mmol, 1 equiv) and Pd/C (10%, 400 mg, 3.77 mmol, 5.62 equiv) in MeOH (20 mL) under nitrogen atmosphere. The flask was then vacuumed and flushed with hydrogen. The reaction mixture was hydrogenated at room temperature for 12 hours under hydrogen atmosphere using a hydrogen balloon. Then the reaction mixture was filtered through a celite pad, and the filtrate was concentrated under reduced pressure. This resulted in 180 mg (crude) of tert-butyl 4-(5-methoxy-5-oxopentyl)piperidine-1-carboxylate as a colorless oil.

Step 5

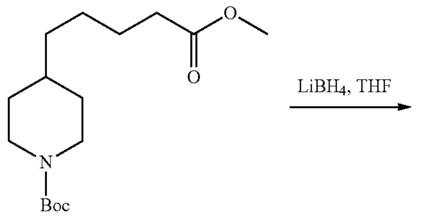

-continued

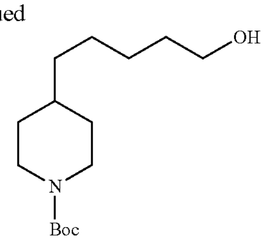

Into a 50-mL round-bottom flask, was placed tert-butyl 4-(5-methoxy-5-oxopentyl)piperidine-1-carboxylate (200 mg, 0.67 mmol, 1 equiv) in THF (5 mL), to which was added $LiBH_4$ (80 mg, 3.67 mmol, 5.50 equiv) at 0° C. The resulting solution was stirred for 1 hr at 25° C. The reaction was then quenched by the addition of 10 mL of water. The resulting solution was extracted with (3×20 mL) of ethyl acetate, and the organic layers combined. The resulting mixture was washed with (3×10 mL) of brine. The organic phase was dried over anhydrous sodium sulfate. The solids were filtered out. The resulting mixture was concentrated under vacuum. This resulted in 160 mg (crude) of tert-butyl 4-(5-hydroxypentyl)piperidine-1-carboxylate as a colorless oil.

tert-Butyl 4-(5-hydroxypentyl)piperidine-1-carboxylate was converted to the title compound according to the scheme below using procedures described for other examples above.

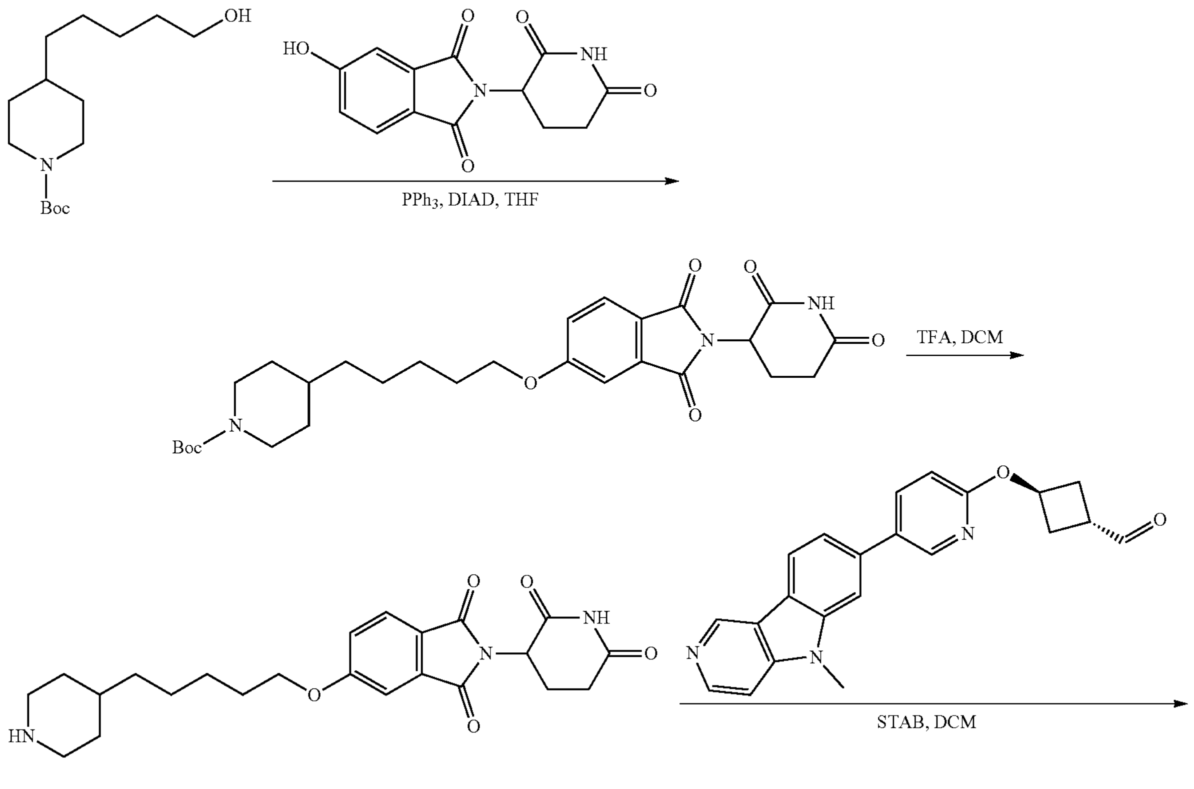

-continued
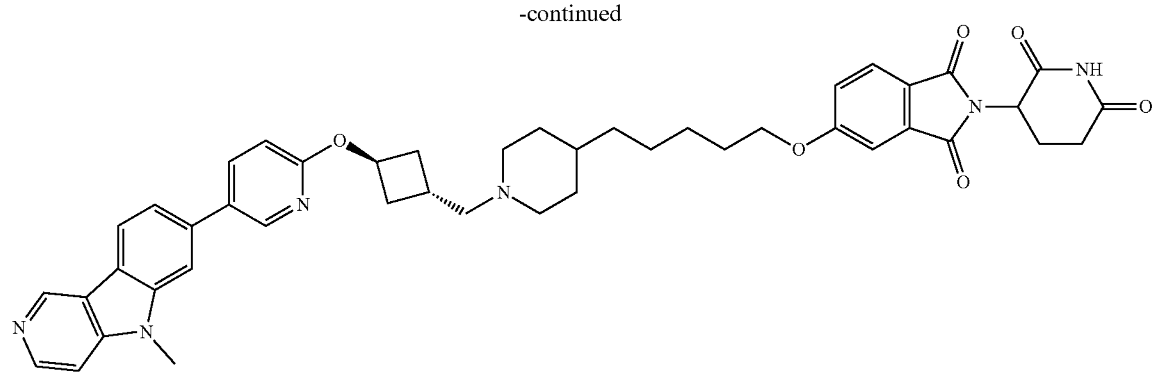
Exemplary Compound 393
Exemplary Synthesis of Exemplary Compound 394
Prepared according to the scheme below using procedures described for examples above.
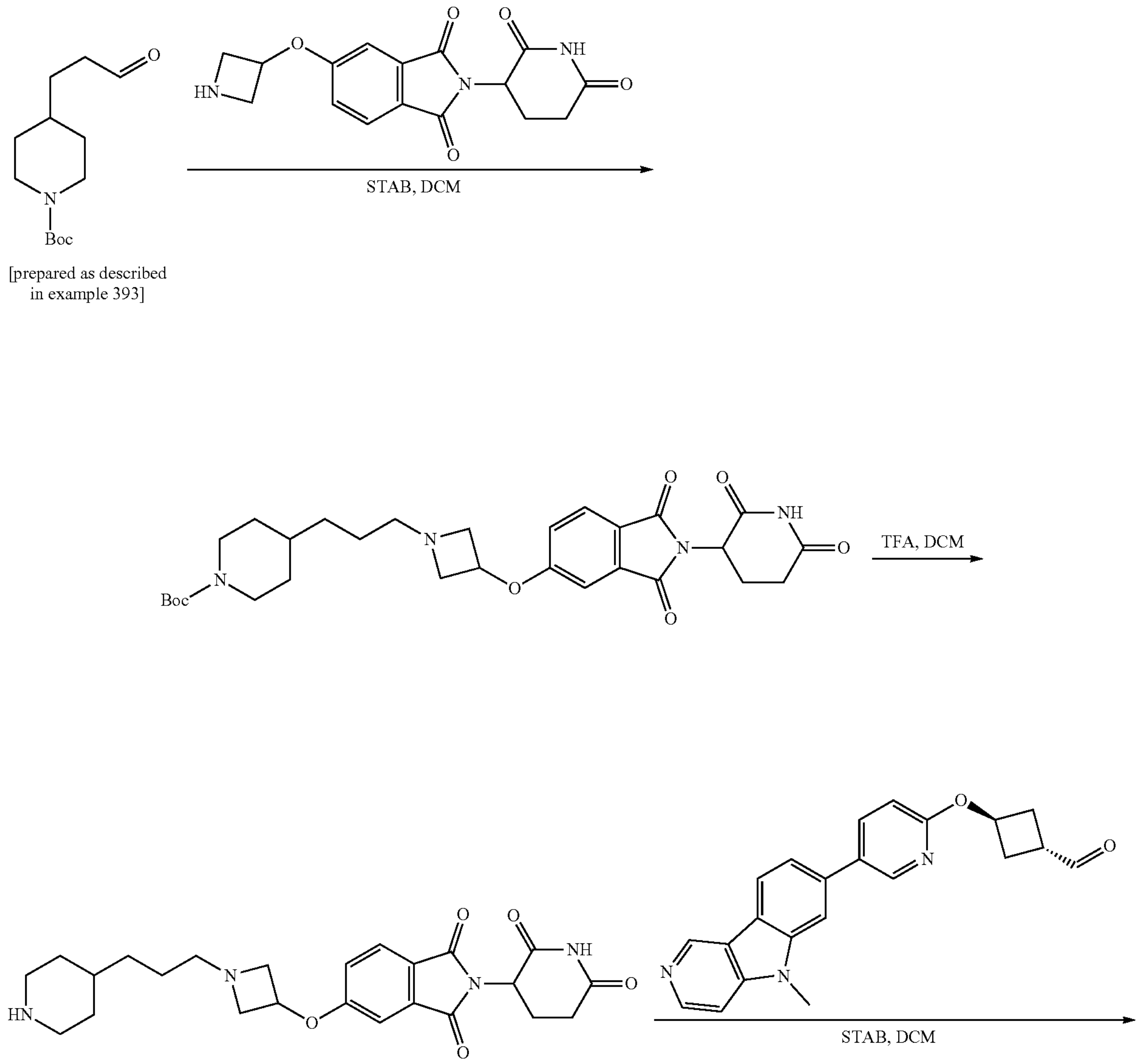

-continued
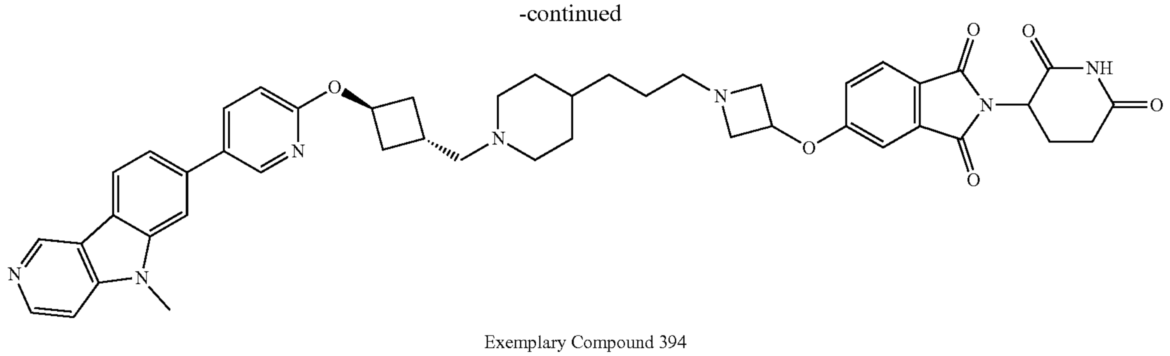
Exemplary Compound 394
Exemplar Synthesis of Exemplary Compounds 395 and 396
Exemplar Compound 395
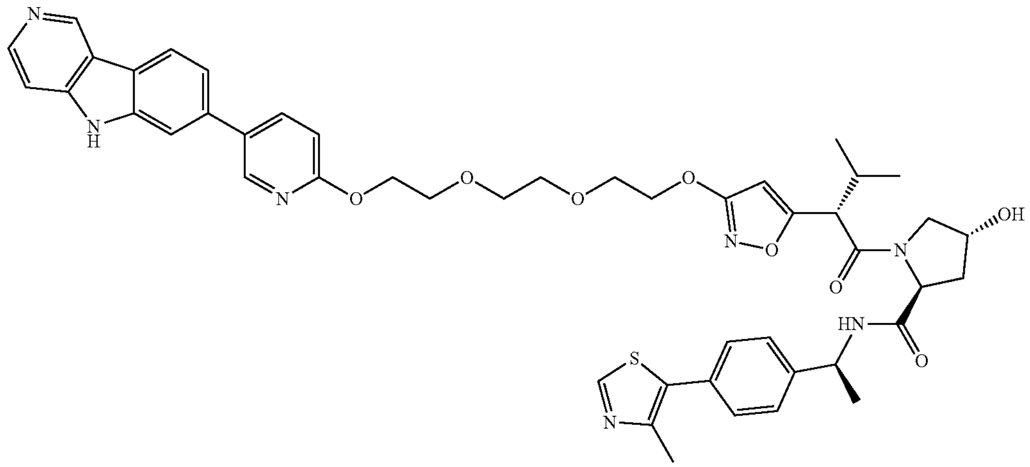
Exemplary Compound 396
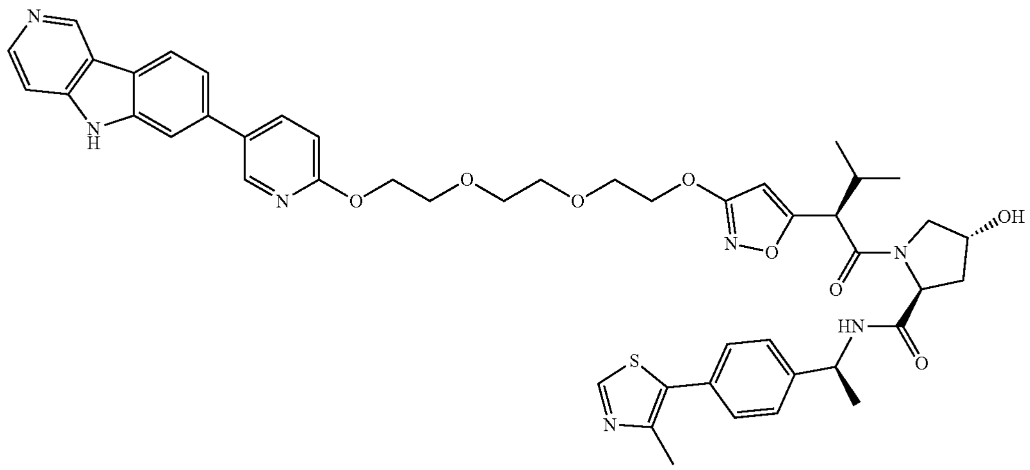
Methylbenzenesulfonyl)oxy]ethoxy]ethoxy)ethoxy]pyridin-3-yl]pyrido[4,3-b]indole-5-carboxylate was prepared according to the scheme below using procedures described in US 20180125821 and those described for other examples above.

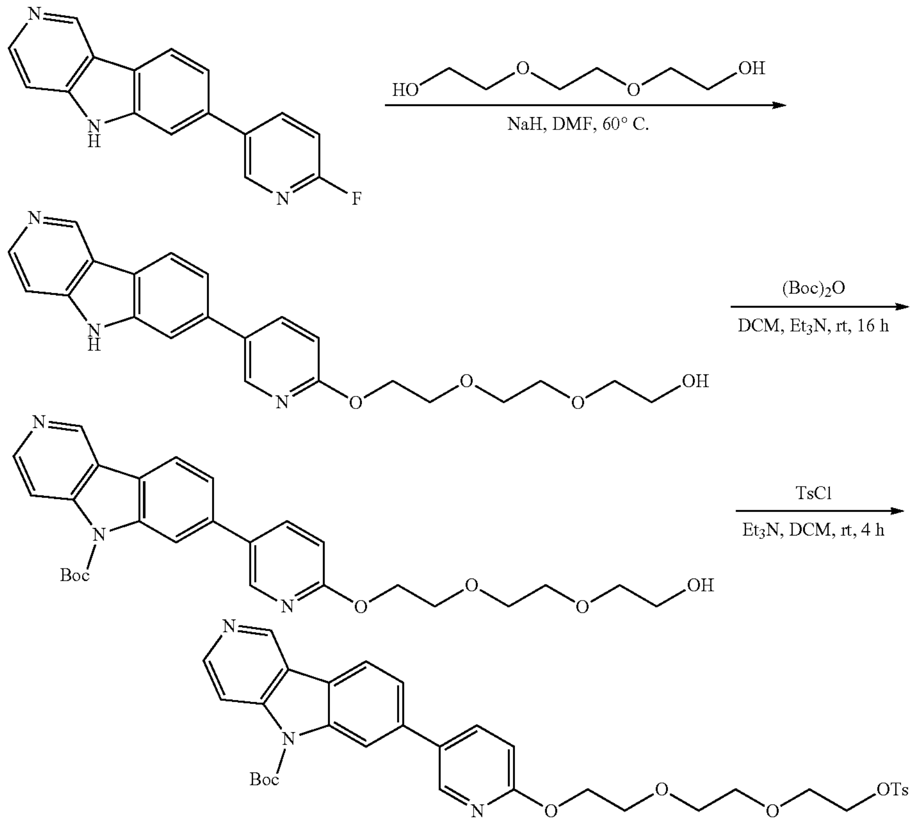

Step 1

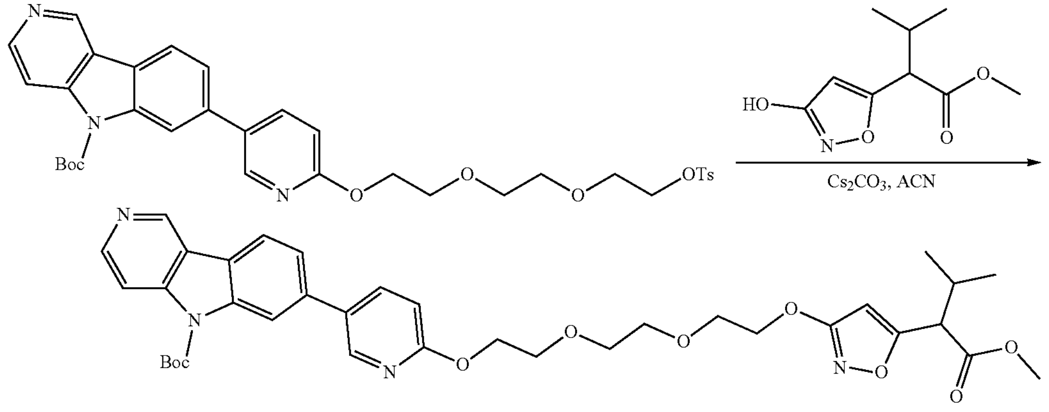

Into a 100-mL round-bottom flask purged and maintained with an inert atmosphere of nitrogen, was placed tert-butyl 7-[6-[2-(2-[2-[(4-methylbenzenesulfonyl)oxy]ethoxy]ethoxy)ethoxy]pyridin-3-yl]pyrido[4,3-b]indole-5-carboxylate (600 mg, 0.93 mmol, 1.00 equiv) and methyl 2-(3-hydroxy-1,2-oxazol-5-yl)-3-methylbutanoate (240 mg, 1.20 mmol, 1.30 equiv) in MeCN (25 mL), to which was added $Cs_2CO_3$ (1.2 g, 3.71 mmol, 4.00 equiv). The resulting solution was stirred for 3 hr at 80° C. The reaction mixture was cooled to room temperature. The resulting mixture was concentrated under vacuum. The residue was applied onto a silica gel column eluting with dichloromethane/methanol (100:1 to 20:1) to give tert-butyl 7-(6-[2-[2-(2-[[5-(1-methoxy-3-methyl-1-oxobutan-2-yl)-1,2-oxazol-3-yl]oxy]ethoxy)ethoxy]ethoxy]pyridin-3-yl)pyrido[4,3-b]indole-5-carboxylate (500 mg, 80%) as a yellow oil.

tert-Butyl 7-(6-[2-[2-(2-[[5-(1-methoxy-3-methyl-1-oxobutan-2-yl)-1,2-oxazol-3-yl]oxy]ethoxy)ethoxy]ethoxy]pyridin-3-yl)pyrido[4,3-b]indole-5-carboxylate was converted to the title compounds according to the scheme below using procedures described for other examples above as well as other procedures known to those skilled in the art.

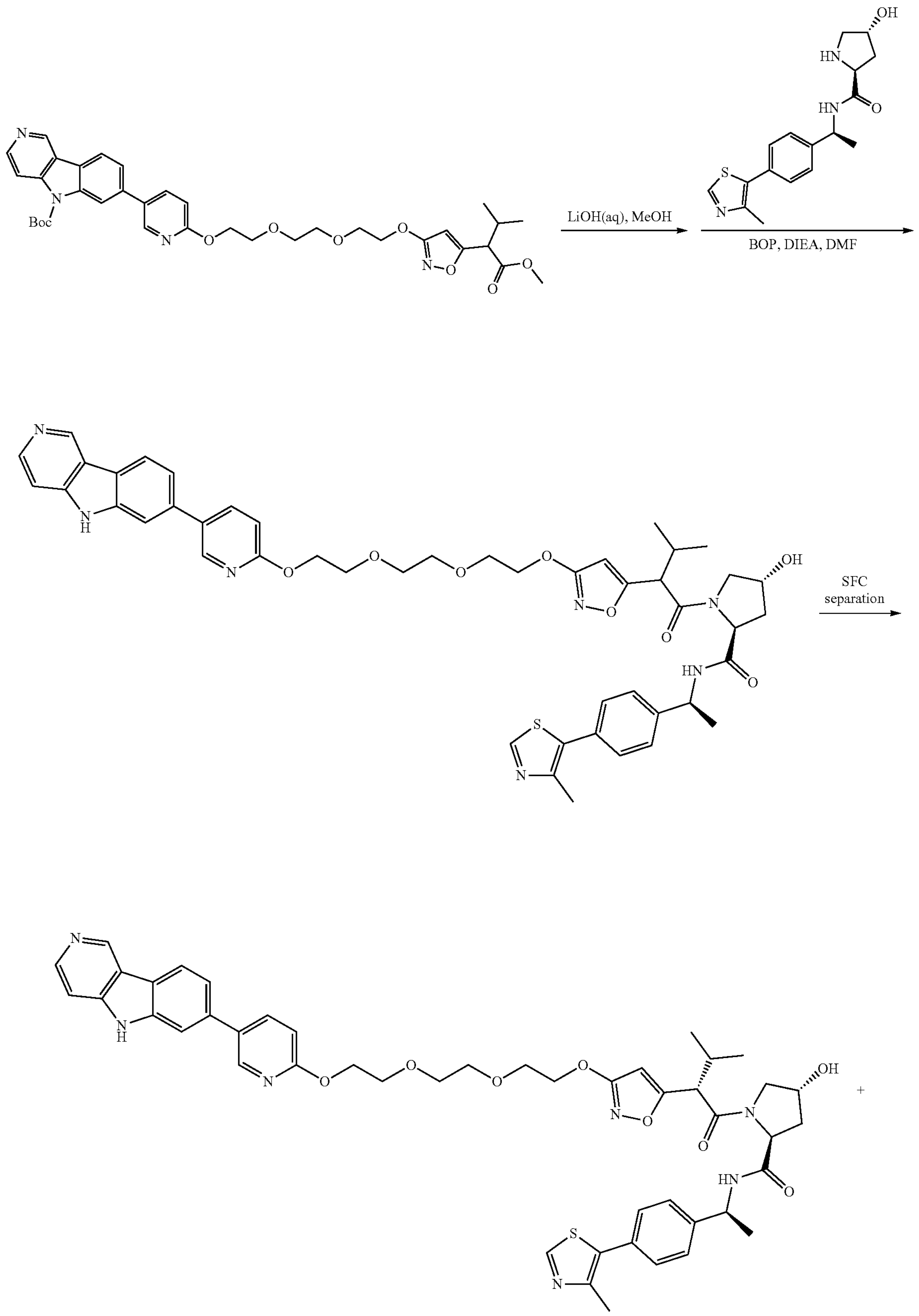
Exemplary Compound 395

-continued
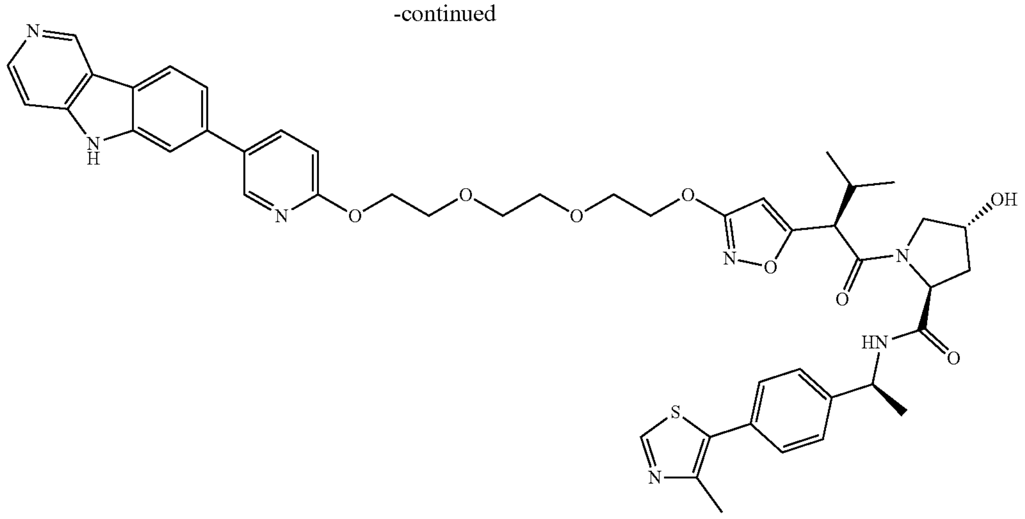
Exemplary Compound 396
Exemplary Synthesis of Exemplary Compound 400
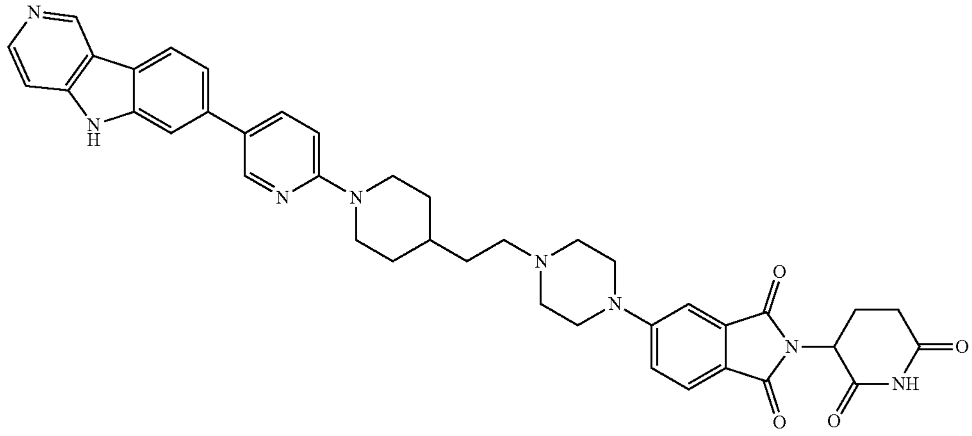
Step 1
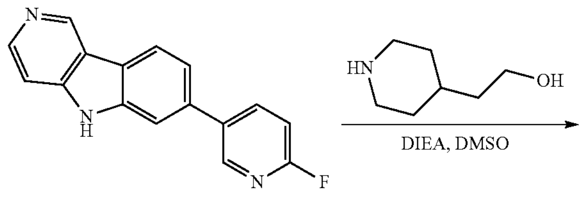
-continued
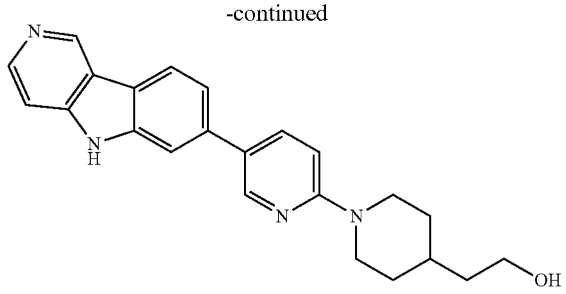
Into a 25-mL sealed tube purged and maintained with an inert atmosphere of nitrogen, was placed 2-fluoro-5-[5H-pyrido[4,3-b]indol-7-yl]pyridine (300 mg, 1.14 mmol, 1.0 equiv) and 2-(piperidin-4-yl)ethan-1-ol (735 mg, 5.69 mmol, 5.0 equiv) in DMSO (4 mL), to which was added DIEA (440 mg, 3.41 mmol, 3.0 equiv). The final reaction mixture was heated under microwave irradiation for 3 hr at 120° C. The reaction mixture was cooled to room temperature. The resulting solution was diluted with 10 mL of $H_2O$. The solids were removed by filtration. The resulting filtrate was concentrated to produce 300 mg (crude) of 2-[1-(5-[5H-pyrido[4,3-b]indol-7-yl]pyridin-2-yl)piperidin-4-yl]ethan-1-ol as a yellow solid.

Step 2

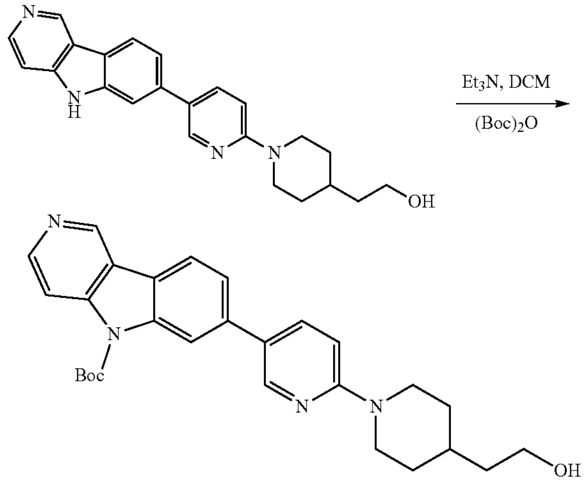

Into a 50-mL round-bottom flask, was placed 2-[1-(5-[5H-pyrido[4,3-b]indol-7-yl]pyridin-2-yl)piperidin-4-yl]ethanol (300 mg, 0.81 mmol, 1.0 equiv) and di-tert-butyl dicarbonate (211 mg, 0.97 mmol, 1.2 equiv) in DCM (10 mL), to which was added $Et_3N$ (163 mg, 1.61 mmol, 2.0 equiv). The resulting solution was stirred for 3 hr at room temperature. The resulting mixture was concentrated. The residue was applied onto a silica gel column eluting with dichloromethane/methanol (15:1). This resulted in 300 mg (79%) of tert-butyl 7-[6-[4-(2-hydroxyethyl)piperidin-1-yl]pyridin-3-yl]pyrido[4,3-b]indole-5-carboxylate as a yellow solid.

Step 3

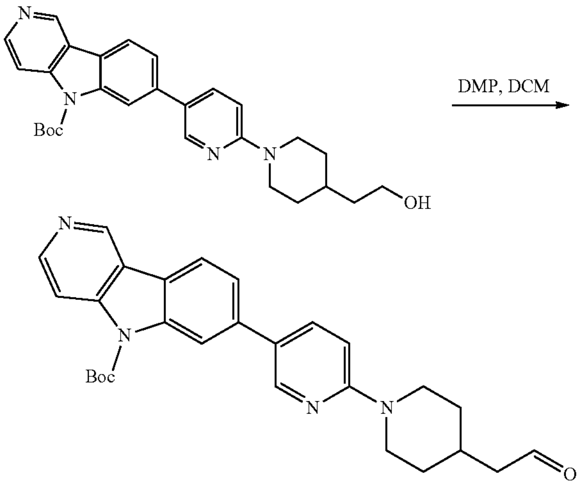

Into a 50-mL round-bottom flask, was placed tert-butyl 7-[6-[4-(2-hydroxyethyl)piperidin-1-yl]pyridin-3-yl]pyrido[4,3-b]indole-5-carboxylate (300 mg, 0.64 mmol, 1.0 equiv) in DCM (5 mL), to which was added DMP (538 mg, 1.27 mmol, 2.0 equiv). The resulting solution was stirred for 3 hr at room temperature. The resulting mixture was concentrated. The residue was applied onto a silica gel column eluting with dichloromethane/methanol (20:1). This resulted in 200 mg (67%) of tert-butyl 7-[6-[4-(2-oxoethyl)piperidin-1-yl]pyridin-3-yl]pyrido[4,3-b]indole-5-carboxylate as a yellow solid.

Step 4

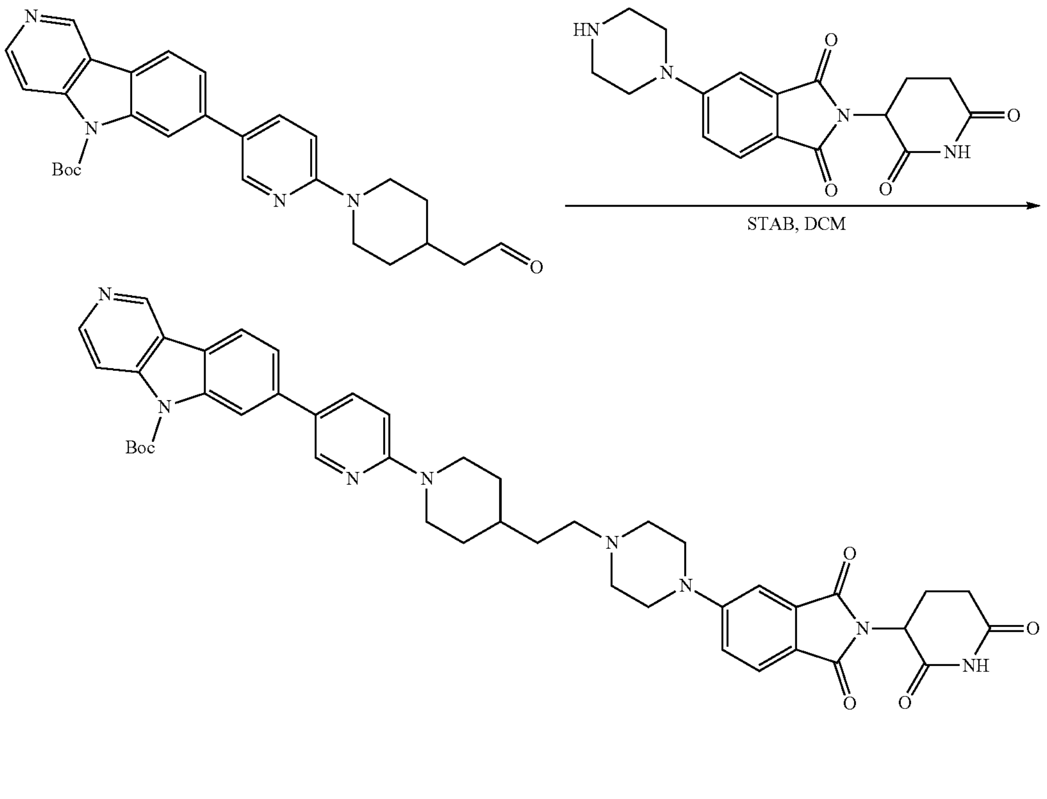

Into a 50-mL round-bottom flask, was placed tert-butyl 7-[6-[4-(2-oxoethyl)piperidin-1-yl]pyridin-3-yl]pyrido[4,3-b]indole-5-carboxylate (100 mg, 0.21 mmol, 1.0 equiv) and 2-(2,6-dioxopiperidin-3-yl)-5-(piperazin-1-yl)isoindole-1,3-dione (72.7 mg, 0.21 mmol, 1.0 equiv) in DCM (2 mL) and MeOH (1 mL), to which was added STAB (90.1 mg, 0.43 mmol, 2.0 equiv). The resulting solution was stirred for 1 hr at room temperature. The reaction was then quenched by the addition of $H_2O$ (1 mL). The resulting mixture was concentrated. The residue was applied onto a silica gel column eluting with dichloromethane/methanol (10:1). This resulted in 120 mg (71%) of tert-butyl 7-[6-[4-(2-[4-[2-(2,6-dioxopiperidin-3-yl)-1,3-dioxoisoindol-5-yl]piperazin-1-yl]ethyl)piperidin-1-yl]pyridin-3-yl]pyrido[4,3-b]indole-5-carboxylate as a yellow solid.

Step 5

Into a 50-mL round-bottom flask, was placed 2-(2,6-dioxopiperidin-3-yl)-5-(4-[2-[1-(5-[5H-pyrido[4,3-b]indol-7-yl]pyridin-2-yl)piperidin-4-yl]ethyl]piperazin-1-yl)isoindole-1,3-dione (120 mg, 0.17 mmol, 1.0 equiv) in DCM (2 mL), to which was added TFA (1 mL). The resulting solution was stirred for 1 hr at room temperature. The resulting mixture was concentrated. The crude product was purified by prep-HPLC with the following conditions: XBridge Prep OBD C18 Column 30*50 mm 5 um; Mobile Phase A: water (0.1% FA), Mobile Phase B: acetonitrile; Flow rate: 60 mL/min; Gradient: 27% B to 58% B in 10 min; 254 nm; This resulted in 52.3 mg (44%) of 2-(2,6-dioxopiperidin-3-yl)-5-(4-[2-[1-(5-[5H-pyrido[4,3-b]indol-7-yl]pyridin-2-yl)piperidin-4-yl]ethyl]piperazin-1-yl)isoindole-1,3-dione as a yellow solid.

Using analogous procedures the following exemplar compound was prepared: 397.

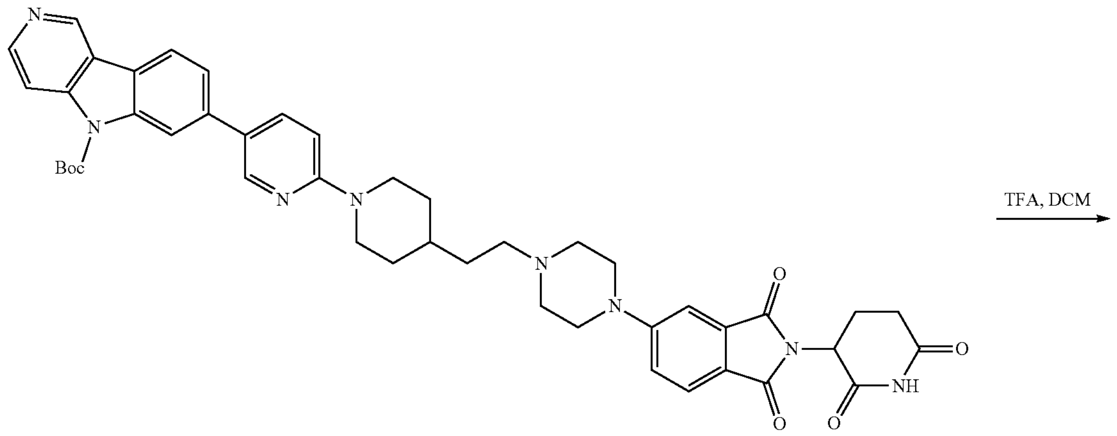

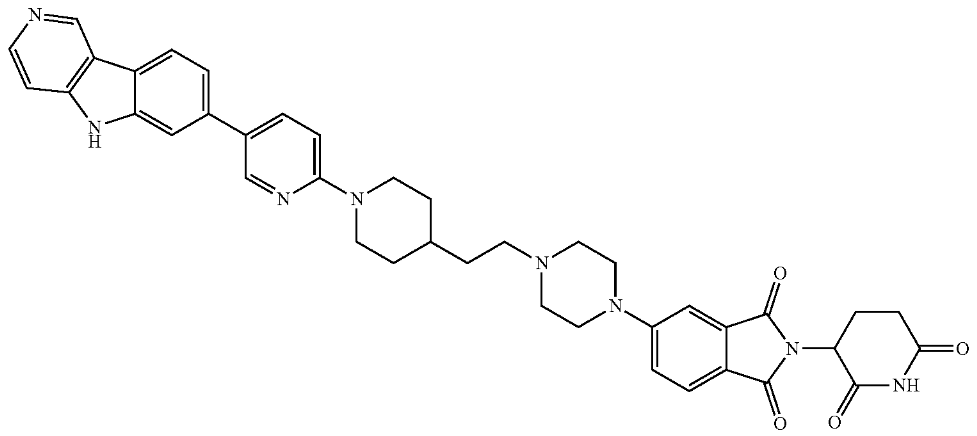 [SMILES: O=C1CCC(N2C(=O)c3ccc(N4CCN(CCC5CCN(c6ccc(-c7ccc8c(c7)[nH]c7ccncc78)cn6)CC5)CC4)cc3C2=O)C(=O)N1]

Exemplary Compound 400

Exemplary Synthesis of Exemplary Compounds 398 and 399

Exemplary Compound 398

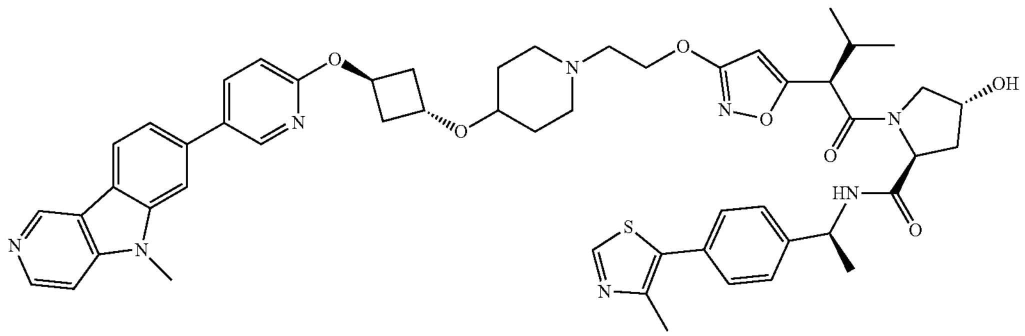

Exemplary Compound 399

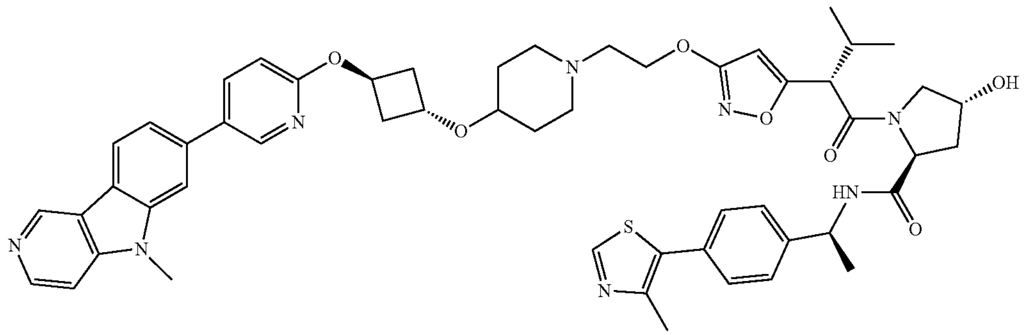

Step 1

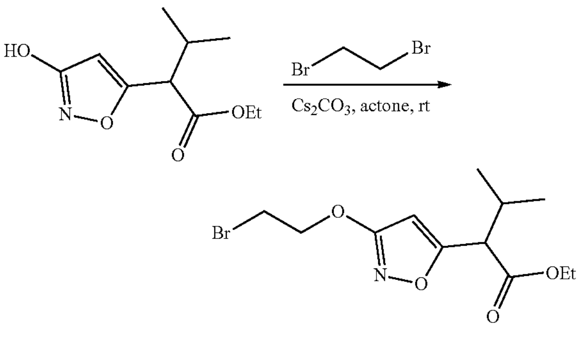

Into a 250-mL round-bottom flask, was placed ethyl 2-(3-hydroxy-1,2-oxazol-5-yl)-3-methylbutanoate (1 g, 4.69 mmol, 1 equiv), $Cs_2CO_3$ (4.5 g, 13.81 mmol, 3.0 equiv), and 1,2-dibromoethane (2.60 g, 13.84 mmol) in acetone (100 mL). The resulting mixture was stirred overnight at room temperature. The reaction was then quenched by water (100 mL). The resulting mixture was extracted with of ethyl acetate (100 mL×3), and the organic layers were combined, dried over anhydrous sodium sulfate and concentrated under reduced pressure. The residue was applied onto a silica gel column eluting with ethyl acetate/petroleum ether (3:10). This resulted in 600 mg (40%) of ethyl 2-[3-(2-bromoethoxy)-1,2-oxazol-5-yl]-3-methylbutanoate as light yellow oil.

Step 2

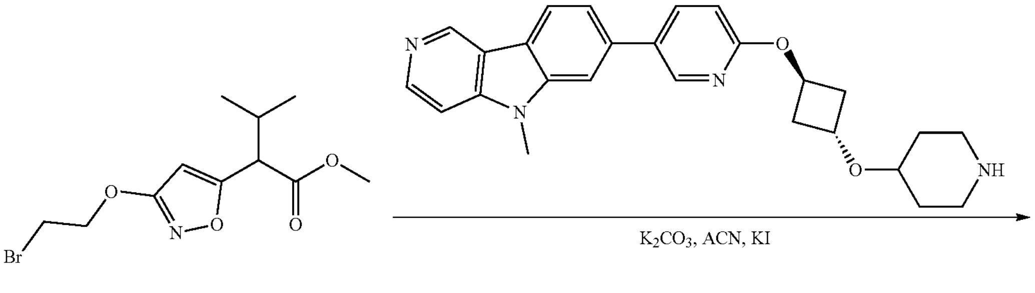

-continued

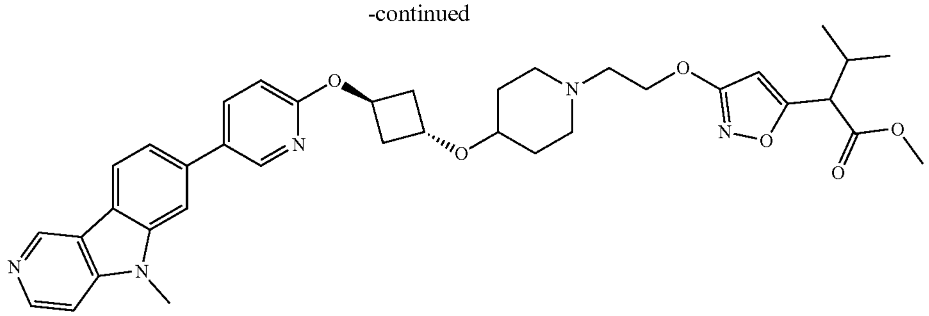

Into a 10-mL sealed tube, was placed methyl 2-(3-ethoxy-1,2-oxazol-5-yl)-3-methylbutanoate (150 mg, 0.66 mmol, 1.0 equiv) and [5-methyl-5H-pyrido[4,3-b]indol-7-yl]-2-[(1r,3r)-3-(piperidin-4-yloxy)cyclobutoxy]pyridine (339 mg, 0.79 mmol, 1.2 equiv) in ACN (3 mL), to which was added $K_2CO3$ (182 mg, 1.32 mmol, 2.0 equiv), KI (110 mg, 0.66 mmol, 1.0 equiv). The resulting solution was stirred for 12 hr at 120° C. in an oil bath. The reaction mixture was cooled to room temperature. The reaction was then quenched by the addition of 30 mL of water. The resulting solution was extracted with (3×50 mL) of ethyl acetate. The resulting mixture was washed with (3×100 mL) of brine. The mixture was dried over anhydrous sodium sulfate and concentrated under vacuum. This resulted in 200 mg (crude) of methyl 3-methyl-2-[3-(2-[4-[(1r,3r)-3-[(5-[5-methyl-5H-pyrido[4,3-b]indol-7-yl]pyridin-2-yl)oxy]cyclobutoxy]piperidin-1-yl]ethoxy)-1,2-oxazol-5-yl]butanoate as a yellow oil.

3-Methyl-2-[3-(2-[4-[(1r,3r)-3-[(5-[5-methyl-5H-pyrido[4,3-b]indol-7-yl]pyridin-2-yl)oxy]cyclobutoxy]piperidin-1-yl]ethoxy)-1,2-oxazol-5-yl]butanoate was converted to the title compounds as described for exemplary compounds 395 and 396.

Exemplary Synthesis of Exemplary Compound 401

Step 1

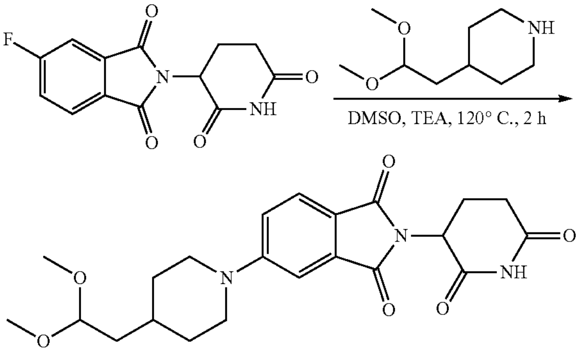

To a mixture of 4-(2,2-dimethoxyethyl)piperidine (200 mg, 1.15 mmol, 1 eq) and 2-(2,6-dioxo-3-piperidyl)-5-fluoro-isoindoline-1,3-dione (318 mg, 1.15 mmol, 1 eq) in dimethyl sulfoxide (2 mL) was added N,N-diisopropylethylamine (447 mg, 3.46 mmol, 3 eq) in one portion. The mixture was stirred at 120° C. for 2 h. The mixture was added brine (30 mL) and extracted with ethyl acetate (30 mL×3). The organic layer was dried over sodium sulfate, filtered and concentrated. The residue was purified by silica gel chromatography (petroleum ether:ethyl acetate=10:1 to 1:1). 5-[4-(2,2-Dimethoxyethyl)-1-piperidyl]-2-(2,6-dioxo-3-piperidyl)isoindoline-1,3-dione (400 mg, 0.93 mmol) was obtained as a yellow solid.

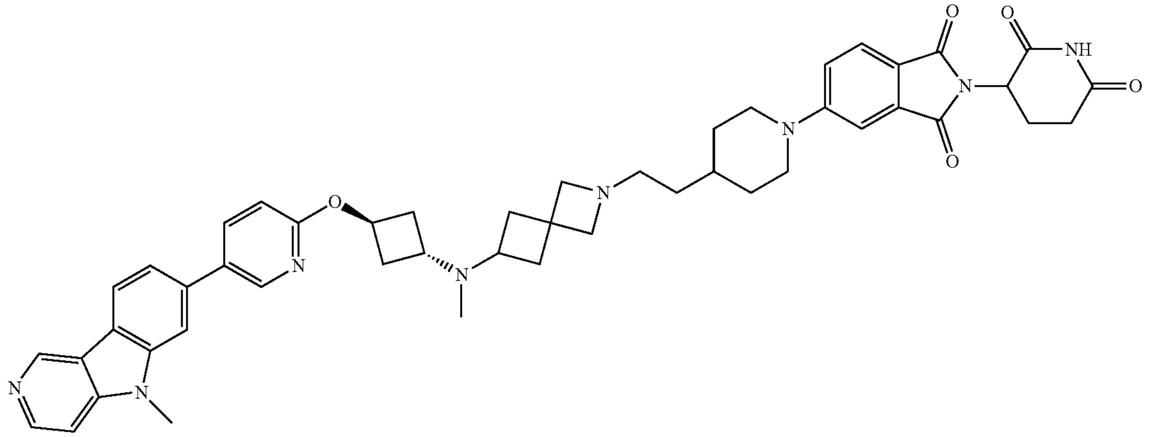 [SMILES: Cn1c2ccncc2c2ccc(-c3ccc(O[C@H]4C[C@H](N(C)C5CC6(C5)CN(CCC5CCN(c7ccc8c(c7)C(=O)N(C7CCC(=O)NC7=O)C8=O)CC5)C6)C4)nc3)cc21]

Step 2

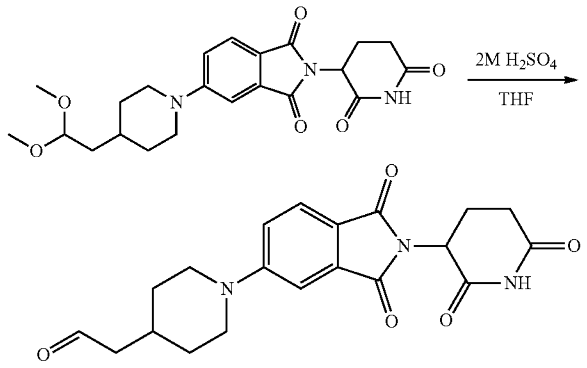

To a solution of 5-[4-(2,2-dimethoxyethyl)-1-piperidyl]-2-(2,6-dioxo-3-piperidyl) isoindoline-1,3-dione (120 mg, 0.27 mmol, 1 eq) in tetrahydrofuran (5 mL) was added sulfuric acid (2 M, 5 mL, 40 eq). The mixture was stirred at 50° C. for 1 h. The mixture was extracted with ethyl acetate (50 mL×3) and washed with saturated sodium bicarbonate (50 mL). The organic layer was dried with sodium sulfate and concentrated. 2-[1-[2-(2,6-Dioxo-3-piperidyl)-1,3-di-oxo-isoindolin-5-yl]-4-piperidyl]acetaldehyde (100 mg, 0.26 mmol) was obtained as a yellow oil and used directly in the next step without further purification.

2-[1-[2-(2,6-Dioxo-3-piperidyl)-1,3-dioxo-isoindolin-5-yl]-4-piperidyl]acetaldehyde was converted to the title compound as shown in the scheme below.

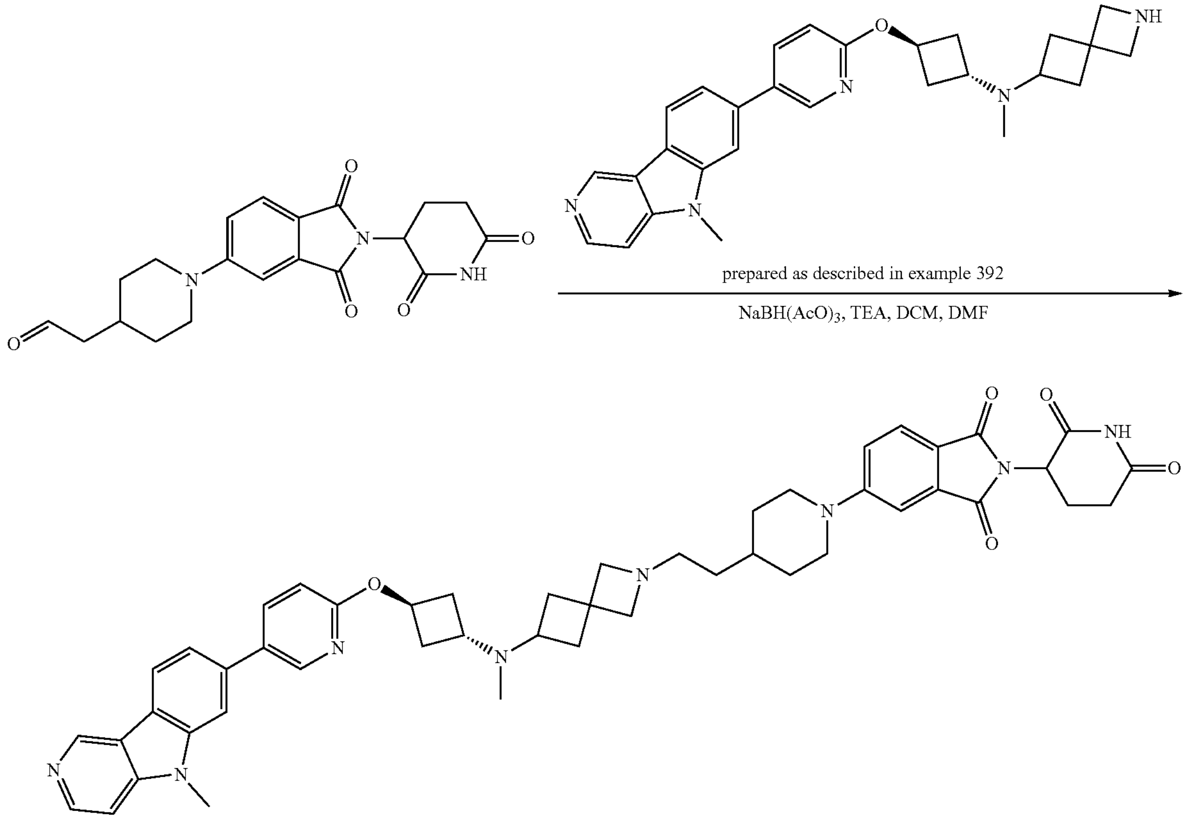

Exemplary Compound 401

Exemplary Synthesis of Exemplary Compound 402

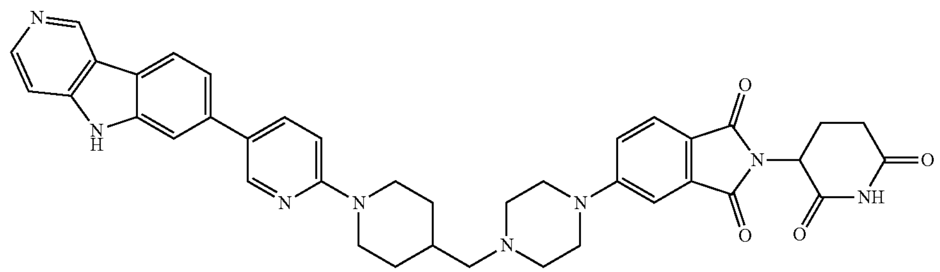 [SMILES: O=C1CCC(N2C(=O)c3ccc(N4CCN(CC5CCN(c6ccc(-c7ccc8c(c7)[nH]c7ccncc78)cn6)CC5)CC4)cc3C2=O)C(=O)N1]

Step 1

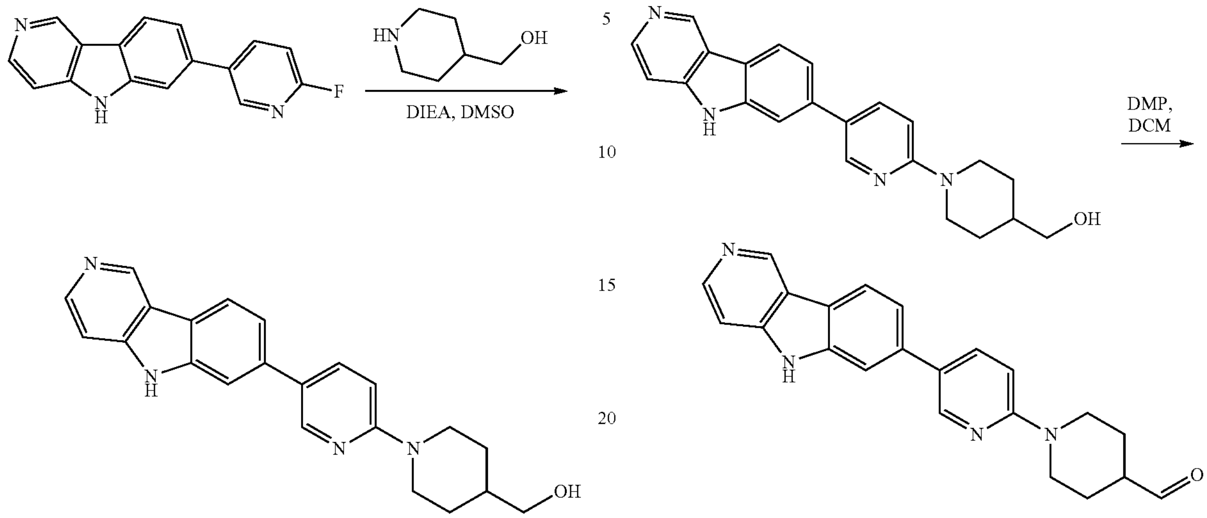

Into a 20-mL sealed tube, was placed 2-fluoro-5-[5H-pyrido[4,3-b]indol-7-yl]pyridine (200 mg, 0.76 mmol, 1.0 equiv) in DMSO (10 mL), to which was added DIEA (196 mg, 1.52 mmol, 2.0 equiv), and piperidin-4-ylmethanol (175 mg, 1.52 mmol, 2.0 equiv). The final reaction mixture was heated under microwave irradiation for 2 hr at 120° C. The reaction mixture was cooled to room temperature. The solids were collected by filtration. The filtrate was concentrated under vacuum to produce 200 mg (crude) of [1-(5-[5H-pyrido[4,3-b]indol-7-yl]pyridin-2-yl)piperidin-4-yl]methanol as a yellow solid.

Step 2

Into a 250-mL round-bottom flask, was placed [l-(5-[5H-pyrido[4,3-b]indol-7-yl]pyridin-2-yl)piperidin-4-yl]methanol (120 mg, 0.34 mmol, 1.0 equiv) in DCM (50 mL), to which was added DMP (426 mg, 1.00 mmol, 3.0 equiv). The resulting solution was stirred for 2 hr at 25° C. The reaction was then quenched by the addition of 50 mL of water. The resulting solution was extracted with (3×50 mL) of dichloromethane, and organic phase was concentrated. The residue was applied onto a silica gel column eluting with dichloromethane/methanol (8/1). The collected fractions were combined and concentrated under vacuum. This resulted in 50 mg (42%) of 1-(5-[5H-pyrido[4,3-b]indol-7-yl]pyridin-2-yl)piperidine-4-carbaldehyde as a yellow oil.

Step 3

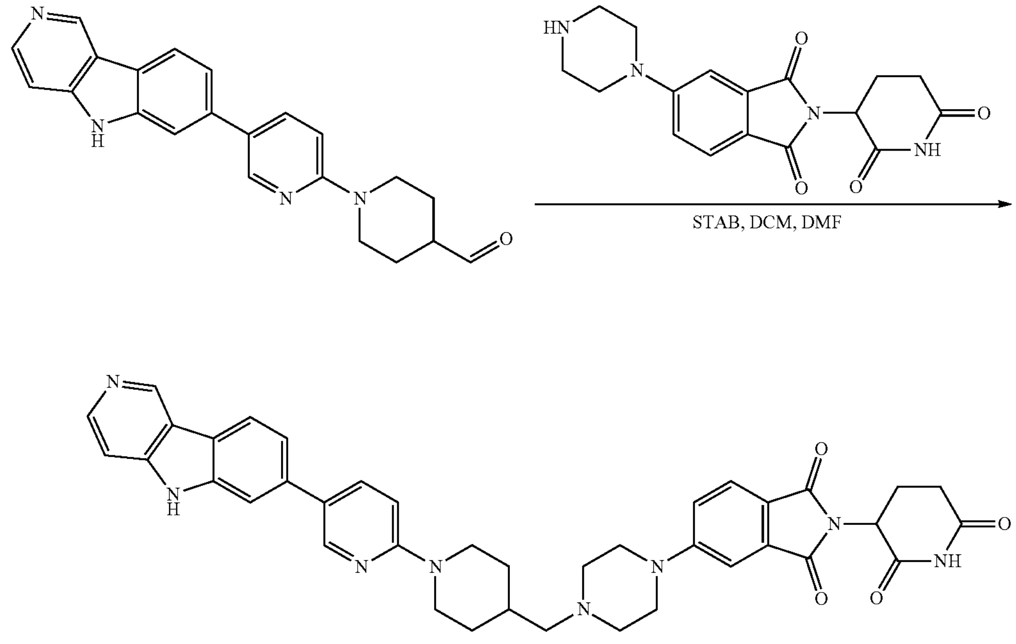

Exemplary Compound 402

Into a 25-mL round-bottom flask, was placed 1-(5-[5H-pyrido[4,3-b]indol-7-yl]pyridin-2-yl)piperidine-4-carbaldehyde (50 mg, 0.14 mmol, 1.0 equiv) and 2-(2,6-dioxopiperidin-3-yl)-5-(piperazin-1-yl)-2,3-dihydro-1H-isoindole-1,3-dione (48 mg, 0.14 mmol, 1.0 equiv) in DCM (5 mL), to which was added STAB (59 mg, 0.28 mmol, 2.0 equiv). The resulting solution was stirred for 2 hr at 25° C. The resulting mixture was concentrated under vacuum. The crude product was purified by Prep-HPLC with the following conditions: Column, XBridge Prep OBD C18 Column, 19*150 mm, 5 um; Mobile Phase A: Water (with 10 mmol/L $NH_4HCO_3$), Mobile Phase B: $CH_3CN$; Gradient: 43% B to 50% B in 9 min; 254 nm; This resulted in 12.1 mg (13%) of 2-(2,6-dioxopiperidin-3-yl)-5-(4-[[1-(5-[5H-pyrido[4,3-b]indol-7-yl]pyridin-2-yl)piperidin-4-yl]methyl]piperazin-1-yl)-2,3-dihydro-1H-isoindole-1,3-dione as a yellow solid.

Exemplary Synthesis of Exemplary Compound 403

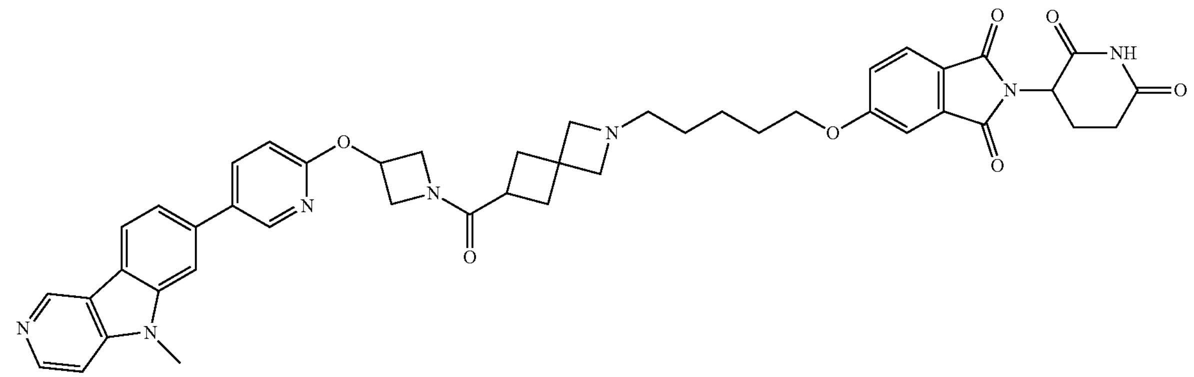 [SMILES: Cn1c2ccncc2c2ccc(-c3ccc(OC4CN(C(=O)C5CC6(C5)CN(CCCCCOc5ccc7c(c5)C(=O)N(C5CCC(=O)NC5=O)C7=O)C6)C4)nc3)cc21]

Step 1

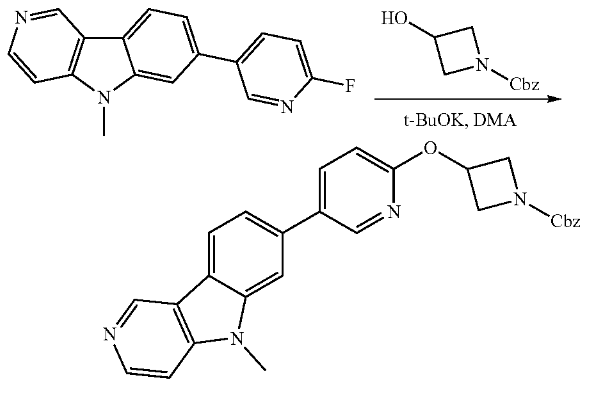

Into a 10-mL sealed tube, was placed 2-fluoro-5-[5-methyl-5H-pyrido[4,3-b]indol-7-yl]pyridine (500 mg, 1.80 mmol, 1.0 equiv) and benzyl 3-hydroxyazetidine-1-carboxylate (374 mg, 1.80 mmol, 1.0 equiv) in DMA (5 mL), t-BuOK (405 mg, 3.61 mmol, 2.0 equiv). The final reaction mixture was heated under microwave irradiation for 2 hr at 120° C. The reaction was then quenched by the addition of 50 mL of water. The resulting solution was extracted with (3x100 mL) of ethyl acetate. The resulting mixture was washed with (3x100 mL) of brine. The mixture was dried over anhydrous sodium sulfate and concentrated. This resulted in 500 mg (crude) of benzyl 3-[(5-[5-methyl-5H-pyrido[4,3-b]indol-7-yl]pyridin-2-yl)oxy]azetidine-1-carboxylate as a yellow oil.

Benzyl 3-[(5-[5-methyl-5H-pyrido[4,3-b]indol-7-yl]pyridin-2-yl)oxy]azetidine-1-carboxylate was converted to the title compound according to the scheme below using procedures described for other examples above and commonly known to those skilled in the art.

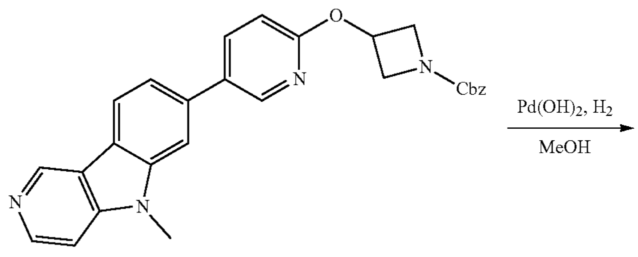

-continued
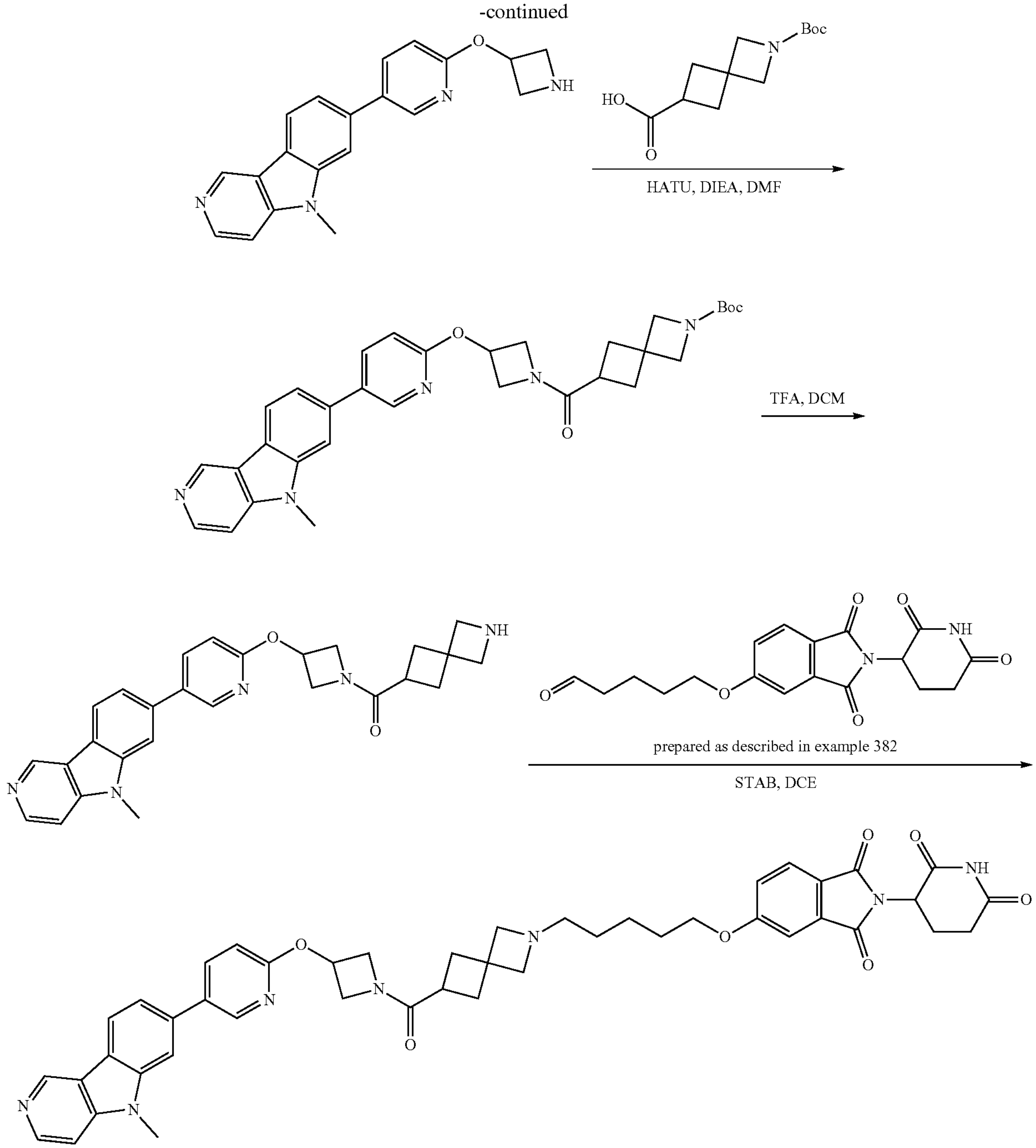
Exemplary Compound 403
Exemplary Synthesis of Exemplary Compound 404
Step 1
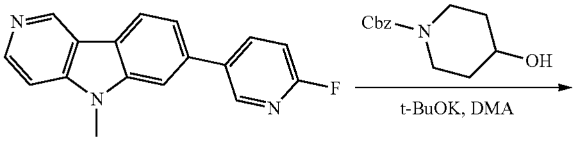
-continued
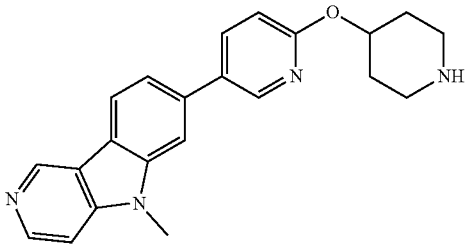

Into a 25-mL sealed tube purged and maintained with an inert atmosphere of nitrogen was placed 2-fluoro-5-[5-methylpyrido[4,3-b]indol-7-yl]pyridine (500 mg, 1.80 mmol, 1.0 equiv) and benzyl 4-hydroxypiperidine-1-carboxylate (636 mg, 2.71 mmol, 1.5 equiv) in DMA (10 mL), to which was added t-BuOK (405 mg, 3.61 mmol, 2.0 equiv). The final reaction mixture was heated under microwave irradiation for 3 hr at 120° C. The reaction mixture was cooled to room temperature. The residue was applied onto a silica gel column eluting with DCM:MeOH=20:1 to 5:1. The collected fractions were combined and concentrated, and the residue was further purified again by prep-TLC (DCM: MeOH=7:1) This resulted in 140 mg (22%) of 5-[5-methylpyrido[4,3-b]indol-7-yl]-2-(piperidin-4-yloxy)pyridine as a yellow oil.

5-[5-methylpyrido[4,3-b]indol-7-yl]-2-(piperidin-4-yloxy)pyridine was converted to the title compound according to the scheme below using procedures described in US 20180125821, other examples above and commonly known to those skilled in the art.

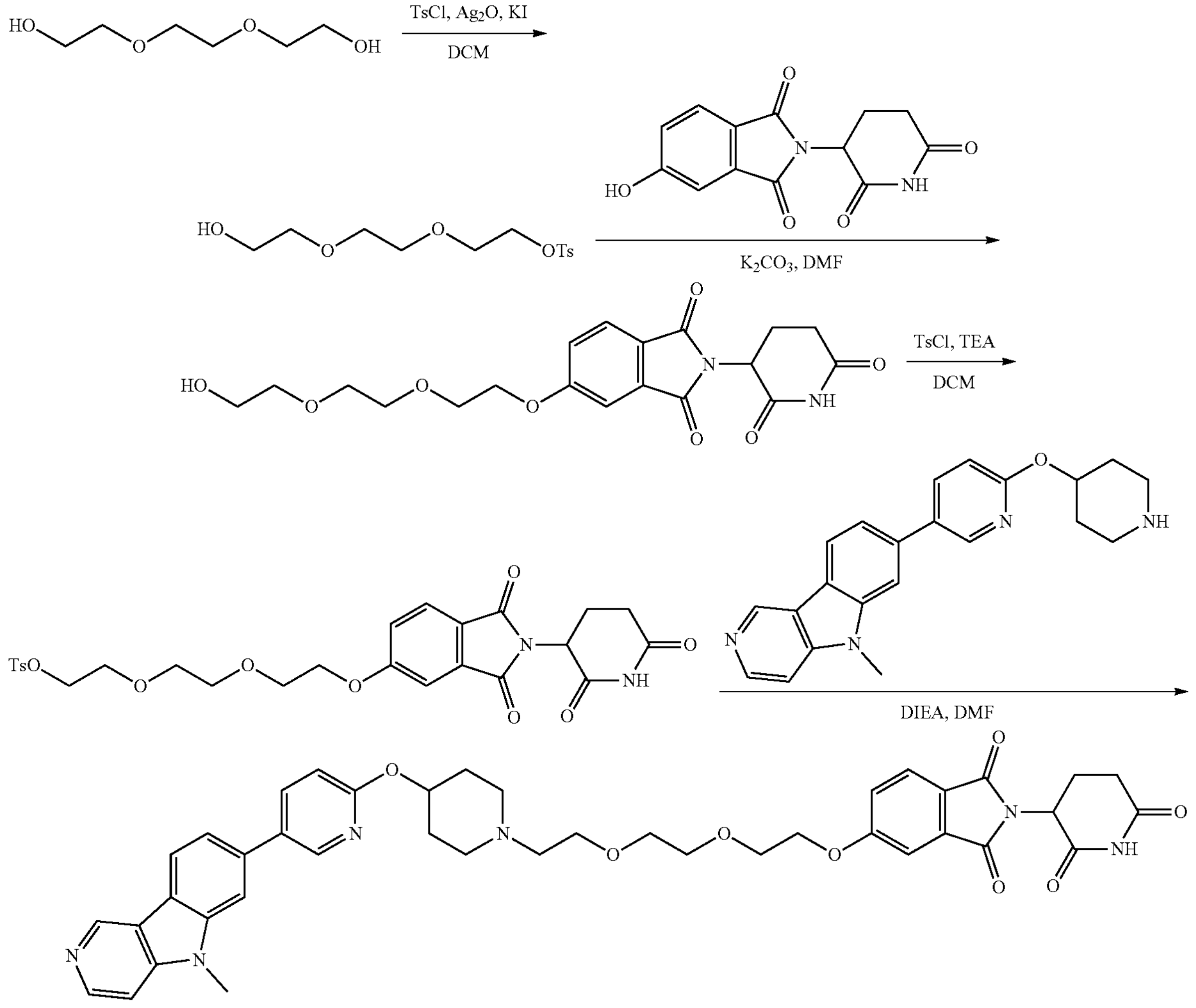

Exemplary Compound 404

The following examples were prepared using procedures described by Crew, A. et al. in US 20180125821 and exemplified by the scheme below: exemplary compound 405 and exemplary compound 407.

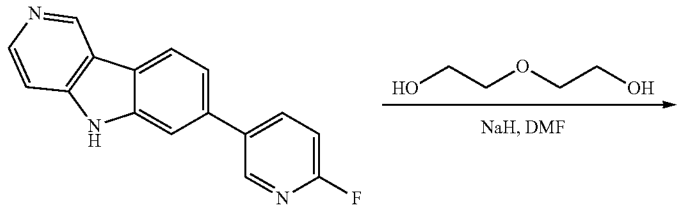

-continued
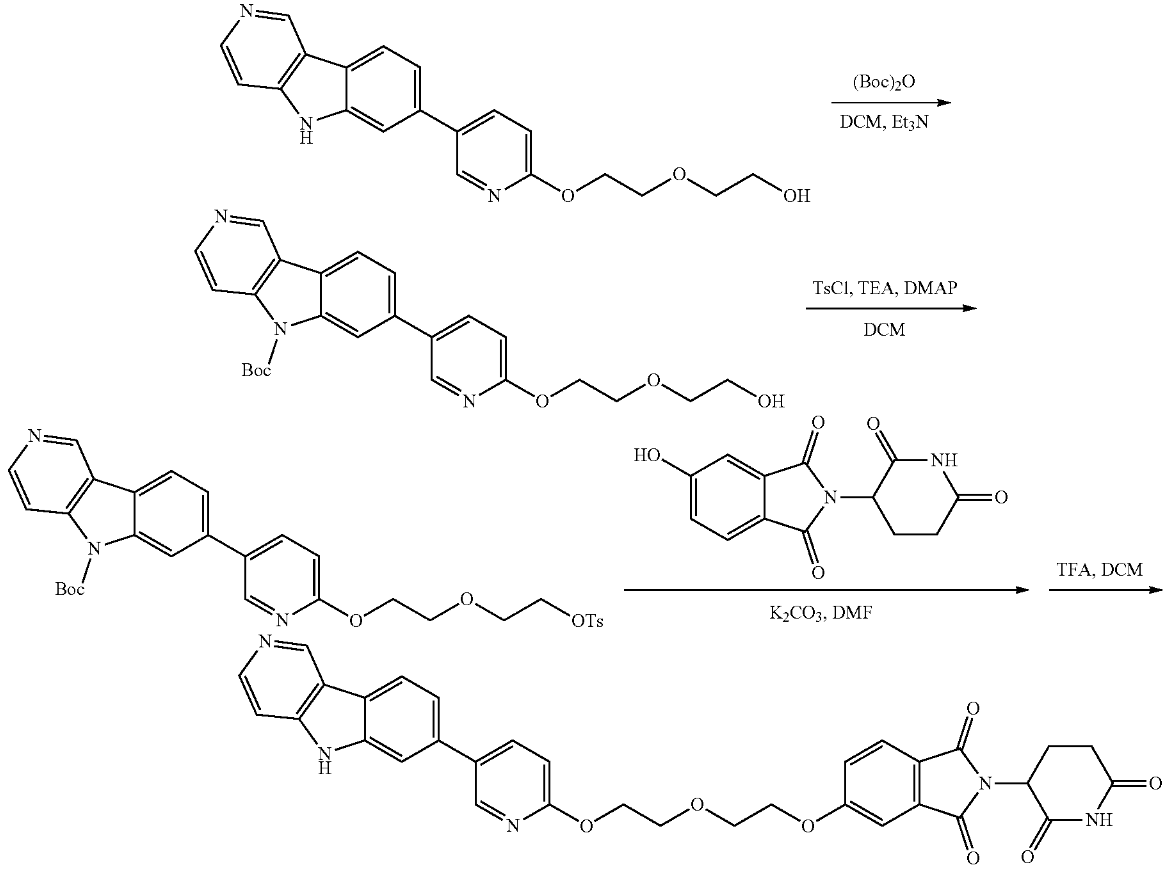
Exemplary Compound 405
Exemplary Synthesis of Exemplary Compound 406
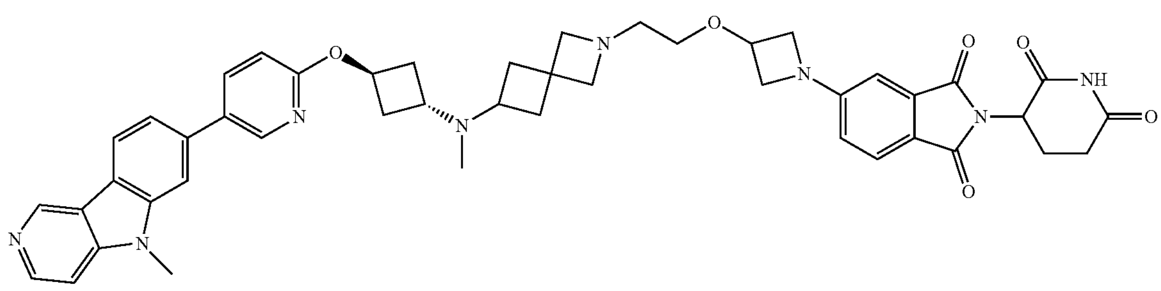 [SMILES: Cn1c2ccncc2c2ccc(-c3ccc(O[C@H]4C[C@H](N(C)C5CC6(C5)CN(CCOC5CN(c7ccc8c(c7)C(=O)N(C7CCC(=O)NC7=O)C8=O)C5)C6)C4)nc3)cc21]
Step 1
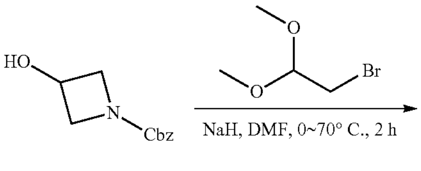
-continued
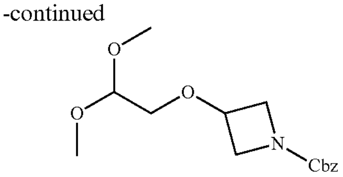
To a mixture of benzyl 3-hydroxyazetidine-1-carboxylate (500 mg, 2.41 mmol, 1 eq) in N,N-dimethylformamide (20 mL) was added sodium hydride (96 mg, 2.41 mmol, 60% in mineral oil, 1 eq) at 0° C. The mixture was stirred at 25° C. for 0.5 h. Then 2-bromo-1,1-dimethoxy-ethane (1.22 g, 7.24 mmol, 3 eq) was added, and the reaction mixture was stirred at 80° C. for 2 h. The mixture was quenched by the addition of water (100 mL), extracted with ethyl acetate (30 mL×3), the combined organic phase was washed with brine (30 mL), dried over anhydrous sodium sulfate, filtered and concentrated under reduced pressure. The residue was purified by silica gel column chromatography (petroleum ether:ethyl acetate=10:0 to 3:1). Compound benzyl 3-(2,2-dimethoxyethoxy) azetidine-1-carboxylate (400 mg, 1.35 mmol, 56% yield) was obtained as a colorless oil.

Step 2

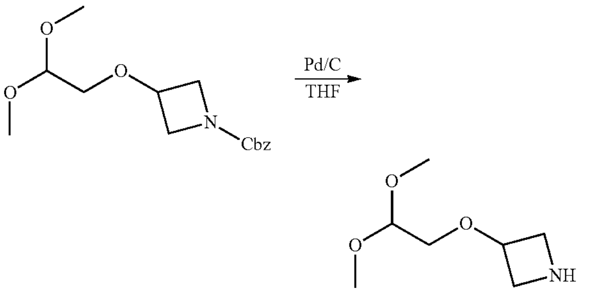

To a solution of benzyl 3-(2, 2-dimethoxyethoxy)azetidine-1-carboxylate (300 mg, 1.02 mmol, 1 eq) in tetrahydrofuran (10 mL) was added 10% palladium on carbon (100 mg) under nitrogen. The suspension was degassed under vacuum and purged with hydrogen several times. The mixture was stirred under hydrogen (15 psi) at 25° C. for 12 h. The mixture was filtered and concentrated under reduced pressure. The desired crude product 3-(2, 2-dimethoxyethoxy)azetidine (150 mg, 0.93 mmol) was obtained as a colorless oil and used directly in the next step.

Step 3

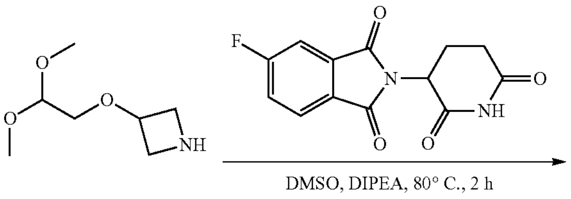

-continued

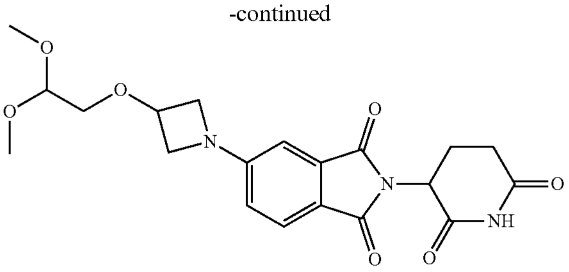

To a solution of 3-(2,2-dimethoxyethoxy)azetidine (150 mg, 0.93 mmol, 1 eq) in dimethyl sulfoxide (3 mL) was added 2-(2,6-dioxo-3-piperidyl)-5-fluoro-isoindoline-1,3-dione (308 mg, 1.12 mmol, 1.2 eq) and N, N-diisopropylethylamine (240 mg, 1.86 mmol, 2 eq). The mixture was stirred at 80° C. for 2 h. The reaction mixture was poured into water (3 mL) and extracted with ethyl acetate (6 mL×3). The combined organic layer was washed with brine (3 mL), dried over anhydrous sodium sulfate, filtered, and the filtrate was concentrated. The crude product was purified by prep-TLC (dichloromethane:methanol=10:1). The desired product 5-[3-(2,2-dimethoxyethoxy)azetidin-1-yl]-2-(2,6-dioxo-3-piperidyl)isoindoline-1,3-dione (200 mg) was obtained as a yellow oil.

5-[3-(2,2-dimethoxyethoxy)azetidin-1-yl]-2-(2,6-dioxo-3-piperidyl)isoindoline-1,3-dione was converted to the title compound as described for exemplary compound 401.

Exemplary Synthesis of Exemplary Compound 408

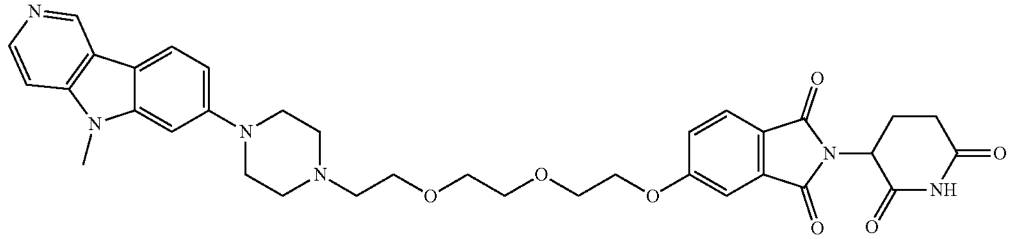 [SMILES: Cn1c2ccncc2c2ccc(N3CCN(CCOCCOCCOc4ccc5c(c4)C(=O)N(C4CCC(=O)NC4=O)C5=O)CC3)cc21]

Step 1

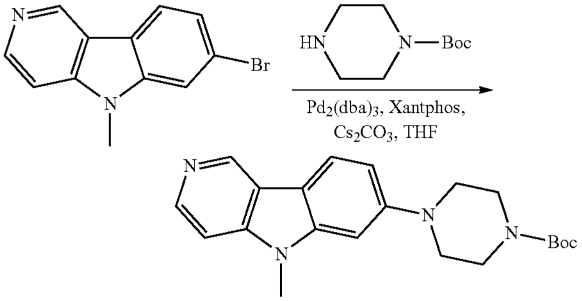

Into a 50-mL round-bottom flask purged and maintained with an inert atmosphere of nitrogen, was placed 7-bromo-5-methylpyrido[4,3-b]indole (100 mg, 0.38 mmol, 1.0 equiv), tert-butyl piperazine-1-carboxylate (107 mg, 0.57 mmol, 1.5 equiv), $Pd_2(dba)_3$ (70 mg, 0.08 mmol, 0.2 equiv), Xantphos (44 mg, 0.08 mmol, 0.2 equiv), and $Cs_2CO_3$ (373 mg, 1.15 mmol, 3.0 equiv) in THF (10 mL). The resulting solution was stirred for 2 hr at 90° C. The reaction mixture was cooled to room temperature. The solids were filtered out. The resulting solution was extracted with (3x30 mL) of ethyl acetate, dried over anhydrous sodium sulfate and concentrated. The residue was applied onto a silica gel column eluting with ethyl acetate/petroleum ether (1:1). This resulted in 80 mg (57%) of tert-butyl 4-[5-methylpyrido[4,3-b]indol-7-yl]piperazine-1-carboxylate as a solid.

tert-Butyl 4-[5-methylpyrido[4,3-b]indol-7-yl]piperazine-1-carboxylate was converted to the title compound as shown below and using procedures described in US 20180125821 and for other examples above.

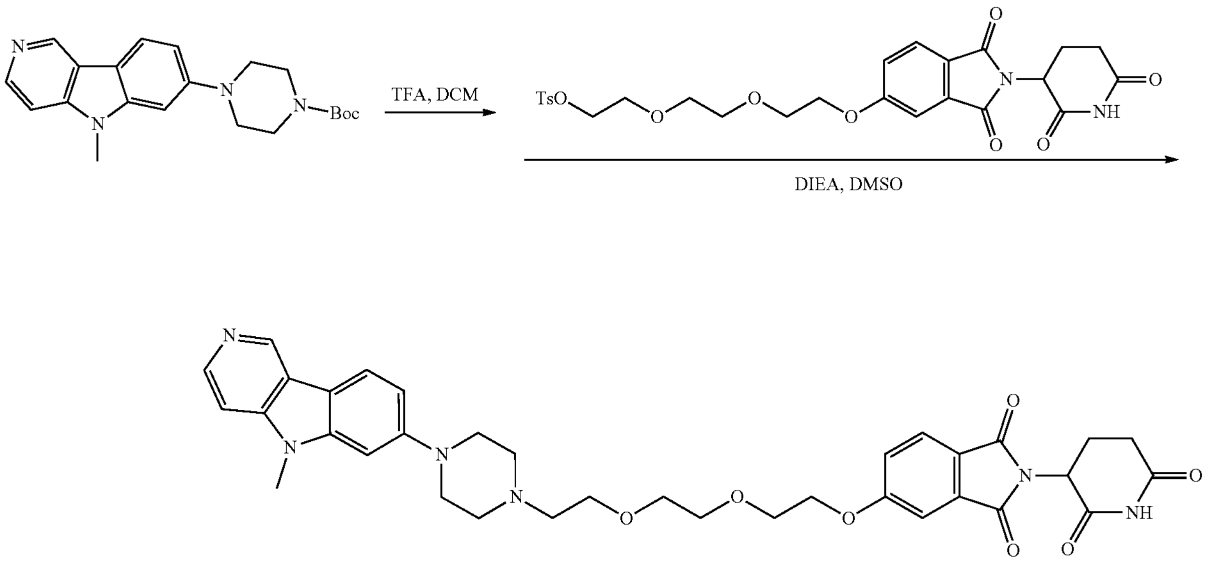

Exemplary Compound 408

Exemplary Synthesis of Exemplary Compound 409

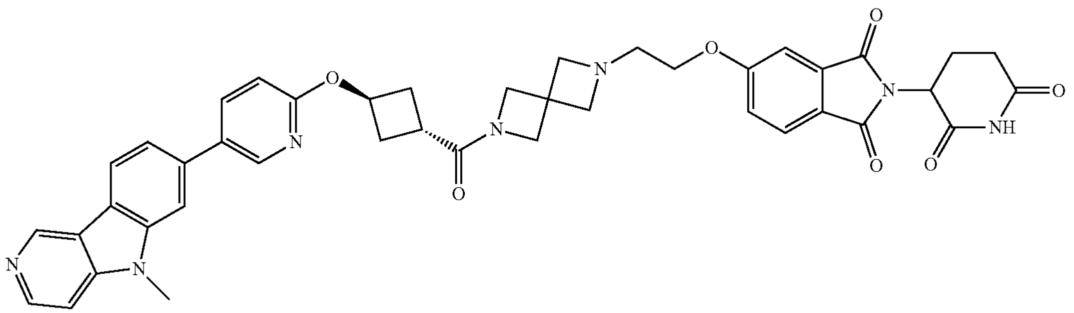 [SMILES: Cn1c2ccncc2c2ccc(-c3ccc(O[C@H]4C[C@H](C(=O)N5CC6(CN(CCOc7ccc8c(c7)C(=O)N(C7CCC(=O)NC7=O)C8=O)C6)C5)C4)nc3)cc21]

Step 1

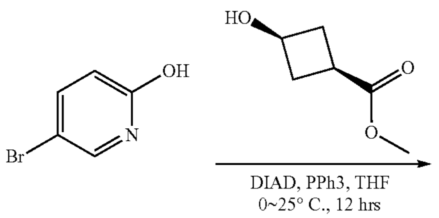

-continued

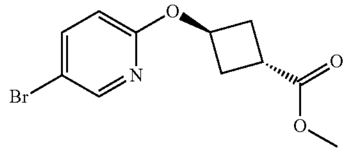

To a mixture of 5-bromopyridin-2-ol (2.94 g, 16.90 mmol, 1.1 eq), triphenylphosphine (4.84 g, 18.44 mmol, 1.2 eq) and methyl 3-hydroxycyclobutanecarboxylate (2.00 g, 15.37 mmol, 1 eq) in tetrahydrofuran (40 mL) was added diisopropyl azodicarboxylate (4.66 g, 23.05 mmol, 4.48 mL, 1.5 eq) at 0° C. Then the mixture was stirred at 25° C. for 12 h. The mixture was quenched by the addition of water (200 mL), extracted with ethyl acetate (40 mL×4), and the combined organic phase was washed with brine (30 mL), dried over anhydrous sodium sulfate, filtered and concentrated under reduced pressure. The residue was purified by silica gel column chromatography (petroleum ether:ethyl acetate=100:1 to 30:1). Compound methyl 3-[(5-bromo-2-pyridyl)oxy]cyclobutanecarboxylate (4 g, 13.98 mmol, 90% yield) was obtained as a colorless oil.

Methyl 3-[(5-bromo-2-pyridyl)oxy]cyclobutanecarboxylate was converted to the title compound according to the scheme below using procedures described for other examples above.
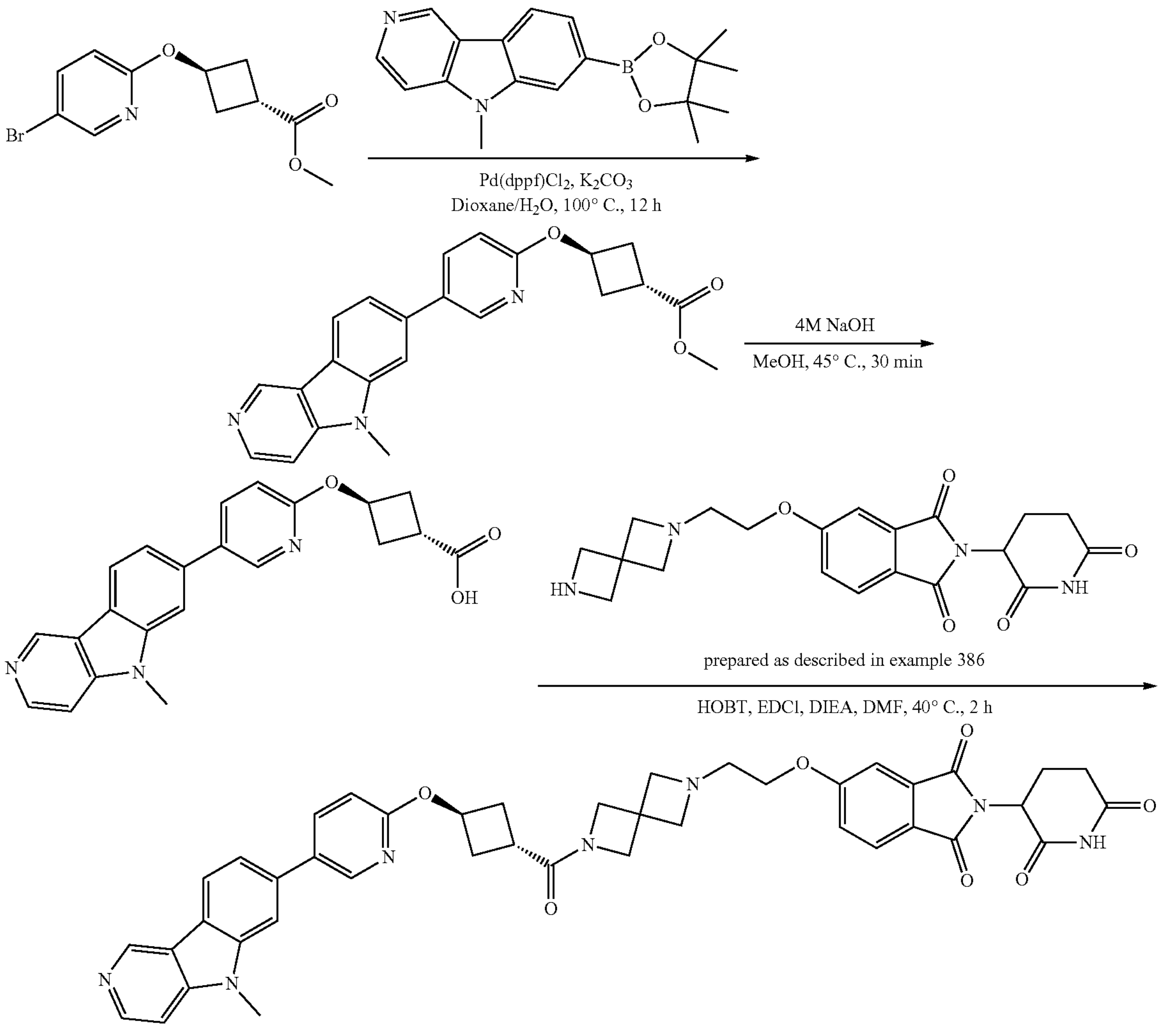
Exemplary Compound 409
Exemplary Synthesis of Exemplary Compound 410
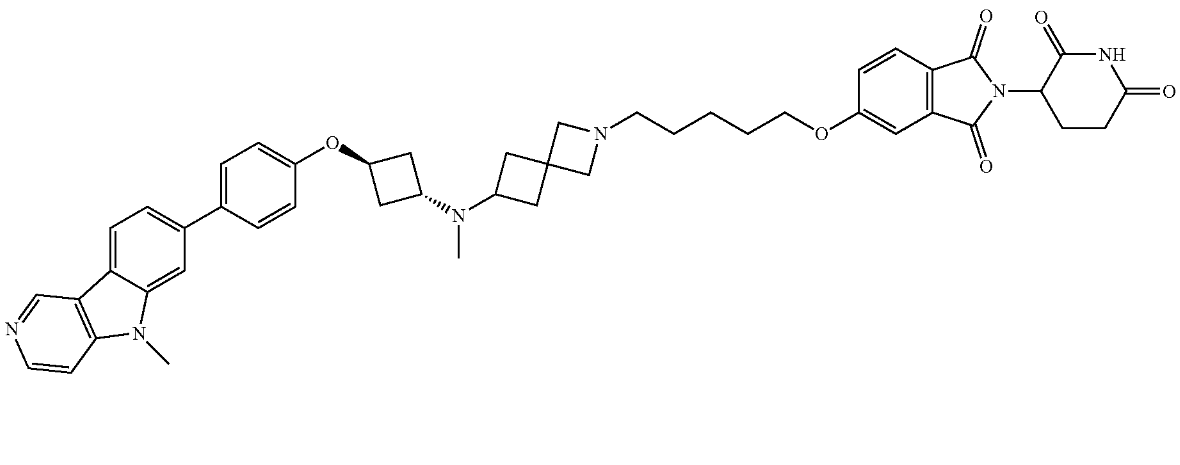

Prepared according to the scheme below using procedures analogous to those described for other examples above and commonly known to those skilled in the art.
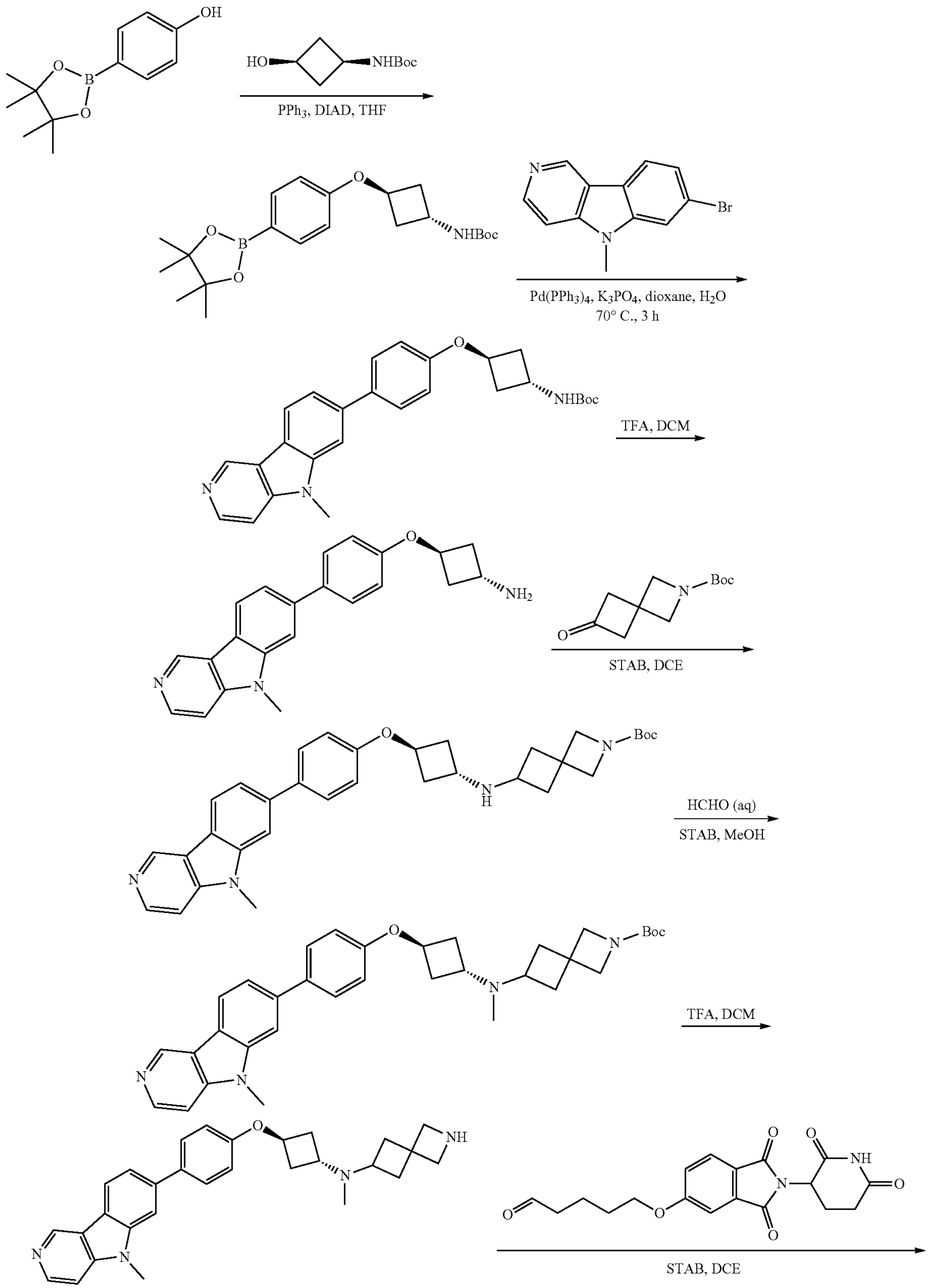

-continued
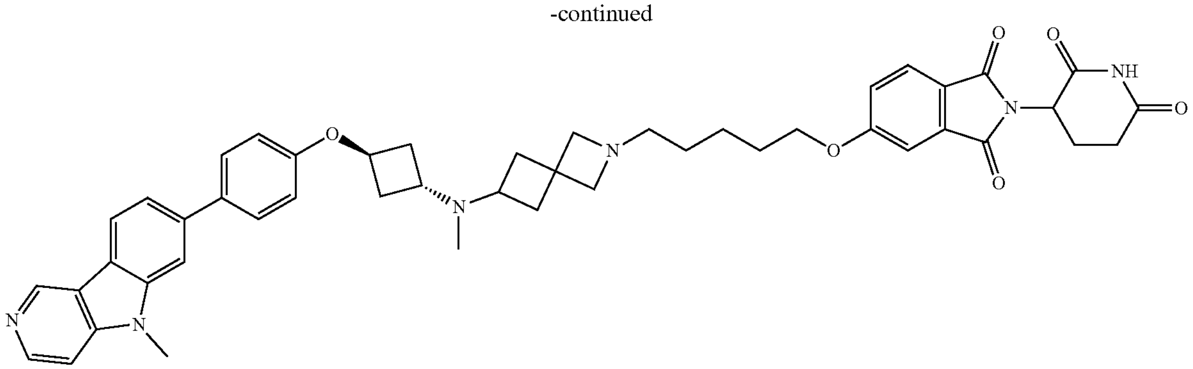
Exemplary Compound 410
Exemplary Synthesis of Exemplary Compound 411
Prepared according to the scheme below using procedures analogous to those described for other examples above and commonly known to those skilled in the art.
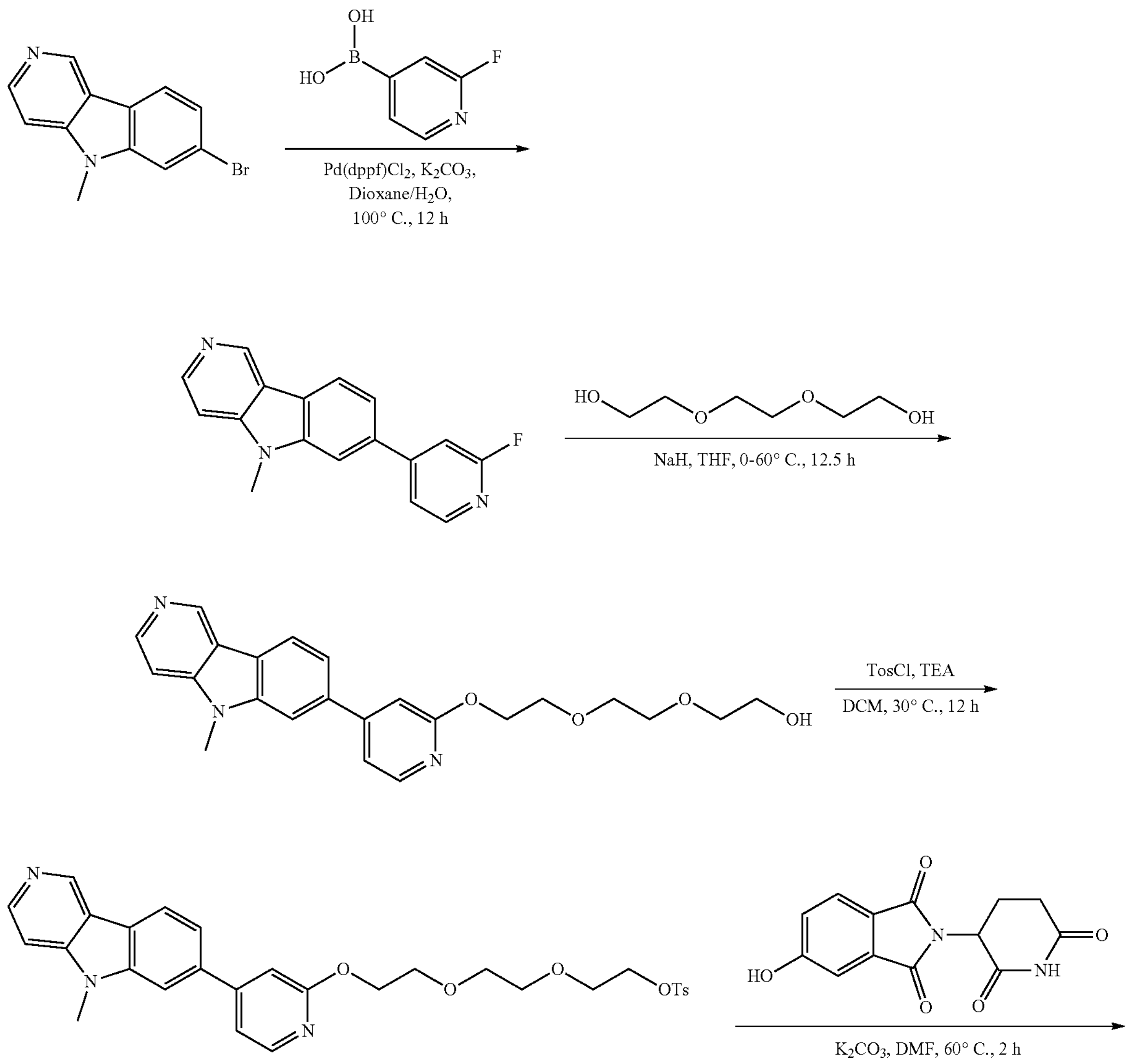

-continued

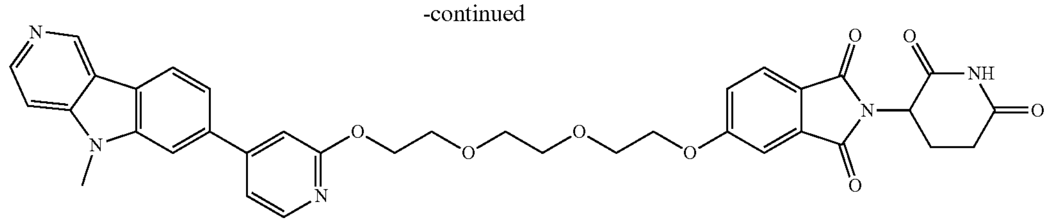

Exemplary Compound 411

Exemplary Synthesis of Exemplary Compound 412

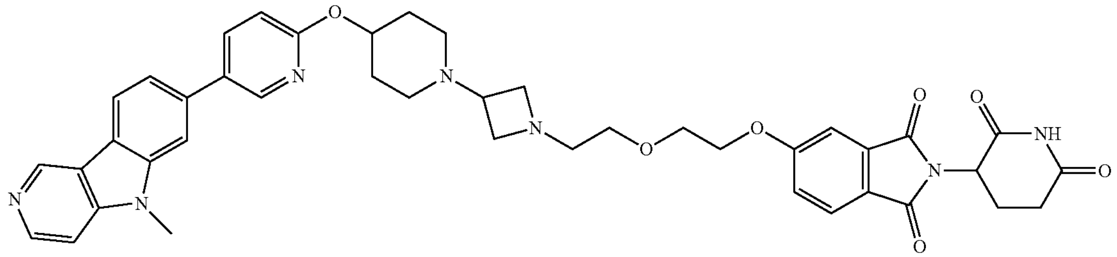 [SMILES: Cn1c2ccncc2c2ccc(-c3ccc(OC4CCN(C5CN(CCOCCOc6ccc7c(c6)C(=O)N(C6CCC(=O)NC6=O)C7=O)C5)CC4)nc3)cc21]

5-Methyl-7-(6-(piperidin-4-yloxy)pyridin-3-yl)-5H-pyrido[4,3-b]indole was prepared according to the scheme below using procedures from other examples above and commonly known to those skilled in the art.

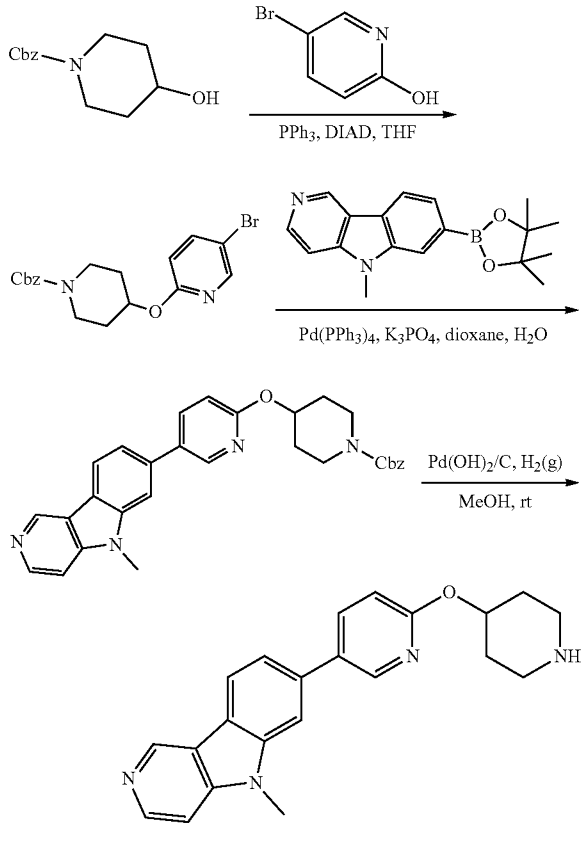

Step 4

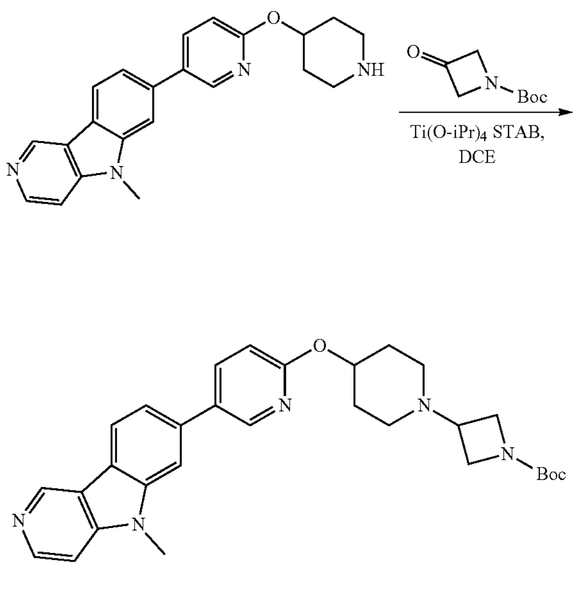

Into a 50-mL round-bottom flask, was placed 5-[5-methylpyrido[4,3-b]indol-7-yl]-2-(piperidin-4-yloxy)pyridine (300 mg, 0.84 mmol, 1.0 equiv) and tert-butyl 3-oxoazetidine-1-carboxylate (716 mg, 4.19 mmol, 5.0 equiv) in DCM (10.00 mL), to which was added Ti(Oi-Pr)$_4$ (0.5 mL) and STAB (532 mg, 2.51 mmol, 3.0 equiv). The resulting solution was stirred for 16 hr at 40° C. The resulting mixture was concentrated. The residue was applied onto a silica gel column eluting with dichloromethane/methanol (100:0 to 24:1). This resulted in 240 mg (56%) of tert-butyl 3-[4-[(5-[5-methylpyrido[4,3-b]indol-7-yl]pyridin-2-yl)oxy]piperidin-1-yl]azetidine-1-carboxylate as a yellow solid.

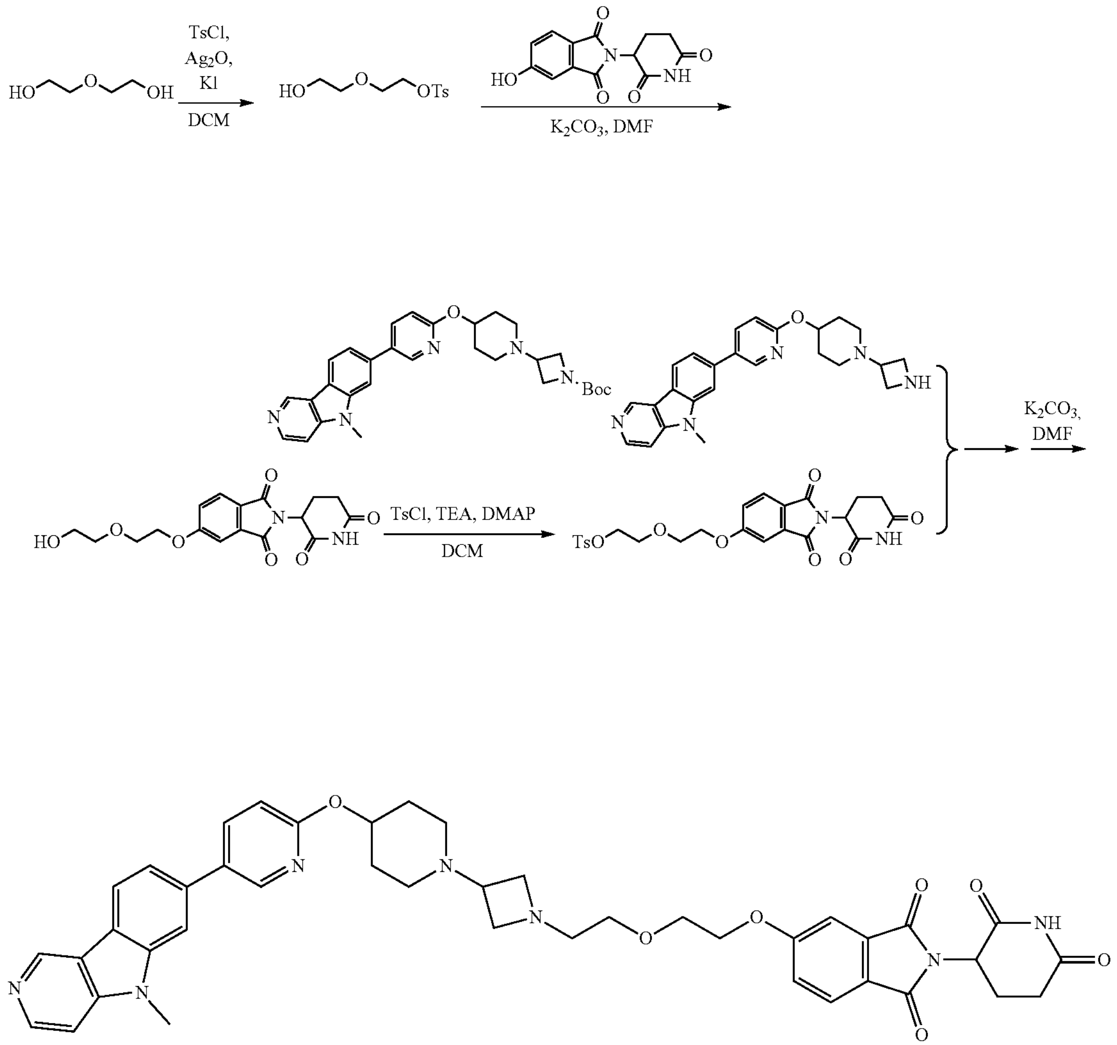

Exemplary Compound 412

Exemplary Synthesis of Exemplary Compound 413

Step 1

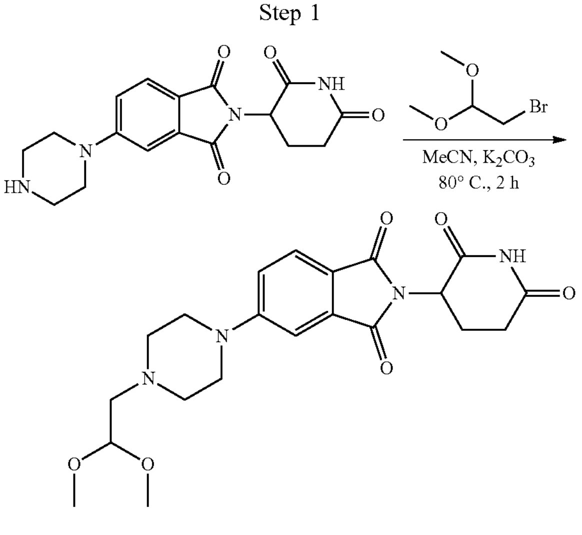

To a mixture of 2-(2,6-dioxo-3-piperidyl)-5-piperazin-1-yl-isoindoline-1,3-dione (500 mg, 1.32 mmol, 1 eq, hydrochloride) in acetonitrile (20 mL) was added diisopropylethylamine (511 mg, 3.96 mmol, 3 eq), potassium iodide (21 mg, 0.13 mmol, 0.1 eq) and 2-bromo-1,1-dimethoxy-ethane (271 mg, 1.60 mmol, 1.22 eq). The mixture was stirred at 80° C. for 2 h. The mixture was filtered and concentrated under reduced pressure. The residue was purified by silica gel column chromatography (dichloromethane:methanol=1:0 to 50:1). Compound 5-[4-(2,2-dimethoxyethyl) piperazin-1-yl]-2-(2,6-dioxo-3-piperidyl)isoindoline-1,3-dione (120 mg, 0.27 mmol, 21% yield) was obtained as a yellow oil.

5-[4-(2,2-Dimethoxyethyl) piperazin-1-yl]-2-(2,6-dioxo-3-piperidyl)isoindoline-1,3-dione was converted to the title compound using procedures analogous to those described for exemplary compound 401.

Exemplary Synthesis of Exemplary Compound 414
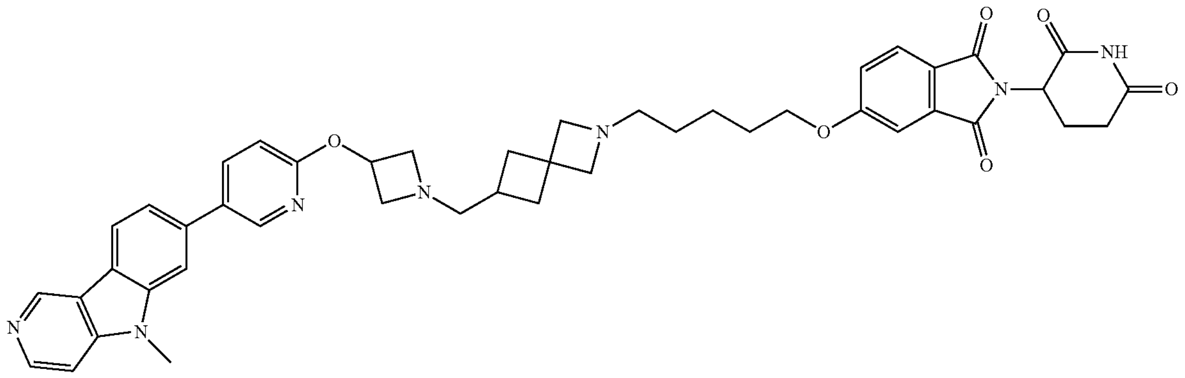 [SMILES: Cn1c2ccncc2c2ccc(-c3ccc(OC4CN(CC5CC6(C5)CN(CCCCCOc5ccc7c(c5)C(=O)N(C5CCC(=O)NC5=O)C7=O)C6)C4)nc3)cc21]
Prepared according to the scheme below using procedures analogous to those described for other examples above and commonly known to those skilled in the art.
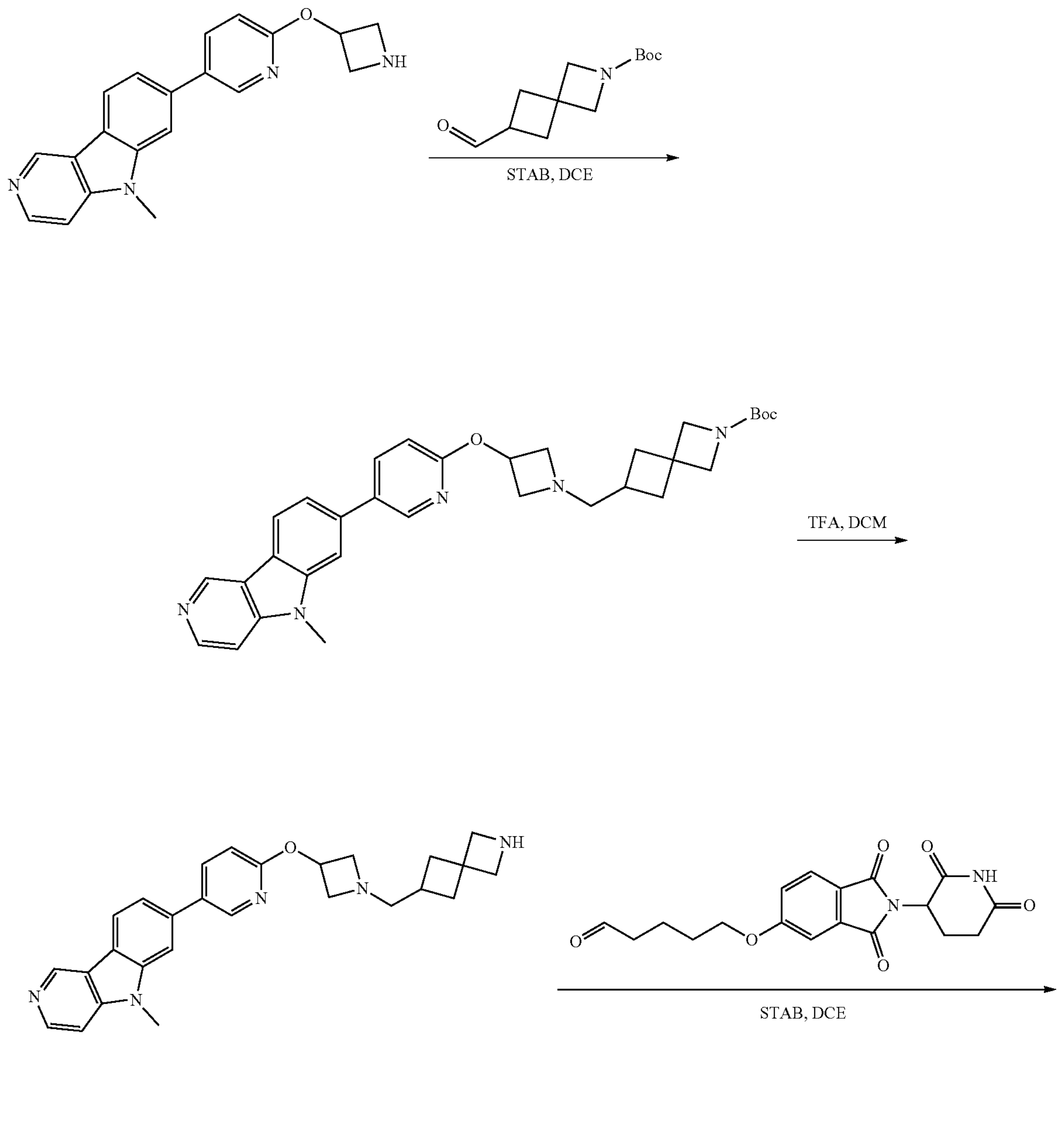

-continued

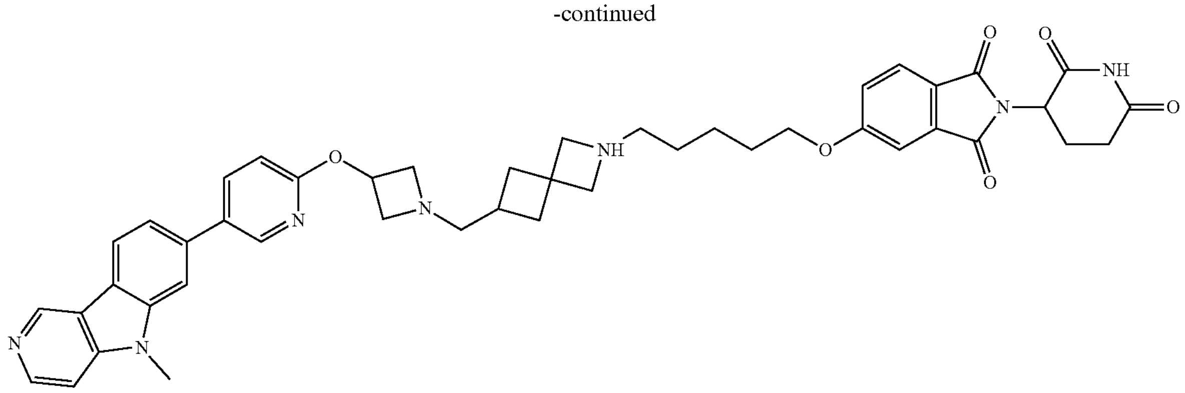

Exemplary Compound 414

Exemplary Synthesis of Exemplary Compound 416

Step 1

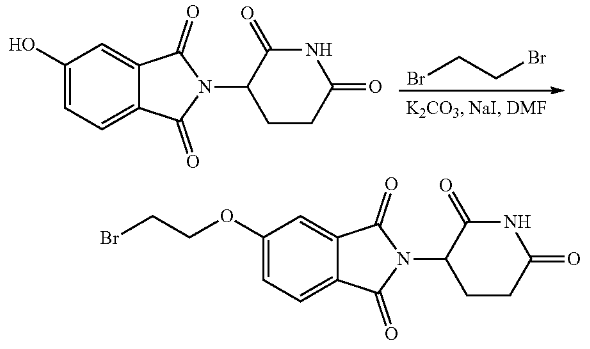

To a stirred solution 2-(2,6-dioxopiperidin-3-yl)-5-hydroxy-2,3-dihydro-1H-isoindole-1,3-dione (300.00 mg, 1.094 mmol, 1.00 equiv) in DMF were added $K_2CO_3$ (454 mg, 3.28 mmol, 3.0 equiv), 1,2-dibromoethane (617 mg, 3.28 mmol, 3.0 equiv), and NaI (16.4 mg, 0.11 mmol, 0.10 equiv) dropwise at room temperature under nitrogen atmosphere. The resulting mixture was stirred for 2 h at 60 degrees C. under nitrogen atmosphere. The resulting mixture was diluted with water and extracted with EtOAc (50 mL). The combined organic layers were washed with water (3×30 mL) and dried over anhydrous $Na_2SO_4$. After filtration the filtrate was concentrated under reduced pressure. The residue was purified by prep-TLC (PE/EtOAc 1:2) to afford 5-(2-bromoethoxy)-2-(2,6-dioxopiperidin-3-yl)-2,3-dihydro-1H-isoindole-1,3-dione (190 mg, 46%) as a yellow solid.

Step 2

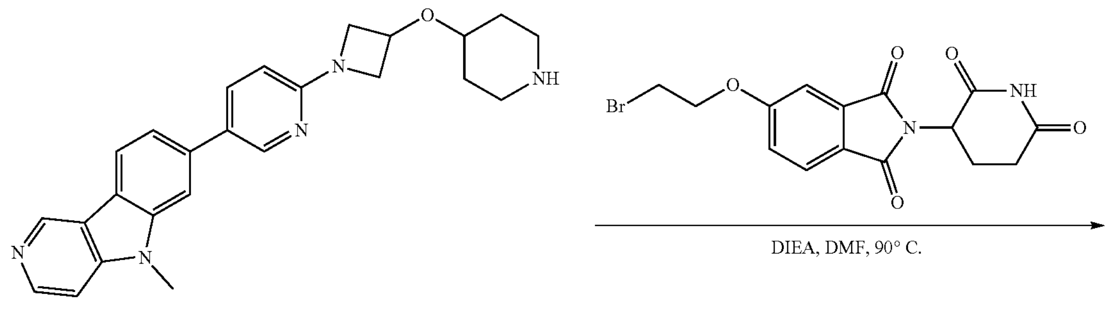

prepared as described in example 382

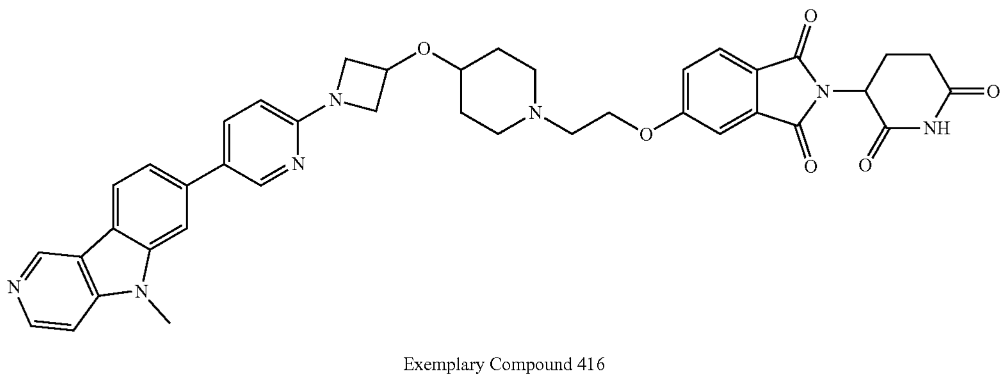

Exemplary Compound 416

Into a 50-mL round-bottom flask purged and maintained with an inert atmosphere of nitrogen, was placed 3-[6-(2-bromoethoxy)-1-oxo-3H-isoindol-2-yl]piperidine-2,6-dione (99 mg, 0.27 mmol, 1.0 equiv) and 5-[5-methylpyrido[4,3-b]indol-7-yl]-2-[3-(piperidin-4-yloxy)azetidin-1-yl]pyridine (90 mg, 0.22 mmol, 0.8 equiv) in DMF (2.00 mL), to which was added DIEA (84 mg, 0.65 mmol, 2.4 equiv). The resulting solution was stirred for 3 hr at 90° C. The reaction mixture was cooled to room temperature. The crude product was purified by prep-HPLC with the following conditions: XBridge Prep OBD C18 Column 30*50 mm 5 um; Mobile Phase A: water (0.1% FA), Mobile Phase B: acetonitrile; Flow rate: 60 mL/min; Gradient: 3% B to 20% B in 9 min; 254 nm; This resulted in 21.4 mg (11%) of 2-(2,6-dioxopiperidin-3-yl)-5-[2-(4-[[1-(5-[5-methylpyrido[4,3-b]indol-7-yl]pyridin-2-yl)azetidin-3-yl]oxy]piperidin-1-yl)ethoxy]isoindole-1,3-dione as a white solid.

Exemplary Synthesis of Exemplary Compound 417

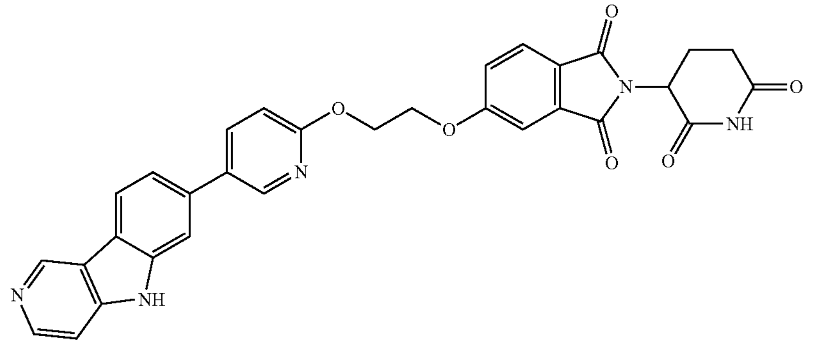 [SMILES: O=C1CCC(N2C(=O)c3ccc(OCCOc4ccc(-c5ccc6c(c5)[nH]c5ccncc56)cn4)cc3C2=O)C(=O)N1]

Prepared according to the scheme below using procedures analogous to those described for other examples above and commonly known to those skilled in the art.

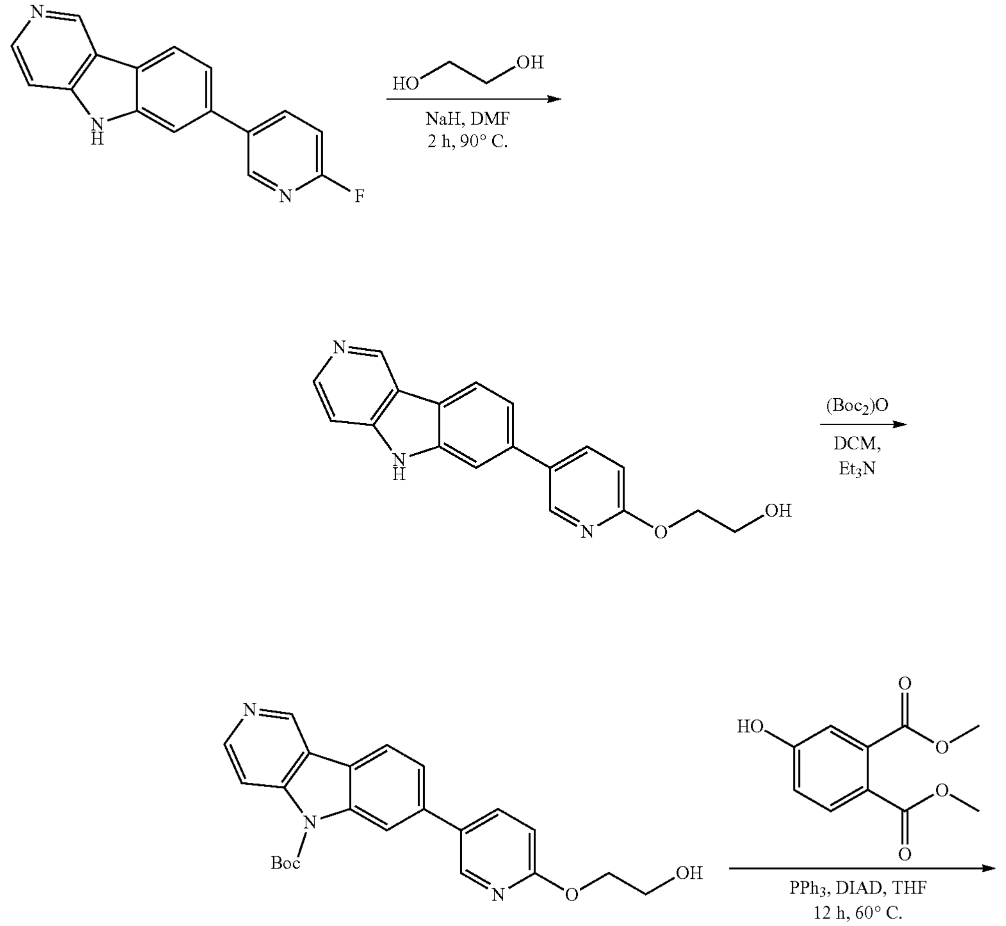

-continued

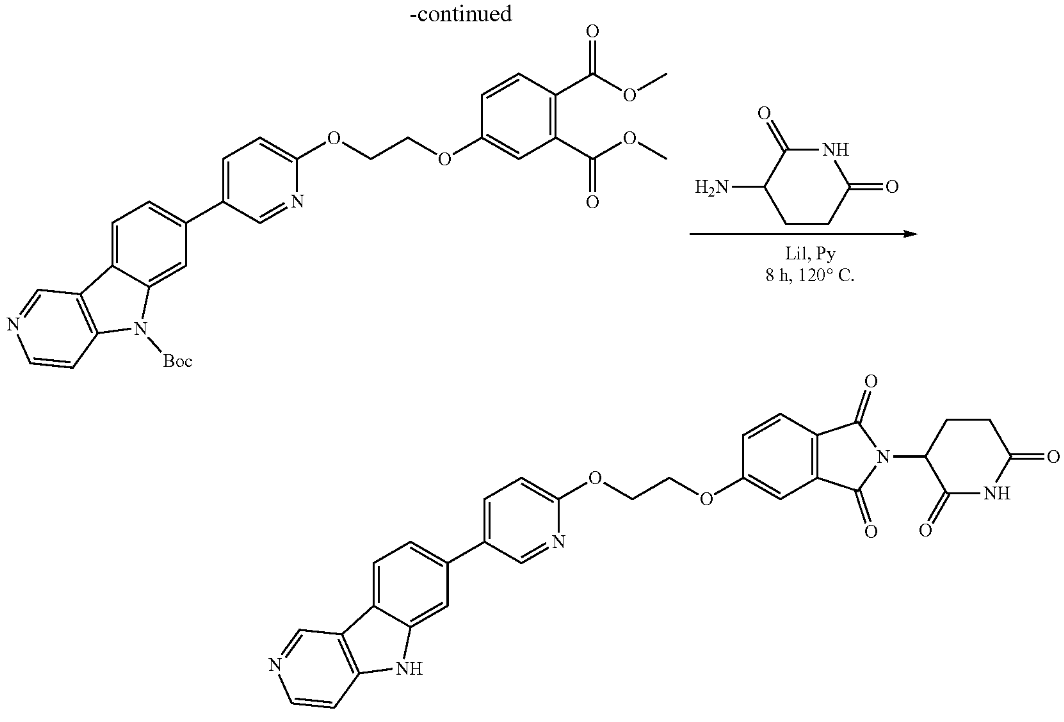

Exemplary Compound 417

Exemplary Synthesis of Exemplary Compound 418

Step 1

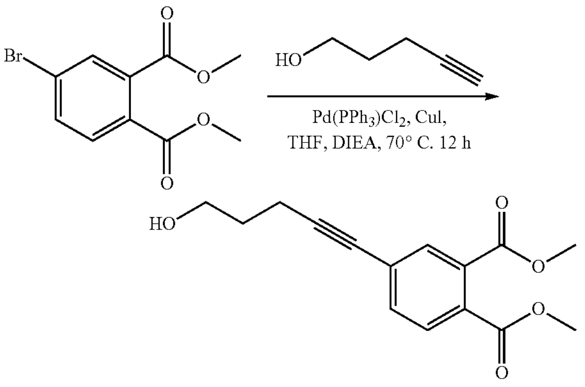

A mixture of dimethyl 4-bromobenzene-1,2-dicarboxylate (5 g, 18.3 mmol, 1 eq), pent-4-yn-1-ol (4.62 g, 54.9 mmol, 3 eq), copper iodide (348 mg, 1.83 mmol, 0.1 eq), bis(triphenylphosphine) palladium(II)dichloride (2.57 g, 3.66 mmol, 0.2 eq), and diisopropylethylamine (23.7 g, 183.1 mmol, 10 eq) in tetrahydrofuran (100 mL) was degassed and then heated to 70° C. for 12 hours under nitrogen. The mixture was concentrated under reduced pressure. The residue was purified by silica gel column chromatography (petroleum ether:ethyl acetate=12:1 to 3:1). Compound dimethyl 4-(5-hydroxypent-1-ynyl)benzene-1,2-dicarboxylate (4 g, 14.48 mmol, 79% yield) was obtained as a brown oil.

Step 2

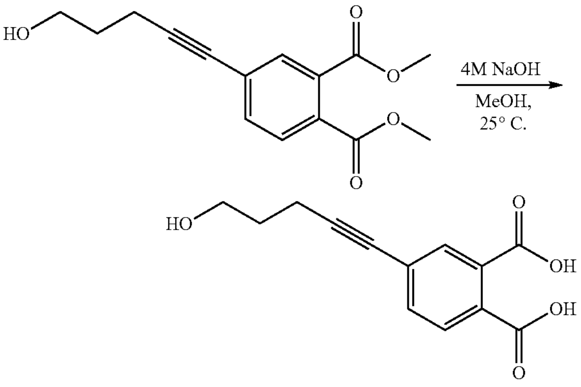

To a solution of dimethyl 4-(5-hydroxypent-1-ynyl)benzene-1,2-dicarboxylate (500 mg, 1.81 mmol, 1 eq) in methanol (5 mL) was added sodium hydroxide (4 M, 2.2 mL, 5 eq). The mixture was stirred at 40° C. for 1 h. pH of the reaction mixture was adjusted to 5 with aqueous HCl (1M, 4 mL). The reaction mixture was extracted with ethyl acetate (8 mL×3). The combined organic layer was washed with brine (16 mL×2), dried over anhydrous sodium sulfate, filtered and the filtrate was concentrated. The crude product was used for next step directly. The crude desired product 4-(5-hydroxypent-1-ynyl)phthalic acid (400 mg, 1.45 mmol) was obtained as a yellow oil and used directly in the next step.

Step 3

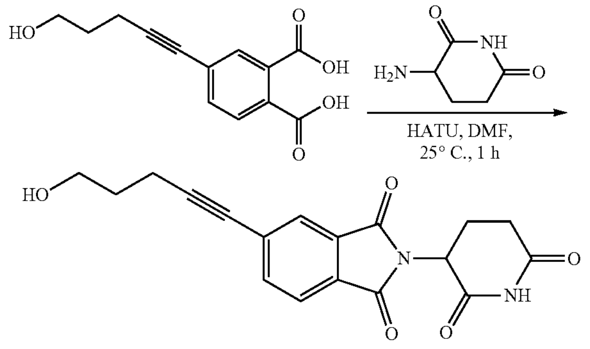

To a solution of 4-(5-hydroxypent-1-ynyl)phthalic acid (300 mg, 1.21 mmol, 1 eq) and 3-aminopiperidine-2,6-dione (238 mg, 1.45 mmol, 1.2 eq, hydrochloride) in N,N-dimethylformamide (6 mL) was added O—(7-azabenzotriazol-1-yl)-N,N,N',N'-tetramethyluronium hexafluorophosphate (919 mg, 2.42 mmol, 2 eq) and triethylamine (611 mg, 6.04 mmol, eq). The mixture was stirred at 50° C. for 2 h. The reaction mixture was poured into water (1 mL) and extracted with ethyl acetate (2 mL×3). The combined organic layer was washed with brine (1 mL×2), dried over anhydrous sodium sulfate, filtered and the filtrate was concentrated. The crude product was purified by prep-TLC (dichloromethane:methanol=10:1). The desired product 2-(2,6-dioxo-3-piperidyl)-5-(5-hydroxypent-1-ynyl)isoindoline-1,3-dione (150 mg, 0.43 mmol, 35% yield) was obtained as a yellow oil.

Step 4

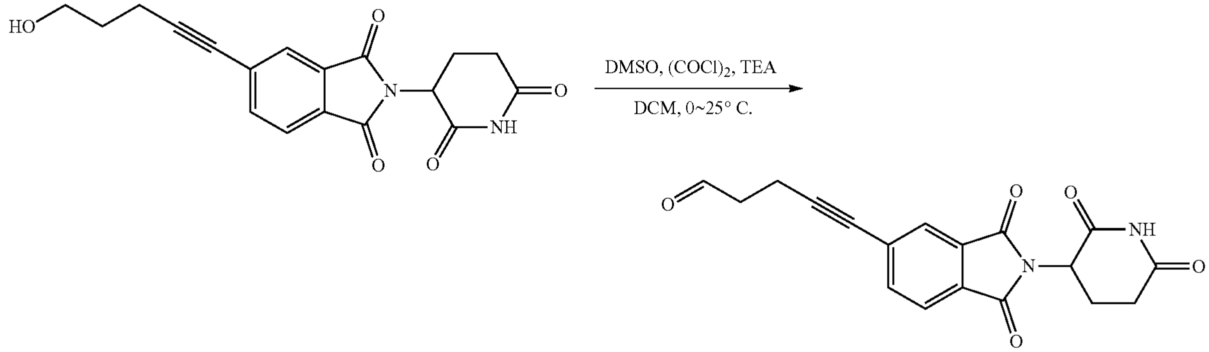

To a solution of oxalyl chloride (223 mg, 1.76 mmol, 0.15 mL, 3 eq) in dichloromethane (2 mL) was added dimethyl sulfoxide (183 mg, 2.35 mmol, 0.18 mL, 4 eq) in dichloromethane (2 mL) dropwise at −68° C. over a period of 1 hr under nitrogen. The mixture was stirred at −68° C. for 0.5 h. Then 2-(2,6-dioxo-3-piperidyl)-5-(5-hydroxypent-1-ynyl) isoindoline-1,3-dione (0.2 g, 0.58 mmol, 1 eq) in dichloromethane (2 mL) was added to the mixture dropwise at −68° C. for 1 h. After the mixture was stirred for 0.5 h, triethylamine (475 mg, 4.70 mmol, 8 eq) was added to the mixture dropwise. The mixture was stirred at −68° C. for 0.5 h. Saturated ammonium chloride (30 mL) solution was added to the mixture, and the mixture was extracted with dichloromethane (30 mL×2). The organic layer was dried over sodium sulfate and concentrated. The residue was purified with silica gel chromatography (dichloromethane: methanol=1:0 to 10:1). 5-[2-(2,6-Dioxo-3-piperidyl)-1,3-dioxo-isoindolin-5-yl]pent-4-ynal (150 mg, 0.44 mmol, 75% yield) was obtained as a yellow oil.

Dioxo-3-piperidyl)-1,3-dioxo-isoindolin-5-yl]pent-4-ynal was converted to the title compound as described for exemplary compound 401.

Exemplary Synthesis of Exemplary Compound 419

Step 1

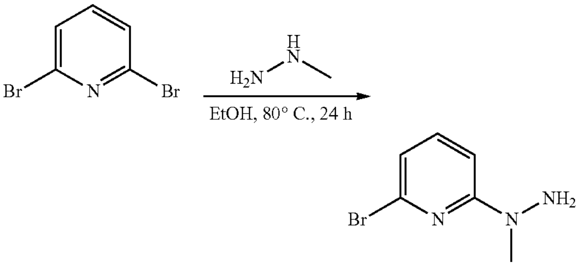

To a solution of 2,6-dibromopyridine (30 g, 126.64 mmol, 1 eq) in ethanol (150 mL) was added methylhydrazine (72.93 g, 633.20 mmol, 5 eq). The mixture was heated to 80° C. and stirred at this temperature for 24 h. The reaction mixture was concentrated, and the crude product was purified by Prep-HPLC (column: Kromasil Eternity XT 250*80 mm*10 um; mobile phase: [water (10 mM NH4HCO3)-ACN]; B %: 25%-50%, 30 MIN/80% min). The desired product 1-(6-bromo-2-pyridyl)-1-methyl-hydrazine (20 g, 98.98 mmol, 78% yield) was obtained as a red oil.

Step 2

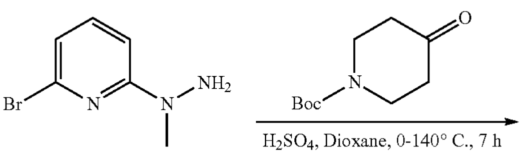

-continued

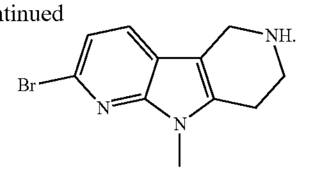

To a solution of 1-(6-bromo-2-pyridyl)-1-methyl-hydrazine (10 g, 49.49 mmol, 1 eq) and tert-butyl 4-oxopiperidine-1-carboxylate (10.85 g, 54.44 mmol, 1.1 eq) in dioxane (100 mL) was added sulfuric acid (18 M, 15 mL, 5.46 eq) at 0° C. Then the mixture was stirred at 140° C. for 7 h. The reaction mixture was cooled to 25° C., the organic layer was discarded, and ice-water (150 mL) was added. The mixture was stirred until the gummy material was dissolved. Then the pH of the reaction mixture was adjusted to pH=12-13 by adding solid sodium hydroxide. The reaction mixture was stirred at 0° C. for 30 minutes, the precipitate was collected by filtration and washed with water (15 mL). The precipitate was suspended in propan-2-ol (80 mL) and heated at reflux for 10 minutes. The reaction mixture was filtered, the precipitate was washed with propan-2-ol (100 mL) and the combined filtrate was evaporated. The residue was purified by silica gel column chromatography (dichloromethane: methanol=1:0 to 20:1). The desired product 2-bromo-9-methyl-6,7,8,9-tetrahydro-5H-pyrrolo[2,3-b:4,5-c']dipyridine (2.3 g, 8.64 mmol, 17% yield) was obtained as a yellow solid.

Step 3

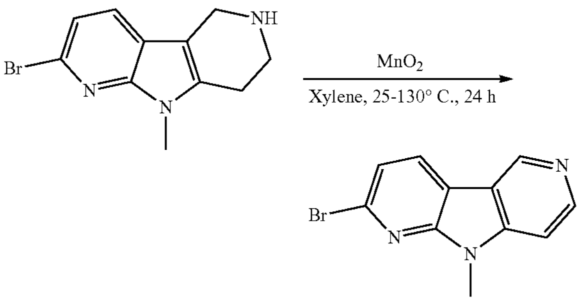

To a mixture of 2-bromo-9-methyl-6,7,8,9-tetrahydro-5H-pyrrolo[2,3-b:4,5-c']dipyridine (4.6 g, 17.28 mmol, 1 eq) in xylene (350 mL) was added manganese dioxide (15.03 g, 172.84 mmol, 10 eq) at 25° C. The mixture was stirred at 130° C. for 24 h. The reaction mixture was filtered, and the filtrate was concentrated. The residue was purified by silica gel column chromatography (dichloromethane:methanol=1:0 to 10:1). The desired product 2-bromo-9-methyl-9H-pyrrolo[2,3-b:4,5-c']dipyridine (2.4 g, 8.22 mmol, 47% yield) was obtained as a yellow solid.

Step 4

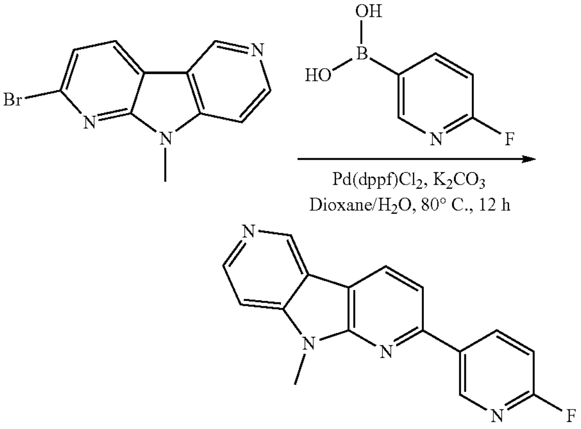

A mixture of 2-bromo-9-methyl-9H-pyrrolo[2,3-b:4,5-c'] dipyridine (1.2 g, 4.58 mmol, 1 eq), (6-fluoro-3-pyridyl) boronic acid (709 mg, 5.04 mmol, 1.1 eq), [1,1'-bis(diphenylphosphino)ferrocene]dichloropalladium(II) (335 mg, 0.45 mmol, 0.1 eq) and potassium carbonate (1.27 g, 9.16 mmol, 2 eq) in dioxane (100 mL) and water (10 mL) was degassed and then heated to 80° C. for 12 hours under nitrogen. The mixture was filtered and concentrated under reduced pressure. The residue was purified by silica gel column chromatography (dichloromethane:methanol=1:0 to 10:1). Compound 2-(6-fluoropyridin-3-yl)-9-methyl-9H-pyrrolo[2,3-b:4,5-c']dipyridine (1.2 g, 4.31 mmol, 94% yield) was obtained as a brown solid.

2-(6-fluoropyridin-3-yl)-9-methyl-9H-pyrrolo[2,3-b:4,5-c']dipyridine was converted to the title compound using procedures described for exemplar compound 405 and 411.

Using analogous procedures the following exemplary compound were prepared: 420, 421, 422, 427.

Exemplary Synthesis of Exemplary Compound 423

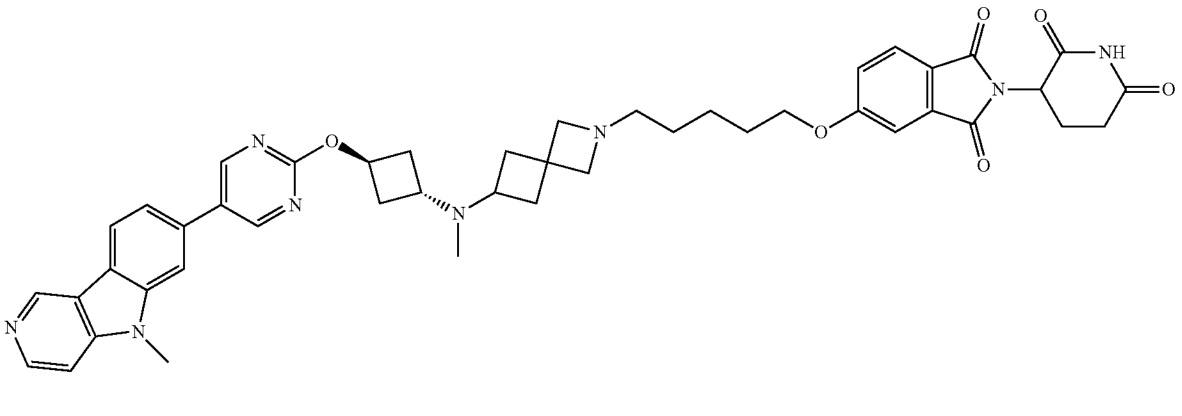 [SMILES: Cn1c2ccncc2c2ccc(-c3cnc(O[C@H]4C[C@H](N(C)C5CC6(C5)CN(CCCCCOc5ccc7c(c5)C(=O)N(C5CCC(=O)NC5=O)C7=O)C6)C4)nc3)cc21]

Step 1

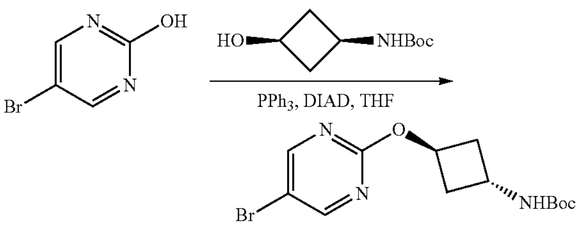

Into a 50-mL round-bottom flask purged and maintained with an inert atmosphere of nitrogen, was placed 5-bromopyrimidin-2-ol (500 mg, 2.86 mmol, 1.0 equiv), tert-butyl N-(3-hydroxycyclobutyl)carbamate (535 mg, 2.86 mmol, 1.0 equiv) and $PPh_3$ (1124 mg, 4.29 mmol, 1.5 equiv) in THF (20 mL). This was followed by the addition of a solution of DIAD (872 mg, 4.32 mmol, 1.5 equiv) in THF (10 mL) dropwise with stirring at 0° C. in 5 min. The resulting solution was stirred for 2 hr at 60° C. The resulting solution was diluted with 20 mL of $H_2O$. The resulting solution was extracted with (2×30 mL) ethyl acetate, dried over anhydrous sodium sulfate and concentrated. The residue was applied to a silica gel column eluting with ethyl acetate/hexane (1:1). This resulted in 400 mg (41%) of tert-butyl N-[3-[(5-bromopyrimidin-2-yl)oxy]cyclobutyl] carbamate as a white solid.

Step 2

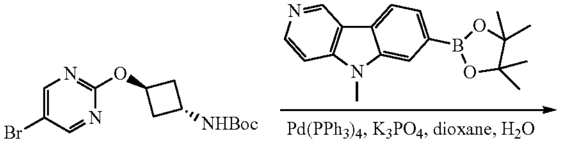

-continued

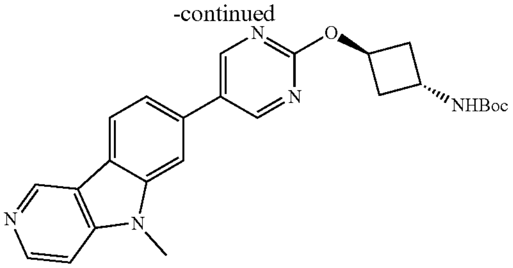

Into a 50-mL round-bottom flask purged and maintained with an inert atmosphere of nitrogen, was placed tert-butyl N-[(1r,3r)-3-((5-bromopyrimidin-2-yl)oxy]cyclobutyl]carbamate (445 mg, 1.29 mmol, 1.0 equiv), 5-methyl-7-(4,4,5,5-tetramethyl-1,3,2-dioxaborolan-2-yl)pyrido[4,3-b]indole (398 mg, 1.29 mmol, 1.0 equiv), $Pd(PPh_3)_4$ (149 mg, 0.13 mmol, 0.1 equiv), $K_3PO_4$ (549 mg, 2.59 mmol, 2.0 equiv) in dioxane (10 mL) and $H_2O$ (2 mL). The resulting solution was stirred for 2 hr at 90° C. The reaction was then quenched by the addition of 10 mL of water. The resulting solution was extracted with (2×10 mL) of ethyl acetate, dried over anhydrous sodium sulfate and concentrated. This resulted in 400 mg (crude) of tert-butyl N-[(1r,3r)-3-[(5-[5-methylpyrido[4,3-b]indol-7-yl]pyrimidin-2-yl)oxy]cyclobutyl] carbamate as a yellow solid.

tert-Butyl N-[(1r,3r)-3-[(5-[5-methylpyrido[4,3-b]indol-7-yl]pyrimidin-2-yl)oxy]cyclobutyl]carbamate was converted to the title compound according to the scheme below using procedures analogous to those described for other examples above and commonly known to skilled in the art.

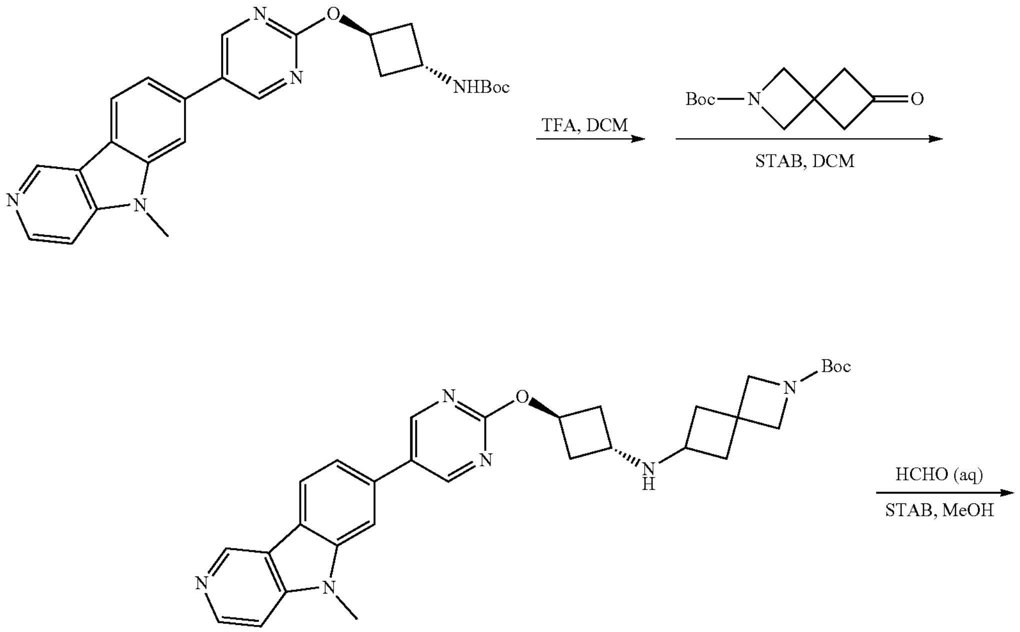

-continued

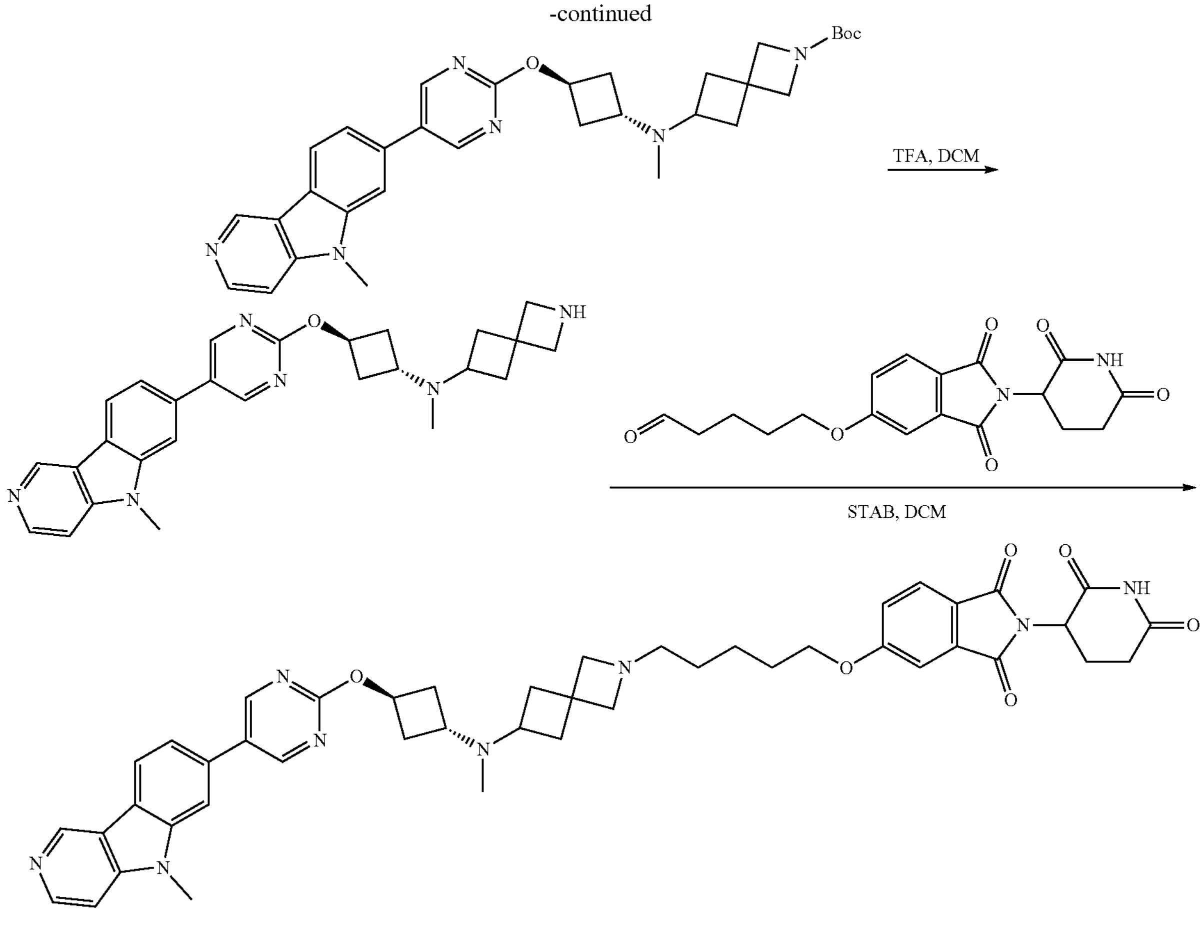

Exemplary Compound 423

Exemplary Synthesis of Exemplary Compound 424

Step 1

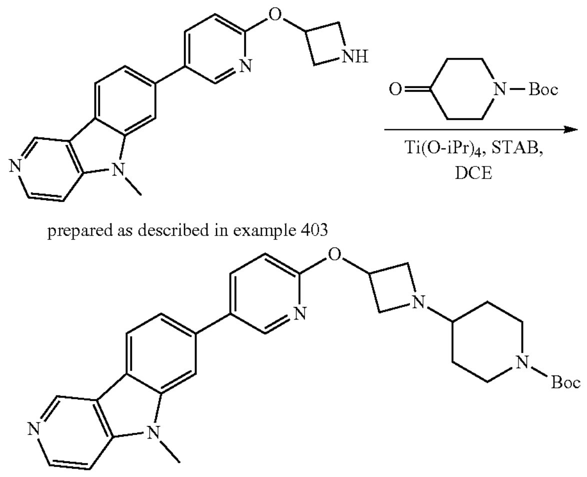

Into a 25-mL round-bottom flask, was placed 2-(azetidin-3-yloxy)-5-[5-methylpyrido[4,3-b]indol-7-yl]pyridine (200 mg, 0.60 mmol, 1.0 equiv) and tert-butyl 4-oxopiperidine-1-carboxylate (121 mg, 0.61 mmol, 1.0 equiv) in DCE (10 mL), to which was added $Ti(Oi\text{-}Pr)_4$ (86 mg, 0.30 mmol, 0.5 equiv), STAB (257 mg, 1.21 mmol, 2.0 equiv). The resulting solution was stirred for 5 hr at 25° C. The resulting mixture was concentrated under vacuum. The residue was applied onto a silica gel column eluting with dichloromethane/methanol (8/1). This resulted in 140 mg (45%) of tert-butyl 4-[3-[(5-[5-methylpyrido[4,3-b]indol-7-yl]pyridin-2-yl)oxy]azetidin-1-yl]piperidine-1-carboxylate as a yellow oil.

tert-Butyl 4-[3-[(5-[5-methylpyrido[4,3-b]indol-7-yl]pyridin-2-yl)oxy]azetidin-1-yl]piperidine-1-carboxylate was converted to the title compound as described for the last two steps of exemplary compound 423.

Exemplary Synthesis of Exemplary Compound 425

Step 1

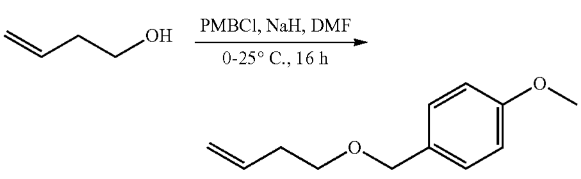

To a mixture of but-3-en-1-ol (7.30 g, 101.24 mmol, 1.00 eq) in N,N-dimethylformamide (105 mL) was added sodium hydride (4.86 g, 121.49 mmol, 60% in mineral oil, 1.2 eq) at 0° C., and the mixture was stirred for 0.5 h under nitrogen. Then to the mixture was added 1-(chloromethyl)-4-methoxybenzene (15.06 g, 96.18 mmol, 0.95 eq) at 0° C., and it was warmed to 25° C. and stirred for 12 h. The mixture was poured into saturated ammonium chloride solution (200 mL) and stirred for 15 min. The aqueous phase was extracted with ethyl acetate (200 mL×3). The combined organic phase was washed with brine (200 mL×3), dried with anhydrous sodium sulfate, filtered and concentrated in vacuum. The residue was purified by silica gel chromatography (petroleum ether/ethyl acetate=200/1 to 20/1) to afford 1-(but-3-enoxymethyl)-4-methoxy-benzene (15.80 g, 82.18 mmol, 81% yield) as a yellow oil.

Step 2

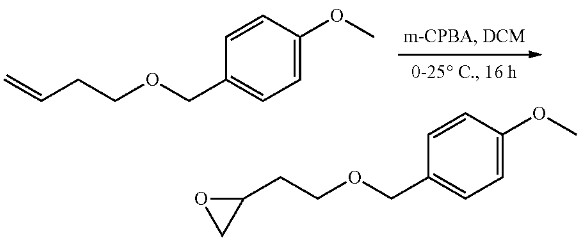

To a mixture of 1-(but-3-enoxymethyl)-4-methoxy-benzene (15.8 g, 82.18 mmol, 1.00 eq) in dichloromethane (300 mL) was added 3-chlorobenzoperoxoic acid (26.70 g, 131.49 mmol, 85% purity, 1.60 eq) at 0° C. under nitrogen. The mixture was stirred at 0° C. for 30 min, then heated to 25° C. and stirred for 6 h. Saturated aqueous sodium thiosulfate (200 mL) was added, and the mixture was stirred at 25° C. for another 0.5 hour. The mixture was extracted with dichloromethane (200 mL). The combined organic phase was washed with brine (200 mL), dried over anhydrous sodium sulfate and then filtered. The filtrate was concentrated in vacuum, and the residue was purified by silica gel column chromatography (petroleum ether/ethyl acetate=100:1 to 10:1) to afford 2-[2-[(4-methoxyphenyl)methoxy]ethyl]oxirane (10.0 g, 48.02 mmol, 58% yield) as a yellow oil.

Step 3

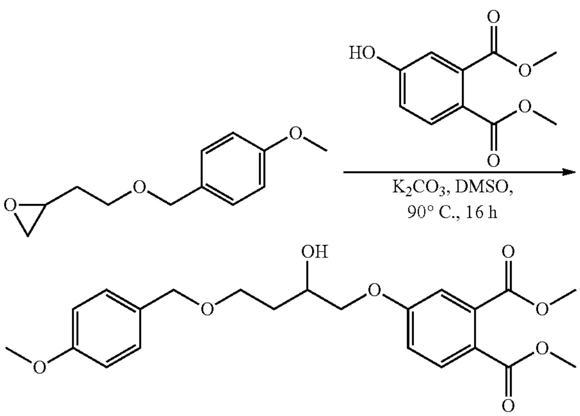

To a mixture of dimethyl 4-hydroxybenzene-1,2-dicarboxylate (11.10 g, 52.82 mmol, 1.10 eq) and 2-[2-[(4-methoxyphenyl)methoxy]ethyl]oxirane (10 g, 48.02 mmol, 1.00 eq) in DMSO (100 mL) was added potassium carbonate (13.27 g, 96.04 mmol, 2 eq) in one portion under nitrogen. The mixture was heated to 90° C. and stirred for 16 h. The reaction mixture was cooled to 25° C., poured into water (100 mL) and stirred for 15 min. The aqueous phase was extracted with ethyl acetate (200 mL×3). The combined organic phase was washed with brine (200 mL×3), dried with anhydrous sodium sulfate, filtered and concentrated in vacuum. The residue was purified by prep-HPLC (column: Phenomenex luna C18 250*50 mm*10 um; mobile phase: [water (0.225% FA)-ACN]; B %: 32acn %-62acn %, 30 min). Dimethyl 4-[2-hydroxy-4-[(4-methoxyphenyl)methoxy]butoxy]benzene-1,2-dicarboxylate (3.98 g, 9.51 mmol, 19% yield) was obtained as a yellow oil.

Step 4

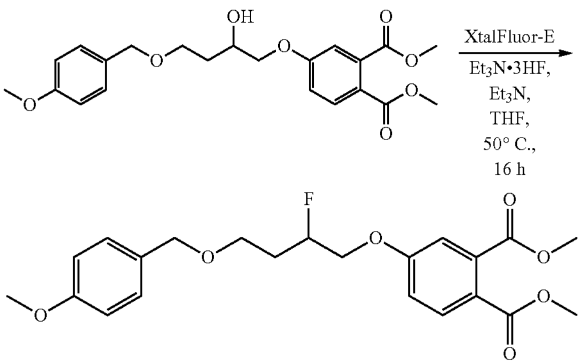

To a mixture of dimethyl 4-[2-hydroxy-4-[(4-methoxyphenyl)methoxy]butoxy]benzene-1,2-dicarboxylate (1.8 g, 4.30 mmol, 1 eq) in dichloromethane (45 mL) was added triethylamine (435 mg, 4.30 mmol, 1.0 eq), triethylamine trihydrofluoride (1.39 g, 8.60 mmol, 2 eq) and N,N-diethylamino-S,S-difluorosulfinium tetrafluoroborate (XtalFluor-E) (1.48 g, 6.45 mmol, 1.5 eq) in one portion at −60° C. under nitrogen. The mixture was warmed to 25° C. and stirred for 1 h. The mixture was cooled to 25° C. and concentrated under reduced pressure at 45° C. The residue was poured into ice-water (w/w=1/1) (30 mL) and stirred for 15 min. The aqueous phase was extracted with ethyl acetate (50 mL×3). The combined organic phase was washed with brine (50 mL×3), dried with anhydrous sodium sulfate, filtered and concentrated under vacuum. The residue was purified by silica gel chromatography (petroleum ether/ethyl acetate=10/1 to 3/1) to afford dimethyl 4-[2-fluoro-4-[(4-methoxyphenyl)methoxy]butoxy]benzene-1,2-dicarboxylate (1.18 g, 2.81 mmol, 65% yield) as a yellow oil.

Step 5

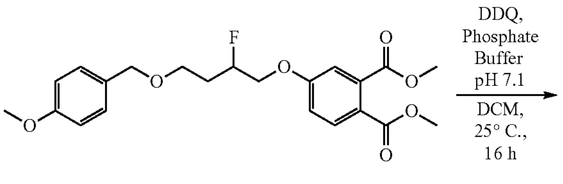

-continued

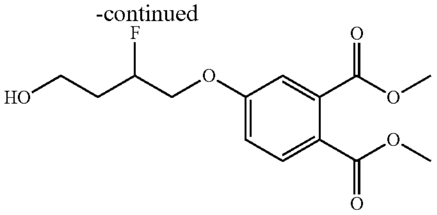

To a solution of dimethyl 4-[2-fluoro-4-[(4-methoxyphenyl)methoxy]butoxy] benzene-1,2-dicarboxylate (570 mg, 1.36 mmol, 1 eq) in dichloromethane (32 mL) and phosphate buffer (8 mL, pH 7.1) was added 2,3-dichloro-5,6-dicyano-1,4-benzoquinone (461 mg, 2.03 mmol, 1.5 eq), and the mixture was stirred at 0° C. for 1 h, then stirred at 25° C. for 2 h. To the mixture was added saturated sodium bicarbonate solution (10 mL), and it was extracted with dichloromethane (20 mL×2). The combined organic phase was washed with saturated sodium bicarbonate solution (20 mL×2), brine (30 mL), dried with anhydrous sodium sulfate, filtered and concentrated in vacuum. The residue was purified by column chromatography (petroleum ether/ethyl acetate=10:1 to 3:1). Dimethyl 4-(2-fluoro-4-hydroxy-butoxy)benzene-1,2-dicarboxylate (480 mg, 1.55 mmol, 57% yield) was obtained as a yellow oil, and starting material, dimethyl 4-[2-fluoro-4-[(4-methoxyphenyl)methoxy]butoxy]benzene-1,2-dicarboxylate, was partly recovered (600 mg, 1.37 mmol) as a yellow oil.

Dimethyl 4-(2-fluoro-4-hydroxy-butoxy)benzene-1,2-dicarboxylate was converted to the title compound according to the scheme below using procedures described in US 20180125821, in other examples above, as well as common procedures known to those skilled in the art.

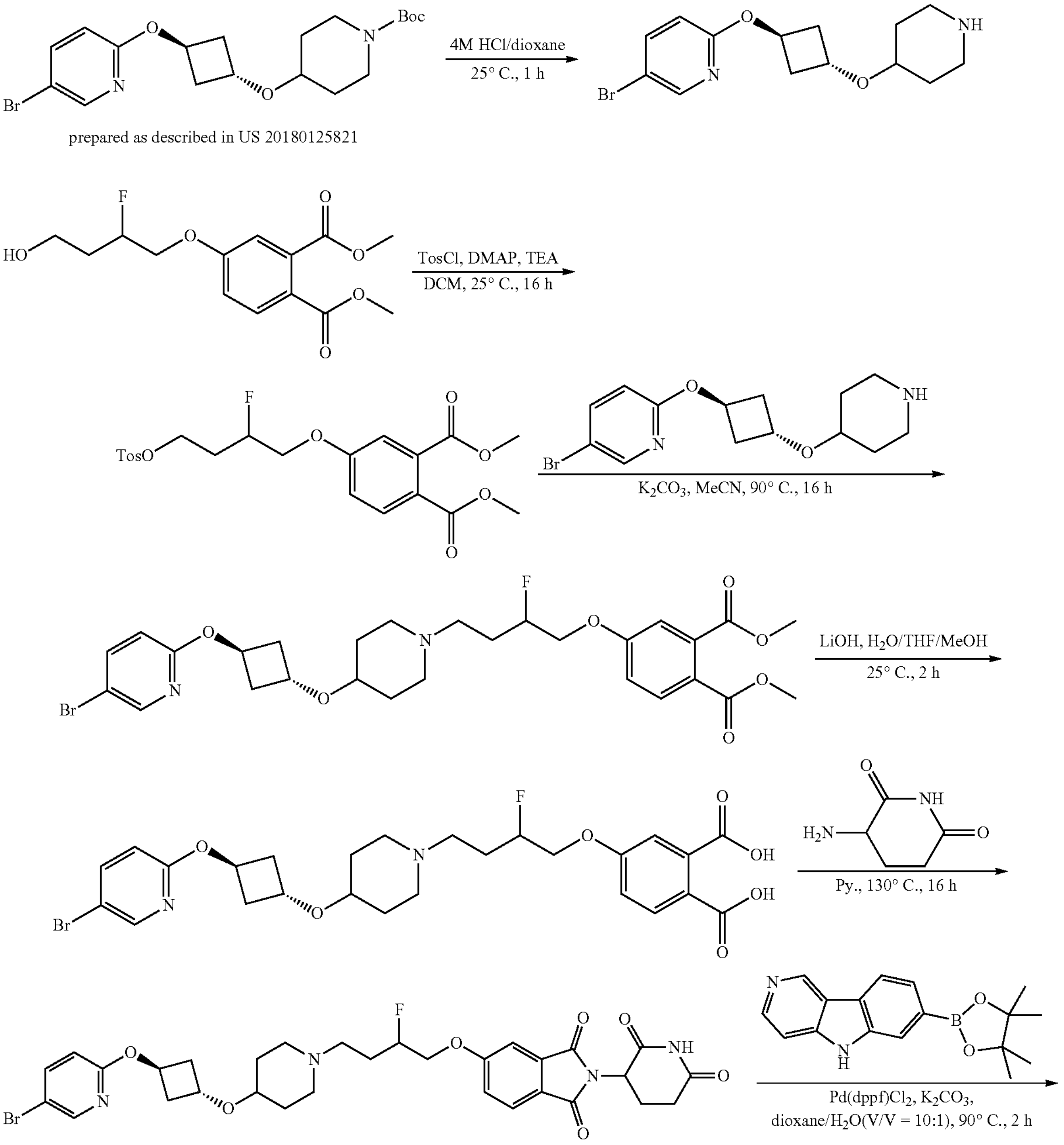

-continued

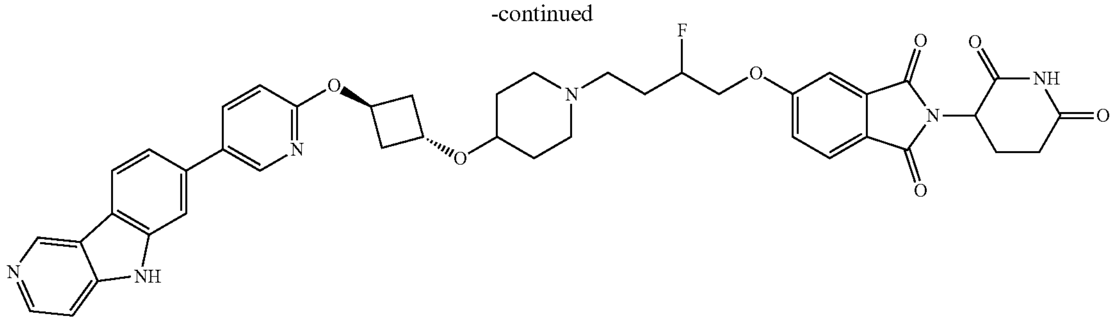

Exemplary Compound 425

Exemplary Synthesis of Exemplary Compound 426

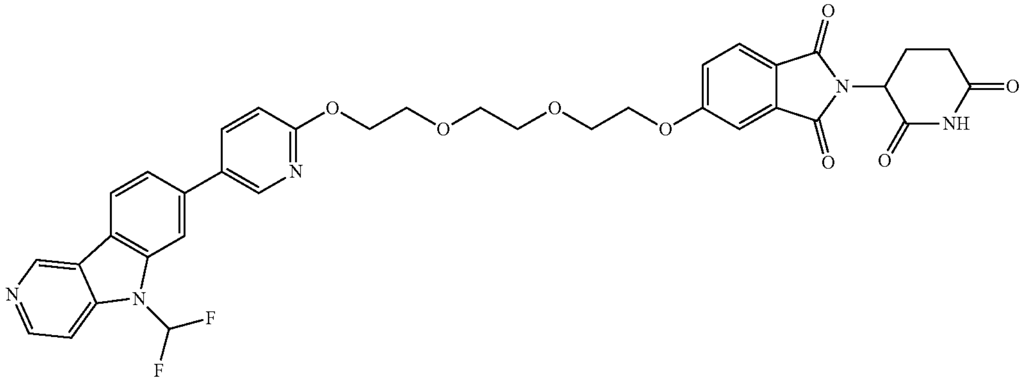 [SMILES: O=C1CCC(N2C(=O)c3ccc(OCCOCCOCCOc4ccc(-c5ccc6c7cnccc7n(C(F)F)c6c5)cn4)cc3C2=O)C(=O)N1]

Step 1

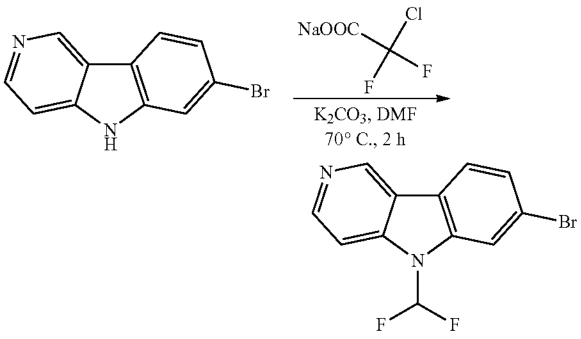

To a solution of 7-bromo-5H-pyrido[4,3-b]indole (500 mg, 2.02 mmol, 1 eq) in dichloromethane (5 mL) was added sodium 2-chloro-2,2-difluoroacetate (617 mg, 4.05 mmol, 2 eq) and potassium carbonate (559 mg, 4.05 mmol, 2 eq). The mixture was stirred at 80° C. for 2 hours. The reaction mixture was poured into water (5 mL) and extracted with ethyl acetate (10 mL×3). The combined organic layer was washed with brine (10 mL), dried over sodium sulfate, filtered, and the filtrate was concentrated. The crude product was purified by prep-HPLC (column: Phenomenex Synergi Max-RP 150*50 mm*10 um; mobile phase: [water (0.225% FA)-ACN]; B %: 10%-40%, 11 min). The desired product 7-bromo-5-(difluoromethyl)pyrido[4,3-b]indole (200 mg, 0.67 mmol, 33% yield) was obtained as a yellow solid.

7-Bromo-5-(difluoromethyl)pyrido[4,3-b]indole was converted to the title compound using procedures described for exemplary compound 411.

Exemplary Synthesis of Exemplary Compound 428

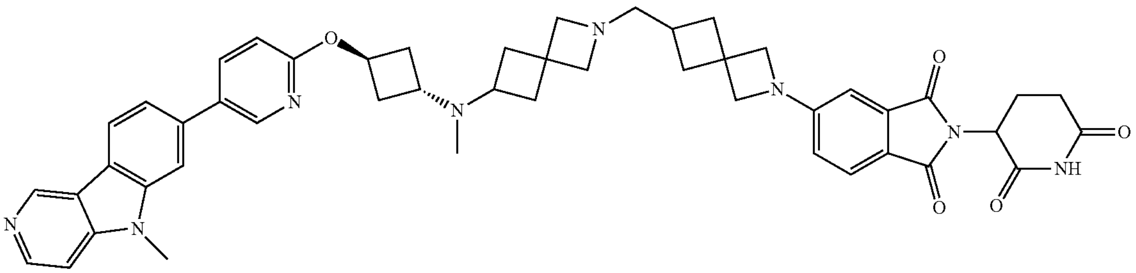 [SMILES: Cn1c2ccncc2c2ccc(-c3ccc(O[C@H]4C[C@H](N(C)C5CC6(C5)CN(CC5CC7(C5)CN(c5ccc8c(c5)C(=O)N(C5CCC(=O)NC5=O)C8=O)C7)C6)C4)nc3)cc21]

Prepared according to the scheme below using procedures analogous to those described for other examples above and commonly known to those skilled in the art.
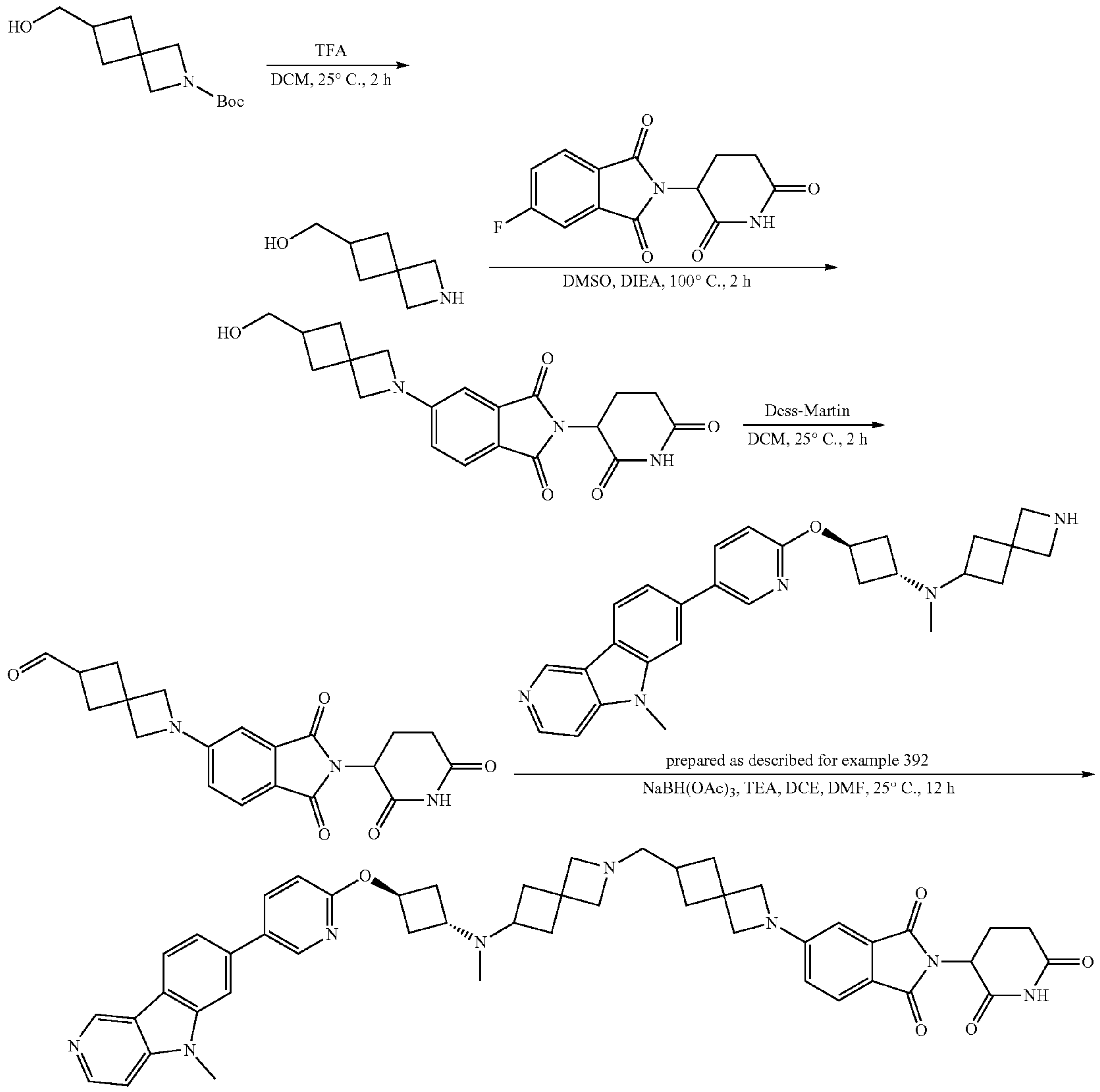
Exemplary Compound 428
Exemplary Synthesis of Exemplary Compound 429
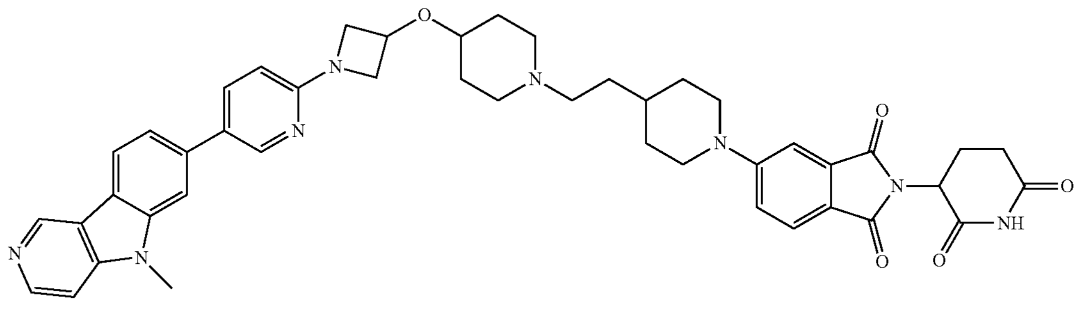 [SMILES: Cn1c2ccncc2c2ccc(-c3ccc(N4CC(OC5CCN(CCC6CCN(c7ccc8c(c7)C(=O)N(C7CCC(=O)NC7=O)C8=O)CC6)CC5)C4)nc3)cc21]

Prepared according to the scheme below using procedures analogous to those described for other examples above and commonly known to those skilled in the art.
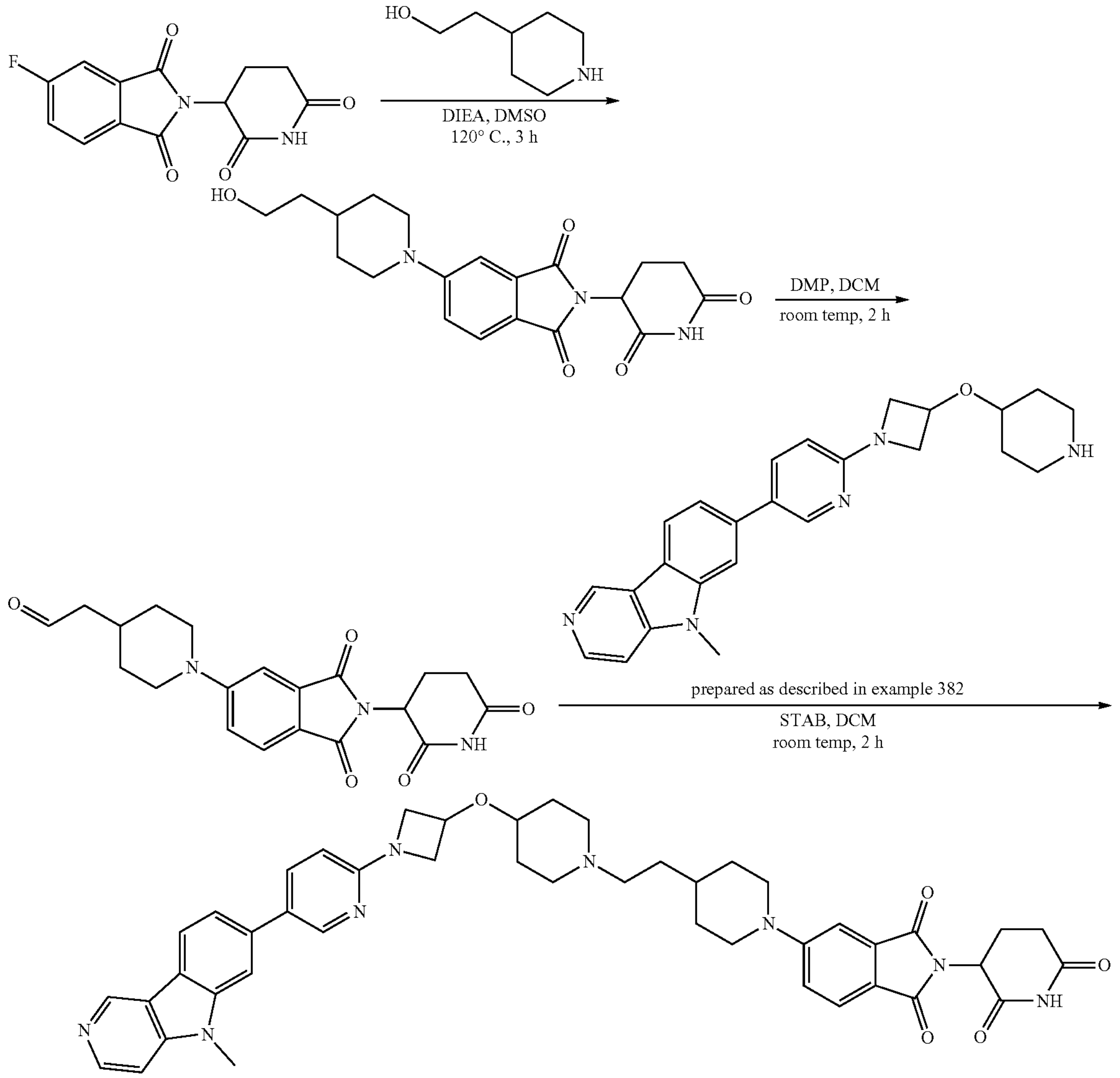
Exemplary Compound 429
Exemplary Synthesis of Exemplary Compound 430
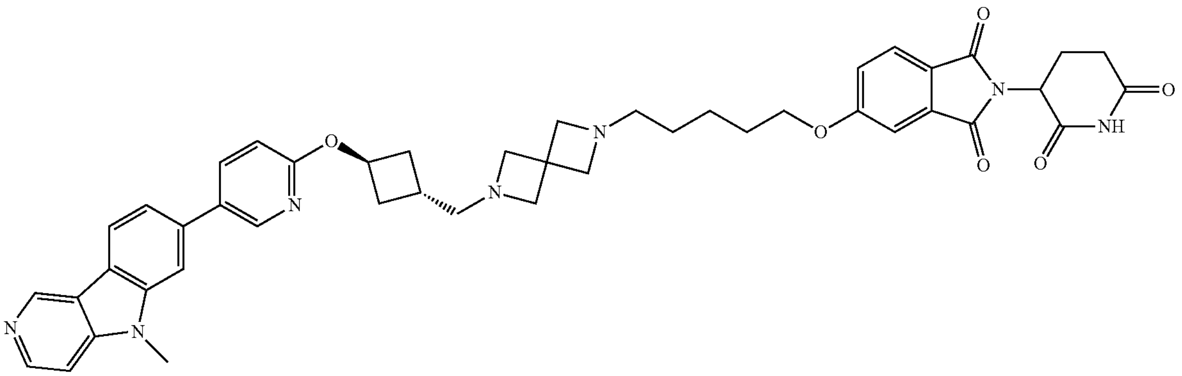 [SMILES: Cn1c2ccncc2c2ccc(-c3ccc(O[C@H]4C[C@H](CN5CC6(CN(CCCCCOc7ccc8c(c7)C(=O)N(C7CCC(=O)NC7=O)C8=O)C6)C5)C4)nc3)cc21]

Prepared according to the scheme below using procedures analogous to those described for other examples above and commonly known to those skilled in the art.
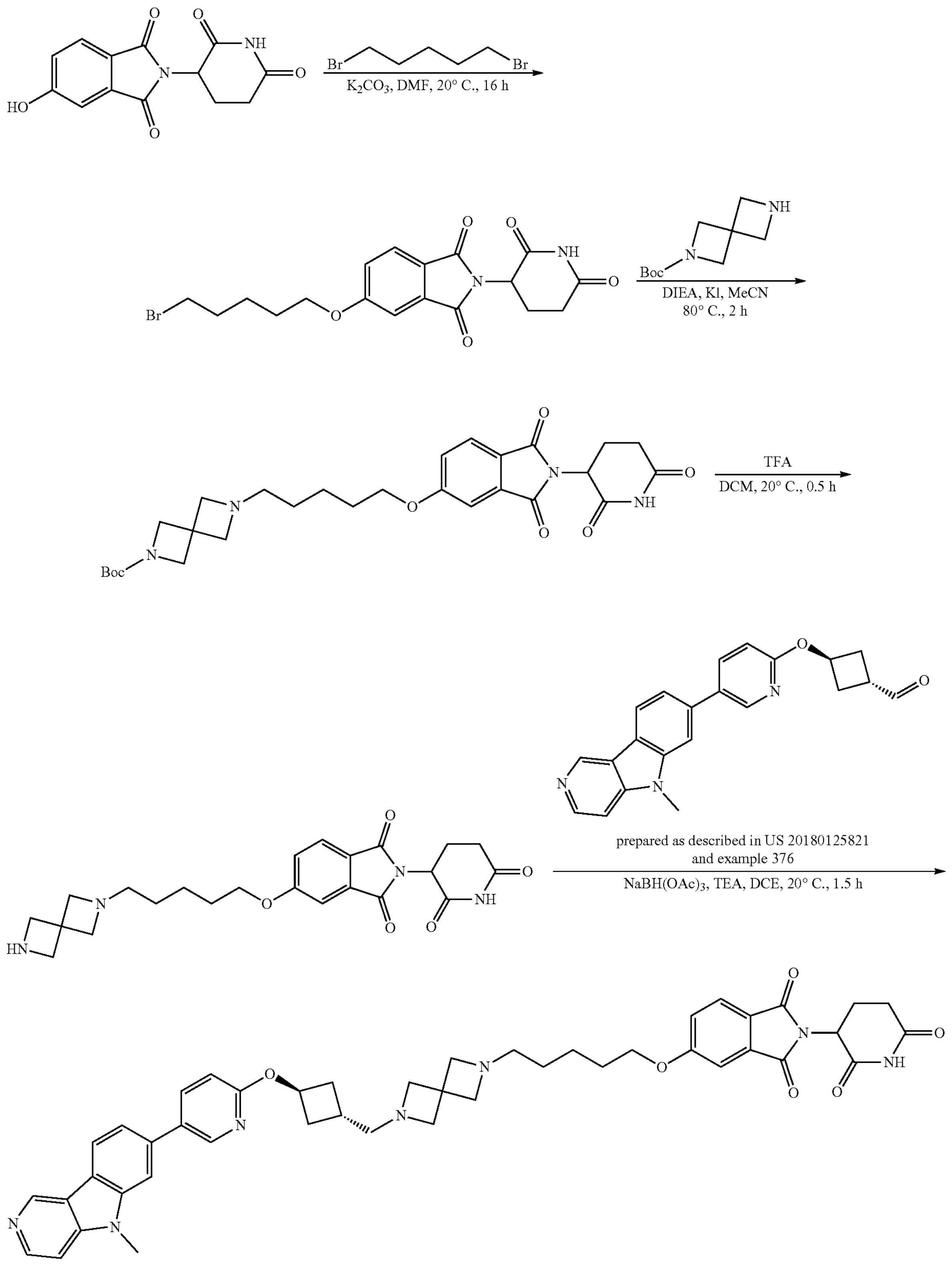
Exemplary Compound 430

Exemplary Synthesis of Exemplary Compound 431

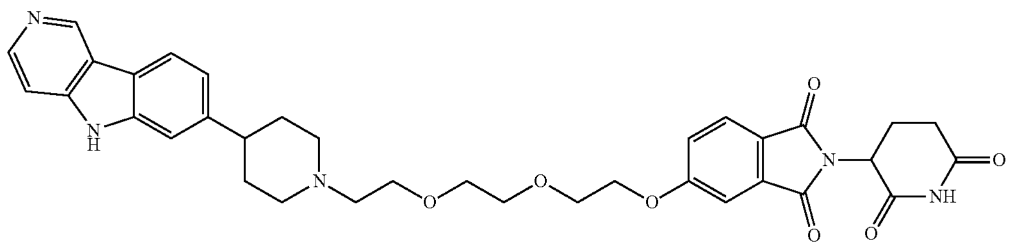 [SMILES: O=C1CCC(N2C(=O)c3ccc(OCCOCCOCCN4CCC(c5ccc6c(c5)[nH]c5ccncc56)CC4)cc3C2=O)C(=O)N1]

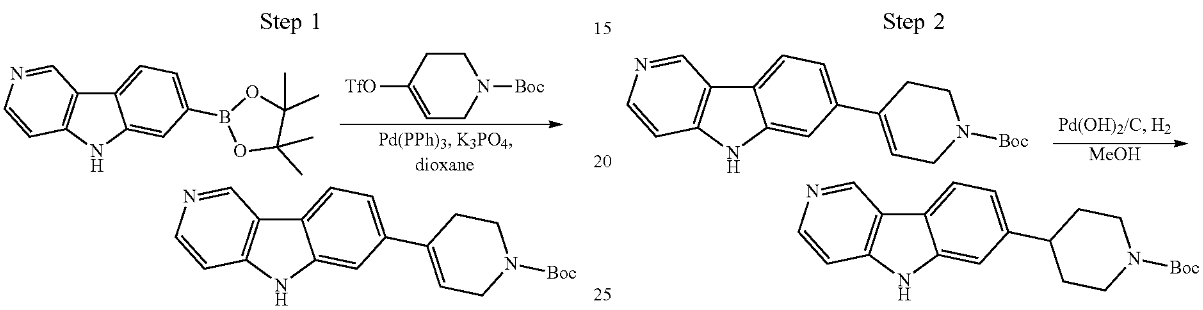

Into a 100-mL round-bottom flask purged and maintained with an inert atmosphere of nitrogen, was placed 7-(4,4,5,5-tetramethyl-1,3,2-dioxaborolan-2-yl)-5H-pyrido[4,3-b]indole (220 mg, 0.74 mmol, 1.0 equiv) in dioxane (10 mL) and $H_2O$ (2 mL), to which was added tert-butyl 4-(trifluoromethanesulfonyloxy)-3,6-dihydro-2H-pyridine-1-carboxylate (322 mg, 0.97 mmol, 1.3 equiv), $Pd(PPh_3)_4$ (86 mg, 0.07 mmol, 0.1 equiv), $K_3PO_4$ (475 mg, 2.23 mmol, 3.0 equiv). The resulting solution was stirred for 2 hr at 80° C. The reaction mixture was cooled to room temperature. The resulting solution was diluted with 50 mL of EA. The resulting mixture was washed with water (3×50 ml). The mixture was dried over anhydrous sodium sulfate and concentrated. The residue was applied onto a silica gel column eluting with ethyl acetate/petroleum ether (1:1). This resulted in 100 mg (38%) of tert-butyl 4-[5H-pyrido[4,3-b]indol-7-yl]-3,6-dihydro-2H-pyridine-1-carboxylate as a yellow solid.

Into a 50-mL round-bottom flask was placed tert-butyl 4-[5H-pyrido[4,3-b]indol-7-yl]-3,6-dihydro-2H-pyridine-1-carboxylate (100 mg, 0.28 mmol, 1.0 equiv) and $Pd(OH)_2/C$ (10%, 100 mg, 0.71 mmol, 2.54 equiv) in methanol (10 mL) under nitrogen atmosphere. The flask was then vacuumed and flushed with hydrogen. The reaction mixture was hydrogenated at room temperature for 2 hours under hydrogen atmosphere using a hydrogen balloon. Then the reaction mixture was filtered through a celite pad, and the filtrate was concentrated under reduced pressure. This resulted in 90 mg (crude) of tert-butyl 4-[5H-pyrido[4,3-b]indol-7-yl]piperidine-1-carboxylate as a colorless oil.

tert-Butyl 4-[5H-pyrido[4,3-b]indol-7-yl]piperidine-1-carboxylate was converted to the title compound according to the scheme below using procedures described for other examples above and commonly known to those skilled in the art.

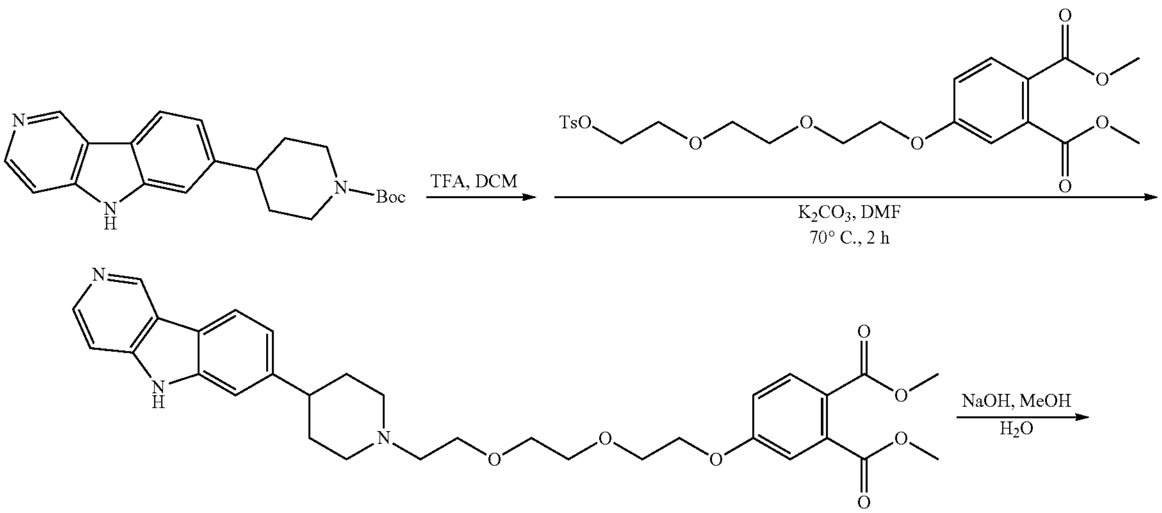

-continued
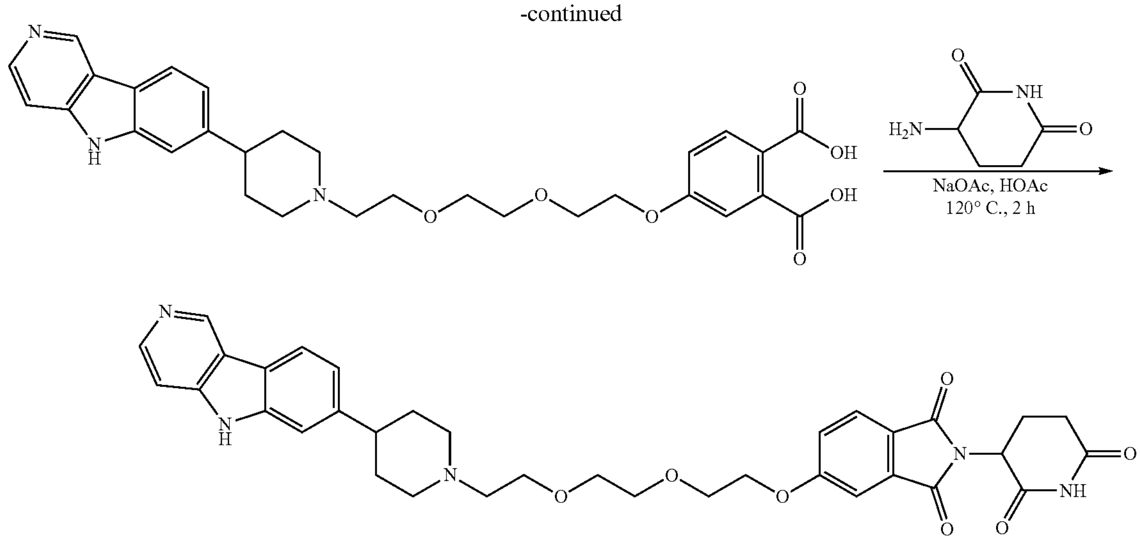
Exemplary Compound 431
Using analogous procedures the following exemplary compound was prepared: 433.
Exemplary Synthesis of Exemplary Compound 432
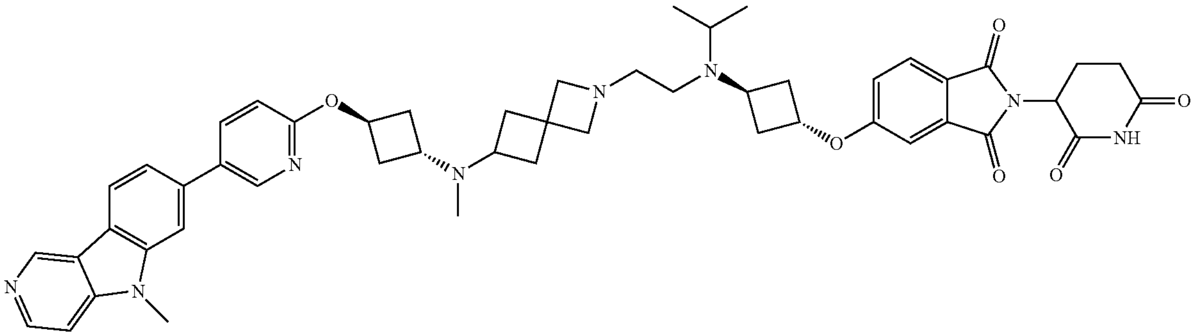 [SMILES: CC(C)N(CCN1CC2(CC(N(C)[C@H]3C[C@H](Oc4ccc(-c5ccc6c7cnccc7n(C)c6c5)cn4)C3)C2)C1)[C@H]1C[C@H](Oc2ccc3c(c2)C(=O)N(C2CCC(=O)NC2=O)C3=O)C1]
Prepared according to the scheme below using procedures analogous to those described for other examples above and commonly known to those skilled in the art.
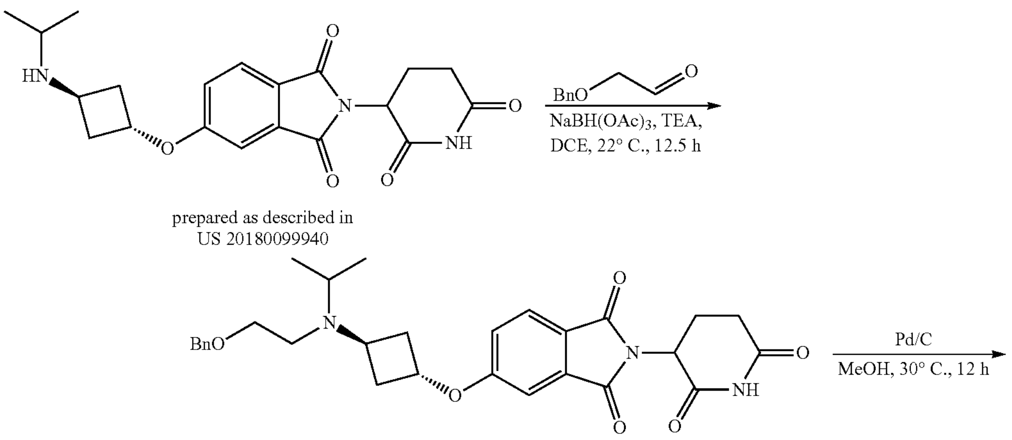

-continued
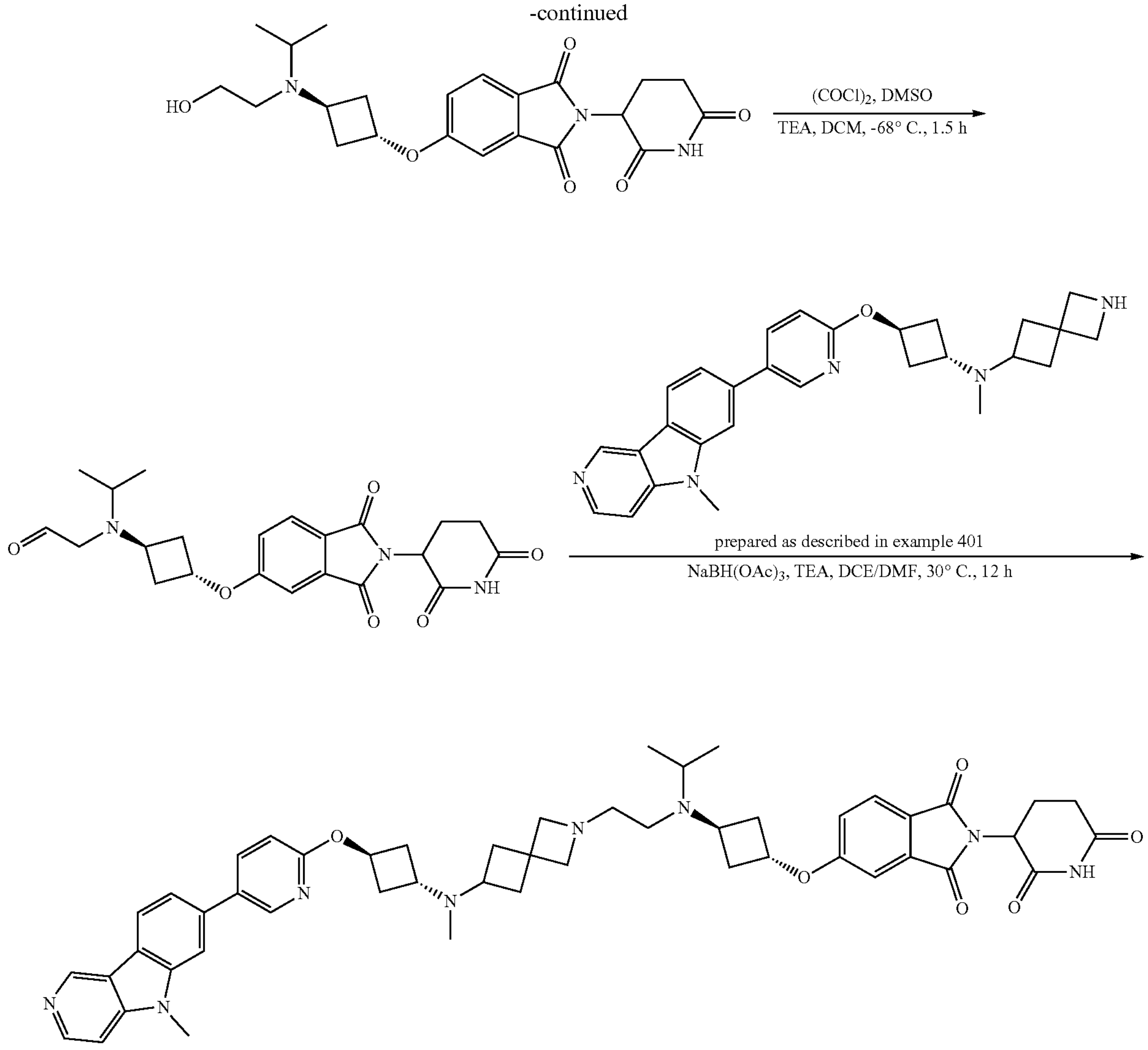
Exemplary Compound 432
Exemplary Synthesis of Exemplary Compound 434
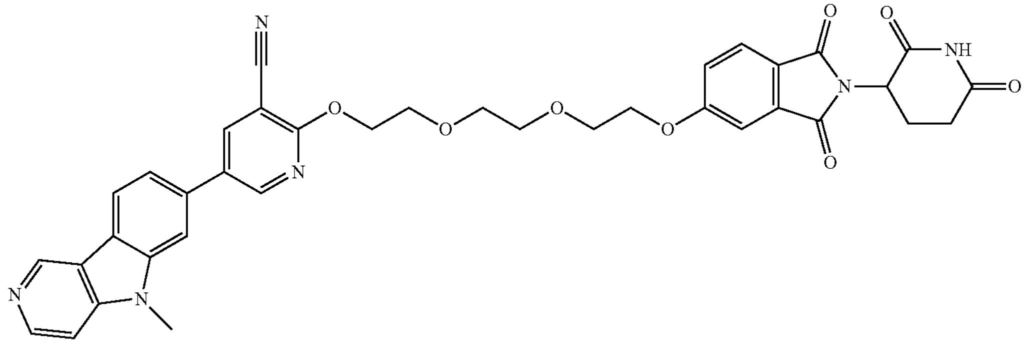 [SMILES: Cn1c2ccncc2c2ccc(-c3cnc(OCCOCCOCCOc4ccc5c(c4)C(=O)N(C4CCC(=O)NC4=O)C5=O)c(C#N)c3)cc21]
Prepared according to the scheme below using procedures described in US 20180125821 and for other examples above.

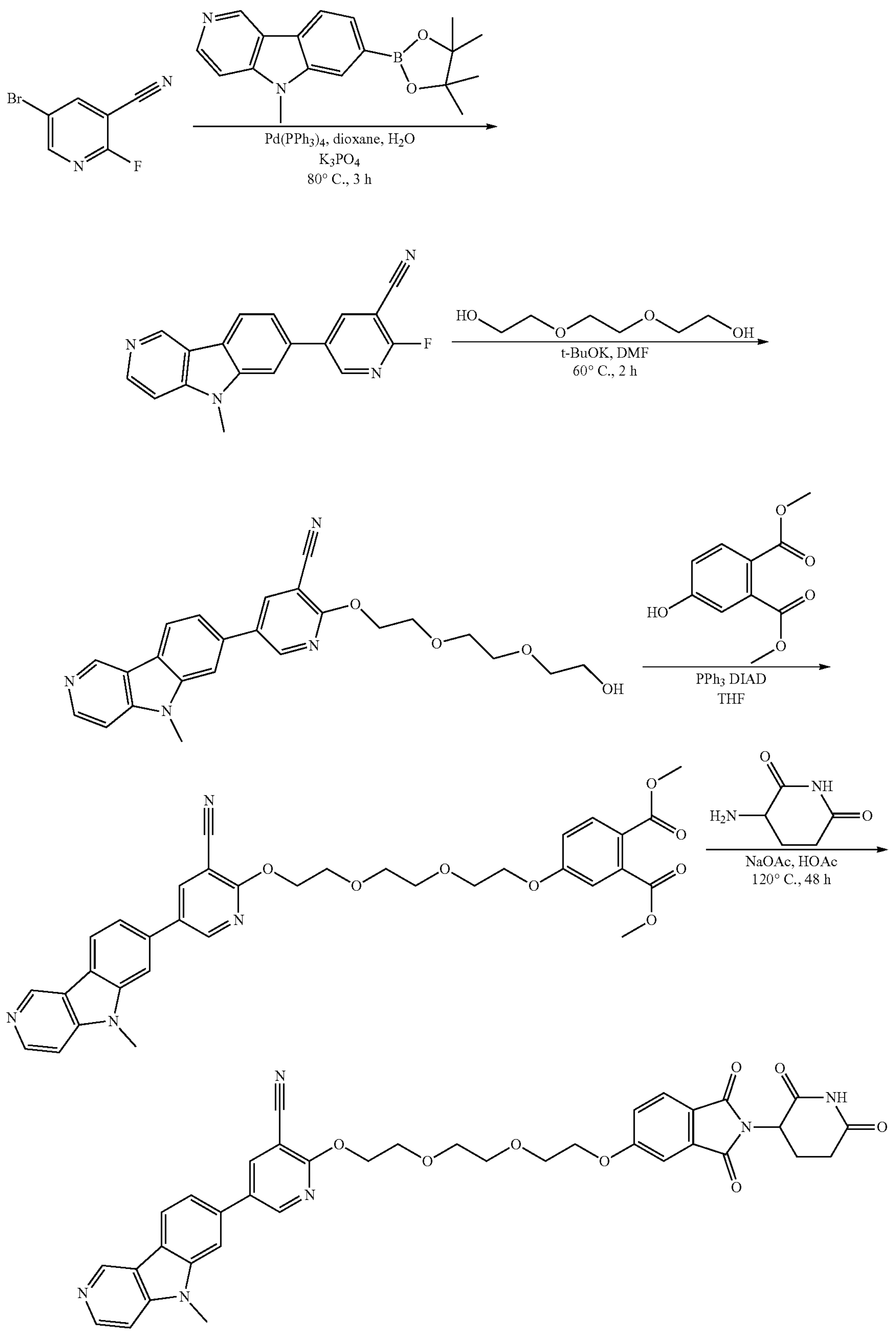
Exemplary Compound 434

Exemplary Synthesis of Exemplary Compound 435
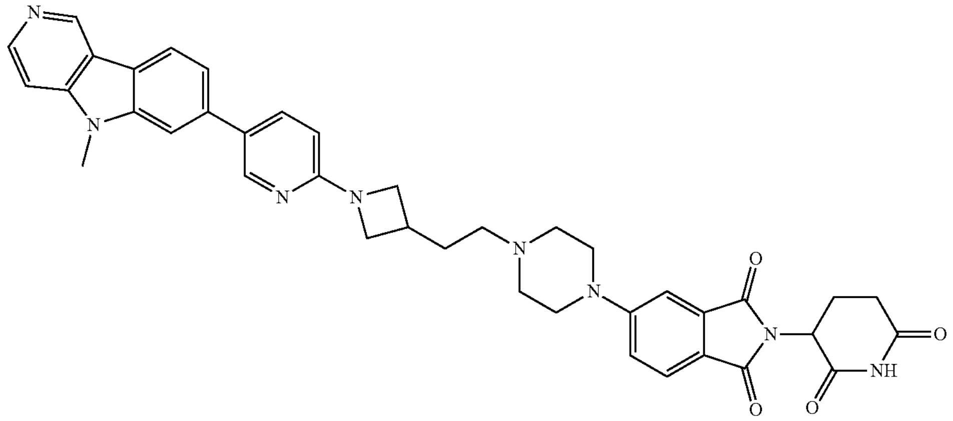 [SMILES: Cn1c2ccncc2c2ccc(-c3ccc(N4CC(CCN5CCN(c6ccc7c(c6)C(=O)N(C6CCC(=O)NC6=O)C7=O)CC5)C4)nc3)cc21]
Prepared according to the scheme below using procedures described for other examples above and commonly known to those skilled in the art.
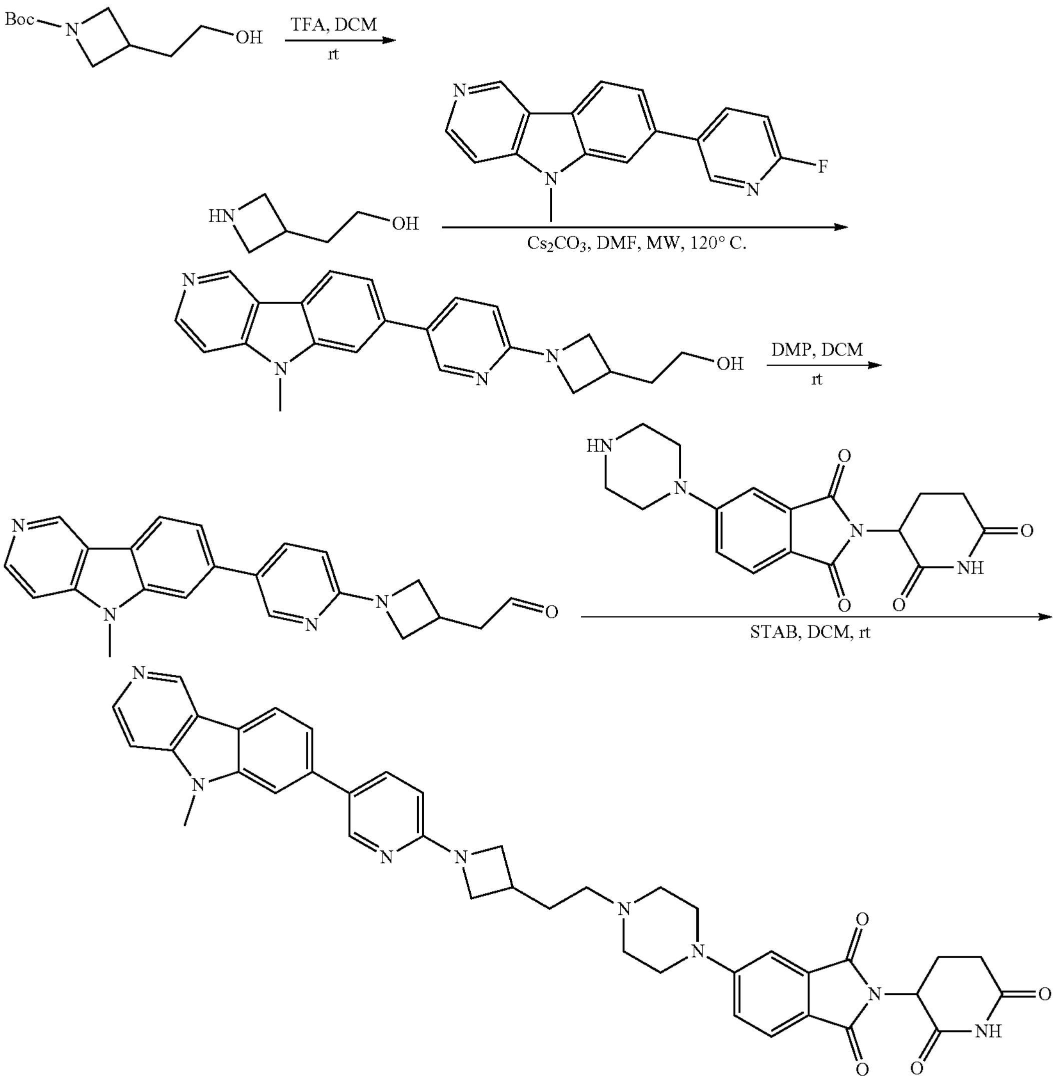
Exemplary Compound 435

Exemplary Synthesis of Exemplary Compound 436

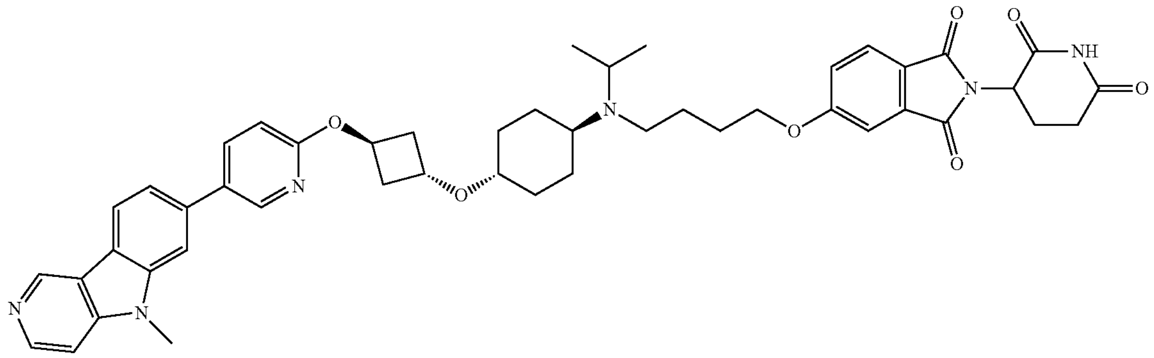 [SMILES: CC(C)N(CCCCOc1ccc2c(c1)C(=O)N(C1CCC(=O)NC1=O)C2=O)[C@H]1CC[C@H](O[C@H]2C[C@H](Oc3ccc(-c4ccc5c6cnccc6n(C)c5c4)cn3)C2)CC1]

Step 1

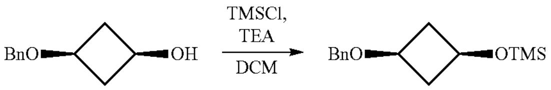

Into a 100-mL round-bottom flask, was placed (Is, 3s)-3-(benzyloxy)cyclobutan-1-ol (1.00 g, 5.62 mmol, 1.0 equiv) and TEA (1.70 g, 16.80 mmol, 3.0 equiv) in THF (40 mL) at 0° C. To the solution was added dropwise TMSCl (0.67 g, 6.17 mmol, 1.1 equiv). The resulting mixture was stirred at the same temperature for 30 min, diluted with 30 ml of hexane and filtered to remove the insoluble salts. The filtrate was concentrated under reduced pressure. This resulted in 1.37 g (crude) of trimethyl[(1s,3s)-3-(benzyloxy)cyclobutoxy]silane as a yellow oil.

Step 2

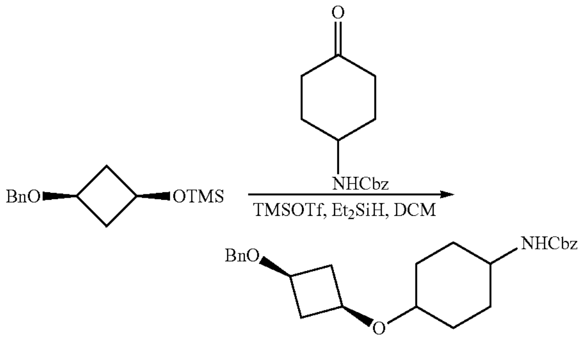

Into a 250-mL 3-neck round-bottom flask, was placed trimethyl[(1s,3s)-3-(benzyloxy)cyclobutoxy]silane (1.11 g, 4.44 mmol, 1.0 equiv) and benzyl N-(4-oxocyclohexyl) carbamate (1.09 g, 4.44 mmol, 1.0 equiv) in DCM (20.00 mL) at −78° C., to which was added $Et_3SiH$ (0.51 g, 4.39 mmol, 1.0 equiv), and TMSOTf (0.50 g, 2.25 mmol, 0.5 equiv) at −78° C. The resulting solution was allowed to warm slowly to 0° C. and stirred for 1 hr at 0° C. The resulting solution was diluted with 100 mL of EA and 100 mL $H_3PO_4$ (1M), and the layers were separated. The resulting mixture was washed with (3×100 mL) of brine. The mixture was dried over anhydrous sodium sulfate and concentrated. The residue was applied onto a silica gel column eluting with ethyl acetate/petroleum ether (1:1). This resulted in 1.24 g (68%) of benzyl N-[4-[(1s,3s)-3-(benzyloxy)cyclobutoxy]cyclohexyl]carbamate as a yellow oil.

Benzyl N-[4-[(1s,3s)-3-(benzyloxy)cyclobutoxy]cyclohexyl]carbamate was converted to tert-butyl (4-((1s,3s)-3-hydroxycyclobutoxy)cyclohexyl)carbamate according to the scheme below using procedures described for other examples above.

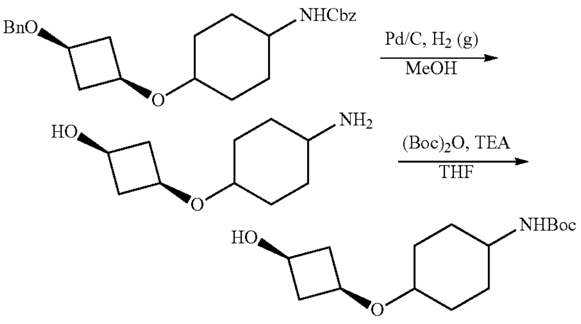

Step 5

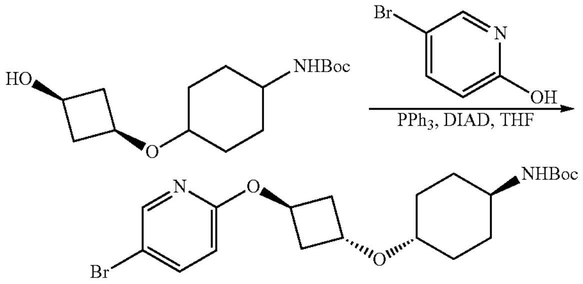

Into a 100-mL round-bottom flask purged and maintained with an inert atmosphere of nitrogen, was placed tert-butyl N-[4-[(1s,3s)-3-hydroxycyclobutoxy]cyclohexyl]carbamate (500 mg, 1.75 mmol, 1.0 equiv) and 5-bromopyridin-2-ol (368 mg, 2.13 mmol, 1.2 equiv) in THF (10 mL), to which was added $PPh_3$ (700 mg, 2.67 mmol, 1.5 equiv). This was followed by the addition of a solution of DIAD (531 mg, 2.63 mmol, 1.5 equiv) in THF (5 mL) dropwise with stirring at 0° C. in 5 min. The resulting solution was stirred for 15 hr at 60° C. The reaction mixture was cooled to room temperature. The resulting solution was diluted with 30 mL of EA. The resulting mixture was washed with (3×30 mL) of $H_2O$. The mixture was dried over anhydrous sodium sulfate and concentrated. The residue was applied onto a silica gel column eluting with ethyl acetate/petroleum ether (1:1).

This resulted in 200 mg (26%) of tert-butyl N-[(1r,4r)-4-[(1r,3r)-3-[(5-bromopyridin-2-yl)oxy]cyclobutoxy]cyclohexyl]carbamate as a yellow solid.

tert-Butyl N-[(1r,4r)-4-[(1r,3r)-3-[(5-bromopyridin-2-yl)oxy]cyclobutoxy]cyclohexyl]carbamate was converted to (1R,4r)-4-((1r,3R)-3-((5-(5-methyl-5H-pyrido[4,3-b]indol-7-yl)pyridin-2-yl)oxy)cyclobutoxy)cyclohexan-1-amine according to the scheme below using procedures described for other examples above.

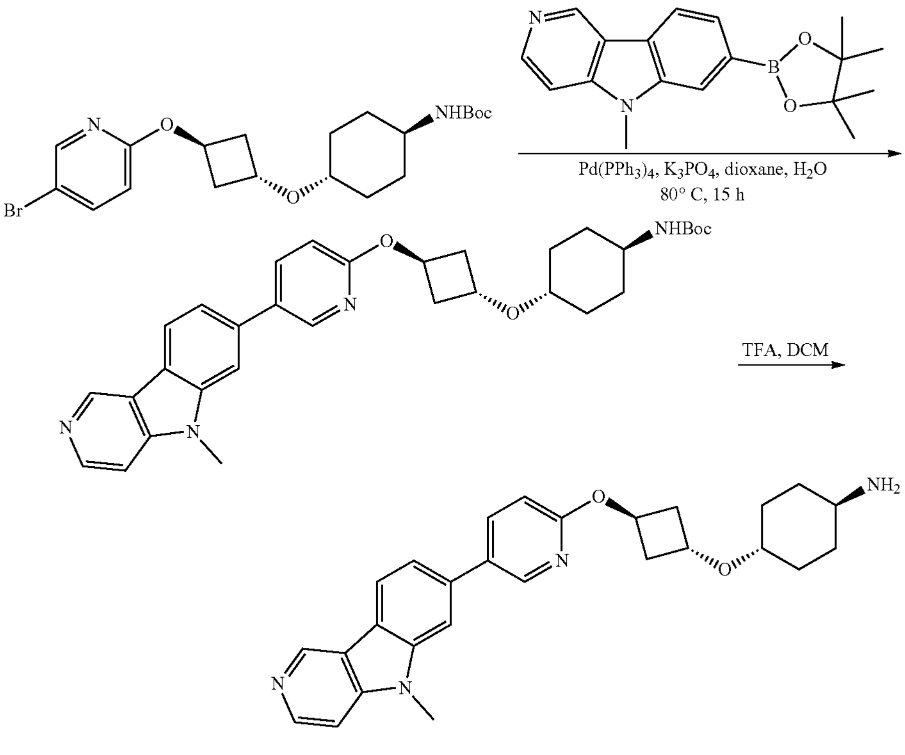

Step 8

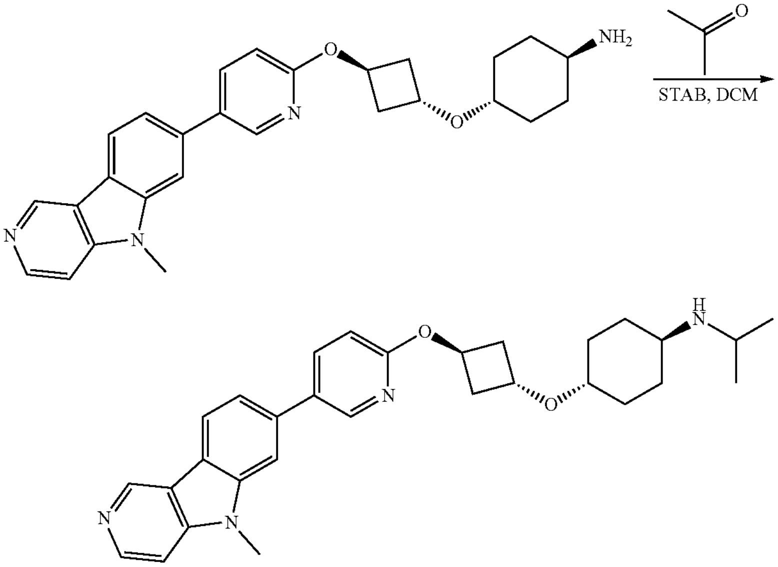

Into a 50-mL round-bottom flask, was placed (1r,4r)-4-[(1r,3r)-3-[(5-[5-methylpyrido[4,3-b]indol-7-yl]pyridin-2-yl)oxy]cyclobutoxy]cyclohexan-1-amine (70 mg, 0.16 mmol, 1.0 equiv) in acetone (2 mL) and DCM (2 mL), to which was added STAB (200 mg, 0.94 mmol, 6.0 equiv). The resulting solution was stirred for 2 hr at room temperature. The resulting mixture was concentrated. The residue was applied onto a silica gel column with dichloromethane/methanol (10:1). This resulted in 50 mg (65%) of (1r,4r)-N-isopropyl-4-[(1r,3r)-3-[(5-[5-methylpyrido[4,3-b]indol-7-yl]pyridin-2-yl)oxy]cyclobutoxy]cyclohexan-1-amine as a yellow solid.

Dimethyl 4-(4-oxobutoxy)phthalate according to the scheme below using procedures described for other examples above and commonly known to those skilled in the art.

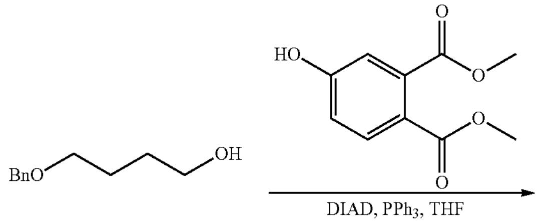

-continued

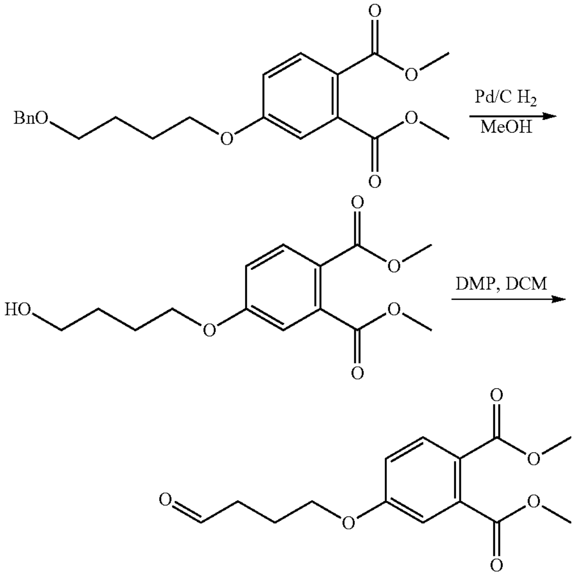

Step 12

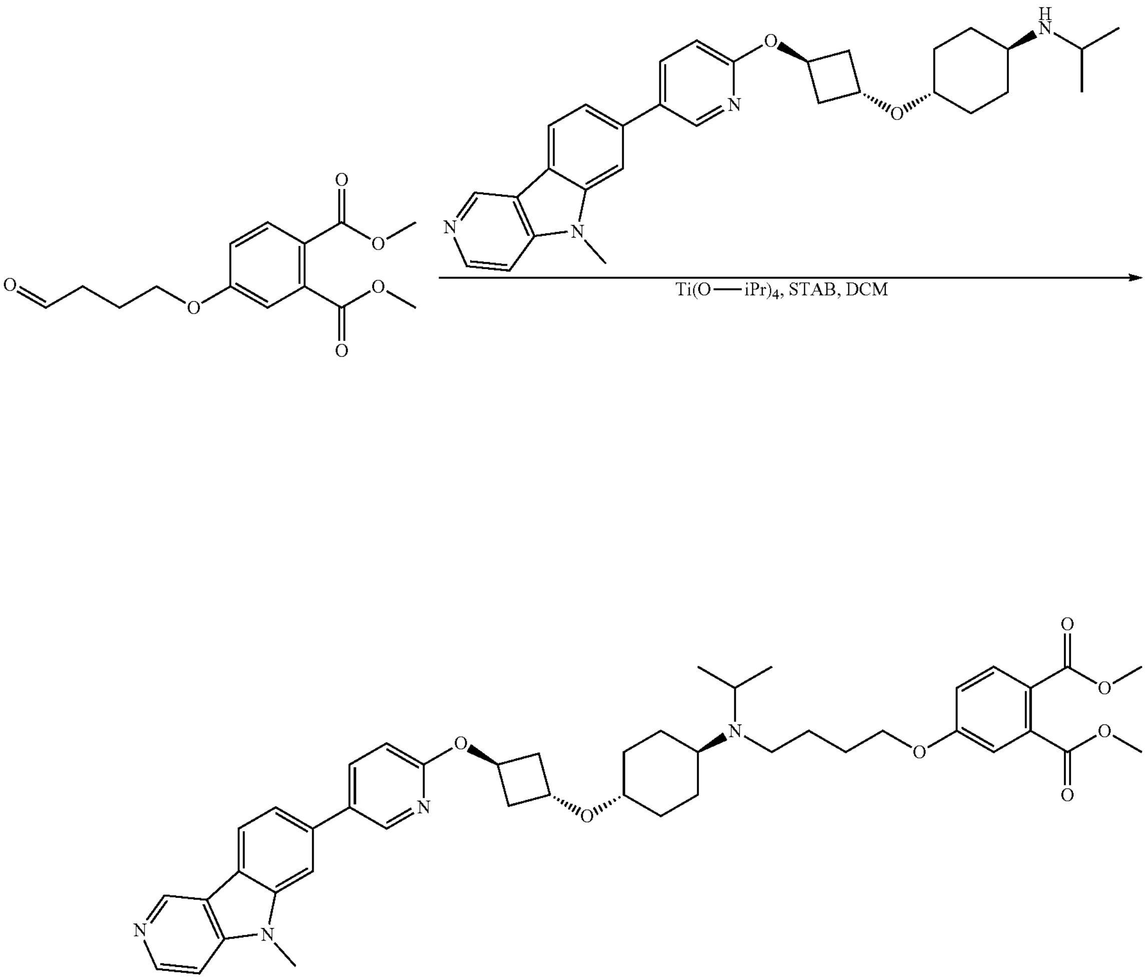

Into a 50-mL round-bottom flask, was placed (1r,4r)-N-isopropyl-4-[(1r,3r)-3-[(5-[5-methylpyrido[4,3-b]indol-7-yl]pyridin-2-yl)oxy]cyclobutoxy]cyclohexan-1-amine (50 mg, 0.10 mmol, 1.0 equiv) and 1,2-dimethyl 4-(4-oxobutoxy)phthalate (35 mg, 0.12 mmol, 1.2 equiv) in DCM (5 mL), to which was added STAB (44 mg, 0.20 mmol, 2.0 equiv). The resulting solution was stirred for 2 hr at room temperature. The resulting mixture was concentrated. The residue was applied onto a silica gel column eluting with dichloromethane/methanol (10:1). This resulted in 50 mg (65%) of 1,2-dimethyl 4-(4-[isopropyl[(1r,4r)-4-[(1r,3r)-3-[(5-[5-methylpyrido[4,3-b]indol-7-yl]pyridin-2-yl)oxy]cyclobutoxy]cyclohexyl]amino]butoxy)phthalate as a yellow solid.

1,2-dimethyl 4-(4-[isopropyl[(1r,4r)-4-[(1r,3r)-3-[(5-[5-methylpyrido[4,3-b]indol-7-yl]pyridin-2-yl)oxy]cyclobutoxy]cyclohexyl]amino]butoxy)phthalate was converted to the title compound using procedures described for other examples above and commonly known to those skilled in the art.

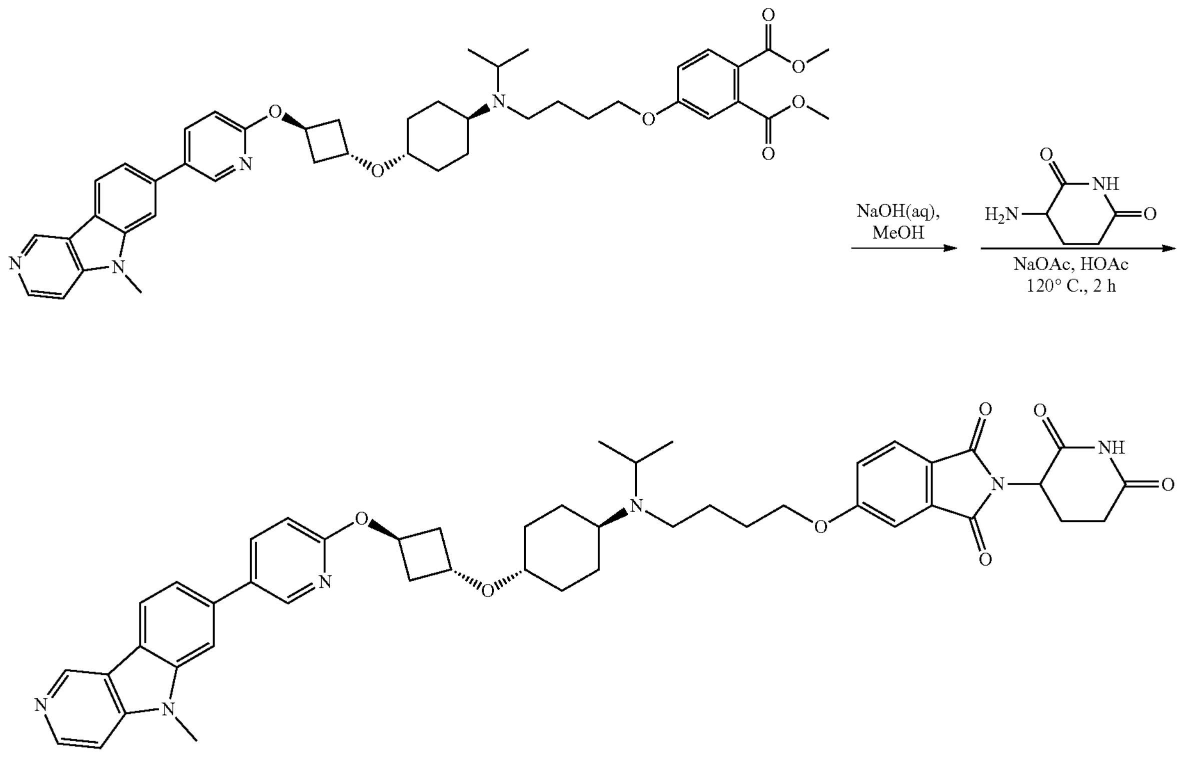

Exemplary Compound 436

Exemplary Synthesis of Exemplary Compound 437

Step 1

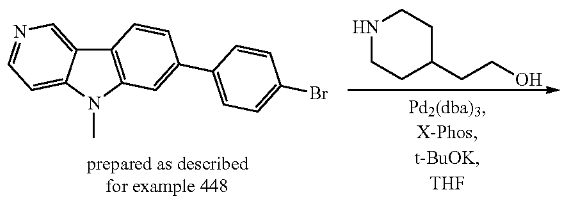

-continued

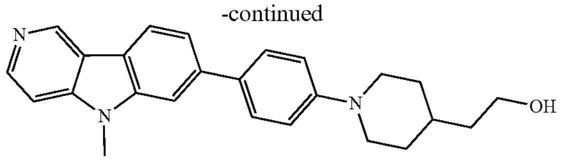

Into a 250-mL round-bottom flask purged and maintained with an inert atmosphere of nitrogen, was placed 7-(4-bromophenyl)-5-methylpyrido[4,3-b]indole (500 mg, 1.48 mmol, 1.0 equiv), 4-piperidineethanol (575 mg, 4.45 mmol, 3.0 equiv), X-Phos (1.41 g, 2.97 mmol, 2.0 equiv) in THF (50 mL), to which was added t-BuOK (183 mg, 1.63 mmol, 1.1 equiv), Pd(dba)$_3$ (136 mg, 0.15 mmol, 0.1 equiv). The resulting solution was stirred for 3 hr at 70° C. in an oil bath. The reaction mixture was cooled to room temperature. The resulting mixture was concentrated under vacuum. The residue was applied onto a silica gel column eluting with dichloromethane/methanol (100/0 to 8/1). This resulted in 200 mg (35%) of 2-[1-(4-[5-methylpyrido[4,3-b]indol-7-yl]phenyl)piperidin-4-yl]ethanol as a solid.

2-[1-(4-[5-Methylpyrido[4,3-b]indol-7-yl]phenyl)piperidin-4-yl]ethanol was converted to the title compound using procedures analogous to those described for steps 3 and 4 of exemplary compound 400.

Exemplary Synthesis of Exemplary Compound 438

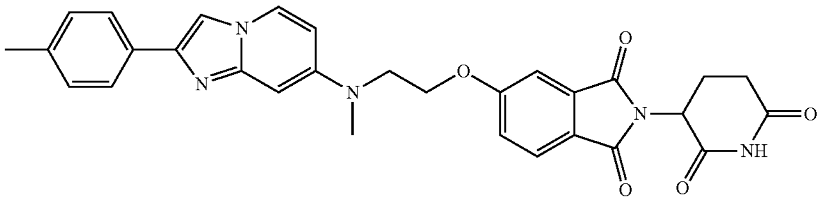 [SMILES: Cc1ccc(-c2cn3ccc(N(C)CCOc4ccc5c(c4)C(=O)N(C4CCC(=O)NC4=O)C5=O)cc3n2)cc1]

Step 1

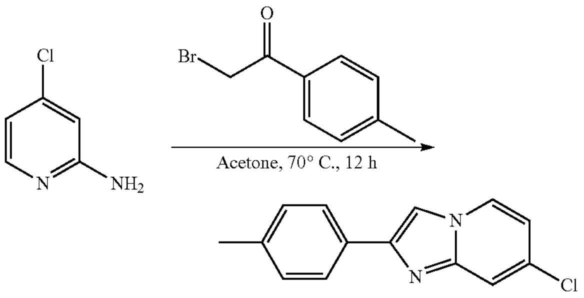

A mixture of 4-chloropyridin-2-amine (3 g, 23.34 mmol, 1 eq) and 2-bromo-1-(p-tolyl)ethanone (5.47 g, 25.67 mmol, 1.1 eq) in acetone (50 mL) was stirred at 70° C. for 12 h. The mixture was filtered, and the solid was washed with ethyl acetate (30 mL×2). The solid was used for the next step without further purification. Crude 7-chloro-2-(p-tolyl)imidazo[1,2-a]pyridine (5 g, 20.60 mmol) was obtained as a white solid.

Step 2

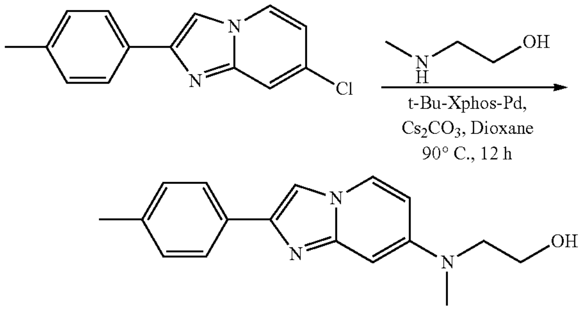

To a solution of 7-chloro-2-(p-tolyl)imidazo[1,2-a]pyridine (1 g, 4.12 mmol, 1 eq) in dioxane (15 mL) was added tBuXPhos-Pd-G3 ([(2-di-tert-butylphosphino-2',4',6'-triisopropyl-1,1'-biphenyl)-2-(2'-amino-1,1'-biphenyl)] palladium(II) methanesulfonate) (163 mg, 0.20 mmol, 0.05 eq), cesium carbonate (2.68 g, 8.24 mmol, 2 eq), and 2-(methylamino)ethanol (340 mg, 4.53 mmol, 1.1 eq). The mixture was stirred at 90° C. for 12 h. LCMS showed WX-ARV-MB-026-AA-1 was consumed completely and one main peak with desired mass was detected. The mixture was filtered and concentrated under reduced pressure. The residue was purified by prep-HPLC column: Phenomenex luna C18 250*50 mm*10 um; mobile phase: [water (10 mM NH4HCO3)-ACN]; B %: 30%-60%, 16 min. 2-[methyl-[2-(p-tolyl)imidazo[1,2-a]pyridin-7-yl]

amino]ethanol (0.7 g, 2.49 mmol, 60% yield) was obtained as a white solid

Step 3

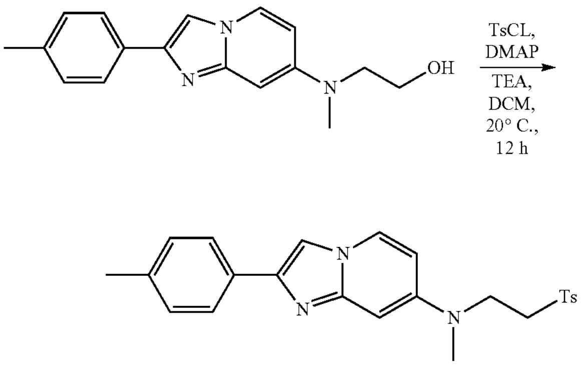

To a mixture of 2-[methyl-[2-(p-tolyl)imidazo[1,2-a]pyridin-7-yl]amino]ethanol (100 mg, 0.35 mmol, 1 eq), triethylamine (71 mg, 2 eq) and dimethylaminopyridine (8 mg, 0.07 mmol, 0.2 eq) in dichloromethane (20 mL) was added p-toluenesulfonyl chloride (135 mg, 0.71 mmol, 2 eq). The mixture stirred at 20° C. for 12 h. The mixture was quenched by addition water (100 mL), extracted with ethyl acetate (30 mL×3), and the combined organic phase was washed with brine (30 mL), dried over anhydrous sodium sulfate, filtered and concentrated under reduced pressure. The residue was purified by prep-TLC (chloromethane:methanol=10:1). Compound 2-[methyl-[2-(p-tolyl)imidazo[1,2-a]pyridin-7-yl]amino]ethyl 4-methylbenzenesulfonate (100 mg, 0.22 mmol, 64% yield) was obtained as a yellow oil.

Step 4

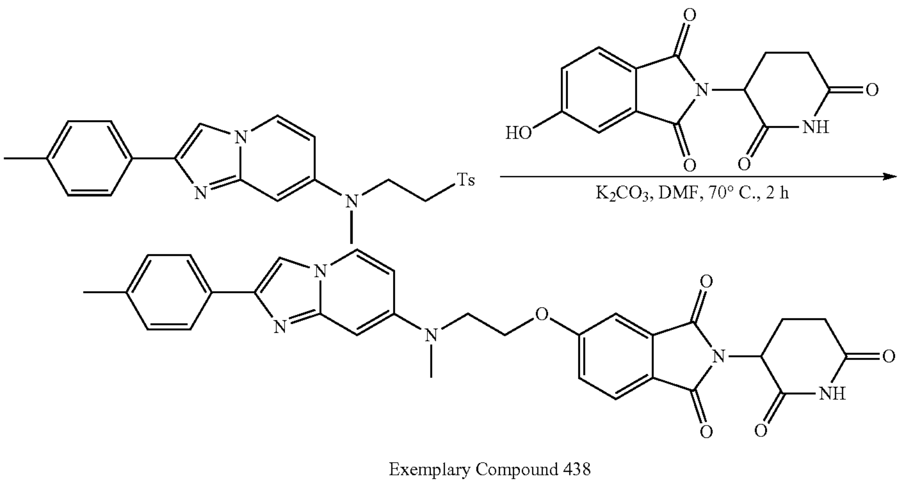

Exemplary Compound 438

To a mixture of 2-[methyl-[2-(p-tolyl)imidazo[1,2-a]pyridin-7-yl]amino]ethyl 4-methylbenzenesulfonate (50 mg, 0.11 mmol, 1 eq) in dimethylformamide (4 mL) was added 2-(2,6-dioxo-3-piperidyl)-5-hydroxy-isoindoline-1,3-dione (34 mg, 0.12 mmol, 1.1 eq) and potassium carbonate (31 mg, 0.22 mmol, 2 eq). The mixture was stirred at 70° C. for 2 h. The mixture was quenched by addition water (100 mL), extracted with ethyl acetate (30 mL×3), the combined organic phase was washed with brine (30 mL), dried over anhydrous sodium sulfate, filtered and concentrated under reduced pressure. The residue was purified by prep-TLC (dichloromethane:methanol=10:1). Compound 2-(2,6-dioxo-3-piperidyl)-5-[2-[ methyl-[2-(p-tolyl)imidazo[1,2-a]pyridin-7-yl]amino] ethoxy]isoindoline-1,3-dione (16.2 mg, 0.02 mmol, 24% yield) was obtained as a yellow solid.

Using analogous procedures the following exemplary compounds were prepared according to the scheme below: 459, 463, 464.

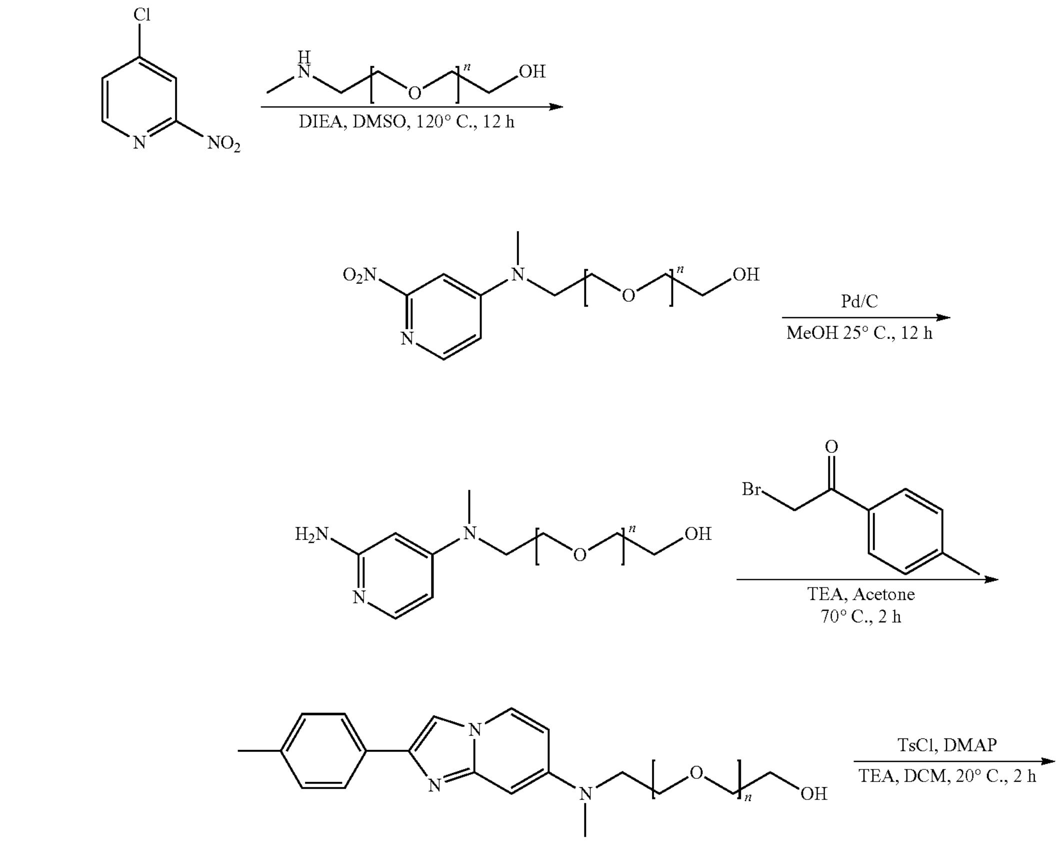

-continued

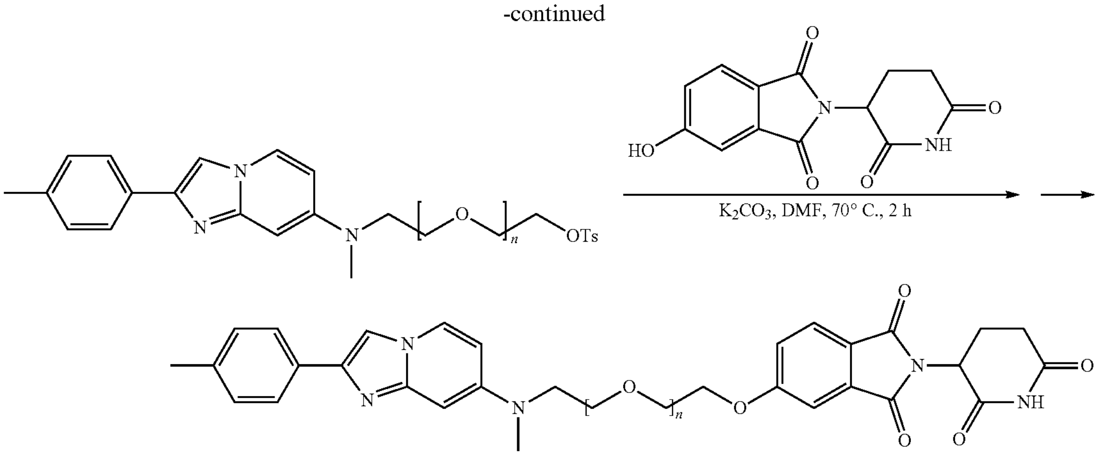

Exemplary Synthesis of Exemplary Compound 439

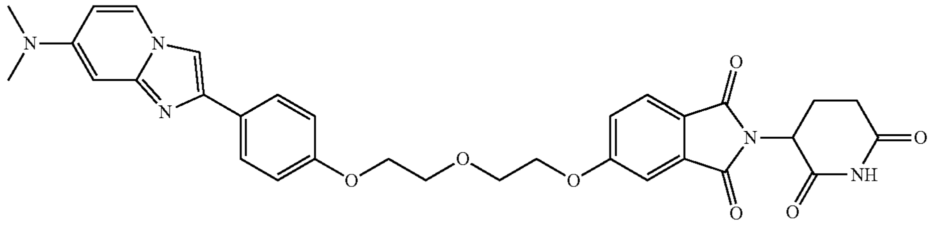 [SMILES: CN(C)c1ccn2cc(-c3ccc(OCCOCCOc4ccc5c(c4)C(=O)N(C4CCC(=O)NC4=O)C5=O)cc3)nc2c1]

Step 1

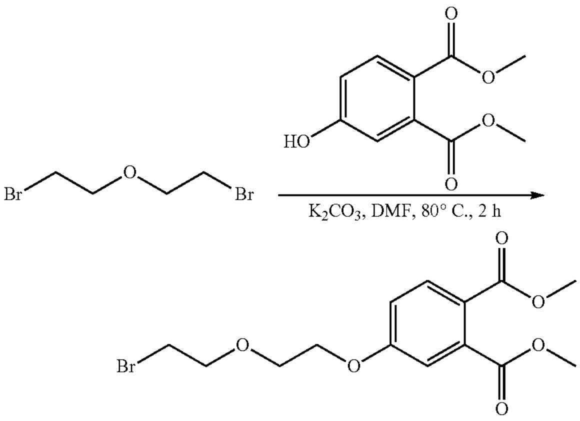

To a mixture of 1-bromo-2-(2-bromoethoxy)ethane (1.66 g, 7.14 mmol, 3 eq) and dimethyl 4-hydroxybenzene-1,2-dicarboxylate (500 mg, 2.38 mmol, 1 eq) in N,N-dimethylformamide (10 mL) was added potassium carbonate (657 mg, 4.76 mmol, 2 eq). The mixture was stirred at 80° C. for 2 h. The mixture was filtered, diluted with water (150 mL), and extracted with ethyl acetate (40 mL×3). The combined organic phase washed with brine (30 mL), dried over anhydrous sodium sulfate, filtered and concentrated under reduced pressure. The residue was purified by silica gel column chromatography (petroleum ether/ethyl acetate=15:1 to 10:1). Compound dimethyl 4-[2-(2-bromoethoxy) ethoxy] benzene-1,2-dicarboxylate (700 mg, 1.94 mmol, 81% yield) as a brown oil was obtained.

Step 2

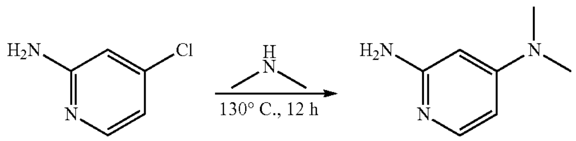

A mixture of 4-chloropyridin-2-amine (10 g, 77.79 mmol, 1 eq) and N-methylmethanamine (43.84 g, 388 mmol, 49 mL, 5 eq) in water (5 mL) was stirred at 130° C. for 12 h. The mixture was concentrated under reduced pressure. Crude N,N-dimethylpyridine-2,4-diamine (6 g, 43.74 mmol) was obtained as a brown solid and used in the next step without purification.

Step 3

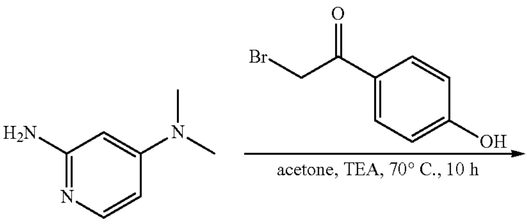

-continued

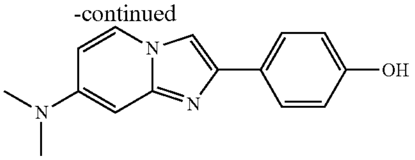

To a mixture of N,N-dimethylpyridine-2,4-diamine (2 g, 14 mmol, 1 eq) in acetone (50 mL) was added 2-bromo-1-(4-hydroxyphenyl)ethanone (3.45 g, 16 mmol, 1.1 eq). The mixture was stirred at 70° C. for 12 h. The mixture was filtered and the solid washed with ethyl acetate (30 mL×3). Crude 4-[7-(dimethylamino)imidazo[1,2-a] pyridin-2-yl] phenol (1.8 g, 7.11 mmol) was obtained as a brown solid and was used in the next step without further purification.

Step 4

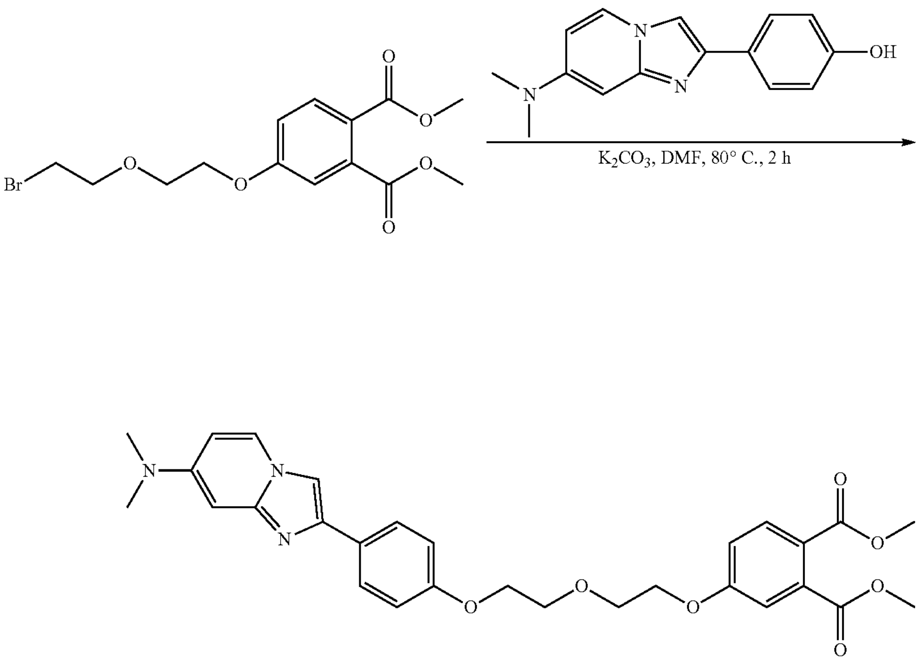

To a solution of dimethyl 4-[2-(2-bromoethoxy)ethoxy] benzene-1,2-dicarboxylate (150 mg, 0.4 mmol, 1 eq) in N,N-dimethylformamide (5 mL) was added potassium carbonate (114 mg, 0.8 mmol, 2 eq) and 4-[7-(dimethylamino) imidazo[1,2-a]pyridin-2-yl]phenol (157 mg, 0.6 mmol, 1.5 eq). The mixture was stirred at 80° C. for 2 h. The reaction mixture was quenched by addition of water (10 mL) at 25° C., and extracted with ethyl acetate (5 mL×3). The combined organic layers were washed with brine (5 mL×2), dried over sodium sulfate, filtered and concentrated under reduced pressure to give a residue. The residue was purified by prep-TLC (petroleum ether/ethyl acetate=3:1). Dimethyl 4-[2-[2-[4-[7-(dimethylamino)imidazo[1,2-a]pyridin-2-yl] phenoxy]ethoxy]ethoxy]benzene-1,2-dicarboxylate (150 mg, 0.3 mmol, 67% yield) was obtained as a yellow solid.

Dimethyl 4-[2-[2-[4-[7-(dimethylamino)imidazo[1,2-a] pyridin-2-yl]phenoxy]ethoxy]ethoxy]benzene-1,2-dicarboxylate was converted to the final compound according to the scheme below using procedures described for other examples above.

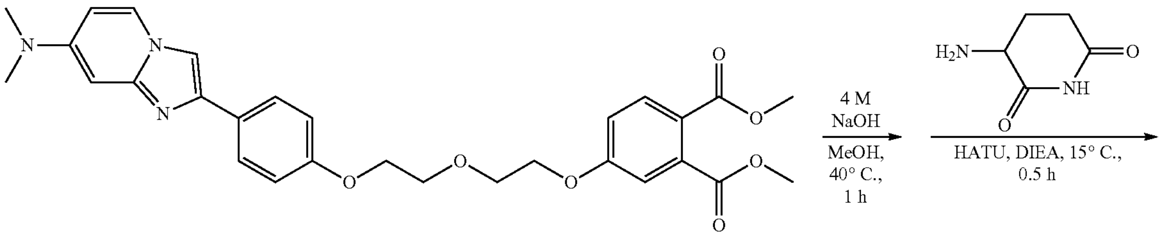

-continued

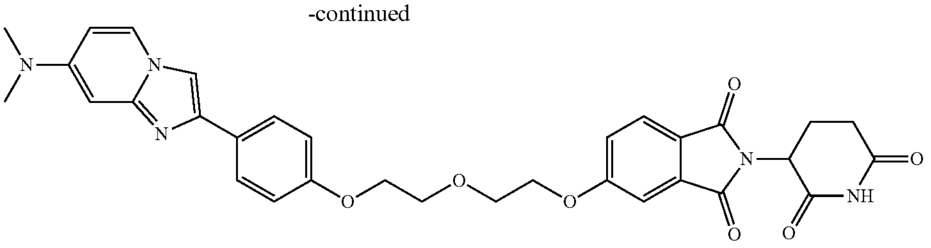

Exemplary Compound 439

Using analogous procedures the following exemplary compounds were prepared: 440, 441.

Exemplary Synthesis of Exemplary Compound 442

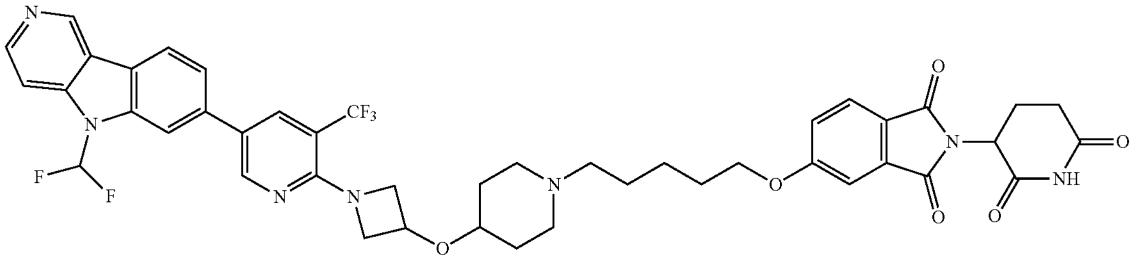 [SMILES: N#Cc1cc(-c2ccc3c4cnccc4n(C(F)F)c3c2)cnc1N1CC(OC2CCN(CCCCCOc3ccc4c(c3)C(=O)N(C3CCC(=O)NC3=O)C4=O)CC2)C1]

Step 1

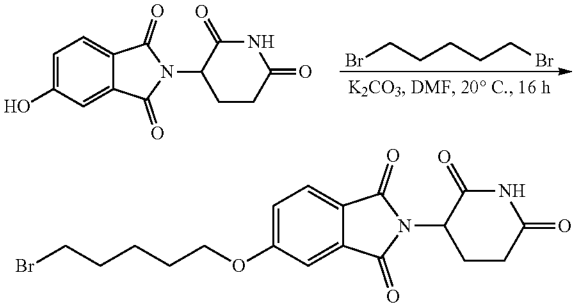

To a mixture of 1,5-dibromopentane (377 mg, 1.64 mmol, 0.22 mL, 0.9 eq) and 2-(2,6-dioxo-3-piperidyl)-5-hydroxy-isoindoline-1,3-dione (500 mg, 1.82 mmol, 1 eq) in N,N-dimethylformamide (40 mL) was added potassium carbonate (252 mg, 1.82 mmol, 1 eq) in one portion. The mixture was stirred at 20° C. for 16 h. The reaction mixture was poured into 1 M hydrochloric acid (40 mL), then diluted with water 20 mL and extracted with ethyl acetate (30 mL×3). The combined organic layers were washed with brine 20 mL, dried over anhydrous sodium sulfate, filtered and concentrated under reduced pressure to give a residue. The residue was purified by silica gel column chromatography (petroleum ether/ethyl acetate=20/1 to 5/1) and then additionally purified by prep-TLC (dichloromethane/methanol=10/1) to give crude product. The crude product was additionally purified by semi-preparative reverse phase HPLC (33-63% acetonitrile+0.225% formic acid in water, over 25 min). 5-(5-Bromopentoxy)-2-(2,6-dioxo-3-piperidyl)isoindoline-1,3-dione (220 mg, 0.52 mmol, 28% yield) was obtained as a light yellow solid.

Step 2

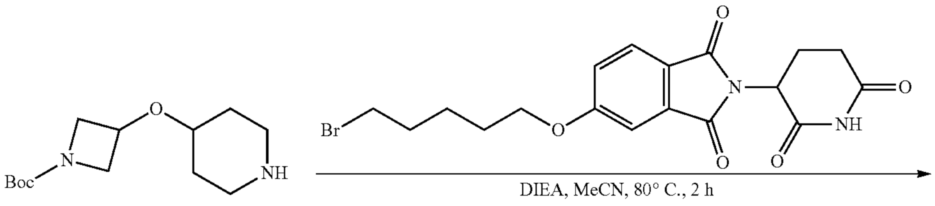

prepared as described for example 382

-continued

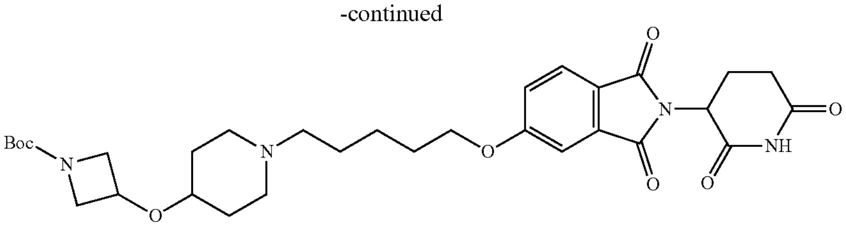

To a solution of tert-butyl 3-(4-piperidyloxy)azetidine-1-carboxylate (400 mg, 1.56 mmol, 1 eq) and 5-(5-bromopentoxy)-2-(2,6-dioxo-3-piperidyl)isoindoline-1,3-dione (660 mg, 1.56 mmol, 1 eq) in acetonitrile (10 mL) was added potassium iodide (259 mg, 1.56 mmol, 1 eq) and N,N-diisopropylethylamine (605 mg, 4.68 mmol, 3 eq). The reaction mixture was stirred at 80° C. for 2 h. The reaction mixture was diluted with water (80 mL) and extracted with ethyl acetate (80 mL×3). The combined organic layers were washed with brine (100 mL×3), dried over anhydrous sodium sulfate, filtered and concentrated under reduced pressure. The residue was purified by column chromatography (dichloromethane:methanol=100:1 to 20:1). tert-Butyl 3-[[1-[5-[2-(2,6-dioxo-3-piperidyl)-1,3-dioxo-isoindolin-5-yl]oxypentyl]-4-piperidyl]oxy]azetidine-1-carboxylate (930 mg, 1.55 mmol, 99% yield) was obtained as a yellow solid.

Step 3

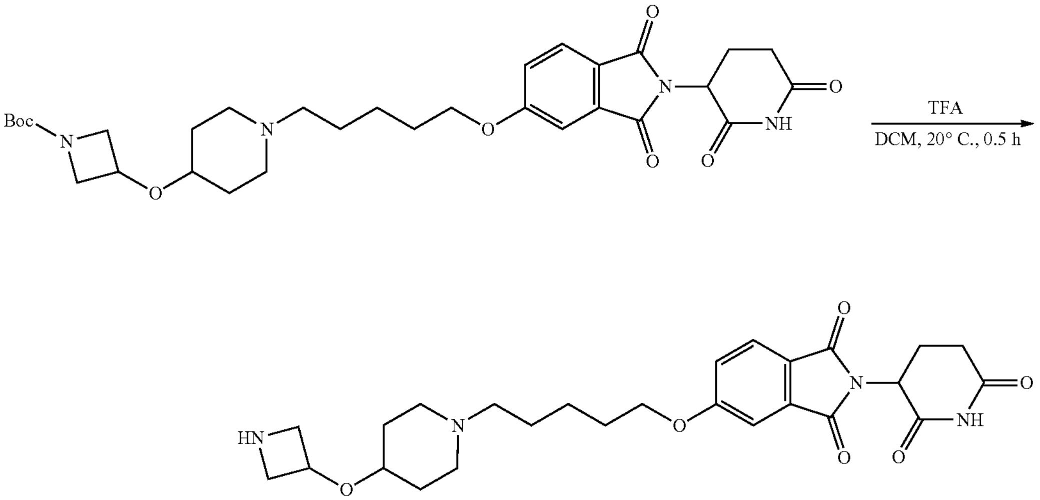

To a solution of tert-butyl 3-[[1-[5-[2-(2,6-dioxo-3-piperidyl)-1,3-dioxo-isoindolin-5-yl] oxypentyl]-4-piperidyl] oxy]azetidine-1-carboxylate (170 mg, 0.28 mmol, 1 eq) in dichloromethane (2 mL) was added trifluoroacetic acid (1.54 g, 13.51 mmol, 1.00 mL). The reaction mixture was stirred at 20° C. for 0.5 h. The reaction mixture was concentrated under reduced pressure. Crude 5-[5-[4-(azetidin-3-yloxy)-1-piperidyl]pentoxy]-2-(2,6-dioxo-3-piperidyl)isoindoline-1,3-dione trifluoroacetate (170 mg, 0.27 mmol) was obtained as a yellow oil and used directly in the next step.

Step 4

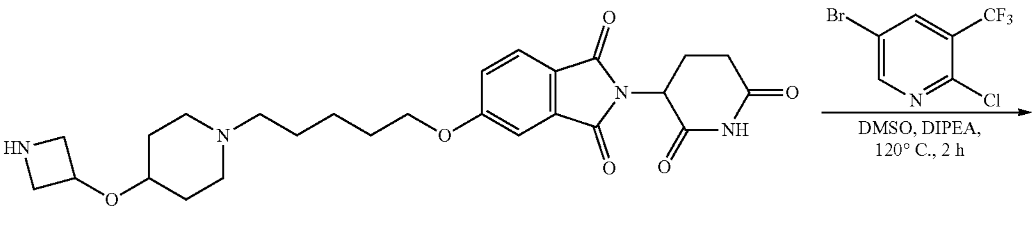

-continued

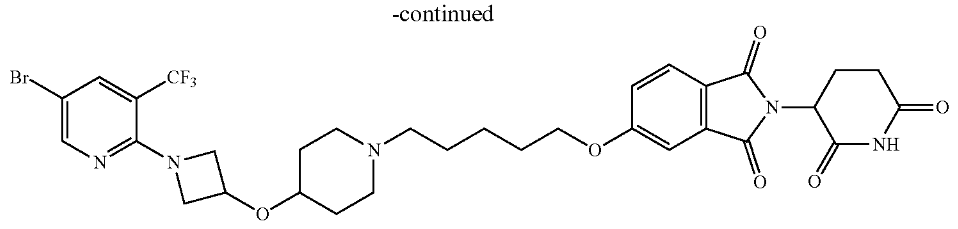

A solution of 5-bromo-2-chloro-3-(trifluoromethyl)pyridine (70 mg, 0.26 mmol, 1 eq), 5-[5-[4-(azetidin-3-yloxy)-1-piperidyl]pentoxy]-2-(2,6-dioxo-3-piperidyl)isoindoline-1,3-dione (164 mg, 0.26 mmol, 1 eq, trifluoroacetate) and N,N-diisopropylethylamine (173 mg, 1.34 mmol, 5 eq) in dimethylsulfoxide (5 mL) was stirred at 120° C. for 2 h. The reaction mixture was diluted with water (50 mL) and extracted with ethyl acetate (50 mL×3). The combined organic layers were washed with brine (50 mL×3), dried over anhydrous sodium sulfate, filtered and concentrated under reduced pressure. The residue was purified by column chromatography (dichloromethane:methanol=100/1 to 10/1). 5-[5-[4-[1-[5-bromo-3-(trifluoromethyl)-2-pyridyl]azetidin-3-yl]oxy-1-piperidyl]pentoxy]-2-(2,6-dioxo-3-piperidyl)isoindoline-1,3-dione (180 mg, 0.24 mmol, 92% yield) was obtained as a yellow oil.

Step 5

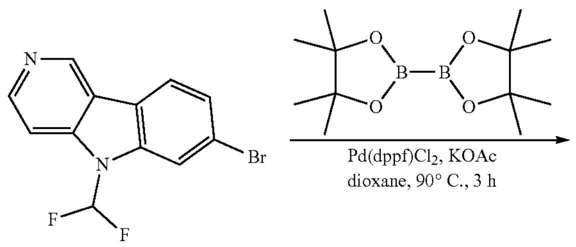

prepared as described for example 426

-continued

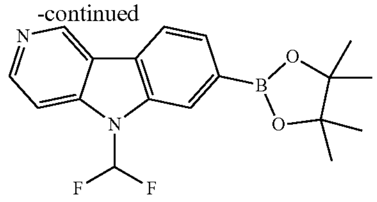

A mixture of 7-bromo-5-(difluoromethyl)pyrido[4,3-b]indole (300 mg, 1.01 mmol, 1 eq), 4,4,5,5-tetramethyl-2-(4,4,5,5-tetramethyl-1,3,2-dioxaborolan-2-yl)-1,3,2-dioxaborolane (307 mg, 1.21 mmol, 1.2 eq), potassium acetate (198 mg, 2.02 mmol, 2 eq), and [1,1-bis(diphenylphosphino)ferrocene]dichloropalladium(II) (73 mg, 0.1 mmol, 0.1 eq) in dioxane (10 mL) and N,N-dimethylformamide (5 mL) was degassed and then heated to 90° C. for 3 hours under nitrogen. The reaction mixture was diluted with water (100 mL) and extracted with ethyl acetate (100 mL×3). The combined organic layers were washed with brine (100 mL×3), dried over anhydrous sodium sulfate, filtered and concentrated under reduced pressure. The residue was purified by column chromatography (dichloromethane:methanol=100/1 to 30/1). 5-(Difluoromethyl)-7-(4,4,5,5-tetramethyl-1,3,2-dioxaborolan-2-yl)pyrido[4,3-b]indole (320 mg, 0.9 mmol, 92% yield) was obtained as a black brown solid.

Step 6

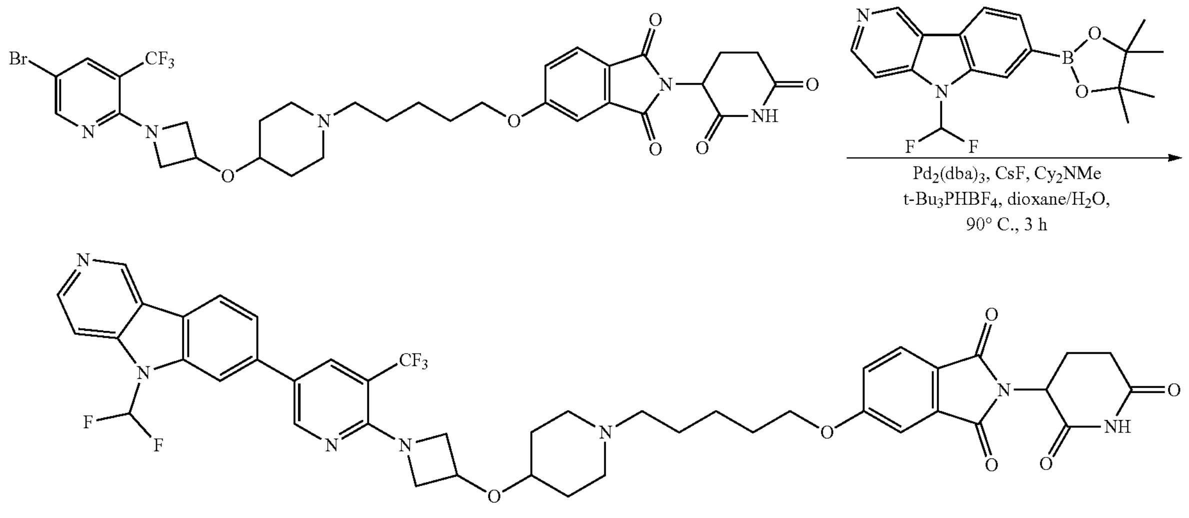

Exemplary compound 442

A mixture of 5-[5-[4-[1-[5-bromo-3-(trifluoromethyl)-2-pyridyl]azetidin-3-yl]oxy-1-piperidyl]pentoxy]-2-(2,6-dioxo-3-piperidyl)isoindoline-1,3-dione (100 mg, 0.1 mmol, 1 eq), 5-(difluoromethyl)-7-(4,4,5,5-tetramethyl-1,3,2-dioxaborolan-2-yl)pyrido[4,3-b]indole (47 mg, 0.13 mmol, 1 eq), tris(dibenzylideneacetone)dipalladium(0) (12 mg, 0.013 mmol, 0.1 eq), tri-tert-butylphosphonium tetrafluoroborate (40 mg, 0.13 mmol, 1 eq) and N-cyclohexyl-N-methyl-cyclohexanamine (54 mg, 0.27 mmol, 2 eq) in dioxane (5 mL) and water (0.5 mL) was degassed and then heated to 90° C. for 3 hours under nitrogen. The reaction mixture was diluted with DMF (3 mL), filtered and concentrated under reduced pressure. The residue was purified by prep-HPLC (column: Phenomenex Synergi C18 150*25*10 um; mobile phase: [water (0.225% FA)-ACN]; B %:13%-43%, 10 min). 5-[5-[14-[1-[5-[5-(Difluoromethyl)pyrido[4,3-b]indol-7-yl]-3-(trifluoromethyl)-2-pyridyl]azetidin-3-yl]oxy-1-piperidyl]pentoxy]-2-(2,6-dioxo-3-piperidyl)isoindoline-1,3-dione formate (33 mg, 0.03 mmol, 25% yield) was obtained as a white solid.

Exemplary Synthesis of Exemplary Compound 443

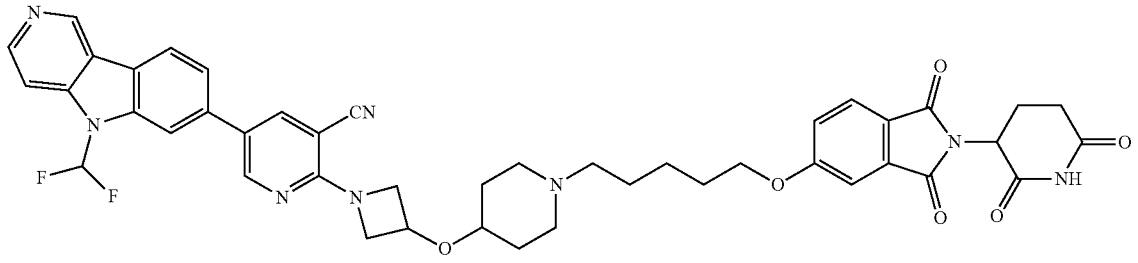

Prepared according to the scheme below using procedures analogous to those described for exemplary compound

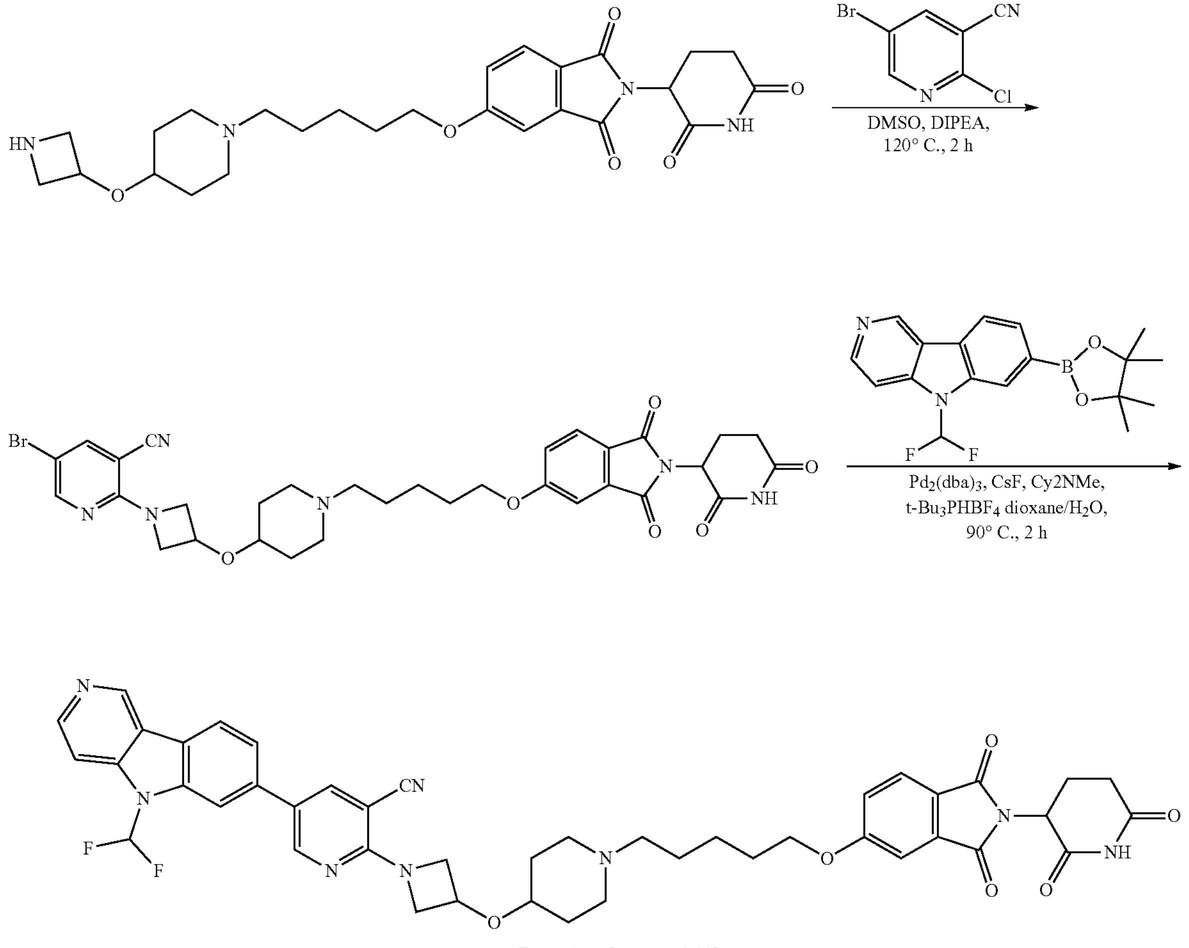

Exemplary Compound 443

Exemplary Synthesis of Exemplary Compound 444
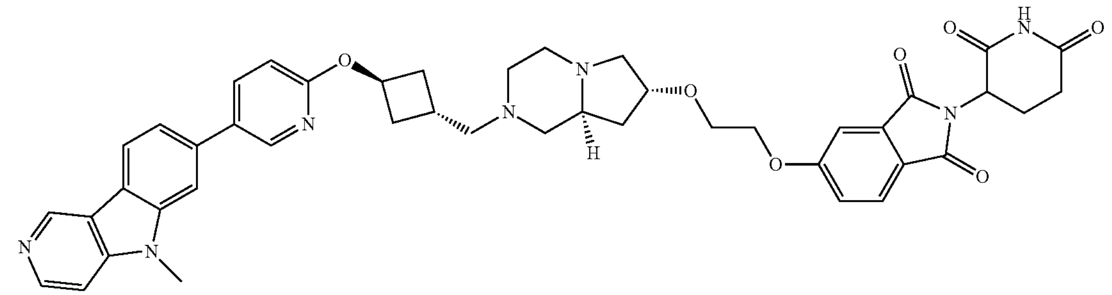 [SMILES: Cn1c2ccncc2c2ccc(-c3ccc(O[C@H]4C[C@H](CN5CCN6C[C@H](OCCOc7ccc8c(c7)C(=O)N(C7CCC(=O)NC7=O)C8=O)C[C@H]6C5)C4)nc3)cc21]
Prepared according to the scheme below using procedures described for other examples as well as those commonly known to skilled in the art.
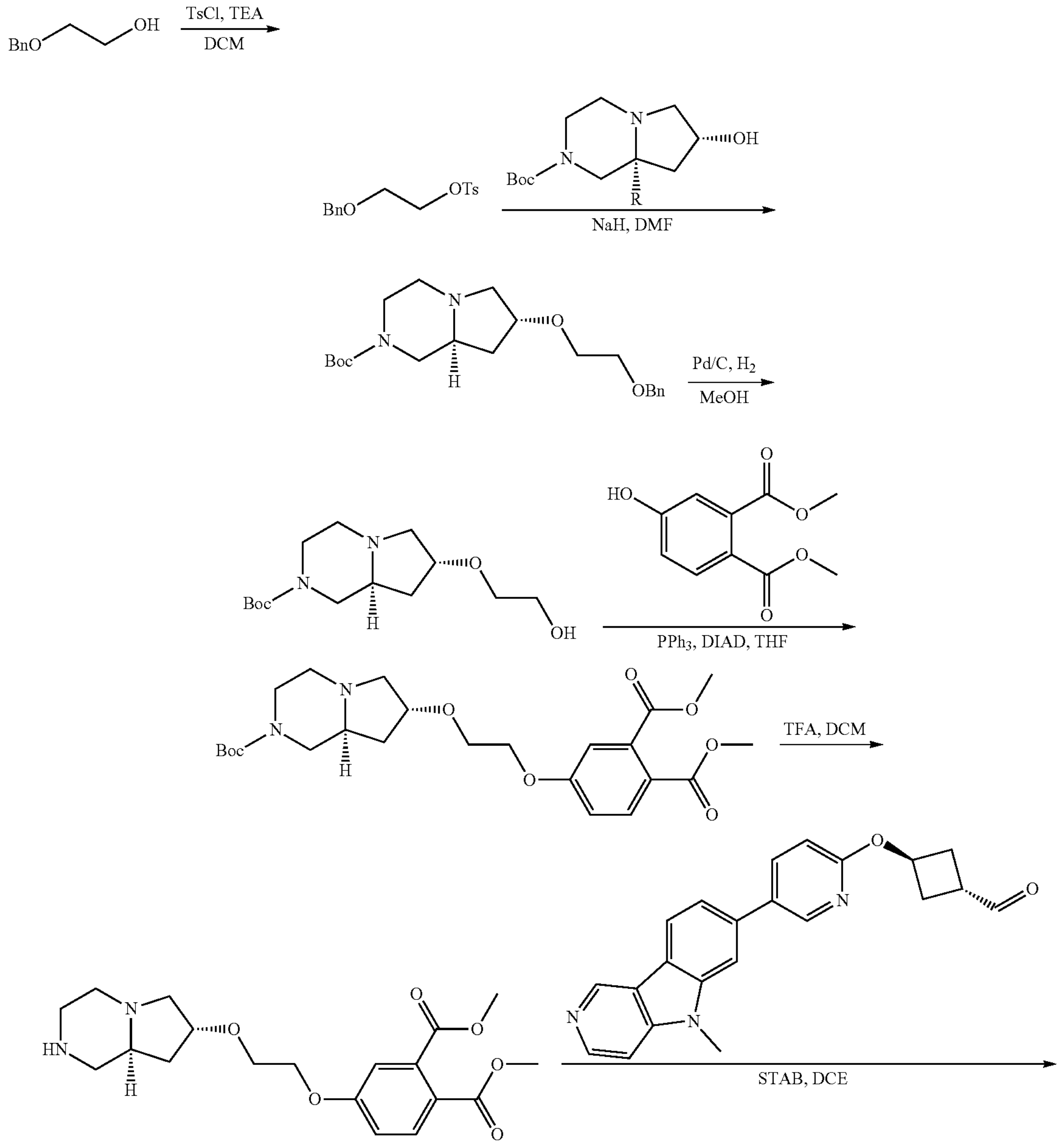

-continued
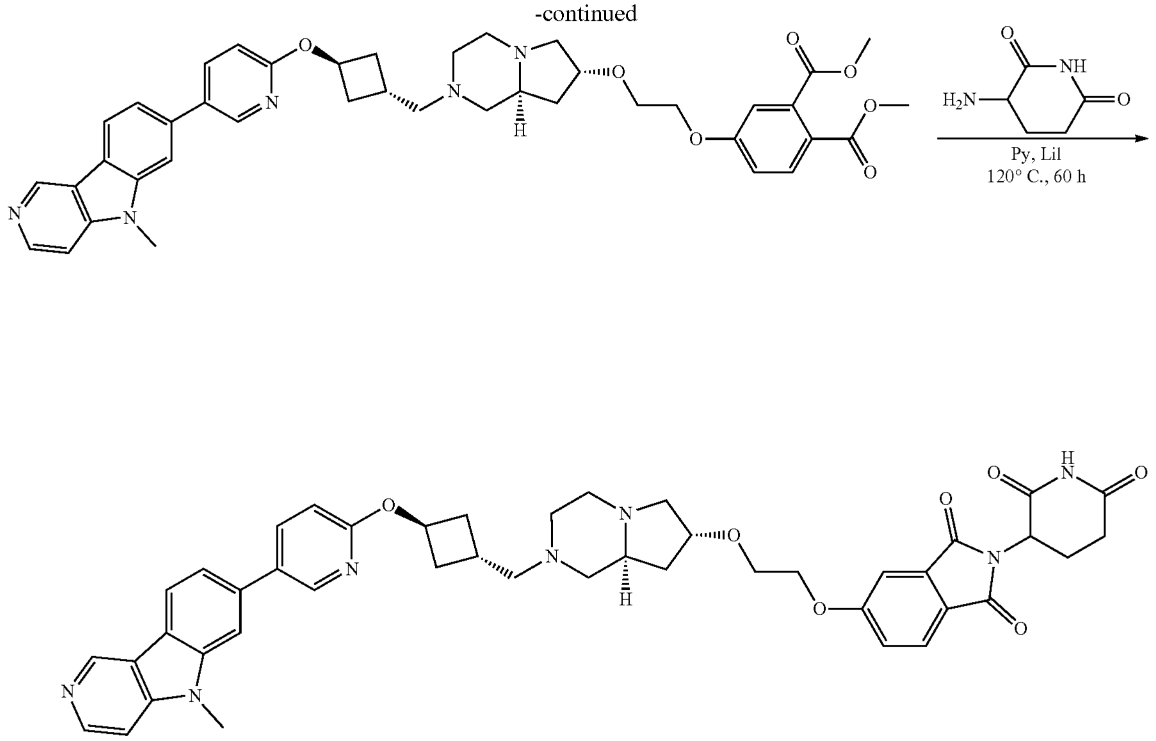
Exemplary Compound 444
Exemplary Synthesis of Exemplary Compound 445
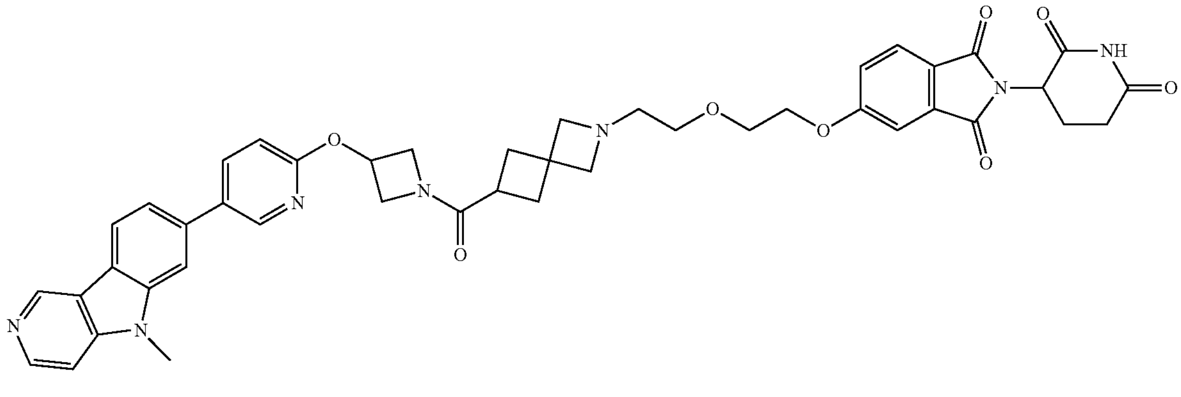 [SMILES: Cn1c2ccncc2c2ccc(-c3ccc(OC4CN(C(=O)C5CC6(C5)CN(CCOCCOc5ccc7c(c5)C(=O)N(C5CCC(=O)NC5=O)C7=O)C6)C4)nc3)cc21]
Prepared according to the scheme below using procedures described for other examples above
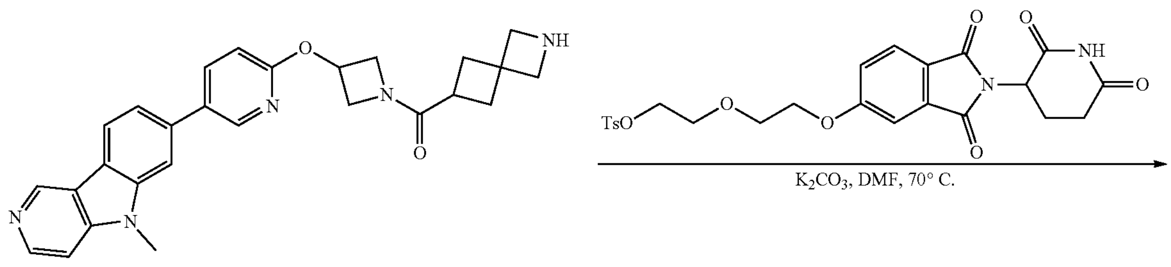
prepared as described in example 403

-continued
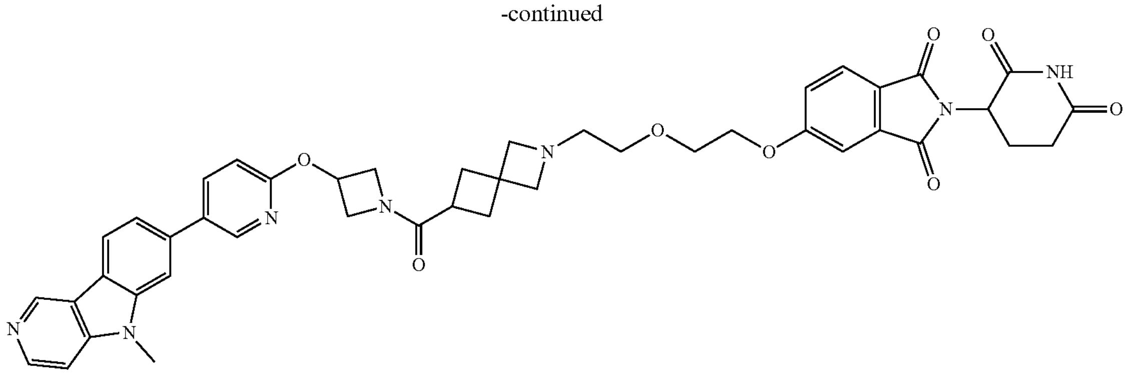
Exemplary Compound 445
Exemplary Synthesis of Exemplary Compound 446
Prepared according to the scheme below using procedures described for other examples above as well as common procedures known to those skilled in the art.

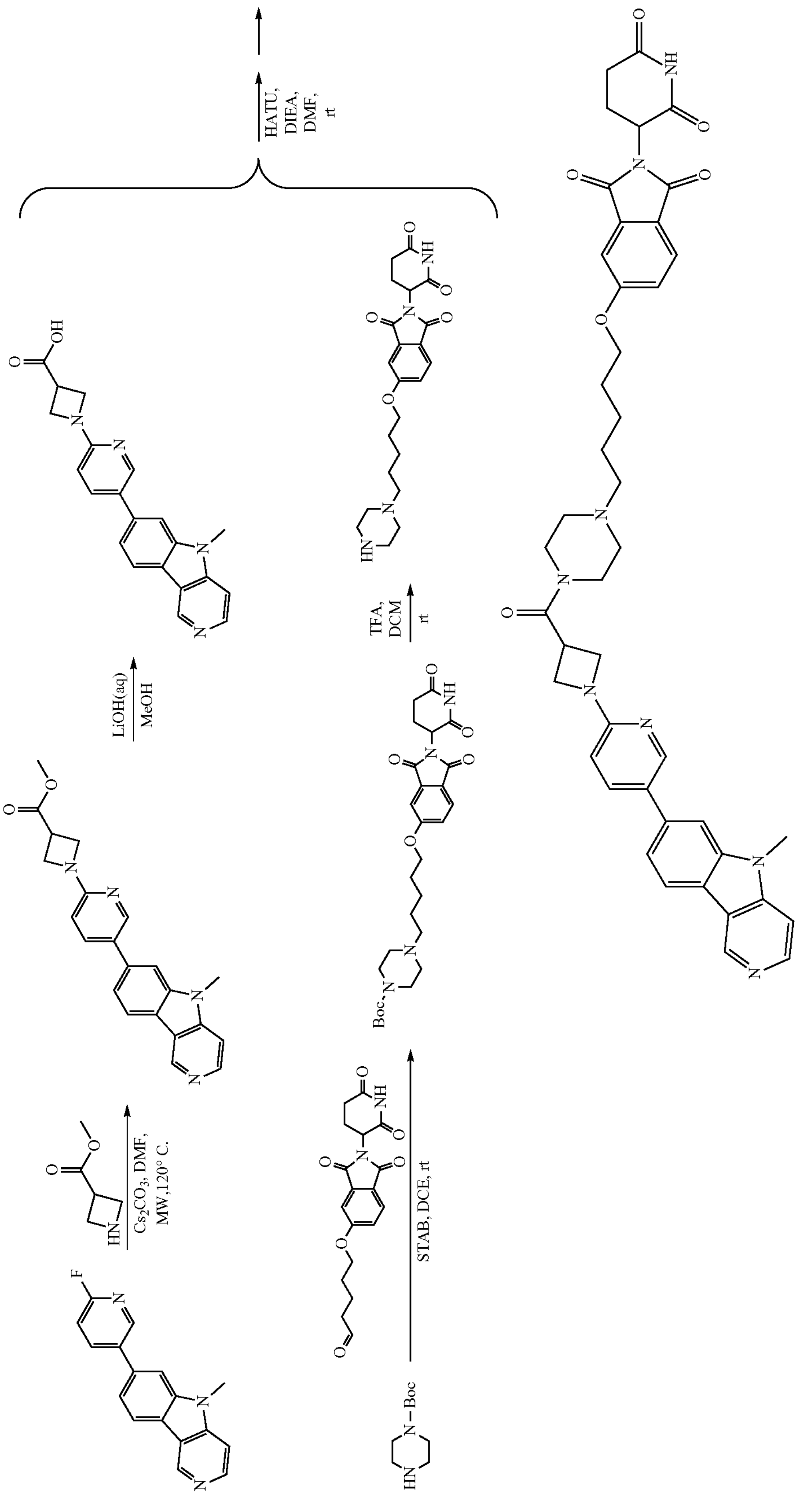
Exemplary compound 446

Exemplary Synthesis of Exemplary Compound 447
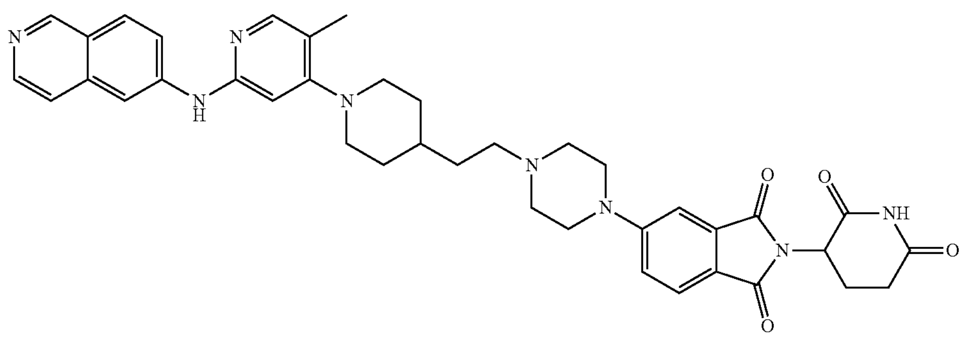 [SMILES: Cc1cnc(Nc2ccc3cnccc3c2)cc1N1CCC(CCN2CCN(c3ccc4c(c3)C(=O)N(C3CCC(=O)NC3=O)C4=O)CC2)CC1]
Prepared according to the scheme below using procedures described for other examples above as well as common procedures known to those skilled in the art.
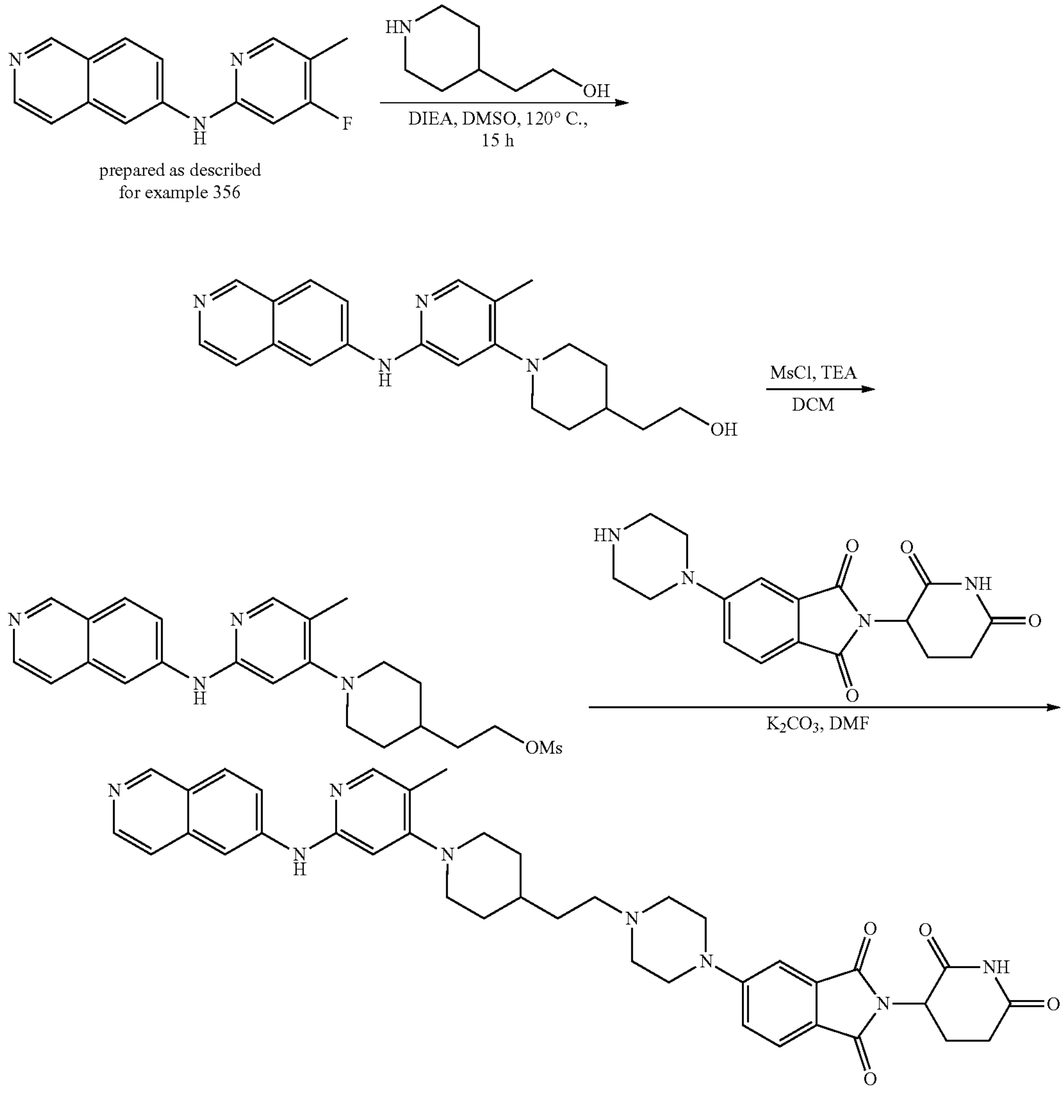
Exemplary Compound 447

Exemplary Synthesis of Exemplary Compound 448

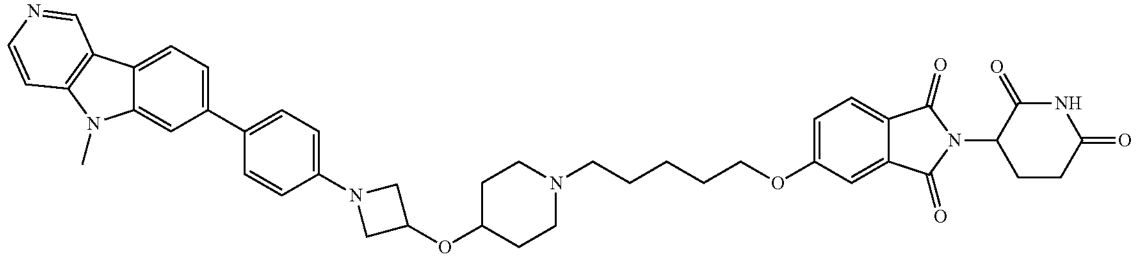 [SMILES: Cn1c2ccncc2c2ccc(-c3ccc(N4CC(OC5CCN(CCCCCOc6ccc7c(c6)C(=O)N(C6CCC(=O)NC6=O)C7=O)CC5)C4)cc3)cc21]

Step 1

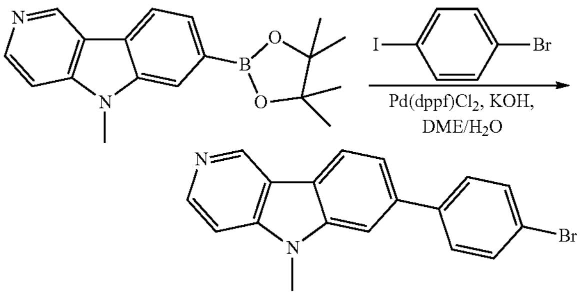

Into a 250-mL round-bottom flask purged and maintained with an inert atmosphere of nitrogen was placed 5-methyl-7-(4,4,5,5-tetramethyl-1,3,2-dioxaborolan-2-yl)pyrido[4,3-b]indole (1.80 g, 5.84 mmol, 1.0 equiv), 4-bromoiodobenzene (4.96 g, 17.52 mmol, 3.0 equiv) in DME (50 mL) and $H_2O$ (2 mL) to which was added KOH (655 mg, 11.68 mmol, 2.0 equiv), Pd(dppfCl$_2$ (427 mg, 0.58 mmol, 0.1 equiv). The resulting solution was stirred for 5 hr at 90° C. in an oil bath. The reaction mixture was cooled to room temperature. The resulting mixture was concentrated under vacuum. The crude product was purified by prep-HPLC with the following conditions: IntelFlash-1 column, silica gel; mobile phase, MeOH/DCM=0/100 increasing to MeOH/DCM=1/49 within 20 min. This resulted in 1.50 g (76%) of 7-(4-bromophenyl)-5-methylpyrido[4,3-b]indole as a dark blue oil.

Step 2

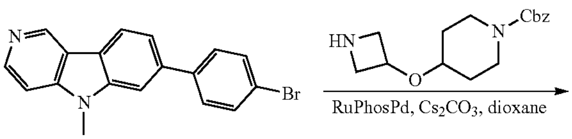

-continued

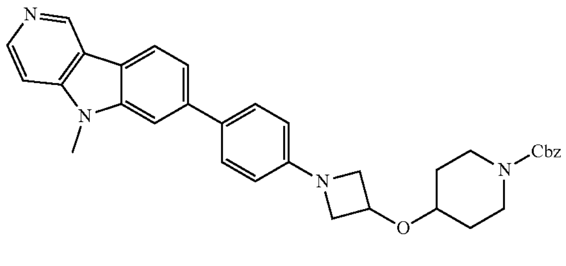

Into a 100-mL round-bottom flask purged and maintained with an inert atmosphere of nitrogen, was placed 7-(4-bromophenyl)-5-methylpyrido[4,3-b]indole (500 mg, 1.48 mmol, 1.0 equiv) and benzyl 4-(azetidin-3-yloxy)piperidine-1-carboxylate (430 mg, 1.48 mmol, 1.0 equiv), $Cs_2CO_3$ (966 mg, 2.96 mmol, 2.0 equiv) in dioxane (30 mL), to which was added RuPhos Pd G2 catalyst (115 mg, 0.15 mmol, 0.1 equiv). The resulting solution was stirred for 5 hr at 90° C. in an oil bath. The reaction mixture was cooled to room temperature. The resulting solution was diluted with 20 mL of $H_2O$. The resulting solution was extracted with (2×20 mL) of ethyl acetate. Organic phase was washed with (2×30 mL) of $H_2O$, dried over anhydrous sodium sulfate and concentrated. The residue was applied onto a silica gel column eluting with dichloromethane/methanol (100/0 to 12/1). This resulted in 600 mg (74%) of benzyl 4-[[1-(4-[5-methylpyrido[4,3-b]indol-7-yl]phenyl)azetidin-3-yl]oxy]piperidine-1-carboxylate as a dark brown oil.

Benzyl 4-[[1-(4-[5-methylpyrido[4,3-b]indol-7-yl]phenyl)azetidin-3-yl]oxy]piperidine-1-carboxylate was converted to the title compound using procedures analogous to those described for exemplary compound 455.

Exemplary Synthesis of Exemplary Compound 449

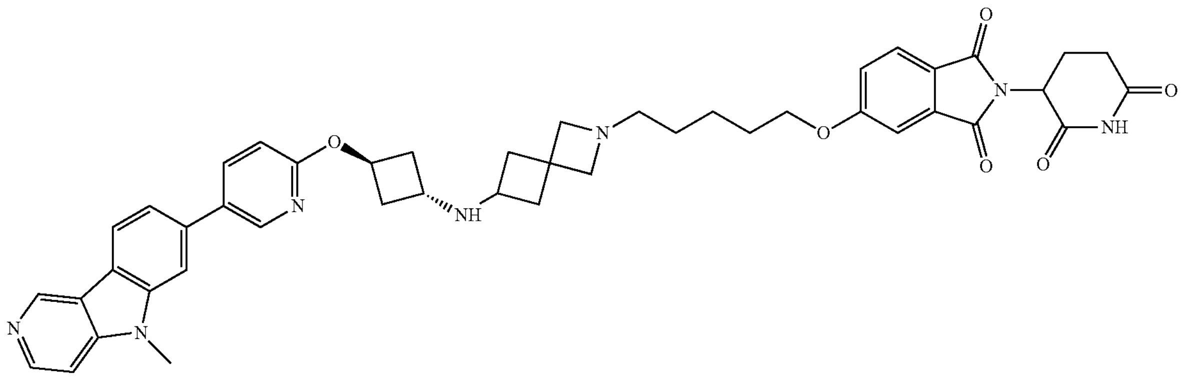 [SMILES: Cn1c2ccncc2c2ccc(-c3ccc(O[C@H]4C[C@H](NC5CC6(C5)CN(CCCCCOc5ccc7c(c5)C(=O)N(C5CCC(=O)NC5=O)C7=O)C6)C4)nc3)cc21]

Prepared according to the scheme below using procedures described for other examples above as well as procedures commonly known to those skilled in the art.
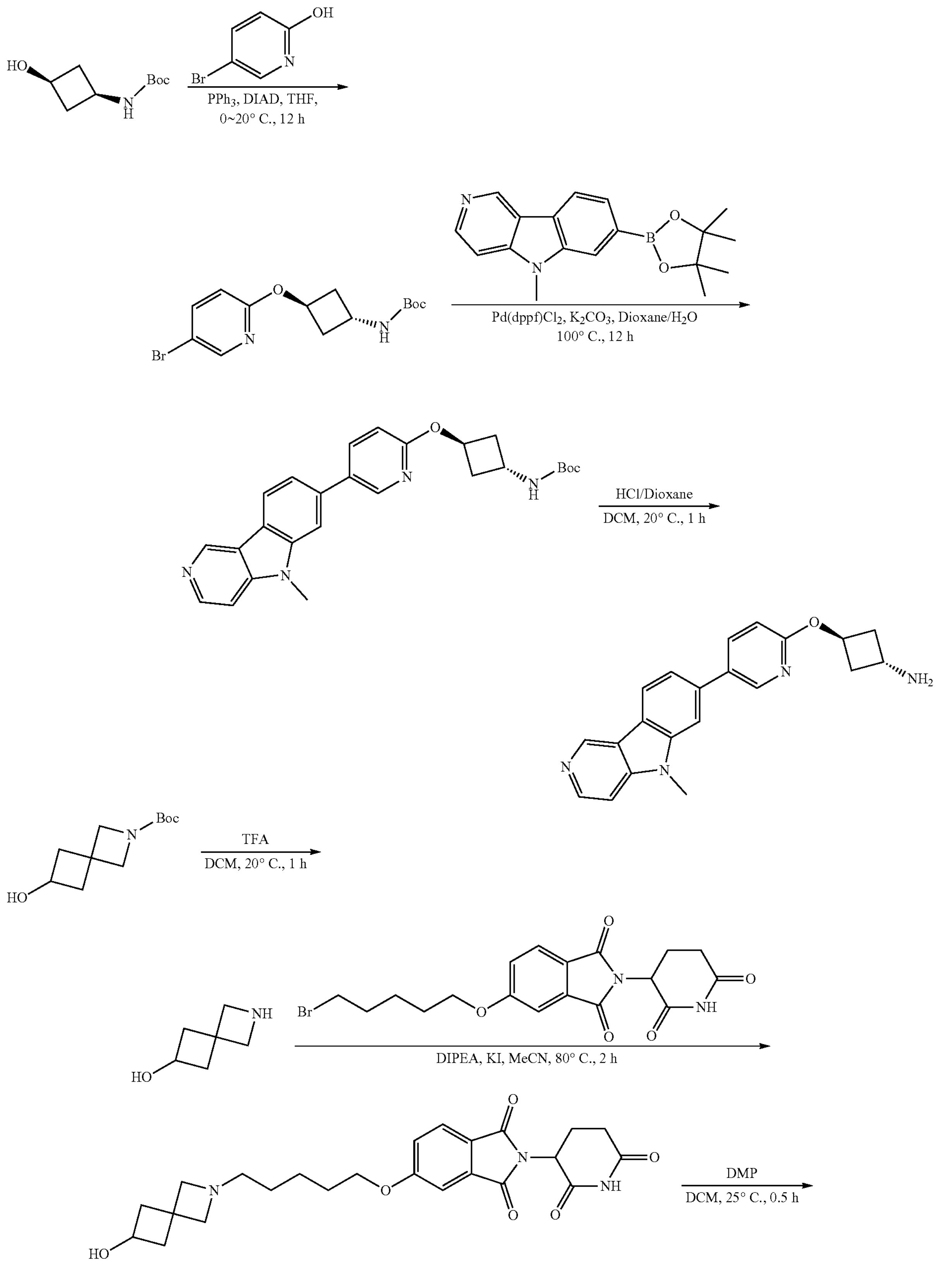

-continued
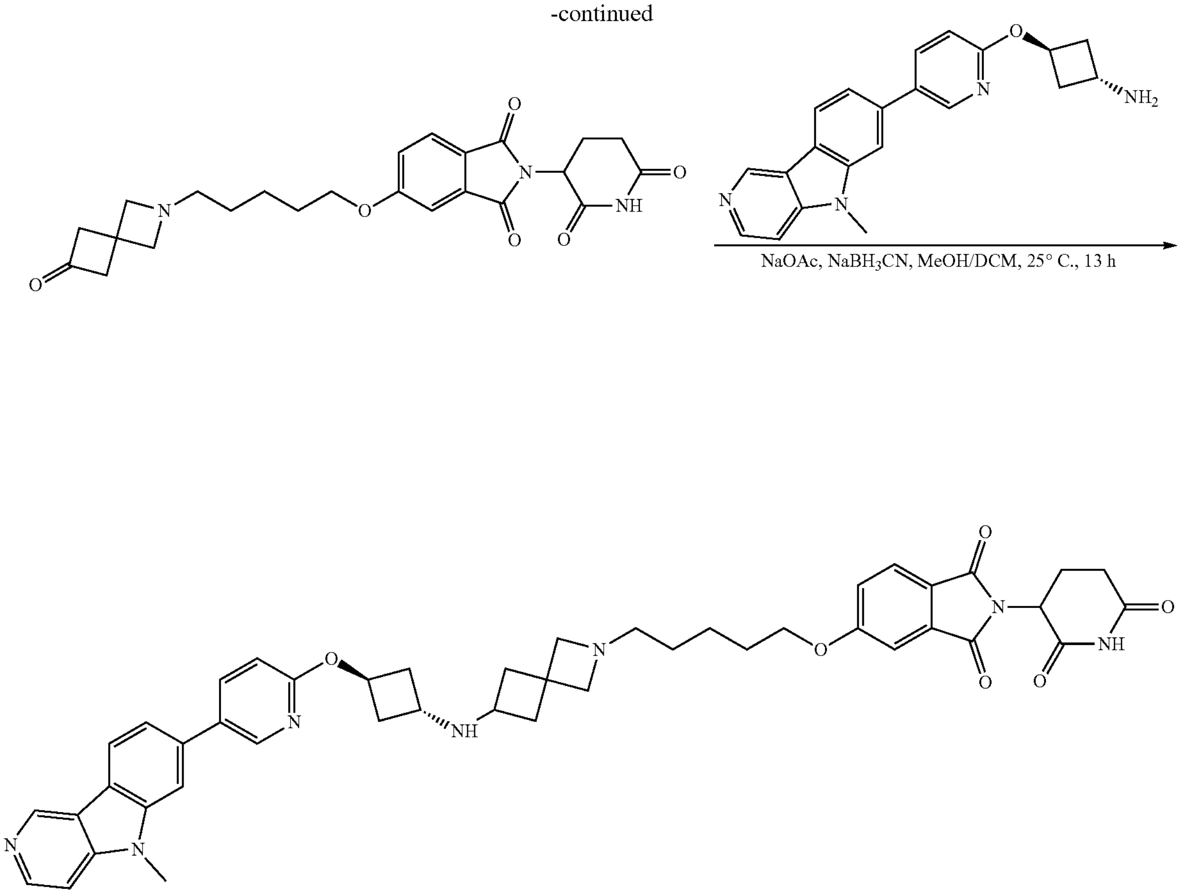
Exemplary Compound 449
Exemplary Synthesis of Exemplary Compound 450
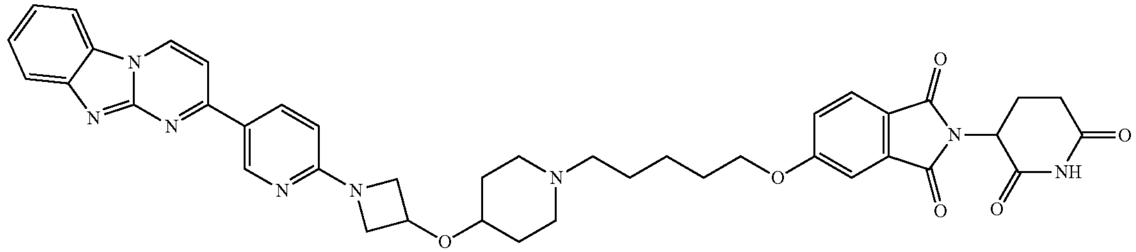 [SMILES: O=C1CCC(N2C(=O)c3ccc(OCCCCCN4CCC(OC5CN(c6ccc(-c7ccn8c(n7)nc7ccccc78)cn6)C5)CC4)cc3C2=O)C(=O)N1]
Step 1
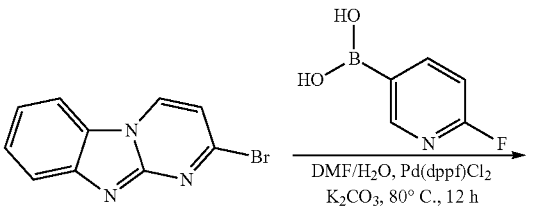
prepared as described in US 20180125821
-continued
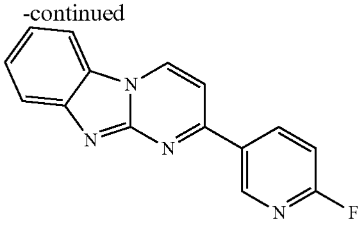
To a mixture of 2-bromopyrimido[1,2-a]benzimidazole (500 mg, 2.02 mmol, 1 eq) and (6-fluoro-3-pyridyl)boronic acid (284 mg, 2.02 mmol, 1 eq) in water (0.5 mL) and dioxane (5 mL) was added potassium carbonate (557 mg, 4.03 mmol, 2 eq) and [1,1'-bis(diphenylphosphino)ferrocene]dichloropalladium(II) (147 mg, 0.2 mmol, 0.1 eq). The mixture was stirred at 80° C. for 12 hours. The reaction mixture was diluted with water (10 mL) and extracted with dichloromethane (10 mL×3). The combined organic layers were dried over anhydrous sodium sulfate, filtered and concentrated under reduced pressure. The residue was purified by prep-TLC (dichloromethane:methanol=10:1) to give 2-(6-fluoro-3-pyridyl)pyrimido[1,2-a] benzimidazole (142 mg, 0.53 mmol, 26% yield) as a yellow solid.

Step 2

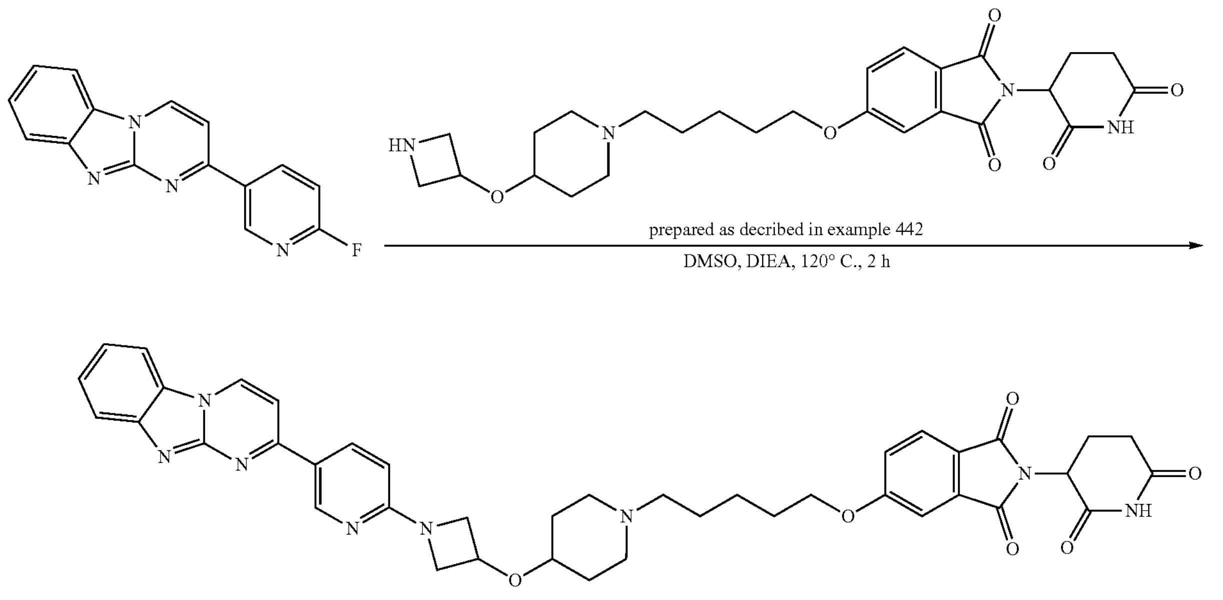

Exemplary Compound 450

To a solution of 2-(6-fluoro-3-pyridyl)pyrimido[1,2-a] benzimidazole (20 mg, 0.075 mmol, 1 eq) in dimethylsulfoxide (1 mL) was added N,N-diisopropylethylamine (48 mg, 0.37 mmol, 5 eq) and 5-[5-[4-(azetidin-3-yloxy)-1-piperidyl]pentoxy]-2-(2,6-dioxo-3-piperidyl)isoindoline-1,3-dione trifluoroacetate (46 mg, 0.075 mmol, 1 eq). The mixture was stirred at 120° C. for 2 hours. The reaction mixture was diluted with water (20 mL×3) and extracted with ethyl acetate (20 mL×3). The combined organic layers were dried over anhydrous sodium sulfate, filtered and concentrated under reduced pressure. The residue was purified by prep-TLC (dichloromethane:methanol=10:1) and further purified by prep-HPLC (column: Phenomenex Synergi C18 150*25*10 um; mobile phase: [water (0.225% formic acid)-acetonitrile]; B %: 17%-47%, 9 min) to give 2-(2,6-dioxo-3-piperidyl)-5-[5-[4-[1-(5-pyrimido[1,2-a] benzimidazol-2-yl-2-pyridyl)azetidin-3-yl]oxy-1-piperidyl] pentoxy]isoindoline-1,3-dione formate (19.7 mg, 0.024 mmol, 33% yield) as a yellow solid.

Exemplary Synthesis of Exemplary Compound 451

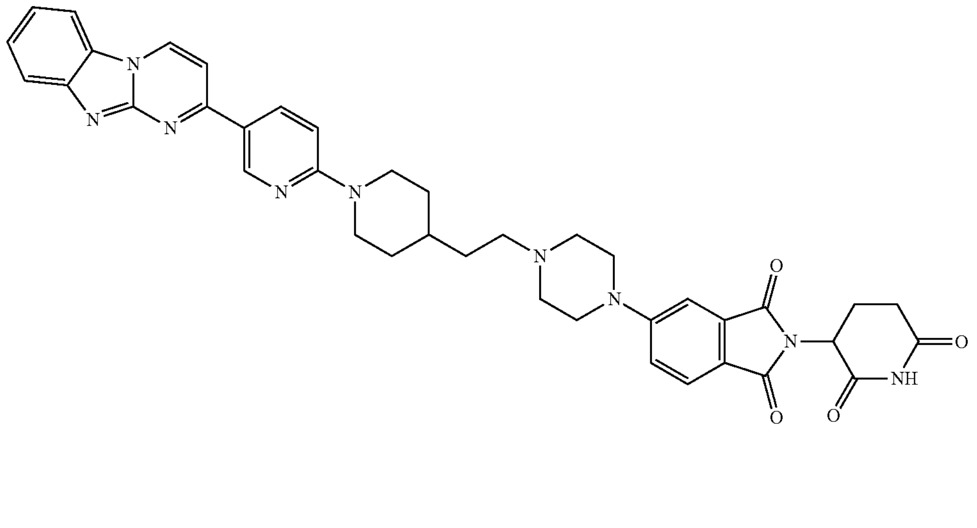 [SMILES: O=C1CCC(N2C(=O)c3ccc(N4CCN(CCC5CCN(c6ccc(-c7ccn8c(n7)nc7ccccc78)cn6)CC5)CC4)cc3C2=O)C(=O)N1]

Step 1

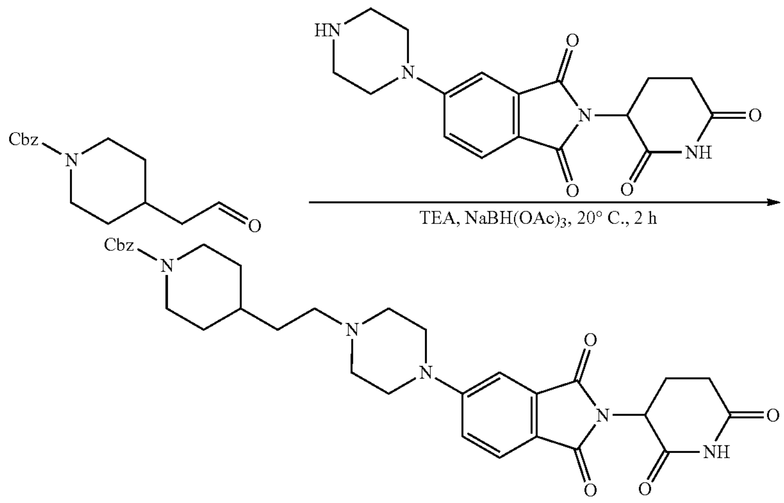

A mixture of 2-(2,6-dioxo-3-piperidyl)-5-piperazin-1-yl-isoindoline-1,3-dione (1.31 g, 3.83 mmol, 1 eq) and triethylamine (2.32 g, 23.0 mmol, 6 eq) in 1,2-dichloroethane (10 mL) and N,N-dimethylformamide (2 mL) was stirred at 25° C. for 0.5 h. Then benzyl 4-(2-oxoethyl) piperidine-1-carboxylate (1 g, 3.83 mmol, 1 eq) was added, and the mixture was stirred at 25° C. for 0.5 h. Sodium triacetoxyborohydride (1.62 g, 7.65 mmol, 2 eq) was added, and the mixture was stirred at 25° C. for 1.5 h. The reaction mixture was poured into water (10 mL) and extracted with ethyl acetate (20 mL×3). The combined organic layer was washed with brine (10 mL×2), dried over anhydrous sodium sulfate, filtered, and the filtrate was concentrated. The residue was purified by column chromatography (dichloromethane: methanol=100:1 to 20:1). The desired product benzyl 4-(2-(4-(2-(2,6-dioxopiperidin-3-yl)-1,3-dioxoisoindolin-5-yl) piperazin-1-yl)ethyl)piperidine-1-carboxylate (2 g, 3.27 mmol, 85% yield) was obtained as a colorless oil.

Step 2

To a solution of benzyl 4-(2-(4-(2-(2,6-dioxopiperidin-3-yl)-1,3-dioxoisoindolin-5-yl) piperazin-1-yl)ethyl)piperidine-1-carboxylate (2 g, 3.40 mmol, 1 eq) in methanol (40 mL) was added 10% palladium on carbon (500 mg) under nitrogen. The suspension was degassed under vacuum and purged with hydrogen several times. The mixture was stirred under hydrogen (15 psi) at 25° C. for 12 h. The mixture was filtered and concentrated under reduced pressure. The desired product 2-(2,6-dioxopiperidin-3-yl)-5-(4-(2-(piperidin-4-yl)ethyl)piperazin-1-yl)isoindoline-1,3-dione (1 g, 2.18 mmol) was obtained as a colorless oil and used directly in the next step.

2-(2,6-Dioxopiperidin-3-yl)-5-(4-(2-(piperidin-4-yl) ethyl)piperazin-1-yl)isoindoline-1,3-dione was converted to the title compound according to the scheme below using procedures described for other examples above.

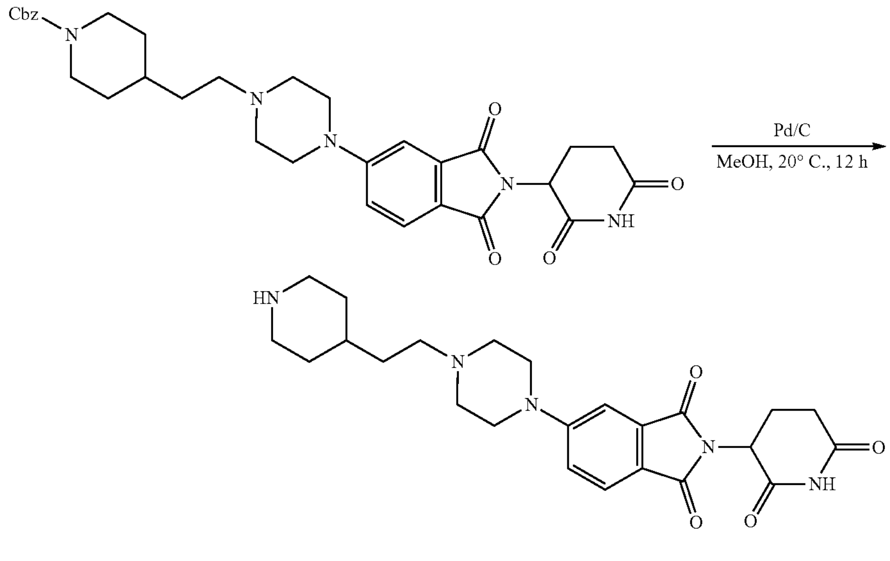

Step 1
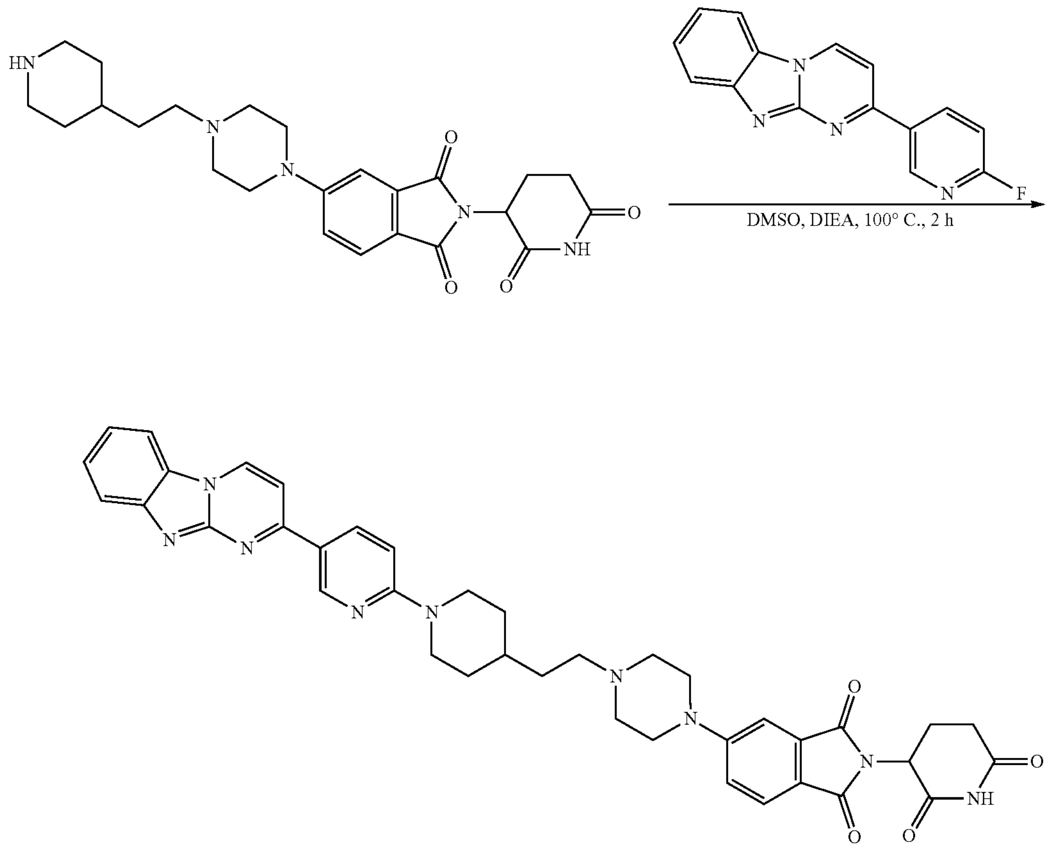
Exemplary Compound 451
Exemplary Synthesis of Exemplary Compound 452
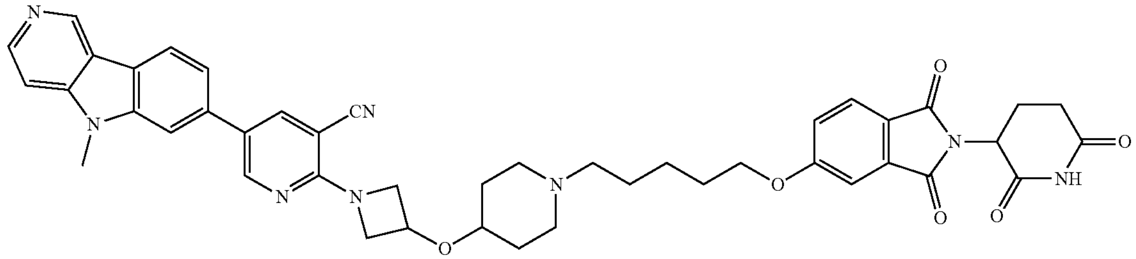 [SMILES: Cn1c2ccncc2c2ccc(-c3cnc(N4CC(OC5CCN(CCCCCOc6ccc7c(c6)C(=O)N(C6CCC(=O)NC6=O)C7=O)CC5)C4)c(C#N)c3)cc21]
Prepared according to the scheme below using procedures analogous to those described for exemplary compounds 450 and 451.
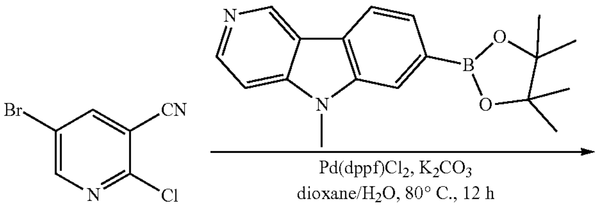

-continued

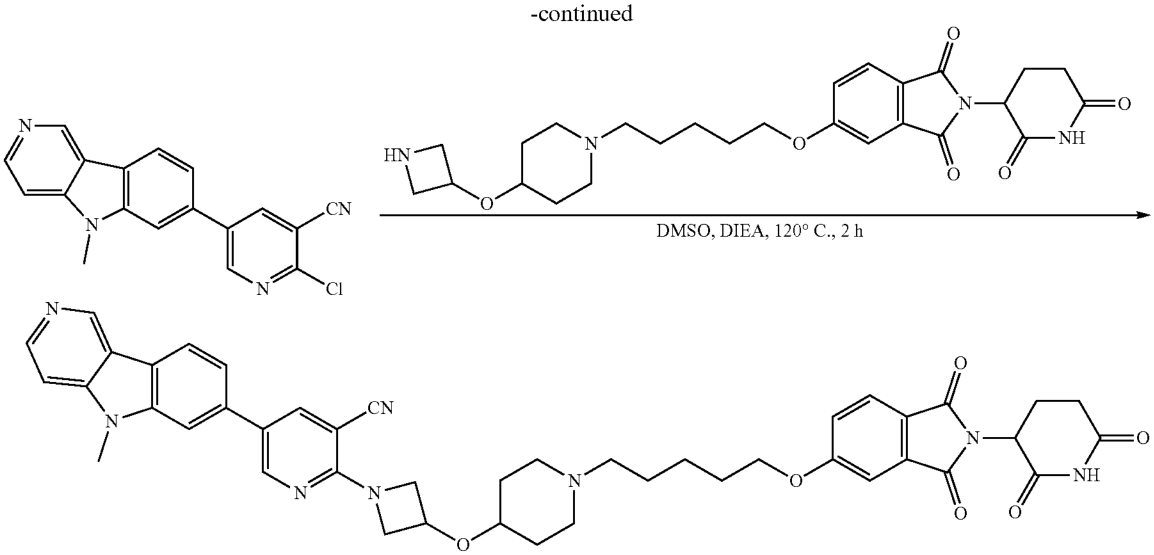

Exemplary Compound 452

Exemplary Synthesis of Exemplary Compound 453

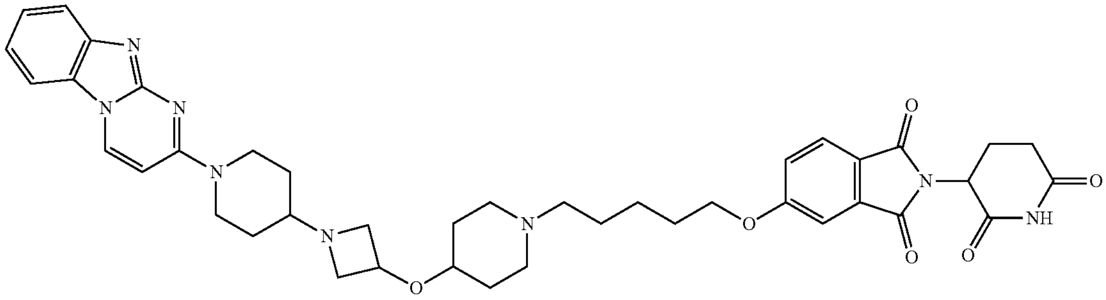 [SMILES: O=C1CCC(N2C(=O)c3ccc(OCCCCCN4CCC(OC5CN(C6CCN(c7ccn8c(n7)nc7ccccc78)CC6)C5)CC4)cc3C2=O)C(=O)N1]

Step 1

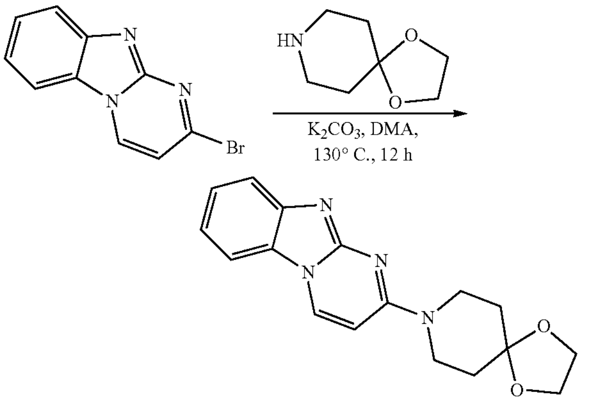

To a solution of 2-bromobenzo[4,5]imidazo[1,2-a]pyrimidine (300 mg, 1.21 mmol, 1 eq) and 1,4-dioxa-8-azaspiro[4.5]decane (259 mg, 1.81 mmol, 1.5 eq) in N,N-dimethylacetamide (3 mL) was added potassium carbonate (334 mg, 2.42 mmol, 2 eq). The mixture was stirred at 130° C. for 12 h. The reaction mixture was poured into water (10 mL) and extracted with ethyl acetate (20 mL×3). The combined organic layer was washed with brine (10 mL×2), dried over anhydrous sodium sulfate, filtered, and the filtrate was concentrated. The residue was purified by column chromatography (dichloromethane:methanol=100:1 to 50:1). The desired product 8-(benzo[4,5]imidazo[1,2-a]pyrimidin-2-yl)-1,4-dioxa-8-azaspiro[4.5]decane (200 mg, 0.64 mmol, 53% yield) was obtained as a colorless oil.

Step 2

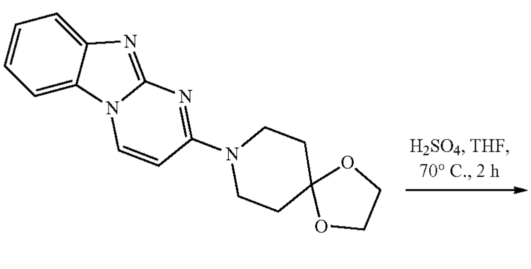

-continued

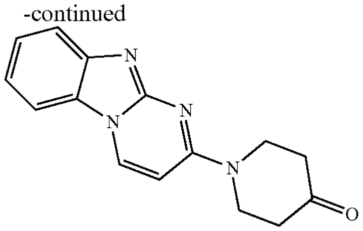

To a solution of 8-pyrimido[1,2-a]benzimidazol-2-yl-1,4-dioxa-8-azaspiro[4.5]decane (100 mg, 0.32 mmol, 1 eq) in tetrahydrofuran (5 mL) was added sulfuric acid (2 M, 3.22 mL, 20 eq). The mixture was stirred at 70° C. for 2 h. The reaction mixture was adjusted to pH 7 with sodium hydroxide solution (2M, 5 mL). The reaction mixture was poured into water (10 mL) and extracted with ethyl acetate (20 mL×3). The combined organic layer was washed with brine (10 mL×2), dried over anhydrous sodium sulfate, filtered, and the filtrate was concentrated. Crude 1-(benzo[4,5]imidazo[1,2-a]pyrimidin-2-yl)piperidin-4-one (60 mg, 0.22 mmol, 69% yield) was obtained as a yellow oil and used directly in the next step.

Step 3

To a mixture of 5-[5-[4-(azetidin-3-yloxy)-1-piperidyl]pentoxy]-2-(2,6-dioxo-3-piperidyl)isoindoline-1,3-dione (60 mg, 0.09 mmol, 1.2 eq, trifluoroacetates) in dichloroethane (10 mL) and dimethylformamide (2 mL) was added triethylamine (49 mg, 0.48 mmol, 6 eq). The mixture was stirred at 20° C. for 15 min. Then 1-(benzo[4,5]imidazo[1,2-a]pyrimidin-2-yl) piperidin-4-one (21 mg, 0.08 mmol, 1 eq) was added, and the mixture was stirred at 20° C. for 15 min. Then sodium triacetoxyborohydride (34 mg, 0.16 mmol, 2 eq) was added, and the mixture was stirred at 20° C. for 1 h. The mixture was quenched by addition water (100 mL), extracted with dichloromethane (30 mL×5). The combined organic phase washed with brine (30 mL), dried over anhydrous sodium sulfate, filtered and concentrated under reduced pressure. The residue was purified by prep-HPLC (column: Plienomenex luna C18 150*25 10 u; mobile phase: [water (0.1% TFA)-ACN]; B %: 5%-35%, 10 min). Compound 5-((5-(4-((1-(1-(benzo[4,5]imidazo[1,2-a]pyrimidin-2-yl)piperidin-4-yl)azetidin-3-yl)oxy)piperidin-1-yl)pentyl)oxy)-2-(2,6-dioxopiperidin-3-yl)isoindoline-1,3-dione trifluoroacetate (21.5 mg, 0.02 mmol, 30% yield) was obtained as a white solid.

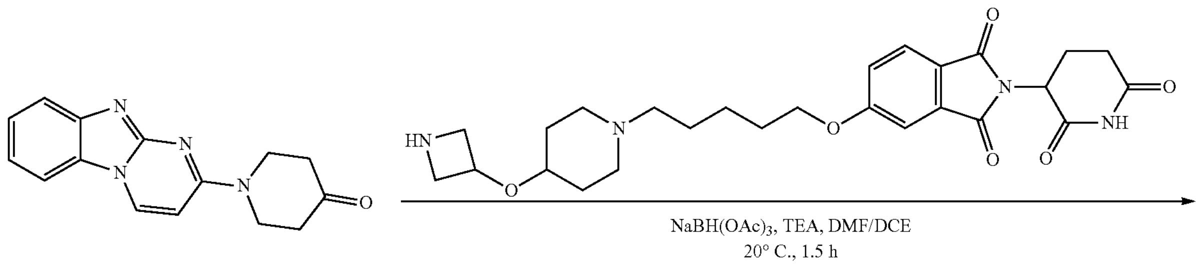

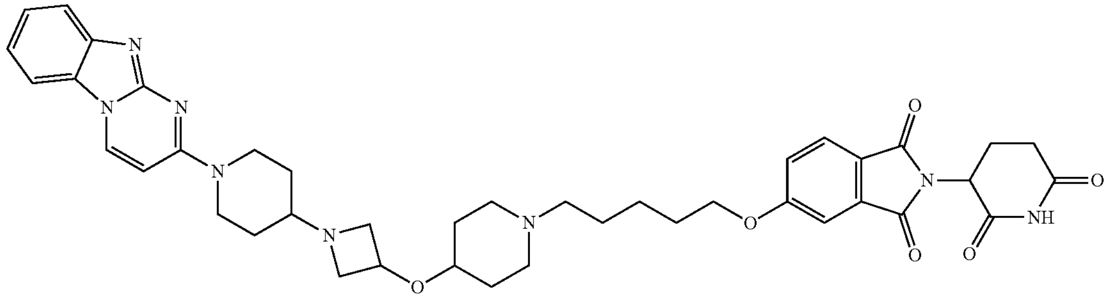

Exemplary Compound 453

Exemplary Synthesis of Exemplary Compound 454
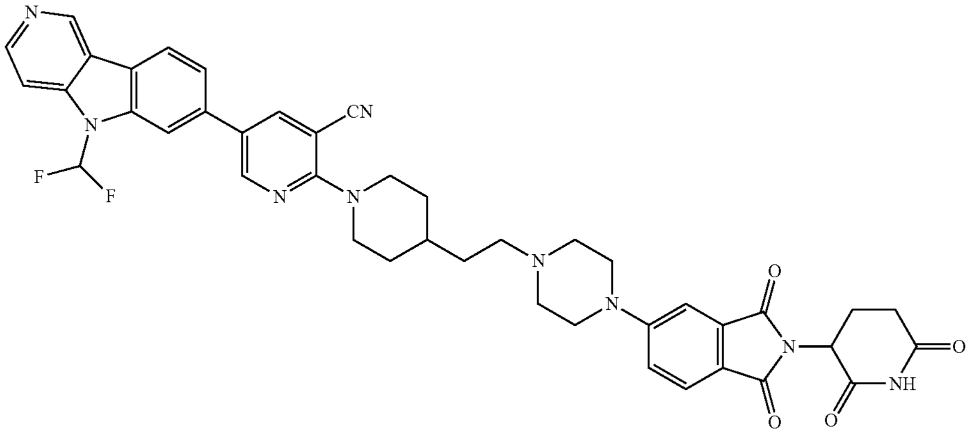 [SMILES: N#Cc1cc(-c2ccc3c4cnccc4n(C(F)F)c3c2)cnc1N1CCC(CCN2CCN(c3ccc4c(c3)C(=O)N(C3CCC(=O)NC3=O)C4=O)CC2)CC1]
Prepared according to the scheme below using procedures analogous to those described for exemplary compounds 400, 450, and 452.
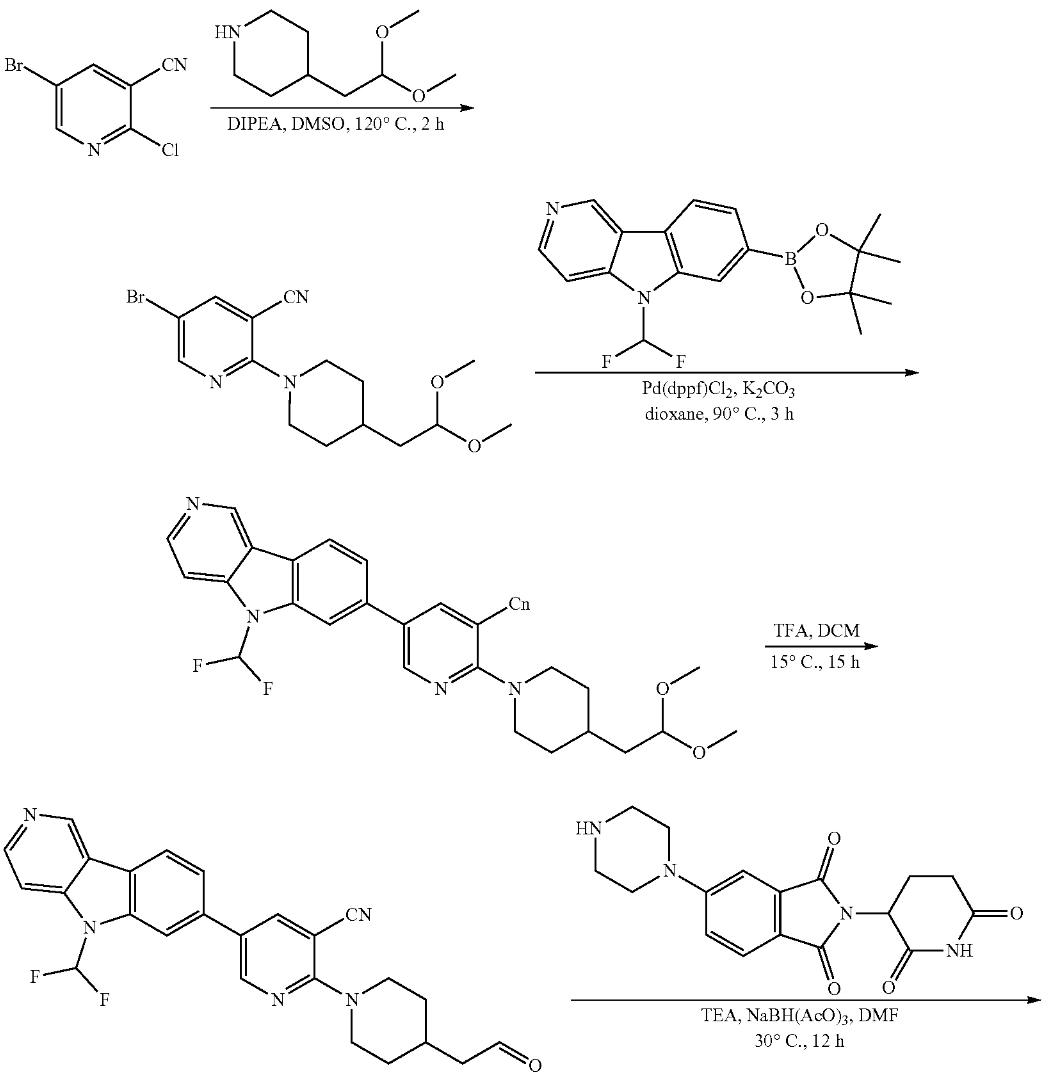

-continued

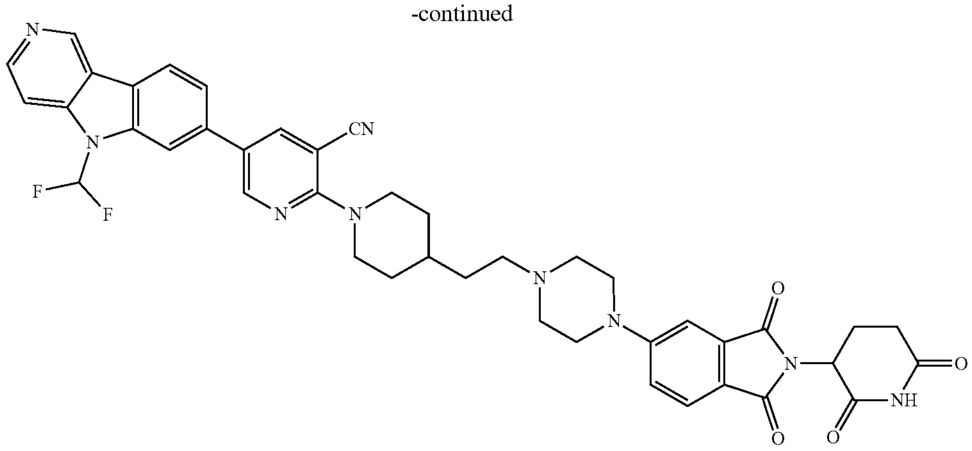

Exemplary Compound 454

Exemplary Synthesis of Exemplary Compound 455

Step 1

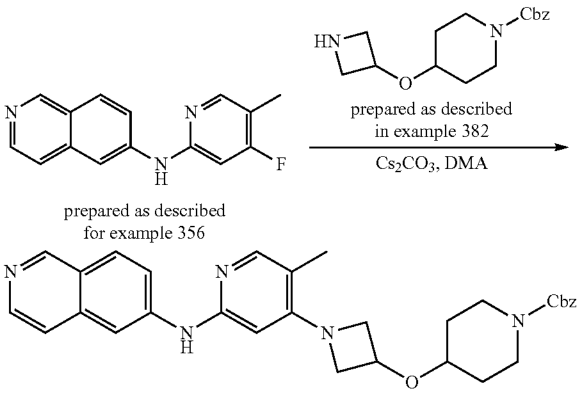

Into a 5-mL vial, was placed N-(4-fluoro-5-methylpyridin-2-yl)isoquinolin-6-amine (100 mg, 0.39 mmol, 1.0 equiv) in DMA (10.00 mL), to which was added benzyl 4-(azetidin-3-yloxy)piperidine-1-carboxylate (230 mg, 0.79 mmol, 2.03 equiv), $Cs_2CO_3$ (325 mg, 1.0 mmol, 2.54 equiv). The resulting solution was stirred for 3 hr at 140° C. The reaction mixture was cooled to room temperature. The resulting solution was diluted with 10 mL of EA. The resulting mixture was washed with (3×10 ml) of $H_2O$. The mixture was dried over anhydrous sodium sulfate and concentrated. The residue was applied onto a silica gel column eluting with dichloromethane/methanol (100:0 to 10:1). This resulted in 50 mg (24%) of benzyl 4-([1-[2-(isoquinolin-6-ylamino)-5-methylpyridin-4-yl]azetidin-3-yl]oxy)piperidine-1-carboxylate as a yellow solid.

Benzyl 4-([1-[2-(isoquinolin-6-ylamino)-5-methylpyridin-4-yl]azetidin-3-yl]oxy)piperidine-1-carboxylate was converted to the title compound according to the scheme below using procedures described for other examples above.

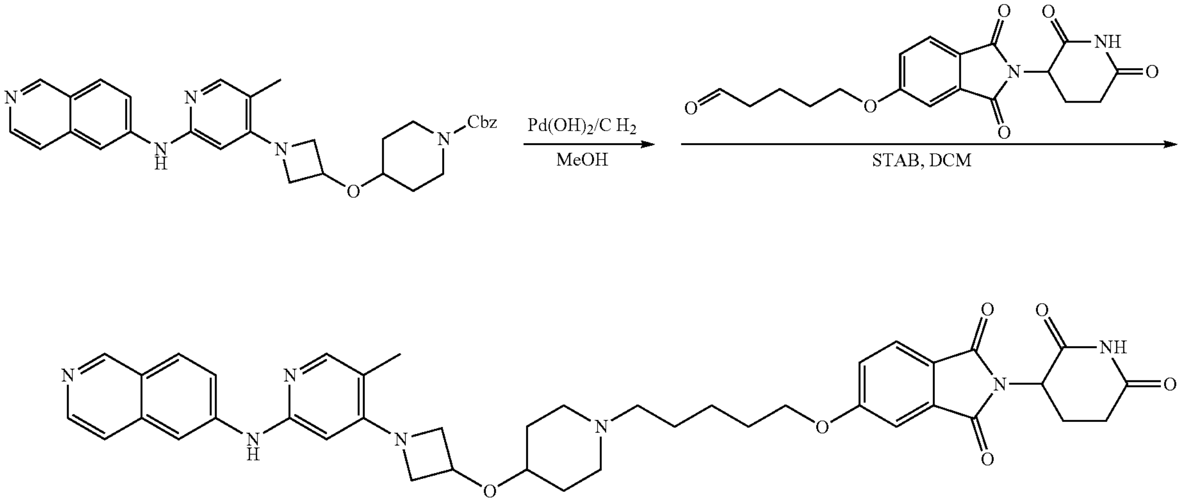

Exemplary Compound 455

Exemplary Synthesis of Exemplary Compound 456
Prepared according to the scheme below using procedures for other examples above, as well as procedures commonly known to those skilled in the art.
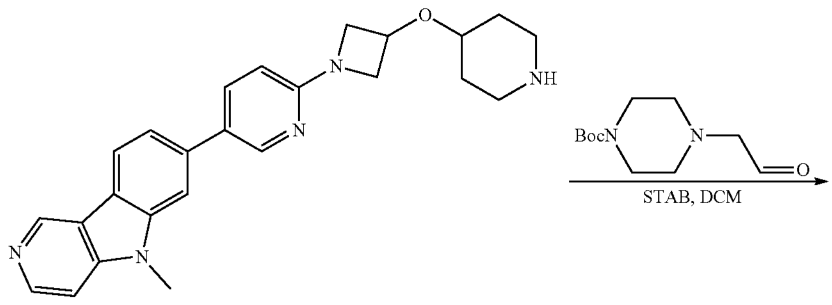
prepared as described in example 382
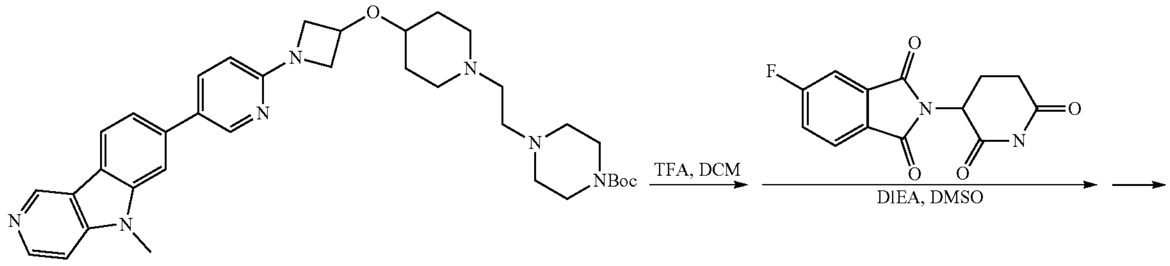
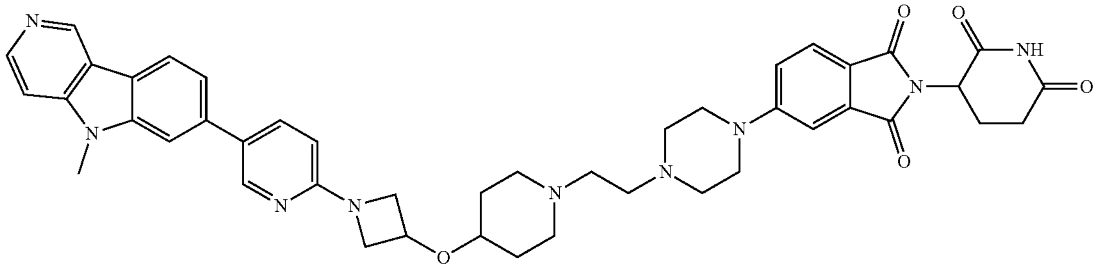
Exemplary compound 456
Exemplary Synthesis of Exemplary Compound 457
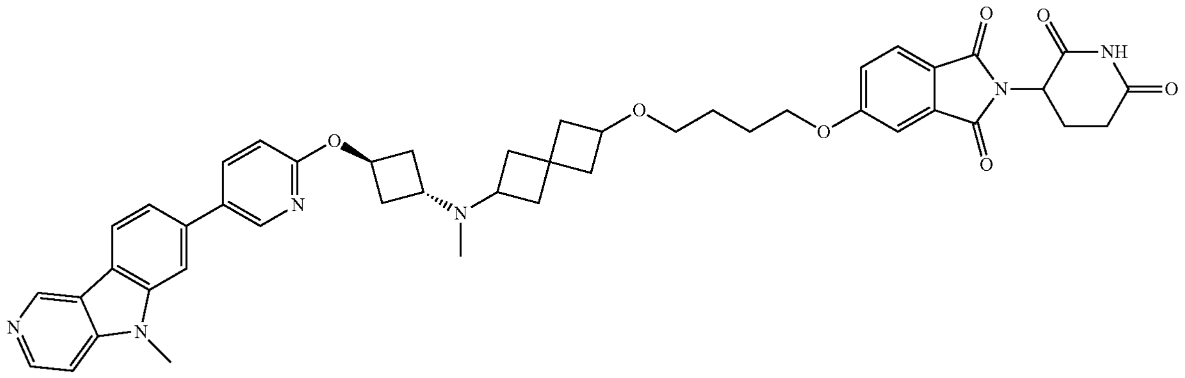 [SMILES: Cn1c2ccncc2c2ccc(-c3ccc(O[C@H]4C[C@H](N(C)C5CC6(CC(OCCCCOc7ccc8c(c7)C(=O)N(C7CCC(=O)NC7=O)C8=O)C6)C5)C4)nc3)cc21]

Prepared according to the scheme below using procedures described for other examples above as well as procedures commonly known to those skilled in the art.
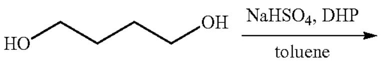
-continued
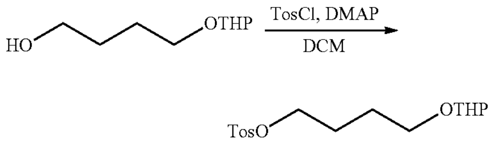
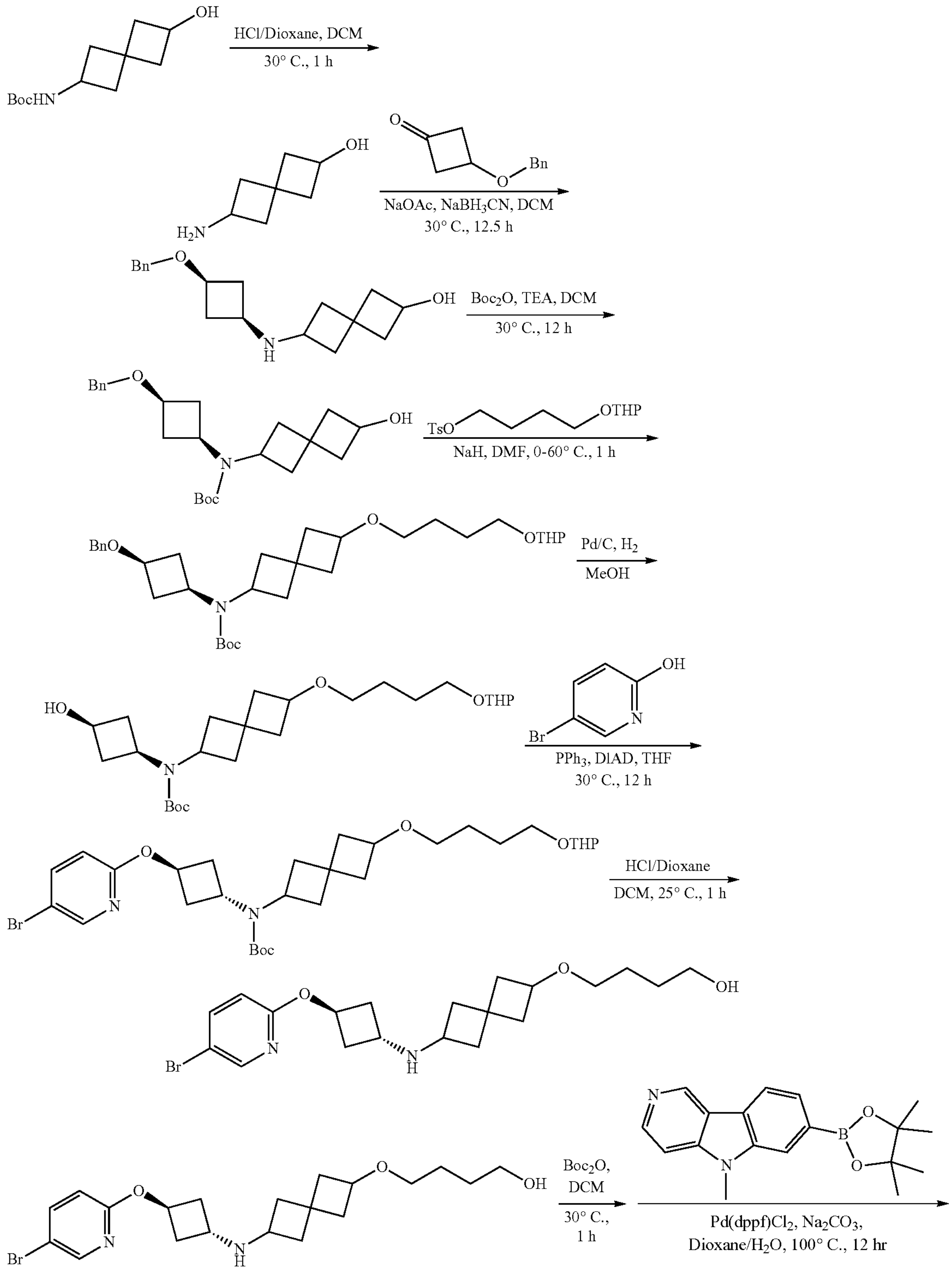

-continued
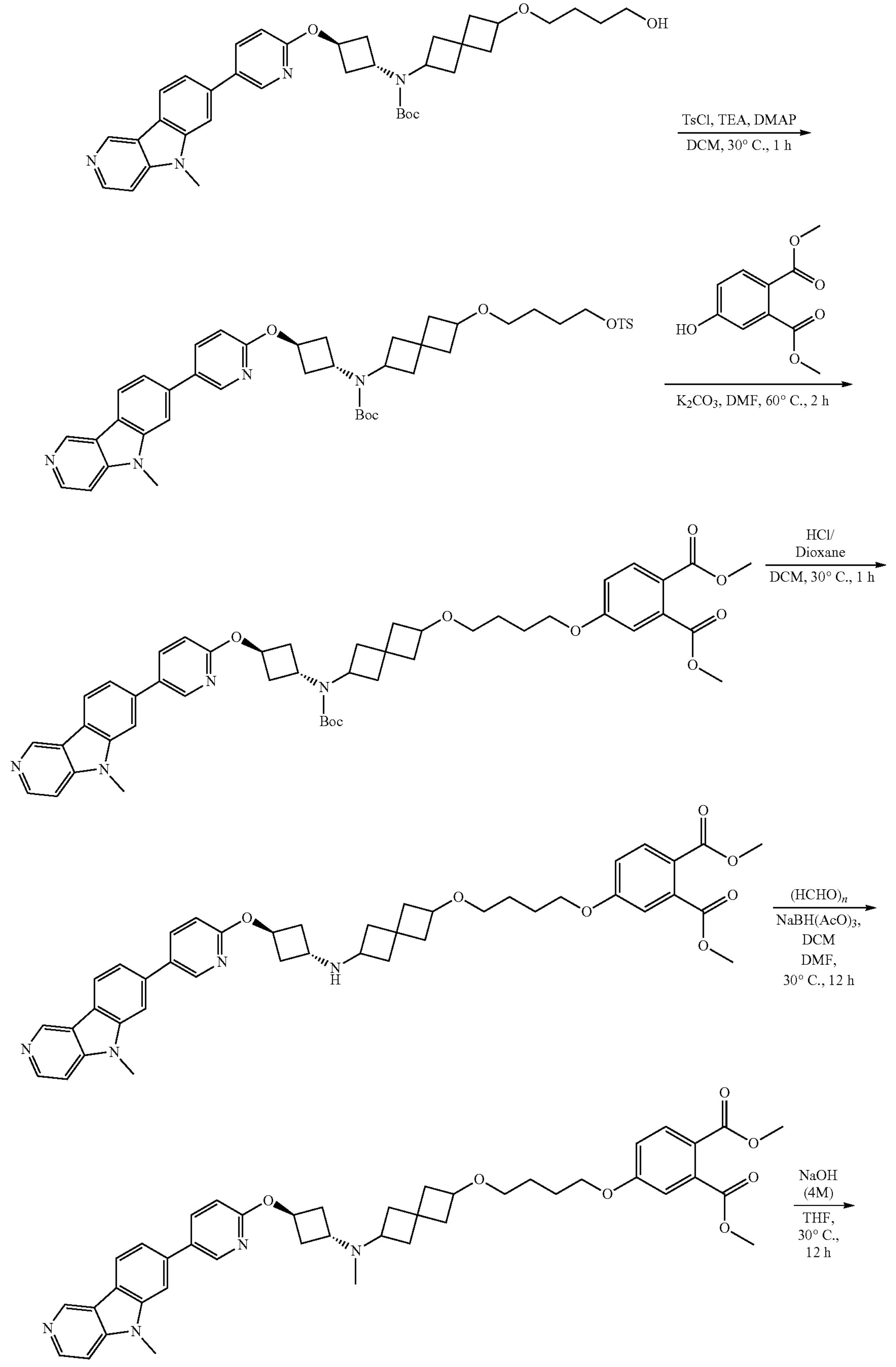

-continued
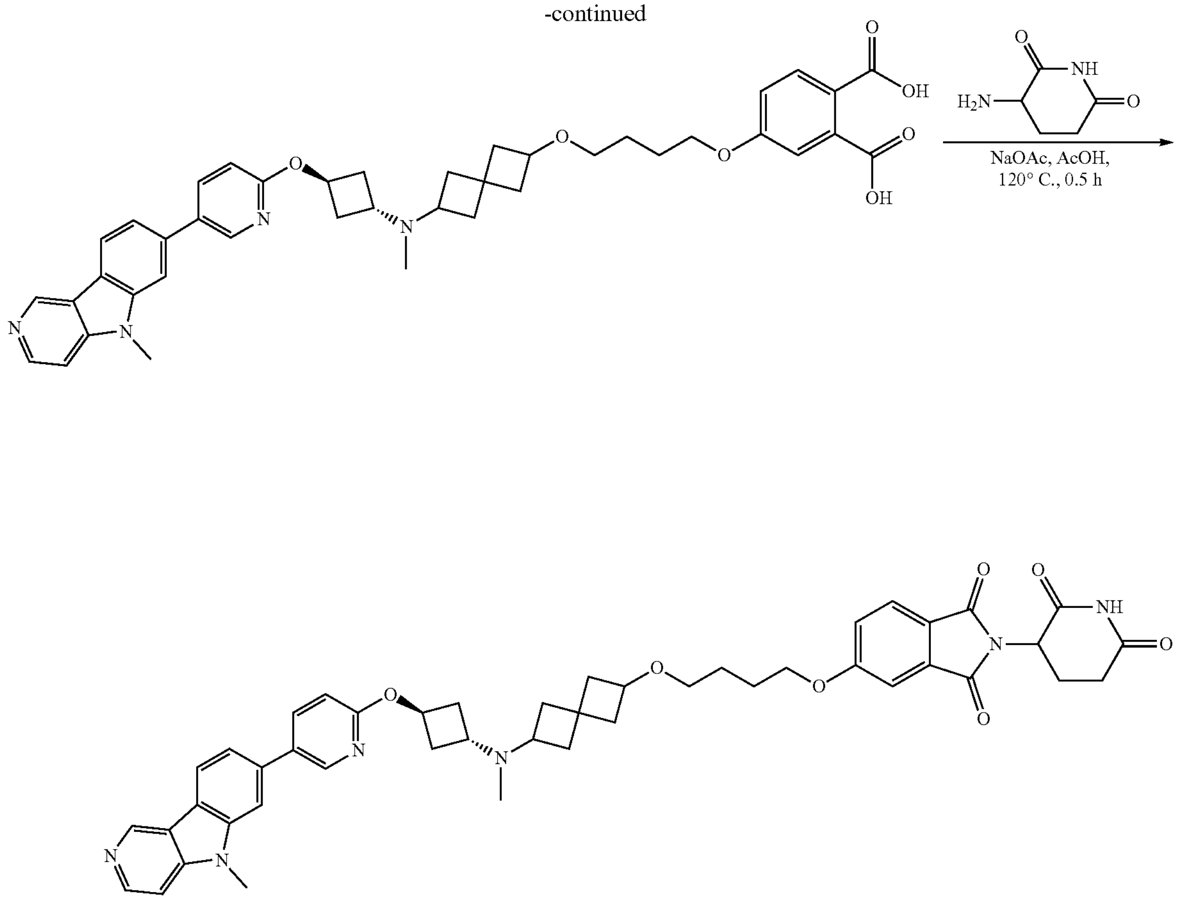
Exemplary Compound 457
Exemplary Synthesis of Exemplary Compound 458
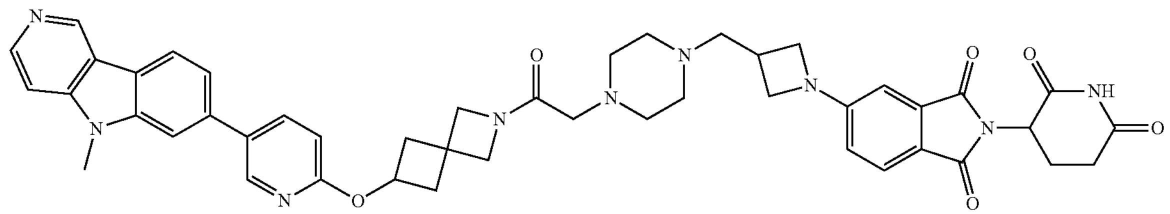 [SMILES: Cn1c2ccncc2c2ccc(-c3ccc(OC4CC5(C4)CN(C(=O)CN4CCN(CC6CN(c7ccc8c(c7)C(=O)N(C7CCC(=O)NC7=O)C8=O)C6)CC4)C5)nc3)cc21]
Prepared according to the scheme below using procedures described for other examples above as well as procedures commonly known to those skilled in the art.
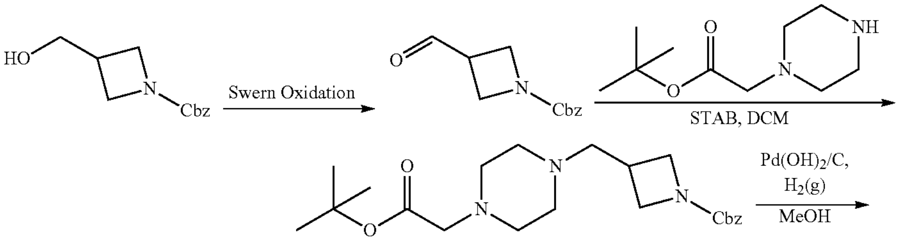

-continued
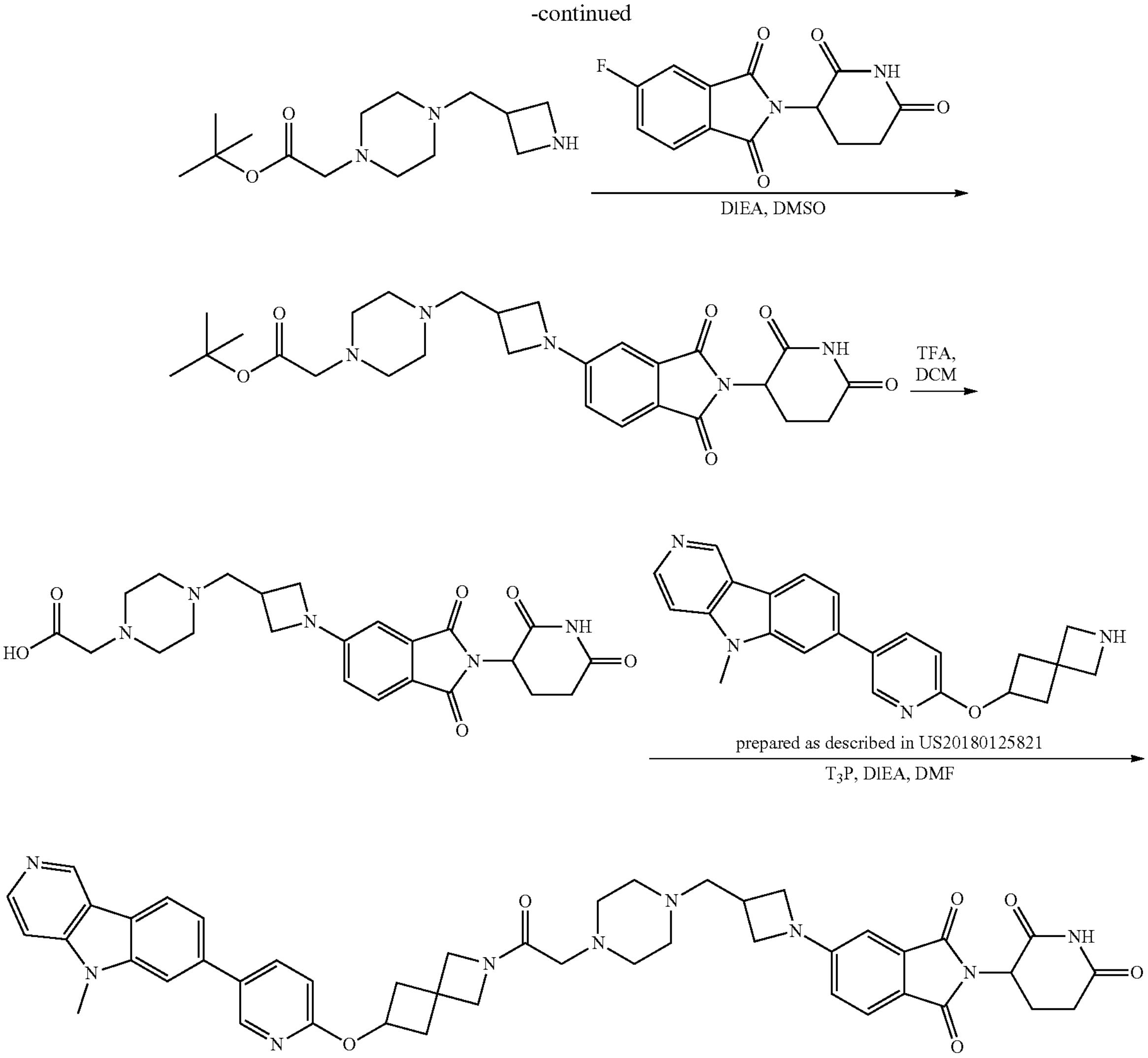
Exemplary Compound 458
Using approach described the following exemplary compounds were also prepared: 462, 472.
Exemplary Synthesis of Exemplary Compound 460
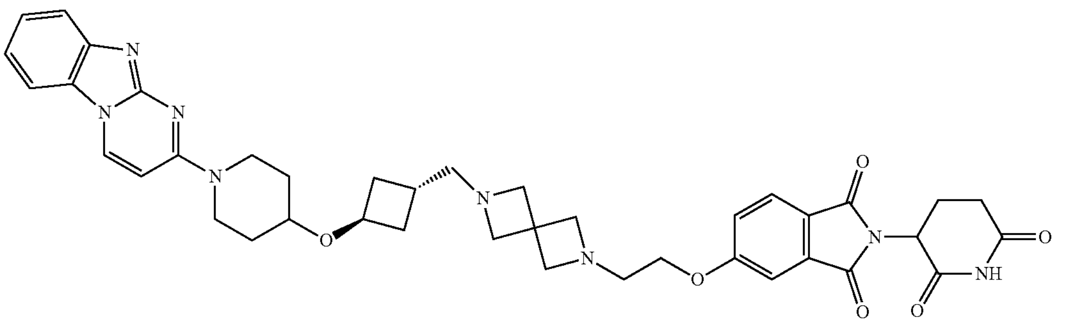 [SMILES: O=C1CCC(N2C(=O)c3ccc(OCCN4CC5(C4)CN(C[C@H]4C[C@H](OC6CCN(c7ccn8c(n7)nc7ccccc78)CC6)C4)C5)cc3C2=O)C(=O)N1]
Prepared according to the scheme below using procedures described above and those known to skilled in the art.

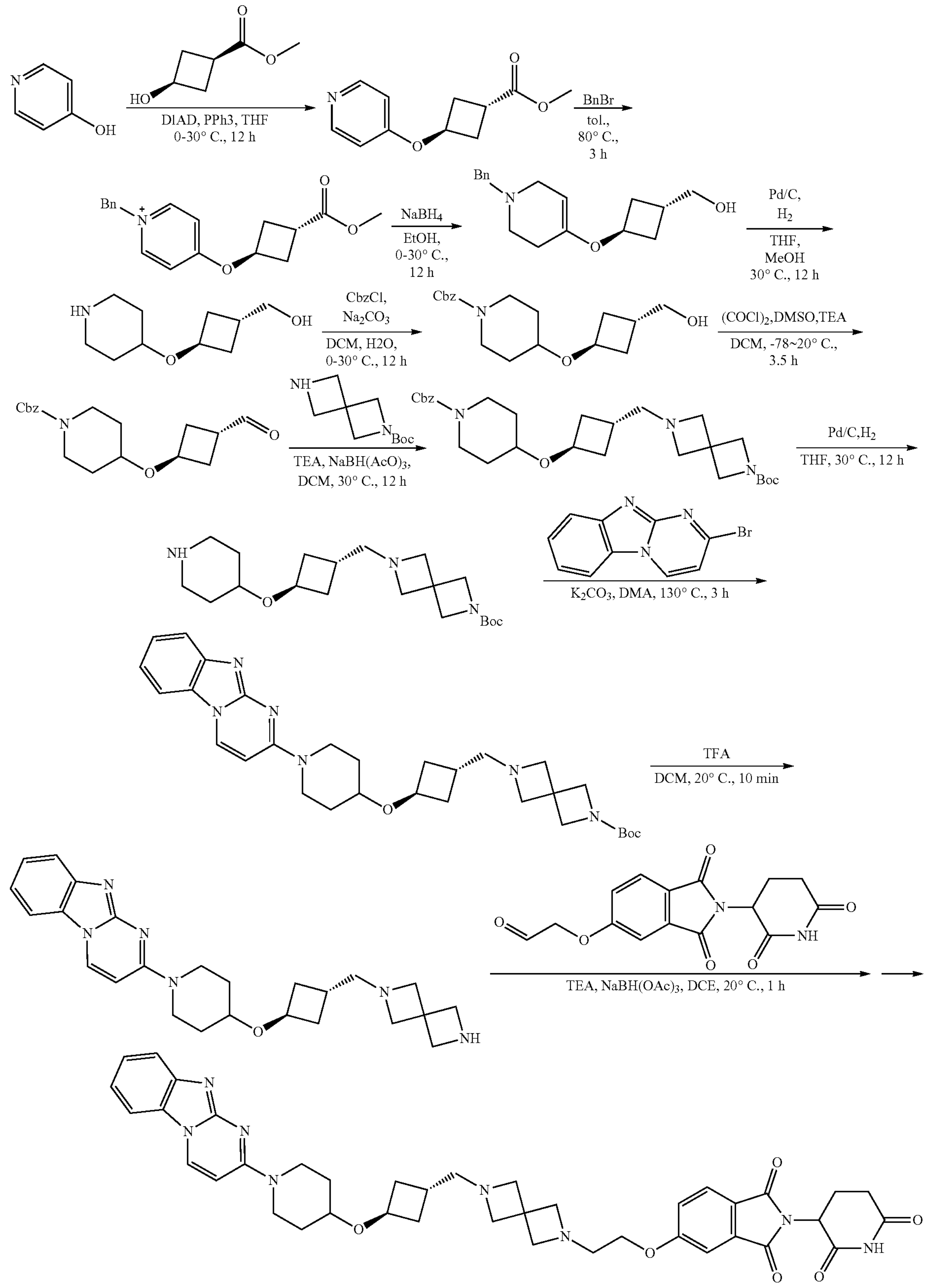
Exemplary Compound 460

Exemplary Synthesis of Exemplary Compound 474
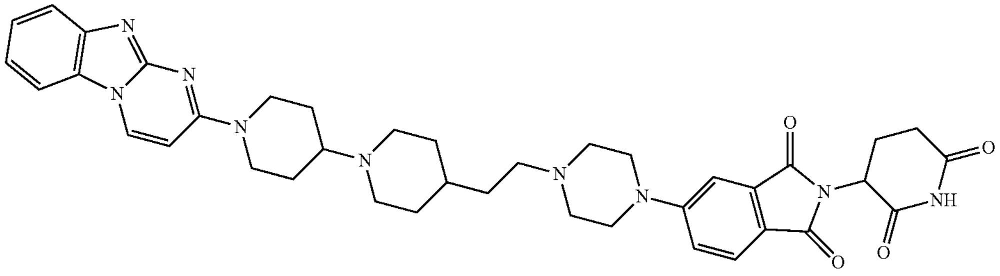 [SMILES: O=C1CCC(N2C(=O)c3ccc(N4CCN(CCC5CCN(C6CCN(c7ccn8c(n7)nc7ccccc78)CC6)CC5)CC4)cc3C2=O)C(=O)N1]
Prepared according to the scheme below using procedures described above and those known to skilled in the art.
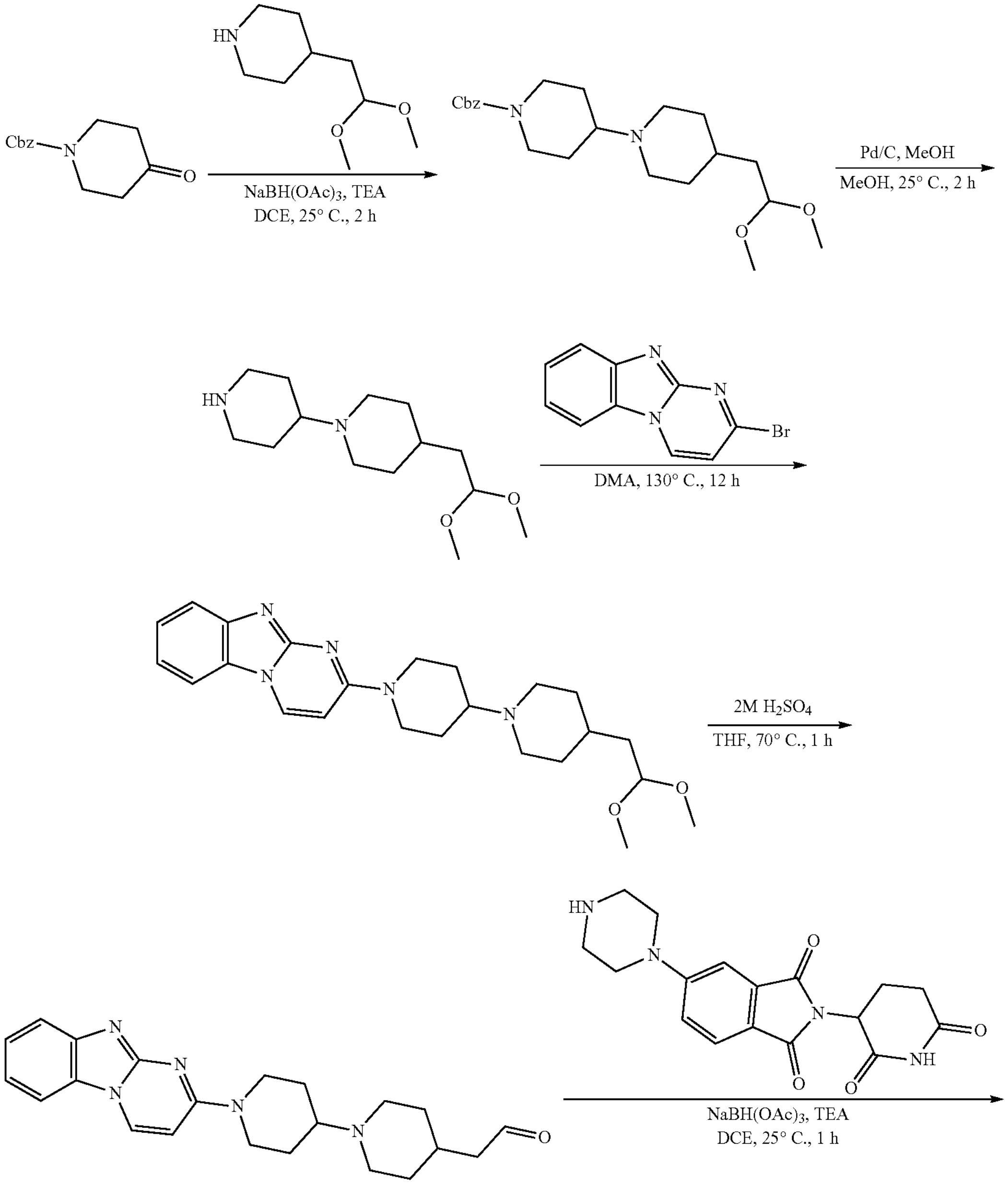

-continued
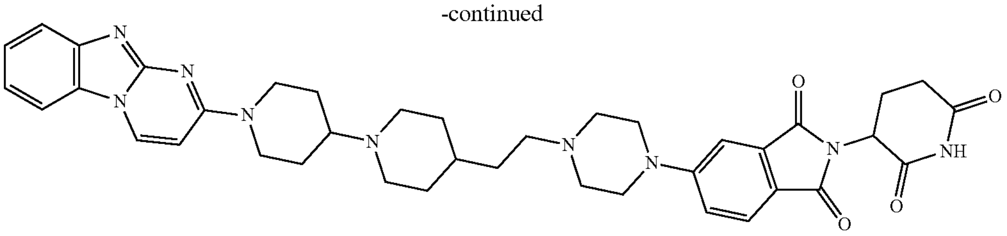
Exemplary Compound 474
Exemplary Synthesis of Exemplary Compound 475
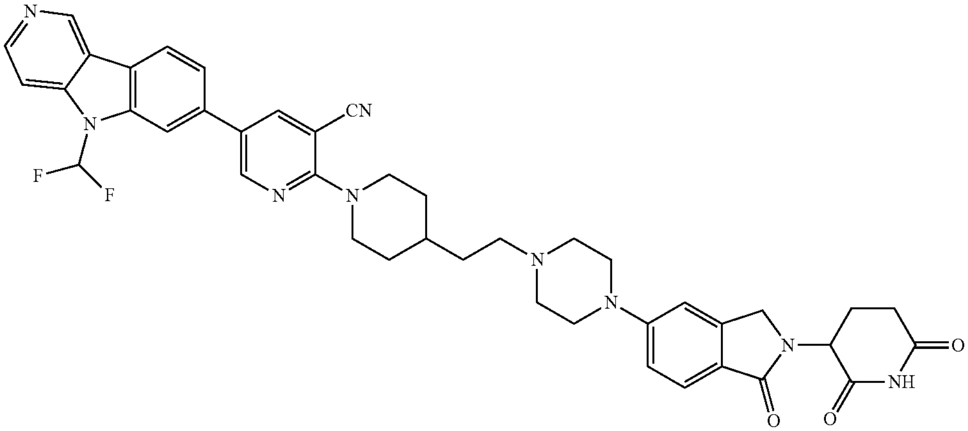 [SMILES: N#Cc1cc(-c2ccc3c4cnccc4n(C(F)F)c3c2)cnc1N1CCC(CCN2CCN(c3ccc4c(c3)CN(C3CCC(=O)NC3=O)C4=O)CC2)CC1]
Prepared according to the scheme below using procedures described for other examples above.
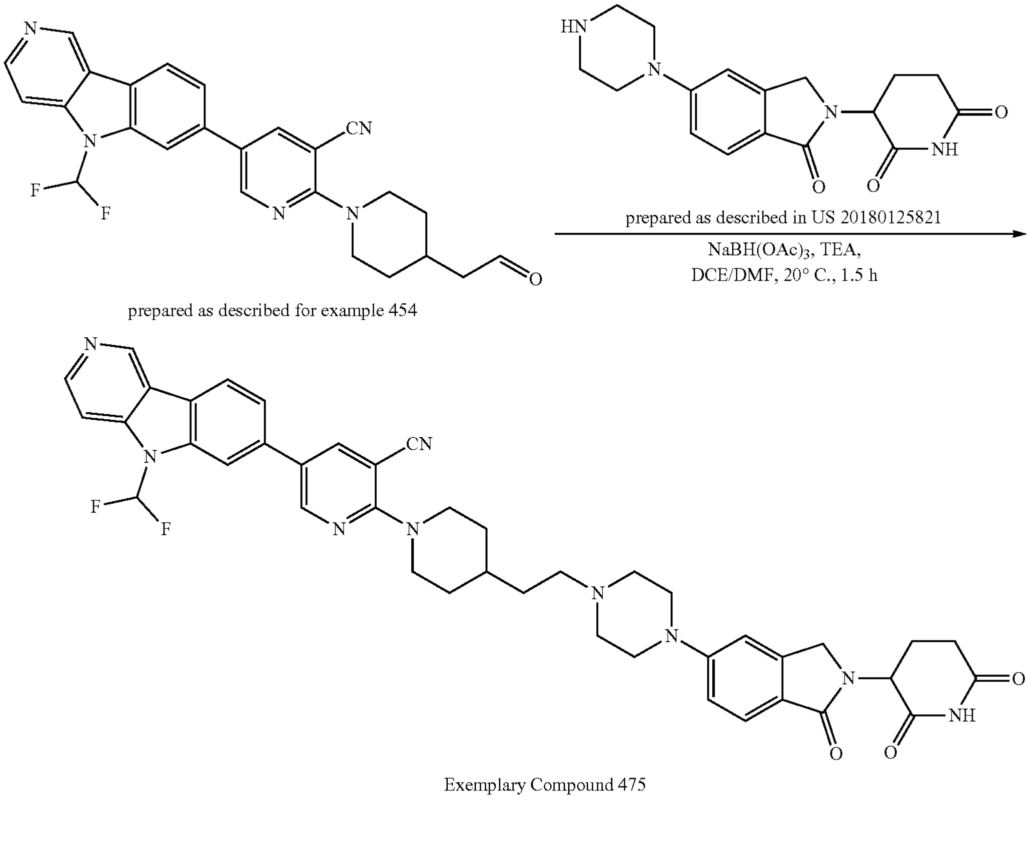
Exemplary Compound 475

Exemplary Synthesis of Exemplary Compound 480

Step 1

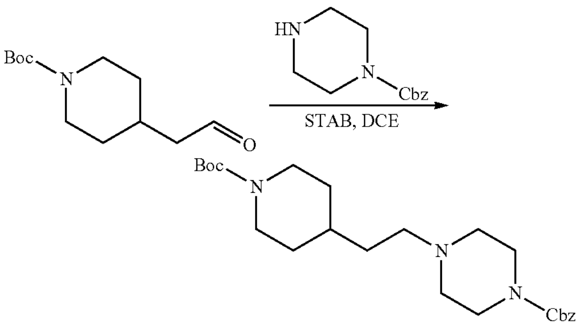

Into a 250-mL round-bottom flask purged and maintained with an inert atmosphere of nitrogen, was placed tert-butyl 4-(2-oxoethyl)piperidine-1-carboxylate (3.00 g, 13.2 mmol, 1.0 equiv), benzyl piperazine-1-carboxylate (3.05 g, 13.9 mmol, 1.1 equiv), $NaBH(OAc)_3$ (8.39 g, 39.6 mmol, 3.0 equiv), DCE (100 mL). The resulting solution was stirred for 2 hr at room temperature. The resulting mixture was concentrated. The residue was applied onto a silica gel column eluting with dichloromethane/methanol (50/1). This resulted in 5.2 g (91%) of benzyl 4-[2-[1-(tert-butoxycarbonyl)piperidin-4-yl]ethyl]piperazine-1-carboxylate as a yellow oil.

Step 2

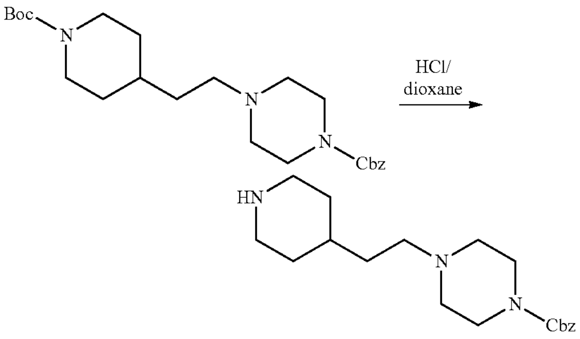

Into a 500-mL round-bottom flask purged and maintained with an inert atmosphere of nitrogen, was placed benzyl 4-[2-[1-(tert-butoxycarbonyl)piperidin-4-yl]ethyl]piperazine-1-carboxylate (5.2 g, 12.1 mmol) and HCl (4 M in 1,4-dioxane, 150 mL). The resulting solution was stirred for 2 hr at room temperature. The resulting mixture was concentrated to dryness. This resulted in 4.1 g (92%) of crude benzyl 4-[2-(piperidin-4-yl)ethyl]piperazine-1-carboxylate hydrochloride as a white solid.

Step 3

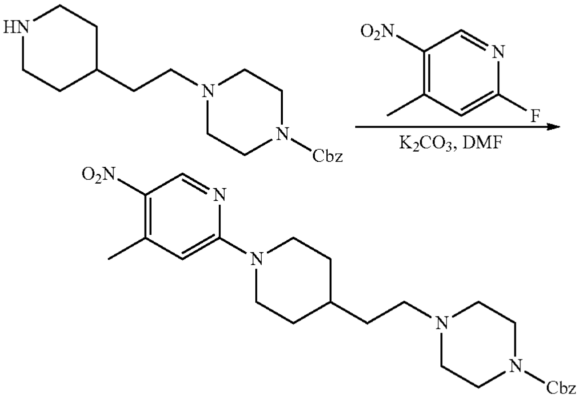

Into a 250-mL round-bottom flask purged and maintained with an inert atmosphere of nitrogen, was placed benzyl 4-[2-(piperidin-4-yl)ethyl]piperazine-1-carboxylate hydrochloride (4.00 g, 10.9 mmol, 1.0 equiv), 2-fluoro-4-methyl-5-nitropyridine (3.39 g, 21.7 mmol, 2.0 equiv), DMF (50 mL), $K_2CO_3$ (4.51 g, 32.6 mmol, 3.0 equiv). The resulting solution was stirred for 2 hr at 100° C. in an oil bath. The resulting mixture was concentrated. The residue was applied onto a silica gel column eluting with dichloromethane/methanol (20/1). This resulted in 4.1 g (81%) of benzyl 4-[2-[1-(4-methyl-5-nitropyridin-2-yl)piperidin-4-yl]ethyl]piperazine-1-carboxylate as a yellow solid.

Step 4

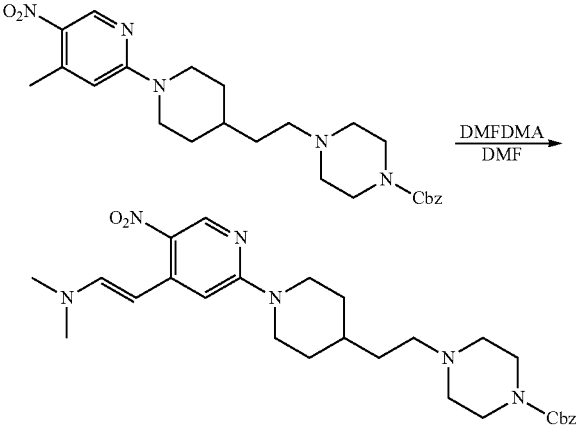

Into a 250-mL round-bottom flask purged and maintained with an inert atmosphere of nitrogen, was placed benzyl 4-[2-[1-(4-methyl-5-nitropyridin-2-yl)piperidin-4-yl]ethyl]piperazine-1-carboxylate (4.00 g, 8.55 mmol, 1.0 equiv), DMF (50.00 mL), DMF-DMA (2.04 g, 17.1 mmol, 2.0 equiv). The resulting solution was stirred for 16 hr at 120° C. in an oil bath. The resulting mixture was concentrated. This resulted in 4.5 g of benzyl 4-[2-(1-[4-[(E)-2-(dimethylamino)ethenyl]-5-nitropyridin-2-yl]piperidin-4-yl)ethyl]piperazine-1-carboxylate as a brown oil.

Step 5

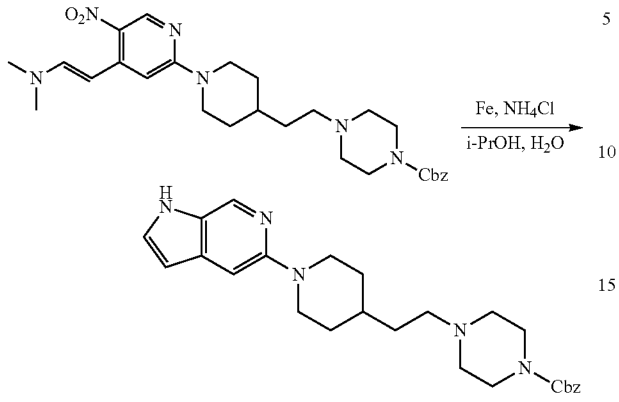

Into a 250-mL round-bottom flask purged and maintained with an inert atmosphere of nitrogen, was placed benzyl 4-[2-(1-[4-[(E)-2-(dimethylamino)ethenyl]-5-nitropyridin-2-yl]piperidin-4-yl)ethyl]piperazine-1-carboxylate (5.00 g, 9.57 mmol, 1.0 equiv), i-PrOH (50 mL), $H_2O$ (50 mL), $NH_4Cl$ (2.56 g, 47.8 mmol, 5.0 equiv), Fe (2.67 g, 47.8 mmol, 5.0 equiv). The resulting solution was stirred for 3 hr at 100° C. The solids were filtered out. The resulting mixture was concentrated. The residue was applied onto a silica gel column eluting with (DCM:MeOH=30:1). This resulted in 510 mg (12%) of benzyl 4-[2-(1-[1H-pyrrolo[2,3-c]pyridin-5-yl]piperidin-4-yl)ethyl]piperazine-1-carboxylate as a yellow solid.

Step 6

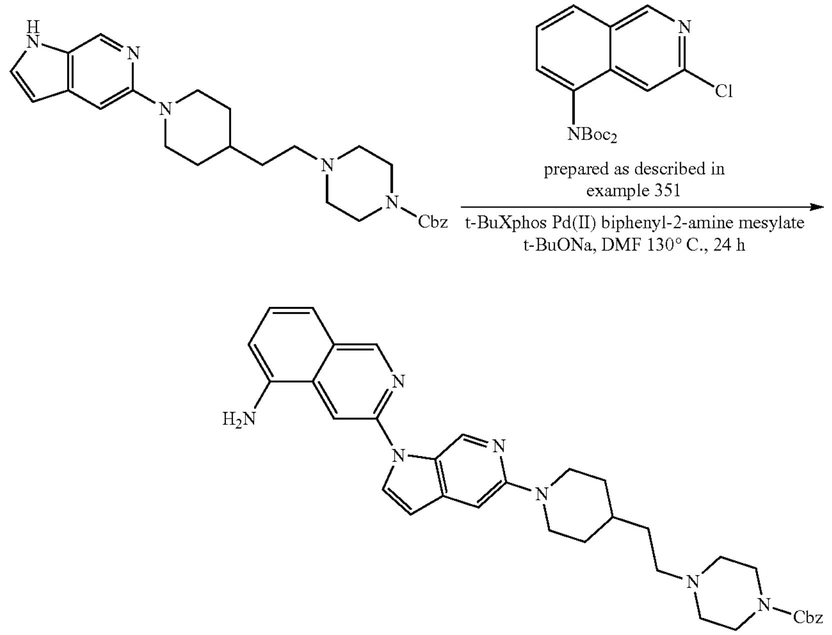

Into a 20-mL sealed tube purged and maintained with an inert atmosphere of nitrogen, was placed benzyl 4-[2-(1-[1H-pyrrolo[2,3-c]pyridin-5-yl]piperidin-4-yl)ethyl]piperazine-1-carboxylate (510 mg, 1.14 mmol, 1.0 equiv), tert-butyl N-(tert-butoxycarbonyl)-N-(3-chloroisoquinolin-5-yl) carbamate (431 mg, 1.14 mmol, 1.0 equiv), DMF (12 mL), t-BuONa (219 mg, 2.28 mmol, 2.0 equiv), t-BuXPhos palladium(II) biphenyl-2-amine mesylate (181 mg, 0.23 mmol, 0.20 equiv). The resulting solution was stirred for 16 hr at 130° C. in an oil bath. The reaction was then quenched by the addition of water (50 mL). The resulting solution was extracted with ethyl acetate (50 mL×3). The combined organic layers were washed with brine (100 mL), dried over $Na_2SO_4$ and concentrated. The residue was applied onto a silica gel column eluting with (DCM:MeOH=20:1). This resulted in 130 mg (19%) of benzyl 4-(2-[1-[1-(5-aminoisoquinolin-3-yl)pyrrolo[2,3-c]pyridin-5-yl]piperidin-4-yl]ethyl)piperazine-1-carboxylate as a yellow solid.

Step 7

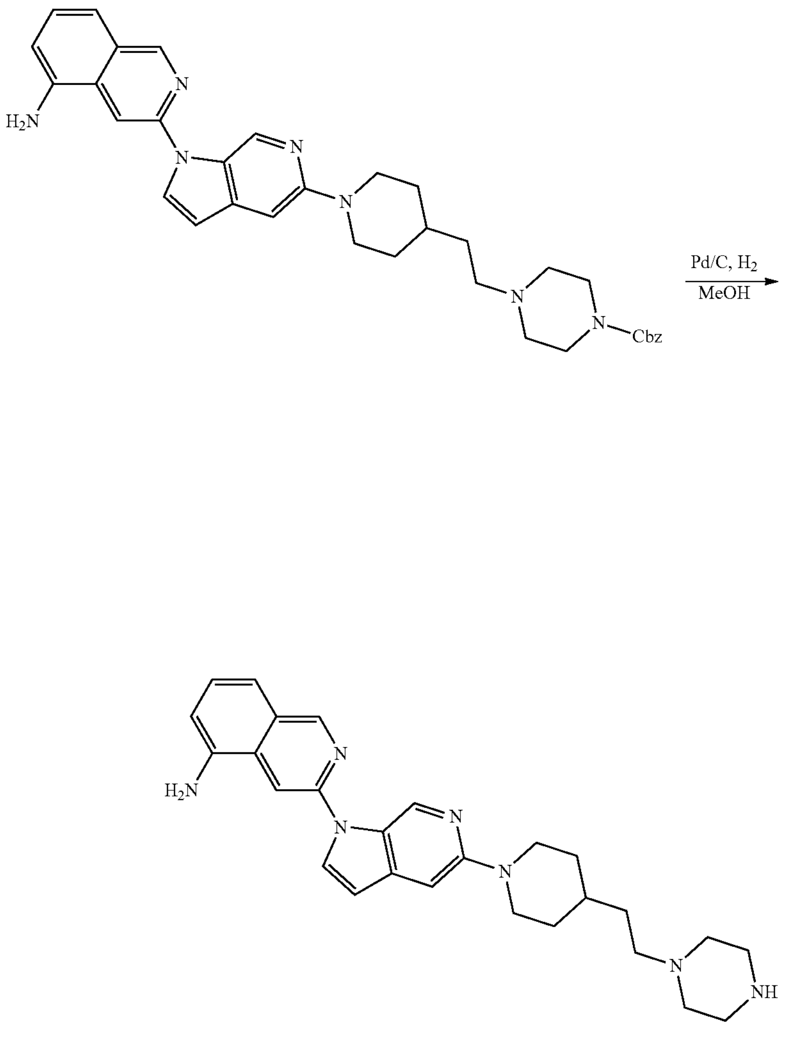

Into a 50-mL round-bottom flask purged and maintained with an inert atmosphere of $N_2$, was placed benzyl 4-(2-[1-[1-(5-aminoisoquinolin-3-yl)pyrrolo[2,3-c]pyridin-5-yl]piperidin-4-yl]ethyl)piperazine-1-carboxylate (130 mg, 0.22 mmol, 1.0 equiv), 10% Pd/C (100 mg, 0.094 mmol, 0.43 equiv), and MeOH (5 mL). The resulting solution was stirred for 1 hr at room temperature under hydrogen atmosphere. The solids were filtered out. The filtrate was concentrated. This resulted in 90 mg (90%) of 3-(5-[4-[2-(piperazin-1-yl)ethyl]piperidin-1-yl]pyrrolo[2,3-c]pyridin-1-yl)isoquinolin-5-amine as a yellow solid.

Step 8

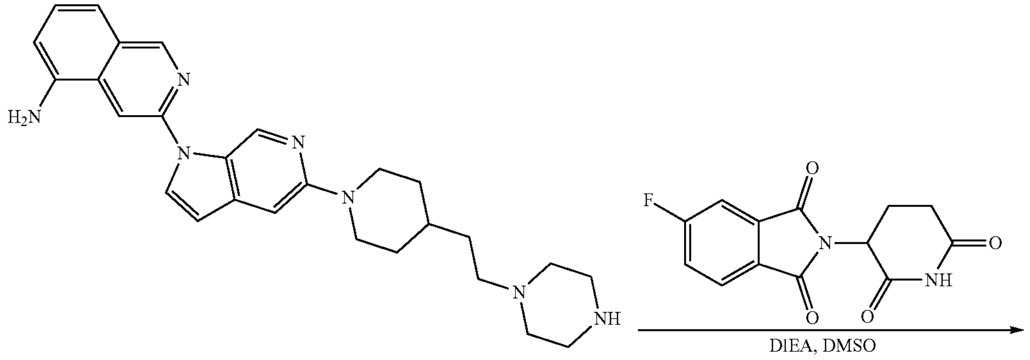

-continued

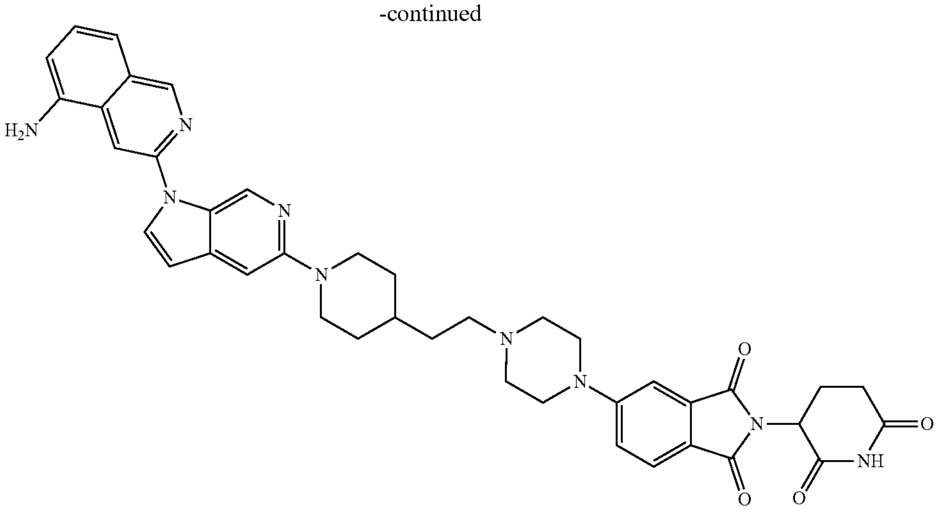

Exemplary Compound 480

Into a 50-mL round-bottom flask purged and maintained with an inert atmosphere of nitrogen, was placed 3-(5-[4-[2-(piperazin-1-yl)ethyl]piperidin-1-yl]pyrrolo[2,3-c]pyridin-1-yl)isoquinolin-5-amine (80 mg, 0.176 mmol, 1.0 equiv), 2-(2,6-dioxopiperidin-3-yl)-5-fluoroisoindole-1,3-dione (169 mg, 0.615 mmol, 3.5 equiv), DMF (5 mL), $K_2CO_3$ (121 mg, 0.878 mmol, 5.0 equiv). The resulting solution was stirred for 3 hr at 90° C. in an oil bath. The reaction was then quenched by the addition of water (30 mL). The resulting solution was extracted with EtOAc (30 mL×3). The combined organic layers were washed with brine (100 mL), dried over $Na_2SO_4$ and concentrated. The crude product was purified by Prep-HPLC with the following conditions: Column, XBridge Prep OBD C18 Column, 150 mm 5 um; mobile phase, Water (10 mmol/L $NH_4HCO_3$) and ACN (58% PhaseB up to 65% in 12 min). This resulted in 6.5 mg (5.2%) of 5-[4-(2-[1-[1-(5-aminoisoquinolin-3-yl)pyrrolo[2,3-c]pyridin-5-yl]piperidin-4-yl]ethyl)piperazin-1-yl]-2-(2,6-dioxopiperidin-3-yl)isoindole-1,3-dione as a yellow solid.

Exemplary Synthesis of Exemplary Compound 484

Prepared according to the scheme below.

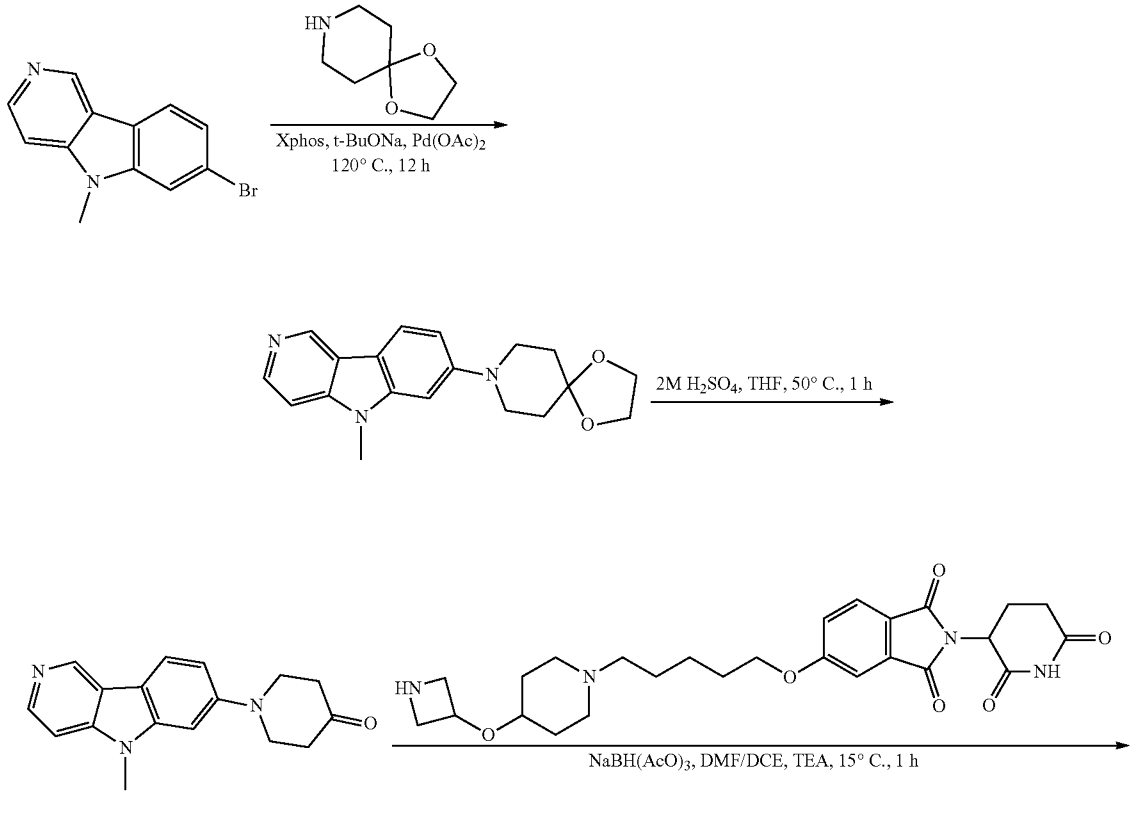

-continued

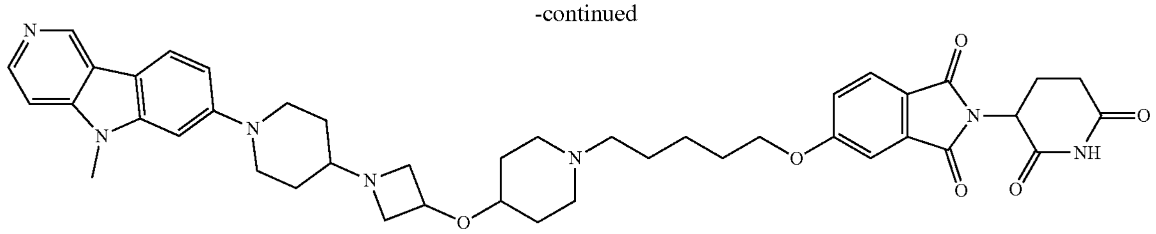

Exemplary Compound 484

Exemplary Synthesis of Exemplary Compound 488

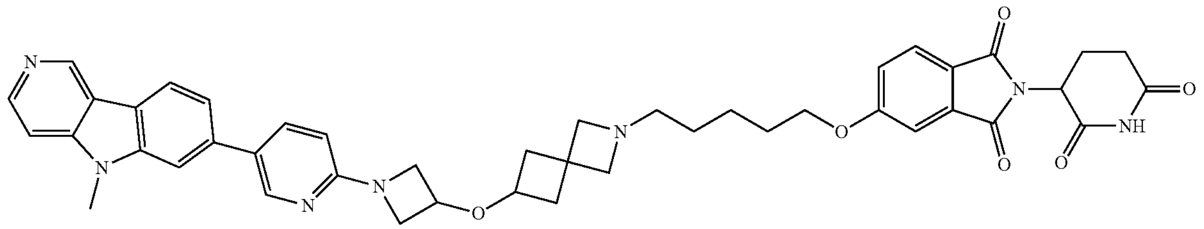 [SMILES: Cn1c2ccncc2c2ccc(-c3ccc(N4CC(OC5CC6(C5)CN(CCCCCOc5ccc7c(c5)C(=O)N(C5CCC(=O)NC5=O)C7=O)C6)C4)nc3)cc21]

Step 1

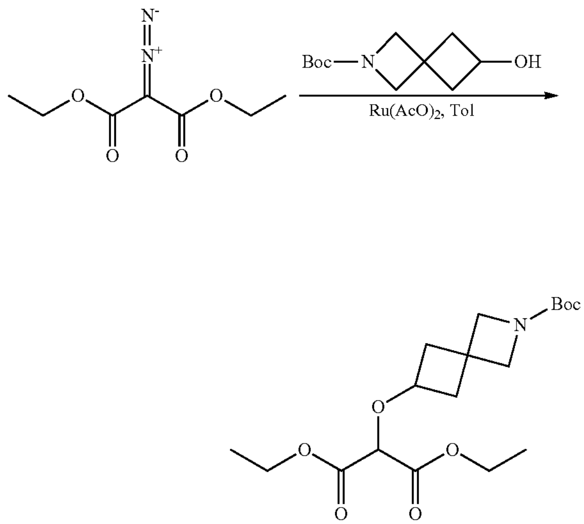

Step 2

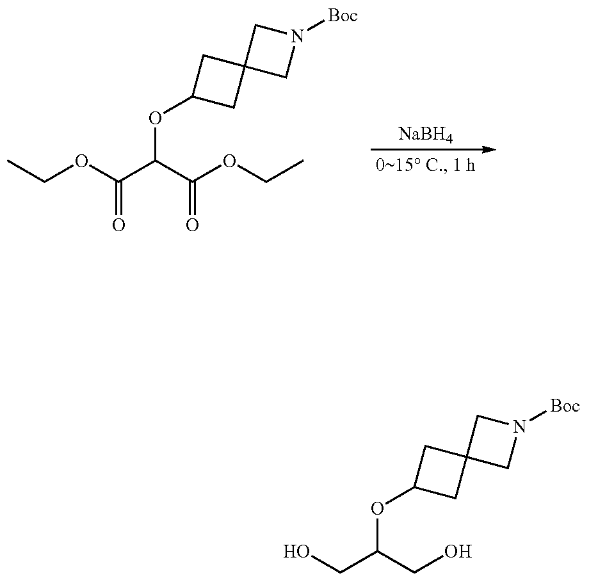

To a suspension of tert-butyl 6-hydroxy-2-azaspiro[3.3]heptane-2-carboxylate (1.07 g, 5.0 mmol, 1.0 eq) and rhodium acetate (110 mg, 0.2 mmol, 0.05 eq) in toluene (20 mL) was added diethyl 2-diazopropanedioate (1.86 g, 9.99 mmol, 2 eq) dropwise. When addition was completed, the mixture was stirred at 60° C. for 15 h. The mixture was poured into brine (50 mL) and extracted with ethyl acetate (50 mL×2). The organic layers were washed with brine dried and concentrated in vacuum. The residue was further purified by column chromatography (petroleum ether/ethyl acetate=10:1 to 3:1). Diethyl 2-[(2-tert-butoxycarbonyl-2-azaspiro[3.3]heptan-6-yl)oxy]propanedioate (1.25 g, 3.37 mmol, 67% yield) was obtained as a colorless oil.

To a solution of diethyl 2-[(2-benzyloxycarbonyl-2-azaspiro[3.3]heptan-6-yl)oxy]propanedioate (1.8 g, 4.44 mmol, 1 eq) in tetrahydrofuran (20 mL) and methanol (20 mL) was added sodium borohydride (1.01 g, 26 mmol, 6 eq). The mixture was stirred at 15° C. for 2 hours. The mixture was poured into 50 mL of saturated brine, and extracted with ethyl acetate (50 mL×2). The combined organic layers were washed with brine, dried and concentrated in vacuum. Benzyl 6-[2-hydroxy-1-(hydroxymethyl)ethoxy]-2-azaspiro[3.3]heptane-2-carboxylate (1.4 g, 4.29 mmol, 96% yield, 98% purity) was obtained as a colorless oil and used without further purification.

Step 3

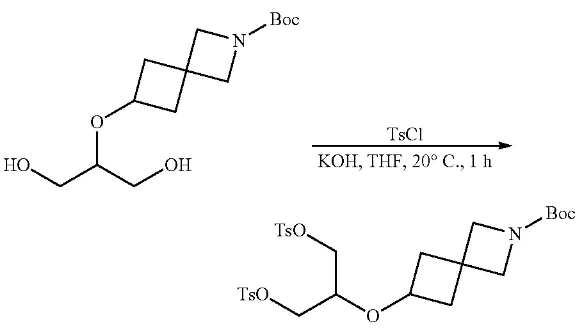

To a solution of tert-butyl 6-[2-hydroxy-1-(hydroxymethyl)ethoxy]-2-azaspiro[3.3]heptanes-2-carboxylate (0.8 g, 2.78 mmol, 1 eq) in tetrahydrofuran (6 mL) was added potassium hydroxide (1.56 g, 27.8 mmol, 10 eq) and p-toluenesulfonyl chloride (1.86 g, 9.74 mmol, 3.5 eq). The mixture was stirred at 15° C. for 0.5 hr. The reaction mixture was quenched by addition water 30 mL at 25° C., and then diluted with ethyl acetate 20 mL and extracted with ethyl acetate (20 mL×3). The combined organic layers were washed with brine (15 mL×2), dried over sodium sulfate, filtered and concentrated under reduced pressure. The residue was purified by column chromatography (petroleum ether/ethyl acetate=20:1 to 10:1). tert-Butyl 6-[2-(p-tolylsulfonyloxy)-1-(p-tolylsulfonyloxymethyl)ethoxy]-2-azaspiro[3.3]heptane-2-carboxylate (1.5 g, 2.52 mmol, 90% yield) was obtained as a yellow solid.

Step 4

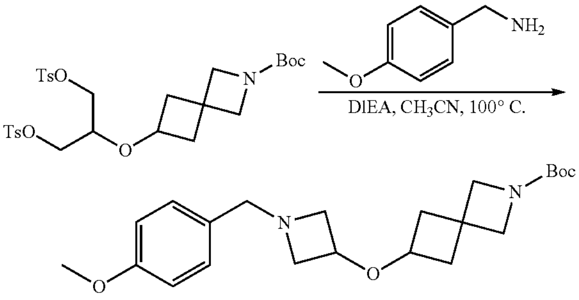

To a solution of (4-methoxyphenyl)methanamine (227 mg, 1.66 mmol, 1.1 eq) in acetonitrile (12 mL) was added N,N-diisopropylethylamine (488 mg, 3.78 mmol, 2.5 eq) and tert-butyl 6-[2-(p-tolylsulfonyloxy)-1-(p-tolylsulfonyloxymethyl)ethoxy]-2-azaspiro[3.3]heptane-2-carboxylate (0.9 g, 1.51 mmol, 1 eq). The mixture was stirred at 100° C. for 12 h. The reaction mixture was quenched by the addition of water (20 mL) at 25° C., and then diluted with ethyl acetate (20 mL) and extracted with ethyl acetate (10 mL×3). The combined organic layers were washed with brine (10 mL×2), dried over sodium sulfate, filtered and concentrated under reduced pressure. The residue was purified by column chromatography (petroleum ether/ethyl acetate=20:1 to 2:1). tert-Butyl 6-[1-[(4-methoxyphenyl)methyl]azetidin-3-yl]oxy-2-azaspiro[3.3]heptane-2-carboxylate (340 mg, 0.8 mmol, 57% yield) was obtained as a white solid.

tert-Butyl 6-[1-[(4-methoxyphenyl)methyl]azetidin-3-yl]oxy-2-azaspiro[3.3]heptane-2-carboxylate was converted to the title compound as described in the scheme below using procedures described for other examples above and known to those skilled in the art.

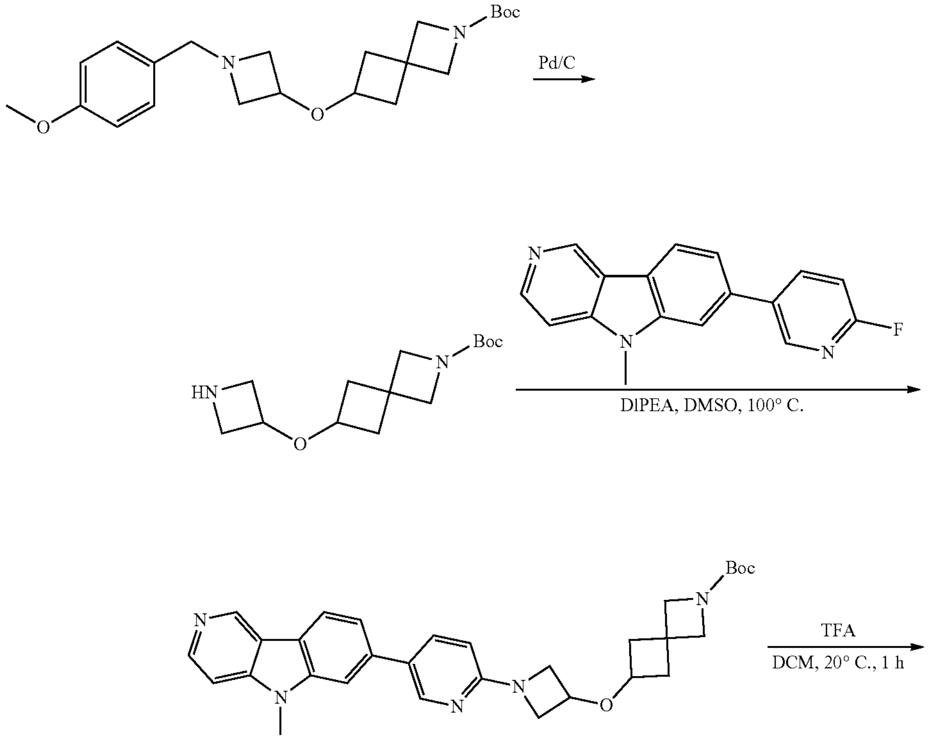

-continued

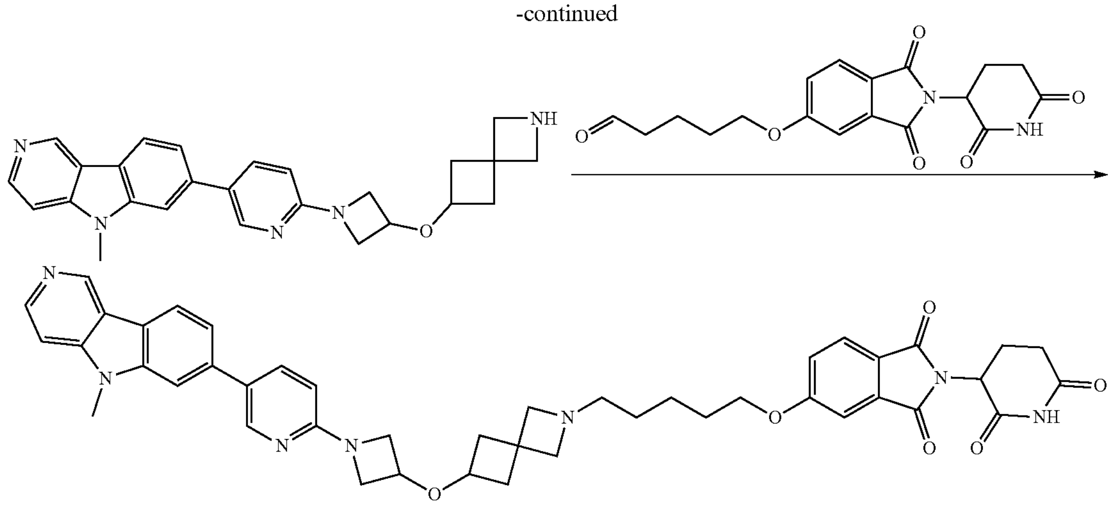

Exemplary Compound 488

Exemplary Synthesis of Exemplary Compound 489

Step 1

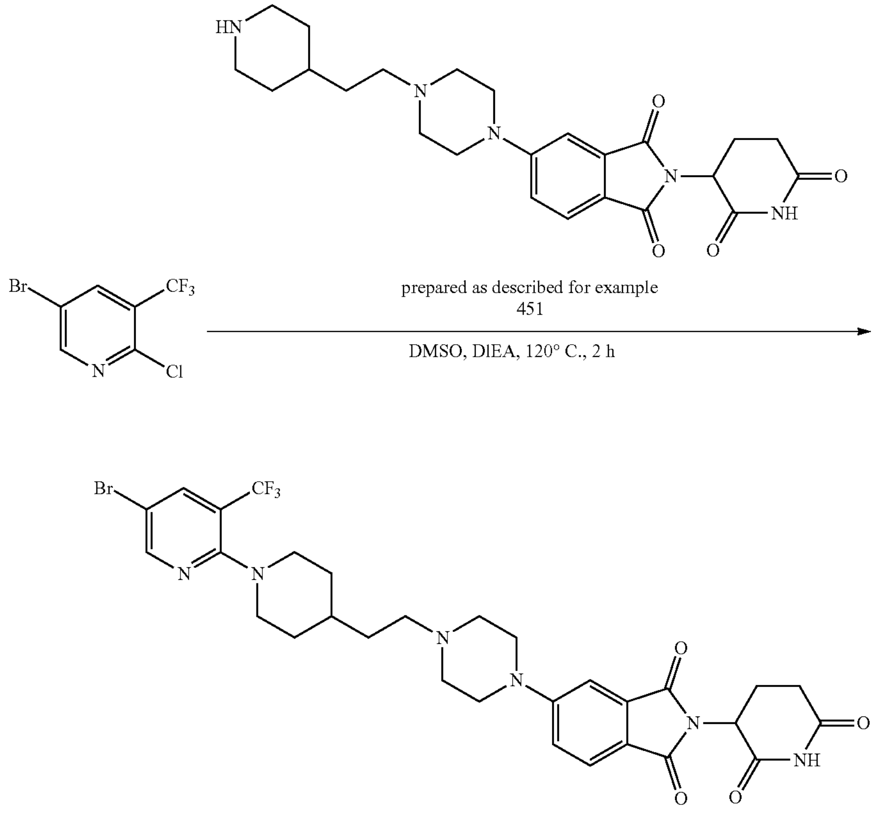

To a solution of 2-(2,6-dioxo-3-piperidyl)-5-[4-[2-(4-piperidyl)ethyl]piperazin-1-yl]isoindoline-1,3-dione (600 mg, 1.22 mmol, 1.00 eq, hydrochloric acid) in dimethylsulfoxide (10 mL) was added diisopropylethyllamine (474 mg, 3.67 mmol, 3.00 eq) and 5-bromo-2-chloro-3-(trifluoromethyl) pyridine (350 mg, 1.35 mmol, 1.10 eq). The mixture was stirred at 120° C. for 2 hours. The reaction mixture was diluted with water (50 mL) and extracted with ethyl acetate (100 mL×3). The combined organic layers were washed with brine (80 mL×3), dried over sodium sulfate, filtered and concentrated under reduced pressure. The residue was purified by silica gel chromatography (dichloromethane:methyl alcohol=100:1 to 10:1) to give 5-[4-[2-[l-[5-bromo-3-(trifluoromethyl)-2-pyridyl]-4-piperidyl]ethyl]piperazin-1-yl]-2-(2,6-dioxo-3-piperidyl)isoindoline-1,3-dione (400 mg, 0.59 mmol, 48% yield) as a yellow oil.

Step 2

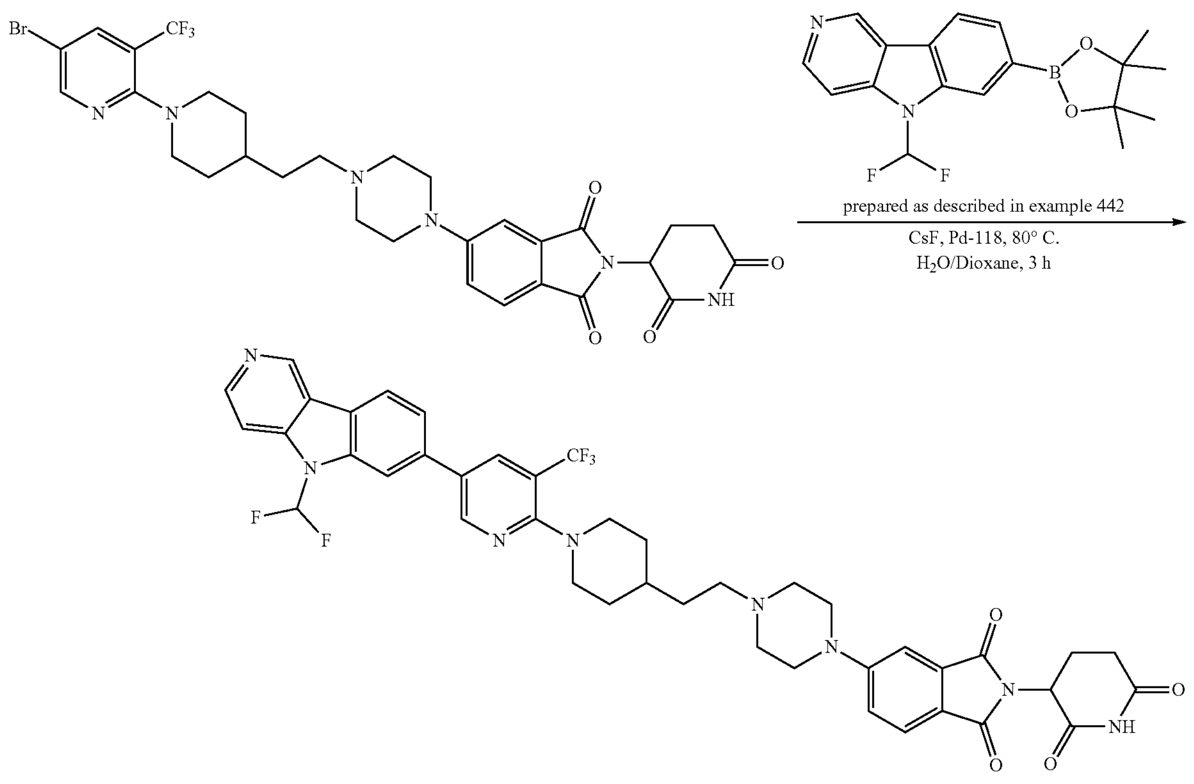

Exemplary compound 489

5-(difluoromethyl)-7-(4,4,5,5-tetramethyl-1,3,2-dioxaborolan-2-yl)pyrido[4,3-b]indole (80 mg, 0.23 mmol, 1.00 eq), 5-[4-[2-[1-[5-bromo-3-(trifluoromethyl)-2-pyridyl]-4-piperidyl]ethyl]piperazin-1-yl]-2-(2,6-dioxo-3-piperidyl) isoindoline-1,3-dione (157 mg, 0.23 mmol, 1.00 eq), cesium fluoride (70 mg, 0.46 mmol, 2.00 eq) and 1,1'-bis(di-tert-butylphosphino)ferrocene]dichloropalladium(II) (15 mg, 0.023 mmol, 0.10 eq) in dioxane (5 mL) and water (0.5 mL) was degassed and then heated to 80° C. for 3 hours under nitrogen. The reaction mixture was filtered and concentrated under reduced pressure. The residue was purified by preparative HPLC (column: Phenomenex Synergi C18 150*25*10 um; mobile phase: [water (0.1% trifluoroacetate)-acetonitrile]; B %: 25%-45%, 10 min) to give 5-[4-[2-[1-[5-[5-(difluoromethyl)pyrido[4,3-b]indol-7-yl]-3-(trifluoromethyl)-2-pyridyl]-4-piperidyl]ethyl]piperazin-1-yl]-2-(2,6-dioxo-3-piperidyl)isoindoline-1,3-dione trifluroacetate (84 mg, 0.09 mmol, 39% yield) as a yellow solid.

Exemplary Synthesis of Exemplary Compound 494

Prepared according to the scheme below using procedures analogous to those described for exemplary compound 489 and other examples above.

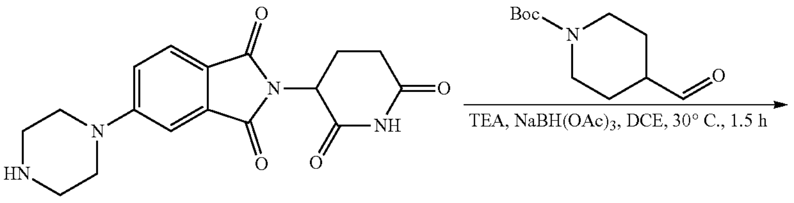

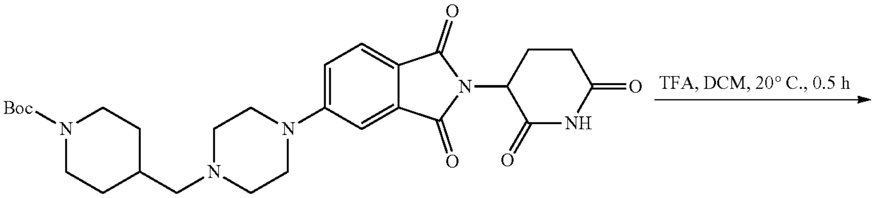

-continued
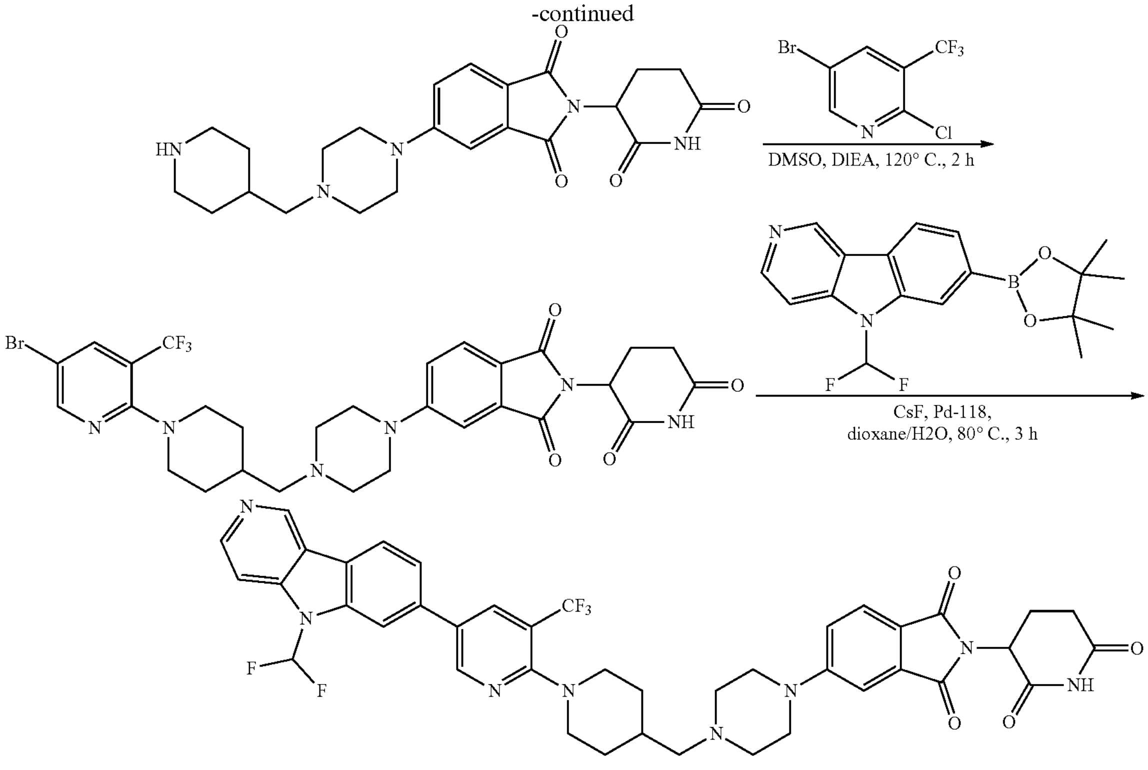
Exemplary Compound 494
Exemplary Synthesis of Exemplary Compound 495
Prepared according to the scheme below using procedures described above for exemplary compound 454.
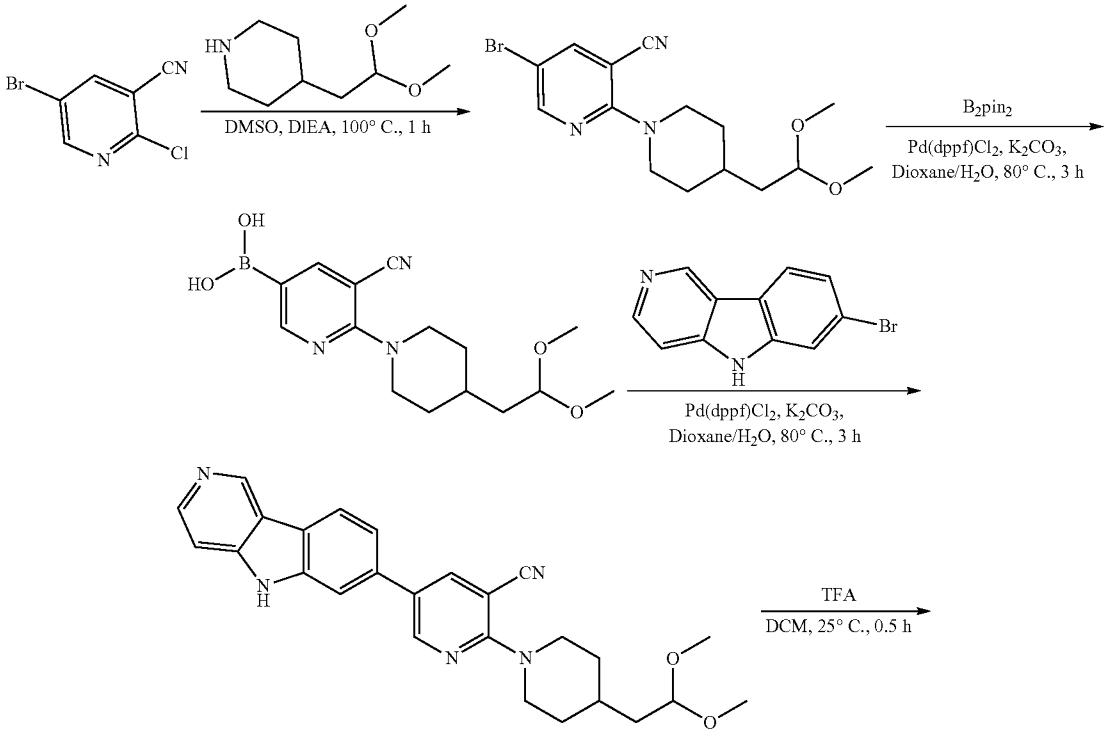

-continued

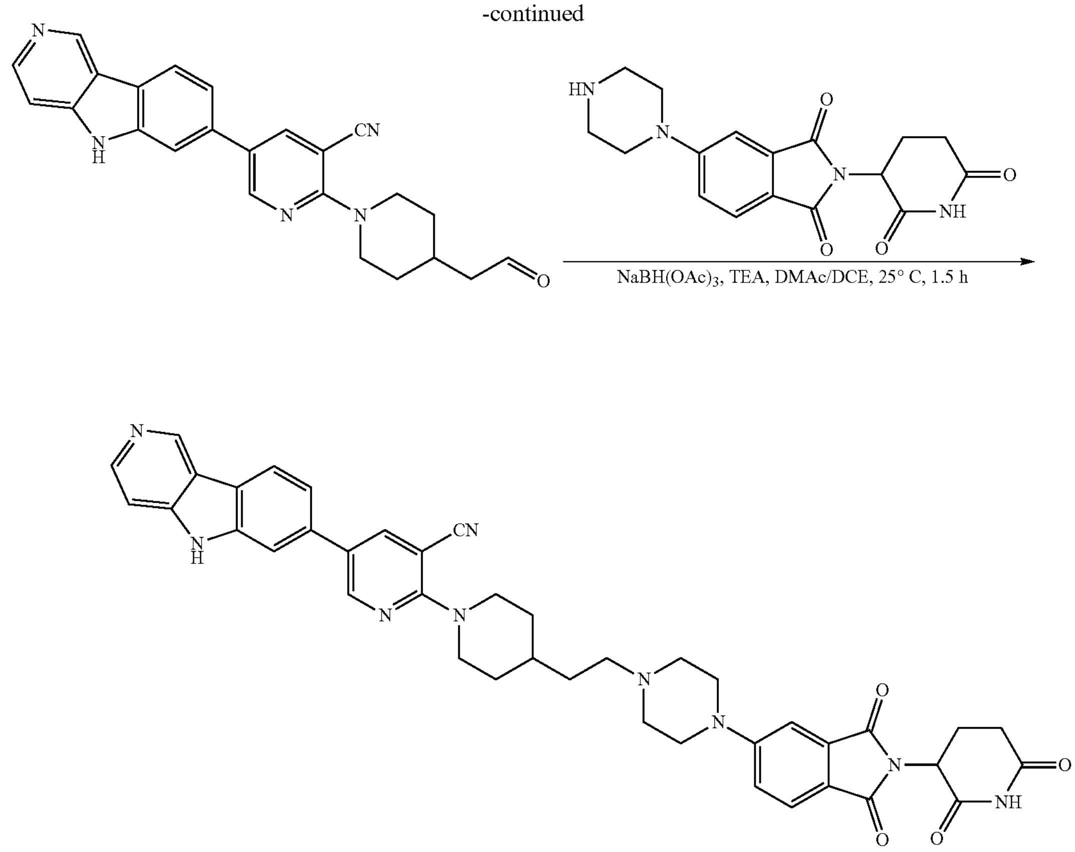

Exemplary Compound 495

Using analogous procedures the following exemplary compounds were prepared: 496, 530.

Exemplary Synthesis of Exemplary Compound 501

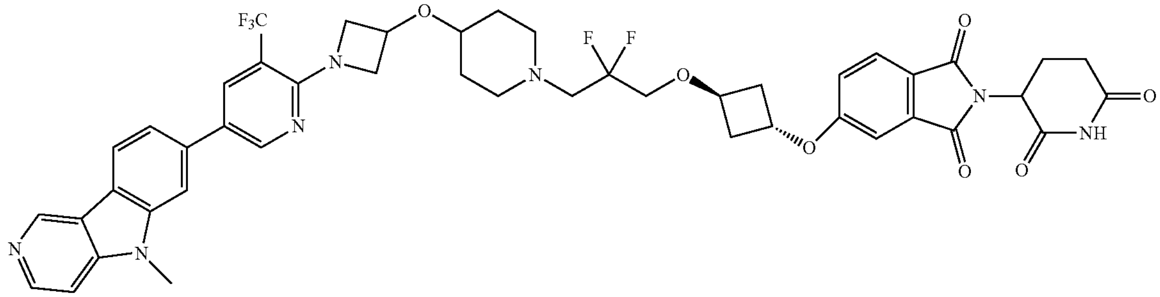 [SMILES: Cn1c2ccncc2c2ccc(-c3cnc(N4CC(OC5CCN(CC(F)(F)CO[C@H]6C[C@H](Oc7ccc8c(c7)C(=O)N(C7CCC(=O)NC7=O)C8=O)C6)CC5)C4)c(C(F)(F)F)c3)cc21]

Step 1

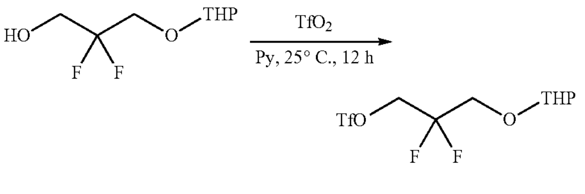

To a mixture of 2,2-difluoro-3-tetrahydropyran-2-yloxy-propan-1-ol (1.9 g, 9.68 mmol, 1 eq) and pyridine (1.53 g, 19.37 mmol, 1.56 mL, 2 eq) in dichloromethane (20 mL) was added trifluoromethanesulfonic anhydride (3.28 g, 11.62 mmol, 1.2 eq). The mixture was stirred at 15° C. for 12 h. The mixture was quenched by addition water (200 mL), extracted with ethyl acetate (30 mL×3), the combined organic phase washed with brine (30 mL), dried over anhydrous sodium sulfate, filtered and concentrated under reduced pressure. The residue was purified by silica gel column chromatography (petroleum ether:ethyl acetate=100:1-30:1). Compound (2,2-difluoro-3-tetrahydro-pyran-2-yloxy-propyl) trifluoromethanesulfonate (2.9 g, 8.83 mmol, 91% yield) was obtained as a yellow oil.

Step 2

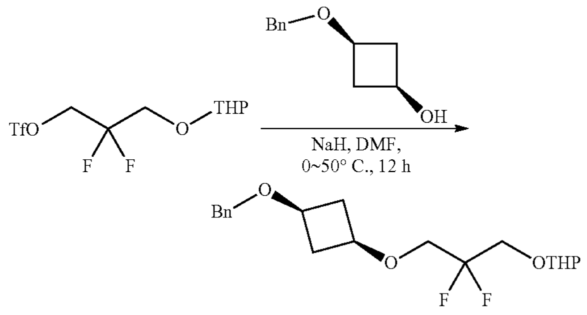

To a mixture of 3-benzyloxycyclobutanol (1.30 g, 7.31 mmol, 1.2 eq) in dimethyl formamide (20 mL) was added sodium hydride (292 mg, 7.31 mmol, 60% purity, 1.2 eq) at 0° C. The mixture was stirred at 0° C. for 30 min. Then (2,2-difluoro-3-tetrahydropyran-2-yloxy-propyl) trifluoromethanesulfonate (2 g, 6.09 mmol, 1 eq) was added, and the mixture was stirred at 50° C. for 12 h. The mixture was quenched by the addition of water (150 mL), extracted with ethyl acetate (40 mL×4), and the combined organic phase was washed with brine (20 mL×3), dried over anhydrous sodium sulfate, filtered and concentrated under reduced pressure. The residue was purified by silica gel column chromatography (petroleum ether:ethyl acetate=100:1 to 30:1). Compound 2-[3-(3-benzyloxycyclobutoxy)-2,2-difluoro-propoxy]tetrahydropyran (1.5 g, 4.21 mmol, 69% yield) was obtained as a colorless oil.

2-[3-(3-Benzyloxycyclobutoxy)-2,2-difluoro-propoxy] tetrahydropyran was converted to the title compound according to the scheme below using procedures described for other examples above and commonly known to those skilled in the art.

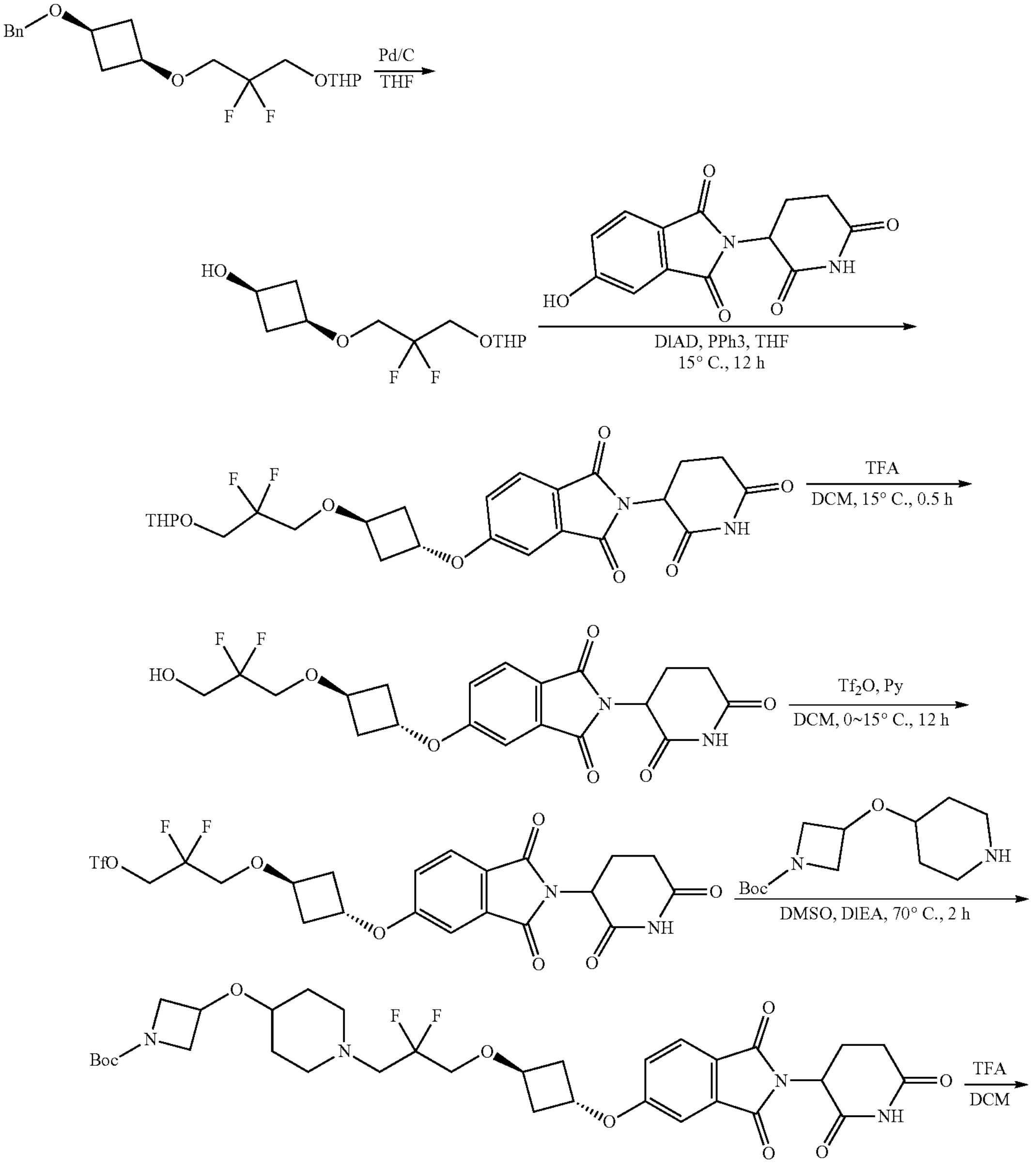

-continued
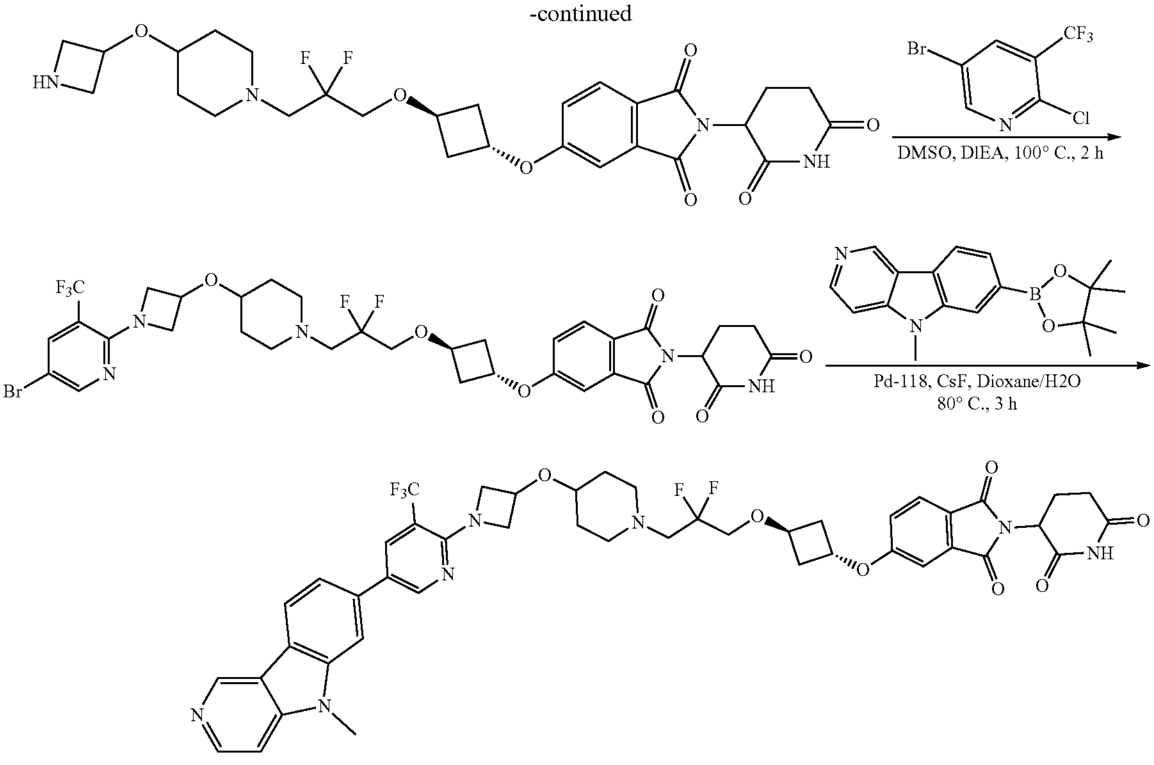
Exemplary Compound 501
Exemplary Synthesis of Exemplary Compound 504
Prepared according to the scheme below using procedures described for other examples above and commonly known to those skilled in the art.
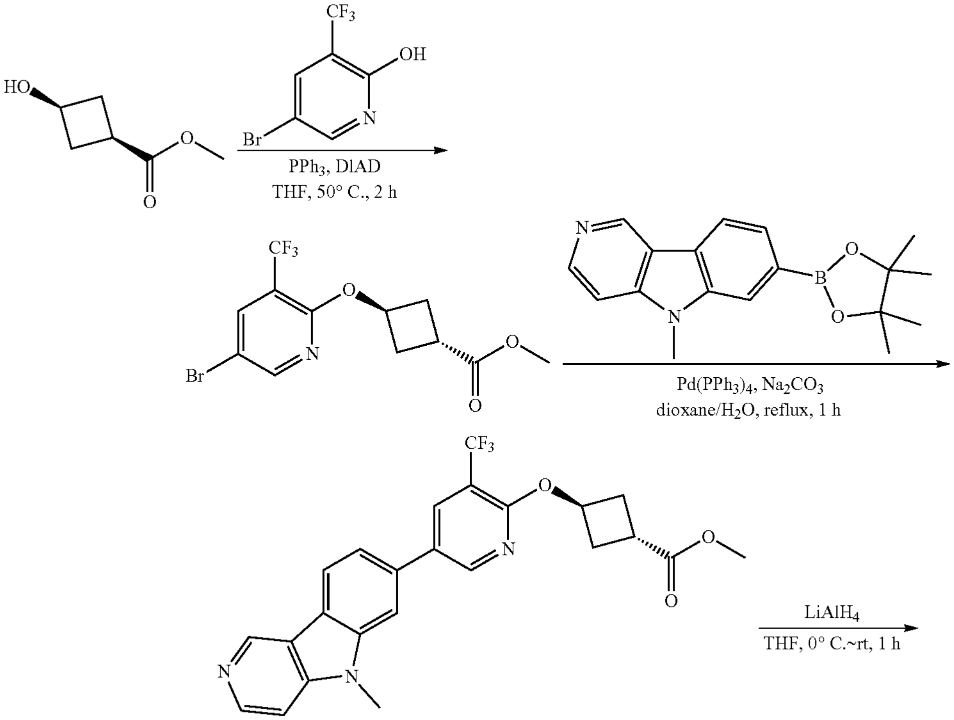

-continued
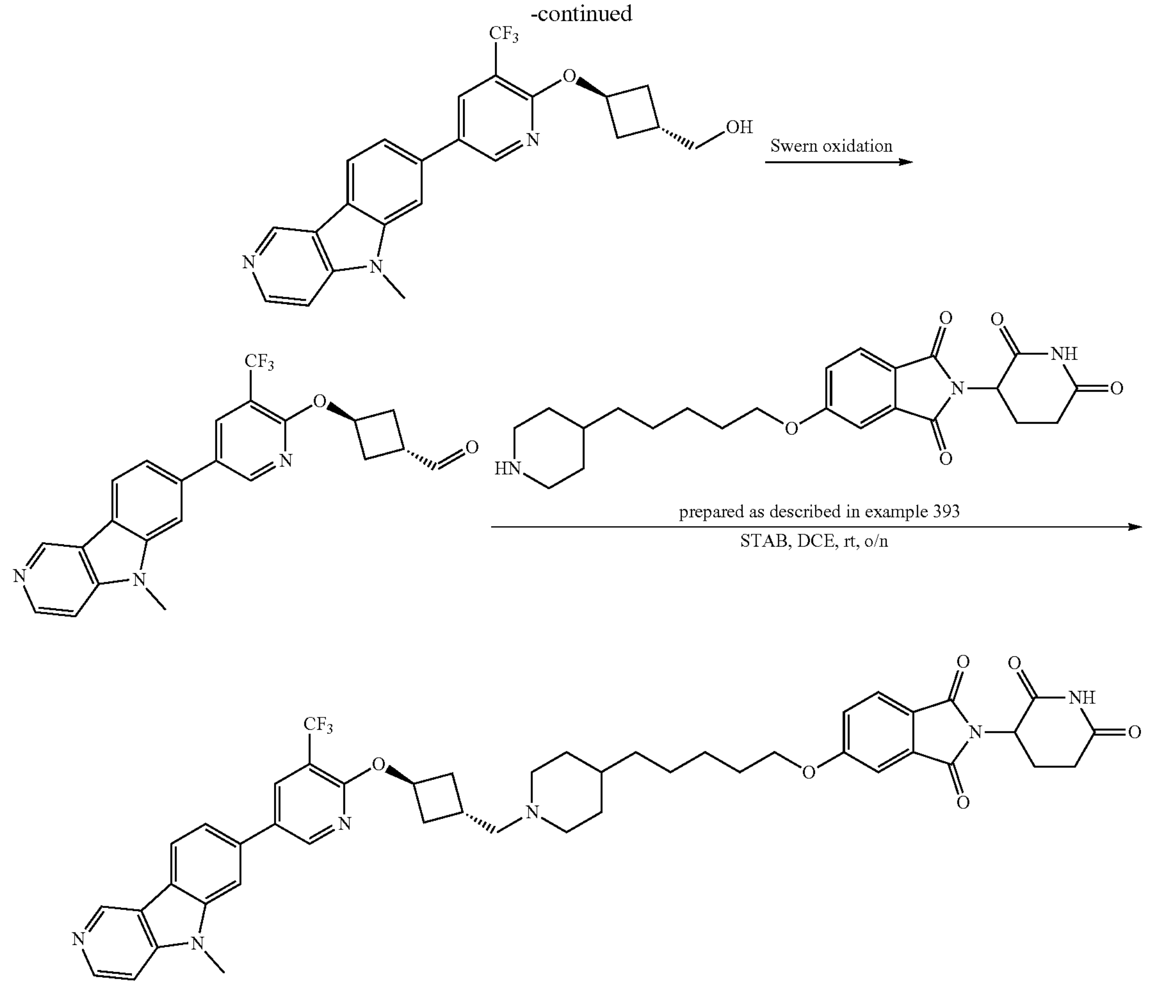
Exemplary Compound 504
Using analogous procedures and the tricyclic intermediate prepared as described for exemplary compound 442 the following exemplary compound was prepared: 516.
Exemplary Synthesis of Exemplary Compound 506
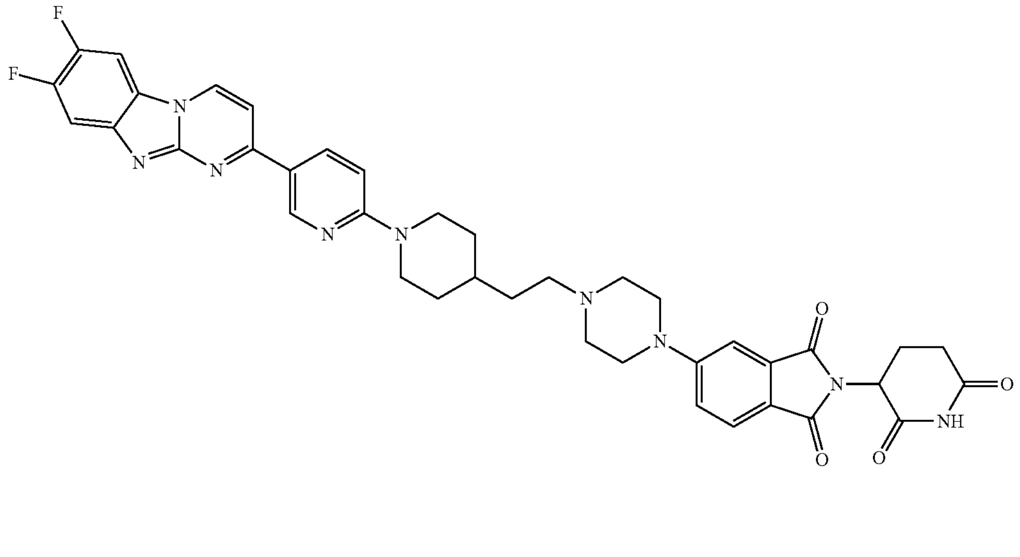 [SMILES: O=C1CCC(N2C(=O)c3ccc(N4CCN(CCC5CCN(c6ccc(-c7ccn8c(n7)nc7cc(F)c(F)cc78)cn6)CC5)CC4)cc3C2=O)C(=O)N1]

Step 1

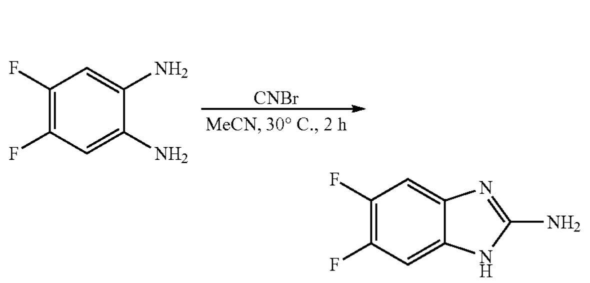

To a solution of 4,5-difluorobenzene-1,2-diamine (5 g, 34.69 mmol, 1 eq) in acetonitrile (70 mL) was added cyanogen bromide (4.41 g, 41.63 mmol, 3.06 mL, 1.2 eq) in acetonitrile (70 mL). The mixture was stirred at 30° C. for 2 hours. The reaction mixture was filtered and used water (70 ml) and sodium carbonate (2M, 70 ml) and was stirred for 0.5 h, then filtered and concentrated under reduced pressure to give 5,6-difluoro-1H-benzimidazol-2-amine (2.2 g, 13.01 mmol, 37% yield) as a brown solid and was used into next step without further purification.

Step 2

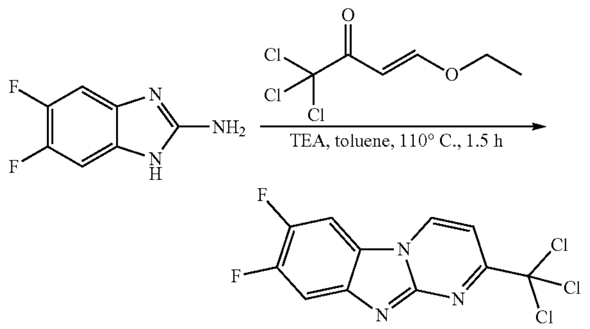

To a solution of 5,6-difluoro-1H-benzimidazol-2-amine (2.2 g, 13.01 mmol, 1.03 eq) in toluene (60 mL) was added triethylamine (1.28 g, 12.63 mmol, 1.76 mL, 1 eq) and (E)-1,1,1-trichloro-4-ethoxy-but-3-en-2-one (2.75 g, 12.63 mmol, 1 eq). The mixture was stirred at 110° C. for 1.5 hours. The reaction mixture was concentrated and filtered under reduced pressure to give 7,8-difluoro-2-(trichloromethyl) pyrimido[1,2-a]benzimidazole (3 g, crude) as a yellow solid which was used in the next step without further purification.

7,8-Difluoro-2-(trichloromethyl) pyrimido[1,2-a]benzimidazole was converted to the title compound using procedures described in US 20180125821 for desfluoro 2-(trichloromethyl) pyrimido[1,2-a]benzimidazole combined with procedures described for exemplary compound 451.

Exemplary Synthesis of Exemplary Compound 509

Prepared according to the scheme below using procedures described for other examples above as well as known to those skilled in the art.

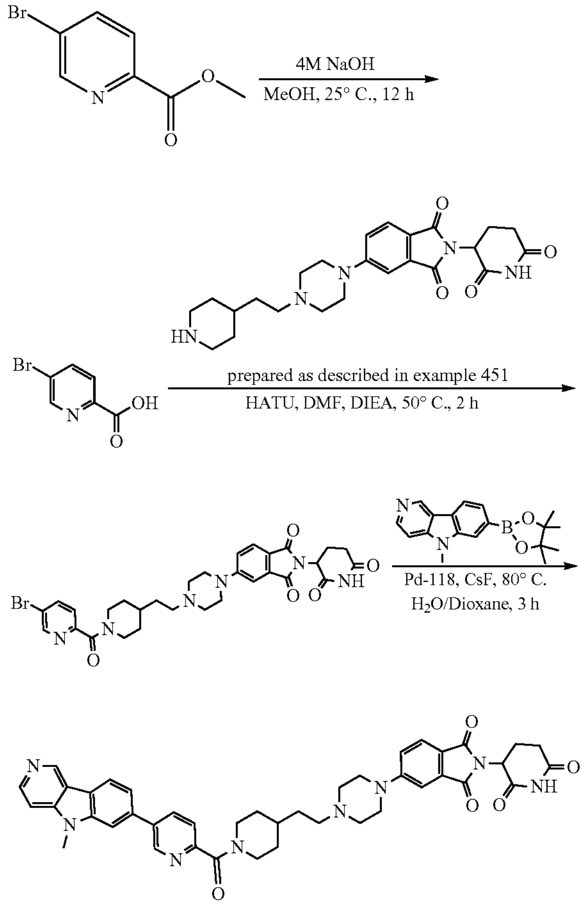

Exemplary Compound 509

Exemplary Synthesis of Exemplary Compound 510

Prepared according to the scheme below using procedures described for other examples above as well as known to those skilled in the art.

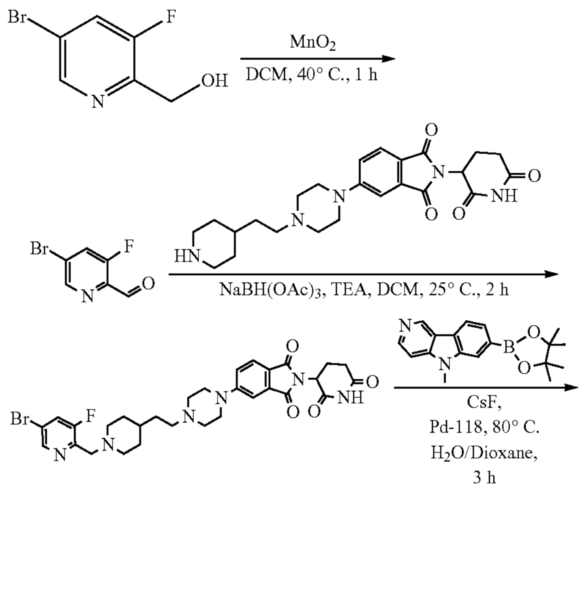

-continued

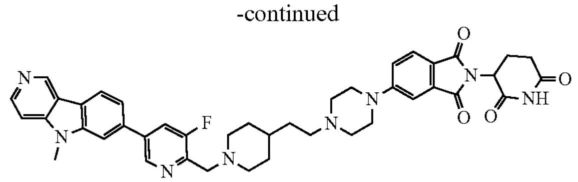

Exemplary Compound 510

Exemplary Synthesis of Exemplary Compound 511

Prepared according to the scheme below using procedures described for other examples above as well as known to those skilled in the art.

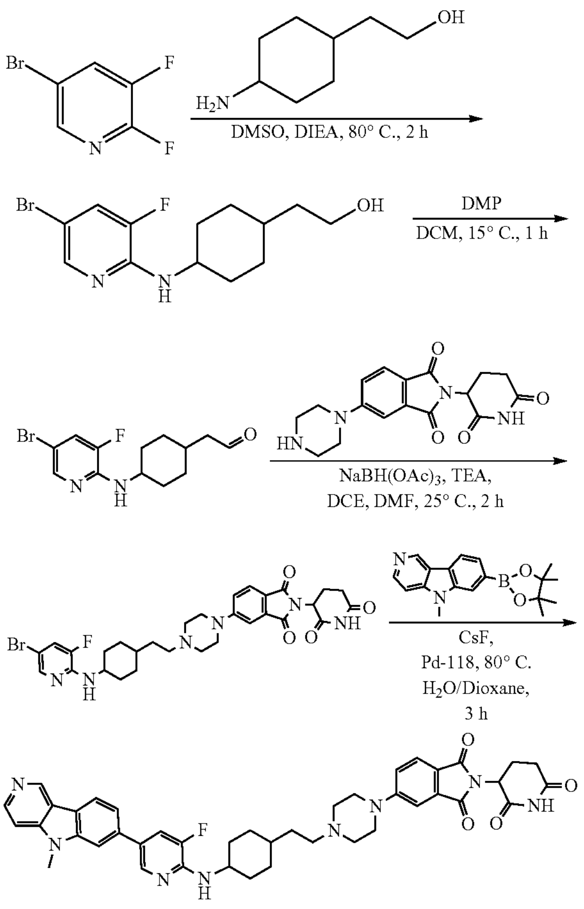

Exmeplary Compound 511

Exemplary Synthesis of Exemplary Compound 512

Prepared according to the scheme below using procedures described for other examples above as well as known to those skilled in the art.

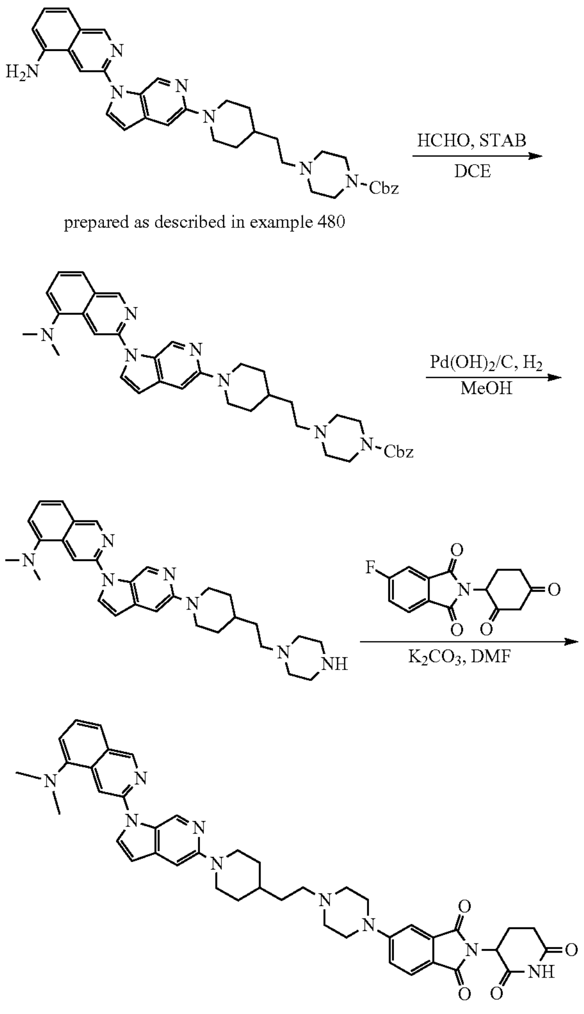

Exemplary Compound 512

Exemplary Synthesis of Exemplary Compound 514

Prepared according to the scheme below using procedures described for other examples above as well as known to those skilled in the art.

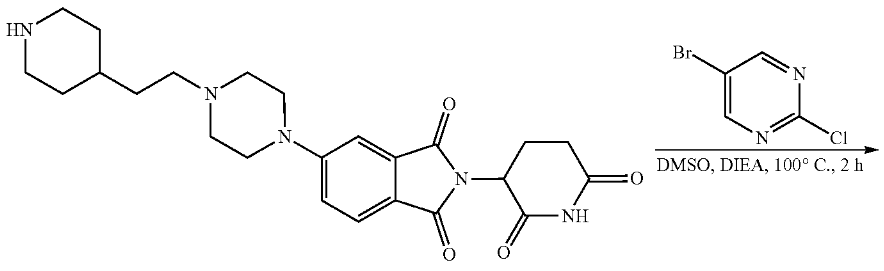

-continued
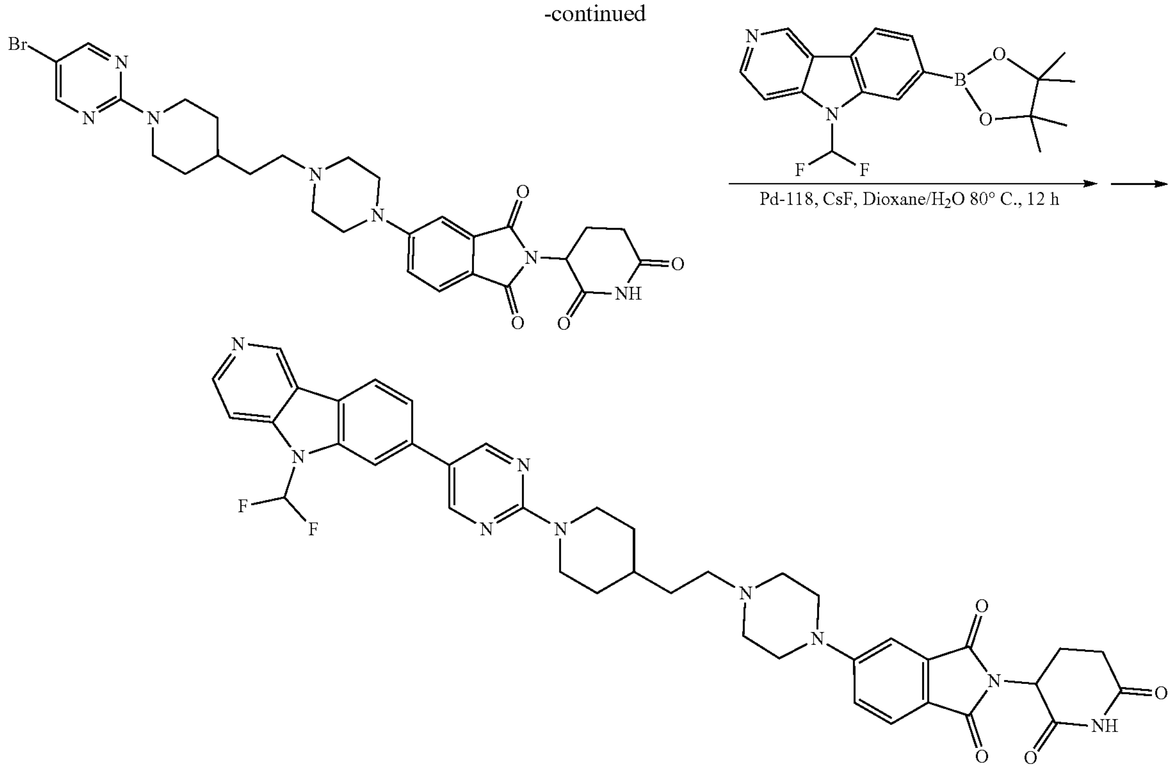
Exemplary Compound 514
Exemplary Synthesis of Exemplary Compound 515
Prepared according to the scheme below using procedures described for other examples above as well as known to those skilled in the art.
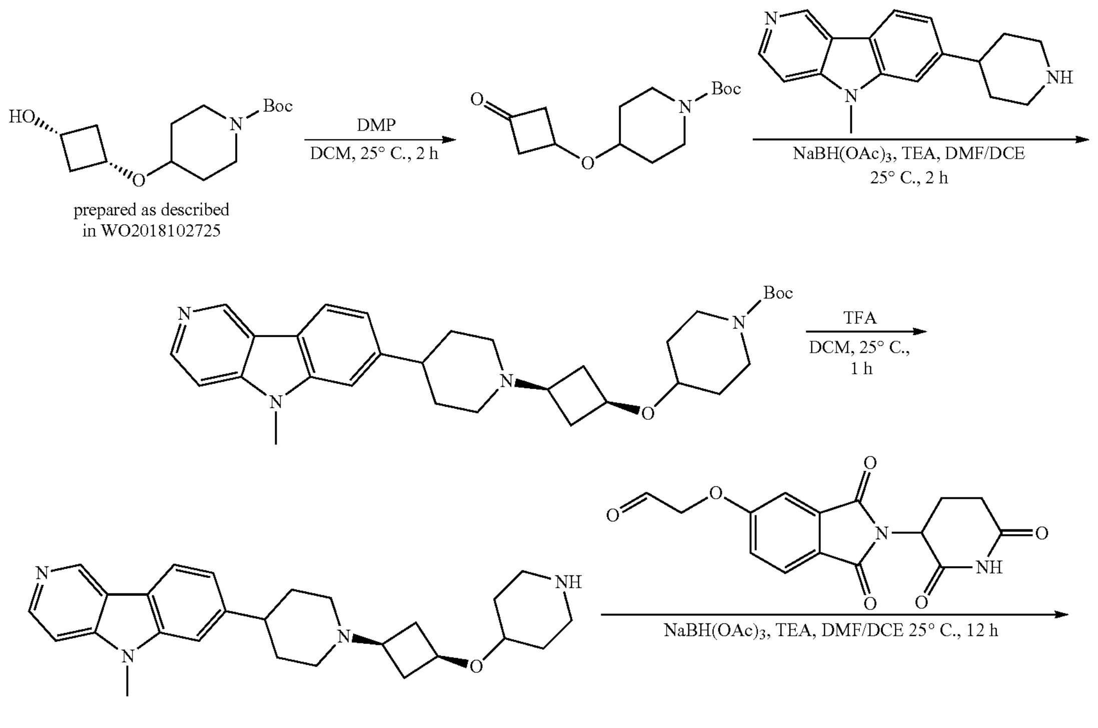

-continued

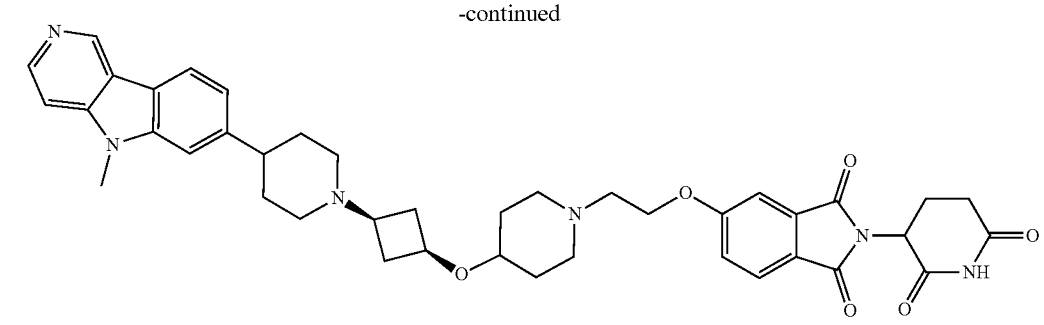

Exemplary Compound 515

Exemplary Synthesis of Exemplary Compound 515

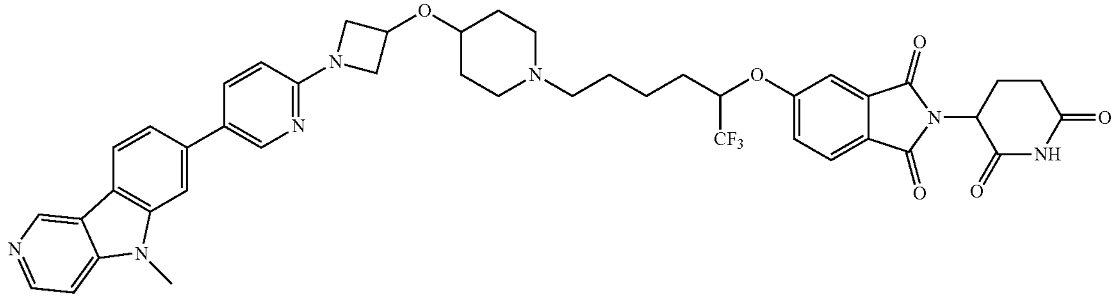 [SMILES: Cn1c2ccncc2c2ccc(-c3ccc(N4CC(OC5CCN(CCCCC(Oc6ccc7c(c6)C(=O)N(C6CCC(=O)NC6=O)C7=O)C(F)(F)F)CC5)C4)nc3)cc21]

Step 1

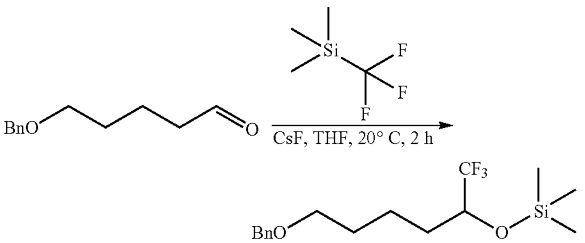

To a solution of 5-benzyloxypentanal (1.8 g, 9.36 mmol, 1 eq) in tetrahydrofuran (30 mL) was added trimethyl (trifluoromethyl)silane (3.99 g, 28.09 mmol, 3 eq), and cesium fluoride (142 mg, 0.93 mmol, 0.1 eq). The mixture was stirred at 20° C. for 2 hours. The mixture was quenched by the addition of water (10 mL), extracted with ethyl acetate (10 mL×3), and the combined organic phase was washed with brine (20 mL), dried over anhydrous sodium, filtered and concentrated under reduced pressure. The residue was purified by silica gel column chromatography (petroleum ether/ethyl acetate=100/1 to 50/1) to give [5-benzyloxy-1-(trifluoromethyl)pentoxy]trimethylsilane (2.6 g, 7.77 mmol) as a colorless oil.

Step 2

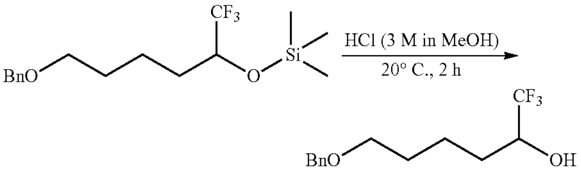

To a solution of [5-benzyloxy-1-(trifluoromethyl)pentoxy]trimethylsilane (2.6 g, 7.77 mmol, 1 eq) was added hydrochloric acid (3 M, 35 mL, 13.84 eq). The mixture was stirred at 20° C. for 2 hours. The mixture was quenched by the addition of sodium bicarbonate saturated solution (10 mL), extracted with ethyl acetate (30 mL×3), and the combined organic phase was washed with brine (30 mL), dried over anhydrous sodium, filtered and concentrated under reduced pressure. The residue was purified by silica gel column chromatography (petroleum ether/ethyl acetate=100/1 to 20/1) to give 6-benzyloxy-1,1,1-trifluoro-hexan-2-ol (1.7 g, 6.48 mmol) as a colorless oil.

Step 3

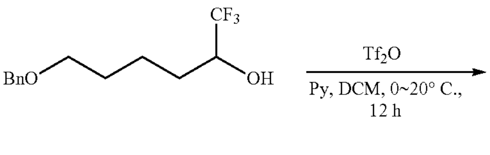

-continued

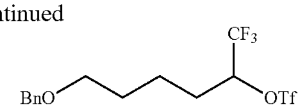

To a solution of 6-benzyloxy-1,1,1-trifluoro-hexan-2-ol (800 mg, 3.05 mmol, 1 eq) and pyridine (482 mg, 6.10 mmol, 2 eq) in dichloromethane (16 mL) was added trifluoromethanesulfonic anhydride (1.03 g, 3.66 mmol, 1.2 eq) at 0° C. The mixture was stirred at 20° C. for 12 hours. The reaction mixture was diluted with water (20 ml) and extracted with ethyl acetate (20 mL×3). The combined organic layers were dried over anhydrous sodium sulfate, filtered and concentrated under reduced pressure to give [5-benzyloxy-1-(trifluoromethyl)pentyl]trifluoromethanesulfonate (1.1 g, crude) as a colorless oil which was used in the next step without further purification.

Step 4

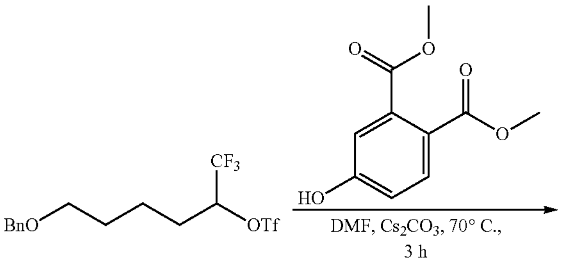

-continued

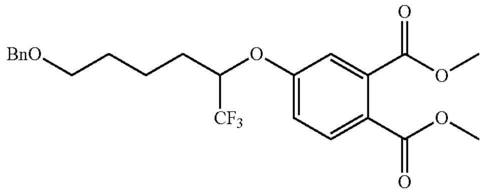

To a solution of [5-benzyloxy-1-(trifluoromethyl)pentyl] trifluoromethanesulfonate (1.1 g, 2.79 mmol, 1 eq) in N,N-dimethylformamide (10 mL) was added cesium carbonate (1.82 g, 5.58 mmol, 2 eq) and dimethyl 4-hydroxybenzene-1,2-dicarboxylate (586 mg, 2.79 mmol, 1 eq). The mixture was stirred at 70° C. for 3 hours. The reaction mixture was diluted with water (20 ml) and extracted with ethyl acetate (20 mL×3). The combined organic layers were dried over anhydrous sodium sulfate, filtered and concentrated under reduced pressure. The residue was purified by silica gel column chromatography (petroleum ether/ethyl acetate=100/1 to 8/1) to give dimethyl 4-[5-benzyloxy-1-(trifluoromethyl)pentoxy]benzene-1,2-dicarboxylate (460 mg, 0.99 mmol) as a white solid.

Dimethyl 4-[5-benzyloxy-1-(trifluoromethyl)pentoxy] benzene-1,2-dicarboxylate was converted to the title compound according to the scheme below using procedures described for other examples above as well as known to those skilled in the art.

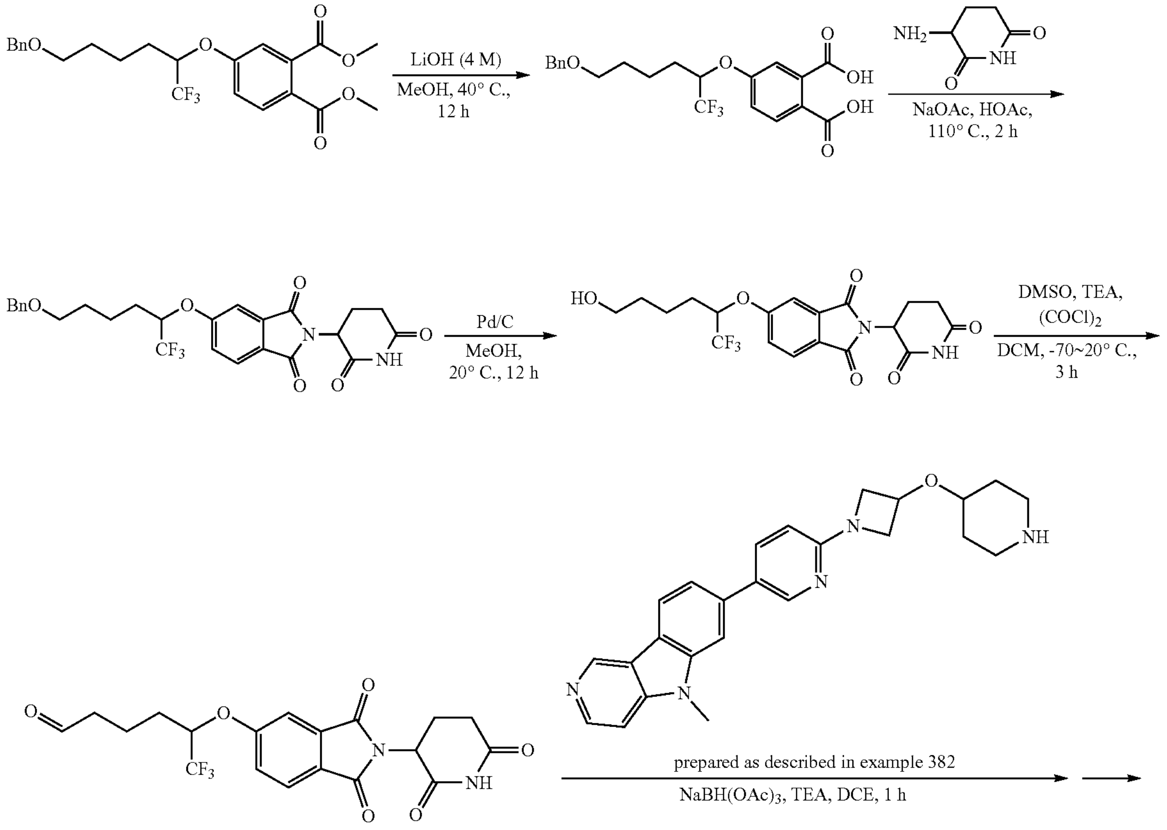

-continued

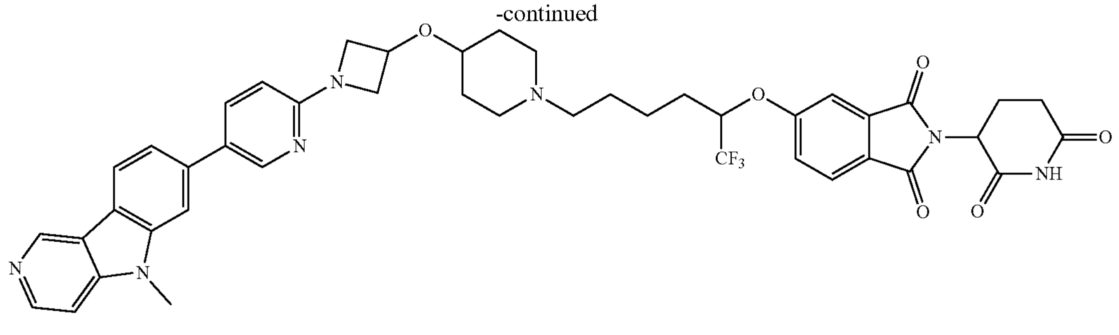

Exemplary Compound 520

Exemplary Synthesis of Exemplary Compound 521

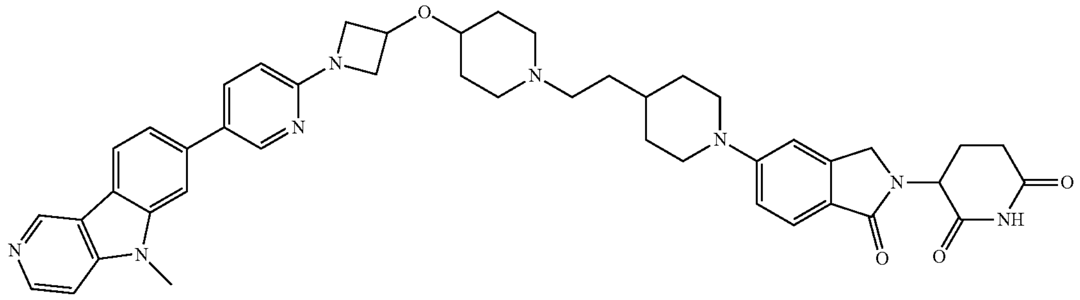 [SMILES: Cn1c2ccncc2c2ccc(-c3ccc(N4CC(OC5CCN(CCC6CCN(c7ccc8c(c7)CN(C7CCC(=O)NC7=O)C8=O)CC6)CC5)C4)nc3)cc21]

Step 1

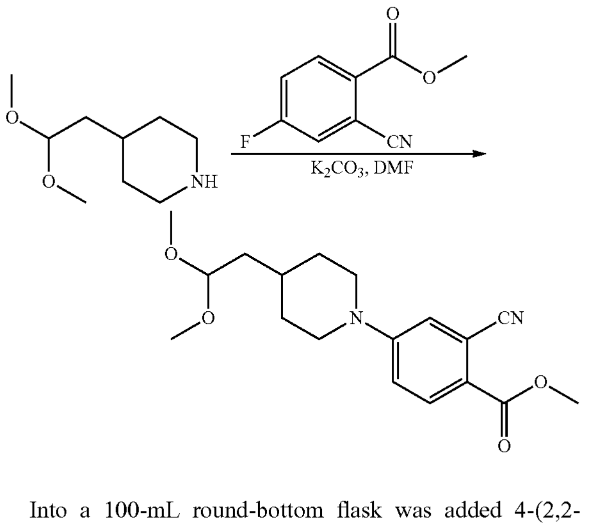

Into a 100-mL round-bottom flask was added 4-(2,2-dimethoxyethyl)piperidine (0.50 g, 2.89 mmol, 1.0 equiv), DMF (35 mL), methyl 2-cyano-4-fluorobenzoate (0.52 g, 2.89 mmol, 1.0 equiv) and $K_2CO_3$ (0.60 g, 4.33 mmol, 1.5 equiv) at room temperature. The resulting mixture was stirred for 2 h at 100° C. under nitrogen atmosphere. The resulting mixture was extracted with EtOAc (3×150 mL). The combined organic layers were washed with brine (3×10 mL), dried over anhydrous $Na_2SO_4$. After filtration, the filtrate was concentrated under reduced pressure. The residue was purified by prep-TLC ($CH_2Cl_2$:MeOH=20:1) to afford methyl 2-cyano-4-[4-(2,2-dimethoxyethyl)piperidin-1-yl]-benzoate (0.98 g) as a yellow oil.

Step 2

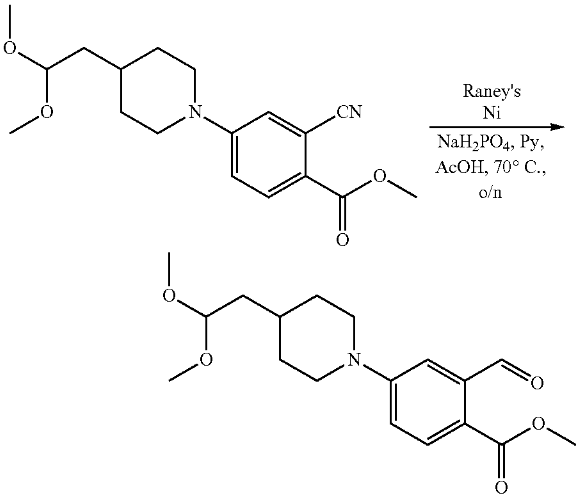

Into a 100-mL round-bottom flask was added methyl 2-cyano-4-[4-(2,2-dimethoxyethyl)piperidin-1-yl]benzoate (300 mg, 0.90 mmol, 1.0 equiv), AcOH (3.0 mL), pyridine (6.0 mL), Raney Ni (300 mg, 3.50 mmol, 3.9 equiv) and $NaH_2PO_4$ (2.17 g, 18.0 mmol, 20 equiv) at room temperature. The resulting mixture was stirred overnight at 70° C. under nitrogen atmosphere. The resulting mixture was filtered; the filter cake was washed with EtOAc (3×100 mL). The filtrate was extracted with EtOAc (2×100 mL). The combined organic layers were washed with brine (3×10 mL), dried over anhydrous $Na_2SO_4$. After filtration, the filtrate was concentrated under reduced pressure. The residue was purified by prep-TLC ($CH_2Cl_2$:MeOH=20:1) to afford methyl 4-[4-(2,2-dimethoxyethyl)piperidin-1-yl]-2-formylbenzoate (140 mg) as a yellow green oil.

Step 3

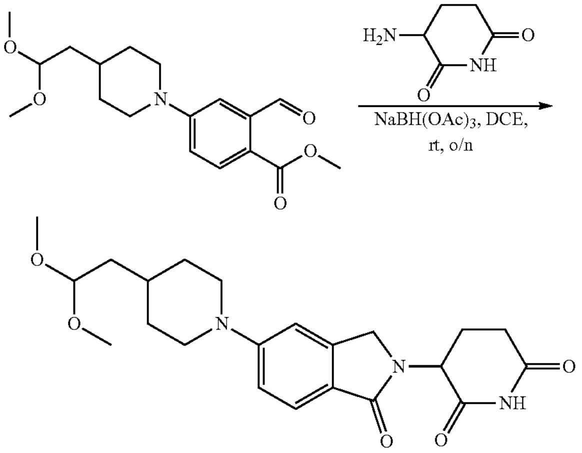

Into a 50 mL round-bottom flask were added methyl 4-[4-(2,2-dimethoxyethyl)-piperidin-1-yl]-2-formylbenzoate (140 mg, 0.42 mmol, 1.0 equiv), DCE (8 mL), 3-aminopiperidine-2,6-dione (80 mg, 0.63 mmol, 1.5 equiv) and $NaBH(OAc)_3$ (265 mg, 1.3 mmol, 3.0 equiv) at 0° C. The resulting mixture was stirred overnight at room temperature under nitrogen atmosphere. The resulting mixture was concentrated under reduced pressure. The residue was purified by prep-TLC ($CH_2Cl_2$:MeOH=15:1) to afford 3-[5-[4-(2,2-dimethoxyethyl)piperidin-1-yl]-1-oxo-3H-isoindol-2-yl]piperidine-2,6-dione (90 mg) as a yellow solid.

3-[5-[4-(2,2-Dimethoxyethyl)piperidin-1-yl]-1-oxo-3H-isoindol-2-yl]piperidine-2,6-dione was converted to the title compound according to the scheme below using procedures described for other examples above as well as commonly known to those skilled in the art.

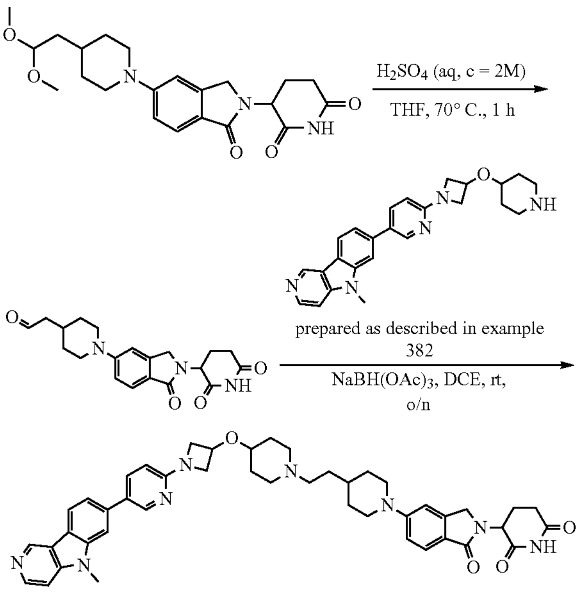

Exemplary Compound 521

Exemplary Synthesis of Exemplary Compound 522

Prepared according to the scheme below using procedures described for other examples above as well as commonly known to those skilled in the art.

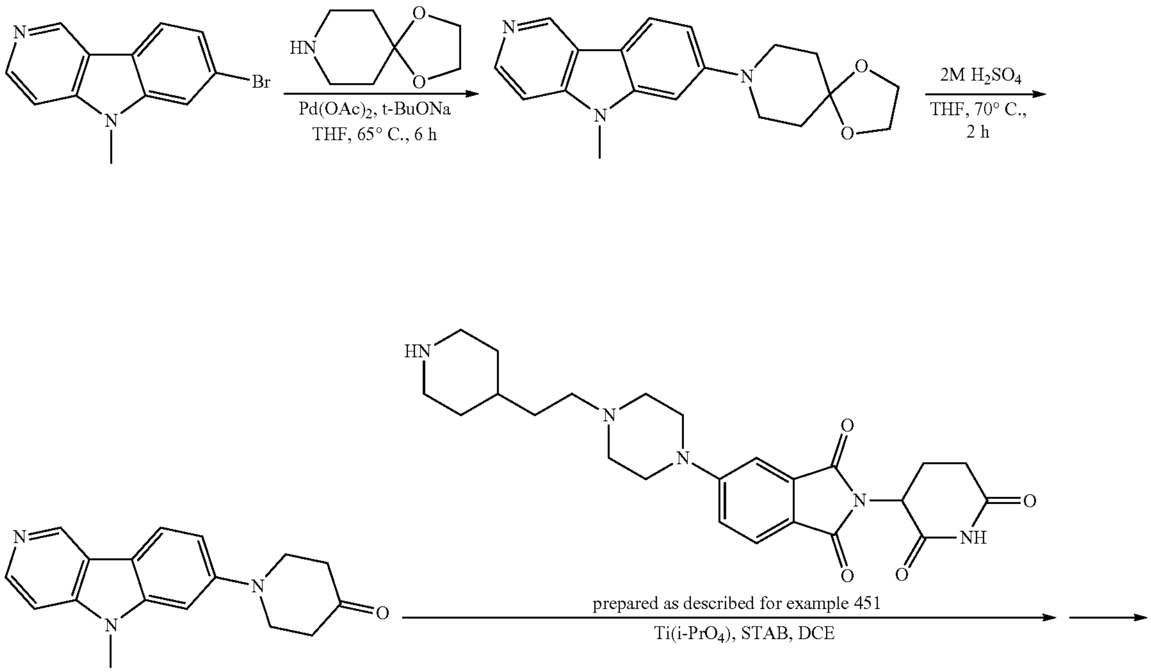

-continued

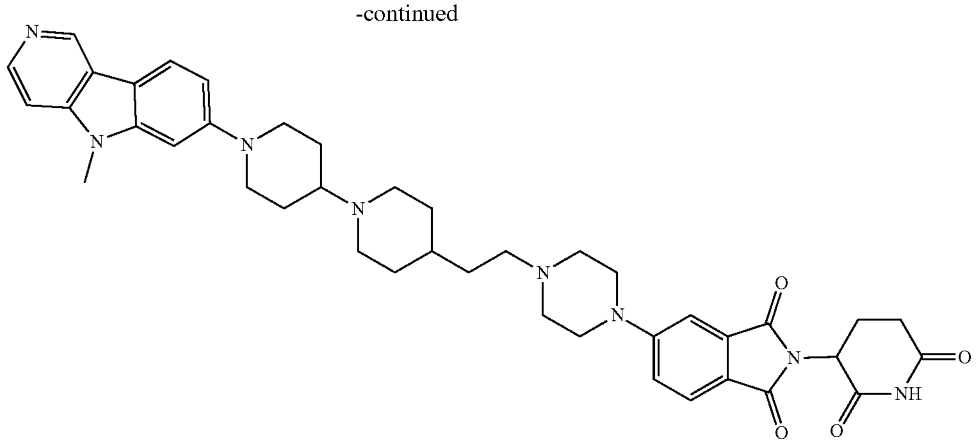

Exemplary Compound 522

Exemplary Synthesis of Exemplary Compound 523

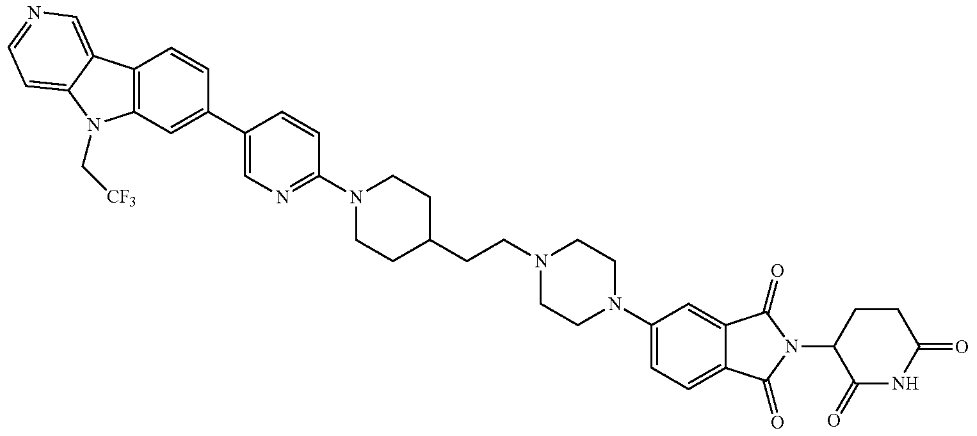 [SMILES: O=C1CCC(N2C(=O)c3ccc(N4CCN(CCC5CCN(c6ccc(-c7ccc8c9cnccc9n(CC(F)(F)F)c8c7)cn6)CC5)CC4)cc3C2=O)C(=O)N1]

Step 1

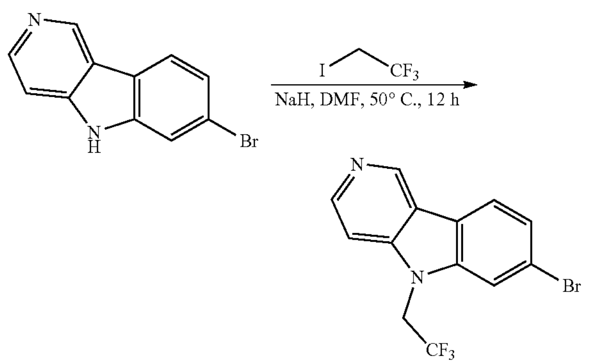

To a solution of 7-bromo-5H-pyrido[4,3-b]indole (200 mg, 0.80 mmol, 1 eq) in N,N-dimethylformamide (2 mL) was added sodium hydride (32 mg, 0.80 mmol, 60% purity, 1 eq). Then to the mixture was added 1,1,1-trifluoro-2-iodo-ethane (169 mg, 0.80 mmol, 1 eq), and the mixture was stirred at 50° C. for 12 h. The reaction mixture was poured into water (10 mL) and extracted with ethyl acetate (10 mL×3). The combined organic layer was washed with brine (10 mL×2), dried over anhydrous sodium sulfate, filtered, and the filtrate was concentrated. The crude product was purified by Prep-HPLC (column: Phenomenex Synergi C18 150*25*10 um; mobile phase: [water (0.225% FA)-ACN]; B %: 20%-50%, 9 min). The desired product, 7-bromo-5-(2,2,2-trifluoroethyl)-5H-pyrido[4,3-b]indole (50 mg, 0.15 mmol), was obtained as a yellow solid.

7-Bromo-5-(2,2,2-trifluoroethyl)-5H-pyrido[4,3-b]indole was converted to the title compound according to the scheme below using procedures described for other examples above as well as known to those skilled in the art.

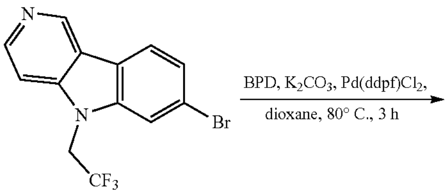

-continued

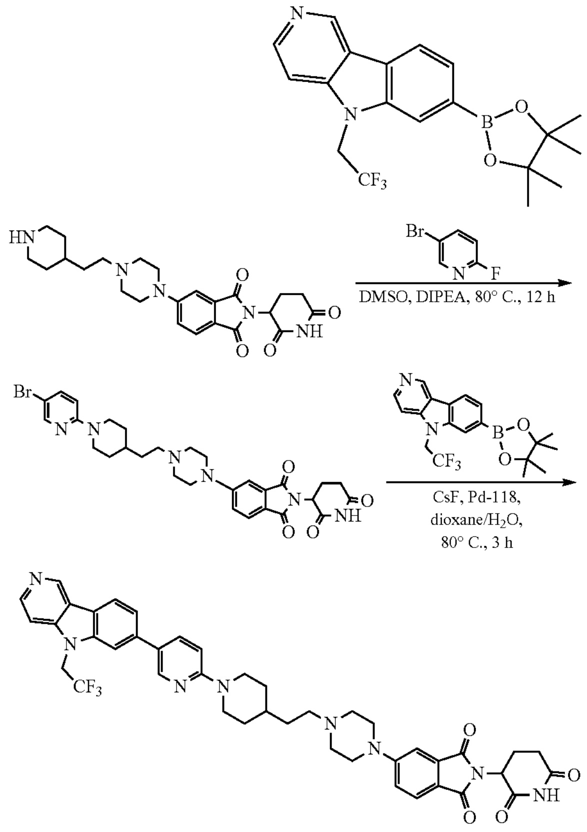

Exemplary Compound 523

Exemplary Synthesis of Exemplary Compound 527

Prepared according to the scheme below using procedures described for other examples above as well as commonly known to those skilled in the art.

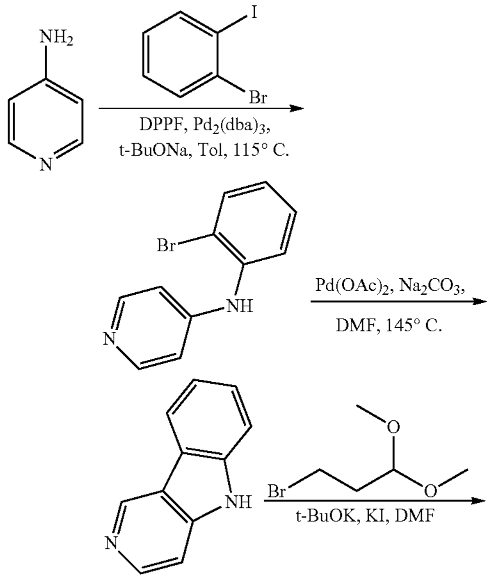

-continued

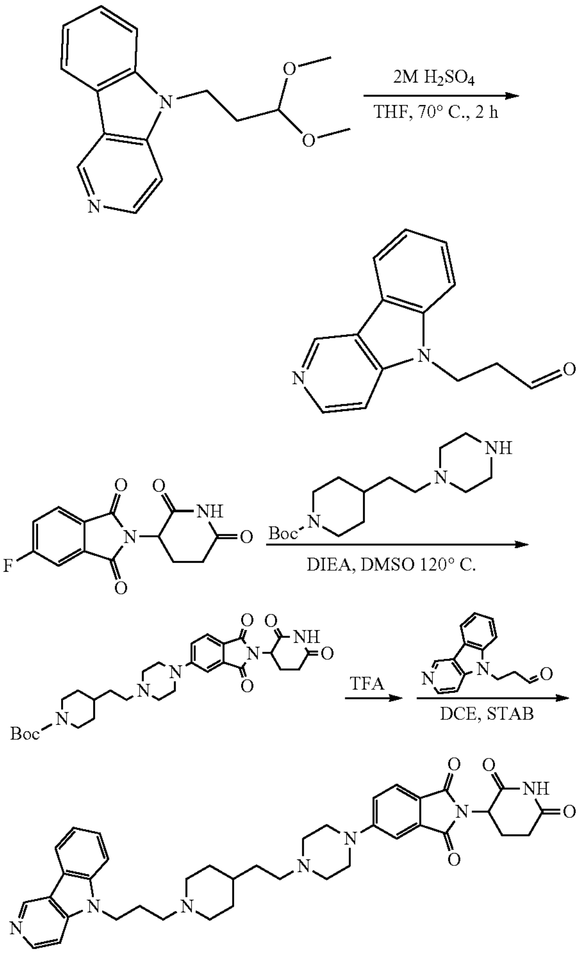

Exemplary compound 527

Using analogous procedures as well as procedures described for other examples above the following exemplary compounds were prepared: 534, 535, 536.

Exemplary Synthesis of Exemplary Compound 528

Prepared according to the scheme below using procedures described for other examples above as well as known to those skilled in the art.

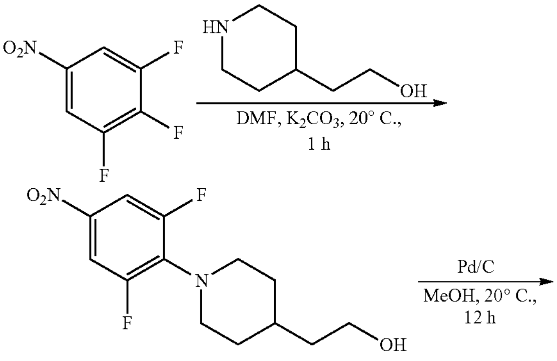

-continued
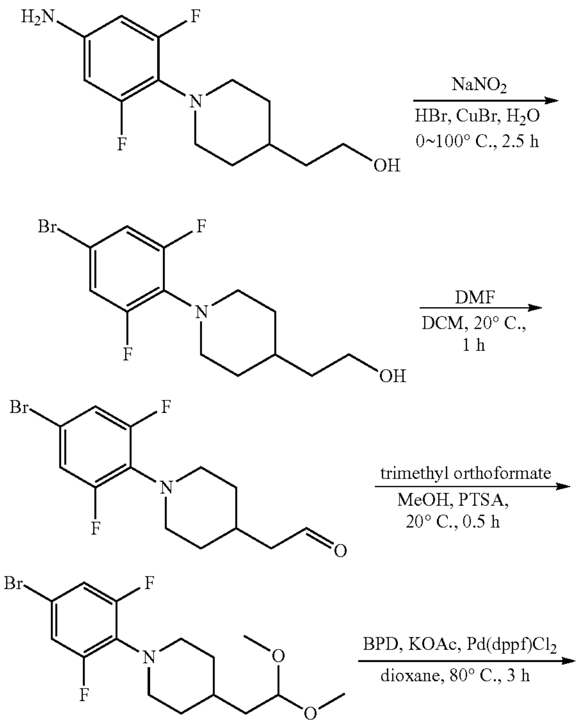
-continued
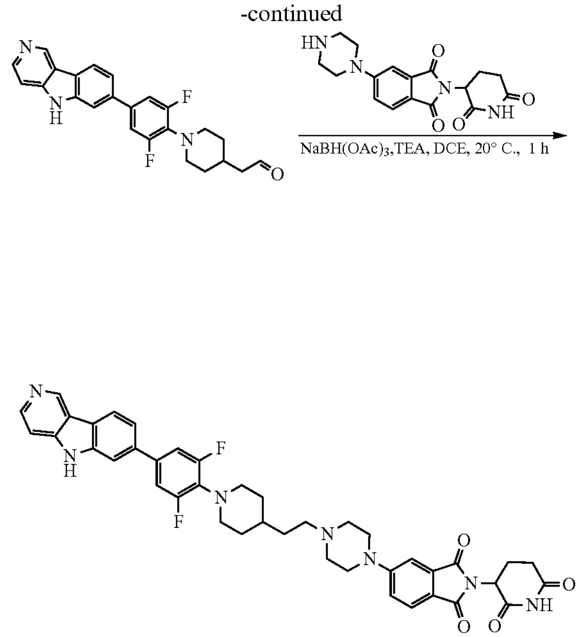
Exemplary Compound 528
Exemplary Synthesis of Exemplary Compound 531
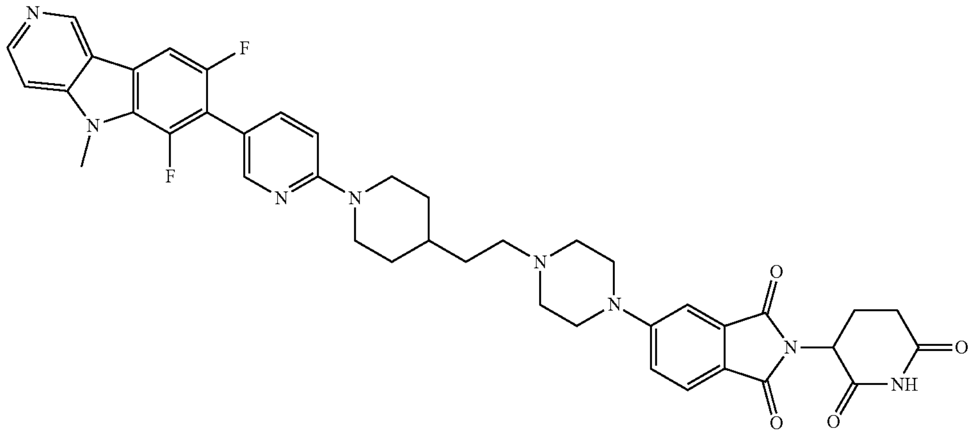 [SMILES: Cn1c2ccncc2c2cc(F)c(-c3ccc(N4CCC(CCN5CCN(c6ccc7c(c6)C(=O)N(C6CCC(=O)NC6=O)C7=O)CC5)CC4)nc3)c(F)c21]
-continued
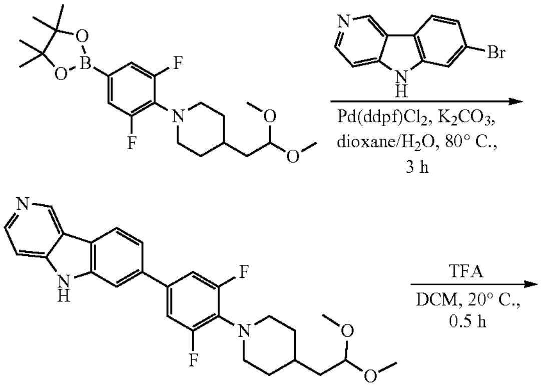
Step 1
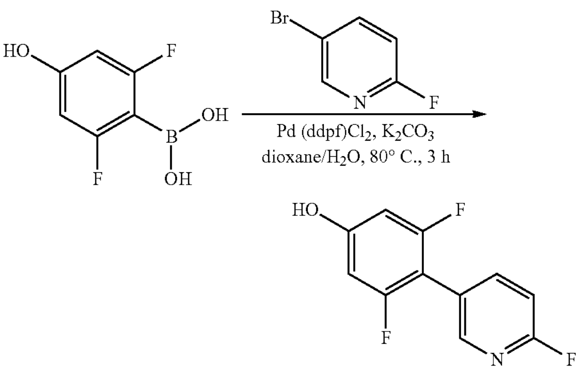

(2,6-difluoro-4-hydroxy-phenyl)boronic acid (2 g, 11.50 mmol, 1 eq), 5-bromo-2-fluoro-pyridine (2.02 g, 11.50 mmol, 1.18 mL, 1 eq), potassium carbonate (3.18 g, 23.00 mmol, 2 eq) and [1,1'-bis(diphenylphosphino)ferrocene]dichloropalladium(ii) (841 mg, 1.15 mmol, 0.1 eq) in dioxane (8 mL) and water (0.8 mL) was degassed and then heated to 80° C. for 3 hours under nitrogen. The reaction mixture was filtered and concentrated under reduced pressure. The residue was purified by silica column chromatography (petroleum ether/ethyl acetate=100/1 to 1/1). 3, 5-difluoro-4-(6-fluoro-3-pyridyl)phenol (1.2 g, 5.33 mmol) was obtained as a pink solid.

Step 2

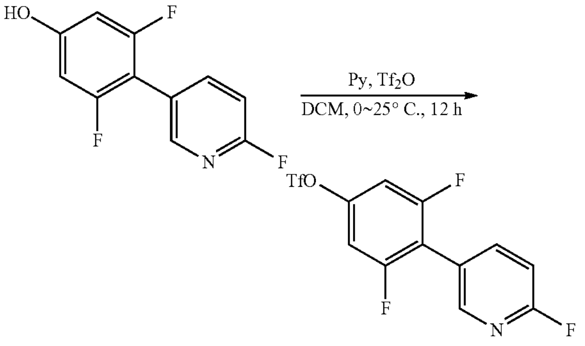

To a solution of 3,5-difluoro-4-(6-fluoro-3-pyridyl)phenol (1.2 g, 5.33 mmol, 1 eq) and pyridine (843 mg, 10.66 mmol, 2 eq) in dichloromethane (20 mL) was added a solution of trifluoromethanesulfonic anhydride (1.80 g, 6.40 mmol, 1.06 mL, 1.2 eq) in dichloromethane (20 mL) at 0° C. The reaction mixture was stirred at 25° C. for 12 h. The reaction mixture was quenched with water (80 mL) and extracted with dichloromethane (80 mL×3). The combined organic layers were washed with brine (100 mL×3), dried over anhydrous sodium sulfate, filtered and concentrated under reduced pressure. The residue was purified by silica column chromatography (Petroleum ether/Ethyl acetate=100/1 to 3/1). [3,5-difluoro-4-(6-fluoro-3-pyridyl)phenyl] trifluoromethanesulfonate (1.4 g, 3.92 mmol) was obtained as a white solid.

[3,5-difluoro-4-(6-fluoro-3-pyridyl)phenyl] trifluoromethanesulfonate was converted to the title compound according to the scheme below using procedures described for other examples above as well as known to those skilled in the art.

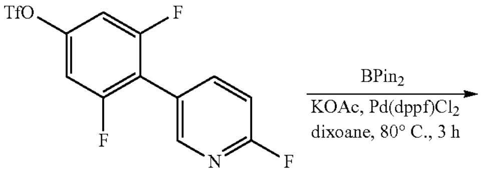

-continued

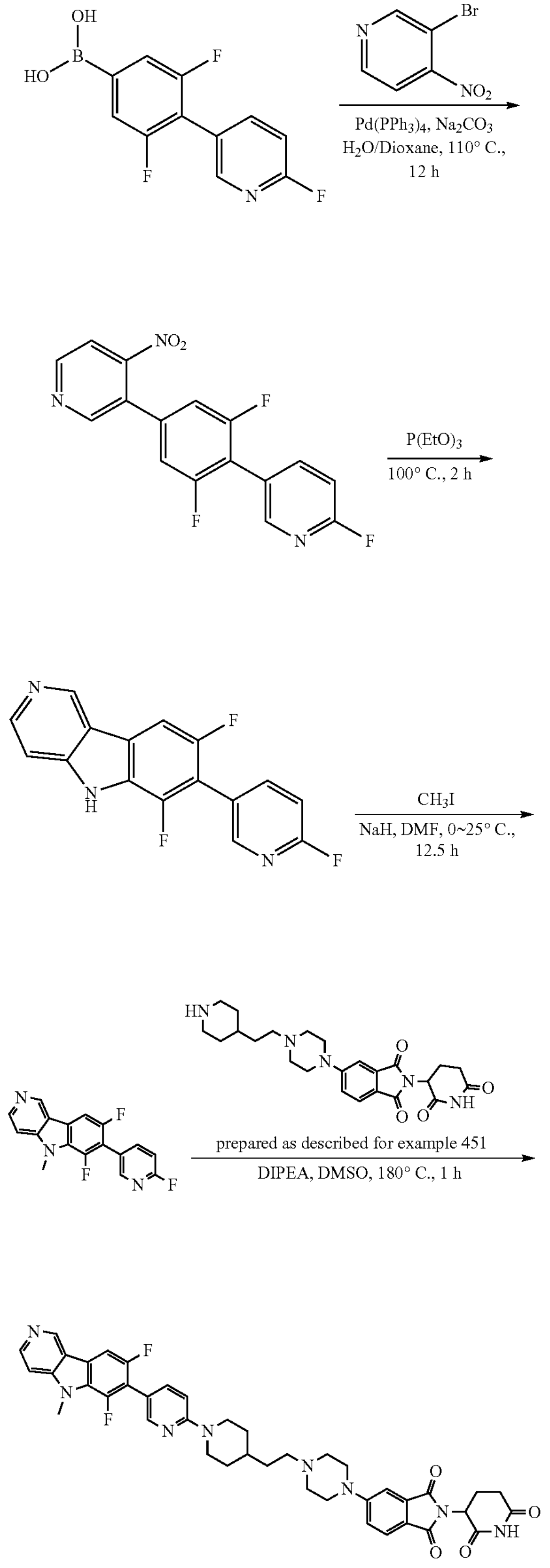

Exemplary Compound 531

Exemplary Synthesis of Exemplary Compound 532

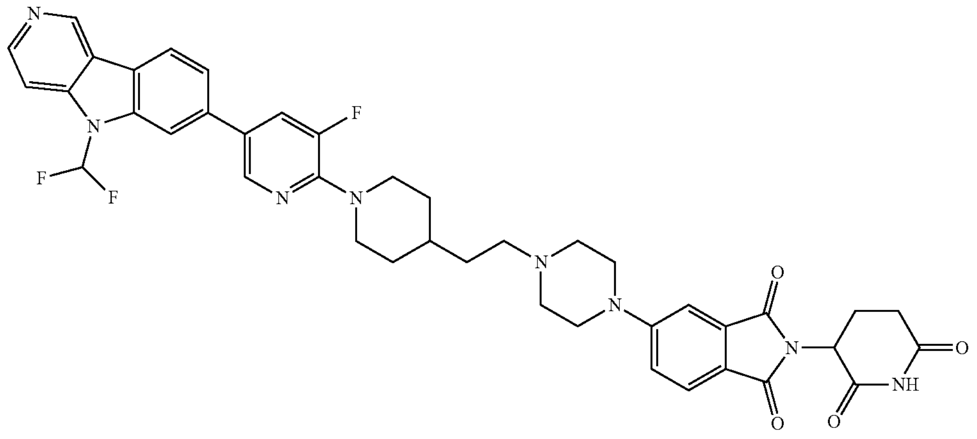 [SMILES: O=C1CCC(N2C(=O)c3ccc(N4CCN(CCC5CCN(c6ncc(-c7ccc8c9cnccc9n(C(F)F)c8c7)cc6F)CC5)CC4)cc3C2=O)C(=O)N1]

Step 1

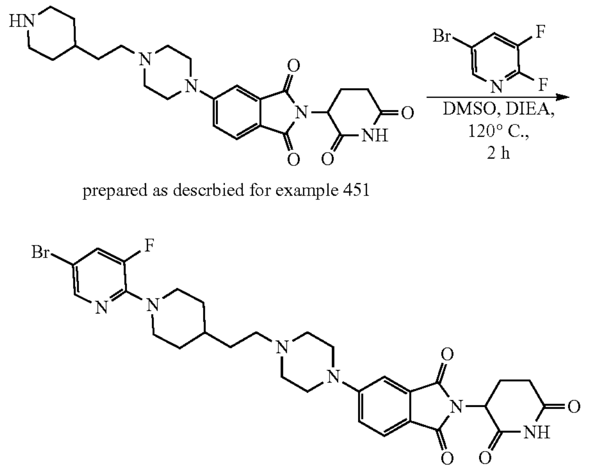 [SMILES: O=C1CCC(N2C(=O)c3ccc(N4CCN(CCC5CCNCC5)CC4)cc3C2=O)C(=O)N1 ; Fc1cc(Br)cnc1F ; O=C1CCC(N2C(=O)c3ccc(N4CCN(CCC5CCN(c6ncc(Br)cc6F)CC5)CC4)cc3C2=O)C(=O)N1]

Step 2

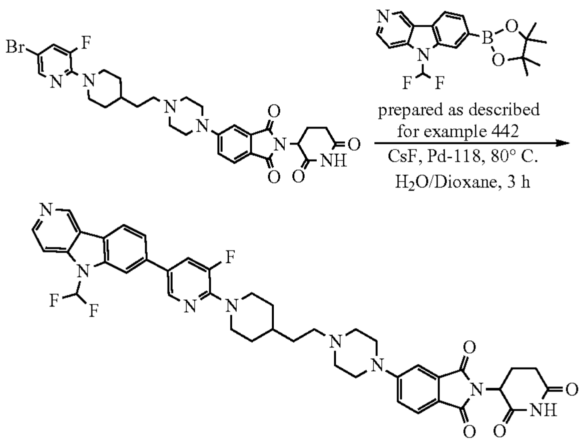

Exemplary Compound 532

To a solution of 2-(2,6-dioxo-3-piperidyl)-5-[4-[2-(4-piperidyl)ethyl]piperazin-1-yl]isoindoline-1,3-dione (500 mg, 1.02 mmol, 1.00 eq, hydrochloric) and 5-bromo-2,3-difluoro-pyridine (217 mg, 1.12 mmol, 1.10 eq) in dimethylsulfoxide (8 mL) was added diisopropylethyllamine (395 mg, 3.06 mmol, 3.00 eq). The mixture was stirred at 120° C. for 2 hours. The reaction mixture was diluted with water (20 mL) and extracted with ethyl acetate (30 mL×3). The combined organic layers were washed with brine (30 mL×3), dried over sodium sulfate anhydrous, filtered and concentrated under reduced pressure. The residue was purified by silica gel chromatography (dichloromethane:methyl alcohol=100:0 to 20:1) to give 5-[4-[2-[1-(5-bromo-3-fluoro-2-pyridyl)-4-piperidyl]ethyl]piperazin-1-yl]-2-(2,6-dioxo-3-piperidyl)isoindoline-1,3-dione (350 mg, 0.55 mmol) as a yellow solid.

5-[4-[2-[1-(5-bromo-3-fluoro-2-pyridyl)-4-piperidyl]ethyl]piperazin-1-yl]-2-(2,6-dioxo-3-piperidyl)isoindoline-1,3-dione (200 mg, 0.31 mmol, 1.00 eq), 5-(difluoromethyl)-7-(4,4,5,5-tetramethyl-1,3,2-dioxaborolan-2-yl)pyrido[4,3-b]indole (109 mg, 0.31 mmol, 1.00 eq), cesium fluoride (96 mg, 0.63 mmol, 2.00 eq) and dichloro[1,1'-bis(di-tert-butylphosphino)ferrocene] palladium(II) (20 mg, 0.031 mmol, 0.10 eq) in dioxane (5 mL) and water (0.5 mL) was degassed and then heated to 80° C. for 3 h under nitrogen. The residue was purified by preparative HPLC (column: Phenomenex luna C18 150*25 mm*10 um; mobile phase: [water (0.1% trifluoroacetate)-methyl cyanide]; B %: 10%-40%, 10 min) to give 5-[4-[2-[1-[5-[5-(difluoromethyl)pyrido[4,3-b]indol-7-yl]-3-fluoro-2-pyridyl]-4-piperidyl]ethyl]piperazin-1-yl]-2-(2,6-dioxo-3-piperidyl)isoindoline-1,3-dione trifluoroacetate (100.3 mg, 0.11 mmol) as a yellow solid.

Exemplary Synthesis of Exemplary Compound 533

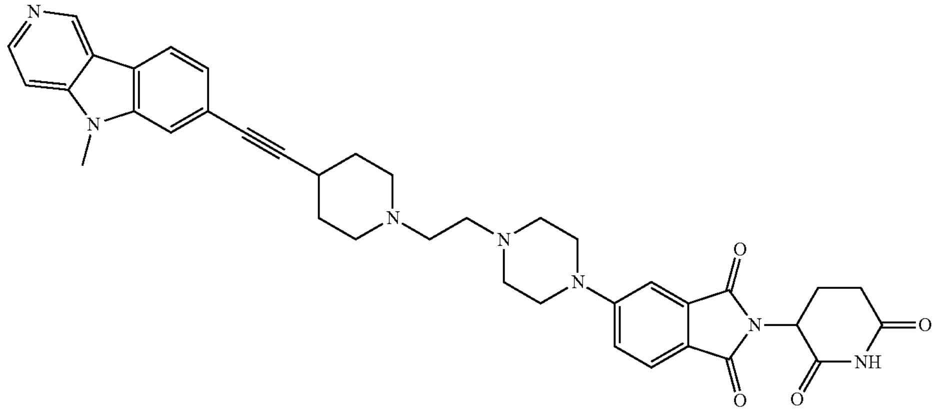 [SMILES: Cn1c2ccncc2c2ccc(C#CC3CCN(CCN4CCN(c5ccc6c(c5)C(=O)N(C5CCC(=O)NC5=O)C6=O)CC4)CC3)cc21]

Step 1

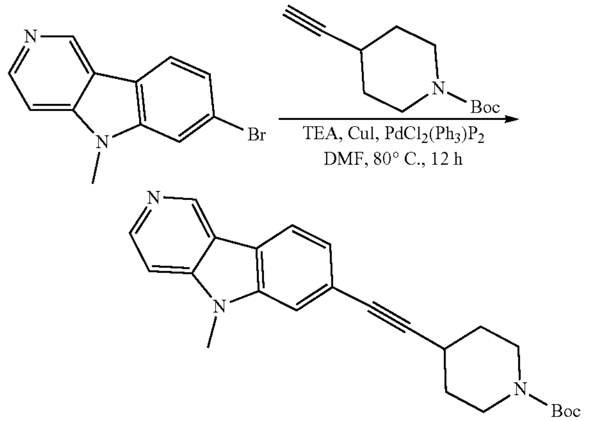

To a solution of 7-bromo-5-methyl-pyrido[4,3-b]indole (200 mg, 0.76 mmol, 1 eq) and tert-butyl 4-ethynylpiperidine-1-carboxylate (320 mg, 1.53 mmol, 2 eq) in N,N-dimethylformamide (4 mL) was added triethylamine (233 mg, 2.30 mmol, 3 eq), copper iodide (14.6 mg, 76.6 umol, 0.1 eq) and bis(triphenylphosphine)palladium dichloride (108 mg, 0.15 mmol, 0.2 eq), then the mixture was stirred at 80° C. under nitrogen atmosphere for 12 hours. The solution was concentrated in the vacuum. The residue was purified by prep-TLC (dichloromethane/methanol=10/1) The product tert-butyl 4-[2-(5-methylpyrido[4,3-b]indol-7-yl)ethynyl]piperidine-1-carboxylate (180 mg, 0.45 mmol) was obtained as a yellow solid.

tert-butyl 4-[2-(5-methylpyrido[4,3-b]indol-7-yl)ethynyl] piperidine-1-carboxylate was converted to the title compound according to the scheme below using procedures described for other examples above as well as known to those skilled in the art.

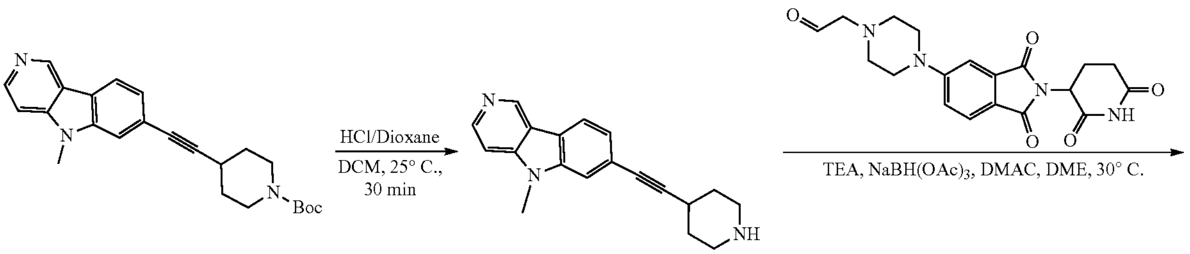

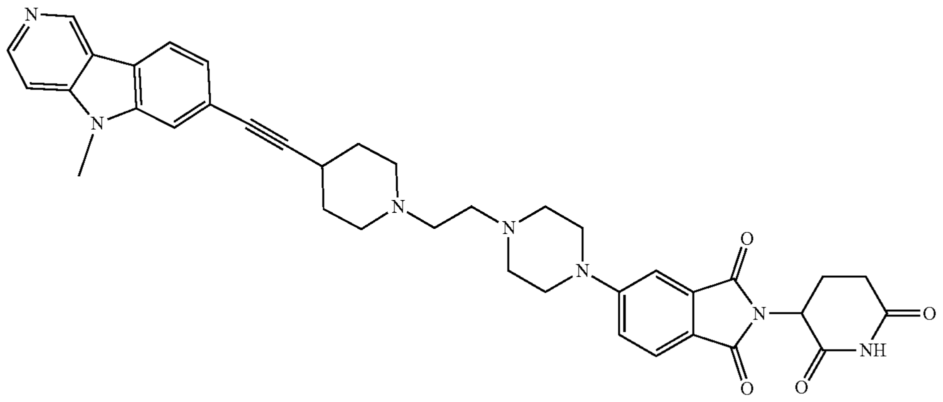

Exemplary Compound 533

Exemplary Synthesis of Exemplary Compound 537

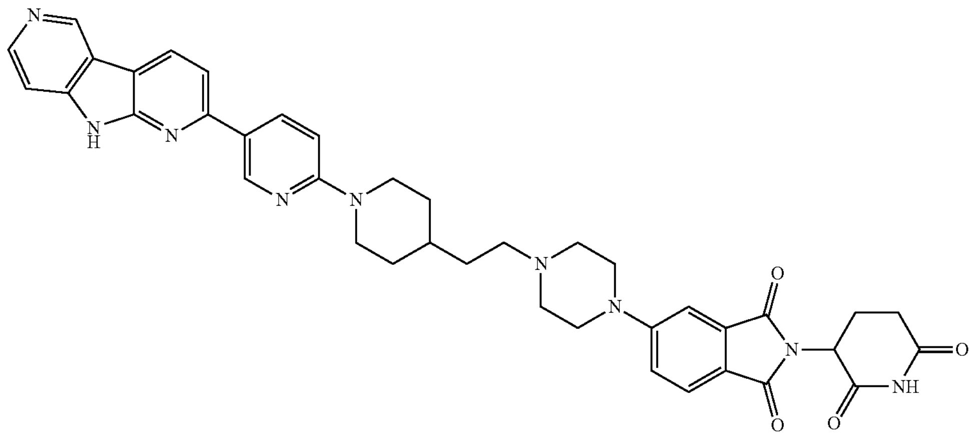 [SMILES: O=C1CCC(N2C(=O)c3ccc(N4CCN(CCC5CCN(c6ccc(-c7ccc8c(n7)[nH]c7ccncc78)cn6)CC5)CC4)cc3C2=O)C(=O)N1]

Step 1

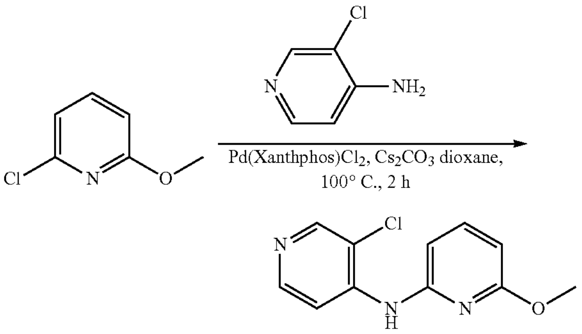

A mixture of 2-chloro-6-methoxy-pyridine (2.0 g, 13.93 mmol, 1.0 equiv), $Cs_2CO_3$ (6.35 g, 19.48 mmol, 1.4 equiv), dichloro[9,9-dimethyl-4,5-bis(diphenyl-phosphino)xanthene]palladium(II) (0.53 g, 0.70 mmol, 0.05 equiv) and 3-chloropyridin-4-amine (2.15 g, 16.73 mmol, 1.2 equiv) in dioxane (15 ml) was stirred for 2 h at 100° C. under nitrogen atmosphere. The resulting mixture was extracted with EtOAc. The combined organic layers were washed with water, dried over anhydrous $Na_2SO_4$. After filtration, the filtrate was concentrated under reduced pressure. The residue was purified by silica gel column chromatography, eluted with $CH_2Cl_2$/MeOH (12:1) to afford 3-chloro-N-(6-methoxypyridin-2-yl)pyridin-4-amine (2.8 g) as a yellow solid.

Step 2

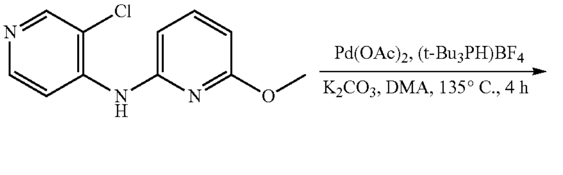

-continued

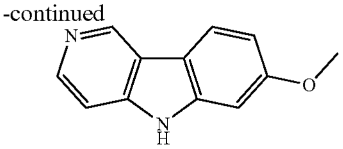

A mixture of 3-chloro-N-(6-methoxypyridin-2-yl)pyridin-4-amine (2.80 g, 11.9 mmol, 1.0 equiv), $K_2CO_3$ (3.28 g, 23.77 mmol, 2.0 equiv), $Pd(OAc)_2$ (0.13 g, 0.58 mmol, 0.05 equiv) and t-$Bu_3P$-$HBF_4$ (0.21 g, 0.72 mmol, 0.06 equiv) in DMA (20 mL) was stirred for 4 h at 135° C. in an oil bath under nitrogen atmosphere. The resulting mixture was extracted with EtOAc. The combined organic layers were washed with water, dried over anhydrous $Na_2SO_4$. After filtration, the filtrate was concentrated under reduced pressure. The residue was purified by silica gel column chromatography, eluted with $CH_2Cl_2$/MeOH (12:1) to afford 2-methoxy-9H-pyrrolo[2,3-b:4,5-c']dipyridine (1.80 g) as a yellow solid.

Step 3

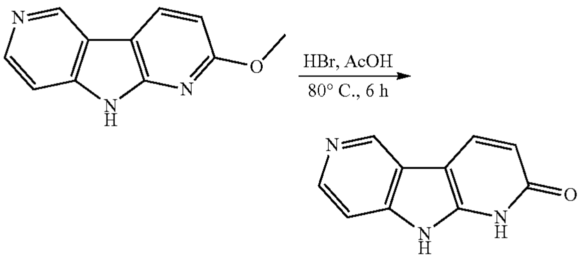

A mixture of 2-methoxy-9H-pyrrolo[2,3-b:4,5-c']dipyridine (1.80 g, 9.0 mmol, 1.0 equiv), and HBr (33 wt % in AcOH, 3.0 mL) in AcOH (6.0 mL) was stirred for 6 h at 80° C. in an oil bath under nitrogen atmosphere. The precipitated solids were collected by filtration and washed with EtOAc to afford 1,9-dihydro-2H-pyrrolo[2,3-b:4,5-c']dipyridin-2-one hydrobromide (1.5 g) as a yellow solid.

Step 4

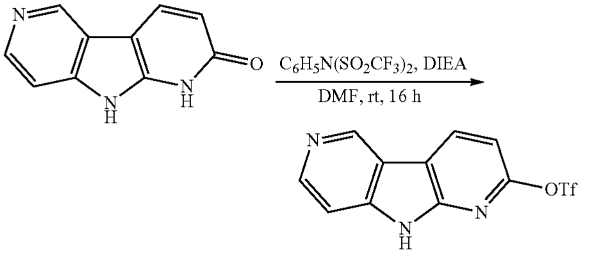

A mixture of 1,9-dihydro-2H-pyrrolo[2,3-b:4,5-c']dipyridin-2-one hydrobromide (1.50 g, 5.64 mmol, 1.0 equiv), 1,1,1-trifluoro-N-phenyl-N-trifluoromethanesulfonylmethanesulfonamide (4.03 g, 11.28 mmol, 2.0 equiv) and DIEA (3.13 g, 24.2 mmol, 4.3 equiv) in DMF (12 ml) was stirred for 16 h at room temperature under nitrogen atmosphere. The orange suspension was treated with $KHCO_3$ (aq) and water (40 mL) and stirred at 50° C. for 18 h. Water (100 mL) was added slowly and the mixture was cooled to 0-5° C. and stirred at that temperature for 90 min. The precipitate was filtered off, washed with water (50 mL) and n-heptane (20 mL) and dried in vacuum to obtain (1.95 g, crude) 9H-pyrrolo[2,3-b:4,5-c']dipyridin-2-yl trifluoromethanesulfonate as a light-yellow solid.

9H-pyrrolo[2,3-b:4,5-c']dipyridin-2-yl trifluoromethanesulfonate was converted to the title product according to the scheme below using procedures described for other examples above as well as common procedures known to those skilled in the art.

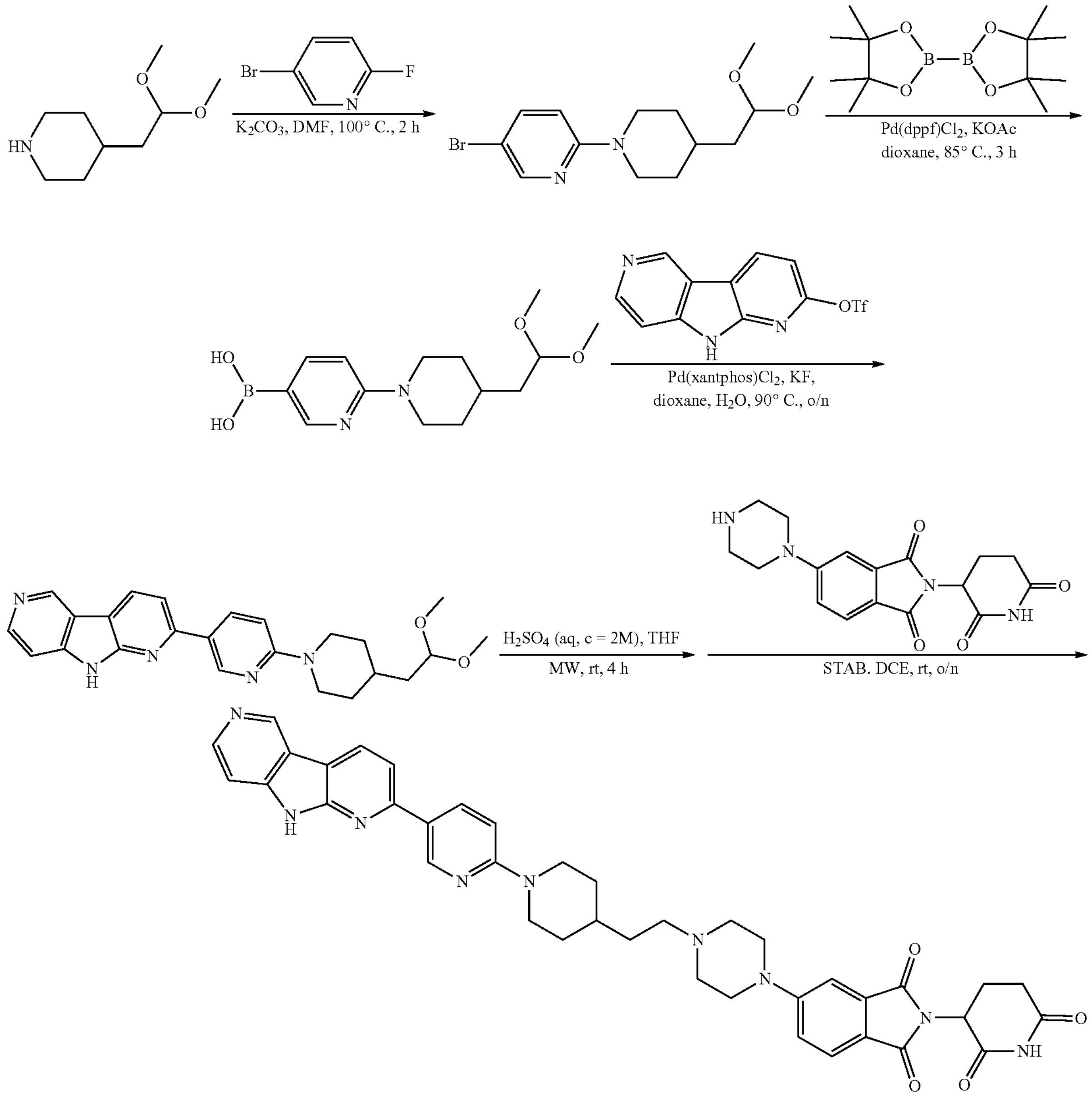

Exemplary Compound 537

Using analogous procedures the following exemplary compound was prepared: 538.

Exemplary Synthesis of Exemplary Compound 478

Prepared according to the schemes below using procedures described for other examples above as well as general procedures known to those skilled in the art.

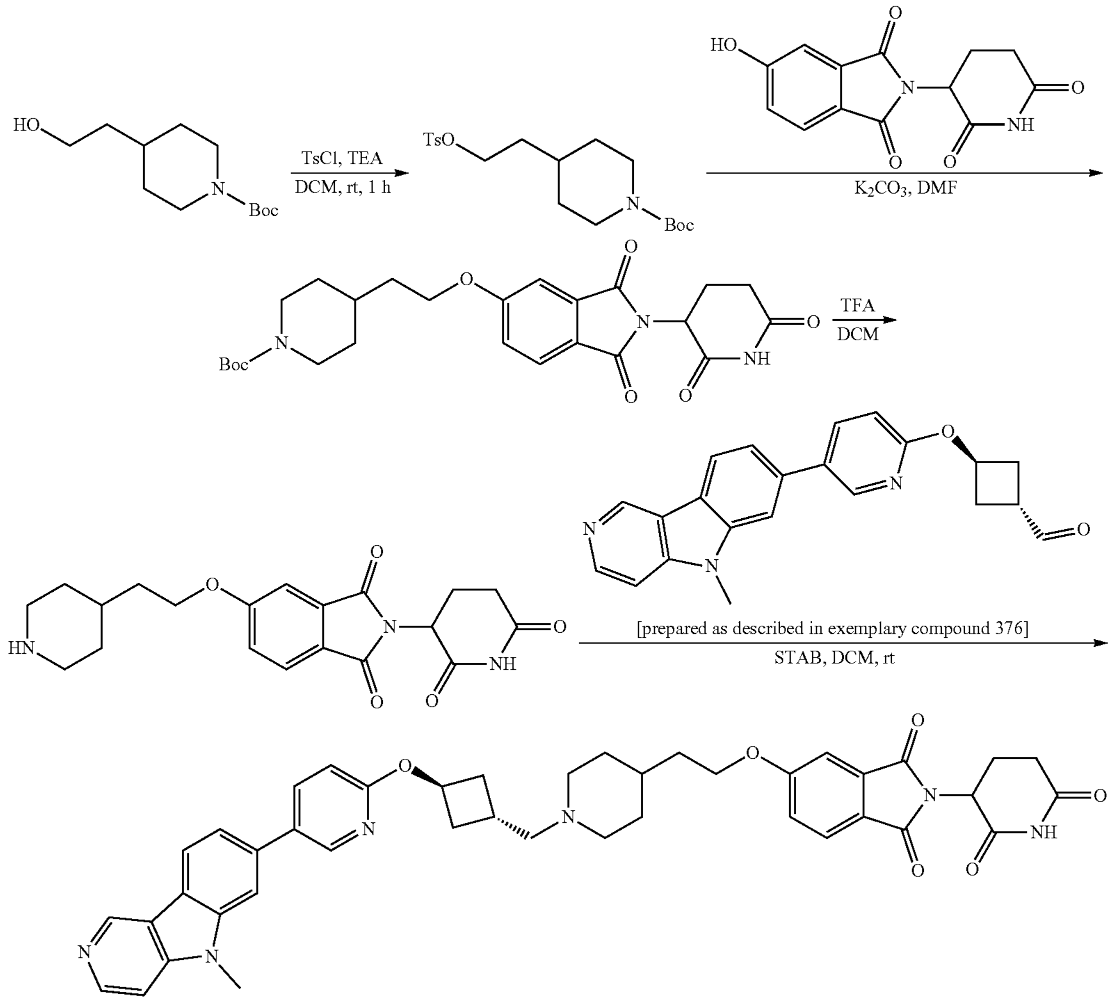

Exemplary Compound 478

Exemplary Synthesis of Exemplary Compound 498

Prepared according to the scheme below using procedures described for other examples above as well as general procedures known to those skilled in the art.

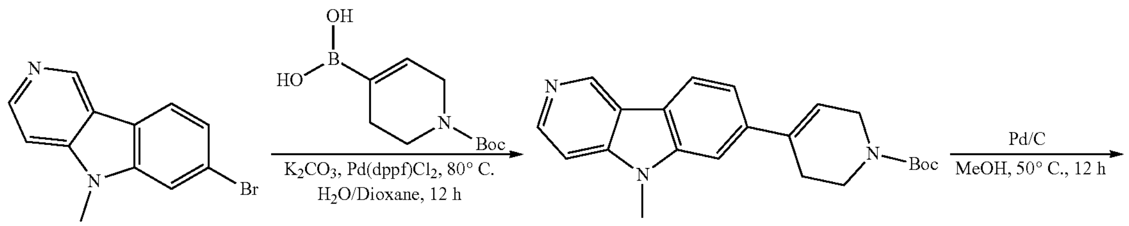

-continued
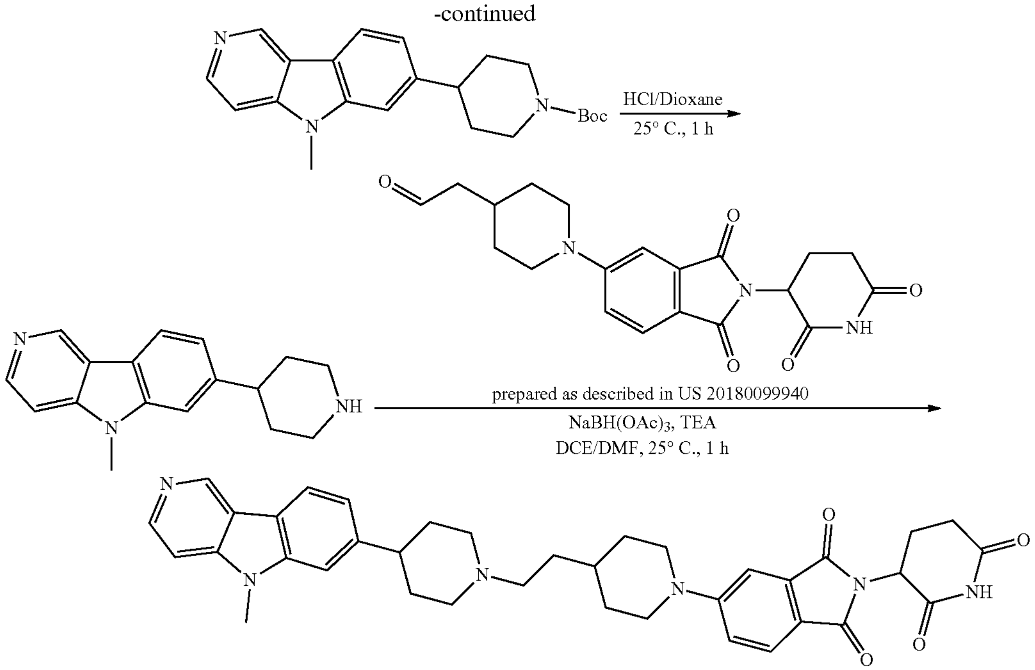
Exemplary Compound 498
Exemplary Synthesis of Exemplary Compound 502
Prepared according to the scheme below using procedures described for other examples above as well as general procedures known to those skilled in the art.
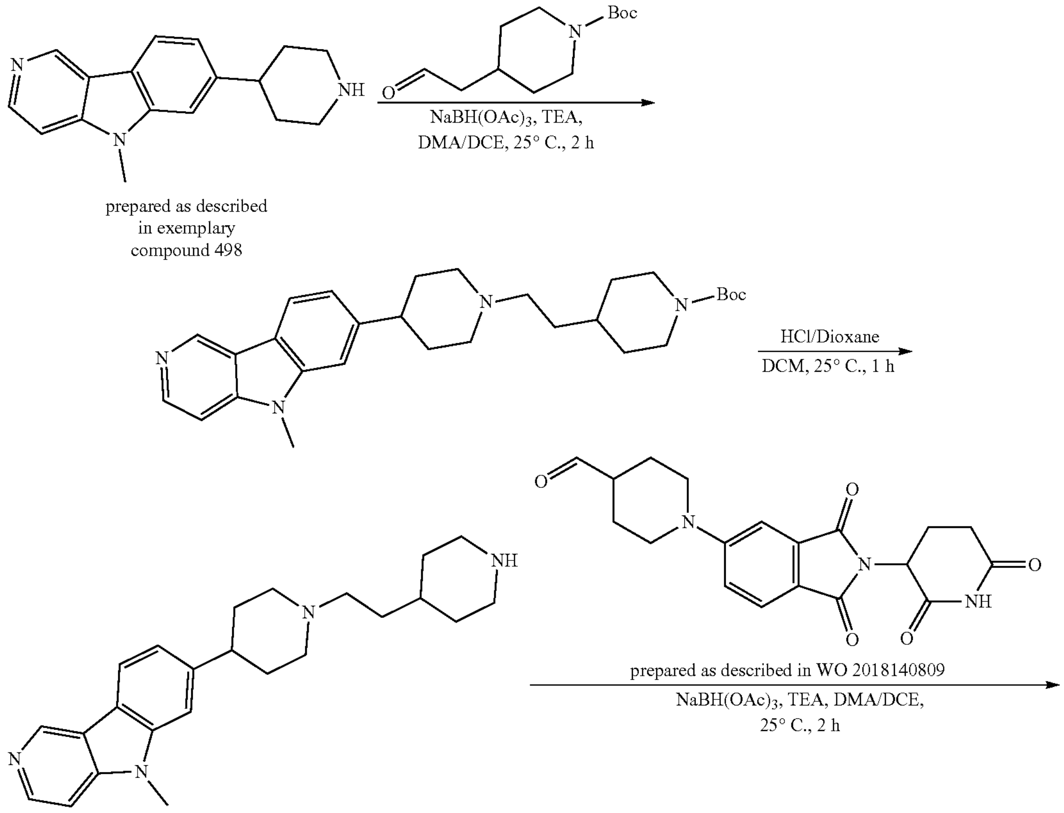

-continued
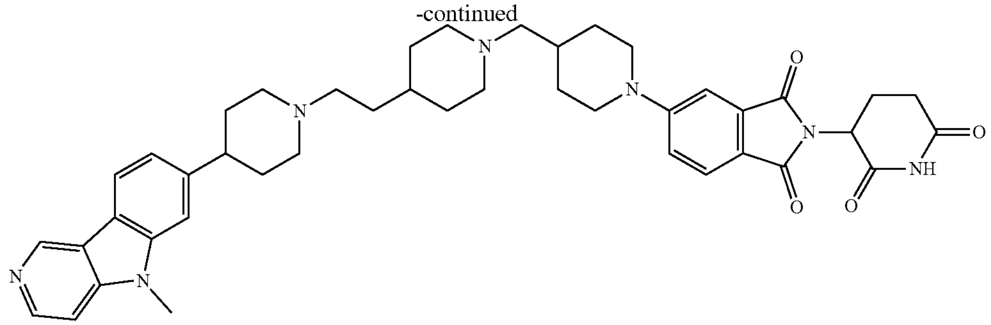
Exemplary Compound 502
Exemplary Synthesis of Exemplary Compound 508
Prepared according to the scheme below using procedures described for other examples above as well as general procedures known to those skilled in the art.
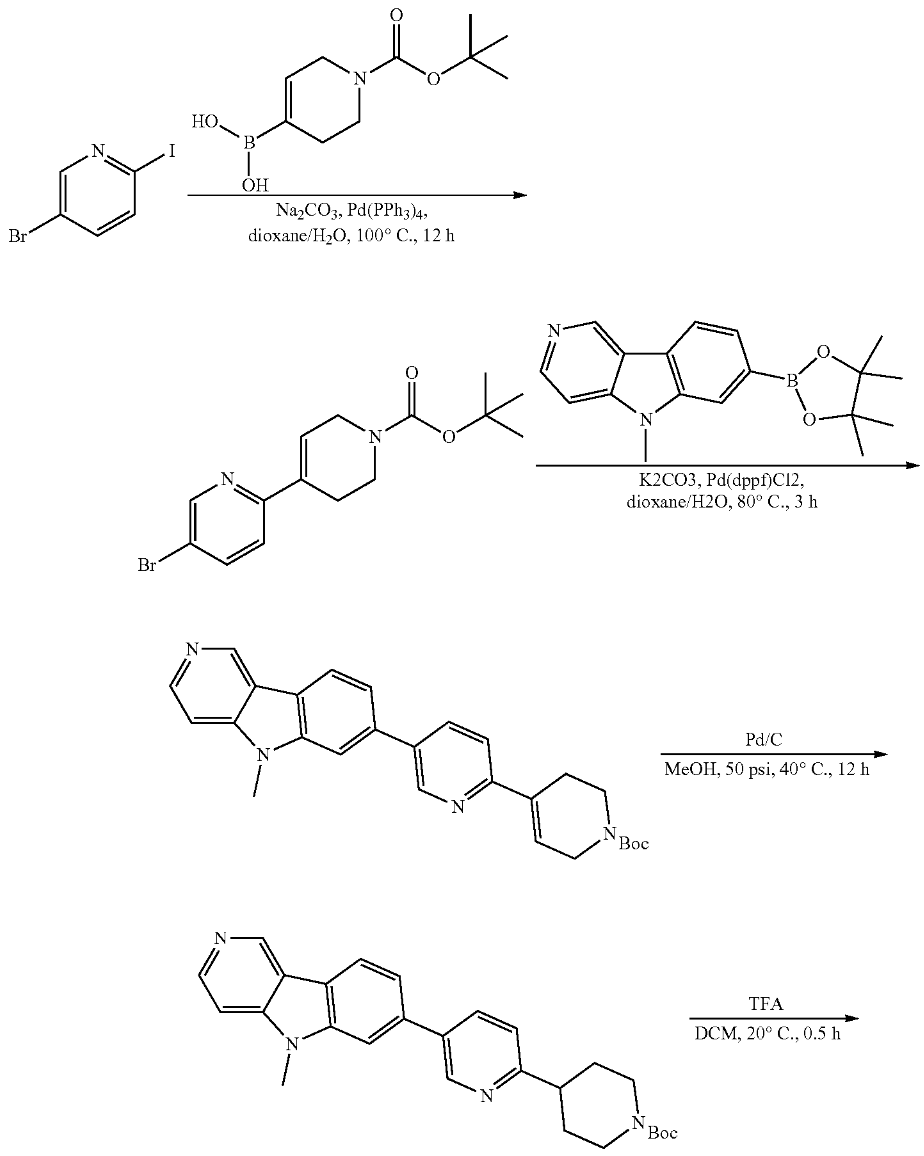

-continued
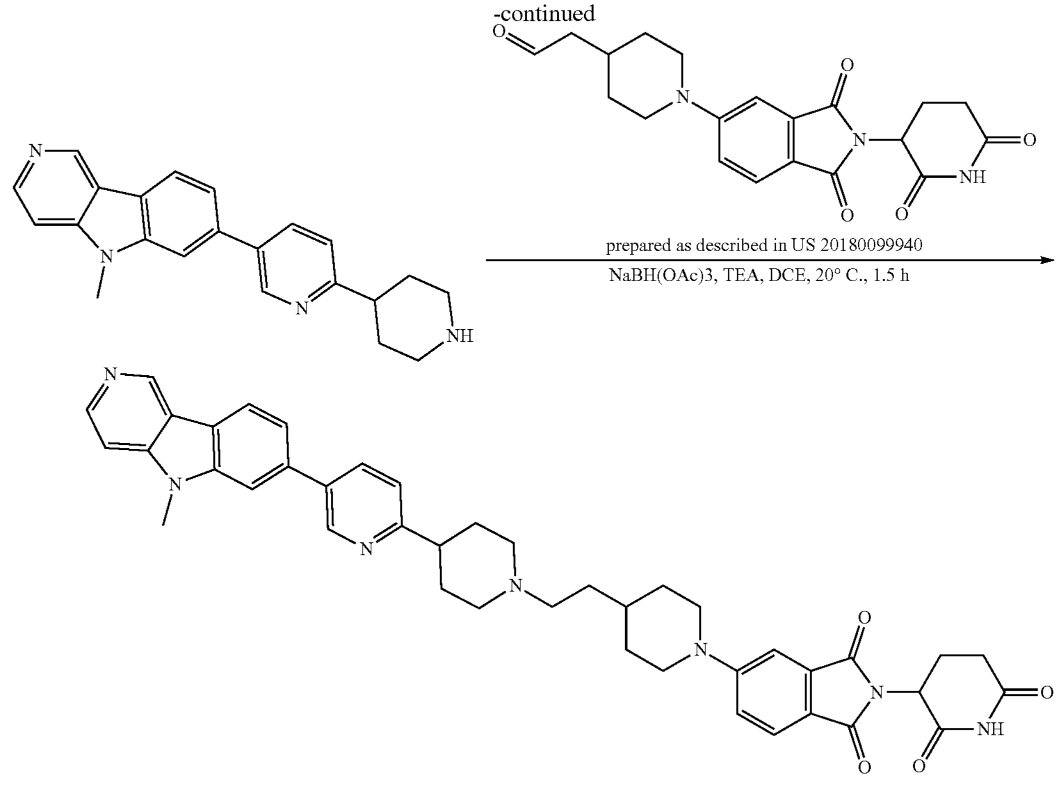
Exemplary Compound 508
Exemplary Synthesis of Exemplary Compound 550 and 559
Prepared according to the scheme below using procedures described for other examples above as well as general procedures known to those skilled in the art.
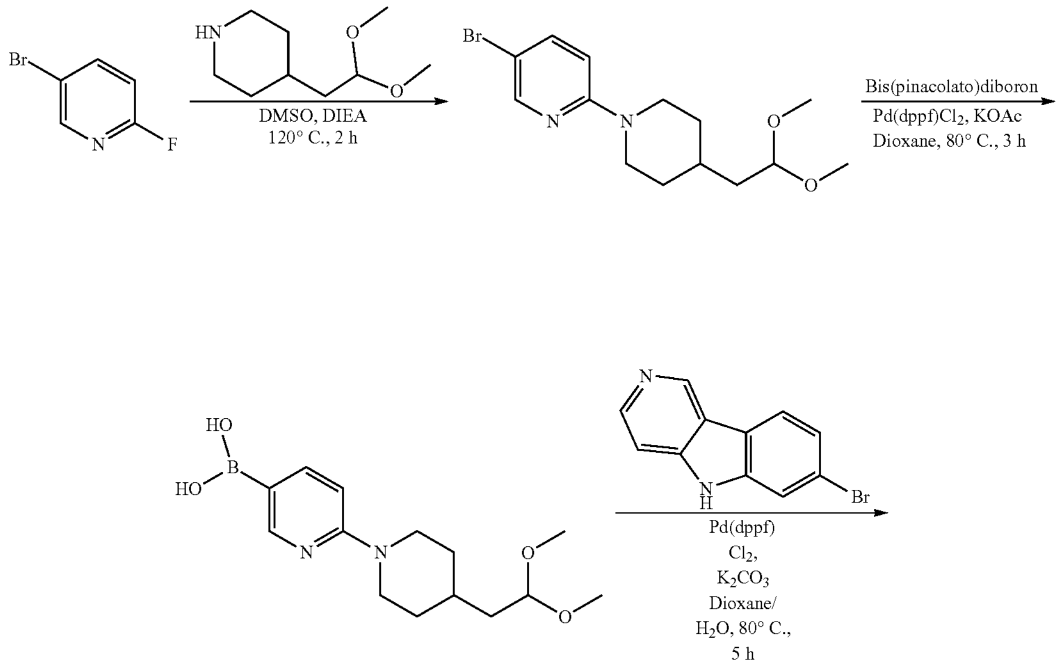

-continued
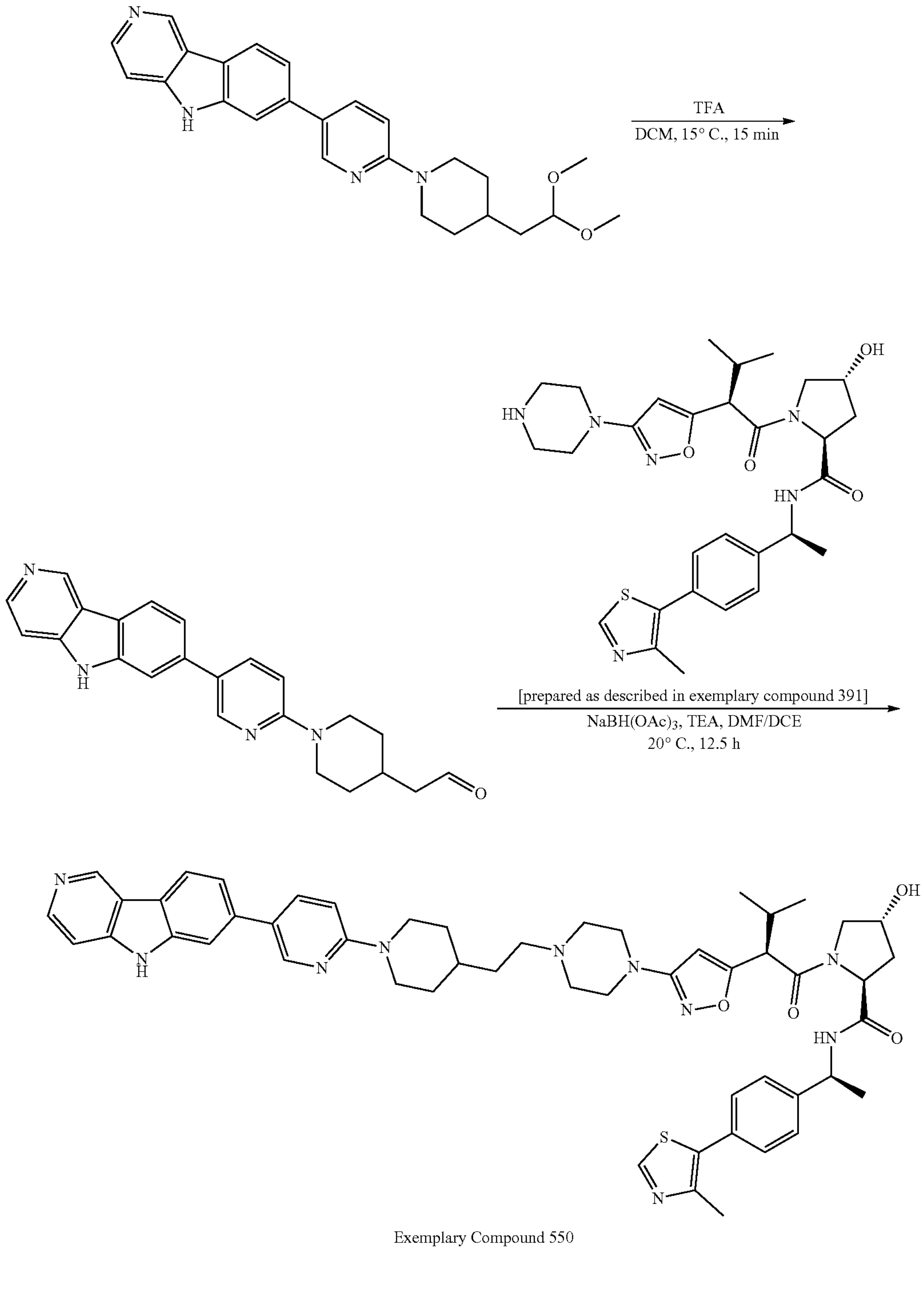
Exemplary Compound 550
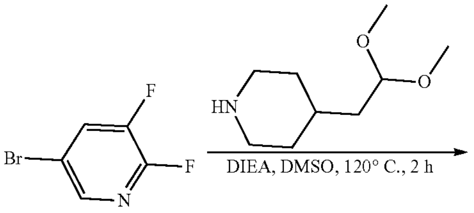

-continued
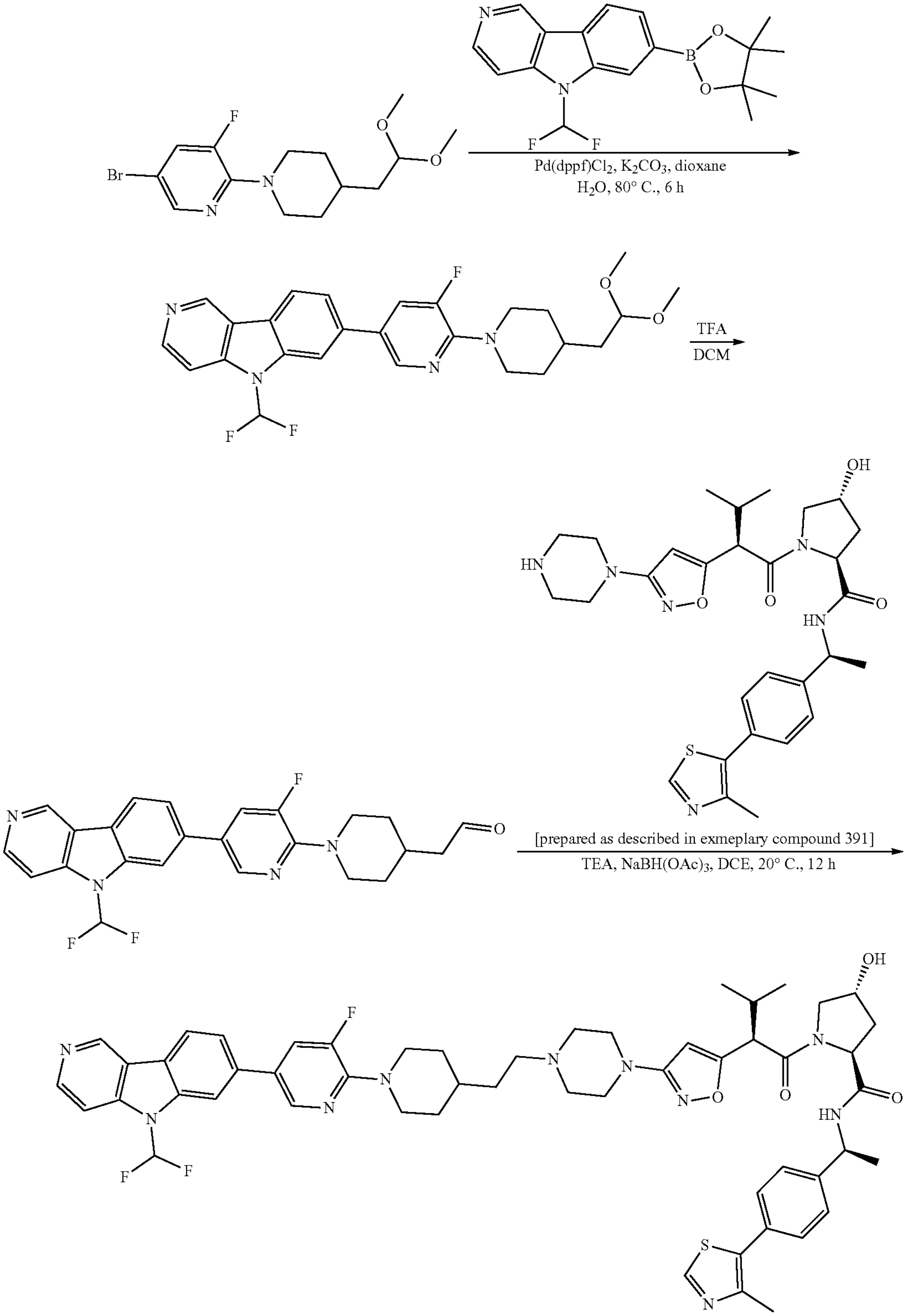
Exemplary Compound 559
Exemplary Synthesis of Exemplary Compound 569
Prepared according to the scheme below using procedures described for other examples above as well as general procedures known to those skilled in the art.

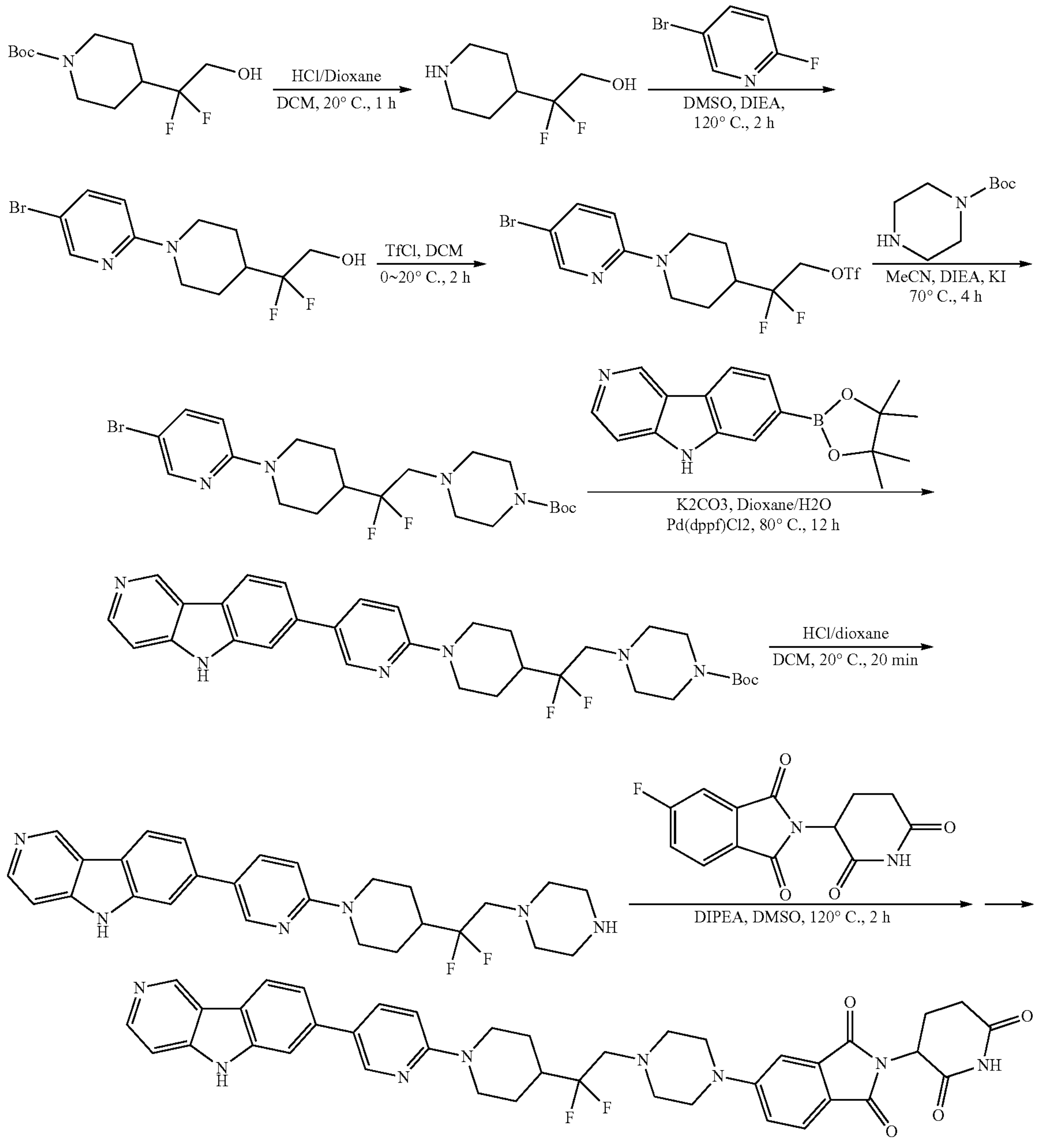
Exemplary Compound 569
Exemplary Synthesis of Exemplary Compound 576
Prepared according to the schemes below using procedures described for Exemplary Compound 583 and other examples above as well as general procedures known to those skilled in the art.
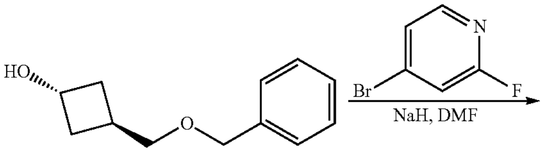

-continued

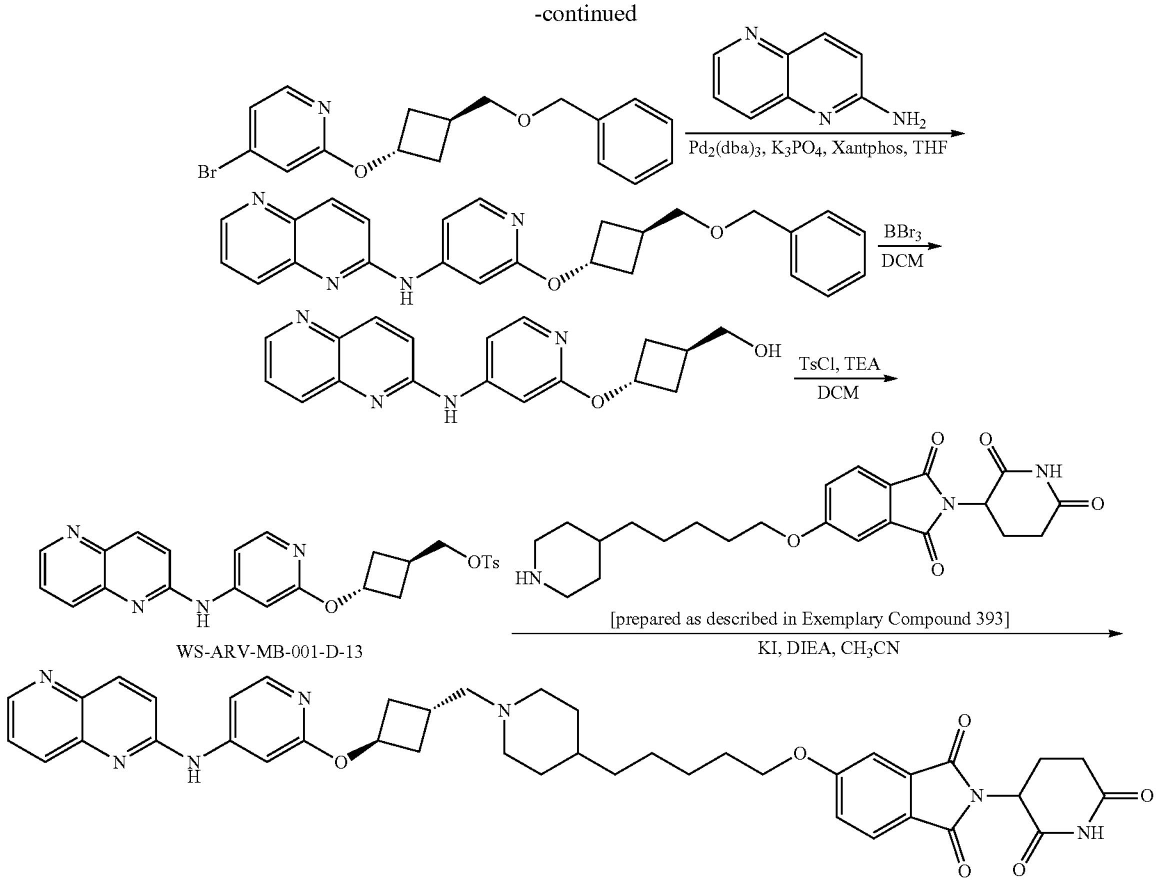

Exemplary Compound 576

Using analogous procedures and those of Exemplary Compound 478, Exemplary Compound 577 was prepared.

Exemplary Synthesis of Exemplary Compound 578

Step 1

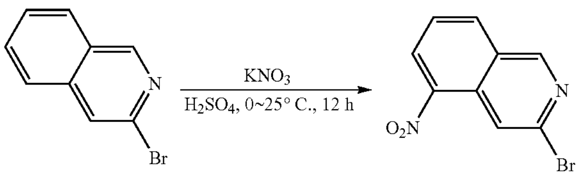

To a solution of 3-bromoisoquinoline (1 g, 4.81 mmol, 1 eq) in sulfuric acid (24 mL) was added dropwise a solution of potassium nitrate (485 mg, 4.81 mmol, 1 eq) in sulfuric acid (5 mL) at 0° C. The reaction was stirred at 25° C. for 12 h. The reaction mixture was poured into ice water (300 mL). The precipitate that formed was collected by filtration and dried under reduced pressure. 3-bromo-5-nitro-isoquinoline (1 g, 3.95 mmol, 82% yield) was obtained as a yellow solid.

Step 2

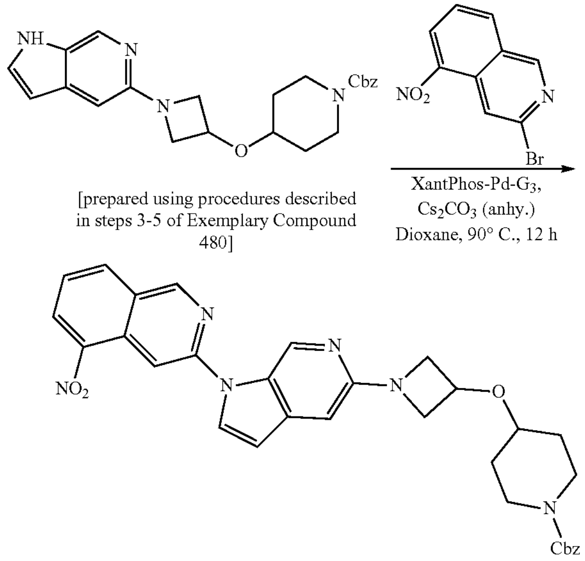 [SMILES: c1cc2cc(N3CC(OC4CCNCC4)C3)ncc2[nH]1 ; O=[N+]([O-])c1cccc2cnc(Br)cc12 ; O=C(OCc1ccccc1)N1CCC(OC2CN(c3cc4ccn(-c5cc6c([N+](=O)[O-])cccc6cn5)c4cn3)C2)CC1]

Benzyl 4-[1-(1H-pyrrolo[2,3-c]pyridin-5-yl)azetidin-3-yl]oxypiperidine-1-carboxylate (400 mg, 0.98 mmol, 1 eq), 3-bromo-5-nitro-isoquinoline (249 mg, 0.98 mmol, 1 eq), cesium carbonate (961 mg, 2.95 mmol, 3 eq) and methanesulfonato[9,9-dimethyl-4,5-bis (diphenylphosphino)xanthene][2-amino-1,1-biphenyl]palladium(II) (93 mg, 0.09 mmol, 0.1 eq) in dioxane (8 mL) were degassed and then heated to 90° C. for 16 h under nitrogen. The reaction mixture was diluted with dichloromethane (100 mL), filtered and washed with brine (80 mL×3), dried over anhydrous sodium sulfate, filtered and concentrated under reduced pressure. The residue was purified by silica gel column chromatography (dichloromethane/methanol=100/1 to 10/1). Benzyl 4-[1-[1-(5-nitro-3-isoquinolyl)pyrrolo[2,3-c]pyridin-5-yl]azetidin-3-yl]oxypiperidine-1-carboxylate (480 mg, 0.82 mmol, 84% yield) was obtained as a red solid.

Benzyl 4-[1-[1-(5-nitro-3-isoquinolyl)pyrrolo[2,3-c]pyridin-5-yl]azetidin-3-yl] oxypiperidine-1-carboxylate was converted to the title compound according to the scheme below using procedures described for other examples above as well as general procedures known to those skilled in the art.

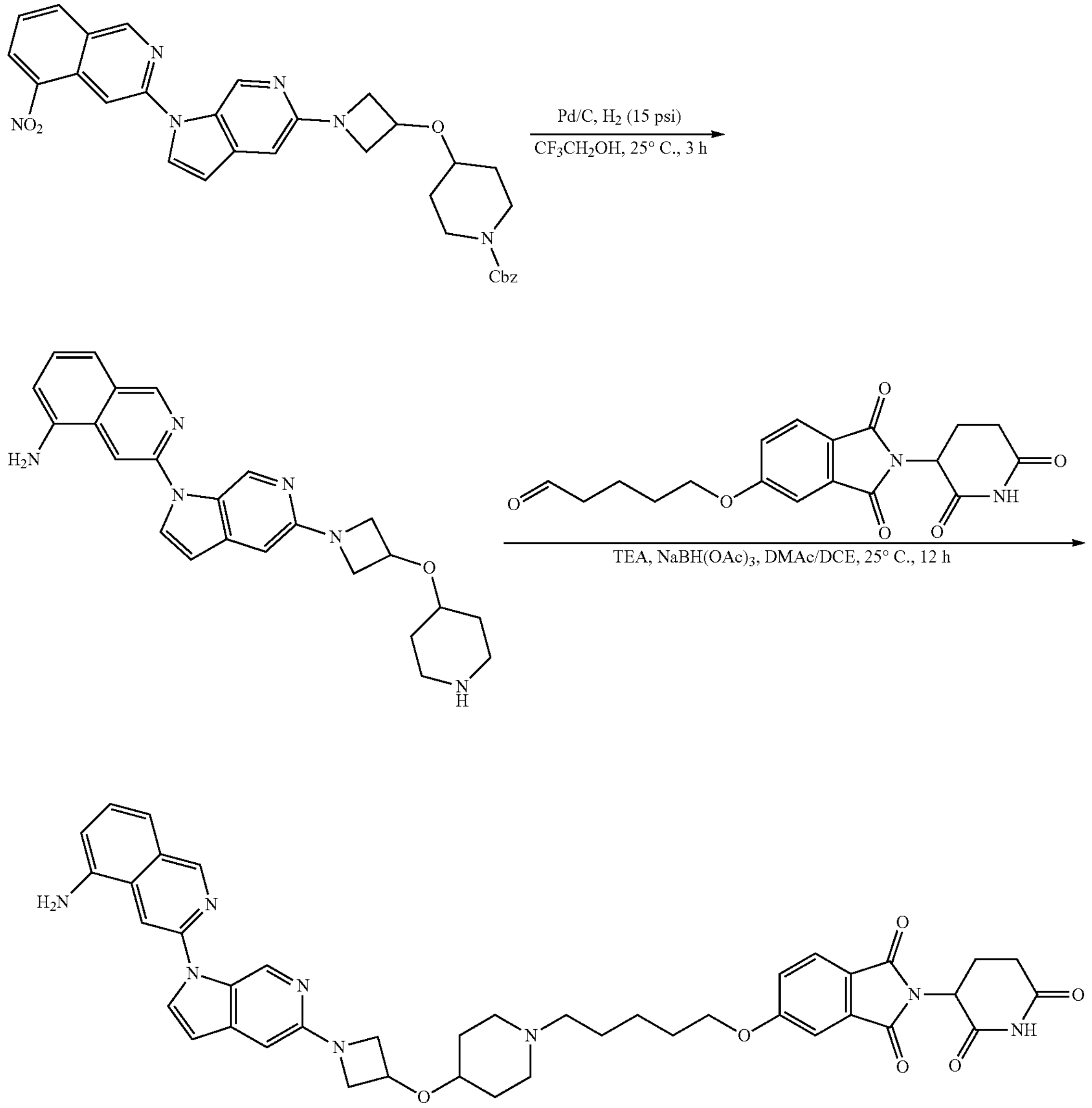

Exemplary Compound 578

Using analogous procedures and those of Exemplary Compound 512, Exemplary Compound 5050 was prepared.

Exemplary Synthesis of Exemplary Compound 579

Step 1

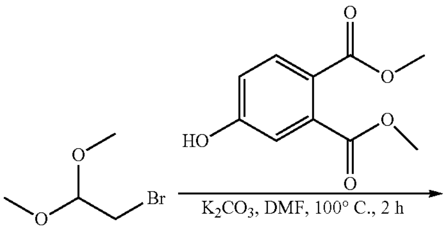

-continued

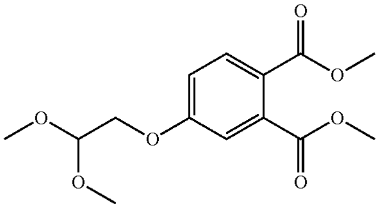

To a solution of 2-bromo-1,1-dimethoxy-ethane (3.22 g, 19.04 mmol, 2 eq) in dimethylformamide (20 mL) was added potassium carbonate (3.95 g, 28.56 mmol, 3 eq) and dimethyl 4-hydroxybenzene-1, 2-dicarboxylate (2 g, 9.52 mmol, 1 eq). The mixture was stirred at 100° C. for 3 hours. The reaction mixture was quenched by water 200 mL at 25° C., and then extracted with ethyl acetate (50 mL×3). The combined organic layers were washed with brine (50 mL×3), dried over anhydrous sodium sulfate, filtered and concentrated under reduced pressure. The residue was purified by column chromatography (petroleum ether:ethyl acetate=15:1 to 8:1). Compound dimethyl 4-(2,2-dimethoxyethoxy)benzene-1,2-dicarboxylate (2.64 g, 8.85 mmol, 92% yield) was obtained as a yellow oil.

Step 2

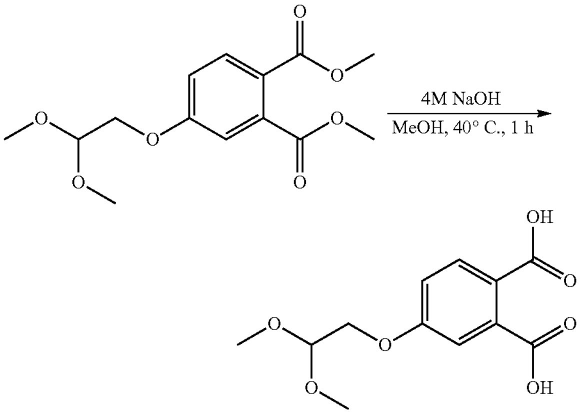

To a solution of dimethyl 4-(2,2-dimethoxyethoxy)benzene-1,2-dicarboxylate (2.64 g, 8.86 mmol, 1 eq) in methyl alcohol (20 mL) was added sodium hydroxide (4 M, 4.43 mL, 2 eq). The mixture was stirred at 40° C. for 12 hours. The reaction mixture was quenched by 1M hydrochloric acid (20 mL) at 20° C., and then diluted with water 100 mL and extracted with ethyl acetate (50 mL×3). The combined organic layers were washed with brine (50 mL×3), dried over anhydrous sodium sulfate, filtered and concentrated under reduced pressure. Crude product 4-(2,2-dimethoxyethoxy)phthalic acid (2.2 g, 8.14 mmol) was obtained as a yellow oil and was used in the next step without further purification.

Step 3

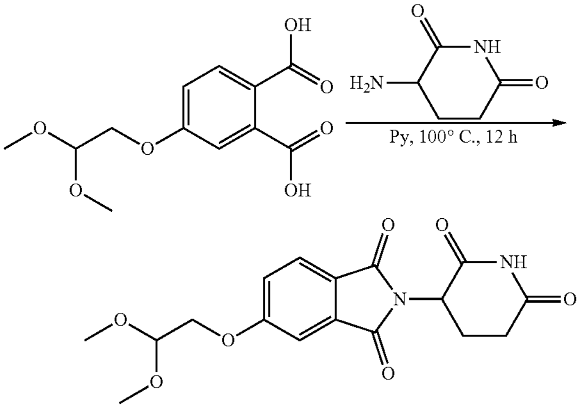

To a solution of 4-(2,2-dimethoxyethoxy)phthalic acid (2.2 g, 8.14 mmol, 1 eq) in pyridine (10 mL) was added 3-aminopiperidine-2,6-dione hydrochloride (2.01 g, 12.21 mmol, 1.5 eq). The mixture was stirred at 100° C. for 12 hours. The reaction mixture was concentrated under reduced pressure to remove pyridine (10 mL). The residue was diluted with water (200 mL) and extracted with ethyl acetate (50 mL×3). The combined organic layers were washed with brine (50 mL×3), dried over anhydrous sodium sulfate, filtered and concentrated under reduced pressure to give a residue. The residue was purified by column chromatography (petroleum ether/ethyl acetate=10:1 to 3:1). Compound 5-(2,2-dimethoxyethoxy)-2-(2,6-dioxo-3-piperidyl)isoindoline-1,3-dione (1.6 g, 4.20 mmol, 51% yield) was obtained as a yellow oil.

Step 4

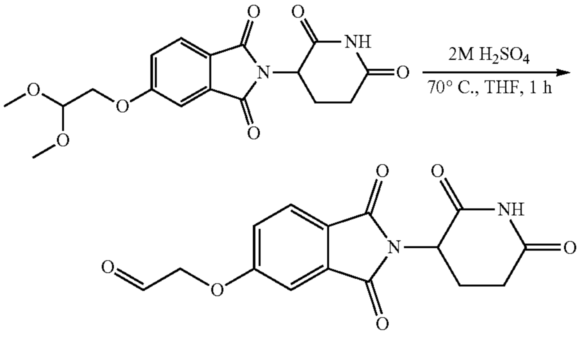

To a solution of 5-(2,2-dimethoxyethoxy)-2-(2,6-dioxo-3-piperidyl)isoindoline-1,3-dione (192 mg, 0.53 mmol, 1 eq) in tetrahydrofuran (10 mL) was added sulfuric acid (2 M, 10.6 mL, 40 eq), and the mixture was stirred at 70° C. for 1 hour. The reaction mixture was quenched by addition sodium bicarbonate 5 mL at 20° C., and then diluted with water (50 mL) and extracted with ethyl acetate (20 mL×3). The combined organic layers were washed with brine (20 mL×3), dried over anhydrous sodium sulfate, filtered and concentrated under reduced pressure. The 2-[2-(2,6-dioxo-3-piperidyl)-1,3-dioxo-isoindolin-5-yl] oxyacetaldehyde (160 mg, 0.50 mmol) was obtained as a white solid and was used in the next step without further purification.

2-[2-(2,6-dioxo-3-piperidyl)-1,3-dioxo-isoindolin-5-yl]oxyacetaldehyde was converted to the title compound by using procedures similar to those of the Exemplary Compound 578.

Exemplary Synthesis of Exemplary Compound 581

Prepared according to the scheme below using procedures described for other examples above as well as general procedures known to those skilled in the art.

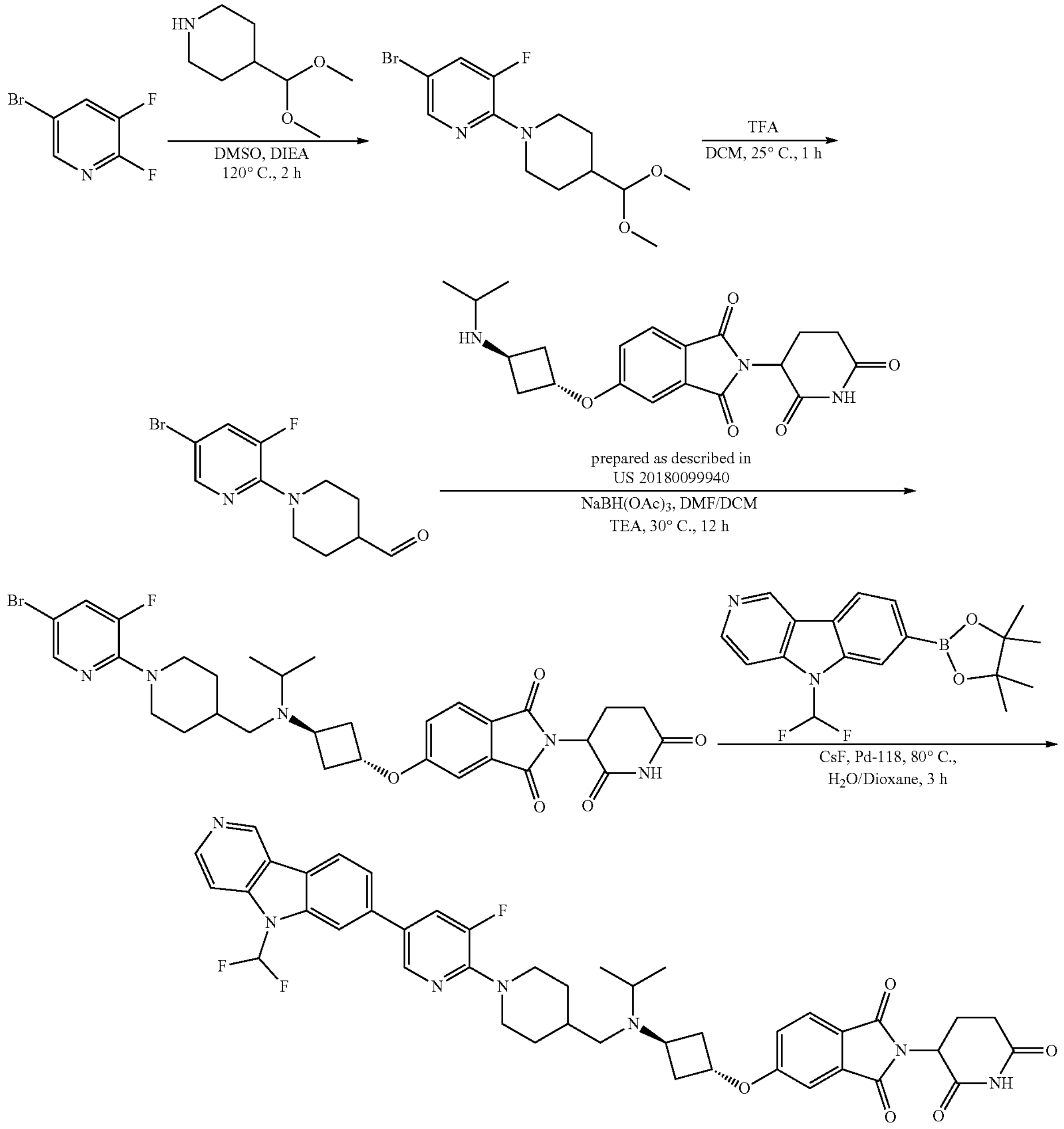

Exemplary Compound 581

Exemplary Synthesis of Exemplary Compound 585

Prepared according to the scheme below using procedures described for other examples above as well as general procedures known to those skilled in the art.

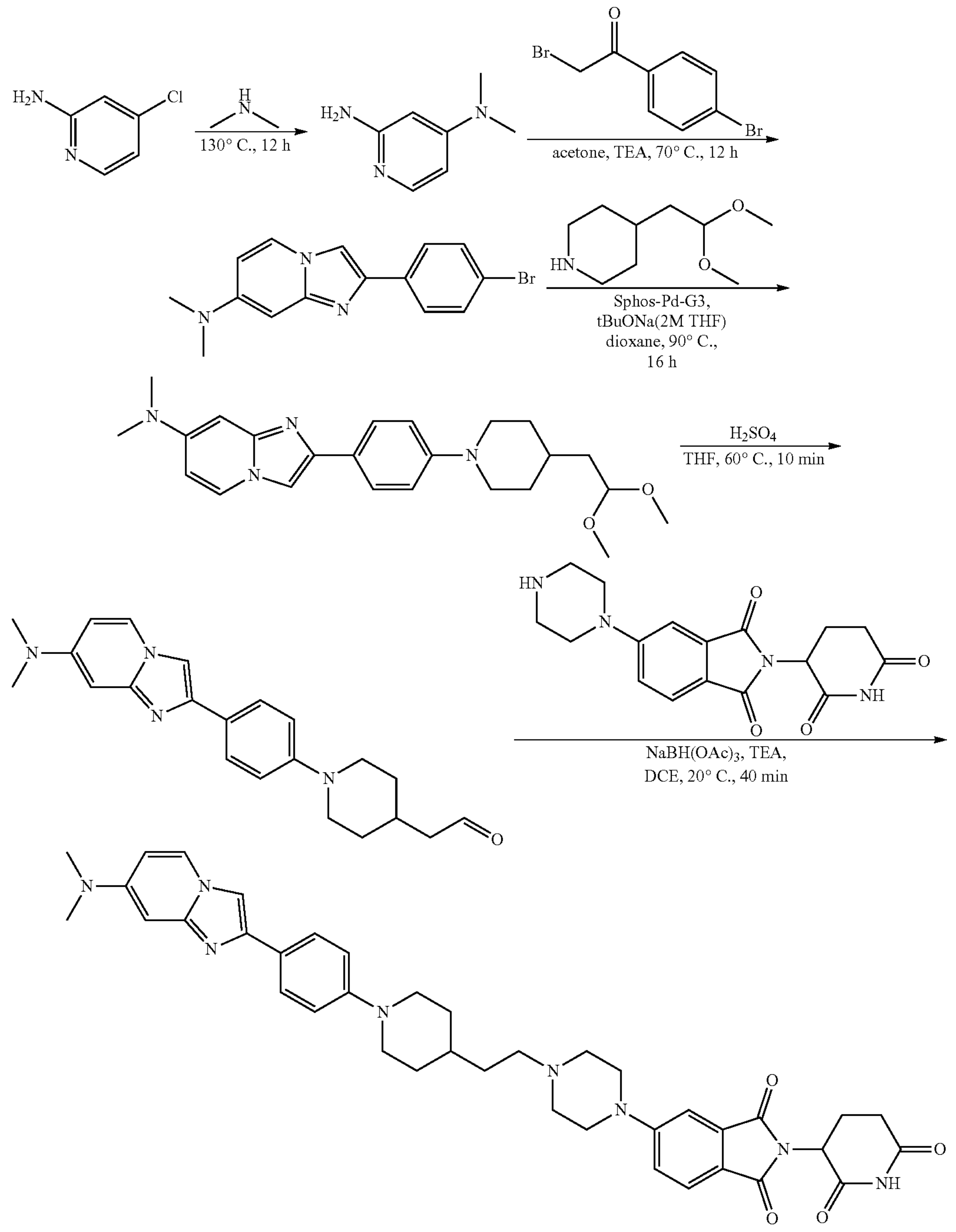
Exemplary Compound 585
Exemplary Synthesis of Exemplary Compound 583
Step 1
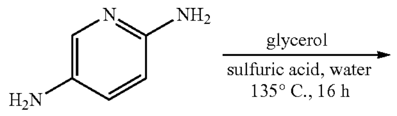
-continued
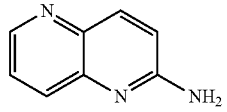
To a solution of pyridine-2,5-diamine (8 g, 73.31 mmol, 1 eq.) in $H_2SO_4$ (40 mL) and $H_2O$ (60 mL) was added sodium 3-nitrobenzenesulphonate (24.76 g, 109.96 mmol, 1.5 eq.) and glycerol (20.25 g, 219.92 mmol, 16.47 mL, 3 eq.). The mixture was stirred at 130° C. for 24 hr. The mixture was poured into ice/water (50 mL). The pH of the mixture was adjusted to ~9 with saturated aqueous NaOH solution. Then the mixture was extracted with EtOAc (200 mL×3) and the combined organic layers were dried over anhydrous $Na_2SO_4$, filtered and concentrated under reduced pressure to afford crude product which was purified by column chromatography (DCM/MeOH=20/1). Compound 1, 5-naphthyridin-2-amine (2 g, 13.78 mmol, 19% yield) was obtained as a brown solid.

Step 2

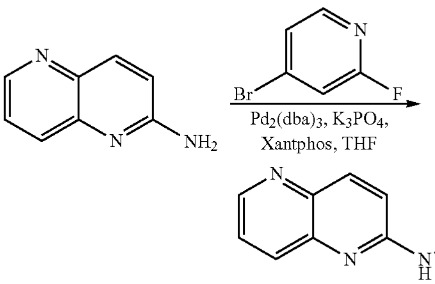

A mixture of 1,5-naphthyridin-2-amine (500 mg, 3.44 mmol, 1 eq.), 4-bromo-2-fluoro-pyridine (727.41 mg, 4.13 mmol, 1.2 eq.), $Pd(dba)_2$ (198.06 mg, 344.45 umol, 0.1 eq.), $K_3PO_4$ (1.46 g, 6.89 mmol, 2 eq.) and Xantphos (199.30 mg, 344.45 umol, 0.1 eq.) in THF (20 mL) was stirred at 80° C. for 18 hr under $N_2$ atmosphere. The reaction solution was diluted with water (50 mL) and extracted with EtOAc (50 mL×2). The combined organic layer was washed with brine, dried over anhydrous $Na_2SO_4$, filtered and concentrated under reduced pressure to afford crude product. The residue was purified by column chromatography (petroleum ether/ethyl acetate=1/1 to 0/1). Compound N-(2-fluoro-4-pyridyl)-1,5-naphthyridin-2-amine (520 mg, 1.86 mmol, 54% yield) was obtained as a light yellow solid.

Step 3

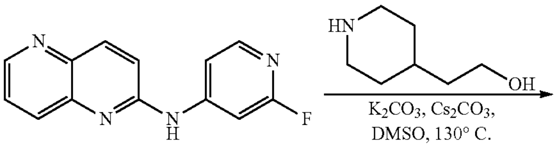

-continued

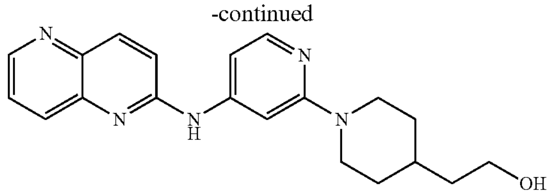

To a solution of N-(2-fluoro-4-pyridyl)-1,5-naphthyridin-2-amine (200 mg, 0.83 mmol, 1 eq.) and 2-(4-piperidyl) ethanol (108 mg, 0.83 mmol, 1 eq.) in DMSO (3 mL) was added $Cs_2CO_3$ (543 mg, 1.67 mmol, 2 eq.) and $K_2CO_3$ (345 mg, 2.50 mmol, 3 eq.). The mixture was stirred at 130° C. for 40 hr. The reaction solution was diluted with water (10 mL) and extracted with EtOAc (10 mL×3). The combined organic layer was washed with brine, dried over anhydrous $Na_2SO_4$, filtered and concentrated under reduced pressure to afford crude product. The residue was purified by column chromatography (DCM/MeOH=9/1). Compound 2-[1-[4-(1, 5-naphthyridin-2-ylamino)-2-pyridyl]-4-piperidyl]ethanol (140 mg, 0.23 mmol, 27% yield, 57% purity) was obtained as a yellow gum.

Step 4

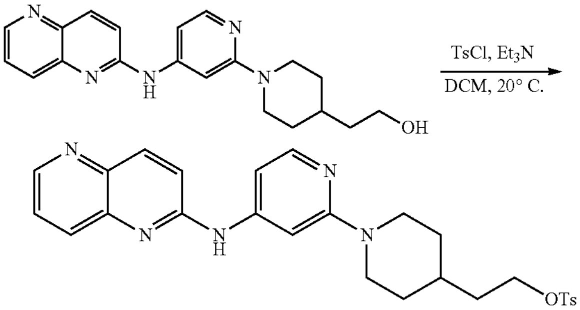

To a solution of 2-[1-[4-(1,5-naphthyridin-2-ylamino)-2-pyridyl]-4-piperidyl]ethanol (140 mg, 0.40 mmol, 1 eq.) in DCM (5 mL) was added TsCl (57 mg, 0.8 mmol, 2 eq.) and TEA (122 mg, 1.20 mmol, 167.30 uL, 3 eq.). The mixture was stirred at 20° C. for 18 hr. The reaction solution was diluted with water (10 mL) and extracted with DCM (10 mL×2). The combined organic layer was washed with brine, dried over anhydrous $Na_2SO_4$, filtered and concentrated under reduced pressure to afford crude product. The residue was purified by column chromatography (petroleum ether/ethyl acetate=1/1 to 0/1). Compound 2-[1-[4-(1,5-naphthyridin-2-ylamino)-2-pyridyl]-4-piperidyl]ethyl 4-methylbenzenesulfonate (100 mg, 131.05 umol, 33% yield, 66% purity) was obtained as a yellow gum.

Step 5

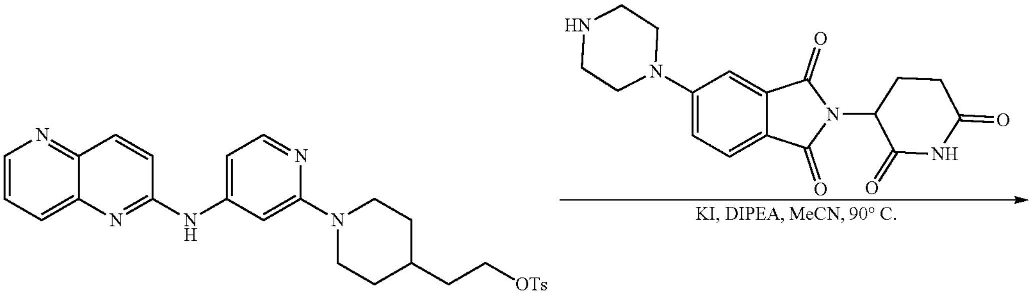

-continued

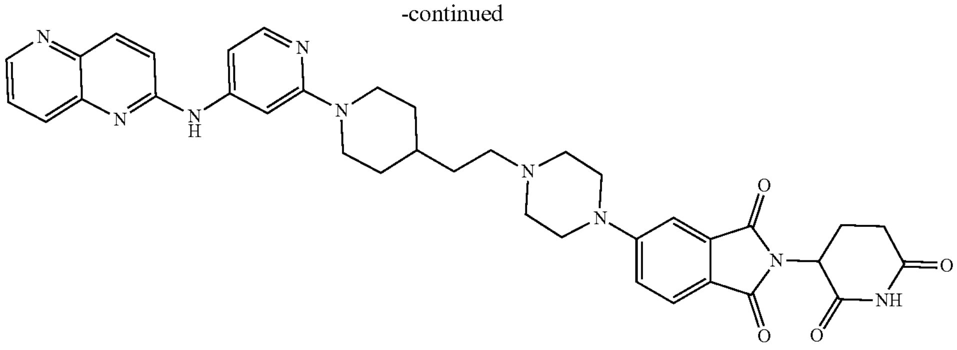

Exemplary Compound 583

To a solution of 2-[1-[4-(1,5-naphthyridin-2-ylamino)-2-pyridyl]-4-piperidyl]ethyl 4-methylbenzenesulfonate (100 mg, 0.20 mmol, 1 eq.) and 2-(2,6-dioxo-3-piperidyl)-5-piperazin-1-yl-isoindoline-1,3-dione (135.93 mg, 0.30 mmol, 1.5 eq., TFA) in $CH_3CN$ (2 mL) and DMSO (1 mL) was added KI (494 mg, 2.98 mmol, 15 eq.) and DIEA (385 mg, 2.98 mmol, 519 uL, 15 eq.). The mixture was stirred at 90° C. for 18 hr. The reaction solution was filtered to remove insoluble substance. The reaction solution was purified by prep-HPLC (FA condition:water (0.225% FA)-CAN) to afford 2-(2, 6-dioxo-3-piperidyl)-5-[4-[2-[1-[4-(1, 5-naphthyridin-2-ylamino)-2-pyridyl]-4-piperidyl]ethyl]piperazin-1-yl]isoindoline-1,3-dione (6.0 mg, 0.0086 mmol, 4.3% yield) as a yellow solid.

Exemplary Synthesis of Exemplary Compound 584

Step 1

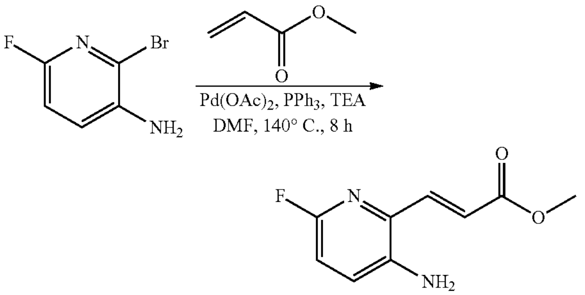

To a solution of 2-bromo-6-fluoro-pyridin-3-amine (10 g, 52.36 mmol, 1 eq) and methyl prop-2-enoate (6.76 g, 78.53 mmol, 7.07 mL, 1.5 eq) in DMF (70 mL) was added $Pd(OAc)_2$ (1.53 g, 6.81 mmol, 0.13 eq), $PPh_3$ (3.16 g, 12.04 mmol, 0.23 eq) and TEA (12.19 g, 120.42 mmol, 16.76 mL, 2.3 eq). Then the mixture was stirred at 140° C. for 2 hours. The mixture was cooled to room temperature and concentrated, then the residue was poured into $H_2O$ (200 mL). The aqueous phase was extracted with ethyl acetate (2×100 mL). The organic layer was washed with water (2×100 mL), brine (100 mL), dried with anhydrous $Na_2SO_4$, filtered and concentrated in vacuum to obtain the residue. The residue was triturated with 50% of ethyl acetate in petroleum ether at 20° C. for 30 minutes to give methyl (E)-3-(3-amino-6-fluoro-pyridin-2-yl)acrylate (7.2 g, 36.70 mmol, 70% yield) as a yellow solid.

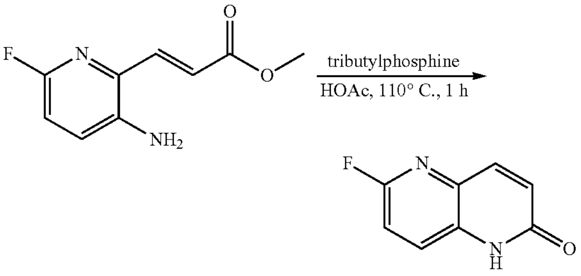

To a solution of methyl (E)-3-(3-amino-6-fluoro-2-pyridyl) prop-2-enoate (7 g, 35.68 mmol, 1 eq) in HOAc (50 mL) was added tributylphosphane (7.22 g, 35.68 mmol, 8.80 mL, 1 eq). Then the mixture was stirred at 110° C. for 3 hours. The solvent was removed in vacuum to obtain the residue. The residue was dissolved in EtOAc (200 mL), washed with $H_2O$ (200 mL) twice, and then two layers were separated. The organic layer was dried over $Na_2SO_4$, filtered, and the solvent was evaporated in vacuum to obtain the residue. The residue was triturated with MTBE at 20° C. for 1 hour to give 6-fluoro-1H-1, 5-naphthyridin-2-one (5.35 g, 32.59 mmol, 91% yield) as a yellow solid.

Step 3

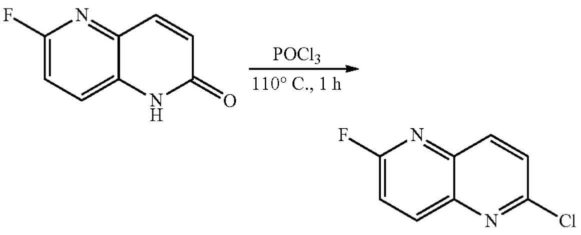

To a solution of $POCl_3$ (5.00 g, 32.59 mmol, 3.03 mL, 1 eq) in dioxane (100 mL) was added 6-fluoro-1H-1, 5-naphthyridin-2-one (5.35 g, 32.59 mmol, 1 eq). Then the mixture was stirred at 110° C. under $N_2$ for 1 hour. The reaction mixture was poured into the ice-water mixture. Saturated $NaHCO_3$ solution was added to the mixture until pH was adjusted to 6. Then the mixture was extracted with dichloromethane (100 mL×2), washed with $H_2O$ (100 mL) twice. The organic layer was washed with brine (100 mL), dried over anhydrous $Na_2SO_4$, filtered and concentrated in vacuum to obtain 2-chloro-6-fluoro-1, 5-naphthyridine (3.6 g, 13.80 mmol, 42% yield, 70% purity) as a yellow solid.

Step 4

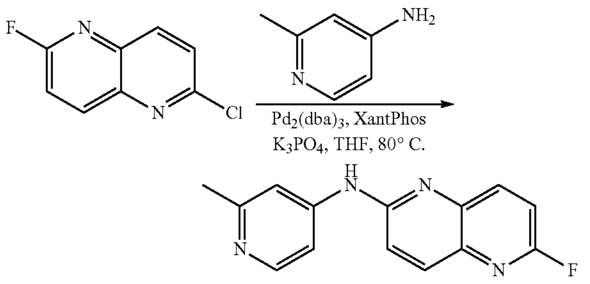

To a solution of 2-chloro-6-fluoro-1,5-naphthyridine (1.6 g, 6.13 mmol, 1 eq) and 2-methylpyridin-4-amine (729.70 mg, 6.75 mmol, 1.1 eq) in tert-butanol (20 mL) was added $Pd(OAc)_2$ (27.54 mg, 122.68 umol, 0.02 eq) and Xantphos (70.99 mg, 122.68 umol, 0.02 eq) and $Cs_2CO_3$ (5.60 g, 17.18 mmol, 2.8 eq) at 20° C. Then the mixture was stirred at 90° C. under $N_2$ for 12 hours. The mixture was cooled to 20° C. Ethyl acetate (100 mL) and $H_2O$ (100 mL) were added to the mixture. Aqueous phase was extracted with ethyl acetate (50 mL×2). The combined organic solutions was washed with brine (100 mL), dried over anhydrous $Na_2SO_4$, concentrated under vacuum to obtain the residue. The residue was purified by silica gel chromatography (50-100% of EA in PE) to give 6-fluoro-N-(2-methyl-4-pyridyl)-1, 5-naphthyridin-2-amine (1.1 g, 4.33 mmol, 70% yield) as a yellow solid.

6-fluoro-N-(2-methyl-4-pyridyl)-1, 5-naphthyridin-2-amine was converted to the title compound according to the scheme below using procedures described for other examples above as well as general procedures known to those skilled in the art.

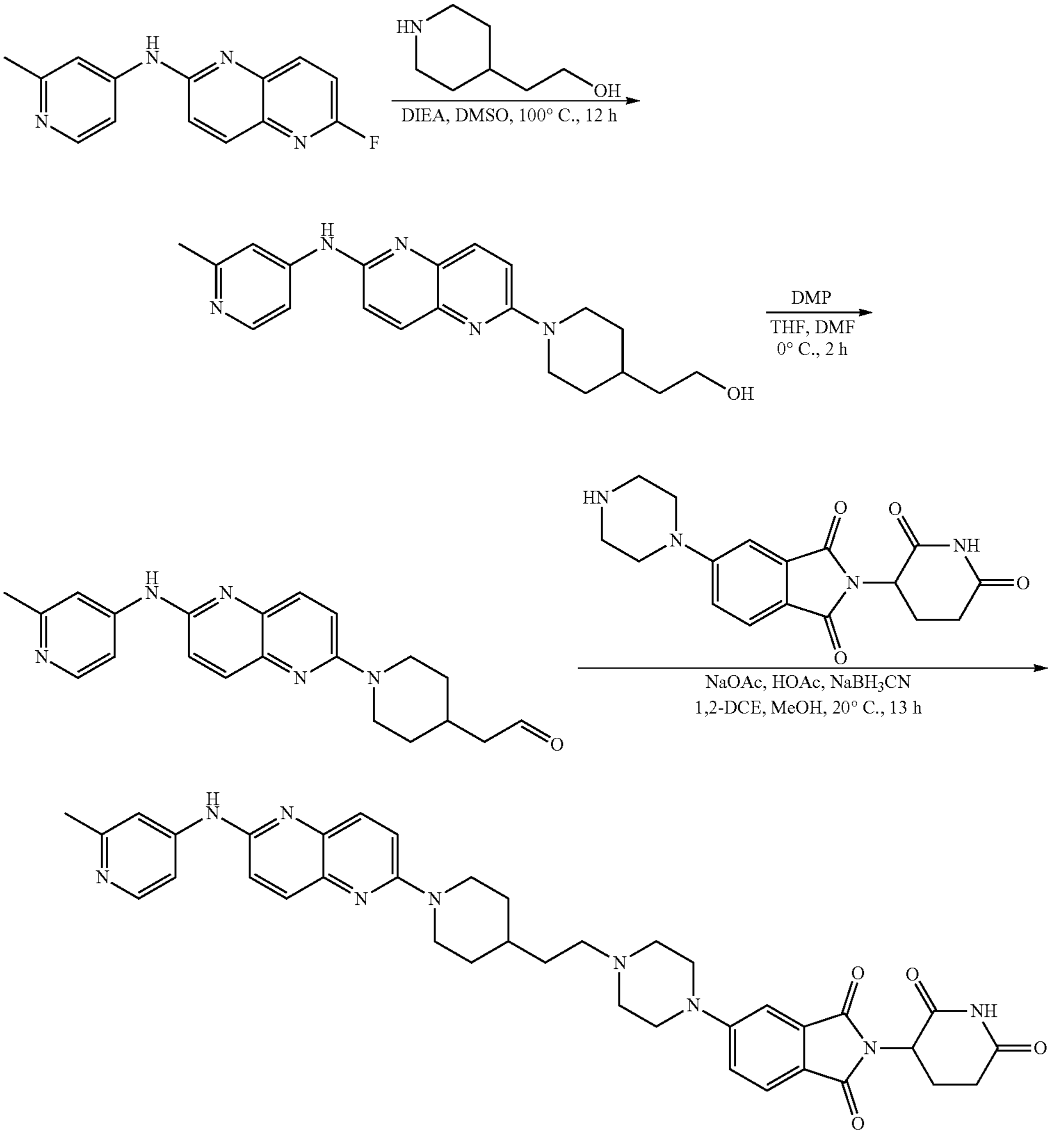

Exemplary Compound 584

Exemplary Synthesis of Exemplary Compound 589

Step 1

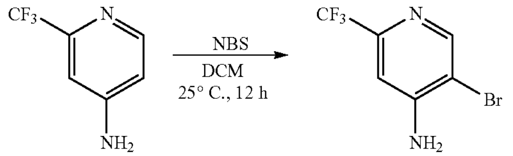

To a solution of 2-(trifluoromethyl)pyridin-4-amine (7.40 g, 45.65 mmol, 1.00 eq) in dichloromethane (105 mL) was added a solution of 1-bromopyrrolidine-2,5-dione (8.12 g, 45.65 mmol, 1.00 eq) in dichloromethane (70 mL). The mixture was stirred at 25° C. for 12 h. The solution was diluted by water (200 mL) and extracted with ethyl acetate (50 mL×3). The organic layer was concentrated under reduced pressure. The residue was purified by column chromatography on silica gel (petroleum ether:ethyl acetate=1:0 to 3:1) to give 5-bromo-2-(trifluoromethyl)pyridin-4-amine (7.50 g, 31.12 mmol, 68% yield) as a yellow solid.

Step 2

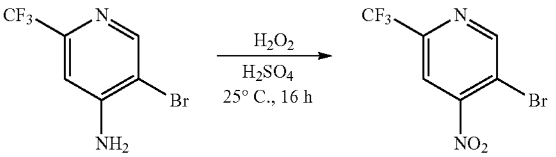 [SMILES: Nc1cc(C(F)(F)F)ncc1Br ; "H2O2" ; O=[N+]([O-])c1cc(C(F)(F)F)ncc1Br]

To a solution of 35% hydrogen peroxide (28.32 g, 291.40 mmol, 24 mL, 17.56 eq) in sulfuric acid (50 mL) was added a solution of 5-bromo-2-(trifluoromethyl)pyridin-4-amine (4.00 g, 16.60 mmol, 1.00 eq) in sulfuric acid (10 mL) dropwise at 0° C. The mixture was stirred at 20° C. for 12 h. The mixture was diluted with water (200 mL) and poured into sodium bicarbonate solution (200 mL). Then the mixture was extracted with ethyl acetate (100 mL×3). The organic layer was washed with sodium sulfite (100 mL), brine (100 mL) dried over anhydrous sodium sulfate and concentrated under reduced pressure. The residue was purified by column chromatography on silica gel (petroleum ether:ethyl acetate=1:0 to 0:1) to give 5-bromo-4-nitro-2-(trifluoromethyl)pyridine (2.60 g, 9.59 mmol, 57% yield) as a yellow oil.

Step 3

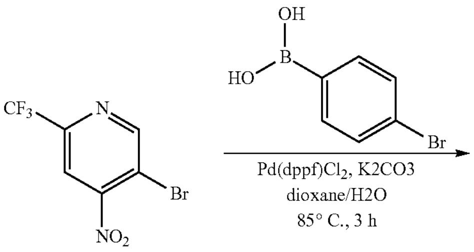

-continued

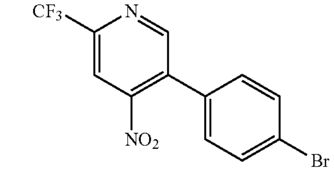

To a solution of 5-bromo-4-nitro-2-(trifluoromethyl)pyridine (200 mg, 0.73 mmol, 1.00 eq) and (4-bromophenyl) boronic acid (148 mg, 0.73 mmol, 1.00 eq) in dioxane (15 mL) and water (3 mL) was added potassium carbonate (816 mg, 5.90 mmol, 8.00 eq) under the atmosphere of nitrogen. Then to the mixture was added [1,1'-bis(diphenylphosphino) ferrocene]dichloropalladium(ii) (108 mg, 0.14 mmol, 0.20 eq). The mixture was stirred at 85° C. for 3 h in nitrogen. The mixture was concentrated under reduced pressure. The residue was diluted with water (10 mL) and extracted with ethyl acetate (10 mL×3). The combined organic layers were concentrated under reduced pressure. The crude product was purified by column chromatography on silica gel (petroleum ether:ethyl acetate=10:1) to give 5-(4-bromophenyl)-4-nitro-2-(trifluoromethyl)pyridine (80 mg, 0.2 mmol, 28% yield) as light yellow solid.

Step 4

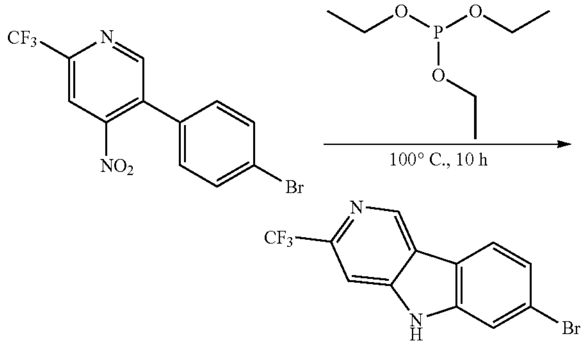

To a solution of 5-(4-bromophenyl)-4-nitro-2-(trifluoromethyl)pyridine (2.90 g, 8.36 mmol, 1.00 eq) in triethyl phosphite (20 mL) was stirred at 100° C. for 10 h. The mixture was concentrated under reduced pressure. The residue was purified by preparative high performance liquid chromatography (column: Phenomenex luna C18 (250*70 mm, 10 um); mobile phase: [water (0.225% FA)-ACN]; B %: 50%-80%, 18 min) to give 7-bromo-3-(trifluoromethyl)-5H-pyrido[4,3-b]indole (1.80 g, 5.71 mmol, 68% yield) as a white solid 7-bromo-3-(trifluoromethyl)-5H-pyrido[4,3-b]indole was converted to the title compound according to the scheme below using procedures described for other examples above as well as general procedures known to those skilled in the art.

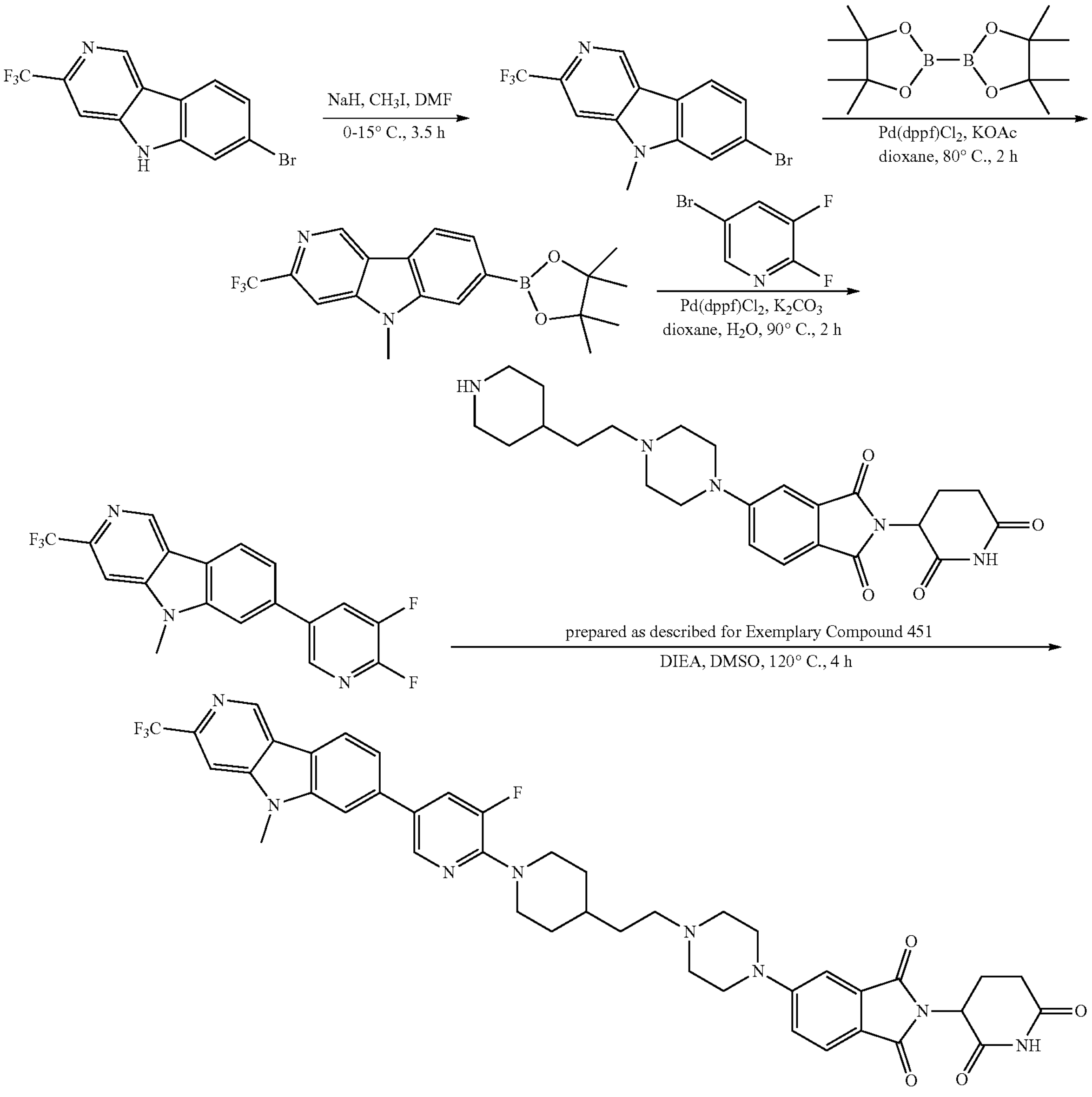

Exemplary Compound 589

Using analogous procedures the following examples were prepared: Exemplary Compound 596, Exemplary Compound 561, and Exemplary Compound 570.

Exemplary Synthesis of Exemplary Compound 590

Step 1

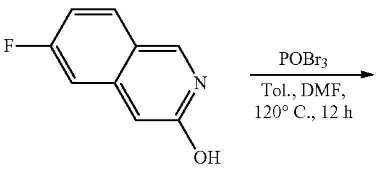

-continued

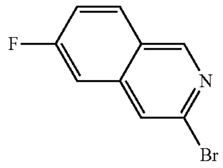

A solution of 6-fluoroisoquinolin-3-ol (1.5 g, 9.19 mmol, 1 eq) and phosphorus oxybromide (13.18 g, 45.97 mmol, 4.67 mL, 5 eq) in toluene (30 mL) and dimethyformamide (0.5 mL) was stirred at 120° C. for 12 h. The pH was adjusted to 8 with ammonium hydroxide and diluted with water (100 mL) and extracted with tetrahydrofuran (100 mL×3). The combined organic layers were washed with brine (100 mL×3), dried over anhydrous sodium sulfate, filtered and concentrated under reduced pressure. The residue was purified by silica gel column chromatography (petroleum ether/ethyl acetate=100/1 to 3/1). 3-bromo-6-fluoro-isoquinoline (1.1 g, 4.87 mmol, 52% yield) was obtained as a yellow solid.

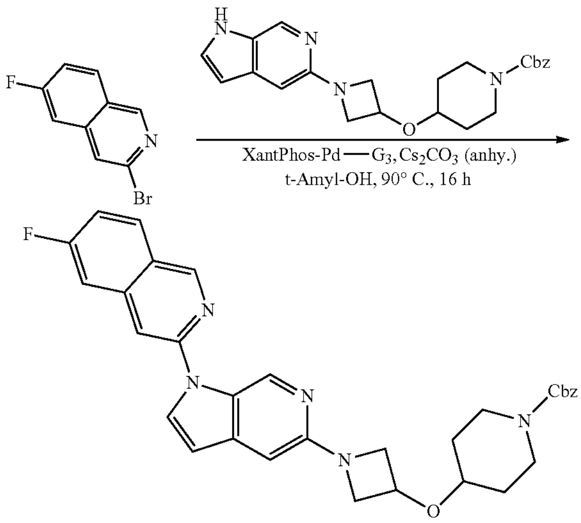

Benzyl 4-[1-(1H-pyrrolo[2,3-c]pyridin-5-yl)azetidin-3-yl]oxypiperidine-1-carboxylate (130 mg, 0.32 mmol, 1 eq), 3-bromo-6-fluoro-isoquinoline (79 mg, 0.35 mmol, 1.1 eq), cesium carbonate (312 mg, 0.96 mmol, 3 eq) and methanesulfonato[4,5-bis(diphenylphosphino)-9,9-dimethylxanthene](2-amino-1,1-biphenyl-2-yl)palladium(II) (30 mg, 0.03 mmol, 0.1 eq) in 2-methylbutan-2-ol (3 mL) was degassed and then heated to 90° C. for 16 h under nitrogen. The reaction mixture was filtered and concentrated under reduced pressure. The residue was purified by silica gel column chromatography (dichloromethane:methanol=100/1 to 10/1). Benzyl 4-[1-[I-(6-fluoro-3-isoquinolyl)pyrrolo[2,3-c]pyridin-5-yl]azetidin-3-yl]oxypiperidine-1-carboxylate (90 mg, 0.16 mmol, 51% yield) was obtained as a yellow oil.

Benzyl 4-[1-[1-(6-fluoro-3-isoquinolyl)pyrrolo[2,3-c]pyridin-5-yl]azetidin-3-yl]oxypiperidine-1-carboxylate was converted to the title compound using procedures described for Exemplary Compound 578.

Using analogous procedures, in combination with procedures described for Exemplary Compound 480, the following examples were prepared: Exemplary Compounds 555 and 598.

Exemplary Synthesis of Exemplary Compound 591

Step 1

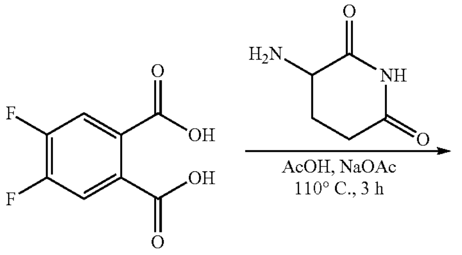

-continued

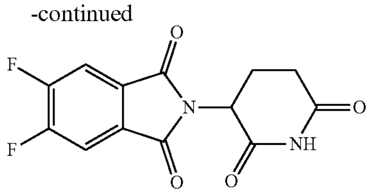

To a solution of 4,5-difluorophthalic acid (1.5 g, 7.42 mmol, 1.0 eq) and 3-aminopiperidine-2,6-dione hydrochloride (1.83 g, 11.13 mmol, 1.5 eq) in acetic acid (15 mL) was added sodium acetate (1.22 g, 14.84 mmol, 2.00 eq). The mixture was stirred at 110° C. for 3 h. The mixture was washed with water 50 mL, filtered and concentrated under reduced pressure, and then the residue was triturated with 120 mL of petroleum ether/ethyl acetate=5:1, filtered and dried under reduced pressure to give 2-(2,6-dioxo-3-piperidyl)-5,6-difluoro-isoindoline-1,3-dione (1.5 g, 5.10 mmol, 68% yield) as a yellow solid which was used in the next step without further purification.

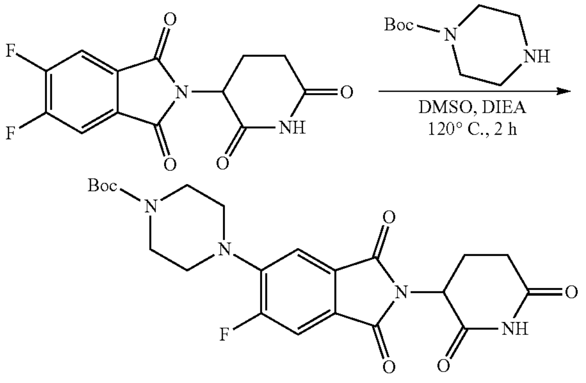

To a solution or 2-(2,6-dioxo-3-piperidyl)-5,6-difluoro-isoindoline-1,3-dione (1.1 g, 3.74 mmol, 1.0 eq) in dimethylsulfoxide (3 mL) was added diisopropylethyllamine (1.45 g, 11.22 mmol, 3.0 eq) and tert-butyl piperazine-1-carboxylate (626 mg, 3.36 mmol, 0.9 eq). The mixture was stirred at 120° C. for 2 hours. The reaction mixture was diluted with water (40 mL) and extracted with ethyl acetate (50 mL×3). The combined organic layers were washed with brine (30 mL×3), dried over sodium sulfate, filtered and concentrated under reduced pressure. The residue was purified by silica gel chromatography (petroleum ether/ethyl acetate=20/1 to 3:1) to give tert-butyl 4-[2-(2,6-dioxo-3-piperidyl)-6-fluoro-1,3-dioxo-isoindolin-5-yl]piperazine-1-carboxylate (1.58 g, 3.43 mmol, 91% yield) as a yellow oil.

Step 3

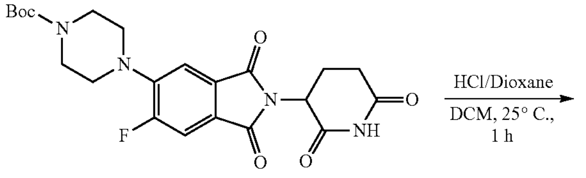

-continued

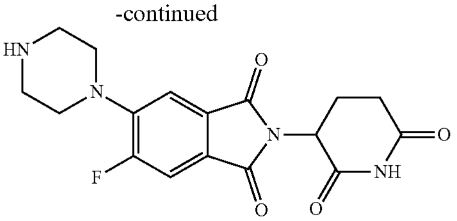

To a solution of tert-butyl 4-[2-(2,6-dioxo-3-piperidyl)-6-fluoro-1,3-dioxo-isoindolin-5-yl]piperazine-1-carboxylate (1.58 g, 3.43 mmol, 1.0 eq) in dichloromethane (5 mL) was added hydrochloric acid/dioxane (4 M, 5 mL). The mixture was stirred at 25° C. for 1 hr. Crude 2-(2,6-dioxo-3-piperidyl)-5-fluoro-6-piperazin-1-yl-isoindoline-1,3-dione hydrochloride (1.3 g, 3.28 mmol) was obtained as a yellow solid was used in the next step without further purification.

2-(2,6-Dioxo-3-piperidyl)-5-fluoro-6-piperazin-1-yl-isoindoline-1,3-dione was converted to the title compound as described for Exemplary Compound 559.

Using analogous procedures, Exemplary Compound 547 was prepared.

Exemplary Synthesis of Exemplary Compound 594

Step 1

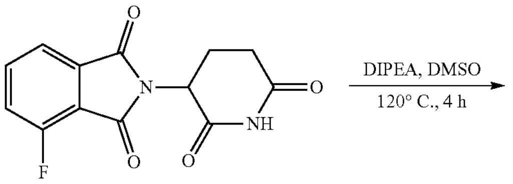

CAS # 835616-60-9

-continued

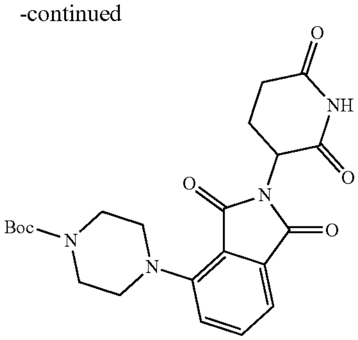

To a solution of 2-(2,6-dioxo-3-piperidyl)-4-fluoro-isoindoline-1,3-dione (2 g, 7.24 mmol, 1 eq) and tert-butyl piperazine-1-carboxylate (1.35 g, 7.24 mmol, 1 eq) in dimethyl sulfoxide (20 mL) was added N,N-diisopropylethylamine (2.81 g, 21.72 mmol, 3 eq). The mixture was stirred at 120° C. for 4 h. The mixture was cooled to 25° C., then water (100 mL) was added, and the mixture extracted with dichloromethane (80 mL×3). The combined organics were washed with brine (80 mL×3) and concentrated to give the crude product. The crude product was triturated with petroleum ether:ethyl acetate=1:1 (30 mL) to produce tert-butyl 4-[2-(2,6-dioxo-3-piperidyl)-1,3-dioxo-isoindolin-4-yl]piperazine-1-carboxylate (2.0 g, 4.47 mmol, 61% yield) as a yellow solid.

tert-Butyl 4-(2-(2,6-dioxopiperidin-3-yl)-1,3-dioxoisoindolin-4-yl)piperazine-1-carboxylate was converted to the title compound according to the scheme below using procedures described for other examples above as well as general procedures known to those skilled in the art.

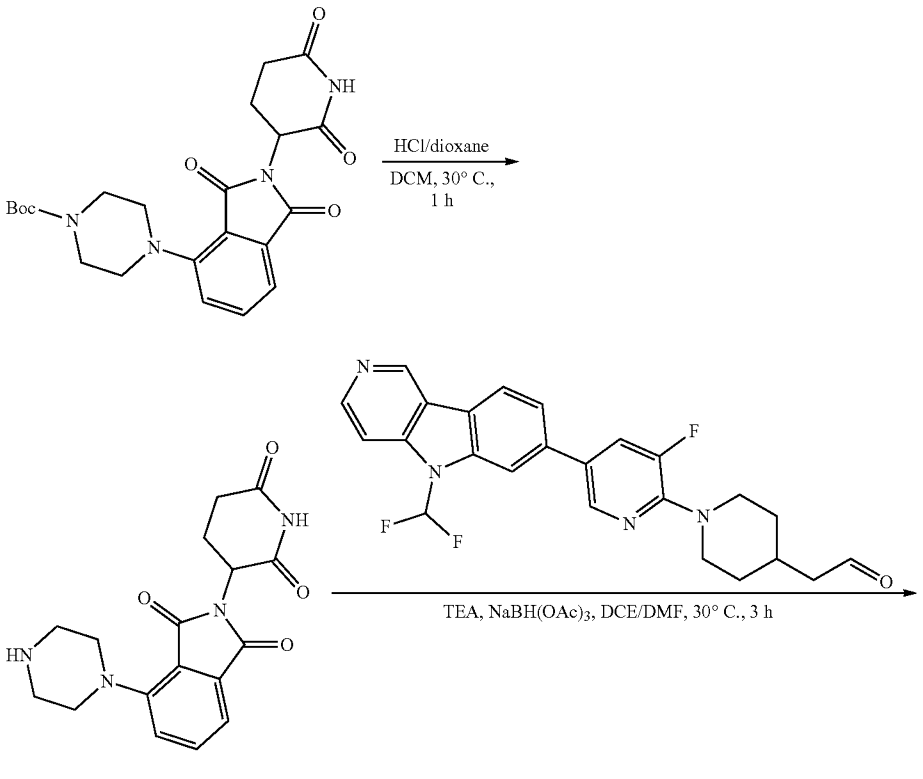

-continued

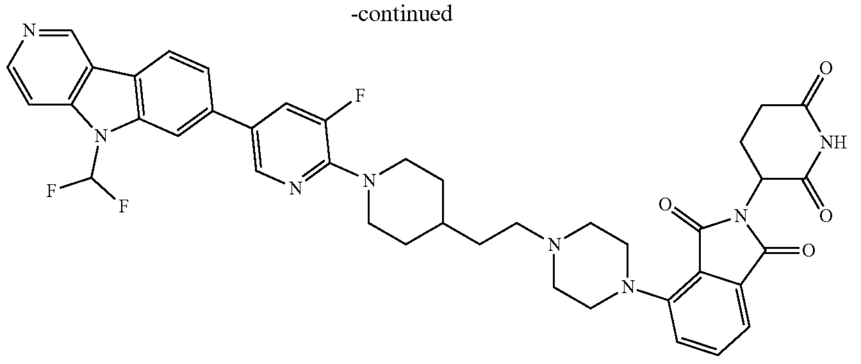

Exemplary Compound 594

Exemplary Synthesis of Exemplary Compound 597

Step 1

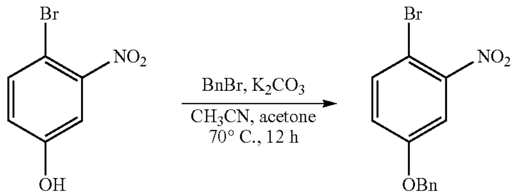

To a solution of 4-bromo-3-nitro-phenol (20 g, 91.74 mmol, 1 eq) and bromomethylbenzene (23.54 g, 137.61 mmol, 1.5 eq) in acetonitrile (300 mL) and acetone (150 mL) was added potassium carbonate (19.02 g, 137.61 mmol, 1.5 eq). The mixture was heated to 80° C. for 16 hr. Solvent was removed in vacuum and residue was partitioned between ethyl acetate (100 mL) and water (150 mL). Aqueous layer was extracted with ethyl acetate (100 mL×2), and organic layers were combined and washed with brine (100 mL) and dried over anhydrous sodium sulfate. Filtrate was concentrated in vacuum. The residue was purified by column chromatography ($SiO_2$, petroleum ether:ethyl acetate=1:0 to 10:1) to give 4-benzyloxy-1-bromo-2-nitro-benzene (14 g, 45.44 mmol, 49% yield) as a red oil.

Step 2

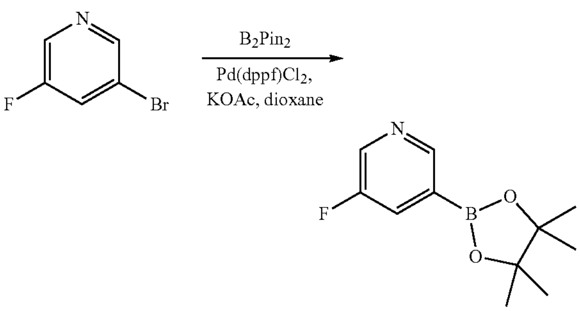

A flask was charged with 3-bromo-5-fluoro-pyridine (25 g, 142.06 mmol, 1 eq), 4,4,5,5-tetra-methyl-2-(4,4,5,5-tetramethyl-1,3,2-dioxaborolan-2-yl)-1,3,2-dioxaborolane (39.68 g, 156 mmol, 1.1 eq), potassium acetate (27.88 g, 284 mmol, 2 eq), [1,1'-bis(diphenylphosphino)ferrocene]dichloropalladium(II) (2.08 g, 2.84 mmol, 0.02 eq) and dioxane (250 mL). The mixture was purged with $N_2$ for 3 times and heated to 110° C. for 4 hr. Solvent was removed in vacuum and residue was partitioned between ethyl acetate (300 mL) and water (150 mL). Aqueous layer was extracted with ethyl acetate (300 mL×2) and organic layers were combined and washed with brine (200 mL) and dried over anhydrous sodium sulfate. Filtrate was concentrated in vacuum. Crude 3-fluoro-5-(4,4,5,5-tetrame-thyl-1,3,2-dioxaborolan-2-yl) pyridine (63 g, 141 mmol, 99% yield, 50% purity) was obtained as a dark solid and used in the next step without further purification.

Step 3

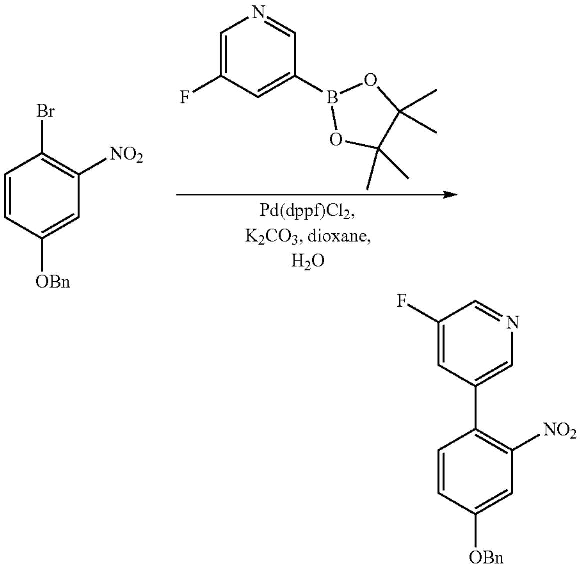

To a solution of 4-benzyloxy-1-bromo-2-nitro-benzene (13.8 g, 44.79 mmol, 1 eq) and 3-fluoro-5-(4,4,5,5-tetramethyl-1,3,2-dioxaborolan-2-yl)pyridine (23.98 g, 53.74 mmol, 1.2 eq) in the mixed solvent of dioxane (200 mL) and water (20 mL) was added potassium carbonate (18.57 g, 134.36 mmol, 3 eq) in the atmosphere of nitrogen. Then [1,1'-bis(diphenylphosphino)ferrocene]dichloropalladium (II) (1.31 g, 1.79 mmol, 0.04 eq) was added, and the mixture was stirred at 100° C. for 4 hours. The reaction mixture was concentrated under reduced pressure to remove solvent. The residue was diluted with water (200 mL) and extracted with ethyl acetate (200 mL×4). The combined organic layers were washed with brine (300 mL×3), dried over anhydrous sodium sulfate, filtered and concentrated under reduced pressure. The residue was purified by column chromatography (petroleum ether:ethyl acetate=50:1 to 5:1) to give 3-(4-benzyloxy-2-nitro-phenyl)-5-fluoro-pyridine (3 g, 8.51 mmol, 19% yield) as a yellow solid.

Step 4

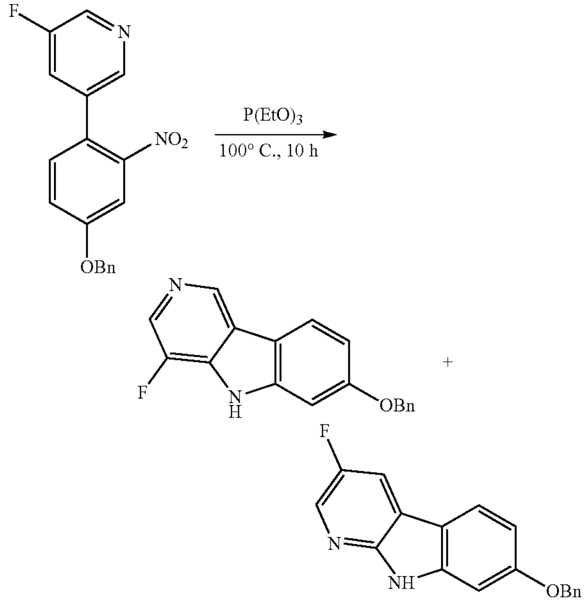

A solution of 3-(4-benzyloxy-2-nitro-phenyl)-5-fluoro-pyridine (3 g, 9.25 mmol, 1 eq) in triethyl phosphite (60 mL) was stirred at 100° C. for 10 hr. LC-MS showed the starting material was consumed completely and one main peak with desired mass was detected. The reaction mixture was concentrated under reduced pressure to remove solvent. The crude product was triturated with ethyl acetate (10 mL) to give 7-benzyloxy-4-fluoro-5H-pyri-do[4,3-b]indole (183 mg, 0.63 mmol, 6% yield) as a yellow solid. The filtrate was concentrated under reduced pressure. The residue was purified by column chromatography (petroleum ether:ethyl acetate=20:1 to 10:1) to give 7-benzyloxy-3-fluoro-9H-pyrido[2,3-b]indole (800 mg, 2.74 mmol, 29% yield) as a yellow solid.

Step 5

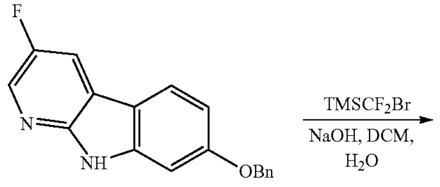

-continued

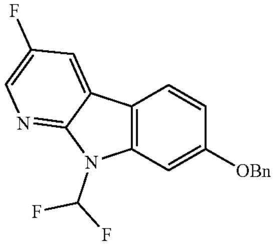

To a mixture of 7-benzyloxy-3-fluoro-9H-pyrido[2,3-b]indole (250 mg, 0.85 mmol, 1 eq) in dichloromethane (10 mL) was added a solution of potassium hydroxide (288 mg, 5.13 mmol, 6 eq) in water (1.2 mL) at 0° C. Then a solution of [bromo(difluoro)methyl]-trimethyl-silane (347 mg, 1.71 mmol, 2 eq) in dichloromethane (2 mL) was added to the mixture at 0° C. The mixture was stirred at 30° C. for 1 hr. LCMS showed the starting material was remained. Additional [bromo(difluoro)methyl]-trimethyl-silane (869 mg, 4.28 mmol, 5 eq) was added. The mixture was stirred at 30° C. for 11 hr. LC-MS showed the starting material was consumed completely. The reaction mixture was diluted with water (20 mL) and extracted with dichloromethane (40 mL×2). Then organic layer was separated and dried over anhydrous sodium sulfate, filtered and concentrated in vacuum. Crude 7-benzyloxy-9-(difluoromethyl)-3-fluoro-pyrido[2,3-b]indole (290 mg, 0.85 mmol) was obtained as a yellow solid.

Step 6

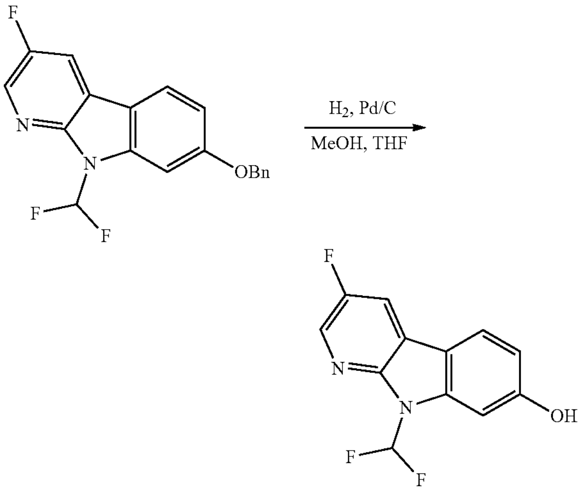

To a solution of 7-benzyloxy-9-(difluoromethyl)-3-fluoro-pyrido[2,3-b]indole (290 mg, 0.85 mmol, 1 eq) in methanol (10 mL) and tetrahydrofuran (10 mL) was added palladium on activated carbon catalyst (100 mg, 0.85 mmol, 10% purity, 1 eq) under $N_2$. The suspension was degassed under vacuum and purged with $H_2$ several times. The mixture was stirred under $H_2$ (15 psi) at 25° C. for 12 hours. The reaction mixture was filtered and concentrated under reduced pressure to give crude 9-(difluoromethyl)-3-fluoro-pyrid-o[2,3-b]indol-7-ol (190 mg, 0.61 mmol) as a white solid.

Step 7

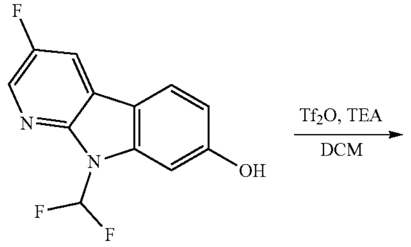

-continued

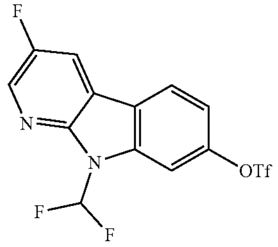

To 9-(difluoromethyl)-3-fluoro-pyrido[2,3-b]indol-7-ol (106 mg, 0.422 mmol, 1 eq) in dichloromethane (4 mL) was added triethylamine (127 mg, 1.26 mmol, 3 eq). Then trifluoromethanesulfonic anhydride (178 mg, 0.63 mmol, 1.5 eq) was added into the mixture at 0° C. The mixture was stirred at 20° C. for 1 h. The reaction mixture was diluted with water (20 mL) and extracted with dichloromethane (40 mL×2). The organic layer was separated and dried over anhydrous sodium sulfate and concentrated in vacuum. The residue was purified by prep-TLC (petroleum ether:ethyl acetate=10:1) to give [9-(difluoromethyl)-3-fluoro-pyrido[2,3-b]indol-7-yl] trifluoromethanesulfonate (120 mg, 0.31 mmol) as a white solid.

[9-(Difluoromethyl)-3-fluoro-pyrido[2,3-b]indol-7-yl] trifluoromethanesulfonate was converted to the title compound according to the scheme below using procedures described for other examples above as well as general procedures known to those skilled in the art.

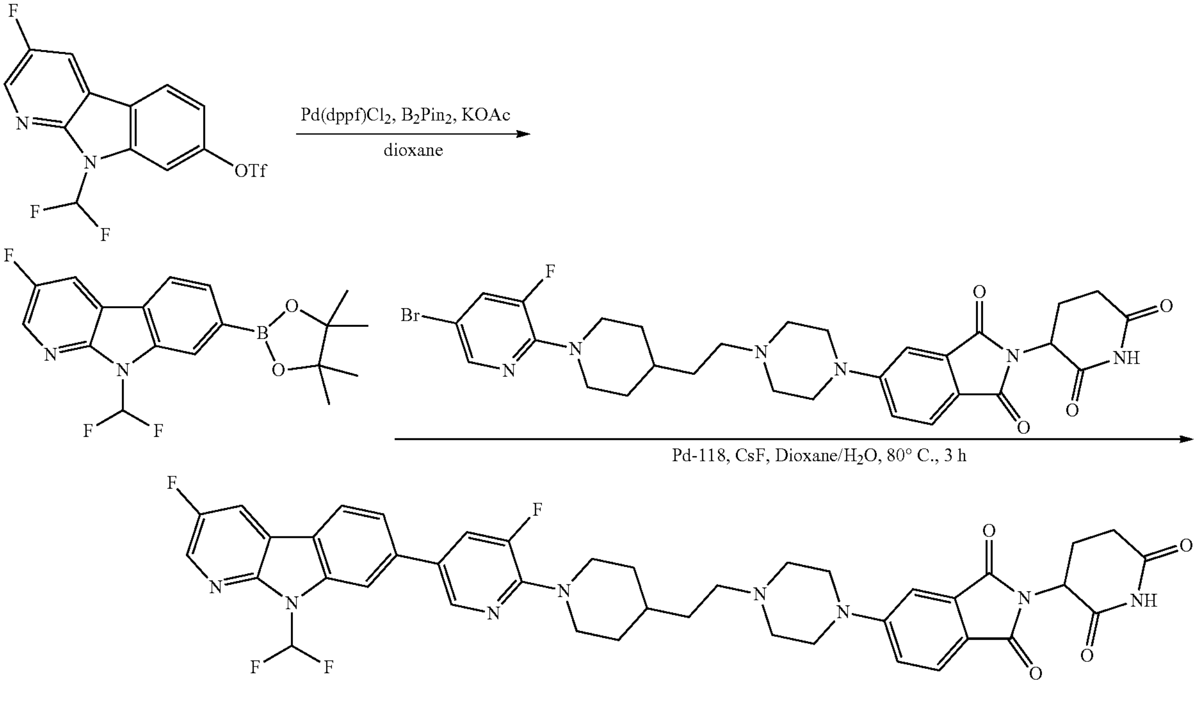

Exemplary Compound 597

Using analogous procedures Exemplary Compound 564 was prepared from 7-(benzyloxy)-4-fluoro-5H-pyrido[4,3-b]indole obtained in step 4.

Exemplary Synthesis of Exemplary Compound 565

Step 1

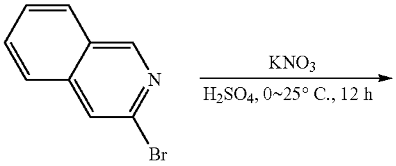

-continued

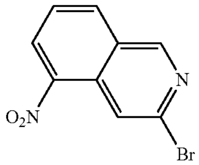

To a solution of 3-bromoisoquinoline (1 g, 4.81 mmol, 1 eq) in sulfuric acid (24 mL) was added dropwise a solution of potassium nitrate (485 mg, 4.81 mmol, 1 eq) in sulfuric acid (5 mL) at 0° C. The reaction was stirred at 25° C. for 12 h. The reaction mixture was poured into ice water (300 mL). The precipitate that formed was collected by filtration and dried under reduced pressure. 3-bromo-5-nitro-isoquinoline (1 g, 3.95 mmol, 82% yield) was obtained as a yellow solid.

Step 2

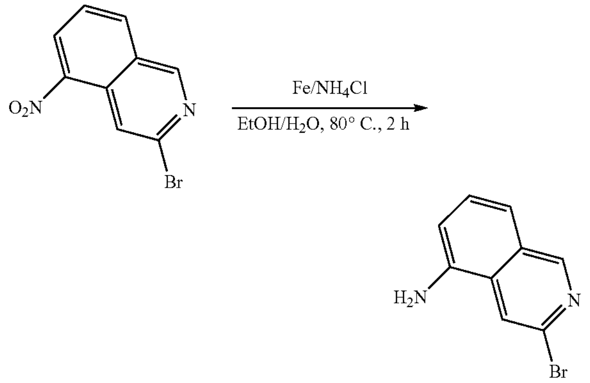

To a solution of 3-bromo-5-nitro-isoquinoline (5 g, 19.76 mmol, 1 eq) in ethyl alcohol (30 mL) and water (20 mL) were added iron powder (5.52 g, 98.79 mmol, 5 eq) and ammonium chloride (5.28 g, 98.79 mmol, 5 eq). The reaction mixture was stirred 80° C. for 2 hr. The reaction mixture was filtered and concentrated under reduced pressure. The residue was diluted with water (100 mL) and extracted with ethyl acetate (100 mL×3). The combined organic layers were washed with brine (100 mL×3), dried over anhydrous sodium sulfate, filtered and concentrated under reduced pressure. 3-Bromoisoquinolin-5-amine (3.9 g, 17.48 mmol, 88% yield) was obtained as a yellow solid and used in the next step directly.

Step 3

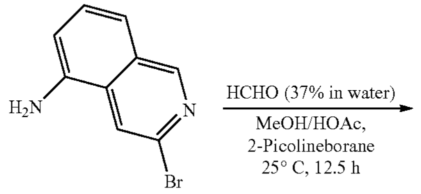

-continued

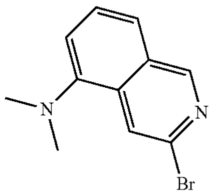

A solution of 3-bromoisoquinolin-5-amine (500 mg, 2.24 mmol, 1 eq) and formaldehyde (0.16 mL, 2.24 mmol, 1 eq) in methyl alcohol (10 mL) and acetic acid (1 mL) was stirred at 25° C. for 0.5 h. Then borane; 2-methylpyridine (479 mg, 4.48 mmol, 2 eq) was added. The reaction mixture was stirred at 25° C. for 12 hr. The reaction mixture was filtered and concentrated under reduced pressure. The residue was purified by prep-HPLC (column: Phenomenex Synergi C18 150*25*10 um; mobile phase: [water (0.225% FA)-ACN]; B %: 50%-80%, 9 min). 3-bromo-N,N-dimethyl-isoquinolin-5-amine (300 mg, 1.19 mmol, 53% yield) was obtained as a white solid.

Step 4

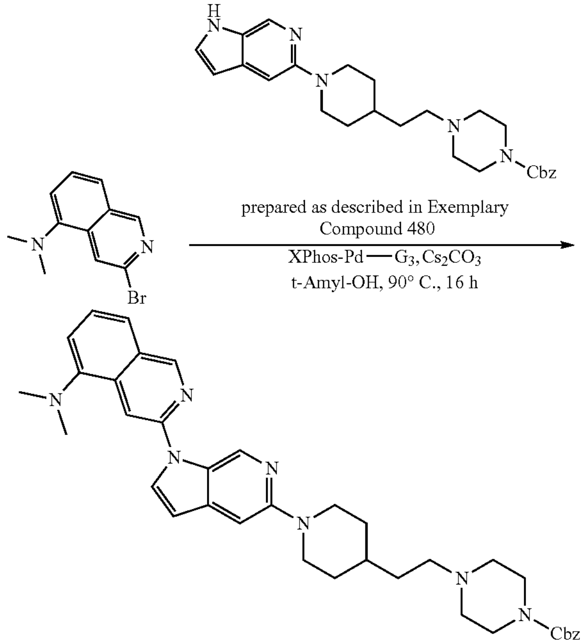

Benzyl 4-[2-[1-(1H-pyrrolo[2,3-c]pyridin-5-yl)-4-piperidyl]ethyl]piperazine-1-carboxylate (200 mg, 0.44 mmol, 1 eq), 3-bromo-N,N-dimethyl-isoquinolin-5-amine (123 mg, 0.49 mmol, 1.1 eq), cesium carbonate (145 mg, 0.44 mmol, 1 eq) and XPhos-Pd-$G_3$ [[2-(2-aminophenyl)phenyl] palladium(II) dicyclohexyl-[2-(2,4,6-triisopropylphenyl)phenyl] phosphane methanesulfonate] (37 mg, 0.04 mmol, 0.1 eq) in 2-methylbutan-2-ol (3 mL) was degassed and then heated to 90° C. for 16 hr under nitrogen. The reaction mixture was diluted with dichloromethane (100 mL), dried over anhydrous sodium sulfate, filtered and concentrated under reduced pressure. The residue was purified by silica gel column chromatography (dichloromethane:methyl alcohol=100/1 to 10/1). Benzyl 4-[2-[1-[1-[5-(dimethylamino)-3-isoquinolyl]pyrrolo[2,3-c]pyridin-5-yl]-4-piperidyl]ethyl] piperazine-1-carboxylate (150 mg, 0.21 mmol, 48% yield) was obtained as a yellow oil.

Step 5

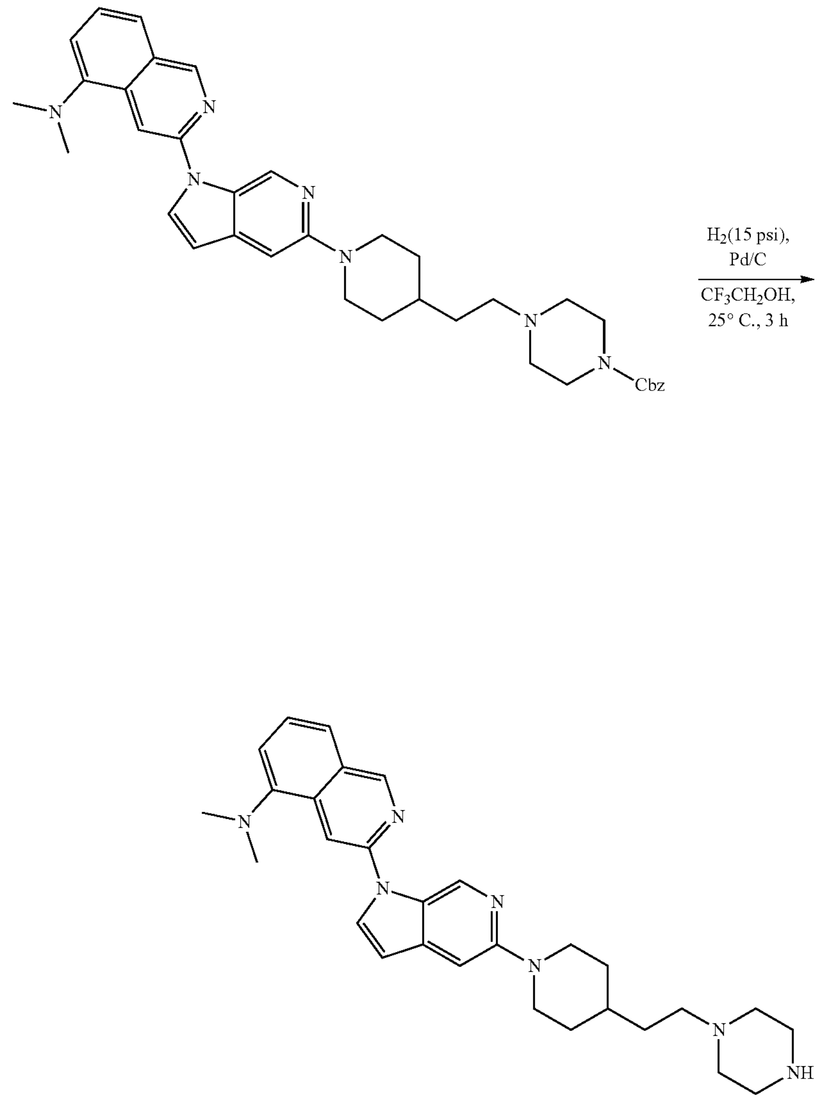

To a solution of benzyl 4-[2-[1-[1-[5-(dimethylamino)-3-isoquinolyl]pyrrolo[2,3-c] pyridin-5-yl]-4-piperidyl]ethyl] piperazine-1-carboxylate (150 mg, 0.21 mmol, 1 eq) in trifluoroethanol (5 mL) was added palladium carbon catalyst (50 mg, 10% purity) under nitrogen. The suspension was degassed under vacuum and purged with hydrogen several times. The mixture was stirred under hydrogen (15 psi) at 25° C. for 3 h. The reaction mixture was filtered and concentrated under reduced pressure. Crude N,N-dimethyl-3-[5-[4-(2-piperazin-1-ylethyl)-1-piperidyl]pyrrolo[2,3-c] pyridine-1-yl]isoquinolin-5-amine (100 mg, 0.2 mmol) was obtained as a yellow oil and used in the next step directly.

Step 6

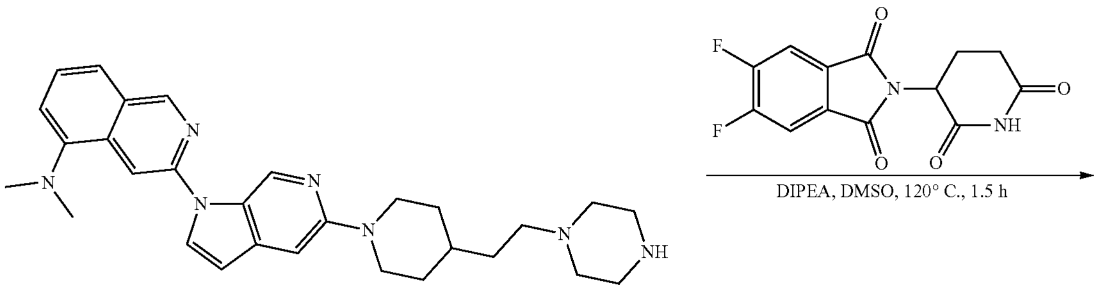

-continued

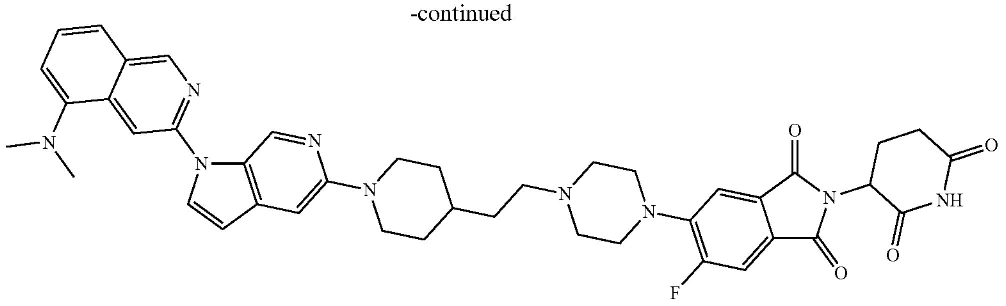

Exemplary Compound 565

A solution of N,N-dimethyl-3-[5-[4-(2-piperazin-1-ylethyl)-1-piperidyl]pyrrolo[2,3-c] pyridin-1-yl]isoquinolin-5-amine (120 mg, 0.24 mmol, 1 eq), 2-(2,6-dioxo-3-piperidyl)-5,6-difluoro-isoindoline-1,3-dione (73 mg, 0.24 mmol, 1 eq) and diisopropylethylamine (96 mg, 0.74 mmol, 129.65 uL, 3 eq) in dimethylsulfoxide (3 mL) was stirred at 120° C. for 1.5 h. The pH was adjusted to 6 with formic acid. The mixture was filtered and concentrated under reduced pressure. The residue was purified by prep-HPLC (column: Shim-pack C18 150*25*10 um; mobile phase: [water (0.225% FA)-ACN]; B %: 15%-45%, 10 min). 5-[4-[2-[1-[1-[5-(Dimethylamino)-3-isoquinolyl] pyrrolo[2,3-c]pyridin-5-yl]-4-piperidyl]ethyl]piperazin-1-yl]-2-(2,6-dioxo-3-piperidyl)-6-fluoro-isoindoline-1,3-dione formate (90 mg, 0.11 mmol, 44% yield) was obtained as a yellow solid.

Using analogous procedures the following examples were prepared by routes alternative to the routes described earlier: Exemplary Compound 480 (from 3-bromo-5-nitro-isoquinoline obtained in step 1—see the scheme below) and Exemplary Compound 512 (from N,N-dimethyl-3-[5-[4-(2-piperazin-1-ylethyl)-1-piperidyl]pyrrolo[2,3-c] pyridine-1-yl]isoquinolin-5-amine obtained in step 5—see the scheme below).

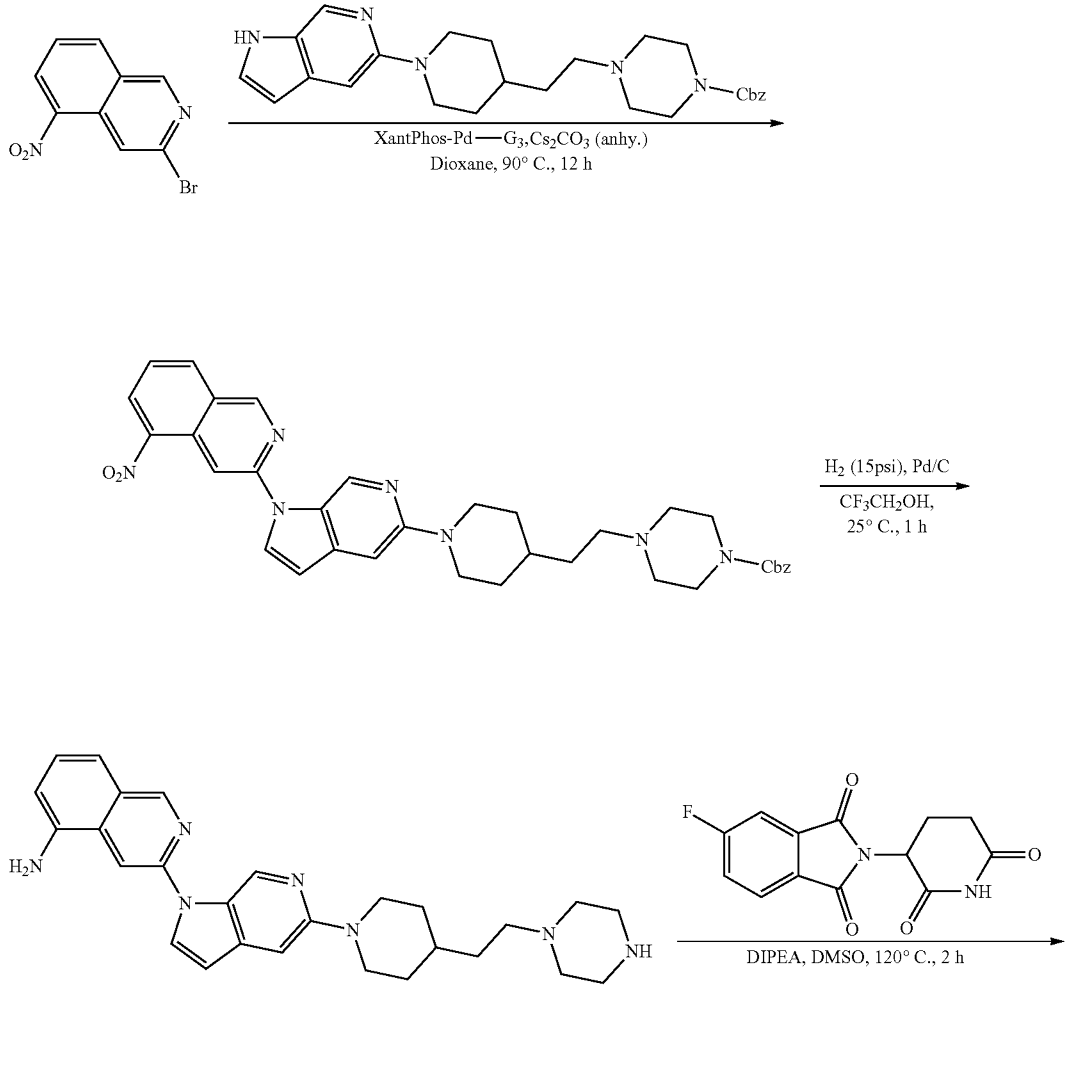

-continued
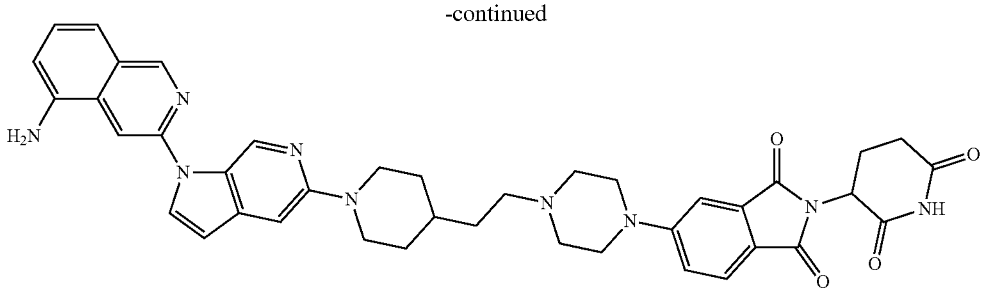
Exemplary Compound 480
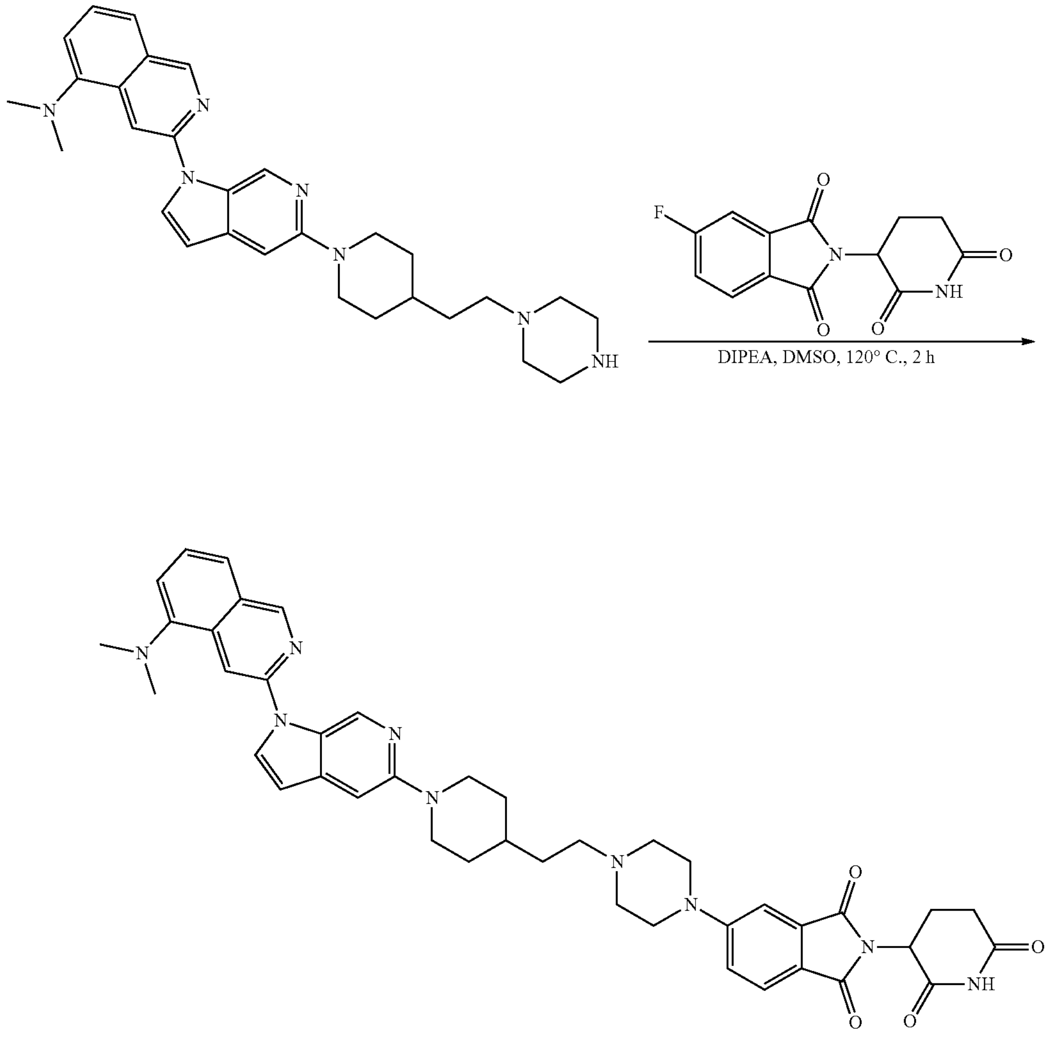
Exemplary Compound 512
Exemplary Synthesis of Exemplary Compound 566
Prepared according to the schemes below using procedures described for other examples above as well as general procedures known to those skilled in the art.

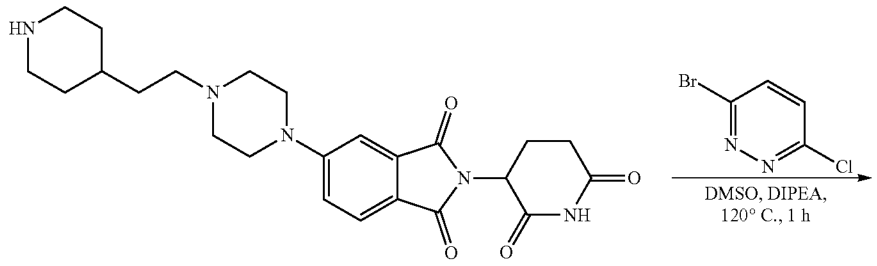
prepared as described for Exemplary Compound 451
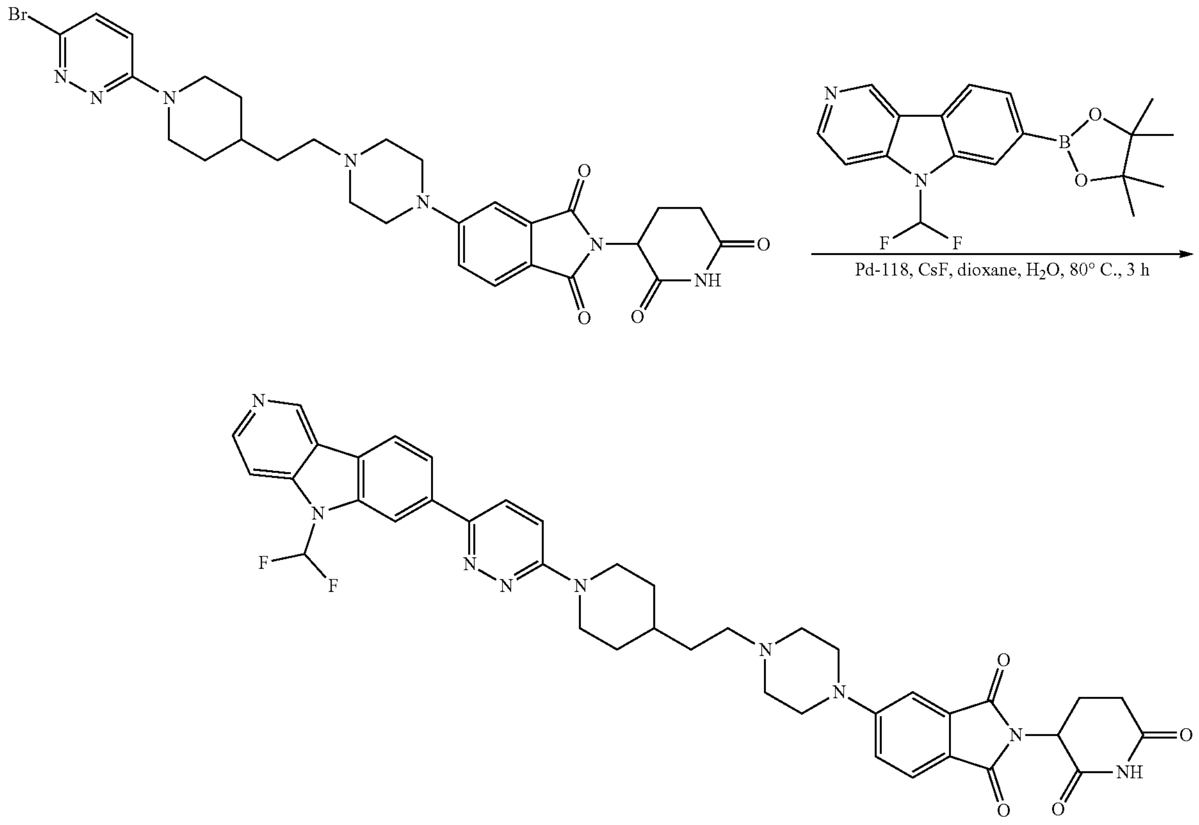
Exemplary Compound 566
Exemplary Synthesis of Exemplary Compound 569
Prepared according to the schemes below using procedures described for other examples above as well as general procedures known to those skilled in the art.
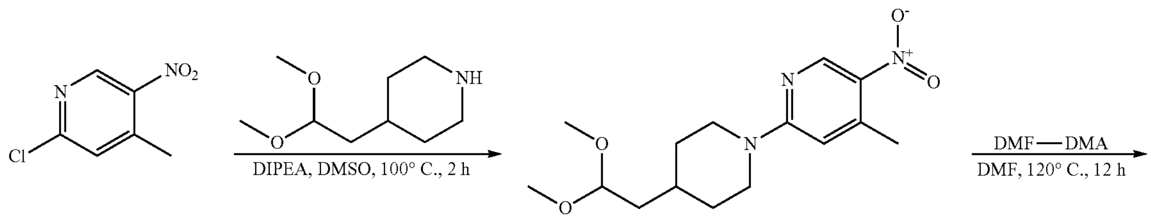

-continued
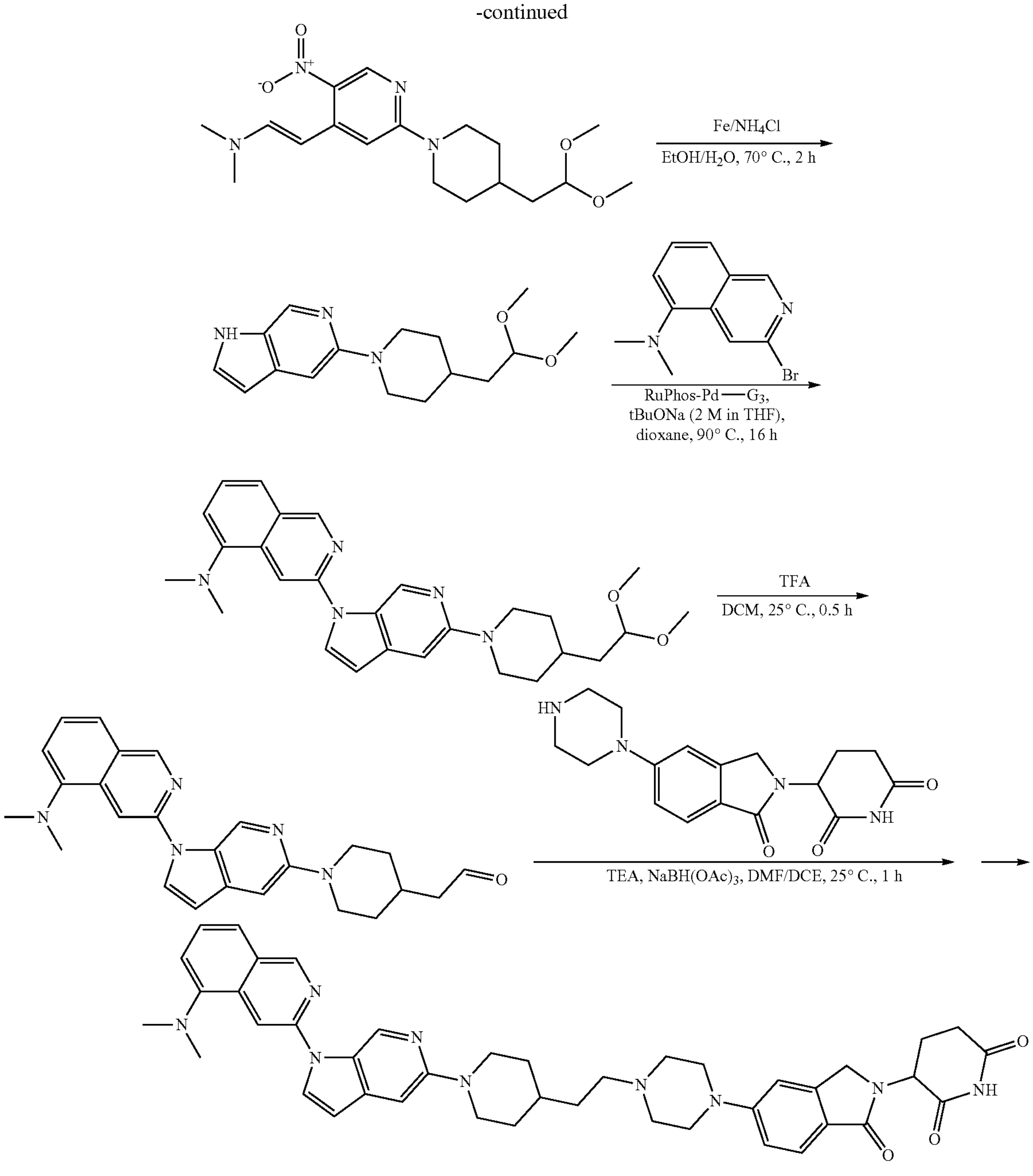
Exemplary Compound 569
Exemplary Synthesis of Exemplary Compound 589
Prepared according to the scheme below using procedures described for other examples above as well as general procedures known to those skilled in the art.
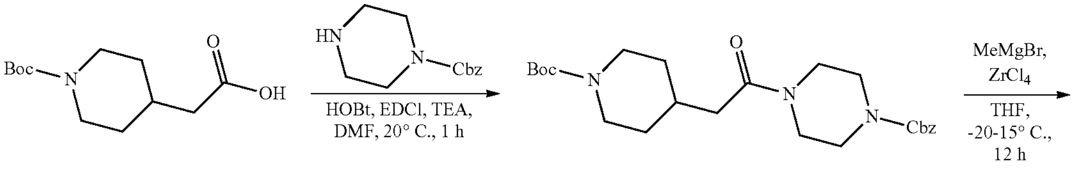

-continued

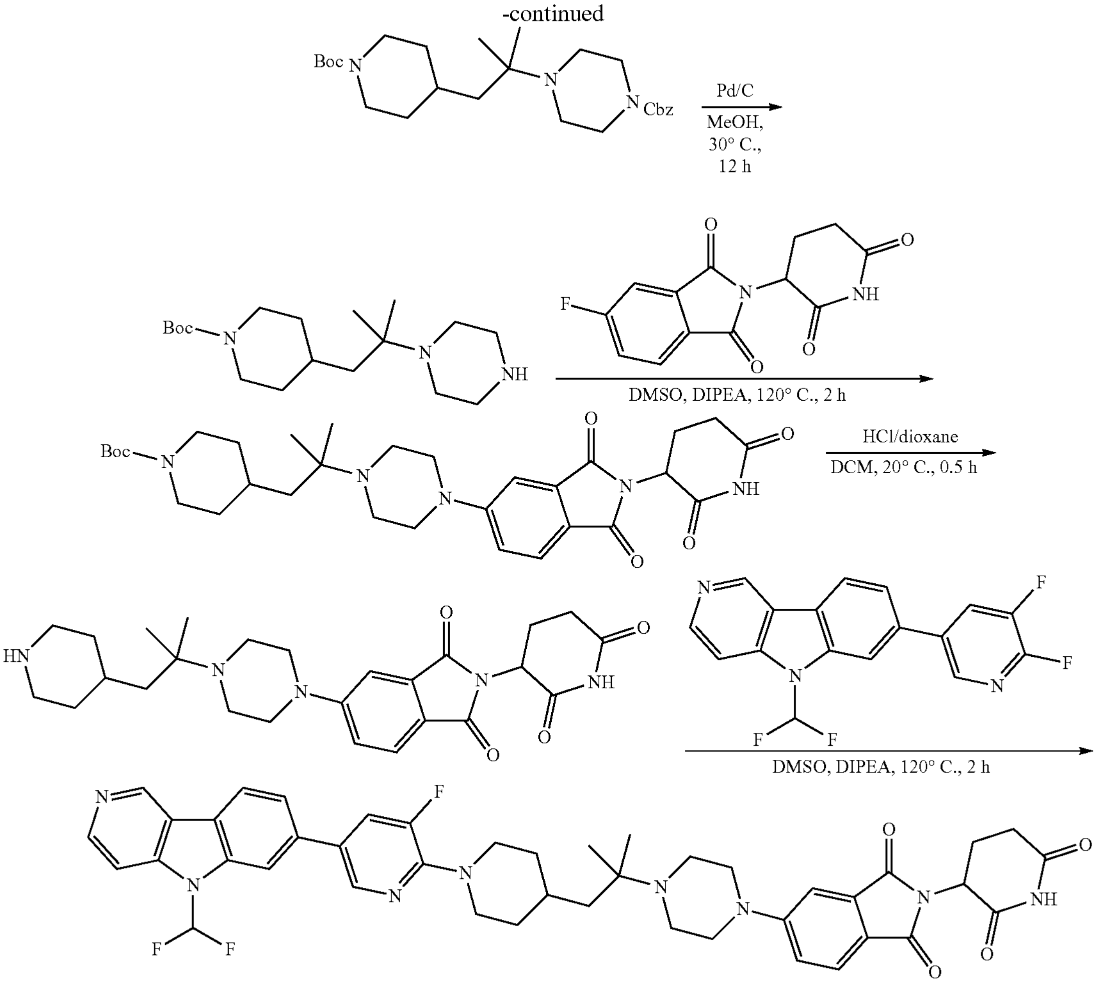

Exemplary Compound 589

Exemplary Synthesis of Exemplary Compound 591

Step 1

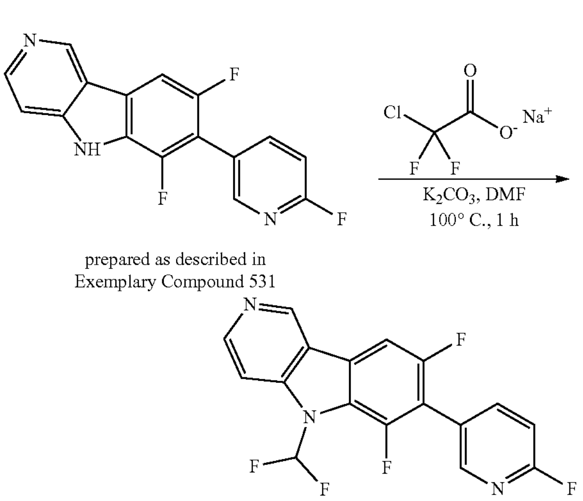

To a solution of 6,8-difluoro-7-(6-fluoro-3-pyridyl)-5H-pyrido[4,3-b]indole (200 mg, 0.66 mmol, 1 eq) and potassium carbonate (184 mg, 1.34 mmol, 2 eq) in dimethylformamide (5 mL) was added sodium 2-chloro-2,2-difluoroacetate (122 mg, 0.8 mmol, 1.2 eq). The reaction mixture was stirred at 100° C. for 1 hr. The reaction mixture was quenched by water (50 mL) and extracted with ethyl acetate (50 mL×3). The combined organic layers were washed with brine (50 mL×3), dried over anhydrous sodium sulfate, filtered and concentrated under reduced pressure. The residue was purified by silica gel column chromatography (dichloromethane:methanol=100/1 to 10/1). 5-(Difluoromethyl)-6,8-difluoro-7-(6-fluoro-3-pyridyl)pyrido[4,3-b]indole (50 mg, 0.14 mmol, 21% yield) was obtained as a yellow oil.

5-(Difluoromethyl)-6,8-difluoro-7-(6-fluoro-3-pyridyl) pyrido[4,3-b]indole was converted to the title compound according to the schemes below using procedures described for other examples above as well as general procedures known to those skilled in the art.

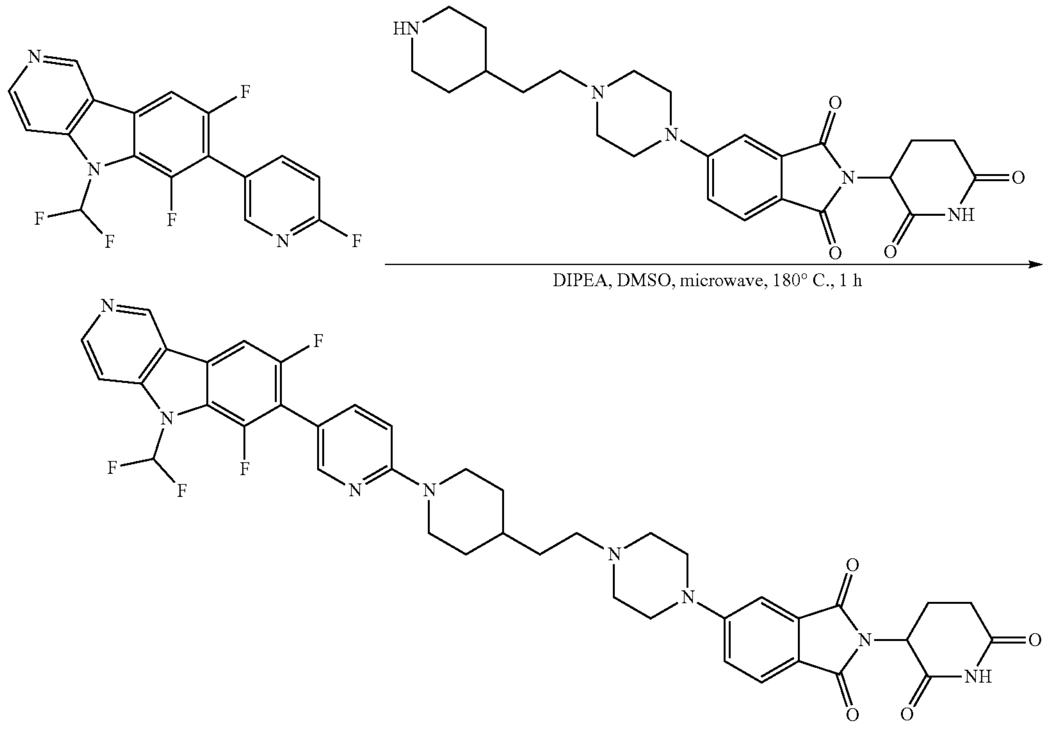

Exemplary Compound 591

Exemplary Synthesis of Exemplary Compounds 634 and 685

Step 1

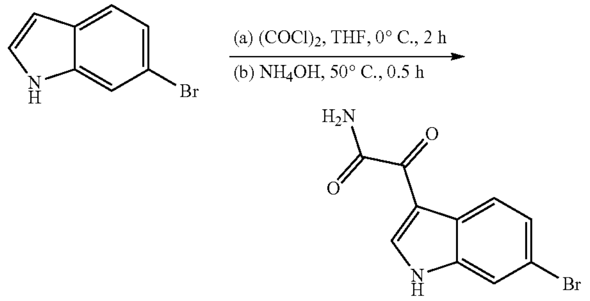

To a stirred of 6-bromo-1H-indole (10 g, 51.01 mmol, 1 eq) in tetrahydrofuran (100 mL) was added oxalyl dichloride (10.00 g, 78.78 mmol, 6.90 mL, 1.54 eq), The mixture was stirred at 0° C. for 2 hr, then the mixture was added to 28% aqueous ammonia (71.43 mL, 519.26 mmol, 10.18 eq). The reaction was stirred at 50° C. for 0.5 h. The reaction mixture was extracted with ethyl acetate (200 mL×3). The organic phase was washed with brine (200 mL), dried over anhydrous sodium sulfate, filtered and concentrated in vacuum to give a residue. The residue was stirred with ethyl acetate/petroleum ether (10/1, 100 mL) at 25° C. for 1 hr, filtered and the cake was collected. Compound 2-(6-bromo-1H-indol-3-yl)-2-oxoacetamide (5.5 g, 20.59 mmol, 40% yield) was obtained as a yellow solid.

Step 2

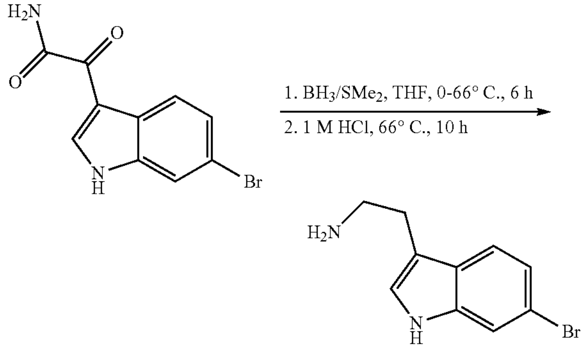

To a solution of 2-(6-bromo-1H-indol-3-yl)-2-oxoacetamide (5.5 g, 20.59 mmol, 1 eq) in tetrahydrofuran (55 mL) was added borane-dimethyl sulfide complex (10 M, 6.18 mL, 3 eq) under nitrogen at 0° C. The resulting mixture was slowly warmed to 25° C. and then stirred at 66° C. for 6 h. The reaction mixture was then cooled to 25° C. and hydrochloric acid (1 M, 91.67 mL, 4.45 eq) was carefully added, and the mixture was stirred at 66° C. for 10 hr. The reaction mixture was poured into water (200 mL). The mixture was extracted with ethyl acetate (200 mL×3). The organic phase was washed with brine (200 mL), dried over anhydrous sodium sulfate, filtered and concentrated in vacuum to give a residue. The residue was purified by silica gel column chromatography (ethyl acetate:methanol=1/0 to 1/1). Compound 2-(6-bromo-1H-indol-3-yl)ethanamine (4.0 g, 14.22 mmol, 69% yield) was obtained as a brown solid.

Step 3

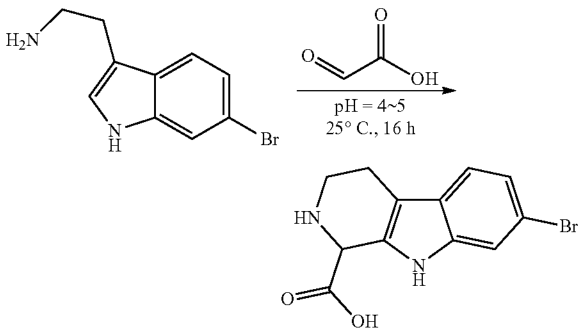

To an solution of 2-(6-bromo-1H-indol-3-yl)ethanamine (4.0 g, 16.73 mmol, 1 eq) in 4 N hydrochloric acid (30 mL) was added 2-oxoacetic acid (3.4 g, 22.96 mmol, 2.56 mL, 1.37 eq) under nitrogen at 25° C., and the mixture was stirred at 25° C. for 0.5 h. The resulting mixture was adjusted to pH 3.5 with 6 N sodium hydroxide solution and stirred at 25° C. for 10 h. The reaction mixture was adjusted to pH 6.0 with 6 N sodium hydroxide solution and stirred at 0° C. for 1 hr, Then filtered and collected the cake. The crude product 7-bromo-2,3,4,9-tetrahydro-1H-pyrido[3,4-b]indole-1-carboxylic acid (4.9 g, crude) was obtained as a brown solid and used in the next step without further purification.

Step 4

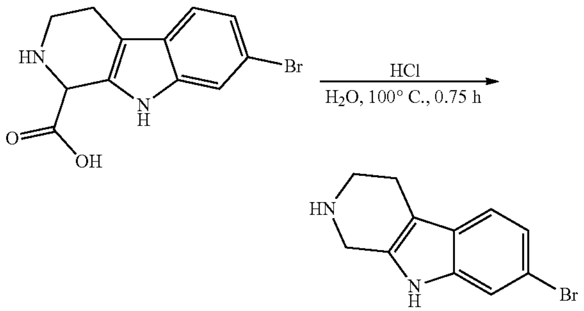

To an solution of 7-bromo-2,3,4,9-tetrahydro-1H-pyrido[3,4-b]indole-1-carboxylic acid (4.9 g, 16.60 mmol, 1 eq) in water (125 mL) was added 36% aqueous hydrochloric acid (15 mL, 151.07 mmol, 9.10 eq), and the mixture was stirred at 100° C. for 0.5 hr. Then additional 36% hydrochloric acid (15 mL, 151.07 mmol, 9.10 eq) was added, and the mixture was stirred at 100° C. for 0.25 h. pH was adjusted to 7.0 with 20% sodium hydroxide solution, and the mixture was stirred at 0° C. for 1 hr, then filtered and the cake was collected. The crude product 7-bromo-2,3,4,9-tetrahydro-1H-pyrido[3,4-b]indole (3.5 g, 10.59 mmol) was obtained as a black-brown solid and used in the next step without further purification.

Step 5

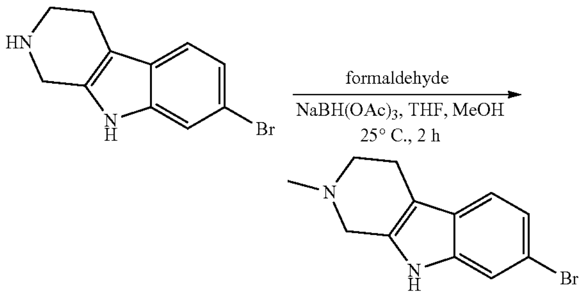

A solution of 7-bromo-2,3,4,9-tetrahydro-1H-pyrido[3,4-b]indole (3.5 g, 13.94 mmol, 1 eq) and 37% aqueous formaldehyde (1.05 g, 12.94 mmol, 0.96 mL, 0.93 eq) in tetrahydrofuran (18 mL) and methanol (18 mL) was stirred at 25° C. for 0.5 h. Then sodium triacetoxyborohydride (4.67 g, 22.02 mmol, 1.58 eq) was added to the mixture, and it was stirred at 25° C. for 1.5 h. The reaction mixture was concentrated in vacuum to give a residue. The residue was purified by silica gel column chromatography (dichloromethane:methanol=5/1). Compound 7-bromo-2-methyl-2,3,4,9-tetrahydro-1H-pyrido[3,4-b]indole (1.5 g, 5.66 mmol, 41% yield) was obtained as a yellow solid.

Step 6

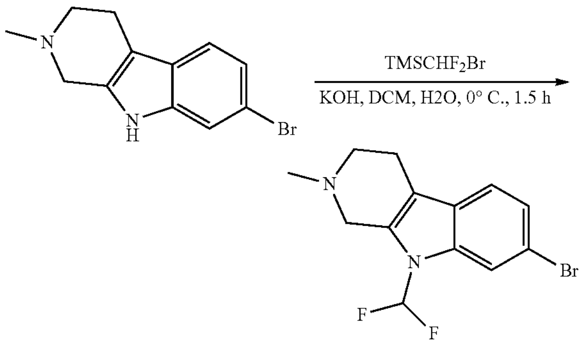

To a solution of 7-bromo-2-methyl-2,3,4,9-tetrahydro-1H-pyrido[3,4-b]indole (500 mg, 1.89 mmol, 1 eq) in dichloromethane (20 mL) was dropwise added potassium hydroxide (625.00 mg, 11.14 mmol, 5.91 eq) in water (5 mL) at 0° C. After stirred at 0° C. for 10 min, (bromodifluoromethyl)trimethylsilane (350 mg, 1.72 mmol, 0.91 eq) in dichloromethane (5 mL) was slowly dropwise added to the above reaction mixture at 0° C. and stirred at 0° C. for 1 h 20 min. The reaction mixture was separated, washed with brine 10 mL, dried over anhydrous sodium sulfate, filtered and concentrated under reduced pressure to give a residue. The residue was purified by silica gel column chromatography (ethyl acetate:methanol=100/1 to 10/1). Compound 7-bromo-9-(difluoromethyl)-2-methyl-2,3,4,9-tetrahydro-1H-pyrido[3,4-b]indole (150 mg, 0.47 mmol, 25% yield) was obtained as a yellow solid.

7-Bromo-9-(difluoromethyl)-2-methyl-2,3,4,9-tetrahydro-1H-pyrido[3,4-b]indole was converted to the Exemplary Compound 634 and the Exemplary Compound 685 according to the schemes below using procedures described for other examples above as well as general procedures known to those skilled in the art.
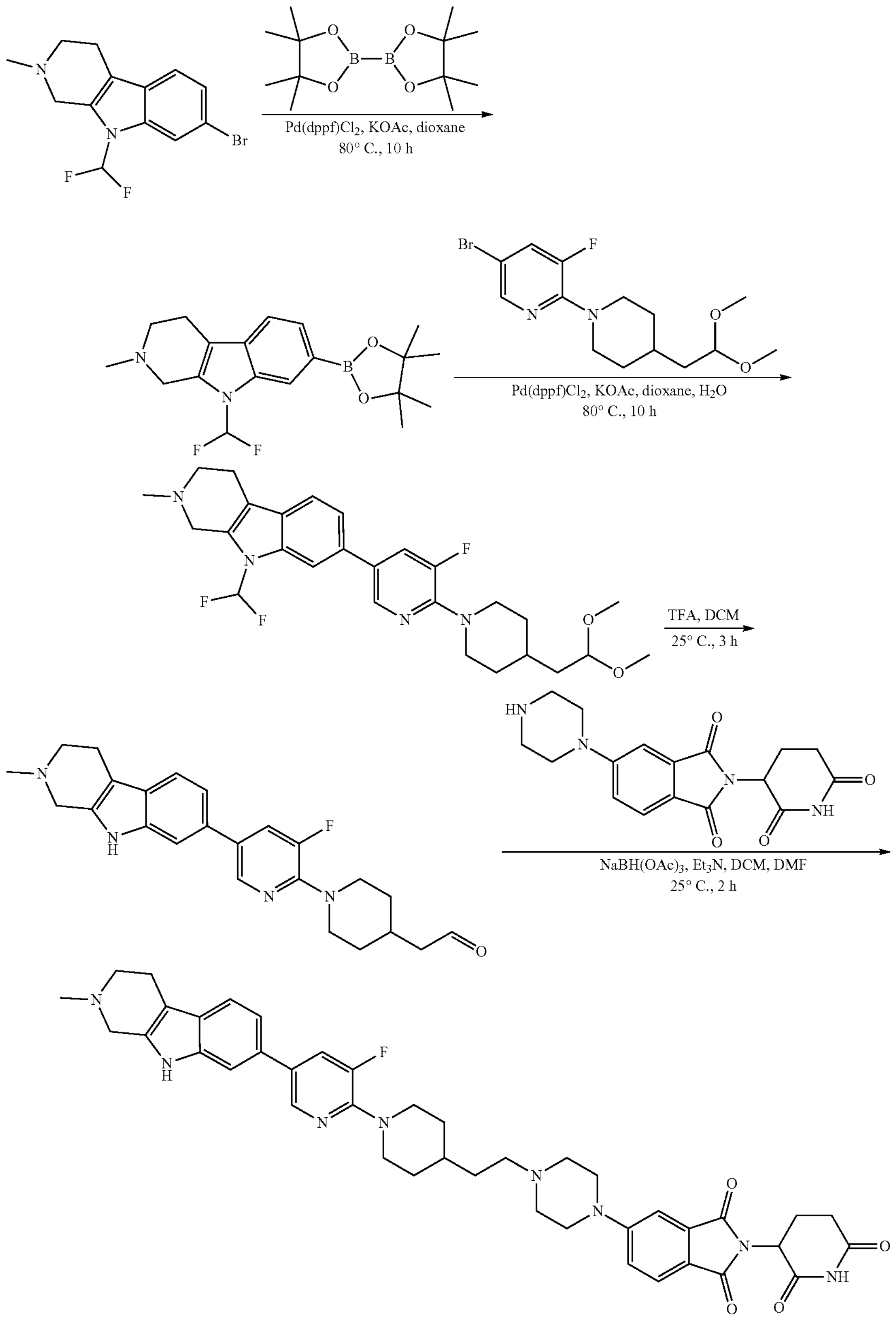
Exemplary Compound 634

-continued

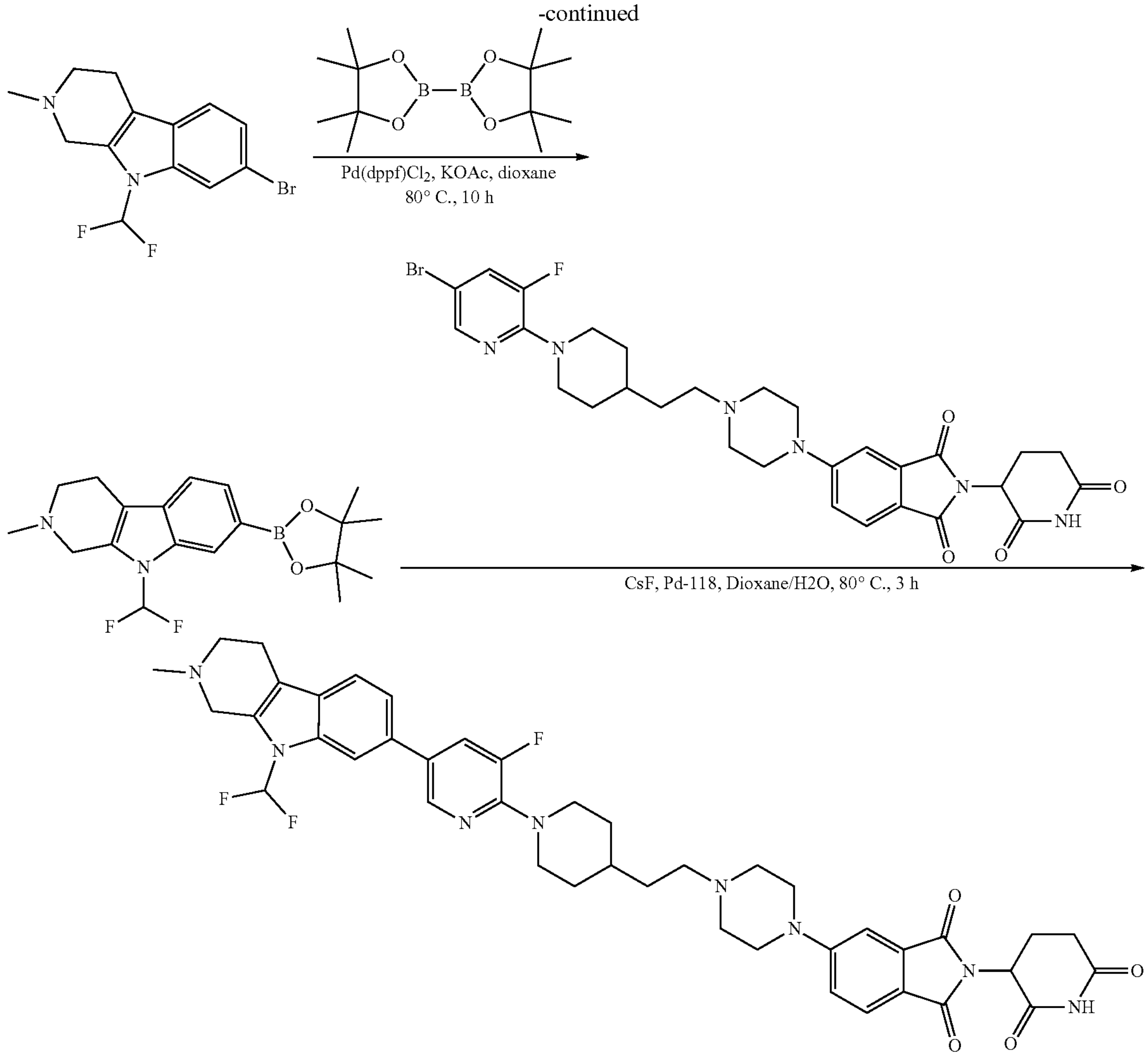

Exemplary Compound 685

Exemplary Synthesis of Exemplary Compound 675

Step 1

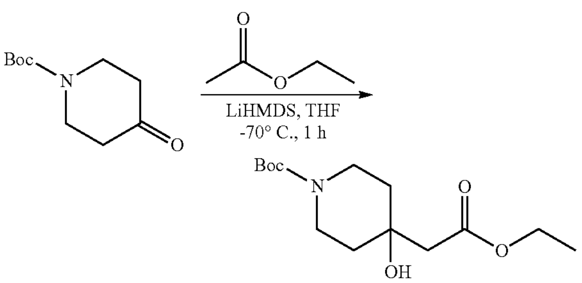

To a stirred solution of Lithium bis(trimethylsilyl)amide (1 M, 50 mL, 1 eq) in tetrahydrofuran (50 mL) under inert atmosphere was added ethyl acetate (4.42 g, 50.1 mmol, 1 eq) dropwise for 10 min at −70° C. The reaction mixture was stirred for 20 min, then tert-butyl 4-oxopiperidine-1-carboxylate (10 g, 50.19 mmol, 1 eq) in tetrahydrofuran (50 mL) was added. The reaction mixture was stirred for 30 min. The reaction mixture was diluted with water (50 mL) and extracted with dichloromethane (2×30 mL). The combined organic extracts were dried over sodium sulfate, filtered and concentrated under reduced pressure. The residue was purified by column chromatography (petroleum ether/ethyl acetate=20/1 to 10:1). tert-Butyl 4-(2-ethoxy-2-oxo-ethyl)-4-hydroxy-piperidine-1-carboxylate (12 g, 41 mmol, 83% yield) was obtained as a colorless oil.

Step 2

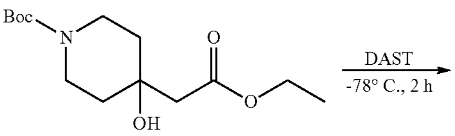

-continued

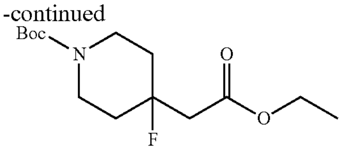

To a solution of tert-butyl 4-(2-ethoxy-2-oxo-ethyl)-4-hydroxy-piperidine-1-carboxylate (5 g, 17.4 mmol, 1 eq) in dichloromethane (50 mL) was added diethylaminosulfur trifluoride (4.21 g, 26.1 mmol, 1.5 eq) at −78° C. The mixture was stirred at −78° C. for 2 hr. The mixture was then poured into aqueous sodium bicarbonate (200 mL), extracted with ethyl acetate (200 mL+100 mL), organic layer was dried over sodium sulfate, and solvent was removed under vacuum. The oily residue was taken into ethanol (150 mL) and water (150 mL). Magnesium sulfate (5.4 g) was then added, followed by potassium permanganate (7.2 g). The mixture was stirred at 25° C. for 1 hour, then extracted with ethyl acetate (600 mL). Organic layer was washed with brine (150 mL), dried over sodium sulfate, and solvent was removed under vacuum. The residue was purified by column chromatography (petroleum ether/ethyl acetate=20/1 to 10/1). tert-Butyl 4-(2-ethoxy-2-oxo-ethyl)-4-fluoro-piperidine-1-carboxylate (0.6 g, 2.07 mmol, 11% yield) was obtained as a colorless oil.

Step 3

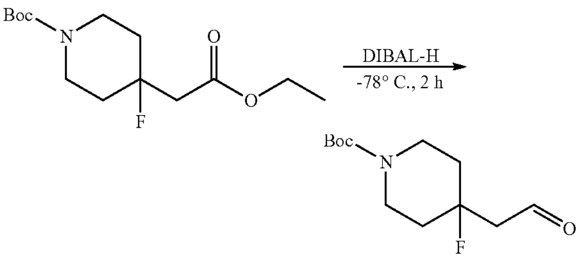

To tert-butyl 4-(2-ethoxy-2-oxo-ethyl)-4-fluoro-piperidine-1-carboxylate (0.5 g, 1.73 mmol, 1 eq) in dichloromethane (8 mL) at −78° C. under nitrogen was added diisobutylaluminum hydride (1 M, 2.5 mL, 1.5 eq) under nitrogen. The mixture was stirred at −78° C. for 2 hr, then warmed up to room temperature. The mixture was then poured on ice (100 g), acidified to pH=3, and extracted with ethyl acetate (20 mL+10 mL×3). Combined ethyl acetate layer was then dried over sodium sulfate, solvent removed. The residue was purified by column chromatography (petroleum ether/ethyl acetate=20/1 to 10/1). tert-Butyl 4-fluoro-4-(2-oxoethyl)piperidine-1-carboxylate (180 mg, 0.7 mmol, 42% yield) was obtained as a colorless oil.

tert-Butyl 4-fluoro-4-(2-oxoethyl)piperidine-1-carboxylate was converted into the title compound according to the schemes below using procedures described for other examples above as well as general procedures known to those skilled in the art.

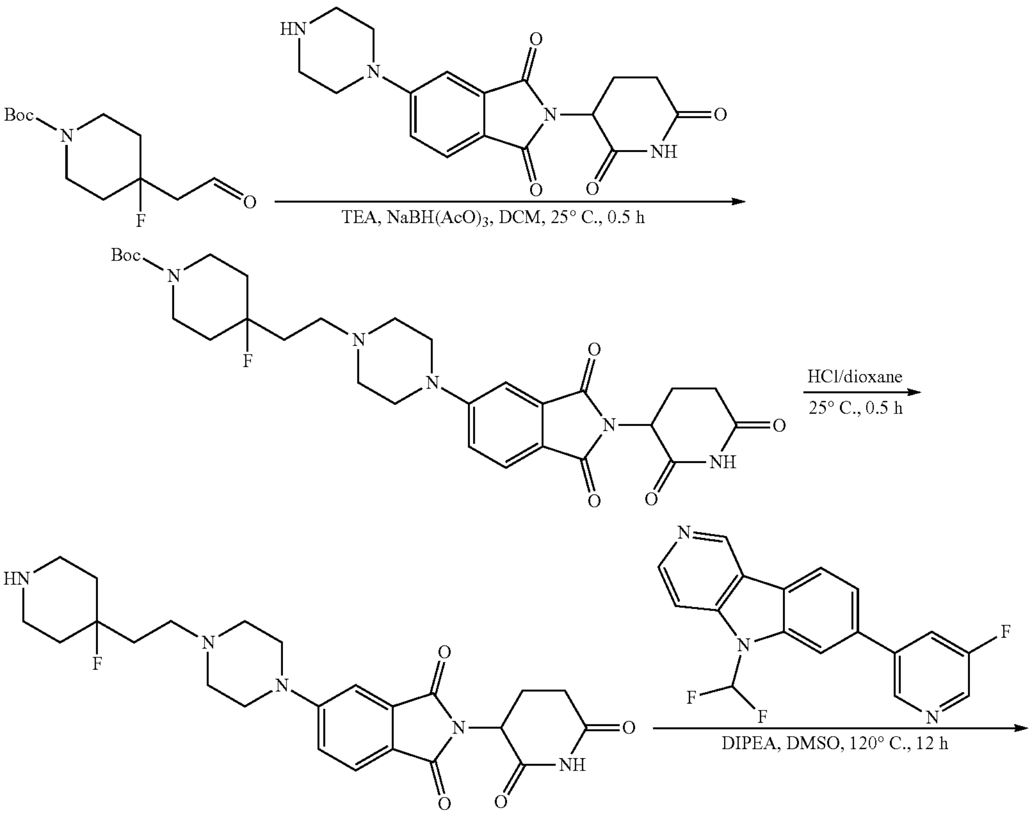

-continued
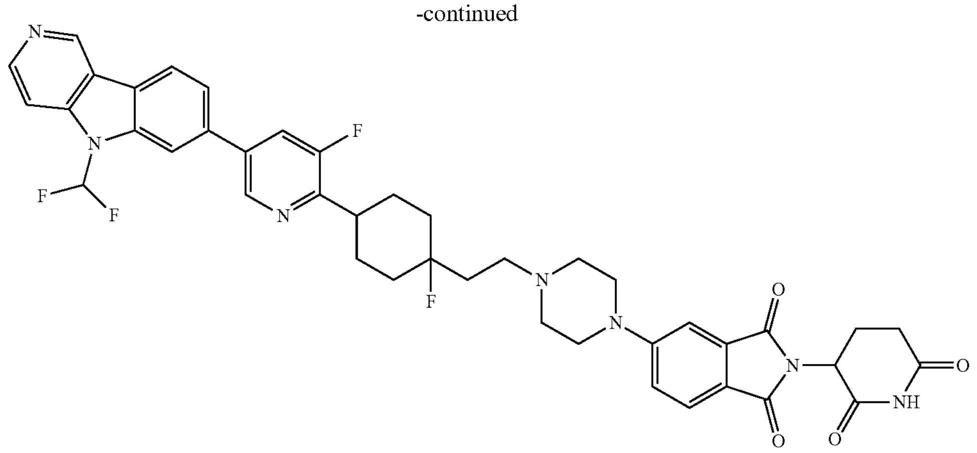
Exemplary Compound 675
Exemplary Synthesis of Exemplary Compound 682
Prepared according to the schemes below using procedures described for other examples above as well as general procedures known to those skilled in the art.
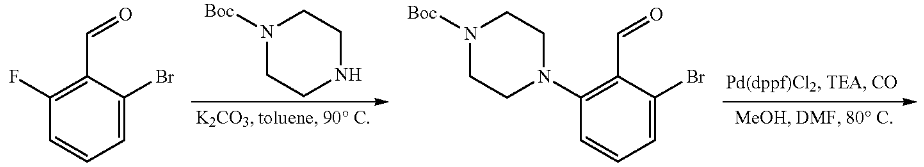
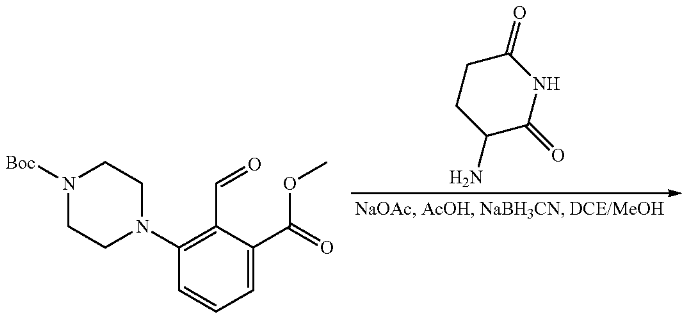
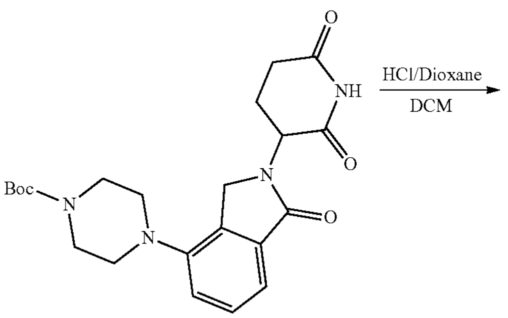

-continued
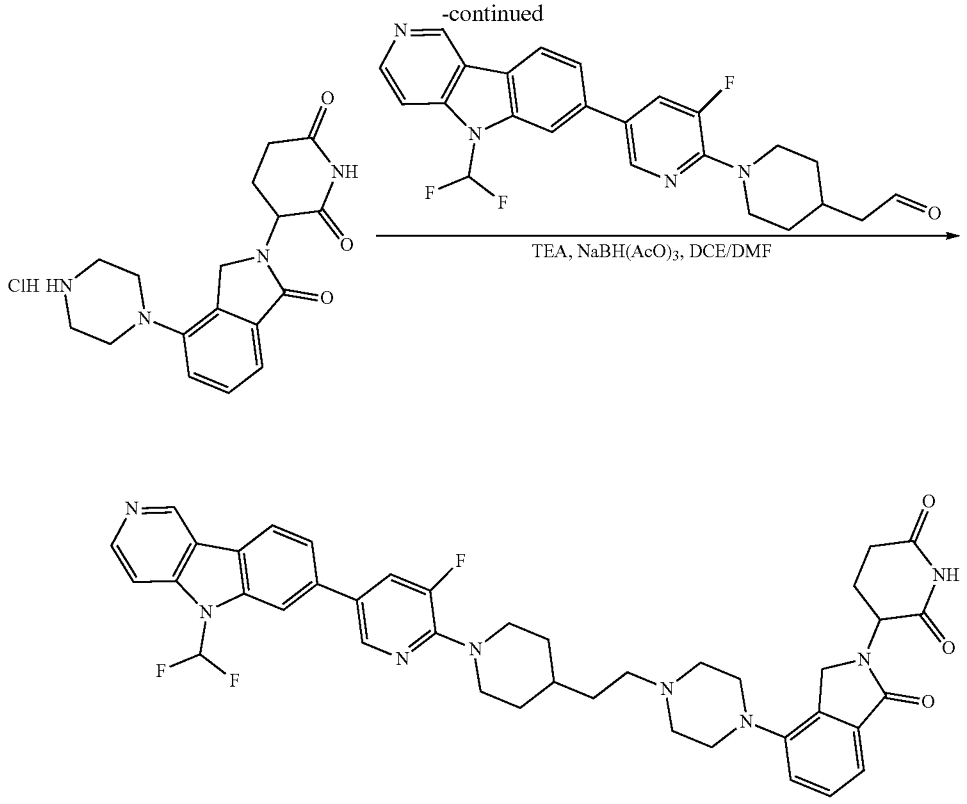
Exemplary Compound 683
Exemplary Synthesis of Exemplary Compound 637
Prepared according to the scheme below using procedures described for other examples above as well as general procedures known to those skilled in the art.
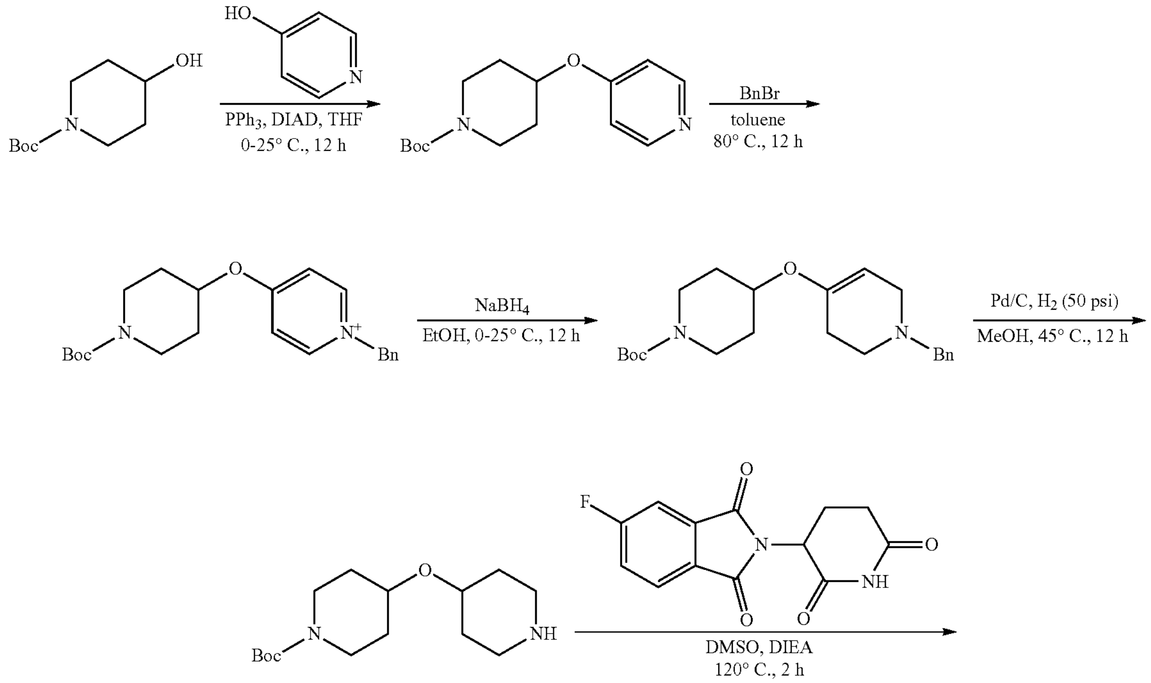

-continued
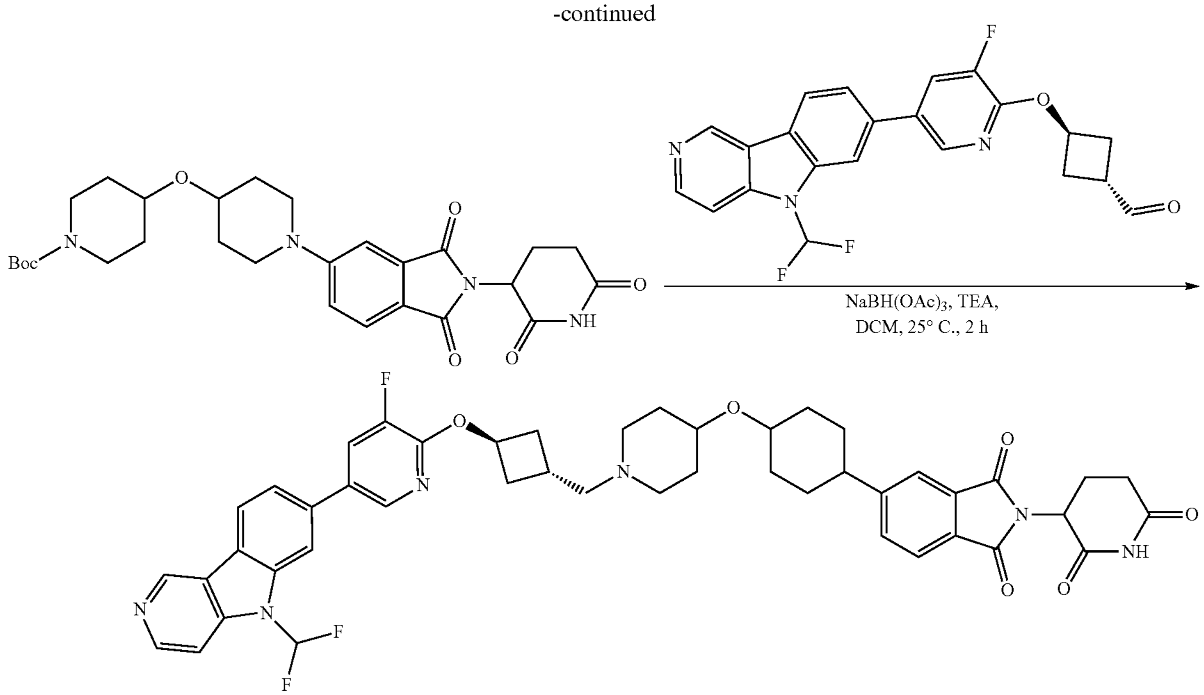
Exemplary Compound 637
Exemplary Synthesis of Exemplary Compound 612
Prepared according to the schemes below using procedures described for other examples above as well as general procedures known to those skilled in the art.
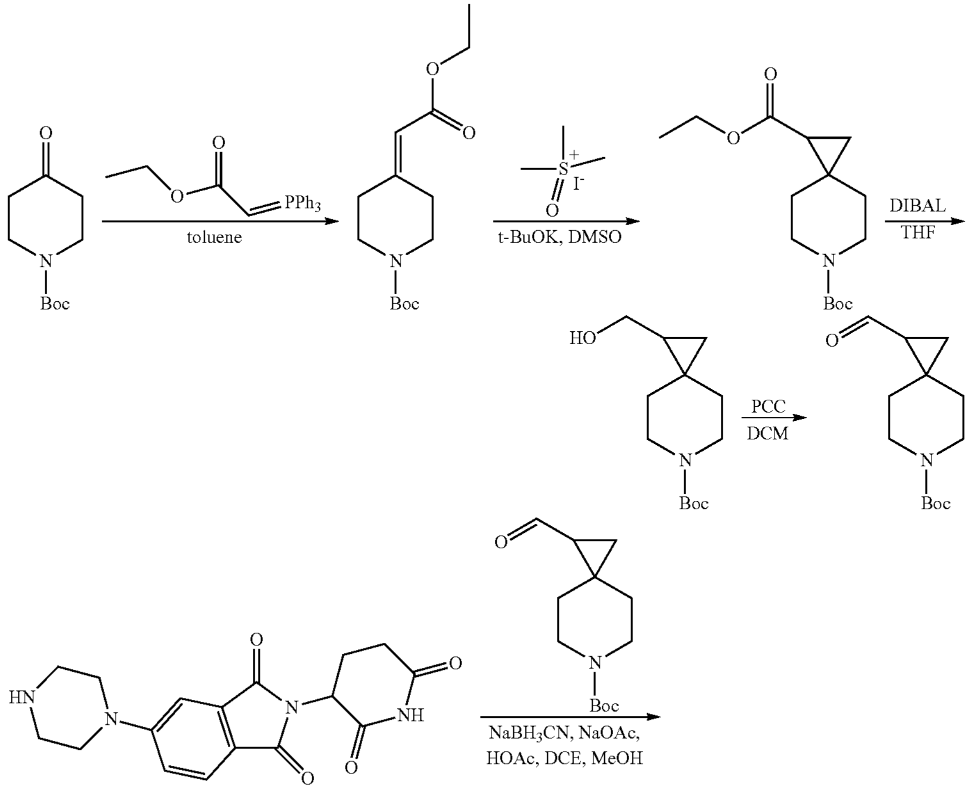

-continued

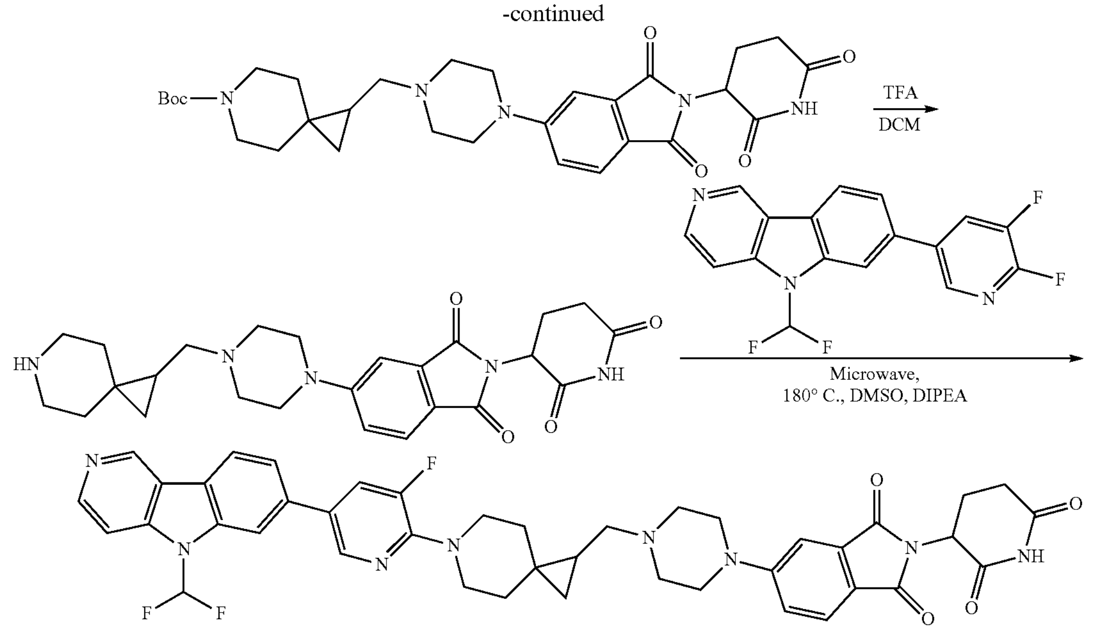

Exemplary Compound 612

Exemplary Synthesis of Exemplary Compound 674

Step 1

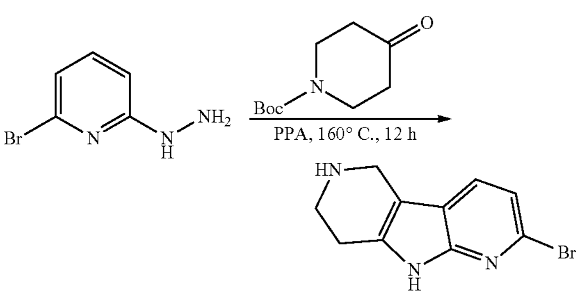

A solution of (6-bromo-2-pyridyl)hydrazine (18 g, 81.37 mmol, 1 eq) and tert-butyl 4-oxopiperidine-1-carboxylate (17.83 g, 89.51 mmol, 1.1 eq) in polyphosphoric acid (140 mL) was stirred at 160° C. for 8 hr. The reaction mixture was cooled to 25° C. and ice-water (400 mL) was added. The mixture was stirred until the gummy material was dissolved. Then the pH of the reaction mixture was adjusted to 12-13 by adding solid sodium hydroxide. After adjusting the pH, the reaction mixture was stirred at 0° C. for 0.5 hr, the precipitate was collected by filtration and washed with water (100 mL). The precipitate was suspended in propan-2-ol (400 mL) and heated at reflux for 10 minutes. The reaction mixture was filtered, the precipitate was washed with propan-2-ol (100 mL) and the combined filtrate was evaporated. The crude product was purified by Prep-HPLC (column: Phenomenex luna C18 250*50 mm*10 um; mobile phase: [water (10 mM NH4HCO3)-ACN]; B %: 20%-50%, 20 min). The desired product 2-bromo-6,7,8,9-tetrahydro-5H-pyrrolo[2,3-b:4,5-c']dipyridine (3 g, 10.83 mmol, 27% yield) was obtained as yellow solid.

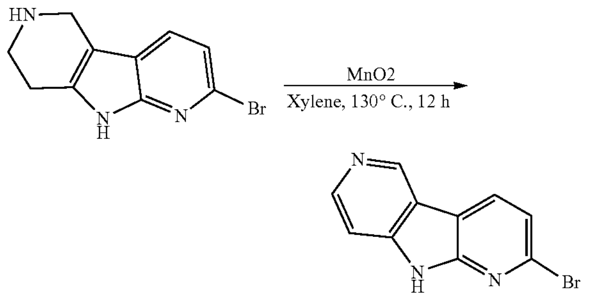

To a mixture of 2-bromo-6,7,8,9-tetrahydro-5H-pyrrolo[2,3-b:4,5-c']dipyridine (0.8 g, 3.17 mmol, 1 eq) in xylene (8 mL) was added manganese dioxide (5.52 g, 63.46 mmol, 20 eq) at 25° C. The mixture was stirred at 130° C. for 16 hr. The reaction mixture was filtered and the filtrate was concentrated. The crude 2-bromo-9H-pyrrolo[2,3-b:4,5-c']dipyridine (750 mg) was obtained as a yellow solid and used directly in the next step.

Step 3

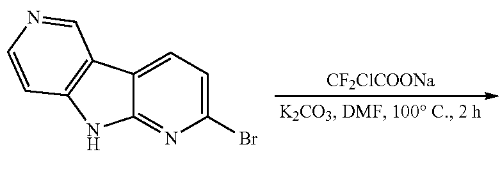

-continued

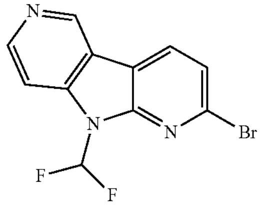

To a solution of 2-bromo-9H-pyrrolo[2,3-b:4,5-c']dipyridine (300 mg, 1.21 mmol, 1 eq) in dimethylformamide (3 mL) was added sodium chlorodifluoroacetate (221 mg, 1.45 mmol, 1.2 eq) and potassium carbonate (334 mg, 2.42 mmol, 2 eq). The mixture was stirred at 100° C. for 2 hr. The reaction mixture was poured into water (10 mL) and extracted with ethyl acetate (20 mL×3). The combined organic layer was washed with brine (20 mL), dried over anhydrous sodium sulfate, filtered and the filtrate was concentrated. The crude product was purified by Prep-HPLC (column: Phenomenex luna C18 150*25 mm*10 um; mobile phase: [water (0.1% TFA)-ACN]; B %: 18%-38%, 10 min). The desired product 2-bromo-9-(difluoromethyl)-9H-pyrrolo[2,3-b:4,5-c']dipyridine (100 mg, 0.33 mmol, 27% yield) was obtained as a yellow solid.

2-Bromo-9-(difluoromethyl)-9H-pyrrolo[2,3-b:4,5-c'] dipyridine was converted to the title compound according to the scheme below using procedures described for other examples above as well as general procedures known to those skilled in the art.

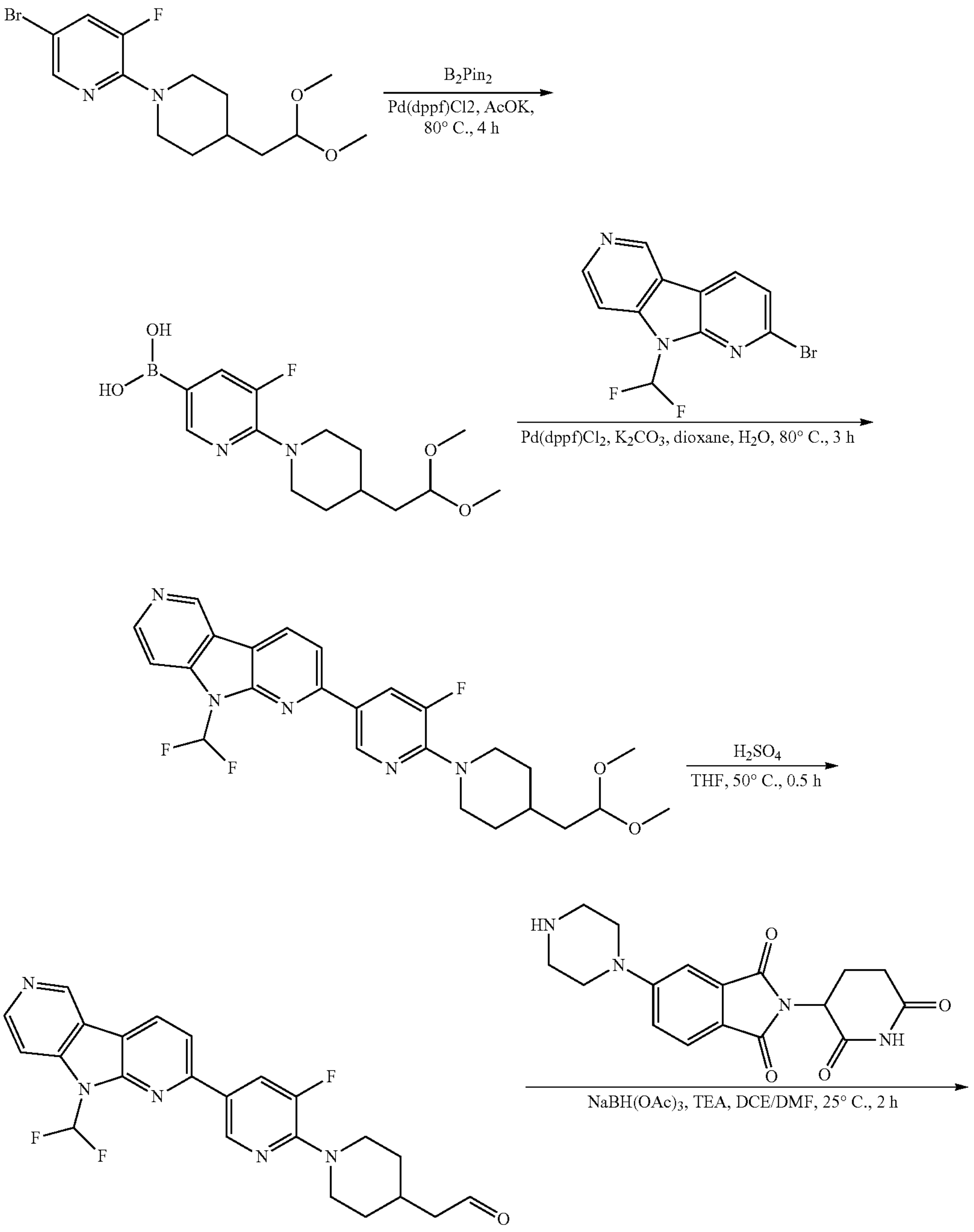

-continued

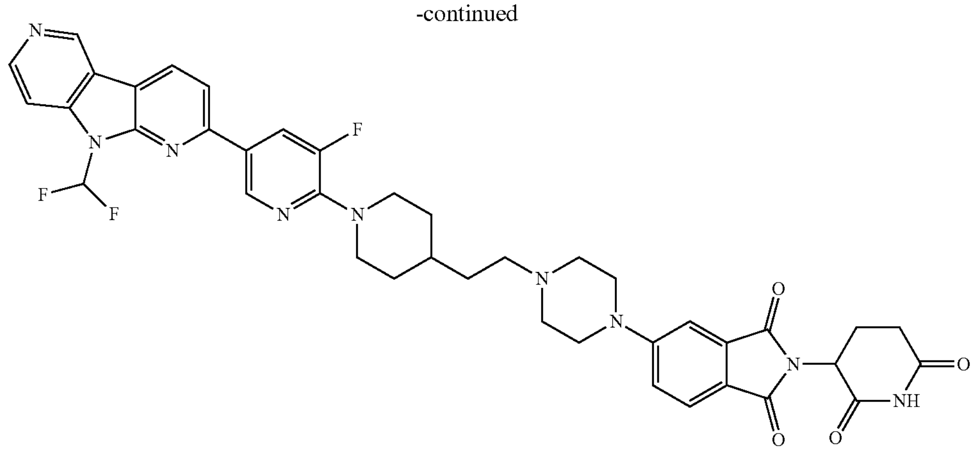

Exemplary Compound 674

Exemplary Synthesis of Exemplary Compound 629

Step 1

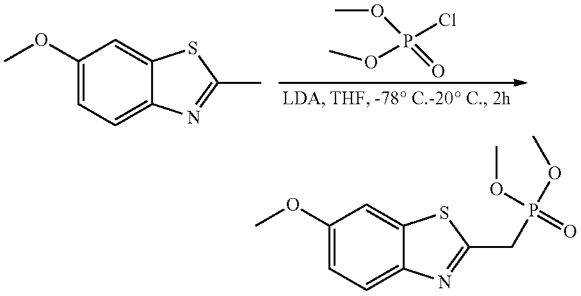

To a solution of lithium diisopropylamide (2 M, 16.74 mL, 3 eq) was added 6-methoxy-2-methyl-1,3-benzothiazole (2 g, 11.16 mmol, 1 eq) in tetrahydrofuran (20 mL) at −70° C. Then the mixture was stirred at −70° C. for 30 min. Dimethyl phosphorochloridate (1.61 g, 11.16 mmol, 1 eq) was added into the mixture at −70° C., and the mixture was stirred at −70° C. for 10 min and at 25° C. for 1 hour 20 min. The mixture was quenched with saturated solution of ammonium chloride (20 mL), extracted with ethyl acetate (20 mL×3), washed with brine (30 mL), dried over sodium sulfate, filtered and then concentrated. The residue was purified by prep-TLC (petroleum ether:ethyl acetate=3:1). 2-(Dimethoxyphosphorylmethyl)-6-methoxy-1,3-benzothiazole (1.7 g, 5.92 mmol, 53% yield) was obtained as a yellow oil.

Step 2

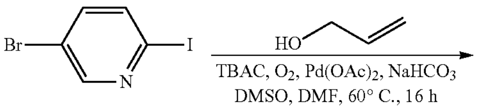

-continued

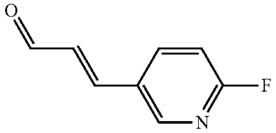

To a solution of 2-fluoro-5-iodo-pyridine (10 g, 44.85 mmol, 1 eq) and prop-2-en-1-ol (3.91 g, 67.27 mmol, 1.5 eq) in N,N-dimethylformamide (50 mL) and dimethyl sulfoxide (50 mL) was added palladium acetate (2.01 g, 8.97 mmol, 0.2 eq), tetrabutylammonium chloride (12.46 g, 44.85 mmol, 12.54 mL, 1 eq) and sodium bicarbonate (9.42 g, 112.11 mmol, 2.5 eq). Then the mixture was purged with $O_2$ (15 Psi) for 3 times and stirred at 60° C. for 12 hours. The mixture was filtered, diluted with water (100 mL), extracted with ethyl acetate (100 mL×3), washed with brine (100 mL), dried over sodium sulfate, filtered and then concentrated. The residue was purified by prep-TLC (petroleum ether: ethyl acetate=3:1). The residue was further purified by prep-HPLC (column: Phenomenex luna C18 250*50 mm*10 um; mobile phase: [water (0.225% FA)-ACN]; B %: 15%-40%, 25 min). (E)-3-(6-fluoro-3-pyridyl)prop-2-enal (2.5 g, 16.54 mmol, 37% yield) was obtained as a white solid.

Step 3

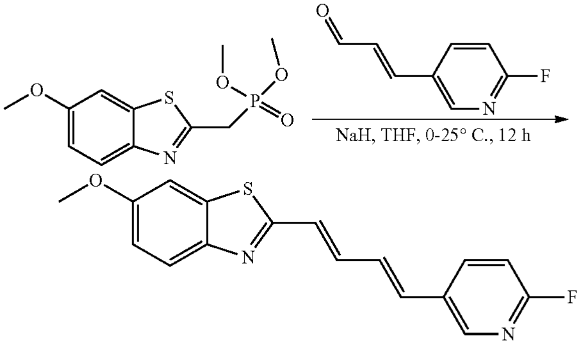

To a solution of 2-(dimethoxyphosphorylmethyl)-6-methoxy-1,3-benzothiazole (700 mg, 2.44 mmol, 1 eq) in tetrahedronfuran (20 mL.) was added sodium hydride (146 mg, 3.66 mmol, 60% purity, 1.5 eq) at 0° C. Then the mixture was stirred at 0° C. for 10 min. The mixture was then warmed to 25° C. and stirred at 25° C. for 20 min. (E)-3-(6-fluoro-3-pyridyl)prop-2-enal (450 mg, 2.68 mmol, 1.1 eq) was added into the mixture at 25° C., and the mixture was stirred at 25° C. for 12 hours. The mixture was quenched with saturated solution of ammonium chloride (20 mL), extracted with ethyl acetate (20 mL×3), washed with brine (30 mL), dried over sodium sulfate, filtered and then concentrated. The residue was purified by prep-TLC (petroleum ether:ethyl acetate=3:1). 2-[(1E,3E)-4-(6-Fluoro-3-pyridyl)buta-1,3-dienyl]-6-methoxy-1,3-benzothiazole (500 mg, 1.50 mmol, 61% yield) was obtained as a yellow solid.

2-[(1E,3E)-4-(6-Fluoro-3-pyridyl)buta-1,3-dienyl]-6-methoxy-1,3-benzothiazole was converted to the title compound according to the scheme below using procedures described for other examples above as well as general procedures known to those skilled in the art.

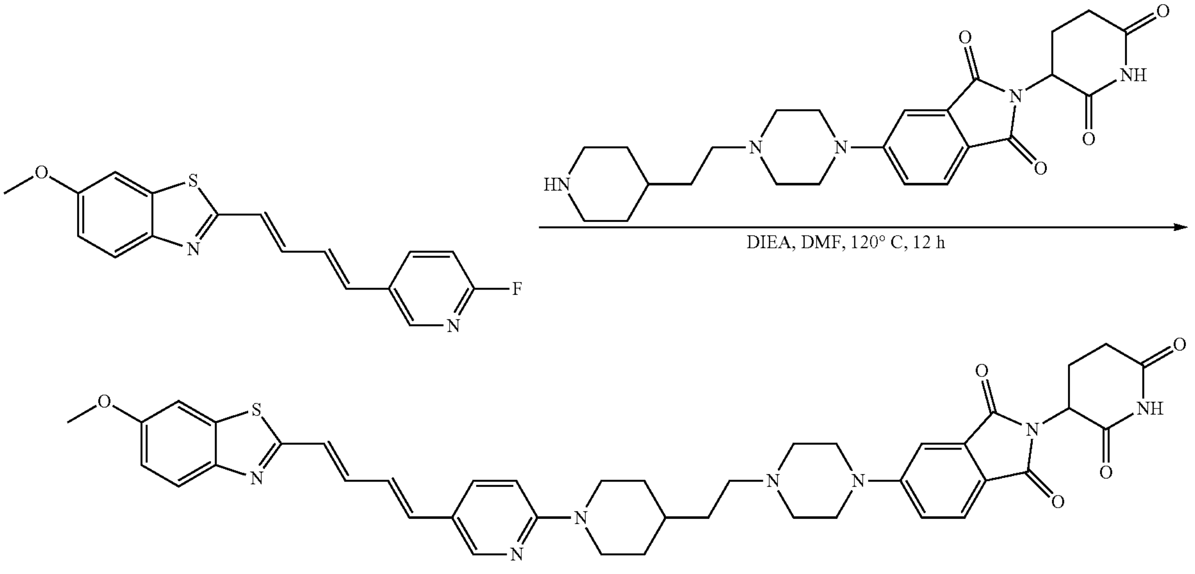

Exemplary Compound 629

Using analogous procedures the following examples were prepared: Exemplary Compounds, 626, 627, and 628.

Exemplary Synthesis of Exemplary Compound 630

Prepared according to the scheme below using procedures described for other examples above as well as general procedures known to those skilled in the art.

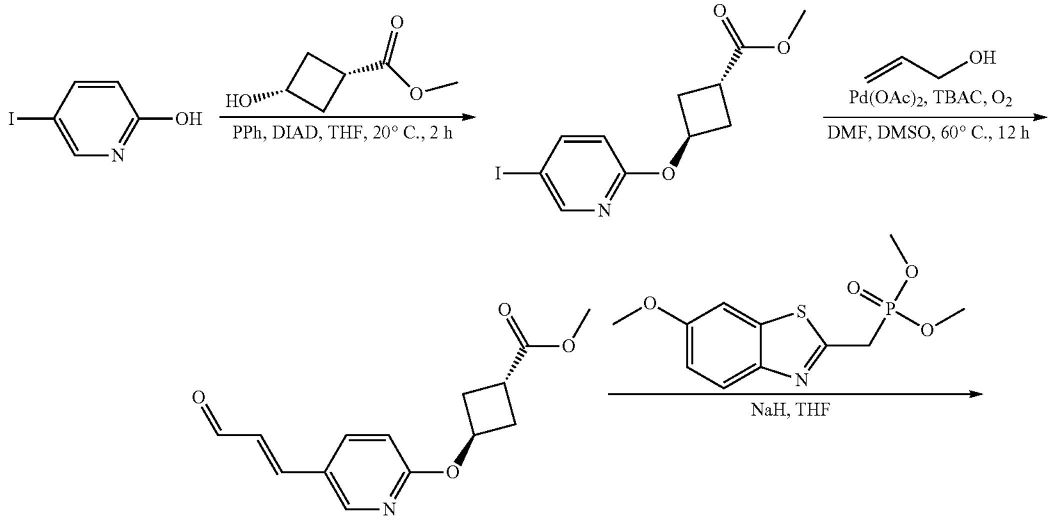

-continued

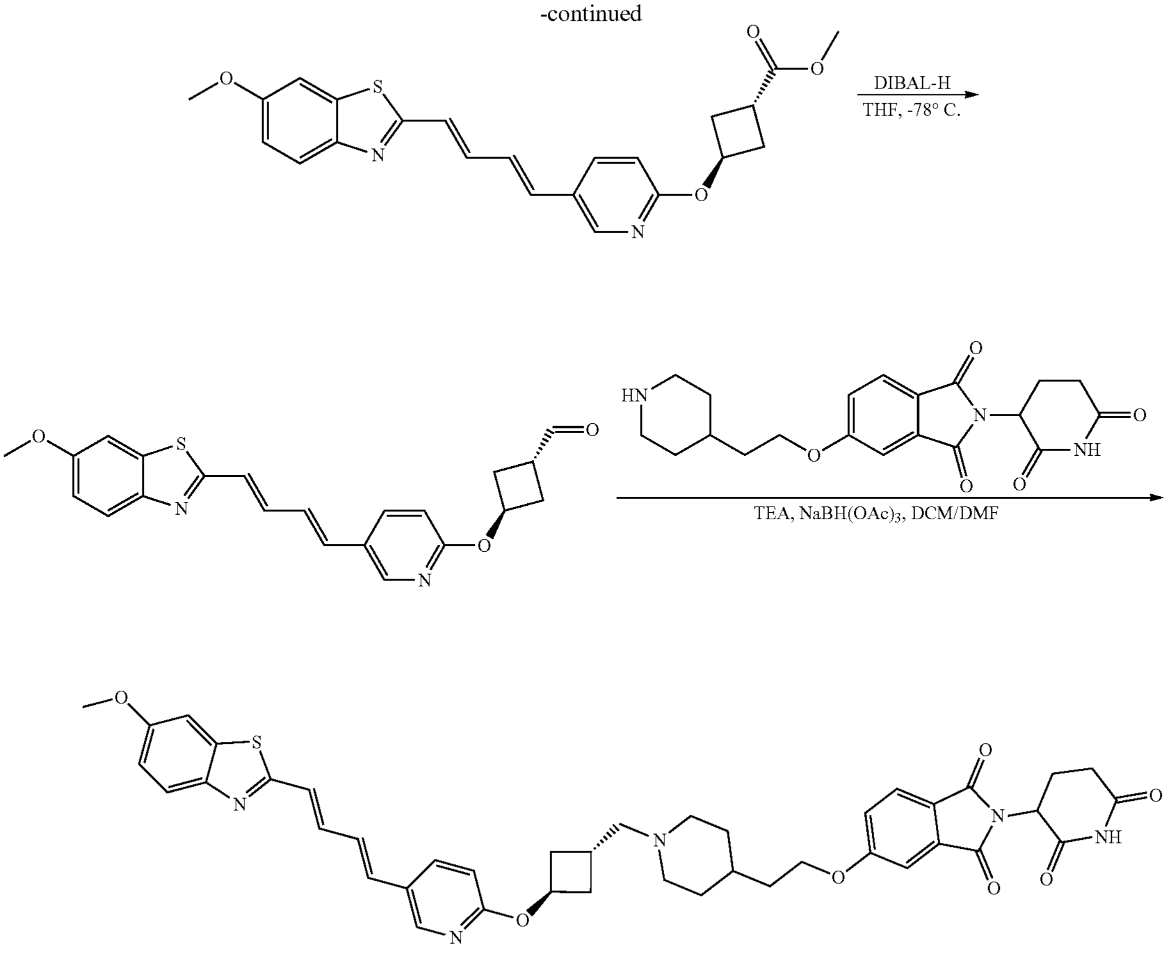

Exemplary Compund 630

Exemplary Synthesis of Exemplary Compound 606

Step 1

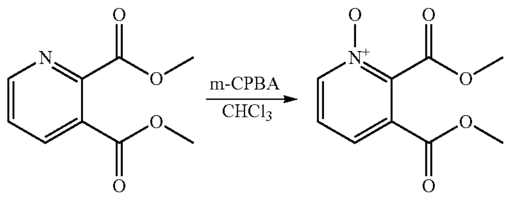

To a solution of dimethyl pyridine-2,3-dicarboxylate (5 g, 25.62 mmol, 1 eq) in $CHCl_3$ (50 mL) was added meta chloroperbenzoic acid (7.80 g, 38.43 mmol, 85% purity, 1.5 eq). After addition, the reaction mixture was stirred at 70° C. for 16 h. The reaction mixture was diluted with saturated sodium bicarbonate (50 mL) and extracted with dichloromethane (3×50 mL). The organic layer was dried over sodium sulfate and concentrated under reduced pressure to afford dimethyl 1-oxidopyridin-1-ium-2,3-dicarboxylate (5.6 g, crude) as a yellow solid. The crude product was used for next step directly.

Step 2

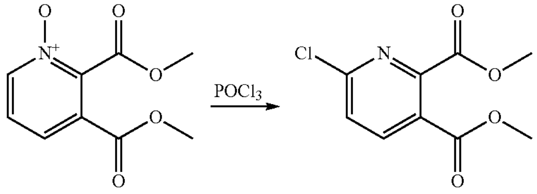

Dimethyl 1-oxidopyridin-1l-ium-2,3-dicarboxylate (5.6 g, 26.52 mmol, 1 eq) was added to $POCl_3$ (81.32 g, 530.38 mmol, 49.29 mL, 20 eq). After addition, the reaction mixture was stirred at 115° C. for 3 h. After being cooled, the mixture was treated with ice-water (80 mL) and dichloromethane (3×60 mL), basified with saturated aq. $NaHCO)_3$ (3×50 mL), and separated. The organic layer was dried over $Na_2SO_4$, filtered, and concentrated in vacuo. The residue was purified by silica gel column chromatography (0 to 20% ethyl acetate in petroleum ether) to afford dimethyl 6-chloropyridine-2, 3-dicarboxylate (3 g, 9.54 mmol, 36% yield) as a light yellow oil.

Step 3

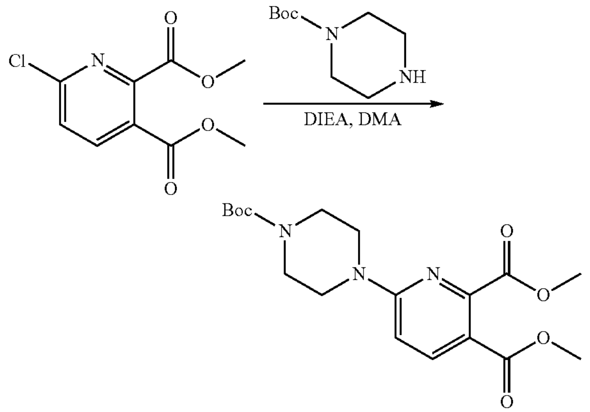

To a solution of dimethyl 6-chloropyridine-2,3-dicarboxylate (2 g, 8.71 mmol, 1 eq) and tert-butyl piperazine-1-carboxylate (4.87 g, 26.13 mmol, 3 eq) in DMA (20 mL) was added DIEA (5.63 g, 43.55 mmol, 7.59 mL, 5 eq). The mixture was stirred at 130° C. for 4 h. The reaction mixture was diluted with ethyl acetate (30 mL) and washed with brine (3×30 mL). The organic layer was dried over sodium sulfate and concentrated under reduced pressure. The residue was purified by silica gel column chromatography (0 to 20% ethyl acetate in petroleum ether) to afford dimethyl 6-(4-tert-butoxycarbonylpiperazin-1-yl)pyridine-2,3-dicarboxylate (3.2 g, 8.18 mmol, 94%) as a yellow solid.

Dimethyl 6-(4-tert-butoxycarbonylpiperazin-1-yl)pyridine-2,3-dicarboxylate was converted to 6-(2,6-dioxopiperidin-3-yl)-2-(piperazin-1-yl)-5H-pyrrolo[3,4-b]pyridine-5,7(6H)-dione according to the scheme below. 6-(2,6-Dioxopiperidin-3-yl)-2-(piperazin-1-yl)-5H-pyrrolo[3,4-b]pyridine-5,7(6H)-dione was converted to the title compound as described for other examples above.

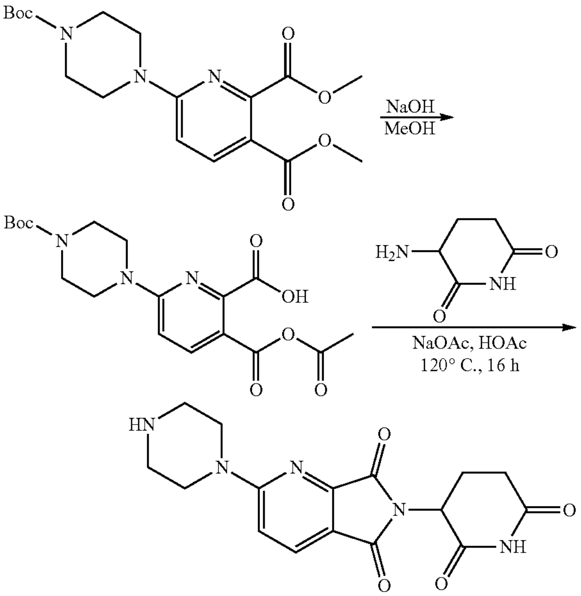

Exemplary Synthesis of Exemplary Compound 607

Prepared according to the schemes below using procedures described for other examples above as well as general procedures known to those skilled in the art.

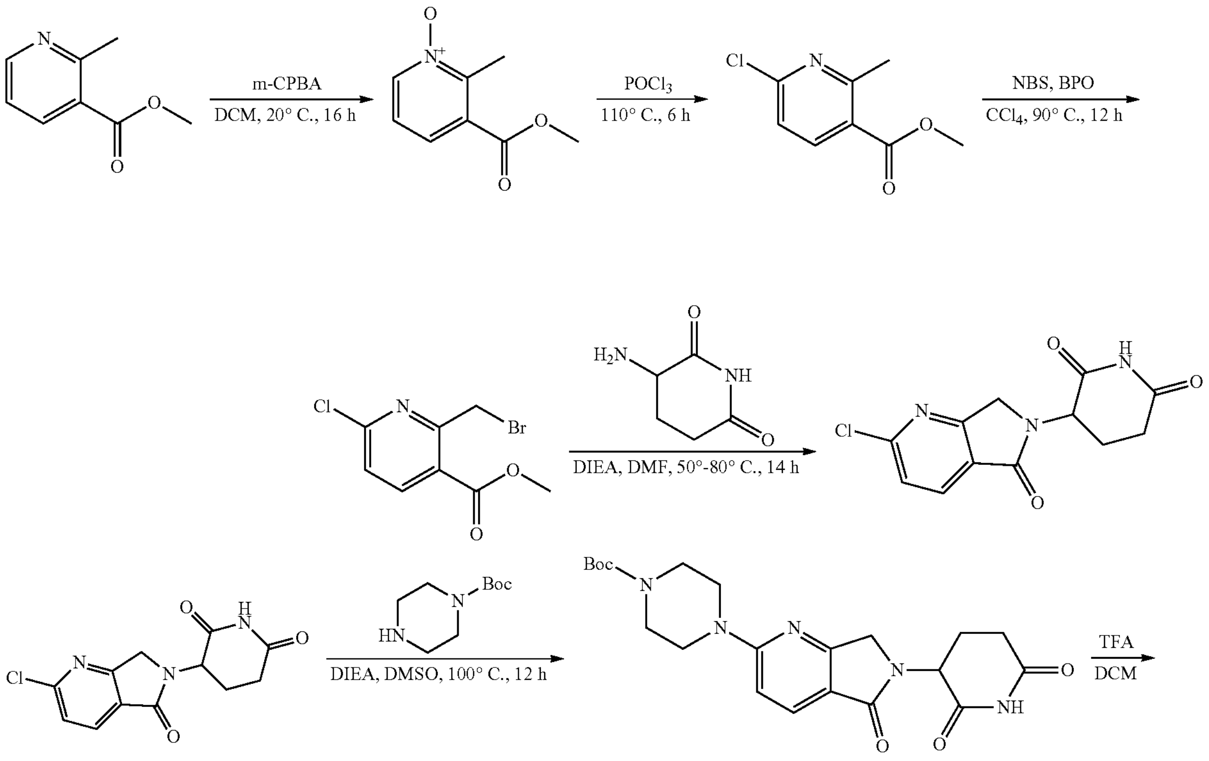

-continued

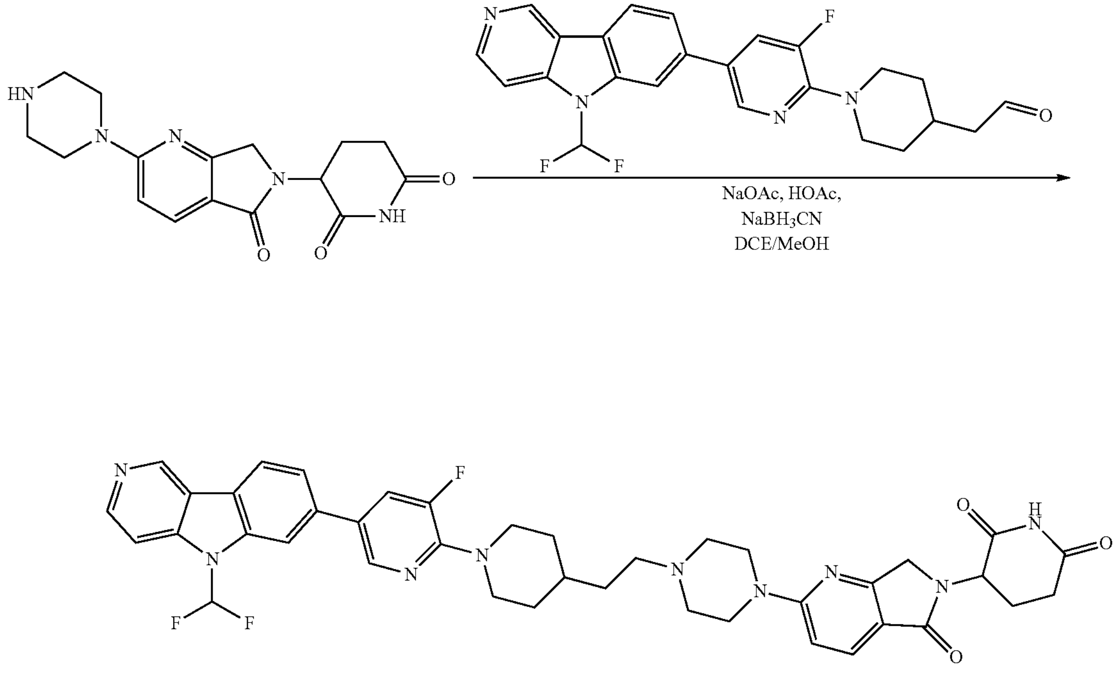

Exemplary Compound 607

Exemplary Synthesis of Exemplary Compound 647

Step 1

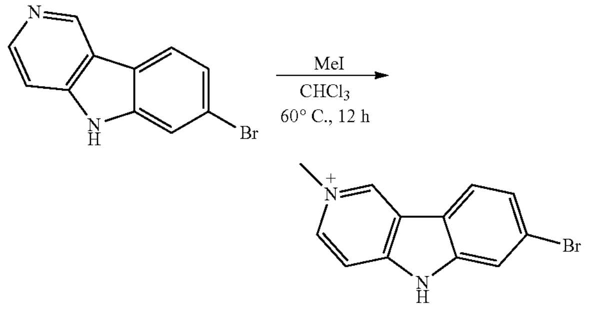

To a solution of 7-bromo-5H-pyrido[4,3-b]indole (1 g, 4.05 mmol, 1.00 eq) in chloroform (10 mL) was added iodomethane (5.74 g, 40.47 mmol, 10.00 eq). The mixture was stirred at 60° C. for 12 hours. The mixture was poured in water (20 mL) and stirred for 1 min. The aqueous phase was extracted with dichloromethane (50 mL×3). The combined organic phase was washed with brine (30 mL×4), dried with anhydrous sodium sulfate, filtered and concentrated in vacuum. Compound 7-bromo-2-methyl-5H-pyrido [4,3-b]indol-2-ium (1 g, 3.81 mmol, 94% yield) was obtained as a yellow solid and was used in the next step without further purification.

Step 2

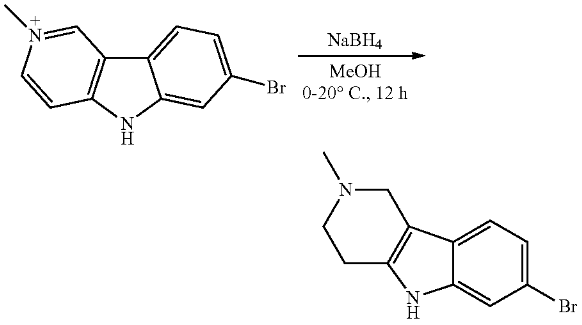

To a solution of 7-bromo-2-methyl-5H-pyrido[4,3-b]indol-2-ium (1 g, 3.81 mmol, 1.00 eq) in methyl alcohol (20 mL) was added sodium borohydride (1.82 g, 48.11 mmol, 12.61 eq) at 0° C. The mixture was stirred at 20° C. for 12 hours. The reaction mixture was diluted with water (30 mL) and extracted with dichloromethane (50 mL×3). The combined organic layers were washed with brine (50 mL×3), dried over sodium sulfate anhydrous, filtered and concentrated under reduced pressure. The residue was purified by preparative High Performance Liquid Chromatography (column: Phenomenex luna C18 150*40 mm*15 um; mobile phase: [water (0.225% formic acid)-methyl cyanide]; B %:1%-31%, 10 min) to give 7-bromo-2-methyl-1,3,4,5-tetrahydropyrido[4,3-b] indole (770 mg, 2.90 mmol, 76% yield) as a white solid.

7-Bromo-2-methyl-1,3,4,5-tetrahydropyrido[4,3-b] indole was converted to the title compound according to the scheme below using procedures described for other examples above as well as general procedures known to those skilled in the art.

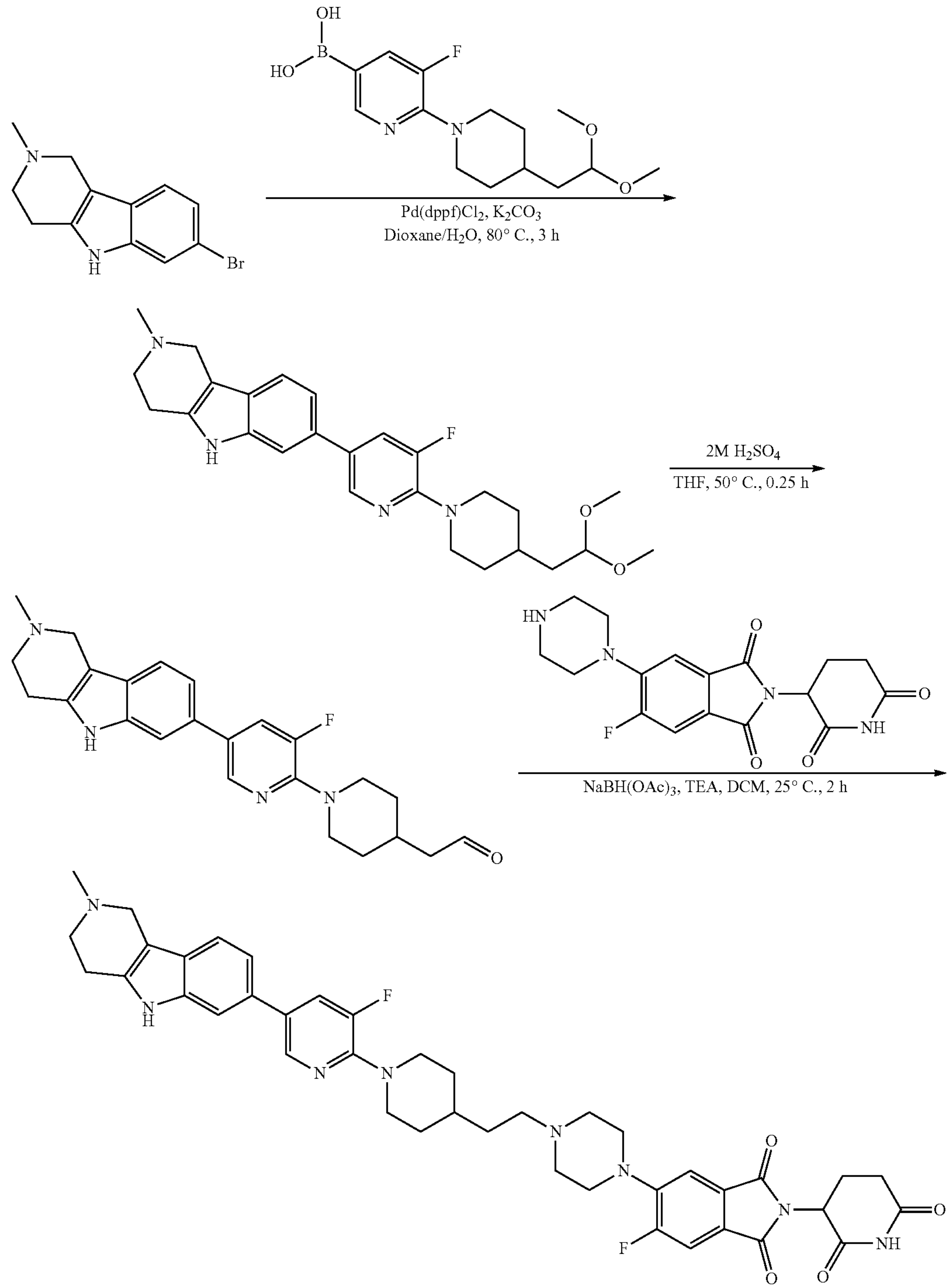

Exemplary Compound 647

Exemplary bifunctional molecules of the present disclosure can be prepared from the PTM embodiments of the present disclosure using the methods of linker and E3 ligase-binding moiety attachment previously described.

Exemplary bifunctional molecules of the present disclosure are represented by the structures in Table 1, which includes associated data. In vitro tau protein degradation data in CHOK1 Tau P301L cells, as described below, is reported based on the remaining tau protein in the sarkosyl insoluble pellet following treatment of cells for 48 hours with test compound at the 1 μM concentration where the last 24 hours doxycycline was removed. The data are represented relative to DMSO doxycycline control:

A ≤50% of tau protein remaining (>50% of tau protein degraded)

B >50% of tau protein remaining (≥50% of tau protein degraded)

TABLE 1

| Exemplary bifunctional compounds of the present disclosure | | | | | |
|---|---|---|---|---|---|
| Ex. No. | Structure | Compound Name | Tau Protein Degradation effect at 1 µM | MH+ | NMR transcript |
| 4 | 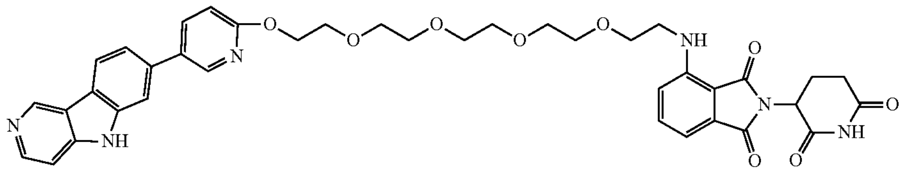 [SMILES: O=C1CCC(N2C(=O)c3cccc(NCCOCCOCCOCCOCCOc4ccc(-c5ccc6c(c5)[nH]c5ccncc56)cn4)c3C2=O)C(=O)N1] | | | 737.4 | 1H NMR (400 MHz, CDCl3): δ 9.30 (s, 1H), 8.90 (br, 1H), 8.52 (d, J = 5.6 Hz, 1H), 8.42 (d, J = 2.8 Hz, 1H), 8.14 (d, J = 8.0 Hz, 1H), 7.49 (dd, J = 2.4, 8.8 Hz, 1H), 7.57 (s, 1H), 7.26-7,46 (m, 3H), 6.97 (d, J = 7.2 Hz, 1H), 6.81-6.87 (m, 2H), 6.35-6.46 (m, 1H), 4.89-4.98 (m, 1H), 4.54 (t, J = 4.8 Hz, 2H), 3.90 (t, J = 4.8 Hz, 2H), 3.61-3.74 (m, 15H), 3.37-3.81 (m, 2H), 2.65-2.92 (m, 3H), 2.07-2.15 (m, 1H). |
| 82 | 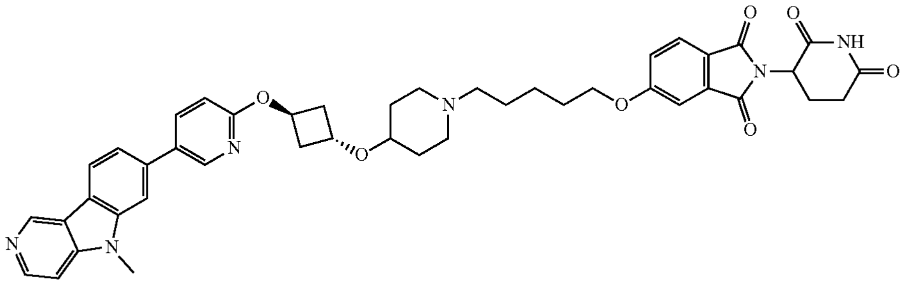 | | | 771.6 | $^1$H NMR (400 MHz, DMSO-$d_6$): δ 11.12 (s, 1H), 9.36 (s, 1H), 8.64 (d, J = 2.2 Hz, 1H), 8.50 (d, J = 5.7 Hz, 1H), 8.32 (d, J = 8.2 Hz, 1H), 8.19 (dd, J = 8.8, 2.6 Hz, 2H), 7.98 (s, 1H), 7.83 (d, J = 8.3 Hz, 1H), 7.62 (d, J = 8.4 Hz, 2H), 7.43 (d, J = 2.0 Hz, 1H), 7.35 (d, J = 8.4 Hz, 1H), 6.94 (d, J = 8.7 Hz, 1H), 5.31 (s, 1H), 5.12 (dd, J = 12.9, 5.3 Hz, 1H), 4.40-4.32 (m, 1H), 4.18 (t, J = 6.4 Hz, 2H), 3.96 (s, 3H), 2.88 (d, J = 13.2 Hz, 2H), 2.74 (s, 2H), 2.36 (m, 6H), 2.07 (s, 3H), 1.88-1.70 (m, 4H), 1.60-1.34 (m, 6H). |
| 332 | 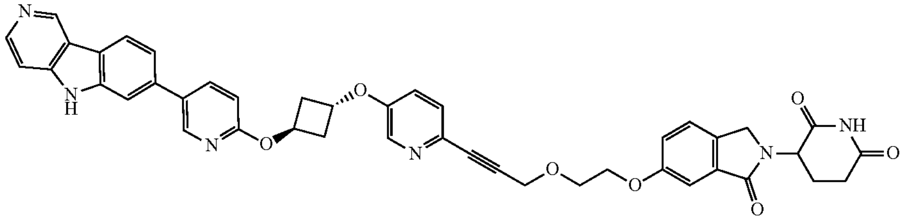 [SMILES: O=C1CCC(N2Cc3ccc(OCCOCC#Cc4ccc(O[C@H]5C[C@H](Oc6ccc(-c7ccc8c(c7)[nH]c7ccncc78)cn6)C5)cn4)cc3C2=O)C(=O)N1] | 3-(6-(2-((3-(5-((1r,3r)-3-((5-(5H-pyrido[4,3-b]indol-7-yl)pyridin-2-yl)oxy)cyclobutoxy) pyridin-2-yl)prop-2-yn-1-yl)oxy)ethoxy)-1-oxoisoindolin-2-yl)piperidine-2,6-dione | | 749.5 | 1H NMR (400 MHz, DMSO-D6): δ 9.76 (s, 1H), 8.67-8.62 (m, 2H), 8.52 (d, J = 8.4 Hz, 1H), 8.25-8.20 (m, 2H), 8.02-8.01 (m, 2H), 7.82-7.80 (m, 1H), 7.52-7.47 (m, 2H), 7.30-7.22 (m, 3H), 7.03-7.00 (m, 1H), 5.44-5.43 (m, 1H), 5.11-5.09 (m, 2H), 4.49 (s, 2H), 4.41-4.36 (m, 1H), 4.28-4.24 (m, 3H), 3.90-3.89 (m, 2H), 2.90-2.80 (m, 1H), 2.68-2.51 (m, 5H), 2.40-2.30 (m, 1H), 2.05-1.98 (m, 1H). |

TABLE 1-continued

| | | | | |
|---|---|---|---|---|
| 335 | 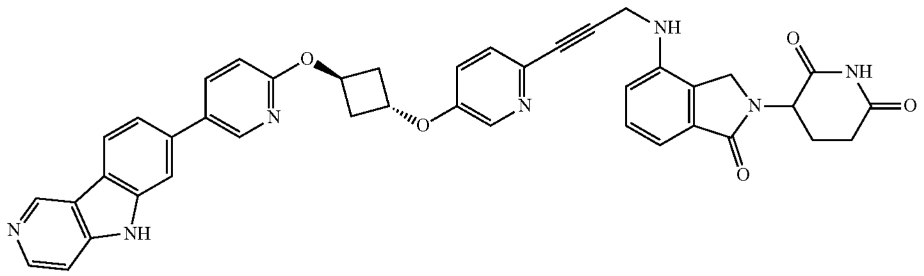 [SMILES: O=C1CCC(N2Cc3c(NCC#Cc4ccc(O[C@H]5C[C@H](Oc6ccc(-c7ccc8c(c7)[nH]c7ccncc78)cn6)C5)cn4)cccc3C2=O)C(=O)N1] | 3-(4-((3-(5-((1r,3r)-3-((5-(5H-pyrido[4,3-b]indol-7-yl)pyridin-2-yl)oxy)cyclobutoxy)pyridin-2-yl)prop-2-yn-1-yl)amino)-1-oxoisoindolin-2-yl)piperidine-2,6-dione | 704.4 | 1H NMR (400 MHz, DMSO-D6): δ 9.80 (s, 1H), 8.67-8.61 (m, 2H), 8.53-8.51 (d, J = 8.4 Hz, 1H), 8.20-8.17 (m, 2H), 8.02-8.01 (m, 2H), 7.82-7.80 (m, 1H), 7.41-7.26 (m, 3H), 7.05-6.96 (m, 3H), 5.44-5.42 (m, 1H), 5.14-5.06 (m, 2H), 4.31-4.17 (m, 4H), 2.92-2.89 (m, 1H), 2.69-2.61 (m, 5H), 2.36-2.32 (m, 1H), 2.07-2.03 (m, 1H). |
| 337 | 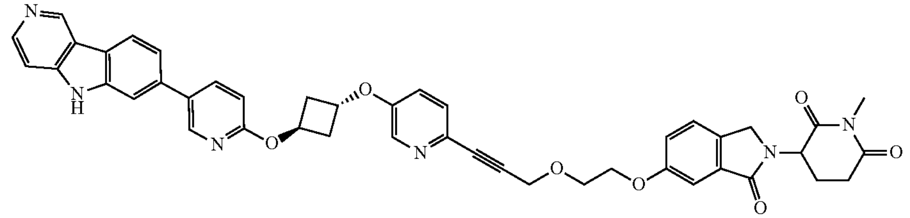 [SMILES: CN1C(=O)CCC(N2Cc3ccc(OCCOCC#Cc4ccc(O[C@H]5C[C@H](Oc6ccc(-c7ccc8c(c7)[nH]c7ccncc78)cn6)C5)cn4)cc3C2=O)C1=O] | 3-(5-(2-((3-(5-((1r,3r)-3-((5-(5H-pyrido[4,3-b]indol-7-yl)pyridin-2-yl)oxy)cyclobutoxy)pyridin-2-yl)prop-2-yn-1-yl)oxy)ethoxy)-1-oxoisoindolin-2-yl)-1-methylpiperidine-2,6-dione | 763.5 | 1H NMR (300 MHz, DMSO-D6): δ 13.14 (s, 1H), 9.76 (s, 1H), 8.68-8.65 (m, 2H), 8.62-8.54 (m, 1H), 8.24-8.21 (m, 2H), 8.02-8.00 (m, 2H), 7.83-7.80 (m, 1H), 7.64-7.61 (m, 1H), 7.47-7.44 (m, 1H), 7.33-7.32 (m, 1H), 7.29-7.26 (m, 1H), 7.09-7.00 (m, 2H), 5.46-5.42 (m, 1H), 5.17-5.08 (m, 2H), 4.49-4.22 (m, 6H), 3.91-3.88 (m, 2H), 3.00-2.90 (m, 4H), 2.70-2.49 (m, 6H), 2.02-1.90 (m, 1H). |
| 338 | 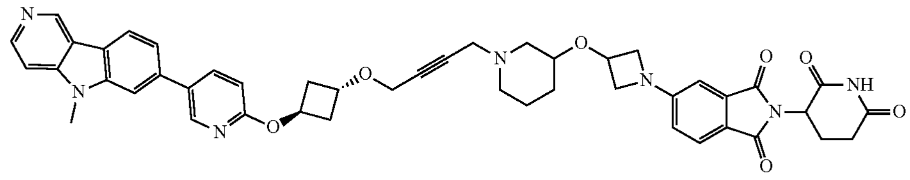 [SMILES: Cn1c2ccncc2c2ccc(-c3ccc(O[C@H]4C[C@H](OCC#CCN5CCCC(OC6CN(c7ccc8c(c7)C(=O)N(C7CCC(=O)NC7=O)C8=O)C6)C5)C4)nc3)cc21] | 2-(2,6-dioxopiperidin-3-yl)-5-(3-((1-(4-((1r,3r)-3-((5-(5-methyl-5H-pyrido[4,3-b]indol-7-yl)pyridin-2-yl)oxy)cyclobutoxy)but-2-yn-1-yl)piperidin-3-yl)oxy)azetidin-1-yl)isoindoline-1,3-dione | 808.5 | 1H NMR (400 MHz, DMSO-D6): δ 11.06 (s, 1H), 9.35 (s, 1H), 8.63 (d, J = 2.6 Hz, 1H), 8.49 (d, J = 5.7 Hz, 1H), 8.31 (d, J = 8.2 Hz, 1H), 8.27 (s, 1H), 8.18 (dd, J = 2.7, 8.4 Hz, 1H), 7.97 (s, 1H), 7.65-7.56 (m, 3H), 6.93 (d, J = 8.8 Hz, 1H), 6.77 (s, 1H), 6.61 (d, J = 8.2 Hz, 1H), 5.32 (s, 1H), 5.07-5.00 (m, 1H), 4.60 (br s, 1H), 4.39 (br d, J = 4.5 Hz, 1H), 4.30-4.22 (m, 3H), 4.17 (s, 3H), 3.95 (s, 3H), 3.80 (br d, J = 5.1 Hz, 3H), 2.84 (br d, J = 10.5 Hz, 2H), 2.61-2.55 (m, 4H), 2.38 (br d, J = 4.3 Hz, 2H), 2.21-2.07 (m, 3H), 1.99 (s, 1H), 1.89-1.77 (m, 1H), 1.68 (br s, 1H), 1.41 (s, 1H), 1.32-1.10 (m, 2H). |
| 339 | 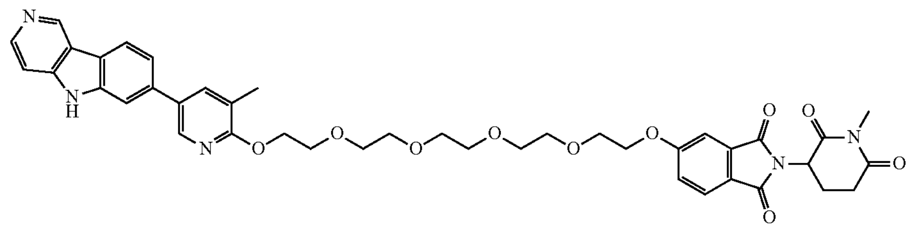 [SMILES: Cc1cc(-c2ccc3c(c2)[nH]c2ccncc23)cnc1OCCOCCOCCOCCOCCOc1ccc2c(c1)C(=O)N(C1CCC(=O)N(C)C1=O)C2=O] | 2-(1-methyl-2,6-dioxopiperidin-3-yl)-5-((14-((3-methyl-5-(5H-pyrido[4,3-b]indol-7-yl)pyridin-2-yl)oxy)-3,6,9,12-tetraoxatetradecyl)oxy)isoindoline-1,3-dione | 766.5 | 1H NMR (400 MHz, DMSO-D6): δ 9.71 (s, 1H), 8.64 (d, J = 6 Hz, 1H), 8.49 (d, J = 6.1 Hz, 1H), 8.48 (s, 1H), 8.02-8.00 (m, 3H), 7.79 (d, J = 6.1 Hz, 2H), 7.34-7.32 (m, 2H), 5.16-5.12 (m, 1H), 4.49-4.47 (m, 2H), 4.27-4.25 (m, 2H), 3.80-3.78 (m, 4H), 3.62-3.52 (m, 13H), 3.00 (s, 3H), 2.92-2.78 (m, 1H), 2.78-2.53 (m, 1H), 2.53-2.25 (m, 1H), 2.25 (s, 3H), 2.25-2.02 (m, 1H). |

TABLE 1-continued

| | | | | | |
|---|---|---|---|---|---|
| 340 | 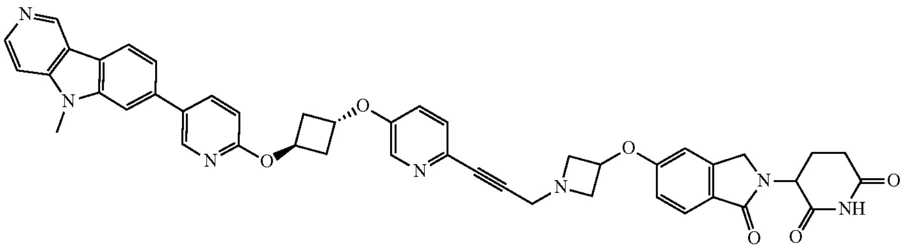 [SMILES: Cn1c2ccncc2c2ccc(-c3ccc(O[C@H]4C[C@H](Oc5ccc(C#CCN6CC(Oc7ccc8c(c7)CN(C7CCC(=O)NC7=O)C8=O)C6)nc5)C4)nc3)cc21] | 3-(5-((1-(3-(5-((1r,3r)-3-((5-(5-methyl-5H-pyrido[4,3-b]indol-7-yl)pyridin-2-yl)oxy)cyclobutoxy)pyridin-2-yl)prop-2-yn-1-yl)azetidin-3-yl)oxy)-1-oxoisoindolin-2-yl)piperidine-2,6-dione | B | 774.5 | 1H NMR (300 MHz, DMSO-D6): δ 9.71 (s, 1H), 8.72 (s, 2H), 8.55-8.52 (m, 1H), 8.29-8.26 (m, 2H), 8.20-8.16 (m, 2H), 7.88-7.86 (m, 1H), 7.73-7.71 (m, 1H), 7.63-7.61 (m, 1H), 7.40-7.36 (m, 1H), 7.11 (s, 1H), 7.06-7.02 (m, 2H), 5.46-5.41 (m, 1H), 5.24-5.21 (m, 1H), 5.16-5.12 (m, 1H), 5.08-4.98 (m, 1H), 4.81-4.65 (m, 2H), 4.51-4.48 (m, 2H), 4.46-4.29 (m, 4H), 4.13 (s, 3H), 2.92-2.84 (m, 1H), 2.81-2.65 (m, 4H), 2.42-2.37 (m, 1H), 2.07-2.01 (m, 1H), 1.36-1.25 (m, 1H), 0.94-0.87 (m, 1H). |
| 341 | 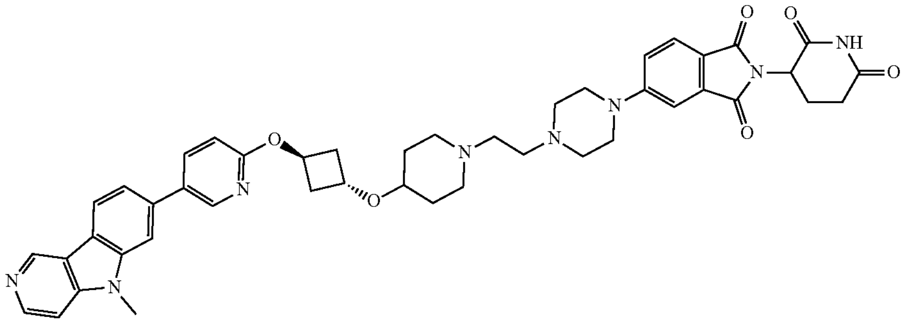 [SMILES: Cn1c2ccncc2c2ccc(-c3ccc(O[C@H]4C[C@H](OC5CCN(CCN6CCN(c7ccc8c(c7)C(=O)N(C7CCC(=O)NC7=O)C8=O)CC6)CC5)C4)nc3)cc21] | 2-(2,6-dioxopiperidin-3-yl)-5-(4-(2-(4-((1r,3r)-3-((5-(5-methyl-5H-pyrido[4,3-b]indol-7-yl)pyridin-2-yl)oxy)cyclobutoxy)piperidin-1-yl)ethyl)piperazin-1-yl)isoindoline-1,3-dione | B | 797.6 | 1H NMR (300 MHz, DMSO-D6): δ 11.06 (s, 1H), 9.36 (s, 1H), 8.65 (s, 1H), 8.51 (d, J = 6 Hz, 1H), 8.33 (d, J = 6 Hz, 1H), 8.20 (d, J = 6 Hz, 1H), 7.98 (s, 1H), 7.69-7.62 (m, 3H), 7.33-7.24 (m, 2H), 6.95 (d, J = 6 Hz, 1H), 5.32 (s, 1H), 5.10-5.05 (m, 1H), 4.38-4.36 (m, 1H), 3.96 (s, 3H), 3.43 (s, 4H), 2.93-2.86 (m, 1H), 2.74-2.61 (m, 2H), 2.54-2.51 (m, 7H), 2.41-2.14 (m, 8H), 2.07-2.01 (m, 3H), 1.79 (s, 2H), 1.44-1.42 (m, 2H). |
| 342 | 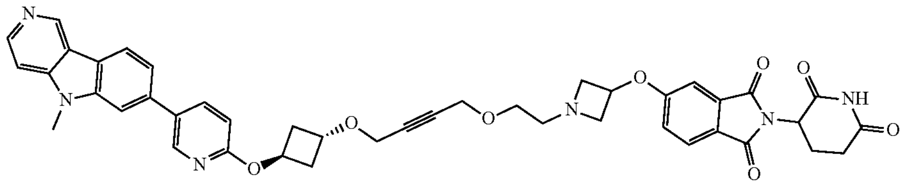 [SMILES: Cn1c2ccncc2c2ccc(-c3ccc(O[C@H]4C[C@H](OCC#CCOCCN5CC(Oc6ccc7c(c6)C(=O)N(C6CCC(=O)NC6=O)C7=O)C5)C4)nc3)cc21] | 2-(2,6-dioxopiperidin-3-yl)-5-((1-(2-((4-((1r,3r)-3-((5-(5-methyl-5H-pyrido[4,3-b]indol-7-yl)pyridin-2-yl)oxy)cyclobutoxy)but-2-yn-1-yl)oxy)ethyl)azetidin-3-yl)oxy)isoindoline-1,3-dione | | 769.5 | 1H NMR (400 MHz, CDCl3): δ 9.38 (d, J = 6.8, 1H), 8.53-8.51 (m, 2H), 8.38-8.32 (m, 2H), 8.13 (dd, J = 2.4 Hz, 8.4 Hz, 1H), 7.90 (s, 1H), 7.83-7.81 (m, 1H), 7.73 (d, J = 8.0 Hz, 1H), 7.67 (d, J = 8.0 Hz, 1H), 7.23-7.17 (m, 2H), 6.93 (d, J = 8.4 Hz, 1H), 5.36-5.33 (m, 1H), 5.07 (m, 2H), 4.69-4.46 (m, 1H), 4.26 (s, 2H), 4.22 (t, J = 1.6 Hz, 4H), 4.06 (s, 3H), 3.76-3.68 (m, 4H), 3.15-3.08 (m, 2H), 2.88-2.67 (m, 3H), 2.60-2.54 (m, 2H), 2.50-2.43 (m, 2H), 2.15-2.10 (m, 1H). |
| 343 | 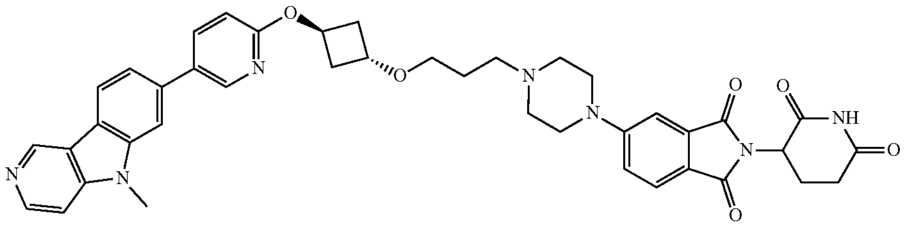 [SMILES: Cn1c2ccncc2c2ccc(-c3ccc(O[C@H]4C[C@H](OCCCN5CCN(c6ccc7c(c6)C(=O)N(C6CCC(=O)NC6=O)C7=O)CC5)C4)nc3)cc21] | 2-(2,6-dioxopiperidin-3-yl)-5-(4-(3-((1r,3r)-3-((5-(5-methyl-5H-pyrido[4,3-b]indol-7-yl)pyridin-2-yl)oxy)cyclobutoxy)propyl)piperazin-1-yl)isoindoline-1,3-dione | A | 728.5 | 1H NMR (300 MHz, DMSO-D6): δ 11.06 (s, 1H), 9.32 (s, 1H) 8.59 (s, 1H), 8.47 (d, J = 6 1H), 8.27 (d, J = 9 Hz, 1H), 8.16-8.13 (m, 1H), 7.93 (s, 1H), 7.64-7.56 (m, 3H), 7.29 (s, 1H), 7.20 (d, J = 9 Hz, 1H), 6.90 (d, J = 9 Hz, 1H), 5.30 (s, 1H), 5.08-5.02 (m, 1H), 4.86-4.84 (m, 1H), 4.16 (s, 3H), 3.98-3.83 (m, 8H), 3.72-3.54 (m, 2H), 3.39-3.34 (m, 1H), 2.91-2.82 (m, 2H), 2.59-2.31 (m, 6H), 2.05-1.97 (m, 1H), 1.71-1.67 (m, 2H). |

TABLE 1-continued

| | | | | | |
|---|---|---|---|---|---|
| 344 | 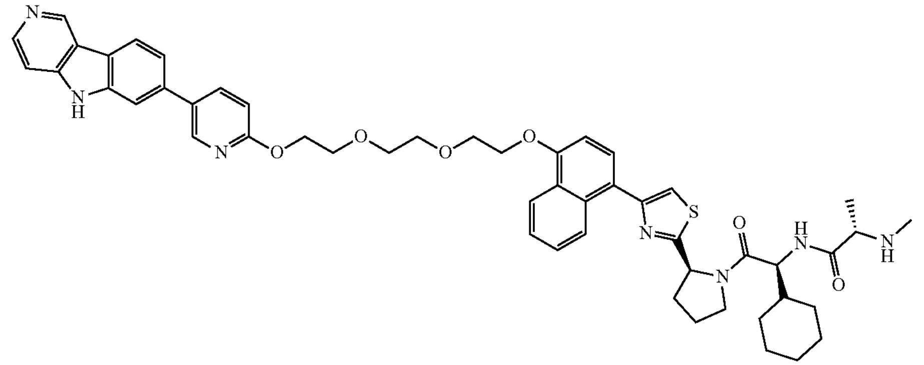 [SMILES: CN[C@@H](C)C(=O)N[C@H](C(=O)N1CCC[C@H]1c1nc(-c2ccc(OCCOCCOCCOc3ccc(-c4ccc5c(c4)[nH]c4ccncc45)cn3)c3ccccc23)cs1)C1CCCCC1] | (S)-N-((S)-2-((S)-2-(4-(4-(2-(2-(2-((5-(5H-pyrido[4,3-b]indol-7-yl)pyridin-2-yl)oxy)ethoxy)ethoxy)ethoxy)naphthalen-1-yl)thiazol-2-yl)pyrrolidin-1-yl)-1-cyclohexyl-2-oxoethyl)-2-(methylamino)propanamide | | 896.8 | 1H NMR (400 MHz, CD3OD): δ 9.52 (s, 1H), 8.54 (d, J = 6.8 Hz, 1H), 8.40 (s, 1H), 8.04 (s, 2H), 7.93-7.83 (m, 5H), 7.48-7.40 (m, 4H), 6.90 (d, J = 7.6 Hz, 2H), 5.51-5.49 (m, 1H), 4.60-4.51 (m, 1H), 4.50-4.49 (m, 2H), 4.33-4.31 (m, 2H), 4.03-4.01 (m, 2H), 3.96-3.90 (m, 5H), 3.89-3.78 (m, 4H), 2.67 (s, 3H), 2.29-2.12 (m, 1H), 2.09-2.03 (m, 3H), 1.82 (s, 4H), 1.62-1.60 (m, 4H), 1.51-1.50 (m, 3H), 1.49-1.15 (m, 5H). |
| 345 | 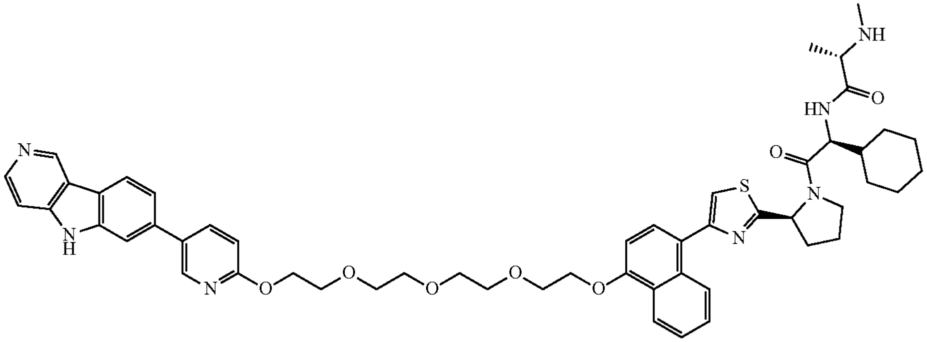 [SMILES: CN[C@@H](C)C(=O)N[C@H](C(=O)N1CCC[C@H]1c1nc(-c2ccc(OCCOCCOCCOCCOc3ccc(-c4ccc5c(c4)[nH]c4ccncc45)cn3)c3ccccc23)cs1)C1CCCCC1] | (S)-N-((S)-2-((S)-2-(4-(4-(2-(2-(2-(2-((5-(5H-pyrido[4,3-b]indol-7-yl)pyridin-2-yl)oxy)ethoxy)ethoxy)ethoxy)ethoxy)napthalen-1-yl)thiazol-2-yl)pyrrolidin-1-yl)-1-cyclohexyl-2-oxoethyl)-2-(methylamino)propanamide | | 940.8 | 1H NMR (400 MHz, CD3OD): δ 9.25 (s 1H), 8.38-8.31 (m, 3H), 8.22 (d, J = 12 Hz, 1H), 8.19-8.00 (m, 1H), 7.91-7.82 (m, 1H), 7.64 (s, 1H), 7.49-7.43 (m, 5H), 7.32 (s, 1H), 6.88-6.80 (m, 2H), 5.60-5.45 (m, 1H), 4.57 (d, J = 8 Hz, 1H), 4.42-4.40 (m, 2H), 4.30-4.28 (m, 2H), 4.01-4.00 (m, 2H), 3.99-3.82 (m, 1H), 3.81-3.30 (m, 11H), 3.14 (d, J = 8 Hz, 1H), 2.60-2.31 (m, 4H), 2.30-2.02 (m, 3H), 1.78-1.57 (m, 6H), 1.23-1.21 (d, J = 8 Hz, 3H), 1.11-1.06 (m, 5H). |
| 346 | 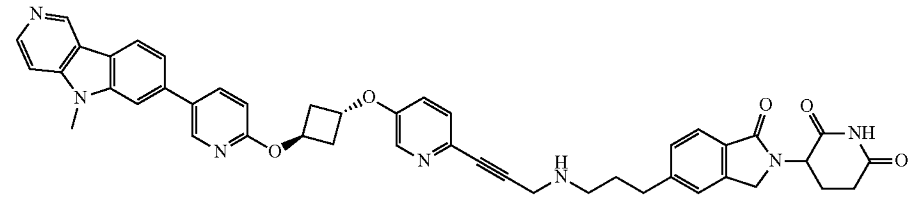 [SMILES: Cn1c2ccncc2c2ccc(-c3ccc(O[C@H]4C[C@H](Oc5ccc(C#CCNCCCc6ccc7c(c6)CN(C6CCC(=O)NC6=O)C7=O)nc5)C4)nc3)cc21] | 3-(5-(3-((3-(5-((1r,3r)-3-((5-(5-methyl-5H-pyrido[4,3-b]indol-7-yl)pyridin-2-yl)oxy)cyclobutoxy)pyridin-2-yl)prop-2-yn-1-yl)amino)propyl)1-oxoisoindolin-2-yl)piperidine-2,6-dione | B | 760.6 | 1H NMR (300 MHz, DMSO-D6): δ 9.71 (s, 1H), 8.74-8.72 (m, 2H), 8.55-8.52 (m, 1H), 8.30-8.8.27 (m, 2H), 8.20-8.16 (m, 2H), 7.91-7.83 (m, 1H), 7.70-.68 (m, 1H), 7.52-7.49 (m, 2H), 7.40-7.36 (m, 2H), 7.08-6.95 (m, 1H), 5.52-5.44 (m, 1H), 5.11-5.04 (m, 2H), 4.51-4.28 (m, 2H), 4.21-4.13 (m, 5H), 3.21-3.03 (m, 2H), 2.99-2.58 (m, 8H), 2.45-2.21 (m, 1H), 2.15-1.87 (m, 3H). |

TABLE 1-continued

| | | | | |
|---|---|---|---|---|
| 347 | 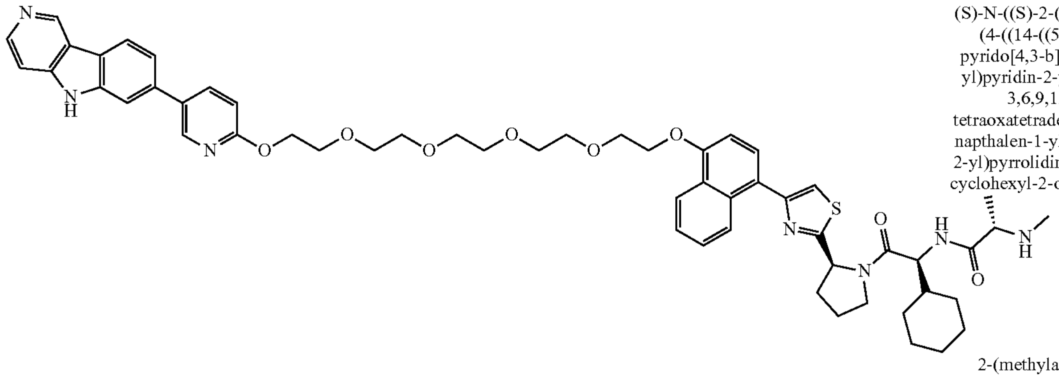 | (S)-N-((S)-2-((S)-2-(4-(4-((14-((5-(5H-pyrido[4,3-b]indol-7-yl)pyridin-2-yl)oxy)-3,6,9,12-tetraoxatetradecyl)oxy)napthalen-1-yl)thiazol-2-yl)pyrrolidin-1-yl)-1-cyclohexyl-2-oxoethyl)-2-(methylamino)propanamide | 948.8 | 1H NMR (400 MHz, $CD_3OD$) δ: 9.23 (s, 1H), 8.40-8.39 (m, 2H), 8.31-8.30 (m, 1H), 8.21-8.19 (d, J = 8.0 Hz, 1H), 8.11-8.09 (m, 1H), 7.95-7.92 (m, 1H), 7.65 (s, 1H), 7.49-7.44 (m, 5H), 7.35 (s, 1H), 6.89-6.83 (m, 2H), 5.61-5.47 (m, 1H), 4.58-4.56 (d, J = 6.8 Hz, 1H), 4.44-4.41 (m, 2H), 4.30-4.28 (m, 2H), 3.99-3.97 (m, 3H), 3.82-3.75 (m, 5H), 3.69-3.62 (m, 10H), 3.15-3.14 (d, J = 7.2 Hz, 1H), 2.39-2.29 (m, 4H), 2.86-2.01 (m, 3H), 1.84-1.72 (m, 3H), 1.69-1.53 (m, 3H), 1.24-1.22 (d, J = 7.2 Hz, 3H), 1.13-1.07 (m, 5H) |
| 348 | 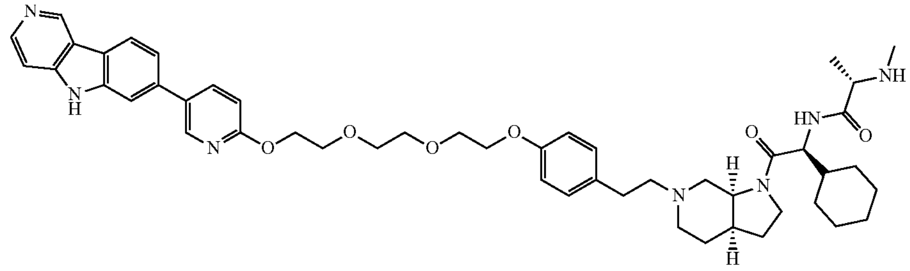 [SMILES: CN[C@@H](C)C(=O)N[C@H](C(=O)N1CC[C@H]2CCN(CCc3ccc(OCCOCCOCCOc4ccc(-c5ccc6c(c5)[nH]c5ccncc56)cn4)cc3)C[C@H]21)C1CCCCC1] | (S)-N-((S)-2-((3aR,7aS)-6-(4-(2-(2-(2-((5-(5H-pyrido[4,3-b]indol-7-yl)pyridin-2-yl)oxy)ethoxy)ethoxy)ethoxy)phenethyl)octahydro-1H-pyrrolo[2,3-c]pyridin-1-yl)-1-cyclohexyl-2-oxoethyl)-2-(methylamino)propanamide | 846.8 | 1H NMR (400 MHz, CD3OD): δ 9.28 (d, J = 2.4 Hz, 1H), 8.47 (s, 1H), 8.41 (d, J = 6.0 Hz, 1H), 8.29 (d, J = 8.0 Hz, 1H), 8.03 (d, J = 8.8 Hz, 1H), 7.74 (s, 1H), 7.56-7.52 (m, 2H), 7.09-7.00 (m, 2H), 6.94-6.92 (m, 1H), 6.83-6.80 (m, 2H), 4.52-4.49 (m, 3H), 4.35-4.10 (m, 1H), 4.08-4.06 (m, 2H), 3.92-3.90 (m, 2H), 3.85-3.76 (m, 6H), 3.68-3.41 (m, 2H), 3.24 (s, 1H), 3.16-3.14 (m, 1H), 2.64 (s, 3H), 2.31-2.29 (m, 5H), 2.11-1.84 (m, 4H), 1.79-1.68 (m, 8H), 1.31-1.21 (m, 9H). |
| 349 | 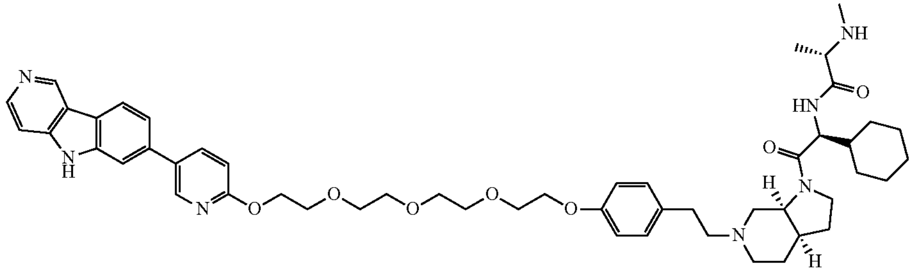 [SMILES: CN[C@@H](C)C(=O)N[C@H](C(=O)N1CC[C@H]2CCN(CCc3ccc(OCCOCCOCCOCCOc4ccc(-c5ccc6c(c5)[nH]c5ccncc56)cn4)cc3)C[C@H]21)C1CCCCC1] | (S)-N-((S)-2-((3aR,7aS)-6-(4-(2-(2-(2-(2-((5-(5H-pyrido[4,3-b]indol-7-yl)pyridin-2-yl)oxy)ethoxy)ethoxy)ethoxy)ethoxy)phenethyl)octahydro-1H-pyrrolo[2,3-c]pyridin-1-yl)-1-cyclohexyl-2-oxoethyl)-2-(methylamino)propanamide | 890.9 | 1H NMR (400 MHz, CD3OD): δ 9.28-9.27 (d, J = 3.2 Hz, 1H), 8.46 (s, 1H), 8.42-8.40 (m, 1H), 8.29-8.27 (d, J = 8.4 Hz, 1H), 7.73 (s, 1H), 7.55-7.52 (m, 2H), 7.07 (s, 1H), 7.02-7.00 (d, J = 8.4 Hz, 1H), 6.94-6.92 (d, J = 8.4 Hz, 1H), 6.83-6.79 (m, 2H), 4.50-4.48 (m, 2H), 4.44 (s, 1H), 431-4.14 (m, 1H), 4.07-4.05 (m, 2H), 3.90-3.88 (m, 2H), 3.84-3.82 (m, 2H), 3.73-3.70 (m, 9H), 3.68-3.41 (m, 2H), 3.27-3.08 (m, 2H), 2.78-2.58 (m, 3H), 2.50-2.39 (m, 2H), 2.31-2.29 (m, 3H), 2.15-1.92 (m, 3H), 1.89-1.67 (m, 9H), 1.25-1.21 (m, 6H), 1.18-1.00 (m, 2H). |

TABLE 1-continued

| | | | | | |
|---|---|---|---|---|---|
| 350 | 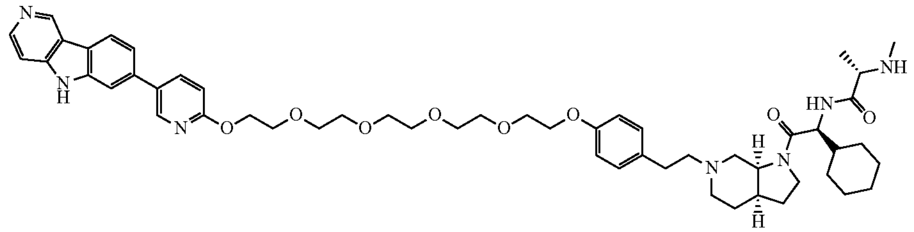 [SMILES: CN[C@@H](C)C(=O)N[C@H](C(=O)N1CC[C@H]2CCN(CCc3ccc(OCCOCCOCCOCCOCCOc4ccc(-c5ccc6c(c5)[nH]c5ccncc56)cn4)cc3)C[C@H]21)C1CCCCC1] | (S)-N-((S)-2-((3aR,7aS)-6-(4-((14-((5-(5H-pyrido[4,3-b]indol-7-yl)pyridin-2-yl)oxy)-3,6,9,12-tetraoxatetradecyl)oxy)phenethyl)octahydro-1H-pyrrolo[2,3-c]pyridin-1-yl)-1-cyclohexyl-2-oxoethyl)-2-(methylamino)propanamide | | 934.9 | 1H NMR (400 MHz, CD3OD): δ 9.27 (s, 1H), 8.47 (s, 1H), 8.40 (s, 1H), 8.29-8.27 (d, J = 8.0 Hz, 1H), 8.04-8.02 (d, J = 8.8 Hz, 1H), 7.74 (s, 1H), 7.55-7.52 (m, 2H), 7.08-7.01 (m, 2H), 6.95-6.93 (d, J = 8.4 Hz, 1H), 6.83-6.79 (m, 2H), 4.57-4.48 (m, 2H), 4.40 (s, 1H), 4.29-4.11 (m, 1H), 4.07-4.05 (m, 2H), 3.92 (s, 1H), 3.90-3.87 (m, 2H), 3.83-3.82 (m, 2H), 3.72-3.69 (m, 8H), 3.68-3.66 (m, 4H), 3.59-3.49 (m, 1H), 3.40-3.37 (m, 1H), 3.34-3.32 (m, 1H), 2.79-2.60 (m, 3H), 2.53-2.41 (m, 2H), 2.31-2.29 (m, 4H), 2.19-1.93 (m, 3H), 1.91-1.59 (m, 9H), 1.25-1.21 (m, 6H), 1.18-1.01 (m, 2H). |
| 351 | 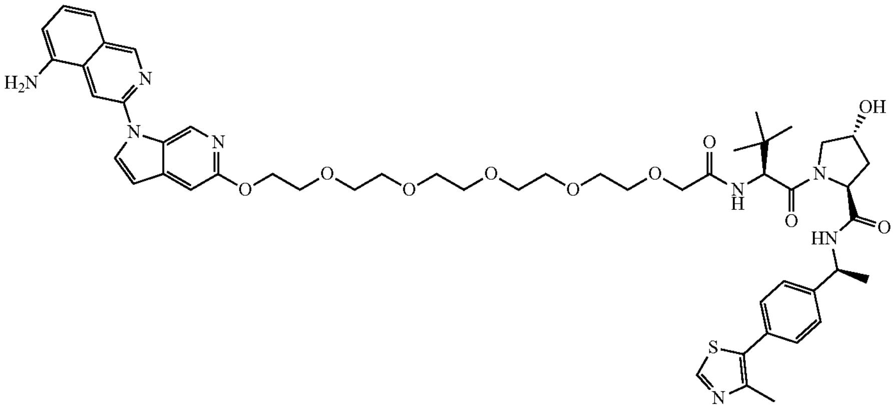 [SMILES: Cc1ncsc1-c1ccc([C@H](C)NC(=O)[C@@H]2C[C@@H](O)CN2C(=O)[C@@H](NC(=O)COCCOCCOCCOCCOCCOc2cc3ccn(-c4cc5c(N)cccc5cn4)c3cn2)C(C)(C)C)cc1] | (2S,4R)-1-((S)-20-((1-(5-aminoisoquinolin-3-yl)-1H-pyrrolo[2,3-c]pyridin-5-yl)oxy)-2-(tert-butyl)-4-oxo-6,9,12,15,18-pentaoxa-3-azaicosanoyl)-4-hydroxy-N-((S)-1-(4-(4-methylthiazol-5-yl)phenyl)ethyl)pyrrolidine-2-carboxamide | B | 981.8 | 1H NMR (300 MHz, DMSO-D6): δ δ 9.33 (s, 1H), 9.21 (s, 1H), 9.03 (s, 1H), 8.49-8.42 (m, 1H), 8.31 (m, 1H), 8.25 (s, 1H), 7.52-7.31 (m, 7H), 7.01 (s, 1H), 6.90 (m, 1H), 6.72 (m, 1H), 6.08 (s, 1H), 5.12 (m, 1H), 4.98-4.82 (m, 1H), 4.61-4.52 (m, 1H), 4.50-4.39 (m, 3H), 4.32-4.23 (m, 1H), 3.95 (s, 3H), 3.81-3.72 (m, 3H), 3.65-3.49 (m, 14H), 2.58-2.41 (s, 3H), 2.10-1.95 (m, 1H), 1.88-1.71 (m, 1H), 1.42-1.35 (m, 3H), 1.25 (m, 1H), 0.97 (m, 11H). |
| 352 | 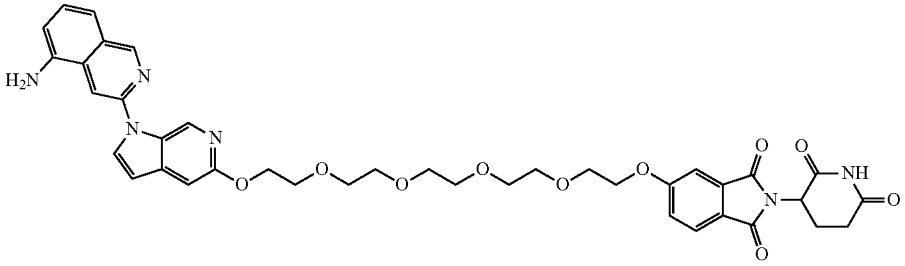 [SMILES: Nc1cccc2cnc(-n3ccc4cc(OCCOCCOCCOCCOCCOc5ccc6c(c5)C(=O)N(C5CCC(=O)NC5=O)C6=O)ncc43)cc12] | 5-((14-((1-(5-aminoisoquinolin-3-yl)-1H-pyrrolo[2,3-c]pyridin-5-yl)oxy)-3,6,9,12-tetraoxatetradecyl)oxy)-2-(2,6-dioxopiperidin-3-yl)isoindoline-1,3-dione | A | 753.6 | $^1$H NMR (300 MHz, DMSO-$d_6$) δ: 11.11 (s, 1H), 9.36 (s, 1H), 9.20 (s, 1H), 8.31-8.17 (d, 2H), 7.89-7.76 (m, 1H), 7.45 (s, 1H), 7.41-7.31 (m, 3H), 7.02 (m, 1H), 6.97-6.87 (m, 1H), 6.74 (m, 1H), 6.10 (s, 2H), 5.18-5.05 (m, 1H), 4.45-4.25 (m, 4H), 3.78 (m, 4H), 3.70-3.50 (m, 12H), 3.12-2.70 (m, 2H), 2.21-1.92 (m, 2H). |

TABLE 1-continued

| | | | | | |
|---|---|---|---|---|---|
| 353 | 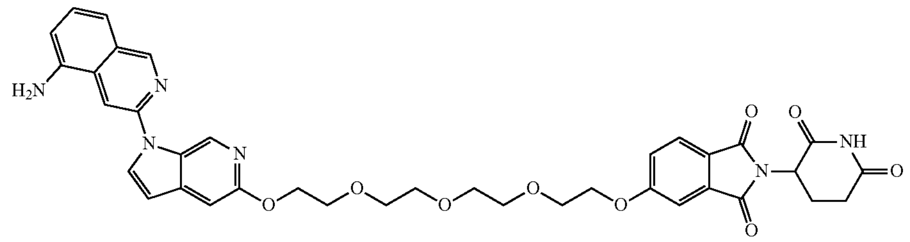 [SMILES: Nc1cccc2cnc(-n3ccc4cc(OCCOCCOCCOCCOc5ccc6c(c5)C(=O)N(C5CCC(=O)NC5=O)C6=O)ncc43)cc12] | 5-(2-(2-(2-(2-((1-(5-aminoisoquinolin-3-yl)-1H-pyrrolo[2,3-c]pyridin-5-yl)oxy)ethoxy)ethoxy)ethoxy)ethoxy)-2-(2,6-dioxopipieridin-3-yl)isoindoline-1,3-dione | A | 709.5 | $^1$H NMR (300 MHz, DMSO-$d_6$) δ: 11.12 (s, 1H), 9.32 (s, 1H), 9.17 (s, 1H), 8.30 (d, 1H), 8.23 (s, 1H), 7.80 (d, 1H), 7.48-7.41 (m, 1H), 7.32 (m, 3H), 7.00 (s, 1H), 6.99 (m, 1H), 6.71 (d, 1H), 6.08 (m, 2H), 5.13-5.07 (m, 1H), 4.48-4.37 (m, 2H), 4.36-4.22 (m, 2H), 4.37-4.25 (m, 2H), 3.77 (m, 4H), 3.59-3.57 (m, 8H), 2.95-2.81 (m, 1H), 2.12-1.95 (m, 1H). |
| 354 | 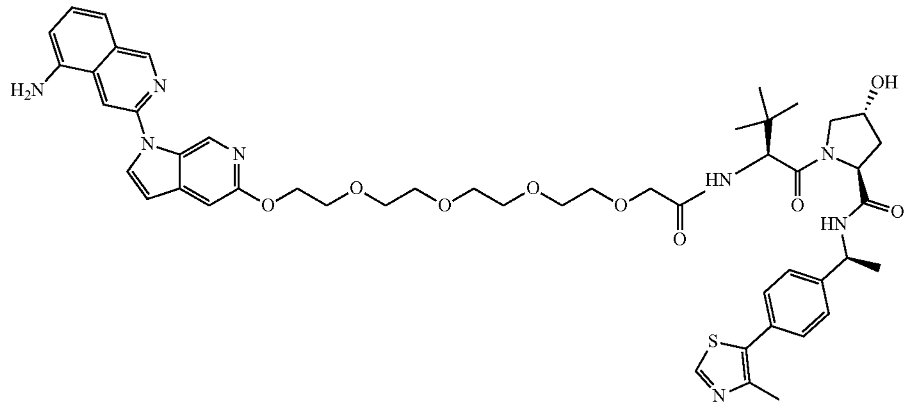 [SMILES: Cc1ncsc1-c1ccc([C@H](C)NC(=O)[C@@H]2C[C@@H](O)CN2C(=O)[C@@H](NC(=O)COCCOCCOCCOCCOc2cc3ccn(-c4cc5c(N)cccc5cn4)c3cn2)C(C)(C)C)cc1] | (2S,4R)-1-((S)-17-((1-(5-aminoisoquinolin-3-yl)-1H-pyrrolo[2,3-c]pyridin-5-yl)oxy)-2-(tert-butyl)-4-oxo-6,9,12,15-tetraoxa-3-azaheptadecanoyl)-4-hydroxy-N-((S)-1-(4-(4-methylthiazol-5-yl)phenyl)ethyl)pyrrolidine-2-carboxamide | | 937.8 | 1H NMR (300 MHz, DMSO-D6): δ 9.34 (s, 1H), 9.19 (s, 1H), 9.00 (s, ,1H), 8.47-8.44 (m, 1H), 8.32 (s, 1H), 8.24 (s, 1H), 7.45-7.34 (m, 7H), 7.02 (s, 1H), 6.93 (m, 1H), 6.75-6.74 (m, 1H), 6.10 (m, 2H), 5.16-5.15 (m, 1H), 4.98-4.82 (m, 1H), 4.57-4.54 (m, 1H), 4.46-4.40 (m, 3H), 4.29 (m, 1H), 3.97 (m, 3H), 3.80-3.77 (m, 3H), 3.61-3.46 (m, 6H), 2.46 (s, 3H), 2.02-2.00 (m, 2H), 1.81-1.78 (m, 1H), 1.48-1.33 (m, 3H), 1.25 (m, 5H), 0.95-0.85 (m, 9H). |
| 355 | 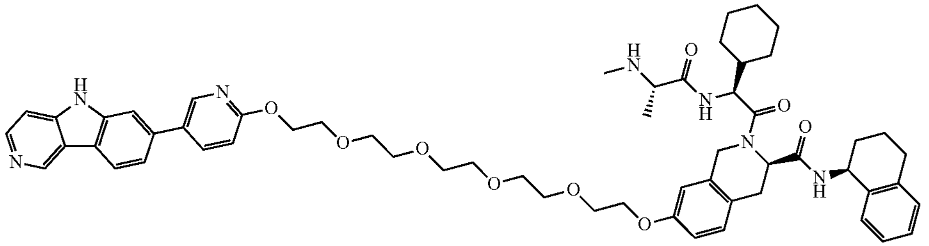 [SMILES: CN[C@@H](C)C(=O)N[C@H](C(=O)N1Cc2cc(OCCOCCOCCOCCOCCOc3ccc(-c4ccc5c(c4)[nH]c4ccncc45)cn3)ccc2C[C@@H]1C(=O)N[C@H]1CCCc2ccccc21)C1CCCCC1] | (R)-7-((14-((5-(5H-pyrido[4,3-c]indol-7-yl)pyridin-2-yl)oxy)-3,6,9,12-tetraoxatetradecyl)oxy)-2-((S)-2-cyclohexyl-2-((S)-2-(methylamino)propanamido)acetyl)-N-((S)-1,2,3,4-tetrahydronaphthalen-1-yl)-1,2,3,4-tetrahydroisoquinoline-3-carboxamide | | 1010.9 | 1H NMR (300 MHz, DMSO-D6): δ 13.2 (s, 1H), 9.76 (s, 1H), 8.76 (s, 1H), 8.67 (s, 1H), 8.65 (d, J = 8.8 Hz, 1H), 8.50 (d, J = 8.8 Hz, 1H), 8.01 (s, 1H), 7.81-7.00 (m, 2H), 7.05-6.94 (m, 5H), 6.93 (d, J = 8.4 Hz, 2H), 6.66 (dd, J = 4, 12 Hz, 1H), 4.91 (d, J = 4.8 Hz, 1H), 4.8-4.75 (m, 2H), 4.7-4.65 (m, 2H), 4.44 (s, 2H), 4.07 (s, 2H), 3.77 (s, 1H), 3.96 (t, J = 5.6 Hz, 2H), 3.74-3.72 (m, 5H), 3.59-3.56 (m, 4H), 3.55-3.54 (m, 9H), 3.09-3.03 (m, 1H), 2.67 (s, 1H), 1.81 (s, 4H), 1.64-1.63 (m, 6H), 1.26-1.14 (m, 8H). |

TABLE 1-continued

| | | | | |
|---|---|---|---|---|
| 356 | 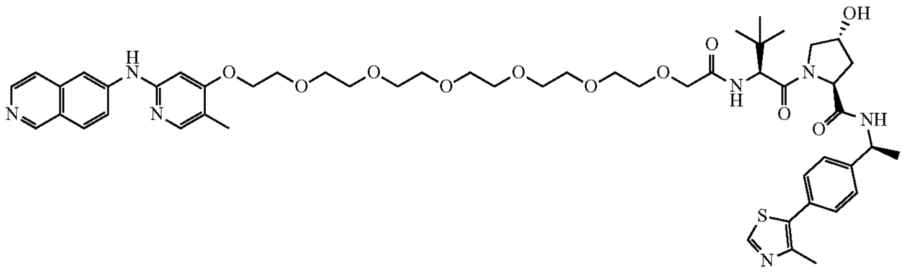 [SMILES: Cc1cnc(Nc2ccc3cnccc3c2)cc1OCCOCCOCCOCCOCCOCCOCC(=O)N[C@H](C(=O)N1C[C@H](O)C[C@H]1C(=O)N[C@@H](C)c1ccc(-c2scnc2C)cc1)C(C)(C)C] | (2S,4R)-1-((S)-2-(tert-butyl)-23-((2-(isoquinolin-6-ylamino)-5-methylpyridin-4-yl)oxy)-4-oxo-6,9,12,15,18,21-hexaoxa-3-azatricosanoyl)-4-hydroxy-N-((S)-1-(4-(4-methylthiazol-5-yl)phenyl)ethyl)pyrrolidine-2-carboxamide | 1000.8 | 1H NMR (400 MHz, Deuterium Oxide): δ 9.47 (s, 1H), 9.35 (s, 1H), 8.35-8.29 (m, 2H), 8.11 (m, 1H), 7.84 (s, 2H), 7.73 (m, 1H), 7.42-7.34 (m, 4H), 6.91 (s, 1H), 4.83-4.70 (m, 2H), 4.47-3.82 (m, 11H), 3.70-3.53 (m, 20H), 2.47-2.43 (s, 3H), 2.22 (m, 1H), 2.12 (s, 2H), 1.75-1.38 (m, 5H), 1.05-0.99 (m, 3H), 0.90-0.87 (m, 9H). |
| 357 | 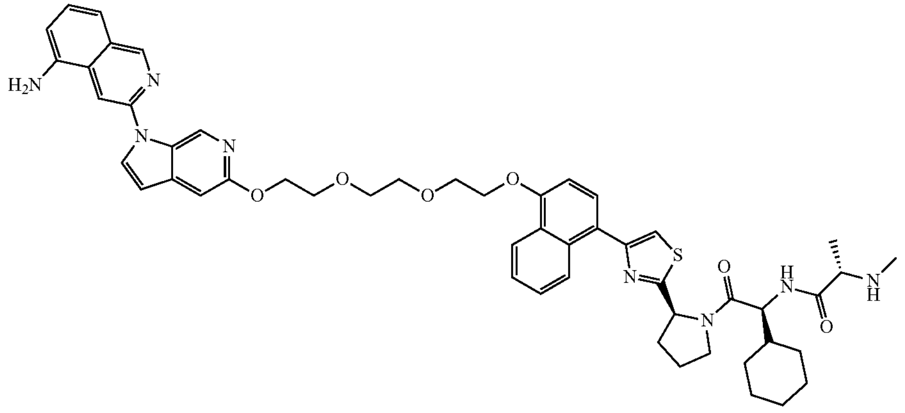 [SMILES: CN[C@@H](C)C(=O)N[C@H](C(=O)N1CCC[C@H]1c1nc(-c2ccc(OCCOCCOCCOc3cc4ccn(-c5cc6c(N)cccc6cn5)c4cn3)c3ccccc23)cs1)C1CCCCC1] | (S)-N-((S)-2-((S)-2-(4-(4-(2-(2-(2-((1-(5-aminoisoquinolin-3-yl)-1H-pyrrolo[2,3-c]pyridin-5-yl)oxy)ethoxy)ethoxy)ethoxy)napthalen-1-yl)thiazol-2-yl)pyrrolidin-1-yl)-1-cyclohexyl-2-oxoethyl)-2-(methylamino)propanamide | 911.8 | $^1$H NMR (300 MHz, DMSO-$d_6$): δ 9.33 (s, 1H), 9.18 (s, 1H), 8.29-8.21 (m, 5H), 8.04 (d, 1H), 7.68 (s, 1H), 7.58-7.51 (m, 3H), 7.35-7.33 (m, 2H), 7.30-6.99 (m, 2H), 6.90 (m, 1H), 6.71-6.70 (m, 1H), 6.09 (m, 1H), 5.48-5.40 (m, 1H), 4.43 (m, 1H), 4.41-4.39 (m, 2H), 4.33-4.30 (m, 2H), 3.95-3.92 (m, 2H), 3.82-3.80 (m, 4H), 3.79-3.67 (m, 5H), 3.13-3.05 (m, 1H), 2.31-2.16 (m, 5H), 2.13-1.91 (m, 3H), 1.72-1.67 (m, 6H), 1.23-1.04 (m, 7H). |
| 358 | 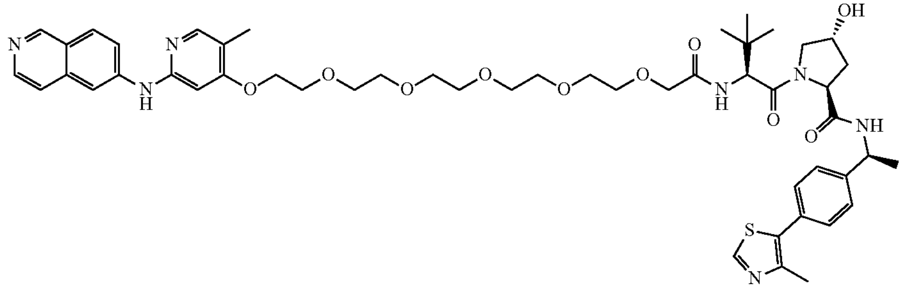 [SMILES: Cc1cnc(Nc2ccc3cnccc3c2)cc1OCCOCCOCCOCCOCCOCC(=O)N[C@H](C(=O)N1C[C@H](O)C[C@H]1C(=O)N[C@@H](C)c1ccc(-c2scnc2C)cc1)C(C)(C)C] | (2S,4R)-1-((S)-2-(tert-butyl)-20-((2-(isoquinolin-6-ylamino)-5-methylpyridin-4-yl)oxy)-4-oxo-6,9,12,15,18-pentaoxa-3-azaicosanoyl)-4-hydroxy-N-((S)-1-(4-(4-methylthiazol-5-yl)phenyl)ethyl)pyrrolidine-2-carboxamide | 956.8 | $^1$H NMR (300 MHz, DMSO-d6) δ 9.42 (s, 1H), 9.03-8.98 (m, 2H), 8.49-8.44 (m, 2H), 8.31-8.29 (m, 1H), 7.96-7.92 (m, 2H), 7.66-7.58 (m, 2H), 7.44-7.35 (m, 5H), 6.51 (s, 1H), 5.15 (m, 1H), 4.90 (m, 1H), 4.56-4.42 (m, 2H), 4.28-4.16 (m, 3H), 3.95-3.82 (m, 4H), 3.62-3.53 (m, 15H), 2.45 (s, 3H), 2.06-2.01 (m, 5H), 1.82-1.65 (m, 1H), 1.46-1.35 (m, 3H), 1.24 (m, 2H), 0.94 (s, 9H). |

TABLE 1-continued

| | | | | |
|---|---|---|---|---|
| 359 | 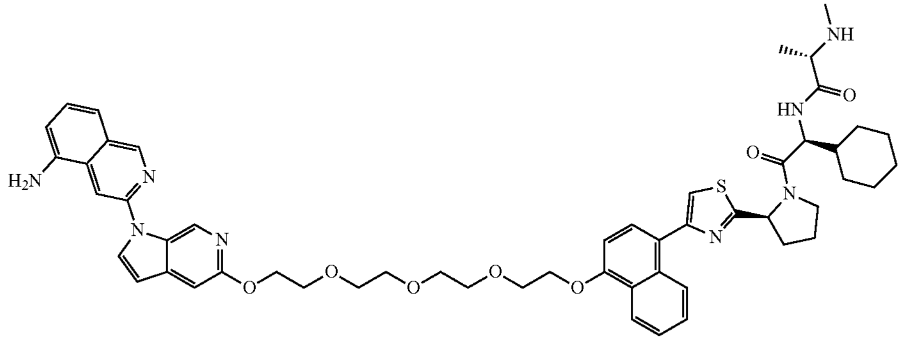 [SMILES: CN[C@@H](C)C(=O)N[C@H](C(=O)N1CCC[C@H]1c1nc(-c2ccc(OCCOCCOCCOCCOc3cc4ccn(-c5cc6c(N)cccc6cn5)c4cn3)c3ccccc23)cs1)C1CCCCC1] | (S)-N-((S)-2-((S)-2-(4-(4-(2-(2-(2-(2-((1-(5-aminoisoquinolin-3-yl)-1H-pyrrolo[2,3-c]pyridin-5-yl)oxy)ethoxy)ethoxy)ethoxy)ethoxy)naphthalen-1-yl)thiazol-2-yl)pyrrolidin-1-yl)-1-cyclohexyl-2-oxoethyl)-2-(methylamino)propanamide | 955.8 | 1H NMR (300 MHz, DMSO-D6): δ 9.33 (s, 1H), 9.18 (s, 1H), 8.30-8.23 (m, 5H), 8.08 (m, 1H), 7.68 (s, 1H), 7.62-7.49 (m, 3H), 7.34 (m, 2H), 7.01 (m, 2H), 6.90 (m, 1H), 6.72 (m, 1H), 6.08 (s, 1H), 5.44 (m, 1H), 4.52-4.31 (m, 4H), 3.92-3.84 (m, 2H), 3.82-3.72 (m, 4H), 3.69-3.63 (m, 2H), 3.59-3.52 (m, 6H), 2.85-2.65 (m, 2H), 2.38-2.15 (m, 4H), 2.15-1.95 (m, 2H), 1.80-1.50 (m, 4H), 1.40-0.98 (m, 12H). |
| 360 | 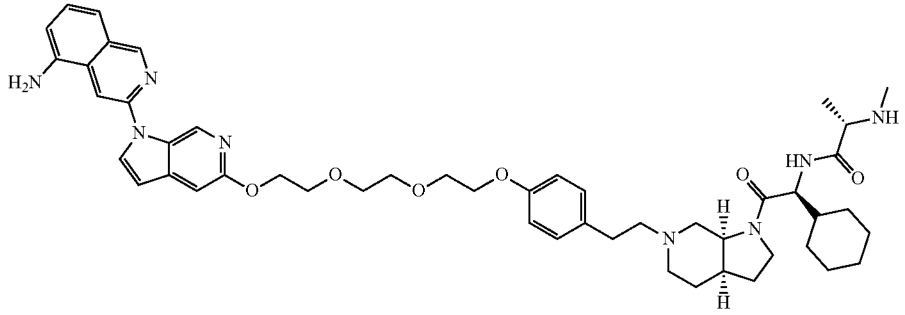 [SMILES: CN[C@@H](C)C(=O)N[C@H](C(=O)N1CC[C@H]2CCN(CCc3ccc(OCCOCCOCCOc4cc5ccn(-c6cc7c(N)cccc7cn6)c5cn4)cc3)C[C@H]21)C1CCCCC1] | (S)-N-((S)-2-((3aR,7aS)-6-(4-(2-(2-(2-((1-(5-aminoisoquinolin-3-yl)-1H-pyrrolo[2,3-c]pyridin-5-yl)oxy)ethoxy)ethoxy)ethoxy)phenethyl)octahydro-1H-pyrrolo[2,3-c]pyridin-1-yl)-1-cyclohexyl-2-oxoethyl)-2-(methylamino)propanamide | 861.8 | $^1$H NMR (300 MHz, DMSO-$d_6$): δ 9.33 (s, 1H), 9.18 (s, 1H), 8.31-8.30 (m, 2H), 8.23 (s, 1H), 7.35-7.33 (m, 2H), 7.11-7.00 (m, 3H), 6.91-6.72 (m, 4H), 6.09 (s, 2H), 4.50-4.40 (m, 2H), 4.02-3.88 (m, 2H), 3.78-3.73 (m, 5H), 3.62 (m, 5H), 2.52 (m, 2H), 2.32-2.27 (m, 5H), 2.10-1.88 (m, 4H) 1.68-1.45 (m, 11H), 1.39-1.19 (m, 10H), 1.02-0.78 (m, 2H). |
| 361 | 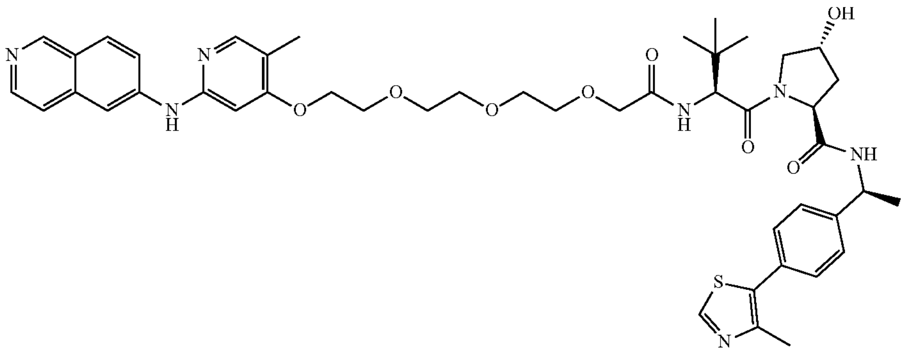 [SMILES: Cc1cnc(Nc2ccc3cnccc3c2)cc1OCCOCCOCCOCC(=O)N[C@H](C(=O)N1C[C@H](O)C[C@H]1C(=O)N[C@@H](C)c1ccc(-c2scnc2C)cc1)C(C)(C)C] | (2S,4R)-1-((S)-2-(tert-butyl)-14-((2-(isoquinolin-6-ylamino)-5-methylpyridin-4-yl)oxy)-4-oxo-6,9,12-trioxa-3-azatetradecanoyl)-4-hydroxy-N-((S)-1-(4-(4-methylthiazol-5-yl)phenyl)ethyl)pyrrolidne-2-carboxamide | 868.7 | 1H NMR (400 MHz, DMSO-D6): δ 9.42 (s, 1H), 9.03 (s, 1H), 8.98 (s, 1H), 8.48 (m, 2H), 8.29 (m, 1H), 7.96 (m, 2H), 7.65-7.60 (m, 2H), 7.42-7.34 (m, 5H), 6.51 (d, 1H), 5.14-5.13 (m, 1H), 4.91-4.87 (m, 1H), 4.56-4.53 (m, 1H), 4.46-4.42 (m, 1H), 4.28 (m, 1H), 4.17-4.16 (m, 2H), 3.96 (s, 2H), 3.84-3.82 (m, 2H), 3.67 (m, 2H), 3.61-3.59 (m, 7H), 2.45 (s, 3H), 2.07 (m, 4H), 1.77 (m, 1H), 1.41-1.36 (m, 4H), 0.94 (s, 9H). |

TABLE 1-continued

| | | | | |
|---|---|---|---|---|
| 362 | 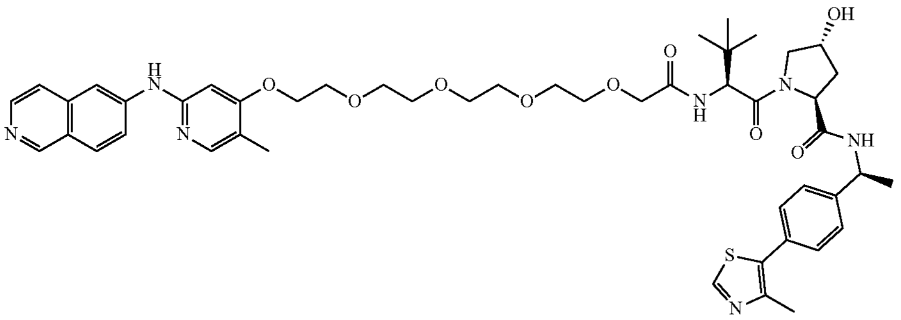 [SMILES: Cc1cnc(Nc2ccc3cnccc3c2)cc1OCCOCCOCCOCCOCC(=O)N[C@H](C(=O)N1C[C@H](O)C[C@H]1C(=O)N[C@@H](C)c1ccc(-c2scnc2C)cc1)C(C)(C)C] | (2S,4R)-1-((S)-2-(tert-butyl)-17-((2-(isoquinolin-6-ylamino)-5-methylpyridin-4-yl)oxy)-4-oxo-6,9,12,15-tetraoxa-3-azaheptadecanoyl)-4-hydroxy-N-((S)-1-(4-(4-methylthiazol-5-yl)phenyl)ethyl) pyrrolidine-2-carboxamide | 912.8 | $^{1}$H NMR (400 MHz, DMSO-d6): δ 9.41 (s, 1H), 9.02 (s, 1H), 8.98 (s, 1H), 8.48-8.43 (m, 2H), 8.31-8.29 (m, 1H), 7.96-7.92 (m, 2H), 7.67-7.63 (m, 1H), 7.59-7.58 (m, 1H), 7.43-7.34 (m, 5H), 6.51 (s, 1H), 5.14-5.13 (d, 1H), 4.92-4.85 (m, 1H), 4.55-4.53 (m, 1H), 4.44 (m, 1H), 4.28 (m, 1H), 4.17-4.15 (m, 2H), 3.95 (s, 2H), 3.84-3.81 (m, 2H), 3.65-3.55 (m, 13H), 2.44 (s, 3H), 2.04-1.95 (m, 3H), 1.77 (m, 1H), 1.36 (m, 3H), 1.24 (m, 2H), 0.94 (s, 9H). |
| 363 | 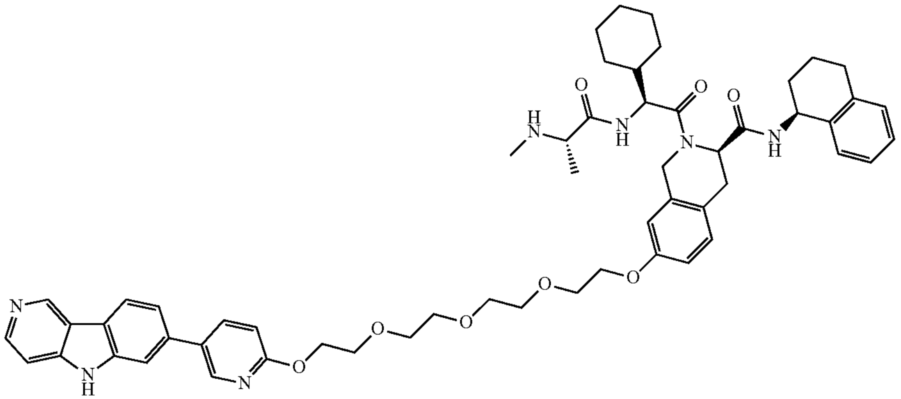 [SMILES: CN[C@@H](C)C(=O)N[C@H](C(=O)N1Cc2cc(OCCOCCOCCOCCOc3ccc(-c4ccc5c(c4)[nH]c4ccncc45)cn3)ccc2C[C@@H]1C(=O)N[C@H]1CCCc2ccccc21)C1CCCCC1] | (R)-7-(2-(2-(2-(2-((5-(5H-pyrido[4,3-b]indol-7-yl)pyridin-2-yl)oxy)ethoxy)ethoxy)ethoxy)ethoxy)-2-((S)-2-cyclohexyl-2-((S)-2-(methylamino)propanamido)acetyl)-N-((S)-1,2,3,4-tetrahydronaphthalen-1-yl)-1,2,3,4-tetrahydroisoquinoline-3-carboxamide | 966.9 | 1H NMR (400 MHz, DMSO-D6): δ 11.79 (s, 1H), 9.35 (s, 1H), 8.56 (s, 1H), 8.43 (d, J = 5.6 Hz, 1H), 8.34-8.25 (m, 1H), 8.21 (s, 2H), 8.14-8.02 (m, 2H), 7.77 (s, 1H), 7.55 (d, J = 8.4 Hz, 1H), 7.48 (d, J = 5.6 Hz, 1H), 7.12-6.94 (m, 5H), 6.85-6.77 (m, 1H), 6.71-6.61 (m, 1H), 5.12-4.65 (m, 5H), 4.46-4.40 (m, 2H), 4.13-4.05 (m, 2H), 3.82-3.73 (m, 4H), 3.59 (d, J = 7.0 Hz, 10H), 3.11-2.94 (m, 2H), 2.76-2.64 (m, 2H), 2.23-2.11 (m, 3H), 1.91-1.44 (m, 11H), 1.18-0.90 (m, 8H). |

TABLE 1-continued

| | | | | |
|---|---|---|---|---|
| 364 | 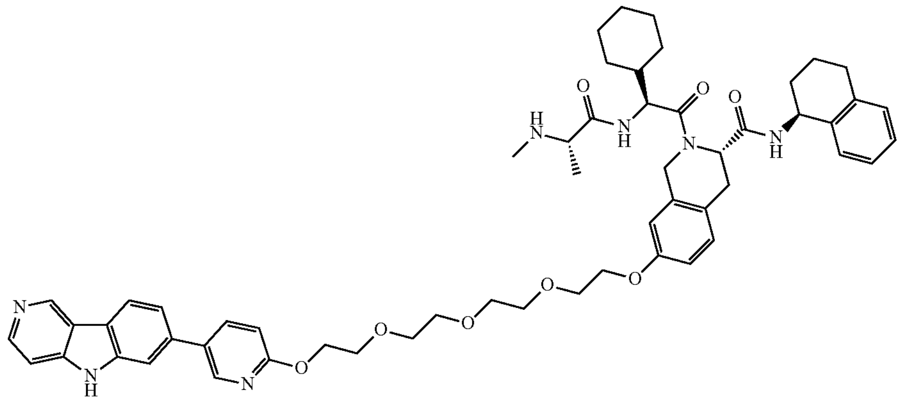 [SMILES: CN[C@@H](C)C(=O)N[C@H](C(=O)N1Cc2cc(OCCOCCOCCOCCOc3ccc(-c4ccc5c(c4)[nH]c4ccncc45)cn3)ccc2C[C@H]1C(=O)N[C@H]1CCCc2ccccc21)C1CCCCC1] | (S)-7-(2-(2-(2-(2-((5-(5H-pyrido[4,3-b]indol-7-yl)pyridin-2-yl)oxy)ethoxy)ethoxy)ethoxy)ethoxy)-2-((S)-2-cyclohexyl-2-((S)-2-(methylamino)propanamido)acetyl)-N-((S)-1,2,3,4-tetrahydronaphtalen-1-yl)-1,2,3,4-tetrahydroisoquinoline-3-carboxamide | 966.9 | 1H NMR (400 MHz, DMSO-D6): δ 11.77 (s, 1H), 9.34 (d, J = 0.8 Hz, 1H), 8.55 (d, J = 2.4, Hz, 1H), 8.42 (d, J = 5.6 Hz, 1H), 8.29 (d, J = 8.4 Hz, 1H), 8.26-8.21 (m, 1H), 8.18 (s, 2H), 8.10 (dd, J = 2.4, 8.8 Hz, 1H), 7.85 (d, J = 8.8 Hz, 1H), 7.77 (s, 1H), 7.54 (dd, J = 1.2, 8.4 Hz, 1H), 7.47 (dd, J = 0.8, 5.6 Hz, 1H), 7.15-7.04 (m, 1H), 7.04-6.98 (m, 1H), 6.95 (d, J = 8.8 Hz, 1H), 6.88 (d, J = 2.8 Hz, 1H), 6.85-6.75 (m, 1H), 5.20-5.08 (m, 1H), 4.91-4.70 (m, 1H), 4.65-4.48 (m, 1H), 4.47-4.37 (m, 1H), 4.07 (d, J = 3.6 Hz, 1H), 3.76 (td, J = 4.4, 14.8 Hz, 1H), 3.62-3.54 (m, 1H), 3.25-3.09 (m, 1H), 3.05-2.87 (m, 1H), 2.66 (d, J = 5.6 Hz, 1H), 2.22 (s, 1H), 1.99 (s, 1H), 1.80-1.45 (m, 9H), 1.15-0.83 (m, 8H). |
| 365 | 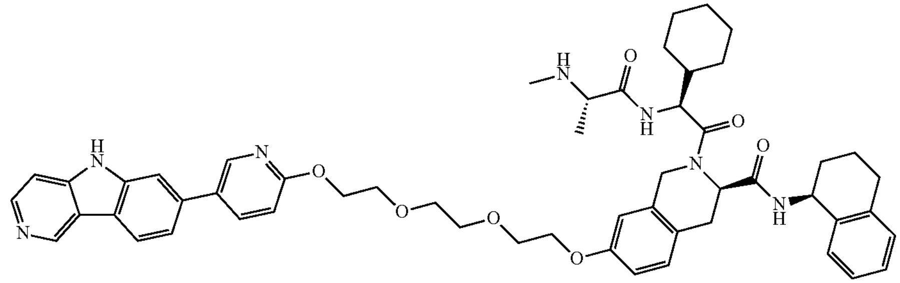 [SMILES: CN[C@@H](C)C(=O)N[C@H](C(=O)N1Cc2cc(OCCOCCOCCOc3ccc(-c4ccc5c(c4)[nH]c4ccncc45)cn3)ccc2C[C@@H]1C(=O)N[C@H]1CCCc2ccccc21)C1CCCCC1] | (R)-7-(2-(2-(2-((5-(5H-pyrido[4,3-b]indol-7-yl)pyridin-2-yl)oxy)ethoxy)ethoxy)ethoxy)-2-((S)-2-cyclohexyl-2-((S)-2-(methylamino)propanamido)acetyl)-N-((S)-1,2,3,4-tetrahydronaphthalen-1-yl)-1,2,3,4-tetra-hydroisoquinoline-3-carboxamide | 922.8 | 1H NMR (400 MHz, DMSO-D6): δ 11.88-11.69 (m, 1H), 9.35 (s, 1H), 8.56 (d, J = 2.0 Hz, 1H), 8.43 (d, J = 5.6 Hz, 1H), 8.33-8.27 (m, 1H), 8.21 (s, 1H), 8.16-7.94 (m, 3H), 7.77 (s, 1H), 7.55 (d, J = 8.0 Hz, 1H), 7.48 (d, J = 5.6 Hz, 1H), 7.14-6.90 (m, 6H), 6.86-6.76 (m, 1H), 6.73-6.62 (m, 1H), 5.11-4.60 (m, 5H), 4.45 (d, J = 4.8 Hz, 2H), 4.10 (d, J = 4.0 Hz, 2H), 3.83-3.73 (m, 4H), 3.66-3.62 (m, 4H), 3.11-2.94 (m, 2H), 2.74-2.60 (m, 2H), 2.20-2.14 (m, 3H), 1.91-1.53 (m, 11H), 1.24-0.89 (m, 9H). |
| 366 | 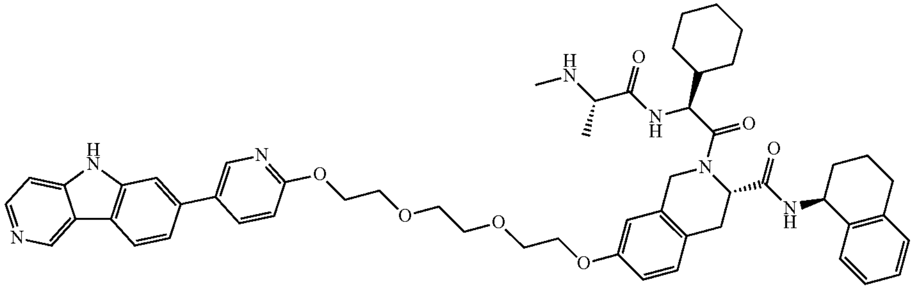 [SMILES: CN[C@@H](C)C(=O)N[C@H](C(=O)N1Cc2cc(OCCOCCOCCOc3ccc(-c4ccc5c(c4)[nH]c4ccncc45)cn3)ccc2C[C@H]1C(=O)N[C@H]1CCCc2ccccc21)C1CCCCC1] | (S)-7-(2-(2-(2-((5-(5H-pyrido[4,3-b]indol-7-yl)pyridin-2-yl)oxy)ethoxy)ethoxy)ethoxy)-2-((S)-2-cyclohexyl-2-((S)-2-(methylamino)propanamido)acetyl)-N-((S)-1,2,3,4-tetrahydronaphthalen-1-yl)-1,2,3,4-tetrahydroisoquinoline-3-carboxamide | 922.8 | 1H NMR (400 MHz, DMSO-D6): δ 11.78 (s, 1H), 9.34 (d, J = 0.8 Hz, 1H), 8.55 (d, J = 2.4 Hz, 1H), 8.42 (d, J = 5.6 Hz, 1H), 8.29 (d, J = 8.4 Hz, 1H), 8.23 (d, J = 8.4 Hz, 1H), 8.19 (s, 2H), 8.10 (dd, J = 2.8, 8.8 Hz, 1H), 7.84 (d, J = 8.8 Hz, 1H), 7.76 (s, 1H), 7.54 (dd, J = 1.5, 8.4 Hz, 1H), 7.47 (dd, J = 0.8, 5.6 Hz, 1H), 7.13-7.03 (m, 2H), 7.03-6.97 (m, 2H), 6.95 (d, J = 8.8 Hz, 1H), 6.89 (d, J = 2.4 Hz, 1H), 6.85-6.75 (m, 2H), 6.65 (d, J = 7.6 Hz, 1H), 5.18-5.09 (m, 1H), 4.90-4.69 (m, 3H), 4.63-4.57 (m, 1H), 4.47-4.41 (m, 2H), 4.11-4.05 (m, 2H), 3.78 (td, J = 4.8, 9.6 Hz, 4H), 3.63 (s, 4H), 3.26-3.08 (m, 4H), 3.05-2.97 (m, 1H), 3.23-2.90 (m, 1H), 2.88 (dd, J = 6.0, 15.2 Hz, 1H), 2.71-2.58 (m, 2H), 2.22 (s, 1H), 1.98 (s, 2H), 1.77-1.50 (m, 9H), 1.16-0.88 (m, 8H). |

TABLE 1-continued

| | | | | | |
|---|---|---|---|---|---|
| 367 | 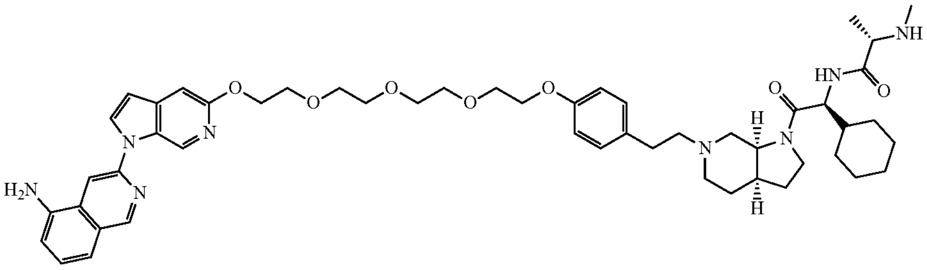 [SMILES: CN[C@@H](C)C(=O)N[C@H](C(=O)N1CC[C@H]2CCN(CCc3ccc(OCCOCCOCCOCCOc4cc5ccn(-c6cc7c(N)cccc7cn6)c5cn4)cc3)C[C@H]21)C1CCCCC1] | (S)-N-((S)-2-((3aR,7aS)-6-(4-(2-(2-(2-(2-((1-(5-aminoisoquinolin-3-yl)-1H-pyrrolo[2,3-c]pyridin-5-yl)oxy)ethoxy)ethoxy)ethoxy)ethoxy)phenethyl)octahydro-1H-pyrrolo[2,3-c]pyridin-1-yl)-1-cyclohexyl-2-oxoethyl)-2-(methylamino)propanamide | | 905.9 | 1H NMR (300 MHz, DMSO-d6): δ 9.33 (s, 1H), 9.18 (s, 1H), 8.34-8.30 (m, 1H), 8.25 (m, 1H), 7.97-7.83 (m, 1H), 7.37-7.31 (m, 2H), 7.12-7.01 (m, 3H), 6.92-6.70 (m, 4H), 6.11-6.00 (m, 2H), 4.48-4.37 (m, 4H), 4.11-3.97 (m, 5H), 3.87-3.70 (m, 8H), 3.69-3.49 (m, 10H), 2.21-2.10 (m, 5H), 1.77-1.47 (m, 9H), 1.28-1.02 (m, 9H), 1.01-0.82 (m, 2H). |
| 368 | 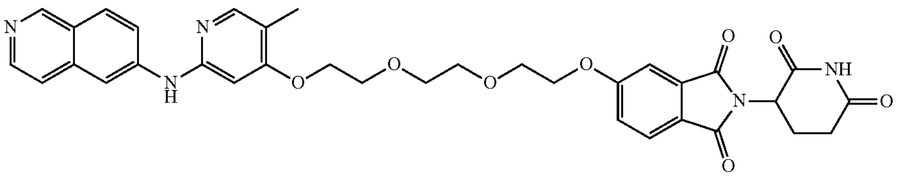 [SMILES: Cc1cnc(Nc2ccc3cnccc3c2)cc1OCCOCCOCCOc1ccc2c(c1)C(=O)N(C1CCC(=O)NC1=O)C2=O] | 2-(2,6-dioxopiperidin-3-yl)-5-(2-(2-(2-((2-(isoquinolin-6-ylamino)-5-methylpyridin-4-yl)oxy)ethoxy)ethoxy)ethoxy)isoindoline-1,3-dione | | 640.5 | 1H NMR (300 MHz, DMSO-d6): δ 11.11 (s, 1H), 9.41 (s, 1H), 9.02 (s, 1H), 8.46-8.27 (m, 2H), 7.93-7.65 (m, 3H), 7.69-7.34 (m, 4H), 6.55 (s, 1H), 5.11 (m, 1H), 4.30-4.16 (m, 5H), 3.82-3.67 (m, 8H), 2.89 (m, 2H), 2.55 (m, 1H), 2.05 (m, 3H). |
| 369 | 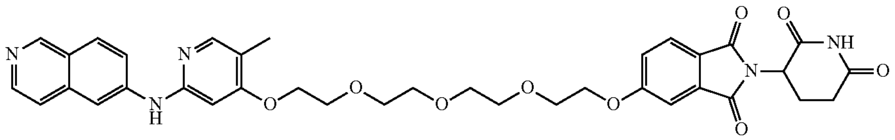 [SMILES: Cc1cnc(Nc2ccc3cnccc3c2)cc1OCCOCCOCCOCCOc1ccc2c(c1)C(=O)N(C1CCC(=O)NC1=O)C2=O] | 2-(2,6-dioxopiperidin-3-yl)-5-(2-(2-(2-(2-((2-(isoquinolin-6-ylamino)-5-methylpyridin-4-yl)oxy)ethoxy)ethoxy)ethoxy)ethoxy)isoindoline-1,3-dione | A | 684.5 | $^1$H NMR (400 MHz, DMSO-$d_6$): δ 11.09 (s, 1H), 9.37 (s, 1H), 9.00 (s, 1H), 8.44 (s, 1H), 8.29-8.27 (d, 1H), 7.92-7.90 (m, 2H), 7.80-7.77 (d, 1H), 7.63-7.55 (m, 2H), 7.41 (s, 1H), 7.33-7.31 (m, 1H), 6.47 (s, 1H), 5.13-5.02 (m, 1H), 4.26 (m, 2H), 4.13 (m, 2H), 3.80-3.75 (m, 5H), 3.60 (m, 8H), 2.92-2.82 (m, 2H), 2.02 (m, 4H). |
| 370 | 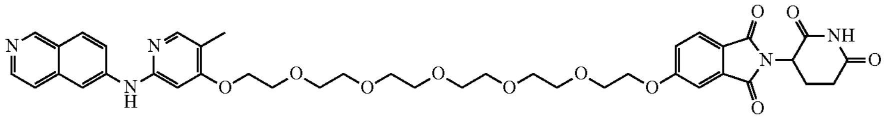 [SMILES: Cc1cnc(Nc2ccc3cnccc3c2)cc1OCCOCCOCCOCCOCCOCCOc1ccc2c(c1)C(=O)N(C1CCC(=O)NC1=O)C2=O] | 2-(2,6-dioxopiperidin-3-yl)-5-((17-((2-(isoquinolin-6-ylamino)-5-methylpyridin-4-yl)oxy)-3,6,9,12,15-pentaoxaheptadecyl)oxy)isoindoline-1,3-dione | | 772.6 | $^1$H NMR (400 MHz, Methanol-d4): δ 8.97 (s, 1H), 8.71-8.48 (m, 1H), 8.30 (m, 1H), 8.29 (m, 1H), 7.95-7.93 (m, 1H), 7.71 (m, 1H), 7.69 (m, 1H), 7.65-7.62 (m, 2H), 7.32 (m, 1H), 7.25-7.22 (m, 1H), 6.49 (s, 1H), 5.08 (m, 1H), 4.27-4.20 (m, 4H), 3.91-3.82 (m, 4H), 3.73-3.71 (m, 2H), 3.67-3.58 (m, 15H), 2.70 (m, 3H), 2.11 (m, 4H). |

TABLE 1-continued

| | | | | | |
|---|---|---|---|---|---|
| 371 | 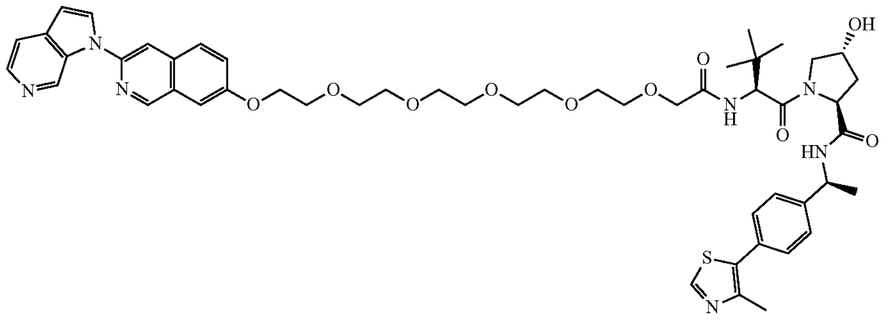 [SMILES: Cc1ncsc1-c1ccc([C@H](C)NC(=O)[C@@H]2C[C@@H](O)CN2C(=O)[C@@H](NC(=O)COCCOCCOCCOCCOCCOc2ccc3cc(-n4ccc5ccncc54)ncc3c2)C(C)(C)C)cc1] | (2S,4R)-1-((S)-20-((3-(1H-pyrrolo[2,3-c]pyridin-1-yl)isoquinolin-7-yl)oxy)-2-(tert-butyl)-4-oxo-6,9,12,15,18-pentaoxa-3-azaicosanoyl)-4-hydroxy-N-((S)-1-(4-(4-methylthiazol-5-yl)phenyl)ethyl)pyrrolidine-2-carboxamide | | 966.8 | 1H NMR (400 MHz, DMSO-d6): δ 9.63 (s, 1H), 9.29 (s, 1H), 8.98 (s, 1H), 8.46-8.44 (d, 1H), 8.31-8.27 (m, 2H), 8.22 (s, 1H), 8.03-8.01 (m, 1H), 7.69-7.64 (m, 2H), 7.54-7.52 (m, 1H), 7.43-7.35 (m, 5H), 6.86-6.85 (s, 1H), 5.15 (m, 1H), 4.89 (m, 1H), 4.55 (m, 1H), 4.44 (m, 1H), 4.29 (m, 3H), 3.96 (s, 2H), 3.87-3.85 (m, 2H), 3.65-3.52 (m, 15H), 2.45 (s, 3H), 2.08-2.00 (m, 2H), 1.75 (m, 1H), 1.38-1.36 (m, 3H), 1.24-1.16 (m, 2H), 0.94 (s, 9H). |
| 372 | 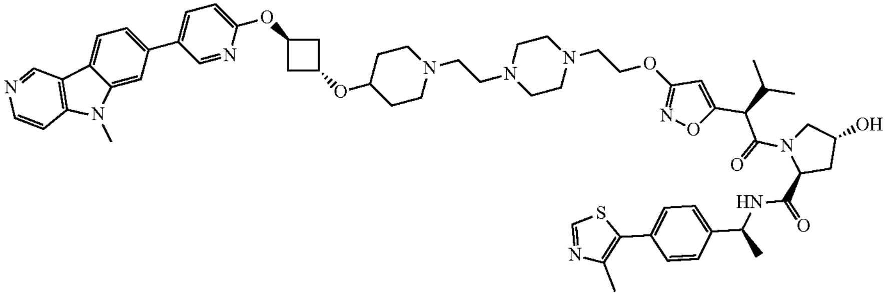 [SMILES: Cc1ncsc1-c1ccc([C@H](C)NC(=O)[C@@H]2C[C@@H](O)CN2C(=O)[C@@H](c2cc(OCCN3CCN(CCN4CCC(O[C@H]5C[C@H](Oc6ccc(-c7ccc8c9cnccc9n(C)c8c7)cn6)C5)CC4)CC3)no2)C(C)C)cc1] | (2S,4R)-4-hydroxy-1-((R)-3-methyl-2-(3-(2-(4-(2-(4-((1r,3r)-3-((5-(5-methyl-5H-pyrido[4,3-b]indol-7-yl)pyridin-2-yl)oxy)cyclobutoxy)piperidin-1-yl)ethyl)piperazin-1-yl)ethoxy)isoxazol-5-yl)butanoyl)-N-((S)-1-(4-(4-methylthiazol-5-yl)phenyl)ethyl)pyrrolidine-2-carboxamide | B | 1065.9 | 1H NMR (400 MHz, DMSO-D6): δ 9.77 (s, 1H), 9.05-8.88 (m, 1H), 8.77 (d, J = 6.8 Hz, 1H), 8.70 (d, J = 2.3 Hz, 1H), 8.55 (d, J = 8.0 Hz, 1H), 8.45-8.14 (m, 4H), 7.96-7.81 (m, 1H), 7.52-7.32 (m, 4H), 6.99 (d, J = 8.8 Hz, 1H), 6.30-5.82 (m, 1H), 5.44-5.29 (m, 1H), 4.91 (t, J = 7.2 Hz, 1H), 4.59-4.30 (m, 4H), 4.15 (s, 3H), 3.81-3.49 (m, 12H), 3.27-2.91 (m, 2H), 2.82-2.71 (m, 3H), 2.53 (s, 9H), 2.47-2.45 (m, 5H), 2.30-1.75 (m, 7H), 1.53-1.33 (m, 3H), 1.04-0.93 (m, 3H), 0.88-0.76 (m, 3H). |
| 373 | 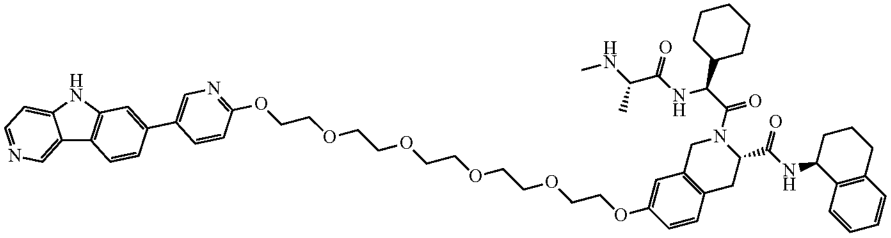 [SMILES: CN[C@@H](C)C(=O)N[C@H](C(=O)N1Cc2cc(OCCOCCOCCOCCOCCOc3ccc(-c4ccc5c(c4)[nH]c4ccncc45)cn3)ccc2C[C@H]1C(=O)N[C@H]1CCCc2ccccc21)C1CCCCC1] | (S)-7-((14-((5-(5H-pyrido[4,3-b]indol-7-yl)pyridin-2-yl)oxy)-3,6,9,12-tetraoxatetradecyl)oxy)-2-((S)-2-cyclohexyl-2-((S)-2-(methylamino)propanamido)acetyl)-N-((S)-1,2,3,4-tetrahydronaphthalen-1-yl)-1,2,3,4-tetrahydroisoquinoline-3-carboxamide | | 1010.9 | 1H NMR (400 MHz, DMSO-D6): δ 13.16 (s, 1H), 9.76 (s, 1H), 8.82-8.68 (m, 1H), 8.66 (s, 1H), 8.63 (d, J = 8.8 Hz, 1H), 8.53-8.51 (d, J = 8.8 Hz, 1H), 8.01 (m, 2H), 7.82 (s, 1H), 7.09 (s, 1H), 7.07 (s, 1 H), 6.99 (d, J = 8.4 Hz, 2H), 6.67 (dd, J = 4, 12 Hz, 1H), 4.81 (d, J = 4.8 Hz, 2H), 4.78-4.46 (m, 2H), 4.46 (m, 1 H), 4.45 (m, 2H), 4.07 (s, 2H), 3.78 (s, 1H), 3.75 (m, 4H), 3.59 (m, 4H), 3.56 (m, 8H), 3.53 (Mm, 2 H), 3.38 (m, 2H), 2.51 (m, 2H), 2.50 (m, 2H), 2.07 (m, 2H), 1.60-1.59 (m, 8H), 1.41-1.08 (m, 6H). |

TABLE 1-continued

| | | | | | |
|---|---|---|---|---|---|
| 374 | 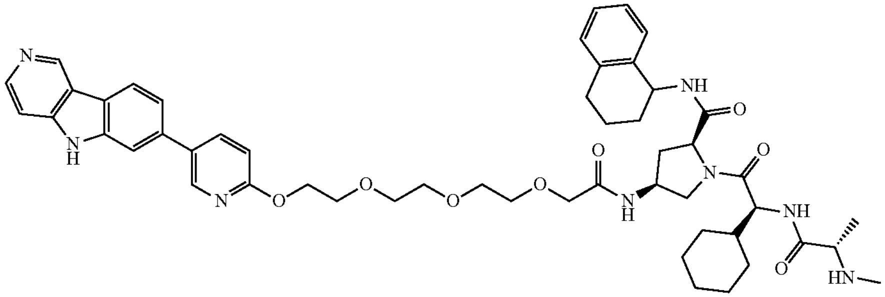 [SMILES: CN[C@@H](C)C(=O)N[C@H](C(=O)N1C[C@@H](NC(=O)COCCOCCOCCOc2ccc(-c3ccc4c(c3)[nH]c3ccncc34)cn2)C[C@H]1C(=O)NC1CCCc2ccccc21)C1CCCCC1] | (2S,4S)-4-(2-(2-(2-(2-((5-(5H-pyrido[4,3-b]indol-7-yl)pyridin-2-yl)oxy)ethoxy)ethoxy)ethoxy)acetamido)-1-((S)-2-cyclohexyl-2-((S)-2-(methylamino)propanamido)acetyl)-N-((R)-1,2,3,4-tetrahydronaphthalen-1-yl)pyrrolidine-2-carboxamide | | 917.8 | 1H NMR (400 MHz, DMSO-D6): δ 9.34 (s, 1H), 8.55 (d, J = 2.4 Hz, 1H), 8.49-8.40 (m, 2H), 8.36 (br d, J = 8.4 Hz, 1H), 8.30 (d, J = 8.4 Hz, 1H), 8.21 (br s, 2H), 8.15-8.08 (m, 2H), 7.77 (s, 1H), 7.55 (d, J = 8.4 Hz, 1H), 7.48 (d, J = 5.6 Hz, 1H), 7.30 (br d, J = 6.8 Hz, 1H), 7.19-7.03 (m, 4H), 6.94 (d, J = 8.4 Hz, 1H), 4.94 (br s, 1H), 4.49-4.31 (m, 6H), 4.05-3.99 (m, 1H), 3.89 (s, 2H), 3.80-3.72 (m, 2H), 3.61-3.57 (m, 5H), 3.17 (br d, J = 6.0 Hz, 1H), 2.70 (br s, 2H), 2.39 (br dd, J = 7.2, 13.6 Hz, 2H), 2.23 (s, 3H), 1.89-1.56 (m, 14H), 1.20-0.89 (m, 10H). |
| 375 | 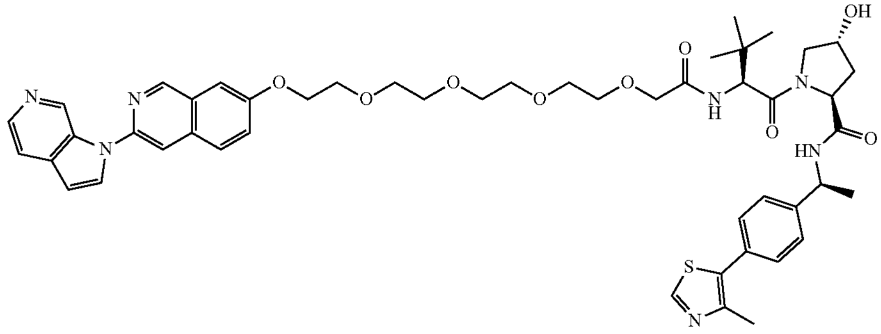 [SMILES: Cc1ncsc1-c1ccc([C@H](C)NC(=O)[C@@H]2C[C@@H](O)CN2C(=O)[C@@H](NC(=O)COCCOCCOCCOCCOc2ccc3cc(-n4ccc5ccncc54)ncc3c2)C(C)(C)C)cc1] | (2S,4R)-1-((S)-17-((3-(1H-pyrrolo[2,3-c]pyridin-1-yl)isoquinolin-7-yl)oxy)-2-(tert-butyl)-4-oxo-6,9,12,15-tetraoxa-3-azaheptadecanoyl)-4-hydroxy-N-((S)-1-(4-(4-methylthiazol-5-yl)phenyl)ethyl)pyrrolidine-2-carboxamide | B | 922.8 | 1H NMR (400 MHz, DMSO-D6): δ 9.63 (s, 1H), 9.28 (s, 1H), 8.97 (s, 1H), 8.45-8.44 (m, 1H), 8.30-8.27 (m, 2H), 8.22 (s, 1H), 8.02-8.00 (m, 1H), 7.68-7.64 (m, 2H), 7.54-7.51 (m, 1H), 7.42-7.34 (m, 5H), 6.85 (d, 1H), 5.15-5.14 (d, 1H), 4.89 (m, 1H), 4.55-4.53 (m, 1H), 4.44 (m, 1H), 4.30-4.29 (m, 3H), 3.96 (m, 2H), 3.86 (m, 2H), 3.66-3.55 (m, 10H), 2.44 (s, 3H), 2.07-2.01 (m, 2H), 1.77 (m, 1H), 1.47 (m, 1H), 1.37-1.35 (m, 3H), 1.24 (m, 2H), 0.93 (s, 9H). |
| 376 | 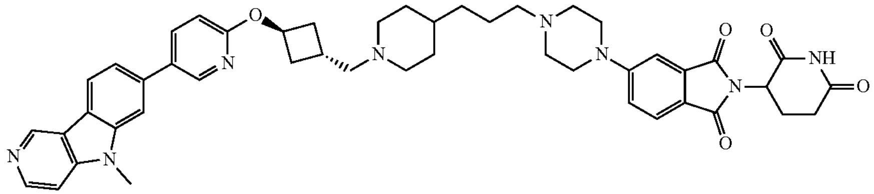 [SMILES: Cn1c2ccncc2c2ccc(-c3ccc(O[C@H]4C[C@H](CN5CCC(CCCN6CCN(c7ccc8c(c7)C(=O)N(C7CCC(=O)NC7=O)C8=O)CC6)CC5)C4)nc3)cc21] | 5-(4-(3-(1-(((1r,3r)-3-((5-(5H-pyrido[4,3-b]indol-7-yl)pyridin-2-yl)oxy)cyclobutyl)methyl)piperidin-4-yl)propyl)piperazin-1-yl)-2-(2,6-dioxopiperidin-3-yl)isoindoline-1,3-dione | B | 795.7 | $^1$H NMR (400 MHz, DMSO-$d_6$): δ 11.80 (s, 1 H), 11.08 (s, 1 H), 9.35 (s, 1 H), 8.53 (d, J = 2.4 Hz, 1 H), 8.42 (d, J = 5.6 Hz, 1 H), 8.29 (d, J = 8.0 Hz, 1 H), 8.20 (s, 1 H), 8.10 (dd, J = 8.4, 2.0 Hz, 1 H), 7.76 (s, 1 H), 7.67 (d, J = 8.4 Hz, 1 H), 7.54 (dd, J = 8.0, 1.2 Hz, 1 H), 7.47 (d, J = 5.6 Hz, 1 H), 7.33 (d, J = 2.0 Hz, 1 H), 7.25 (dd, J = 8.8, 2.0 Hz, 1 H), 6.87-6.93 (m, 1 H), 5.03-5.31 (m, 2 H), 3.42 (s, 8 H), 2.80-2.96 (m, 4 H), 2.56-2.68 (m, 3 H), 2.12-2.31 (m, 4 H), 1.91-2.07 (m, 3 H), 1.68-1.82 (m, 2 H), 1.64 (d, J = 11.2 Hz, 2 H), 1.41-1.50 (m, 2 H), 1.04-1.21 (m, 6 H). |

TABLE 1-continued

| | | | | | |
|---|---|---|---|---|---|
| 377 | 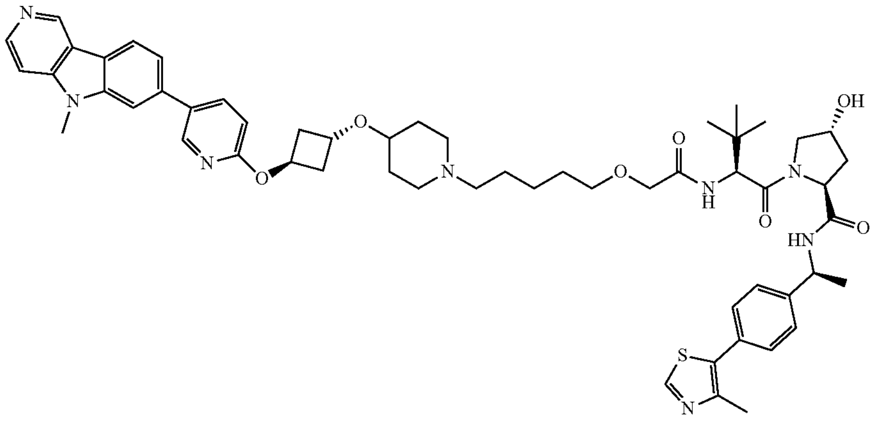 | (2S,4R)-1-((S)-3,3-dimethyl-2-(2-((5-(4-((1r,3r)-3-((5-(5-methyl-5H-pyrido[4,3-b]indol-7-yl)pyridin-2-yl)oxy)cyclobutoxy)piperidin-1-yl)pentyl)oxy)acetamido)butanoyl)-4-hydroxy-N-((S)-1-(4-(4-methythiazol-5-yl)phenyl)ethyl)pyrrolidine-2-carboxamide | B | 999.9 | $^1$H NMR (400 MHz, DMSO-$d_6$) δ: 9.77 (s, 1H), 9.20 (s, 1H), 9.02-8.91 (m, 1H), 8.77 (d, J = 7.2 Hz, 1H), 8.70 (s, 1H), 8.54 (d, J = 8.4 Hz, 1H), 8.46-8.39 (m, 1H), 8.43 (d, J = 8.0 Hz, 1H), 8.29-8.19 (m, 3H), 7.87 (d, J = 8.0 Hz, 1H), 7.45-7.41 (m, 2H), 7.39-7.31 (m, 3H), 6.98 (d, J = 8.8 Hz, 1H), 5.34 (d, J = 4.8 Hz, 1H), 4.90 (m, 1H), 4.58-4.52 (m, 1H), 4.48-4.37 (m, 2H), 4.29 (s, 1H), 4.14 (s, 3H), 3.93 (s, 2H), 3.72 (s, 1H), 3.14-3.01 (m, 3H), 2.93 (d, J = 10.4 Hz, 1H), 2.46-2.39 (m, 8H), 2.20-1.99 (m, 2H), 1.93-1.73 (m, 4H), 1.73-1.52 (m, 6H), 1.47 (d, J = 7.2 Hz, 1H), 1.37 (d, J = 6.4 Hz, 5H), 1.23 (s, 1H), 0.94 (s, 9H) |
| 378 | 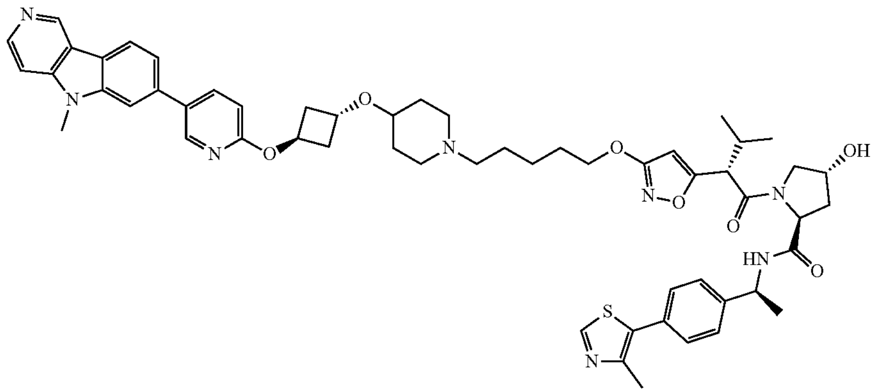 [SMILES: Cc1ncsc1-c1ccc([C@H](C)NC(=O)[C@@H]2C[C@@H](O)CN2C(=O)[C@H](c2cc(OCCCCCN3CCC(O[C@H]4C[C@H](Oc5ccc(-c6ccc7c8cnccc8n(C)c7c6)cn5)C4)CC3)no2)C(C)C)cc1] | (2S,4R)-4-hydroxy-1-((S)-3-methyl-2-(3-((5-(4-((1r,3r)-3-((5-(5-methyl-5H-pyrido[4,3-b]indol-7-yl)pyridin-2-yl)oxy)cyclobutoxy)piperidin-1-yl)pentyl)oxy)isoxazol-5-yl)butanoyl)-N-((S)-1-(4-(4-methylthiazol-5-yl)phenyl)ethyl)pyrrolidine-2-carboxamide | B | 995.8 | 1H NMR (400 MHz, DMSO-$d_6$) δ: 9.36 (s, 1H), 9.01-8.87 (m, 1H), 8.64 (d, J = 2.4 Hz, 1H), 8.50 (d, J = 5.6 Hz, 1H), 8.36-8.27 (m, 2H), 8.19 (m, 1H), 7.98 (s, 1H), 7.66-7.58 (m, 2H), 7.49-7.30 (m, 4H), 6.94 (d, J = 8.4 Hz, 1H), 6.17-6.02 (m, 1H), 5.32 (s, 1H), 5.11 (d, J = 3.6 Hz, 1H), 4.98-4.87 (m, 1H), 4.56-4.32 (m, 2H), 4.31-4.23 (m, 1H), 4.19-4.09 (m, 2H), 3.96 (s, 3H), 3.79-3.45 (m, 4H), 2.44 (s, 10H), 2.31-2.22 (m, 2H), 2.12-2.01 (m, 2H), 1.89-1.63 (m, 6H), 1.55-1.30 (m, 9H), 1.02-0.80 (m, 6H) |

TABLE 1-continued

| | | | | | |
|---|---|---|---|---|---|
| 379 | 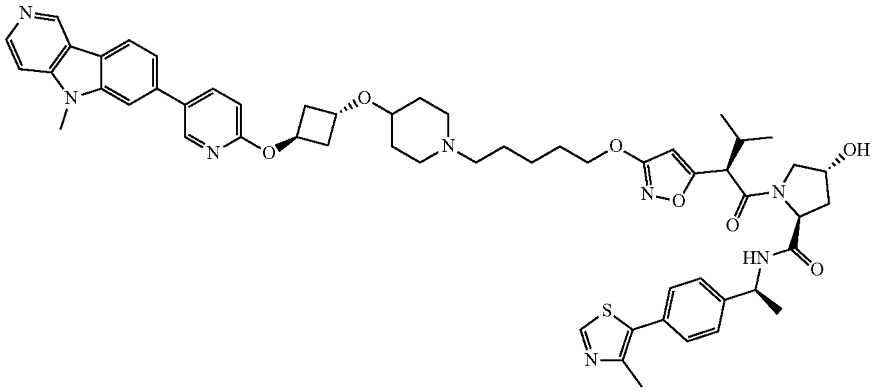 [SMILES: Cc1ncsc1-c1ccc([C@H](C)NC(=O)[C@@H]2C[C@@H](O)CN2C(=O)[C@@H](c2cc(OCCCCCN3CCC(O[C@H]4C[C@H](Oc5ccc(-c6ccc7c8cnccc8n(C)c7c6)cn5)C4)CC3)no2)C(C)C)cc1] | (2S,4R)-4-hydroxy-1-((R)-3-methyl-2-(3-((5-(4-((1r,3r)-3-((5-(5-methyl-5H-pyrido[4,3-b]indol-7-yl)pyridin-2-yl)oxy)cyclobutoxy)piperidin-1-yl)pentyl)oxy)isoxazol-5-yl)butanoyl)-N-((S)-1-(4-(4-methylthiazol-5-yl)phenyl)ethyl)pyrrolidine-2-carboxamide | B | 995.8 | 1H NMR (400 MHz, DMSO-$d_6$) δ: 9.36 (d, J = 0.4 Hz, 1H), 9.04-8.94 (m, 1H), 8.64 (d, J = 2.3 Hz, 1H), 8.50 (d, J = 5.6 Hz, 1H), 8.40 (d, J = 7.2 Hz, 1H), 8.33 (d, J = 8.0 Hz, 1H), 8.20 (m, 1H), 7.98 (s, 1H), 7.66-7.58 (m, 2H), 7.49-7.36 (m, 4H), 6.95 (d, J = 8.8 Hz, 1H), 6.12-5.88 (m, 1H), 5.39-5.26 (m, 1H), 5.10 (d, J = 3.6 Hz, 1H), 5.02 (d, J = 3.2 Hz, 1H), 4.14-4.33 (m, 2H), 4.32-4.25 (m, 1H), 4.18-4.10 (m, 2H), 3.96 (s, 3H), 3.78-3.43 (m, 4H), 2.47-2.36 (m, 9H), 2.29 (m, 2H), 2.11-1.97 (m, 2H), 1.93-1.69 (m, 6H), 1.54-1.34 (m, 9H), 0.99-0.94 (m, 3H), 0.85-0.79 (m, 3H) |
| 380 | 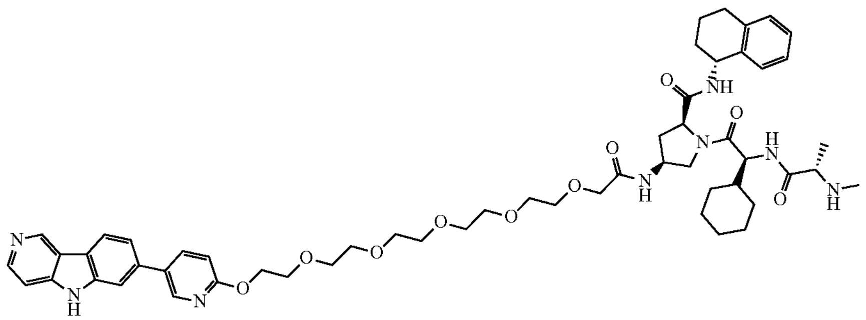 [SMILES: CN[C@@H](C)C(=O)N[C@H](C(=O)N1C[C@@H](NC(=O)COCCOCCOCCOCCOCCOc2ccc(-c3ccc4c(c3)[nH]c3ccncc34)cn2)C[C@H]1C(=O)N[C@@H]1CCCc2ccccc21)C1CCCCC1] | (2S,4S)-4-(17-((5-(5H-pyrido[4,3-b]indol-7-yl)pyridin-2-yl)oxy)-3,6,9,12,15-pentaoxaheptadecanamido)-1-((S)-2-cyclohexyl-2-((S)-2-(methylamino)propanamido)acetyl)-N-((R)-1,2,3,4-tetrahydronaphthalen-1-yl)pyrrolidine-2-carboxamide | | 1005.9 | 1H NMR (400 MHz, DMSO-D6): δ 11.83 (br d, J = 13.0 Hz, 1H), 9.35 (s, 1H), 8.56 (d, J = 2.4 Hz, 1H), 8.49-8.40 (m, 2H), 8.38-8.28 (m, 2H), 8.24 (s, 2H), 8.17-8.08 (m, 2H), 7.78 (s, 1H), 7.56 (dd, J = 1.2, 8.4 Hz, 1H), 7.49 (d, J = 5.6 Hz, 1H), 7.30 (d, J = 7.6 Hz, 1H), 7.16-7.05 (m, 3H), 6.96 (d, J = 8.6 Hz, 1H), 4.95 (br d, J = 4.2 Hz, 1H), 4.58-4.22 (m, 6H), 4.02 (br dd, J = 6.8, 10.3 Hz, 1H), 3.93-3.87 (m, 2H), 3.82-3.75 (m, 3H), 3.59 (br d, J = 2.4 Hz, 10H), 3.24-3.15 (m, 1H), 2.72 (br d, J = 5.6 Hz, 2H), 2.43-2.31 (m, 2H), 2.24 (s, 3H), 1.94-1.48 (m, 13H), 1.35-0.82 (m, 10H). |

TABLE 1-continued

| | | | | | |
|---|---|---|---|---|---|
| 381 | 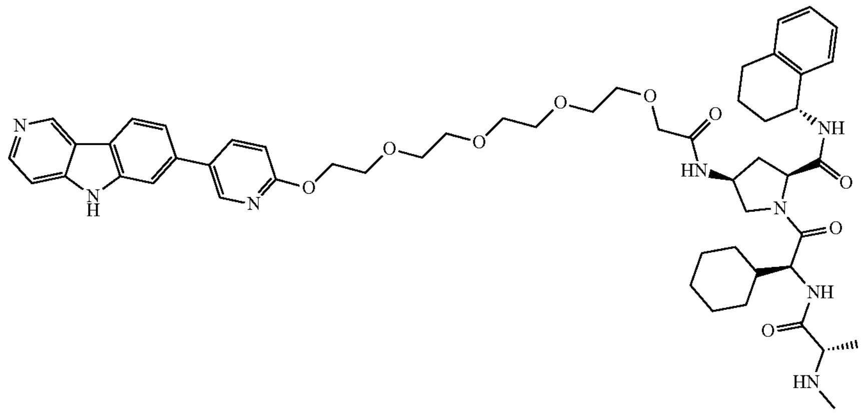 [SMILES: CN[C@@H](C)C(=O)N[C@H](C(=O)N1C[C@@H](NC(=O)COCCOCCOCCOCCOc2ccc(-c3ccc4c(c3)[nH]c3ccncc34)cn2)C[C@H]1C(=O)N[C@@H]1CCCc2ccccc21)C1CCCCC1] | (2S,4S)-4-(14-((5-(5H-pyrido[4,3-b]indol-7-yl)pyridin-2-yl)oxy)-3,6,9,12-tetraoxatetra-decanamido)-1-((S)-2-cyclohexyl-2-((S)-2-(methylamino) propanamido)acetyl)-N-((R)-1,2,3,4-tetrahydronaphthalen-1-yl)pyrrolidine-2-carboxamide | | 961.9 | 1H NMR (400 MHz, DMSO-D6) δ: 12.35-11.37 (m, 1H), 9.36 (s, 1H), 8.56 (d, J = 2.4 Hz, 1H), 8.48-8.41 (m, 2H), 8.38-8.28 (m, 2H), 8.27-8.21 (m, 3H), 8.11 (m, 1H), 7.78 (d, J = 0.9 Hz, 1H), 7.56 (m, 1H), 7.49 (d, J = 5.6 Hz, 1H), 7.30 (d, J = 7.2 Hz, 1H), 7.20-7.03 (m, 3H), 6.96 (d, J = 8.8 Hz, 1H), 4.95 (d, J = 4.4 Hz, 1H), 4.48-4.33 (m, 5H), 4.08-3.91 (m, 5H), 3.63-3.53 (m, 14H), 3.36-3.23 (m, 1H), 2.80-2.62 (m, 2H), 2.44-2.25 (m, 4H), 1.90-1.59 (m, 10H), 1.29-0.88 (m, 8H) |
| 382 | 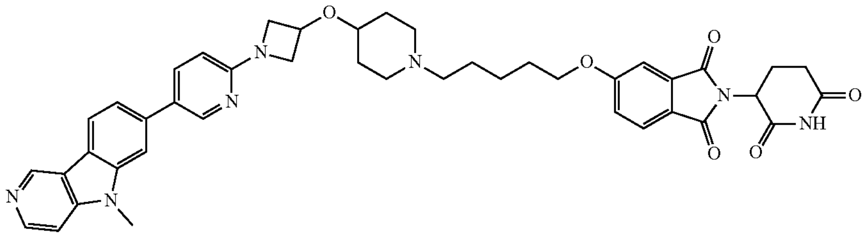 [SMILES: Cn1c2ccncc2c2ccc(-c3ccc(N4CC(OC5CCN(CCCCCOc6ccc7c(c6)C(=O)N(C6CCC(=O)NC6=O)C7=O)CC5)C4)nc3)cc21] | 2-(2,6-dioxopiperidin-3-yl)-5-((5-(4-((1-(5-(5-methyl-5H-pyrido[4,3-b]indol-7-yl)pyridin-2-yl)azetidin-3-yl)oxy)piperidin-1-yl)pentyl)oxy) isoindoline-1,3-dione | A | 756.7 | 1H NMR (300 MHz, DMSO-d6): δ 11.12 (s, 1H), 9.34 (s, 1H), 8.59-8.58 (s, 1H), 8.49-8.48 (m, 1H), 8.30-8.28 (m, 1H), 8.18 (s, 1H), 8.04-8.02 (m, 1H), 7.90 (m, 1H), 7.85-7.83 (m, 1H), 7.62-7.56 (m, 1H), 7.44-7.43 (s, 1H), 7.37-7.34 (m, 1H), 6.55-6.53 (m, 1H), 5.15-5.09 (m, 1H), 4.60-4.53 (m, 1H), 4.27-4.17 (m, 4H), 3.96 (s, 3H), 3.81-3.77 (m, 2H), 2.94-2.81 (m, 1H), 2.78-2.71 (m, 2H), 2.65-2.60 (m, 1H), 2.58-2.51 (m, 2H), 2.33-2.30 (m, 2H), 2.07 (m, 3H), 1.82-1.78 (m, 4H), 1.49-1.43 (m, 6H). |
| 383 | 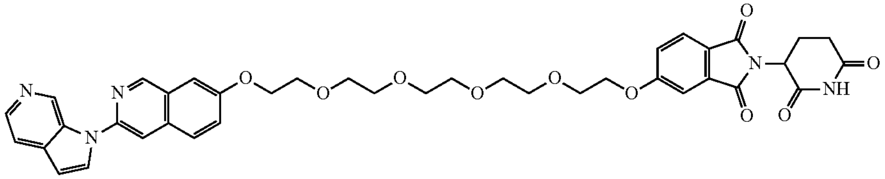 [SMILES: O=C1CCC(N2C(=O)c3ccc(OCCOCCOCCOCCOCCOc4ccc5cc(-n6ccc7ccncc76)ncc5c4)cc3C2=O)C(=O)N1] | 5-((14-((3-(1H-pyrrolo[2,3-c]pyridin-1-yl)isoquinolin-7-yl)oxy)-3,6,9,12-tetraoxatetradecyl)oxy)-2-(2,6-dioxopiperidin-3-yl)isoindoline-1,3-dione | | 738.6 | 1H NMR (400 MHz, DMSO-d6): δ 11.13 (s, 1H), 9.62 (s, 1H), 9.27 (s, 1H), 8.30-8.28 (m, 2H), 8.27-8.21 (s, 1H), 8.01-7.97 (m, 1H), 7.80-7.78 (m, 1H), 7.68-7.67 (m, 1H), 7.62 (m, 1H), 7.53-7.50 (m, 1H), 7.42-7.41 (m, 1H), 7.35-7.32 (m, 1H), 6.86-6.85 (m, 1H), 5.11 (m, 1H), 4.30-4.27 (m, 4H), 3.86-3.84 (m, 2H), 3.78-3.76 (m, 2H), 3.65-3.51 (m, 14H), 2.88 (m, 1H), 2.56-2.51 (m, 1H). |
| 384 | 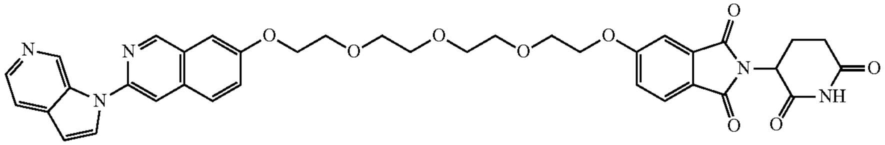 [SMILES: O=C1CCC(N2C(=O)c3ccc(OCCOCCOCCOCCOc4ccc5cc(-n6ccc7ccncc76)ncc5c4)cc3C2=O)C(=O)N1] | 5-(2-(2-(2-(2-((3-(1H-pyrrolo[2,3-c]pyridin-1-yl)isoquinolin-7-yl)oxy)ethoxy)ethoxy) ethoxy)ethoxy)-2-(2,6-dioxopiperidin-3-yl)isoindoline-1,3-dione | B | 694.5 | 1H NMR (300 MHz, DMSO-d6): δ 11.16 (s, 1H), 9.67 (s, 1H), 9.29 (s, 1H), 8.36 (m, 1H), 8.32 (m, 1H), 8.23 (m, 1H), 8.03-8.00 (m, 1H), 7.82-7.80 (m, 1H), 7.75 (m, 1H), 7.64 (m, 1H), 7.55-7.52 (m, 1H), 7.44 (m, 1H), 7.37 (m, 1H), 6.91 (s, 1H), 5.15-5.12 (m, 1H), 4.43 (s, 5H), 3.88-3.82 (m, 6H), 3.62 (m, 6H), 2.95-2.87 (m, 1H), 2.63 (m, 1H), 2.06-2.02 (m, 1H). |

TABLE 1-continued

| | | | | | |
|---|---|---|---|---|---|
| 385 | 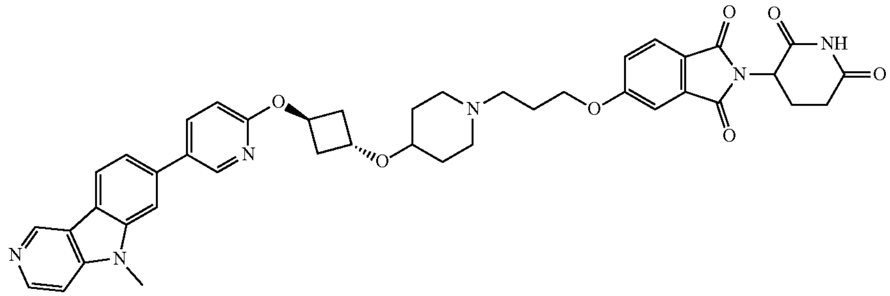 [SMILES: Cn1c2ccncc2c2ccc(-c3ccc(O[C@H]4C[C@H](OC5CCN(CCCOc6ccc7c(c6)C(=O)N(C6CCC(=O)NC6=O)C7=O)CC5)C4)nc3)cc21] | 2-(2,6-dioxopiperidin-3-yl)-5-(3-(4-((1r,3r)-3-((5-(5-methyl-5H-pyrido[4,3-b]indol-7-yl)pyridin-2-yl)oxy)cyclobutoxy)piperidin-1-yl)propoxy)isoindoline-1,3-dione | B | 743.6 | 1H NMR (400 MHz, DMSO) δ 11.11 (s, 1H), 9.36 (s, 1H), 8.64 (s, 1H), 8.50-8.49 (m, 1H), 8.33-8.31 (m, 1H), 8.21-8.18 (m, 1H), 7.98 (m, 1H), 7.84-7.82 (m, 1H), 7.63-7.60 (m, 2H), 7.43-7.34 (m, 2H), 6.95-6.93 (m, 1H), 5.31-5.30 (m, 1H), 5.14-5.10 (m, 1H), 4.36 (m, 1H), 4.22-4.19 (m, 2H), 3.96 (m, 3H), 2.89-2.67 (m, 6H), 2.41-2.39 (m, 6H), 2.04-1.90 (m, 3H), 1.88-1.75 (m, 4H), 1.43-1.34 (m, 2H). |
| 386 | 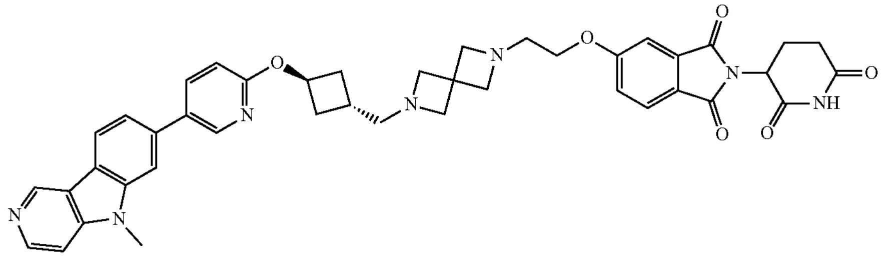 [SMILES: Cn1c2ccncc2c2ccc(-c3ccc(O[C@H]4C[C@H](CN5CC6(CN(CCOc7ccc8c(c7)C(=O)N(C7CCC(=O)NC7=O)C8=O)C6)C5)C4)nc3)cc21] | 2-(2,6-dioxopiperidin-3-yl)-5-(2-(6-(((1r,3r)-3-((5-(5-methyl-5H-pyrido[4,3-b]indol-7-yl)pyridin-2-yl)oxy)cyclobutyl)methyl)-2,6-diazaspiro[3.3]heptan-2-yl)ethoxy)isoindoline-1,3-dione | A | 740.6 | $^1$H NMR (400 MHz, DMSO-d6) δ 11.11 (s, 1H), 9.38 (s, 1H), 8.62 (m, 1H), 8.51 (d, J = 5.6 Hz, 1H), 8.34 (d, J = 8.0 Hz, 1H), 8.20 (m, 1H), 8.15 (s, 2H), 7.98 (s, 1H), 7.86 (d, J = 8.4 Hz, 1H), 7.67-7.58 (m, 2H), 7.43 (s, 1H), 7.37-7.30 (m, 1H), 6.93 (t, J = 8.0 Hz, 1H), 5.36-5.21 (m, 1H), 5.17-5.04 (m, 2H), 4.19 (s, 2H), 3.97 (s, 3H), 3.91 (s, 4H), 3.07-2.99 (m, 3H), 2.96 (s, 4H), 2.56 (s, 4H), 2.31-2.19 (m, 2H), 2.15-1.98 (m, 2H), 1.85 (d, J = 10.2 Hz, 2H). |
| 387 | 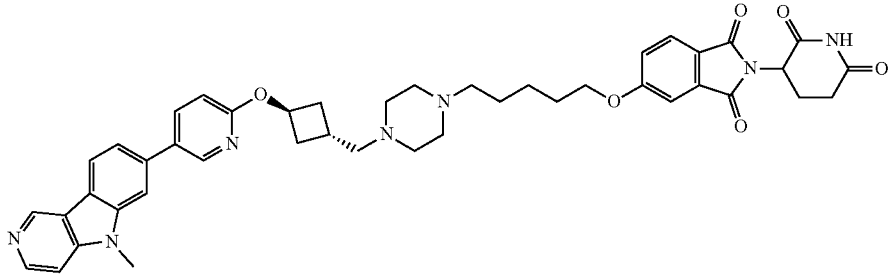 [SMILES: Cn1c2ccncc2c2ccc(-c3ccc(O[C@H]4C[C@H](CN5CCN(CCCCCOc6ccc7c(c6)C(=O)N(C6CCC(=O)NC6=O)C7=O)CC5)C4)nc3)cc21] | 2-(2,6-dioxopiperidin-3-yl)-5-((5-(4-(((1r,3r)-3-((5-(5-methyl-5H-pyrido[4,3-b]indol-7-yl)pyridin-2-yl)oxy)cyclobutyl)methyl)piperazin-1-yl)pentyl)oxy)isoindoline-1,3-dione | A | 770.7 | $^1$H NMR (300 MHz, DMSO-$d_6$) δ 11.12 (s, 1H), 9.37 (s, 1H), 8.63 (m, 1H), 8.50 (m, 1H), 8.34-8.32 (m, 1H), 8.20-8.17 (m, 2H), 7.98 (s, 1H), 7.85-7.83 (m, 1H), 7.64-7.61 (m, 2H), 7.44 (s, 1H), 7.37-7.34 (m, 1H), 6.95-6.93 (m, 1H), 5.30 (m, 1H), 5.16 (m, 1H), 4.20-4.17 (m, 2H), 3.97 (s, 3H), 2.95-2.82 (m, 1H), 2.62-2.52 (m, 3H), 2.47-2.21 (m, 15H), 2.07 (m, 1H), 1.79-1.76 (m, 2 H), 1.50-1.43 (m, 4H). |
| 388 | 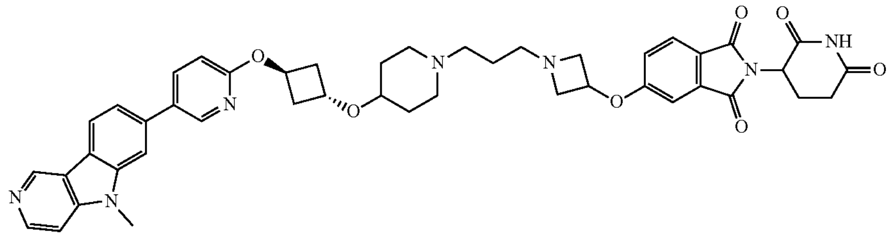 [SMILES: Cn1c2ccncc2c2ccc(-c3ccc(O[C@H]4C[C@H](OC5CCN(CCCN6CC(Oc7ccc8c(c7)C(=O)N(C7CCC(=O)NC7=O)C8=O)C6)CC5)C4)nc3)cc21] | 2-(2,6-dioxopiperidin-3-yl)-5-((1-(3-(4-((1r,3r)-3-((5-(5-methyl-5H-pyrido[4,3-b]indol-7-yl)pyridin-2-yl)oxy)cyclobutoxy)piperidin-1-yl)propyl)azetidin-3-yl)oxy)isoindoline-1,3-dione | A | 798.7 | 1H NMR (400 MHz, DMSO): δ 11.11 (s, 1H), 9.36 (s, 1H), 8.64-8.63 (s, 1H), 8.50-8.49 (m, 1H), 8.33-8.31 (m, 1H), 8.20-8.17 (m, 1H), 7.98 (m, 1H), 7.82 (m, 1H), 7.63-7.62 (m, 2H), 7.28 (m, 2H), 6.95-6.93 (m, 1H), 5.33-5.28 (m, 1H), 5.18-5.03 (m, 2H), 4.36 (m, 1H), 3.96 (s, 3H), 3.74 (m, 2H), 3.18-3.16 (m, 2H), 2.99-2.76 (m, 2H), 2.69-2.51 (m, 2H), 2.43-2.33 (m, 4H), 2.26-2.22 (m, 2H), 2.01-1.96 (m, 2H), 1.80-1.79 (m, 2H), 1.58-1.54 (m, 2H), 1.44-1.43 (m, 2H), 1.40-1.23 (m, 3H), 0.95-0.85 (m, 2H). |

TABLE 1-continued

| | | | | | |
|---|---|---|---|---|---|
| 389 | 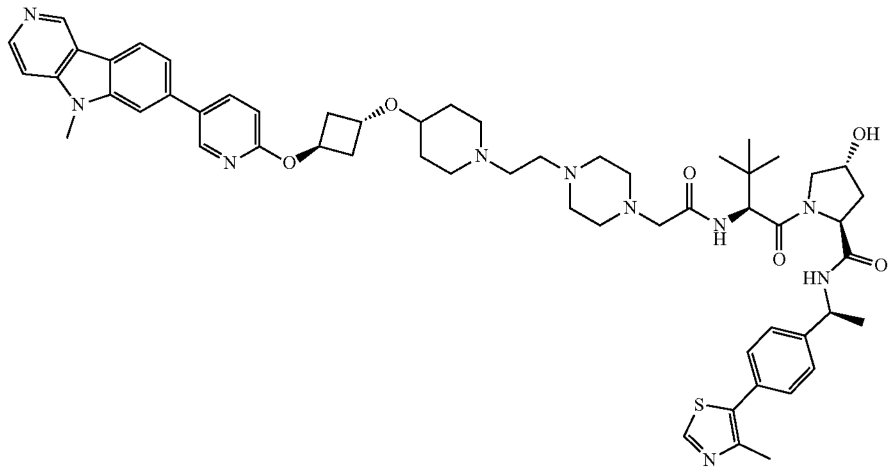 [SMILES: Cc1ncsc1-c1ccc([C@H](C)NC(=O)[C@@H]2C[C@@H](O)CN2C(=O)[C@@H](NC(=O)CN2CCN(CCN3CCC(O[C@H]4C[C@H](Oc5ccc(-c6ccc7c8cnccc8n(C)c7c6)cn5)C4)CC3)CC2)C(C)(C)C)cc1] | (2S,4R)-1-((S)-3,3-dimethyl-2-(2-(4-(2-(4-((1r,3r)-3-((5-(5-methyl-5H-pyrido[4,3-b]indol-7-yl)pyridin-2-yl)oxy)cyclobutoxy)piperidin-1-yl)ethyl)piperazin-1-yl)acetamido)butanoyl)-4-hydroxy-N-((S)-1-(4-(4-methylthiazol-5-yl)phenyl)ethyl)pyrrolidine-2-carboxamide | A | 1025.9 | $^1$H NMR (400 MHz, DMSO-$d_6$) δ: 9.36 (s, 1H), 8.98 (s, 1H), 8.64 (s, 1H), 8.55-8.41 (m, 2H), 8.33 (d, J = 8.0 Hz, 1H), 8.20 (s, 3H), 7.98 (s, 1H), 7.78-7.68 (m, 1H), 7.65-7.56 (m, 2H), 7.47-7.35 (m, 4H), 7.25 (m, 1H), 6.94 (d, J = 8.8 Hz, 1H), 5.31 (s, 1H), 4.92-4.86 (m, 1H), 4.54-4.27 (m, 5H), 3.96 (s, 3H), 3.55-3.51 (m, 10H), 3.07-2.79 (m, 3H), 2.47-2.40 (m, 12H), 2.25-2.01 (m, 3H), 1.85-1.67 (m, 3H), 1.59-1.30 (m, 5H), 1.23-0.99 (m, 1H), 0.94 (s, 9H) |
| 390 | 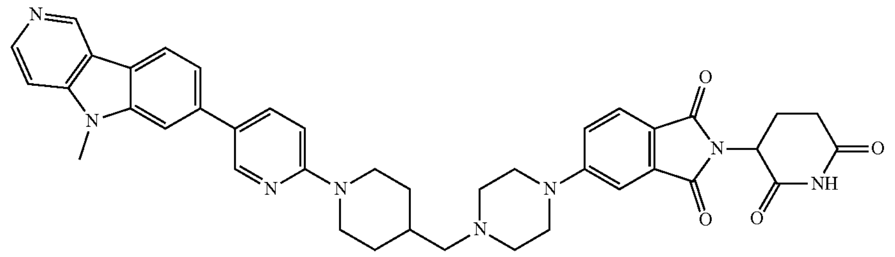 | 2-(2,6-dioxopiperidin-3-yl)-5-(4-((1-(5-(5-methyl-5H-pyrido[4,3-b]indol-7-yl)pyridin-2-yl)piperidin-4-yl)methyl)piperazin-1-yl)isoindoline-1,3-dione | B | 697.6 | $^1$H NMR (400 MHz, DMSO) δ 11.11 (s, 1H), 9.32 (s, 1H), 8.62 (m, 1H), 8.49 (m, 1H), 8.33 (m, 1H), 8.03 (m, 1H), 7.98 (s, 1H), 7.72 (m, 1H), 7.65 (m, 2H), 7.38 (m, 1H), 7.29 (m, 1H), 6.97 (m, 1H), 5.11 (m, 1H), 4.35 (m, 3H), 3.98 (s, 3H), 3.68-3.55 (m, 4H), 2.92-2.83 (m, 2H), 2.22 (m, 3H), 2.03 (m, 2H), 1.94-1.87 (m, 2H), 1.45 (m, 1H), 1.23 (m, 4H), 1.16 (m, 2H) |

TABLE 1-continued

| | | | | | |
|---|---|---|---|---|---|
| 391 | 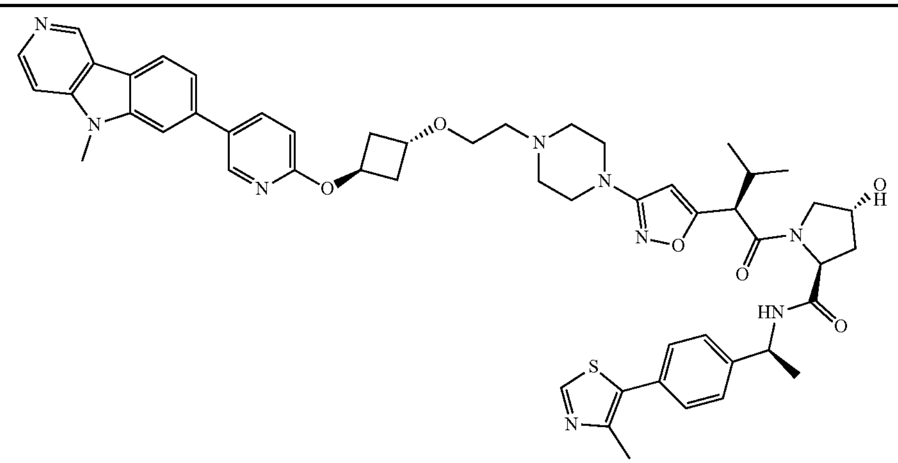 | (2S,4R)-4-hydroxy-1-((R)-3-methyl-2-(3-(4-(2-((1r,3R)-3-((5-(5-methyl-5H-pyrido[4,3-b]indol-7-yl)pyridin-2-yl)oxy)cyclobutoxy)ethyl)piperazin-1-yl)isoxazol-5-yl)butanoyl)-N-((S)-1-(4-(4-methylthiazol-5-yl)phenyl)ethyl)pyrrolidine-2-carboxamide | A | 938.8 | $^1$H NMR (400 MHz, DMSO-d6) δ 9.36 (s, 1H), 8.98 (s, 1H), 8.64 (d, J = 2.8 Hz, 1H), 8.49 (d, J = 5.6 Hz, 1H), 8.41 (d, J = 7.6 Hz, 1H), 8.32 (d, J = 8.4 Hz, 1H), 8.19 (dd, J = 2.4, 8.4 Hz, 1H), 8.14 (s, 1H), 7.98 (s, 1H), 7.65-7.59 (m, 2H), 7.47-7.41 (m, 2H), 7.39-7.34 (m, 2H), 6.94 (d, J = 8.4 Hz, 1H), 6.14 (s, 1H), 5.32 (br d, J = 4.4 Hz, 1H), 5.12 (br s, 1H), 4.94-4.85 (m, 1H), 4.36 (t, J = 8.0 Hz, 1H), 4.29-4.21 (m, 2H), 3.96 (s, 3H), 3.71 (br dd, J = 4.8, 10.8 Hz, 1H), 3.57 (br d, J = 9.6 Hz, 6H), 3.17 (br s, 4H), 2.56-2.54 (m, 2H), 2.45 (s, 3H), 2.39-2.34 (m, 2H), 2.29-2.13 (m, 2H), 2.03 (b r d, J = 10.8 Hz, 1H), 1.83-1.73 (m, 1H), 1.46-1.35 (m, 3H), 0.99-0.91 (m, 3H), 0.84-0.74 (m, 3H). |
| 392 | 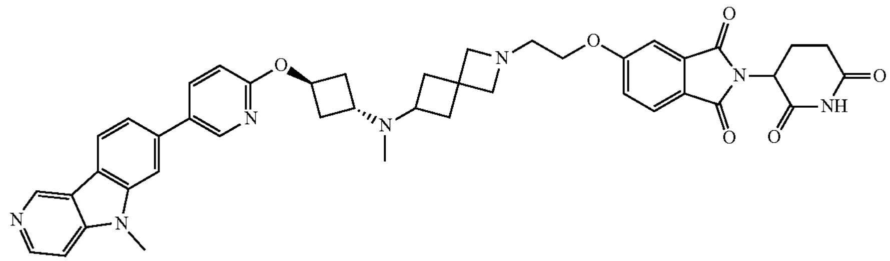 [SMILES: Cn1c2ccncc2c2ccc(-c3ccc(O[C@H]4C[C@H](N(C)C5CC6(C5)CN(CCOc5ccc7c(c5)C(=O)N(C5CCC(=O)NC5=O)C7=O)C6)C4)nc3)cc21] | 2-(2,6-dioxopiperidin-3-yl)-5-(2-(6-(methyl((1r,3r)-3-((5-(5-methyl-5H-pyrido[4,3-b]indol-7-yl)pyridin-2-yl)oxy)cyclobutyl)amino)-2-azaspiro[3.3]heptan-2-yl)ethoxy)isindoline-1,3-dione | B | 754.6 | $^1$H NMR (400 MHz, DMSO-d6) δ 11.11 (s, 1H), 9.37 (s, 1H), 8.64 (d, J = 2.4 Hz, 1H), 8.50 (d, J = 5.6 Hz, 1H), 8.33 (d, J = 8.0 Hz, 1H), 8.22-8.16 (m, 3H), 7.98 (s, 1H), 7.84 (d, J = 8.4 Hz, 1H), 7.66-7.58 (m, 2H), 7.42 (d, J = 2.0 Hz, 1H), 7.34 (m, 1H), 6.95 (d, J = 8.8 Hz, 1H), 5.25-5.09 (m, 2H), 4.14 (t, J = 5.2 Hz, 2H), 3.96 (s, 3H), 3.15 (d, J = 7.6 Hz, 2H), 2.96-2.86 (m, 2H), 2.80 (d, J = 4.8 Hz, 2H), 2.70-2.64 (m, 6H), 2.42 (m, 2H), 2.20-2.12 (m, 4H), 2.01-1.92 (m, 5H). |
| 393 | 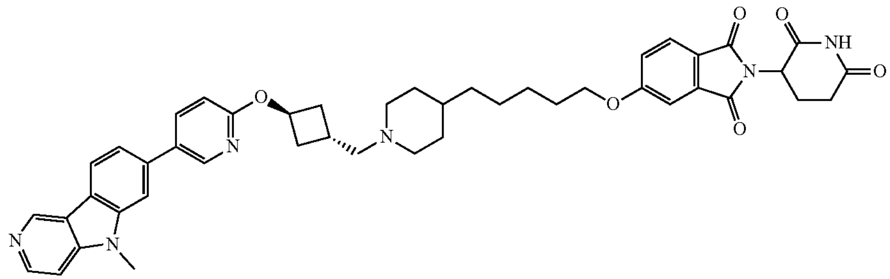 [SMILES: Cn1c2ccncc2c2ccc(-c3ccc(O[C@H]4C[C@H](CN5CCC(CCCCCOc6ccc7c(c6)C(=O)N(C6CCC(=O)NC6=O)C7=O)CC5)C4)nc3)cc21] | 2-(2,6-dioxopiperidin-3-yl)-5-((5-(1-(((1r,3r)-3-((5-(5-methyl-5H-pyrido[4,3-b]indol-7-yl)pyridin-2-yl)oxy)cyclobutyl)methyl)piperidin-4-yl)pentyl)oxy)isoindoline-1,3-dione | A | 769.5 | $^1$H NMR (400 MHz, DMSO-d6) δ 11.12 (s, 1H), 9.35 (s, 1H), 8.62 (s, 1H), 8.49 (m, 1H), 8.32-8.31 (m, 1H), 8.18-8.17 (m, 1H), 7.97 (s, 1H), 7.83-7.81 (m, 1H), 7.61 (m, 2H), 7.41-7.33 (m, 2H), 6.93-6.91 (m, 1H), 5.27-5.11 (m, 2H), 4.15 (m, 2H), 3.95 (s, 3H), 2.89-2.80 (m, 3H), 2.62-2.57 (m, 2H), 2.31 (m, 2H), 2.21 (m, 3H), 2.06-2.03 (m, 1H), 1.84 (m, 2H), 1.74 (m, 2H), 1.59 (m, 2H), 1.47-1.34 (m, 4H), 1.22-1.11 (m, 7H). |

TABLE 1-continued

| | | | | | |
|---|---|---|---|---|---|
| 394 | 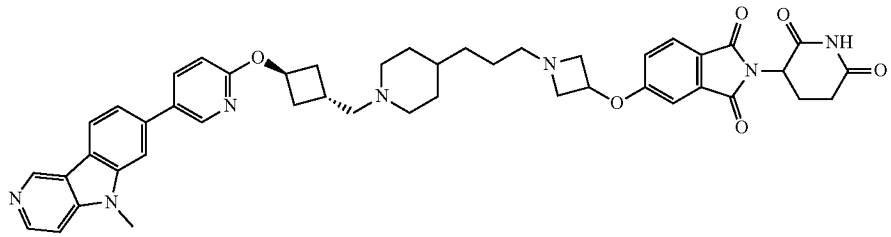 [SMILES: Cn1c2ccncc2c2ccc(-c3ccc(O[C@H]4C[C@H](CN5CCC(CCCN6CC(Oc7ccc8c(c7)C(=O)N(C7CCC(=O)NC7=O)C8=O)C6)CC5)C4)nc3)cc21] | 2-(2,6-dioxopiperidin-3-yl)-5-((1-(3-(1-(((1r,3r)-3-((5-(5-methyl-5H-pyrido[4,3-b]indol-7-yl)pyridin-2-yl)oxy)cyclobutyl)methyl)piperidin-4-yl)propyl)azetidin-3-yl)oxy)isoindoline-1,3-dione | B | 796.5 | $^1$H NMR (400 MHz, DMSO-d6) δ 11.08 (s, 1H), 9.35 (s, 1H), 8.62-8.49 (m, 2H), 8.41-8.18 (m, 2H), 8.09-7.84 (m, 2H), 7.76-7.61 (m, 2H), 7.27 (m, 2H), 6.92 (m, 1H), 5.27 (m, 1H), 5.20-4.95 (m, 2H), 3.95 (s, 3H), 3.72-3.61 (m, 2H), 3.08-2.80 (m, 6H), 2.56 (m, 1H), 2.40 (m, 4H), 2.21 (m, 2H), 2.05 (m, 1H), 1.84 (m, 2H), 1.72-1.43 (m, 3H), 1.28-0.50 (m, 9H). |
| 395 | 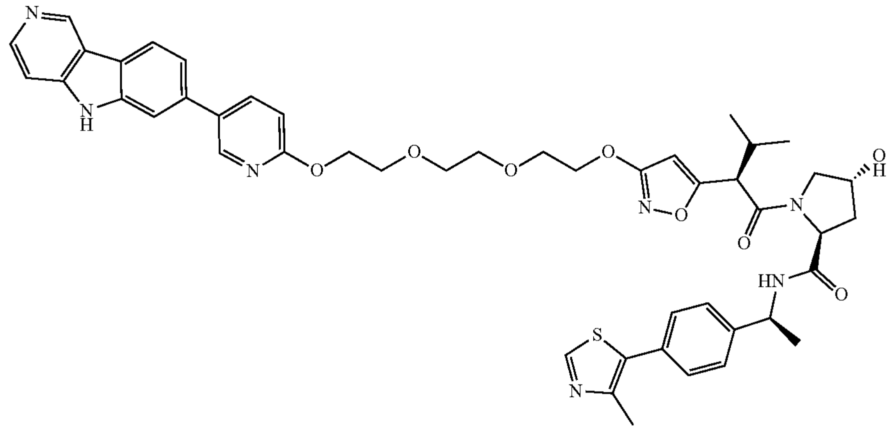 [SMILES: Cc1ncsc1-c1ccc([C@H](C)NC(=O)[C@@H]2C[C@@H](O)CN2C(=O)[C@@H](c2cc(OCCOCCOCCOc3ccc(-c4ccc5c(c4)[nH]c4ccncc45)cn3)no2)C(C)C)cc1] | (2S,4R)-1-((S)-2-(3-(2-(2-(2-((5-(5H-pyrido[4,3-b]indol-7-yl)pyridin-2-yl)oxy)ethoxy)ethoxy)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | B | 874.5 | $^1$H NMR (300 MHz, DMSO-$d_6$): δ 11.85 (s, 1H), 9.35 (s, 1H), 8.99 (m, 1H), 8.56-8.55 (s, 1H), 8.43-8.28 (m, 3H), 8.12-8.11 (m, 1H), 7.78 (s, 1H), 7.57-7.29 (m, 5H), 6.97-6.94 (m, 1H), 6.10 (m, 1H), 5.14-4.80 (m, 2H), 4.45-4.43 (m, 3H), 4.24 (m, 3H), 3.78-3.72 (m, 5H), 3.61-3.53 (m, 5H), 3.47 (m, 1H), 2.45-2.43 (m, 3H), 2.26 (m, 1H), 2.06 (m, 2H), 1.76 (m, 2H), 1.46-1.23 (m, 3H), 0.97-0.94 (m, 2H), 0.83-0.74 (m, 3H). |
| 396 | 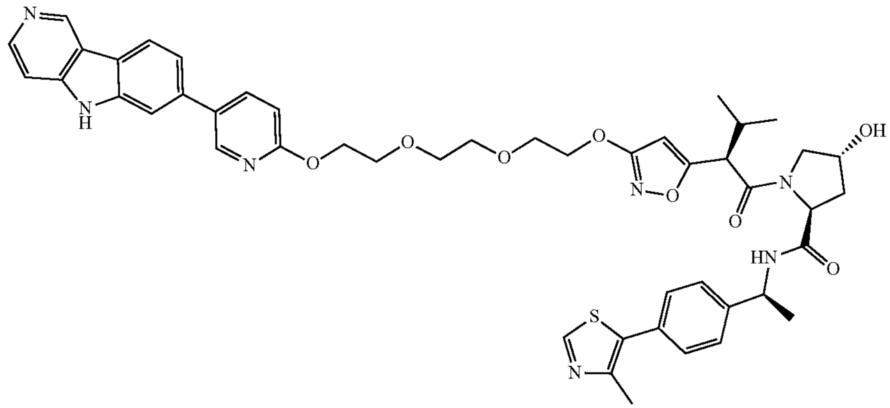 [SMILES: Cc1ncsc1-c1ccc([C@H](C)NC(=O)[C@@H]2C[C@@H](O)CN2C(=O)[C@@H](c2cc(OCCOCCOCCOc3ccc(-c4ccc5c(c4)[nH]c4ccncc45)cn3)no2)C(C)C)cc1] | (2S,4R)-1-((R)-2-(3-(2-(2-(2-((5-(5H-pyrido[4,3-b]indol-7-yl)pyridin-2-yl)oxy)ethoxy)ethoxy)ethoxy)isoxazol-5-yl)-3-(methylbutanoyl)-4-hydroxy-N-((S)-1-(4-(4-methylthiazol-5-yl)phenyl)ethyl)pyrrolidine-2-carboxamide | A | 874.5 | $^1$H NMR (300 MHz, DMSO-$d_6$): δ 11.85 (s, 1H), 9.35 (s, 1H), 8.98 (s, 1H), 8.57 (s, 1H), 8.45-8.41 (m, 2H), 8.31-8.29 (m, 1H), 8.14-8.10 (m, 1H), 7.78 (s, 1H), 7.58-7.34 (m, 5H), 6.98-6.96 (m, 1H), 6.11 (s, 1H), 5.13-5.11 (m, 1H), 4.90 (m, 1H), 4.46-4.37 (m, 3H), 4.26 (m, 3H), 3.80-3.66 (m, 5H), 3.61 (m, 5H), 3.46 (m, 1H), 2.45 (m, 3H), 2.26 (m, 1H), 2.06 (m, 1H), 1.77 (m, 1H), 1.46-1.23 (m, 4H), 0.96-0.94 (m, 3H), 0.83-0.77 (m, 3H). |

TABLE 1-continued

| | | | | | |
|---|---|---|---|---|---|
| 397 | 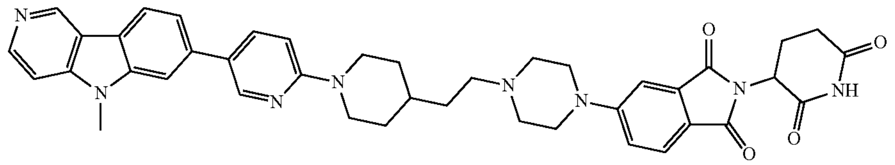 | 2-(2,6-dioxopiperidin-3-yl)-5-(4-(2-(1-(5-(5-methyl-5H-pyrido[4,3-b]indol-7-yl)pyridin-2-yl)piperidin-4-yl)ethyl)piperazin-1-yl)isindoline-1,3-dione | A | 711.4 | 1H NMR (400 MHz, DMSO-d6): δ 11.09 (s, 1H), 9.33 (s, 1H), 8.62 (s, 1H), 8.49-8.48 (m, 1H), 8.29-8.27 (m, 1H), 8.18 (m, 1H), 8.02-8.00 (m, 1H), 7.91 (m, 1H), 7.69-7.67 (m, 1H), 7.62-7.58 (m, 1H), 7.34 (s, 1H), 7.27-7.25 (m, 1H), 6.97-6.95 (m, 1H), 5.10-5.06 (m, 1H), 4.39-4.36 (m, 2H), 3.95 (s, 2H), 3.71-3.51 (m, 8H), 2.92-2.82 (m, 3H), 2.68-2.57 (m, 2H), 2.42-2.38 (m, 2H), 2.04-2.01 (m, 1H), 1.80-1.77 (m, 2H), 1.61 (m, 2H), 1.45 (m, 2H), 1.20 (m, 2H). |
| 398 | 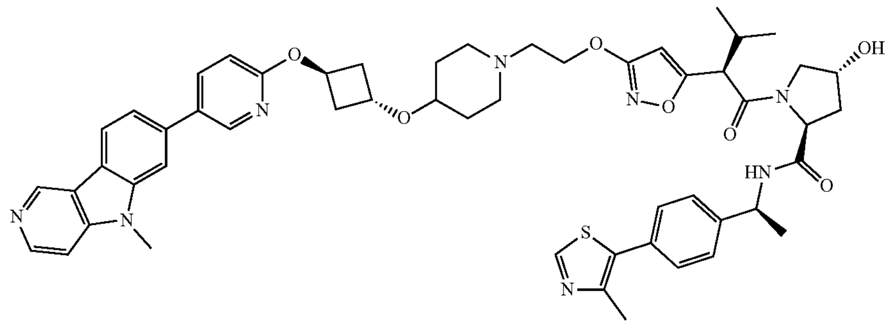 [SMILES: Cc1ncsc1-c1ccc([C@H](C)NC(=O)[C@@H]2C[C@@H](O)CN2C(=O)[C@@H](c2cc(OCCN3CCC(O[C@H]4C[C@H](Oc5ccc(-c6ccc7c8cnccc8n(C)c7c6)cn5)C4)CC3)no2)C(C)C)cc1] | (2S,4R)-4-hydroxy-1-((R)-3-methyl-2-(3-(2-(4-((1r,3R)-3-((5-(5-methyl-5H-pyrido[4,3-b]indol-7-yl)pyridin-2-yl)oxy)cyclobutoxy) piperidin-1-yl)ethoxy)isoxazol-5-yl)butanoyl)-N-((S)-1-(4-(4-methylthiazol-5-yl)phenyl)ethyl) pyrrolidine-2-carboxamide | A | 953.6 | $^1$H NMR (400 MHz, DMSO): δ 9.35 (s, 1H), 8.92-8.91 (m, 1H), 8.57 (s, 1H), 8.44-8.42 (m, 1H), 8.26-8.23 (m, 2H), 8.13-8.11 (m, 1H), 7.91 (s, 1H), 7.55-7.54 (m, 2H), 7.40-7.24 (m, 4H), 6.88-6.86 (m, 1H), 6.09-6.02 (m, 1H), 5.24 (m, 1H), 5.05 (m, 1H), 4.82 (m, 1H), 4.35-4.13 (m, 5H), 3.89 (s, 3H), 3.69-3.67 (m, 1H), 3.48-3.42 (m, 2H), 2.69-2.57 (m, 4H), 2.43-1.98 (m, 12H), 1.71-1.69 (m, 3H), 1.40-1.28 (m, 5H), 0.90 (m, 2H), 0.77-0.76 (m, 4H). |
| 399 | 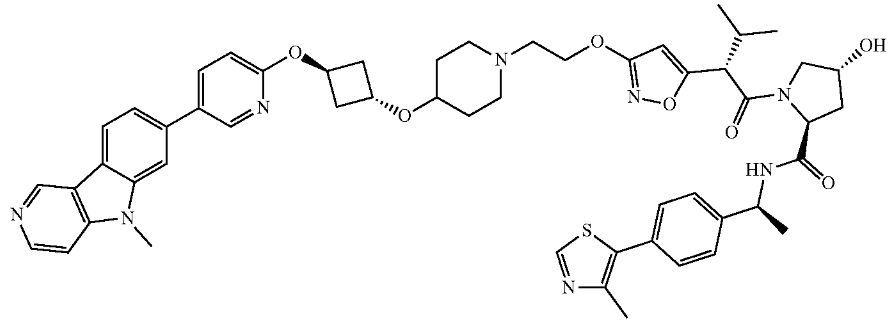 [SMILES: Cc1ncsc1-c1ccc([C@H](C)NC(=O)[C@@H]2C[C@@H](O)CN2C(=O)[C@H](c2cc(OCCN3CCC(O[C@H]4C[C@H](Oc5ccc(-c6ccc7c8cnccc8n(C)c7c6)cn5)C4)CC3)no2)C(C)C)cc1] | (2S,4R)-4-hydroxy-1-((S)-3-methyl-2-(3-(2-(4-((1r,3S)-3-((5-(5-methyl-5H-pyrido[4,3-b]indol-7-yl)pyridin-2-yl)oxy) cyclobutoxy) piperidin-1-yl)ethoxy)isoxazol-5-yl)butanoyl)-N-((S)-1-(4-(4-methylthiazol-5-yl)phenyl)ethyl) pyrrolidine-2-carboxamide | B | 953.6 | $^1$H NMR (400 MHz, DMSO): δ 9.35 (s, 1H), 8.98 (m, 1H), 8.64 (m, 1H), 8.50 (m, 1H), 8.41 (m, 1H), 8.33-8.31 (m, 1H), 8.20-8.18 (m, 1H), 7.98 (m, 1H), 7.63-7.61 (m, 2H), 7.45-7.36 (m, 4H), 6.95-6.93 (m, 1H), 6.10 (m, 1H), 5.31 (m, 1H), 5.11 (m, 1H), 4.93-4.89 (m, 1H), 4.39-4.35 (m, 2H), 4.28-4.22 (m, 3H), 3.96 (s, 3H), 3.71-3.64 (m, 2H), 3.47 (m, 1H), 2.79-2.76 (m, 2H), 2.67 (m, 2H), 2.46-2.40 (m, 8H), 2.24-2.12 (m, 3H), 2.03 (m, 1H), 1.81-1.78 (m, 3H), 1.45-1.37 (m, 5H), 0.97-0.95 (m, 3H), 0.81-0.79 (m, 3H). |
| 400 | 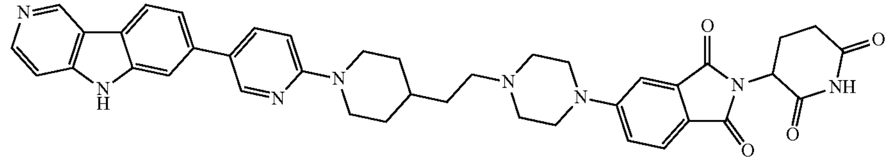 [SMILES: O=C1CCC(N2C(=O)c3ccc(N4CCN(CCC5CCN(c6ccc(-c7ccc8c(c7)[nH]c7ccncc78)cn6)CC5)CC4)cc3C2=O)C(=O)N1] | 5-(4-(2-(1-(5-(5H-pyrido[4,3-b]indol-7-yl)pyridin-2-yl) piperidin-4-yl)ethyl) piperazin-1-yl)-2-(2,6-dioxopiperidin-3-yl)isoindoline-1,3-dione | A | 697.4 | 1H NMR (400 MHz, DMSO-d6): δ 12.74 (s, 1H), 11.10 (s, 1H), 9.63 (s, 1H), 8.60-8.57 (m, 2H), 8.43-8.41 (m, 1H), 8.14 (s, 1H), 8.00-7.86 (m, 3H), 7.76-7.71 (m, 2H), 7.46-7.33 (m, 2H), 6.98 (m, 1H), 5.12-5.07 (m, 1H), 4.42-4.39 (m, 2H), 3.87-3.64 (m, 3H), 3.22-3.02 (m, 6H), 2.94-2.85 (m, 3H), 2.68-2.52 (m, 2H), 2.05-2.02 (m, 1H), 1.81-1.78 (m, 2H), 1.63 (m, 3H), 1.24-1.19 (m, 2H). |

TABLE 1-continued

| | | | | | |
|---|---|---|---|---|---|
| 401 | 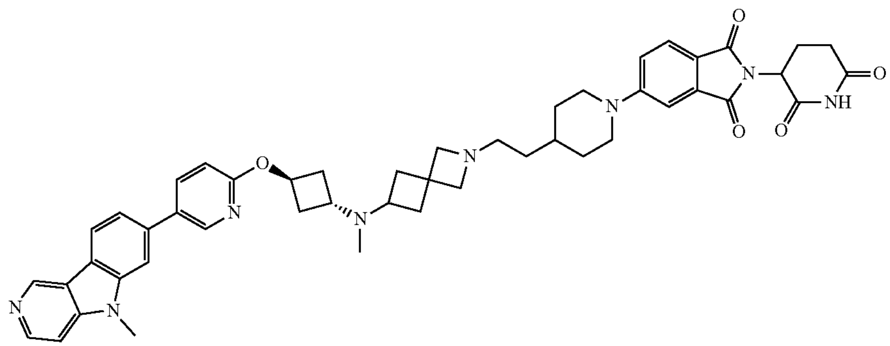 [SMILES: Cn1c2ccncc2c2ccc(-c3ccc(O[C@H]4C[C@H](N(C)C5CC6(C5)CN(CCC5CCN(c7ccc8c(c7)C(=O)N(C7CCC(=O)NC7=O)C8=O)CC5)C6)C4)nc3)cc21] | 2-(2,6-dioxopiperidin-3-yl)-5-(4-(2-(6-(methyl((1r,3r)-3-((5-(5-methyl-5H-pyrido[4,3-b]indol-7-yl)pyridin-2-yl)oxy)cyclobutyl)amino)-2-azaspiro[3.3]heptan-2-yl)ethyl)piperidin-1-yl)isoindoline-1,3-dione | A | 821.5 | $^1$H NMR (400 MHz, DMSO-d6): δ 11.07 (s, 1H), 9.36 (s, 1H), 8.63 (d, J = 2.4 Hz, 1H), 8.49 (d, J = 5.6 Hz, 1H), 8.32 (d, J = 8.0 Hz, 1H), 8.20-8.17 (m, 3H), 7.97 (s, 1H), 7.68-7.56 (m, 3H), 7.29 (s, 1H), 7.22 (br d, J = 8.8 Hz, 1H), 6.94 (d, J = 8.8 Hz, 1H), 5.19 (br s, 1H), 5.06 (dd, J = 5.2, 13.1 Hz, 1H), 4.02 (br d, J = 12.0 Hz, 2H), 3.96 (s, 3H), 2.98-2.83 (m, 5H), 2.43-2.36 (m, 4H), 2.14 (br s, 6H), 2.03-1.93 (m, 7H), 1.80-1.43 (m, 5H), 1.27-1.07 (m, 5H). |
| 402 | 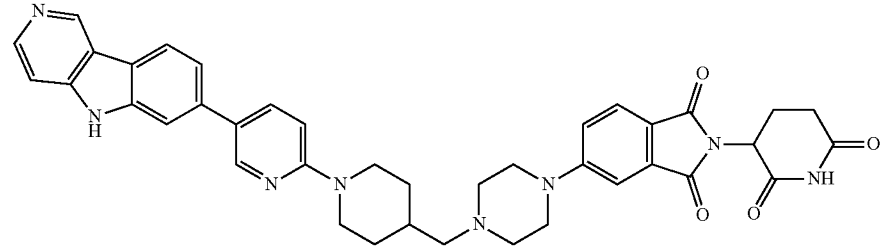 | 5-(4-((1-(5-(5H-pyrido[4,3-b]indol-7-yl)pyridin-2-yl)piperidin-4-yl)methyl)piperazin-1-yl)-2-(2,6-dioxopiperidin-3-yl)isoindoline-1,3-dione | | 683.5 | $^1$H NMR (400 MHz, DMSO): δ 11.75 (s, 1H), 11.11 (s, 1H), 9.32 (s, 1H), 8.56-8.22 (m, 3H), 7.94 (m, 1H), 7.73 (m, 2H), 7.55-7.46 (m, 2H), 7.38-7.23 (m, 2H), 6.98 (m, 1H), 5.11 (m, 1H), 4.35 (m, 2H), 3.55 (m, 6H), 2.91-2.83 (m, 3H), 2.58 (m, 3H), 2.22 (m, 2H), 2.07 (m, 1H), 1.92-1.79 (m, 3H), 1.31-1.08 (m, 3H). |
| 403 | 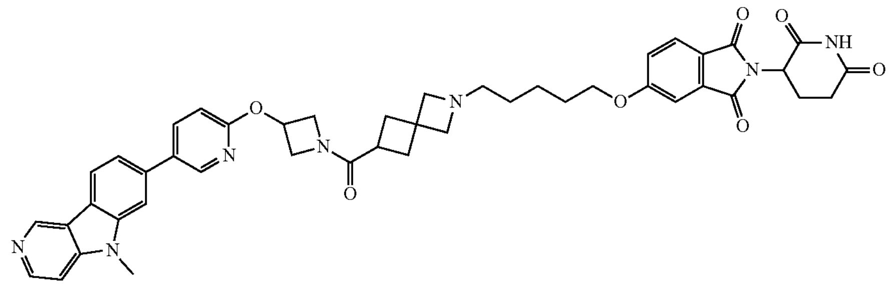 [SMILES: Cn1c2ccncc2c2ccc(-c3ccc(OC4CN(C(=O)C5CC6(C5)CN(CCCCCOc5ccc7c(c5)C(=O)N(C5CCC(=O)NC5=O)C7=O)C6)C4)nc3)cc21] | 2-(2,6-dioxopiperidin-3-yl)-5-((5-(6-(3-((5-(5-methyl-5H-pyrido[4,3-b]indol-7-yl)pyridin-2-yl)oxy)azetidine-1-carbonyl)-2-azaspiro[3.3]heptan-2-yl)pentyl)oxy)isoindoline-1,3-dione | | 796.6 | $^1$H NMR (300 MHz, DMSO): δ 11.13 (m, 1H), 9.38 (s, 1H), 8.67-8.66 (s, ,1H), 8.53-8.51 (m, 1H), 8.36-8.34 (m, 1H), 8.29-8.25 (m, 1H), 8.01 (s, 1H), 7.86-7.83 (m, 1H), 7.66-7.64 (m, 2H), 7.44-7.34 (m, 2H), 7.08-7.05 (m, 1H), 5.45 (m, 1H) 5.13 (m, 1H), 4.53 (m, 1H), 4.35 (m, 2H), 4.19-4.15 (m, 2H), 4.03 (m, 1H), 3.98 (m, 3H), 3.87 (m, 1H), 3.11 (m, 2H), 3.00-2.97 (m, 3H), 2.29-2.21 (m, 2H), 2.19-2.18 (m, 2H), 2.02 (m, 1H), 1.91 (m, 2H), 1.77-1.72 (m, 2H), 1.41-1.16 (m, 6H). |

TABLE 1-continued

| | | | | |
|---|---|---|---|---|
| 404 | 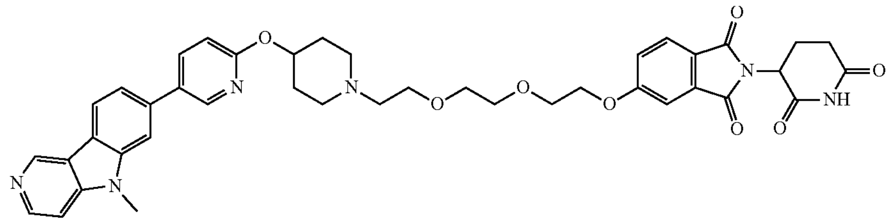 [SMILES: Cn1c2ccncc2c2ccc(-c3ccc(OC4CCN(CCOCCOCCOc5ccc6c(c5)C(=O)N(C5CCC(=O)NC5=O)C6=O)CC4)nc3)cc21] | 2-(2,6-dioxopiperidin-3-yl)-5-(2-(2-(2-(4-((5-(5-methyl-5H-pyrido[4,3-b]indol-7-yl)pyridin-2-yl)oxy)piperidin-1-yl)ethoxy)ethoxy)ethoxy)isoindoline-1,3-dione | 747.6 | $^1$H NMR (300 MHz, DMSO-$d_6$): δ 11.11 (s, 1H), 9.36 (s, 1H), 8.63 (m, 1H), 8.49 (m, 1H), 8.31 (m, 1H), 8.16 (m, 1H), 7.97 (s, 1H), 7.83-7.82 (m, 1H), 7.62 (m, 2H), 7.46-7.37 (m, 2H), 6.92-6.90 (m, 1H), 5.12-5.05 (m, 2H), 5.18-5.08 (m, 1H), 4.32 (m, 2H), 3.96 (s, 3H), 3.89-3.61 (m, 2H), 3.55 (m, 5H) 2.99-2.71 (m, 3H), 2.59 (m, 1H), 2.39-2.19 (m, 3H), 2.01-1.92 (m, 3H), 1.76-1.62 (m 2H). |
| 405 | 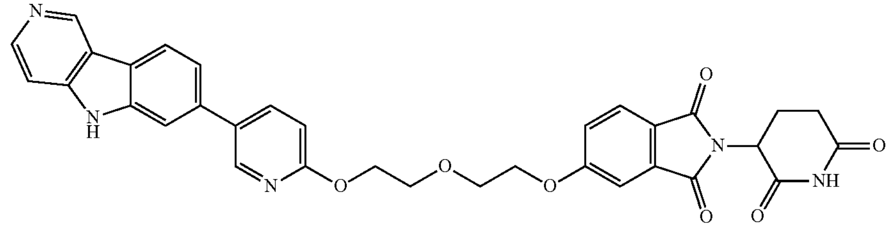 [SMILES: O=C1CCC(N2C(=O)c3ccc(OCCOCCOc4ccc(-c5ccc6c(c5)[nH]c5ccncc56)cn4)cc3C2=O)C(=O)N1] | 5-(2-(2-((5-(5H-pyrido[4,3-b]indol-7-yl)pyridin-2-yl)oxy)ethoxy)ethoxy)-2-(2,6-dioxopiperidin-3-yl)isoindoline-1,3-dione | 606.4 | $^1$H NMR (300 MHz, DMSO): δ 11.79 (s, 1H), 11.12 (s, 1H), 9.35 (s, 1H), 8.56 (s, 1H), 8.43-8.41 (m, 1H), 8.31-8.29 (m, 2H), 8.13-8.09 (m, 1H), 7.84-7.81 (m, 1H), 7.77 (m, 1H), 7.57-7.54 (m, 1H), 7.49-7.47 (m, 1H), 7.39-7.36 (m, 1H), 6.96-6.93 (m, 1H), 5.14-5.08 (m, 1H), 4.49-4.46 (m, 2H), 4.36 (m, 2H), 3.87 (m, 4H), 2.87-2.73 (m, 1H), 2.51 (m, 2H), 2.04-2.00 (m, 1H). |
| 406 | 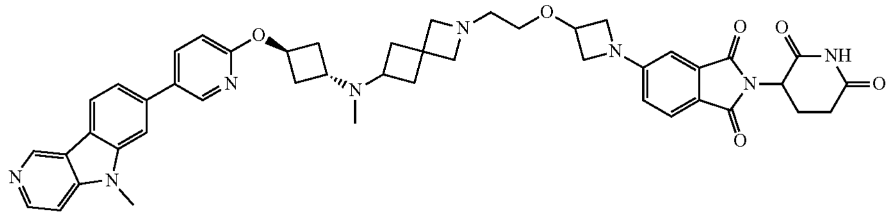 [SMILES: Cn1c2ccncc2c2ccc(-c3ccc(O[C@H]4C[C@H](N(C)C5CC6(C5)CN(CCOC5CN(c7ccc8c(c7)C(=O)N(C7CCC(=O)NC7=O)C8=O)C5)C6)C4)nc3)cc21] | 2-(2,6-dioxopiperidin-3-yl)-5-(3-(2-(6-(methyl((1r,3r)-3-((5-(5-methyl-5H-pyrido[4,3-b]indol-7-yl)pyridin-2-yl)oxy)cyclobutyl)amino)-2-azaspiro[3.3]heptan-2-yl)ethoxy)azetidin-1-yl)isoindoline-1,3-dione | 809.6 | $^1$H NMR (400 MHz, DMSO-d6): δ 1.93-2.31 (m, 10 H), 2.53-2.57 (m, 6 H), 2.79-2.99 (m, 3 H), 3.57 (s, 2 H), 3.88 (m, 2 H), 4.00 (s, 5 H), 4.09 (s, 2 H), 4.22-4.36 (m, 2 H), 4.51 (s, 1 H), 5.06 (m, 1 H), 5.23 (s, 1 H), 6.70 (d, J = 8.4 Hz, 1 H), 6.84 (d, J = 2.0 Hz, 1 H), 6.96 (d, J = 8.8 Hz, 1 H), 7.63-7.76 (m, 3 H), 8.02 (s, 1 H), 8.14 (s, 1 H), 8.22 (m, 1 H), 8.37 (d, J = 8.0 Hz, 1 H), 8.55 (d, J = 6.0 Hz, 1 H), 8.65 (d, J = 2.4 Hz, 1 H), 9.44 (s, 1 H), 11.07 (s, 1 H) |
| 407 | 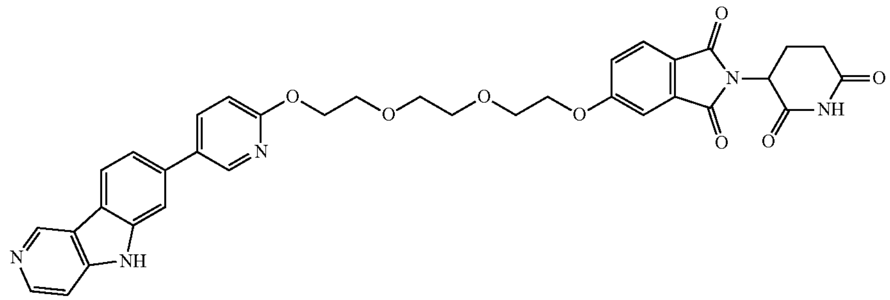 [SMILES: O=C1CCC(N2C(=O)c3ccc(OCCOCCOCCOc4ccc(-c5ccc6c(c5)[nH]c5ccncc56)cn4)cc3C2=O)C(=O)N1] | 5-(2-(2-(2-((5-(5H-pyrido[4,3-b]indol-7-yl)pyridin-2-yl)oxy)ethoxy)ethoxy)ethoxy)-2-(2,6-dioxopiperidin-3-yl)isoindoline-1,3-dione | 650.4 | $^1$H NMR (300 MHz, DMSO-$d_6$): δ 11.77 (s, 1H), 11.14 (s, 1H), 9.35 (s, 1H), 8.56 (s, 1H), 8.43-8.42 (m, 1H), 8.30-8.28 (m, 1H), 8.11-8.09 (m, 1H), 7.82-7.76 (m, 2H), 7.56-7.53 (m, 1H), 7.48-7.46 (m, 2H), 7.37-7.35 (m, 1H), 6.96-6.93 (m, 1H), 5.11 (m, 1H), 4.45-4.43 (m, 2H), 4.31 (m, 2H), 3.80-3.79 (m, 4H), 3.64 (m, 4H), 2.89 (m, 1H), 2.63 (m, 1H), 2.07 (m, 2H). |

TABLE 1-continued

| | | | | |
|---|---|---|---|---|
| 408 | 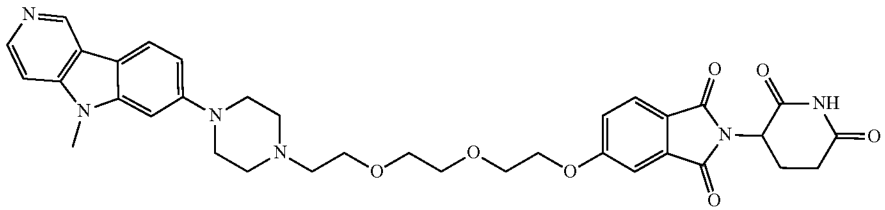 [SMILES: Cn1c2ccncc2c2ccc(N3CCN(CCOCCOCCOc4ccc5c(c4)C(=O)N(C4CCC(=O)NC4=O)C5=O)CC3)cc21] | 2-(2,6-dioxopiperidin-3-yl)-5-(2-(2-(2-(4-(5-methyl-5H-pyrido[4,3-b]indol-7-yl)piperazin-1-yl)ethoxy)ethoxy)ethoxy)isoindoline-1,3-dione | 655.5 | $^1$H NMR (300 MHz, DMSO): δ 11.10 (s, 1H), 9.13 (s, 1H), 8.36-8.34 (m, 1H), 8.15 (s, 1H), 8.00-7.96 (m, 1H), 7.82-7.79 (m, 1H), 7.49-7.45 (m, 2H), 7.38-7.34 (m, 1H), 7.03 (s, 1H), 6.96-6.92 (m, 1H), 5.12-5.06 (m, 1H), 4.33-4.30 (m, 2H), 3.90 (m, 5H), 3.61 (m, 6H), 3.25-3.14 (m, 6H), 2.97-2.80 (m, 2H), 2.60 (m, 4H), 2.06-1.97 (m, 1H). |
| 409 | 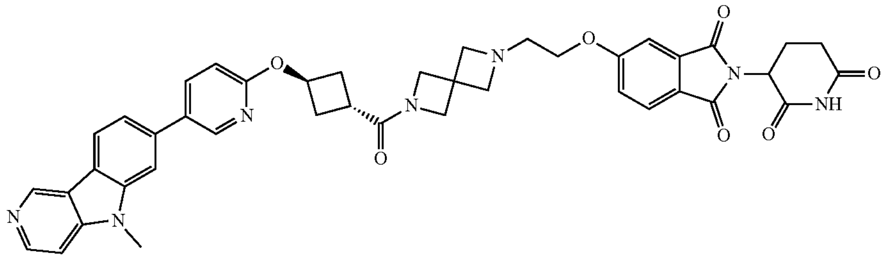 [SMILES: Cn1c2ccncc2c2ccc(-c3ccc(O[C@H]4C[C@H](C(=O)N5CC6(CN(CCOc7ccc8c(c7)C(=O)N(C7CCC(=O)NC7=O)C8=O)C6)C5)C4)nc3)cc21] | 2-(2,6-dioxopiperidin-3-yl)-5-(2-(6-((1r,3r)-3-((5-(5-methyl-5H-pyrido[4,3-b]indol-7-yl)pyridin-2-yl)oxy)cyclobutane-1-carbonyl)-2,6-diazaspiro[3.3]heptan-2-yl)ethoxy)isoindoline-1,3-dione | 754.6 | $^1$H NMR (400 MHz, DMSO-d6): δ 11.12 (s, 1H), 9.37 (s, 1H), 8.63 (d, J = 2.3 Hz, 1H), 8.50 (d, J = 5.6 Hz, 1H), 8.33 (d, J = 8.0 Hz, 1H), 8.19 (m, 1H), 7.98 (d, J = 0.8 Hz, 1H), 7.84 (d, J = 8.4 Hz, 1H), 7.70-7.56 (m, 2H), 7.42 (d, J = 2.0 Hz, 1H), 7.34 (m, 1H), 6.94 (d, J = 8.6 Hz, 1H), 5.30 (t, J = 6.8 Hz, 1H), 5.12 (m, 1H), 4.18-4.11 (m, 4H), 3.99-3.93 (m, 5H), 3.35 (s, 4H), 3.15-3.04 (m, 1H), 2.95-2.82 (m, 1H), 2.76 (t, J = 4.8 Hz, 2H), 2.64-2.55 (m, 4H), 2.34-2.25 (m, 2H), 2.08-2.00 (m, 1H). |
| 410 | 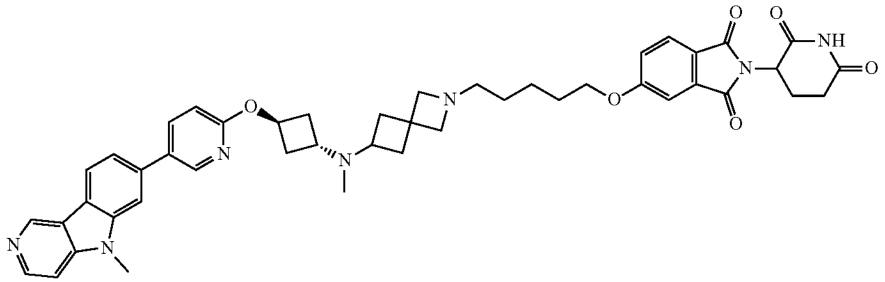 [SMILES: Cn1c2ccncc2c2ccc(-c3ccc(O[C@H]4C[C@H](N(C)C5CC6(C5)CN(CCCCCOc5ccc7c(c5)C(=O)N(C5CCC(=O)NC5=O)C7=O)C6)C4)nc3)cc21] | 2-(2,6-dioxopiperidin-3-yl)-5-((5-(6-(methyl((1r,3r)-3-(4-(5-methyl-5H-pyrido[4,3-b]indol-7-yl)phenoxy)cyclobutyl)amino)-2-azaspiro[3.3]heptan-2-yl)pentyl)oxy)isindoline-1,3-dione | 795.6 | $^1$H NMR (400 MHz, DMSO-d6): δ 9.67 (s, 1H), 8.68-8.67 (m, 1H), 8.48-8.47 (m, 1H), 8.16-8.07 (m, 2H), 7.86-7.80 (m, 4H), 7.39-7.32 (m, 2H), 7.01-6.99 (m, 2H), 5.68 (s, 1H), 5.11-5.06 (m, 1H), 4.91 (m, 1H), 4.22-3.99 (m, 11H), 3.72 (m, 3H), 3.15-3.10 (m, 2H), 2.76 (m, 3H), 2.63-2.62 (m, 6H), 2.47 (m, 3H), 2.06 (m, 2H), 1.75 (m, 2H), 1.52-1.36 (m, 2H). . |
| 411 | 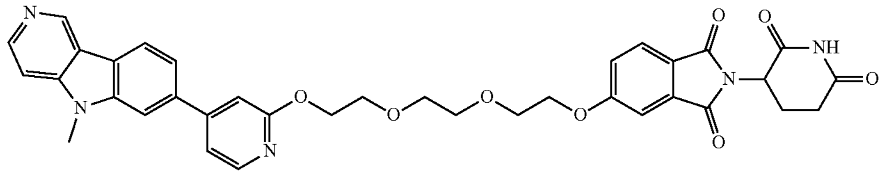 [SMILES: Cn1c2ccncc2c2ccc(-c3ccnc(OCCOCCOCCOc4ccc5c(c4)C(=O)N(C4CCC(=O)NC4=O)C5=O)c3)cc21] | 2-(2,6-dioxopiperidin-3-yl)-5-(2-(2-(2-((4-(5-methyl-5H-pyrido[4,3-b]indol-7-yl)pyridin-2-yl)oxy)ethoxy)ethoxy)ethoxy)isoindoline-1,3-dione | 664.5 | $^1$H NMR (400 MHz, DMSO-d6): δ 11.11 (s, 1H), 9.39 (s, 1H), 8.51 (d, J = 5.6 Hz, 1H), 8.35 (d, J = 8.4 Hz, 1H), 8.24 (d, J = 5.2 Hz, 1H), 8.14 (s, 1H), 7.80-7.72 (m, 2H), 7.64 (d, J = 5.2 Hz, 1H), 7.50 (d, J = 5.6 Hz, 1H), 7.43 (d, J = 2.4 Hz, 1H), 7.36-7.32 (m, 2H), 5.09 (br d, J = 12.8 Hz, 1H), 4.52-4.42 (m, 2H), 4.37-4.25 (m, 2H), 4.02-3.94 (m, 1H), 4.00-3.94 (m, 3H), 3.90-3.76 (m, 4H), 3.66-3.61 (m, 3H), 2.58-2.55 (m, 4H) |

TABLE 1-continued

| | | | | |
|---|---|---|---|---|
| 412 | 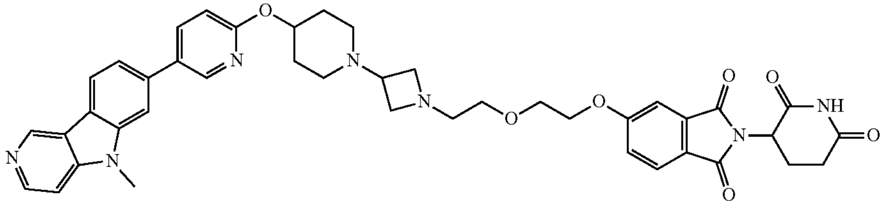 [SMILES: Cn1c2ccncc2c2ccc(-c3ccc(OC4CCN(C5CN(CCOCCOc6ccc7c(c6)C(=O)N(C6CCC(=O)NC6=O)C7=O)C5)CC4)nc3)cc21] | 2-(2,6-dioxopiperidin-3-yl)-5-(2-(2-(3-(4-((5-(5-methyl-5H-pyrido[4,3-b]indol-7-yl)pyridin-2-yl)oxy)piperidin-1-yl)azetidin-1-yl)ethoxy)ethoxy)isoindoline-1,3-dione | 758.6 | 1H NMR (400 MHz, DMSO-d6): δ 11.10 (s, 1H), 9.35 (s, 1H), 8.63 (s, 1H), 8.49 (d, 1H), 8.33 (m, 1H), 8.18 (m, 1H), 7.97 (s, 1H), 7.84 (m, 1H), 7.66-7.58 (m, 2H), 7.45-7.38 (m, 2H), 6.92 (m, 1H), 5.16-5.01 (m, 3H), 4.31 (m, 3H), 3.96 (m, 4H), 3.75 (m, 4H), 2.91-2.74 (m, 5H), 2.07-1.94 (m, 6H), 1.65 (m, 2H), 1.24 (m, 3H). |
| 413 | 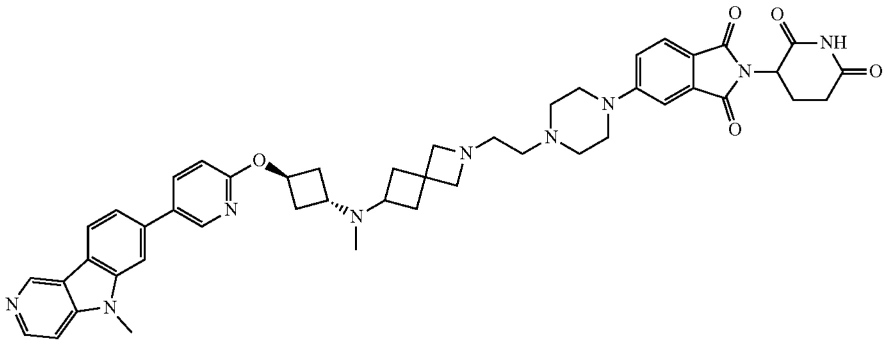 [SMILES: Cn1c2ccncc2c2ccc(-c3ccc(O[C@H]4C[C@H](N(C)C5CC6(C5)CN(CCN5CCN(c7ccc8c(c7)C(=O)N(C7CCC(=O)NC7=O)C8=O)CC5)C6)C4)nc3)cc21] | 2-(2,6-dioxopiperidin-3-yl)-5-(4-(2-(6-(methyl((1r,3r)-3-((5-(5-methyl-5H-pyrido[4,3-b]indol-7-yl)pyridin-2-yl)oxy)cyclobutyl)amino)-2-azaspiro[3.3]heptan-2-yl)ethyl)piperazin-1-yl)isoindoline-1,3-dione | 822.7 | $^1$H NMR (400 MHz, DMSO-d6): δ 11.07 (s, 1H), 9.37 (s, 1H), 8.64 (d, J = 2.4 Hz, 1H), 8.50 (d, J = 5.6 Hz, 1H), 8.33 (d, J = 8.0 Hz, 1H), 8.19 (m, 3H), 7.98 (s, 1H), 7.71-7.59 (m, 3H), 7.34 (d, J = 1.2 Hz, 1H), 7.29-7.20 (m, 1H), 6.95 (d, J = 8.8 Hz, 1H), 5.25-5.15 (m, 1H), 5.07 (m, 1H), 3.96 (s, 3H), 3.42 (s, 5H), 3.25-3.02 (m, 1H), 2.99-2.80 (m, 2H), 2.74-2.57 (m, 5H), 2.53 (s, 3H), 2.43-2.34 (m, 5H), 2.43-2.34 (m, 1H), 2.24-2.09 (m, 5H), 2.03-1.90 (m, 6H). |
| 414 | 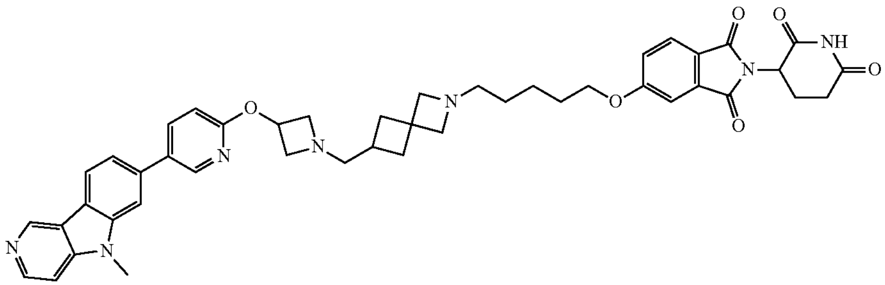 [SMILES: Cn1c2ccncc2c2ccc(-c3ccc(OC4CN(CC5CC6(C5)CN(CCCCCOc5ccc7c(c5)C(=O)N(C5CCC(=O)NC5=O)C7=O)C6)C4)nc3)cc21] | 2-(2,6-dioxopiperidin-3-yl)-5-((5-(6-((3-((5-(5-methyl-5H-pyrido[4,3-b]indol-7-yl)pyridin-2-yl)oxy)azetidin-1-yl)methyl)-2-azaspiro[3.3]heptan-2-yl)pentyl)oxy)isoindoline-1,3-dione | 782.6 | $^1$H NMR (400 MHz, DMSO): δ 11.12 (s, 1H), 9.83 (s, 1H), 9.39 (s, 1H), 9.06-9.04 (m, 1H), 8.84-8.82 (m, 1H), 8.68-8.66 (m, 1H), 8.40-8.26 (m, 4H), 7.99-7.97 (m, 1H), 7.86-7.84 (m, 2H), 7.42-7.33 (m, 2H), 5.82-5.72 (m, 1H), 5.14-5.10 (m, 2H), 4.85 (m, 1H), 4.20-4.17 (m, 6H), 3.17-2.97 (m, 6H), 2.63-2.55 (m, 2H), 2.35 (m, 2H), 2.08-2.02 (m, 3H), 1.81-1.68 (m, 7H). |

TABLE 1-continued

| | | | | | |
|---|---|---|---|---|---|
| 415 | 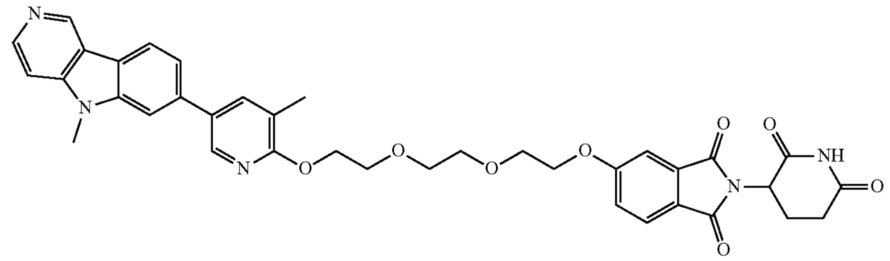 [SMILES: Cc1cc(-c2ccc3c4cnccc4n(C)c3c2)cnc1OCCOCCOCCOc1ccc2c(c1)C(=O)N(C1CCC(=O)NC1=O)C2=O] | 2-(2,6-dioxopiperidin-3-yl)-5-(2-(2-(2-((3-methyl-5-(5-methyl-5H-pyrido[4,3-b]indol-7-yl)pyridin-2-yl)oxy)ethoxy)ethoxy)ethoxy)isoindoline-1,3-dione | | 678.5 | $^1$H NMR (300 MHz, DMSO-$d_6$) δ: 11.12 (s, 1H), 9.37 (s, 1H), 8.52-8.25 (m, 2H), 8.30 (d, 1H), 8.20 (s, 1H), 8.04 (d, 1H), 7.95 (s, 1H), 7.80 (d, 1H), 7.69-7.58 (m, 2H), 7.43 (d, 1H), 7.35 (dd, 1H), 5.15-5.06 (m, 1H), 4.52-4.43 (m, 2H), 4.37-4.26 (m, 2H), 3.94 (s, 3H), 3.88-3.78 (m, 4H), 3.65 (s, 4H), 2.98-2.80 (m, 1H), 2.62-2.52 (m, 2H), 2.25 (s, 3H), 2.07-1.95 (m, 1H). |
| 416 | 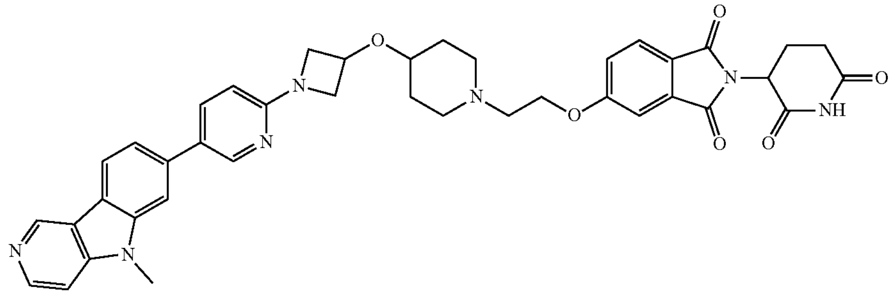 [SMILES: Cn1c2ccncc2c2ccc(-c3ccc(N4CC(OC5CCN(CCOc6ccc7c(c6)C(=O)N(C6CCC(=O)NC6=O)C7=O)CC5)C4)nc3)cc21] | 2-(2,6-dioxopiperidin-3-yl)-5-(2-(4-((1-(5-(5-methyl-5H-pyrido[4,3-b]indol-7-yl)pyridin-2-yl)azetidin-3-yl)oxy)piperidin-1-yl)ethoxy)isoindoline-1,3-dione | A | 714.5 | 1H NMR (400 MHz, DMSO-d6): δ 11.10 (s, 1H), 9.33 (s, 1H), 8.58 (s, 1H), 8.49-8.47 (m, 1H), 8.29-8.27 (m, 1H), 8.18 (s, 1H), 8.04-8.01 (m, 1H), 7.90 (s, 1H), 7.84-7.82 (m, 1H), 7.61-7.56 (m, 2H), 7.47-7.46 (s, 1H), 7.38-7.35 (m, 1H), 6.54-6.52 (m, 1H), 5.13-5.05 (m, 1H), 4.61-4.53 (m, 1H), 4.29-4.23 (m, 4H), 3.95 (s, 3H), 3.81-3.77 (m, 2H), 3.48 (m, 1H), 2.90-2.79 (m, 3H), 2.74 (m, 2H), 2.67-2.66 (m, 2H), 2.22-2.16 (m, 2H), 2.07 (m, 1H), 1.86 (m, 2H), 1.49 (m, 2H). |
| 417 | 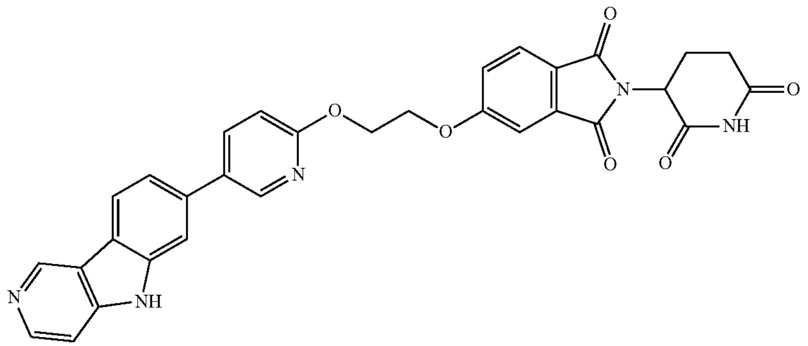 [SMILES: O=C1CCC(N2C(=O)c3ccc(OCCOc4ccc(-c5ccc6c(c5)[nH]c5ccncc56)cn4)cc3C2=O)C(=O)N1] | 5-(2-((5-(5H-pyrido[4,3-b]indol-7-yl)pyridin-2-yl)oxy)ethoxy)-2-(2,6-dioxopiperidin-3-yl)isoindoline-1,3-dione | | 562.4 | $^1$H NMR (300 MHz, DMSO-$d_6$): δ 11.77 (s, 1H), 11.11 (s, 1H) 9.35 (s, 1H), 8.59 (s, 1H), 8.43-8.42 (m, 1H), 8.31-8.29 (m, 1H), 8.20-8.13 (m, 2H), 7.87-7.85 (m, 1H), 7.78 (s, 1H), 7.58-7.54 (m, 2H), 7.49-7.42 (m, 1H), 7.02-6.99 (m, 1H), 5.15-5.10 (m, 1H), 4.71 (m, 2H), 4.60 (m, 2H), 2.93-2.85 (m, 2H), 2.76-2.55 (m, 2H). |

TABLE 1-continued

| | | | | | |
|---|---|---|---|---|---|
| 418 | 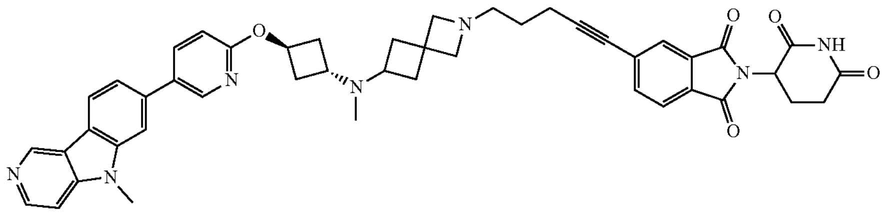 [SMILES: Cn1c2ccncc2c2ccc(-c3ccc(O[C@H]4C[C@H](N(C)C5CC6(C5)CN(CCCC#Cc5ccc7c(c5)C(=O)N(C5CCC(=O)NC5=O)C7=O)C6)C4)nc3)cc21] | 2-(2,6-dioxopiperidin-3-yl)-5-(5-(6-(methyl((1r,3r)-3-((5-(5-methyl-5H-pyrido[4,3-b]indol-7-yl)pyridin-2-yl)oxy)cyclobutyl)amino)-2-azaspiro[3.3]heptan-2-yl)pent-1-yn-1-yl)isindoline-1,3-dione | | 776.6 | $^1$H NMR (400 MHz, DMSO-d6): δ 11.14 (s, 1H), 10.64 (s, 1H), 10.82-10.54 (m, 1H), 10.35 (s, 1H), 10.42-10.23 (m, 1H), 9.79 (s, 1H), 8.81-8.77 (m, 1H), 8.79 (d, J = 6.8 Hz, 1H), 8.73-8.70 (m, 1H), 8.72 (d, J = 2.4 Hz, 1H), 8.59-8.54 (m, 1H), 8.56 (d, J = 8.4 Hz, 1H), 8.31 (m, 1H), 8.26-8.18 (m, 2H), 7.97-7.84 (m, 4H), 7.04 (d, J = 8.4 Hz, 1H), 5.30 (s, 1H), 5.17 (m, J = 1H), 4.58 (m, 1H), 4.26 (s, 1H), 4.20-3.96 (m, 7H), 3.78-3.63 (m, 1H), 2.98-2.77 (m, 4H), 2.24-1.91 (m, 2H), 1.84-1.71 (m, 2H), 1.56-1.49 (m, 1H), 1.53 (d, J = 6.8 Hz, 1H), 1.59-1.46 (m, 1H), 1.59-1.43 (m, 1H) |
| 419 | 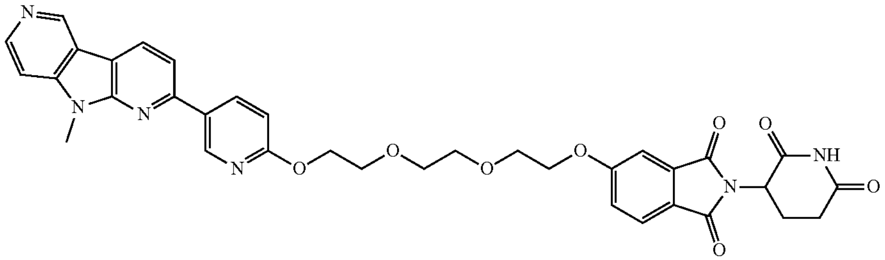 [SMILES: Cn1c2ccncc2c2ccc(-c3ccc(OCCOCCOCCOc4ccc5c(c4)C(=O)N(C4CCC(=O)NC4=O)C5=O)nc3)nc21] | 2-(2,6-dioxopiperidin-3-yl)-5-(2-(2-(2-((5-(9-methyl-9H-pyrrolo[2,3-b:4,5-c']dipyridin-2-yl)pyridin-2-yl)oxy)ethoxy)ethoxy)ethoxy)isoindoline-1,3-dione | B | 665.4 | $^1$H NMR (400 MHz, DMSO-d6): δ 1.97-2.08 (m, 1 H), 2.53 (m, 2 H), 2.84-2.93 (m, 1 H), 3.65 (s, 4 H), 3.78-3.85 (m, 4 H), 3.98 (s, 3 H), 4.26-4.37 (m, 2 H), 4.45-4.51 (m, 2 H), 5.10 (m, 1 H), 6.99 (d, J = 8.4 Hz, 1 H), 7.35 (m, 1 H), 7.44 (d, J = 2.0 Hz, 1 H), 7.69 (d, J = 5.6 Hz, 1 H), 7.80 (d, J = 8.0 Hz, 1 H), 7.95 (d, J = 8.0 Hz, 1 H), 8.22 (s, 1 H), 8.57 (d, J = 6.0 Hz, 2 H), 8.70 (d, J = 8.0 Hz, 1 H), 9.05 (s, 1 H), 9.39 (s, 1 H), 11.11 (s, 1 H) |
| 420 | 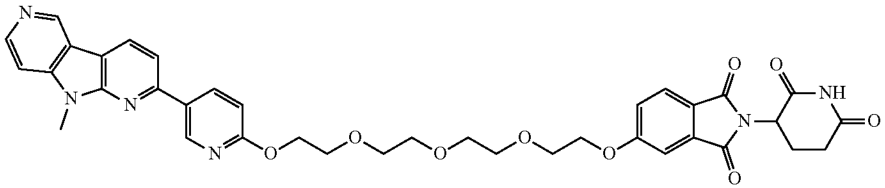 [SMILES: Cn1c2ccncc2c2ccc(-c3ccc(OCCOCCOCCOCCOc4ccc5c(c4)C(=O)N(C4CCC(=O)NC4=O)C5=O)nc3)nc21] | 2-(2,6-dioxopiperidin-3-yl)-5-(2-(2-(2-(2-((5-(9-methyl-9H-pyrrolo[2,3-b:4,5-c']dipyridin-2-yl)pyridin-2-yl)oxy)ethoxy)ethoxy)ethoxy)ethoxy)isoindoline-1,3-dione | | 709.5 | $^1$H NMR (400 MHz, DMSO-d6): δ 1.97-2.08 (m, 1 H), 2.56 (s, 2 H), 2.82-2.96 (m, 1 H), 3.59 (m, 8 H), 3.75-3.82 (m, 4 H), 3.98 (s, 3 H), 4.24-4.33 (m, 2 H), 4.42-4.52 (m, 2 H), 5.10 (m, 1 H), 6.95-7.04 (m, 1 H), 7.34 (m 1 H), 7.42 (s, 1 H), 7.69 (d, J = 5.6 Hz, 1 H), 7.79 (d, J = 8.4 Hz, 1 H), 7.95 (d, J = 8.0 Hz, 1 H), 8.26 (s, 1 H), 8.57 (m, 2 H), 8.70 (d, J = 8.0 Hz, 1 H), 9.05 (s, 1 H), 9.38 (s, 1 H), 11.11 (s, 1 H) |
| 421 | 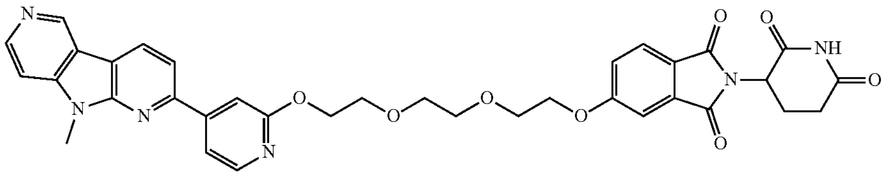 [SMILES: Cn1c2ccncc2c2ccc(-c3ccnc(OCCOCCOCCOc4ccc5c(c4)C(=O)N(C4CCC(=O)NC4=O)C5=O)c3)nc21] | 2-(2,6-dioxopiperidin-3-yl)-5-(2-(2-(2-((4-(9-methyl-9H-pyrrolo[2,3-b:4,5-c']dipyridin-2-yl)pyridin-2-yl)oxy)ethoxy)ethoxy)ethoxy)isoindoline-1,3-dione | | 665.4 | $^1$H NMR (400 MHz, DMSO-$d_6$): δ 11.09 (s, 1 H) 9.42 (s, 1 H) 8.76 (d, J = 8.0 Hz, 1 H) 8.59 (d, J = 5.6 Hz, 1 H) 8.29 (d, J = 5.2 Hz, 1 H) 8.20 (s, 1 H) 8.10 (d, J = 8.0 Hz, 1 H) 7.83 (d, J = 5.6 Hz, 1 H) 7.75 (d, J = 8.4 Hz, 1 H) 7.71 (d, J = 5.6 Hz, 1 H) 7.67 (s, 1 H) 7.40 (d, J = 2.4 Hz, 1 H) 7.32 (dd, J = 8.4, 2.4 Hz, 1 H) 5.09 (dd, J = 12.8, 5.6 Hz, 1 H) 4.44-4.48 (m, 2 H) 4.26-4.31 (m, 2 H) 3.98 (s, 3 H) 3.80 (d, J = 4.4 Hz, 4 H) 3.64 (s, 4 H) 2.88 (ddd, J = 17.2, 13.2, 5.6 Hz, 2 H) 2.60 (d, J = 2.7 Hz, 1 H) 2.55 (s, 1 H) 1.96-2.07 (m, 1 H) |

TABLE 1-continued

| | | | | | |
|---|---|---|---|---|---|
| 422 | 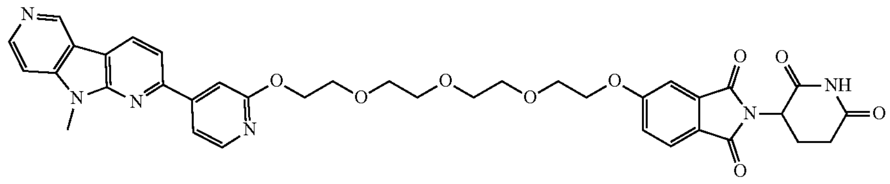 [SMILES: Cn1c2ccncc2c2ccc(-c3ccnc(OCCOCCOCCOCCOc4ccc5c(c4)C(=O)N(C4CCC(=O)NC4=O)C5=O)c3)nc21] | 2-(2,6-dioxopiperidin-3-yl)-5-(2-(2-(2-(4-((4-(9-methyl-9H-pyrrolo[2,3-b:4,5-c']pyridin-2-yl)pyridin-2-yl)oxy)ethoxy)ethoxy)ethoxy)ethoxy)isoindoline-1,3-dione | | 709.5 | $^1$H NMR (400 MHz, DMSO-$d_6$): δ 11.10 (s, 1 H) 9.40 (s, 1 H) 8.74 (d, J = 8.0 Hz, 1 H) 8.58 (d, J = 5.6 Hz, 1 H), 8.28 (d, J = 5.6 Hz, 1 H), 8.17 (s, 1 H) 8.08 (d, J = 8.0 Hz, 1 H) 7.82 (dd, J = 5.6, 1.6 Hz, 1 H) 7.73 (d, J = 8.4 Hz, 1H) 7.69 (d, J = 5.6 Hz, 1 H) 7.66 (d, J = 0.8 Hz, 1 H) 7.36 (d, J = 2.4 Hz, 1 H) 7.28 (dd, J = 8.4, 2.4 Hz, 1 H) 5.09 (dd, J = 12.8, 5.6 Hz, 1 H) 4.42-4.49 (m, 2 H) 4.22-4.28 (m, 2 H) 3.96-4.00 (m, 3 H) 3.75-3.81 (m, 4 H) 3.66 (dd, J = 9.2, 4.0 Hz, 1 H) 3.60 (dd, J = 5.6, 3.2 Hz, 5 H) 3.55-3.57 (m, 2 H) 2.88 (ddd, J = 17.2, 13.6, 5.2 Hz, 1 H) 2.60 (d, J = 2.4 Hz, 1 H) 2.56 (s, 1 H) 1.97-2.08 (m, 1 H) |
| 423 | 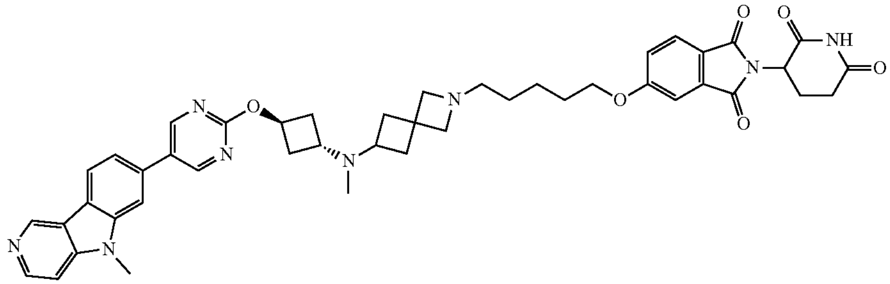 | 2-(2,6-dioxopiperidin-3-yl)-5-((5-(6-(methyl((1r,3r)-3-((5-(5-methyl-5H-pyrido[4,3-b]indol-7-yl)pyrimidin-2-yl)oxy)cyclobutyl)amino)-2-azaspiro[3.3]heptan-2-yl)pentyl)oxy)isoindoline-1,3-dione | | 797.6 | 1H NMR (400 MHz, DMSO-d6): δ 9.28 (s, 1H), 8.93 (s, 1H), 8.44-8.30 (m, 4H), 8.33-8.25 (m, 2H), 7.88 (s, 1H), 7.78-7.76 (m, 1H), 7.66-7.59 (m, 2H), 7.32-7.27 (m, 2H), 5.14-4.99 (m, 2H), 4.18-3.89 (m, 10H), 3.53-3.51 (m, 1H), 3.14-3.02 (m, 3H), 2.79-2.76 (m, 1H), 2.65-2.60 (m, 1H), 2.47-2.02 (m, 10H), 1.74-1.70 (m, 2H), 1.46-1.38 (m, 4H). |
| 424 | 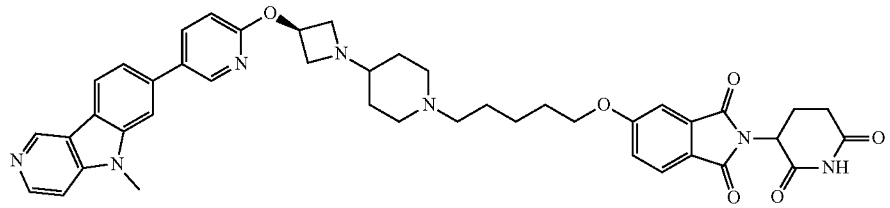 | 2-(2,6-dioxopiperidin-3-yl)-5-((5-(4-(3-((5-(5-methyl-5H-pyrido[4,3-b]indol-7-yl)pyridin-2-yl)oxy)azetidin-1-yl)piperidin-1-yl)pentyl)oxy)isoindoline-1,3-dione | B | 756.6 | 1H NMR (400 MHz, DMSO-d6): δ 9.82 (s, 1H), 9.40 (s, 1H), 9.04 (m, 1H), 8.81-8.80 (m, 1H), 8.68-8.66 (m, 1H), 8.38 (s, 1H), 8.27-8.25 (m, 1H), 7.98-7.96 (m, 1H), 7.98-7.96 (m, 1H), 7.86-7.79 (m, 1H), 7.43-7.42 (s, 1H), 7.37-7.35 (m, 1H), 5.85-5.79 (m, 1H), 5.29-5.26 (m, 1H), 5.17-5.02 (m, 1H), 4.86 (m, 1H0, 4.21-4.17 (m, 5H), 3.85-3.65 (m, 4H), 3.37 (m, 1H), 3.09 (m, 4H), 2.94-2.83 (m, 1H), 2.64 (m, 2H), 2.34-2.29 (m, 2H), 2.13-2.01 (m, 1H), 1.83-1.74 (m, 6H), 1.48 (m, 2H), 1.26-1.25 (m, 1H). |
| 425 | 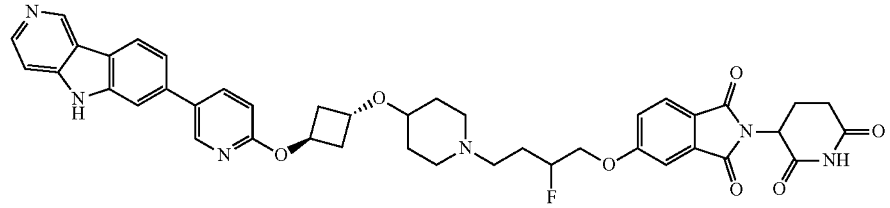 [SMILES: O=C1CCC(N2C(=O)c3ccc(OCC(F)CCN4CCC(O[C@H]5C[C@H](Oc6ccc(-c7ccc8c(c7)[nH]c7ccncc78)cn6)C5)CC4)cc3C2=O)C(=O)N1] | 5-(4-(4-((1r,3r)-3-((5-(5H-pyrido[4,3-b]indol-7-yl)pyridin-2-yl)oxy)cyclobutoxy)piperidin-1-yl)-2-fluorobutoxy)-2-(2,6-dioxopiperidin-3-yl)isoindoline-1,3-dione | | 761.5 | $^1$H NMR (400 MHz, DMSO-$d_6$): δ 9.59 (s, 1 H) 8.45-8.59 (m, 3 H) 8.13 (dd, J = 8.68, 2.57 Hz, 1 H) 7.99 (d, J = 6.72 (Hz, 1 H) 7.96 (s, 1 H), 7.87 (d, J = 8.31 Hz, 1 H) 7.78 (dd, J = 8.25, 1.41 Hz, 1 H) 7.49 (s, 1 H) 7.40 (br d, J = 8.56 Hz, 1 H) 6.96 (d, J = 8.56 Hz, 1 H) 5.39 (br s, 1 H) 5.11-5.14 (m, 1.5 H) 4.98 (br s, 0.5 H) 4.39-4.52 (m, 3 H) 3.85 (br s, 1 H) 3.56-3.76 (m, 1 H) 3.37-3.55 (m, 4 H) 3.09-3.16 (m, 1H), 2.90-2.86 (m, 1H), 2.70-2.80 (m, 2H), 2.49-2.59 (m, |

TABLE 1-continued

| | | | | |
|---|---|---|---|---|
| | | | | 4H), 2.27-2.40 (m, 3H), 2.14-2.17 (m, 2H), 1.91-2.03 (m, 1 H) 1.76 (br d, J = 11.74 Hz, 1 H). |
| 426 | 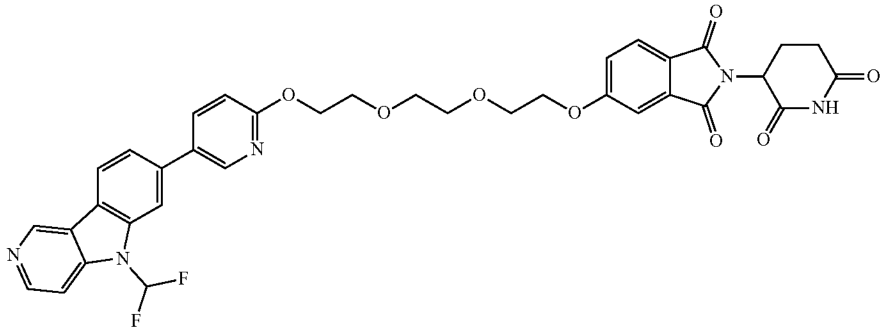 [SMILES: O=C1CCC(N2C(=O)c3ccc(OCCOCCOCCOc4ccc(-c5ccc6c7cnccc7n(C(F)F)c6c5)cn4)cc3C2=O)C(=O)N1] | 5-(2-(2-(2-((5-(5-(difluoromethyl)-5H-pyrido[4,3-b]indol-7-yl)pyridin-2-yl)oxy)ethoxy)ethoxy)ethoxy)-2-(2,6-dioxopiperidin-3-yl)isoindoline-1,3-dione | 700.4 | $^1$H NMR (400 MHz, DMSO-$d_6$): δ 11.09 (s, 1 H) 9.79 (d, J = 2.0 Hz, 1 H) 8.84 (d, J = 6.4 Hz, 1 H) 8.64 (d, J = 2.4 Hz, 1 H) 8.53 (d, J = 8.4 Hz, 1 H) 8.27 (s, 1 H) 8.15-8.23 (m, 2 H) 7.91 (d, J = 8.4 Hz, 1 H) 7.80 (d, J = 8.4 Hz, 1 H) 7.44 (d, J = 2.0 Hz, 1 H) 7.35 (dd, J = 8.4, 2.4 Hz, 1 H) 7.00 (d, J = 8.8 Hz, 1 H) 5.10 (dd, J = 12.8, 5.2 Hz, 1 H) 4.44-4.47 (m, 2 H) 4.29-4.32 (m, 2 H) 3.80 (t, J = 4.4 Hz, 4 H) 3.64 (s, 4 H) 2.82-2.93 (m, 2 H) 2.59 (d, J = 2.4 Hz, 1 H) 2.55 (s, 1 H) 1.98-2.06 (m, 1 H). |
| 427 | 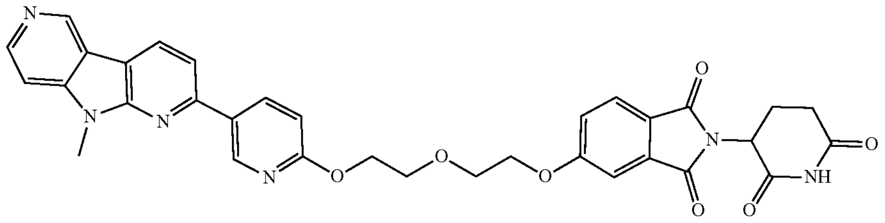 [SMILES: Cn1c2ccncc2c2ccc(-c3ccc(OCCOCCOc4ccc5c(c4)C(=O)N(C4CCC(=O)NC4=O)C5=O)nc3)nc21] | 2-(2,6-dioxopiperidin-3-yl)-5-(2-(2-((5-(9-methyl-9H-pyrrolo[3,2-b:4,5-c']pyridin-2-yl)pyridin-2-yl)oxy)ethoxy)ethoxy)isoindoline-1,3-dione | 621.4 | $^1$H NMR (400 MHz, DMSO-d6) δ 1.99-2.06 (m, 1 H), 2.56 (m, 2 H), 2.88 (m, 1 H), 3.87-3.92 (m, 4 H), 3.99 (s, 3 H), 4.31-4.39 (m, 2 H), 4.49-4.54 (m, 2 H), 5.11 (m, 1 H), 6.98 (d, J = 8.8 Hz, 1 H), 7.37 (m, J = 8.31, 1 H), 7.47 (d, J = 2.0 Hz, 1 H), 7.70 (d, J = 5.6 Hz, 1 H), 7.82 (d, J = 8.2 Hz, 1 H), 7.97 (d, J = 8.0 Hz, 1 H), 8.28 (s, 1 H), 8.55-8.59 (m, 2 H), 8.72 (d, J = 8.4 Hz, 1 H), 9.06 (d, J = 2.4 Hz, 1 H), 9.40 (s, 1 H), 11.10 (s, 1 H). |
| 428 | 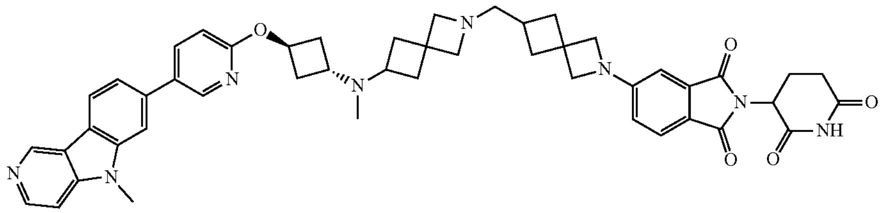 [SMILES: Cn1c2ccncc2c2ccc(-c3ccc(O[C@H]4C[C@H](N(C)C5CC6(C5)CN(CC5CC7(C5)CN(c5ccc8c(c5)C(=O)N(C5CCC(=O)NC5=O)C8=O)C7)C6)C4)nc3)cc21] | 2-(2,6-dioxopiperidin-3-yl)-5-(6-((6-(methyl((1r,3r)-3-((5-(5-methyl-5H-pyrido[4,3-b]indol-7-yl)pyridin-2-yl)oxy)cyclobutyl)amino)-2-azaspiro[3.3]heptan-2-yl)methyl)-2-azaspiro[3.3]heptan-2-yl)isindoline-1,3-dione | 819.6 | $^1$H NMR (400 MHz, DMSO-d6): δ 1.81-2.00 (m, 10 H), 2.06-2.30 (m, 11 H), 2.40 (m, 4 H), 3.84-4.09 (m, 10 H), 4.97-5.09 (m, 1 H), 5.20 (m, 1 H), 6.61 (d, J = 8.4 Hz, 1 H), 6.74 (d, J = 1.6 Hz, 1 H), 6.95 (d, J = 8.8 Hz, 1 H), 7.60-7.66 (m, 3 H), 7.98 (s, 1 H), 8.19 (m, 1 H), 8.22 (s, 3 H), 8.33 (d, J = 8.4 Hz, 1 H), 8.50 (d, J = 5.6 Hz, 1 H), 8.64 (d, J = 2.4 Hz, 1 H), 9.36 (s, 1 H), 11.06 (s, 1 H) |

TABLE 1-continued

| | | | | | |
|---|---|---|---|---|---|
| 429 | 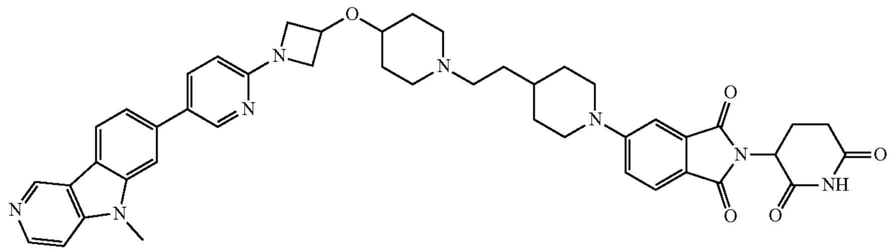 [SMILES: Cn1c2ccncc2c2ccc(-c3ccc(N4CC(OC5CCN(CCC6CCN(c7ccc8c(c7)C(=O)N(C7CCC(=O)NC7=O)C8=O)CC6)CC5)C4)nc3)cc21] | 2-(2,6-dioxopiperidin-3-yl)-5-(4-(2-(4-((1-(5-(5-methyl-5H-pyrido[4,3-b]indol-7-yl)pyridin-2-yl)azetidin-3-yl)oxy)piperidin-1-yl)ethyl)piperidin-1-yl)isoindoline-1,3-dione | | 781.6 | 1H NMR (400 MHz, DMSO-d6): δ 11.10 (s, 1H), 9.34 (s, 1H), 8.59-8.58 (s, 1H), 8.49 (m, 1H), 8.30-8.28 (m, 1H), 8.19 (s, 1H), 8.04-8.02 (m, 1H), 7.90 (m, 1H), 7.66-7.62 (m, 3H), 7.30-7.22 (m, 2H), 6.55-6.53 (m, 1H), 5.10-5.00 (m, 1H), 4.56 (m, 1H), 4.27-4.23 (m, 2H), 4.05-3.96 (m, 6H), 3.80-3.78 (m, 2H), 2.98-2.86 (m, 3H), 2.77 (m, 2H), 2.40-2.37 (m, 2H), 2.13-1.94 (m, 4H), 1.86-1.74 (m, 4H), 1.51-1.39 (m, 5H), 1.20-1.17 (m 3H). |
| 430 | 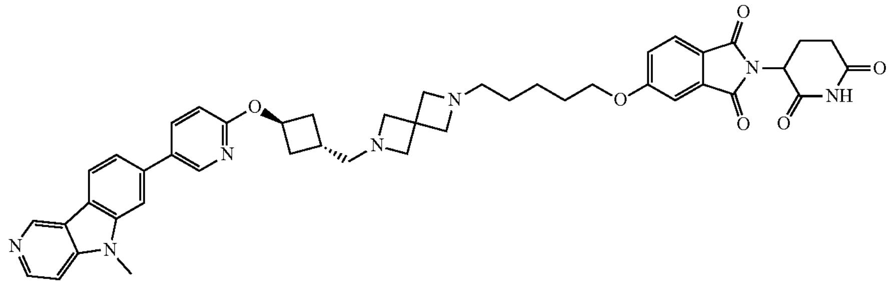 [SMILES: Cn1c2ccncc2c2ccc(-c3ccc(O[C@H]4C[C@H](CN5CC6(CN(CCCCCOc7ccc8c(c7)C(=O)N(C7CCC(=O)NC7=O)C8=O)C6)C5)C4)nc3)cc21] | 2-(2,6-dioxopiperidin-3-yl)-5-((5-(6-(((1r,3r)-3-((5-(5-methyl-5H-pyrido[4,3-b]indol-7-yl)pyridin-2-yl)oxy)cyclobutyl)methyl)-2,6-diazaspiro[3.3]heptan-2-yl)pentyl)oxy)isoindoline-1,3-dione | | 782.6 | $^{1}$H NMR (400 MHz, DMSO-$d_6$): δ 11.11 (s, 1 H) 9.77 (s, 1 H) 8.62-8.83 (m, 2 H) 8.54 (d, J = 8.4 Hz, 1H) 8.15-8.34 (m, 3 H) 7.86 (t, J = 9.6 Hz, 2 H) 7.28-7.47 (m, 2 H) 6.92-7.03 ( m, 1 H) 4.26-4.39 (m, 5 H) 4.12-4.21 (m, 6 H) 3.28 (s, 3 H) 3.15 (d, J = 1.2 Hz, 2 H) 2.60-2.70 (m, 3 H) 2.26-2.37 (m, 2 H) 1.99-2.09 (m, 1 H) 1.71-1.97 (m, 4 H) 1.38-1.55 (m 4 H) |
| 431 | 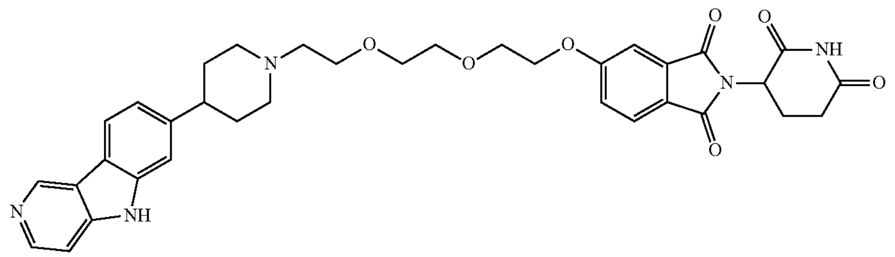 [SMILES: O=C1CCC(N2C(=O)c3ccc(OCCOCCOCCN4CCC(c5ccc6c(c5)[nH]c5ccncc56)CC4)cc3C2=O)C(=O)N1] | 5-(2-(2-(4-(5H-pyrido[4,3-b]indol-7-yl)piperidin-1-yl)ethoxy)ethoxy)ethoxy)-2-(2,6-dioxo-piperidin-3-yl)isoindoline-1,3-dione | B | 640.5 | 1H NMR (400 MHz, DMSO-d6): δ 13.07 (s, 1H), 11.12 (s, 1H), 9.70 (s, 1H), 9.48 (m, 1H), 8.67-8.65 (d, 1H), 8.39-8.37 (d, 1H), 8.02-8.00 (d, 1H), 7.79-7.77 (d, 1H), 7.57-7.46 (m, 2H), 7.37-7.33 (m, 2H), 5.09 (m, 1H), 4.34-4.32 (m, 2H), 3.84-3.82 (m, 4H), 3.68-3.65 (m, 6H), 3.17-2.97 (m, 3H), 2.92-2.84 (m, 1H), 2.68 (m, 2H), 2.50-2.48 (m, 1H), 2.04-2.00 (m, 5H). |
| 432 | 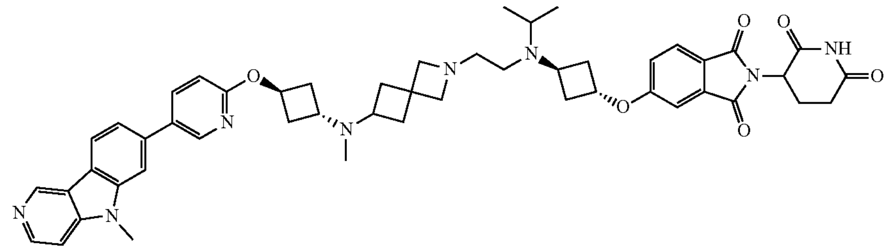 [SMILES: CC(C)N(CCN1CC2(CC(N(C)[C@H]3C[C@H](Oc4ccc(-c5ccc6c7cnccc7n(C)c6c5)cn4)C3)C2)C1)[C@H]1C[C@H](Oc2ccc3c(c2)C(=O)N(C2CCC(=O)NC2=O)C3=O)C1] | 2-(2,6-dioxopiperidin-3-yl)-5-((1R,3r)-3-(isopropyl(2-(6-(methyl((1r,3R)-3-((5-(5-methyl-5H-pyrido[4,3-b]indol-7-yl)pyridin-2-yl)oxy)cyclobutyl)amino)-2-azaspiro[3.3]heptan-2-yl)ethyl)amino)cyclobutoxy)isoindoline-1,3-dione | | 865.7 | $^{1}$H NMR (400 MHz, DMSO-$d_6$): δ 11.12 (d, J = 0.8 Hz, 1H), 9.36 (s, 1H), 8.67-8.60 (m, 1H), 8.50 (d, J = 6.0 Hz, 1H), 8.36-8.25 (m, 5H), 8.20 (m, 1H), 7.98 (s, 1H), 7.90-7.81 (m, 1H), 7.66-7.60 (m, 2H), 7.35-7.17 (m, 2H), 6.95 (d, J = 8.8 Hz, 1H), 5.28-5.03 (m, 1H), 4.92 (s, 1H), 4.03-3.93 (m, 4H), 3.32 (s, 8H), 2.95-2.85 (m, 2H), 2.63-2.55 (m, 4H), 2.44-2.36 (m, 4H), 2.22-2.00 (m, 8H), 1.99-1.90 (m, 5H), 1.15 (s, 2H) |

TABLE 1-continued

| | | | | |
|---|---|---|---|---|
| 433 | 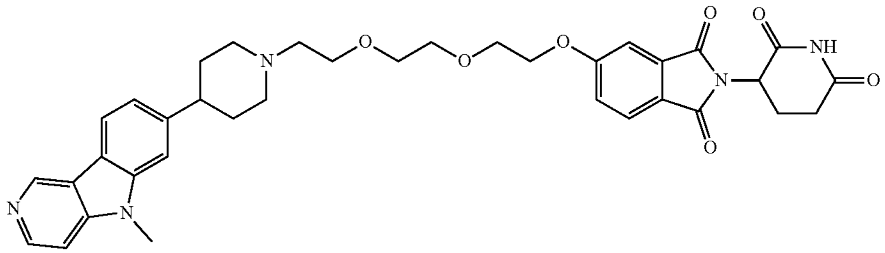 [SMILES: Cn1c2ccncc2c2ccc(C3CCN(CCOCCOCCOc4ccc5c(c4)C(=O)N(C4CCC(=O)NC4=O)C5=O)CC3)cc21] | 2-(2,6-dioxopiperidin-3-yl)-5-(2-(2-(2-(4-(5-methyl-5H-pyrido[4,3-b]indol-7-yl)piperidin-1-yl)ethoxy)ethoxy)ethoxy)isoindoline-1,3-dione | 654.5 | 1H NMR (300 MHz, DMSO-d6): δ 11.12 (s, 1H), 9.73-9.67 (m, 2H), 8.78-8.76 (m, 1H), 8.44-8.41 (m, 1H), 8.24-8.21 (m, 1H), 7.79-7.72 (m, 2H), 7.46-7.33 (m, 3H), 5.12-5.06 (m, 2H), 4.34-4.33 (m, 2H), 4.08 (s, 3H), 3.83 (m, 4H), 3.68-3.54 (m, 6H), 3.37-2.82 (m, 4H), 2.62 (m, 1H), 2.09-1.91 (m, 5H), 1.24 (m, 1H). |
| 434 | 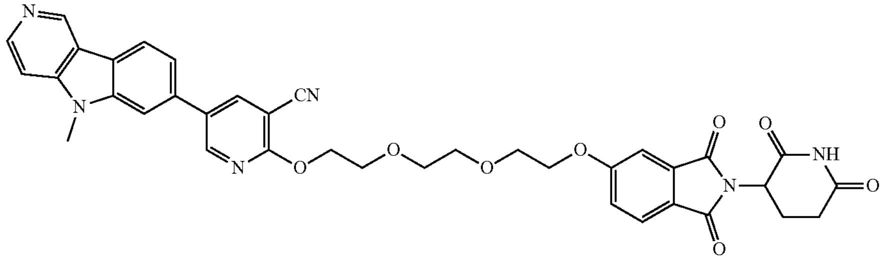 | 2-(2-(2-(2-((2-(2,6-dioxopiperidin-3-yl)-1,3-dioxoisoindolin-5-yl)oxy)ethoxy)ethoxy)ethoxy)-5-(5-methyl-5H-pyrido[4,3-b]indol-7-yl)nicotinonitrile | 689.5 | $^1$H NMR (300 MHz, DMSO-$d_6$) δ 11.11 (s, 1H), 9.41 (s, 1H), 8.96 (s, 1H), 8.81 (s, 1H), 8.53 (m, 1H), 8.38 (m, 1H), 8.11 (m, 1H), 7.80 (m, 3H), 7.43-7.33 (m, 2H), 5.10 (m, 1H), 4.62 (m, 2H), 4.30 (m, 2H), 3.98 (s, 3H), 3.86 (m, 5H), 3.67 (m, 5H), 2.08-1.92 (m, 2H). |
| 435 | 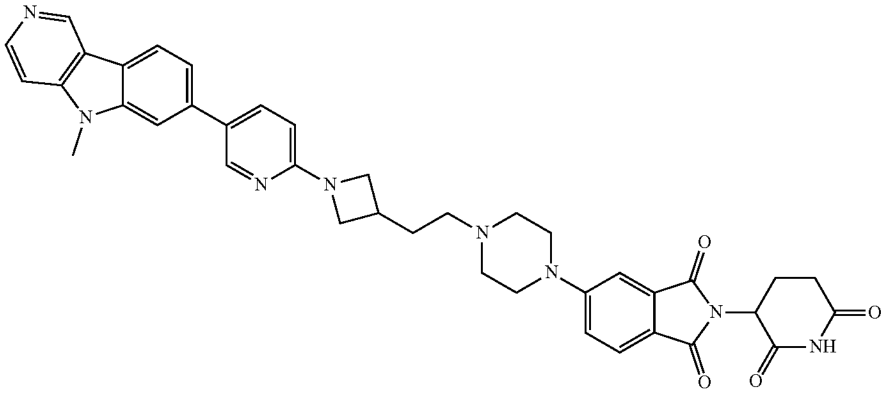 [SMILES: Cn1c2ccncc2c2ccc(-c3ccc(N4CC(CCN5CCN(c6ccc7c(c6)C(=O)N(C6CCC(=O)NC6=O)C7=O)CC5)C4)nc3)cc21] | 2-(2,6-dioxopiperidin-3-yl)-5-(4-(2-(1-(5-(5-methyl-5H-pyrido[4,3-b]indol-7-yl)pyridin-2-yl)azetidin-3-yl)ethyl)piperazin-1-yl)isoindoline-1,3-dione | 683.5 | 1H NMR (300 MHz, DMSO-d6): δ 11.25-10.82 (s, 1H), 9.34 (s, 1H), 8.59-8.58 (m, 1H), 8.50-8.48 (m, 1H), 8.30-8.27 (m, 1H), 8.03-8.00 (m, 1H), 7.90 (s, 1H), 7.71 (m, 1H), 7.68-7.56 (m, 2H), 7.36-7.27 (m, 2H), 6.52-6.49 (m, 1H), 5.12-5.06 (m, 1H), 4.16-4.10 (m, 2H), 3.96 (s, 3H), 3.71-3.66 (m, 2H), 3.46-3.33 (m, 4H), 2.90-2.77 (m, 2H), 2.62-2.53 (m, 6H), 2.40-2.36 (m, 2H), 2.05-2.01 (m, 1H), 1.88-1.84 (m, 2H). |

TABLE 1-continued

| | | | | | |
|---|---|---|---|---|---|
| 436 | 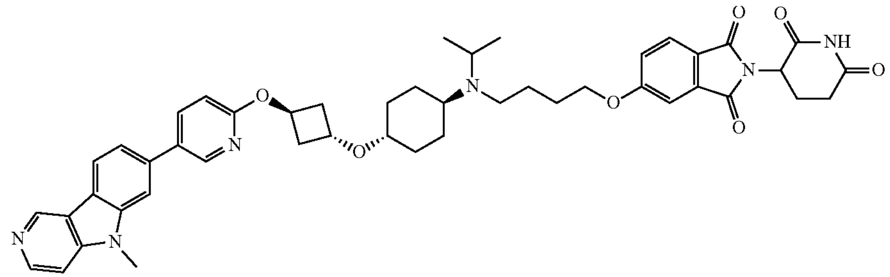 [SMILES: CC(C)N(CCCCOc1ccc2c(c1)C(=O)N(C1CCC(=O)NC1=O)C2=O)[C@H]1CC[C@H](O[C@H]2C[C@H](Oc3ccc(-c4ccc5c6cnccc6n(C)c5c4)cn3)C2)CC1] | 2-(2,6-dioxopiperidin-3-yl)-5-(4-(isopropyl((1R,4r)-4-((1r,3R)-3-((5-(5-methyl-5H-pyrido[4,3-b]indol-7-yl)pyridin-2-yl)oxy)cyclobutoxy)cyclohexyl)amino)butoxy)isoindoline-1,3-dione | A | 813.5 | 1H NMR (400 MHz, DMSO-d6): δ 11.12 (s, 1H), 9.77 (s, 1H), 8.77 (m, 1H), 8.70-8.69 (m, 1H), 8.56-8.54 (m, 1H), 8.44 (m, 1H), 8.28-8.21 (m, 3H), 7.89-7.86 (m, 2H), 7.48-7.47 (s, 1H), 7.39-7.37 (m, 1H), 6.98 (m, 1H), 5.35 (m, 1H), 5.15-5.10 (m, 1H), 4.36-4.33 (m, 1H), 4.26 (m, 2H), 4.15 (s, 3H), 3.76-3.74 (m, 1H), 3.32-3.12 (m, 5H), 2.92-2.83 (m, 1H), 2.43-2.42 (m, 4H), 2.08-2.04 (m, 1H), 1.94-1.74 (m, 10H), 1.53-1.50 (m, 2H), 1.30-1.23 (m, 6H). |
| 437 | 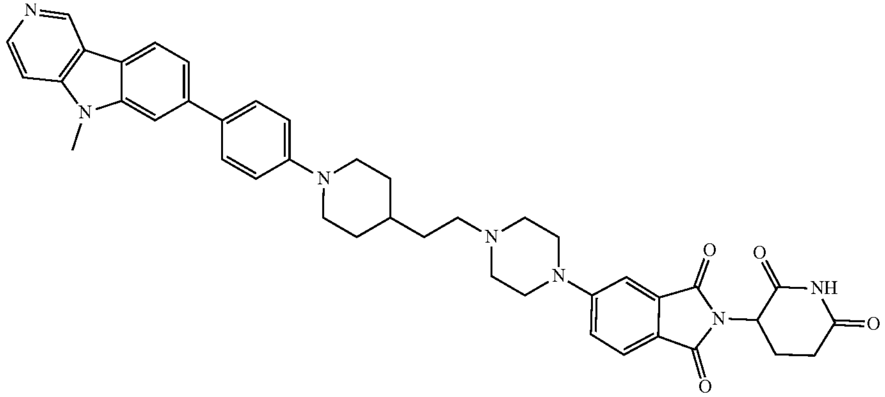 [SMILES: Cn1c2ccncc2c2ccc(-c3ccc(N4CCC(CCN5CCN(c6ccc7c(c6)C(=O)N(C6CCC(=O)NC6=O)C7=O)CC5)CC4)cc3)cc21] | 2-(2,6-dioxopiperidin-3-yl)-5-(4-(2-(1-(4-(5-methyl-5H-pyrido[4,3-b]indol-7-yl)phenyl)piperidin-4-yl)ethyl)piperazin-1-yl)isoindoline-1,3-dione | | 710.4 | 1H NMR (400 MHz, CDCL3) δ 9.36 (m, 1H), 8.58-8.57 (m, 1H), 8.21-8.19 (m, 1H), 7.98 (s, 1H), 7.74-7.72 (s, 1H), 7.67-7.62 (m, 5H), 7.09-7.02 (m, 4H), 4.99-4.95 (m, 1H), 3.97-3.91 (s, 3H), 3.83-3.80 (m, 2H), 3.49 (m, 4H), 2.94-2.75 (m, 4H), 2.67-2.45 (m, 4H), 2.26-1.97 (m, 4H), 1.90-1.87 (m, 2H), 1.52-1.48 (m, 2H), 1.29 (m, 3H). |
| 438 | 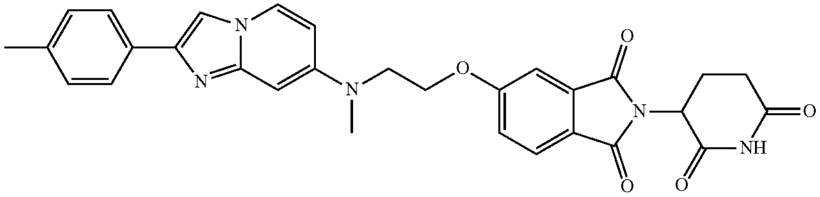 [SMILES: Cc1ccc(-c2cn3ccc(N(C)CCOc4ccc5c(c4)C(=O)N(C4CCC(=O)NC4=O)C5=O)cc3n2)cc1] | 2-(2,6-dioxopiperidin-3-yl)-5-(2-(methyl(2-(p-tolyl)imidazo[1,2-a]pyridin-7-yl)amino)ethoxy)isoindoline-1,3-dione | | 538.3 | $^1$H NMR (400 MHz, DMSO-$d_6$): δ 11.09 (s, 1H), 8.25 (d, J = 7.6 Hz, 1H), 7.97 (s, 1H), 7.82 (d, J = 8.4 Hz, 1H), 7.76 (d, J = 8.0 Hz, 2H), 7.44 (d, J = 2.0 Hz, 1H), 7.34 (m, 1H), 7.21 (d, J = 8.0 Hz, 2H), 6.77 (m, 1H), 6.48 (d, J = 2.0 Hz, 1H), 5.10 (m, 1H), 4.40 (t, J = 5.2 Hz, 2H), 3.87 (t, J = 5.2 Hz, 2H), 3.06 (s, 3H), 2.93-2.82 (m, 1H), 2.62-2.54 (m, 2H), 2.32 (s, 3H), 2.09-1.98 (m, 1H). |

TABLE 1-continued

| | | | | | |
|---|---|---|---|---|---|
| 439 | 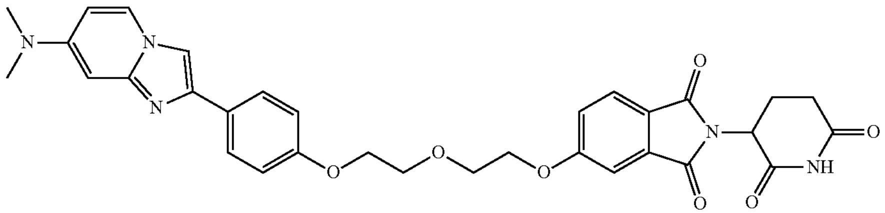 [SMILES: CN(C)c1ccn2cc(-c3ccc(OCCOCCOc4ccc5c(c4)C(=O)N(C4CCC(=O)NC4=O)C5=O)cc3)nc2c1] | 5-(2-(2-(4-(7-(dimethylamino)imidazo[1,2-a]pyridin-2-yl)phenoxy)ethoxy)ethoxy)-2-(2,6-dioxopiperidin-3-yl)isoindoline-1,3-dione | | 598.3 | $^1$H NMR (400 MHz, DMSO-$d_6$): δ 13.32 (s, 1 H), 11.10 (s, 1 H), 8.47 (d, J = 7.6 Hz, 1 H), 8.17 (s, 1 H), 7.80 (d, J = 8.4 Hz, 1 H), 7.74 (d, J = 8.8 Hz, 2 H), 7.44 (d, J = 2.0 Hz, 1 H), 7.11 (dd, J = 8.4, 2.4 Hz, 1 H), 7.13 (d, J = 8.8 Hz, 2 H), 7.08 (dd, J = 7.6, 2.4 Hz, 1 H), 6.44 (d, J = 2.4 Hz, 1 H), 5.11 (d, J = 4.4 Hz, 1 H), 4.34-4.21 (m, 2 H), 4.20-4.19 (m, 2 H), 3.86-3.84, (dd, J = 6.0, 9.6 Hz, 1 H), 3.14 (s, 6 H) 2.81-2.94 (m, 1 H) 2.60-2.50 (m, 2 H), 2.32-2.06 (m, 1 H). |
| 440 | 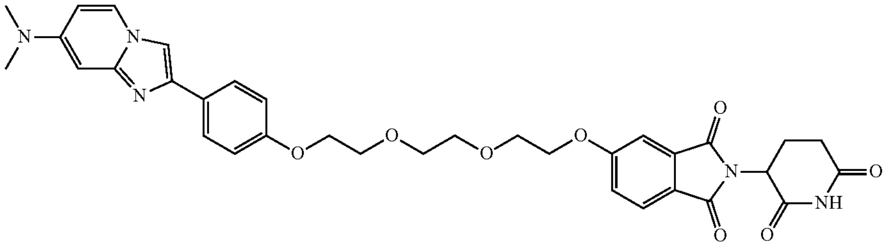 [SMILES: CN(C)c1ccn2cc(-c3ccc(OCCOCCOCCOc4ccc5c(c4)C(=O)N(C4CCC(=O)NC4=O)C5=O)cc3)nc2c1] | 5-(2-(2-(2-(4-(7-(dimethylamino)imidazo[1,2-a]pyridin-2-yl)phenoxy)ethoxy)ethoxy)ethoxy)-2-(2,6-dioxopiperidin-3-yl)isoindoline-1,3-dione | B | 642.3 | $^1$H NMR (400 MHz, DMSO-$d_6$) δ: 13.41 (s, 1 H) 11.11 (s, 1 H) 8.48 (d, J = 7.6 Hz, 1 H) 8.18 (s, 1 H) 7.80 (d, J = 8.4 Hz, 1 H) 7.73 (d, J = 8.8 Hz, 2 H) 7.44 (d, J = 2.4 Hz, 1 H) 7.34 (dd, J = 8.4, 2.4 Hz, 1 H) 7.06-7.15 (m, 3 H) 6.45 (d, J = 2.4 Hz, 1 H) 5.11 (dd, J = 12.8, 5.2 Hz, 1 H) 4.27-4.33 (m, 2 H) 4.15-4.20 (m, 2 H) 3.76-3.81 (m, 4 H) 3.63 (s, 4 H) 3.14 (s, 7 H) 2.82-2.98 (m, 1 H) 2.55-2.62 (m, 1 H) 1.98-2.08 (m, 1 H) |
| 441 | 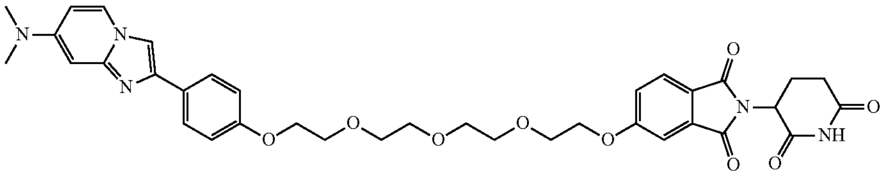 [SMILES: CN(C)c1ccn2cc(-c3ccc(OCCOCCOCCOCCOc4ccc5c(c4)C(=O)N(C4CCC(=O)NC4=O)C5=O)cc3)nc2c1] | 5-(2-(2-(2-(2-(4-(7-(dimethylamino)imidazo[1,2-a]pyridin-2-yl)phenoxy)ethoxy)ethoxy)ethoxy)ethoxy)-2-(2,6-dioxopiperidin-3-yl)isoindoline-1,3-dione | | 686.4 | $^1$H NMR (400 MHz, DMSO-$d_6$) δ: 13.40 (s, 1 H) 11.11 (s, 1 H) 8.47 (d, J = 7.6 Hz, 1 H) 8.17 (s, 1 H) 7.80 (d, J = 8.4 Hz, 1 H) 7.73 (d, J = 8.8 Hz, 2 H) 7.42 (d, J = 2.0 Hz, 1 H) 7.34 (dd, J = 8.4, 2.4 Hz, 1 H) 7.13 (d, J = 8.8 Hz, 2 H) 7.08 (dd, J = 7.6, 2.4 Hz, 1 H) 6.45 (d, J = 2.4 Hz, 1 H) 5.11 (dd, J = 12.8, 5.2 Hz, 1 H) 4.14-4.19 (m, 2 H) 3.75-3.80 (m, 5 H) 3.58-3.61 (m 5 H) 3.56 (d, J = 2.4 Hz, 4 H) 3.14 (s, 6 H) 2.81-2.94 (m, 1 H) 2.55-2.63 (m, 2 H) 1.98-2.08 (m, 1 H) |
| 442 | 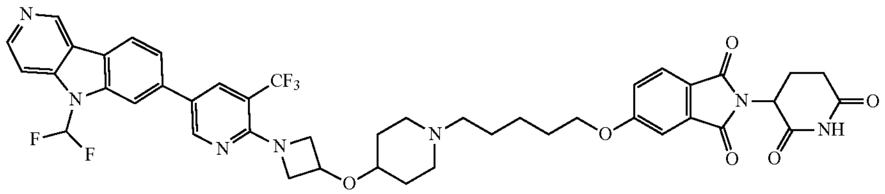 | 5-((5-(4-((1-(5-(5-(difluoromethyl)-5H-pyrido[4,3-b]indol-7-yl)-3-(trifluoromethyl)pyridin-2-yl)azetidin-3-yl)oxy)piperidin-1-yl)pentyl)oxy)-2-(2,6-dioxopiperidin-3-yl)isoindoline-1,3-dione | A | 860.4 | $^1$H NMR (400 MHz, DMSO-$d_6$) δ: 11.11 (s, 1H), 9.49 (s, 1H), 8.84 (d, J = 2.1 Hz, 1H), 8.62 (d, J = 5.6 Hz, 1H), 8.42-8.34 (m, 1H), 8.31-8.24 (m, 2H), 8.21 (s, 1H), 7.86-7.78 (m, 3H), 7.43 (d, J = 2.2 Hz, 1H), 7.39-7.31 (m, 1H), 5.18-5.03 (m, 1H), 4.61-4.50 (m, 1H), 4.47-4.38 (m, 2H), 4.18 (br t, J = 6.5 Hz, 2H), 4.03-3.94 (m, 2H), 2.95-2.86 (m, 1H), 2.78-2.69 (m, 2H), 2.65-2.54 (m, 3H), 2.28 (br t, J = 6.8 Hz, 2H), 2.10-1.96 (m, 3H), 1.87-1.72 (m, 5H), 1.50-1.43 (m, 4H), 1.29-1.08 (m, 2H) |

TABLE 1-continued

| | | | | | |
|---|---|---|---|---|---|
| 443 | 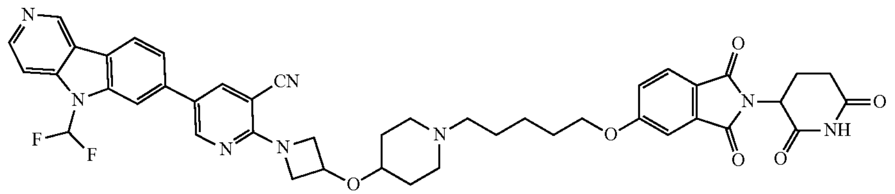 [SMILES: O=C1CCC(N2C(=O)c3ccc(OCCCCCN4CCC(OC5CN(c6ncc(-c7ccc8c9cnccc9n(C(F)F)c8c7)cc6C(F)(F)F)C5)CC4)cc3C2=O)C(=O)N1] | 5-(5-(difluoromethyl)-5H-pyrido[4,3-b]indol-7-yl)-2-(3-((1-(5-((2-(2,6-dioxopiperidin-3-yl)-1,3-dioxoisoindolin-5-yl)oxy)pentyl)piperidin-4-yl)oxy)azetidin-1-yl)nicotinonitrile | | 817.4 | $^1$H NMR (400 MHz, DMSO-$d_6$) δ: 11.10 (s, 1H), 9.47 (s, 1H), 8.81 (d, J = 2.4 Hz, 1H), 8.64-8.57 (m, 1H), 8.47-8.45 (m, 1H), 8.38 (d, J = 8.3 Hz, 1H), 8.25-8.17 (m, 2H), 7.87-7.75 (m, 3H), 7.42 (d, J = 2.1 Hz, 1H), 7.37-7.30 (m, 1H), 5.20-5.04 (m, 1H), 4.61-4.47 (m, 3H), 4.20-4.14 (m, 2H), 4.11-4.04 (m, 2H), 3.47-3.35 (m, 2H), 2.95-2.79 (m, 2H), 2.78-2.69 (m, 2H), 2.64-2.53 (m, 2H), 2.34-2.28 (m, 2H), 2.13-1.98 (m, 3H), 1.87-1.78 (m, 4H), 1.51-1.43 (m, 4H), 1.29-1.22 (m, 2H) |
| 444 | 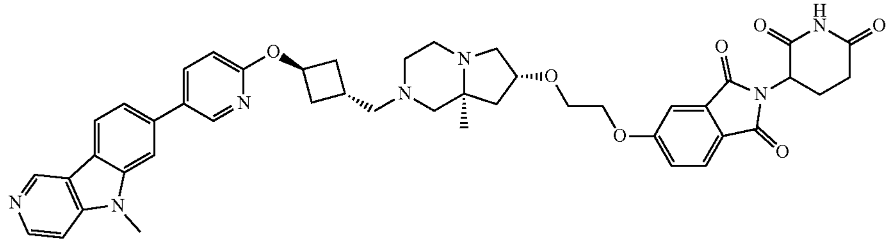 [SMILES: Cn1c2ccncc2c2ccc(-c3ccc(O[C@H]4C[C@H](CN5CCN6C[C@H](OCCOc7ccc8c(c7)C(=O)N(C7CCC(=O)NC7=O)C8=O)C[C@@]6(C)C5)C4)nc3)cc21] | 2-(2,6-dioxopiperidin-3-yl)-5-(2-(((7R,8aS)-2-(((1r,3S)-3-((5-(5-methyl-5H-pyrido[4,3-b]indol-7-yl)pyridin-2-yl)oxy)cyclobutyl)methyl)octahydro-pyrrolo[1,2-a]pyrazin-7-yl)oxy)ethoxy)isoindoline-1,3-dione | | 784.5 | $^1$H NMR (400 MHz, DMSO-$d_6$): δ 11.13 (s, 1H), 9.36 (s, 1H), 8.62 (s, 1H), 8.50 (m, 1H), 8.32-8.30 (m, 1H), 8.18 (m, 1H), 7.96 (m, 1H), 7.83-7.81 (m, 1H), 7.62 (m, 2H), 7.45 (m, 1H), 7.37-7.35 (m, 1H), 6.93-6.92 (m, 1H), 5.36-5.28 (m, 1H), 5.15-5.12 (m, 1H), 4.29 (m, 2H), 4.09 (m, 1H), 3.95 (s, 3H), 3.72 (m, 2H), 2.86-2.58 (m, 8H), 2.46 (m, 3H), 2.22-1.92 (m, 8H), 1.72-1.70 (m, 2H), 1.53-1.51 (m, 1H). |
| 445 | 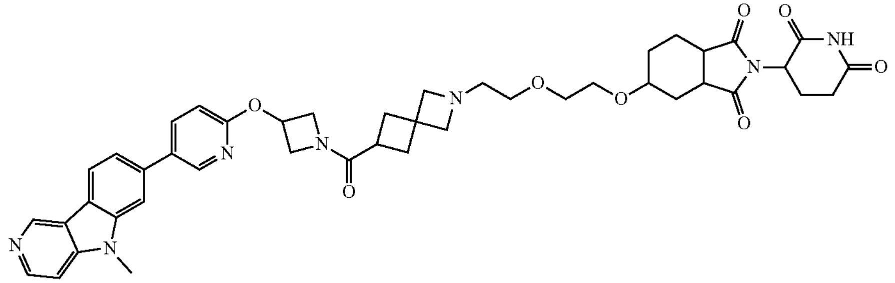 [SMILES: Cn1c2ccncc2c2ccc(-c3ccc(OC4CN(C(=O)C5CC6(C5)CN(CCOCCOC5CCC7C(=O)N(C8CCC(=O)NC8=O)C(=O)C7C5)C6)C4)nc3)cc21] | 2-(2,6-dioxopiperidin-3-yl)-5-(2-(2-(6-(3-((5-(5-methyl-5H-pyrido[4,3-b]indol-7-yl)pyridin-2-yl)oxy)azetidine-1-carbonyl)-2-azaspiro[3.3]heptan-2-yl)ethoxy)ethoxy)isoindoline-1,3-dione | | 798.4 | $^1$H NMR (400 MHz, CD3OD): δ 9.29 (s, 1H), 8.56-8.55 (m, 1H), 8.50-8.49 (m, 1H), 8.35-8.33 (m, 1H), 8.19-8.16 (m, 1H), 7.88-7.85 (m, 2H), 7.68-7.62 (m, 2H), 7.49 (s, 1H), 7.39-7.37 (m, 1H), 7.03-7.01 (m, 1H), 5.49 (m, 1H), 5.14-5.10 (m, 1H), 4.61 (m, 1H), 4.45 (m, 1H), 4.38-4.36 (m, 2H), 4.18 (m, 1H), 4.12 (m, 4H), 4.05-4.02 (m, 5H), 3.93-3.91 (m, 2H), 3.78-3.76 (m, 2H), 3.10 (m, 1H), 2.91-2.83 (m, 1H), 2.77 (m, 2H), 2.52-2.46 (m, 5H), 2.14-2.08 (m, 2H). |
| 446 | 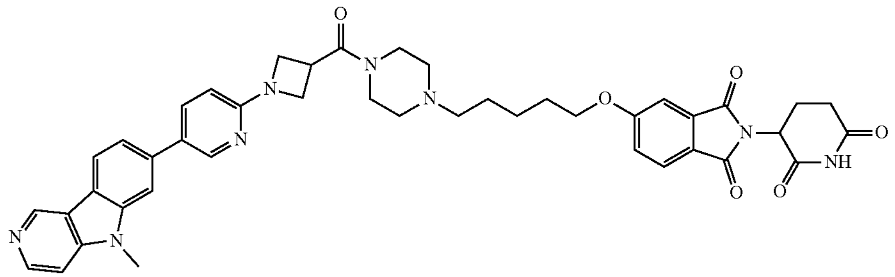 [SMILES: Cn1c2ccncc2c2ccc(-c3ccc(N4CC(C(=O)N5CCN(CCCCCOc6ccc7c(c6)C(=O)N(C6CCC(=O)NC6=O)C7=O)CC5)C4)nc3)cc21] | 2-(2,6-dioxopiperidin-3-yl)-5-((5-(4-(1-(5-(5-methyl-5H-pyrido[4,3-b]indol-7-yl)pyridin-2-yl)azetidine-3-carbonyl)piperazin-1-yl)pentyl)oxy)isoindoline-1,3-dione | B | 769.5 | $^1$H NMR (300 MHz, DMSO-$d_6$): δ 10.11 (s, 1H), 9.72 (s, 1H), 8.76 (s, 1H), 8.51 (s, 1H), 7.98-7.71 (m, 2H), 7.47 (s, 1H), 7.32 (s, 1H), 7.19 (s, 1H), 7.10 (s, 1H), 7.00 (s, 1H), 6.61 (s, 1H), 5.12 (s, 1H), 4.71-4.35 (m, 2H), 4.31-4.02 (m, 7H), 3.84-3.75 (m, 2H), 3.10-2.90 (m, 6H), 2.08 (s, 1H), 1.82-1.71 (m, 4H), 1.24-1.21 (m, 9H) |

TABLE 1-continued

| | | | | | |
|---|---|---|---|---|---|
| 447 | 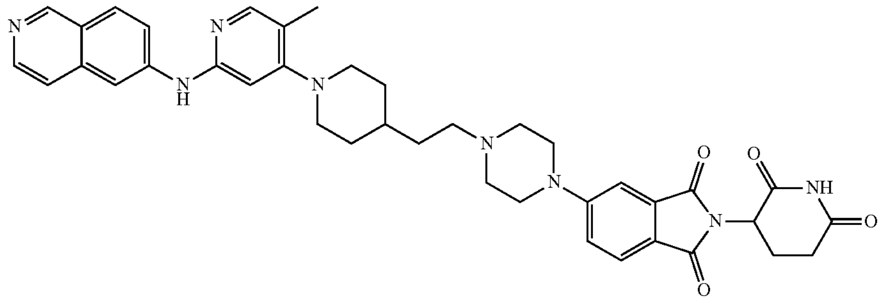 [SMILES: Cc1cnc(Nc2ccc3cnccc3c2)cc1N1CCC(CCN2CCN(c3ccc4c(c3)C(=O)N(C3CCC(=O)NC3=O)C4=O)CC2)CC1] | 2-(2,6-dioxopiperidin-3-yl)-5-(4-(2-(1-(2-(isoquinolin-6-ylamino)-5-methylpyridin-4-yl)piperidin-4-yl)ethyl)piperazin-1-yl)isoindoline-1,3-dione | A | 687.4 | 1H NMR (300 MHz, DMSO-d6): δ 9.35 (s, 1H), 9.03 (s, 1H), 8.46 (s, 1H), 8.30 (m, 1H), 8.16-8.13 (s, 1H), 7.96-7.92 (m, 2H), 7.78-7.75 (m, 1H), 7.67-7.58 (m, 2H), 7.47 (s, 1H), 7.36-7.33 (m, 1H), 6.51 (s, 1H), 5.23-5.17 (m, 1H), 3.74 (m, 2H), 3.66 (m, 4H), 3.52 (m, 1H), 3.37-3.22 (m, 5H), 3.07-2.96 (m, 1H), 2.87-2.75 (m, 1H), 2.63-2.52 (m, 3H), 2.28 (s, 3H), 2.14-2.07 (m, 1H), 1.85-1.82 (m, 2H), 1.46 (m, 3H), 1.37-1.30 (m, 2H). |
| 448 | 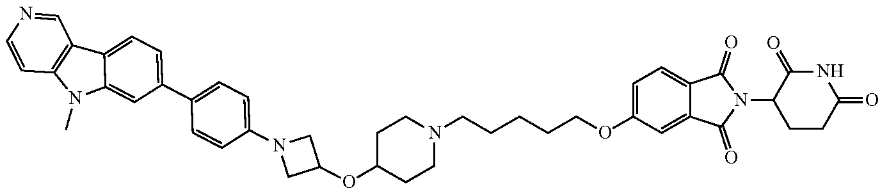 [SMILES: Cn1c2ccncc2c2ccc(-c3ccc(N4CC(OC5CCN(CCCCCOc6ccc7c(c6)C(=O)N(C6CCC(=O)NC6=O)C7=O)CC5)C4)cc3)cc21] | 2-(2,6-dioxopiperidin-3-yl)-5-((5-(4-((1-(4-(5-methyl-5H-pyrido[4,3-b]indol-7-yl)phenyl)azetidin-3-yl)oxy)piperidin-1-yl)pentyl)oxy) isoindoline-1,3-dione | | 755.5 | 1H NMR (400 MHz, DMSO-d6): δ 11.11 (s, 1H), 9.32 (s, 1H), 8.48-8.47 (m, 1H), 8.25 (m, 1H), 7.85-7.83 (m, 2H), 7.70-7.68 (m, 2H), 7.64-7.53 (m, 2H), 7.43 (s, 1H), 7.35 (m, 1H), 6.59-6.53 (m, 2H), 5.14 (m, 1H), 4.63-4.54 (m, 1H), 4.19-4.17 (m, 3H), 3.95 (s, 3H), 3.62-3.59 (m, 2H), 3.45 (m, 1H), 2.94-2.67 (m, 3H), 2.34-2.27 (m, 2H), 2.11-1.95 (m, 4H), 1.85-1.72 (m, 3H), 1.47-1.44 (m, 6H), 1.24 (m, 3H). |
| 449 | 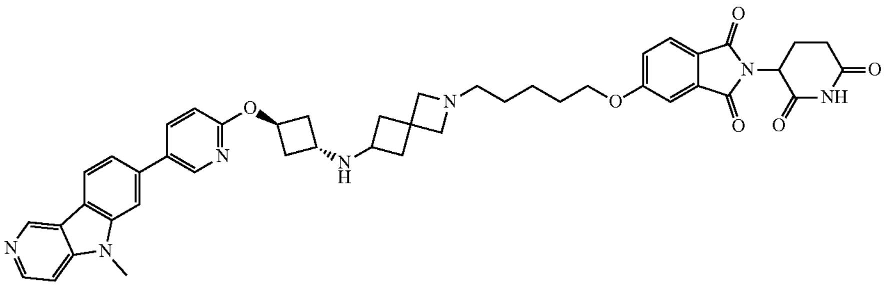 [SMILES: Cn1c2ccncc2c2ccc(-c3ccc(O[C@H]4C[C@H](NC5CC6(C5)CN(CCCCCOc5ccc7c(c5)C(=O)N(C5CCC(=O)NC5=O)C7=O)C6)C4)nc3)cc21] | 2-(2,6-dioxopiperidin-3-yl)-5-((5-(6-(((1r,3r)-3-((5-(5-methyl-5H-pyrido[4,3-b]indol-7-yl)pyridin-2-yl)oxy)cyclobutyl) amino)-2-azaspiro[3.3] heptan-2-yl)pentyl)oxy) isoindoline-1,3-dione | | 782.5 | $^1$H NMR (400 MHz, DMSO-$d_6$) δ: 11.30-10.93 (m, 1H), 9.36 (s, 1H), 8.62 (d, J = 2.4 Hz, 1H), 8.49 (d, J = 5.8 Hz, 1H), 8.32 (d, J = 8.1 Hz, 1H), 8.25 (s, 2H), 8.21-8.15 (m, 1H), 7.97 (s, 1H), 7.83 (d, J = 8.4 Hz, 1H), 7.67-7.58 (m, 2H), 7.42 (d, J = 2.1 Hz, 1H), 7.37-7.32 (m, 1H), 6.92 (d, J = 8.5 Hz, 1H), 5.45-5.26 (m, 1H), 5.16-5.07 (m, 1H), 4.16 (br t, J = 6.4 Hz, 2H), 3.96 (s, 3H), 3.39-3.32 (m, 3H), 3.29-3.22 (m, 2H), 3.10-3.02 (m, 1H), 2.95-2.86 (m, 1H), 2.62-2.51 (m, 5H), 2.30-2.19 (m, 5H), 2.07-2.02 (m, 1H), 1.89-1.81 (m, 2H), 1.78-1.68 (m, 2H), 1.50-1.29 (m, 4H) |
| 450 | 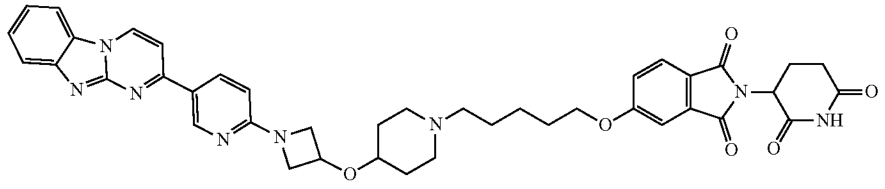 [SMILES: O=C1CCC(N2C(=O)c3ccc(OCCCCCN4CCC(OC5CN(c6ccc(-c7ccn8c(n7)nc7ccccc78)cn6)C5)CC4)cc3C2=O)C(=O)N1] | 5-((5-(4-((1-(5-(benzo[4,5]imidazo[1,2-a]pyrimidin-2-yl) pyridin-2-yl)azetidin-3-yl)oxy)piperidin-1-yl)pentyl)oxy)-2-(2,6-dioxopiperidin-3-yl)isoindoline-1,3-dione | A | 743.4 | $^1$H NMR (400 MHz, DMSO-$d_6$) δ: 11.11 (s, 1H), 9.45 (d, J = 7.2 Hz, 1H), 9.06 (d, J = 2.4 Hz, 1H), 8.45 (dd, J = 2.4, 8.8 Hz, 1H), 8.27 (d, J = 8.0 Hz, 1H), 8.21 (s, 1H), 7.83 (d, J = 8.4 Hz, 1H), 7.79 (d, J = 8.4 Hz, 1H), 7.73 (d, J = 7.2 Hz, 1H), 7.54-7.48 (m, 1H), 7.43 (d, J = 2.0 Hz, 1H), 7.41-7.33 (m, 2H), 6.56 (d, J = 8.0 Hz, 1H), 5.12 (dd, J = 5.6, 12.8 Hz, 1H), 4.65-4.58 (m, 1H), 4.34 (dd, J = 6.4, 9.2 Hz, 2H), 4.18 (t, J = 6.4 Hz, 2H), 3.89 (dd, J = 4.4, 9.6 Hz, 2H), 2.95-2.84 (m, 2H), 2.76-2.71 (m, 2H), 2.63-2.61 (m, 2H), 2.29 (t, J = 6.4 Hz, 2H), |

TABLE 1-continued

| | | | | |
|---|---|---|---|---|
| | | | | 2.09-1.99 (m, 3H), 1.87-1.74 (m, 4H), 1.53-1.40 (m, 6H). |
| 451 | 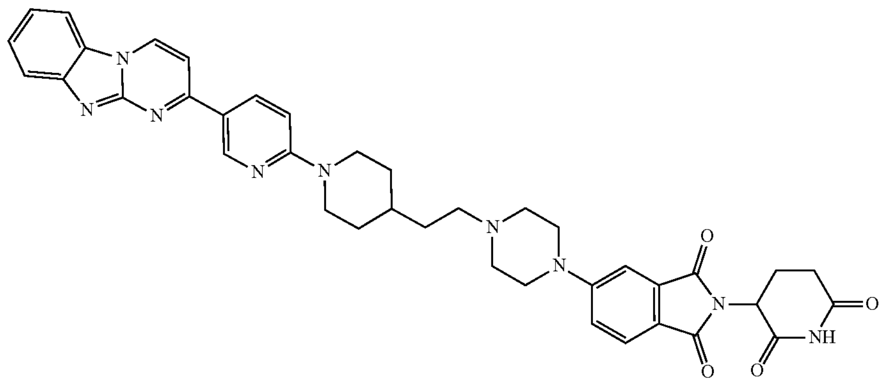 [SMILES: O=C1CCC(N2C(=O)c3ccc(N4CCN(CCC5CCN(c6ccc(-c7ccn8c(n7)nc7ccccc78)cn6)CC5)CC4)cc3C2=O)C(=O)N1] | 5-(4-(2-(1-(5-(benzo[4,5]imidazo[1,2-a]pyrimidin-2-yl)pyridin-2-yl)piperidin-4-yl)ethyl)piperazin-1-yl)-2-(2,6-dioxopiperidin-3-yl)isoindoline-1,3-dione | 698.4 | 1H NMR (400 MHz, DMSO-d6) δ: 1.14-1.24 (m, 2 H), 1.46 (m, 2 H), 1.67 (m, 1 H), 1.81 (d, J = 14.0 Hz, 2 H), 2.04 (s, 2 H), 2.22-2.34 (m, 2 H), 2.37-2.41 (m, 1 H), 2.40 (s, 2 H), 2.87-3.03 (m, 4 H), 3.44-3.46 (m, 1 H), 4.50 (d, J = 12.0 Hz, 2 H), 5.07 (d, J = 12.8 Hz, 1 H), 7.02 (d, = 8.8 Hz, 1 H), 7.26 (d, J = 8.4 Hz, 1 H), 7.36 (d, J = 12.4 Hz, 2 H), 7.50 (t, J = 7.6 Hz, 1 H), 7.69 (s, 1 H), 7.73 (d, J = 7.2 Hz, 1 H), 7.78 (d, J = 8.0 Hz, 1 H), 8.26 (d, J = 8.4 Hz, 1 H), 8.36 (s, 2 H), 8.43 (d, J = 9.6 Hz, 1 H), 9.08 (s, 1 H), 9.43 (d, J = 7.2 Hz, 1 H), 11.08 (s, 1 H) |
| 452 | 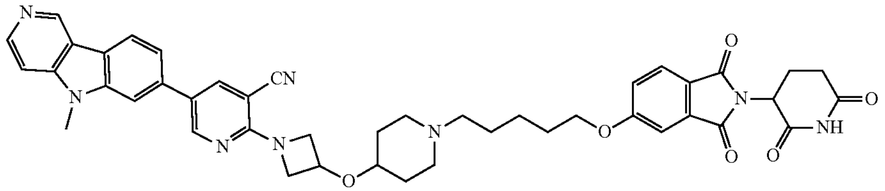 [SMILES: Cn1c2ccncc2c2ccc(-c3cnc(N4CC(OC5CCN(CCCCCOc6ccc7c(c6)C(=O)N(C6CCC(=O)NC6=O)C7=O)CC5)C4)c(C#N)c3)cc21] | 2-(3-((1-(5-((2-(2,6-dioxopiperidin-3-yl)-1,3-dioxoisoindolin-5-yl)oxy)pentyl)piperidin-4-yl)oxy)azetidin-1-yl)-5-(5-methyl-5H-pyrido[4,3-b]indol-7-yl)nicotinonitrile | 781.5 | $^1$H NMR (400 MHz, DMSO-$d_6$) δ: 11.11 (s, 1H), 9.35 (s, 1H), 8.86 (d, J = 1.8 Hz, 1H), 8.56-8.44 (m, 2H), 8.30 (br d, J = 7.9 Hz, 1H), 8.24 (s, 1H), 8.02 (s, 1H), 7.83 (d, J = 8.2 Hz, 1H), 7.68-7.58 (m, 2H), 7.42 (s, 1H), 7.35 (d, J = 8.1 Hz, 1H), 5.21-5.03 (m, 1H), 4.62-4.49 (m, 3H), 4.17 (br t, J = 6.4 Hz, 2H), 4.10-4.03 (m, 2H), 3.95 (s, 3H), 2.92-2.84 (m, 1H), 2.57 (br s, 6H), 2.35-2.26 (m, 3H), 2.09-2.01 (m, 3H), 1.88-1.74 (m, 4H), 1.53-1.37 (m, 6H) |
| 453 | 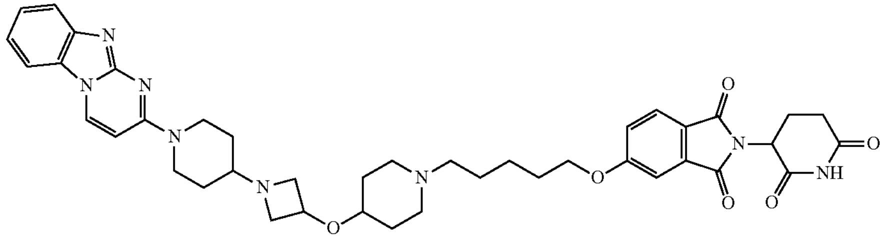 [SMILES: O=C1CCC(N2C(=O)c3ccc(OCCCCCN4CCC(OC5CN(C6CCN(c7ccn8c(n7)nc7ccccc78)CC6)C5)CC4)cc3C2=O)C(=O)N1] | 5-((5-(4-((1-(1-(benzo[4,5]imidazo[1,2-a]pyrimidin-2-yl)piperidin-4-yl)azetidin-3-yl)oxy)piperidin-1-yl)pentyl)oxy)-2-(2,6-dioxopiperidin-3-yl)isoindoline-1,3-dione | 749.5 | $^1$H NMR (400 MHz, DMSO-$d_6$): δ 11.11 (s, 1H), 10.01-9.59 (m, 1H), 9.30 (d, J = 8.0 Hz, 1H), 8.22 (d, J = 8.0 Hz, 1H), 7.85 (d, J = 8.4 Hz, 1H), 7.67-7.62 (m, 1H), 7.61-7.55 (m, 1H), 7.53-7.47 (m, 1H), 7.45-7.40 (m, 2H), 7.35 (m, J = 2.0, 8.4 Hz, 1H), 5.12 (m, J = 5.2, 12.8 Hz, 1H), 5.02-4.88 (m, 1H), 4.61-4.37 (m, 4H), 4.20 (t, J = 6.0 Hz, 2H), 4.10 (s, 2H), 3.56-3.34 (m, 4H), 3.09 (s, 4H), 2.96-2.84 (m, 2H), 2.66-2.54 (m, 2H), 2.25-2.05 (m, 4H), 2.00-1.56 (m, 8H), 1.47 (d, J = 6.8 Hz, 4H). |

TABLE 1-continued

| | | | | | |
|---|---|---|---|---|---|
| 454 | 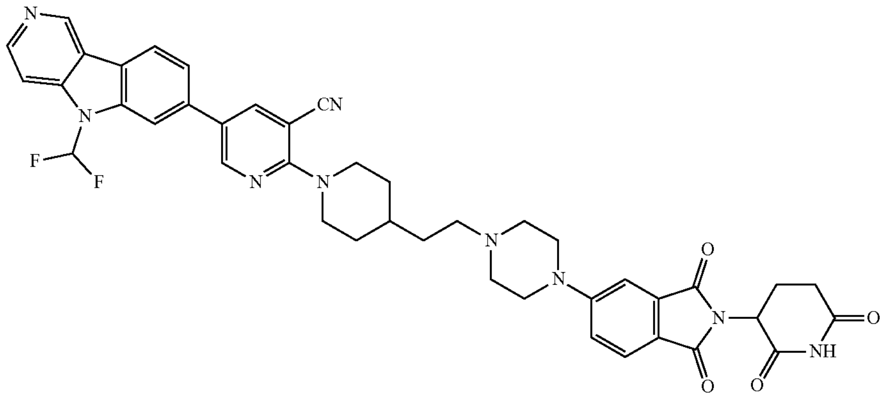 [SMILES: N#Cc1cc(-c2ccc3c4cnccc4n(C(F)F)c3c2)cnc1N1CCC(CCN2CCN(c3ccc4c(c3)C(=O)N(C3CCC(=O)NC3=O)C4=O)CC2)CC1] | 5-(5-(difluoromethyl)-5H-pyrido[4,3-b]indol-7-yl)-2-(4-(2-(4-(2-(2,6-dioxopiperidin-3-yl)-1,3-dioxoisoindolin-5-yl)piperazin-1-yl)ethyl)piperidin-1-yl)nicotinonitrile | A | 772.4 | $^1$H NMR (400 MHz, DMSO-$d_6$) δ: 11.09 (s, 1H), 9.76 (s, 1H), 8.91 (d, J = 2.6 Hz, 1H), 8.81 (d, J = 6.4 Hz, 1H), 8.60-8.57 (m, 1H), 8.52 (d, J = 8.2 Hz, 1H), 8.33 (s, 1H), 8.17 (d, J = 6.2 Hz, 1H), 8.01-7.91 (m, 1H), 7.77 (d, J = 8.4 Hz, 1H), 7.50 (d, J = 1.8 Hz, 1H), 7.41-7.32 (m, 1H), 5.18-5.02 (m, 1H), 4.45-4.37 (m, 2H), 4.31-4.14 (m, 2H), 3.25-3.06 (m, 10H), 2.97-2.80 (m, 2H), 2.64-2.53 (m, 3H), 2.07-1.97 (m, 1H), 1.86 (br d, J = 11.1 Hz, 2H), 1.73-1.68 (m, 2H), 1.33 (br d, J = 10.3 Hz, 2H) |
| 455 | 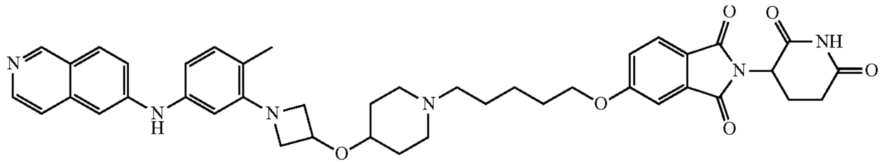 [SMILES: Cc1ccc(Nc2ccc3cnccc3c2)cc1N1CC(OC2CCN(CCCCCOc3ccc4c(c3)C(=O)N(C3CCC(=O)NC3=O)C4=O)CC2)C1] | 2-(2,6-dioxopiperidin-3-yl)-5-((5-(4-((1-(2-(isoquinolin-6-ylamino)-5-methylpyridin-4-yl)azetidin-3-yl)oxy)piperidin-1-yl)pentyl)oxy) isoindoline-1,3-dione | | 732.5 | 1H NMR (400 MHz, DMSO-d6): δ 11.11 (s, 1H), 9.20 (s, 1H), 9.00 (s, 1H), 8.42 (s, 1H), 8.29-8.28 (d, 1H), 7.91-7.89 (m, 1H), 7.85-7.83 (m, 1H), 7.73 (s, 1H), 7.64-7.61 (m, 1H), 7.56-7.55 (m, 1H), 7.43 (s, 1H), 7.36-7.34 (m, 1H), 5.90 (s, 1H), 5.11 (m, 1H), 4.51 (m, 1H), 4.30-4.27 (m, 2H), 4.20-4.16 (m, 2H), 3.80-3.77 (m, 2H), 2.91-2.82 (m, 1H), 2.72-2.68 (m, ,2H), 2.28-2.25 (m, 2H), 2.11-2.03 (m, 5H), 1.85-1.71 (m, 5H), 1.49-1.38 (m, 7H), 1.24 (s, 1H), 0.85 (s, 1H). |
| 456 | 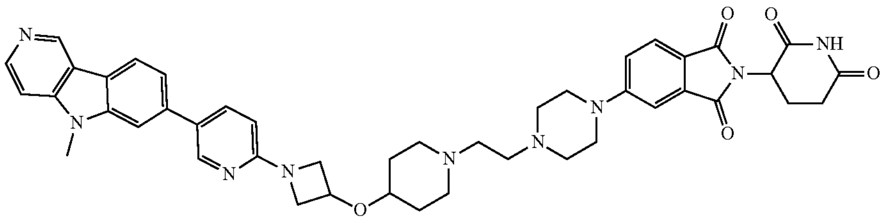 [SMILES: Cn1c2ccncc2c2ccc(-c3ccc(N4CC(OC5CCN(CCN6CCN(c7ccc8c(c7)C(=O)N(C7CCC(=O)NC7=O)C8=O)CC6)CC5)C4)nc3)cc21] | 2-(2,6-dioxopiperidin-3-yl)-5-(4-(2-(4-((1-(5-(5-methyl-5H-pyrido[4,3-b]indol-7-yl)pyridin-2-yl)azetidin-3-yl)oxy)piperidin-1-yl)ethyl)piperazin-1-yl)isoindoline-1,3-dione | | 782.5 | 1H NMR (300 MHz, DMSO-d6) δ 11.09 (s, 1H), 9.42 (s, 1H), 8.62-8.53 (m, 2H), 8.35-8.32 (m, 1H), 8.15 (s, 1H), 8.08-8.04 (m, 1H), 7.95 (s, 1H), 7.73-7.69 (m, 2H), 7.64-7.61 (m, 1H), 7.39-7.28 (m, 2H), 6.58-6.56 (m, 1H), 5.12-5.07 (m, 1H), 4.64 (m, 1H), 4.32-4.26 (m, 2H), 4.00 (s, 3H), 3.87-3.83 (m, 3H), 3.49-3.40 (m, 6H), 3.18-3.02 (m, 5H), 2.96-2.84 (m, 1H), 2.73-2.71 (m, 3H), 2.64-2.52 (m, 3H), 2.04-2.01 (m, 3H), 1.79 (m, 2H). |

TABLE 1-continued

| | | | | | |
|---|---|---|---|---|---|
| 457 | 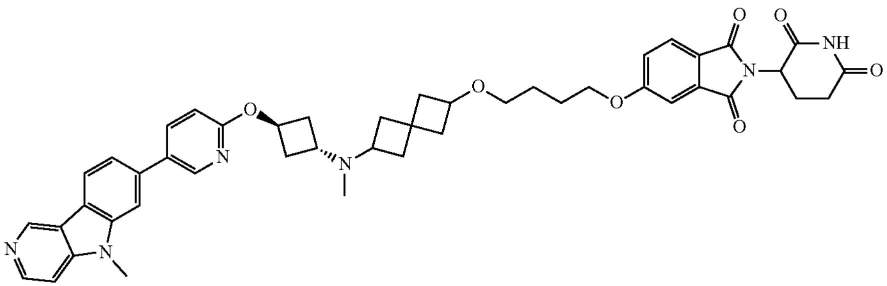 [SMILES: Cn1c2ccncc2c2ccc(-c3ccc(O[C@H]4C[C@H](N(C)C5CC6(CC(OCCCCOc7ccc8c(c7)C(=O)N(C7CCC(=O)NC7=O)C8=O)C6)C5)C4)nc3)cc21] | 2-(2,6-dioxopiperidin-3-yl)-5-(4-((6-(methyl((1r,3r)-3-((5-(5-methyl-5H-pyrido[4,3-b]indol-7-yl)pyridin-2-yl)oxy)cyclobutyl)amino)spiro[3.3]heptan-2-yl)oxy)butoxy)isoindoline-1,3-dione | | 797.5 | $^1$H NMR (400 MHz, DMSO-d6) δ: 11.13 (s, 1H), 10.71-10.12 (m, 1H), 9.69 (br s, 1H), 8.73-8.69 (m, 2H), 8.51 (d, J = 8.0 Hz, 1H), 8.33-8.24 (m, 1H), 8.18 (s, 1H), 8.08 (br d, J = 6.4 Hz, 1H), 7.88-7.77 (m, 2H), 7.42 (d, J = 2.0 Hz, 1H), 7.35 (dd, J = 2.4, 8.3 Hz, 1H), 7.06-6.97 (m, 1H), 5.28 (br t, J = 6.8 Hz, 1H), 5.12 (dd, J = 5.6, 12.9 Hz, 1H), 4.47 (br s, 1H), 4.19 (br t, J = 6.4 Hz, 2H), 4.11 (s, 3H), 3.98 (br d, J = 7.6 Hz, 1H), 3.90-3.79 (m, 1H), 3.68-3.55 (m, 1H), 2.98-2.70 (m, 5H), 2.64-2.54 (m, 6H), 2.31-2.16 (m, 6H), 2.10-2.00 (m, 1H), 1.91-1.86 (m, 2H), 1.81-1.75 (m, 2H), 1.66-1.59 (m, 2H). |
| 458 | 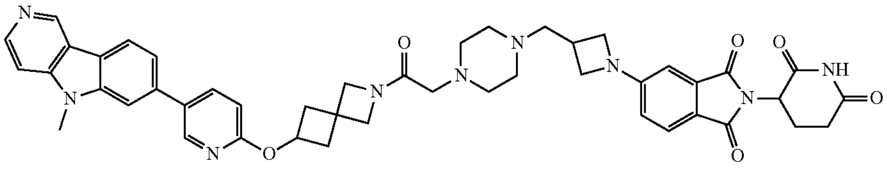 | 2-(2,6-dioxopiperidin-3-yl)-5-(3-((4-(2-(6-((5-(5-methyl-5H-pyrido[4,3-b]indol-7-yl)pyridin-2-yl)oxy)-2-azaspiro[3.3]heptan-2-yl)-2-oxoethyl)piperazin-1-yl)methyl)azetidin-1-yl)isoindoline-1,3-dione | B | 822.5 | 1H NMR (400 MHz, DMSO-d6): δ 11.05 (s, 1H), 9.35 (s, 1H), 8.62-8.49 (m, 2H), 8.40-8.18 (m, 2H), 7.97 (s, 1H), 7.61-7.51 (m, 3H), 7.00-6.85 (m, 1H), 6.82-6.57 (m, 2H), 5.19-5.03 (m, 2H), 4.39-3.87 (m, 10H), 3.66 (m, 2H), 3.08-2.84 (m, 5H), 2.74 (m, 3H), 2.49-2.10 (m, 11H), 2.06-1.88 (m, 1H). |
| 459 | 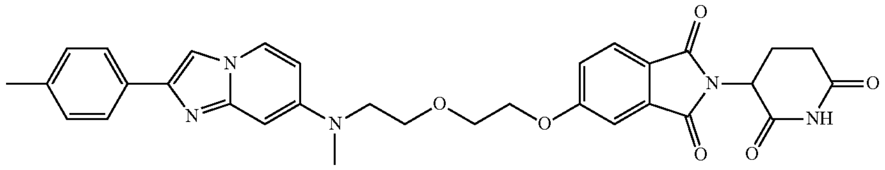 [SMILES: Cc1ccc(-c2cn3ccc(N(C)CCOCCOc4ccc5c(c4)C(=O)N(C4CCC(=O)NC4=O)C5=O)cc3n2)cc1] | 2-(2,6-dioxopiperidin-3-yl)-5-(2-(2-(methyl(2-(p-tolyl)imidazo[1,2-a]pyridin-7-yl)amino)ethoxy)ethoxy)isoindoline-1,3-dione | | | $^1$H NMR (400 MHz, DMSO-$d_6$) δ: 11.21-11.00 (m, 1 H), 8.20 (s, 1 H), 8.17 (d, J = 7.6 Hz, 1 H), 7.94-7.89 (m, 1 H), 7.84-7.67 (m, 3 H), 7.42 (d, J = 2.00 Hz, 1 H), 7.31 (m, 1 H), 7.23-7.17 (m, 2 H), 6.66 (m, 1 H), 6.39 (d, J = 2.40 Hz, 1 H), 5.10 (m, 1 H), 4.31-4.25 (m, 2 H), 3.80-3.77 (m, 2 H), 3.69-3.66 (m, 2 H), 3.59 (d, J = 5.20 Hz, 2 H), 2.97 (s, 3 H), 2.92-2.83 (m, 1 H), 2.62-2.53 (m, 2 H), 2.32-2.29 (m, 3 H), 2.05-1.96 (m, 1 H). |
| 460 | 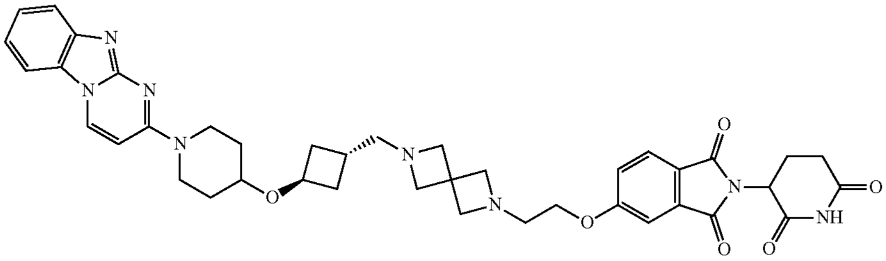 [SMILES: O=C1CCC(N2C(=O)c3ccc(OCCN4CC5(C4)CN(C[C@H]4C[C@H](OC6CCN(c7ccn8c(n7)nc7ccccc78)CC6)C4)C5)cc3C2=O)C(=O)N1] | 5-(2-(6-(((1r,3r)-3-((1-(benzo[4,5]imidazo[1,2-a]pyrimidin-2-yl)piperidin-4-yl)oxy)cyclobutyl)methyl)-2,6-diazaspiro[3.3]heptan-2-yl)ethoxy)-2-(2,6-dioxopiperidin-3-yl)isoindoline-1,3-dione | B | 733.5 | $^1$H NMR (400 MHz, DMSO-$d_6$) δ: 11.11 (s, 1H), 10.88-10.15 (m, 2H), 9.24 (d, J = 8.0 Hz, 1H), 8.20 (d, J = 8.0 Hz, 1H), 7.90 (d, J = 8.4 Hz, 1H), 7.65-7.59 (m, 1H), 7.58-7.53 (m, 1H), 7.51-7.46 (m, 2H), 7.40-7.35 (m, 2H), 5.13 (dd, J = 5.2, 12.8 Hz, 1H), 4.41 (s, 4H), 4.33 (s, 3H), 4.29 (s, 2H), 4.25-4.16 (m, 2H), 4.12-3.94 (m, 2H), 3.67 (d, J = 3.2 Hz, 5H), 3.29-3.15 (m, 2H), 2.96-2.82 (m, 1H), 2.65-2.54 (m, 2H), 2.36 (d, J = 7.2 Hz, 1H), 2.10-2.01 (m, 2H), 2.00-1.87 (m, 3H), 1.70-1.59 (m, 2H), 1.58-1.47 (m, 2H) |

TABLE 1-continued

| | | | | | |
|---|---|---|---|---|---|
| 461 | 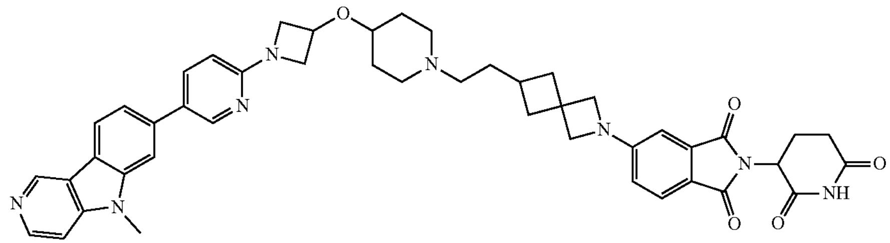 [SMILES: Cn1c2ccncc2c2ccc(-c3ccc(N4CC(OC5CCN(CCC6CC7(C6)CN(c6ccc8c(c6)C(=O)N(C6CCC(=O)NC6=O)C8=O)C7)CC5)C4)nc3)cc21] | 2-(2,6-dioxopiperidin-3-yl)-5-(6-(2-(4-((1-(5-(5-methyl-5H-pyrido[4,3-b]indol-7-yl)pyridin-2-yl)azetidin-3-yl)oxy)piperidin-1-yl)ethyl)-2-azaspiro[3.3]heptan-2-yl)isoindoline-1,3-dione | | 793.5 | 1H NMR (300 MHz, DMSO-d6): δ 11.08 (s, 1H), 9.36 (s, 1H), 8.61-8.60 (s, 1H), 8.51-8.49 (m, 1H), 8.32-8.29 (m, 1H), 8.17 (m, 1H), 8.07-8.03 (m, 1H), 7.92 (m, 1H), 7.66-7.58 (m, 3H), 6.77 (m, 1H), 6.65-6.55 (m, 2H), 5.06 (m, 1H), 4.65-4.51 (m, 1H), 4.30-4.25 (m, 2H), 4.07 (m, 2H), 3.97 (m, 5H), 3.84-3.80 (m, 3H), 2.89-2.86 (m, 3H), 2.62-2.56 (m, 2H), 2.39-2.29 (m, 4H), 2.21-2.10 (m, 2H), 2.09-1.98 (m, 1H), 1.93-1.88 (m, 4H), 1.61-1.58 (m, 4H). |
| 462 | 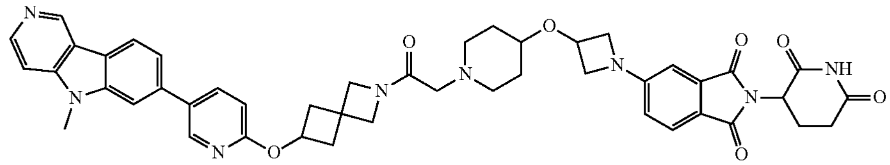 [SMILES: Cn1c2ccncc2c2ccc(-c3ccc(OC4CC5(C4)CN(C(=O)CN4CCC(OC6CN(c7ccc8c(c7)C(=O)N(C7CCC(=O)NC7=O)C8=O)C6)CC4)C5)nc3)cc21] | 2-(2,6-dioxopiperidin-3-yl)-5-(3-((1-(2-(6-((5-(5-methyl-5H-pyrido[4,3-b]indol-7-yl)pyridin-2-yl)oxy)-2-azaspiro[3.3]heptan-2-yl)-2-oxoethyl)piperidin-4-yl)oxy)azetidin-1-yl)isoindoline-1,3-dione | B | 823.5 | 1H NMR (400 MHz, DMSO-d6): δ 11.06 (s, 1H), 9.36 (s, 1H), 8.63 (m, 1H), 8.51-8.49 (m, 1H), 8.33-8.31 (m, 1H), 8.20-8.18 (m, 1H), 7.97 (s, 1H), 7.65-7.61 (m, 3H), 6.94-6.92 (m, 1H), 6.80 (s, 1H), 6.66-6.54 (m, 1H), 5.15-5.04 (m, 2H), 4.60-4.59 (m, 1H), 4.30-4.21 (m, 4H), 3.96 (s, 4H), 3.88-3.82 (m, 3H), 3.39 (m, 1H), 2.96-2.84 (m, 3H), 2.75-2.61 (m, 4H), 2.56-2.55 (m, 2H), 2.36-2.32 (m, 2H), 2.19-2.11 (m, 2H), 2.07-1.96 (m, 1H), 1.87-1.74 (m, 2H), 1.55-1.41 (m, 2H). |
| 463 | 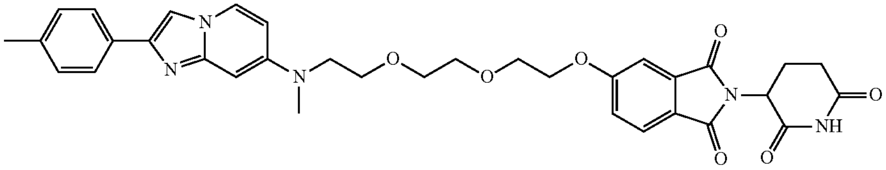 [SMILES: Cc1ccc(-c2cn3ccc(N(C)CCOCCOCCOc4ccc5c(c4)C(=O)N(C4CCC(=O)NC4=O)C5=O)cc3n2)cc1] | 2-(2,6-dioxopiperidin-3-yl)-5-(2-(2-(2-(methyl(2-(p-tolyl)imidazo[1,2-a]pyridin-7-yl)amino)ethoxy)ethoxy)ethoxy)isoindoline-1,3-dione | A | 626.4 | $^1$H NMR (400 MHz, DMSO-$d_6$) δ: 13.51-13.32 (m, 1 H), 11.11 (s, 1 H), 8.44 (d, J = 7.6 Hz, 1 H), 8.21 (s, 1 H), 7.76 (d, J = 8.4 Hz, 1 H), 7.66 (d, J = 8.0 Hz, 2 H), 7.39-7.33 (m, 3 H), 7.28 (dd, J = 8.4, 2.4 Hz, 1 H), 7.14 (dd, J = 7.6, 2.4 Hz, 1 H), 6.50 (d, J = 3.6 Hz, 1 H), 5.10 (dd, J = 12.8, 5.2 Hz, 1 H), 4.25-4.19 (m, 2 H), 3.73-3.58 (m, 10 H), 3.12 (s, 3 H), 2.95-2.83 (m, 1 H), 2.63-2.53 (m, 2 H), 2.36 (s, 3 H), 2.08-1.94 (m, 1 H). |
| 464 | 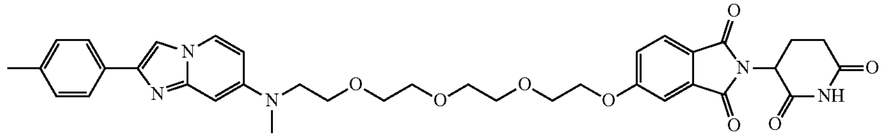 [SMILES: Cc1ccc(-c2cn3ccc(N(C)CCOCCOCCOCCOc4ccc5c(c4)C(=O)N(C4CCC(=O)NC4=O)C5=O)cc3n2)cc1] | 2-(2,6-dioxopiperidin-3-yl)-5-((2-(2-(p-tolyl)imidazo[1,2-a]pyridin-7-yl)-5,8,11-trioxa-2-azatridecan-13-yl)oxy)isoindoline-1,3-dione | | 670.4 | $^1$H NMR (400 MHz, DMSO-$d_6$) δ: 13.42 (s, 1 H), 11.10 (s, 1 H), 8.44 (d, J = 7.6 Hz, 1 H), 8.22 (s, 1 H), 7.78 (d, J = 8.4 Hz, 1 H), 7.68 (d, J = 8.8 Hz, 2 H), 7.39-7.32 (m, 4 H), 7.13 (d J = 8.8 Hz, 1 H), 6.48 (d, J = 2.4 Hz, 1 H), 5.11 (d, J = 4.4 Hz, 1 H), 4.25 (d, J = 4.4 Hz, 1 H), 3.72 (s, 4 H), 3.53-3.52 (m, 2 H), 3.50-3.49 (m, 8 H), 3.11 (s, 3 H), 2.94-2.91 (m, 1 H), 2.49 (s, 3 H), 2.02-1.98 (m, 1 H). |

TABLE 1-continued

| | | | | | |
|---|---|---|---|---|---|
| 465 | 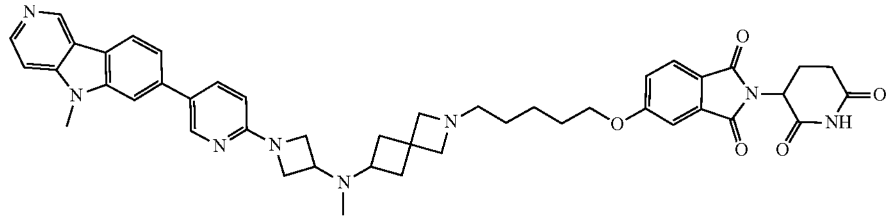 [SMILES: CN(C1CN(c2ccc(-c3ccc4c5cnccc5n(C)c4c3)cn2)C1)C1CC2(C1)CN(CCCCCOc1ccc3c(c1)C(=O)N(C1CCC(=O)NC1=O)C3=O)C2] | 2-(2,6-dioxopiperidin-3-yl)-5-((5-(6-(methyl(1-(5-(5-methyl-5H-pyrido[4,3-b]indol-7-yl)pyridin-2-yl)azetidin-3-yl)amino)-2-azaspiro[3.3]heptan-2-yl)pentyl)oxy)isoindoline-1,3-dione | | 781.5 | $^1$H NMR (400 MHz, DMSO-$d_6$) δ: 11.10 (s, 1H), 10.28-10.12 (m, 1H), 9.75 (s, 1H), 8.76 (d, J = 6.8 Hz, 1H), 8.70 (d, J = 2.2 Hz, 1H), 8.52 (d, J = 8.3 Hz, 1H), 8.29-8.10 (m, 3H), 7.85 (d, J = 8.3 Hz, 2H), 7.43 (d, J = 2.2 Hz, 1H), 7.38-7.30 (m, 1H), 6.68 (d, J = 8.7 Hz, 1H), 5.18-5.08 (m, 1H), 4.26 (s, 4H), 4.21-4.16 (m, 5H), 4.14 (s, 3H), 4.12-4.05 (m, 4H), 3.75-3.68 (m, 1H), 3.22-3.08 (m, 2H), 2.98-2.81 (m, 1H), 2.78-2.67 (m, 3H), 2.55 (s, 4H), 2.11-2.00 (m, 1H), 1.78 (t, J = 6.8 Hz, 2H), 1.57-1.41 (m, 4H) |
| 466 | 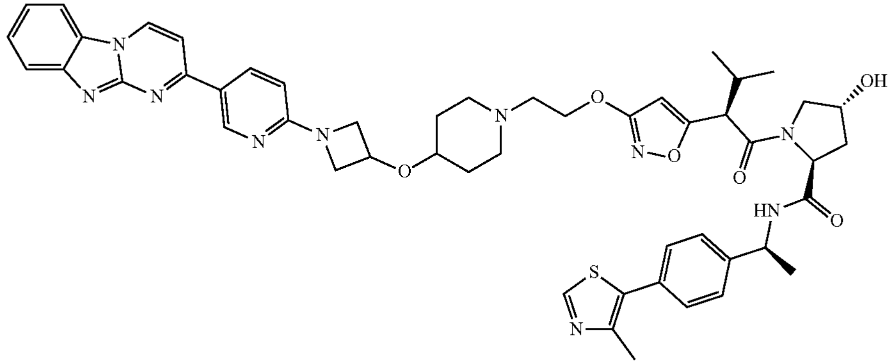 [SMILES: Cc1ncsc1-c1ccc([C@H](C)NC(=O)[C@@H]2C[C@@H](O)CN2C(=O)[C@@H](c2cc(OCCN3CCC(OC4CN(c5ccc(-c6ccn7c(n6)nc6ccccc67)cn5)C4)CC3)no2)C(C)C)cc1] | (2S,4R)-1-((R)-2-(3-(2-(4-((1-(5-(benzo[4,5]imidazo[1,2-a]pyrimidin-2-yl)pyridin-2-yl)azetidin-3-yl)oxy)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | | 925.6 | $^1$H NMR (400 MHz, DMSO-$d_6$) δ: 9.76 (d, J = 7.3 Hz, 2H), 9.20 (d, J = 1.5 Hz, 1H), 8.99 (s, 1H), 8.54-8.45 (m, 2H), 8.44-8.35 (m, 1H), 8.28 (d, J = 7.3 Hz, 1H), 7.84 (d, J = 8.1 Hz, 1H), 7.74 (t, J = 7.8 Hz, 1H), 7.67-7.60 (m, 1H), 7.50-7.42 (m, 2H), 7.40-7.34 (m, 2H), 6.68-6.58 (m, 1H), 6.04 (s, 1H), 4.97-4.86 (m, 2H), 4.71-4.63 (m, 2H), 4.53 (d, J = 4.3 Hz, 2H), 4.38 (s, 3H), 4.08-3.93 (m, 3H), 3.69-3.43 (m, 7H), 3.13-3.17 (m, 1H), 2.45 (s, 3H), 2.29-2.15 (m, 2H), 1.93 (s, 3H), 1.79 (s, 2H), 1.47 (d, J = 7.0 Hz, 3H), 0.97 (d, J = 6.2 Hz, 3H), 0.81 (d, J = 6.6 Hz, 3H) |
| 467 | 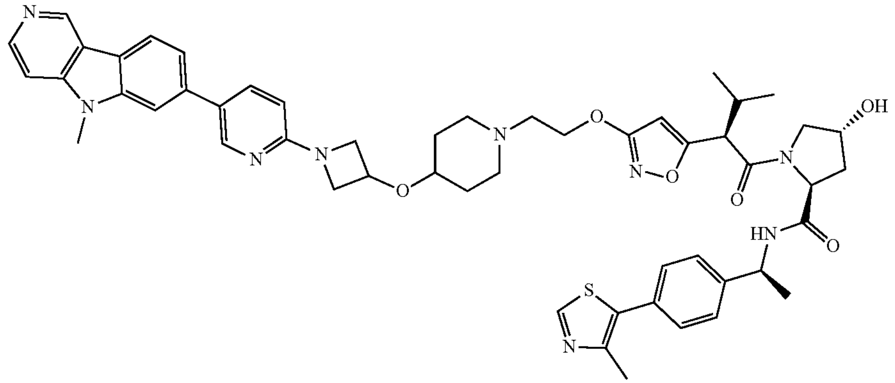<br>isomer 1 | (2S,4R)-4-hydroxy-1-((R)-3-methyl-2-(3-(2-(4-((1-(5-(5-methyl-5H-pyrido[4,3-b]indol-7-yl)pyridin-2-yl)azetidin-3-yl)oxy)piperidin-1-yl)ethoxy)isoxazol-5-yl)butanoyl)-N-((S)-1-(4-(4-methylthiazol-5-yl)phenyl)ethyl)pyrrolidine-2-carboxamide | B | 938.6 | $^1$H NMR (300 MHz, MeOD) δ: 9.24 (s, 1H), 8.84 (m, 1H), 8.44-8.42 (m, 2H), 8.26-8.23 (m, 1H), 8.02-7.95 (m, 1H), 7.75 (s, 1H), 7.57-7.52 (m, 2H), 7.46-7.35 (m, 4H), 6.56-6.53 (m, 1H), 6.04 (s, 1H), 4.98 (m, 1H), 4.59-4.57 (m, 2H), 4.45 (m, 1H), 4.33-4.28 (m, 4H), 3.95-3.87 (m, 4H), 3.78-3.68 (m, 2H), 3.52-3.41 (m, 1H), 2.86-2.75 (m, 4H), 2.49-2.46 (m, 3H), 2.36-2.19 (m, 3H), 1.95-1.91 (m, 3H), 1.71-1.52 (m, 3H), 1.49-1.47 (m, 2H), 1.28 (m, 3H), 1.06-1.04 (m, 3H), 0.94-0.86 (m, 5H). |

TABLE 1-continued

| | | | | |
|---|---|---|---|---|
| 468 | 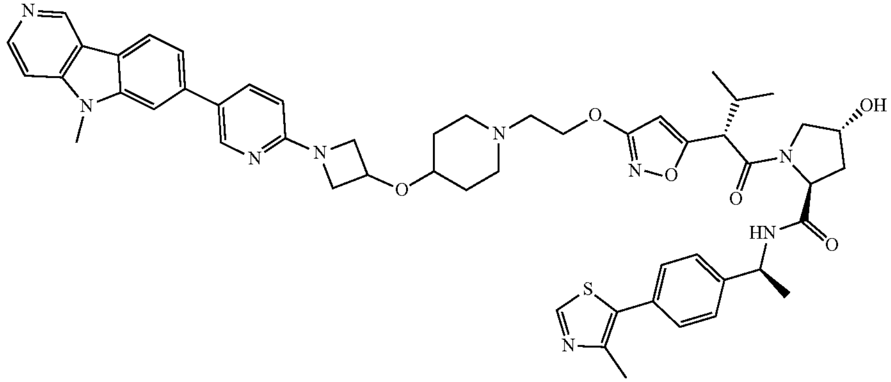 isomer 2 | (2S,4R)-4-hydroxy-1-((S)-3-methyl-2-(3-(2-(4-((1-(5-(5-methyl-5H-pyrido[4,3-b]indol-7-yl)pyridin-2-yl)azetidin-3-yl)oxy)piperidin-1-yl)ethoxy)isoxazol-5-yl)butanoyl)-N-((S)-1-(4-(4-methylthiazol-5-yl)phenyl)ethyl)pyrrolidine-2-carboxamide | 938.6 | $^1$H NMR (300 MHz, MeOD) δ: 9.22 (s, 1H), 8.86 (m, 1H), 8.45-8.43 (m, 2H), 8.27-2.24 (m, 1H), 8.05-7.97 (m, 1H), 7.77 (s, 1H), 7.58-7.53 (m, 2H), 7.43-7.42 (m, 4H), 6.59-6.56 (m, 1H), 6.01 (s, 1H), 5.02 (m, 1H), 4.88-4.82 (m, 1H), 4.68-4.63 (m, 1H), 4.51 (m, 1H), 4.36-3.32 (m, 4H), 3.97 (s, 3H), 3.92-3.88 (m, 2H), 3.69-3.66 (m, 1H), 3.54 (m, 2H), 3.34 (m, 3H), 2.83-2.81 (m, 4H), 2.47 (s, 3H), 2.36-2.35 (m, 3H), 2.03-1.95 (m, 3H), 1.66 (m, 2H), 1.53-1.51 (m, 3H), 1.29 (m, 1H), 1.06-1.04 (m, 3H), 0.90-0.88 (m, 3H). |
| 469 | 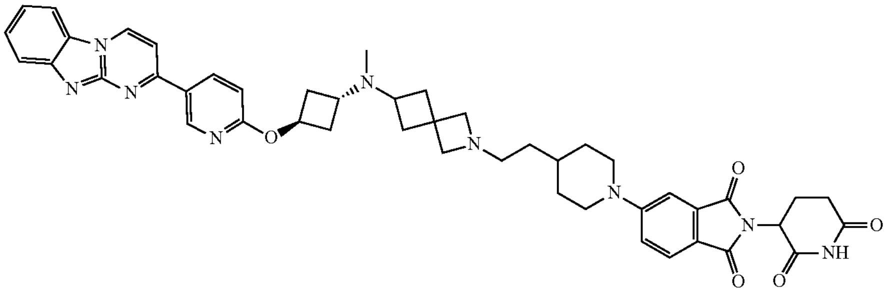 | 5-(4-(2-(6-(((1r,3r)-3-((5-(benzo[4,5]imidazo[1,2-a]pyrimidin-2-yl)pyridin-2-yl)oxy)cyclobutyl)(methyl)amino)-2-azaspiro[3.3]heptan-2-yl)ethyl)piperidin-1-yl)-2-(2,6-dioxopiperidin-3-yl)isoindoline-1,3-dione | 808.5 | $^1$H NMR (400 MHz, DMSO-$d_6$) δ: 11.07 (s, 1H), 10.82-10.62 (m, 1H), 10.30-10.10 (m, 1H), 9.80 (d, J = 7.3 Hz, 1H), 9.21 (d, J = 2.2 Hz, 1H), 8.77-8.65 (m, 1H), 8.45 (d, J = 8.3 Hz, 1H), 8.16 (d, J = 7.0 Hz, 1H), 7.88 (d, J = 8.2 Hz, 1H), 7.72-7.64 (m, 2H), 7.58 (d, J = 7.8 Hz, 1H), 7.32 (d, J = 1.6 Hz, 1H), 7.28-7.20 (m, 1H), 7.12 (d, J = 8.8 Hz, 1H), 5.35 (s, 1H), 5.10-5.02 (m, 1H), 4.29-4.14 (m, 2H), 4.06 (d, J = 13.1 Hz, 6H), 3.73-3.64 (m, 1H), 3.22-3.07 (m, 2H), 3.03-2.73 (m, 5H), 2.61 (s, 3H), 2.58-2.51 (m, 4H), 2.49-2.45 (m, 3H), 2.08-1.93 (m, 1H), 1.71 (d, J = 12.0 Hz, 2H), 1.58 (d, J = 6.0 Hz, 1H), 1.42-1.32 (m, 2H), 1.24-1.13 (m, 2H) |

TABLE 1-continued

| | | | | | |
|---|---|---|---|---|---|
| 470 | 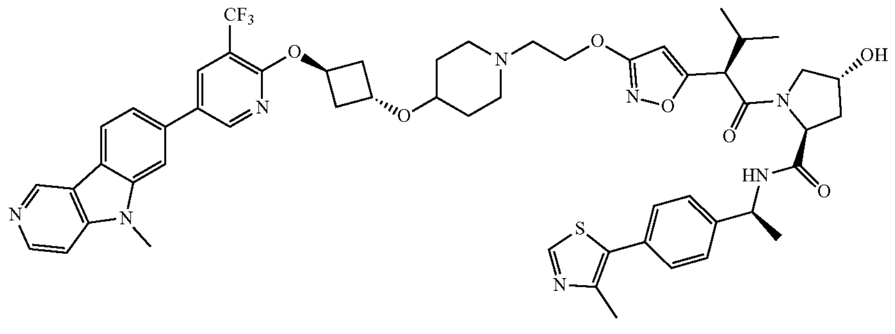 isomer 1 | (2S,4R)-4-hydroxy-1-((R)-3-methyl-2-(3-(2-(4-((1r,3R)-3-((5-(5-methyl-5H-pyrido[4,3-b]indol-7-yl)-3-(trifluoromethyl)pyridin-2-yl)oxy)cyclobutoxy)piperidin-1-yl)ethoxy)isoxazol-5-yl)butanoyl)-N-((S)-1-(4-(4-methylthiazol-5-yl)phenyl)ethyl)pyrrolidine-2-carboxamide | | 1021.6 | $^1$H NMR (400 MHz, $CDOD_3$): δ 9.28 (s, 1H), 8.86 (m, 1H), 8.72 (m, 1H), 8.46-8.45 (m, 1H), 8.33-8.29 (m, 2H), 7.84 (m, 1H), 7.59-7.56 (m, 2H), 7.48-7.37 (m, 4H), 6.06 (s, 1H), 5.51 (m, 1H), 5.02-5.00 (m, 1H), 4.61-4.57 (m, 1H), 4.45-4.33 (m, 4H), 3.96 (s, 3H), 3.80-3.69 (m, 3H), 3.45 (m, 1H), 2.87-2.77 (m, 4H), 2.50-2.31 (m, 11H), 1.97-1.89 (m, 3H), 1.65-1.60 (m, 3H), 1.51-1.49 (m, 3H), 1.08-1.06 (m, 3H), 0.98-0.88 (m, 4H). |
| 471 | 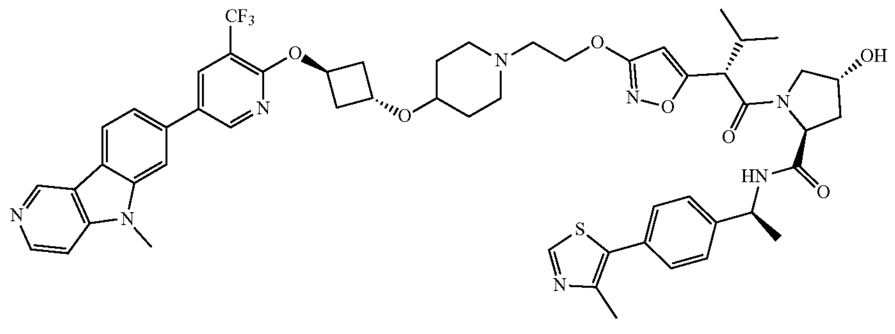 isomer 2 | (2S,4R)-4-hydroxy-1-((S)-3-methyl-2-(3-(2-(4-((1r,3S)-3-((5-(5-methyl-5H-pyrido[4,3-b]indol-7-yl)-3-(trifluoromethyl)pyridin-2-yl)oxy)cyclobutoxy)piperidin-1-yl)ethoxy)isoxazol-5-yl)butanoyl)-N-((S)-1-(4-(4-methylthiazol-5-yl)phenyl)ethyl)pyrrolidine-2-carboxamide | | 1021.6 | $^1$H NMR (400 MHz, $CDOD_3$) δ 9.28 (s, 1H), 8.88 (s, 1H), 8.73 (s, 1H), 8.47-8.45 (m, 1H), 8.32-8.30 (m, 2H), 7.85 (s, 1H), 7.61-7.57 (m, 2H), 7.46-7.41 (m, 4H), 6.03 (s, 1H), 5.51 (m, 1H), 5.06-5.04 (m, 1H), 4.54 (m, 1H), 4.45-4.34 (m, 4H), 3.98 (s, 3H), 3.85 (m, 1H), 3.71-3.64 (m, 2H), 3.45 (m, 1H), 2.90-2.81 (m, 4H), 2.54-2.50 (m, 7H), 2.49-2.36 (m, 3H), 2.16 (m, 1H), 1.95-1.92 (m, 3H), 1.67-1.62 (m, 3H), 1.54-1.53 (m, 3H), 1.28-1.21 (m, 1H), 1.08-1.06 (m, 3H), 0.92-0.90 (m, 3H). |
| 472 | 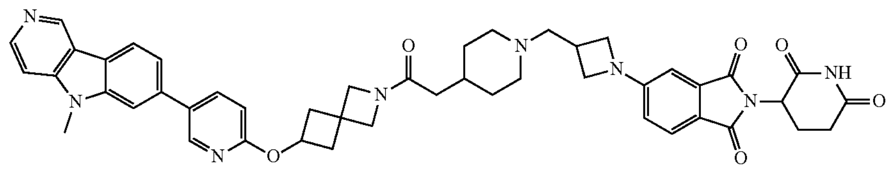 [SMILES: Cn1c2ccncc2c2ccc(-c3ccc(OC4CC5(C4)CN(C(=O)CC4CCN(CC6CN(c7ccc8c(c7)C(=O)N(C7CCC(=O)NC7=O)C8=O)C6)CC4)C5)nc3)cc21] | 2-(2,6-dioxopiperidin-3-yl)-5-(3-((4-(2-(6-((5-(5-methyl-5H-pyrido[4,3-b]indol-7-yl)pyridin-2-yl)oxy)-2-azaspiro[3.3]heptan-2-yl)-2-oxoethyl)piperidin-1-yl)methyl)azetidin-1-yl)isoindoline-1,3-dione | A | 821.5 | $^1$H NMR (400 MHz, DMSO-d6) δ: 11.08 (s, 1H), 9.77 (s, 1H), 9.24 (m, 1H), 8.79-8.78 (m, 1H), 8.71-8.69 (m, 1H), 8.54 (m, 1H), 8.28-8.22 (m, 3H), 7.90-7.88 (m, 1H), 7.70-7.68 (m, 1H), 6.99-6.97 (m, 1H), 6.82 (m, 1H), 6.69-6.67 (m, 1H), 5.17 (m, 1H), 5.06 (m, 1H), 4.26-4.22 (m, 2H), 4.15-4.14 (m, 3H), 3.97 (m, 2H), 3.88-3.82 (m, 4H), 3.26 (m, 2H), 3.12-3.09 (m, 1H), 2.94-2.82 (m, 2H), 2.77 (m, 3H), 2.36-2.33 (m, 3H), 2.04-1.87 (m, 5H), 1.42 (m, 2H), 1.24-1.16 (m, 3H). |

TABLE 1-continued

| | | | | | |
|---|---|---|---|---|---|
| 473 | 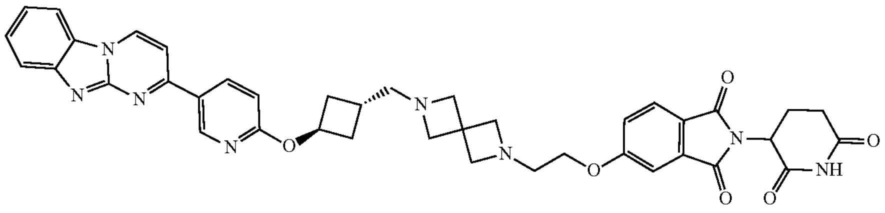 [SMILES: O=C1CCC(N2C(=O)c3ccc(OCCN4CC5(C4)CN(C[C@H]4C[C@H](Oc6ccc(-c7ccn8c(n7)nc7ccccc78)cn6)C4)C5)cc3C2=O)C(=O)N1] | 5-(2-(6-(((1r,3r)-3-((5-(benzo[4,5]imidazo[1,2-a]pyrimidin-2-yl)pyridin-2-yl)oxy)cyclobutyl)methyl)-2,6-diazaspiro[3.3]heptan-2-yl)ethoxy)-2-(2,6-dioxopiperidin-3-yl)isoindoline-1,3-dione | A | 727.4 | $^1$H NMR (400 MHz, DMSO-$d_6$) δ: 11.11 (s, 1H), 10.34-9.97 (m, 1H), 9.59 (d, J = 7.2 Hz, 1H), 9.79-9.50 (m, 1H), 9.14-9.08 (m, 1H), 8.64 (dd, J = 2.4, 8.8 Hz, 1H), 8.33 (d, J = 8.4 Hz, 1H), 7.95-7.88 (m, 1H), 7.87-7.80 (m, 2H), 7.55 (t, J = 7.2 Hz, 1H), 7.49 (s, 1H), 7.46-7.41 (m, 1H), 7.40-7.35 (m, 1H), 7.03 (d, J = 8.8 Hz, 1H), 5.40-5.32 (m, 1H), 5.17-5.10 (m, 1H), 4.48-4.36 (m, 4H), 4.35-4.13 (m, 5H), 3.74-3.51 (m, 2H), 2.83 (s, 1H), 2.61 (d, J = 18.4 Hz, 1H), 2.55 (s, 1H), 2.52 (d, J = 2.0 Hz, 5H), 2.38-2.35 (m, 1H), 2.31-2.26 (m, 1H), 2.11-1.83 (m, 2H) |
| 474 | 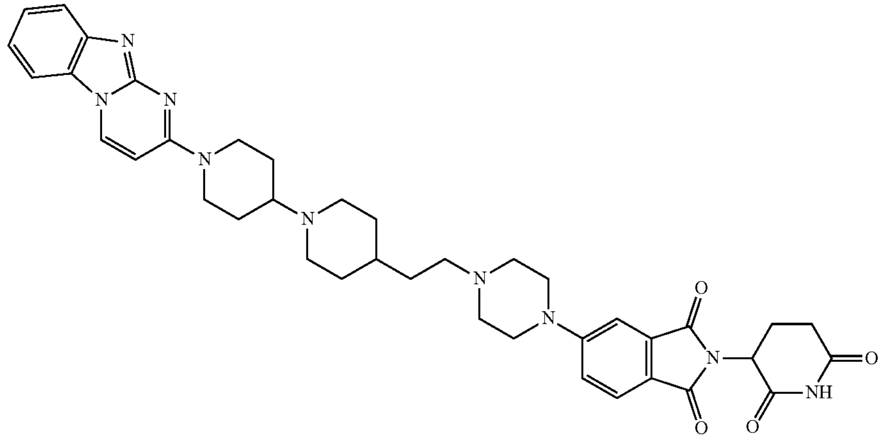 [SMILES: O=C1CCC(N2C(=O)c3ccc(N4CCN(CCC5CCN(C6CCN(c7ccn8c(n7)nc7ccccc78)CC6)CC5)CC4)cc3C2=O)C(=O)N1] | 5-(4-(2-(1'-(benzo[4,5]imidazo[1,2-a]pyrimidin-2-yl)-[1,4'-bipiperidin]-4-yl)ethyl)piperazin-1-yl)-2-(2,6-dioxopiperidin-3-yl)isoindoline-1,3-dione | | 704.5 | 1H NMR (400 MHz, DMSO-d6): δ 1.10-1.32 (m, 3 H), 1.34-1.53 (m, 4 H), 1.67 (d, J = 11.2 Hz, 2 H), 1.87 (d, J = 11.2 Hz, 2 H), 2.01 (d, J = 5.4 Hz, 1 H), 2.16 (t, J = 10.0 Hz, 3 H), 2.60 (s, 8 H), 2.81-3.07 (m, 9 H), 4.60 (s, 2 H), 5.08 (d, J = 12.8 Hz, 1 H), 6.90 (d, J = 7.6 Hz, 1 H), 7.15 (t, J = 8.0 Hz, 1 H), 7.21-7.38 (m, 3 H), 7.51 (d, J = 8.4 Hz, 1 H), 7.68 (d, J = 8.4 Hz, 1 H), 7.95 (d, J = 8.0 Hz, 1 H), 8.25 (s, 3 H), 8.96 (d, J = 7.6 Hz, 1 H), 11.10 (s, 1 H) |

TABLE 1-continued

| | | | | | |
|---|---|---|---|---|---|
| 475 | 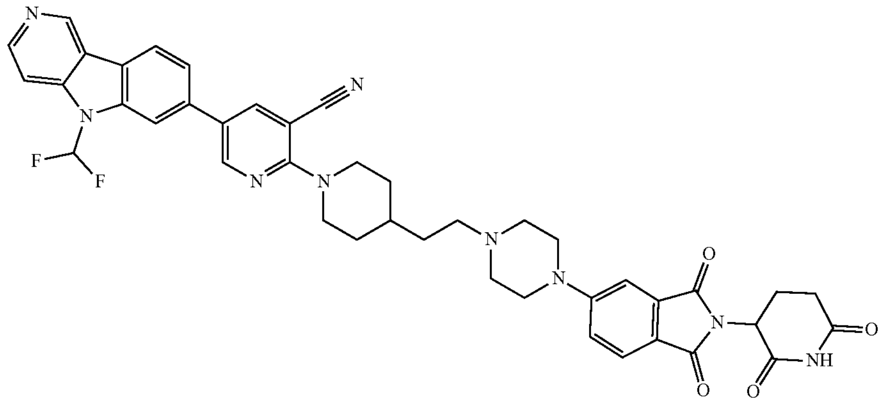 [SMILES: N#Cc1cc(-c2ccc3c4cnccc4n(C(F)F)c3c2)cnc1N1CCC(CCN2CCN(c3ccc4c(c3)C(=O)N(C3CCC(=O)NC3=O)C4=O)CC2)CC1] | 5-(5-(difluoromethyl)-5H-pyrido[4,3-b]indol-7-yl)-2-(4-(2-(4-(2-(2,6-dioxopiperidin-3-yl)-1-oxoisoindolin-5-yl)piperazin-1-yl)ethyl)piperidin-1-yl)nicotinonitrile | B | 758.4 | $^1$H NMR (400 MHz, DMSO-$d_6$) δ: 10.96 (s, 1H), 9.50 (s, 1H), 8.89 (d, J = 2.4 Hz, 1H), 8.62 (d, J = 6.0 Hz, 1H), 8.55 (d, J = 2.4 Hz, 1H), 8.50-8.41 (m, 1H), 8.41-8.33 (m, 1H), 8.26 (s, 1H), 8.17 (s, 2H), 7.89-7.79 (m, 2H), 7.53 (d, J = 8.8 Hz, 1H), 7.13-7.02 (m, 2H), 5.06 (m, 1H), 4.43-4.36 (m, 2H), 4.31 (s, 1H), 4.23-4.18 (m, 1H), 3.32-3.29 (m, 6H), 3.09 (t, J = 12 Hz, 2H), 2.91 (s, 2H), 2.61 (d, J = 2.4 Hz, 1H), 2.46-2.37 (m, 4H), 1.96 (d, J = 5.6 Hz, 1H), 1.86 (d, J = 13.2 Hz, 2H), 1.68 (s, 1H), 1.54-1.43 (m, 2H), 1.38-1.20 (m, 2H) |
| 476 | 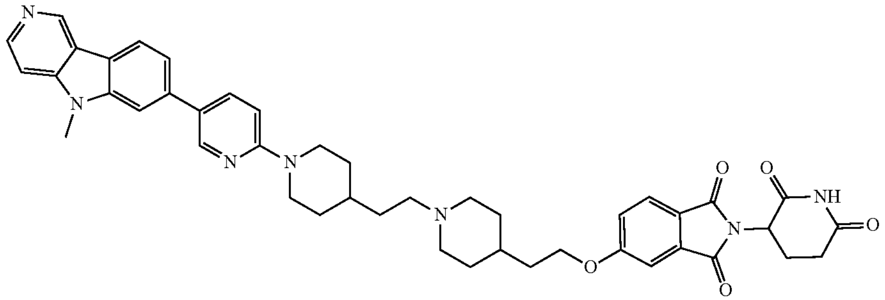 [SMILES: Cn1c2ccncc2c2ccc(-c3ccc(N4CCC(CCN5CCC(CCOc6ccc7c(c6)C(=O)N(C6CCC(=O)NC6=O)C7=O)CC5)CC4)nc3)cc21] | 2-(2,6-dioxopiperidin-3-yl)-5-(2-(1-(2-(1-(5-(5-methyl-5H-pyrido[4,3-b]indol-7-yl)pyridin-2-yl)piperidin-4-yl)ethyl)piperidin-4-yl)ethoxy)isoindoline-1,3-dione | | 754.5 | |
| 477 | 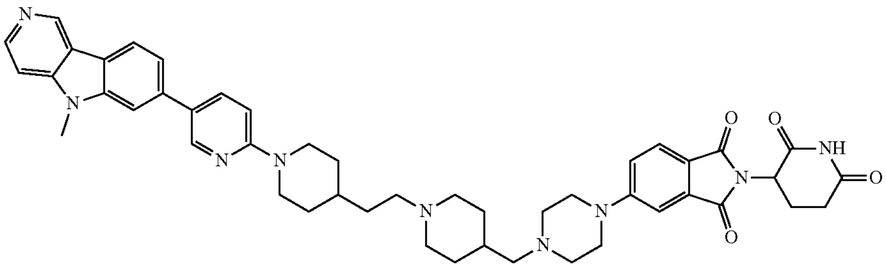 [SMILES: Cn1c2ccncc2c2ccc(-c3ccc(N4CCC(CCN5CCC(CN6CCN(c7ccc8c(c7)C(=O)N(C7CCC(=O)NC7=O)C8=O)CC6)CC5)CC4)nc3)cc21] | 2-(2,6-dioxopiperidin-3-yl)-5-(4-((1-(2-(1-(5-(5-methyl-5H-pyrido[4,3-b]indol-7-yl)pyridin-2-yl)piperidin-4-yl)ethyl)piperidin-4-yl)methyl)piperazin-1-yl)isoindoline-1,3-dione | | 808.6 | |

TABLE 1-continued

| | | | | | |
|---|---|---|---|---|---|
| 478 | 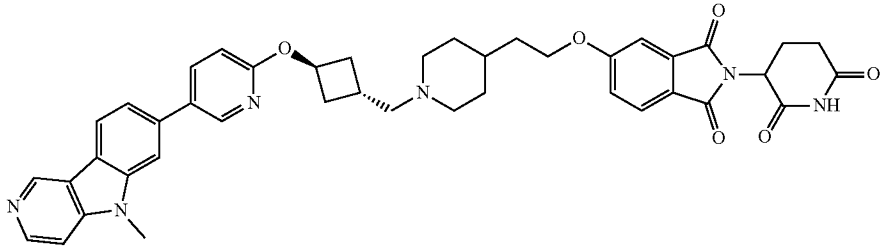 [SMILES: Cn1c2ccncc2c2ccc(-c3ccc(O[C@H]4C[C@H](CN5CCC(CCOc6ccc7c(c6)C(=O)N(C6CCC(=O)NC6=O)C7=O)CC5)C4)nc3)cc21] | 2-(2,6-dioxopiperidin-3-yl)-5-(2-(1-(((1r,3r)-3-((5-(5-methyl-5H-pyrido[4,3-b]indol-7-yl)pyridin-2-yl)oxy)cyclobutyl) methyl)piperidin-4-yl)ethoxy)isoindoline-1,3-dione | B | 727.4 | $^1$H NMR (400 MHz, methanol-$d_4$): δ 9.26 (s, 1H), 8.54-8.44 (m, 2H), 8.31 (d, J = 8.1 Hz, 1H), 8.15-8.08 (m, 0H), 7.82 (d, J = 10.2 Hz, 2H), 7.64-7.56 (m, 2H), 7.41 (s, 1H), 7.33 (d, J = 6.5 Hz, 1H), 6.90 (d, J = 8.7 Hz, 1H), 4.56 (s, 2H), 4.24 (t, J = 6.4 Hz, 1H), 4.00 (s, 3H), 3.65 (s, 1H), 3.36 (s, 1H), 2.77 (d, J = 14.7 Hz, 3H), 2.05 (s, 1H), 1.94 (d, J = 11.5 Hz, 2H), 1.88-1.80 (m, 2H), 1.61 (s, 1H), 1.41 (d, J = 12.3 Hz, 1H), 1.30 (s, 9H), 0.92 (d, J = 6.2 Hz, 2H), 0.90 (s, 7H), 0.11 (s, 4H). |
| 479 | 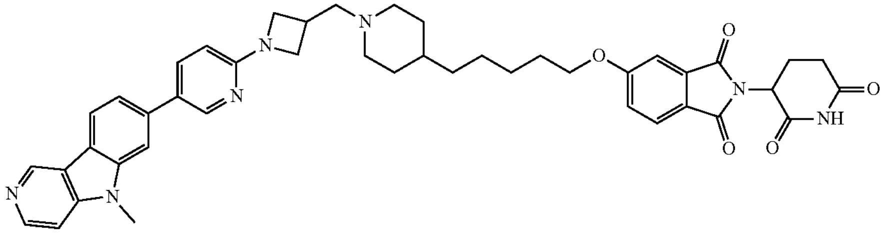 [SMILES: Cn1c2ccncc2c2ccc(-c3ccc(N4CC(CN5CCC(CCCCCOc6ccc7c(c6)C(=O)N(C6CCC(=O)NC6=O)C7=O)CC5)C4)nc3)cc21] | 2-(2,6-dioxopiperidin-3-yl)-5-((5-(1-((1-(5-(5-methyl-5H-pyrido[4,3-b]indol-7-yl)pyridin-2-yl)azetidin-3-yl)methyl)piperidin-4-yl)pentyl)oxy) isoindoline-1,3-dione | | 754.5 | 1H NMR (300 MHz, DMSO-d6) δ: 11.11 (s, 1H), 9.34 (s, 1H), 8.58-8.57 (s, 1H), 8.49-8.48 (m, 1H), 8.29-8.27 (m, 1H), 8.02-8.00 (m, 1H), 7.89-7.83 (m, 2H), 7.62-7.56 (m, 2H), 7.43-7.34 (m, 2H), 6.52-6.50 (m, 1H), 5.12 (m, 1H), 4.20-4.17 (m, 2H), 4.11-4.07 (m, 2H), 3.95 (s, 3H), 3.66-3.62 (m, 2H), 2.84-2.81 (m, 4H), 2.58-2.56 (m, 4H), 2.08-1.90 (m, 2H), 1.88 (m, 2H), 1.78-1.75 (m, 2H), 1.65 (m, 2H), 1.47-1.32 (m, 3H), 1.28-1.03 (m 5H). |
| 480 | 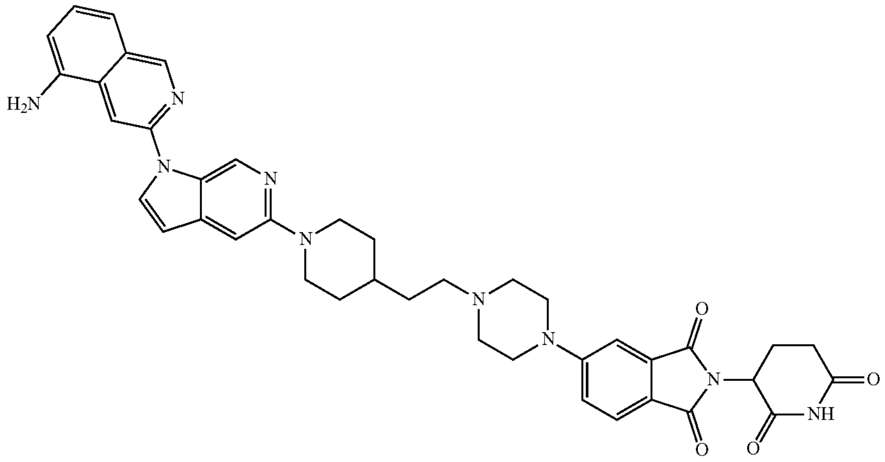 [SMILES: Nc1cccc2cnc(-n3ccc4cc(N5CCC(CCN6CCN(c7ccc8c(c7)C(=O)N(C7CCC(=O)NC7=O)C8=O)CC6)CC5)ncc43)cc12] | 5-(4-(2-(1-(1-(5-aminoisoquinolin-3-yl)-1H-pyrrolo[2,3-c]pyridin-5-yl) piperidin-4-yl)ethyl) piperazin-1-yl)-2-(2,6-dioxopiperidin-3-yl) isoindoline-1,3-dione | B | 712.4 | $^1$H NMR (400 MHz, Chloroform-d) δ: 9.29 (s, 1H), 9.16 (s, 1H), 8.03 (d, J = 3.4 Hz, 1H), 7.94 (s, 1H), 7.75-7.68 (m, 2H), 7.48 (d, J = 8.3 Hz, 1H), 7.44-7.35 (m, 1H), 7.31 (d, J = 2.3 Hz, 1H), 7.08 (dd, J = 8.6, 2.3 Hz, 1H), 6.94 (s, 1H), 6.60 (d, J = 3.4 Hz, 1H), 4.96 (dd, J = 12.3, 5.3 Hz, 1H), 4.24 (d, J = 12.1 Hz, 3H), 3.48 (s, 3H), 2.96-2.81 (m, 2H), 2.85-2.71 (m, 1H), 2.65 (s, 3H), 2.52 (s, 2H), 2.28 (d, J = 7.1 Hz, 0H), 2.21-2.13 (m, 1H), 2.06 (s, 1H), 1.93-1.84 (m, 2H), 1.70 (s, 1H), 1.45 (s, 2H), 1.40 (s, 1H), 1.28 (s, 26H), 0.94-0.83 (m, 4H), 0.88 (s, 18H), 0.13-0.06 (m, 7H). |

TABLE 1-continued

| | | | | | |
|---|---|---|---|---|---|
| 481 | 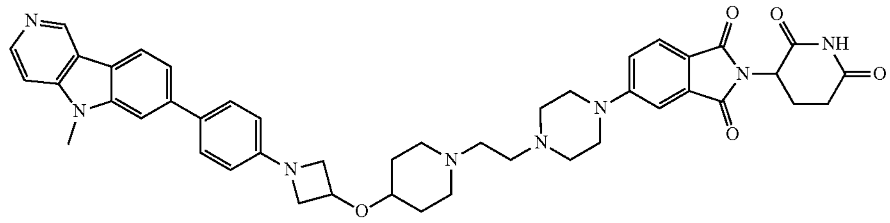 | 2-(2,6-dioxopiperidin-3-yl)-5-(4-(2-(4-((1-(4-(5-methyl-5H-pyrido[4,3-b]indol-7-yl)phenyl)azetidin-3-yl)oxy)piperidin-1-yl)ethyl)piperazin-1-yl)isoindoline-1,3-dione | | 781.5 | 1H NMR (400 MHz, DMSO-d6): δ 11.07 (s, 1H), 9.32 (s, 1H), 8.48-8.47 (m, 1H), 8.26-8.24 (m, 1H), 7.85 (s, 1H), 7.70-7.55 (m, 5H), 7.34 (m, 2H), 6.59-6.57 (m, 2H), 5.07 (m, 1H), 4.57 (m, 1H), 4.19-4.16 (m, 2H), 3.95 (s, 3H), 3.63 (m, 2H), 3.43 (m, 7H), 2.90-2.74 (m, 5H), 2.55 (m, 1H), 2.17-1.98 (m, 4H), 1.83 (m, 2H), 1.50-1.48 (m, 3H), 1.24 (m, 3H). |
| 482 | 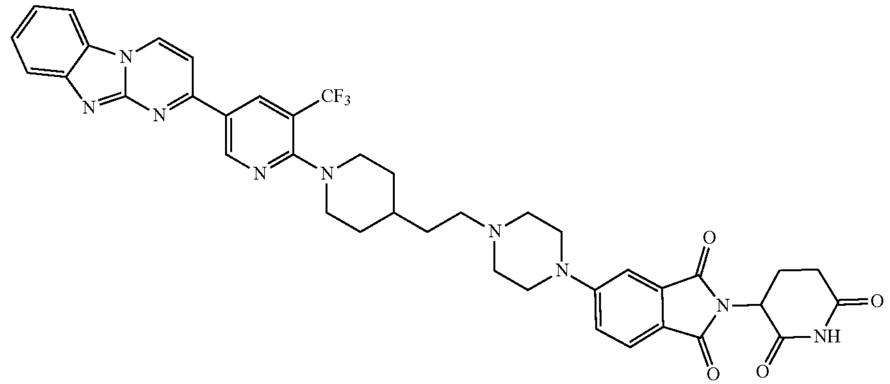 [SMILES: O=C1CCC(N2C(=O)c3ccc(N4CCN(CCC5CCN(c6ncc(-c7ccn8c(n7)nc7ccccc78)cc6C(F)(F)F)CC5)CC4)cc3C2=O)C(=O)N1] | 5-(4-(2-(1-(5-(benzo[4,5]imidazo[1,2-a]pyrimidin-2-yl)-3-(trifluoromethyl) pyridin-2-yl)piperidin-4-yl)ethyl)piperazin-1-yl)-2-(2,6-dioxo-piperidin-3-yl) isoindoline-1,3-dione | | 766.3 | 1H NMR (400 MHz, DMSO-d6) δ: 1.04-1.43 (m, 4 H), 1.48 (d, J = 7.2 Hz, 2 H), 1.63 (s, 1 H), 1.67-1.96 (m, 3 H), 1.99-2.19 (m, 2 H), 2.33 (s, 4 H), 2.78-2.97 (m, 2 H), 3.07 (t, J = 12.0 Hz, 2 H), 3.45 (s, 3 H), 3.98 (d, J = 12.4 Hz, 2 H), 5.08 (d, J = 12.8 Hz, 1 H), 7.27 (d, J = 8.4 Hz, 1 H), 7.35 (s, 1 H), 7.43 (t, J = 7.2 Hz, 1 H), 7.55 (t, J = 8.0 Hz, 1 H), 7.68 (d, J = 8.4 Hz, 1 H), 7.84 (d, J = 8.4 Hz, 1 H), 7.91 (d, J = 7.2 Hz, 1 H), 8.21 (s, 1 H), 8.32 (d, J = 8.0 Hz, 1 H), 8.83 (d, J = 2.4 Hz, 1 H), 9.33 (s, 1 H), 9.59 (d, J = 7.2 Hz, 1 H), 11.08 (s, 1 H). |
| 483 | 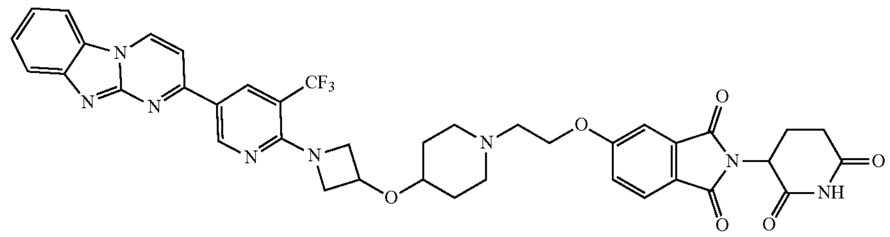 [SMILES: O=C1CCC(N2C(=O)c3ccc(OCCN4CCC(OC5CN(c6ncc(-c7ccn8c(n7)nc7ccccc78)cc6C(F)(F)F)C5)CC4)cc3C2=O)C(=O)N1] | 5-(2-(4-((1-(5-(benzo[4,5]imidazo[1,2-a]pyrimidin-2-yl)-3-(trifluoromethyl)pyridin-2-yl)azetidin-3-yl)oxy)piperidin-1-yl)ethoxy)-2-(2,6-dioxopiperidin-3-yl)isoindoline-1,3-dione | B | 769.3 | 1H NMR (400 MHz, DMSO-d6) δ: 1.44-1.57 (m, 2 H), 1.84 (s, 2 H), 2.08 (s, 2 H), 2.22 (t, J = 9.6 Hz, 2 H), 2.73-2.92 (m, 4 H), 3.45 (s, 3 H), 4.07 (d, J = 9.6 Hz, 2 H), 4.30 (t, J = 5.6 Hz, 2 H), 4.45-4.66 (m, 3 H), 5.12 (d, J = 12.8 Hz, 1 H), 7.33-7.59 (m, 4 H), 7.77-7.92 (m, 3 H), 8.18 (s, 1 H), 8.30 (d, J = 8.4 Hz, 1 H), 8.75 (d, J = 2.0 Hz, 1 H), 9.30 (d, J = 2.0 Hz, 1 H), 9.54 (d, J = 7.2 Hz, 1 H), 11.11 (s, 1 H) |
| 484 | 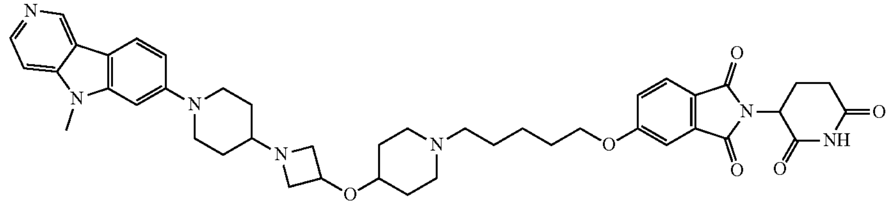 [SMILES: Cn1c2ccncc2c2ccc(N3CCC(N4CC(OC5CCN(CCCCCOc6ccc7c(c6)C(=O)N(C6CCC(=O)NC6=O)C7=O)CC5)C4)CC3)cc21] | 2-(2,6-dioxopiperidin-3-yl)-5-((5-(4-((1-(1-(5-methyl-5H-pyrido[4,3-b]indol-7-yl)piperidin-4-yl)azetidin-3-yl)oxy)piperidin-1-yl)pentyl)oxy) isoindoline-1,3-dione | | 762.4 | $^{1}$H NMR (400 MHz, DMSO-$d_6$) δ: 11.10 (s, 1H), 10.80 (d, J = 6.4 Hz, 1H), 9.75-9.53 (m, 1H), 9.50 (s, 1H), 8.63 (d, J = 6.8 Hz, 1H), 8.24 (d, J = 8.8 Hz, 1H), 8.07 (d, J = 6.8 Hz, 1H), 7.85 (d, J = 8.4 Hz, 1H), 7.42 (d, J = 2.0 Hz, 1H), 7.35 (dd, J = 2.4, 8.4 Hz, 1H), 7.29 (s, 1H), 7.24 (d, J = 8.8 Hz, 1H), 5.12 (dd, J = 5.6, 12.8 Hz, 1H), 4.53-4.33 (m, 3H), 4.20 (t, J = 5.6 Hz, 2H), 4.17-4.08 (m, 3H), 4.01 (s, 3H), 3.96-3.77 (m, 1H), 3.64-3.57 (m, 1H), 3.08 (s, 3H), |

TABLE 1-continued

| | | | | | |
|---|---|---|---|---|---|
| | | | | | 2.95-2.83 (m, 4H), 2.62 (s, 1H), 2.58 (s, 1H), 2.54 (d, J = 4.8 Hz, 1H), 2.53-2.52 (m, 2H), 2.13-2.01 (m, 4H), 1.96-1.84 (m, 2H), 1.80 (s, 2H), 1.76-1.67 (m, 2H), 1.66-1.55 (m, 1H), 1.48 (s, 4H) |
| 485 | 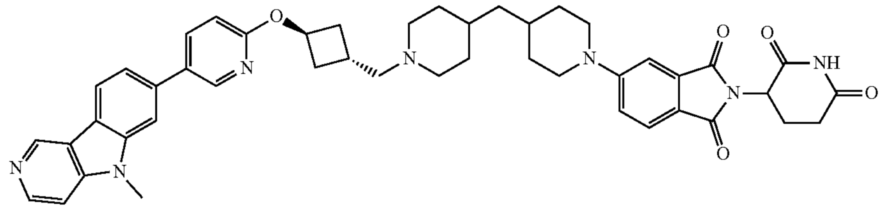 [SMILES: Cn1c2ccncc2c2ccc(-c3ccc(O[C@H]4C[C@H](CN5CCC(CC6CCN(c7ccc8c(c7)C(=O)N(C7CCC(=O)NC7=O)C8=O)CC6)CC5)C4)nc3)cc21] | 2-(2,6-dioxopiperidin-3-yl)-5-(4-((1-(((1r,3r)-3-((5-(5-methyl-5H-pyrido[4,3-b]indol-7-yl)pyridin-2-yl)oxy)cyclobutyl) methyl)piperidin-4-yl)methyl)piperidin-1-yl)isoindoline-1,3-dione | A | 780.4 | $^1$H NMR (400 MHz, methanol-$d_4$): δ 9.25 (s, 1H), 8.54-8.48 (m, 1H), 8.46 (d, J = 5.9 Hz, 1H), 8.29 (d, J = 8.2 Hz, 1H), 8.16-8.07 (m, 1H), 7.82 (s, 1H), 7.65 (d, J = 8.6 Hz, 1H), 7.62-7.54 (m, 2H), 7.35-7.30 (m, 1H), 7.19 (dd, J = 8.7, 2.4 Hz, 1H), 6.95-6.86 (m, 1H), 5.35-5.27 (m, 1H), 5.06 (dd, J = 12.5, 5.4 Hz, 1H), 4.57 (s, 1H), 4.03 (d, J = 13.1 Hz, 2H), 3.98 (s, 3H), 3.25 (d, J = 11.4 Hz, 2H), 3.03-2.99 (m, 1H), 2.99-2.92 (m, 2H), 2.89-2.66 (m, 3H), 2.59-2.54 (m, 2H), 2.48-2.38 (m, 3H), 2.14-2.06 (m, 1H), 1.97-1.92 (m, 1H), 1.92-1.78 (m, 4H), 1.72-1.58 (m, 2H), 1.43-1.19 (m, 4H). |
| 486 | 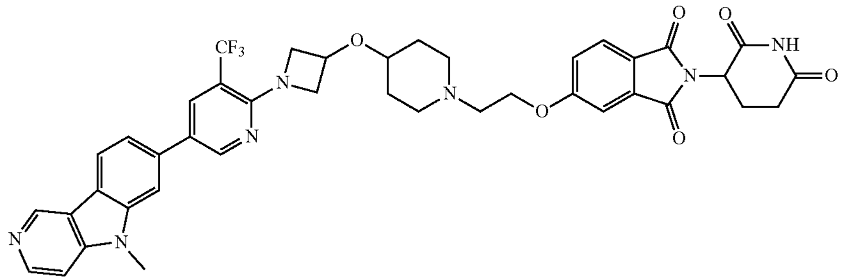 [SMILES: Cn1c2ccncc2c2ccc(-c3cnc(N4CC(OC5CCN(CCOc6ccc7c(c6)C(=O)N(C6CCC(=O)NC6=O)C7=O)CC5)C4)c(C(F)(F)F)c3)cc21] | 2-(2,6-dioxopiperidin-3-yl)-5-(2-(4-((1-(5-(5-methyl-5H-pyrido[4,3-b]indol-7-yl)-3-(trifluoromethyl)pyridin-2-yl)azetidin-3-yl)oxy)piperidin-1-yl)ethoxy)isoindoline-1,3-dione | | 782.3 | $^1$H NMR (400 MHz, DMSO-$d_6$): δ 11.12 (s, 1H), 9.36 (s, 1H), 8.88 (d, J = 2.2 Hz, 1H), 8.50 (d, J = 5.7 Hz, 1H), 8.35-8.28 (m, 2H), 8.16 (s, 1H), 8.03 (d, J = 1.5 Hz, 1H), 7.84 (d, J = 8.3 Hz, 1H), 7.69-7.60 (m, 2H), 7.47 (d, J = 2.2 Hz, 1H), 7.37 (dd, J = 8.3, 2.3 Hz, 1H), 5.12 (dd, J = 13.0, 5.4 Hz, 1H), 4.58 (dq, J = 10.8, 4.7 Hz, 1H), 4.42 (t, J = 7.8 Hz, 2H), 4.29 (t, J = 5.7 Hz, 2H), 4.00 (d, J = 4.3 Hz, 1H), 3.97 (s, 4H), 2.95-2.81 (m, 3H), 2.75 (t, J = 5.7 Hz, 2H), 2.59 (dd, J = 20.1, 6.5 Hz, 1H), 2.22 (t, J = 10.3 Hz, 2H), 2.05 (ddd, J = 12.2, 5.9, 3.5 Hz, 1H), 1.85 (d, J = 11.8 Hz, 2H), 1.56-1.43 (m, 2H). |
| 487 | 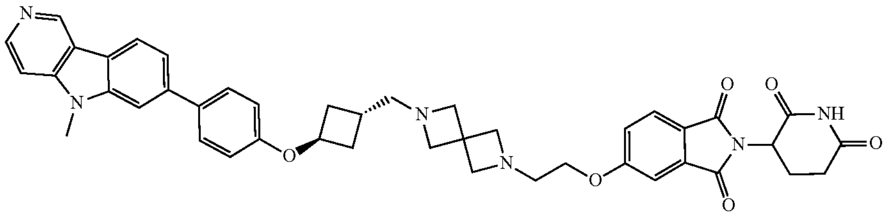 [SMILES: Cn1c2ccncc2c2ccc(-c3ccc(O[C@H]4C[C@H](CN5CC6(CN(CCOc7ccc8c(c7)C(=O)N(C7CCC(=O)NC7=O)C8=O)C6)C5)C4)cc3)cc21] | 2-(2,6-dioxopiperidin-3-yl)-5-(2-(6-(((1r,3r)-3-(4-(5-methyl-5H-pyrido[4,3-b]indol-7-yl)phenoxy)cyclobutyl) methyl)-2,6-diazaspiro[3.3]heptan-2-yl)ethoxy) isoindoline-1,3-dione | | 739.3 | $^1$H NMR (400 MHz, DMSO-d6) δ 11.11 (s, 1H), 9.34 (s, 1H), 8.49-8.27 (m, 2H), 7.89-7.74 (m, 4H), 7.62-7.56 (m, 2H), 7.42-7.33 (m, 2H), 6.95-6.93 (m, 2H), 5.77 (m, 8H), 5.14-5.10 (m, 1H), 4.85-4.84 (m, 1H), 4.13-4.03 (m, 2H), 3.89 (m, 3H), 3.51 (m, 2H), 3.14 (m, 2H), 2.74 (m, 2H), 2.22-2.16 (m, 3H), 2.08-2.00 (m, 2H), 1.77 (m, 2H). |

TABLE 1-continued

| | | | | | |
|---|---|---|---|---|---|
| 488 | 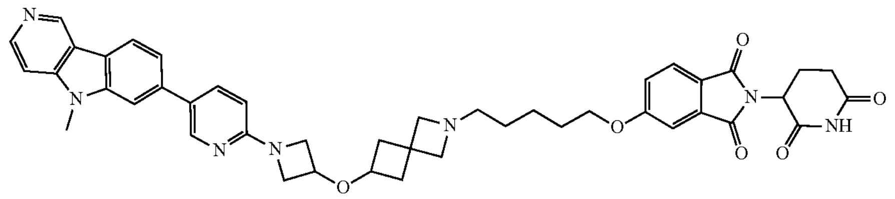 [SMILES: Cn1c2ccncc2c2ccc(-c3ccc(N4CC(OC5CC6(C5)CN(CCCCCOc5ccc7c(c5)C(=O)N(C5CCC(=O)NC5=O)C7=O)C6)C4)nc3)cc21] | 2-(2,6-dioxopiperidin-3-yl)-5-((5-(6-((1-(5-(5-methyl-5H-pyrido[4,3-b]indol-7-yl)pyridin-2-yl)azetidin-3-yl)oxy)-2-azaspiro[3.3]heptan-2-yl)pentyl)oxy)isoindoline-1,3-dione | | 768.3 | $^1$H NMR (400 MHz, DMSO-$d_6$) δ: 11.11 (s, 1H), 9.87 (s, 1H), 9.74 (s, 1H), 8.76 (d, J = 7.2, 1H), 8.63 (s, 1H), 8.51 (d, J = 8.4 Hz, 1H), 8.21-8.16 (m, 3H), 7.86-7.82 (m, 1H), 6.65 (d, J = 8.0 Hz, 1H), 5.14-5.10 (m, 1H), 6.56 (d, J = 8.0 Hz, 1H), 5.12 (dd, J = 5.6, 12.8 Hz, 1H), 4.65-4.58 (m, 1H), 4.14-4.16 (m, 8H), 3.86-3.56 (m, 5H), 3.2 (s, 2H), 2.9 (s, 1H), 2.61 (s, 1H), 2.57-2.52 (m, 3H), 2.20-2.0 (m, 3H), 1.50 (s, 1H), 1.46-1.43 (m, 4H) |
| 489 | 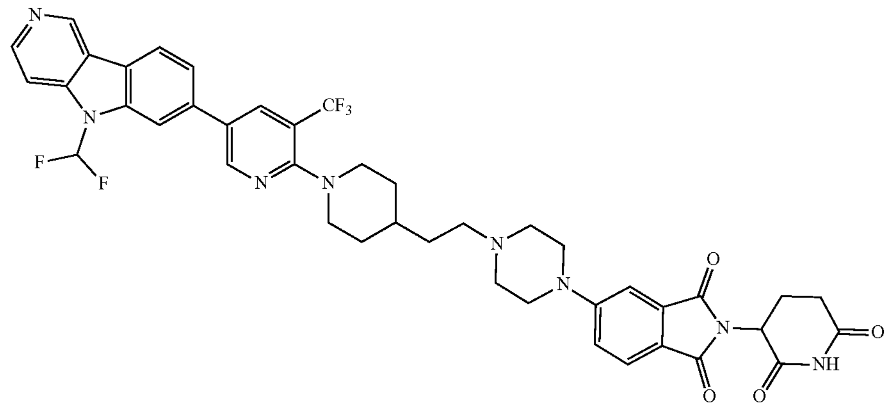 [SMILES: O=C1CCC(N2C(=O)c3ccc(N4CCN(CCC5CCN(c6ncc(-c7ccc8c9cnccc9n(C(F)F)c8c7)cc6C(F)(F)F)CC5)CC4)cc3C2=O)C(=O)N1] | 5-(4-(2-(1-(5-(5-(difluoromethyl)-5H-pyrido[4,3-b]indol-7-yl)-3-(trifluoromethyl)pyridin-2-yl)piperidin-4-yl)ethyl)piperazin-1-yl)-2-(2,6-dioxopiperidin-3-yl)isoindoline-1,3-dione | A | 815.3 | $^1$H NMR (400 MHz, DMSO-$d_6$) δ: 11.09 (s, 1 H), 9.94-9.68 (m, 2 H), 9.00-8.97 (m, 1 H), 8.86 (d, J = 6.40 Hz, 1 H), 8.49 (s, 2 H), 8.46 (d, J = 2.40 Hz, 1 H), 8.38 (s, 1 H), 8.25 (d, J = 6.40 Hz, 1 H), 8.04-7.99 (m, 1 H), 7.77 (d, J = 8.40 Hz, 1 H), 7.50 (d, J = 2.00 Hz, 1 H), 7.37 (dd, J = 8.8, 2.00 Hz, 1 H), 5.10 (dd, J = 12.8, 5.20 Hz, 1 H), 4.30-4.20 (m, 2 H), 3.70 (d, J = 12.40 Hz, 6 H), 3.25 (dd, J = 8.00, 7.20 Hz, 4 H), 3.02-2.92 (m, 3 H), 2.91-2.84 (m, 1 H), 2.60 (d, J = 16.40 Hz, 1 H), 2.06-1.99 (m, 1 H), 1.83 (d, J = 11.20 Hz, 2 H), 1.76-1.67 (m, 2 H), 1.63-1.54 (m, 1 H), 1.41-1.30 (m, 2 H). |
| 490 | 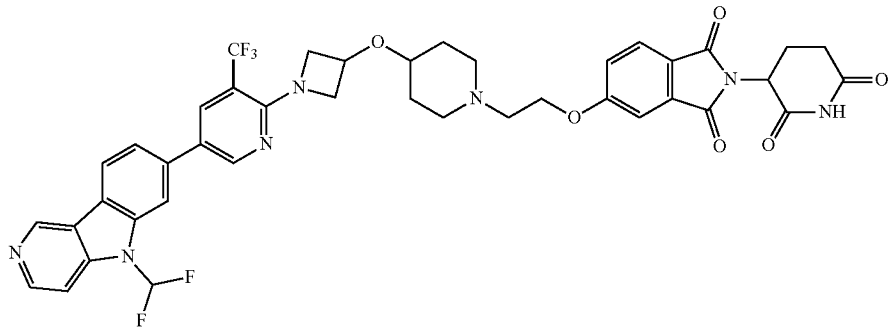 [SMILES: O=C1CCC(N2C(=O)c3ccc(OCCN4CCC(OC5CN(c6ncc(-c7ccc8c9cnccc9n(C(F)F)c8c7)cc6C(F)(F)F)C5)CC4)cc3C2=O)C(=O)N1] | 5-(2-(4-((1-(5-(5-(difluoromethyl)-5H-pyrido[4,3-b]indol-7-yl)-3-(trifluoromethyl)pyridin-2-yl)azetidin-3-yl)oxy)piperidin-1-yl)ethoxy)-2-(2,6-dioxopiperidin-3-yl)isoindoline-1,3-dione | | 818.3 | $^1$H NMR (400 MHz, DMSO-$d_6$) δ: 11.11 (s, 1 H), 9.85-9.76 (m, 1 H), 9.71-9.42 (m, 1 H), 8.90-8.82 (m, 2 H), 8.80-8.39 (m, 2 H), 8.32 (s, 2 H), 8.23 (d, J = 6.4 Hz, 1 H), 8.00-7.86 (m, 2 H), 7.56 (d, J = 2.40 Hz, 1 H), 7.43 (dd, J = 8.40, 2.40 Hz, 1 H), 5.13 (dd, J = 13.20, 5.20 Hz, 1 H), 4.63-4.52 (m, 3 H), 4.49-4.40 (m, 2 H), 4.11-3.95 (m, 3 H), 3.88-3.78 (m, 2 H), 3.16-3.07 (m, 2 H), 2.98-2.81 (m, 2 H), 2.64-2.55 (m, 3 H), 2.24-2.14 (m, 1 H), 2.08-1.91 (m, 3 H), 1.77-1.65 (m, 1 H). |

TABLE 1-continued

| | | | | | |
|---|---|---|---|---|---|
| 491 | 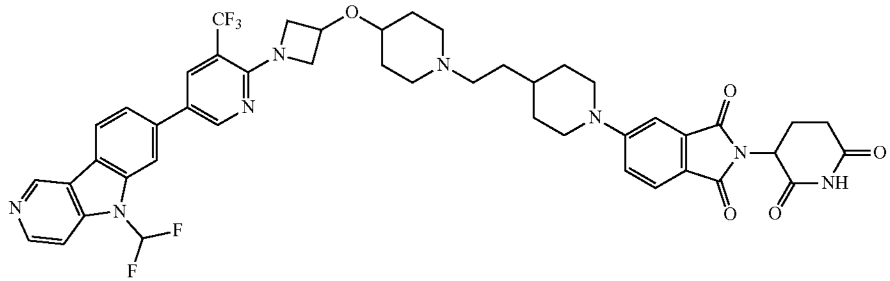 [SMILES: O=C1CCC(N2C(=O)c3ccc(N4CCC(CCN5CCC(OC6CN(c7ncc(-c8ccc9c%10cnccc%10n(C(F)F)c9c8)cc7C(F)(F)F)C6)CC5)CC4)cc3C2=O)C(=O)N1] | 5-(4-(2-(4-((1-(5-(5-(difluoromethyl)-5H-pyrido[4,3-b]indol-7-yl)-3-(trifluoromethyl)pyridin-2-yl)azetidin-3-yl)oxy)piperidin-1-yl)ethyl)piperidin-1-yl)-2-(2,6-dioxopiperidin-3-yl)isoindoline-1,3-dione | | 885.3 | $^1$H NMR (400 MHz, DMSO-$d_6$) δ: 11.06 (s, 1H), 9.48 (s, 1H), 8.84 (d, J = 2.1 Hz, 1H), 8.67-8.33 (m, 3H), 8.27 (d, J = 2.2 Hz, 1H), 8.22 (d, J = 8.4 Hz, 2H), 7.84-7.76 (m, 2H), 7.64 (d, J = 8.6 Hz, 1H), 7.29 (d, J = 2.2 Hz, 1H), 7.25-7.20 (m, 1H), 5.11-5.00 (m, 1H), 4.61-4.51 (m, 1H), 4.46-4.38 (m, 2H), 4.05-3.96 (m, 4H), 3.00-2.83 (m, 4H), 2.77-2.69 (m, 2H), 2.60-2.55 (m, 2H), 2.32 (br s, 2H), 2.06-1.98 (m, 3H), 1.85-1.72 (m, 4H), 1.64-1.52 (m, 1H), 1.51-1.35 (m, 4H), 1.22-1.13 (m, 2H) |
| 492 | 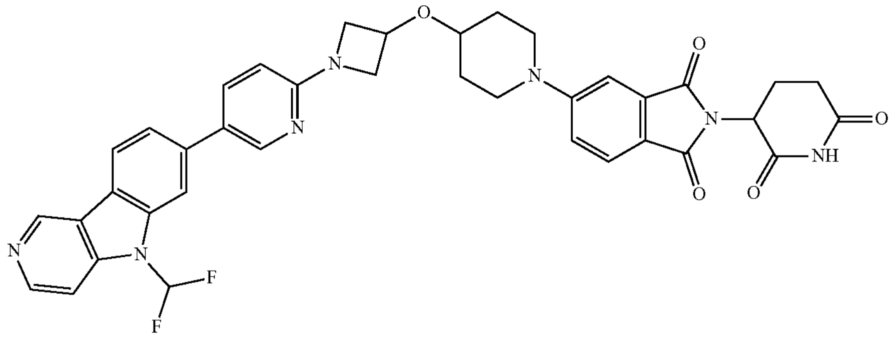 [SMILES: O=C1CCC(N2C(=O)c3ccc(N4CCC(OC5CN(c6ccc(-c7ccc8c9cnccc9n(C(F)F)c8c7)cn6)C5)CC4)cc3C2=O)C(=O)N1] | 2-(2,6-dioxopiperidin-3-yl)-5-(4-((1-(5-(5-methyl-5H-pyrido[4,3-b]indol-7-yl)pyridin-2-yl)azetidin-3-yl)oxy)piperidin-1-yl)isoindoline-1,3-dione | | 670.3 | 1H NMR (400 MHz, DMSO-d6) δ: 1.55 (q, J = 9.2 Hz, 2 H), 1.89-2.03 (m, 3 H), 2.54-2.64 (m, 2 H), 3.16-3.29 (m, 2 H), 3.66-3.77 (m, 2 H), 3.83 (d, J = 8.8 Hz, 4 H), 3.95 (s, 3 H), 4.25-4.31 (m, 2 H), 4.60-4.69 (m, 1 H), 5.07 (d, J = 12.8 Hz, 1 H), 6.55 (d, J = 8.4 Hz, 1 H), 7.28 (d, J = 8.8 Hz, 1 H), 7.36 (d, J = 2.0 Hz, 1 H), 7.55-7.63 (m, 2 H), 7.67 (d, J = 8.4 Hz, 1 H), 7.90 (s, 1 H), 8.03 (d, J = 8.8 Hz, 1 H), 8.20 (br s, 1 H), 8.29 (d, J = 8.0 Hz, 1 H), 8.49 (d, J = 5.6 Hz, 1 H), 8.59 (d, J = 2.4 Hz, 1 H), 9.34 (s, 1 H), 11.08 (s, 1 H) |
| 493 | 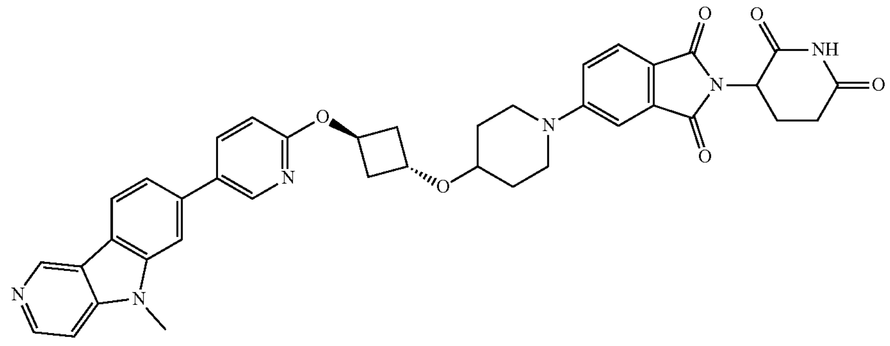 [SMILES: Cn1c2ccncc2c2ccc(-c3ccc(O[C@H]4C[C@H](OC5CCN(c6ccc7c(c6)C(=O)N(C6CCC(=O)NC6=O)C7=O)CC5)C4)nc3)cc21] | 2-(2,6-dioxopiperidin-3-yl)-5-(4-((1r,3r)-3-((5-(5-methyl-5H-pyrido[4,3-b]indol-7-yl)pyridin-2-yl)oxy)cyclobutoxy)piperidin-1-yl)isoindoline-1,3-dione | A | 685.3 | $^1$H NMR (400 MHz, DMSO-$d_6$) δ: 11.09 (s, 1H), 9.38 (s, 1H), 8.66 (d, J = 2.4 Hz, 1H), 8.51 (d, J = 5.6 Hz, 1H), 8.34 (d, J = 8.2 Hz, 1H), 8.27 (s, 1H), 8.21 (m, 1H), 8.00 (s, 1H), 7.73-7.60 (m, 3H), 7.36 (d, J = 2.0 Hz, 1H), 7.28 (m, 1H), 6.97 (d, J = 8.7 Hz, 1H), 5.35 (t, J = 4.4 Hz, 1H), 5.08 (m, 1H), 4.44 (t, J = 6.0 Hz, 1H), 3.98 (s, 3H), 3.90-3.82 (m, 2H), 3.64 (m, 1H), 3.28 (s, 2H), 2.90 (s, 1H), 2.64-2.55 (m, 2H), 2.48-2.40 (m, 4H), 2.07-1.99 (m, 1H), 1.97-1.89 (m, 2H), 1.60-1.42 (m, 2H) |

TABLE 1-continued

| | | | | | |
|---|---|---|---|---|---|
| 494 | 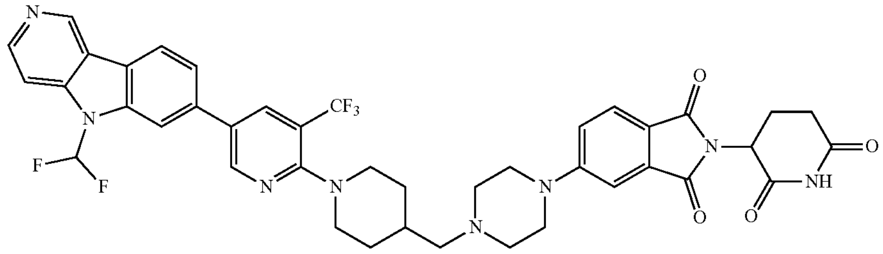 [SMILES: O=C1CCC(N2C(=O)c3ccc(N4CCN(CC5CCN(c6ncc(-c7ccc8c9cnccc9n(C(F)F)c8c7)cc6C(F)(F)F)CC5)CC4)cc3C2=O)C(=O)N1] | 5-(4-((1-(5-(5-(difluoromethyl)-5H-pyrido[4,3-b]indol-7-yl)-3-(trifluoromethyl)pyridin-2-yl)piperidin-4-yl)methyl)piperazin-1-yl)-2-(2,6-dioxopiperidin-3-yl)isoindoline-1,3-dione | A | 801.3 | $^1$H NMR (400 MHz, DMSO-$d_6$) δ: 11.09 (s, 1H), 9.81 (s, 1H), 9.01 (d, J = 2.4 Hz, 1H), 8.85 (d, J = 6.4 Hz, 1H), 8.79-8.54 (m, 2H), 8.47 (d, J = 2.4 Hz, 1H), 8.38 (s, 1H), 8.21 (d, J = 6.4 Hz, 1H), 8.02 (dd, J = 1.2, 8.4 Hz, 1H), 7.78 (d, J = 8.4 Hz, 1H), 7.51 (d, J = 1.6 Hz, 1H), 7.38 (dd, J = 2.0, 8.4 Hz, 1H), 5.10 (dd, J = 5.6, 12.8 Hz, 1H), 4.23 (dd, J = 3.6, 9.6 Hz, 2H), 3.70 (d, J = 12.8 Hz, 5H), 3.18 (s, 3H), 2.02 (t, J = 11.6 Hz, 3H), 2.96-2.84 (m, 2H), 2.64-2.54 (m, 2H), 2.20-2.09 (m, 1H), 2.08-2.00 (m, 1H), 1.92 (d, J = 10.8 Hz, 2H), 1.47-1.34 (m, 2H) |
| 495 | 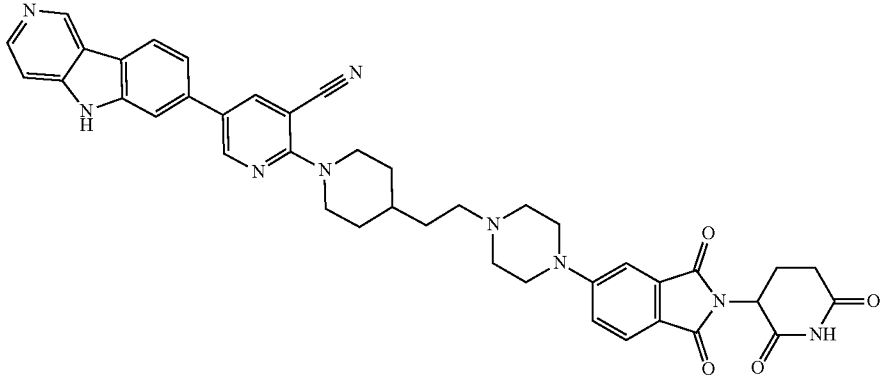 [SMILES: N#Cc1cc(-c2ccc3c(c2)[nH]c2ccncc23)cnc1N1CCC(CCN2CCN(c3ccc4c(c3)C(=O)N(C3CCC(=O)NC3=O)C4=O)CC2)CC1] | 2-(4-(2-(4-(2-(2,6-dioxopiperidin-3-yl)-1,3-dioxoisoindolin-5-yl)piperazin-1-yl)ethyl)piperidin-1-yl)-5-(5H-pyrido[4,3-b]indol-7-yl)nicotinonitrile | | 722.3 | $^1$H NMR (400 MHz, DMSO-$d_6$) δ: 13.20-12.89 (m, 1H), 11.10 (s, 1H), 9.72 (s, 1H), 8.89 (d, J = 2.6 Hz, 1H), 8.65 (d, J = 6.7 Hz, 1H), 8.55 (d, J = 2.4 Hz, 1H), 8.50 (d, J = 8.3 Hz, 1H), 8.05 (s, 1H), 7.95 (d, J = 6.6 Hz, 1H), 7.84 (d, J = 8.4 Hz, 1H), 7.77 (d, J = 8.4 Hz, 1H), 7.49 (s, 1H), 7.40-7.32 (m, 1H), 5.18-5.02 (m, 1H), 4.38 (d, J = 13.1 Hz, 2H), 3.45-3.27 (m, 8H), 3.09 (s, 2H), 2.92-2.84 (m, 1H), 2.52 (s, 4H), 2.07-2.00 (m, 1H), 1.86 (d, J = 11.2 Hz, 2H), 1.69 (s, 3H), 1.38-1.28 (m, 2H) |
| 496 | 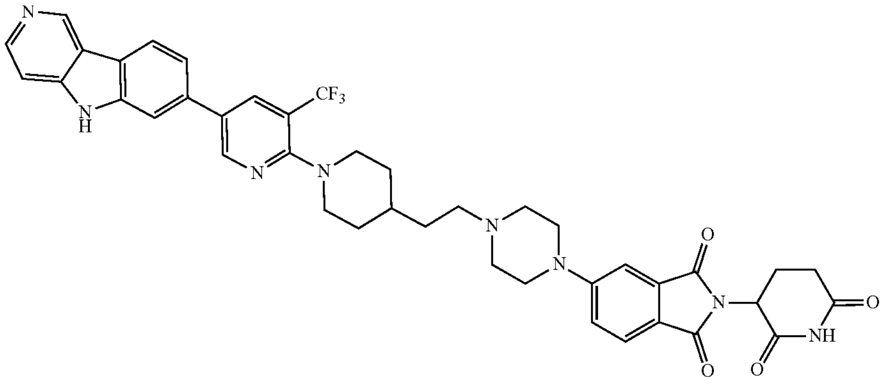 [SMILES: O=C1CCC(N2C(=O)c3ccc(N4CCN(CCC5CCN(c6ncc(-c7ccc8c(c7)[nH]c7ccncc78)cc6C(F)(F)F)CC5)CC4)cc3C2=O)C(=O)N1] | 5-(4-(2-(1-(5-(5H-pyrido[4,3-b]indol-7-yl)-3-(trifluoromethyl)pyridin-2-yl)piperidin-4-yl)ethyl)piperazin-1-yl)-2-(2,6-dioxopiperidin-3-yl)isoindoline-1,3-dione | | 765.3 | $^1$H NMR (400 MHz, DMSO-$d_6$) δ: 13.31-13.06 (m, 1 H), 11.21-10.98 (m, 1 H), 9.95-9.70 (m, 2 H), 8.97 (d, J = 2.00 Hz, 1 H), 8.68 (d, J = 6.80 Hz, 1 H), 8.55 (d, J = 8.40 Hz, 1 H), 8.41 (d, J = 2.40 Hz, 1 H), 8.12 (s, 1 H), 8.03 (d, J = 6.80 Hz, 1 H), 7.90 (d, J = 8.80 Hz, 1 H), 7.78 (d, J = 8.40 Hz, 1 H), 7.50 (s, 1 H), 7.38 (dd, J = 8.80, 1.60 Hz, 1 H), 5.10 (dd, J = 12.80, 5.60 Hz, 1 H), 4.36-4.09 (m, 2 H), 3.74-3.59 (m, 5 H), 3.31-3.14 (m, 6 H), 2.97 (t, J = 11.20 Hz, 2 H), 2.63-2.54 (m, 2 H), 2.06-2.00 (m, 1 H), 1.87-1.80 (m, 2 H), 1.76-1.67 (m, 2 H), 1.61-1.52 (m, 1 H), 1.40-1.30 (m, 2 H). |

TABLE 1-continued

| | | | | | |
|---|---|---|---|---|---|
| 497 | 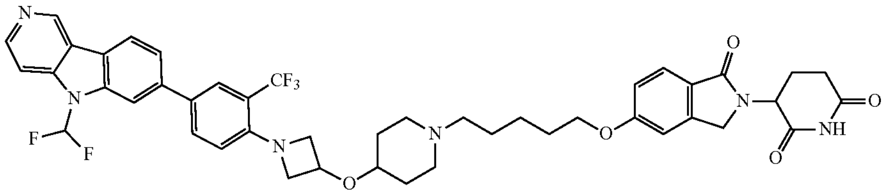 [SMILES: O=C1CCC(N2Cc3cc(OCCCCCN4CCC(OC5CN(c6ccc(-c7ccc8c9cnccc9n(C(F)F)c8c7)cc6C(F)(F)F)C5)CC4)ccc3C2=O)C(=O)N1] | 3-(5-((5-(4-((1-(5-(5-(difluoromethyl)-5H-pyrido[4,3-b]indol-7-yl)-3-(trifluoromethyl)pyridin-2-yl)azetidin-3-yl)oxy)piperidin-1-yl)pentyl)oxy)-1-oxoisoindolin-2-yl)piperidine-2,6-dione | | 846.3 | $^1$H NMR (400 MHz, DMSO-$d_6$) δ: 10.96 (s, 1 H), 9.85 (s, 1 H), 9.53-9.35 (m, 1 H), 8.92-8.81 (m, 2 H), 8.80-8.45 (m, 2 H), 8.36-8.23 (m, 3 H), 7.97 (d, J = 8.40 Hz, 1 H), 7.63 (dd, J = 8.40, 1.60 Hz, 1 H), 7.16 (s, 1 H), 7.05 (d, J = 8.40 Hz, 1 H), 5.07 (dd, J = 13.20, 4.80 Hz, 1 H), 4.65-4.58 (m, 1 H), 4.46-4.26 (m, 4 H), 4.09-4.01 (m, 4 H), 3.36 (d, J = 11.60 Hz, 2 H), 3.10 (d, J = 5.60 Hz, 3 H), 3.00-2.86 (m, 3 H), 2.62 (s, 2 H), 2.38 (d, J = 13.60 Hz, 1 H), 2.19-2.13 (m, 1 H), 1.99-1.90 (m, 2 H), 1.84-1.67 (m, 5 H), 1.52-1.41 (m, 2 H). |
| 498 | 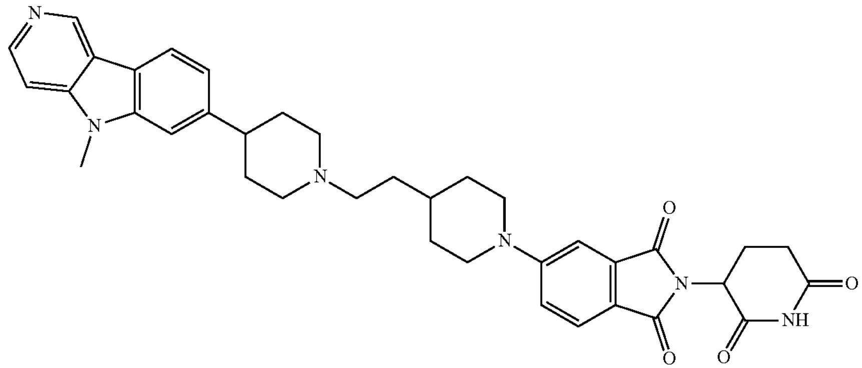 [SMILES: Cn1c2ccncc2c2ccc(C3CCN(CCC4CCN(c5ccc6c(c5)C(=O)N(C5CCC(=O)NC5=O)C6=O)CC4)CC3)cc21] | 2-(2,6-dioxopiperidin-3-yl)-5-(4-(2-(4-(5-methyl-5H-pyrido[4,3-b]indol-7-yl)piperidin-1-yl)ethyl)piperidin-1-yl)isoindoline-1,3-dione | A | 633.3 | 1H NMR (400 MHz, DMSO-d6) δ: 1.18-1.31 (m, 2 H), 1.46 (q, J = 6.8 Hz, 2 H), 1.64 (br s, 1 H), 1.80-1.91 (m, 5 H), 1.97-2.10 (m, 3 H), 2.42 (d, J = 7.2 Hz, 2 H), 2.56-2.80 (m, 2 H), 2.80-3.12 (m, 6 H), 3.89 (s, 3 H), 4.06 (d, J = 12.8 Hz, 3 H), 5.07 (d, J = 12.8 Hz, 1 H), 7.18-7.28 (m, 2 H), 7.32 (s, 1 H), 7.52-7.62 (m, 2 H), 7.62-7.70 (m, 1 H), 8.15 (d, J = 8.0 Hz, 1 H), 8.24 (s, 2 H), 8.46 (d, J = 5.6 Hz, 1 H), 9.28 (s, 1 H), 11.08 (s, 1 H) |
| 499 | 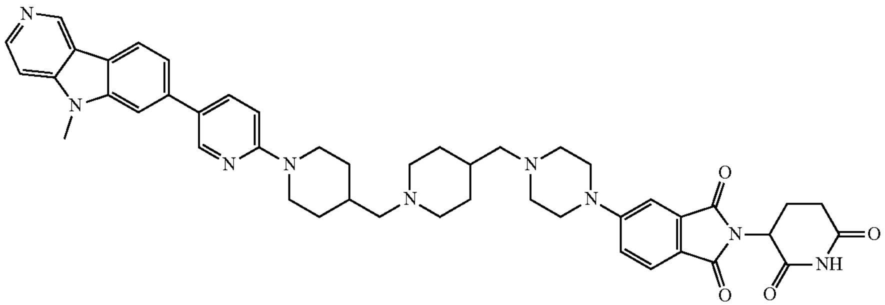 [SMILES: Cn1c2ccncc2c2ccc(-c3ccc(N4CCC(CN5CCC(CN6CCN(c7ccc8c(c7)C(=O)N(C7CCC(=O)NC7=O)C8=O)CC6)CC5)CC4)nc3)cc21] | 2-(2,6-dioxopiperidin-3-yl)-5-(4-((1-((1-(5-(5-methyl-5H-pyrido[4,3-b]indol-7-yl)pyridin-2-yl)piperidin-4-yl)methyl)piperidin-4-yl)methyl)piperazin-1-yl)isoindoline-1,3-dione | | | |

TABLE 1-continued

| | | | | | |
|---|---|---|---|---|---|
| 500 | 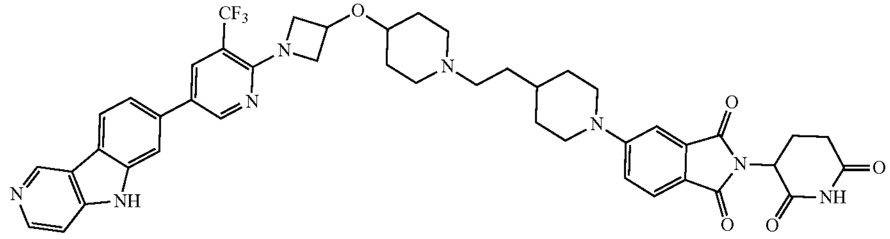 [SMILES: O=C1CCC(N2C(=O)c3ccc(N4CCC(CCN5CCC(OC6CN(c7ncc(-c8ccc9c(c8)[nH]c8ccncc89)cc7C(F)(F)F)C6)CC5)CC4)cc3C2=O)C(=O)N1] | 5-(4-(2-(4-((1-(5-(5H-pyrido[4,3-b]indol-7-yl)-3-(trifluoromethyl)pyridin-2-yl)azetidin-3-yl)oxy)piperidin-1-yl)ethyl)piperidin-1-yl)-2-(2,6-dioxopiperidin-3-yl)isoindoline-1,3-dione | | 835.3 | $^1$H NMR (400 MHz, methanol-$d_4$) δ 9.26 (s, 1H), 8.47 (d, J = 5.5 Hz, 1H), 8.29 (d, J = 8.2 Hz, 1H), 8.04 (d, J = 6.4 Hz, 1H), 7.81 (s, 1H), 7.67-7.54 (m, 2 H), 7.09 (d, J = 9.6 Hz, 1H), 6.61 (d, J = 8.9 Hz, 1H), 4.44-4.32 (m, 3H), 4.00 (s, 1H), 3.94 (d, J = 9.6 Hz, 2H), 2.90 (d, J = 12.7 Hz, 2H), 1.95 (s, 1H), 1.31 (s, 1H). |
| 501 | 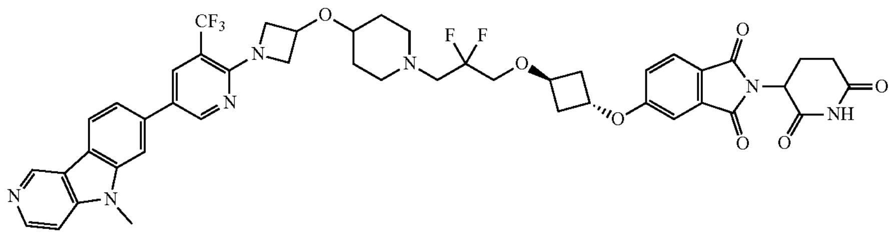 [SMILES: Cn1c2ccncc2c2ccc(-c3cnc(N4CC(OC5CCN(CC(F)(F)CO[C@H]6C[C@H](Oc7ccc8c(c7)C(=O)N(C7CCC(=O)NC7=O)C8=O)C6)CC5)C4)c(C(F)(F)F)c3)cc21] | 5-((1r,3r)-3-(2,2-difluoro-3-(4-((1-(5-(5-methyl-5H-pyrido[4,3-b]indol-7-yl)-3-(trifluoromethyl)pyridin-2-yl)azetidin-3-yl)oxy)piperidin-1-yl)propoxy)cyclobutoxy)-2-(2,6-dioxopiperidin-3-yl)isoindoline-1,3-dione | | 902.3 | $^1$H NMR (400 MHz, DMSO-$d_6$) δ: 11.11 (s, 1H), 9.36 (s, 1H), 8.88 (d, J = 2.0 Hz, 1H), 8.50 (d, J = 6.0 Hz, 1H), 8.33 (s, 2H), 8.26 (s, 1H), 8.03 (s, 1H), 7.85 (d, J = 8.8 Hz, 1H), 7.72-7.57 (m, 2H), 7.39-7.20 (m, 2H), 5.12 (m, 2H), 4.72-4.52 (m, 2H), 4.46-4.35 (m, 2H), 4.02-3.90 (m, 6H), 3.73-3.66 (m, 2H), 3.02-2.72 (m, 7H), 2.55 (s, 3H), 2.43-2.35 (m, 2H), 2.03 (s, 2H), 1.82 (s, 2H), 1.59-1.43 (m, 2H) |
| 502 | 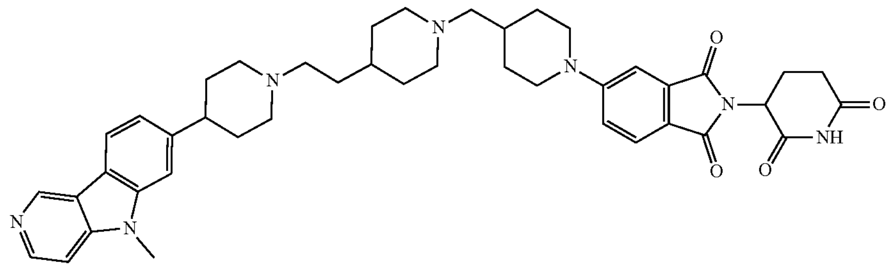 [SMILES: Cn1c2ccncc2c2ccc(C3CCN(CCC4CCN(CC5CCN(c6ccc7c(c6)C(=O)N(C6CCC(=O)NC6=O)C7=O)CC5)CC4)CC3)cc21] | 2-(2,6-dioxopiperidin-3-yl)-5-(4-((4-(2-(4-(5-methyl-5H-pyrido[4,3-b]indol-7-yl)piperidin-1-yl)ethyl)piperidin-1-yl)methyl)piperidin-1-yl)isoindoline-1,3-dione | A | 730.4 | $^1$H NMR (400 MHz, DMSO-$d_6$) δ: 11.07 (s, 1 H), 9.97-9.65 (m, 2 H), 9.15-9.01 (m, 1 H), 8.76 (d, J = 6.80 Hz, 1 H), 8.44 (d, J = 8.00 Hz, 1 H), 8.21 (d, J = 6.80 Hz, 1 H), 7.76 (s, 1 H), 7.68 (d, J = 8.40 Hz, 1 H), 7.46 (d, J = 8.40 Hz, 1 H), 7.36 (s, 1 H), 7.28 (d, J = 8.80 Hz, 1 H), 5.07 (dd, J = 12.80, 5.20 Hz, 1 H), 4.11 (s, 1 H), 4.08 (s, 3 H), 3.67 (d, J = 11.20 Hz, 2 H), 3.56 (d, J = 11.60 Hz, 3 H), 3.19-3.07 (m, 5 H), 3.05-2.96 (m, 4 H), 2.94-2.83 (m, 3 H), 2.63-2.53 (m, 2 H), 2.19-1.89 (m, 6 H), 1.93-1.81 (m, 4 H), 1.71-1.42 (m, 5 H), 1.34-1.23 (m, 2 H). |

TABLE 1-continued

| | | | | |
|---|---|---|---|---|
| 503 | 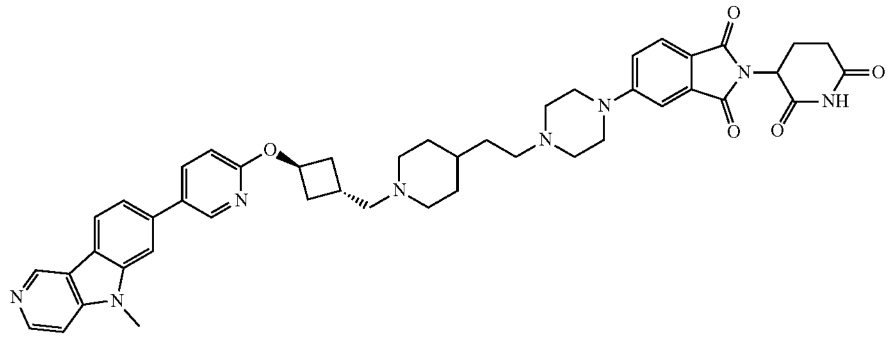 [SMILES: Cn1c2ccncc2c2ccc(-c3ccc(O[C@H]4C[C@H](CN5CCC(CCN6CCN(c7ccc8c(c7)C(=O)N(C7CCC(=O)NC7=O)C8=O)CC6)CC5)C4)nc3)cc21] | 2-(2,6-dioxopiperidin-3-yl)-5-(4-(2-(1-(((1r,3r)-3-((5-(5-methyl-5H-pyrido[4,3-b]indol-7-yl)pyridin-2-yl)oxy)cyclobutyl)methyl)piperidin-4-yl)ethyl)piperazin-1-yl)isoindoline-1,3-dione | 795.4 | $^{1}$H NMR (400 MHz, methanol-$d_4$): δ 9.34 (s, 1H), 8.57-8.48 (m, 3H), 8.36 (d, J = 8.2 Hz, 1H), 8.15 (ddd, J = 8.4, 5.0, 2.6 Hz, 2H), 7.90 (s, 1H), 7.75-7.68 (m, 2H), 7.65 (d, J = 8.1 Hz, 1H), 7.40 (d, J = 2.2 Hz, 1H), 7.27 (dd, J = 8.6, 2.3 Hz, 2H), 6.94 (dd, J = 12.7, 8.9 Hz, 2H), 5.26-5.18 (m, 1H), 5.09 (dd, J = 12.5, 5.4 Hz, 2H), 4.05 (s, 2H), 3.50 (s, 2H), 2.86 (dd, J = 14.4, 4.9 Hz, 2H), 2.81-2.73 (m, 2H), 2.70 (d, J = 4.8 Hz, 4H), 2.53 (dd, J = 16.3, 8.3 Hz, 4H), 2.06 (d, J = 11.9 Hz, 1H). |
| 504 | 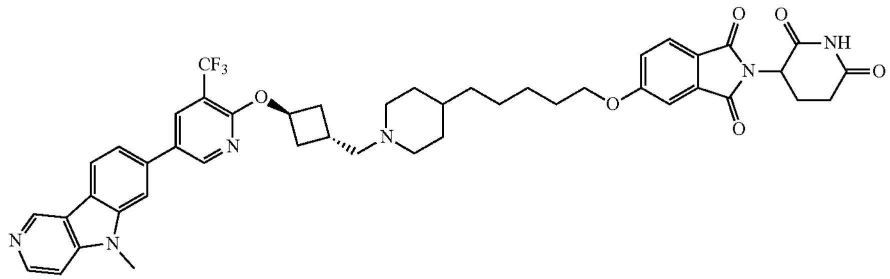 [SMILES: Cn1c2ccncc2c2ccc(-c3cnc(O[C@H]4C[C@H](CN5CCC(CCCCCOc6ccc7c(c6)C(=O)N(C6CCC(=O)NC6=O)C7=O)CC5)C4)c(C(F)(F)F)c3)cc21] | 2-(2,6-dioxopiperidin-3-yl)-5-((5-(1-(((1r,3r)-3-((5-(5-methyl-5H-pyrido[4,3-b]indol-7-yl)-3-(trifluoromethyl)pyridin-2-yl)oxy)cyclobutyl)methyl)piperidin-4-yl)pentyl)oxy)isoindoline-1,3-dione | 837.3 | $^{1}$H NMR (400 MHz, methanol-$d_4$): δ 9.29 (s, 1H), 8.75 (s, 1H), 8.49 (d, J = 5.9 Hz, 2H), 8.40-8.32 (m, 4H), 7.91 (s, 1H), 7.82 (d, J = 8.3 Hz, 2H), 7.63 (d, J = 6.5 Hz, 2H), 7.41 (d, J = 2.2 Hz, 2H), 7.33 (d, J = 8.3 Hz, 2H), 5.50 (s, 1H), 5.12 (dd, J = 12.6, 5.3 Hz, 3H), 4.18 (t, J = 6.4 Hz, 4H), 4.02 (s, 3H), 3.37 (s, 1H), 2.77 (d, J = 13.3 Hz, 2H), 2.42 (d, J = 6.0 Hz, 2H), 1.31 (s, 3H), 0.17 (s, 1H), −0.12 (s, 1H). |
| 505 | 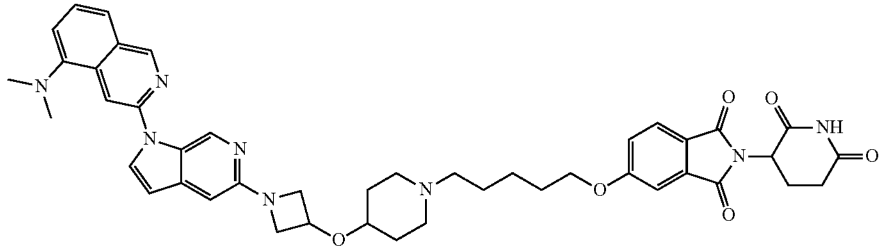 [SMILES: CN(C)c1cccc2cnc(-n3ccc4cc(N5CC(OC6CCN(CCCCCOc7ccc8c(c7)C(=O)N(C7CCC(=O)NC7=O)C8=O)CC6)C5)ncc43)cc12] | 5-((5-(4-((1-(1-(5-(dimethylamino)isoquinolin-3-yl)-1H-pyrrolo[2,3-c]pyridin-5-yl)azetidin-3-yl)oxy)piperidin-1-yl)pentyl)oxy)-2-(2,6-dioxopiperidin-3-yl)isoindoline-1,3-dione | 785.4 | $^{1}$H NMR (300 MHz, DMSO-$d_6$): δ 11.12 (s, 1H), 9.34 (s, 1H), 9.21 (s, 1H), 8.28 (s, 1H), 8.03 (s, 1H), 7.88-7.77 (m, 2H), 7.53 (t, 1H), 7.44-7.30 (m, 3H), 6.69-6.56 (m, 2H), 5.18-5.06 (m, 1H), 4.60-4.50 (m, 1H), 4.18 (s, 4H), 3.73-3.65 (m, 2H), 2.90 (s, 7H), 2.80-2.66 (m, 2H), 2.35-2.20 (m, 3H), 2.10-1.95 (m, 3H), 1.89-1.70 (m, 5H), 1.52-1.35 (m, 7H). |

TABLE 1-continued

| | | | | | |
|---|---|---|---|---|---|
| 506 | 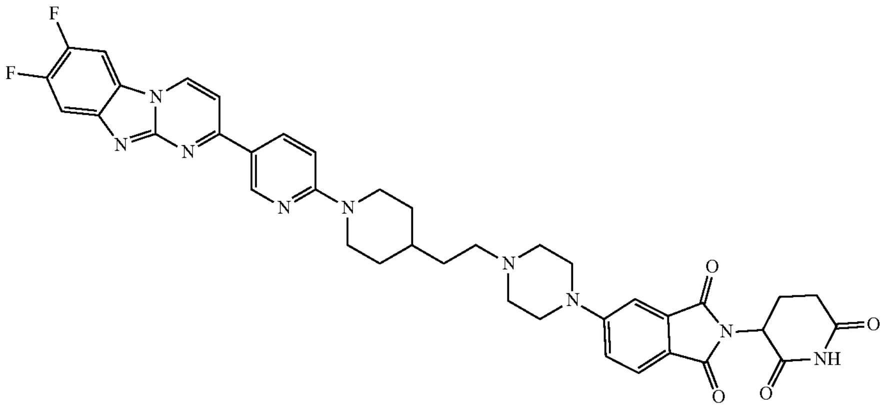 [SMILES: O=C1CCC(N2C(=O)c3ccc(N4CCN(CCC5CCN(c6ccc(-c7ccn8c(n7)nc7cc(F)c(F)cc78)cn6)CC5)CC4)cc3C2=O)C(=O)N1] | 5-(4-(2-(1-(5-(7,8-difluorobenzo[4,5]imidazo[1,2-a]pyrimidin-2-yl)pyridin-2-yl)piperidin-4-yl)ethyl)piperazin-1-yl)-2-(2,6-dioxopiperidin-3-yl)isoindoline-1,3-dione | | 734.3 | $^1$H NMR (400 MHz, DMSO-$d_6$) δ: 11.11 (s, 1H), 9.66-9.55 (m, 1H), 9.44 (d, J = 7.2 Hz, 1H), 9.11 (d, J = 2.4 Hz, 1H), 8.54 (dd, J = 7.2, 10.0 Hz, 1H), 8.44 (dd, J = 2.4, 9.2 Hz, 1H), 7.97-7.87 (m, 2H), 7.77 (d, J = 8.4 Hz, 1H), 7.50 (s, 1H), 7.37 (dd, J = 1.6, 8.4 Hz, 1H), 7.08 (d, J = 9.6 Hz, 1H), 5.10 (dd, J = 5.4, 12.8 Hz, 1H), 4.54 (d, J = 13.2 Hz, 2H), 4.26 (d, J = 1.6 Hz, 2H), 3.63 (s, 2H), 3.22-3.13 (m, 4H), 2.92 (s, 4H), 2.61-2.55 (m, 3H), 2.05-2.00 (m, 1H), 1.81 (d, J = 12.4 Hz, 2H), 1.67 (s, 3H), 1.23-1.17 (m, 2H) |
| 507 | 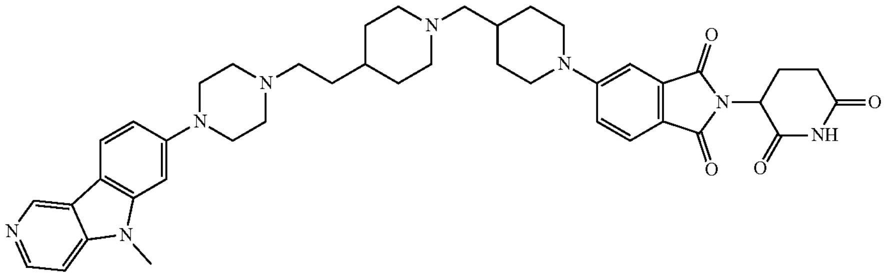 [SMILES: Cn1c2ccncc2c2ccc(N3CCN(CCC4CCN(CC5CCN(c6ccc7c(c6)C(=O)N(C6CCC(=O)NC6=O)C7=O)CC5)CC4)CC3)cc21] | 2-(2,6-dioxopiperidin-3-yl)-5-(4-((4-(2-(4-(5-methyl-5H-pyrido[4,3-b]indol-7-yl)piperazin-1-yl)ethyl)piperidin-1-yl)methyl)piperidin-1-yl)isoindoline-1,3-dione | | 731.4 | $^1$H NMR (400 MHz, DMSO-$d_6$) δ: 11.10 (s, 1 H), 10.27-10.04 (m, 1 H), 9.55 (s, 1 H), 9.11-8.99 (m, 1 H), 8.71-8.61 (m, 1 H), 8.31 (d, J = 8.80 Hz, 1 H), 8.11 (d, J = 6.80 Hz, 1 H), 7.74-7.62 (m, 1 H), 7.37 (d, J = 5.60 Hz, 2 H), 7.29 (t, J = 9.60 Hz, 2 H), 5.07 (dd, J = 12.80, 5.20 Hz, 1 H), 4.24-4.06 (m, 4 H), 4.03 (s, 3 H), 3.76-3.61 (m, 2 H), 3.59-3.52 (m, 2 H), 3.25-3.17 (m, 6 H), 3.03-2.95 (m, 4 H), 2.94-2.84 (m, 3 H), 2.63-2.54 (m, 2 H), 2.20-2.10 (m, 1 H), 2.07-1.99 (s, 1 H), 2.05 (m, 1 H), 1.97-1.80 (m, 4 H), 1.72-1.64 (m, 2 H), 1.53-1.42 (m, 2 H), 1.30-1.21 (m, 2 H). |
| 508 | 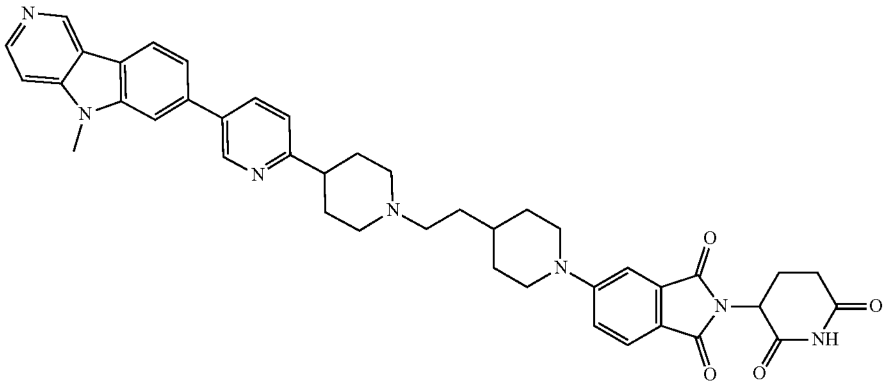 [SMILES: Cn1c2ccncc2c2ccc(-c3ccc(C4CCN(CCC5CCN(c6ccc7c(c6)C(=O)N(C6CCC(=O)NC6=O)C7=O)CC5)CC4)nc3)cc21] | 2-(2,6-dioxopiperidin-3-yl)-5-(4-(2-(4-(5-(5-methyl-5H-pyrido[4,3-b]indol-7-yl)pyridin-2-yl)piperidin-1-yl)ethyl)piperidin-1-yl)isoindoline-1,3-dione | A | 710.3 | $^1$H NMR (400 MHz, DMSO-$d_6$) δ: 11.08 (s, 1H), 9.79 (s, 1H), 9.27-9.13 (m, 1H), 9.08 (d, J = 2.4 Hz, 1H), 8.79 (d, J = 7.2 Hz, 1H), 8.59 (d, J = 8.4 Hz, 1H), 8.32-8.27 (m, 2H), 8.23 (d, J = 7.2 Hz, 1H), 7.94 (dd, J = 1.2, 8.4 Hz, 1H), 7.68 (d, J = 8.8 Hz, 1H), 7.50 (d, J = 8.8 Hz, 1H), 7.35 (s, 1H), 7.27 (dd, J = 2.1, 8.8 Hz, 1H), 5.07 (dd, J = 5.2, 12.8 Hz, 1H), 4.16 (s, 3H), 4.09 (dd, J = 1.2, 11.6 Hz, 2H), 3.67 (s, 3H), 3.22-3.15 (m, 2H), 3.14-3.04 (m, 3H), 3.02-2.87 (m, 3H), 2.63-2.53 (m, 2H), 2.14-2.00 (m, 4H), 1.80 (d, J = 13.6 Hz, 2H), 1.70-1.60 (m, 3H), 1.30-1.21 (m, 2H) |

TABLE 1-continued

| | | | | |
|---|---|---|---|---|
| 509 | 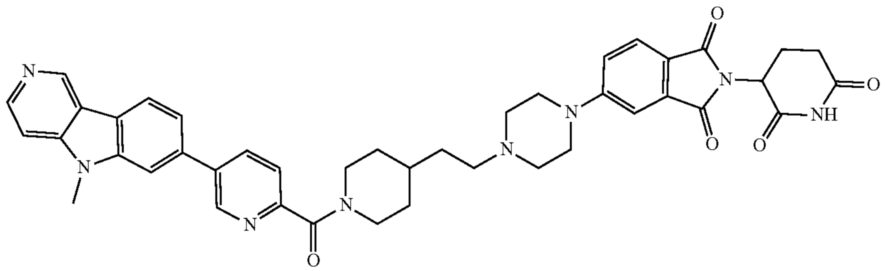 [SMILES: Cn1c2ccncc2c2ccc(-c3ccc(C(=O)N4CCC(CCN5CCN(c6ccc7c(c6)C(=O)N(C6CCC(=O)NC6=O)C7=O)CC5)CC4)nc3)cc21] | 2-(2,6-dioxopiperidin-3-yl)-5-(4-(2-(1-(5-(5-methyl-5H-pyrido[4,3-b]indol-7-yl)picolinoyl)piperidin-4-yl)ethyl)piperazin-1-yl)isoindoline-1,3-dione | 739.3 | 1H NMR (400 MHz, DMSO-d6) δ: 1.00-1.31 (m, 3 H), 1.48 (d, J = 6.4 Hz, 2 H), 1.60-1.72 (m, 2 H), 1.85 (d, J = 12.4 Hz, 1 H), 1.96-2.08 (m, 1 H), 2.55 (s, 4 H), 2.78-2.91 (m, 2 H), 3.08 (t, J = 12.0 Hz, 2 H), 3.46 (s, 6 H), 3.80 (d, J = 12.8 Hz, 1 H), 4.00 (s, 3 H), 4.53 (d, J = 13.2 Hz, 1 H), 5.08 (d, J = 12.8 Hz, 1 H), 7.27 (d, J = 8.8 Hz, 1 H), 7.36 (s, 1 H), 7.65-7.71 (m, 3 H), 7.76 (d, J = 8.0 Hz, 1 H), 8.14 (s, 1 H), 8.16 (s, 1 H), 8.36-8.44 (m, 2 H), 8.54 (d, J = 6.0 Hz, 1 H), 9.10 (d, J = 2.0 Hz, 1 H), 9.42 (s, 1 H), 11.09 (s, 1 H) |
| 510 | 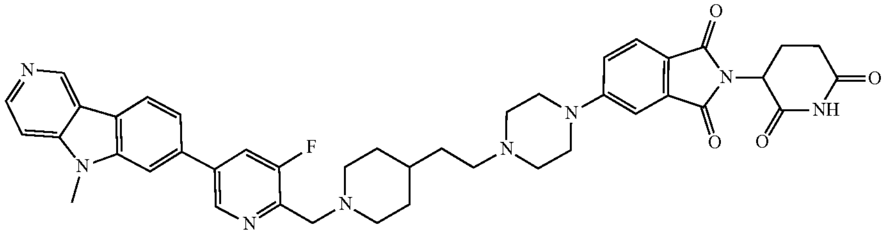 [SMILES: Cn1c2ccncc2c2ccc(-c3cnc(CN4CCC(CCN5CCN(c6ccc7c(c6)C(=O)N(C6CCC(=O)NC6=O)C7=O)CC5)CC4)c(F)c3)cc21] | 2-(2,6-dioxopiperidin-3-yl)-5-(4-(2-(1-((3-fluoro-5-(5-methyl-5H-pyrido[4,3-b]indol-7-yl)pyridin-2-yl)methyl)piperidin-4-yl)ethyl)piperazin-1-yl)isoindoline-1,3-dione | 743.3 | $^1$H NMR (400 MHz, DMSO-$d_6$) δ: 11.10 (s, 1 H), 10.32-10.12 (m, 1 H), 9.83 (s, 1 H), 9.15 (s, 1 H), 8.82 (d, J = 6.80 Hz, 1 H), 8.64 (d, J = 8.00 Hz, 1 H), 8.52 (dd, J = 11.20, 1.60 Hz, 1 H), 8.45 (s, 1 H), 8.25 (d, J = 6.80 Hz, 1 H), 8.09-8.05 (m, 1 H), 7.77 (d, J = 8.40 Hz, 1 H), 7.49 (s, 1 H), 7.37 (dd, J = 8.40, 1.60 Hz, 1 H), 5.10 (dd, J = 12.80, 5.60 Hz, 1 H), 4.62 (s, 2 H), 4.28-4.20 (m, 1 H), 4.18 (s, 3 H), 3.56 (d, J = 12.40 Hz, 6 H), 3.17 (dd, J = 13.60, 5.60 Hz, 7 H), 2.95-2.85 (m, 1 H), 2.64-2.52 (m, 2 H), 2.06-1.99 (m, 1 H), 1.91 (d, J = 12.80 Hz, 2 H), 1.73-1.41 (m, 5 H). |
| 511 | 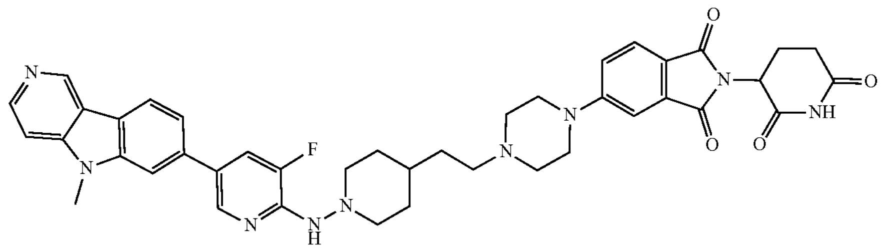 [SMILES: Cn1c2ccncc2c2ccc(-c3cnc(NN4CCC(CCN5CCN(c6ccc7c(c6)C(=O)N(C6CCC(=O)NC6=O)C7=O)CC5)CC4)c(F)c3)cc21] | 2-(2,6-dioxopiperidin-3-yl)-5-(4-(2-(4-((3-fluoro-5-(5-methyl-5H-pyrido[4,3-b]indol-7-yl)pyridin-2-yl)amino)cyclohexyl)ethyl)piperazin-1-yl)isoindoline-1,3-dione | 743.3 | $^1$H NMR (400 MHz, DMSO-$d_6$) δ: 11.07 (s, 1 H), 9.33 (s, 1 H), 8.53-8.45 (m, 1 H), 8.39 (s, 1 H), 8.27 (s, 1 H), 8.25 (s, 2 H), 7.96-7.88 (m, 2 H), 7.68 (d, J = 8.40 Hz, 1 H), 7.60 (d, J = 6.40 Hz, 2 H), 7.34 (s, 1 H), 7.26 (d, J = 8.40 Hz, 1 H), 6.56-6.28 (m, 1 H), 5.07 (dd, J = 12.80, 5.40 Hz, 1 H), 4.10-4.02 (m, 1 H), 4.10-3.95 (m, 1 H), 3.94 (s, 3 H), 2.93-2.83 (m, 2 H), 2.63-2.53 (m, 3 H), 2.44-2.34 (m, 3 H), 2.07-1.93 (m, 3 H), 1.89-1.62 (m, 4 H), 1.61-1.45 (m, 4 H), 1.45-1.25 (m, 4 H), 1.12-1.05 (m, 1 H). |

TABLE 1-continued

| | | | | | |
|---|---|---|---|---|---|
| 512 | 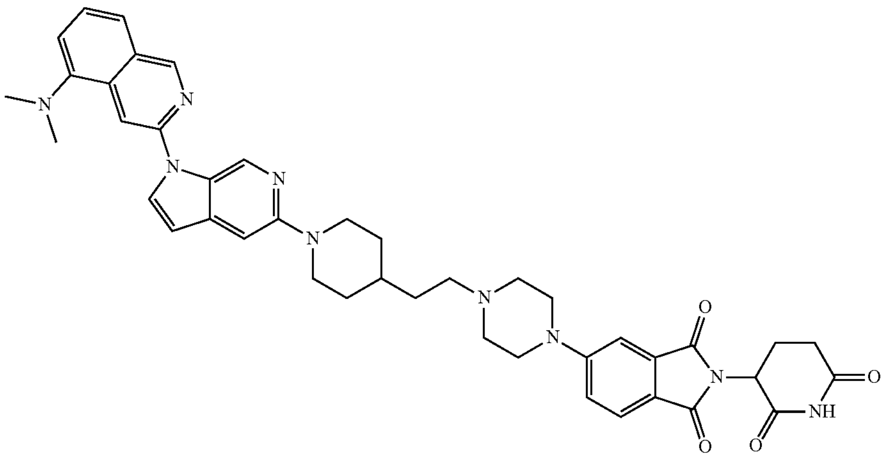 [SMILES: CN(C)c1cccc2cnc(-n3ccc4cc(N5CCC(CCN6CCN(c7ccc8c(c7)C(=O)N(C7CCC(=O)NC7=O)C8=O)CC6)CC5)ncc43)cc12] | 5-(4-(2-(1-(1-(5-(dimethylamino)iso-quinolin-3-yl)-1H-pyrrolo[2,3-c]pyridin-5-yl)piperidin-4-yl)ethyl)piperazin-1-yl)-2-(2,6-dioxopiperidin-3-yl)isoindoline-1,3-dione | A | 740.4 | $^1$H NMR (300 MHz, $CDCl_3$) δ 9.33 (s, 1H), 9.20 (s, 1H), 8.16-8.02 (m, 3H), 7.75-7.65 (m, 2H), 7.48 (t, 1H), 7.29-7.32 (m, 1H), 7.08 (d, 1H), 6.93 (s, 1H), 6.63 (s, 1H), 5.00-4.92 (m, 1H), 4.30-4.20 (m, 2H), 3.50 (s, 4H), 2.95 (s, 6H), 2.91-2.49 (m, 11H), 2.20-2.12 (m, 1H), 1.93-1.84 (m, 2H), 1.80-1.40 (m, 6H). |
| 513 | 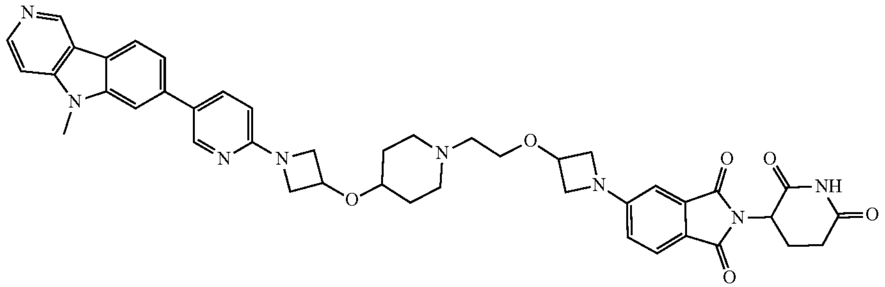 [SMILES: Cn1c2ccncc2c2ccc(-c3ccc(N4CC(OC5CCN(CCOC6CN(c7ccc8c(c7)C(=O)N(C7CCC(=O)NC7=O)C8=O)C6)CC5)C4)nc3)cc21] | 2-(2,6-dioxopiperidin-3-yl)-5-(3-(2-(4-((1-(5-(5-methyl-5H-pyrido[4,3-b]indol-7-yl)pyridin-2-yl)azetidin-3-yl)oxy)piperidin-1-yl)ethoxy)azetidin-1-yl)isoindoline-1,3-dione | | 769.3 | 1H NMR (300 MHz, DMSO-d6) δ 11.08 (s, 1H), 9.33 (s, 1H), 8.58 (s, 1H), 8.47 (m, 1H), 8.29-8.27 (m, 1H), 8.03-8.01 (m, 1H), 7.90 (s, 1H), 7.66-7.56 (m, 3H), 6.81 (s, 1H), 6.67-6.52 (m, 2H), 5.07-5.05 (m, 1H), 4.58-4.48 (m, 2H), 4.25 (m, 4H), 3.87-3.79 (m, 8H), 3.53 (m, 2H), 3.05-2.59 (m, 4H), 2.39-1.97 (m, 4H), 1.84 (m, 3H), 1.55-1.43 (m, 3H). |

TABLE 1-continued

| | | | | | |
|---|---|---|---|---|---|
| 514 | 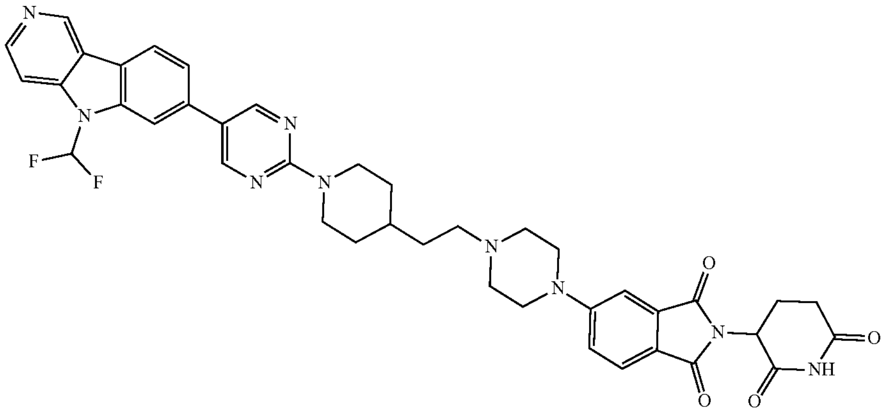 [SMILES: O=C1CCC(N2C(=O)c3ccc(N4CCN(CCC5CCN(c6ncc(-c7ccc8c9cnccc9n(C(F)F)c8c7)cn6)CC5)CC4)cc3C2=O)C(=O)N1] | 5-(4-(2-(1-(5-(5-(difluoromethyl)-5H-pyrido[4,3-b]indol-7-yl)pyrimidin-2-yl)piperidin-4-yl)ethyl)piperazin-1-yl)-2-(2,6-dioxopiperidin-3-yl)isoindoline-1,3-dione | A | 748.3 | 1H NMR (400 MHz, DMSO-d6) δ: 1.14 (d, J = 10.4 Hz, 2 H), 1.45 (s, 2 H), 1.67 (s, 1 H), 1.81 (d, J = 12.0 Hz, 2 H), 2.06 (d, J = 15.6 Hz, 1 H), 2.40 (s, 2 H), 2.62 (s, 2 H), 2.86-3.07 (m, 3 H), 3.45 (s, 8 H), 4.74 (d, J = 12.0 Hz, 2 H), 5.02-5.14 (m, 1 H), 7.27 (d, J = 8.0 Hz, 1 H), 7.35 (s, 1 H), 7.65-7.86 (m, 3 H), 8.16 (s, 1 H), 8.33-8.41 (m, 1 H), 8.48 (s, 1 H), 8.61 (d, J = 6.0 Hz, 1 H), 8.83 (s, 2 H), 9.48 (s, 1 H), 11.08 (s, 1 H) |
| 515 | 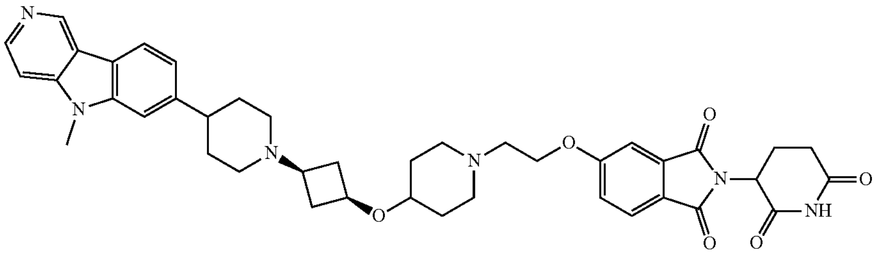 [SMILES: Cn1c2ccncc2c2ccc(C3CCN([C@H]4C[C@@H](OC5CCN(CCOc6ccc7c(c6)C(=O)N(C6CCC(=O)NC6=O)C7=O)CC5)C4)CC3)cc21] | 2-(2,6-dioxopiperidin-3-yl)-5-(2-(4-((1s,3s)-3-(4-(5-methyl-5H-pyrido[4,3-b]indol-7-yl)piperidin-1-yl)cyclobutoxy)piperidin-1-yl)ethoxy)isoindoline-1,3-dione | A | 719.3 | $^1$H NMR (400 MHz, DMSO-d6) δ: 1.45 (d, J = 9.6 Hz, 2 H), 1.74-1.91 (m, 8 H), 2.01-2.15 (m, 3 H), 2.25 (t, J = 8.8 Hz, 2 H), 2.54-2.66 (m, 2 H), 2.75-2.86 (m, 5 H), 3.05 (d, J = 10.8 Hz, 2 H), 3.33 (s, 1 H), 3.90 (s, 3 H), 4.30 (t, J = 5.2 Hz, 2 H), 5.13 (d, J = 12.8 Hz, 1 H), 7.22 (d, J = 8.0 Hz, 1 H), 7.37 (d, J = 8.4 Hz, 1 H), 7.47 (s, 1 H), 7.52-7.65 (m, 2 H), 7.84 (d, J = 8.4 Hz, 1 H), 8.16 (s, 1 H), 8.18 (s, 2 H), 8.47 (d, J = 5.6 Hz, 1 H), 9.30 (s, 1 H), 11.13 (s, 1 H) |
| 516 | 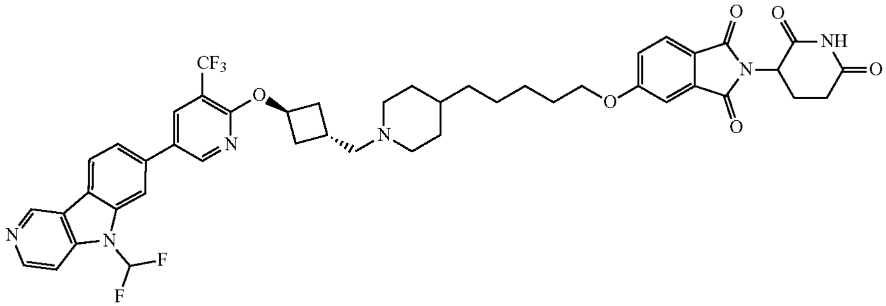 [SMILES: O=C1CCC(N2C(=O)c3ccc(OCCCCCC4CCN(C[C@H]5C[C@H](Oc6ncc(-c7ccc8c9cnccc9n(C(F)F)c8c7)cc6C(F)(F)F)C5)CC4)cc3C2=O)C(=O)N1] | 5-((5-(1-(((1r,3r)-3-((5-(5-(difluoromethyl)-5H-pyrido[4,3-b]indol-7-yl)-3-(trifluoromethyl)pyridin-2-yl)oxy)cyclobutyl)methyl)piperidin-4-yl)pentyl)oxy)-2-(2,6-dioxopiperidin-3-yl)isoindoline-1,3-dione | | 873.3 | $^1$H NMR (400 MHz, DMSO-$d_6$) δ: 11.11 (s, 1H), 9.52 (s, 1H), 8.86 (d, J = 2.5 Hz, 1H), 8.64 (d, J = 5.8 Hz, 1H), 8.53-8.41 (m, 3H), 8.28 (d, J = 1.8 Hz, 1H), 8.15 (s, 1H), 7.91-7.80 (m, 3H), 7.43 (d, J = 2.3 Hz, 1H), 7.35 (dd, J = 8.3, 2.3 Hz, 1H), 5.46 (q, J = 6.2 Hz, 1H), 5.12 (dd, J = 12.9, 5.4 Hz, 1H), 4.18 (t, J = 6.5 Hz, 2H), 3.04 (s, 2H), 2.90 (ddd, J = 18.1, 14.1, 5.4 Hz, 1H), 2.75 (s, 3H), 2.63 (s, 1H), 2.57 (d, J = 9.8 Hz, 1H), 2.32 (s, 8H), 2.07 (s, 1H), 1.85 (d, J = 9.4 Hz, 1H), 1.81-1.67 (m, 5H), 1.45-1.33 (m, 6H), 1.27-1.20 (m, 5H). |

TABLE 1-continued

| | | | | |
|---|---|---|---|---|
| 517 | 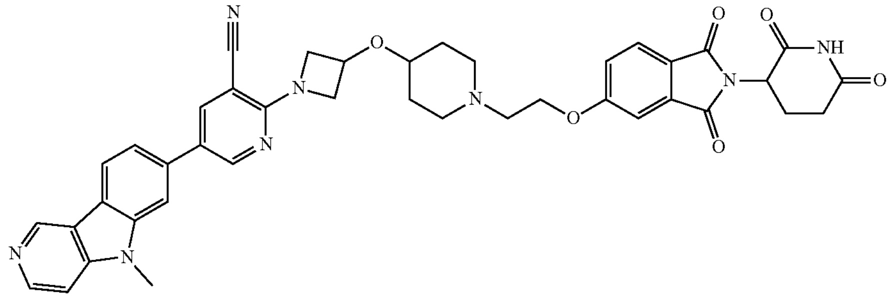 [SMILES: Cn1c2ccncc2c2ccc(-c3cnc(N4CC(OC5CCN(CCOc6ccc7c(c6)C(=O)N(C6CCC(=O)NC6=O)C7=O)CC5)C4)c(C#N)c3)cc21] | 2-(3-((1-(2-((2-(2,6-dioxopiperidin-3-yl)-1,3-dioxoisoindolin-5-yl)oxy)ethyl)piperidin-4-yl)oxy)azetidin-1-yl)-5-(5-methyl-5H-pyrido[4,3-b]indol-7-yl)nicotinonitrile | 732.3 | $^1$H NMR (400 MHz, DMSO-$d_6$): δ (ppm): 11.12 (s, 1H), 9.43 (s, 1H), 8.89 (d, J = 2.5 Hz, 1H), 8.55 (s, 2H), 8.36 (d, J = 8.3 Hz, 1H), 8.14-8.08 (m, 1H), 7.88 (d, J = 8.2 Hz, 1H), 7.72 (s, 2H), 7.52 (s, 1H), 7.41 (d, J = 8.5 Hz, 1H), 5.13 (dd, J = 12.9, 5.4 Hz, 1H), 4.64-4.54 (m, 3H), 4.41 (brs, 1H), 4.11 (d, J = 8.2 Hz, 2H), 4.00 (s, 3H), 3.82-3.44 (m, 5 H), 3.24-3.01 (m, 2H), 2.88 (d, J = 12.3 Hz, 1H), 2.63-2.55 (m, 2H), 2.14-1.85 (m, 4H), 1.74-1.44 (m, 2H). |
| 518 | 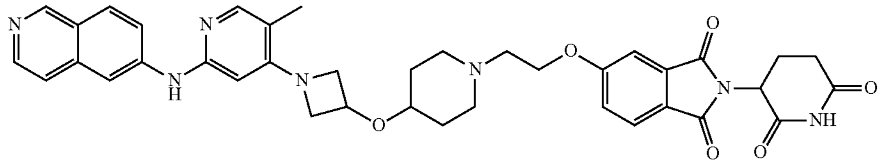 [SMILES: Cc1cnc(Nc2ccc3cnccc3c2)cc1N1CC(OC2CCN(CCOc3ccc4c(c3)C(=O)N(C3CCC(=O)NC3=O)C4=O)CC2)C1] | 2-(2,6-dioxopiperidin-3-yl)-5-(2-(4-((1-(2-(isoquinolin-6-ylamino)-5-methylpyridin-4-yl)azetidin-3-yl)oxy)piperidin-1-yl)ethoxy)isoindoline-1,3-dione | 690.3 | $^1$H NMR (400 MHz, Methanol-$d_4$): δ 9.03 (s, 1H), 8.40 (s, 1H), 8.27 (d, J = 6.0 Hz, 1H), 8.04-1.97 (m, 2H), 7.83 (d, J = 8.3 Hz, 1H), 7.67 (d, J = 6.0 Hz, 1H), 7.64-7.61 (m, 1H), 7.57 (dd, J = 8.9, 2.2 Hz, 1H), 7.46 (d, J = 2.3 Hz, 1H), 7.37 (dd, J = 8.3, 2.3 Hz, 1H), 5.95 (s, 1H), 5.11 (dd, J = 12.6, 5.5 Hz, 1H), 4.63-4.54 (m, 1H), 4.49-4.41 (m, 2H), 4.38 (t, J = 5.2 Hz, 2H), 4.00 (dd, J = 8.9, 4.6 Hz, 2H), 3.14-3.10 (m, 4H), 2.94-2.80 (m, 1H), 2.80-2.72 (m, 1H), 2.76-2.64 (m, 3H), 2.21 (s, 3H), 2.12 (ddd, J = 12.7, 5.3, 3.0 Hz, 1H), 1.81-1.74 (m, 2H). |
| 519 | 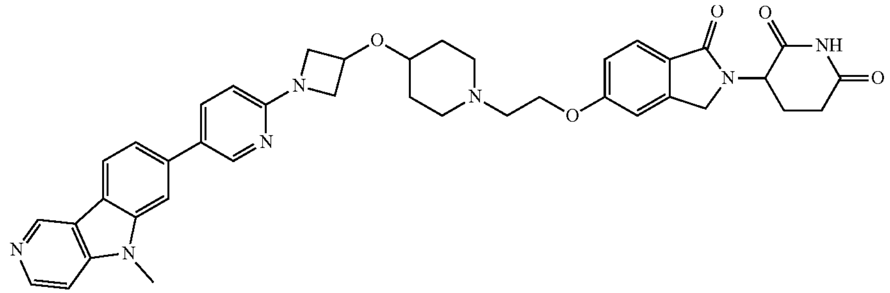 [SMILES: Cn1c2ccncc2c2ccc(-c3ccc(N4CC(OC5CCN(CCOc6ccc7c(c6)CN(C6CCC(=O)NC6=O)C7=O)CC5)C4)nc3)cc21] | 3-(5-(2-(4-((1-(5-(5-methyl-5H-pyrido[4,3-b]indol-7-yl)pyridin-2-yl)azetidin-3-yl)oxy)piperidin-1-yl)ethoxy)-1-oxoisoindolin-2-yl)piperidine-2,6-dione | 700.3 | $^1$H NMR (400 MHz, DMSO-$d_6$) δ 11.00 (d, J = 16.4 Hz, 1H), 9.40-9.29 (m, 2H), 8.61 (d, J = 15.8 Hz, 2H), 8.51 (q, J = 7.5, 6.6 Hz, 2H), 8.30 (dt, J = 18.4, 8.8 Hz, 2H), 8.11-7.99 (m, 2H), 7.93 (d, J = 17.5 Hz, 2H), 7.70-7.54 (m, 6H), 7.21 (d, J = 15.9 Hz, 2H), 7.09 (q, J = 9.4, 9.0 Hz, 2H), 6.62-6.50 (m, 2H), 5.10 (s, 1H), 4.61 (s, 1H), 4.44-4.12 (m, 12H), 3.98 (d, J = 16.5 Hz, 6H), 3.87-3.76 (m, 4H), 2.87 (s, 2H), 2.80-2.70 (m, 5H), 2.50 (d, J = 12.1 Hz, 21H), 2.23 (d, J = 16.9 Hz, 3H), 2.01 (s, 1H), 1.86 (s, 2H), 1.53 (d, J = 17.9 Hz, 3H). |

TABLE 1-continued

| | | | | |
|---|---|---|---|---|
| 520 | 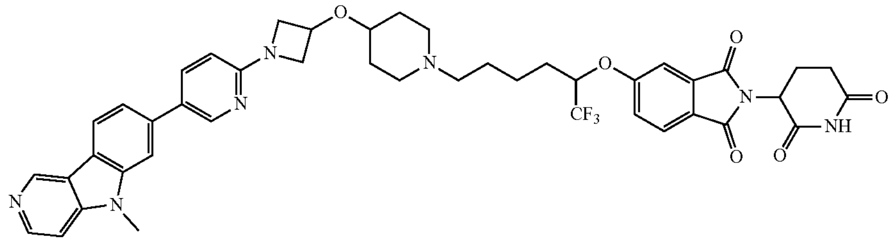 [SMILES: Cn1c2ccncc2c2ccc(-c3ccc(N4CC(OC5CCN(CCCCC(Oc6ccc7c(c6)C(=O)N(C6CCC(=O)NC6=O)C7=O)C(F)(F)F)CC5)C4)nc3)cc21] | 2-(2,6-dioxopiperidin-3-yl)-5-((1,1,1-trifluoro-6-(4-((1-(5-(5-methyl-5H-pyrido[4,3-b]indol-7-yl)pyridin-2-yl)azetidin-3-yl)oxy)piperidin-1-yl)hexan-2-yl)oxy)isindoline-1,3-dione | 824.3 | $^1$H NMR (400 MHz, DMSO-$d_6$) δ: 11.13 (s, 1H), 9.74 (s, 1H), 9.23-9.10 (m, 1H), 8.76 (d, J = 6.8 Hz, 1H), 8.64 (s, 1H), 8.51 (d, J = 8.4 Hz, 1H), 8.23-8.01 (m, 3H), 7.94-7.88 (m, 1H), 7.84 (d, J = 8.0 Hz, 1H), 7.77 (s, 1H), 7.53 (dd, J = 2.0, 8.4 Hz, 1H), 6.67-6.58 (m, 1H), 5.70-5.57 (m, 1H), 5.19-5.07 (m, 1H), 4.67-4.55 (m, 1H), 4.36-4.26 (m, 2H), 4.14 (s, 3H), 3.88 (dd, J = 2.0, 8.0 Hz, 2H), 3.34-3.28 (m, 2H), 3.10-3.02 (m, 3H), 2.97-2.82 (m, 3H), 2.64-2.57 (m, 1H), 2.17-2.03 (m, 3H), 1.95-1.84 (m, 4H), 1.75-1.65 (m, 3H), 1.50-1.42 (m, 2H) |
| 521 | 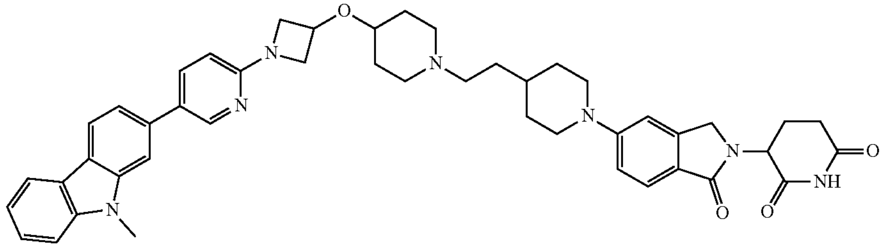 [SMILES: Cn1c2ccccc2c2ccc(-c3ccc(N4CC(OC5CCN(CCC6CCN(c7ccc8c(c7)CN(C7CCC(=O)NC7=O)C8=O)CC6)CC5)C4)nc3)cc21] | 3-(5-(4-(2-(4-((1-(5-(5-methyl-5H-pyrido[4,3-b]indol-7-yl)pyridin-2-yl)azetidin-3-yl)oxy)piperidin-1-yl)ethyl)piperidin-1-yl)-1-oxoisoindolin-2-yl)piperidine-2,6-dione | 767.4 | $^1$H NMR (400 MHz, methanol-$d_4$): δ 9.26 (s, 1H), 8.47 (d, J = 5.5 Hz, 1H), 8.29 (d, J = 8.2 Hz, 1H), 8.04 (d, J = 6.4 Hz, 1H), 7.81 (s, 1H), 7.67-7.54 (m, 2H), 7.09 (d, J = 9.6 Hz, 1H), 6.61 (d, J = 8.9 Hz, 1H), 4.44-4.32 (m, 3H), 4.00 (s, 1H), 3.94 (d, J = 9.6 Hz, 2H), 2.90 (d, J = 12.7 Hz, 2H), 1.95 (s, 1H), 1.31 (s, 1H). |
| 522 | 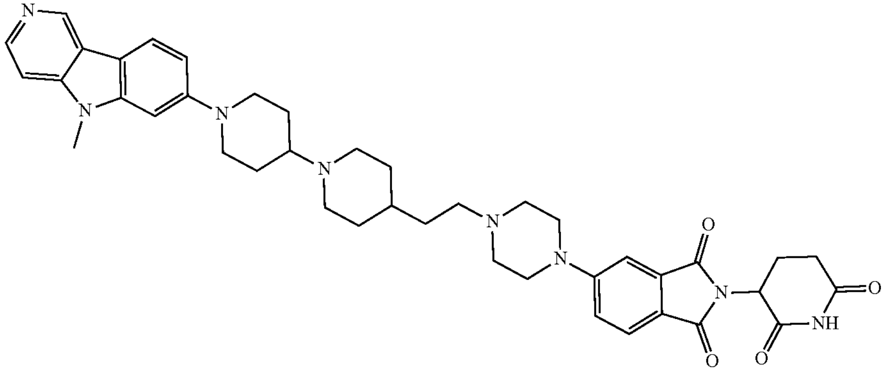 [SMILES: Cn1c2ccncc2c2ccc(N3CCC(N4CCC(CCN5CCN(c6ccc7c(c6)C(=O)N(C6CCC(=O)NC6=O)C7=O)CC5)CC4)CC3)cc21] | 2-(2,6-dioxopiperidin-3-yl)-5-(4-(2-(1'-(5-methyl-5H-pyrido[4,3-b]indol-7-yl)-[1,4'-bipiperidin]-4-yl)ethyl)piperazin-1-yl)isoindoline-1,3-dione | 717.4 | $^1$H NMR (300 MHz, methanol-$d_4$): δ 9.29 (s, 1H), 8.47 (s, 1H), 8.17 (s, 1H), 7.95 (s, 1H), 7.73 (s, 1H), 7.44 (s, , 1H), 7.32 (s, 1H), 7.25 (m, 2H), 5.09 (s, 1H), 4.21 (m, 2H), 4.03 (m, 3H), 3.67 (m, 2H), 3.45 (m, 10H), 3.29 (s, 1H), 3.07 (m, 4H), 2.89-2.79 (s, 1H), 2.77 (s, 1H), 2.77-2.65 (s, 1H), 2.28 (s, 1H), 2.06 (m, 6H), 1.82 (m, 4H), 1.64 (m, 2H). |

TABLE 1-continued

| | | | | |
|---|---|---|---|---|
| 523 | 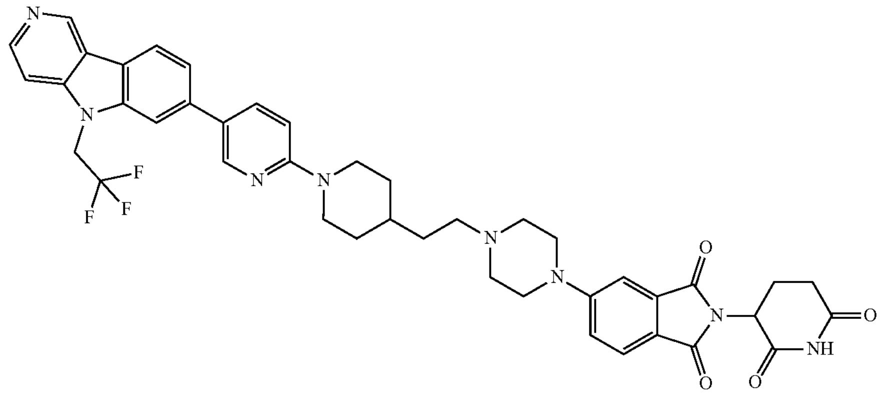 [SMILES: O=C1CCC(N2C(=O)c3ccc(N4CCN(CCC5CCN(c6ccc(-c7ccc8c9cnccc9n(CC(F)(F)F)c8c7)cn6)CC5)CC4)cc3C2=O)C(=O)N1] | 2-(2,6-dioxopiperidin-3-yl)-5-(4-(2-(1-(5-(5-(2,2,2-trifluoroethyl)-5H-pyrido[4,3-b]indol-7-yl)pyridin-2-yl) piperidin-4-yl)ethyl) piperazin-1-yl)isoindoline-1,3-dione | 779.3 | $^1$H NMR (400 MHz, DMSO-d6) δ: 1.00-1.32 (m, 3 H), 1.66 (s, 3 H), 1.79 (d, J = 11.6 Hz, 2 H), 1.97-2.12 (m, 2 H), 2.54-2.65 (m, 2 H), 2.83-2.98 (m, 3 H), 3.08-3.36 (m, 5 H), 3.61 (s, 1 H), 4.25 (d, J = 12.8 Hz, 2 H), 4.42 (d, J = 13.2 Hz, 2 H), 5.10 (d, J = 12.8 Hz, 1 H), 5.69-5.91 (m, 2 H), 7.00-7.11 (m, 1 H), 7.38 (d, J = 8.4 Hz, 1 H), 7.51 (s, 1 H), 7.78 (d, J = 8.4 Hz, 1 H), 7.90 (d, J = 8.8 Hz, 1 H), 8.02-8.16 (m, 1 H), 8.34-8.38 (m, 2 H), 8.52 (d, J = 8.4 Hz, 1 H), 8.68 (d, J = 2.4 Hz, 1 H), 8.86 (d, J = 7.0 Hz, 1 H), 9.67 (s, 1 H), 9.82 (s, 1 H), 11.10 (s, 1 H) |
| 524 | 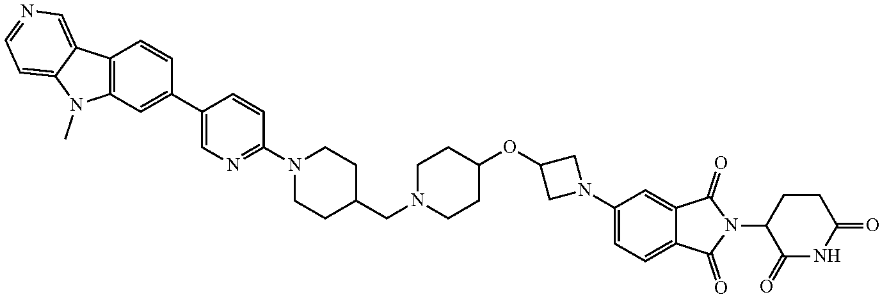 [SMILES: Cn1c2ccncc2c2ccc(-c3ccc(N4CCC(CN5CCC(OC6CN(c7ccc8c(c7)C(=O)N(C7CCC(=O)NC7=O)C8=O)C6)CC5)CC4)nc3)cc21] | 2-(2,6-dioxopiperidin-3-yl)-5-(3-((1-((1-(5-(5-methyl-5H-pyrido[4,3-b]indol-7-yl)pyridin-2-yl)piperidin-4-yl)methyl)piperidin-4-yl)oxy)azetidin-1-yl)isoindoline-1,3-dione | | |
| 525 | 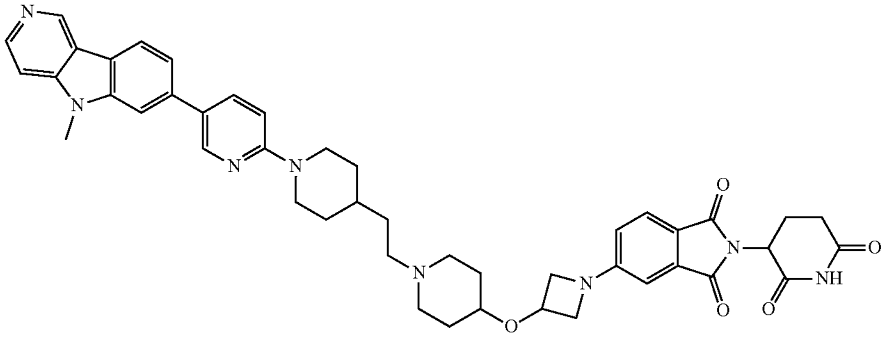 [SMILES: Cn1c2ccncc2c2ccc(-c3ccc(N4CCC(CCN5CCC(OC6CN(c7ccc8c(c7)C(=O)N(C7CCC(=O)NC7=O)C8=O)C6)CC5)CC4)nc3)cc21] | 2-(2,6-dioxopiperidin-3-yl)-5-(3-((1-(2-(1-(5-(5-methyl-5H-pyrido[4,3-b]indol-7-yl)pyridin-2-yl)piperidin-4-yl)ethyl)piperidin-4-yl)oxy)azetidin-1-yl)isoindoline-1,3-dione | | |

TABLE 1-continued

| | | | | | |
|---|---|---|---|---|---|
| 526 | 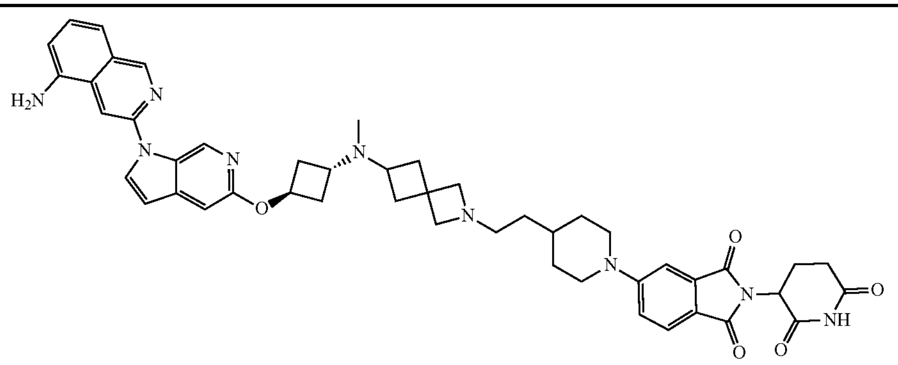 | 5-(4-(2-(6-(((1r,3r)-3-((1-(5-aminoisoquinolin-3-yl)-1H-pyrrolo[2,3-c]pyridin-5-yl)oxy)cyclobutyl)(methyl)amino)-2-azaspiro[3.3]heptan-2-yl)ethyl)piperidin-1-yl)-2-(2,6-dioxopiperidin-3-yl)isoindoline-1,3-dione | | 822.4 | $^1$H NMR (400 MHz, Methanol-$d_4$): δ 9.28 (s, 1H), 9.17 (s, 1H), 8.39 (m, 2H), 8.19 (s, 1H), 8.10 (s, 1H), 7.68 (s, 1H), 7.45 (s, 1H), 7.46-7.38 (s, 1H), 7.38-7.32 (s, 1H), 7.22 (s, 1H), 7.06 (s, 1H), 6.96 (s, 1H), 6.74 (s, 1H), 5.14-5.04 (m, 2H), 4.15 (m, 2H), 4.06 (m, 4H), 3.46 (s, 1H), 3.24-3.15 (m, 2H), 3.03 (s, 1H), 2.98 (m, 2H), 2.86 (s, 1H), 2.80-2.68 (s, 1H), 2.58-2.49 (m, 2H), 2.48 (m, 2H), 2.35 (m, 4H), 2.22 (m, 3H), 2.12 (s, 1H), 1.84 (m, 2H), 1.66 (s, 1H), 1.55-1.47 (m, 3H), 1.35 (m, 4H). |
| 527 | 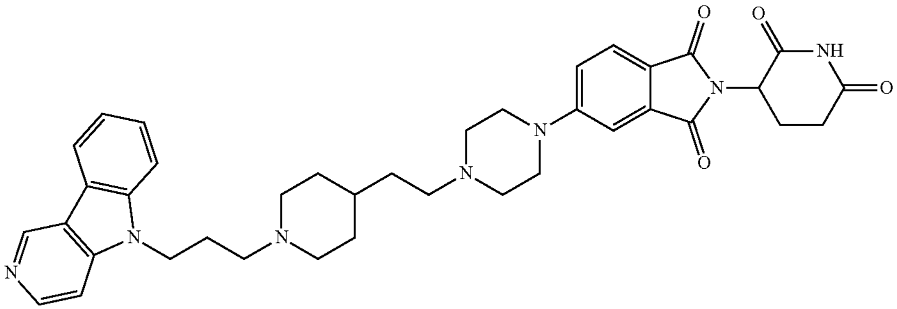 [SMILES: O=C1CCC(N2C(=O)c3ccc(N4CCN(CCC5CCN(CCCn6c7ccccc7c7cnccc76)CC5)CC4)cc3C2=O)C(=O)N1] | 5-(4-(2-(1-(3-(5H-pyrido[4,3-b]indol-5-yl)propyl)piperidin-4-yl)ethyl)piperazin-1-yl)-2-(2,6-dioxopiperidin-3-yl)isoindoline-1,3-dione | A | 662.3 | $^1$H NMR (300 MHz, methanol-$d_4$): δ 9.57 (s, 1H), 8.62 (s, 1H), 8.41 (s, 1H), 8.18 (s, 1H), 7.92 (s, 1H), 7.80 (s, 1H), 7.70 (s, 1H), 7.58 (s, 1H), 7.41 (s, 1H), 7.29 (s, 1H), 5.07 (s, 1H), 4.71 (m, 2H), 3.58 (m, 2H), 3.25 (m, 6H), 3.01-2.58 (m, 4H), 2.50-2.33 (m, 8H), 2.11 (s, 1H), 2.04-1.99 (m, 2H), 1.88-1.75 (m, 3H), 1.63-1.49 (m, 4H). |
| 528 | 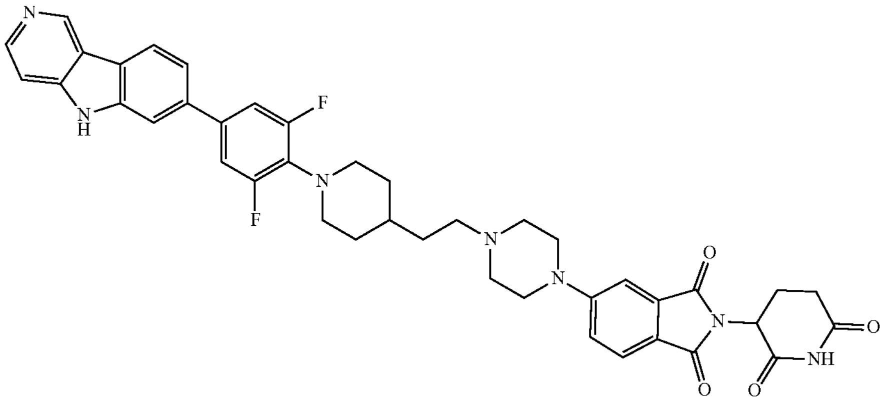 [SMILES: O=C1CCC(N2C(=O)c3ccc(N4CCN(CCC5CCN(c6c(F)cc(-c7ccc8c(c7)[nH]c7ccncc78)cc6F)CC5)CC4)cc3C2=O)C(=O)N1] | 5-(4-(2-(1-(2,6-difluoro-4-(5H-pyrido[4,3-b]indol-7-yl)phenyl)piperidin-4-yl)ethyl)piperazin-1-yl)-2-(2,6-dioxopiperidin-3-yl)isoindoline-1,3-dione | | 732.3 | $^1$H NMR (400 MHz, DMSO-$d_6$) δ: 13.13 (s, 1H), 11.10 (s, 1H), 9.76 (s, 2H), 8.67 (d, J = 7.2 Hz, 1H), 8.51 (d, J = 8.4 Hz, 1H), 8.05-7.99 (m, 2H), 7.84 (dd, J = 1.6, 8.4 Hz, 1H), 7.78 (d, J = 8.4 Hz, 1H), 7.61-7.53 (m, 2H), 7.51 (d, J = 1.6 Hz, 1H), 7.38 (dd, J = 2.0, 8.4 Hz, 1H), 5.10 (dd, J = 5.2, 12.8 Hz, 1H), 4.34-4.18 (m, 2H), 3.68-3.59 (m, 2H), 3.30 (s, 2H), 3.27 (s, 5H), 3.14-3.04 (m, 3H), 2.89 (ddd, J = 5.4, 14.4, 17.2 Hz, 1H), 2.64-2.54 (m, 2H), 2.07-1.98 (m, 1H), 1.81-1.67 (m, 4H), 1.57-1.45 (m, 1H), 1.42-1.30 (m, 2H) |

TABLE 1-continued

| | | | | |
|---|---|---|---|---|
| 529 | 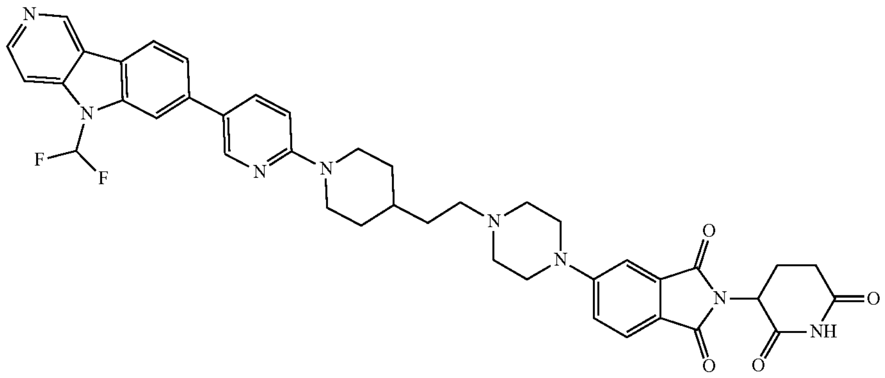 [SMILES: O=C1CCC(N2C(=O)c3ccc(N4CCN(CCC5CCN(c6ccc(-c7ccc8c9cnccc9n(C(F)F)c8c7)cn6)CC5)CC4)cc3C2=O)C(=O)N1] | 5-(4-(2-(1-(5-(5-(difluoromethyl)-5H-pyrido[4,3-b]indol-7-yl)pyridin-2-yl)piperidin-4-yl)ethyl)piperazin-1-yl)-2-(2,6-dioxopiperidin-3-yl)isoindoline-1,3-dione | 747.3 | $^1$H NMR (400 MHz, DMSO-d6) δ: 1.18 (d, J = 10.4 Hz, 2 H), 1.45 (d, J = 7.6 Hz, 2 H), 1.62 (s, 1 H), 1.78 (d, J = 12.0 Hz, 2 H), 1.95-2.10 (m, 2 H), 2.41 (d, J = 6.8 Hz, 2 H), 2.82-2.95 (m, 3 H), 3.44 (s, 8 H), 4.39 (d, J = 12.8 Hz, 3 H), 5.07 (d, J = 12.8 Hz, 1 H), 6.97 (d, J = 9.2 Hz, 1 H), 7.26 (d, J = 8.8 Hz, 1 H), 7.34 (s, 1 H), 7.68 (d, J = 8.8 Hz, 1 H), 7.74 (d, J = 8.0 Hz, 1 H), 7.81 (d, J = 5.6 Hz, 1 H), 7.97 (d, J = 8.8 Hz, 1 H), 8.14 (d, J = 15.6 Hz, 2 H), 8.35 (d, J = 8.0 Hz, 1 H), 8.50 (s, 1 H), 8.56-8.63 (m, 2 H), 9.46 (s, 1 H), 11.08 (s, 1 H) |
| 530 | 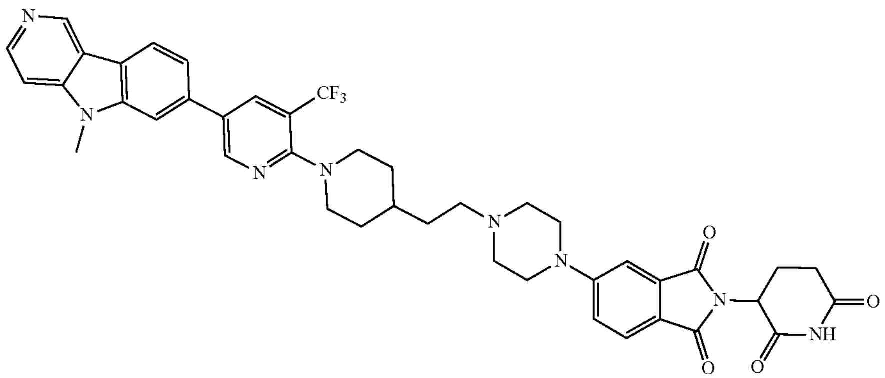 [SMILES: Cn1c2ccncc2c2ccc(-c3cnc(N4CCC(CCN5CCN(c6ccc7c(c6)C(=O)N(C6CCC(=O)NC6=O)C7=O)CC5)CC4)c(C(F)(F)F)c3)cc21] | 2-(2,6-dioxopiperidin-3-yl)-5-(4-(2-(1-(5-(5-methyl-5H-pyrido[4,3-b]indol-7-yl)-3-(trifluoromethyl)pyridin-2-yl)piperazin-1-yl)isoindoline-1,3-dione | 779.3 | $^1$H NMR (400 MHz, DMSO-$d_6$) δ: 11.17-11.10 (m, 1 H), 10.01-9.87 (m, 1 H), 9.79 (s, 1 H), 9.05 (d, J = 2.40 Hz, 1 H), 8.78 (d, J = 6.80 Hz, 1 H), 8.61-8.48 (m, 2 H), 8.34 (s, 1 H), 8.22 (d, J = 6.80 Hz, 1 H), 8.04-7.90 (m, 1 H), 7.77 (d, J = 8.40 Hz, 1 H), 7.50 (d, J = 1.60 Hz, 1 H), 7.41-7.31 (m, 1 H), 5.10 (d, J = 12.80, 5.40 Hz, 1 H), 4.29-4.22 (m, 1 H), 4.16 (s, 3 H), 3.72-3.56 (m, 5 H), 3.32-3.22 (m, 4 H), 3.21-3.10 (m, 2 H), 2.97 (t, J = 12.40 Hz, 2 H), 2.88 (d, J = 16.80, 5.60 Hz, 1 H), 2.64-2.53 (m, 2 H), 2.07-2.00 (m, 1 H), 1.83 (d, J = 10.80 Hz, 2 H), 1.76-1.67 (m, 2 H), 1.64-1.53 (m, 1 H), 1.42-1.29 (m, 2 H). |

TABLE 1-continued

| | | | | | |
|---|---|---|---|---|---|
| 531 | 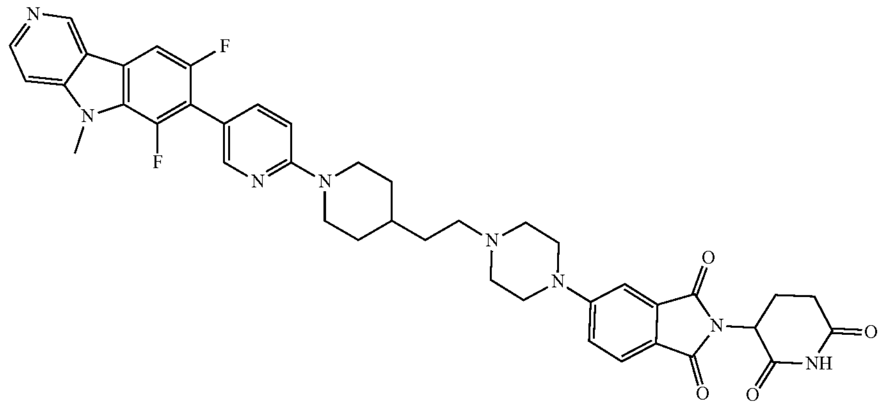 [SMILES: Cn1c2ccncc2c2cc(F)c(-c3ccc(N4CCC(CCN5CCN(c6ccc7c(c6)C(=O)N(C6CCC(=O)NC6=O)C7=O)CC5)CC4)nc3)c(F)c21] | 5-(4-(2-(1-(5-(6,8-difluoro-5-methyl-5H-pyrido[4,3-b]indol-7-yl)pyridin-2-yl) piperidin-4-yl)ethyl) piperazin-1-yl)-2-(2,6-dioxopiperidin-3-yl)isoindoline-1,3-dione | | 747.3 | $^1$H NMR (400 MHz, DMSO-$d_6$) δ: 11.10 (s, 1H), 9.80 (s, 2H), 8.84 (d, J = 6.8 Hz, 1H), 8.36 (d, J = 8.9 Hz, 1H), 8.29 (br d, J = 6.5 Hz, 2H), 7.82-7.69 (m, 2H), 7.51 (d, J = 1.7 Hz, 1H), 7.41-7.33 (m, 1H), 7.04 (d, J = 9.0 Hz, 1H), 5.20-5.00 (m, 1H), 4.46-4.39 (m, 2H), 4.26-4.20 (m, 4H), 3.67-3.64 (m, 1H), 3.32-3.10 (m, 4H), 2.97-2.85 (m, 3H), 2.64-2.54 (m, 2H), 2.08-2.00 (m, 1H), 1.80 (br d, J = 11.7 Hz, 2H), 1.72-1.62 (m, 3H), 1.29-1.16 (m, 2H) |
| 532 | 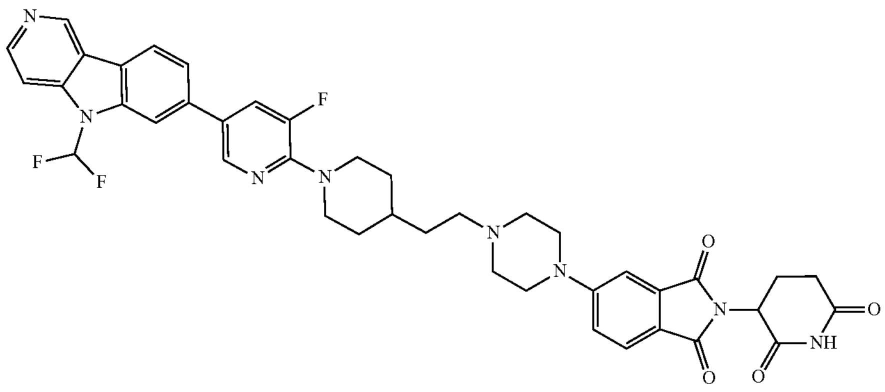 [SMILES: O=C1CCC(N2C(=O)c3ccc(N4CCN(CCC5CCN(c6ncc(-c7ccc8c9cnccc9n(C(F)F)c8c7)cc6F)CC5)CC4)cc3C2=O)C(=O)N1] | 5-(4-(2-(1-(5-(5-(difluoromethyl)-5H-pyrido[4,3-b]indol-7-yl)-3-fluoropyridin-2-yl)piperidin-4-yl)ethyl)piperazin-1-yl)-2-(2,6-dioxopiperidin-3-yl)isoindoline-1,3-dione | A | 765.3 | $^1$H NMR (400 MHz, DMSO-$d_6$) δ: 11.16-11.07 (m, 1 H), 10.12-9.87 (m, 1 H), 9.83 (s, 1 H), 8.93-8.91 (m, 1 H), 8.89-8.75 (m, 1 H), 8.71-8.41 (m, 3 H), 8.35-8.23 (m, 2 H), 8.06 (dd, J = 14.80, 1.60 Hz, 1 H), 7.99-7.92 (m, 1 H), 7.77 (d, J = 8.40 Hz, 1 H), 7.49 (s, 1 H), 7.41-7.32 (m, 1 H), 5.09 (dd, J = 12.80, 5.40 Hz, 1 H), 4.23 (s, 1 H), 4.13 (d, J = 12.40 Hz, 2 H), 3.27-3.22 (m, 4 H), 3.00-2.88 (m, 4 H), 2.64-2.55 (m, 4 H), 2.06-2.00 (m, 1 H), 1.80 (d, J = 11.60 Hz, 2 H), 1.71-1.65 (m, 2 H), 1.63 (d, J = 2.69 Hz, 1 H), 1.37-1.27 (m, 2 H), 1.13 (d, J = 13.60 Hz, 1 H). |

TABLE 1-continued

| | | | | | |
|---|---|---|---|---|---|
| 533 | 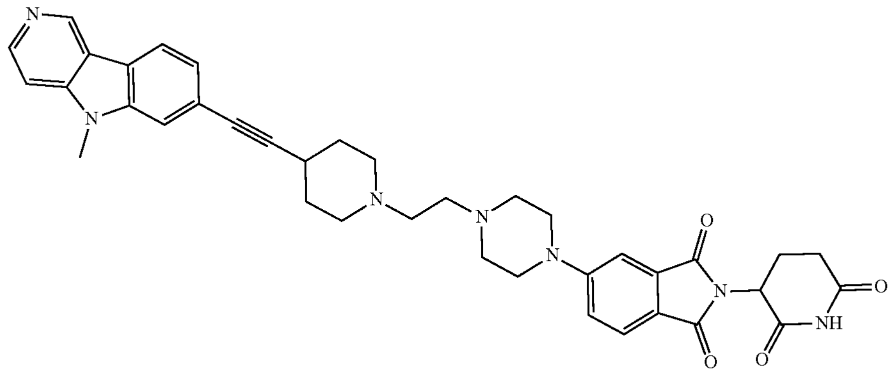 [SMILES: Cn1c2ccncc2c2ccc(C#CC3CCN(CCN4CCN(c5ccc6c(c5)C(=O)N(C5CCC(=O)NC5=O)C6=O)CC4)CC3)cc21] | 2-(2,6-dioxopiperidin-3-yl)-5-(4-(2-(4-((5-methyl-5H-pyrido[4,3-b]indol-7-yl)ethynyl)piperidin-1-yl)ethyl)piperazin-1-yl)isoindoline-1,3-dione | A | 658.3 | $^1$H NMR (400 MHz, DMSO-$d_6$) δ: 11.09 (s, 1H), 9.76 (s, 1H), 8.78 (d, J = 6.7 Hz, 1H), 8.45 (d, J = 7.9 Hz, 1H), 8.21 (d, J = 6.5 Hz, 1H), 7.99 (s, 1H), 7.67 (s, 1H), 7.59 (d, J = 9.2 Hz, 1H), 7.39 (s, 1H), 7.26 (s, 1H), 5.08 (dd, J = 5.3, 12.3 Hz, 1H), 4.06 (s, 3H), 3.66-3.33 (m, 6H), 3.25 (s, 2H), 3.09 (s, 2H), 2.99-2.71 (m, 6H), 2.64-2.53 (m, 4H), 2.16 (s, 2H), 2.07-1.88 (m, 3H). |
| 534 | 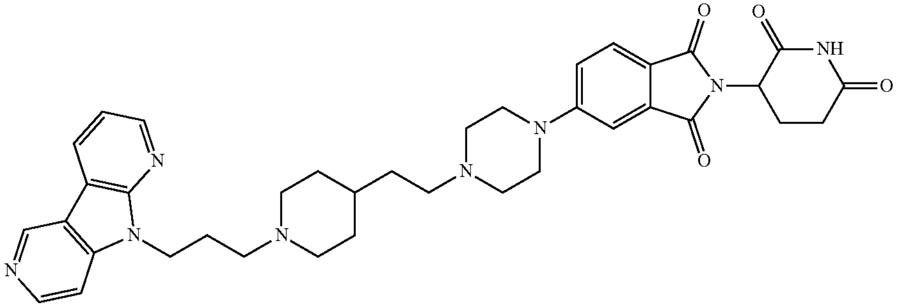 | 5-(4-(2-(1-(3-(9H-pyrrolo[2,3-b:4,5-c']dipyridin-9-yl)propyl)piperidin-4-yl)ethyl)piperazin-1-yl)-2-(2,6-dioxopiperidin-3-yl)isoindoline-1,3-dione | | 662.3 | $^1$H NMR (400 MHz, methanol-$d_4$): δ 9.70 (s, 1H), 8.83 (m, 2H), 8.76 (s, 1H), 8.29 (s, 1H), 7.76 (s, 1H), 7.64 (s, 1H), 7.48 (s, 1H), 7.35 (s, 1H), 5.11 (s, 1H), 4.83 (m, 2H), 3.62 (m, 2H), 3.51-3.46 (m, 7H), 3.29 (m, 4H), 2.97 (m, 2H), 2.94-2.82 (m, 1H), 2.82-2.65 (m, 2H), 2.56-2.44 (m, 2H), 2.13 (s, 1H), 2.03 (m, 2H), 1.85-1.75 (m, 2H), 1.79 (m, 2H), 1.58 (m, 2H). |
| 535 | 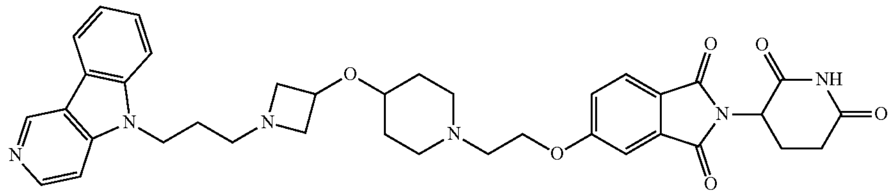 [SMILES: O=C1CCC(N2C(=O)c3ccc(OCCN4CCC(OC5CN(CCCn6c7ccccc7c7cnccc76)C5)CC4)cc3C2=O)C(=O)N1] | 5-(2-(4-((1-(3-(5H-pyrido[4,3-b]indol-5-yl)propyl)azetidin-3-yl)oxy)piperidin-1-yl)ethoxy)-2-(2,6-dioxopiperidin-3-yl)isoindoline-1,3-dione | | 665.3 | $^1$H NMR (400 MHz, DMSO-$d_6$): δ 11.11 (s, 1H), 9.34 (s, 1H), 8.47 (s, 1H), 8.25 (s, 1H), 7.82 (s, 1H), 7.68 (s, 1H), 7.61 (s, 1H), 7.54 (s, 1H), 7.45 (s, 1H), 7.38-7.26 (m, 2H), 5.11 (s, 1H), 4.41 (m, 2H), 4.26 (m, 2H), 4.14 (s, 1H), 3.59-3.51 (m, 2H), 2.94-2.82 (s, 1H), 2.81-2.73 (m, 2H), 2.69 (m, 4H), 2.64-2.53 (s, 1H), 2.33 (m, 2H), 2.16 (m, 2H), 2.09-1.95 (s, 1H), 1.76 (m, 4H), 1.45-1.32 (m, 2H), 1.23 (s, 2H). |

TABLE 1-continued

| | | | | | |
|---|---|---|---|---|---|
| 536 | 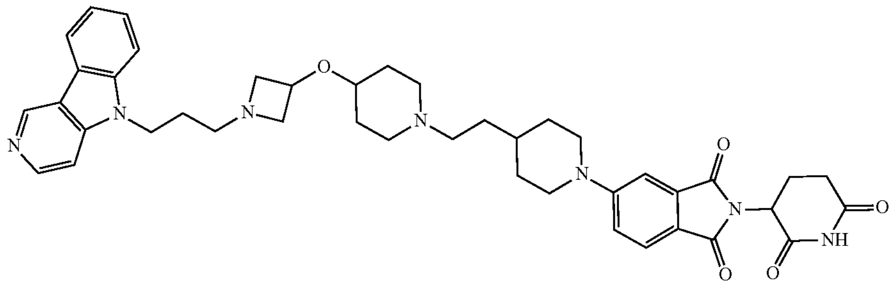 [SMILES: O=C1CCC(N2C(=O)c3ccc(N4CCC(CCN5CCC(OC6CN(CCCn7c8ccccc8c8cnccc87)C6)CC5)CC4)cc3C2=O)C(=O)N1] | 5-(4-(2-(4-((1-(3-(5H-pyrido[4,3-b]indol-5-yl)propyl)azetidin-3-yl)oxy)piperidin-1-yl)ethyl)piperidin-1-yl)-2-(2,6-dioxopiperidin-3-yl)isoindoline-1,3-dione | | 732.4 | $^1$H NMR (400 MHz, methanol-$d_4$): δ 9.60 (s, 1H), 8.64 (s, 1H), 8.44 (s, 1H), 8.20 (s, 1H), 7.94 (s, 1H), 7.83 (s, 1H), 7.66 (s, 1H), 7.61 (s, 1H), 7.34 (s, 1H), 7.21 (s, 1H), 5.07 (s, 1H), 4.78-4.69 (m, 2H), 4.58-4.53 (m, 2H), 4.22 (m, 5H), 4.05 (m, 3H), 3.85 (s, 1H), 3.63 (s, 2H), 3.41 (m, 3H), 3.19 (m, 3H), 3.00 (m, 3H), 2.94-2.81 (s, 1H), 2.81-2.64 (m, 2H), 2.05 (s, 1H), 1.97 (s, 1H), 1.86 (m, 2H), 1.72 (m, 4H), 1.37 (m, 3H). |
| 537 | 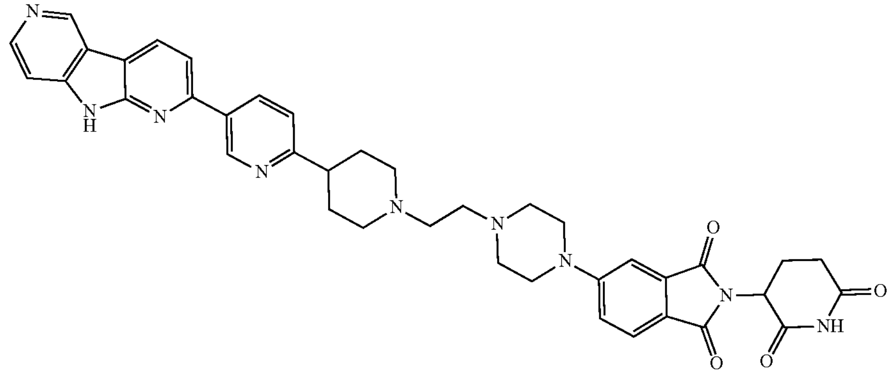 [SMILES: O=C1CCC(N2C(=O)c3ccc(N4CCN(CCN5CCC(c6ccc(-c7ccc8c(n7)[nH]c7ccncc78)cn6)CC5)CC4)cc3C2=O)C(=O)N1] | 5-(4-(2-(1-(5-(9H-pyrrolo[2,3-b:4,5-c']dipyridin-2-yl)pyridin-2-yl)piperidin-4-yl)ethyl)piperazin-1-yl)-2-(2,6-dioxopiperidin-3-yl)isoindoline-1,3-dione | A | 698.3 | 1H NMR (400 MHz, methanol-d4): δ 7.79 (d, J = 8.4 Hz, 1H), 7.73 (s, 1H), 7.61 (d, J = 7.9 Hz, 1H), 7.43 (d, J = 2.3 Hz, 1H), 7.37-7.29 (m, 2H), 7.12-7.04 (m, 2H), 7.04-6.94 (m, 3H), 6.87 (d, J = 9.1 Hz, 2H), 5.12 (dd, J = 12.6, 5.4 Hz, 2H), 4.37-4.26 (m, 3H), 4.15-4.09 (m, 2H), 3.98 (dd, J = 5.6, 3.4 Hz, 2H), 3.90 (dd, J = 5.6, 3.5 Hz, 2H), 3.68 (t, J = 5.2 Hz, 3H), 3.18 (d, J = 5.2 Hz, 3H), 3.00 (d, J = 6.6 Hz, 2H), 2.88 (ddd, J = 19.0, 14.1, 5.0 Hz, 2H), 2.80-2.67 (m, 3H), 2.14 (d, J = 5.2 Hz, 1H), 1.67 (s, 1H), 1.60-1.56 (m, 1H), 1.35 (d, J = 17.3 Hz, 3H), 1.31 (s, 3H), 0.90 (q, J = 7.0, 6.3 Hz, 3H). |
| 538 | 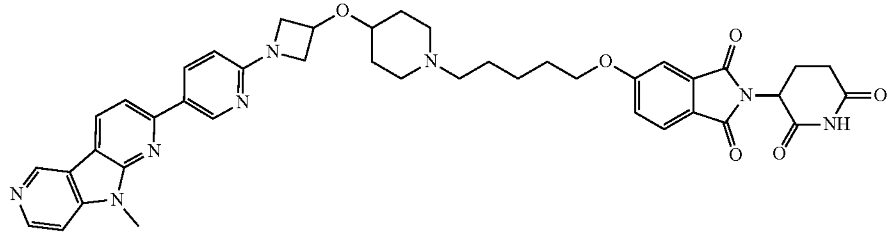 [SMILES: Cn1c2ccncc2c2ccc(-c3ccc(N4CC(OC5CCN(CCCCCOc6ccc7c(c6)C(=O)N(C6CCC(=O)NC6=O)C7=O)CC5)C4)nc3)nc21] | 2-(2,6-dioxopiperidin-3-yl)-5-((5-(4-((1-(5-(9-methyl-9H-pyrrolo[2,3-b:4,5-c']dipyridin-2-yl)pyridin-2-yl)azetidin-3-yl)oxy)piperidin-1-yl)pentyl)oxy) isoindoline-1,3-dione | | 757.3 | |

TABLE 1-continued

| | | | | |
|---|---|---|---|---|
| 539 | 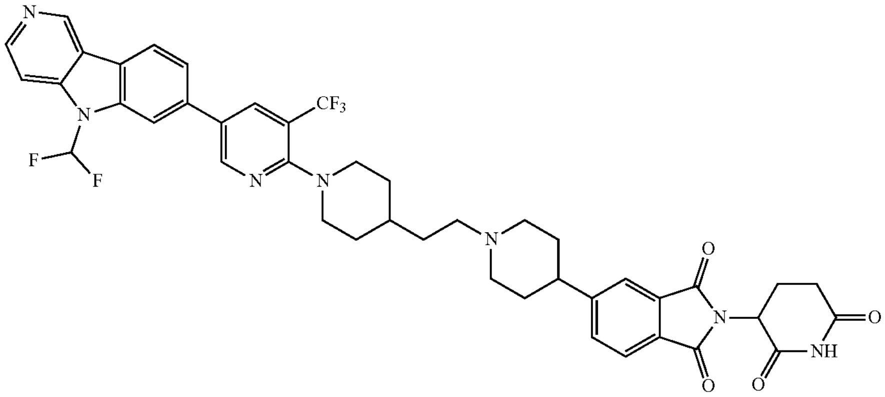 [SMILES: O=C1CCC(N2C(=O)c3ccc(C4CCN(CCC5CCN(c6ncc(-c7ccc8c9cnccc9n(C(F)F)c8c7)cc6C(F)(F)F)CC5)CC4)cc3C2=O)C(=O)N1] | 5-(1-(2-(1-(5-(5-(difluoromethyl)-5H-pyrido[4,3-b]indol-7-yl)-3-(trifluoromethyl)pyridin-2-yl)piperidin-4-yl)ethyl)piperidin-4-yl)-2-(2,6-dioxopiperidin-3-yl)isoindoline-1,3-dione | 814.3 | $^1$H NMR (400 MHz, DMSO-$d_6$) δ: 11.12 (s, 1 H), 9.82 (s, 1 H), 9.43 (s, 1 H), 8.99 (d, J = 6.40 Hz, 1 H), 8.86 (d, J = 6.4 Hz, 1 H), 8.62 (s, 2 H), 8.57 (d, J = 4.0 Hz, 1 H), 8.46 (d, J = 6.40 Hz, 1 H), 8.37 (s, 1 H), 8.02 (d, J = 8.0 Hz, 1 H), 7.93 (d, J = 4.0 Hz, 1 H), 7.80 (dd, J = 8.8, 2.00 Hz, 2 H), 5.17-5.12 (m, 1 H), 3.72-3.65 (m, 4 H), 3.21 (d, J = 12 Hz, 1 H), 3.19 (dd, J = 8.00, 7.20 Hz, 3 H), 3.07-2.98 (m, 3 H), 2.60-2.58 (m, 1 H), 2.10 (d, J = 8.0 Hz, 1 H), 1.86-1.82 (m, 2 H), 1.60 (s, 3 H), 1.37-1.35 (m, 2 H). |
| 540 | 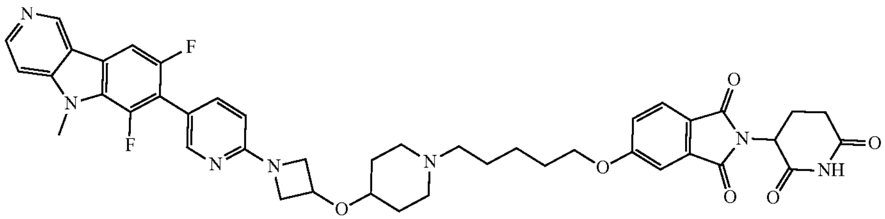 [SMILES: Cn1c2ccncc2c2cc(F)c(-c3ccc(N4CC(OC5CCN(CCCCCOc6ccc7c(c6)C(=O)N(C6CCC(=O)NC6=O)C7=O)CC5)C4)nc3)c(F)c21] | 5-((5-(4-((1-(5-(6,8-difluoro-5-methyl-5H-pyrido[4,3-b]indol-7-yl)pyridin-2-yl)azetidin-3-yl)oxy)piperidin-1-yl)pentyl)oxy)-2-(2,6-dioxopiperidin-3-yl)isoindoline-1,3-dione | 792.3 | $^1$H NMR (400 MHz, DMSO-$d_6$) δ: 11.11 (s, 1H), 9.80 (s, 1H), 9.23 (d, J = 5.0 Hz, 1H), 8.84 (d, J = 7.0 Hz, 1H), 8.36 (d, J = 8.9 Hz, 1H), 8.32-8.25 (m, 2H), 7.89-7.82 (m, 1H), 7.77 (d, J = 8.7 Hz, 1H), 7.44 (s, 1H), 7.36 (d, J = 9.0 Hz, 1H), 6.66-6.58 (m, 1H), 5.18-5.07 (m, 1H), 4.72-4.58 (m, 1H), 4.36-4.27 (m, 2H), 4.24-4.19 (m, 5H), 3.94-3.81 (m, 3H), 3.15-3.04 (m, 4H), 2.95-2.85 (m, 2H), 2.62 (d, J = 1.6 Hz, 1H), 2.22-2.09 (m, 2H), 2.01-1.95 (m, 1H), 1.86-1.78 (m, 3H), 1.73 (s, 3H), 1.55-1.39 (m, 3H) |
| 541 | 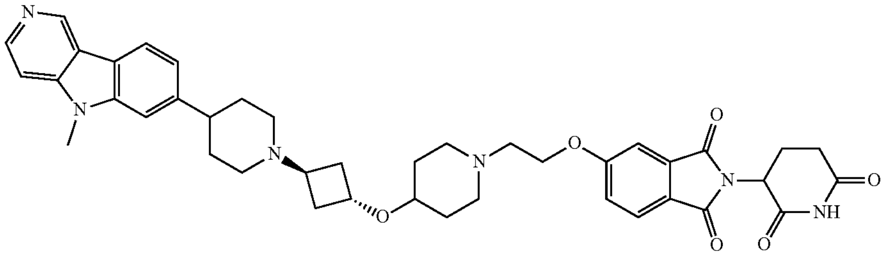 [SMILES: Cn1c2ccncc2c2ccc(C3CCN([C@H]4C[C@H](OC5CCN(CCOc6ccc7c(c6)C(=O)N(C6CCC(=O)NC6=O)C7=O)CC5)C4)CC3)cc21] | 2-(2,6-dioxopiperidin-3-yl)-5-(2-(4-((1r,3r)-3-(4-(5-methyl-5H-pyrido[4,3-b]indol-7-yl)piperidin-1-yl)cyclobutoxy) piperidin-1-yl)ethoxy) isoindoline-1,3-dione | 719.3 | $^1$H NMR (400 MHz, DMSO-d6) δ: 1.45 (d, J = 9.6 Hz, 2 H), 1.74-1.91 (m, 8 H), 2.01-2.15 (m, 3 H), 2.25 (t, J = 8.8 Hz, 2 H), 2.54-2.66 (m, 2 H), 2.75-2.86 (m, 5 H), 3.05 (d, J = 10.8 Hz, 2 H), 3.33 (s, 1 H), 3.90 (s, 3 H), 4.30 (t, J = 5.2 Hz, 2 H), 5.13 (d, J = 12.8 Hz, 1 H), 7.22 (d, J = 8.0 Hz, 1 H), 7.37 (d, J = 8.4 Hz, 1 H), 7.47 (s, 1 H), 7.52-7.65 (m, 2 H), 7.84 (d, J = 8.4 Hz, 1 H), 8.16 (s, 1 H), 8.18 (s, 2 H), 8.47 (d, J = 5.6 Hz, 1 H), 9.30 (s, 1 H), 11.13 (s, 1 H) |

TABLE 1-continued

| | | | | | |
|---|---|---|---|---|---|
| 542 | 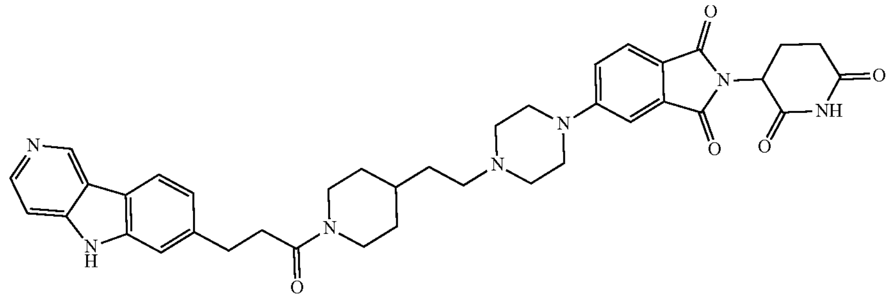 [SMILES: O=C1CCC(N2C(=O)c3ccc(N4CCN(CCC5CCN(C(=O)CCc6ccc7c(c6)[nH]c6ccncc67)CC5)CC4)cc3C2=O)C(=O)N1] | 5-(4-(2-(1-(3-(5H-pyrido[4,3-b]indol-7-yl)propanoyl)piperidin-4-yl)ethyl)piperazin-1-yl)-2-(2,6-dioxopiperidin-3-yl)isoindoline-1,3-dione | | 676.3 | |
| 543 | 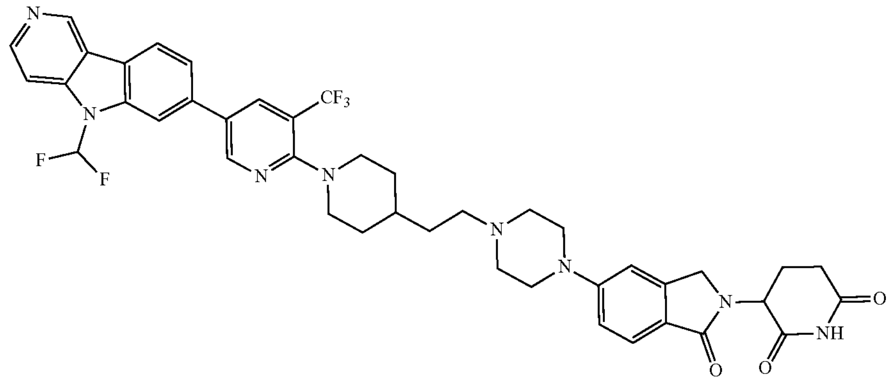 [SMILES: O=C1CCC(N2Cc3cc(N4CCN(CCC5CCN(c6ncc(-c7ccc8c9cnccc9n(C(F)F)c8c7)cc6C(F)(F)F)CC5)CC4)ccc3C2=O)C(=O)N1] | 3-(5-(4-(2-(1-(5-(5-(difluoromethyl)-5H-pyrido[4,3-b]indol-7-yl)-3-(trifluoromethyl)pyridin-2-yl)piperidin-4-yl)ethyl)piperazin-1-yl)-1-oxoisoindolin-2-yl)piperidine-2,6-dione | A | 801.3 | $^1$H NMR (400 MHz, DMSO-$d_6$) δ: 1.01 (t, J = 7.2 Hz, 1 H), 1.26-1.39 (m, 2 H), 1.43-1.64 (m, 3 H), 1.82 (d, J = 10.0 Hz, 2 H), 1.92-1.99 (m, 1 H), 2.29-2.48 (m, 9 H), 2.55-2.71 (m, 2 H), 2.86-3.02 (m, 3 H), 3.67 (d, J = 12.0 Hz, 2 H), 4.15-4.26 (m, 1 H), 4.29-4.39 (m, 1 H), 5.05 (d, J = 13.2 Hz, 1 H), 7.03-7.11 (m, 2 H), 7.52 (d, J = 8.4 Hz, 1 H), 7.78-7.91 (m, 2 H), 8.19 (s, 1 H), 8.27 (s, 1 H), 8.36-8.45 (m, 2 H), 8.48-8.67 (m, 1 H), 8.51 (s, 1 H), 8.95 (s, 1 H), 9.51 (s, 1 H), 10.95 (s, 1 H) |
| 544 | 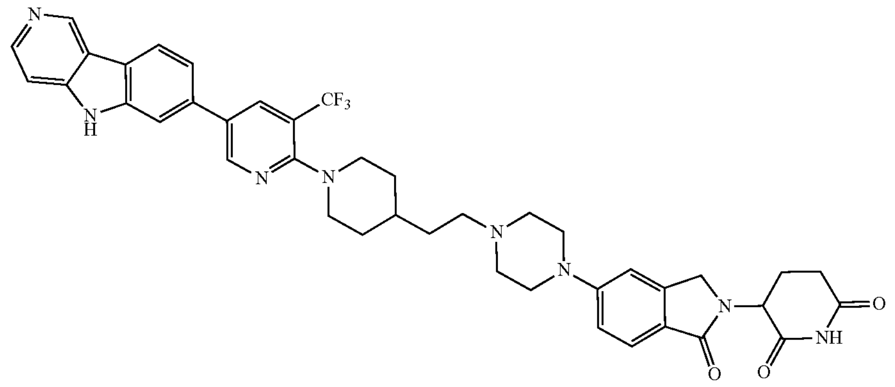 [SMILES: O=C1CCC(N2Cc3cc(N4CCN(CCC5CCN(c6ncc(-c7ccc8c(c7)[nH]c7ccncc78)cc6C(F)(F)F)CC5)CC4)ccc3C2=O)C(=O)N1] | 3-(5-(4-(2-(1-(5-(5H-pyrido[4,3-b]indol-7-yl)-3-(trifluoromethyl)pyridin-2-yl)piperidin-4-yl)ethyl)piperazin-1-yl)-1-oxoisoindolin-2-yl)piperidine-2,6-dione | | 751.3 | $^1$H NMR (400 MHz, DMSO-$d_6$) δ: 1.15-1.40 (m, 3 H), 1.52 (s, 4 H), 1.83 (d, J = 12.0 Hz, 2 H), 1.97 (d, J = 10.0 Hz, 1 H), 2.40 (s, 3 H), 2.59 (d, J = 16.8 Hz, 6 H), 2.82-3.09 (m, 4 H), 3.63 (d, J = 11.2 Hz, 2 H), 4.18-4.39 (m, 2 H), 5.00-5.11 (m, 1 H), 7.04-7.13 (m, 2 H), 7.51-7.58 (m, 2 H), 7.65 (d, J = 8.0 Hz, 1 H), 7.88 (s, 1 H), 8.34 (s, 2 H), 8.45 (d, J = 6.0 Hz, 1 H), 8.93 (s, 1 H), 9.39 (s, 1 H), 10.95 (s, 1 H), 11.85 (br s, 1 H) |

TABLE 1-continued

| | | | | |
|---|---|---|---|---|
| 545 | 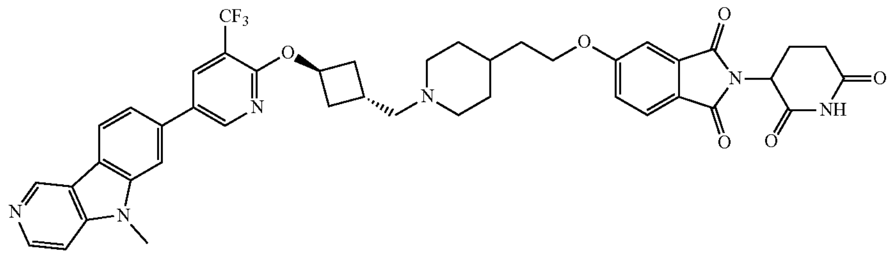 [SMILES: Cn1c2ccncc2c2ccc(-c3cnc(O[C@H]4C[C@H](CN5CCC(CCOc6ccc7c(c6)C(=O)N(C6CCC(=O)NC6=O)C7=O)CC5)C4)c(C(F)(F)F)c3)cc21] | 2-(2,6-dioxopiperidin-3-yl)-5-(2-(1-(((1r,3r)-3-((5-(5-methyl-5H-pyrido[4,3-b]indol-7-yl)-3-(trifluoromethyl)pyridin-2-yl)oxy)cyclobutyl)methyl)piperidin-4-yl)ethoxy)isoindoline-1,3-dione | 795.3 | $^1$H NMR (400 MHz, DMSO-$d_6$) δ: 11.10 (s, 1H), 9.77 (s, 1H), 9.04-8.89 (m, 2H), 8.78 (d, J = 6.8 Hz, 1H), 8.61-8.55 (m, 2H), 8.34 (s, 1H), 8.21 (d, J = 6.8 Hz, 1H), 7.96 (d, J = 8.0 Hz, 1H), 7.85 (d, J = 8.4 Hz, 1H), 7.45 (d, J = 2.4 Hz, 1H), 7.35 (dd, J = 2.0, 8.4 Hz, 1H), 5.47 (dd, J = 5.6, 6.4 Hz, 1H), 5.12 (dd, J = 5.4, 12.8 Hz, 1H), 4.25 (t, J = 5.6 Hz, 2H), 4.17-4.14 (m, 3H), 2.97-2.83 (m, 6H), 2.78-2.74 (m, 1H), 2.62 (d, J = 1.2 Hz, 3H), 2.08-2.01 (m, 2H), 2.00-1.93 (m, 3H), 1.75 (d, J = 2.8 Hz, 4H), 1.50-1.37 (m, 3H) |
| 546 | 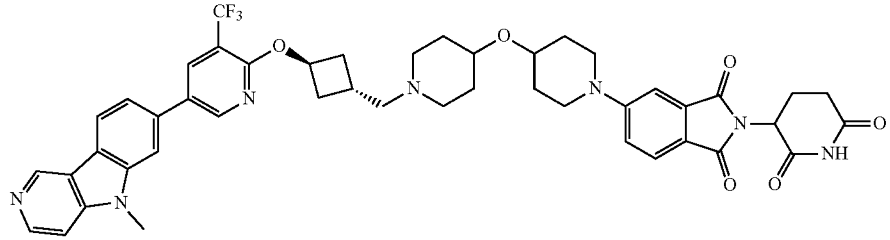 [SMILES: Cn1c2ccncc2c2ccc(-c3cnc(O[C@H]4C[C@H](CN5CCC(OC6CCN(c7ccc8c(c7)C(=O)N(C7CCC(=O)NC7=O)C8=O)CC6)CC5)C4)c(C(F)(F)F)c3)cc21] | 2-(2,6-dioxopiperidin-3-yl)-5-(4-((1-(((1r,3r)-3-((5-(5-methyl-5H-pyrido[4,3-b]indol-7-yl)-3-(trifluoromethyl)pyridin-2-yl)oxy)cyclobutyl)methyl)piperidin-4-yl)oxy)piperidin-1-yl)isoindoline-1,3-dione | 850.3 | $^1$H NMR (400 MHz, DMSO-$d_6$) δ: 11.07 (s, 1 H), 9.79 (s, 1 H), 9.46-9.03 (m, 1 H), 9.01-8.89 (m, 1 H), 8.79 (d, J = 6.80 Hz, 1 H), 8.64-8.50 (m, 2 H), 8.35 (s, 1 H), 8.23 (d, J = 7.20 Hz, 1 H), 7.97 (d, J = 8.00 Hz, 1 H), 7.67 (d, J = 8.40 Hz, 1 H), 7.41-7.16 (m, 2 H), 5.55-5.21 (m, 1 H), 5.06 (dd, J = 13.20, 5.60 Hz, 1 H), 4.16 (s, 3 H), 3.89-3.73 (m, 4 H), 3.32-3.24 (m, 4 H), 3.08-2.83 (m, 4 H), 2.80-2.71 (m, 2 H), 2.61 (s, 1 H), 2.55 (d, J = 8.40 Hz, 2 H), 2.44-2.39 (m, 2 H), 2.14-2.06 (m, 1 H), 2.05-1.97 (m, 2 H), 1.95-1.83 (m, 4 H), 1.62-1.43 (m, 3 H). |
| 547 | 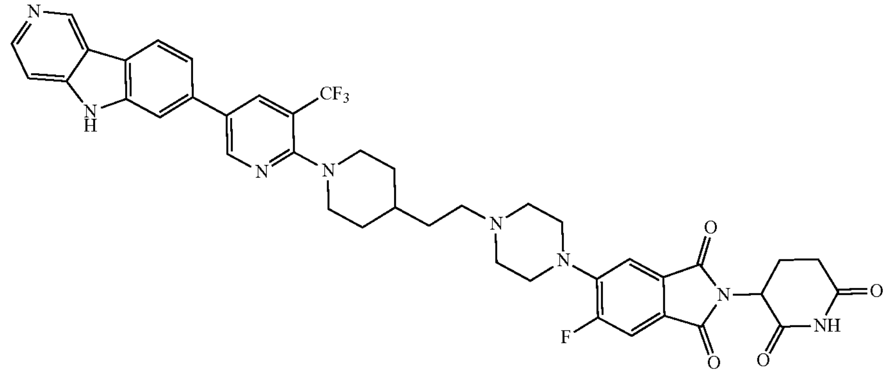 [SMILES: O=C1CCC(N2C(=O)c3cc(F)c(N4CCN(CCC5CCN(c6ncc(-c7ccc8c(c7)[nH]c7ccncc78)cc6C(F)(F)F)CC5)CC4)cc3C2=O)C(=O)N1] | 5-(4-(2-(1-(5-(5H-pyrido[4,3-b]indol-7-yl)-3-(trifluoromethyl)pyridin-2-yl)piperidin-4-yl)ethyl)piperazin-1-yl)-2-(2,6-dioxopiperidin-3-yl)-6-fluoroisoindoline-1,3-dione | 783.3 | $^1$H NMR: (400 MHz, DMSO-$d_6$) δ: 13.25 (s, 1 H), 11.11 (s, 1 H), 9.89 (d, J = 3.60 Hz, 1 H), 9.78 (s, 1 H), 8.97 (d, J = 2.40 Hz, 1 H), 8.68 (d, J = 6.80 Hz, 1 H), 8.55 (d, J = 8.40 Hz, 1 H), 8.40 (d, J = 2.40 Hz, 1 H), 8.12 (d, J = 0.80 Hz, 1 H), 8.03 (d, J = 6.80 Hz, 1 H), 7.89 (dd, J = 8.40, 1.60 Hz, 1 H), 7.82 (d, J = 11.20 Hz, 1 H), 7.61 (d, J = 7.20 Hz, 1 H), 5.13 (dd, J = 12.80, 5.20 Hz, 1 H), 3.90-3.74 (m, 2 H), 3.68 (d, J = 12.40 Hz, 3 H), 3.35-3.16 (m, 6 H), 2.97 (t, J = 11.60 Hz, 2 H), 2.92-2.84 (m, 1 H), 2.53-2.65 (m, 2 H), 2.52 (d, J = 1.60 Hz, 1 H), 2.07-1.98 (m, 1 H), 1.83 (d, J = 11.20 Hz, 2 H), 1.76-1.67 (m, 2 H), 1.64-1.53 (m, 1 H), 1.42-1.29 (m, 2 H). |

TABLE 1-continued

| | | | | |
|---|---|---|---|---|
| 548 | 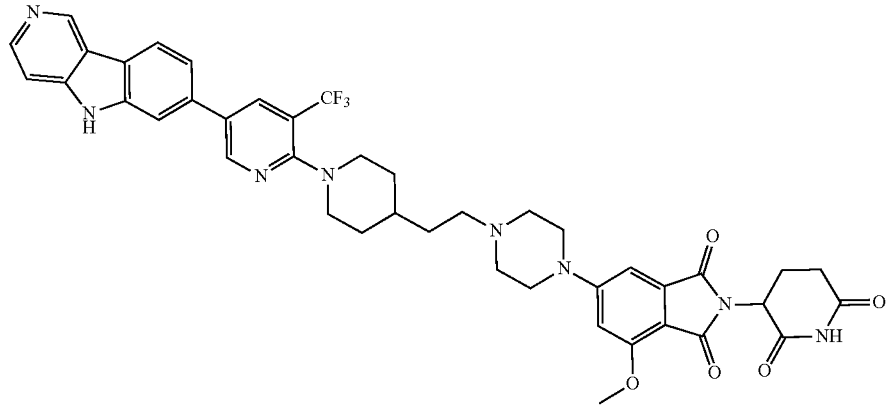 [SMILES: COc1cc(N2CCN(CCC3CCN(c4ncc(-c5ccc6c(c5)[nH]c5ccncc56)cc4C(F)(F)F)CC3)CC2)cc2c1C(=O)N(C1CCC(=O)NC1=O)C2=O] | 6-(4-(2-(1-(5-(5H-pyrido[4,3-b]indol-7-yl)-3-(trifluoromethyl)pyridin-2-yl)piperidin-4-yl)ethyl)piperazin-1-yl)-2-(2,6-dioxopiperidin-3-yl)-4-methoxyisoindoline-1,3-dione | 795.3 | $^1$H NMR (400 MHz, DMSO-$d_6$) δ: 13.17 (s, 1 H), 11.06 (s, 1 H), 10.08-9.53 (m, 2 H), 8.97 (d, J = 2.00 Hz, 1 H), 8.68 (d, J = 6.80 Hz, 1 H), 8.55 (d, J = 8.40 Hz, 1 H), 8.41 (d, J = 2.40 Hz, 1 H), 8.12 (s, 1 H), 8.03 (d, J = 6.80 Hz, 1 H), 7.94-7.82 (m, 1 H), 7.10 (s, 1 H), 6.81 (s, 1 H), 5.10-4.97 (m, 1 H), 4.39-4.22 (m, 2 H), 3.96 (s, 3 H), 3.67 (d, J = 12.80 Hz, 3 H), 3.28-3.22 (m, 3 H), 3.20-3.11 (m, 2 H), 3.03-2.78 (m, 4 H), 2.62-2.56 (m, 3 H), 2.06-1.93 (m, 1 H), 1.83 (d, J = 11.60 Hz, 2 H), 1.77-1.65 (m, 2 H), 1.63-1.52 (m, 1 H), 1.43-1.29 (m, 2 H). |
| 549 | 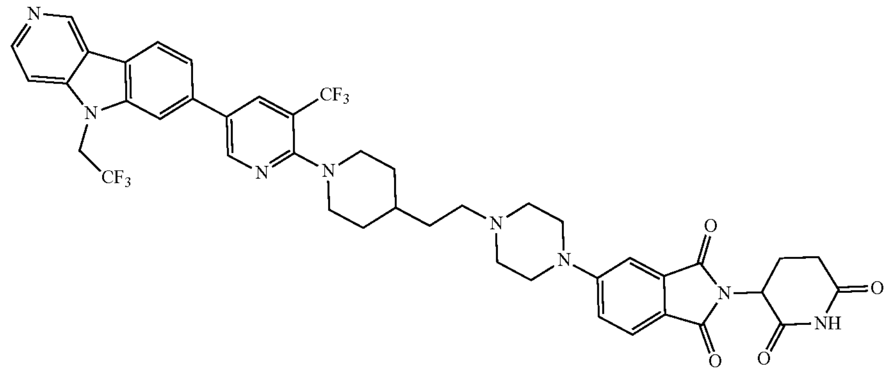 [SMILES: O=C1CCC(N2C(=O)c3ccc(N4CCN(CCC5CCN(c6ncc(-c7ccc8c9cnccc9n(CC(F)(F)F)c8c7)cc6C(F)(F)F)CC5)CC4)cc3C2=O)C(=O)N1] | 2-(2,6-dioxopiperidin-3-yl)-5-(4-(2-(1-(5-(5-(2,2,2-trifluoroethyl)-5H-pyrido[4,3-b]indol-7-yl)-3-(trifluoromethyl)pyridin-2-yl)piperidin-4-yl)ethyl)piperazin-1-yl)isoindoline-1,3-dione | 847.3 | 1H NMR (400 MHz, DMSO-d6) δ: 1.29-1.43 (m, 2 H), 1.59 (s, 1 H), 1.70 (s, 2 H), 1.83 (d, J = 10.8 Hz, 2 H), 1.98-2.06 (m, 1 H), 2.53-2.70 (m, 3 H), 2.81-3.05 (m, 3 H), 3.26 (d, J = 8.0 Hz, 8 H), 3.72 (s, 1 H), 4.23 (s, 2 H), 5.10 (d, J = 12.8 Hz, 1 H), 5.82 (d, J = 8.8 Hz, 2 H), 7.31-7.42 (m, 1 H), 7.50 (s, 1 H), 7.78 (d, J = 8.4 Hz, 1 H), 8.02 (d, J = 8.4 Hz, 1 H), 8.35 (d, J = 6.8 Hz, 1 H), 8.44-8.52 (m, 2 H), 8.58 (d, J = 8.0 Hz, 1 H), 8.87 (d, J = 6.8 Hz, 1 H), 9.03 (d, J = 2.0 Hz, 1 H), 9.85 (s, 1 H), 11.10 (s, 1 H) |

TABLE 1-continued

| | | | | |
|---|---|---|---|---|
| 550 | 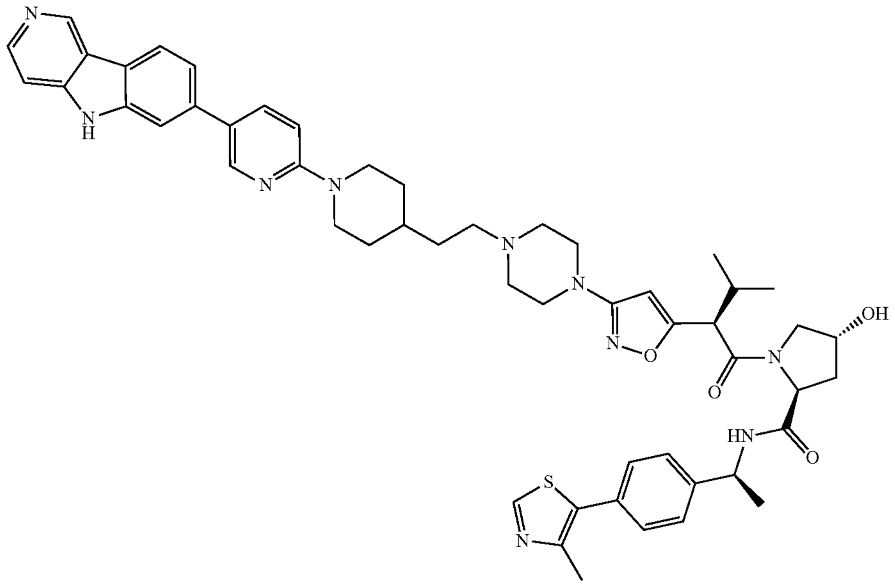 [SMILES: Cc1ncsc1-c1ccc([C@H](C)NC(=O)[C@@H]2C[C@@H](O)CN2C(=O)[C@@H](c2cc(N3CCN(CCC4CCN(c5ccc(-c6ccc7c(c6)[nH]c6ccncc67)cn5)CC4)CC3)no2)C(C)C)cc1] | (2S,4R)-1-((R)-2-(3-(4-(2-(1-(5-(5H-pyrido[4,3-b]indol-7-yl)pyridin-2-yl)piperidin-4-yl)ethyl)piperazin-1-yl)isoxazol-5-yl)-3-methylbutanoyl)-4-hydroxy-N-((S)-1-(4-(4-methylthiazol-5-yl)phenyl)ethyl) pyrrolidine-2-carboxamide | 921.4 | $^1$H NMR: (400 MHz, CHLOROFORM-d) δ: 13.16 (s, 1H), 9.88-9.68 (m, 2H), 9.04-8.83 (m, 1H), 8.66 (d, J = 6.8 Hz, 1H), 8.57 (d, J = 2.4 Hz, 1H), 8.49 (d, J = 8.4 Hz, 1H), 8.39 (d, J = 7.6 Hz, 1H), 8.09 (dd, J = 2.4, 9.2 Hz, 1H), 8.02-7.96 (m, 2H), 7.79 (dd, J = 1.2, 8.4 Hz, 1H), 7.49-7.42 (m, 2H), 7.41-7.35 (m, 2H), 7.11 (d, J = 9.2 Hz, 1H), 6.31-6.18 (m, 1H), 4.97-4.86 (m, 1H), 4.99-4.24 (m, 5H), 3.49-3.40 (m, 4H), 3.27-3.07 (m, 7H), 2.95 (t, J = 11.6 Hz, 2H), 2.47-2.44 (m, 3H), 2.30-2.11 (m, 2H), 2.08-1.98 (m, 1H), 1.83-1.75 (m, 3H), 1.65 (s, 3H), 1.46 (d, J = 6.8 Hz, 1H), 1.38 (d, J = 7.2 Hz, 2H), 1.28-1.17 (m, 2H), 1.02-0.94 (m, 3H), 0.87-0.77 (m, 3H) |
| 551 | 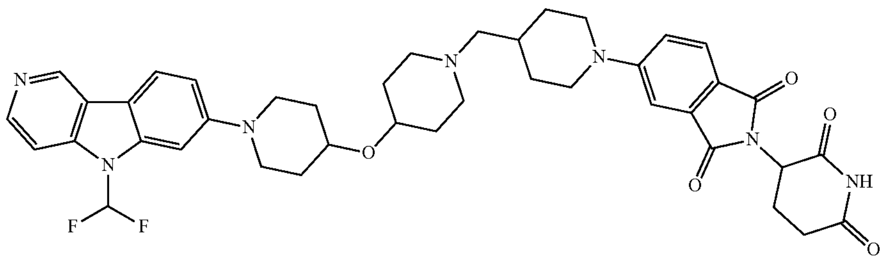 [SMILES: O=C1CCC(N2C(=O)c3ccc(N4CCC(CN5CCC(OC6CCN(c7ccc8c9cnccc9n(C(F)F)c8c7)CC6)CC5)CC4)cc3C2=O)C(=O)N1] | 5-(4-((4-((1-(5-(difluoromethyl)-5H-pyrido[4,3-b]indol-7-yl)piperidin-4-yl)oxy)piperidin-1-yl)methyl)piperidin-1-yl)-2-(2,6-dioxopiperidin-3-yl)isoindoline-1,3-dione | 754.3 | 1H NMR (DMSO-$d_6$) δ: 11.08 (s, 1H), 9.64 (s, 1H), 9.37-9.09 (m, 1H), 8.77 (d, J = 6.8 Hz, 1H), 8.73-8.41 (m, 1H), 8.30-8.17 (m, 2H), 7.67 (d, J = 8.4 Hz, 1H), 7.45-7.15 (m, 4H), 5.07 (dd, J = 5.2, 13.2 Hz, 1H), 4.09 (d, J = 12.8 Hz, 3H), 3.90 (s, 1H), 3.78-3.68 (m, 3H), 3.54 (d, J = 12.8 Hz, 1H), 3.37 (d, J = 11.2 Hz, 1H), 3.26-2.83 (m, 9H), 2.62-2.53 (m, 1H), 2.18-1.78 (m, 9H), 1.73-1.50 (m, 3H), 1.35-1.16 (m, 2H) |
| 552 | 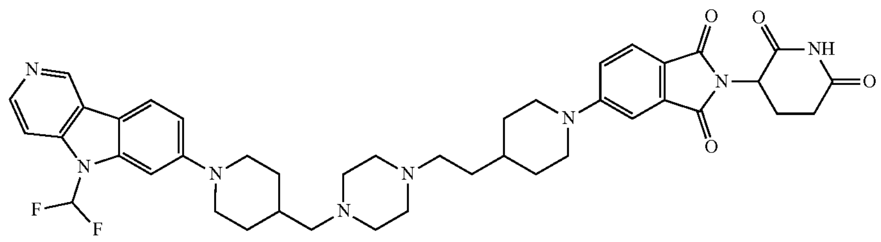 [SMILES: O=C1CCC(N2C(=O)c3ccc(N4CCC(CCN5CCN(CC6CCN(c7ccc8c9cnccc9n(C(F)F)c8c7)CC6)CC5)CC4)cc3C2=O)C(=O)N1] | 5-(4-(2-(4-((1-(5-(difluoromethyl)-5H-pyrido[4,3-b]indol-7-yl)piperidin-4-yl)methyl)piperazin-1-yl)ethyl)piperidin-1-yl)-2-(2,6-dioxopiperidin-3-yl)isoindoline-1,3-dione | 767.4 | 1H NMR (DMSO-$d_6$) δ: 11.08 (s, 1H), 9.64 (s, 1H), 8.77 (d, J = 6.8 Hz, 1H), 8.73-7.40 (m, 1H), 8.29-8.20 (m, 2H), 7.67 (d, J = 8.8 Hz, 1H), 7.38-7.24 (m, 4H), 5.06 (dd, J = 5.2, 12.8 Hz, 1H), 4.11-3.97 (m, 10H), 3.15 (d, J = 1.2 Hz, 2H), 3.03-2.70 (m, 9H), 2.63-2.53 (m, 1H), 2.05-1.53 (m, 10H), 1.34-1.13 (m, 4H). |

TABLE 1-continued

| | | | | | |
|---|---|---|---|---|---|
| 553 | 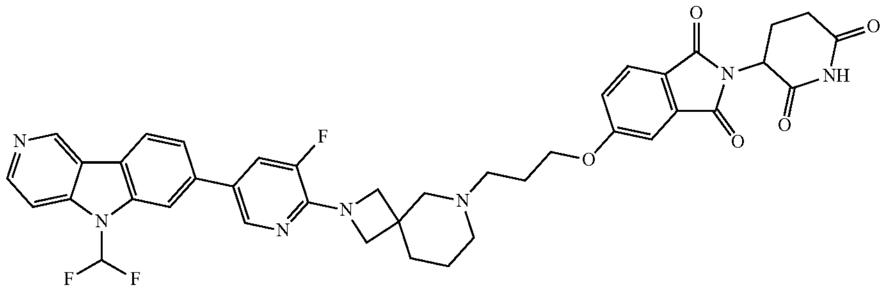 [SMILES: O=C1CCC(N2C(=O)c3ccc(OCCCN4CCCC5(C4)CN(c4ncc(-c6ccc7c8cnccc8n(C(F)F)c7c6)cc4F)C5)cc3C2=O)C(=O)N1] | 5-(3-(2-(5-(5-(difluoromethyl)-5H-pyrido[4,3-b]indol-7-yl)-3-fluoropyridin-2-yl)-2,6-diazaspiro[3.5]nonan-6-yl)propoxy)-2-(2,6-dioxopiperidin-3-yl)isoindoline-1,3-dione | | 752.3 | 1H NMR (400 MHz, METHANOL-d4) δ: 9.3 (s, 1 H), 8.6 (d, J = 5.6 Hz, 1 H), 8.0-8.4 (m, 3 H), 8.0 (s, 1 H), 7.7-7.8 (m, 3 H), 7.7-7.7 (m, 1 H), 7.4 (d, J = 2.0 Hz, 1 H), 7.3 (dd, J = 8.4, 2.4 Hz, 1 H), 5.1 (dd, J = 12.4, 5.4 Hz, 1 H), 4.6 (br s, 3 H), 4.3 (t, J = 5.6 Hz, 2 H), 3.9-4.1 (m, 4 H), 3.0 (br s, 2 H), 2.6-2.9 (m, 4 H), 2.0-2.3 (m, 3 H), 1.8-2.0 (m 4 H) |
| 554 | 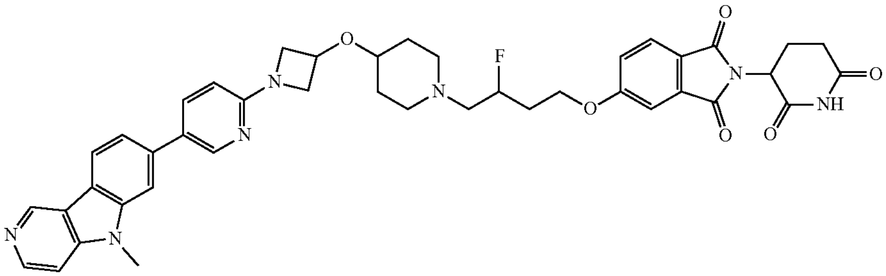 [SMILES: Cn1c2ccncc2c2ccc(-c3ccc(N4CC(OC5CCN(CC(F)CCOc6ccc7c(c6)C(=O)N(C6CCC(=O)NC6=O)C7=O)CC5)C4)nc3)cc21] | 2-(2,6-dioxopiperidin-3-yl)-5-(3-fluoro-4-(4-((1-(5-(5-methyl-5H-pyrido[4,3-b]indol-7-yl)pyridin-2-yl)azetidin-3-yl)oxy)piperidin-1-yl)butoxy)isoindoline-1,3-dione | | 762.3 | $^1$H NMR (400 MHz, DMSO-$d_6$) δ: 11.13 (s, 1H), 10.05 (s, 1H), 9.77 (s, 1H), 8.77 (d, J = 6.8 Hz, 1H), 8.63 (s, 1H), 8.53 (d, J = 8.0 Hz, 1H), 8.31-8.15 (m, 3H), 7.87 (t, J = 8.0 Hz, 2H), 7.49 (s, 1H), 7.40 (m, 1H), 6.76 (d, J = 8.8 Hz, 1H), 5.47-5.23 (m, 1H), 5.13 (m, 1H), 4.70-4.61 (m, 1H), 4.45-4.34 (m, 4H), 4.15 (s, 4H), 3.98 (d, J = 2.8 Hz, 1H), 3.70-3.39 (m, 5H), 3.30-3.05 (m, 2H), 2.97-2.84 (m, 1H), 2.74-2.53 (m, 2H), 2.24-1.93 (m, 6H), 1.80-1.63 (m, 1H) |
| 555 | 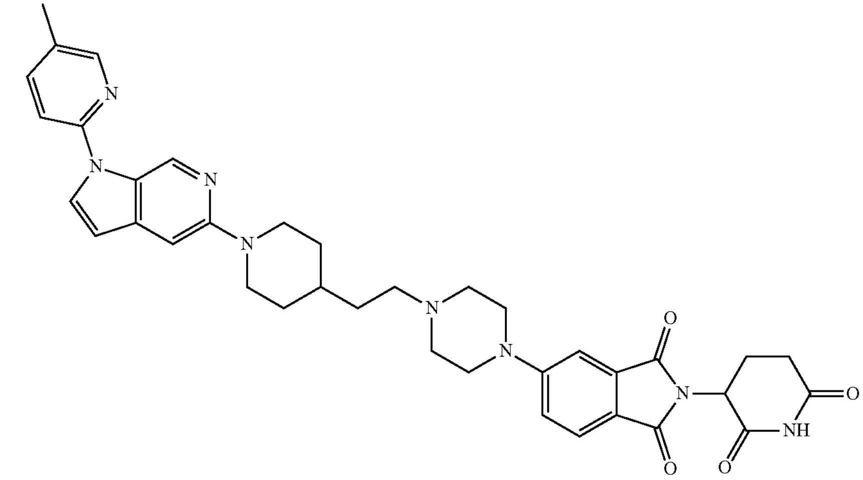 [SMILES: Cc1ccc(-n2ccc3cc(N4CCC(CCN5CCN(c6ccc7c(c6)C(=O)N(C6CCC(=O)NC6=O)C7=O)CC5)CC4)ncc32)nc1] | 2-(2,6-dioxopiperidin-3-yl)-5-(4-(2-(1-(1-(5-methylpyridin-2-yl)-1H-pyrrolo[2,3-c]pyridin-5-yl)piperidin-4-yl)ethyl)piperazin-1-yl)isoindoline-1,3-dione | A | 661.3 | $^1$H NMR (400 MHz, DMSO-$d_6$) δ: 11.09 (s, 1H), 10.10-9.77 (m, 1H), 9.36 (s, 1H), 8.61 (s, 1H), 8.42 (s, 1H), 7.90-7.84 (m, 1H), 7.83-7.75 (m, 2H), 7.49 (s, 1H), 7.43-7.31 (m, 2H), 6.82 (d, J = 3.1 Hz, 1H), 5.17-5.01 (m, 1H), 4.30-4.18 (m, 2H), 4.06 (d, J = 12.9 Hz, 2H), 3.22-3.12 (m, 4H), 3.07-2.95 (m, 3H), 2.64-2.53 (m, 6H), 2.36 (s, 3H), 2.05-1.97 (m, 1H), 1.84 (d, J = 11.4 Hz, 2H), 1.75-1.60 (m, 3H), 1.32 (d, J = 11.5 Hz, 2H) |

TABLE 1-continued

| | | | | | |
|---|---|---|---|---|---|
| 556 | 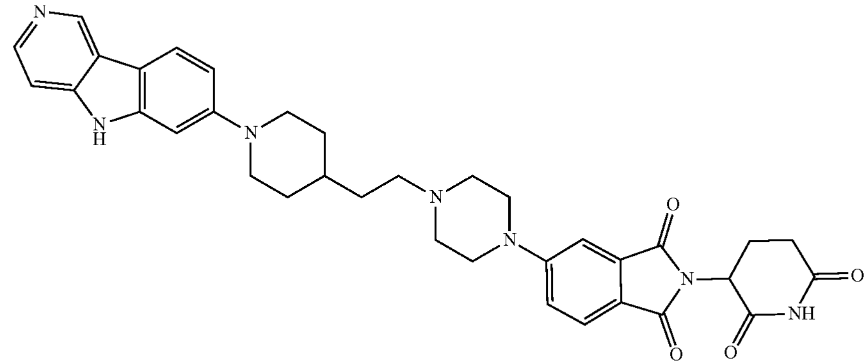 [SMILES: O=C1CCC(N2C(=O)c3ccc(N4CCN(CCC5CCN(c6ccc7c(c6)[nH]c6ccncc67)CC5)CC4)cc3C2=O)C(=O)N1] | 5-(4-(2-(1-(5H-pyrido[4,3-b]indol-7-yl)piperidin-4-yl)ethyl)piperazin-1-yl)-2-(2,6-dioxopiperidin-3-yl)isoindoline-1,3-dione | | 620.3 | $^1$H NMR (400 MHz, DMSO-$d_6$) δ: 14.54 (s, 1H), 12.68 (s, 1H), 11.10 (s, 1H), 9.90-9.60 (m, 1H), 9.47 (s, 1H), 8.53 (d, J = 6.4 Hz, 1H), 8.19 (d, J = 8.8 Hz, 1H), 7.87 (d, J = 6.8 Hz, 1H), 7.78 (d, J = 8.4 Hz, 1H), 7.51 (s, 1H), 7.38 (d, J = 9.2 Hz, 1H), 7.21 (d, J = 8.8 Hz, 1H), 7.11 (s, 1H), 5.20-4.97 (m, 1H), 4.23 (s, 2H), 3.92 (d, J = 12.6 Hz, 3H), 3.62 (s, 2H), 3.25 (s, 5H), 2.88-2.81 (m, 3H), 2.05 (s, 1H), 1.84 (d, J = 11.6 Hz, 2H), 1.73-1.53 (m, 3H), 1.34 (d, J = 12.0 Hz, 2H) |
| 557 | 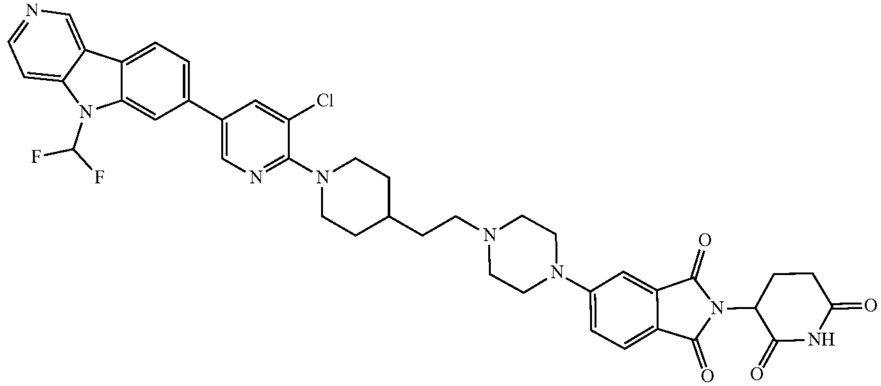 [SMILES: O=C1CCC(N2C(=O)c3ccc(N4CCN(CCC5CCN(c6ncc(-c7ccc8c9cnccc9n(C(F)F)c8c7)cc6Cl)CC5)CC4)cc3C2=O)C(=O)N1] | 5-(4-(2-(1-(3-chloro-5-(5-(difluoromethyl)-5H-pyrido[4,3-b]indol-7-yl)pyridin-2-yl)piperidin-4-yl)ethyl)piperazin-1-yl)-2-(2,6-dioxopiperidin-3-yl)isoindoline-1,3-dione | | 781.3 | $^1$H NMR (400 MHz, DMSO-$d_6$) δ: 11.08 (s, 1 H), 9.49 (s, 1 H), 8.77-8.59 (m, 2 H), 8.52-8.31 (m, 2 H), 8.28-8.21 (m, 2 H), 7.86-7.79 (m, 2 H), 7.70-7.65 (m, 1 H), 7.34 (s, 1 H), 7.28-7.22 (m, 1 H), 5.15-4.92 (m, 1 H), 3.88-3.82 (m, 2 H), 3.46-3.43 (m, 8 H), 2.86-2.81 (m, 3 H), 2.60 (d, J = 3.60 Hz, 2 H), 2.42-2.39 (m, 2 H), 2.08-2.00 (m, 1 H), 1.82 (d, J = 10.40 Hz, 2 H), 1.52-1.47 (m, 2 H), 1.38-1.32 (m, 2 H), 1.23 (s, 1 H). |
| 558 | 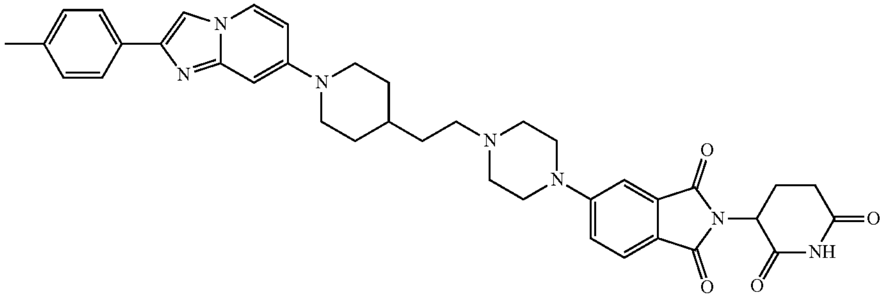 [SMILES: Cc1ccc(-c2cn3ccc(N4CCC(CCN5CCN(c6ccc7c(c6)C(=O)N(C6CCC(=O)NC6=O)C7=O)CC5)CC4)cc3n2)cc1] | 2-(2,6-dioxopiperidin-3-yl)-5-(4-(2-(1-(2-(p-tolyl)imidazo[1,2-a]pyridin-7-yl)piperidin-4-yl)ethyl)piperazin-1-yl)isoindoline-1,3-dione | A | 660.3 | $^1$H NMR (400 MHz, DMSO-$d_6$) δ: 11.09 (s, 1H), 9.88-9.62 (m, 1H), 8.50 (d, J = 7.6 Hz, 1H), 8.28 (s, 1H), 7.80-7.70 (m, 3H), 7.50 (d, J = 2.4 Hz, 1H), 7.42-7.28 (m, 4H), 6.75 (s, 1H) 5.10 (dd, J = 5.2, 12.8 Hz, 1H), 4.30-4.18 (m, 2H), 4.11-4.02 (m, 2H), 3.65-3.56 (m, 2H), 3.27-3.19 (m, 4H), 3.19-3.11 (m, 2H), 3.10-3.02 (m, 2H), 2.95-2.83 (m, 1H), 2.64-2.55 (m, 2H), 2.38 (s, 3H), 2.08-1.96 (m, 1H), 1.88-1.78 (m, 2H), 1.73-1.61 (m, 3H), 1.30-1.17 (m, 2H) |

TABLE 1-continued

| | | | | |
|---|---|---|---|---|
| 559 | 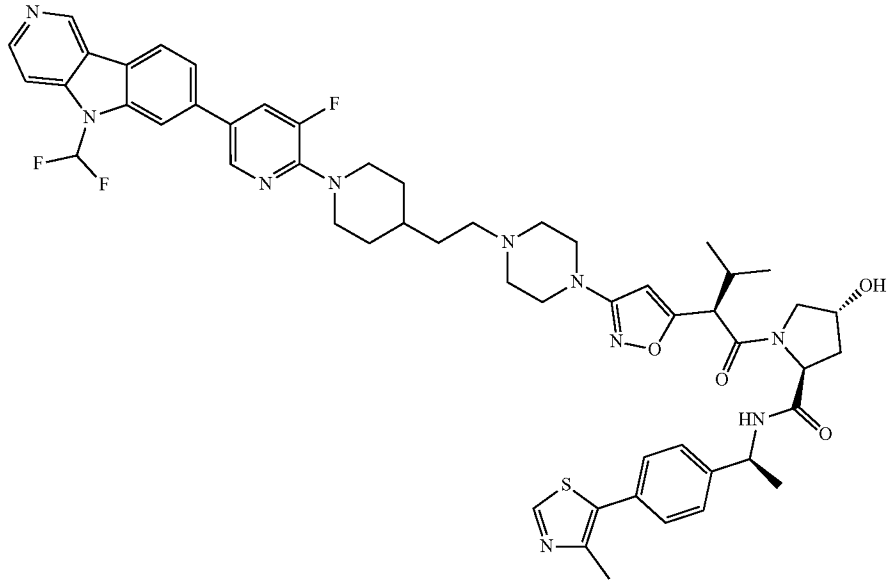 [SMILES: Cc1ncsc1-c1ccc([C@H](C)NC(=O)[C@@H]2C[C@@H](O)CN2C(=O)[C@@H](c2cc(N3CCN(CCC4CCN(c5ncc(-c6ccc7c8cnccc8n(C(F)F)c7c6)cc5F)CC4)CC3)no2)C(C)C)cc1] | (2S,4R)-1-((R)-2-(3-(4-(2-(1-(5-(5-(difluoromethyl)-5H-pyrido[4,3-b]indol-7-yl)-3-fluoropyridin-2-yl)piperidin-4-yl)ethyl)piperazin-1-yl)isoxazol-5-yl)-3-methylbutanoyl)-4-hydroxy-N-((S)-1-(4-(4-methylthiazol-5-yl)phenyl)ethyl) pyrrolidine-2-carboxamide | 989.4 | $^1$H NMR: (400 MHz, CHLOROFORM-d) δ: 9.93-9.60 (m, 2H), 9.04-8.94 (m, 1H), 8.93-8.85 (m, 1H), 8.80-8.48 (m, 3H), 8.42-8.28 (m, 3H), 8.12-7.97 (m, 2H), 7.52-7.29 (m, 4H), 6.35-6.17 (m, 1H), 4.94-4.89 (m, 1H), 4.35 (t, J = 8.0 Hz, 1H), 4.32-4.28 (m, 1H), 4.14 (d, J = 12.4 Hz, 2H), 3.89-3.68 (m, 4H), 3.66-3.53 (m, 3H), 3.49-3.41 (m, 1H), 3.26-3.18 (m, 2H), 3.13 (d, J = 10.8 Hz, 3H), 3.01-2.87 (m, 2H), 2.46 (s, 3H), 2.26-2.15 (m, 3H), 2.08-1.98 (m, 2H), 1.84-1.74 (m, 3H), 1.70-1.59 (m, 3H), 1.47 (d, J = 7.2 Hz, 1H), 1.38 (d, J = 7.2 Hz, 2H), 1.34-1.26 (m, 2H), 1.01-0.93 (m, 3H), 0.86-0.78 (m, 3H) |
| 560 | 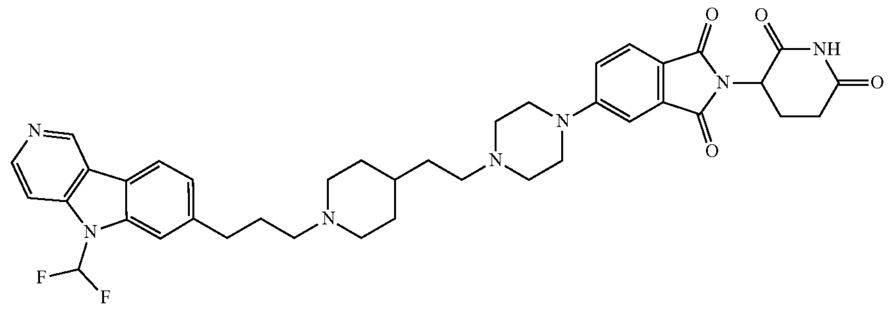 [SMILES: O=C1CCC(N2C(=O)c3ccc(N4CCN(CCC5CCN(CCCc6ccc7c8cnccc8n(C(F)F)c7c6)CC5)CC4)cc3C2=O)C(=O)N1] | 5-(4-(2-(1-(3-(5-(difluoromethyl)-5H-pyrido[4,3-b]indol-7-yl)propyl)piperidin-4-yl)ethyl)piperazin-1-yl)-2-(2,6-dioxopiperidin-3-yl)isoindoline-1,3-dione | 712.3 | |

TABLE 1-continued

| | | | | | |
|---|---|---|---|---|---|
| 561 | 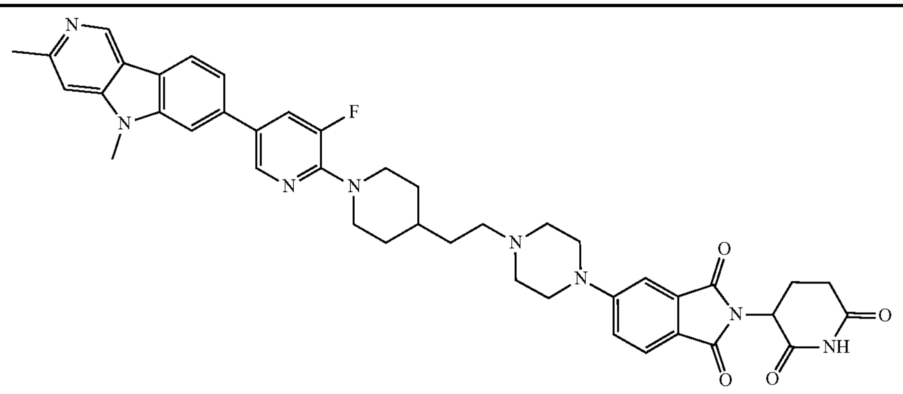 | 5-(4-(2-(1-(5-(3,5-dimethyl-5H-pyrido[4,3-b]indol-7-yl)-3-fluoropyridin-2-yl)piperidin-4-yl)ethyl)piperazin-1-yl)-2-(2,6-dioxopiperidin-3-yl)isoindoline-1,3-dione | A | 743.3 | $^1$H NMR (400 MHz, DMSO-d6) δ: 11.10 (s, 1H), 9.62 (s, 2H), 8.63-8.59 (m, 1H), 8.46 (d, J = 8.2 Hz, 1H), 8.21 (s, 1H), 8.12 (dd, J = 1.9, 15.1 Hz, 1H), 8.05 (s, 1H), 7.88 (dd, J = 1.3, 8.4 Hz, 1H), 7.78 (d, J = 8.4 Hz, 1H), 7.53-7.48 (m, 1H), 7.37 (dd, J = 2.0, 8.5 Hz, 1H), 5.10 (dd, J = 5.3, 12.9 Hz, 1H), 4.32-4.18 (m, 2H), 4.15-4.05 (m, 5H), 3.74-3.54 (m, 2H), 3.28-3.09 (m, 5H), 2.86-2.79 (m, 2H), 2.80 (s, 3H), 2.03 (td, J = 2.3, 8.0 Hz, 2H), 1.80-1.50 (m, 7H), 1.40-1.25 (m, 2H). |
| 562 | 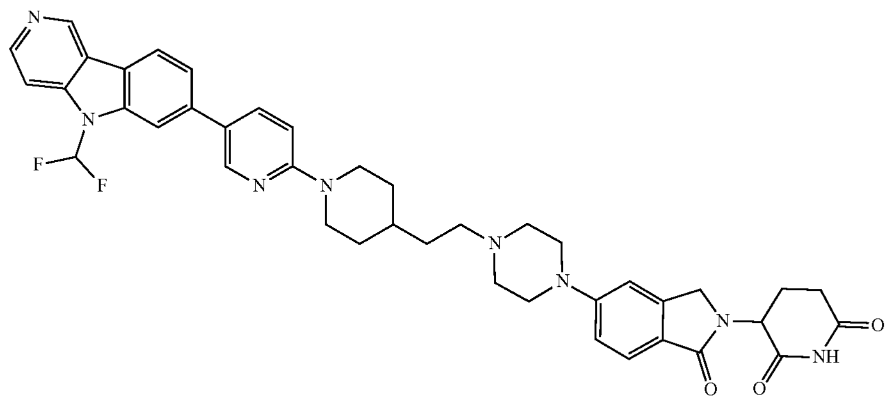 [SMILES: O=C1CCC(N2Cc3cc(N4CCN(CCC5CCN(c6ccc(-c7ccc8c9cnccc9n(C(F)F)c8c7)cn6)CC5)CC4)ccc3C2=O)C(=O)N1] | 3-(5-(4-(2-(1-(5-(5-(difluoromethyl)-5H-pyrido[4,3-b]indol-7-yl)pyridin-2-yl)piperidin-4-yl)ethyl)piperazin-1-yl)-1-oxoisoindolin-2-yl)piperidine-2,6-dione | | 733.3 | $^1$H NMR (400 MHz, DMSO-d6) δ: 1.00-1.33 (m, 3 H), 1.68 (s, 2 H), 1.76-1.86 (m, 2 H), 1.93-2.01 (m, 1 H), 2.31-2.42 (m, 1 H), 2.56-2.72 (m, 2 H), 2.88-2.99 (m, 3 H), 3.14 (d, J = 10.0 Hz, 3 H), 3.26 (s, 4 H), 4.05 (d, J = 10.0 Hz, 2 H), 4.22-4.29 (m, 1 H), 4.34-4.46 (m, 3 H), 5.07 (d, J = 13.2 Hz, 1 H), 7.08 (d, J = 8.8 Hz, 1 H), 7.14-7.24 (m, 2 H), 7.61 (d, J = 8.8 Hz, 1 H), 7.90-7.98 (m, 1 H), 8.08 (d, J = 9.2 Hz, 1 H), 8.21-8.29 (m, 1 H), 8.32 (d, J = 6.4 Hz, 1 H), 8.47-8.68 (m, 3 H), 8.89 (d, J = 6.4 Hz, 1 H), 9.72 (s, 1 H), 9.86 (s, 1 H), 10.97 (s, 1 H) |

TABLE 1-continued

| | | | | | |
|---|---|---|---|---|---|
| 563 | 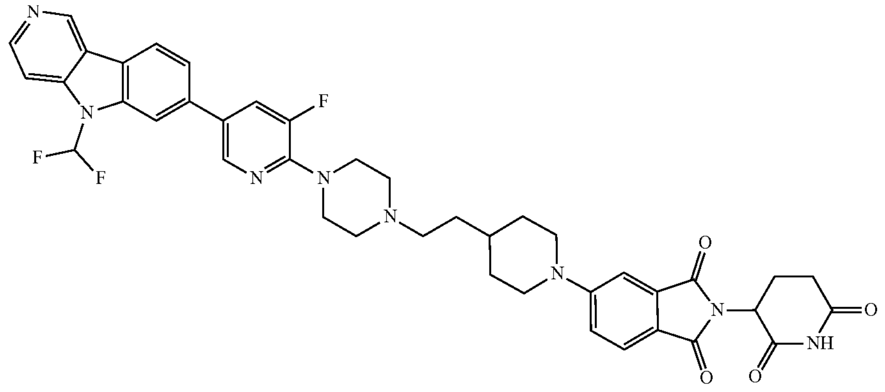 [SMILES: O=C1CCC(N2C(=O)c3ccc(N4CCC(CCN5CCN(c6ncc(-c7ccc8c9cnccc9n(C(F)F)c8c7)cc6F)CC5)CC4)cc3C2=O)C(=O)N1] | 5-(4-(2-(4-(5-(5-(difluoromethyl)-5H-pyrido[4,3-b]indol-7-yl)-3-fluoropyridin-2-yl)piperazin-1-yl)ethyl)piperidin-1-yl)-2-(2,6-dioxopiperidin-3-yl)isoindoline-1,3-dione | | 765.3 | $^1$H NMR (400 MHz, DMSO-$d_6$) δ: 11.07 (s, 1H), 9.48 (s, 1H), 8.63-8.60 (m, 1H), 8.56-8.32 (m, 3H), 8.21 (s, 1H), 8.07-7.98 (m, 1H), 7.84-7.77 (m, 2H), 7.65 (d, J = 8.8 Hz, 1H), 7.31 (d, J = 1.6 Hz, 1H), 7.23 (dd, J = 2.0, 8.8 Hz, 1H), 5.06 (dd, J = 5.4, 12.8 Hz, 1H), 4.04 (d, J = 12.8 Hz, 2H), 3.56-3.41 (m, 5H), 3.11-3.02 (m, 1H), 3.01-2.82 (m, 4H), 2.60 (d, J = 2.4 Hz, 2H), 2.43-2.37 (m 2H), 2.04-1.97 (m, 1H), 1.78 (d, J = 11.2 Hz, 2H), 1.66-1.58 (m, 1H), 1.45 (d, J = 5.2 Hz, 2H), 1.25-1.14 (m, 3H) |
| 564 | 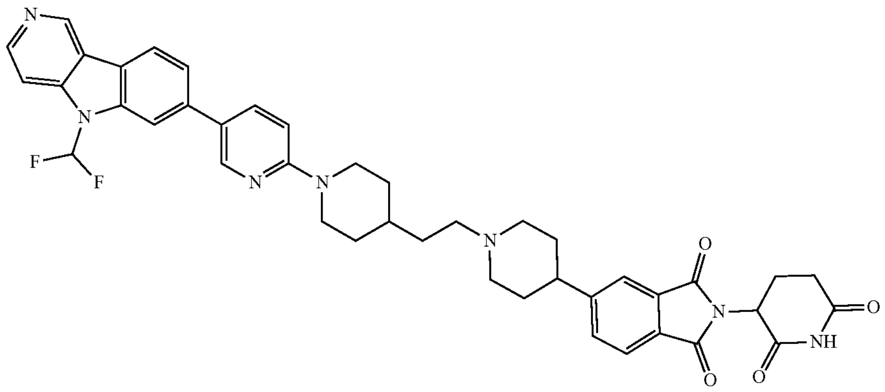 [SMILES: O=C1CCC(N2C(=O)c3ccc(C4CCN(CCC5CCN(c6ccc(-c7ccc8c9cnccc9n(C(F)F)c8c7)cn6)CC5)CC4)cc3C2=O)C(=O)N1] | 5-(1-(2-(1-(5-(5-(difluoromethyl)-5H-pyrido[4,3-b]indol-7-yl)pyridin-2-yl)piperidin-4-yl)ethyl)piperidin-4-yl)-2-(2,6-dioxopiperidin-3-yl)isoindoline-1,3-dione | | 746.3 | $^1$H NMR (400 MHz, DMSO-$d_6$) δ: 1.23 (d, J = 8.4 Hz, 2 H), 1.69 (s, 3 H), 1.82 (d, J = 12.0 Hz, 2 H), 1.89-1.99 (m, 2 H), 2.03-2.14 (m, 3 H), 2.58-2.72 (m, 2 H), 2.84-2.99 (m, 4 H), 3.07-3.23 (m, 6 H), 4.42 (d, J = 12.4 Hz, 2 H), 5.16 (d, J = 12.8 Hz, 1 H), 7.10 (d, J = 9.2 Hz, 1 H), 7.75-7.89 (m, 2 H), 7.94 (d, J = 8.0 Hz, 2 H), 8.10 (d, J = 8.8 Hz, 1 H), 8.26 (s, 1 H), 8.33 (d, J = 6.4 Hz, 1 H), 8.49-8.82 (m, 3 H), 8.89 (d, J = 6.4 Hz, 1 H), 9.41 (s, 1 H), 9.87 (s, 1 H), 11.14 (s, 1 H) |
| 565 | 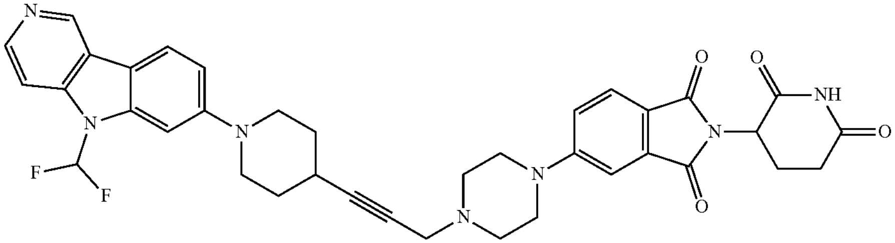 [SMILES: O=C1CCC(N2C(=O)c3ccc(N4CCN(CC#CC5CCN(c6ccc7c8cnccc8n(C(F)F)c7c6)CC5)CC4)cc3C2=O)C(=O)N1] | 5-(4-(3-(1-(5-(difluoromethyl)-5H-pyrido[4,3-b]indol-7-yl)piperidin-4-yl)prop-2-yn-1-yl)piperazin-1-yl)-2-(2,6-dioxopiperidin-3-yl)isoindoline-1,3-dione | A | 680.3 | $^1$H NMR (400 MHz, DMSO-$d_6$) δ: 11.08 (s, 1 H), 9.00-9.58 (m, 1 H), 8.02-8.54 (m, 3 H), 7.61-7.80 (m, 2 H), 7.22-7.37 (m, 3 H), 7.11 (m 1 H), 5.07 (m, 1 H), 3.60 (m, 2 H), 3.46 (br s, 4 H), 3.36 (br s, 5 H), 3.08-3.16 (m, 2 H), 2.88 (m, 1 H), 2.71 (br s, 1 H), 2.60 (br s, 4 H), 1.87-2.04 (m, 3 H), 1.60-1.71 (m, 2 H) |

TABLE 1-continued

| | | | | | |
|---|---|---|---|---|---|
| 566 | 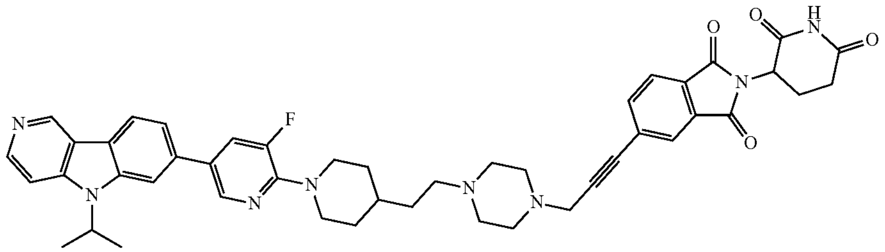 [SMILES: CC(C)n1c2ccncc2c2ccc(-c3cnc(N4CCC(CCN5CCN(CC#Cc6ccc7c(c6)C(=O)N(C6CCC(=O)NC6=O)C7=O)CC5)CC4)c(F)c3)cc21] | 5-(3-(4-(2-(1-(5-(5-(difluoromethyl)-5H-pyrido[4,3-b]indol-7-yl)-3-fluoropyridin-2-yl)piperidin-4-yl)ethyl)piperazin-1-yl)prop-1-yn-1-yl)-2-(2,6-dioxopiperidin-3-yl)isoindoline-1,3-dione | A | 803.3 | $^1$H NMR (400 MHz, DMSO-$d_6$) δ: 11.14 (br s, 1 H), 9.48 (d, J = 0.6 Hz, 1 H), 8.33-8.66 (m, 4 H), 8.21 (s, 1 H), 7.89-8.03 (m, 4 H), 7.81 (d, J = 6.8 Hz, 2 H), 5.17 (m, 1 H), 4.09 (d, J = 12.8 Hz, 2 H), 3.59 (s, 2 H), 2.84-2.96 (m, 3 H), 2.54-2.65 (m, 5 H), 2.27-2.41 (m, 5 H), 2.03-2.10 (m, 1 H), 1.78 (d, J = 12.4 Hz, 2 H), 1.51-1.61 (m, 1 H), 1.14-1.48 (m, 6 H) |
| 567 | 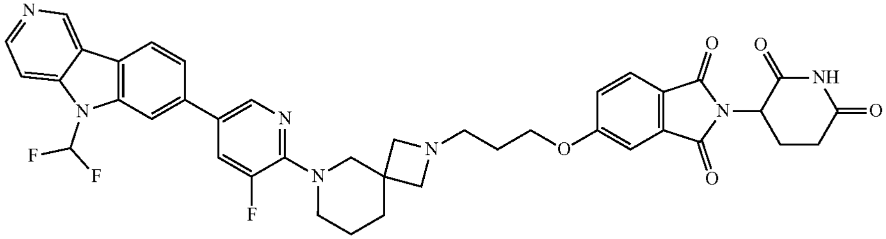 [SMILES: O=C1CCC(N2C(=O)c3ccc(OCCCN4CC5(CCCN(c6ncc(-c7ccc8c9cnccc9n(C(F)F)c8c7)cc6F)C5)C4)cc3C2=O)C(=O)N1] | 5-(3-(6-(5-(5-(difluoromethyl)-5H-pyrido[4,3-b]indol-7-yl)-3-fluoropyridin-2-yl)-2,6-diazaspiro[3.5]nonan-2-yl)propoxy)-2-(2,6-dioxopiperidin-3-yl)isoindoline-1,3-dione | | 752.3 | 1H NMR (400 MHz, METHANOL-$d_4$) δ: 9.35 (s, 1H), 8.56 (d, J = 5.8 Hz, 1H), 8.49-8.33 (m, 2H), 8.33-8.18 (m, 1H), 8.05 (s, 1H), 7.87 (dd, J = 2.1, 14.1 Hz, 1H), 7.83-7.76 (m, 2H), 7.73 (d, J = 9.8 Hz, 1H), 7.44 (d, J = 2.1 Hz, 1H), 7.33 (dd, J = 2.3, 8.4 Hz, 1H), 5.09 (dd, J = 5.5, 12.4 Hz, 1H), 4.24 (t, J = 5.8 Hz, 2H), 3.75 (br s, 1H), 3.67 (s, 2H), 3.60 (br s, 2H), 3.50-3.42 (m, 2H), 3.16 (br d, J = 17.6 Hz, 2H), 2.91-2.63 (m, 4H), 2.14-2.02 (m, 3H), 1.93 (br d, J = 6.1 Hz, 2H), 1.75 (br s, 2H) |
| 568 | 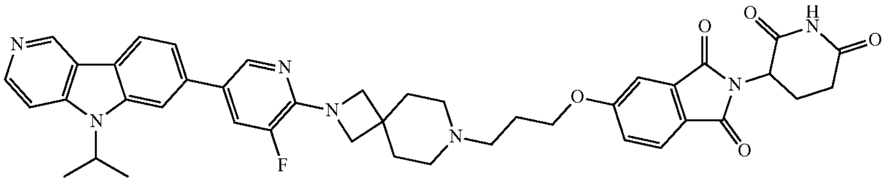 [SMILES: CC(C)n1c2ccncc2c2ccc(-c3cnc(N4CC5(CCN(CCCOc6ccc7c(c6)C(=O)N(C6CCC(=O)NC6=O)C7=O)CC5)C4)c(F)c3)cc21] | 5-(3-(2-(5-(5-(difluoromethyl)-5H-pyrido[4,3-b]indol-7-yl)-3-fluoropyridin-2-yl)-2,7-diazaspiro[3.5]nonan-7-yl)propoxy)-2-(2,6-dioxopiperidin-3-yl)isoindoline-1,3-dione | A | 752.3 | 1H NMR (400 MHz, METHANOL-d4) δ: 9.32 (s, 1 H), 8.54 (d, J = 6.0 Hz, 1 H), 8.02-8.36 (m, 3 H), 7.99 (s, 1 H), 7.78-7.84 (m, 2 H), 7.75 (dd, J = 13.2, 2.0 Hz, 1 H), 7.67 (dd, J = 8.4, 1.2 Hz, 1 H), 7.39-7.44 (m, 1 H), 7.33 (dd, J = 8.4, 2.4 Hz, 1 H), 5.11 (dd, J = 12.8, 5.6 Hz, 1 H), 4.57 (br s, 1 H), 4.24 (t, J = 6.0 Hz, 2 H), 3.99 (d, J = 1.6 Hz, 4 H), 2.67-2.93 (m, 8 H), 2.08-2.20 (m, 3 H), 2.00 (br s, 4 H,) 1.34-1.40 (m 1 H). |

TABLE 1-continued

| | | | | | |
|---|---|---|---|---|---|
| 569 | 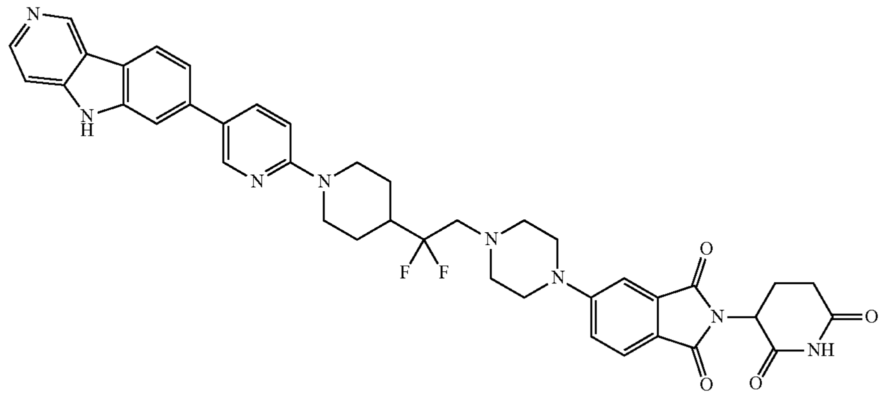 [SMILES: O=C1CCC(N2C(=O)c3ccc(N4CCN(CC(F)(F)C5CCN(c6ccc(-c7ccc8c(c7)[nH]c7ccncc78)cn6)CC5)CC4)cc3C2=O)C(=O)N1] | 5-(4-(2-(1-(5-(5H-pyrido[4,3-b]indol-7-yl)pyridin-2-yl)piperidin-4-yl)-2,2-difluoroethyl)piperazin-1-yl)-2-(2,6-dioxopiperidin-3-yl)isoindoline-1,3-dione | A | 733.2 | $^1$H NMR (400 MHz, DMSO-$d_6$) δ: 13.09 (s, 1H), 11.09 (ss, 1H), 9.74 (s, 1H), 8.69-8.60 (m, 2H), 8.49 (d, J = 8.4 Hz, 1H), 8.07-7.96 (m, 3H), 7.82-7.74 (m, 2H), 7.50 (s, 1H), 7.40-7.33 (m, 1H), 7.13 (d, J = 9.2 Hz, 1H), 5.14-5.03 (m, 1H), 4.83-4.67 (m, 1H), 4.43-4.33 (m, 1H), 4.30-4.18 (m, 2H), 3.70-3.61 (m, 3H), 3.12-3.02 (m, 3H), 2.94-2.84 (m, 3H), 2.62 (d, J = 2.0 Hz, 2H), 2.14-1.94 (m, 5H), 1.82-1.65 (m, 2H), 1.58-1.38 (m, 2H) |
| 570 | 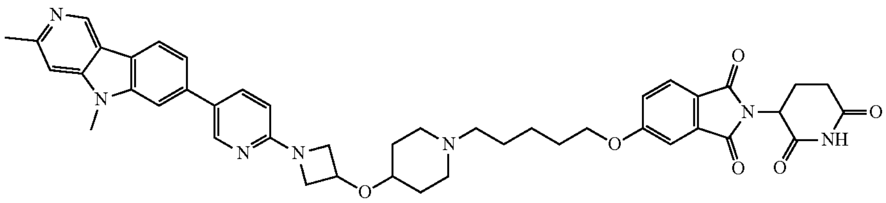 [SMILES: Cc1cc2c(cn1)c1ccc(-c3ccc(N4CC(OC5CCN(CCCCCOc6ccc7c(c6)C(=O)N(C6CCC(=O)NC6=O)C7=O)CC5)C4)nc3)cc1n2C] | 5-((5-(4-((1-(5-(3,5-dimethyl-5H-pyrido[4,3-b]indol-7-yl)pyridin-2-yl)azetidin-3-yl)oxy)piperidin-1-yl)pentyl)oxy)-2-(2,6-dioxopiperidin-3-yl)isoindoline-1,3-dione | | 770.2 | $^1$H NMR (400 MHz, DMSO-$d_6$) δ: 15.16-14.77 (m, 1H), 11.12 (s, 1H), 9.74-9.55 (m, 2H), 8.66-8.56 (m, 1H), 8.47 (d, J = 8.4 Hz, 1H), 8.21 (d, J = 7.6 Hz, 1H), 8.13 (s, 1H), 8.05 (s, 1H), 7.83 (dd, J = 8.4, 16.0 Hz, 2H), 7.44 (s, 1H), 7.36 (d, J = 8.0 Hz, 1H), 6.71 (d, J = 9.2 Hz, 1H), 5.18-5.08 (m, 1H), 4.69-4.61 (m, 1H), 4.37 (t, J = 7.6 Hz, 2H), 4.21 (t, J = 5.2 Hz, 2H), 4.08 (s, 3H), 3.95-3.89 (m, 3H), 3.56-3.49 (m, 2H), 3.39-3.33 (m, 1H), 3.15-3.05 (m, 3H), 2.99-2.79 (m, 5H), 2.60 (d, J = 17.2 Hz, 2H), 2.18-1.91 (m, 4H), 1.83-1.68 (m, 4H), 1.52-1.41 |
| 571 | 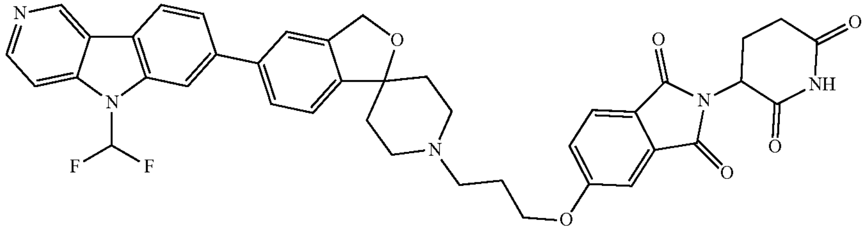 [SMILES: O=C1CCC(N2C(=O)c3ccc(OCCCN4CCC5(CC4)OCc4cc(-c6ccc7c8cnccc8n(C(F)F)c7c6)ccc45)cc3C2=O)C(=O)N1] | 5-(3-(5-(5-(difluoromethyl)-5H-pyrido[4,3-b]indol-7-yl)-3H-spiro[isobenzofuran-1,4'-piperidin]-1'-yl)propoxy)-2-(2,6-dioxopiperidin-3-yl)isoindoline-1,3-dione | | 720.1 | 1H NMR (400 MHz, DMSO-d6) δ: 1.91-2.10 (m, 3 H), 2.25 (s, 4 H), 2.53-2.76 (m, 6 H), 3.63 (s, 3 H), 4.32 (s, 2 H), 5.08-5.20 (m, 3 H), 7.28-7.44 (m, 2 H), 7.50 (s, 1 H), 7.80 (s, 2 H), 7.90 (d, J = 7.6 Hz, 2 H), 8.06-8.65 (m, 3 H), 8.71-8.85 (m, 1 H), 9.49 (s, 1 H), 9.72 (s, 1 H), 11.12 (s, 1 H). |

TABLE 1-continued

| | | | | | |
|---|---|---|---|---|---|
| 572 | 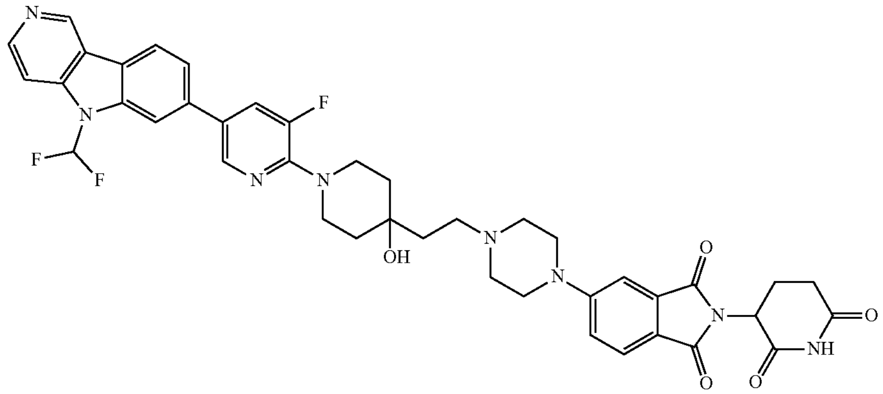 [SMILES: O=C1CCC(N2C(=O)c3ccc(N4CCN(CCC5(O)CCN(c6ncc(-c7ccc8c9cnccc9n(C(F)F)c8c7)cc6F)CC5)CC4)cc3C2=O)C(=O)N1] | 5-(4-(2-(1-(5-(5-(difluoromethyl)-5H-pyrido[4,3-b]indol-7-yl)-3-fluoropyridin-2-yl)-4-hydroxypiperidin-4-yl)ethyl)piperazin-1-yl)-2-(2,6-dioxopiperidin-3-yl)isoindoline-1,3-dione | | 781.2 | $^1$H NMR (400 MHz, DMSO-$d_6$) δ: 11.01 (s, 1 H), 9.79 (s, 1 H), 9.71-9.54 (m, 1 H), 8.84 (d, J = 6.40 Hz, 1 H), 8.75-8.45 (m, 3 H), 8.30 (s, 1 H), 8.21 (d, J = 5.60 Hz, 1 H), 8.11-8.02 (m, 1 H), 7.95 (d, J = 7.60 Hz, 1 H), 7.77 (d, J = 8.00 Hz, 1 H), 7.50 (s, 1 H), 7.37 (d, J = 8.00 Hz, 1 H), 5.10 (dd, J = 12.40, 5.20 Hz, 1 H), 4.85-4.67 (m, 1 H), 4.29-4.22 (m, 2 H), 3.84-3.80 (m, 2 H), 3.43-3.38 (m, 4 H), 3.33-3.29 (m, 2 H), 3.25-3.20 (m, 2 H), 2.95-2.83 (m, 3 H), 2.68-2.60 (m, 3 H), 2.06-2.01 (m, 1 H), 1.87 (d, J = 2.80 Hz, 2 H), 1.67 (s, 3 H). |
| 573 | 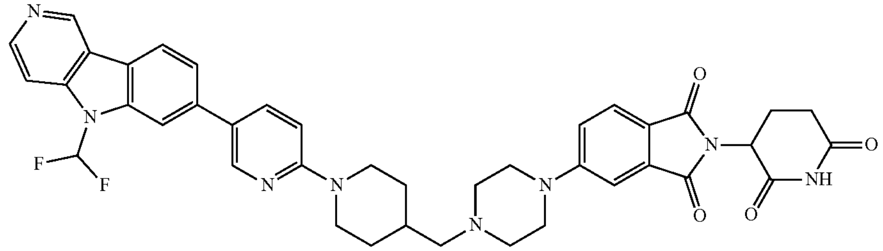 [SMILES: O=C1CCC(N2C(=O)c3ccc(N4CCN(CC5CCN(c6ccc(-c7ccc8c9cnccc9n(C(F)F)c8c7)cn6)CC5)CC4)cc3C2=O)C(=O)N1] | 5-(4-((1-(5-(5-(difluoromethyl)-5H-pyrido[4,3-b]indol-7-yl)pyridin-2-yl)piperidin-4-yl)methyl)piperazin-1-yl)-2-(2,6-dioxopiperidin-3-yl)isoindoline-1,3-dione | | 733.2 | $^1$H NMR (400 MHz, DMSO-$d_6$) δ: 11.10 (s, 1H), 9.85 (s, 1H), 9.74-9.47 (m, 1H), 8.88 (d, J = 6.4 Hz, 1H), 8.82-8.59 (m, 2H), 8.56-8.48 (m, 1H), 8.31 (d, J = 6.4 Hz, 1H), 8.24 (s, 1H), 8.08 (dd, J = 2.4, 9.2 Hz, 1H), 7.93 (dd, J = 1.2, 8.4 Hz, 1H), 7.78 (d, J = 8.4 Hz, 1H), 7.51 (d, J = 1.6 Hz, 1H), 7.38 (dd, J = 2.0, 8.8 Hz, 1H), 7.08 (d, J = 9.2 Hz, 1H), 5.10 (dd, J = 5.2, 13.0 Hz, 1H), 4.44 (d, J = 13.2 Hz, 2H), 4.26-4.19 (m, 2H), 3.39-3.29 (m, 3H), 3.23-3.16 (m, 2H), 3.13 (d, J = 5.6 Hz, 2H), 3.04-2.83 (m, 4H), 2.64-2.53 (m, 2H), 2.23-2.14 (m, 1H), 2.08-2.00 (m, 1H), 1.92-1.83 (m, 2H), 1.26 (q, J = 10.4 Hz, 2H) |
| 574 | 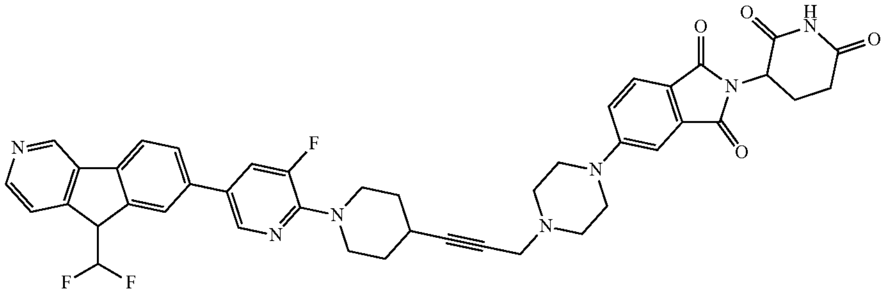 [SMILES: O=C1CCC(N2C(=O)c3ccc(N4CCN(CC#CC5CCN(c6ncc(-c7ccc8c(c7)C(C(F)F)c7ccncc7-8)cc6F)CC5)CC4)cc3C2=O)C(=O)N1] | 5-(4-(3-(1-(5-(5-(difluoromethyl)-5H-pyrido[4,3-b]indol-7-yl)-3-fluoropyridin-2-yl)piperidin-4-yl)prop-2-yn-1-yl)piperazin-1-yl)-2-(2,6-dioxopiperidin-3-yl)isoindoline-1,3-dione | A | 775.2 | $^1$H NMR (400 MHz, DMSO-$d_6$) δ: 11.08 (s, 1 H), 9.49 (d, J = 0.8 Hz, 1 H), 8.61-8.64 (m, 1 H), 8.16-8.56 (m, 4 H), 8.01 (m, 1 H), 7.77-7.84 (m, 2 H), 7.67 (d, J = 8.4 Hz, 1 H), 7.36 (d, J = 2.0 Hz, 1 H), 7.27 (m, 1 H), 5.07 (m, 1 H), 3.71-3.84 (m, 2 H), 3.47 (d, J = 5.2 Hz, 5 H), 3.22-3.30 (m, 3 H), 2.83-2.94 (m, 1 H), 2.72-2.81 (m, 1 H), 2.53-2.66 (m, 6 H), 1.87-2.05 (m, 3 H), 1.58-1.69 (m, 2 H) |

TABLE 1-continued

| | | | | | |
|---|---|---|---|---|---|
| 575 | 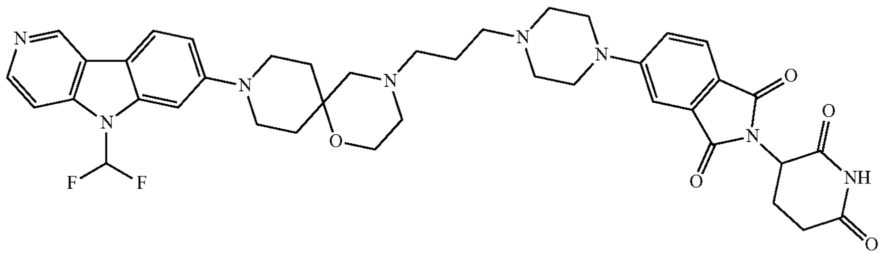 [SMILES: O=C1CCC(N2C(=O)c3ccc(N4CCN(CCCN5CCOC6(CCN(c7ccc8c9cnccc9n(C(F)F)c8c7)CC6)C5)CC4)cc3C2=O)C(=O)N1] | 5-(4-(3-(9-(5-(difluoromethyl)-5H-pyrido[4,3-b]indol-7-yl)-1-oxa-4,9-diazaspiro[5.5]undecan-4-yl)propyl)piperazin-1-yl)-2-(2,6-dioxopiperidin-3-yl)isoindoline-1,3-dione | A | 775.2 | $^1$H NMR (400 MHz, DMSO-$d_6$) δ: 11.09 (s, 1H), 9.61 (s, 1H), 8.75 (d, J = 6.4 Hz, 1H), 8.71-8.40 (m, 1H), 8.25 (d, J = 8.8 Hz, 1H), 8.20 (d, J = 6.4 Hz, 1H), 7.77 (d, J = 8.4 Hz, 1H), 7.50 (d, J = 1.6 Hz, 1H), 7.40 (s, 1H), 7.34 (ddd, J = 2.0, 8.8, 18.0 Hz, 2H), 5.09 (dd, J = 5.2, 12.8 Hz, 1H), 3.89 (s, 2H), 3.75-3.68 (m, 6H), 3.28-3.10 (m, 10H), 2.96-2.83 (m, 4H), 2.62-2.57 (m, 3H), 2.19-1.97 (m, 4H), 1.83-1.64 (m, 3H) |
| 576 | 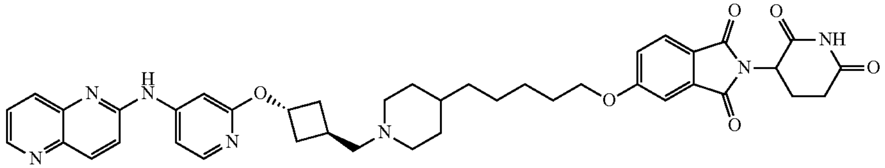 [SMILES: O=C1CCC(N2C(=O)c3ccc(OCCCCCC4CCN(C[C@H]5C[C@H](Oc6cc(Nc7ccc8ncccc8n7)ccn6)C5)CC4)cc3C2=O)C(=O)N1] | 5-((5-(1-(((1r,3r)-3-((4-((1,5-naphthyridin-2-yl)amino)pyridin-2-yl)oxy)cyclobutyl) methyl)piperidin-4-yl)pentyl)oxy)-2-(2,6-dioxopiperidin-3-yl)isoindoline-1,3-dione | | 732.3 | 1H NMR (400 MHz, Acetonitrile-$d_6$) δ: 8.95 (s, 1H), 8.75 (dd, J = 1.6, 4.4 Hz, 1H), 8.41 (s, 1H), 8.25-8.11 (m, 3H), 7.98 (d, J = 5.6 Hz, 1H), 7.79 (d, J = 8.4 Hz, 1H), 7.70 (d, J = 1.6 Hz, 1H), 7.62 (dd, J = 4.4, 8.8 Hz, 1H), 7.37 (d, J = 2.0 Hz, 1H), 7.32 (dd, J = 2.0, 6.0 Hz, 1H), 7.30-7.28 (m, 1H), 7.27 (s, 1H), 5.30-5.21 (m, 1H), 5.05-4.93 (m, 1H), 4.16 (t, J = 6.4 Hz, 2H), 3.33 (d, J = 12.4 Hz, 2H), 3.09 (d, J = 8.0 Hz, 2H), 2.94-2.79 (m, 2H), 2.78-2.66 (m, 5H), 2.41-2.40 (m, 2H), 2.21-2.09 (m, 1H), 1.90-1.79 (m, 5H), 1.53-1.44 (m, 5H), 1.43-1.38 (m, 2H), 1.36-1.28 (m, 2H) |
| 577 | 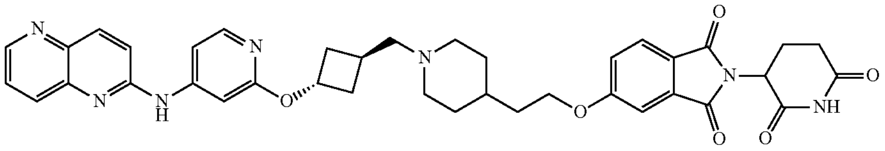 [SMILES: O=C1CCC(N2C(=O)c3ccc(OCCC4CCN(C[C@H]5C[C@H](Oc6cc(Nc7ccc8ncccc8n7)ccn6)C5)CC4)cc3C2=O)C(=O)N1] | 5-(2-(1-(((1r,3r)-3-((4-((1,5-napthyridin-2-yl)amino)pyridin-2-yl)oxy)cyclobutyl) methyl)piperidin-4-yl) ethoxy)-2-(2,6-dioxopiperidin-3-yl)isoindoline-1,3-dione | B | 690.3 | 1H NMR (400 MHz, DMSO-$d_6$) δ: $^1$H NMR (400 MHz, DMSO-$d_6$) δ = 11.10 (s, 1H), 10.04 (s, 1H), 8.75-8.68 (m, 1H), 8.21 (d, J = 9.2 Hz, 2H), 8.16 (d, J = 8.0 Hz, 1H), 7.96 (d, J = 6.0 Hz, 1H), 7.82 (d, J = 8.4 Hz, 1H), 7.70 (s, 1H), 7.65 (dd, J = 4.0, 8.4 Hz, 1H), 7.43 (d, J = 2.0 Hz, 1H), 7.35 (d, J = 8.4 Hz, 2H), 7.26 (dd, J = 1.6, 6.0 Hz, 1H), 5.25-5.16 (m, 1H), 5.11 (dd, J = 5.6, 13.2 Hz, 1H), 4.21 (t, J = 6.0 Hz, 2H), 2.96-2.83 (m, 3H), 2.68-2.54 (m, 5H), 2.22 (d, J = 6.0 Hz, 4H), 2.09-2.01 (m, 3H), 1.75-1.67 (m, 4H), 1.50 (s, 1H), 1.31-1.22 (m, 2H) |
| 578 | 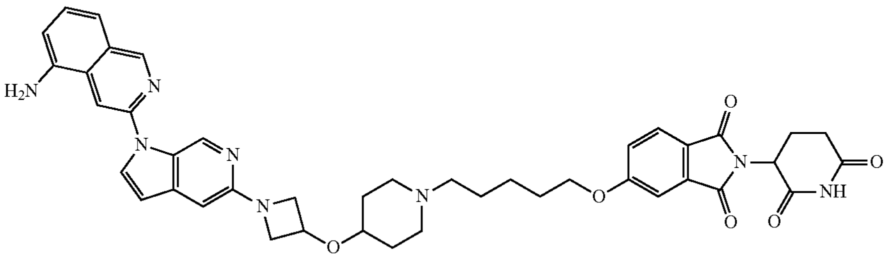 [SMILES: Nc1cccc2cnc(-n3ccc4cc(N5CC(OC6CCN(CCCCCOc7ccc8c(c7)C(=O)N(C7CCC(=O)NC7=O)C8=O)CC6)C5)ncc43)cc12] | 5-((5-(4-((1-(1-(5-aminoisoquinolin-3-yl)-1H-pyrrolo[2,3-c]pyridin-5-yl)azetidin-3-yl)oxy)piperidin-1-yl)pentyl)oxy)-2-(2,6-dioxopiperidin-3-yl)isoindoline-1,3-dione | | 757.2 | $^1$H NMR (400 MHz, DMSO-$d_6$) δ: 11.11 (s, 1H), 9.31 (d, J = 4.0 Hz, 1H), 9.27-9.11 (m, 2H), 8.65 (d, J = 1.2 Hz, 1H), 8.33 (s, 1H), 7.91-7.79 (m, 1H), 7.43 (t, J = 2.4 Hz, 1H), 7.41-7.31 (m, 3H), 6.98 (s, 1H), 6.94-6.90 (m, 1H), 6.88 (s, 1H), 5.19-5.05 (m, 1H), 4.76-4.58 (m, 1H), 4.45-4.35 (m, 2H), 4.25-4.15 (m, 2H), 4.01-3.93 (m, 2H), 3.83 (s, 1H), 3.69-3.60 (m, 3H), 3.17-3.04 (m, 4H), 3.02-2.80 (m, 3H), 2.64-2.55 (m 1H), 2.19-2.13 (m, 1H), 2.09-2.03 (m, 1H), 1.99-1.86 (m, 2H), 1.84-1.77 (m, |

TABLE 1-continued

| | | | | | |
|---|---|---|---|---|---|
| | | | | | 2H), 1.76-1.68 (m, 2H), 1.62 (d, J = 12.4 Hz, 1H), 1.48 (d, J = 6.0 Hz, 2H) |
| 579 | 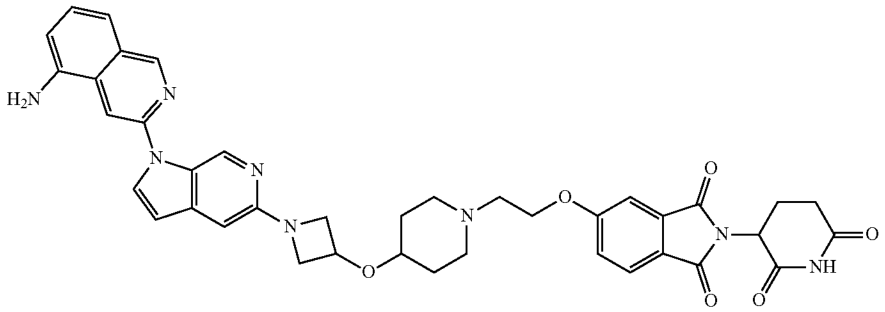 [SMILES: Nc1cccc2cnc(-n3ccc4cc(N5CC(OC6CCN(CCOc7ccc8c(c7)C(=O)N(C7CCC(=O)NC7=O)C8=O)CC6)C5)ncc43)cc12] | 5-(2-(4-((1-(1-(5-aminoisoquinolin-3-yl)-1H-pyrrolo[2,3-c]pyridin-5-yl)azetidin-3-yl)oxy)piperidin-1-yl)ethoxy)-2-(2,6-dioxopiperidin-3-yl)isoindoline-1,3-dione | | 715.2 | $^1$H NMR (400 MHz, DMSO-$d_6$) δ: 11.12 (s, 1H), 9.45 (s, 1H), 9.31 (s, 1H), 9.21 (s, 1H), 8.72-8.55 (m, 1H), 8.33 (s, 1H), 7.95-7.87 (m, 1H), 7.56 (d, J = 1.6 Hz, 1H), 7.46-7.41 (m, 1H), 7.41-7.32 (m, 2H), 7.03-6.94 (m, 1H), 6.92 (d, J = 7.2 Hz, 1H), 6.89 (s, 1H), 5.20-5.08 (m, 1H), 4.71-4.62 (m, 1H), 4.57 (d, J = 4.0 Hz, 2H), 4.46-4.35 (m, 2H), 4.05-3.94 (m, 2H), 3.87-3.80 (m, 1H), 3.63 (d, J = 6.4 Hz, 4H), 3.18-3.09 (m, 2H), 2.93-2.86 (m, 1H), 2.61 (d, J = 18.4 Hz, 1H), 2.57-2.52 (m, 2H), 2.15 (s, 1H), 2.07-1.92 (m, 3H), 1.73-1.65 (m, 1H) |
| 580 | 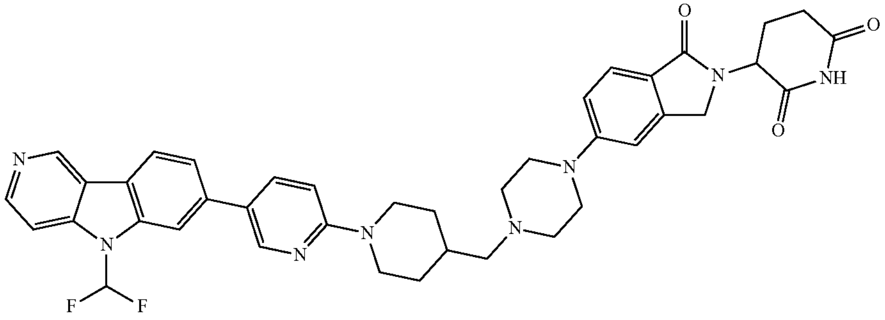 [SMILES: O=C1CCC(N2Cc3cc(N4CCN(CC5CCN(c6ccc(-c7ccc8c9cnccc9n(C(F)F)c8c7)cn6)CC5)CC4)ccc3C2=O)C(=O)N1] | 3-(5-(4-((1-(5-(5-(difluoromethyl)-5H-pyrido[4,3-b]indol-7-yl)pyridin-2-yl)piperidin-4-yl)methyl)piperazin-1-yl)-1-oxoisoindolin-2-yl)piperidine-2,6-dione | | 719.2 | $^1$H NMR (400 MHz, DMSO-$d_6$) δ: 10.96 (s, 1H), 9.85 (s, 1H), 9.66-9.42 (m, 1H), 8.88 (d, J = 6.4 Hz, 1H), 8.81-8.61 (m, 2H), 8.53 (d, J = 8.4 Hz, 1H), 8.34-8.29 (m, 1H), 8.27-8.22 (m, 1H), 8.08 (dd, J = 2.4, 8.8 Hz, 1H), 7.96-7.90 (m, 1H), 7.61 (d, J = 8.4 Hz, 1H), 7.21-7.14 (m, 2H), 7.08 (d, J = 9.2 Hz, 1H), 5.07 (dd, J = 5.2, 13.2 Hz, 1H), 4.46-4.39 (m, 2H), 4.35 (s, 1H), 4.30-4.20 (m, 2H), 4.05-4.00 (m, 2H), 3.20 (s, 2H), 3.14-(d, J = 6.4 Hz, 2H), 3.02-2.87 (m, 4H), 2.62 (d, J = 2.4 Hz, 1H), 2.57 (s, 1H), 2.43-2.36 (m, 1H), 2.24-2.16 (m, 1H), 2.01-1.94 (m, 1H), 1.91-1.82 (m, 2H), 1.80-1.47 (m, 1H), 1.32-1.21 (m, 2H) |
| 581 | 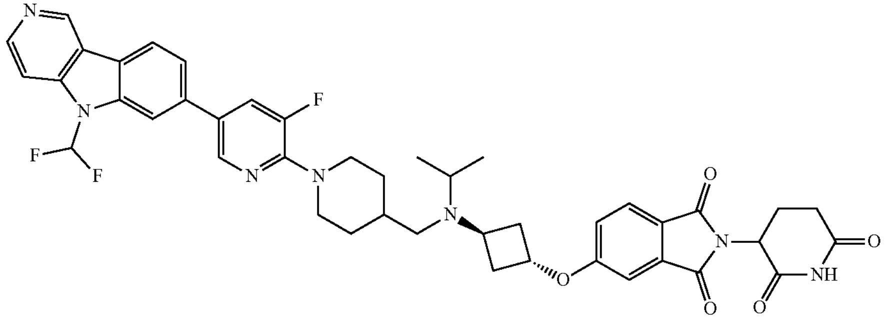 [SMILES: CC(C)N(CC1CCN(c2ncc(-c3ccc4c5cnccc5n(C(F)F)c4c3)cc2F)CC1)[C@H]1C[C@H](Oc2ccc3c(c2)C(=O)N(C2CCC(=O)NC2=O)C3=O)C1] | 5-((1r,3r)-3-(((1-(5-(5-(difluoromethyl)-5H-pyrido[4,3-b]indol-7-yl)-3-fluoropyridin-2-yl)piperidin-4-yl)methyl)(isopropyl)amino)cyclobutoxy)-2-(2,6-dioxopiperidin-3-yl)isoindoline-1,3-dione | A | 794.2 | $^1$H NMR (400 MHz, DMSO-$d_6$) δ: 11.12 (s, 1 H), 9.80 (s, 1 H), 8.88 (s, 1 H), 8.85 (d, J = 6.40 Hz, 1 H), 8.82-8.35 (m, 3 H), 8.30 (s, 1 H), 8.23 (d, J = 5.60 Hz, 1 H), 8.07 (dd, J = 15.20, 2.00 Hz, 1 H), 7.95 (d, J = 8.60 Hz, 1 H), 7.89 (d, J = 8.40 Hz, 1 H), 7.39-7.29 (m, 2 H), 5.11 (dd, J = 13.20, 5.60 Hz, 2 H), 4.25 (d, J = 8.40 Hz, 1 H), 4.21-4.14 (m, 2 H), 3.17-3.08 (m, 2 H), 3.04-2.86 (m, 6 H), 2.64-2.55 (m 3 H), 2.52 (d, J = 1.60 Hz, 2 H), 2.07-1.97 (m, 2 H), 1.88 (dd, J = 13.20, 1.60 Hz, 1 H), 1.42-1.32 (m, 2 H), 1.30 (d, J = 6.40 Hz, 3 H), 1.25-1.17 (m, 3 H). |

TABLE 1-continued

| | | | | | |
|---|---|---|---|---|---|
| 582 | 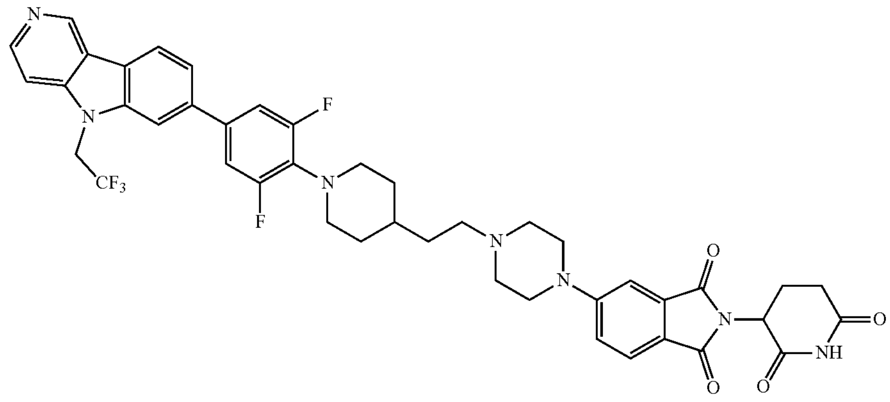 [SMILES: O=C1CCC(N2C(=O)c3ccc(N4CCN(CCC5CCN(c6c(F)cc(-c7ccc8c9cnccc9n(CC(F)(F)F)c8c7)cc6F)CC5)CC4)cc3C2=O)C(=O)N1] | 5-(4-(2-(1-(2,6-difluoro-4-(5-(2,2,2-trifluoroethyl)-5H-pyrido[4,3-b]indol-7-yl)phenyl)piperidin-4-yl)ethyl)piperazin-1-yl)-2-(2,6-dioxopiperidin-3-yl)isoindoline-1,3-dione | | 814.2 | 1H NMR (400 MHz, DMSO-d6) δ: 1.24-1.60 (m, 4 H), 1.70-1.84 (m, 4 H), 1.90-2.18 (m, 2 H), 2.86-2.97 (m, 1 H), 3.13 (s, 3 H), 3.25-3.35 (m, 8 H), 3.62 (s, 1 H), 4.25 (s, 2 H), 5.11 (d, J = 12.8 Hz, 1 H), 5.81 (d, J = 8.8 Hz, 2 H), 7.39 (d, J = 8.4 Hz, 1 H), 7.52 (s, 1 H), 7.67 (d, J = 10.8 Hz, 2 H), 7.79 (d, J = 8.4 Hz, 1 H), 7.97 (d, J = 8.0 Hz, 1 H), 8.32 (s, 1 H), 8.45 (s, 1 H), 8.54 (d, J = 8.4 Hz, 1 H), 8.86 (d, J = 6.8 Hz, 1 H), 9.82 (s, 1 H), 11.11 (s, 1 H) |
| 583 | 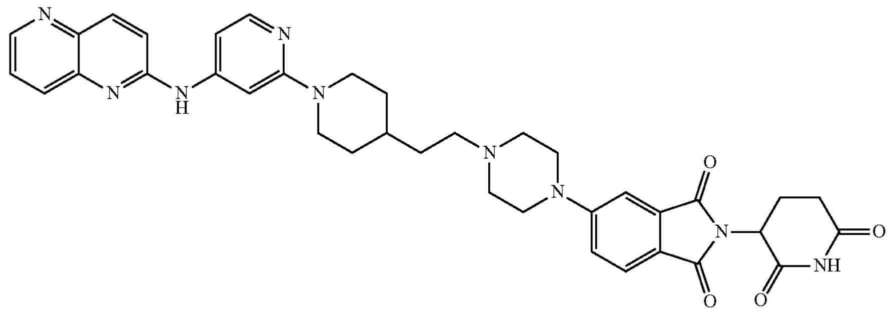 [SMILES: O=C1CCC(N2C(=O)c3ccc(N4CCN(CCC5CCN(c6cc(Nc7ccc8ncccc8n7)ccn6)CC5)CC4)cc3C2=O)C(=O)N1] | 5-(4-(2-(1-(4-((1,5-naphthyridin-2-yl)amino)pyridin-2-yl)piperidin-4-yl)ethyl)piperazin-1-yl)-2-(2,6-dioxopiperidin-3-yl)isoindoline-1,3-dione | A | 674.2 | 1H NMR (400 MHz, MeOD) δ: 8.18-8.80 (m, 1H), 8.78 (d, J = 2.8 Hz, 1H), 8.39 (s, 1H), 8.29 (d, J = 9.2 Hz, 2H), 7.84 (d, J = 6.8 Hz, 1H), 7.78-7.67 (m, 3H), 7.46-7.41 (m, 1H), 7.38 (s, 1H), 7.33-7.22 (m, 1H), 7.22-7.22 (m, 1H), 7.13 (d, J = 6.4 Hz, 1H), 5.04-5.03 (m, 1H), 4.23-4.08 (m, 3H), 3.62 (s, 3H), 3.23 (t, J = 12.4 Hz, 2H), 3.02 (s, 2H), 2.90-2.85 (m, 2H), 2.82-2.68 (m, 2H), 2.37 (s, 2H), 2.26 (s, 1H), 2.20-2.10 (m, 1H), 2.00 (d, J = 11.6 Hz, 1H), 1.81 (s, 1H), 1.72 (s, 1H), 1.55-1.34 (m, 2H) |
| 584 | 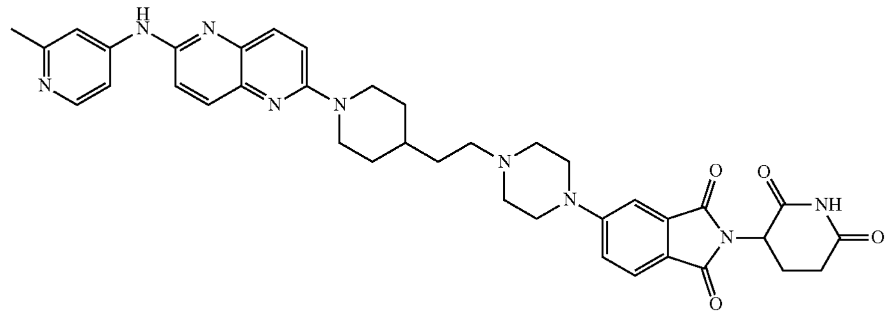 [SMILES: Cc1cc(Nc2ccc3nc(N4CCC(CCN5CCN(c6ccc7c(c6)C(=O)N(C6CCC(=O)NC6=O)C7=O)CC5)CC4)ccc3n2)ccn1] | 2-(2,6-dioxopiperidin-3-yl)-5-(4-(2-(1-(6-((2-methylpyridin-4-yl)amino)-1,5-naphthyridin-2-yl)piperidin-4-yl)ethyl)piperazin-1-yl)isoindoline-1,3-dione | A | 687.2 | 1H NMR (400 MHz, DMSO-d6) δ: 11.07 (s, 1 H), 9.78 (s, 1 H), 8.24 (d, J = 8.0 Hz, 1 H), 8.15 (s, 2 H), 7.94 (d, J = 8.0 Hz, 1 H), 7.85 (d, J = 12.0 Hz, 1 H), 7.77 (s, 2 H), 7.69 (d, J = 8.0 Hz, 1 H), 7.37-7.35 (m, 2 H), 7.27 (d, J = 8.0 Hz, 1 H), 7.19 (d, J = 8.0 Hz, 1 H), 5.10-5.05 (m, 1 H), 4.47 (d, J = 12.0 Hz, 2 H), 3.46 (m, 9 H), 2.93-2.85 (m, 3 H), 2.45 (s, 3 H), 2.44-2.42 (m, 3 H), 2.04-2.01 (m, 1 H), 1.81 (d, J = 12.0 Hz, 2 H), 1.62 (s, 1 H), 1.46 (d, J = 8.0 Hz, 2 H), 1.24-1.16 (m, 2 H). |

TABLE 1-continued

| | | | | | |
|---|---|---|---|---|---|
| 585 | 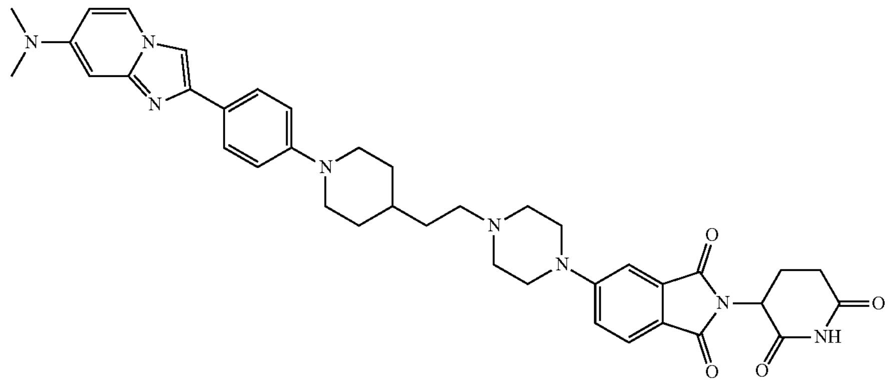 [SMILES: CN(C)c1ccn2cc(-c3ccc(N4CCC(CCN5CCN(c6ccc7c(c6)C(=O)N(C6CCC(=O)NC6=O)C7=O)CC5)CC4)cc3)nc2c1] | 5-(4-(2-(1-(4-(7-(dimethylamino)imidazo[1,2-a]pyridin-2-yl)phenyl)piperidin-4-yl)ethyl)piperazin-1-yl)-2-(2,6-dioxopiperidin-3-yl)isoindoline-1,3-dione | | 689.3 | $^1$H NMR (400 MHz, DMSO-$d_6$) δ: 13.36 (s, 1H), 11.09 (s, 1H), 9.94-9.65 (m, 1H), 8.46 (d, J = 7.6 Hz, 1H), 8.12 (s, 1H), 7.77 (d, J = 8.4 Hz, 1H), 7.64 (d, J = 8.8 Hz, 2H), 7.50 (d, J = 1.6 Hz, 1H), 7.37 (dd, J = 2.0, 8.8 Hz, 1H), 7.13-7.04 (m, 3H), 6.47 (d, J = 2.4 Hz, 1H), 5.10 (dd, J = 5.2, 13.2 Hz, 1H), 4.24 (d, J = 11.2 Hz, 2H), 3.87 (d, J = 13.2 Hz, 2H), 3.64-3.59 (m, 2H), 3.26-3.21 (m, 3H), 3.14 (s, 8H), 3.05-2.84 (m, 2H), 2.81-2.73 (m, 2H), 2.62 (d, J = 2.8 Hz, 1H), 2.08-1.98 (m, 1H), 1.78 (d, J = 10.8 Hz, 2H), 1.71-1.62 (m, 2H), 1.59-1.49 (m, 1H), 1.34-1.21 (m, 2H) |
| 586 | 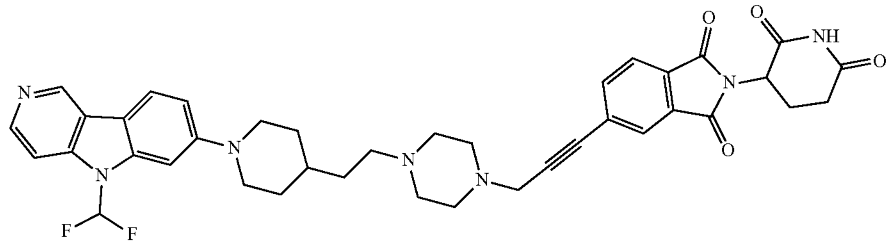 [SMILES: O=C1CCC(N2C(=O)c3ccc(C#CCN4CCN(CCC5CCN(c6ccc7c8cnccc8n(C(F)F)c7c6)CC5)CC4)cc3C2=O)C(=O)N1] | 5-(3-(4-(2-(1-(5-(difluoromethyl)-5H-pyrido[4,3-b]indol-7-yl)piperidin-4-yl)ethyl)piperazin-1-yl)prop-1-yn-1-yl)-2-(2,6-dioxopiperidin-3-yl)isoindoline-1,3-dione | A | 708.2 | $^1$H NMR (400 MHz, DMSO-$d_6$) δ: 11.15 (s, 1 H), 9.25 (d, J = 0.8 Hz, 1 H), 8.21-8.57 (m, 2 H), 8.06 (d, J = 8.8 Hz, 1 H), 7.93 (s, 3 H), 7.69 (d, J = 6.0 Hz, 1 H), 7.31 (d, J = 2.0 Hz, 1 H), 7.11 (m, 1 H), 5.17 (m, 1 H), 3.86 (d, J = 12.8 Hz, 2 H), 3.61 (br s, 2 H), 3.31 (br s, 2 H), 2.74-2.96 (m, 4 H), 2.54-2.65 (m, 6 H), 2.42-2.48 (m, 2 H), 2.03-2.11 (m, 1 H), 1.81 (d, J = 10.8 Hz, 2 H), 1.23-1.56 (m, 6 H). |
| 589 | 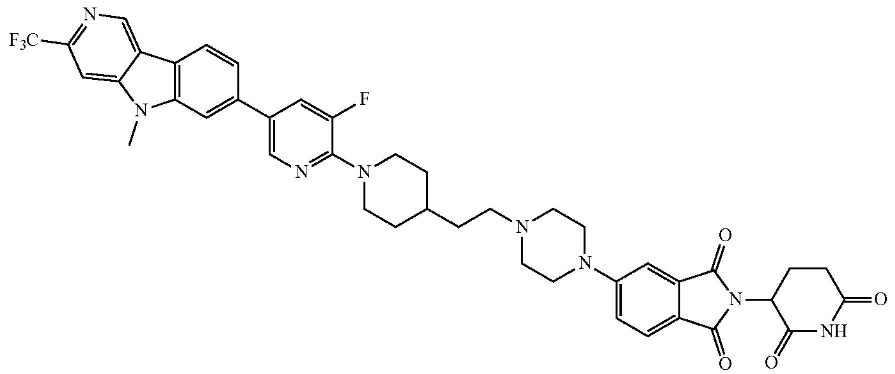 [SMILES: Cn1c2cc(-c3cnc(N4CCC(CCN5CCN(c6ccc7c(c6)C(=O)N(C6CCC(=O)NC6=O)C7=O)CC5)CC4)c(F)c3)ccc2c2cnc(C(F)(F)F)cc21] | 2-(2,6-dioxopiperidin-3-yl)-5-(4-(2-(1-(3-fluoro-5-(5-methyl-3-(trifluoromethyl)-5H-pyrido[4,3-b]indol-7-yl)pyridin-2-yl)piperidin-4-yl)ethyl)piperazin-1-yl)isoindoline-1,3-dione | | 797.3 | $^1$H NMR (400 MHz, DMSO-$d_6$) δ: 11.08 (s, 1H), 9.51 (s, 1H) 8.59 (s, 1H), 8.43 (d, J = 8.0 Hz, 1H), 8.32-8.38 (m, 1H), 8.21 (s, 1H), 8.09-8.14 (m, 2H), 7.76 (d, J = 7.6 Hz, 1H), 7.69 (d, J = 8.8 Hz, 1H), 7.35 (s, 1H), 7.23-7.29 (m, 1H), 5.08 (dd, J = 12.8, 5.2 Hz, 1 H), 4.03-4.17 (m, 5 H), 3.45 (br d, J = 4.8 Hz, 5 H), 2.87-2.99 (m, 3 H), 2.55-2.64 (m, 4 H), 2.38-2.45 (m, 3 H), 1.97-2.07 (m, 1 H), 1.78-1.86 (m, 2 H), 1.55-1.68 (m, 1 H), 1.42-1.52 (m, 2 H), 1.23-1.38 (m, 2 H). |

TABLE 1-continued

| | | | | | |
|---|---|---|---|---|---|
| 590 | 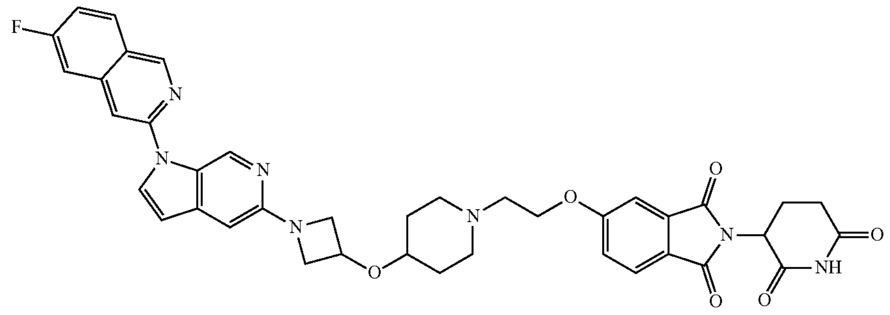 [SMILES: O=C1CCC(N2C(=O)c3ccc(OCCN4CCC(OC5CN(c6cc7ccn(-c8cc9cc(F)ccc9cn8)c7cn6)C5)CC4)cc3C2=O)C(=O)N1] | 2-(2,6-dioxopiperidin-3-yl)-5-(2-(4-((1-(1-(6-fluoroisoquinolin-3-yl)-1H-pyrrolo[2,3-c]pyridin-5-yl)azetidin-3-yl)oxy)piperidin-1-yl)ethoxy)isoindoline-1,3-dione | | 718.2 | $^1$H NMR (400 MHz, DMSO-$d_6$) δ: 11.12 (s, 1H), 9.82-9.56 (m, 1H), 9.42 (s, 1H), 9.32 (s, 1H), 8.59 (s, 1H), 8.37-8.31 (m, 1H), 8.25 (s, 1H), 7.96-7.87 (m, 1H), 7.81-7.71 (m, 1H), 7.63-7.53 (m, 2H), 7.47-7.39 (m, 1H), 6.97-6.74 (m, 2H), 5.23-5.04 (m, 1H), 4.70-4.61 (m, 1H), 4.57 (br d, J = 4.4 Hz, 2H), 4.36 (t, J = 7.2 Hz, 2H), 4.02-3.79 (m, 3H), 3.70-3.57 (m, 5H), 3.18-3.05 (m, 2H), 2.94-2.85 (m, 1H), 2.65-2.66 (m, 1H), 2.22-2.15 (m, 1H), 2.10-1.89 (m, 3H), 1.76-1.64 (m, 1H) |
| 591 | 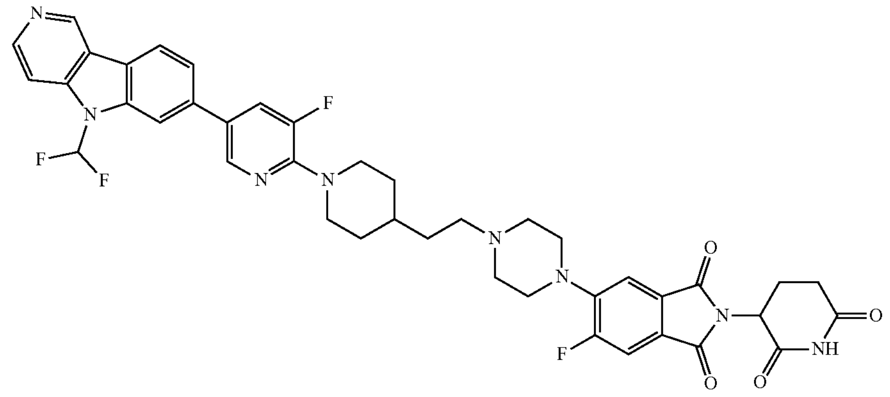 [SMILES: O=C1CCC(N2C(=O)c3cc(F)c(N4CCN(CCC5CCN(c6ncc(-c7ccc8c9cnccc9n(C(F)F)c8c7)cc6F)CC5)CC4)cc3C2=O)C(=O)N1] | 5-(4-(2-(1-(5-(5-(difluoromethyl)-5H-pyrido[4,3-b]indol-7-yl)-3-fluoropyridin-2-yl)piperidin-4-yl)ethyl)piperazin-1-yl)-2-(2,6-dioxopiperidin-3-yl)-6-fluoroisoindoline-1,3-dione | | 783.1 | $^1$H NMR: (400 MHz, DMSO-$d_6$) δ: 11.11 (s, 1 H), 10.14-9.67 (m, 2 H), 8.92-8.80 (m, 1 H), 8.76 (s, 3 H), 8.33-8.24 (m, 2 H), 8.05 (dd, J = 14.80, 1.60 Hz, 1 H), 7.96 (d, J = 8.80 Hz, 1 H), 7.81 (d, J = 11.20 Hz, 1 H), 7.60 (d, J = 7.60 Hz, 1 H), 5.12 (dd, J = 12.80, 5.20 Hz, 1 H), 4.13 (d, J = 12.80 Hz, 3 H), 3.26 (s, 4 H), 3.00-2.84 (m, 6 H), 2.62 (s, 2 H), 2.58 (s, 1 H), 2.54 (d, J = 3.20 Hz, 1 H), 2.05-2.00 (m, 1 H), 1.80 (d, J = 11.60 Hz, 2 H), 1.72-1.62 (m, 3 H), 1.38-1.28 (m, 2 H). |
| 592 | 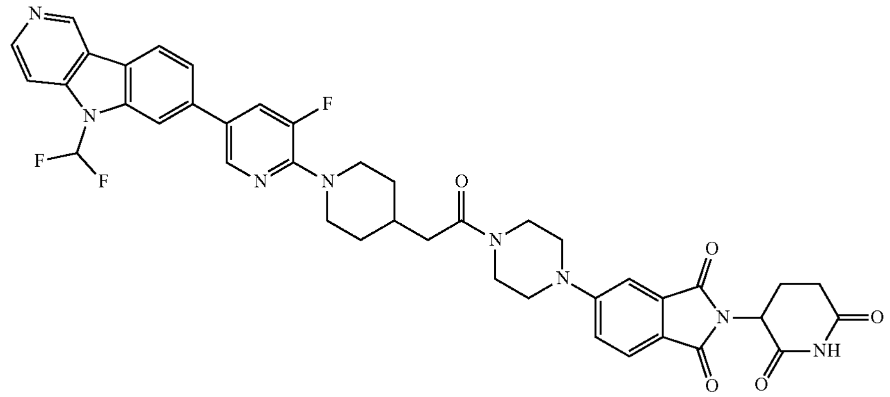 [SMILES: O=C1CCC(N2C(=O)c3ccc(N4CCN(C(=O)CC5CCN(c6ncc(-c7ccc8c9cnccc9n(C(F)F)c8c7)cc6F)CC5)CC4)cc3C2=O)C(=O)N1] | 5-(4-(2-(1-(5-(5-(difluoromethyl)-5H-pyrido[4,3-b]indol-7-yl)-3-fluoropyridin-2-yl)piperidin-4-yl)acetyl)piperazin-1-yl)-2-(2,6-dioxopiperidin-3-yl)isoindoline-1,3-dione | A | 779.2 | $^1$H NMR (400 MHz, DMSO-$d_6$) δ: 11.08 (s, 1H), 9.85 (s, 1H), 8.88 (d, J = 6.8 Hz, 1H), 8.78-8.47 (m, 3H), 8.35-8.28 (m, 2H), 8.05 (dd, J = 2.0, 15.2 Hz, 1H), 8.01-7.96 (m, 1H), 7.71 (d, J = 8.8 Hz, 1H), 7.36 (d, J = 2.0 Hz, 1H), 7.26 (dd, J = 2.4, 8.8 Hz, 1H), 5.08 (dd, J = 5.6, 13.2 Hz, 1H), 4.13 (d, J = 13.6 Hz, 2H), 3.69-3.62 (m, 6H), 3.01-2.92 (m, 2H), 2.92-2.83 (m, 1H), 2.62-2.53 (m, 3H), 2.52 (s, 1H), 2.37 (d, J = 6.4 Hz, 2H), 2.08-1.97 (m, 2H), 1.81 (d, J = 12.4 Hz, 2H), 1.39-1.26 (m, 2H) |

TABLE 1-continued

| | | | | | |
|---|---|---|---|---|---|
| 593 | 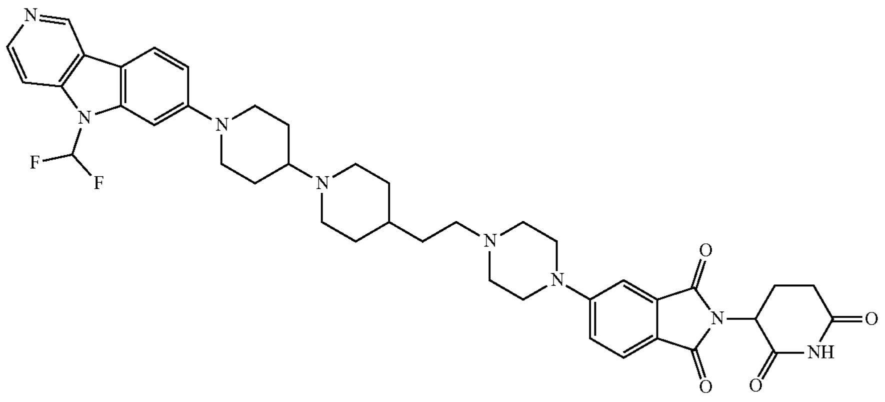 [SMILES: O=C1CCC(N2C(=O)c3ccc(N4CCN(CCC5CCN(C6CCN(c7ccc8c9cnccc9n(C(F)F)c8c7)CC6)CC5)CC4)cc3C2=O)C(=O)N1] | 5-(4-(2-(1'-(5-(difluoromethyl)-5H-pyrido[4,3-b]indol-7-yl)-[1,4'-bipyridin]-4-yl)ethyl)piperazin-1-yl)-2-(2,6-dioxopiperidin-3-yl)isoindoline-1,3-dione | A | 753.2 | 1H NMR (DMSO-$d_6$) δ: 11.10 (s, 1H), 10.54-10.02 (m, 1H), 9.87-9.53 (m, 2H), 8.87-8.38 (m, 2H), 8.33-8.18 (m, 2H), 7.78 (dd, J = 8.4 Hz, 1H), 7.57-7.29 (m, 4H), 5.11 (d, J = 5.2, 12.8 Hz, 1H), 4.49-4.11 (m, 5H), 3.32-2.83 (m, 13H), 2.66-2.53 (m, 2H), 2.22-1.40 (m, 13H). |
| 594 | 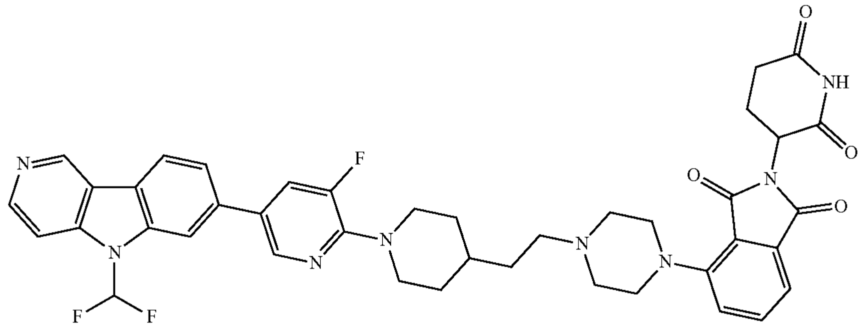 [SMILES: O=C1CCC(N2C(=O)c3cccc(N4CCN(CCC5CCN(c6ncc(-c7ccc8c9cnccc9n(C(F)F)c8c7)cc6F)CC5)CC4)c3C2=O)C(=O)N1] | 4-(4-(2-(1-(5-(5-(difluoromethyl)-5H-pyrido[4,3-b]indol-7-yl)-3-fluoropyridin-2-yl)piperidin-4-yl)ethyl)piperazin-1-yl)-2-(2,6-dioxopiperidin-3-yl)isoindoline-1,3-dione | A | 765.1 | 1H NMR: (DMSO-d6) δ 11.11 (s, 1H), 9.83 (s, 2H), 8.91-8.46 (m, 4H), 8.33-8.23 (m, 2H), 8.13-7.94 (m, 2H), 7.78 (dd, J = 7.2, 8.4 Hz, 1H), 7.46 (dd, J = 8.0, 17.2 Hz, 2H), 5.12 (dd, J = 5.6, 12.4 Hz, 1H), 4.15 (d, J = 13.2 Hz, 3H), 3.36-3.17 (m, 8H), 3.04-2.83 (m, 4H), 2.66-2.53 (m, 2H), 2.13-2.00 (m, 1H), 1.87-1.59 (m, 5H), 1.41-1.28 (m, 2H). |
| 595 | 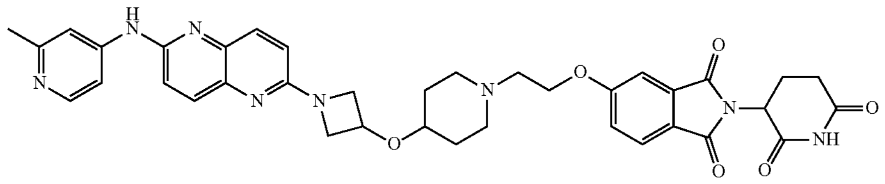 [SMILES: Cc1cc(Nc2ccc3nc(N4CC(OC5CCN(CCOc6ccc7c(c6)C(=O)N(C6CCC(=O)NC6=O)C7=O)CC5)C4)ccc3n2)ccn1] | 2-(2,6-dioxopiperidin-3-yl)-5-(2-(4-((1-(6-((2-methylpyridin-4-yl)amino)-1,5-naphthyridin-2-yl)azetidin-3-yl)oxy)piperidin-1-yl)ethoxy)isoindoline-1,3-dione | | 691.2 | $^1$H NMR (400 MHz, DMSO-$d_6$) δ: 11.11 (s, 1H), 9.64 (s, 1H), 8.23-8.17 (m, 2H), 7.94 (d, J = 9.2 Hz, 1H), 7.87-7.81 (m, 2H), 7.75-7.66 (m, 2H), 7.46 (d, J = 2.0 Hz, 1H), 7.36 (dd, J = 2.0, 8.4 Hz, 1H), 7.18 (d, J = 8.8 Hz, 1H), 6.86 (d, J = 9.0 Hz, 1H), 5.14-5.09 (m 1H), 4.62-4.53 (m, 1H), 4.37-4.20 (m, 4H), 3.87-3.83 (m, 3H), 3.46-3.36 (m, 1H), 2.95-2.79 (m, 3H), 2.74 (br t, J = 5.4 Hz, 2H), 2.64-2.54 (m, 1H), 2.42 (s, 3H), 2.21 (br t, J = 9.8 Hz, 2H), 2.09-1.99 (m, 1H), 1.83 (br d, J = 10.0 Hz, 2H), 1.52-1.44 (m, 2H) |

TABLE 1-continued

| | | | | | |
|---|---|---|---|---|---|
| 596 | 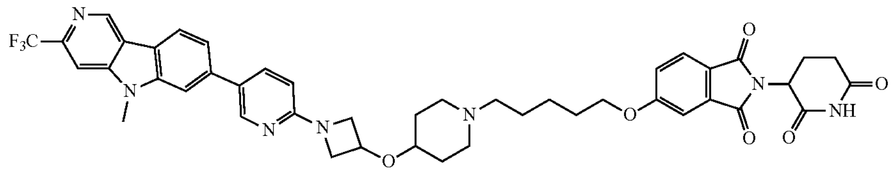 [SMILES: Cn1c2cc(-c3ccc(N4CC(OC5CCN(CCCCCOc6ccc7c(c6)C(=O)N(C6CCC(=O)NC6=O)C7=O)CC5)C4)nc3)ccc2c2cnc(C(F)(F)F)cc21] | 2-(2,6-dioxopiperidin-3-yl)-5-((5-(4-((1-(5-(5-methyl-3-(trifluoromethyl)-5H-pyrido[4,3-b]indol-7-yl)pyridin-2-yl)azetidin-3-yl)oxy)piperidin-1-yl)pentyl)oxy) isoindoline-1,3-dione | | 824.2 | $^1$H NMR (400 MHz, DMSO-$d_6$) δ: 9.49 (s, 1H), 8.61 (d, J = 2.3 Hz, 1H), 8.40 (d, J = 8.4 Hz, 1H), 8.20 (s, 1H), 8.05 (dd, J = 2.5, 8.8 Hz, 1H), 8.00 (s, 1H), 7.83 (d, J = 8.4 Hz, 1H), 7.67 (d, J = 9.6 Hz, 1H), 7.43 (d, J = 2.0 Hz, 1H), 7.35 (dd, J = 2.2, 8.4 Hz, 1H), 6.55 (d, J = 8.8 Hz, 1H), 5.12 (d, J = 12.8 Hz, 1H), 4.58 (s, 1H), 4.31-4.15 (m, 4H), 3.86-3.75 (m, 2H), 2.96-2.93 (m, 1H), 2.94-2.83 (m, 1H), 2.70 (s, 2H), 2.27 (t, J = 6.9 Hz, 3H), 2.02 (d, J = 8.8 Hz, 4H), 1.86-1.76 (m, 1H), 1.78 (dd, J = 6.6, 13.6 Hz, 4H), 1.46 (d, J = 10.4 Hz, 8H) |
| 597 | 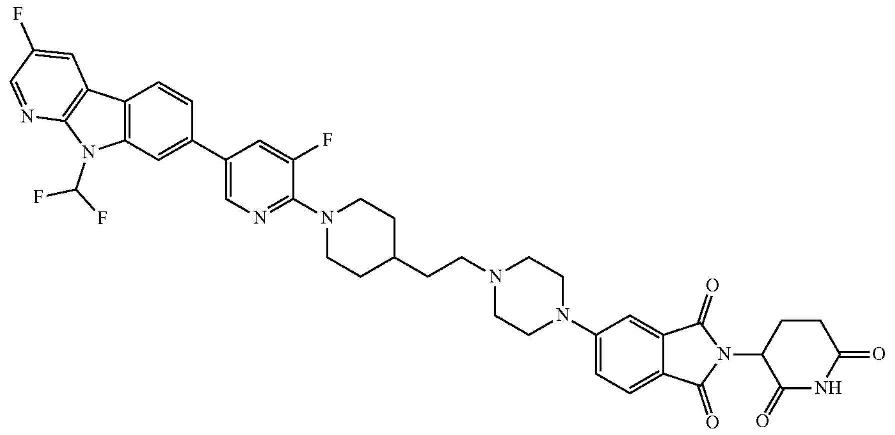 [SMILES: O=C1CCC(N2C(=O)c3ccc(N4CCN(CCC5CCN(c6ncc(-c7ccc8c9cc(F)cnc9n(C(F)F)c8c7)cc6F)CC5)CC4)cc3C2=O)C(=O)N1] | 5-(4-(2-(1-(5-(9-(difluoromethyl)-3-fluoro-9H-pyrido[2,3-b] indol-7-yl)-3-fluoropyridin-2-yl)piperidin-4-yl)ethyl)piperazin-1-yl)-2-(2,6-dioxopiperidin-3-yl)isoindoline-1,3-dione | A | 783.3 | $^1$H NMR (400 MHz, DMSO-$d_6$) δ: 11.16-10.97 (m, 1H), 8.70-8.63 (m, 1H), 8.57-8.21 (m, 5H), 8.07-8.03 (m, 1H), 7.98 (dd, J = 2.0, 14.8 Hz, 1H), 7.79 (d, J = 9.2 Hz, 1H), 7.67 (d, J = 8.4 Hz, 1H), 7.33 (s, 1H), 7.28-7.23 (m, 1H), 5.10-5.03 (m, 1H), 4.11 (d, J = 12.8 Hz, 2H), 3.43 (r d, J = 5.2 Hz, 4H), 2.98-2.83 (m, 4H), 2.63-2.56 (m, 2H), 2.43-2.36 (m, 3H), 2.06-1.98 (m, 1H), 1.80 (d, J = 12.0 Hz, 2H), 1.67-1.40 (m, 4H), 1.39-1.19 (m, 3H) |

TABLE 1-continued

| | | | | | |
|---|---|---|---|---|---|
| 598 | 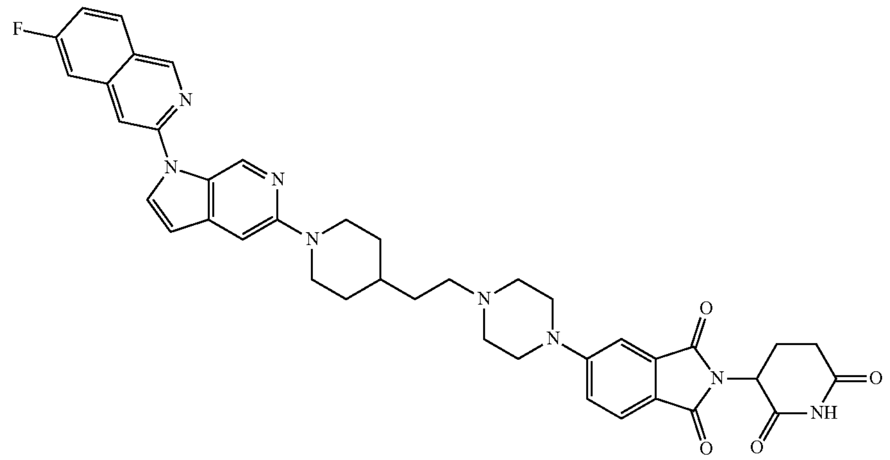 [SMILES: O=C1CCC(N2C(=O)c3ccc(N4CCN(CCC5CCN(c6cc7ccn(-c8cc9cc(F)ccc9cn8)c7cn6)CC5)CC4)cc3C2=O)C(=O)N1] | 2-(2,6-dioxopiperidin-3-yl)-5-(4-(2-(1-(1-(6-fluoroisoquinolin-3-yl)-1H-pyrrolo[2,3-c]pyridin-5-yl)piperidin-4-yl)ethyl)piperazin-1-yl)isoindoline-1,3-dione | A | 715.2 | $^{1}$H NMR (400 MHz, DMSO-$d_6$) δ: 11.10 (s, 1H), 9.84-9.57 (m, 1H), 9.39 (d, J = 18.8 Hz, 2H), 8.52 (d, J = 3.2 Hz, 1H), 8.38-8.29 (m, 1H), 8.24 (s, 1H), 7.82-7.73 (m, 2H), 7.61-7.54 (m, 1H), 7.49 (s, 1H), 7.40-7.34 (m, 1H), 7.33-7.24 (m, 1H), 6.82 (s, 1H), 5.12-5.05 (m, 1H), 4.31-4.06 (m, 5H), 3.76-3.60 (m, 6H), 3.01-2.79 (m, 4H), 2.63-2.56 (m, 2H), 2.06-2.00 (m, 1H), 1.86-1.79 (m, 2H), 1.56 (d, J = 1.2 Hz, 3H), 1.36-1.25 (m, 2H) |
| 599 | 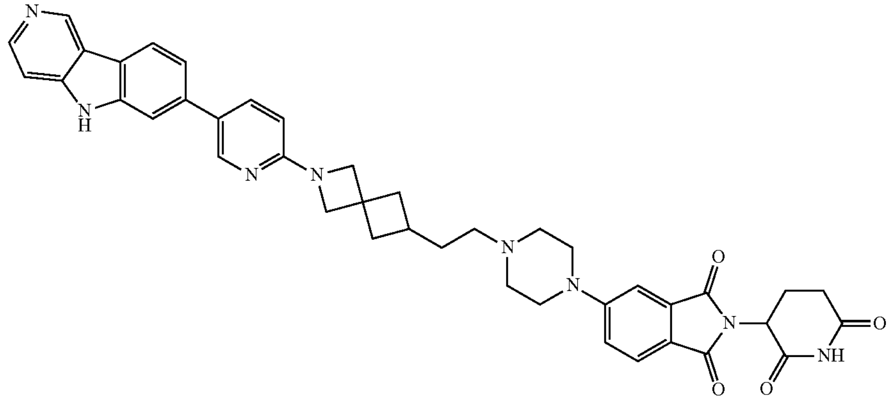 [SMILES: O=C1CCC(N2C(=O)c3ccc(N4CCN(CCC5CC6(C5)CN(c5ccc(-c7ccc8c(c7)[nH]c7ccncc78)cn5)C6)CC4)cc3C2=O)C(=O)N1] | 5-(4-(2-(2-(5-(5H-pyrido[4,3-b]indol-7-yl)pyridin-2-yl)-2-azaspiro[3.3]heptan-6-yl)ethyl)piperazin-1-yl)-2-(2,6-dioxopiperidin-3-yl)isoindoline-1,3-dione | A | 709.2 | $^{1}$H NMR (400 MHz, DMSO-$d_6$) δ: 13.15 (s, 1 H), 11.09 (s, 1 H), 10.12-9.47 (m, 2 H), 8.66 (d, J = 6.80 Hz, 1 H), 8.55-8.43 (m, 2 H), 8.17-8.07 (m, 1 H), 8.04-7.97 (m, 2 H), 7.77 (d, J = 8.40 Hz, 2 H), 7.50 (d, J = 2.00 Hz, 1 H), 7.37 (dd, J = 8.80, 2.00 Hz, 1 H), 6.64 (d, J = 8.80 Hz, 1 H), 5.10 (dd, J = 12.80, 5.20 Hz, 1 H), 4.34-4.18 (m, 2 H), 4.14 (s, 2 H), 4.03 (s, 2 H), 3.31-3.22 (m, 3 H), 3.19 3.12 (m, 2 H), 3.07 (dd, J = 8.40, 7.60 Hz, 2 H), 2.94-2.85 (m, 1 H), 2.63-2.52 (m, 3 H), 2.42-2.36 (m, 2 H), 2.23-2.15 (m, 1 H), 2.03 (dd, J = 10.40, 4.80, 3.20 Hz, 1 H), 1.98-1.91 (m, 2 H), 1.85-1.76 (m, 2 H). |

TABLE 1-continued

| | | | | |
|---|---|---|---|---|
| 648 | 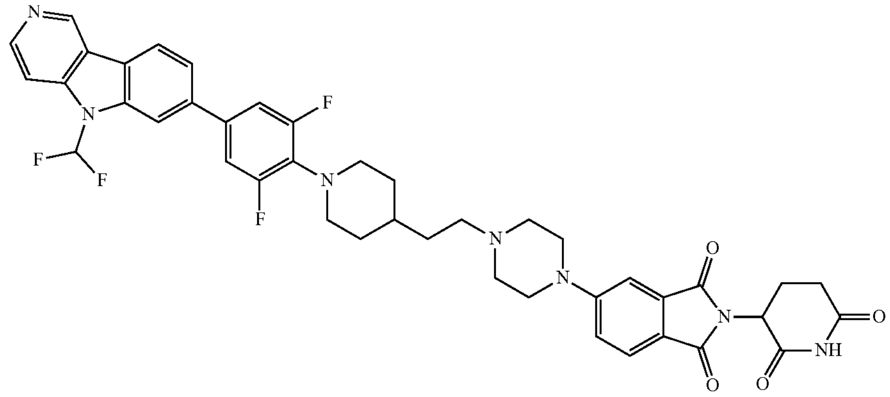 [SMILES: O=C1CCC(N2C(=O)c3ccc(N4CCN(CCC5CCN(c6c(F)cc(-c7ccc8c9cnccc9n(C(F)F)c8c7)cc6F)CC5)CC4)cc3C2=O)C(=O)N1] | 5-(4-(2-(1-(4-(5-(difluoromethyl)-5H-pyrido[4,3-b]indol-7-yl)-2,6-difluorophenyl)piperidin-4-yl)ethyl)piperazin-1-yl)-2-(2,6-dioxopiperidin-3-yl)isoindoline-1,3-dione | 782.2 | 1H NMR (400 MHz, DMSO-d6) δ: 1.27-1.43 (m, 2 H), 1.53 (s, 1 H), 1.71-1.84 (m, 4 H), 1.97-2.16 (m, 4 H), 2.54-2.70 (m, 3 H), 2.81-2.97 (m, 1 H), 3.29 (s, 8 H), 4.24 (s, 2 H), 5.10 (d, J = 12.8, 5.4 Hz, 1 H), 7.38 (d, J = 8.8, 2.0 Hz, 1 H), 7.51 (d, J = 2.0 Hz, 1 H), 7.57-7.66 (m, 2 H), 7.78 (d, J = 8.4 Hz, 1 H), 7.95 (d, J = 9.6 Hz, 1 H), 8.18 (d, J = 6.0 Hz, 1 H), 8.31 (s, 1 H), 8.42-8.76 (m, 2 H), 8.82 (d, J = 6.4 Hz, 1 H), 9.77 (s, 1 H), 11.10 (s, 1 H) |
| 649 | 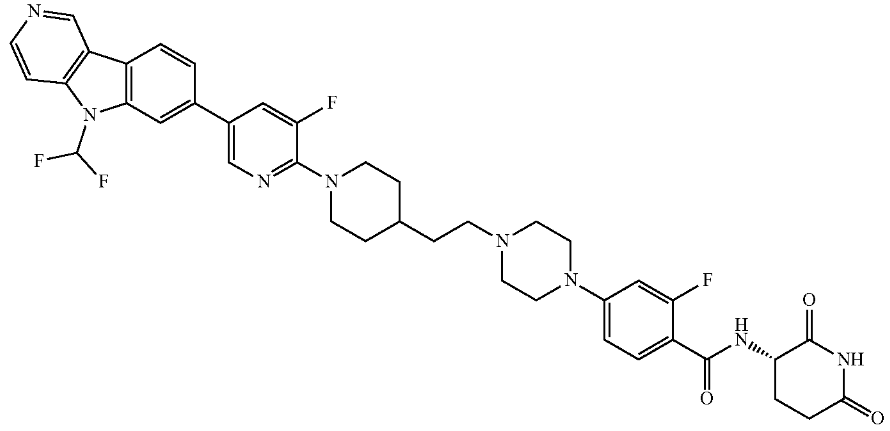 [SMILES: O=C1CC[C@H](NC(=O)c2ccc(N3CCN(CCC4CCN(c5ncc(-c6ccc7c8cnccc8n(C(F)F)c7c6)cc5F)CC4)CC3)cc2F)C(=O)N1] | (S)-4-(4-(2-(1-(5-(5-(difluoromethyl)-5H-pyrido[4,3-b]indol-7-yl)-3-fluoropyridin-2-yl)piperidin-4-yl)ethyl)piperazin-1-yl)-N-(2,6-dioxopiperidin-3-yl)-2-fluorobenzamide | 757.2 | $^1$H NMR (400 MHz, DMSO-$d_6$) δ: 10.84 (s, 1H), 9.87-9.67 (m, 2H), 8.85 (d, J = 6.4 Hz, 1H), 8.76-8.45 (m, 3H), 8.30 (s, 1H), 8.24 (d, J = 6.4 Hz, 1H), 8.16-8.10 (m, 1H), 8.09-8.03 (m, 1H), 7.96 (dd, J = 1.2, 8.4 Hz, 1H), 7.72-7.65 (m, 1H), 6.97-6.89 (m, 2H), 4.78-4.68 (m, 1H), 4.16-4.05 (m, 4H), 3.24 (d, J = 5.2 Hz, 3H), 3.14 (d, J = 3.6 Hz, 3H), 3.01-2.92 (m, 3H), 2.80-2.72 (m, 2H), 2.19-1.97 (m, 2H), 1.85-1.76 (m, 2H), 1.74-1.58 (m, 3H), 1.40-1.27 (m, 2H) |
| 650 | 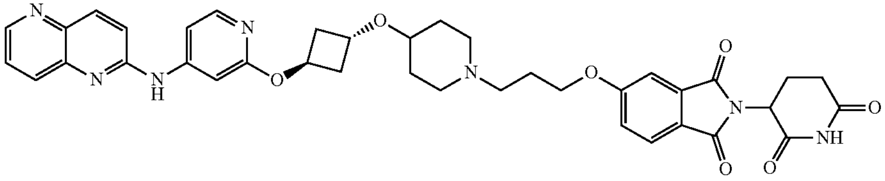 [SMILES: O=C1CCC(N2C(=O)c3ccc(OCCCN4CCC(O[C@H]5C[C@H](Oc6cc(Nc7ccc8ncccc8n7)ccn6)C5)CC4)cc3C2=O)C(=O)N1] | 5-(3-(4-((1r,3r)-3-((4-((1,5-naphthyridin-2-yl)amino)pyridin-2-yl)oxy)cyclobutoxy)piperidin-1-yl)propoxy)-2-(2,6-dioxopiperidin-3-yl)isoindoline-1,3-dione | 706.2 | 1H NMR (400 MHz, DMSO) δ: 11.12 (s, 1H), 10.04 (s, 1H), 8.73 (dd, J = 1.2, 4.4 Hz, 1H), 8.25-8.15 (m, 3H), 7.98 (d, J = 5.6 Hz, 1H), 7.84 (d, J = 8.4 Hz, 1H), 7.75-7.71 (m, 1H), 7.66 (dd, J = 4.4, 8.4 Hz, 1H), 7.43 (d, J = 2.0 Hz, 1H), 7.38-7.32 (m, 2H), 7.28 (dd, J = 1.6, 5.6 Hz, 1H), 5.27-5.20 (m, 1H), 5.13 (dd, J = 5.6, 12.8 Hz, 1H), 4.38-4.34 (m, 1H), 4.22 (t, J = 6.0 Hz, 3H), 3.34 (s, 1H), 2.96-2.71 (m, 4H), 2.70-2.54 (m, 3H), 2.40-2.30 (m, 3H), 2.21-2.01 (m, 3H), 1.98-1.77 (m, 4H), 1.55-1.39 (m, 2H) |

TABLE 1-continued

| | | | | | |
|---|---|---|---|---|---|
| 651 | 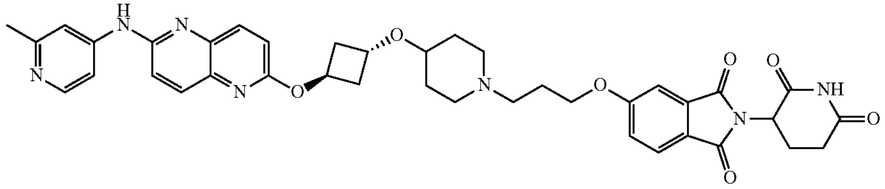 [SMILES: Cc1cc(Nc2ccc3nc(O[C@H]4C[C@H](OC5CCN(CCCOc6ccc7c(c6)C(=O)N(C6CCC(=O)NC6=O)C7=O)CC5)C4)ccc3n2)ccn1] | 2-(2,6-dioxopiperidin-3-yl)-5-(3-(4-((1r,3r)-3-((6-((2-methylpyridin-4-yl)amino)-1,5-naphthyridin-2-yl)oxy)cyclobutoxy)piperidin-1-yl)propoxy)isoindoline-1,3-dione | | 720.2 | 1H NMR (400 MHz, MeOD) δ: 8.08 (d, J = 8.0 Hz, 1 H), 7.99 (d, J = 12.0 Hz, 1 H), 7.88 (d, J = 8.0 Hz, 1 H), 7.74-7.68 (m, 3 H), 7.31 (d, J = 4.0 Hz, 1 H), 7.21 (dd, J = 8.0, 4.0 Hz, 1 H), 7.10 (d, J = 8.0 Hz, 1 H), 6.99 (d, J = 8.0 Hz, 1 H), 5.37-5.32 (m, 1 H), 5.00 (dd, J = 12.0, 4.0 Hz, 1 H), 4.37-4.31 (m, 1 H), 4.11 (t, J = 6.0 Hz, 2 H), 3.38-3.35 (m, 1 H), 2.80-2.72 (m, 3 H), 2.68-2.60 (m, 2 H), 2.53-2.49 (m, 2 H), 2.43-2.41 (m, 1 H), 2.39 (s, 3 H), 2.38-2.37 (m, 1 H), 2.23-2.20 (m, 2 H), 2.05-1.91 (m, 4 H), 1.85-1.82 (m, 2 H), 1.59-1.52 (m, 2 H), 1.19 (br (s, 2 H). |
| 652 | 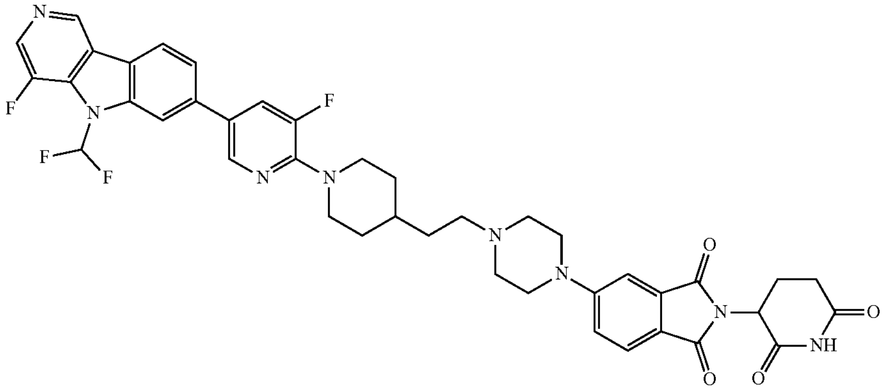 [SMILES: O=C1CCC(N2C(=O)c3ccc(N4CCN(CCC5CCN(c6ncc(-c7ccc8c9cncc(F)c9n(C(F)F)c8c7)cc6F)CC5)CC4)cc3C2=O)C(=O)N1] | 5-(4-(2-(1-(5-(5-(difluoromethyl)-4-fluoro-5H-pyrido[4,3-b]indol-7-yl)-3-fluoropyridin-2-yl)piperidin-4-yl)ethyl)piperazin-1-yl)-2-(2,6-dioxopiperidin-3-yl)isoindoline-1,3-dione | A | 783.2 | $^1$H NMR (400 MHz, DMSO-d6) δ: 11.18-10.97 (m, 1H), 9.38 (d, J = 1.6 Hz, 1H), 8.69-8.28 (m, 5H), 8.04 (dd, J = 1.6, 15.1 Hz, 1H), 7.90-7.83 (m, 1H), 7.69 (d, J = 8.8 Hz, 1H), 7.35 (s, 1H), 7.27 (dd, J = 1.6, 8.8 Hz, 1H), 5.08 (dd, J = 5.2, 12.8 Hz, 1H), 4.17-4.08 (m, 2H), 3.45 (s, 5H), 2.98-2.54 (m, 4H), 2.64-2.59 (m, 3H), 2.43-2.37 (m, 3H), 2.08-1.97 (m, 1H), 1.87-1.76 (m, 2H), 1.66-1.56 (m, 1H), 1.51-1.42 (m, 2H), 1.37-1.24 (m, 2H) |

TABLE 1-continued

| | | | | | |
|---|---|---|---|---|---|
| 653 | 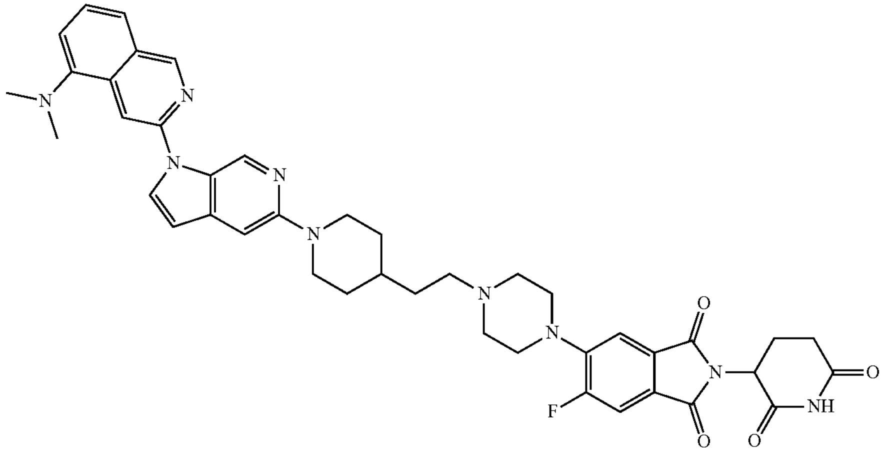 [SMILES: CN(C)c1cccc2cnc(-n3ccc4cc(N5CCC(CCN6CCN(c7cc8c(cc7F)C(=O)N(C7CCC(=O)NC7=O)C8=O)CC6)CC5)ncc43)cc12] | 5-(4-(2-(1-(1-(5-(dimethylamino)isoquinolin-3-yl)-1H-pyrrolo[2,3-c]pyridin-5-yl)piperidin-4-yl)ethyl)piperazin-1-yl)-2-(2,6-dioxopiperidin-3-yl)-6-fluoroisoindoline-1,3-dione | A | 758.2 | $^1$H NMR (400 MHz, DMSO-$d_6$) δ: 11.10 (s, 1H), 9.32 (s, 1H), 9.24 (s, 1H), 8.24 (d, J = 3.2 Hz, 1H), 8.14 (s, 1H), 8.02 (s, 1H), 7.79 (d, J = 8.4 Hz, 1H), 7.72 (d, J = 11.6 Hz, 1H), 7.53 (t, J = 7.6 Hz, 1H), 7.45 (d, J = 7.6 Hz, 1H), 7.36 (d, J = 7.0 Hz, 1H), 6.96 (s, 1H), 6.63 (d, J = 3.2 Hz, 1H), 5.17-5.04 (m, 1H), 4.23 (d, J = 12.4 Hz, 2H), 3.26 (d, J = 3.2 Hz, 6H), 2.90 (s, 6H), 2.79-2.69 (m, 2H), 2.57 (s, 5H), 2.47-2.42 (m, 2H), 2.09-1.97 (m, 1H), 1.78 (d, J = 11.2 Hz, 2H), 1.45 (d, J = 6.8 Hz, 3H), 1.32-1.19 (m, 2H) |
| 654 | 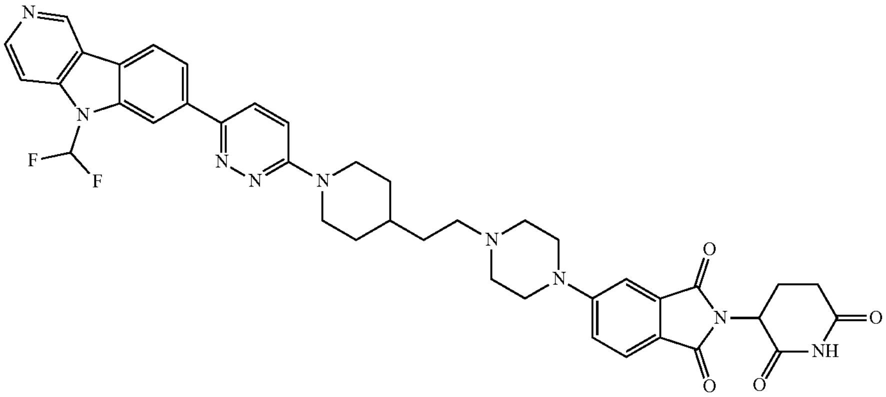 [SMILES: O=C1CCC(N2C(=O)c3ccc(N4CCN(CCC5CCN(c6ccc(-c7ccc8c9cnccc9n(C(F)F)c8c7)nn6)CC5)CC4)cc3C2=O)C(=O)N1] | 5-(4-(2-(1-(6-(5-(difluoromethyl)-5H-pyrido[4,3-b]indol-7-yl)pyridazin-3-yl)piperidin-4-yl)ethyl)piperazin-1-yl)-2-(2,6-dioxopiperidin-3-yl)isoindoline-1,3-dione | | 748.3 | 1H NMR (400 MHz, DMSO-d6) δ: 1.14-1.31 (m, 3 H), 1.47 (d, J = 6.8 Hz, 2 H), 1.68 (s, 1 H), 1.83 (d, J = 12.0 Hz, 2 H), 1.97-2.09 (m, 2 H), 2.80-3.05 (m, 5 H), 3.45 (s, 8 H), 4.49 (d, J = 12.4 Hz, 2 H), 5.08 (d, J = 12.8, 5.2 Hz, 1 H), 7.27 (d, J = 8.4, 2.0 Hz, 1 H), 7.35 (d, J = 2.0 Hz, 1 H), 7.42 (d, J = 9.6 Hz, 1 H), 7.69 (d, J = 8.4 Hz, 1 H), 7.85 (d, J = 6.0 Hz, 1 H), 8.08 (d, J = 9.6 Hz, 1 H), 8.14 (d, J = 8.4, 1.2 Hz, 1 H), 8.31-8.47 (m, 2 H), 8.58-8.65 (m, 2 H), 9.50 (s, 1 H), 11.08 (s, 1 H) |
| 655 | 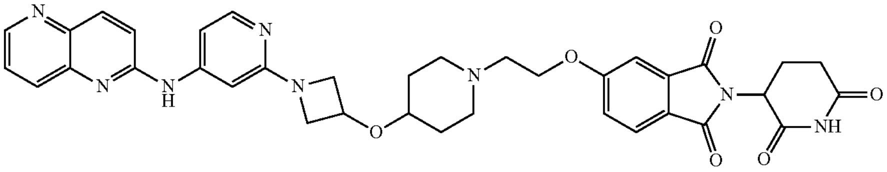 [SMILES: O=C1CCC(N2C(=O)c3ccc(OCCN4CCC(OC5CN(c6cc(Nc7ccc8ncccc8n7)ccn6)C5)CC4)cc3C2=O)C(=O)N1] | 5-(2-(4-((1-(4-((1,5-naphthyridin-2-yl)amino)pyridin-2-yl)azetidin-3-yl)oxy)piperidin-1-yl)ethoxy)-2-(2,6-dioxopiperidin-3-yl)isoindoline-1,3-dione | | 677.3 | 1H NMR (400 MHz, MeOD) δ: 8.74 (d, J = 3.60 Hz, 1 H), 8.25 (dd, J = 16.40, 8.40 Hz, 2 H), 7.92-7.77 (m, 3 H), 7.70 (dd, J = 8.40, 4.00 Hz, 1 H), 7.48 (s, 1 H), 7.40-7.33 (m, 2 H), 6.98 (d, J = 5.60 Hz, 1 H), 5.11 (dd, J = 12.80, 5.40 Hz, 1 H), 4.74-4.67 (m, 1 H), 4.49-4.36 (m, 4 H), 4.12-4.02 (m, 2 H), 3.78-3.68 (m, 1 H), 3.28-3.22 (m, 4 H), 3.02-2.63 (m, 5 H), 2.17-2.00 (m, 3 H), 1.96-1.82 (m, 2 H). |

TABLE 1-continued

| | | | | | |
|---|---|---|---|---|---|
| 656 | 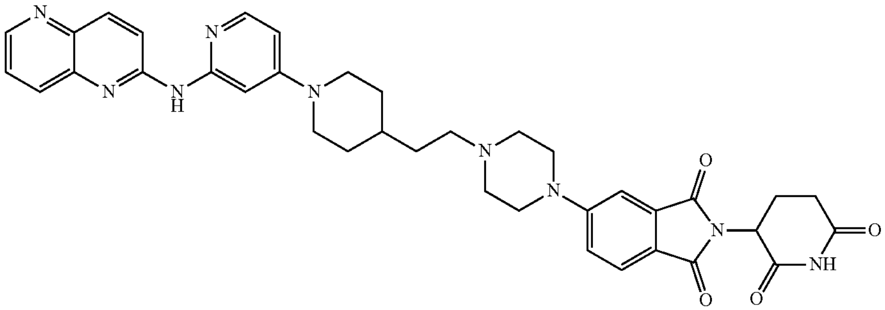 [SMILES: O=C1CCC(N2C(=O)c3ccc(N4CCN(CCC5CCN(c6ccnc(Nc7ccc8ncccc8n7)c6)CC5)CC4)cc3C2=O)C(=O)N1] | 5-(4-(2-(1-(2-((1,5-naphthyridin-2-yl)amino)pyridin-4-yl)piperidin-4-yl)ethyl)piperazin-1-yl)-2-(2,6-dioxopiperidin-3-yl)isoindoline-1,3-dione | A | 674.2 | $^1$H NMR (400 MHz, METHANOL, $d_4$) δ: 8.83 (d, J = 4.4 Hz, 1H), 8.56 (d, J = 8.4 Hz, 1H), 8.43 (s, 1H), 8.38 (d, J = 9.2 Hz, 1H), 8.02 (d, J = 7.6 Hz, 1H), 7.78 (dd, J = 4.4, 8.4 Hz, 1H), 7.70 (d, J = 8.4 Hz, 1H), 7.46-7.34 (m, 2H), 7.25 (dd, J = 2.0, 8.8 Hz, 1H), 6.94 (dd, J = 2.4, 7.6 Hz, 1H), 6.53 (br s, 1H), 5.07 (dd, J = 5.4, 12.4 Hz, 1H), 4.17 (br d, J = 13.6 Hz, 2H), 3.53-3.46 (m, 4H), 3.21 (br s, 2H), 2.92-2.68 (m, 7H), 2.60-2.53 (m, 2H), 2.16-2.07 (m, 1H), 1.97 (br d, J = 13.4 Hz, 2H), 1.82 (br s, 1H), 1.64-1.55 (m, 2H), 1.40-1.32 (m, 2H) |
| 657 | 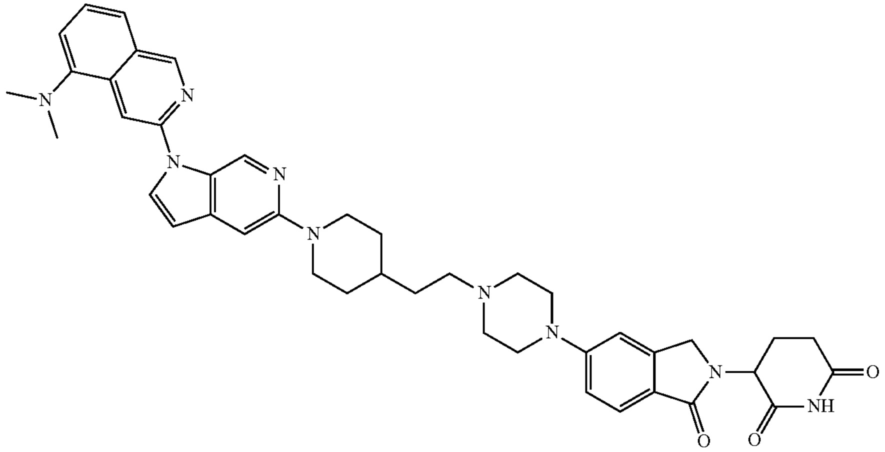 [SMILES: CN(C)c1cccc2cnc(-n3ccc4cc(N5CCC(CCN6CCN(c7ccc8c(c7)CN(C7CCC(=O)NC7=O)C8=O)CC6)CC5)ncc43)cc12] | 3-(5-(4-(2-(1-(1-(5-(dimethylamino)isoquinolin-3-yl)-1H-pyrrolo[2,3-c]pyridin-5-yl)piperidin-4-yl)ethyl)piperazin-1-yl)-1-oxoisoindolin-2-yl)piperidine-2,6-dione | | 726.3 | $^1$H NMR (400 MHz, DMSO-$d_6$) δ: 10.95 (s, 1H), 9.32 (s, 1H), 9.25 (s, 1H), 8.25 (d, J = 3.2 Hz, 1H), 8.14 (s, 1H), 8.03 (s, 1H), 7.80 (d, J = 8.4 Hz, 1H), 7.60-7.49 (m, 2H), 7.36 (d, J = 7.2 Hz, 1H), 7.12 (s, 2H), 6.98 (s, 1H), 6.64 (d, J = 3.2 Hz, 1H), 5.16-4.93 (m, 1H), 4.37-4.20 (m, 4H), 3.31-3.20 (m, 5H), 2.90 (s, 10H), 2.81-2.69 (m, 4H), 2.60 (d, J = 2.8 Hz, 1H), 2.41-2.32 (m, 1H), 2.03-1.90 (m, 1H), 1.78 (d, J = 11.6 Hz, 2H), 1.55 (s, 3H), 1.27 (d, J = 9.2 Hz, 2H) |

TABLE 1-continued

| | | | | |
|---|---|---|---|---|
| 658 | 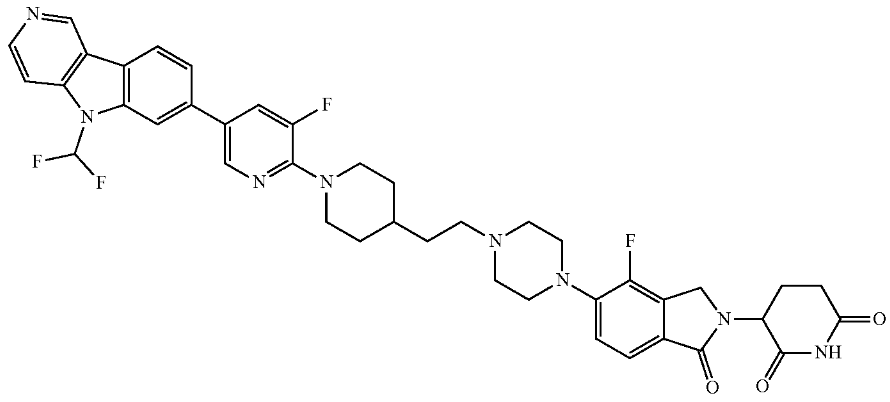 [SMILES: O=C1CCC(N2Cc3c(ccc(N4CCN(CCC5CCN(c6ncc(-c7ccc8c9cnccc9n(C(F)F)c8c7)cc6F)CC5)CC4)c3F)C2=O)C(=O)N1] | 3-(5-(4-(2-(1-(5-(5-(difluoromethyl)-5H-pyrido[4,3-b]indol-7-yl)-3-fluoropyridin-2-yl)piperidin-4-yl)ethyl)piperazin-1-yl)-4-fluoro-1-oxoisindolin-2-yl)piperidine-2,6-dione | 769.2 | $^1$H NMR (400 MHz, DMSO-$d_6$) δ: 10.98 (s, 1 H), 9.48 (s, 1 H), 8.66-8.07 (m, 6 H), 7.99 (dd, J = 15.20, 2.00 Hz, 1 H), 7.80 (d, J = 6.40 Hz, 2 H), 7.48 (d, J = 8.40 Hz, 1 H), 7.17 (t, J = 7.80 Hz, 1 H), 5.07 (dd, J = 13.20, 4.80 Hz, 1 H), 4.49 (d, J = 17.20 Hz, 1 H), 4.32 (d, J = 16.80 Hz, 1 H), 4.10 (d, J = 12.40 Hz, 2 H), 3.17 (s, 4 H), 2.97-2.86 (m, 4 H), 2.67-2.60 (m, 4 H), 2.57 (s, 1 H), 2.42 (dd, J = 13.20, 4.40 Hz, 2 H), 2.00-1.93 (m, 1 H), 1.79 (d, J = 11.60 Hz, 2 H) 1.62-1.54 (m, 1 H), 1.47 (d, J = 6.80 Hz, 2 H), 1.34-1.24 (m, 2 H). |
| 659 | 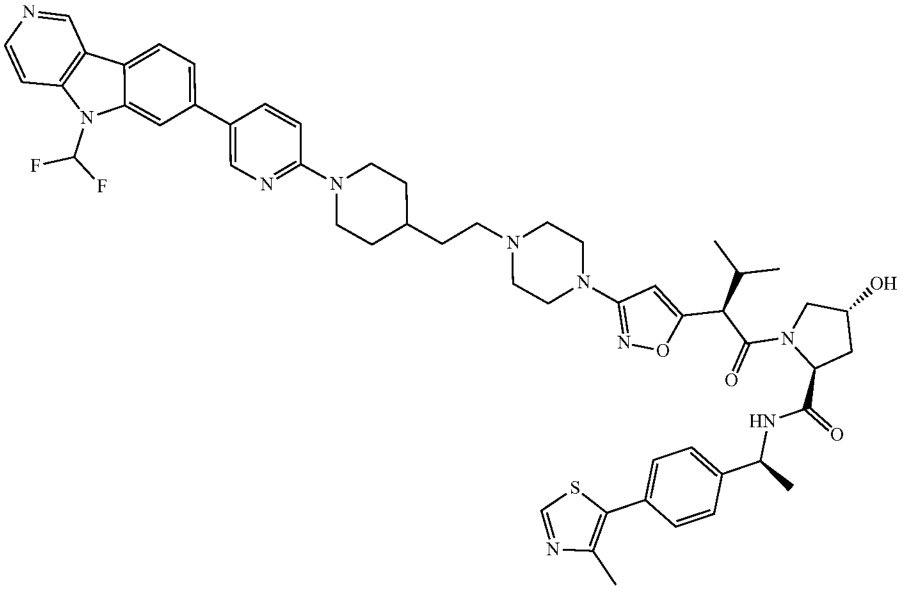 | (2S,4R)-1-((R)-2-(3-(4-(2-(1-(5-(5-(difluoromethyl)-5H-pyrido[4,3-b]indol-7-yl)pyridin-2-yl)piperidin-4-yl)ethyl)piperazin-1-yl)isoxazol-5-yl)-3-methylbutanoyl)-4-hydroxy-N-((S)-1-(4-(4-methylthiazol-5-yl)phenyl)ethyl) pyrrolidine-2-carboxamide | 971.3 | $^1$H NMR (400 MHz, DMSO-$d_6$) δ: 9.46 (s, 1H), 9.02-8.96 (m, 1H), 8.83-8.46 (m, 3H), 8.44-8.32 (m, 2H), 8.12 (s, 1H), 7.96 (dd, J = 2.4, 9.2 Hz, 1H), 7.80 (d, J = 5.6 Hz, 1H), 7.73 (dd, J = 1.2, 8.4 Hz, 1H), 7.49-7.40 (m, 2H), 7.39-7.32 (m, 2H), 6.96 (d, J = 8.8 Hz, 1H), 6.14 (s, 1H), 5.12 (d, J = 3.6 Hz, 1H), 4.96-4.86 (m, 1H), 4.39-4.34 (m, 2H), 4.28 (s, 1H), 3.71 (dd, J = 4.4, 10.8 Hz, 1H), 3.57 (d, J = 9.6 Hz, 1H), 3.47-3.46 (m, 1H), 3.47-3.39 (m, 1H), 3.16 (s, 4H), 2.85 (t, J = 12.0 Hz, 2H), 2.47-2.43 (m, 6H), 2.39-2.34 (m, 2H), 2.27-2.16 (m, 1H), 2.05-1.98 (m, 1H), 1.82-1.72 (m, 3H), 1.64-1.52 (m, 1H), 1.47-1.36 (m, 5H), 1.25-1.09 (m, 3H), 0.99-0.92 (m, 3H), 0.85-0.76 (m, 3H) |

TABLE 1-continued
| | | | | |
|---|---|---|---|---|
| 660 | 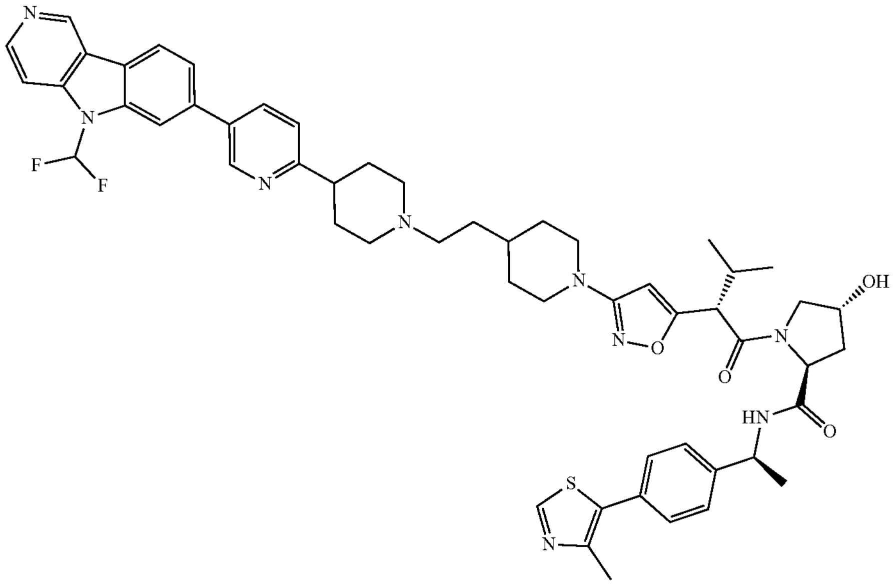 [SMILES: Cc1ncsc1-c1ccc([C@H](C)NC(=O)[C@@H]2C[C@@H](O)CN2C(=O)[C@H](c2cc(N3CCC(CCN4CCC(c5ccc(-c6ccc7c8cnccc8n(C(F)F)c7c6)cn5)CC4)CC3)no2)C(C)C)cc1] | (2S,4R)-1-((S)-2-(3-(4-(2-(4-(5-(5-(difluoromethyl)-5H-pyrido[4,3-b]indol-7-yl)pyridin-2-yl)piperidin-1-yl)ethyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 970.3 | $^1$H NMR (400 MHz, DMSO-$d_6$) δ: 9.51 (s, 1H), 9.00-8.91 (m, 2H), 8.66-8.37 (m, 3H), 8.23-8.20 (m, 2H), 8.18-8.13 (m, 2H), 7.86-7.78 (m, 2H), 7.49-7.39 (m, 4H), 7.32 (d, J = 8.4 Hz, 1H), 6.14 (s, 1H), 5.18-4.80 (m, 2H), 4.61-4.22 (m, 3H), 3.68 (d, J = 8.8 Hz, 1H), 3.58 (s, 3H), 3.13-3.10 (m, 2H), 2.82-2.75 (m, 2H), 2.74-2.70 (m, 1H), 2.46 (s, 1H), 2.44 (s, 3H), 2.25 (td, J = 6.4, 8.8 Hz, 3H), 2.06-2.00 (m, 1H), 1.94-1.82 (m, 5H), 1.75-1.62 (m, 3H), 1.47-1.42 (m, 3H), 1.35 (d, J = 7.2 Hz, 2H), 1.19-1.11 (m, 2H), 0.96 (d, J = 6.4 Hz, 3H), 0.83-0.80 (m, 3H), 0.75 (d, J = 6.4 Hz, 1H) |

TABLE 1-continued

| | | | | |
|---|---|---|---|---|
| 661 | 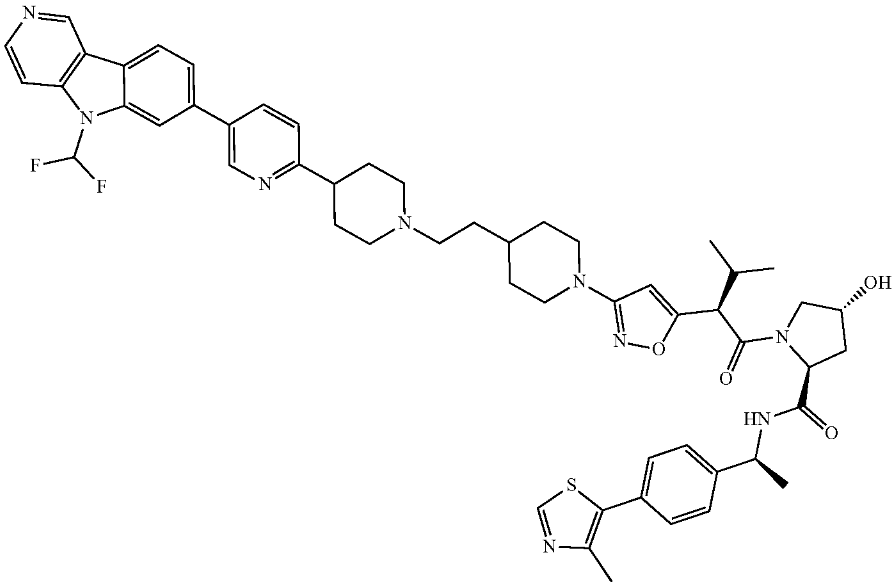 [SMILES: Cc1ncsc1-c1ccc([C@H](C)NC(=O)[C@@H]2C[C@@H](O)CN2C(=O)[C@@H](c2cc(N3CCC(CCN4CCC(c5ccc(-c6ccc7c8cnccc8n(C(F)F)c7c6)cn5)CC4)CC3)no2)C(C)C)cc1] | (2S,4R)-1-((R)-2-(3-(4-(2-(4-(5-(5-(difluoromethyl)-5H-pyrido[4,3-b]indol-7-yl)pyridin-2-yl)piperidin-1-yl)ethyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 970.3 | $^1$H NMR (400 MHz, DMSO-$d_6$) δ: 9.51 (s, 1H), 9.00-8.92 (m, 2H), 8.80-8.50 (m, 2H), 8.44 (d, J = 8.4 Hz, 1H), 8.41-8.35 (m, 1H), 8.24-8.10 (m, 3H), 7.86-7.80 (m, 2H), 7.48-7.42 (m, 3H), 7.39-7.35 (m, 2H), 6.14 -5.98 (m, 1H), 5.20-4.83 (m, 2H), 4.37 (t, J = 7.6 Hz, 1H), 4.28 (d, J = 2.4 Hz, 1H), 3.71 (dd, J = 4.0, 10.0 Hz, 1H), 3.64-3.60 (m, 2H), 3.56 (d, J = 10.0 Hz, 2H), 3.08 (d, J = 11.2 Hz, 3H), 2.78-2.71 (m, 4H), 2.45 (s, 3H), 2.22-2.12 (m, 4H), 2.04-1.99 (m, 1H), 1.89 (s, 2H), 1.85-1.76 (m, 3H), 1.73 (s, 1H), 1.46 (d, J = 6.8 Hz, 3H), 1.38 (d, J = 7.2 Hz, 3H), 1.22-1.14 (m, 2H), 0.95 (d, J = 6.8 Hz, 3H), 0.84-0.78 (m, 3H) |
| 662 | 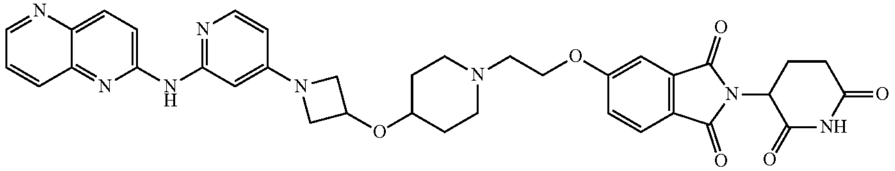 [SMILES: O=C1CCC(N2C(=O)c3ccc(OCCN4CCC(OC5CN(c6ccnc(Nc7ccc8ncccc8n7)c6)C5)CC4)cc3C2=O)C(=O)N1] | 5-(2-(4-((1-(2-((1,5-naphthyridin-2-yl)amino)pyridin-4-yl)azetidin-3-yl)oxy)piperidin-1-yl)ethoxy)-2-(2,6-dioxopiperidin-3-yl)isoindoline-1,3-dione | 677.3 | 1H NMR (400 MHz, DMSO-$d_6$) δ: 11.24 (s, 1H), 10.20 (br s, 1H), 8.83 (d, J = 4.0 Hz, 1H), 8.30-8.26 (m, 3H), 8.05 (d, J = 4.0 Hz, 1H), 7.96 (d, J = 8.0 Hz, 1H), 7.82-7.80 (m, 2H), 7.60 (m, 1H), 7.51-7.48 (m, 1H), 6.24 (br d, J = 8.0 Hz, 1H), 5.27-5.22 (m, 1H), 4.74-4.75 (m, 1H), 4.44-4.36 (m, 4H), 3.93-3.91 (m, 2H), 3.01-2.94 (m, 6H), 2.80-2.70 (m, 4H), 2.19-2.16 (m, 1H), 2.00-1.98 (m, 2H), 1.66-1.63 (m, 2H). |
| 663 | 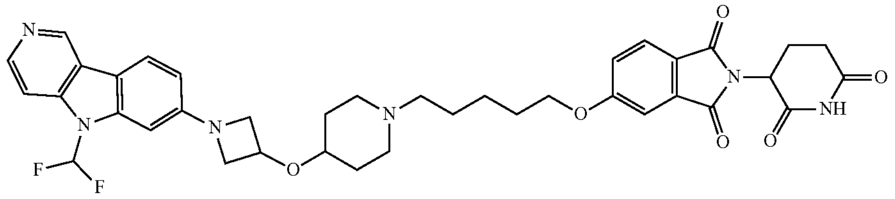 [SMILES: O=C1CCC(N2C(=O)c3ccc(OCCCCCN4CCC(OC5CN(c6ccc7c8cnccc8n(C(F)F)c7c6)C5)CC4)cc3C2=O)C(=O)N1] | 5-((5-(4-((1-(5-(difluoromethyl)-5H-pyrido[4,3-b]indol-7-yl)azetidin-3-yl)oxy)piperidin-1-yl)pentyl)oxy)-2-(2,6-dioxopiperidin-3-yl)isoindoline-1,3-dione | 715.2 | 1H NMR (400 MHz, METHANOL-d4) δ: 9.09 (s, 1 H), 8.39 (d, J = 6.0 Hz, 1 H) 7.85-8.19 (m, 2 H), 7.80 (d, J = 8.4 Hz, 1H), 7.67 (d, J = 6.0 Hz, 1 H), 7.39 (d, J = 2.0 Hz, 1 H), 7.31 (dd, J = 8.4, 2.0 Hz, 1 H), 6.77 (s, 1 H), 6.62 (br d, J = 8.8 Hz, 1 H), 5.07-5.12 (m, 1 H), 4.66-4.67 (m, 1 H), 4.28 (br t, J = 6.8 Hz, 2 H), 4.18 (br t, J = 6.4 Hz, 2 H), 3.79 (br dd, J = 7.6, 4.4 Hz, 2 H), 3.65 (br s, 1 H), 2.80-3.14 (m, 5 H), 2.68-2.76 (m, 3 H), 1.71-2.15 (m, 10 H), 1.57 (br d, J = 7.6 Hz, 2 H) |

TABLE 1-continued

| | | | | |
|---|---|---|---|---|
| 664 | 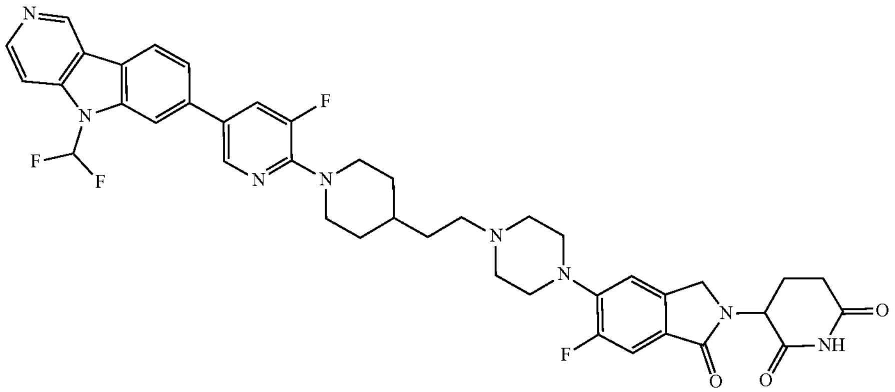 [SMILES: O=C1CCC(N2Cc3cc(N4CCN(CCC5CCN(c6ncc(-c7ccc8c9cnccc9n(C(F)F)c8c7)cc6F)CC5)CC4)c(F)cc3C2=O)C(=O)N1] | 3-(5-(4-(2-(1-(5-(5-(difluoromethyl)-5H-pyrido[4,3-b]indol-7-yl)-3-fluoropyridin-2-yl)piperidin-4-yl)ethyl)piperazin-1-yl)-6-fluoro-1-oxoisoindolin-2-yl)piperidine-2,6-dione | 769.3 | $^1$H NMR (400 MHz, DMSO-$d_6$) δ: 10.98 (s, 1H), 9.49 (s, 1H), 8.67-8.33 (m, 4H), 8.21 (s, 1H), 8.15 (s, 1H), 8.00 (m, 1H), 7.82 (d, J = 6.4 Hz, 2H), 7.43 (d, J = 11.6 Hz, 1H), 7.25 (d, J = 7.6 Hz, 1H), 5.08 (m, 1H), 4.42-4.22 (m, 2H), 4.11 (d, J = 13.2 Hz, 2 H), 3.15-3.06 (m, 4H), 2.99-2.83 (m, 3H), 2.61 (s, 4H), 2.48-2.36 (m, 4H), 2.02-1.93 (m, 1H), 1.86-1.76 (m, 2H), 1.67-1.56 (m, 1H), 1.52-1.43 (m, 2H), 1.37-1.23 (m, 2H) |
| 665 | 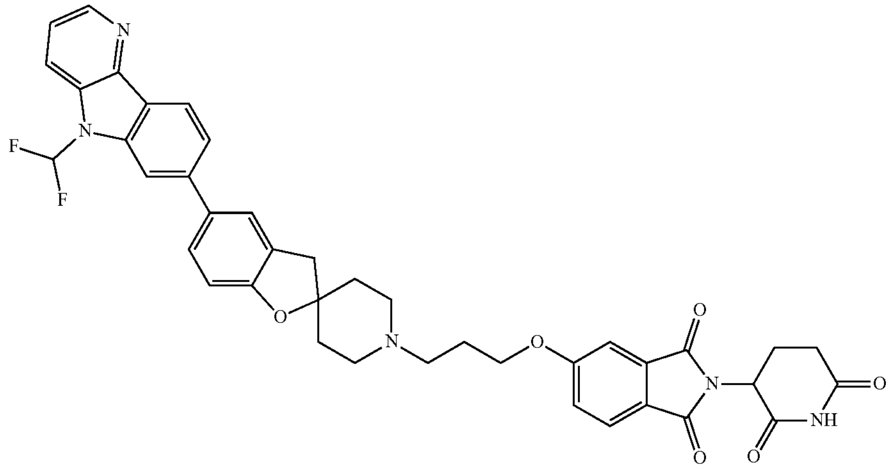 [SMILES: O=C1CCC(N2C(=O)c3ccc(OCCCN4CCC5(CC4)Cc4cc(-c6ccc7c8ncccc8n(C(F)F)c7c6)ccc4O5)cc3C2=O)C(=O)N1] | 5-(3-(5-(5-(difluoromethyl)-5H-pyrido[4,3-b]indol-7-yl)-3H-spiro[benzofuran-2,4'-piperidin]-1'-yl)propoxy)-2-(2,6-dioxopiperidin-3-yl)isoindoline-1,3-dione | 720.1 | $^1$H NMR (400 MHz, DMSO-$d_6$) δ: 11.11 (s, 1 H), 9.45 (s, 1 H), 9.43 (s, 1 H), 8.60-8.52 (m, 3 H), 8.32-8.26 (m, 1 H), 8.07 (s, 1 H), 7.85-7.83 (m, 2 H), 7.81-7.79 (m, 2 H), 7.64 (s, 1 H), 7.45-7.38 (m, 3 H), 6.89 (d, J = 8 Hz, 1 H), 5.14-5.10 (m, 1 H), 3.09 (s, 3 H), 2.95-2.85 (m, 2 H), 2.61-2.55 (m, 2 H), 1.97-1.81 (m, 7 H). |

TABLE 1-continued

| | | | | | |
|---|---|---|---|---|---|
| 666 | 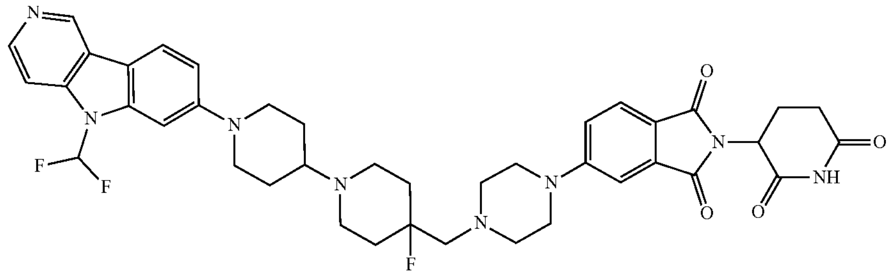 [SMILES: O=C1CCC(N2C(=O)c3ccc(N4CCN(CC5(F)CCN(C6CCN(c7ccc8c9cnccc9n(C(F)F)c8c7)CC6)CC5)CC4)cc3C2=O)C(=O)N1] | 5-(4-((1'-(5-(difluoromethyl)-5H-pyrido[4,3-b]indol-7-yl)-4-fluoro-[1,4'-bipiperidin]-4-yl)methyl)piperazin-1-yl)-2-(2,6-dioxopiperidin-3-yl)isoindoline-1,3-dione | | 757.2 | 1H NMR (400 MHz, DMSO-d6, ppm): δ 11.07 (s, 1 H), 9.24 (s, 1 H), 8.46-8.38 (m, 2 H), 8.06 (d, J = 8.8 Hz, 1 H), 7.68-7.66 (m, 2 H), 7.33-7.31 (m, 2 H), 7.23 (s, 1 H), 7.13 (d, J = 8.8 Hz, 1 H), 5.09 (dd, J = 4.8 Hz, 12.4 Hz 1 H), 3.92 (d, J = 3.6 Hz, 1 H), 3.43 (s, 4 H), 3.29 (s, 8 H), 2.67-2.61 (m, 2 H), 2.1 (s, 1 H), 1.88-1.85 (m, 4 H), 1.24-1.23 (m, 3 H) |
| 667 | 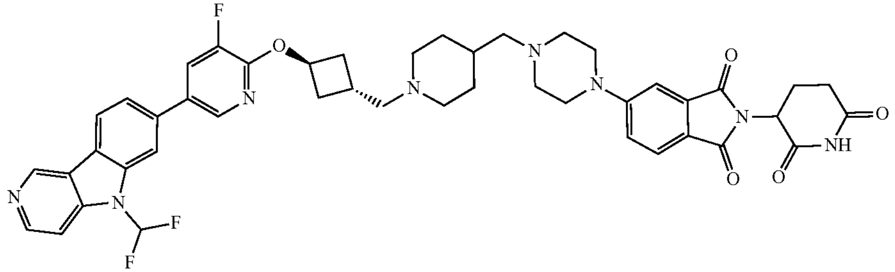 [SMILES: O=C1CCC(N2C(=O)c3ccc(N4CCN(CC5CCN(C[C@H]6C[C@H](Oc7ncc(-c8ccc9c%10cnccc%10n(C(F)F)c9c8)cc7F)C6)CC5)CC4)cc3C2=O)C(=O)N1] | 5-(4-((1-(((1r,3r)-3-((5-(5-(difluoromehtyl)-5H-pyrido[4,3-b]indol-7-yl)-3-fluoropyridin-2-yl)oxy)cyclobutyl) methyl)piperidin-4-yl)methyl)piperazin-1-yl)-2-(2,6-dioxopiperidin-3-yl) isoindoline-1,3-dione | A | 835.2 | $^1$H NMR (400 MHz, DMSO-$d_6$) δ: 11.08 (s, 1H), 9.49 (s, 1H), 8.61 (d, J = 5.6 Hz, 1H), 8.51-8.31 (m, 3H), 8.24 (s, 2H), 8.22-8.15 (m, 2H), 7.84-7.76 (m, 2H), 7.67 (d, J = 8.4 Hz, 1H), 7.32 (d, J = 1.6 Hz, 1H), 7.27-7.19 (m, 1H), 5.38-5.15 (m, 1H), 5.10-5.03 (m, 1H), 3.42 (s, 4H), 3.01-2.87 (m, 3H), 2.65-2.56 (m, 4H), 2.45 (s, 4H), 2.35-2.23 (m, 3H), 2.21-2.08 (m, 4H), 2.05-1.97 (m, 1H), 1.90-1.78 (m, 1H), 1.71 (d, J = 12.4 Hz, 2H), 1.60-1.49 (m, 1H), 1.22-1.08 (m, 2H) |
| 668 | 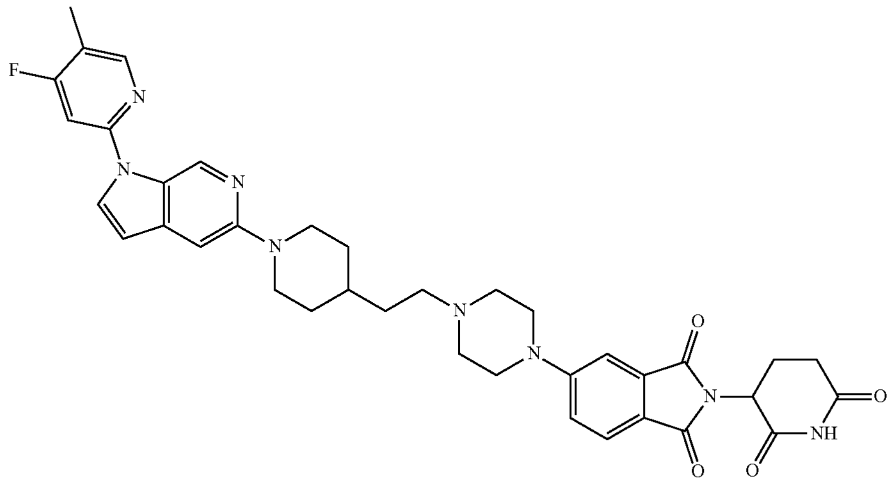 [SMILES: Cc1cnc(-n2ccc3cc(N4CCC(CCN5CCN(c6ccc7c(c6)C(=O)N(C6CCC(=O)NC6=O)C7=O)CC5)CC4)ncc32)cc1F] | 2-(2,6-dioxopiperidin-3-yl)-5-(4-(2-(1-(1-(4-fluoro-5-methylpyridin-2-yl)-1H-pyrrolo[2,3-c]pyridin-5-yl)piperidin-4-yl)ethyl)piperazin-1-yl)isoindoline-1,3-dione | | 679.2 | $^1$H NMR (400 MHz, DMSO-$d_6$) δ: 11.09 (s, 1H), 9.41 (s, 1H), 8.46 (d, J = 10.8 Hz, 1H), 8.17 (d, J = 3.6 Hz, 2H), 7.80-7.63 (m, 2H), 7.35 (d, J = 1.6 Hz, 1H), 7.31-7.18 (m, 1H), 6.93 (s, 1H), 6.62 (d, J = 3.6 Hz, 1H), 5.14-5.03 (m, 1H), 4.23 (d, J = 12.8 Hz, 2H), 3.44 (d, J = 4.4 Hz, 8H), 2.94-2.86 (m, 1H), 2.78-2.69 (m, 2H), 2.64-2.56 (m, 2H), 2.44-2.39 (m, 2H), 2.27 (s, 3H), 2.08-1.97 (m, 1H), 1.78 (d, J = 10.8 Hz, 2H), 1.59-1.43 (m, 3H), 1.30-1.17 (m, 2H) |

TABLE 1-continued

| | | | | |
|---|---|---|---|---|
| 669 | 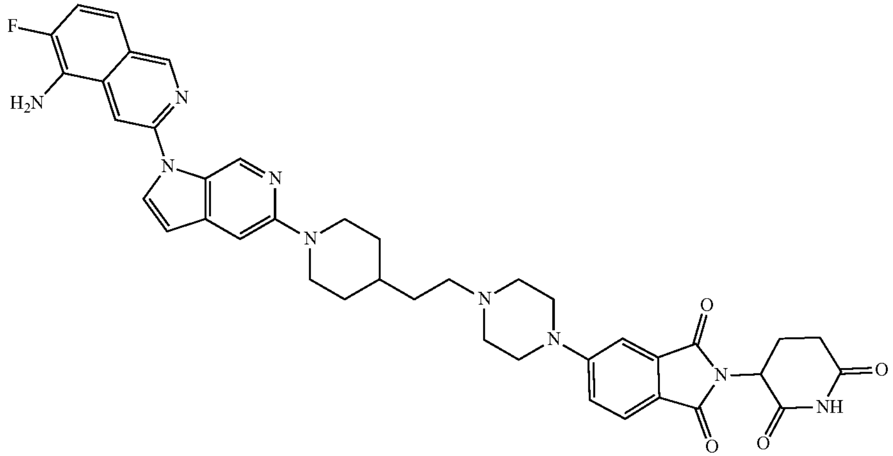 [SMILES: Nc1c(F)ccc2cnc(-n3ccc4cc(N5CCC(CCN6CCN(c7ccc8c(c7)C(=O)N(C7CCC(=O)NC7=O)C8=O)CC6)CC5)ncc43)cc12] | 5-(4-(2-(1-(1-(5-amino-6-fluoroisoquinolin-3-yl)-1H-pyrrolo[2,3-c]pyridin-5-yl)piperidin-4-yl)ethyl)piperazin-1-yl)-2-(2,6-dioxopiperidin-3-yl)isoindoline-1,3-dione | 730.4 | $^1$H NMR (400 MHz, DMSO-d6) δ: 11.09 (s, 1H), 9.39 (s, 1H), 9.21 (s, 1H), 8.28 (s, 1H), 8.22 (d, J = 3.2 Hz, 1H), 8.15 (s, 1H), 7.68 (d, J = 8.8 Hz, 1H), 7.42 (s, 1H), 7.40 (s, 1H), 7.35 (s, 1H), 7.30-7.23 (m, 1H), 6.96 (s, 1H), 6.67 (d, J = 3.2 Hz, 1H), 6.11-5.91 (m, 2H), 5.19-4.98 (m, 1H), 4.24 (d, J = 12.8 Hz, 2H), 3.45 (s, 8H), 2.96-2.82 (m, 1H), 2.78-2.69 (m, 2H), 2.64-2.54 (m, 2H), 2.40 (d, J = 6.4 Hz, 2H), 2.08-1.97 (m, 1H), 1.79 (d, J = 12.8 Hz, 2H), 1.59-1.43 (m, 3H), 1.32-1.19 (m, 2H) |
| 670 | 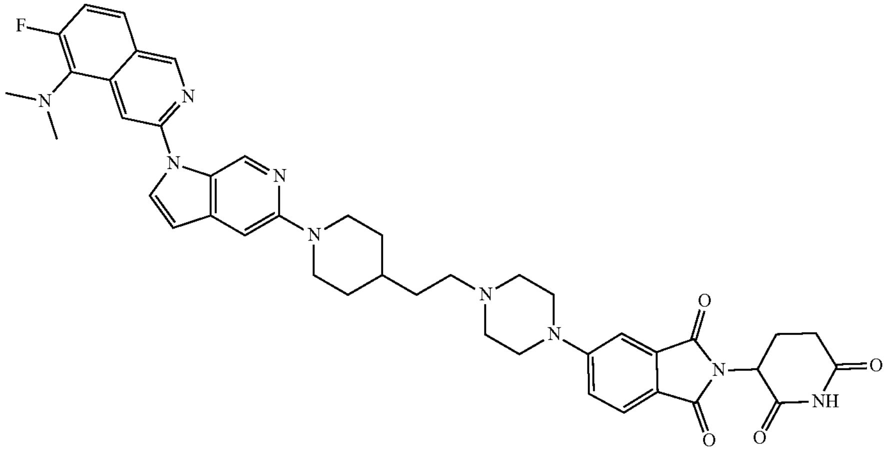 [SMILES: CN(C)c1c(F)ccc2cnc(-n3ccc4cc(N5CCC(CCN6CCN(c7ccc8c(c7)C(=O)N(C7CCC(=O)NC7=O)C8=O)CC6)CC5)ncc43)cc12] | 5-(4-(2-(1-(1-(5-(dimethylamino)-6-fluoroisoquinolin-3-yl)-1H-pyrrolo[2,3-c]pyridin-5-yl)piperidin-4-yl)ethyl)piperazin-1-yl)-2-(2,6-dioxopiperidin-3-yl)isoindoline-1,3-dione | 758.4 | $^1$H NMR (400 MHz, DMSO-$d_6$) δ: 11.08 (s, 1H), 9.34 (s, 1H), 9.24 (s, 1H), 8.24 (d, J = 3.2 Hz, 1H), 8.21 (s, 1H), 8.13 (s, 1H), 8.07-7.98 (m, 1H), 7.67 (d, J = 8.4 Hz, 1H), 7.53-7.41 (m, 1H), 7.33 (d, J = 1.6 Hz, 1H), 7.29-7.22 (m, 1H), 6.97 (s, 1H), 6.65 (d, J = 3.2 Hz, 1H), 5.15-4.96 (m, 1H), 4.23 (d, J = 12.4 Hz, 2H), 3.43 (d, J = 4.4 Hz, 8H), 2.95 (d, J = 2.4 Hz, 6H), 2.90-2.82 (m, 1H), 2.73 (t, J = 11.2 Hz, 2H), 2.63-2.53 (m, 2H), 2.40 (t, J = 7.2 Hz, 2H), 2.06-1.97 (m, 1H), 1.82-1.74 (m, 2H), 1.60-1.49 (m, 1H), 1.49-1.39 (m, 2H), 1.30-1.19 (m, 2H) |

TABLE 1-continued

| | | | | |
|---|---|---|---|---|
| 671 | 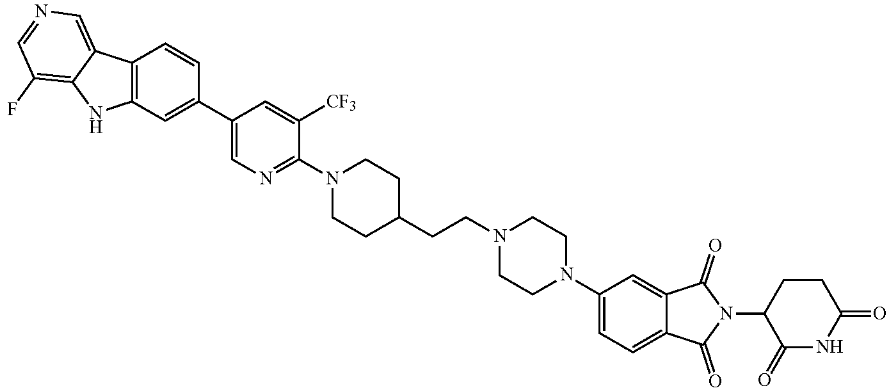 [SMILES: O=C1CCC(N2C(=O)c3ccc(N4CCN(CCC5CCN(c6ncc(-c7ccc8c(c7)[nH]c7c(F)cncc78)cc6C(F)(F)F)CC5)CC4)cc3C2=O)C(=O)N1] | 2-(2,6-dioxopiperidin-3-yl)-5-(4-(2-(1-(5-(4-fluoro-5H-pyrido[4,3-b]indol-7-yl)-3-(trifluoromethyl)pyridin-2-yl)piperidin-4-yl)ethyl)piperazin-1-yl)isoindoline-1,3-dione | 783.2 | $^1$H NMR (400 MHz, DMSO-d6) δ: 12.43 (s, 1H), 11.08 (s, 1H), 9.25 (d, J = 2.0 Hz, 1H), 8.91 (d, J = 2.0 Hz, 1H), 8.46 (d, J = 2.8 Hz, 1H), 8.40-8.31 (m, 2H), 7.85 (s, 1H), 7.69 (dd, J = 5.6, 8.3 Hz, 2H), 7.36-7.33 (m, 1H), 7.28-7.23 (m, 1H), 5.07 (dd, J = 5.2, 12.8 Hz, 1H), 3.64 (d, J = 12.4 Hz, 2H), 3.45 (s, 4H), 3.00-2.82 (m, 3H), 2.63-2.54 (m, 4H), 2.44-2.36 (m, 2H), 2.02 (td, J = 5.2, 10.3 Hz, 1H), 1.90-1.75 (m, 2H), 1.63-1.14 (m, 7H) |
| 672 | 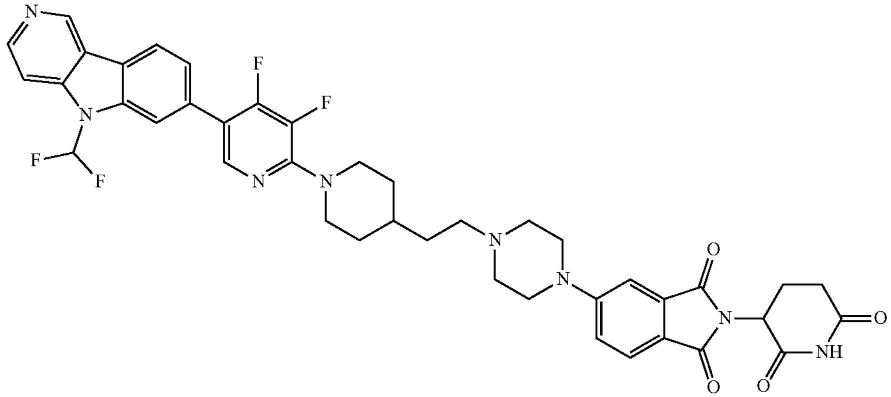 [SMILES: O=C1CCC(N2C(=O)c3ccc(N4CCN(CCC5CCN(c6ncc(-c7ccc8c9cnccc9n(C(F)F)c8c7)c(F)c6F)CC5)CC4)cc3C2=O)C(=O)N1] | 5-(4-(2-(1-(5-(5-(difluoromethyl)-5H-pyrido[4,3-b]indol-7-yl)-3,4-difluoropyridin-2-yl)piperidin-4-yl)ethyl)piperazin-1-yl)-2-(2,6-dioxopiperidin-3-yl)isoindoline-1,3-dione | | |

TABLE 1-continued

| | | | | | |
|---|---|---|---|---|---|
| 673 | 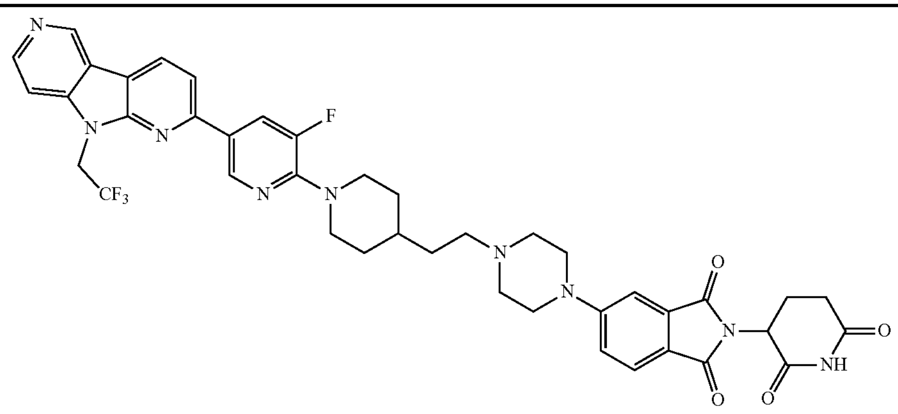 | 2-(2,6-dioxopiperidin-3-yl)-5-(4-(2-(1-(3-fluoro-5-(9-(2,2,2-trifluoroethyl)-9H-pyrrolo[2,3-b:4,5-c']dipyridin-2-yl)pyridin-2-yl)piperidin-4-yl)ethyl)piperazin-1-yl)isoindoline-1,3-dione | A | 798.2 | 1H NMR (400 MHz, DMSO-d6) δ: 1.22-1.32 (m, 2 H), 1.47 (d, J = 8.4 Hz, 2 H), 1.64 (s, 1 H), 1.81 (d, J = 11.6 Hz, 2 H), 2.00-2.07 (m, 1 H), 2.61 (s, 2 H), 2.73-3.04 (m, 5 H), 3.45 (s, 8 H), 4.19 (d, J = 13.2 Hz, 2 H), 5.08 (d, J = 12.8, 5.6 Hz, 1 H), 5.47-5.64 (m, 2 H), 7.27 (d, J = 8.8, 2.0 Hz, 1 H), 7.35 (s, 1 H), 7.69 (d, J = 8.4 Hz, 1 H), 7.83 (d, J = 5.6 Hz, 1 H), 8.05 (d, J = 8.4 Hz, 1 H), 8.29-8.34 (m, 1 H), 8.37 (d, J = 2.0 Hz, 1 H), 8.62 (d, J = 6.0 Hz, 1 H), 8.74 (d, J = 8.0 Hz, 1 H), 8.96 (s, 1 H), 9.43 (s, 1 H) 11.09 (s, 1 H) |
| 674 | 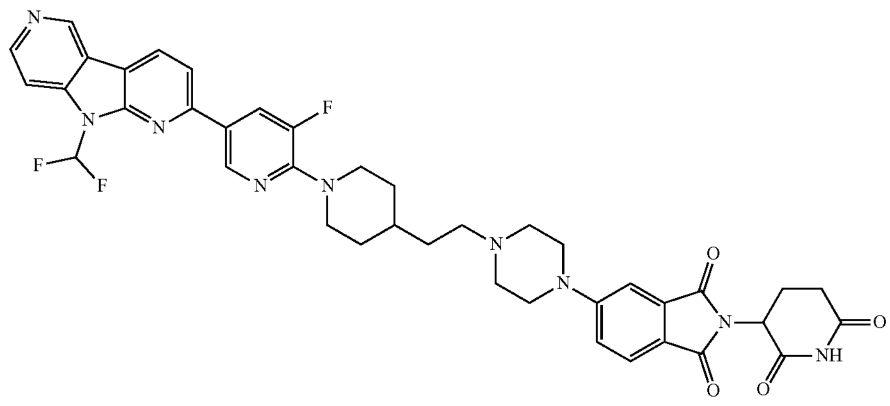 [SMILES: O=C1CCC(N2C(=O)c3ccc(N4CCN(CCC5CCN(c6ncc(-c7ccc8c9cnccc9n(C(F)F)c8n7)cc6F)CC5)CC4)cc3C2=O)C(=O)N1] | 5-(4-(2-(1-(5-(9-(difluoromethyl)-9H-pyrrolo[2,3-b:4,5-c']dipyridin-2-yl)-3-fluoropyridin-2-yl)piperidin-4-yl)ethyl)piperazin-1-yl)-2-(2,6-dioxopiperidin-3-yl)isoindoline-1,3-dione | A | 766.3 | 1H NMR (400 MHz, DMSO-d6) δ: 1.33 (d, J = 9.6 Hz, 2 H), 1.69 (s, 3 H), 1.82 (d, J = 12.0 Hz, 2 H), 2.02-2.08 (m, 1 H), 2.59 (s, 2 H), 2.82-3.07 (m, 3 H), 3.26 (s, 8 H), 4.24 (d, J = 12.8 Hz, 4 H), 5.11 (d, J = 13.2, 4.8 Hz, 1 H), 7.38 (d, J = 8.4 Hz, 1 H), 7.51 (s, 1 H), 7.78 (d, J = 8.4 Hz, 1 H), 8.07 (d, J = 6.0 Hz, 1 H), 8.24 (d, J = 8.4 Hz, 1 H), 8.47 (d, J = 14.0 Hz, 1 H), 8.56-8.91 (m, 3 H), 9.01 (s, 1 H), 9.69 (s, 1 H), 11.01 (s, 1 H) |

TABLE 1-continued

| | | | | | |
|---|---|---|---|---|---|
| 675 | 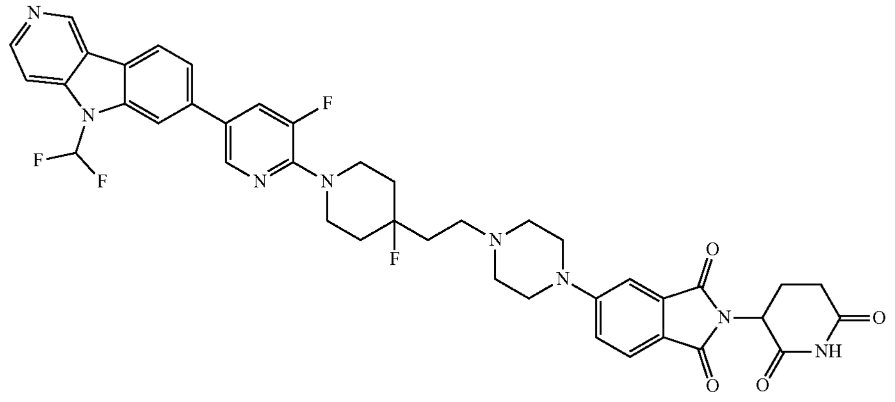 [SMILES: O=C1CCC(N2C(=O)c3ccc(N4CCN(CCC5(F)CCN(c6ncc(-c7ccc8c9cnccc9n(C(F)F)c8c7)cc6F)CC5)CC4)cc3C2=O)C(=O)N1] | 5-(4-(2-(1-(5-(5-(difluoromethyl)-5H-pyrido[4,3-b]indol-7-yl)-3-fluoropyridin-2-yl)-4-fluoropiperidin-4-yl)ethyl)piperazin-1-yl)-2-(2,6-dioxopiperidin-3-yl)isoindoline-1,3-dione | | 783.2 | $^1$H NMR (400 MHz, DMSO-$d_6$) δ: 11.07 (s, 1H), 9.48 (s, 1H), 8.62-8.53 (m, 3H), 8.48 (s, 1H), 8.39 (d, J = 8.8 Hz, 2H), 8.20 (s, 2H), 8.05 (s, 1H), 7.81 (d, J = 6.4 Hz, 2H), 7.67-7.65 (d, J = 6.4 Hz, 2H), 7.34 (s, 1H), 7.26 (s, 1H), 5.09-5.04 (m, 1H), 3.96 (d, J = 12.0 Hz, 2H), 3.45-3.41 (m, 6H), 3.32-3.31 (m, 2H), 2.96-2.93 (m, 2H), 2.53-2.52 (m, 6H), 2.32-1.92 (m, 6H) |
| 676 | 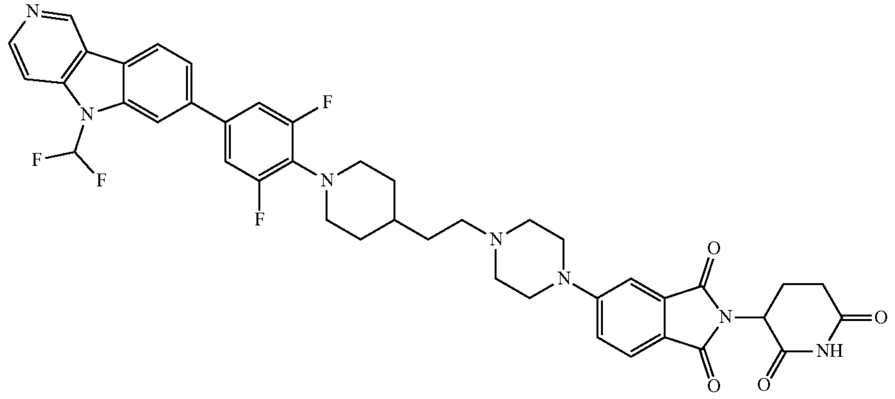 [SMILES: O=C1CCC(N2C(=O)c3ccc(N4CCN(CCC5CCN(c6c(F)cc(-c7ccc8c9cnccc9n(C(F)F)c8c7)cc6F)CC5)CC4)cc3C2=O)C(=O)N1] | 5-(4-(2-(1-(4-(9-(difluoromethyl)-9H-pyrrolo[2,3-b:4,5-c']dipyridin-2-yl)-2,6-difluorophenyl)piperidin-4-yl)ethyl)piperazin-1-yl)-2-(2,6-dioxopiperidin-3-yl)isoindoline-1,3-dione | A | 783.2 | 1H NMR (400 MHz, DMSO-d6) δ: 1.30-1.55 (m, 6 H), 1.78 (d, J = 11.6 Hz, 2 H), 1.88-2.09 (m, 2 H), 2.42 (s, 2 H), 2.81-2.97 (m, 2 H), 3.09 (t, J = 11.2 Hz, 2 H), 3.45 (d, J = 5.4 Hz, 8 H), 4.38 (s, 1 H), 5.08 (d, J = 13.2, 5.6 Hz, 1 H), 7.27 (d, J = 8.4 Hz, 1 H), 7.35 (s, 1 H), 7.69 (d, J = 8.8 Hz, 1 H), 7.82 (d, J = 5.6 Hz, 1 H), 8.05-8.22 (m, 3 H), 8.29-8.55 (m, 1 H), 8.64-8.85 (m, 3 H), 9.52 (s, 1 H), 11.10 (s, 1 H) |

TABLE 1-continued

| | | | | | |
|---|---|---|---|---|---|
| 677 | 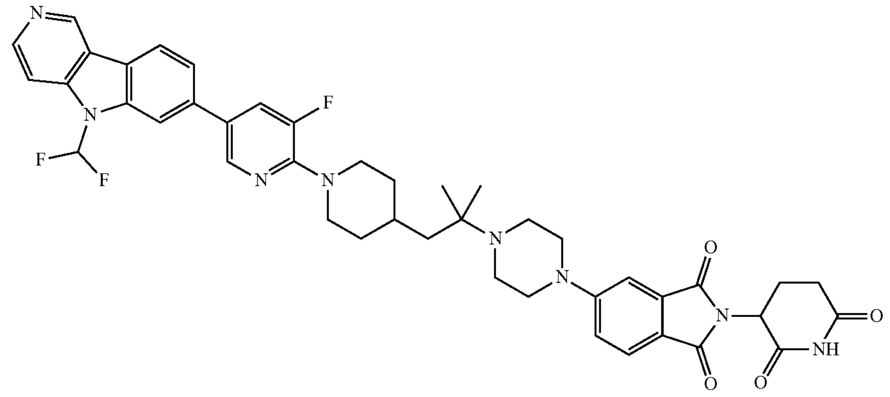 [SMILES: CC(C)(CC1CCN(c2ncc(-c3ccc4c5cnccc5n(C(F)F)c4c3)cc2F)CC1)N1CCN(c2ccc3c(c2)C(=O)N(C2CCC(=O)NC2=O)C3=O)CC1] | 5-(4-(1-(1-(5-(5-(difluoromethyl)-5H-pyrido[4,3-b]indol-7-yl)-3-fluoropyridin-2-yl)piperidin-4-yl)-2-methylpropan-2-yl)piperazin-1-yl)-2-(2,6-dioxopiperidin-3-yl)isoindoline-1,3-dione | A | 793.2 | $^1$H NMR (400 MHz, DMSO-$d_6$) δ: 11.08 (s, 1H), 9.47 (s, 1H), 8.64-8.58 (m, 1H), 8.51-8.47 (m, 1H), 8.40-8.32 (m, 1H), 8.19 (s, 2H), 8.01-7.94 (m, 1H), 7.80 (d, J = 6.8 Hz, 2H), 7.69-7.63 (m, 1H), 7.35-7.14 (m, 3H), 5.07 (dd, J = 5.4, 12.8 Hz, 1H), 4.09-3.97 (m, 4H), 2.97 (s, 2H), 2.91-2.85 (m, 3H), 2.64 (s, 1H), 2.05-1.98 (m, 2H), 1.93-1.85 (m, 3H), 1.84-1.74 (m, 2H), 1.45-1.23 (m, 6H), 1.06-1.02 (m, 6H) |
| 678 | 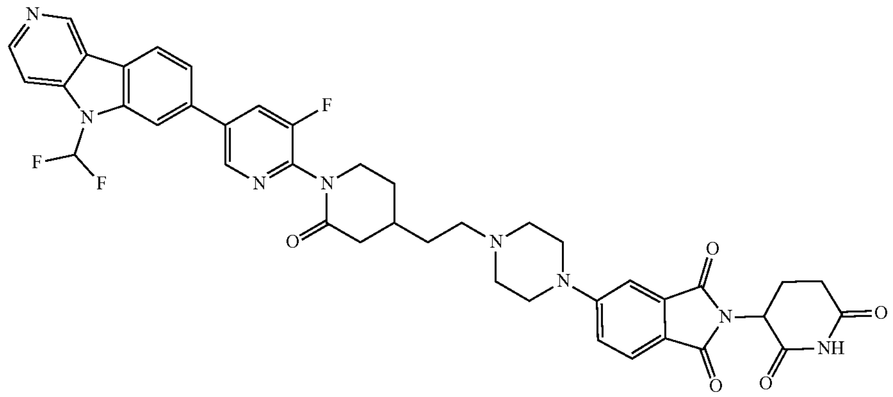 [SMILES: O=C1CCC(N2C(=O)c3ccc(N4CCN(CCC5CCN(c6ncc(-c7ccc8c9cnccc9n(C(F)F)c8c7)cc6F)C(=O)C5)CC4)cc3C2=O)C(=O)N1] | 5-(4-(2-(1-(5-(5-(difluoromethyl)-5H-pyrido[4,3-b]indol-7-yl)-3-fluoropyridin-2-yl)-2-oxopiperidin-4-yl)ethyl)piperazin-1-yl)-2-(2,6-dioxopiperidin-3-yl)isoindoline-1,3-dione | | 779.1 | $^1$H NMR: (400 MHz, DMSO-d6) δ: 11.15-11.00 (m, 1H), 9.52 (s, 1H), 8.81 (s, 1H), 8.68-8.24 (m, 5H), 7.97-7.80 (m, 2H), 7.68 (d, J = 8.4 Hz, 1H), 7.41-7.19 (m, 2H), 5.13-5.02 (m, 1H), 3.86-3.74 (m, 2H), 3.51-3.40 (m, 6H), 2.96-2.81 (m, 1H), 2.64-2.56 (m, 3H), 2.46-2.40 (m, 3H), 2.29-2.20 (m, 1H), 2.16-1.93 (m, 4H), 1.74-1.49 (m, 3H) |

TABLE 1-continued

| | | | | | |
|---|---|---|---|---|---|
| 679 | 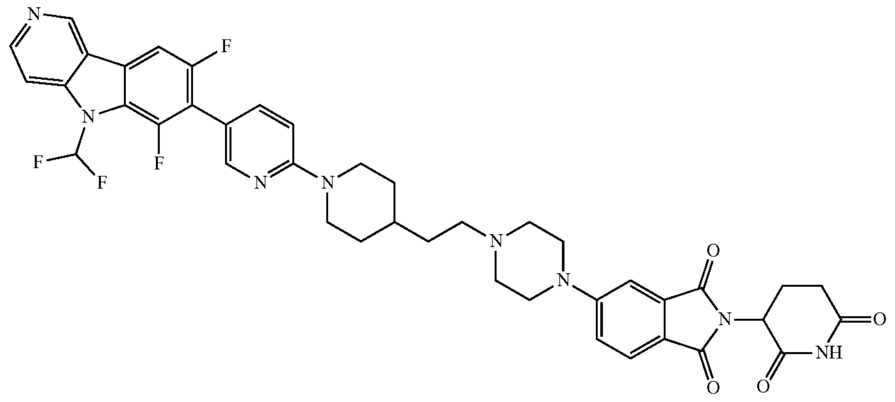 [SMILES: O=C1CCC(N2C(=O)c3ccc(N4CCN(CCC5CCN(c6ccc(-c7c(F)cc8c9cnccc9n(C(F)F)c8c7F)cn6)CC5)CC4)cc3C2=O)C(=O)N1] | 5-(4-(2-(1-(5-(5-(difluoromethyl)-6,8-difluoro-5H-pyrido[4,3-b]indol-7-yl)pyridin-2-yl)piperidin-4-yl)ethyl)piperazin-1-yl)-2-(2,6-dioxopiperidin-3-yl)isoindoline-1,3-dione | A | 783.2 | $^1$H NMR (400 MHz, DMSO-$d_6$) δ: 11.09 (s, 1H), 9.53 (s, 1H), 8.68 (d, J = 5.6 Hz, 1H), 8.53-8.28 (m, 1H), 8.27-8.23 (m, 2H), 7.93 (d, J = 6.0 Hz, 1H), 7.73-7.62 (m, 2H), 7.34 (d, 1.6 Hz, 1H), 7.30-7.21 (m, 1H), 6.98 (d, J = 9.2 Hz, 1H), 5.18-5.00 (m, 1H), 4.39 (d, J = 12.8 Hz, 2H), 3.47-3.42 (m, 8H), 2.94-2.85 (m, 3H), 2.63-2.54 (m, 2H), 2.40 (t, J = 7.2 Hz, 2H), 2.05-1.98 (m, 1H), 1.79 (d, J = 10.4 Hz, 2H), 1.68-1.55 (m, 1H), 1.50-1.41 (m, 2H), 1.25-1.12 (m, 2H) |
| 680 | 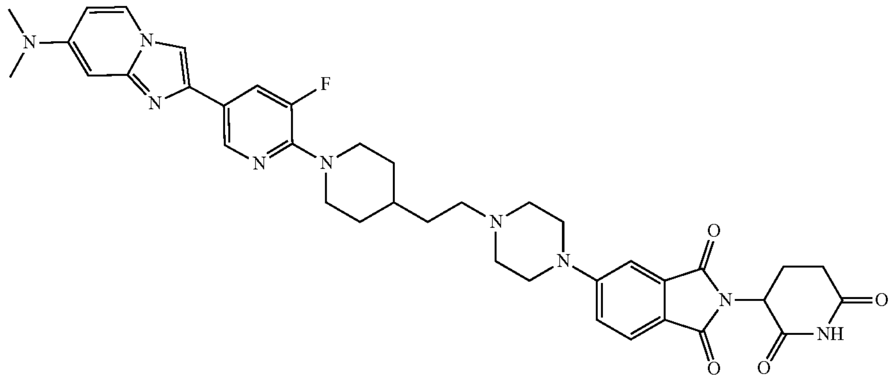 [SMILES: CN(C)c1ccn2cc(-c3cnc(N4CCC(CCN5CCN(c6ccc7c(c6)C(=O)N(C6CCC(=O)NC6=O)C7=O)CC5)CC4)c(F)c3)nc2c1] | 5-(4-(2-(1-(5-(7-(dimethylamino)imidazo[1,2-a]pyridin-2-yl)-3-fluoropyridin-2-yl)piperidin-4-yl)ethyl)piperazin-1-yl)-2-(2,6-dioxopiperidin-3-yl)isoindoline-1,3-dione | A | 708.2 | $^1$H NMR (400 MHz, DMSO-d6) δ = 11.08 (s, 1H), 8.50 (d, J = 1.6 Hz, 1H), 8.25 (d, J = 7.2 Hz, 1H), 8.00 (s, 1H), 7.85 (d, J = 14.8 Hz, 1H), 7.68 (d, J = 7.6 Hz, 1H), 7.34 (s, 1H), 7.26 (d, J = 8.0 Hz, 1H), 6.70 (d, J = 7.6 Hz, 1H), 6.42 (s, 1H), 5.07 (dd, J = 4.4, 12.8 Hz, 1H), 4.00 (d, J = 12.0 Hz, 2H), 3.45 (s, 4H), 2.98 (d, J = 1.2 Hz, 6H), 2.86 (t, J = 11.2 Hz, 4H), 2.60 (s, 2H), 2.42 (d, J = 6.0 Hz, 2H), 2.09-1.93 (m, 2H), 1.78 (d, J = 12.4 Hz, 2H), 1.63-1.41 (m, 4H), 1.36-1.20 (m, 3H) |
| 681 | 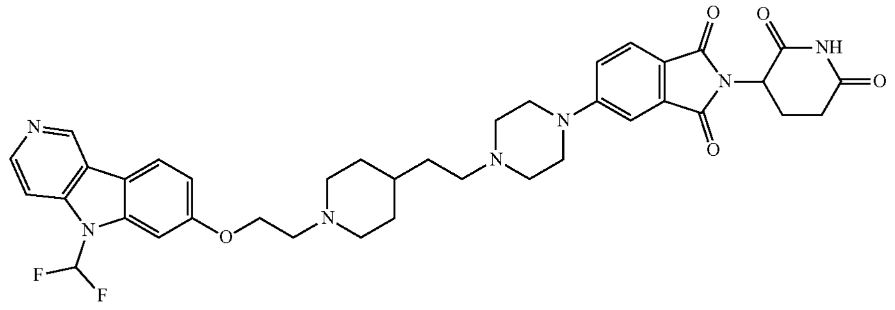 [SMILES: O=C1CCC(N2C(=O)c3ccc(N4CCN(CCC5CCN(CCOc6ccc7c8cnccc8n(C(F)F)c7c6)CC5)CC4)cc3C2=O)C(=O)N1] | 5-(4-(2-(1-(2-((5-(difluoromethyl)-5H-pyrido[4,3-b]indol-7-yl)oxy)ethyl)piperidin-4-yl)ethyl)piperazin-1-yl)-2-(2,6-dioxopiperidin-3-yl)isoindoline-1,3-dione | | 714.2 | |

TABLE 1-continued

| | | | | | |
|---|---|---|---|---|---|
| 682 | 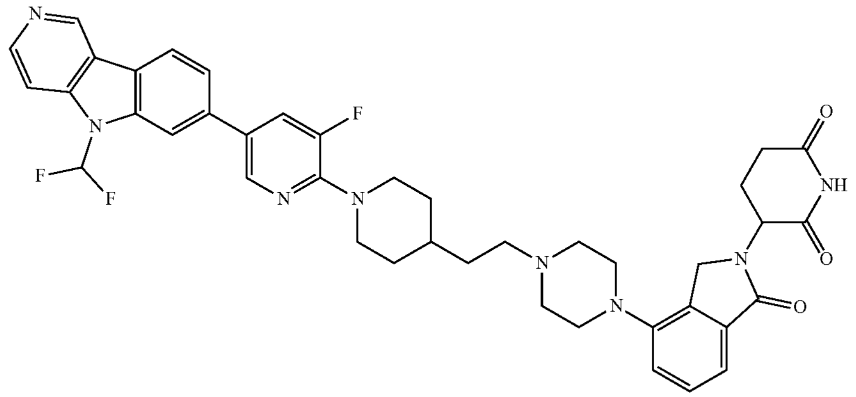 [SMILES: O=C1CCC(N2Cc3c(cccc3N3CCN(CCC4CCN(c5ncc(-c6ccc7c8cnccc8n(C(F)F)c7c6)cc5F)CC4)CC3)C2=O)C(=O)N1] | 3-(4-(4-(2-(1-(5-(5-(difluoromethyl)-5H-pyrido[4,3-b]indol-7-yl)-3-fluoropyridin-2-yl)piperidin-4-yl)ethyl)piperazin-1-yl)-1-oxoisoindolin-2-yl)piperidine-2,6-dione | A | 751.2 | $^1$H NMR (400 MHz, DMSO-$d_6$) δ: 11.02 (s, 1 H), 9.50 (s, 1 H), 8.33-8.67 (m, 4 H), 8.22 (s, 1 H), 8.02 (m, 1 H), 7.82 (d, J = 6.8 Hz, 2 H), 7.44-7.52 (m, 1 H), 7.38 (d, J = 6.4 Hz, 1 H), 7.17-7.27 (m, 1 H), 5.15 (m, 1 H), 4.43-4.53 (m, 1 H), 4.32 (d, J = 17.2 Hz, 1 H), 4.12 (d, J = 12.8 Hz, 2 H), 3.05-3.26 (m, 5 H), 2.95 (t, J = 12.4 Hz, 4 H), 2.62 (d, J = 17.6 Hz, 2 H), 2.38-2.48 (m, 3 H), 2.03 (m, 1 H), 1.82 (d, J = 12.4 Hz, 2 H), 1.52-1.73 (m, 3 H), 1.17-1.39 (m, 3 H) |
| 683 | 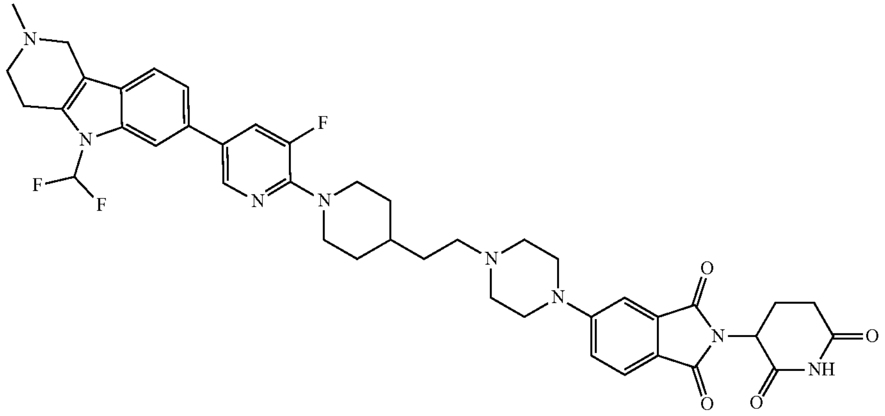 [SMILES: CN1CCc2c(c3ccc(-c4cnc(N5CCC(CCN6CCN(c7ccc8c(c7)C(=O)N(C7CCC(=O)NC7=O)C8=O)CC6)CC5)c(F)c4)cc3n2C(F)F)C1] | 5-(4-(2-(1-(5-(5-(difluoromethyl)-2-methyl-2,3,4,5-tetrahydro-1H-pyrido[4,3-b]indol-7-yl)-3-fluoropyridin-2-yl)piperidin-4-yl)ethyl)piperazin-1-yl)-2-(2,6-dioxopiperidin-3-yl)isoindoline-1,3-dione | | | |

TABLE 1-continued

| | | | | |
|---|---|---|---|---|
| 684 | 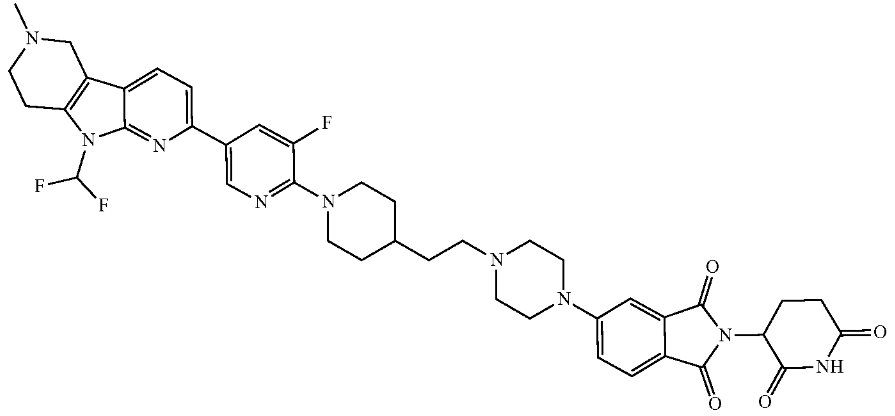 [SMILES: CN1CCc2c(c3ccc(-c4cnc(N5CCC(CCN6CCN(c7ccc8c(c7)C(=O)N(C7CCC(=O)NC7=O)C8=O)CC6)CC5)c(F)c4)nc3n2C(F)F)C1] | 5-(4-(2-(1-(5-(9-(difluoromethyl)-6-methyl-6,7,8,9-tetrahydro-5H-pyrrolo[2,3-b:4,5-c']dipyridin-2-yl)-3-fluoropyridin-2-yl)piperidin-4-yl)ethyl)piperazin-1-yl)-2-(2,6-dioxopiperidin-3-yl)isoindoline-1,3-dione | | |
| 685 | 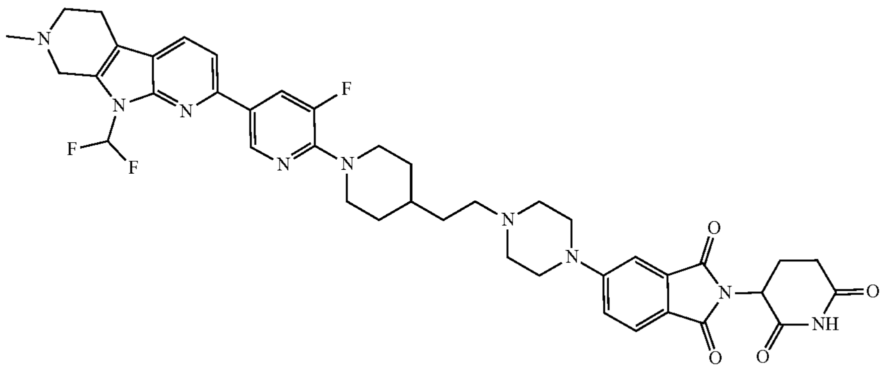 [SMILES: CN1CCc2c(n(C(F)F)c3nc(-c4cnc(N5CCC(CCN6CCN(c7ccc8c(c7)C(=O)N(C7CCC(=O)NC7=O)C8=O)CC6)CC5)c(F)c4)ccc23)C1] | 5-(4-(2-(1-(5-(9-(difluoromethyl)-2-methyl-2,3,4,9-tetrahydro-1H-pyrido[3,4-b]indol-7-yl)-3-fluoropyridin-2-yl)piperidin-4-yl)ethyl)piperazin-1-yl)-2-(2,6-dioxopiperidin-3-yl)isoindoline-1,3-dione | 783.4 | $^1$H NMR (400 MHz, DMSO-$d_6$) δ: 11.08 (s, 1 H), 8.44-8.37 (m, 1 H), 8.28-7.94 (m, 3 H), 7.94-7.84 (m, 1 H), 7.72-7.63 (d, J = 8.8 Hz 1 H), 7.56-7.51 (m, 2 H), 7.38-7.32 (m, 1 H), 7.30-7.22 (m, 1 H), 5.12-5.02 (m, 1 H), 4.12-3.98 (d, J = 13.6 Hz 2 H), 3.77-3.70 (d, J = 10.4 Hz 2 H), 3.50-3.38 (m, 5 H) 2.95-2.82 (m, 3 H), 2.80-2.69 (m, 4 H), 2.63-2.57 (m, 1 H), 2.52 (s, 4 H), 2.52-2.51 (m, 2 H), 2.46-2.48 (m, 3 H), 2.08-1.96 (m, 1 H), 1.83-1.73 (m, 2 H), 1.65-1.53 (m, 1 H), 1.50-1.41 (m, 2 H), 1.34-1.21 (m, 2 H) |

TABLE 1-continued
| | | | |
|---|---|---|---|
| 686 | 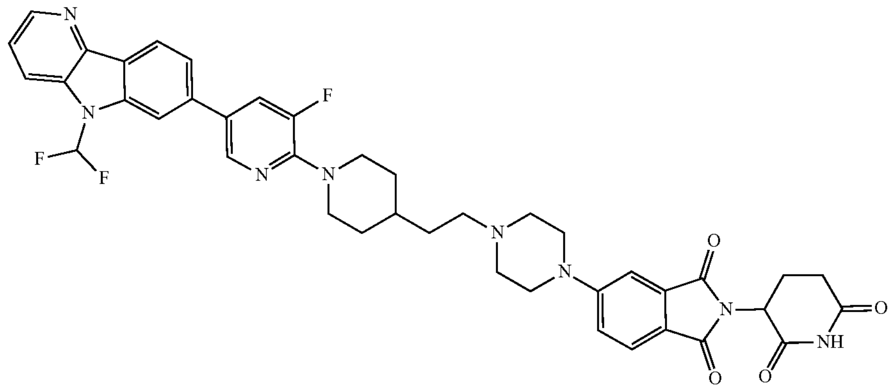 [SMILES: O=C1CCC(N2C(=O)c3ccc(N4CCN(CCC5CCN(c6ncc(-c7ccc8c9ncccc9n(C(F)F)c8c7)cc6F)CC5)CC4)cc3C2=O)C(=O)N1] | 5-(4-(2-(1-(5-(5-(difluoromethyl)-5H-pyrido[3,2-b]indol-7-yl)-3-fluoropyridin-2-yl)piperidin-4-yl)ethyl)piperazin-1-yl)-2-(2,6-dioxopiperidin-3-yl)isoindoline-1,3-dione | 765.2 |
| 687 | 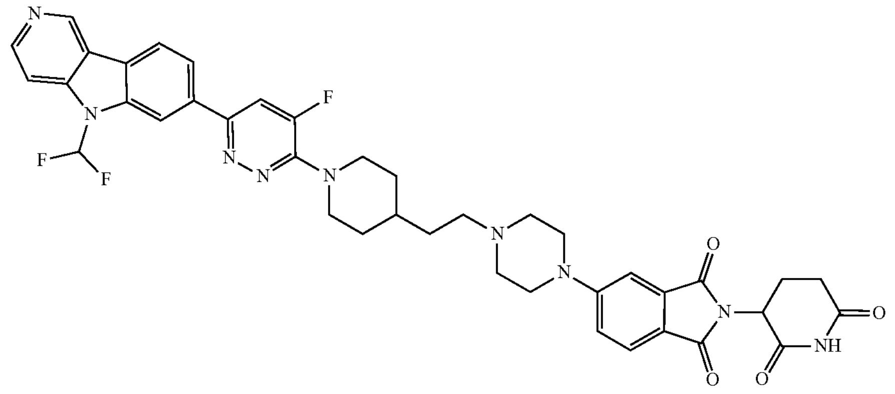 [SMILES: O=C1CCC(N2C(=O)c3ccc(N4CCN(CCC5CCN(c6nnc(-c7ccc8c9cnccc9n(C(F)F)c8c7)cc6F)CC5)CC4)cc3C2=O)C(=O)N1] | 5-(4-(2-(1-(6-(5-(difluoromethyl)-5H-pyrido[4,3-b]indol-7-yl)-4-fluoropyridazin-3-yl)piperidin-4-yl)ethyl)piperazin-1-yl)-2-(2,6-dioxopiperidin-3-yl)isoindoline-1,3-dione | |

TABLE 1-continued

| | | | |
|---|---|---|---|
| 600 | 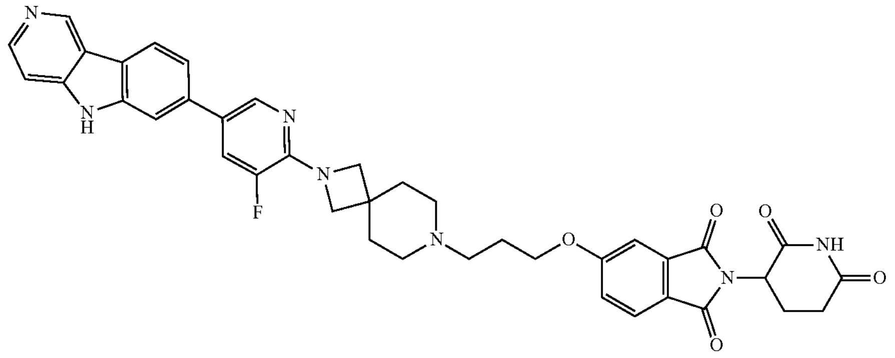 [SMILES: O=C1CCC(N2C(=O)c3ccc(OCCCN4CCC5(CC4)CN(c4ncc(-c6ccc7c(c6)[nH]c6ccncc67)cc4F)C5)cc3C2=O)C(=O)N1] | 2-(2,6-dioxopiperidin-3-yl)-5-(3-(2-(3-fluoro-5-(5H-pyrido[4,3-b]indol-7-yl)pyridin-2-yl)-2,7-diazaspiro[3.5]nonan-7-yl)propoxy)isoindoline-1,3-dione | 702.2 |
| 601 | 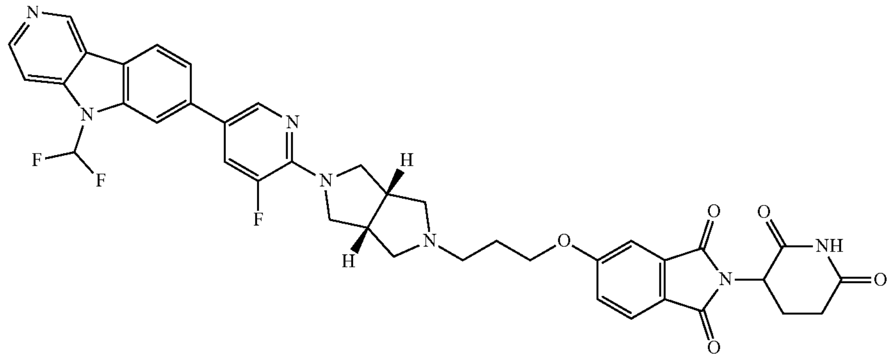 [SMILES: O=C1CCC(N2C(=O)c3ccc(OCCCN4C[C@@H]5CN(c6ncc(-c7ccc8c9cnccc9n(C(F)F)c8c7)cc6F)C[C@@H]5C4)cc3C2=O)C(=O)N1] | 5-(3-((3aR,6aS)-5-(5-(5-(difluoromethyl)-5H-pyrido[4,3-b]indol-7-yl)-3-fluoropyridin-2-yl)hexahydropyrrolo[3,4-c]pyrrol-2(1H)-yl)propoxy)-2-(2,6-dioxopiperidin-3-yl)isoindoline-1,3-dione | 738.1 |
| 602 | 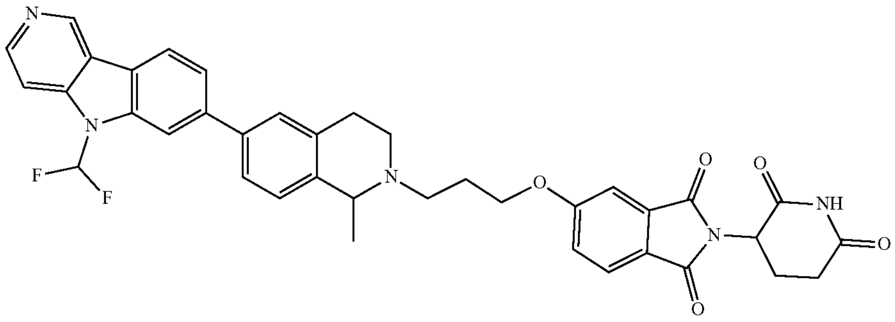 [SMILES: CC1c2ccc(-c3ccc4c5cnccc5n(C(F)F)c4c3)cc2CCN1CCCOc1ccc2c(c1)C(=O)N(C1CCC(=O)NC1=O)C2=O] | 5-(3-(6-(5-(difluoromethyl-5H-pyrido[4,3-b]indol-7-yl)-1-methyl-3,4-dihydroisoquinolin-2(1H)-yl)propoxy)-2-(2,6-dioxopiperidin-3-yl)isoindoline-1,3-dione | 678.2<br>678.2 |

TABLE 1-continued

| | | | | | |
|---|---|---|---|---|---|
| 603 | 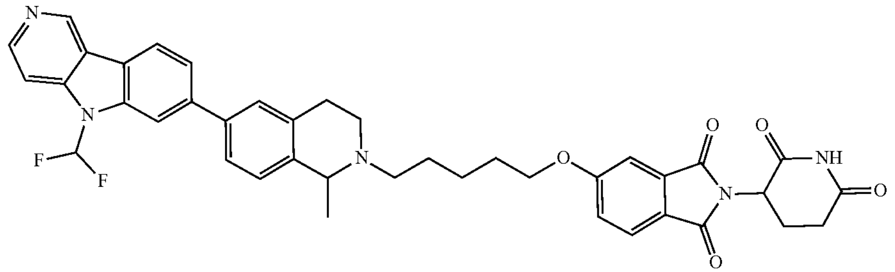 [SMILES: CC1c2ccc(-c3ccc4c5cnccc5n(C(F)F)c4c3)cc2CCN1CCCCCOc1ccc2c(c1)C(=O)N(C1CCC(=O)NC1=O)C2=O] | 5-((5-(6-(5-(difluoromethyl)-5H-pyrido[4,3-b]indol-7-yl)-1-methyl-3,4-dihydroisoquinolin-2(1H)-yl)pentyl)oxy)-2-(2,6-dioxopiperidin-3-yl)isoindoline-1,3-dione | B | 706.2<br>706.2 | |
| 604 | 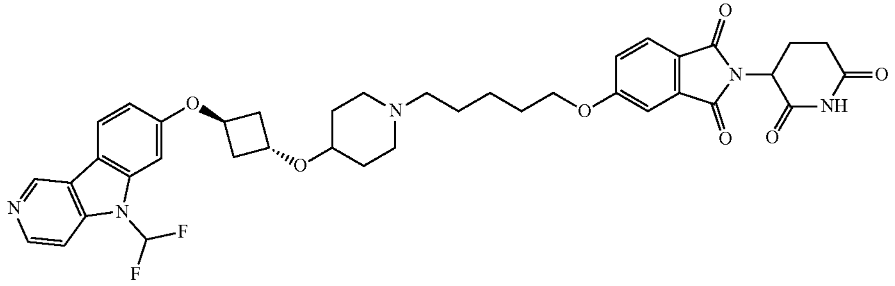 [SMILES: O=C1CCC(N2C(=O)c3ccc(OCCCCCN4CCC(O[C@H]5C[C@H](Oc6ccc7c8cnccc8n(C(F)F)c7c6)C5)CC4)cc3C2=O)C(=O)N1] | 5-((5-(4-((1r,3r)-3-((5-(difluoromethyl)-5H-pyrido[4,3-b]indol-7-yl)oxy)cyclobutoxy)piperidin-1-yl)pentyl)oxy)-2-(2,6-dioxopiperidin-3-yl)isoindoline-1,3-dione | | 730.1 | |
| 605 | 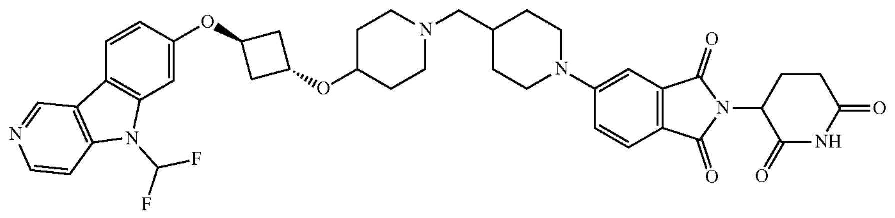 [SMILES: O=C1CCC(N2C(=O)c3ccc(N4CCC(CN5CCC(O[C@H]6C[C@H](Oc7ccc8c9cnccc9n(C(F)F)c8c7)C6)CC5)CC4)cc3C2=O)C(=O)N1] | 5-(4-((4-((1r,3r)-3-((5-(difluoromethyl)-5H-pyrido[4,3-b]indol-7-yl)oxy)cyclobutoxy)piperidin-1-yl)methyl)piperidin-1-yl)-2-(2,6-dioxopiperidin-3-yl)isoindoline-1,3-dione | A | 741.2 | 1H NMR (400 MHz, $CDCl_3$) δ: 9.24 (s, 1H), 8.59 (d, J = 5.6 Hz, 1H), 8.05-7.95 (m, 2H), 7.70 (d, J = 8.8 Hz, 1H), 7.68-7.37 (m, 2H), 7.07 (br d, J = 8.8 Hz, 1H), 7.03 (s, 1H), 6.93 (br d, J = 8.4 Hz, 1H), 5.04-4.91 (m, 2H), 4.52-4.34 (m, 1H), 3.98 (br d, J = 13.6 Hz, 2H), 3.47-3.32 (m, 1H), 3.20-2.89 (m, 5H), 2.88-2.68 (m, 4H), 2.54 (br s, 5H), 2.46-2.08 (m, 5H), 1.95 (br s, 4H), 1.70-1.64 (m, 1H), 1.44-1.34 (m, 1H) |

TABLE 1-continued

| | | | | | |
|---|---|---|---|---|---|
| 606 | 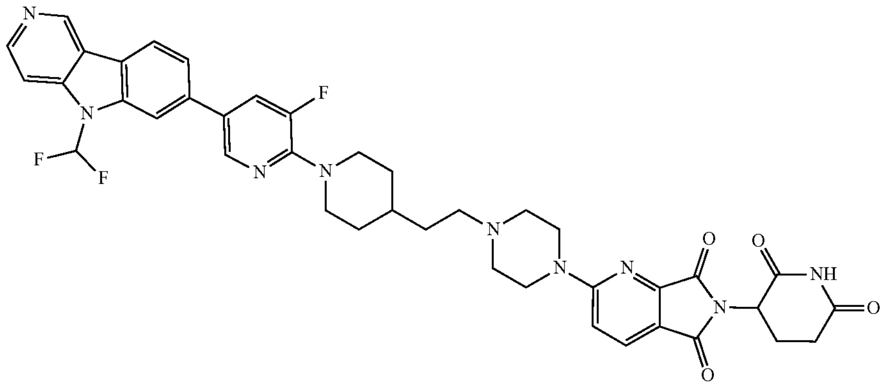 [SMILES: O=C1CCC(N2C(=O)c3ccc(N4CCN(CCC5CCN(c6ncc(-c7ccc8c9cnccc9n(C(F)F)c8c7)cc6F)CC5)CC4)nc3C2=O)C(=O)N1] | 2-(4-(2-(1-(5-(5-(difluoromethyl)-5H-pyrido[4,3-b]indol-7-yl)-3-fluoropyridin-2-yl)piperidin-4-yl)ethyl)piperazin-1-yl)-6-(2,6-dioxopiperidin-3-yl)-5H-pyrrolo[3,4-b]pyridine-5,7(6H)-dione | | 766.2 | $^1$H NMR (400 MHz, MeOD) δ: 9.33 (s, 1H), 8.54 (d, J = 5.9 Hz, 1H), 8.37 (s, 1H), 8.34-8.17 (m, 2H), 8.03 (s, 1H), 7.89 (d, J = 8.9 Hz, 1H), 7.83-7.77 (m, 2h), 7.71 (dd, J = 1.4, 8.3 Hz, 1H), 7.05 (d, J = 8.9 Hz, 1H), 5.11 (dd, J = 5.6, 12.6 Hz, 1H), 4.15 (br d, J = 13.3 Hz, 2H), 3.87 (br s, 4H), 2.95 (br t, J = 11.9 Hz, 2H), 2.89-2.80 (m, 1H), 2.78-2.65 (m, 6H), 2.59 (br d, J = 7.8 Hz, 2H), 2.16-2.08 (m, 1H), 1.86 (br d, J = 13.3 Hz, 2H), 1.66-1.56 (m, 3H), 1.46-1.36 (m, 2H) |
| 607 | 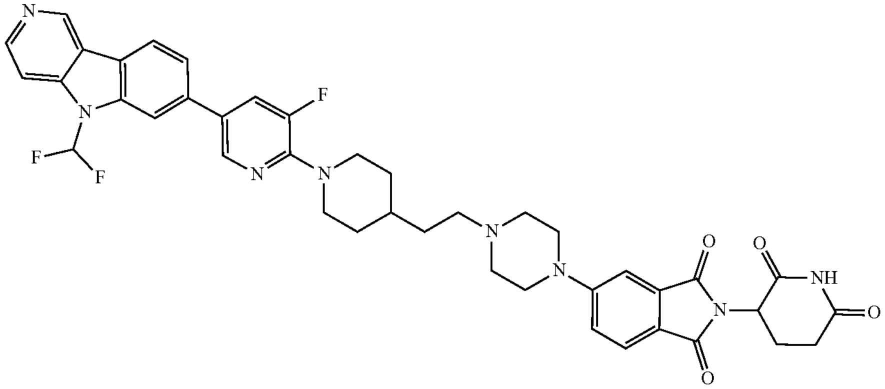 [SMILES: O=C1CCC(N2C(=O)c3ccc(N4CCN(CCC5CCN(c6ncc(-c7ccc8c9cnccc9n(C(F)F)c8c7)cc6F)CC5)CC4)cc3C2=O)C(=O)N1] | 3-(2-(4-(2-(1-(5-(5-(difluoromethyl)-5H-pyrido[4,3-b]indol-7-yl)-3-fluoropyridin-2-yl)piperidin-4-yl)ethyl)piperazin-1-yl)-5-oxo-5,7-dihydro-6H-pyrrolo[3,4-b]pyridin-6-yl)piperidine-2,6-dione | B | 752.2 | $^1$H NMR (400 MHz, DMSO) δ: 10.96 (s, 1H), 9.49 (s, 1H), 8.64-8.60 (m, 1H), 8.53-8.48 (m, 1H), 8.41-8.28 (m, 2H), 8.21 (s, 1H), 8.01 (dd, J = 1.6, 15.2 Hz, 1H), 7.86-7.73 (m, 3H), 6.91 (d, J = 8.8 Hz, 1H), 5.08 (dd, J = 5.6, 13.2 Hz, 1H), 4.28 (d, J = 17.6 Hz, 1H), 4.11 (br d, J = 17.6 Hz, 3H), 3.65 (br s, 4H), 2.98-2.80 (m, 3H), 2.64-2.53 (m, 3H), 2.42-2.35 (m, 5H), 2.00-1.93 (m, 1H), 1.86-1.76 (m, 2H), 1.61 (s, 1H), 1.51-1.40 (m, 2H), 1.38-1.16 (m, 2H) |
| 608 | 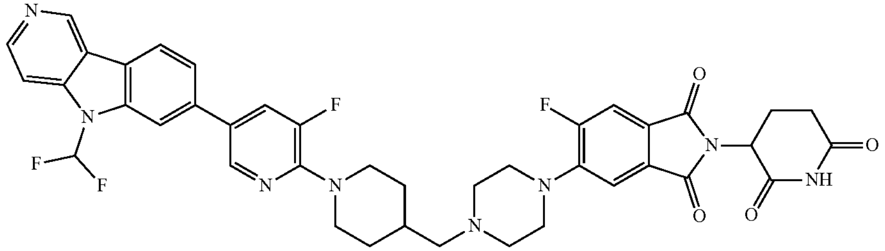 [SMILES: O=C1CCC(N2C(=O)c3cc(F)c(N4CCN(CC5CCN(c6ncc(-c7ccc8c9cnccc9n(C(F)F)c8c7)cc6F)CC5)CC4)cc3C2=O)C(=O)N1] | 5-(4-((1-(5-(5-(difluoromethyl)-5H-pyrido[4,3-b]indol-7-yl)-3-fluoropyridin-2-yl)piperidin-4-yl)methyl)piperazin-1-yl)-2-(2,6-dioxopiperidin-3-yl)-6-fluoroisoindoline-1,3-dione | B | 769.2 | 1H NMR (400 MHz, CHLOROFORM-d) δ: 9.35 (s, 1 H), 8.65 (d, J = 5.6 Hz, 1 H), 8.37 (s, 1 H), 8.19 (d, J = 8.4 Hz, 1 H), 8.00 (s, 1 H), 7.78 (s, 1 H), 7.47-7.62 (m, 5 H), 7.41 (br d, J = 7.6 Hz, 1 H), 4.95 (dd, J = 1.24, 5.6 Hz, 1 H), 4.22 (br d, J = 13.2 Hz, 2 H), 3.34 (br s, 4 H), 2.89-3.04 (m, 3 H), 2.61-2.87 (m, 6 H), 2.36 (br s, 2 H), 2.15 (br d, J = 5.6 Hz, 1 H), 1.94 (br d, J = 10.6 Hz, 2 H), 1.36-1.42 (m, 2 H), 0.90 (br d, J = 6.8 Hz, 1 H) |

TABLE 1-continued

| | | | | | |
|---|---|---|---|---|---|
| 609 | 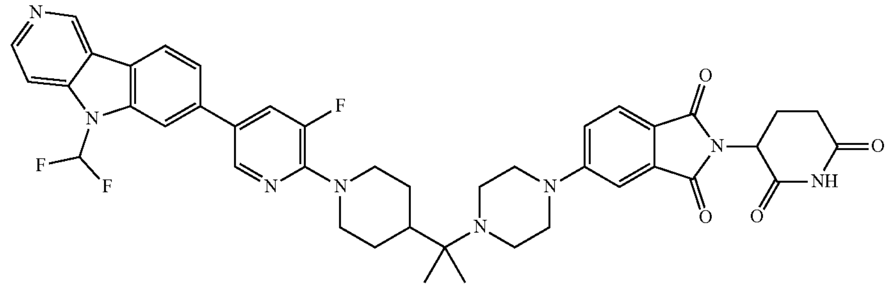 [SMILES: CC(C)(C1CCN(c2ncc(-c3ccc4c5cnccc5n(C(F)F)c4c3)cc2F)CC1)N1CCN(c2ccc3c(c2)C(=O)N(C2CCC(=O)NC2=O)C3=O)CC1] | 5-(4-(2-(1-(5-(5-(difluoromethyl)-5H-pyrido[4,3-b]indol-7-yl)-3-fluoropyridin-2-yl)piperidin-4-yl)propan-2-yl)piperazin-1-yl)-2-(2,6-dioxopiperidin-3-yl)isoindoline-1,3-dione | A | 779.2 | $^1$H NMR (400 MHz, DMSO) δ: 11.09 (s, 1H), 9.48 (s, 1H), 8.63-8.60 (m, 1H), 8.54-8.19 (m, 4H), 7.99 (dd, J = 1.6, 15.2 Hz, 1H), 7.83-7.78 (m, 2H), 7.68 (d, J = 8.8 Hz, 1H), 7.33 (d, J = 1.6 Hz, 1H), 7.24 (dd, J = 1.6, 8.8 Hz, 1H), 5.08 (dd, J = 5.4, 12.8 Hz, 1H), 4.19 (br d, J = 12.8 Hz, 2H), 2.95-2.83 (m, 3H), 2.72-2.58 (m, 5H), 2.58-2.51 (m, 5H), 2.07-1.98 (m, 1H), 1.83 (br d, J = 10.4 Hz, 3H), 1.43-1.29 (m, 2H), 0.92 (s, 6H) |
| 610 | 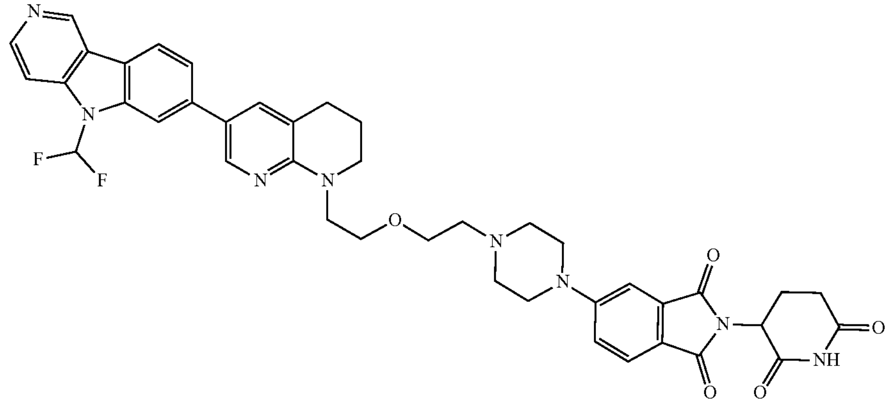 | 5-(4-(2-(2-(6-(5-(difluoromethyl)-5H-pyrido[4,3-b]indol-7-yl)-3,4-dihydro-1,8-naphthyridin-1(2H)-yl)ethoxy)ethyl) piperazin-1-yl)-2-(2,6-dioxopiperidin-3-yl)isoindoline-1,3-dione | | 763.2 | 1H NMR (400 MHz, MeOD) δ: 9.29 (s, 1H), 8.57-8.51 (m, 1H), 8.32-7.77 (m, 5H), 7.66-7.58 (m, 2H), 7.39 (d, J = 8.4 Hz, 1H), 7.13 (s, 1H), 6.99 (d, J = 6.4 Hz, 1H), 4.99 (s, 1H), 3.94-3.84 (m, 2H), 3.82-3.76 (m, 2H), 3.70 (t, J = 4.8 Hz, 2H), 3.64-3.57 (m, 2H), 3.29-3.26 (m, 3H), 3.01-2.70 (m, 5H), 2.70-2.52 (m, 7H), 2.09-1.96 (m, 3H). |
| 611 | 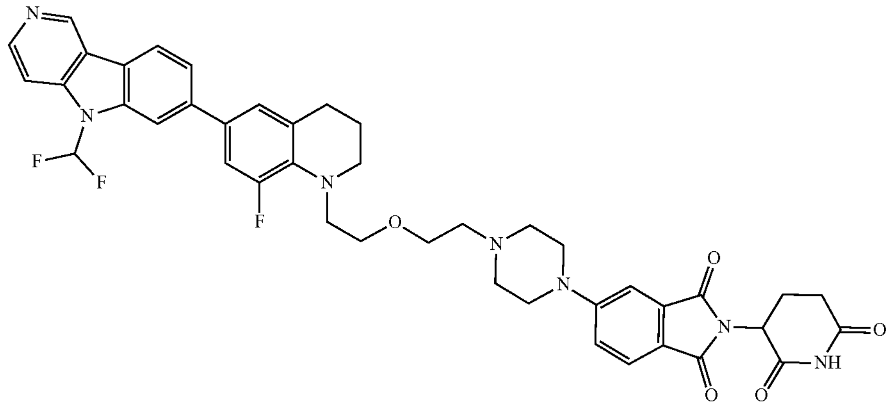 [SMILES: O=C1CCC(N2C(=O)c3ccc(N4CCN(CCOCCN5CCCc6cc(-c7ccc8c9cnccc9n(C(F)F)c8c7)cc(F)c65)CC4)cc3C2=O)C(=O)N1] | 5-(4-(2-(2-(6-(5-(difluoromethyl)-5H-pyrido[4,3-b]indol-7-yl)-8-fluoro-3,4-dihydroquinolin-1(2H)-yl)ethoxy)ethyl) piperazin-1-yl)-2-(2,6-dioxopiperidin-3-yl)isoindoline-1,3-dione | A | 780.2 | 1H NMR (400 MHz, $D_2O$) δ: 9.36 (s, 1H), 8.64 (d, J = 6.4 Hz, 1H), 8.25-7.98 (m, 3H), 7.94-7.68 (m, 2H), 7.48-7.32 (m, 2H), 6.80 (d, J = 8.8 Hz, 1H), 6.62 (s, 2H), 5.05 (dd, J = 5.6, 12.8 Hz, 1H), 3.92-3.74 (m, 6H), 3.70-3.23 (m, 9H), 3.01-2.91 (m, 2H), 2.89-2.75 (m, 4H), 2.71-2.36 (m, 3H), 2.06 (s, 3H) |

TABLE 1-continued

| | | | | | |
|---|---|---|---|---|---|
| 612 | 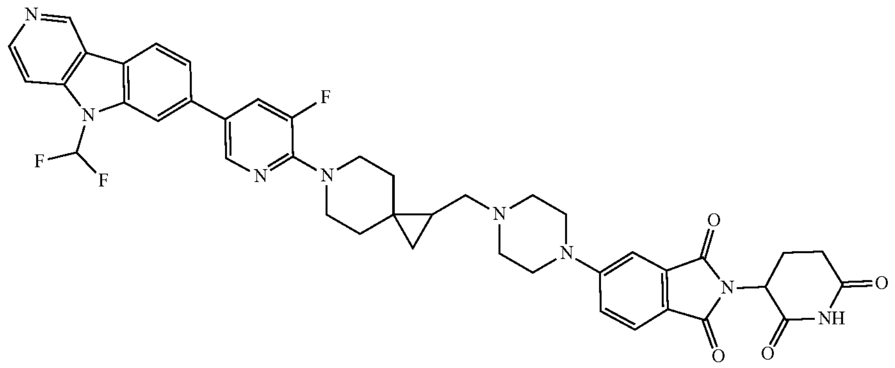 [SMILES: O=C1CCC(N2C(=O)c3ccc(N4CCN(CC5CC56CCN(c5ncc(-c7ccc8c9cnccc9n(C(F)F)c8c7)cc5F)CC6)CC4)cc3C2=O)C(=O)N1] | 5-(4-((6-(5-(5-(difluoromethyl)-5H-pyrido[4,3-b]indol-7-yl)-3-fluoropyridin-2-yl)-6-azaspiro[2.5]octan-1-yl)methyl)piperazin-1-yl)-2-(2,6-dioxopiperidin-3-yl)isoindoline-1,3-dione | | 777.2 | $^1$H NMR (400 MHz, DMSO-$d_6$) δ: 11.07 (s, 1 H), 9.48 (s, 1 H), 8.59-8.64 (m, 1 H), 8.31-8.56 (m, 3 H), 8.21 (s, 1 H), 8.00 (dd, J = 14.8, 1.81 Hz, 1 H), 7.78-7.84 (m, 2 H), 7.67 (d, J = 8.8 Hz, 1 H), 7.34 (s, 1 H), 7.25 (dd, J = 8.8, 1.6 Hz, 1 H), 5.06 (dd, J = 12.8, 5.6 Hz, 1 H), 3.67-3.88 (m, 2 H), 3.40-3.50 (m, 4 H), 3.15-3.25 (m, 4 H), 2.80-2.93 (m, 1 H), 2.55-2.65 (m, 2 H), 2.30-2.41 (m, 4 H), 1.97-2.05 (m, 1 H), 1.61-1.77 (m, 2 H), 1.47-1.51 (m, 1 H), 1.29-1.33 (m, 1 H), 0.80-0.89 (m, 1 H), 0.61-0.64 (m, 1 H), 0.20-0.22 (m, 1 H) |
| 613 | 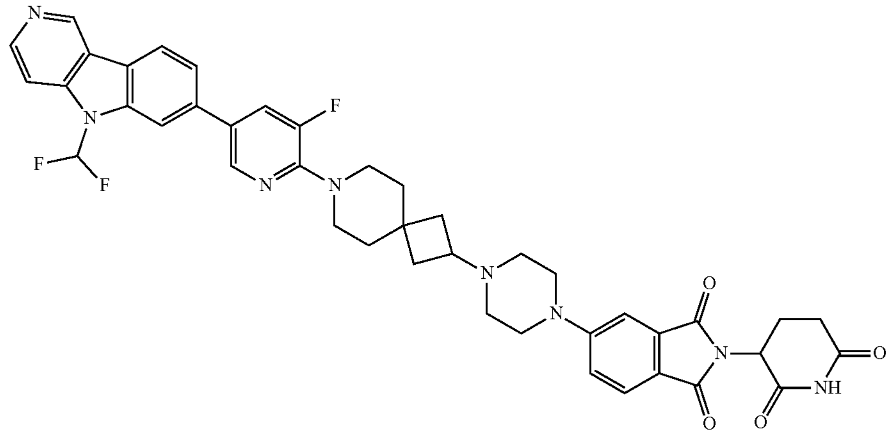 [SMILES: O=C1CCC(N2C(=O)c3ccc(N4CCN(C5CC6(CCN(c7ncc(-c8ccc9c%10cnccc%10n(C(F)F)c9c8)cc7F)CC6)C5)CC4)cc3C2=O)C(=O)N1] | 5-(4-(7-(5-(5-(difluoromethyl)-5H-pyrido[4,3-b]indol-7-yl)-3-fluoropyridin-2-yl)-7-azaspiro[3.5]nonan-2-yl)piperazin-1-yl)-2-(2,6-dioxopiperidin-3-yl)isoindoline-1,3-dione | B | 777.2 | $^1$H NMR (400 MHz, METHANOL-$d_4$) δ: 9.34 (s, 1H), 8.56 (d, J = 6.0 Hz, 1H), 8.38 (s, 1H), 8.35-8.03 (m, 2H), 7.84-7.77 (m, 2H), 7.75-7.67 (m, 2H), 7.40 (d, J = 2.4 Hz, 1H), 7.29-7.25 (m, 1H), 5.11-5.05 (m, 1H), 3.53 (br s, 6H), 3.48 (br s, 2H), 2.99-2.69 (m, 5H), 2.64 (br s, 4H), 2.20 (br t, J = 9.8 Hz, 2H), 2.16-2.07 (m, 1H), 1.81 (br s, 4H), 1.75 (br d, J = 5.6 Hz, 2H) |

TABLE 1-continued

| | | | | | |
|---|---|---|---|---|---|
| 614 | 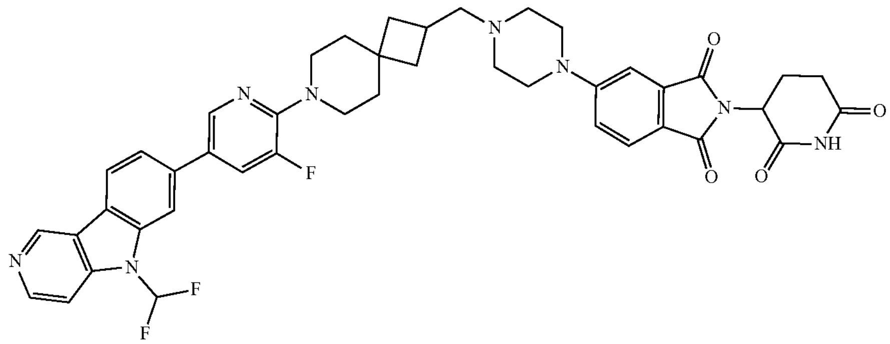 [SMILES: O=C1CCC(N2C(=O)c3ccc(N4CCN(CC5CC6(CCN(c7ncc(-c8ccc9c%10cnccc%10n(C(F)F)c9c8)cc7F)CC6)C5)CC4)cc3C2=O)C(=O)N1] | 5-(4-((7-(5-(5-(difluoromethyl)-5H-pyrido[4,3-b]indol-7-yl)-3-fluoropyridin-2-yl)-7-azaspiro[3.5]nonan-2-yl)methyl)piperazin-1-yl)-2-(2,6-dioxopiperidin-3-yl)isindoline-1,3-dione | B | 791.2 | $^1$H NMR (400 MHz, METHANOL-$d_4$) δ: 9.34 (s, 1H), 8.56 (d, J = 6.0 Hz, 1H), 8.37-8.01 (m, 4H), 7.84-7.78 (m, 2H), 7.75-7.69 (m, 2H), 7.40 (d, J = 2.0 Hz, 1H), 7.30-7.26 (m, 1H), 5.11-5.05 (m, 1H), 3.57-3.50 (m, 5H), 3.44-3.39 (m, 2H), 2.90-2.64 (m, 11H), 2.20-2.10 (m, 3H), 1.87-1.81 (m, 2H), 1.71-1.60 (m, 4H) |
| 615 | 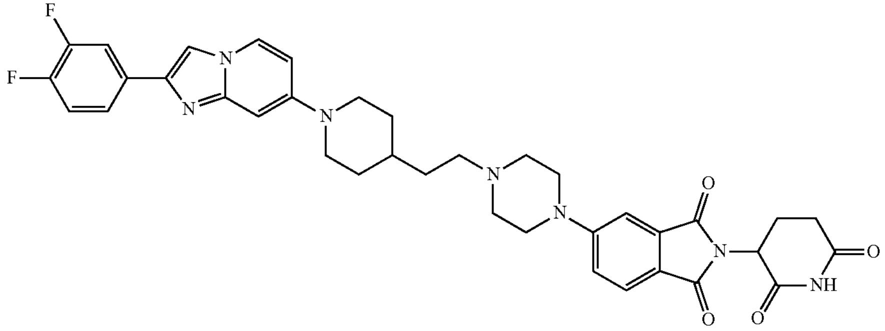 [SMILES: O=C1CCC(N2C(=O)c3ccc(N4CCN(CCC5CCN(c6ccn7cc(-c8ccc(F)c(F)c8)nc7c6)CC5)CC4)cc3C2=O)C(=O)N1] | 5-(4-(2-(1-(2-(3,4-difluorophenyl)imidazo[1,2-a]pyridin-7-yl)piperidin-4-yl)ethyl)piperazin-1-yl)-2-(2,6-dioxopiperidin-3-yl)isoindoline-1,3-dione | | 682.2 | |
| 616 | 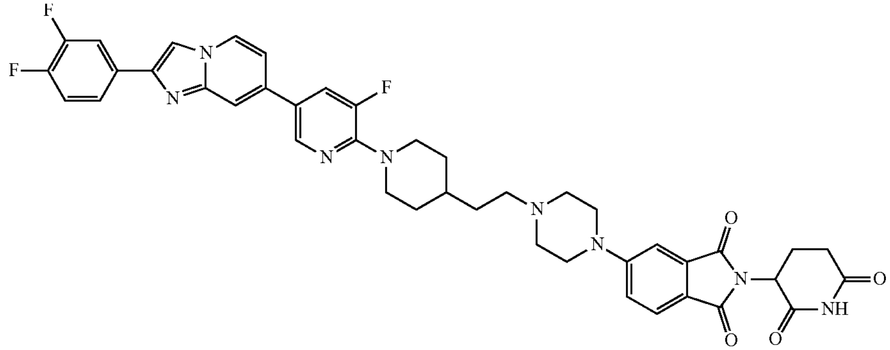 [SMILES: O=C1CCC(N2C(=O)c3ccc(N4CCN(CCC5CCN(c6ncc(-c7ccn8cc(-c9ccc(F)c(F)c9)nc8c7)cc6F)CC5)CC4)cc3C2=O)C(=O)N1] | 5-(4-(2-(1-(5-(2-(3,4-difluorophenyl)imidazo[1,2-a]pyridin-7-yl)-3-fluoropyridin-2-yl)piperidin-4-yl)ethyl)piperazin-1-yl)-2-(2,6-dioxopiperidin-3-yl)isoindoline-1,3-dione | | 777.3 | |

TABLE 1-continued

| | | | |
|---|---|---|---|
| 617 | 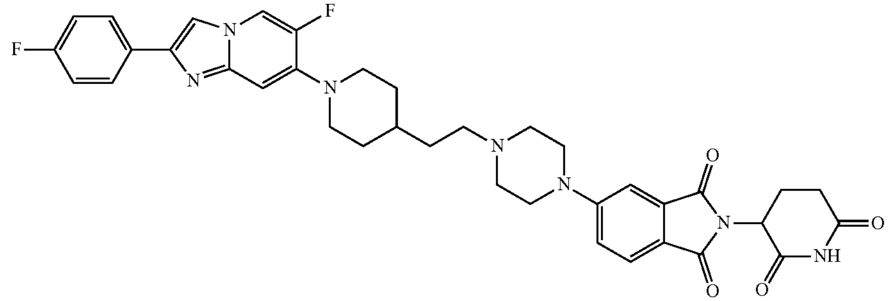 [SMILES: O=C1CCC(N2C(=O)c3ccc(N4CCN(CCC5CCN(c6cc7nc(-c8ccc(F)cc8)cn7cc6F)CC5)CC4)cc3C2=O)C(=O)N1] | 2-(2,6-dioxopiperidin-3-yl)-5-(4-(2-(1-(6-fluoro-2-(4-fluorophenyl)imidazo[1,2-a]pyridin-7-yl)piperidin-4-yl)ethyl)piperazin-1-yl)isoindoline-1,3-dione | |
| 618 | 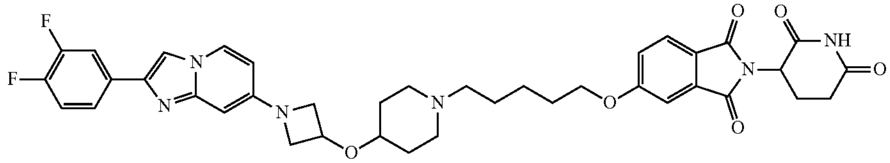 [SMILES: O=C1CCC(N2C(=O)c3ccc(OCCCCCN4CCC(OC5CN(c6ccn7cc(-c8ccc(F)c(F)c8)nc7c6)C5)CC4)cc3C2=O)C(=O)N1] | 5-((5-(4-((1-(2-(3,4-difluorophenyl)imidazo[1,2-a]pyridin-7-yl)azetidin-3-yl)oxy)piperidin-1-yl)pentyl)oxy)-2-(2,6-dioxopiperidin-3-yl)isoindoline-1,3-dione | |
| 619 | 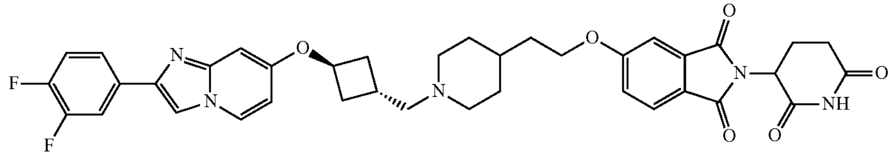 [SMILES: O=C1CCC(N2C(=O)c3ccc(OCCC4CCN(C[C@H]5C[C@H](Oc6ccn7cc(-c8ccc(F)c(F)c8)nc7c6)C5)CC4)cc3C2=O)C(=O)N1] | 5-(2-(1-(((1r,3r)-3-((2-(3,4-difluorophenyl)imidazo[1,2-a]pyridin-7-yl)oxy)cyclobutyl)methyl)piperidin-4-yl)ethoxy)-2-(2,6-dioxopiperidin-3-yl)isoindoline-1,3-dione | 698.4 |
| 620 | 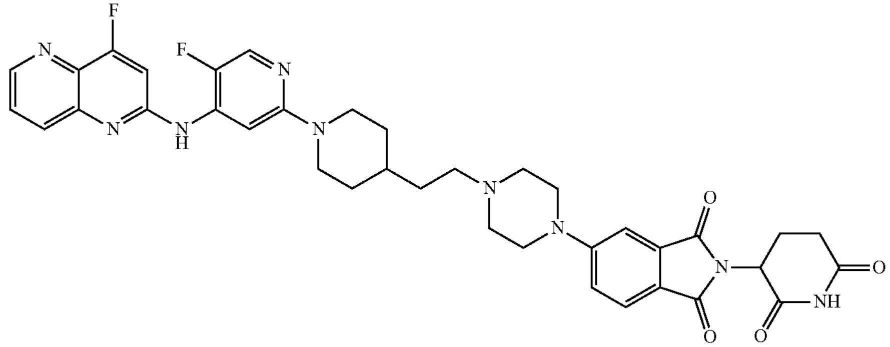 [SMILES: O=C1CCC(N2C(=O)c3ccc(N4CCN(CCC5CCN(c6cc(Nc7cc(F)c8ncccc8n7)c(F)cn6)CC5)CC4)cc3C2=O)C(=O)N1] | 2-(2,6-dioxopiperidin-3-yl)-5-(4-(2-(1-(5-fluoro-4-((4-fluoro-1,5-naphthyridin-2-yl)amino)pyridin-2-yl)piperidin-4-yl)ethyl)piperazin-1-yl)isoindoline-1,3-dione | |

TABLE 1-continued

| | | |
|---|---|---|
| 621 | 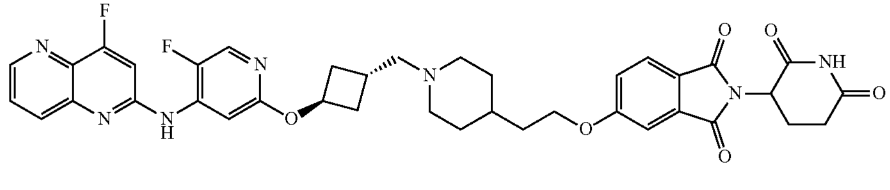 [SMILES: O=C1CCC(N2C(=O)c3ccc(OCCC4CCN(C[C@H]5C[C@H](Oc6cc(Nc7cc(F)c8ncccc8n7)c(F)cn6)C5)CC4)cc3C2=O)C(=O)N1] | 2-(2,6-dioxopiperidin-3-yl)-5-(2-(1-(((1r,3r)-3-((5-fluoro-4-((4-fluoro-1,5-naphthyridin-2-yl)amino)pyridin-2-yl)oxy)cyclobutyl)methyl)piperidin-4-yl)ethoxy)isoindoline-1,3-dione |
| 622 | 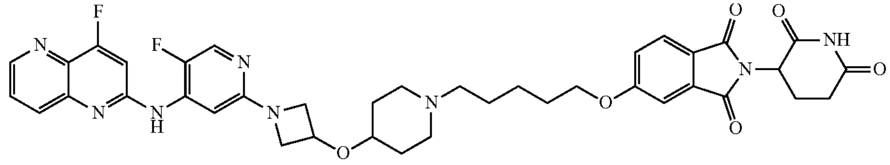 [SMILES: O=C1CCC(N2C(=O)c3ccc(OCCCCCN4CCC(OC5CN(c6cc(Nc7cc(F)c8ncccc8n7)c(F)cn6)C5)CC4)cc3C2=O)C(=O)N1] | 2-(2,6-dioxopiperidin-3-yl)-5-((5-(4-(1-(5-fluoro-4-((4-fluoro-1,5-naphthyridin-2-yl)amino)pyridin-2-yl)azetidin-3-yl)oxy)piperidin-1-yl)pentyl)oxy)isoindoline-1,3-dione |
| 623 | 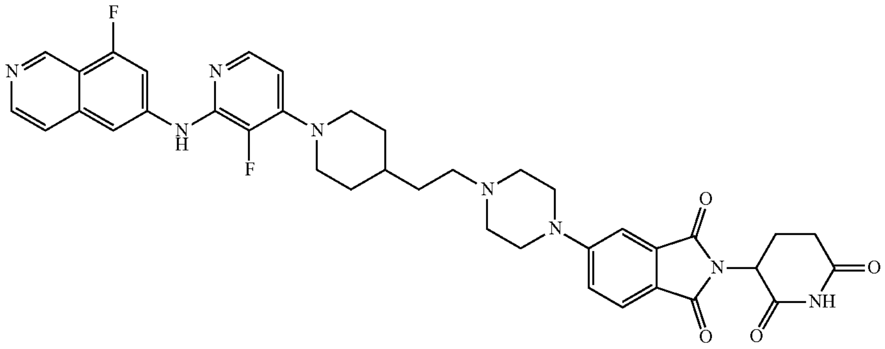 [SMILES: O=C1CCC(N2C(=O)c3ccc(N4CCN(CCC5CCN(c6ccnc(Nc7cc(F)c8cnccc8c7)c6F)CC5)CC4)cc3C2=O)C(=O)N1] | 2-(2,6-dioxopiperidin-3-yl)-5-(4-(2-(1-(3-fluoro-2-((8-fluoroisoquinolin-6-yl)amino)pyridin-4-yl)piperidin-4-yl)ethyl)piperazin-1-yl)isoindoline-1,3-dione |
| 624 | 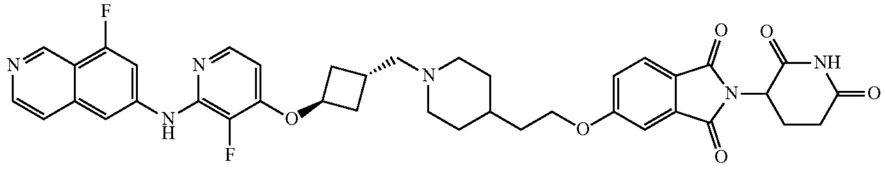 [SMILES: O=C1CCC(N2C(=O)c3ccc(OCCC4CCN(C[C@H]5C[C@H](Oc6ccnc(Nc7cc(F)c8cnccc8c7)c6F)C5)CC4)cc3C2=O)C(=O)N1] | 2-(2,6-dioxopiperidin-3-yl)-5-(2-(1-(((1r,3r)-3-((3-fluoro-2-((8-fluoroisoquinolin-6-yl)amino)pyridin-4-yl)oxy)cyclobutyl)methyl)piperidin-4-yl)ethoxy)isoindoline-1,3-dione |

TABLE 1-continued

| | | | | | |
|---|---|---|---|---|---|
| 625 | 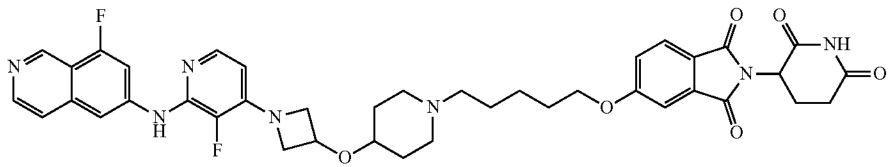 [SMILES: O=C1CCC(N2C(=O)c3ccc(OCCCCCN4CCC(OC5CN(c6ccnc(Nc7cc(F)c8cnccc8c7)c6F)C5)CC4)cc3C2=O)C(=O)N1] | 2-(2,6-dioxopiperidin-3-yl)-5-((5-(4-((1-(3-fluoro-2-((8-fluoroisoquinolin-6-yl)amino)pyridin-4-yl)azetidin-3-yl)oxy)piperidin-1-yl)pentyl)oxy)isoindoline-1,3-dione | | | |
| 626 | 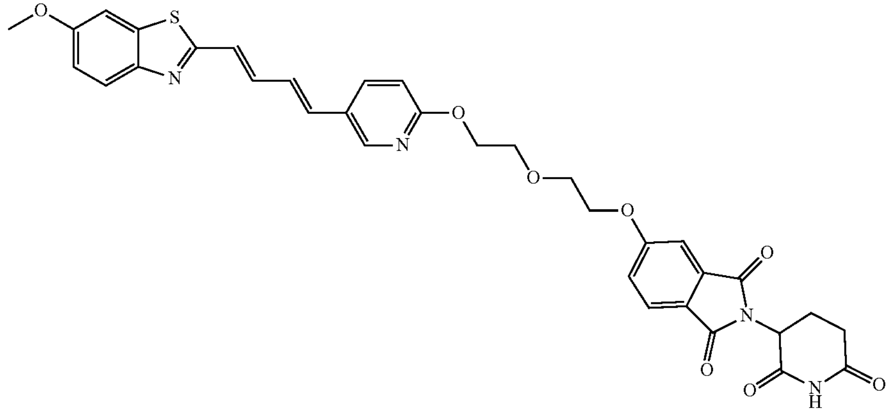 [SMILES: COc1ccc2nc(/C=C/C=C/c3ccc(OCCOCCOc4ccc5c(c4)C(=O)N(C4CCC(=O)NC4=O)C5=O)nc3)sc2c1] | 2-(2,6-dioxopiperidin-3-yl)-5-(2-(2-((5-((1E,3E)-4-(6-methoxybenzo[d]thiazol-2-yl)buta-1,3-dien-1-yl)pyridin-2-yl)oxy)ethoxy)ethoxy)isoindoline-1,3-dione | A | 655.1 | $^1$H NMR (400 MHz, DMSO-$d_6$) δ: 11.12 (br s, 1H), 8.27 (d, J = 2.4 Hz, 1H), 7.99 (dd, J = 2.5, 8.7 Hz, 1H), 7.83 (dd, J = 3.6, 8.6 Hz, 2H), 7.66 (d, J = 2.6 Hz, 1H), 7.45 (d, J = 2.1 Hz, 1H), 7.40-7.28 (m, 2H), 7.23-7.07 (m, 2H), 7.03-6.95 (m, 2H), 6.85 (d, J = 8.7 Hz, 1H), 5.12 (dd, J = 5.3, 1.9 Hz, 1H), 4.54-4.28 (m, 4H), 3.93-3.77 (m, 7H), 2.98-2.82 (m, 1H), 2.56-2.55 (m, 2H), 2.11-2.00 (m, 1H). |
| 627 | 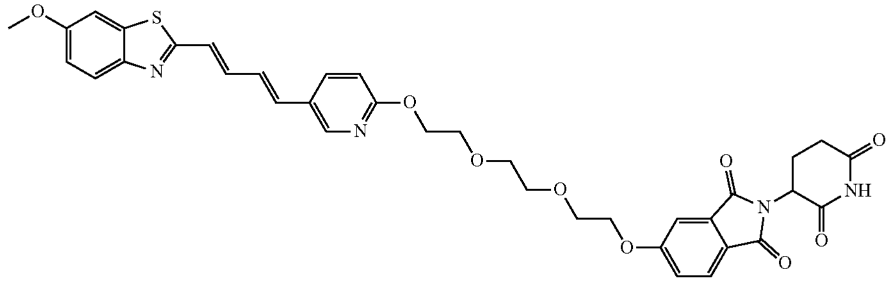 [SMILES: COc1ccc2nc(/C=C/C=C/c3ccc(OCCOCCOCCOc4ccc5c(c4)C(=O)N(C4CCC(=O)NC4=O)C5=O)nc3)sc2c1] | 2-(2,6-dioxopiperidin-3-yl)-5-(2-(2-(2-((5-((1E,3E)-4-(6-methoxybenzo[d]thiazol-2-yl)buta-1,3-dien-1-yl)pyridin-2-yl)oxy)ethoxy)ethoxy)ethoxy)isoindoline-1,3-dione | | 699.1 | $^1$H NMR (400 MHz, DMSO-$d_6$) δ: 11.12 (br s, 1 H), 8.24-8.38 (m, 1 H), 7.94-8.03 (m, 1 H), 7.79-7.87 (m, 2 H), 7.63-7.70 (m, 1 H), 7.45 (d, J = 2.4 Hz, 1 H), 7.27-7.40 (m, 2 H), 7.07-7.22 (m, 2 H), 6.62-7.03 (m, 3 H), 5.12 (m, 1 H), 4.37-4.44 (m, 2 H), 4.26-4.34 (m, 2 H), 3.83-3.87 (m, 3 H), 3.74-3.82 (m, 4 H), 3.63 (s, 4 H), 2.81-2.97 (m, 1 H), 2.53-2.65 (m, 2 H), 1.99-2.10 (m, 1 H) |

TABLE 1-continued

| | | | | | |
|---|---|---|---|---|---|
| 628 | 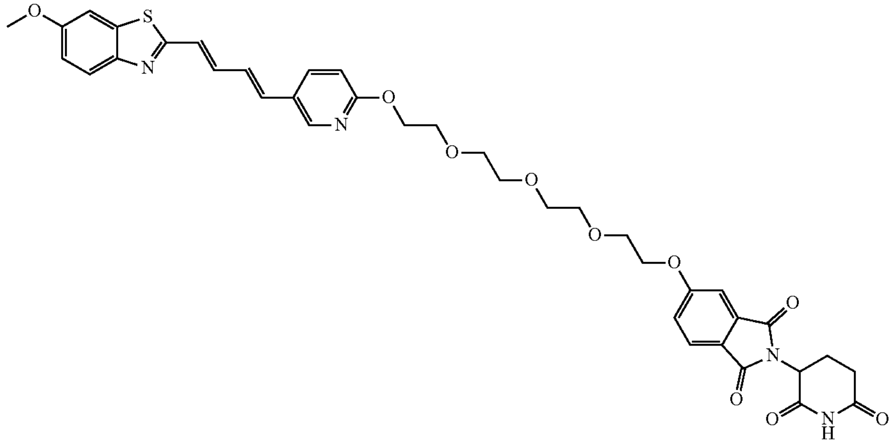 [SMILES: COc1ccc2nc(/C=C/C=C/c3ccc(OCCOCCOCCOCCOc4ccc5c(c4)C(=O)N(C4CCC(=O)NC4=O)C5=O)nc3)sc2c1] | 2-(2,6-dioxopiperidin-3-yl)-5-(2-(2-(2-(2-((5-((1E,3E)-4-(6-methoxybenzo[d]thiazol-2-yl)buta-1,3-dien-1-yl)pyridin-2-yl)oxy)ethoxy)ethoxy)ethoxy)ethoxy)isoindoline-1,3-dione | A | 743.1 | $^1$H NMR (400 MHz, DMSO-$d_6$) δ: 11.11 (br s, 1 H), 8.24-8.33 (m, 1 H), 7.95-8.02 (m, 1 H), 7.78-7.89 (m, 2 H), 7.59-7.71 (m, 1 H), 7.42-7.48 (m, 1 H), 7.26-7.40 (m, 2 H), 7.06-7.21 (m, 2 H), 6.61-7.04 (m, 3 H), 5.12 (m, 1 H), 4.36-4.43 (m, 2 H), 4.28-4.33 (m, 2 H), 3.83-3.89 (m, 3 H), 3.75-3.81 (m, 4 H), 3.53-3.61 (m, 8 H), 2.82-2.95 (m, 1 H), 2.57-2.64 (m, 2 H), 2.00-2.08 (m, 1 H) |
| 629 | 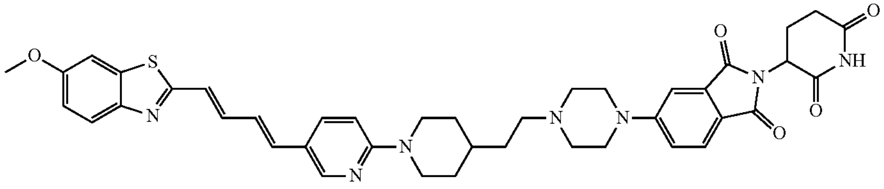 [SMILES: COc1ccc2nc(/C=C/C=C/c3ccc(N4CCC(CCN5CCN(c6ccc7c(c6)C(=O)N(C6CCC(=O)NC6=O)C7=O)CC5)CC4)nc3)sc2c1] | 2-(2,6-dioxopiperidin-3-yl)-5-(4-(2-(1-(5-((1E,3E)-4-(6-methoxybenzo[d]thiazol-2-yl)buta-1,3-dien-1-yl)pyridin-2-yl)piperidin-4-yl)ethyl)piperazin-1-yl)isoindoline-1,3-dione | | 746.2 | $^1$H NMR (400 MHz, DMSO-$d_6$) δ: 11.02-11.15 (m, 1 H), 8.17-8.27 (m, 1 H), 7.75-7.97 (m, 2 H), 7.61-7.73 (m, 2 H), 7.23-7.38 (m, 3 H), 6.51-7.19 (m, 5 H), 5.08 (m, 1 H), 4.31-4.44 (m, 2 H), 3.81-3.88 (m, 3 H), 3.44 (br s, 4 H), 3.31 (br s, 2 H), 2.79-2.95 (m 3 H), 2.53-2.64 (m, 4 H), 2.39 (t, J = 7.2 Hz, 2 H), 1.98-2.08 (m, 1 H), 1.72-1.82 (m, 2 H), 1.54-1.67 (m, 1 H), 1.39-1.51 (m, 2 H), 1.06-1.21 (m, 2 H) |
| 630 | 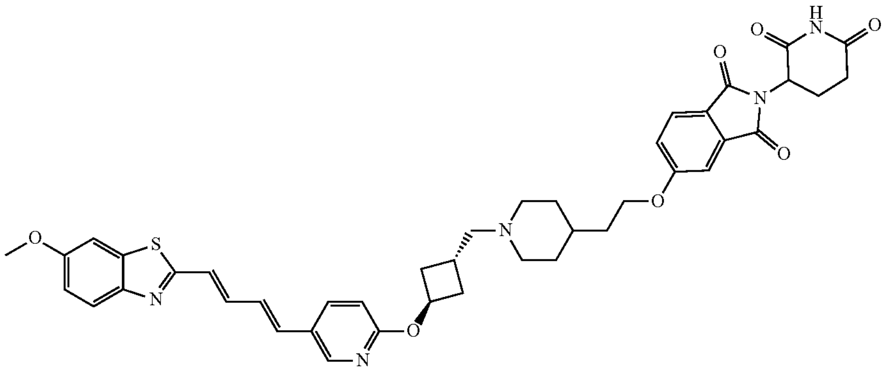 [SMILES: COc1ccc2nc(/C=C/C=C/c3ccc(O[C@H]4C[C@H](CN5CCC(CCOc6ccc7c(c6)C(=O)N(C6CCC(=O)NC6=O)C7=O)CC5)C4)nc3)sc2c1] | 2-(2,6-dioxopiperidin-3-yl)-5-(2-(1-(((1r,3r)-3-((5-((1E,3E)-4-(6-methoxybenzo[d]thiazol-2-yl)buta-1,3-dien-1-yl)pyridin-2-yl)oxy)cyclobutyl)methyl)piperidin-4-yl)ethoxy)isoindoline-1,3-dione | | 762.2 | $^1$H NMR (400 MHz, DMSO-$d_6$) δ: 11.13 (s, 1H), 8.33-8.11 (m, 2H), 7.99 (dd, J = 2.4, 8.7 Hz, 1H), 7.83 (d, J = 8.8 Hz, 2H), 7.71-7.64 (m, 1H), 7.45 (d, J = 2.0 Hz, 1H), 7.38-6.64 (m, 6H), 5.29-4.99 (m, 2H), 4.22 (t, J = 6.8 Hz, 2H), 3.87-3.83 (m, 3H), 2.95-2.80 (m, 3H), 2.63-2.57 (m, 2H), 2.44-2.39 (m, 2H), 2.27-2.01 (m, 4H), 1.91 (t, J = 11.2 Hz, 2H), 1.70 (d, J = 6.8 Hz, 6H), 1.52-1.39 (m, 1H), 1.28-1.17 (m, 2H) |

TABLE 1-continued

| | | | | | |
|---|---|---|---|---|---|
| 631 | 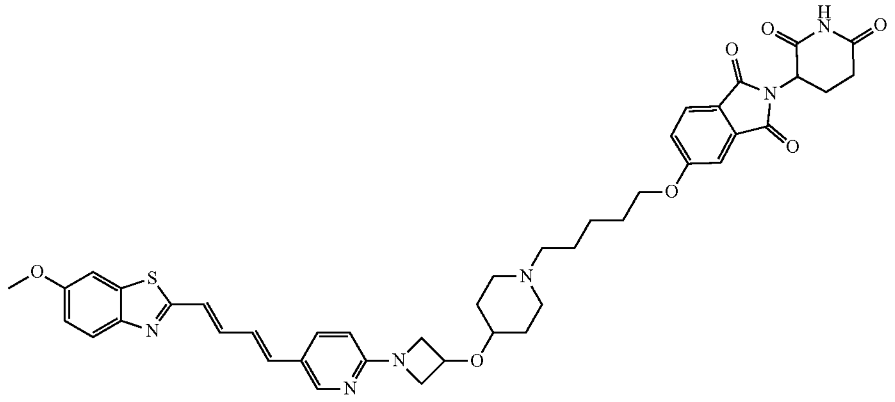 [SMILES: COc1ccc2nc(/C=C/C=C/c3ccc(N4CC(OC5CCN(CCCCCOc6ccc7c(c6)C(=O)N(C6CCC(=O)NC6=O)C7=O)CC5)C4)nc3)sc2c1] | 2-(2,6-dioxopiperidin-3-yl)-5-((5-(4-((1-(5-((1E,3E)-4-(6-methoxybenzo[d]thiazol-2-yl)buta-1,3-dien-1-yl)pyridin-2-yl)azetidin-3-yl)oxy)piperidin-1-yl)pentyl)oxy)isoindoline-1,3-dione | | | |
| 632 | 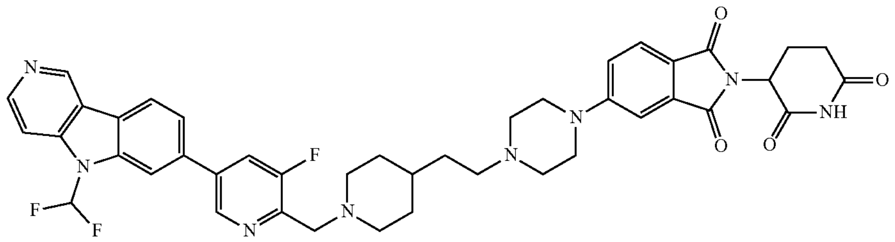 [SMILES: O=C1CCC(N2C(=O)c3ccc(N4CCN(CCC5CCN(Cc6ncc(-c7ccc8c9cnccc9n(C(F)F)c8c7)cc6F)CC5)CC4)cc3C2=O)C(=O)N1] | 5-(4-(2-(1-((5-(5-(difluoromethyl)-5H-pyrido[4,3-b]indol-7-yl)-3-fluoropyridin-2-yl)methyl)piperidin-4-yl)ethyl)piperazin-1-yl)-2-(2,6-dioxopiperidin-3-yl)isoindoline-1,3-dione | A | 779.2 | $^1$H NMR (400 MHz, DMSO-$d_6$) δ: 11.08 (s, 1 H), 9.51 (s, 1 H), 8.86 (s, 1 H), 8.66-8.30 (m, 4 H), 8.14 (dd, J = 11.20, 1.60 Hz, 1 H), 7.94-7.77 (m, 2 H), 7.65 (d, J = 8.4 Hz, 1 H), 7.35-7.09 (m, 2 H), 5.06 (dd, J = 12.80, 5.20 Hz, 1 H), 3.68 (s, 2 H), 3.39 (d, J = 4.80 Hz, 4 H), 2.94-2.82 (m, 3 H), 2.63-2.53 (m, 2 H), 2.45 (s, 4 H), 2.30 (t, J = 7.20 Hz, 2 H), 2.10-1.98 (m, 3 H), 1.62 (d, J = 11.20 Hz, 2 H), 1.36 (q, J = 6.40 Hz, 2 H), 1.27-1.20 (m, 1 H), 1.19-1.08 (m, 2 H). |
| 633 | 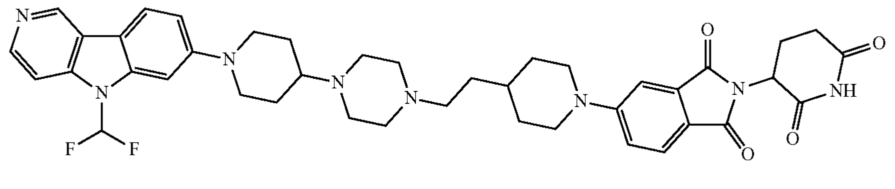 [SMILES: O=C1CCC(N2C(=O)c3ccc(N4CCC(CCN5CCN(C6CCN(c7ccc8c9cnccc9n(C(F)F)c8c7)CC6)CC5)CC4)cc3C2=O)C(=O)N1] | 5-(4-(2-(4-(1-(5-(difluoromethyl)-5H-pyrido[4,3-b]indol-7-yl)piperidin-4-yl)piperazin-1-yl)ethyl)piperidin-1-yl)-2-(2,6-dioxopiperidin-3-yl)isoindoline-1,3-dione | A | 753.2 | $^1$H NMR (400 MHz, DMSO-$d_6$) δ: 11.08 (s, 1H), 9.25 (s, 1H), 8.47-8.39 (m, 2H), 8.18 (s, 1H), 8.07 (d, J = 8.8 Hz, 1H), 7.69-7.63 (m, 2H), 7.31 (d, J = 6.4 Hz, 1H), 7.13 (d, J = 6.4 Hz, 1H), 5.09-5.04 (m, 1H), 4.04-4.01 (m, 1H), 3.90-3.87 (m, 1H), 2.94-2.81 (m, 6H), 2.50-2.42 (m, 5H), 2.05-2.03 (m, 1H), 1.85-1.84 (m, 2H), 1.75-1.73 (m, 2H), 1.55-1.22 (m, 3H), 1.37-1.19 (m, 4H) |
| 634 | 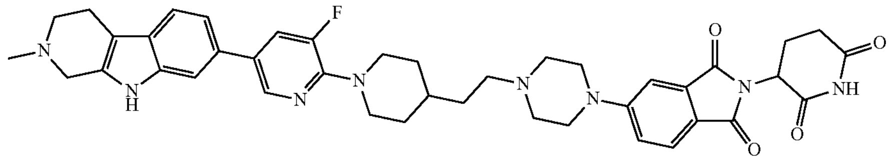 [SMILES: CN1CCc2c([nH]c3cc(-c4cnc(N5CCC(CCN6CCN(c7ccc8c(c7)C(=O)N(C7CCC(=O)NC7=O)C8=O)CC6)CC5)c(F)c4)ccc23)C1] | 2-(2,6-dioxopiperidin-3-yl)-5-(4-(2-(1-(3-fluoro-5-(2-methyl-2,3,4,9-tetrahydro-1H-pyrido[3,4-b]indol-7-yl)pyridin-2-yl)piperidin-4-yl)ethyl)piperazin-1-yl)isoindoline-1,3-dione | A | 733.3 | $^1$H NMR (400 MHz, DMSO-$d_6$) δ = 11.08 (s, 1H), 10.84 (s, 1H), 8.33 (t, J = 1.6 Hz, 1H), 8.25-8.20 (s, 2H), 7.79 (dd, J = 2.0, 14.8 Hz, 1H), 7.68 (d, J = 8.4 Hz, 1H), 7.52 (d, J = 0.8 Hz, 1H), 7.41 (d, J = 8.4 Hz, 1H), 7.34 (d, J = 2.0 Hz, 1H), 7.25 (dd, J = 1.2, 8.0 Hz, 2H), 5.07 (dd, J = 5.6, 12.8 Hz, 1H), 4.02-3.95 (m, 2H), 3.60-3.55 (m, 7H), 2.95-2.80 (m, 4H), 2.70-2.69 (s, 4H), 2.62-2.52 (m, 5H), 2.43-2.36 (m, 5H), 2.05-1.98 (m, 1H), 1.83-1.75 |

TABLE 1-continued

| | | | | | |
|---|---|---|---|---|---|
| | | | | | (m, 2H), 1.61-1.51 (m, 1H), 1.49-1.41 (m, 2H), 1.35-1.23 (m, 2H) |
| 635 | 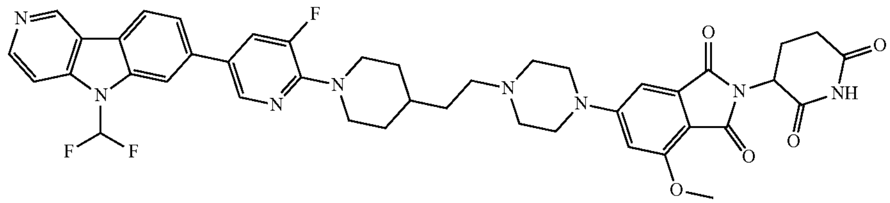 [SMILES: COc1cc(N2CCN(CCC3CCN(c4ncc(-c5ccc6c7cnccc7n(C(F)F)c6c5)cc4F)CC3)CC2)cc2c1C(=O)N(C1CCC(=O)NC1=O)C2=O] | 6-(4-(2-(1-(5-(5-(difluoromethyl)-5H-pyrido[4,3-b]indol-7-yl)-3-fluoropyridin-2-yl)piperidin-4-yl)ethyl)piperazin-1-yl)-2-(2,6-dioxopiperidin-3-yl)-4-methoxyisoindoline-1,3-dione | A | 795.2 | $^1$H NMR (400 MHz, DMSO-$d_6$) δ: 11.05 (s, 1 H), 9.49 (s, 1 H), 8.65-8.61 (m, 1 H), 8.57-8.31 (m, 3 H), 8.21 (s, 1 H), 8.14 (s, 1 H), 8.01 (d, J = 14.80, 1.60 Hz, 1 H), 7.82 (d, J = 6.40 Hz, 2 H), 6.98 (s, 1 H), 6.70 (s, 1 H), 5.01 (d, J = 12.80, 5.20 Hz, 1 H), 4.11 (d, J = 12.40 Hz, 2 H), 3.93 (s, 3 H), 3.50 (d, J = 2.40 Hz, 4 H), 3.16-3.04 (m, 1 H), 2.97-2.83 (m, 3 H), 2.59 (d, J = 2.00 Hz, 2 H), 2.57-2.53 (m, 4 H), 2.02-1.95 (m, 1 H), 1.81 (d, J = 12.40 Hz, 2 H), 1.66-1.38 (m, 4 H), 1.36-1.26 (m, 4 H). |
| 636 | 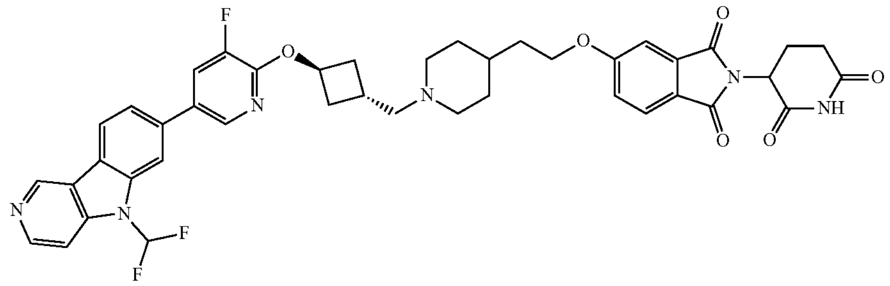 [SMILES: O=C1CCC(N2C(=O)c3ccc(OCCC4CCN(C[C@H]5C[C@H](Oc6ncc(-c7ccc8c9cnccc9n(C(F)F)c8c7)cc6F)C5)CC4)cc3C2=O)C(=O)N1] | 5-(2-(1-(((1r,3r)-3-((5-(5-(difluoromethyl)-5H-pyrido[4,3-b]indol-7-yl)-3-fluoropyridin-2-yl)oxy)cyclobutyl) methyl)piperidin-4-yl) ethoxy)-2-(2,6-dioxopiperidin-3-yl)isoindoline-1,3-dione | B | 781.2 | $^1$H NMR (400 MHz, DMSO-$d_6$) δ: 11.11 (s, 1 H), 9.49 (s, 1 H), 8.62 (d, J = 5.60 Hz, 1 H), 8.49-8.32 (m, 3 H), 8.28-8.11 (m, 3 H), 7.87-7.78 (m, 3 H), 7.43 (d, J = 1.20 Hz, 1 H), 7.34 (d, J = 8.40, 1.60 Hz, 1 H), 5.40-5.07 (m, 2 H), 4.21 (t, J = 6.40 Hz, 3 H), 2.91-2.84 (m, 3 H), 2.65-2.61 (m, 2 H), 2.56 (d, J = 10.40 Hz, 2 H), 2.29-2.21 (m, 2 H), 2.05-1.94 (m, 3 H), 1.89-1.75 (m, 2 H), 1.69 (d, J = 6.40 Hz, 4 H), 1.51-1.42 (m, 1 H), 1.28-1.17 (m, 2 H). |
| N637 | 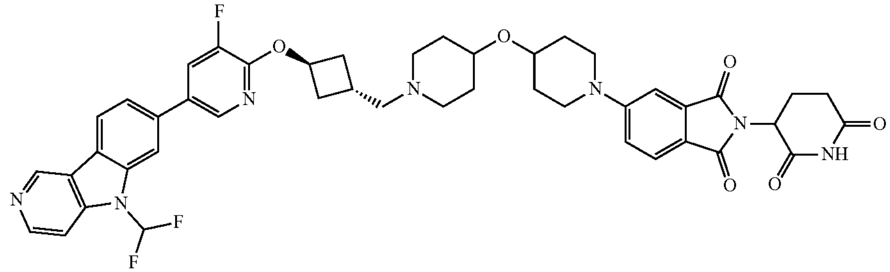 [SMILES: O=C1CCC(N2C(=O)c3ccc(N4CCC(OC5CCN(C[C@H]6C[C@H](Oc7ncc(-c8ccc9c%10cnccc%10n(C(F)F)c9c8)cc7F)C6)CC5)CC4)cc3C2=O)C(=O)N1] | 5-(4-((1-(((1r,3r)-3-((5-(5-(difluoromethyl)-5H-pyrido[4,3-b]indol-7-yl)-3-fluoropiperidin-2-yl)oxy)cyclobutyl) methyl)piperidin-4-yl)oxy)piperidin-1-yl)-2-(2,6-dioxopiperidin-3-yl)isoindoline-1,3-dione | A | 836.2 | $^1$H NMR (400 MHz, DMSO-$d_6$) δ: 11.08 (s, 1 H), 9.51-9.49 (m, 1 H), 9.60-9.41 (m, 1 H), 8.69-8.32 (m, 4 H), 8.29-8.13 (m, 3 H), 7.89-7.72 (m, 2 H), 7.66 (d, J = 8.80 Hz, 1 H), 7.37-7.29 (m, 1 H), 7.28-7.19 (m, 1 H), 5.43-5.32 (m, 1 H), 5.07 (d, J = 12.40, 5.40 Hz, 1 H), 3.83-3.77 (m, 2 H), 3.74-3.68 (m, 2 H), 3.26-3.20 (m, 4 H), 2.99-2.82 (m, 3 H), 2.75-2.70 (m, 3 H), 2.31-2.23 (m, 3 H), 2.15-2.06 (m, 2 H), 2.05-1.99 (m, 1 H), 1.92-1.77 (m, 4 H), 1.53-1.36 (m, 4 H). |

TABLE 1-continued

| | | | | | |
|---|---|---|---|---|---|
| 638 | 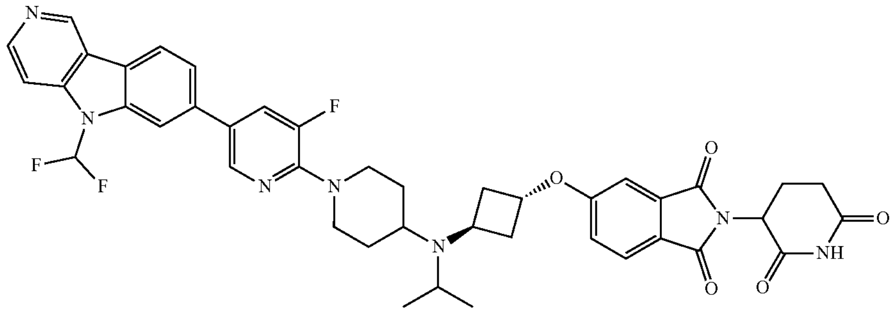 [SMILES: CC(C)N(C1CCN(c2ncc(-c3ccc4c5cnccc5n(C(F)F)c4c3)cc2F)CC1)[C@H]1C[C@H](Oc2ccc3c(c2)C(=O)N(C2CCC(=O)NC2=O)C3=O)C1] | 5-((1r,3r)-3-((1-(5-(5-(difluoromethyl)-5H-pyrido[4,3-b]indol-7-yl)-3-fluoropiperidin-2-yl)piperidin-4-yl)(isopropyl)amino) cyclobutoxy)-2-(2,6-dioxopiperidin-3-yl)isoindoline-1,3-dione | A | 780.3 | $^1$H NMR (400 MHz, DMSO-$d_6$) δ: 11.10 (s, 1H), 10.86-10.74 (m, 1H), 9.98 (s, 1H), 8.91 (d, J = 6.4 Hz, 1H), 8.89-8.62 (m, 1H), 8.61-8.54 (m, 2H), 8.41 (d, J = 6.4 Hz, 1H), 8.38 (s, 1H), 8.11 (d, J = 14.8 Hz, 1H), 7.99 (d, J = 8.4 Hz, 1H), 7.85 (d, J = 8.0 Hz, 1H), 7.35-7.24 (m, 2H), 5.17-5.02 (m, 2H), 4.46-4.32 (m, 1H), 4.21 (d, J = 12.0 Hz, 2H), 3.45-3.40 (m, 2H), 3.38-3.21 (m, 4H), 3.13-3.02 (m, 2H), 2.95-2.85 (m, 1H), 2.58 (d, J = 18.0 Hz, 2H), 2.35-2.21 (m, 2H), 2.06-1.97 (m, 1H), 1.93-1.76 (m, 2H), 1.46-1.37 (m, 3H), 1.32 (d, J = 6.8 Hz, 3H) |
| 639 | 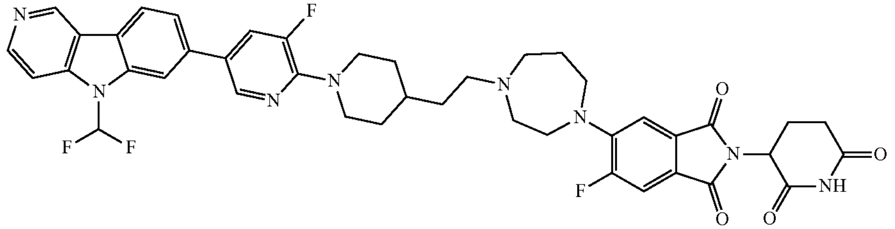 [SMILES: O=C1CCC(N2C(=O)c3cc(F)c(N4CCCN(CCC5CCN(c6ncc(-c7ccc8c9cnccc9n(C(F)F)c8c7)cc6F)CC5)CC4)cc3C2=O)C(=O)N1] | 5-(4-(2-(1-(5-(5-(difluoromethyl)-5H-pyrido[4,3-b]indol-7-yl)-3-fluoropyridin-2-yl)piperidin-4-yl)ethyl)-1,4-diazepan-1-yl)-2-(2,6-dioxopiperidin-3-yl)-6-fluoroisoindoline-1,3-dione | A | 797.2 | $^1$H NMR (400 MHz, CHLOROFORM-d) δ: 9.34 (s, 1H), 8.65 (d, J = 5.6 Hz, 1H), 8.35 (s, 1H), 8.18 (d, J = 8.4 Hz, 1H), 8.04 (br s, 1H), 7.77 (s, 1H), 7.66-7.40 (m, 5H), 7.24 (s, 1H), 4.93 (dd, J = 5.2, 12.2 Hz, 1H), 4.18 (br (d, J =13.6 Hz, 2H), 3.69 (br s, 2H), 3.58 (br t, J = 5.6 Hz, 2H), 3.01-2.69 (m, 11H), 2.21-2.09 (m, 3H), 1.81 (br d, J = 12.8 Hz, 1H), 1.58 (br s, 4H), 1.48-1.33 (m, 2H) |
| 640 | 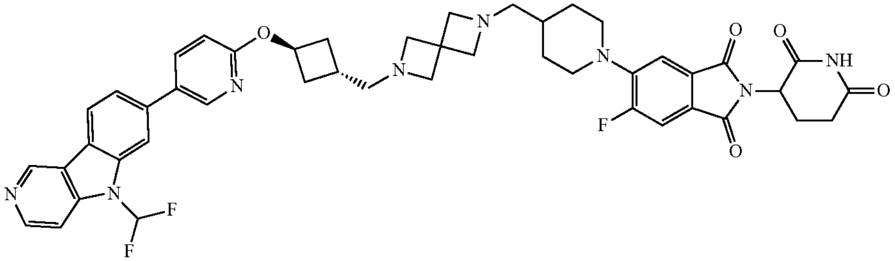 [SMILES: O=C1CCC(N2C(=O)c3cc(F)c(N4CCC(CN5CC6(C5)CN(C[C@H]5C[C@H](Oc7ccc(-c8ccc9c%10cnccc%10n(C(F)F)c9c8)cn7)C5)C6)CC4)cc3C2=O)C(=O)N1] | 5-(4-((6-(((1r,3r)-3-((5-(5-(difluoromethyl)-5H-pyrido[4,3-b]indol-7-yl)pyridin-2-yl)oxy)cyclobutyl) methyl)-2,6-diazaspiro[3.3]heptan-2-yl)methyl)piperidin-1-yl)-2-(2,6-dioxopiperidin-3-yl)-6-fluoroisoindoline-1,3-dione | A | 847.3 | 1H NMR (400 MHz, DMSO-d6, ppm): δ 11.12 (s, 1H), 10.13-9.82 (m, 2H), 8.85 (s, 1H), 8.75-8.47 (m, 3H), 8.27-8.15 (m, 3H), 7.90 (d, J = 8.0 Hz, 1H), 7.74 (d, J = 11.2 Hz, 1H), 7.48 (d, J = 7.6 Hz, 1H), 6.99 (d, J = 8.8 Hz, 1H), 5.32 (t, J = 6.4 Hz, 1H), 5.11 (m, 1H), 4.47-4.20 (m, 9H), 3.63 (d, J = 12.0 Hz, 1H), 3.39 (m, 1H), 3.14 (s, 2H), 2.94-2.84 (m, 3H), 2.64-2.55 (m, 3H), 2.37-2.31 (m, 4H), 2.08-2.02 (m, 1H), 1.84-1.68 (m, 4H), 1.40-1.30 (m, 2H) |

TABLE 1-continued

| | | | | | |
|---|---|---|---|---|---|
| 641 | 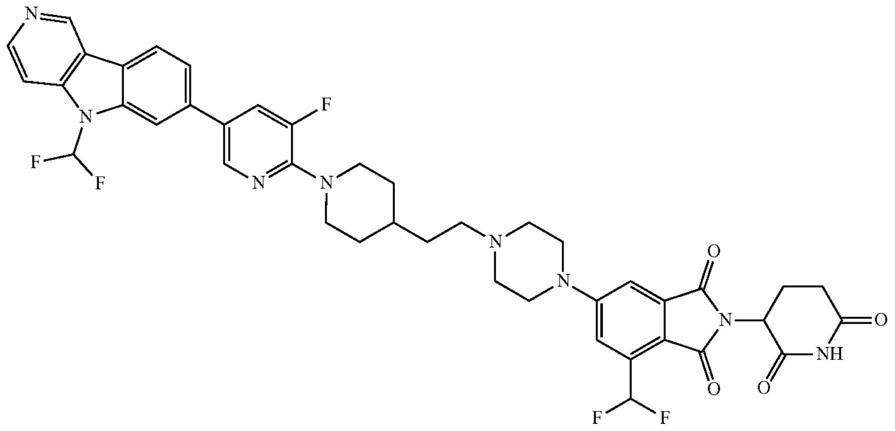 [SMILES: O=C1CCC(N2C(=O)c3cc(N4CCN(CCC5CCN(c6ncc(-c7ccc8c9cnccc9n(C(F)F)c8c7)cc6F)CC5)CC4)cc(C(F)F)c3C2=O)C(=O)N1] | 4-(difluoromethyl)-6-(4-(2-(1-(5-(5-(difluoromethyl)-5H-pyrido[4,3-b]indol-7-yl)-3-fluoropyridin-2-yl)piperidin-4-yl)ethyl)piperazin-1-yl)-2-(2,6-dioxopiperidin-3-yl)isoindoline-1,3-dione | A | 815.2 | 1H NMR (400 MHz, DMSO-d6) δ: 11.12 (s, 1 H), 9.49 (s, 1 H), 8.30-8.68 (m, 4 H), 8.20 (d, J = 11.6 Hz, 1 H), 8.01 (dd, J = 15.2, 1.6 Hz, 1 H), 7.81 (d, J = 6.0 Hz, 2 H), 7.25-7.57 (m, 3 H), 5.10 (dd, J = 12.8, 5.6 Hz, 1 H), 4.11 (d, J = 12.8 Hz, 2 H), 3.41-3.52 (m, 8 H), 2.80-2.98 (m, 4 H), 2.56-2.64 (m, 2 H), 2.42 (d, J = 6.8 Hz, 2 H), 1.98-2.06 (m, 1 H), 1.81 (d, J = 12.4 Hz, 2 H), 1.61 (s, 1 H), 1.47 (d, J = 6.8 Hz, 2 H), 1.25-1.37 (m, 2 H) |
| 642 | 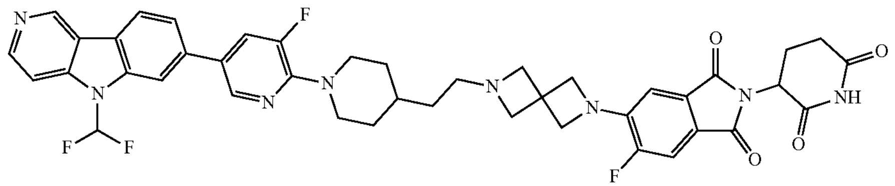 [SMILES: O=C1CCC(N2C(=O)c3cc(F)c(N4CC5(CN(CCC6CCN(c7ncc(-c8ccc9c%10cnccc%10n(C(F)F)c9c8)cc7F)CC6)C5)C4)cc3C2=O)C(=O)N1] | 5-(6-(2-(1-(5-(5-(difluoromethyl)-5H-pyrido[4,3-b]indol-7-yl)-3-fluoropyridin-2-yl)piperidin-4-yl)ethyl)-2,6-diazaspiro[3.3]heptan-2-yl)-2-(2,6-dioxopiperidin-3-yl)-6-fluoroisoindoline-1,3-dione | A | 795.2 | 1H NMR (400 MHz, DMSO-$d_6$) δ: 11.09 (s, 1H), 9.48 (s, 1H), 8.66-8.31 (m, 4H), 8.19 (d, J = 8.0 Hz, 2H), 8.06-7.93 (m, 1H), 7.80 (d, J = 6.0 Hz, 2H), 7.60 (d, J = 11.2 Hz, 1H), 6.92 (d, J = 7.6 Hz, 1H), 5.06 (dd, J = 5.4, 12.8 Hz, 1H), 4.24 (s, 4H), 4.08 (d, J = 12.8 Hz, 2H), 3.37 (s, 4H), 2.93-2.83 (m, 3H), 2.59-2.55 (m, 4H), 2.05-1.97 (m, 1H), 1.74 (d, J = 12.0 Hz, 2H), 1.56 (s, 1H), 1.31-1.18 (m, 4H) |
| 643 | 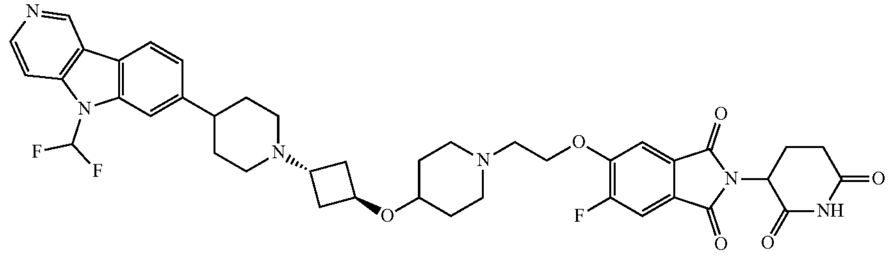 [SMILES: O=C1CCC(N2C(=O)c3cc(F)c(OCCN4CCC(O[C@H]5C[C@H](N6CCC(c7ccc8c9cnccc9n(C(F)F)c8c7)CC6)C5)CC4)cc3C2=O)C(=O)N1] | 5-(2-(4-((1r,3r)-3-(4-(5-(difluoromethyl)-5H-pyrido[4,3-b]indol-7-yl)piperidin-1-yl)cyclobutoxy)piperidin-1-yl)ethoxy)-2-(2,6-dioxopiperidin-3-yl)-6-fluoroisoindoline-1,3-dione | | 773.3 | $^1$H NMR (400 MHz, DMSO-$d_6$) δ: 11.13 (s, 1H), 9.42 (s, 1H), 8.59 (d, J = 5.6 Hz, 1H), 8.45 (s, 1H), 8.31-8.27 (m, 1H), 8.13 (s, 1H), 7.91-7.73 (m, 4H), 7.38 (d, J = 8.0 Hz, 1H), 5.13 (dd, J = 5.6, 12.8 Hz, 1H), 4.51-4.42 (m, 2H), 4.22 (d, J = 0.8 Hz, 1H), 3.76-3.66 (m, 2H), 3.06-2.83 (m, 8H), 2.65-2.51 (m, 5H), 2.46-2.37 (m, 3H), 2.21 (s, 2H), 2.09-2.02 (m, 3H), 1.95-1.82 (m, 4H), 1.61-1.45 (m, 2H). |

TABLE 1-continued

| | | | | | |
|---|---|---|---|---|---|
| 644 | 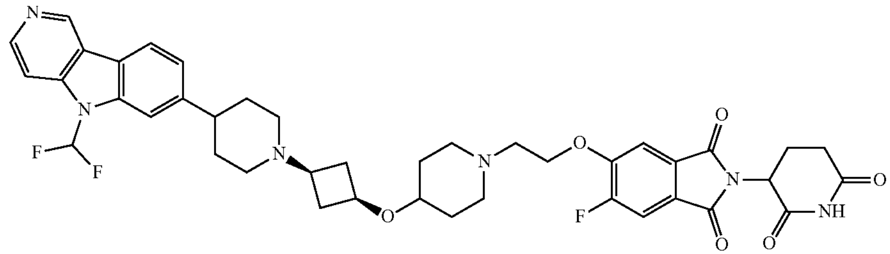 [SMILES: O=C1CCC(N2C(=O)c3cc(F)c(OCCN4CCC(O[C@H]5C[C@@H](N6CCC(c7ccc8c9cnccc9n(C(F)F)c8c7)CC6)C5)CC4)cc3C2=O)C(=O)N1] | 5-(2-(4-((1s,3s)-3-(4-(5-(difluoromethyl)-5H-pyrido[4,3-b]indol-7-yl)-yl)piperidin-1-yl)cyclobutoxy)piperidin-1-yl)ethoxy)-2-(2,6-dioxopiperidin-3-yl)-6-fluoroisoindoline-1,3-dione | A | 773.3 | $^1$H NMR (400 MHz, DMSO-$d_6$) δ: 11.12 (s, 1H), 9.40 (s, 1H), 8.57 (d, J = 5.6 Hz, 1H), 8.47-8.12 (m, 4H), 7.85 (d, J = 9.5 Hz, 1H), 7.81-7.76 (m, 3H), 7.36 (d, J = 8.4 Hz, 1H), 5.13 (dd, J = 5.6, 12.8 Hz, 1H), 4.38 (t, J = 5.6 Hz, 2H), 3.34-3.24 (m, 3H), 2.97 (d, J = 10.4 Hz, 2H), 2.83-2.66 (m, 6H), 2.64-2.56 (m, 1H), 2.45-2.38 (m, 3H), 2.21 (t, J = 9.6 Hz, 2H), 2.09-2.02 (m, 1H), 1.95 (t, J = 8.4 Hz, 2H), 1.89-1.82 (m, 2H), 1.81-1.68 (m, 6H), 1.47-1.35 (m, 2H). |
| 645 | 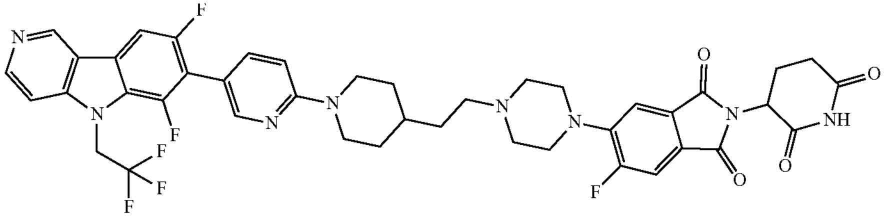 [SMILES: O=C1CCC(N2C(=O)c3cc(F)c(N4CCN(CCC5CCN(c6ccc(-c7c(F)cc8c9cnccc9n(CC(F)(F)F)c8c7F)cn6)CC5)CC4)cc3C2=O)C(=O)N1] | 5-(4-(2-(1-(5-(6,8-difluoro-5-(2,2,2-trifluoroethyl)-5H-pyrido[4,3-b]indol-7-yl)pyrimidin-2-yl)piperidin-4-yl)ethyl)piperazin-1-yl)-2-(2,6-dioxopiperidin-3-yl)-6-fluoroisoindoline-1,3-dione | A | 834.2 | 1H NMR (400 MHz, DMSO-d6) δ: 11.12 (s, 1 H), 9.49 (s, 1 H), 8.64 (d, J = 5.6 Hz, 1 H), 8.53 (s, 2 H), 8.24-8.29 (m, 1 H), 7.88 (d, J = 6.0 Hz, 1 H), 7.73 (d, J = 11.2 Hz, 1 H), 7.46 (d, J = 7.2 Hz, 1 H), 5.51 (d, J = 8.8 Hz, 2 H), 5.06-5.13 (m, 1 H), 4.74 (d, J = 11.6 Hz, 3 H), 2.83-3.02 (m, 8 H), 2.62 (s, 2 H), 2.42 (s, 2 H), 2.03-2.07 (m, 1 H), 1.56-1.87 (m, 5 H), 1.47 (s, 3 H), 1.06-1.25 (m, 3 H) |
| 646 | 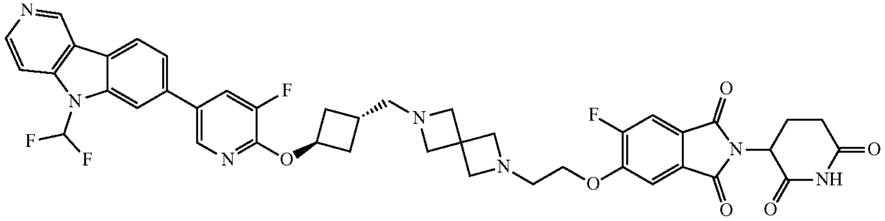 [SMILES: O=C1CCC(N2C(=O)c3cc(F)c(OCCN4CC5(C4)CN(C[C@H]4C[C@H](Oc6ncc(-c7ccc8c9cnccc9n(C(F)F)c8c7)cc6F)C4)C5)cc3C2=O)C(=O)N1] | 5-(2-(6-(((1r,3r)-3-((5-(5-(difluoromethyl)-5H-pyrido[4,3-b]indol-7-yl)-3-fluoropyridin-2-yl)oxy)cyclobutyl)methyl)-2,6-diazaspiro[3.3]heptan-2-yl)ethoxy)-2-(2,6-dioxopiperidin-3-yl)-6-fluoroisoindoline-1,3-dione | A | 812.2 | $^1$H NMR (400 MHz, DMSO-$d_6$) δ: 11.19-11.10 (m, 1H), 10.41-9.88 (m, 1H), 9.63 (s, 1H), 8.79-8.65 (m, 1H), 8.59-8.36 (m, 3H), 8.30-8.19 (m, 2H), 8.11-7.76 (mm, 4H), 7.48-7.26 (m, 1H), 5.38 (quin, J = 6.4 Hz, 1H), 5.14 (dd, J = 5.6, 12.4 Hz, 1H), 4.52 (s, 2H), 4.41-4.27 (m, 6H), 3.67 (s, 4H), 2.94-2.84 (m, 2H), 2.63 (s, 1H), 2.58 (s, 4H), 2.36 (d, J = 6.4 Hz, 3H), 2.03-1.94 (m, 1H). |
| 647 | 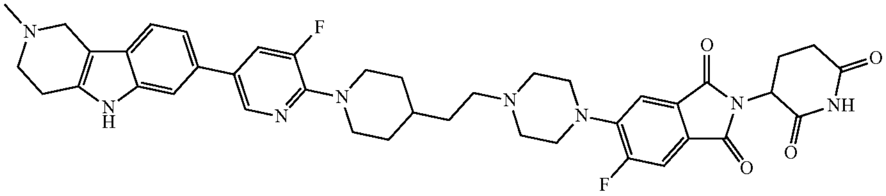 [SMILES: CN1CCc2[nH]c3cc(-c4cnc(N5CCC(CCN6CCN(c7cc8c(cc7F)C(=O)N(C7CCC(=O)NC7=O)C8=O)CC6)CC5)c(F)c4)ccc3c2C1] | 2-(2,6-dioxopiperidin-3-yl)-5-fluoro-6-(4-(2-(1-(3-fluoro-5-(2-methyl-2,3,4,5-tetrahydro-1H-pyrido[4,3-b]indol-7-yl)pyridin-2-yl)piperidin-4-yl)ethyl)piperazin-1-yl)isoindoline-1,3-dione | B | 751.2 | $^1$H NMR (400 MHz, DMSO-$d_6$) δ: 11.10 (s, 1H), 10.93 (s, 1H), 8.33 (s, 1H), 8.16 (s, 1H), 7.85-7.65 (m, 2H), 7.56-7.35 (m, 3H), 7.25 (d, J = 8.0 Hz, 1H), 5.10 (dd, J = 5.6, 12.8 Hz, 1H), 3.99 (d, J = 12.4 Hz, 2H), 3.64 (s, 2H), 3.25 (s, 8H), 2.90-2.82 (m, 6H), 2.61 (d, J = 2.4 Hz, 1H), 2.54 (s, 5H), 2.41 (t, J = 7.2 Hz, 2H), 2.06-1.99 (m, 1H), 1.78 (d, J = 11.2 Hz, 2H), 1.61-1.51 (m, 1H), 1.50-1.41 (m, 2H), 1.34-1.21 (m, 2H). |

A ≤50% of tau protein remaining (>50% of tau protein degraded)
B >50% of tau protein remaining (≤50% of tau protein degraded)

DESCRIPTIONS OF FIGURES

Data for compounds in Table 1 was generated using in vitro tau Degradation Assay protocol as described in Methods for FIGS. 2A and 2B below.

Tau Protein In Vivo Degradation in Wildtype Mice

FIG. 1. In the study 21 male BI6 wildtype mice, divided into seven groups of three mice, were treated single time via a bilateral intrahippocampal injection with vehicle ECP-1 ([5% EtOH and 5% Cremophore RH40 in pH 7.4 phosphate buffer]; group A; see FIG. 1) or Compound 4 tau bifunctional compound ([3 μL of 1 mg/mL solution in ECP-1]; groups B to G; see FIG. 1). All animals were sacrificed at certain time points after the test item or vehicle injection as shown in FIG. 1, and brain samples were collected. The hippocampus was resected, and levels of total tau were measured with Meso Scale Discovery assay kit. Results are presented in FIG. 1.

Tau Targeting Bifunctional Molecules are Potent P301L Tau Degraders In Vitro, which Depends Upon Both Binding to the Tau Binding Moiety and the E3 Ligase Binding Moiety (ULM).

Figure 2A:
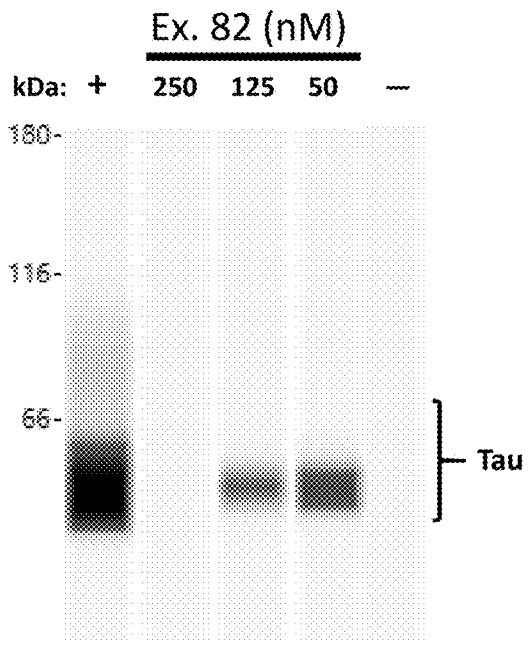
FIGS. 2A, 2B, and 2C. Tau targeting bifunctional molecules are potent P301L tau degraders in vitro, which depends upon both binding to the tau binding moiety and the E3 ligase binding moiety (ULM). (2A) Tau expression was induced by addition (+) of doxycycline (1 μg/ml) to ChoK1-Tau P301L clone D1 for 24 hours followed by a 24 hour doxycycline washout period where only bifunctional molecule was present. 250 nM, 125 nM, or 50 nM exemplary compound 82 treatment caused concentration-dependent degradation of tau compared to the negative (−) control treatment with 0.1% DMSO and demonstrated a DC50 of less than 50 nM. (2B) Degradation by exemplary compound 82 was completely inhibited by 10-fold molar excess incubation with the ligand against the E3 ligase (pomalidomide.
Figure 2B:
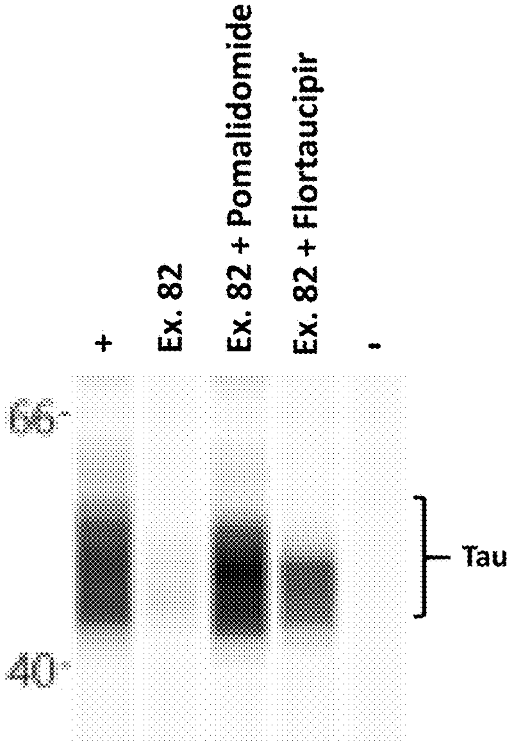
Figure 2C:
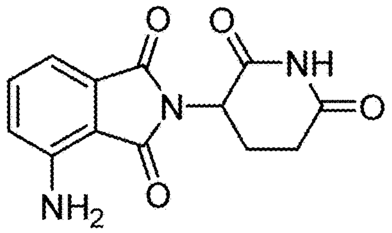
Figure 2C:
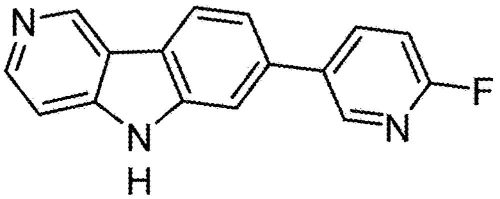

FIGS. 2A and 2B. (2A) Tau expression was induced by addition (+) of doxycycline (1 μg/ml) to ChoK1-Tau P301L clone D1. 250 nM, 125 nM, or 50 nM exemplary bifunctional compound 82 treatment caused concentration-dependent degradation of tau compared to the negative (−) control treatment with 0.1% DMSO and demonstrated a DC50 of less than 50 nM. (2B) Degradation by exemplary bifunctional compound 82 was completely inhibited by 10-fold molar excess incubation with the ligand against the E3 ligase (pomalidomide; FIG. 2C). Partial inhibition of tau degradation was observed by similar competition with the tau warhead ligand (flortaucipir; FIG. 2C). These data indicate that tau degradation is dependent on both the E3 ligase and tau binding components of the bifunctional compounds, thereby confirming that the targeted degradation of tau is mediated by the bifunctional compound through the proteolysis targeting chimeric mechanism.

Exemplary Bifunctional Compounds Degrade >95% of Pathologic Tau in Tg2508 Brain Following Parenteral Administration In Vivo.

Figure 3A:
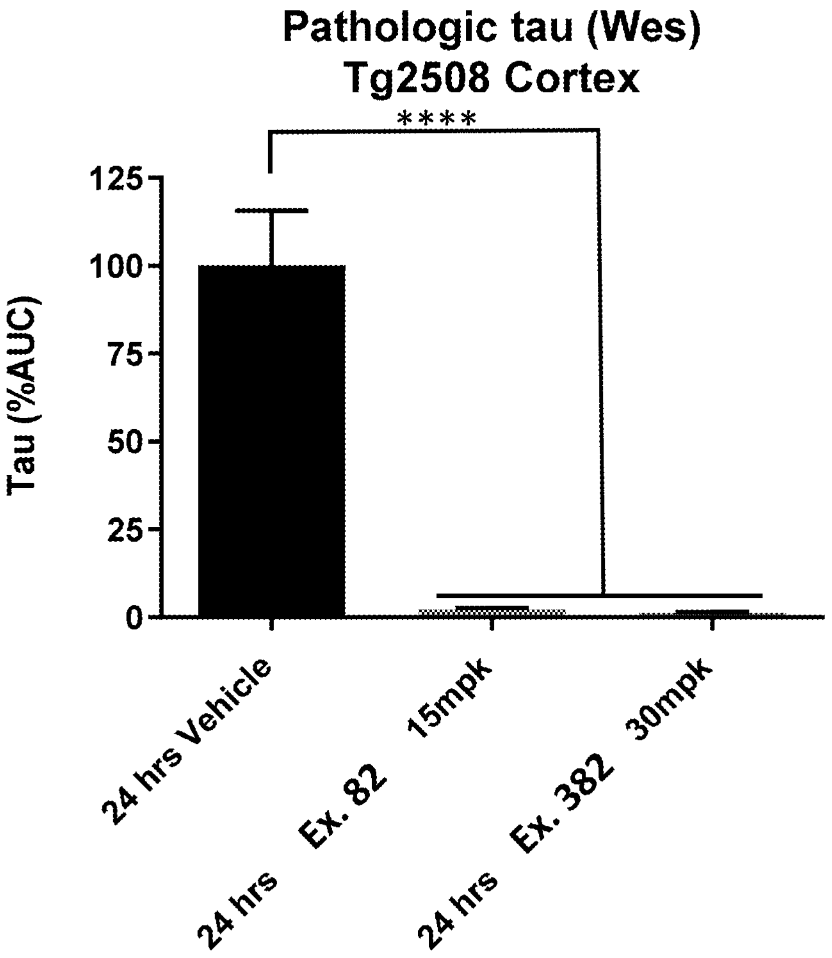
FIGS. 3A and 3B. Exemplary bifunctional compounds degrade greater than 95% of pathologic tau in Tg2508 brain following parenteral administration in vivo. Tg2508 tauopathy mice were dosed (12 animals per group) with either 15 mpk exemplary compound 82 or 30 mpk exemplary compound 382 or vehicle intravenously. Twenty-four hours post dose, the animals were sacrificed, and cortical brain samples were analyzed for pathologic tau by Wes capillary gel electrophoresis.
Figure 3B:
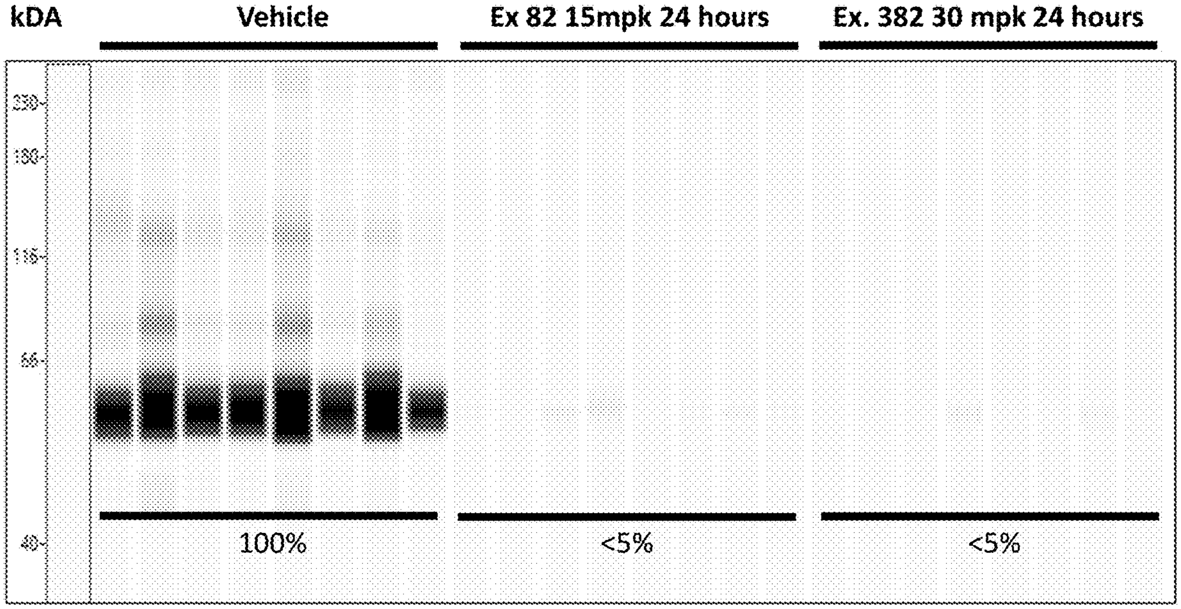

FIGS. 3A and 3B. Tg2508 tauopathy mice were dosed (12 animals per group) with either 15 mpk exemplary compound 82 or 30 mpk exemplary compound 382 or vehicle parenterally, as described below (Lewis et al., 2000). Twenty-four hours post dose, the animals were sacrificed and cortical brain samples were analyzed for pathologic tau by Wes capillary gel electrophoresis. FIG. 3A is a graphical representation of the averaged analysis of pathologic tau shown for each animal tested comparing lanes from the vehicle control to either exemplary compound 82 or exemplary compound 382 as indicated in FIG. 3B. Greater than 95% reduction of pathologic tau was observed following treatment of the Tg2508 animals with either exemplary compound 82 or exemplary compound 382.

Exemplary Bifunctional Compounds Inhibit Tg2508 Ex-Vivo Seeding of P301L CHO MC1 by High Content Image Analysis.

Figure 4A:
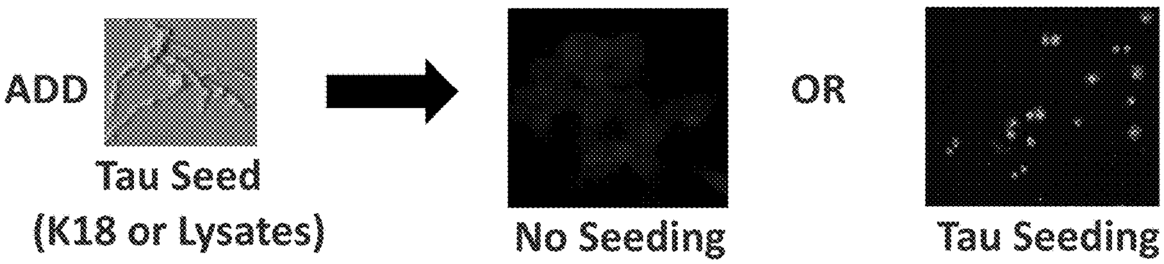
FIGS. 4A, 4B, and 4C. Exemplary bifunctional compounds inhibit Tg2508 ex-vivo seeding of P301L CHO MC1 by high content image analysis. The schematic for the assay is shown in FIG. 4A. Briefly, ChoK1-Tau P301L cells were treated with K18 tau preformed fibrils (PFFs) or extracts from Tg2508 brain samples. Seeded conformational tau species were detected by MC1 antibody positivity and quantified as MC1 spot average intensity per cell on the Image Express high content platform.
Figure 4B:
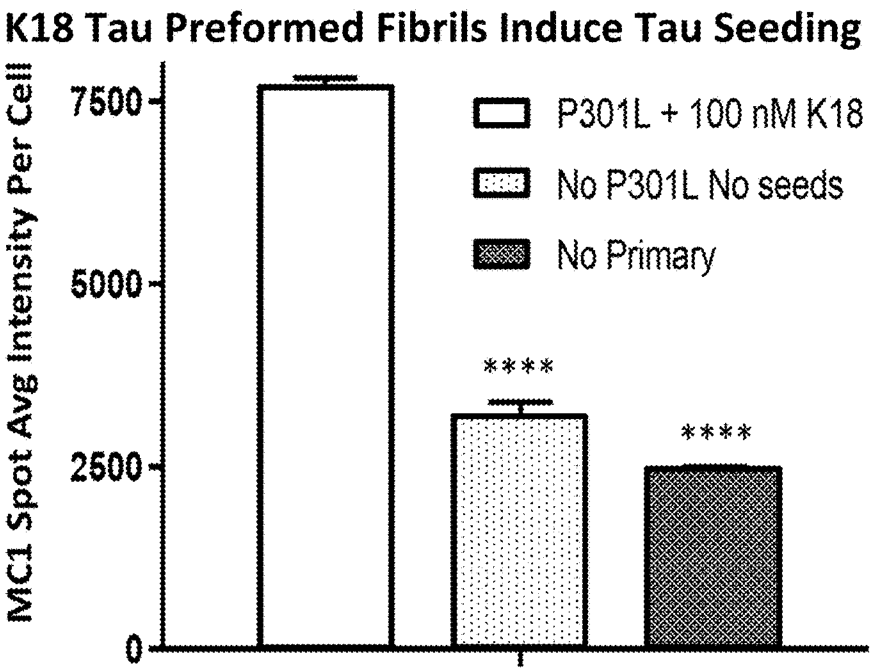
Figure 4C:
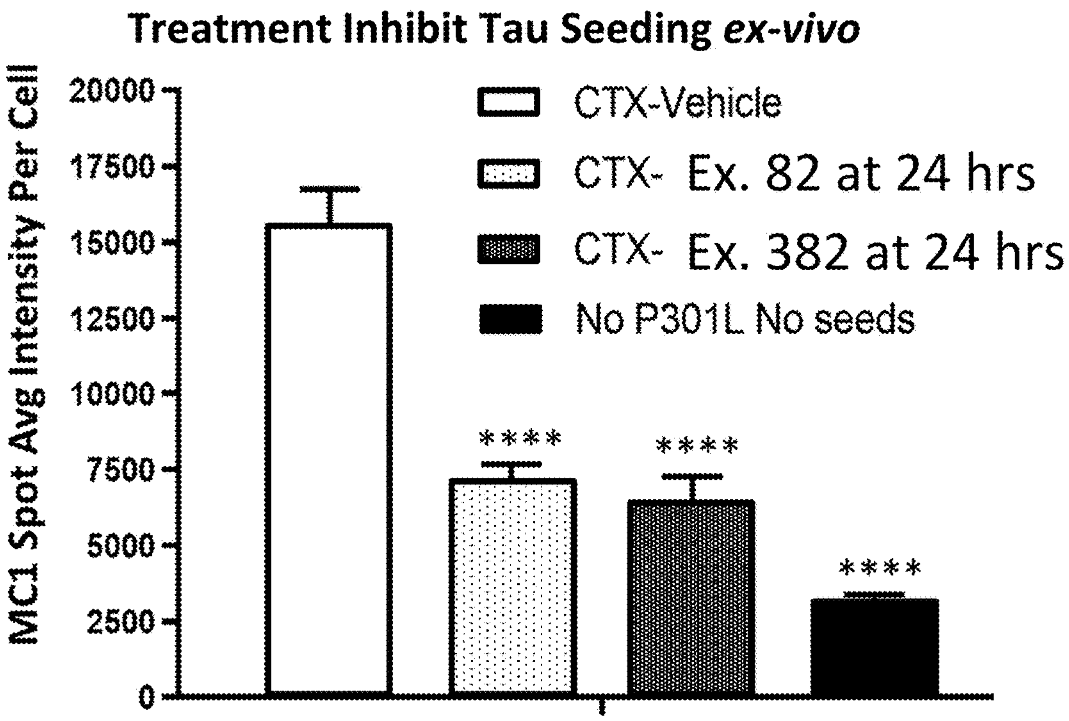

FIGS. 4A, 4B, and 4C. The schematic for the assay is shown in FIG. 4A. Briefly, ChoK1-Tau P301L cells were treated with K18 tau preformed fibrils (PFFs) or extracts from Tg2508 brain samples (as described in Materials and Methods; PFF generation modified from Holmes et al. PNAS. 2014. Proteopathic tau seeding predicts tauopathy in vivo. Oct. 111 (41) E4376-85). Seeded conformational tau species are detected by MC1 antibody positivity and quantified as MC1 spot average intensity per cell on the Image Express™ high content platform. FIG. 4B shows induction of seeded conformational tau induced by K18 PFFs compared to no doxycycline-induced tau or the negative control antibody background staining. FIG. 4C shows significant seeding induction by Tg2508 cortical (CTX) brain extracts and that this seeding competent tau species has been effectively degraded by 24 hours of a single parenteral treatment of Tg2508 mice with 15 mpk exemplary compound 82 or with 30 mpk exemplary compound 382.

Exemplary Bifunctional Compound Reduced Tau in the Brains of Tauopathy Mice in a Dose Dependent Manner.

Figure 5:
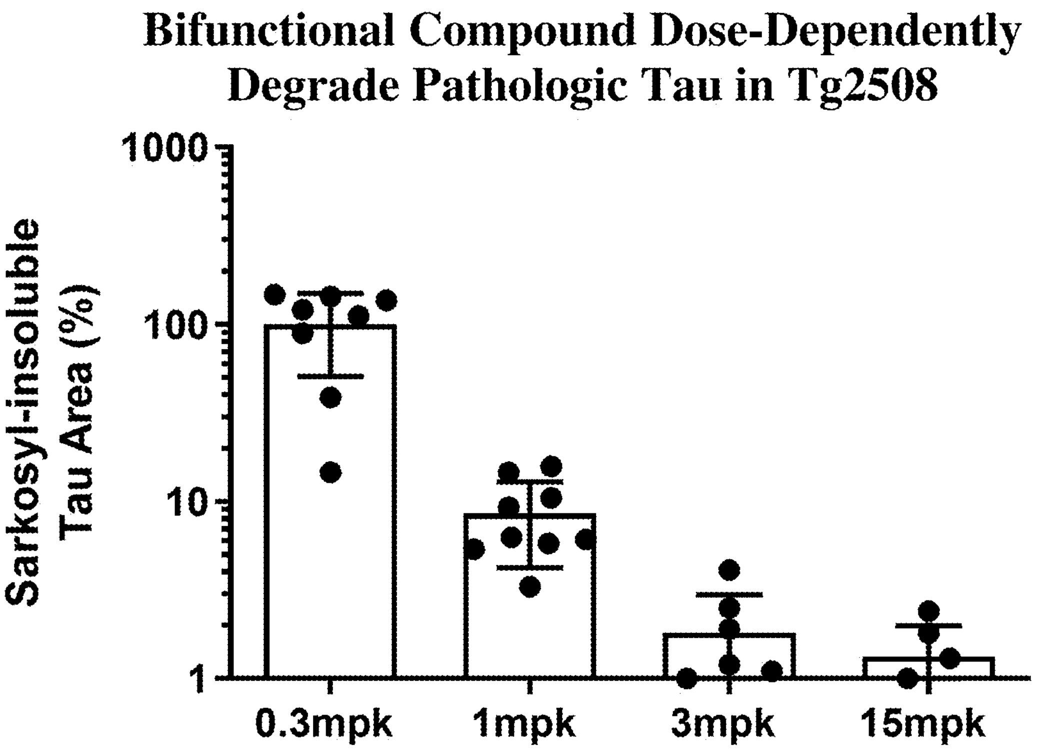
FIG. 5. Exemplary bifunctional compound reduced Tau in the Brains of Tauopathy Mice in a dose dependent manner. Tg2508 animals were dosed with either 15, 3, 1 or 0.3 mpk of bifunctional compound 382 intravenously, as described in materials and methods. Hippocampal extracts were analyzed for either pathologic tau levels by Wes or bifunctional compound levels at each given dose as shown. A clear dose-response relationship is demonstrated. In particular, FIG. 5 demonstrates that the concentration of tau protein is does-dependently reduced in the hippocampi of Tg2508 at 24 hours post dose with the exemplary bifunctional compound.

FIG. 5. Tg2508 animals were dosed with either 15, 3, 1 or 0.3 mpk of bifunctional compound exemplary compound 382 parenterally, as described in materials and methods. Hippocampal extracts were analyzed for either pathologic tau levels by Wes or bifunctional compound levels at each given dose as shown. A clear dose-response relationship is demonstrated. In particular, FIG. 5 demonstrates that the concentration of tau protein is dose-dependently reduced in the hippocampi of Tg2508 mice at 24 hours post dose with the exemplary bifunctional compound.

Methods

In vitro tau Degradation Assay for FIGS. 2A and 2B. T-Rex CHOK1 cells are maintained in Ham's F-12 Nutrient Mix (ThermoFisher) plus 10% Fetal Bovine Serum Tetracycline Negative (Corning) with 10 ug/mL Blasticidin S HCl (Gibco) and 200 ug/mL Zeocin (100 mg/mL, Invitrogen). A stable clone expressing Tau P301L in the presence of doxycycline (1 μg/ml), clone D1 was selected. Compounds were diluted to indicated concentrations and used to treat cells for the indicated times. Cells were harvested from either 96, 24, 6, or 10 cm dishes coated with Poly-D-Lysine (Corning) in ice cold PBS or Buffer H+HALT Protease and phosphatase inhibitors (Thermofisher). Sarkosyl Insoluble tau was isolated as described in Eckermann et al. and Greenberg and Davies, accordingly. WES™ capillary electrophoresis analysis was performed on the Sarkosyl Insoluble tau fraction using Tau1 antibody (Milipore) unless otherwise indicated, as specified in the manufacturers specification (ProteinSimple).

In vivo tau Degradation Assay for FIGS. 3A, 3B and 5. Tg2508 mice (Taconic; Lewis et. al., 2000), were dosed intravenously with the indicated hetero-bifunctional compound formulated in 10% HP-b-CD and 50 mM sodium acetate in water pH 4.0 at the indicated dose and treatment times. All animals had ad libitum access to food and water throughout the studies. Animals were maintained in accordance with the guidelines of the Animal Care and Use Committee of the Arvinas Company, and the "Guide for Care and Use of Laboratory Animals" published by the National Institutes of Health. Research protocols were approved by the Arvinas Animal Care and Use Committee. Brains were harvested and tissue was extracted for sarkosyl insoluble fractionation as described in methods by Eckermann et al., Greenberg and Davies, and Julien et. al., 2012, accordingly. WES™ capillary electrophoresis was performed using Taul antibody (Milipore) unless otherwise indicated as specified in the manufacturers specification (ProteinSimple). Hetero-bifunctional degrader molecule concentrations were determined using standand liquid chromatography and mass spectroscopy methodologies (Drumetix).

In vitro tau Seeding Assay for FIGS. 4A, 4B, and 4C. Tau P301L T-Rex CHO Cells were plated on BioCoat Collagen 96 well microplates that were also poly-D-lysine coated. Media was removed, cells were washed with DPBS, trypsinized and plated at 50,000 cells per mL with Doxycycline 1 mg/mL and no doxycycline control for 24 hours. 96-well plates containing 5,000 cells/well were then transfected with either lysates (at 3 mg/ml) or K18 tau diluted to 100 nM in TBS (2× serial dilutions in optimum with lipofectamine at manufacturer (Thermo) specifications for 24 hours. 96-well plates were then washed 3 times with DPBS, fixed 4% PFA in DPBS+1% Triton X-100, aspirated, blocked using 3% BSA/TBST blocking solution (stored at 4° C.) for 1 hour. MC1 antibody (kindly provided by P. Davies-Einstein-Concentration 5.2 mg/mL, Lot #919) was diluted in 1% BSA/TBST overnight in cold room, washed 3 times with TBST and then secondary antibody cocktail was added (1:5000) of Goat anti-Mouse IgG-488 (Thermofisher) . Plates were incubated at room temperature, protected from light for one hour, then washed three times with TBST. Hoechst 33342 1:1000 in TBST was then added and incubated for 1 hour at room temperature, washed with TBST three times and stored in TBST at 4° C. protected from light until imaging. Imaging was performed on the Molecular Devices High-Content imaging with appropriate algorithm looking at spot, and total, average intensity per cell as well as any other parameters of interest.

Tau Protein In Vitro SK-N-SUH Degradation Assay

An alternative assay for measuring tau protein degradation in vitro is tau protein degradation in SK-N-SH cells. To determine the effect of the bifunctional molecules on tau protein degradation SK-N-SH cells were seeded in a 24-well tissue culture-treated plate for at least 18-hours prior to compound addition. Tau bifunctional molecules were evaluated for tau degradation by lysing the cells in lysis buffer with protease inhibitors following a 72-hour incubation with tau bifunctional molecules at 300 nM, 100 nM, 33 nM and 11 nM. Cell lysates were run on standard SDS-PAGE gels, and tau levels were detected by Western blotting using Tau-13 antibody from Abcam (Cambridge, UK) that binds to all forms of human tau.

Tau Quantitative Immunocytochemistry. An alternative method for measuring tau protein degradation in vitro is tau quantitative immunocytochemistry assay Immunocytochemistry based methods for measuring degradation of tau in either primary rodent Neurons, human induced pluripotent cell derived neurons or in doxycycline induced CHOK1 Tau P301L cells is performed in three formats with and without seeding with P301L preformed fibrils. The assay is also performed using fixation with and without 1% Triton-X to differentiate between soluble larger oligomer versus smaller monomeric aggregates (as described in Guo and Lee, 2011).

Tau P301L CHOK1 cells are trypsinized and diluted in medium (Ham's F12 Nutrient media, 10% Tet Free FBS, 10 ug/mL Blasticidin and 200 ug/mL Zeocin). Cells are then plated into PDL coated 96-well imaging quality plates at a final concentration of 2,000 cells per well. The plates are incubated at 37° C., 5% $CO_2$ overnight. The next day the P301L Tau mutant protein is induced with 500 ng/ml Doxycycline and treated with 500 nM hetero-bifunctional compounds in 0.5% DMSO. Wells that are not treated with Doxycycline serve as control wells. Cells are incubated at 37° C. for 24 hours. For treatment of cells with preformed fibrils of tau (PFF), cells are seeded with P301L preformed fibrils (PFF obtained from Stressmarq and prepared using manufacture specifications), the transfection solution is prepared using Lipofectamine 2000 in OptiMEM and the K18 PFF. 10 uL of PFF transfection solution is added to the wells dropwise for a final concentration of 30 nM PFF. For wells not receiving PFF, 10 uL of OptiMEM is added to those wells. The plates are returned to the 37° C. incubator for 24 and 48 hours. The cells are fixed by adding a final concentration of 4% paraformaldehyde with or without 1% Triton-X for 15 minutes and then washed 3 times with PBS.

Immunocytochemical staining of the fixed cells is performed using antibodies to measure Total tau (Tau 5, Tau 1, HT7, as specified), Tau aggregates (MC1), and phospho-tau (PHF-1, p181). Due to species incompatibility, the antibodies are prelabeled with their secondary antibodies using labeling kits. PBS is removed, and fixed cells are blocked with 3% BSA in PBS for 1 hour at room temperature. The blocking buffer is then removed, the antibody cocktail added and incubated at 4° C., to protect from light overnight. The plates are washed twice with PBS, stained with Hoechst 33342 and Phalloidin (actin stain) and incubated for 10 minutes at room temperature. Cells are washed twice with PBS and the plates are sealed to protect from light.

The plates are imaged using widefield or confocal optics with a 20× objective acquiring 4 channels at the optimal exposure times. ~40-50% saturation of the camera is found to be optimal for detection of the aggregates to detect degradation of the proteins.

The images are analyzed on Thermo Cell Insight CX7 High-Content Screening Platform by first performing background correction to eliminate nonspecific background signal. Then the individual objects are defined based on the Hoechst nuclear staining. A threshold is then defined for determining the positive signal from the background for each antibody. Spot detection is used to define the aggregate formation and eliminate the inclusion of background signal in the measurement. The morphology of the phalloidin (actin) staining is determined by the fiber intensity, size, shape and texture. The mean of the well for the total and average intensity and area of the identified spot regions from each antibody channel is calculated along with the total object count for each well. The individual results are normalized by the plate as a percent of the negative DMSO control where DMSO represents 100% of tau and heterobifunctional compound that degrade the tau antibodies would result in significantly less tau than the 100% control.

REFERENCES

Lewis J., McGowan E., Rockwood J., Melrose H., Nacharaju P., Van Slegtenhorst M., Gwinn-Hardy K., Paul Murphy M., Baker M., Yu X., Duff K., Hardy J., Corral A., Lin W. L., Yen S. H., Dickson D. W., Davies P., Hutton M. Nat Genet. 2000. Neurofibrillary tangles, amyotrophy and progressive motor disturbance in mice expressing mutant (P301L) tau protein. August; 25(4):402-5.

Holmes B. B., Furman J. L., Mahan T. E., Yamasaki T. R., Mirbaha H., Eades W. C., Belaygorod L., Cairns N. J., Holtzman D. M., and Diamond M. I. PNAS. 2014. Proteopathic tau seeding predicts tauopathy in vivo. October 111 (41) E4376-85.

Yanamandra K., Kfoury N., Jiang H., Mahan T. E., Ma S., Maloney S. E., Wozniak D. F., Diamond M. I., Holtzman D. M. Neuron. 2013. Anti-Tau Antibodies that Block Tau Aggregate Seeding In Vitro Markedly Decrease Pathology and Improve Cognition In Vivo. October; 80(2):402-414.

Eckermann K., Mocanu, M.-M., Khlistunova I., Biernat J., Nissen A., Hofmann A., Schönig K., Bujard H., Haemisch A., Mandelkow E., Zhou L., Rune G., Mandelkow E.-M. JBC. 2007. The β-Propensity of Tau Determines Aggregation and Synaptic Loss in Inducible Mouse Models of Tauopathy 282: 31755-65.

Greenberg and Davies. PNAS. 1990 A preparation of Alzheimer paired helical filaments that displays distinct tau proteins by polyacrylamide gel electrophoresis. August; 87(15):5827-31.

Julien C., Bretteville A., Planel E. 2012. Methods Mol Biol. Biochemical isolation of insoluble tau in transgenic mouse models of tauopathies. 849:473-91.

Guo, J. L. and Lee, V. M.-Y. Seeding of Normal Tau by Pathological Tau Conformers Drives Pathogenesis of Alzheimer-like Tangles J Biol Chem. 2011 Apr. 29; 286 (17): 15317-15331.

What is claimed is:

1. A compound selected from:

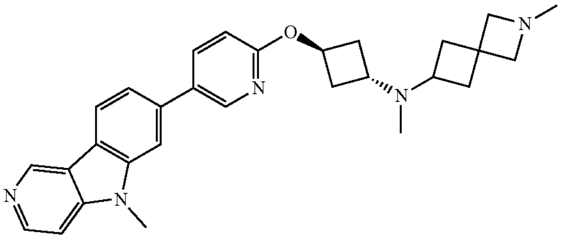

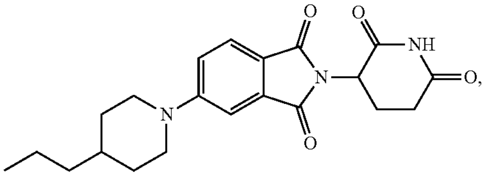
,

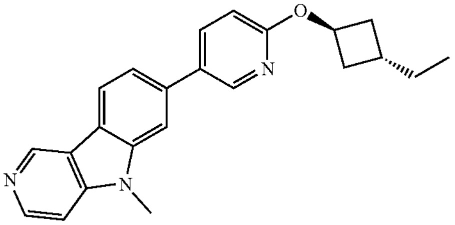

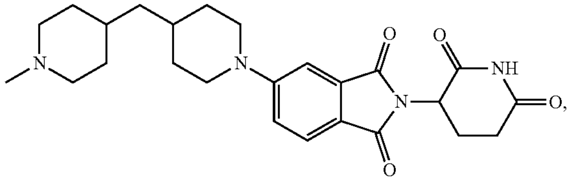
,

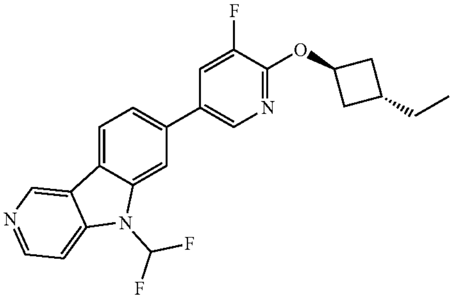

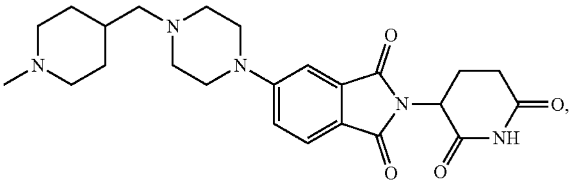
,

-continued

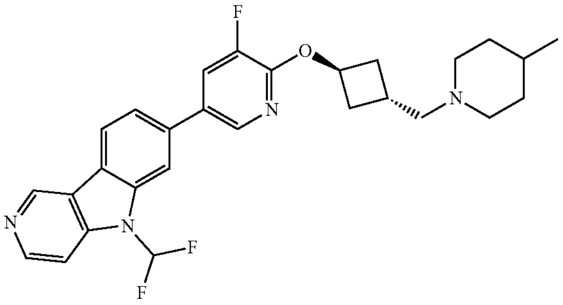

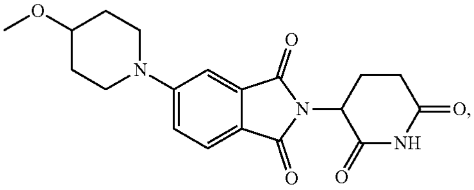
,

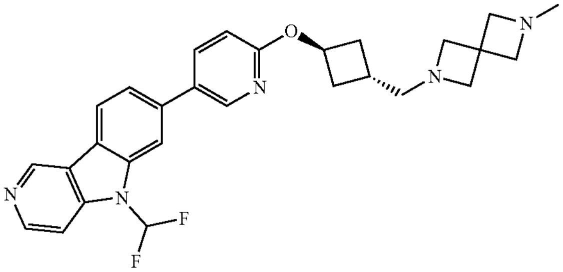

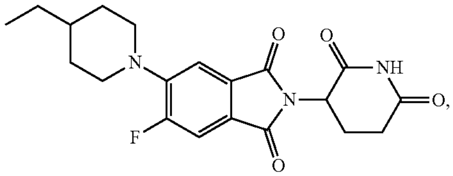
,

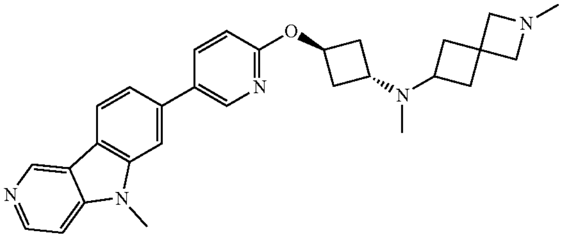

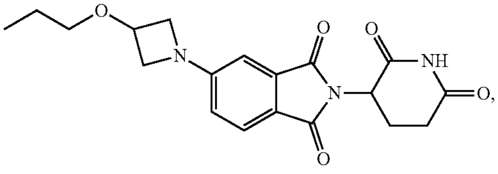
,

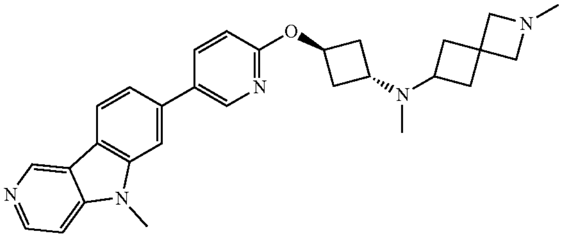

-continued
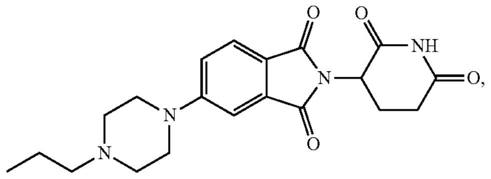
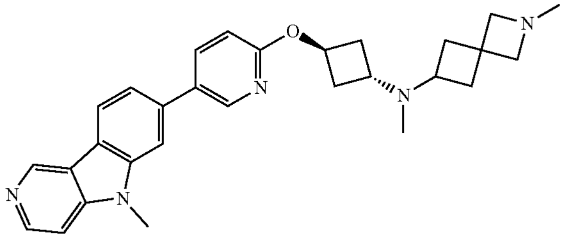
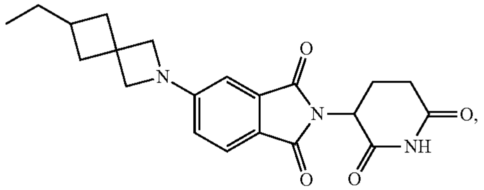
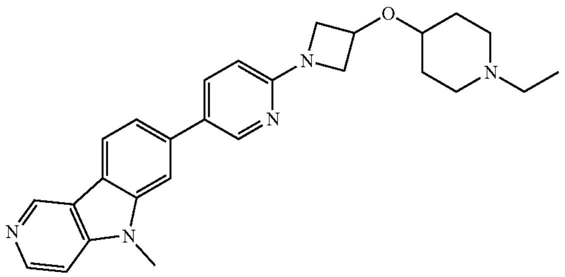
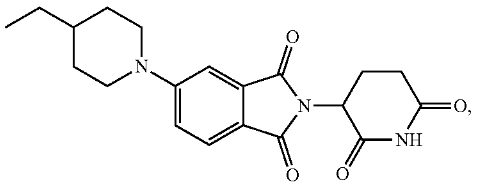
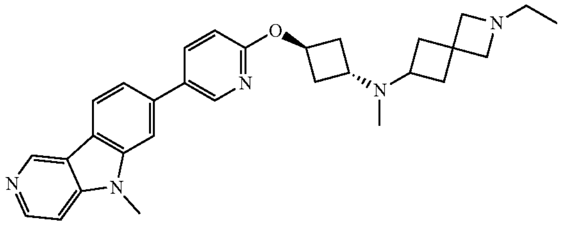
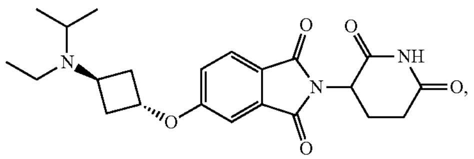
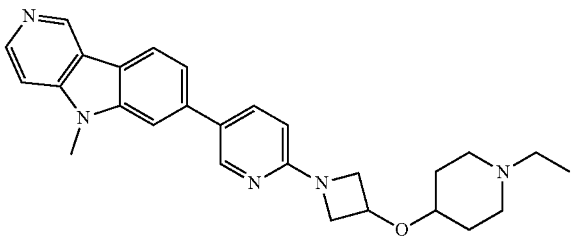
-continued
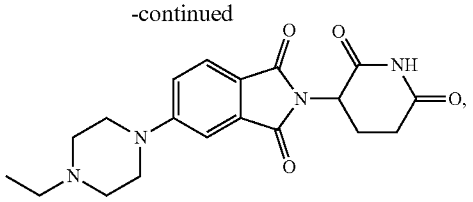
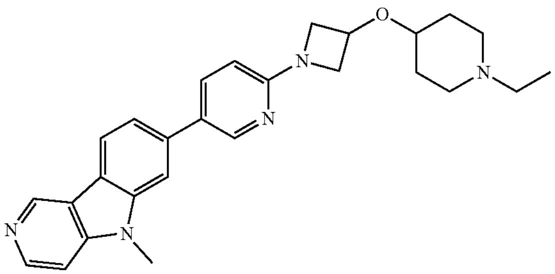
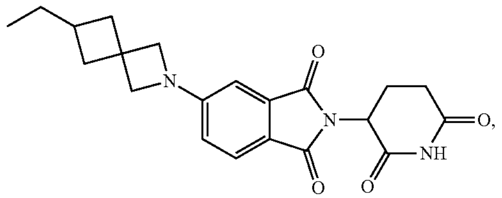
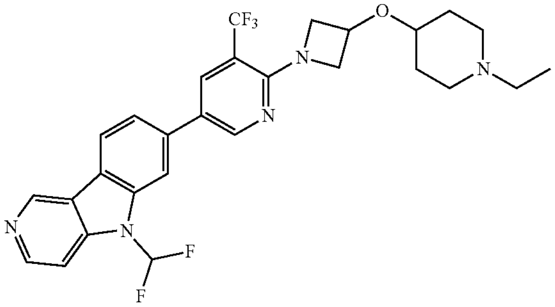
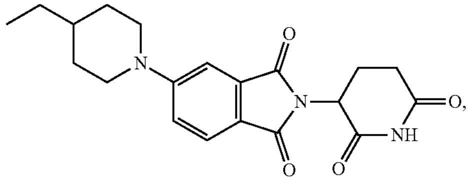
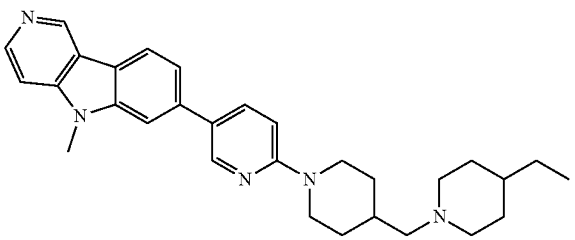
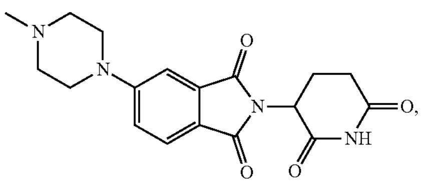

-continued
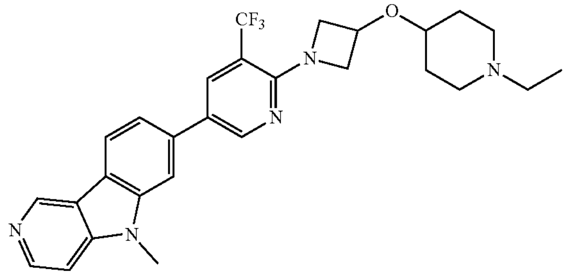
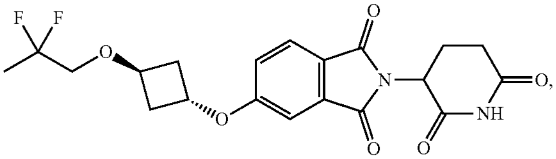,
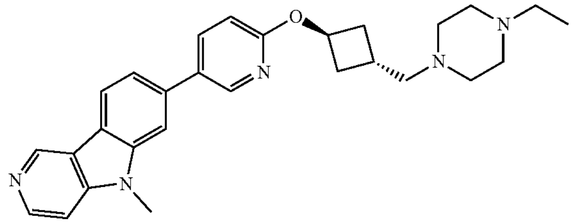
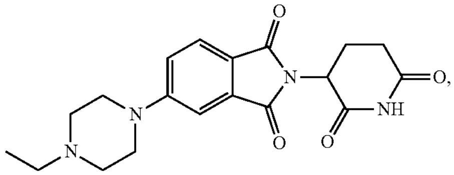,
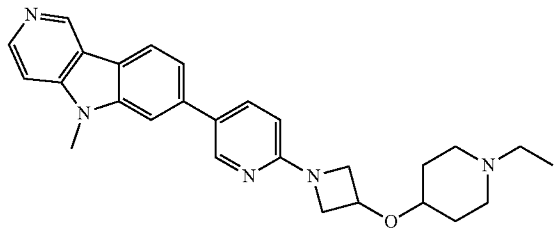
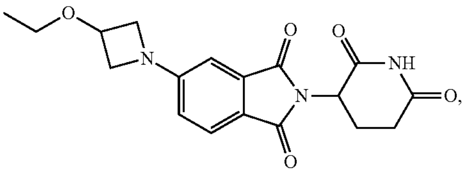,
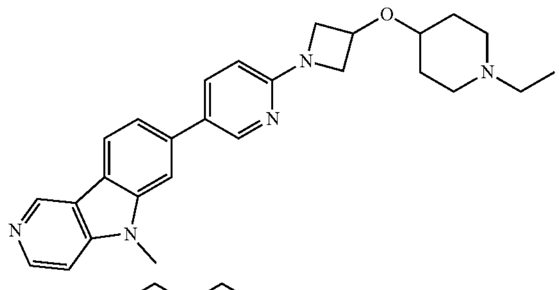
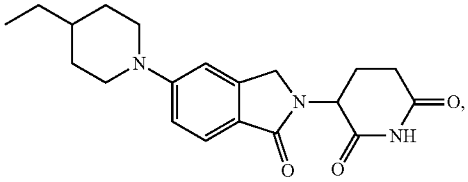,
-continued
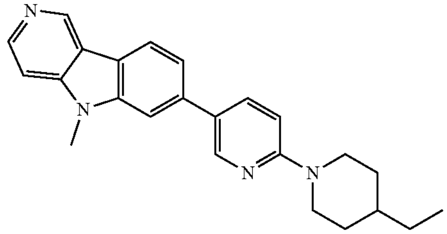
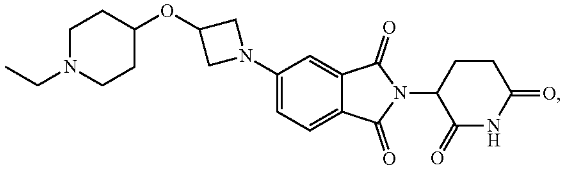,
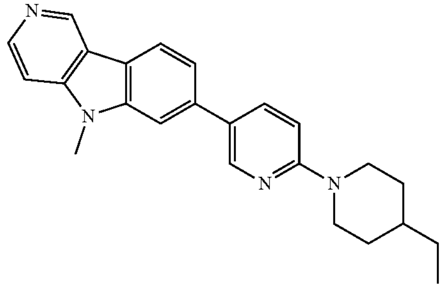
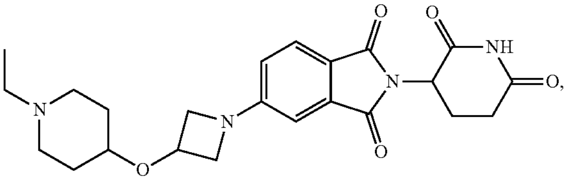,
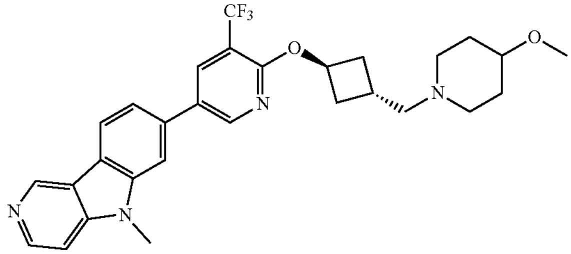
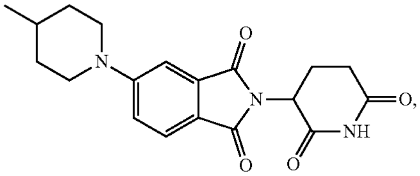, and
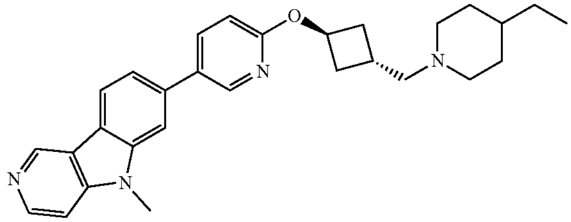
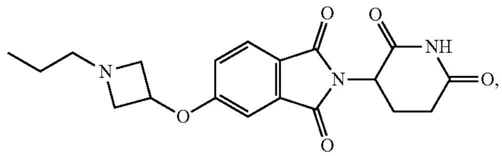,
or a pharmaceutically acceptable salt thereof.

2. The compound of claim 1, wherein the compound demonstrates Tau protein degradation of greater than 50% as determined in CHOK1 Tau P301 L cells treated with 1 μM of compound for 48 hours as compared to untreated cells.

3. The compound of claim 1, wherein the compound demonstrates Tau protein degradation of less than or equal to 50% as determined in CHOK1 Tau P301 L cells treated with 1 μM of compound for 48 hours as compared to untreated cells.

4. The compound of claim 1, wherein the compound demonstrates Tau protein degradation in an in vivo tauopathy mouse model.

5. The compound of claim 1, wherein the compound demonstrates Tau protein degradation of seed-competent pathologic tau aggregates in vitro and in vivo.

6. A pharmaceutical composition comprising a compound of claim 1, and a pharmaceutically acceptable carrier.

7. The pharmaceutical composition of claim 6, wherein the composition further comprises an additional bioactive agent.

8. The pharmaceutical composition of claim 7, wherein the additional bioactive agent is an anti-neurodegenerative agent.

9. The pharmaceutical composition of claim 7, wherein the additional bioactive agent is a P-gp inhibitor.

10. The pharmaceutical composition of claim 9, wherein the P-gp inhibitor is Amiodarone, Azithromycin, Captopril, Clarithromycin, Cyclosporine, Piperine, Quercetin, Quinidine, Quinine, Reserpine, Ritonavir, Tariquidar, Elacridar or Verapamil.

11. The compound of claim 1, wherein the compound is selected from:

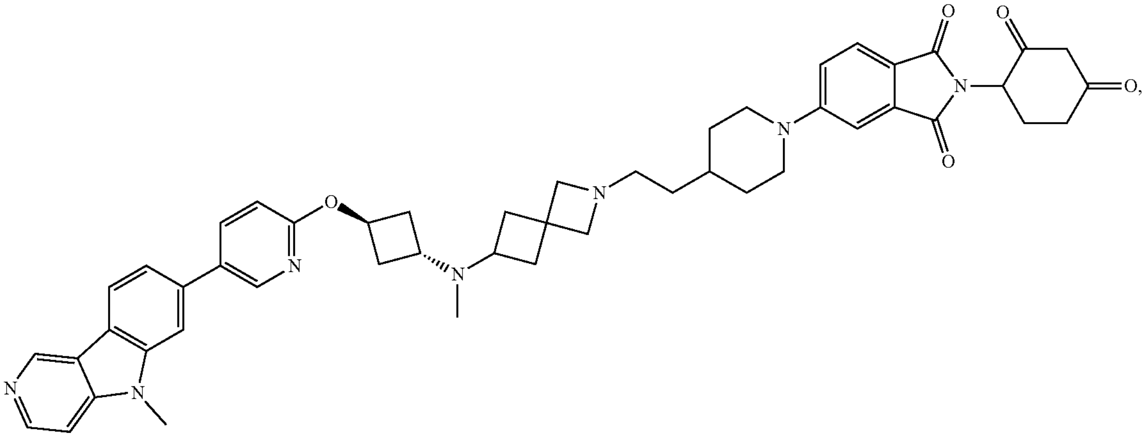

,

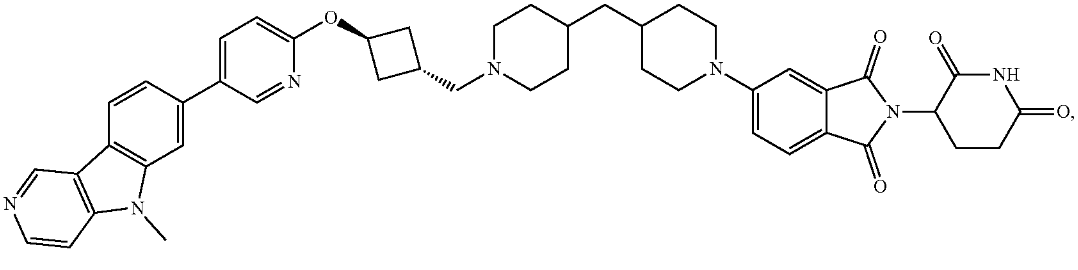

,

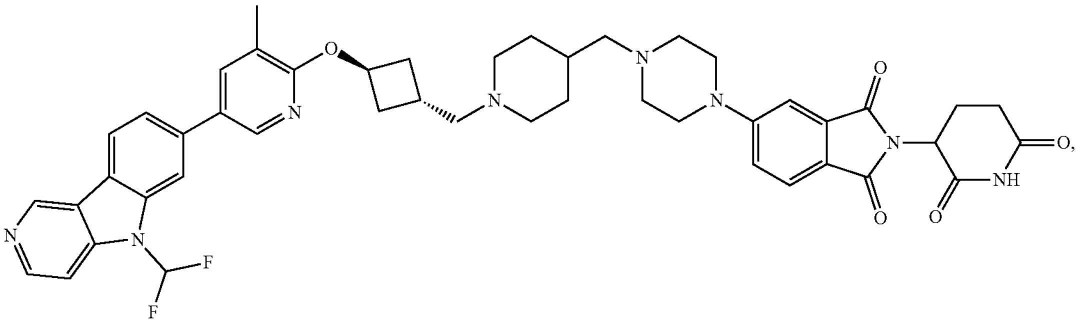

,

-continued
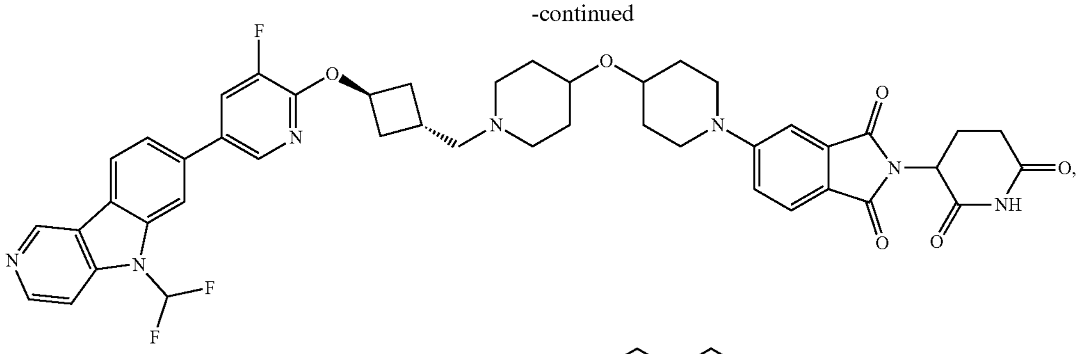
and
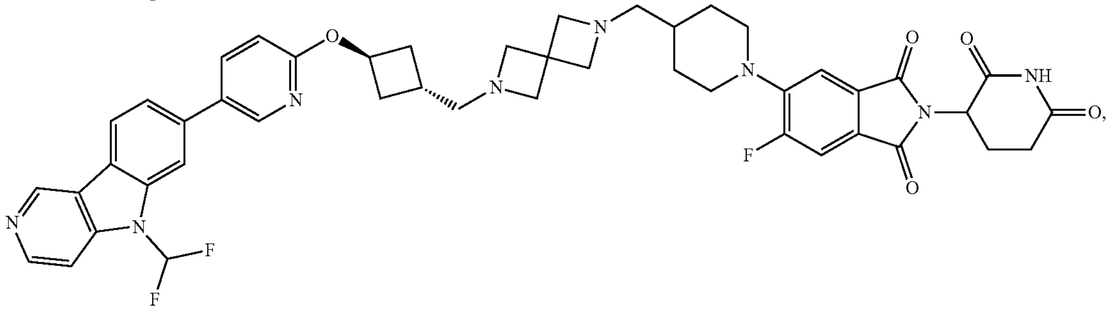
or a pharmaceutically acceptable salt thereof.
12. The compound of claim 1, wherein the compound is:
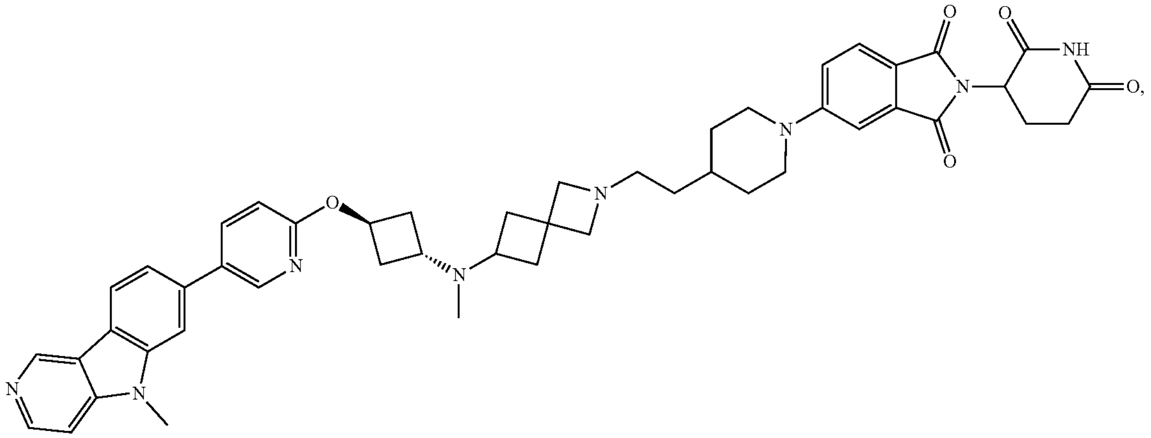 [SMILES: Cn1c2ccncc2c2ccc(-c3ccc(O[C@H]4C[C@H](N(C)C5CC6(C5)CN(CCC5CCN(c7ccc8c(c7)C(=O)N(C7CCC(=O)NC7=O)C8=O)CC5)C6)C4)nc3)cc21]
or a pharmaceutically acceptable salt thereof.
13. The compound of claim 1, wherein the compound is:
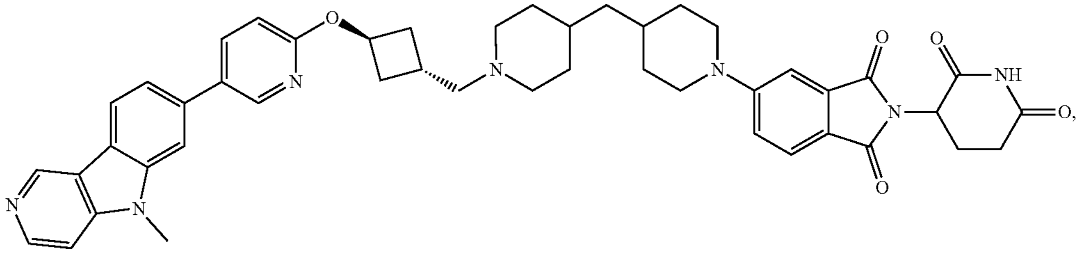 [SMILES: Cn1c2ccncc2c2ccc(-c3ccc(O[C@H]4C[C@H](CN5CCC(CC6CCN(c7ccc8c(c7)C(=O)N(C7CCC(=O)NC7=O)C8=O)CC6)CC5)C4)nc3)cc21]
or a pharmaceutically acceptable salt thereof.

14. The compound of claim 1, wherein the compound is:

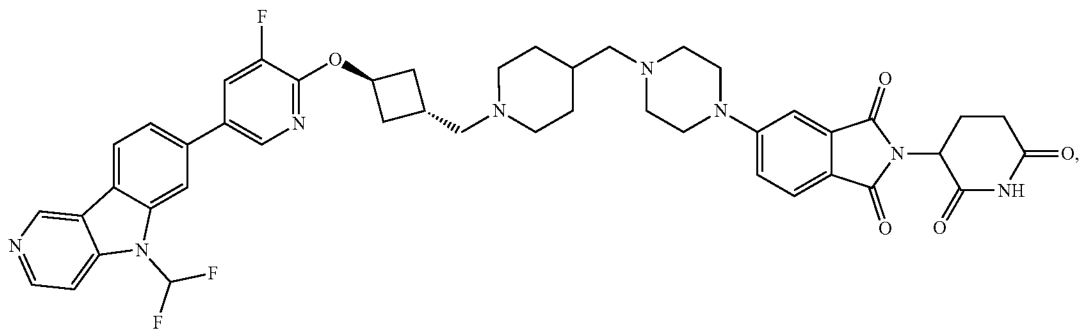 [SMILES: O=C1CCC(N2C(=O)c3ccc(N4CCN(CC5CCN(C[C@H]6C[C@H](Oc7ncc(-c8ccc9c%10cnccc%10n(C(F)F)c9c8)cc7F)C6)CC5)CC4)cc3C2=O)C(=O)N1]

or a pharmaceutically acceptable salt thereof.

15. The compound of claim 1, wherein the compound is:

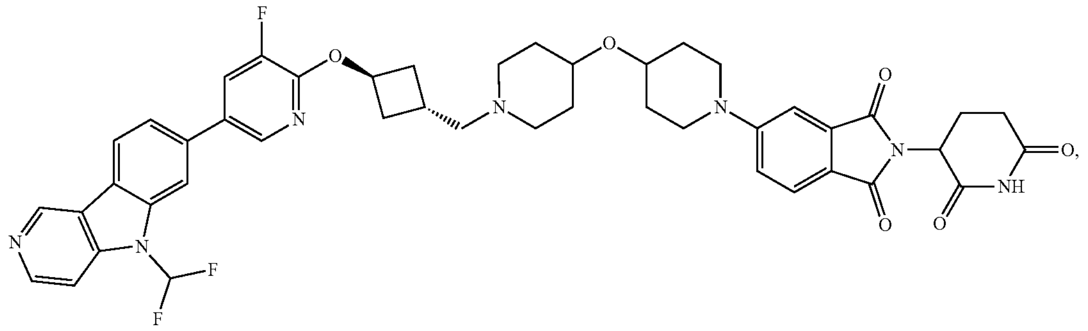 [SMILES: O=C1CCC(N2C(=O)c3ccc(N4CCC(OC5CCN(C[C@H]6C[C@H](Oc7ncc(-c8ccc9c%10cnccc%10n(C(F)F)c9c8)cc7F)C6)CC5)CC4)cc3C2=O)C(=O)N1]

or a pharmaceutically acceptable salt thereof.

16. The compound of claim 1, wherein the compound is:

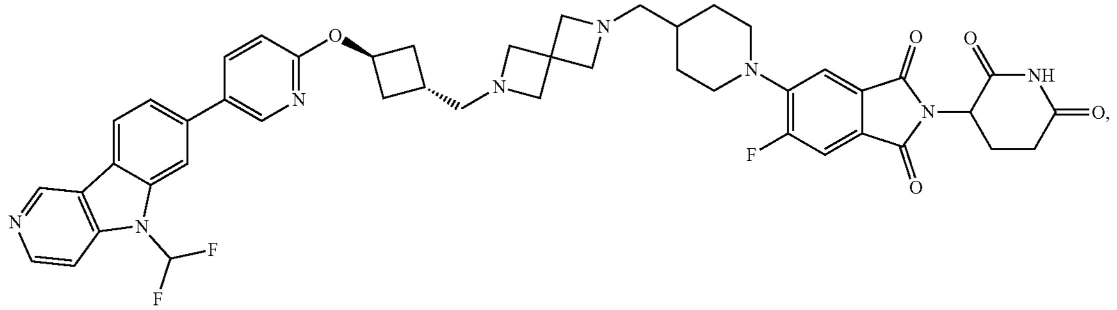 [SMILES: O=C1CCC(N2C(=O)c3cc(F)c(N4CCC(CN5CC6(C5)CN(C[C@H]5C[C@H](Oc7ccc(-c8ccc9c%10cnccc%10n(C(F)F)c9c8)cn7)C5)C6)CC4)cc3C2=O)C(=O)N1]

or a pharmaceutically acceptable salt thereof.

17. The compound of claim 1, wherein the compound is:

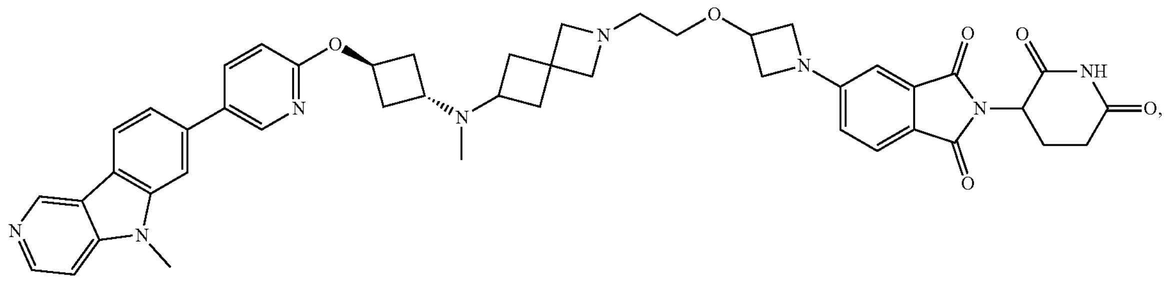 [SMILES: Cn1c2ccncc2c2ccc(-c3ccc(O[C@H]4C[C@H](N(C)C5CC6(C5)CN(CCOC5CN(c7ccc8c(c7)C(=O)N(C7CCC(=O)NC7=O)C8=O)C5)C6)C4)nc3)cc21]

or a pharmaceutically acceptable salt thereof.

18. The compound of claim 1, wherein the compound is:

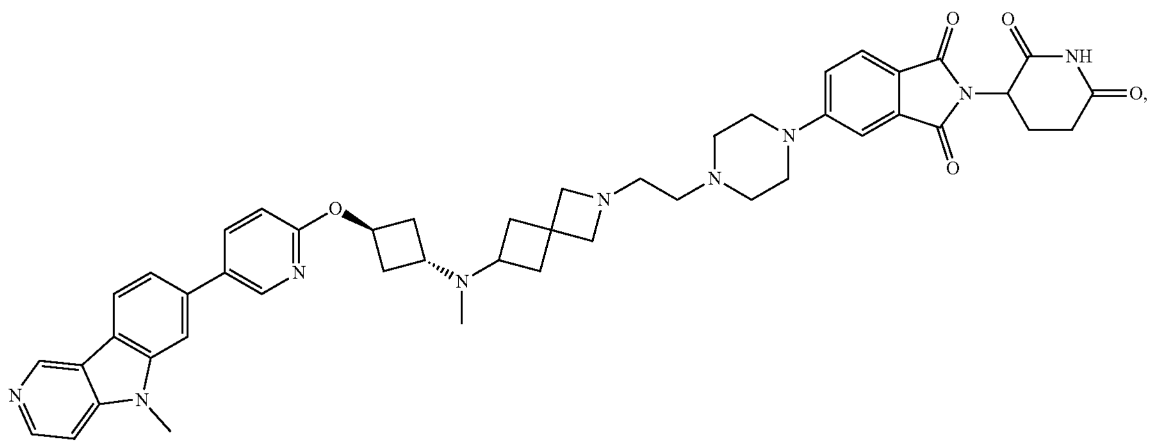 [SMILES: Cn1c2ccncc2c2ccc(-c3ccc(O[C@H]4C[C@H](N(C)C5CC6(C5)CN(CCN5CCN(c7ccc8c(c7)C(=O)N(C7CCC(=O)NC7=O)C8=O)CC5)C6)C4)nc3)cc21]

or a pharmaceutically acceptable salt thereof.

19. The compound of claim 1, wherein the compound is:

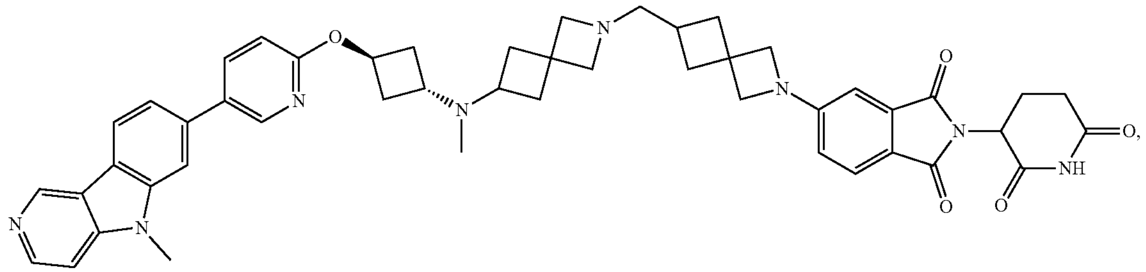 [SMILES: Cn1c2ccncc2c2ccc(-c3ccc(O[C@H]4C[C@H](N(C)C5CC6(C5)CN(CC5CC7(C5)CN(c5ccc8c(c5)C(=O)N(C5CCC(=O)NC5=O)C8=O)C7)C6)C4)nc3)cc21]

or a pharmaceutically acceptable salt thereof.

20. The compound of claim 1, wherein the compound is:

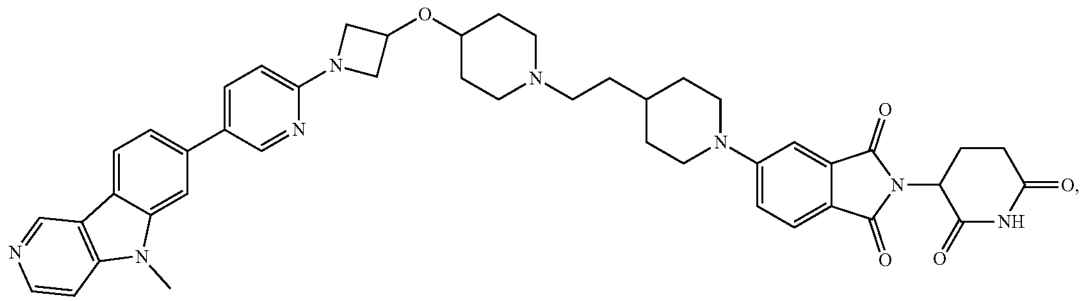 [SMILES: Cn1c2ccncc2c2ccc(-c3ccc(N4CC(OC5CCN(CCC6CCN(c7ccc8c(c7)C(=O)N(C7CCC(=O)NC7=O)C8=O)CC6)CC5)C4)nc3)cc21]

or a pharmaceutically acceptable salt thereof.

21. A method of treating Alzheimer's disease in a subject comprising administering to a subject in need thereof, the compounds of claim 1 and pharmaceutically acceptable salts thereof.

* * * * *